US012559506B2

(12) United States Patent
Araujo et al.

(10) Patent No.: US 12,559,506 B2

(45) Date of Patent: Feb. 24, 2026

(54) INDAZOLE BASED COMPOUNDS AND ASSOCIATED METHODS OF USE

(71) Applicant: Arvinas Operations, Inc., New Haven, CT (US)

(72) Inventors: Erika Marina Vieira Araujo, Woodbridge, CT (US); Michael Berlin, Flemington, NJ (US); Hanqing Dong, Madison, CT (US); Steven M. Sparks, Guilford, CT (US); Jing Wang, Milford, CT (US); Wei Zhang, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

(21) Appl. No.: 18/659,374

(22) Filed: May 9, 2024

(65) Prior Publication Data

US 2024/0360152 A1 Oct. 31, 2024

Related U.S. Application Data

(63) Continuation of application No. 17/699,082, filed on Mar. 19, 2022, now Pat. No. 11,981,683.

(60) Provisional application No. 63/245,411, filed on Sep. 17, 2021, provisional application No. 63/243,014, filed on Sep. 10, 2021, provisional application No. 63/228,731, filed on Aug. 3, 2021, provisional application No. 63/163,328, filed on Mar. 19, 2021.

(51) Int. Cl.

| | |
|---|---|
| ***C07D 498/10*** | (2006.01) |
| ***A61K 45/06*** | (2006.01) |
| ***C07D 401/14*** | (2006.01) |
| ***C07D 413/14*** | (2006.01) |
| ***C07D 417/14*** | (2006.01) |
| ***C07D 471/04*** | (2006.01) |
| ***C07D 471/10*** | (2006.01) |
| ***C07D 487/08*** | (2006.01) |
| ***C07D 487/10*** | (2006.01) |

(52) U.S. Cl.

CPC ............ *C07D 498/10* (2013.01); *A61K 45/06* (2013.01); *C07D 401/14* (2013.01); *C07D 413/14* (2013.01); *C07D 417/14* (2013.01); *C07D 471/04* (2013.01); *C07D 471/10* (2013.01); *C07D 487/08* (2013.01); *C07D 487/10* (2013.01)

(58) Field of Classification Search

CPC ................................ A61P 25/16; A61P 25/28

See application file for complete search history.

(56) References Cited

U.S. PATENT DOCUMENTS

| | | | | |
|---|---|---|---|---|
| 11,981,683 | B2 * | 5/2024 | Araujo .................... | A61P 25/16 |
| 12,053,469 | B2 | 8/2024 | Araujo et al. | |
| 2011/0301141 | A1 | 12/2011 | Baker-Glenn et al. | |
| 2016/0009681 | A1 | 1/2016 | Miller et al. | |
| 2016/0009689 | A1 | 1/2016 | Miller et al. | |
| 2016/0176916 | A1 | 6/2016 | Bradner et al. | |
| 2018/0099940 | A1 | 4/2018 | Crew et al. | |
| 2021/0238193 | A1 | 8/2021 | Mainolfi et al. | |
| 2021/0361774 | A1 | 11/2021 | Gray et al. | |
| 2023/0083376 | A1 | 3/2023 | Lu et al. | |
| 2023/0097358 | A1 | 3/2023 | Araujo et al. | |
| 2025/0114356 | A1 | 4/2025 | Araujo et al. | |

FOREIGN PATENT DOCUMENTS

| | | | | |
|---|---|---|---|---|
| CN | 110621322 | A | 12/2019 | |
| CN | 112888460 | A | 6/2021 | |
| WO | 2011/141756 | A1 | 11/2011 | |
| WO | 2014/134774 | A1 | 9/2014 | |
| WO | 2014/134776 | A1 | 9/2014 | |
| WO | WO-2014137723 | A1 * | 9/2014 | ......... C07D 491/107 |
| WO | 2015/160842 | A1 | 10/2015 | |
| WO | 2015/160845 | A2 | 10/2015 | |
| WO | 2018/148443 | A1 | 8/2018 | |
| WO | 2019/199816 | A1 | 10/2019 | |
| WO | 2019/222173 | A1 | 11/2019 | |
| WO | 2020/081682 | A1 | 4/2020 | |
| WO | 2021/127278 | A1 | 6/2021 | |
| WO | 2021/194878 | A1 | 9/2021 | |

(Continued)

OTHER PUBLICATIONS

International Search Report for Application No. PCT/US2022/021049, dated Jun. 30, 2022, 5 pages.

(Continued)

*Primary Examiner* — Jeffrey S Lundgren

*Assistant Examiner* — Eric Tran

(74) *Attorney, Agent, or Firm* — McCarter & English, LLP; Michael J. DeGrazia; James M. Alburger

(57) ABSTRACT

Bifunctional compounds, which find utility as modulators of leucine-rich repeat kinase 2 (LRRK2), are described herein. In particular, the hetero-bifunctional compounds of the present disclosure contain on one end a moiety that binds to the cereblon E3 ubiquitin ligase and on the other end a moiety which binds LRRK2, such that the target protein is placed in proximity to the ubiquitin ligase to effect degradation (and inhibition) of target protein. The hetero-bifunctional compounds of the present disclosure exhibit a broad range of pharmacological activities associated with degradation/inhibition of target protein. Diseases or disorders that result from aberrant regulation of the target protein are treated or prevented with compounds and compositions of the present disclosure.

20 Claims, 1 Drawing Sheet

(56) References Cited

FOREIGN PATENT DOCUMENTS

| | | | |
|---|---|---|---|
| WO | 2021/194879 | A1 | 9/2021 |
| WO | 2022/198101 | A1 | 9/2022 |
| WO | 2022/198112 | A1 | 9/2022 |
| WO | 2023/283606 | A1 | 1/2023 |
| WO | 2023/011456 | A1 | 2/2023 |
| WO | 2024/054876 | A1 | 3/2024 |

OTHER PUBLICATIONS

U.S. Appl. No. 17/699,082, filed Mar. 19, 2022, U.S. Pat. No. 11,981,683, Issued.

Liu et al., Discovery of XL01126: A Potent, Fast, Cooperative, Selective, Orally Bioavailable, and Blood-Brain Barrier Penetrant Protac Degrader of Leucine-Rich Repeat Kinase 2. Journal of the American Chemical Society. 2022;144:16930-16952.

PubChem SID No. 447021161, LIJMLEVZYKFYAF-YYFFZOGMSA-N. 3 pages, Nov. 10, 2021.

International Search Report and Written Opinion for Application No. PCT/US2021/023179, dated Jun. 10, 2021, 10 pages.

International Search Report and Written Opinion for Application No. PCT/US2021/023183, dated Jun. 10, 2021, 13 pages.

International Preliminary Report on Patentability for Application No. PCT/US2021/023183, dated Oct. 8, 2022, 8 pages.

International Search Report and Written Opinion for Application No. PCT/US2024/048800, dated Jan. 23, 2025, 9 pages.

International Preliminary Report on Patentability for Application No. PCT/US2022/021049, dated Sep. 28, 2023, 8 pages.

International Preliminary Report on Patentability for Application No. PCT/US2023/075389, dated Mar. 20, 2025, 6 pages.

International Preliminary Report on Patentability for Application No. PCT/US2022/021049, dated Jun. 30, 2022, 5 pages.

* cited by examiner

INDAZOLE BASED COMPOUNDS AND ASSOCIATED METHODS OF USE

CROSS-REFERENCE TO RELATED APPLICATIONS

The application is a continuation application of U.S. patent application Ser. No. 17/699,082, filed on 19 Mar. 2022, which claims priority to and the benefit of U.S. Provisional Application No. 63/163,328, filed on 19 Mar. 2021, and U.S. Provisional Application No. 63/228,731, filed 3 Aug. 2021, and U.S. Provisional Application No. 63/243,014, filed 10 Sep. 2021, and U.S. Provisional Application No. 63/245,411, filed 17 Sep. 2021, each of which is titled "INDAZOLE BASED COMPOUNDS AND ASSOCIATED METHODS OF USE" and incorporated herein by reference in its entirety for all purposes.

INCORPORATION BY REFERENCE

All cited references are hereby incorporated herein by reference in their entirety, including U.S. application Ser. No. 17/207,325, filed 19 Mar. 2021, titled INDAZOLE BASED COMPOUNDS AND ASSOCIATED METHODS OF USE, published as U.S. Patent Application Publication No. 2021/0315896, U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 15/953,108, filed on Apr. 13, 2018, published as U.S. Patent Application Publication No. 2018/0228907; and U.S. Patent Application Publication No. 2016/0009689 A1, filed 2 Sep. 2015; and U.S. Patent Application Publication No. 2016/0200722 A1, filed 18 Feb. 2016.

FIELD OF THE INVENTION

The invention provides hetero-bifunctional compounds comprising a target protein binding moiety and a E3 ubiquitin ligase binding moiety, and associated methods of use. The bifunctional compounds are useful as modulators of targeted ubiquitination of leucine-rich repeat kinase 2 (LRRK2), which is then degraded and/or inhibited.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands that bind to these ligases. For example, since the discovery of nutlins, the first small molecule E3 ligase inhibitors, additional compounds have been reported that target E3 ligases.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Bifunctional compounds such as those described in U.S. Patent Application Publications 2015/0291562 and 2014/0356322 (incorporated herein by reference), function to recruit endogenous proteins to an E3 ubiquitin ligase for ubiquitination and subsequent degradation in the proteasome degradation pathway. In particular, the publications cited above describe bifunctional or proteolysis-targeting chimeric (PROTAC®) protein degrader compounds, which find utility as modulators of targeted ubiquitination of a variety of polypeptides and proteins, which are then degraded and/or inhibited by the bifunctional compounds.

Leucine-rich repeat kinase 2 (LRRK2) is a member of the leucine-rich repeat kinase family and is a large multi-domain protein with an N-terminal armadillo domain, ankryin repeat region, a leucine-rich repeat (LRR) domain, a tandem Roco type GTPase domain, a kinase domain containing a DFG-like motif, and a C-terminal WD40 domain. The LRRK2 protein is 2527 amino acids and a molecular weight of 280 kDa. Catalytic activities of LRRK2 are associated with the kinase and GTPase domain, and LRRK2 is a heterodimer in its active form (Greggio E, et al.: The Parkinson disease-associated leucine-rich repeat kinase 2 (LRRK2) is a dimer that undergoes intramolecular autophosphorylation. *J Biol Chem* 2008, 283:16906-16914). GTP binding is essential for kinase activity, and mutations that prevent GTP binding have been shown to ablate LRRK2 kinase activity (Ito G, et al.: GTP binding is essential to the protein kinase activity of LRRK2, a causative gene product for familial Parkinson's disease. Biochemistry 2007, 46:1380-1388). The only validated physiological substrates (other than LRRK2 itself) are a subset of low-molecular weight G-proteins including Rab8a and Rab10, which are involved in regulation of vesicle trafficking and endosome function and trafficking on cytoskeletal networks (Steger M, et al.: Phosphoproteomics reveals that Parkinson's disease kinase LRRK2 regulates a subset of Rab GTPases. *Elife* 2016, 5. e12813). Expression levels of LRRK2 are highest in immune cells (neutrophils, monocytes and B cells), lung and kidney, with lower levels in the brain where it is expressed in dopaminergic neurons of the substantia nigra (West A B, et al.: Differential LRRK2 expression in the cortex, striatum, and substantia nigra in transgenic and nontransgenic rodents. *J Comp Neurol* 2014, 522:2465-2480).

There are several dominant gain-of-function pathogenic and characterized mutations to LRRK2, located either in the Roco domains (N1437H, R1441G/C/H, Y1699C), effecting GTP hydrolysis, or in the kinase domain (G2019S and I2020T). The G2019S is the most common LRRK2 mutation linked to Parkinson's disease (PD), which is a progressive neurodegenerative disorder characterized by resting tremors, rigidity, decreased movement (bradykinesia), and postural instability. The histological hallmarks of PD include neurodegeneration of the dopaminergic neurons in the substantia nigra pars *compacta* as well as intracellular inclusions called Lewy bodies and neurites consisting of the aggregated form of the alpha-synuclein protein. G2019S is associated with 1-2% of all PD patients and causes an increase in kinase activity of 2-fold in vitro (West A B, et al.: Parkinson's disease associated mutations in leucine-rich repeat kinase 2 augment kinase activity. *Proc Natl Acad Sci USA* 2005, 102: 16842-16847) and autophosphorylation at Ser1292 is increased 4-fold (Sheng Z, et al.: Ser1292 autophosphorylation is an indicator of LRRK2 kinase activity and contributes to the cellular effects of PD mutations. *Sci Transl Med* 2012, 4:164ra161). The G2019S and 12020T mutations lie within the DFG motif (DYGI in the case of LRRK2), common to all kinases, which controls catalytic activity. These mutations are thought to disrupt the inactive conformation and thus increase catalytic activity (Schmidt S H, et al.: The dynamic switch mechanism that leads to activation of LRRK2 is embedded in the DFGpsi motif in the kinase domain. *Proc Natl Acad Sci USA* 2019, 116: 14979-14988). Several of the above Parkinson disease-associated mutations (R1441C/G, Y1699C and 12020T) suppress phosphorylation of LRRK2 at Ser910 and Ser935, which in turn reduces LRRK2 association with 14-3-3 proteins, thought to represent an inactive form of LRRK2 (Nichols J, et al.: 14-3-3 binding to LRRK2 is disrupted by multiple Parkinson's disease associated mutations and regulates cytoplasmic localisation. *Biochem J* 2010, 430:393-404).

Furthermore, LRRK2 is linked to autosomal dominant inherited PD through a mutation within a region of chromosome 12, termed PARK8, which is linked to the LRRK2 gene (Funayama M, et al.: A new locus for Parkinson's disease (PARK8) maps to chromosome 12p11.2-q13.1. Ann Neurol 2002, 51:296-301; Zimprich A, et al.: Mutations in LRRK2 cause autosomal-dominant parkinsonism with pleomorphic pathology. *Neuron* 2004, 44:601-607; Paisan-Ruiz C, et al.: Cloning of the gene containing mutations that cause PARK8-linked Parkinson's disease. *Neuron* 2004, 44:595-600). LRRK2 was first described as having a link to autosomal dominant inherited Parkinson's disease in 1978, where it was traced to a family in Japan (Nukada H, et al.: [A big family of paralysis agitans (author's transl)]. *Rinsho Shinkeigaku* 1978, 18:627-634). The most common pathogenic LRRK2 mutation (G2019S) occurs in 4-8% of familial and 1-3% of sporadic PD cases. In addition, the G2019S mutation is common among PD patients of select ancestry, with 30-40% of North African Berber and 14% of Jewish patients harboring the mutation.

LRRK2 kinase inhibitors have been proposed as having the potential to treat mutation-driven PD, where there is an increase in LRRK2 activity, such as G2019S, and idiopathic PD, where the activity of LRRK2 is increased (Chen J, et al.: Leucine-rich repeat kinase 2 in Parkinson's disease: updated from pathogenesis to potential therapeutic target. *Eur Neurol* 2018, 79:256-265; Alessi D R, et al.: LRRK2 kinase in Parkinson's disease. *Science* 2018, 360:36-37; Di Maio R, et al.: LRRK2 activation in idiopathic Parkinson's disease. *Sci Transl Med* 2018, 10). Several therapeutics are progressing into the clinic, including LRRK2 kinase inhibitors that will directly affect phosphorylation of downstream targets, and oligonucleotides (ASO's) directly infused into the CNS to block translation of LRRK2 protein, thereby reducing LRRK2 protein levels.

Lewy bodies are the main histological hallmark of PD. Lewy bodies are composed primarily of alpha-synuclein aggregates, and mutations in alpha-synuclein that increase this aggregation also increase the risk of developing PD (Meade R M, et al.: Alpha-synuclein structure and Parkinson's disease lessons and emerging principles. Mol Neurodegener 2019, 14.29-29). Depletion of LRRK2 with ASOs (Zhao H T, et al.: LRRK2 antisense oligonucleotides ameliorate a-synuclein inclusion formation in a Parkinson's disease mouse model. Molecular therapy. Nucleic acids 2017, 8:508-519) and deletion of LRRK2 at a genomic level have been shown to reduce alpha-synuclein mediated pathology in mouse models of PD (Lin X, et al.: Leucine-rich repeat kinase 2 regulates the progression of neuropathology induced by Parkinson's-disease-related mutant alpha-synuclein. *Neuron* 2009, 64:807-827). Mutations increasing LRRK2 activity, such as G2019S, increase the aggregation of alpha-synuclein in neurons and mouse models of PD. This increase was reversed with LRRK2 kinase inhibitors (Volpicelli-Daley L A, et al. G2019S-LRRK2 Expression Augments α-Synuclein Sequestration into Inclusions in Neurons. *J Neurosci.* 2016 Jul. 13; 36(28):7415-27. doi: 10.1523/JNEUROSCI.3642-15.2016). There is some evidence to suggest that the G2019S mutant form of LRRK2 is resistant to inhibition by kinase inhibitors in the CNS, potentially reducing their disease modifying effect (Kelly K, et al. The G2019S mutation in LRRK2 imparts resiliency to kinase inhibition. *Exp Neurol.* 2018 November; 309:1-13). Even though most cases of PD also have Lewy bodies upon post-mortem examination, Lewy bodies are not present in a high number of LRRK2 G2019S mutation associated PD cases (Kalia L V, et al.: Clinical correlations with Lewy body pathology in LRRK2-related Parkinson disease. *JAMA neurol* 2015, 72:100-105). In addition to Lewy bodies being a common feature of PD, Tau pathology is also a major feature of LRRK2 mutation carriers at post-mortem (Henderson M X, et al.: Alzheimer's disease tau is a prominent pathology in LRRK2 Parkinson's disease. *Acta Neuropathol* Commun 2019, 7. 183-183). In one study, Tau pathology was observed in 100% of LRRK2 mutation carriers, thereby highlighting LRRK2 as an important target linking PD with Tau pathology in the context of PD, even though the genetic causal link was not as strong between LRRK2 and primary tau-opathies, such as supranuclear palsy (PSP) or corticobasal degeneration (CBD) (Ross O A, et al. (2006) Lrrk2 R1441 substitution and progressive supranuclear palsy. *Neuropathol Appl Neurobiol* 32(1):23-25; Sanchez-Contreras M, et al. (2017) Study of LRRK2 variation in tauopathy: progressive supranuclear palsy and corticobasal degeneration. *Mov Disord* 32(1):115-123). A common variation at the LRRK2 locus as a genetic determinant of PSP survival was recently reported (Jabbari E, et al., Common variation at the LRRK2 locus is associated with survival in the primary tauopathy progressive supranuclear palsy. bioRxiv 2020.02.04.932335; doi: https://doi.org/10.1101/2020.02.04.932335). It has been reported that increased LRRK2 expression in PSP by expression quantitative trait loci (eQTL) analysis may result in a reactive microglia-induced proinflammatory state which drives ongoing accumulation of misfolded Tau protein and clinical disease progression. Functional variants of LRRK2 have also been linked to Crohn's Disease and leprosy type 1 inflammatory reactions (Hui K Y, et al., Functional variants in the LRRK2 gene confer shared effects on risk for Crohn's disease and Parkinson's disease. *Sci Transl Med.* 2018 Jan. 10; 10 (423). pii: eaai7795. doi: 10.1126/scitranslmed.aai7795; Fava et al. Pleiotropic effects for Parkin and LRRK2 in leprosy type-1 reactions and Parkinson's disease. *Proc Natl Acad Sci USA.* 2019 Jul. 30; 116(31):15616-15624. doi: 10.1073/pnas.1901805116. Epub 2019 Jul. 15).

LRRK2 is highly expressed in the immune system in neutrophils, monocytes and macrophages, as well as in brain microglia, and is a modulator of the intrinsic regulation of microglial activation and of lysosomal degradation processes (Ma et al. Genetic comorbidities in Parkinson's disease. *Hum Mol Genet.* 2014 Feb. 1; 23(3):831-41. doi: 10.1093/hmg/ddt465. Epub 2013 Sep. 20, which was reviewed in Schapansky et al. The complex relationships between microglia, alpha-synuclein, and LRRK2 in Parkinson's disease. *Neuroscience.* 2015 Aug. 27; 302:74-88. doi: 10.1016/j.neuroscience.2014.09.049. Epub 2014 Oct. 2). Prolonged activation of these immune cells through PD disease processes or mutations in LRRK2 could increase neuroinflammation and lead to a greater risk of developing PD and/or Tau pathology. Treatment with anti-TNF agents reduces the risk of developing PD by 78% in patients with inflammatory bowel disorder (Peter I, et al.: Anti-tumor necrosis factor therapy and incidence of Parkinson disease among patients with inflammatory bowel disease. *JAMA Neurol* 2018), thereby demonstrating the strong linkage between inflammation and PD. In addition to PD, LRRK2 has been linked to other diseases such as cancer, leprosy, and Crohn's disease (Lewis P A, Manzoni C. LRRK2 and human disease: a complicated question or a question of complexes? (2012). *Sci Signal.* 5(207), pe2).

An ongoing need exists in the art for effective treatments for LRRK2 related disease and discorders, e.g., idiopathic PD, LRRK2 mutation associated PD (e.g., PD associated with one or more LRRK2 activating mutations), primary tauopathies (e.g., supranuclear palsy (PSP) or corticobasal degeneration (CBD)), lewy body dementia, Crohn's Disease, Leprosy (e.g., Leprosy with type 1 inflammatory reactions), and/or neuroinflammation.

SUMMARY

The present disclosure describes hetero-bifunctional compounds that function to recruit leucine-rich repeat kinase 2 (LRRK2) to an E3 ubiquitin ligase for targeted ubiquitination and subsequent proteasomal degradation, and methods of making and using the same. In addition, the description provides methods of using an effective amount of a compound of the present disclosure for the treatment or amelioration of a disease condition, such as an LRRK2-related disease or disorder, e.g., accumulation or overactivity of an LRRK2 protein or a mutated LRRK2 protein or a mis-folded LRRK2 protein, or alpha-synuclein aggregation or accumulation, or Tau aggregation or accumulation, or idiopathic PD, or a LRRK2 mutation associated PD (e.g., PD associated with one or more LRRK2 activating mutations), or a primary tauopathy (e.g., supranuclear palsy (PSP) or corticobasal degeneration (CBD)), or lewy body dementia, or Crohn's Disease, or Leprosy (e.g., Leprosy with type 1 inflammatory reactions), or neuroinflammation.

As such, in one aspect the disclosure provides hetero-bifunctional compounds, which comprise an E3 ubiquitin ligase binding moiety (i.e., a ligand for an E3 ubiquitin ligase (a "ULM" group)), and a moiety that binds LRRK2 or a mutated version thereof (i.e., a protein targeting moiety or "PTM" group, that is, a LRRK2 targeting ligand or a "LTM" group) such that the LRRK2 protein is thereby placed in proximity to the ubiquitin ligase to effect ubiquitination and subsequent degradation (and/or inhibition) of the LRRK2 protein. In a preferred embodiment, the ULM (ubiquitination ligase binding moiety) is a cereblon E3 ubiquitin ligase binding moiety (CLM). For example, the structure of the bifunctional compound can be depicted as:

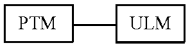

The respective positions of the PTM and ULM moieties (e.g., CLM), as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

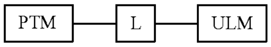

where PTM is a LRRK2-targeting moiety (LTM), L is a linker, e.g., a bond or a chemical linking group coupling PTM to ULM, and ULM is a cereblon E3 ubiquitin ligase binding moiety (CLM).

For example, the structure of the bifunctional compound can be depicted as:

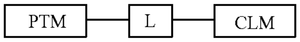

wherein: PTM is a LRRK2-targeting moiety (LTM); "L" is a linker (e.g. a bond or a chemical linking group) coupling the PTM and CLM; and CLM is cereblon E3 ubiquitin ligase binding moiety that binds to cereblon.

In any of the aspects or embodiments described herein, the PTM is a small molecule that binds LRRK2 or a mutant thereof. In any of the aspects or embodiments described herein, the PTM is a small molecule that binds LRRK2. In any of the aspects or embodiments described herein, the PTM is a small molecule that binds both an LRRK2 wild type protein and an LRRK2 mutant, such as a LRRK2 mutant including one or more mutation selected from G2019S, 12020T, N1437H, R1441G/C/H, and Y1699C. In any of the aspects or embodiments described herein, the PTM is a small molecule that binds both an LRRK2 wild type protein and an LRRK2 mutant such as, but not limited to, G2019S, 12020T, N1437H, R1441G/C/H, Y1699C, or a combination thereof. In any aspect or embodiment described herein, the small molecule binds the LRRK2 is as described herein.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is selected from thalidomide, lenalidomide, pomalidomide, analogs thereof, isosteres thereof, and derivatives thereof. Other contemplated CLMs are described in U.S. Patent Application Publication No. 2015/0291562, which is incorporated herein by reference in its entirety.

In certain embodiments, "L" is a bond. In additional embodiments, the linker "L" is a connector with a linear non-hydrogen atom number in the range of 1 to 20. The connector "L" can contain, but is not limited to, one or more functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic or tricyclic moieties. Substitution with halogen, such as Cl, F, Br and I can be included in the linker. In the case of fluorine substitution, single or multiple fluorines can be included.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but are not limited to, pomalidomide, lenalidomide and thalidomide and their analogs.

In an additional aspect, the description provides therapeutic compositions comprising an effective amount of a compound as described herein, or a salt form thereof, and a pharmaceutically acceptable carrier. The therapeutic compositions can be used to trigger targeted degradation of LRRK2 or a mutated version thereof and/or inhibition of LRRK2 or a mutated version thereof, in a patient or subject, for example, an animal such as a human, and can be used for treating or ameliorating one or more disease states, conditions, or symptoms causally related to LRRK2 or mutated version thereof, which treatment is accomplished through degradation or inhibition of the LRRK2 protein or mutated version thereof, or controlling or lowering LRRK2 protein levels or protein levels of a mutated version thereof, in a patient or subject. In certain embodiments, the therapeutic compositions as described herein may be used to effectuate the degradation of LRRK2, or a mutant form thereof, for the treatment or amelioration of a disease such as, e.g., LRRK2 accumulation or overeactivity, alpha-synuclein aggregation or accumulation, Tau aggregation or accumulation, idiopathic PD. LRRK2 mutation associated PD (e.g., PD associated with one or more LRRK2 activating mutations), primary tauopathies (e.g., supranuclear palsy (PSP) or corticobasal degeneration (CBD)), lewy body dementia, Crohn's Disease, Leprosy (e.g., Leprosy with type 1 inflammatory reactions), and/or neuroinflammation.

In yet another aspect, the present disclosure provides a method of ubiquitinating LRRK2 or a mutated form thereof in a cell. In certain embodiments, the method comprises administering a hetero-bifunctional compound as described herein comprising a PTM that binds LRRK2 or a mutant form thereof, and a CLM, preferably linked through a chemical linker moiety, as described or exemplified herein, to effectuate degradation of the LRRK2 protein or mutant form thereof. Though not wanting to be limited by theory, the inventors believe that, pursuant to the invention, poly-ubiquitination of the LRRK2 wild-type or mutant protein will occur when it is placed in proximity to the E3 ubiquitin ligase via use of the hetero-bifunctional compound, thereby triggering subsequent degradation of the LRRK2 or mutant protein via the proteasomal pathway and control or reduction of LRRK2 protein levels in cells, such as cells of a subject in need of such treatment. The control or reduction in levels of the LRRK2 protein or mutated form thereof afforded by the present disclosure provides treatment of a LRRK2 causally related disease state, condition or related symptom, as modulated through a lowering of the amount of LRRK2 protein or mutated form thereof in cells of the subject.

In still another aspect, the description provides methods for treating or ameliorating a disease, condition, or symptom thereof causally related to LRRK2 or mutated form thereof in a subject or a patient, e.g., an animal such as a human, comprising administering to a subject in need thereof a composition comprising an effective amount, e.g., a therapeutically effective amount, of a hetero-bifunctional compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of LRRK2 protein in a biological system using compounds according to the present disclosure.

In another aspect, the description provides processes and intermediates for making a hetero-bifunctional compound of the present disclosure capable of targeted ubiquitination and degradation of the LRRK2 protein in a cell (e.g., in vivo or in vitro).

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure. Further objects, features and advantages of the disclosure will become apparent from the following detailed description taken in conjunction with the accompanying figures showing illustrative embodiments of the disclosure.

FIG. 1A. Exemplary hetero-biofunctional protein degrading compounds comprise a protein targeting moiety (PTM; darkly shaded rectangle), a ubiquitin ligase binding moiety (ULM; lightly shaded triangle), and optionally a linker moiety (L; black line) coupling the PTM to the ULM. FIG. 1B Illustrates the functional use of the hetero-bifunctional protein degrading compounds (commercially known as PROTAC® protein degrader compounds) as described herein. Briefly, the ULM (triangle) recognizes and binds to a specific E3 ubiquitin ligase, and the PTM (large rectangle) binds and recruits a target protein bringing it into close proximity to the E3 ubiquitin ligase. Typically, the E3 ubiquitin ligase is complexed with an E2 ubiquitin-conjugating protein (E2), and either alone or via the E2 protein catalyzes attachment of multiple ubiquitin molecules (black circles) to a lysine on the target protein via an isopeptide bond. The poly-ubiquitinated protein (far right) has thereby been targeted for degradation by the proteosomal machinery of the cell.

DETAILED DESCRIPTION

Figure 1A:
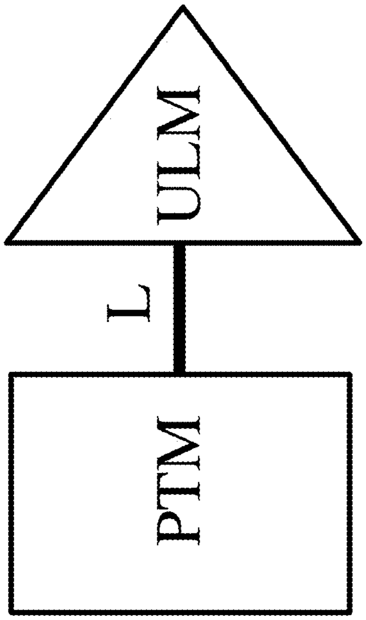
FIGS. 1A and 1B. Illustration of general principle for hetero-bifunctional protein-degrading compounds.
Figure 1B:
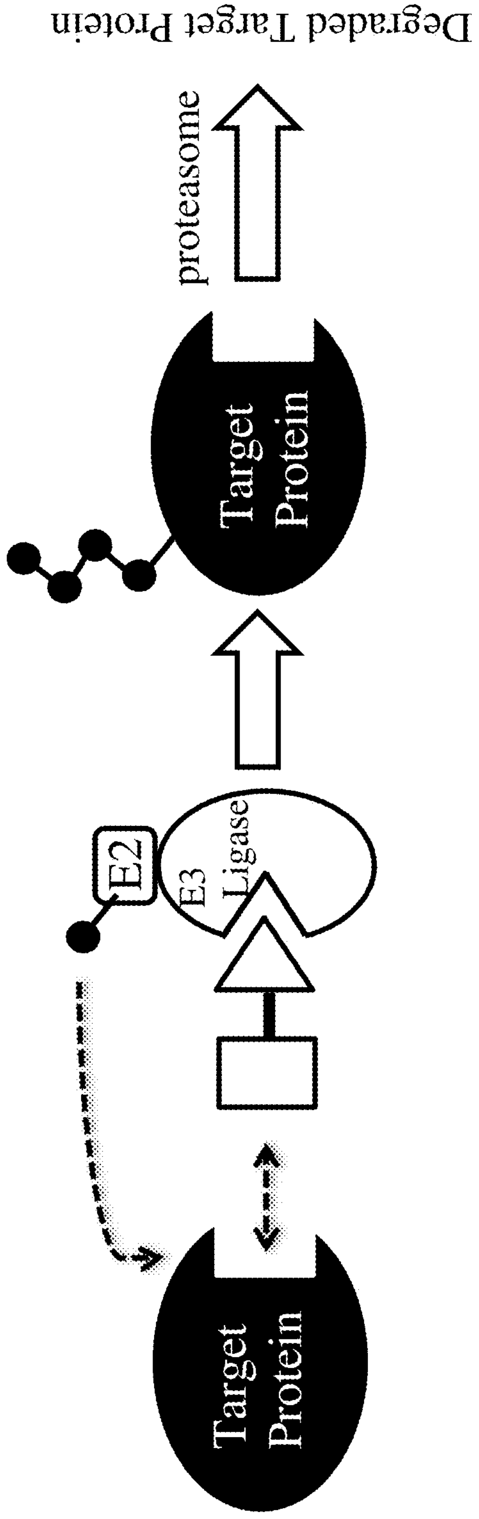

Presently described are compounds, compositions and methods that relate to the surprising discovery that an E3 ubiquitin ligase (e.g., a cereblon E3 ubiquitin ligase) ubiquitinates the LRRK2 protein or mutated form thereof once the E3 ubiquitin ligase and the LRRK2 protein are placed in proximity via a bifunctional compound that binds both the E3 ubiquitin ligase and the LRRK2 protein. Accordingly the present disclosure provides compounds and compositions comprising an E3 ubiquitin ligase binding moiety ("ULM") coupled by a bond or chemical linking group (L) to a protein targeting moiety ("PTM") that targets the LRRK2 protein, which results in the ubiquitination of the LRRK2 protein, and which leads to degradation of the LRRK2 protein by the proteasome (see FIG. 1).

In one aspect, the description provides compounds in which the PTM binds to the LRRK2 protein and/or a mutated form thereof. The present disclosure also provides a library of compositions and the use thereof to produce targeted degradation of the LRRK2 protein in a cell.

In certain aspects, the present disclosure provides hetero-bifunctional compounds which comprise a ligand, e.g., a small molecule ligand (i.e., having a molecular weight of below 2,000, 1,000, 500, or 200 Daltons), which is capable of binding to an E3 ubiquitin ligase, such as cereblon. The compounds also comprise a small molecule moiety that is capable of binding to the LRRK2 protein or mutated form thereof in such a way that the LRRK2 protein or mutated form is placed in proximity to the ubiquitin ligase to effect ubiquitination and degradation (and/or inhibition) of the LRRK2 protein or mutated form. "Small molecule" means, in addition to the above, that the molecule is non-peptidyl, that is, it is not considered a peptide, e.g., comprises fewer than 4, 3, or 2 amino acid residues. In accordance with the present description, each of the PTM, ULM and hetero-bifunctional molecule is a small molecule.

The term "LRRK2" as used throughout the Specification, unless specifically indicated to the contrary, is intended to include both wild-type LRRK2 and mutant forms therefore, such as a LRRK2 mutant protein including one or more mutation selected from G2019S, 12020T, N1437H, R1441G/C/H, and Y1699C.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value in the range, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either/or both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element, unless otherwise indicated.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood that, in certain methods or processes described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time-varied administration (administration of one or more therapeutic agents at a time different from that of the administration of an additional therapeutic agent or agents), as long as the two or more therapeutic agents are present in the patient to some extent, preferably at effective amounts, at the same time. In certain preferred aspects, one or more of the hetero-bifunctional compounds described herein are coadministered with at least one additional bioactive agent, e.g., an anticancer agent. In particularly preferred aspects, the co-administration of such compounds results in synergistic activity and/or therapy such as, e.g., anticancer activity.

The term "compound", as used herein, unless otherwise indicated, refers to any specific hetero-bifunctional compound disclosed herein, pharmaceutically acceptable salts and solvates thereof, and deuterated forms of any of the aforementioned molecules, where applicable. Deuterated compounds contemplated are those in which one or more of the hydrogen atoms contained in the drug molecule have been replaced by deuterium. Such deuterated compounds preferably have one or more improved pharmacokinetic or pharmacodynamic properties (e.g., longer half-life) compared to the equivalent "undeuterated" compound.

The term "ubiquitin ligase" refers to a family of proteins that facilitate the transfer of one or more ubiquitins to a specific substrate protein. Addition of a chain of several ubiquitins (poly-ubiquitination) targets the substrate protein for degradation. For example, cereblon is an E3 ubiquitin ligase that alone, or in combination with an E2 ubiquitin-conjugating enzyme, can ultimately cause the attachment of a chain of four ubiquitins to a lysine residue on the target protein, thereby targeting the protein for degradation by the proteasome. The ubiquitin ligase is involved in poly-ubiquitination such that a first ubiquitin is attached to a lysine on the target protein; a second ubiquitin is attached to the first; a third is attached to the second, and a fourth is attached to the third. Such poly-ubiquitination marks proteins for degradation by the proteasome.

The term "patient" or "subject" is used throughout the specification to describe an animal, preferably a human or a domesticated animal, to whom treatment, including prophylactic treatment, with the compositions according to the present disclosure is provided. For treatment of those diseases, conditions or symptoms that are specific for a specific animal, such as a human patient, the term "patient" refers to that specific animal, including a domesticated animal such as a dog or cat, or a farm animal such as a horse, cow, sheep, etc. In general, in the present disclosure, the terms "patient" and "subject" refer to a human patient unless otherwise stated or implied from the context of the use of the term.

The terms "effective" and "therapeutically effective" are used to describe an amount of a compound or composition which, when used within the context of its intended use, and either in a single dose or, more preferably after multiple doses within the context of a treatment regimen, effects an intended result such as an improvement in a disease or condition, or amelioration or reduction in one or more symptoms associated with a disease or condition. The terms “effective” and “therapeutically effective” subsume all other “effective amount” or “effective concentration” terms, which are otherwise described or used in the present application.

Compounds and Compositions

In one aspect, the description provides hetero-bifunctional compounds comprising an E3 ubiquitin ligase binding moiety (“ULM”) that is a cereblon E3 ubiquitin ligase binding moiety (a “CLM”), The CLM is covalently coupled to a protein targeting moiety (PTM) that binds to the protein, which coupling is either directly by a bond or via a chemical linking group (L) according to the structure:

PTM-L-CLM (A)

wherein L is the bond or chemical linking group, and PTM is a protein targeting moiety that binds to the protein LRRK2 or a mutant form thereof, e.g., G2019S, where the PTM is a LRRK2 targeting moiety (LTM). The term CLM is inclusive of all cereblon binding moieties.

In any of the aspects or embodiments, the CLM demonstrates a half maximal inhibitory concentration ($IC_{50}$) for the E3 ubiquitin ligase (e.g., cereblon E3 ubiquitin ligase) of less than about 200 μM. The $IC_{50}$ can be determined according to any suitable method known in the art, e.g., a fluorescent polarization assay.

In certain embodiments, the hetero-bifunctional compounds described herein demonstrate an $IC_{50}$ or a half maximal degradation concentration ($DC_{50}$) of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 μM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 μM.

In any aspect or embodiment described herein, the hetero-bifunctional compound is represented by the chemical structure:

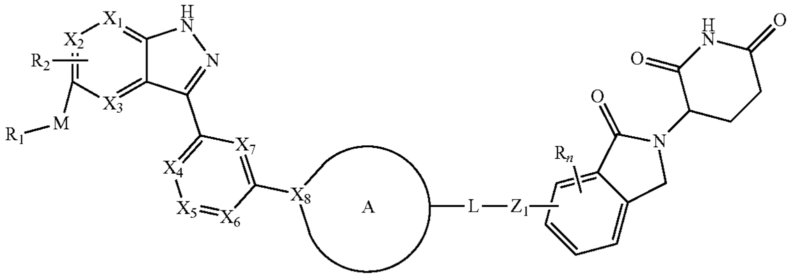

or

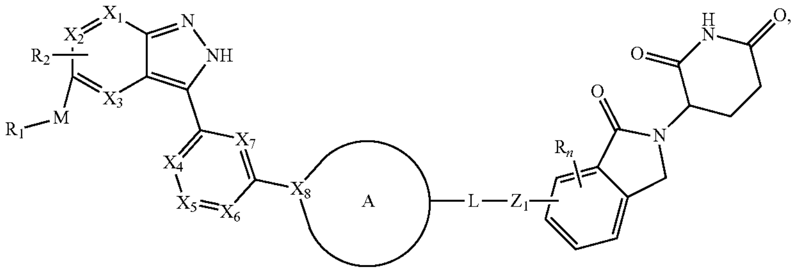

(Formula Ia)

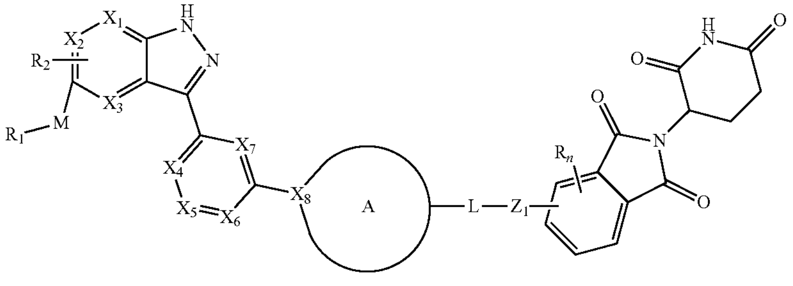

or

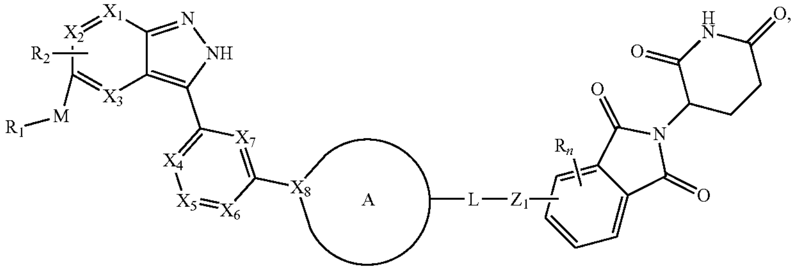

(Formula Ib)

-continued

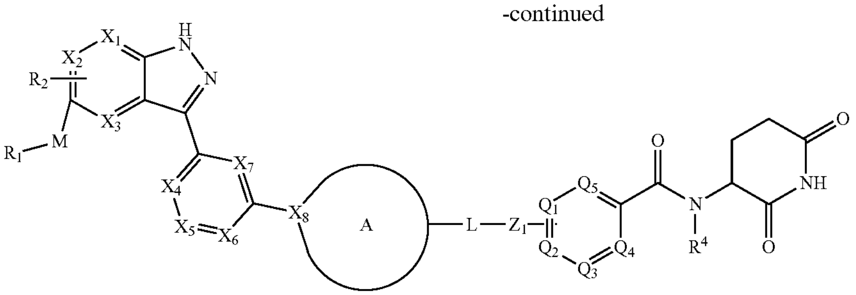

or (Formula Ic)

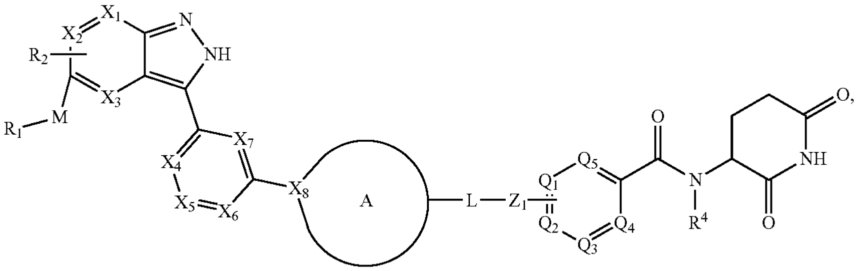

wherein:

$Z_1$ is an R group of a CLM as described in any aspect or embodiment described herein that is modified to be covalently linked to L, such a a group selected from a bond, —C(═O)—, —CONR'—, —O—, —NR'—, a carbon shared with a cyclic group of L, or a nitrogen shared with a cyclic group of L;

n is an integer from 0 to 3 (e.g., 0, 1, 2, or 3);

R is selected from a bond, H, O, OH, N, NH, $NH_2$, Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy; and $Q_1$, $Q_2$, $Q_3$, $Q_4$, $Q_5$, $R^4$, L, $R_1$, $R_2$, M, $X_1$, $X_2$, $X_3$, $X_4$, $X_5$, $X_6$, $X_7$, $X_8$, and

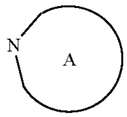

are defined as in any aspect or embodiment described herein.

In any aspect or embodiment described herein, the hetero-bifunctional compound is represented by the chemical structure:

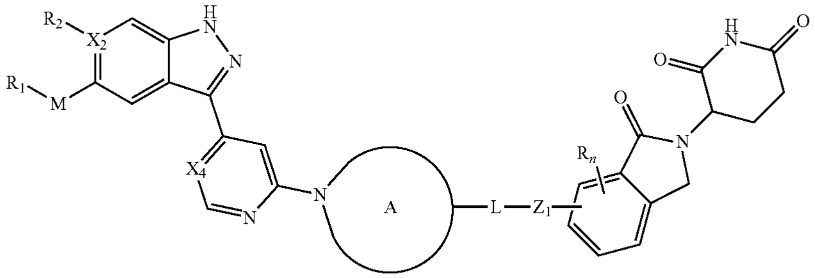

or (Formula IIa)

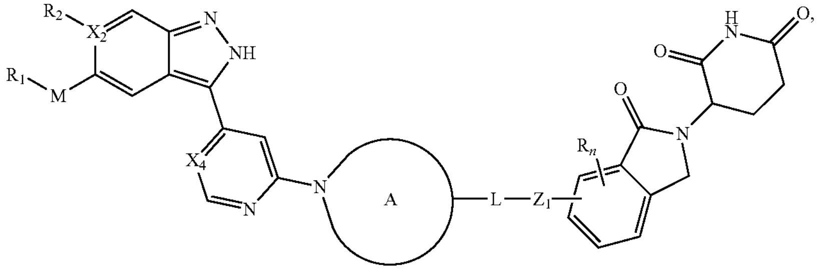

-continued
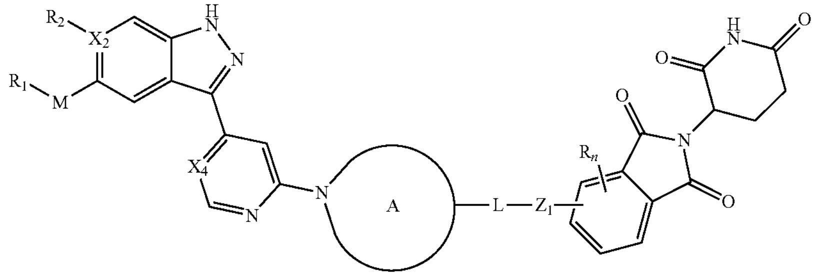
or
(Formula IIb)
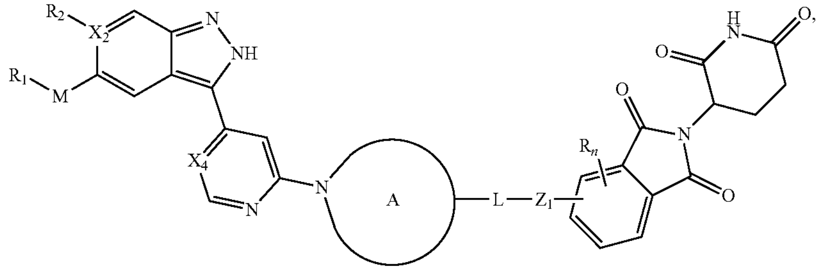
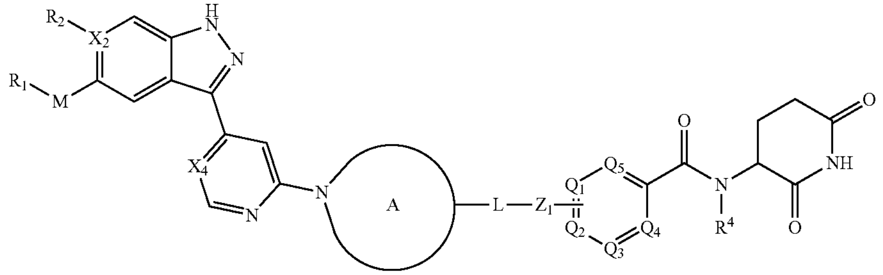
or
(Formula IIc)
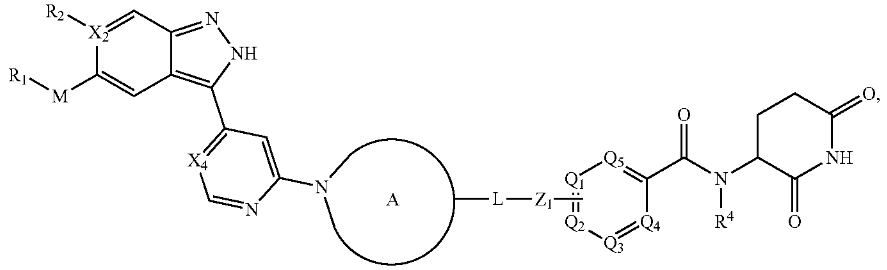
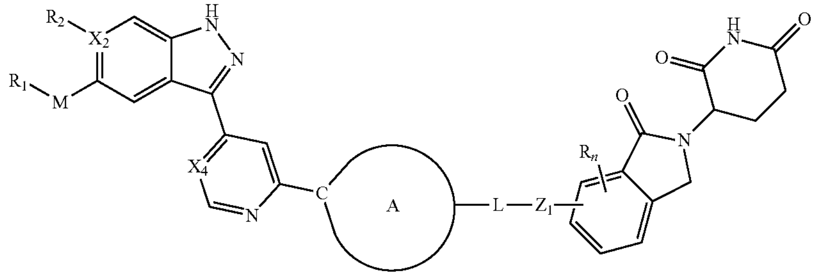
or
(Formula IId)
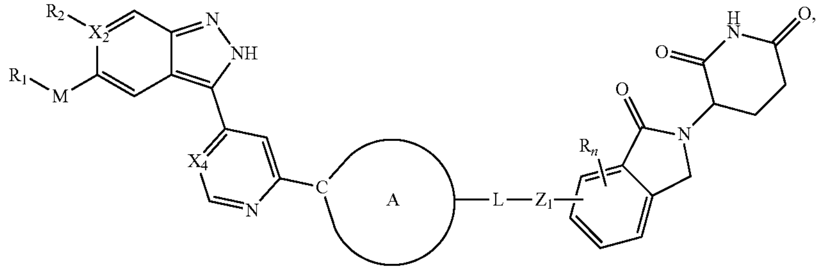

-continued
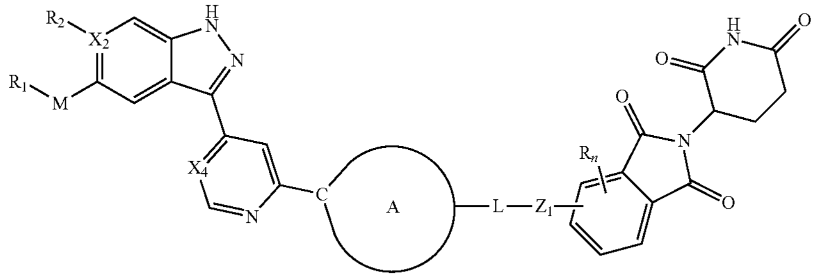
or
(Formula IIe)
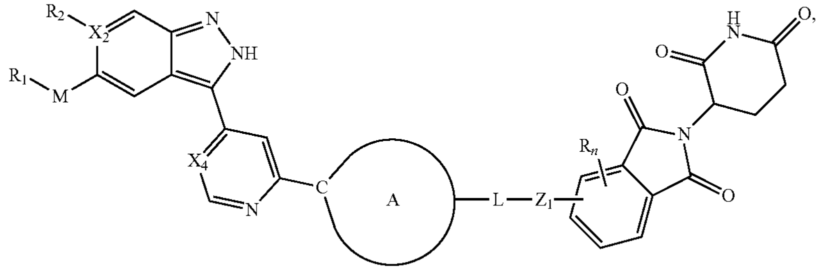
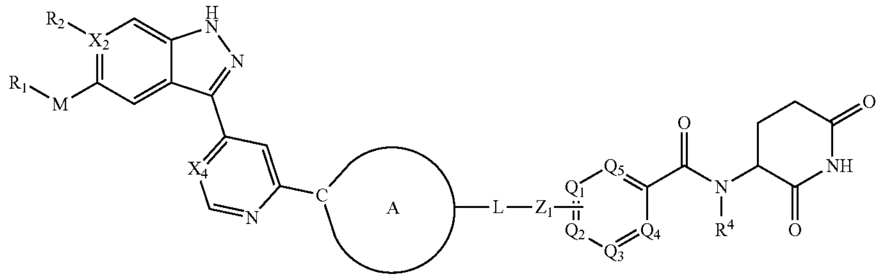
or
(Formula IIf)
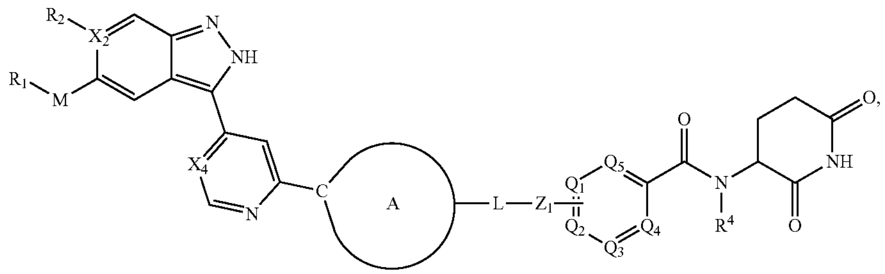
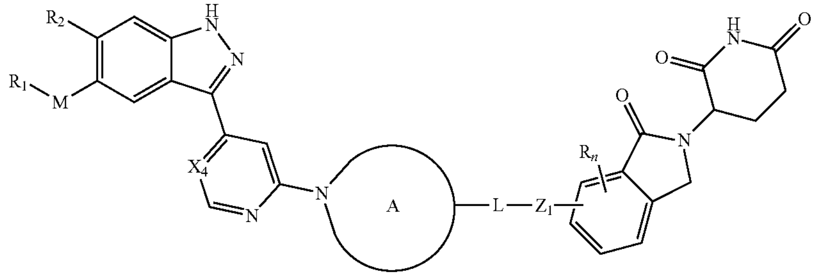
or
(Formula Va)
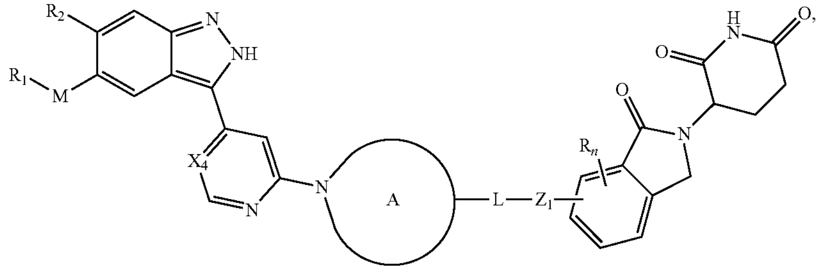

-continued
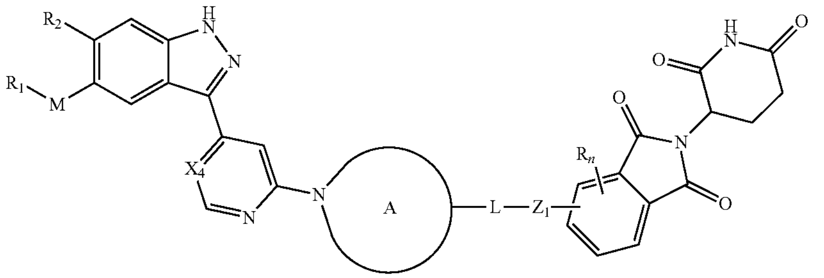
or
(Formula Vb)
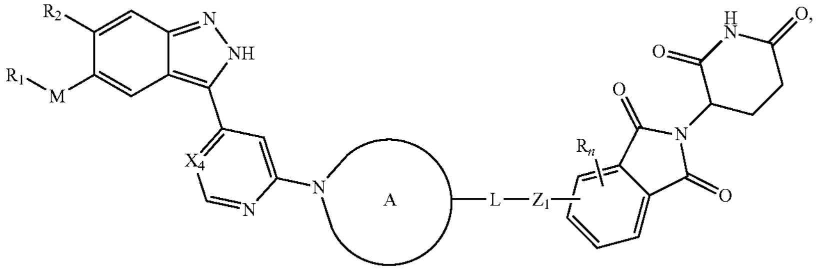
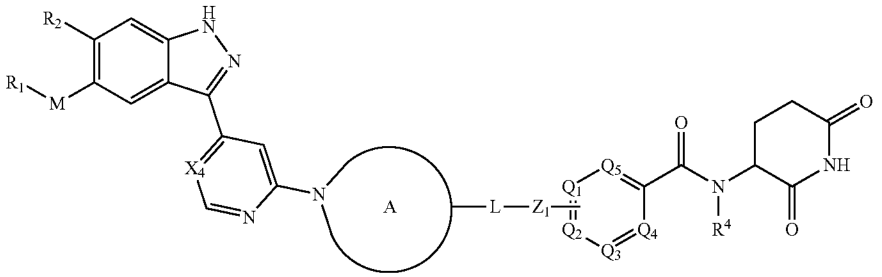
or
(Formula Vc)
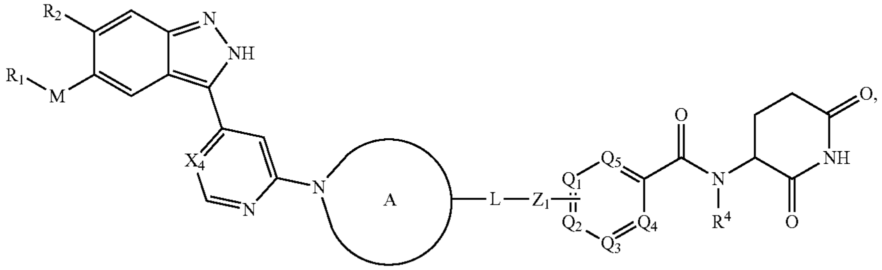
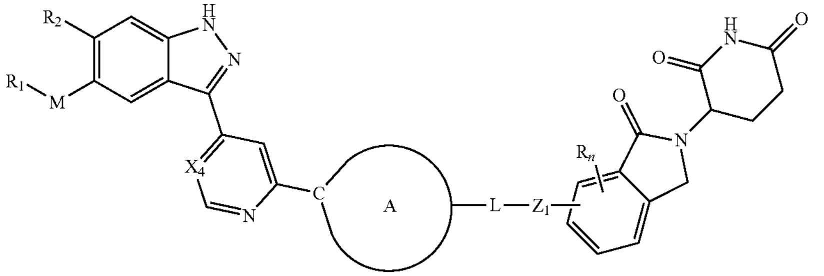
or
(Formula Vd)
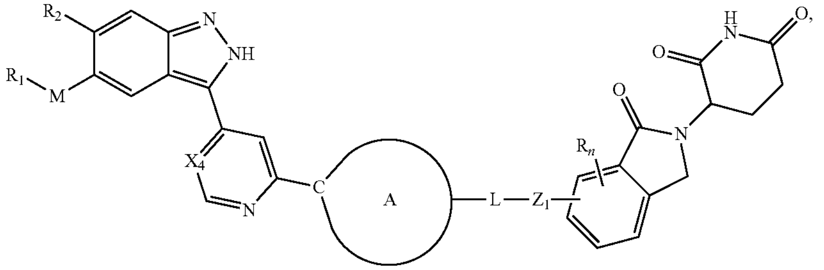

-continued

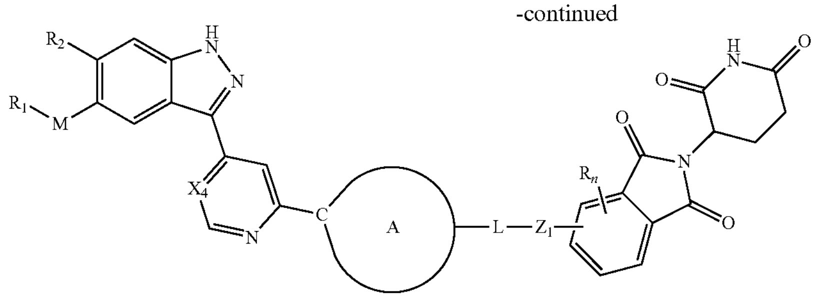

or (Formula Ve)

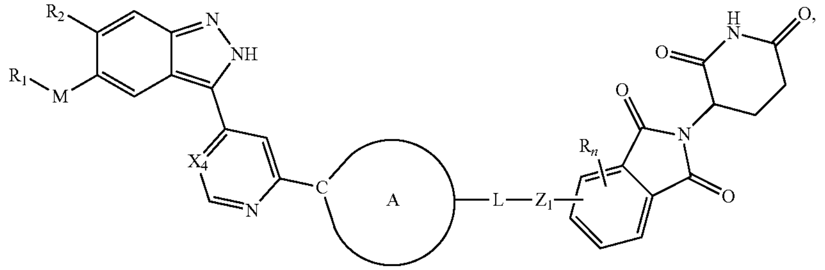

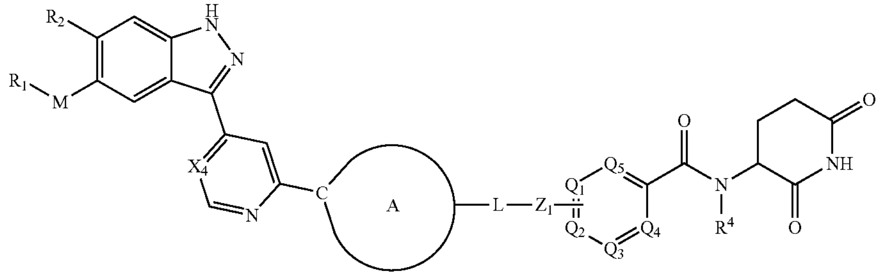

or (Formula Vf)

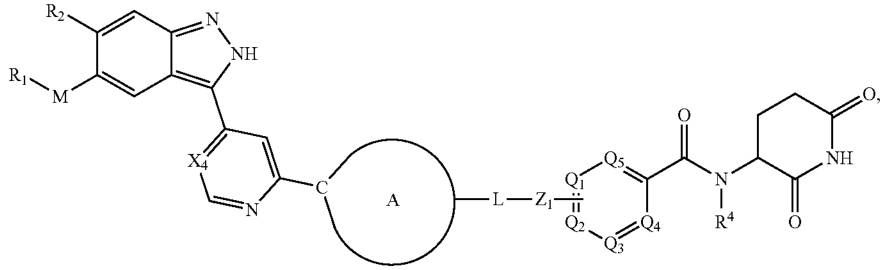

wherein:

$Z_1$ is an R group of a CLM as described in any aspect or embodiment described herein that is modified to be covalently linked to L, such a a group selected from a bond, —C(═O)—, —CONR'—, —O—, —NR'—, a carbon shared with a cyclic group of L, or a nitrogen shared with a cyclic group of L;

n is an integer from 0 to 3 (e.g., 0, 1, 2, or 3);

R is selected from a bond, H, O, OH, N, NH, $NH_2$, Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy; and $Q_1$, $Q_2$, $Q_3$, $Q_4$, $Q_5$, $R^4$, L, $R_1$, $R_2$, $R^4$, $X_2$, $X_4$,

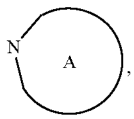, and 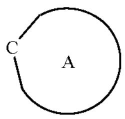

are defined as in any aspect or embodiment described herein.

In any aspect or embodiment described herein, the hetero-bifunctional compound is represented by the chemical structure:
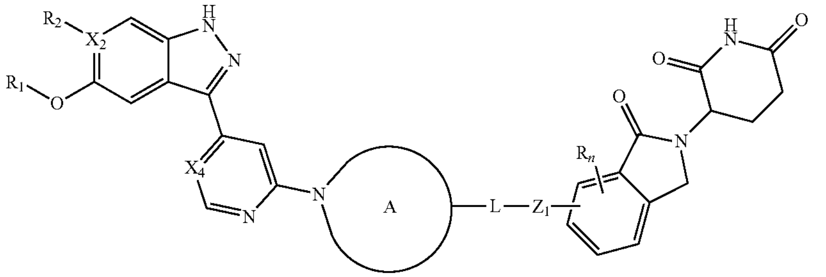
or
(Formula IIIa)
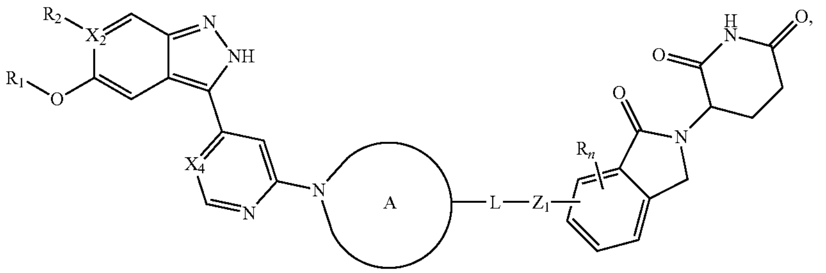
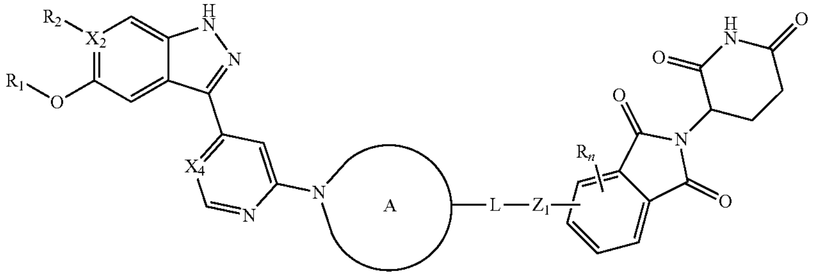
or
(Formula IIIb)
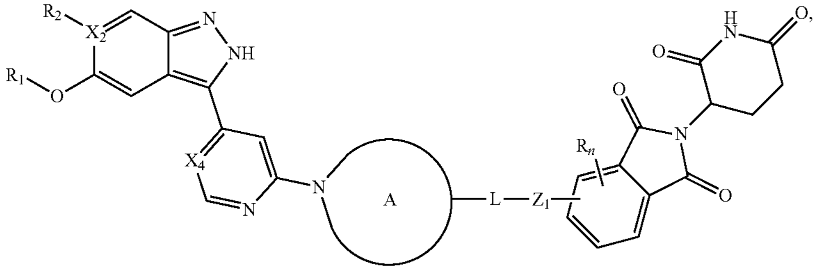
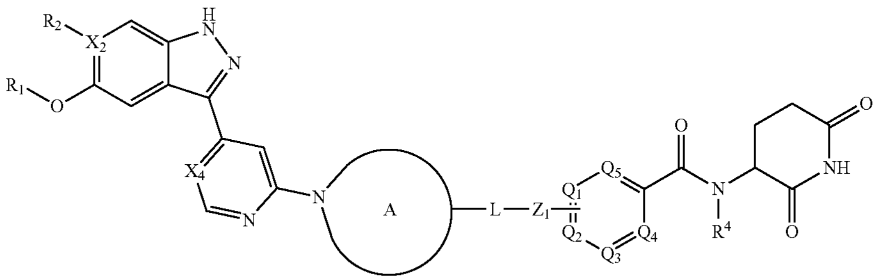
or -continued
(Formula IIIc)
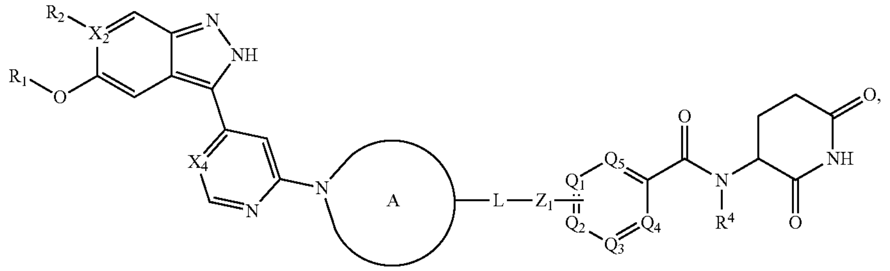
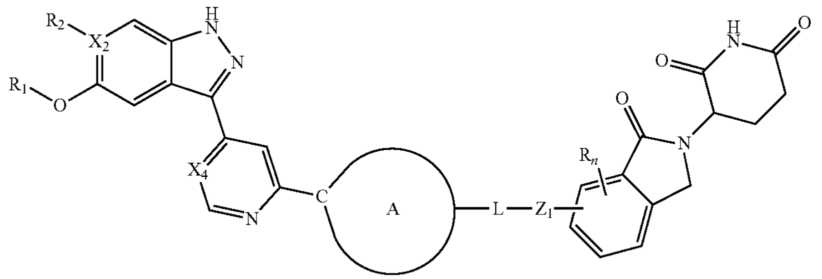
or
(Formula IIId)
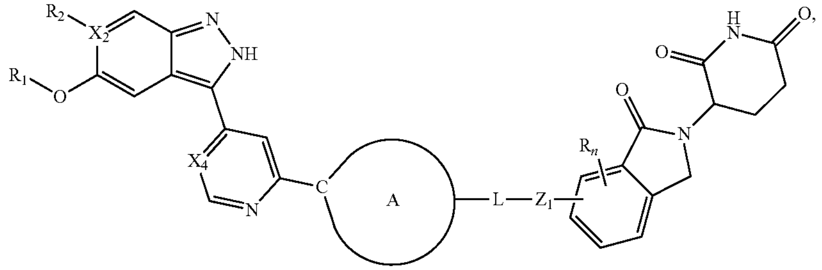
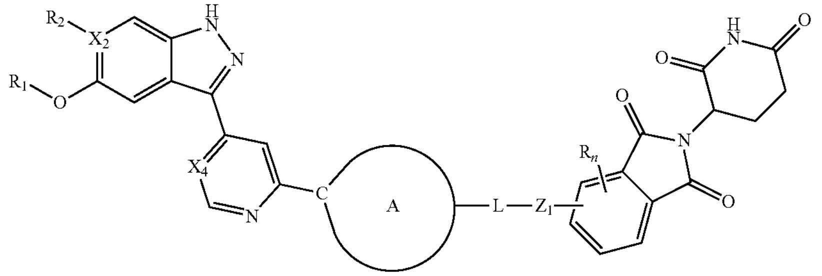
or
(Formula IIIe)
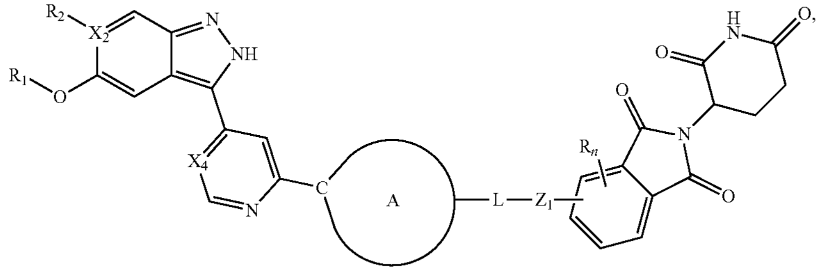
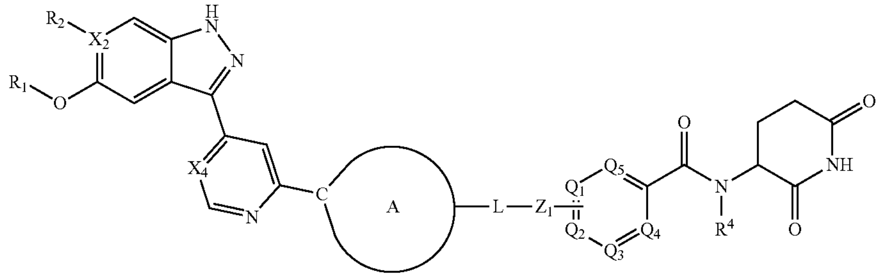
or -continued
(Formula IIIf)
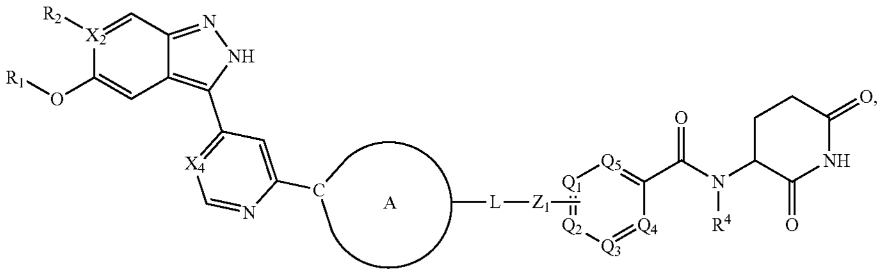
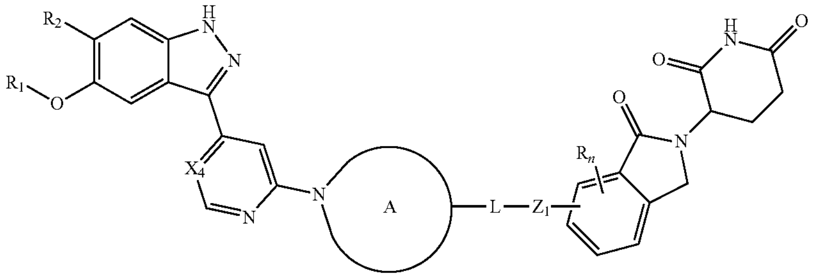
or
(Formula VIa)
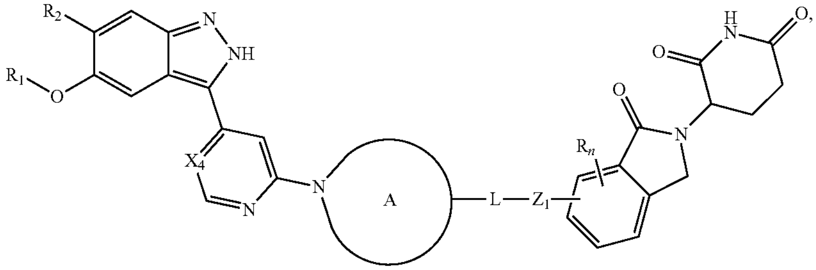
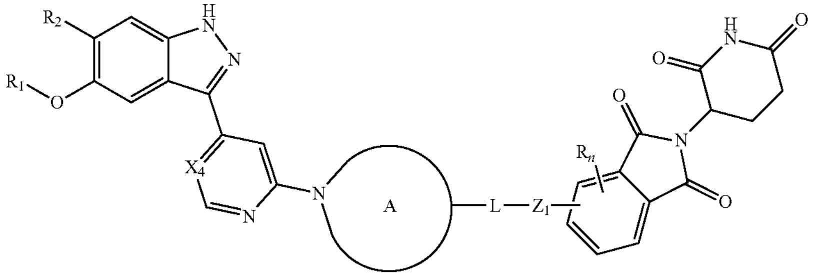
or
(Formula VIb)
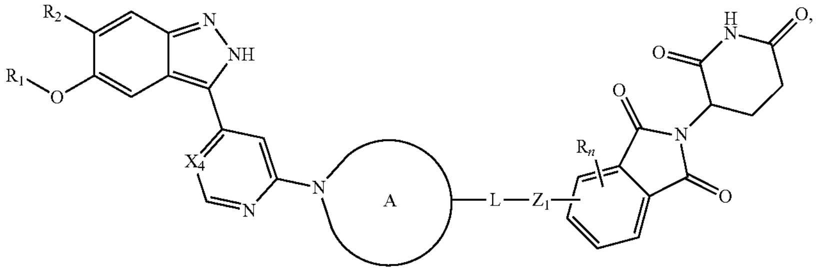
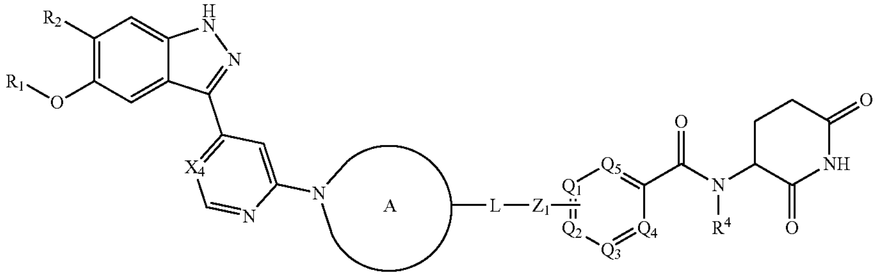
or -continued
(Formula VIc)
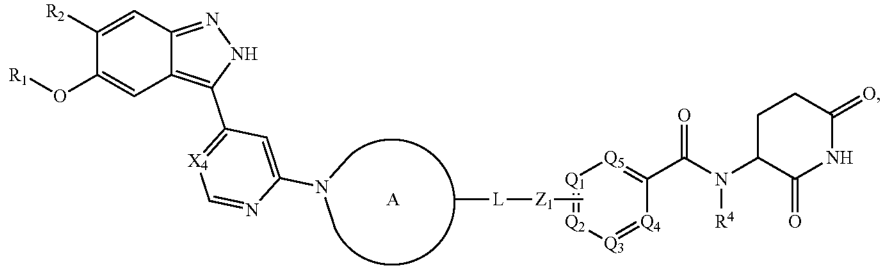
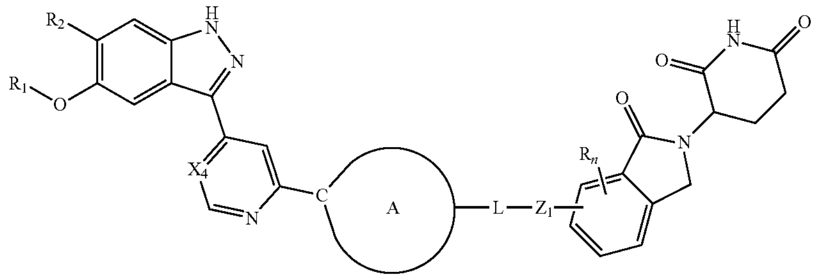
or
(Formula VId)
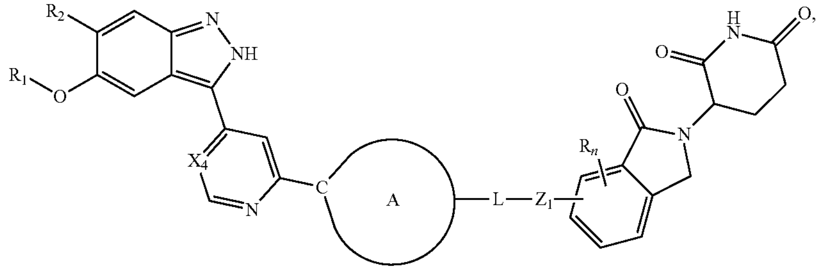
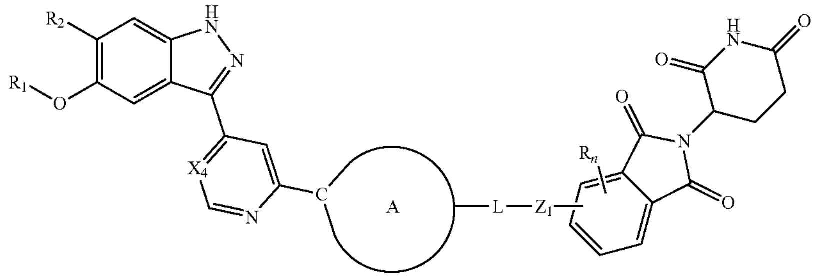
or
(Formula VIe)
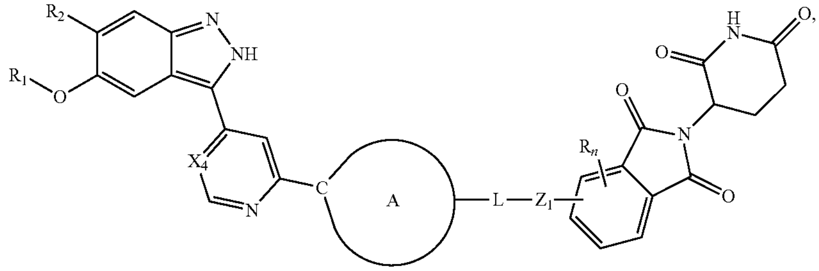
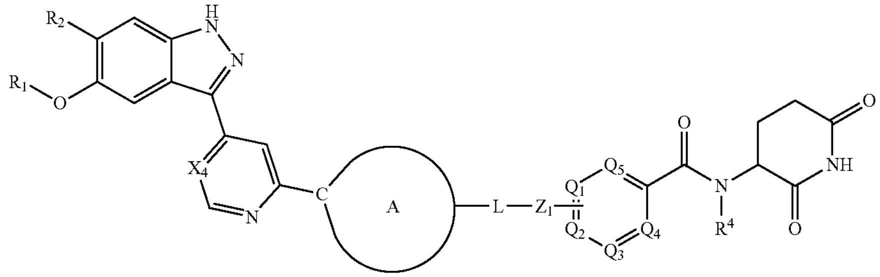
or -continued (Formula VIf)

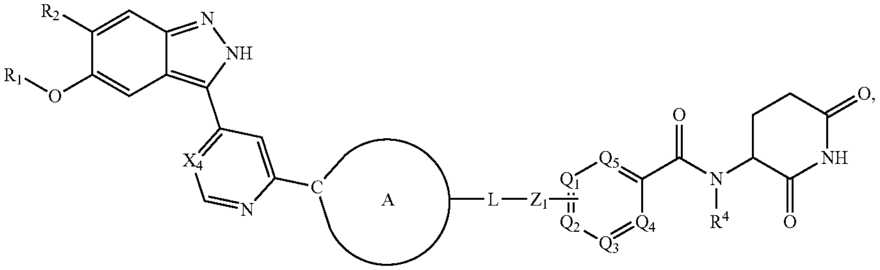

wherein:

$Z_1$ is an R group of a CLM as described in any aspect or embodiment described herein that is modified to be covalently linked to L, such a group selected from a bond, —C(═O)—, —CONR'—, —O—, —NR'—, a carbon shared with a cyclic group of L, or a nitrogen shared with a cyclic group of L;

n is an integer from 0 to 3 (e.g., 0, 1, 2, or 3);

R is selected from a bond, H, O, OH, N, NH, $NH_2$, Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy; and $Q_1$, $Q_2$, $Q_3$, $Q_4$, $Q_5$, $R^4$, L, $R_1$, $R_2$, $X_2$, $X_4$,

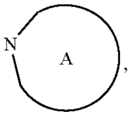

, and

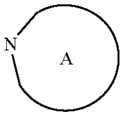

and are defined as in any aspect or embodiment described herein.

In any aspect or embodiment described herein, the hetero-bifunctional compound is represented by the chemical structure:

(Formula IVa)

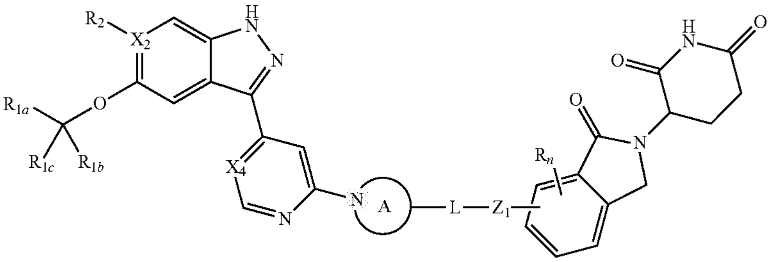

or

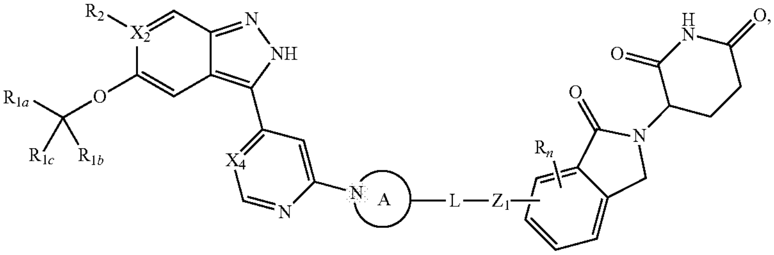

, (Formula IVb)

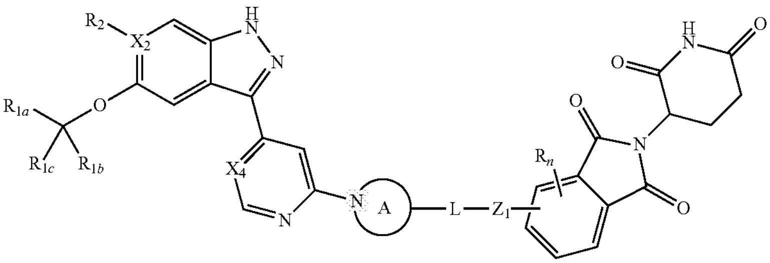

or

-continued
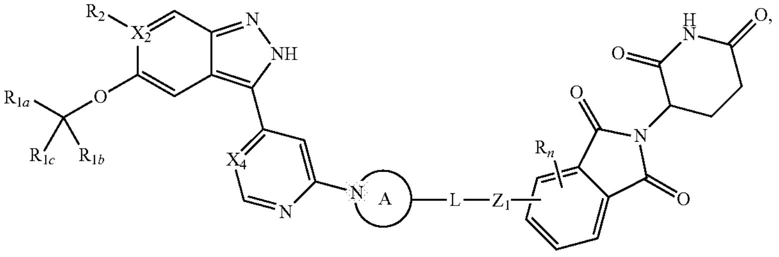
and
(Formula IVc)
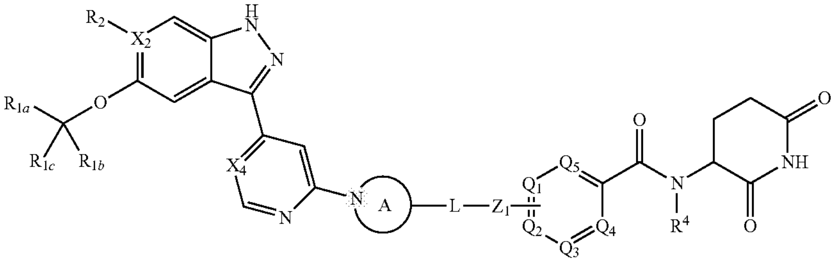
or
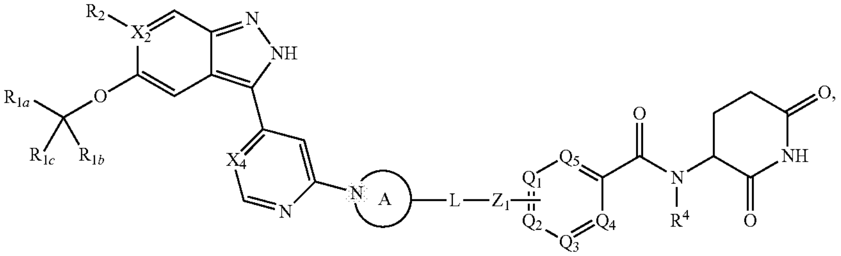
(Formula VIIa)
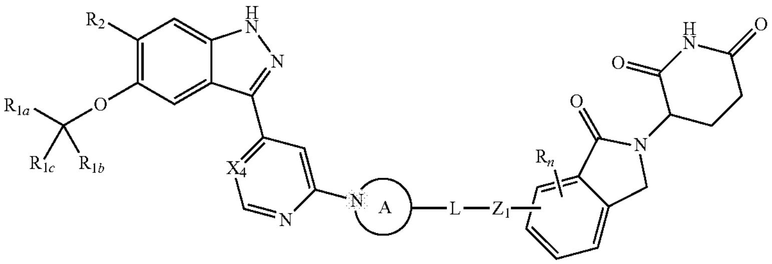
or
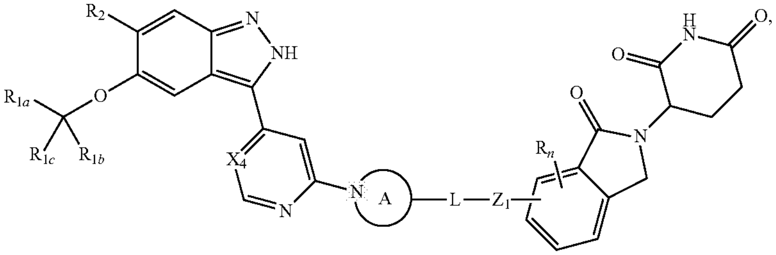
(Formula VIIb)
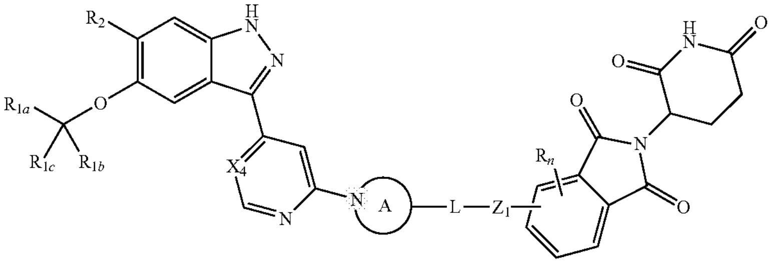
or -continued

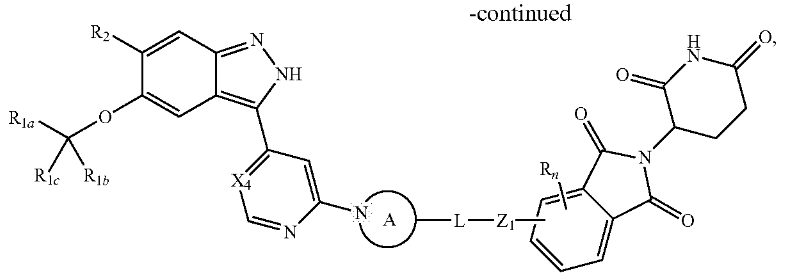

(Formula VIIc)

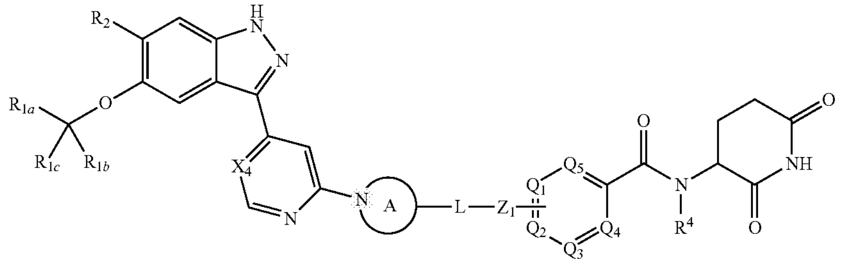

or

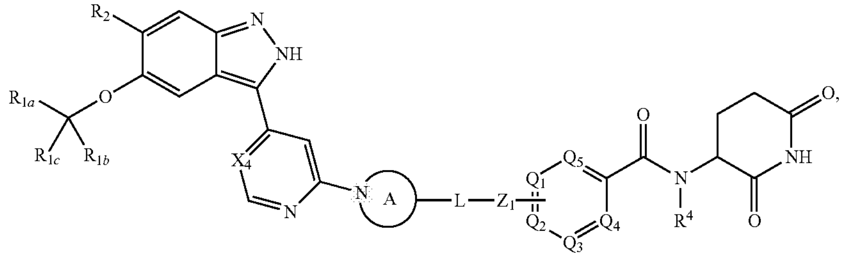

wherein:

$Z_1$ is an R group of a CLM as described in any aspect or embodiment described herein that is modified to be covalently linked to L, such a a group selected from a bond, —C(═O)—, —CONR'—, —O—, —NR'—, a carbon shared with a cyclic group of L, or a nitrogen shared with a cyclic group of L;

n is an integer from 0 to 3 (e.g., 0, 1, 2, or 3);

R is selected from a bond, H, O, OH, N, NH, $NH_2$, Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy; and $Q_1$, $Q_2$, $Q_3$, $Q_4$, $Q_5$, $R^4$, L, $R_{1a}$, $R_{1b}$, $R_{1c}$, $R_2$, $X_2$, $X_4$, and

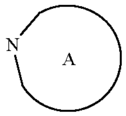

are defined as in any aspect or embodiment described herein.

In any aspect or embodiment described herein, the heterobifunctional compound is represented by Formula IIIa, Formula IIIb, VIa, or VIb:

(Formula IIIa)

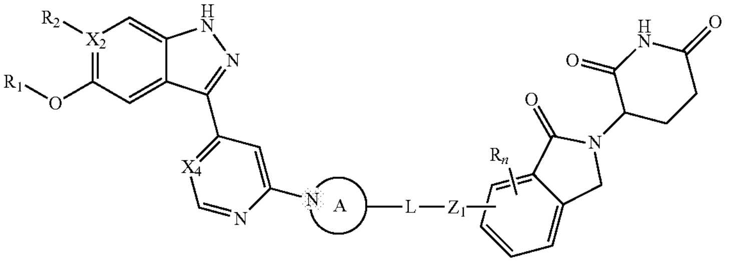

or

-continued
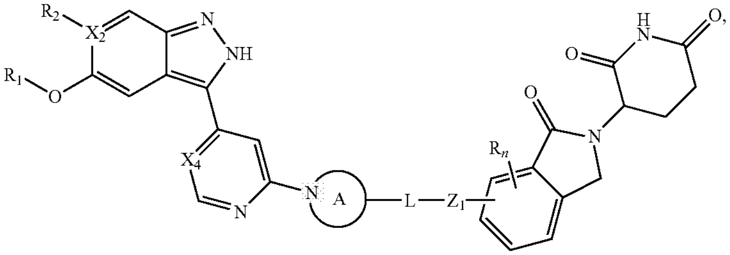
or
(Formula IIIb)
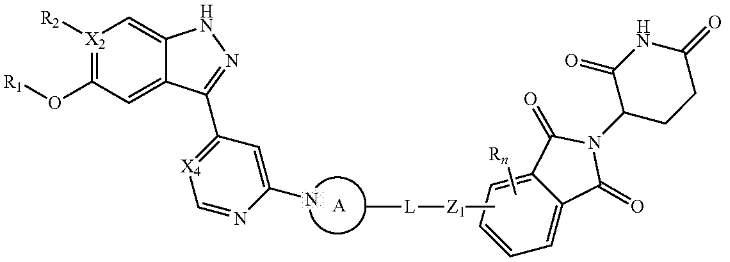
or
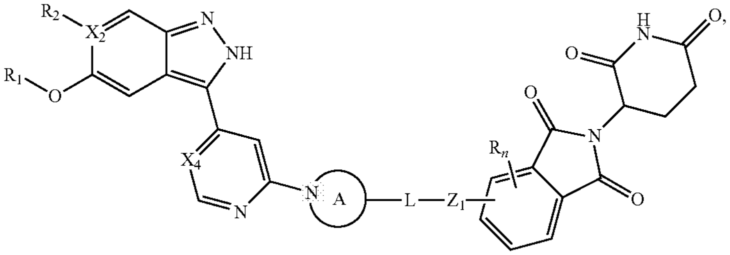
(Formula VIa)
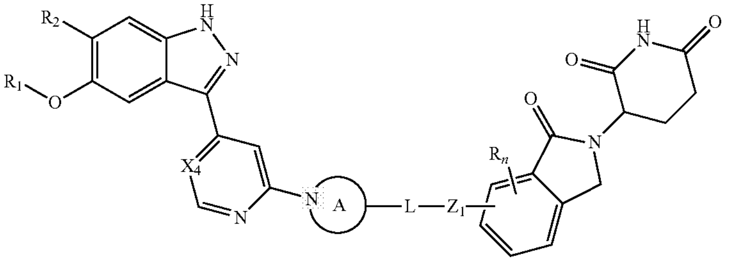
or
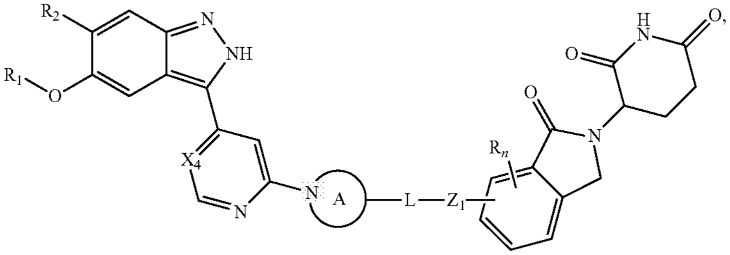
(Formula VIb)
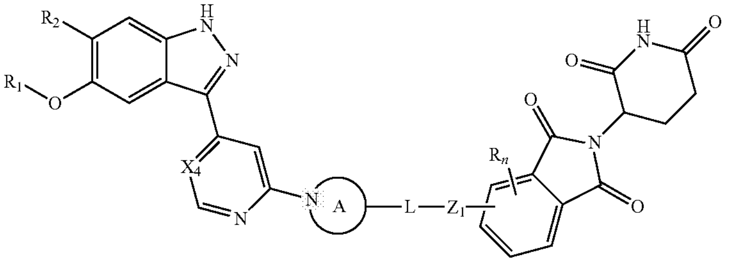
or -continued

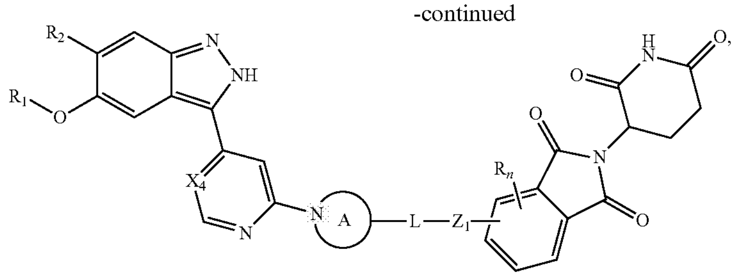

wherein:

n is 0 or 1;

R is H, OH, —Cl, —F, or Br;

$Z_1$ is a nitrogen or carbon shared with a cyclic group of L;

$X_4$ is CH or N (preferably N);

$R_1$ is

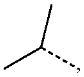 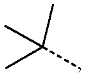 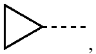 , or

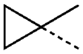 (preferably 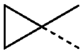 ), wherein the dashed line is the point of attachment to the oxygen of the PTM;

$R_2$ is a H or a halogen;

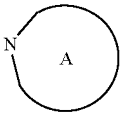

is:

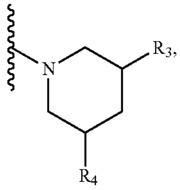 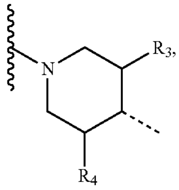 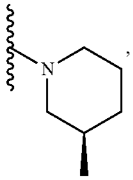

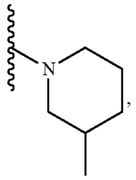 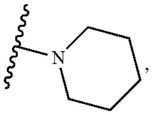 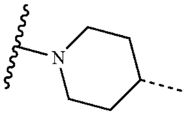

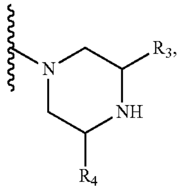 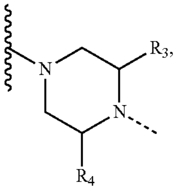

-continued

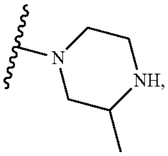 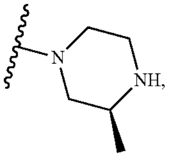

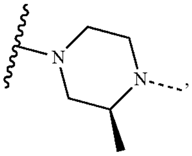 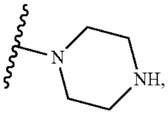 or

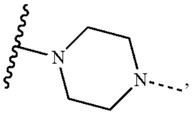 (preferably,

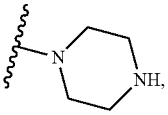

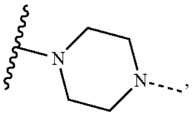

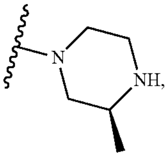

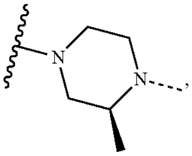

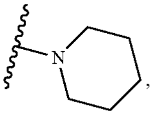 , or

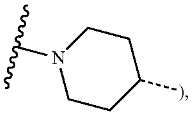 ), wherein:

$R_3$ is H or linear or branched C1-C3 alkyl (e.g., methyl or ethyl);

$R_{3a}$ is H, halogen, or linear or branched C1-C3 alkyl (e.g., methyl);

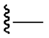 indicates the point of attachment of the (i.e., the point of attachment with the 6-membered heteroaryl of the PTM); and

 indicates the point of attachment of the

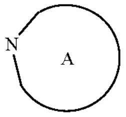

(i.e., the point of attachment with the 6-membered heteroaryl of the PTM); and 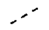 indicates the point of attachment of the PTM with the L or ULM, and where not present, the

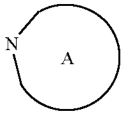

may be attached to the L via an atom of the cyclic group; L is represented by the chemical structure:

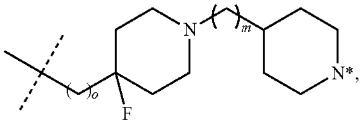

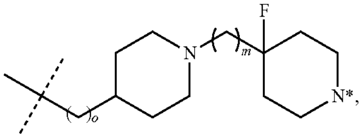

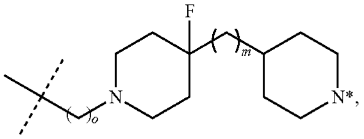

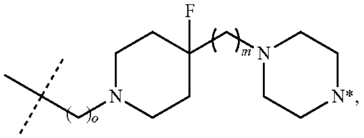

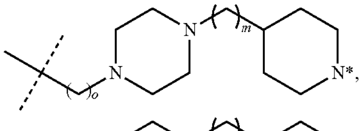

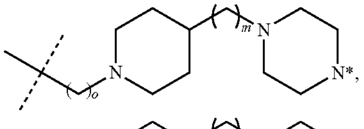

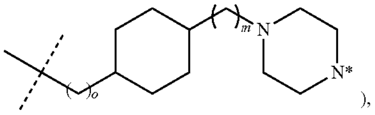

wherein:

$W_{L1}$ is a 6-membered aromatic ring have 0, 1, 2, or 3 heteroatoms (preferably 0, 1, or 2 heteroatoms) selected from 0 and N (preferably N);

$W_{L2}$ is a 6-membered aromatic ring have 0, 1, 2, or 3 heteroatoms (preferably 0, 1, or 2 heteroatoms) selected from 0 and N (preferably N);

m and n are integers independently selected from 0, 1, 2, or 3 (preferably 1); and the L is optionally substituted with 0, 1, 2, or 3 (preferably 0 or 1) groups selected from: —Cl, —F, and $C_{1-3}$ alkyl (e.g., methyl or ethyl).

An aspect of the present disclosure relates to a hetero-bifunctional compound having the chemical structure:

PTM-L-CLM, or a pharmaceutically acceptable salt or solvate thereof, wherein:

(a) the CLM is a small molecule E3 ubiquitin ligase binding moiety that binds a cereblon E3 ubiquitin ligase and represented by the chemical structure:

(a1)

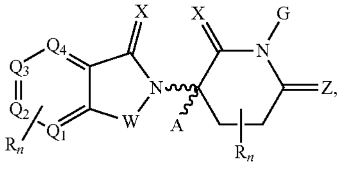

(a2)

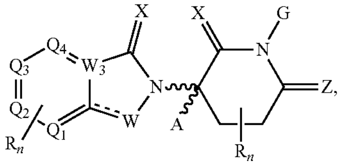

(a3)

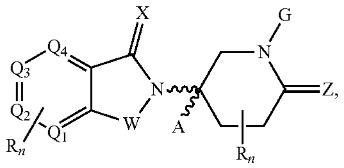

or (a4)

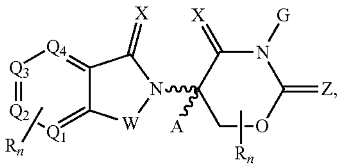

wherein:

W is $CH_2$, C═O, $SO_2$, or NH;

each X is independently selected from absent, O, and S;

Z is absent, O, or S;

G is H or unsubstituted or substituted linear or branched alkyl;

each $Q_1$, $Q_2$, $Q_3$, and $Q_4$ is independently N, CH, or CR;

A is H or unsubstituted or substituted linear or branched alkyl;

n is an integer from 1 to 10 (e.g., 1-4, 1, 2, 3, 4, 5, 6, 7, 8, 9, or 10);

R is a bond, H, O, —CONR'R", —C(═O)R', —OR', —NR'R", unsubstituted or substituted linear or branched alkyl optionally substituted alkoxyl group, —Cl, —F, —Br, —$CF_3$, or —CN, wherein one R is covalently joined to the L; and R' and R" are independently selected from a bond, H, and optionally substituted alkyl;

 represents a single bond or a double bond; and represents a bond that may be stereospecific ((R) or (S)) or non-stereospecific;

(b) the PTM is a small molecule leucine-rich repeat kinase 2 (LRRK2) targeting moiety that binds to LRRK2 or a mutant form thereof represented by the chemical structure:

(PTM-IA)

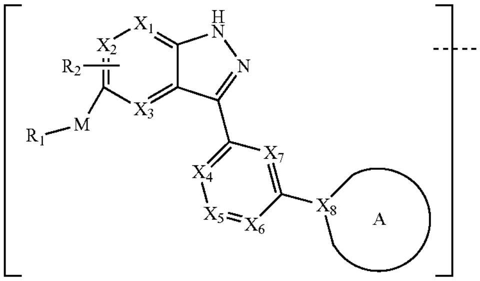

, (PTM-IIIA1)

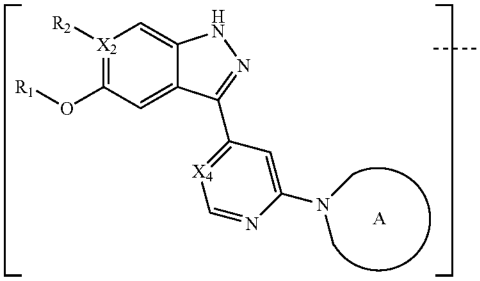

, or (PTM-IIIA2)

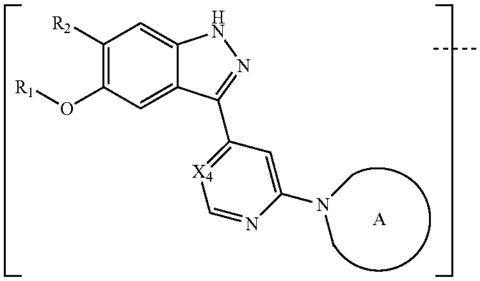

, or (PTM-IIIA3)

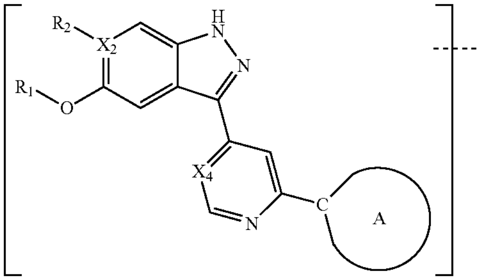

, or

-continued (PTM-IIIA4)

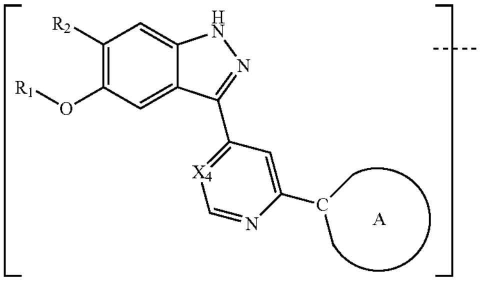

, wherein:

$R_1$ is a isopropyl, tert-butyl,

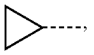 , or 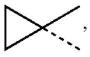 , wherein  is the point of attachment to the oxygen atom of the PTM;

$R^2$ is hydrogen, F, C1, OH, C1-C3 alkyl, or C1-C3 fluoroalkyl;

$X_6$ and $X_7$ are each independently CH or N;

$X_1$, $X_2$, $X_3$, $X_4$, and $X_5$ are each independently a N or CH that is optionally substituted with $R_2$ when CH;

$X_8$ is CH or N;

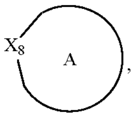 , 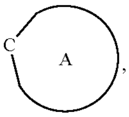 , or 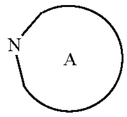

or is an optionally substituted 3-10 membered cycloalkyl, heterocyloalkyl, bicycloalkyl, biheterocycloalkyl, spirocycloalkyl, or spiroheterocycloalkyl containing 1-4 (e.g., 1, 2, 3, or 4) heteroatoms selected from N, O, and S (e.g., optionally substituted with one or more (e.g., 1, 2, 3, or 4) substitutions; and  of the PTM indicates the point of attachment with the L; and (c) the L is a chemical linker group that covalently couples the CLM to the PTM.

An aspect of the present disclosure relates to a hetero-bifunctional compound having the chemical structure:

PTM-L-CLM, or a pharmaceutically acceptable salt or solvate thereof, wherein:

(a) the CLM is a small molecule E3 ubiquitin ligase binding moiety that binds a cereblon E3 ubiquitin ligase and represented by the chemical structure:

(a1)

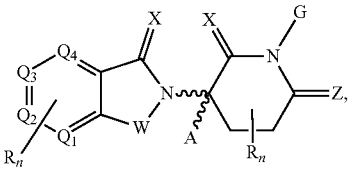

,

-continued (a2)

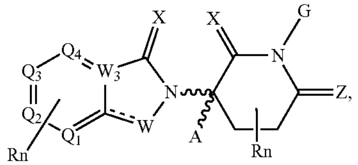

(a3)

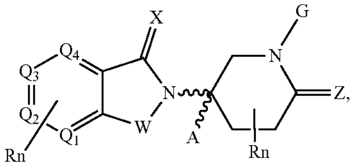

(a4)

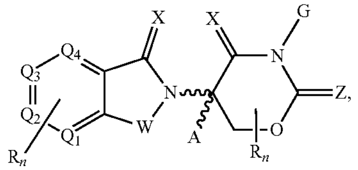

wherein:

W is $CH_2$, C═O, $SO_2$, or NH;

each X is independently selected from absent, O, and S;

Z is absent, O, or S;

G is H or unsubstituted or substituted linear or branched alkyl;

each $Q_1$, $Q_2$, $Q_3$, and $Q_4$ is independently N, CH, or CR; A is H or unsubstituted or substituted linear or branched alkyl;

n is an integer from 1 to 10 (e.g., 1-4, 1, 2, 3, 4, 5, 6, 7, 8, 9, or 10);

R is a bond, H, O, —CONR'R", —C(═O)R', —OR', —NR'R", unsubstituted or substituted linear or branched alkyl optionally substituted alkoxyl group, —Cl, —F, —Br, —$CF_3$, or —CN, wherein one R is covalently joined to the L; and R' and R" are independently selected from a bond, H, and optionally substituted alkyl;

 represents a single bond or a double bond; and represents a bond that may be stereospecific ((R) or (S)) or non-stereospecific;

(b) the PTM is a small molecule leucine-rich repeat kinase 2 (LRRK2) targeting moiety that binds to LRRK2 or a mutant form thereof represented by the chemical structure:

(PTM-IA)

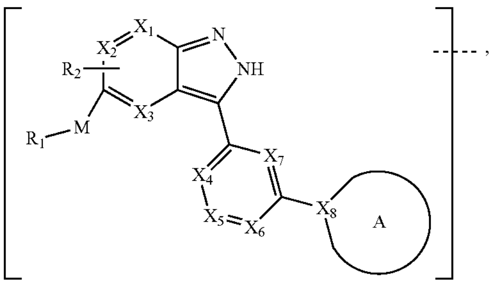

-continued (PTM-IIIA1)

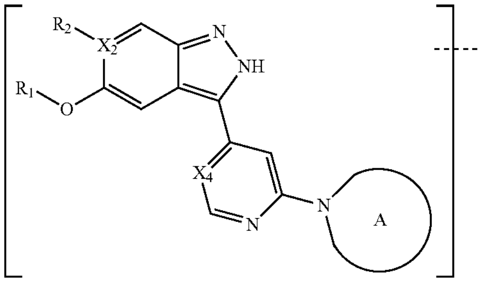

(PTM-IIIA2)

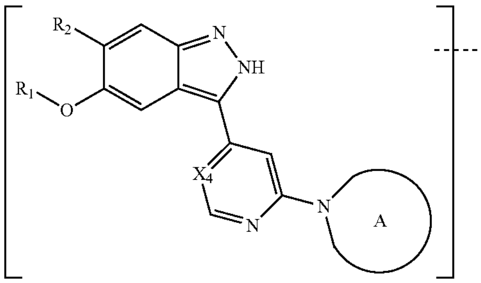

(PTM-IIIA3)

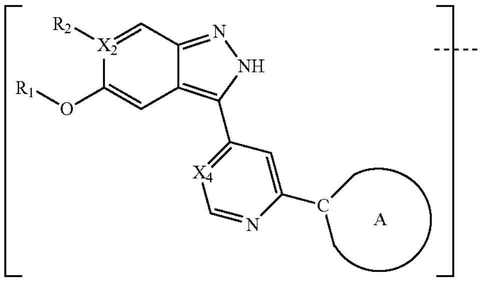

or (PTM-IIIA4)

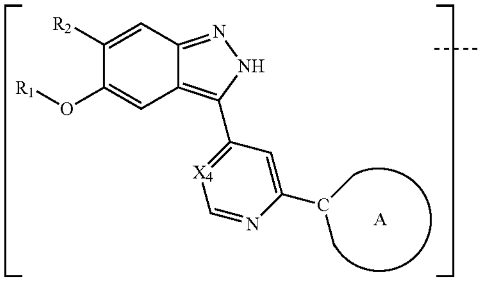

wherein:

$R_1$ is a isopropyl, tert-butyl,

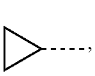, or 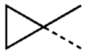, wherein  is the point of attachment to the oxygen atom of the PTM;

$R^2$ is hydrogen, F, C1, OH, C1-C3 alkyl, or C1-C3 fluoroalkyl;

$X_6$ and $X_7$ are each independently CH or N;

$X_1$, $X_2$, $X_3$, $X_4$, and $X_5$ are each independently a N or CH that is optionally substituted with $R_2$ when CH;

$X_8$ is CH or N;

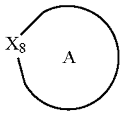, 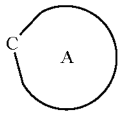, or 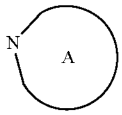

is an optionally substituted 3-10 membered cycloalkyl, heterocyloalkyl, bicycloalkyl, biheterocycloalkyl, spirocycloalkyl, or spiroheterocycloalkyl containing 1-4 (e.g., 1, 2, 3, or 4) heteroatoms selected from N, O, and S (e.g., optionally substituted with one or more (e.g., 1, 2, 3, or 4) substitutions; and

 of the PTM indicates the point of attachment with the L; and (c) the L is a bond or a chemical linker group that covalently couples the CLM to the PTM.

In any aspect or embodiment described herein, the compound is represented by a chemical structure selected from:

(Formula Ia)

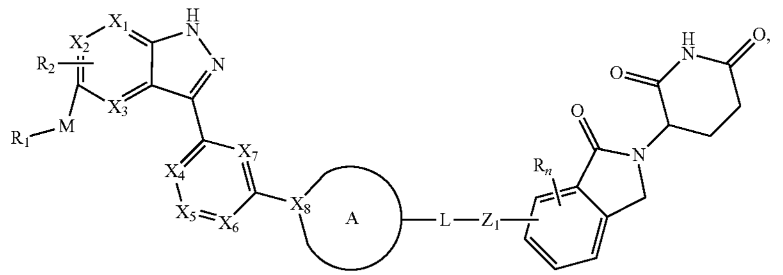

(Formula IIIa)

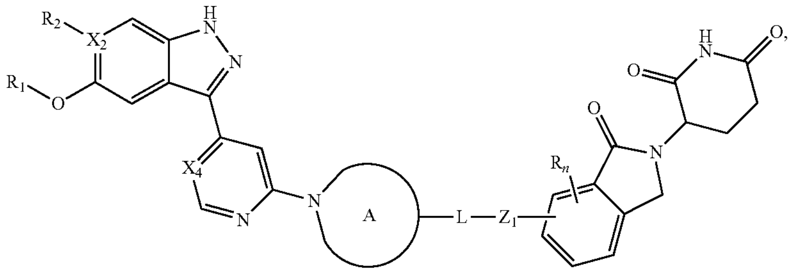

and (Formula IIIb)

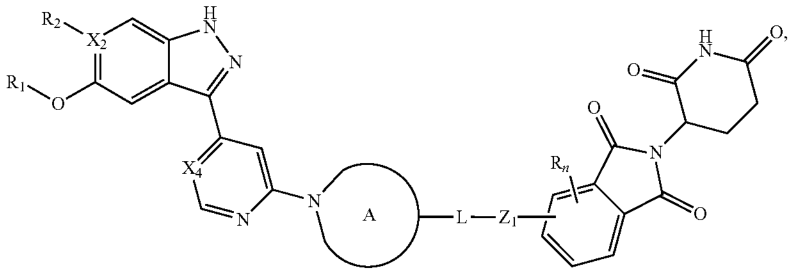

wherein:

$X_2$ is C, CH or N;

$Z_1$ is a bond a carbon shared with a cyclic group of L, or a nitrogen shared with a cyclic group of L;

n is an integer from 0 to 3 (e.g., 0, 1, 2, or 3);

R is a bond, H, O, OH, N, NH, $NH_2$, Cl, —F, methyl, methoxy, or ethoxy; and $R^2$ is H, Cl, F, OH, C1-C3 alkyl, or C1-3 fluoralkyl.

In any aspect or embodiment described herein, the compound is represented by a chemical structure selected from:

(Formula IIId)

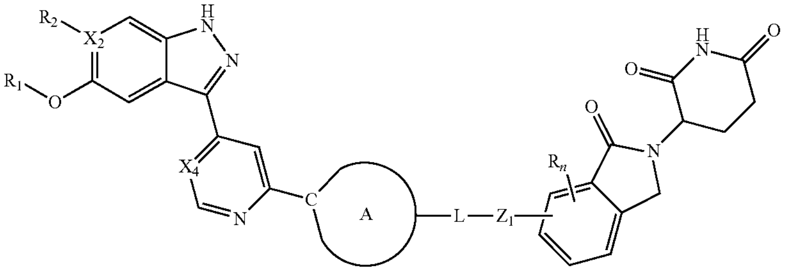

and (Formula IIIe)

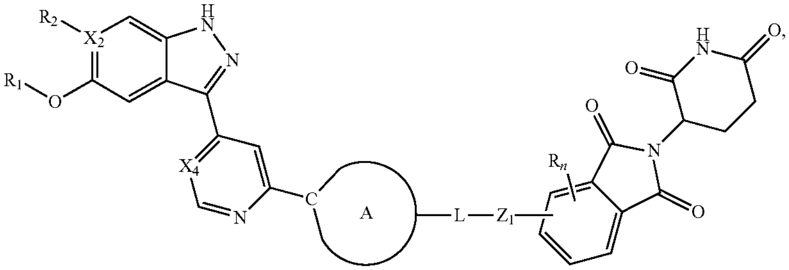

, wherein:

$X_2$ is C, CH or N;

$Z_1$ is a bond a carbon shared with a cyclic group of L, or a nitrogen shared with a cyclic group of L;

n is an integer from 0 to 3 (e.g., 0, 1, 2, or 3);

R is a bond, H, O, OH, N, NH, $NH_2$, Cl, —F, methyl, methoxy, or ethoxy; and $R^2$ is H, Cl, F, OH, C1-C3 alkyl, or C1-3 fluoralkyl.

In any aspect or embodiment described herein, the compound is represented by the chemical structure:

(Formula VIa)

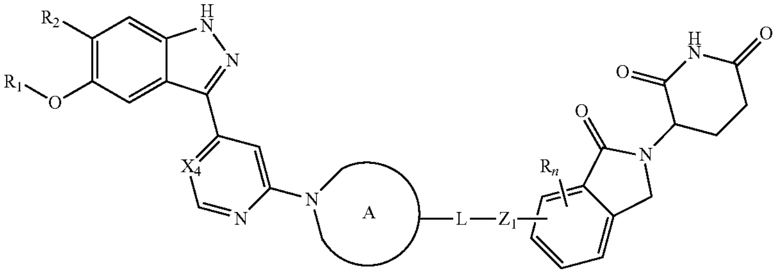

or (Formula VIb)

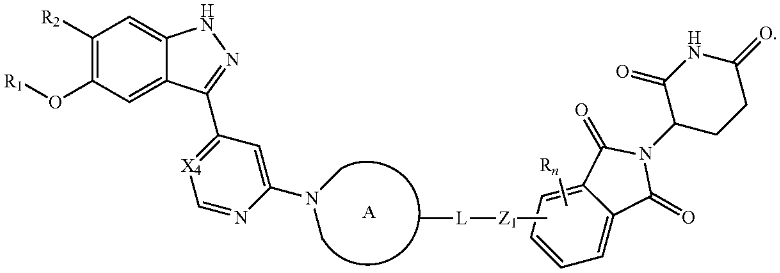

.

In any aspect or embodiment described herein, the compound is represented by the chemical structure:
(Formula VId)
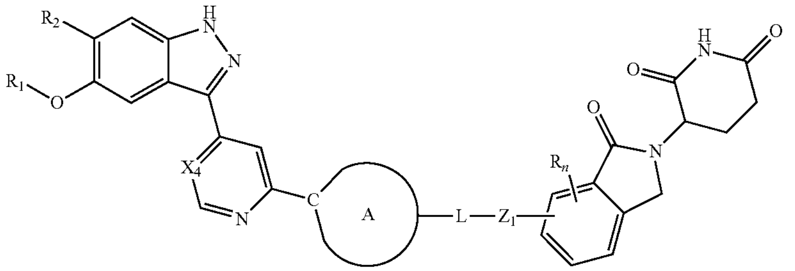
or
(Formula VIe)
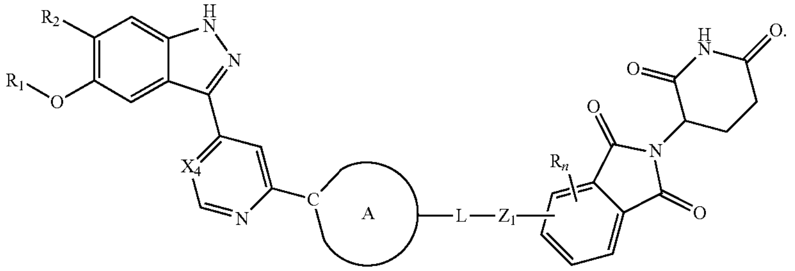
In any aspect or embodiment described herein, one or more of:
(a) the CLM is represented by:
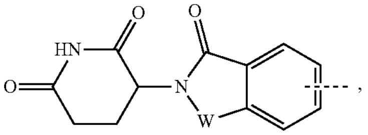
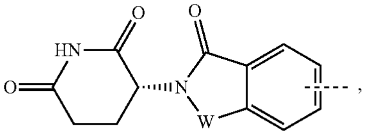
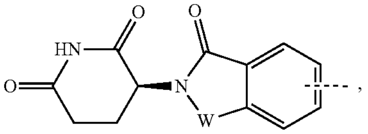
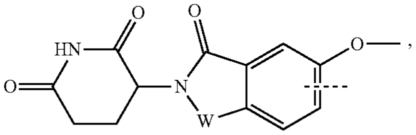
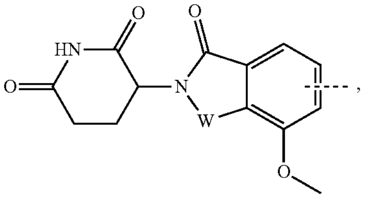
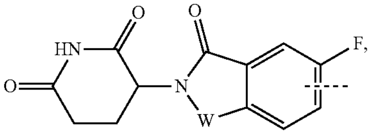
-continued
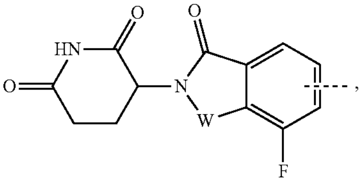
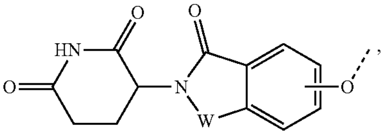
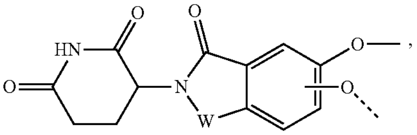
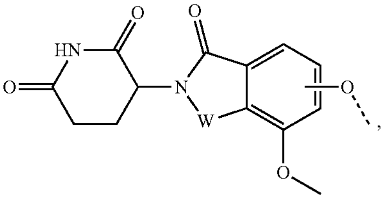
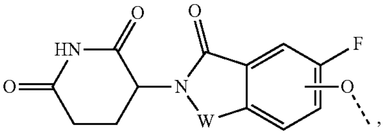
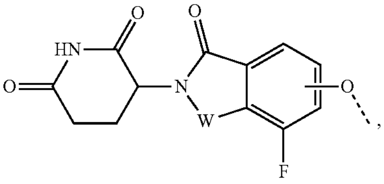

-continued
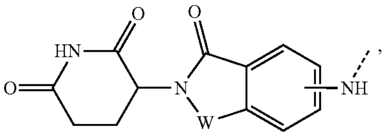
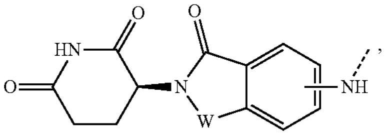
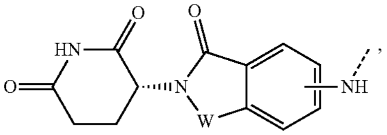
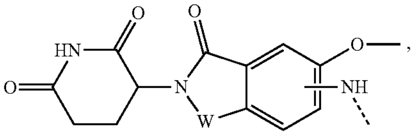
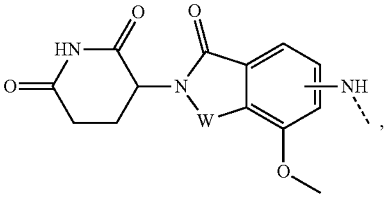
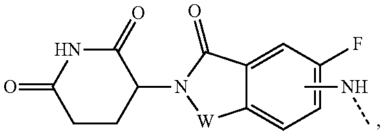
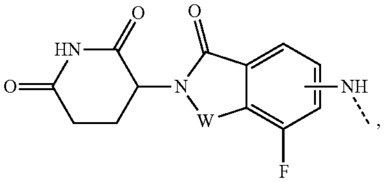
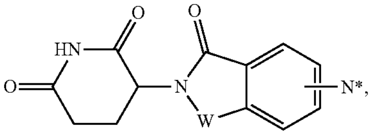
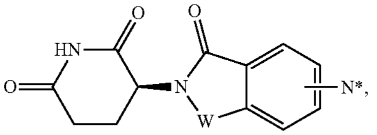
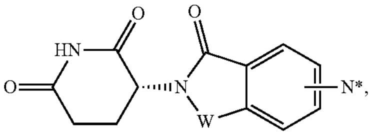
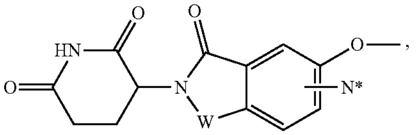
-continued
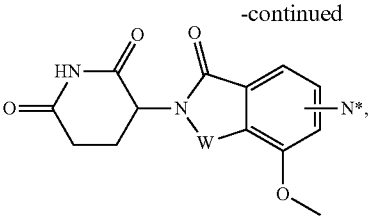
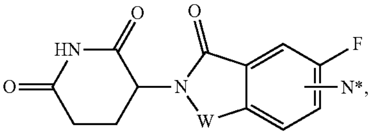
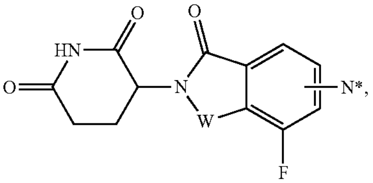
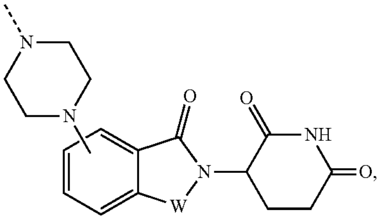
or
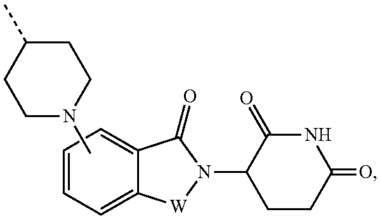
wherein:
⸝⸝ of the ULM indicates the point of attachment with the L; and
N* is a nitrogen atom that is shared with the L;
(b) the PTM is represented by:
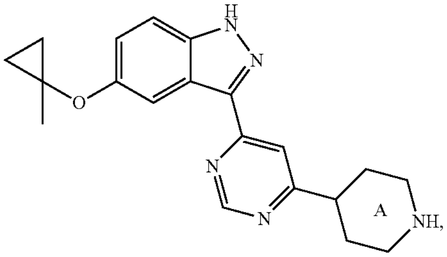
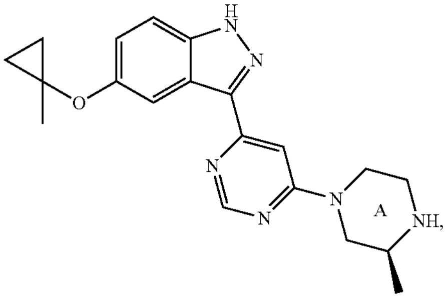

-continued
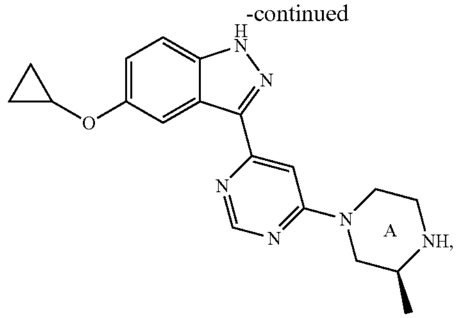
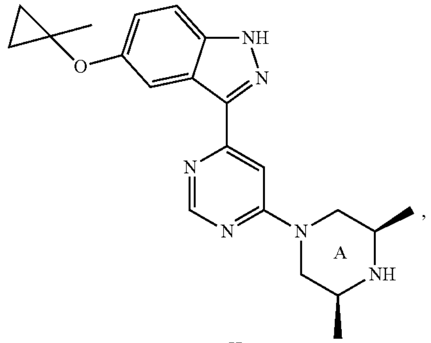
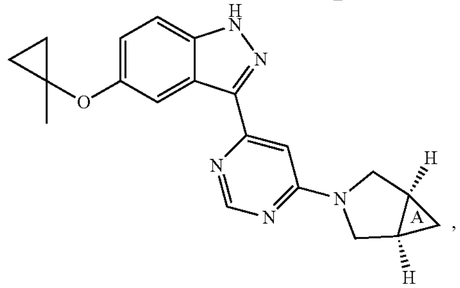
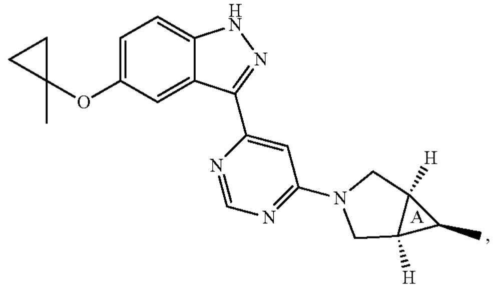
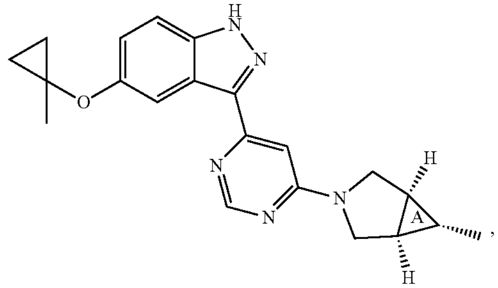
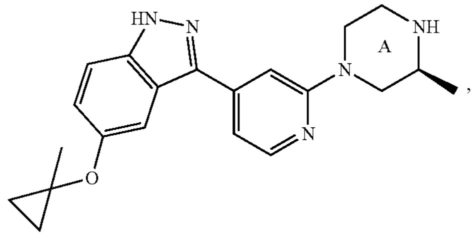
-continued
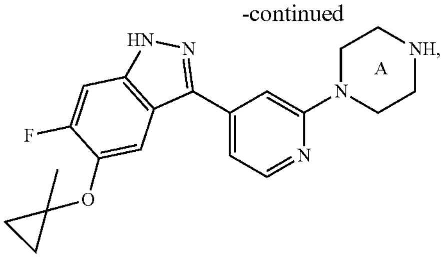
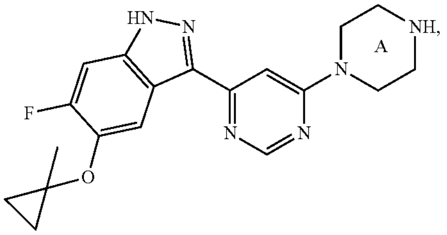
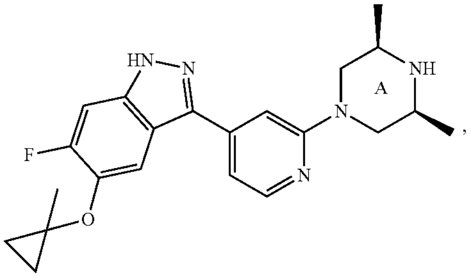
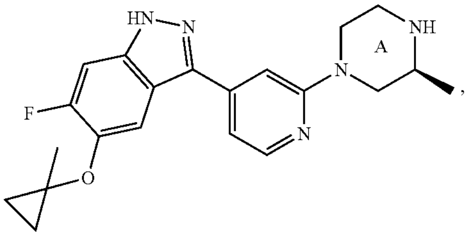
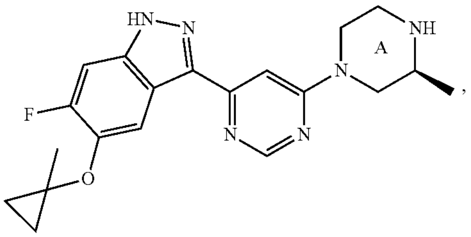
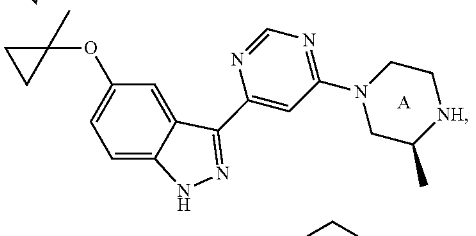
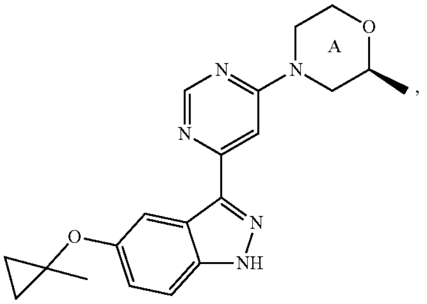

-continued
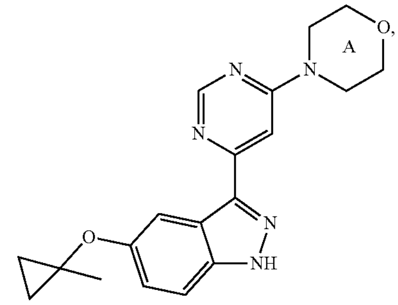
,
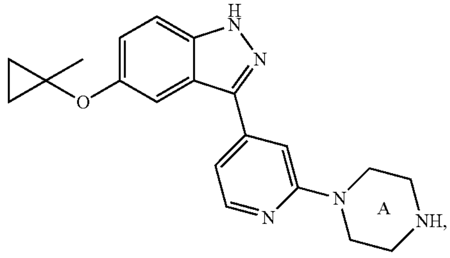
,
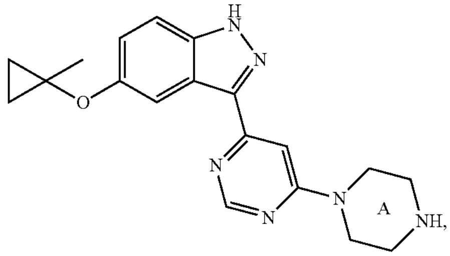
,
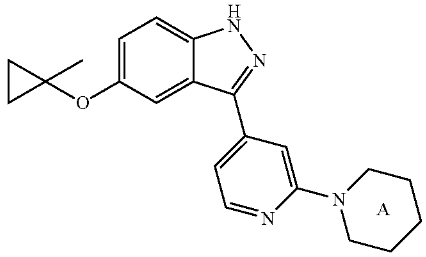
,
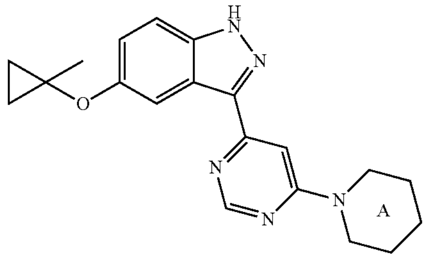
,
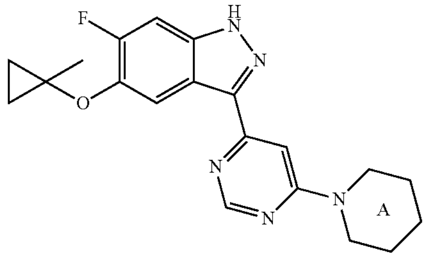
,
-continued
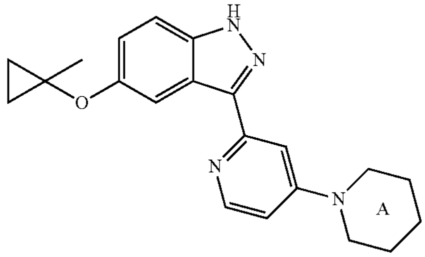
,
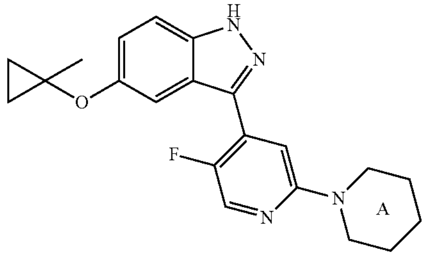
,
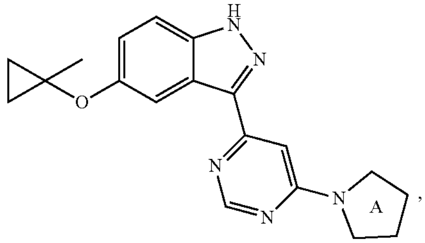
,
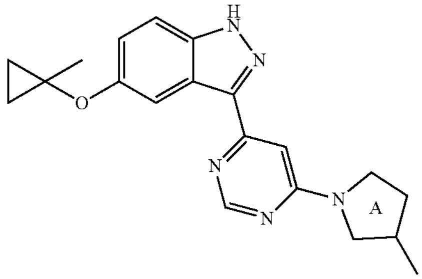
,
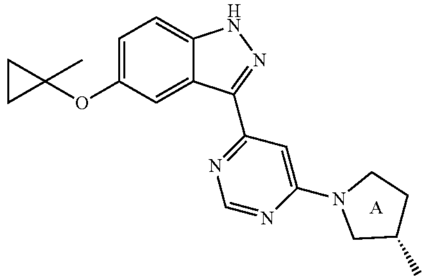
,
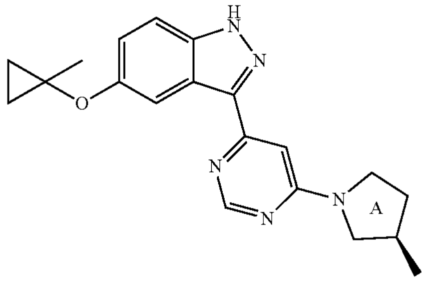
, -continued
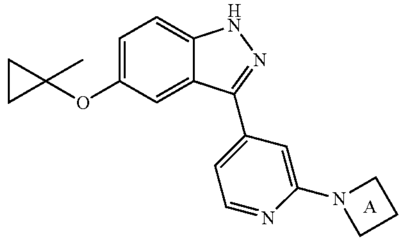
,
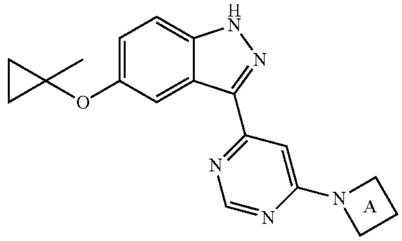
,
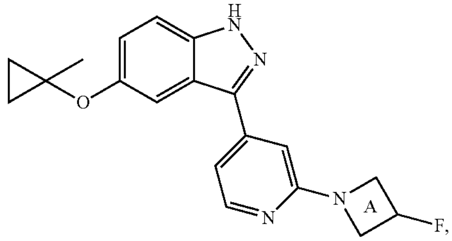
,
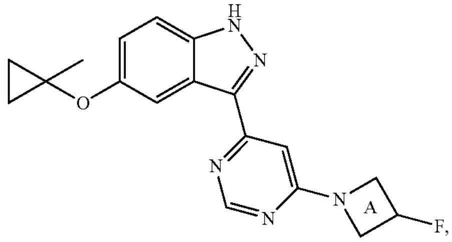
,
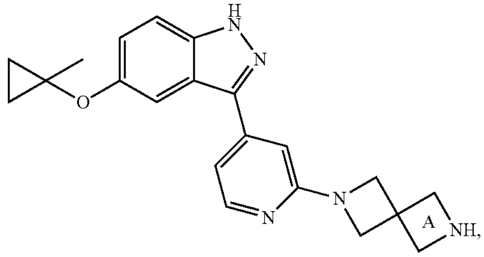
,
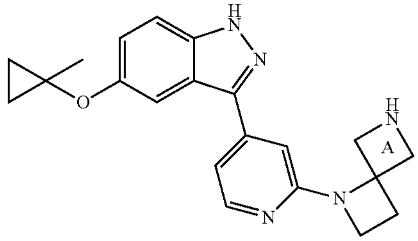
,
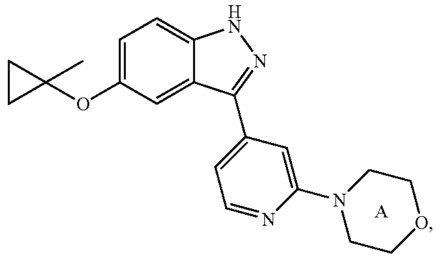
,
-continued
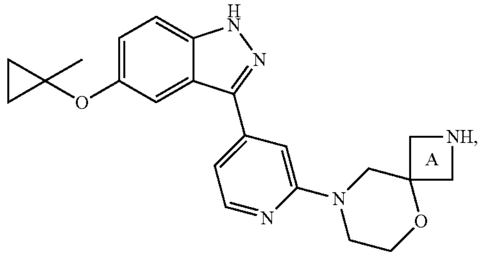
,
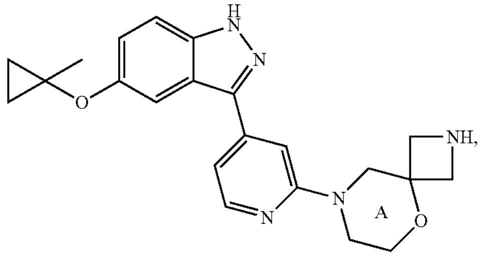
,
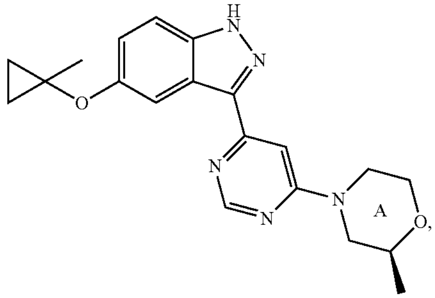
,
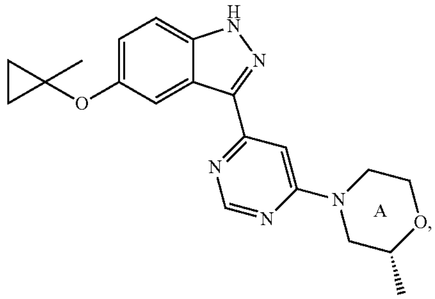
, and
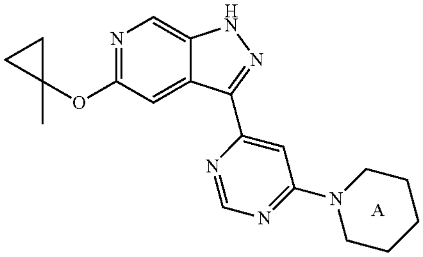
,
wherein the PTM is covalently linked to the L via an atom of heterocycloalkyl A or a substituent thereof;
(c) the L is a linker group (L) selected from:
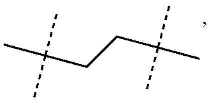
,
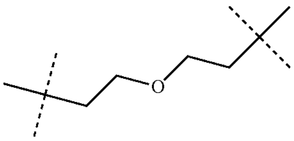
, -continued
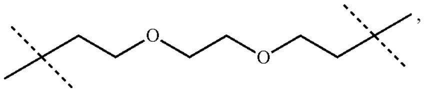
,
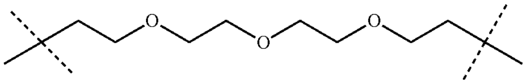
,
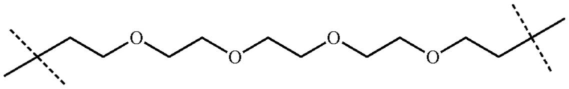
,
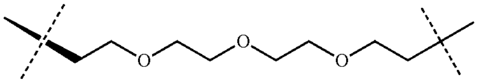
,
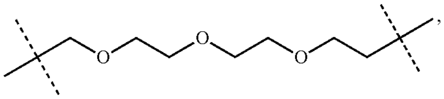
,
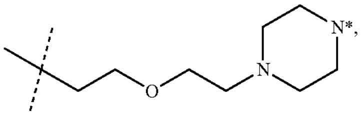
,
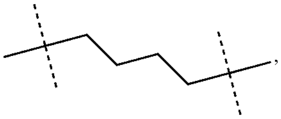
,
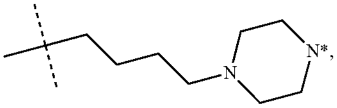
,
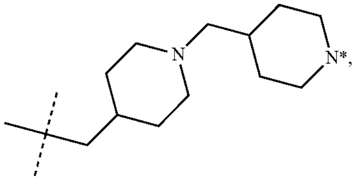
,
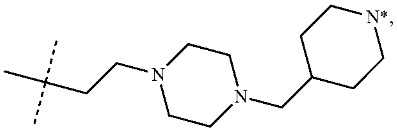
,
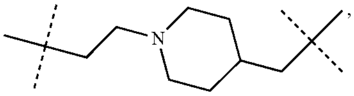
,
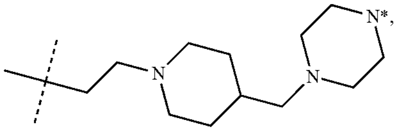
,
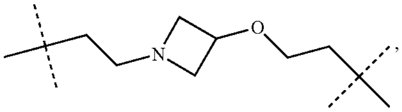
,
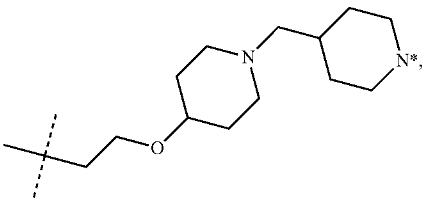
,
-continued
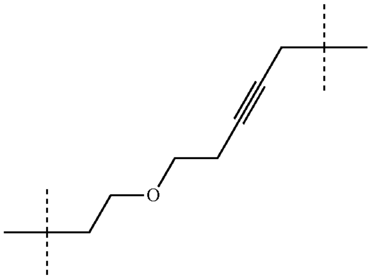
,
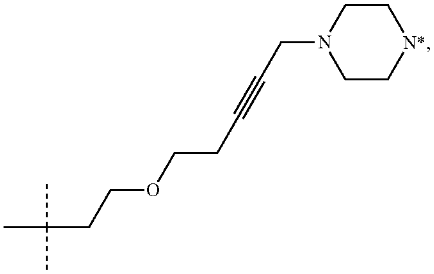
,
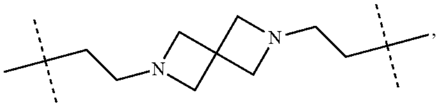
,
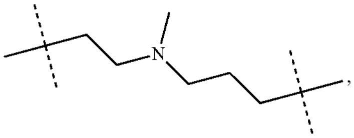
,
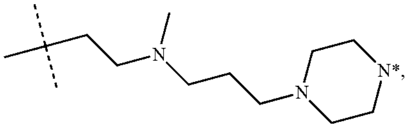
,
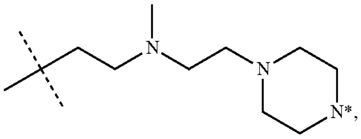
,
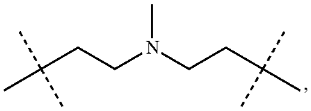
,
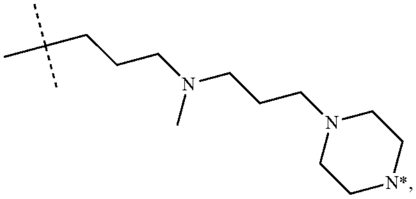
,
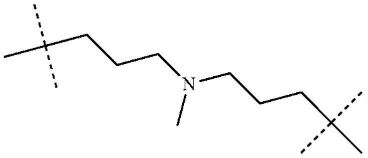
,
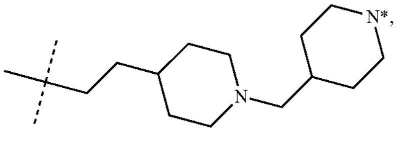
, -continued
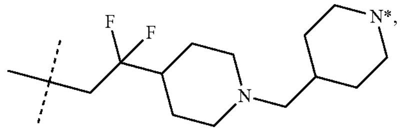
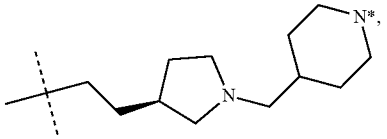
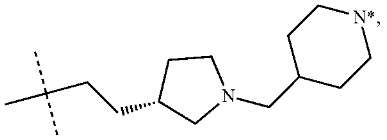
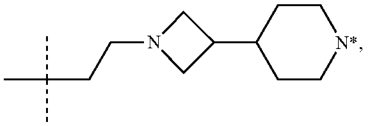
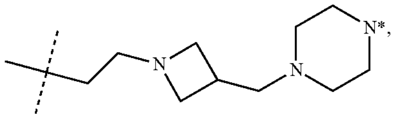
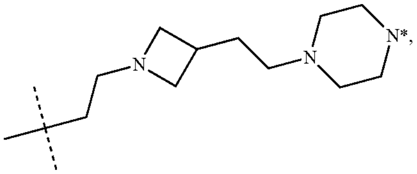
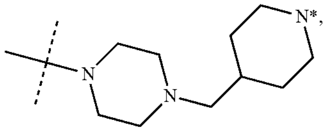
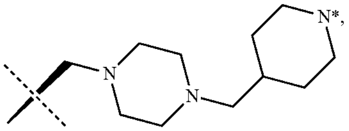
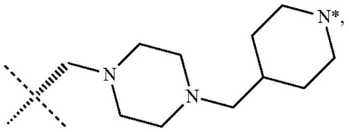
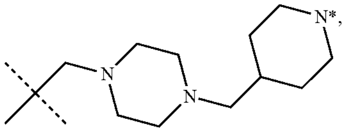
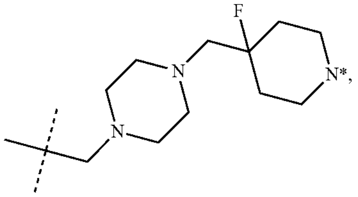
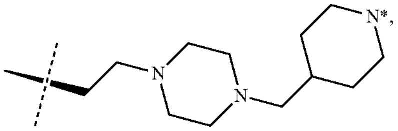
-continued
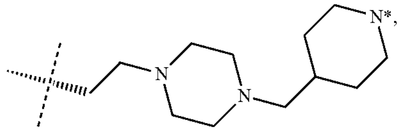
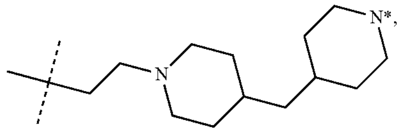
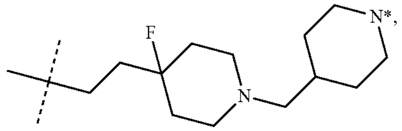
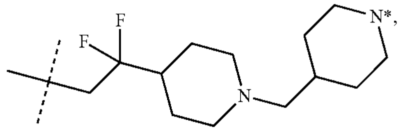
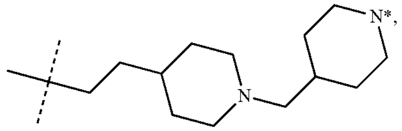
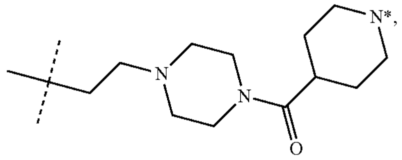
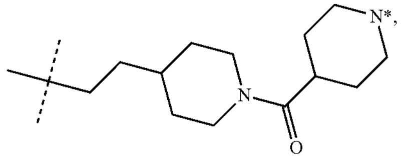
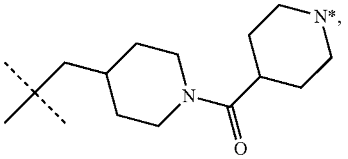
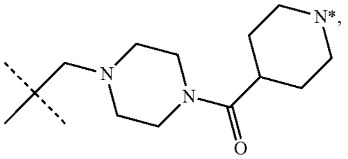
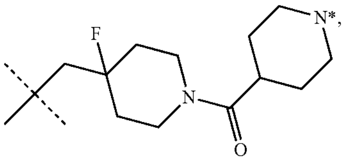
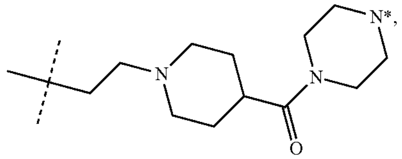

-continued
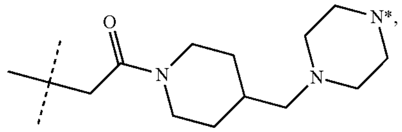
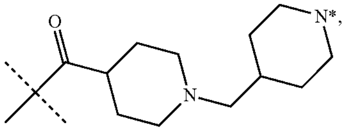
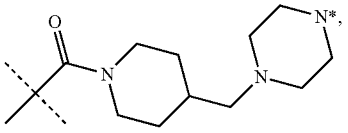
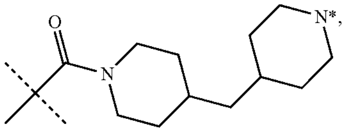
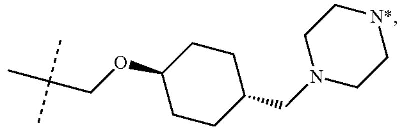
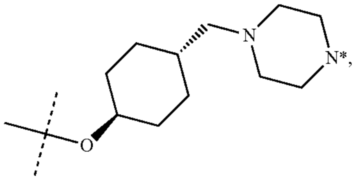
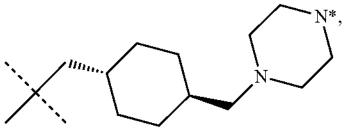
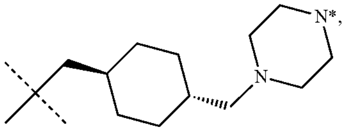
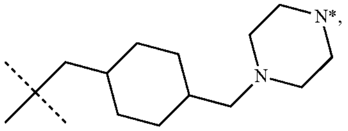
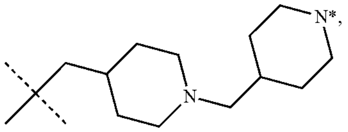
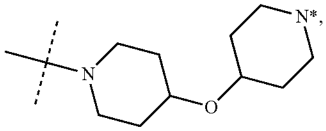
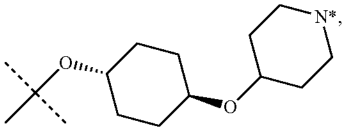
-continued
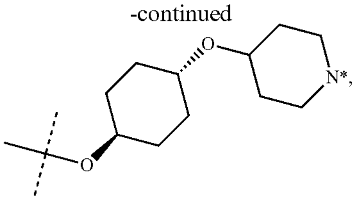
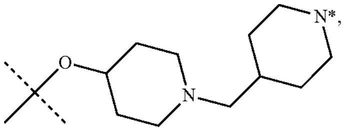
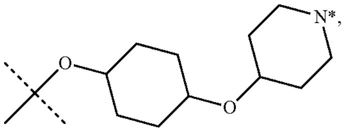
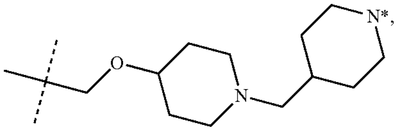
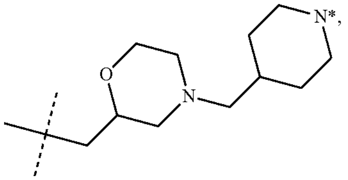
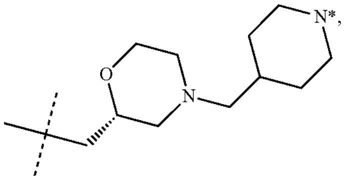
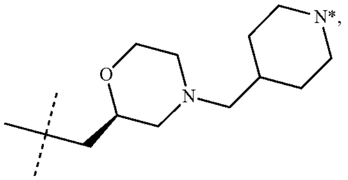
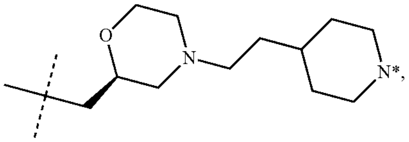
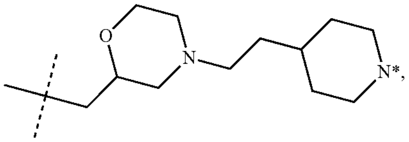
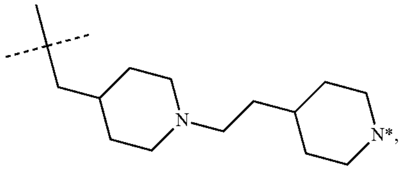
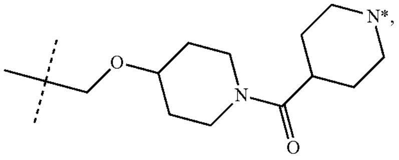

-continued
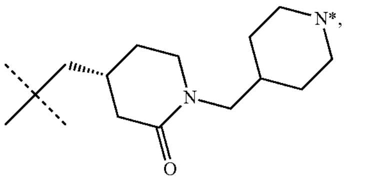
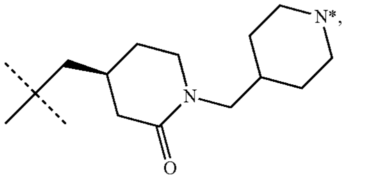
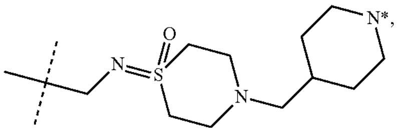
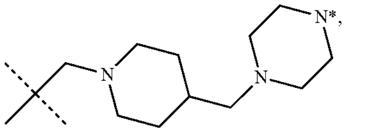
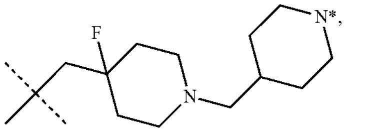
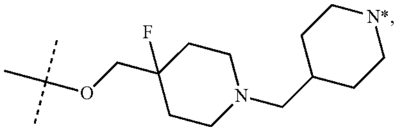
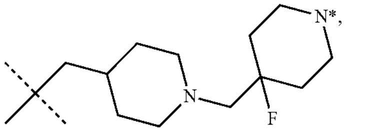
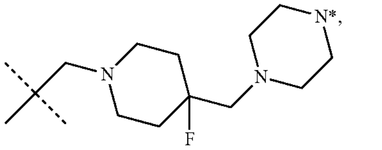
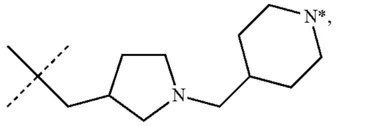
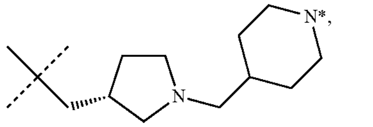
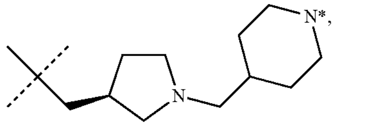
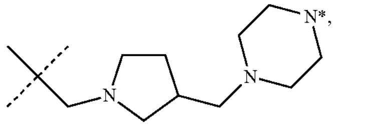
-continued
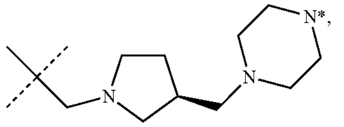
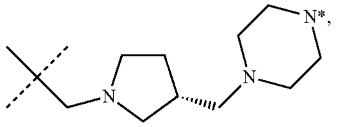
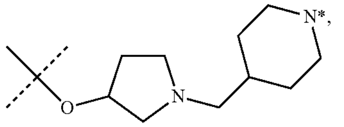
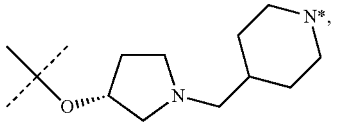
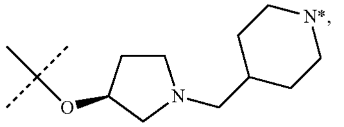
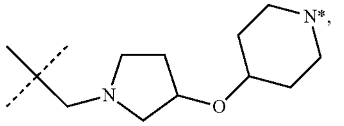
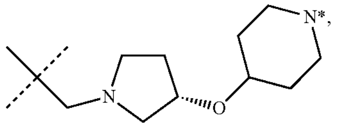
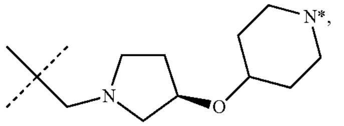
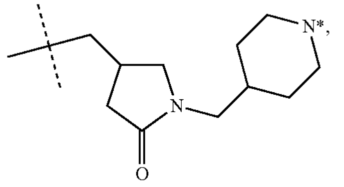
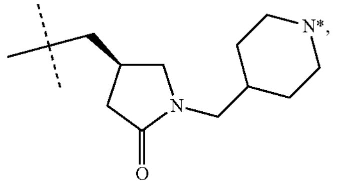
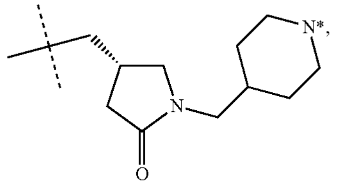
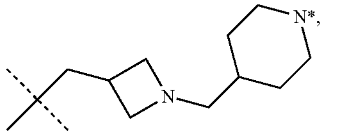

-continued
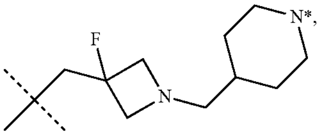,
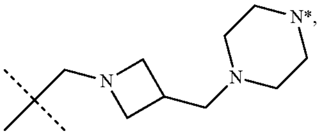,
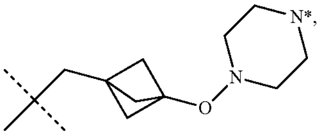,
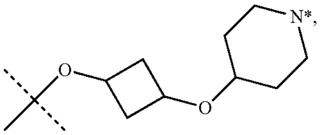,
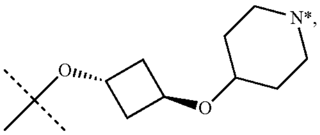,
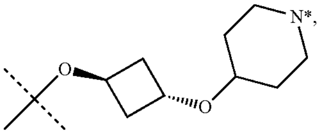,
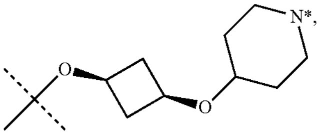,
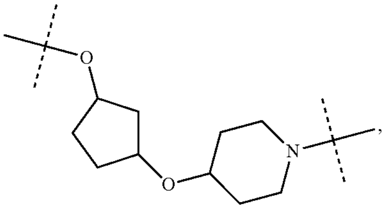,
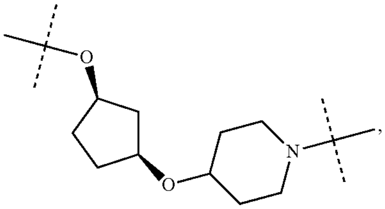,
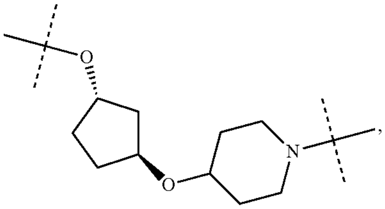,
-continued
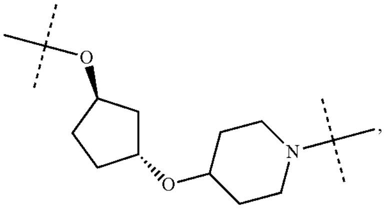,
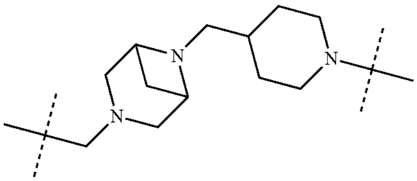,
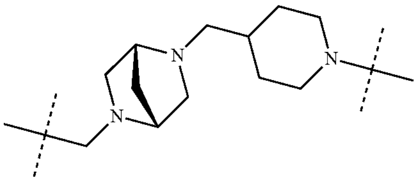,
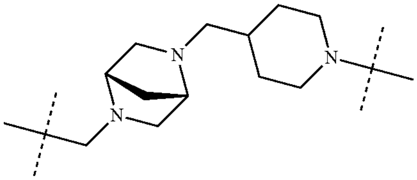,
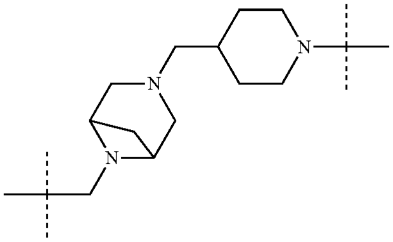,
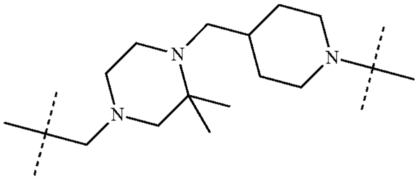
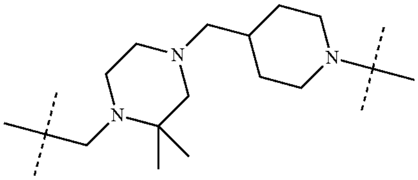
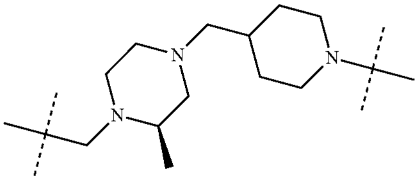
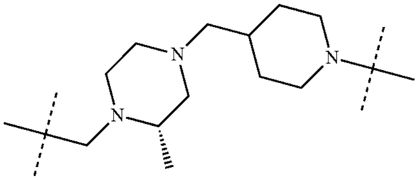

-continued
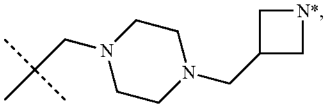
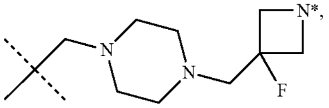
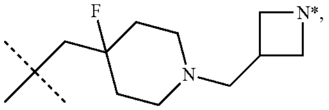
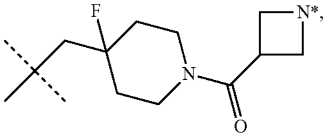
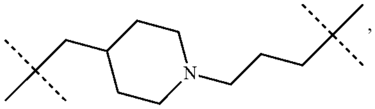
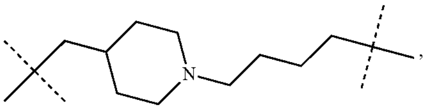
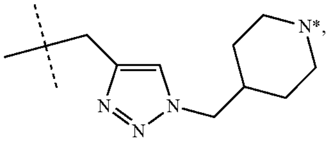
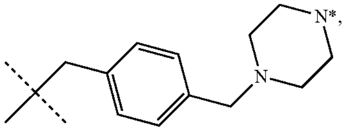
-continued
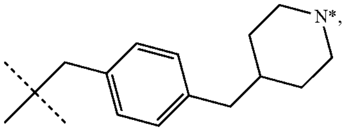
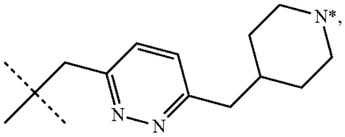
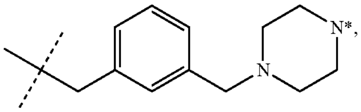
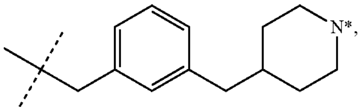
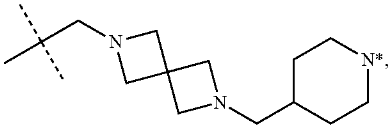
and
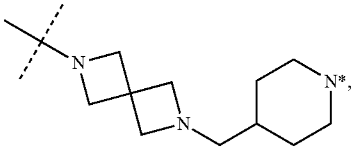
wherein:
N* is a nitrogen atom that is covalently linked to or ed wi CLM or the PTM; and
 and  represented the point of attachment to the CLM or the PTM; or
(d) a combination thereof.
In any aspect or embodiment described herein, the compound has the chemical structure:
(Formula Ia)
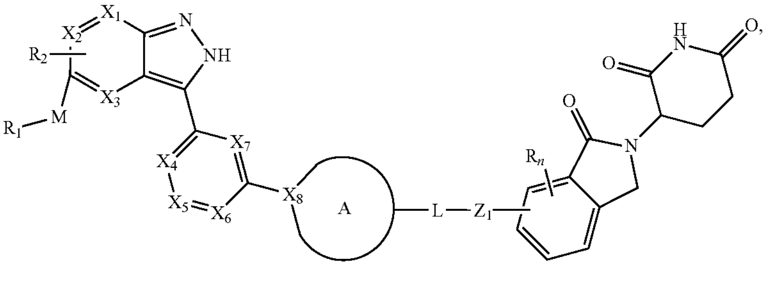
(Formula IIIa)
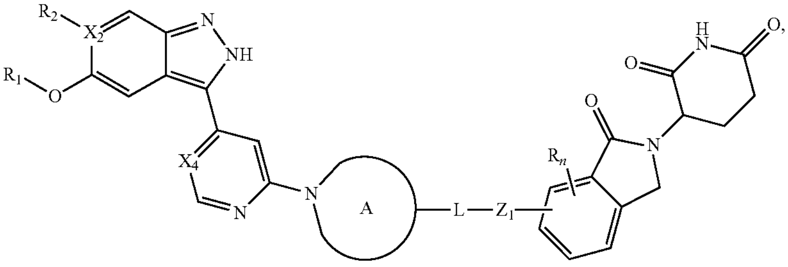
and -continued (Formula IIIb)

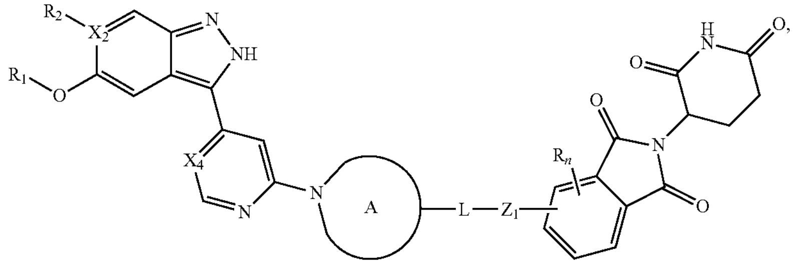

wherein:

$X_2$ is C, CH or N;

$Z_1$ is a bond a carbon shared with a cyclic group of L, or a nitrogen shared with a cyclic group of L;

n is an integer from 0 to 3 (e.g., 0, 1, 2, or 3);

R is a bond, H, O, OH, N, NH, $NH_2$, Cl, —F, methyl, methoxy, or ethoxy; and $R^2$ is H, Cl, F, OH, C1-C3 alkyl, or C1-3 fluoralkyl.

In any aspect or embodiment described herein, the compound is represented by the chemical structure:

(Formula VIa)

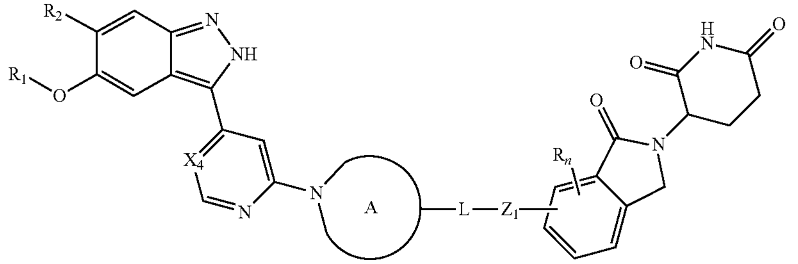

or (Formula VIb)

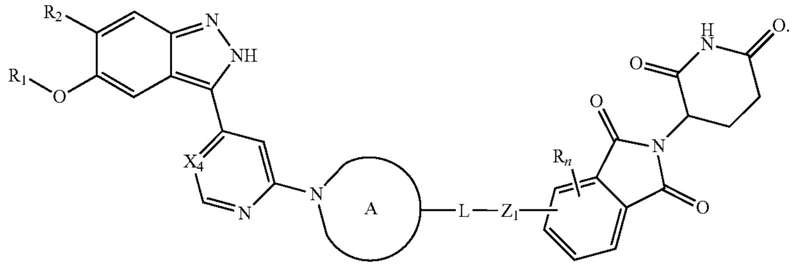

In any aspect or embodiment described herein, the compound is represented by the chemical structure:

(Formula VId)

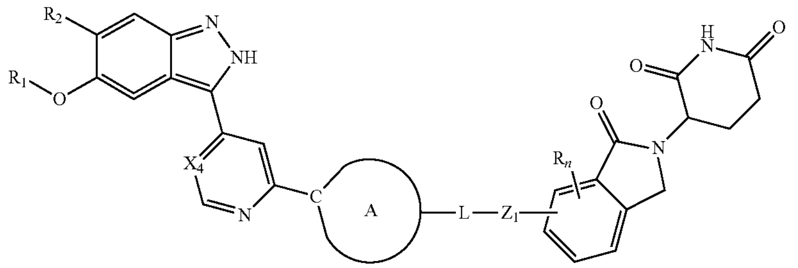

or

-continued
(Formula VIe)
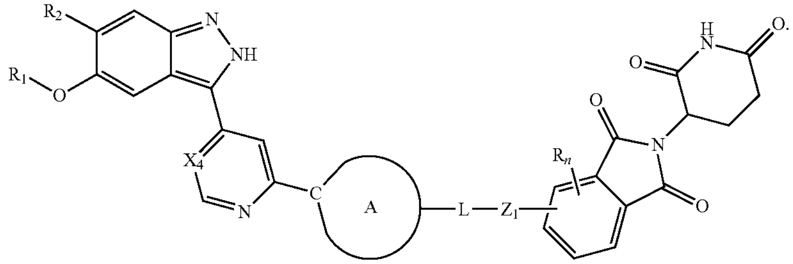
In any aspect or embodiment described herein, one or more of:
(a) the CLM is represented by:
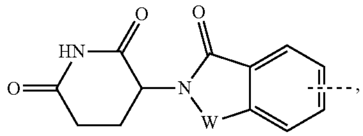
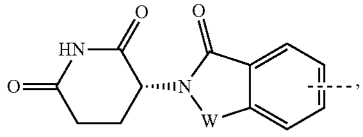
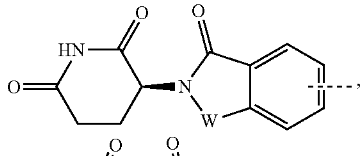
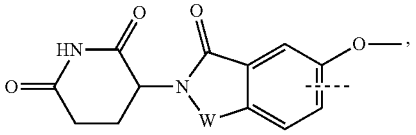
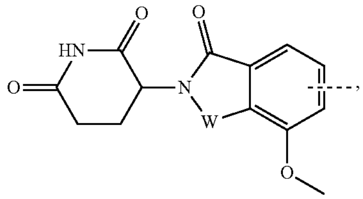
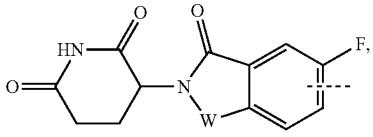
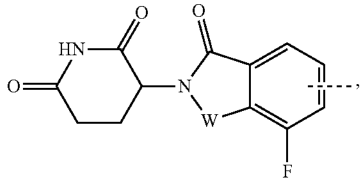
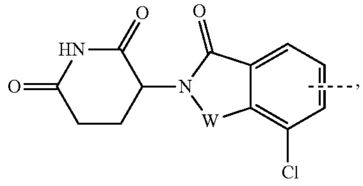
-continued
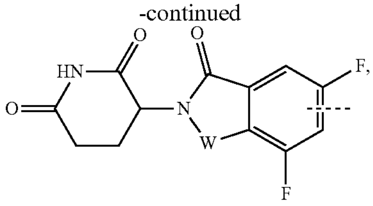
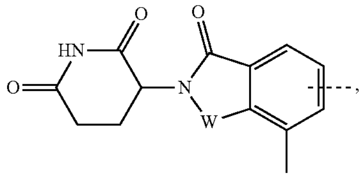
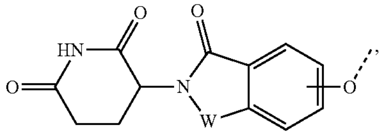
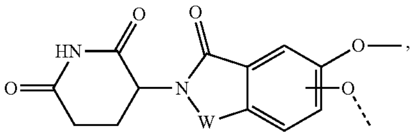
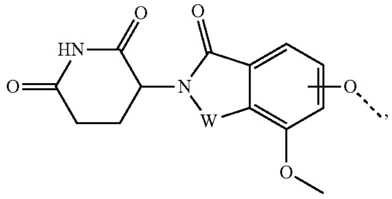
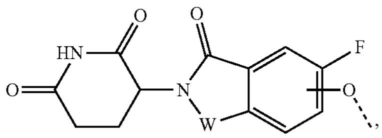
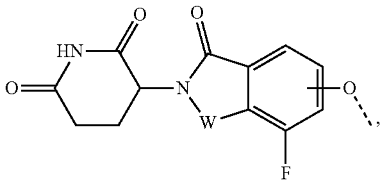
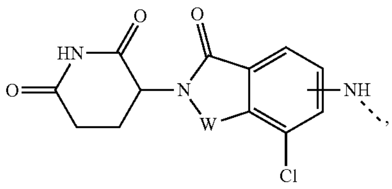

-continued
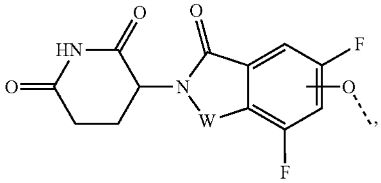
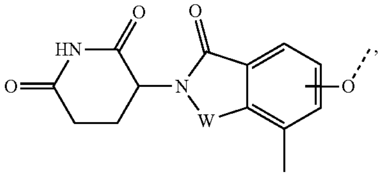
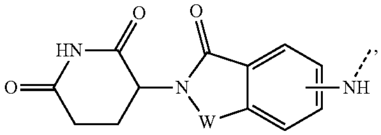
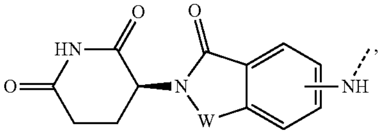
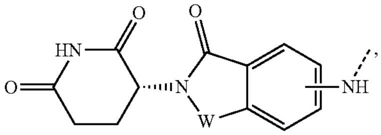
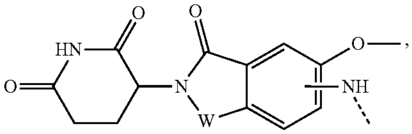
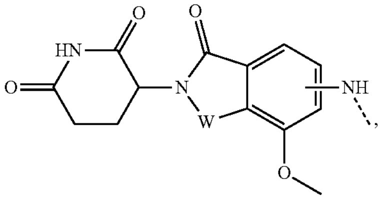
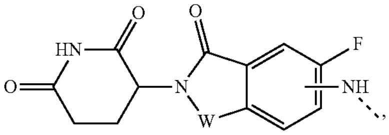
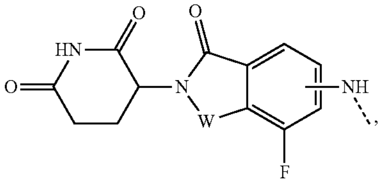
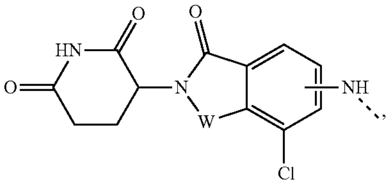
-continued
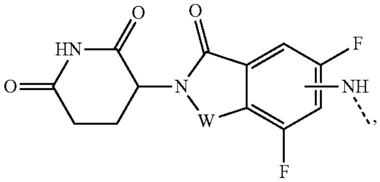
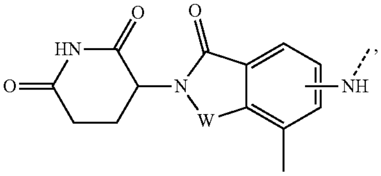
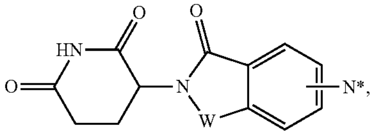
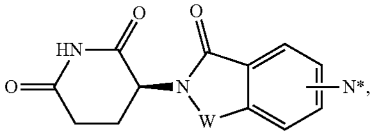
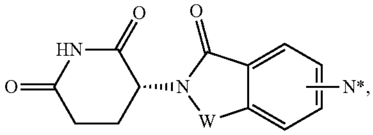
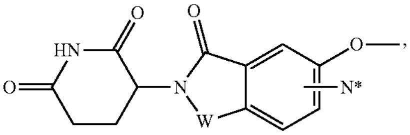
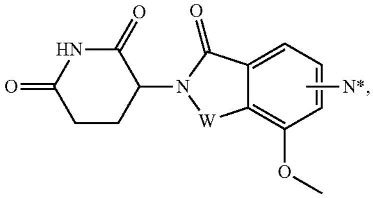
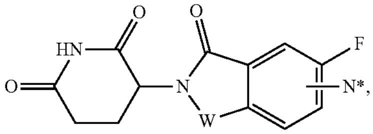
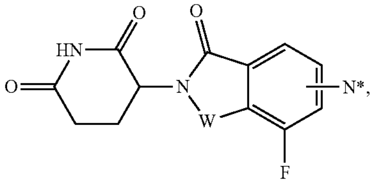
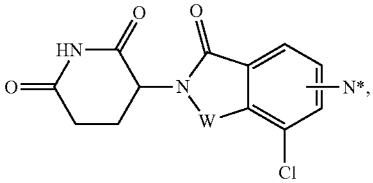

-continued
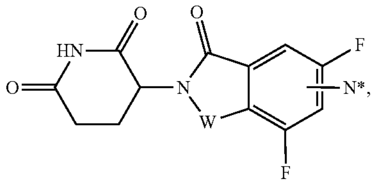
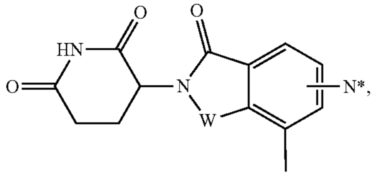
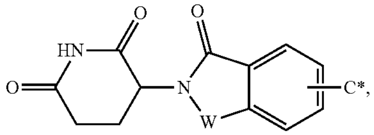
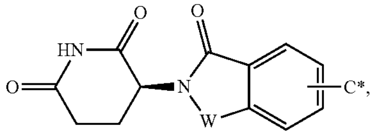
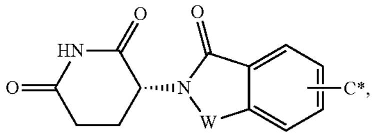
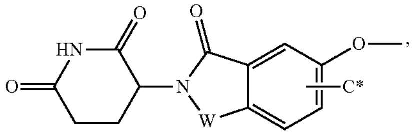
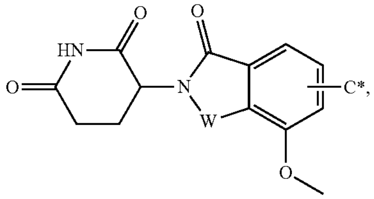
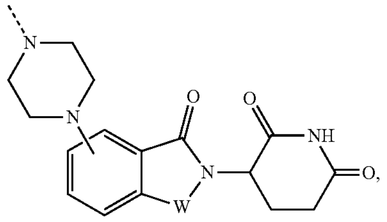
or
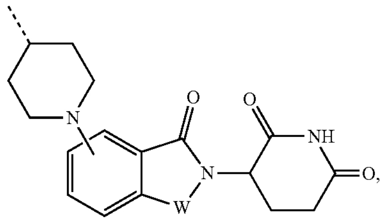
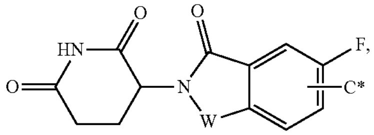
-continued
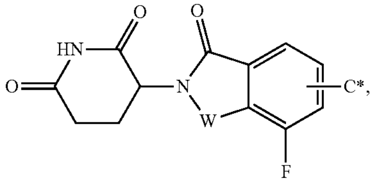
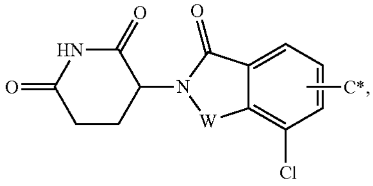
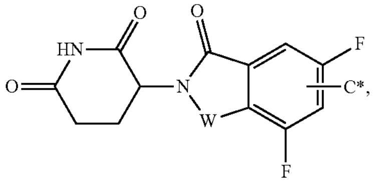
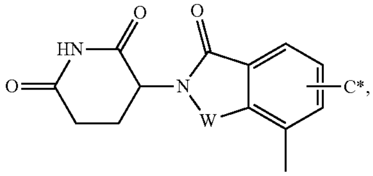
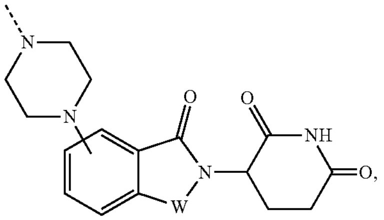
or
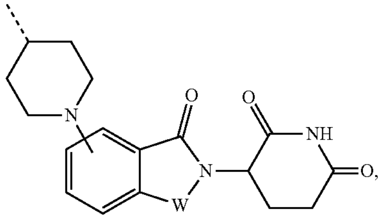
wherein:
⸝⸝ of the ULM indicates the point of attachment with the L;
C* is a carbon atom that is shared with the L; and
N* is a nitrogen atom that is shared with the L;
(b) the PTM is represented by:
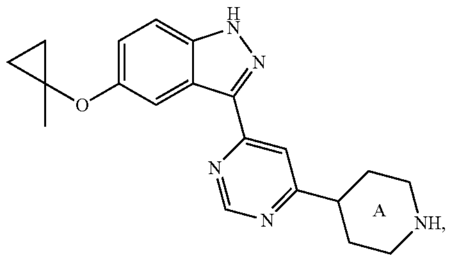

-continued
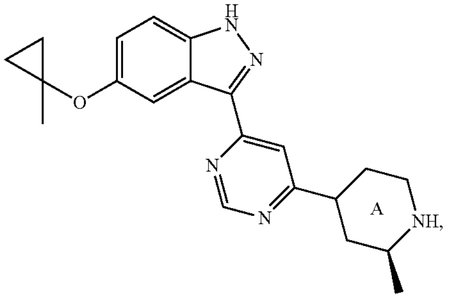
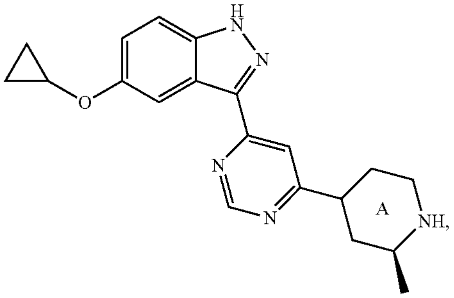
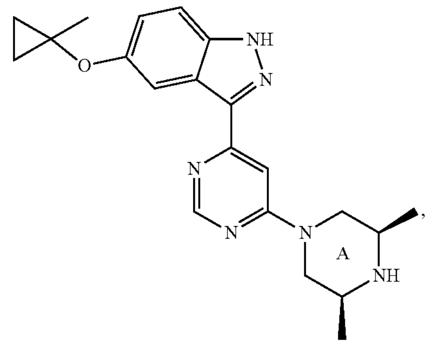
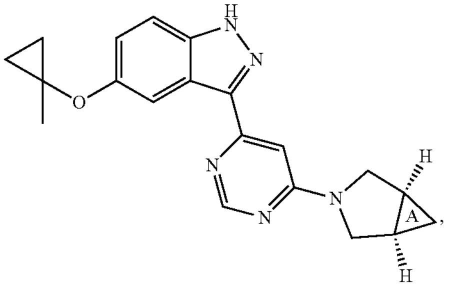
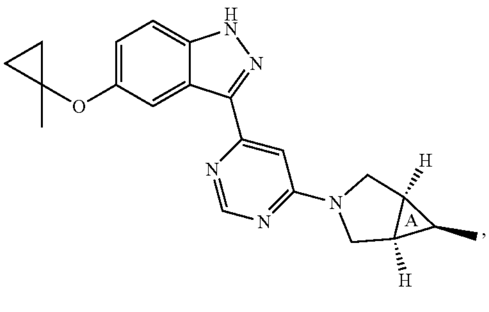
-continued
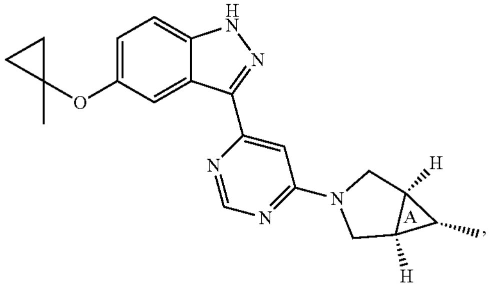
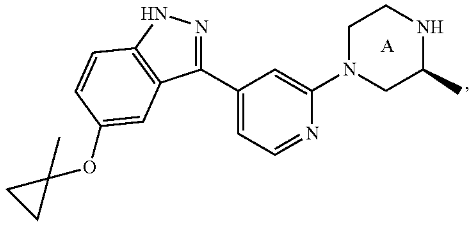
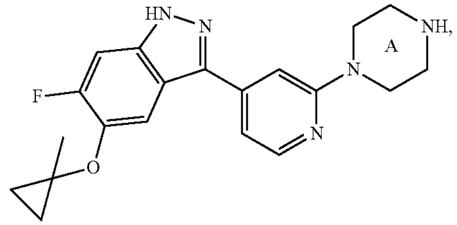
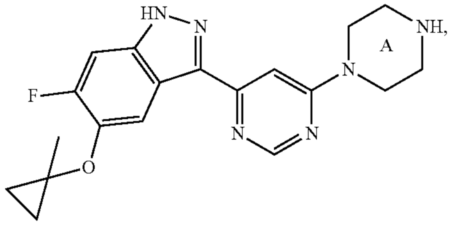
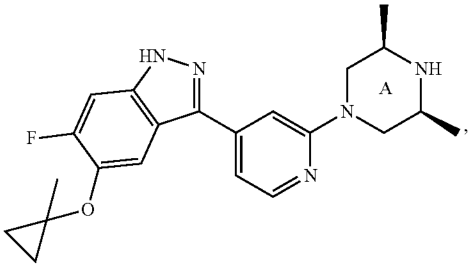
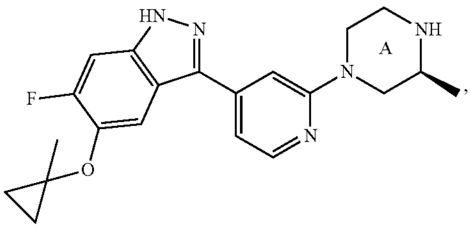
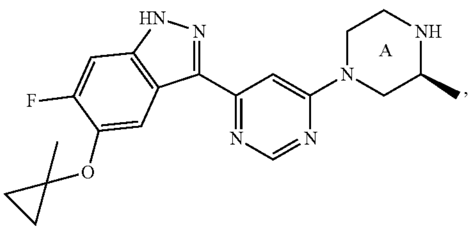

-continued
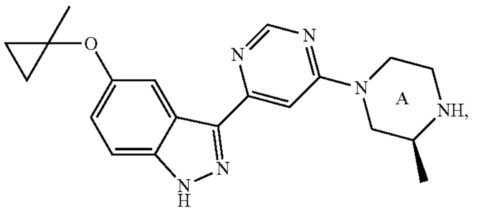
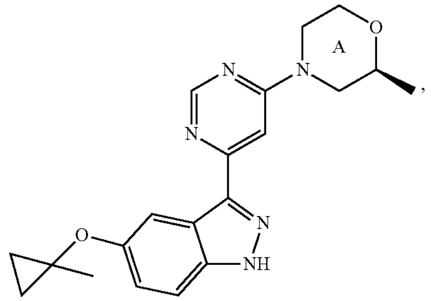
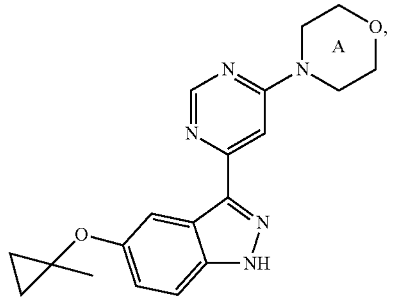
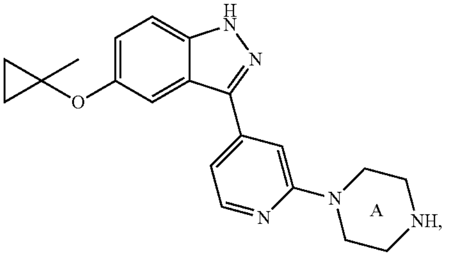
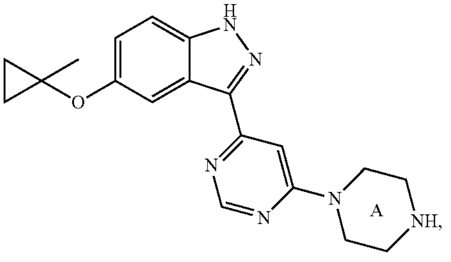
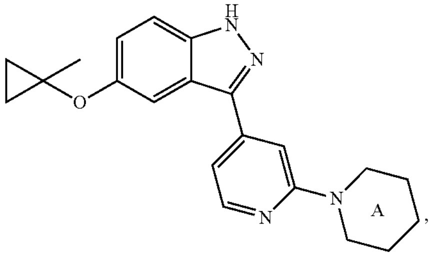
-continued
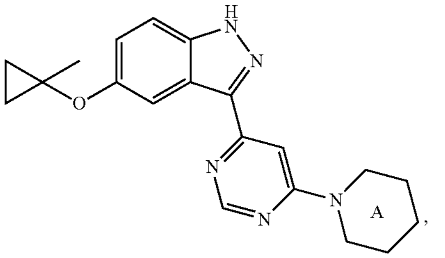
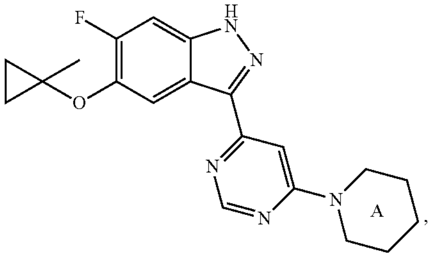
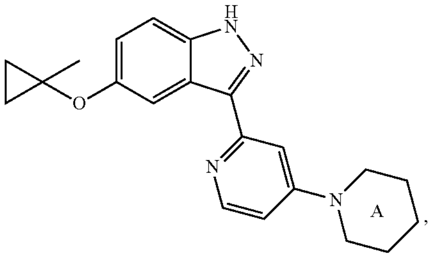
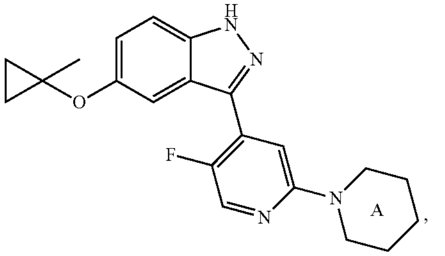
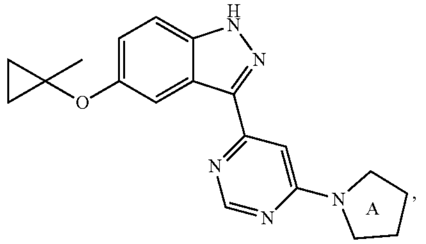
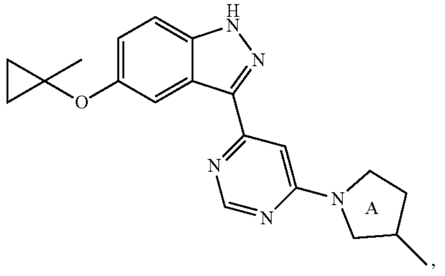

-continued
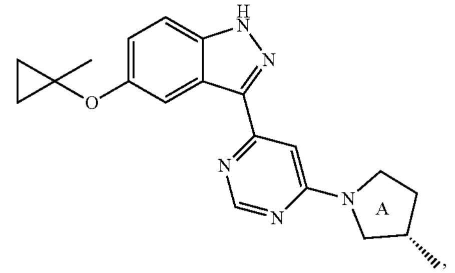
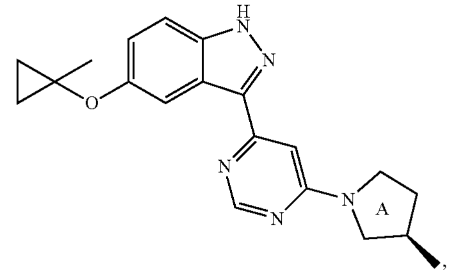
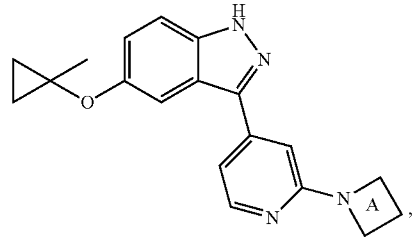
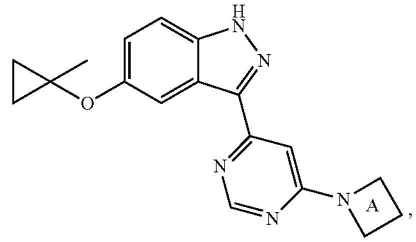
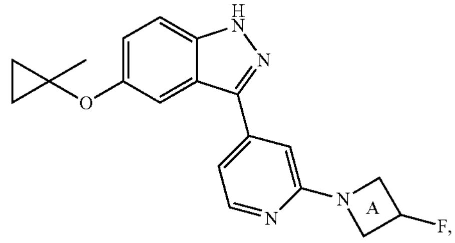
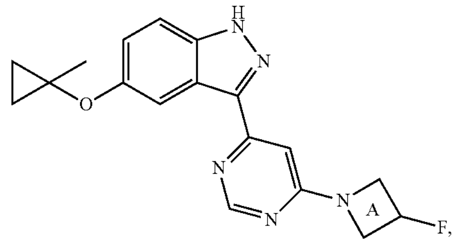
-continued
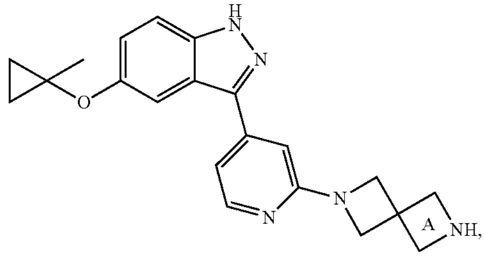
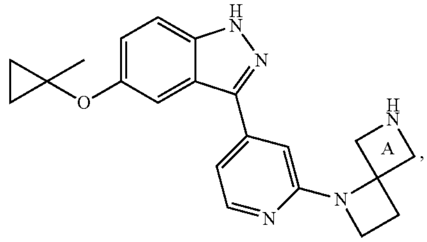
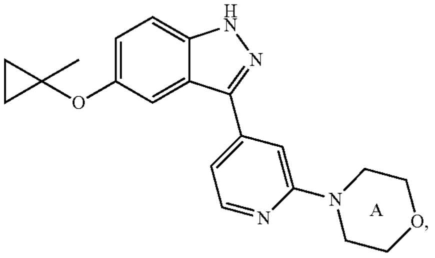
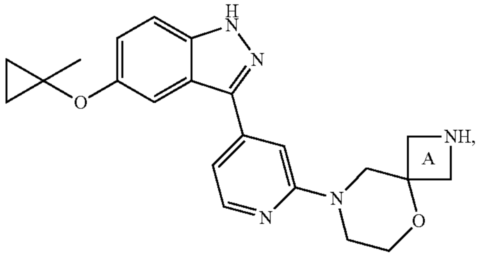
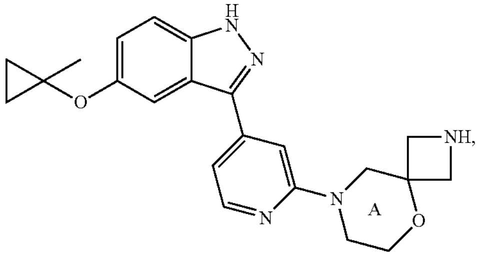
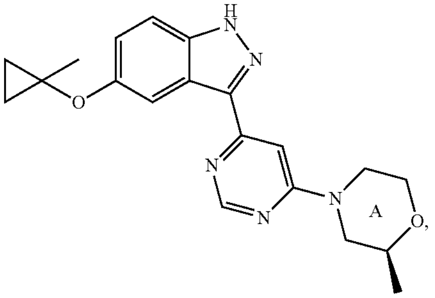

-continued
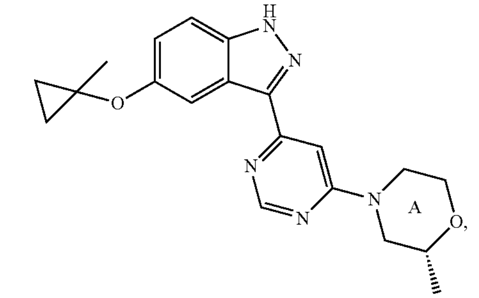
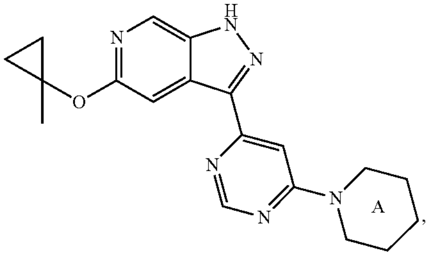
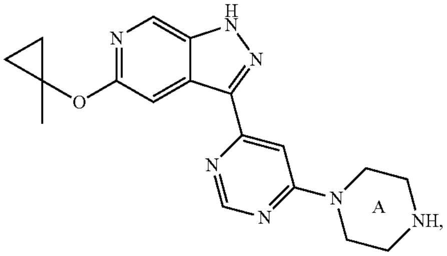
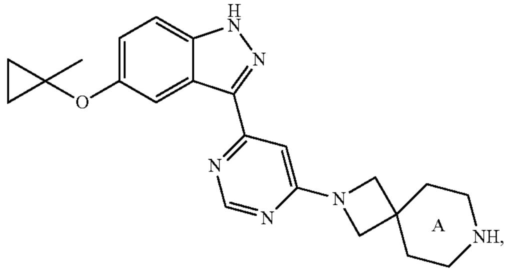
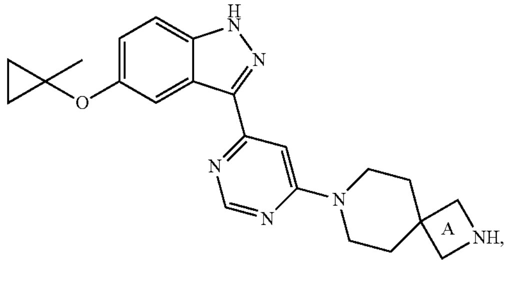
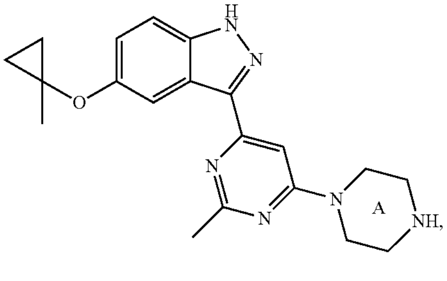
-continued
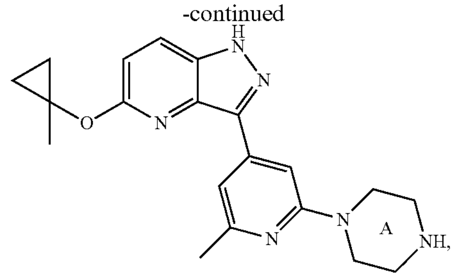
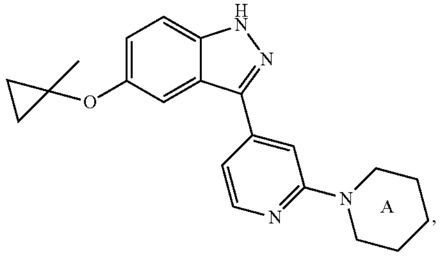
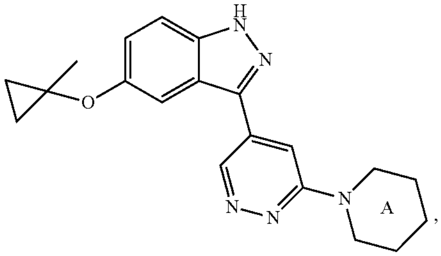
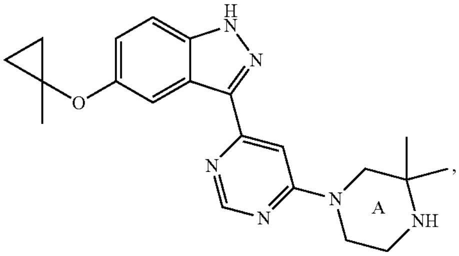
or
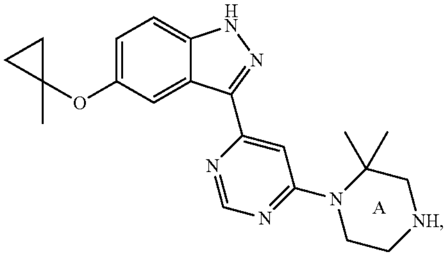
wherein the PTM is covalently linked to the L via an atom of heterocyloalkyl A or a substituent thereof;
(c) the L is a linker group (L) selected from:
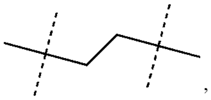
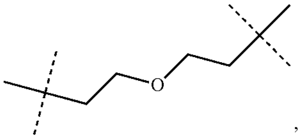
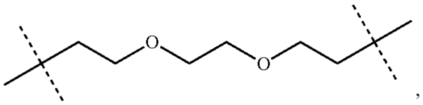

-continued
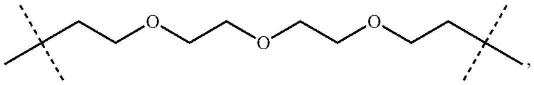
,
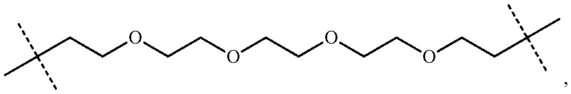
,
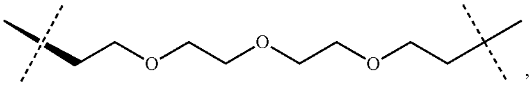
,
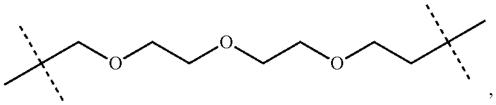
,
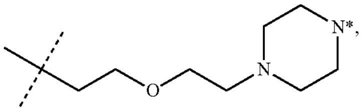
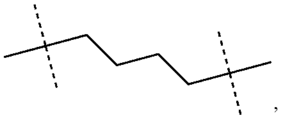
,
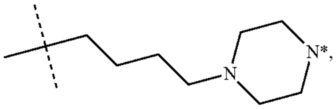
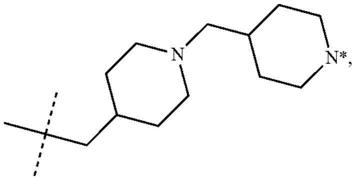
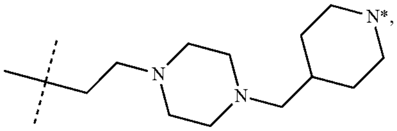
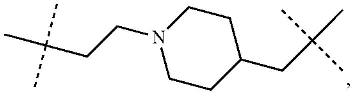
,
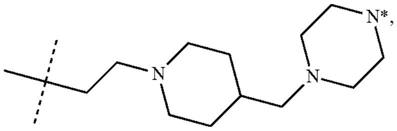
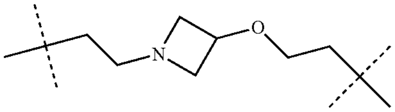
,
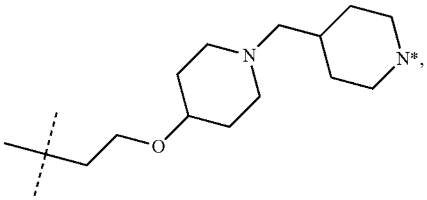
-continued
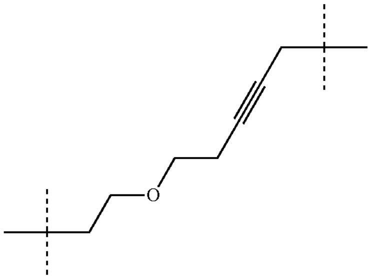
,
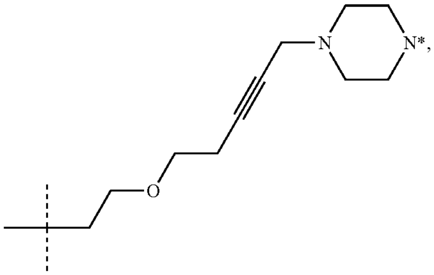
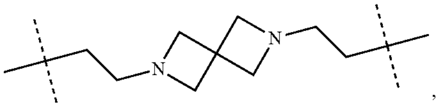
,
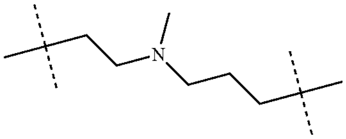
,
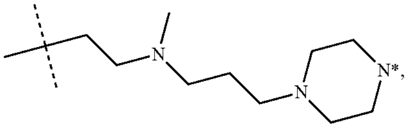
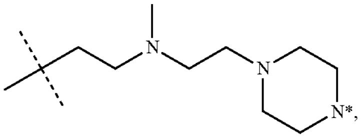
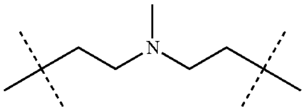
,
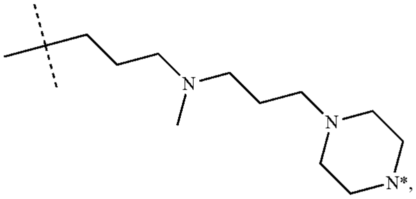
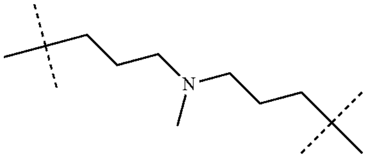
,
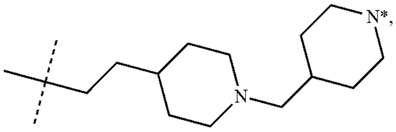

-continued
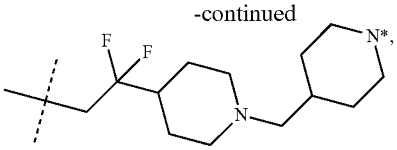
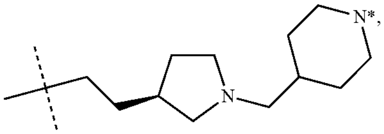
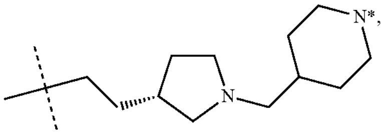
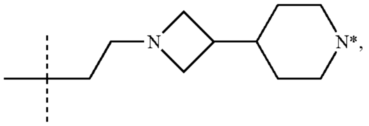
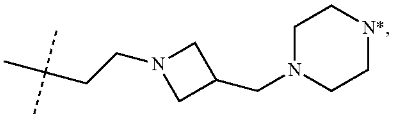
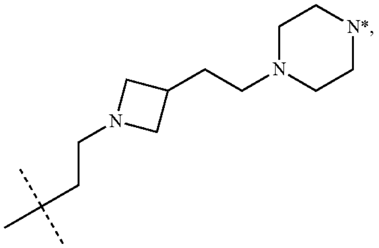
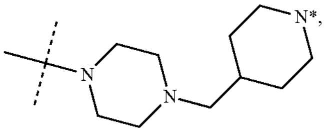
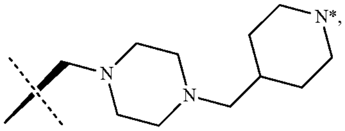
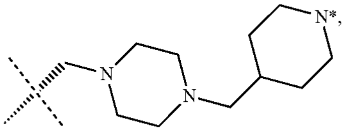
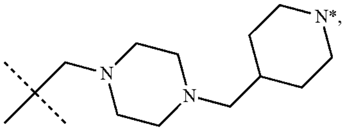
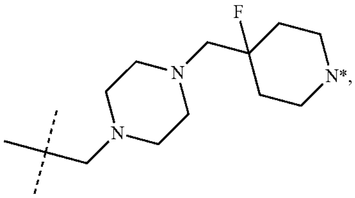
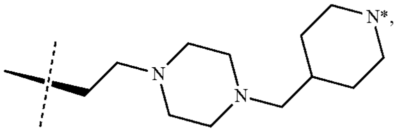
-continued
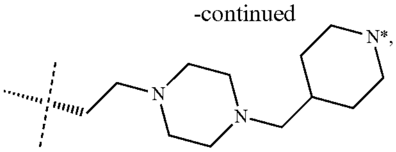
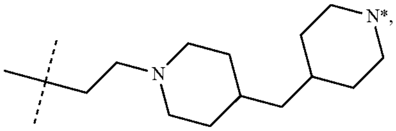
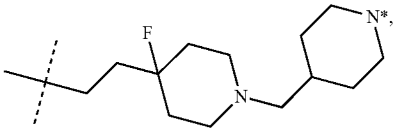
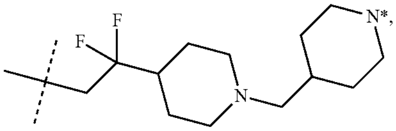
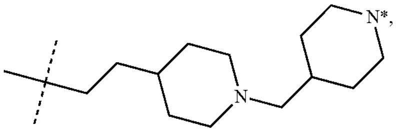
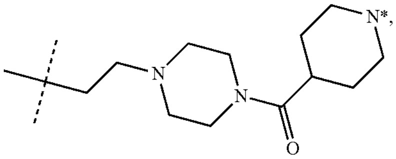
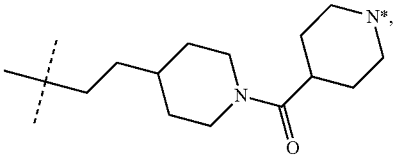
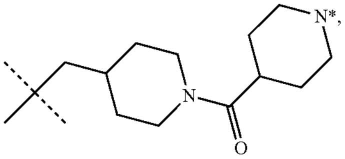
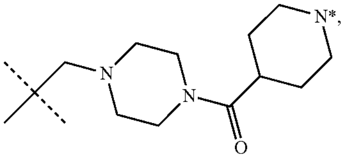
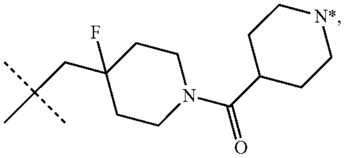
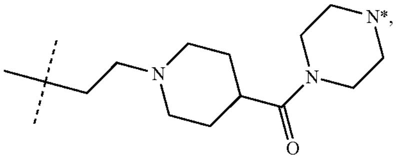
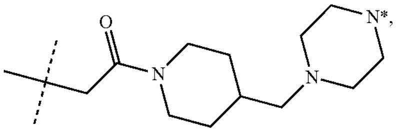

-continued
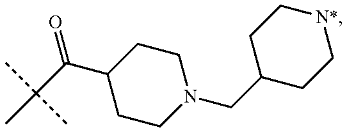
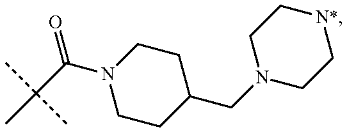
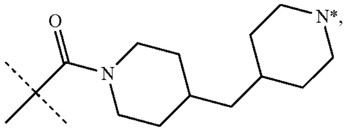
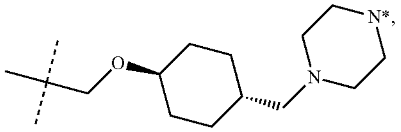
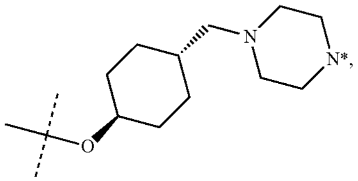
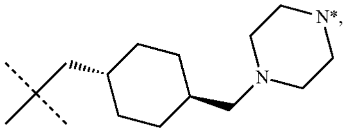
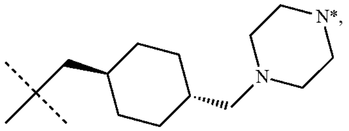
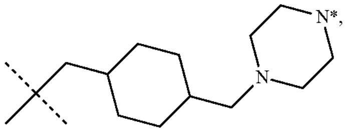
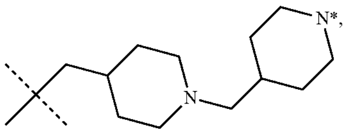
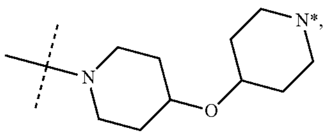
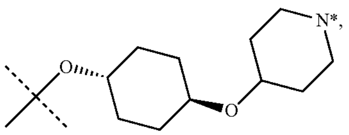
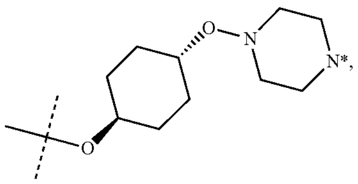
-continued
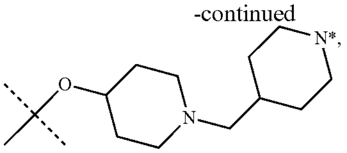
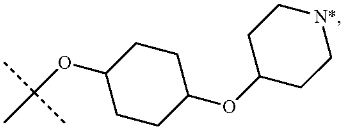
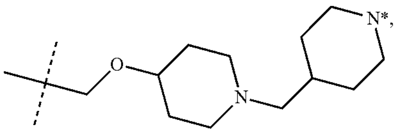
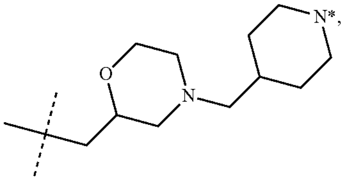
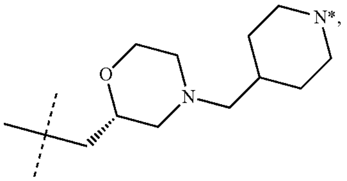
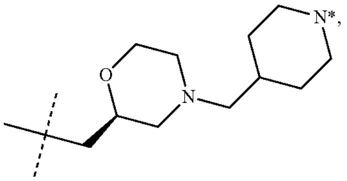
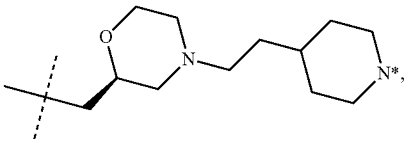
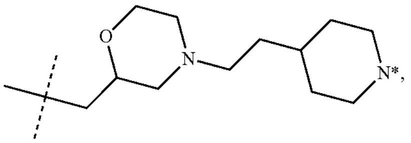
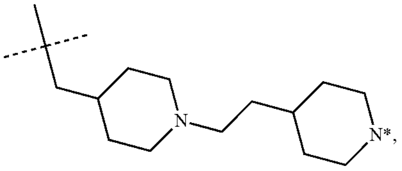
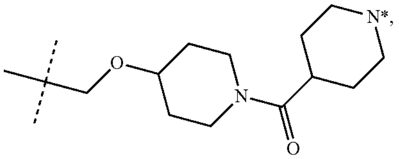
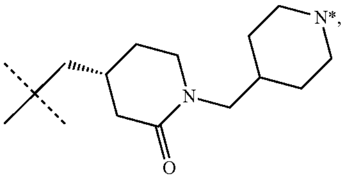

-continued
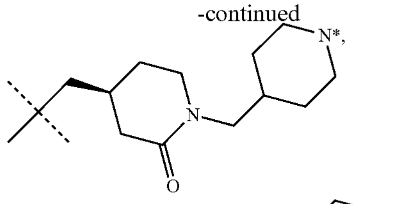
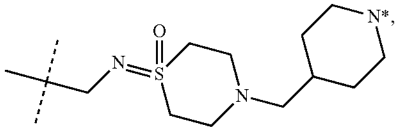
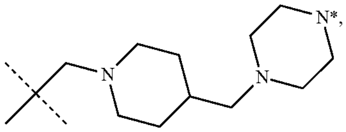
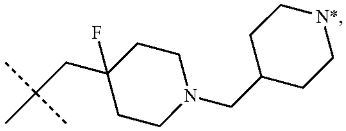
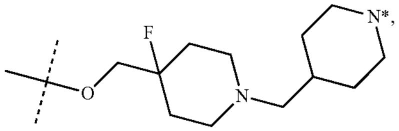
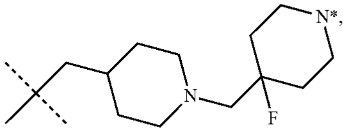
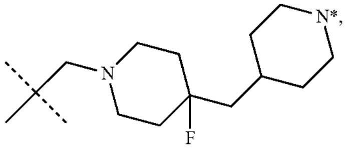
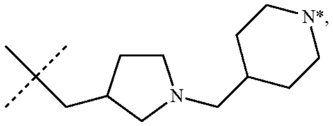
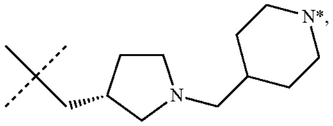
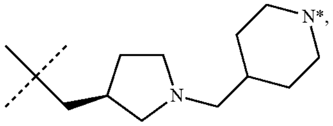
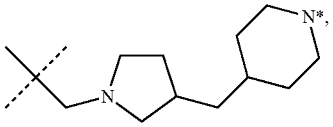
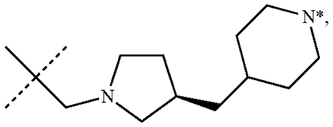
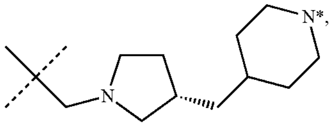
-continued
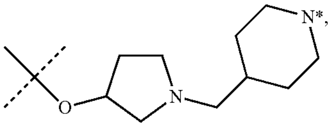
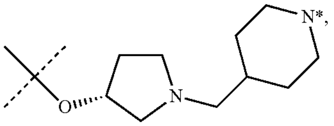
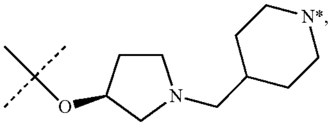
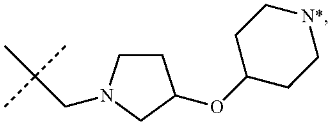
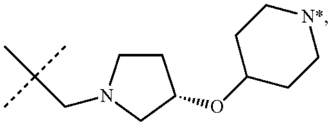
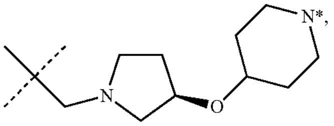
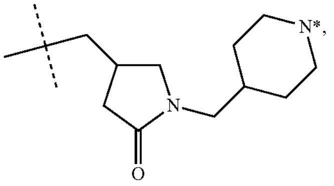
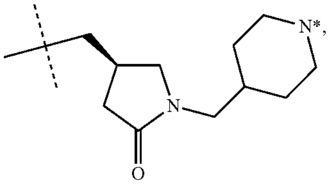
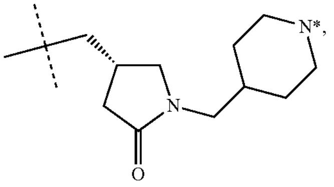
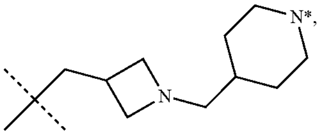
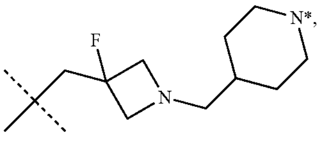

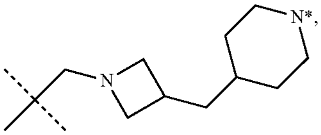
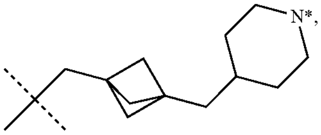
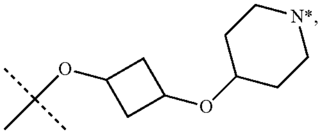
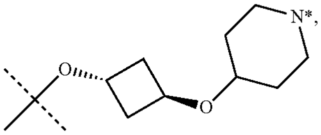
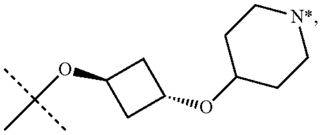
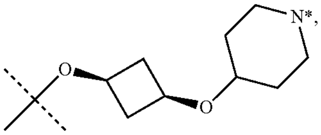
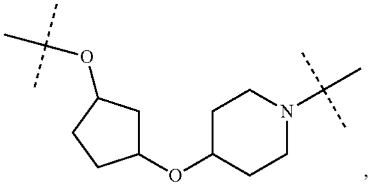
,
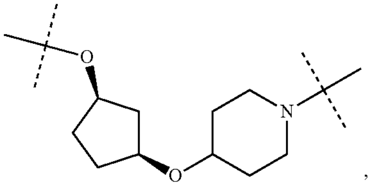
,
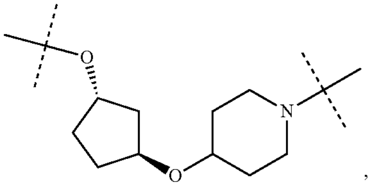
,
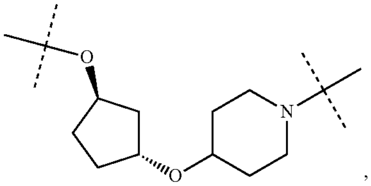
,
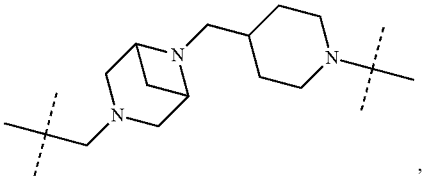
,
-continued
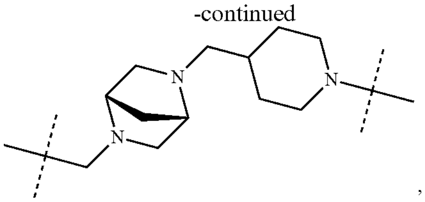
,
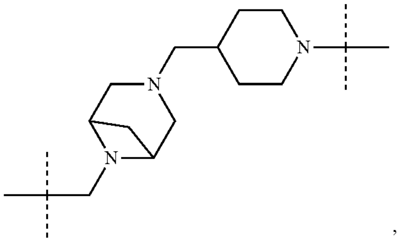
,
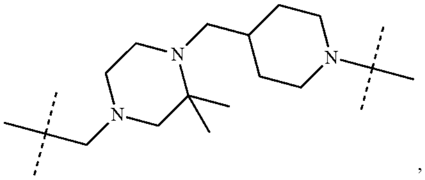
,
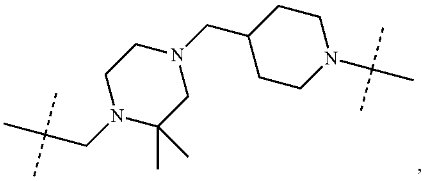
,
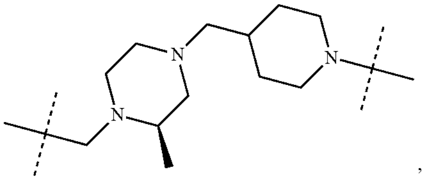
,
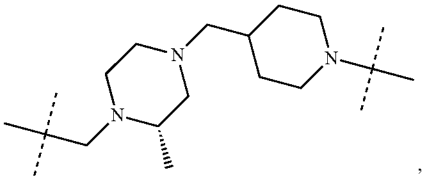
,
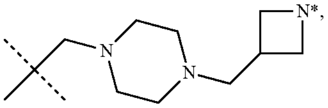
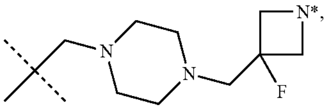
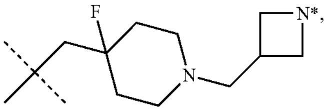
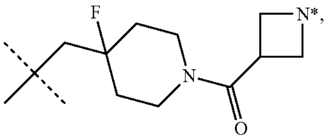
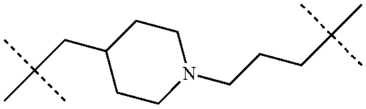
, -continued
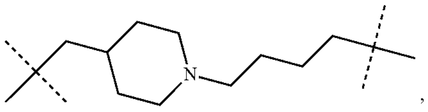
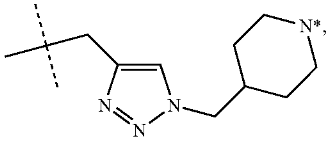
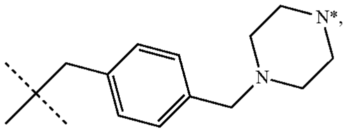
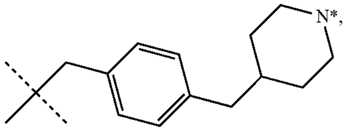
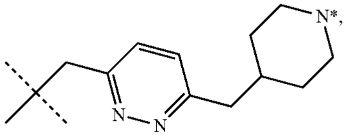
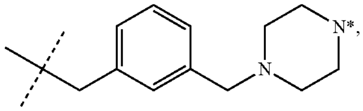
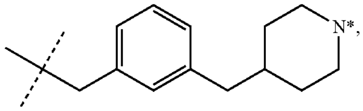
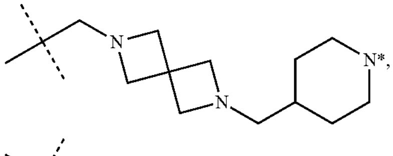
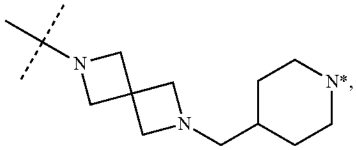
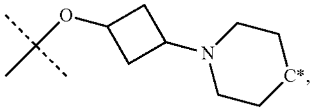
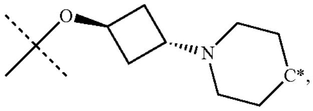
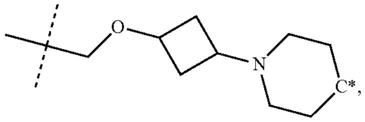
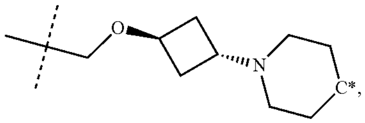
-continued
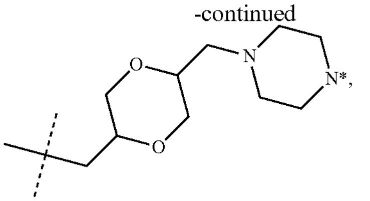
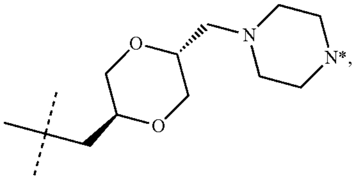
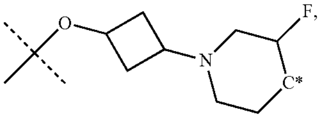
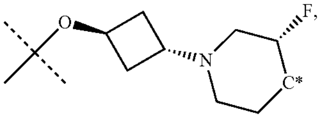
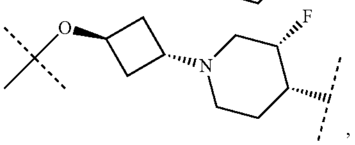
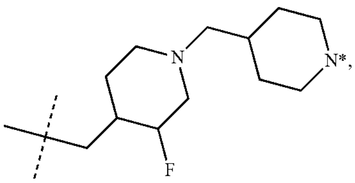
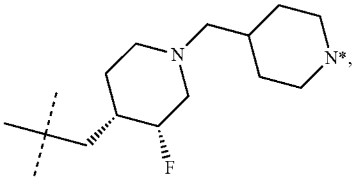
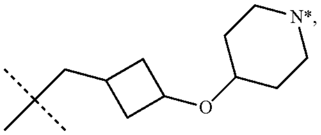
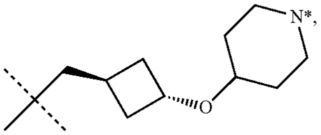
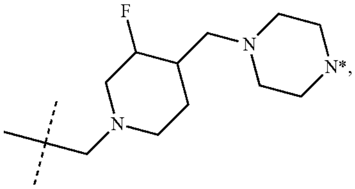
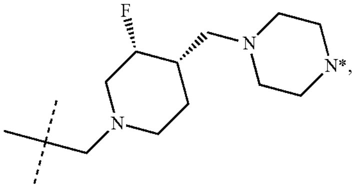

-continued
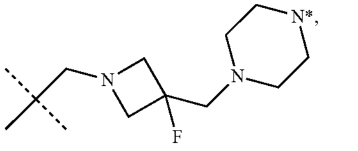
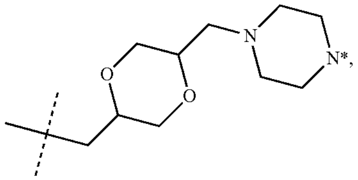
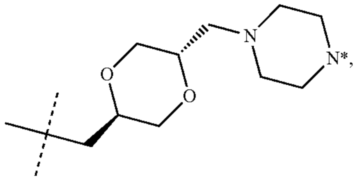
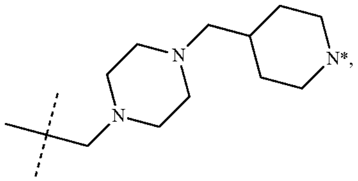
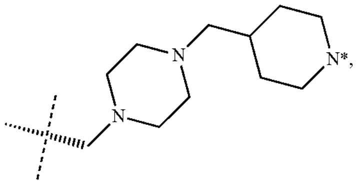
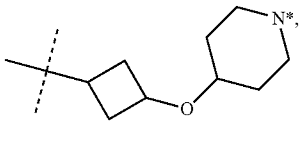
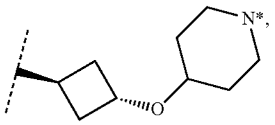
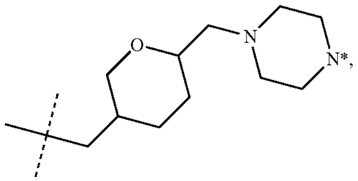
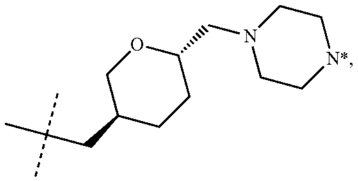
-continued
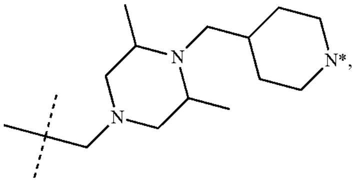
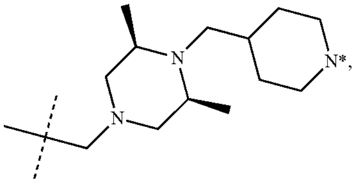
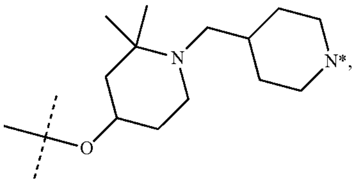
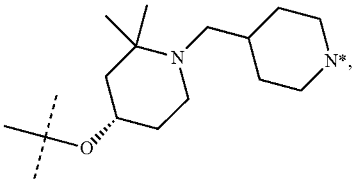
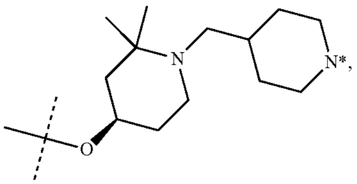
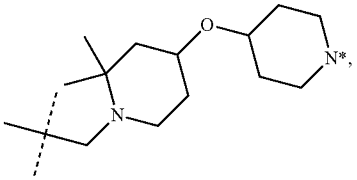
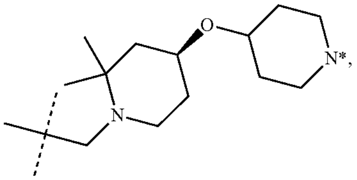
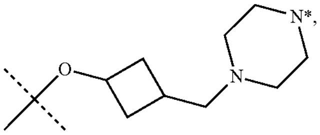
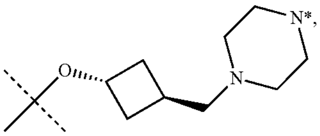
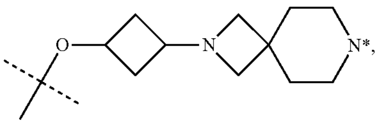

-continued
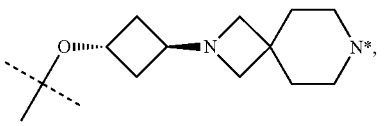
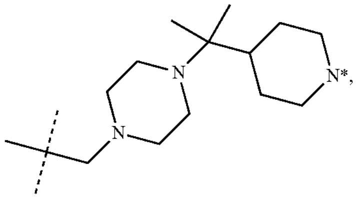
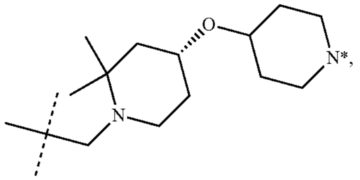
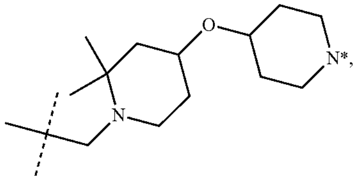
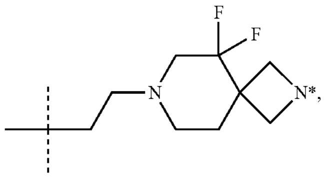
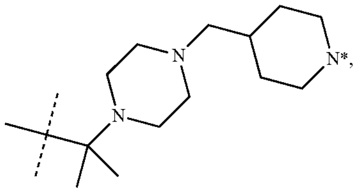
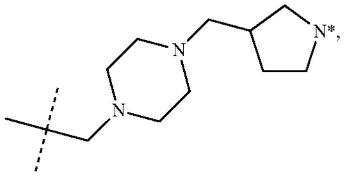
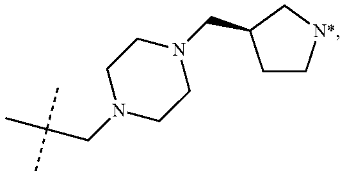
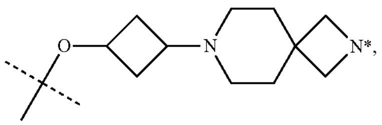
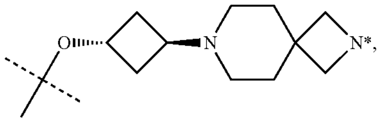
-continued
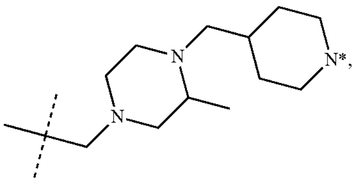
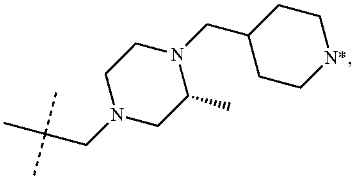
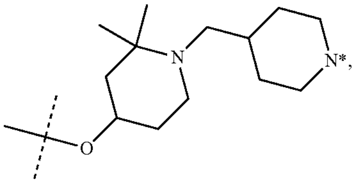
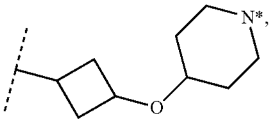
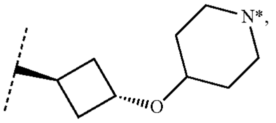
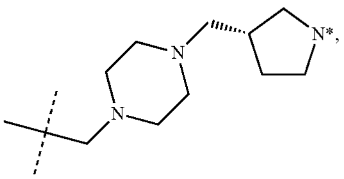
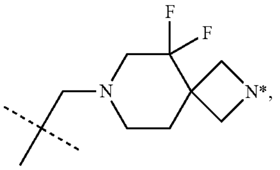
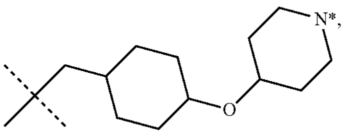
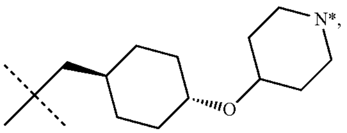
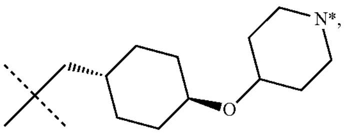
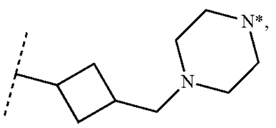

-continued
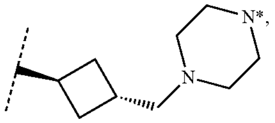
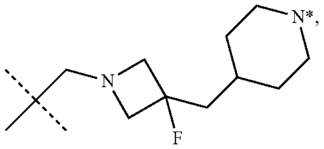
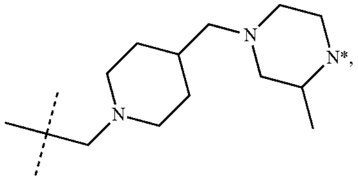
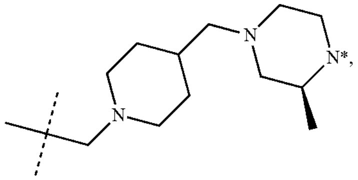
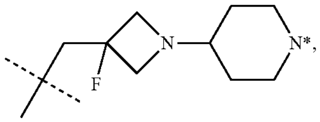
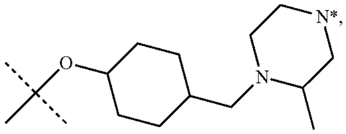
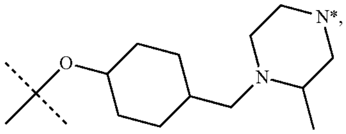
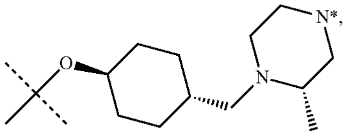
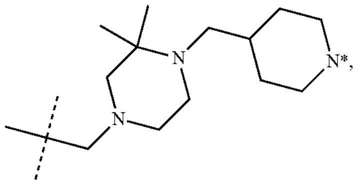
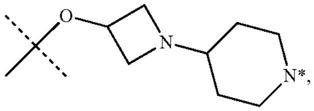
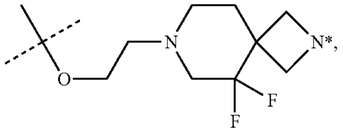
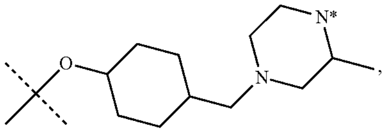
-continued
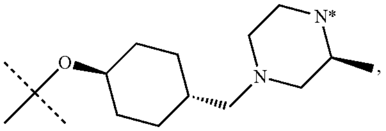
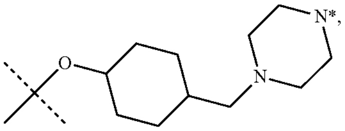
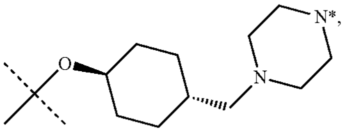
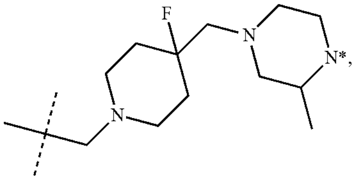
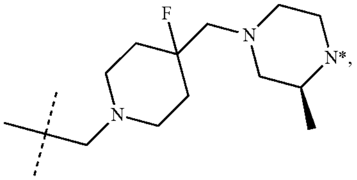
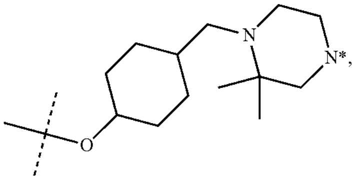
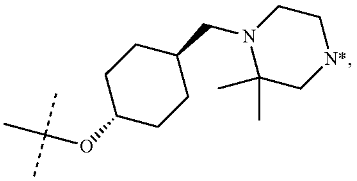
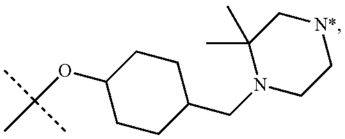
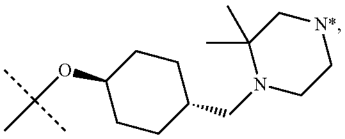
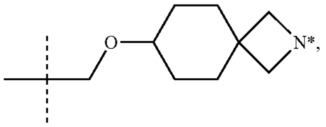
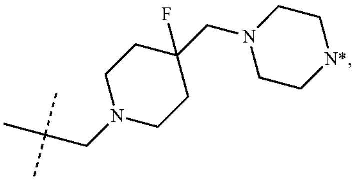

-continued

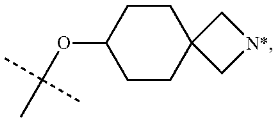

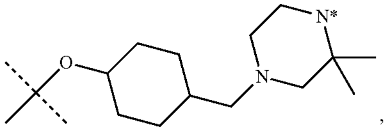

, and

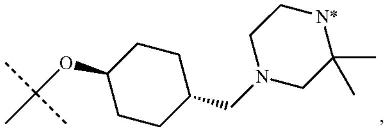

, wherein:

N* is a nitrogen atom that is covalently linked to or shared with the CLM or the PTM;

C* is a carbon atom that is covalently linked to or shared with the CLM or the PTM; and

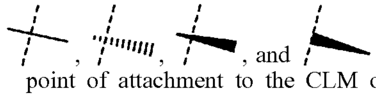 represented the point of attachment to the CLM or the PTM; or

(d) a combination thereof.

In any aspect or embodiment described herein, one or more of: the PTM is a PTM selected from a compound of Table 1, the CLM is a CLM selected from a compound of Table 1, and the L is an L selected from a compound of Table 1.

In any aspect or embodiment described herein, one or more of: the PTM is a PTM selected from compound 52-288, the CLM is a CLM selected from compound 52-288, and the L is an L selected from compound 52-288.

In any aspect or embodiment described herein, the compound is represented by the chemical structure: the compound is represented by the chemical structure:

(Formula IIIa)

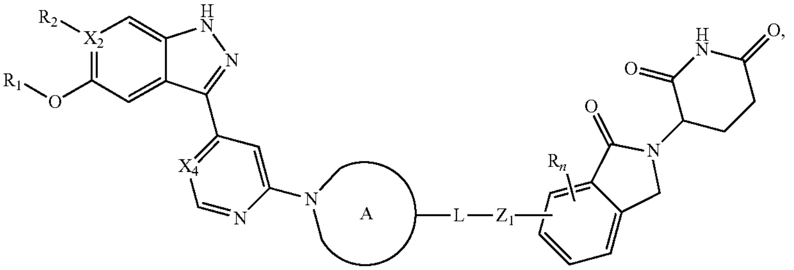

or (Formula IIIb)

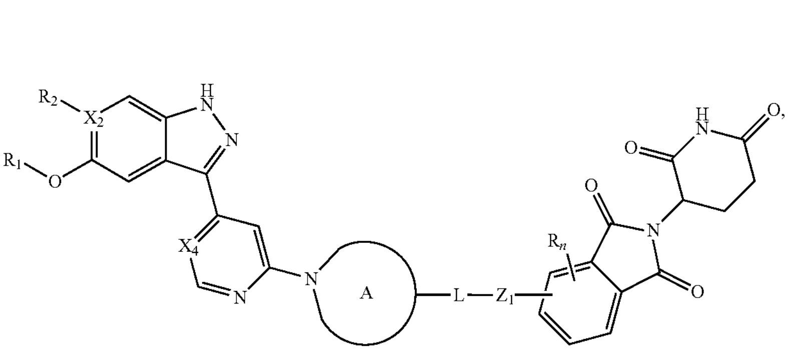

wherein:

n is 0 or 1;

R is H, OH, —Cl, —F, or Br;

$Z_1$ is a nitrogen or carbon shared with a cyclic group of L;

$X_2$ is C or N;

$X_4$ is CH or N (preferably N);

$R_1$ is

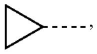 or 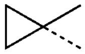 (preferably 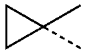), wherein is the point of attachment to the oxygen of the PTM;

$R_2$ is a H, —Cl, or —F;

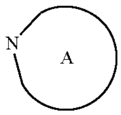

is

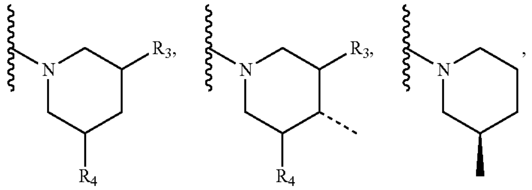

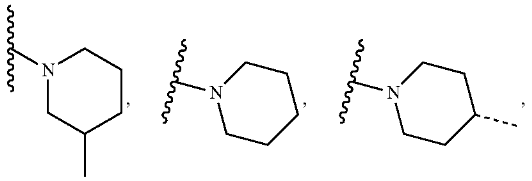

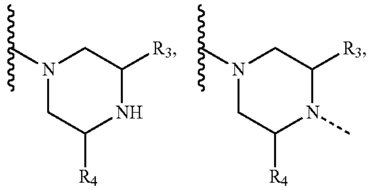

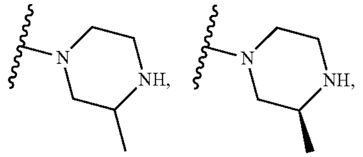

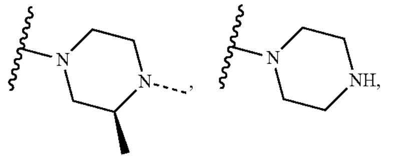 or

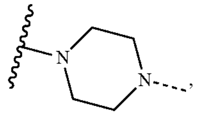, (preferably,

-continued

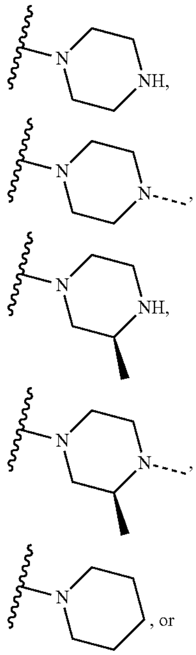, or

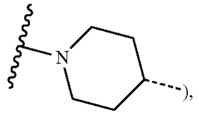), wherein:

$R_3$ is H, methyl, or ethyl;

$R_4$ is H, methyl, or ethyl;

indicates the point of attachment of the

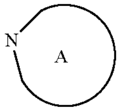

to the PTM; and indicates the point of attachment of the PTM with the L or the CLM, and when is not present, the

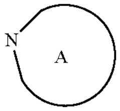

may be attached to the L via an atom of the cyclic group (e.g., a carbon or nitrogen);

L is represented by the chemical structure:

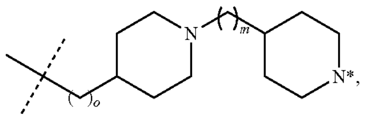

-continued

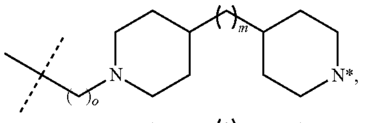
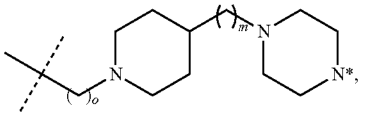
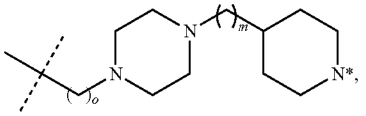
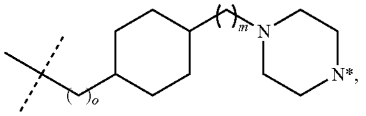
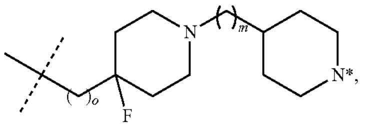
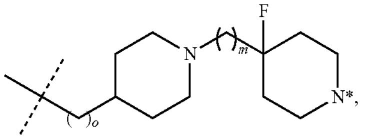
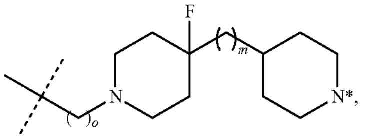
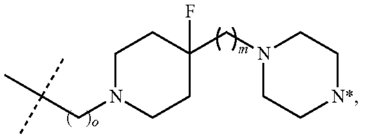
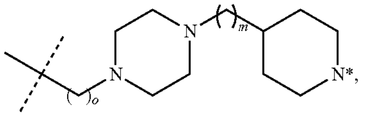
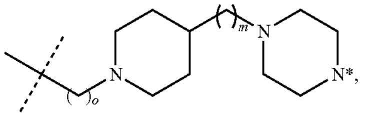
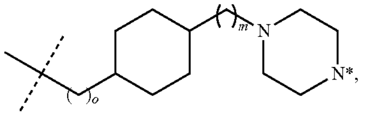

wherein:

m and n are integers independently selected from 0, 1, 2, or 3 (preferably 1); and the L is optionally substituted with 0, 1, 2, or 3 (preferably 0 or 1) groups selected from: —Cl, —F, and $C_{1-3}$ alkyl (e.g., methyl or ethyl).

In any aspect or embodiment described herein, one or more of:

G is H or unsubstituted or substituted linear or branched $C_{1-6}$ alkyl;

A is H or unsubstituted or substituted linear or branched $C_{1-6}$ alkyl;

R is a bond, H, O, —CONR'R", —C(═O)R', —OR', —NR'R", unsubstituted or substituted linear or branched $C_{1-6}$ alkyl optionally substituted $C_{1-6}$ alkoxyl group, —Cl, —F, —Br, —$CF_3$, or —CN, wherein one R is covalently joined to the L;

R' and R" are independently selected from a bond, H, and optionally $C_{1-6}$ substituted alkyl; and

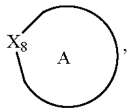, 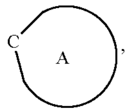, or 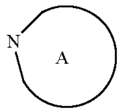

is an optionally substituted 3-10 membered cycloalkyl, optionally substituted 3-10 membered heterocyloalkyl containing 1 to 4 (e.g., 1, 2, 3, or 4) heteroatoms, optionally substituted 3-10 membered bicycloalkyl, optionally substituted 3-10 membered biheterocycloalkyl containing 1 to 4 (e.g., 1, 2, 3, or 4) heteroatoms, optionally substituted 3-10 membered spirocycloalkyl, or optionally substituted 3-10 membered spiroheterocycloalkyl containing 1 to 4 (e.g., 1, 2, 3, or 4) heteroatoms, wherein the heteroatoms are independently selected from N, O, and S.

A further aspect of the present disclosure relates to a composition comprising an effective amount of a bifunctional compound of the present disclosure and a pharmaceutically acceptable carrier.

In any aspect or embodiment described herein, the composition further comprises additional bioactive agent.

In any aspect or embodiment described herein, the additional bioactive agent is an anti-inflammatory, a chemotherapy agent, or an immunomodulatory agent.

Another aspect of the present disclosure relates to a composition comprising a pharmaceutically acceptable carrier and an effective amount of at least one compound of the present disclosure for treating a disease, a disorder or a symptom causally related to LRRK2 in a subject, wherein the composition is effective in treating or ameliorating the disease, disorder, or at least one symptom of the disease or disorder.

An aspect of the present disclosure relates to a method for treating a disease, disorder, or a symptom causally related to LRRK2, wherein the method comprising administering a composition comprising a pharmaceutically acceptable carrier and an effective amount of at least one compound of the present disclosure to a subject in need thereof, wherein the composition is effective in treating or ameliorating the disease, disorder, or at least one symptom of the disease or disorder. In any aspect or embodiment described herein.

An additional aspect of the present disclosure relates to a method of treating or preventing a disease, a disorder, or symptom associated with LRRK2 comprising, providing a patient in need thereof, and administering an effective amount of a compound as described herein or composition comprising the same to the patient, wherein the compound or composition is effective in treating or ameliorating the disease, disorder, or at least one symptom of the disease or disorder.

In any aspect or embodiment described herein, the disease or disorder is idiopathic Parkinson's disease (PD), LRRK2 mutation associated PD, primary tauopathies, lewy body dementia, Crohn's Disease, Leprosy, neuroinflammation, Progressive Supranuclear Palsy, Picks disease, FTDtau, TDP-43 Frontal Temporal Dementia, TDP-43 ALS, c9orf ALS, Huntington's disease, spinocerebellar ataxias (SCAs)

1, 2, 3, 6, 7 and 17, dentatorubral pallidoluysian atrophy (DRPLA) or Kennedy's disease.

The term "alkyl" shall mean within its context a linear, branch-chained or cyclic fully saturated hydrocarbon radical, preferably a $C_1$-$C_{10}$, preferably a $C_1$-$C_6$, or more preferably a $C_1$-$C_3$ alkyl group, which may be optionally substituted with any suitable functional group or groups. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, C1, F, or I).

The term "alkenyl" refers to linear, branch-chained or cyclic $C_2$-$C_{10}$ (preferably $C_2$-$C_6$) hydrocarbon radicals containing at least one C═C bond.

The term "alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a $—(CH_2)_n—$ group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other suitable functional group) which may be further substituted with a polyethylene glycol chain (of from 1 to 10, preferably 1 to 6, or more preferably 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (e.g., methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than one substituent occurs, each substituent is selected independent of another substituent) one or more substituents (independently up to five substituents, preferably up to three substituents, more preferably 1 or 2 substituents on a moiety in a compound according to the present disclosure and may include substituents which themselves may be further substituted) at a carbon (or nitrogen) position anywhere on a molecule within context, and includes as possible substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, C1-$C_6$), aryl (especially phenyl and substituted phenyl, for example benzyl or benzoyl), alkoxy group (preferably, $C_1$-$C_6$ alkyl or aryl, including phenyl and substituted phenyl), thioether (preferably, $C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), halogen (preferably, F or C1), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which are preferably independently substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example $—SiR_1R^2R_3$ groups where each of $R_1$ and $R_2$ is as otherwise described herein and $R_3$ is H or a $C_1$-$C_6$ alkyl group, preferably $R_1$, $R_2$, $R_3$ together is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted $—(CH_2)_m—$ or alternatively an optionally substituted $—(OCH_2)_m—$, $—(OCH_2CH_2)_m—$ or $—(CH_2CH_2O)_m—$ group, which may be substituted with any one or more of the above-described substituents. Alkylene groups $—(CH_2)_m—$ or $—(CH_2)_n—$ groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (0-$C_1$-$C_6$ groups), up to three halo groups (preferably F), or a side chain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane $—O—C(O)—NR_1R_2$ or $—N(R_1)—C(O)—O—R_1$, nitro, cyano and amine (especially including a $C_1$-$C_6$ alkylene-$NR_1R^2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, ═O, $—(CH_2)_m$ (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R^2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R^2$, —$S(O)_2$—$R_S$, —S(O)—$R_S$($R_S$ is $C_1$-$C_6$ alkyl or a —$(CH_2)_m$—$NR_1R_2$ group), $NO_2$, CN or halogen (F, Cl, Br, I, preferably F or $C_1$), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical (e.g., a 5-16 membered ring) having a single ring (e.g., benzene, phenyl, benzyl, or 5, 6, 7 or 8 membered ring) or condensed rings (e.g., naphthyl, anthracenyl, phenanthrenyl, 10-16 membered ring, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methyl substituted isoxazole, an optionally substituted oxazole including a methyl substituted oxazole, an optionally substituted thiazole including a methyl substituted thiazole, an optionally substituted isothiazole including a methyl substituted isothiazole, an optionally substituted pyrrole including a methyl substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methyl substituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to a 5-16 membered heteroaryl (e.g., 5, 6, 7 or 8 membered monocylic ring or a 10-16 membered heteroaryl having multiple condensed rings), an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

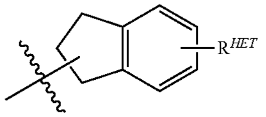

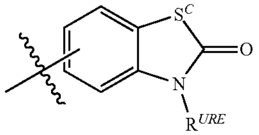

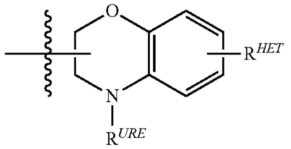

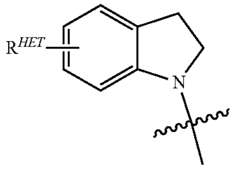

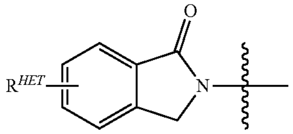

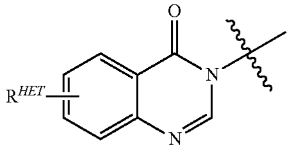

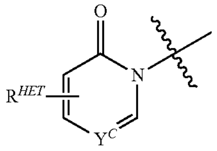

wherein:

$S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or $C_1$), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{Y}$c, where $R^{Y}$c is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylaikyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO— substituted alkyl, —SOaryl, —SO-heteroaryl, —SO2-alkyl, —SO2-substituted alkyl, —SO2-aryl, oxo (═O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

Exemplary CLMs

Neo-Imide Compounds

In one aspect the description provides CLMs useful for binding and recruiting cereblon. In certain embodiments, the CLM is selected from the group consisting of chemical structures:

(a1)

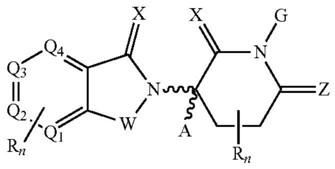

(b)

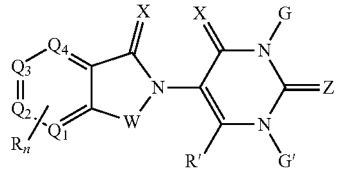

(c)

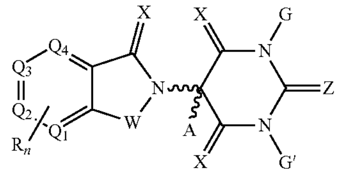

(d1)

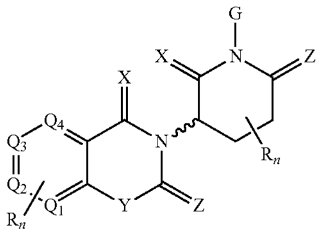

(e)

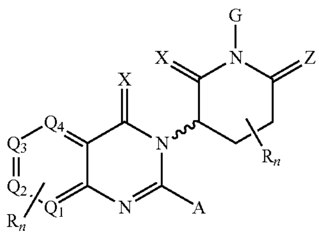

(a2)

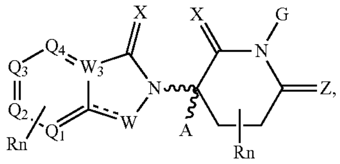

(d2)

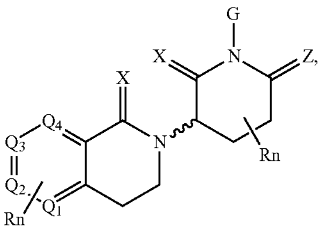

(a3)

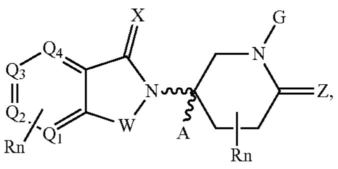

and

-continued (a4)

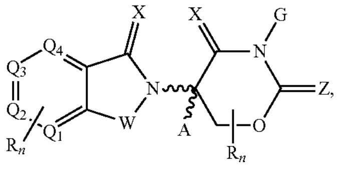

wherein:

W of Formulas (a1) through (e) [e.g., (a1), (a2), (a3), (a4), (b), (c), (d1), (d2), and (e)] is independently selected from the group $CH_2$, O, CHR, C═O, $SO_2$, NH, N, optionally substituted cyclopropyl group, optionally substituted cyclobutyl group, and N-alkyl;

$W_3$ of Formulas (a1) through (e) is C or N;

each X of Formulas (a1) through (e) is independently selected from the group absent, O, S, and $CH_2$;

Y of Formulas (a1) through (e) is selected from the group $CH_2$, —C═CR', NH, N-alkyl, N-aryl, N-heteroaryl, N-cycloalkyl, N-heterocyclyl, O, and S;

each Z of Formulas (a1) through (e) is independently selected from the group absent, O, S, and $CH_2$ except that both X and Z cannot be $CH_2$ or absent;

G and G' of Formulas (a1) through (e) are independently selected from the group H, optionally substituted linear or branched alkyl, OH, R'OCOOR, R'OCONRR", $CH_2$-heterocyclyl optionally substituted with R', and benzyl optionally substituted with R';

Each of $Q_1$-$Q_4$ of Formulas (a1) through (e) independently represent a N, CH, or CR;

A of Formulas (a1) through (e) is selected from the group H, optionally substituted linear or branched alkyl, cycloalkyl, $C_1$ and F;

n of Formulas (a1) through (e) represent an integer from 1 to 10 (e.g., 1-4, 1, 2, 3, 4, 5, 6, 7, 8, 9, or 10);

each R of Formulas (a1) through (e) independently comprises, but is not limited to: a bond, H, —C(═O)R' (e.g., a carboxy group), —CONR'R" (e.g., an amide group), —OR' (e.g., OH), —NR'R" (e.g., an amine group), —SR', —$SO_2$R', —$SO_2$NR'R", —CR'R"—, —CR'NR'R"—, (—CR'O)$_n$R", optionally substituted heterocyclyl, optionally substituted aryl, (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted heteroaryl, optionally substituted alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$ and —$OCF_3$, wherein at least one W, X, Y, Z, G, G', R, R', R", $Q_1$-$Q_4$, or A is modified to be covalently joined to a PTM, a chemical linking group (L), a ULM, CLM, or combination thereof;

each of x, y, and z of Formulas (a1) through (e) is independently 0, 1, 2, 3, 4, 5, or 6;

each R' and R" of Formulas (a1) through (e) is independently selected from a bond, H, optionally substituted linear or branched alkyl, optionally substituted cycloalkyl, optionally substituted aryl, optionally substituted heteroaryl, optionally substituted heterocyclic, —C(═O)A, and optionally substituted heterocyclyl;

n' of Formulas (a1) through (e) is an integer from 1 to 10 (e.g. 1-4, 1, 2, 3, 4, 5, 6, 7, 8, 9, or 10);

 represents a single bond or a double bond; and of Formulas (a1) through (e) represents a bond that may be stereospecific ((R) or (S)) or non-stereospecific.

In any aspect or embodiment described herein, the CLM comprises a chemical structure selected from the group consisting of:

(a1)

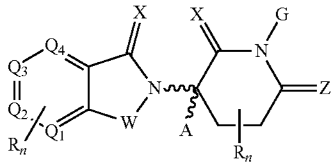

(b)

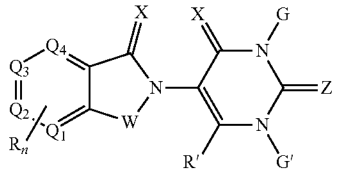

(c)

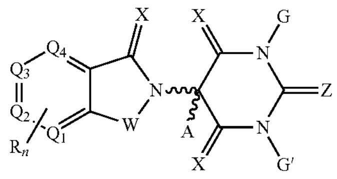

(d1)

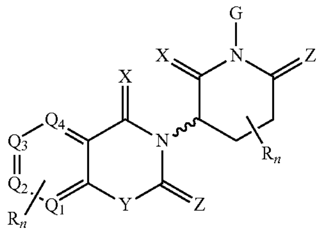

(e)

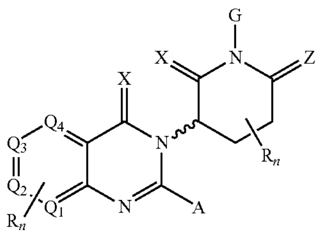

-continued (a2)

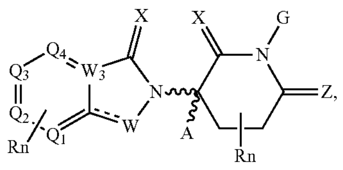

(d2)

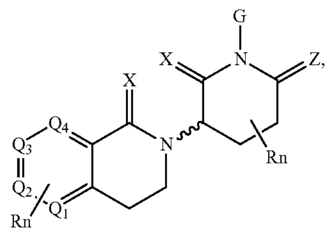

(a3)

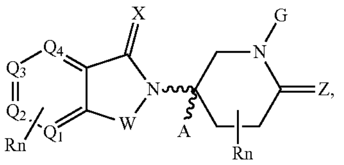

and (a4)

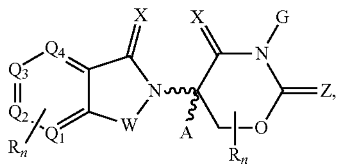

wherein:

W of Formulas (a1) through (e) [e.g., (a1), (a2), (a3), (a4), (b), (c), (d1), (d2), and (e)] is selected from the group $CH_2$, O, CHR, C═O, $SO_2$, NH, N, optionally substituted cyclopropyl group, optionally substituted cyclobutyl group, and N-alkyl;

$W_3$ of Formulas (a1) through (e) is selected from C or N;

each X of Formulas (a1) through (e) is independently selected from the group O, S and $CH_2$;

Y of Formulas (a1) through (e) is selected from the group $CH_2$, —C═CR', NH, N-alkyl, N-aryl, N-hetaryl, N-cycloalkyl, N-heterocyclyl, O, and S;

each Z of Formulas (a1) through (e) is independently selected from the group O, S, and $CH_2$, except that both X and Z cannot be $CH_2$ or absent;

G and G' of Formulas (a1) through (e) are independently selected from the group H, optionally substituted linear or branched alkyl, OH, R'OCOOR, R'OCONRR", $CH_2$-heterocyclyl optionally substituted with R', and benzyl optionally substituted with R';

each of $Q_1$-$Q_4$ of Formulas (a1) through (e) independently represent a N, CH, or CR;

A of Formulas (a1) through (e) is selected from the group H, optionally substituted linear or branched alkyl, cycloalkyl, C1, and F;

n of Formulas (a1) through (e) represent an integer from 1 to 10 (e.g., 1-4, 1, 2, 3, 4, 5, 6, 7, 8, 9, or 10);

each R of Formulas (a1) through (e) independently comprises, but is not limited to: a bond, H, —C(═O)R' (e.g., a carboxy group), —CONR'R" (e.g., an amide group), —OR' (e.g., OH), —NR'R" (e.g. an amine group), —SR', —$SO_2$R', —$SO_2$NR'R", —CR'R"—, —CR'NR'R"—, $(—CR'O)_n$R", optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted hetaryl, -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(═N—CN)NR'R", —C(═N—CN)NR'R", —NR'C(═N—CN)R", —NR'C(═C—$NO_2$)NR'R", —$SO_2$NR'COR", —$NO_2$, —$CO_2$R', —C(C═N—OR')R", —CR'═CR'R", —CCR', —S(C═O)(C═N—R')R", —$SF_5$, and —$OCF_3$, wherein at least one of W, X, Y, Z, G, G', R, R', R", $Q_1$-$Q_4$, or A is covalently joined (directly or indirectly, e.g., via a functional group or an atom, such as O, S, N) to a PTM, a chemical linking group (L), a ULM, CLM, or combination thereof;

each of x, y, and z of Formulas (a1) through (e) are independently 0, 1, 2, 3, 4, 5, or 6;

each R' and R" of Formulas (a1) through (e) is independently selected from a bond, H, optionally substituted linear or branched alkyl, optionally substituted cycloalkyl, optionally substituted aryl, optionally substituted heteroaryl, optionally substituted heterocyclic, —C(═O)A, and optionally substituted heterocyclyl;

n' of Formulas (a1) through (e) is an integer from 1-10 (e.g., 1-4, 1, 2, 3, 4, 5, 6, 7, 8, 9, or 10); and ∿∿∿ of Formulas (a) through (f) represents a bond that may be stereospecific ((R) or (S)) or non-stereospecific.

In any aspect or embodiment described herein, the CLM or ULM is selected from the structure of Formula (g):

Formula (g)

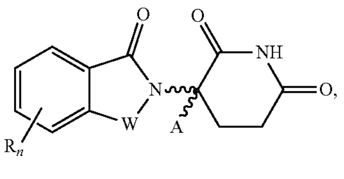

wherein:

W of Formula (g) is selected from the group $CH_2$, O, C═O, NH, and N-alkyl;

A of Formula (g) is a H, methyl, or optionally substituted linear or branched alkyl;

n is an integer from 1 to 4;

each R of Formula (g) is independently selected from a bond, H, O, OH, N, NH, $NH_2$, —Cl, —F, —Br, —I, methyl, optionally substituted linear or branched alkyl (e.g., optionally substituted linear or branched C1-C6 alkyl), optionally substitute linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy), wherein at least one R or W is modified to be covalently joined to a PTM, a chemical linking group (L), a ULM, CLM, or combination thereof; and ∿∿ of Formula (g) represents a bond that may be stereospecific ((R) or (S)) or non-stereospecific.

In any aspect or embodiment described herein, the CLM or ULM is selected from the group consisting of:

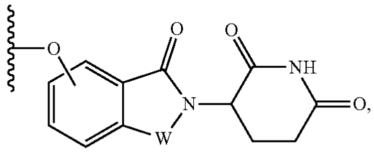
,
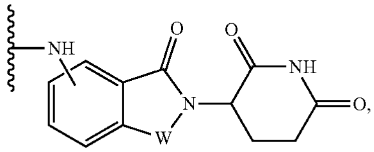
,
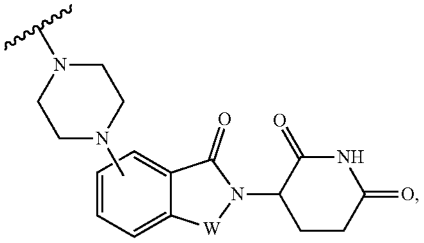
,
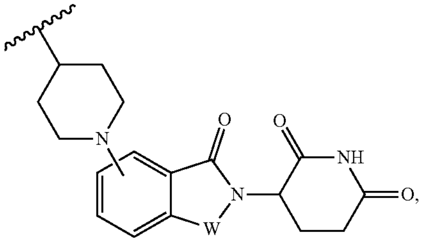
, or
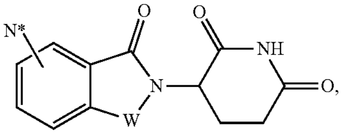
, wherein:

W is C═O or $CH_2$;

N* is a nitrogen atom that is covalently linked to the PTM or linker, or that is shared with the PTM or linker (L) (e.g., a heteroatom shared with an optionally substituted heterocylyl of the linker (L) PTM); and ⌇— indicates the point of attachment of the CLM or ULM to the linker (L) or PTM.

In any aspect or embodiment described herein, each R is independently selected from: H, O, OH, N, NH, $NH_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy).

In any aspect or embodiment described herein, at least one R (e.g. an R group selected from the following H, O, OH, N, NH, $NH_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) or W is modified to be covalently joined to a PTM, a chemical linker group (L), a ULM, a CLM, or a combination thereof.

In any aspect or embodiment described herein, the W, X, Y, Z, G, G', R, R', R'', Q1-Q4, and A of Formulas (a) through (g) can independently be covalently coupled to a linker and/or a linker to which is attached one or more PTM, ULM, or CLM groups.

In any of the aspects or embodiments described herein, n is an integer from 1 to 4, and each R is independently selected functional groups or atoms, for example, O, OH, N, —Cl, —F, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, on the aryl or heteroaryl of the CLM, and optionally, one of which is modified to be covalently joined to a PTM, a chemical linker group (L), a ULM, CLM or combination thereof.

More specifically, non-limiting examples of CLMs include those shown below as well as those "hybrid" molecules that arise from the combination of one or more of the different features shown in the molecules below wherein at least one R or W is modified to be covalently joined to a PTM, a chemical linking group (L), a ULM, CLM, or combination thereof.

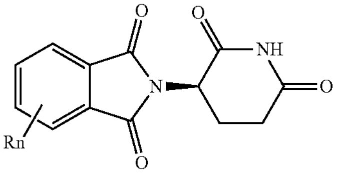

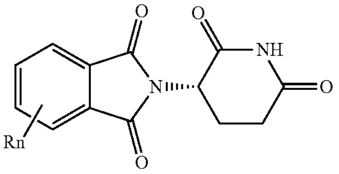

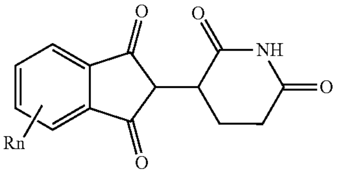

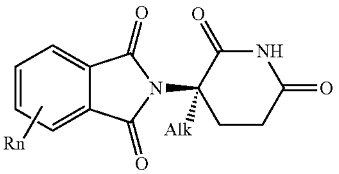

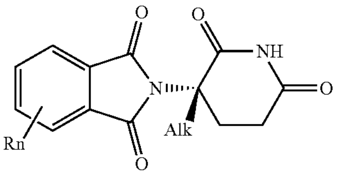

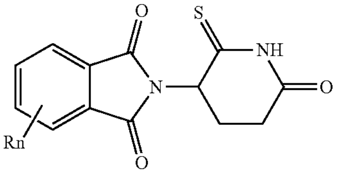

-continued
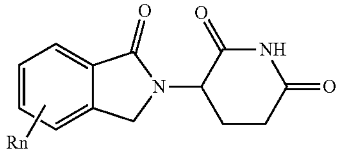
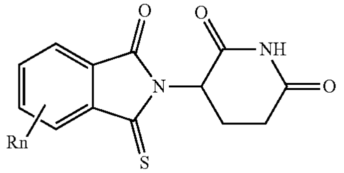
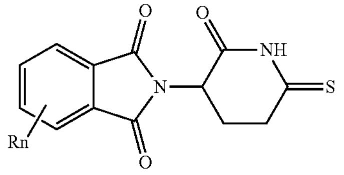
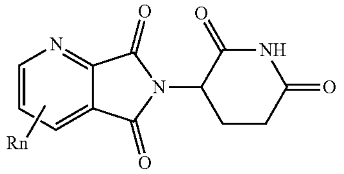
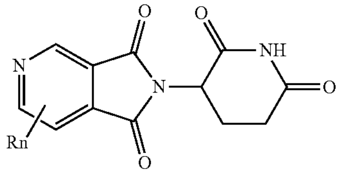
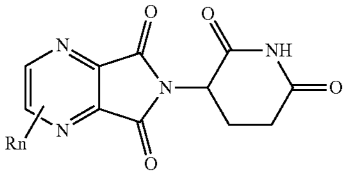
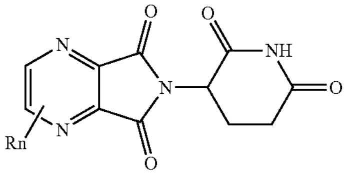
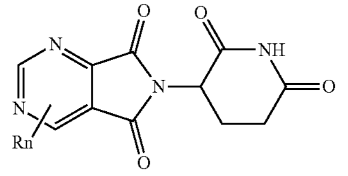
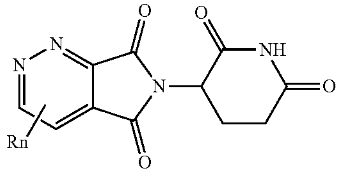
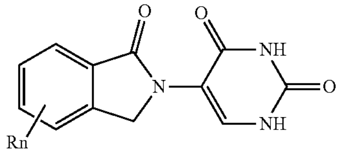
-continued
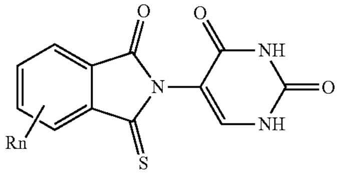
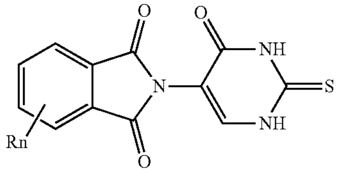
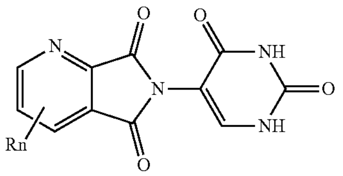
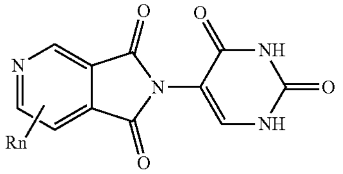
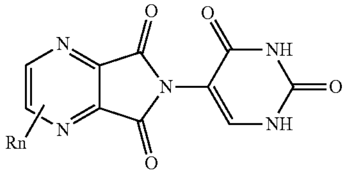
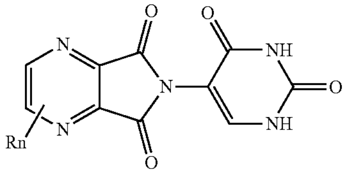
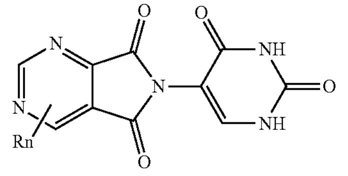
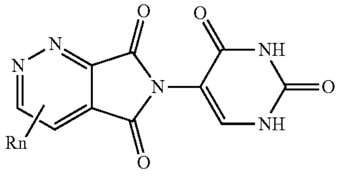
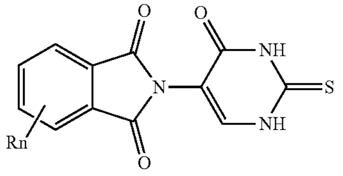
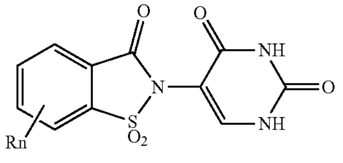

-continued
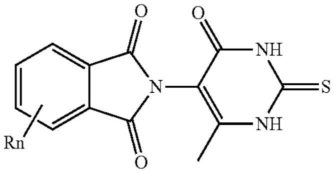
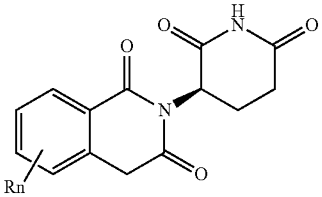
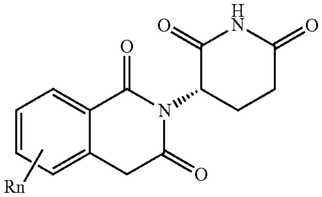
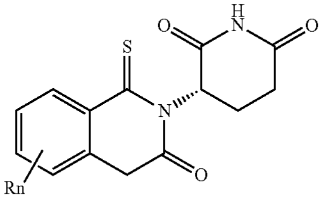
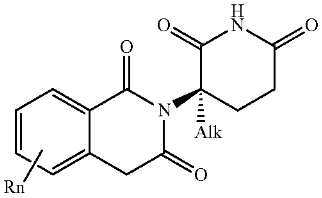
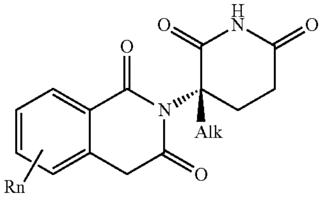
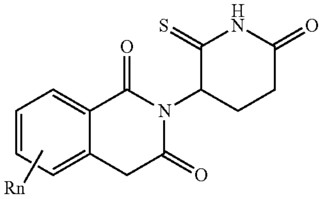
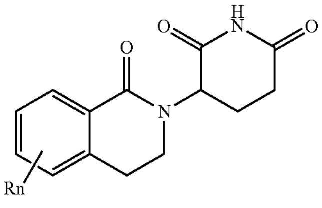
-continued
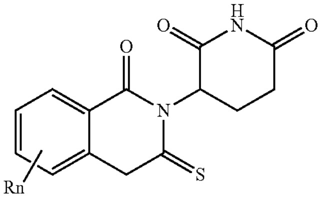
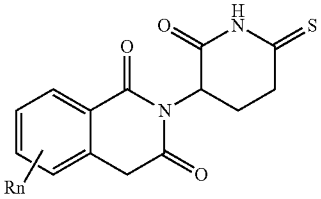
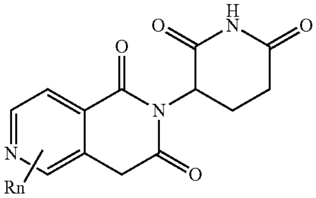
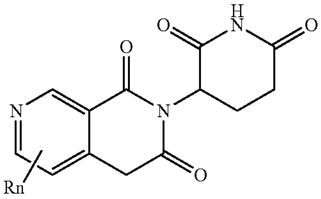
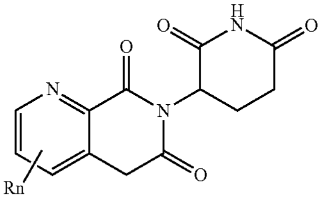
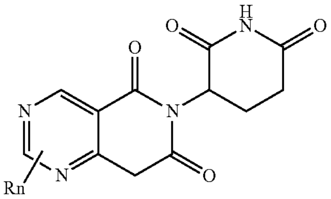
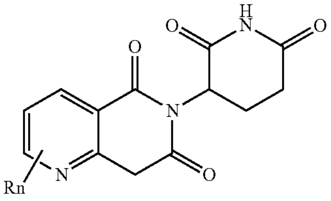
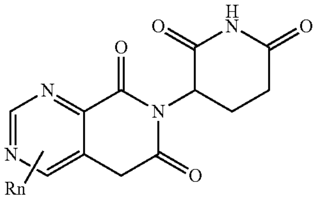

-continued
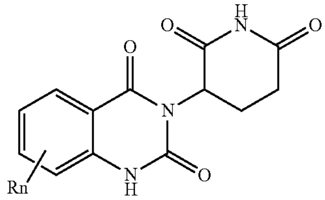
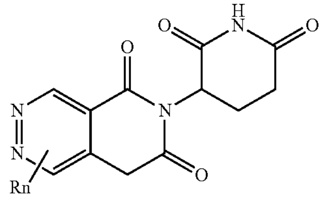
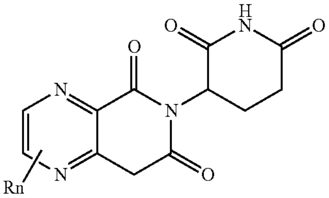
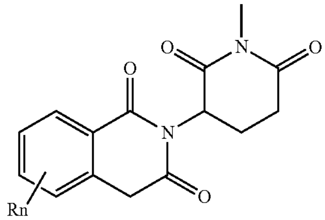
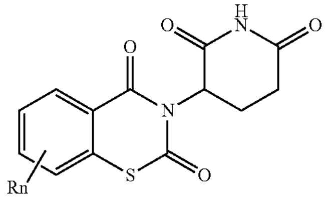
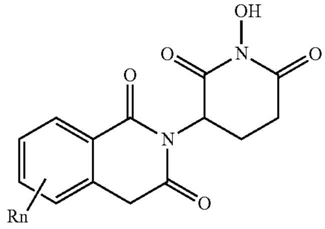
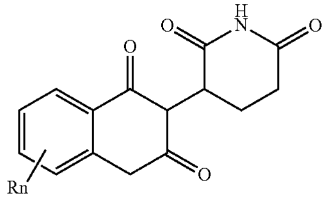
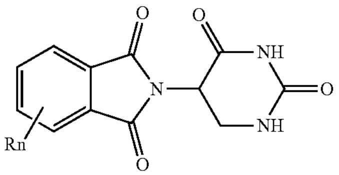
-continued
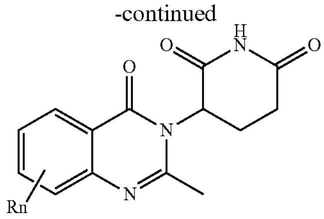
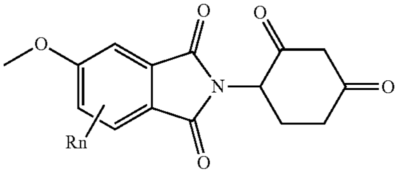
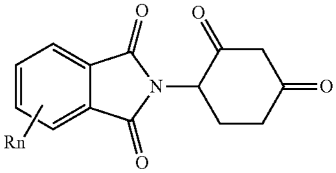
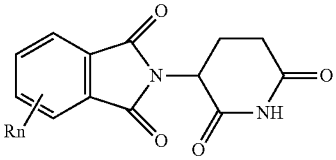
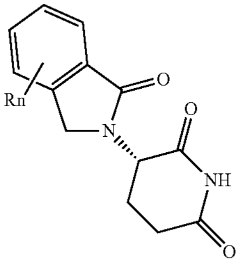
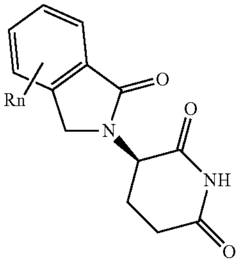
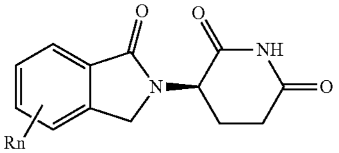
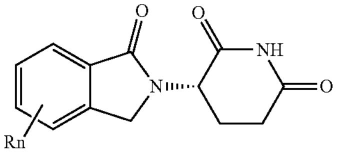
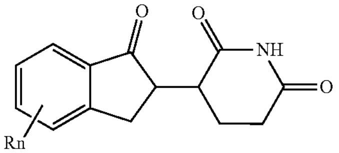
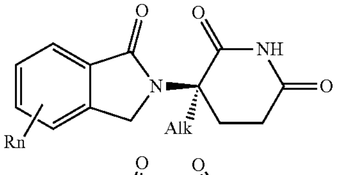
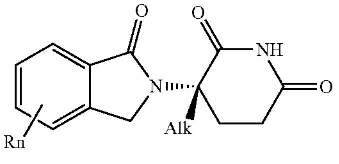

-continued
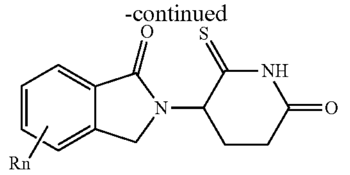
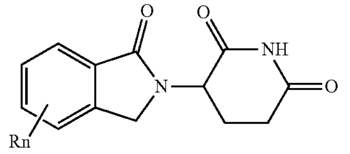
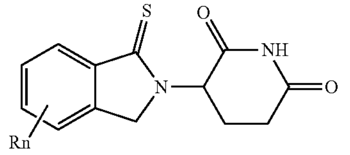
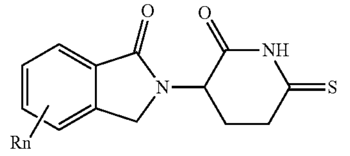
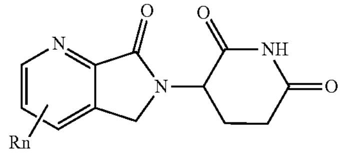
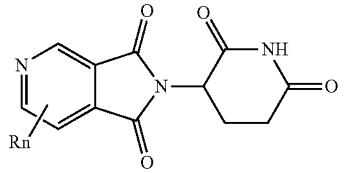
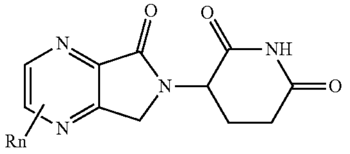
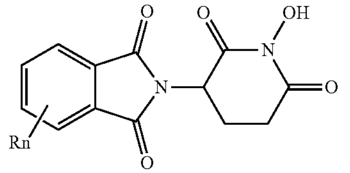
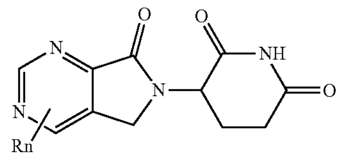
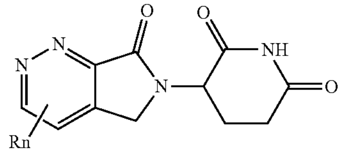
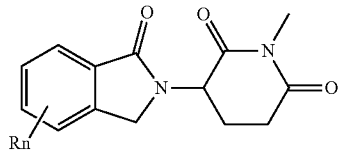
-continued
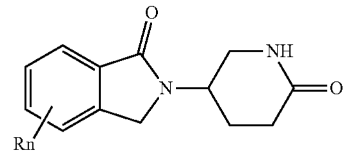
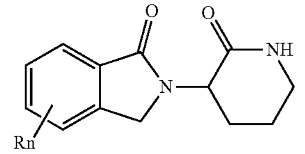
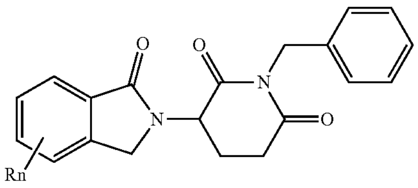
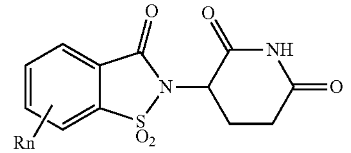
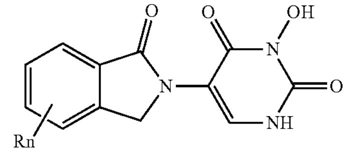
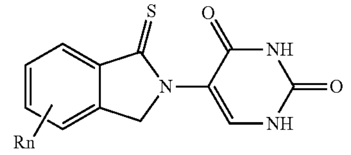
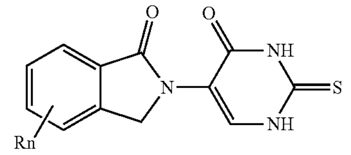
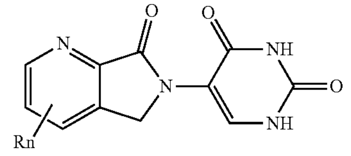
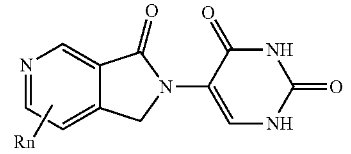
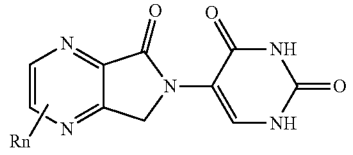
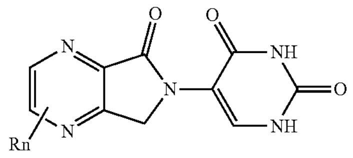

-continued
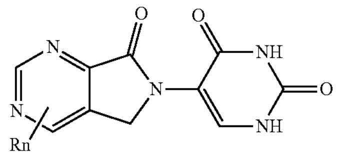
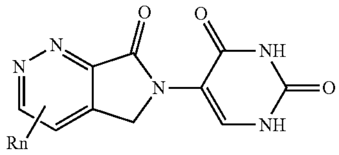
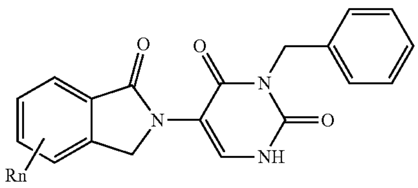
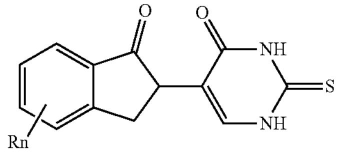
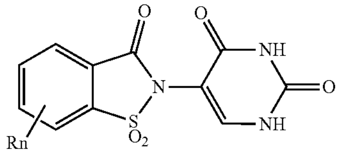
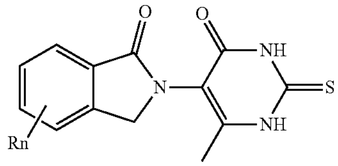
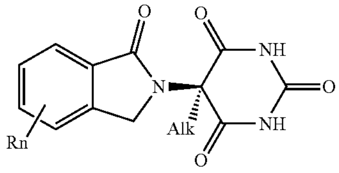
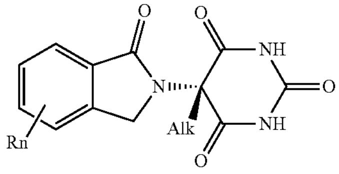
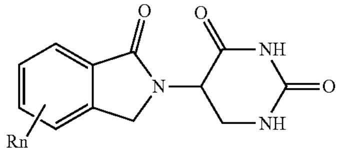
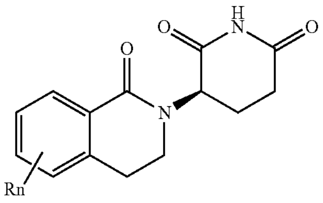
-continued
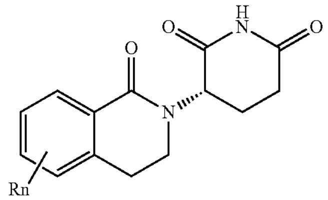
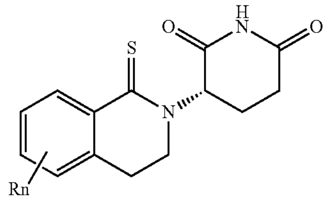
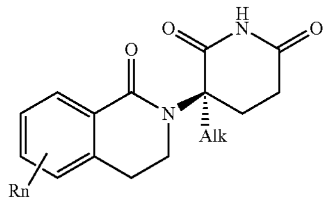
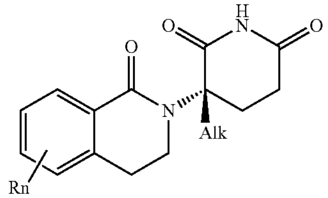
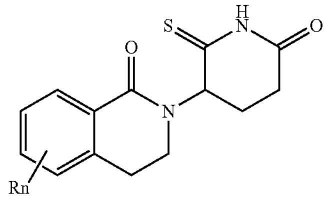
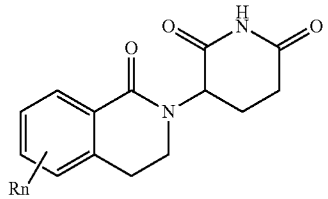
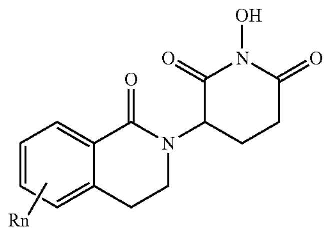
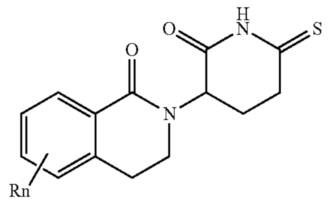

-continued
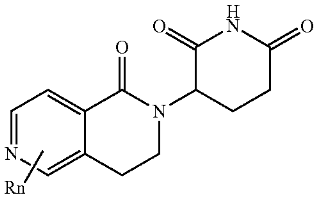
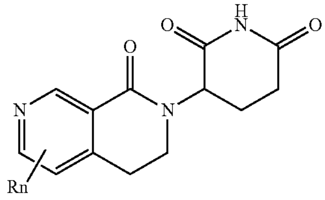
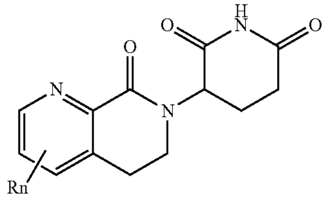
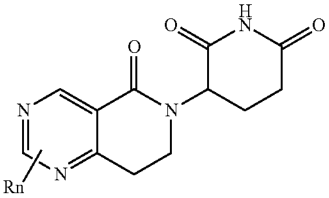
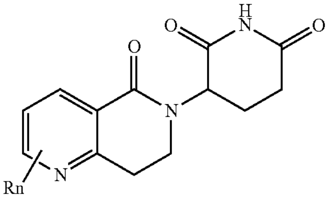
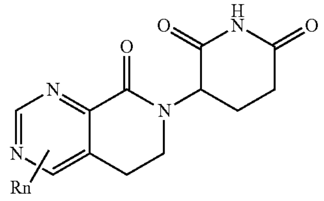
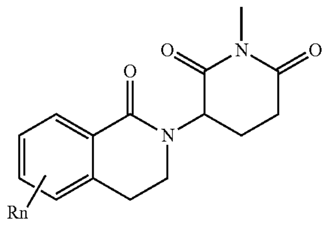
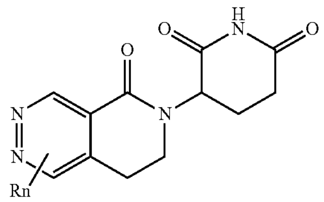
-continued
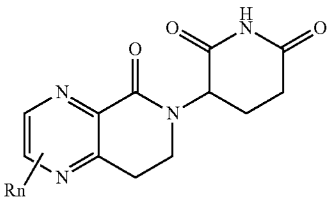
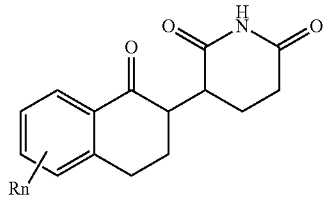
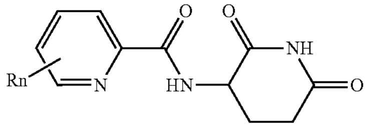
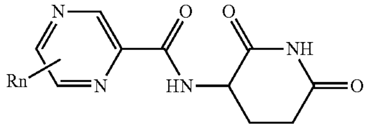
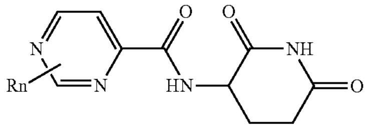
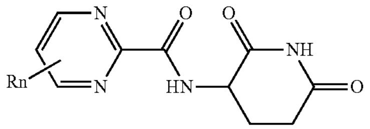
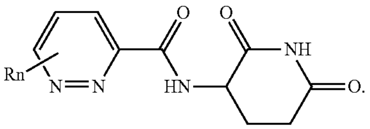
In any aspect or embodiment described herein, the CLM comprises a chemical structure selected from the group:
(h)
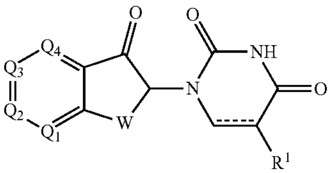
(i)
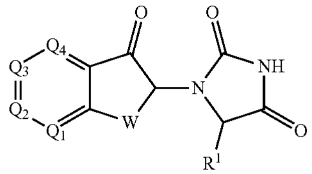

-continued
(j)
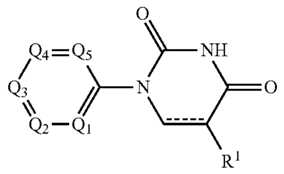
(k)
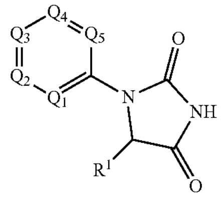
(l)
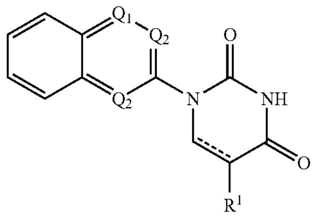
(m)
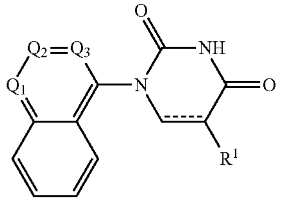
(n)
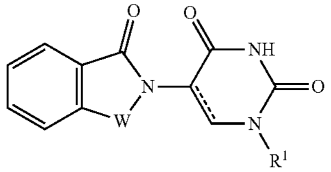
(o)
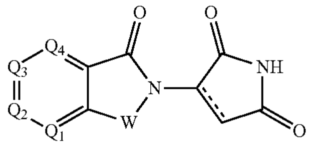
(p)
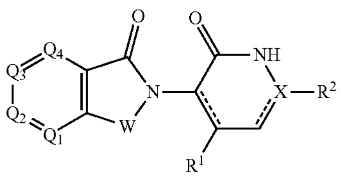
(q)
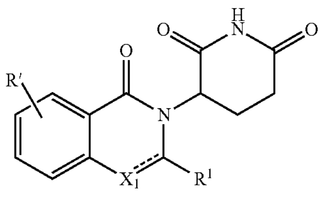
-continued
(r)
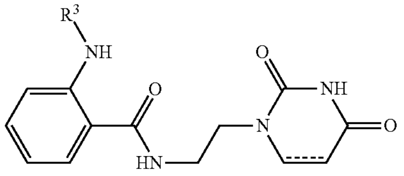
(s)
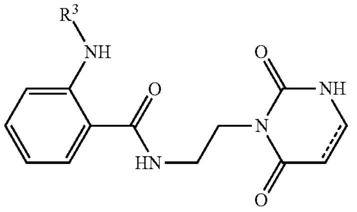
(t)
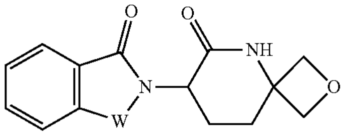
(u)
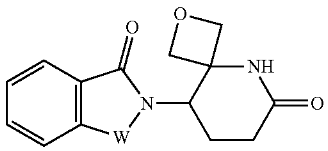
(v)
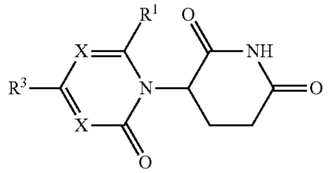
(w)
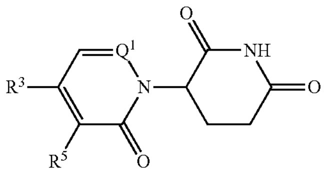
(x)
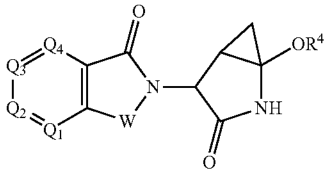
(y)
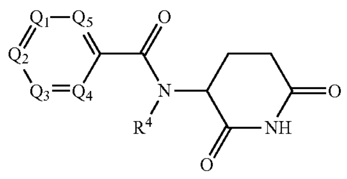

-continued (z)

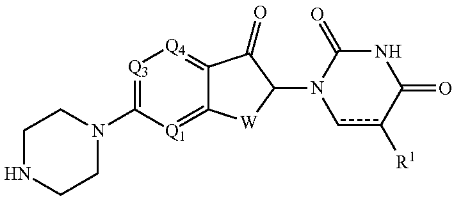

(aa)

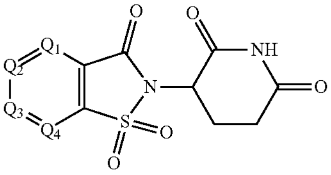

(ab)

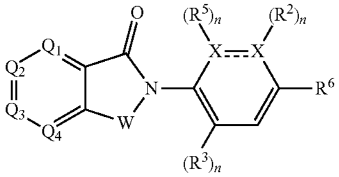

(ac)

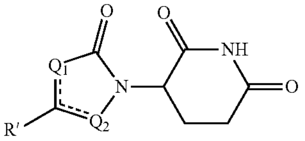

(ad)

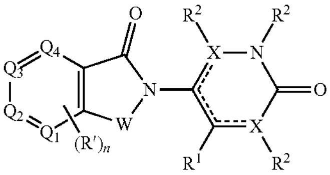

(ae)

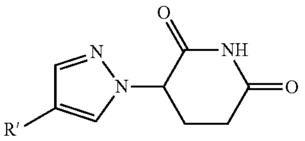

(af)

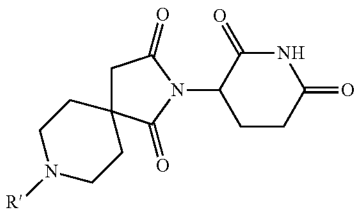

(ag)

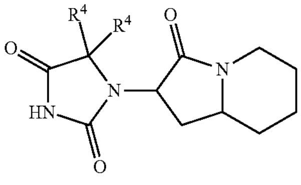

-continued (ah)

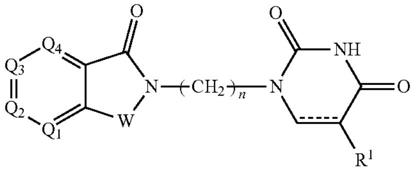

(ai)

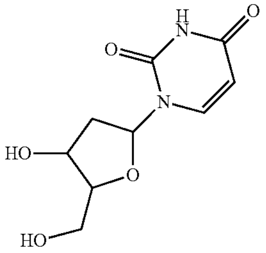

(aj)

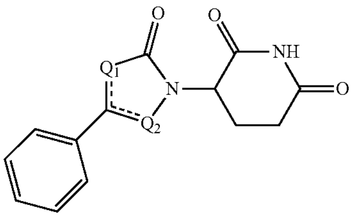

(ak)

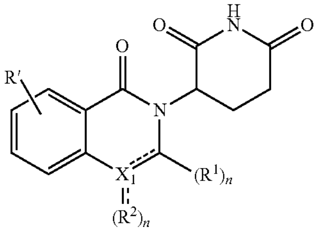

(al)

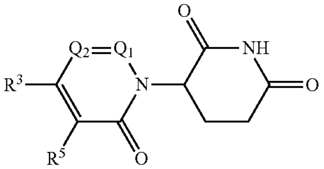

(am)

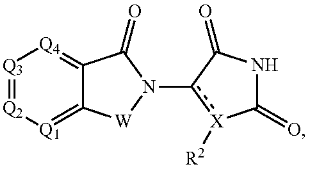

wherein:

W is selected from $CH_2$, O, CHR, C═O, $SO_2$, NH, N, optionally substituted cyclopropyl group, optionally substituted cyclobutyl group, and N-alkyl (e.g., $CH_2$, CHR, C═O, $SO_2$, NH, and N-alkyl);

each of $Q_1$, $Q_2$, $Q_3$, $Q_4$, and $Q_5$ is independently a N, CH, or CR';

$R^1$ is a bond, H, OH, CN, C1-C3 alkyl, or C═O;

$R^2$ is absent, H, OH, CN, C1-C3 alkyl, $CHF_2$, $CF_3$, CHO, or C(═O)$NH_2$;

$R^3$ is a bond, H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), or substituted alkoxy (e.g., substituted C1-C6 or C1-C3 alkoxyl);

$R^4$ is a bond, H, alkyl, or substituted alkyl;

$R^5$ and $R^6$ are each independently a bond, H, halogen, C(=O)R', CN, OH, or $CF_3$;

X is C, CH, C=O, or N;

$X_1$ is C=O, N, CH, or $CH_2$;

each R' is independently a bond, H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, C(=O)$OR^2$, or optionally substituted phenyl;

n is an integer 0 to 4;

⫽ is a single or double bond; and the CLM is covalently joined to a PTM, a chemical linker group (L), a ULM, CLM or combination thereof.

In any aspect or embodiment described herein, the CLM is represented by the chemical structure:

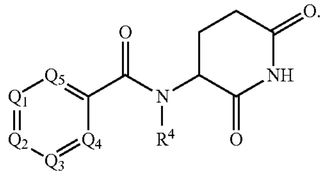

In any aspect or embodiment described herein, the CLM is covalently joined to a PTM, or a chemical linker group (L) via an R group (such as, R, $R^1$, $R^2$, $R^3$, $R^4$ or R'), W, X, or a Q group (such as, $Q_1$, $Q_2$, $Q_3$, $Q_4$, or $Q_5$).

In any aspect or embodiment described herein, the CLM is covalently joined to a PTM, or a chemical linker group (L) via W, X, R, $R^1$, $R^2$, $R^3$, $R^4$, $R^5$, R', $Q_1$, $Q_2$, $Q_3$, $Q_4$, and $Q_5$.

In any aspect or embodiment described herein, the W, X, $R^1$, $R^2$, $R^3$, $R^4$, R', $Q_1$, $Q_2$, $Q_3$, $Q_4$, and $Q_5$ can independently be covalently coupled to a linker and/or a linker to which is attached to one or more PTM, ULM, CLM groups.

More specifically, non-limiting examples of CLMs include those shown below as well as "hybrid" molecules or compounds that arise from combining one or more features of the following compounds:

(an)

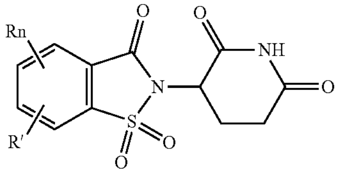

(ao)

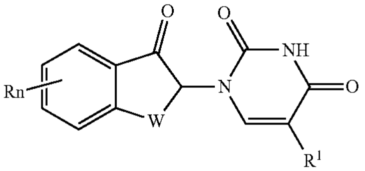

(ap)

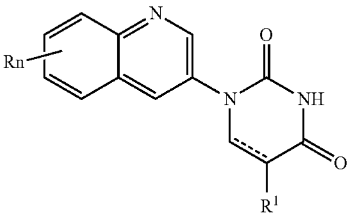

-continued (aq)

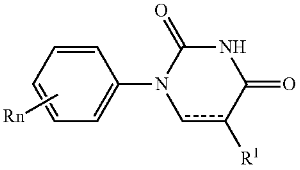

(ar)

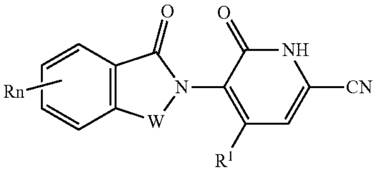

(as)

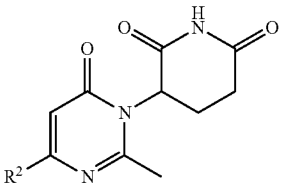

(at)

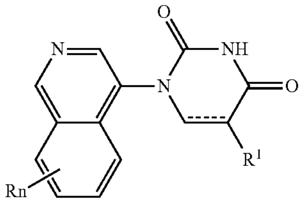

(au)

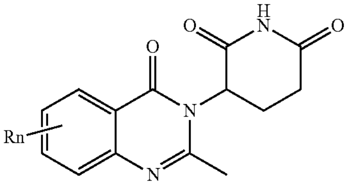

(av)

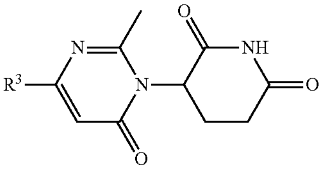

(aw)

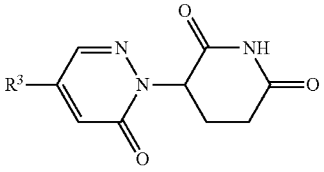

(ax)

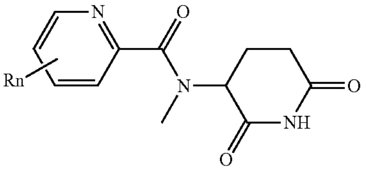

-continued (ay)

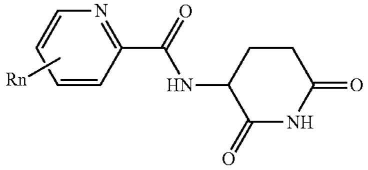

(ay')

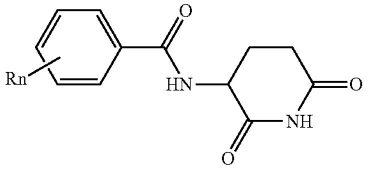

(az)

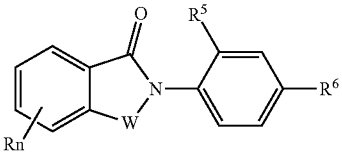

(ba)

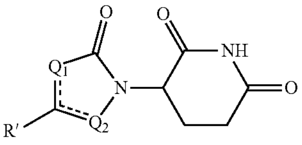

(bb)

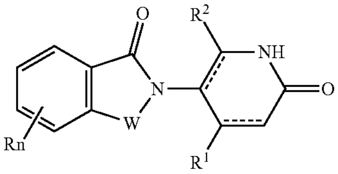

(bc)

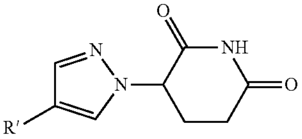

(bd)

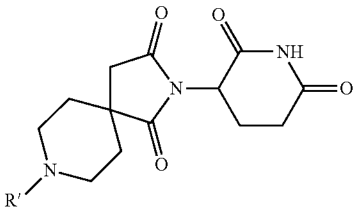

(be)

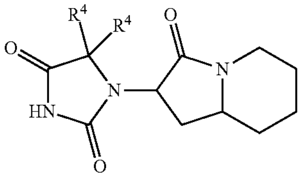

(bf)

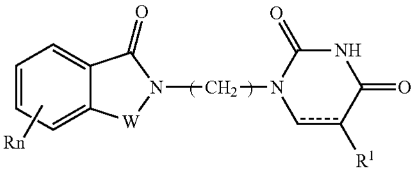

-continued (bg)

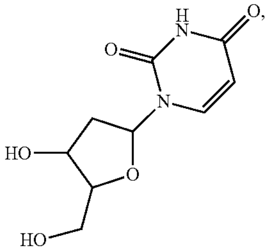

wherein:

W is selected from the group $CH_2$, CHR, C=O, $SO_2$, NH, and N-alkyl;

$R^1$ is absent (i.e., a bond), H, CH, CN, or C1-C3 alkyl;

$R^2$ is a bond, H or a C1-C3 alkyl;

$R^3$ is a bond, H, alkyl, substituted alkyl, alkoxy, or substituted alkoxy;

$R^4$ is a bond, methyl or ethyl;

$R^5$ is a bond, H or halogen;

$R^6$ is a bond, H or halogen;

n is an integer from 0 to 4;

each R and R' is independently a bond, H, a functional group or an atom (e.g., H, halogen (e.g., —Cl or —F), amine, C1-C3 alkyl, C1-C3 alkyl, C1-C3 alkoxyl, $NR^2R^3$, or C(=O)$OR^2$); or an attachment point for a PTM, or a chemical linker group (L), $Q_1$ and $Q_2$ are each independently N or C substituted with a group independently selected from H and C1-C3 alkyl; and

 is a single or double bond.

In any aspect or embodiment described herein, the W, $R^1$, $R^2$, $Q_1$, $Q_2$, $Q_3$, $Q_4$, R, and R' can independently be covalently coupled to a linker and/or a linker to which is attached one or more PTM groups.

In any aspect or embodiment described herein, the $R^1$, $R^2$, $Q_1$, $Q_2$, $Q_3$, $Q_4$, R, and R' can independently be covalently coupled to a linker and/or a linker to which is attached one or more PTM groups.

In any aspect or embodiment described herein, the $Q_1$, $Q_2$, $Q_3$, $Q_4$, R, and R' can independently be covalently coupled to a linker and/or a linker to which is attached one or more PTM groups.

In any aspect or embodiment described herein, R is a bond or modified to be covalently joined to the linker group (L) or, a PTM or combination thereof.

As would be readily apparent, in any aspect or embodiment described herein, R, R', R'', $R^1$, $R^2$, $R^3$, $R^4$, $R_5$, and $R^6$ of the CLM can be a bond.

In any aspect or embodiment described herein, the CLM is selected from:

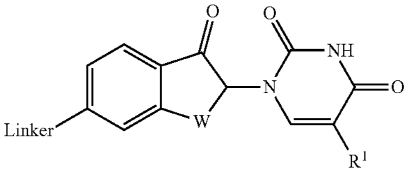

-continued
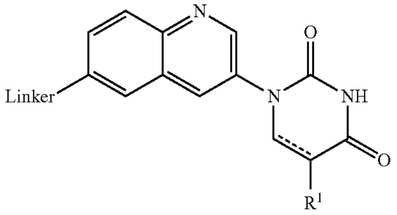
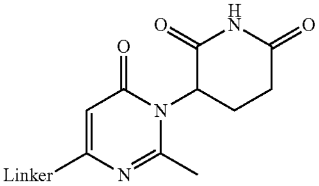
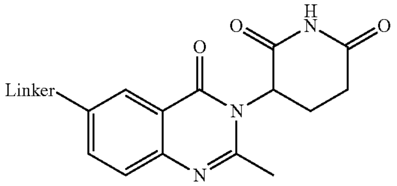
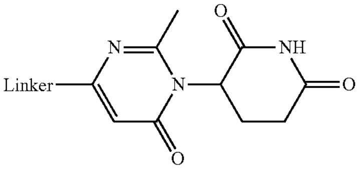
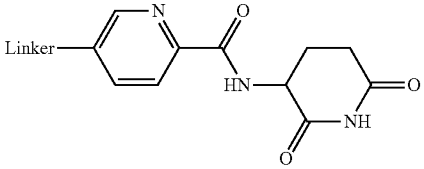
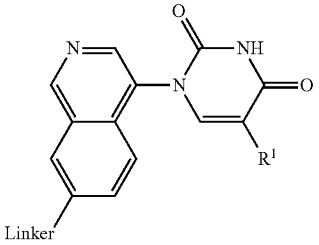
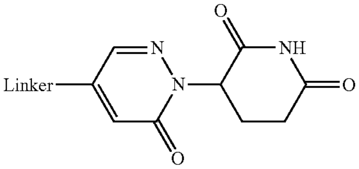
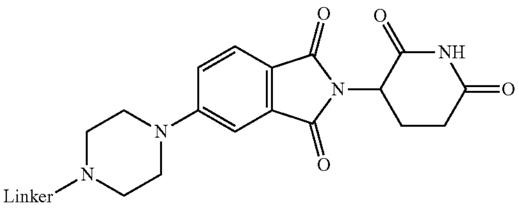
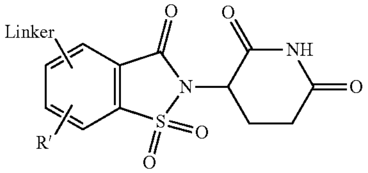
-continued
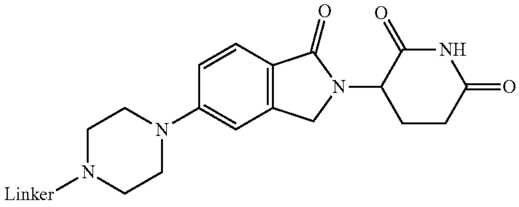
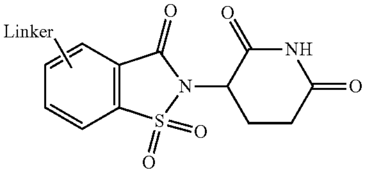
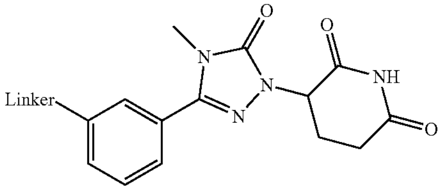
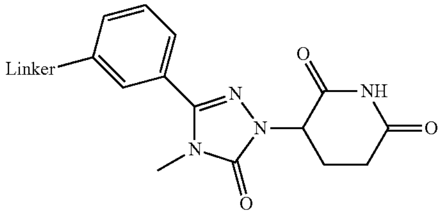
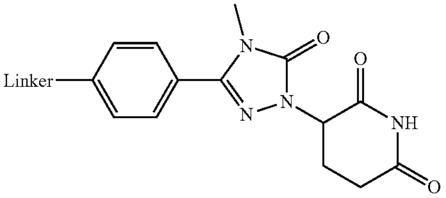
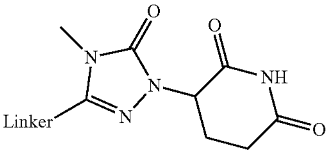
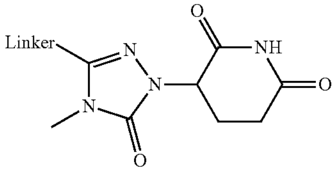
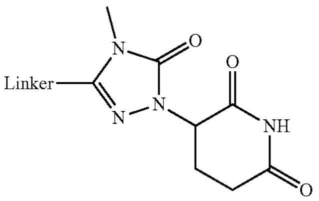
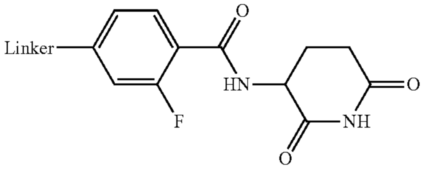

-continued
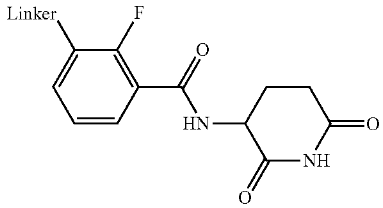
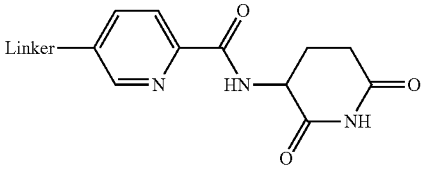
and
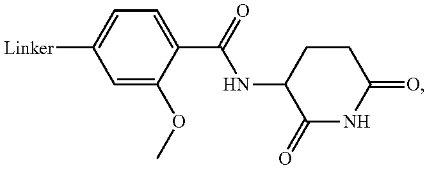
wherein R' is a halogen and $R^1$ is as described herein.
In certain cases, "CLM" can be an imide that binds to cereblon E3 ligase. These imides and linker attachment point can be, but not be limited to one of the following structures:
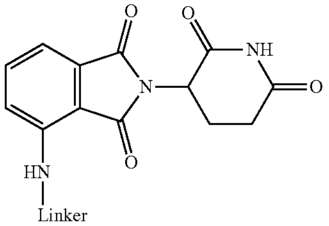
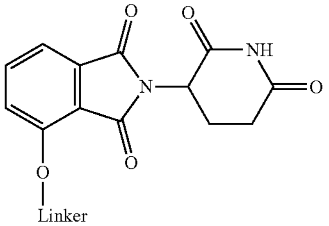
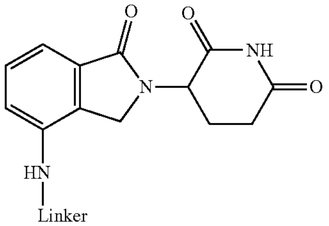
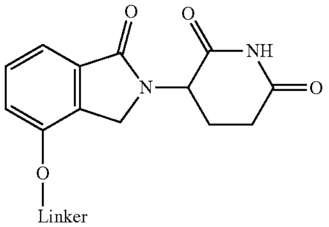
-continued
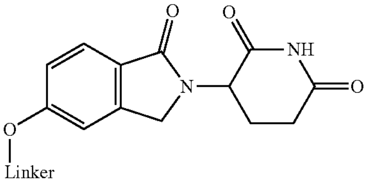
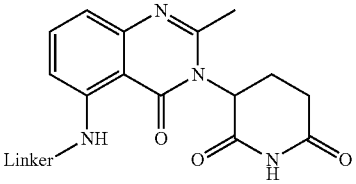
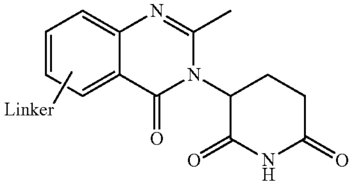
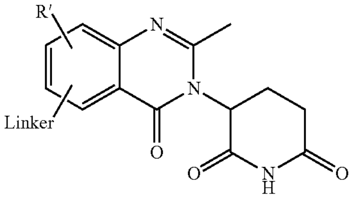
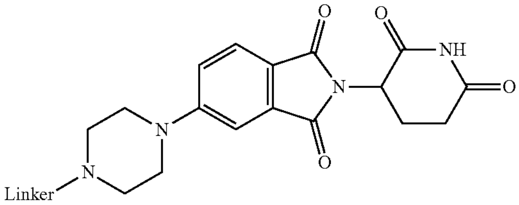
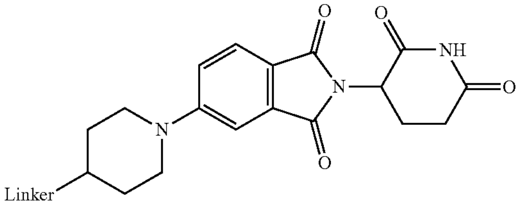
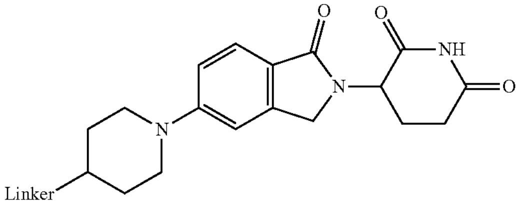
or
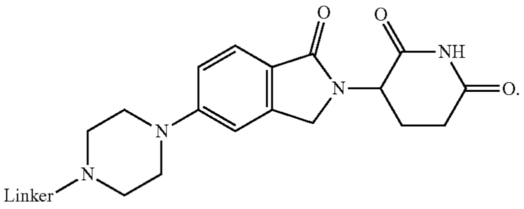

In any aspect or embodiment described herein, the ULM is selected from the group consisting of:
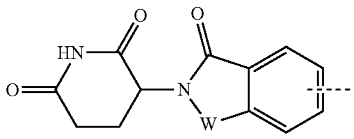
,
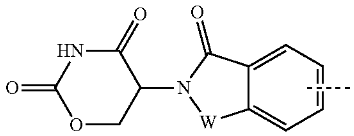
,
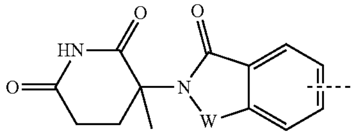
,
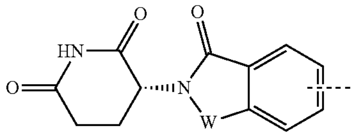
,
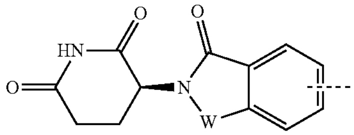
,
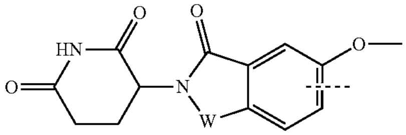
,
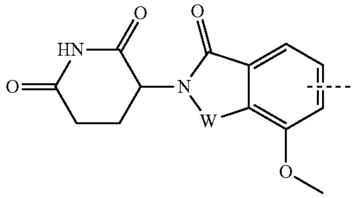
,
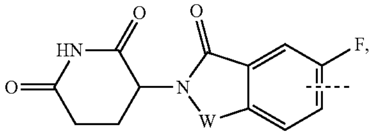
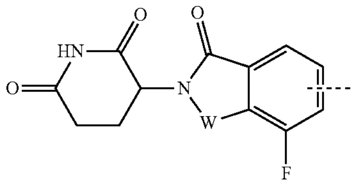
,
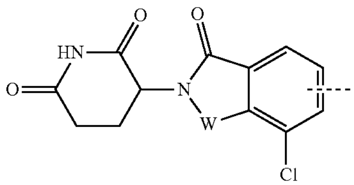
,
-continued
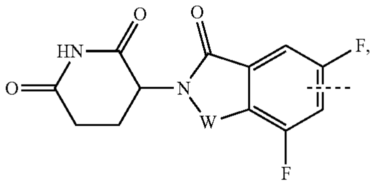
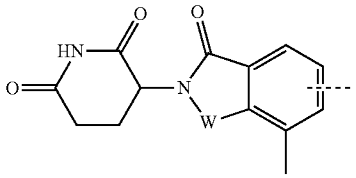
,
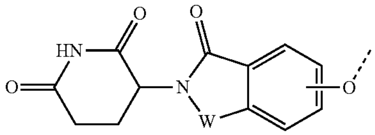
,
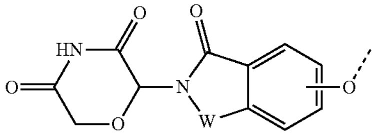
,
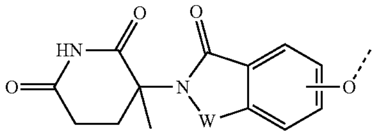
,
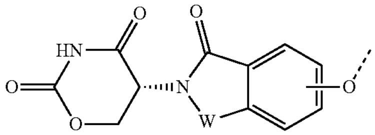
,
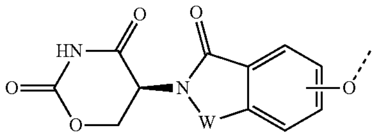
,
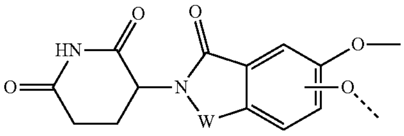
,
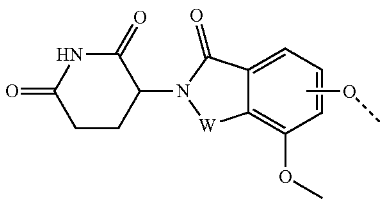
,
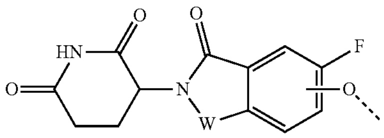
,
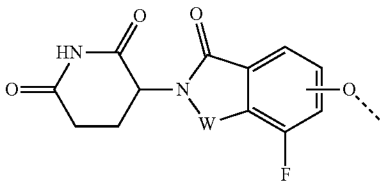
, -continued
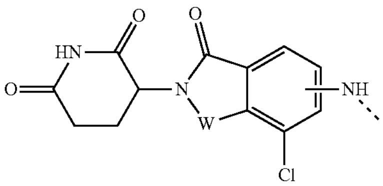
,
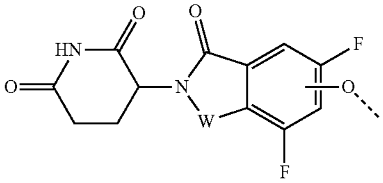
,
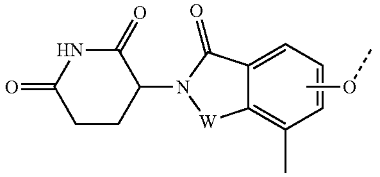
,
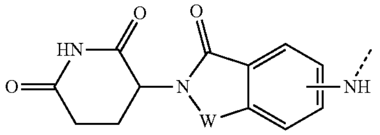
,
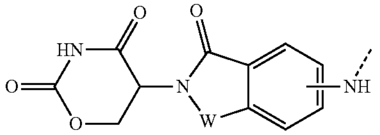
,
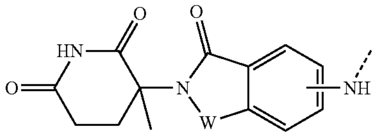
,
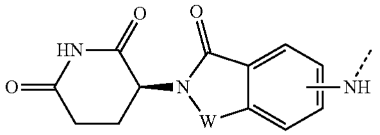
,
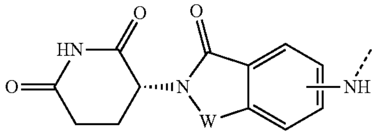
,
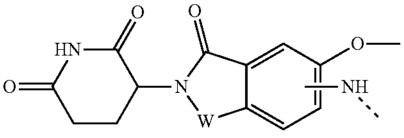
,
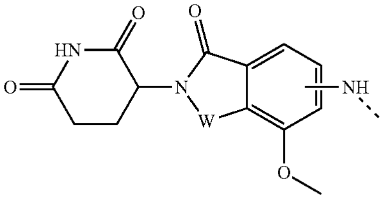
,
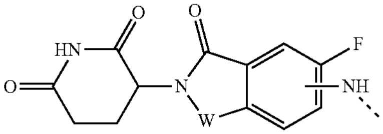
,
-continued
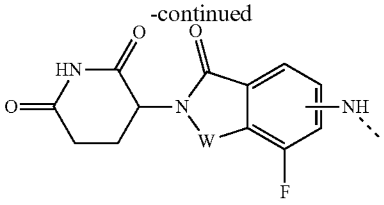
,
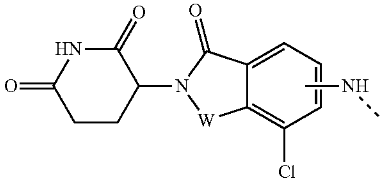
,
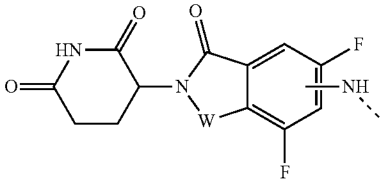
,
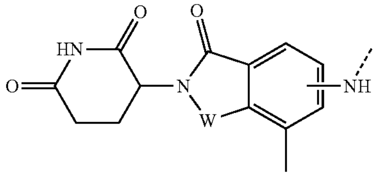
,
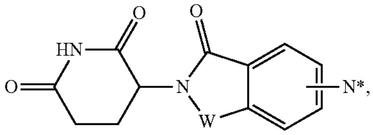
,
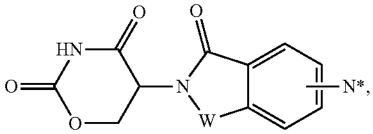
,
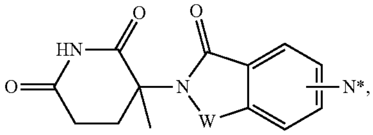
,
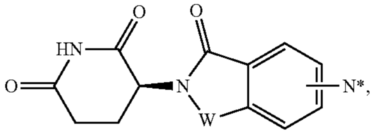
,
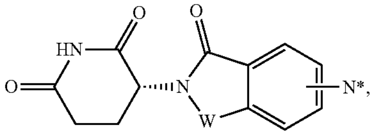
,
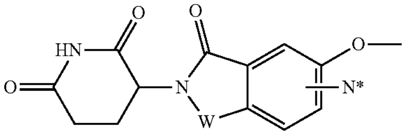
,
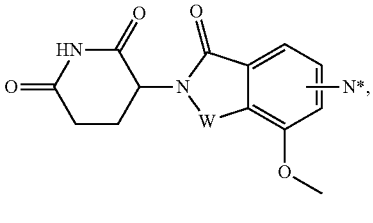
, -continued
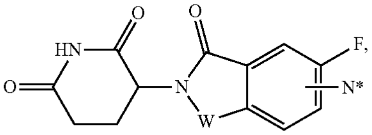
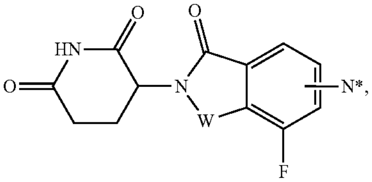
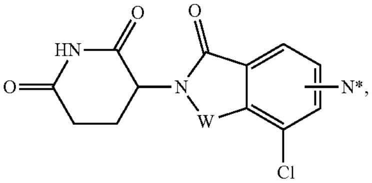
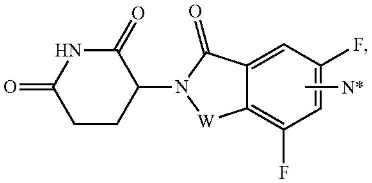
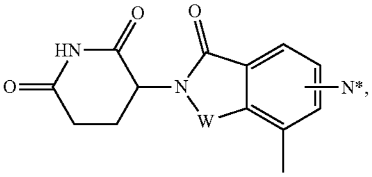
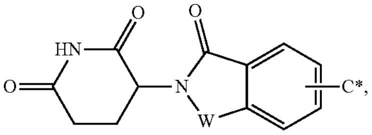
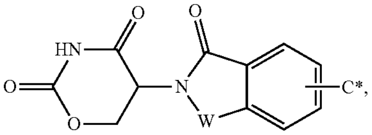
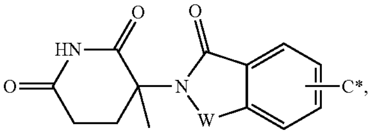
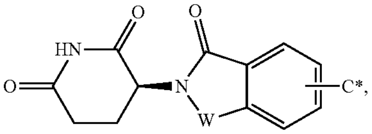
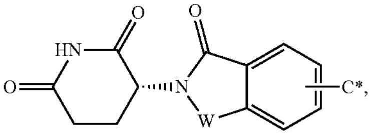
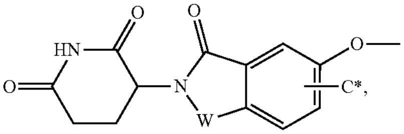
,
-continued
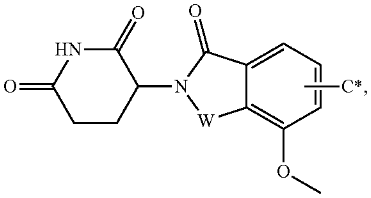
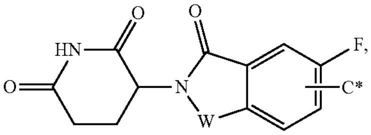
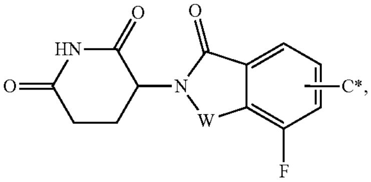
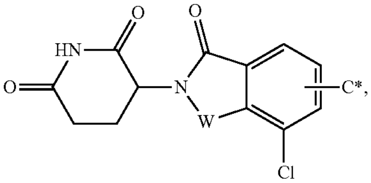
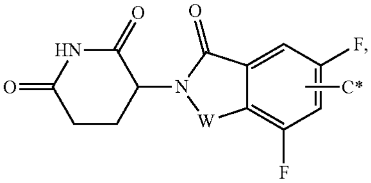
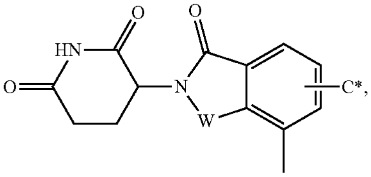
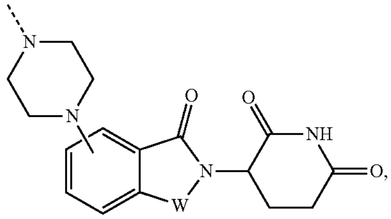
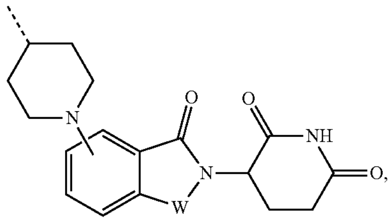
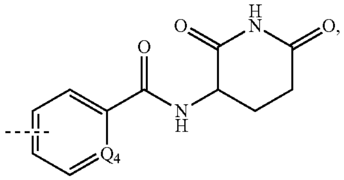

-continued

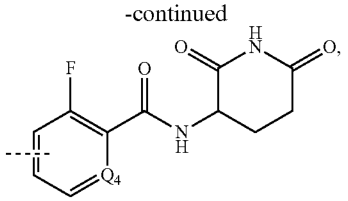

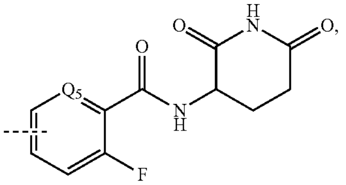

or

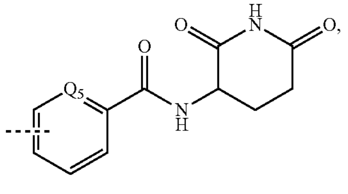

wherein:

- - - of the ULM indicates the point of attachment with a linker group or a PTM;

N* is a nitrogen atom that is shared with the chemical linker group or PTM;

C* is a carbon atom that is shared with the chemical linker group or PTM and

W, $Q_4$, and $Q_5$ are each defined as described in any aspect or embodiment described herein.

In any aspect or embodiment described herein, each R of the CLM is selected from a H, O, OH, N, NH, $NH_2$, Cl, —F, —Br, —I, CN, $CF_3$, optionally substituted linear or branched $C_{1-3}$ alkyl, optionally substituted linear or branched $C_{1-3}$ alkoxy, amide, and carboxy.

In any aspect or embodiment described herein, each R of the CLM is selected from a H, O, OH, N, NH, $NH_2$, Cl, —F, —Br, —I, CN, $CF_3$, methyl, methoxy, ethoxy, amide, and carboxy.

In any aspect or embodiment described herein, each R of the CLM is selected from a H, O, OH, N, NH, $NH_2$, Cl, —F, —Br, —I, CN, $CF_3$, methyl, methoxy, and ethoxy.

In any aspect or embodiment described herein, the CLM is represented by the chemical structure

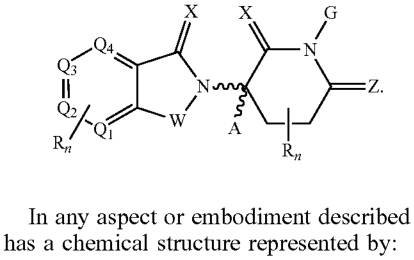

In any aspect or embodiment described herein, the CLM has a chemical structure represented by:

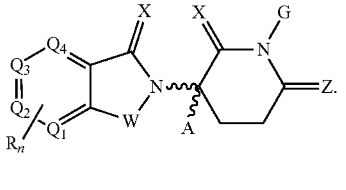

In any aspect or embodiment described herein, each R is selected from a H, O, OH, NH, $NH_2$, —Cl, —F, CN, $CF_3$, optionally substituted linear or branched $C_{1-3}$ alkyl, optionally substituted linear or branched $C_{1-3}$ alkoxy.

In any aspect or embodiment described herein, each R is selected from a H, O, OH, NH, $NH_2$, —Cl, —F, —CN, $CF_3$, methyl, methoxy, and ethoxy.

Exemplary Linkers

In certain embodiments, the compounds as described herein include a PTM chemically linked to a ULM (e.g., CLM) via a chemical linker (L). In certain embodiments, the linker group L comprises one or more covalently connected structural units (e.g., $-A^L_1 \ldots (A^L)_q-$ or $-(A^L)_q-$), wherein $A^L_1$ is a group coupled to PTM, and $(A^L)_q$ is a group coupled to ULM.

In any aspect or embodiment described herein, the linker (L) to a ULM (e.g., CLM) connection is a stable L-ULM connection. For example, in any aspect or embodiment described herein, when a linker (L) and a ULM are connected via a heteroatom (e.g., N, O, S), any additional heteroatom, if present, is separated by at least a carbon atom (e.g., $—CH_2—$), such as with an acetal or aminal group. By way of further example, in any aspect or embodiment described herein, when a linker (L) and a ULM are connected via a heteroatom, the heteroatom is not part of an ester.

In any aspect or embodiment described herein, the linker group L is a bond or a chemical linker group represented by the formula $-(A^L)_q-$, wherein A is a chemical moiety and q is an integer from 1-100 or 1-80 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80), and wherein L is covalently bound to both the PTM and the ULM, and provides for binding of the PTM to the protein target and the ULM to an E3 ubiquitin ligase to effectuate target protein ubiquitination.

In any aspect or embodiment described herein, the linker group L is a bond or a chemical linker group represented by the formula $-(A^L)_q-$, wherein A is a chemical moiety and q is an integer from 6-30 (e.g., 1, 2, 3, 4, 5, 6, 7, 8, 9, 10, 11, 12, 13, 14, 15, 16, 17, 18, 19, 20, 21, 22, 23, 24, or 25), and wherein L is covalently bound to both the PTM and the ULM, and provides for binding of the PTM to the protein target and the ULM to an E3 ubiquitin ligase in sufficient proximity to result in target protein ubiquitination.

In any aspect or embodiment described herein, the linker group L is $-(A^L)_q-$, wherein:

$(A^L)_q$ is a group which connects a ULM (e.g., CLM), to PTM;

q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, and heteroaryl optionally substituted with 1-6 $R^{L1}$ and/or $R^{L2}$ groups, where $R^{L1}$ or $R^{L2}$, each independently are optionally linked to other groups to form a cycloalkyl or heterocyclyl moiety, optionally substituted with 1-4 $R^{L5}$ groups; and $R^{L1}$, $R^{L2}$, $R^{L3}$, $R^{L4}$ and $R^{L5}$ are, each independently, H, halogen $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$ heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH═CH($C_{1-8}$alkyl), C($C_{1-8}$alkyl)═CH($C_{1-8}$alkyl), C($C_{1-8}$alkyl)═C($C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2$ $NH(C_{1-8}alkyl)$, NH $SO_2N(C_{1-8}alkyl)_2$, or NH $SO_2NH_2$.

In certain embodiments, q is an integer greater than or equal to 1.

In any aspect or embodiment described herein, e.g., where q of the linker is greater than 2, $(A^L)_q$ is a group which is $A^L{}_1$ and $(A^L)_q$ wherein the linker couples a PTM to a ULM.

In any aspect or embodiment described herein, e.g., where q of the linker is 2, $A^L{}_2$ is a group which is connected to $A^L{}_1$ and to a ULM.

In any aspect or embodiment described herein, e.g., where q of the linker is 1, the structure of the linker group L is -$A^L{}_1$-, and $A^L{}_1$ is a group which connects a ULM moiety to a PTM moiety.

In any aspect or embodiment described herein, the unit $A^L$ of linker (L) comprises a group represented by a general structure selected from the group consisting of:

—$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —$NR(CH_2)_n$-(cycloalkyl)-(lower alkyl)-$OCH_2$—, —$NR(CH_2)_n$-(heterocycloalkyl)-, —$NR(CH_2CH_2O)_n$-(lower alkyl)-O—$CH_2$—, —$NR(CH_2CH_2O)_n$-(heterocycloalkyl)-O—$CH_2$—, —$NR(CH_2CH_2O)_n$-Aryl-O—$CH_2$—, —$NR(CH_2CH_2O)_n$-(heteroaryl)-O—$CH_2$—, —$NR(CH_2CH_2O)_n$-(cyclo alkyl)-O-(heteroaryl)-O—$CH_2$—, —$NR(CH_2CH_2O)_n$-(cyclo alkyl)-O-Aryl-O—$CH_2$—, —$NR(CH_2CH_2O)_n$-(lower alkyl)-NH-Aryl-O—$CH_2$—, —$NR(CH_2CH_2O)_n$-(lower alkyl)-O-Aryl-$CH_2$, —$NR(CH_2CH_2O)_n$-cycloalkyl-O-Aryl-, —$NR(CH_2CH_2O)_n$-cycloalkyl-O-(heteroaryl)I—, —$NR(CH_2CH_2)_n$-(cycloalkyl)-O-(heterocyclyl)-$CH_2$, —$NR(CH_2CH_2)_n$-(heterocyclyl)-(heterocyclyl)-$CH_2$, and —$N(R^1R^2)$-(heterocyclyl)-$CH_2$; where n of the linker can be 0 to 10;

R of the linker can be H, or lower alkyl; and

R1 and R2 of the linker can form a ring with the connecting N.

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl, and including all implied subranges, e.g., $C_1$-$C_{10}$, $C_1$-$C_{20}$; $C_2$-$C_{10}$, $C_{2-20}$; $C_{10}$-$C_{20}$, $C_{10}$-$C_{50}$ etc.), wherein each carbon is optionally independently substituted or replaced with (1) a heteroatom selected from N, O, S, P, or Si atoms that has an appropriate number of hydrogens, substitutions, or both to complete valency, (2) an optionally substituted cycloalkyl or bicyclic cycloalkyl, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linked or adjacently located).

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally independently replaced with $CR^{L1}R^{L2}$, O, S, SO, $SO_2$, $NR^{L3}$, $SO_2NR^{L3}SONR^{L3}$, $CONR^{L3}$, $NR^{L3}CONR^{L4}$, $NR^{L3}SO_2NR^{L4}$, CO, $CR^{L1}$═$CR^{L2}$, C≡C, $SiR^{L1}R^{L2}$, $P(O)R^{L1}$, $P(O)OR^{L1}$, $NR^{L3}C$(═NCN)$NR^{L4}$, $NR^{L3}C$(═NCN), $NR^{L3}C(═CNO_2)NR^{L4}$, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_5$-13 spiroheterocyclyl optionally substituted with 1-8 $R^{L1}$ and/or $R^{L2}$ groups, aryl optionally substituted with 1-6 $R^{L1}$ and/or $R^{L2}$ groups, or heteroaryl optionally substituted with 0-6 $R^{L1}$ and/or $R^{L2}$ groups, where $R^{L1}$ or $R^{L2}$, each independently are optionally linked to other groups to form a cycloalkyl or heterocyclyl moiety, optionally substituted with 1-4 $R^{L5}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$ heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH═CH($C_{1-8}$alkyl), C($C_{1-8}$alkyl)═CH($C_{1-8}$alkyl), C($C_{1-8}$alkyl)═C($C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, or NH $SO_2NH_2$.

In any aspect or embodiment described herein, the linker group is optionally substituted an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl, and including all implied subranges, e.g., C1-C10, C1-C20; C2-C10, C2-20; C10-C20, C10-C50 etc.), wherein each carbon atom optionally substituted or replaced with: a O, N, S, P or Si atom that has an appropriate number of hydrogens, substitutions (e.g., OH, halo, alkyl, methyl, ethyl, haloalkyl, hydroxyalkyl, alkoxy, methoxy, etc.), or both to complete valency; an optionally substituted aryl (e.g., an optionally substituted C5 or C6 aryl) or bicyclic aryl (e.g, an optionally substituted C5-C20 bicyclic heterary1); an optionally substituted heteroaryl (e.g., an optionally substituted C5 or C6 heteroaryl) or bicyclic heteroaryl (e.g., an optionally substituted heteroaryl or bicyclic heteroaryl having one or more heteroatoms selected from N, O, S, P, and Si that has an appropriate number of hydrogens, substitutions (e.g., OH, halo, alkyl, methyl, ethyl, haloalkyl, hydroxyalkyl, alkoxy, methoxy, etc.), or both to complete valency); an optionally substituted C1-C6 alkyl; an optionally substituted C1-C6 alkenyl; an optionally substituted C1-C6 alkynyl; an optionally substituted cycloalkyl (e.g., an optionally substituted C3-C7 cycloalkyl) or bicyclic cycloalkyl (e.g., an optionally substituted C5-C20 bicyclic cycloalkyl); or an optionally substituted heterocycloalkyl (e.g., an optionally substituted 3-, 4-, 5-, 6-, or 7-membered heterocyclic group) or bicyclicheteroalkyl (e.g., an optionally substituted heterocycloalkyl bicyclicheteroalkyl having one or more heteroatoms selected from N, O, S, P, or Si atoms that has an appropriate number of hydrogens, substitutions (e.g., OH, halo, alkyl, methyl, ethyl, haloalkyl, hydroxyalkyl, alkoxy, methoxy, etc.), or both to complete valency). In any aspect or embodiment described herein, the optionally substituted alkyl linker is optionally substituted with one or more OH, halo, linear or branched C1-C6 alkyl (such as methyl or ethyl), linear or branched C1-C6 haloalkyl, linear or branched C1-C6 hydroxyalkyl, or linear or branched C1-C6 alkoxy (e.g., methoxy).

In any aspect or embodiment described herein, the linker (L) does not have heteroatom-heteroatom bonding (e.g., no heteroatoms are covalently linked or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency.

In any aspect or embodiment described herein, the unit $A^L$ of the linker (L) comprises a structure selected from the group consisting of:

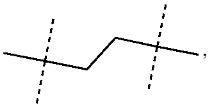
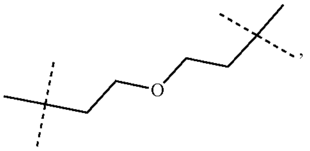
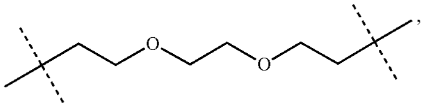
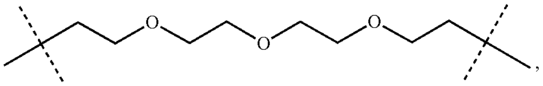
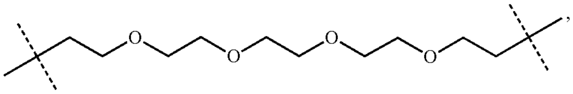
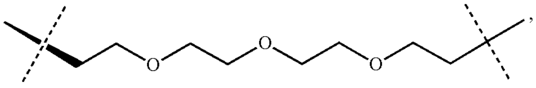
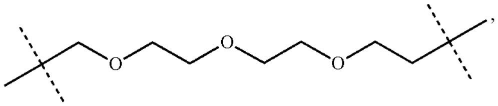

-continued

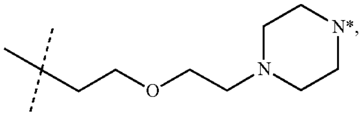
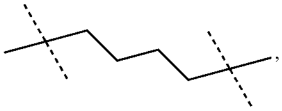
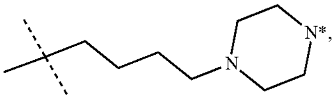
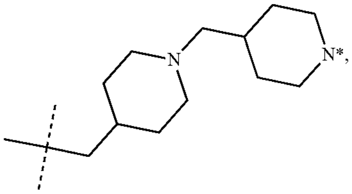
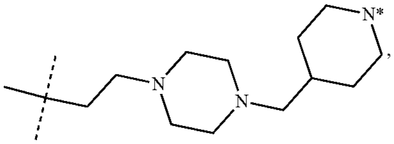
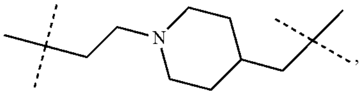
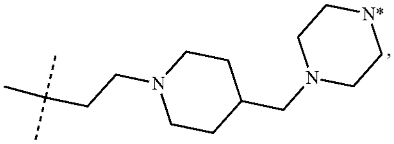
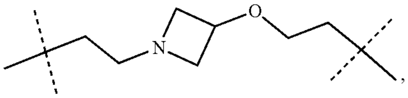
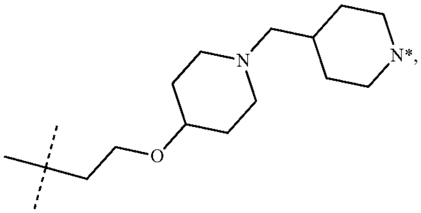
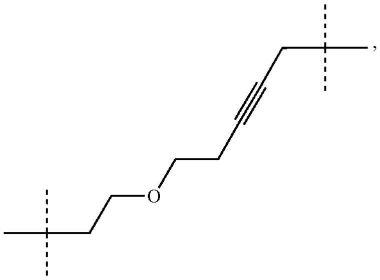

-continued
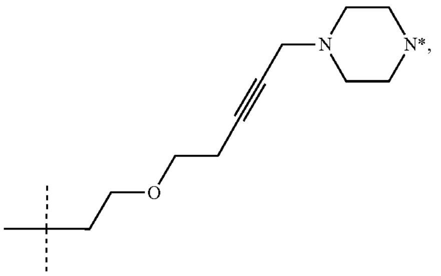
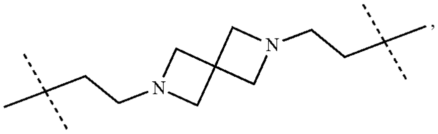
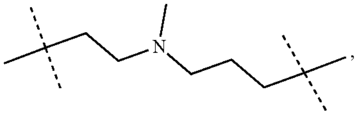
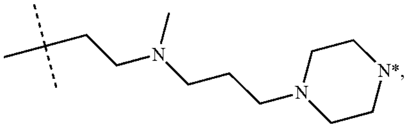
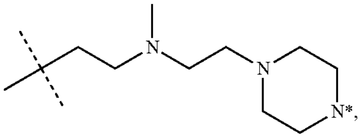
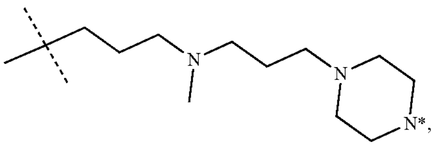
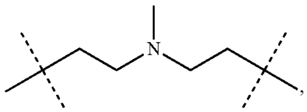
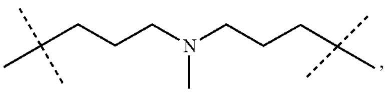
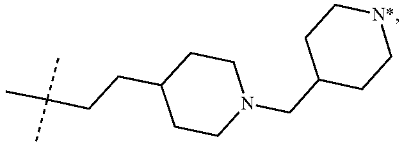
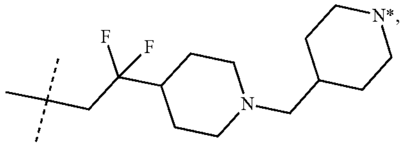
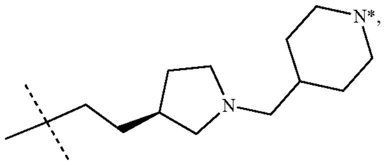
-continued
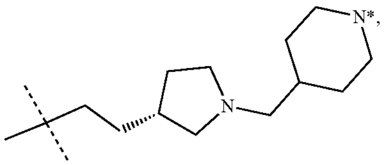
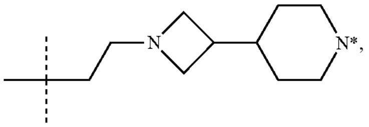
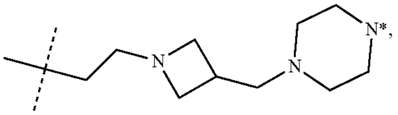
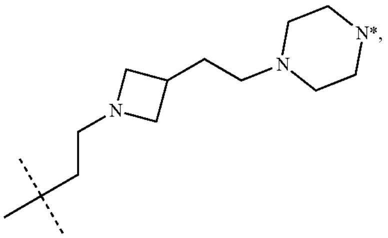
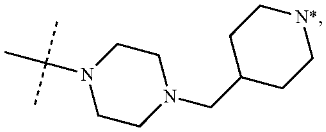
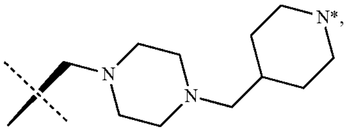
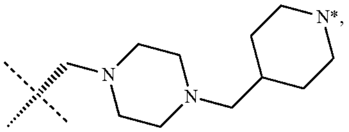
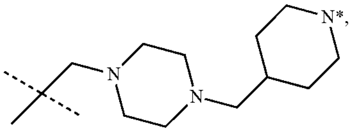
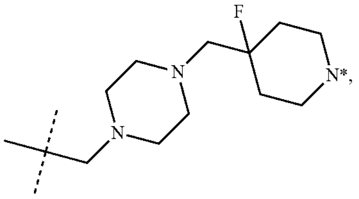
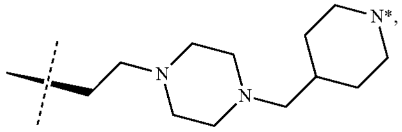
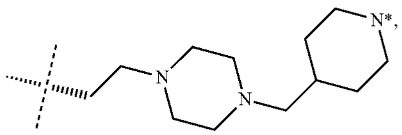

-continued
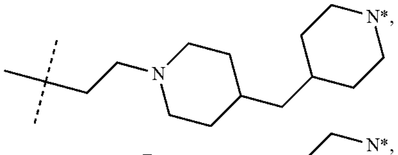
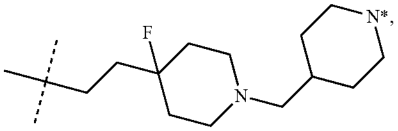
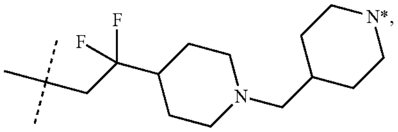
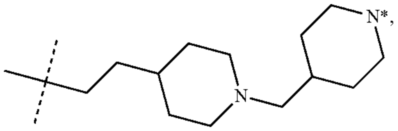
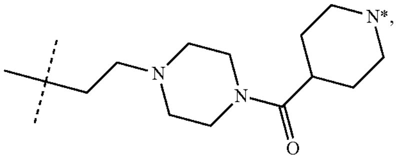
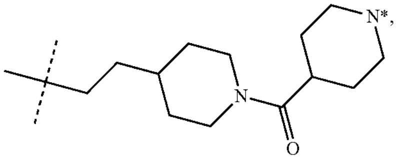
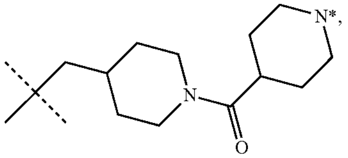
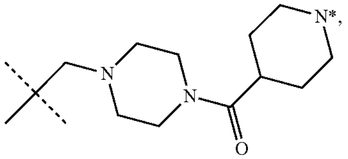
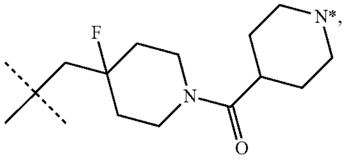
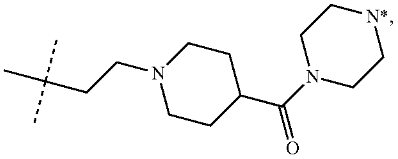
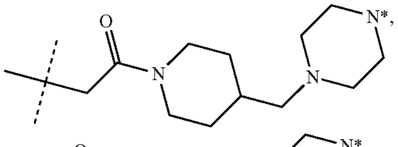
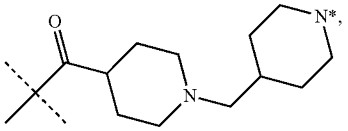
-continued
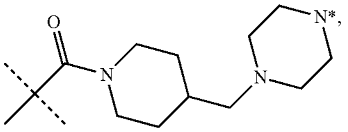
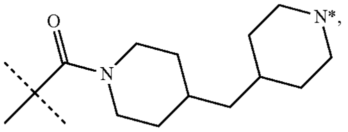
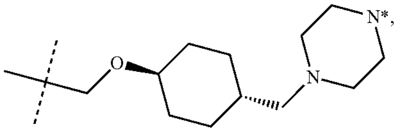
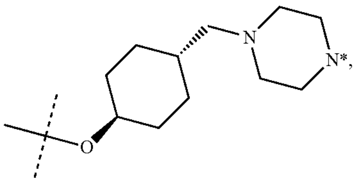
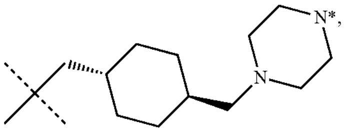
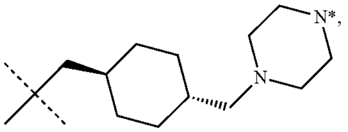
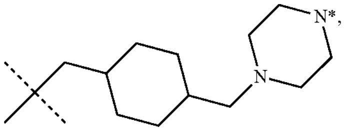
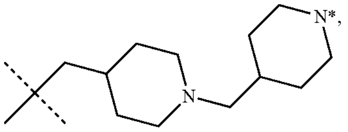
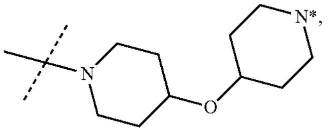
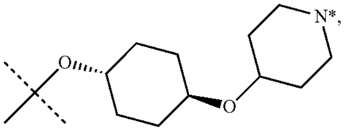
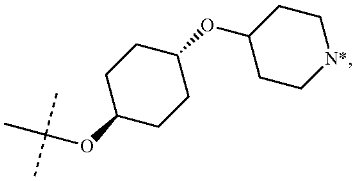

-continued
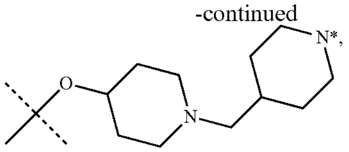
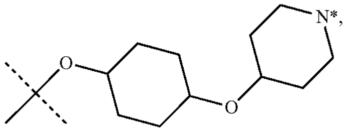
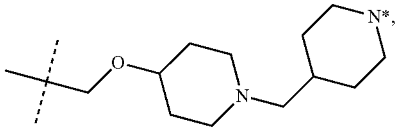
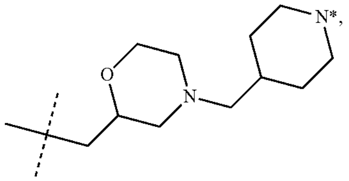
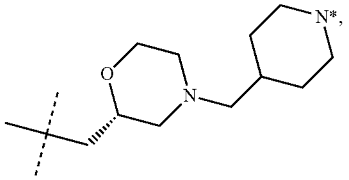
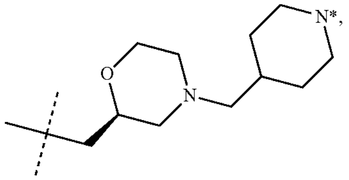
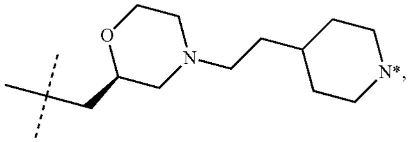
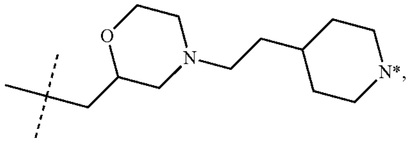
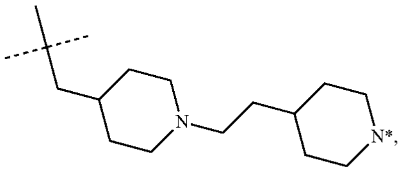
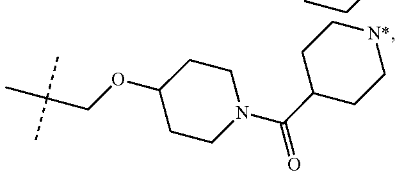
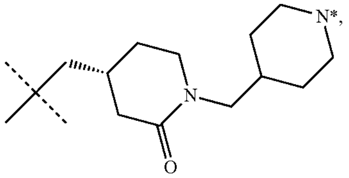
-continued
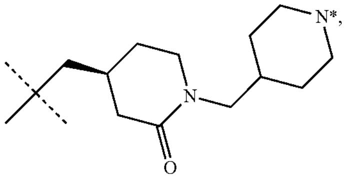
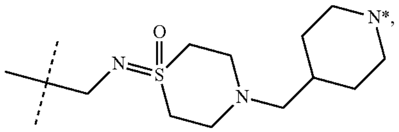
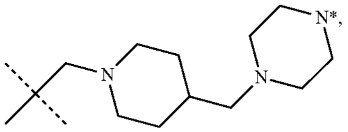
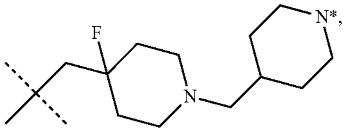
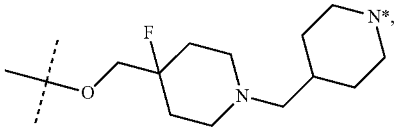
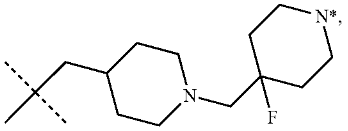
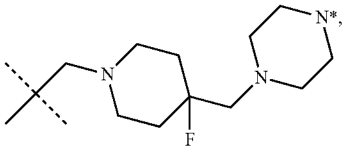
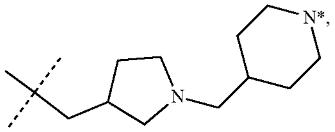
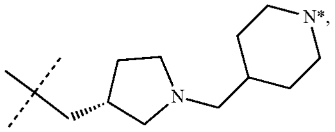
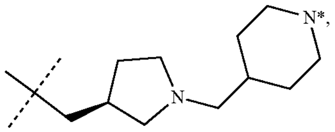
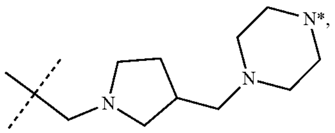
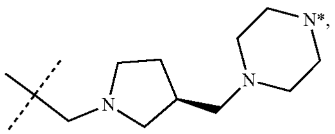

-continued
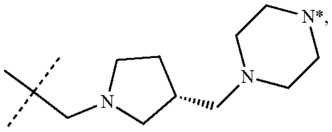
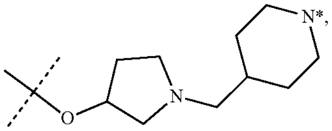
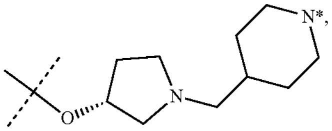
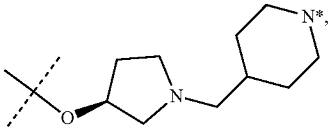
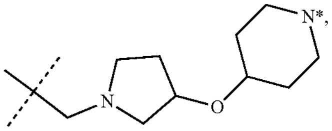
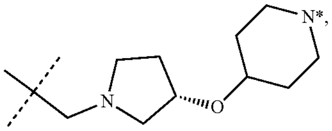
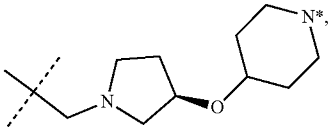
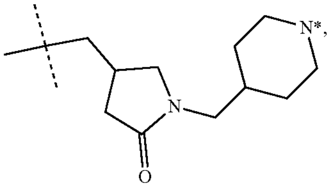
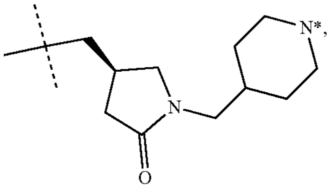
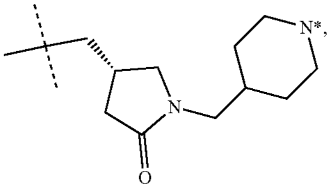
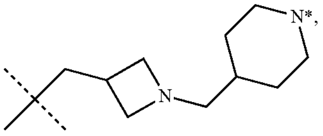
-continued
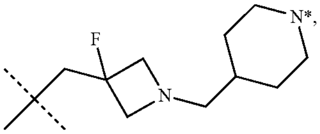
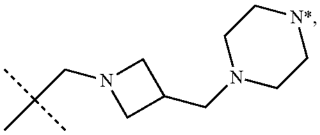
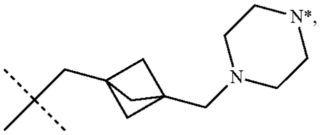
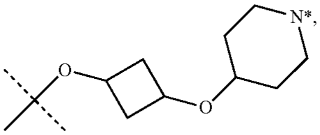
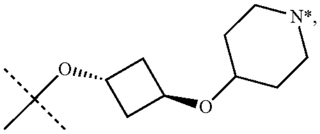
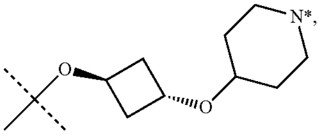
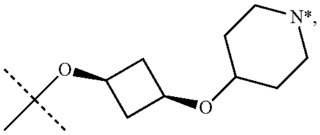
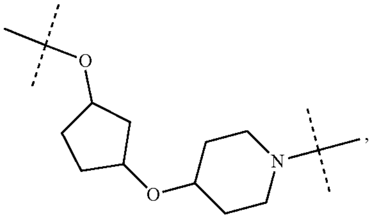
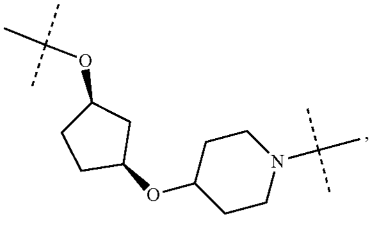
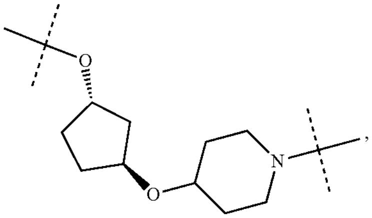

-continued
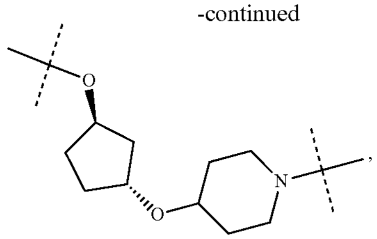
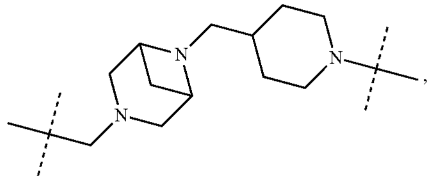
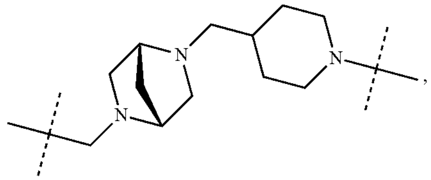
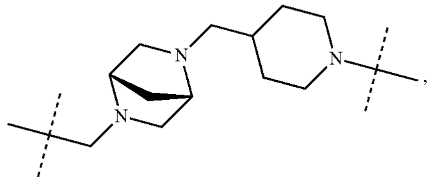
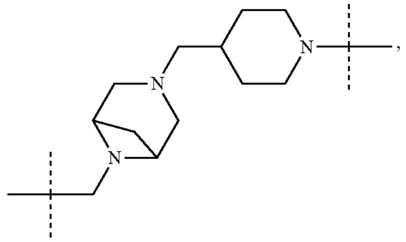
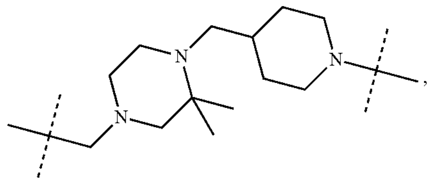
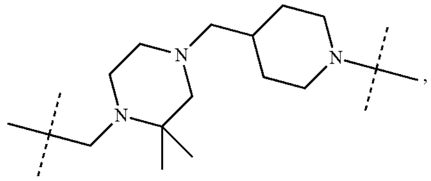
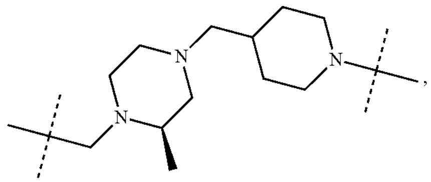
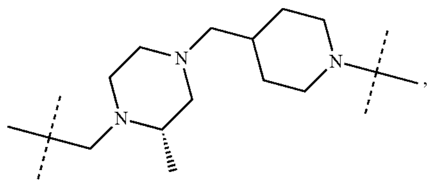
-continued
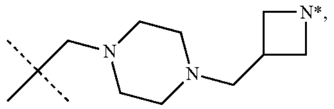
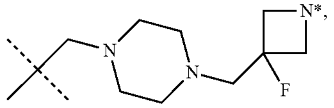
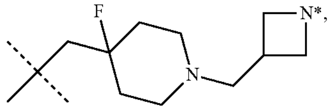
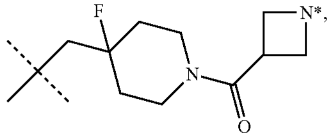
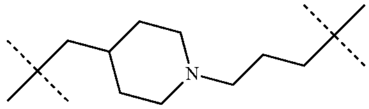
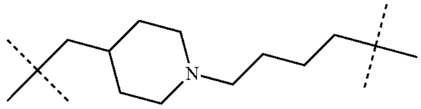
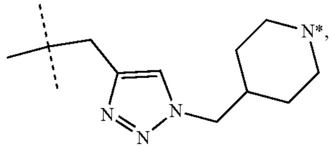
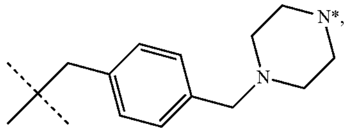
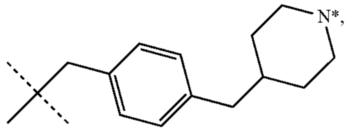
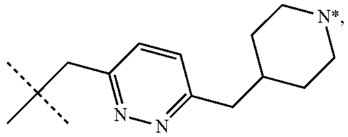
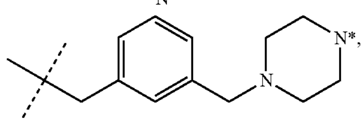
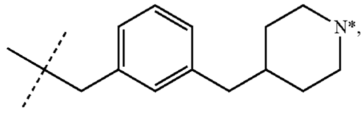
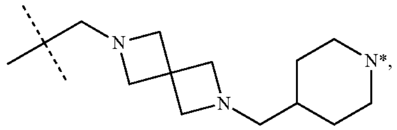
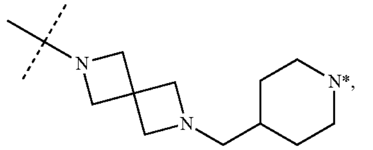

-continued
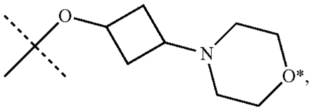
, or
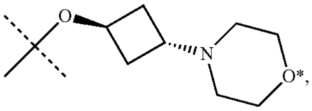
,
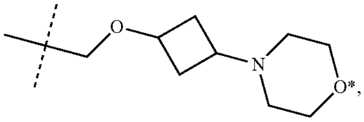
,
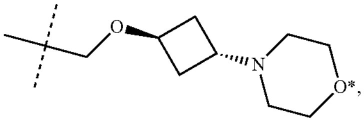
,
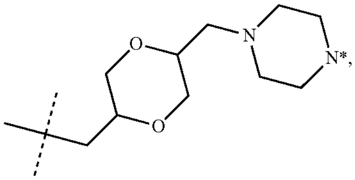
,
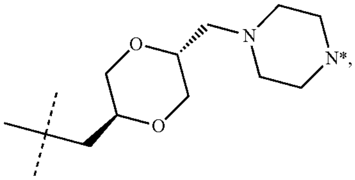
,
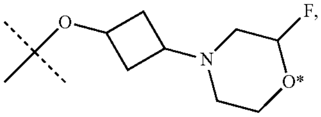
,
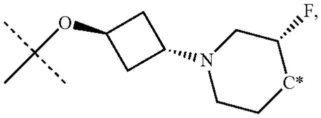
,
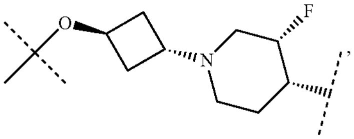
,
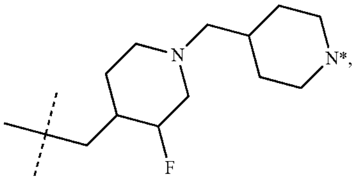
,
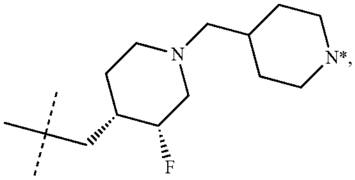
,
-continued
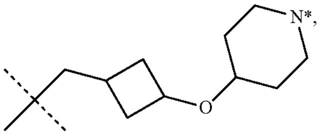
,
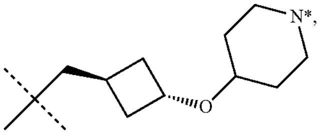
,
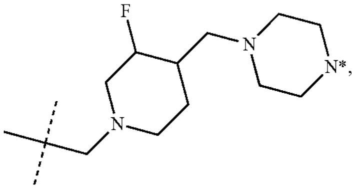
,
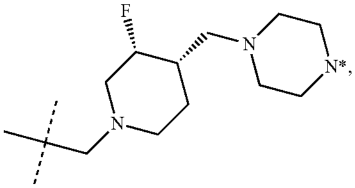
,
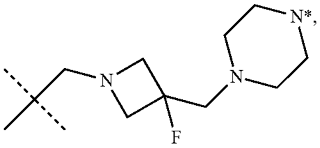
,
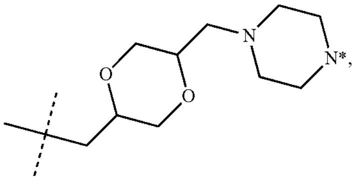
,
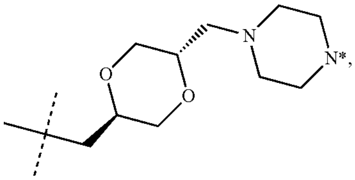
,
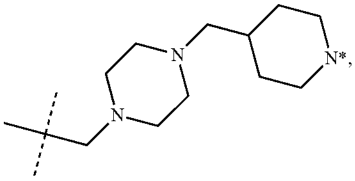
,
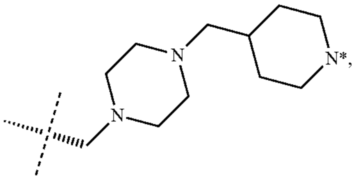
,
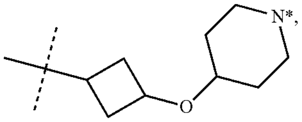
, -continued
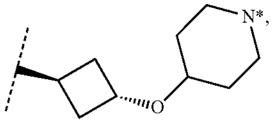
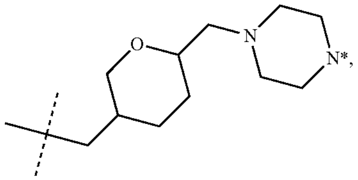
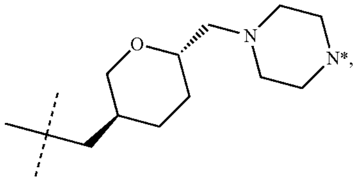
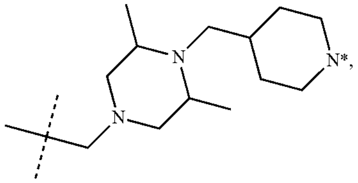
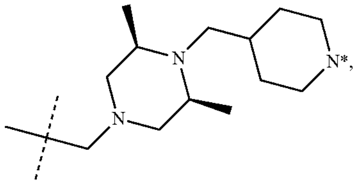
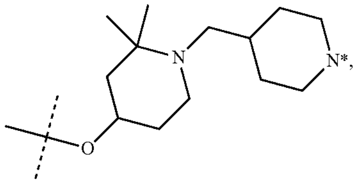
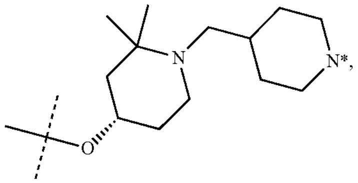
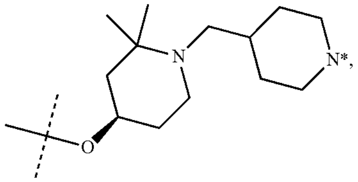
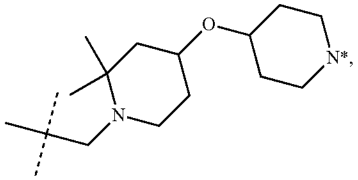
-continued
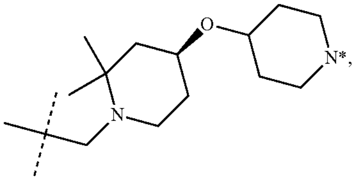
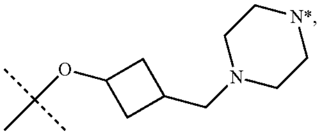
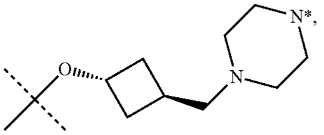
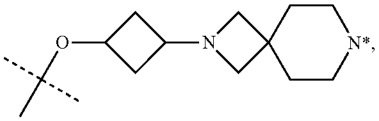
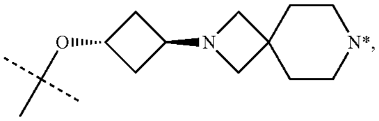
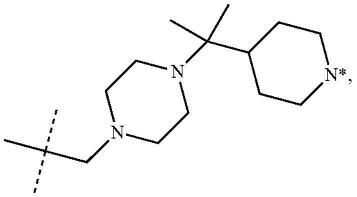
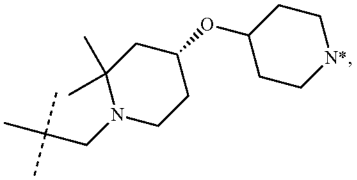
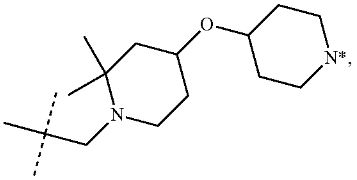
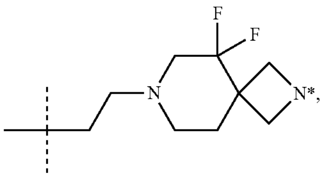
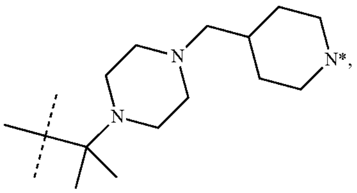

-continued
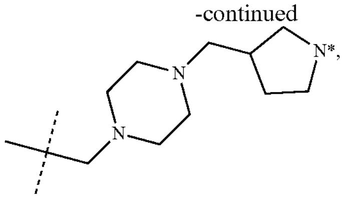
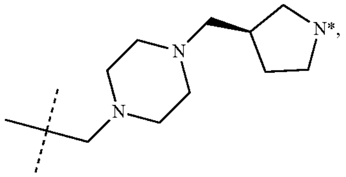
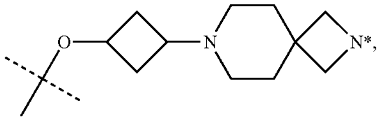
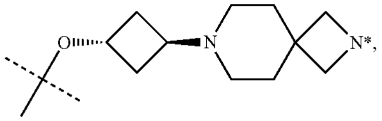
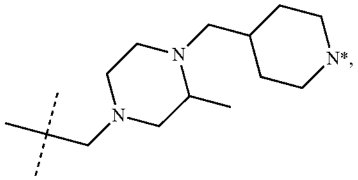
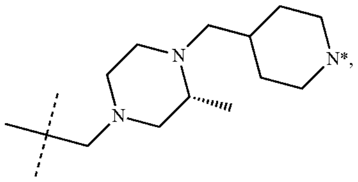
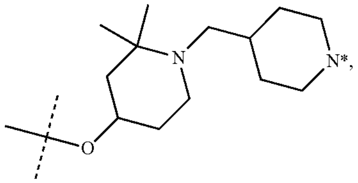
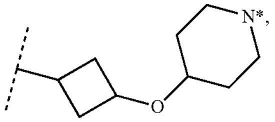
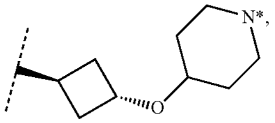
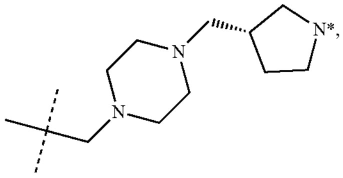
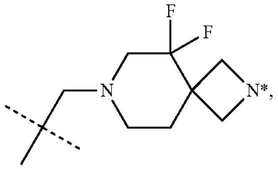
-continued
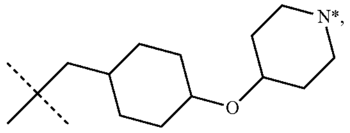
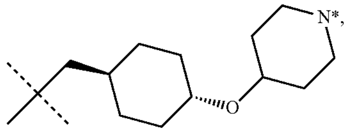
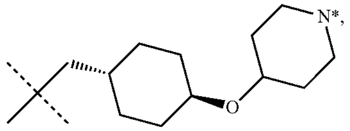
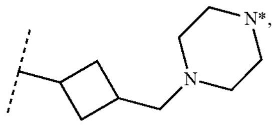
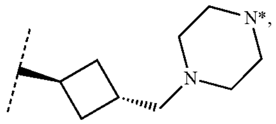
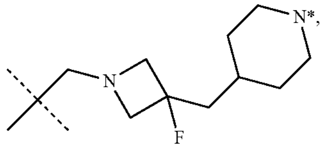
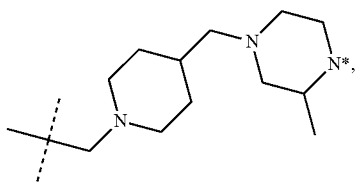
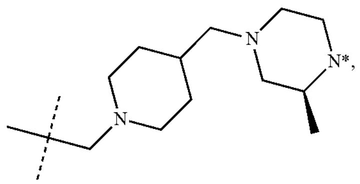
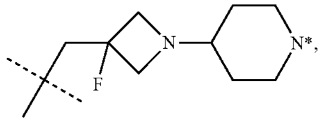
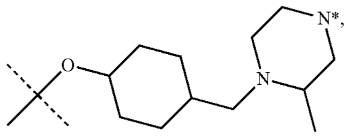
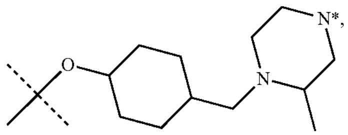
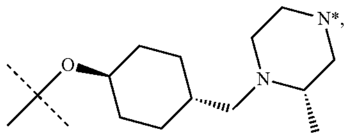

-continued

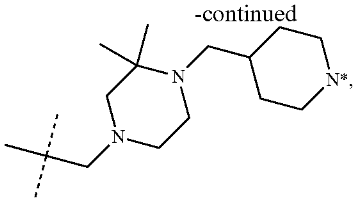

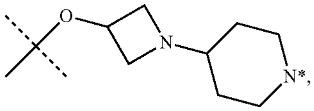

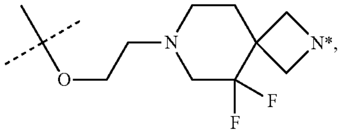

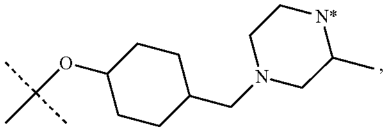

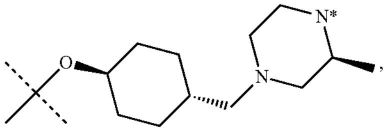

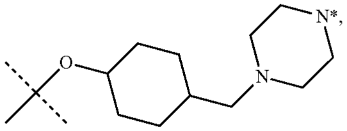

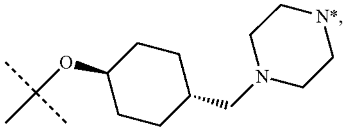

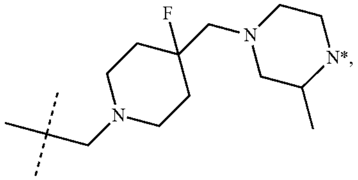

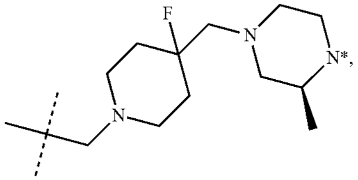

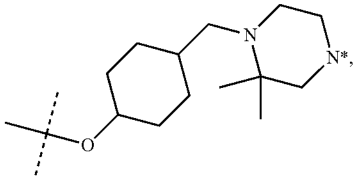

-continued

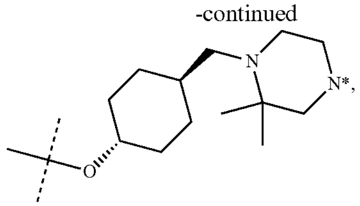

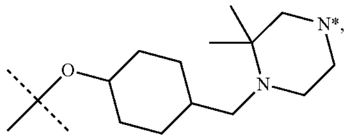

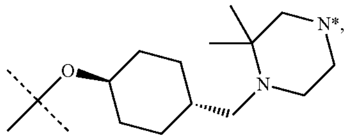

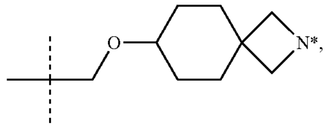

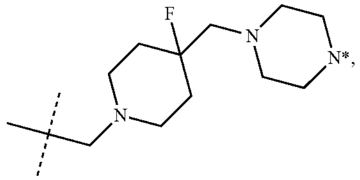

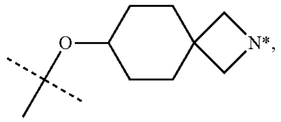

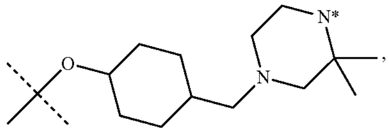

or

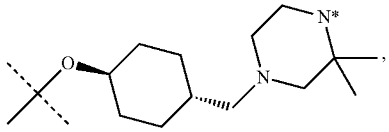

wherein N* is a nitrogen atom that is covalently linked to or shared with the ULM or the PTM, C* is a carbon atom that is covalently linked to or shared with the ULM or the PTM, and , , , and  represented the point of attachment to the CLM or the PTM.

In any aspect or embodiment described herein, the unit $A^L$ of the linker (L) comprises a structure selected from the group consisting of:

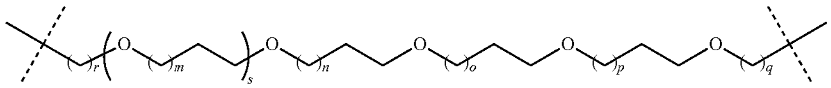

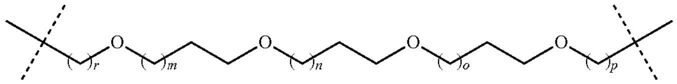

-continued
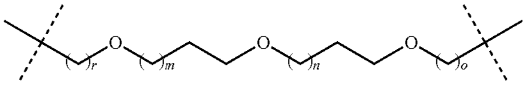
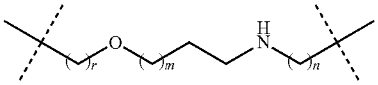
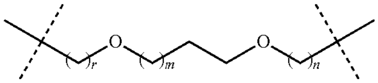
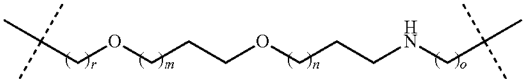
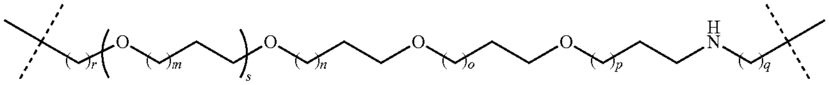
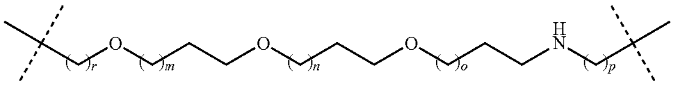
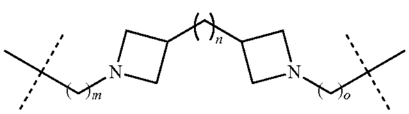
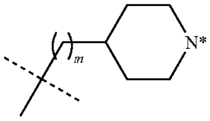
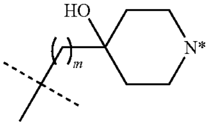
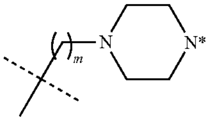
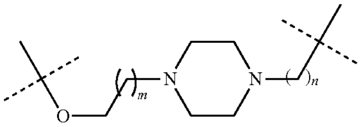
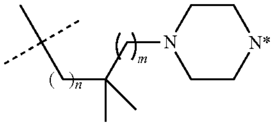
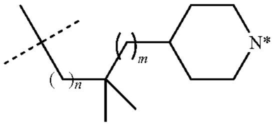
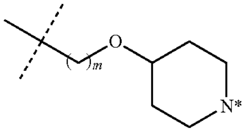
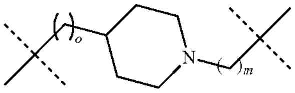
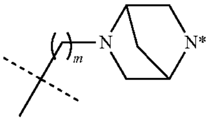
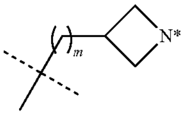
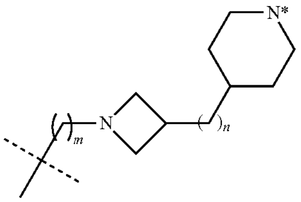
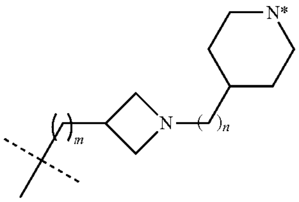
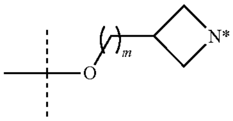
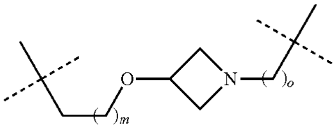
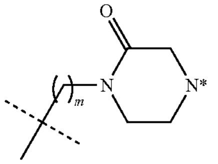
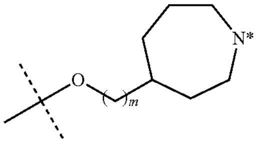
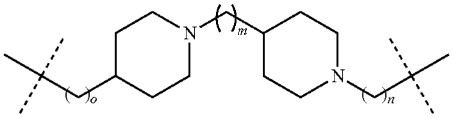
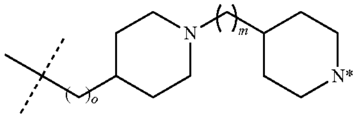
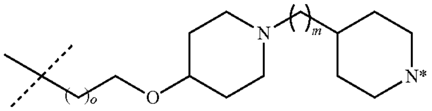
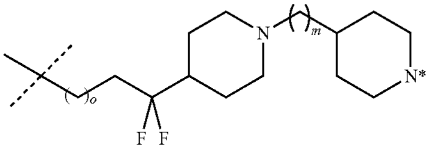
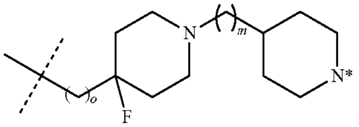
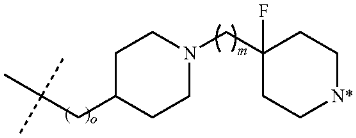
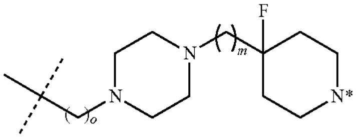
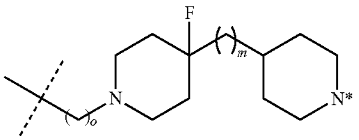
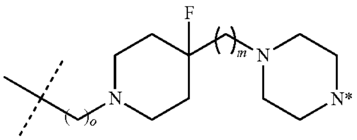
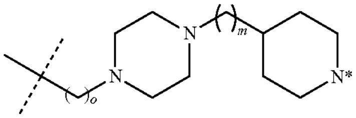

-continued
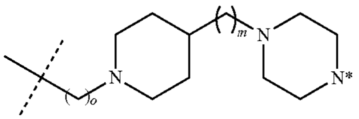 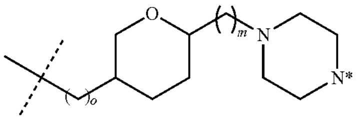 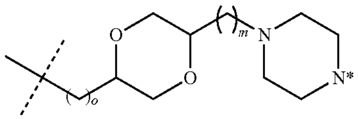
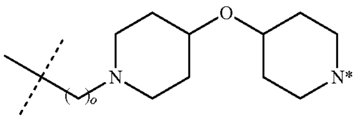 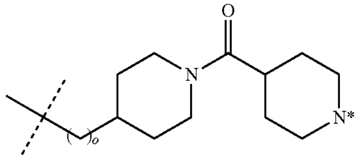 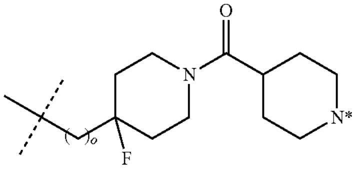
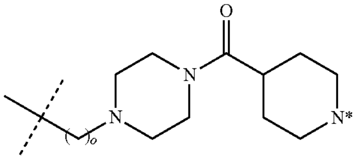 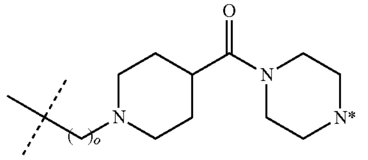 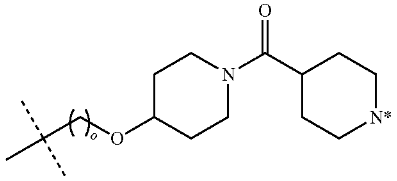
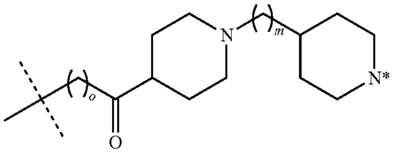 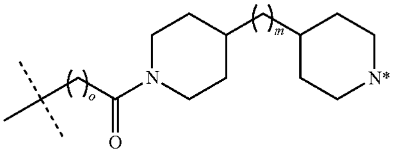
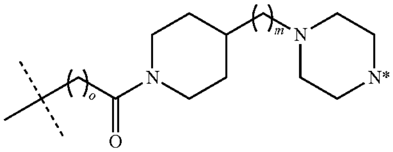 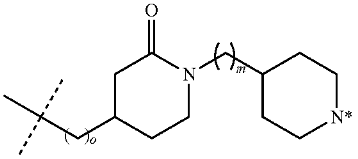 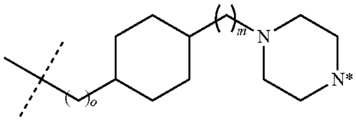
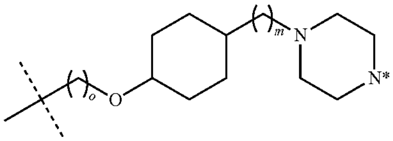 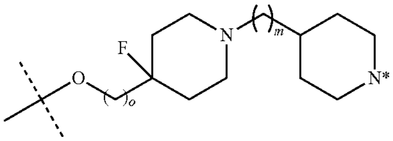
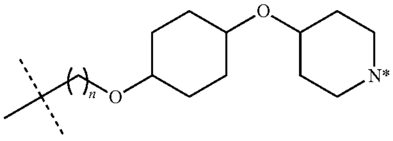 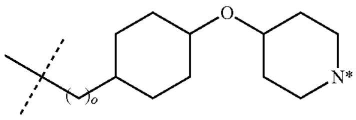 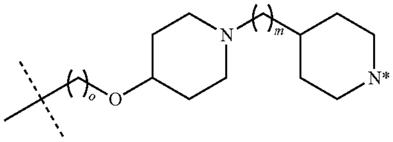
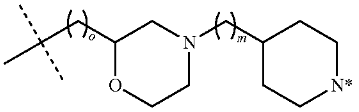 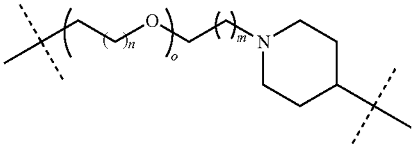 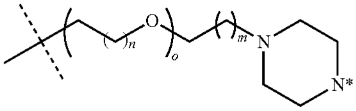
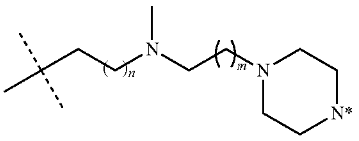 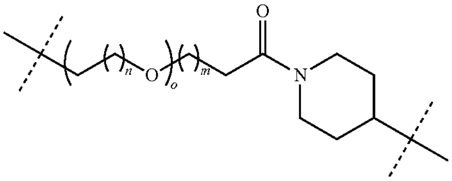
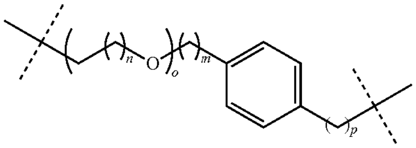 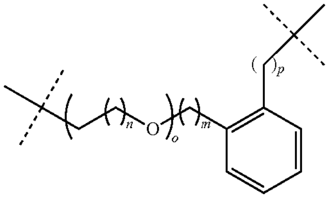 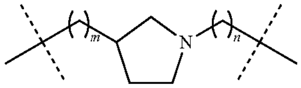

-continued
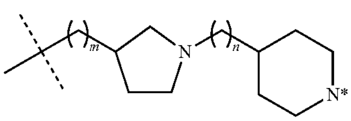
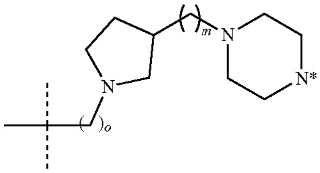
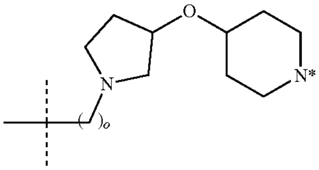
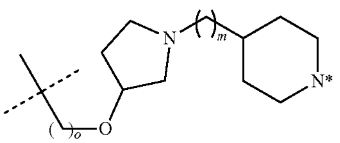
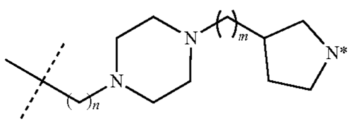
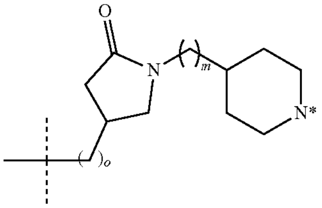
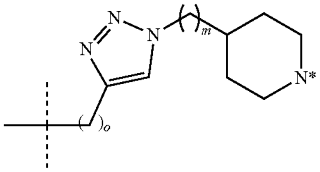
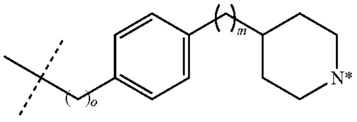
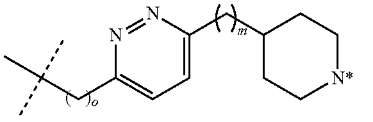
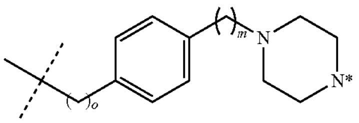
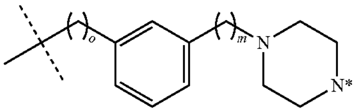
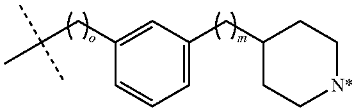
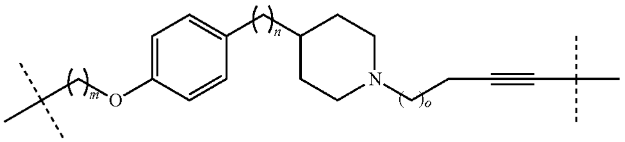
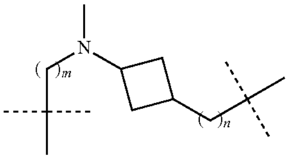
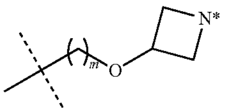
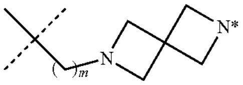
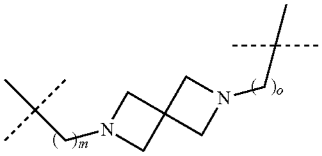
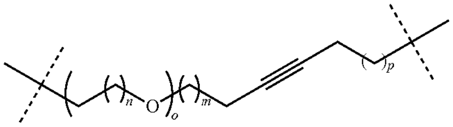
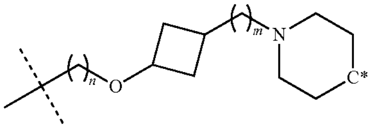
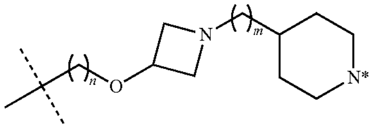
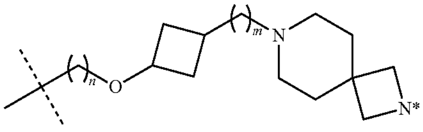
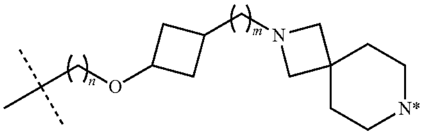
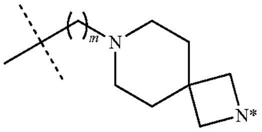
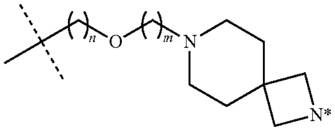
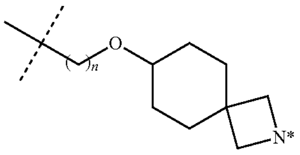
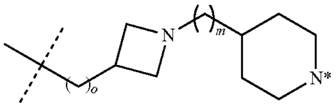
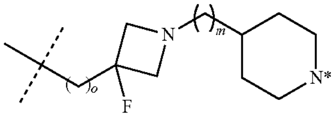
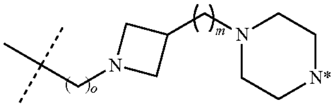
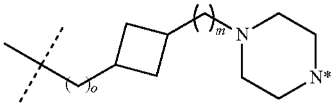
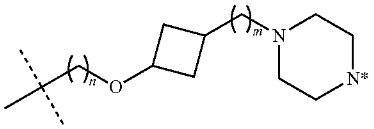
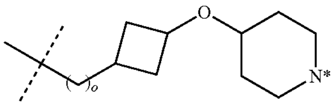
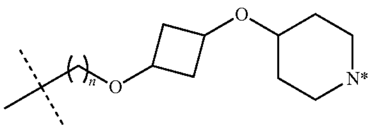

-continued

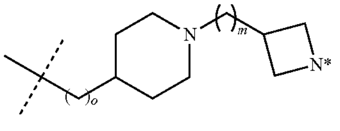

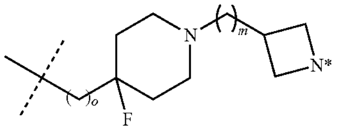

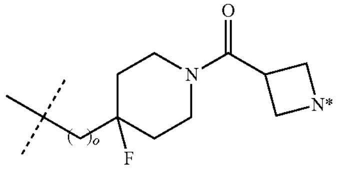

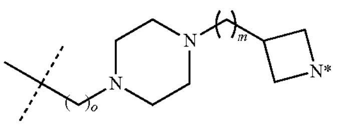

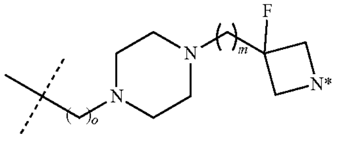

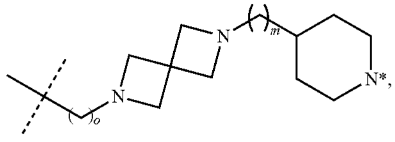, wherein:

the linker is optionally substituted with 0, 1, 2, or 3 substituents independently selected from halogen and methyl (preferably independently selected halogens);

C* is a carbon atom that is covalently linked to or shared with the CLM or the PTM;

N* is a nitrogen atom that is covalently linked to or shared with the ULM or the PTM; and each m, n, o, p, q, and r is independently 0, 1, 2, 3, 4, 5, 6, 7, 8, 9, 10, 11, 12, 13, 14, 15, 16, 17, 18, 19, or 20 (preferably, independently 0, 1, 2, or 3).

In any aspect or embodiment described herein, the unit $A^L$ of the linker (L) is selected from:

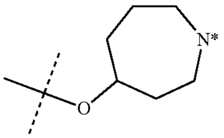

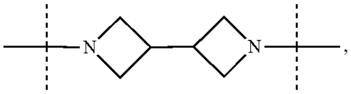,

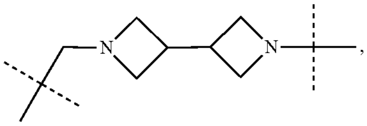,

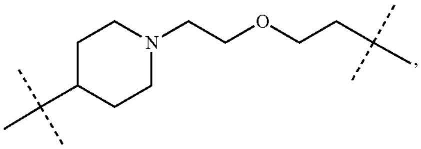,

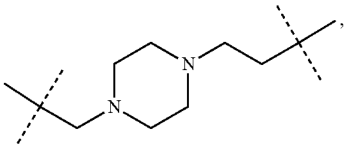,

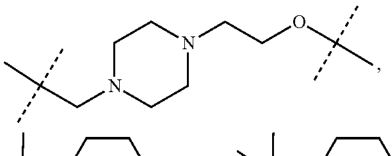,

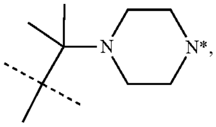,

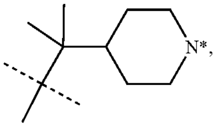,

-continued

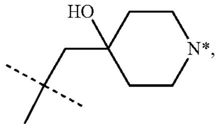,

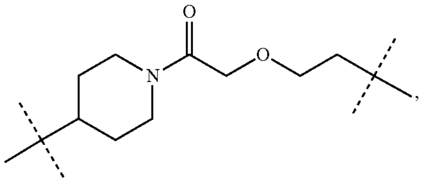,

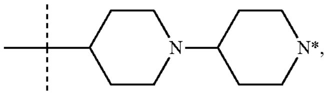,

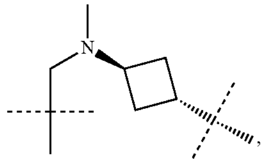,

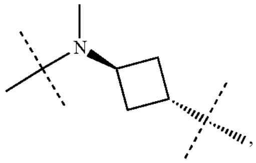,

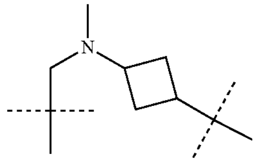,

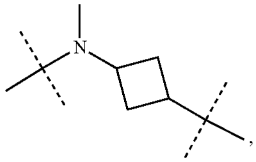,

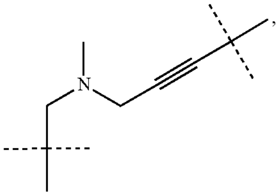,

-continued
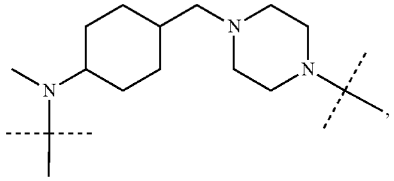
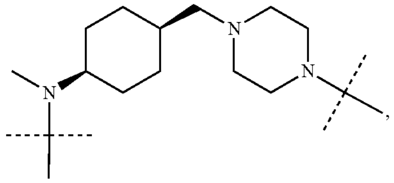
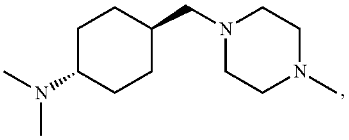
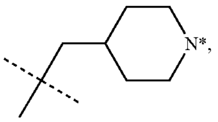
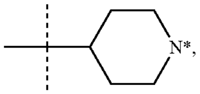
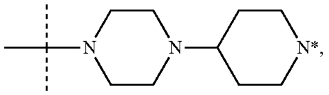
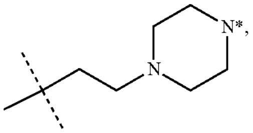
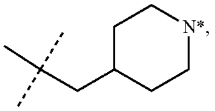
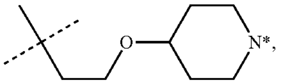
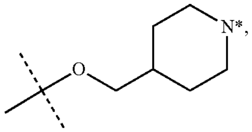
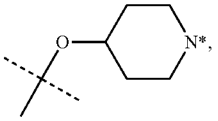
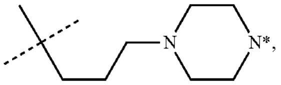
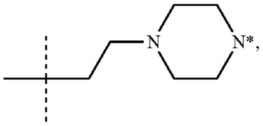
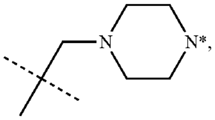
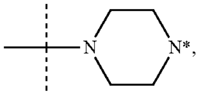
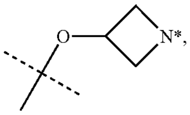
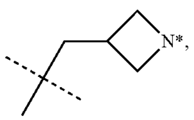
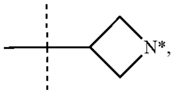
-continued
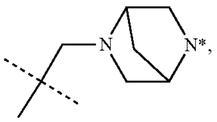
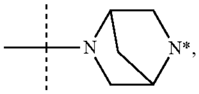
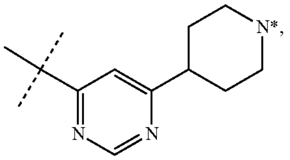
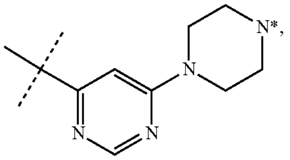
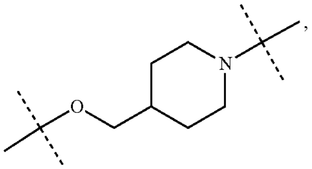
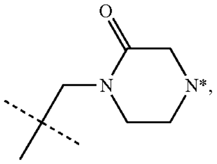
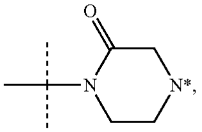
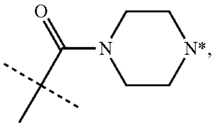
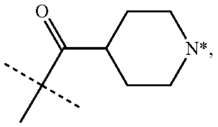
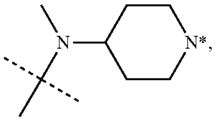
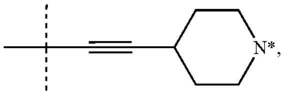
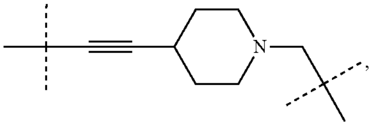
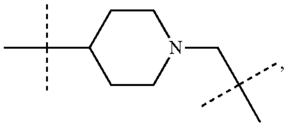
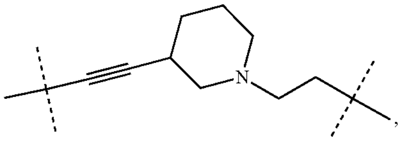
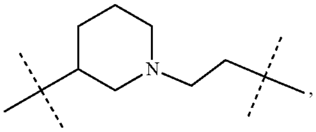
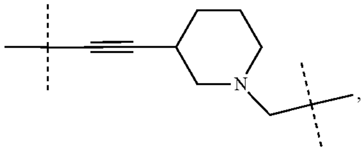

-continued
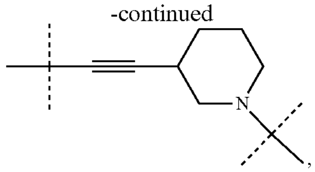
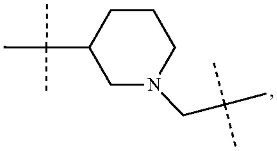
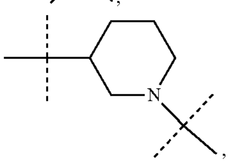
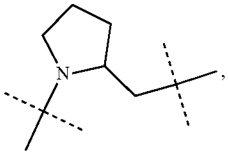
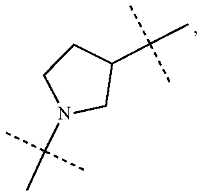
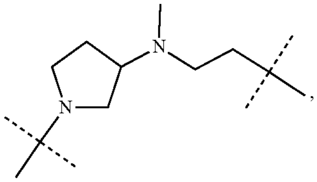
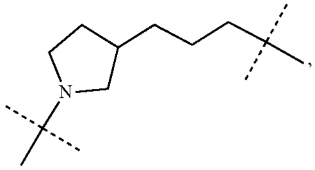
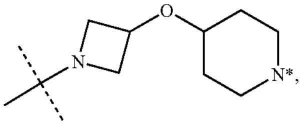
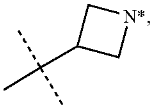
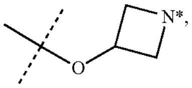
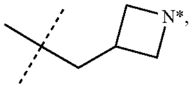
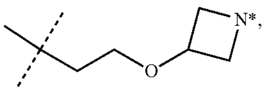
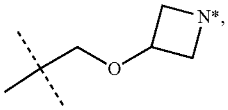
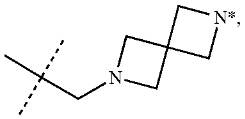
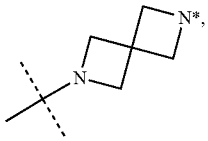
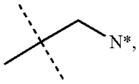
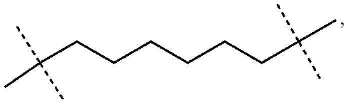
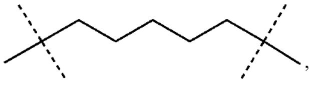
-continued
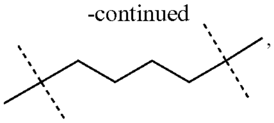
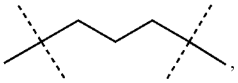
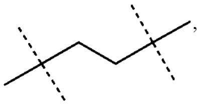
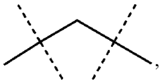
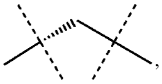
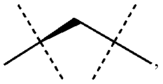
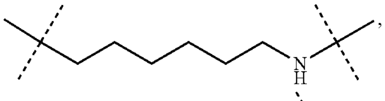
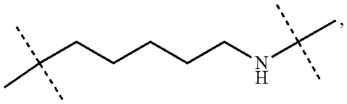
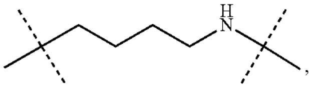
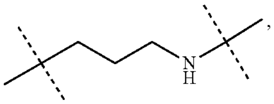
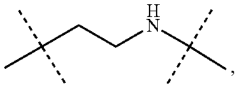
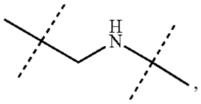
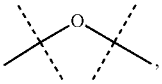
wherein N* is a nitrogen atom that is covalently linked to the ULM or PTM, or that is shared with the ULM or PTM.
In any aspect or embodiment described herein, the unit $A^L$ of linker (L) comprises a group represented by a general structure selected from the group consisting of:
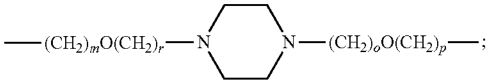
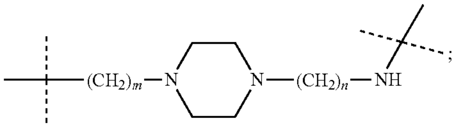
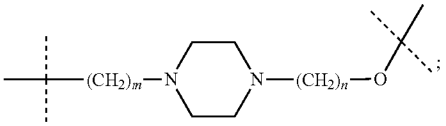
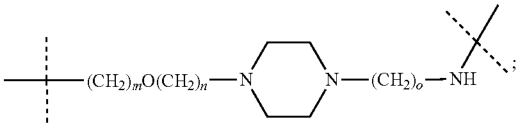
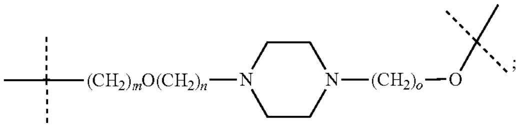

-continued
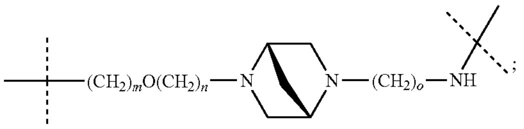
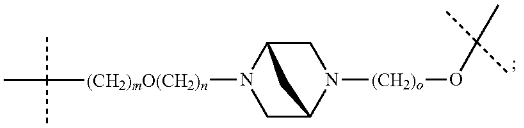
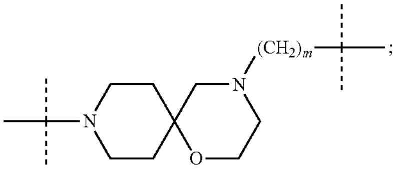
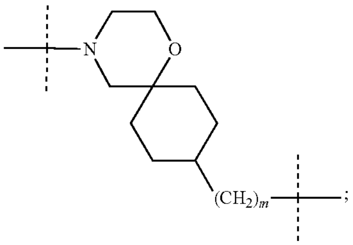
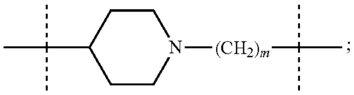
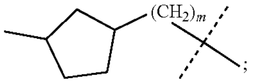
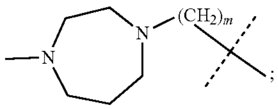
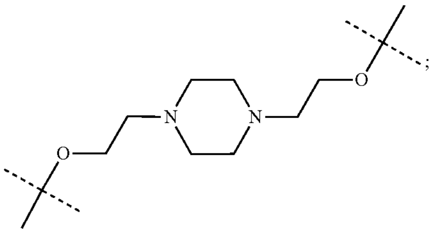
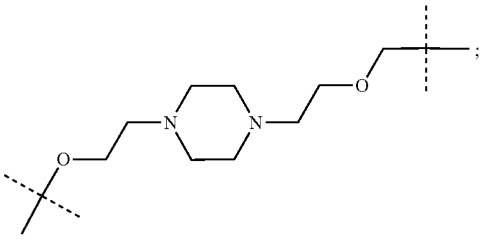
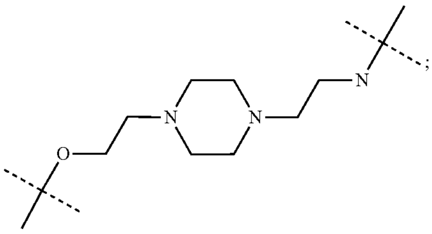
-continued
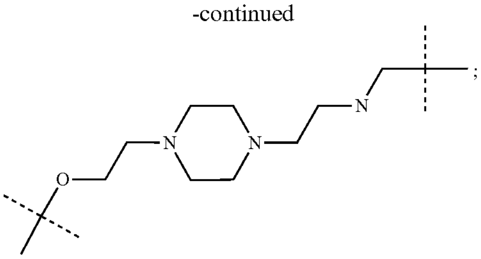
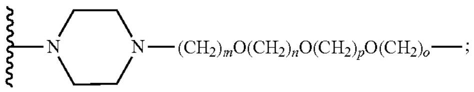
and
wherein
m, n, o, p, q, and r of the linker are independently 0, 1, 2, 3, 4, 5, 6, 7, 8, 9, 10, 11, 12, 13, 14, 15, 16, 17, 18, 19, or 20;
when m, n, o, p, q, and r are zero, N—O or O—O bond is absent,
X of the linker is H or F;
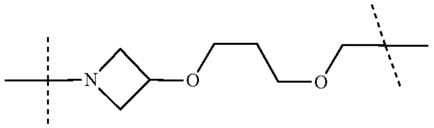
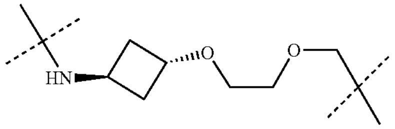
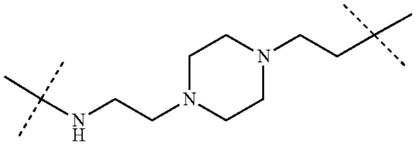
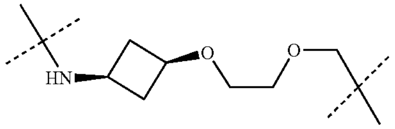
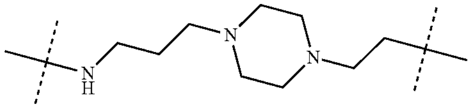
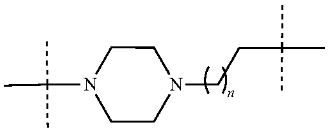
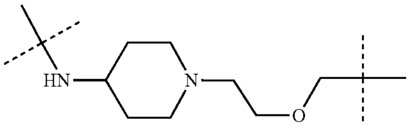
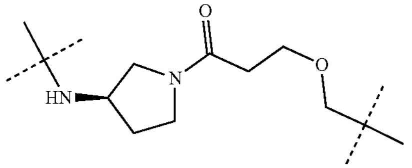

-continued
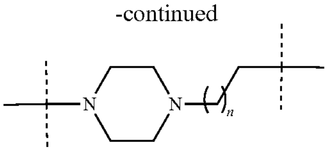
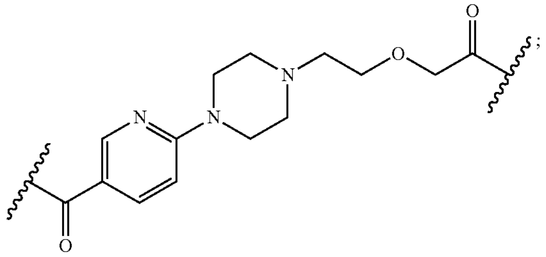
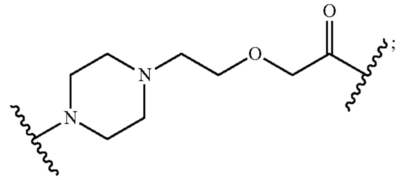
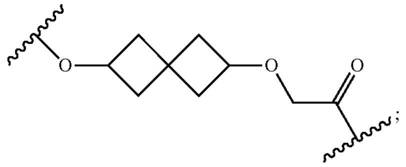
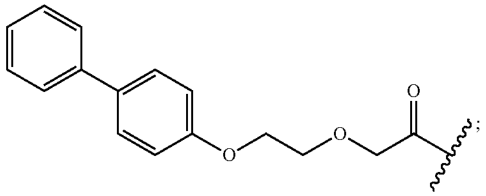
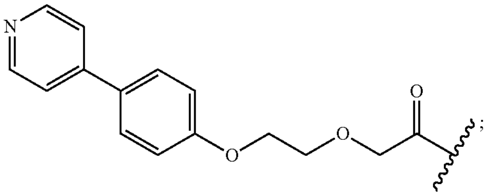
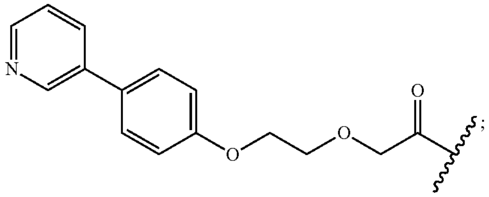
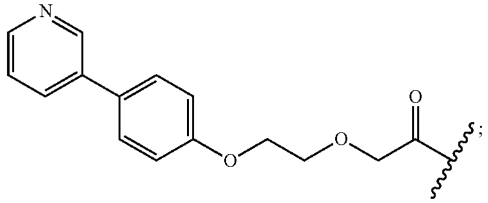
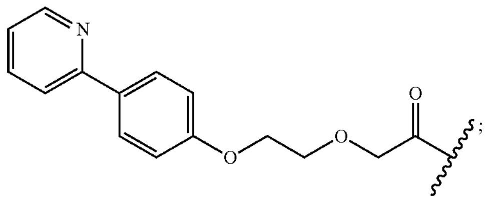
-continued
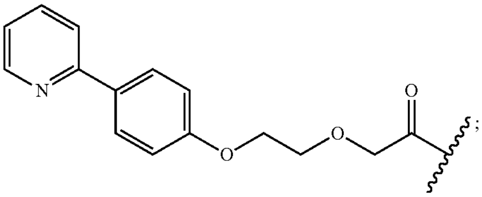
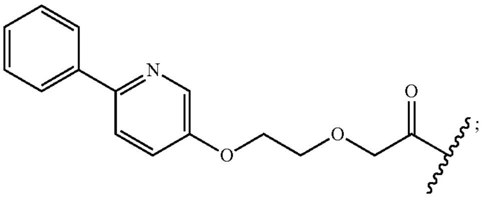
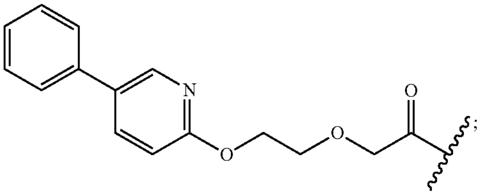
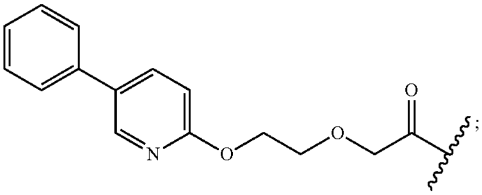
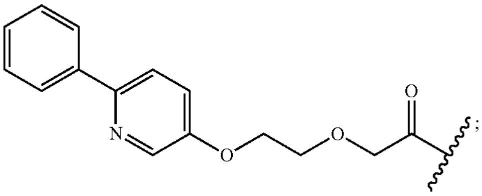
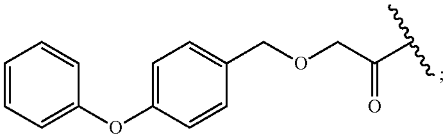
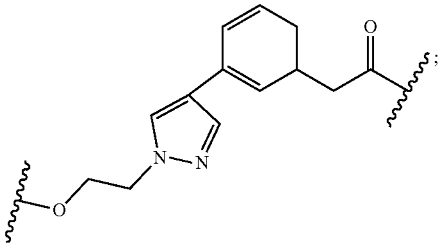
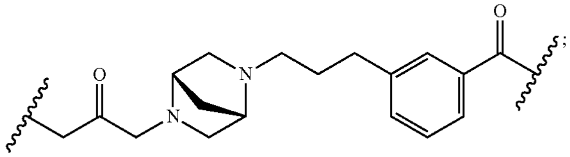
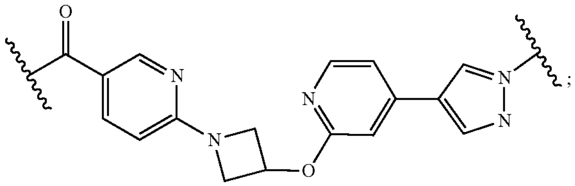

-continued
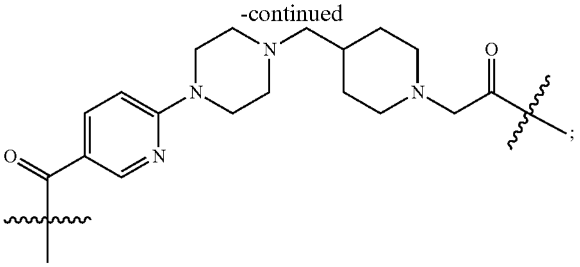
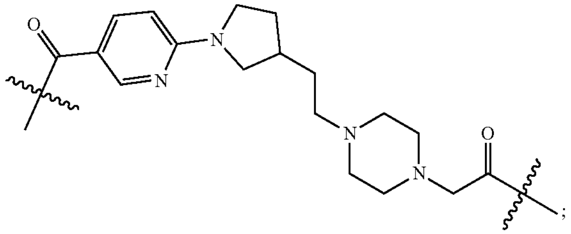
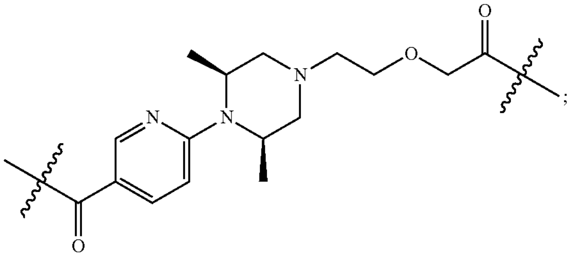
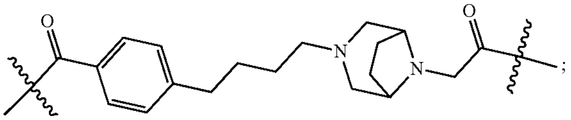
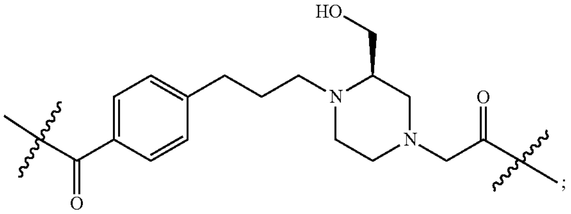
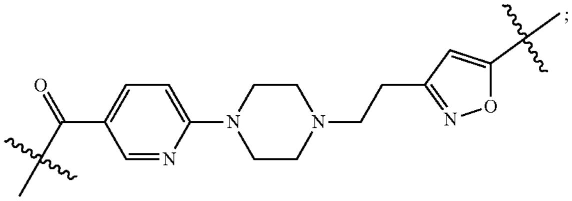
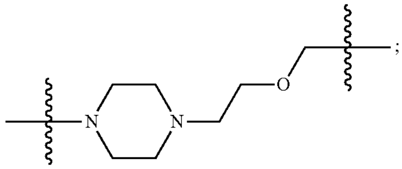
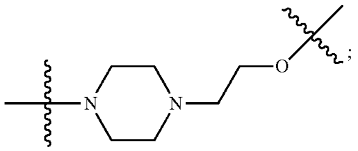
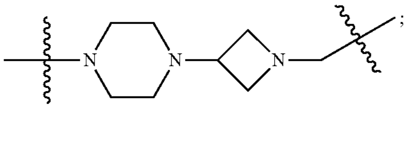
-continued
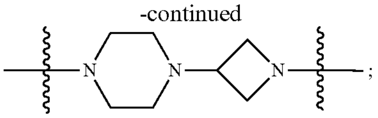
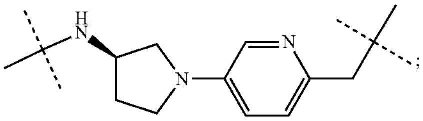
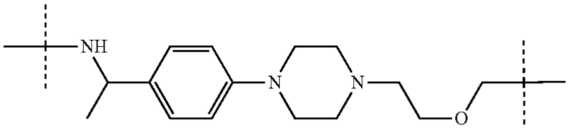
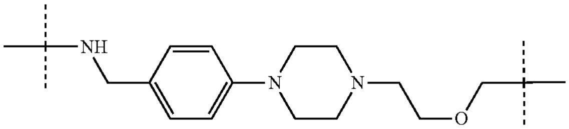
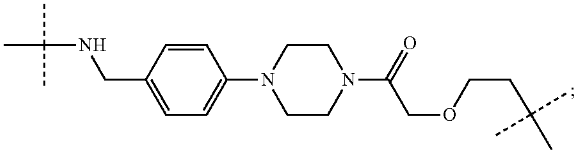
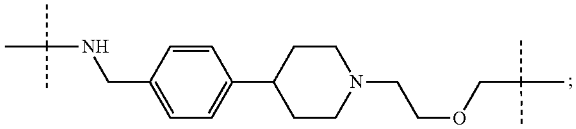
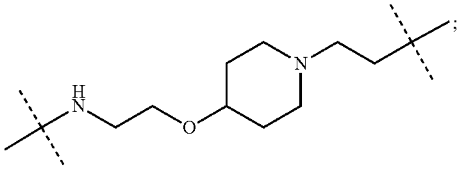
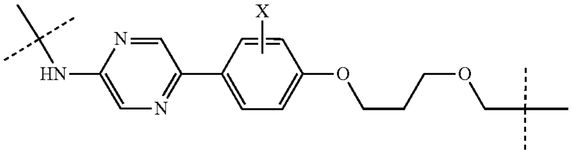
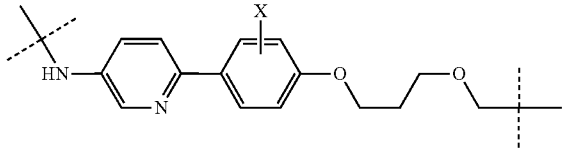
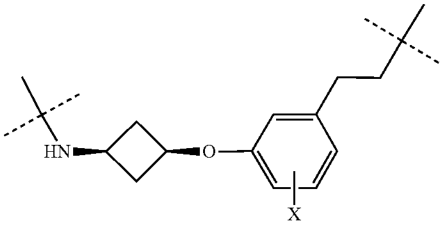
X=H, F
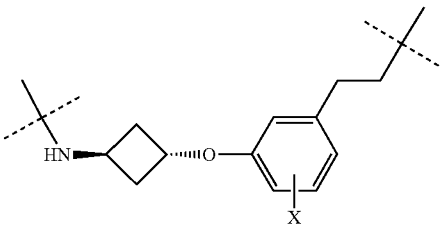

-continued
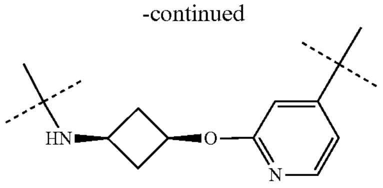
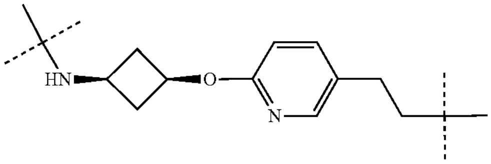
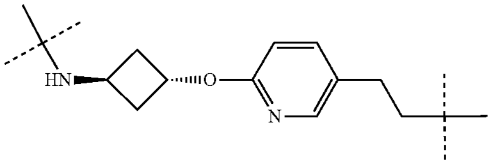
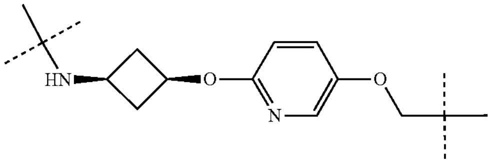
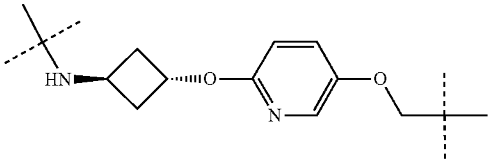
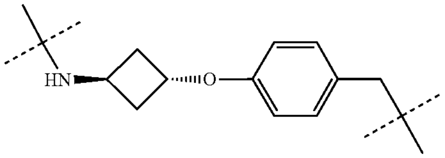
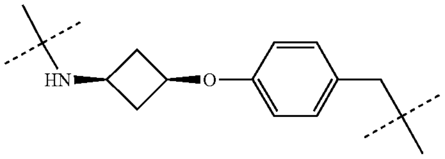
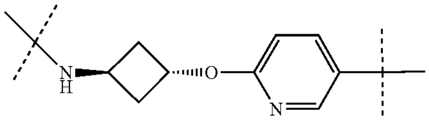
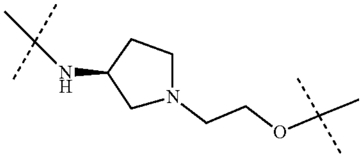
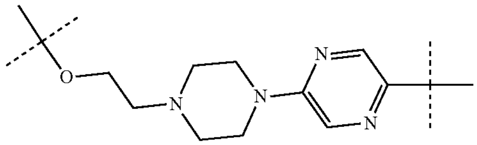
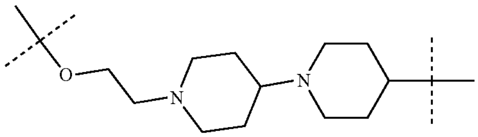
-continued
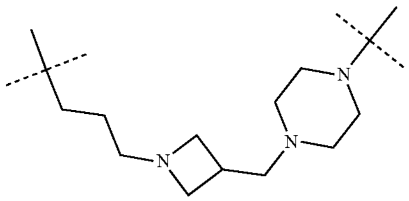
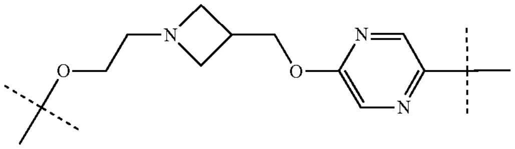
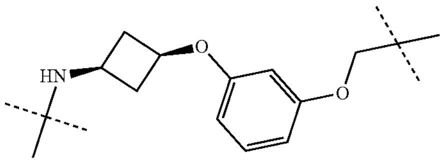
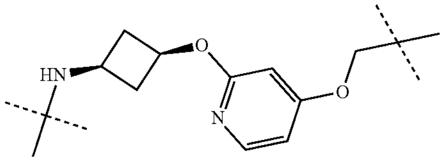
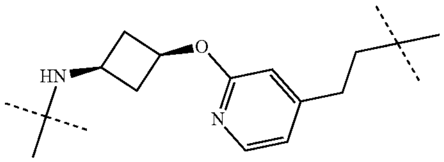
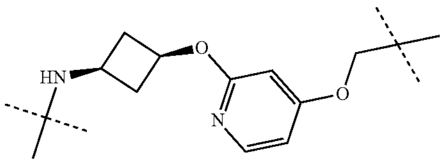
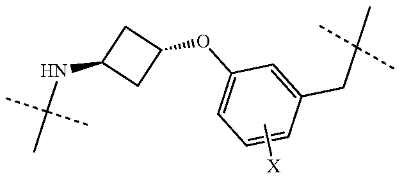
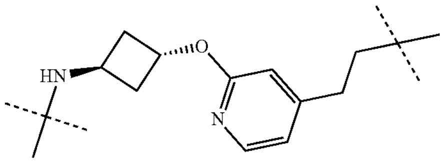
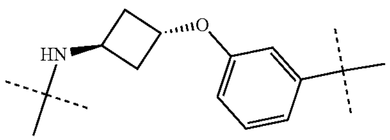
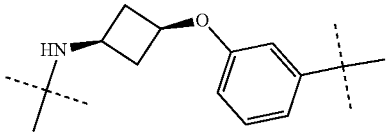

-continued
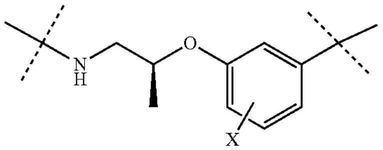
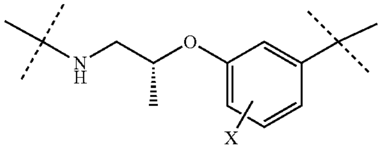
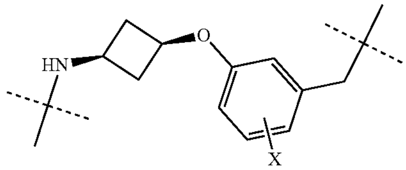
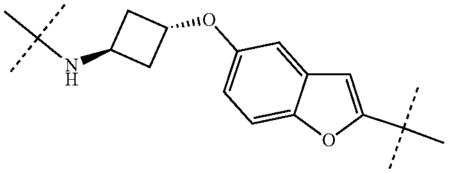
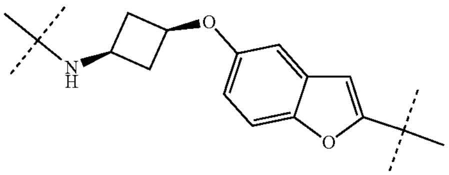
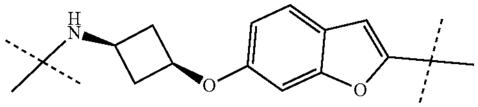
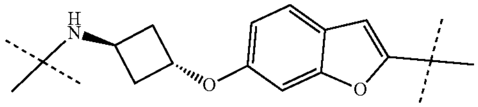
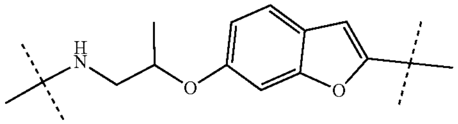
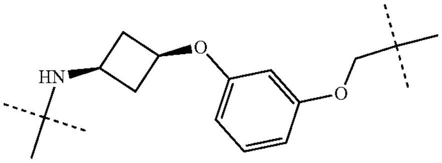
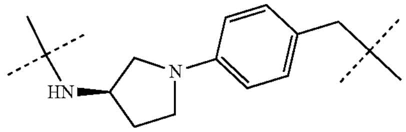
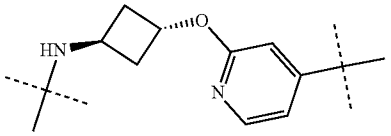
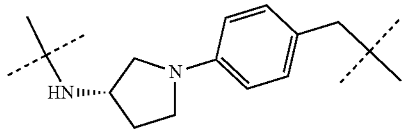
-continued
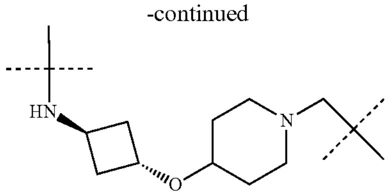
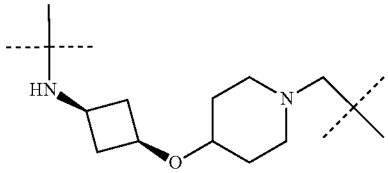
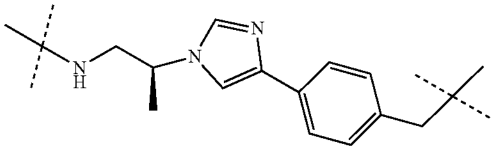
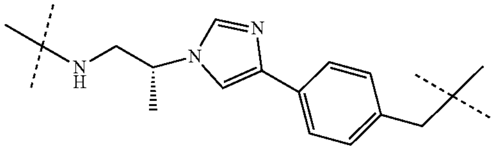
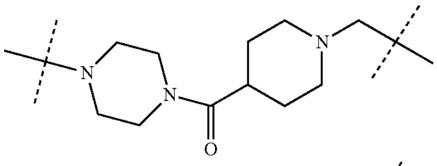
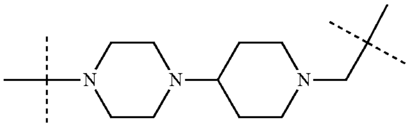
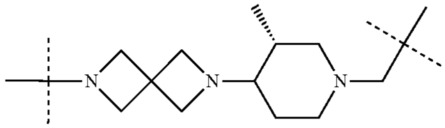
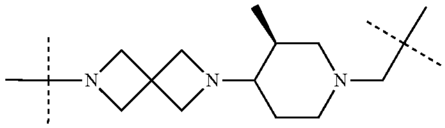
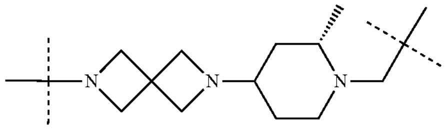
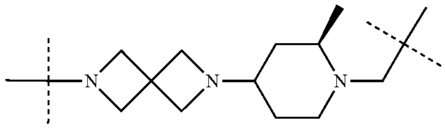
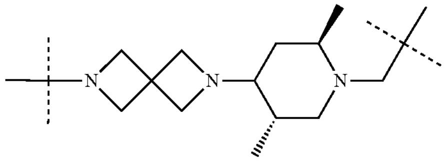
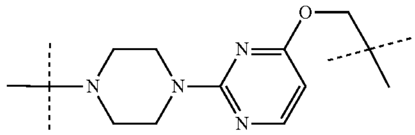

-continued
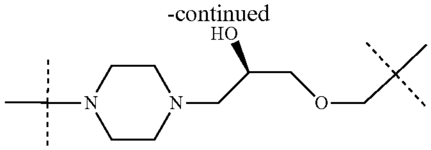
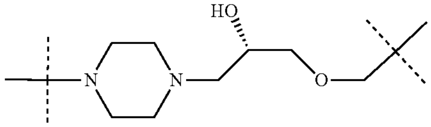
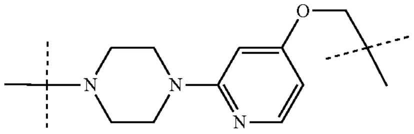
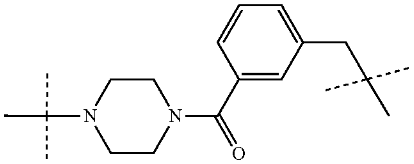
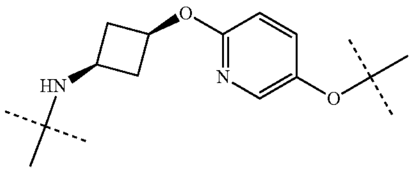
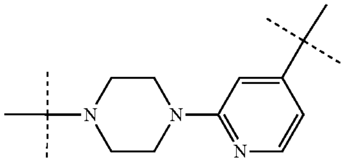
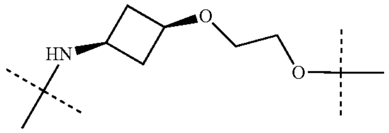
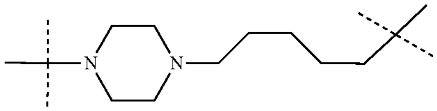
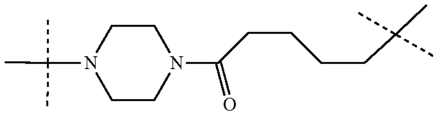
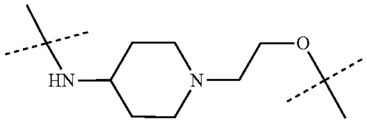
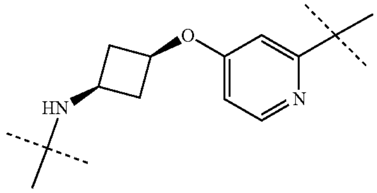
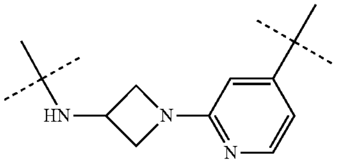
-continued
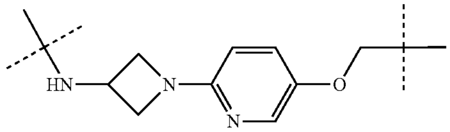
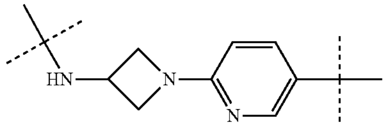
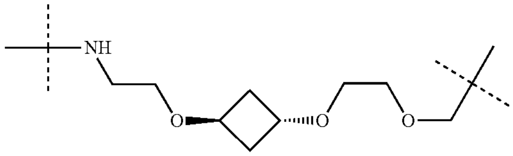
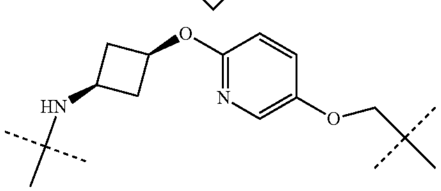
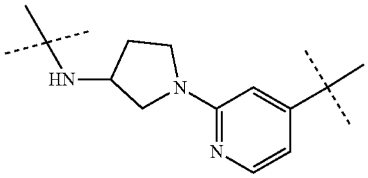
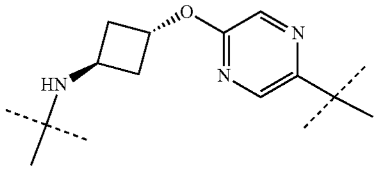
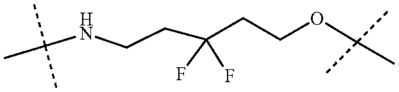
wherein each n and m of the linker can independently be 0, 1, 2, 3, 4, 5, or 6.
In any aspect or embodiment described herein, the unit $A^L$ of linker (L) is selected from the group consisting of:
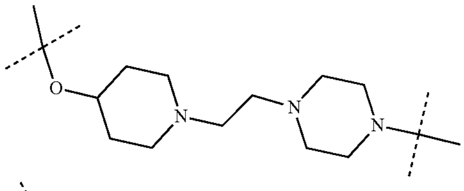
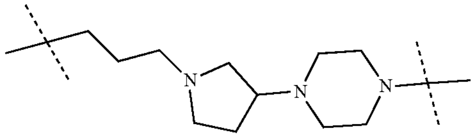
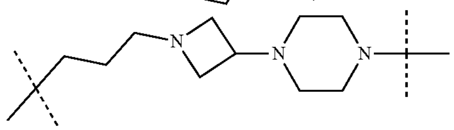

-continued
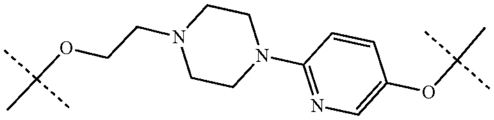
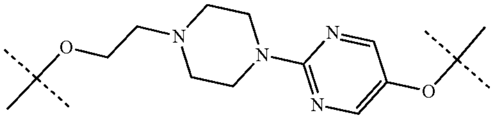
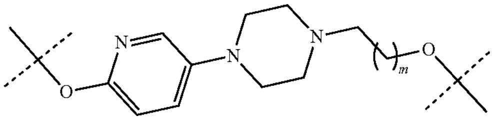
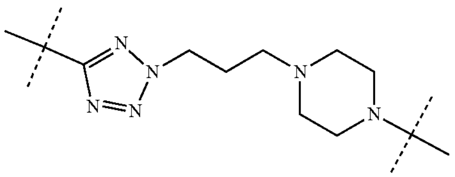
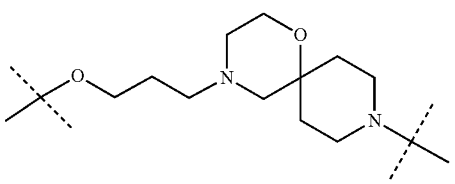
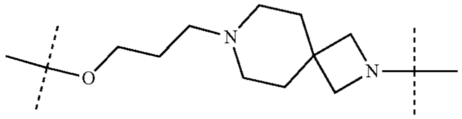
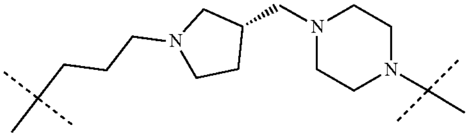
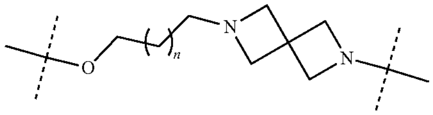
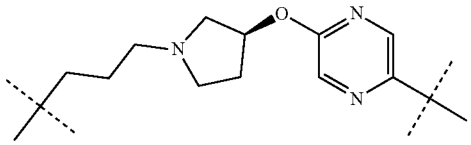
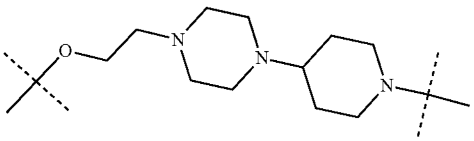
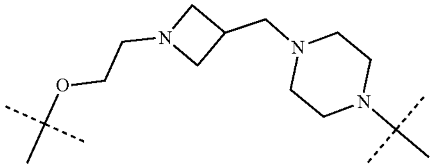
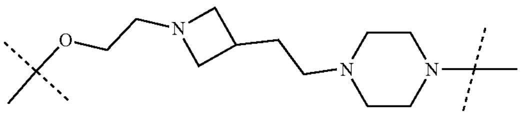
-continued
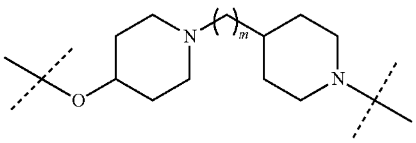
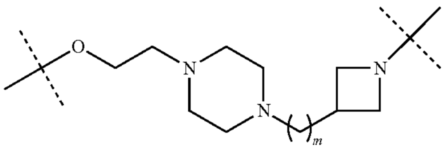
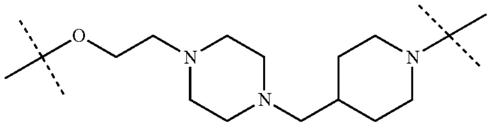
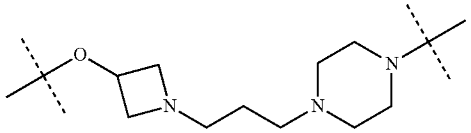
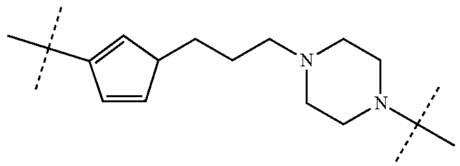
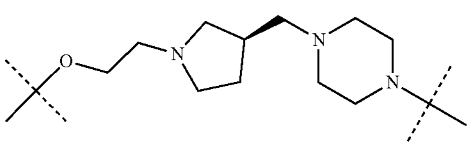
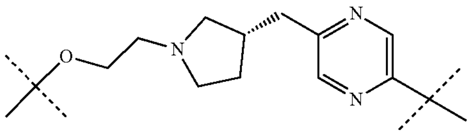
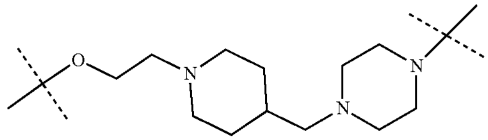
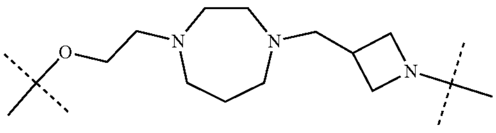
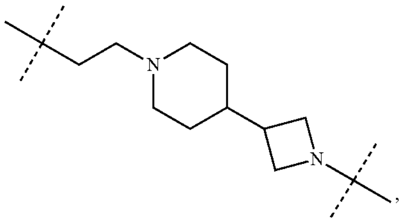
,
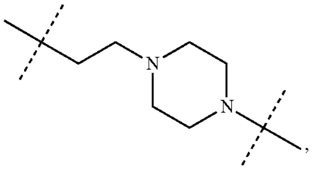
, -continued
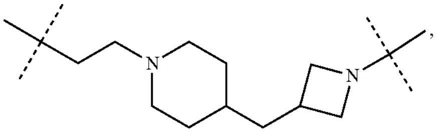
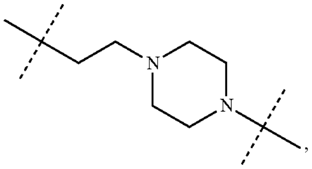
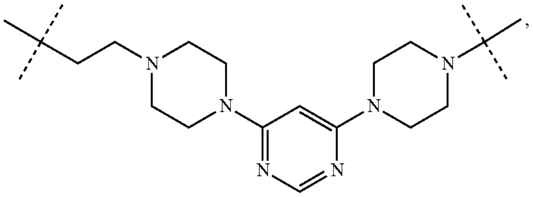
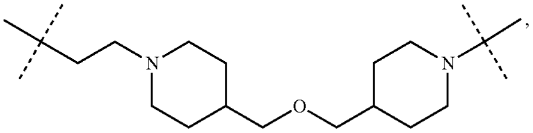
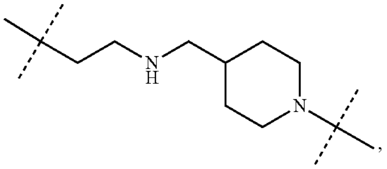
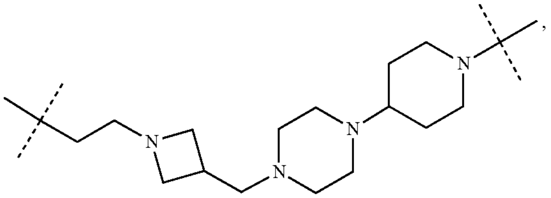
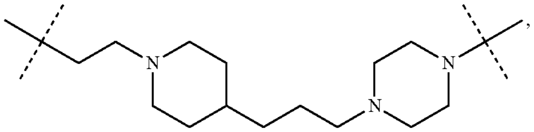
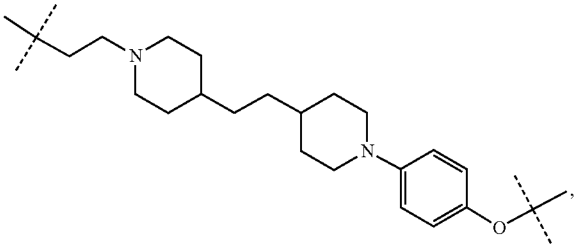
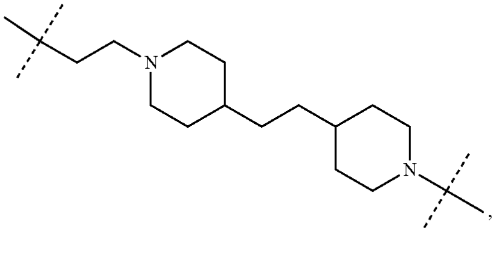
and
-continued
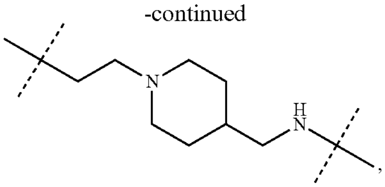
wherein each m and n is independently selected from 0, 1, 2, 3, 4, 5, or 6.
In any aspect or embodiment described herein, the unit $A^L$ of linker (L) is selected from the group consisting of:
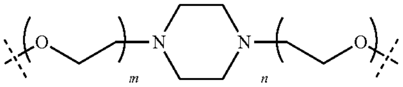
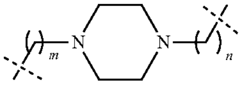
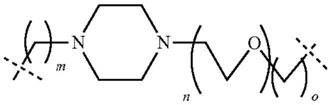
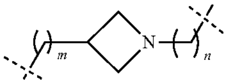
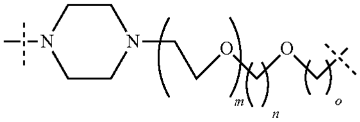
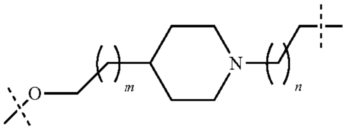
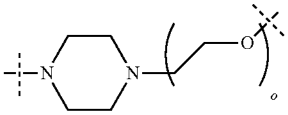
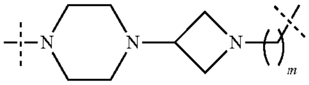
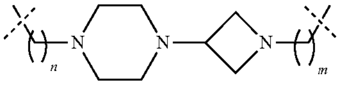
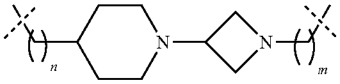
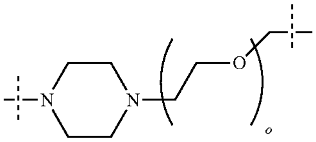
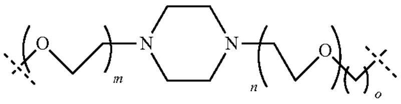
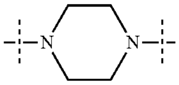
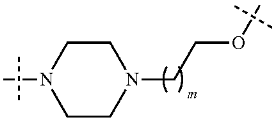

-continued
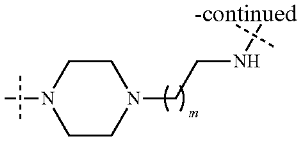
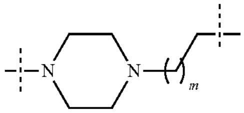
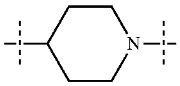
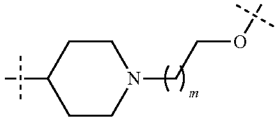
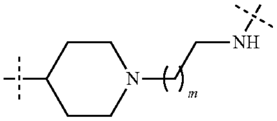
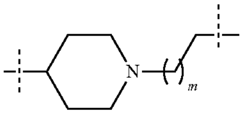
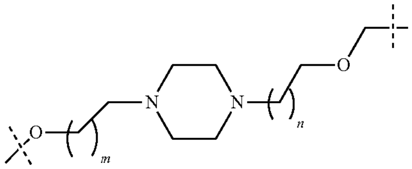
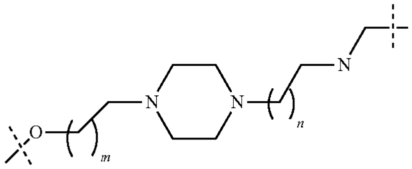
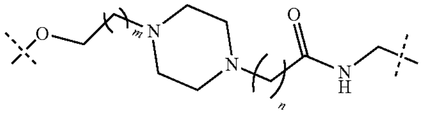
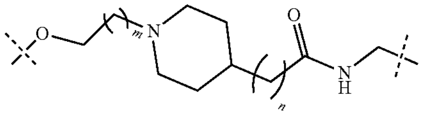
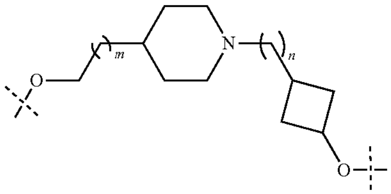
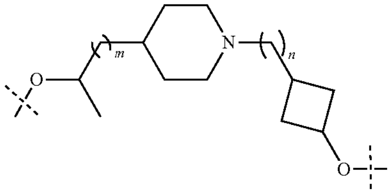
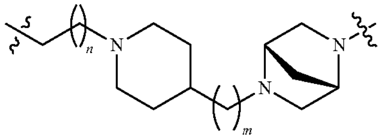
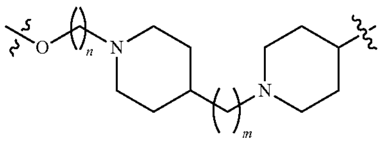
-continued
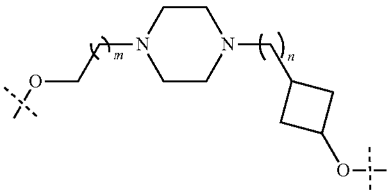
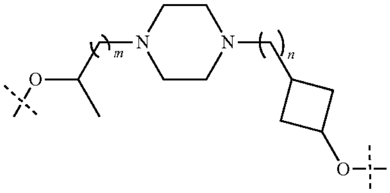
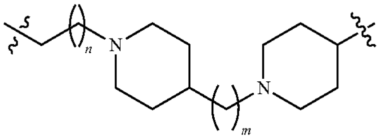
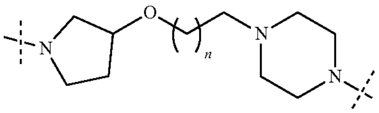
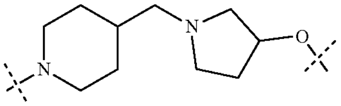
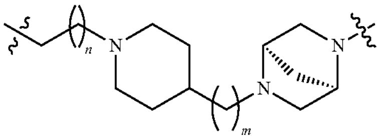
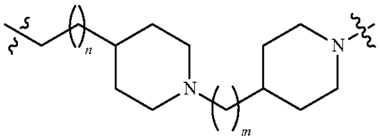
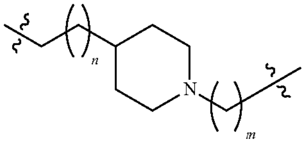
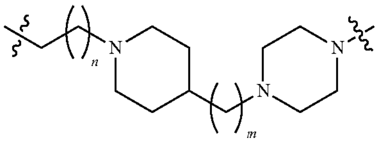
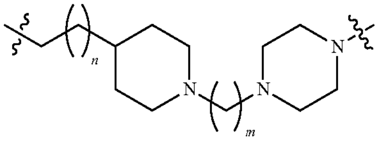
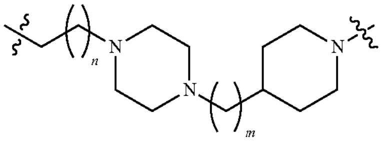

-continued
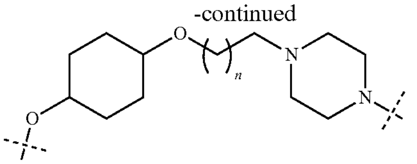
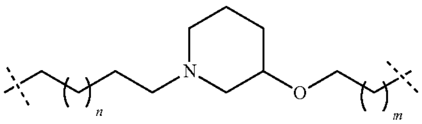
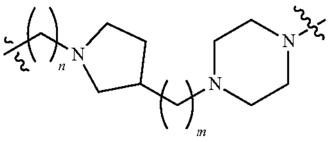
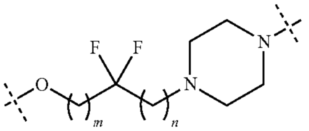
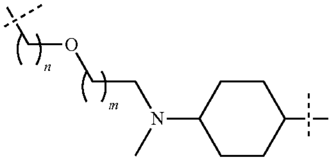
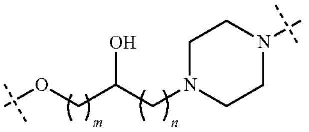
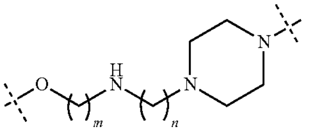
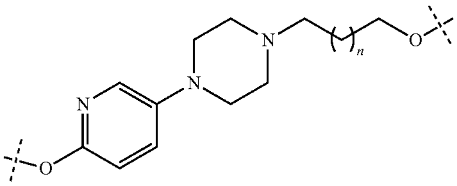
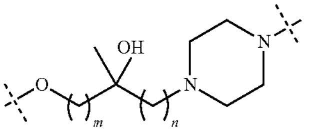
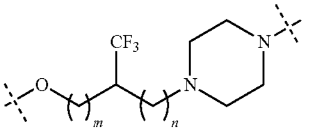
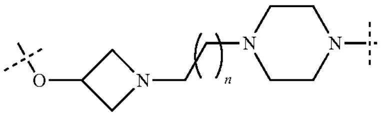
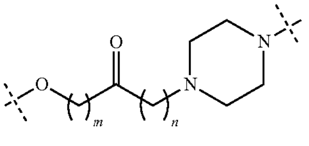
-continued
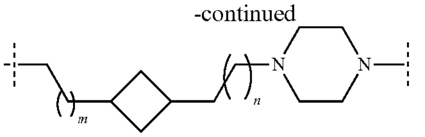
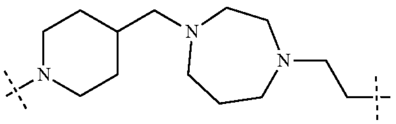
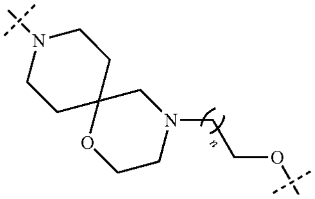
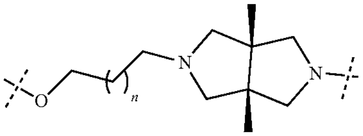
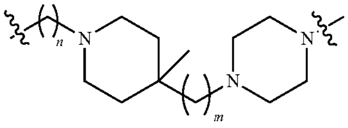
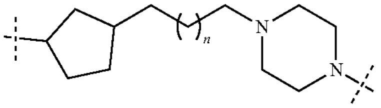
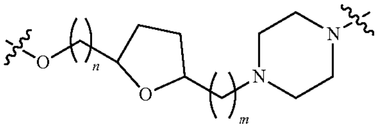
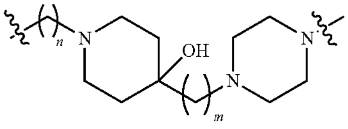
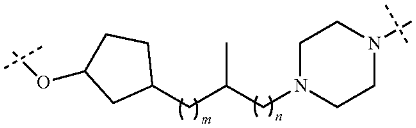
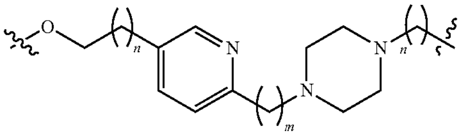
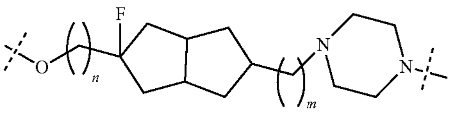
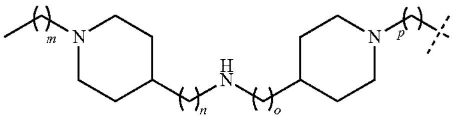
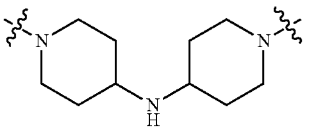

-continued
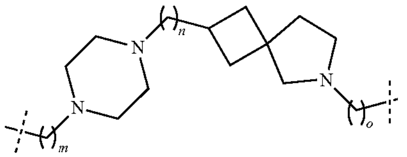
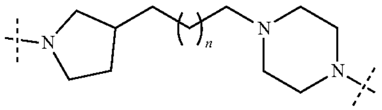
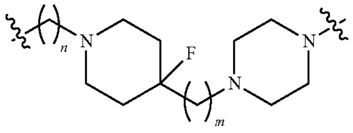
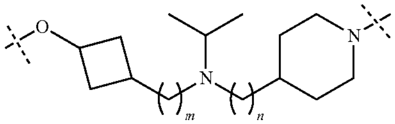
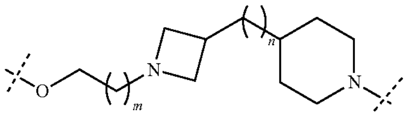
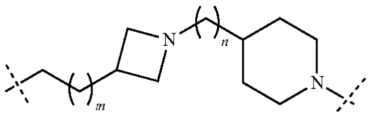
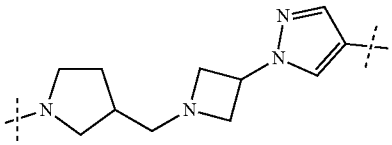
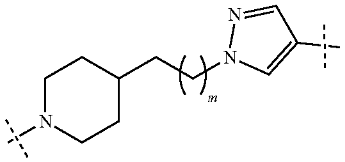
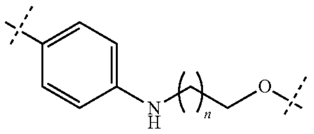
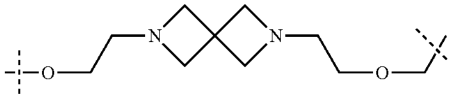
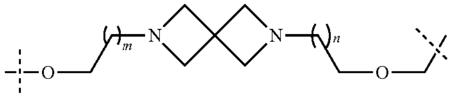
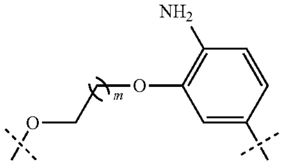
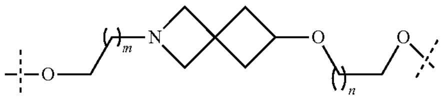
-continued
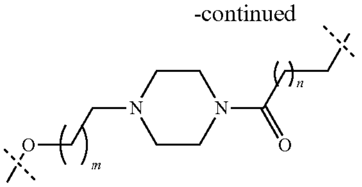
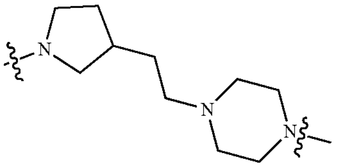
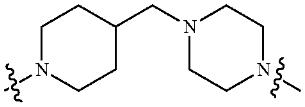
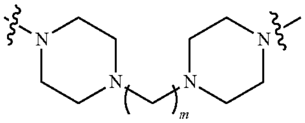
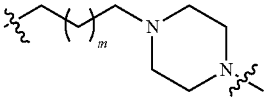
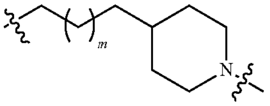
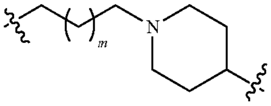
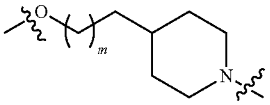
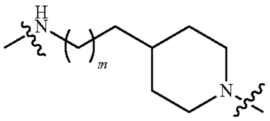
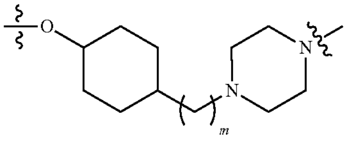
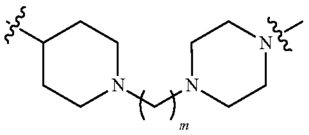
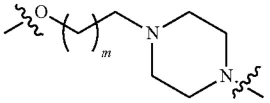
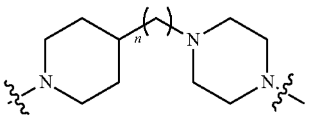
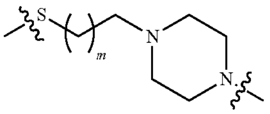

-continued
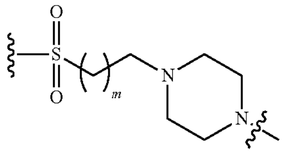
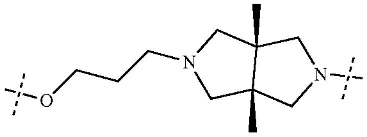
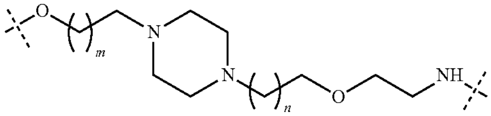
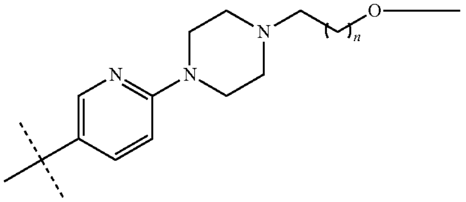
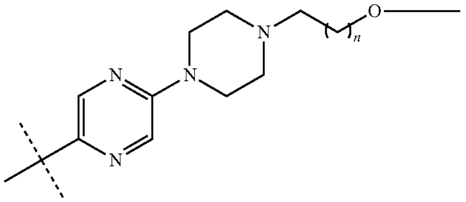
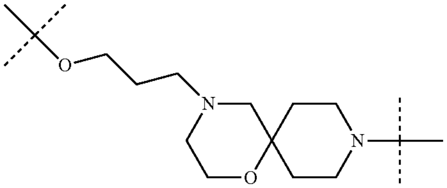
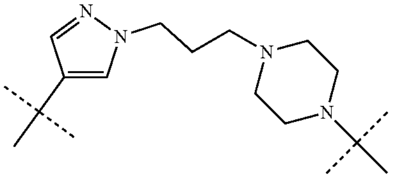
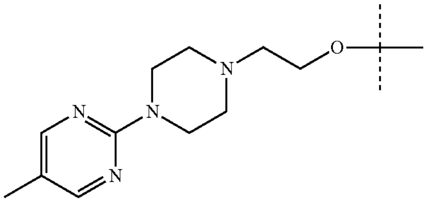
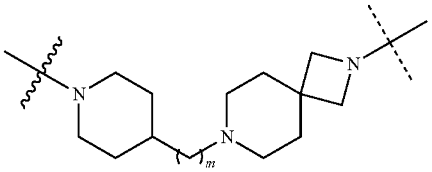
-continued
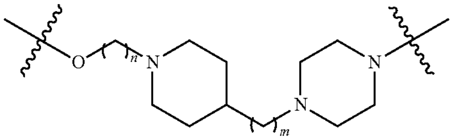
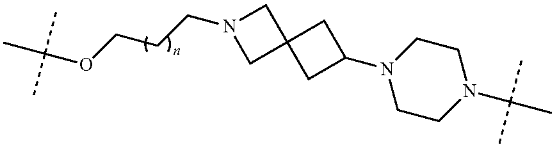
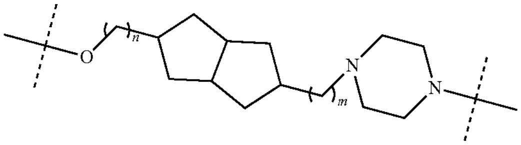
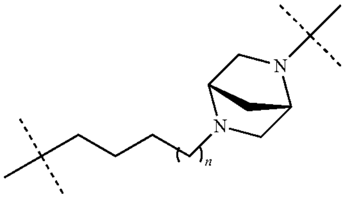
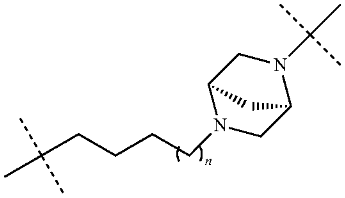
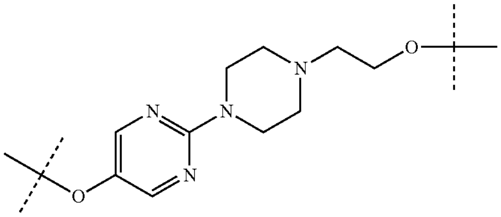
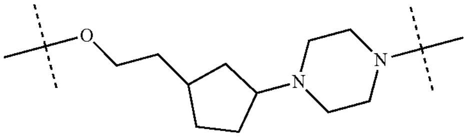
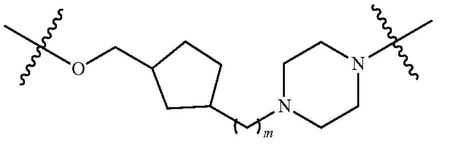
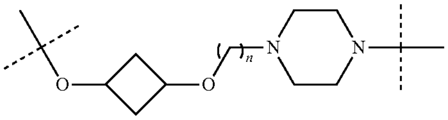
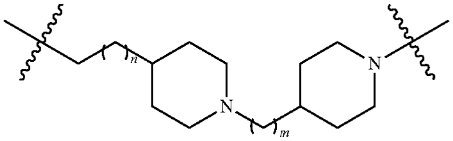
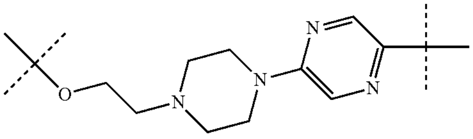

-continued
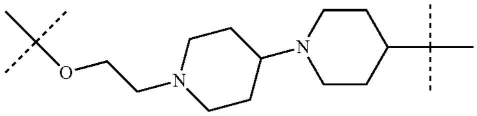
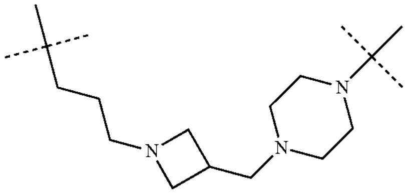
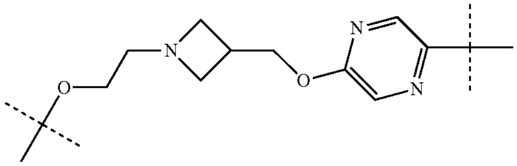
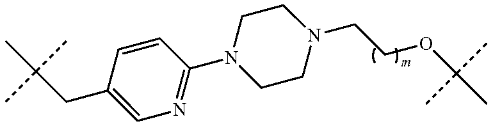
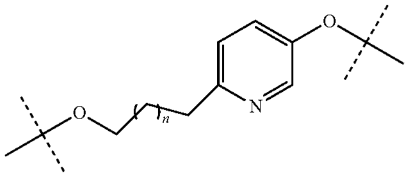
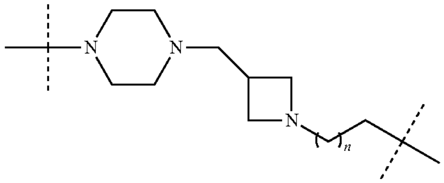
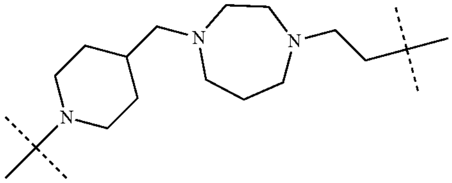
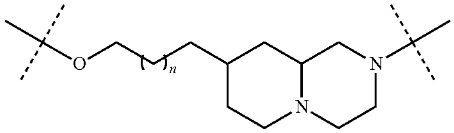
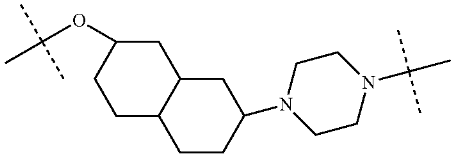
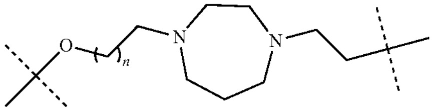
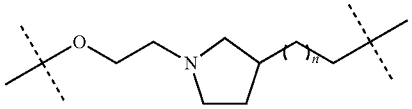
-continued
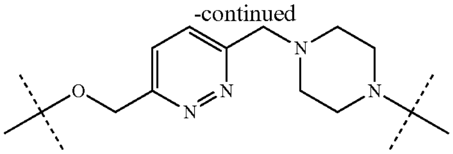
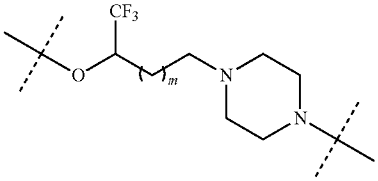
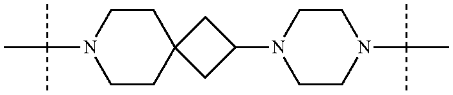
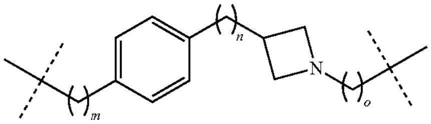
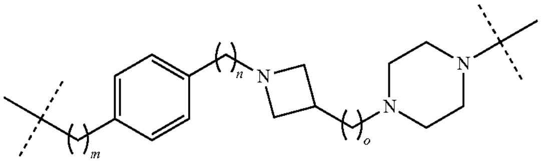
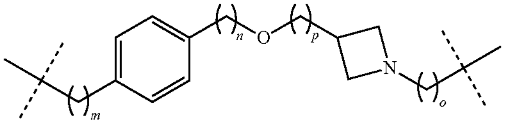
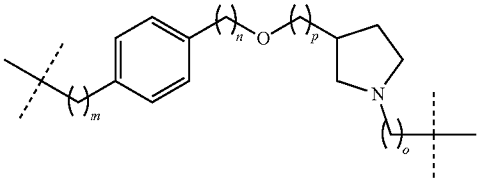
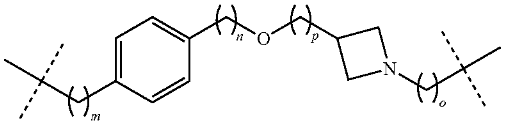
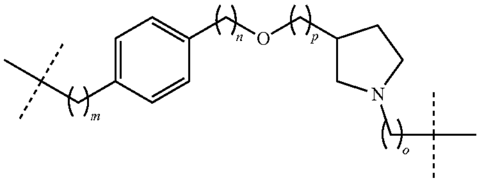
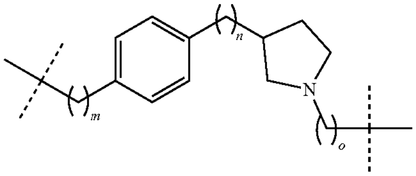
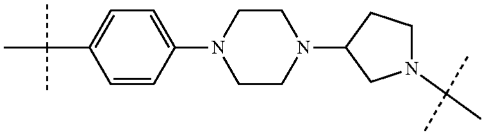

-continued
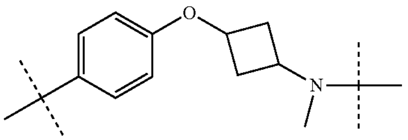
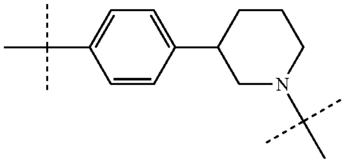
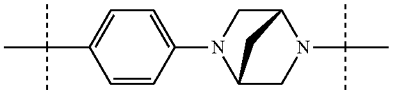
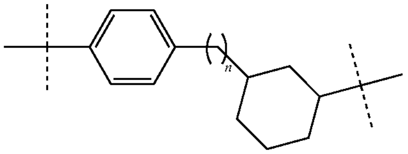
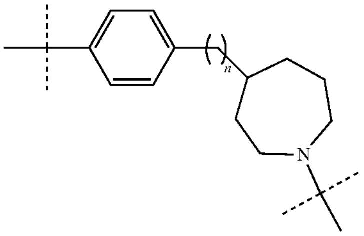
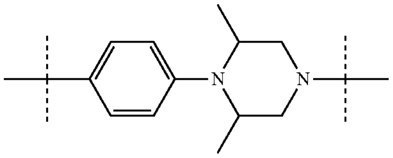
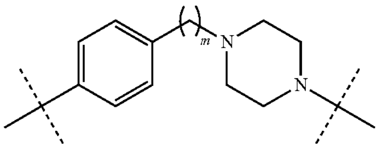
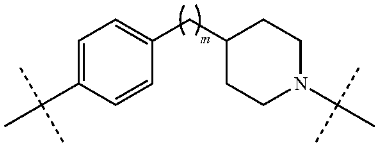
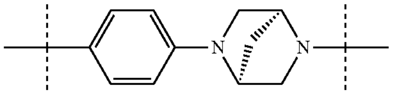
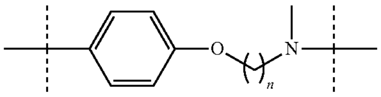
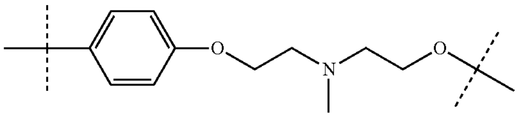
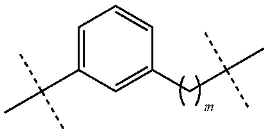
-continued
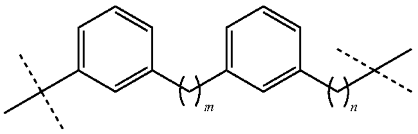
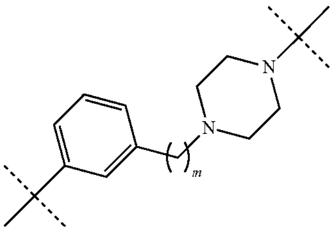
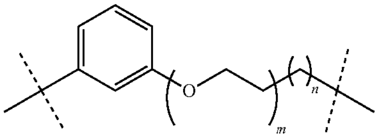
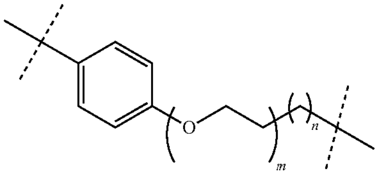
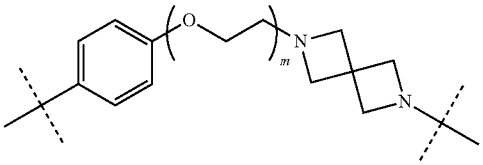
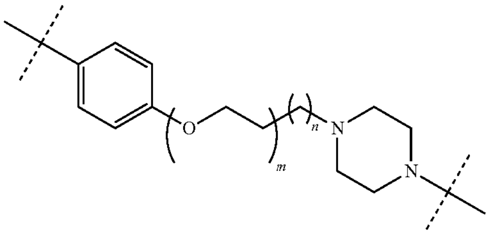
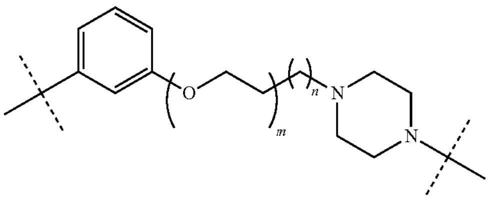
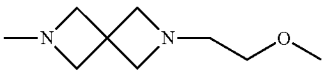
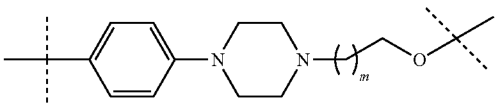
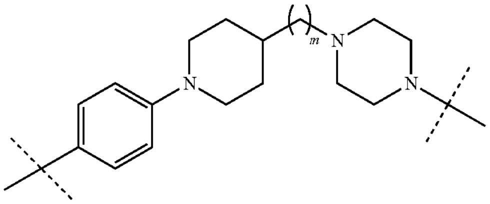

-continued
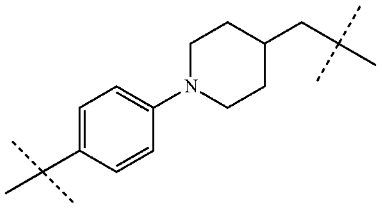
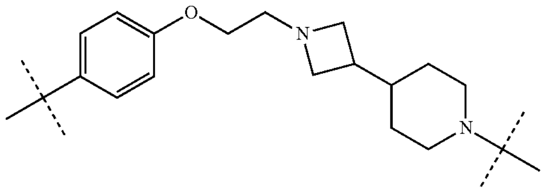
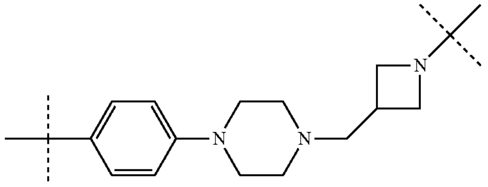
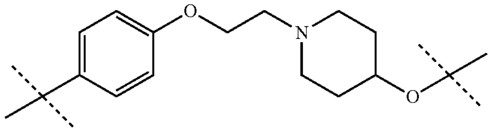
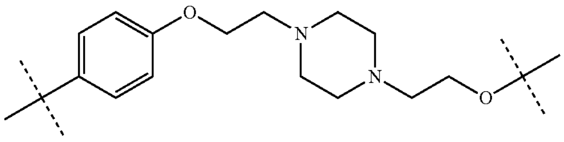
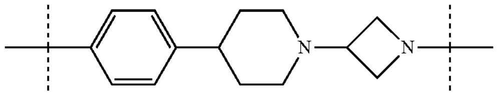
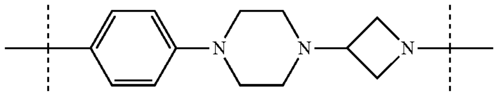
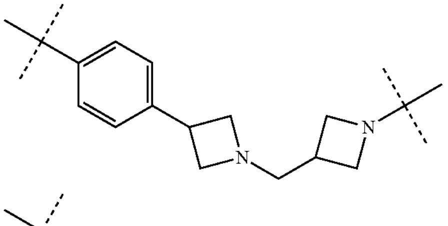
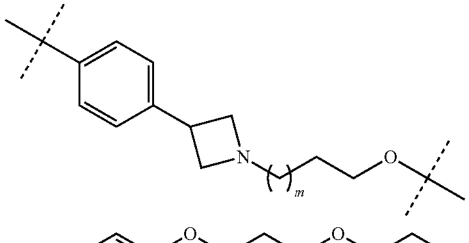
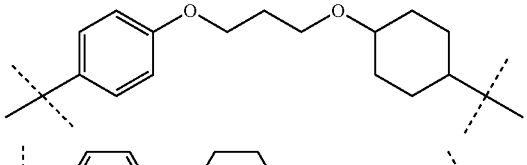
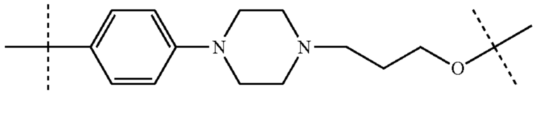
-continued
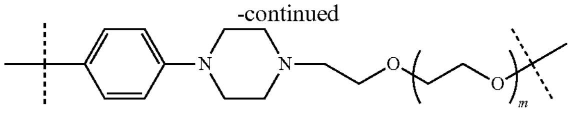
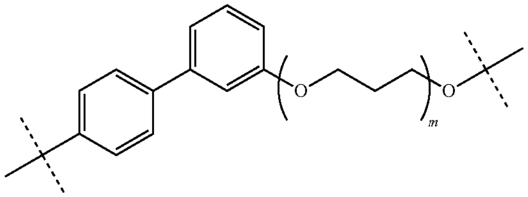
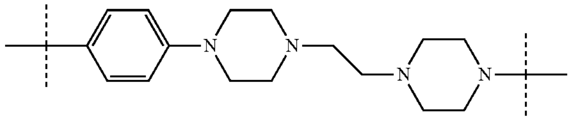
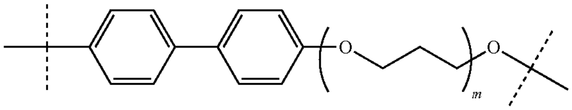
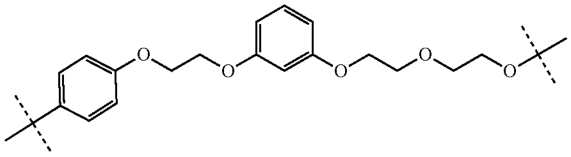
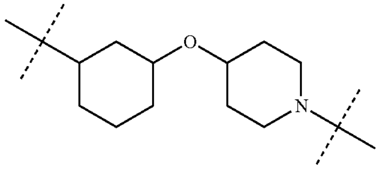
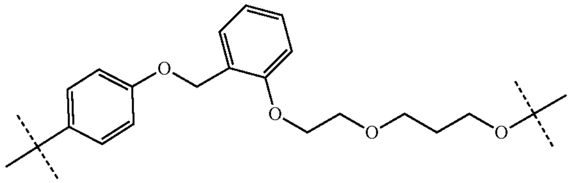
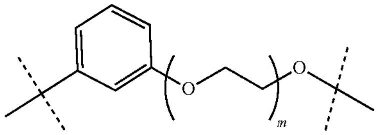
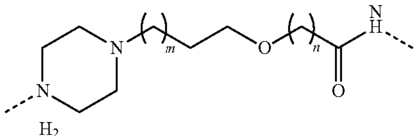
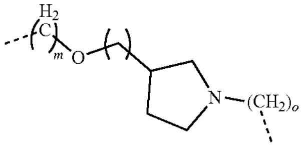
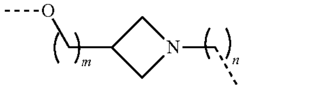
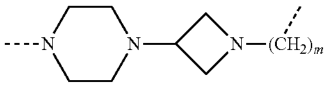
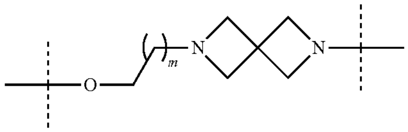

-continued
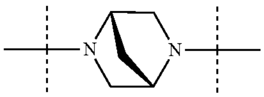
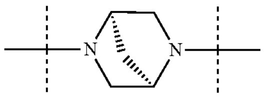
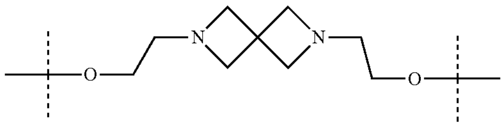
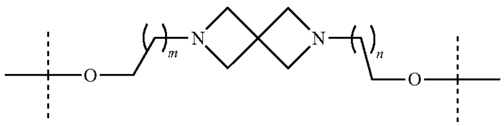
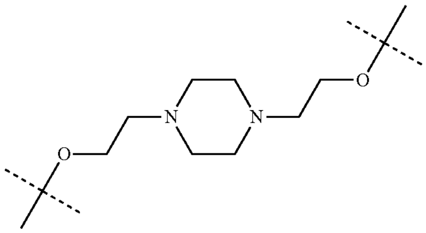
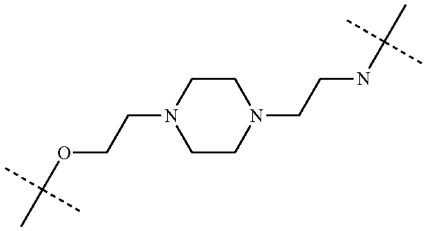
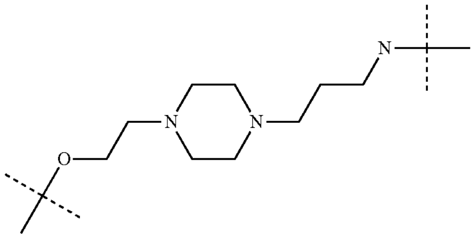
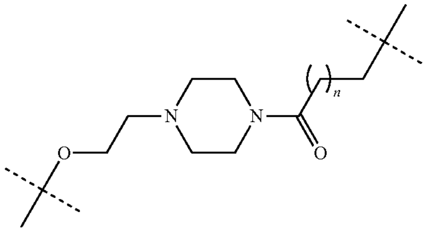
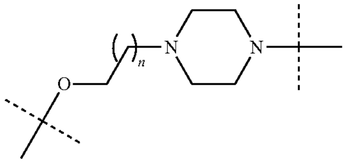
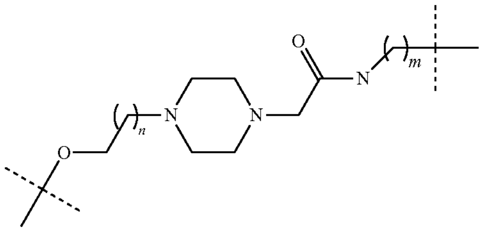
-continued
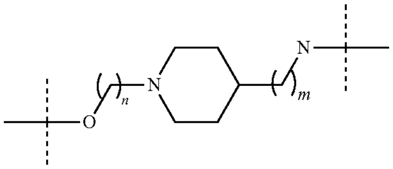
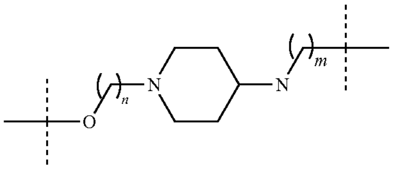
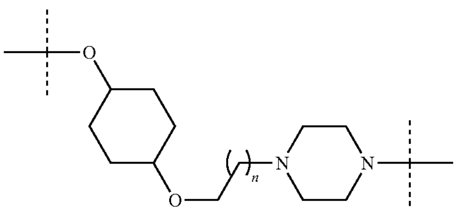
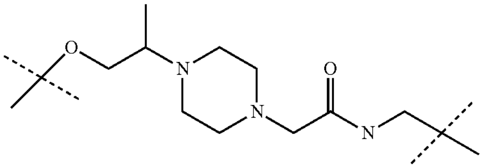
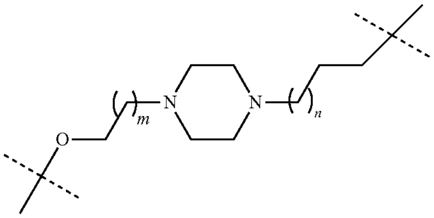
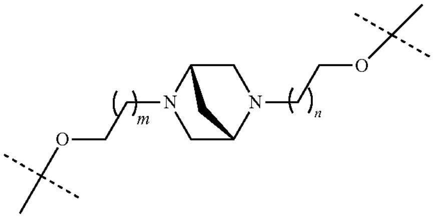
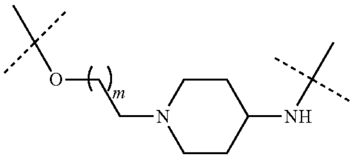
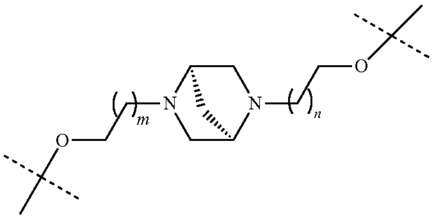
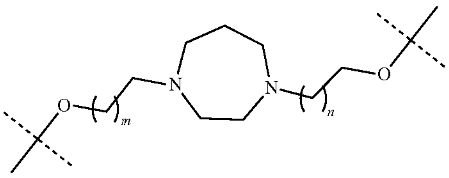

-continued
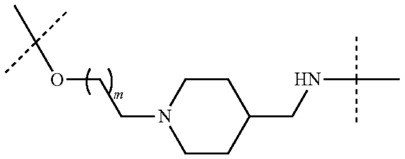
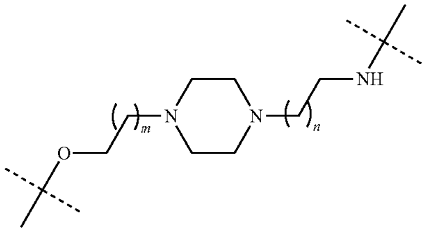
-continued
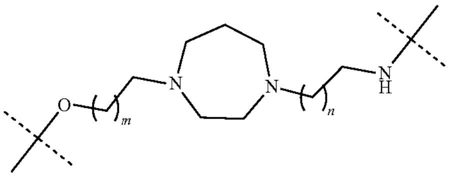
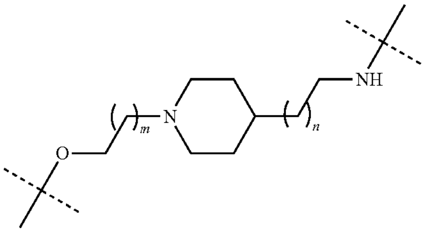
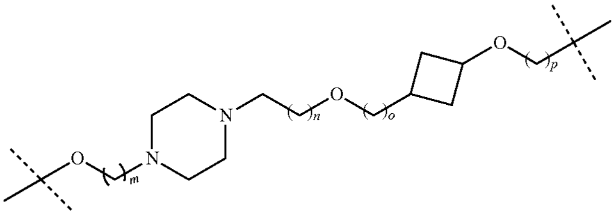
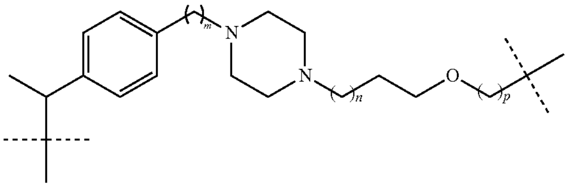
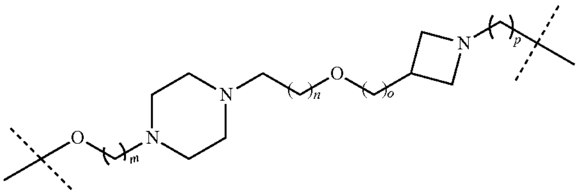
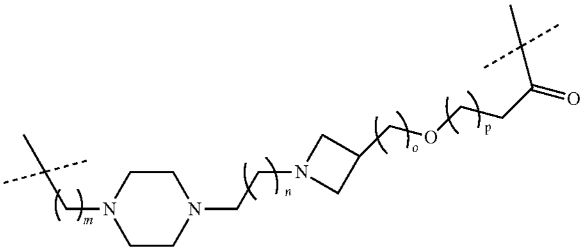
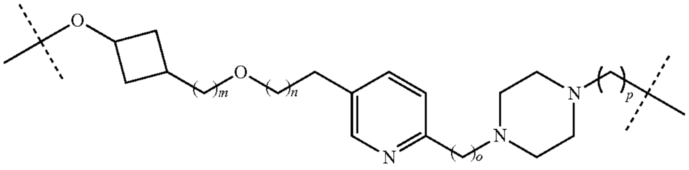

-continued
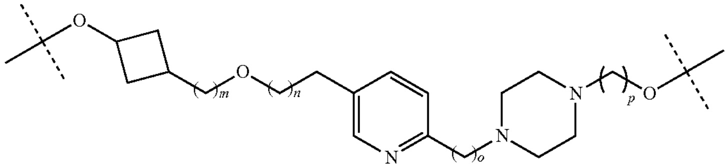
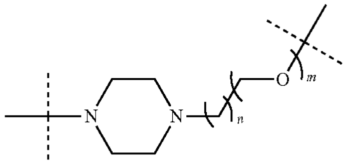
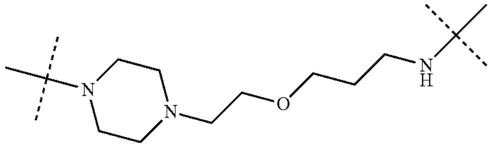
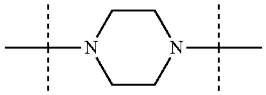
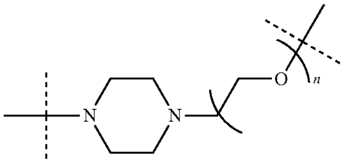
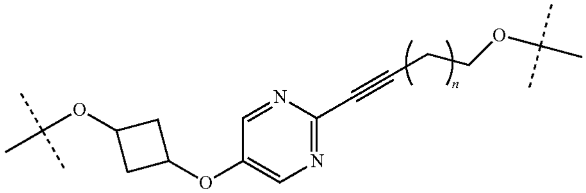
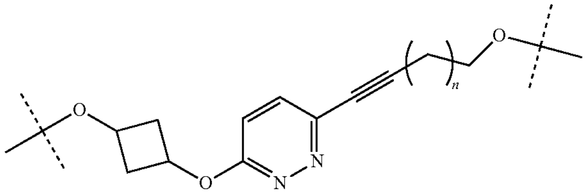
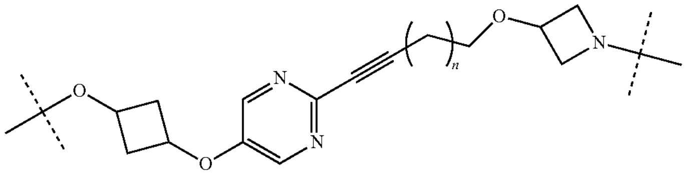
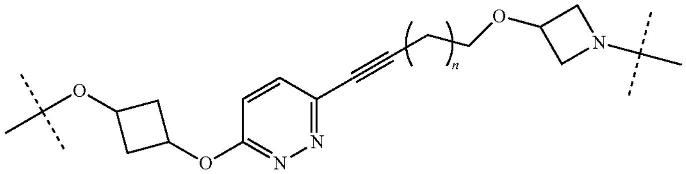
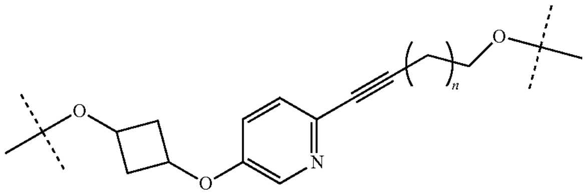
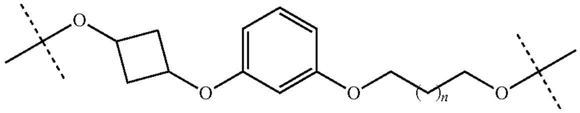
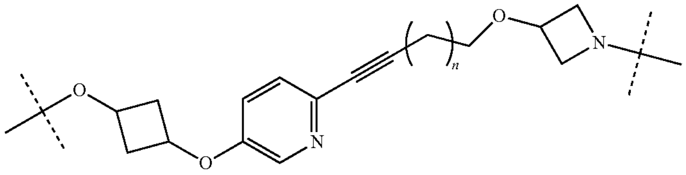

-continued
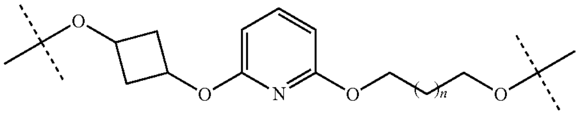
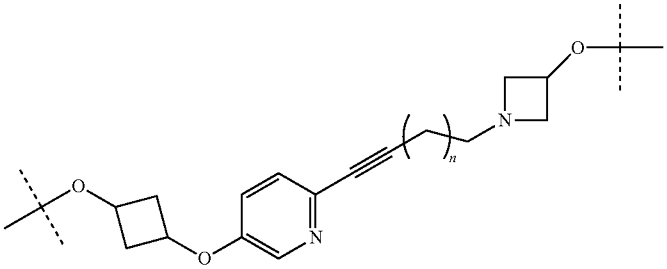
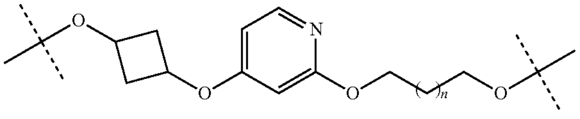
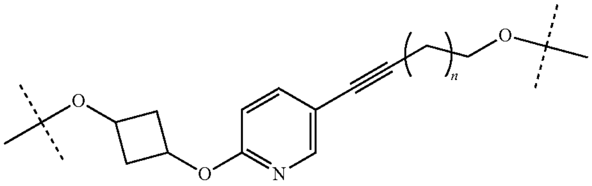
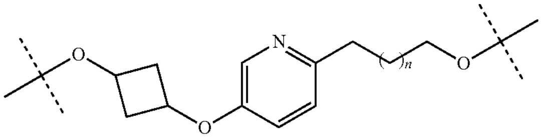
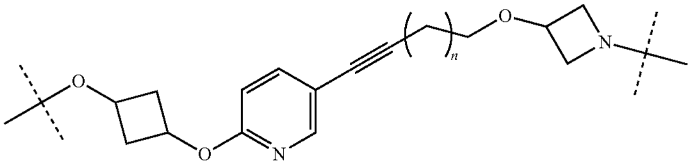
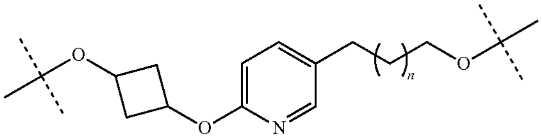
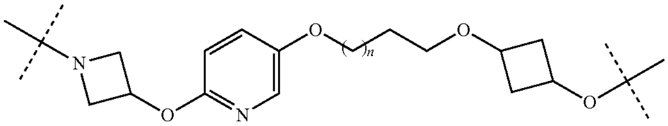
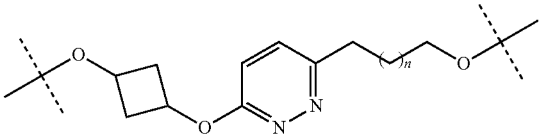
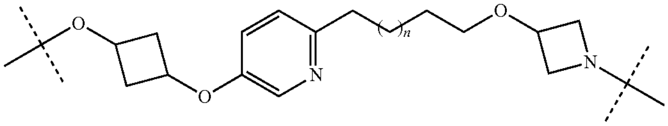
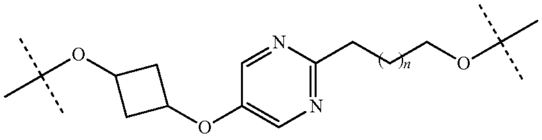

-continued
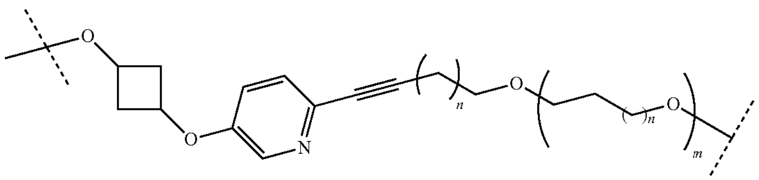
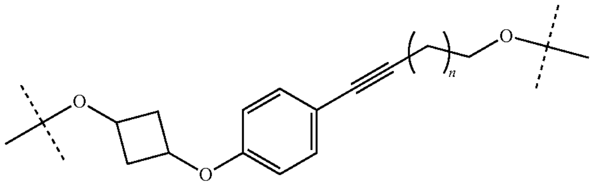
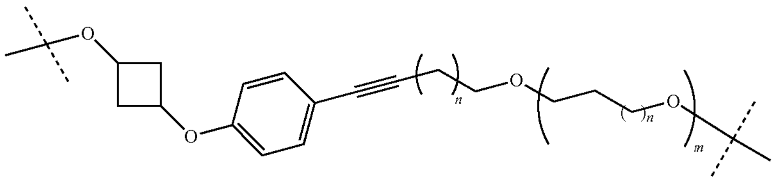
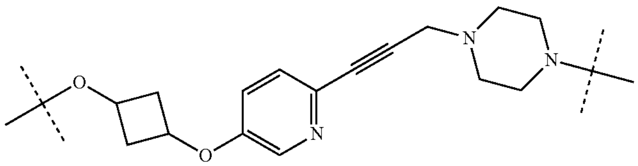
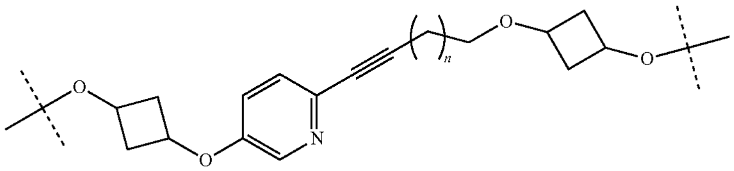
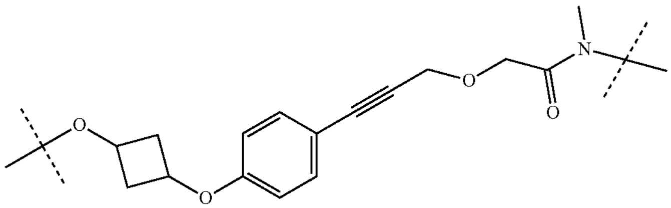
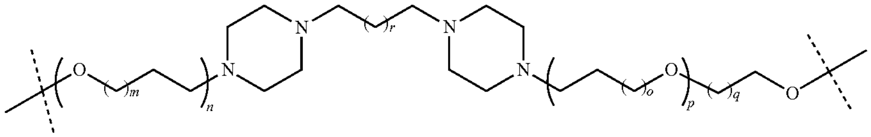
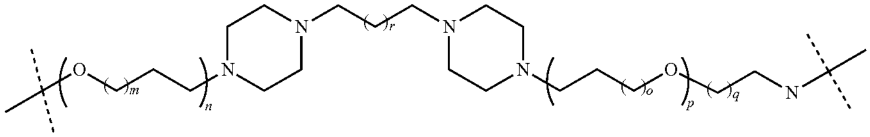
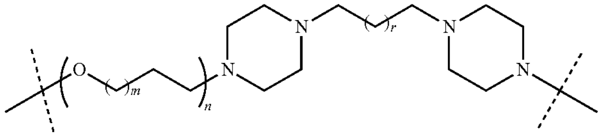
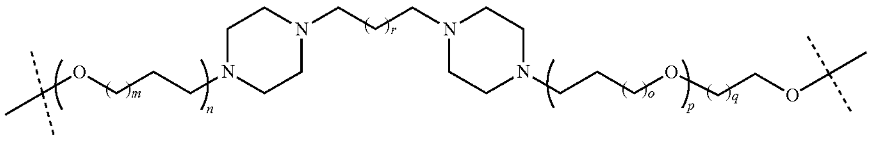

-continued
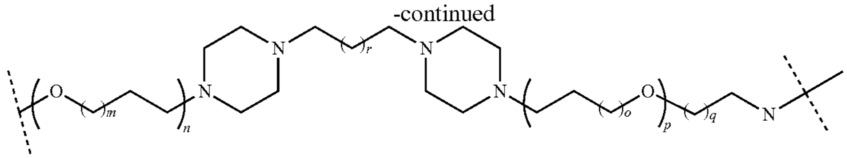
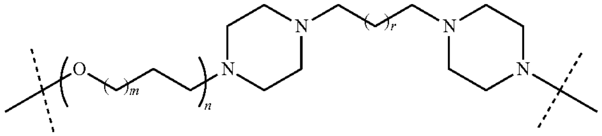
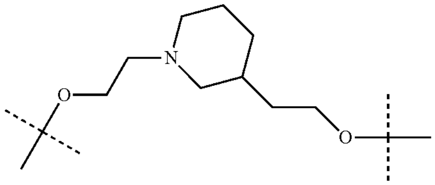
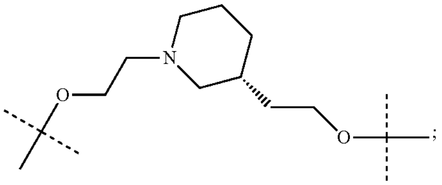
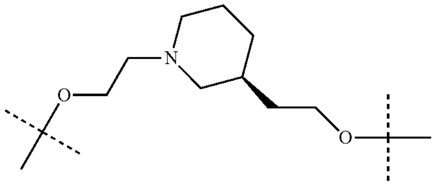
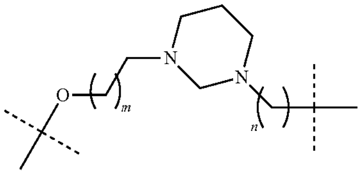
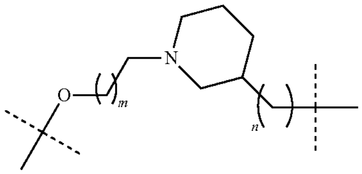
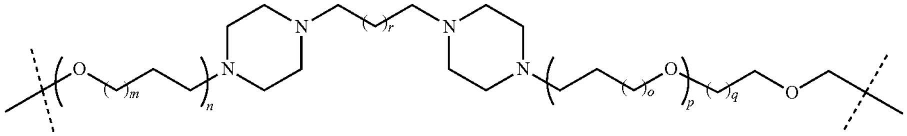
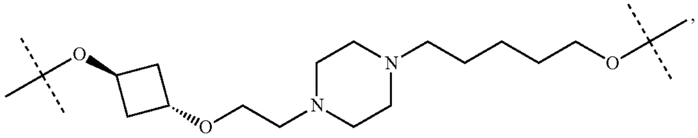
wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of linker (L) is selected from the group consisting of:
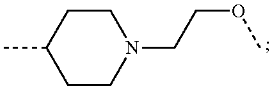
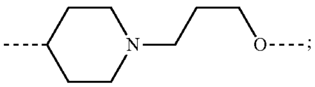
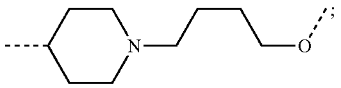
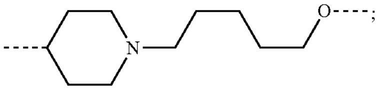
-continued
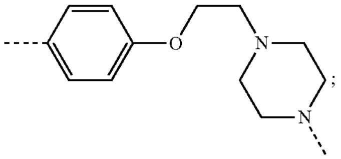
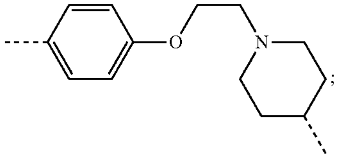
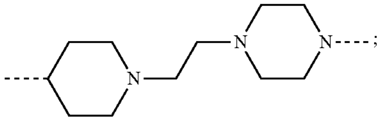
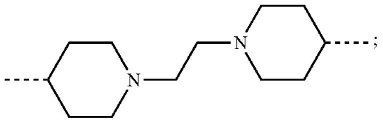

-continued
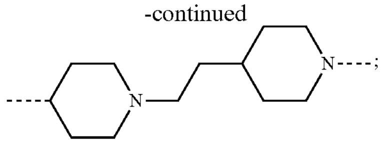
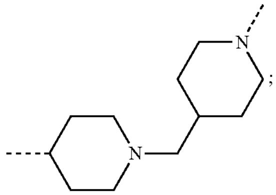
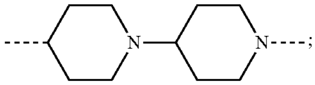
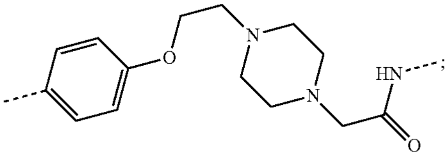
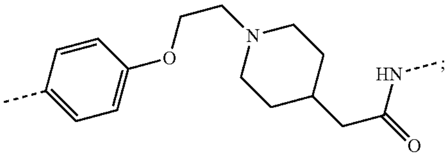
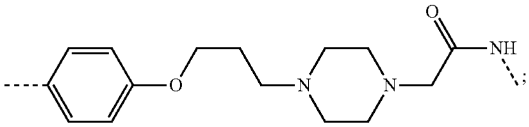
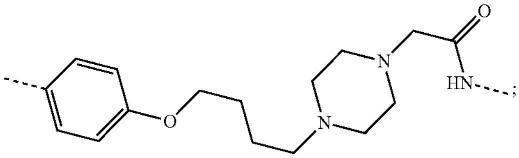
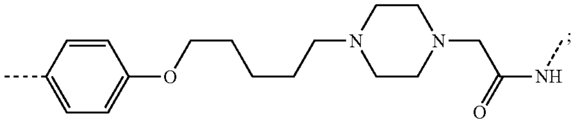
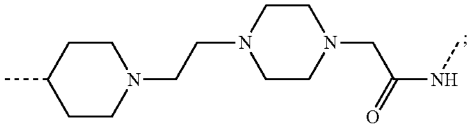
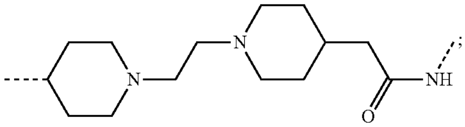
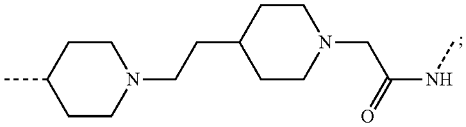
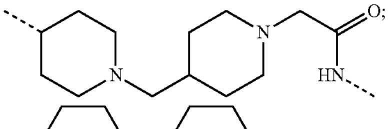
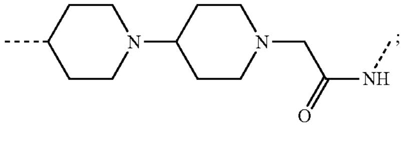
-continued
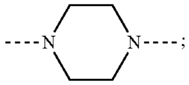
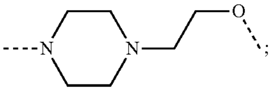
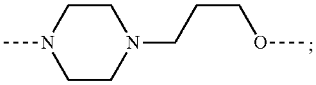
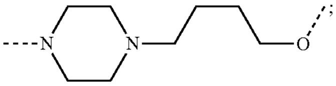
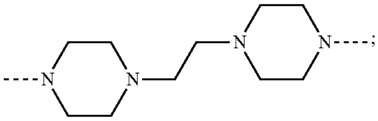
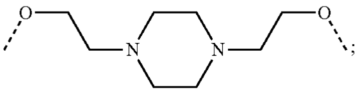
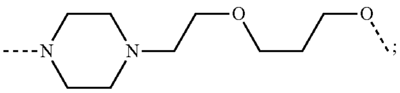
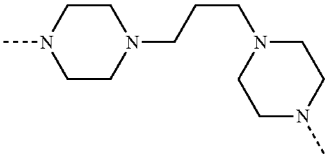
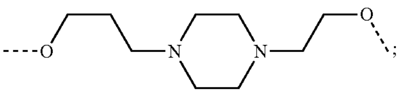
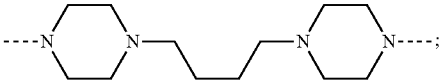
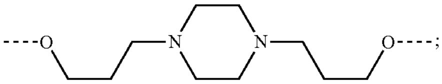
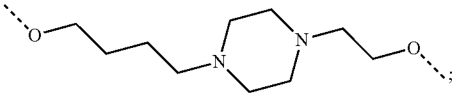
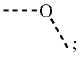
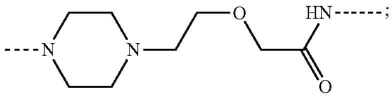
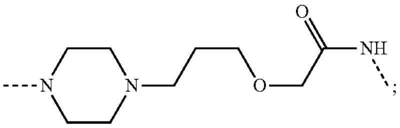
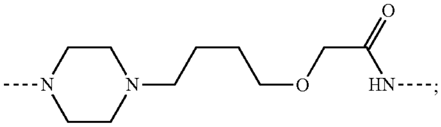
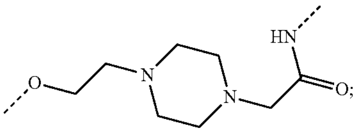

-continued
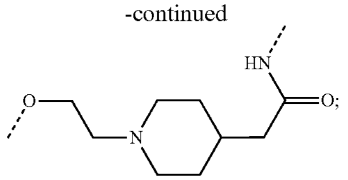
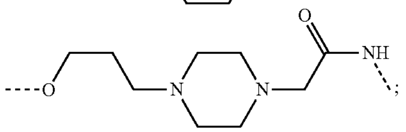
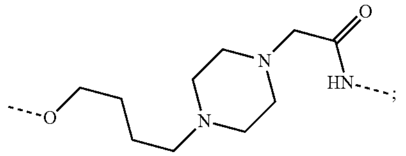
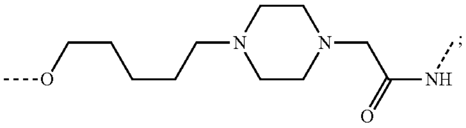
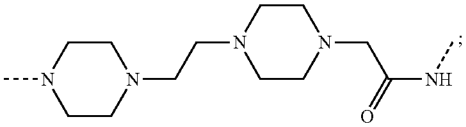
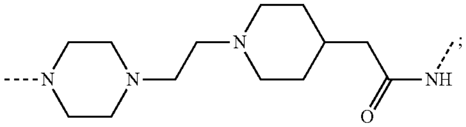
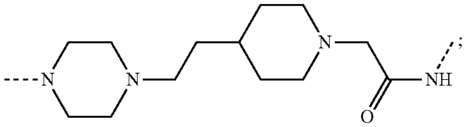
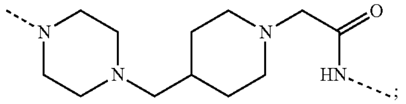
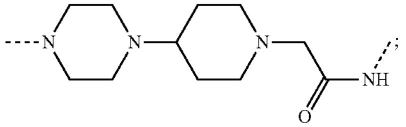
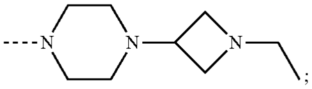
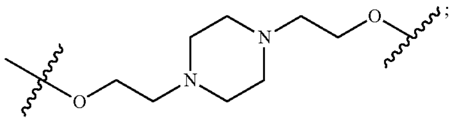
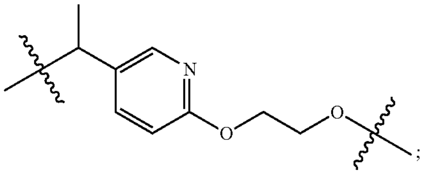
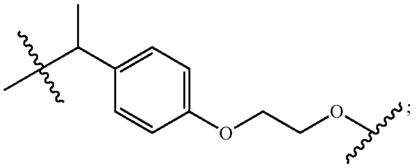
-continued
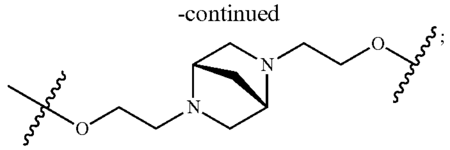
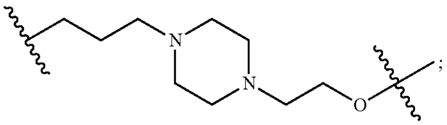
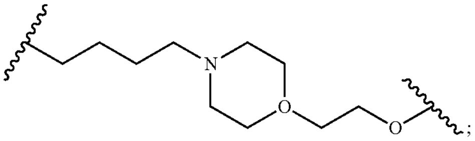
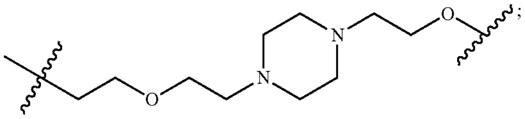
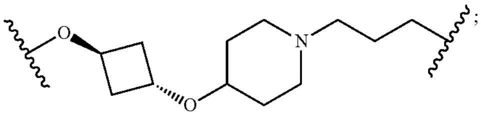
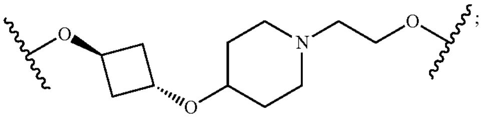
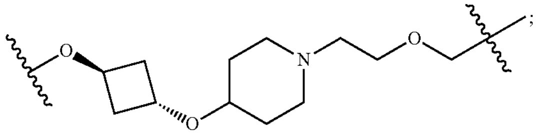
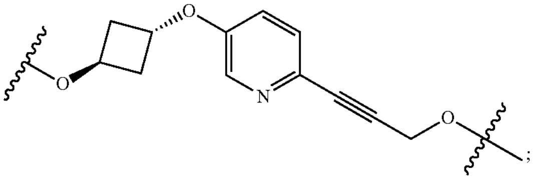
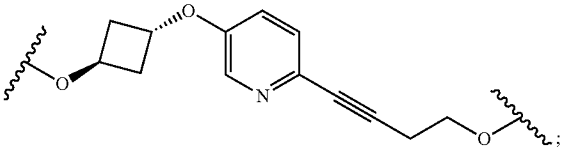
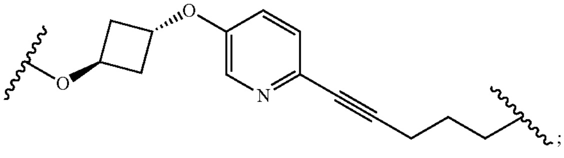
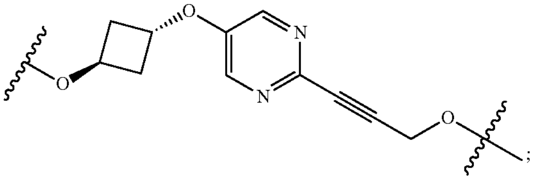
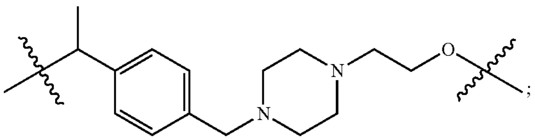

-continued
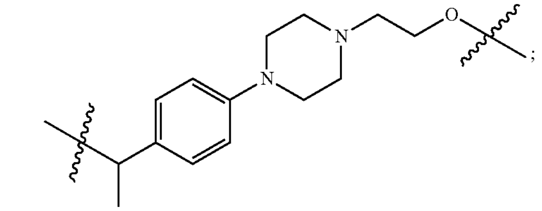
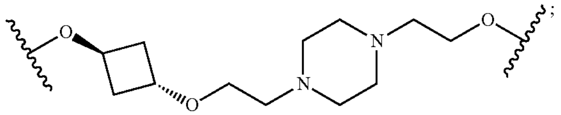
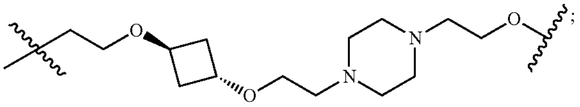
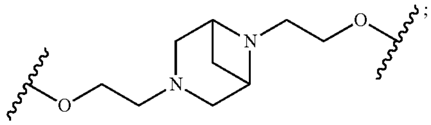
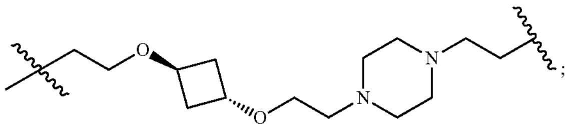
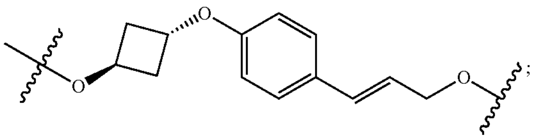
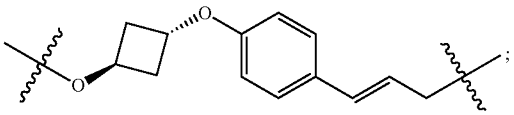
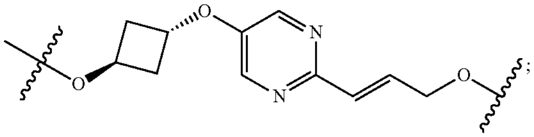
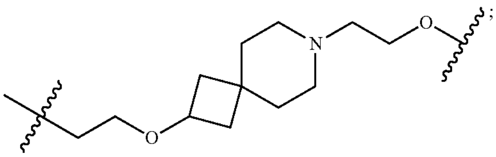
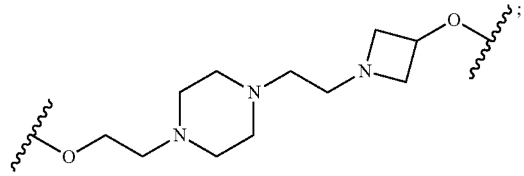
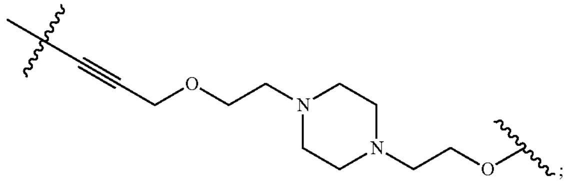
-continued
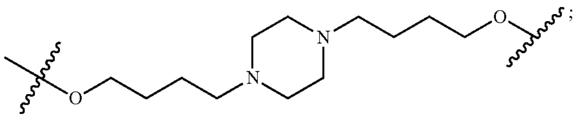
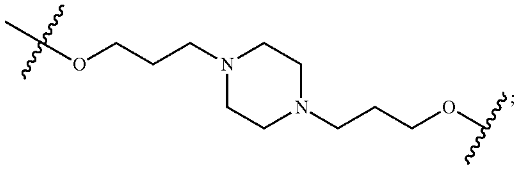
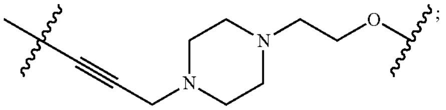
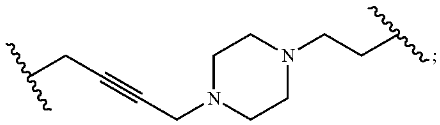
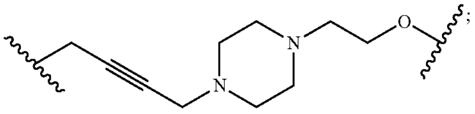
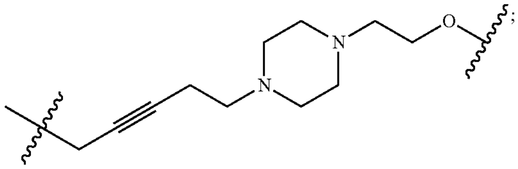
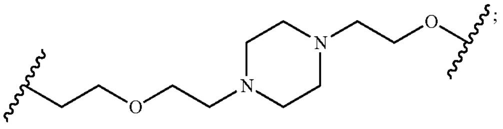
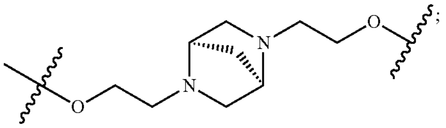
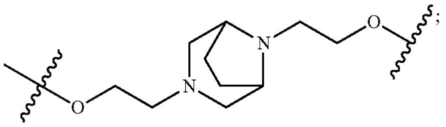
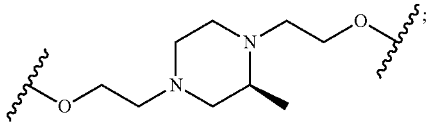
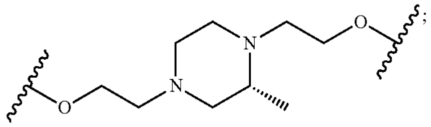
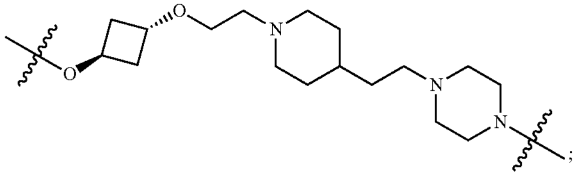

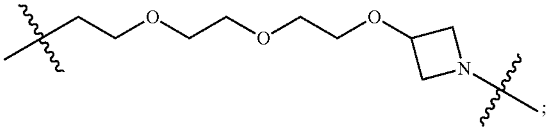
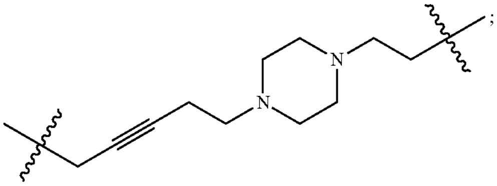
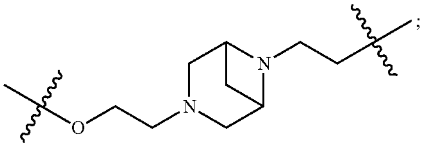
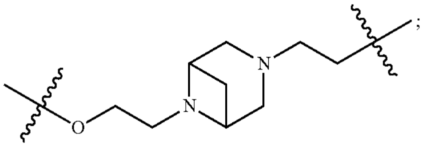
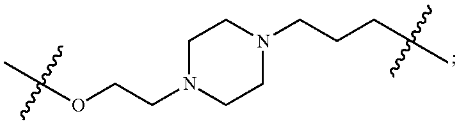
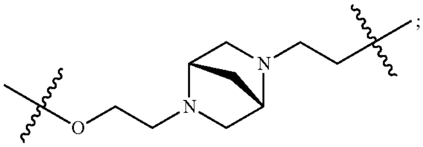
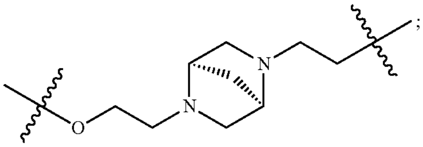
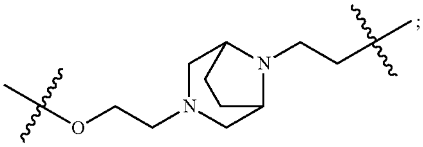
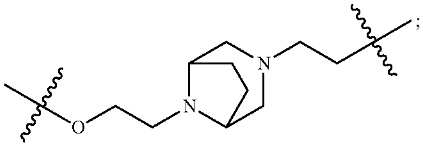
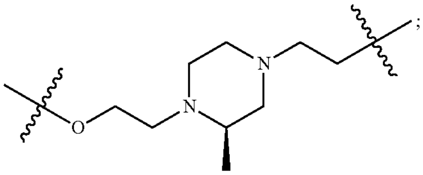
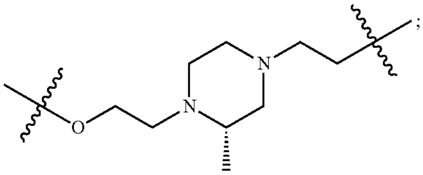
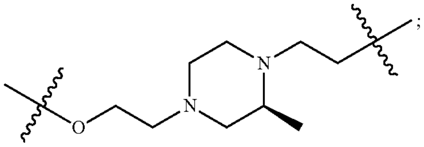
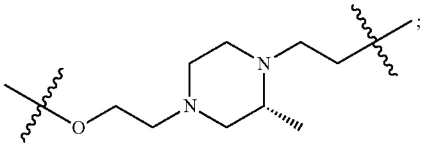
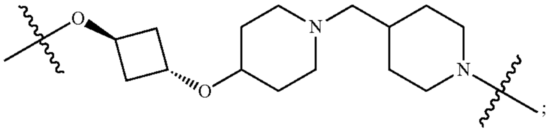
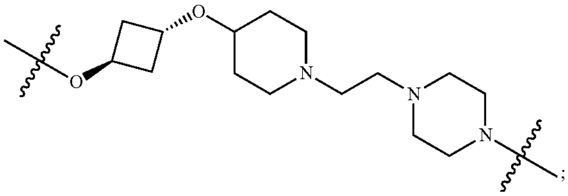
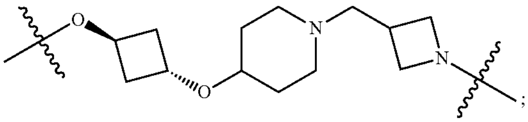
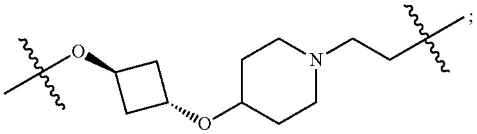
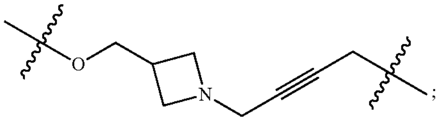
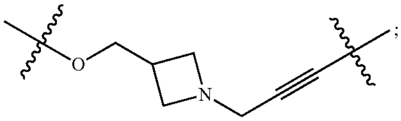
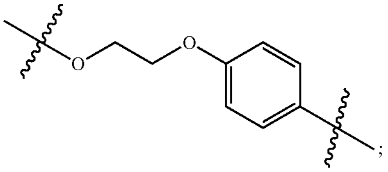
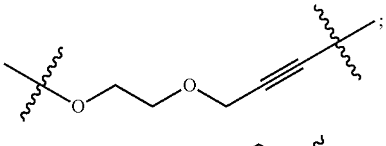
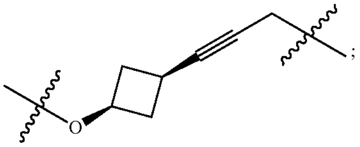
and
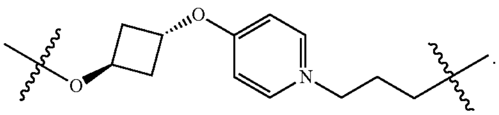

-continued

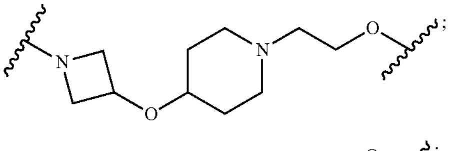

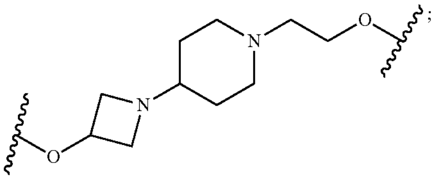

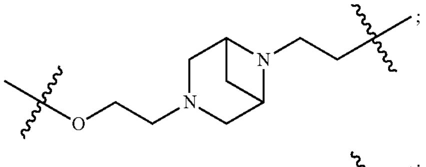

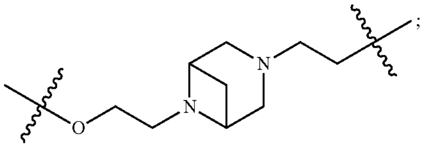

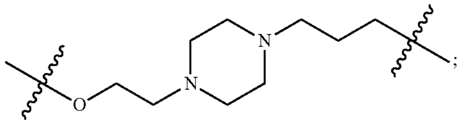

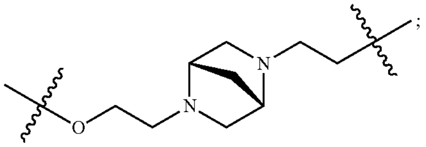

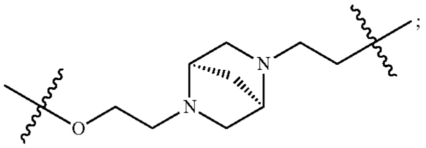

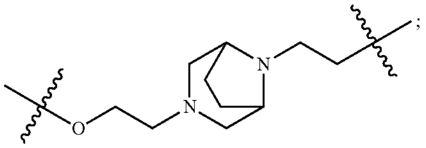

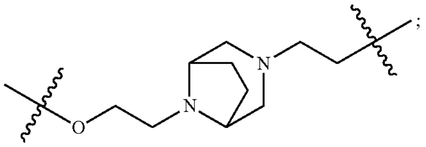

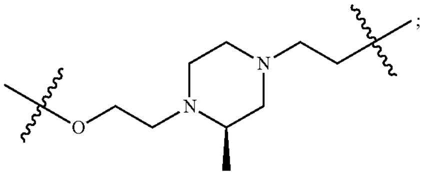

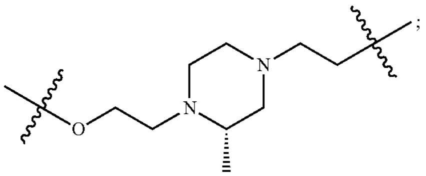

-continued

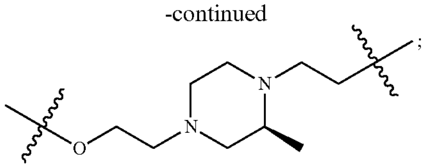

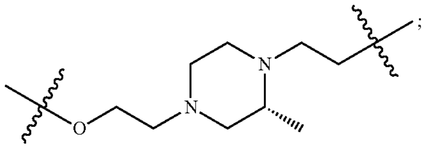 [SMILES: *CCN1CCN(CCO*)C[C@H]1C]

In any aspect or embodiment described herein, the linker (L) comprises a structure selected from the structure shown below:

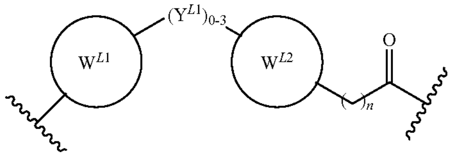

or

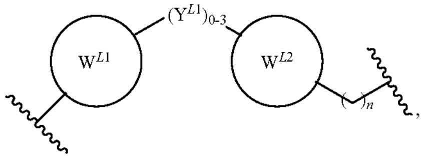

wherein:

$W^{L1}$ and $W^{L2}$ are each independently absent, a 4-8 membered ring with 0-4 heteroatoms, optionally substituted with $R^Q$, each $R^Q$ is independently a H, halo, OH, CN, $CF_3$, optionally substituted linear or branched $C_{1-6}$ alkyl, optionally substituted linear or branched $C_{1-6}$ alkoxy, or 2 $R^Q$ groups taken together with the atom to which they are attached form a 4-8 membered ring system containing 0-4 heteroatoms;

each $Y^{L1}$ is independently a bond, optionally substituted linear or branched $C_{1-6}$ alkoxy, optionally substituted linear or branched $C_{1-6}$ alkyl with one or more C atoms optionally replaced with O or $NR^{YL1}$, optionally substituted $C_{2-6}$ alkene with one or more C atoms optionally replaced with O, or optionally substituted $C_{2-6}$ alkyne with one or more C atoms optionally replaced with O;

each $R^{YL1}$ is H or optionally substituted linear or branched $C_{1-6}$ alkyl;

n is an integer from 0 to 10; and

 and  indicates the attachment point to the PTM or the ULM.

In any aspect or embodiment described herein, the linker (L) comprises a structure selected from the structure shown below:

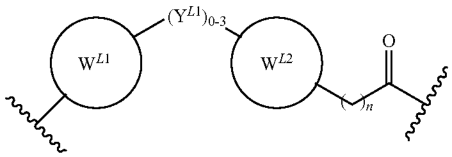

or

-continued

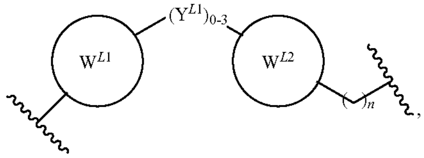

wherein:

$W^{L1}$ and $W^{L2}$ are each independently absent, piperazine, piperidine, morpholine, optionally substituted with $R^Q$, each $R^Q$ is independently a H, —Cl—, —F—, OH, CN, $CF_3$, optionally substituted linear or branched $C_{1-6}$ alkyl (e.g. methyl, ethyl), optionally substituted linear or branched $C_{1-6}$ alkoxy (e.g. methoxy, ethoxy);

each $Y^{L1}$ is independently a bond, optionally substituted linear or branched $C_1$-$C_6$ alkoxy, optionally substituted linear or branched $C_{1-6}$ alkyl with one or more C atoms optionally replaced with O or $NR^{YL1}$, optionally substituted $C_{2-6}$ alkene with one or more C atoms optionally replaced with O, optionally substituted $C_{2-6}$ alkyne with one or more C atoms optionally replaced with O;

each $R^{YL1}$ is H or optionally substituted linear or branched $C_{1-6}$ alkyl (e.g. methyl, ethyl);

n is an integer from 0 to 10; and and indicates the attachment point to the PTM or the ULM.

In any aspect or embodiment described herein, the linker (L) comprises a structure selected from the structure shown below:

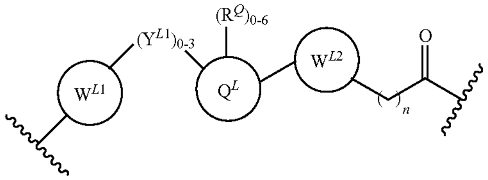

or

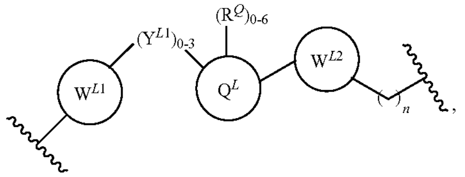

, wherein:

$W^{L1}$ and $W^{L2}$ are each independently absent, aryl, heteroaryl, cyclic, heterocyclic, $C_{1-6}$ alkyl with one or more C atoms optionally replaced with O or $N^{RY1}$, $C_{2-6}$ alkene with one or more C atoms optionally replaced with O, $C_{2-6}$ alkyne with one or more C atoms optionally replaced with O, bicyclic, biaryl, biheteroaryl, or biheterocyclic, each optionally substituted with $R^Q$, each $R^Q$ is independently a H, halogen, OH, CN, $CF_3$, hydroxyl, nitro, C≡CH, $C_{2-6}$ alkenyl, $C_{2-6}$ alkynyl, optionally substituted linear or branched $C_1$-$C_6$ alkyl, optionally substituted linear or branched $C_{1-6}$ alkoxy, optionally substituted $OC_{1-3}$alkyl (e.g., optionally substituted by 1 or more —F), OH, $NH_2$, $NR^{Y1}R^{Y2}$, CN, or 2 RQ groups taken together with the atom to which they are attached form a 4-8 membered ring system containing 0-4 heteroatoms;

each $Y^{L1}$ is independently a bond, $NR^{YL1}$, O, S, $NR^{YL2}$, $CR^{YL1}R^{YL2}$, C═O, C═S, SO, $SO_2$, optionally substituted linear or branched $C_1$-$C_6$ alkoxy, or optionally substituted linear or branched $C_1$-$C_6$ alkyl with one or more C atoms optionally replaced with O;

$Q^L$ is a 3-6 membered alicyclic, bicyclic or aromatic ring with 0-4 heteroatoms, optionally bridged, optionally substituted with 0-6 $R^Q$, each $R^Q$ is independently H, optionally substitute linear or branched $C_{1-6}$ alkyl (e.g., optionally substituted by 1 or more halogen or $C_{1-6}$ alkoxyl), or 2 $R^Q$ groups taken together with the atom to which they are attached form a 3-8 membered ring system containing 0-2 heteroatoms;

each $R^{YL1}$ and $R^{YL2}$ is independently H, OH, optionally substituted linear or branched $C_{1-6}$ alkyl (e.g., optionally substituted by 1 or more halogen or $C_{1-6}$ alkoxyl), or $R^{YL1}$ and $R^{YL2}$ together with the atom to which they are attached form a 3-8 membered ring system containing 0-2 heteroatoms;

n is an integer from 0 to 10; and and indicates the attachment point to the PTM or the ULM.

In any aspect or embodiment described herein, the PTM, ULM or L is a chemical moiety as described or exemplified herein. That is, any of the described PTMs, ULMs, or Ls can be combined in any combination with any other PTM, ULM, or L as described herein.

In any aspect or embodiment described herein, the linker (L) comprises a structure selected from the structure shown below:

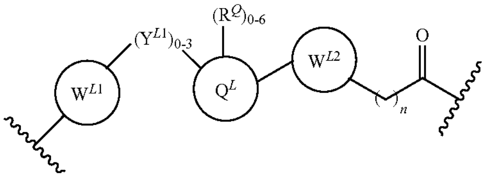

or

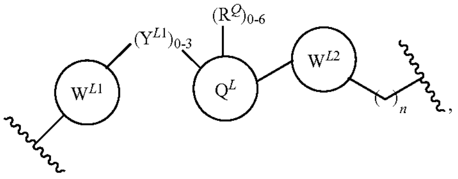

, wherein:

$W^{L1}$ and $W^{L2}$ are each independently absent, cyclohexane, cyclopentane, piperazine, piperidine, morpholine, $C_{1-6}$ alkyl with one or more C atoms optionally replaced with O or $NR^{YL1}$, $C_{2-6}$ alkene with one or more C atoms optionally replaced with O, $C_{2-6}$ alkene with one or more C atoms optionally replaced with O, or $C_{2-6}$ alkyne with one or more C atoms optionally replaced with O, each optionally substituted with $R^Q$, each $R^Q$ is independently a H, —Cl, —F, OH, CN, $CF_3$, hydroxyl, optionally substituted linear or branched $C_{1-6}$ alkyl (e.g., methyl, ethyl), or optionally substituted linear or branched $C_{1-6}$ alkoxy;

each $Y^{L1}$ is independently a bond, $NR^{YL1}$, O, $CR^{YL1}R^{YL2}$, C═O, optionally substituted linear or branched $C_1$-$C_6$ alkoxy, or optionally substituted linear or branched $C_{1-6}$ alkyl with one or more C atoms optionally replaced with O or $NR^{YL1}$, $C_{2-6}$ alkene with one or more C atoms optionally replaced with O, $C_{2-6}$ alkyne with one or more C atoms optionally replaced with O;

$Q^L$ is a 3-6 membered heterocyclic, heterobicyclic, or heteroaryl ring, optionally substituted with 0-6 $R^Q$, each $R^Q$ is independently H, or optionally substituted linear or branched $C_{1-6}$ alkyl (e.g., optionally substituted by 1 or more halo, $C_{1-6}$ alkoxyl);

each $R^{YL1}$ and $R^{YL2}$ is independently H or optionally substituted linear or branched $C_{1-6}$ alkyl (e.g., methyl, ethyl, optionally substituted by 1 or more halogen or $C_{1-6}$ alkoxyl);

n is an integer from 0 to 10; and

 and  indicates the attachment point to the PTM or the ULM.

In any aspect or embodiment described herein, the L comprises a chemical structural unit represented by the formula: $-(A^L)_q-$, wherein:

$-(A^L)_q-$ is a group which is connected to the CLM and the PTM;

q is an integer greater than or equal to 1;

each $A^L$ is independently selected from $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C—C, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 0-6 $R^{L1}$ and/or $R^{L2}$ groups, and heteroaryl optionally substituted with 1-6 $R^{L1}$ and/or $R^{L2}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}alkyl)_2$, $C_{3-11}$ cycloalkyl, aryl, heteroaryl, $C_{3-11}$ heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, or NH $SO_2NH_2$.

In any aspect or embodiment described herein, the L includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally replaced with $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}{=}CR^{L2}$, C≡C, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$ heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, or NH $SO_2NH_2$.

In any aspect or embodiment described herein, the L is selected from the group consisting of:

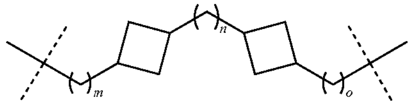

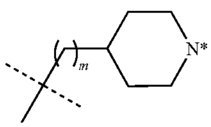 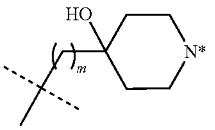

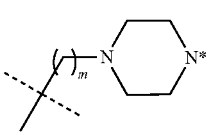 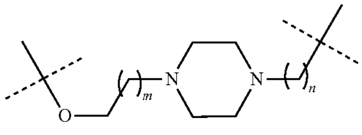

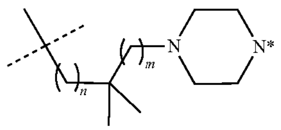 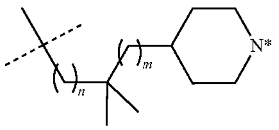

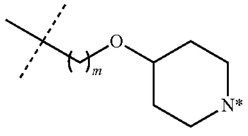 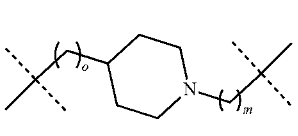

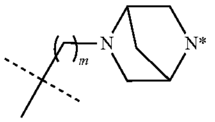 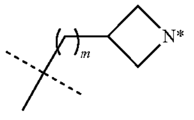

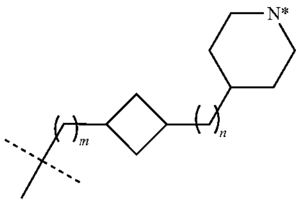 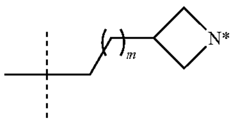

-continued
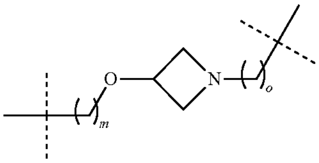
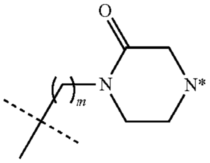
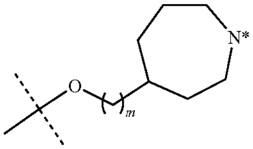
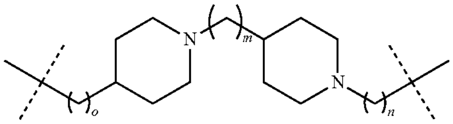
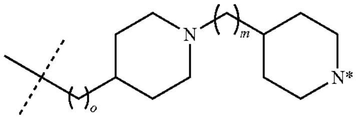
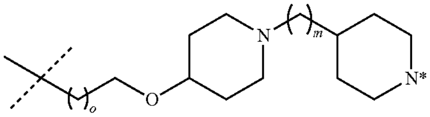
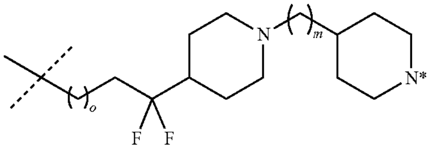
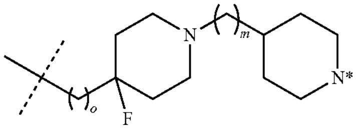
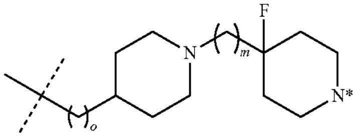
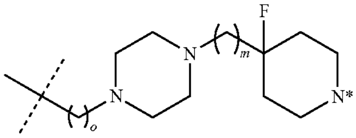
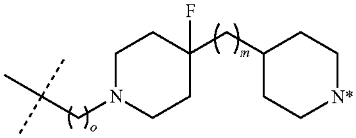
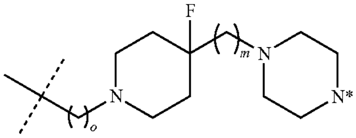
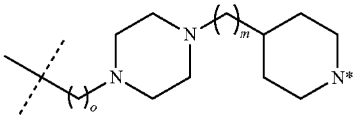
-continued
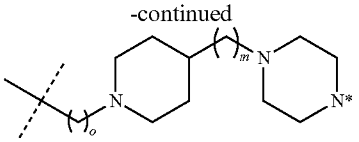
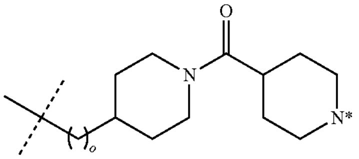
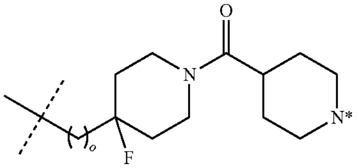
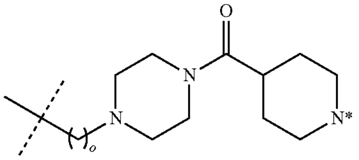
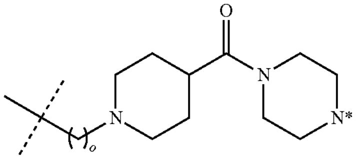
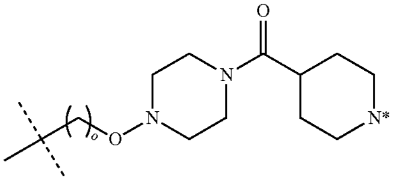
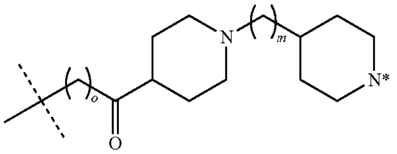
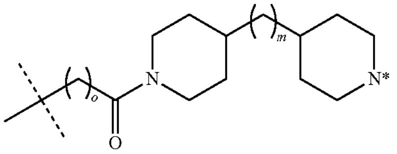
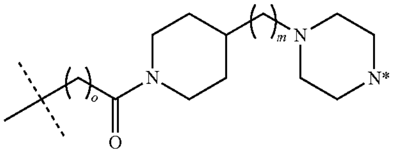
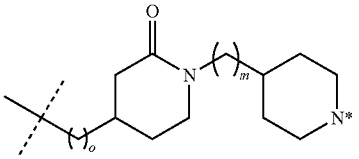
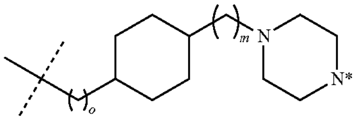

-continued
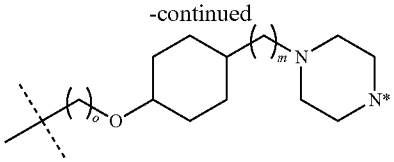
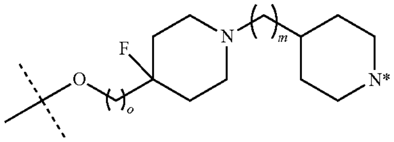
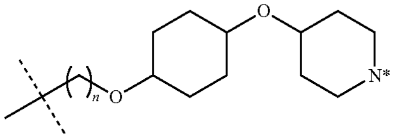
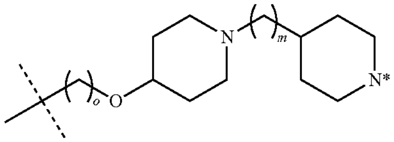
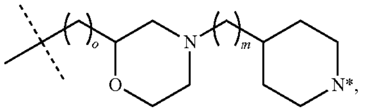
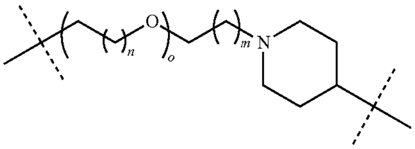
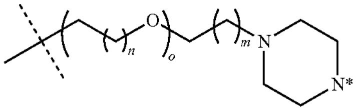
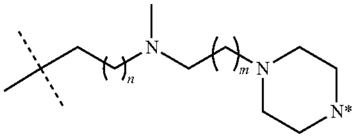
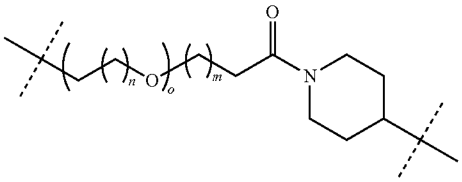
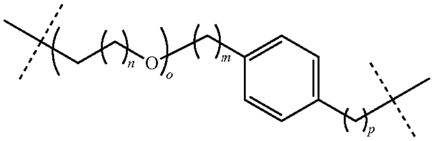
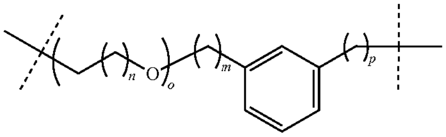
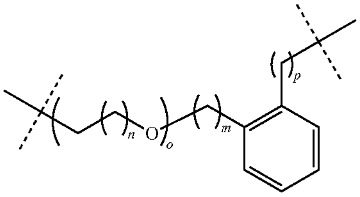
-continued
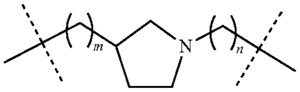
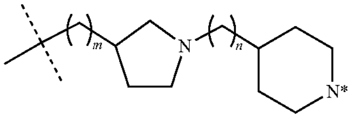
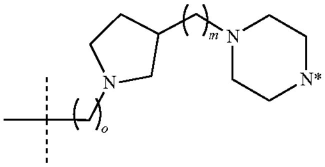
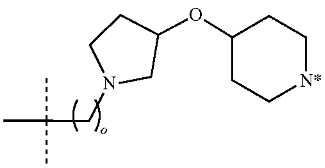
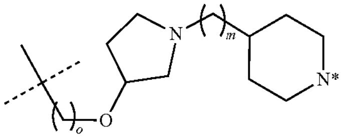
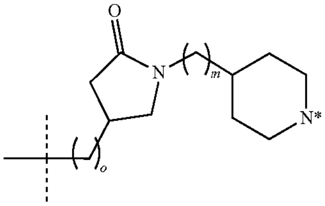
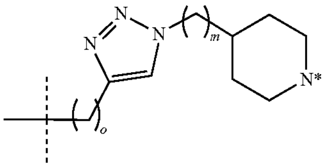
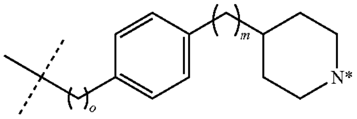
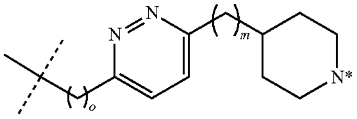
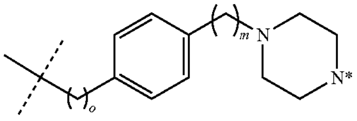
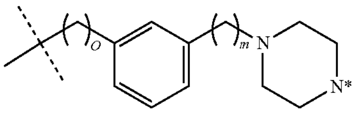
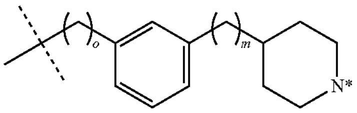

-continued
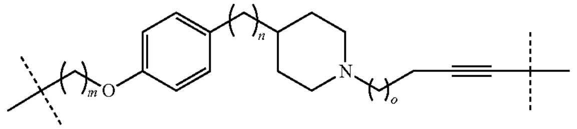
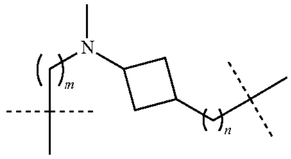
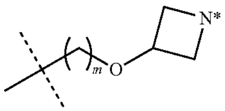
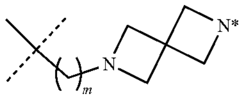
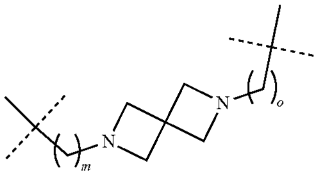
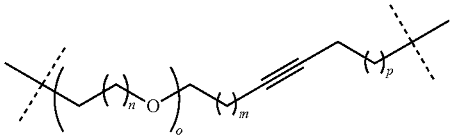
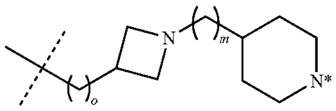
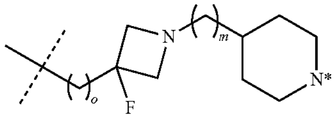
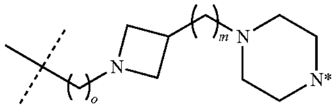
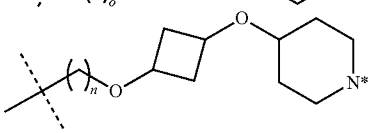
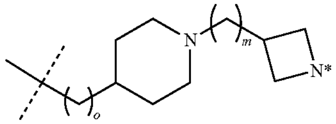
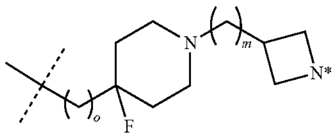
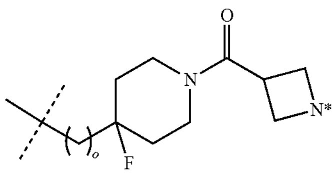
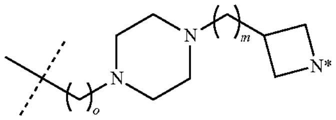
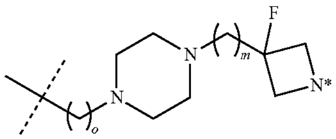
-continued
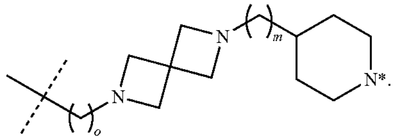
wherein:
the chemical linker group is optionally substituted with a halogen;
N* is a nitrogen atom that is covalently linked to or shared with the CLM or the PTM; and
each m, n, o, p, q, and r of the L is independently 0, 1, 2, 3, 4, 5, 6, 7, 8, 9, 10, 11, 12, 13, 14, 15, 16, 17, 18, 19, or 20.
In any aspect or embodiment described herein, the L is selected from the group consisting of:
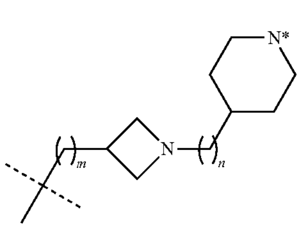
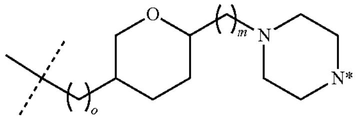
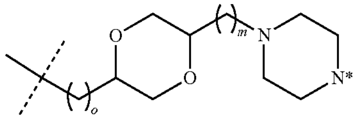
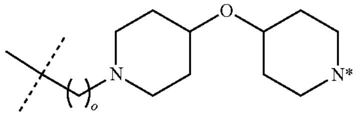
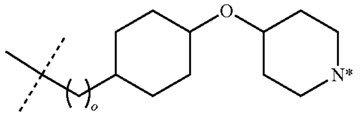
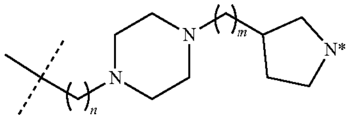
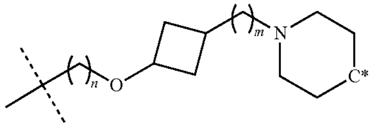
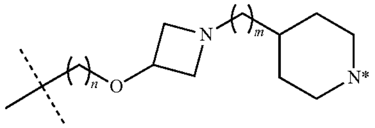
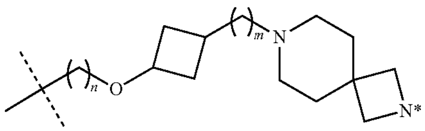

-continued

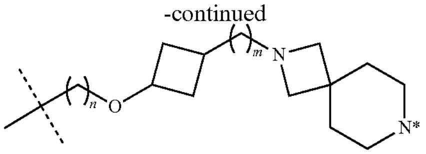

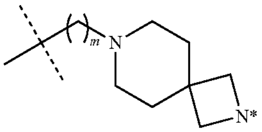

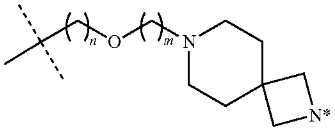

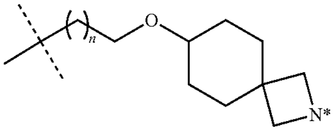

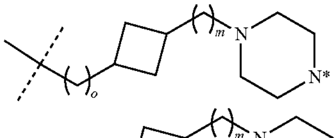

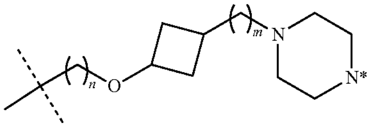

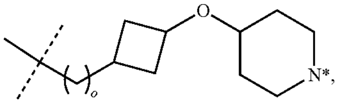

wherein:

the chemical linker group is optionally substituted with 0, 1, 2, or 3 substituents independently selected from halogen and methyl (preferably independently selected halogens);

C* is a carbon atom that is covalently linked to or shared with the CLM or the PTM;

N* is a nitrogen atom that is covalently linked to or shared with the CLM or the PTM; and each m, n, and o of the L is independently 0, 1, 2, 3, 4, 5, 6, 7, 8, 9, 10, 11, 12, 13, 14, 15, 16, 17, 18, 19, or 20.

Exemplary PTMs

In one aspect of the disclosure, the PTM group (also referred as the LTM group) binds to the target protein, LRRK2 or mutated form thereof.

The compositions described below exemplify members of LRRK2 binding moieties that can be used according to the present invention. These binding moieties are linked to the ubiquitin ligase binding moiety (CLM) preferably through a chemical linking group in order to present the LRRK2 protein (to which LTM is bound) in proximity to the ubiquitin ligase for ubiquitination and subsequent degradation.

In certain contexts, the term "target protein" is used to refer to the LRRK2 protein, a member of the leucine-rich repeat kinase family, which is a target protein to be ubiquitinated and degraded. In other contexts, the term "target protein" is used to refer to a mutated form of the LRRK2 protein, such as a LRRK protein having one or mutation selected from the group consisting of G2019S, 12020T, N1437H, R1441G/C/H, and Y1699C.

The term "protein target moiety" or PTM is used to describe a small molecule which binds to LRRK2 or mutated form thereof, and can be used to target the protein for ubiquitination and degradation.

The compositions described herein exemplify the use of some of these PTMs.

In any aspect or embodiment described herein, the PTM is a small molecule that binds LRRK2. For example, in any aspect or embodiment described herein, the PTM is represented by the chemical structure PTM-IA or PTM-IB:

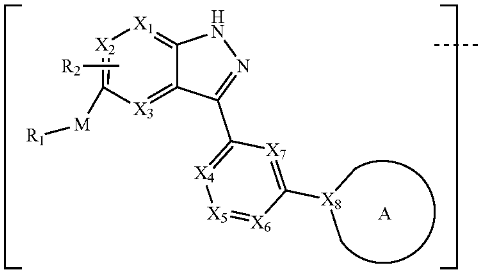

or (PTM-IA)

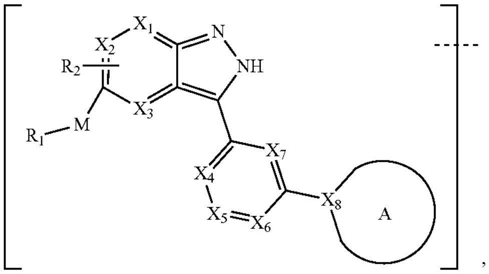

, or

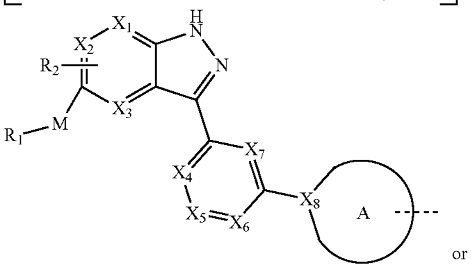

or (PTM-IB)

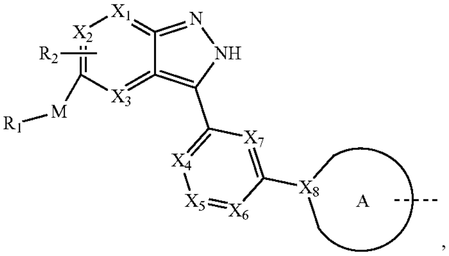

, $R_1$ is selected from a linear or branched $C_1$-$C_6$ alkyl (e.g., isopropyl or tert-butyl), an optionally substituted C3-C6 cycloalkyl (e.g., an optionally substituted C3-C5 cycloalkyl, a methylated C3-C5 cycloalkyl,

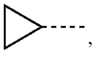, or 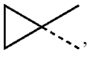, wherein  is the point of attachment to the M of the PTM), linear or branched C1-C6 haloalkyl (e.g., linear or branched C1-C4 haloalkyl), an optionally substituted C3-C6 halocycloalkyl (e.g., C3-C5 halocycloalkyl), an optionally substituted alkylnitrile (e.g., a C1-C4 alkyl nitrile), an optionally substituted C3-C6 cyclonitrile (e.g, a C3-C5 cyclonitrile);

$R_2$ is selected from hydrogen, halogen (e.g., F, Cl, or Br), C1-C3 alkyl, or C1-C3 fluoroalkyl;

$X_1$, $X_2$, $X_3$, $X_4$, $X_5$, $X_6$, and $X_7$ are each independently C, CH or N, wherein $X_1$, $X_2$, $X_3$, and $X_4$ are each optionally substituted with $R_2$ when CH, and $X_5$ is optionally substituted with a C1-C3 alkyl when CH;

$X_8$ is CH, S, or N;

M is a $CH_2$, NH, or O;

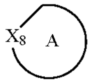

is an optionally substituted 3-10 membered cycloalkyl, optionally substituted 3-10 membered heterocyloalkyl containing 1 to 4 (e.g., 1, 2, 3, or 4) heteroatoms, optionally substituted 3-10 membered bicycloalkyl, optionally substituted 3-10 membered biheterocycloalkyl containing 1 to 4 (e.g., 1, 2, 3, or 4) heteroatoms, optionally substituted 3-10 membered spirocycloalkyl, or optionally substituted 3-10 membered spiroheterocycloalkyl containing 1 to 4 (e.g., 1, 2, 3, or 4) heteroatoms, wherein the heteroatoms are independently selected from N, O, and S (e.g., each is optionally substituted with one or more (e.g., 1, 2, 3, or 4) substituents), and

 of the PTM indicates the point of attachment with a linker (L) or a ULM.

In any aspect or embodiment described herein, the PTM is represented by the chemical structure PTM-IIA, PTM-IIB, PTM-IIIA, PTM-IIIB, PTM-IVA, PTM-IVB, PTM-VA, and PTM-VB.

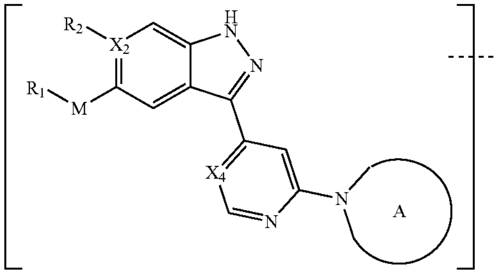

or (PTM-IIA1)

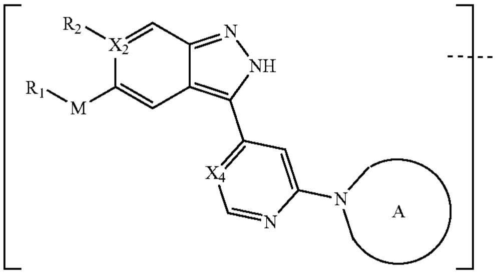

, or

-continued

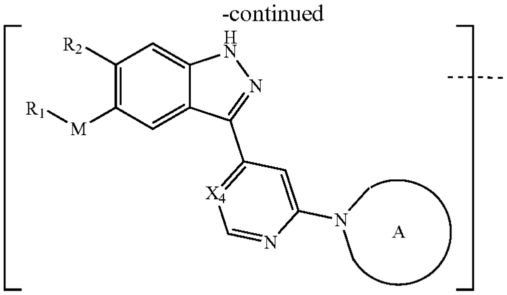

or (PTM-IIA2)

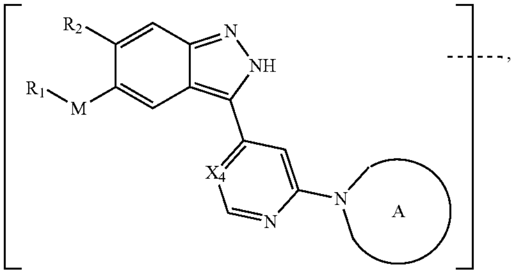

, or

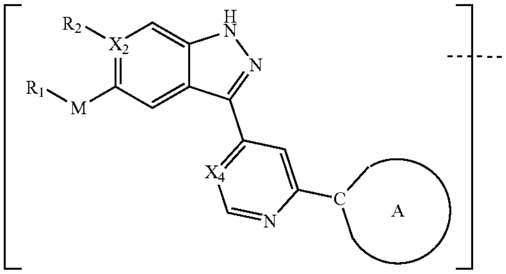

or (PTM-IIA3)

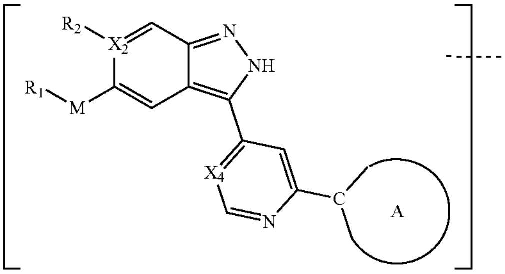

, or

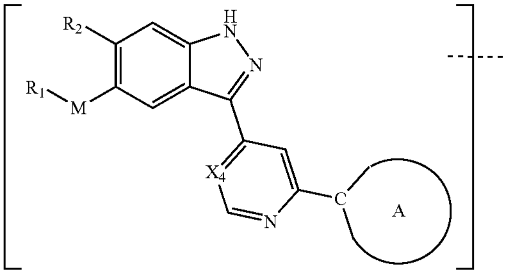

or

-continued
(PTM-IIA4)
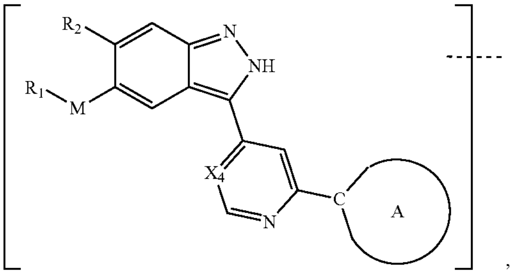
, or
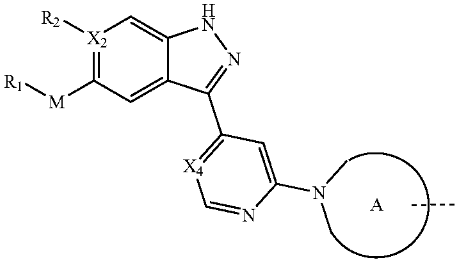
or
(PTM-IIB1)
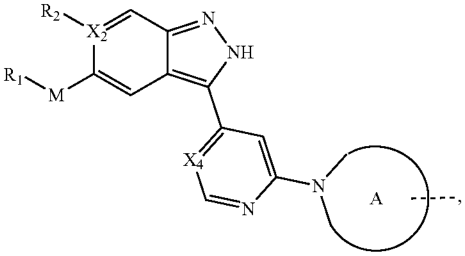
, or
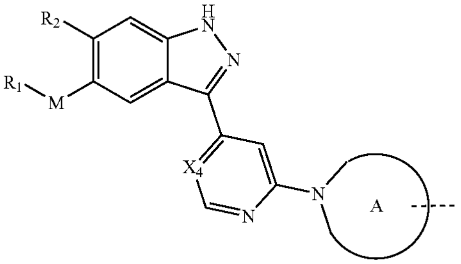
or
(PTM-IIB2)
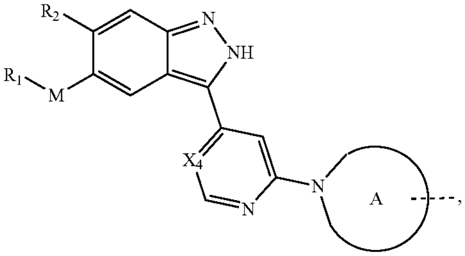
, or
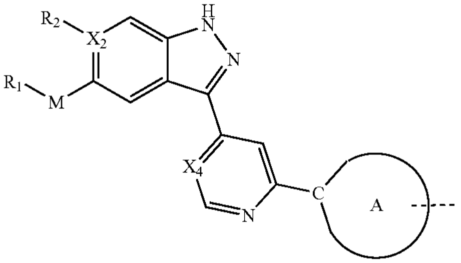
or
-continued
(PTM-IIB3)
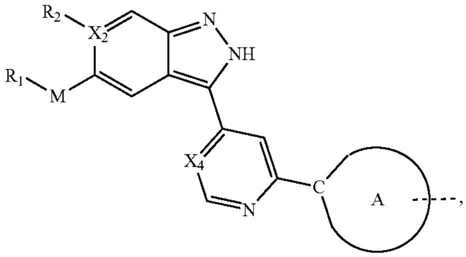
, or
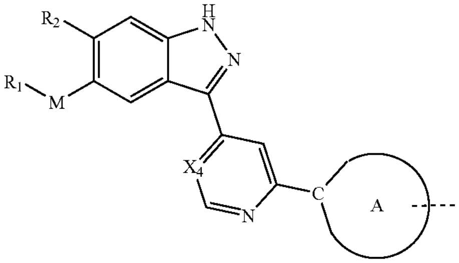
or
(PTM-IIB4)
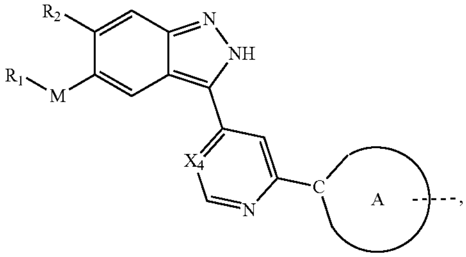
, or
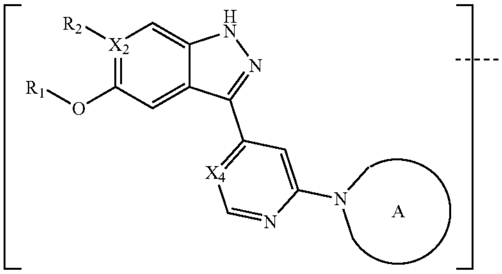
or
(PTM-IIIA1)
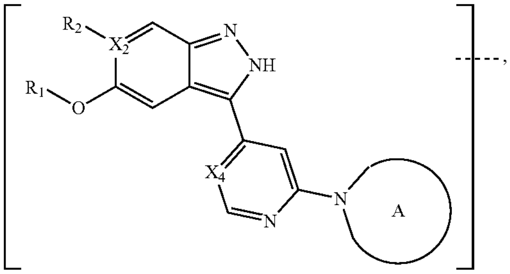
, or
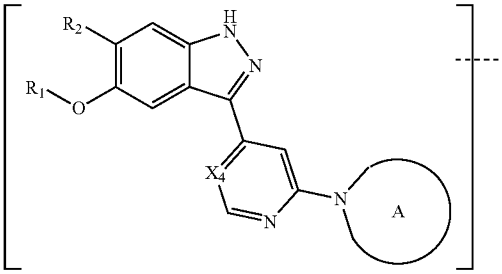
or (PTM-IIIA2)
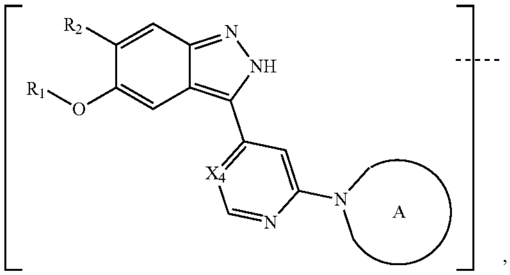
, or
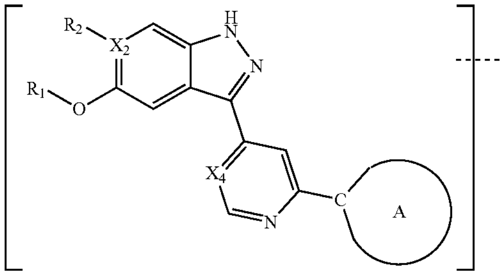
or
(PTM-IIIA3)
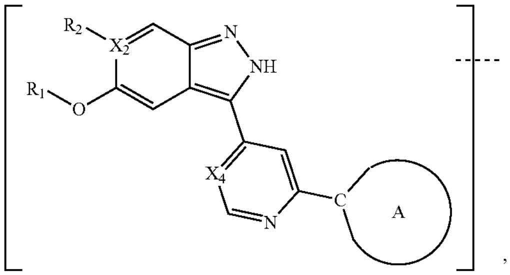
, or
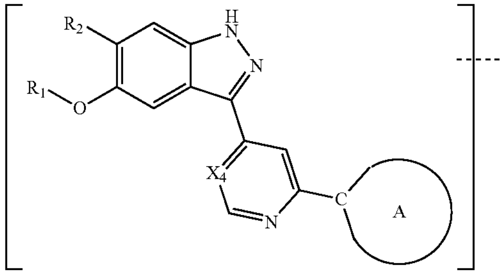
or
(PTM-IIIA4)
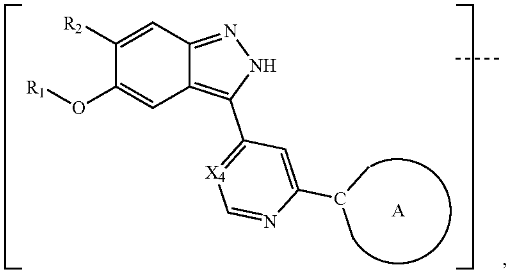
, or
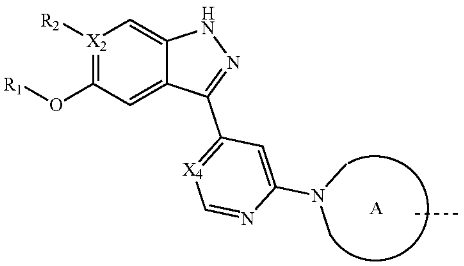
or
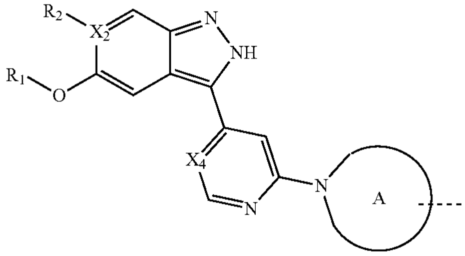
,
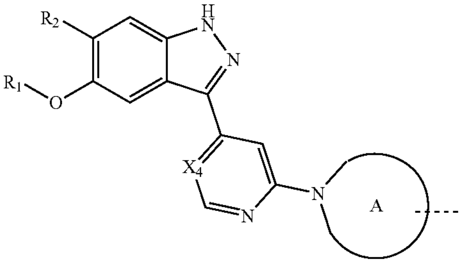
or
(PTM-IIIB2)
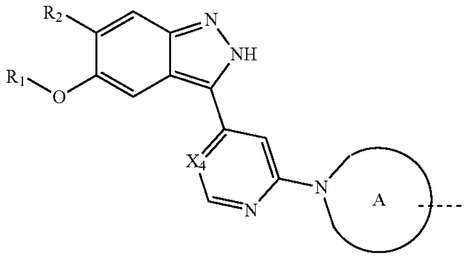
,
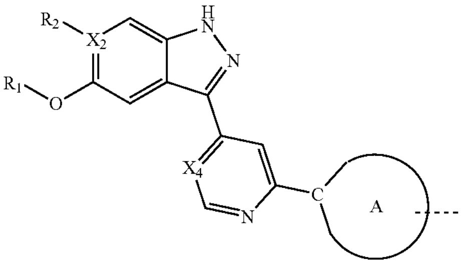
or
(PTM-IIIB3)
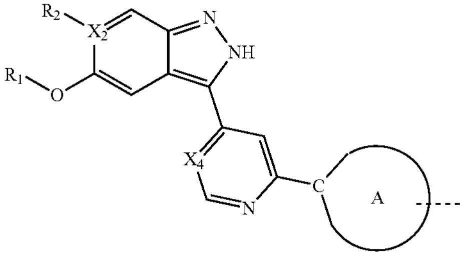
, or -continued

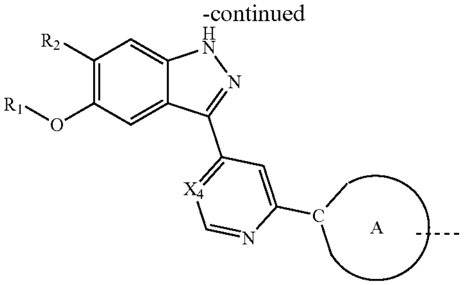

or (PTM-IIIB4)

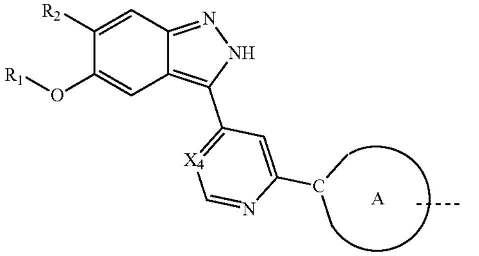

wherein:

$R_1$ is a linear or branched C1-C6 alkyl (e.g., isopropyl or tert-butyl), an optionally substituted C3-C6 cycloalkyl (e.g., an optionally substituted C3-C5 cycloalkyl, a methylated C3-C5 cycloalkyl,

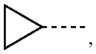, or 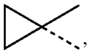, wherein  is the point of attachment to the M of the PTM), linear or branched C1-C6 haloalkyl (e.g., linear or branched C1-C4 haloalkyl), an optionally substituted C3-C6 halocycloalkyl (e.g., C3-C5 halocycloalkyl), an optionally substituted alkylnitrile (e.g., a C1-C4 alkyl nitrile), an optionally substituted C3-C6 cyclonitrile (e.g, a C3-C5 cyclonitrile);

R is absent, hydrogen, halogen (e.g., F, Cl, or Br), OH, C1-C3 alkyl, or C1-C3 fluoroalkyl;

$X_4$ CH or N;

M is a $CH_2$, NH, or O;

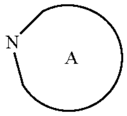 or 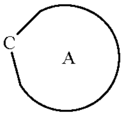

is optionally substituted 3-10 membered cycloalkyl, optionally substituted 3-10 membered heterocyloalkyl containing 1 to 4 (e.g., 1, 2, 3, or 4) heteroatoms, optionally substituted 3-10 membered bicycloalkyl, optionally substituted 3-10 membered biheterocycloalkyl containing 1 to 4 (e.g., 1, 2, 3, or 4) heteroatoms, optionally substituted 3-10 membered spirocycloalkyl, or optionally substituted 3-10 membered spiroheterocycloalkyl containing 1 to 4 (e.g., 1, 2, 3, or 4) heteroatoms, wherein the heteroatoms are independently selected from N, O, and S (e.g., each is optionally substituted with one or more (e.g., 1, 2, 3, or 4) substituents), and

 of the PTM indicates the point of attachment with a chemical linker group or a ULM.

In any aspect or embodiment described herein,

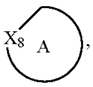, 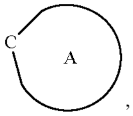, or 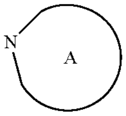

includes 1-4 substitution, each independently selected from a halogen, OH, $NH_2$, N(C1-C3 alkyl)$_2$, linear or branched C1-C4 alkyl (e.g., methyl or ethyl), linear or branched C1-C4 hydroxyalkyl, linear or branched C1-C4 alkoxy, and linear or branched C1-C4 haloalkyl).

In any aspect or embodiment described herein, the PTM is covalently linked to L or ULM via an atom of the heterocycloalkyl of

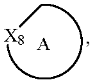, 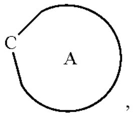, or 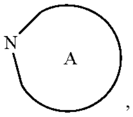, or a substituent thereof.

In any aspect or embodiment described herein,

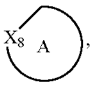, 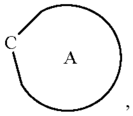, or 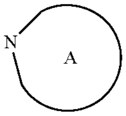

is a 4-7 (e.g., 4, 5, 6, or 7) membered cycloalkyl or heterocycloalkyl containing 1-4 (e.g., 1, 2, 3, or 4) heteroatoms selected from N, O, and S, optionally substituted with one or more (e.g., 1, 2, 3, or 4) substitutions, each independently selected from a halogen, OH, $NH_2$, N(C1-C3 alkyl)$_2$, linear or branched C1-C4 alkyl, linear or branched C1-C4 hydroxyalkyl, linear or branched C1-C4 alkoxy, and linear or branched C1-C4 haloalkyl.

In any aspect or embodiment described herein,

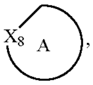, 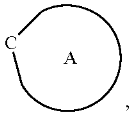, or 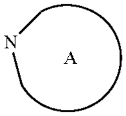

is a 4-7 (e.g., 5 or 6) membered cycloalkyl or heterocycloalkyl containing 1-4 (e.g., 1, 2, 3, or 4) heteroatoms selected from N, O, and S, the ring optionally substituted with one or more (e.g., 1, 2, 3, or 4) substitutions, each independently selected from linear or branched C1-C3 alkyl (e.g., methyl), linear or branched C1-C3 alkoxy (e.g., methoxy), and linear or branched C1-C3 haloalkyl.

In any aspect or embodiment described herein described herein,

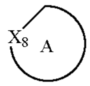

is:

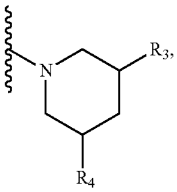 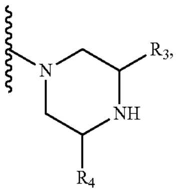

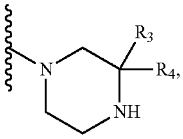 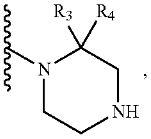 ,

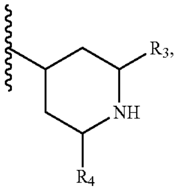 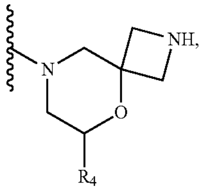

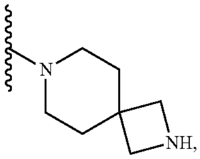 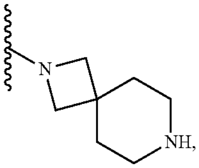

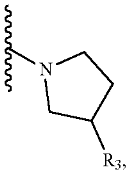 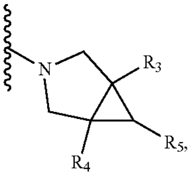

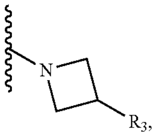 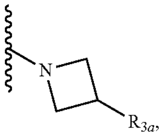

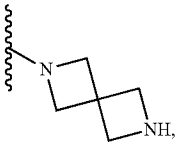 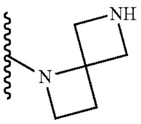 , 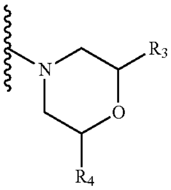 ,

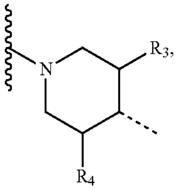 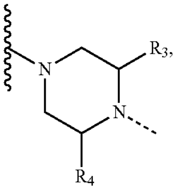

-continued

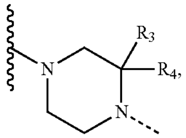 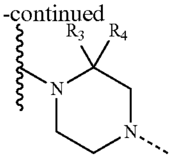 ,

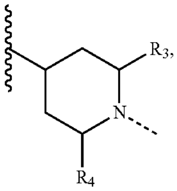 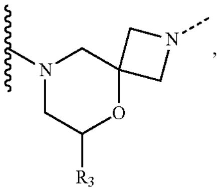 ,

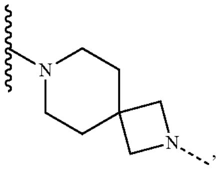 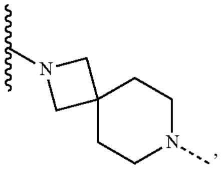

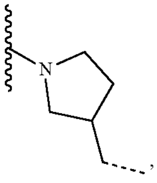 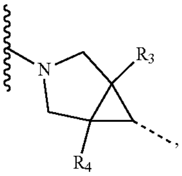

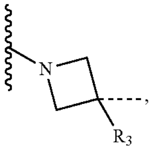 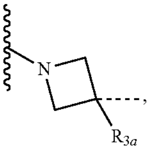 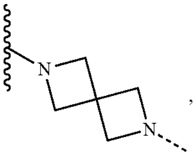 ,

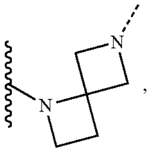 , or 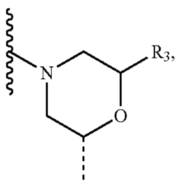

wherein $R_3$, $R_4$, and $R_5$ are each independently selected from a H, halogen, OH, $NH_2$, N(C1-C3 alkyl)$_2$, linear or branched C1-C4 alkyl, linear or branched C1-C4 hydroxyalkyl, linear or branched C1-C4 alkoxy, and linear or branched C1-C4 haloalkyl;

⌇— indicates the point of attachment of the

(i.e., the point of attachment with the 6-membered heteroaryl of the PTM); and

⸝⸝ indicates the point of attachment of the PTM with the L or ULM, and where not present, the

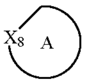

may be attached to the L or ULM via an atom of the cyclic group (e.g., a carbon or nitrogen), $R_3$, $R_4$, or $R_5$.

In any aspect or embodiment described herein described herein, is:

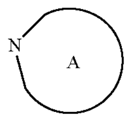

is

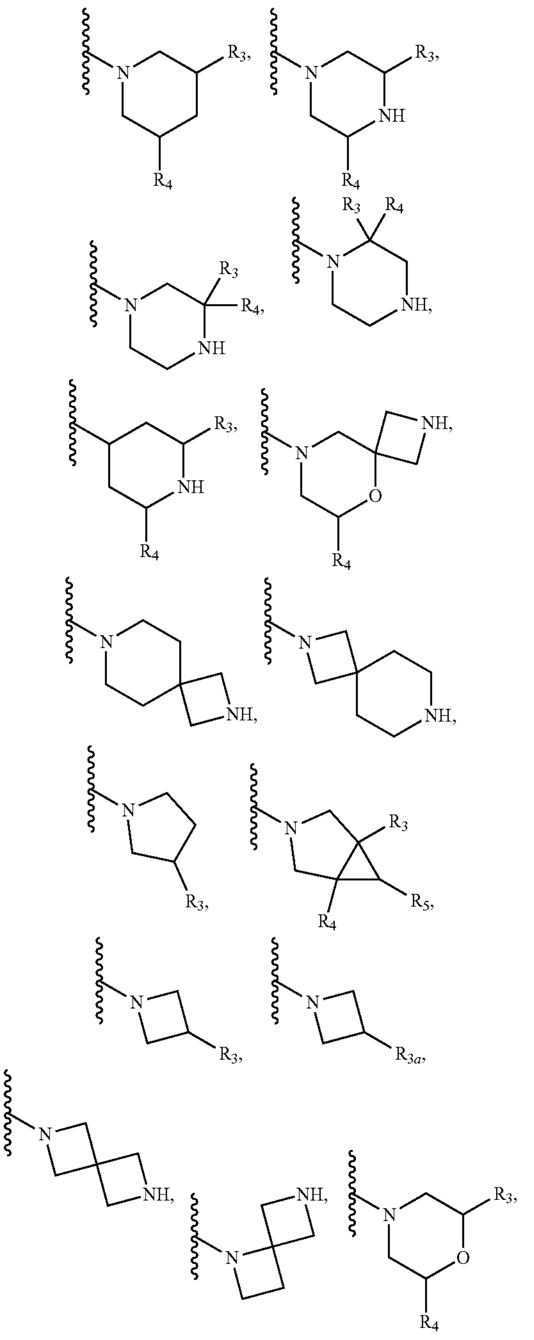

-continued

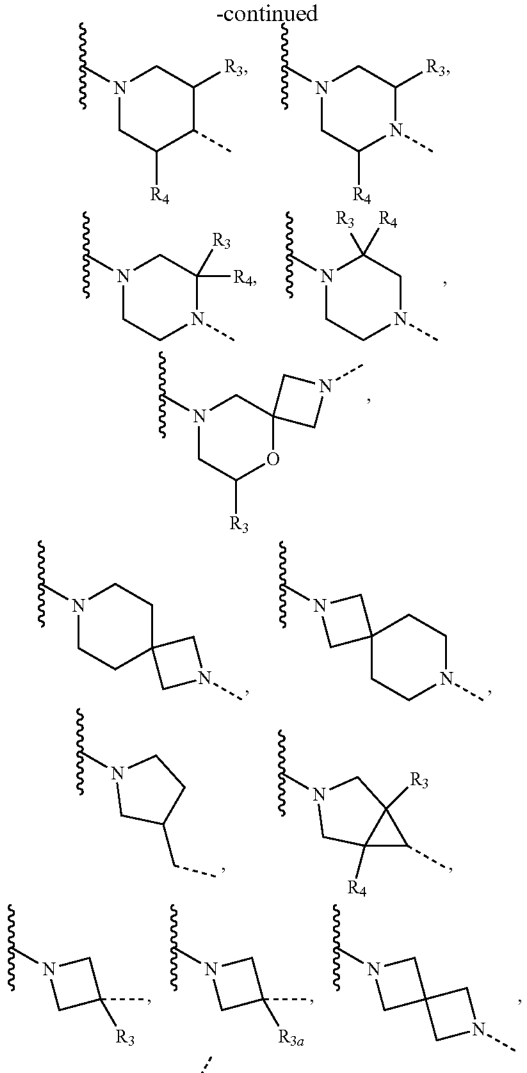

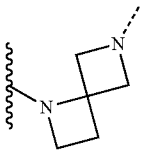

, or

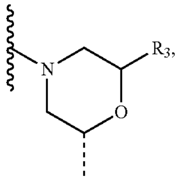

wherein:

$R_3$, $R_4$, and $R_5$ are each independently selected from a H, halogen, OH, $NH_2$, N(C1-C3 alkyl)$_2$, linear or branched C1-C4 alkyl, linear or branched C1-C4 hydroxyalkyl, linear or branched C1-C4 alkoxy, and linear or branched C1-C4 haloalkyl;

 indicates the point of attachment of the

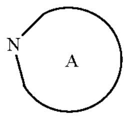

(i.e., the point of attachment with the 6-membered heteroaryl of the PTM); and indicates the point of attachment of the PTM with the L or ULM, and where not present, the

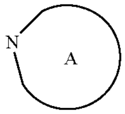

may be attached to the L or ULM via an atom of the cyclic group (e.g., a carbon or nitrogen), $R_3$, $R_4$, or $R_5$.

In any aspect or embodiment described herein, such as but not limited to that in the preceding paragraph or the following paragraph,

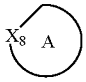

or

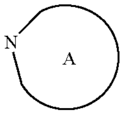

is

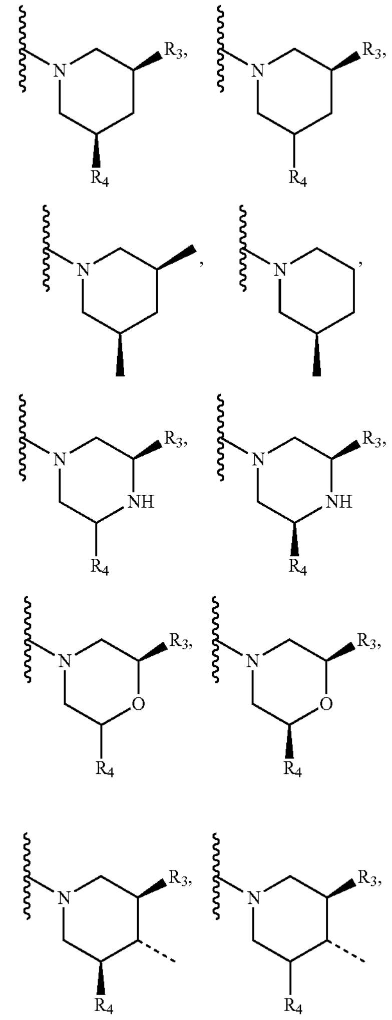

-continued

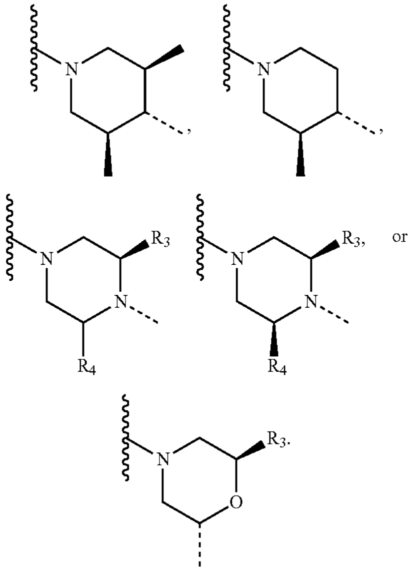

In any aspect or embodiment described herein, such as but not limited to that in the preceding paragraph or the following paragraph,

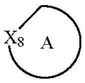

or

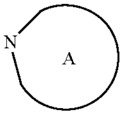

or

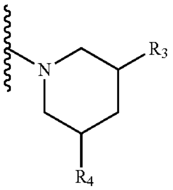

is:

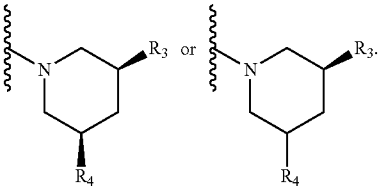

In any aspect or embodiment described herein, such as but not limited to that in the preceding paragraph or the following paragraph,

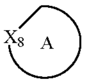

or

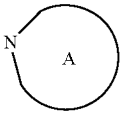

is:

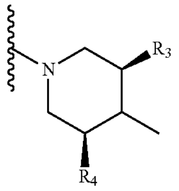 or 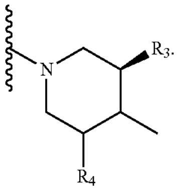

In any aspect or embodiment described herein, such as but not limited to that in the preceding paragraph,

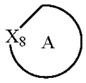 or 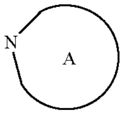 or

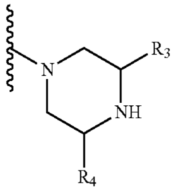

is:

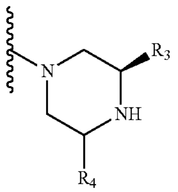 or 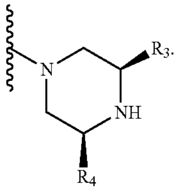

In any aspect or embodiment described herein, such as but not limited to that in the preceding paragraph,

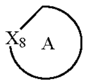 or 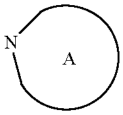 or

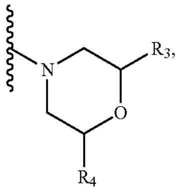

is:

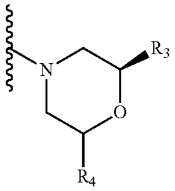 or 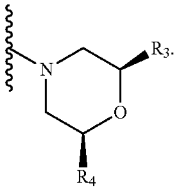

In any aspect or

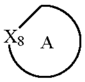 or 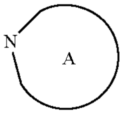 or

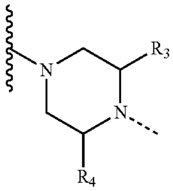

is:

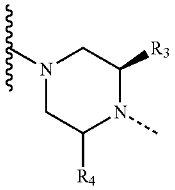 or 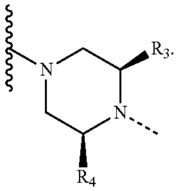

In any aspect or embodiment described herein, such as but not limited to that in the preceding paragraph,

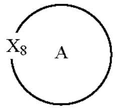 or 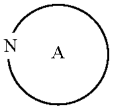 or

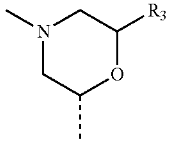

is:

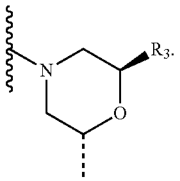

In any aspect or embodiment described herein described herein,

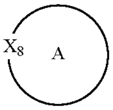

is:

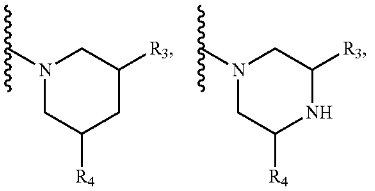

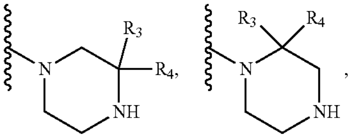

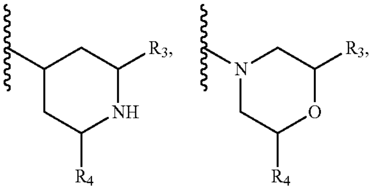

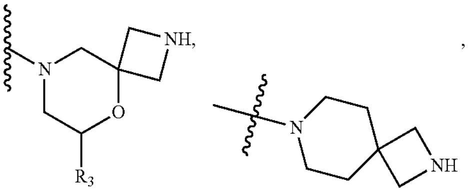

,

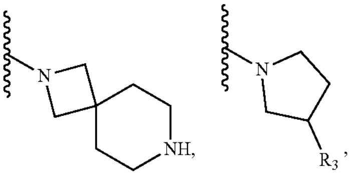

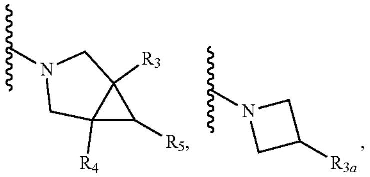

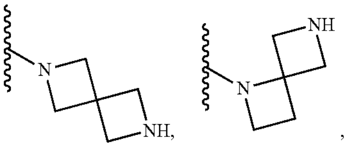

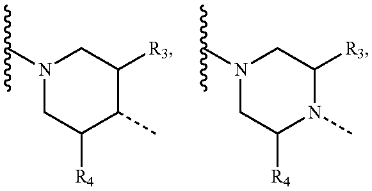

-continued

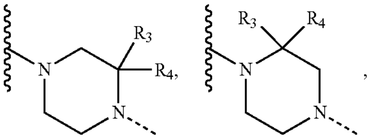

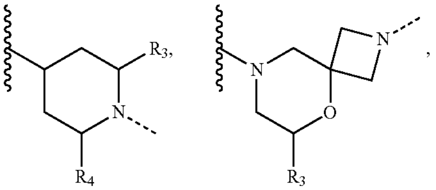

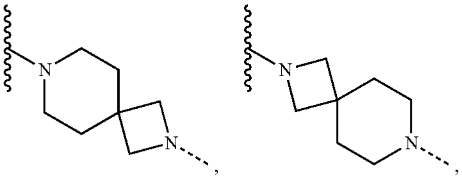

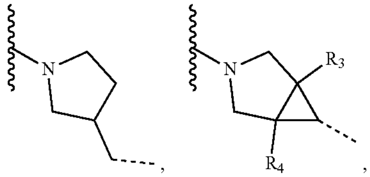

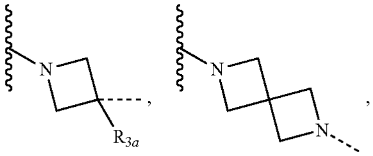

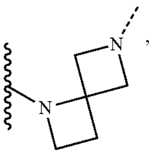

or

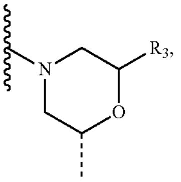

wherein:

$R_3$ is H or linear or branched C1-C3 alkyl (e.g., methyl or ethyl);

$R_{3a}$ is H, halogen, or linear or branched C1-C3 alkyl (e.g., methyl);

$R_4$ is H or linear or branched C1-C3 alkyl (e.g., methyl or ethyl);

$R_5$ is H or linear or branched C1-C3 alkyl (e.g., methyl);

⌇— indicates the point of attachment of the

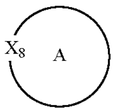

(i.e., the point of attachment with the 6-membered heteroaryl of the PTM); and

-‑' indicates the point of attachment of the PTM with the L or ULM, and where not present, the

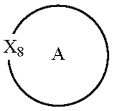
may be attached to the L or ULM via an atom of the cyclic group (e.g., a carbon or nitrogen of the 6-membered heterocycloalkyl), $R_3$, $R_4$, or $R_5$.
In any aspect or embodiment described herein described herein,
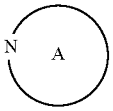
is:
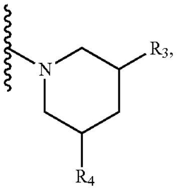
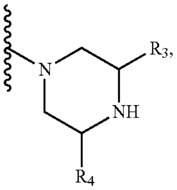
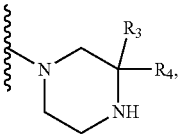
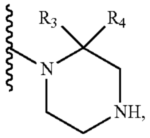
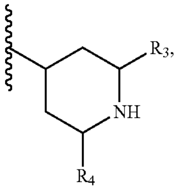
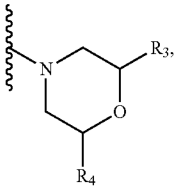
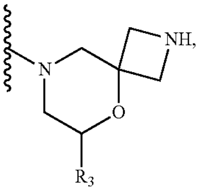
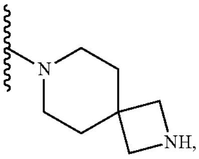
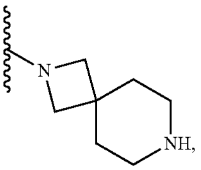
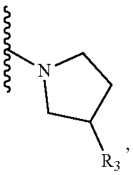
-continued
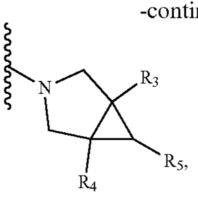
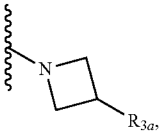
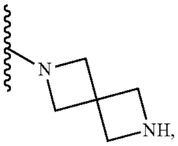
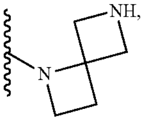
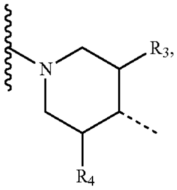
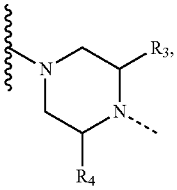
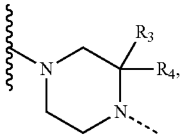
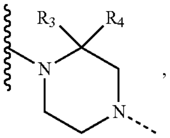
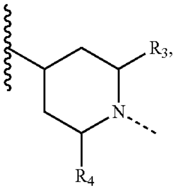
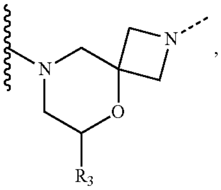
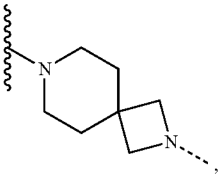
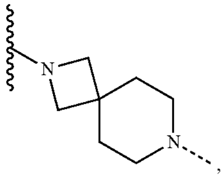
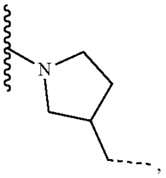
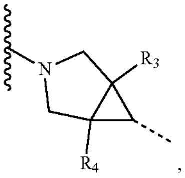
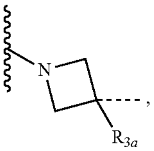
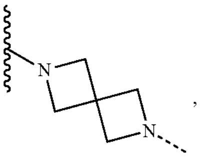
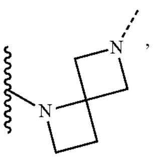
or
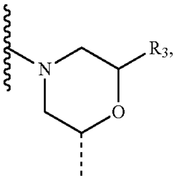
wherein:
$R_3$ is H or linear or branched C1-C3 alkyl (e.g., methyl or ethyl);

$R_{3a}$ is H, halogen, or linear or branched C1-C3 alkyl (e.g., methyl);

$R_4$ is H or linear or branched C1-C3 alkyl (e.g., methyl or ethyl);

$R_5$ is H or linear or branched C1-C3 alkyl (e.g., methyl);

— indicates the point of attachment of the

(i.e., the point of attachment with the 6-membered heteroaryl of the PTM); and indicates the point of attachment of the PTM with the L or ULM, and where not present, the

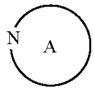

may be attached to the L or ULM via an atom of the cyclic group (e.g., a carbon or nitrogen of the 6-membered heterocycloalkyl), $R_3$, $R_4$, or $R_5$.

In any aspect or embodiment described herein,

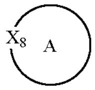

is selected from:

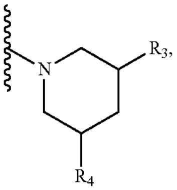 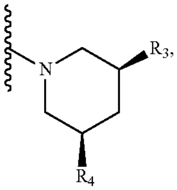

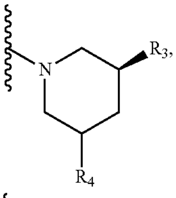 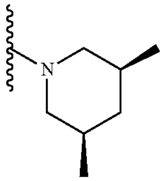 , 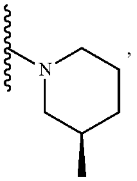 ,

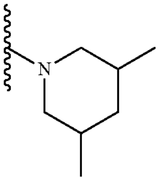 , 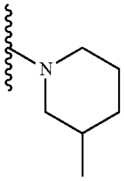 , 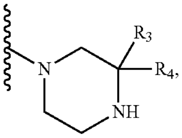

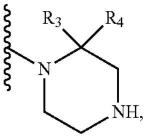 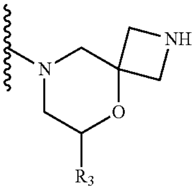 ,

-continued

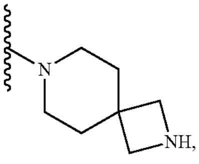 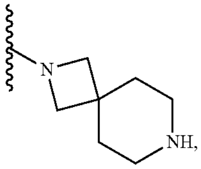

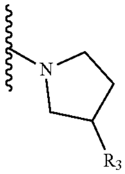 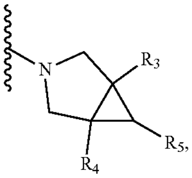

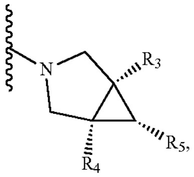 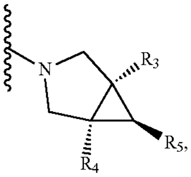

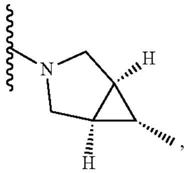 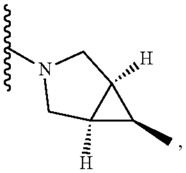

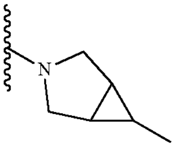 , 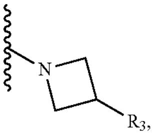

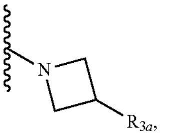 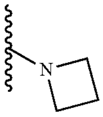 , 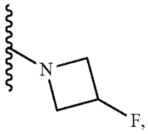

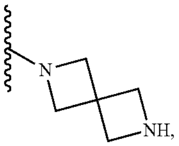 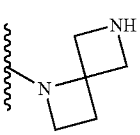 ,

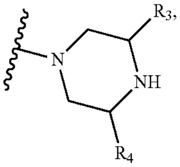 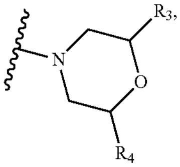

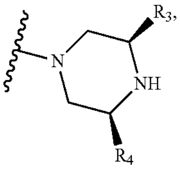 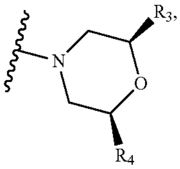

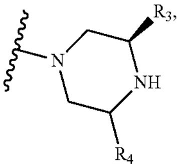 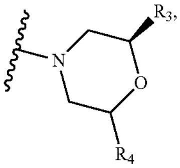

-continued
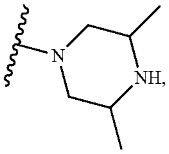 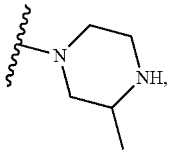
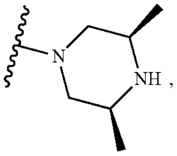 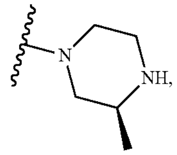
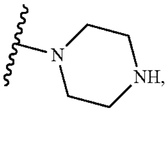 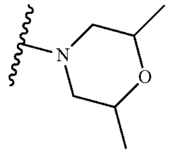,
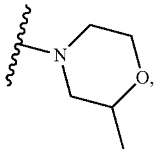 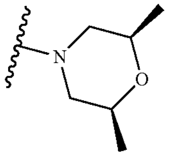,
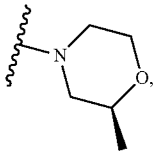 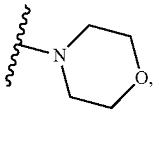
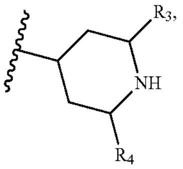 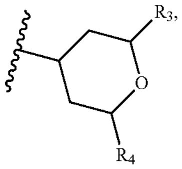
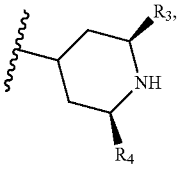 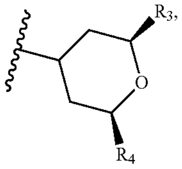
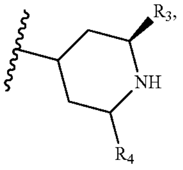 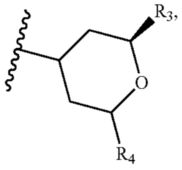
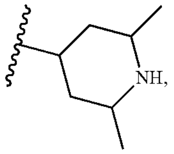 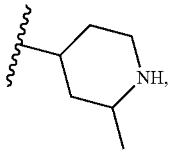
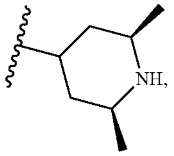 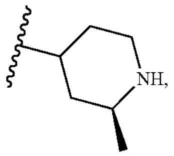
-continued
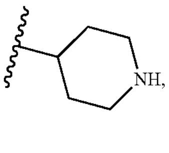 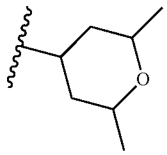,
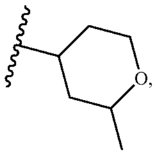 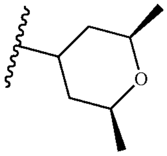,
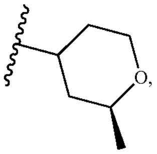 and 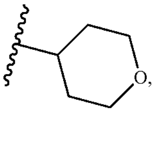
wherein $R_3$ and $R_4$ are defined as described in any aspect or embodiment described herein.
In any aspect or embodiment described herein,
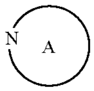
is selected from:
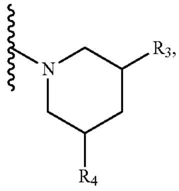 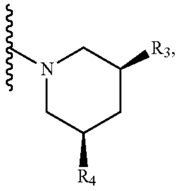
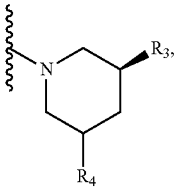 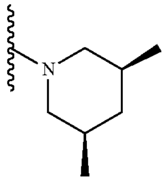, 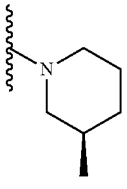,
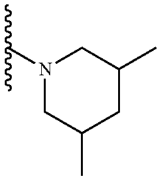, 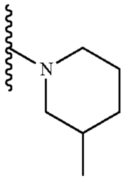, 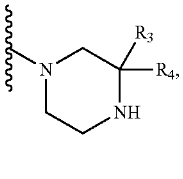
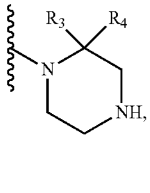 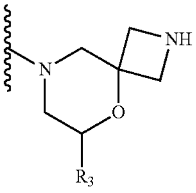, -continued
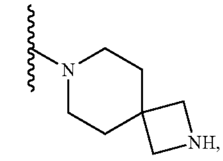 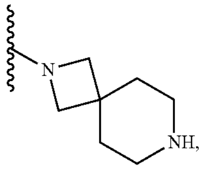
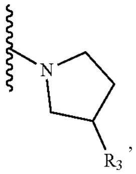 , 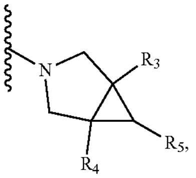
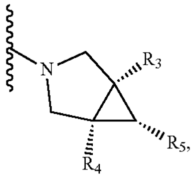 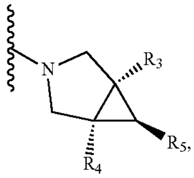
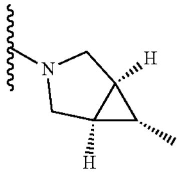 , 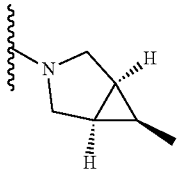 ,
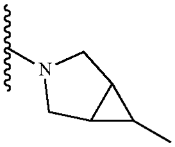 , 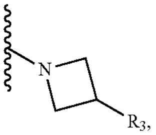
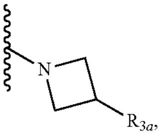 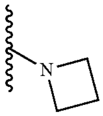 , 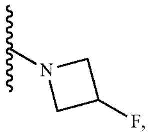
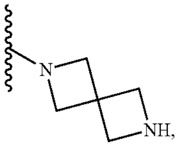 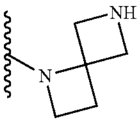 ,
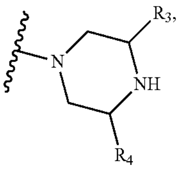 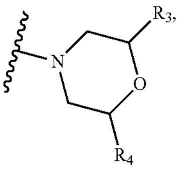
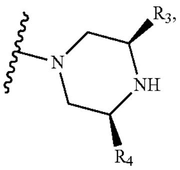 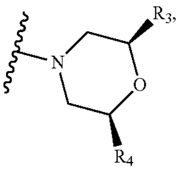
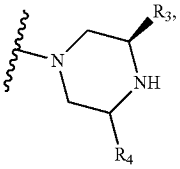 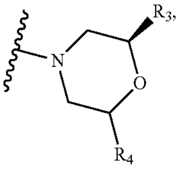
-continued
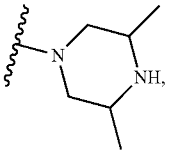 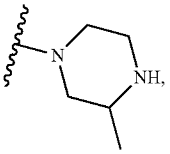
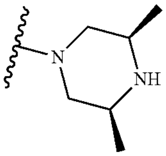 , 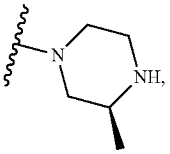
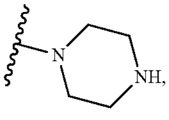 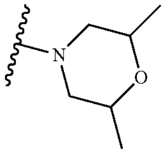 ,
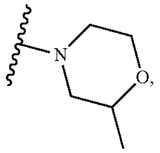 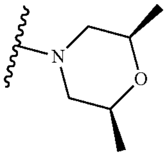 ,
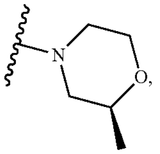 and 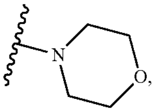
wherein $R_3$ and $R_4$ are defined as described in any aspect or embodiment described herein
In any aspect or embodiment described herein,
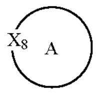
is selected from:
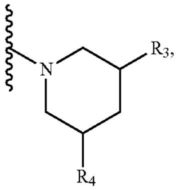 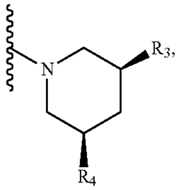
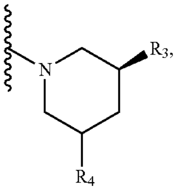 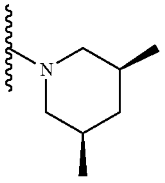 , 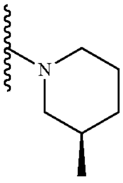 ,
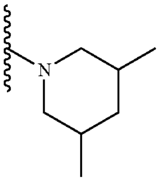 , 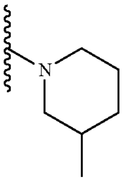 , 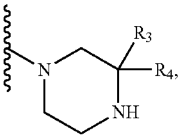

-continued
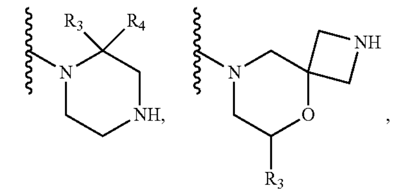
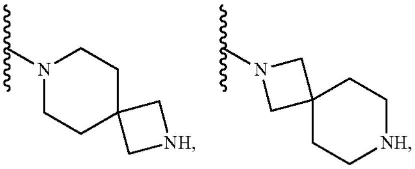
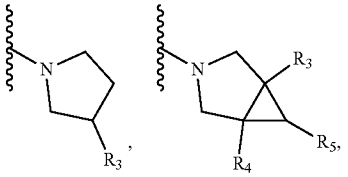
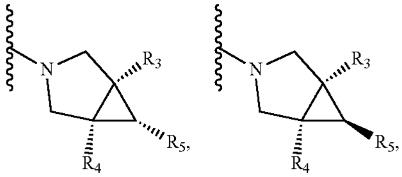
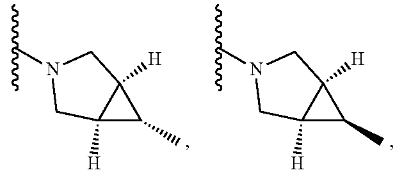
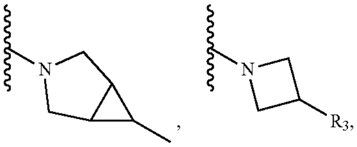
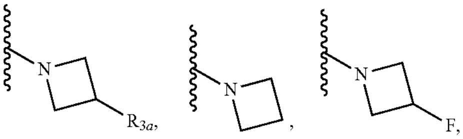
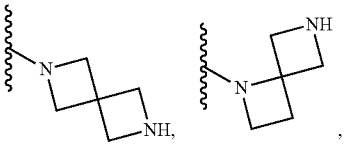
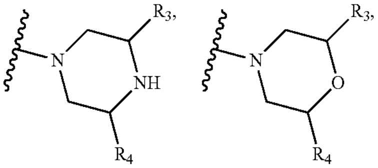
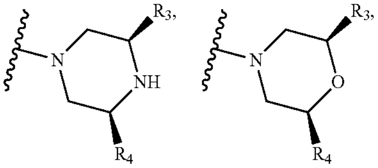
-continued
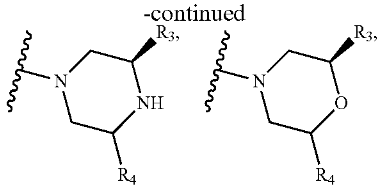
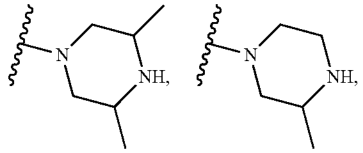
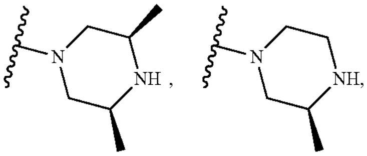
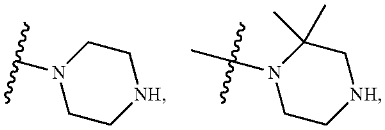
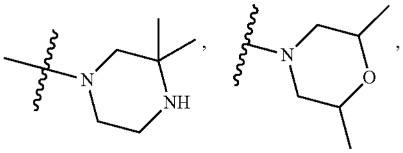
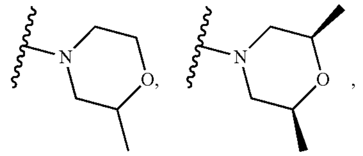
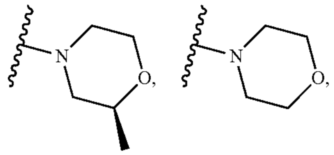
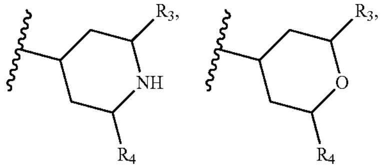
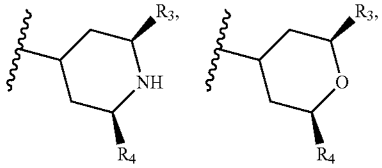
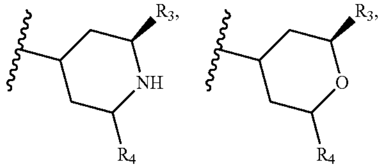
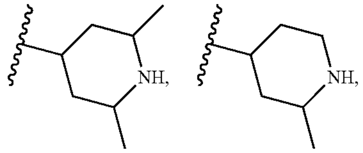

-continued
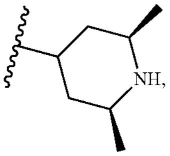 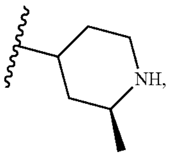
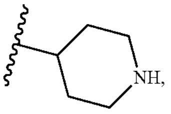 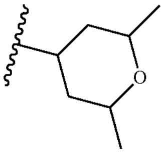 ,
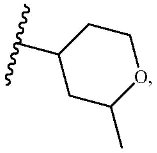 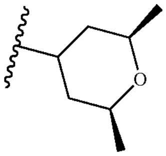 ,
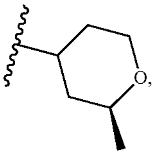 and 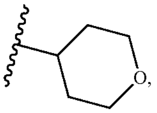
wherein:
$R_3$, $R_{3a}$, $R_4$, and $R_5$ are defined as described in any aspect or embodiment described herein; and
the heterocycloalkyl is attached to L or PTM via an atom of the heterocycloalkyl or a substituent thereof (e.g., $R_3$, $R_{3a}$, $R_4$, $R_5$, or a methyl group).
In any aspect or embodiment described herein,
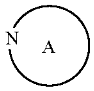
is selected from:
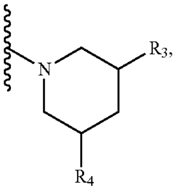 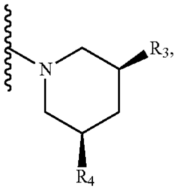
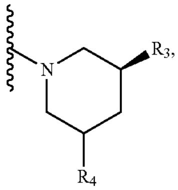 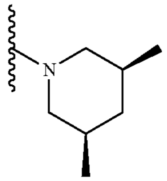 , 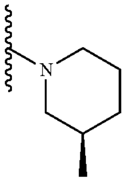 ,
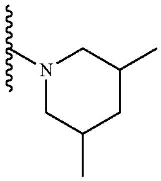 , 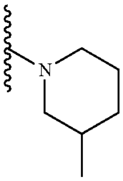 , 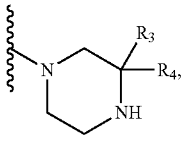
-continued
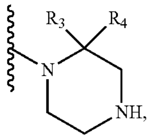 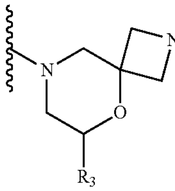 ,
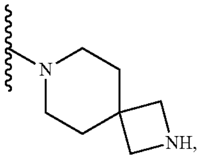 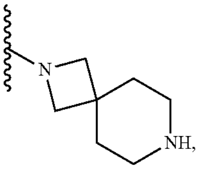
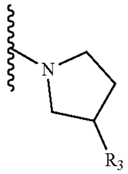 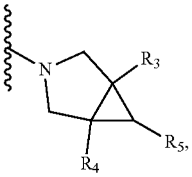
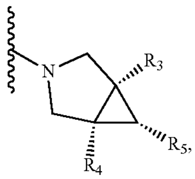 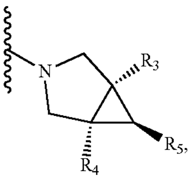
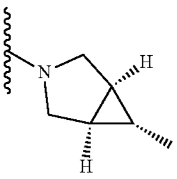 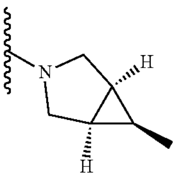
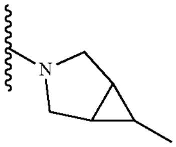 , 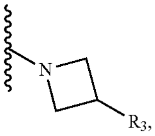
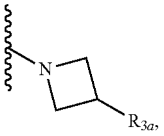 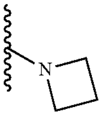 , 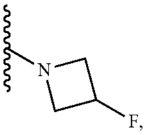
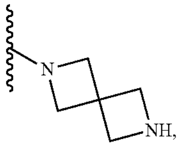 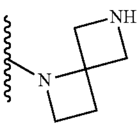 ,
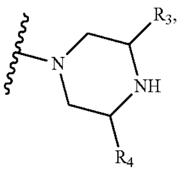 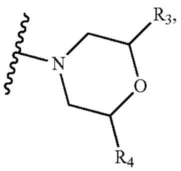
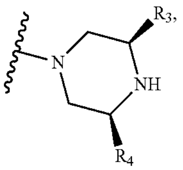 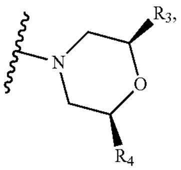

-continued

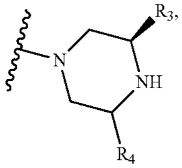
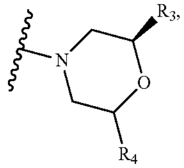
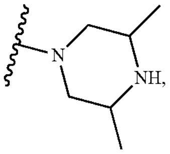
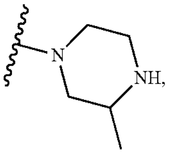
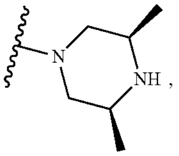
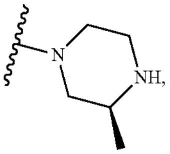
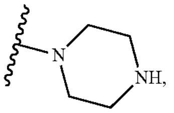
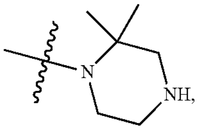
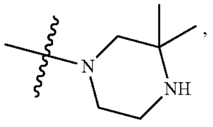
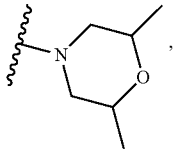
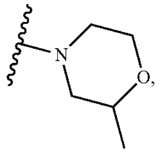
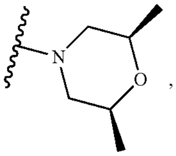
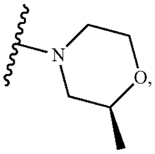
and
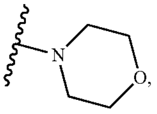

wherein:

$R_3$, $R_{3a}$, $R_4$, and $R_5$ are defined as described in any aspect or embodiment described herein; and the heterocycloalkyl is attached to L or PTM via an atom of the heterocycloalkyl or a substituent thereof (e.g., $R_3$, $R_{3a}$, $R_4$, $R_5$, or a methyl group).

In any aspect or embodiment described herein, the PTM has the chemical structure:

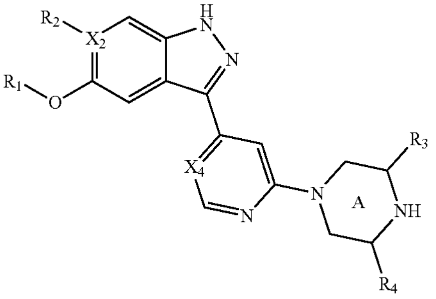
or

-continued (PTM-IIIA)

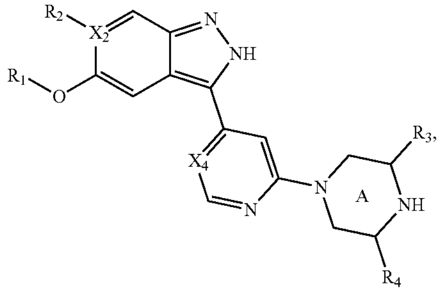

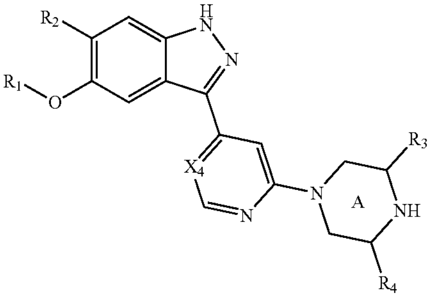
or (PTM-IIIB)

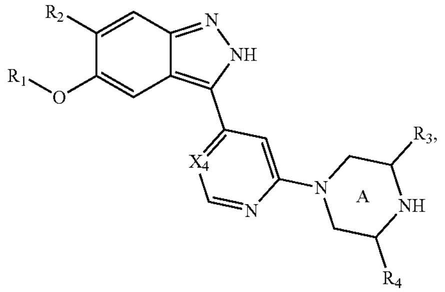

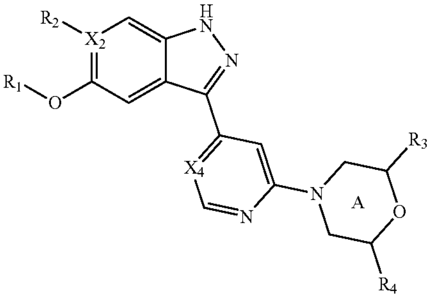
or (PTM-IVA)

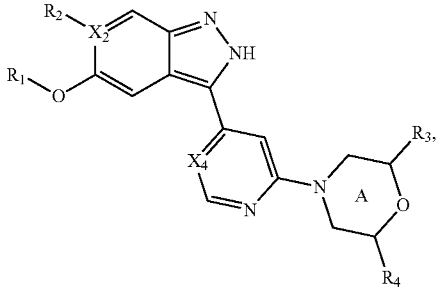

-continued
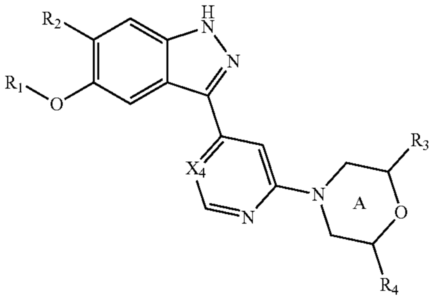
or
(PTM-IVB)
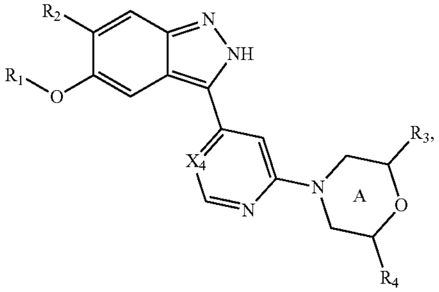
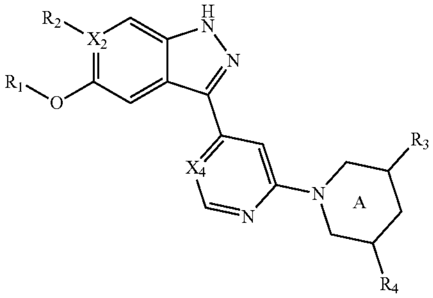
or
(PTM-VA)
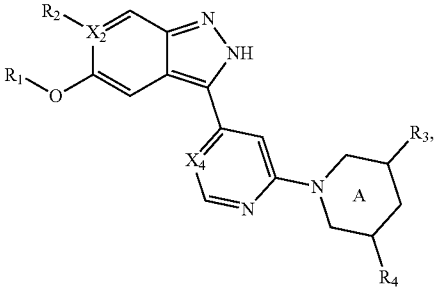
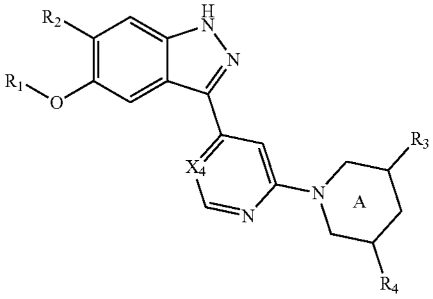
or
-continued
(PTM-VB)
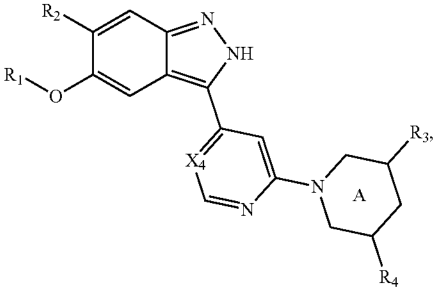
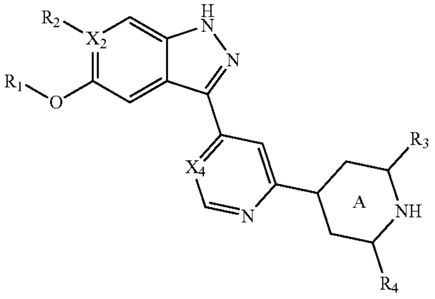
or
(PTM-VIA)
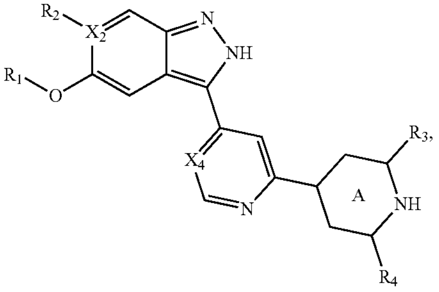
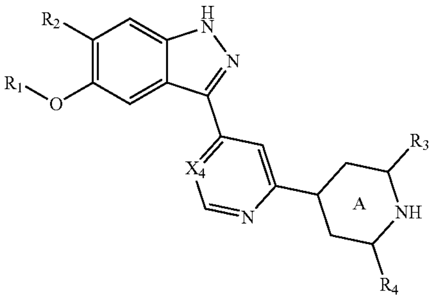
or
(PTM-VIB)
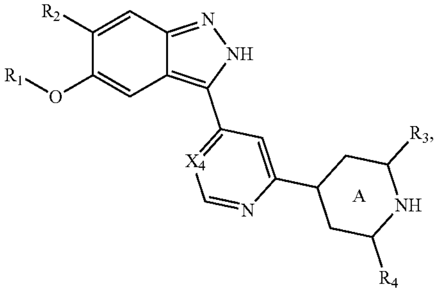

-continued
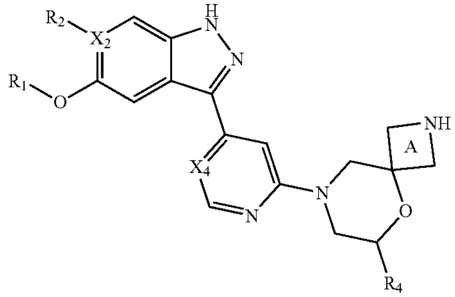
or
(PTM-VIIA)
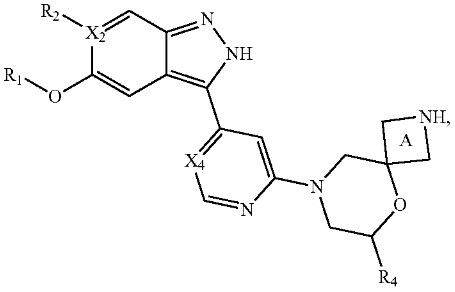
,
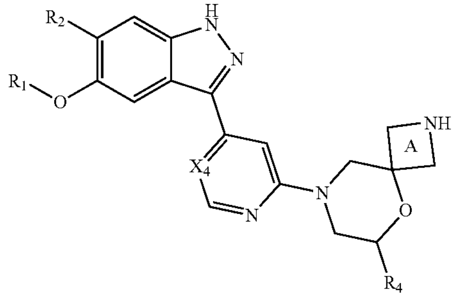
or
(PTM-VIIB)
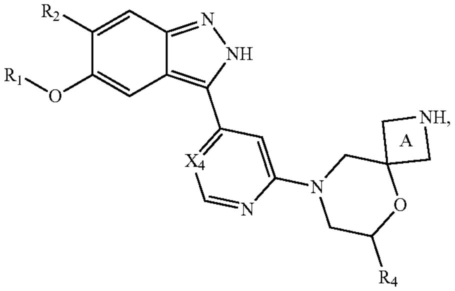
,
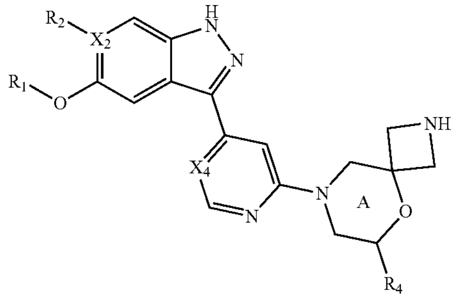
or
-continued
(PTM-VIIIA)
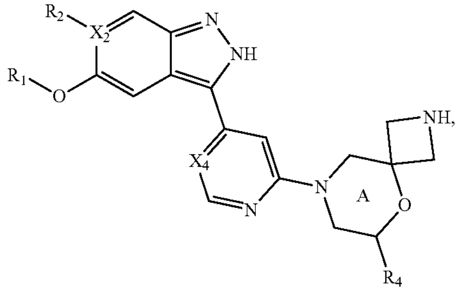
,
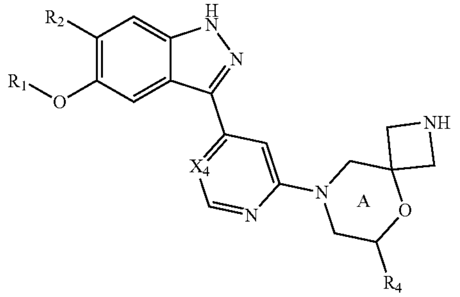
or
(PTM-VIIIB)
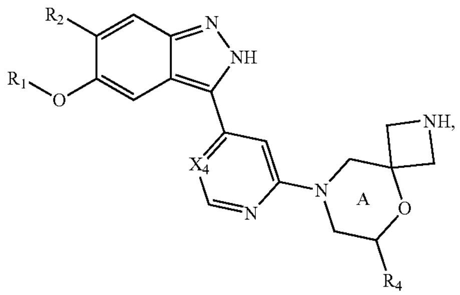
,
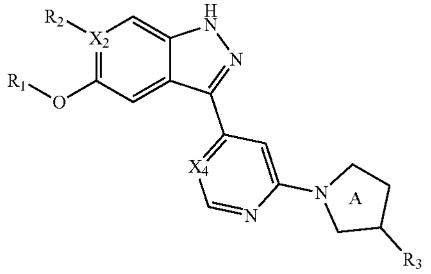
or
(PTM-IXA)
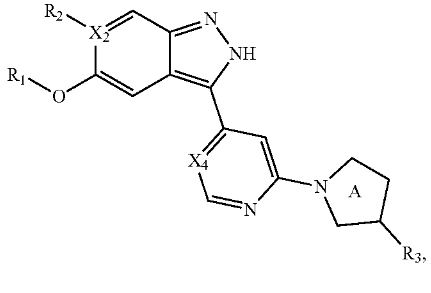
, -continued
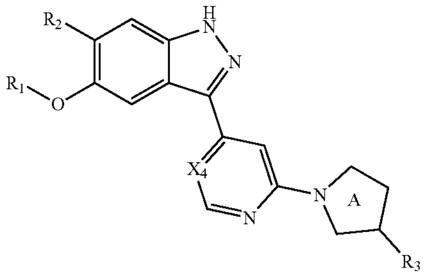
or
(PTM-IXB)
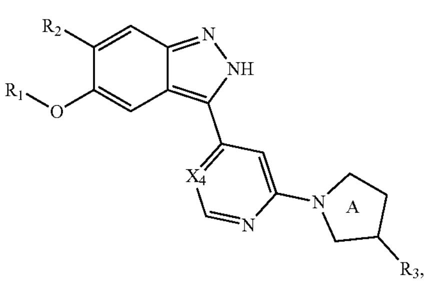
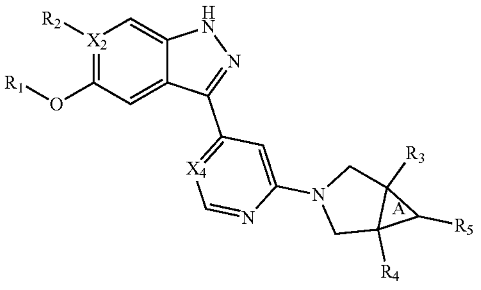
or
(PTM-XA)
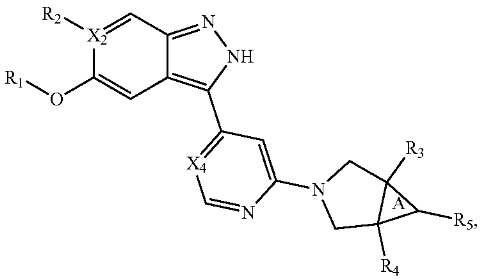
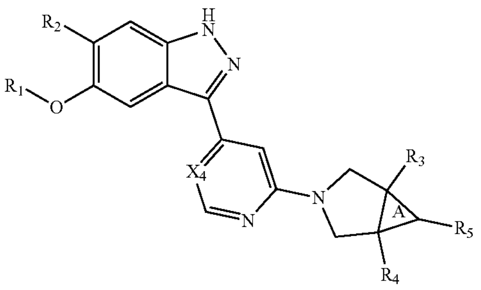
or
-continued
(PTM-XB)
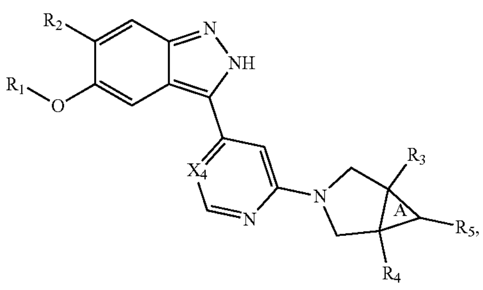
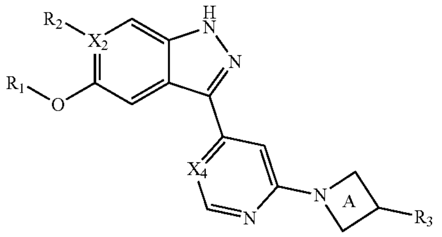
or
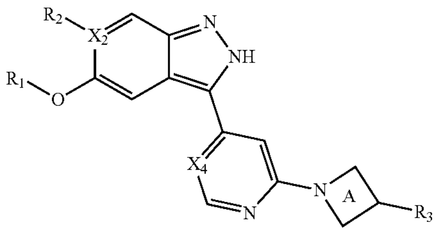
or
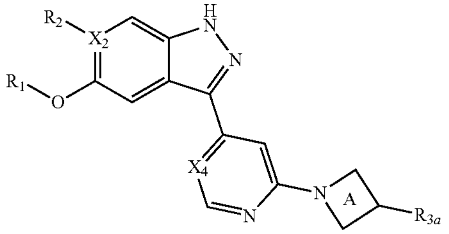
or
(PTM-XIA)
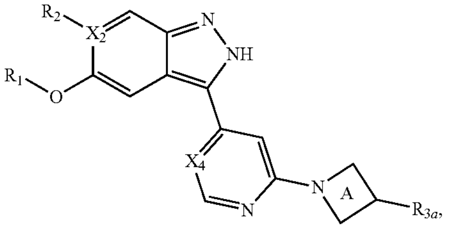
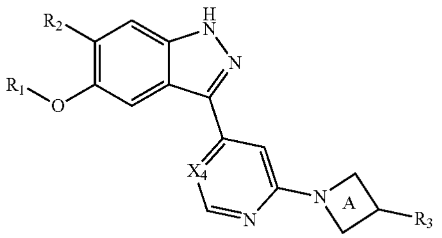
or -continued
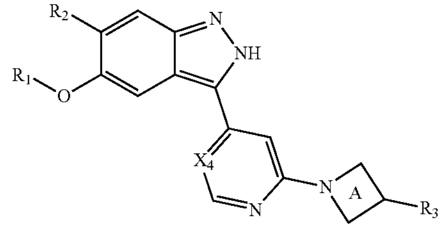
or
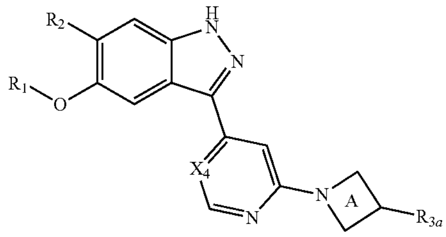
or
(PTM-XIB)
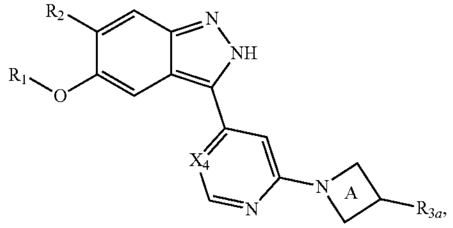
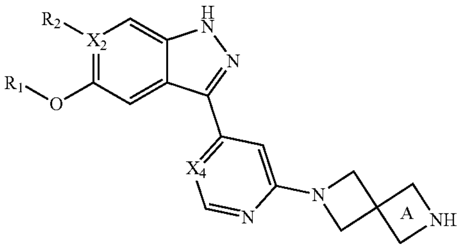
or
(PTM-XIIA)
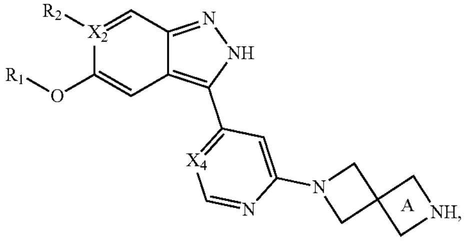
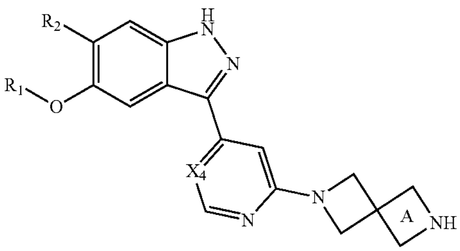
or
-continued
(PTM-XIIB)
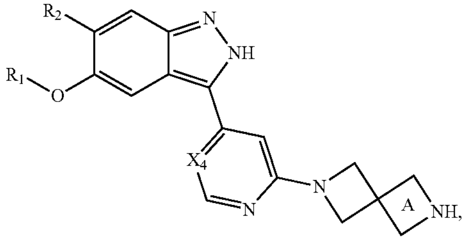
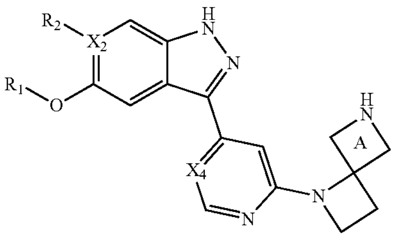
or
(PTM-XIIIA)
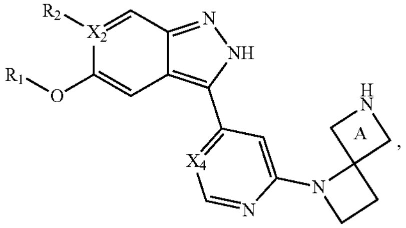
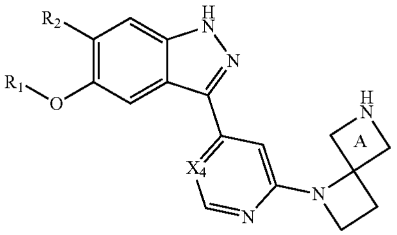
or
(PTM-XIIIB)
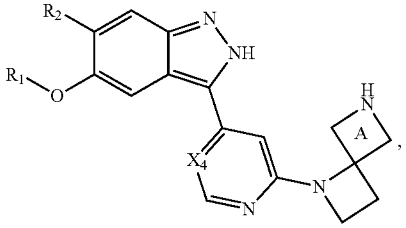
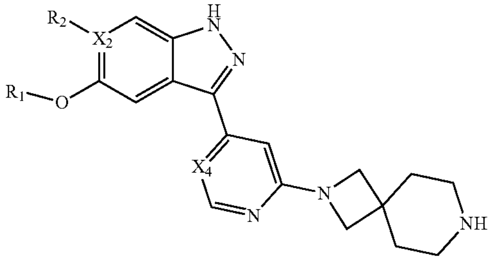
or -continued
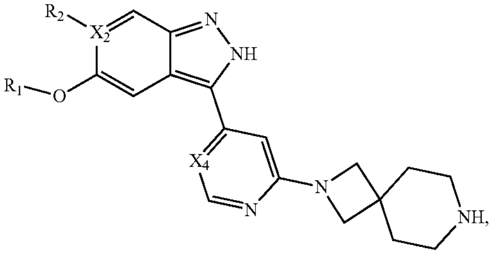
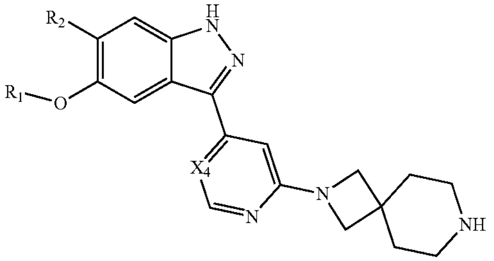
or
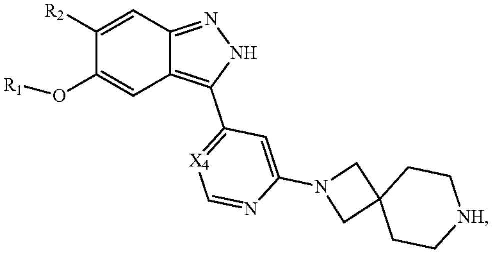
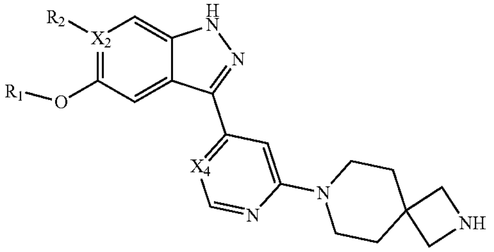
or
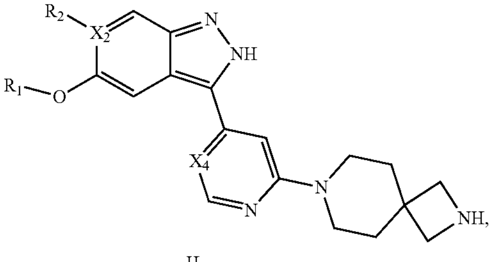
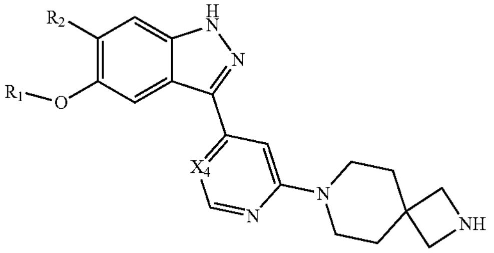
or
-continued
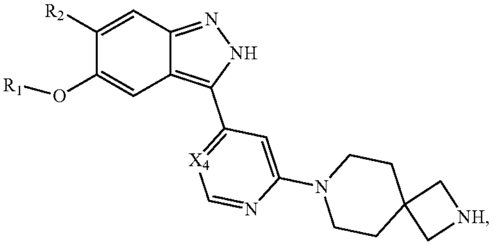
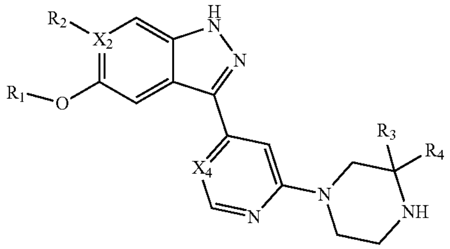
or
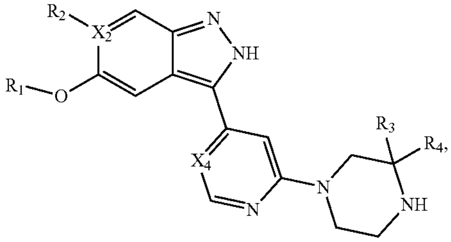
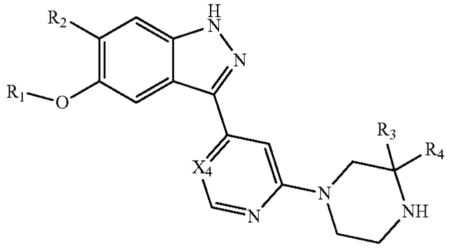
or
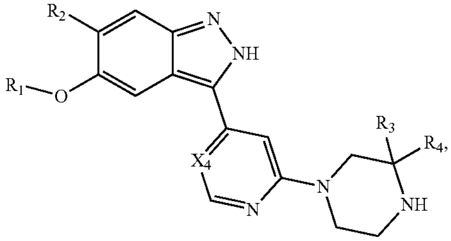
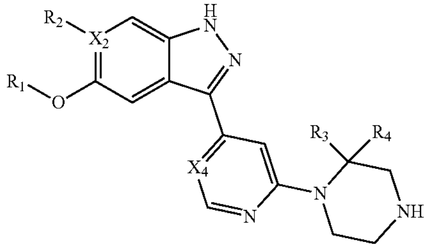
or
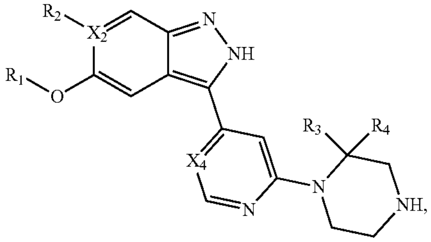
or -continued

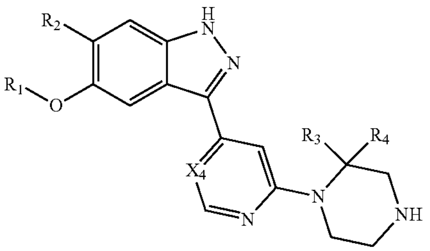

or

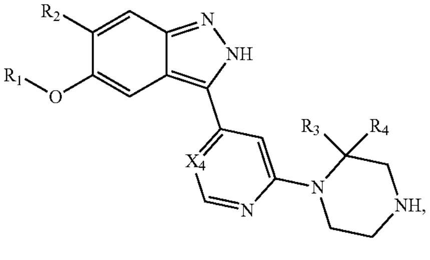

wherein:

$X_2$, $X_4$, $R^1$, $R_2$, $R_3$, $R_{3a}$, $R_4$, and $R_5$ are defined as described in any aspect or embodiment described herein; and the PTM is attached to the L or ULM via an atom of heterocyloalkyl A (e.g, a carbon or nitrogen of the heterocycloalkyl), $R_3$, $R_4$, or $R_5$.

In any aspect or embodiment described herein, the PTM has the chemical structure:

(PTM-XIVA)

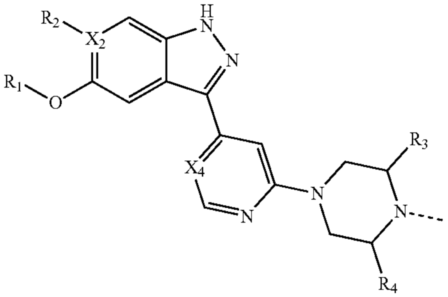

or

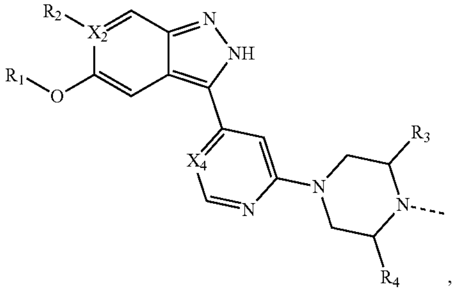

,

-continued (PTM-XIVB)

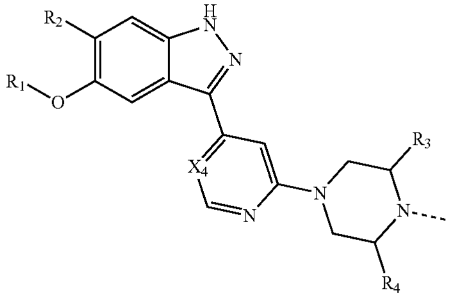

or

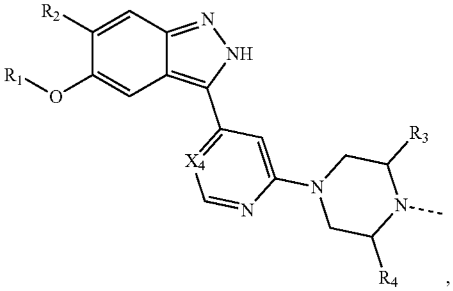

, (PTM-XVA)

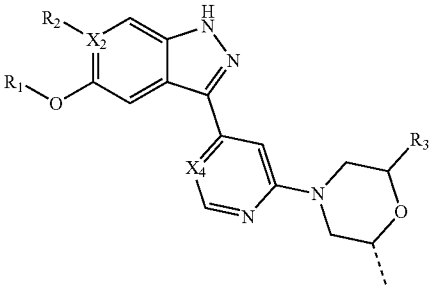

or

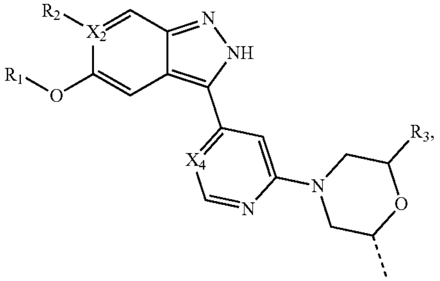

(PTM-XVB)

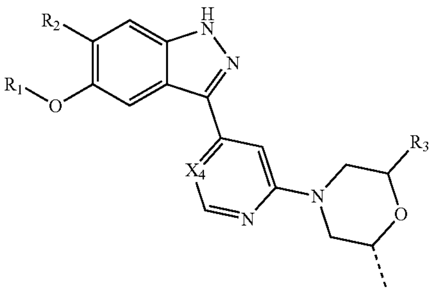

or

-continued
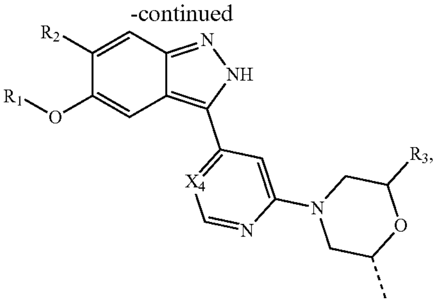
(PTM-XVIA)
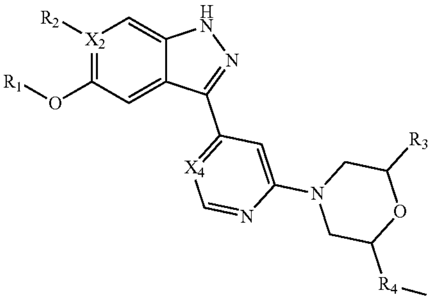
or
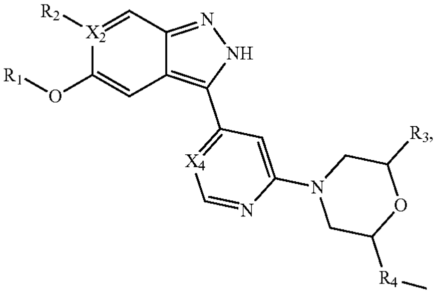
(PTM-XVIB)
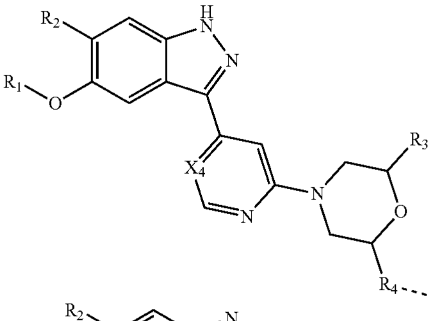
or
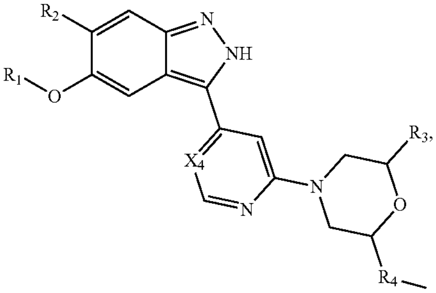
-continued
(PTM-XVIIA)
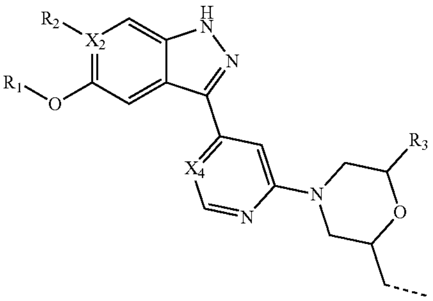
or
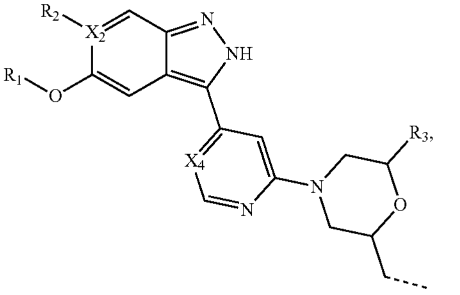
(PTM-XVIIB)
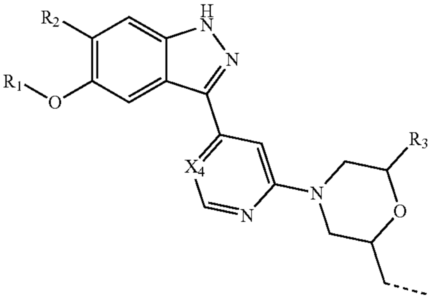
or
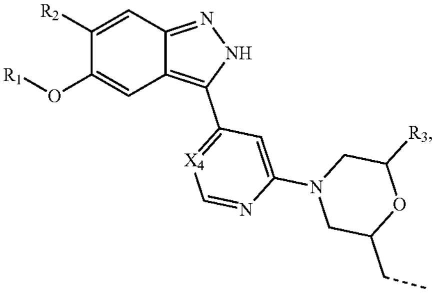
(PTM-XVIIIA)
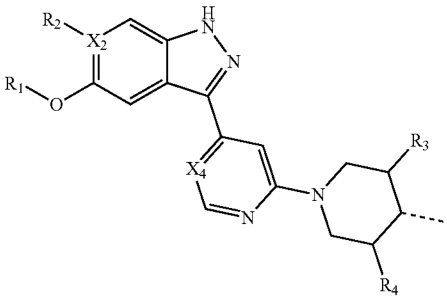
or -continued
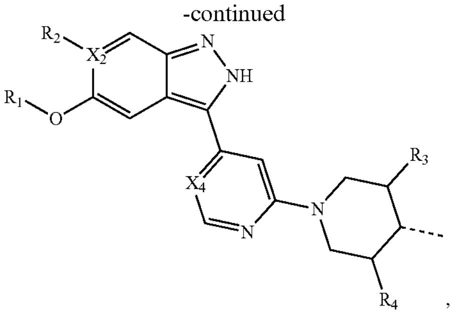
,
(PTM-XVIIIB)
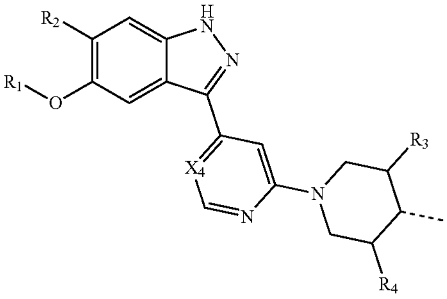
or
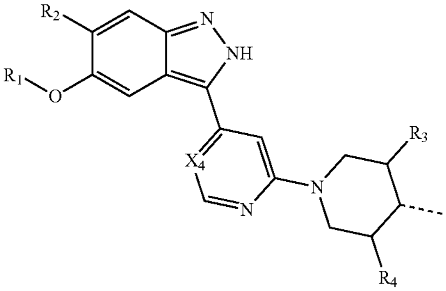
,
(PTM-XIXA)
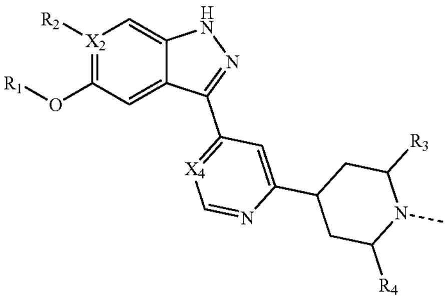
or
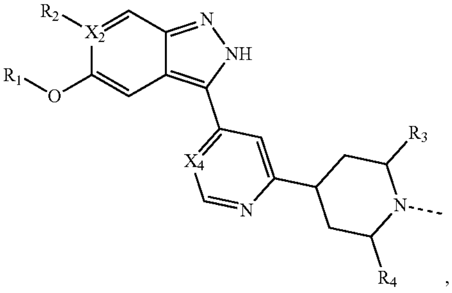
,
-continued
(PTM-XIXB)
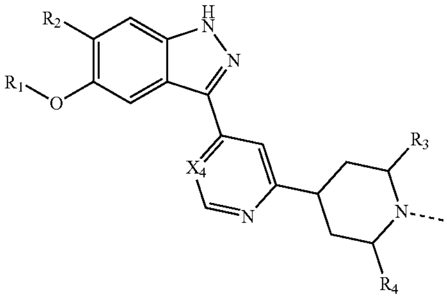
or
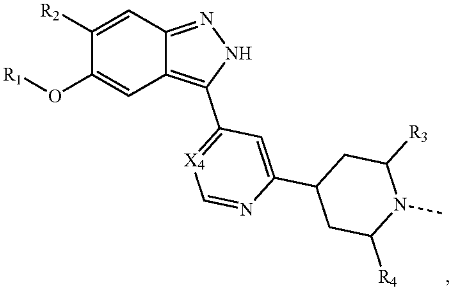
,
(PTM-XXA)
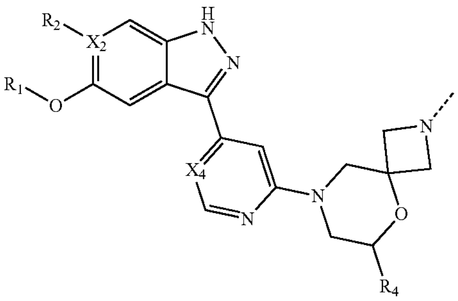
or
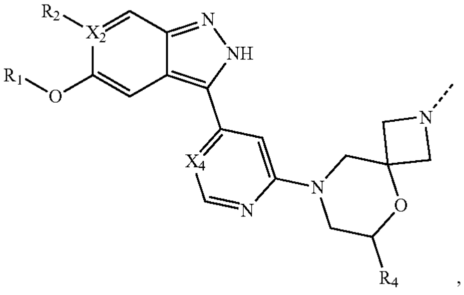
,
(PTM-XXB)
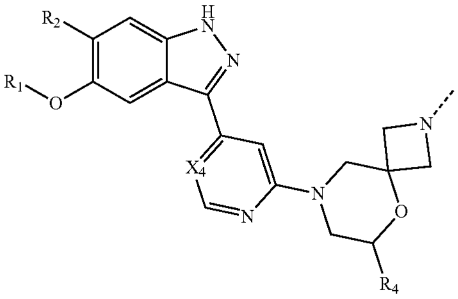
or -continued
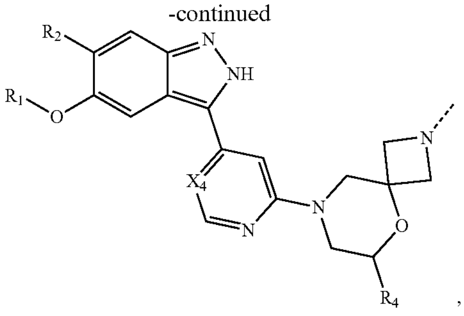
,
(PTM-XXIA)
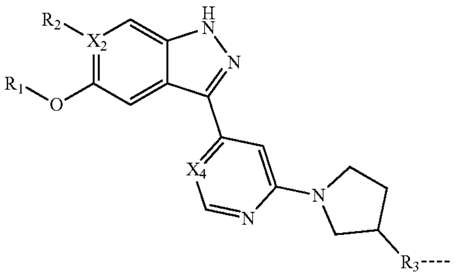
or
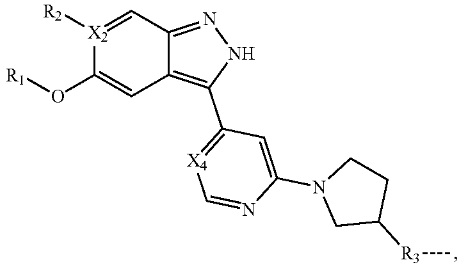
,
(PTM-XXIB)
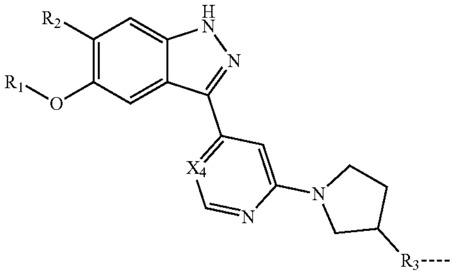
or
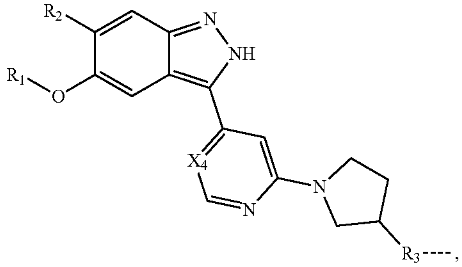
,
-continued
(PTM-XXIIA)
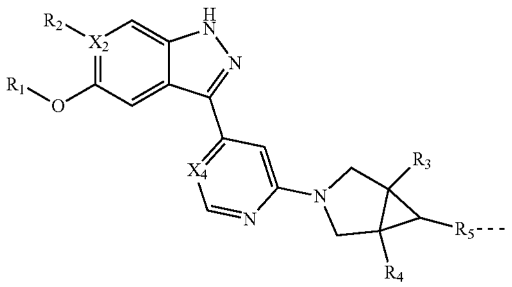
or
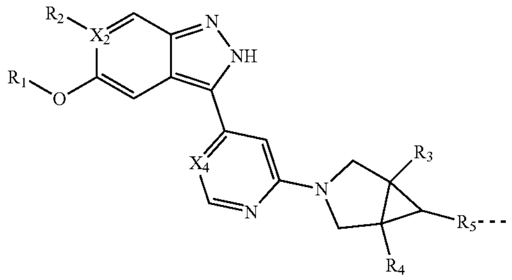
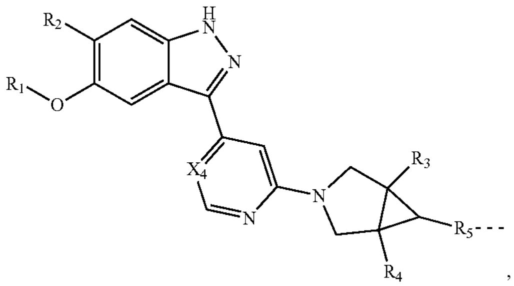
, or
(PTM-XXIIB)
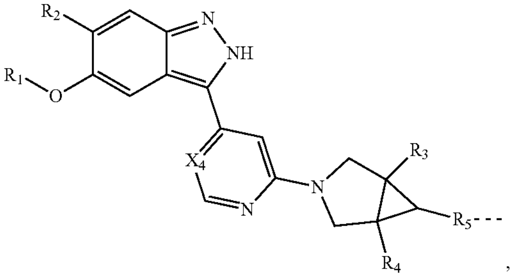
,
(PTM-IIIA)
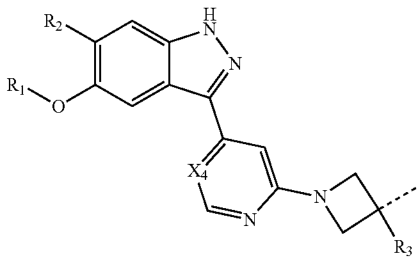
or

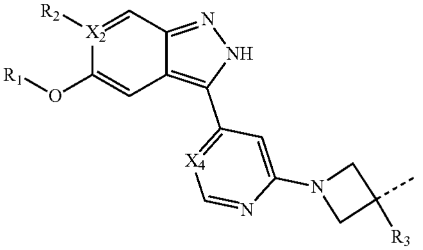
or
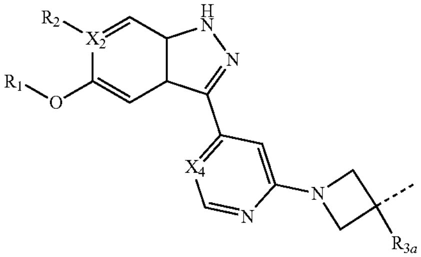
or
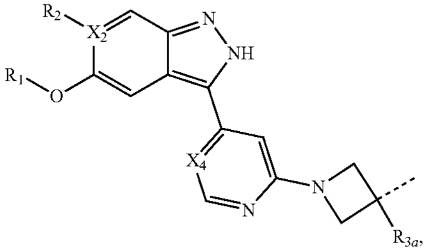
(PTM-XXIIIB)
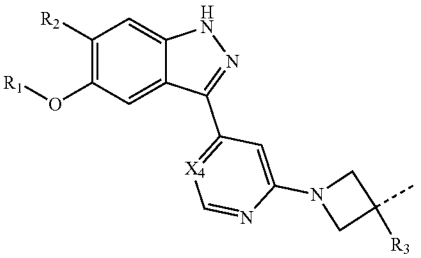
or
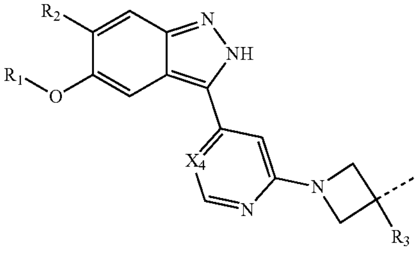
or
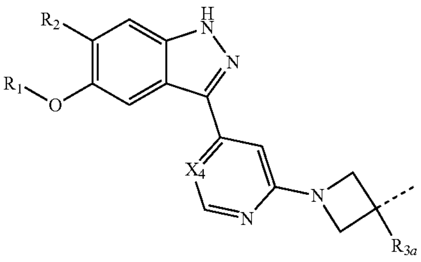
or
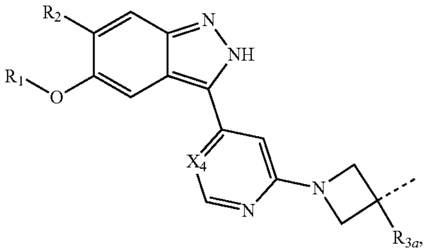
(PTM-XXIVA)
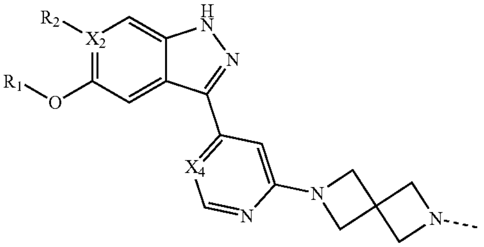
or
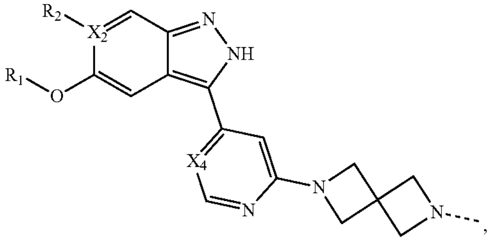
(PTM-XXIVB)
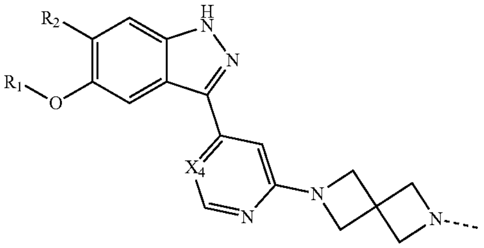
or
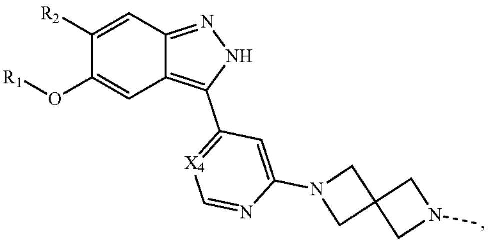
(PTM-XXVA)
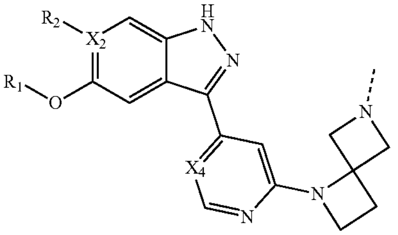
or -continued
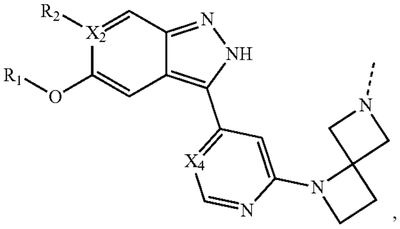
,
(PTM-XXVB)
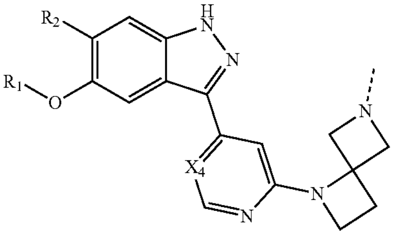
or
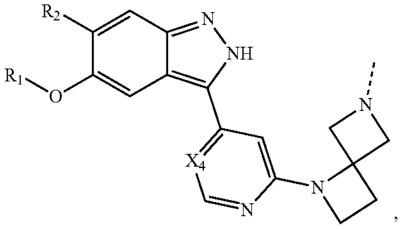
,
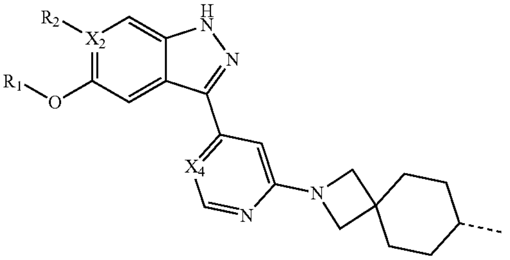
or
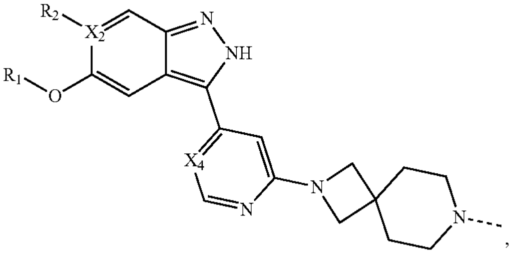
,
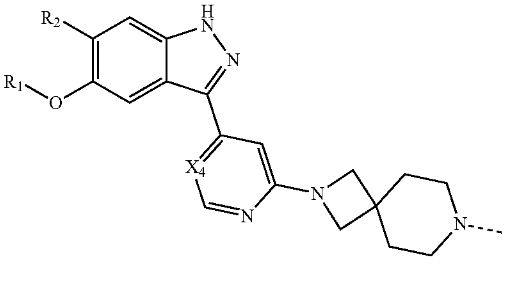
or
-continued
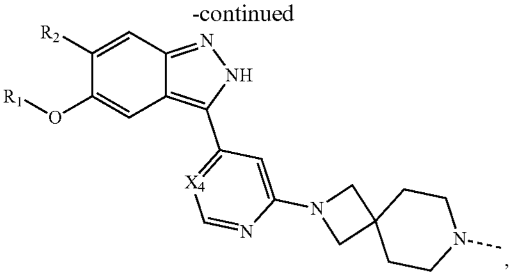
,
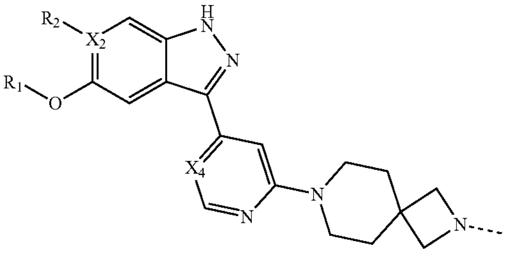
or
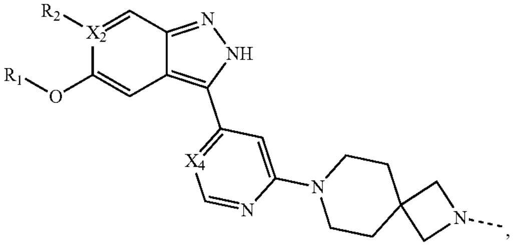
,
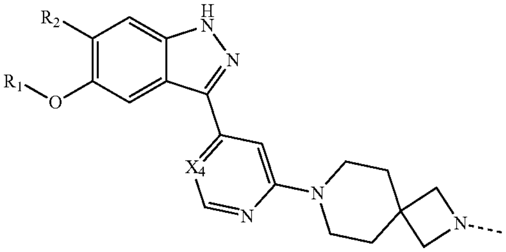
or
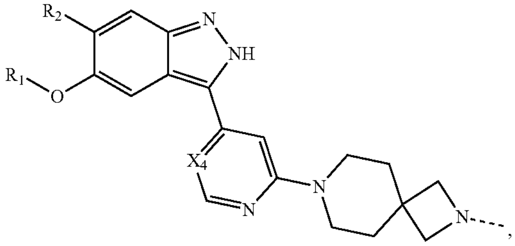
,
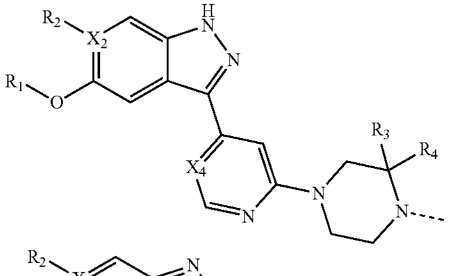
or
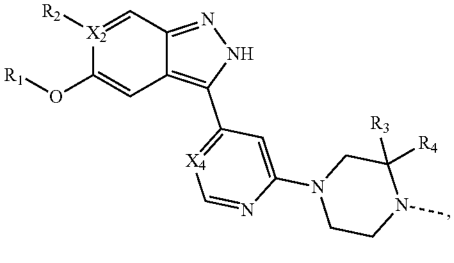
, -continued

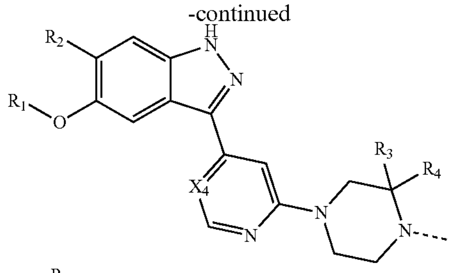

or

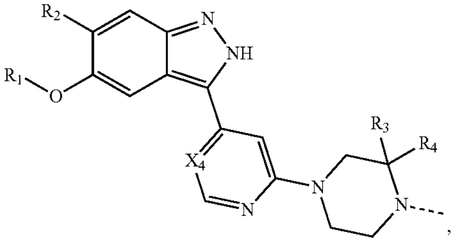

,

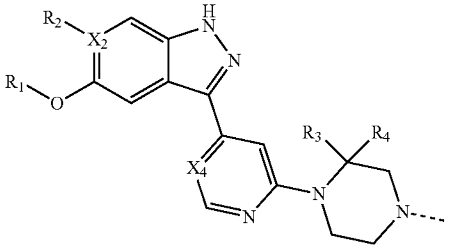

or

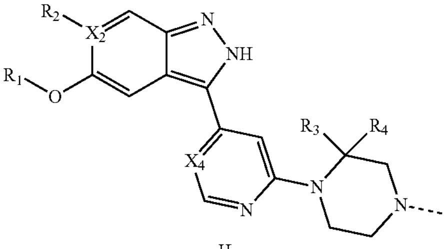

, or

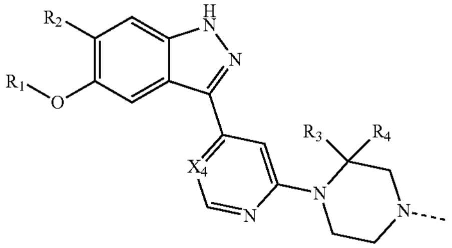

or

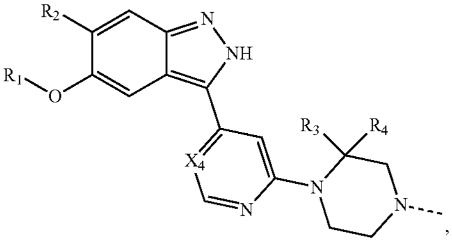

, wherein:

$X_2$, $X_4$, $R^1$, $R_2$, $R_{3a}$, $R_4$, and $R_5$ are defined as described in any aspect or embodiment described herein; and --- of the PTM indicates the point of attachment with the L or the ULM.

In any aspect or embodiment described herein, the $R^1$ is selected from an optionally substituted C3-C5 cycloalkyl and a liner or branched C1-C4 alkyl.

In any aspect or embodiment described herein, $R_1$ is

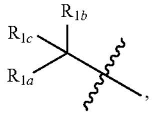

, wherein: $R_{1a}$, $R_{1b}$, and $R_{1C}$ are each independently a H or a linear or branched C1-C2 alkyl, each optionally substituted with one or more halogen or nitrile group; or $R_{1a}$ or $R_{1b}$ together with the carbon to which they are attached form a C3-C6 cycloalkyl that is optionally substituted with one or more C1-C3 alkyl, nitrile group, or halogen.

In any aspect or embodiment described herein, $R_1$ is

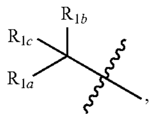

, wherein: $R_{1a}$, $R_{1b}$, and $R_{1C}$ are each independently a H, or a linear or branched C1-C2 alkyl; or $R_{1a}$ or $R_{1b}$ together with the carbon to which they are attached form a C3-C6 cycloalkyl.

In any aspect or embodiment described herein, the PTM is selected from:

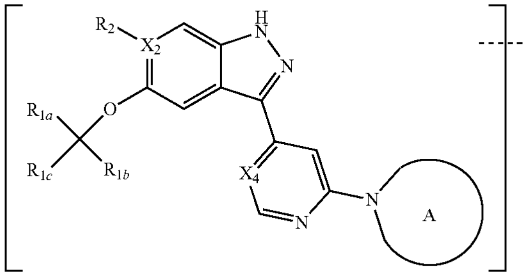

,

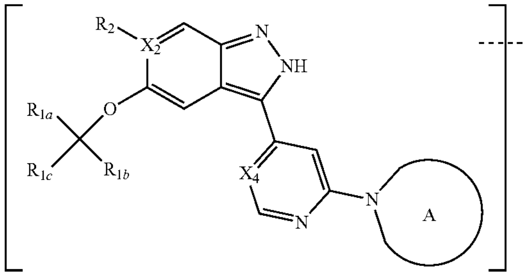

,

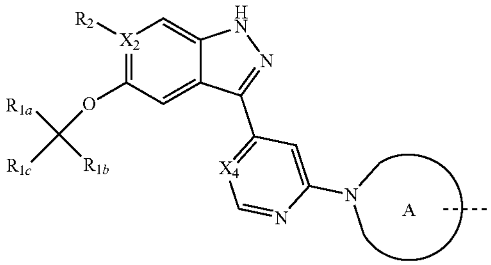

,

-continued
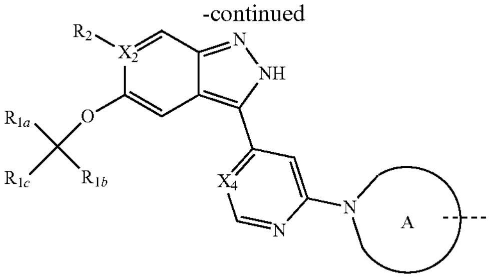
,
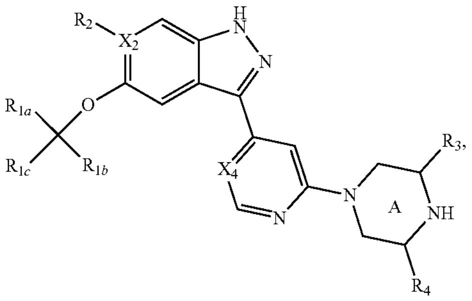
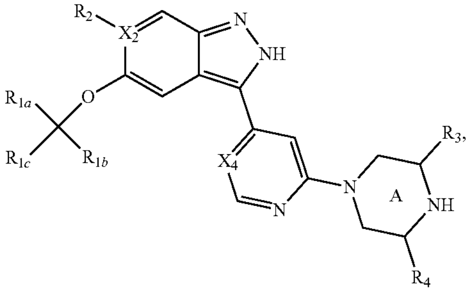
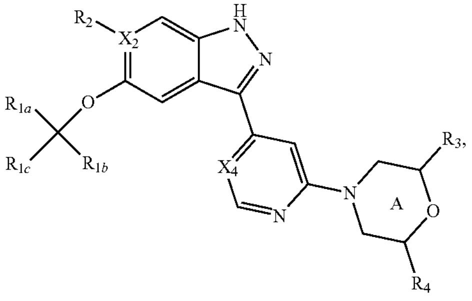
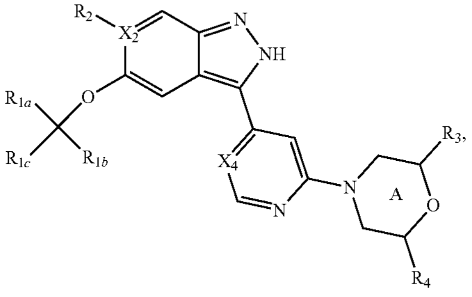
-continued
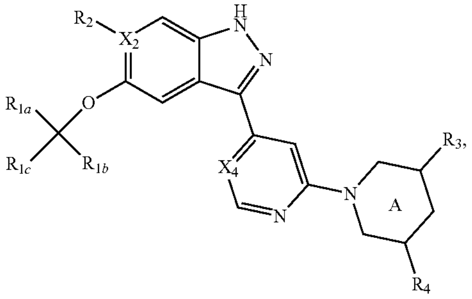
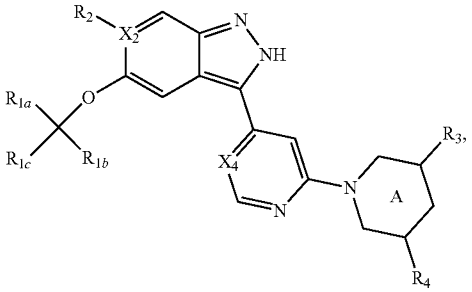
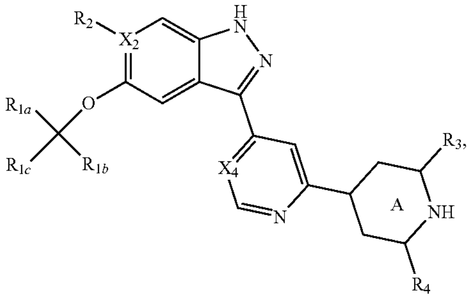
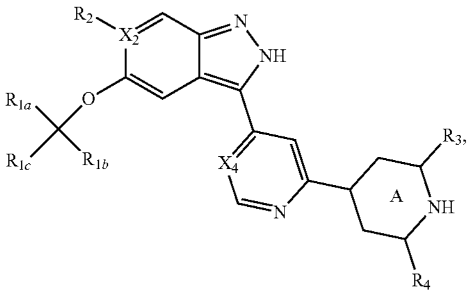
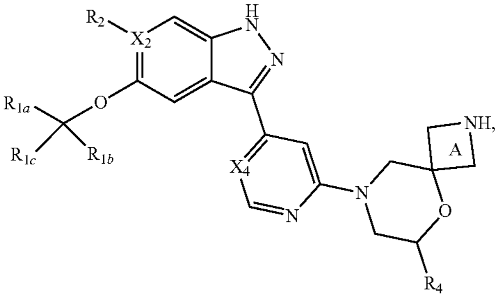

-continued
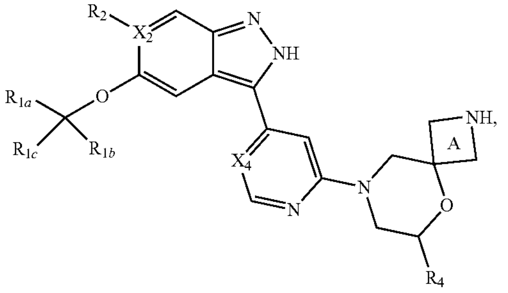
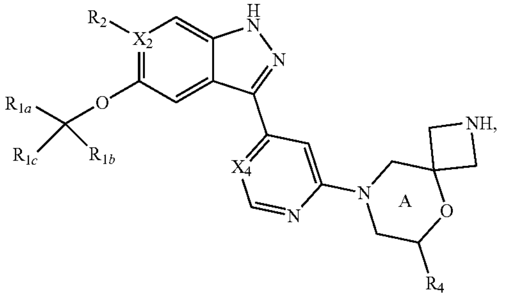
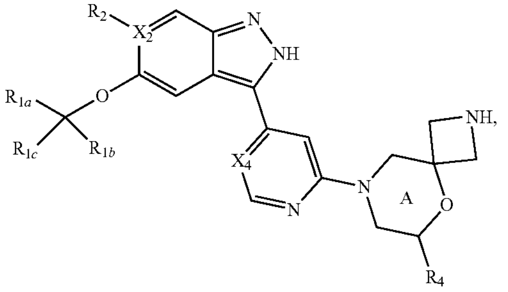
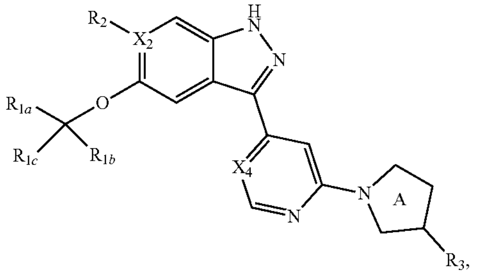
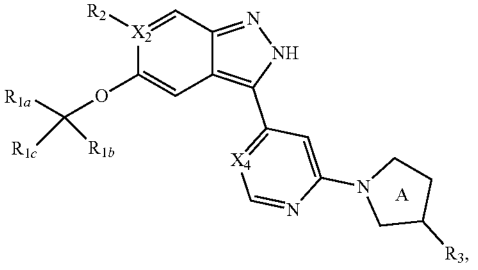
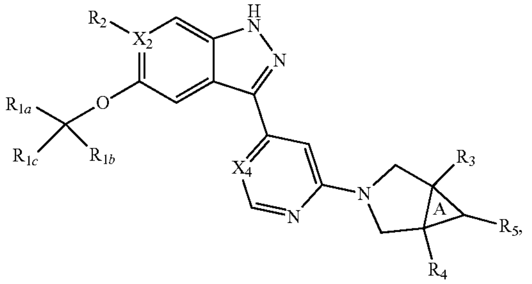
-continued
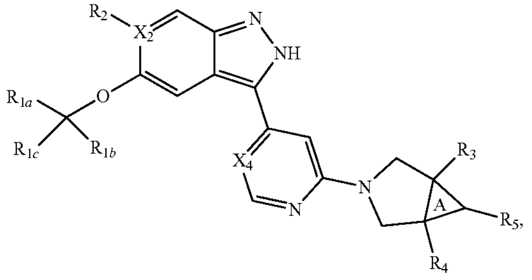
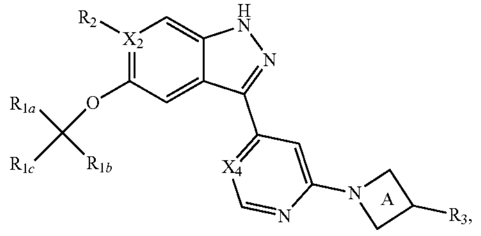
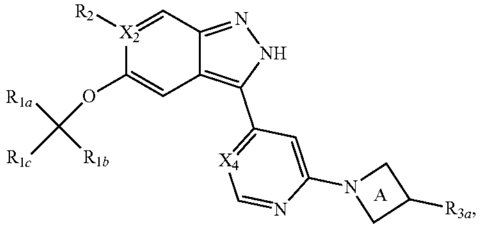
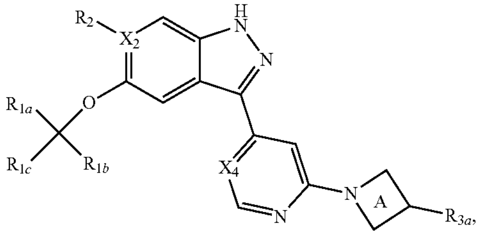
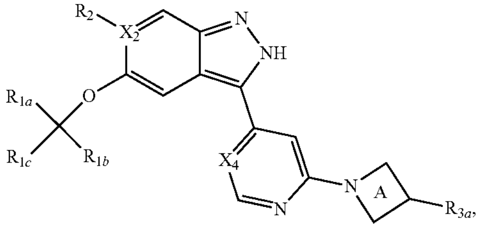
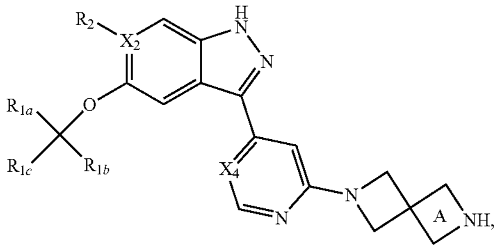
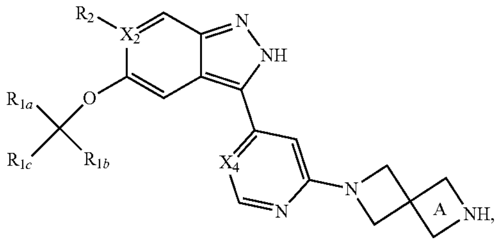

-continued
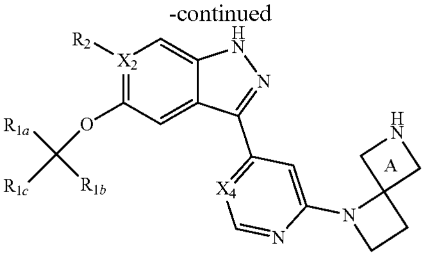
,
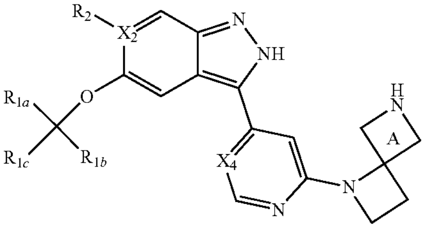
,
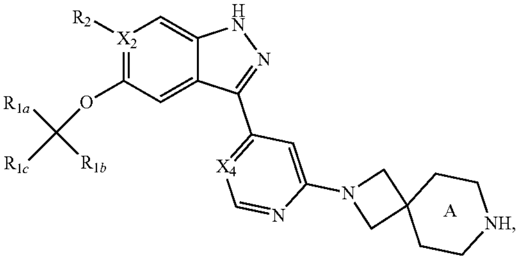
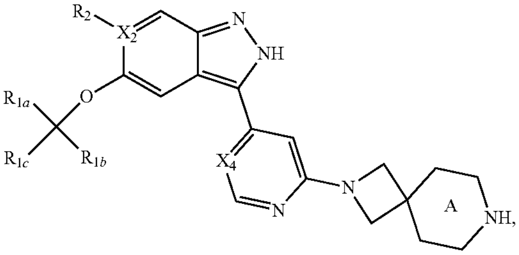
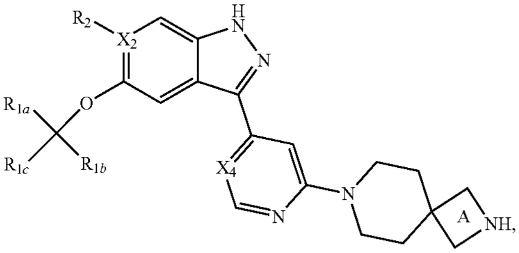
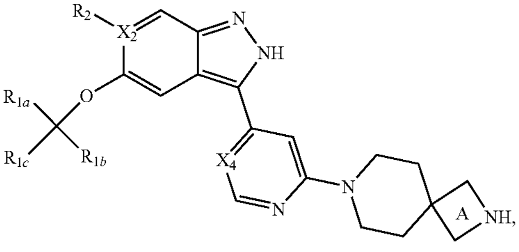
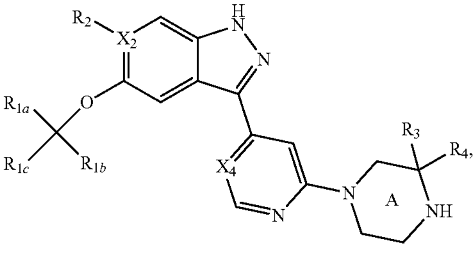
-continued
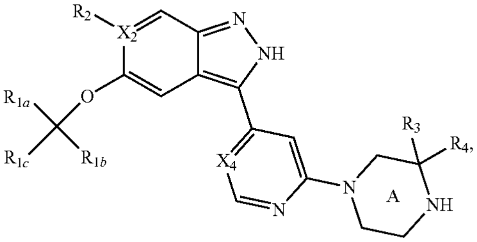
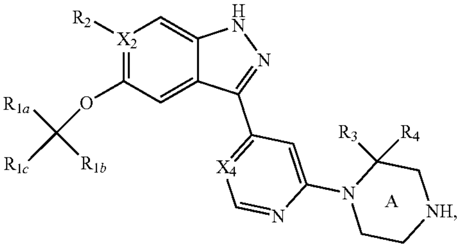
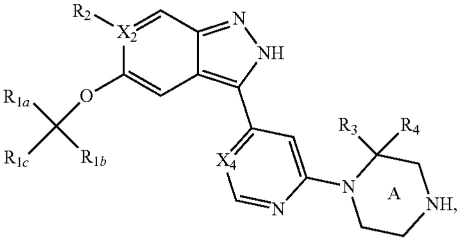
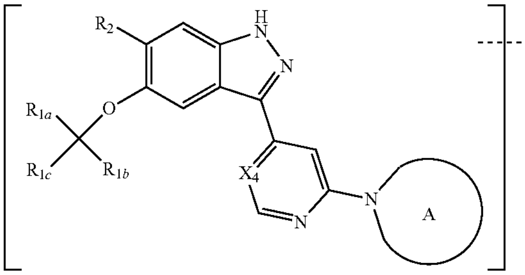
,
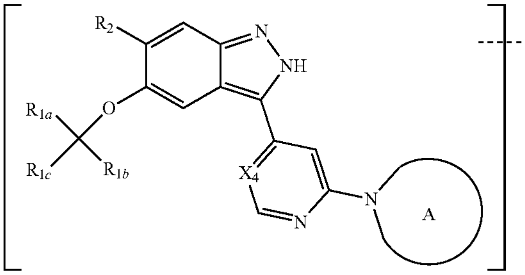
,
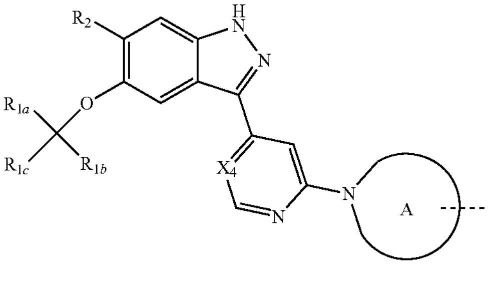
, -continued
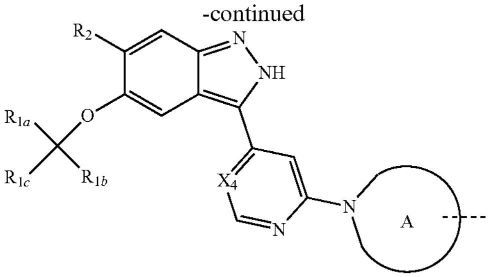
,
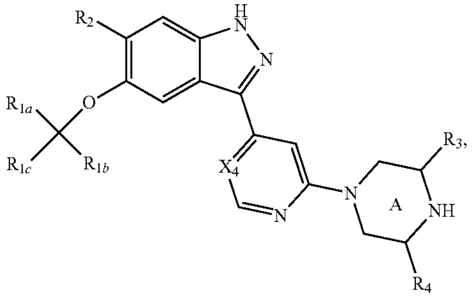
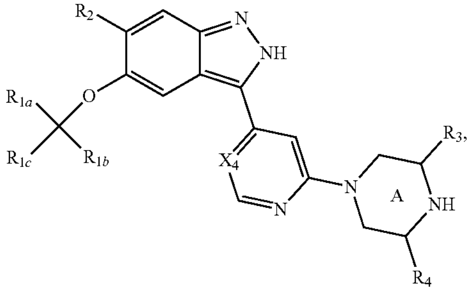
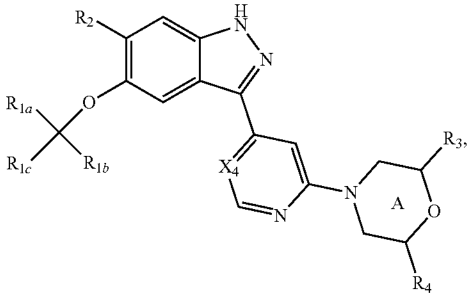
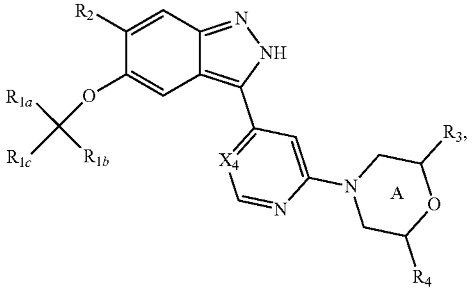
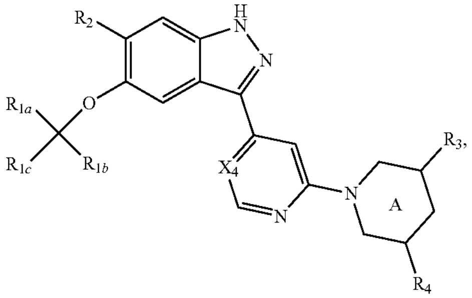
-continued
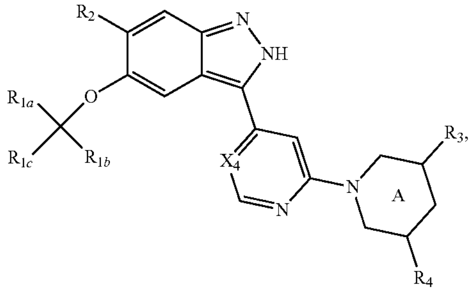
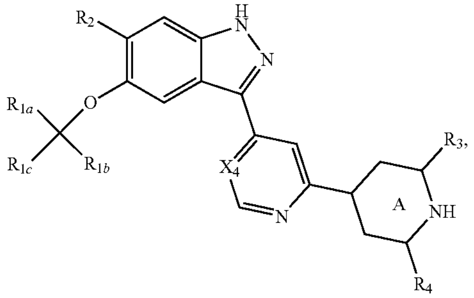
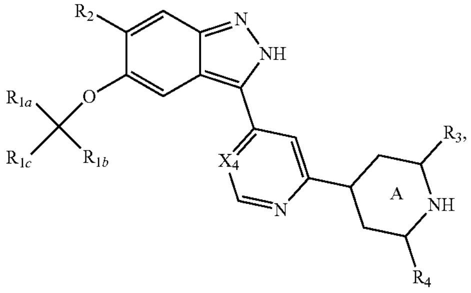
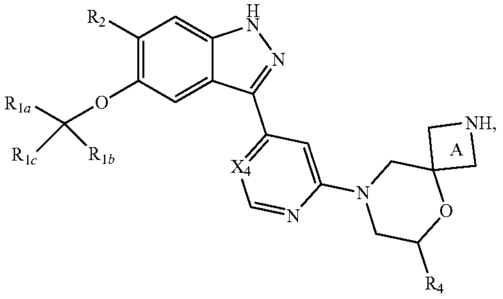
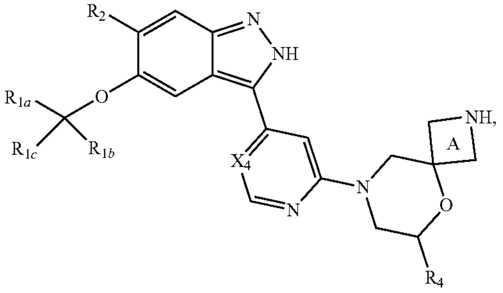

-continued
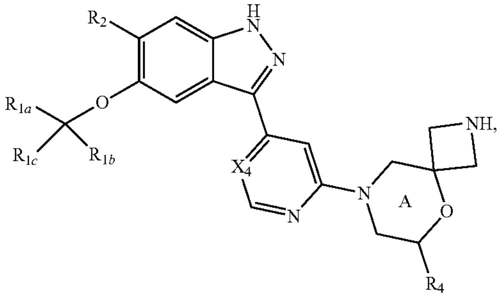
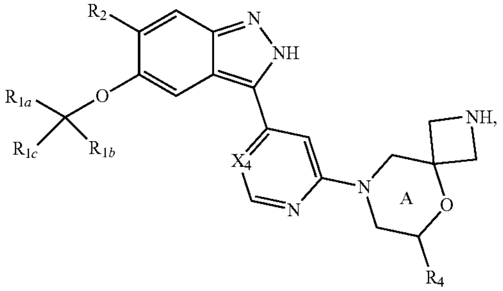
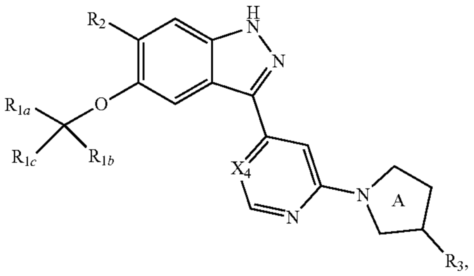
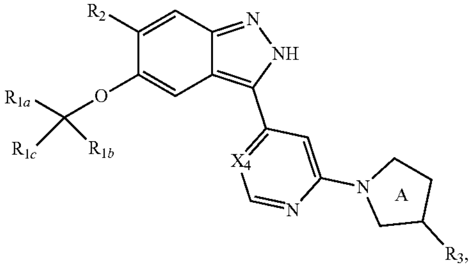
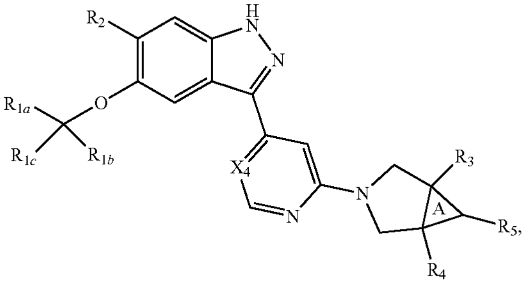
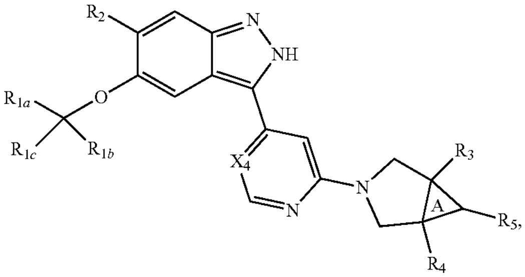
-continued
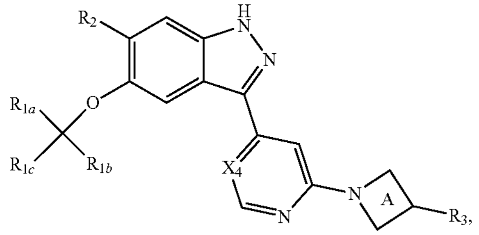
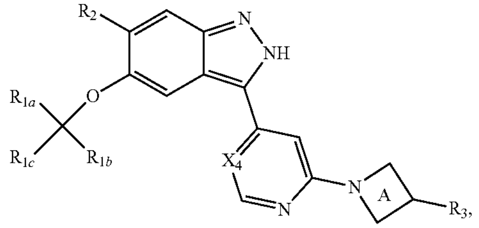
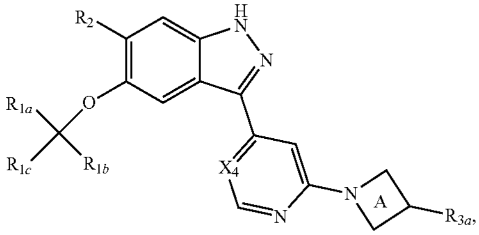
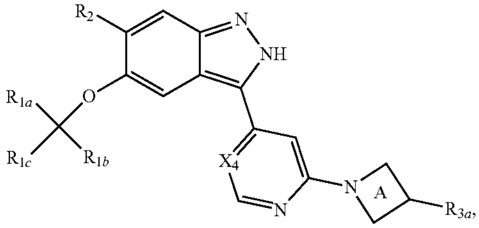
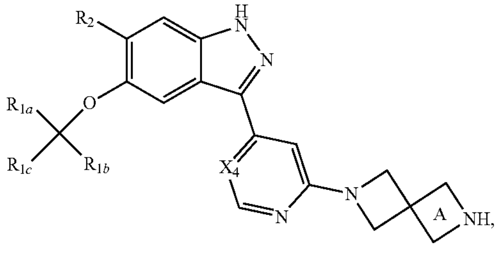
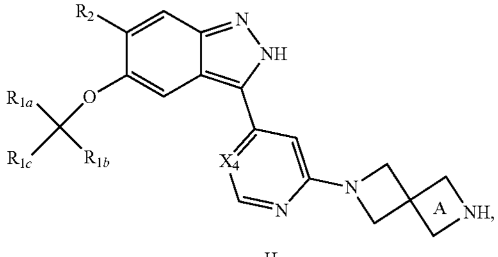
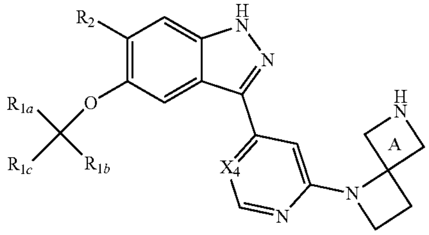
, -continued
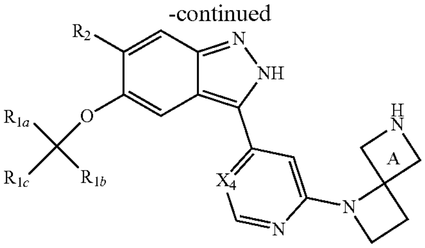
,
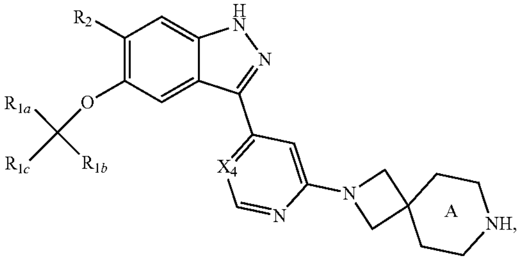
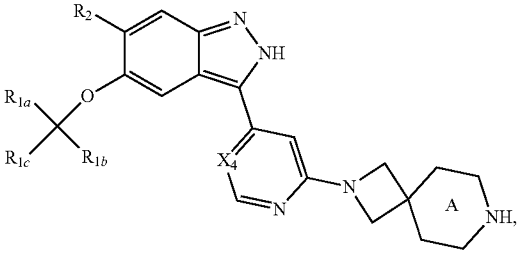
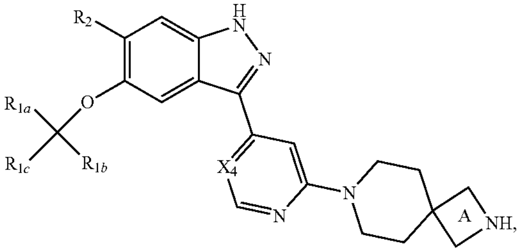
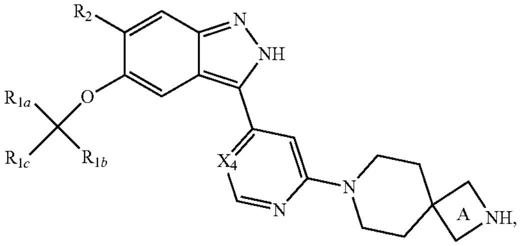
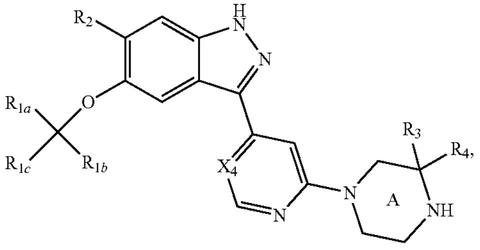
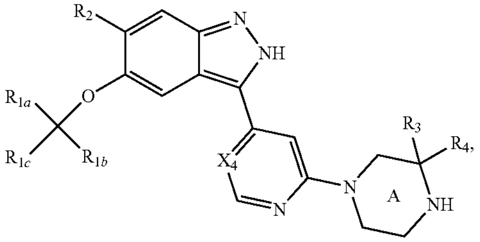
-continued
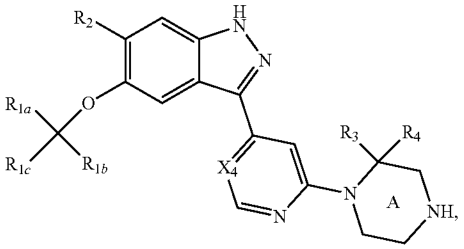
or
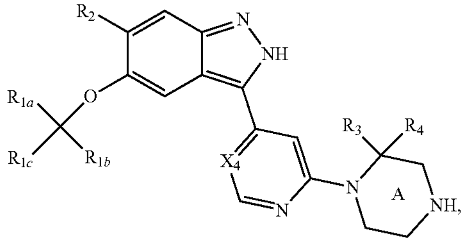
wherein:
each of $X_2$, $X_4$, $R_{1a}$, $R_{1b}$, $R_{1c}$, $R_3$, $R_{3a}$, $R_4$, $R_5$, and
are defined as described in any aspect or embodiment described herein; and
the L or ULM is attached via an atom of the heterocycloalkyl A (e.g., a carbon or nitrogen of the heterocycloalkyl), $R_3$, or $R_4$.
In any aspect or embodiment described herein, the PTM is selected from:
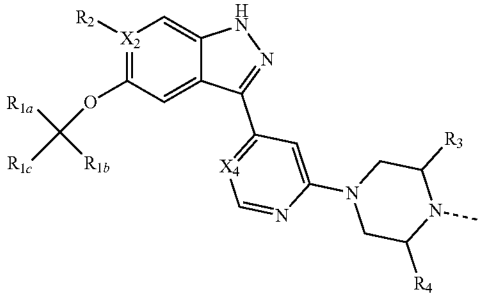
,
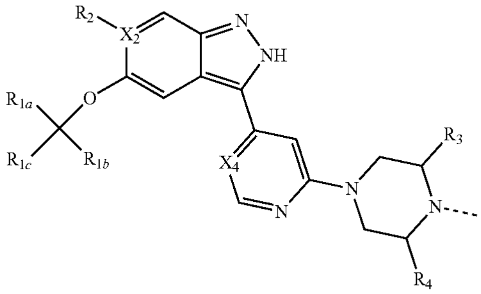
, -continued
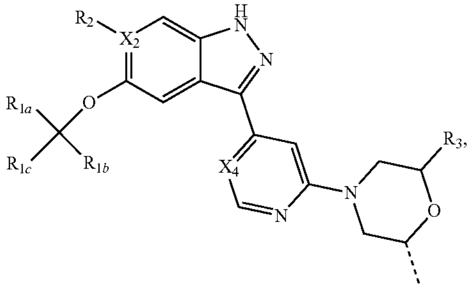
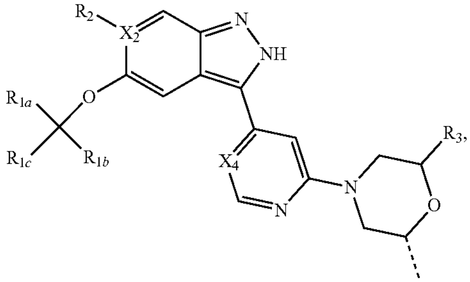
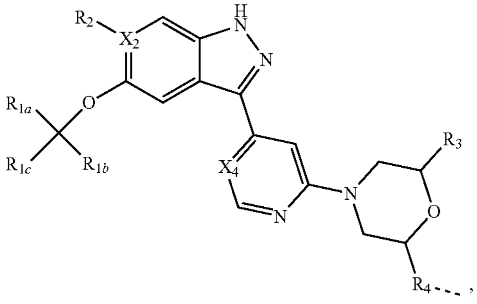
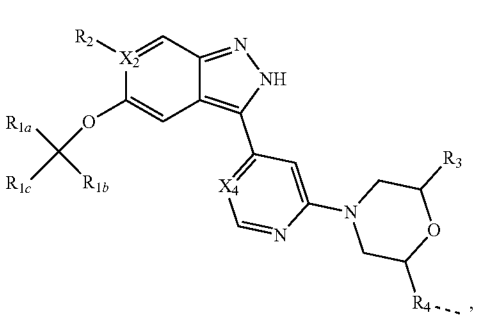
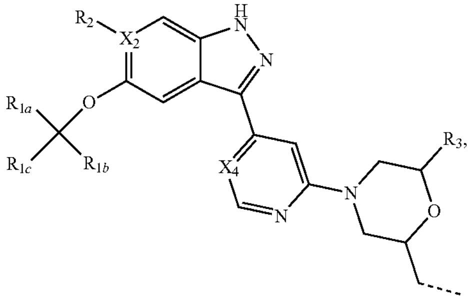
-continued
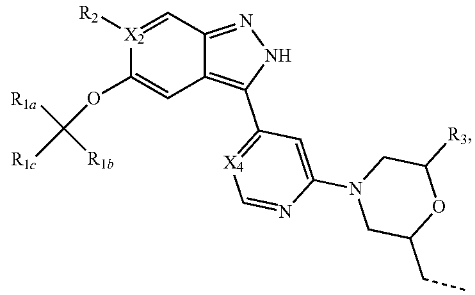
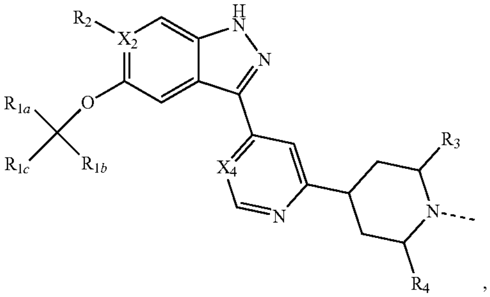
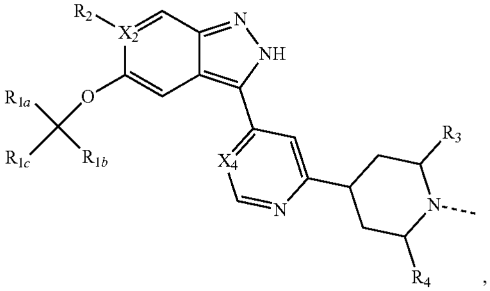
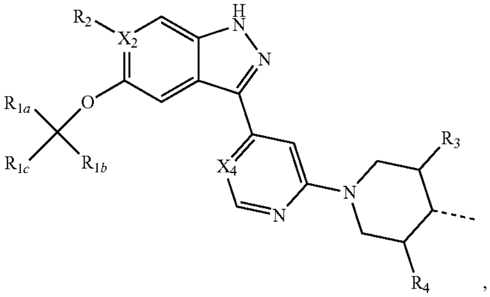
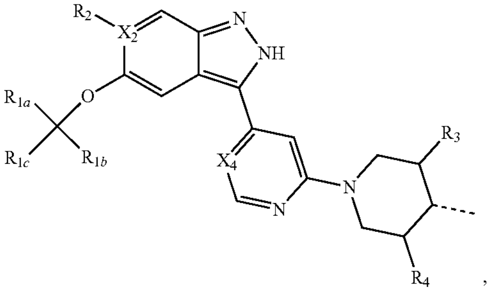

-continued
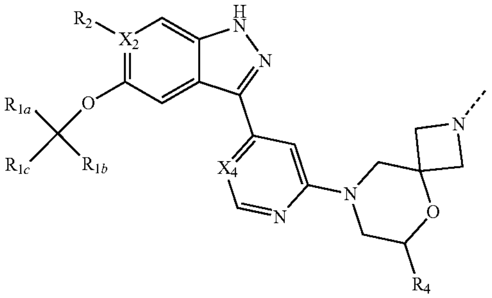
,
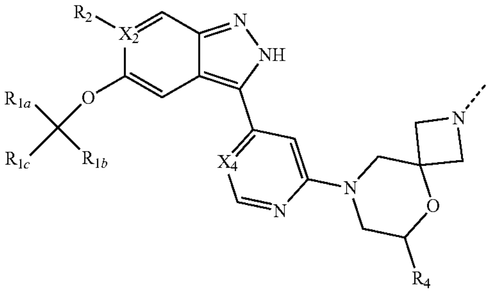
,
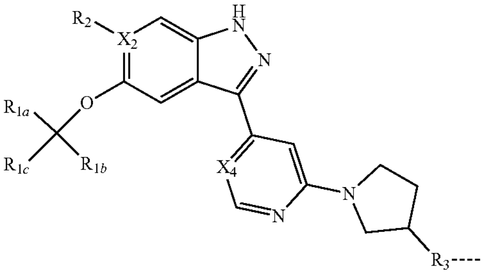
,
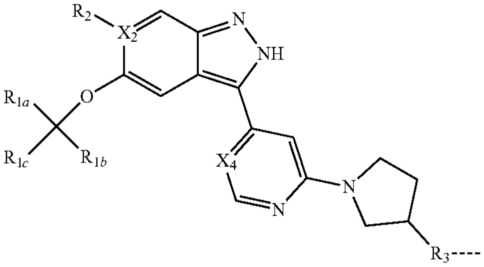
,
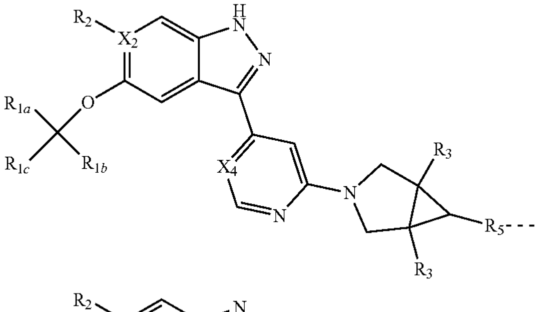
,
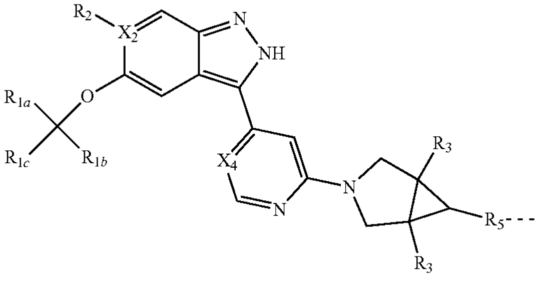
,
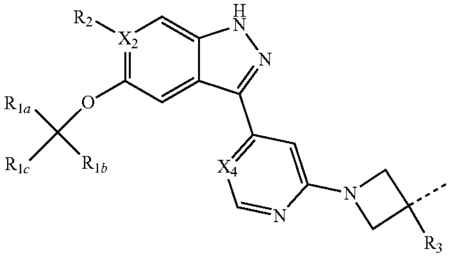
,
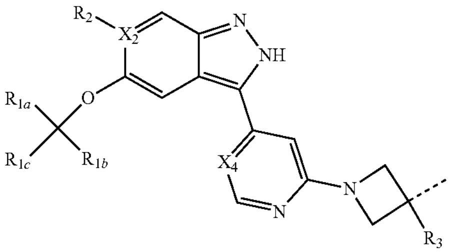
,
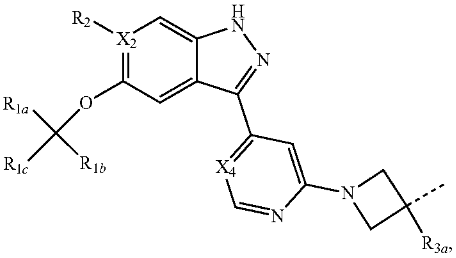
,
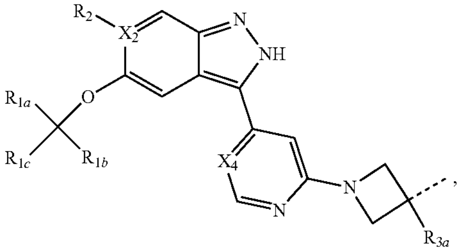
,
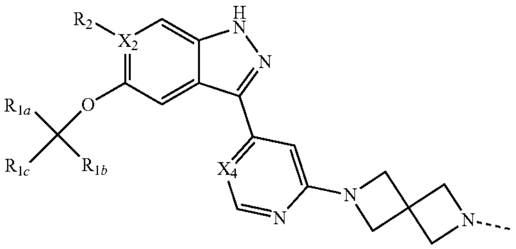
,
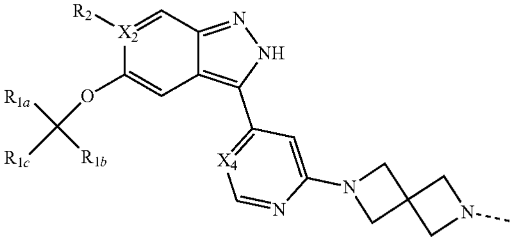
, -continued
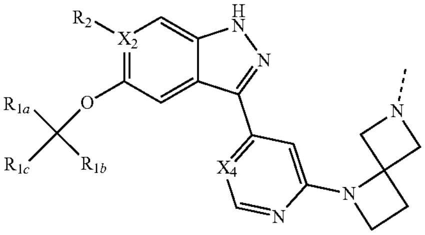
,
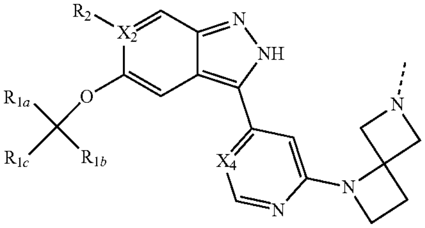
,
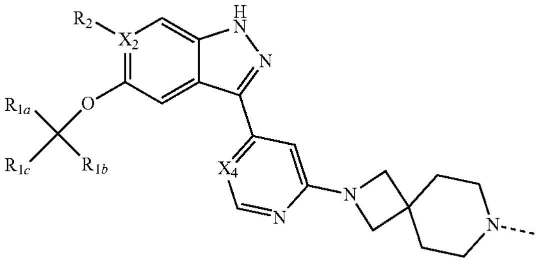
,
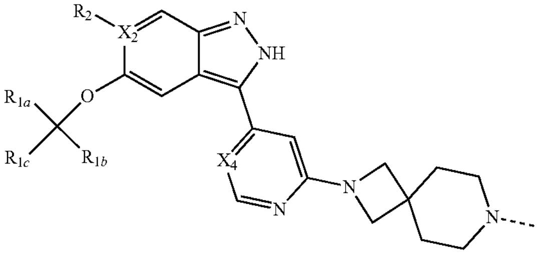
,
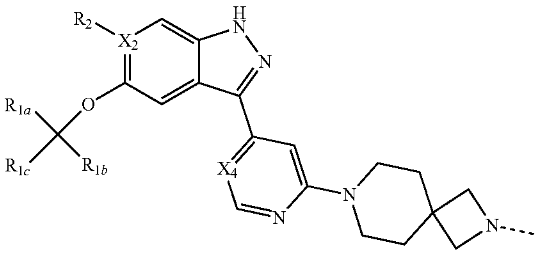
,
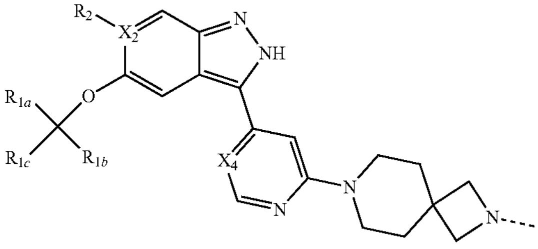
,
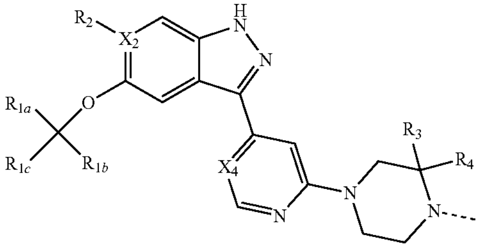
,
-continued
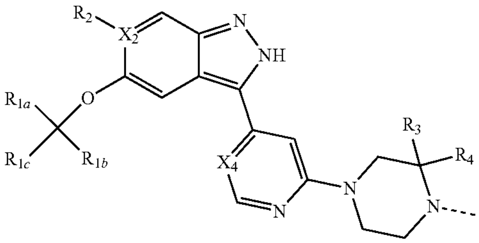
,
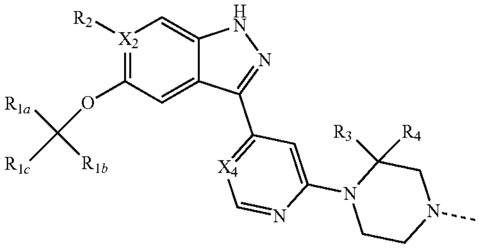
,
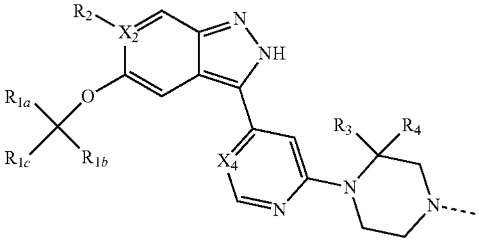
,
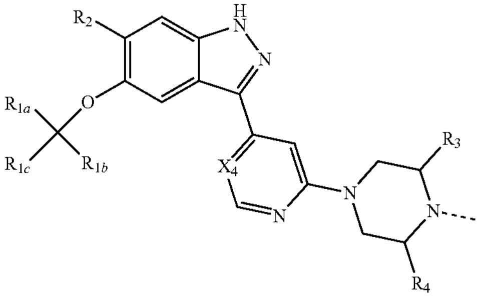
,
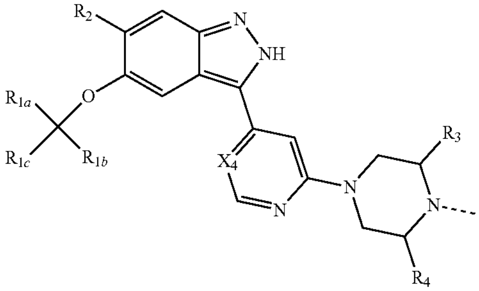
,
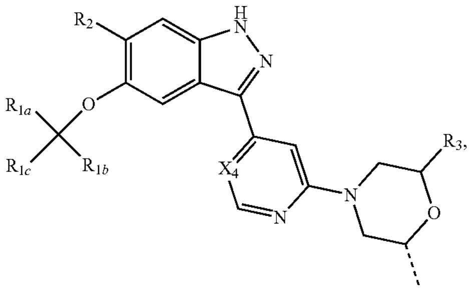

-continued
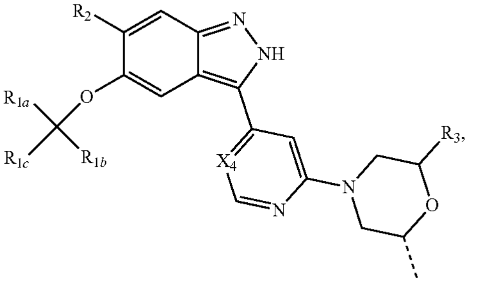
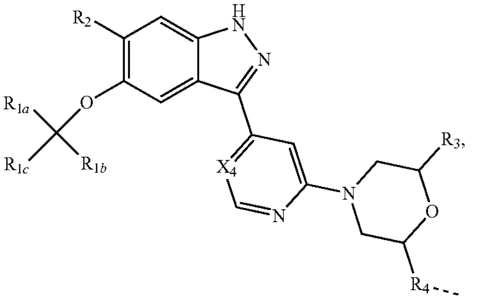
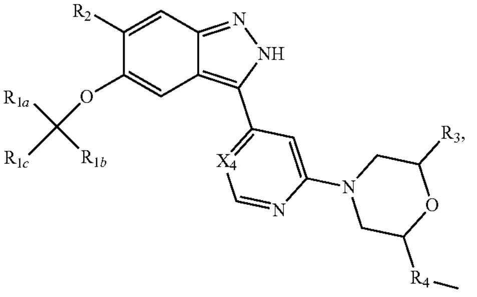
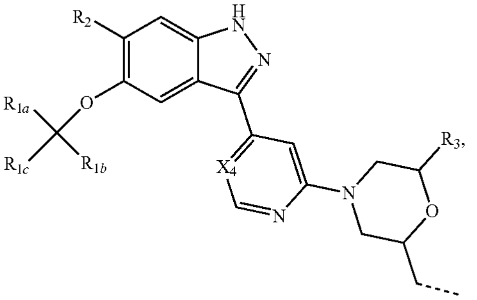
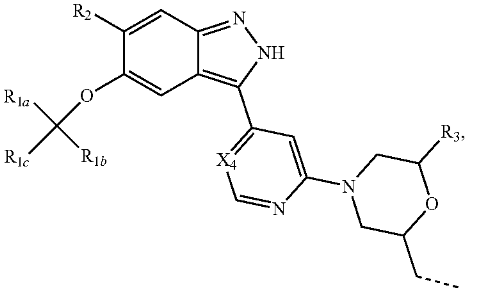
-continued
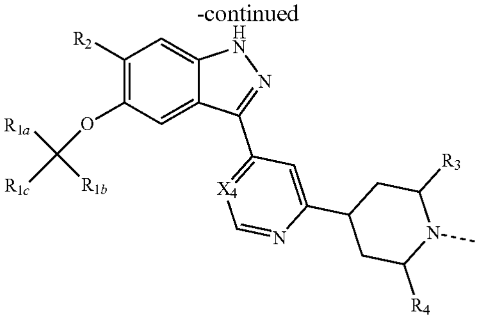
,
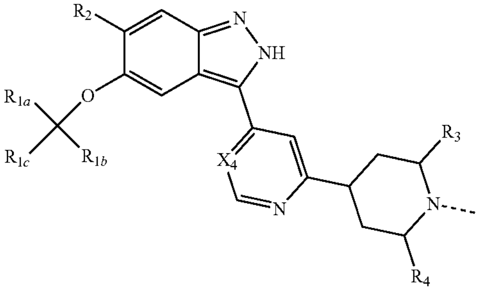
,
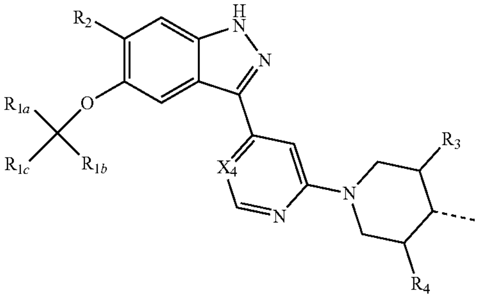
,
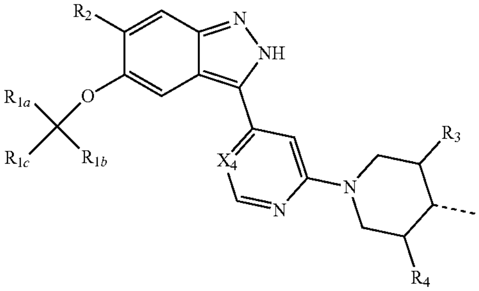
,
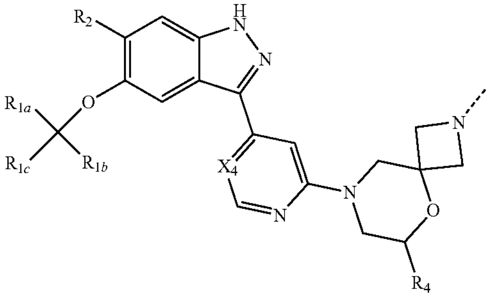
, -continued
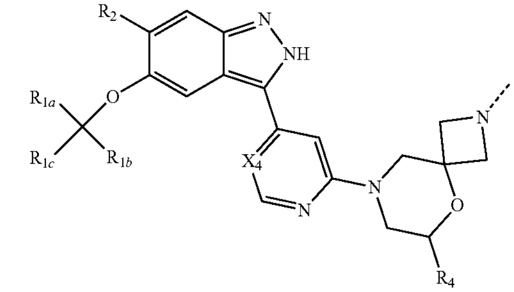
,
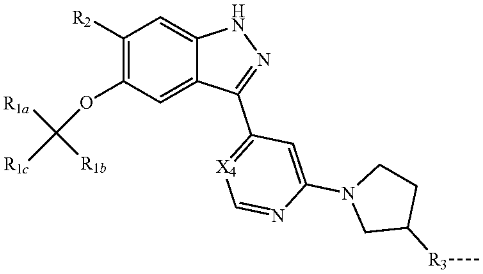
,
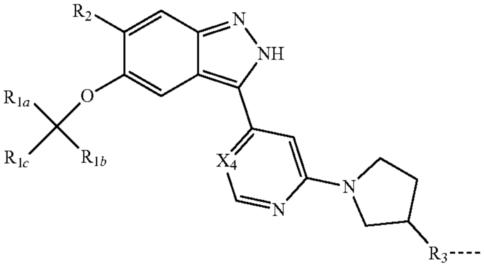
,
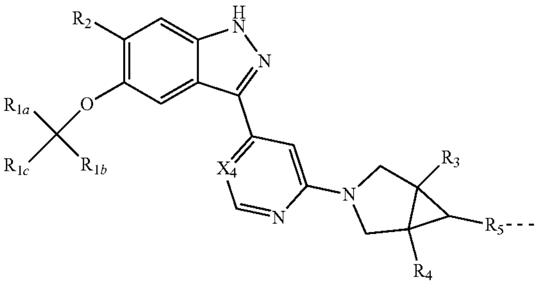
,
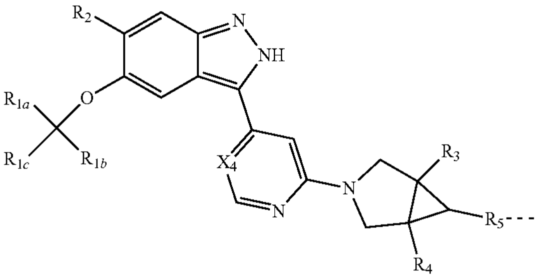
,
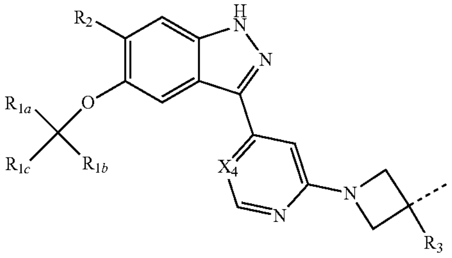
,
-continued
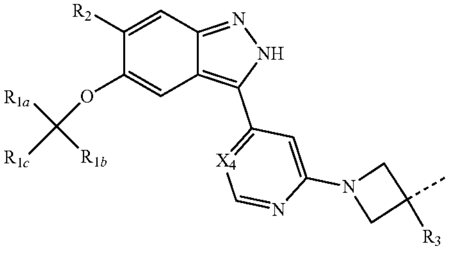
,
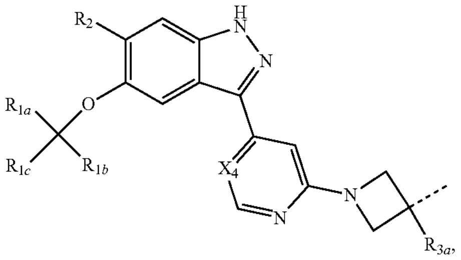
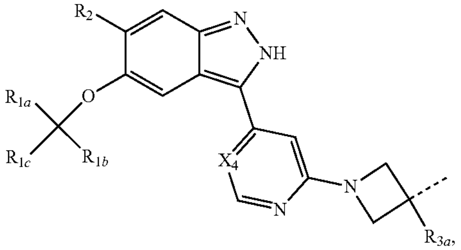
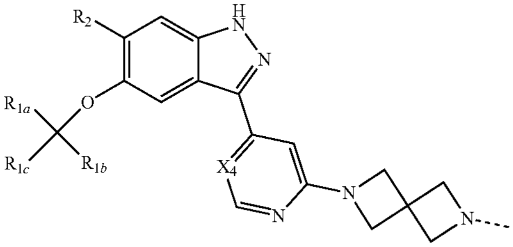
,
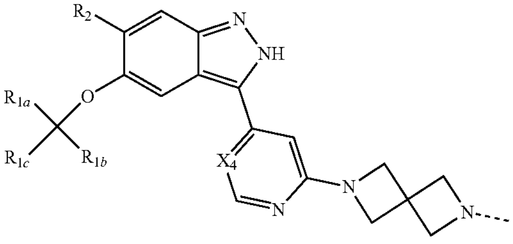
,
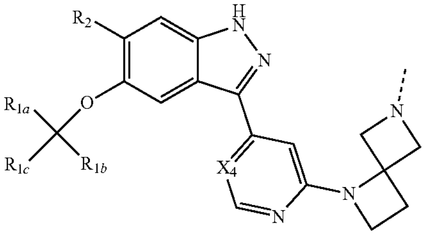
,
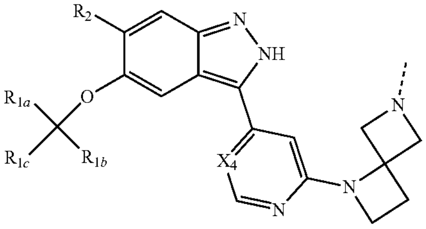
, -continued

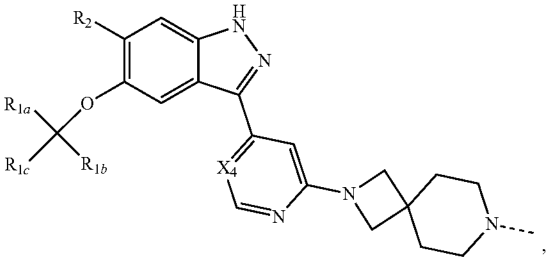

,

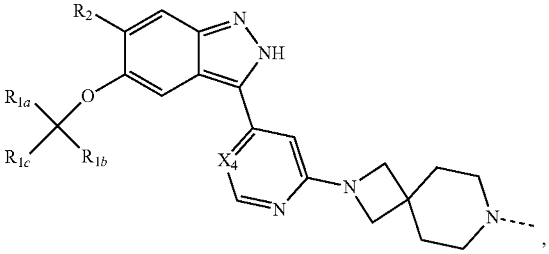

,

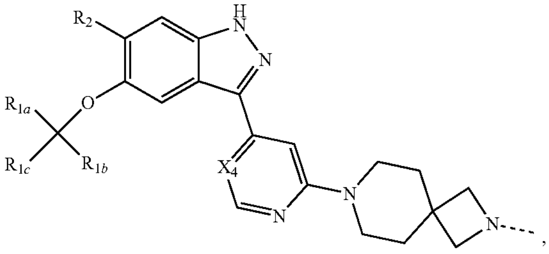

,

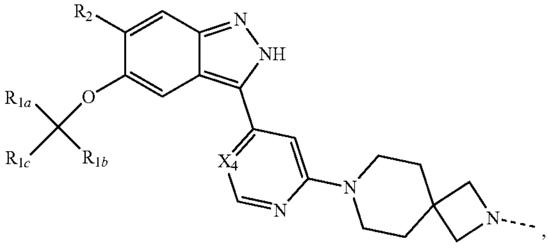

,

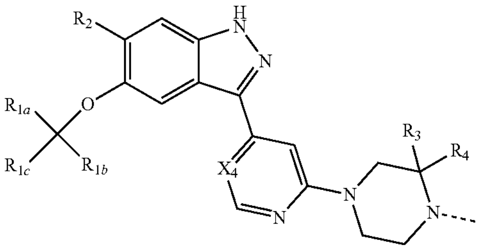

,

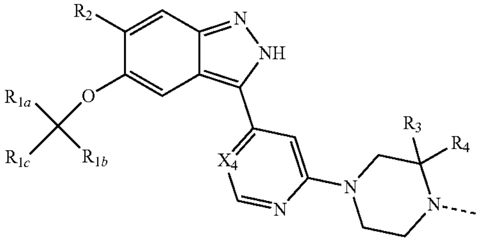

,

-continued

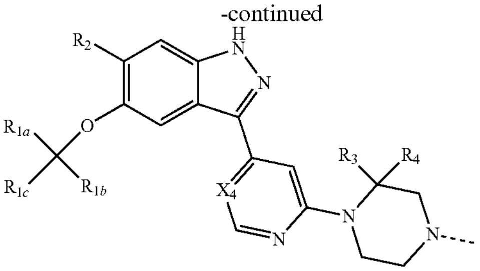

, or

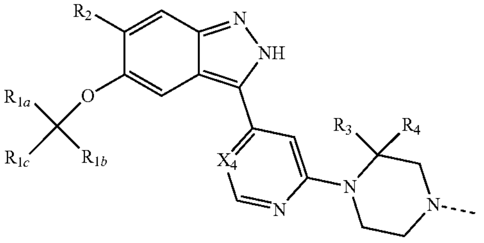

, wherein:

each of $X_2$, $X_4$, $R_{1a}$, $R_{1b}$, $R_{1c}$, $R_3$, $R_{3a}$, $R_4$, and $R_5$ are defined as described in any aspect or embodiment described herein; and

 of the PTM indicates the point of attachment with the L or ULM, and where not present.

In any aspect or embodiment described herein, the $R_1$ is selected from

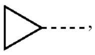, 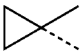, 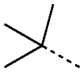, and 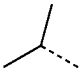, wherein  is the point of attachment to the M (e.g., oxygen atom) of the PTM.

In any aspect or embodiment described herein, the $R_2$ is H or F.

In any aspect or embodiment described herein, the PTM has the chemical structure:

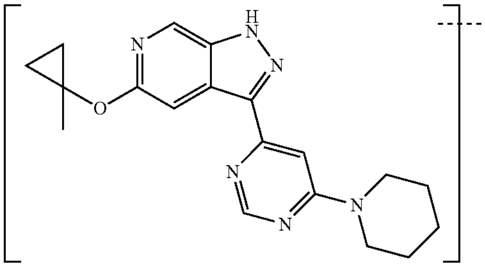

,

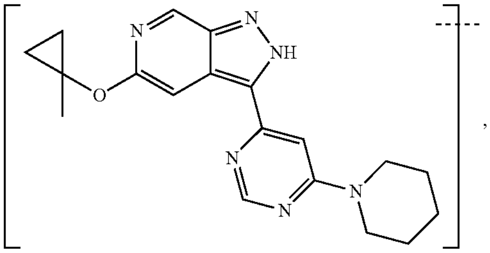

,

-continued
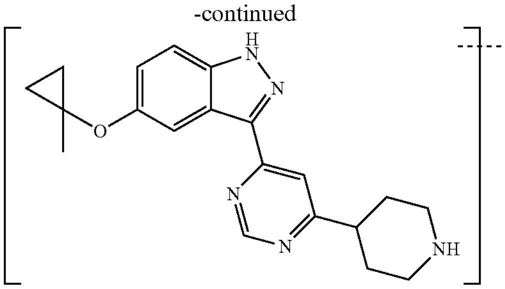
,
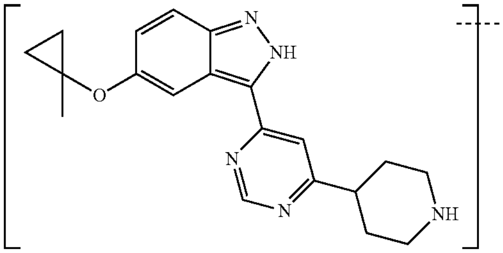
,
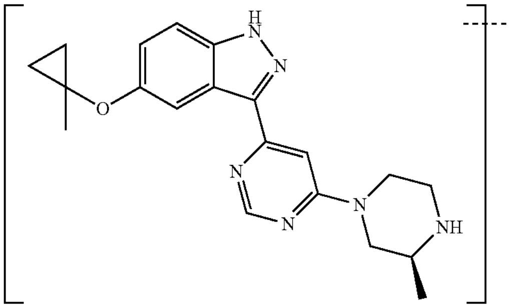
,
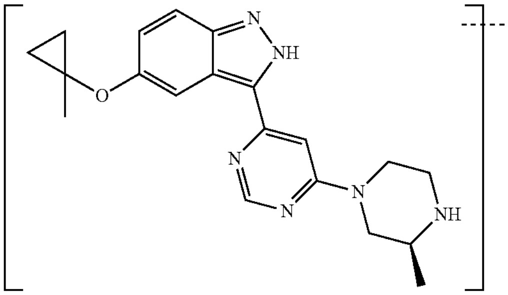
,
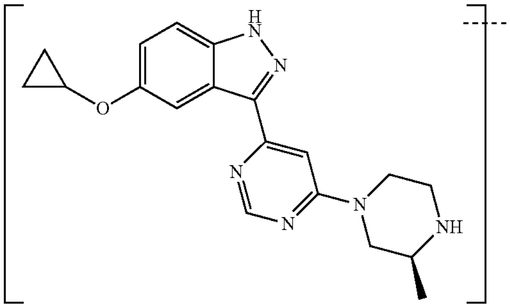
,
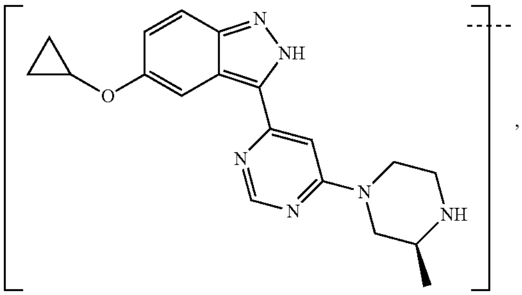
,
-continued
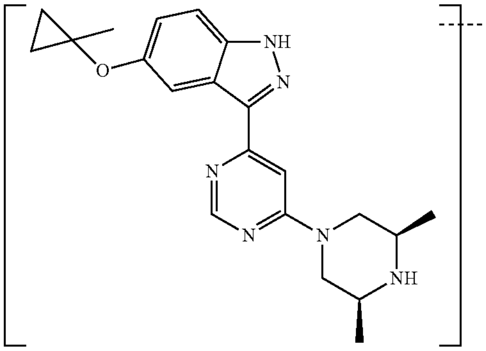
,
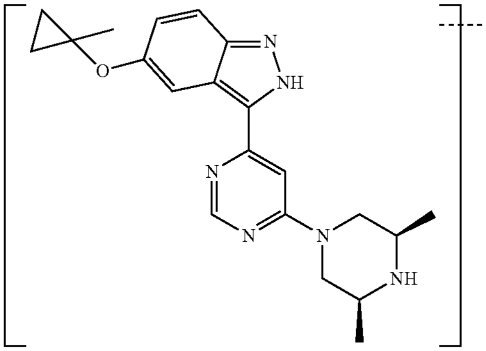
,
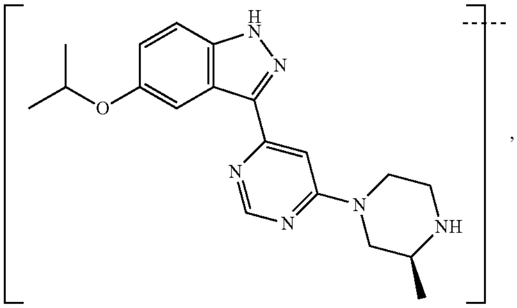
,
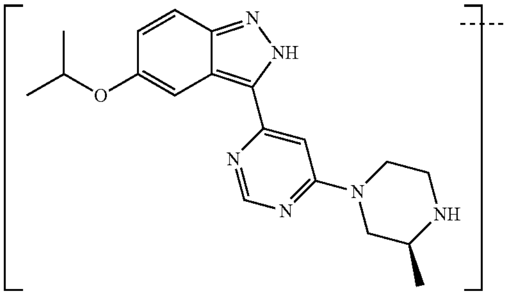
,
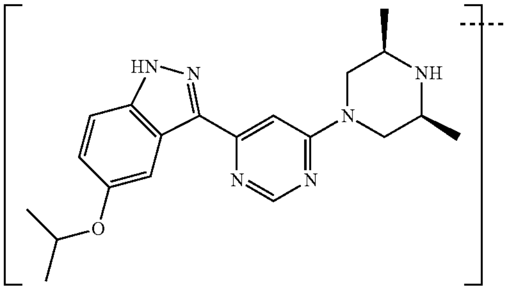
, -continued
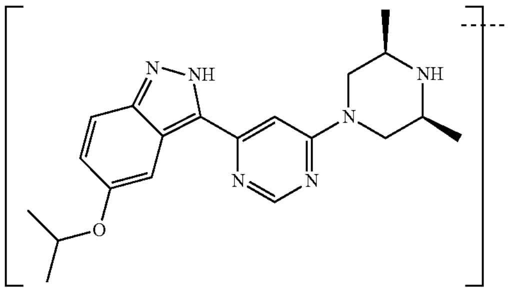
,
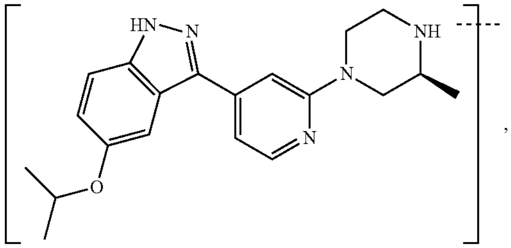
,
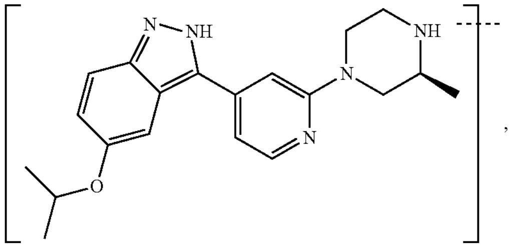
,
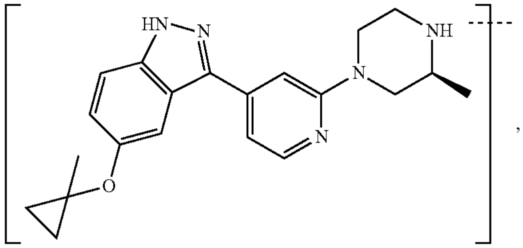
,
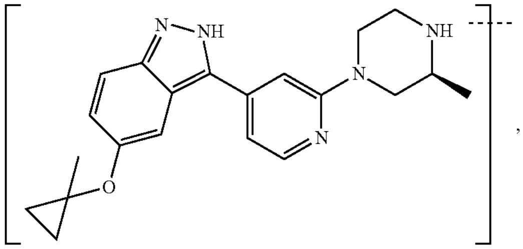
,
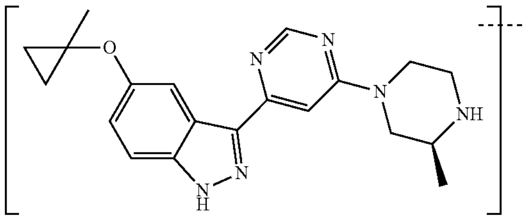
,
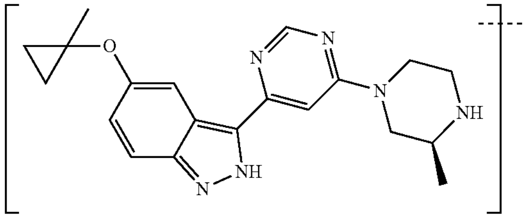
,
-continued
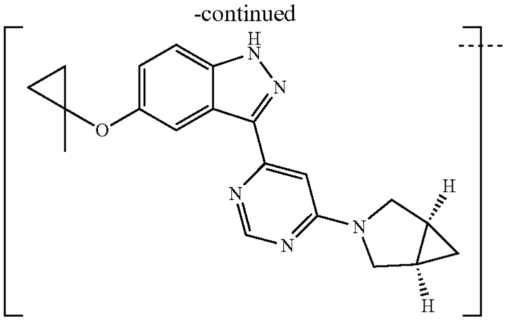
,
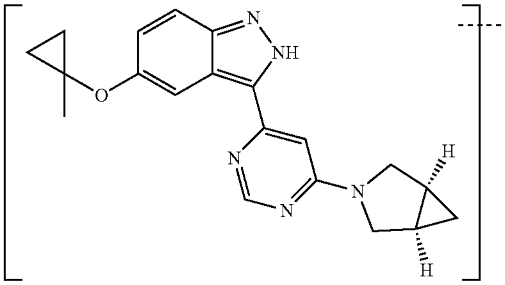
,
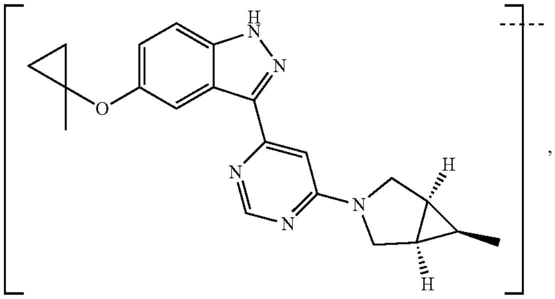
,
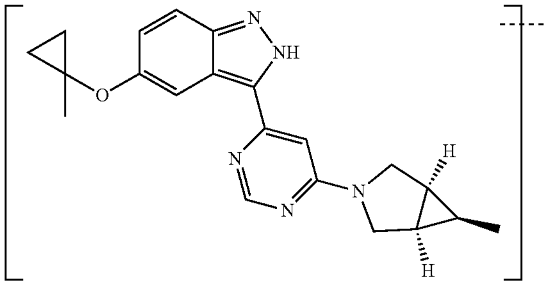
,
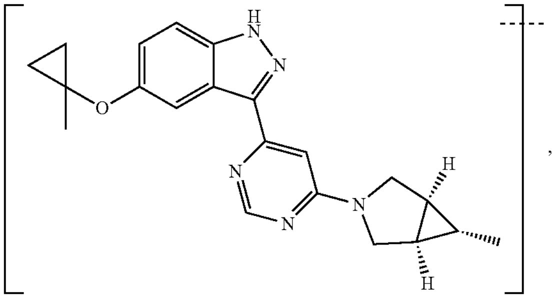
, -continued
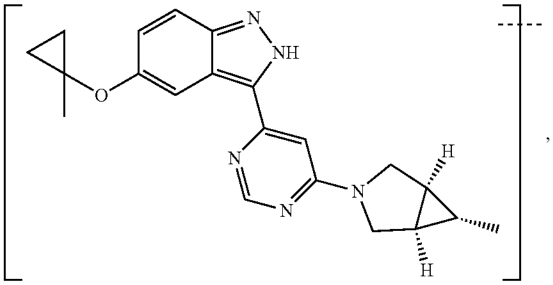
,
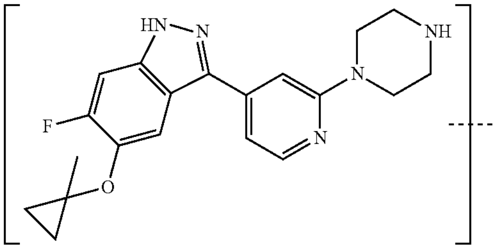
,
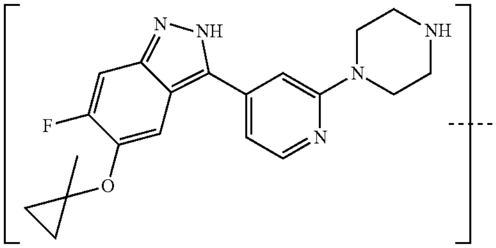
,
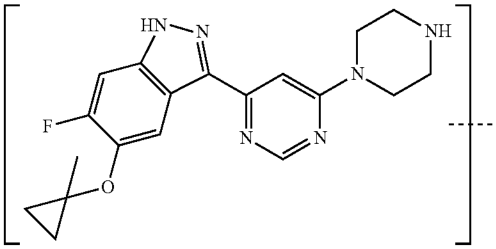
,
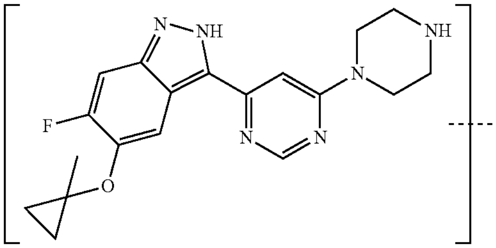
,
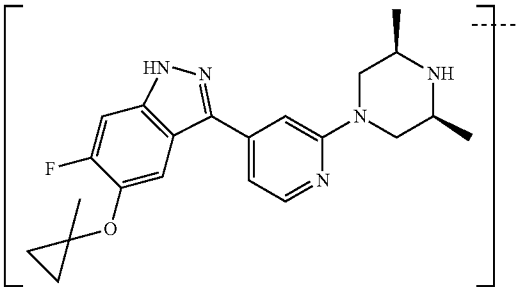
,
-continued
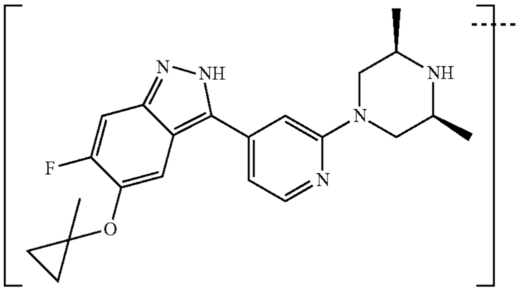
,
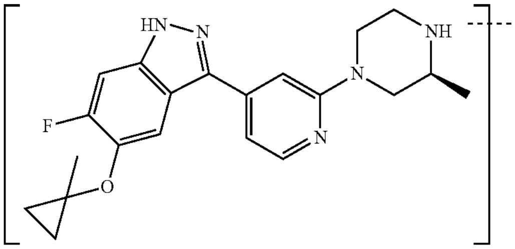
,
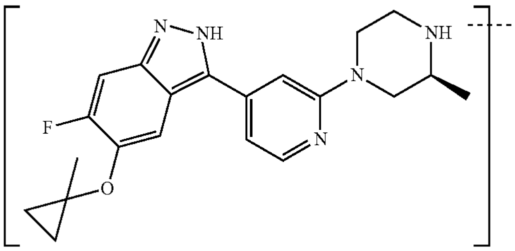
,
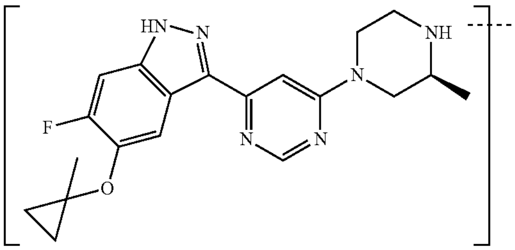
,
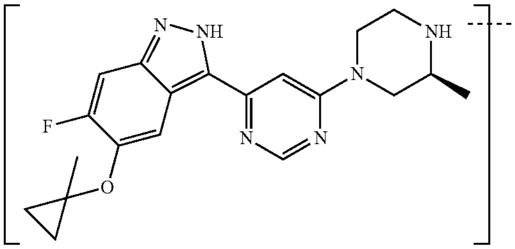
,
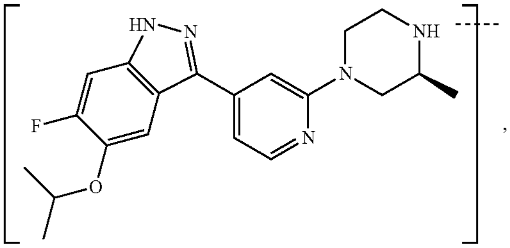
, -continued
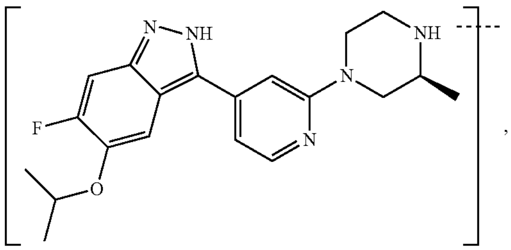
,
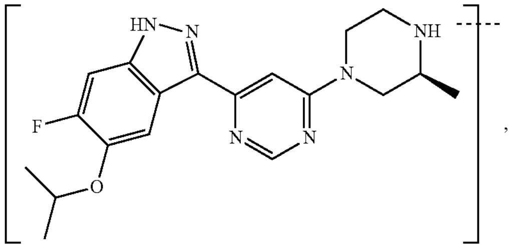
,
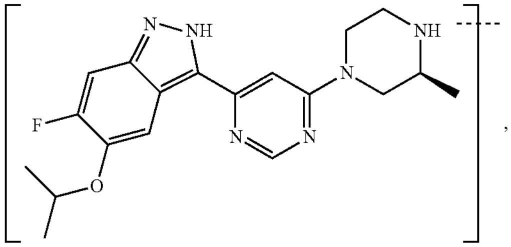
,
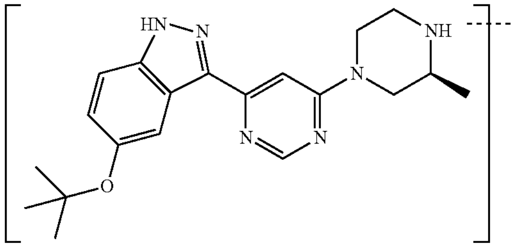
,
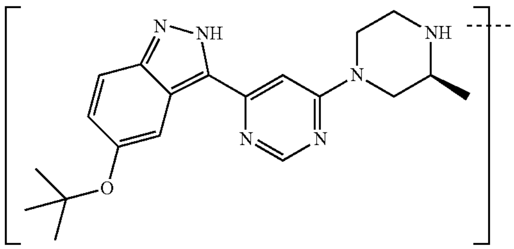
,
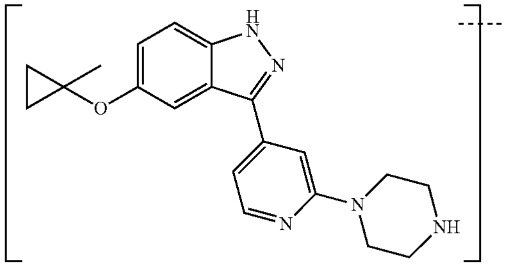
,
-continued
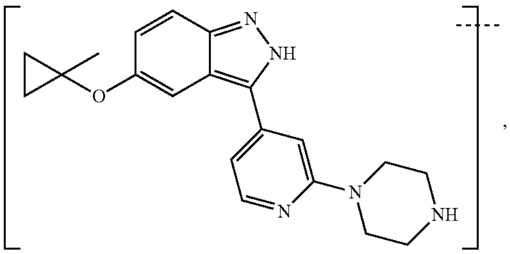
,
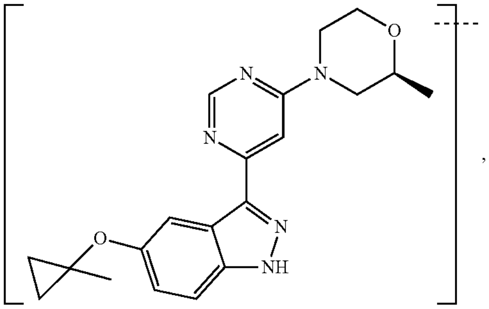
,
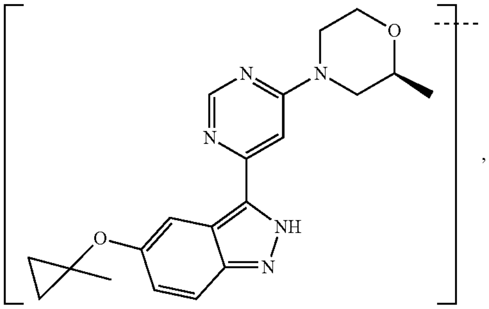
,
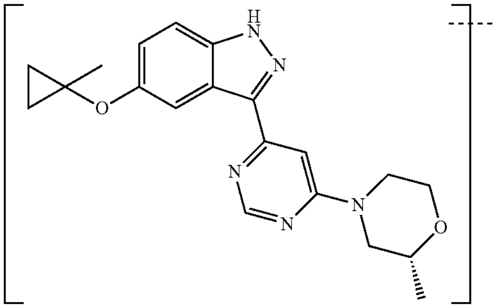
,
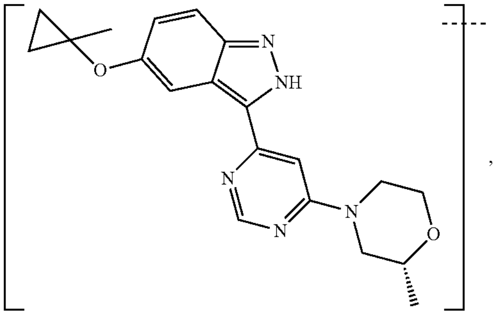
, -continued
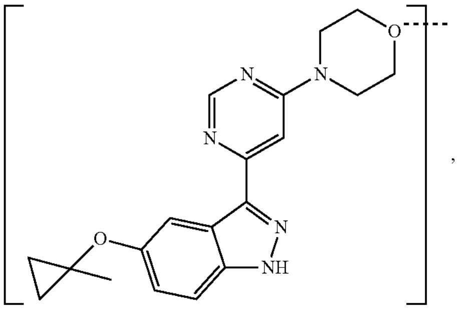
,
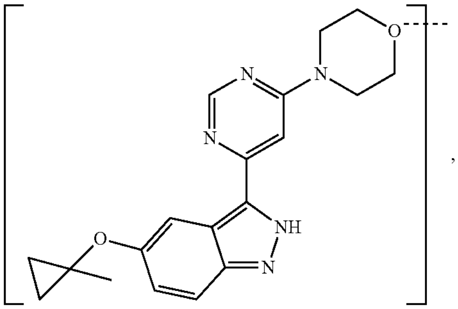
,
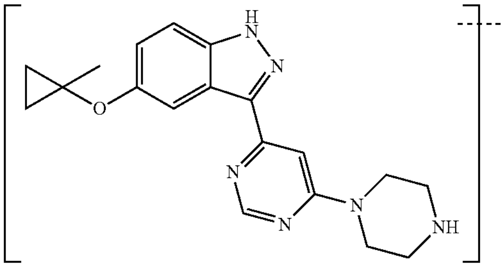
,
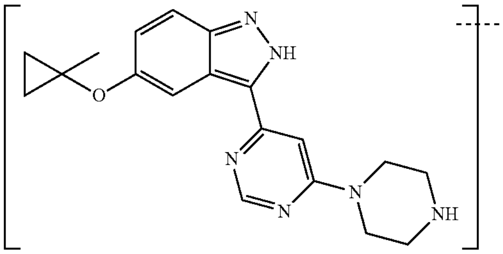
,
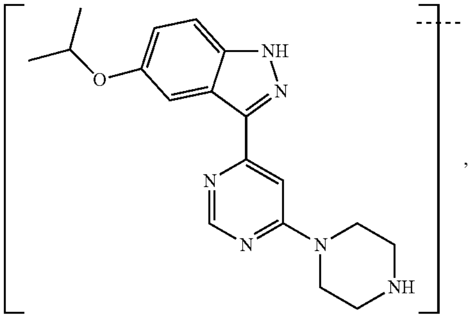
,
-continued
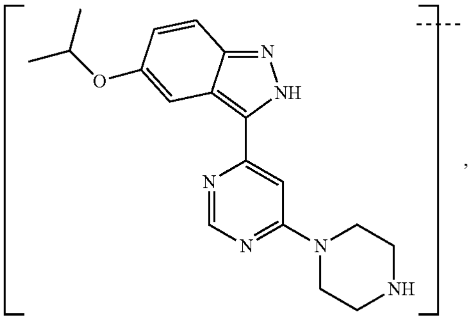
,
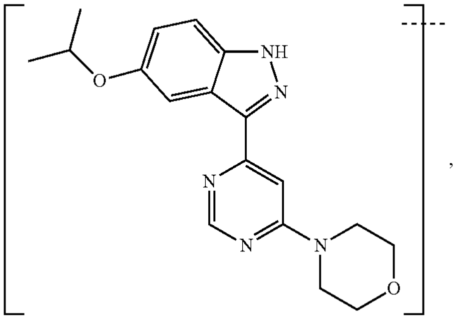
,
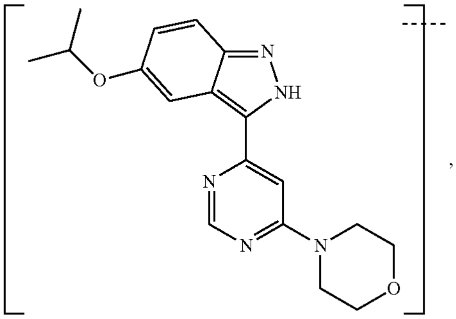
,
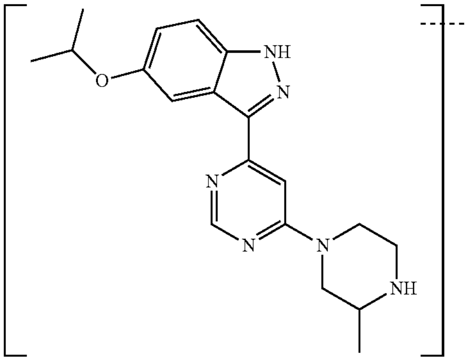
,
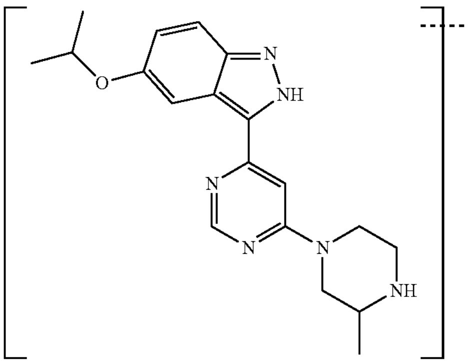
, -continued
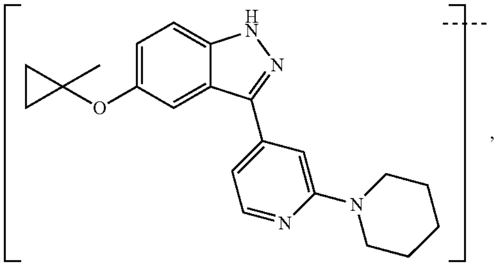
,
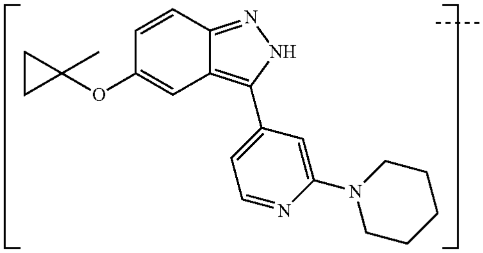
,
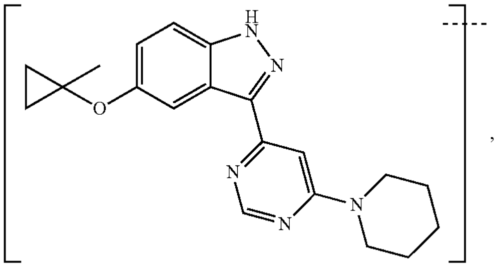
,
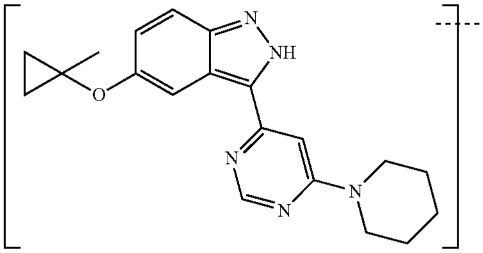
,
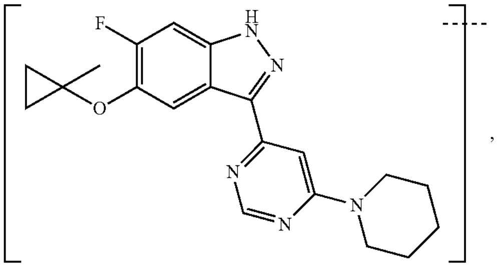
,
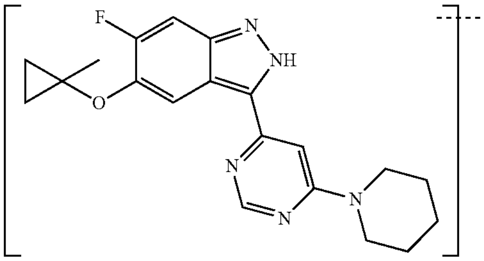
,
-continued
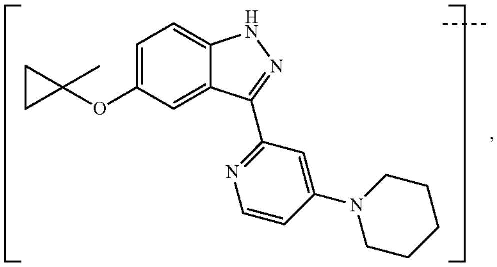
,
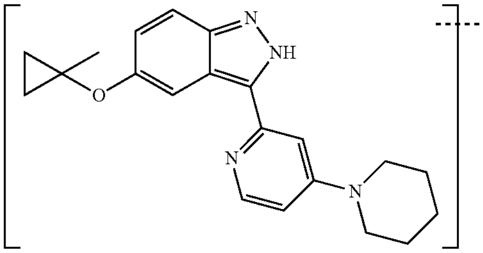
,
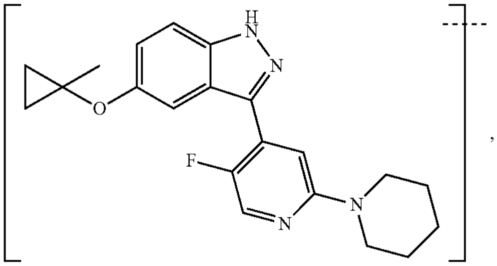
,
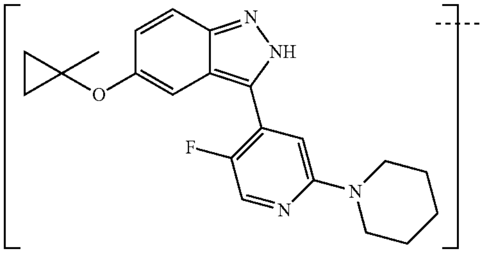
,
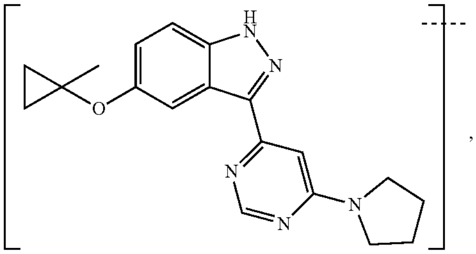
,
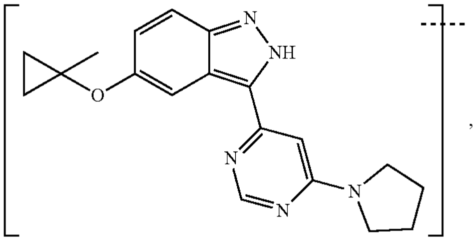
, -continued
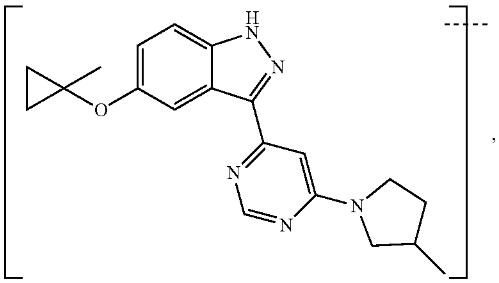
,
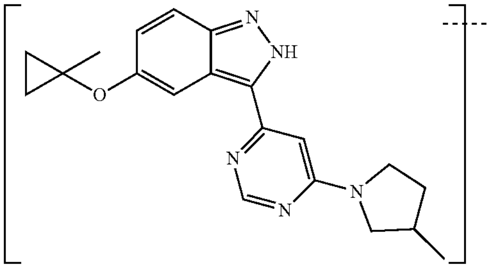
,
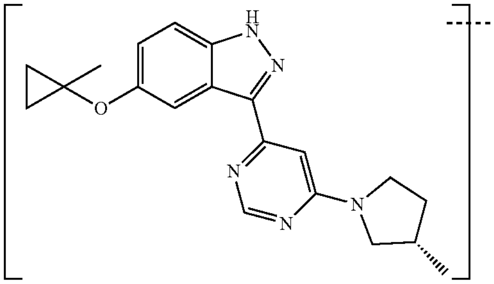
,
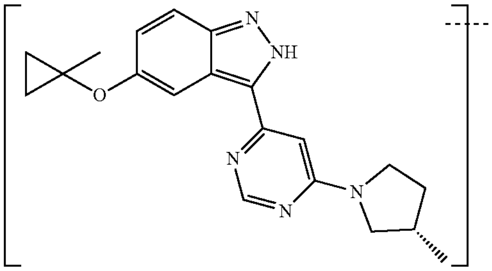
,
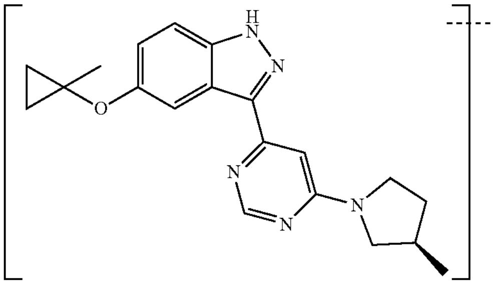
,
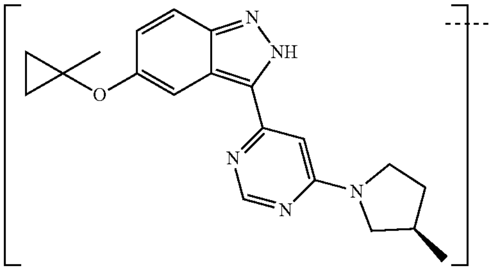
,
-continued
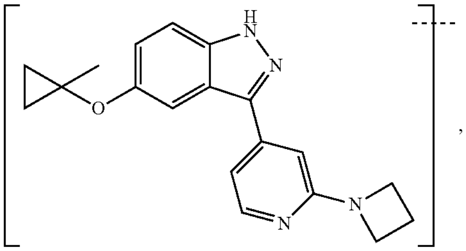
,
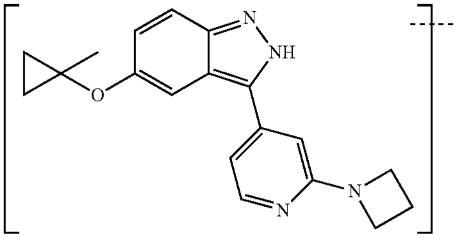
,
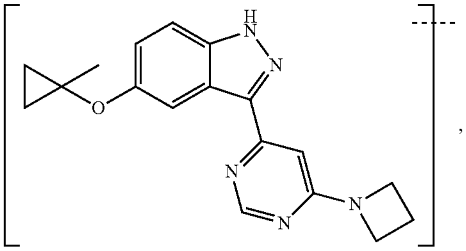
,
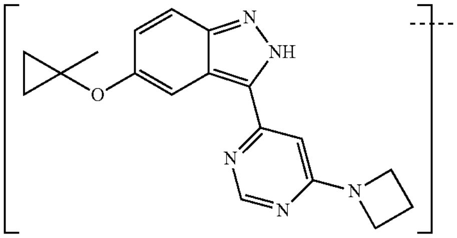
,
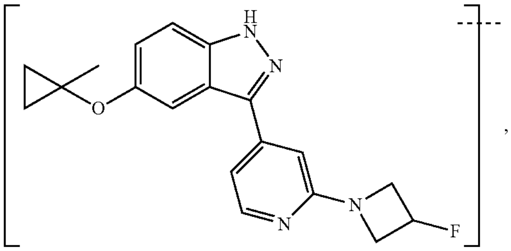
,
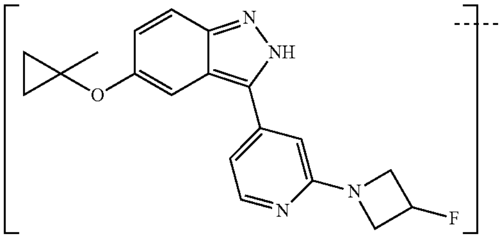
,
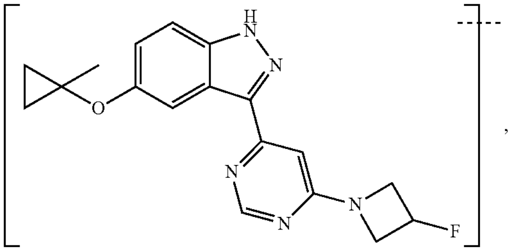
, -continued
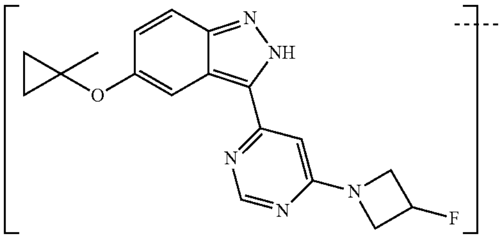
,
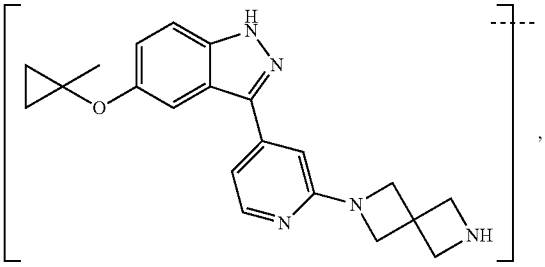
,
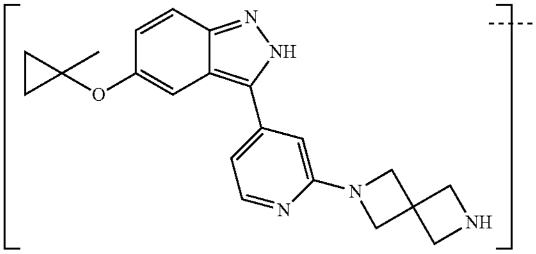
,
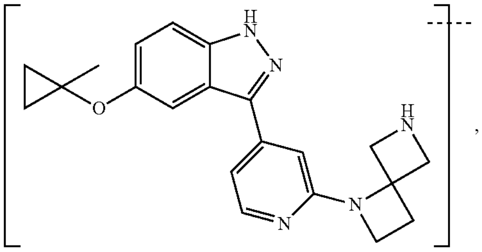
,
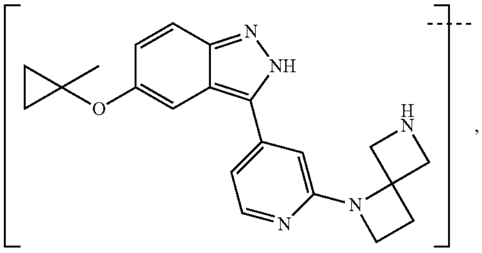
,
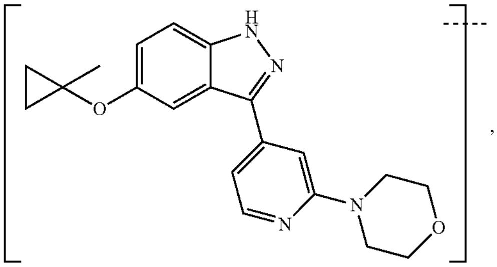
,
-continued
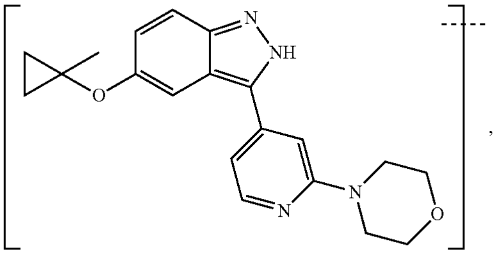
,
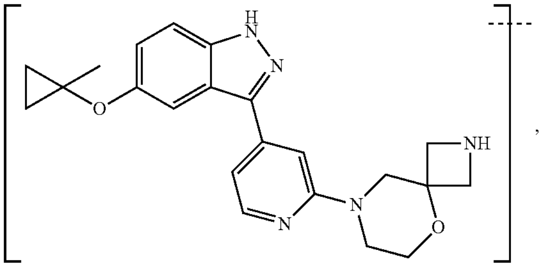
,
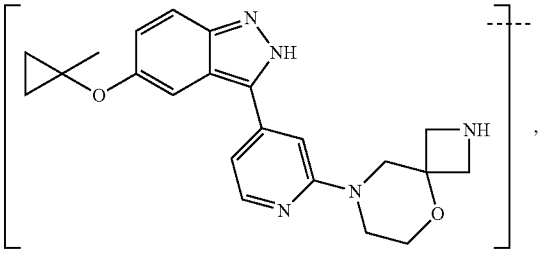
,
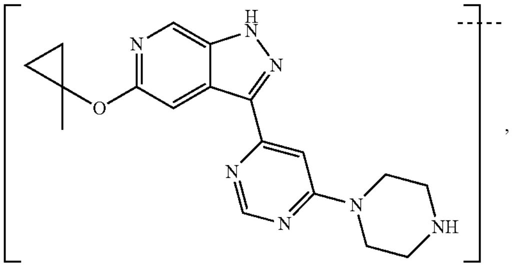
,
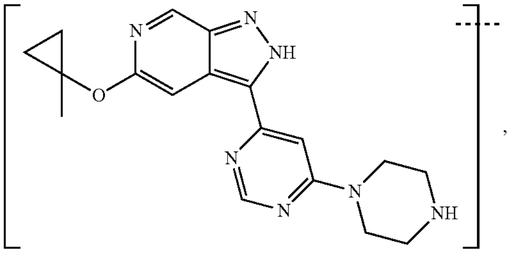
,
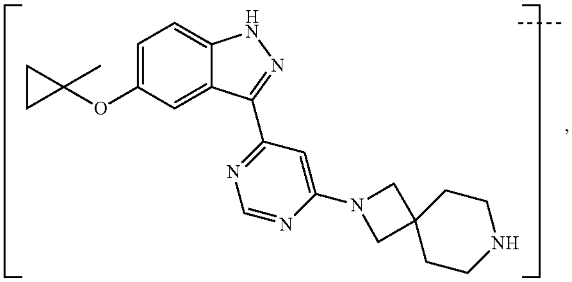
, -continued
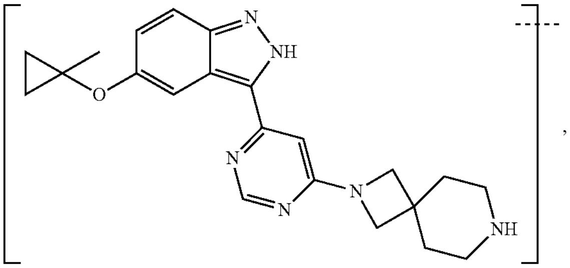
,
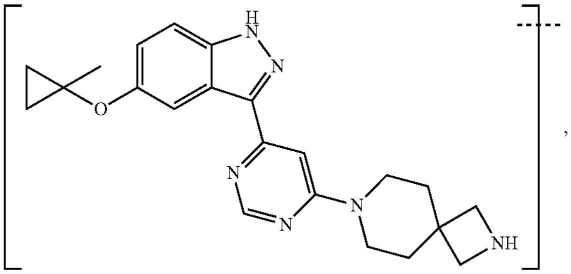
,
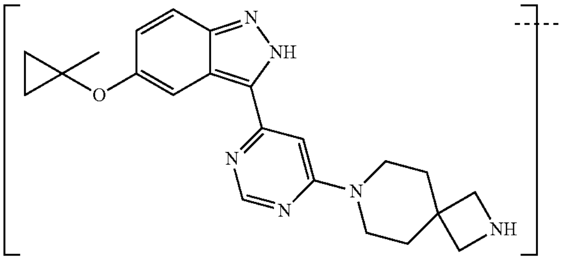
,
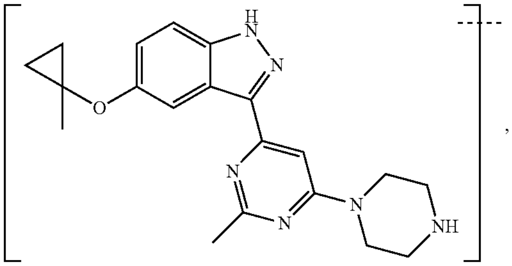
,
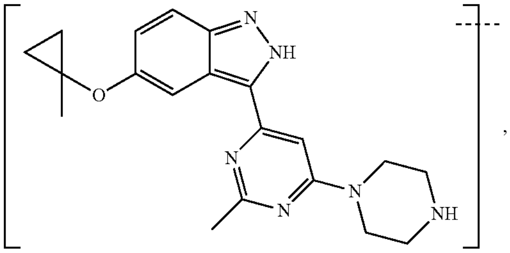
,
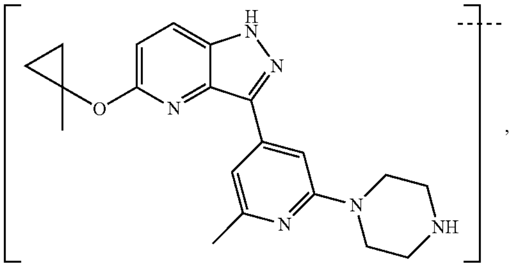
,
-continued
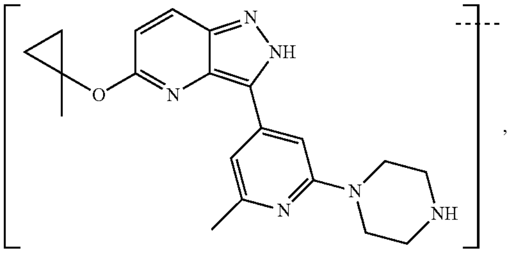
,
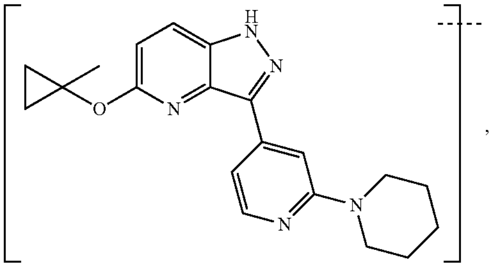
,
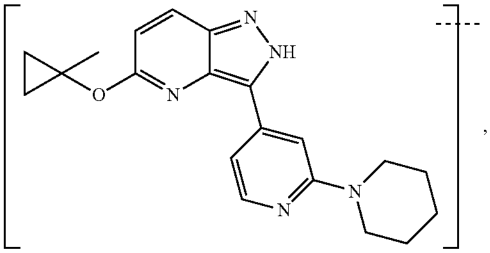
,
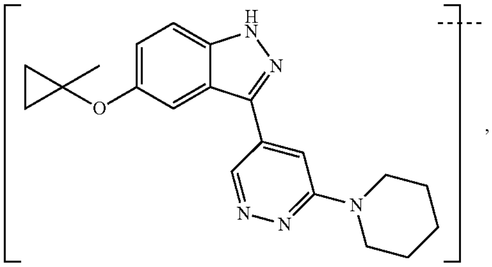
,
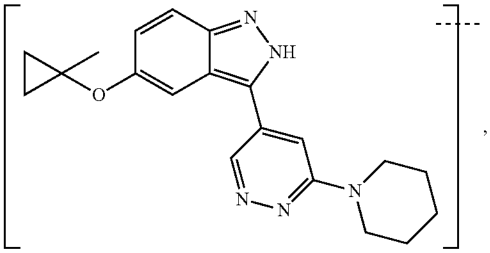
,
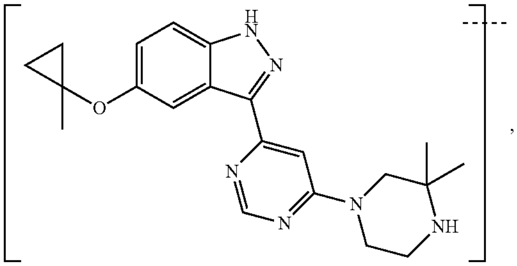
, -continued
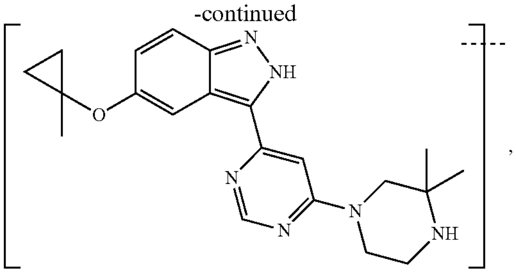
,
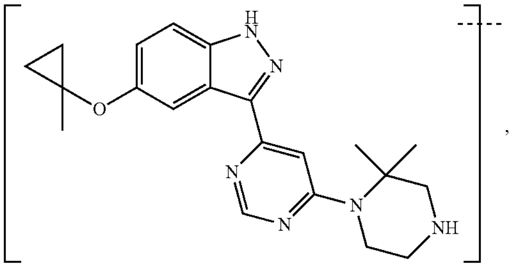
, and
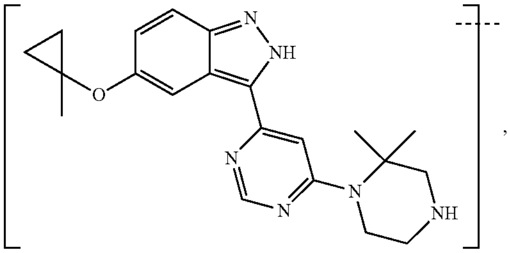
,
wherein  of the PTM indicates the point of attachment with a chemical linker group or a ULM.
In any aspect embodiment described herein, the PTM has the chemical structure:
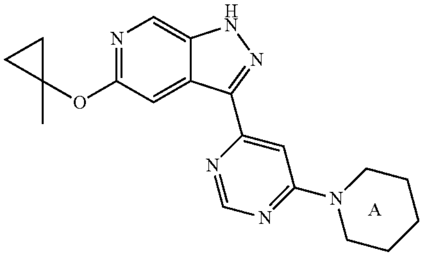
,
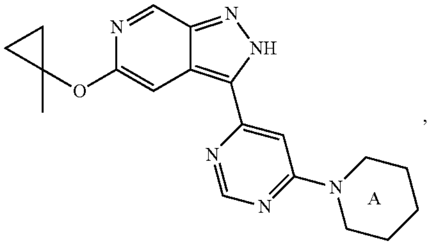
,
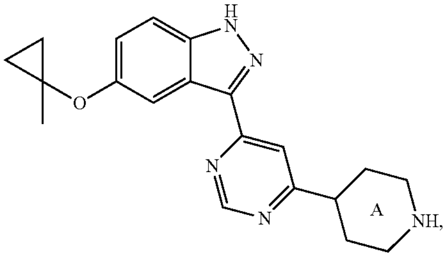
-continued
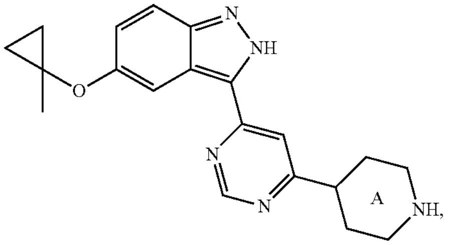
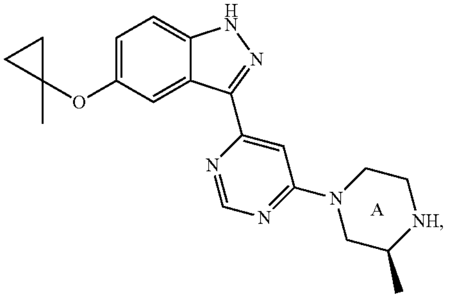
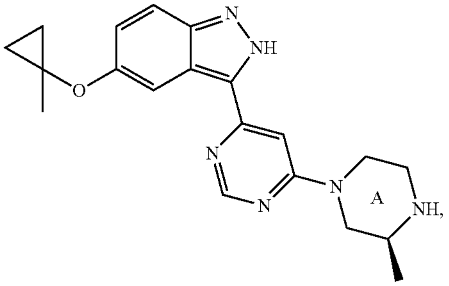
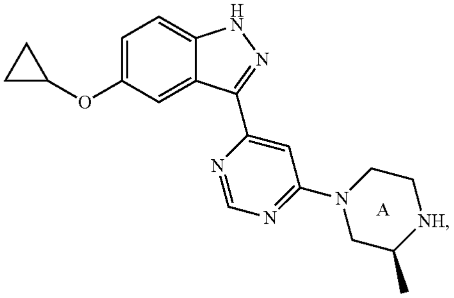
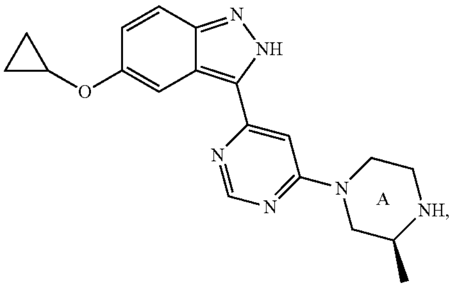

-continued
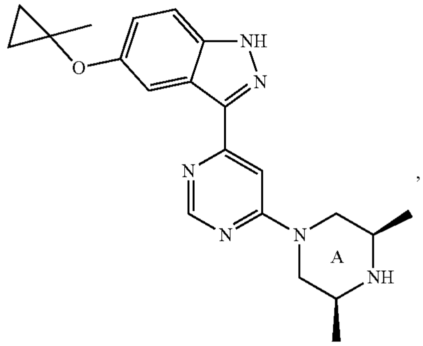
,
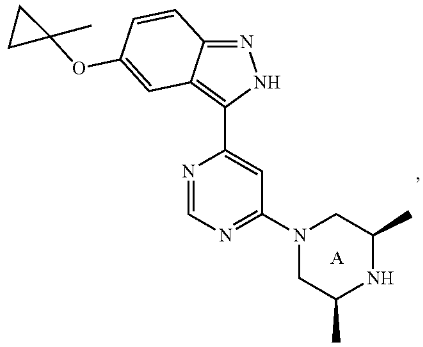
,
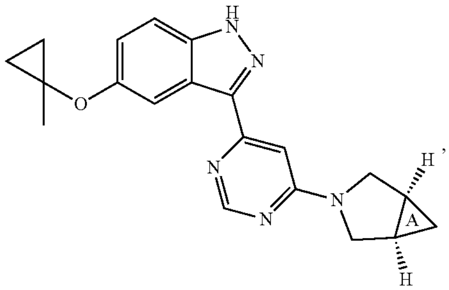
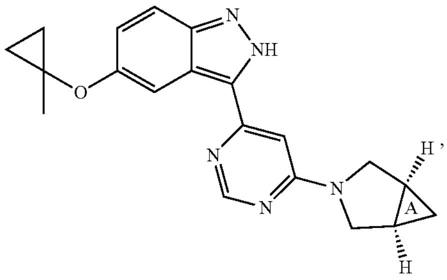
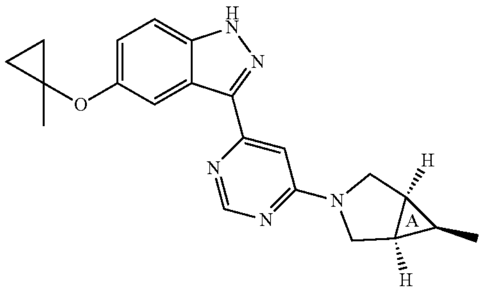
,
-continued
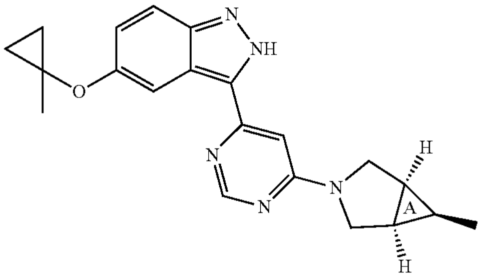
,
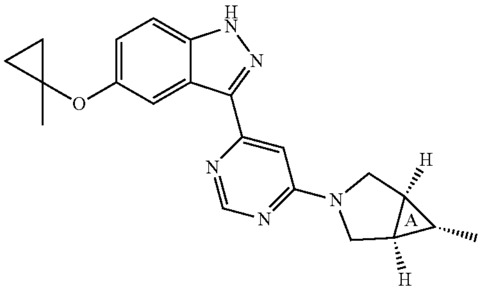
,
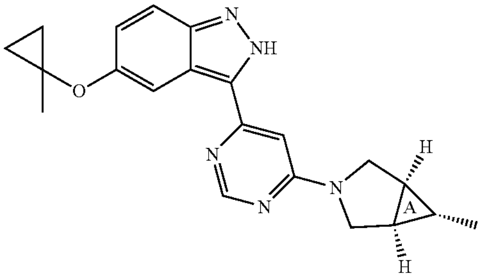
,
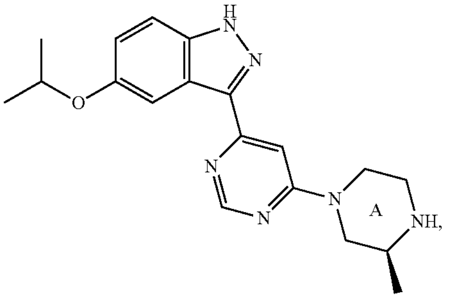
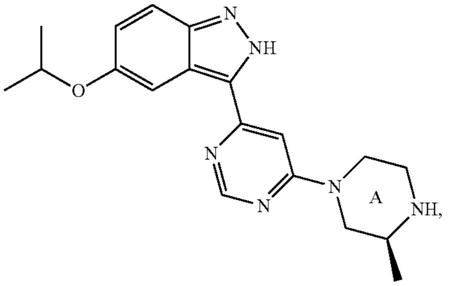
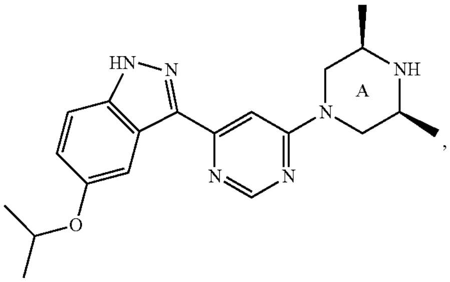
, -continued
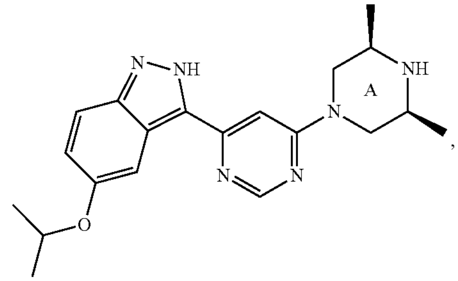
,
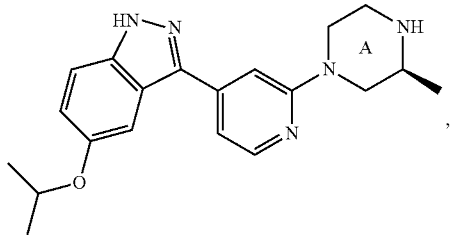
,
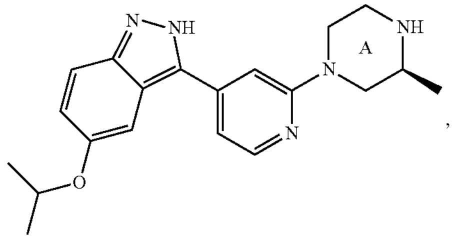
,
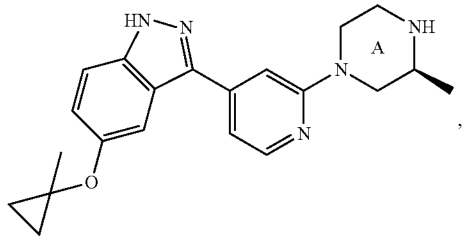
,
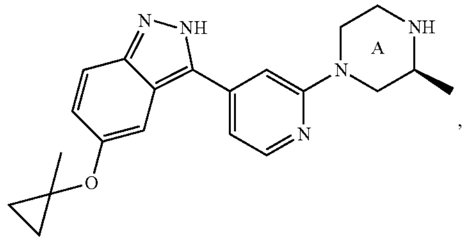
,
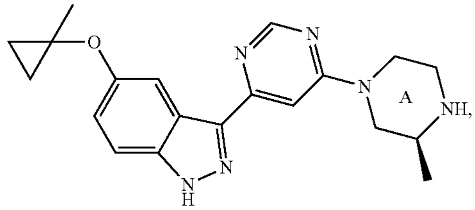
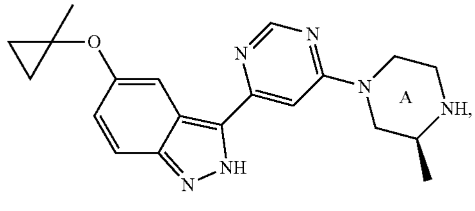
-continued
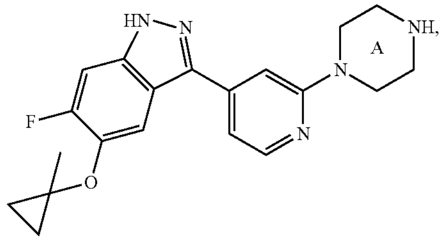
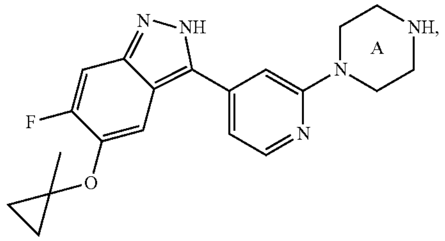
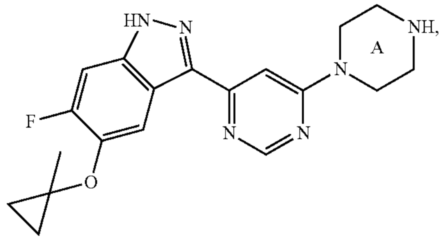
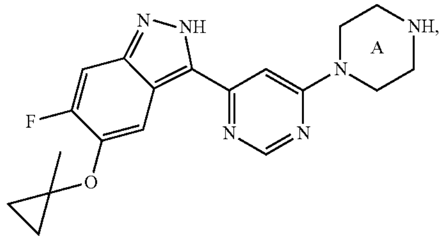
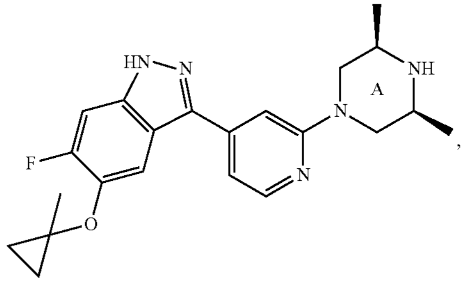
,
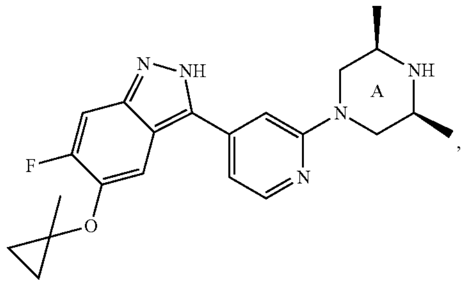
, -continued
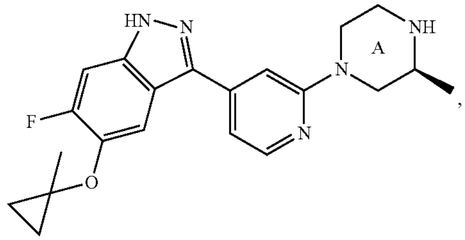
,
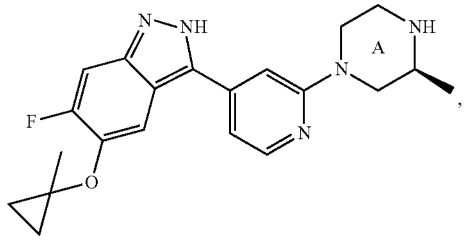
,
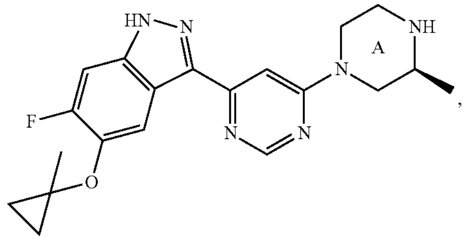
,
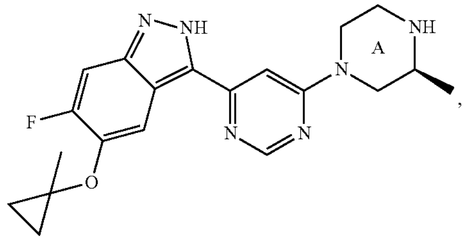
,
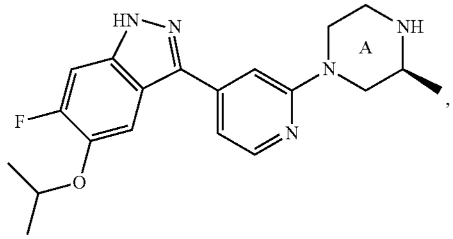
,
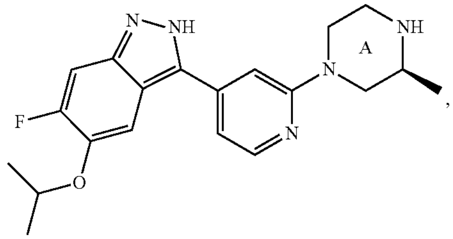
,
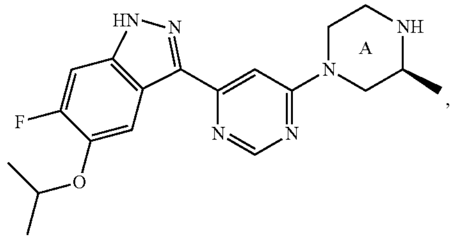
,
-continued
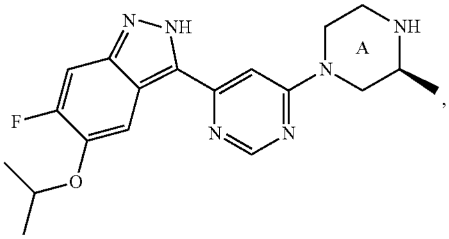
,
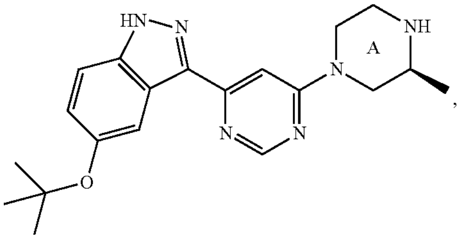
,
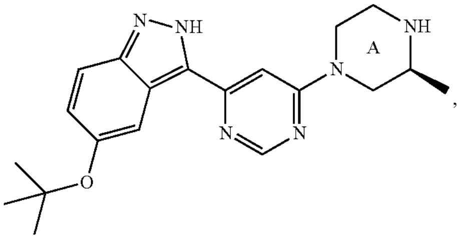
,
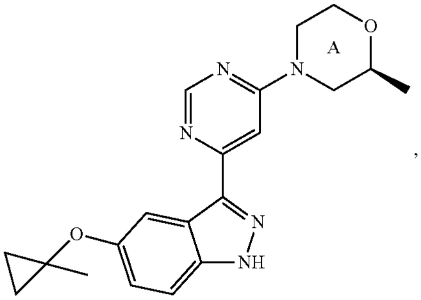
,
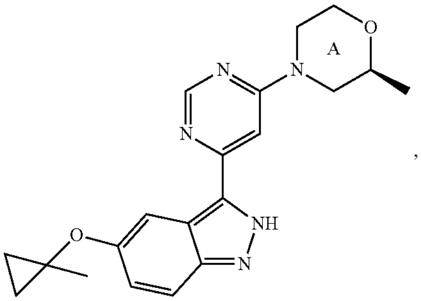
,
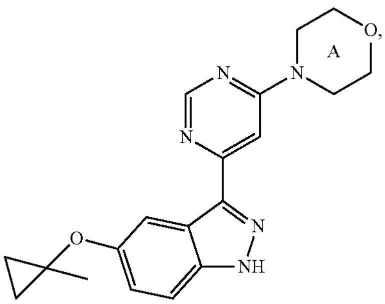
, -continued
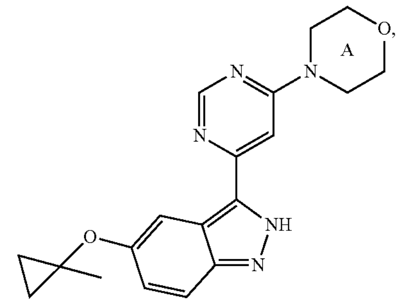
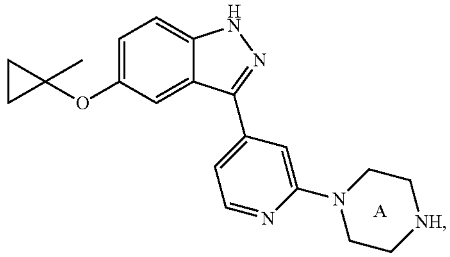
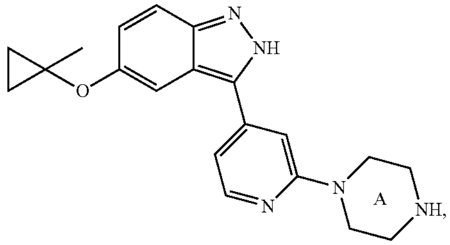
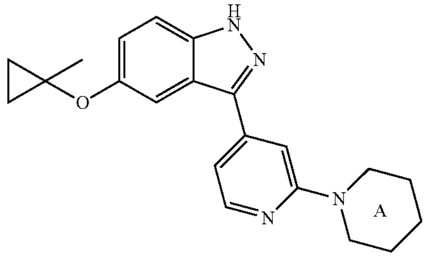
,
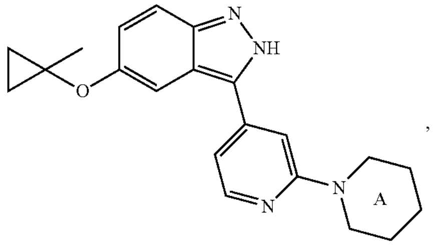
,
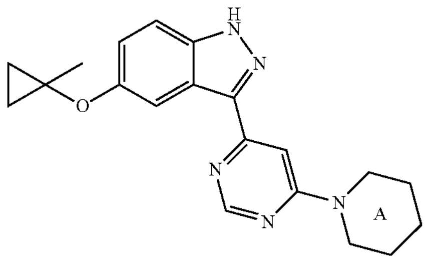
,
-continued
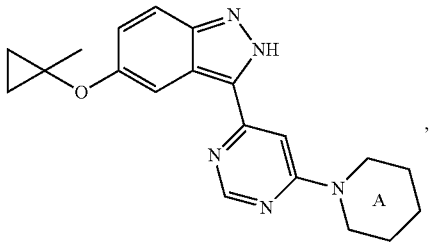
,
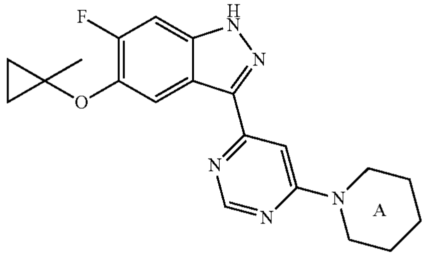
,
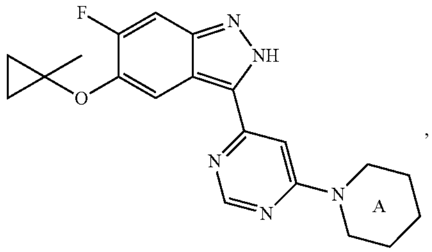
,
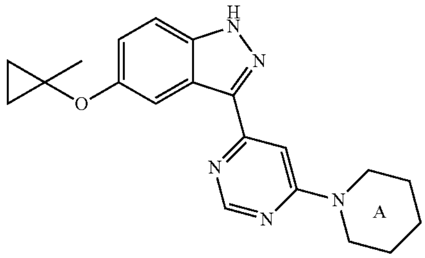
,
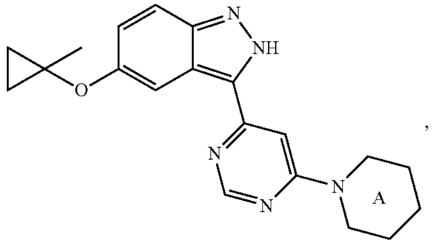
,
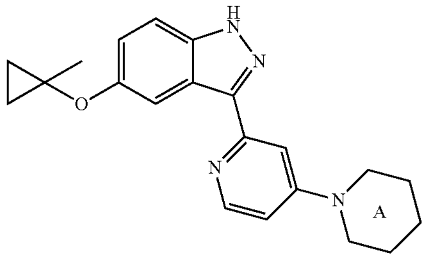
, -continued
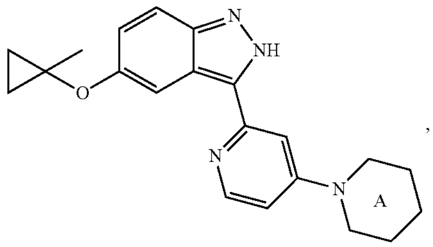
,
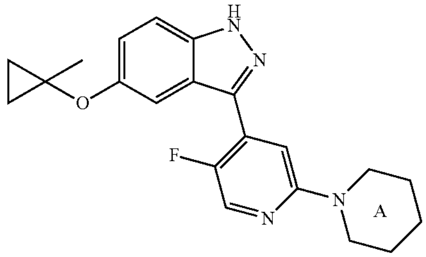
,
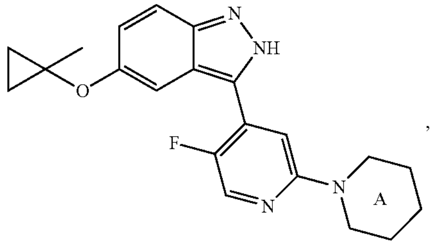
,
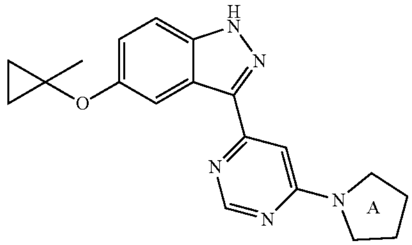
,
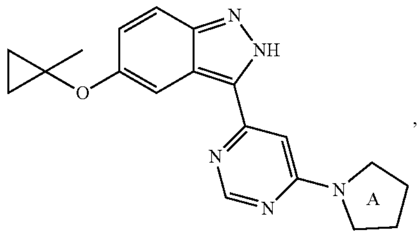
,
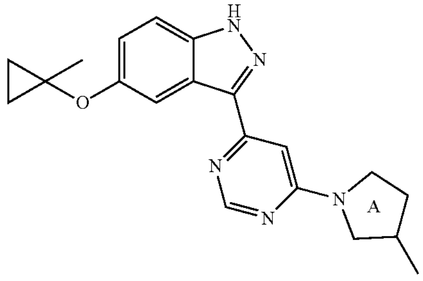
,
-continued
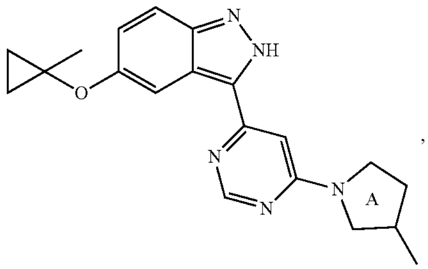
,
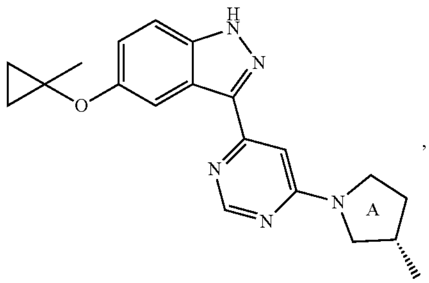
,
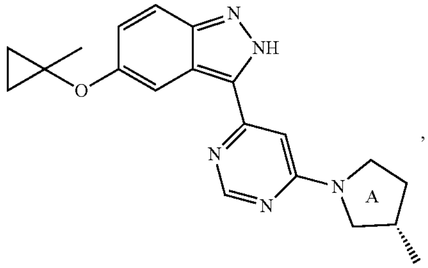
,
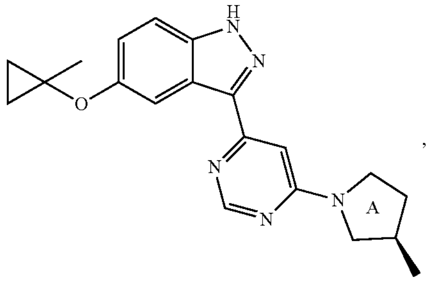
,
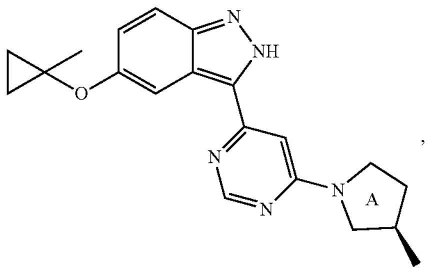
,
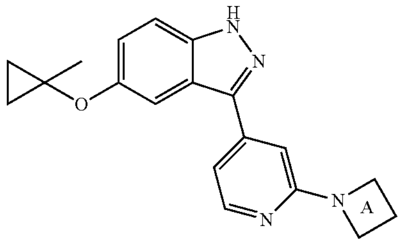
, -continued
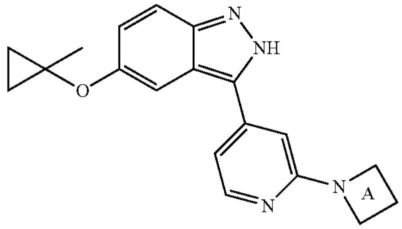
,
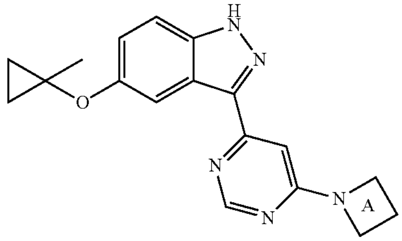
,
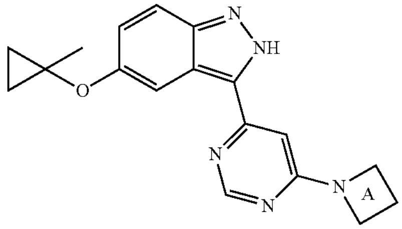
,
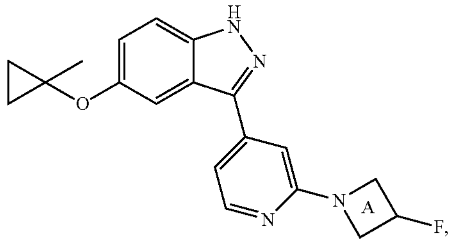
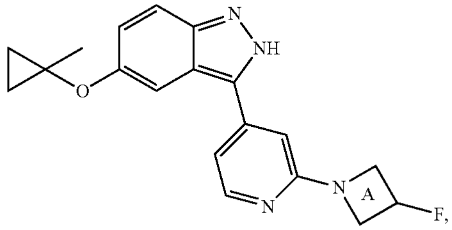
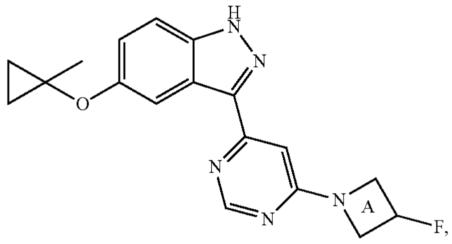
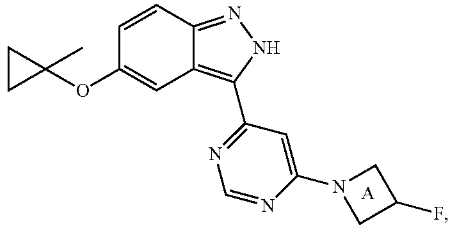
-continued
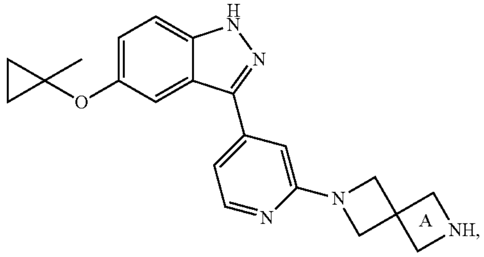
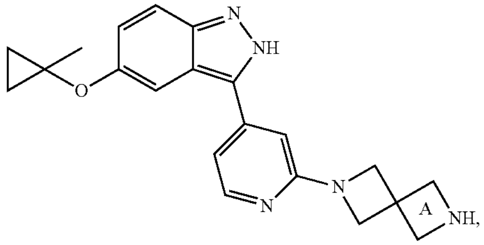
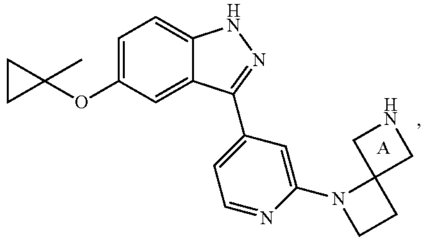
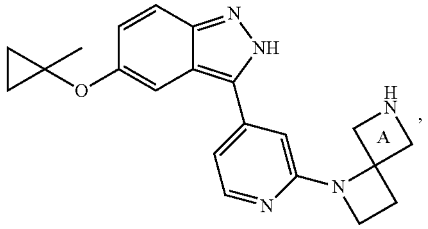
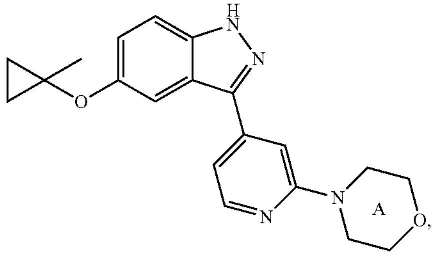
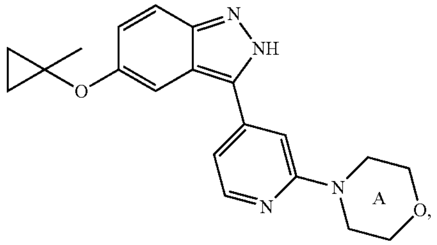
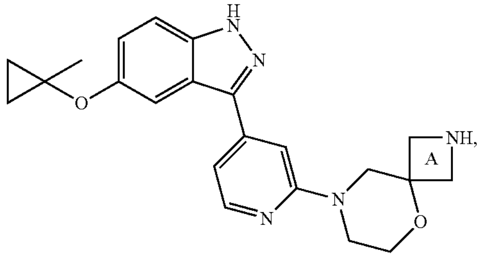

-continued
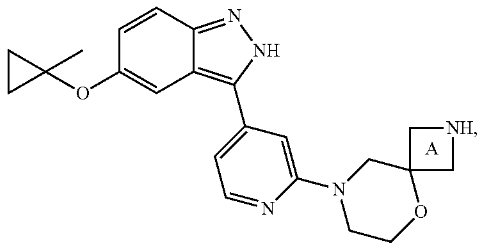
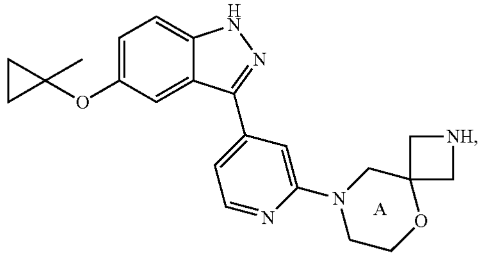
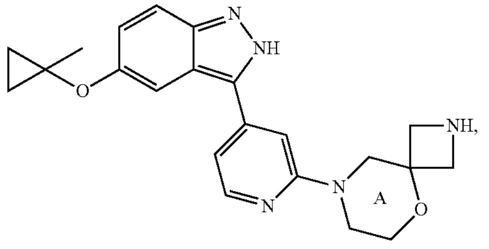
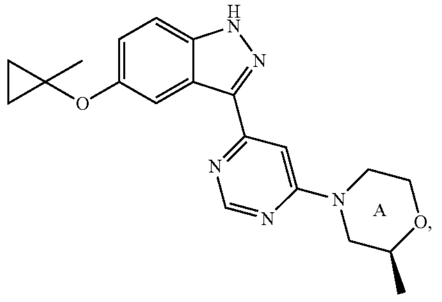
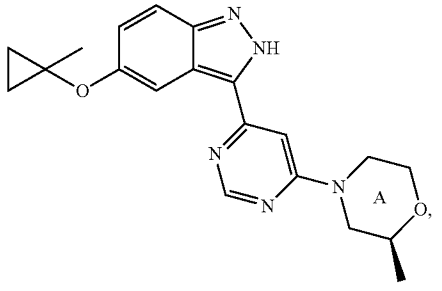
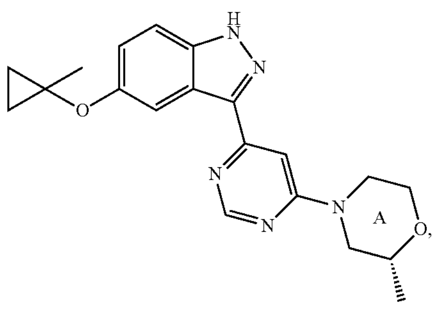
-continued
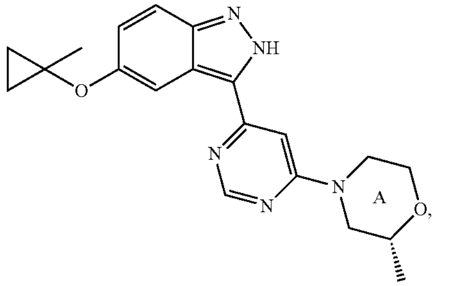
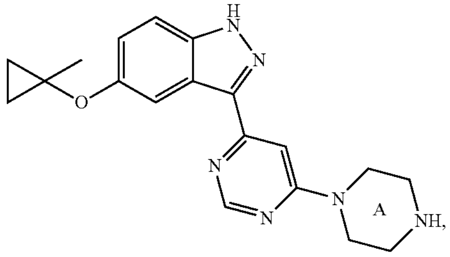
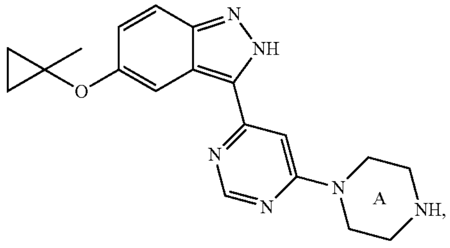
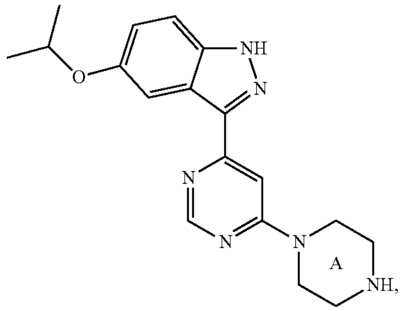
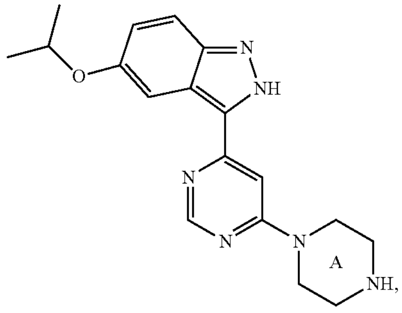
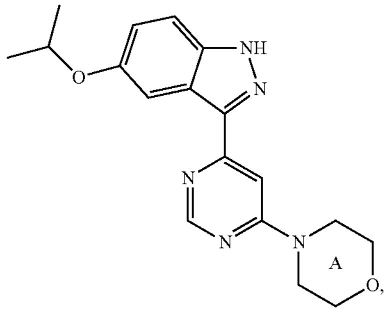

-continued
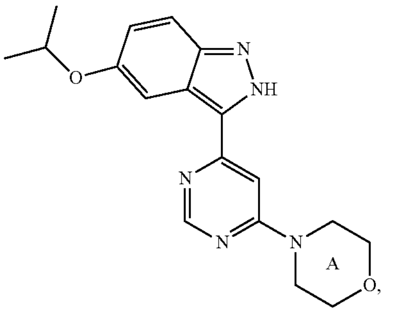
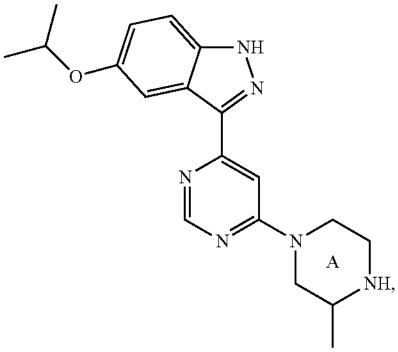
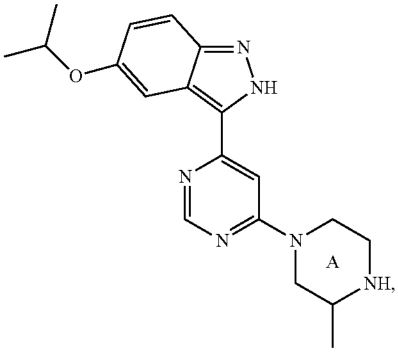
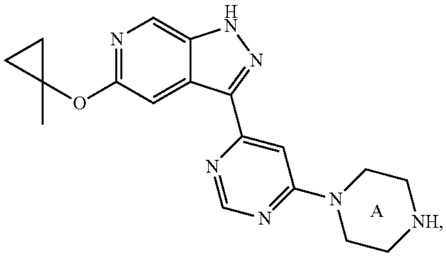
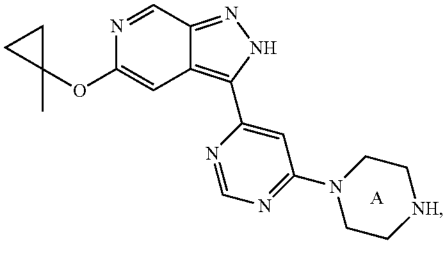
-continued
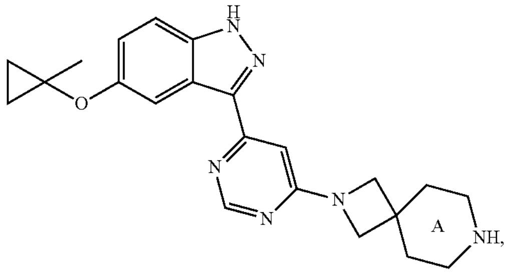
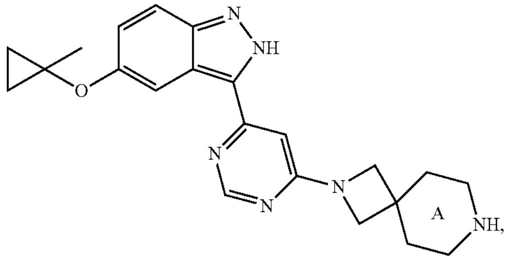
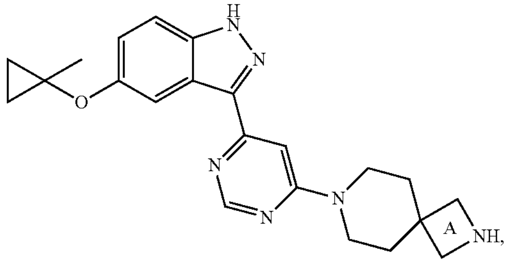
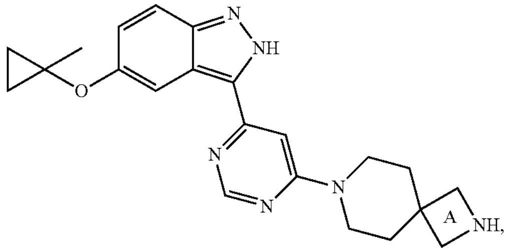
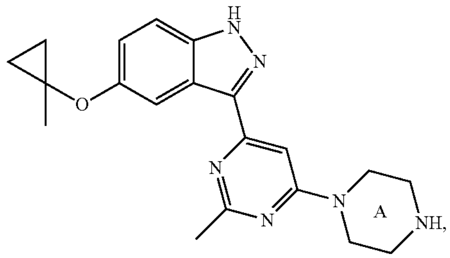
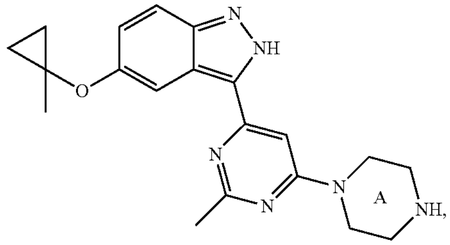

-continued
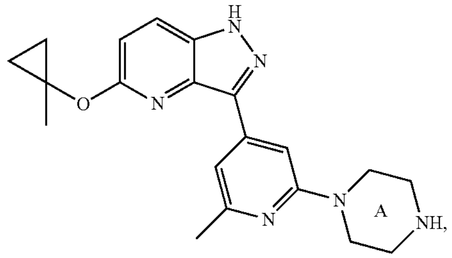
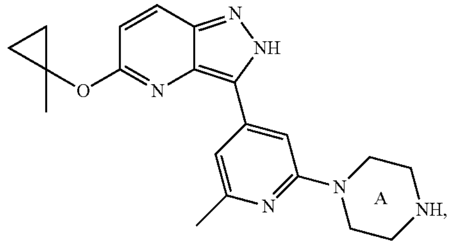
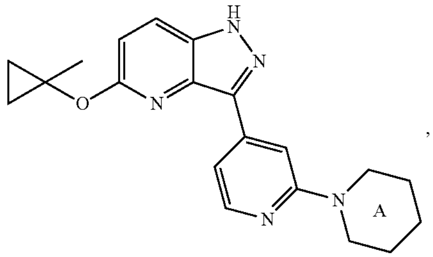
,
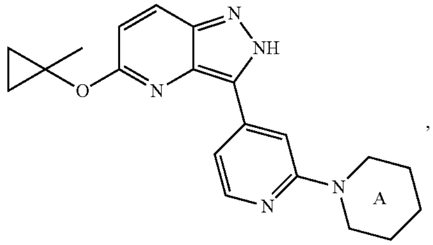
,
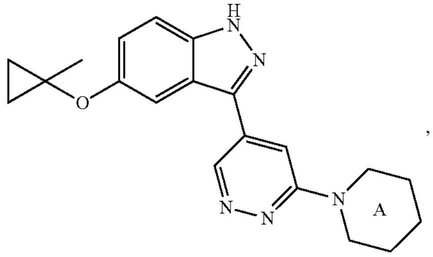
,
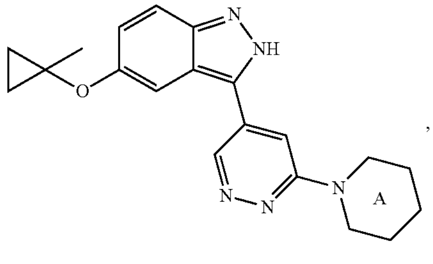
,
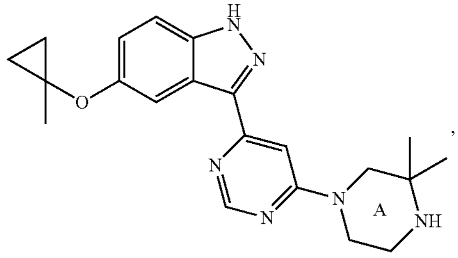
,
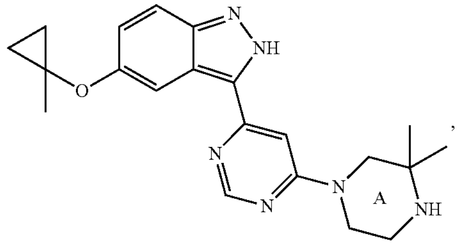
,
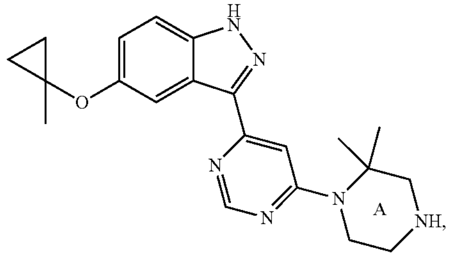
and
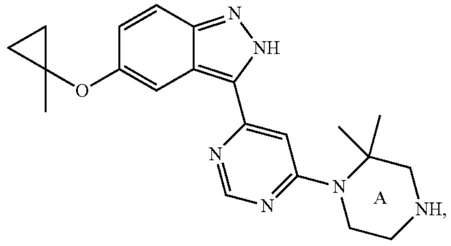
wherein the PTM is covalently linked to the L or ULM via an atom of the heterocycloalkyl A or a substituent thereof.
In any aspect or embodiment described herein, the PTM has the chemical structure:
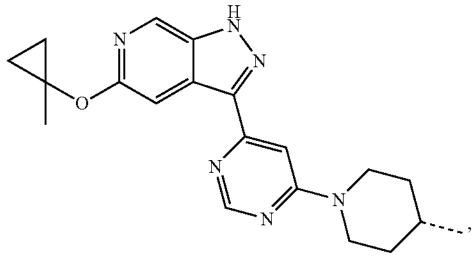
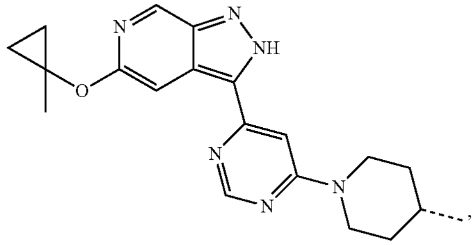

-continued
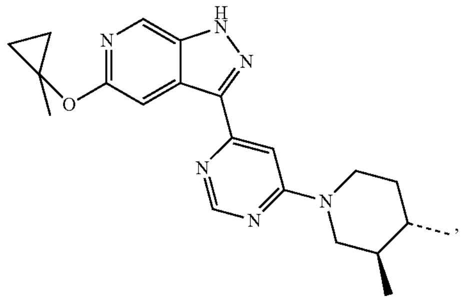
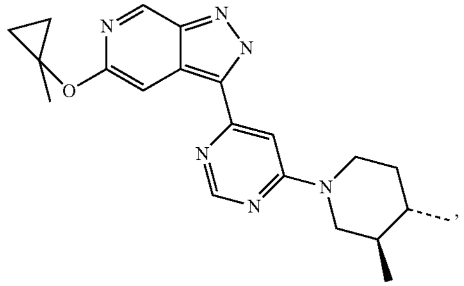
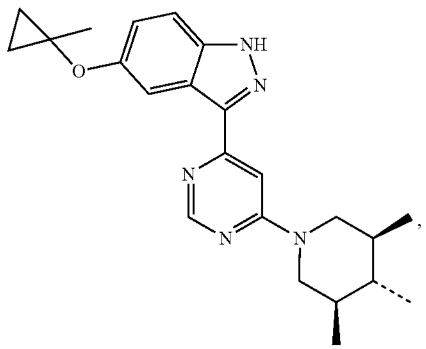
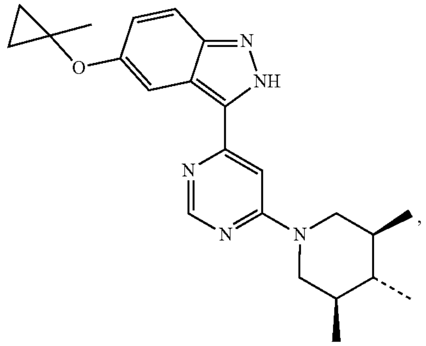
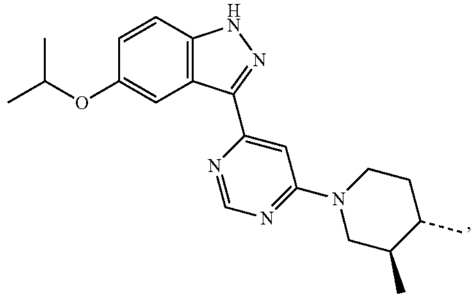
-continued
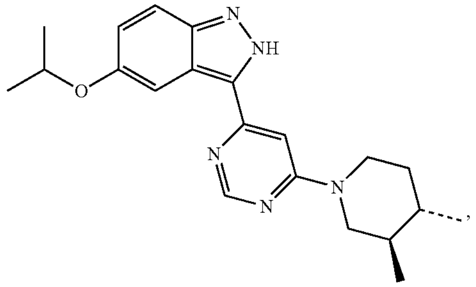
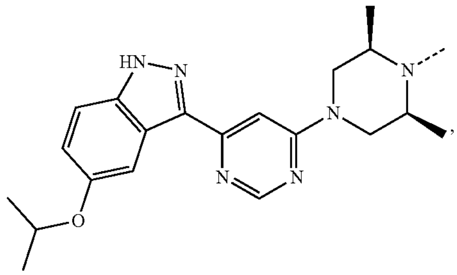
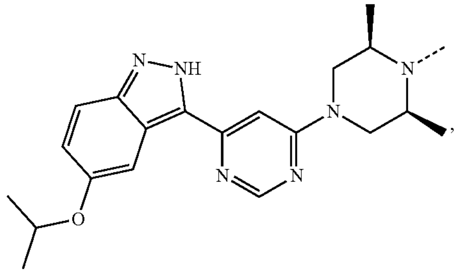
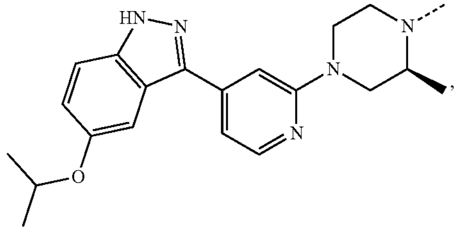
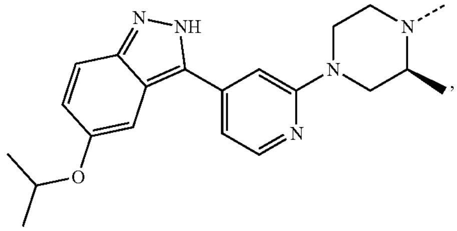
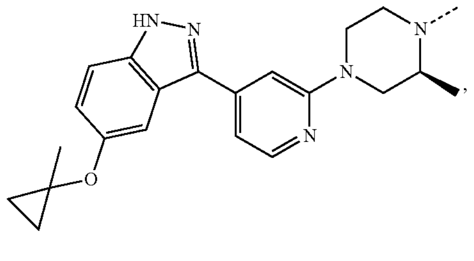

-continued
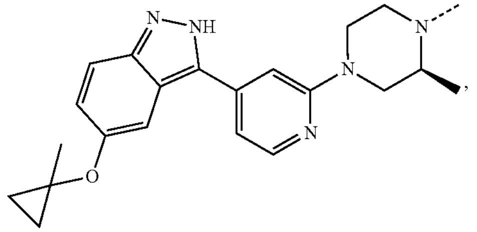
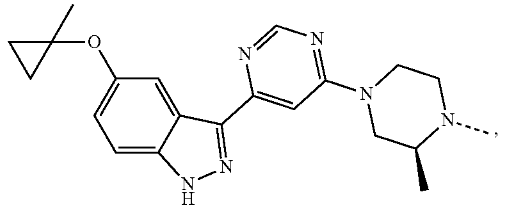
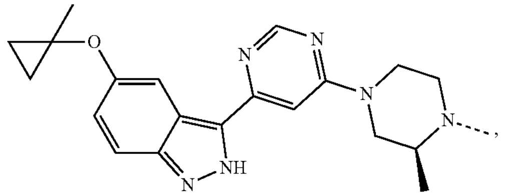
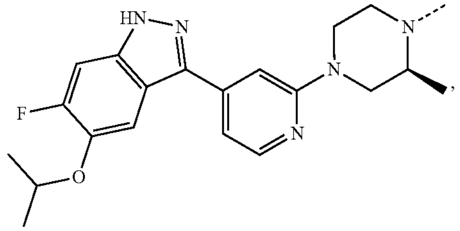
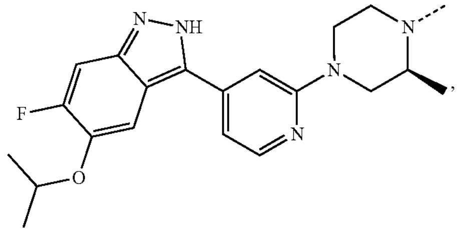
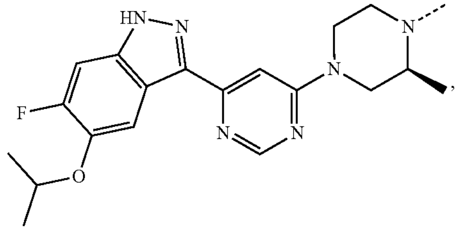
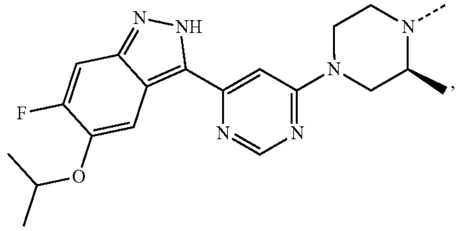
-continued
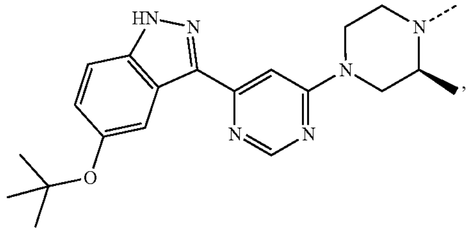
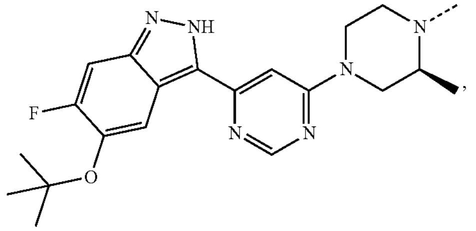
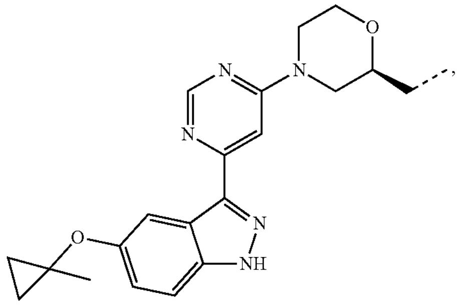
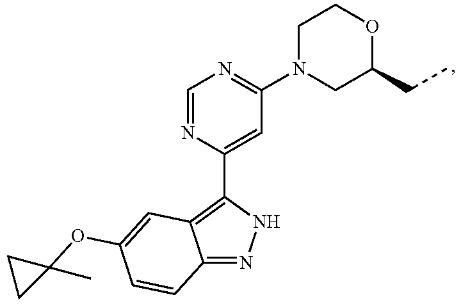
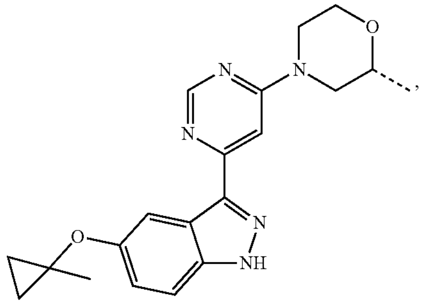
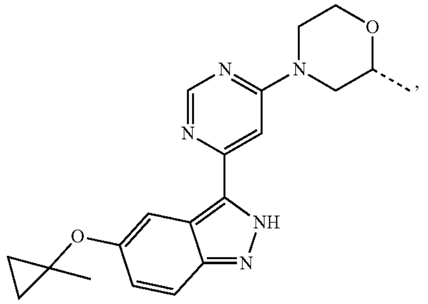

-continued
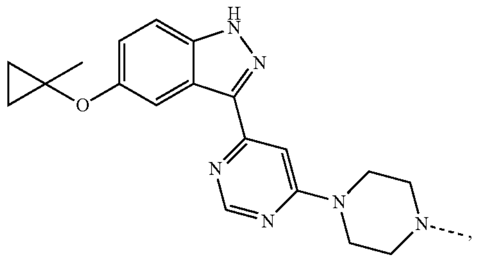
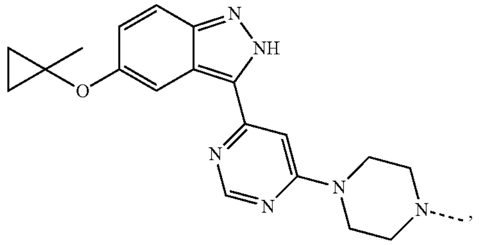
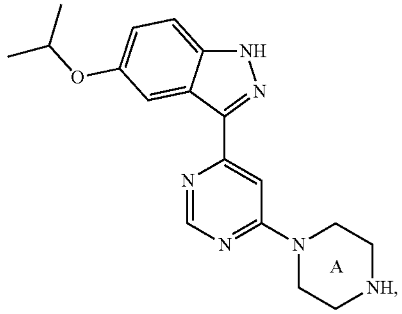
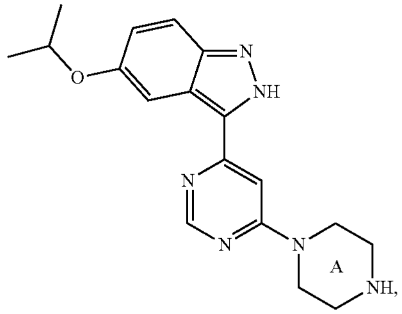
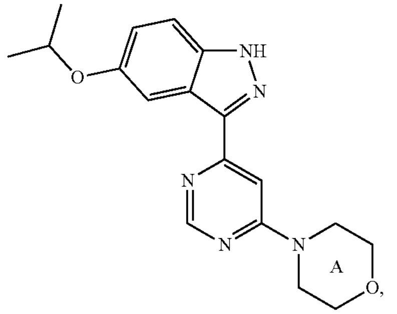
-continued
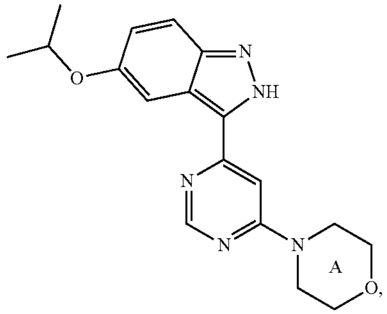
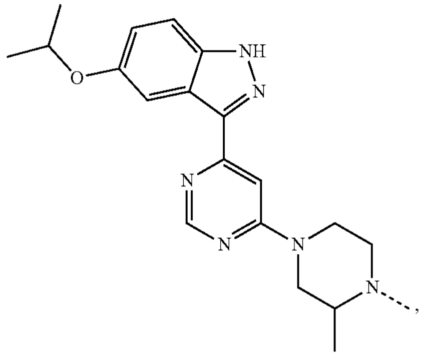
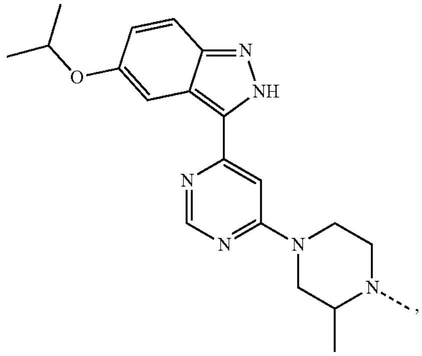
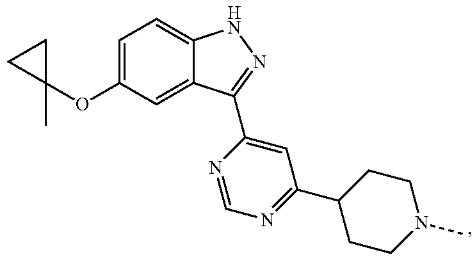
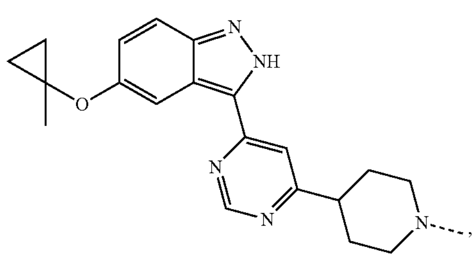

-continued
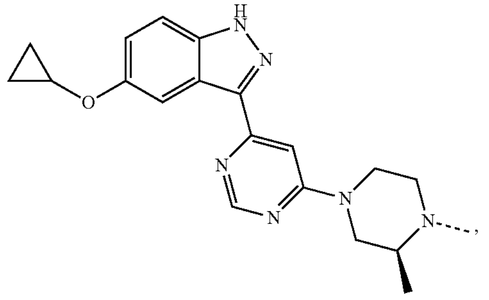
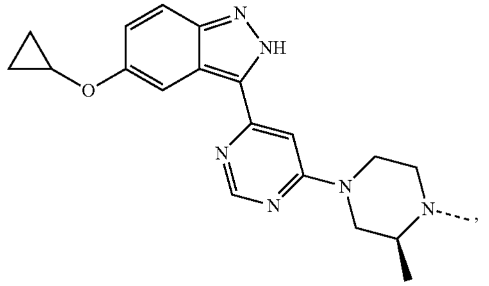
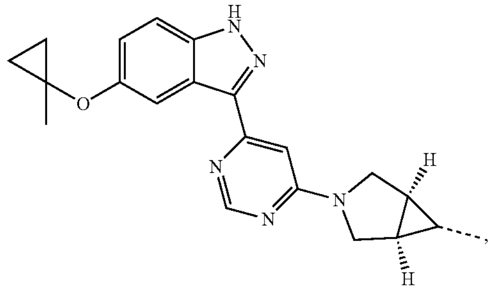
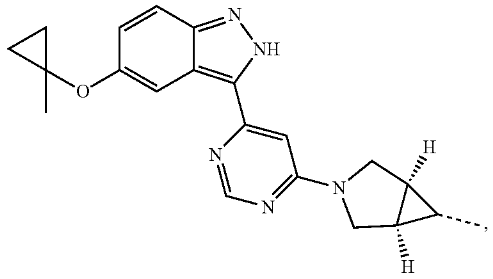
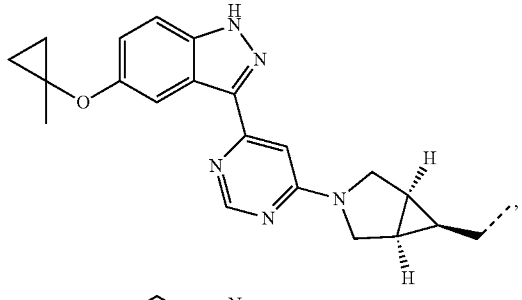
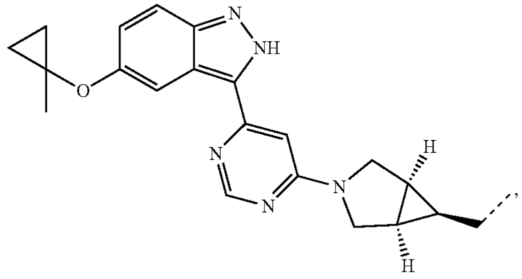
-continued
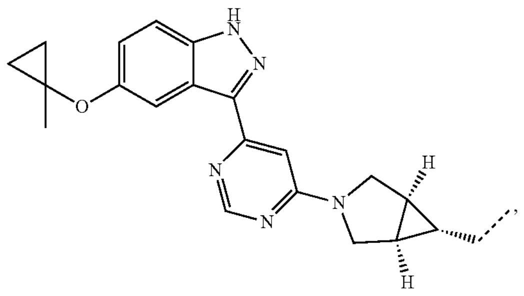
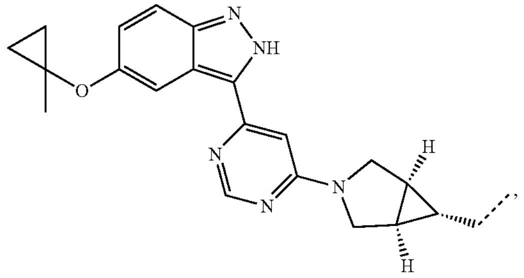
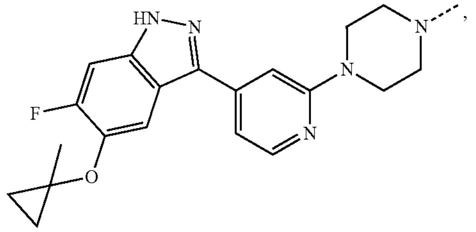
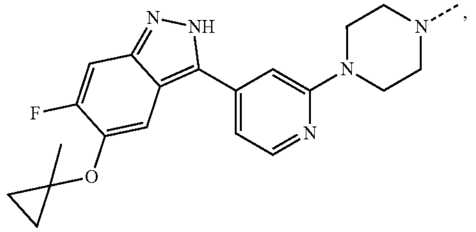
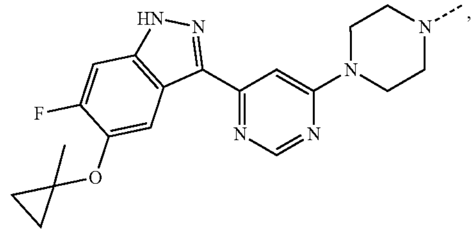
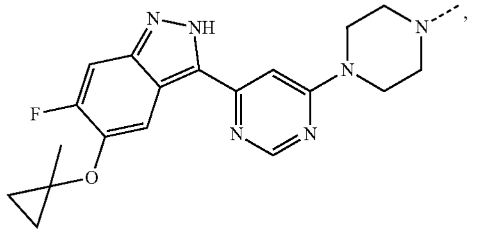

-continued
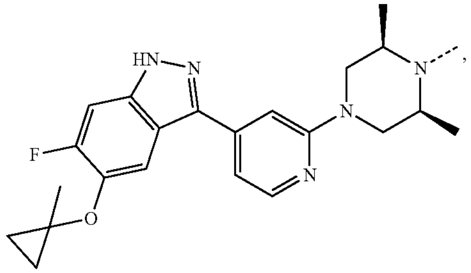
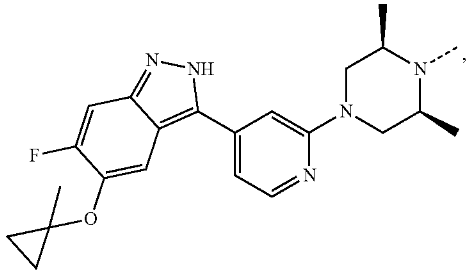
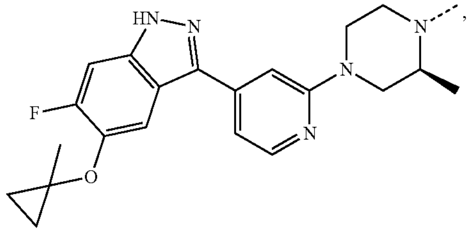
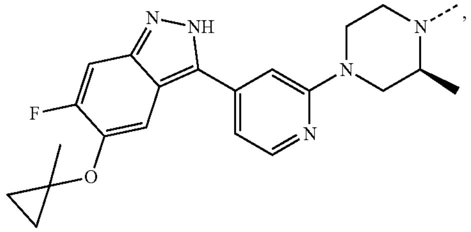
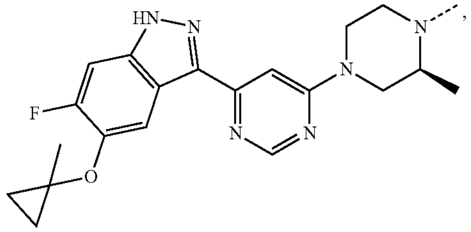
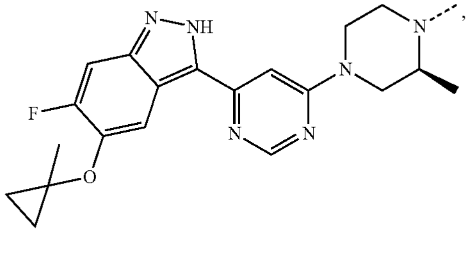
-continued
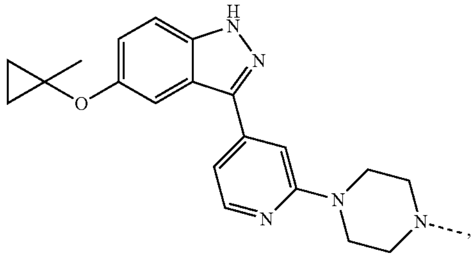
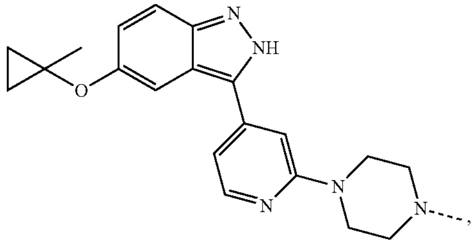
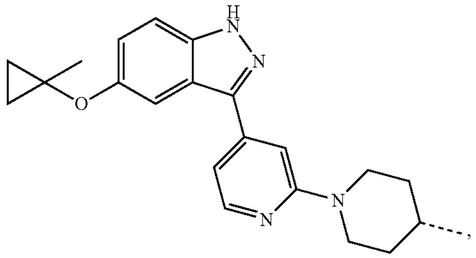
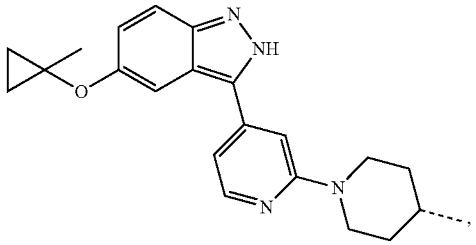
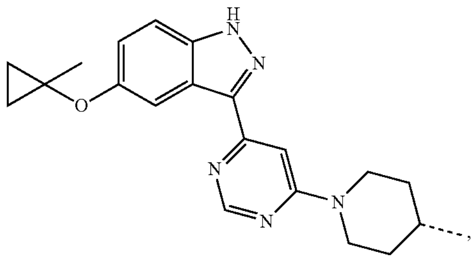
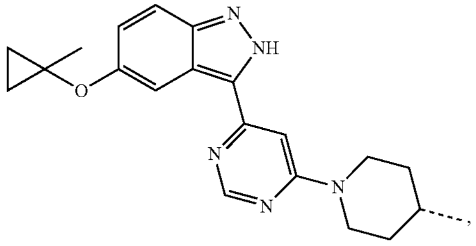

-continued
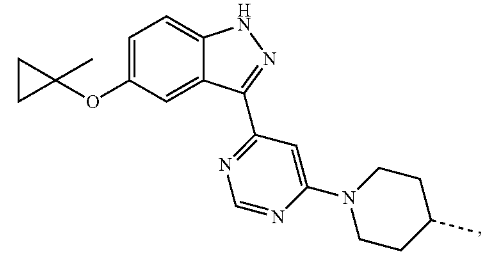
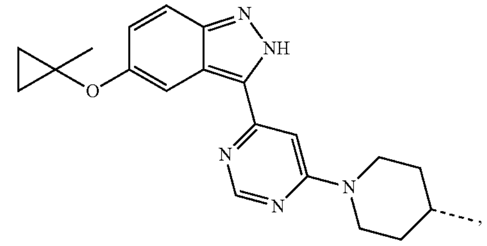
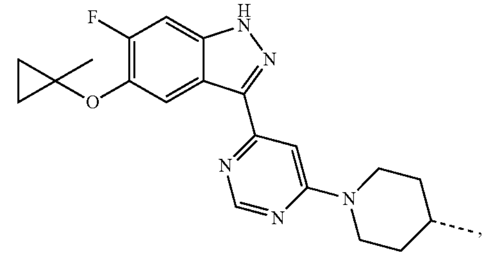
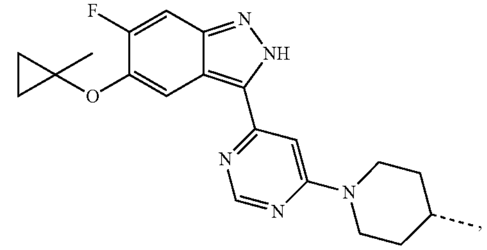
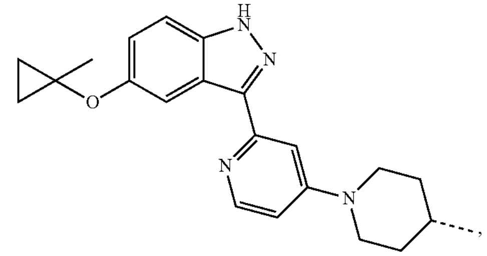
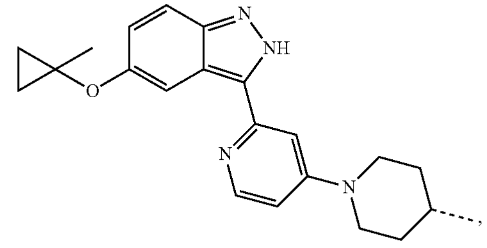
-continued
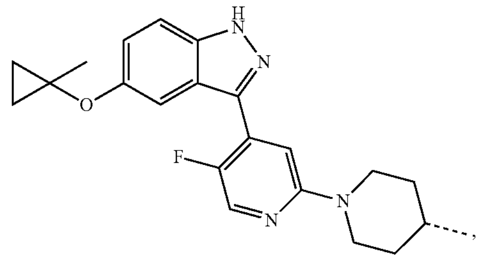
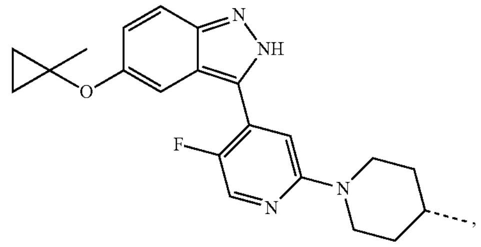
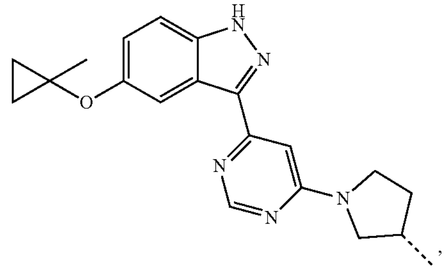
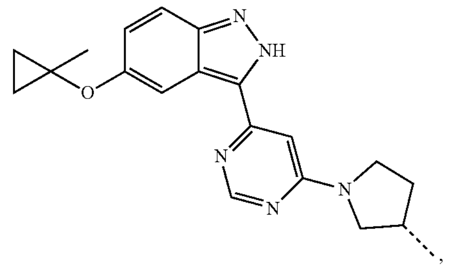
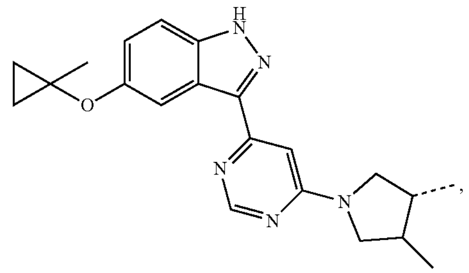
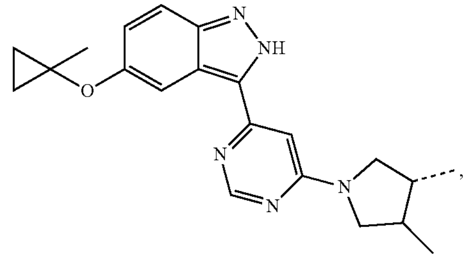

-continued
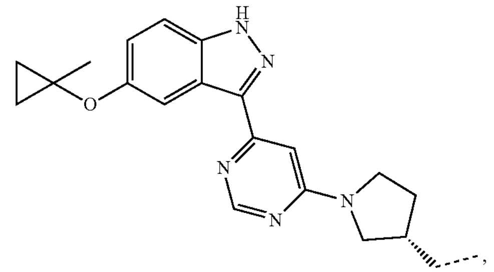
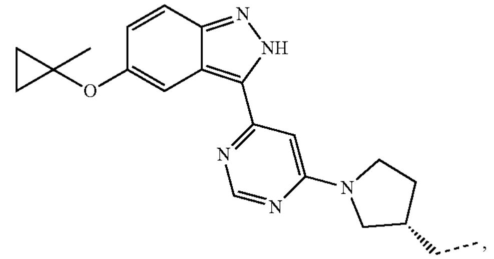
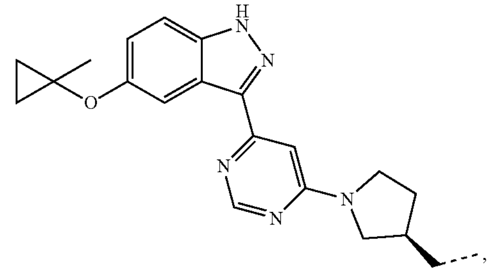
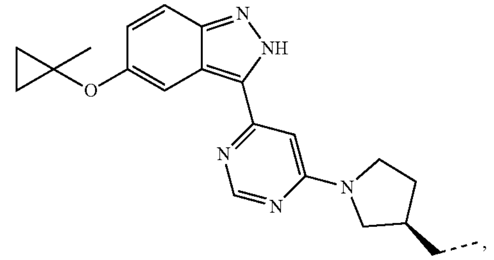
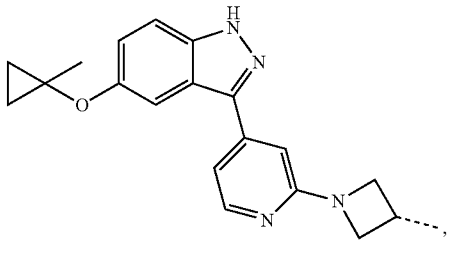
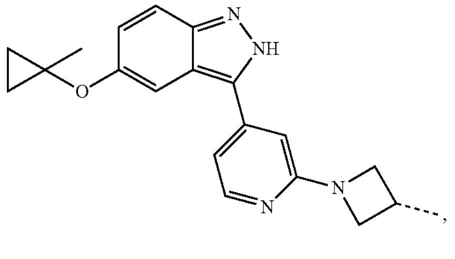
-continued
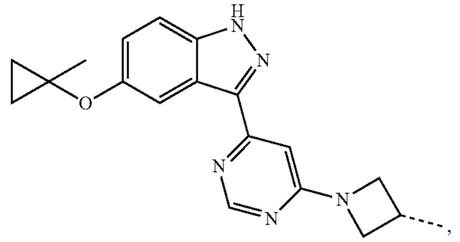
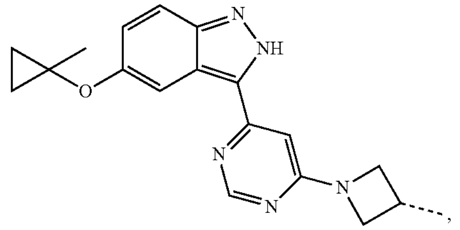
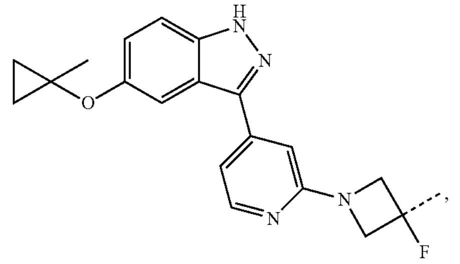
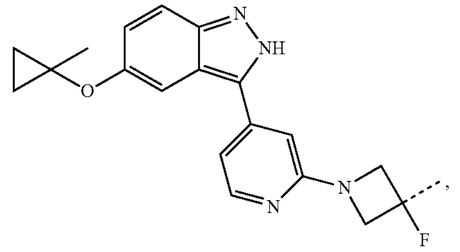
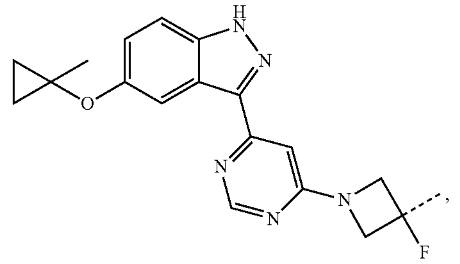
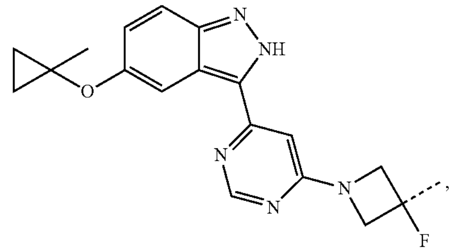

-continued
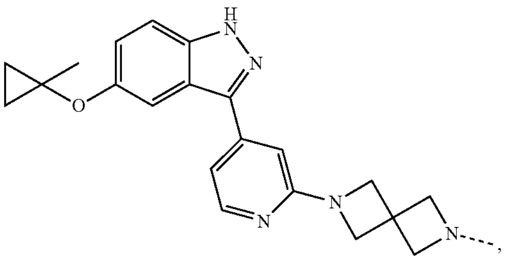
,
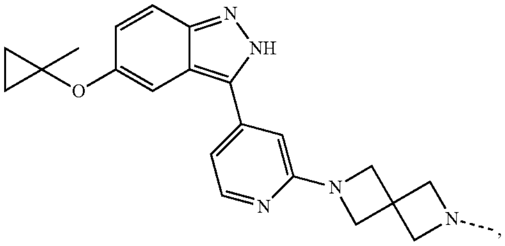
,
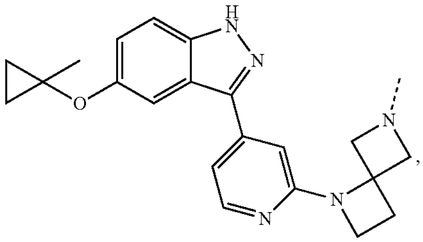
,
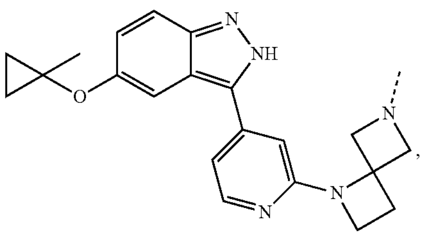
,
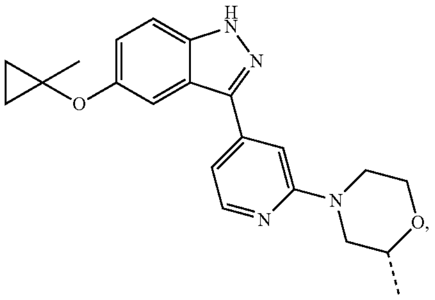
,
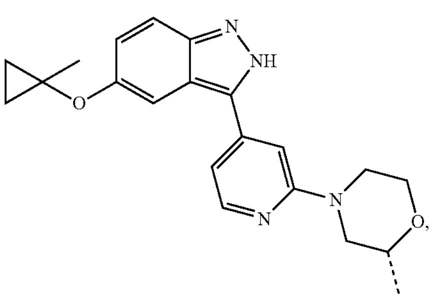
,
-continued
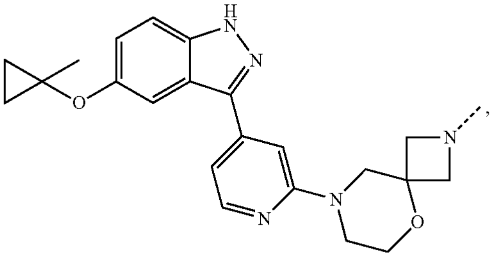
,
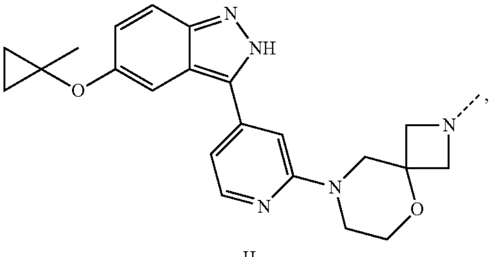
,
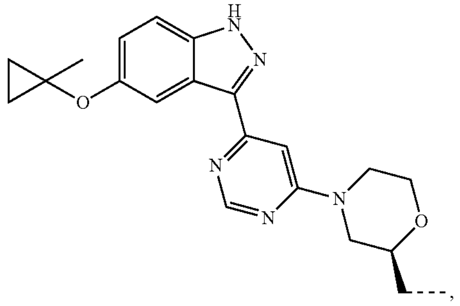
,
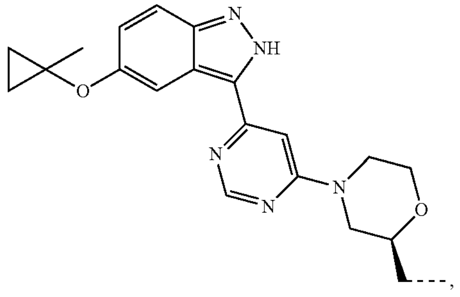
,
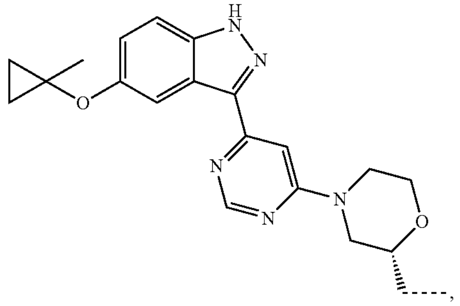
,
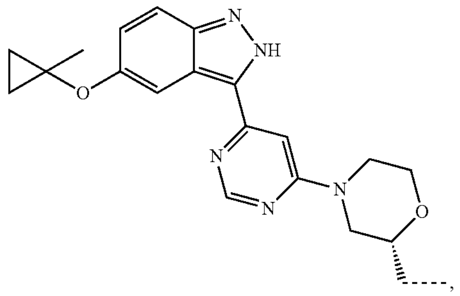
, -continued
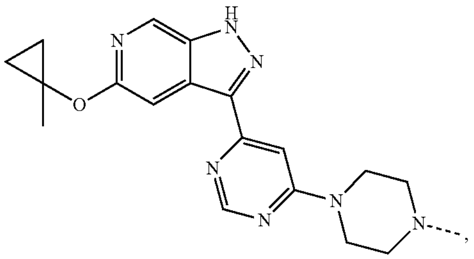
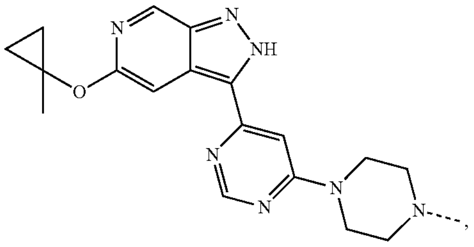
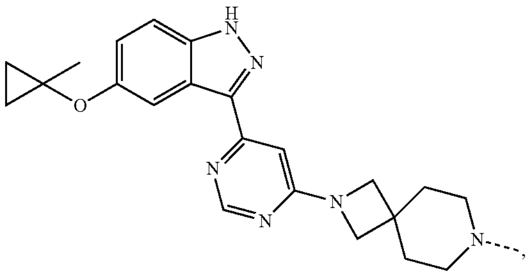
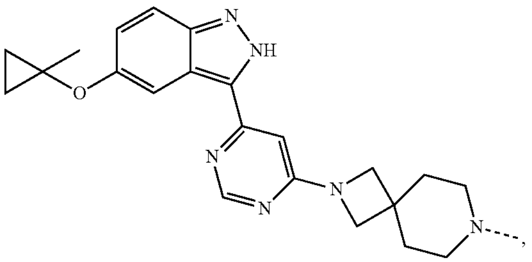
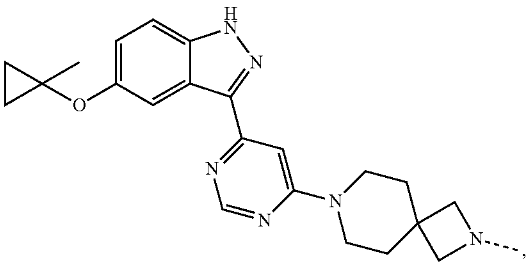
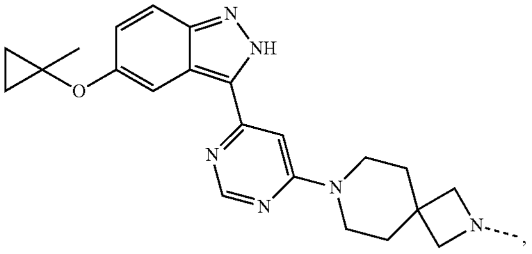
-continued
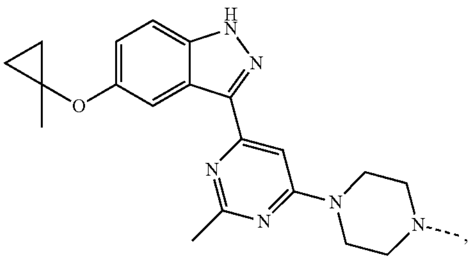
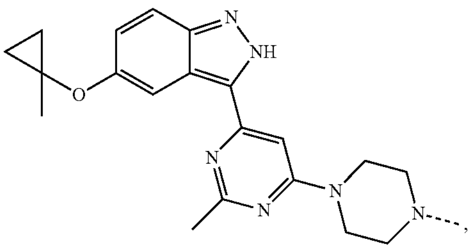
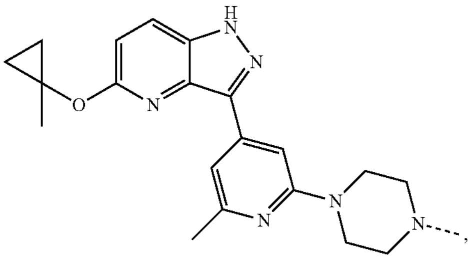
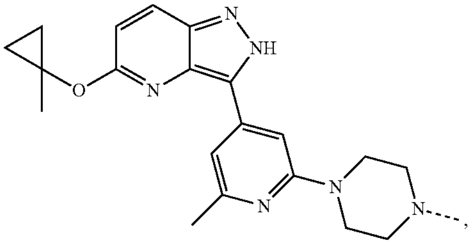
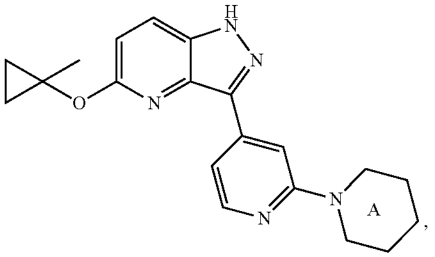
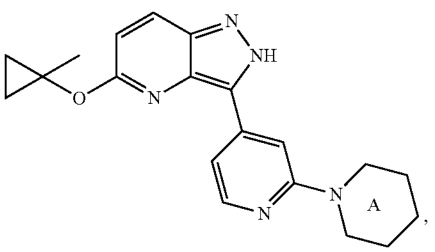

-continued

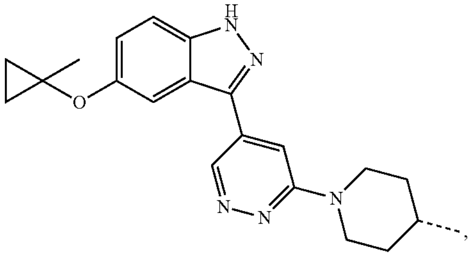

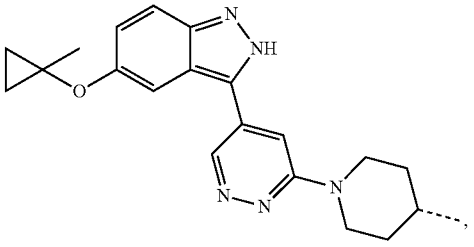

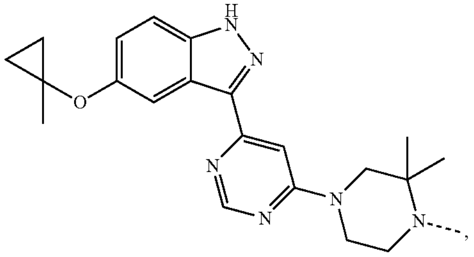

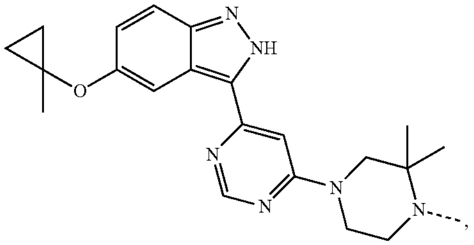

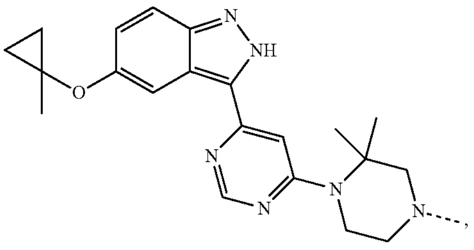

or

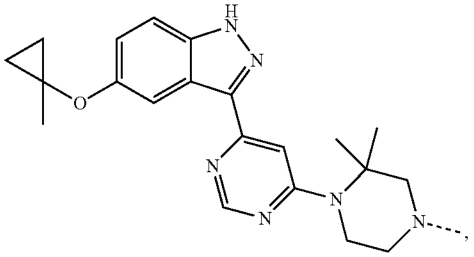

wherein the indicates the point of attachment with a L or a ULM.

In any aspect or embodiment described herein, the PTM is represented by:

(PTM-IIIB1)

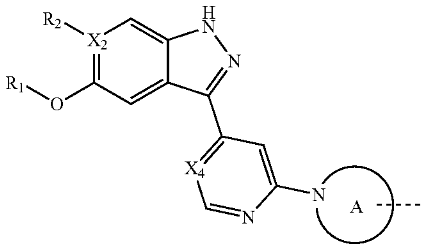

or (PTM-IIIB2)

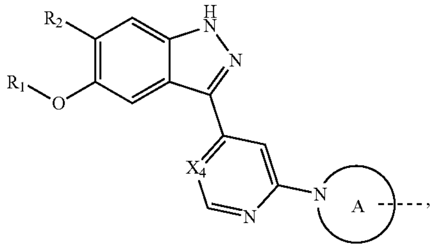

wherein of the PTM indicates the point of attachment with the L.

In any aspect or embodiment described herein, the PTM is represented by:

(PTM-IIIB3)

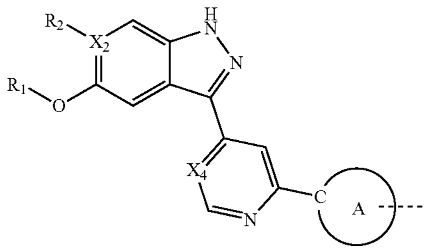

or (PTM-IIIB4)

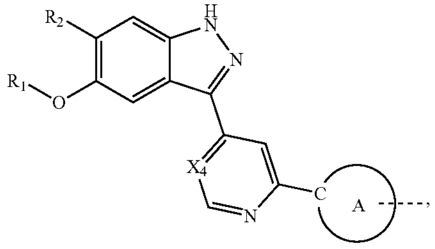

wherein of the PTM indicates the point of attachment with the L.

In any aspect or embodiment described herein, the PTM is represented by:

(PTM-IIIB1)

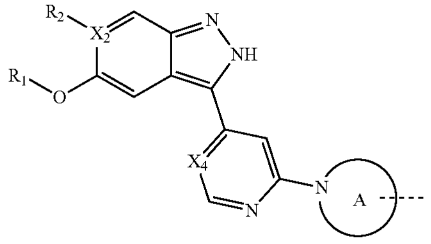

or (PTM-IIIB2)

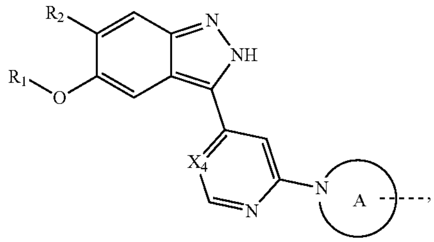

wherein ⸝⸍ of the PTM indicates the point of attachment with the L.

In any aspect or embodiment described herein, the PTM is represented by:

(PTM-IIIB3)

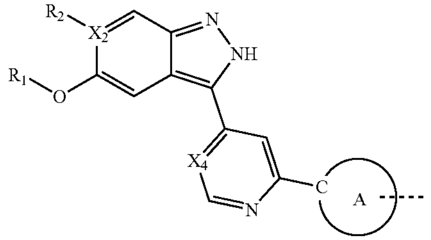

or (PTM-IIIB4)

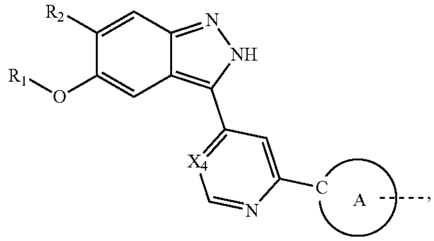

wherein ⸝⸍ of the PTM indicates the point of attachment with the L.

In any aspect or embodiment described herein, one or more of:

(a)

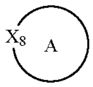

or

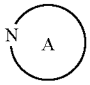

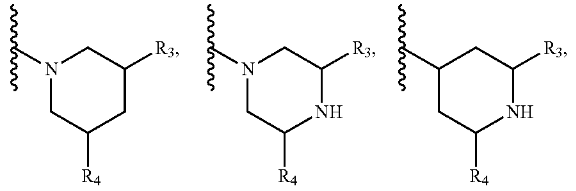

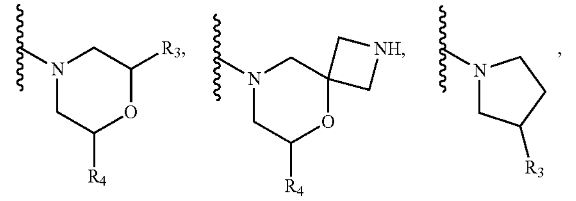

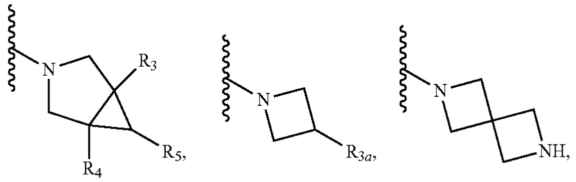

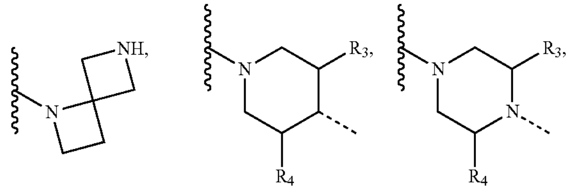

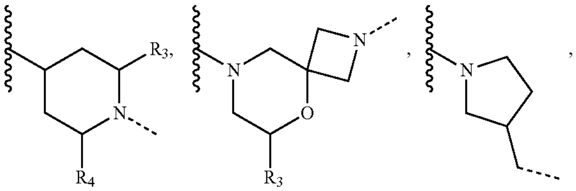

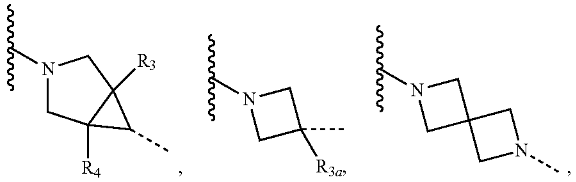

, or

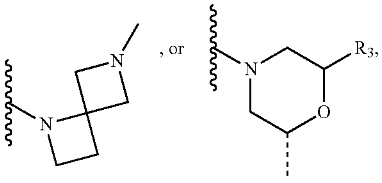

wherein:

$R_3$ is H or methyl;

$R_{3a}$ is H, halogen, or methyl;

$R_4$ is H or methyl;

$R_5$ is H or methyl;

⌇— indicates the point of attachment to the PTM; and ⸝⸍ indicates the point of attachment with the L, and where ⸝⸍ is not present, the

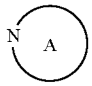

or

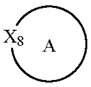

is attached to the L via an atom of a N or CH of the cyclic group, $R_3$, $R_4$, or $R_5$;

(b) $R_2$ is H or F; or (c) a combination thereof.

In any aspect or embodiment described herein,

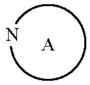

is selected from the group consisting of

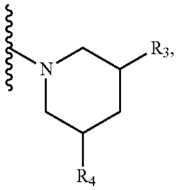 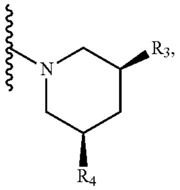

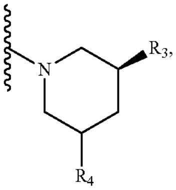 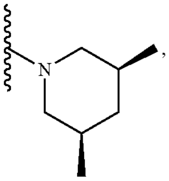 , 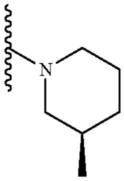 ,

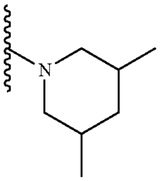 , 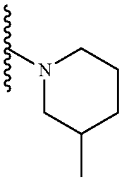 , 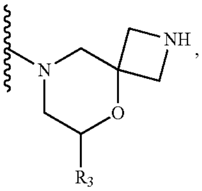

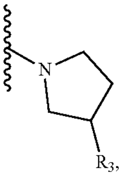 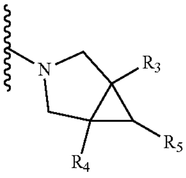 , 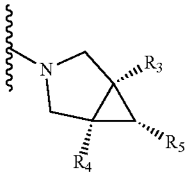 ,

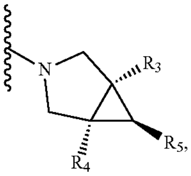 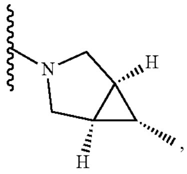

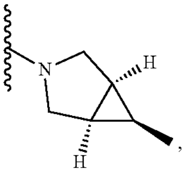 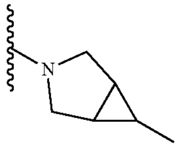

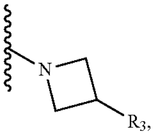 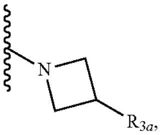 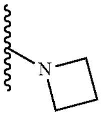 ,

-continued

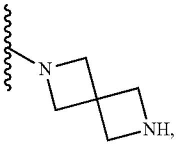 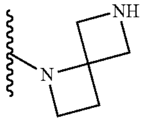 , 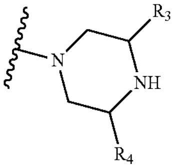 ,

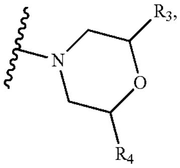 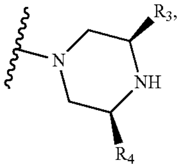

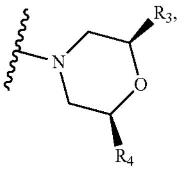 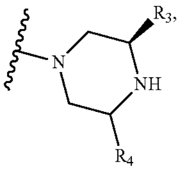

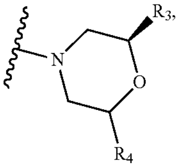 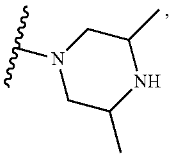 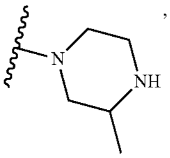 ,

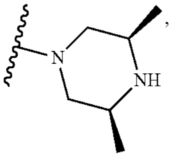 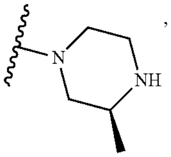 , 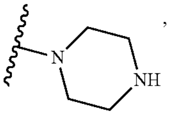 ,

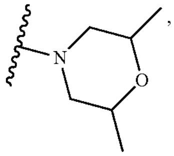 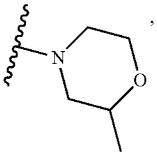 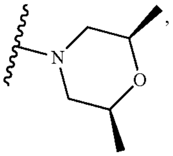

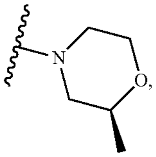 and 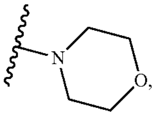

wherein the heterocycloalkyl is attached to the L or the PTM via an atom of the cyclic group or a substituent thereof.

In any aspect or embodiment described herein, the PTM is represented by chemical structure:

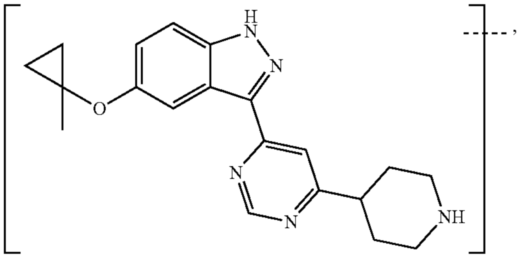

-continued
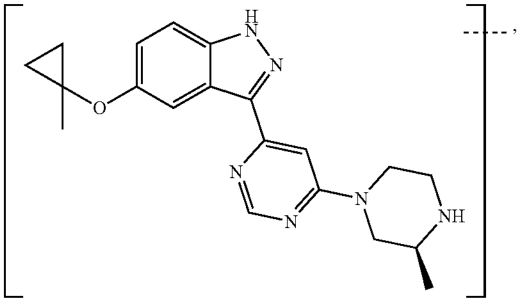
,
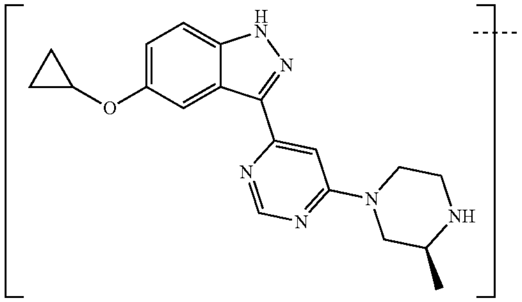
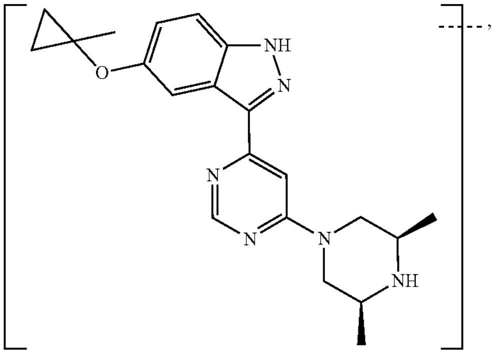
,
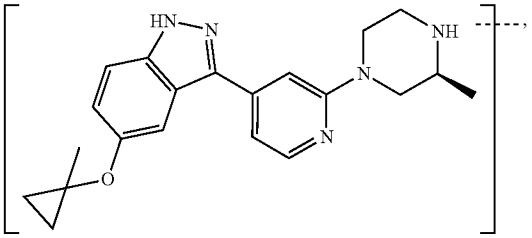
,
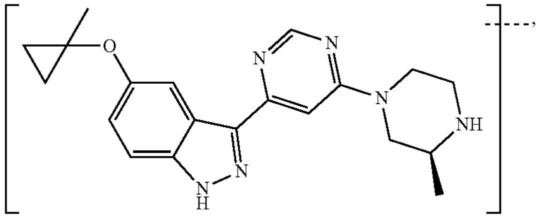
,
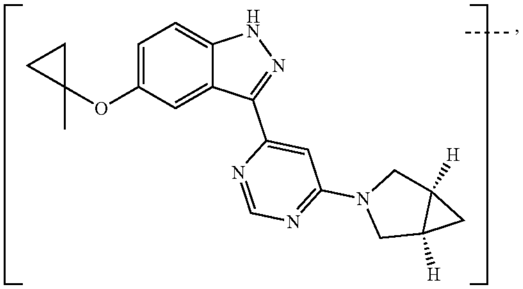
,
-continued
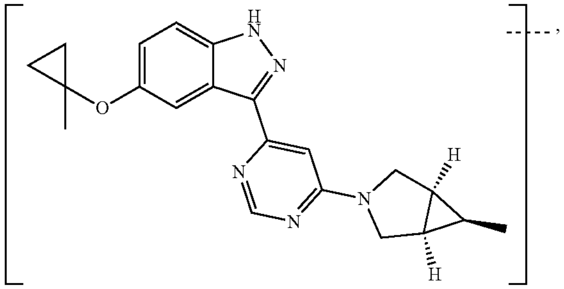
,
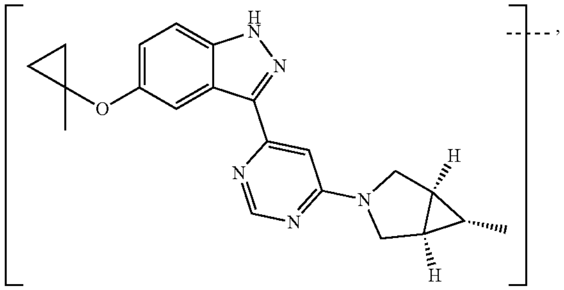
,
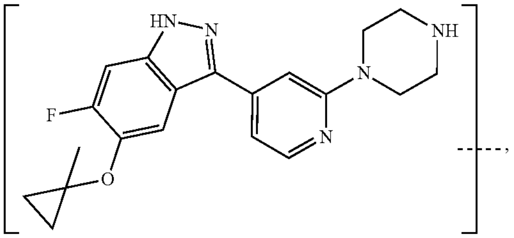
,
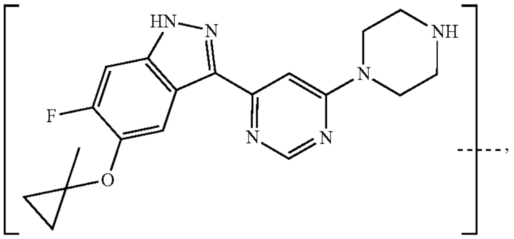
,
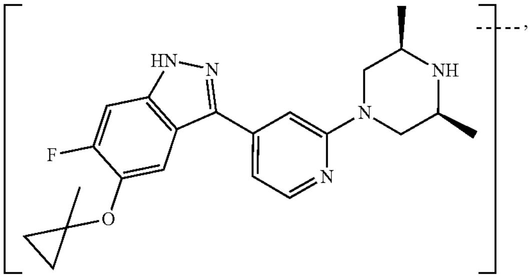
,
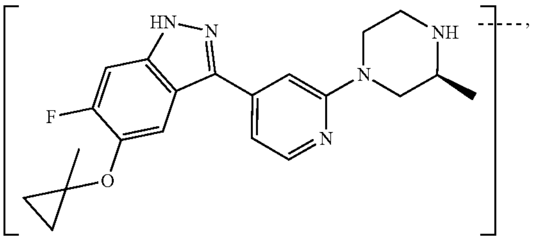
, -continued
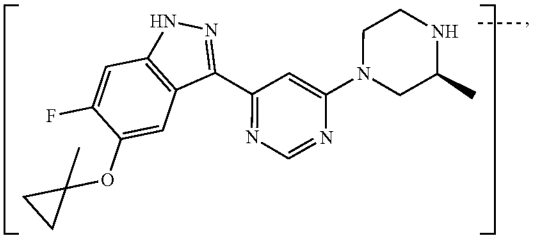
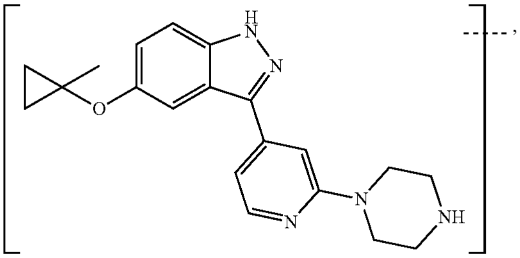
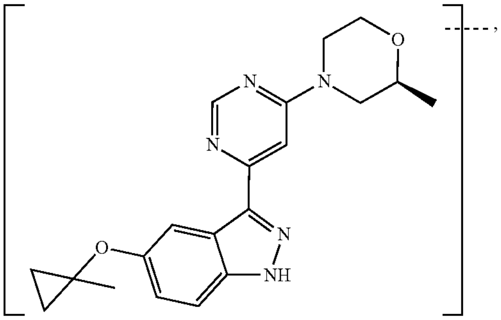
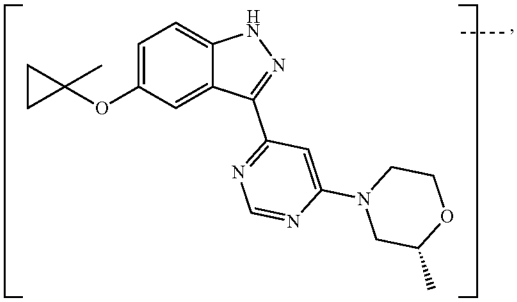
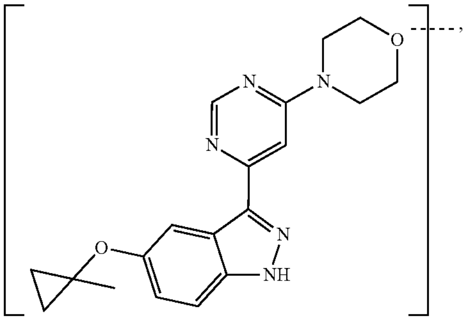
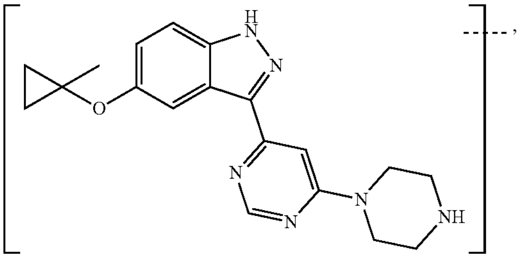
-continued
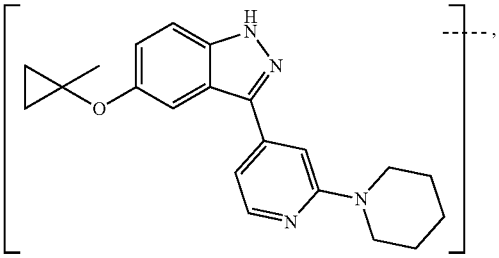
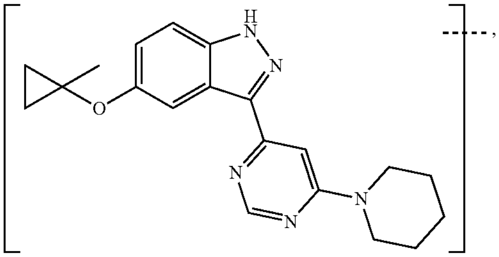
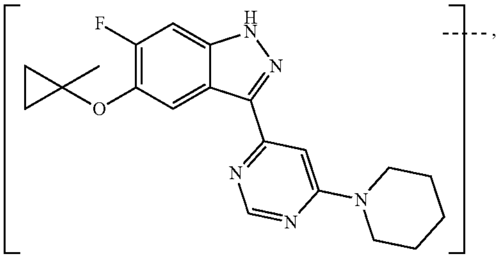
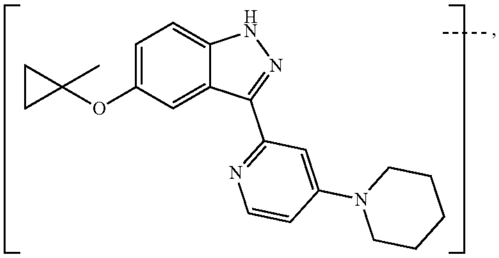
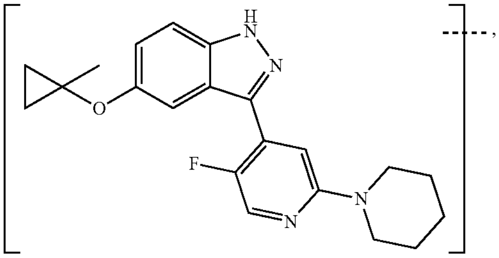
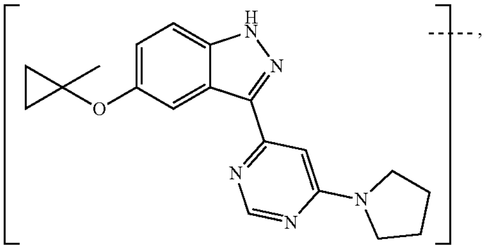

-continued
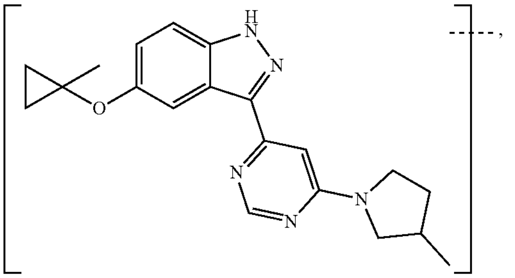
,
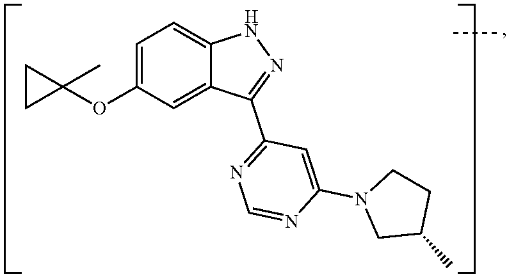
,
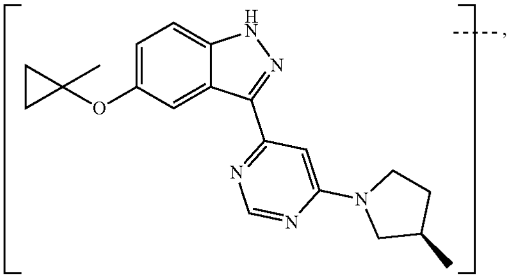
,
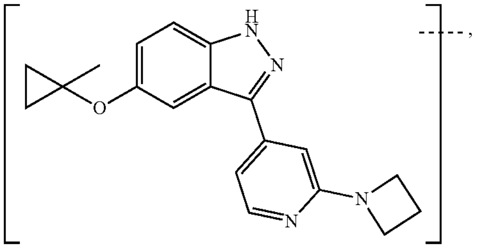
,
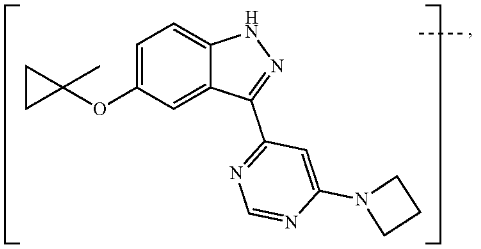
,
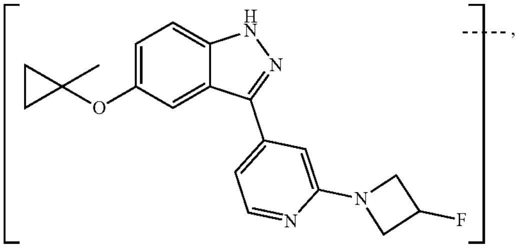
,
-continued
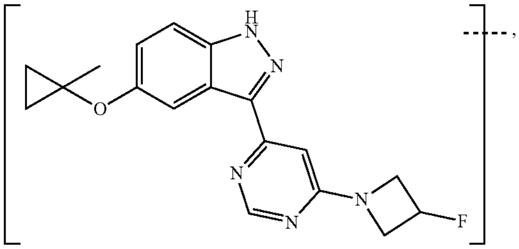
,
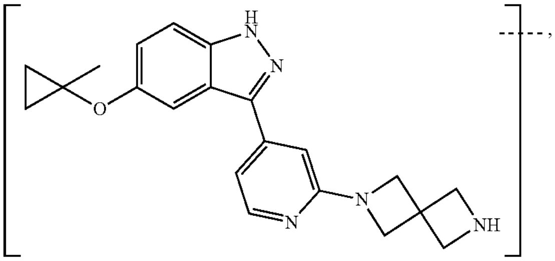
,
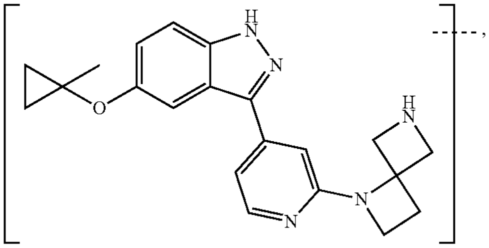
,
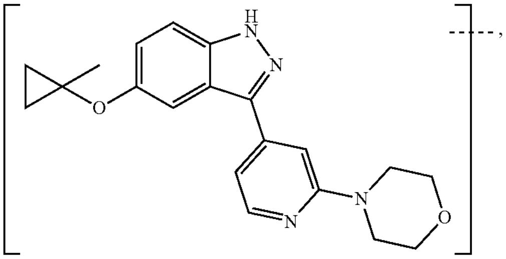
,
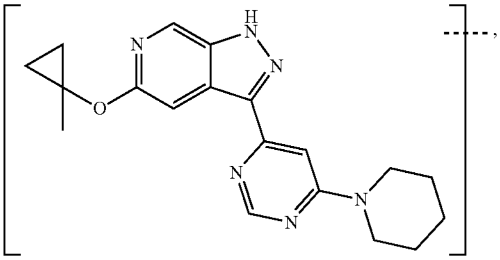
, or
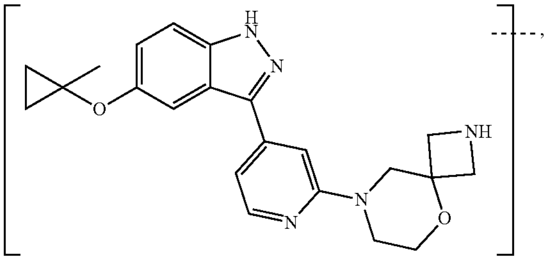
,
wherein indicates a site of attachment of the L or the CLM.

In any aspect or embodiment described herein, the PTM has the chemical structure:

(PTM-IA1)

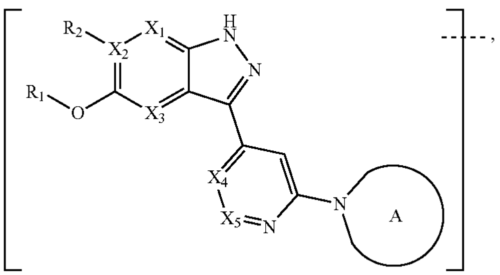

(PTM-IA2)

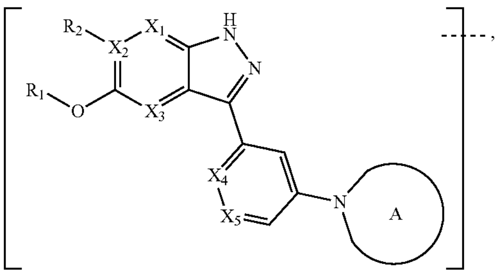

(PTM-IA1)

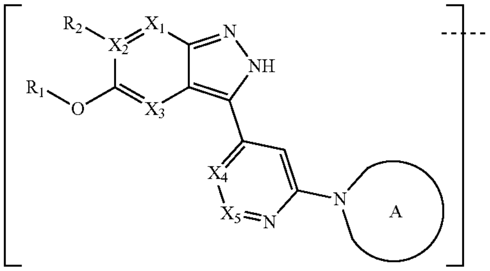

or (PTM-IA2)

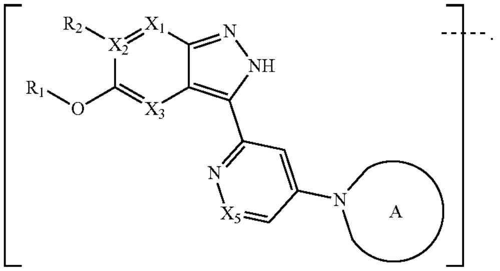

In any aspect or embodiment described herein, one or more of:

(a)

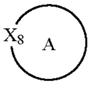 or 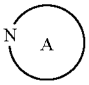

is

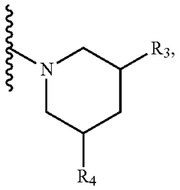 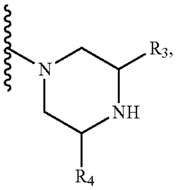 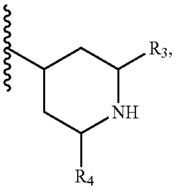

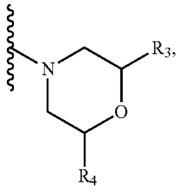 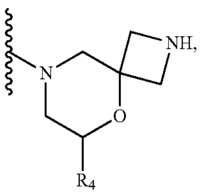 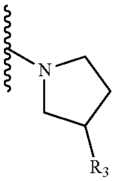 ,

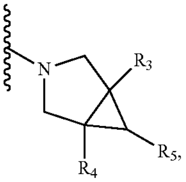 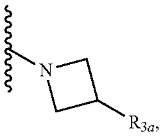 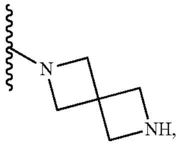

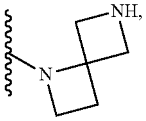 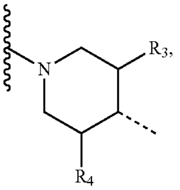 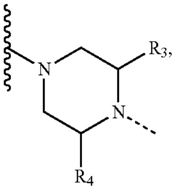

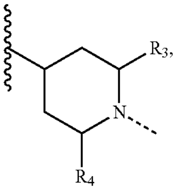 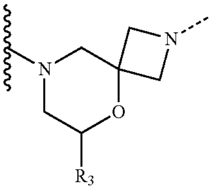 , 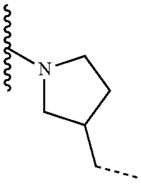 ,

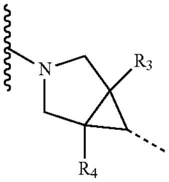 , 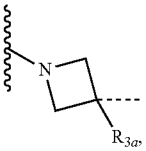 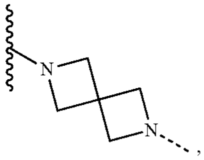

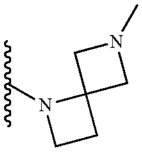 , or 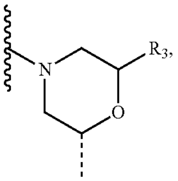

wherein:

$R_3$ is H or methyl;

$R_{3a}$ is H, halogen, or methyl;

$R_4$ is H or methyl;

$R_5$ is H or methyl;

⌇— indicates the point of attachment to the PTM; and ⸝⸝ indicates the point of attachment with the L, and where ⸝⸝ is not present, the

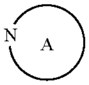 or 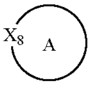

is attached to the L via an atom of a N or CH of the cyclic group, $R_3$, $R_4$, or $R_5$;

(b) $R_2$ is H or F; or (c) a combination thereof.

In any aspect or embodiment described herein,

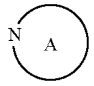

is selected from the group consisting

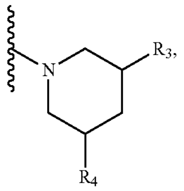 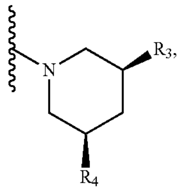

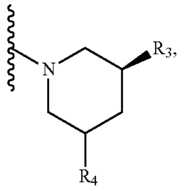 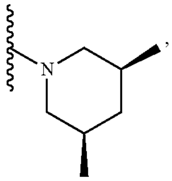, 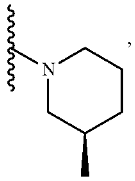,

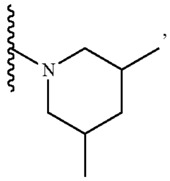, 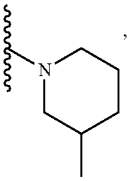, 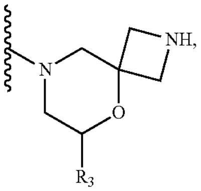

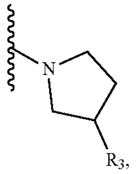 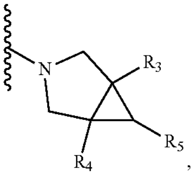,

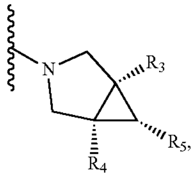 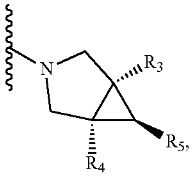

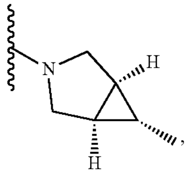 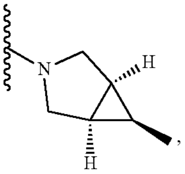

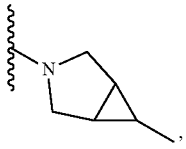 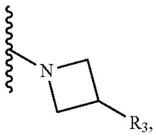 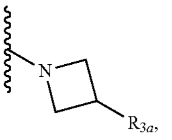

-continued

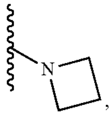 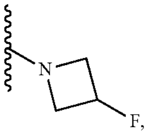 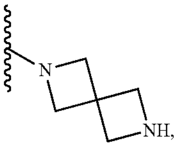

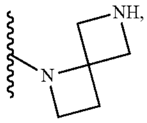 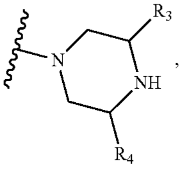, 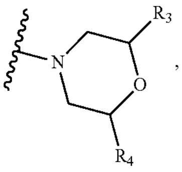,

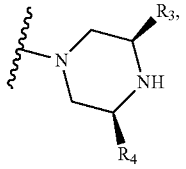 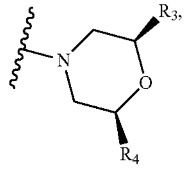

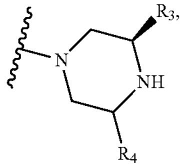 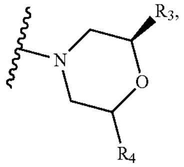

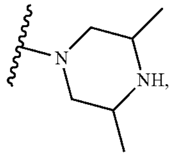 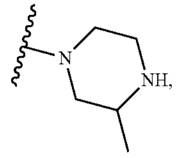

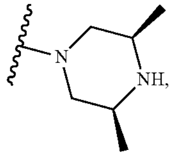 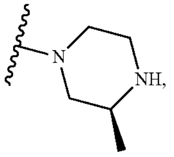

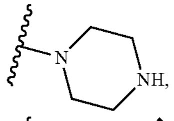 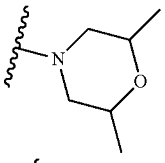, 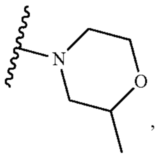,

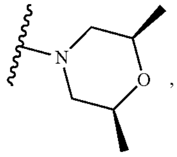, 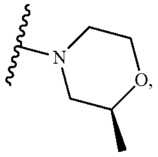 and

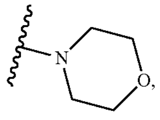

wherein the heterocycloalkyl is attached to the L or the PTM via an atom of the cyclic group or a substituent thereof.

In any aspect or embodiment described herein, one or more of:

(a)

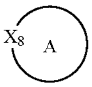 or 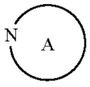

is

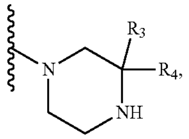

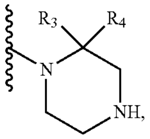

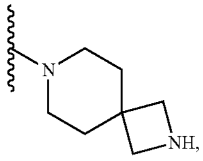

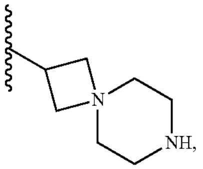

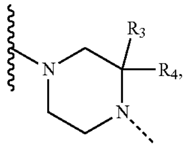

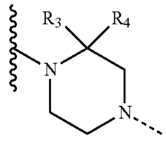
,

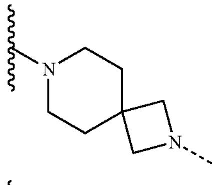
, or

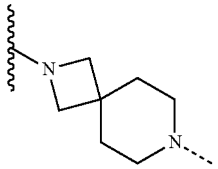
, wherein:

$R_3$ is H or methyl;

$R_{3a}$ is H, halogen, or methyl;

$R_4$ is H or methyl;

$R_5$ is H or methyl;

— indicates the point of attachment to the PTM; and indicates the point of attachment with the L, and where is not present, the

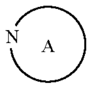
or
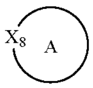

is attached to the L via an atom of a N or CH of the cyclic group, $R_3$, or $R_4$;

(b) $R_2$ is H or F; or (c) a combination thereof.

In any aspect or embodiment described herein,

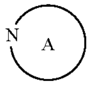

is selected from the group consisting of

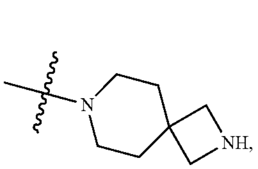

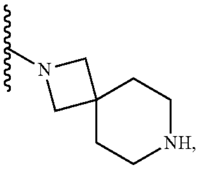

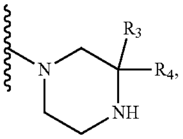

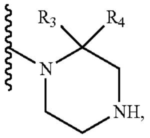

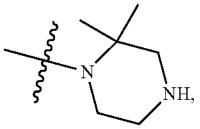
and
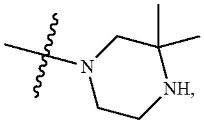

wherein the heterocycloalkyl is attached to the L or the PTM via an atom of the cyclic group or a substituent thereof.

In any aspect or embodiment described herein, the PTM is represented by chemical structure:

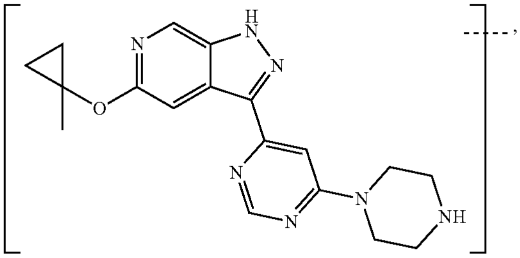

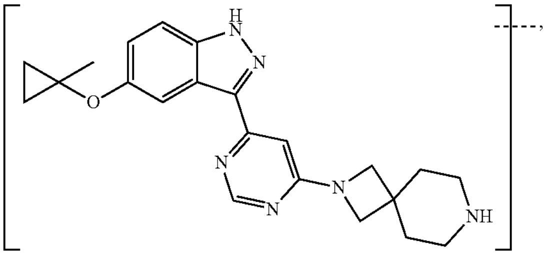

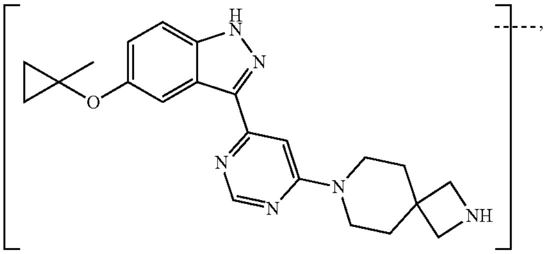

-continued

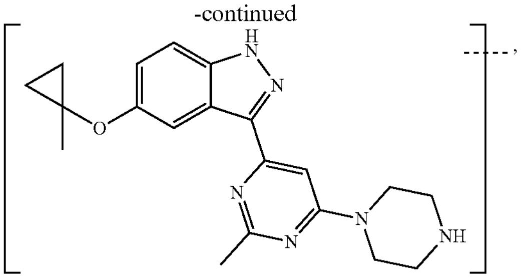

,

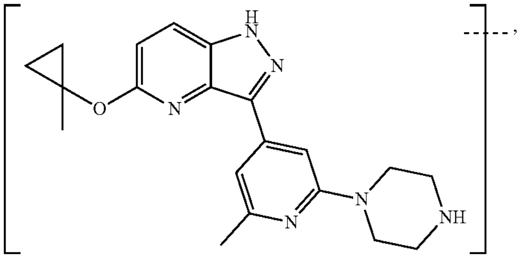

,

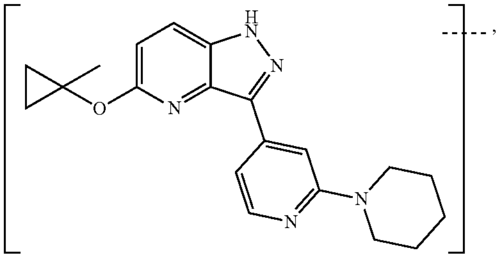

,

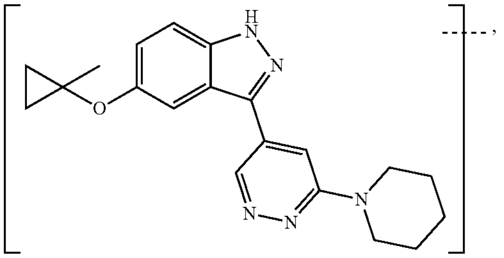

,

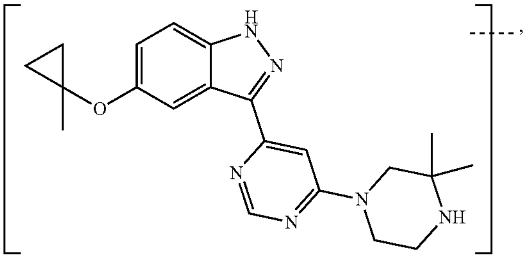

, or

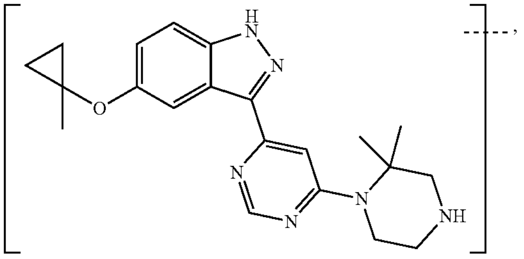

, wherein  indicates a site of attachment of the L or the CLM.

Therapeutic Compositions

The present invention further provides pharmaceutical compositions comprising therapeutically effective amounts of at least one bifunctional compound as described herein, in combination with a pharmaceutically acceptable carrier, additive or excipient.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions effect targeted protein degradation in a patient or subject, for example, an animal such as a human, and can be used for treating or ameliorating disease states or conditions which are modulated by degrading the target protein. In certain embodiments, the therapeutic compositions as described herein may be used to effectuate the degradation of protein for the treatment or amelioration of LRRK2-mediated inflammatory diseases, autoimmune diseases or cancer. In certain additional embodiments, the disease is idiopathic PD, LRRK2 mutation-associated PD (e.g., PD associated with one or more LRRK2 activating mutations), primary tauopathies (e.g., supranuclear palsy (PSP) or corticobasal degeneration (CBD)), lewy body dementia, Crohn's Disease, Leprosy (e.g., Leprosy with type 1 inflammatory reactions), and/or neuroinflammation.

In alternative aspects, the present disclosure relates to a method for treating a disease state or ameliorating one or more symptoms of a disease or condition in a subject in need thereof by degrading the LRRK2 protein (e.g., a wildtype LRRK2 protein or an LRRK2 mutant protein (e.g., a LRRK2 mutant protein including one or more mutation selected from G2019S, I2020T, N1437H, R1441G/C/H, and Y1699C) comprising administering to said patient or subject an effective amount, e.g., a therapeutically effective amount, of at least one compound as described herein, optionally in combination with a pharmaceutically acceptable carrier, additive or excipient, and optionally coadministered with an additional bioactive agent, wherein the composition is effective for treating or ameliorating the disease or disorder or one or more symptoms thereof in the subject. The method according to the present disclosure may be used to treat certain disease states, conditions or symptoms including inflammatory disease, autoimmune disease, or cancer, by virtue of the administration of effective amounts of at least one compound described herein. For example, the method according to the present disclosure may be used to treat one or more of Parkinson's Disease (PD), idiopathic PD, LRRK2 mutation associated PD (e.g., PD associated with one or more LRRK2 activating mutations), primary tauopathies (e.g., supranuclear palsy (PSP) or corticobasal degeneration (CBD)), lewy body dementia, Crohn's Disease, Leprosy (e.g., Leprosy with type 1 inflammatory reactions), and neuroinflammation (such as is observed in Alzheimer's disease, PD, multiple sclerosis, traumatic brain injury, spinal cord injury, etc.).

The present disclosure further includes pharmaceutical compositions comprising a pharmaceutically acceptable salt, in particular, acid or base addition salts of the compounds as described herein. The acids which are used to prepare the pharmaceutically acceptable acid addition salts of the aforementioned compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds according to the present disclosure. The chemical bases that may be used as reagents to prepare pharmaceutically acceptable base salts of the present compounds are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual, intranasal, intraocular, intrathecal, vaginal, and suppository administration, among other routes of administration. The term "parenteral" as used herein includes subcutaneous, intravenous, intramuscular, intra-articular, intra-synovial, intrasternal, intrathecal, intrahepatic, intralesional and intracranial injection or infusion techniques. Enteric coated oral tablets may also be used to enhance bioavailability of the compounds from an oral route of administration. The most effective dosage form will depend upon the pharmacokinetics of the particular agent chosen as well as the type, location and severity of disease, condition or symptom, and the health of the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form or in depot formulation may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch, among others known in the art. For oral administration in a capsule form, useful diluents include lactose and corn starch. When aqueous suspensions are required for oral use, the active ingredient may be combined with emulsifying and suspending agents. If desired, certain sweetening, flavoring or coloring agents may also be added. Lubricating agents, such as magnesium stearate, are also typically added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. For topical applications, the pharmaceutical composition can be formulated in a transdermal patch, which can either be a reservoir patch or a matrix patch comprising the active compound combined with one or more carriers, buffers, absorption enhancers, and providing from 1 day to two weeks of continuous administration.

Alternatively, the pharmaceutical compositions of the present disclosure may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water.

Alternatively, the pharmaceutical compositions of the present disclosure can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Alternatively, the pharmaceutical compositions of the present disclosure can be formulated for ophthalmic use. For example, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active pharmaceutical ingredient in a pharmaceutical composition as described herein that may be combined with the carrier materials to produce a single dosage form will vary depending upon the condition of the subject and disease, condition or symptom treated, the particular mode of administration, and the condition of the subject. Preferably, the compositions should be formulated to contain between about 0.05 milligram and about 750 milligrams or more, more preferably about 1 milligram to about 600 milligrams, and even more preferably about 10 milligrams to about 500 milligrams of active ingredient, alone or in combination with another compound according to the present disclosure.

It should also be understood that a specific dosage and treatment regimen for any particular patient will depend upon a variety of factors, including the activity and bioavailability of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure depending upon the pharmaceutically acceptable salt or solvate thereof, optionally in a pharmaceutically acceptable carrier or diluent, either alone, or in combination with another known therapeutic agent.

In certain aspects, the active compound is combined with the pharmaceutically acceptable carrier or diluent in an amount sufficient to deliver to a patient a therapeutically effective amount for the desired indication, without causing an undue degree of serious toxic effects in the patient treated. A preferred dose of the active compound for all of the herein-mentioned conditions is in the range from about 10 nanograms per kilograms (ng/kg) to 300 milligrams per kilograms (mg/kg), preferably 0.1 to 100 mg/kg per day, more generally 0.5 to about 25 mg per kilogram body weight of the recipient/patient per day. A typical topical dosage will range from 0.01-5% wt/wt in a suitable carrier.

In certain aspects, the compound is conveniently administered in any suitable unit dosage form, including but not limited to a dosage form containing less than 1 milligrams (mg), 1 mg to 3000 mg, or 5 mg to 500 mg of active ingredient per unit dosage form. An oral dosage of about 25 mg-250 mg is often convenient.

In certain aspects, the active ingredient is preferably administered to achieve peak plasma concentrations of the active compound of about 0.00001-30 millimole (mM), preferably about 0.1-30 micromole (μM). This may be achieved, for example, by the intravenous injection of a solution or formulation of the active ingredient, optionally in saline, or an aqueous medium or administered as a bolus of the active ingredient. Oral administration may also be appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, as described herein among others. In certain preferred aspects of the disclosure, one or more compounds according to the present disclosure are coadministered with another bioactive agent, such as an anti-cancer agent or a wound healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In any aspect or embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic methods comprising administration of an effective amount of a compound as described herein or salt form thereof, and a pharmaceutically acceptable carrier. The therapeutic methods are useful to effect protein degradation in a patient or subject in need thereof, for example, an animal such as a human, for treating or ameliorating a disease state, condition or related symptom that may be treated through targeted protein degradation.

The terms "treat", "treating", and "treatment", etc., as used herein, refer to any action providing a benefit to a patient for which the present compounds may be administered, including the treatment of any disease state, condition, or symptom which is related to the protein to which the present compounds bind. Disease states or conditions, including cancer, which may be treated using compounds according to the present disclosure are set forth hereinabove.

The description provides therapeutic methods for effectuating the degradation of proteins of interest for the treatment or amelioration of a disease, e.g., Parkinson's Disease (PD), primary tauopathies, lewy body dementia, Crohn's Disease, Leprosy, and/or neuroinflammation (such as is observed in. In any aspect or embodiment, the disease is idiopathic PD, LRRK2 mutation associated PD (e.g. PD associated with one or more LRRK2 activating mutations), PSP, CBD, Leprosy with type 1 inflammatory reactions, Alzheimer's disease, PD, multiple sclerosis, traumatic brain injury, and/or spinal cord injury. As such, in another aspect, the description provides a method of ubiquitinating/degrading a target protein in a cell. In certain embodiments, the method comprises administering a bifunctional compound of the invention. The control or reduction of specific protein levels in cells of a subject as afforded by the present disclosure provides treatment of a disease state, condition, or symptom. In any aspect or embodiment, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another aspect, the description provides a process for making a molecule that can cause degradation of LRRK2 in a cell, comprising the steps of: (i) providing a small molecule that binds to the LRRK2 or a mutated form thereof; (ii) providing an E3 ubiquitin ligase binding moiety (ULM), preferably a CLM such as thalidomide, pomalidomide, lenalidomide or an analog thereof; and (iii) covalently coupling the small molecule of step (i) to the ULM of step (ii) via a chemical linking group (L) to form a compound which binds to both a cereblon E3 ubiquitin ligase and LRRK2 protein and/or mutated form in the cell, such that the cereblon E3 ubiquitin ligase is in proximity to, and ubiquitinates the LRRK2 protein bound thereto, such that the ubiquitinated LRRK2 is then degraded.

In another aspect, the description provides a method for detecting whether a molecule can trigger degradation of a LRRK2 protein in a cell, the method comprising the steps of: (i) providing a molecule for which the ability to trigger degradation of LRRK2 protein in a cell is to be detected, said molecule comprising the structure: CLM-L-PTM, wherein CLM is a cereblon E3 ubiquitin ligase binding moiety capable of binding a cereblon E3 ubiquitin ligase in a cell, which CLM is thalidomide, pomalidomide, lenalidomide, or an analog thereof; PTM is a protein targeting moiety, which is a small molecule that binds to LRRK2 and/or mutated LRRK form thereof, said LRRK2 having at least one lysine residue available to be ubiquitinated by a cereblon E3 ubiquitin ligase bound to the CLM of the molecule; and L is a chemical linking group that covalently links the CLM to the PTM to form the molecule; (ii) incubating a LRRK2 protein-expressing cell in the presence of the molecule of step (i); and (iii) detecting whether the LRRK2 protein in the cell has been degraded.

In any of the aspects or embodiments described herein, the small molecule capable of binding LRRK2, is a small molecule that binds of LRRK2. In certain embodiments, the small molecule that binds the LRRK2 is as described herein.

In another aspect of said treatment, the present disclosure provides a method of treating a human patient in need of said treatment of a disease state, condition, or symptom causally related to LRRK2, and/or LRRK2 mutated form, expression, over-expression, mutation, aggregation, accumulation, misfolding or dysregulation where the degradation of the LRRK2 protein will produce a therapeutic effect in the patient, the method comprising administering to the patient an effective amount of a compound according to the present disclosure, optionally in combination with another bioactive agent.

In another aspect of said treatment, the present disclosure provides a method of treating a human patient in need of said treatment of a disease state, condition, or symptom causally related to alpha-synuclein expression, over-expression, mutation, aggregation, accumulation, misfolding or dysregulation where the degradation of the LRRK2 protein and/or mutated form thereof will produce a therapeutic effect in the patient, the method comprising administering to the patient an effective amount of a compound according to the present disclosure, optionally in combination with another bioactive agent.

In another aspect of said treatment, the present disclosure provides a method of treating a human patient in need of said treatment of a disease state, condition, or symptom causally related to alpha-synuclein expression, over-expression, mutation, aggregation, misfolding or dysregulation where the degradation of the LRRK2 protein and/or mutated form thereof will produce a therapeutic effect in the patient, the method comprising administering to the patient an effective amount of a compound according to the present disclosure, optionally in combination with another bioactive agent.

In another aspect of said treatment, the present disclosure provides a method of treating a human patient in need of said treatment of a disease state, condition, or symptom causally related to Tau expression, over-expression, mutation, aggregation, misfolding or dysregulation where the degradation of the LRRK2 protein and/or mutated form thereof will produce a therapeutic effect in the patient, the method comprising administering to the patient an effective amount of a compound according to the present disclosure, optionally in combination with another bioactive agent.

The disease state, condition, or symptom may be caused by a microbial agent or other exogenous agent such as a virus, bacteria, fungus, protozoa or other microbe, or may be a disease state, which is caused by expression, overexpression, mutation, misfolding, or dysregulation of the protein, which leads to a disease state, condition, or symptom.

In another aspect, the present disclosure provides a method of treating or ameliorating at least one symptom of a disease or condition in a subject, comprising the steps of: providing a subject identified as having a symptom of a disease or condition causally related to expression, overexpression, mutation, misfolding, or dysregulation of LRRK2 protein and/or mutated form thereof in the subject, and the symptom of the disease or condition is treated or ameliorated by degrading LRRK2 protein and/or mutated form thereof in cells of the subject; and administering to the subject therapeutically effective amount of a compound comprising a small molecule of the present invention such that the LRRK2 protein and/or mutated form thereof is degraded, thereby treating or ameliorating at least one symptom of a disease or condition in the subject.

The term "disease state or condition" is used to describe any disease state or condition wherein protein expression overexpression, mutation, misfolding, or dysregulation (e.g., the amount of protein expressed in a patient is elevated) occurs and where degradation of the LRRK2 protein and/or mutated form thereof to reduce or stabilize the level of LRRK2 protein (whether mutated or not) in a patient provides beneficial therapy or relief of symptoms to a patient in need thereof. In certain instances, the disease state, condition, or symptom may be cured.

Disease state, condition, or symptom which may be treated using compounds according to the present disclosure include, for example, Parkinson's Disease (PD), idiopathic PD, LRRK2 mutation associated PD (e.g, PD associated with one or more LRRK2 activating mutations), primary tauopathies (e.g., supranuclear palsy (PSP) or corticobasal degeneration (CBD)), lewy body dementia, Crohn's Disease, Leprosy (e.g., Leprosy with type 1 inflammatory reactions), and/or neuroinflammation (such as is observed in Alzheimer's disease, PD, multiple sclerosis, traumatic brain injury, spinal cord injury, etc.).

The term "bioactive agent" is used to describe an agent, other than a compound according to the present disclosure, which is used in combination with a present compound as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-autoimmune disease agent" is used to describe an anti-autoimmune disease therapeutic agent, which may be combined with a compound according to the present disclosure to treat autoimmune disease. These agents include, for example, infliximab, tofacitinib, baricitinib, secukinumab, adalimumab, etanercept, golimumab, certolizumab pepol, anti-proliferative drugs (for example, mycophenolate mofetil) and corticosteroids.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

Abbreviations

ACN Acetonitrile
AcOH Acetic acid
Boc tert-butoxycarbonyl
dba Dibenzylideneacetone
DBU 1,8-Diazabicyclo[5.4.0]undec-7-ene
DCM Dichloromethane
DMA Dimethylacetamide
DME Dimethoxyethane
DMF Dimethylformamide
DMSO Dimethyl Sulfoxide
DMAC/DMA Dimethylacetamide
DIEA N. N-Diisopropylethylanine
EDTA Ethylenedianinetetraacetic acid
EtOAc/EA Ethyl Acetate
EtOH Ethanol
FA Formic Acid
HPLC High pressure liquid chromatography
Hz Hertz
IBX 2-Iodoxybenzoic acid
LAH Lithium aluminium hydride
LCMS Liquid Chromatography/Mass Spectrometry
LiHMDS Lithium bis(trimethylsilyl)amide
MHz Megahertz
NBS N-Bromosuccinimide
NCS N-Chlorosuccinimide
NMR Nuclear Magnetic Resonance
NMP N-Methyl-2-pyrrolidone
MeOH Methanol
MPLC Medium pressure liquid chromatography
MTBE Methyl tert-butyl ether PE Petroleum ether
Psi Pound-force per square inch
RT or r.t. Room temperature
SFC Supercritical fluid chromatography
TEA Triethylamine
THF Tetrahydrofuran
TFA Trifluoracetic acid
TLC Thin layer chromatography
TMS Trimethylsilyl
* number of repetitions General Synthetic Approach The synthetic realization and optimization of the bifunctional molecules as described herein may be approached in a stepwise or modular fashion. For example, identification of compounds that bind to the target protein, i.e., LRRK2 can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the chemical linking group previously referred to herein. Where crystallographic or NMR structural data are available, these can be used to focus such a synthetic effort.

In a very analogous way one can identify and optimize ligands for an E3 Ligase.

With PTMs and ULMs (e.g. CLMs) in hand, one skilled in the art can use known synthetic methods for their combination with or without a chemical linking group(s). Chemical linking group(s) can be synthesized with a range of compositions, lengths and flexibility and functionalized such that the PTM and ULM groups can be attached sequentially to distal ends of the linker. Thus, a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Synthetic Procedures

General Synthetic Scheme

Scheme 1

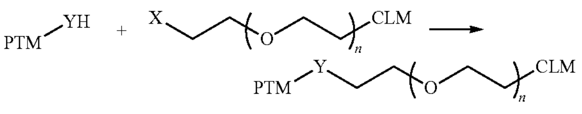

Scheme 2

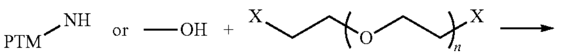

-continued

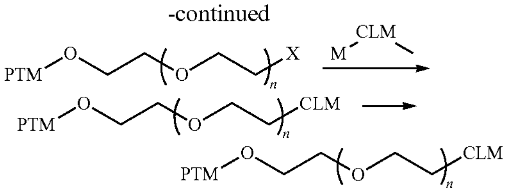

Scheme 3

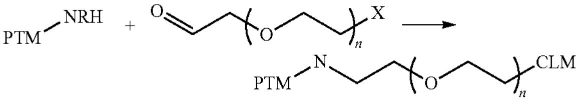

X represents a suitable leaving group (e.g. OTs, OMs, Cl, Br, etc.)

Y represents either a primary or secondary amine or alcohol

M represents a metalated version of the TLM ($Na^+$, $Cs^+$, $Li^+$, etc)

PG represents a suitable protecting group

Exemplary Synthesis of Intermediates 2-[[3-(6-chloropyrimidin-4-yl)-5-(1-methylcyclopropoxy)indazol-2-yl]methoxy]ethyl-trimethyl-silane and 5-(1-methylcyclopropoxy)-3-[6-[(3S)-3-methylpiperazin-1-yl]pyrimidin-4-yl]-1H-indazole

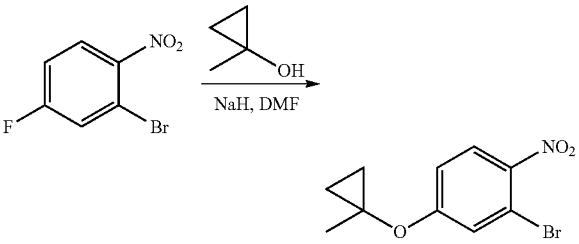

Step 1

To a solution of 2-bromo-4-fluoro-1-nitro-benzene (16.78 g, 76.28 mmol, 1.1 eq) and 1-methylcyclopropanol (5 g, 69.34 mmol, 1 eq) in DMF (160 mL) was added NaH (4.16 g, 104.01 mmol, 60% in mineral oil, 1.5 eq) in one portion at 0° C. under $N_2$. Then the mixture was heated to 20° C. and stirred for 4 hours. TLC showed there were new spots. The residue was poured into water (200 mL) and stirred for 10 min. The aqueous phase was extracted with ethyl acetate (3×300 mL). The combined organic phase was washed with brine (2×200 mL), dried with anhydrous $Na_2SO_4$, filtered and concentrated in vacuum. The residue was purified by silica gel column chromatography (100-200 mesh silica gel, 0-2% of Ethyl acetate in Petroleum ether) to afford 2-bromo-4-(1-methylcyclopropoxy)-1-nitro-benzene (14.3 g, 52.56 mmol, 75.79% yield) as a yellow oil.

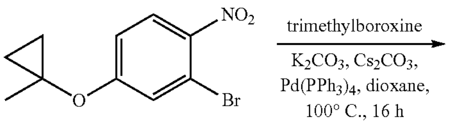

-continued

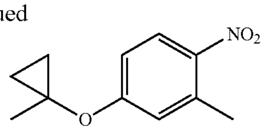

Step 2

To a mixture of 2-bromo-4-(1-methylcyclopropoxy)-1-nitro-benzene (14.3 g, 52.56 mmol, 1 eq), $K_2CO_3$ (14.53 g, 105.11 mmol, 2 eq) and $Cs_2CO_3$ (17.12 g, 52.56 mmol, 1 eq) in 1,4-dioxane (100 mL) was added 2,4,6-trimethyl-1,3,5,2,4,6-trioxatriborinane (32.99 g, 131.39 mmol, 36.73 mL, 50% purity in EtOAc, 2.5 eq) and $Pd(PPh_3)_4$ (6.07 g, 5.26 mmol, 0.1 eq)) at 20° C., then heated to 100° C. and stirred for 16 hours to give yellow solution. TLC showed the reaction was completed. The reaction was cooled to 20° C. and concentrated under vacuum. To this residue was added PE:EtOAc (10:1, 100 mL), and the mixture was filtered through a pad of silica. The filter pad was washed with petroleum ether:EtOAc (10:1, 1000 mL) solvent. The residue was purified by silica gel chromatography (100-200 mesh silica gel, 0-1% of Ethyl acetate in Petroleum ether) to afford 2-methyl-4-(1-methylcyclopropoxy)-1-nitro-benzene (11 g, crude) as a yellow oil.

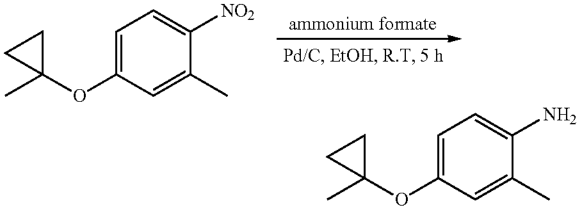

Step 3

To a mixture of 2-methyl-4-(1-methylcyclopropoxy)-1-nitro-benzene (11 g, 53.08 mmol, 1 eq) in EtOH (100 mL) was added 10% of Pd/C (4 g, 5.31 mmol, 0.1 eq) and ammonium formate (40.17 g, 636.99 mmol, 12 eq) in one portion at 20° C. under $N_2$. The mixture was stirred at 20° C. for 2 h to give a black mixture. TLC showed the reaction was completed. The mixture was filtered through a pad of silica gel, washed with EtOAc (3×200 mL) and concentrated in vacuum. The residue was purified by silica gel chromatography (0-10% of Ethyl acetate in Petroleum ether) to afford 2-methyl-4-(1-methylcyclopropoxy) aniline (9.8 g, crude) as a red oil.

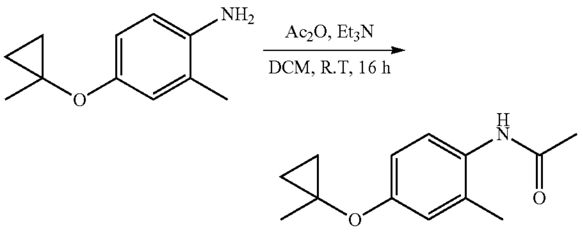

Step 4

To a mixture of 2-methyl-4-(1-methylcyclopropoxy) aniline (9.8 g, 55.29 mmol, 1 eq) and $Et_3N$ (13.99 g, 138.23 mmol, 19.24 mL, 2.5 eq) in DCM (100 mL) was added $Ac_2O$ (11.29 g, 110.58 mmol, 10.36 mL, 2 eq) in one portion at 0° C. under $N_2$. The mixture was stirred at 0° C. for 30 min, then heated to 20° C. and stirred for 16 hours. TLC showed the reaction was completed. The reaction was quenched with a saturated solution of aqueous $NaHCO_3$ (30 mL) to adjusted pH=7-8 and extracted with DCM (3×50 mL). The combined organic phase was washed with brine (3×50 mL), dried with anhydrous $Na_2SO_4$, filtered and concentrated in vacuum. The residue was purified by silica gel chromatography (20-40% Ethyl acetate in Petroleum ether) to afford N-[2-methyl-4-(1-methylcyclopropoxy) phenyl]acetamide (9.3 g, 42.41 mmol, 76.71% yield) as a yellow oil.

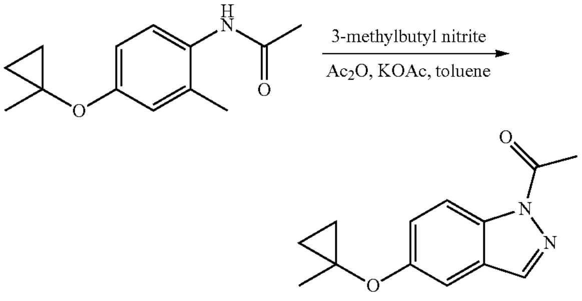

Step 5

To a solution of N-[2-methyl-4-(1-methylcyclopropoxy) phenyl]acetamide (9.3 g, 42.41 mmol, 1 eq) in toluene (100 mL) was added KOAc (6.24 g, 63.62 mmol, 1.5 eq) and $Ac_2O$ (19.92 g, 195.09 mmol, 18.27 mL, 4.6 eq) at 20° C., the solution was heated to 80° C., then 3-methylbutyl nitrite (19.87 g, 169.65 mmol, 22.84 mL, 4 eq) was added drop-wise. After addition, the mixture was stirred at 80° C. for 2 h. TLC showed the reaction was completed. The reaction was then filtered, the wet cake was washed with EtOAc (70 mL), and the filtrate was concentrated in vacuum. The residue was purified by silica gel chromatography (100-200 mesh silica gel, 0-10% Ethyl acetate in Petroleum ether) to afford 1-[5-(1-methylcyclopropoxy) indazol-1-yl] ethanone (8 g, crude) as a yellow solid.

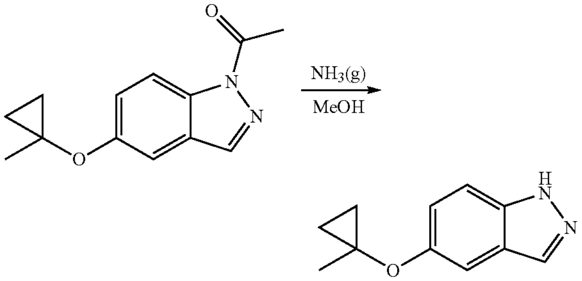

Step 6

To a mixture of 1-[5-(1-methylcyclopropoxy)indazol-1-yl]ethanone (8 g, 34.74 mmol, 1 eq) in MeOH (80 mL) was added $NH_3$ (g/)MeOH (7 M, 24.82 mL, 5 eq) in one portion at 20° C. The mixture was stirred at 20° C. for 2 hours to give a yellow solution. TLC showed the reaction was completed. The solution was concentrated in vacuum to afford 5-(1-methylcyclopropoxy)-1H-indazole (7.8 g, crude) as a yellow solid.

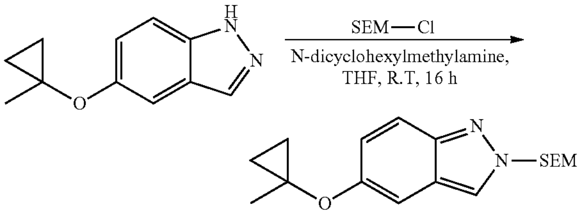

Step 7

To a mixture of 5-(1-methylcyclopropoxy)-1H-indazole (7.8 g, 41.44 mmol, 1 eq) in THF (80 mL) was added N-dicyclohexylmethylamine (10.52 g, 53.87 mmol, 1.3 eq) and SEM-Cl (8.29 g, 49.73 mmol, 8.80 mL, 1.2 eq) in one portion at 20° C. The mixture was stirred at 20° C. for 16 hours to give an orange solution. TLC showed the reaction was completed. The residue was poured into water (60 mL). The aqueous phase was extracted with ethyl acetate (3×50 mL). The combined organic phase was washed with brine (2×50 mL), dried with anhydrous $Na_2SO_4$, filtered and concentrated in vacuum. The residue was purified by silica gel chromatography (100-200 mesh silica gel, 0-10% of ethyl acetate in Petroleum ether) to afford trimethyl-[2-[[5-(1-methylcyclopropoxy) indazol-2-yl] methoxy] ethyl] silane (5.4 g, 16.96 mmol, 40.92% yield) as a yellow oil.

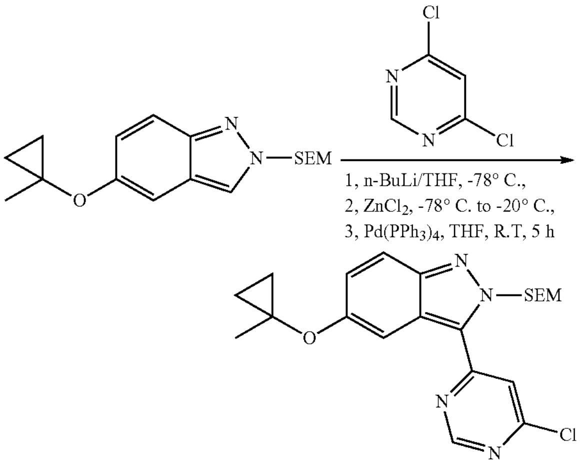

Step 8

To a mixture of trimethyl-[2-[[5-(1-methylcyclopropoxy) indazol-2-yl]methoxy]ethyl]silane (4.36 g, 13.70 mmol, 5.32 e-1 eq) in THF (6 mL) was dropwise added n-BuLi (2.5 M, 13.40 mL, 1.3 eq) dropwise at −70° C. under $N_2$. The mixture was then stirred at −20° C. for 1 h, and a solution of $ZnCl_2$ (0.7 M, 55.20 mL, 1.5 eq) was dropwise added at −70° C. The mixture was stirred for 1 h at −40° C. A mixture of 4, 6-dichloropyrimidine (4.22 g, 28.34 mmol, 1.1 eq) and $Pd(PPh_3)_4$ (1.49 g, 1.29 mmol, 0.05 eq) in THF (4 mL) was stirred at 20° C. for 1 h and was added to that solution. The cold bath was removed, and the mixture was stirred at 20° C. for 16 h to give a yellow solution. TLC showed there was starting material remained and at the same time some new spots were formed. The residue was poured into water (10 mL). The aqueous phase was extracted with ethyl acetate (3×20 mL). The combined organic phase was washed with brine (2×20 mL), dried with anhydrous $Na_2SO_4$, filtered and concentrated in vacuum. The residue was purified by silica gel chromatography (100-200 mesh silica gel, 0-10% of Ethyl acetate in Petroleum ether) to afford 2-[[3-(6-chloropyrimidin-4-yl)-5-(1-methylcyclopropoxy) indazol-2-yl] methoxy] ethyl-trimethyl-silane (2.9 g, crude) as a yellow oil.

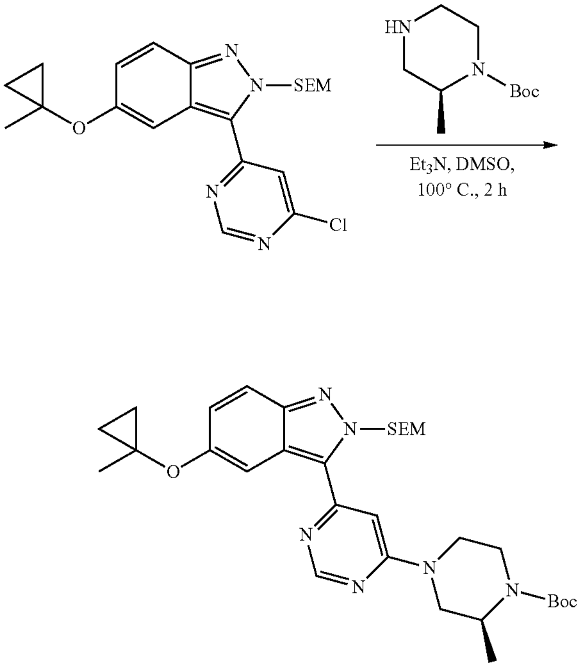

Step 9

To a mixture of 2-[[3-(6-chloropyrimidin-4-yl)-5-(1-methylcyclopropoxy) indazol-2-yl]methoxy]ethyl-trimethyl-silane (500 mg, 1.16 mmol, 1 eq) and tert-butyl (2S)-2-methylpiperazine-1-carboxylate (697.02 mg, 3.48 mmol, 3 eq) in DMSO (5 mL) was added $Et_3N$ (704.34 mg, 6.96 mmol, 968.82 μL, 6 eq) in one portion and then the mixture was stirred at 100° C. for 1 h. TLC showed the reaction was completed. The mixture was cooled to 20° C. The residue was poured into water (5 mL). The aqueous phase was extracted with ethyl acetate (3×5 mL). The combined organic phase was washed with brine (2×5 mL), dried with anhydrous $Na_2SO_4$, filtered and concentrated in vacuum to give tert-butyl (2S)-2-methyl-4-[6-[5-(1-methylcyclopropoxy)-2-(2-trimethylsilylethoxymethyl) indazol-3-yl] pyrimidin-4-yl] piperazine-1-carboxylate (802 mg, crude) as a yellow oil.

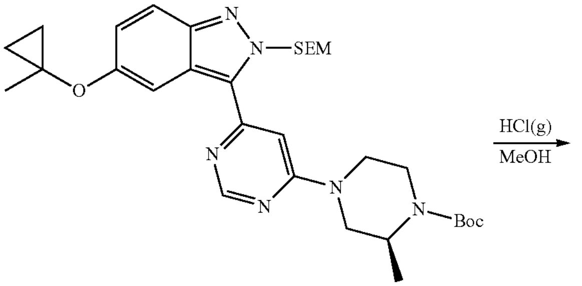

-continued

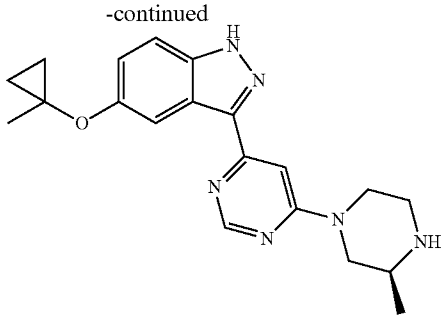

Step 10

To a mixture of tert-butyl (2S)-2-methyl-4-[6-[5-[(1-methylcyclopropyl)methyl]-2-(2-trimethylsilylethoxymethyl)indazol-3-yl]pyrimidin-4-yl]piperazine-1-carboxylate (802 mg, 1.35 mmol, 1 eq) in DCM (5 mL) was added TFA (771.25 mg, 6.76 mmol, 500.81 μL, 5 eq) in one portion at 25° C. The mixture was stirred at 25° C. for 16 hours. The HCl (4 M, 338.20 μL, 1 eq) in MeOH (5 mL) was added at 25° C., then heated to 60° C. and stirred for 0.5 hours. LCMS showed the reaction was completed. The mixture was cooled to 20° C. The residue was poured into $NaHCO_3$ (5 mL) to adjust pH=7-8. The aqueous phase was extracted with ethyl acetate (3×10 mL). The combined organic phase was washed with brine (2×10 mL), dried with anhydrous $Na_2SO_4$, filtered and concentrated in vacuum. The residue was purified by silica gel chromatography (0-40% of Ethyl acetate in MeOH) to give 5-(1-methylcyclopropoxy)-3-[6-[(3S)-3-methylpiperazin-1-yl]pyrimidin-4-yl]-1H-indazole (450 mg, 1.18 mmol, 87.41% yield, 95.77% purity) as a yellow solid.

Exemplary Synthesis of Intermediate 5-(1-methylcyclopropoxy)-3-(6-piperazin-1-ylpyrimidin-4-yl)-1H-indazole

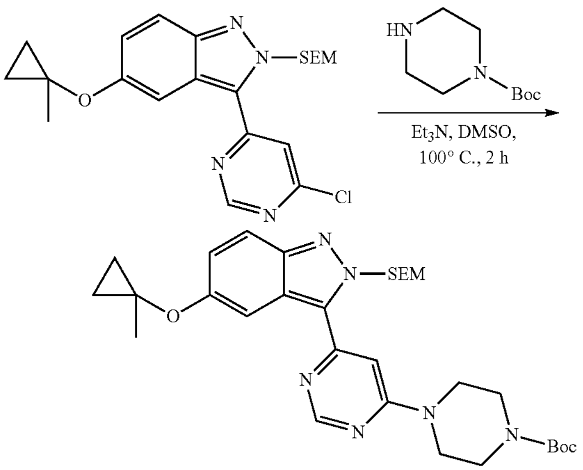

Step 1

To a solution of 2-[[3-(6-chloropyrimidin-4-yl)-5-(1-methylcyclopropoxy)indazol-2-yl] methoxy]ethyl-trimethyl-silane (500 mg, 1.16 mmol, 1 eq) and tert-butyl piperazine-1-carboxylate (648.20 mg, 3.48 mmol, 3 eq) in DMSO (5 mL) was added $Et_3N$ (704.34 mg, 6.96 mmol, 968.82 μL, 6 eq) in one portion and then the mixture was stirred at 100° C. for 1 h. TLC showed the reaction was completed. The mixture was cooled to 20° C. The residue was poured into water (5 mL). The aqueous phase was extracted with ethyl acetate (3×5 mL). The combined organic phase was washed with brine (2×5 mL), dried with anhydrous $Na_2SO_4$, filtered and concentrated in vacuum to give Tert-butyl 4-[6-[5-(1-methylcyclopropoxy)-2-(2-trimethylsilylethoxymethyl)indazol-3-yl]pyrimidin-4-yl] piperazine-1-carboxylate (812 mg, crude) as a yellow oil.

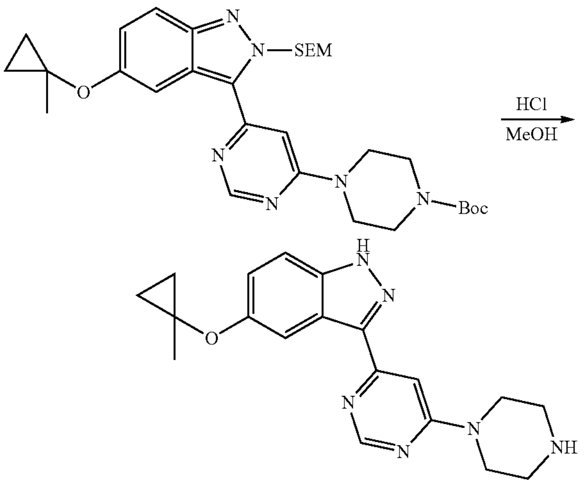

Step 2

To a mixture of tert-butyl 4-[6-[5-[(1-methylcyclopropyl)methyl]-2-(2-trimethylsilylethoxymethyl)indazol-3-yl]pyrimidin-4-yl]piperazine-1-carboxylate (812 mg, 1.40 mmol, 1 eq) in DCM (5 mL) was added TFA (799.77 mg, 7.01 mmol, 519.33 μL, 5 eq) in one portion at 25° C. and was stirred at 25° C. for 16 h. The HCl (g) (4 M, 5.26 mL, 15 eq) in MeOH (5 mL) was added at 25° C., then heated to 60° C. and stirred for 0.5 hours. The mixture was cooled to 20° C. LCMS showed the reaction was completed. The residue was poured into $NaHCO_3$ (5 mL) to adjust pH=7-8. The aqueous phase was extracted with ethyl acetate (3×10 mL). The combined organic phase was washed with brine (2×10 mL), dried with anhydrous $Na_2SO_4$, filtered and concentrated in vacuum. The residue was purified by silica gel chromatography (100-200 mesh silica gel, 0-40% of Ethyl acetate in MeOH) to give 5-(1-methylcyclopropoxy)-3-(6-piperazin-1-ylpyrimidin-4-yl)-1H-indazole (290 mg, 827.59 μmol, 58.99% yield) as a white solid.

Exemplary Synthesis of Intermediate 2-[[3-iodo-5-(1-methylcyclopropoxy)indazol-1-yl]methoxy]ethyl-trimethyl-silane

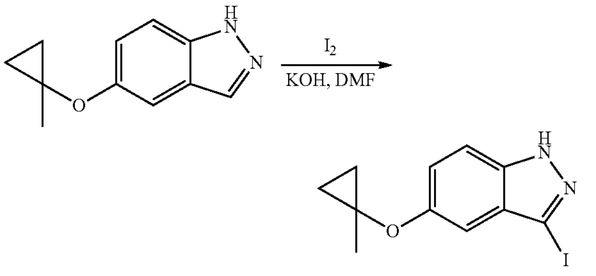

Step 1

To a solution of 5-(1-methylcyclopropoxy)-1H-indazole (1 g, 4.45 mmol, 1 eq, HCl) in DMF (10 mL) was added 12 (2.26 g, 8.90 mmol, 1.79 mL, 2 eq) and KOH (749.18 mg, 13.35 mmol, 3 eq). After addition, the reaction mixture was stirred at 25° C. for 3 h. LCMS showed desired MS. TLC (petroleum ether:ethyl acetate=5:1) showed a major new spot. The reaction mixture was quenched by saturated Na2S2O3 (20 mL) and extracted with ethyl acetate (2×20 mL). The organic layer was dried over sodium sulfate and concentrated under reduced pressure. The residue was purified by silica gel column chromatography (0 to 15% ethyl acetate in petroleum ether) to afford 3-iodo-5-(1-methylcyclopropoxy)-1H-indazole (1.4 g, 4.35 mmol, 97.84% yield, 97.7% purity) as a light yellow oil.

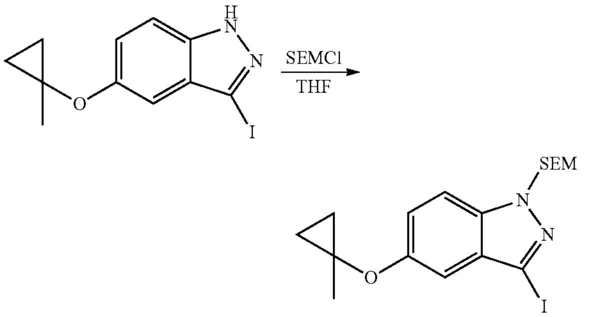

Step 2

To a mixture of 3-iodo-5-(1-methylcyclopropoxy)-1H-indazole (1.2 g, 3.82 mmol, 1 eq) in THF (15 mL) was added N-cyclohexyl-N-methyl-cyclohexanamine (2.24 g, 11.46 mmol, 2.43 mL, 3 eq) and SEM-Cl (1.27 g, 7.64 mmol, 1.35 mL, 2 eq). After addition, the reaction mixture was stirred at 25° C. for 2 hours to give white suspension. LCMS showed desired MS. TLC (petroleum ether:ethyl acetate=5:1) showed several new spots. The reaction mixture was diluted with water (150 mL) and extracted with ethyl acetate (150 mL). The organic layer was dried over sodium sulfate and concentrated under reduced pressure. The residue was purified by silica gel column chromatography (0 to 12% ethyl acetate in petroleum ether) to afford 2-[[3-iodo-5-(1-methylcyclopropoxy)indazol-1-yl]methoxy]ethyl-trimethyl-silane (630 mg, 1.36 mmol, 35.55% yield, 95.8% purity) as a light yellow oil.

Exemplary Synthesis of Intermediate 2-(2,6-dioxopiperidin-3-yl)-5-(piperazin-1-yl)isoindoline-1,3-dione hydrochloride

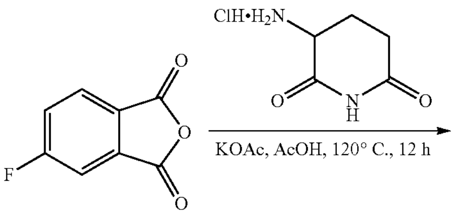

-continued

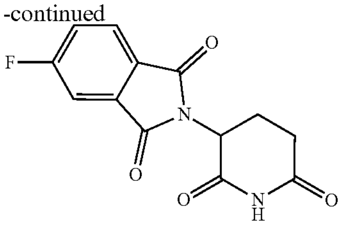

Step 1

To a solution of 5-fluoroisobenzofuran-1,3-dione (1 g, 6.02 mmol, 1 eq) and 3-aminopiperidine-2,6-dione HCl salt (1.49 g, 9.03 mmol, 1.5 eq) in $CH_3COOH$ (10 mL) was added KOAc (1.18 g, 12.04 mmol, 2 eq). After addition, the reaction mixture was stirred at 120° C. for 12 hours. The mixture was diluted with water (40 mL). The mixture was filtered, and the filtrate cake was washed with water (100 mL) to afford 2-(2,6-dioxo-3-piperidyl)-5-fluoro-isoindoline-1,3-dione (1.4 g, 5.07 mmol, 84.19% yield) as a black solid.

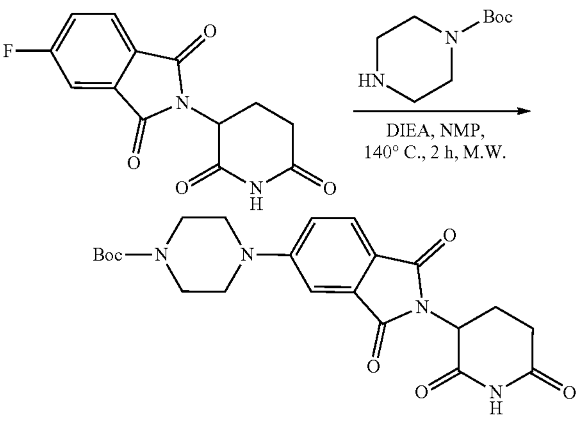

Step 2

To a solution of 2-(2,6-dioxo-3-piperidyl)-5-fluoro-isoindoline-1,3-dione (1.15 g, 4.16 mmol, 1 eq) and tert-butyl piperazine-1-carboxylate (852.97 mg, 4.58 mmol, 1.1 eq) in NMP (10 mL) was added DIEA (1.61 g, 12.49 mmol, 2.18 mL, 3 eq). The sealed tube was heated at 140° C. for 2 hours under microwave. The mixture was combined with second batch and diluted with water (50 mL) and extracted with ethyl acetate (2×50 mL). The combined organic phase was washed with saturated brine (2×30 mL), dried over anhydrous sodium sulfate and concentrated under reduced pressure. The residue was purified by silica gel column chromatography (0 to 50% ethyl acetate in petroleum ether) to afford tert-butyl 4-[2-(2,6-dioxo-3-piperidyl)-1,3-dioxo-isoindolin-5-yl]piperazine-1-carboxylate (1.4 g, 3.16 mmol) as a yellow solid. The average yield is 62.49% based on the combined batches.

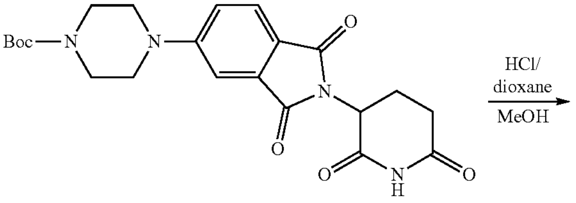

-continued

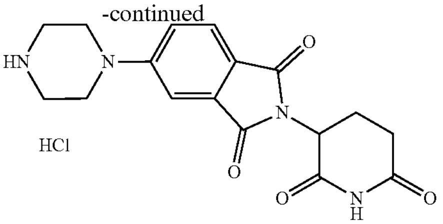

Step 3

To a solution of tert-butyl 4-[2-(2,6-dioxo-3-piperidyl)-1,3-dioxo-isoindolin-5-yl]piperazine-1-carboxylate (1.2 g, 2.71 mmol, 1 eq) in MeOH (10 mL) was added HCl/dioxane (4 M, 2.00 mL, 2.95 eq). After addition, the reaction solution was stirred at 65° C. for 1 h. The reaction solution was combined with a second batch. The mixture was concentrated under reduced pressure to afford 2-(2,6-dioxopiperidin-3-yl)-5-(piperazin-1-yl)isoindoline-1,3-dione hydrochloride (1.1 g, crude) as a yellow solid. The average yield is 91.04% based on the combined batches.

Exemplary Synthesis of Intermediate [1-[2-(2,6-dioxo-3-piperidyl)-1,3-dioxo-isoindolin-5-yl]-4-piperidyl]methyl 4-methylbenzenesulfonate

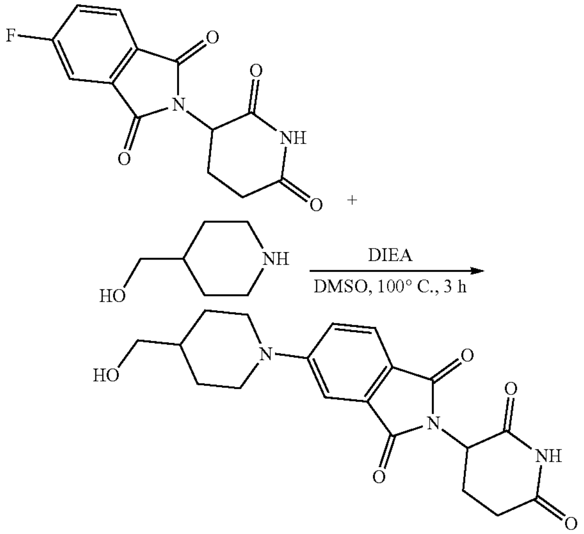

Step 1

To a mixture of 2-(2,6-dioxo-3-piperidyl)-5-fluoro-isoindoline-1,3-dione (100 mg, 362.03 μmol, 1 eq) and 4-piperidylmethanol (83.39 mg, 724.06 μmol, 2 eq) in DMSO (2 mL) was added DIEA (140.37 mg, 1.09 mmol, 189.18 μL, 3 eq) in one portion at 20° C. The mixture was stirred at 100° C. for 3 h. TLC (DCM:MeOH=10:1, Rf=0.36) showed the reaction was completed. The mixture was cooled to 20° C. The residue was poured into $NaHCO_3$ (10 mL) to adjust pH=7-8. The aqueous phase was extracted with ethyl acetate (3×10 mL). The combined organic phase was washed with brine (2×10 mL), dried with anhydrous $Na_2SO_4$, filtered and concentrated in vacuum. The residue was purified by silica gel chromatography (100-200 mesh silica gel, 0-10% of MeOH in DCM) to give 2-(2,6-dioxo-3-piperidyl)-5-[4-(hydroxymethyl)-1-piperidyl]isoindoline-1,3-dione (120 mg, 283.18 μmol, 78.22% yield, 87.640% purity) as a yellow gum.

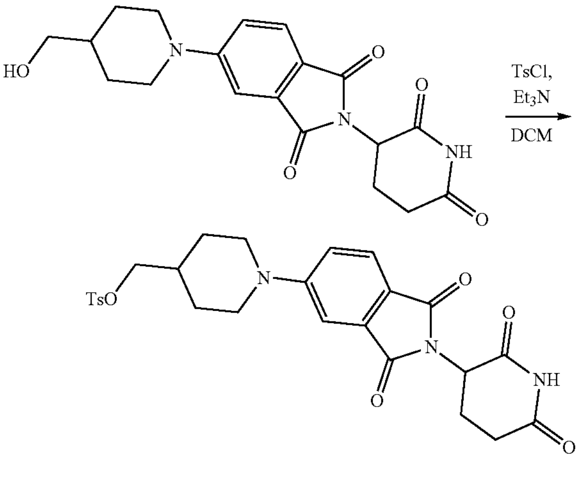

Step 2

To a solution of 2-(2,6-dioxo-3-piperidyl)-5-[4-(hydroxymethyl)-1-piperidyl]isoindoline-1,3-dione (120 mg, 323.11 μmol, 1 eq) and TEA (98.09 mg, 969.34 μmol, 134.92 μL, 3 eq) in DCM (5 mL) was added TsCl (27.35 mg, 387.74 μmol, 1.2 eq) in one portion at 0° C. under $N_2$. The mixture was stirred at 20° C. for 20 hours to give yellow solution. TLC (DCM:MeOH=10:1, Rf=0.45) showed the reaction was completed. The residue was poured into water (5 mL). The aqueous phase was extracted with ethyl acetate (3×5 mL). The combined organic phase was washed with brine (2×5 mL), dried with anhydrous $Na_2SO_4$, filtered and concentrated in vacuum. The residue was purified by silica gel chromatography (100-200 mesh silica gel, 0-50% of Ethyl acetate in Petroleum ether for 5 min, 50-100 of Ethyl acetate in Petroleum ether for 10 min) to give [1-[2-(2,6-dioxo-3-piperidyl)-1,3-dioxo-isoindolin-5-yl]-4-piperidyl] methyl 4-methylbenzenesulfonate (160 mg, 228.91 μmol, 70.85% yield, 75.194% purity) as a yellow solid.

Exemplary Synthesis of Intermediate 1-[2-(2,6-dioxo-3-piperidyl)-1,3-dioxo-isoindolin-5-yl]piperidine-4-carbaldehyde

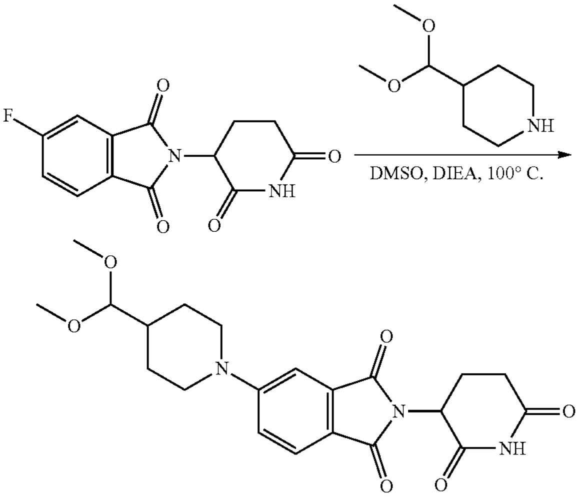

Step 1

To a solution of 2-(2,6-dioxo-3-piperidyl)-5-fluoro-isoindoline-1,3-dione (300 mg, 1.09 mmol, 1 eq) and 4-(dimethoxymethyl)piperidine (207.52 mg, 1.30 mmol, 1.2 eq) in DMSO (5 mL) was added DIEA (421.11 mg, 3.26 mmol, 567.53 μL, 3 eq) at 25° C., then the reaction was stirred at 100° C. for 1 h to give a brown solution. The desired product was detected by TLC (Dichloromethane:Methanol=10:1, Rf=0.5). The reaction mixture was poured into $H_2O$ (5 mL). The mixture was extracted with ethyl acetate (10 mL*3). The organic phase was washed with brine (10 mL), dried over anhydrous $Na_2SO_4$, concentrated in vacuum to give a residue. The residue was purified by silica gel chromatography (column height: 250 mm, diameter: 100 mm, 100-200 mesh silica gel, Petroleum ether/Ethyl acetate=100/1, 1/1) to afford 5-[4-(dimethoxymethyl)-1-piperidyl]-2-(2,6-dioxo-3-piperidyl)isoindoline-1,3-dione (326 mg, 580.69 μmol, 53.47% yield, 74% purity) as a yellow solid.

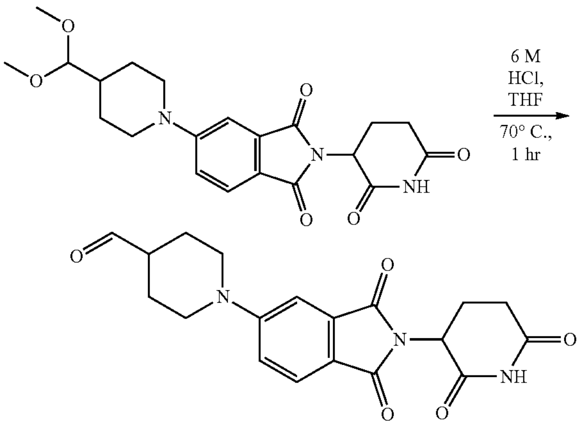

Step 2

To a solution of 5-[4-(dimethoxymethyl)-1-piperidyl]-2-(2,6-dioxo-3-piperidyl)isoindoline-1,3-dione (140 mg, 336.99 μmol, 1 eq) in THF (3 mL) was added HCl (2 M, 3 mL, 17.80 eq). After addition, the reaction solution was stirred at 70° C. for 1 h. LCMS showed desired MS. The reaction solution was quenched by saturated $NaHCO_3$ (pH-8) and extracted with ethyl acetate (3×15 mL). The organic layer was dried over sodium sulfate and concentrated under reduced pressure to afford 1-[2-(2,6-dioxo-3-piperidyl)-1,3-dioxo-isoindolin-5-yl]piperidine-4-carbaldehyde (124 mg, 302.14 μmol, 89.66% yield, 90% purity) as a yellow solid. The crude product was used directly.

Exemplary Synthesis of Compound 52

Step 1

To a solution of EtOAc (4.42 g, 50.19 mmol, 4.91 mL, 1 eq) in THF (100 mL) was added a solution of LiHMDS (1 M, 50.19 mL, 1 eq) drop-wise at −70° C. over a period of 30 mins under N2. Then tert-butyl 4-oxopiperidine-1-carboxylate (10 g, 50.19 mmol, 1 eq) in THF (50 mL) was added to a solution. The reaction mixture was stirred at −70° C. for 1 hour. TLC (Petroleum ether/Ethyl acetate=10:1, Rf=0.19) showed the starting material was consumed completely. The residue was poured into water (100 mL). The aqueous phase was extracted with ethyl acetate (100 mL*3). The combined organic phase was washed with brine (100 mL*2), dried with anhydrous Na2SO4, filtered and concentrated in vacuum. The residue was purified by silica gel chromatography (80 g, 0-40% (20 min) of Ethyl acetate in Petroleum ether, 40% (10 min) of Ethyl acetate in Petroleum ether) to give tert-butyl 4-(2-ethoxy-2-oxo-ethyl)-4-hydroxy-piperidine-1-carboxylate (11.2 g, 38.98 mmol, 77.66% yield) as a colourless oil.

Step 2

To a mixture of tert-butyl 4-(2-ethoxy-2-oxo-ethyl)-4-hydroxy-piperidine-1-carboxylate (5 g, 17.40 mmol, 1 eq) in THF (50 mL) was added LiAlH4 (726.38 mg, 19.14 mmol, 1.1 eq) at 0° C. under N2. Then the mixture was stirred at 25° C. for 1 h to give white suspension. TLC (Petroleum ether:Ethyl acetate=10:1, Rf=0.10) showed no start material and a new spot. The reaction mixture was quenched with water (1 mL), then 15% sodium hydroxide aqueous solution (1 mL) and water (3 mL) was added. The solid was removed by filtration. The filtrate was concentrated under reduced pressure to give tert-butyl 4-hydroxy-4-(2-hydroxyethyl)piperidine-1-carboxylate (3.3 g, 13.45 mmol, 77.31% yield) as a colourless oil.

Step 3

To a mixture of tert-butyl 4-hydroxy-4-(2-hydroxyethyl)piperidine-1-carboxylate (3.3 g, 13.45 mmol, 1 eq) and TosCl (3.85 g, 20.18 mmol, 1.5 eq) in DCM (30 mL) was added TEA (4.08 g, 40.36 mmol, 5.62 mL, 3 eq) in one portion at 25° C. under N2. The mixture was stirred at 25° C. for 16 hours. TLC (Petroleum ether:Ethyl acetate=10:1, Rf=0.34, PMA) showed there was no starting material and a new spot was showed by TLC. LCMS showed desired MS. The residue was poured into water (30 mL). The aqueous phase was extracted with ethyl acetate (50 mL*3). The combined organic phase was washed with brine (50 mL*2), dried with anhydrous Na2SO4, filtered and concentrated in vacuum. The residue was purified by silica gel chromatography (40 g, 0-50% (10 min) of Ethyl acetate Petroleum ether, 50% (10 min) of Ethyl acetate Petroleum ether) to give tert-butyl 4-hydroxy-4-[2-(p-tolylsulfonyloxy)ethyl]piperidine-1-carboxylate (4.6 g, 11.51 mmol, 85.60% yield) as a yellow oil.

Step 4

To a mixture of tert-butyl 4-hydroxy-4-[2-(p-tolylsulfonyloxy)ethyl]piperidine-1-carboxylate (2 g, 5.01 mmol, 1 eq) and benzyl (3S)-3-methylpiperazine-1-carboxylate (3.52 g, 15.02 mmol, 3 eq) in MeCN (10 mL) was added KI (1.66 g, 10.01 mmol, 2 eq) and DIPEA (1.29 g, 10.01 mmol, 1.74 mL, 2 eq) in one portion at 20° C. under N2. The mixture was stirred at 80° C. for 10 hours. LCMS showed desired MS. The mixture was cooled to 25° C. and concentrated in reduced pressure at 25° C. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The crude product was purified by reversed-phase HPLC (Column: 33_Phenomenex Luna C18 75*30 mm*3 um; Condition: water (0.225% FA)-ACN; Begin B: 0; End B: 35; FlowRate: 25 mL/min; Gradient Time: 40 min; 100% B Hold Time: 3 min) to give benzyl (3S)-4-[2-(1-tert-butoxycarbonyl-4-hydroxy-4-piperidyl)ethyl]-3-methyl-piperazine-1-carboxylate (150 mg, 298.96 μmol, 5.97% yield, 92% purity) as a yellow gum.

Step 5

To a mixture of benzyl (3S)-4-[2-(1-tert-butoxycarbonyl-4-hydroxy-4-piperidyl)ethyl]-3-methyl-piperazine-1-carboxylate (150 mg, 324.96 μmol, 1 eq) in DCM (10 mL) was added DAST (52.38 mg, 324.96 μmol, 42.93 μL, 1 eq) drop-wise at −40° C. under N2. Then heated to 25° C. and stirred for 2 hours to give colourless solution. TLC (Petroleum ether:Ethyl acetate=1:1, Rf=0.13, PMA) showed the reaction was completed, LCMS showed there was desired MS. The residue was poured into $NaHCO_3$ to adjusted the pH=7-8. The aqueous phase was extracted with Petroleum ether (10 mL*3). The combined organic phase was washed with brine (10 mL*2), dried with anhydrous Na2SO4, filtered and concentrated in vacuum. The residue was purified by silica gel chromatography (0-100% (20 min) of Ethyl acetate in Petroleum ether) to give benzyl (3S)-4-[2-(1-tert-butoxycarbonyl-4-fluoro-4-piperidyl)ethyl]-3-methyl-piperazine-1-carboxylate (122 mg, 223.69 μmol, 68.84% yield, 85% purity) as a yellow gum Step 6

To a mixture of benzyl (3S)-4-[2-(1-tert-butoxycarbonyl-4-fluoro-4-piperidyl)ethyl]-3-methyl-piperazine-1-carboxylate (122 mg, 263.17 μmol, 1 eq) in DCM (5 mL) was added TFA (3.08 g, 27.01 mmol, 2 mL, 102.65 eq) in one portion at 20° C. under N2. The mixture was stirred at 25° C. for 30 min. TLC showed the reaction was completed. The mixture was concentrated in vacuum to give benzyl (3S)-4-[2-(4-fluoro-4-piperidyl)ethyl]-3-methyl-piperazine-1-carboxylate (150 mg, 229.32 μmol, 87.14% yield, 73% purity, TFA) as a yellow gum.

Step 7

To a mixture of benzyl (3S)-4-[2-(4-fluoro-4-piperidyl)ethyl]-3-methyl-piperazine-1-carboxylate (150 mg, 229.32 μmol, 73% purity, 1 eq, TFA) and 1-[2-(2,6-dioxo-3-piperidyl)-1,3-dioxo-isoindolin-5-yl]piperidine-4-carbaldehyde (84.71 mg, 229.32 μmol, 1 eq) in MeOH (10 mL) was added borane; 2-methylpyridine (49.06 mg, 458.65 μmol, 2 eq) and HOAc (1 mL) in one portion at 25° C. under N2. The mixture was stirred at 25° C. for 1 h. TLC (Dichloromethane:Methanol=10:1, Rf=0.43) showed the reaction was completed, LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (Dichloromethane:Methanol=10:1, Rf=0.43, 0-100% (20 min) of Ethyl acetate in Petroleum ether, 100% (10 min) of Ethyl acetate in Petroleum ether) to give benzyl (3S)-4-[2-[1-[[1-[2-(2,6-dioxo-3-piperidyl)-1,3-dioxo-isoindolin-5-yl]-4-piperidyl]methyl]-4-fluoro-4-piperidyl]ethyl]-3-methyl-piperazine-1-carboxylate (193 mg, crude) as a yellow oil.

Step 8

To a mixture of benzyl (3S)-4-[2-[1-[[1-[2-(2,6-dioxo-3-piperidyl)-1,3-dioxo-isoindolin-5-yl]-4-piperidyl]methyl]-4-fluoro-4-piperidyl]ethyl]-3-methyl-piperazine-1-carboxylate (193 mg, 269.24 μmol, 1 eq) in TFA (2.78 g, 24.39 mmol, 1.81 mL, 90.60 eq) in one portion at 20° C. under N2. The mixture was stirred at 70° C. for 1 h to give yellow solution. TLC showed the reaction was completed. The residue was concentrated in vacuum to give 2-(2,6-dioxo-3-piperidyl)-5-[4-[[4-fluoro-4-[2-[(2S)-2-methylpiperazin-1-yl]ethyl]-1-piperidyl]methyl]-1-piperidyl]isoindoline-1,3-dione (150 mg, 131.36 μmol, 48.79% yield, 71% purity, 2TFA) as a yellow gum.

Step 9

To a mixture of 2-(2,6-dioxo-3-piperidyl)-5-[4-[[4-fluoro-4-[2-[(2S)-2-methylpiperazin-1-yl]ethyl]-1-piperidyl]methyl]-1-piperidyl]isoindoline-1,3-dione (150 mg, 185.01 μmol, 1.11 eq, 2TFA) and 3-(6-chloropyrimidin-4-yl)-5-(1-methylcyclopropoxy)-1H-indazole (50 mg, 166.26 μmol, 1 eq) in DMSO (5 mL) was added DIEA (171.89 mg, 1.33 mmol, 231.66 μL, 8 eq) in one portion at 20° C. under N2. The mixture was stirred at 80° C. for 16 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 40; FlowRate: 25 mL/min; Gradient Time: 40 min; 100% B Hold Time: 3 min) to give 2-(2,6-dioxo-3-piperidyl)-5-[4-[[4-fluoro-4-[2-[(2S)-2-methyl-4-[6-[5-(1-methylcyclopropoxy)-1H-indazol-3-yl]pyrimidin-4-yl]piperazin-1-yl]ethyl]-1-piperidyl]methyl]-1-piperidyl]isoindoline-1,3-dione (16.9 mg, 19.45 μmol, 11.70% yield, 97.5% purity) as a yellow solid.

Exemplary Synthesis of Compound 53

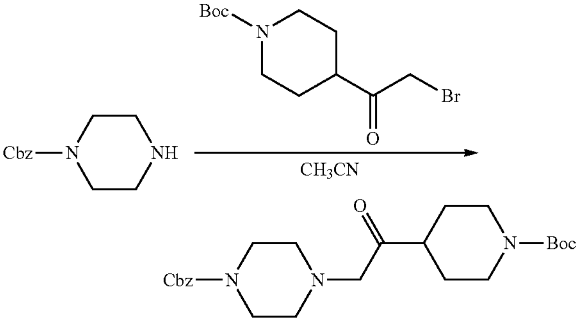

Step 1

To a solution of tert-butyl 4-(2-bromoacetyl)piperidine-1-carboxylate (695.05 mg, 2.27 mmol, 1 eq) in MeCN (10 mL) was stirred at 20° C. Then the mixture was added benzyl piperazine-1-carboxylate (500 mg, 2.27 mmol, 438.60 μL, 1 eq) and stirred at 25° C. for 2 hr under $N_2$. TLC (Dichloromethane:Methanol=10:1) showed started material consumed completed and two new major points found. The residue was concentrated under reduced pressure to give a residue. The residue was purified by silica gel column chromatography (0 to 10% Dichloromethane in Methanol) to give benzyl 4-[2-(1-tert-butoxycarbonyl-4-piperidyl)-2-oxo-ethyl]piperazine-1-carboxylate (690 mg, 774.32 μmol, 34.11% yield, 50% purity) as a yellow gum

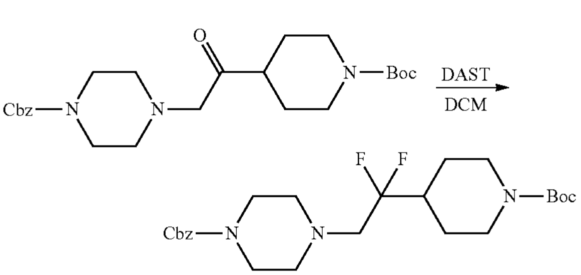

Step 2

To a solution of benzyl 4-[2-(1-tert-butoxycarbonyl-4-piperidyl)-2-oxo-ethyl]piperazine-1-carboxylate (690 mg, 1.55 mmol, 1 eq) in DCM (10 mL) was stirred at 0° C. for 20 min. Then the mixture was added DAST (8.74 g, 54.20 mmol, 7.16 mL, 35 eq) and stirred at 25° C. for 16 hrs under $N_2$. LCMS showed desired MS. TLC (Petroleum ether:Ethyl acetate=1:1) showed started material consumed completed and two new major points found. The residue was concentrated under reduced pressure to give a residue. The residue was purified by silica gel column chromatography (0 to 50% Dichloromethane in Methanol) to give compound benzyl 4-[2-(1-tert-butoxycarbonyl-4-piperidyl)-2,2-difluoro-ethyl]piperazine-1-carboxylate (298 mg, 254.95 μmol, 16.46% yield, 40% purity) as a colorless gum.

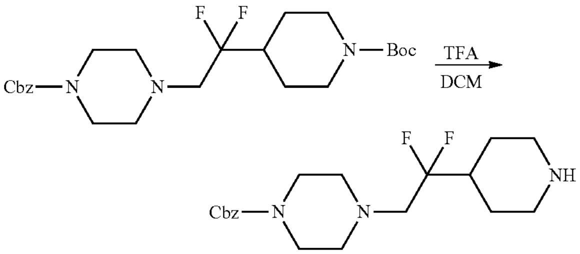

Step 3

To a solution of benzyl 4-[2-(1-tert-butoxycarbonyl-4-piperidyl)-2,2-difluoro-ethyl]piperazine-1-carboxylate (298 mg, 637.37 μmol, 1 eq) in DCM (3 mL) was added TFA (4.62 g, 40.52 mmol, 3 mL, 63.57 eq). Then the mixture was stirred at 25° C. for 0.5 hr under $N_2$. LCMS showed desired MS. The residue was concentrated under reduced pressure to give benzyl 4-[2, 2-difluoro-2-(4-piperidyl)ethyl]piperazine-1-carboxylate (480 mg, crude, TFA) as a brown oil.

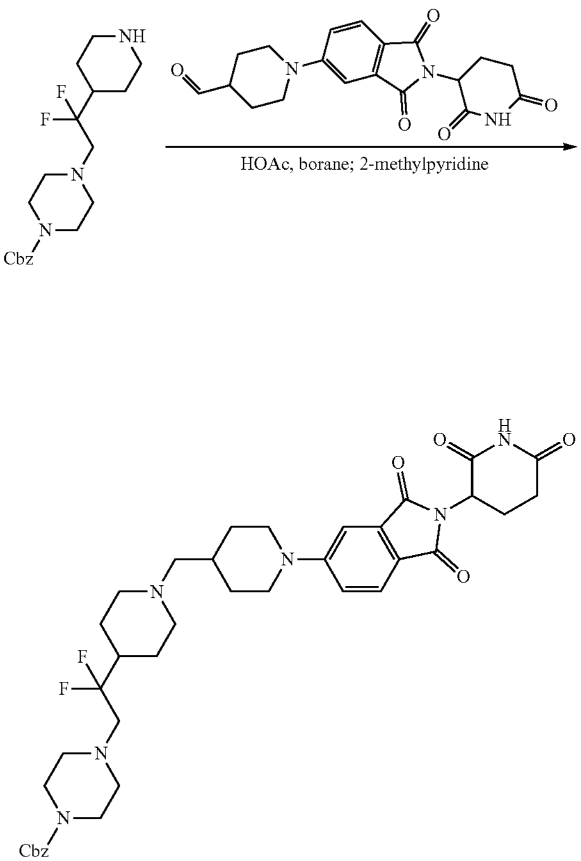

Step 4

To a solution of benzyl 4-[2,2-difluoro-2-(4-piperidyl)ethyl]piperazine-1-carboxylate (380 mg, 1.03 mmol, 1 eq), 1-[2-(2,6-dioxo-3-piperidyl)-1,3-dioxo-isoindolin-5-yl]piperidine-4-carbaldehyde (114.60 mg, 310.26 μmol, 0.3 eq) in MeOH (10 mL) was added AcOH (2 mL), borane; 2-methylpyridine (221.24 mg, 2.07 mmol, 2 eq). Then the mixture was stirred at 20° C. for 2 hr under $N_2$. LCMS showed desired MS. The residue was concentrated under reduced pressure to give a residue. The residue was purified by silica gel column chromatography (0 to 10% Dichloromethane in Methanol) to give benzyl 4-[2-[1-[[1-[2-(2,6-dioxo-3-piperidyl)-1,3-dioxo-isoindolin-5-yl]-4-piperidyl]methyl]-4-piperidyl]-2,2-difluoro-ethyl]piperazine-1-carboxylate (1 g, crude) as a yellow gum.

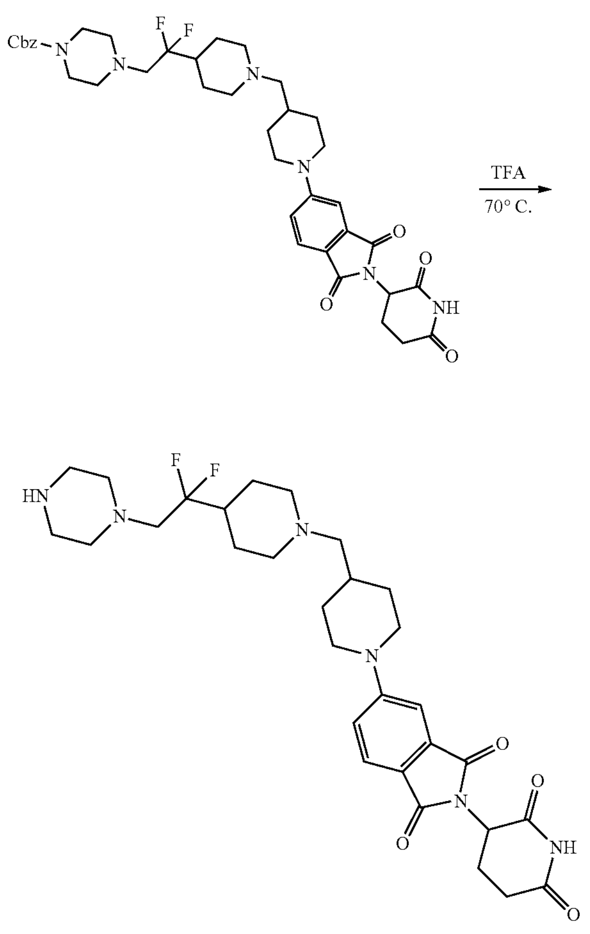

Step 5

A mixture of benzyl 4-[2-[1-[[1-[2-(2,6-dioxo-3-piperidyl)-1,3-dioxo-isoindolin-5-yl]-4-piperidyl]methyl]-4-piperidyl]-2,2-difluoro-ethyl]piperazine-1-carboxylate (200 mg, 277.47 μmol, 1 eq) was added TFA (31.64 mg, 277.47 μmol, 20.54 μL, 1 eq). Then the mixture was stirred at 70° C. for 0.5 hr under $N_2$. TLC (Dichloromethane:Methanol=10:1) showed started material consumed completed and one new major point found The residue was concentrated under reduced pressure to give 5-[4-[[4-(1,1-difluoro-2-piperazin-1-yl-ethyl)-1-piperidyl]methyl]-1-piperidyl]-2-(2,6-dioxo-3-piperidyl)isoindoline-1,3-dione (200 mg, crude, TFA) as a brown oil.

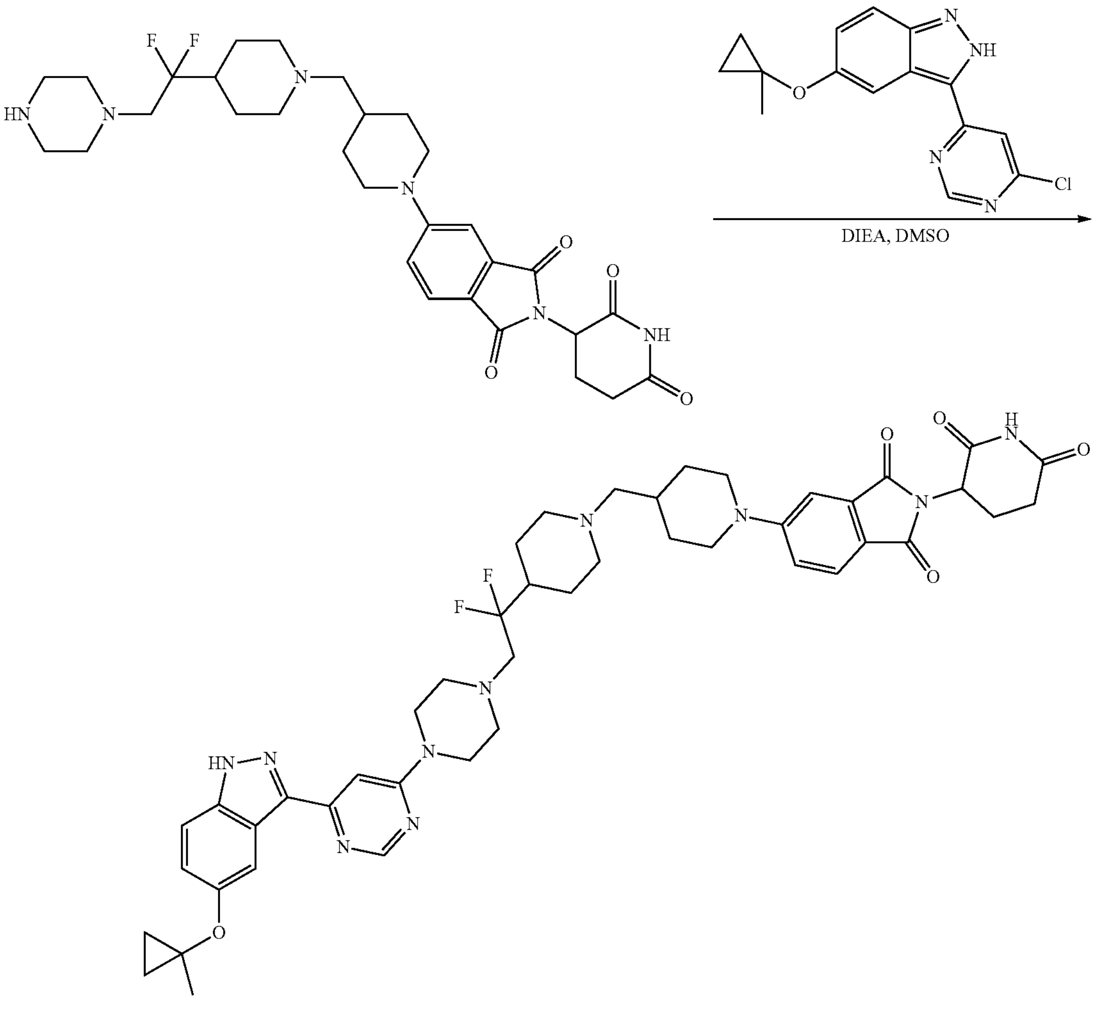

Step 6

To a solution of 5-[4-[[4-(1,1-difluoro-2-piperazin-1-yl-ethyl)-1-piperidyl]methyl]-1-piperidyl]-2-(2,6-dioxo-3-piperidyl)isoindoline-1,3-dione (162 mg, 276.13 μmol, 1 eq) in DMSO (10 mL) was added 3-(6-chloropyrimidin-4-yl)-5-(1-methylcyclopropoxy)-2H-indazole (66.44 mg, 220.91 μmol, 0.8 eq), DIEA (2.23 g, 17.22 mmol, 3 mL, 62.37 eq). Then the mixture was stirred at 70° C. for 16 hr under $N_2$. LCMS showed desired MS. The reaction mixture was concentrated under reduced pressure to give a residue. The crude product was purified by reversed-phase HPLC (column: 3_Phenomenex Luna C18 75*30 mm*3 um; mobile phase: [water (0.225% FA)-ACN]; B %: 0%-40%, 40 min). to give 5-[4-[[4-[1,1-difluoro-2-[4-[6-[5-(1-methylcyclopropoxy)-1H-indazol-3-yl]pyrimidin-4-yl]piperazin-1-yl]ethyl]-1-piperidyl]methyl]-1-piperidyl]-2-(2,6-dioxo-3-piperidyl)isoindoline-1,3-dione (13.5 mg, 15.23 μmol, 5.52% yield, 96% purity) as a yellow solid.

Exemplary Synthesis of Compound 54

Compound 54 was prepared in a manner analogous to compound 53 using benzyl 4-(2-piperazin-1-ylethyl)piperazine-1-carboxylate.

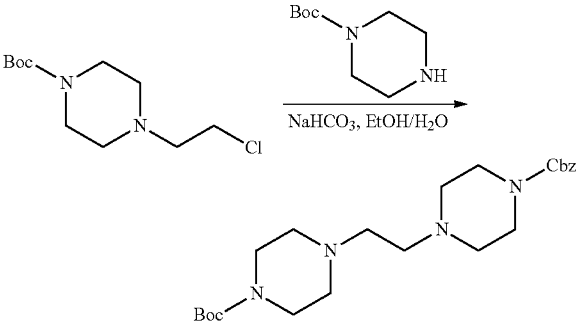

Step 1

To a mixture of tert-butyl 4-(2-chloroethyl)piperazine-1-carboxylate (1 g, 4.02 mmol, 1 eq) and benzyl piperazine-1-carboxylate (1.33 g, 6.03 mmol, 1.17 mL, 1.5 eq) in EtOH (10 mL) and $H_2O$ (1 mL) was added $NaHCO_3$ (675.43 mg, 8.04 mmol, 312.70 μL, 2 eq) in one portion at 25° C. under $N_2$. The mixture was stirred at 80° C. 3 hours. LCMS showed there was desired MS. The mixture was cooled to 25° C. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by silica gel chromatography (20 g, 0-40% (10 min) of Ethyl acetate in Petroleum ether, 40% (10 min) of Ethyl acetate in Petroleum ether) to give benzyl 4-[2-(4-tert-butoxycarbonylpiperazin-1-yl)ethyl]piperazine-1-carboxylate (800 mg, 1.85 mmol, 46.01% yield) as a yellow solid.

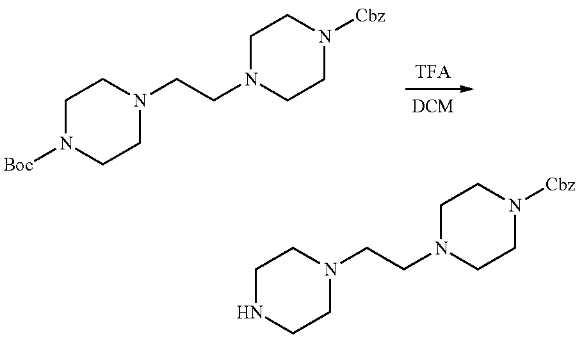

Step 2

To a mixture of benzyl 4-[2-(4-tert-butoxycarbonylpiperazin-1-yl)ethyl]piperazine-1-carboxylate (200 mg, 462.37 μmol, 1 eq) in DCM (5 mL) was added TFA (1.85 g, 16.25 mmol, 1.20 mL, 35.15 eq) in one portion at 25° C. The mixture was stirred at 25° C. for 30 min. LCMS (EB16-1124-P1A1) showed the reaction was completed. The residue concentrated in vacuum to give benzyl 4-(2-piperazin-1-ylethyl)piperazine-1-carboxylate (200 mg, 277.74 μmol, 60.07% yield, 62% purity, TFA) as a yellow gum.

Exemplary Synthesis of Compound 55

Compound 55 was prepared in a manner analogous to compound 54 starting with tert-butyl (2S)-2-methylpiperazine-1-carboxylate.

Exemplary Synthesis of Compound 56

Step 1

To a solution of tert-butyl piperidine-4-carboxylate (503.03 mg, 2.72 mmol, 1.5 eq) and 2-(2,6-dioxo-3-piperidyl)-5-fluoro-isoindoline-1,3-dione (500 mg, 1.81 mmol, 1 eq) in DMSO (5 mL) and DIEA (2.34 g, 18.10 mmol, 3.15 mL, 10 eq). The mixture was stirred at 80° C. for 16 h. LCMS showed desired product MS. The resulting product was poured into H2O (20 mL). The mixture was extracted with ethyl acetate (20 mL*3). The organic phase was washed with brine (15 mL*2), dried over anhydrous Na2SO4, concentrated in vacuum to give a residue. The residue was purified by silica gel chromatography (0-50% (10 min) of Ethyl acetate in Petroleum ether, 50% (10 min) of Ethyl acetate in Petroleum ether) to give tert-butyl 1-[2-(2,6-dioxo-3-piperidyl)-1,3-dioxo-isoindolin-5-yl]piperidine-4-carboxylate (660 mg, 1.49 mmol, 82.59% yield) as a yellow solid.

Step 2

To a solution of tert-butyl 1-[2-(2,6-dioxo-3-piperidyl)-1,3-dioxo-isoindolin-5-yl]piperidine-4-carboxylate (660 mg, 1.49 mmol, 1 eq) in DCM (5 mL) and TFA (3.08 g, 27.01 mmol, 2 mL, 18.07 eq). The mixture was stirred at 25° C. for 30 min. LCMS showed desired product MS. The resulting product was concentrated in vacuum to give a residue. The residue was purified by prep-HPLC (column: Xtimate C18 150*40 mm*10 um; mobile phase: [water (0.05% HCl)-ACN]; B %: 15%-45%, 10 min) to give 1-[2-(2,6-dioxo-3-piperidyl)-1,3-dioxo-isoindolin-5-yl]piperidine-4-carboxylic acid (550 mg, 1.40 mmol, 93.49% yield, 97.93% purity) as a yellow solid.

Step 3

To a solution of benzyl (3S)-3-methyl-4-(2-piperazin-1-ylethyl)piperazine-1-carboxylate (130 mg, 339.49 μmol, 1.31 eq, HCl) and 1-[2-(2,6-dioxo-3-piperidyl)-1,3-dioxo-isoindolin-5-yl]piperidine-4-carboxylic acid (100 mg, 259.49 μmol, 1 eq) in DMF (3 mL) was added DIEA (100.61 mg, 778.47 μmol, 135.60 μL, 3 eq) and HATU (98.67 mg, 259.49 μmol, 1 eq). After addition, the reaction mixture was stirred at 20° C. for 1 h. LCMS and TLC (dichloromethane: methanol=10:1) showed the reaction completed. The reaction mixture was diluted with ethyl acetate (20 mL) and washed with brine (10 mL*3). The organic layer was dried over sodium sulfate and concentrated under reduced pressure. The residue was purified by silica gel column chromatography (0 to 15% methanol in dichloromethane) to afford benzyl (3S)-4-[2-[4-[1-[2-(2,6-dioxo-3-piperidyl)-1,3-dioxo-isoindolin-5-yl]piperidine-4-carbonyl]piperazin-1-yl]ethyl]-3-methyl-piperazine-1-carboxylate (95 mg, 101.01 μmol, 38.93% yield, 75.9% purity) as a yellow solid.

Step 4

A mixture of benzyl (3S)-4-[2-[4-[1-[2-(2,6-dioxo-3-piperidyl)-1,3-dioxo-isoindolin-5-yl]piperidine-4-carbonyl]piperazin-1-yl]ethyl]-3-methyl-piperazine-1-carboxylate (95 mg, 133.09 μmol, 1 eq) and TFA (3.08 g, 27.01 mmol, 2 mL, 202.97 eq) was stirred at 80° C. for 1 h. LCMS (EB12-916-P1B) showed the reaction was completed. The reaction mixture was concentrated under reduced pressure to afford 2-(2,6-dioxo-3-piperidyl)-5-[4-[4-[2-[(2S)-2-methylpiperazin-1-yl]ethyl]piperazine-1-carbonyl]-1-piperidyl]isoindoline-1,3-dione (80 mg, crude) as a yellow gum.

Step 5

To a solution of 2-(2,6-dioxo-3-piperidyl)-5-[4-[4-[2-[(2S)-2-methylpiperazin-1-yl]ethyl]piperazine-1-carbonyl]-1-piperidyl]isoindoline-1,3-dione (67.46 mg, 116.38 μmol, 1 eq) and 3-(6-chloropyrimidin-4-yl)-5-(1-methylcyclopropoxy)-2H-indazole (35 mg, 116.38 μmol, 1 eq) in DMSO (2 mL) was added DIEA (75.21 mg, 581.89 μmol, 101.36 μL, 5 eq). After addition, the reaction solution was stirred at 90° C. for 16 h. LCMS showed the reaction completed. The reaction mixture was diluted with brine (10 mL) and extracted with dichloromethane (20 mL*3). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 0%-35%, 40 min) to afford 2-(2,6-dioxo-3-piperidyl)-5-[4-[4-[2-[(2S)-2-methyl-4-[6-[5-(1-methylcyclopropoxy)-2H-indazol-3-yl]pyrimidin-4-yl]piperazin-1-yl]ethyl]piperazine-1-carbonyl]-1-piperidyl]isoindoline-1,3-dione (15.2 mg, 17.53 μmol, 15.07% yield, 97.35% purity) as a yellow solid.

Exemplary Synthesis of Compound 57

Compound 57 was prepared in a manner analogous to compound 56 using benzyl (3S)-3-methyl-4-[2-(4-piperidyl)ethyl]piperazine-1-carboxylate.

Step 1

To a solution of tert-butyl 4-(2-oxoethyl)piperidine-1-carboxylate (291.04 mg, 1.28 mmol, 1 eq) and benzyl (3S)-3-methylpiperazine-1-carboxylate (300 mg, 1.28 mmol, 1 eq) in MeOH (5 mL) and AcOH (0.5 mL) was added borane; 2-methylpyridine (273.92 mg, 2.56 mmol, 2 eq). After addition, the mixture was stirred at 50° C. for 3 hours. LCMS showed there was desired MS. The residue was poured into $NaHCO_3$ to adjust the pH=7-8. The aqueous phase was extracted with ethyl acetate (20 mL*3). The combined organic phase was washed with brine (20 mL*2), dried with anhydrous Na2SO4, filtered and concentrated in vacuum. The residue was purified by silica gel chromatography (12 g, 100-200 mesh silica gel, 0-100%(15 min) of Ethyl acetate in Petroleum ether, 100% (10 min) of Ethyl acetate in Petroleum ether) to afford benzyl (3S)-4-[2-(1-tert-butoxycarbonyl-4-piperidyl)ethyl]-3-methyl-piperazine-1-carboxylate (500 mg, 1.12 mmol, 87.63% yield) as a colorless oil.

Step 2

To a mixture of benzyl (3S)-4-[2-(1-tert-butoxycarbonyl-4-piperidyl)ethyl]-3-methyl-piperazine-1-carboxylate (100 mg, 224.42 μmol, 1 eq) in EtOAc (2 mL) was added HCl/EtOAc (2 M, 2 mL, 17.82 eq). The mixture was stirred at 20° C. for 1 h. TLC showed the reaction was completed. The reaction mixture was concentrated under reduced pressure to afford benzyl (3S)-3-methyl-4-[2-(4-piperidyl)ethyl] piperazine-1-carboxylate (77 mg, crude, HCl) as a white solid.

Exemplary Synthesis of Compound 58

Compound 58 was prepared in a manner analogous to compound 56 using 1-[2-[(2S)-4-benzyloxycarbonyl-2-methyl-piperazin-1-yl]ethyl]piperidine-4-carboxylic acid and 2-(2,6-dioxo-3-piperidyl)-5-piperazin-1-yl-isoindoline-1,3-dione.

Step 1

Benzyl (3S)-4-(2-chloroethyl)-3-methyl-piperazine-1-carboxylate (1.23 g, 4.16 mmol, 1.1 eq) and tert-butyl piperidine-4-carboxylate (700 mg, 3.78 mmol, 1 eq) were dissolved in EtOH (5 mL) and H2O (0.5 mL), then $NaHCO_3$ (952.24 mg, 11.34 mmol, 440.85 μL, 3 eq) were added the reaction and stirred at 80° C. for 4 hr. LCMS showed ~60% of desired compound and TLC (Dichloromethane:Methanol=10:1, Rf=0.39, 12) showed a main spot formed. The reaction mixture was concentrated under reduced pressure to give a residue. The residue was purified by flash silica gel chromatography (ISCO®; 20 g SepaFlash® Silica Flash Column, Eluent of 0-4% Dichloromethane:Methanol@ 40 mL/min). Compound benzyl (3S)-4-[2-(4-tert-butoxycarbonyl-1-piperidyl)ethyl]-3-methyl-piperazine-1-carboxylate (1.24 g, 2.78 mmol, 73.65% yield) was obtained as a light yellow gum.

Step 2

To a solution of benzyl (3S)-4-[2-(4-tert-butoxycarbonyl-1-piperidyl)ethyl]-3-methyl-piperazine-1-carboxylate (300 mg, 673.26 μmol, 1 eq) in DCM (5 mL) was added TFA (3.46 g, 30.39 mmol, 2.25 mL, 45.14 eq), then then mixture was stirred at 25° C. for 4 hours. LCMS showed desire compound and no the starting materials was remained. The reaction mixture was concentrated under reduced pressure to give a residue. Compound 1-[2-[(2S)-4-benzyloxycarbonyl-2-methyl-piperazin-1-yl]ethyl]piperidine-4-carboxylic acid (300 mg, crude) was obtained as a light yellow oil.

Exemplary Synthesis of Compound 59

Step 1

A mixture of 4-piperidylmethanol (1 g, 8.68 mmol, 1 eq), 2-chloroacetyl chloride (1.18 g, 10.42 mmol, 828.71 μL, 1.2 eq) and TEA (1.82 g, 17.96 mmol, 2.50 mL, 2.07 eq) in DCM (20 mL) was degassed and purged with N2 for 3 times, and then the mixture was stirred at 0° C. for 3 hr under N2 atmosphere. TLC indicated no Reactant 1 remained, and one major new spot with lower polarity was detected. The aqueous HCl solution (0.5 M, 30 mL) was added to the reaction mixture. The reaction mixture was diluted with water (10 mL) and extracted with Ethyl acetate (15 mL). The combined organic layers were washed with brine (10 mL), dried over Na2SO4, filtered and concentrated under reduced pressure to give a residue. The residue was purified by flash silica gel chromatography (ISCO®; 20 g SepaFlash® Silica Flash Column, Eluent of 0-100% Ethyl acetate/Petroleum ether gradient @ 45 mL/min) to afford 2-chloro-1-[4-(hydroxymethyl)-1-piperidyl] ethanone (479 mg, 1.72 mmol, 19.86% yield, 69% purity) as a light yellow oil.

Step 2

To a solution of 2-chloro-1-[4-(hydroxymethyl)-1-piperidyl] ethanone (100 mg, 521.77 μmol, 1.1 eq) and benzyl (3S)-3-methylpiperazine-1-carboxylate (111.13 mg, 474.34 μmol, 1 eq) in MeCN (2 mL) was added DIEA (306.52 mg, 2.37 mmol, 413.10 μL, 5 eq) at 25° C. The mixture was stirred at 60° C. for 16 hr. LC-MS (EB2049-138-P1A) showed Reactant 1 was consumed completely and desired mass was detected. The mixture was cooled to room temperature and concentrated, and then the residue was extracted with Ethyl acetate (10 mL). The organic layer was washed with water (10 mL×2), brine (10 mL×2), dried over anhydrous Na2SO4, filtered and concentrated in vacuo to afford benzyl (3S)-4-[2-[4-(hydroxymethyl)-1-piperidyl]-2-oxo-ethyl]-3-methyl-piperazine-1-carboxylate (84 mg, 109.99 μmol, 23.19% yield, 51% purity) as a light yellow oil. The crude product was used into the next step without further purification.

Step 3

To a solution of tert-butyl (3S)-4-[2-[4-(hydroxymethyl)-1-piperidyl]-2-oxo-ethyl]-3-methyl-piperazine-1-carboxylate (500 mg, 1.41 mmol, 1 eq) in DCM (5 mL) was added DMP (1.19 g, 2.81 mmol, 870.93 μL, 2 eq). The mixture was stirred at 25° C. for 2 hr. LC-MS (EB2049-145-P1A) showed Reactant 1 was consumed completely and desired mass was detected. The reaction mixture was diluted with water (10 mL) and extracted with Ethyl acetate (10 mL). The combined organic layers were washed with brine (10 mL), dried over Na2SO4, filtered and concentrated under reduced pressure to give a residue. The residue was purified by flash silica gel chromatography (ISCO®; 20 SepaFlash® Silica Flash Column, Eluent of 0-100% Ethyl acetate/Petroleum ether gradient @ 40 mL/min). tert-butyl (3S)-4-[2-(4-formyl-1-piperidyl)-2-oxo-ethyl]-3-methyl-piperazine-1-carboxylate (240 mg, 679.01 μmol, 48.27% yield) as a colorless oil Step 4

To a solution of tert-butyl (3S)-4-[2-(4-formyl-1-piperidyl)-2-oxo-ethyl]-3-methyl-piperazine-1-carboxylate (110 mg, 311.21 μmol, 1 eq) and 2-(2,6-dioxo-3-piperidyl)-5-piperazin-1-yl-isoindoline-1,3-dione (127.85 mg, 373.46 μmol, 1.2 eq) in MeOH (5 mL) and HOAc (1 mL) was added borane; 2-methylpyridine (66.58 mg, 622.43 μmol, 2 eq) and DIEA (80.44 mg, 622.43 μmol, 108.42 μL, 2 eq). The mixture was stirred at 25° C. for 16 hr. LC-MS (EB2049-148-P1A) showed Reactant 1 was consumed completely and desired mass was detected. The reaction mixture was diluted with water (10 mL) and extracted with Ethyl acetate (10 mL). The combined organic layers were washed with brine (10 mL), dried over Na2SO4, filtered and concentrated under reduced pressure to give a residue. The residue was purified by flash silica gel chromatography (ISCO®; 12 g SepaFlash® Silica Flash Column, Eluent of 0-100% (20 min) Ethyl acetate/Petroleum ether gradient @ 40 mL/min, 0-10% (15 min) MeOH/DCM @ 35 mL/min) to afford tert-butyl (3S)-4-[2-[4-[[4-[2-(2,6-dioxo-3-piperidyl)-1,3-dioxo-isoindolin-5-yl]piperazin-1-yl]methyl]-1-piperidyl]-2-oxo-ethyl]-3-methyl-piperazine-1-carboxylate (200 mg, 294.20 μmol, 94.53% yield) as a light yellow oil Step 5

To a solution of tert-butyl (3S)-4-[2-[4-[[4-[2-(2,6-dioxo-3-piperidyl)-1,3-dioxo-isoindolin-5-yl]piperazin-1-yl]methyl]-1-piperidyl]-2-oxo-ethyl]-3-methyl-piperazine-1-carboxylate (200 mg, 294.20 μmol, 1 eq) in DCM (5 mL) was added TFA (5 mL). The mixture was stirred at 25° C. for 1 hr. TLC indicated no Reactant 1 remained, and one major new spot with larger polarity was detected. The reaction mixture was concentrated under reduced pressure to remove solvent to afford 2-(2, 6-dioxo-3-piperidyl)-5-[4-[[1-[2-[(2S)-2-methylpiperazin-1-yl] acetyl]-4-piperidyl] methyl] piperazin-1-yl] isoindoline-1, 3-dione (560 mg, crude, 12TFA) as a light yellow oil. The crude product was used into the next step without further purification.

Step 6

To a solution of 2-(2,6-dioxo-3-piperidyl)-5-[4-[[1-[2-[(2S)-2-methylpiperazin-1-yl]acetyl]-4-piperidyl]methyl]piperazin-1-yl]isoindoline-1,3-dione (560 mg, 287.48 μmol, 1 eq, 12TFA) and 3-(6-chloropyrimidin-4-yl)-5-(1-methylcyclopropoxy)-2H-indazole (35 mg, 116.38 μmol, 4.05 e-1 eq) in DMSO (3 mL) was added DIEA (445.86 mg, 3.45 mmol, 600.88 μL, 12 eq). The mixture was stirred at 110° C. for 16 hr. LC-MS (EB2049-152-P1A) showed Reactant 1 was consumed completely and desired mass was detected. The reaction mixture was diluted with water (20 mL) and extracted with Ethyl acetate (30 mL). The combined organic layers were washed with brine (20 mL), dried over Na2SO4, filtered and concentrated under reduced pressure to give a residue. The crude product was purified by reversed-phase HPLC (column: Phenomenex Luna C18 75*30 mm*3 um; mobile phase: [water (0.225% FA)-ACN]; B %: 18%-48%, 35 min) to afford 2-(2,6-dioxo-3-piperidyl)-5-[4-[[1-[2-[(2S)-2-methyl-4-[6-[5-(1-methylcyclopropoxy)-2H-indazol-3-yl]pyrimidin-4-yl]piperazin-1-yl]acetyl]-4-piperidyl]methyl]piperazin-1-yl]isoindoline-1,3-dione (41 mg, 48.58 μmol, 16.90% yield, 100% purity) as a yellow solid.

Exemplary Synthesis of Compound 60

Step 1

To a solution of ethyl 4-hydroxycyclohexanecarboxylate (1 g, 5.81 mmol, 1 eq) in THF (15 mL) was added TEA (881.33 mg, 8.71 mmol, 1.21 mL, 1.5 eq) and TMSCl (693.91 mg, 6.39 mmol, 810.65 μL, 1.1 eq) at 0° C., and the reaction mixture was stirred at 25° C. for 1 hour. The reaction mixture was filtered and the filtrate was concentrated under reduced pressure to give a residue. Then to a stirred solution of above residue and benzyl 4-formylpiperidine-1-carboxylate (1.72 g, 6.97 mmol, 1.2 eq) in DCM (15 mL) was added Et3SiH (810.19 mg, 6.97 mmol, 1.11 mL, 1.2 eq) and TMSOTf (709.80 mg, 3.19 mmol, 577.07 μL, 0.55 eq) dropwise at −60° C., and the reaction mixture was stirred at 0° C. under N2 for 2 hours. TLC (Petroleum ether:Ethyl acetate=3:1, PMA, Rf=0.52) showed a main spot formed. The reaction mixture was quenched by addition water (30 mL) and extracted with DCM (30 mL*3). The combined organic layers were washed with brine (30 mL), dried over Na2SO4, filtered and concentrated under reduced pressure to give a residue. The residue was purified by flash silica gel chromatography (ISCO®; 40 g SepaFlash® Silica Flash Column, Eluent of 0-17% Ethyl acetate/Petroleum ethergradient @ 50 mL/min). Compound benzyl 4-[(4-ethoxycarbonylcyclohexoxy)methyl]piperidine-1-carboxylate (1.88 g, 4.66 mmol, 80.24% yield) was obtained as a colorless oil.

Step 2

To a solution of benzyl 4-[(4-ethoxycarbonylcyclohexoxy)methyl]piperidine-1-carboxylate (500 mg, 1.24 mmol, 1 eq) in DCM (10 mL) was added DIBALH (1 M, 1.36 mL, 1.1 eq) drop-wise at −70° C. over a period of 30 mins under N2. During which the temperature was maintained below −70° C. The reaction mixture was warmed to 0° C. stirred for 1.5 hours. LCMS showed ~71% desire compound and the starting materials was consumed completely. To the reaction mixture was added sat NH4Cl under ice-cooling. Saturated brine was added thereto, followed by extraction with DCM (80 mL×3). The organic layer was dried over anhydrous magnesium sulfate and concentrated. Compound benzyl 4-[[4-(hydroxymethyl)cyclohexoxy]methyl]piperidine-1-carboxylate Step 3

To a mixture of benzyl 4-[[4-(hydroxymethyl)cyclohexoxy]methyl]piperidine-1-carboxylate (440 mg, 1.22 mmol, 1 eq), DMAP (44.61 mg, 365.17 μmol, 0.3 eq) and TEA (369.51 mg, 3.65 mmol, 508.27 μL, 3 eq) in DCM (10 mL) was added TosCl (348.09 mg, 1.83 mmol, 1.5 eq) at 0° C. The mixture was stirred at 25° C. for 4 hours. LCMS showed ~36% of desired compound and TLC (Petroleum ether:Ethyl acetate=1:1, Rf=0.57, PMA) showed a main new spot formed. The reaction mixture was quenched by addition water (30 mL) and extracted with DCM (30 mL*3). The combined organic layers were washed with brine (30 mL), dried over Na2SO4, filtered and concentrated under reduced pressure to give a residue. The residue was purified by flash silica gel chromatography (ISCO®; 20 g SepaFlash® Silica Flash Column, Eluent of 0-38% Ethyl acetate/Petroleum ethergradient @ 40 mL/min). Compound benzyl 4-[[4-(p-tolylsulfonyloxymethyl)cyclohexoxy]methyl]piperidine-1-carboxylate (300 mg, 523.60 μmol, 43.02% yield, 90% purity) was obtained as a colorless oil.

Step 4

To a solution of benzyl 4-[[4-(p-tolylsulfonyloxymethyl)cyclohexoxy]methyl]piperidine-1-carboxylate (300 mg, 581.78 μmol, 1 eq) and 2-(2,6-dioxo-3-piperidyl)-5-piperazin-1-yl-isoindoline-1,3-dione (239.01 mg, 698.13 μmol, 1.2 eq) in CH3CN (10 mL) was added KI (965.76 mg, 5.82 mmol, 10 eq) and DIEA (751.91 mg, 5.82 mmol, 1.01 mL, 10 eq), then the mixture was stirred at 100° C. for 16 hours. LCMS showed desired compound and the starting materials was consumed completely, TLC (Methanol:Dichloromethane=10:1, Rf=0.43, UV=254 nm) showed new spots formed. The reaction mixture was concentrated under reduced pressure to give a residue. The residue was purified by flash silica gel chromatography (ISCO®; 12 g SepaFlash® Silica Flash Column, Eluent of 0-3% Methanol:Dichloromethane @ 40 mL/min). Compound benzyl 4-[[4-[[4-[2-(2,6-dioxo-3-piperidyl)-1,3-dioxo-isoindolin-5-yl]piperazin-1-yl]methyl]cyclohexoxy]methyl]piperidine-1-carboxylate (760 mg, 554.09 μmol, 95.24% yield, 50% purity) was obtained as a yellow solid.

Step 5

To a solution of benzyl 4-[[4-[[4-[2-(2,6-dioxo-3-piperidyl)-1,3-dioxo-isoindolin-5-yl]piperazin-1-yl]methyl]cyclohexoxy]methyl]piperidine-1-carboxylate (300 mg, 437.44 μmol, 1 eq) in TFA (6.93 g, 60.78 mmol, 4.50 mL, 138.94 eq) and the solution was stirred at 70° C. for 40 min. LCMS showed ~66% desire compound and the starting materials was consumed completely. The reaction mixture was concentrated under reduced pressure to give a residue. Compound 2-(2,6-dioxo-3-piperidyl)-5-[4-[[4-(4-piperidylmethoxy)cyclohexyl]methyl]piperazin-1-yl]isoindoline-1,3-dione (310 mg, crude, TFA) was obtained as a light yellow oil.

Step 6

To a solution of 2-(2,6-dioxo-3-piperidyl)-5-[4-[[4-(4-piperidylmethoxy)cyclohexyl]methyl]piperazin-1-yl]isoindoline-1,3-dione (50 mg, 90.63 μmol, 1 eq) and 3-(6-chloropyrimidin-4-yl)-5-(1-methylcyclopropoxy)-2H-indazole (35.43 mg, 117.82 μmol, 1.3 eq) in DMSO (3 mL) was added DIEA (117.14 mg, 906.33 μmol, 157.87 μL, 10 eq), then the mixture was stirred at 90° C. for 16 hours. LCMS showed ~42.8% of desired compound and the starting materials was consumed. The residue was purified by prep-HPLC (column: 3_Phenomenex Luna C18 75*30 mm*3 um; mobile phase: [water (0.225% FA)-ACN]; B %: 0%-40%, 40 min). Compound 2-(2,6-dioxo-3-piperidyl)-5-[4-[[4-[[1-[6-[5-(1-methylcyclopropoxy)-2H-indazol-3-yl] pyrimidin-4-yl]-4-piperidyl]methoxy]cyclohexyl]methyl] piperazin-1-yl]isoindoline-1,3-dione (16.5 mg, 19.98 μmol, 22.04% yield, 98.8% purity) was obtained as a yellow solid.

Exemplary Synthesis of Compound 61

Step 1

A mixture of tert-butyl 4-(hydroxymethyl)piperidine-1-carboxylate (1 g, 4.64 mmol, 1 eq), MsCl (585.29 mg, 5.11 mmol, 395.46 μL, 1.1 eq) in DCM (20 mL) at 0° C. was treated dropwise with TEA (940.03 mg, 9.29 mmol, 1.29 mL, 2 eq). The reaction mixture was stirred at 0° C. for 1.5 h. TLC (Petroleum ether:Ethyl acetate=5:1, Rf=0.53) showed no start material and a new spot. The mixture was diluted with DCM (25 mL*3) and washed with 1 M $NaHCO_3$ (200 mL×2) and brine (25 mL). The DCM layer was dried over Na2SO4, filtered, and the filtrate was concentrated to colourless oil.

Step 2

To a solution of benzyl 4-hydroxypiperidine-1-carboxylate (1.13 g, 4.81 mmol, 1 eq) in DMF (12 mL) was added NaH (433.33 mg, 10.83 mmol, 60% purity, 2.25 eq) at 0° C. The mixture was stirred at 0° C. for 0.5 hr. After that, tert-butyl 4-(methylsulfonyloxymethyl) piperidine-1-carboxylate (1.41 g, 4.81 mmol, 1 eq) was added, the mixture was stirred at 60° C. for 16 h. LCMS showed desired MS and no start material. On completion, the reaction mixture was quenched by water (30 mL) at 0° C. and extracted with EtOAc (15 mL*3). The combined organic layers were dried over Na2SO4, filtered and concentrated in vacuo to give a residue. The residue was by silica gel column chromatography (petroleum ether/ethyl acetate=10:1) to give the tert-butyl 4-[(1-benzyloxycarbonyl-4-piperidyl)oxymethyl]piperidine-1-carboxylate (277 mg, 640.39 μmol, 13.31% yield) as colourless oil.

Step 3

To a solution of tert-butyl 4-[(1-benzyloxycarbonyl-4-piperidyl)oxymethyl]piperidine-1-carboxylate (270 mg, 624.20 μmol, 1 eq) in EtOH (5 mL) was added Pd/C (30 mg, 25.45 μmol, 10% purity, 4.08 e-2 eq) under N2. The suspension was degassed under vacuum and purged with H2 three times. The mixture was stirred under H2 (15 psi) at 25° C. for 1 h. LCMS was showed desired MS and no start material. The reaction mixture was concentrated in vacuo to give the crude product as colourless oil.

Step 4

To a solution of tert-butyl 4-(4-piperidyloxymethyl)piperidine-1-carboxylate (180 mg, 603.18 μmol, 1 eq) and 1-[2-(2,6-dioxo-3-piperidyl)-1,3-dioxo-isoindolin-5-yl]piperidine-4-carbaldehyde (222.80 mg, 603.18 μmol, 1 eq) in MeOH (10 mL) was added HOAc (1 mL) and stirred at 25° C. for 10 min. Then borane; 2-methylpyridine (129.03 mg, 1.21 mmol, 2 eq) was added and the mixture was stirred at 25° C. for 16 h under N2. The LCMS showed the reaction completed. The residue was added water (5 mL). The aqueous phase was extracted with ethyl acetate (8 mL*3). The combined organic phase was washed with brine (10 mL*2) and dried with anhydrous Na2SO4, filtered and concentrated in vacuum. The residue was purified by Combi Flash (0-8% MeOH in DCM) to afford tert-butyl 4-[[1-[[1-[2-(2,6-dioxo-3-piperidyl)-1,3-dioxo-isoindolin-5-yl]-4-piperidyl]methyl]-4-piperidyl]oxymethyl]piperidine-1-carboxylate (390 mg, 598.35 μmol, 99.20% yield) as green oil.

Step 5

To a mixture of tert-butyl 4-[[1-[[1-[2-(2,6-dioxo-3-piperidyl)-1,3-dioxo-isoindolin-5-yl]-4-piperidyl]methyl]-4-piperidyl]oxymethyl]piperidine-1-carboxylate (120 mg, 184.11 μmol, 1 eq) in DCM (4 mL) was added TFA (1.54 g, 13.51 mmol, 1 mL, 73.36 eq) at 25° C. then stirred for 1 hour. LCMS was desired 91% of the compound and no start material. The mixture was concentrated in vacuum to afford 2-(2,6-dioxo-3-piperidyl)-5-[4-[[4-(4-piperidylmethoxy)-1-piperidyl]methyl]-1-piperidyl]isoindoline-1,3-dione (105 mg, crude, TFA) as yellow oil Step 6

To mixture of 2-(2,6-dioxo-3-piperidyl)-5-[4-[[4-(4-piperidylmethoxy)-1-piperidyl]methyl]-1-piperidyl]isoindoline-1,3-dione (100 mg, 150.22 μmol, 1 eq, TFA) and 3-(6-chloropyrimidin-4-yl)-5-(1-methylcyclopropoxy)-2H-indazole (24.86 mg, 82.67 μmol, 0.55 eq) in DMSO (3 mL) was added DIEA (232.97 mg, 1.80 mmol, 313.98 μL, 12 eq) and stirred at 90° C. for 16 hr. The LCMS showed 64% of desired compound and no start material. The mixture was poured water (15 mL). The aqueous phase was extracted with ethyl acetate (10 mL*3). The combined organic phase was washed with brine (10 mL), dried with anhydrous Na2SO4, filtered and concentrated in vacuum. The residue was purified by prep-HPLC (column: 3_Phenomenex Luna C18 75*30 mm*3 um; mobile phase: [water (0.225% FA)-ACN]; B %: 0%-40%, 40 min) to afford 2-(2,6-dioxo-3-piperidyl)-5-[4-[[4-[[1-[6-[5-(1-methylcyclopropoxy)-2H-indazol-3-yl]pyrimidin-4-yl]-4-piperidyl]methoxy]-1-piperidyl]methyl]-1-piperidyl]isoindoline-1,3-dione (30.1 mg, 35.41 μmol, 23.57% yield, 96% purity) as a yellow solid.

Exemplary Synthesis of Compound 62

Step 1

To a mixture of 1-[2-(2,6-dioxo-3-piperidyl)-1,3-dioxo-isoindolin-5-yl]piperidine-4-carboxylic acid (103.31 mg, 268.08 μmol, 1 eq) in DMF (6 mL) was added HATU (132.51 mg, 348.50 μmol, 1.3 eq) then the mixture was stirred at 25° C. for 30 min, then tert-butyl 4-(4-piperidyloxymethyl)piperidine-1-carboxylate (80 mg, 268.08 μmol, 1 eq) and DIEA (103.94 mg, 804.24 μmol, 140.08 μL, 3 eq) was added the mixture and stirred for 1 h. TLC (DCM: MeOH=10:1, Rf=0.58) showed no start material and a new spot. The residue was added water (5 mL). The aqueous phase was extracted with ethyl acetate (8 mL*3). The combined organic phase was washed with brine (10 mL*2), dried with anhydrous Na2SO4, filtered and concentrated in vacuum. It was purified by Combi Flash (SiO2 11% DCM in MeOH) to afford tert-butyl 4-[[1-[1-[2-(2,6-dioxo-3-piperidyl)-1,3-dioxo-isoindolin-5-yl]piperidine-4-carbonyl]-4- piperidyl]oxymethyl]piperidine-1-carboxylate (150 mg, 225.30 μmol, 84.04% yield) as green oil.

Step 2

To a mixture of tert-butyl 4-[[1-[1-[2-(2,6-dioxo-3-piperidyl)-1,3-dioxo-isoindolin-5-yl]piperidine-4-carbonyl]-4-piperidyl]oxymethyl]piperidine-1-carboxylate (150 mg, 225.30 μmol, 1 eq) in DCM (6 mL) was added TFA (2.31 g, 20.26 mmol, 1.5 mL, 89.92 eq) at 25° C. then stirred for 1 h. TLC (petroleum ether/ethyl acetate=1:1) showed no start material and a new spot. The mixture was concentrated in vacuum to afford 2-(2,6-dioxo-3-piperidyl)-5-[4-[4-(4-piperidylmethoxy)piperidine-1-carbonyl]-1-piperidyl]isoindoline-1,3-dione (150 mg, crude, TFA) as yellow oil.

Step 3

To mixture of 2-(2,6-dioxo-3-piperidyl)-5-[4-[4-(4-piperidylmethoxy)piperidine-1-carbonyl]-1-piperidyl]isoindoline-1,3-dione (150 mg, 220.69 μmol, 1 eq, TFA), 3-(6-chloropyrimidin-4-yl)-5-(1-methylcyclopropoxy)-2H-indazole (40 mg, 133.00 μmol, 6.03 e-1 eq) in DMSO (4 mL) was added DIEA (342.27 mg, 2.65 mmol, 461.29 μL, 12 eq) and stirred at 90° C. for 16 h. LCMS was showed the reaction completed. The residue was concentrated under reduced pressure to give a residue. It was purified by prep-HPLC (column: 3_Phenomenex Luna C18 75*30 mm*3 um; mobile phase: [water (0.225% FA)-ACN]; B %: 0%-40%, 40 min) to afford 2-(2,6-dioxo-3-piperidyl)-5-[4-[4-[[1-[6-[5-(1-methylcyclopropoxy)-2H-indazol-3-yl]pyrimidin-4-yl]-4-piperidyl]methoxy]piperidine-1-carbonyl]-1-piperidyl]isoindoline-1,3-dione (14.3 mg, 16.89 μmol, 7.65% yield, 98% purity) as a yellow solid.

Exemplary Synthesis of Compound 63

Step 1

A mixture of tert-butyl 1-imino-1-oxo-1,4-thiazinane-4-carboxylate (100 mg, 426.78 μmol, 1 eq), benzyl 4-formylpiperidine-1-carboxylate (158.31 mg, 640.16 μmol, 1.5 eq), borane; 2-methylpyridine (136.95 mg, 1.28 mmol, 3 eq) in MeOH (10 mL) was added AcOH (2 mL) borane; 2-methylpyridine (136.95 mg, 1.28 mmol, 3 eq) and then the mixture was stirred at 25° C. for 16 hr under N2 atmosphere. LCMS showed the starting material was consumed completely and desired MS found. TLC (Petroleum ether:Ethyl acetate=0:1) showed several new spots. The reaction mixture was concentrated under reduced pressure. The residue was purified by silica gel column chromatography (0 to 80% Ethyl acetate in Petroleum ether) to give tert-butyl 1-[(1-benzyloxycarbonyl-4-piperidyl)methylimino]-1-oxo-1,4-thiazinane-4-carboxylate (199 mg, 260.71 μmol, 61.09% yield, 61% purity) as a colorless gum.

Step 2

A mixture of tert-butyl 1-[(1-benzyloxycarbonyl-4-piperidyl)methylimino]-1-oxo-1,4-thiazinane-4-carboxylate (199 mg, 427.40 μmol, 1 eq) in DCM (3 mL) was added TFA (4.62 g, 40.52 mmol, 3 mL, 94.80 eq) and then the mixture was stirred at 25° C. for 1 hr. TLC (Petroleum ether:Ethyl acetate=0:1) showed one new major spot. The reaction mixture was concentrated under reduced pressure to give benzyl 4-[[(1-oxo-1,4-thiazinan-1-ylidene)amino]methyl]piperidine-1-carboxylate (200 mg, crude, TFA) as a yellow gum.

Step 3

A mixture of benzyl 4-[[(1-oxo-1,4-thiazinan-1-ylidene)amino]methyl]piperidine-1-carboxylate (156 mg, 426.83 μmol, 1 eq), 1-[2-(2,6-dioxo-3-piperidyl)-1,3-dioxo-isoindolin-5-yl]piperidine-4-carbaldehyde (157.66 mg, 426.83 μmol, 1 eq) in MeOH (10 mL) was added AcOH (1 mL), borane; 2-methylpyridine (91.31 mg, 853.65 μmol, 2 eq) and then the mixture was stirred at 25° C. for 2 hr under N2 atmosphere. LCMS showed the starting material was consumed completely and desired MS found. TLC (Dichloromethane:Methanol=10:1) showed several new spots The reaction mixture was filtered and the filtrate was concentrated under reduced pressure. The residue was purified by silica gel column chromatography (0 to 30% Methanol in Dichloromethane) to give benzyl 4-[[[4-[[1-[2-(2,6-dioxo-3-piperidyl)-1,3-dioxo-isoindolin-5-yl]-4-piperidyl]methyl]-1-oxo-1,4-thiazinan-1-ylidene]amino]methyl]piperidine-1-carboxylate (200 mg, 180.84 μmol, 42.37% yield, 65% purity) as a yellow gum Step 4

A mixture of benzyl 4-[[[4-[[1-[2-(2,6-dioxo-3-piperidyl)-1,3-dioxo-isoindolin-5-yl]-4-piperidyl]methyl]-1-oxo-1,4-thiazinan-1-ylidene]amino]methyl]piperidine-1-carboxylate (200 mg, 278.22 μmol, 1 eq) in TFA (31.72 mg, 278.22 μmol, 20.60 μL, 1 eq) and then the mixture was stirred at 70° C. for 1 hr under N2 atmosphere. TLC (Dichloromethane:Methanol=10:1) showed one new spot. The reaction mixture was concentrated under reduced pressure to give 2-(2,6-dioxo-3-piperidyl)-5-[4-[[1-oxo-1-(4-piperidylmethylimino)-1,4-thiazinan-4-yl]methyl]-1-piperidyl]isoindoline-1,3-dione (200 mg, crude, TFA) as a yellow gum.

Step 5

A mixture of 2-(2,6-dioxo-3-piperidyl)-5-[4-[[1-oxo-1-(4-piperidylmethylimino)-1,4-thiazinan-4-yl]methyl]-1-piperidyl]isoindoline-1,3-dione (58.33 mg, 99.75 μmol, 1 eq), 3-(6-chloropyrimidin-4-yl)-5-(1-methylcyclopropoxy)-2H-indazole (30 mg, 99.75 μmol, 1 eq) in DMSO (3 mL) was added DIEA (38.68 mg, 299.26 μmol, 52.13 μL, 3 eq) and then the mixture was stirred at 100° C. for 12 hr under N2 atmosphere. LCMS showed the starting material was consumed completely and desired MS found. The reaction mixture was filtered and concentrated under reduced pressure. The crude product was purified by reversed-phase HPLC (column: 3_Phenomenex Luna C18 75*30 mm*3 um; mobile phase: [water (0.225% FA)-ACN]; B %: 0%-35%, 40 min) to give 2-(2,6-dioxo-3-piperidyl)-5-[4-[[1-[[1-[6-[5-(1-methylcyclopropoxy)-1H-indazol-3-yl]pyrimidin-4-yl]-4-piperidyl]methylimino]-1-oxo-1,4-thiazinan-4-yl]methyl]-1-piperidyl]isoindoline-1,3-dione (25.3 mg, 29.50 μmol, 29.57% yield, 99% purity) as a yellow solid.

Exemplary Synthesis of Compound 64

Step 1

To a solution of 3-(5-bromo-1-oxo-isoindolin-2-yl)piperidine-2,6-dione (600 mg, 1.86 mmol, 1 eq) and 4-(dimethoxymethyl)piperidine (739.11 mg, 4.64 mmol, 2.5 eq) in DMSO (10 mL) was added Pd-PEPPSI-pent Cl-Opicoline (100.82 mg, 185.68 μmol, 0.1 eq) and Cs2CO3 (1.21 g, 3.71 mmol, 2 eq) stirred at 80° C. for 16 h under N2. TLC (Petroleum ether:Ethyl acetate=0:1, Rf=0.4) showed the reaction a new spot. The reaction was quenched by NH4Cl (20 mL) solution and extracted with ethyl acetate (3*20 mL). The combined organic phases were washed with water, dried with Na2SO4, concentrated in vacuum to give a residue. The residue was purified by silica gel chromatography (Petroleum ether/Ethyl acetate=100/1, 1/100) to afford 3-[5-[4-(dimethoxymethyl)-1-piperidyl]-1-oxo-isoindolin-2-yl]piperidine-2,6-dione (560 mg, 1.39 mmol, 75.13% yield) as a yellow solid.

Step 2

A solution of 3-[5-[4-(dimethoxymethyl)-1-piperidyl]-1-oxo-isoindolin-2-yl]piperidine-2,6-dione (70 mg, 174.37 μmol, 1 eq) in THF (2 mL) and HCl (2 M, 2 mL, 22.94 eq) was stirred at 20° C. for 2 hr. The reaction mixture was poured into H2O (20 mL) and basified with aqueous NaHCO3 till PH=8. The mixture was extracted with ethyl acetate (20 mL*5) and dried over anhydrous Na2SO4, concentrated in vacuum to give a residue. The residue was without any purification, which used directly in the next step. Compound 1-[2-(2,6-dioxo-3-piperidyl)-1-oxo-isoindolin-5-yl]piperidine-4-carbaldehyde (61 mg, 159.63 μmol, 91.55% yield, 93% purity) as yellow solid.

Step 3

To a solution of benzyl (3S)-4-[2-(1-tert-butoxycarbonyl-4-fluoro-4-piperidyl)ethyl]-3-methyl-piperazine-1-carboxylate (410 mg, 884.41 μmol, 1 eq) in EtOH (20 mL) was added Pd/C (500 mg, 1.77 mmol, 197.63 μL, 10% purity, 2 eq) under N2. The suspension was degassed under vacuum and purged with H2 several times. The mixture was stirred under H2 (15 psi) at 25° C. for 1 h. TLC showed the reaction was completed. The suspension was filtered through a pad of Celite or silica gel and filter cake was washed with Ethyl acetate (50 mL×3). The combined filtrates were concentrated in vacuum to give tert-butyl 4-fluoro-4-[2-[(2S)-2-methylpiperazin-1-yl]ethyl]piperidine-1-carboxylate (270 mg, crude) as a yellow gum.

Step 4

To a mixture of 2-[[3-(6-chloropyrimidin-4-yl)-5-(1-methylcyclopropoxy)indazol-2-yl]methoxy]ethyl-trimethyl-silane (250 mg, 580.04 μmol, 1 eq), ert-butyl 4-fluoro-4-[2-[(2S)-2-methylpiperazin-1-yl]ethyl]piperidine-1-carboxylate (270 mg, 819.54 μmol, 1.41 eq) in DMSO (5 mL) was added Et3N (176.08 mg, 1.74 mmol, 242.21 μL, 3 eq) in one portion and then was stirred at 100° C. for 1 h. TLC and LCMS showed the starting material was consumed completely. The mixture was cooled to 20° C., then the residue was poured into water (5 mL). The aqueous phase was extracted with ethyl acetate (3×5 mL). The combined organic phase was washed with brine (2×5 mL), dried with anhydrous Na2SO4, filtered and concentrated in vacuum. The residue was purified by silica gel chromatography (100-200 mesh silica gel, 0-5% (5 min) of Ethyl acetate in Petroleum ether, 5% (10 min) of Ethyl acetate in Petroleum ether, 5%-30% (5 min) of Ethyl acetate in Petroleum ether, 30% (5 min) of Ethyl acetate in Petroleum ether). The crude was purified by prep-TLC (Petroleum ether:Ethyl acetate=10:1) to give tert-butyl 4-fluoro-4-[2-[(2S)-2-methyl-4-[6-[5-(1-methylcyclopropoxy)-2-(2-trimethylsilylethoxymethyl)indazol-3-yl]pyrimidin-4-yl]piperazin-1-yl]ethyl]piperidine-1-carboxylate (140 mg, 190.59 μmol, 32.86% yield, 98.56% purity) as a yellow oil.

Step 5

To a mixture of tert-butyl 4-fluoro-4-[2-[(2S)-2-methyl-4-[6-[5-(1-methylcyclopropoxy)-2-(2-trimethylsilylethoxymethyl)indazol-3-yl]pyrimidin-4-yl]piperazin-1-yl]ethyl]piperidine-1-carboxylate (140 mg, 193.37 μmol, 1 eq) in MeOH (5 mL) was added HCl/EtOAc (4 M, 2 mL, 41.37 eq) in one portion at 25° C. The mixture was stirred at 65° C. for 0.5 h. LCMS showed the reaction was completed. The mixture was concentrated in vacuum to give 3-[6-[(3S)-4-[2-(4-fluoro-4-piperidyl)ethyl]-3-methyl-piperazin-1-yl]pyrimidin-4-yl]-5-(1-methylcyclopropoxy)-2H-indazole (100 mg, 181.63 μmol, 93.93% yield, 96.28% purity, HCl) as a yellow solid.

Step 6

To a mixture of 3-[6-[(3S)-4-[2-(4-fluoro-4-piperidyl)ethyl]-3-methyl-piperazin-1-yl]pyrimidin-4-yl]-5-(1-methylcyclopropoxy)-2H-indazole (100 mg, 202.59 μmol, 1.33 eq) and 1-[2-(2,6-dioxo-3-piperidyl)-1-oxo-isoindolin-5-yl]piperidine-4-carbaldehyde (54 mg, 151.95 μmol, 1 eq) in MeOH (10 mL) was added borane; 2-methylpyridine (32.50 mg, 303.89 μmol, 2 eq) and HOAc (1 mL) in one portion at 20° C. under N2. The mixture was stirred at 20° C. for 16 h. LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (0.225% FA)-ACN]; B %: 0%-30%, 40 min) to give 3-[5-[4-[[4-fluoro-4-[2-[(2S)-2-methyl-4-[6-[5-(1-methylcyclopropoxy)-2H-indazol-3-yl]pyrimidin-4-yl]piperazin-1-yl]ethyl]-1-piperidyl]methyl]-1-piperidyl]-1-oxo-isoindolin-2-yl]piperidine-2,6-dione (22.5 mg, 26.69 μmol, 17.57% yield, 98.82% purity) as an off-white solid.

Exemplary Synthesis of Compound 65

Compound 65 was prepared in a manner analogous to compound 64.

Exemplary Synthesis of Compound 66

Compound 66 was prepared in a manner analogous to compound 64.

Exemplary Synthesis of Compound 67

Step 1

To a solution of 2-(2,6-dioxo-3-piperidyl)-5-[4-(4-piperidylmethyl)piperazin-1-yl]isoindoline-1,3-dione (300 mg, 682.58 μmol, 1 eq, TFA) and tert-butyl 4-formylpiperidine-1-carboxylate (218.36 mg, 1.02 mmol, 1.5 eq) in MeOH (5 mL) was added HOAc (0.5 mL) and borane; 2-methylpyridine (146.02 mg, 1.37 mmol, 2 eq) in one portion at 20° C. under N2. The solution was stirred at 20° C. for 16 h. TLC (DCM:MeOH=10:1, Rf=0.43) showed the reaction was completed, and a main spot (Rf=0.43) was showed on TLC. LCMS showed there was desired MS. The residue was poured into water (20 mL). The aqueous phase was extracted with ethyl acetate (3×20 mL). The combined organic phase was washed with brine (2×20 mL), dried with anhydrous Na2SO4, filtered and concentrated in vacuum. The residue was purified by silica gel chromatography (column: 12 g, 100-200 mesh silica gel, 0-10% (5 min) of MeOH in DCM, 10% (10 min) of MeOH in DCM) to give tert-butyl 4-[[4-[[4-[2-(2,6-dioxo-3-piperidyl)-1,3-dioxo-isoindolin-5-yl]piperazin-1-yl]methyl]-1-piperidyl]methyl]piperidine-1-carboxylate (430 mg, 675.27 μmol, 98.93% yield) was obtained as a yellow gum.

Step 2

To a solution of tert-butyl 4-[[4-[[4-[2-(2,6-dioxo-3-piperidyl)-1,3-dioxo-isoindolin-5-yl]piperazin-1-yl]methyl]-1-piperidyl]methyl]piperidine-1-carboxylate (430 mg, 675.27 μmol, 1 eq) in DCM (2 mL) was added TFA (230.98 mg, 2.03 mmol, 149.99 μL, 3 eq) in one portion at 20° C. under N2. The mixture was stirred at 20° C. for 30 min to give yellow solution. TLC (DCM:MeOH=10:1, Rf=0.43) showed the starting material was completed. The solution was concentrated in vacuum to give 2-(2,6-dioxo-3-piperidyl)-5-[4-[[1-(4-piperidylmethyl)-4-piperidyl]methyl]piperazin-1-yl]isoindoline-1,3-dione (500 mg, 621.15 μmol, 91.99% yield, 95% purity, 2TFA) as a yellow gum.

Step 3

To a mixture of 3-(6-chloropyrimidin-4-yl)-5-(1-methylcyclopropoxy)-1H-indazole (60 mg, 199.51 μmol, 1 eq) and 2-(2,6-dioxo-3-piperidyl)-5-[4-[[1-(4-piperidylmethyl)-4-piperidyl]methyl]piperazin-1-yl]isoindoline-1,3-dione (107.07 mg, 199.51 μmol, 1 eq) in DMSO (5 mL) was added DIEA (77.35 mg, 598.52 μmol, 104.25 μL, 3 eq) in one portion at 20° C. under N2. The mixture was stirred at 80° C. for 16 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 30; FlowRate: 25 mL/min; Gradient Time: 35 min; 100% B Hold Time: 1 min) to give 2-(2,6-dioxo-3-piperidyl)-5-[4-[[1-[[1-[6-[5-(1-methylcyclopropoxy)-2H-indazol-3-yl]pyrimidin-4-yl]-4-piperidyl]methyl]-4-piperidyl]methyl]piperazin-1-yl]isoindoline-1,3-dione (15.6 mg, 19.36 μmol, 9.70% yield, 99.39% purity) as a yellow solid.

Exemplary Synthesis of Compound 68

Step 1

To a solution of 2-(2,6-dioxo-3-piperidyl)-5-[4-(piperazin-1-ylmethyl)-1-piperidyl]isoindoline-1,3-dione (325 mg, 587.14 μmol, 1 eq, TFA) in DCM (5 mL) was added DIEA (379.42 mg, 2.94 mmol, 511.35 μL, 5 eq) and stirred at 20° C. for 10 min. Then the mixture was concentrated. The residue and tert-butyl 4-formylpiperidine-1-carboxylate (125.22 mg, 587.14 μmol, 1 eq) in HOAC (1 mL) and MeOH (10 mL) was stirred at 20° C. for 20 min, then was added borane; 2-methylpyridine (125.60 mg, 1.17 mmol, 2 eq). Then the mixture was stirred at 25° C. for 16 h under N2. TLC (Dichloromethane:Methanol=10:1, Rf=0.3) showed no start material and a new spot. The residue was concentrated under reduced pressure to give a residue. The residue was purified by silica gel column chromatography (0 to 20% Dichloromethane in Methanol) to give tert-butyl 4-[[4-[[1-[2-(2,6-dioxo-3-piperidyl)-1,3-dioxo-isoindolin-5-yl]-4-piperidyl]methyl]piperazin-1-yl]methyl]piperidine-1-carboxylate (460 mg, 570.68 μmol, 97.20% yield, 79% purity) as a yellow solid.

Step 2

To a solution of tert-butyl 4-[[4-[[1-[2-(2,6-dioxo-3-piperidyl)-1,3-dioxo-isoindolin-5-yl]-4-piperidyl]methyl]piperazin-1-yl]methyl]piperidine-1-carboxylate (460 mg, 722.38 μmol, 1 eq) in DCM (3 mL) then was added TFA (3.08 g, 27.01 mmol, 2 mL, 37.39 eq). Then the mixture was stirred at 20° C. for 1 h. TLC (Dichloromethane:Methanol=10:1, Rf=0.01) showed no start material and a new spot. The residue was concentrated under reduced pressure to give 2-(2,6-dioxo-3-piperidyl)-5-[4-[[4-(4-piperidylmethyl)piperazin-1-yl]methyl]-1-piperidyl]isoindoline-1,3-dione (387 mg, crude, TFA) as a yellow gum.

Step 3

To a solution of 2-(2,6-dioxo-3-piperidyl)-5-[4-[[4-(4-piperidylmethyl)piperazin-1-yl]methyl]-1-piperidyl]isoindoline-1,3-dione (89.23 mg, 137.13 μmol, 8.25 e-1 eq, TFA) and 3-(6-chloropyrimidin-4-yl)-5-(1-methylcyclopropoxy)-1H-indazole (50 mg, 166.26 μmol, 1 eq) in DMSO (5 mL) then was added DIEA (107.44 mg, 831.30 μmol, 144.79 μL, 5 eq). Then the mixture was stirred at 80° C. for 16 h. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 15%-35%, 35 min) to give 2-(2,6-dioxo-3-piperidyl)-5-[4-[[4-[[1-[6-[5-(1-methylcyclopropoxy)-2H-indazol-3-yl]pyrimidin-4-yl]-4-piperidyl]methyl]piperazin-1-yl]methyl]-1-piperidyl]isoindoline-1,3-dione (22.7 mg, 26.94 μmol, 16.20% yield, 95.05% purity) as a yellow solid.

Exemplary Synthesis of Compound 69

Step 1

To a mixture of tert-butyl 1-oxa-6-azaspiro[2.5]octane-6-carboxylate (910.28 mg, 4.27 mmol, 1 eq) in EtOH (10 mL) was added benzyl (3S)-3-methylpiperazine-1-carboxylate (1 g, 4.27 mmol, 1 eq) at 20° C. under N2. The mixture was stirred at 90° C. for 16 hours. TLC (Dichloromethane: Methanol=10:1, Rf=0.57) and LCMS showed the reaction was completed. The residue was poured into water (10 mL). The aqueous phase was extracted with DCM (10 mL*3). The combined organic phase was washed with brine (10 mL*2), dried with anhydrous Na2SO4, filtered and concentrated in vacuum. The residue was purified by silica gel chromatography (20 g, 30 mL/min, 0-100% (20 min) of Ethyl acetate in Petroleum ether) to give benzyl (3S)-4-[(1-tert-butoxycarbonyl-4-hydroxy-4-piperidyl)methyl]-3-methyl-piperazine-1-carboxylate (1.4 g, 3.13 mmol, 73.29% yield) as a yellow oil.

Step 2

To a mixture of benzyl (3S)-4-[(1-tert-butoxycarbonyl-4-hydroxy-4-piperidyl)methyl]-3-methyl-piperazine-1-carboxylate (1.4 g, 3.13 mmol, 1 eq) in DCM (10 mL) was added DAST (605.04 mg, 3.75 mmol, 495.94 μL, 1.2 eq) drop-wise at −40° C. under N2. Then heated to 25° C. and stirred for 1 h to give colourless solution. LCMS showed there was desired MS. TLC (Petroleum ether:Ethyl acetate=1:1, Rf=0.74) showed no start material and a new spot. The reaction was cooled to 0° C. and quenched with aqueous $NaHCO_3$ to adjusted the pH=7-8. The aqueous phase was extracted with DCM (10 mL*3). The combined organic layers were washed with brine (10 mL*2) mL, dried over anhydrous sodium sulfate, filtered and concentrated under reduced pressure to give a residue. The residue was purified by silica gel chromatography (12 g, 0-18% (5 min) of Ethyl acetate in Petroleum ether, 18% (15 min) Ethyl acetate in Petroleum ether) to give benzyl (3S)-4-[(1-tert-butoxycarbonyl-4-fluoro-4-piperidyl)methyl]-3-methyl-piperazine-1-carboxylate (764 mg, 1.70 mmol, 54.35% yield) as a yellow oil.

Step 3

To a solution of benzyl (3S)-4-[(1-tert-butoxycarbonyl-4-fluoro-4-piperidyl)methyl]-3-methyl-piperazine-1-carboxylate (300 mg, 667.32 μmol, 1 eq) in DCM (20 mL) was added TFA (228.26 mg, 2.00 mmol, 148.22 μL, 3 eq) in one portion at 20° C. under N2. The mixture was stirred at 20° C. for 30 min to give colourless solution. LCMS showed the reaction was completed. The residue was poured into $NaHCO_3$ to adjusted the pH=7-8. The aqueous phase was extracted with DCM (30 mL*3). The combined organic phase was washed with brine (30 mL*2), dried with anhydrous Na2SO4, filtered and concentrated in vacuum to give benzyl (3S)-4-[(4-fluoro-4-piperidyl)methyl]-3-methyl-piperazine-1-carboxylate (200 mg, 475.04 μmol, 71.19% yield, 83% purity) as a colourless oil.

Step 4

To a mixture of benzyl (3S)-4-[(4-fluoro-4-piperidyl)methyl]-3-methyl-piperazine-1-carboxylate (200 mg, 572.34 μmol, 1 eq) and 1-[2-(2,6-dioxo-3-piperidyl)-1,3-dioxo-isoindolin-5-yl]piperidine-4-carbaldehyde (211.41 mg, 572.34 μmol, 1 eq) in MeOH (10 mL) was added borane; 2-methylpyridine (122.44 mg, 1.14 mmol, 2 eq) and HOAc (1 mL) in one portion at 20° C. under N2. The mixture was stirred at 20° C. for 1 h to give yellow solution. LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (0-20% of MeOH in DCM) to give benzyl (3S)-4-[[1-[[1-[2-(2,6-dioxo-3-piperidyl)-1,3-dioxo-isoindolin-5-yl]-4-fluoro-4-piperidyl]methyl]-4-piperidyl]methyl]-3-methyl-piperazine-1-carboxylate (373 mg, 530.72 μmol, 92.73% yield) as a yellow solid.

Step 5

To a mixture of benzyl (3S)-4-[[1-[[1-[2-(2,6-dioxo-3-piperidyl)-1,3-dioxo-isoindolin-5-yl]-4-piperidyl]methyl]-4-fluoro-4-piperidyl]methyl]-3-methyl-piperazine-1-carboxylate (370 mg, 526.46 μmol, 1 eq) in TFA (7.70 g, 67.53 mmol, 5 mL, 128.28 eq) in one portion at 20° C. under N2. The mixture was stirred at 70° C. for 2 hours to give yellow solution. LCMS showed desired MS. The residue was concentrated in vacuum to give 2-(2,6-dioxo-3-piperidyl)-5-[4-[[4-fluoro-4-[[(2S)-2-methylpiperazin-1-yl]methyl]-1-piperidyl]methyl]-1-piperidyl]isoindoline-1,3-dione (529 mg, 433.62 μmol, 82.37% yield, 84% purity, 4TFA) as a yellow gum.

Step 6

To a mixture of 2-(2,6-dioxo-3-piperidyl)-5-[4-[[4-fluoro-4-[[(2S)-2-methylpiperazin-1-yl]methyl]-1-piperidyl]methyl]-1-piperidyl]isoindoline-1,3-dione (281.12 mg, 274.32 μmol, 1.1 eq, 4TFA) and 3-(6-chloropyrimidin-4-yl)-5-(1-methylcyclopropoxy)-1H-indazole (75 mg, 249.38 μmol, 1 eq) in DMSO (5 mL) was added DIEA (257.84 mg, 2.00 mmol, 347.50 μL, 8 eq) in one portion at 20° C. under N2. The mixture was stirred at 80° C. for 36 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 35; FlowRate: 25 mL/min; Gradient Time: 35 min; 100% B Hold Time: 3 min) to give 2-(2,6-dioxo-3-piperidyl)-5-[4-[[4-fluoro-4-[[(2S)-2-methyl-4-[6-[5-(1-methylcyclopropoxy)-1H-indazol-3-yl]pyrimidin-4-yl]piperazin-1-yl]methyl]-1-piperidyl]methyl]-1-piperidyl]isoindoline-1,3-dione (23.9 mg, 28.46 μmol, 11.41% yield, 99.20% purity) as a yellow solid.

Exemplary Synthesis of Compound 70

Step 1

To a mixture of benzyl (3S)-3-methylpiperazine-1-carboxylate (500 mg, 2.13 mmol, 1 eq) and tert-butyl 4-formylpiperidine-1-carboxylate (546.17 mg, 2.56 mmol, 1.2 eq) in MeOH (10 mL) was added NaOAc (175.07 mg, 2.13 mmol, 1 eq), borane; 2-methylpyridine (456.52 mg, 4.27 mmol, 2 eq) and HOAc (128.15 mg, 2.13 mmol, 122.05 μL, 1 eq) in one portion at 25° C. under N2. The mixture was stirred at 25° C. for 1 h. TLC (Dichloromethane:Methanol=10:1, Rf=0.43, PMA) showed the reaction was completed. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (Dichloromethane:Methanol=10:1, Rf=0.43, 0-100% (20 min) of Ethyl acetate in Petroleum ether, 100% (10 min) of Ethyl acetate in Petroleum ether) to give benzyl (3S)-4-[(1-tert-butoxycarbonyl-4-piperidyl)methyl]-3-methyl-piperazine-1-carboxylate (690 mg, 1.31 mmol, 61.43% yield, 82% purity) as a yellow oil.

Step 2

To a mixture of benzyl (3S)-4-[(1-tert-butoxycarbonyl-4-piperidyl)methyl]-3-methyl-piperazine-1-carboxylate (690 mg, 1.60 mmol, 1 eq) in DCM (10 mL) was added TFA (3.08 g, 27.01 mmol, 2 mL, 16.90 eq) in one portion at 20° C. under N2. The mixture was stirred at 20° C. for 30 min. LCMS showed the reaction completed. The residue was concentrated in vacuum to give benzyl (3S)-3-methyl-4-(4-piperidylmethyl)piperazine-1-carboxylate (1.3 g, 1.52 mmol, 95.37% yield, 79% purity, 3TFA) as a colourless oil.

Step 3

To a mixture of benzyl (3S)-3-methyl-4-(4-piperidylmethyl)piperazine-1-carboxylate (1.3 g, 1.93 mmol, 1 eq, 3TFA) in EtOH (10 mL) was added tert-butyl 1-oxa-6-azaspiro[2.5]octane-6-carboxylate (823.30 mg, 3.86 mmol, 2 eq) at 20° C. under N2. The mixture was stirred at 90° C. for 16 hours. TLC (Dichloromethane:Methanol=10:1, Rf=0.57) and LCMS showed the reaction was completed. The residue was poured into water (10 mL). The aqueous phase was extracted with DCM (10 mL*3). The combined organic phase was washed with brine (10 mL*2), dried with anhydrous Na2SO4, filtered and concentrated in vacuum. The residue was purified by silica gel chromatography (20 g, 30 mL/min, 0-100% (20 min) of Ethyl acetate in Petroleum ether) to give benzyl (3S)-4-[[1-[(1-tert-butoxycarbonyl-4-hydroxy-4-piperidyl)methyl]-4-piperidyl]methyl]-3-methyl-piperazine-1-carboxylate (370 mg, 679.24 μmol, 35.19% yield) as a yellow oil.

Step 4

To a mixture of benzyl (3S)-4-[[1-[(1-tert-butoxycarbonyl-4-hydroxy-4-piperidyl)methyl]-4-piperidyl]methyl]-3-methyl-piperazine-1-carboxylate (368.65 mg, 676.77 μmol, 1 eq) in DCM (10 mL) was added DAST (130.91 mg, 812.12 μmol, 107.30 μL, 1.2 eq) drop-wise at −40° C. under N2. Then heated to 25° C. and stirred for 1 h to give colourless solution. LCMS showed there was desired MS. TLC (Dichloromethane:Methanol=20:1, Rf=0.67) showed no start material and a new spot. The reaction was cooled to 0° C. and quenched with aqueous $NaHCO_3$ to adjusted the pH=7-8. The aqueous phase was extracted with DCM (10 mL*3). The combined organic layers were washed with brine (10 mL*2), dried over anhydrous sodium sulfate, filtered and concentrated under reduced pressure to give a residue. The residue was purified by silica gel chromatography (12 g, 0-18% (5 min) of Ethyl acetate in Petroleum ether, 18% (15 min) Ethyl acetate in Petroleum ether) to give benzyl (3S)-4-[[1-[(1-tert-butoxycarbonyl-4-fluoro-4-piperidyl)methyl]-4-piperidyl]methyl]-3-methyl-piperazine-1-carboxylate (210 mg, 384.11 μmol, 56.76% yield) as a yellow oil.

Step 5

To a solution of benzyl (3S)-4-[[1-[(1-tert-butoxycarbonyl-4-fluoro-4-piperidyl)methyl]-4-piperidyl]methyl]-3- methyl-piperazine-1-carboxylate (210 mg, 384.11 μmol, 1 eq) in DCM (5 mL) was added TFA (3.08 g, 27.01 mmol, 2 mL, 70.33 eq) in one portion at 20° C. under N2. The mixture was stirred at 20° C. for 30 min to give colourless solution. LCMS showed the reaction was completed. The residue was concentrated in vacuum to give benzyl (3S)-4-[[1-[(4-fluoro-4-piperidyl)methyl]-4-piperidyl]methyl]-3-methyl-piperazine-1-carboxylate (310 mg, 310.52 μmol, 80.84% yield, 79% purity, 3TFA) as a yellow oil.

Step 6

To a mixture of 2-(2,6-dioxo-3-piperidyl)-5-fluoro-isoindoline-1,3-dione (108.57 mg, 393.07 μmol, 1 eq) and benzyl (3S)-4-[[1-[(4-fluoro-4-piperidyl)methyl]-4-piperidyl]methyl]-3-methyl-piperazine-1-carboxylate (310 mg, 393.07 μmol, 1 eq, 3TFA) in DMSO (5 mL) was added DIEA (508.00 mg, 3.93 mmol, 684.64 μL, 10 eq) in one portion at 20° C. The mixture was stirred at 100° C. for 16 h. LCMS showed the reaction was completed. The mixture was cooled to 20° C. The aqueous phase was extracted with ethyl acetate (3×10 mL). The combined organic phase was washed with brine (2×10 mL), dried with anhydrous Na2SO4, filtered and concentrated in vacuum. The residue was purified by silica gel chromatography (100-200 mesh silica gel, 0-100% of Ethyl acetate in Petroleum ether) to give benzyl (3S)-4-[[1-[[1-[2-(2,6-dioxo-3-piperidyl)-1,3-dioxo-isoindolin-5-yl]-4-fluoro-4-piperidyl]methyl]-4-piperidyl]methyl]-3-methyl-piperazine-1-carboxylate (150 mg, 168.61 μmol, 42.90% yield, 79% purity) as a yellow gum.

Step 7

To a mixture of benzyl (3S)-4-[[1-[[1-[2-(2,6-dioxo-3-piperidyl)-1,3-dioxo-isoindolin-5-yl]-4-fluoro-4-piperidyl]methyl]-4-piperidyl]methyl]-3-methyl-piperazine-1-carboxylate (150 mg, 213.43 μmol, 1 eq) in TFA (3.12 g, 27.38 mmol, 2.03 mL, 128.28 eq) in one portion at 20° C. under N2. The mixture was stirred at 70° C. for 2 hours to give yellow solution. LCMS showed there was desired MS. The residue was concentrated in vacuum to give 2-(2,6-dioxo-3-piperidyl)-5-[4-fluoro-4-[[4-[[(2S)-2-methylpiperazin-1-yl]methyl]-1-piperidyl]methyl]-1-piperidyl]isoindoline-1,3-dione (300 mg, 194.94 μmol, 91.34% yield, 74% purity, 5TFA) as a yellow gum.

Step 8

To a mixture of 2-(2,6-dioxo-3-piperidyl)-5-[4-fluoro-4-[[4-[[(2S)-2-methylpiperazin-1-yl]methyl]-1-piperidyl]methyl]-1-piperidyl]isoindoline-1,3-dione (300 mg, 527.54 μmol, 2.12 eq) and 3-(6-chloropyrimidin-4-yl)-5-(1-methylcyclopropoxy)-1H-indazole (75 mg, 249.38 μmol, 1 eq) in DMSO (5 mL) was added DIEA (257.84 mg, 2.00 mmol, 347.50 μL, 8 eq) in one portion at 20° C. under N2. The mixture was stirred at 80° C. for 24 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 35; FlowRate: 25 mL/min; Gradient Time: 35 min; 100% B Hold Time: 3 min) to give 2-(2,6-dioxo-3-piperidyl)-5-[4-fluoro-4-[[4-[[(2S)-2-methyl-4-[6-[5-(1-methylcyclopropoxy)-1H-indazol-3-yl]pyrimidin-4-yl]piperazin-1-yl]methyl]-1-piperidyl]methyl]-1-piperidyl]isoindoline-1,3-dione (25 mg, 28.29 μmol, 11.35% yield, 94.27% purity) as a yellow solid.

Exemplary Synthesis of Compound 71

Compound 71 was prepared in method analogous to compound 70 using 3-(6-chloropyrimidin-4-yl)-6-fluoro-5-(1-methylcyclopropoxy)-2H-indazole and 2-(2,6-dioxopiperidin-3-yl)-5-(4-((4-(((S)-2-methylpiperazin-1-yl)methyl)piperidin-1-yl)methyl)piperidin-1-yl)isoindoline-1,3-dione.

Step 1

To a solution of 1-bromo-4,5-difluoro-2-nitro-benzene (10 g, 42.02 mmol, 1 eq) and 1-methylcyclopropanol (3.03 g, 42.02 mmol, 1 eq) in DMF (50 mL) was added NaH (2.52 g, 63.03 mmol, 60% purity, 1.5 eq) in one portion at 0° C. under N2. Then heated to 20° C. and stirred for 2 hours to give brown suspension. TLC showed the reaction was completed. The residue was poured into NH4Cl (100 mL) and stirred for 10 min. The aqueous phase was extracted with ethyl acetate (3×100 mL). The combined organic phase was washed with NH4Cl (2×100 mL), dried with anhydrous Na2SO4, filtered and concentrated in vacuum. The residue was purified by silica gel chromatography (column height: 80 g, 100-200 mesh silica gel, 100% (30 min) of Petroleum ether) to give 1-bromo-4-fluoro-5-(1-methylcyclopropoxy)-2-nitro-benzene (9 g, 31.03 mmol, 73.84% yield) as a yellow oil.

Step 2

To a mixture of 1-bromo-4-fluoro-5-(1-methylcyclopropoxy)-2-nitro-benzene (9 g, 31.03 mmol, 1 eq), K2CO3 (8.58 g, 62.05 mmol, 2 eq) and Cs2CO3 (10.11 g, 31.03 mmol, 1 eq) in 1,4-dioxane (200 mL) was added Trimethylboroxine (19.47 g, 77.56 mmol, 21.69 mL, 50% purity, 2.5 eq) and $Pd(PPh3)_4$ (3.59 g, 3.10 mmol, 0.1 eq) at 20° C., then heated to 100° C. and stirred for 16 h to give yellow solution. TLC showed the reaction was completed. The reaction was cooled to 20° C. and concentrated under vacuum. The residue was purified by silica gel chromatography (330 g, 100-200 mesh silica gel, 100% (30 min) of Petroleum ether) to give 1-fluoro-4-methyl-2-(1-methylcyclopropoxy)-5-nitro-benzene (5.9 g, 26.20 mmol, 84.44% yield) as a yellow oil.

Step 3

To a mixture of 1-fluoro-4-methyl-2-(1-methylcyclopropoxy)-5-nitrobenzene (5.9 g, 26.20 mmol, 1 eq) in EtOH (10 mL) was added Pd/C (3 g, 26.20 mmol, 10% purity, 1 eq) and ammonium formate (19.82 g, 314.37 mmol, 12 eq) in one portion at 20° C. under N2. The mixture was stirred at 20° C. for 2 h to give black solution. LCMS showed there was desired MS. TLC (Petroleum ether:Ethyl acetate=10:1, Rf=0.23, UV 254 nm) showed no starting material and a new spot was showed by TLC. The suspension was filtered through a pad of Celite or silica gel and the pad or filter cake was washed with EtOH (100 mL*3). The combined filtrates were concentrated. The residue was purified by silica gel chromatography (Petroleum ether:Ethyl acetate=10:1, Rf=0.16, 20 g, 0-5% (3 min) of Ethyl acetate in Petroleum ether, 5% (5 min) of Ethyl acetate in Petroleum ether) to give 5-fluoro-2-methyl-4-(1-methylcyclopropoxy)aniline (5.3 g, crude) as a yellow oil.

Step 4

To a stirred solution of 5-fluoro-2-methyl-4-(1-methylcyclopropoxy)aniline (5.3 g, 27.15 mmol, 1 eq) in AcOH (60 mL) was added NaNO2 (2.06 g, 29.86 mmol, 1.1 eq) in H2O (15 mL) at 0° C. The reaction mixture was stirred at 20° C. for 16 hrs. The reaction mixture colour was changed from yellow to brown. LCMS and TLC (Petroleum ether:Ethyl acetate=3:1, Rf=0.16, UV 254 nm) showed the reaction was completed. The residue was added saturated $NaHCO_3$ solution (40 mL) and extracted with EA (40 mL). The combined organic layers were washed with brine (40 mL), dried over Na2SO4, filtered and concentrated under reduced pressure to give the residue. The residue was purified by column chromatography on silica gel (column height: 40 g, 100-200 mesh silica gel, 0-30% (10 min) of Ethyl acetate in Petroleum ether, 30% (20 min) of Ethyl acetate in Petroleum ether) to give 6-fluoro-5-(1-methylcyclopropoxy)-1H-indazole (1 g, 4.85 mmol, 17.86% yield) as a yellow oil.

Step 5

To a mixture of 6-fluoro-5-(1-methylcyclopropoxy)-1H-indazole (1 g, 4.85 mmol, 1 eq) in THF (40 mL) was added N-cyclohexyl-N-methyl-cyclohexanamine (2.84 g, 14.55 mmol, 3.09 mL, 3 eq) and SEM-Cl (1.62 g, 9.70 mmol, 1.72 mL, 2 eq) in one portion at 20° C. The mixture was stirred at 20° C. for 1 h to give orange suspension. TLC showed the reaction was completed. LCMS showed desired MS. The residue was poured into water (20 mL). The aqueous phase was extracted with ethyl acetate (3×30 mL). The combined organic phase was washed with brine (2×30 mL), dried with anhydrous Na2SO4, filtered and concentrated in vacuum. The residue was purified by silica gel chromatography (100-200 mesh silica gel, 0-3% (20 min) of ethyl acetate in Petroleum ether, 3-10% (10 min) of ethyl acetate in Petroleum ether) to give 2-[[6-fluoro-5-(1-methylcyclopropoxy) indazol-2-yl]methoxy]ethyl-trimethyl-silane (1.1 g, 3.27 mmol, 67.42% yield) as a yellow oil.

Step 6

To a mixture of 2-[[6-fluoro-5-(1-methylcyclopropoxy) indazol-2-yl]methoxy]ethyl-trimethyl-silane (1.1 g, 3.27 mmol, 1 eq) in THF (5 mL) was dropwise added n-BuLi (2.5 M, 1.57 mL, 1.2 eq) at −70° C. under N2. The mixture was then stirred at −20° C. for 5 min, and a solution of ZnCl2 (1 M, 4.90 mL, 1.5 eq) was dropwise added at −70° C. The mixture was stirred for 10 min at −40° C. A mixture of 4,6-dichloropyrimidine (487.04 mg, 3.27 mmol, 1 eq) and $Pd(PPh3)_4$ (188.89 mg, 163.46 μmol, 0.05 eq) in THF (5 mL) was stirred at 20° C. for 30 min and was added to that solution. The cold bath was removed, and the mixture was stirred at 20° C. for 10 h to give yellow solution. TLC (Petroleum ether:Ethyl acetate=3:1, Rf=0.83) showed the reaction was completed. LCMS showed there was desired MS. The residue was poured into water (20 mL). The aqueous phase was extracted with ethyl acetate (3×20 mL). The combined organic phase was washed with brine (2×20 mL), dried with anhydrous Na2SO4, filtered and concentrated in vacuum. The residue was purified by silica gel chromatography (100-200 mesh silica gel, 0-5% (30 min) of Ethyl acetate in Petroleum ether, 5% (60 min) of Ethyl acetate in Petroleum ether) to give 2-[[3-(6-chloropyrimidin-4-yl)-6-fluoro-5-(1-methylcyclopropoxy)indazol-2-yl] methoxy]ethyl-trimethyl-silane (271 mg, 603.57 μmol, 18.46% yield) as a yellow oil Step 7

To a solution of 2-[[3-(6-chloropyrimidin-4-yl)-6-fluoro-5-(1-methylcyclopropoxy)indazol-2-yl]methoxy]ethyl-trimethyl-silane (271 mg, 603.57 μmol, 1 eq) in DCM (2 mL) was added TFA (4.01 g, 35.13 mmol, 2.60 mL, 58.21 eq). Then the mixture was stirred at 20° C. for 30 min. LCMS was showed the reaction completed. The reaction mixture was poured into H2O (10 mL). The aqueous phase was adjusted to pH 9 with solid $NaHCO_3$. The mixture was extracted with ethyl acetate (15 mL*3). The organic phase was washed with brine (10 mL), dried over anhydrous Na2SO4, concentrated in vacuum to give a residue. The crude product in dioxane (2 mL) was added NH3 H2O (1 mL) and stirred at 20° C. for 1 h. LCMS showed desired MS. Then the mixture was extracted with ethyl acetate (15 mL*3). The organic phase was washed with brine (10 mL), dried over anhydrous Na2SO4, concentrated in vacuum to give a residue. The residue was purified by silica gel chromatography (0-10% of Ethyl acetate in Petroleum ether) to give 3-(6-chloropyrimidin-4-yl)-6-fluoro-5-(1-methylcyclopropoxy)-2H-indazole (20 mg, 57.73 μmol, 9.56% yield, 92% purity) as a white solid.

Exemplary Synthesis of Compound 72

Compound 72 was prepared in a manner analogous to compound 71 using 3-(6-chloropyrimidin-4-yl)-5-(cyclopropoxy)-2H-indazole and 2-(2,6-dioxopiperidin-3-yl)-5-(4-((4-(((S)-2-methylpiperazin-1-yl)methyl)piperidin-1-yl) methyl)piperidin-1-yl)isoindoline-1,3-dione.

Exemplary Synthesis of Compound 73

Step 1

To a solution of 5-(1-methylcyclopropoxy)-3-[6-[(3S)-3-methyl-4-(4-piperidylmethyl)piperazin-1-yl]pyrimidin-4-yl]-2H-indazole (80 mg, 173.31 μmol, 1 eq) and tert-butyl 4-formylpiperidine-1-carboxylate (55.44 mg, 259.96 μmol, 1.5 eq) in MeOH (5 mL) was added AcOH (1 mL) and borane; 2-methylpyridine (18.54 mg, 173.31 μmol, 1 eq). The mixture was stirred at 25° C. for 16 hr. LCMS showed desired MS. The reaction mixture was concentrated in vacuum to give a residue. The residue was purified by silica gel chromatography (Dichloromethane:Methanol=10:1, 0-100% (20 min) of Ethyl acetate in Petroleum ether, 100% (10 min) of Ethyl acetate in Petroleum ether) to give tert-butyl 4-[[4-[[(2S)-2-methyl-4-[6-[5-(1-methylcyclopropoxy)-2H-indazol-3-yl]pyrimidin-4-yl]piperazin-1-yl] methyl]-1-piperidyl]methyl]piperidine-1-carboxylate (120 mg, 160.27 μmol, 92.48% yield, 88% purity) as a colorless oil.

Step 2

To a solution of tert-butyl 4-[[4-[[(2S)-2-methyl-4-[6-[5-(1-methylcyclopropoxy)-2H-indazol-3-yl]pyrimidin-4-yl] piperazin-1-yl]methyl]-1-piperidyl]methyl]piperidine-1-carboxylate (120 mg, 182.13 umol, 1 eq) in DCM (5 mL) was added TFA (3.08 g, 27.01 mmol, 2 mL, 148.31 eq). The mixture was stirred at 25° C. for 1 hr. LCMS showed desired MS. The mixture was concentrated in vacuum to give 5-(1-methylcyclopropoxy)-3-[6-[(3S)-3-methyl-4-[[1-(4-piperidylmethyl)-4-piperidyl]methyl]piperazin-1-yl]pyrimidin-4-yl]-2H-indazole (150 mg, crude) as a brown oil.

Step 3

To a solution of 4,5-difluorophthalic acid (450 mg, 2.23 mmol, 1 eq) and 3-aminopiperidine-2,6-dione; hydrochloride (549.69 mg, 3.34 mmol, 1.5 eq) in AcOH (5 mL) was added NaOAc (547.92 mg, 6.68 mmol, 3 eq) The mixture was stirred at 120° C. for 15 hr. LCMS showed desired MS. The mixture was diluted with water (50 mL). The mixture was filtered and the filtrate cake was washed with water (50 mL). The mixture was concentrated in vacuum to give 2-(2,6-dioxo-3-piperidyl)-5,6-difluoro-isoindoline-1,3-dione (300 mg, 948.30 μmol, 42.59% yield, 93% purity) as a black solid.

Step 4

A mixture of 5-(1-methylcyclopropoxy)-3-[6-[(3S)-3-methyl-4-[[1-(4-piperidylmethyl)-4-piperidyl]methyl]piperazin-1-yl]pyrimidin-4-yl]-2H-indazole (50 mg, 89.48 μmol, 1 eq) and 2-(2,6-dioxo-3-piperidyl)-5,6-difluoro-isoindoline-1,3-dione (39.49 mg, 134.23 μmol, 1.5 eq) in MeCN (2 mL) was added DIEA (371.00 mg, 2.87 mmol, 0.5 mL, 32.08 eq). The mixture was stirred at 60° C. for 16 h. LCMS showed Reactant 1 was consumed completely and desired MS found. The reaction mixture was concentrated in vacuum. The crude product was purified by reversed-phase HPLC (column: Column: 3_Phenomenex Luna C18 75*30 mm*3 um; Condition: [water (0.225% FA)-ACN]; Begin B: 0 End B: 35; Flow Rate: 25 mL/min; Gradient Time: 35 min; 100% B Hold Time: 3 min) to give a residue to give 2-(2,6-dioxo-3-piperidyl)-5-fluoro-6-[4-[[4-[[(2S)-2-methyl-4-[6-[5-(1-methylcyclopropoxy)-2H-indazol-3-yl] pyrimidin-4-yl]piperazin-1-yl]methyl]-1-piperidyl]methyl]-1-piperidyl]isoindoline-1,3-dione (7.8 mg, 9.18 μmol, 10.26% yield, 98% purity) as a green solid.

Exemplary Synthesis of Compound 74

Step 1

To a solution of tert-butyl 2,5-dihydropyrrole-1-carboxylate (5 g, 29.55 mmol, 1 eq) in DCM (50 mL) was added rhodium(ii) acetate dimer (320 mg, 724.00 μmol, 2.45 e-2 eq) under nitrogen atmosphere. Then, ethyl 2-diazoacetate (3.37 g, 29.55 mmol, 1 eq) dissolved in DCM (40 mL) was slowly added dropwise for 1 h. After addition, the reaction mixture was stirred at 25° C. for 12 h. TLC (petroleum ether:ethyl acetate=10:1) showed several new spots. The reaction mixture was filtered and filtrate was concentrated under reduced pressure. The residue was purified by silica gel column chromatography (0 to 10% ethyl acetate in petroleum ether) to afford O3-tert-butyl O6-ethyl (1s, 5s, 6r)-3-azabicyclo[3.1.0]hexane-3,6-dicarboxylate (650 mg, 2.55 mmol, 8.62% yield) as a colorless oil and O3-tert-butyl O6-ethyl (1s, 5r, 6s)-3-azabicyclo[3.1.0]hexane-3,6-dicarboxylate (460 mg, 1.80 mmol, 6.10% yield) as a light yellow oil.

Step 2

To a solution of O3-tert-butyl O6-ethyl (1s, 5r, 6s)-3-azabicyclo[3.1.0]hexane-3,6-dicarboxylate (770 mg, 3.02 mmol, 1 eq) in EtOH (6 mL) was added NaOH (2 M, 3.02 mL, 2 eq) dropwise at 0° C. After addition, the reaction solution was stirred at 25° C. for 12 h. TLC (petroleum ether:ethyl acetate=10:1) showed starting material consumed and a new spot formed. The reaction mixture was concentrated under reduced pressure. The residue was diluted with water (10 mL) and washed with ethyl acetate (10 mL*2). The aqueous phase was acidified to pH 2 with 2 M HCl and extracted with ethyl acetate (10 mL*2). The organic layer was dried over sodium sulfate and concentrated under reduced pressure to afford (1s, 5r, 6s)-3-tert-butoxycarbonyl-3-azabicyclo[3.1.0]hexane-6-carboxylic acid (600 mg, crude) as a brown solid. The crude product was used for next step directly.

Step 3

A solution of (1s, 5r, 6s)-3-tert-butoxycarbonyl-3-azabicyclo[3.1.0]hexane-6-carboxylic acid (600 mg, 2.64 mmol, 1 eq) in THF (10 mL) was cooled to −10° C. borane; tetrahydrofuran (1 M, 5.28 mL, 2 eq) was added slowly to the flask while maintaining the temperature lower than 0° C. The solution was warmed to 25° C. and stirred for 12 h. TLC (PE:EtOAc=1:1) showed starting material consumed and a new spot formed. The solution was cooled to 0° C., and a 15% sodium hydroxide solution (10 mL) was added dropwise over a 5 minute period to control gas evolution. The mixture was diluted with water (10 mL) and extracted with ethyl acetate (3×20 mL). The organic layer was washed with brine (30 mL), dried over sodium sulfate and concentrated under reduced pressure. The residue was purified by silica gel column chromatography (0 to 50% ethyl acetate in petroleum ether) to afford tert-butyl (1s, 5r, 6s)-6-(hydroxymethyl)-3-azabicyclo[3.1.0]hexane-3-carboxylate (350 mg, 1.64 mmol, 62.16% yield) as a colorless oil.

Step 4

To a solution of tert-butyl (1s, 5r, 6s)-6-(hydroxymethyl)-3-azabicyclo[3.1.0]hexane-3-carboxylate (50 mg, 234.44 μmol, 1 eq) in DCM (2 mL) was added DMP (198.87 mg, 468.88 μmol, 2 eq). After addition, the reaction mixture was stirred at 25° C. for 1 h. TLC (petroleum ether:ethyl acetate=1:1) showed the reaction completed. The reaction mixture was filtered and filtrate was concentrated under reduced pressure to afford tert-butyl (1s, 5r, 6s)-6-formyl-3-azabicyclo[3.1.0]hexane-3-carboxylate (49 mg, crude) as a white solid. The crude product was used for next step directly.

Step 5

To a solution of tert-butyl (1s, 5r, 6s)-6-formyl-3-azabicyclo[3.1.0]hexane-3-carboxylate (49 mg, 231.94 μmol, 1 eq) and 2-(2,6-dioxo-3-piperidyl)-5-[4-(piperazin-1-ylmethyl)-1-piperidyl]isoindoline-1,3-dione (101.94 mg, 231.94 μmol, 1 eq) in MeOH (2 mL) and HOAc (0.2 mL) was added borane; 2-methylpyridine (49.62 mg, 463.89 μmol, 2 eq). After addition, the reaction mixture was stirred at 25° C. for 12 h. LCMS showed desired MS. TLC (dichloromethane:methanol=10:1) showed several new spots. The reaction mixture was concentrated under reduced pressure. The residue was purified by silica gel column chromatography (0 to 10% methanol in dichloromethane) to afford tert-butyl (1r, 5s, 6s)-6-[[4-[[1-[2-(2,6-dioxo-3-piperidyl)-1,3-dioxo-isoindolin-5-yl]-4-piperidyl]methyl]piperazin-1-yl]methyl]-3-azabicyclo[3.1.0]hexane-3-carboxylate (100 mg, 157.54 μmol, 67.92% yield) as a yellow solid.

Step 6

To a solution of tert-butyl (1r, 5s, 6s)-6-[[4-[[1-[2-(2,6-dioxo-3-piperidyl)-1,3-dioxo-isoindolin-5-yl]-4-piperidyl] methyl]piperazin-1-yl]methyl]-3-azabicyclo[3.1.0]hexane-3-carboxylate (100 mg, 157.54 μmol, 1 eq) in DCM (2 mL) was added TFA (1.54 g, 13.51 mmol, 1 mL, 85.73 eq). After addition, the reaction solution was stirred at 25° C. for 1 h. LCMS showed starting material consumed and desired MS formed. The reaction mixture was concentrated under reduced pressure to afford 5-[4-[[4-[[(1s, 5r, 6s)-3-azabicyclol[3.1.0]hexan-6-yl]methyl]piperazin-1-yl]methyl]-1-piperidyl]-2-(2,6-dioxo-3-piperidyl)isoindoline-1,3-dione (84 mg, crude) as a yellow gum. The crude product was used for next step directly.

Step 7

To a solution of 5-[4-[[4-[[(1s, 5r, 6s)-3-azabicyclo[3.1.0] hexan-6-yl]methyl]piperazin-1-yl]methyl]-1-piperidyl]-2-(2,6-dioxo-3-piperidyl)isoindoline-1,3-dione (84 mg, 157.11 μmol, 1.43 eq) and 3-(6-chloropyrimidin-4-yl)-5-(1-methylcyclopropoxy)-2H-indazole (33 mg, 109.73 μmol, 1 eq) in DMSO (2 mL) was added DIEA (70.91 mg, 548.64 μmol, 95.56 μL, 5 eq). After addition, the reaction solution was stirred at 90° C. for 12 h. LCMS showed starting material consumed and desired MS was found. The residue was diluted with dichloromethane (20 mL) and washed with water (10 mL*2). The organic layer was dried over sodium sulfate and concentrated under reduced pressure. The residue was purified by prep.HPLC (column: Phenomenex Luna C18 75*30 mm*3 um; mobile phase: [water (0.225% FA)-ACN]; B %: 0%-35%, 35 min) to afford 2-(2,6-dioxo-3-piperidyl)-5-[4-[[4-[[(r, 5s, 6s)-3-[6-[5-(1-methylcyclopropoxy)-1H-indazol-3-yl]pyrimidin-4-yl]-3-azabicyclo [3.1.0]hexan-6-yl]methyl]piperazin-1-yl]methyl]-1-piperidyl]isoindoline-1,3-dione (31.1 mg, 38.72 μmol, 35.28% yield, 99.46% purity) as a yellow solid.

Exemplary Synthesis of Compound 75

Compound 75 was prepared in a method analogous to compound 74 using 3-(tert-butyl) 6-ethyl (1r, 5s, 6r)-3-azabicyclo[3.1.0]hexane-3,6-dicarboxylate.

Exemplary Synthesis of Compound 76

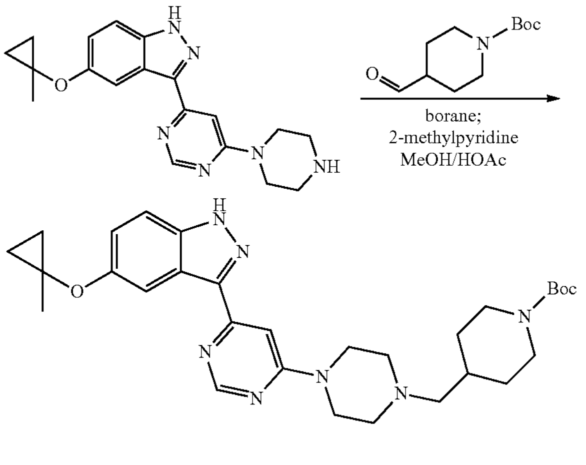

Step 1

To a solution of 5-(1-methylcyclopropoxy)-3-(6-piperazin-1-ylpyrimidin-4-yl)-1H-indazole (80 mg, 228.30 μmol, 1 eq) in HOAc (0.4 mL) and MeOH (4 mL) was added tert-butyl 4-formylpiperidine-1-carboxylate (97.38 mg, 456.60 μmol, 2 eq) and borane; 2-methylpyridine (48.84 mg, 456.60 μmol, 2 eq). After addition, the reaction solution was stirred at 25° C. for 12 h. LCMS (EB12-770-P1D) showed desired MS. TLC (ethyl acetate:petroleum ether=2:1) showed several new spots. The reaction mixture was diluted with water (10 mL) and extracted with ethyl acetate (2×10 mL). The combined organic layers were washed with brine (20 mL), dried over $Na_2SO_4$, filtered and concentrated under reduced pressure. The residue was purified by silica gel column chromatography (0 to 100% ethyl acetate in petroleum ether) to afford tert-butyl 4-[[4-[6-[5-(1-methylcyclopropoxy)-1H-indazol-3-yl]pyrimidin-4-yl]piperazin-1-yl]methyl]piperidine-1-carboxylate (75 mg, 133.93 μmol, 58.66% yield, 97.8% purity) as a white solid.

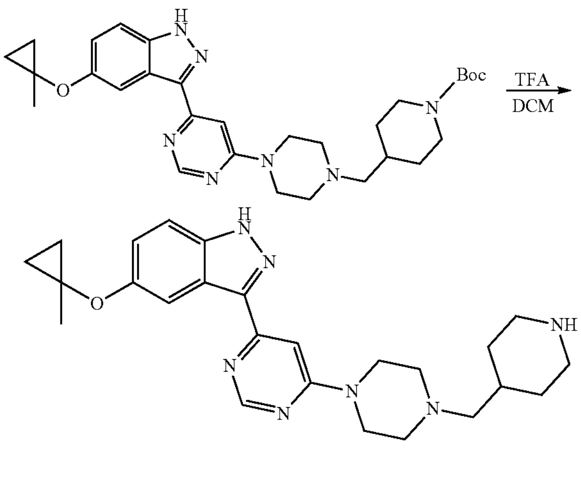

Step 2

To a solution of tert-butyl 4-[[4-[6-[5-(1-methylcyclopropoxy)-1H-indazol-3-yl]pyrimidin-4-yl]piperazin-1-yl]methyl]piperidine-1-carboxylate (75 mg, 136.94 μmol, 1 eq) in DCM (3 mL) was added TFA (2.31 g, 20.26 mmol, 1.5 mL, 147.94 eq). After addition, the reaction solution was stirred at 25° C. for 1 h. TLC (pure ethyl acetate) showed starting material consumed and a new spot formed. The reaction mixture was concentrated under reduced pressure. The residue was dissolved in DMC (1 mL) and treated with DIEA (0.5 mL). The mixture was concentrated under reduced pressure to afford 5-(1-methylcyclopropoxy)-3-[6-[4-(4-piperidylmethyl)piperazin-1-yl]pyrimidin-4-yl]-1H-indazole (65 mg, crude) as a yellow gum. The crude product was used for next step directly.

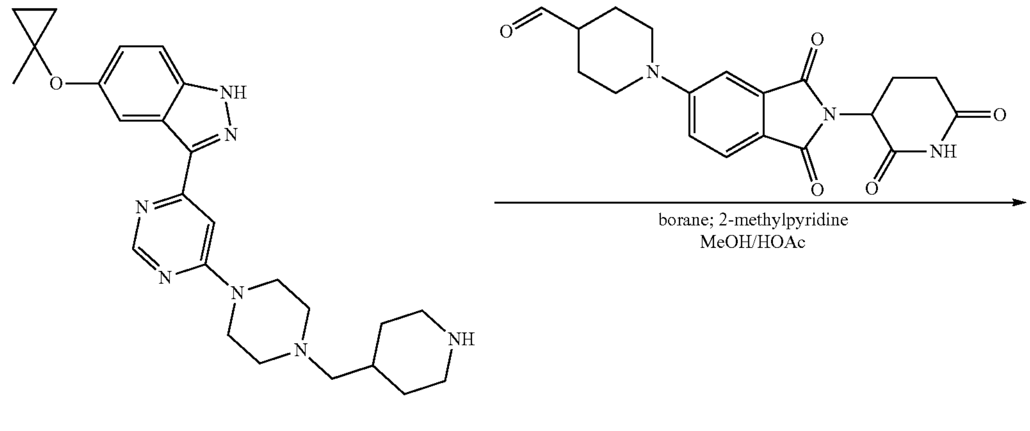

-continued

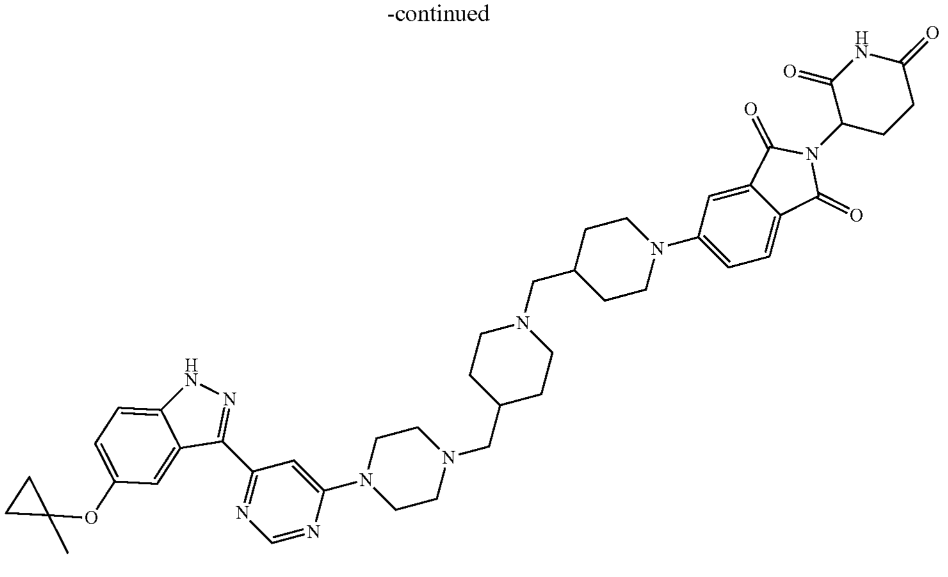

Step 3

To a solution of 5-(1-methylcyclopropoxy)-3-[6-[4-(4-piperidylmethyl)piperazin-1-yl]pyrimidin-4-yl]-1H-indazole (65 mg, 145.23 μmol, 1 eq) in MeOH (5 mL) and HOAc (0.5 mL) was added 1-[2-(2,6-dioxo-3-piperidyl)-1,3-dioxo-isoindolin-5-yl]piperidine-4-carbaldehyde (55 mg, 148.90 μmol, 1.03 eq) and borane; 2-methylpyridine (40 mg, 373.97 μmol, 2.58 eq). After addition, the reaction mixture was stirred at 25° C. for 12 h. LCMS (EB12-774-P1B1) showed starting material consumed and desired MS formed. The reaction was diluted with water (10 mL) and extracted with ethyl acetate (8 mL*3). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 0-35%; 40 min) to afford 2-(2,6-dioxo-3-piperidyl)-5-[4-[[4-[[4-[6-[5-(1-methylcyclopropoxy)-1H-indazol-3-yl]pyrimidin-4-yl]piperazin-1-yl]methyl]-1-piperidyl]methyl]-1-piperidyl]isoindoline-1,3-dione (37.7 mg, 46.93 μmol, 32.31% yield, 99.70% purity) as a yellow solid.

Exemplary Synthesis of Compound 77

Compound 77 was prepared in a method analogous to compound 68.

Step 1

To a mixture of 2-(2,6-dioxo-3-piperidyl)-5-[4-[[4-(4-piperidylmethyl)-1-piperidyl]methyl]-1-piperidyl]isoindoline-1,3-dione (199.64 mg, 307.28 μmol, 1.18 eq, TFA) and 3-(6-chloropyrimidin-4-yl)-6-fluoro-5-(1-methylcyclopropoxy)-2H-indazole (83.00 mg, 260.41 μmol, 1 eq) in DMSO (5 mL) was added DIEA (269.24 mg, 2.08 mmol, 362.86 μL, 8 eq) in one portion at 20° C. under N2. The mixture was stirred at 80° C. for 16 h. LCMS showed desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 35; FlowRate: 25 mL/min; Gradient Time: 40 min; 100% B Hold Time: 3 min) to give 2-(2,6-dioxo-3-piperidyl)-5-[4-[[4-[[1-[6-[6-fluoro-5-(1-methylcyclopropoxy)-1H-indazol-3-yl]pyrimidin-4-yl]-4-piperidyl]methyl]-1-piperidyl]methyl]-1-piperidyl]isoindoline-1,3-dione (19 mg, 22.91 μmol, 8.80% yield, 98.61% purity) as a yellow solid.

Exemplary Synthesis of Compound 78

Step 1

A mixture of 4-piperidylmethanol (2 g, 17.37 mmol, 1 eq), 4-bromo-2-fluoro-pyridine (3.06 g, 17.37 mmol, 1 eq) in DMSO (10 mL) was added K2CO3 (4.80 g, 34.73 mmol, 2 eq), and then the mixture was stirred at 100° C. for 4 h under N2 atmosphere. LCMS showed desired MS. TLC (Petroleum ether:Ethyl acetate=3:1) showed one new major point. The reaction mixture was concentrated under reduced pressure to give a residue. The crude was purified by a flash chromatography on silica (0-50% Ethyl acetate in Petroleum ether) to give [1-(4-bromo-2-pyridyl)-4-piperidyl]methanol (4.3 g, 15.70 mmol, 90.41% yield, 99% purity) was obtained as a white solid.

Step 2

To a mixture of [1-(4-bromo-2-pyridyl)-4-piperidyl]methanol (2 g, 7.38 mmol, 1 eq) and TosCl (2.81 g, 14.75 mmol, 2 eq) in DCM (10 mL) was added TEA (1.49 g, 14.75 mmol, 2.05 mL, 2 eq) and DMAP (450.56 mg, 3.69 mmol, 0.5 eq) in one portion at 0° C. under N2. The mixture was stirred at 20° C. for 1 hour. LCMS showed desired MS. The reaction mixture was filtered and the filtrate was concentrated under reduced pressure. The residue was purified by silica gel column chromatography (0 to 50% ethyl acetate in petroleum ether) to give [1-(4-bromo-2-pyridyl)-4-piperidyl]methyl 4-methylbenzenesulfonate (3.12 g, 6.38 mmol, 86.52% yield, 87% purity) as a white solid.

Step 3

To a mixture of [1-(4-bromo-2-pyridyl)-4-piperidyl]methyl 4-methylbenzenesulfonate (3.12 g, 7.34 mmol, 1 eq) and tert-butyl piperazine-1-carboxylate (2.05 g, 11.00 mmol, 1.5 eq) in MeCN (20 mL) was added KI (6.09 g, 36.68 mmol, 5 eq) and DIEA (4.74 g, 36.68 mmol, 6.39 mL, 5 eq) in one portion at 0° C. under N2. The mixture was stirred at 80° C. for 12 hours. LCMS showed desired MS. The reaction mixture was filtered and the filtrate was concentrated under reduced pressure The residue was purified by silica gel column chromatography (0 to 100% ethyl acetate in petroleum ether) to give tert-butyl 4-[[1-(4-bromo-2-pyridyl)-4-piperidyl]methyl]piperazine-1-carboxylate (880 mg, 1.44 mmol, 19.66% yield, 72% purity) as a white solid.

Step 4

To a solution of tert-butyl 4-[[1-(4-bromo-2-pyridyl)-4-piperidyl]methyl]piperazine-1-carboxylate (500 mg, 1.14 mmol, 1 eq) and 4,4,5,5-tetramethyl-2-(4,4,5,5-tetramethyl-1,3,2-dioxaborolan-2-yl)-1,3,2-dioxaborolane (288.97 mg, 1.14 mmol, 1 eq) in dioxane (10 mL) was added KOAc (335.03 mg, 3.41 mmol, 3 eq) and Pd(dppf)Cl2 (83.26 mg, 113.79 μmol, 0.1 eq). After addition, the reaction mixture was stirred at 100° C. for 12 h under N2. LCMS showed desired MS The reaction mixture was filtered and concentrated under reduced pressure. to give tert-butyl 4-[[1-[4-(4,4,5,5-tetramethyl-1,3,2-dioxaborolan-2-yl)-2-pyridyl]-4-piperidyl]methyl]piperazine-1-carboxylate (1 g, crude) as a black oil.

Step 5

To a solution of tert-butyl 4-[[1-[4-(4,4,5,5-tetramethyl-1,3,2-dioxaborolan-2-yl)-2-pyridyl]-4-piperidyl]methyl] piperazine-1-carboxylate (553 mg, 1.14 mmol, 1 eq) in dioxane (10 mL) and H2O (2 mL) was added 2-[[3-iodo-5-(1-methylcyclopropoxy)indazol-1-yl]methoxy]ethyl-trimethyl-silane (350 mg, 787.61 μmol, 6.93 e-1 eq), Na2CO3 (361.46 mg, 3.41 mmol, 3 eq) and Pd(dppf)Cl2 (83.18 mg, 113.68 μmol, 0.1 eq). After addition, the reaction mixture was stirred at 100° C. under N2 for 16 h. LCMS showed desired MS. The reaction mixture was filtered and concentrated under reduced pressure to give tert-butyl 4-[[1-[4-[5-(1-methylcyclopropoxy)-1-(2-trimethylsilylethoxymethyl)indazol-3-yl]-2-pyridyl]-4-piperidyl]methyl]piperazine-1-carboxylate (850 mg, crude) as a light yellow gum.

Step 6

To a solution of tert-butyl 4-[[1-[4-[5-(1-methylcyclopropoxy)-1-(2-trimethylsilylethoxymethyl)indazol-3-yl]-2-pyridyl]-4-piperidyl]methyl]piperazine-1-carboxylate (850 mg, 1.26 mmol, 1 eq) in DCM (2 mL) was added TFA (3.08 g, 27.01 mmol, 2 mL, 21.51 eq). After addition, the reaction mixture was stirred at 25° C. for 2 h. LCMS showed desired MS. The reaction mixture was poured into H2O (10 mL). The aqueous phase was adjusted to pH=9 with solid $NaHCO_3$. The mixture was extracted with ethyl acetate (15 mL*3). The organic phase was washed with brine (10 mL), dried over anhydrous Na2SO4, concentrated in vacuum to give a residue. The crude product in dioxane (2 mL) was added NH3 H2O (1 mL) and stirred at 20° C. for 1 h. Then the mixture was extracted with ethyl acetate (15 mL*3). The organic phase was washed with brine (10 mL), dried over anhydrous Na2SO4, concentrated in vacuum to give 5-(1-methylcyclopropoxy)-3-[2-[4-(piperazin-1-ylmethyl)-1-piperidyl]-4-pyridyl]-1H-indazole (720 mg, crude, TFA) as a yellow gum.

Step 7

To a solution of 5-(1-methylcyclopropoxy)-3-[2-[4-(piperazin-1-ylmethyl)-1-piperidyl]-4-pyridyl]-1H-indazole (280 mg, 626.98 μmol, 1 eq) and 1-[2-(2,6-dioxo-3-piperidyl)-1,3-dioxo-isoindolin-5-yl]piperidine-4-carbaldehyde (150 mg, 406.10 μmol, 6.48 e-1 eq) in MeOH (5 mL) was added AcOH (0.5 mL) and borane; 2-methylpyridine (67.06 mg, 626.98 μmol, 1 eq). After addition, the reaction mixture was stirred at 25° C. for 16 h. LCMS showed desired MS. The reaction mixture was filtered and concentrated under reduced pressure. The crude product was purified by reversed-phase HPLC (column: 3_Phenomenex Luna C18 75*30 mm*3 um; mobile phase: [water (0.225% FA)-ACN]; B %: 0%-40%, 40 min). to give 2-(2,6-dioxo-3-piperidyl)-5-[4-[[4-[[1-[4-[5-(1-methylcyclopropoxy)-1H-indazol-3-yl]-2-pyridyl]-4-piperidyl]methyl]piperazin-1-yl]methyl]-1-piperidyl]isoindoline-1,3-dione (125.5 mg, 146.86 μmol, 23.42% yield, 99% purity, FA) as a yellow solid.

Exemplary Synthesis of Compound 79

Compound 79 was prepared in a manner analogous to compound 69.

Step 1

A mixture of 2-(2,6-dioxo-3-piperidyl)-5-[4-[[4-fluoro-4-(piperazin-1-ylmethyl)-1-piperidyl]methyl]-1-piperidyl] isoindoline-1,3-dione (110.66 mg, 199.51 μmol, 1 eq), 3-(6-chloropyrimidin-4-yl)-5-(1-methylcyclopropoxy)-2H-indazole (60 mg, 199.51 μmol, 1 eq) in DMSO (5 mL) was added DIEA (25.78 mg, 199.51 μmol, 34.75 μL, 1 eq), and then the mixture was stirred at 80° C. for 16 hr. LCMS showed the starting material was consumed completely and desired MS found. The reaction mixture was filtered and concentrated under reduced pressure. The crude product was purified by reversed-phase HPLC (column: 3_Phenomenex Luna C18 75*30 mm*3 um; mobile phase: [water (0.225% FA)-ACN]; B %: 0%-40%, 40 min). to give 2-(2,6-dioxo-3-piperidyl)-5-[4-[[4-fluoro-4-[[4-[6-[5-(1-methylcyclopropoxy)-1H-indazol-3-yl]pyrimidin-4-yl]piperazin-1-yl] methyl]-1-piperidyl]methyl]-1-piperidyl]isoindoline-1,3-dione (23.3 mg, 28.17 μmol, 14.12% yield, 99% purity) as a yellow solid.

Exemplary Synthesis of Compound 80

Step 1

To a mixture of 4-bromo-2-fluoro-pyridine (175.17 mg, 995.36 μmol, 1 eq) and tert-butyl 4-fluoro-4-(piperazin-1-ylmethyl)piperidine-1-carboxylate (300 mg, 995.36 μmol, 1 eq) in DMSO (10 mL) was added K2CO3 (687.84 mg, 4.98 mmol, 70.14 mL, 5 eq) in one portion at 100° C. under N2. The mixture was stirred at 100° C. for 2 h to give yellow solution. LCMS showed the reaction was completed. The mixture was cooled to 20° C. and concentrated in reduced pressure at 20° C. The residue was poured into water (50 mL). The aqueous phase was extracted with ethyl acetate (50 mL*4). The combined organic phase was washed with brine (50 mL*2), dried with anhydrous Na2SO4, filtered and concentrated in vacuum. The residue was purified by silica gel chromatography (Petroleum ether:Ethyl acetate=1:1, Rf=0.56, 12 g, 0-20% (10 min) of Ethyl acetate in Petroleum ether, 20% (10 min) of Ethyl acetate in Petroleum ether) to give tert-butyl 4-[[4-(4-bromo-2-pyridyl)piperazin-1-yl] methyl]-4-fluoro-piperidine-1-carboxylate (234 mg, 511.61 μmol, 51.40% yield) as a yellow oil.

Step 2

To a mixture of tert-butyl 4-[[4-(4-bromo-2-pyridyl)piperazin-1-yl]methyl]-4-fluoro-piperidine-1-carboxylate (150 mg, 327.96 μmol, 1 eq), Pin2B2 (166.56 mg, 655.91 μmol, 2 eq) and KOAc (96.56 mg, 983.87 μmol, 3 eq) in dioxane (10 mL) was added Pd(dppf)Cl2 (12.00 mg, 16.40 μmol, 0.05 eq) in one portion at 25° C. under N2. The mixture was stirred at 100° C. for 1 h. TLC showed the reaction was completed. The mixture was cooled to 25° C., filtered and concentrated in vacuum to give [2-[4-[(1-tert-butoxycarbonyl-4-fluoro-4-piperidyl)methyl]piperazin-1-yl]-4-pyridyl] boronic acid (500 mg, 284.16 μmol, 86.65% yield, 24% purity) as a black oil.

Step 3

To a mixture of [2-[4-[(1-tert-butoxycarbonyl-4-fluoro-4-piperidyl)methyl]piperazin-1-yl]-4-pyridyl]boronic acid (500 mg, 284.16 μmol, 24% purity, 1 eq), 2-[[3-iodo-5-(1-methylcyclopropoxy)indazol-1-yl]methoxy]ethyl-trimethyl-silane (138.90 mg, 312.57 μmol, 1.1 eq) and Na2CO3 (90.35 mg, 852.47 μmol, 3 eq) in 1,4-dioxane (10 mL) and H2O (2 mL) was added Pd(dppf)Cl2 (31.19 mg, 42.62 μmol, 0.15 eq) in one portion at 25° C. under N2. The mixture was stirred at 100° C. for 16 hours. LCMS showed there was desired MS. The mixture was cooled to 25° C., filtered and concentrated in vacuum. The residue was purified by silica gel chromatography (0-20% of Ethyl acetate in Petroleum ether) to give tert-butyl 4-fluoro-4-[[4-[4-[5-(1-methylcyclopropoxy)-1-(2-trimethylsilylethoxymethyl)indazol-3-yl]-2-pyridyl]piperazin-1-yl]methyl]piperidine-1-carboxylate (210 mg, crude) as a yellow gum Step 4

To a mixture of tert-butyl 4-fluoro-4-[[4-[4-[5-(1-methylcyclopropoxy)-1-(2-trimethylsilylethoxymethyl)indazol-3-yl]-2-pyridyl]piperazin-1-yl]methyl]piperidine-1-carboxylate (205.85 mg, 296.20 μmol, 1 eq) in MeOH (5 mL) was added HCl/EtOAc (4 M, 222.15 μL, 3 eq) in one portion at 20° C. The mixture was stirred at 65° C. for 15 min. LCMS showed the reaction was completed. The residue was poured into $NaHCO_3$ to adjusted the pH=7-8. The aqueous phase was extracted with ethyl acetate (5 mL*3). The combined organic phase was washed with brine (5 mL*2), dried with anhydrous Na2SO4, filtered and concentrated in vacuum to give 3-[2-[4-[(4-fluoro-4-piperidyl)methyl]piperazin-1-yl]-4-pyridyl]-5-(1-methylcyclopropoxy)-1H-indazole (137 mg, 245.03 μmol, 82.72% yield, 83.09% purity) as a yellow solid.

Step 5

To a mixture of 3-[2-[4-[(4-fluoro-4-piperidyl)methyl]piperazin-1-yl]-4-pyridyl]-5-(1-methylcyclopropoxy)-1H-indazole (130 mg, 279.82 μmol, 1 eq) and 1-[2-(2,6-dioxo-3-piperidyl)-1,3-dioxo-isoindolin-5-yl]piperidine-4-carbaldehyde (103.36 mg, 279.82 μmol, 1 eq) in MeOH (5 mL) was added borane; 2-methylpyridine (59.86 mg, 559.65 μmol, 2 eq) and HOAc (16.80 mg, 279.82 μmol, 16.00 μL, 1 eq) in one portion at 25° C. under N2. The mixture was stirred at 25° C. for 16 h. LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (0.225% FA)-ACN]; B %: 0%-40%, 40 min) to give 2-(2,6-dioxo-3-piperidyl)-5-[4-[[4-fluoro-4-[[4-[4-[5-(1-methylcyclopropoxy)-1H-indazol-3-yl]-2-pyridyl]piperazin-1-yl]methyl]-1-piperidyl]methyl]-1-piperidyl]isoindoline-1,3-dione (60.9 mg, 73.70 μmol, 26.34% yield, 98.99% purity) as a yellow solid.

Exemplary Synthesis of Compound 81

Compound 81 was prepared in a manner analogous to compound 80.

Exemplary Synthesis of Compound 82

Step 1

A mixture of benzyl 4-[(1-tert-butoxycarbonyl-4-fluoro-4-piperidyl)methyl]piperazine-1-carboxylate (400 mg, 918.42 μmol, 1 eq) in DCM (3 mL) was added TFA (9.24 g, 81.04 mmol, 6.00 mL, 88.24 eq), and then the mixture was stirred at 25° C. for 1 hr under. TLC (Petroleum ether:Ethyl acetate=1:1) showed started material consumed completed and one new spot found. The reaction mixture was concentrated under reduced pressure to give benzyl 4-[(4-fluoro-4-piperidyl)methyl]piperazine-1-carboxylate (400 mg, crude, TFA) as a yellow oil.

Step 2

A mixture of 1-(4-bromo-2-pyridyl)piperidine-4-carbaldehyde (240.72 mg, 894.41 μmol, 1 eq), benzyl 4-[(4-fluoro-4-piperidyl)methyl]piperazine-1-carboxylate (300 mg, 894.41 μmol, 1 eq) in MeOH (10 mL) was added AcOH (1 mL), borane; 2-methylpyridine (95.67 mg, 894.41 μmol, 1 eq), and then the mixture was stirred at 25° C. for 1 hr under. TLC (Petroleum ether:Ethyl acetate=1:1) showed started material consumed completed and several new spots found. LCMS showed desired MS. The reaction mixture was filtered and the filtrate was concentrated under reduced pressure. The residue was purified by silica gel column chromatography (0 to 100% petroleum in ethyl acetate) to give benzyl 4-[[1-[[1-(4-bromo-2-pyridyl)-4-piperidyl]methyl]-4-fluoro-4-piperidyl]methyl]piperazine-1-carboxylate (480 mg, 791.09 μmol, 88.45% yield, 97% purity) as a colorless gum.

Step 3

To a solution of benzyl 4-[[1-[[1-(4-bromo-2-pyridyl)-4-piperidyl]methyl]-4-fluoro-4-piperidyl]methyl]piperazine-1-carboxylate (480 mg, 815.56 μmol, 1 eq) and 4,4,5,5-tetramethyl-2-(4,4,5,5-tetramethyl-1,3,2-dioxaborolan-2-yl)-1,3,2-dioxaborolane (207.10 mg, 815.56 μmol, 1 eq) in dioxane (10 mL) was added Pd(dppf)Cl2 (59.68 mg, 81.56 μmol, 0.1 eq) and KOAc (240.12 mg, 2.45 mmol, 3 eq). After addition, the reaction mixture was stirred at 100° C. for 12 h under N2. LCMS showed desired MS. The reaction mixture was filtered and the filtrate was concentrated under reduced pressure to give benzyl 4-[[4-fluoro-1-[[1-[4-(4,4,5,5-tetramethyl-1,3,2-dioxaborolan-2-yl)-2-pyridyl]-4-piperidyl]methyl]-4-piperidyl]methyl]piperazine-1-carboxylate (520 mg, crude) as a black solid.

Step 4

To a solution of benzyl 4-[[4-fluoro-1-[[1-[4-(4,4,5,5-tetramethyl-1,3,2-dioxaborolan-2-yl)-2-pyridyl]-4-piperidyl]methyl]-4-piperidyl]methyl]piperazine-1-carboxylate (518 mg, 814.96 μmol, 1 eq), 2-[[3-iodo-5-(1-methylcyclopropoxy)indazol-1-yl]methoxy]ethyl-trimethyl-silane (362.15 mg, 814.96 μmol, 1 eq) in dioxane (10 mL) and H2O (2 mL) was added Pd(dppf)Cl2 (59.63 mg, 81.50 μmol, 0.1 eq) and Na2CO3 (86.38 mg, 814.96 μmol, 1 eq). After addition, the reaction mixture was stirred at 100° C. under N2 for 16 h LCMS showed desired MS. TLC (Petroleum ether:Ethyl acetate=1:1) showed several new spots. The reaction mixture was filtered and concentrated under reduced pressure. The residue was purified by silica gel column chromatography (0 to 100% Petroleum ether in Ethyl acetate) to give benzyl 4-[[4-fluoro-1-[[1-[4-[5-(1-methylcyclopropoxy)-1-(2-trimethylsilylethoxymethyl)indazol-3-yl]-2-pyridyl]-4-piperidyl]methyl]-4-piperidyl]methyl]piperazine-1-carboxylate (630 mg, 579.57 μmol, 71.12% yield, 76% purity) as a brown oil.

Step 5

To a solution of benzyl 4-[[4-fluoro-1-[[1-[4-[5-(1-methylcyclopropoxy)-1-(2-trimethylsilylethoxymethyl)indazol-3-yl]-2-pyridyl]-4-piperidyl]methyl]-4-piperidyl]methyl]piperazine-1-carboxylate (630 mg, 762.60 μmol, 1 eq) in MeOH (2 mL) was added HCl/dioxane (4 M, 2 mL, 10.49 eq). The reaction mixture was stirred at 65° C. under N2 for 1 h. The reaction mixture was filtered and concentrated under reduced pressure. After addition, the crude product was in TFA (3.08 g, 27.01 mmol, 2 mL, 35.42 eq) then the reaction mixture was stirred at 70° C. under N2 for 1 h. LCMS showed desired MS. The reaction mixture was filtered and concentrated under reduced pressure to give 3-[2-[4-[[4-fluoro-4-(piperazin-1-ylmethyl)-1-piperidyl]methyl]-1-piperidyl]-4-pyridyl]-5-(1-methylcyclopropoxy)-1H-indazole (428 mg, crude) as a brown oil.

Step 6

To a solution of 3-[2-[4-[[4-fluoro-4-(piperazin-1-ylmethyl)-1-piperidyl]methyl]-1-piperidyl]-4-pyridyl]-5-(1-methylcyclopropoxy)-1H-indazole (100 mg, 178.02 μmol, 1 eq), 2-(2,6-dioxo-3-piperidyl)-5-fluoro-isoindoline-1,3-dione (49.17 mg, 178.02 μmol, 1 eq) in DMSO (3 mL) was added DIEA (2.23 g, 17.22 mmol, 3 mL, 96.75 eq). After addition, the reaction mixture was stirred at 100° C. under N2 for 16 h. LCMS showed desired MS. The reaction mixture was filtered and concentrated under reduced pressure. The crude product was purified by reversed-phase HPLC (column: 3_Phenomenex Luna C18 75*30 mm*3 um; mobile phase: [water (10 mM NH4HCO3)-ACN]; B %: 30%-80%, 40 min) to give 2-(2,6-dioxo-3-piperidyl)-5-[4-[[4-fluoro-1-[[1-[4-[5-(1-methylcyclopropoxy)-1H-indazol-3-yl]-2-pyridyl]-4-piperidyl]methyl]-4-piperidyl]methyl]piperazin-1-yl]isoindoline-1,3-dione (23 mg, 28.12 μmol, 15.80% yield, 100% purity) as a yellow solid.

Exemplary Synthesis of Compound 83

Step 1

To a solution of tert-butyl 4-fluoro-4-(piperazin-1-ylmethyl)piperidine-1-carboxylate (600 mg, 1.99 mmol, 1 eq) and 2-(2,6-dioxo-3-piperidyl)-5-fluoro-isoindoline-1,3-dione (604.86 mg, 2.19 mmol, 1.1 eq) in DMSO (10 mL) was added DIEA (771.84 mg, 5.97 mmol, 1.04 mL, 3 eq). The mixture was stirred at 120° C. for 2 hr. TLC (Petroleum ether:Ethyl acetate=0:1, Rf=0.3) showed no start material and a new spot. The residue was diluted with H2O (50 mL) extracted with ethyl acetate (40 mL×3). The combined organic layers were washed with brine (3×30 mL) dried over anhydrous sodium sulfate, filtered and concentrated under reduced pressure to give a residue. The residue was purified by silica gel column chromatography (0 to 70% Ethyl acetate in Petroleum ether) to give tert-butyl 4-[[4-[2-(2,6-dioxo-3-piperidyl)-1,3-dioxo-isoindolin-5-yl]piperazin-1-yl]methyl]-4-fluoro-piperidine-1-carboxylate (1.0 g, 1.70 mmol, 85.58% yield, 95% purity) as yellow solid.

Step 2

To a solution of tert-butyl 4-[[4-[2-(2,6-dioxo-3-piperidyl)-1,3-dioxo-isoindolin-5-yl]piperazin-1-yl]methyl]-4-fluoro-piperidine-1-carboxylate (160 mg, 286.94 μmol, 1 eq) in DCM (2 mL) was added TFA (3.08 g, 27.01 mmol, 2 mL, 94.14 eq). The mixture was stirred at 25° C. for 1 hr. TLC (Petroleum ether:Ethyl acetate=0:1, Rf=0.01) showed no start material and a new spot. The residue was concentrated under reduced pressure to afford 2-(2,6-dioxo-3-piperidyl)-5-[4-[(4-fluoro-4-piperidyl)methyl]piperazin-1-yl]isoindoline-1,3-dione (163 mg, crude, TFA) as yellow gum.

Step 3

To a solution of 2-(2,6-dioxo-3-piperidyl)-5-[4-[(4-fluoro-4-piperidyl)methyl]piperazin-1-yl]isoindoline-1,3-dione (163 mg, 285.20 μmol, 1 eq, TFA) in DCM (5 mL) was added DIEA (184.30 mg, 1.43 mmol, 248.38 μL, 5 eq) and stirred at 25° C. 10 min. Then the mixture was concentrated. The residue tert-butyl 4-formylpiperidine-1-carboxylate (72.99 mg, 342.25 μmol, 1.2 eq) in MeOH (10 mL) and HOAC (1 mL) was stirred at 25° C. for 5 min, then was added borane; 2-methylpyridine (61.01 mg, 570.41 μmol, 2 eq). Then the mixture was stirred at 25° C. for 16 under N2. TLC (Dichloromethane:Methanol=10:1, Rf=0.3) was showed the reaction completed. The reaction mixture was poured into H2O (20 mL). The mixture was extracted with ethyl acetate (30 mL*3). The organic phase was washed with brine (20 mL), dried over anhydrous Na2SO4, concentrated in vacuum to give a residue. The residue was purified by silica gel column chromatography (0-10% Methanol in Dichloromethane) to give tert-butyl 4-[[4-[[4-[2-(2,6-dioxo-3-piperidyl)-1,3-dioxo-isoindolin-5-yl]piperazin-1-yl]methyl]-4-fluoro-1-piperidyl]methyl]piperidine-1-carboxylate (180 mg, 203.43 μmol, 71.33% yield, 74% purity) as a yellow gum.

Step 4

To a solution of tert-butyl 4-[[4-[[4-[2-(2,6-dioxo-3-piperidyl)-1,3-dioxo-isoindolin-5-yl]piperazin-1-yl]methyl]-4-fluoro-1-piperidyl]methyl]piperidine-1-carboxylate (180 mg, 274.91 μmol, 1 eq) in DCM (2 mL) was added TFA (3.08 g, 27.01 mmol, 2 mL, 98.26 eq). The mixture was stirred at 25° C. for 2 hr. TLC (Dichloromethane:Methanol=10:1, Rf=0.01) was showed the reaction completed. The residue was concentrated under reduced pressure to afford 2-(2,6-dioxo-3-piperidyl)-5-[4-[[4-fluoro-1-(4-piperidylmethyl)-4-piperidyl]methyl]piperazin-1-yl]isoindoline-1,3-dione (180 mg, crude, TFA) as yellow gum.

Step 5

To a solution of 2-(2,6-dioxo-3-piperidyl)-5-[4-[[4-fluoro-1-(4-piperidylmethyl)-4-piperidyl]methyl]piperazin-1-yl]isoindoline-1,3-dione (150 mg, 224.32 μmol, 1 eq, TFA) and 3-(6-chloropyrimidin-4-yl)-6-(1-methylcyclopropoxy)-1H-indazole (53.97 mg, 179.46 μmol, 0.8 eq) in DMSO (5 mL) and DIEA (289.92 mg, 2.24 mmol, 390.72 μL, 10 eq). The mixture was stirred at 80° C. for 16 h. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-30%, 40 min) to afford 2-(2,6-dioxo-3-piperidyl)-5-[4-[[4-fluoro-1-[[1-[6-[5-(1-methylcyclopropoxy)-1H-indazol-3-yl]pyrimidin-4-yl]-4-piperidyl]methyl]-4-piperidyl]methyl]piperazin-1-yl]isoindoline-1,3-dione (38.8 mg, 47.09 μmol, 20.99% yield, 99.39% purity) as a yellow solid.

Exemplary Synthesis of Compound 84

Step 1

To a solution of benzyl 4-(1-tert-butoxycarbonylpiperidine-4-carbonyl) piperazine-1-carboxylate (2.3 g, 5.33 mmol, 1 eq) in DCM (12 mL) was added TFA (5.45 g, 47.79 mmol, 3.54 mL, 8.97 eq). The mixture was stirred at 25° C. for 1 hr. LC-MS (EB2049-70-P1A) showed Reactant 1 was consumed completely and one main peak with desired m/z was detected. The reaction mixture was concentrated under reduced pressure to remove solvent, and then the residue was quenched with sat.$NaHCO_3$ (30 mL) and extracted with EA (30 mL). The organic layer was washed with water (30 mL×2), brine (30 mL×2), dried over anhydrous Na2SO4, filtered and concentrated in vacuo to afford benzyl 4-(piperidine-4-carbonyl) piperazine-1-carboxylate (1.9 g, 4.27 mmol, 80.03% yield, TFA) as a yellow oil. The crude product was used into the next step without further purification.

Step 2

To a solution of benzyl 4-(piperidine-4-carbonyl)piperazine-1-carboxylate (220 mg, 663.83 μmol, 1 eq) and 1-[2-(2,6-dioxo-3-piperidyl)-1,3-dioxo-isoindolin-5-yl]piperidine-4-carbaldehyde (245.20 mg, 663.83 μmol, 1 eq) in MeOH (5 mL) and AcOH (2 mL) and MeOH (5 mL) was added borane; 2-methylpyridine (142.01 mg, 1.33 mmol, 2 eq). The mixture was stirred at 25° C. for 16 hr. LC-MS (EB2049-71-P1B) showed Reactant 1 was consumed completely and one main peak with desired m/z was detected. The reaction mixture was concentrated under reduced pressure to remove solvent. The residue was purified by flash silica gel chromatography (0-10% MeOH/DCM) to give benzyl 4-[1-[[1-[2-(2,6-dioxo-3-piperidyl)-1,3-dioxo-isoindolin-5-yl]-4-piperidyl]methyl]piperidine-4-carbonyl]piperazine-1-carboxylate (202 mg, 294.99 μmol, 44.44% yield) as a yellow oil Step 3

To a solution of benzyl 4-[1-[[1-[2-(2,6-dioxo-3-piperidyl)-1,3-dioxo-isoindolin-5-yl]-4-piperidyl]methyl]piperidine-4-carbonyl]piperazine-1-carboxylate (202 mg, 294.99 μmol, 1 eq) in TFA (3 mL). The mixture was stirred at 70° C. for 1 hr. TLC indicated Reactant 1 was consumed completely and one new spot formed. The reaction mixture was concentrated under reduced pressure to remove solvent to afford 2-(2,6-dioxo-3-piperidyl)-5-[4-[[4-(piperazine-1-carbonyl)-1-piperidyl]methyl]-1-piperidyl]isoindoline-1,3-dione (400 mg, 248.83 μmol, 84.35% yield, 91% purity, 8TFA) as a light yellow oil. The crude product was used into the next step without further purification.

Step 4

To a solution of 2-(2,6-dioxo-3-piperidyl)-5-[4-[[4-(piperazine-1-carbonyl)-1-piperidyl]methyl]-1-piperidyl]isoindoline-1,3-dione (400 mg, 273.44 μmol, 1 eq, 8TFA) and 3-(6-chloropyrimidin-4-yl)-5-(1-methylcyclopropoxy)-1H-indazole (82.24 mg, 273.44 μmol, 1 eq) in DMSO (3 mL) was added DIEA (353.40 mg, 2.73 mmol, 476.29 μL, 10 eq). The mixture was stirred at 80° C. for 16 hr. LCMS showed Reactant 1 was consumed completely and one main peak with desired m/z was detected. The reaction mixture was concentrated under reduced pressure to remove solvent. The crude product was purified by reversed-phase HPLC (column: Phenomena Luna C18 75*30 mm*3 um; mobile phase: [water (0.225% FA)-ACN]; B %: 5%-35%, 35 min) to afford 2-(2,6-dioxo-3-piperidyl)-5-[4-[[4-[4-[6-[5-(1-methylcyclopropoxy)-2H-indazol-3-yl]pyrimidin-4-yl]piperazine-1-carbonyl]-1-piperidyl]methyl]-1-piperidyl]isoindoline-1,3-dione (17.6 mg, 19.86 μmol, 7.26% yield, 91.967% purity) as a white solid Exemplary Synthesis of Compound 85

Step 1

To a solution of 1-tert-butoxycarbonylpiperidine-4-carboxylic acid (10.41 g, 45.40 mmol, 1 eq) in DMF (100 mL) was added DIEA (17.60 g, 136.20 mmol, 23.72 mL, 3 eq) and HATU (22.44 g, 59.02 mmol, 1.3 eq). The mixture was stirred at 25° C. for 0.5 h. The reaction solution was added benzyl piperazine-1-carboxylate (10 g, 45.40 mmol, 8.77 mL, 1 eq). The mixture was stirred for 2 h at 25° C. TLC (Petroleum ether/Ethyl acetate=1/1, RF=0.17) indicated no reactant 1 was remained, and one major new spot with lower polarity was detected. The reaction mixture was diluted with water (20 mL*3) and extracted with EA (30 mL). The combined organic layers were washed with brine (20 mL), dried over Na2SO4, filtered and concentrated under reduced pressure to give a residue. The crude product was purified by column chromatography on silica gel (0-60% (15 min) of Ethyl acetate in Petroleum ether, 60% (10 min) of Ethyl acetate in Petroleum ether) to give benzyl 4-(1-tert-butoxycarbonylpiperidine-4-carbonyl)piperazine-1-carboxylate (13 g, 30.13 mmol, 66.36% yield) as a yellow oil.

Step 2

To a solution of benzyl 4-(1-tert-butoxycarbonylpiperidine-4-carbonyl)piperazine-1-carboxylate (3 g, 6.95 mmol, 1 eq) in EtOAc (50 mL) was added Pd/C (500 mg, 6.95 mmol, 10% purity, 1 eq) under N2. The suspension was degassed under vacuum and purged with H2 several times. The mixture was stirred under H2 (15 psi) at 25° C. for 3 hours. TLC (Petroleum ether/Ethyl acetate=1/1, RF=0) indicated no reactant 1 was remained, and one major new spot with lower polarity was detected. The reaction mixture was filtered and the filter was concentrated to give tert-butyl 4-(piperazine-1-carbonyl)piperidine-1-carboxylate (1.8 g, 6.05 mmol, 87.06% yield) as a yellow oil.

Step 3

To a solution of tert-butyl 4-(piperazine-1-carbonyl)piperidine-1-carboxylate (900 mg, 3.03 mmol, 1 eq) in DMSO (10 mL) was added K2CO3 (1.25 g, 9.08 mmol, 3 eq) and 4-bromo-2-fluoro-pyridine (692.37 mg, 3.93 mmol, 1.3 eq). The mixture was stirred at 100° C. for 16 hr. LC-MS showed no reactant 1 was remained. Several new peaks were shown on LC-MS and ~53% of desired compound was detected. The reaction mixture was diluted with water (20 mL) and extracted with EA (30 mL). The combined organic layers were washed with brine (20 mL), dried over Na2SO4, filtered and concentrated under reduced pressure to give a residue. The crude product was purified by column chromatography on silica gel (column height: 20 g, 100-200 mesh silica gel, 0-20% (15 min) of Ethyl acetate in Petroleum ether, 20% (10 min) of Ethyl acetate in Petroleum ether) to give tert-butyl 4-[4-(4-bromo-2-pyridyl)piperazine-1-carbonyl]piperidine-1-carboxylate (1.1 g, 2.43 mmol, 80.17% yield) as a yellow oil.

Step 4

A mixture of tert-butyl 4-[4-(4-bromo-2-pyridyl)piperazine-1-carbonyl]piperidine-1-carboxylate (300 mg, 661.71 μmol, 1 eq), 4,4,5,5-tetramethyl-2-(4,4,5,5-tetramethyl-1,3,2-dioxaborolan-2-yl)-1,3,2-dioxaborolane (252.05 mg, 992.56 μmol, 1.5 eq), Pd(dppf)Cl2 (72.63 mg, 99.26 μmol, 0.15 eq), KOAc (194.82 mg, 1.99 mmol, 3 eq) and 4,4,5,5-tetramethyl-2-(4,4,5,5-tetramethyl-1,3,2-dioxaborolan-2-yl)-1,3,2-dioxaborolane (252.05 mg, 992.56 μmol, 1.5 eq) in dioxane (15 mL) was degassed and purged with N2 for 3 times, and then the mixture was stirred at 90° C. for 12 hr under N2 atmosphere. LC-MS (EB134-911-P1A) showed no reactant 1 was remained. Several new peaks were shown on LC-MS and ~61% of desired compound was detected. The reaction mixture was diluted with water (20 mL) and extracted with EA (30 mL). The combined organic layers were washed with brine (20 mL), dried over Na2SO4, filtered and concentrated under reduced pressure to give a residue to give [2-[4-(1-tert-butoxycarbonylpiperidine-4-carbonyl)piperazin-1-yl]-4-pyridyl]boronic acid (260 mg, 444.42 μmol, 67.16% yield, 71.5% purity) as a black oil.

Step 5

A mixture of [2-[4-(1-tert-butoxycarbonylpiperidine-4-carbonyl)piperazin-1-yl]-4-pyridyl]boronic acid (140 mg, 334.69 μmol, 1 eq), 2-[[3-iodo-5-(1-methylcyclopropoxy)indazol-1-yl]methoxy]ethyl-trimethyl-silane (148.73 mg, 334.69 μmol, 1 eq), Pd(dppf)Cl2 (24.49 mg, 33.47 μmol, 0.1 eq), Na2CO3 (106.42 mg, 1.00 mmol, 3 eq) in dioxane (6 mL) and H2O (1 mL) was degassed and purged with N2 for 3 times, and then the mixture was stirred at 90° C. for 3 hr under N2 atmosphere. LC-MS (EB134-917-P1A) showed no reactant 1 was remained. Several new peaks were shown on LC-MS and ~47% of desired compound was detected. The reaction mixture was diluted with water (20 mL) and extracted with EA (30 mL). The combined organic layers were washed with brine (20 mL), dried over Na2SO4, filtered and concentrated under reduced pressure to give a residue. The crude product was purified by column chromatography on silica gel (0-60% (25 min) of Ethyl acetate in Petroleum ether, 60% (10 min) of Ethyl acetate in Petroleum ether) to give tert-butyl 4-[4-[4-[5-(1-methylcyclopropoxy)-1-(2-trimethylsilylethoxymethyl)indazol-3-yl]-2-pyridyl]piperazine-1-carbonyl]piperidine-1-carboxylate (130 mg, 174.98 μmol, 52.28% yield, 93% purity) as a yellow gum.

Step 6

To a solution of tert-butyl 4-[4-[4-[5-(1-methylcyclopropoxy)-1-(2-trimethylsilylethoxymethyl)indazol-3-yl]-2-pyridyl]piperazine-1-carbonyl]piperidine-1-carboxylate (130 mg, 188.15 μmol, 1 eq) in MeOH (2 mL) was added HCl/dioxane (4 M, 1.44 mL, 30.71 eq). The mixture was stirred at 25° C. for 2 hr. LC-MS (EB134-919-P1B) showed no reactant 1 was remained. Several new peaks were shown on LC-MS and ~80% of desired compound was detected. The mixture was quenched with sat.$NaHCO_3$ (30 mL) and extracted with EA (30 mL). The organic layer was washed with water (30 mL×2), brine (30 mL×2), dried over anhydrous Na2SO4, filtered and concentrated in vacuo to give [4-[4-[5-(1-methylcyclopropoxy)-1H-indazol-3-yl]-2-pyridyl]piperazin-1-yl]-(4-piperidyl)methanone (100 mg, 187.81 μmol, 99.82% yield, 86.5% purity) as a yellow gum.

Step 7

To a solution of [4-[4-[5-(1-methylcyclopropoxy)-1H-indazol-3-yl]-2-pyridyl]piperazin-1-yl]-(4-piperidyl)methanone (100 mg, 217.12 μmol, 1 eq) and 1-[2-(2,6-dioxo-3-piperidyl)-1,3-dioxo-isoindolin-5-yl]piperidine-4-carbaldehyde (88.22 mg, 238.83 μmol, 1.1 eq) in MeOH (3 mL) and AcOH (0.3 mL) was added borane; 2-methylpyridine (116.12 mg, 1.09 mmol, 5 eq). The mixture was stirred at 25° C. for 12 hr. LC-MS (EB134-920-P1A) showed no reactant 1 was remained. Several new peaks were shown on LC-MS and ~61% of desired compound was detected. The resulting product was filtered to remove the insoluble. The impure product was purified by Prep-HPLC (column: 3_Phenomenex Luna C18 75*30 mm*3 um; mobile phase: [water (0.225% FA)-ACN]; B %: 0%-35%, 40 min) to give 2-(2,6-dioxo-3-piperidyl)-5-[4-[[4-[4-[4-[5-(1-methylcyclopropoxy)-2H-indazol-3-yl]-2-pyridyl]piperazine-1-carbonyl]-1-piperidyl]methyl]-1-piperidyl]isoindoline-1,3-dione (101 mg, 122.97 μmol, 56.64% yield, 99.101% purity) as a yellow solid.

Exemplary Synthesis of Compound 86

Compound 86 was prepared in a manner analogous to compound 84.

Exemplary Synthesis of Compound 87

Step 1

A mixture of 1-tert-butoxycarbonylpiperidine-4-carboxylic acid (3.80 g, 16.57 mmol, 1 eq), HATU (9.45 g, 24.86 mmol, 1.5 eq), DIEA (6.43 g, 49.71 mmol, 8.66 mL, 3 eq) in DCM (10 mL) was added benzyl 4-(4-piperidylmethyl)piperazine-1-carboxylate (5.26 g, 16.57 mmol, 1 eq), and then the mixture was stirred at 25° C. for 1 hr. LCMS showed desired MS. TLC (Dichloromethane:Methanol=10:1) showed started material consumed completed and several new spots found. The reaction mixture was filtered and the filtrate was concentrated under reduced pressure The residue was purified by silica gel column chromatography (0 to 30% Dichloromethane in Methanol) to give benzyl 4-[[1-(1-tert-butoxycarbonylpiperidine-4-carbonyl)-4-piperidyl]methyl]piperazine-1-carboxylate (11 g, 15.19 mmol, 91.66% yield, 73% purity) as a yellow gum.

Step 2

A mixture of benzyl 4-[[1-(1-tert-butoxycarbonylpiperidine-4-carbonyl)-4-piperidyl]methyl]piperazine-1-carboxylate (3.6 g, 6.81 mmol, 1 eq) in DCM (3 mL) was added TFA (33.26 g, 291.73 mmol, 21.60 mL, 42.84 eq), and then the mixture was stirred at 25° C. for 1 hr. TLC (Dichloromethane:Methanol=10:1) showed one new spot. The reaction mixture was concentrated under reduced pressure to give benzyl 4-[[1-(piperidine-4-carbonyl)-4-piperidyl]methyl]piperazine-1-carboxylate (3 g, crude, TFA) as a yellow oil.

Step 3

A mixture of benzyl 4-[[1-(piperidine-4-carbonyl)-4-piperidyl]methyl]piperazine-1-carboxylate (1.4 g, 3.27 mmol, 1 eq), 4-bromo-2-fluoro-pyridine (574.90 mg, 3.27 mmol, 1 eq) in DMSO (5 mL) was added DIEA (1.27 g, 9.80 mmol, 1.71 mL, 3 eq), and then the mixture was stirred at 80° C. for 16 hr. LCMS showed the starting material was consumed completely and desired MS found. TLC (Dichloromethane:Methanol=10:1) showed several new spots. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel column chromatography (0 to 30% Dichloromethane in Methanol) to give benzyl 4-[[1-[1-(4-bromo-2-pyridyl)piperidine-4-carbonyl]-4-piperidyl]methyl]piperazine-1-carboxylate (1.22 g, 1.11 mmol, 33.86% yield, 53% purity) as a yellow gum.

Step 4

To a solution of benzyl 4-[[1-[1-(4-bromo-2-pyridyl)piperidine-4-carbonyl]-4-piperidyl]methyl]piperazine-1-carboxylate (300 mg, 513.22 umol, 1 eq) and 4,4,5,5-tetramethyl-2-(4,4,5,5-tetramethyl-1,3,2-dioxaborolan-2-yl)-1,3,2-dioxaborolane (130.33 mg, 513.22 μmol, 1 eq) in dioxane (10 mL) was added Pd(dppf)Cl2 (37.55 mg, 51.32 μmol, 0.1 eq) and KOAc (151.10 mg, 1.54 mmol, 3 eq). After addition, the reaction mixture was stirred at 100° C. for 12 h under N2. LCMS showed desired MS. The reaction mixture was filtered and concentrated under reduced pressure. to give benzyl 4-[[1-[1-[4-(4,4,5,5-tetramethyl-1,3,2-dioxaborolan-2-yl)-2-pyridyl]piperidine-4-carbonyl]-4-piperidyl]methyl]piperazine-1-carboxylate (400 mg, crude) as a black solid.

Step 5

To a solution of benzyl 4-[[1-[1-[4-(4,4,5,5-tetramethyl-1,3,2-dioxaborolan-2-yl)-2-pyridyl]piperidine-4-carbonyl]-4-piperidyl]methyl]piperazine-1-carboxylate (142.13 mg, 225.03 μmol, 1 eq), 2-[[3-iodo-5-(1-methylcyclopropoxy)indazol-1-yl]methoxy]ethyl-trimethyl-silane (100 mg, 225.03 μmol, 1 eq) in dioxane (10 mL) and H2O (2 mL) was added Pd(dppf)Cl2 (16.47 mg, 22.50 μmol, 0.1 eq) and Na2CO3 (71.55 mg, 675.09 μmol, 3 eq). After addition, the reaction mixture was stirred at 100° C. under N2 for 16 h. LCMS showed desired MS. TLC (Petroleum ether:Ethyl acetate=1:1) showed several new spots. The reaction mixture was filtered and concentrated under reduced pressure. The residue was purified by silica gel column chromatography (0 to 30% Methanol in Dichloromethane) to give benzyl 4-[[1-[1-[4-[5-(1-methylcyclopropoxy)-1-(2-trimethylsilylethoxymethyl)indazol-3-yl]-2-pyridyl]piperidine- 4-carbonyl]-4-piperidyl]methyl]piperazine-1-carboxylate (90 mg, 53.64 μmol, 23.84% yield, 49% purity) as a black solid.

Step 6

To a solution of benzyl 4-[[1-[1-[4-[5-(1-methylcyclopropoxy)-1-(2-trimethylsilylethoxymethyl)indazol-3-yl]-2-pyridyl]piperidine-4-carbonyl]-4-piperidyl]methyl]piperazine-1-carboxylate (90 mg, 109.47 μmol, 1 eq) in TFA (12.48 mg, 109.47 μmol, 8.11 μL, 1 eq). After addition, the reaction mixture was stirred at 70° C. under N2 for 0.5 h. LCMS showed desired MS The reaction mixture was filtered and concentrated under reduced pressure to give [1-[4-[5-(1-methylcyclopropoxy)-1H-indazol-3-yl]-2-pyridyl]-4-piperidyl]-[4-(piperazin-1-ylmethyl)-1-piperidyl]methanone (80 mg, crude, TFA) as a brown oil.

Step 7

A mixture of [1-[4-[5-(1-methylcyclopropoxy)-1H-indazol-3-yl]-2-pyridyl]-4-piperidyl]-[4-(piperazin-1-ylmethyl)-1-piperidyl]methanone (50 mg, 89.65 μmol, 1 eq), 2-(2,6-dioxo-3-piperidyl)-5-fluoro-isoindoline-1,3-dione (24.76 mg, 89.65 μmol, 1 eq) in DMSO (3 mL) was added DIEA (11.59 mg, 89.65 μmol, 15.62 μL, 1 eq), and then the mixture was stirred at 100° C. for 16 hr. LCMS showed the starting material was consumed completely and desired MS found. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (10 mM NH4HCO3)-ACN]; B %: 20%-70%, 40 min) to give 2-(2,6-dioxo-3-piperidyl)-5-[4-[[1-[1-[4-[5-(1-methylcyclopropoxy)-1H-indazol-3-yl]-2-pyridyl]piperidine-4-carbonyl]-4-piperidyl]methyl]piperazin-1-yl]isoindoline-1,3-dione (13.5 mg, 16.41 μmol, 18.31% yield, 98.95% purity) as a yellow solid.

Exemplary Synthesis of Compound 88

Step 1

To a solution of 1-benzyloxycarbonylpiperidine-4-carboxylic acid (5.59 g, 21.24 mmol, 1.2 eq) in DCM (60 mL) was added HATU (8.75 g, 23.02 mmol, 1.3 eq), then the mixture was stirred at 25° C. under N2 for 1 hour. And then tert-butyl 4-(4-piperidylmethyl)piperidine-1-carboxylate (5 g, 17.70 mmol, 1 eq) and DIEA (4.58 g, 35.41 mmol, 6.17 mL, 2 eq) was added the above mixture. The mixture was stirred at 25° C. under N2 for 15 hours. TLC (Petroleum ether:Ethyl acetate=1:2, Rf=0.46, PMA) showed a main new spot formed. The reaction mixture was added water 100 mL and extracted with DCM (100 mL*3). The combined organic layers were washed with brine (100 mL*3), dried over Na2SO4, filtered and concentrated under reduced pressure to give a residue. The residue was purified by flash silica gel chromatography (0-55% Ethyl acetate/Petroleum ether). Compound tert-butyl 4-[[1-(1-benzyloxycarbonylpiperidine-4-carbonyl)-4-piperidyl]methyl]piperidine-1-carboxylate (7.6 g, crude) was obtained as a light yellow gum.

Step 2

To a solution of tert-butyl 4-[[1-(1-benzyloxycarbonylpiperidine-4-carbonyl)-4-piperidyl]methyl]piperidine-1-carboxylate (2.1 g, 3.98 mmol, 1 eq) in DCM (20 mL) was added HCl/dioxane (4 M, 10 mL, 10.05 eq), the mixture was stirred at 25° C. for 2 hours. TLC (Petroleum ether:Ethyl acetate=1:1, PMA, Plate1) showed new spots formed. The reaction mixture was concentrated under reduced pressure to give a residue. Compound benzyl 4-[4-(4-piperidylmethyl)piperidine-1-carbonyl]piperidine-1-carboxylate (1.45 g, crude, HCl) was obtained as a white solid.

Step 3

To a solution of 2-(2,6-dioxo-3-piperidyl)-5-fluoro-isoindoline-1,3-dione (200 mg, 724.06 μmol, 1 eq) and benzyl 4-[4-(4-piperidylmethyl)piperidine-1-carbonyl]piperidine-1-carboxylate (503.99 mg, 1.09 mmol, 1.50 eq, HCl) in DMSO (5 mL) was added DIEA (467.90 mg, 3.62 mmol, 630.59 μL, 5 eq) and then the mixture was stirred at 90° C. for 16 hours. TLC (Petroleum ether:Ethyl acetate=3:1, Rf=0.49, UV=254 nm, Plate1) showed new spots formed. The reaction mixture was added water 30 mL and extracted with EtOAc (30 mL*3). The combined organic layers were washed with brine (30 mL*3), dried over Na2SO4, filtered and concentrated under reduced pressure to give a residue. The residue was purified by flash silica gel chromatography (of 0-10% Ethyl acetate/Petroleum ether). Compound benzyl 4-[4-[[1-[2-(2,6-dioxo-3-piperidyl)-1,3-dioxo-isoindolin-5-yl]-4-piperidyl]methyl]piperidine-1-carbonyl]piperidine-1-carboxylate (210 mg, 270.26 μmol, 37.33% yield, 88% purity) was obtained as a yellow solid.

Step 4

To a solution of benzyl 4-[4-[[1-[2-(2,6-dioxo-3-piperidyl)-1,3-dioxo-isoindolin-5-yl]-4-piperidyl]methyl]piperidine-1-carbonyl]piperidine-1-carboxylate (210 mg, 307.11 μmol, 1 eq) in TFA (4.62 g, 40.52 mmol, 3 mL, 131.93 eq), then the mixture was stirred at 80° C. for 1 hour. LCMS showed ~88.53% compound and the starting materials was consumed completely. The reaction mixture was concentrated under reduced pressure to give a residue. Compound 2-(2,6-dioxo-3-piperidyl)-5-[4-[[1-(piperidine-4-carbonyl)-4-piperidyl]methyl]-1-piperidyl]isoindoline-1,3-dione (200 mg, 155.11 μmol, 50.51% yield, 78% purity, 4TFA) was obtained as a light yellow gum.

Step 5

To a solution 2-(2,6-dioxo-3-piperidyl)-5-[4-[[1-(piperidine-4-carbonyl)-4-piperidyl]methyl]-1-piperidyl]isoindoline-1,3-dione (200 mg, 198.86 μmol, 1 eq, 4TFA) and 3-(6-chloropyrimidin-4-yl)-5-(1-methylcyclopropoxy)-1H-indazole (59.80 mg, 198.86 μmol, 1 eq) in DMSO (3 mL) was added DIEA (257.01 mg, 1.99 mmol, 346.37 μL, 10 eq), then the mixture was stirred at 90° C. for 16 hours. LCMS showed ~50.5% desire compound and the starting materials was consumed completely. The residue was purified by prep-HPLC (column: 3_Phenomenex Luna C18 75*30 mm*3 um; mobile phase: [water (0.225% FA)-ACN]; B %: 10%-60%, 40 min). Compound 2-(2,6-dioxo-3-piperidyl)-5-[4-[[1-[1-[6-[5-(1-methylcyclopropoxy)-1H-indazol-3-yl]pyrimidin-4-yl]piperidine-4-carbonyl]-4-piperidyl]methyl]-1-piperidyl]isoindoline-1,3-dione (45 mg, 53.27 μmol, 26.79% yield, 96.346% purity) was obtained as a yellow solid.

Exemplary Synthesis of Compound 89

Compound 89 was prepared in a manner analogous to compound 82 using afford tert-butyl 4-[[1-[1-(4-bromo-2-pyridyl)piperidine-4-carbonyl]-4-piperidyl]methyl]piperidine-1-carboxylate.

Step 1

To a solution of tert-butyl 4-[[1-(1-benzyloxycarbonylpiperidine-4-carbonyl)-4-piperidyl]methyl]piperidine-1-carboxylate (2 g, 3.79 mmol, 1 eq) in EtOH (20 mL) and EtOAc (20 mL) was added Pd/C (0.54 g, 10% purity) under N2. The suspension was degassed under vacuum and purged with H2 (15 psi) several times. The reaction mixture was stirred at 25° C. for 1 h. TLC (petroleum ether:ethyl acetate=1:2)

showed the reaction completed. The reaction mixture was filtered and filtrate was concentrated under reduced pressure to afford tert-butyl 4-[[1-(piperidine-4-carbonyl)-4-piperidyl]methyl]piperidine-1-carboxylate (1.45 g, 3.44 mmol, 90.89% yield, 93.5% purity) as a white gum.

Step 2

To a solution of tert-butyl 4-[[1-(piperidine-4-carbonyl)-4-piperidyl]methyl]piperidine-1-carboxylate (500 mg, 1.27 mmol, 1 eq) and 4-bromo-2-fluoro-pyridine (290.66 mg, 1.65 mmol, 1.3 eq) in DMSO (8 mL) was added K2CO3 (526.75 mg, 3.81 mmol, 3 eq). After addition, the reaction solution was stirred at 100° C. for 12 h. LCMS showed desired MS. TLC (petroleum ether:ethyl acetate=1:1) showed several spots. After cooling, the reaction mixture was filtered and filtrate was diluted with ethyl acetate (20 mL) and washed with brine (20 mL*3). The organic layer was concentrated under reduced pressure. The residue was purified by silica gel column chromatography (0 to 65% ethyl acetate in petroleum ether) to afford tert-butyl 4-[[1-[1-(4-bromo-2-pyridyl)piperidine-4-carbonyl]-4-piperidyl]methyl]piperidine-1-carboxylate (300 mg, 510.97 μmol, 40.22% yield, 93.6% purity) as a white solid.

Exemplary Synthesis of Compound 90

Compound 90 was prepared in a manner analogous to compound 84.

Exemplary Synthesis of Compound 91

Compound 91 was prepared in a manner analogous to compound 82.

Exemplary Synthesis of Compound 92

Step 1

To a solution of tert-butyl 4-[[1-(piperidine-4-carbonyl)-4-piperidyl]methyl]piperidine-1-carboxylate (300 mg, 762.27 μmol, 1 eq) and 2-(2,6-dioxo-3-piperidyl)-5-fluoro-isoindoline-1,3-dione (210.55 mg, 762.27 μmol, 1 eq in DMSO (5 mL) was added DIEA (492.59 mg, 3.81 mmol, 663.87 μL, 5 eq). After addition, the mixture was stirred at 100° C. for 16 hours. LCMS showed there was desired MS. The residue was poured into water (20 mL). The aqueous phase was extracted with ethyl acetate (20 mL*3). The combined organic phase was washed with brine (20 mL*2), dried with anhydrous Na2SO4, filtered and concentrated in vacuum. The residue was purified by silica gel chromatography (4 g, 0-80% (12 min) of Ethyl acetate in Petroleum ether, 80% (10 min) of Ethyl acetate in Petroleum ether) to afford tert-butyl 4-[[1-[1-[2-(2,6-dioxo-3-piperidyl)-1,3-dioxo-isoindolin-5-yl]piperidine-4-carbonyl]-4-piperidyl]methyl]piperidine-1-carboxylate (401 mg, 598.62 μmol, 78.53% yield, 97% purity) as a yellow solid.

Step 2

To a solution of tert-butyl 4-[[1-[1-[2-(2,6-dioxo-3-piperidyl)-1,3-dioxo-isoindolin-5-yl]piperidine-4-carbonyl]-4-piperidyl]methyl]piperidine-1-carboxylate (200 mg, 307.80 μmol, 1 eq) in DCM (3 mL) was added TFA (1.23 g, 10.80 mmol, 0.8 mL, 35.10 eq). After addition, the reaction solution was stirred at 25° C. for 1 h. TLC showed the reaction was completed. The reaction mixture was concentrated under reduced pressure to remove solvent to afford 2-(2,6-dioxo-3-piperidyl)-5-[4-[4-(4-piperidylmethyl)piperidine-1-carbonyl]-1-piperidyl]isoindoline-1,3-dione (150 mg, 198.89 μmol, 64.62% yield, 88% purity, TFA) as a brown solid.

Step 3

To a solution of 2-(2,6-dioxo-3-piperidyl)-5-[4-[4-(4-piperidylmethyl)piperidine-1-carbonyl]-1-piperidyl]isoindoline-1,3-dione (118.80 mg, 216.13 μmol, 1 eq) and 3-(6-chloropyrimidin-4-yl)-5-(1-methylcyclopropoxy)-1H-indazole (65 mg, 216.13 μmol, 1 eq) in DMSO (3 mL) was added DIEA (371.00 mg, 2.87 mmol, 0.5 mL, 13.28 eq). After addition, the mixture was stirred at 90° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous Na2SO4, filtered and concentrated in vacuum. The residue was purified by prep.HPLC (column: 3_Phenomenex Luna C18 75*30 mm*3 um; mobile phase: [water (0.225% FA)-ACN]; B %: 10%-50%, 40 min) to afford 2-(2,6-dioxo-3-piperidyl)-5-[4-[4-[[1-[6-[5-(1-methylcyclopropoxy)-1H-indazol-3-yl]pyrimidin-4-yl]-4-piperidyl]methyl]piperidine-1-carbonyl]-1-piperidyl]isoindoline-1,3-dione (13.1 mg, 15.97 μmol, 7.39% yield, 99.2% purity) as a yellow solid.

Exemplary Synthesis of Compound 93

Compound 93 was prepared in a manner analogous to compound 82.

Exemplary Synthesis of Compound 94

Compound 94 was prepared in a manner analogous to compound 92.

Exemplary Synthesis of Compound 95

Compound 95 was prepared in a manner analogous to compound 82.

Exemplary Synthesis of Compound 96

Step 1

To a mixture of 2-[[3-(6-chloropyrimidin-4-yl)-5-(1-methylcyclopropoxy)indazol-2-yl]methoxy]ethyl-trimethyl-silane (257.40 mg, 597.21 μmol, 1 eq) and tert-butyl 4-fluoro-4-(piperazin-1-ylmethyl)piperidine-1-carboxylate (180 mg, 597.21 μmol, 1 eq) in DMSO (5 mL) was added Et3N (181.29 mg, 1.79 mmol, 249.37 μL, 3 eq) in one portion at 25° C. The mixture was stirred at 100° C. for 1 h to give yellow solution. LCMS showed the reaction was completed. The mixture was cooled to 25° C. and concentrated in reduced pressure at 25° C. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel chromatography (Petroleum ether: Ethyl acetate=3:1, Rf=0.43, 0-100% (15 min) of Ethyl acetate in Petroleum ether) to give tert-butyl 4-fluoro-4-[[4-[6-[5-(1-methylcyclopropoxy)-2-(2-trimethylsilylethoxymethyl)indazol-3-yl]pyrimidin-4-yl]piperazin-1-yl]methyl]piperidine-1-carboxylate (300 mg, 431.07 μmol, 72.18% yield) as a yellow solid.

Step 2

To a mixture of tert-butyl 4-fluoro-4-[[4-[6-[5-(1-methylcyclopropoxy)-2-(2-trimethylsilylethoxymethyl)indazol-3-yl]pyrimidin-4-yl]piperazin-1-yl]methyl]piperidine-1-carboxylate (300 mg, 431.07 μmol, 1 eq) in MeOH (5 mL) was added HCl/EtOAc (4 M, 2 mL, 18.56 eq) in one portion and then was stirred at 65° C. for 30 min. TLC showed the starting material was consumed completely. The mixture was concentrated in vacuum to give 3-[6-[4-[(4-fluoro-4-piperidyl)methyl]piperazin-1-yl]pyrimidin-4-yl]-5-(1-methylcyclopropoxy)-2H-indazole (199 mg, 418.89 μmol, 97.17% yield, 98% purity) as a yellow solid Step 3

To a mixture of 1-[2-(2,6-dioxo-3-piperidyl)-1,3-dioxo-isoindolin-5-yl]piperidine-4-carboxylic acid (74.50 mg, 193.31 μmol, 1 eq) and 3-[6-[4-[(4-fluoro-4-piperidyl) methyl]piperazin-1-yl]pyrimidin-4-yl]-5-(1-methylcyclopropoxy)-1H-indazole (90 mg, 193.31 μmol, 1 eq) in DMF (5 mL) was added HATU (73.50 mg, 193.31 μmol, 1 eq) in one portion at 0° C. under N2. The mixture was stirred at 0° C. for 3 hours. LCMS showed desired product MS. The resulting product was poured into H2O (20 mL). The mixture was extracted with ethyl acetate (20 mL*3). The organic phase was washed with brine (15 mL*2), dried over anhydrous Na2SO4, concentrated in vacuum to give a residue. The residue was purified by prep-HPLC (column: Phenomenex Luna C18 75*30 mm*3 um; mobile phase: [water (0.225% FA)-ACN]; B %: 15%-45%, 35 min) to give 2-(2,6-dioxo-3-piperidyl)-5-[4-[4-fluoro-4-[[4-[6-[5-(1-methylcyclopropoxy)-1H-indazol-3-yl]pyrimidin-4-yl]piperazin-1-yl]methyl]piperidine-1-carbonyl]-1-piperidyl] isoindoline-1,3-dione (68.8 mg, 82.49 μmol, 42.67% yield, 99.87% purity) as a yellow solid.

Exemplary Synthesis of Compound 97

Compound 97 was prepared in manner analogous to compound 87.

Step 1

To a mixture of [2-[4-[(1-tert-butoxycarbonyl-4-fluoro-4-piperidyl)methyl]piperazin-1-yl]-4-pyridyl]boronic acid (280 mg, 225.43 μmol, 34% purity, 1 eq), 2-[[3-iodo-5-(1-methylcyclopropoxy)indazol-1-yl]methoxy]ethyl-trimethyl-silane (110.20 mg, 247.98 μmol, 1.1 eq) and Na2CO3 (71.68 mg, 676.30 μmol, 3 eq) in 1,4-dioxane (10 mL) and H2O (2 mL) was added Pd(dppf)Cl2 (24.74 mg, 33.81 μmol, 0.15 eq) in one portion at 25° C. under N2. The mixture was stirred at 100° C. for 16 hours. LCMS showed there was desired MS. The mixture was cooled to 25° C., filtered and concentrated in vacuum. The residue was purified by silica gel chromatography (0-20% of Ethyl acetate in Petroleum ether) to give tert-butyl 4-fluoro-4-[[4-[4-[5-(1-methylcyclopropoxy)-1-(2-trimethylsilylethoxymethyl)indazol-3-yl]-2-pyridyl]piperazin-1-yl]methyl]piperidine-1-carboxylate (134 mg, 176.04 μmol, 78.09% yield, 91.3% purity) as a yellow gum.

Step 2

To a mixture of tert-butyl 4-fluoro-4-[[4-[4-[5-(1-methyl-cyclopropoxy)-1-(2-trimethylsilylethoxymethyl)indazol-3-yl]-2-pyridyl]piperazin-1-yl]methyl]piperidine-1-carboxylate (134 mg, 192.82 μmol, 1 eq) in MeOH (5 mL) was added HCl/EtOAc (4 M, 48.20 μL, 1 eq) in one portion and then was stirred at 65° C. for 30 min to give yellow solution. TLC showed the starting material was consumed completely. The mixture was concentrated in vacuum to give 3-[2-[4-[(4-fluoro-4-piperidyl)methyl]piperazin-1-yl]-4-pyridyl]-5-(1-methylcyclopropoxy)-2H-indazole (76.3 mg, 146.17 μmol, 75.81% yield, 89% purity) as a yellow oil.

Step 3

To a mixture of 1-[2-(2,6-dioxo-3-piperidyl)-1,3-dioxo-isoindolin-5-yl]piperidine-4-carboxylic acid (61.30 mg, 159.07 μmol, 1 eq) and 3-[2-[4-[(4-fluoro-4-piperidyl) methyl]piperazin-1-yl]-4-pyridyl]-5-(1-methylcyclopropoxy)-1H-indazole (73.9 mg, 159.07 μmol, 1 eq) in DMF (5 mL) was added HATU (60.48 mg, 159.07 μmol, 1 eq) in one portion at 0° C. under N2. The mixture was stirred at 0° C. and stirred for 3 hours. LCMS showed there was desired MS. The resulting product was poured into H2O (20 mL). The mixture was extracted with ethyl acetate (20 mL*3). The organic phase was washed with brine (15 mL*2), dried over anhydrous Na2SO4, concentrated in vacuum to give a residue. The residue was purified by prep-HPLC (column: Phenomenex Luna C18 75*30 mm*3 um; mobile phase: [water (0.225% FA)-ACN]; B %: 20%-50%, 35 min) to give 2-(2,6-dioxo-3-piperidyl)-5-[4-[4-fluoro-4-[[4-[4-[5-(1-methylcyclopropoxy)-1H-indazol-3-yl]-2-pyridyl]piperazin-1-yl]methyl]piperidine-1-carbonyl]-1-piperidyl]isoindoline-1,3-dione (9.3 mg, 11.13 μmol, 7.00% yield, 99.59% purity) as a yellow solid.

Exemplary Synthesis of Compound 98

Step 1

To a mixture of 4-(dimethoxymethyl)piperidine (1.81 g, 11.36 mmol, 1 eq) and 2-bromo-4-fluoro-pyridine (2 g, 11.36 mmol, 1 eq) in MeCN (50 mL) was added Cs2CO3 (7.41 g, 22.73 mmol, 2 eq) in one portion at 25° C. under N2. The mixture was stirred at 50° C. for 3 hours. The mixture was filtered and concentrated in vacuum. The residue was purified by silica gel chromatography (Petroleum ether/Ethyl acetate=100/1, 10/1) to afford 2-bromo-4-[4-(dimethoxymethyl)-1-piperidyl]pyridine (3.1 g, 9.24 mmol, 81.35% yield, 94% purity) as yellow solid.

Step 2

To a mixture of 2-bromo-4-[4-(dimethoxymethyl)-1-piperidyl]pyridine (1.5 g, 4.76 mmol, 1 eq) in THF (10 mL) was added HCl (2 M, 10 mL, 4.20 eq) in one portion at 25° C. The mixture was stirred at 25° C. for 2 hours. TLC showed the reaction was completed. The mixture was poured into sat. aq. $NaHCO_3$ (30 mL). The aqueous phase was extracted with ethyl acetate (30 mL*3). The combined organic phase was washed with brine (30 mL), dried with anhydrous Na2SO4, filtered and concentrated in vacuum to afford 1-(2-bromo-4-pyridyl)piperidine-4-carbaldehyde (1.3 g, crude) as yellow oil.

Step 3

To a mixture of 1-(2-bromo-4-pyridyl)piperidine-4-carbaldehyde (1.3 g, 4.83 mmol, 1 eq) and tert-butyl piperazine-1-carboxylate (989.60 mg, 5.31 mmol, 1.1 eq) in MeOH (20 mL) and HOAc (2 mL) was added borane; 2-methylpyridine (1.03 g, 9.66 mmol, 2 eq) in one portion at 25° C. under N2. The mixture was stirred at 25° C. for 12 hours. The mixture was concentrated in vacuum. The residue was purified by silica gel chromatography (Petroleum ether/Ethyl acetate=100/1, 1/1) to afford tert-butyl 4-[[1-(2-bromo-4-pyridyl)-4-piperidyl]methyl]piperazine-1-carboxylate (2.0 g, 4.55 mmol, 94.23% yield) as white solid.

Step 4

To a mixture of trimethyl(trimethylstannyl)stannane (110.59 mg, 337.55 μmol, 69.99 μL, 2 eq) and 2-[[3-iodo-5-(1-methylcyclopropoxy)indazol-1-yl]methoxy]ethyl-trimethyl-silane (75.00 mg, 168.77 μmol, 1 eq) in toluene (3 mL) was added Pd(PPh3)2Cl2 (11.85 mg, 16.88 μmol, 0.1 eq) in one portion at 25° C. under N2. The mixture was stirred at 140° C. for 1 hours. TLC showed the reaction was completed. The mixture was filtered and concentrated in vacuum to afford trimethyl-[2-[[5-(1-methylcyclopropoxy)-3-trimethylstannyl-indazol-1-yl]methoxy]ethyl]silane (80 mg, 101.39 μmol, 60.08% yield, 61% purity) as yellow solid.

Step 5

To a mixture of trimethyl-[2-[[5-(1-methylcyclopropoxy)-3-trimethylstannyl-indazol-1-yl]methoxy]ethyl]silane (80.00 mg, 166.22 μmol, 1 eq) and tert-butyl 4-[[1-(2-bromo-4-pyridyl)-4-piperidyl]methyl]piperazine-1-carboxylate (146.07 mg, 332.44 μmol, 2 eq) in THF (5 mL) was added LiCl (35.23 mg, 831.10 μmol, 17.02 μL, 5 eq), CuI (4.75 mg, 24.93 μmol, 0.15 eq) and $Pd(PPh3)_4$ (28.81 mg, 24.93 μmol, 0.15 eq) in one portion at 25° C. under N2. The mixture was stirred at 100° C. for 2 hours by MW. The mixture was filtered and concentrated in vacuum. The residue was purified by prep-TLC (Petroleum ether/Ethyl acetate=1/1) to afford tert-butyl 4-[[1-[2-[5-(1-methylcyclopropoxy)-1-(2-trimethylsilylethoxymethyl)indazol-3-yl]-4-pyridyl]-4-piperidyl]methyl]piperazine-1-carboxylate (200 mg, crude) as yellow solid.

Step 6

To a mixture of tert-butyl 4-[[1-[2-[5-(1-methylcyclopropoxy)-1-(2-trimethylsilylethoxymethyl)indazol-3-yl]-4-pyridyl]-4-piperidyl]methyl]piperazine-1-carboxylate (200 mg, 295.44 μmol, 1 eq) in DCM (5 mL) was added HCl/dioxane (4 M, 5 mL, 67.70 eq) in portions at 25° C. under N2. The mixture was stirred at 25° C. for 2 hours. TLC showed the reaction was completed. The mixture was concentrated in vacuum to afford 5-(1-methylcyclopropoxy)-3-[4-[4-(piperazin-1-ylmethyl)-1-piperidyl]-2-pyridyl]-1H-indazole (200 mg, crude, HCl) as a yellow solid.

Step 7

To a mixture of 5-(1-methylcyclopropoxy)-3-[4-[4-(piperazin-1-ylmethyl)-1-piperidyl]-2-pyridyl]-1H-indazole (78.47 mg, 162.44 μmol, 1 eq, HCl) and DIEA (41.99 mg, 324.88 μmol, 56.59 μL, 2 eq) in MeOH (5 mL) was added 1-[2-(2,6-dioxo-3-piperidyl)-1,3-dioxo-isoindolin-5-yl]piperidine-4-carbaldehyde (60 mg, 162.44 μmol, 1 eq), CH3COOH (0.5 mL) and (2-methylpyridin-1-ium-1-yl)boranuide (52.12 mg, 487.32 μmol, 3 eq) in one portion at 25° C. under N2. The mixture was stirred at 25° C. for 12 hours. The mixture was concentrated in vacuum. The residue was purified by prep-HPLC (column: 3_Phenomenex Luna C18 75*30 mm*3 um; mobile phase: [water (0.225% FA)-ACN]; B %: 0%-35%, 40 min) to afford 2-(2,6-dioxo-3-piperidyl)-5-[4-[[4-[[1-[2-[5-(1-methylcyclopropoxy)-1H-indazol-3-yl]-4-pyridyl]-4-piperidyl]methyl]piperazin-1-yl]methyl]-1-piperidyl]isoindoline-1,3-dione (14.4 mg, 16.68 μmol, 10.27% yield, 98% purity, FA) as yellow solid.

Exemplary Synthesis of Compound 99

Step 1

To a solution of 4-bromo-2,5-difluoro-pyridine (300 mg, 1.55 mmol, 729.93 μL, 1 eq) in DMSO (5 mL) was added K2CO3 (427.50 mg, 3.09 mmol, 2 eq) and 4-piperidylmethanol (267.19 mg, 2.32 mmol, 1.5 eq). The mixture was stirred at 90° C. for 30 min. TLC (Petroleum ether:Ethyl acetate=3:1, Rf=0.24, UV 254 nm) showed the reaction was completed. The mixture was cooled to 25° C. and concentrated in reduced pressure at 25° C. The residue was poured into water (5 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel chromatography (12 g, 0-40% (10 min) of Ethyl acetate in Petroleum ether, 40% (10 min) of Ethyl acetate in Petroleum ether) to give [1-(4-bromo-5-fluoro-2-pyridyl)-4-piperidyl]methanol (500 mg, crude) as a yellow solid.

Step 2

To a mixture of [1-(4-bromo-5-fluoro-2-pyridyl)-4-piperidyl]methanol (500 mg, 933.79 μmol, 54% purity, 1 eq) in DCM (10 mL) was added DMP (792.12 mg, 1.87 mmol, 578.19 μL, 2 eq) in one portion at 25° C. under N2. The mixture was stirred at 25° C. for 30 min. TLC (Petroleum ether:Ethyl acetate=1:1, Rf=0.43, UV 254 nm) showed the reaction was completed. The residue was poured into $NaHCO_3$ to adjusted the pH=7-8, and Na2SO3 (20 mL). The aqueous phase was extracted with DCM (10 mL*3). The combined organic phase was washed with brine (10 mL*2), dried with anhydrous Na2SO4, filtered and concentrated in vacuum. The residue was purified by silica gel chromatography (column height: 12 g, 100-200 mesh silica gel, 0-10% (10 min) of Ethyl acetate in Petroleum ether, 10-20% (10 min) of Ethyl acetate in Petroleum ether) to give 1-(4-bromo-5-fluoro-2-pyridyl)piperidine-4-carbaldehyde (163 mg, 533.63 μmol, 57.15% yield, 94% purity) as a yellow oil.

Step 3

To a mixture of 1-(4-bromo-5-fluoro-2-pyridyl)piperidine-4-carbaldehyde (163 mg, 567.69 μmol, 1 eq) and tert-butyl piperazine-1-carboxylate (105.73 mg, 567.69 μmol, 1 eq) in MeOH (10 mL) was added HOAc (1 mL) and borane; 2-methylpyridine (121.44 mg, 1.14 mmol, 2 eq) in one portion at 25° C. under N2. The mixture was stirred at 25° C. for 16 h. LCMS showed there was desired MS. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel chromatography (12 g, 100-200 mesh silica gel, 0-20% (15 min) of Ethyl acetate in Petroleum ether, 20% (20 min) of Ethyl acetate in Petroleum ether) to give tert-butyl 4-[[1-(4-bromo-5-fluoro-2-pyridyl)-4-piperidyl]methyl]piperazine-1-carboxylate (169 mg, 369.50 μmol, 65.09% yield) as a yellow oil.

Step 4

To a mixture of tert-butyl 4-[[1-(4-bromo-5-fluoro-2-pyridyl)-4-piperidyl]methyl]piperazine-1-carboxylate (169 mg, 369.50 μmol, 1 eq), Pin2B2 (187.66 mg, 738.99 μmol, 2 eq) and KOAc (108.79 mg, 1.11 mmol, 3 eq) in dioxane (10 mL) was added Pd(dppf)Cl2 (13.52 mg, 18.47 μmol, 0.05 eq) in one portion at 25° C. under N2. The mixture was stirred at 100° C. for 1 h. TLC showed the reaction was completed. The mixture was cooled to 25° C., filtered and concentrated in vacuum to give [2-[4-[(4-tert-butoxycarbonylpiperazin-1-yl)methyl]-1-piperidyl]-5-fluoro-4-pyridyl]boronic acid (430 mg, 356.38 μmol, 96.45% yield, 35% purity) as a black oil.

Step 5

To a mixture of [2-[4-[(4-tert-butoxycarbonylpiperazin-1-yl)methyl]-1-piperidyl]-5-fluoro-4-pyridyl]boronic acid (430 mg, 356.38 μmol, 35% purity, 1 eq), 2-[[3-iodo-5-(1-methylcyclopropoxy)indazol-1-yl]methoxy]ethyl-trimethyl-silane (174.21 mg, 392.02 μmol, 1.1 eq) and Na2CO3 (113.32 mg, 1.07 mmol, 3 eq) in 1,4-dioxane (10 mL) and H2O (2 mL) was added Pd(dppf)Cl2 (39.12 mg, 53.46 μmol, 0.15 eq) in one portion at 25° C. under N2. The mixture was stirred at 100° C. for 16 hours. LCMS showed there was desired MS. The mixture was cooled to 25° C., filtered and concentrated in vacuum. The residue was purified by silica gel chromatography (0-10% of Ethyl acetate in Petroleum ether) to give tert-butyl 4-[[1-[5-fluoro-4-[5-(1-methylcyclopropoxy)-1-(2-trimethylsilylethoxymethyl)indazol-3-yl]-2-pyridyl]-4-piperidyl]methyl]piperazine-1-carboxylate (76 mg, 109.36 μmol, 30.69% yield) as a yellow gum Step 6

To a mixture of tert-butyl 4-[[1-[5-fluoro-4-[5-(1-methylcyclopropoxy)-1-(2-trimethylsilylethoxymethyl)indazol-3-yl]-2-pyridyl]-4-piperidyl]methyl]piperazine-1-carboxylate (76 mg, 109.36 μmol, 1 eq) in MeOH (5 mL) was added HCl/EtOAc (4 M, 2 mL, 73.15 eq) in one portion at 20° C. The mixture was stirred at 65° C. for 15 min. LCMS showed the reaction was completed. The residue was concentrated in vacuum to give 3-[5-fluoro-2-[4-(piperazin-1-ylmethyl)-1-piperidyl]-4-pyridyl]-5-(1-methylcyclopropoxy)-1H-indazole (51 mg, 93.65 μmol, 85.63% yield, 92% purity, HCl) as a yellow solid.

Step 7

To a mixture of 3-[5-fluoro-2-[4-(piperazin-1-ylmethyl)-1-piperidyl]-4-pyridyl]-5-(1-methylcyclopropoxy)-1H-indazole (50 mg, 107.62 μmol, 1 eq) and 1-[2-(2,6-dioxo-3-piperidyl)-1,3-dioxo-isoindolin-5-yl]piperidine-4-carbaldehyde (39.75 mg, 107.62 μmol, 1 eq) in MeOH (5 mL) was added borane; 2-methylpyridine (23.02 mg, 215.25 μmol, 2 eq) and HOAc (6.46 mg, 107.62 μmol, 6.16 μL, 1 eq) in one portion at 25° C. under N2. The mixture was stirred at 25° C. for 1 h to give yellow solution. LCMS showed there was ~57% of desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (0.225% FA)-ACN]; B %: 10%-50%, 40 min) to give 2-(2,6-dioxo-3-piperidyl)-5-[4-[[4-[[1-[5-fluoro-4-[5-(1-methylcyclopropoxy)-1H-indazol-3-yl]-2-pyridyl]-4-piperidyl]methyl]piperazin-1-yl]methyl]-1-piperidyl]isoindoline-1,3-dione (30.7 mg, 35.71 μmol, 33.18% yield, 95.13% purity) as a yellow solid.

Exemplary Synthesis of Compound 100

Compound 100 was prepared in a manner analogous to compound 82 starting from tert-butyl 4-[4-[[1-(4-bromo-2-pyridyl)-4-piperidyl]oxy]cyclohexoxy]piperidine-1-carboxylate.

Step 1

To a mixture of 4-hydroxycyclohexanone (30 g, 262.83 mmol, 1 eq) in pyridine (300 mL) 2,2-dimethylpropanoyl chloride (47.54 g, 394.25 mmol, 48.51 mL, 1.5 eq) was added drop-wise at 0° C. under N2. The mixture was stirred at 0° C. for 30 min, then heated to 25° C. and stirred for 10 hours. TLC (Petroleum ether:Ethyl acetate=10:1, Rf=0.72) showed the reaction was completed. The residue was poured into water (200 mL). The aqueous phase was extracted with ethyl acetate (200 mL*3). The combined organic phase was washed with brine (200 mL*2), dried with anhydrous Na2SO4, filtered and concentrated in vacuum. The residue was purified by silica gel chromatography (220 g, 0-7% (20 min) of Ethyl acetate in Petroleum ether, 7% (30 min) of Ethyl acetate in Petroleum ether) to give (4-oxocyclohexyl) 2,2-dimethylpropanoate (50 g, 252.20 mmol, 95.95% yield) as a colorless oil.

Step 2

To a solution of (4-oxocyclohexyl) 2,2-dimethylpropanoate (50 g, 252.20 mmol, 1 eq) in EtOH (500 mL) was added NaBH4 (10.04 g, 265.40 mmol, 1.05 eq) at 0° C. under N2. Then the mixture was stirred at 0° C. for 1 h to give colourless solution. TLC (PE:EtOAc=3:1, Rf=0.24) showed the reaction was completed. The mixture was poured into HCl (100 mL, 2 M) and extracted with EtOAc (50 mL*2). The organic layer was washed with brine (50 mL), dried over anhydrous Na2SO4, filtered and concentrated in vacuum. The residue was purified by silica gel chromatography (0-30% (20 min) of Ethyl acetate in Petroleum ether, 30% (30 min) of Ethyl acetate in Petroleum ether) to give (4-hydroxycyclohexyl) 2,2-dimethylpropanoate (49 g, 244.66 mmol, 97.01% yield) as a colorless oil.

Step 3

To a solution of (4-hydroxycyclohexyl) 2,2-dimethylpropanoate (49 g, 244.66 mmol, 1 eq) in THF (500 mL) was added TEA (28.47 g, 281.36 mmol, 39.16 mL, 1.15 eq) and TMSCl (29.24 g, 269.13 mmol, 34.16 mL, 1.1 eq) at 0° C., and the reaction mixture was stirred at 25° C. for 0.5 hour. The reaction mixture was filtered and the filtrate was concentrated under reduced pressure to give a residue. Then to a stirred solution of above residue and benzyl 4-oxopiperidine-1-carboxylate (61.64 g, 264.24 mmol, 52.68 mL, 1.08 eq) in DCM (500 mL) was added Et3SiH (32.72 g, 281.36 mmol, 44.94 mL, 1.15 eq) and TMSOTf (27.19 g, 122.33 mmol, 22.11 mL, 0.5 eq) dropwise at −60° C., and the reaction mixture was stirred at 0° C. under N2 for 1.5 hours. TLC (Petroleum ether:Ethyl acetate=3:1, Rf=0.75, PMA) showed new spots formed. The reaction mixture was quenched by addition sat. $NaHCO_3$ adjust PH=8 at 0° C., and then extracted with ethyl acetate (500 mL*3). The combined organic layers were washed with brine (500 mL), dried over Na2SO4, filtered and concentrated under reduced pressure to give a residue. The residue was purified by silica gel chromatography (0-10% (10 min) of Ethyl acetate in Petroleum ether, 10% (50 min) of Ethyl acetate in Petroleum ether) to give benzyl 4-[4-(2,2-dimethylpropanoyloxy)cyclohexoxy]piperidine-1-carboxylate (86.96 g, 208.27 mmol, 85.12% yield) as a yellow gum.

Step 4

To a mixture of benzyl 4-[4-(2,2-dimethylpropanoyloxy) cyclohexoxy]piperidine-1-carboxylate (50.00 g, 119.75 mmol, 1 eq) in EtOH (500 mL) was added NaOH (23.95 g, 598.75 mmol, 5 eq) and H2O (150 mL) in one portion at 25° C. under N2. The mixture was stirred at 80° C. for 16 hours. TLC (PE:EtOAc=1:1) showed the starting material was consumed completely and a new spot was showed by TLC. LCMS showed there was desired MS. The mixture was cooled to 25° C. The residue was poured into water (500 mL). The aqueous phase was extracted with ethyl acetate (500 mL*3). The combined organic phase was washed with brine (500 mL*2), dried with anhydrous Na2SO4, filtered and concentrated in vacuum. The residue was purified by silica gel chromatography (0-45% (20 min) of Ethyl acetate in Petroleum ether, 45% (50 min) of Ethyl acetate in Petroleum ether) to give benzyl 4-(((1s, 4s)-4-hydroxycyclohexyl)oxy)piperidine-1-carboxylate (10 g, 29.99 mmol, 25.05% yield) as a light yellow gum and benzyl 4-(((1r, 4r)-4-hydroxycyclohexyl)oxy)piperidine-1-carboxylate (3.68 g, 11.04 mmol, 9.22% yield) as a light yellow gum.

Step 5

To a solution of benzyl 4-(4-hydroxycyclohexoxy)piperidine-1-carboxylate (1.50 g, 4.50 mmol, 1 eq) in THF (500 mL) was added TEA (523.52 mg, 5.17 mmol, 720.11 μL, 1.15 eq) and TMSCl (537.63 mg, 4.95 mmol, 628.07 μL, 1.1 eq) at 0° C., and the reaction mixture was stirred at 25° C. for 0.5 hour. The reaction mixture was filtered and the filtrate was concentrated under reduced pressure to give a residue. Then to a stirred solution of above residue and benzyl 4-oxopiperidine-1-carboxylate (1.13 g, 4.86 mmol, 968.94 μL, 1.08 eq) in DCM (500 mL) was added Et3SiH (601.59 mg, 5.17 mmol, 826.36 μL, 1.15 eq) and TMSOTf (499.95 mg, 2.25 mmol, 406.47 μL, 0.5 eq) dropwise at −60° C., and the reaction mixture was stirred at 0° C. under N2 for 1.5 hours. TLC (Petroleum ether:Ethyl acetate=0:1, Rf=0.75, PMA) showed new spots formed. LCMS showed there was desired MS. The reaction mixture was quenched by addition sat. $NaHCO_3$ adjust PH=8 at 0° C., and then extracted with Ethyl acetate (500 mL*3). The combined organic layers were washed with brine (500 mL), dried over Na2SO4, filtered and concentrated under reduced pressure to give a residue. The residue was purified by silica gel chromatography (0-10% (10 min) of Ethyl acetate in Petroleum ether, 10% (50 min) of Ethyl acetate in Petroleum ether) to give benzyl 4-[4-[(1-benzyloxycarbonyl-4-piperidyl)oxy]cyclohexoxy]piperidine-1-carboxylate (700 mg, 1.27 mmol, 28.25% yield) as a yellow gum.

Step 6

To a solution of benzyl 4-[4-[(1-benzyloxycarbonyl-4-piperidyl)oxy]cyclohexoxy]piperidine-1-carboxylate (700 mg, 1.27 mmol, 1 eq) in MeOH (50 mL) was added Pd/C (100 mg, 1.27 mmol, 10% purity, 1 eq) under N2. The suspension was degassed under vacuum and purged with H2 several times. The mixture was stirred under H2 (50 psi) at 60° C. for 16 h. TLC (DCM/MeOH=10/1, RF=0.51) indicated no reactant 1 was remained, and one major new spot with larger polarity was detected. The reaction mixture was filtered and the filter was concentrated to give 4-[4-(4-piperidyloxy)cyclohexoxy]piperidine (510 mg, crude) as a white solid Step 7

To a solution of 4-bromo-2-fluoro-pyridine (96.59 mg, 548.83 μmol, 0.5 eq) and 4-[4-(4-piperidyloxy)cyclohexoxy]piperidine (310 mg, 1.10 mmol, 1 eq) in DMSO (10 mL) was added DIEA (425.58 mg, 3.29 mmol, 573.56 μL, 3 eq). The mixture was stirred at 100° C. for 0.5 h. LCMS showed there was desired MS, the Boc2O (359.34 mg, 1.65 mmol, 378.25 μL, 1.5 eq) was added to the mixture and the mixture was stirred at 25° C. for 0.5 h. LCMS showed there was ~29.8% of desired MS. The resulting product was poured into H2O (20 mL). The mixture was extracted with ethyl acetate (20 mL*3). The organic phase was washed with brine (15 mL*2), dried over anhydrous Na2SO4, concentrated in vacuum to give a residue. The residue was purified by silica gel chromatography (0-17% (10 min) of Ethyl acetate in petroleum ether, 17% (10 min) of Ethyl acetate in petroleum ether), LCMS showed there was ~47% of desired MS. The crude product was purified by reversed-phase HPLC (column: Phenomenex Luna C18 75*30 mm*3 um; mobile phase: [water (0.225% FA)-ACN]; B %: 45%-85%, 35 min) to give tert-butyl 4-[4-[[1-(4-bromo-2-pyridyl)-4-piperidyl]oxy]cyclohexoxy]piperidine-1-carboxylate (230 mg, 369.65 μmol, 33.68% yield, 86.55% purity) as a yellow solid.

Exemplary Synthesis of Compound 101

Step 1

To a solution of methyl 4-formylcyclohexanecarboxylate (2 g, 11.75 mmol, 1 eq) and benzyl piperazine-1-carboxylate (2.85 g, 12.93 mmol, 2.50 mL, 1.1 eq) in MeOH (30 mL) and AcOH (3 mL) was added borane; 2-methylpyridine (6.28 g, 58.75 mmol, 5 eq). The mixture was stirred at 25° C. for 4 hr. LC-MS (EB134-923-P1A) showed no reactant 1 was remained. Several new peaks were shown on LC-MS and ~89% of desired compound was detected. The reaction mixture was concentrated under reduced pressure to remove solvent. The crude product was purified by column chromatography on silica gel (column height: 40 g, 100-200 mesh silica gel, 0-100% (30 min) of Ethyl acetate in Petroleum ether) to get benzyl 4-[(4-methoxycarbonylcyclohexyl)methyl]piperazine-1-carboxylate (4 g, 10.68 mmol, 90.90% yield) as a yellow gum.

Step 2

To a solution of benzyl 4-[(4-methoxycarbonylcyclohexyl)methyl]piperazine-1-carboxylate (1 g, 2.67 mmol, 1 eq) in DCM (30 mL) was added DIBALH (1 M, 5.34 mL, 2 eq) dropwise at −78° C. over a period of 30 mins under N2. During which the temperature was maintained below −78° C. The reaction mixture was warmed to 25° C. stirred for 4 hours. LC-MS (EB134-939-P1C) showed 27% of reactant 1 was remained. Several new peaks were shown on LC-MS and ~50% of desired compound was detected. To the reaction mixture was added sat NH4Cl under ice-cooling. Saturated brine was added thereto, followed by extraction with ethyl acetate (50 mL×2). The organic layer was dried over anhydrous magnesium sulfate and concentrated. The crude product was purified by column chromatography on silica gel (column height: 40 g, 100-200 mesh silica gel, 0-80% (15 min) of Ethyl acetate in Petroleum ether) to get benzyl 4-[[4-(hydroxymethyl)cyclohexyl]methyl]piperazine-1-carboxylate (310 mg, 894.76 μmol, 33.51% yield) as a colorless oil.

Step 3

To a solution of benzyl 4-[[4-(hydroxymethyl)cyclohexyl]methyl]piperazine-1-carboxylate (310 mg, 894.76 μmol, 1 eq) in DCM (6 mL) was added DMP (569.26 mg, 1.34 mmol, 415.52 μL, 1.5 eq). The mixture was stirred at 25° C. for 2 hr. LC-MS (EB134-941-P1B) showed no effective information. TLC (Petroleum ether/Ethyl acetate=1/2, RF=0.51) indicated no reactant 1 was remained, and one major new spot with lower polarity was detected. The mixture was quenched with sat.$NaHCO_3$ (30 mL*3) and extracted with DCM (30 mL). The organic layer was washed with water (30 mL×2), brine (30 mL×2), dried over anhydrous Na2SO4, filtered and concentrated in vacuo to get benzyl 4-[(4-formylcyclohexyl)methyl]piperazine-1-carboxylate (300 mg, 870.96 μmol, 97.34% yield) as a yellow gum.

Step 4

To a solution of benzyl 4-[(4-formylcyclohexyl)methyl]piperazine-1-carboxylate (300 mg, 870.96 μmol, 1 eq) and tert-butyl piperazine-1-carboxylate (243.33 mg, 1.31 mmol, 1.5 eq) in MeOH (6 mL) and AcOH (0.6 mL) was added borane; 2-methylpyridine (465.79 mg, 4.35 mmol, 5 eq). The mixture was stirred at 25° C. for 4 hr. LC-MS (EB134-943-P1B) showed no reactant 1 was remained. Several new peaks were shown on LC-MS and ~42% of desired compound was detected. The reaction mixture was diluted with water (20 mL) and extracted with EA (30 mL). The combined organic layers were washed with brine (20 mL), dried over Na2SO4, filtered and concentrated under reduced pressure to give a residue. The crude product was purified by column chromatography on silica gel (column height: 8 g, 100-200 mesh silica gel, 0-100% (30 min) of Ethyl acetate in Petroleum ether) to get benzyl 4-[[4-[(4-tert-butoxycarbonylpiperazin-1-yl)methyl]cyclohexyl]methyl]piperazine-1-carboxylate (350 mg, 680.01 μmol, 78.08% yield) as a yellow gum.

Step 5

To a solution of benzyl 4-[[4-[(4-tert-butoxycarbonylpiperazin-1-yl)methyl]cyclohexyl]methyl]piperazine-1-carboxylate (350.00 mg, 680.01 μmol, 1 eq) in EtOH (15 mL) was added Pd/C (60 mg, 680.01 μmol, 10% purity, 1 eq) under N2. The suspension was degassed under vacuum and purged with H2 several times. The mixture was stirred under H2 (50 psi) at 60° C. for 16 hours. TLC (Petroleum ether/Ethyl acetate=0/1, Rf=0) indicated no reactant 1 was remained, and one major new spot with larger polarity was detected. The reaction mixture was filtered and the filter was concentrated to get tert-butyl 4-[[4-(piperazin-1-ylmethyl) cyclohexyl]methyl]piperazine-1-carboxylate (210 mg, 551.81 μmol, 81.15% yield) as a white solid.

Step 6

To a solution of tert-butyl 4-[[4-(piperazin-1-ylmethyl) cyclohexyl]methyl]piperazine-1-carboxylate (210 mg, 551.81 μmol, 1 eq) in DMSO (5 mL) was added DIEA (356.59 mg, 2.76 mmol, 480.58 μL, 5 eq) and 2-(2,6-dioxo-3-piperidyl)-5-fluoro-isoindoline-1,3-dione (167.66 mg, 606.99 μmol, 1.1 eq). The mixture was stirred at 100° C. for 12 hr. LC-MS (EB134-949-P1A) showed no reactant 1 was remained. Several new peaks were shown on LC-MS and ~23.6% of desired compound was detected. TLC (Petroleum ether/Ethyl acetate=0/1, Rf=0.24) indicated one major new spot with larger polarity was detected. The reaction mixture was diluted with water (20 mL) and extracted with EA (30 mL). The combined organic layers were washed with brine (20 mL*3), dried over Na2SO4, filtered and concentrated under reduced pressure to give a residue. The crude product was purified by column chromatography on silica gel (column height: 8 g, 100-200 mesh silica gel, 0-80% (130 min) of Ethyl acetate in Petroleum ether) to get tert-butyl 4-[[4-[[4-[2-(2,6-dioxo-3-piperidyl)-1,3-dioxo-isoindolin-5-yl] piperazin-1-yl]methyl]cyclohexyl]methyl]piperazine-1-carboxylate (170 mg, 266.97 μmol, 48.38% yield) as a yellow gum.

Step 7

To a solution of tert-butyl 4-[[4-[[4-[2-(2,6-dioxo-3-piperidyl)-1,3-dioxo-isoindolin-5-yl]piperazin-1-yl]methyl]cyclohexyl]methyl]piperazine-1-carboxylate (170 mg, 266.97 μmol, 1 eq) in DCM (5 mL) was added TFA (1.54 g, 13.51 mmol, 1 mL, 50.59 eq). The mixture was stirred at 25° C. for 2 hr. TLC (Petroleum ether/Ethyl acetate=0/1, Rf=0) indicated no reactant 1 was remained, and one major new spot with larger polarity was detected. The reaction mixture was concentrated under reduced pressure to remove solvent to get 2-(2,6-dioxo-3-piperidyl)-5-[4-[[4-(piperazin-1-ylmethyl)cyclohexyl]methyl]piperazin-1-yl]isoindoline-1,3-dione (160 mg, 230.16 μmol, 86.21% yield, 93.6% purity, TFA) as a yellow gum.

Step 8

To a solution of 2-(2,6-dioxo-3-piperidyl)-5-[4-[[4-(piperazin-1-ylmethyl)cyclohexyl]methyl]piperazin-1-yl]isoindoline-1,3-dione (62.46 mg, 116.38 μmol, 1 eq) in DMSO (5 mL) was added DIEA (150.41 mg, 1.16 mmol, 202.71 μL, 10 eq) and 3-(6-chloropyrimidin-4-yl)-5-(1-methylcyclopropoxy)-1H-indazole (35 mg, 116.38 μmol, 1 eq). The mixture was stirred at 80° C. for 12 hr. LC-MS (EB134-962-P1A) showed no reactant 1 was remained. Several new peaks were shown on LC-MS and ~80% of desired compound was detected. The reaction mixture was diluted with water (20 mL) and extracted with EA (30 mL). The combined organic layers were washed with brine (20 mL), dried over Na2SO4, filtered and concentrated under reduced pressure to give a residue. The impure product was purified by Prep-HPLC (column: 3_Phenomenex Luna C18 75*30 mm*3 um; mobile phase: [water (0.225% FA)-ACN]; B %: 0%-30%, 40 min) to get 2-(2,6-dioxo-3-piperidyl)-5-[4-[[4-[[4-[6-[5-(1-methylcyclopropoxy)-1H-indazol-3-yl]pyrimidin-4-yl]piperazin-1-yl]methyl]cyclohexyl]methyl]piperazin-1-yl]isoindoline-1,3-dione (48.3 mg, 57.80 μmol, 49.66% yield, 95.844% purity) as a yellow solid.

Exemplary Synthesis of Compound 102

Compound 101 was prepared in a manner analogous to compound 82 using tert-butyl 4-[[4-(piperazin-1-ylmethyl) cyclohexyl]methyl]piperazine-1-carboxylate.

Exemplary Synthesis of Compound 103

Step 1

To a solution of methyl 2-oxo-1H-pyridine-4-carboxylate (15.00 g, 97.95 mmol, 1 eq) in MeOH (250 mL) was added Pd/C (6 g, 10% purity, 1.00 eq) under N2. The suspension was degassed under vacuum and purged with H2 several times. The mixture was stirred under H2 (15 psi) at 25° C. for 12 hours. TLC (DCM/MeOH=10:1) showed the starting material was consumed completely. The reaction mixture was filtered and the filter was concentrated to give methyl 2-oxopiperidine-4-carboxylate (16 g, crude) as white solid.

Step 2

To a mixture of methyl 2-oxopiperidine-4-carboxylate (7 g, 44.54 mmol, 1 eq) in THF (150 mL) was added LAH (3.38 g, 89.08 mmol, 2 eq) in one portion at −40° C. under N2. The mixture was stirred at −40° C. for 3 hours. TLC showed the reaction was completed. Water (5 mL) and 10% aq. NaOH (5 mL) were added into the mixture at 0° C. The aqueous phase was dried with anhydrous Na2SO4, filtered and concentrated in vacuum to afford 4-(hydroxymethyl) piperidin-2-one (5.3 g, 41.04 mmol, 92.13% yield) as yellow oil.

Step 3

To a mixture of 4-(hydroxymethyl)piperidin-2-one (5.3 g, 41.04 mmol, 1 eq) and TEA (12.46 g, 123.11 mmol, 17.13 mL, 3 eq) in DCM (120 mL) was added DMAP (501.32 mg, 4.10 mmol, 0.1 eq) and TosCl (15.65 g, 82.07 mmol, 2 eq) in portions at 0° C. under N2. The mixture was stirred at 25° C. for 12 hours. TLC showed the reaction was completed. The mixture was filtered and concentrated in vacuum. The residue was purified by silica gel chromatography (DCM/MeOH=100/1, 10/1) to afford (2-oxo-4-piperidyl)methyl 4-methylbenzenesulfonate (5.6 g, 19.76 mmol, 48.16% yield) as white solid.

Step 4

To a mixture of benzyl piperazine-1-carboxylate (466.43 mg, 2.12 mmol, 409.15 μL, 1.5 eq) and (2-oxo-4-piperidyl) methyl 4-methylbenzenesulfonate (400 mg, 1.41 mmol, 1 eq) in MeCN (20 mL) was added DIEA (1.82 g, 14.12 mmol, 2.46 mL, 10 eq) in one portion at 25° C. under N2. The mixture was stirred at 90° C. for 12 h, then (Boc)2O (616.21 mg, 2.82 mmol, 648.64 μL, 2 eq) was added at 25° C. and the mixture was stirred at 25° C. for 2 hours. LCMS showed the reaction was completed. The mixture was concentrated in vacuum. The residue was purified by silica gel chromatography (DCM/MeOH=100/1,10/1) to afford benzyl 4-[(2-oxo-4-piperidyl)methyl]piperazine-1-carboxylate (370 mg, 848.50 μmol, 60.10% yield, 76% purity) as yellow oil.

Step 5

To a mixture of benzyl 4-[(2-oxo-4-piperidyl)methyl] piperazine-1-carboxylate (3 g, 9.05 mmol, 1 eq) in DMF (40 mL) was added NaH (724.11 mg, 18.10 mmol, 60% purity, 2 eq) in one portion at 0° C. under N2. The mixture was stirred at 0° C. for 30 min, then tert-butyl 4-(p-tolylsulfonyloxymethyl)piperidine-1-carboxylate (4.01 g, 10.86 mmol, 1.2 eq) and KI (150.27 mg, 905.23 μmol, 0.1 eq) was added at 0° C. and the mixture was stirred at 25° C. for 11.5 hours. TLC showed the reaction was completed. The mixture was poured into EtOAc (100 mL). The aqueous phase was washed with brine (100 mL*3), dried with anhydrous Na2SO4, filtered and concentrated in vacuum. The residue was purified by prep-HPLC (column: 3_Phenomenex Luna C18 75*30 mm*3 um; mobile phase: [water (0.225% FA)-ACN]; B %: 0%-40%, 40 min) to afford benzyl 4-[[1-[(1-tert-butoxycarbonyl-4-piperidyl)methyl]-2-oxo-4-piperidyl]methyl]piperazine-1-carboxylate (500 mg, 582.91 μmol, 6.44% yield, 67% purity, FA) as yellow solid.

Step 6

A mixture of benzyl 4-[[1-[(1-tert-butoxycarbonyl-4-piperidyl)methyl]-2-oxo-4-piperidyl]methyl]piperazine-1-carboxylate (400 mg, 756.60 μmol, 1 eq) was purified by SFC (column: DAICEL CHIRALCEL OJ (250 mm*30 mm, 10 um); mobile phase: [0.1% NH3H2O ETOH]; B %: 20%-20%, min) to give benzyl 4-[[(4R)-1-[(1-tert-butoxycarbonyl-4-piperidyl)methyl]-2-oxo-4-piperidyl]methyl]piperazine-1-carboxylate or the enantiomer thereof (180 mg, 340.47 μmol, 45.00% yield) as yellow oil and benzyl 4-[[(4S)-1-[(1-tert-butoxycarbonyl-4-piperidyl)methyl]-2-oxo-4-piperidyl]methyl]piperazine-1-carboxylate or the enantiomer thereof (200 mg, 378.30 μmol, 50.00% yield) as yellow oil.

Step 7

To a solution of benzyl 4-[[(4R)-1-[(1-tert-butoxycarbonyl-4-piperidyl)methyl]-2-oxo-4-piperidyl]methyl]piperazine-1-carboxylate or the enantiomer thereof (90 mg, 170.23 μmol, 1 eq) in DCM (2 mL) was added TFA (1.54 g, 13.51 mmol, 1 mL, 79.34 eq). After addition, the reaction solution was stirred at 20° C. for 1 h. TLC showed the reaction was completed. The reaction mixture was concentrated under reduced pressure to remove solvent to afford benzyl 4-[[(4R)-2-oxo-1-(4-piperidylmethyl)-4-piperidyl]methyl]piperazine-1-carboxylate or the enantiomer thereof (72 mg, crude, TFA) as a yellow gum.

Step 8

To a solution of benzyl 4-[[(4R)-2-oxo-1-(4-piperidylmethyl)-4-piperidyl]methyl]piperazine-1-carboxylate or the enantiomer thereof (72 mg, 168.00 μmol, 1.16 eq) and 2-(2,6-dioxo-3-piperidyl)-5-fluoro-isoindoline-1,3-dione (40 mg, 144.81 μmol, 1 eq) in DMSO (3 mL) was added DIEA (56.15 mg, 434.44 μmol, 75.67 μL, 3 eq). After addition, the mixture was stirred at 100° C. for 16 hours. LCMS showed there was desired MS. The residue was poured into water (20 mL). The aqueous phase was extracted with ethyl acetate (20 mL*3). The combined organic phase was washed with brine (20 mL*2), dried with anhydrous Na2SO4, filtered and concentrated in vacuum. The residue was purified by silica gel chromatography (12 g, 0-100% (20 min) of Ethyl acetate in Petroleum ether, 0-16% (10 min) of Dichloromethane in Methanol, 16% (10 min) of Dichloromethane in Methanol) to afford benzyl 4-[[(4R)-1-[[1-[2-(2,6-dioxo-3-piperidyl)-1,3-dioxo-isoindolin-5-yl]-4-piperidyl]methyl]-2-oxo-4-piperidyl]methyl]piperazine-1-carboxylate or the enantiomer thereof (120 mg, crude) as a yellow gum.

Step 9

To a mixture of benzyl 4-[[(4R)-1-[[1-[2-(2,6-dioxo-3-piperidyl)-1,3-dioxo-isoindolin-5-yl]-4-piperidyl]methyl]-2-oxo-4-piperidyl]methyl]piperazine-1-carboxylate or the enantiomer thereof (120 mg, 175.24 μmol, 1 eq) was added TFA (3.08 g, 27.01 mmol, 2 mL, 154.14 eq). The mixture was stirred at 80° C. for 1 h. TLC showed the reaction was completed. The reaction mixture was concentrated under reduced pressure to remove solvent to afford 2-(2,6-dioxo-3-piperidyl)-5-[4-[[(4R)-2-oxo-4-(piperazin-1-ylmethyl)-1-piperidyl]methyl]-1-piperidyl]isoindoline-1,3-dione or the enantiomer thereof (96 mg, 135.99 μmol, 77.60% yield, 78% purity) as a yellow gum.

Step 10

To a solution of 2-(2,6-dioxo-3-piperidyl)-5-[4-[[(4R)-2-oxo-4-(piperazin-1-ylmethyl)-1-piperidyl]methyl]-1-piperidyl]isoindoline-1,3-dione or the enantiomer thereof (96 mg, 174.34 μmol, 1.42 eq) and 3-(6-chloropyrimidin-4-yl)-5-(1-methylcyclopropoxy)-1H-indazole (37 mg, 123.03 μmol, 1 eq) in DMSO (2.5 mL) was added DIEA (371.00 mg, 2.87 mmol, 0.5 mL, 23.33 eq). After addition, the mixture was stirred at 100° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous Na2SO4, filtered and concentrated in vacuum. The residue was purified by prep.HPLC (column: 3_Phenomenex Luna C18 75*30 mm*3 um; mobile phase: [water (0.225% FA)-ACN]; B %: 0%-35%, 40 min) to afford 2-(2,6-dioxo-3-piperidyl)-5-[4-[[(4R)-4-[[4-[6-[5-(1-methylcyclopropoxy)-1H-indazol-3-yl]pyrimidin-4-yl]piperazin-1-yl]methyl]-2-oxo-1-piperidyl]methyl]-1-piperidyl]isoindoline-1,3-dione or the enantiomer thereof (25.1 mg, 30.34 μmol, 24.66% yield, 98.5% purity) as a white solid.

Exemplary Synthesis of Compound 104

Compound 104 was prepared in a manner analogous to compound 103 using benzyl 4-[[(4S)-1-[(1-tert-butoxycarbonyl-4-piperidyl)methyl]-2-oxo-4-piperidyl]methyl]piperazine-1-carboxylate or the enantiomer thereof.

Exemplary Synthesis of Compound 105

Step 1

To a solution of 4,6-dibromopyrimidine (1 g, 4.20 mmol, 1 eq) and tert-butyl 4-(4,4,5,5-tetramethyl-1,3,2-dioxaborolan-2-yl)-3,6-dihydro-2H-pyridine-1-carboxylate (1.56 g, 5.04 mmol, 1.2 eq) in dioxane (20 mL) and H2O (2 mL) was added Na2CO3 (1.11 g, 10.51 mmol, 2.5 eq) and Pd(dppf)Cl2 (153.80 mg, 210.19 μmol, 0.05 eq). After addition, the reaction mixture was stirred at 80° C. under N2 for 16 h. LCMS showed desired MS. TLC (petroleum ether=3:1) showed several spots. After cooling, the reaction mixture was diluted with water (30 mL) and extracted with ethyl acetate (30 mL*3). The organic layer was dried over sodium sulfate and concentrated under reduced pressure. The residue was purified by silica gel column chromatography (0 to 30% ethyl acetate in petroleum ether) to afford tert-butyl 4-(6-bromopyrimidin-4-yl)-3,6-dihydro-2H-pyridine-1-carboxylate (650 mg, 1.87 mmol, 44.54% yield, 98% purity) as a white solid.

Step 2

To a solution of trimethyl-[2-[[5-(1-methylcyclopropoxy)-3-trimethylstannyl-indazol-1-yl]methoxy]ethyl]silane (685 mg, 1.42 mmol, 1.38 eq) in THF (4 mL) was added tert-butyl 4-(6-bromopyrimidin-4-yl)-3,6-dihydro-2H-pyridine-1-carboxylate (350 mg, 1.03 mmol, 1 eq), LiCl (218.05 mg, 5.14 mmol, 105.34 μL, 5 eq), CuI (29.39 mg, 154.31 μmol, 0.15 eq) and Pd(PPh3)4 (178.32 mg, 154.31 μmol, 0.15 eq). After addition, the reaction mixture was stirred at 100° C. under N2 for 1.5 h by microwave. LCMS showed the reaction completed. The reaction mixture was diluted with water (10 mL) and extracted with ethyl acetate (3×10 mL). The organic layer was dried over sodium sulfate and concentrated under reduced pressure. The residue was purified by silica gel column chromatography (0 to 25% ethyl acetate in petroleum ether) to afford tert-butyl 4-[6-[5-(1-methylcyclopropoxy)-1-(2-trimethylsilylethoxymethyl)indazol-3-yl]pyrimidin-4-yl]-3,6-dihydro-2H-pyridine-1-carboxylate (310 mg, 480.19 μmol, 46.68% yield, 89.5% purity) as a yellow gum.

Step 3

To a solution of tert-butyl 4-[6-[5-(1-methylcyclopropoxy)-1-(2-trimethylsilylethoxymethyl)indazol-3-yl]pyrimidin-4-yl]-3,6-dihydro-2H-pyridine-1-carboxylate (310.00 mg, 536.53 μmol, 1 eq) in MeOH (2 mL) was added Pd/C (100 mg, 10% purity) under Ar. After addition, the reaction mixture was degassed for 3 times with H2 and stirred at 65° C. under H2 (50 psi) for 16 h. TLC (petroleum ether:ethyl acetate=1:1) showed the reaction completed. After cooling, the reaction mixture was filtered and filtrate was concentrated under reduced pressure. The residue was purified by silica gel column chromatography (0 to 33% ethyl acetate in petroleum ether) to afford tert-butyl 4-[6-[5-(1-methylcyclopropoxy)-1-(2-trimethylsilylethoxymethyl)indazol-3-yl]pyrimidin-4-yl]piperidine-1-carboxylate (150 mg, 240.60 μmol, 44.84% yield, 93% purity) as a yellow gum.

Step 4

To a solution of tert-butyl 4-[6-[5-(1-methylcyclopropoxy)-1-(2-trimethylsilylethoxymethyl)indazol-3-yl]pyrimidin-4-yl]piperidine-1-carboxylate (150 mg, 258.71 μmol, 1 eq) in MeOH (2 mL) was added HCl/EtOAc (4 M, 2 mL, 30.92 eq). After addition, the reaction solution was stirred at 65° C. for 30 min. LCMS showed the reaction completed. After cooling, the reaction mixture was concentrated under reduced pressure. The resulting mixture was dissolved in DCM (5 mL) and DIEA (1 mL). The mixture was stirred at 25° C. for 5 min and concentrated under reduced pressure to afford 5-(1-methylcyclopropoxy)-3-[6-(4-piperidyl)pyrimidin-4-yl]-1H-indazole (90 mg, crude) as a brown solid. The crude product was used for next step directly.

Step 5

To a solution of 5-(1-methylcyclopropoxy)-3-[6-(4-piperidyl)pyrimidin-4-yl]-1H-indazole (90 mg, 257.56 μmol, 1 eq) and tert-butyl 4-formylpiperidine-1-carboxylate (109.86 mg, 515.13 μmol, 2 eq) in MeOH (4 mL) and HOAc (0.4 mL) was added borane; 2-methylpyridine (55.10 mg, 515.13 μmol, 2 eq). After addition, the reaction was stirred at 20° C. for 12 h. LCMS and TLC (pure ethyl acetate) showed the reaction completed. The reaction mixture was concentrated under reduced pressure. The residue was purified by silica gel column chromatography (0 to 100% ethyl acetate in petroleum ether) to afford tert-butyl 4-[[4-[6-[5-(1-methylcyclopropoxy)-1H-indazol-3-yl]pyrimidin-4-yl]-1-piperidyl]methyl]piperidine-1-carboxylate (120 mg, 212.25 μmol, 82.41% yield, 96.7% purity) as a light yellow solid.

Step 6

To a solution of tert-butyl 4-[[4-[6-[5-(1-methylcyclopropoxy)-1H-indazol-3-yl]pyrimidin-4-yl]-1-piperidyl]methyl]piperidine-1-carboxylate (55 mg, 100.60 μmol, 1 eq) in MeOH (2 mL) was added HCl/EtOAc (4 M, 25.15 μL, 1 eq). After addition, the reaction solution was stirred at 25° C. for 3 h. LCMS showed the reaction completed. The reaction mixture was concentrated under reduced pressure. The resulting mixture was dissolved in DCM (5 mL) and DIEA (1 mL). The mixture was stirred at 25° C. for 5 min and concentrated under reduced pressure to afford 5-(1-methylcyclopropoxy)-3-[6-[1-(4-piperidylmethyl)-4-piperidyl]pyrimidin-4-yl]-1H-indazole (45 mg, crude) as a brown solid. The crude product was used for next step directly.

Step 7

To a solution of 5-(1-methylcyclopropoxy)-3-[6-[1-(4-piperidylmethyl)-4-piperidyl]pyrimidin-4-yl]-1H-indazole (45.00 mg, 100.76 μmol, 1.01 eq) and 1-[2-(2,6-dioxo-3-piperidyl)-1,3-dioxo-isoindolin-5-yl]piperidine-4-carbaldehyde (37 mg, 100.17 μmol, 1 eq) in MeOH (5 mL) and HOAc (0.5 mL) was added borane; 2-methylpyridine (21.43 mg, 200.34 μmol, 2 eq). After addition, the reaction solution was stirred at 20° C. for 12 h. LCMS showed the reaction completed. The mixture was diluted with water (10 mL) and extracted with dichloromethane (10 mL*3). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 0%-35%, 40 min) to afford 2-(2,6-dioxo-3-piperidyl)-5-[4-[[4-[[4-[6-[5-(1-methylcyclopropoxy)-1H-indazol-3-yl]pyrimidin-4-yl]-1-piperidyl]methyl]-1-piperidyl]methyl]-1-piperidyl]isoindoline-1,3-dione (52.2 mg, 65.11 μmol, 65.00% yield, 99.78% purity) as a yellow solid.

Exemplary Synthesis of Compound 106

Compound 106 was prepared in manner analogous to compound 71 using 2-(2,6-dioxo-3-piperidyl)-5-[4-[[4-fluoro-4-[[(2S)-2-methylpiperazin-1-yl]methyl]-1-piperidyl]methyl]-1-piperidyl]isoindoline-1,3-dione.

Step 1

To a mixture of 2-(2,6-dioxo-3-piperidyl)-5-[4-[[4-fluoro-4-[[(2S)-2-methylpiperazin-1-yl]methyl]-1-piperidyl]methyl]-1-piperidyl]isoindoline-1,3-dione (68.69 mg, 120.79 μmol, 1.1 eq, 3TFA) and 3-(6-chloropyrimidin-4-yl)-6-fluoro-5-(1-methylcyclopropoxy)-1H-indazole (35 mg, 109.81 μmol, 1 eq) in DMSO (5 mL) was added DIEA (113.53 mg, 878.48 μmol, 153.01 μL, 8 eq) in one portion at 20° C. under N2. The mixture was stirred at 80° C. for 16 h. LCMS showed desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 35; FlowRate: 25 mL/min; Gradient Time: 40 min; 100% B Hold Time: 3 min) to give 2-(2,6-dioxo-3-piperidyl)-5-[4-[[4-fluoro-4-[[(2S)-4-[6-[6-fluoro-5-(1-methylcyclopropoxy)-1H-indazol-3-yl]pyrimidin-4-yl]-2-methyl-piperazin-1-yl]methyl]-1-piperidyl]methyl]-1-piperidyl]isoindoline-1,3-dione (20 mg, 23.39 μmol, 21.30% yield, 99.51% purity) as a yellow solid.

Exemplary Synthesis of Compound 107

Compound 107 was prepared in a manner analogous to compound 73.

Step 1

A mixture of 5-(1-methylcyclopropoxy)-3-[6-[4-[[4-(4-piperidylmethyl)piperazin-1-yl]methyl]-1-piperidyl]pyrimidin-4-yl]-2H-indazole (50 mg, 91.79 μmol, 1 eq) and 2-(2,6-dioxo-3-piperidyl)-5,6-difluoro-isoindoline-1,3-dione (30 mg, 101.97 μmol, 1.11 eq) in MeCN (5 mL) was added DIEA (371.00 mg, 2.87 mmol, 0.5 mL, 31.27 eq). The mixture was stirred at 60° C. for 2 h. LCMS showed desired MS. The crude product was purified by reversed-phase HPLC(Column: 3_Phenomenex Luna C18 75*30 mm*3 um; Condition: water (0.225% FA)-ACN; Begin B: 0 End B: 35; Flow Rate: 25 mL/min; Gradient Time: 35 min; 100% B Hold Time: 3 min) to give 2-(2,6-dioxo-3-piperidyl)-5- fluoro-6-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]isoindoline-1,3-dione (10.7 mg, 12.94 μmol, 14.09% yield, 99% purity) as a green solid.

Exemplary Synthesis of Compound 108

Compound 108 was prepared in a manner analogous to compound 84 using trans-1,4-bis(piperidin-4-yloxy)cyclohexane.

Step 1

To a mixture of 2-(2,6-dioxo-3-piperidyl)-5-[4-[4-(4-piperidyloxy)cyclohexoxy]-1-piperidyl]isoindoline-1,3-dione (35 mg, 64.98 μmol, 1 eq) and 3-(6-chloropyrimidin-4-yl)-5-(1-methylcyclopropoxy)-1H-indazole (19.54 mg, 64.98 μmol, 1 eq) in DMSO (5 mL) was added DIEA (67.18 mg, 519.83 μmol, 90.54 μL, 8 eq) in one portion at 25° C. under N2. The mixture was stirred at 90° C. for 16 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (0.225% FA)-ACN]; B %: 10%-50%, 40 min) to give 2-(2,6-dioxo-3-piperidyl)-5-[4-[4-[[1-[6-[5-(1-methylcyclopropoxy)-1H-indazol-3-yl]pyrimidin-4-yl]-4-piperidyl]oxy]cyclohexoxy]-1-piperidyl]isoindoline-1,3-dione (9.1 mg, 11.23 μmol, 17.29% yield, 99.10% purity) as a yellow solid.

Exemplary Synthesis of Compound 109

Step 1

To a mixture of DIEA (1.29 g, 9.96 mmol, 1.73 mL, 2.42 eq) and 3-aminopiperidine-2,6-dione (812.61 mg, 4.94 mmol, 1.2 eq, HCl) in DCM (30 mL) was added methyl 4-bromo-2-formyl-benzoate (1 g, 4.11 mmol, 1 eq) and AcOH (0.8 mL) in one portion at 25° C. under N2. The mixture was stirred at 40° C. for 12 hr, then NaBH3CN (775.65 mg, 12.34 mmol, 3 eq) was added and the mixture was stirred at 40° C. for 4 hours. LCMS showed the reaction was completed. The mixture was concentrated in vacuum. The residue was purified by silica gel chromatography (Petroleum ether/Ethyl acetate=100/1, 1/100) to afford 3-(5-bromo-1-oxo-isoindolin-2-yl)piperidine-2,6-dione (500 mg, 1.55 mmol, 37.61% yield) as green solid.

Step 2

To a mixture of 4-(dimethoxymethyl)piperidine (68.00 mg, 427.06 μmol, 1.2 eq) and 3-(5-bromo-1-oxo-isoindolin-2-yl)piperidine-2,6-dione (115 mg, 355.88 μmol, 1 eq) in DMSO (4 mL) was added Cs2CO3 (231.91 mg, 711.76 μmol, 2 eq) and Pd-PEPPSI-pent Cl—O-picoline (19.32 mg, 35.59 μmol, 0.1 eq) in one portion at 25° C. under N2. The mixture was stirred at 80° C. for 12 hours. The mixture was filtered and poured into ice-sat. aq. NH4Cl (30 mL). The aqueous phase was extracted with ethyl acetate (30 mL*3). The combined organic phase was dried with anhydrous Na2SO4, filtered and concentrated in vacuum. The residue was purified by silica gel chromatography (Petroleum ether/Ethyl acetate=100/1, 1/100) to afford 3-[5-[4-(dimethoxymethyl)-1-piperidyl]-1-oxo-isoindolin-2-yl]piperidine-2,6-dione (90 mg, 224.18 μmol, 62.99% yield) as yellow solid.

Step 3

To a mixture of 3-[5-[4-(dimethoxymethyl)-1-piperidyl]-1-oxo-isoindolin-2-yl]piperidine-2,6-dione (90 mg, 224.18 μmol, 1 eq) in THF (4 mL) was added HCl (2 M, 2 mL, 17.84 eq) in one portion at 25° C. under N2. The mixture was stirred at 25° C. for 2 hours. LCMS showed the reaction was completed. The mixture was poured into sat. aq. $NaHCO_3$ (40 mL). The aqueous phase was extracted with ethyl acetate (40 mL*3). The combined organic phase was washed with brine (40 mL*2), dried with anhydrous Na2SO4, filtered and concentrated in vacuum to afford 1-[2-(2,6-dioxo-3-piperidyl)-1-oxo-isoindolin-5-yl]piperidine-4-carbaldehyde (60 mg, 143.51 μmol, 64.01% yield, 85% purity) as yellow solid.

Step 4

To a mixture of 1-[2-(2,6-dioxo-3-piperidyl)-1-oxo-isoindolin-5-yl]piperidine-4-carbaldehyde (30 mg, 84.42 μmol, 1 eq) and 5-(1-methylcyclopropoxy)-3-[6-[(3S)-3-methyl-4-(4-piperidylmethyl)piperazin-1-yl]pyrimidin-4-yl]-2H-indazole (42.86 mg, 92.86 μmol, 1.1 eq) in DCM (2 mL) and MeOH (0.2 mL) was added HOAc (506.93 ug, 8.44 μmol, 4.83 e-1 μL, 0.1 eq) in one portion at 25° C. under N2. The mixture was stirred at 35° C. for 12 hr. Then NaBH3CN (15.91 mg, 253.25 μmol, 3 eq) was added and the mixture was stirred at 25° C. for 4 hours. The mixture was concentrated in vacuum. The residue was purified by prep-HPLC (column: 3_Phenomenex Luna C18 75*30 mm*3 um; mobile phase: [water (0.225% FA)-ACN]; B %: 0%-30%, 40 min) to afford 3-[5-[4-[[4-[[(2S)-2-methyl-4-[6-[5-(1-methylcyclopropoxy)-2H-indazol-3-yl]pyrimidin-4-yl]piperazin-1-yl]methyl]-1-piperidyl]methyl]-1-piperidyl]-1-oxo-isoindolin-2-yl]piperidine-2,6-dione (10.4 mg, 12.87 μmol, 15.24% yield, 99.11% purity) as white solid.

Exemplary Synthesis of Compound 110

Compound 110 was prepared in a manner analogous to compound 109.

Step 1

To a mixture of DIEA (20.60 mg, 159.35 μmol, 27.76 μL, 2 eq) and 3-[6-[4-[(4-fluoro-4-piperidyl)methyl]piperazin-1-yl]pyrimidin-4-yl]-5-(1-methylcyclopropoxy)-1H-indazole (40 mg, 79.68 μmol, 1 eq, HCl) in MeOH (10 mL) and HOAc (1 mL) was added 1-[2-(2,6-dioxo-3-piperidyl)-1-oxo-isoindolin-5-yl]piperidine-4-carbaldehyde (56.63 mg, 159.35 μmol, 2 eq) and (2-methylpyridin-1-ium-1-yl)boranuide (25.57 mg, 239.03 μmol, 3 eq) in one portion at 25° C. under N2. The mixture was stirred at 25° C. for 16 hours. The mixture was concentrated in vacuum. The residue was purified by prep-HPLC (column: Phenomenex Luna C18 75*30 mm*3 um; mobile phase: [water (0.225% FA)-ACN]; B %: 10%-40%, 35 min) to give 3-[5-[4-[[4-fluoro-4-[[4-[6-[5-(1-methylcyclopropoxy)-1H-indazol-3-yl]pyrimidin-4-yl]piperazin-1-yl]methyl]-1-piperidyl]methyl]-1-piperidyl]-1-oxo-isoindolin-2-yl]piperidine-2,6-dione (23.3 mg, 28.37 μmol, 35.60% yield, 98% purity) as white solid.

Exemplary Synthesis of Compound 111

Step 1

To a mixture of tert-butyl (3S)-3-(hydroxymethyl)pyrrolidine-1-carboxylate (1 g, 4.97 mmol, 1 eq) and TosCl (1.89 g, 9.94 mmol, 2 eq) in DCM (10 mL) was added TEA (1.01 g, 9.94 mmol, 1.38 mL, 2 eq) and DMAP (607.01 mg, 4.97 mmol, 1 eq) in one portion at 0° C. under N2. The mixture was stirred at 20° C. for 1 hour. LCMS showed desired MS. The reaction mixture was filtered and the filtrate was concentrated under reduced pressure. The residue was purified by silica gel column chromatography (0 to 50% ethyl acetate in petroleum ether) to give tert-butyl (3S)-3-(p-tolylsulfonyloxymethyl)pyrrolidine-1-carboxylate (2.2 g, crude) as a white solid.

Step 2

To a mixture of tert-butyl (3S)-3-(p-tolylsulfonyloxymethyl)pyrrolidine-1-carboxylate (462.53 mg, 1.30 mmol, 1.5 eq) and benzyl (3S)-3-methylpiperazine-1-carboxylate (500 mg, 867.51 μmol, 1 eq, 3TFA) in MeCN (10 mL) was added KI (720.04 mg, 4.34 mmol, 5 eq) and DIPEA (560.60 mg, 4.34 mmol, 755.52 μL, 5 eq) in one portion at 20° C. under N2. The mixture was stirred at 100° C. for 16 hours. TLC (DCM:MeOH=10:1, Rf=0.10) showed the reaction was completed. The mixture was cooled to 20° C. and concentrated in reduced pressure at 20° C. The residue was poured into water (10 mL). The reaction mixture was filtered and filtrate was concentrated under reduced pressure. The residue was purified by silica gel column chromatography (0 to 100% ethyl acetate in petroleum ether) to give benzyl (3S)-4-[[(3R)-1-tert-butoxycarbonylpyrrolidin-3-yl]methyl]-3-methyl-piperazine-1-carboxylate (460 mg, crude) as a yellow oil.

Step 3

To a mixture of benzyl (3S)-4-[[(3R)-1-tert-butoxycarbonylpyrrolidin-3-yl]methyl]-3-methyl-piperazine-1-carboxylate (460 mg, 1.10 mmol, 1 eq) in DCM (10 mL) was added TFA (1.54 g, 13.51 mmol, 1 mL, 12.26 eq) in one portion at 25° C. under N2. The mixture was stirred at 25° C. for 1 hours. LCMS showed the reaction was completed. The mixture was concentrated in vacuum to give benzyl (3S)-3-methyl-4-[[(3S)-pyrrolidin-3-yl]methyl]piperazine-1-carboxylate (500 mg, crude) as a yellow oil.

Step 4

To a mixture of benzyl (3S)-3-methyl-4-[[(3S)-pyrrolidin-3-yl]methyl]piperazine-1-carboxylate (350 mg, 1.10 mmol, 1 eq) and 1-[2-(2,6-dioxo-3-piperidyl)-1,3-dioxo-isoindolin-5-yl]piperidine-4-carbaldehyde (407.28 mg, 1.10 mmol, 1 eq) in MeOH (10 mL) was added HOAc (1 mL) and borane; 2-methylpyridine (235.88 mg, 2.21 mmol, 2 eq) in one portion at 25° C. under N2. The mixture was stirred at 25° C. for 1 h. LCMS showed desired MS. The mixture was concentrated in vacuum. The residue was purified by silica gel chromatography (Dichloromethane:Methanol=10:1, 0-100% (20 min) of Ethyl acetate in Petroleum ether, 100% (10 min) of Ethyl acetate in Petroleum ether) to give benzyl (3S)-4-[[(3S)-1-[[1-[2-(2,6-dioxo-3-piperidyl)-1,3-dioxo-isoindolin-5-yl]-4-piperidyl]methyl]pyrrolidin-3-yl]methyl]-3-methyl-piperazine-1-carboxylate (1 g, crude) as a yellow oil.

Step 5

To a mixture of benzyl (3S)-4-[[(3S)-1-[[1-[2-(2,6-dioxo-3-piperidyl)-1,3-dioxo-isoindolin-5-yl]-4-piperidyl]methyl]pyrrolidin-3-yl]methyl]-3-methyl-piperazine-1-carboxylate (740 mg, 1.10 mmol, 1 eq) was added TFA (3.08 g, 27.01 mmol, 2 mL, 24.49 eq) in one portion at 70° C. under N2. The mixture was stirred at 70° C. for 3 h. LCMS showed desired MS. The residue was concentrated in vacuum to give 2-(2,6-dioxo-3-piperidyl)-5-[4-[[(3S)-3-[[(2S)-2-methylpiperazin-1-yl]methyl]pyrrolidin-1-yl]methyl]-1-piperidyl]isoindoline-1,3-dione (1.2 g, crude) as a yellow oil Step 6

To a mixture of 2-(2,6-dioxo-3-piperidyl)-5-[4-[[(3S)-3-[[(2S)-2-methylpiperazin-1-yl]methyl]pyrrolidin-1-yl]methyl]-1-piperidyl]isoindoline-1,3-dione (182.02 mg, 339.16 μmol, 1.70 eq) and 3-(6-chloropyrimidin-4-yl)-5-(1-methylcyclopropoxy)-2H-indazole (60 mg, 199.51 μmol, 1 eq) in DMSO (5 mL) was added DIEA (206.28 mg, 1.60 mmol, 278.00 μL, 8 eq) in one portion at 20° C. under N2. The mixture was stirred at 80° C. for 12 h. LCMS showed starting material was consumed completely. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 35; Flow Rate: 25 mL/min; Gradient Time: 40 min; 100% B Hold Time: 3 min) to give 2-(2,6-dioxo-3-piperidyl)-5-[4-[[(3S)-3-[[(2S)-2-methyl-4-[6-[5-(1-methylcyclopropoxy)-1H-indazol-3-yl]pyrimidin-4-yl]piperazin-1-yl]methyl]pyrrolidin-1-yl]methyl]-1-piperidyl]isoindoline-1,3-dione (62.6 mg, 77.38 μmol, 38.78% yield, 99% purity) as a yellow solid.

Exemplary Synthesis of Compound 112

Compound 112 was prepared in a method analogous to compound 109.

Step 1

To the mixture of 5-(1-methylcyclopropoxy)-3-[6-[4-(piperazin-1-ylmethyl)-1-piperidyl]pyrimidin-4-yl]-2H-indazole (75.56 mg, 168.83 μmol, 1 eq) and 1-[2-(2,6-dioxo-3-piperidyl)-1-oxo-isoindolin-5-yl]piperidine-4-carbaldehyde (60 mg, 168.83 μmol, 1 eq) in HOAC (1 mL) and MeOH (10 mL) was stirred at 20° C. for 20 min, then was added borane; 2-methylpyridine (36.12 mg, 337.66 μmol, 2 eq). Then the mixture was stirred at 20° C. for 16 h under N2. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-30%, 40 min) to afford 3-[5-[4-[[4-[[1-[6-[5-(1-methylcyclopropoxy)-2H-indazol-3-yl]pyrimidin-4-yl]-4-piperidyl]methyl]piperazin-1-yl]methyl]-1-piperidyl]-1-oxo-isoindolin-2-yl]piperidine-2,6-dione (32.9 mg, 41.81 μmol, 24.76% yield, 100% purity) as white solid.

Exemplary Synthesis of Compound 113

Compound 113 was prepared in a manner analogous to compound 111 starting with tert-butyl (3R)-3-(hydroxymethyl)pyrrolidine-1-carboxylate.

Exemplary Synthesis of Compound 114

Step 1

To a mixture of tert-butyl (3S)-3-(p-tolylsulfonyloxymethyl)pyrrolidine-1-carboxylate (778.43 mg, 2.19 mmol, 1.5 eq) and 2-(2,6-dioxo-3-piperidyl)-5-piperazin-1-yl-isoindoline-1,3-dione (500 mg, 1.46 mmol, 1 eq) in MeCN (10 mL) was added KI (1.21 g, 7.30 mmol, 5 eq) and DIPEA (943.80 mg, 7.30 mmol, 1.27 mL, 5 eq) in one portion at 20° C. under N2. The mixture was stirred at 100° C. for 16 hours. LCMS showed desired product. The reaction mixture was filtered and filtrate was concentrated under reduced pressure. The residue was purified by silica gel column chromatography (0 to 100% ethyl acetate in petroleum ether) to give tert-butyl (3R)-3-[[4-[2-(2,6-dioxo-3-piperidyl)-1,3-dioxo-isoindolin-5-yl]piperazin-1-yl]methyl]pyrrolidine-1-carboxylate (400 mg, 738.21 μmol, 50.56% yield, 97% purity) as a yellow oil.

Step 2

To a mixture of tert-butyl (3R)-3-[[4-[2-(2,6-dioxo-3-piperidyl)-1,3-dioxo-isoindolin-5-yl]piperazin-1-yl]methyl]pyrrolidine-1-carboxylate (400 mg, 761.04 μmol, 1 eq) in DCM (5 mL) was added TFA (1.54 g, 13.51 mmol, 1 mL, 17.75 eq) in one portion at 20° C. The mixture was stirred at 25° C. for 1 hour. LCMS showed Reactant 1 was consumed completely and desired MS found. The mixture was concentrated in vacuum to give 2-(2,6-dioxo-3-piperidyl)-5-[4-[[(3S)-pyrrolidin-3-yl]methyl]piperazin-1-yl]isoindoline-1,3-dione (400 mg, crude) as a yellow oil.

Step 3

To a mixture of 2-(2,6-dioxo-3-piperidyl)-5-[4-[[(3S)-pyrrolidin-3-yl]methyl]piperazin-1-yl]isoindoline-1,3-dione (323 mg, 759.14 μmol, 1 eq) and tert-butyl 4-formylpiperidine-1-carboxylate (242.86 mg, 1.14 mmol, 1.5 eq) in MeOH (5 mL) was added HOAc (1 mL) and borane; 2-methylpyridine (162.40 mg, 1.52 mmol, 2 eq) in one portion at 25° C. under N2. The mixture was stirred at 25° C. for 1 h. LCMS showed the reaction was completed. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (Dichloromethane:Methanol=10:1, 0-100% (20 min) of Ethyl acetate in Petroleum ether, 100% (10 min) of Ethyl acetate in Petroleum ether) to give tert-butyl 4-[[(3S)-3-[[4-[2-(2,6-dioxo-3-piperidyl)-1,3-dioxo-isoindolin-5-yl]piperazin-1-yl]methyl]pyrrolidin-1-yl]methyl]piperidine-1-carboxylate (600 mg, crude) as a yellow oil.

Step 4

To a mixture of tert-butyl 4-[[(3S)-3-[[4-[2-(2,6-dioxo-3-piperidyl)-1,3-dioxo-isoindolin-5-yl]piperazin-1-yl]methyl]pyrrolidin-1-yl]methyl]piperidine-1-carboxylate (600 mg, 963.46 μmol, 1 eq) in DCM (10 mL) was added TFA (3.08 g, 27.01 mmol, 2 mL, 28.04 eq) in one portion at 25° C. under N2. The mixture was stirred at 25° C. for 1 h. LCMS showed Reactant 1 was consumed completely and desired MS found. The mixture was concentrated in vacuum to give 2-(2,6-dioxo-3-piperidyl)-5-[4-[[(3S)-1-(4-piperidylmethyl)pyrrolidin-3-yl]methyl]piperazin-1-yl]isoindoline-1,3-dione (1 g, crude, TFA) as a yellow oil.

Step 5

To a mixture of 2-(2,6-dioxo-3-piperidyl)-5-[4-[[(3S)-1-(4-piperidylmethyl)pyrrolidin-3-yl]methyl]piperazin-1-yl]isoindoline-1,3-dione (177.26 mg, 339.16 μmol, 1.70 eq) and 3-(6-chloropyrimidin-4-yl)-5-(1-methylcyclopropoxy)-2H-indazole (60 mg, 199.51 μmol, 1 eq) in DMSO (5 mL) was added DIEA (206.28 mg, 1.60 mmol, 278.00 μL, 8 eq) in one portion at 20° C. under N2. The mixture was stirred at 80° C. for 16 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 35; Flow Rate: 25 mL/min; Gradient Time: 35 min; 100% B Hold Time: 3 min). The residue was concentrated in vacuum to give 2-(2,6-dioxo-3-piperidyl)-5-[4-[[(3S)-1-[[1-[6-[5-(1-methylcyclopropoxy)-1H-indazol-3-yl]pyrimidin-4-yl]-4-piperidyl]methyl]pyrrolidin-3-yl]methyl]piperazin-1-yl]isoindoline-1,3-dione (38.2 mg, 48.54 μmol, 24.33% yield, 100% purity) as a yellow solid.

Exemplary Synthesis of Compound 115

Compound 115 was prepared in a manner analogous to compound 114 starting with tert-butyl (3R)-3-(p-tolylsulfonyloxymethyl)pyrrolidine-1-carboxylate.

Exemplary Synthesis of Compound 116

Step 1 tert-butyl (3S)-3-hydroxypyrrolidine-1-carboxylate (5.00 g, 26.70 mmol, 1 eq), pyridin-4-ol (2.54 g, 26.70 mmol, 1 eq) and PPh3 (7.70 g, 29.37 mmol, 1.1 eq) were added to THF (50 mL) and stirred for 30 minutes. To this was dropwise added DIAD (5.94 g, 29.37 mmol, 5.71 mL, 1.1 eq) at 0° C. Once the addition was complete the reaction was stirred at 50° C. for 15.5 hour. TLC (Dichloromethane: Methanol=10:1, Rf=0.45) showed the reaction was completed. LCMS showed there was desired MS. Solvent was evaporated in vacuo. The resulting oil was treated with a 1.0 M HCl aqueous solution (100 mL). The acidic mixture was washed with CH2Cl2 (100 mL×2). The combined CH2Cl2 washings were re-extracted with a 1.0 M HCl aqueous solution (100 mL) and H2O (200 mL), then discarded. The aqueous fractions were combined, basified to pH~12 using a 1.0 M NaOH aqueous solution, and extracted with CH2Cl2 (50 mL×4). The organic extracts were washed with brine, dried over anhydrous Na2SO4, and concentrated in vacuo to a residue. The residue was purified by silica gel chromatography (40 g, 100-200 mesh silica gel, 0-100% (20 min) of Ethyl acetate in Petroleum ether) to give tert-butyl (3R)-3-(4-pyridyloxy)pyrrolidine-1-carboxylate (1.8 g, 6.81 mmol, 25.50% yield) as yellow oil.

Step 2

To a solution of tert-butyl (3R)-3-(4-pyridyloxy)pyrrolidine-1-carboxylate (1.8 g, 6.81 mmol, 1 eq) in EtOH (20 mL) and HOAc (408.94 mg, 6.81 mmol, 389.46 μL, 1 eq) was added Pt2O (257.73 mg, 6.81 mmol, 1 eq) at 25° C. Then the mixture was stirred at 70° C. for 16 h under H2 (50 psi). LCMS showed there was desired MS. The suspension was filtered through a pad of Celite and the pad or filter cake was washed with EtOH (100 mL×3). The combined filtrates were concentrated to dryness to give tert-butyl (3R)-3-(4-piperidyloxy)pyrrolidine-1-carboxylate (1.5 g, 5.55 mmol, 81.47% yield) as a colorless oil Step 3

To a mixture of 2-[[3-(6-chloropyrimidin-4-yl)-5-(1-methylcyclopropoxy)indazol-2-yl]methoxy]ethyl-trimethyl-silane (100 mg, 232.02 μmol, 1 eq), tert-butyl (3R)-3-(4-piperidyloxy)pyrrolidine-1-carboxylate (150 mg, 554.80 μmol, 2.39 eq) in DMSO (5 mL) was added Et3N (70.43 mg, 696.05 μmol, 96.88 μL, 3 eq) in one portion and then was stirred at 100° C. for 1 h. TLC showed the starting material was consumed completely. The mixture was cooled to 20° C., then the residue was poured into water (5 mL). The aqueous phase was extracted with ethyl acetate (3×5 mL). The combined organic phase was washed with brine (2×5 mL), dried with anhydrous Na2SO4, filtered and concentrated in vacuum. The residue was purified by silica gel chromatography (100-200 mesh silica gel, 0-5% (5 min) of Ethyl acetate in Petroleum ether, 5% (10 min) of Ethyl acetate in Petroleum ether, 5%-30% (5 min) of Ethyl acetate in Petroleum ether, 30% (5 min) of Ethyl acetate in Petroleum ether) to give tert-butyl (3R)-3-[[1-[6-[5-(1-methylcyclopropoxy)-1-(2-trimethylsilylethoxymethyl)indazol-3-yl]pyrimidin-4-yl]-4-piperidyl]oxy]pyrrolidine-1-carboxylate (100 mg, 147.09 μmol, 63.40% yield, 97.8% purity) as a yellow oil.

Step 4

To a mixture of tert-butyl (3R)-3-[[1-[6-[5-(1-methylcyclopropoxy)-1-(2-trimethylsilylethoxymethyl)indazol-3-yl]pyrimidin-4-yl]-4-piperidyl]oxy]pyrrolidine-1-carboxylate (100.00 mg, 150.40 μmol, 1 eq) in MeOH (5 mL) was added HCl/EtOAc (4 M, 112.80 μL, 3 eq) in one portion at 25° C. The mixture was stirred at 65° C. for 0.5 h. TLC (Petroleum ether:Ethyl acetate=5:1, Rf=0.03) showed the reaction was completed. The mixture was concentrated in vacuum to give 5-(1-methylcyclopropoxy)-3-[6-[4-[(3R)-pyrrolidin-3-yl]oxy-1-piperidyl]pyrimidin-4-yl]-1H-indazole (80 mg, 118.90 μmol, 79.06% yield, 70% purity, HCl) as a yellow solid.

Step 5

To a mixture of 5-(1-methylcyclopropoxy)-3-[6-[4-[(3R)-pyrrolidin-3-yl]oxy-1-piperidyl]pyrimidin-4-yl]-1H-indazole (80 mg, 128.87 μmol, 70% purity, 1 eq) and 1-[2-(2,6-dioxo-3-piperidyl)-1,3-dioxo-isoindolin-5-yl]piperidine-4-carbaldehyde (47.60 mg, 128.87 μmol, 1 eq) in MeOH (20 mL) was added borane; 2-methylpyridine (27.57 mg, 257.75 μmol, 2 eq) and HOAc (1 mL) in one portion at 25° C. under N2. The mixture was stirred at 25° C. for 16 h. LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (0.225% FA)-ACN]; B %: 0%-35%, 40 min) to give 2-(2,6-dioxo-3-piperidyl)-5-[4-[[(3R)-3-[[1-[6-[5-(1-methylcyclopropoxy)-1H-indazol-3-yl]pyrimidin-4-yl]-4-piperidyl]oxy]pyrrolidin-1-yl]methyl]-1-piperidyl]isoindoline-1,3-dione (45.4 mg, 57.19 μmol, 44.38% yield, 99.25% purity) as a yellow solid.

Exemplary Synthesis of Compound 117

Compound 117 was prepared in a manner analogous to compound 116 starting with tert-butyl (3R)-3-hydroxypyrrolidine-1-carboxylate.

Exemplary Synthesis of Compound 118

Step 1

To a solution of tert-butyl (3S)-3-(4-piperidyloxy)pyrrolidine-1-carboxylate (734.05 mg, 2.72 mmol, 1.5 eq) and 2-(2,6-dioxo-3-piperidyl)-5-fluoro-isoindoline-1,3-dione (500 mg, 1.81 mmol, 1 eq) in DMSO (10 mL) and DIEA (2.34 g, 18.10 mmol, 3.15 mL, 10 eq). The mixture was stirred at 80° C. for 16 h. LCMS showed desired product MS. The resulting product was poured into H2O (20 mL). The mixture was extracted with ethyl acetate (20 mL*3). The organic phase was washed with brine (15 mL*2), dried over anhydrous Na2SO4, concentrated in vacuum to give a residue. The residue was purified by silica gel chromatography (0-50% (10 min) of Ethyl acetate in Petroleum ether, 50% (10 min) of Ethyl acetate in Petroleum ether) to give tert-butyl (3S)-3-[[1-[2-(2,6-dioxo-3-piperidyl)-1,3-dioxo-isoindolin-5-yl]-4-piperidyl]oxy]pyrrolidine-1-carboxylate (760 mg, 1.44 mmol, 79.74% yield) as a yellow solid.

Step 2

To a mixture of tert-butyl (3S)-3-[[1-[2-(2,6-dioxo-3-piperidyl)-1,3-dioxo-isoindolin-5-yl]-4-piperidyl]oxy]pyrrolidine-1-carboxylate (300 mg, 569.71 μmol, 1 eq) in DCM (5 mL) was added TFA (3.08 g, 27.01 mmol, 2 mL, 47.41 eq) in one portion at 25° C. The mixture was stirred at 25° C. for 0.5 h. TLC (Petroleum ether:Ethyl acetate=5:1, Rf=0.03) showed the reaction was completed. The mixture was concentrated in vacuum to give 2-(2,6-dioxo-3-piperidyl)-5-[4-[(3S)-pyrrolidin-3-yl]oxy-1-piperidyl]isoindoline-1,3-dione (300 mg, 438.49 μmol, 76.97% yield, 79% purity, TFA) as a yellow solid.

Step 3

To a mixture of 2-(2,6-dioxopiperidin-3-yl)-5-(4-((S)-pyrrolidin-3-yloxy)piperidin-1-yl)isoindoline-1,3-dione (242 mg, 567.46 μmol, 1 eq) and tert-butyl 4-formylpiperidine-1-carboxylate (181.53 mg, 851.18 μmol, 1.5 eq) in MeOH (10 mL) was added HOAc (1 mL) and borane; 2-methylpyridine (121.39 mg, 1.13 mmol, 2 eq) in one portion at 25° C. under N2. The mixture was stirred at 25° C. for 1 h. TLC (Dichloromethane:Methanol=10:1, Rf=0.50) showed the reaction was completed. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (Dichloromethane:Methanol=10:1, Rf=0.50, 0-100% (20 min) of Ethyl acetate in Petroleum ether, 100% (10 min) of Ethyl acetate in Petroleum ether) to give tert-butyl 4-(((3S)-3-((1-(2-(2,6-dioxopiperidin-3-yl)-1,3-dioxoisoindolin-5-yl)piperidin-4-yl)oxy)pyrrolidin-1-yl)methyl)piperidine-1-carboxylate (270 mg, 388.72 μmol, 68.50% yield, 89.8% purity) as a yellow oil.

Step 4

To a mixture of tert-butyl 4-[[(3S)-3-[[1-[2-(2,6-dioxo-3-piperidyl)-1,3-dioxo-isoindolin-5-yl]-4-piperidyl]oxy]pyrrolidin-1-yl]methyl]piperidine-1-carboxylate (120 mg, 192.39 μmol, 1 eq) in DCM (5 mL) was added TFA (3.08 g, 27.01 mmol, 2 mL, 140.41 eq) in one portion at 25° C. The mixture was stirred at 25° C. for 0.5 h. TLC (Petroleum ether:Ethyl acetate=5:1, Rf=0.03) showed the reaction was completed. The mixture was concentrated in vacuum to give 2-(2,6-dioxo-3-piperidyl)-5-[4-[(3S)-1-(4-piperidylmethyl)pyrrolidin-3-yl]oxy-1-piperidyl]isoindoline-1,3-dione (100 mg, 148.99 μmol, 77.44% yield, 95% purity, TFA) as a yellow gum.

Step 5

To a mixture of 2-(2,6-dioxo-3-piperidyl)-5-[4-[(3S)-1-(4-piperidylmethyl)pyrrolidin-3-yl]oxy-1-piperidyl]isoindoline-1,3-dione (100 mg, 156.83 μmol, 1.57 eq, TFA) and 3-(6-chloropyrimidin-4-yl)-5-(1-methylcyclopropoxy)-1H-indazole (30 mg, 99.75 μmol, 1 eq) in DMSO (5 mL) was added DIEA (103.14 mg, 798.03 μmol, 139.00 μL, 8 eq) in one portion at 25° C. under N2. The mixture was stirred at 90° C. for 16 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (0.225% FA)-ACN]; B %: 0%-35%, 40 min) to give 2-(2,6-dioxo-3-piperidyl)-5-[4-[(3S)-1-[[1-[6-[5-(1-methylcyclopropoxy)-1H-indazol-3-yl]pyrimidin-4-yl]-4-piperidyl]methyl]pyrrolidin-3-yl]oxy-1-piperidyl]isoindoline-1,3-dione (21.5 mg, 26.91 μmol, 26.98% yield, 98.63% purity) as a yellow solid.

Exemplary Synthesis of Compound 119

Compound 119 was prepared in a manner analogous to compound 118 using tert-butyl (3S)-3-(4-piperidyloxy)pyrrolidine-1-carboxylate.

Exemplary Synthesis of Compound 120

Step 1

To a solution of methyl 5-oxopyrrolidine-3-carboxylate (10 g, 69.86 mmol, 1 eq) in THF (200 mL) was added LiAlH4 (3.98 g, 104.79 mmol, 1.5 eq) at 0° C. under N2 in portions. After addition, the reaction mixture was stirred at 0° C. for 1 h. TLC (ethyl acetate:Methanol=10:1) showed several new spots. The reaction mixture was quenched by addition of H2O (2 mL), followed by 15% aqueous NaOH (2 mL) and water (6 mL). After being stirred at room temperature for 30 min, the mixture was filtered through Celite pad to remove the solid. The filtrate was concentrated to dryness to give crude product. The residue was purified by silica gel column chromatography (0 to 10% Methanol in ethyl acetate) to give 4-(hydroxymethyl)pyrrolidin-2-one (7.84 g, crude) as a white solid.

Step 2

To a mixture of 4-(hydroxymethyl)pyrrolidin-2-one (390 mg, 3.39 mmol, 1 eq) and TosCl (1.29 g, 6.77 mmol, 2 eq) in DCM (10 mL) was added TEA (685.56 mg, 6.77 mmol, 942.99 μL, 2 eq) and DMAP (206.92 mg, 1.69 mmol, 0.5 eq) in one portion at 0° C. under N2. The mixture was stirred at 20° C. for 1 hour. LCMS showed desired MS. TLC (Petroleum ether:Ethyl acetate=0:1) showed several new spots. The reaction mixture was concentrated under reduced pressure. The residue was purified by silica gel column chromatography (0 to 100% ethyl acetate in petroleum ether) to give (5-oxopyrrolidin-3-yl)methyl 4-methylbenzenesulfonate (550 mg, 1.67 mmol, 49.44% yield, 82% purity) as a brown solid.

Step 3

To a solution of (5-oxopyrrolidin-3-yl)methyl 4-methylbenzenesulfonate (7 g, 25.99 mmol, 1 eq) in MeCN (200 mL) was added benzyl piperazine-1-carboxylate (6.87 g, 31.19 mmol, 6.03 mL, 1.2 eq), KI (12.94 g, 77.98 mmol, 3 eq) and Cs2CO3 (21.17 g, 64.98 mmol, 2.5 eq). Then the mixture was stirred at 80° C. for 16 hr. TLC (Dichloromethane:Methanol=10:1, Rf=0.4) showed no start material and a new spot. The residue was diluted with H2O (50 mL) extracted with ethyl acetate (100 mL×3). The combined organic layers were washed with brine (2×50 mL), dried over anhydrous sodium sulfate, filtered and concentrated under reduced pressure to give a residue. The residue was purified by silica gel column chromatography (0-10% Methanol in Dichloromethane) to give benzyl 4-[(5-oxopyrrolidin-3-yl)methyl]piperazine-1-carboxylate (4.2 g, 11.65 mmol, 44.80% yield, 88% purity) as a colorless gum.

Step 4

A solution of NaH (1.06 g, 26.47 mmol, 60% purity, 3 eq) suspended in DMF (10 mL) was cooled to 0° C. before benzyl 4-[(5-oxopyrrolidin-3-yl)methyl]piperazine-1-carboxylate (2.8 g, 8.82 mmol, 1 eq) was added slowly. The solution was stirred at 0° C. for another 10 minutes tert-butyl 4-(p-tolylsulfonyloxymethyl)piperidine-1-carboxylate (4.24 g, 11.47 mmol, 1.3 eq), KI (4.39 g, 26.47 mmol, 3 eq) was added. The reaction mixture was stirred at 25° C. for 16 hours. LCMS showed desired MS. The resulting product was poured into H2O (10 mL). The mixture was extracted with ethyl acetate (50 mL*3). The organic phase was washed with brine (50 mL), dried over anhydrous Na2SO4, concentrated in vacuum to give a residue. The residue was purified by prep-HPLC (column: 3_Phenomenex Luna C18 75*30 mm*3 um; mobile phase: [water (0.225% FA)-ACN]; B %: 0%-40%, 40 min) to give benzyl 4-[[1-[(1-tert-butoxycarbonyl-4-piperidyl)methyl]-5-oxo-pyrrolidin-3-yl]methyl] piperazine-1-carboxylate (450 mg, 874.37 μmol, 9.91% yield) as a colorless oil.

Step 5

Benzyl 4-[[1-[(1-tert-butoxycarbonyl-4-piperidyl) methyl]-5-oxo-pyrrolidin-3-yl]methyl]piperazine-1-carboxylate (450 mg, 874.37 μmol, 1 eq) was purificated by SFC. The residue was purified by SFC (column: DAICEL CHIRALPAK AD (250 mm*30 mm, 10 um); mobile phase: [0.1% NH3H2O IPA]; B %: 25%-25%, min) to give benzyl 4-[[(3R)-1-[(1-tert-butoxycarbonyl-4-piperidyl)methyl]-5-oxo-pyrrolidin-3-yl]methyl]piperazine-1-carboxylate or the enantiomer thereof (160 mg, 310.89 μmol, 35.56% yield, 100% purity) and benzyl 4-[[(3S)-1-[(1-tert-butoxycarbonyl-4-piperidyl)methyl]-5-oxo-pyrrolidin-3-yl]methyl]piperazine-1-carboxylate or the enantiomer thereof (160 mg, 296.90 μmol, 33.96% yield, 95.5% purity) as a colorless oil.

Step 6

A mixture of benzyl 4-[[(3R)-1-[(1-tert-butoxycarbonyl-4-piperidyl)methyl]-5-oxo-pyrrolidin-3-yl]methyl]piperazine-1-carboxylate or the enantiomer thereof (50 mg, 97.15 μmol, 1 eq) in DCM (3 mL) was added TFA (11.08 mg, 97.15 μmol, 7.19 μL, 1 eq) and then the mixture was stirred at 25° C. for 1 hr. TLC (Dichloromethane:Methanol=10:1) showed one new spot. The resulting product was concentrated in vacuum to give a residue to give benzyl 4-[[(3R)-5-oxo-1-(4-piperidylmethyl)pyrrolidin-3-yl]methyl]piperazine-1-carboxylate or the enantiomer thereof (50 mg, crude, TFA) as a colorless oil.

Step 7

A mixture of benzyl 4-[[(3R)-5-oxo-1-(4-piperidylmethyl)pyrrolidin-3-yl]methyl]piperazine-1-carboxylate or the enantiomer thereof (40.27 mg, 97.15 μmol, 1 eq), 2-(2,6-dioxo-3-piperidyl)-5-fluoro-isoindoline-1,3-dione (26.83 mg, 97.15 μmol, 1 eq) in DMSO (5 mL) was added DIEA (12.56 mg, 97.15 μmol, 16.92 μL, 1 eq), and then the mixture was stirred at 100° C. for 12 hr under N2 atmosphere. LCMS showed desired MS. TLC (Methanol:Dichloromethane=1:10) showed one new major spot. The resulting product was poured into H2O (10 mL). The mixture was extracted with ethyl acetate (50 mL*3). The organic phase was washed with brine (50 mL), dried over anhydrous Na2SO4, concentrated in vacuum to give a residue. The residue was purified by silica gel column chromatography (0 to 10% Methanol in Dichloromethane) to give benzyl 4-[[(3R)-1-[[1-[2-(2,6-dioxo-3-piperidyl)-1,3-dioxo-isoindolin-5-yl]-4-piperidyl]methyl]-5-oxo-pyrrolidin-3-yl] methyl]piperazine-1-carboxylate or the enantiomer thereof (100 mg, 73.05 μmol, 75.20% yield, 49% purity) as a yellow oil.

Step 8

A mixture of benzyl 4-[[(3R)-1-[[1-[2-(2,6-dioxo-3-piperidyl)-1,3-dioxo-isoindolin-5-yl]-4-piperidyl]methyl]-5-oxo-pyrrolidin-3-yl]methyl]piperazine-1-carboxylate or the enantiomer thereof (65 mg, 96.91 μmol, 1 eq) in TFA (11.05 mg, 96.91 μmol, 7.18 μL, 1 eq), and then the mixture was stirred at 70° C. for 1 hr under N2 atmosphere. TLC (Dichloromethane:Methanol=10:1) showed starting material consumed completed and one new spot found. The reaction mixture was filtered and concentrated under reduced pressure to give 2-(2,6-dioxo-3-piperidyl)-5-[4-[[(4R)-2-oxo-4-(piperazin-1-ylmethyl)pyrrolidin-1-yl]methyl]-1-piperidyl]

isoindoline-1,3-dione or the enantiomer thereof (70 mg, crude, TFA) as a colorless oil.

Step 9

A mixture of 2-(2,6-dioxo-3-piperidyl)-5-[4-[[(4R)-2-oxo-4-(piperazin-1-ylmethyl)pyrrolidin-1-yl]methyl]-1-piperidyl]isoindoline-1,3-dione or the enantiomer thereof (53.53 mg, 99.75 μmol, 1 eq), 3-(6-chloropyrimidin-4-yl)-5-(1-methylcyclopropoxy)-1H-indazole (30 mg, 99.75 μmol, 1 eq), DIEA (12.89 mg, 99.75 μmol, 17.38 μL, 1 eq) in DMSO (5 mL) was added DIEA (12.89 mg, 99.75 μmol, 17.38 μL, 1 eq) and then the mixture was stirred at 100° C. for 12 hr under N2 atmosphere. LCMS showed the starting material was consumed completely and desired MS found. The reaction mixture was concentrated under reduced pressure to give a residue. The crude product was purified by reversed-phase HPLC (column: 3_Phenomenex Luna C18 75*30 mm*3 um; mobile phase: [water (0.225% FA)-ACN]; B %: 0%-40%, 40 min) to give 2-(2,6-dioxo-3-piperidyl)-5-[4-[[(4R)-4-[[4-[6-[5-(1-methylcyclopropoxy)-1H-indazol-3-yl]pyrimidin-4-yl]piperazin-1-yl]methyl]-2-oxo-pyrrolidin-1-yl]methyl]-1-piperidyl]isoindoline-1,3-dione or the enantiomer thereof (11.5 mg, 13.78 μmol, 13.82% yield, 96% purity) as a yellow solid.

Exemplary Synthesis of Compound 121

Compound 121 was prepared in a manner analogous to compound 120 using benzyl 4-[[(3S)-1-[(1-tert-butoxycarbonyl-4-piperidyl)methyl]-5-oxo-pyrrolidin-3-yl]methyl] piperazine-1-carboxylate or the enantiomer thereof.

Exemplary Synthesis of Compound 122

Step 1

To a mixture of tert-butyl 3-(hydroxymethyl)azetidine-1-carboxylate (500 mg, 2.67 mmol, 1 eq) and TosCl (1.02 g, 5.34 mmol, 2 eq) in DCM (10 mL) was added TEA (270.22 mg, 2.67 mmol, 371.69 μL, 1 eq) and DMAP (326.25 mg, 2.67 mmol, 1 eq) in one portion at 0° C. under N2. The mixture was stirred at 20° C. for 1 hour to give light-yellow mixture. TLC (Petroleum ether:Ethyl acetate=1:1, Rf=0.30) showed the reaction was completed. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel chromatography (12 g, 0-22% (5 min) of Ethyl acetate in Petroleum ether, 22% (5 min) of Ethyl acetate in Petroleum ether) to give tert-butyl 3-(p-tolylsulfonyloxymethyl)azetidine-1-carboxylate (1 g, crude) as a colourless oil.

Step 2

To a mixture of tert-butyl 3-(p-tolylsulfonyloxymethyl) azetidine-1-carboxylate (444.28 mg, 1.30 mmol, 1.5 eq) and benzyl (3S)-3-methylpiperazine-1-carboxylate (500 mg, 867.51 μmol, 1 eq, 3 TFA) in MeCN (5 mL) was added KI (720.03 mg, 4.34 mmol, 5 eq) and DIPEA (560.58 mg, 4.34 mmol, 755.50 μL, 5 eq) in one portion at 20° C. under N2. The mixture was stirred at 100° C. for 16 hours. TLC showed the reaction was completed. The mixture was cooled to 20° C. and concentrated in reduced pressure at 20° C. The residue was poured into water (10 mL). The aqueous phase was extracted with ethyl acetate (10 mL*3). The combined organic phase was washed with brine (10 mL*3), dried with anhydrous Na2SO4, filtered and concentrated in vacuum. The residue was purified by silica gel chromatography (12 g, 30 mL/min, 0-10% (10 min) of MeOH in DCM, 10% (10 min) of MeOH in DCM) to give benzyl (3S)-4-[(1-tert-butoxycarbonylazetidin-3-yl)methyl]-3-methyl-piperazine-1-carboxylate (170 mg, 311.76 μmol, 35.94% yield, 74% purity) as a yellow gum.

Step 3

To a mixture of (S)-benzyl 4-((1-(tert-butoxycarbonyl) azetidin-3-yl)methyl)-3-methylpiperazine-1-carboxylate (170 mg, 421.30 μmol, 1 eq) in DCM (5 mL) was added TFA (4.62 g, 40.52 mmol, 3 mL, 96.17 eq) in one portion at 25° C. under N2. The mixture was stirred at 25° C. for 30 min. TLC showed the reaction was completed. The mixture was concentrated in vacuum to give (S)-benzyl 4-(azetidin-3-ylmethyl)-3-methylpiperazine-1-carboxylate (200 mg, 244.36 μmol, 58.00% yield, 51% purity, TFA) as a yellow gum.

Step 4

To a mixture of benzyl (3S)-4-(azetidin-3-ylmethyl)-3-methyl-piperazine-1-carboxylate (200 mg, 479.13 μmol, 1 eq, TFA) and 1-[2-(2,6-dioxo-3-piperidyl)-1,3-dioxo-isoindolin-5-yl]piperidine-4-carbaldehyde (176.98 mg, 479.13 μmol, 1 eq) in MeOH (10 mL) was added HOAc (1 mL) and borane; 2-methylpyridine (102.50 mg, 958.26 μmol, 2 eq) in one portion at 25° C. under N2. The mixture was stirred at 25° C. for 1 h. TLC (Dichloromethane:Methanol=10:1, Rf=0.59) showed the reaction was completed. LCMS showed desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (Dichloromethane:Methanol=10:1, Rf=0.43, 0-100% (20 min) of Ethyl acetate in Petroleum ether, 100% (10 min) of Ethyl acetate in Petroleum ether) to give benzyl (3S)-4-[[1-[[1-[2-(2,6-dioxo-3-piperidyl)-1,3-dioxo-isoindolin-5-yl]-4-piperidyl]methyl]azetidin-3-yl] methyl]-3-methyl-piperazine-1-carboxylate (150 mg, 212.40 μmol, 44.33% yield, 93% purity) as a yellow oil.

Step 5

To a mixture of benzyl (3S)-4-[[1-[[1-[2-(2,6-dioxo-3-piperidyl)-1,3-dioxo-isoindolin-5-yl]-4-piperidyl]methyl] azetidin-3-yl]methyl]-3-methyl-piperazine-1-carboxylate (150 mg, 228.39 μmol, 1 eq) in TFA (3.34 g, 29.30 mmol, 2.17 mL, 128.28 eq) in one portion at 20° C. under N2. The mixture was stirred at 70° C. for 2 hours to give yellow solution. LCMS showed desired MS. The residue was concentrated in vacuum to give 2-(2,6-dioxo-3-piperidyl)-5-[4-[[3-[[(2S)-2-methylpiperazin-1-yl]methyl]azetidin-1-yl]methyl]-1-piperidyl]isoindoline-1,3-dione (150 mg, 149.86 μmol, 65.62% yield, 75% purity, 2TFA) as a yellow gum.

Step 6

To a mixture of 2-(2,6-dioxo-3-piperidyl)-5-[4-[[3-[[(2S)-2-methylpiperazin-1-yl]methyl]azetidin-1-yl]methyl]-1-piperidyl]isoindoline-1,3-dione (150 mg, 199.82 μmol, 1.00 eq, 2TFA) and 3-(6-chloropyrimidin-4-yl)-5-(1-methylcyclopropoxy)-1H-indazole (60 mg, 199.51 μmol, 1 eq) in DMSO (5 mL) was added DIEA (206.27 mg, 1.60 mmol, 278.00 μL, 8 eq) in one portion at 20° C. under N2. The mixture was stirred at 80° C. for 36 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition:

water (0.225% FA)-ACN; Begin B: 0 End B: 35; FlowRate: 25 mL/min; Gradient Time: 40 min; 100% B Hold Time: 3 min) to give 2-(2,6-dioxo-3-piperidyl)-5-[4-[[3-[[(2S)-2-methyl-4-[6-[5-(1-methylcyclopropoxy)-1H-indazol-3-yl]pyrimidin-4-yl]piperazin-1-yl]methyl]azetidin-1-yl]methyl]-1-piperidyl]isoindoline-1,3-dione (13 mg, 15.85 μmol, 7.94% yield, 95.95% purity) as a yellow solid.

Exemplary Synthesis of Compound 123

Compound 123 was prepared in a manner analogous to compound 122 starting with tert-butyl 3-fluoro-3-(hydroxymethyl)azetidine-1-carboxylate.

Exemplary Synthesis of Compound 124

Step 1

To a solution of methyl 3-formylbicyclo[1.1.1]pentane-1-carboxylate (250 mg, 1.62 mmol, 1 eq) and benzyl piperazine-1-carboxylate (535.80 mg, 2.43 mmol, 470.00 μL, 1.5 eq) in MeOH (5 mL) and HOAc (0.5 mL) was added borane; 2-methylpyridine (520.36 mg, 4.86 mmol, 3 eq). After addition, the reaction solution was stirred at 25° C. for 1 h. LCMS showed desired MS. The reaction mixture was concentrated under reduced pressure. The residue was purified by silica gel column chromatography (0 to 50% ethyl acetate in petroleum ether) to afford benzyl 4-[(3-methoxycarbonyl-1-bicyclo[1.1.1]pentanyl)methyl]piperazine-1-carboxylate (370 mg, 1.03 mmol, 63.66% yield) as a colorless oil.

Step 2

To a solution of benzyl 4-[(3-methoxycarbonyl-1-bicyclo[1.1.1]pentanyl)methyl]piperazine-1-carboxylate (370 mg, 1.03 mmol, 1 eq) in DCM (5 mL) at −78° C. was added DIBAL-H (1 M, 3.10 mL, 3 eq) and the resulting mixture was stirred at −78° C. under N2 for 1 h. Then the reaction was warmed to 25° C. for 12 h. TLC (petroleum ether:ethyl acetate=1:1) showed several new spots. The reaction mixture was quenched by NH4Cl (15 mL) and filtered. The resulting filtrate was extracted with ethyl acetate (50 mL). The organic layer was dried over sodium sulfate and concentrated under reduced pressure. The residue was purified by silica gel column chromatography (0 to 70% ethyl acetate in petroleum ether) to afford benzyl 4-[[3-(hydroxymethyl)-1-bicyclo[1.1.1]pentanyl]methyl]piperazine-1-carboxylate (120 mg, 337.75 μmol, 32.72% yield, 93% purity) as a light yellow oil.

Step 3

To a solution of benzyl 4-[[3-(hydroxymethyl)-1-bicyclo[1.1.1]pentanyl]methyl]piperazine-1-carboxylate (120 mg, 363.17 μmol, 1 eq) in DCM (2 mL) was added DMP (308.07 mg, 726.35 μmol, 224.87 μL, 2 eq). After addition, the reaction mixture was stirred at 25° C. for 1 h. TLC (petroleum ether:ethyl acetate=1:2) showed the reaction completed. The reaction mixture was filtered and filtrate was concentrated under reduced pressure to afford benzyl 4-[(3-formyl-1-bicyclo[1.1.1]pentanyl)methyl]piperazine-1-carboxylate (120 mg, crude) as a yellow gum. The crude product was used for next step directly.

Step 4

To a solution of benzyl 4-[(3-formyl-1-bicyclo[1.1.1]pentanyl)methyl]piperazine-1-carboxylate (120 mg, 365.40 μmol, 1 eq) and tert-butyl piperazine-1-carboxylate (136.11 mg, 730.81 μmol, 2 eq) in MeOH (3 mL) and HOAc (0.3 mL) was added borane; 2-methylpyridine (195.42 mg, 1.83 mmol, 5 eq). After addition, the reaction mixture was stirred at 25° C. for 12 h. TLC (pure ethyl acetate) showed the reaction was completed and several new spots formed. The reaction mixture was neutralized to pH 7 with saturated $NaHCO_3$. The resulting mixture was extracted with ethyl acetate (10 mL*3). The organic layer was dried over sodium sulfate and concentrated under reduced pressure. The residue was purified by silica gel column chromatography (0-100% ethyl acetate in petroleum ether to 0-20% methanol in dichloromethane) to afford benzyl 4-[[3-[(4-tert-butoxycarbonylpiperazin-1-yl)methyl]-1-bicyclo[1.1.1]pentanyl]methyl]piperazine-1-carboxylate (100 mg, 200.54 μmol, 54.88% yield, 100% purity) as a light yellow oil.

Step 5

To a solution of benzyl 4-[[3-[(4-tert-butoxycarbonylpiperazin-1-yl)methyl]-1-bicyclo[1.1.1]pentanyl]methyl]piperazine-1-carboxylate (100 mg, 200.54 μmol, 1 eq) in DCM (2 mL) was added TFA (1.08 g, 9.45 mmol, 0.7 mL, 47.14 eq). After addition, the reaction solution was stirred at 25° C. for 2 hr. LCMS showed the reaction completed. The reaction mixture was concentrated under reduced pressure to afford benzyl 4-[[3-(piperazin-1-ylmethyl)-1-bicyclo[1.1.1]pentanyl]methyl]piperazine-1-carboxylate (100 mg, crude, TFA) as a yellow gum. The crude product was used for next step directly.

Step 6

To a solution of benzyl 4-[[3-(piperazin-1-ylmethyl)-1-bicyclo[1.1.1]pentanyl]methyl]piperazine-1-carboxylate (100 mg, 195.10 μmol, 1 eq, TFA) and 2-(2,6-dioxo-3-piperidyl)-5-fluoro-isoindoline-1,3-dione (53.89 mg, 195.10 μmol, 1 eq) in DMSO (2 mL) was added DIEA (176.51 mg, 1.37 mmol, 237.88 μL, 7 eq). After addition, the reaction solution was stirred at 100° C. for 12 hr. LCMS showed the reaction was completed. After cooling, the reaction mixture was diluted with ethyl acetate (20 mL) and washed with brine (20 mL*2). The organic layer was dried over sodium sulfate and concentrated under reduced pressure. The residue was purified by prep.TLC (Dichloromethane:Methanol=10:1) to afford benzyl 4-[[3-[[4-[2-(2,6-dioxo-3-piperidyl)-1,3-dioxo-isoindolin-5-yl]piperazin-1-yl]methyl]-1-bicyclo[1.1.1]pentanyl]methyl]piperazine-1-carboxylate (50 mg, 75.60 μmol, 38.75% yield, 99% purity) as a yellow solid.

Step 7

A mixture of benzyl 4-[[3-[[4-[2-(2,6-dioxo-3-piperidyl)-1,3-dioxo-isoindolin-5-yl]piperazin-1-yl]methyl]-1-bicyclo[1.1.1]pentanyl]methyl]piperazine-1-carboxylate (50 mg, 76.36 μmol, 1 eq) and TFA (2 mL) was stirred at 80° C. for 1 h. TLC (dichloromethane:methanol=10:1) showed the reaction completed. The reaction mixture was concentrated under reduced pressure to afford 2-(2,6-dioxo-3-piperidyl)-5-[4-[[3-(piperazin-1-ylmethyl)-1-bicyclo[1.1.1]pentanyl]methyl]piperazin-1-yl]isoindoline-1,3-dione (40 mg, crude) as a yellow gum. The crude product was used for next step directly.

Step 8

To a solution of 2-(2,6-dioxo-3-piperidyl)-5-[4-[[3-(piperazin-1-ylmethyl)-1-bicyclo[1.1.1]pentanyl]methyl]piperazin-1-yl]isoindoline-1,3-dione (40.00 mg, 76.83 μmol, 1.00 eq) in DMSO (2 mL) was added 3-(6-chloropyrimidin-4-yl)-5-(1-methylcyclopropoxy)-1H-indazole (23 mg, 76.48 μmol, 1 eq) and DIEA (59.31 mg, 458.86 μmol, 79.93 μL, 6 eq). After addition, the reaction solution was stirred at 90° C. for 12 hr. LCMS showed ~37% of desired MS. After cooling, the reaction mixture was diluted with ethyl acetate (20 mL) and washed with brine (20 mL*2). The organic layer was dried over sodium sulfate and concentrated under reduced pressure. The residue was purified by prep.HPLC (column: 3_Phenomenex Luna C18 75*30 mm*3 um;

mobile phase: [water (0.225% FA)-ACN]; B %: 0%-40%, 40 min) to afford 2-(2,6-dioxo-3-piperidyl)-5-[4-[[3-[[4-[6-[5-(1-methylcyclopropoxy)-2H-indazol-3-yl]pyrimidin-4-yl]piperazin-1-yl]methyl]-1-bicyclo[1.1.1]pentanyl]methyl]piperazin-1-yl]isoindoline-1,3-dione (18.3 mg, 22.99 μmol, 30.06% yield, 98.6% purity) as a yellow solid.

Exemplary Synthesis of Compound 125

Step 1

A mixture of 3-(6-chloropyrimidin-4-yl)-5-(1-methylcyclopropoxy)-2H-indazole (200 mg, 665.02 μmol, 1 eq), 4-(dimethoxymethyl)piperidine (158.83 mg, 997.53 μmol, 1.5 eq) in DMSO (5 mL) was added DIEA (5.94 g, 45.93 mmol, 8.00 mL, 69.06 eq), and then the mixture was stirred at 80° C. for 2 hr under N2. LCMS showed the starting material was consumed completely and desired MS found. TLC (Petroleum ether:Ethyl acetate=1:1) showed one new major point. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel column chromatography (0 to 50% petroleum in ethyl acetate) to give 3-[6-[4-(dimethoxymethyl)-1-piperidyl]pyrimidin-4-yl]-5-(1-methylcyclopropoxy)-1H-indazole (268 mg, 601.17 μmol, 90.40% yield, 95% purity) as a yellow solid.

Step 2

A mixture of 3-[6-[4-(dimethoxymethyl)-1-piperidyl]pyrimidin-4-yl]-5-(1-methylcyclopropoxy)-1H-indazole (140 mg, 330.57 μmol, 1 eq) in THF (2 mL) was added HCl (2 M, 5.09 mL, 30.80 eq), and then the mixture was stirred at 80° C. for 2 hr under N2. LCMS showed the starting material was consumed completely and desired MS found. The residue was poured into $NaHCO_3$ to adjust the pH=7-8. The aqueous phase was extracted with ethyl acetate (10 mL*3). The combined organic phase was washed with brine (10 mL*2), dried with anhydrous Na2SO4, filtered and concentrated in vacuum to give 1-[6-[5-(1-methylcyclopropoxy)-1H-indazol-3-yl]pyrimidin-4-yl]piperidine-4-carbaldehyde (140 mg, 259.64 μmol, 78.54% yield, 70% purity) as a white solid.

Step 3

To a solution of 1-[6-[5-(1-methylcyclopropoxy)-1H-indazol-3-yl]pyrimidin-4-yl]piperidine-4-carbaldehyde (60 mg, 158.97 μmol, 1 eq) and 5-[4-(azetidin-3-ylmethyl)piperazin-1-yl]-2-(2,6-dioxo-3-piperidyl)isoindoline-1,3-dione (80 mg, 194.43 μmol, 1.22 eq) in MeOH (10 mL) and HOAc (1 mL) was added borane; 2-methylpyridine (45 mg, 420.71 μmol, 2.65 eq). After addition, the reaction solution was stirred at 25° C. for 3 h. LCMS showed the reaction completed. The reaction mixture was concentrated under reduced pressure to give a residue. The residue was purified by prep.HPLC (column: 3_Phenomenex Luna C18 75*30 mm*3 um; mobile phase: [water (0.225% FA)-ACN]; B %: 0%-35%, 40 min) to afford 2-(2,6-dioxo-3-piperidyl)-5-[4-[[11-[[1-[6-[5-(1-methylcyclopropoxy)-1H-indazol-3-yl]pyrimidin-4-yl]-4-piperidyl]methyl]azetidin-3-yl]methyl]piperazin-1-yl]isoindoline-1,3-dione (68.3 mg, 87.57 μmol, 55.09% yield, 99.10% purity) as a yellow solid.

Exemplary Synthesis of Compound 126

Step 1

To a solution of tert-butyl 4-(3-hydroxycyclobutoxy)piperidine-1-carboxylate (3 g, 11.06 mmol, 1 eq) and pyridin-4-ol (1.58 g, 16.58 mmol, 1.5 eq) in THF (150 mL) was added PPh3 (4.35 g, 16.58 mmol, 1.5 eq), then the mixture was stirred at 25° C. for 0.5 hour. And DIAD (3.35 g, 16.58 mmol, 3.22 mL, 1.5 eq) was added the above mixture at 0° C. under N2, and then the mixture was stirred at 90° C. under N2 for 16 hours. TLC (pure ethyl acetate) showed the reaction was completed. After cooling, the reaction mixture was concentrated under reduced pressure. The resulting was diluted with 1 M HCl (50 mL) and washed with ethyl acetate (50 mL*2). The aqueous phase was neutralized with 1 M NaOH to pH-7 and extracted with ethyl acetate (40 mL*3). The organic layer was dried over sodium sulfate and concentrated under reduced pressure. The residue was purified by prep.HPLC (column: Phenomenex luna C18 250*80 mm*10 um; mobile phase: [water (0.225% FA)-ACN]; B %: 20%-50%, 15 min) to afford tert-butyl 4-[3-(4-pyridyloxy)cyclobutoxy]piperidine-1-carboxylate (2.7 g, 6.66 mmol, 60.28% yield, 86% purity) as a light yellow oil.

Step 2

To a solution of tert-butyl 4-[3-(4-pyridyloxy)cyclobutoxy]piperidine-1-carboxylate (2.7 g, 7.75 mmol, 1 eq) in tolune (50 mL) was added BnBr (1.33 g, 7.75 mmol, 920.37 μL, 1 eq). After addition, the reaction was stirred at 80° C. for 12 h. After cooling, the reaction mixture was concentrated under reduced pressure. The residue was dissolved in MeOH (50 mL) and washed with petroleum ether (50 mL*3). The MeOH phase was concentrated under reduced pressure to afford tert-butyl 4-[3-(1-benzylpyridin-1-ium-4-yl)oxycyclobutoxy]piperidine-1-carboxylate (3.69 g, crude) as a light yellow gum.

Step 3

To a solution of tert-butyl 4-[3-(1-benzylpyridin-1-ium-4-yl)oxycyclobutoxy]piperidine-1-carboxylate (3.69 g, 8.39 mmol, 1 eq) in EtOH (50 mL) was added NaBH4 (1.020 g, 26.96 mmol, 3.21 eq) at 0° C. After addition, the reaction solution was stirred at 25° C. for 12 h. TLC (petroleum ether:ethyl acetate=5:1) and LCMS showed the reaction was completed. The reaction mixture was diluted with brine (60 mL) and extracted with ethyl acetate (60 mL*3). The organic layer was dried over sodium sulfate and concentrated under reduced pressure. The residue was purified by silica gel column chromatography (0 to 40% ethyl acetate in petroleum ether) to afford tert-butyl 4-[3-[(1-benzyl-3,6-dihydro-2H-pyridin-4-yl)oxy]cyclobutoxy]piperidine-1-carboxylate (1.8 g, 3.90 mmol, 46.51% yield, 96% purity) as a light yellow oil.

Step 4

To a solution of tert-butyl 4-[3-[(1-benzyl-3,6-dihydro-2H-pyridin-4-yl)oxy]cyclobutoxy]piperidine-1-carboxylate (1.8 g, 4.07 mmol, 1 eq) in MeOH (20 mL) was added Pd/C (0.2 g, 10% purity) and Pd(OH)2 (0.2 g, 142.41 μmol, 10% purity) at 25° C. under N2. The suspension was degassed under vacuum and pored with H2 several times. Then the mixture was stirred at 60° C. for 16 h under H2 (50 psi). LCMS showed the reaction completed. After cooling, the reaction mixture was filtered and filtrate was concentrated under reduced pressure to afford tert-butyl 4-[3-(4-piperidyloxy)cyclobutoxy]piperidine-1-carboxylate (1.42 g, 4.01 mmol, 98.50% yield) as a pale red oil.

Step 5

To a solution of tert-butyl 4-[3-(4-piperidyloxy)cyclobutoxy]piperidine-1-carboxylate (200 mg, 564.20 μmol, 1 eq) and 2-(2,6-dioxo-3-piperidyl)-5-fluoro-isoindoline-1,3-dione (155.84 mg, 564.20 μmol, 1 eq) in DMSO (5 mL) was added DIEA (218.76 mg, 1.69 mmol, 294.82 μL, 3 eq). After addition, the reaction mixture was stirred at 100° C. for 12 hr. LCMS showed starting material consumed and desired MS formed. After cooling, the reaction mixture was diluted with ethyl acetate (20 mL) and washed with water (20 mL*2). The organic layer was dried over sodium sulfate and concentrated under reduced pressure. The residue was purified by silica gel column chromatography (0 to 75% ethyl acetate in petroleum ether) to afford tert-butyl 4-[3-[[1-[2-(2,6-dioxo-3-piperidyl)-1,3-dioxo-isoindolin-5-yl]-4-piperidyl]oxy]cyclobutoxy]piperidine-1-carboxylate (300 mg, 382.68 μmol, 67.83% yield, 77.9% purity) as a yellow solid.

Step 6

To a solution of tert-butyl 4-[3-[[1-[2-(2,6-dioxo-3-piperidyl)-1,3-dioxo-isoindolin-5-yl]-4-piperidyl]oxy]cyclobutoxy]piperidine-1-carboxylate (300 mg, 491.24 μmol, 1 eq) in EtOAc (3 mL) was added HCl/EtOAc (4 M, 3 mL, 24.43 eq). After addition, the reaction solution was stirred at 25° C. for 1 h. LCMS showed the reaction completed. The reaction mixture was concentrated under reduced pressure to afford 2-(2,6-dioxo-3-piperidyl)-5-[4-[3-(4-piperidyloxy)cyclobutoxy]-1-piperidyl]isoindoline-1,3-dione (260 mg, 384.98 μmol, 78.37% yield, 81% purity, HCl) as a yellow solid. The crude product was used for next step directly.

Step 7

To a solution of 2-(2,6-dioxo-3-piperidyl)-5-[4-[3-(4-piperidyloxy)cyclobutoxy]-1-piperidyl]isoindoline-1,3-dione (84.89 mg, 166.26 μmol, 1 eq) and 3-(6-chloropyrimidin-4-yl)-5-(1-methylcyclopropoxy)-1H-indazole (50 mg, 166.26 μmol, 1 eq) in DMSO (2 mL) was added DIEA (107.44 mg, 831.28 μmol, 144.79 μL, 5 eq). After addition, the reaction solution was stirred at 90° C. for 12 h. LCMS showed the reaction completed. After cooling, the reaction solution was diluted with water (10 mL) and extracted with dichloromethane (10 mL*3). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 10%-50%, 40 min) to afford 2-(2,6-dioxo-3-piperidyl)-5-[4-[3-[[1-[6-[5-(1-methylcyclopropoxy)-1H-indazol-3-yl]pyrimidin-4-yl]-4-piperidyl]oxy]cyclobutoxy]-1-piperidyl]isoindoline-1,3-dione (37.7 mg, 48.02 μmol, 28.88% yield, 98.7% purity) as a yellow solid.

Exemplary Synthesis of Compound 127

Step 1

To a solution of tert-butyl 4-[3-(4-piperidyloxy)cyclobutoxy]piperidine-1-carboxylate (320 mg, 902.72 μmol, 1 eq) and 4-bromo-2-fluoro-pyridine (320 mg, 1.82 mmol, 2.01 eq) in $CH_3CN$ (5 mL) was added $Cs_2CO_3$ (588.25 mg, 1.81 mmol, 2 eq). After addition, the reaction mixture was stirred at 80° C. for 12 hr. LCMS showed the reaction completed. After cooling, the reaction mixture was filtered and filtrate was concentrated under reduced pressure. The residue was purified by silica gel column chromatography (0 to 50% ethyl acetate in petroleum ether) to afford tert-butyl 4-[3-[[1-(4-bromo-2-pyridyl)-4-piperidyl]oxy]cyclobutoxy]piperidine-1-carboxylate (240 mg, 446.65 μmol, 49.48% yield, 95% purity) as a white solid.

Step 2

To a mixture of tert-butyl 4-[3-[[1-(4-bromo-2-pyridyl)-4-piperidyl]oxy]cyclobutoxy]piperidine-1-carboxylate (240 mg, 470.16 μmol, 1 eq) and Pin2B2 (238.78 mg, 940.32 μmol, 2 eq) in dioxane (5 mL) was added KOAc (92.29 mg, 940.32 μmol, 2 eq) and Pd(dppf)Cl2 (17.20 mg, 23.51 μmol, 0.05 eq) in one portion at 25° C. under N2. The mixture was stirred at 100° C. for 16 h. LCMS showed desired MS. The reaction mixture was concentrated under reduced pressure to remove solvent to afford tert-butyl 4-[3-[[1-[4-(4,4,5,5-tetramethyl-1,3,2-dioxaborolan-2-yl)-2-pyridyl]-4-piperidyl]oxy]cyclobutoxy]piperidine-1-carboxylate (500 mg, crude) as a black oil.

Step 3

To a solution of tert-butyl 4-[3-[[1-[4-(4,4,5,5-tetramethyl-1,3,2-dioxaborolan-2-yl)-2-pyridyl]-4-piperidyl]oxy]cyclobutoxy]piperidine-1-carboxylate (262.00 mg, 469.93 μmol, 2.09 eq) in dioxane (5 mL) and H2O (1 mL) was added 2-[[3-iodo-5-(1-methylcyclopropoxy)indazol-1-yl]methoxy]ethyl-trimethyl-silane (100 mg, 225.03 μmol, 1 eq), Pd(dppf)Cl2 (8.23 mg, 11.25 μmol, 0.05 eq) and Na2CO3 (71.55 mg, 675.10 μmol, 3 eq). After addition, the reaction mixture was stirred at 90° C. under N2 for 16 h. LCMS showed desired MS. After cooling, the reaction mixture was filtered to remove insoluble substance and filtrate was concentrated under reduced pressure. The residue was purified by silica gel chromatography (12 g, 0-30% (8 min) of Ethyl acetate in Petroleum ether, 30% (10 min) of Ethyl acetate in Petroleum ether) to afford tert-butyl 4-[3-[[1-[4-[5-(1-methylcyclopropoxy)-1-(2-trimethylsilylethoxymethyl)indazol-3-yl]-2-pyridyl]-4-piperidyl]oxy]cyclobutoxy]piperidine-1-carboxylate (200 mg, crude) as a yellow gum.

Step 4

To a mixture of tert-butyl 4-[3-[[1-[4-[5-(1-methylcyclopropoxy)-1-(2-trimethylsilylethoxymethyl)indazol-3-yl]-2-pyridyl]-4-piperidyl]oxy]cyclobutoxy]piperidine-1-carboxylate (200 mg, 267.37 μmol, 1 eq) in MeOH (3 mL) was added HCl/dioxane (4 M, 3 mL, 44.88 eq). The mixture was stirred at 65° C. for 30 min. TLC showed the reaction was completed. The reaction mixture was concentrated under reduced pressure to remove solvent to afford 5-(1-methylcyclopropoxy)-3-[2-[4-[3-(4-piperidyloxy)cyclobutoxy]-1-piperidyl]-4-pyridyl]-1H-indazole (138 mg, crude, HCl) as a yellow solid.

Step 5

To a solution of 5-(1-methylcyclopropoxy)-3-[2-[4-[3-(4-piperidyloxy)cyclobutoxy]-1-piperidyl]-4-pyridyl]-1H-indazole (138 mg, 266.58 μmol, 1 eq) and 2-(2,6-dioxo-3-piperidyl)-5-fluoro-isoindoline-1,3-dione (73.64 mg, 266.58 μmol, 1 eq) in DMSO (3 mL) was added DIEA (172.27 mg, 1.33 mmol, 232.17 μL, 5 eq). After addition, the mixture was stirred at 100° C. for 16 hours. LCMS showed desired MS. The residue was poured into water (10 mL). The aqueous phase was extracted with ethyl acetate (10 mL*3). The combined organic phase was washed with brine (20 mL*2), dried with anhydrous Na2SO4, filtered and concentrated in vacuum. The residue was purified by prep.HPLC (column: 3_Phenomenex Luna C18 75*30 mm*3 um; mobile phase: [water (0.225% FA)-ACN]; B %: 10%-60%, 40 min) to afford 2-(2,6-dioxo-3-piperidyl)-5-[4-[3-[[1-[4-[5-(1-methylcyclopropoxy)-1H-indazol-3-yl]-2-pyridyl]-4-piperidyl]oxy]cyclobutoxy]-1-piperidyl]isoindoline-1,3-dione (21.2 mg, 26.71 μmol, 10.02% yield, 97.5% purity) as a yellow solid.

Exemplary Synthesis of Compound 128

Compound 128 was prepared in a manner analogous to compound 78 starting with azetidin-3-ylmethanol.

Exemplary Synthesis of Compound 129

Step 1

To a mixture of 2-(2,6-dioxo-3-piperidyl)-5-[4-(piperazin-1-ylmethyl)-1-piperidyl]isoindoline-1,3-dione (250 mg, 568.82 μmol, 1 eq), tert-butyl 3-(p-tolylsulfonyloxymethyl)azetidine-1-carboxylate (233.05 mg, 682.58 μmol, 1.2 eq) and KI (472.12 mg, 2.84 mmol, 5 eq) in MeCN (5 mL) was added DIEA (367.57 mg, 2.84 mmol, 495.38 μL, 5 eq) in one portion at 25° C. The mixture was stirred at 100° C. for 12 hours. TLC (Dichloromethane:Methanol=10/1) showed the reaction was completed. The mixture was cooled to 25° C. and concentrated in reduced pressure. The residue was purified by silica gel chromatography (Dichloromethane/Methanol=10/1) to afford tert-butyl 3-[[4-[[1-[2-(2,6-dioxo-3-piperidyl)-1,3-dioxo-isoindolin-5-yl]-4-piperidyl]methyl]piperazin-1-yl]methyl]azetidine-1-carboxylate (300 mg, 482.98 μmol, 84.91% yield, 98% purity) as yellow solid.

Step 2

To a mixture of tert-butyl 3-[[4-[[1-[2-(2,6-dioxo-3-piperidyl)-1,3-dioxo-isoindolin-5-yl]-4-piperidyl]methyl]piperazin-1-yl]methyl]azetidine-1-carboxylate (150 mg, 246.42 μmol, 1 eq) in DCM (2 mL) was added TFA (1.54 g, 13.51 mmol, 1 mL, 54.81 eq) in one portion. The mixture was stirred at 25° C. for 1 hours. TLC (Dichloromethane:Methanol=10/1) showed the reaction was completed. The mixture was concentrated in reduced pressure at 35° C. The crude product was used into the next step without further purification. The product 5-[4-[[4-(azetidin-3-ylmethyl)piperazin-1-yl]methyl]-1-piperidyl]-2-(2,6-dioxo-3-piperidyl)isoindoline-1,3-dione (100 mg, 188.75 μmol, 76.60% yield, 96% purity) as light yellow oil.

Step 3

To a mixture of 5-[4-[[4-(azetidin-3-ylmethyl)piperazin-1-yl]methyl]-1-piperidyl]-2-(2,6-dioxo-3-piperidyl)isoindoline-1,3-dione (100 mg, 196.61 μmol, 1 eq) and 3-(6-chloropyrimidin-4-yl)-5-(1-methylcyclopropoxy)-2H-indazole (59.13 mg, 196.61 μmol, 1 eq) in DMSO (2 mL) was added DIEA (254.11 mg, 1.97 mmol, 342.47 μL, 10 eq) in one portion. The mixture was stirred at 84° C. for 3 hours. LCMS showed the reaction EB153-509-P1 was remained 9% and the desired product was produced 51%. The mixture was cooled to 25° C. and poured into water (10 mL). The aqueous phase was extracted with ethyl acetate (20 mL*2). The combined organic phase was washed with brine (10 mL*2), dried with anhydrous Na2SO4, filtered and concentrated in vacuum. The residue was purified by prep-HPLC (column: Phenomenex Luna C18 75*30 mm*3 um; mobile phase: [water (0.225% FA)-ACN]; B %: 0%-40%, 35 min) to afford 2-(2,6-dioxo-3-piperidyl)-5-[4-[[4-[[1-[6-[5-(1-methylcyclopropoxy)-1H-indazol-3-yl]pyrimidin-4-yl]azetidin-3-yl]methyl]piperazin-1-yl]methyl]-1-piperidyl]isoindoline-1,3-dione (45.7 mg, 55.53 μmol, 28.24% yield, 99.5% purity, FA) as yellow solid.

Exemplary Synthesis of Compound 130

Step 1 tert-butyl 3-hydroxyazetidine-1-carboxylate (5 g, 28.87 mmol, 1 eq), pyridin-4-ol (2.75 g, 28.87 mmol, 1 eq) and PPh3 (8.33 g, 31.75 mmol, 1.1 eq) were added to THF (50 mL) and stirred for 30 minutes. To this was dropwise added DIAD (6.42 g, 31.75 mmol, 6.17 mL, 1.1 eq) at 0° C. Once the addition was complete the reaction was stirred at 50° C. for 15.5 hour. TLC (Dichloromethane:Methanol=10:1, Rf=0.45) showed the reaction was completed. LCMS showed there was desired MS. Solvent was evaporated in vacuo. The resulting oil was treated with a 1.0 M HCl aqueous solution (100 mL). The acidic mixture was washed with CH2Cl2 (100 mL×2). The combined CH2Cl2 washings were re-extracted with a 1.0 M HCl aqueous solution (100 mL) and H2O (200 mL), then discarded. The aqueous fractions were combined, basified to pH~12 using a 1.0 M NaOH aqueous solution, and extracted with CH2Cl2 (50 mL×4). The organic extracts were washed with brine, dried over anhydrous Na2SO4, and concentrated in vacuo to a residue. The residue was purified by silica gel chromatography (40 g, 100-200 mesh silica gel, 0-100% (20 min) of Ethyl acetate in Petroleum ether) to give tert-butyl 3-(4-pyridyloxy)azetidine-1-carboxylate (1.8 g, 7.19 mmol, 24.91% yield) as yellow oil.

Step 2

To a solution of tert-butyl 3-(4-pyridyloxy)azetidine-1-carboxylate (1.8 g, 7.19 mmol, 1 eq) in EtOH (20 mL) and HOAc (431.85 mg, 7.19 mmol, 411.29 μL, 1 eq) was added Pt2O (257.73 mg, 7.19 mmol, 1 eq) at 25° C. Then the mixture was stirred at 70° C. for 16 h under H2 (50 psi). TLC showed the reaction was completed. The suspension was filtered through a pad of Celite and the pad or filter cake was washed with EtOH (100 mL×3). The combined filtrates were concentrated to dryness to give tert-butyl 3-(4-piperidyloxy)azetidine-1-carboxylate (2.1 g, crude) as a colorless oil Step 3

To a mixture of tert-butyl 3-(4-piperidyloxy)azetidine-1-carboxylate (208.20 mg, 812.19 μmol, 2 eq) and 1-[2-(2,6-dioxo-3-piperidyl)-1,3-dioxo-isoindolin-5-yl]piperidine-4-carbaldehyde (150 mg, 406.10 μmol, 1 eq) in MeOH (5 mL) was added borane; 2-methylpyridine (86.87 mg, 812.19 μmol, 2 eq) and HOAc (0.5 mL) in one portion at 20° C. under N2. The mixture was stirred at 20° C. for 1 h to give yellow solution. LCMS showed there was ~50% of desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (12 g, 0-100% (15 min) of Ethyl acetate in Petroleum ether, 100% (15 min) of Ethyl acetate in Petroleum ether) to give tert-butyl 3-[[1-[[1-[2-(2,6-dioxo-3-piperidyl)-1,3-dioxo-isoindolin-5-yl]-4-piperidyl]methyl]-4-piperidyl]oxy]azetidine-1-carboxylate (130 mg, 213.22 μmol, 52.50% yield) as a yellow solid.

Step 4

To a mixture of tert-butyl 3-[[1-[[1-[2-(2,6-dioxo-3-piperidyl)-1,3-dioxo-isoindolin-5-yl]-4-piperidyl]methyl]-4-piperidyl]oxy]azetidine-1-carboxylate (130 mg, 213.22 μmol, 1 eq) in DCM (5 mL) was added TFA (3.41 g, 29.94 mmol, 2.22 mL, 140.41 eq) in one portion at 20° C. The mixture was stirred at 20° C. for 0.5 h. TLC (Dichloromethane:Methanol=10:1, Rf=0.03) showed the reaction was completed. The mixture was concentrated in vacuum to give 5-[4-[[4-(azetidin-3-yloxy)-1-piperidyl]methyl]-1-piperidyl]-2-(2,6-dioxo-3-piperidyl)isoindoline-1,3-dione (120 mg, 169.33 μmol, 79.42% yield, 88% purity, TFA) as a yellow gum.

Step 5

To a mixture of 5-[4-[[4-(azetidin-3-yloxy)-1-piperidyl]methyl]-1-piperidyl]-2-(2,6-dioxo-3-piperidyl)isoindoline-1,3-dione (120 mg, 192.43 μmol, 1.16 eq, TFA) and 3-(6-chloropyrimidin-4-yl)-5-(1-methylcyclopropoxy)-1H-indazole (50 mg, 166.26 μmol, 1 eq) in DMSO (5 mL) was added DIEA (1.48 g, 11.48 mmol, 2 mL, 69.07 eq) in one portion at 20° C. under N2. The mixture was stirred at 80° C. for 16 h. LCMS showed there was desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (column: 3_Phenomenex Luna C18 75*30 mm*3 um; mobile phase: [water (0.225% FA)-ACN]; B %: 0%-35%, 40 min) to give 2-(2,6-dioxo-3-piperidyl)-5-[4-[[4-[1-[6-[5-(1-methylcyclopropoxy)-2H-indazol-3-yl] pyrimidin-4-yl]azetidin-3-yl]oxy-1-piperidyl]methyl]-1-piperidyl]isoindoline-1,3-dione (72.1 mg, 93.06 μmol, 55.98% yield, 99.89% purity) as a yellow solid.

Exemplary Synthesis of Compound 131

Step 1

To a mixture of tert-butyl 3-fluoro-3-(hydroxymethyl) azetidine-1-carboxylate (500 mg, 2.44 mmol, 1 eq) and TEA (739.60 mg, 7.31 mmol, 1.02 mL, 3 eq) in DCM (10 mL) was added TosCl (696.73 mg, 3.65 mmol, 1.5 eq) and DMAP (29.76 mg, 243.63 μmol, 0.1 eq) in one portion at 0° C. under N2. The mixture was stirred at 25° C. for 12 hours. TLC showed the reaction was completed. The mixture was concentrated in vacuum. The residue was purified by silica gel chromatography (Petroleum ether/Ethyl acetate=100/1, 1/1) to afford tert-butyl 3-fluoro-3-(p-tolylsulfonyloxymethyl)azetidine-1-carboxylate (800 mg, 2.09 mmol, 85.88% yield, 94% purity) as yellow solid.

Step 2

To a mixture of benzyl piperazine-1-carboxylate (520.93 mg, 2.36 mmol, 456.95 μL, 1 eq) and tert-butyl 3-fluoro-3-(p-tolylsulfonyloxymethyl)azetidine-1-carboxylate (850 mg, 2.36 mmol, 1 eq) in DMSO (3 mL) was added DIEA (1.53 g, 11.82 mmol, 2.06 mL, 5 eq) in one portion at 25° C. under N2. The mixture was stirred at 90° C. for 12 hours. TLC showed desired product was formed. The residue was poured into ethyl acetate (30 mL). The combined organic phase was washed with brine (30 mL*3), dried with anhydrous Na2SO4, filtered and concentrated in vacuum. The residue was purified by silica gel chromatography (Petroleum ether/Ethyl acetate=100/1, 1/1) to afford benzyl 4-[(1-tert-butoxycarbonyl-3-fluoro-azetidin-3-yl)methyl]piperazine-1-carboxylate (900 mg, 2.21 mmol, 93.39% yield) as yellow oil.

Step 3

To a mixture of benzyl 4-[(1-tert-butoxycarbonyl-3-fluoro-azetidin-3-yl)methyl]piperazine-1-carboxylate (200 mg, 490.82 μmol, 1 eq) in DCM (4 mL) was added TFA (1.54 g, 13.51 mmol, 1 mL, 27.52 eq) in one portion at 25° C. under N2. The mixture was stirred at 25° C. for 2 hours. TLC showed the reaction was completed. The mixture was concentrated in vacuum to afford benzyl 4-[(3-fluoroazetidin-3-yl)methyl]piperazine-1-carboxylate (200 mg, 365.46 μmol, 74.46% yield, 77% purity, TFA) as yellow solid.

Step 4

To a mixture of benzyl 4-[(3-fluoroazetidin-3-yl)methyl] piperazine-1-carboxylate (200 mg, 474.63 μmol, 1 eq, TFA) and 2-[[3-(6-chloropyrimidin-4-yl)-5-(1-methylcyclopropoxy)indazol-2-yl]methoxy]ethyl-trimethyl-silane (409.13 mg, 474.63 μmol, 50% purity, 1 eq) in DMSO (5 mL) was added DIEA (613.43 mg, 4.75 mmol, 826.72 μL, 10 eq) in one portion at 25° C. under N2. The mixture was stirred at 90° C. for 12 hours. TLC showed the reaction was completed. The mixture was poured into ethyl acetate (20 mL). The combined organic phase was washed with brine (20 mL*3), dried with anhydrous Na2SO4, filtered and concentrated in vacuum. The residue was purified by silica gel chromatography (Petroleum ether/Ethyl acetate=100/1, 1/1) to afford benzyl 4-[[3-fluoro-1-[6-[5-(1-methylcyclopropoxy)-2-(2-trimethylsilylethoxymethyl)indazol-3-yl]pyrimidin-4-yl]azetidin-3-yl]methyl]piperazine-1-carboxylate (300 mg, 414.59 μmol, 87.35% yield, 97% purity) as a yellow solid.

Step 5

A mixture of benzyl 4-[[3-fluoro-1-[6-[5-(1-methylcyclopropoxy)-2-(2-trimethylsilylethoxymethyl)indazol-3-yl]pyrimidin-4-yl]azetidin-3-yl]methyl]piperazine-1-carboxylate (70 mg, 99.73 μmol, 1 eq) in TFA (3 mL) was stirred at 70° C. for 1 hours. TLC showed the reaction was completed. The mixture was concentrated in reduced pressure. The residue was poured into THF (5 mL) and NH3H2O (1 mL). The mixture was stirred at 25° C. for 20 min, dried with anhydrous Na2SO4, filtered and concentrated in vacuum to afford 3-[6-[3-fluoro-3-(piperazin-1-ylmethyl)azetidin-1-yl] pyrimidin-4-yl]-5-(1-methylcyclopropoxy)-2H-indazole (50 mg, 51.67 μmol, 51.81% yield, 57% purity, TFA) as yellow solid.

Step 6

To a mixture of 3-[6-[3-fluoro-3-(piperazin-1-ylmethyl) azetidin-1-yl]pyrimidin-4-yl]-5-(1-methylcyclopropoxy)-2H-indazole (50 mg, 90.66 μmol, 1 eq, TFA) and 1-[2-(2,6-dioxo-3-piperidyl)-1,3-dioxo-isoindolin-5-yl]piperidine-4-carbaldehyde (33.49 mg, 90.66 μmol, 1 eq) in MeOH (10 mL) and CH3COOH (1 mL) was added (2-methylpyridin-1-ium-1-yl)boranuide (29.09 mg, 271.97 μmol, 3 eq) in one portion at 25° C. under N2. The mixture was stirred at 25° C. for 12 hours. TLC showed the reaction was completed. The mixture was concentrated in vacuum. The residue was purified by prep-HPLC (column: 3_Phenomenex Luna C18 75*30 mm*3 um; mobile phase: [water (0.225% FA)-ACN]; B %: 0%-35%, 40 min and column: 3_Phenomenex Luna C18 75*30 mm*3 um; mobile phase: [water (10 mM NH4HCO3)-ACN]; B %: 20%-70%, 40 min) to afford 2-(2,6-dioxo-3-piperidyl)-5-[4-[[4-[[3-fluoro-1-[6-[5-(1-methylcyclopropoxy)-2H-indazol-3-yl]pyrimidin-4-yl]azetidin-3-yl]methyl]piperazin-1-yl]methyl]-1-piperidyl]isoindoline-1,3-dione (14.4 mg, 18.03 μmol, 19.88% yield, 99% purity) as yellow solid.

Exemplary Synthesis of Compound 132

Compound 132 was prepared in a manner analogous to compound 78 starting with afford benzyl 4-[(3-fluoroazetidin-3-yl)methyl]piperazine-1-carboxylate.

Exemplary Synthesis of Compound 133

Step 1

To a solution of tert-butyl 3-(hydroxymethyl) azetidine-1-carboxylate (1 g, 5.34 mmol, 1 eq) in DCM (3 mL) was added TFA (4.62 g, 40.52 mmol, 3 mL, 7.59 eq). The mixture was stirred at 25° C. for 1 hr. LC-MS (EB2049-122-P1A) showed Reactant 1 was consumed completely and desired mass was detected. The reaction mixture was concentrated under reduced pressure to remove solvent to afford azetidin-3-ylmethanol (1 g, 4.97 mmol, 93.09% yield, TFA) as a light yellow oil. The crude product was used into the next step without further purification.

Step 2

To a solution of azetidin-3-ylmethanol (1 g, 4.97 mmol, 1 eq, TFA) and 2-(2,6-dioxo-3-piperidyl)-5-fluoro-isoindoline-1,3-dione (1.37 g, 4.97 mmol, 1 eq) in DMSO (6 mL) was added DIEA (3.21 g, 24.86 mmol, 4.33 mL, 5 eq). The mixture was stirred at 100° C. for 16 hr. LC-MS (EB2049-123-P1A) showed Reactant 1 was consumed completely and desired mass was detected. The reaction mixture was diluted with water (20 mL) and extracted with EA (30 mL). The combined organic layers were washed with brine (20 mL), dried over Na2SO4, filtered and concentrated under reduced pressure to give a residue. The residue was purified by flash silica gel chromatography (ISCO®; 12 g SepaFlash® Silica Flash Column, Eluent of 0-50% Ethyl acetate/Petroleum ether gradient @ 45 mL/min) to afford 2-(2, 6-dioxo-3-piperidyl)-5-[3-(hydroxymethyl) azetidin-1-yl] isoindoline-1, 3-dione (520 mg, 1.51 mmol, 30.46% yield) as a yellow solid Step 3

To a solution of 2-(2,6-dioxo-3-piperidyl)-5-[3-(hydroxymethyl)azetidin-1-yl]isoindoline-1,3-dione (500 mg, 1.46 mmol, 1 eq) in DCM (5 mL) was added DMAP (35.58 mg, 291.26 μmol, 0.2 eq), Toscl (555.29 mg, 2.91 mmol, 2 eq) and TEA (294.73 mg, 2.91 mmol, 405.40 μL, 2 eq). The mixture was stirred at 25° C. for 16 hr. LC-MS (EB2049-124-P1A) showed Reactant 1 was consumed completely and desired mass was detected. The reaction mixture was concentrated under reduced pressure to remove solvent. The residue was purified by flash silica gel chromatography (ISCO®; 12 g SepaFlash® Silica Flash Column, Eluent of 0-100% Ethyl acetate/Petroleum ether gradient @ 45 mL/min) to afford [1-[2-(2, 6-dioxo-3-piperidyl)-1, 3-dioxo-isoindolin-5-yl] azetidin-3-yl] methyl 4-methylbenzenesulfonate (186 mg, 373.85 μmol, 25.67% yield) as a yellow solid Step 4

To a solution of tert-butyl 4-(4-piperidylmethyl)piperazine-1-carboxylate (98.63 mg, 348.03 μmol, 1.5 eq) and 2-[[3-(6-chloropyrimidin-4-yl)-5-(1-methylcyclopropoxy) indazol-2-yl]methoxy]ethyl-trimethyl-silane (100 mg, 232.02 μmol, 1 eq) in DMSO (3 mL) was added DIEA (89.96 mg, 696.05 μmol, 121.24 μL, 3 eq). The mixture was stirred at 100° C. for 1 hr. LC-MS (EB2049-126-P1B) showed Reactant 1 was consumed completely and desired mass was detected. The mixture was cooled to room temperature and concentrated, and then the residue was quenched with sat.$NaHCO_3$ (30 mL) and extracted with EtOAc (30 mL). The organic layer was washed with water (30 mL×2), brine (30 mL×2), dried over anhydrous Na2SO4, filtered and concentrated in vacuo. The residue was purified by flash silica gel chromatography (ISCO®; 12 g SepaFlash® Silica Flash Column, Eluent of 0-35% Ethyl acetate/Petroleum ether gradient @ 45 mL/min) to afford tert-butyl 4-[[1-[6-[5-(1-methylcyclopropoxy)-2-(2-trimethylsilylethoxymethyl)indazol-3-yl]pyrimidin-4-yl]-4-piperidyl]methyl]piperazine-1-carboxylate (107 mg, 157.83 μmol, 68.02% yield) as a light yellow oil.

Step 5

To a solution of tert-butyl 4-[[1-[6-[5-(1-methylcyclopropoxy)-2-(2-trimethylsilylethoxymethyl) indazol-3-yl] pyrimidin-4-yl]-4-piperidyl] methyl] piperazine-1-carboxylate (107 mg, 157.83 μmol, 1 eq) in MeOH (3 mL) was added HCl/dioxane (4 M, 39.46 μL, 1 eq). The mixture was stirred at 65° C. for 0.5 hr. LC-MS (EB2049-128-P1A) showed Reactant 1 was consumed completely and one desired mass was detected. The reaction mixture was concentrated under reduced pressure to remove solvent to afford 5-(1-methylcyclopropoxy)-3-[6-[4-(piperazin-1-ylmethyl)-1-piperidyl]pyrimidin-4-yl]-2H-indazole (80 mg, 139.87 μmol, 88.62% yield, 91% purity, 2 HCl) as a light yellow oil. The crude product was used into the next step without further purification.

Step 6

To a solution of 5-(1-methylcyclopropoxy)-3-[6-[4-(piperazin-1-ylmethyl)-1-piperidyl]pyrimidin-4-yl]-2H-indazole (80 mg, 165.28 μmol, 1 eq, HCl) and [1-[2-(2,6-dioxo-3-piperidyl)-1,3-dioxo-isoindolin-5-yl]azetidin-3-yl]methyl 4-methylbenzenesulfonate (82.23 mg, 165.28 μmol, 1 eq) in MeCN (3 mL) was added KI (274.36 mg, 1.65 mmol, 10 eq) and DIEA (213.61 mg, 1.65 mmol, 287.88 μL, 10 eq). The mixture was stirred at 100° C. for 16 hr. LC-MS (EB2049-129-P1C) showed Reactant 1 was consumed completely and desired mass was detected. The reaction mixture was concentrated under reduced pressure to remove solvent. The crude product was purified by reversed-phase HPLC (column: 3_Phenomenex Luna C18 75*30 mm*3 um; mobile phase: [water (0.225% FA)-ACN]; B %: 0%-40%, 40 min) to afford 2-(2,6-dioxo-3-piperidyl)-5-[3-[[4-[[1-[6-[5-(1-methylcyclopropoxy)-1H-indazol-3-yl]pyrimidin-4-yl]-4-piperidyl]methyl]piperazin-1-yl]methyl]azetidin-1-yl]isoindoline-1,3-dione (26.6 mg, 33.73 μmol, 20.41% yield, 98% purity) as a yellow solid Exemplary Synthesis of Compound 134

Step 1

To a mixture of 1-[6-[5-(1-methylcyclopropoxy)-2H-indazol-3-yl]pyrimidin-4-yl]piperidine-4-carbaldehyde (100 mg, 264.94 μmol, 1 eq) and tert-butyl 3-fluoro-3-(piperazin-1-ylmethyl)azetidine-1-carboxylate (72.42 mg, 264.94 μmol, 1 eq) in MeOH (10 mL) and CH3COOH (1 mL) was added (2-methylpyridin-1-ium-1-yl)boranuide (85.02 mg, 794.83 μmol, 3 eq) in one portion at 25° C. under N2. The mixture was stirred at 25° C. for 12 hours. TLC showed the reaction was completed. The mixture was concentrated in vacuum. The residue was purified by silica gel chromatography (DCM/MeOH=100/1, 10/1) to afford tert-butyl 3-fluoro-3-[[4-[[1-[6-[5-(1-methylcyclopropoxy)-2H-indazol-3-yl]pyrimidin-4-yl]-4-piperidyl]methyl]piperazin-1-yl] methyl]azetidine-1-carboxylate (110 mg, 86.64 μmol, 32.70% yield, 50% purity) as yellow solid.

Step 2

To a mixture of tert-butyl 3-fluoro-3-[[4-[[1-[6-[5-(1-methylcyclopropoxy)-2H-indazol-3-yl]pyrimidin-4-yl]-4-piperidyl]methyl]piperazin-1-yl]methyl]azetidine-1-carboxylate (100 mg, 78.77 μmol, 50% purity, 1 eq) in DCM (4 mL) was added TFA (1.54 g, 13.51 mmol, 1 mL, 171.47 eq) in one portion at 25° C. under N2. The mixture was stirred at 25° C. for 2 hours. TLC showed the reaction was completed. The mixture was concentrated in vacuum to afford 3-[6-[4-[[4-[(3-fluoroazetidin-3-yl)methyl]piperazin-1-yl]methyl]-1-piperidyl]pyrimidin-4-yl]-5-(1-methylcyclopropoxy)-2H-indazole (100 mg, crude, TFA) as yellow oil.

Step 3

To a mixture of 3-[6-[4-[[4-[(3-fluoroazetidin-3-yl) methyl]piperazin-1-yl]methyl]-1-piperidyl]pyrimidin-4-yl]-5-(1-methylcyclopropoxy)-2H-indazole (100 mg, 77.08 μmol, 50% purity, 1 eq, TFA) and 2-(2,6-dioxo-3-piperidyl)-5-fluoro-isoindoline-1,3-dione (27.68 mg, 100.20 μmol, 1.3 eq) in DMSO (3 mL) was added DIEA (99.62 mg, 770.78 μmol, 134.26 μL, 10 eq) in one portion at 25° C. under N2. The mixture was stirred at 100° C. for 12 hours. TLC showed the reaction was completed. The mixture was concentrated in vacuum. The mixture was purified by prep-HPLC (column: 3_Phenomenex Luna C18 75*30 mm*3 um; mobile phase: [water (10 mM NH4HCO3)-ACN]; B %: 30%-80%, 40 min) to afford 2-(2,6-dioxo-3-piperidyl)-5-[3-fluoro-3-[[4-[[1-[6-[5-(1-methylcyclopropoxy)-2H-indazol-3-yl]pyrimidin-4-yl]-4-piperidyl]methyl]piperazin-1-yl] methyl]azetidin-1-yl]isoindoline-1,3-dione (10.6 mg, 13.13 μmol, 17.04% yield, 98% purity) as yellow solid.

Exemplary Synthesis of Compound 135

Step 1

To a solution of tert-butyl 4-fluoro-4-(piperazin-1-ylmethyl)piperidine-1-carboxylate (139.86 mg, 464.03 μmol, 2 eq) and 2-[[3-(6-chloropyrimidin-4-yl)-5-(1-methylcyclopropoxy)indazol-2-yl]methoxy]ethyl-trimethyl-silane (100 mg, 232.02 μmol, 1 eq) in DMSO (3 mL) was added DIEA (371.00 mg, 2.87 mmol, 0.5 mL, 12.37 eq). After addition, the reaction solution was stirred at 100° C. for 2 h. LCMS showed desired MS. The residue was poured into water (15 mL). The aqueous phase was extracted with ethyl acetate (15 mL*3). The combined organic phase was washed with brine (15 mL*2), dried with anhydrous Na2SO4, filtered and concentrated in vacuum. The residue was purified by silica gel chromatography (12 g, 0-37% (10 min) of Ethyl acetate in Petroleum ether, 37% (10 min) of Ethyl acetate in Petroleum ether) to afford tert-butyl 4-fluoro-4-[[4-[6-[5-(1-methylcyclopropoxy)-2-(2-trimethylsilylethoxymethyl)indazol-3-yl]pyrimidin-4-yl]piperazin-1-yl]methyl]piperidine-1-carboxylate (140 mg, 181.05 μmol, 78.03% yield, 90% purity) as a yellow oil.

Step 2

To a mixture of tert-butyl 4-fluoro-4-[[4-[6-[5-(1-methylcyclopropoxy)-2-(2-trimethylsilylethoxymethyl)indazol-3-yl]pyrimidin-4-yl]piperazin-1-yl]methyl]piperidine-1-carboxylate (140 mg, 201.17 μmol, 1 eq) in MeOH (2 mL) was added HCl/dioxane (4 M, 2 mL, 39.77 eq). The mixture was stirred at 65° C. for 30 min. LCMS showed desired MS. The reaction mixture was concentrated under reduced pressure to remove solvent to afford 3-[6-[4-[(4-fluoro-4-piperidyl)methyl]piperazin-1-yl]pyrimidin-4-yl]-5-(1-methylcyclopropoxy)-2H-indazole (93 mg, crude, HCl) as a white solid.

Step 3

To a solution of 3-[6-[4-[(4-fluoro-4-piperidyl)methyl]piperazin-1-yl]pyrimidin-4-yl]-5-(1-methylcyclopropoxy)-2H-indazole (93.66 mg, 201.17 μmol, 1 eq) and [1-[2-(2,6-dioxo-3-piperidyl)-1,3-dioxo-isoindolin-5-yl]azetidin-3-yl]methyl 4-methylbenzenesulfonate (100.09 mg, 201.17 μmol, 1 eq) in MeCN (3 mL) was added DIEA (130.00 mg, 1.01 mmol, 175.20 μL, 5 eq) and KI (166.97 mg, 1.01 mmol, 5 eq). After addition, the reaction solution mixture was stirred at 80° C. for 16 h. LCMS showed desired MS. The residue was poured into water (20 mL). The aqueous phase was extracted with ethyl acetate (20 mL*3). The combined organic phase was washed with brine (20 mL*2), dried with anhydrous Na2SO4, filtered and concentrated in vacuum. The residue was purified by prep.HPLC (column: 3_Phenomenex Luna C18 75*30 mm*3 um; mobile phase: [water (0.225% FA)-ACN]; B %: 0%-40%, 40 min) to afford 2-(2,6-dioxo-3-piperidyl)-5-[3-[[4-fluoro-4-[[4-[6-[5-(1-methylcyclopropoxy)-2H-indazol-3-yl]pyrimidin-4-yl]piperazin-1-yl]methyl]-1-piperidyl]methyl]azetidin-1-yl]isoindoline-1,3-dione (43.8 mg, 53.17 μmol, 26.43% yield, 96% purity) as a yellow solid.

Exemplary Synthesis of Compound 136

Step 1

To a mixture of 1-tert-butoxycarbonylazetidine-3-carboxylic acid (273.56 mg, 1.36 mmol, 1.2 eq) and HATU (516.93 mg, 1.36 mmol, 1.2 eq) in DCM (4 mL) was added DIEA (732.11 mg, 5.66 mmol, 986.67 μL, 5 eq) in one portion at 25° C. The mixture was stirred at 25° C. for 10 min, then benzyl 4-[(4-fluoro-4-piperidyl)methyl]piperazine-1-carboxylate (380 mg, 1.13 mmol, 1 eq) was added. The mixture was stirred at 25° C. for 120 min. TLC (Petroleum ether: Ethyl acetate=0/1) showed a new spot was formed and the desired compound was detected by LCMS. The mixture was poured into water (5 mL). The aqueous phase was extracted with ethyl acetate (10 mL*2). The combined organic phase was washed with brine (5 mL*1), dried with anhydrous Na2SO4, filtered and concentrated in vacuum. The residue was purified by silica gel chromatography (Petroleum ether/Ethyl acetate=1/1) to give benzyl 4-[[1-(1-tert-butoxycarbonylazetidine-3-carbonyl)-4-fluoro-4-piperidyl]methyl]piperazine-1-carboxylate (380 mg, 732.71 μmol, 64.67% yield) as black brown liquid.

Step 2

A solution of benzyl 4-[[1-(1-tert-butoxycarbonylazetidine-3-carbonyl)-4-fluoro-4-piperidyl]methyl]piperazine-1-carboxylate (380 mg, 732.71 μmol, 1 eq) in EA (4 mL) and EtOH (4 mL) was added Pd/C (100 mg, 10% purity), then the mixture was stirred at 25° C. for 12 hours under H2 (15 psi). TLC (Petroleum ether:Ethyl acetate=0/1) showed the reaction was completed. The mixture was filtered and concentrated in vacuum. The crude product was used into the next step without further purification. The product tert-butyl 3-[4-fluoro-4-(piperazin-1-ylmethyl)piperidine-1-carbonyl]azetidine-1-carboxylate (240 mg, 624.21 μmol, 85.19% yield) as brown liquid.

Step 3

To a mixture of 2-[[3-(6-chloropyrimidin-4-yl)-5-(1-methylcyclopropoxy)indazol-2-yl]methoxy]ethyl-trimethyl-silane (100 mg, 232.02 μmol, 1 eq) and tert-butyl 3-[4-fluoro-4-(piperazin-1-ylmethyl)piperidine-1-carbonyl]azetidine-1-carboxylate (178.42 mg, 464.03 μmol, 2 eq) in DMSO (2 mL) was added DIEA (89.96 mg, 696.05 μmol, 121.24 μL, 3 eq) in one portion at 25° C. The mixture was stirred at 100° C. for 1 hours. TLC (Petroleum ether:Ethyl acetate=0/1) showed the reaction was completed. The mixture was poured into water (10 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel chromatography (Petroleum ether/Ethyl acetate=0/1) to give tert-butyl 3-[4-fluoro-4-[[4-[6-[5-(1-methylcyclopropoxy)-2-(2-trimethylsilylethoxymethyl)indazol-3-yl]pyrimidin-4-yl]piperazin-1-yl]methyl]piperidine-1-carbonyl]azetidine-1-carboxylate (180 mg, 221.81 μmol, 95.60% yield, 96% purity) as brown oil.

Step 4

To a mixture of tert-butyl 3-[4-fluoro-4-[[4-[6-[5-(1-methylcyclopropoxy)-2-(2-trimethylsilylethoxymethyl)indazol-3-yl]pyrimidin-4-yl]piperazin-1-yl]methyl]piperidine-1-carbonyl]azetidine-1-carboxylate (90 mg, 115.53 μmol, 1 eq) in DCM (2 mL) was added TFA (1.54 g, 13.51 mmol, 1 mL, 116.91 eq) in one portion at 25° C. The mixture was stirred at 25° C. for 1 hours. TLC (Petroleum ether: Ethyl acetate=0/1) showed the reaction was completed. The mixture was concentrated in reduced pressure at 40° C. The crude product was used into the next step without further purification. The product azetidin-3-yl-[4-fluoro-4-[[4-[6-[5-(1-methylcyclopropoxy)-2H-indazol-3-yl]pyrimidin-4-yl]piperazin-1-yl]methyl]-1-piperidyl]methanone (52 mg, 78.67 μmol, 68.09% yield, 83% purity) as gray solid.

Step 5

To a mixture of azetidin-3-yl-[4-fluoro-4-[[4-[6-[5-(1-methylcyclopropoxy)-2H-indazol-3-yl]pyrimidin-4-yl]piperazin-1-yl]methyl]-1-piperidyl]methanone (52 mg, 94.78 μmol, 1 eq) and 2-(2,6-dioxo-3-piperidyl)-5-fluoro-isoindoline-1,3-dione (31.42 mg, 113.73 μmol, 1.2 eq) in DMSO (2 mL) was added DIEA (36.75 mg, 284.33 μmol, 49.53 μL, 3 eq) in one portion at 25° C. under N2. The mixture was stirred at 100° C. for 12 hours. LCMS showed the reaction was completed. The mixture was cooled to 25° C. and poured into water (15 mL). The aqueous phase was extracted with ethyl acetate (10 mL*3). The combined organic phase was washed with brine (10 mL*2), dried with anhydrous Na2SO4, filtered and concentrated in vacuum. The residue was purified by prep-HPLC (3_Phenomenex Luna C18 75*30 mm*3 um; mobile phase: [water (0.225% FA)-ACN]; B %: 0%-45%, 40 min) to give 2-(2,6-dioxo-3-piperidyl)-5-[3-[4-fluoro-4-[[4-[6-[5-(1-methylcyclopropoxy)-2H-indazol-3-yl]pyrimidin-4-yl]piperazin-1-yl]methyl]piperidine-1-carbonyl]azetidin-1-yl]isoindoline-1,3-dione (10.2 mg, 12.14 μmol, 12.81% yield, 95.8% purity) as yellow solid.

Exemplary Synthesis of Compound 137

Step 1

To a solution of 2-(2,6-dioxo-3-piperidyl)-4-fluoro-isoindoline-1,3-dione (500 mg, 1.81 mmol, 1 eq) and 4-(dimethoxymethyl)piperidine (1 g, 6.28 mmol, 3.47 eq) in DMSO (10 mL) was added DIEA (701.79 mg, 5.43 mmol, 945.81 μL, 3 eq). The mixture was stirred at 120° C. for 2 hr. The residue was diluted with H2O (50 mL) extracted with ethyl acetate (40 mL×3). The combined organic layers were washed with brine (3×30 mL), dried over anhydrous sodium sulfate, filtered and concentrated under reduced pressure to give a residue. Then the residue was dissolved in ethyl acetate (8 mL), then petroleum ether (50 mL) was added and then was stirred at 25° C. for 16 h. The mixture was filtered and filtrate cake was dried under concentrated under reduced pressure to afford 4-[4-(dimethoxymethyl)-1-piperidyl]-2-(2,6-dioxo-3-piperidyl)isoindoline-1,3-dione (800 mg, crude) as yellow solid.

Step 2

A solution of 4-[4-(dimethoxymethyl)-1-piperidyl]-2-(2,6-dioxo-3-piperidyl)isoindoline-1,3-dione (800 mg, 1.93 mmol, 1 eq) in THF (4 mL) and HCl (2 M, 4.21 mL, 4.37 eq) was stirred at 70° C. for 1 hr. After cooling, the reaction diluted with water (20 mL) and neutralized to pH 7 with saturated $NaHCO_3$. Then the mixture was filtered and filtrate cake was dried under reduced pressure to give 1-[2-(2,6-dioxo-3-piperidyl)-1,3-dioxo-isoindolin-4-yl]piperidine-4-carbaldehyde (600 mg, 1.53 mmol, 79.29% yield, 94% purity) as yellow solid.

Step 3

To a solution of 5-(1-methylcyclopropoxy)-3-[6-[(3S)-3-methyl-4-(4-piperidylmethyl)piperazin-1-yl]pyrimidin-4-yl]-2H-indazole (45 mg, 97.49 μmol, 1 eq) in DCM (5 mL) was added DIEA (63.00 mg, 487.43 μmol, 84.90 μL, 5 eq) and stirred at 20° C. for 10 min. Then the mixture was concentrated. The residue and 1-[2-(2,6-dioxo-3-piperidyl)-1,3-dioxo-isoindolin-4-yl]piperidine-4-carbaldehyde (43.21 mg, 116.98 μmol, 1.2 eq) in HOAC (1 mL) and MeOH (10 mL) was stirred at 20° C. for 20 min, then was added borane; 2-methylpyridine (20.85 mg, 194.97 μmol, 2 eq). Then the mixture was stirred at 25° C. for 16 h under N2. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-35%, 35 min) to afford 2-(2,6-dioxo-3-piperidyl)-4-[4-[[4-[[(2S)-2-methyl-4-[6-[5-(1-methylcyclopropoxy)-2H-indazol-3-yl]pyrimidin-4-yl]piperazin-1-yl]methyl]-1-piperidyl]methyl]-1-piperidyl]isoindoline-1,3-dione (33.4 mg, 40.82 μmol, 41.87% yield, 99.60% purity) as a yellow solid.

Exemplary Synthesis of Compound 138

Step 1

To a solution of 5-(1-methylcyclopropoxy)-3-[6-[(3S)-3-methylpiperazin-1-yl]pyrimidin-4-yl]-2H-indazole (80 mg, 219.51 μmol, 1 eq) and tert-butyl 4-(2-oxoethyl)piperidine-1-carboxylate (64.86 mg, 285.37 μmol, 1.3 eq) in MeOH (10 mL) and HOAC (1 mL) was added borane; 2-methylpyridine (46.96 mg, 439.03 μmol, 2 eq). The mixture was stirred at 25° C. for 4 hr. TLC (Dichloromethane:Methanol=10:1, Rf=0.4) showed no start material and a new spot. The residue was concentrated under reduced pressure to give a residue. The residue was purified by silica gel column chromatography (0 to 10% Dichloromethane in Methanol) to give tert-butyl 4-[2-[(2S)-2-methyl-4-[6-[5-(1-methylcyclopropoxy)-2H-indazol-3-yl]pyrimidin-4-yl]piperazin-1-yl]ethyl]piperidine-1-carboxylate (60 mg, 92.75 μmol, 42.25% yield, 89% purity) as a yellow solid.

Step 2

To a solution of tert-butyl 4-[2-[(2S)-2-methyl-4-[6-[5-(1-methylcyclopropoxy)-2H-indazol-3-yl]pyrimidin-4-yl]piperazin-1-yl]ethyl]piperidine-1-carboxylate (60 mg, 104.21 μmol, 1 eq) in DCM (3 mL) was added TFA (3.08 g, 27.01 mmol, 2 mL, 259.20 eq). The mixture was stirred at 25° C. for 1 hr. TLC (Dichloromethane:Methanol=10:1, Rf=0.01) showed no start material and a new spot. The residue was concentrated under reduced pressure to give 5-(1-methylcyclopropoxy)-3-[6-[(3S)-3-methyl-4-[2-(4-piperidyl)ethyl]piperazin-1-yl]pyrimidin-4-yl]-2H-indazole (60 mg, crude, TFA) as a yellow gum.

Step 3

To a solution of 5-(1-methylcyclopropoxy)-3-[6-[(3S)-3-methyl-4-[2-(4-piperidyl)ethyl]piperazin-1-yl]pyrimidin-4-yl]-2H-indazole (60 mg, 101.76 μmol, 1 eq, TFA) in DCM (5 mL) was added DIEA (65.76 mg, 508.78 μmol, 88.62 μL, 5 eq) and stirred at 20° C. for 10 min. Then the mixture was concentrated. The residue and 1-[2-(2,6-dioxo-3-piperidyl)-1,3-dioxo-isoindolin-4-yl]piperidine-4-carbaldehyde (45.10 mg, 122.11 μmol, 1.2 eq) in HOAC (1 mL) and MeOH (10 mL) was stirred at 20° C. for 20 min, then was added borane; 2-methylpyridine (21.77 mg, 203.51 μmol, 2 eq). Then the mixture was stirred at 25° C. for 16 h under N2. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-35%, 35 min) to afford 2-(2,6-dioxo-3-piperidyl)-4-[4-[[4-[2-[(2S)-2-methyl-4-[6-[5-(1-methylcyclopropoxy)-2H-indazol-3-yl]pyrimidin-4-yl]piperazin-1-yl]ethyl]-1-piperidyl]methyl]-1-piperidyl]isoindoline-1,3-dione (34.3 mg, 40.96 μmol, 40.25% yield, 98.99% purity) as a yellow solid.

Exemplary Synthesis of Compound 139

Step 1

To a mixture of 3-hydroxypropyl 4-methylbenzenesulfonate (500 mg, 2.17 mmol, 1 eq) and 2-(2,6-dioxo-3-piperidyl)-4-hydroxy-isoindoline-1,3-dione (595.42 mg, 2.17 mmol, 1 eq) in DMSO (5 mL) was added Na2CO3 (690.39 mg, 6.51 mmol, 3 eq) in one portion at 25° C. The mixture was stirred at 60° C. for 2 hours. LCMS showed the reaction was completed. The mixture was cooled to 25° C., filtered and poured into water (10 mL). The aqueous phase was extracted with ethyl acetate (30 mL*3). The combined organic phase was washed with brine (20 mL*2), dried with anhydrous Na2SO4, filtered and concentrated in vacuum. The residue was purified by prep-HPLC (3_Phenomenex Luna C18 75*30 mm*3 um; mobile phase: [water (0.225% FA)-ACN]; B %: 0%-30%, 35 min) to give 2-(2,6-dioxo-3-piperidyl)-4-(3-hydroxypropoxy)isoindoline-1,3-dione (110 mg, 331.02 μmol, 15.25% yield, 100% purity) as a gray solid.

Step 2

To a mixture of 2-(2,6-dioxo-3-piperidyl)-4-(3-hydroxypropoxy)isoindoline-1,3-dione (110 mg, 331.02 μmol, 1 eq), DMAP (8.09 mg, 66.20 μmol, 0.2 eq) and TEA (167.48 mg, 1.66 mmol, 230.37 μL, 5 eq) in DMF (2 mL) was added 4-methylbenzenesulfonyl chloride (189.32 mg, 993.06 μmol, 3 eq) at 0° C. The mixture was stirred for 12 hours 25° C. TLC (Petroleum ether:Ethyl acetate=1/1) showed the reaction was completed. The mixture was poured into water (10 mL) and extracted with ethyl acetate (15 mL*3). The combined organic phase was washed with brine (10 mL*2), dried with anhydrous Na2SO4, filtered and concentrated in vacuum. The residue was purified by silica gel chromatography (Petroleum ether/Ethyl acetate=1/1) to afford 3-[2-(2,6-dioxo-3-piperidyl)-1,3-dioxo-isoindolin-4-yl]oxypropyl 4-methylbenzenesulfonate (80 mg, 88.80 μmol, 26.83% yield, 54% purity) as light yellow oil Step 3

To a mixture of 3-[2-(2,6-dioxo-3-piperidyl)-1,3-dioxo-isoindolin-4-yl]oxypropyl 4-methylbenzenesulfonate (40 mg, 82.22 μmol, 1 eq) and 5-(1-methylcyclopropoxy)-3-[6-[(3S)-3-methyl-4-(4-piperidylmethyl)piperazin-1-yl]pyrimidin-4-yl]-2H-indazole (56.93 mg, 123.33 μmol, 1.5 eq) in MeCN (1 mL) was added DIEA (53.13 mg, 411.11 μmol, 71.61 μL, 5 eq), KI (13.65 mg, 82.22 μmol, 1 eq) in one portion at 25° C. The mixture was stirred at 66° C. for 12 hours. LCMS showed the reaction was completed. The mixture was cooled to 25° C., filtered and concentrated in vacuum. The residue was purified by prep-HPLC (3_Phenomenex Luna C18 75*30 mm*3 um; mobile phase: [water (0.225% FA)-ACN]; B %: 0%-35%, 40 min) to afford 2-(2,6-dioxo-3-piperidyl)-4-[3-[4-[[(2S)-2-methyl-4-[6-[5-(1-methylcyclopropoxy)-2H-indazol-3-yl]pyrimidin-4-yl]piperazin-1-yl]methyl]-1-piperidyl]propoxy]isoindoline-1,3-dione (10.5 mg, 12.28 μmol, 14.93% yield, 96.1% purity, FA) as a gray solid.

Exemplary Synthesis of Compound 140

Step 1

To a mixture of 2-(2,6-dioxo-3-piperidyl)-4-fluoro-isoindoline-1,3-dione (500 mg, 1.81 mmol, 1 eq) and 3-aminopropan-1-ol (271.90 mg, 3.62 mmol, 279.16 μL, 2 eq) in DMSO (5 mL) was added DIEA (701.77 mg, 5.43 mmol, 945.79 μL, 3 eq) in one portion at 20° C. The mixture was stirred at 100° C. for 2 h. LCMS showed the reaction was completed. The mixture was cooled to 20° C. The aqueous phase was extracted with ethyl acetate (3×10 mL). The combined organic phase was washed with brine (2×10 mL), dried with anhydrous Na2SO4, filtered and concentrated in vacuum. The residue was purified by silica gel chromatography (100-200 mesh silica gel, 0-10% of MeOH in DCM) to give 2-(2,6-dioxo-3-piperidyl)-4-(3-hydroxypropylamino)isoindoline-1,3-dione (146 mg, 440.66 μmol, 24.35% yield) as a yellow gum.

Step 2

To a mixture of 2-(2,6-dioxo-3-piperidyl)-4-(3-hydroxypropylamino)isoindoline-1,3-dione (126 mg, 380.29 μmol, 1 eq) and TosCl (72.50 mg, 380.29 μmol, 1 eq) in DCM (10 mL) was added DMAP (46.46 mg, 380.29 μmol, 1 eq) and Et3N (76.96 mg, 760.59 μmol, 105.86 μL, 2 eq) in one portion at 25° C. under N2. The mixture was stirred at 25° C. for 2 hours. TLC showed the reaction was completed. The residue was poured into water (10 mL). The aqueous phase was extracted with DCM (10 mL*3). The combined organic phase was washed with brine (10 mL*2), dried with anhydrous Na2SO4, filtered and concentrated in vacuum. The residue was purified by silica gel chromatography (12 g, 0-100% (20 min) of Ethyl acetate in Petroleum ether) to give 3-[[2-(2,6-dioxo-3-piperidyl)-1,3-dioxo-isoindolin-4-yl]amino]propyl 4-methylbenzenesulfonate (98 mg, 189.74 μmol, 49.89% yield, 94% purity) as a yellow gum.

Step 3

To a mixture of 5-(1-methylcyclopropoxy)-3-[6-[(3S)-3-methyl-4-(4-piperidylmethyl)piperazin-1-yl]pyrimidin-4-yl]-1H-indazole (60 mg, 129.98 μmol, 1 eq) and 3-[[2-(2,6-dioxo-3-piperidyl)-1,3-dioxo-isoindolin-4-yl]amino]propyl 4-methylbenzenesulfonate (98 mg, 201.85 μmol, 1.55 eq) in MeCN (5 mL) was added DIPEA (84.00 mg, 649.91 μmol, 113.20 μL, 5 eq) and KI (107.89 mg, 649.91 μmol, 5 eq) in one portion at 20° C. under N2. The mixture was stirred at 80° C. for 16 h. LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0; End B: 35; Flow Rate: 35 mL/min; Gradient Time: 35 min; 100% B Hold Time: 1 min) to give 2-(2,6-dioxo-3-piperidyl)-4-[3-[4-[[(2S)-2-methyl-4-[6-[5-(1-methylcyclopropoxy)-2H-indazol-3-yl]pyrimidin-4-yl]piperazin-1-yl]methyl]-1-piperidyl]propylamino]isoindoline-1,3-dione (50.1 mg, 64.11 μmol, 49.32% yield, 99.16% purity) as a yellow solid.

Exemplary Synthesis of Compound 141

Step 1

To a solution of benzyl 4-(4-piperidylmethyl)piperazine-1-carboxylate (1.9 g, 4.40 mmol, 1 eq, TFA) and 4-(tert-butoxycarbonylamino)butyl 4-methylbenzenesulfonate (1.6 g, 4.66 mmol, 1.06 eq) in CH3CN (15 mL) was added KI (1.46 g, 8.81 mmol, 2 eq) and DIEA (2.85 g, 22.02 mmol, 3.84 mL, 5 eq). After addition, the reaction mixture was stirred at 80° C. for 12 h. LCMS showed desired MS. TLC (dichloromethane:methanol=10:1) showed several new spots. After cooling, the reaction mixture was diluted with water (30 mL) and extracted with ethyl acetate (3×20 mL). The organic layer was dried over sodium sulfate and concentrated under reduced pressure. The residue was purified by silica gel column chromatography (0 to 10% methanol in dichloromethane) to afford benzyl 4-[[1-[4-(tert-butoxycarbonylamino)butyl]-4-piperidyl]methyl]piperazine-1-carboxylate (680 mg, 1.15 mmol, 26.10% yield, 82.6% purity) as a yellow oil.

Step 2

To a solution of benzyl 4-[[1-[4-(tert-butoxycarbonylamino)butyl]-4-piperidyl]methyl]piperazine-1-carboxylate (680 mg, 1.39 mmol, 1 eq) in DCM (5 mL) was added TFA (4.62 g, 40.52 mmol, 3 mL, 29.12 eq). After addition, the reaction solution was stirred at 25° C. for 1 h. LCMS showed starting material consumed and desired MS found. The reaction mixture was concentrated under reduced pressure to afford benzyl 4-[[1-(4-aminobutyl)-4-piperidyl]methyl]piperazine-1-carboxylate (840 mg, crude, TFA) as a yellow oil. The crude product was used for next step directly.

Step 3

To a solution of benzyl 4-[[1-(4-aminobutyl)-4-piperidyl]methyl]piperazine-1-carboxylate (840 mg, 1.67 mmol, 1 eq, TFA) in DMF (10 mL) was added 2-(2,6-dioxo-3-piperidyl)-4-fluoro-isoindoline-1,3-dione (461.68 mg, 1.67 mmol, 1 eq) and DIEA (1.08 g, 8.36 mmol, 1.46 mL, 5 eq). After addition, the reaction mixture was stirred at 90° C. for 12 h. LCMS showed desired MS. TLC (dichloromethane:methanol=10:1) showed several new spots. After addition, the reaction was diluted with ethyl acetate (20 mL) and washed with brine (2×20 mL). The organic layer was dried over sodium sulfate and concentrated under reduced pressure. The residue was purified by silica gel column chromatography (0 to 20% methanol in dichloromethane) to afford benzyl 4-[[1-[4-[[2-(2,6-dioxo-3-piperidyl)-1,3-dioxo-isoindolin-4-yl]amino]butyl]-4-piperidyl]methyl]piperazine-1-carboxylate (84 mg, 111.72 μmol, 6.68% yield, 85.75% purity) as a yellow solid.

Step 4

A mixture of benzyl 4-[[1-[4-[[2-(2,6-dioxo-3-piperidyl)-1,3-dioxo-isoindolin-4-yl]amino]butyl]-4-piperidyl]methyl]piperazine-1-carboxylate (84 mg, 130.28 μmol, 1 eq) and TFA (2 mL) was stirred at 80° C. for 1 h. TLC (dichloromethane:methanol=5:1) showed starting material consumed and a new spot formed. The reaction mixture was concentrated under reduced pressure to afford 2-(2,6-dioxo-3-piperidyl)-4-[4-[4-(piperazin-1-ylmethyl)-1-piperidyl]butylamino]isoindoline-1,3-dione (81 mg, crude, TFA) as a yellow gum. The crude product was used for next step directly.

Step 5

To a solution of 2-(2,6-dioxo-3-piperidyl)-4-[4-[4-(piperazin-1-ylmethyl)-1-piperidyl]butylamino]isoindoline-1,3-dione (81.00 mg, 129.67 μmol, 1 eq, TFA) and 3-(6-chloropyrimidin-4-yl)-6-(1-methylcyclopropoxy)-1H-indazole (45 mg, 149.63 μmol, 1.15 eq) in DMSO (2 mL) was added DIEA (83.80 mg, 648.36 μmol, 112.93 μL, 5 eq). After addition, the reaction was stirred at 90° C. for 24 h to give brown solution. LCMS showed starting material consumed and desired MS found. The reaction mixture was diluted with water (15 mL) and extracted with ethyl acetate (3×10 mL). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 0-30%; 40 min) to afford 2-(2,6-dioxo-3-piperidyl)-4-[4-[4-[[4-[6-[6-(1-methylcyclopropoxy)-1H-indazol-3-yl]pyrimidin-4-yl]piperazin-1-yl]methyl]-1-piperidyl]butylamino]isoindoline-1,3-dione (13.8 mg, 17.32 μmol, 13.36% yield, 97.27% purity) as a yellow solid.

Exemplary Synthesis of Compound 142

Step 1

To a mixture of 5-(1-methylcyclopropoxy)-3-[6-[(3S)-3-methyl-4-(4-piperidylmethyl)piperazin-1-yl]pyrimidin-4-yl]-2H-indazole (200 mg, 217.94 μmol, 1 eq, 4TFA) and 3-bromo-1,1-dimethoxy-propane (79.78 mg, 435.88 μmol, 59.54 μL, 2 eq) in DMF (5 mL) was added DIEA (225.34 mg, 1.74 mmol, 303.69 μL, 8 eq) in one portion at 25° C. The mixture was stirred at 90° C. for 2 hours. TLC (Dichloromethane:Methanol=10/1) showed the reaction was completed. The mixture was cooled to 25° C. The residue was poured into water (20 mL). The aqueous phase was extracted with ethyl acetate (20 mL*2). The combined organic phase was washed with brine (10 mL*2), dried with anhydrous Na2SO4, filtered and concentrated in vacuum. The residue was purified by silica gel chromatography (Dichloromethane:Methanol=10/1) to give 3-[6-[(3S)-4-[[1-(3,3-dimethoxypropyl)-4-piperidyl]methyl]-3-methyl-piperazin-1-yl]pyrimidin-4-yl]-5-(1-methylcyclopropoxy)-1H-indazole (70 mg, 120.45 μmol, 55.27% yield, 97% purity) as light yellow oil.

Step 2

To a mixture of 3-[6-[(3S)-4-[[1-(3,3-dimethoxypropyl)-4-piperidyl]methyl]-3-methyl-piperazin-1-yl]pyrimidin-4-yl]-5-(1-methylcyclopropoxy)-1H-indazole (70 mg, 124.17 μmol, 1 eq) in THF (1 mL) was added H2SO4 (2 M, 310.43 μL, 5 eq). The mixture was stirred at 60° C. for 1 hr. LCMS showed the reaction completed. The mixture was poured into water (1 mL). The pH of the mixture was adjusted to 7-8 by adding Na2CO3. The mixture was extracted with DCM (5 mL*3). The combined organic layer was washed with brine (5 mL), dried over Na2SO4, filtered and concentrated in vacuum to give 3-[4-[[(2S)-2-methyl-4-[6-[5-(1-methylcyclopropoxy)-1H-indazol-3-yl]pyrimidin-4-yl]piperazin-1-yl]methyl]-1-piperidyl]propanal (56 mg, 106.01 μmol, 85.38% yield, 98% purity) as a brown oil. The crude product was used into the next step without further purification.

Step 3

To a mixture of 3-(4-amino-1-oxo-isoindolin-2-yl)piperidine-2,6-dione (42.07 mg, 162.27 μmol, 1.5 eq) in HOAc (0.3 mL) and MeOH (3 mL) was added 3-[4-[[(2S)-2-methyl-4-[6-[5-(1-methylcyclopropoxy)-1H-indazol-3-yl]pyrimidin-4-yl]piperazin-1-yl]methyl]-1-piperidyl]propanal (56 mg, 108.18 μmol, 1 eq) in one portion at 25° C., then borane; 2-methylpyridine (23.14 mg, 216.36 μmol, 2 eq) was added. The mixture was stirred at 25° C. for 12 hours. LCMS showed the desired product was produced 44%. The mixture was concentrated in reduced pressure. The residue was purified by prep-HPLC (column: Phenomenex Luna C18 75*30 mm*3 um; mobile phase: [water (0.225% FA)-ACN]; B %: 0%-30%, 35 min) to afford 3-[4-[3-[4-[[(2S)-2-methyl-4-[6-[5-(1-methylcyclopropoxy)-1H-indazol-3-yl]pyrimidin-4-yl]piperazin-1-yl]methyl]-1-piperidyl]propylamino]-1-oxo-isoindolin-2-yl]piperidine-2,6-dione (13.2 mg, 16.19 μmol, 14.97% yield, 99% purity, FA) as a gray solid.

Exemplary Synthesis of Compound 143

Step 1

To a solution of benzyl 4-(4-piperidylmethyl)piperazine-1-carboxylate (3 g, 8.48 mmol, 1 eq, HCl) and 4-bromobutan-1-ol (1.62 g, 8.48 mmol, 80% purity, 1 eq) in THF (10 mL) was added K2CO3 (3.51 g, 25.43 mmol, 3 eq). Then the mixture was stirred at 60° C. for 16 hours under N2. LCMS showed no start material. TLC (Dichloromethane:Methanol=10:1, Rf=0.2) showed the reaction new spot. The reaction mixture was filtered and the filtrate was concentrated to give benzyl 4-[[1-(4-hydroxybutyl)-4-piperidyl]methyl]piperazine-1-carboxylate (3.1 g, crude) as a white gum.

Step 2

A solution of OXALYL CHLORIDE (716.88 mg, 5.65 mmol, 494.40 μL, 1.1 eq) in DCM (10 mL) was cooled to −60° C. under an atmosphere of dry nitrogen. A solution of DMSO (1.00 g, 12.84 mmol, 1.00 mL, 2.5 eq) in DCM (10 mL) was added dropwise, and the mixture was subsequently stirred for 15 min at −60° C. Next, a solution of benzyl 4-[[1-(4-hydroxybutyl)-4-piperidyl]methyl]piperazine-1-carboxylate (2 g, 5.13 mmol, 1 eq) in DCM (10 mL) was added dropwise and the mixture stirred for 45 min at −60° C. Subsequently, TEA (1.56 g, 15.40 mmol, 2.14 mL, 3 eq) was added, and the mixture was warmed to −60° C. for 1 h. TLC (Dichloromethane:Methanol=10:1, Rf=0.4) showed the reaction new spot. The reaction mixture was filtered and the filtrate was used directly in the next step, benzyl 4-[[1-(4-oxobutyl)-4-piperidyl]methyl]piperazine-1-carboxylate (1.5 g, crude) in DCM solution as yellow liquid, which was used directly in the next step.

Step 3

To a solution of benzyl 4-[[1-(4-oxobutyl)-4-piperidyl]methyl]piperazine-1-carboxylate (1.5 g, 3.87 mmol, 1.43 eq) and 3-(4-amino-1-oxo-isoindolin-2-yl)piperidine-2,6-dione (700 mg, 2.70 mmol, 1 eq) in DCM (15 mL) and MeOH (15 mL) was added HOAc (16.21 mg, 270.00 μmol, 15.44 μL, 0.1 eq) and the mixture was stirred at 20° C. for 20 min. Then the NaBH3CN (509.00 mg, 8.10 mmol, 3 eq) was added of the solution and was stirred at 20° C. for 16 hr. TLC (Dichloromethane:Methanol=10:1, Rf=0.2) was showed the reaction completed. The reaction mixture was poured into H2O (20 mL). The mixture was extracted with ethyl acetate (30 mL*3). The organic phase was washed with brine (20 mL), dried over anhydrous Na2SO4, concentrated in vacuum to give a residue. The residue was purified by silica gel column chromatography (0-20% Methanol in Dichloromethane) to give compound. The residue was purified by prep-HPLC (column: Xtimate C18 150*40 mm*10 um; mobile phase: [water (0.225% FA)-ACN]; B %: 5%-35%, 10 min) to afford benzyl 4-[[1-[4-[[2-(2,6-dioxo-3-piperidyl)-1-oxo-isoindolin-4-yl]amino]butyl]-4-piperidyl]methyl]piperazine-1-carboxylate (300 mg, 461.34 μmol, 17.09% yield, 97% purity) as a white solid.

Step 4

To a solution of benzyl 4-[[1-[4-[[2-(2,6-dioxo-3-piperidyl)-1-oxo-isoindolin-4-yl]amino]butyl]-4-piperidyl]methyl]piperazine-1-carboxylate (100 mg, 158.54 μmol, 1 eq) was added TFA (4.62 g, 40.52 mmol, 3 mL, 255.58 eq) and the mixture was stirred at 70° C. for 1 h. TLC (Dichloromethane:Methanol=10:1, Rf=0.01) was showed the reaction completed. The reaction mixture was concentrated in vacuum to give 3-[1-oxo-4-[4-[4-(piperazin-1-ylmethyl)-1-piperidyl]butylamino]isoindolin-2-yl]piperidine-2,6-dione (78 mg, crude) as a colorless gum.

Step 5

To a solution of 3-(6-chloropyrimidin-4-yl)-6-(1-methylcyclopropoxy)-1H-indazole (35 mg, 116.38 μmol, 7.41 e-1 eq) and 3-[1-oxo-4-[4-[4-(piperazin-1-ylmethyl)-1-piperidyl]butylamino]isoindolin-2-yl]piperidine-2,6-dione (78 mg, 157.05 μmol, 1 eq) in DMSO (5 mL) and DIEA (202.98 mg, 1.57 mmol, 273.55 μL, 10 eq). The mixture was stirred at 80° C. for 16 h. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-30%, 40 min) to give 3-[4-[4-[4-[[4-[6-[5-(1-methylcyclopropoxy)-1H-indazol-3-yl]pyrimidin-4-yl]piperazin-1-yl]methyl]-1-piperidyl]butylamino]-1-oxo-isoindolin-2-yl]piperidine-2,6-dione (8.3 mg, 10.91 μmol, 6.95% yield, 100% purity) as a white solid.

Exemplary Synthesis of Compound 144

Step 1

To a solution of tert-butyl 3-(aminomethyl)-3-hydroxy-azetidine-1-carboxylate (5 g, 24.72 mmol, 1 eq) in DCM (50 mL) was added Et3N (3.75 g, 37.08 mmol, 5.16 mL, 1.5 eq) followed by drop-wise addition of 2-chloroacetyl chloride (3.35 g, 29.67 mmol, 2.36 mL, 1.2 eq) at 0° C. The mixture was stirred at 25° C. for 2 hrs. LCMS showed desired MS. TLC (dichloromethane:methanol=10:1) showed several spots. The reaction mixture was diluted with water (40 mL) and extracted with dichloromethane (2×50 mL). The organic layer was dried over sodium sulfate and concentrated under reduced pressure. The residue was purified by silica gel column chromatography (0 to 5% methanol in dichloromethane) to afford tert-butyl 3-[[(2-chloroacetyl)amino]methyl]-3-hydroxy-azetidine-1-carboxylate (4 g, 14.35 mmol, 58.05% yield, 100% purity) as a white solid.

Step 2

To a solution of tert-butyl 3-[[(2-chloroacetyl)amino]methyl]-3-hydroxy-azetidine-1-carboxylate (3 g, 10.76 mmol, 1 eq) in dioxane (30 mL) was added NaH (753.34 mg, 18.84 mmol, 60% purity, 1.75 eq) at 25° C. The reaction solution was stirred at 80° C. for 12 h. TLC (dichloromethane:methanol=10:1) showed several new spots. After cooling, the reaction mixture was quenched by water (20 mL) and extracted with ethyl acetate (15 mL*3). The organic layer was dried over sodium sulfate and concentrated under reduced pressure. The residue was purified by silica gel column chromatography (0 to 10% methanol in dichloromethane) to afford tert-butyl 7-oxo-5-oxa-2,8-diazaspiro[3.5]nonane-2-carboxylate (520 mg, 2.15 mmol, 19.94% yield) as a white solid.

Step 3

To a solution of tert-butyl 7-oxo-5-oxa-2,8-diazaspiro[3.5]nonane-2-carboxylate (520 mg, 2.15 mmol, 1 eq) in THF (8 mL) was added BH3·THF (1 M, 6.44 mL, 3 eq) at 0° C. under N2. After addition, the reaction solution was stirred at 25° C. for 12 h. TLC (dichloromethane:methanol=10:1) showed several new spots. The solution was quenched by 15% sodium hydroxide solution (10 mL) was added drop-wise over a 5 minute period to control gas evolution. The mixture was diluted with water (10 mL) and extracted with ethyl acetate (20 mL). The organic layer was dried over sodium sulfate and concentrated under reduced pressure. The residue was purified by silica gel column chromatography (0 to 10% methanol in dichloromethane) to afford tert-butyl 5-oxa-2,8-diazaspiro[3.5]nonane-2-carboxylate (430 mg, 1.88 mmol, 87.76% yield) as a white solid.

Step 4

To a solution of 4-bromo-2-fluoropyridine (331.49 mg, 1.88 mmol, 1 eq) in DMSO (5 mL) was added tert-butyl 5-oxa-2,8-diazaspiro[3.5]nonane-2-carboxylate (430 mg, 1.88 mmol, 1 eq) and K2CO3 (520.65 mg, 3.77 mmol, 2 eq). After addition, the reaction solution was stirred at 90° C. for 12 h. TLC (petroleum ether:ethyl acetate=3:1) showed several new spots. After cooling, the reaction mixture was filtered and filtrate was diluted with ethyl acetate (50 mL) and washed with brine (3×30 mL). The organic layer was dried over sodium sulfate and concentrated under reduced pressure. The residue was purified by silica gel column chromatography (0 to 20% ethyl acetate in petroleum ether) to afford tert-butyl 8-(4-bromo-2-pyridyl)-5-oxa-2,8-diazaspiro[3.5]nonane-2-carboxylate (430 mg, 1.05 mmol, 55.84% yield, 94% purity) as a colorless oil.

Step 5

To a solution of tert-butyl 8-(4-bromo-2-pyridyl)-5-oxa-2,8-diazaspiro[3.5]nonane-2-carboxylate (560 mg, 1.46 mmol, 1 eq) in dioxane (10 mL) was added Pin2B2 (740.14 mg, 2.91 mmol, 2 eq), KOAc (429.06 mg, 4.37 mmol, 3 eq) and Pd(dppf)Cl2 (106.63 mg, 145.73 μmol, 0.1 eq). After addition, the reaction mixture was stirred at 100° C. under N2 for 12 h. LCMS showed starting material consumed and desired MS formed. After cooling, the reaction mixture was filtered and filtrate was concentrated under reduced pressure to afford [2-(2-tert-butoxycarbonyl-5-oxa-2,8-diazaspiro[3.5]nonan-8-yl)-4-pyridyl]boronic acid (800 mg, crude) as a black oil. The crude product was used for next step directly.

Step 6

To a solution of [2-(2-tert-butoxycarbonyl-5-oxa-2,8-diazaspiro[3.5]nonan-8-yl)-4-pyridyl]boronic acid (800 mg, 2.29 mmol, 1.85 eq) in dioxane (10 mL) and H2O (2 mL) was added 2-[[3-iodo-5-(1-methylcyclopropoxy)indazol-1-yl]methoxy]ethyl-trimethyl-silane (550 mg, 1.24 mmol, 1 eq), Na2CO3 (393.54 mg, 3.71 mmol, 3 eq) and Pd(dppf)Cl2 (90.56 mg, 123.77 μmol, 0.1 eq). After addition, the reaction mixture was stirred at 100° C. under N2 for 4 h. LCMS showed desired MS. TLC (petroleum ether:ethyl acetate=5:1) showed several new spots. After cooling, the reaction mixture was filtered and filtrated was concentrated under reduced pressure. The residue was purified by silica gel column chromatography (0 to 20% ethyl acetate in petroleum ether) to afford tert-butyl 8-[4-[5-(1-methylcyclopropoxy)-1-(2-trimethylsilylethoxymethyl)indazol-3-yl]-2-pyridyl]-5-oxa-2,8-diazaspiro[3.5]nonane-2-carboxylate (558 mg, 825.55 μmol, 66.70% yield, 92% purity) as a yellow gum.

Step 7

To a solution of tert-butyl 8-[4-[5-(1-methylcyclopropoxy)-1-(2-trimethylsilylethoxymethyl)indazol-3-yl]-2-pyridyl]-5-oxa-2,8-diazaspiro[3.5]nonane-2-carboxylate (558 mg, 897.34 μmol, 1 eq) in DCM (3 mL) was added TFA (4.62 g, 40.52 mmol, 3 mL, 45.15 eq). After addition, the reaction solution was stirred at 25° C. for 12 h. LCMS showed the starting material was consumed. The reaction mixture was concentrated under reduced pressure. The residue was dissolved in dioxane (10 mL) and ammonium hydroxide (5 mL) was added. Then the mixture was stirred at 25° C. for 30 min. The mixture was diluted with water (10 mL) and extracted with ethyl acetate (10 mL*3). The organic layer was dried over sodium sulfate and concentrated under reduced pressure to afford 8-[4-[5-(1-methylcyclopropoxy)-1H-indazol-3-yl]-2-pyridyl]-5-oxa-2,8-diazaspiro[3.5]nonane (220 mg, 485.56 μmol, 54.11% yield, 86.4% purity) as a yellow solid.

Step 8

To a solution of 8-[4-[5-(1-methylcyclopropoxy)-1H-indazol-3-yl]-2-pyridyl]-5-oxa-2,8-diazaspiro[3.5]nonane (220 mg, 561.99 μmol, 1 eq) in MeOH (5 mL) as added tert-butyl 4-formylpiperidine-1-carboxylate (239.72 mg, 1.12 mmol, 2 eq) and borane; 2-methylpyridine (120.22 mg, 1.12 mmol, 2 eq). After addition, the reaction solution was stirred at 25° C. for 12 h. LCMS showed starting material consumed and desired MS formed. TLC (dichloromethane: methanol=10:1) showed several new spots. The reaction mixture was concentrated under reduced pressure. The residue was purified by silica gel column chromatography (0 to 10% methanol in dichloromethane) to afford tert-butyl 4-[[8-[4-[5-(1-methylcyclopropoxy)-1H-indazol-3-yl]-2-pyridyl]-5-oxa-2,8-diazaspiro[3.5]nonan-2-yl]methyl]piperidine-1-carboxylate (200 mg, 328.50 μmol, 58.45% yield, 96.7% purity) as a light yellow solid.

Step 9

To a solution of tert-butyl 4-[[8-[4-[5-(1-methylcyclopropoxy)-1H-indazol-3-yl]-2-pyridyl]-5-oxa-2,8-diazaspiro[3.5]nonan-2-yl]methyl]piperidine-1-carboxylate (100 mg, 169.85 μmol, 1 eq) in DCM (2 mL) was added TFA (1.54 g, 13.51 mmol, 1 mL, 79.52 eq). After addition, the reaction solution was stirred at 25° C. for 1 h. TLC (dichloromethane: methanol=10:1) showed starting material consumed and a new spot formed. The reaction mixture was concentrated under reduced pressure. The residue was dissolved in DCM (5 mL) and treated with DIEA (1.5 mL). The mixture was concentrated under reduced pressure to afford 8-[4-[5-(1-methylcyclopropoxy)-1H-indazol-3-yl]-2-pyridyl]-2-(4-piperidylmethyl)-5-oxa-2,8-diazaspiro[3.5]nonane (90 mg, crude) as a red solid. The crude product was used for next step directly.

Step 10

To a solution of 8-[4-[5-(1-methylcyclopropoxy)-1H-indazol-3-yl]-2-pyridyl]-2-(4-piperidylmethyl)-5-oxa-2,8-diazaspiro[3.5]nonane (45 mg, 92.10 μmol, 1 eq) in MeOH (5 mL) and HOAc (0.5 mL) was added 1-[2-(2,6-dioxo-3-piperidyl)-1,3-dioxo-isoindolin-4-yl]piperidine-4-carbaldehyde (34.02 mg, 92.10 μmol, 1 eq) and borane; 2-methylpyridine (19.70 mg, 184.20 μmol, 2 eq). After addition, the reaction solution was stirred at 25° C. for 12 h. LCMS showed starting material consumed and desired MS formed. The reaction mixture was concentrated under reduced pressure. The residue was purified by prep.HPLC (column: 3_Phenomenex Luna C18 75*30 mm*3 um; mobile phase: [water (0.225% FA)-ACN]; B %: 0-35%; 40 min) to afford 2-(2,6-dioxo-3-piperidyl)-4-[4-[[4-[[8-[4-[5-(1-methylcyclopropoxy)-1H-indazol-3-yl]-2-pyridyl]-5-oxa-2,8-diazaspiro[3.5]nonan-2-yl]methyl]-1-piperidyl]methyl]-1-piperidyl]isoindoline-1,3-dione (29.4 mg, 34.84 μmol, 37.82% yield, 99.77% purity) as a yellow solid.

Exemplary Synthesis of Compound 145

Step 1

To a solution of methyl 3-bromo-2-(bromomethyl)benzoate (1 g, 3.25 mmol, 1 eq) and 3-aminopiperidine-2,6-dione (641.33 mg, 3.90 mmol, 1.2 eq, HCl) in MeCN (10 mL) was added DIEA (2.10 g, 16.24 mmol, 2.83 mL, 5 eq) stirred at 90° C. for 16 h. LCMS showed all desired product. The resultant solids were collected by filtration. The solid was washed with MeCN (5 mL×3) then concentrated under reduced pressure to give 3-(4-bromo-1-oxo-isoindolin-2-yl)piperidine-2,6-dione (900 mg, crude) as an off-white solid.

Step 2

To a solution of 3-(4-bromo-1-oxo-isoindolin-2-yl)piperidine-2,6-dione (300 mg, 928.39 μmol, 1 eq) and 4-(dimethoxymethyl)piperidine (443.47 mg, 2.79 mmol, 3 eq) in DMSO (5 mL) was added Pd-PEPPSI-pent Cl-Opicoline (50.41 mg, 92.84 μmol, 0.1 eq) and Cs2CO3 (604.97 mg, 1.86 mmol, 2 eq) stirred at 80° C. for 16 h under N2. TLC (Petroleum ether:Ethyl acetate=0:1, Rf=0.3) showed the reaction a new spot. The reaction was quenched by NH4Cl (20 mL) solution and extracted with ethyl acetate (3*20 mL). The combined organic phases were washed with water, dried with Na2SO4, concentrated in vacuum to give a residue. The residue was purified by prep-TLC (Ethyl acetate. Rf=0.3) to give 3-[4-[4-(dimethoxymethyl)-1-piperidyl]-1-oxo-isoindolin-2-yl]piperidine-2,6-dione (172 mg, 304.19 μmol, 32.77% yield, 71% purity) as a white solid.

Step 3

A solution of 3-[4-[4-(dimethoxymethyl)-1-piperidyl]-1-oxo-isoindolin-2-yl]piperidine-2,6-dione (100 mg, 249.09 μmol, 1 eq) in THF (2 mL) and HCl (2 M, 6.67 mL, 53.53 eq) was stirred at 20° C. for 8 hr. The reaction mixture was poured into H2O (20 mL) and basified with aqueous NaHCO3 till pH=8. The mixture was extracted with ethyl acetate (20 mL*5) and dried over anhydrous Na2SO4, concentrated in vacuum to give 1-[2-(2,6-dioxo-3-piperidyl)-1-oxo-isoindolin-4-yl]piperidine-4-carbaldehyde (70 mg, crude) as yellow solid.

Step 4

To the mixture of 1-[2-(2,6-dioxo-3-piperidyl)-1-oxo-isoindolin-4-yl]piperidine-4-carbaldehyde (70 mg, 98.48 μmol, 50% purity, 1 eq) and 5-(1-methylcyclopropoxy)-3-[6-[(3S)-3-methyl-4-(4-piperidylmethyl)piperazin-1-yl]pyrimidin-4-yl]-2H-indazole (45.46 mg, 98.48 μmol, 1 eq) in HOAC (1 mL) and MeOH (10 mL) was stirred at 25° C. for 20 min, then was added borane; 2-methylpyridine (21.07 mg, 196.96 μmol, 2 eq). Then the mixture was stirred at 25° C. for 16 h under N2. LCMS showed desired product. The residue was concentrated under reduced pressure to give a residue. The residue was purified by prep-HPLC (column: 3_Phenomenex Luna C18 75*30 mm*3 um; mobile phase: [water (10 mM NH4HCO3)-ACN]; B %: 30%-90%, 40 min) to afford 3-[4-[4-[[4-[[(2S)-2-methyl-4-[6-[5-(1-methylcyclopropoxy)-2H-indazol-3-yl]pyrimidin-4-yl]piperazin-1-yl]methyl]-1-piperidyl]methyl]-1-piperidyl]-1-oxo-isoindolin-2-yl]piperidine-2,6-dione (14.8 mg, 18.48 μmol, 18.76% yield, 100% purity) as white solid.

Exemplary Synthesis of Compound 146

Step 1

To a mixture of 5-(1-methylcyclopropoxy)-3-[6-[4-(piperazin-1-ylmethyl)-1-piperidyl]pyrimidin-4-yl]-2H-indazole (48 mg, 107.24 μmol, 1 eq) and 1-[2-(2,6-dioxo-3-piperidyl)-1,3-dioxo-isoindolin-4-yl]piperidine-4-carbaldehyde (51.50 mg, 139.42 μmol, 1.3 eq) in MeOH (5 mL) was added AcOH (1 mL) and borane; 2-methylpyridine (22.94 mg, 214.49 μmol, 2 eq) in one portion at 25° C. under N2. The mixture was stirred at 25° C. for 4 h. LCMS showed there was desired MS. The crude product was purified by reversed-phase HPLC(Column: 3_Phenomenex Luna C18 75*30 mm*3 um; Condition: water (0.225% FA)-ACN; Begin B: 0 End B: 35; Flow Rate: 25 mL/min; Gradient Time: 35 min; 100% B Hold Time: 3 min) to give 2-(2,6-dioxo-3-piperidyl)-4-[4-[[4-[[1-[6-[5-(1-methylcyclopropoxy)-2H-indazol-3-yl]pyrimidin-4-yl]-4-piperidyl]methyl]piperazin-1-yl]methyl]-1-piperidyl]isoindoline-1,3-dione (42 mg, 52.44 μmol, 48.90% yield, 100% purity) as a yellow solid.

Exemplary Synthesis of Compound 147

Step 1

To the mixture of 5-(1-methylcyclopropoxy)-3-[6-[4-(piperazin-1-ylmethyl)-1-piperidyl]pyrimidin-4-yl]-2H-indazole (31.49 mg, 70.35 μmol, 0.5 eq) and 1-[2-(2,6-dioxo-3-piperidyl)-1-oxo-isoindolin-4-yl]piperidine-4-carbaldehyde (50 mg, 140.69 μmol, 1 eq) in HOAC (1 mL) and MeOH (10 mL) was stirred at 25° C. for 20 min, then was added borane; 2-methylpyridine (30.10 mg, 281.38 μmol, 2 eq). Then the mixture was stirred at 25° C. for 16 h under N2. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-35%, 40 min) to afford 3-[4-[4-[[4-[[1-[6-[5-(1-methylcyclopropoxy)-2H-indazol-3-yl]pyrimidin-4-yl]-4-piperidyl]methyl]piperazin-1-yl]methyl]-1-piperidyl]-1-oxo-isoindolin-2-yl]piperidine-2,6-dione (35 mg, 43.83 μmol, 31.16% yield, 98.56% purity) as white solid.

Exemplary Synthesis of Compound 148

Step 1

A mixture of benzyl 4-[2,2-difluoro-2-(4-piperidyl)ethyl]piperazine-1-carboxylate (117.88 mg, 320.82 μmol, 1 eq), 1-[2-(2,6-dioxo-3-piperidyl)-1,3-dioxo-isoindolin-4-yl]piperidine-4-carbaldehyde (71.10 mg, 192.49 μmol, 0.6 eq) in MeOH (10 mL) was added AcOH (1 mL), borane; 2-methylpyridine (34.32 mg, 320.82 μmol, 1 eq), and then the mixture was stirred at 25° C. for 12 h. LCMS showed desired MS. TLC (Petroleum ether:Ethyl acetate=3:1) showed starting material consumed completed and two new major points found. The reaction mixture was concentrated under reduced pressure to give a residue. The crude was purified by a flash chromatography on silica (0-50% Ethyl acetate in Petroleum ether) to give benzyl 4-[2-[1-[[1-[2-(2,6-dioxo-3-piperidyl)-1,3-dioxo-isoindolin-4-yl]-4-piperidyl]methyl]-4-piperidyl]-2,2-difluoro-ethyl]piperazine-1-carboxylate (115 mg, crude) as a yellow solid.

Step 2

A mixture of benzyl 4-[2-[1-[[1-[2-(2,6-dioxo-3-piperidyl)-1,3-dioxo-isoindolin-4-yl]-4-piperidyl]methyl]-4-piperidyl]-2,2-difluoro-ethyl]piperazine-1-carboxylate (115 mg, 159.54 μmol, 1 eq) was added TFA (18.19 mg, 159.54 μmol, 11.81 μL, 1 eq), and then the mixture was stirred at 70° C. for 1 h. TLC (Petroleum ether:Ethyl acetate=3:1) showed started material consumed completed and one new major point found. The reaction mixture was concentrated in vacuum to give 4-[4-[[4-(1,1-difluoro-2-piperazin-1-yl-ethyl)-1-piperidyl]methyl]-1-piperidyl]-2-(2,6-dioxo-3-piperidyl)isoindoline-1,3-dione (110 mg, crude, TFA) as a brown oil.

Step 3

To a solution of 4-[4-[[4-(1,1-difluoro-2-piperazin-1-yl-ethyl)-1-piperidyl]methyl]-1-piperidyl]-2-(2,6-dioxo-3-piperidyl)isoindoline-1,3-dione (93 mg, 158.52 μmol, 1 eq) and 3-(6-chloropyrimidin-4-yl)-5-(1-methylcyclopropoxy)-2H-indazole (47.67 mg, 158.52 μmol, 1 eq) in DMSO (10 mL) was added DIEA (102.44 mg, 792.61 μmol, 138.05 μL, 5 eq). The mixture was stirred at 70° C. for 16 hr under N2 and cooled. The residue was concentrated under reduced pressure to give a residue. The crude product was purified by reversed-phase HPLC (column: 3_Phenomenex Luna C18 75*30 mm*3 um; mobile phase: [water (0.225% FA)-ACN]; B %: 0%-40%, 40 min) to give 4-[4-[[4-[1,1-difluoro-2-[4-[6-[5-(1-methylcyclopropoxy)-1H-indazol-3-yl]pyrimidin-4-yl]piperazin-1-yl]ethyl]-1-piperidyl]methyl]-1-piperidyl]-2-(2,6-dioxo-3-piperidyl)isoindoline-1,3-dione (15.5 mg, 17.85 μmol, 11.26% yield, 98% purity) as a yellow solid.

Exemplary Synthesis of Compound 149

Step 1

To a mixture of 2-(2,6-dioxo-3-piperidyl)-5-fluoro-isoindoline-1,3-dione (230 mg, 832.67 μmol, 9.47 e-1 eq) and tert-butyl 4-(4-piperidyloxy)piperidine-1-carboxylate (250 mg, 879.06 μmol, 1 eq) in DMSO (5 mL) was added DIEA (340.83 mg, 2.64 mmol, 459.34 μL, 3 eq) in one portion at 20° C. The mixture was stirred at 100° C. for 16 h. LCMS showed the reaction was completed. The mixture was cooled to 20° C. The residue was poured into HCl (2 M) to adjust pH=7-8. The aqueous phase was extracted with ethyl acetate (3×10 mL). The combined organic phase was washed with brine (2×10 mL), dried with anhydrous Na2SO4, filtered and concentrated in vacuum. The residue was purified by silica gel chromatography (100-200 mesh silica gel, 0-10% of MeOH in DCM) to give tert-butyl 4-[[1-[2-(2,6-dioxo-3-piperidyl)-1,3-dioxo-isoindolin-5-yl]-4-piperidyl]oxy]piperidine-1-carboxylate (420 mg, 776.91 μmol, 88.38% yield) as a yellow gum.

Step 2

To a mixture of tert-butyl 4-[[1-[2-(2,6-dioxo-3-piperidyl)-1,3-dioxo-isoindolin-5-yl]-4-piperidyl]oxy]piperidine-1-carboxylate (440.58 mg, 814.97 μmol, 1 eq) in DCM (5 mL) was added TFA (3.08 g, 27.01 mmol, 2 mL, 33.15 eq) in one portion at 25° C. under N2. The mixture was stirred at 25° C. for 2 hours to give yellow solution TLC showed the reaction was completed. The residue was concentrated in vacuum to give 2-(2,6-dioxo-3-piperidyl)-5-[4-(4-piperidyloxy)-1-piperidyl]isoindoline-1,3-dione (500 mg, 732.94 μmol, 89.94% yield, 98% purity, 2TFA) as a yellow oil.

Step 3

To a mixture of 2-(2,6-dioxo-3-piperidyl)-5-[4-(4-piperidyloxy)-1-piperidyl]isoindoline-1,3-dione (180 mg, 408.63 μmol, 1 eq) and tert-butyl (2R)-2-(p-tolylsulfonyloxymethyl)morpholine-4-carboxylate (227.68 mg, 612.95 μmol, 1.5 eq) in MeCN (10 mL) was added KI (339.17 mg, 2.04 mmol, 5 eq) and DIPEA (264.07 mg, 2.04 mmol, 355.88 μL, 5 eq) in one portion at 20° C. under N2. The mixture was stirred at 100° C. for 16 hours to give yellow suspension. LCMS desired MS. The mixture was cooled to 25° C. and concentrated in reduced pressure at 25° C. The residue was poured into water (20 mL). The aqueous phase was extracted with ethyl acetate (3×20 mL). The combined organic phase was washed with brine (2×20 mL), dried with anhydrous Na2SO4, filtered and concentrated in vacuum. The residue was purified by silica gel chromatography (column: 12 g, 100-200 mesh silica gel, 0-10% (5 min) of MeOH in DCM, 10% (10 min) of MeOH in DCM) to give tert-butyl (2S)-2-[[4-[[1-[2-(2,6-dioxo-3-piperidyl)-1,3-dioxo-isoindolin-5-yl]-4-piperidyl]oxy]-1-piperidyl]methyl]morpholine-4-carboxylate (255 mg, 362.73 μmol, 88.77% yield, 91% purity) as a yellow gum.

Step 4

To a solution of tert-butyl (2S)-2-[[4-[[1-[2-(2,6-dioxo-3-piperidyl)-1,3-dioxo-isoindolin-5-yl]-4-piperidyl]oxy]-1-piperidyl]methyl]morpholine-4-carboxylate (255 mg, 398.60 μmol, 1 eq) in DCM (5 mL) was added TFA (3.08 g, 27.01 mmol, 2 mL, 67.77 eq) in one portion at 25° C. under N2. The mixture was stirred at 25° C. for 20 min to give yellow solution. LCMS (EB16-910-P1A1) showed the reaction was completed. The solution was concentrated in vacuum to give 2-(2,6-dioxo-3-piperidyl)-5-[4-[[1-[[(2R)-morpholin-2-yl]methyl]-4-piperidyl]oxy]-1-piperidyl]isoindoline-1,3-dione (330 mg, 344.34 μmol, 86.39% yield, 92% purity, 3TFA) as a yellow gum.

Step 5

To a mixture of 2-(2,6-dioxo-3-piperidyl)-5-[4-[[1-[[(2R)-morpholin-2-yl]methyl]-4-piperidyl]oxy]-1-piperidyl]isoindoline-1,3-dione (330 mg, 374.28 μmol, 1.13 eq, 3TFA) and 3-(6-chloropyrimidin-4-yl)-5-(1-methylcyclopropoxy)-1H-indazole (100 mg, 332.51 μmol, 1 eq) in DMSO (5 mL) was added DIEA (343.79 mg, 2.66 mmol, 463.33 μL, 8 eq) in one portion at 20° C. under N2. The mixture was stirred at 80° C. for 36 h. LCMS showed there was desired MS. The mixture was cooled to 20° C. and concentrated in reduced pressure at 20° C. The residue was poured into water (5 mL). The aqueous phase was extracted with ethyl acetate (5 Ml*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 35; FlowRate: 25 mL/min; Gradient Time: 35 min; 100% B Hold Time: 3 min) to give 2-(2,6-dioxo-3-piperidyl)-5-[4-[[1-[[(2S)-4-[6-[5-(1-methylcyclopropoxy)-1H-indazol-3-yl]pyrimidin-4-yl]morpholin-2-yl]methyl]-4-piperidyl]oxy]-1-piperidyl]isoindoline-1,3-dione (45.5 mg, 55.01 μmol, 16.54% yield, 97.19% purity) as a yellow solid.

Exemplary Synthesis of Compound 150

Compound 150 was prepared in a manner analogous to compound 149 using and tert-butyl (2S)-2-(p-tolylsulfonyloxymethyl)morpholine-4-carboxylate.

Exemplary Synthesis of Compound 151

Step 1

To a solution of 8-[4-[5-(1-methylcyclopropoxy)-1H-indazol-3-yl]-2-pyridyl]-2-(4-piperidylmethyl)-5-oxa-2,8-diazaspiro[3.5]nonane (45 mg, 92.10 μmol, 1 eq) in MeOH (5 mL) and HOAc (0.5 mL) was added 1-[2-(2,6-dioxo-3-piperidyl)-1,3-dioxo-isoindolin-5-yl]piperidine-4-carbaldehyde (34.02 mg, 92.10 μmol, 1 eq) and borane; 2-methylpyridine (19.70 mg, 184.19 μmol, 2 eq). After addition, the reaction solution was stirred at 25° C. for 12 h. LCMS showed starting material consumed and desired MS formed. The reaction mixture was concentrated under reduced pressure. The residue was purified by prep.HPLC (column: 3_Phenomenex Luna C18 75*30 mm*3 um; mobile phase: [water (0.225% FA)-ACN]; B %: 0-40%; 40 min) to afford 2-(2,6-dioxo-3-piperidyl)-5-[4-[[4-[[8-[4-[5-(1-methylcyclopropoxy)-1H-indazol-3-yl]-2-pyridyl]-5-oxa-2,8-diazaspiro[3.5]nonan-2-yl]methyl]-1-piperidyl]methyl]-1-piperidyl]isoindoline-1,3-dione (37.3 mg, 43.97 μmol, 47.75% yield, 99.26% purity) as a yellow solid.

Exemplary Synthesis of Compound 152

Step 1

To a solution of 2-(2,6-dioxo-3-piperidyl)-5-[4-(piperazin-1-ylmethyl)-1-piperidyl]isoindoline-1,3-dione (300 mg, 541.98 μmol, 1.34 eq, TFA) and tert-butyl (2S)-2-(p-tolylsulfonyloxymethyl)morpholine-4-carboxylate (150 mg, 403.82 μmol, 1 eq) in CH3CN (5 mL) was added DIEA (260.96 mg, 2.02 mmol, 351.69 μL, 5 eq) and KI (134.07 mg, 807.65 μmol, 2 eq). After addition, the reaction solution mixture was stirred at 80° C. for 12 h. LCMS showed desired MS. TLC (dichloromethane:methanol=10:1) showed several new spots. After cooling, the reaction mixture was diluted with water (10 mL) and extracted with ethyl acetate (3×10 mL). The organic layer was dried over sodium sulfate and concentrated under reduced pressure. The residue was purified by silica gel column chromatography (0 to 10% methanol in dichloromethane) to afford tert-butyl (2R)-2-[[4-[[1-[2-(2,6-dioxo-3-piperidyl)-1,3-dioxo-isoindolin-5-yl]-4-piperidyl]methyl]piperazin-1-yl]methyl]morpholine-4-carboxylate (107 mg, 150.76 μmol, 37.33% yield, 90% purity) as a yellow solid.

Step 2

To a solution of tert-butyl (2R)-2-[[4-[[1-[2-(2,6-dioxo-3-piperidyl)-1,3-dioxo-isoindolin-5-yl]-4-piperidyl]methyl]piperazin-1-yl]methyl]morpholine-4-carboxylate (105 mg, 164.38 μmol, 1 eq) in DCM (5 mL) was added TFA (4.62 g, 40.52 mmol, 3 mL, 246.49 eq). After addition, the reaction solution mixture was stirred at 25° C. for 1 h. LCMS showed desired MS. The reaction mixture was concentrated under pressure to afford 2-(2,6-dioxo-3-piperidyl)-5-[4-[[4-[[(2S)-morpholin-2-yl]methyl]piperazin-1-yl]methyl]-1-piperidyl]isoindoline-1,3-dione (110 mg, crude, TFA) as a yellow solid. The crude product was used for next step directly.

Step 3

To a solution of 2-(2,6-dioxo-3-piperidyl)-5-[4-[[4-[[(2S)-morpholin-2-yl]methyl]piperazin-1-yl]methyl]-1-piperidyl]isoindoline-1,3-dione (88 mg, 134.83 μmol, 1.01 eq, TFA) and 3-(6-chloropyrimidin-4-yl)-5-(1-methylcyclopropoxy)-2H-indazole (40 mg, 133.00 μmol, 1 eq) in DMSO (1.5 mL) was added DIEA (85.95 mg, 665.02 μmol, 115.83 μL, 5 eq). After addition, the reaction solution was stirred at 90° C. for 16 h. LCMS showed major desired MS. After cooling, the reaction mixture was diluted with ethyl acetate (10 mL) and washed with brine (2×5 mL). The organic layer was concentrated under reduced pressure. The residue was purified by prep.HPLC (column: 3_Phenomenex Luna C18 75*30 mm*3 um; mobile phase: [water (0.225% FA)-ACN]; B %: 0-35%; 40 min) to afford 2-(2,6-dioxo-3-piperidyl)-5-[4-[[4-[[(2R)-4-[6-[5-(1-methylcyclopropoxy)-1H-indazol-3-yl]pyrimidin-4-yl]morpholin-2-yl]methyl]piperazin-1-yl]methyl]-1-piperidyl]isoindoline-1,3-dione (22.1 mg, 27.40 μmol, 20.60% yield, 99.53% purity) as a yellow solid.

Exemplary Synthesis of Compound 153

Compound 153 was prepared in a manner analogous to compound 152 using and tert-butyl (2R)-2-(p-tolylsulfonyloxymethyl)morpholine-4-carboxylate.

Exemplary Synthesis of Compound 154

Step 1

To a mixture of 2-[[3-(6-chloropyrimidin-4-yl)-5-(1-methylcyclopropoxy)indazol-2-yl]methoxy]ethyl-trimethyl-silane (1 g, 2.32 mmol, 1 eq), 2-morpholin-2-ylethanol (304.34 mg, 2.32 mmol, 1 eq) in DMSO (10 mL) was added Et3N (704.34 mg, 6.96 mmol, 968.82 μL, 3 eq) in one portion and then was stirred at 100° C. for 1 h. TLC showed the starting material was consumed completely. The mixture was cooled to 20° C., then the residue was poured into water (10 mL). The aqueous phase was extracted with ethyl acetate (3×10 mL). The combined organic phase was washed with brine (2×10 mL), dried with anhydrous Na2SO4, filtered and concentrated in vacuum. The residue was purified by silica gel chromatography (0-10% (10 min) of Ethyl acetate in Petroleum ether, 10% (5 min) of Ethyl acetate in Petroleum ether) to give 2-[4-[6-[5-(1-methylcyclopropoxy)-2-(2-trimethylsilylethoxymethyl)indazol-3-yl]pyrimidin-4-yl]morpholin-2-yl]ethanol (1.1 g, 2.09 mmol, 90.18% yield) as a yellow oil.

Step 2

To a mixture of 2-[4-[6-[5-(1-methylcyclopropoxy)-2-(2-trimethylsilylethoxymethyl)indazol-3-yl]pyrimidin-4-yl]morpholin-2-yl]ethanol (1.1 g, 2.09 mmol, 1 eq) and 4-methylbenzenesulfonyl chloride (796.90 mg, 4.18 mmol, 2 eq) in DCM (5 mL) was added TEA (211.49 mg, 2.09 mmol, 290.90 μL, 1 eq) and DMAP (255.34 mg, 2.09 mmol, 1 eq) in one portion at 20° C. under N2. The mixture was stirred at 20° C. for 1 h to give yellow solution. TLC (Petroleum ether:Ethyl acetate=3:1, Rf=0.23, UA 254 nm) showed the reaction was completed. The residue was poured into water (5 mL). The aqueous phase was extracted with DCM (5 mL*3). The combined organic phase was washed with brine (5 mL*3), dried with anhydrous Na2SO4, filtered and concentrated in vacuum. The residue was purified by silica gel chromatography (0-10% (10 min) of Ethyl acetate in Petroleum ether, 10% (10 min) of Ethyl acetate in Petroleum ether) to give 2-[4-[6-[5-(1-methylcyclopropoxy)-2-(2-trimethylsilylethoxymethyl)indazol-3-yl]pyrimidin-4-yl]morpholin-2-yl]ethyl 4-methylbenzenesulfonate (830 mg, 1.22 mmol, 58.41% yield) as a yellow solid.

Step 3

To a mixture of 2-[4-[6-[5-(1-methylcyclopropoxy)-2-(2-trimethylsilylethoxymethyl)indazol-3-yl]pyrimidin-4-yl]morpholin-2-yl]ethyl 4-methylbenzenesulfonate (830 mg, 1.22 mmol, 1 eq) and tert-butyl piperazine-1-carboxylate (454.74 mg, 2.44 mmol, 2 eq) in MeCN (10 mL) was added KI (405.29 mg, 2.44 mmol, 2 eq) and DIPEA (315.54 mg, 2.44 mmol, 425.26 μL, 2 eq) in one portion at 20° C. under N2. The mixture was stirred at 80° C. for 2 hours. LCMS showed desired MS. The mixture was cooled to 20° C. and concentrated in reduced pressure at 20° C. The residue was poured into water (10 mL). The aqueous phase was extracted with ethyl acetate (10 mL*3). The combined organic phase was washed with brine (10 mL*2), dried with anhydrous Na2SO4, filtered and concentrated in vacuum. The residue was purified by silica gel chromatography (0-40% (15 min) of Ethyl acetate in Petroleum ether, 40% (5 min) of Ethyl acetate in Petroleum ether) to give tert-butyl 4-[2-[4-[6-[5-(1-methylcyclopropoxy)-1-(2-trimethylsilylethoxymethyl)indazol-3-yl]pyrimidin-4-yl]morpholin-2-yl]ethyl]piperazine-1-carboxylate (800 mg, 1.15 mmol, 94.43% yield) as a yellow gum.

Step 4

To a mixture of tert-butyl 4-[2-[4-[6-[5-(1-methylcyclopropoxy)-1-(2-trimethylsilylethoxymethyl)indazol-3-yl]pyrimidin-4-yl]morpholin-2-yl]ethyl]piperazine-1-carboxylate (800 mg, 1.15 mmol, 1 eq) in MeOH (5 mL) was added HCl/dioxane (4 M, 5.72 mL, 19.84 eq) in one portion at 25° C. The mixture was stirred at 65° C. for 1 h. TLC showed the reaction was completed. The residue was adjusted the pH=9-10, the aqueous phase was extracted with DCM (10 mL*3). The combined organic phase was washed with brine (10 mL*2), dried with anhydrous Na2SO4, filtered and concentrated in vacuum to give 4-[6-[5-(1-methylcyclopropoxy)-1H-indazol-3-yl]pyrimidin-4-yl]-2-(2-piperazin-1-ylethyl)morpholine (500 mg, 1.06 mmol, 91.69% yield, 98% purity) as a yellow gum.

Step 5

4-[6-[5-(1-methylcyclopropoxy)-1H-indazol-3-yl]pyrimidin-4-yl]-2-(2-piperazin-1-ylethyl)morpholine (500 mg, 1.08 mmol, 1 eq) was separated by SFC (Column: DAICEL CHIRALPAK IE (250 mm*30 mm, 10 um); Condition: 0.1% NH3H2O ETOH; Begin B: 55; End B: 55; FlowRate: 80 mL/min) to give (2S)-4-[6-[5-(1-methylcyclopropoxy)-1H-indazol-3-yl]pyrimidin-4-yl]-2-(2-piperazin-1-ylethyl)morpholine or the enantiomer thereof (212 mg, crude) (Rt=2.224 min, 212 mg) and (2R)-4-[6-[5-(1-methylcyclopropoxy)-1H-indazol-3-yl]pyrimidin-4-yl]-2-(2-piperazin-1-ylethyl)morpholine or the enantiomer thereof (291 mg, crude) (Rt=2.712 min, 291 mg) both as yellow solid.

Step 6

To a mixture of (2R)-4-[6-[5-(1-methylcyclopropoxy)-1H-indazol-3-yl]pyrimidin-4-yl]-2-(2-piperazin-1-ylethyl)morpholine or the enantiomer thereof (100.00 mg, 215.72 μmol, 1 eq) and 1-[2-(2,6-dioxo-3-piperidyl)-1,3-dioxo-isoindolin-5-yl]piperidine-4-carbaldehyde (79.68 mg, 215.72 μmol, 1 eq) in MeOH (5 mL) and HOAc (0.5 mL) was added borane; 2-methylpyridine (46.15 mg, 431.43 μmol, 2 eq) in one portion at 20° C. under N2. The mixture was stirred at 30° C. for 16 h. LCMS showed desired MS. The residue was poured into water (2 mL). The aqueous phase was extracted with ethyl acetate (2 mL*3). The combined organic phase was washed with brine (2 mL*2), dried with anhydrous Na2SO4, filtered, and concentrated in vacuum. The crude product was purified by reversed-phase HPLC (column: 3_Phenomenex Luna C18 75*30 mm*3 um; mobile phase: [water (0.225% FA)-ACN]; B %: 0%-35%, 40 min) to give 2-(2,6-dioxo-3-piperidyl)-5-[4-[[4-[2-[(2S)-4-[6-[5-(1-methylcyclopropoxy)-1H-indazol-3-yl]pyrimidin-4-yl]morpholin-2-yl]ethyl]piperazin-1-yl]methyl]-1-piperidyl]isoindoline-1,3-dione or the enantiomer thereof (59.6 mg, 72.73 μmol, 33.72% yield, 99.69% purity) as a yellow solid.

Exemplary Synthesis of Compound 155

Compound 155 was prepared in a manner analogous to compound 154 using (2S)-4-[6-[5-(1-methylcyclopropoxy)-1H-indazol-3-yl]pyrimidin-4-yl]-2-(2-piperazin-1-ylethyl)morpholine or the enantiomer thereof.

Exemplary Synthesis of Compound 156

Step 1

To a solution of 5-(1-methylcyclopropoxy)-3-(6-piperazin-1-ylpyrimidin-4-yl)-1H-indazole (300 mg, 775.44 μmol, 1 eq, HCl) and tert-butyl (2S)-2-(p-tolylsulfonyloxymethyl)morpholine-4-carboxylate (500 mg, 1.35 mmol, 1.74 eq) in CH3CN (5 mL) was added DIEA (501.10 mg, 3.88 mmol, 675.34 μL, 5 eq) and KI (386.17 mg, 2.33 mmol, 3 eq). After addition, the reaction mixture was stirred at 80° C. for 12 h. Then the reaction mixture was heated to 100° C. for 12 h. TLC (dichloromethane:methanol=10:1) showed major one new spot. The reaction mixture was diluted with water (15 mL) and extracted with dichloromethane (3×10 mL). The organic layer was dried over sodium sulfate and concentrated under reduced pressure. The residue was purified by silica gel column chromatography (0 to 6% methanol in chloromethane) to afford tert-butyl (2R)-2-[[4-[6-[5-(1-methylcyclopropoxy)-1H-indazol-3-yl]pyrimidin-4-yl]piperazin-1-yl]methyl]morpholine-4-carboxylate (450 mg, 736.82 μmol, 95.02% yield, 90% purity) as a light yellow solid.

Step 2

To a solution of tert-butyl (2R)-2-[[4-[6-[5-(1-methylcyclopropoxy)-1H-indazol-3-yl]pyrimidin-4-yl]piperazin-1-yl]methyl]morpholine-4-carboxylate (450 mg, 818.68 μmol, 1 eq) in DCM (3 mL) was added TFA (4.62 g, 40.52 mmol, 3 mL, 49.49 eq). After addition, the reaction solution was stirred at 20° C. for 1 h. LCMS showed starting material consumed and desired MS found. The reaction mixture was concentrated under reduced pressure. The resulting mixture was dissolved in dichloromethane (3 mL) and treated with DIEA (1 mL). The mixture was concentrated in vacuo to afford (2S)-2-[[4-[6-[5-(1-methylcyclopropoxy)-1H-indazol-3-yl]pyrimidin-4-yl]piperazin-1-yl]methyl]morpholine (340 mg, crude) as a yellow solid. The crude product was used for next step directly.

Step 3

To a solution of (2S)-2-[[4-[6-[5-(1-methylcyclopropoxy)-1H-indazol-3-yl]pyrimidin-4-yl]piperazin-1-yl]methyl]morpholine (162.00 mg, 360.36 μmol, 1.48 eq) in MeOH (3 mL), DMSO (0.5 mL) and HOAc (0.5 mL) was added 1-[2-(2,6-dioxo-3-piperidyl)-1,3-dioxo-isoindolin-5-yl]piperidine-4-carbaldehyde (90 mg, 243.66 μmol, 1 eq) and borane; 2-methylpyridine (52.12 mg, 487.32 μmol, 2 eq). After addition, the reaction solution was stirred at 20° C. for 12 h. LCMS showed starting material consumed and desired MS found. The reaction mixture was diluted with water (15 mL) and extracted with dichloromethane (3×15 mL). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 0-30%; 35 min) to afford 2-(2,6-dioxo-3-piperidyl)-5-[4-[[(2R)-2-[[4-[6-[5-(1-methylcyclopropoxy)-1H-indazol-3-yl]pyrimidin-4-yl]piperazin-1-yl]methyl]morpholin-4-yl]methyl]-1-piperidyl]isoindoline-1,3-dione (112.9 mg, 139.18 μmol, 57.12% yield, 98.98% purity) as a yellow solid.

Exemplary Synthesis of Compound 157

Compound 157 was prepared in a manner analogous to compound 156 using tert-butyl (2R)-2-(p-tolylsulfonyloxymethyl)morpholine-4-carboxylate.

Exemplary Synthesis of Compound 158

Step 1

To a solution of (2S)-2-[[4-[6-[5-(1-methylcyclopropoxy)-1H-indazol-3-yl]pyrimidin-4-yl]piperazin-1-yl]methyl]morpholine (140.00 mg, 311.42 μmol, 1.71 eq) in MeOH (3 mL) and HOAc (0.3 mL) was added 2-[1-[2-(2,6-dioxo-3-piperidyl)-1,3-dioxo-isoindolin-5-yl]-4-piperidyl]acetaldehyde (70 mg, 182.58 μmol, 1 eq) and borane; 2-methylpyridine (39.06 mg, 365.16 μmol, 2 eq). After addition, the reaction solution was stirred at 20° C. for 12 h. LCMS showed desired MS. The reaction mixture was diluted with water (15 mL) and extracted with dichloromethane (3×15 mL). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 0-35%; 35 min) to afford 2-(2,6-dioxo-3-piperidyl)-5-[4-[2-[(2R)-2-[[4-[6-[5-(1-methylcyclopropoxy)-1H-indazol-3-yl]pyrimidin-4-yl]piperazin-1-yl]methyl]morpholin-4-yl]ethyl]-1-piperidyl]isoindoline-1,3-dione (94.3 mg, 114.86 μmol, 62.91% yield, 99.51% purity) as a yellow solid.

Exemplary Synthesis of Compound 159

Step 1

To a mixture of 2-(2,6-dioxo-3-piperidyl)-5-fluoro-isoindoline-1,3-dione (450 mg, 1.63 mmol, 9.41 e-1 eq) and 4-(2,2-dimethoxyethyl)piperidine (300 mg, 1.73 mmol, 1 eq) in DMSO (5 mL) was added DIEA (2.24 g, 17.32 mmol, 3.02 mL, 10 eq) in one portion at 20° C. The mixture was stirred at 100° C. for 16 h. LCMS showed the reaction was completed. The mixture was cooled to 20° C. The residue was poured into HCl (2 M) to adjust pH=7-8. The aqueous phase was extracted with ethyl acetate (3×10 mL). The combined organic phase was washed with brine (2×10 mL), dried with anhydrous Na2SO4, filtered and concentrated in vacuum. The residue was purified by silica gel chromatography (100-200 mesh silica gel, 0-10% of MeOH in DCM) to give 5-[4-(2,2-dimethoxyethyl)-1-piperidyl]-2-(2,6-dioxo-3-piperidyl)isoindoline-1,3-dione (673 mg, 1.57 mmol, 90.50% yield) as a yellow gum.

Step 2

To a mixture of 5-[4-(2,2-dimethoxyethyl)-1-piperidyl]-2-(2,6-dioxo-3-piperidyl)isoindoline-1,3-dione (350 mg, 814.97 μmol, 1 eq) in THF (5 mL) was added HCl (2 M, 69.94 mL, 171.63 eq) in one portion at 25° C. under N2. The mixture was stirred at 25° C. for 2 hours to give yellow solution. LCMS showed desired MS. The residue was poured into saturated $NaHCO_3$ to adjusted the pH=7-8. The aqueous phase was extracted with ethyl acetate (20 mL*3). The combined organic phase was washed with brine (20 mL*2), dried with anhydrous Na2SO4, filtered and concentrated in vacuum to give 2-[l-[2-(2,6-dioxo-3-piperidyl)-1,3-dioxo-isoindolin-5-yl]-4-piperidyl]acetaldehyde (290 mg, 658.06 μmol, 80.75% yield, 87% purity) as a yellow solid.

Step 3

To a mixture of 5-(1-methylcyclopropoxy)-3-[6-[(3S)-3-methyl-4-(4-piperidylmethyl)piperazin-1-yl]pyrimidin-4-yl]-1H-indazole (60 mg, 129.98 μmol, 1 eq) and 2-[1-[2-(2,6-dioxo-3-piperidyl)-1,3-dioxo-isoindolin-5-yl]-4-piperidyl]acetaldehyde (59.80 mg, 155.98 μmol, 1.2 eq) in MeOH (5 mL) was added HOAc (0.5 mL) and borane; 2-methylpyridine (27.81 mg, 259.96 μmol, 2 eq) in one portion at 20° C. under N2. The mixture was stirred at 20° C. for 16 h. LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0; End B: 35; FlowRate: 35 mL/min; Gradient Time: 35 min; 100% B Hold Time: 1 min) to give 2-(2,6-dioxo-3-piperidyl)-5-[4-[2-[4-[[(2S)-2-methyl-4-[6-[5-(1-methylcyclopropoxy)-1H-indazol-3-yl]pyrimidin-4-yl]piperazin-1-yl]methyl]-1-piperidyl]ethyl]-1-piperidyl]isoindoline-1,3-dione (61.9 mg, 73.82 μmol, 56.79% yield, 98.86% purity) as a yellow solid.

Exemplary Synthesis of Compound 160

Step 1

To a solution of tert-butyl 3-methyleneazetidine-1-carboxylate (2.5 g, 14.77 mmol, 1 eq) was added 9-BBN (0.5 M, 29.55 mL, 1 eq) at 25° C. The reaction mixture was stirred at 80° C. for 1 h under N2. After cooling, 4-bromopyridine (2.33 g, 14.77 mmol, 1 eq), Pd(dppf)Cl2 (648.59 mg, 886.41 μmol, 0.06 eq), K2CO3 (3.06 g, 22.16 mmol, 1.5 eq), DMF (20 mL) and H2O (5 mL) were added to the reaction. The resultant mixture was heated to 60° C. for 12 h. LCMS showed desired MS. After cooling, the reaction mixture was diluted with water (20 mL) and extracted with ethyl acetate (3×50 mL). The organic layer was washed with brine (2×50 mL), dried over sodium sulfate and concentrated under reduced pressure. The residue was purified by silica gel column chromatography (0 to 40% ethyl acetate in petroleum ether) to give tert-butyl 3-(4-pyridylmethyl)azetidine-1-carboxylate (2.1 g, 8.46 mmol, 57.24% yield) as a yellow oil.

Step 2

To a solution of tert-butyl 3-(4-pyridylmethyl)azetidine-1-carboxylate (2.1 g, 8.46 mmol, 1 eq) in EtOH (20 mL) and HOAc (507.85 mg, 8.46 mmol, 483.67 μL, 1 eq) was added PtO2 (288.05 mg, 1.27 mmol, 0.15 eq) at 25° C. Then the mixture was stirred at 70° C. for 16 h under H2 (50 psi). TLC (PE:EA=1:1) showed starting material consumed and a new spot formed. After cooling, the reaction was filtered and filtrate was concentrated under reduced pressure to give tert-butyl 3-(4-piperidylmethyl)azetidine-1-carboxylate (2.7 g, crude) as a yellow gum.

Step 3

To a mixture of tert-butyl 3-(4-piperidylmethyl)azetidine-1-carboxylate (1 g, 3.93 mmol, 1 eq) and benzyl 4-formylpiperidine-1-carboxylate (972.17 mg, 3.93 mmol, 1 eq) in MeOH (10 mL) was added HOAc (236.08 mg, 3.93 mmol, 224.83 μL, 1 eq), borane; 2-methylpyridine (841.00 mg, 7.86 mmol, 2 eq) and HOAc (236.08 mg, 3.93 mmol, 224.83 μL, 1 eq) in one portion at 25° C. under N2. The mixture was stirred at 25° C. for 1 h. TLC (Dichloromethane:Methanol=10:1, Rf=0.21, PMA) showed the reaction was completed. LCMS showed there was desired MS. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The residue was purified by silica gel chromatography (Dichloromethane:Methanol=10:1, Rf=0.43, 0-100% (20 min) of Ethyl acetate in Petroleum ether, 100% (10 min) of Ethyl acetate in Petroleum ether) to give benzyl 4-[[4-[(1-tert-butoxycarbonylazetidin-3-yl)methyl]-1-piperidyl]methyl]piperidine-1-carboxylate (1 g, 1.89 mmol, 48.19% yield, 92% purity) as a yellow oil.

Step 4

To a mixture of benzyl 4-[[4-[(1-tert-butoxycarbonylazetidin-3-yl)methyl]-1-piperidyl]methyl]piperidine-1-carboxylate (1 g, 2.06 mmol, 1 eq) in DCM (10 mL) was added TFA (7.70 g, 67.53 mmol, 5 mL, 32.80 eq) in one portion at 25° C. under N2. The mixture was stirred at 25° C. for 30 min. TLC showed the reaction was completed. The residue was poured into $NaHCO_3$ aq to adjust pH=7-8. The aqueous phase was extracted with ethyl acetate (10 mL*3). The combined organic phase was washed with brine (10 mL*3), dried with anhydrous Na2SO4, filtered and concentrated in vacuum to give benzyl 4-[[4-(azetidin-3-ylmethyl)-1-piperidyl]methyl]piperidine-1-carboxylate (800 mg, 1.39 mmol, 67.52% yield, 67% purity) as a yellow oil.

Step 5

To a mixture of 4-bromo-2-fluoro-pyridine (365.17 mg, 2.08 mmol, 1 eq) and benzyl 4-[[4-(azetidin-3-ylmethyl)-1-piperidyl]methyl]piperidine-1-carboxylate (800 mg, 2.08 mmol, 1 eq) in DMSO (10 mL) was added K2CO3 (1.43 g, 10.38 mmol, 70.14 mL, 5 eq) in one portion at 100° C. under N2. The mixture was stirred at 100° C. for 2 h to give yellow solution. LCMS showed the reaction was completed. The mixture was cooled to 20° C. and concentrated in reduced pressure at 20° C. The residue was poured into water (50 mL). The aqueous phase was extracted with ethyl acetate (50 mL*4). The combined organic phase was washed with brine (50 mL*2), dried with anhydrous Na2SO4, filtered and concentrated in vacuum. The residue was purified by silica gel chromatography (Petroleum ether:Ethyl acetate=1:1, Rf=0.56, 20 g, 0-50% (10 min) of Ethyl acetate in Petroleum ether, 50% (10 min) of Ethyl acetate in Petroleum ether) to give benzyl 4-[[4-[[11-(4-bromo-2-pyridyl)azetidin-3-yl]methyl]-1-piperidyl]methyl]piperidine-1-carboxylate (830 mg, 1.53 mmol, 73.87% yield) as a yellow oil.

Step 6

To a solution of benzyl 4-[[4-[[1-(4-bromo-2-pyridyl)azetidin-3-yl]methyl]-1-piperidyl]methyl]piperidine-1-carboxylate (423 mg, 781.13 μmol, 1 eq) and 4,4,5,5-tetramethyl-2-(4,4,5,5-tetramethyl-1,3,2-dioxaborolan-2-yl)-1,3,2-dioxaborolane (396.72 mg, 1.56 mmol, 2. eq) in dioxane (10 mL) was added Pd(dppf)Cl2 (57.16 mg, 78.11 μmol, 0.1 eq), KOAc (229.98 mg, 2.34 mmol, 3 eq). Then the mixture was stirred at 100° C. for 16 hr under N2. TLC (Dichloromethane:Methanol=10:1, Rf=0.5) showed the reaction a new spot. The reaction mixture was filtered and concentrated under reduced pressure to afford [2-[3-[[1-[(1-benzyloxycarbonyl-4-piperidyl)methyl]-4-piperidyl]methyl]azetidin-1-yl]-4-pyridyl]boronic acid (395 mg, crude) as a brown solid.

Step 7

To a solution of [2-[3-[[1-[(1-benzyloxycarbonyl-4-piperidyl)methyl]-4-piperidyl]methyl]azetidin-1-yl]-4-pyridyl] boronic acid (395 mg, 779.95 μmol, 1 eq) and 2-[[3-iodo-5-(1-methylcyclopropoxy)indazol-1-yl]methoxy]ethyl-trimethyl-silane (250 mg, 562.34 μmol, 7.21 e-1 eq) in dioxane (10 mL) and H2O (2 mL) was added Pd(dppf)Cl2 (85.60 mg, 116.99 μmol, 0.15 eq), Na2CO3 (248.00 mg, 2.34 mmol, 3 eq). Then the mixture was stirred at 100° C. for 3 hr under N2. TLC (Petroleum ether:Ethyl acetate=0:1, Rf=0.02) showed no start material and one major new spot with larger polarity was detected. The reaction mixture was filtered and concentrated under reduced pressure. The residue was purified by silica gel column chromatography (0 to 100% Ethyl acetate in Petroleum ether) to give benzyl 4-[[4-[[1-[4-[5-(1-methylcyclopropoxy)-1-(2-trimethylsilylethoxymethyl)indazol-3-yl]-2-pyridyl]azetidin-3-yl]methyl]-1-piperidyl]methyl]piperidine-1-carboxylate (175 mg, 141.51 μmol, 18.14% yield, 63% purity) as a yellow solid.

Step 8

To a solution of benzyl 4-[[4-[[1-[4-[5-(1-methylcyclopropoxy)-1-(2-trimethylsilylethoxymethyl)indazol-3-yl]-2-pyridyl]azetidin-3-yl]methyl]-1-piperidyl]methyl]piperidine-1-carboxylate (175 mg, 224.62 μmol, 1 eq) in MeOH (4 mL) was added HCl/dioxane (4 M, 4 mL, 71.23 eq) the mixture was stirred at 65° C. for 1 h. The reaction mixture was filtered and concentrated under reduced pressure. The crude product was in TFA (6.16 g, 54.02 mmol, 4.00 mL, 240.51 eq) and stirred at 90° C. for 1 h under N2. The reaction mixture was filtered and concentrated under reduced pressure to afford 5-(1-methylcyclopropoxy)-3-[2-[3-[[1-(4-piperidylmethyl)-4-piperidyl]methyl]azetidin-1-yl]-4-pyridyl]-1H-indazole (115 mg, crude) as a yellow gum.

Step 9

To a solution of 5-(1-methylcyclopropoxy)-3-[2-[3-[[1-(4-piperidylmethyl)-4-piperidyl]methyl]azetidin-1-yl]-4-pyridyl]-1H-indazole (115 mg, 223.43 μmol, 1 eq) and 2-(2,6-dioxo-3-piperidyl)-5-fluoro-isoindoline-1,3-dione (92.57 mg, 335.14 μmol, 1.5 eq) in DMSO (5 mL) and DIEA (288.76 mg, 2.23 mmol, 389.17 μL, 10 eq). The mixture was stirred at 80° C. for 16 h. LCMS showed desired product MS. The resulting product was poured into H2O (20 mL). The mixture was extracted with ethyl acetate (20 mL*3). The organic phase was washed with brine (15 mL*2), dried over anhydrous Na2SO4, concentrated in vacuum to give a residue. The residue was purified by prep-HPLC (column: 3_Phenomenex Luna C18 75*30 mm*3 um; mobile phase: [water (0.225% FA)-ACN; B %: 0%-40%, 40 min) to afford 2-(2,6-dioxo-3-piperidyl)-5-[4-[[4-[[1-[4-[5-(1-methylcyclopropoxy)-1H-indazol-3-yl]-2-pyridyl]azetidin-3-yl]methyl]-1-piperidyl]methyl]-1-piperidyl]isoindoline-1,3-dione (8.8 mg, 11.30 μmol, 5.06% yield, 99% purity) as yellow solid.

Exemplary Synthesis of Compound 161

Compound 161 was prepared in a manner analogous to compound 99 starting from tert-butyl 2,6-diazaspiro[3.3]heptane-2-carboxylate.

Step 1

To a solution of 5-(1-methylcyclopropoxy)-3-[2-[6-(4-piperidylmethyl)-2,6-diazaspiro[3.3]heptan-2-yl]-4-pyridyl]-1H-indazole (82 mg, 178.81 μmol, 1 eq) and 1-[2-(2,6-dioxo-3-piperidyl)-1,3-dioxo-isoindolin-5-yl]piperidine-4-carbaldehyde (100 mg, 270.73 μmol, 1.51 eq) in MeOH (3 mL) and HOAc (0.3 mL) was added borane; 2-methylpyridine (57.38 mg, 536.42 μmol, 3 eq). After addition, the reaction solution was stirred at 25° C. for 2 h. LCMS showed starting material consumed and desired MS was detected. The reaction mixture was concentrated under reduced pressure. The residue was purified by prep.HPLC (column: 3_Phenomenex Luna C18 75*30 mm*3 um; mobile phase: [water (0.225% FA)-ACN]; B %: 0-30%; 30 min) to afford 2-(2,6-dioxo-3-piperidyl)-5-[4-[[4-[[2-[4-[5-(1-methylcyclopropoxy)-1H-indazol-3-yl]-2-pyridyl]-2,6-diazaspiro[3.3]heptan-6-yl]methyl]-1-piperidyl]methyl]-1-piperidyl]isoindoline-1,3-dione (45.8 mg, 55.53 μmol, 31.06% yield, 98.45% purity) as a yellow solid.

Exemplary Synthesis of Compound 162

Compound 162 was prepared in a manner analogous to compound 99 starting from tert-butyl 1,6-diazaspiro[3.3]heptane-6-carboxylate.

Step 1

To a mixture of 5-(1-methylcyclopropoxy)-3-[2-[6-(4-piperidylmethyl)-1,6-diazaspiro[3.3]heptan-1-yl]-4-pyridyl]-1H-indazole (80 mg, 174.45 μmol, 1 eq) in MeOH (2 mL) and HOAc (0.2 mL) was added borane; 2-methylpyridine (37.32 mg, 348.89 μmol, 2 eq) 1-[2-(2,6-dioxo-3-piperidyl)-1,3-dioxo-isoindolin-5-yl]piperidine-4-carbaldehyde (96.65 mg, 261.67 μmol, 1.5 eq) in one portion at 25° C., then borane; 2-methylpyridine (37.32 mg, 348.89 μmol, 2 eq) was added. The mixture was stirred at 25° C. for 12 hours. LCMS showed the reaction was completed. The mixture was poured into H2O (0.5 mL) and concentrated in reduced pressure. The residue was purified by prep-HPLC (column: 3_Phenomenex Luna C18 75*30 mm*3 um; mobile phase: [water (0.225% FA)-ACN]; B %: 10%-40%, 30 min) to afford 2-(2,6-dioxo-3-piperidyl)-5-[4-[[4-[[1-[4-[5-(1-methylcyclopropoxy)-1H-indazol-3-yl]-2-pyridyl]-1,6-diazaspiro[3.3]heptan-6-yl]methyl]-1-piperidyl]methyl]-1-piperidyl]isoindoline-1,3-dione (124.4 mg, 151.68 μmol, 86.95% yield, 99% purity) as a light yellow solid.

Exemplary Synthesis of Compound 163

Compound 163 was prepared in a manner analogous to compound 99 starting from tert-butyl 1,6-diazaspiro[3.3]heptane-6-carboxylate.

Step 1

To a solution of 5-(1-methylcyclopropoxy)-3-[2-[1-(4-piperidylmethyl)-1,6-diazaspiro[3.3]heptan-6-yl]-4-pyridyl]-1H-indazole (83 mg, 144.95 μmol, 1 eq, TFA) in DCM (5 mL) was added DIEA (93.67 mg, 724.74 μmol, 126.23 μL, 5 eq) and stirred at 20° C. for 10 min. Then the mixture was concentrated. The residue and 1-[2-(2,6-dioxo-3-piperidyl)-1,3-dioxo-isoindolin-5-yl]piperidine-4-carbaldehyde (58.89 mg, 159.44 μmol, 1.1 eq) in HOAC (1 mL) and MeOH (10 mL) was stirred at 20° C. for 20 min, then was added borane; 2-methylpyridine (31.01 mg, 289.90 μmol, 2 eq). Then the mixture was stirred at 25° C. for 16 h under N2. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-35%, 35 min) to afford 2-(2,6-dioxo-3-piperidyl)-5-[4-[[4-[[6-[4-[5-(1-methylcyclopropoxy)-1H-indazol-3-yl]-2-pyridyl]-1,6-diazaspiro[3.3]heptan-1-yl]methyl]-1-piperidyl]methyl]-1-piperidyl]

isoindoline-1,3-dione (22.2 mg, 26.99 μmol, 18.62% yield, 98.73% purity) as a yellow solid.

Exemplary Synthesis of Compound 164

Step 1

A mixture of tert-butyl 3-(4-piperidylmethyl)azetidine-1-carboxylate (68.86 mg, 270.73 μmol, 1 eq), 1-[2-(2,6-dioxo-3-piperidyl)-1,3-dioxo-isoindolin-5-yl]piperidine-4-carbaldehyde (100 mg, 270.73 μmol, 1 eq) in MeOH (10 mL) was added AcOH (1 mL), borane; 2-methylpyridine (57.92 mg, 541.46 μmol, 2 eq) and then the mixture was stirred at 25° C. for 2 hr under N2. LCMS showed the starting material was consumed completely and desired MS found. The reaction mixture was concentrated under reduced pressure to give a residue. The residue was purified by silica gel column chromatography (0 to 30% Dichloromethane in Methanol) to give tert-butyl 3-[[1-[[1-[2-(2,6-dioxo-3-piperidyl)-1,3-dioxo-isoindolin-5-yl]-4-piperidyl]methyl]-4-piperidyl] methyl]azetidine-1-carboxylate (133 mg, 94.10 μmol, 34.76% yield, 43% purity) as a yellow solid.

Step 2

A mixture of tert-butyl 3-[[1-[[1-[2-(2,6-dioxo-3-piperidyl)-1,3-dioxo-isoindolin-5-yl]-4-piperidyl]methyl]-4-piperidyl]methyl]azetidine-1-carboxylate (133 mg, 218.84 μmol, 1 eq) in DCM (2 mL) was added TFA (3.08 g, 27.01 mmol, 2 mL, 123.43 eq). and then the mixture was stirred at 25° C. for 2 hr under N2. TLC (Petroleum ether:Ethyl acetate=3:1) found one new spot. The reaction mixture was concentrated under reduced pressure to give 5-[4-[[4-(azetidin-3-ylmethyl)-1-piperidyl]methyl]-1-piperidyl]-2-(2,6-dioxo-3-piperidyl)isoindoline-1,3-dione (100 mg, crude, TFA) as a brown oil.

Step 3

To a solution of 5-[4-[[4-(azetidin-3-ylmethyl)-1-piperidyl]methyl]-1-piperidyl]-2-(2,6-dioxo-3-piperidyl)isoindoline-1,3-dione (100 mg, 197.00 μmol, 1 eq) in DMSO (4 mL) was added 3-(6-chloropyrimidin-4-yl)-5-(1-methylcyclopropoxy)-2H-indazole (59.25 mg, 197.00 μmol, 1 eq), DIEA (25.46 mg, 197.00 μmol, 34.31 μL, 1 eq). Then the mixture was stirred at 70° C. for 16 hr under N2. LCMS showed desired MS. The residue was concentrated under reduced pressure to give a residue. The crude product was purified by reversed-phase HPLC (column: 3_Phenomenex Luna C18 75*30 mm*3 um; mobile phase: [water (0.225% FA)-ACN]; B %: 0%-40%, 40 min). to give 2-(2,6-dioxo-3-piperidyl)-5-[4-[[4-[[1-[6-[5-(1-methylcyclopropoxy)-1H-indazol-3-yl]pyrimidin-4-yl]azetidin-3-yl]methyl]-1-piperidyl]methyl]-1-piperidyl]isoindoline-1,3-dione (8 mg, 10.23 μmol, 5.19% yield, 98.7% purity) as a yellow solid.

Exemplary Synthesis of Compound 165

Compound 165 was prepared in a manner analogous to compound 99 using tert-butyl 4-[2-(azetidin-3-yl)ethyl]piperidine-1-carboxylate.

Step 1

To a mixture of tert-butyl 4-(2-bromoethyl)piperidine-1-carboxylate (900 mg, 3.08 mmol, 1 eq) and dimethyl propanedioate (488.29 mg, 3.70 mmol, 424.60 μL, 1.2 eq) in MeCN (10 mL) was added K2CO3 (1.28 g, 9.24 mmol, 3 eq) in one portion at 25° C. under N2. The mixture was stirred at 90° C. for 12 hours. TLC showed the reaction was completed. The mixture was filtered and concentrated in vacuum. The residue was purified by silica gel chromatography (Petroleum ether/Ethyl acetate=100/1, 10/1) to afford dimethyl 2-[2-(1-tert-butoxycarbonyl-4-piperidyl)ethyl]propanedioate (920 mg, 2.68 mmol, 86.98% yield) as yellow solid.

Step 2

To a mixture of dimethyl 2-[2-(1-tert-butoxycarbonyl-4-piperidyl)ethyl]propanedioate (920 mg, 2.68 mmol, 1 eq) in THF (10 mL) was added LAH (305.04 mg, 8.04 mmol, 3 eq) in one portion at −40° C. under N2. The mixture was stirred at −40° C. for 4 hours. TLC showed the reaction was completed. Water (0.5 mL) and 10% aq. NaOH (0.5 mL) was added into the mixture. The aqueous phase was anhydrous Na2SO4, filtered and concentrated in vacuum to afford tert-butyl 4-[4-hydroxy-3-(hydroxymethyl)butyl]piperidine-1-carboxylate (750 mg, 2.61 mmol, 97.41% yield) as yellow solid.

Step 3

To a mixture of tert-butyl 4-[4-hydroxy-3-(hydroxymethyl)butyl]piperidine-1-carboxylate (750.00 mg, 2.61 mmol, 1 eq) and TEA (2.64 g, 26.10 mmol, 3.63 mL, 10 eq) in DCM (5 mL) was added TosCl (2.49 g, 13.05 mmol, 5 eq) and DMAP (31.88 mg, 260.97 μmol, 0.1 eq) in one portion at 0° C. under N2. The mixture was stirred at 25° C. for 12 hours. TLC showed the reaction was completed. The mixture was concentrated in vacuum. The residue was purified by silica gel chromatography (Petroleum ether/Ethyl acetate=100/1, 5/1) to afford tert-butyl 4-[4-(p-tolylsulfonyloxy)-3-(p-tolylsulfonyloxymethyl)butyl]piperidine-1-carboxylate (560 mg, 939.97 μmol, 36.02% yield) as yellow solid.

Step 4

To a mixture of tert-butyl 4-[4-(p-tolylsulfonyloxy)-3-(p-tolylsulfonyloxymethyl)butyl]piperidine-1-carboxylate (500 mg, 839.26 μmol, 1 eq) and PMBNH2 (172.69 mg, 1.26 mmol, 162.92 μL, 1.5 eq) in MeCN (15 mL) was added DIEA (325.40 mg, 2.52 mmol, 438.55 μL, 3 eq) in one portion at 25° C. under N2. The mixture was stirred at 90° C. for 12 hours. LCMS showed desired MS. The mixture was concentrated in vacuum. The residue was purified by prep-HPLC (column: 3_Phenomenex Luna C18 75*30 mm*3 um; mobile phase: [water (0.225% FA)-ACN]; B %: 10%-50%, 40 min) to afford tert-butyl 4-[2-[1-[(4-methoxyphenyl)methyl]azetidin-3-yl]ethyl]piperidine-1-carboxylate (150 mg, 150.56 μmol, 17.94% yield, 39% purity) as yellow solid.

Step 5

To a mixture of tert-butyl 4-[2-[1-[(4-methoxyphenyl)methyl]azetidin-3-yl]ethyl]piperidine-1-carboxylate (20 mg, 51.47 μmol, 1 eq) in t-BuOH (2 mL) and HOAc (0.1 mL) was added Pd(OH)2 (10 mg, 71.21 μmol, 1.38 eq) in one portion at 25° C. under N2. The mixture was stirred at 45° C. for 12 hours. The mixture was filtered and concentrated in vacuum to afford tert-butyl 4-[2-(azetidin-3-yl)ethyl]piperidine-1-carboxylate (15 mg, 45.67 μmol, 88.72% yield, HOAC) as yellow solid.

Step 6

To a mixture of 5-(1-methylcyclopropoxy)-3-[2-[3-[2-(4-piperidyl)ethyl]azetidin-1-yl]-4-pyridyl]-1H-indazole (120 mg, 219.94 μmol, 1 eq, TFA) and DIEA (28.43 mg, 219.94 μmol, 38.31 μL, 1 eq) in MeOH (10 mL) was added 1-[2-(2,6-dioxo-3-piperidyl)-1,3-dioxo-isoindolin-5-yl]piperidine-4-carbaldehyde (81.24 mg, 219.94 μmol, 1 eq) and HOAc (1 mL) in one portion at 25° C. under N2. The mixture was stirred at 25° C. for 30 min, then (2-methylpyridin-1-ium-1-yl)boranuide (70.58 mg, 659.83 μmol, 3 eq) was added and the mixture was stirred at 25° C. for 11.5 hours. The mixture was concentrated in vacuum. The residue was purified by prep-HPLC (column: 3_Phenomenex Luna C18 75*30 mm*3 um; mobile phase: [water (0.225% FA)-ACN]; B %: 10%-50%, 40 min) to afford 2-(2,6-dioxo-3-piperidyl)-5-[4-[[4-[2-[1-[4-[5-(1-methylcyclopropoxy)-1H-indazol-3-yl]-2-pyridyl]azetidin-3-yl]ethyl]-1-piperidyl]methyl]-1-piperidyl]isoindoline-1,3-dione (57.2 mg, 70.98 μmol, 32.27% yield, 97.40% purity) as yellow solid.

Exemplary Synthesis of Compound 166

Step 1

To a solution of 2-(2,6-dioxo-3-piperidyl)-5-[4-(piperazin-1-ylmethyl)-1-piperidyl]isoindoline-1,3-dione (300 mg, 541.98 μmol, 1.28 eq, TFA) and tert-butyl (3S)-3-(p-tolylsulfonyloxymethyl)pyrrolidine-1-carboxylate (150 mg, 422.00 μmol, 1 eq) in CH3CN (5 mL) was added DIEA (272.70 mg, 2.11 mmol, 367.52 μL, 5 eq) and KI (140.10 mg, 844.01 μmol, 2 eq). After addition, the reaction solution mixture was stirred at 80° C. for 12 h. LCMS showed desired MS. After cooling, the reaction mixture was diluted with water (10 mL) and extracted with ethyl acetate (3×10 mL). The organic layer was dried over sodium sulfate and concentrated under reduced pressure. The residue was purified by silica gel column chromatography (0 to 10% methanol in dichloromethane) to afford tert-butyl (3R)-3-[[4-[[1-[2-(2,6-dioxo-3-piperidyl)-1,3-dioxo-isoindolin-5-yl]-4-piperidyl]methyl]piperazin-1-yl]methyl]pyrrolidine-1-carboxylate (320 mg, crude) as a yellow solid.

Step 2

To a solution of tert-butyl (3R)-3-[[4-[[1-[2-(2,6-dioxo-3-piperidyl)-1,3-dioxo-isoindolin-5-yl]-4-piperidyl]methyl]piperazin-1-yl]methyl]pyrrolidine-1-carboxylate (160 mg, 256.92 μmol, 1 eq) in DCM (5 mL) was added TFA (29.29 mg, 256.92 μmol, 19.02 μL, 1 eq). After addition, the reaction solution mixture was stirred at 25° C. for 1 h. LCMS showed starting material consumed and desired MS found. The reaction mixture was concentrated under reduced pressure to afford 2-(2,6-dioxo-3-piperidyl)-5-[4-[[4-[[(3S)-pyrrolidin-3-yl]methyl]piperazin-1-yl]methyl]-1-piperidyl]isoindoline-1,3-dione (165 mg, crude, TFA) as a yellow gum. The crude product was used for next step directly.

Step 3

To a solution of 2-(2,6-dioxo-3-piperidyl)-5-[4-[[4-[[(3S)-pyrrolidin-3-yl]methyl]piperazin-1-yl]methyl]-1-piperidyl]isoindoline-1,3-dione (135 mg, 212.04 μmol, 1.28 eq, TFA) and 3-(6-chloropyrimidin-4-yl)-5-(1-methylcyclopropoxy)-2H-indazole (50 mg, 166.26 μmol, 1 eq) in DMSO (1.5 mL) was added DIEA (107.44 mg, 831.28 μmol, 144.79 μL, 5 eq). After addition, the reaction solution was stirred at 90° C. for 16 h. LCMS showed desired MS. After cooling, the reaction mixture was diluted with ethyl acetate (10 mL) and washed with brine (2×5 mL). The organic layer was concentrated under reduced pressure. The residue was purified by prep.HPLC (column: 3_Phenomenex Luna C18 75*30 mm*3 um; mobile phase: [water (0.225% FA)-ACN]; B %: 0-35%; 40 min) to afford 2-(2,6-dioxo-3-piperidyl)-5-[4-[[4-[[(3R)-1-[6-[5-(1-methylcyclopropoxy)-1H-indazol-3-yl]pyrimidin-4-yl]pyrrolidin-3-yl]methyl]piperazin-1-yl]methyl]-1-piperidyl]isoindoline-1,3-dione (18.5 mg, 23.21 μmol, 13.96% yield, 98.71% purity) as a yellow solid.

Exemplary Synthesis of Compound 167

Compound 167 was prepared in a manner analogous to compound 166 starting from tert-butyl (3R)-3-(p-tolylsulfonyloxymethyl)pyrrolidine-1-carboxylate.

Step 1

To a mixture of 2-(2,6-dioxo-3-piperidyl)-5-[4-[[4-[[(3R)-pyrrolidin-3-yl]methyl]piperazin-1-yl]methyl]-1-piperidyl]isoindoline-1,3-dione (400 mg, 462.58 μmol, 2.32 eq, 3TFA) and 3-(6-chloropyrimidin-4-yl)-5-(1-methylcyclopropoxy)-1H-indazole (60 mg, 199.51 μmol, 1 eq) in DMSO (5 mL) was added DIPEA (206.28 mg, 1.60 mmol, 278.00 μL, 8 eq) in one portion at 20° C. under N2. The mixture was stirred at 80° C. for 16 h. LCMS showed desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous Na2SO4, filtered and concentrated in vacuum. The crude product was purified by reversed-phase HPLC (Column: 3_Phenomenex Luna C18 75*30 mm*3 um; Condition: water (0.225% FA)-ACN; Begin B: 0 End B: 30; FlowRate: 25 mL/min; Gradient Time: 40 min; 100% B Hold Time: 3 min) to give 2-(2,6-dioxo-3-piperidyl)-5-[4-[[4-[[(3S)-1-[6-[5-(1-methylcyclopropoxy)-1H-indazol-3-yl]pyrimidin-4-yl]pyrrolidin-3-yl]methyl]piperazin-1-yl]methyl]-1-piperidyl]isoindoline-1,3-dione (15.7 mg, 19.28 μmol, 9.66% yield, 96.63% purity) as a yellow solid.

Exemplary Synthesis of Compound 168

Step 1

To a mixture of tert-butyl (3S)-3-methylpiperazine-1-carboxylate (1 g, 4.99 mmol, 1 eq) and 3-bromoprop-1-yne (742.47 mg, 4.99 mmol, 538.02 μL, 80% purity, 1 eq) in MeCN (10 mL) was added DIEA (1.29 g, 9.99 mmol, 1.74 mL, 2 eq) in one portion at 25° C. The mixture was stirred at 25° C. for 120 min. TLC (Petroleum ether:Ethyl acetate=1/1) showed the reaction was completed. The mixture was s poured into water (20 mL). The aqueous phase was extracted with ethyl acetate (20 mL*3). The combined organic phase was washed with brine (15 mL*2), dried with anhydrous Na2SO4, filtered and concentrated in vacuum. The residue was purified by silica gel chromatography (Petroleum ether/Ethyl acetate=3/1) to give tert-butyl (3S)-3-methyl-4-prop-2-ynyl-piperazine-1-carboxylate (1.0 g, 4.20 mmol, 84.04% yield) as light yellow liquid.

Step 2

To a mixture of benzyl 4-(hydroxymethyl)piperidine-1-carboxylate (4 g, 16.04 mmol, 1 eq), DMAP (392.03 mg, 3.21 mmol, 0.2 eq) and TEA (4.87 g, 48.13 mmol, 6.70 mL, 3 eq) in DCM (50 mL) was added 4-methylbenzenesulfonyl chloride (6.12 g, 32.09 mmol, 2 eq) at 0° C. The mixture was stirred for 2 hours 25° C. TLC (Petroleum ether:Ethyl acetate=3/1) showed a new spot was formed and the desired compound was detected by LCMS. The mixture was poured into water (50 mL). The aqueous phase was extracted with DCM (30 mL*2). The combined organic phase was washed with brine (20 mL*2), dried with anhydrous Na2SO4, filtered and concentrated in vacuum. The residue was purified by silica gel chromatography (Petroleum ether/Ethyl acetate=3/1) to give benzyl 4-(p-tolylsulfonyloxymethyl)piperidine-1-carboxylate (5.7 g, 14.13 mmol, 88.05% yield) as gray solid.

Step 3

To a mixture of benzyl 4-(p-tolylsulfonyloxymethyl)piperidine-1-carboxylate (2 g, 4.96 mmol, 1 eq) in DMF (20 mL) and H2O (2 mL) was added NaN3 (500 mg, 7.69 mmol, 1.55 eq) in one portion at 25° C. The mixture was stirred at 80° C. for 8 hours. LCMS showed the reaction was completed. The mixture was cooled to 25° C. and poured into water (50 mL). The aqueous phase was extracted with DCM (20 mL*3). The combined organic phase was washed with brine (20 mL*3), dried with anhydrous Na2SO4, filtered and concentrated in vacuum. The crude product was used into the next step without further purification. The product benzyl 4-(azidomethyl)piperidine-1-carboxylate (1.1 g, 4.01 mmol, 80.90% yield) as light yellow liquid.

Step 4

A mixture of benzyl 4-(azidomethyl)piperidine-1-carboxylate (900 mg, 3.28 mmol, 1 eq), tert-butyl (3S)-3-methyl-4-prop-2-ynyl-piperazine-1-carboxylate (781.91 mg, 3.28 mmol, 1 eq), CuSO4.5H2O (409.60 mg, 1.64 mmol, 0.5 eq) and sodium ascorbate (454.98 mg, 2.30 mmol, 0.7 eq) in t-BuOH (5 mL) and H2O (5 mL) was stirred at 25° C. for 12 h. LCMS showed the reaction was completed. The reaction mixture was poured into H2O (10 mL). The mixture was extracted with ethyl acetate (20 mL*3). The organic phase was washed with brine (20 mL), dried over anhydrous Na2SO4, concentrated in vacuum to give a residue. The residue was purified by silica gel chromatography (Dichloromethane/Methanol=10/1) to give tert-butyl (3S)-4-[[1-[((1-benzyloxycarbonyl-4-piperidyl) methyl]triazol-4-yl]methyl]-3-methyl-piperazine-1-carboxylate (1.5 g, 2.93 mmol, 89.18% yield) as brown solid.

Step 5

A solution of tert-butyl (3S)-4-[[1-[(1-benzyloxycarbonyl-4-piperidyl)methyl]triazol-4-yl]methyl]-3-methyl-piperazine-1-carboxylate (240 mg, 468.16 μmol, 1 eq) in MeOH (10 mL) was added NH3·H2O (117.19 mg, 936.32 μmol, 128.78 μL, 28% purity, 2 eq) and Pd/C (468.16 μmol, 10% purity, 1 eq), then the mixture was stirred at 25° C. for 12 hours under H2 (15 psi). LCMS showed the reaction was completed. The mixture was filtered and concentrated in vacuum. The crude product was used into the next step without further purification. The product tert-butyl (3S)-3-methyl-4-[[1-(4-piperidylmethyl)triazol-4-yl]methyl]piperazine-1-carboxylate (170 mg, 449.13 μmol, 95.93% yield) as gray solid.

Step 6

To a mixture of tert-butyl (3S)-3-methyl-4-[[1-(4-piperidylmethyl)triazol-4-yl]methyl]piperazine-1-carboxylate (170 mg, 449.13 μmol, 1 eq) and 2-(2,6-dioxo-3-piperidyl)-5-fluoro-isoindoline-1,3-dione (124.06 mg, 449.13 μmol, 1 eq) in DMSO (3 mL) was added DIEA (290.23 mg, 2.25 mmol, 391.15 μL, 5 eq) in one portion. The mixture was stirred at 100° C. for 2 hours. TLC (Dichloromethane: Methanol=10/1) showed the reaction was completed. The mixture was cooled to 25° C. and poured into water (10 mL). The aqueous phase was extracted with ethyl acetate (15 mL*3). The combined organic phase was washed with brine (10 mL*2), dried with anhydrous Na2SO4, filtered and concentrated in vacuum. The residue was purified by silica gel chromatography (Dichloromethane:Methanol=10/1) to give tert-butyl (3S)-4-[[1-[[1-[2-(2,6-dioxo-3-piperidyl)-1,3-dioxo-isoindolin-5-yl]-4-piperidyl]methyl]triazol-4-yl] methyl]-3-methyl-piperazine-1-carboxylate (100 mg, 152.82 μmol, 34.03% yield, 97% purity) as yellow solid.

Step 7

To a mixture of tert-butyl (3S)-4-[[1-[[1-[2-(2,6-dioxo-3-piperidyl)-1,3-dioxo-isoindolin-5-yl]-4-piperidyl]methyl] triazol-4-yl]methyl]-3-methyl-piperazine-1-carboxylate (100 mg, 157.55 μmol, 1 eq) in DCM (1 mL) was added TFA (1.54 g, 13.51 mmol, 1 mL, 85.73 eq) in one portion. The mixture was stirred at 25° C. for 1 hour. TLC (Methanol: Dichloromethane=1/10) showed the reaction was completed. The mixture was concentrated in reduced pressure at 35° C. The crude product was used into the next step without further purification. The product 2-(2,6-dioxo-3-piperidyl)-5-[4-[[4-[[(2S)-2-methylpiperazin-1-yl]methyl]triazol-1-yl] methyl]-1-piperidyl]isoindoline-1,3-dione (75 mg, 138.89 μmol, 88.15% yield, 99% purity) as light yellow oil.

Step 8

To a mixture of 2-(2,6-dioxo-3-piperidyl)-5-[4-[[4-[[(2S)-2-methylpiperazin-1-yl]methyl]triazol-1-yl]methyl]-1-piperidyl]isoindoline-1,3-dione (75 mg, 140.29 μmol, 1 eq) and 3-(6-chloropyrimidin-4-yl)-5-(1-methylcyclopropoxy)-2H-indazole (42.19 mg, 140.29 μmol, 1 eq) in DMSO (3 mL) was added DIEA (181.31 mg, 1.40 mmol, 244.36 μL, 10 eq) in one portion. The mixture was stirred at 84° C. for 3 hours. LCMS showed the reaction EB153-506-P1 was remained 8% and the desired product was produced 44%. The mixture was cooled to 25° C. and poured into water (10 mL). The aqueous phase was extracted with ethyl acetate (15 mL*2). The combined organic phase was washed with brine (5 mL*2), dried with anhydrous Na2SO4, filtered and concentrated in vacuum. The residue was purified by prep-HPLC (column: Phenomenex Luna C18 75*30 mm*3 um; mobile phase: [water (10 mM NH4HCO3)-ACN]; B %: 0%-70%, 35 min) to afford 2-(2,6-dioxo-3-piperidyl)-5-[4-[[4-[[(2S)-2-methyl-4-[6-[5-(1-methylcyclopropoxy)-2H-indazol-3-yl] pyrimidin-4-yl]piperazin-1-yl]methyl]triazol-1-yl]methyl]-1-piperidyl]isoindoline-1,3-dione (30 mg, 37.10 μmol, 26.45% yield, 98.8% purity) as yellow solid.

Exemplary Synthesis of Compound 169

Step 1

To a mixture of 4-(bromomethyl)benzaldehyde (2 g, 10.05 mmol, 1 eq) and tert-butyl piperazine-1-carboxylate; hydrochloride (2.24 g, 10.05 mmol, 1 eq) in MeCN (15 mL) was added K2CO3 (4.17 g, 30.15 mmol, 3 eq) in one portion. The mixture was stirred at 25° C. for 4 hours. LCMS showed the reaction was completed. The mixture was filtered and concentrated in vacuum. The residue was purified by silica gel chromatography (Petroleum ether/Ethyl acetate=4/1) to afford tert-butyl 4-[(4-formylphenyl)methyl] piperazine-1-carboxylate (2.7 g, 8.87 mmol, 88.26% yield) as light yellow oil.

Step 2

To a mixture of tert-butyl 4-[(4-formylphenyl)methyl] piperazine-1-carboxylate (2.5 g, 8.21 mmol, 1 eq) in HOAc (1.5 mL) and MeOH (15 mL) was added benzyl piperazine-1-carboxylate (2.17 g, 9.86 mmol, 1.90 mL, 1.2 eq) in one portion at 25° C., then borane; 2-methylpyridine (1.76 g, 16.43 mmol, 2 eq) was added. The mixture was stirred at 25° C. for 12 hours. LCMS showed the reaction was completed. The mixture was concentrated in reduced pressure. The residue was purified by silica gel chromatography (Petroleum ether/Ethyl acetate=1/1) to give benzyl 4-[[4-[(4-tert-butoxycarbonylpiperazin-1-yl)methyl]phenyl]methyl]piperazine-1-carboxylate (3.5 g, 6.88 mmol, 83.78% yield) as a gray solid.

Step 3

A solution of benzyl 4-[[4-[(4-tert-butoxycarbonylpiperazin-1-yl)methyl]phenyl]methyl]piperazine-1-carboxylate (300 mg, 589.80 μmol, 1 eq) in DCM (2 mL) was added TFA (1.54 g, 13.51 mmol, 1 mL, 22.90 eq), then the mixture was stirred at 25° C. for 1 hour. LCMS showed the reaction was completed. The mixture was cooled to 25° C. and concentrated in reduced pressure at 40° C. The crude product was used into the next step without further purification. The product benzyl 4-[[4-(piperazin-1-ylmethyl)phenyl]methyl] piperazine-1-carboxylate (220 mg, 527.74 μmol, 89.48% yield, 98% purity) as light yellow liquid.

Step 4

To a mixture of benzyl 4-[[4-(piperazin-1-ylmethyl)phenyl]methyl]piperazine-1-carboxylate (110 mg, 269.25 μmol, 1 eq) and 2-(2,6-dioxo-3-piperidyl)-5-fluoro-isoindoline-1,3-dione (74.37 mg, 269.25 μmol, 1 eq) in DMSO (2 mL) was added DIEA (174.00 mg, 1.35 mmol, 234.50 μL, 5 eq) in one portion. The mixture was stirred at 100° C. for 12 hours. LCMS showed the reaction was completed. The mixture was cooled to 25° C. and poured into water (10 mL). The aqueous phase was extracted with ethyl acetate (15 mL*2). The combined organic phase was washed with brine (5 mL*2), dried with anhydrous Na2SO4, filtered and concentrated in vacuum. The residue was purified by silica gel chromatography (Dichloromethane/Methanol=10/1) to give benzyl 4-[[4-[[4-[2-(2,6-dioxo-3-piperidyl)-1,3-dioxo-isoindolin-5-yl]piperazin-1-yl]methyl]phenyl]methyl]piperazine-1-carboxylate (100 mg, 150.43 μmol, 55.87% yield) as a light yellow solid.

Step 5

To a mixture of benzyl 4-[[4-[[4-[2-(2,6-dioxo-3-piperidyl)-1,3-dioxo-isoindolin-5-yl]piperazin-1-yl]methyl]phenyl]methyl]piperazine-1-carboxylate (100 mg, 150.43 μmol, 1 eq) in TFA (2 mL), the mixture was stirred at 80° C. for 1 hours. TLC (Dichloromethane:Methanol=10/1) showed the reaction was completed. The mixture was cooled to 25° C. and concentrated in reduced pressure at 60° C. The crude product was used into the next step without further purification. The product 2-(2,6-dioxo-3-piperidyl)-5-[4-[[4-(piperazin-1-ylmethyl)phenyl]methyl]piperazin-1-yl]isoindoline-1,3-dione (75 mg, 126.79 μmol, 84.28% yield, 89.7% purity) as a light yellow oil.

Step 6

To a mixture of 2-(2,6-dioxo-3-piperidyl)-5-[4-[[4-(piperazin-1-ylmethyl)phenyl]methyl]piperazin-1-yl]isoindoline-1,3-dione (37 mg, 69.73 μmol, 1 eq) and 3-(6-chloropyrimidin-4-yl)-5-(1-methylcyclopropoxy)-1H-indazole (20.97 mg, 69.73 μmol, 1 eq) in DMSO (2 mL) was added DIEA (90.12 mg, 697.30 μmol, 121.46 μL, 10 eq) in one portion. The mixture was stirred at 83° C. for 3 hours. LCMS showed the reaction was completed. The mixture was cooled to 25° C. and poured into water (10 mL). The aqueous phase was extracted with ethyl acetate (10 mL*2). The combined organic phase was washed with brine (5 mL*2), dried with anhydrous Na2SO4, filtered and concentrated in vacuum. The residue was purified by prep-HPLC (column: 3_Phenomenex Luna C18 75*30 mm*3 um; mobile phase: [water (0.225% FA)-ACN]; B %: 0%-30%, 40 min) to give 2-(2,6-dioxo-3-piperidyl)-5-[4-[[4-[[4-[6-[5-(1-methylcyclopropoxy)-2H-indazol-3-yl]pyrimidin-4-yl]piperazin-1-yl]methyl]phenyl]methyl]piperazin-1-yl]isoindoline-1,3-dione (9.5 mg, 10.98 μmol, 15.75% yield, 97.19% purity, FA) as a light yellow solid.

Exemplary Synthesis of Compound 170

Compound 170 was prepared in a manner analogous to compound 169 starting with 3-(bromomethyl)benzaldehyde.

Step 1

To a solution of 2-(2,6-dioxo-3-piperidyl)-5-[4-[[3-(piperazin-1-ylmethyl)phenyl]methyl]piperazin-1-yl]isoindoline-1,3-dione (100 mg, 188.46 μmol, 1 eq) and 3-(6-chloropyrimidin-4-yl)-5-(1-methylcyclopropoxy)-1H-indazole (56.68 mg, 188.46 μmol, 1 eq) in DMSO (3.5 mL) was added DIEA (371.00 mg, 2.87 mmol, 500.00 μL, 15.23 eq). After addition, the mixture was stirred at 80° C. for 16 hours. LCMS showed desired MS. The residue was poured into water (30 mL). The aqueous phase was extracted with ethyl acetate (30 mL*3). The combined organic phase was washed with brine (30 mL*2), dried with anhydrous Na2SO4, filtered and concentrated in vacuum. The residue was purified by prep.HPLC (column: 3_Phenomenex Luna C18 75*30 mm*3 um; mobile phase: [water (0.225% FA)-ACN]; B %: 0%-30%, 40 min) to afford 2-(2,6-dioxo-3-piperidyl)-5-[4-[[3-[[4-[6-[5-(1-methylcyclopropoxy)-2H-indazol-3-yl]pyrimidin-4-yl]piperazin-1-yl]methyl]phenyl]methyl]piperazin-1-yl]isoindoline-1,3-dione (19.2 mg, 24.03 μmol, 12.75% yield, 99.50% purity) as a yellow solid.

Exemplary Synthesis of Compound 171

Compound 171 was prepared in a manner analogous to compound 169 using benzyl 4-[[4-(4-piperidylmethyl)phenyl]methyl]piperidine-1-carboxylate.

Step 1

To a solution of tert-butyl 4-methylenepiperidine-1-carboxylate (3.84 g, 19.44 mmol, 1.1 eq) was added 9-BBN (0.5 M, 42.42 mL, 1.2 eq) and the mixture was stirred for 1 h at 70° C. under N2. The solution was then cooled to 30° C. and 1-bromo-4-iodo-benzene (5 g, 17.67 mmol, 1 eq) was added, followed by K2CO3 (7.33 g, 53.02 mmol, 3 eq), DMF (40 mL), Water (4 mL) and Pd(dppf)Cl2 (1.94 g, 2.65 mmol, 0.15 eq). The solution was heated to 70° C. under N2 for 3 hours. LCMS showed desire MS value and TLC (Petroleum ether:Ethyl acetate=7:1, Rf=0.66, UV=254 nm) showed new spots formed. The reaction mixture was added water (50 mL) and extracted with EA (80 mL*3). The combined organic layers were washed with brine (80 mL), dried over Na2SO4, filtered and concentrated under reduced pressure to give a residue. The residue was purified by flash silica gel chromatography (0-7% Ethyl acetate/Petroleum ether) to afford tert-butyl 4-[(4-bromophenyl)methyl]piperidine-1-carboxylate (2 g, 4.65 mmol, 26.29% yield, 82.3% purity) as a light yellow oil.

Step 2

To a solution of benzyl 4-methylenepiperidine-1-carboxylate (783.41 mg, 3.39 mmol, 1.2 eq) was added 9-borabicyclo[3.3.1]nonane (0.5 M, 6.77 mL, 1.2 eq) and the mixture was stirred for 1 h at 80° C. under N2. The solution was then cooled to 30° C. and tert-butyl 4-[(4-bromophenyl)methyl]piperidine-1-carboxylate (1 g, 2.82 mmol, 1 eq) was added, followed by K2CO3 (1.17 g, 8.47 mmol, 3 eq), DMF (20 mL), Water (5 mL) and Pd(dppf)Cl2 (165.23 mg, 225.81 μmol, 0.08 eq). The solution was heated to 80° C. under N2 for 15 hours. LCMS showed ~38% desire compound and TLC (Petroleum ether:Ethyl acetate=10:1, 12, Rf=0.28) showed new spots formed and the starting materials was consumed completely. The reaction mixture was added water 50 mL and extracted with EA (80 mL*3). The combined organic layers were washed with brine 80 mL, dried over Na2SO4, filtered and concentrated under reduced pressure to give a residue. The residue was purified by flash silica gel chromatography (0-7% Ethyl acetate/Petroleum ether) to afford benzyl 4-[[4-[(1-tert-butoxycarbonyl-4-piperidyl)methyl]phenyl]methyl]piperidine-1-carboxylate (655 mg, 1.18 mmol, 41.95% yield, 91.6% purity) as a yellow solid.

Step 3

To a solution of benzyl 4-[[4-[(1-tert-butoxycarbonyl-4-piperidyl)methyl]phenyl]methyl]piperidine-1-carboxylate (655 mg, 1.29 mmol, 1 eq) in DCM (10 mL) was added HCl/EtOAc (4 M, 5 mL, 15.47 eq), then the mixture was stirred at 25° C. for 1 hour. LCMS showed desire MS value and the starting materials was consumed complete. The reaction mixture was concentrated under reduced pressure to afford benzyl 4-[[4-(4-piperidylmethyl)phenyl]methyl]piperidine-1-carboxylate (550 mg, 1.24 mmol, 96.03% yield, HCl) as a yellow solid.

Step 4

To a solution of 2-(2,6-dioxo-3-piperidyl)-5-[4-[[4-(4-piperidylmethyl)phenyl]methyl]-1-piperidyl]isoindoline-1,3-dione (260.57 mg, 492.90 μmol, 2.47 eq) and 3-(6-chloropyrimidin-4-yl)-5-(1-methylcyclopropoxy)-1H-indazole (60 mg, 199.51 μmol, 1 eq) in DMSO (3 mL) was added DIEA (206.28 mg, 1.60 mmol, 278.00 μL, 8 eq), then the mixture was stirred at 90° C. for 4 hours. LCMS showed desire MS value and the starting materials was consumed completely. Without workup. The residue was purified by prep-HPLC (column: 3_Phenomenex Luna C18 75*30 mm*3 um; mobile phase: [water (0.225% FA)-ACN]; B %: 20%-70%, 40 min) to afford 2-(2,6-dioxo-3-piperidyl)-5-[4-[[4-[[1-[6-[5-(1-methylcyclopropoxy)-2H-indazol-3-yl]pyrimidin-4-yl]-4-piperidyl]methyl]phenyl]methyl]-1-piperidyl]isoindoline-1,3-dione (10.5 mg, 13.19 μmol, 6.61% yield, 99.57% purity) as a yellow solid.

Exemplary Synthesis of Compound 172

Compound 172 was prepared in a manner analogous to compound 169 using benzyl 4-[[6-(piperazin-1-ylmethyl) pyridazin-3-yl]methyl]piperazine-1-carboxylate.

Step 1

To a solution of methyl 6-methylpyridazine-3-carboxylate (5.5 g, 36.15 mmol, 1 eq) in DMF (200 mL) was added NBS (7.72 g, 43.38 mmol, 1.2 eq) and AIBN (629.21 mg, 3.83 mmol, 0.106 eq). The mixture was stirred at 80° C. for 2 hr. LC-MS (EB134-925-P1C) showed ~27% of reactant 1 was remained. Several new peaks were shown on LC-MS and ~22% of desired compound was detected. The reaction mixture was diluted with water (200 mL*5) and extracted with EA (300 mL). The combined organic layers were washed with brine (200 mL) dried over Na2SO4, filtered and concentrated under reduced pressure to give a residue. The crude product was purified by column chromatography on silica gel (column height: 80 g, 100-200 mesh silica gel, 0-20% (25 min) of Ethyl acetate in Petroleum ether, 20% (10 min) of Ethyl acetate in Petroleum ether) to get methyl 6-(bromomethyl)pyridazine-3-carboxylate (740 mg, 3.20 mmol, 8.86% yield) as a yellow solid.

Step 2

To a solution of methyl 6-(bromomethyl)pyridazine-3-carboxylate (300 mg, 1.30 mmol, 1 eq) in THF (3 mL) was added DIEA (503.44 mg, 3.90 mmol, 678.49 μL, 3 eq) and tert-butyl piperazine-1-carboxylate (483.67 mg, 2.60 mmol, 2 eq). The mixture was stirred at 60° C. for 16 hr. LC-MS (EB134-926-P1A) showed no reactant 1 was remained. Several new peaks were shown on LC-MS and ~93% of desired compound was detected. The reaction mixture was concentrated under reduced pressure to remove solvent. The crude product was purified by column chromatography on silica gel (column height: 12 g, 100-200 mesh silica gel, 0-40% (15 min) of Ethyl acetate in Petroleum ether, 40% (10 min) of Ethyl acetate in Petroleum ether) to get methyl 6-[(4-tert-butoxycarbonylpiperazin-1-yl)methyl]pyridazine-3-carboxylate (380 mg, 1.13 mmol, 87.00% yield) as a white solid.

Step 3

A solution of methyl 6-[(4-tert-butoxycarbonylpiperazin-1-yl)methyl]pyridazine-3-carboxylate (380 mg, 1.13 mmol, 1 eq) in THF (20 mL) was cooled at 0° C. Diisobutyl aluminium hydride (1 M, 2.26 mL, 2 eq) was slowly added over 30 minutes. The mixture was stirred at 25° C. for 4 h. LC-MS (EB134-928-P1A) showed no reactant 1 was remained. Several new peaks were shown on LC-MS and ~23% of desired compound was detected. The reaction mixture was diluted with NH4Cl (30 mL). The reaction solution was filtered to remove insoluble and extracted with EA (30 mL). The combined organic layers were washed with brine (20 mL), dried over Na2SO4, filtered and concentrated under reduced pressure to give tert-butyl 4-[(6-formylpyridazin-3-yl)methyl]piperazine-1-carboxylate (260 mg, 848.68 μmol, 75.13% yield) as a yellow solid.

Step 4

To a solution of tert-butyl 4-[(6-formylpyridazin-3-yl) methyl]piperazine-1-carboxylate (260 mg, 848.68 μmol, 1 eq) in MeOH (6 mL) and AcOH (0.6 mL) was added borane; 2-methylpyridine (453.88 mg, 4.24 mmol, 5 eq) and benzyl piperazine-1-carboxylate (280.40 mg, 1.27 mmol, 245.97 μL, 1.5 eq). The mixture was stirred at 25° C. for 2 hr. LC-MS (EB134-930-P1A) showed no reactant 1 was remained. Several new peaks were shown on LC-MS and ~76% of desired compound was detected. TLC (SiO2, DCM/MeOH=10/1, RF=0.24) indicated one major new spot with larger polarity was detected. The reaction mixture was concentrated under reduced pressure to remove solvent. The crude product was purified by column chromatography on silica gel (column height: 12 g, 100-200 mesh silica gel, 0-10% (15 min) of MeOH in DCM) to get benzyl 4-[[6-[(4-tert-butoxycarbonylpiperazin-1-yl)methyl]pyridazin-3-yl] methyl]piperazine-1-carboxylate (330 mg, 646.26 μmol, 76.15% yield) as a yellow solid.

Step 5

To a solution of benzyl 4-[[6-[(4-tert-butoxycarbonylpiperazin-1-yl)methyl]pyridazin-3-yl]methyl]piperazine-1-carboxylate (150 mg, 293.76 μmol, 1 eq) in DCM (2.5 mL) was added TFA (770.00 mg, 6.75 mmol, 0.5 mL, 22.99 eq). The mixture was stirred at 25° C. for 0.5 hr. TLC (DCM/MeOH=10/1, Rf=0) indicated no reactant 1 was remained, and one major new spot with larger polarity was detected. The reaction mixture was concentrated under reduced pressure to remove solvent to get benzyl 4-[[6-(piperazin-1-ylmethyl)pyridazin-3-yl]methyl]piperazine-1-carboxylate (150 mg, 248.79 μmol, 84.69% yield, 87% purity, TFA) as a yellow gum.

Step 6

To a solution of 2-(2,6-dioxo-3-piperidyl)-5-[4-[[6-(piperazin-1-ylmethyl)pyridazin-3-yl]methyl]piperazin-1-yl] isoindoline-1,3-dione (100 mg, 154.65 μmol, 1 eq, TFA) in DMSO (3 mL) was added DIEA (199.88 mg, 1.55 mmol, 269.37 μL, 10 eq) and 3-(6-chloropyrimidin-4-yl)-5-(1-methylcyclopropoxy)-1H-indazole (46.51 mg, 154.65 μmol, 1 eq). The mixture was stirred at 80° C. for 2 hr. LC-MS (EB134-936-P1B) showed no reactant 1 was remained. Several new peaks were shown on LC-MS and ~53% of desired compound was detected. The resulting product was filtered to remove the insoluble. The impure product was purified by Prep-HPLC (column: 3_Phenomenex Luna C18 75*30 mm*3 um; mobile phase: [water (0.225% FA)-ACN]; B %: 0%-35%, 40 min) to get 2-(2,6-dioxo-3-piperidyl)-5-[4-[[6-[[4-[6-[5-(1-methylcyclopropoxy)-2H-indazol-3-yl] pyrimidin-4-yl]piperazin-1-yl]methyl]pyridazin-3-yl] methyl]piperazin-1-yl]isoindoline-1,3-dione (33.8 mg, 42.36 μmol, 27.39% yield, 99.86% purity) as a yellow solid.

Exemplary Synthesis of Compound 173

Step 1

To a solution of 4-bromo-2-fluoropyridine (600 mg, 3.41 mmol, 1 eq) in DMSO (20 mL) was added tert-butyl 4-[[4-(4-piperidylmethyl)phenyl]methyl]piperidine-1-carboxylate (1.5 g, 4.03 mmol, 1.18 eq) and K2CO3 (1.41 g, 10.23 mmol, 3 eq). After addition, the reaction solution was stirred at 90° C. for 12 h. TLC (petroleum ether:ethyl acetate=5:1) showed the reaction was completed. After cooling, the reaction mixture was filtered and filtrate was diluted with ethyl acetate (50 mL) and washed with brine (3×30 mL). The organic layer was dried over sodium sulfate and concentrated under reduced pressure. The residue was purified by silica gel column chromatography (0 to 20% ethyl acetate in petroleum ether) to afford tert-butyl 4-[[4-[[1-(4-bromo-2-pyridyl)-4-piperidyl]methyl]phenyl]methyl]piperidine-1-carboxylate (1.4 g, 2.35 mmol, 68.84% yield, 88.6% purity) as a white solid.

Step 2

To a solution of tert-butyl 4-[[4-[[1-(4-bromo-2-pyridyl)-4-piperidyl]methyl]phenyl]methyl]piperidine-1-carboxylate (400 mg, 756.83 μmol, 1 eq) in dioxane (10 mL) was added Pin2B2 (384.37 mg, 1.51 mmol, 2 eq), Pd(dppf)Cl2 (55.38 mg, 75.68 μmol, 0.1 eq) and KOAc (222.83 mg, 2.27 mmol, 3 eq). After addition, the reaction mixture was stirred at 100° C. under N2 for 12 h. LCMS showed starting material consumed and desired MS formed. After cooling, the reaction mixture was filtered and filtrate was concentrated under reduced pressure to afford tert-butyl 4-[[4-[[1-[4-(4,4,5,5-tetramethyl-1,3,2-dioxaborolan-2-yl)-2-pyridyl]-4-piperidyl]methyl]phenyl]methyl]piperidine-1-carboxylate (800 mg, crude) as a black oil. The crude product was used for next step directly.

Step 3

To a solution of tert-butyl 4-[[4-[[1-[4-(4,4,5,5-tetramethyl-1,3,2-dioxaborolan-2-yl)-2-pyridyl]-4-piperidyl]methyl]phenyl]methyl]piperidine-1-carboxylate (800 mg, 1.39 mmol, 4.12 eq) in dioxane (5 mL) and H2O (1 mL) was added 2-[[3-iodo-5-(1-methylcyclopropoxy)indazol-1-yl]methoxy]ethyl-trimethyl-silane (150 mg, 337.55 μmol, 1 eq), Na2CO3 (107.33 mg, 1.01 mmol, 3 eq) and Pd(dppf)Cl2 (17.29 mg, 23.63 μmol, 0.07 eq). After addition, the reaction mixture was stirred at 90° C. under N2 for 12 h. LCMS showed the reaction was completed. TLC (petroleum ether:ethyl acetate=5:1) showed several new spots. After cooling, the reaction mixture was filtered to remove insoluble substance and filtrate was concentrated under reduced pressure. The residue was purified by silica gel column chromatography (0 to 20% ethyl acetate in petroleum ether) to afford tert-butyl 4-[[4-[[1-[4-[5-(1-methylcyclopropoxy)-1-(2-trimethylsilylethoxymethyl)indazol-3-yl]-2-pyridyl]-4-piperidyl]methyl]phenyl]methyl]piperidine-1-carboxylate (140 mg, 172.69 μmol, 51.16% yield, 94.5% purity) as a light yellow gum.

Step 4

To a solution of tert-butyl 4-[[4-[[1-[4-[5-(1-methylcyclopropoxy)-1-(2-trimethylsilylethoxymethyl)indazol-3-yl]-2-pyridyl]-4-piperidyl]methyl]phenyl]methyl]piperidine-1-carboxylate (140 mg, 182.74 μmol, 1 eq) in MeOH (2 mL) was added HCl/EtOAc (4 M, 2 mL, 43.78 eq). After addition, the reaction solution was stirred at 65° C. for 0.5 hr. LCMS showed the reaction completed. After cooling, the reaction solution was concentrated under reduced pressure to afford 5-(1-methylcyclopropoxy)-3-[2-[4-[[4-(4-piperidylmethyl)phenyl]methyl]-1-piperidyl]-4-pyridyl]-1H-indazole (110 mg, crude, HCl) as a light yellow solid. The crude product was used for next step directly.

Step 5

To a solution of 5-(1-methylcyclopropoxy)-3-[2-[4-[[4-(4-piperidylmethyl)phenyl]methyl]-1-piperidyl]-4-pyridyl]-1H-indazole (110 mg, 192.25 μmol, 1 eq, HCl) in DMSO (3 mL) was added 2-(2,6-dioxo-3-piperidyl)-5-fluoro-isoindoline-1,3-dione (53 mg, 191.88 μmol, 1 eq) and DIEA (123.99 mg, 959.38 μmol, 167.11 μL, 5 eq). After addition, the reaction solution was stirred at 100° C. for 12 hr. LCMS showed the reaction completed. After cooling, the reaction mixture was diluted with ethyl acetate (20 mL) and washed with brine (10 mL*3). The organic layer was dried over sodium sulfate and concentrated under reduced pressure. The residue was purified by silica gel column chromatography (0 to 72% ethyl acetate in petroleum ether) to afford 2-(2,6-dioxo-3-piperidyl)-5-[4-[[4-[[1-[4-[5-(1-methylcyclopropoxy)-1H-indazol-3-yl]-2-pyridyl]-4-piperidyl]methyl]phenyl]methyl]-1-piperidyl]isoindoline-1,3-dione (40.6 mg, 49.46 μmol, 25.78% yield, 96.48% purity) as a yellow solid.

Exemplary Synthesis of Compound 174

Compound 174 was prepared in a manner analogous to compound 171 starting with 1-bromo-3-iodo-benzene.

Step 1

To a solution of 2-(2,6-dioxo-3-piperidyl)-5-[4-[[3-(4-piperidylmethyl)phenyl]methyl]-1-piperidyl]isoindoline-1,3-dione (90 mg, 170.25 μmol, 1 eq) and 3-(6-chloropyrimidin-4-yl)-5-(1-methylcyclopropoxy)-1H-indazole (51.20 mg, 170.25 μmol, 1 eq) in DMSO (3 mL) was added DIEA (371.00 mg, 2.87 mmol, 0.5 mL, 16.86 eq). After addition, the mixture was stirred at 90° C. for 16 hours. LCMS showed there was desired MS. The residue was poured into water (20 mL). The aqueous phase was extracted with ethyl acetate (20 mL*3). The combined organic phase was washed with brine (20 mL*2), dried with anhydrous Na2SO4, filtered and concentrated in vacuum. The residue was purified by prep.HPLC (column: Phenomenex Luna C18 75*30 mm*3 um; mobile phase: [water (0.225% FA)-ACN]; B %: 30%-60%, 35 min) to afford 2-(2,6-dioxo-3-piperidyl)-5-[4-[[3-[[1-[6-[5-(1-methylcyclopropoxy)-2H-indazol-3-yl]pyrimidin-4-yl]-4-piperidyl]methyl]phenyl]methyl]-1-piperidyl]isoindoline-1,3-dione (14.7 mg, 18.17 μmol, 10.67% yield, 98% purity) as a yellow solid.

Exemplary Synthesis of Compound 175

Step 1

A mixture of 1-[2-(2,6-dioxo-3-piperidyl)-1,3-dioxo-isoindolin-5-yl]piperidine-4-carbaldehyde (200 mg, 541.46 μmol, 1 eq), tert-butyl 2,6-diazaspiro[3.3]heptane-2-carboxylate; oxalic acid (158.07 mg, 324.88 μmol, 0.6 eq) in MeOH (10 mL) was added AcOH (1 mL), borane; 2-methylpyridine (57.92 mg, 541.46 μmol, 1 eq) and then the mixture was stirred at 25° C. for 12 hr under N2. LCMS showed the starting material was consumed completely and desired MS found. The reaction mixture was concentrated under reduced pressure to give a residue. The residue was purified by silica gel column chromatography (0 to 30% Dichloromethane in Methanol) to give tert-butyl 6-[[1-[2-(2,6-dioxo-3-piperidyl)-1,3-dioxo-isoindolin-5-yl]-4-piperidyl]methyl]-2,6-diazaspiro[3.3]heptane-2-carboxylate (560 mg, crude) as a yellow gum.

Step 2

A mixture of tert-butyl 6-[[1-[2-(2,6-dioxo-3-piperidyl)-1,3-dioxo-isoindolin-5-yl]-4-piperidyl]methyl]-2,6-diazaspiro[3.3]heptane-2-carboxylate (300 mg, 543.84 μmol, 1 eq) in DCM (2 mL) was added TFA (1.65 g, 14.47 mmol, 1.07 mL, 26.61 eq). and then the mixture was stirred at 25° C. for 2 hr under N2. TLC (Dichloromethane:Methanol=10:1) showed started material consumed completed and one new major point found. The reaction mixture was concentrated under reduced pressure to give 5-[4-(2,6-diazaspiro[3.3]heptan-2-ylmethyl)-1-piperidyl]-2-(2,6-dioxo-3-piperidyl)isoindoline-1,3-dione (700 mg, crude, TFA) as a brown gum.

Step 3

A mixture of 5-[4-(2,6-diazaspiro[3.3]heptan-2-ylmethyl)-1-piperidyl]-2-(2,6-dioxo-3-piperidyl)isoindoline-1,3-dione (64.60 mg, 143.07 μmol, 1 eq), 1-[6-[5-(1-methylcyclopropoxy)-1H-indazol-3-yl]pyrimidin-4-yl]piperidine-4-carbaldehyde (54 mg, 143.07 μmol, 1 eq) in MeOH (10 mL) was added AcOH (1 mL), borane; 2-methylpyridine (30.61 mg, 286.14 μmol, 2 eq) and then the mixture was stirred at 25° C. for 12 hr under N2. LCMS showed the starting material was consumed completely and desired MS found. The reaction mixture was concentrated under reduced pressure to give a residue. The crude product was purified by reversed-phase HPLC (column: 3_Phenomenex Luna C18 75*30 mm*3 um; mobile phase: [water (0.225% FA)-ACN]; B %: 0%-30%, 40 min) to give 2-(2,6-dioxo-3-piperidyl)-5-[4-[[2-[[1-[6-[5-(1-methylcyclopropoxy)-1H-indazol-3-yl]pyrimidin-4-yl]-4-piperidyl]methyl]-2,6-diazaspiro[3.3]heptan-6-yl]methyl]-1-piperidyl]isoindoline-1,3-dione (22.2 mg, 27.03 μmol, 18.90% yield, 99% purity) as a yellow solid.

Exemplary Synthesis of Compound 176

Compound 176 was prepared in a manner analogous to compound 175 starting from tert-butyl 1,6-diazaspiro[3.3]heptane-6-carboxylate.

Step 1

A mixture of 5-[4-(1,6-diazaspiro[3.3]heptan-1-ylmethyl)-1-piperidyl]-2-(2,6-dioxo-3-piperidyl)isoindoline-1,3-dione (77.76 mg, 172.21 μmol, 1 eq), 1-[6-[5-(1-methylcyclopropoxy)-1H-indazol-3-yl]pyrimidin-4-yl]piperidine-4-carbaldehyde (65 mg, 172.21 μmol, 1 eq) in MeOH (10 mL) was added AcOH (1 mL) and borane; 2-methylpyridine (18.42 mg, 172.21 μmol, 1 eq) and then the mixture was stirred at 25° C. for 16 hr under N2 atmosphere. LCMS showed the starting material was consumed completely and desired MS found. The reaction mixture was concentrated under reduced pressure to give a residue. The crude product was purified by reversed-phase HPLC (column: 3_Phenomenex Luna C18 75*30 mm*3 um; mobile phase: [water (0.225% FA)-ACN]; B %: 0%-40%, 40 min). to give 2-(2,6-dioxo-3-piperidyl)-5-[4-[[6-[[1-[6-[5-(1-methylcyclopropoxy)-1H-indazol-3-yl]pyrimidin-4-yl]-4-piperidyl]methyl]-1,6-diazaspiro[3.3]heptan-1-yl]methyl]-1-piperidyl]isoindoline-1,3-dione (19.6 mg, 23.15 μmol, 13.44% yield, 96% purity) as a yellow solid Exemplary Synthesis of Compound 177

Step 1

A mixture of tert-butyl 2-formyl-7-azaspiro[3.5]nonane-7-carboxylate (500 mg, 1.97 mmol, 1 eq), benzyl piperazine-1-carboxylate (434.73 mg, 1.97 mmol, 381.34 μL, 1 eq), borane; 2-methylpyridine (633.31 mg, 5.92 mmol, 3 eq) in MeOH (10 mL) was added AcOH (2 mL) borane; 2-methylpyridine (633.31 mg, 5.92 mmol, 3 eq) and then the mixture was stirred at 25° C. for 16 hr under N2 atmosphere. LCMS showed the starting material was consumed completely and desired MS found. TLC (Petroleum ether:Ethyl acetate=0:1) showed several new spots. The reaction mixture was concentrated under reduced pressure. The residue was purified by silica gel column chromatography (0 to 80% Ethyl acetate in Petroleum ether) to give compound to give tert-butyl 2-[(4-benzyloxycarbonylpiperazin-1-yl)methyl]-7-azaspiro[3.5]nonane-7-carboxylate (933 mg, 1.53 mmol, 77.48% yield, 75% purity) as a colorless gum.

Step 2

A mixture of tert-butyl 2-[(4-benzyloxycarbonylpiperazin-1-yl)methyl]-7-azaspiro[3.5]nonane-7-carboxylate (200 mg, 437.06 μmol, 1 eq) in DCM (3 mL) was added TFA (4.62 g, 40.52 mmol, 3 mL, 92.71 eq) and then the mixture was stirred at 25° C. for 1 hr under N2 atmosphere. TLC (Petroleum ether:Ethyl acetate=0:1) showed one new spot. The reaction mixture was concentrated under reduced pressure to give benzyl 4-(7-azaspiro[3.5]nonan-2-ylmethyl)piperazine-1-carboxylate (200 mg, crude, TFA) as a yellow gum Step 3

A mixture of benzyl 4-(7-azaspiro[3.5]nonan-2-ylmethyl)piperazine-1-carboxylate (156 mg, 436.38 μmol, 1 eq), 1-[2-(2,6-dioxo-3-piperidyl)-1,3-dioxo-isoindolin-5-yl]piperidine-4-carbaldehyde (161.19 mg, 436.38 μmol, 1 eq), in MeOH (10 mL) was added AcOH (2 mL), borane; 2-methylpyridine (140.03 mg, 1.31 mmol, 3 eq) and then the mixture was stirred at 25° C. for 16 hr under N2 atmosphere. LCMS showed the starting material was consumed completely and desired MS found. TLC (Dichloromethane:Methanol=10:1) showed several new spots The resulting product was poured into H2O (10 mL). The mixture was extracted with ethyl acetate (20 mL*3). The organic phase was washed with brine (50 mL), dried over anhydrous Na2SO4, concentrated in vacuum to give a residue. The residue was purified by silica gel column chromatography (0 to 30% Methanol in Dichloromethane) to give benzyl 4-[[7-[[1-[2-(2,6-dioxo-3-piperidyl)-1,3-dioxo-isoindolin-5-yl]-4-piperidyl]methyl]-7-azaspiro[3.5]nonan-2-yl]methyl]piperazine-1-carboxylate (233 mg, 219.61 μmol, 50.33% yield, 67% purity) as a yellow gum Step 4

A mixture of benzyl 4-[[7-[[1-[2-(2,6-dioxo-3-piperidyl)-1,3-dioxo-isoindolin-5-yl]-4-piperidyl]methyl]-7-azaspiro[3.5]nonan-2-yl]methyl]piperazine-1-carboxylate (223 mg, 313.70 μmol, 1 eq), TFA (4.62 g, 40.52 mmol, 3 mL, 129.16 eq) in TFA (4.62 g, 40.52 mmol, 3 mL, 129.16 eq) and then the mixture was stirred at 70° C. for 1 hr under N2 atmosphere. TLC (Dichloromethane:Methanol=10:1) showed the starting material was consumed completely and one new spot found. The reaction mixture was concentrated under reduced pressure. The residue was purified by silica gel column chromatography (0 to 30% Dichloromethane in Methanol) to give 2-(2,6-dioxo-3-piperidyl)-5-[4-[[1-oxo-1-(4-piperidylmethylimino)-1,4-thiazinan-4-yl]methyl]-1-piperidyl]isoindoline-1,3-dione (200 mg, crude, TFA) as a yellow gum Step 5

A mixture of 2-(2,6-dioxo-3-piperidyl)-5-[4-[[2-(piperazin-1-ylmethyl)-7-azaspiro[3.5]nonan-7-yl]methyl]-1-piperidyl]isoindoline-1,3-dione (76.71 mg, 133.00 μmol, 1 eq), 3-(6-chloropyrimidin-4-yl)-5-(1-methylcyclopropoxy)-2H-indazole (40 mg, 133.00 μmol, 1 eq), DIEA (17.19 mg, 133.00 μmol, 23.17 uL, 1 eq) in DMSO (5 mL) was added DIEA (17.19 mg, 133.00 μmol, 23.17 μL, 1 eq) and then the mixture was stirred at 100° C. for 12 hr under N2 atmosphere. LCMS showed the starting material was consumed completely and desired MS found. The reaction mixture was filtered and concentrated under reduced pressure. The crude product was purified by reversed-phase HPLC (column: 3_Phenomenex Luna C18 75*30 mm*3 um; mobile phase: [water (0.225% FA)-ACN]; B %: 0%-35%, 40 min) to give 2-(2,6-dioxo-3-piperidyl)-5-[4-[[2-[[4-[6-[5-(1-methylcyclopropoxy)-2H-indazol-3-yl]pyrimidin-4-yl]piperazin-1-yl]methyl]-7-azaspiro[3.5]nonan-7-yl]methyl]-1-piperidyl]isoindoline-1,3-dione (40.8 mg, 48.03 μmol, 36.11% yield, 99% purity) as a yellow solid.

Exemplary Synthesis of Compound 178

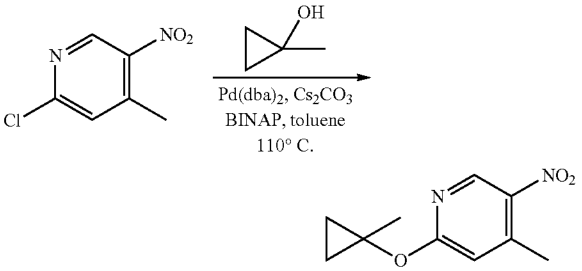

Step 1:

To a mixture of 2-chloro-4-methyl-5-nitro-pyridine (5 g, 28.97 mmol, 1 eq) and 1-methylcyclopropanol (2.09 g, 28.97 mmol, 1 eq) in toluene (10 mL) was added $Pd(dba)_2$ (333.21 mg, 579.48 μmol, 0.02 eq), $Cs_2CO3$ (11.33 g, 34.77 mmol, 1.2 eq) and BINAP (1.08 g, 1.74 mmol, 0.06 eq) in one portion at 20° C. under $N_2$. The mixture was heated to 110° C. and stirred for 3 hours. LCMS showed there was desired MS. The mixture was cooled to 20° C. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by silica gel chromatography (Petroleum ether) to give 4-methyl-2-(1-methylcyclopropoxy)-5-nitro-pyridine (5.1 g, 24.49 mmol, 84.54% yield) as a yellow oil.

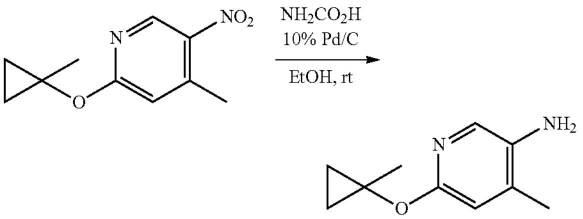

Step 2:

To a mixture of 4-methyl-2-(1-methylcyclopropoxy)-5-nitro-pyridine (5.1 g, 24.49 mmol, 1 eq) in EtOH (10 mL) was added Pd/C (500 mg, 24.49 mmol, 10% purity, 1 eq) and ammonium formate (18.54 g, 293.93 mmol, 12 eq) in one portion at 20° C. under $N_2$. The mixture was stirred at 20° C. for 1 h to give black solution. TLC showed the reaction was completed. The mixture was filtered through a pad of silica gel with EtOAc (3×200 mL) and concentrated in vacuum. The residue was purified by silica gel chromatography (100-200 mesh silica gel, 0-10% of Ethyl acetate in Petroleum ether) to give 4-methyl-6-(1-methylcyclopropoxy)pyridin-3-amine (3.3 g, 18.19 mmol, 74.26% yield, 98.24% purity) as a red oil.

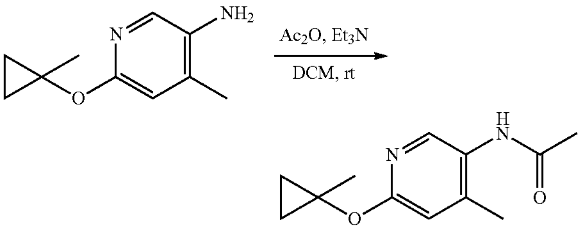

Step 3:

To a mixture of 4-methyl-6-(1-methylcyclopropoxy)pyridin-3-amine (3.3 g, 18.52 mmol, 1 eq) and $Et_3N$ (4.68 g, 46.29 mmol, 6.44 mL, 2.5 eq) in DCM (10 mL) was added $Ac_2O$ (3.78 g, 37.03 mmol, 3.47 mL, 2 eq) in one portion at 0° C. under $N_2$. The mixture was stirred at 0° C. for 30 min, then heated to 20° C. and stirred for 1 hour. TLC showed the reaction was completed. LCMS showed there was desired MS. The reaction was quenched with a saturated solution of aqueous $NaHCO_3$ (30 mL) to adjusted pH=7-8 and extracted with $CH_2Cl_2$ (3×50 mL). The combined organic phase was washed with brine (3×50 mL), dried with anhydrous $Na_2SO_4$, filtered and concentrated in vacuum. The residue was purified by silica gel chromatography (100-200 mesh silica gel, 20-40% Ethyl acetate in Petroleum ether) to give N-[4-methyl-6-(1-methylcyclopropoxy)-3-pyridyl]acetamide (4 g, 18.16 mmol, 98.08% yield) as a red oil.

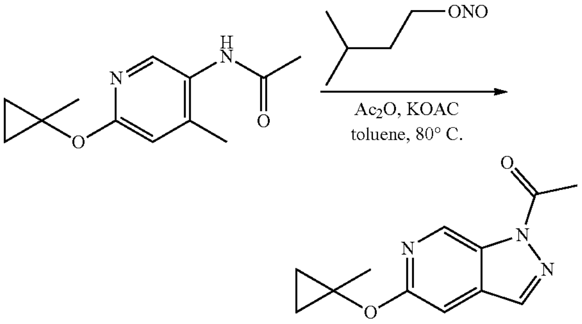

Step 4:

To a solution of N-[4-methyl-6-(1-methylcyclopropoxy)-3-pyridyl]acetamide (4 g, 18.16 mmol, 1 eq) in toluene (10 mL) was added KOAc (2.67 g, 27.24 mmol, 1.5 eq) and $Ac_2O$ (8.53 g, 83.53 mmol, 7.82 mL, 4.6 eq) at 20° C., then the solution was heated to 80° C., then isopentyl nitrite (8.51 g, 72.64 mmol, 9.78 mL, 4 eq) was dropwise added. The mixture was stirred at 80° C. for 2 h. TLC and LCMS showed the reaction was completed. The reaction was then filtered with EtOAc (70 mL), and the filtrate was concentrated in vacuum. The residue was purified by silica gel chromatography (100-200 mesh silica gel, 0-10% Ethyl acetate in Petroleum ether) to give 1-[5-(1-methylcyclopropoxy)pyrazolo[3,4-c]pyridin-1-yl]ethanone (2.9 g, 12.54 mmol, 69.06% yield) as a yellow oil.

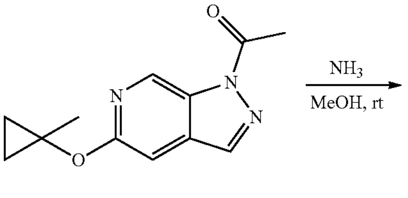

-continued

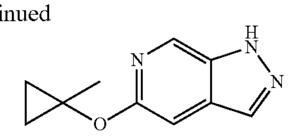

Step 5:

To a solution of 1-[5-(1-methylcyclopropoxy)pyrazolo[3,4-c]pyridin-1-yl]ethanone (2.9 g, 12.54 mmol, 1 eq) in MeOH (50 mL) was added ammonia (7 M, 1.79 mL, 1 eq) (NH3 (g)/MeOH) in one portion at 20° C. The mixture was stirred at 20° C. for 30 min to give red solution. LCMS showed the reaction was completed. The solution was concentrated in vacuum to give 5-(1-methylcyclopropoxy)-1H-pyrazolo[3,4-c]pyridine (2.1 g, crude) as a yellow solid.

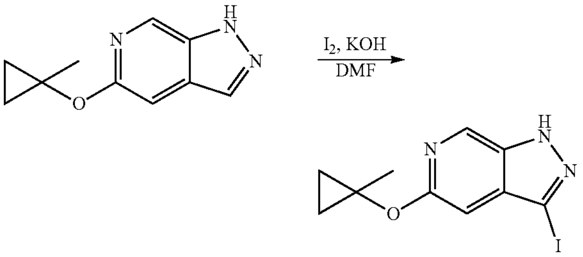

Step 6:

To a solution of 5-(1-methylcyclopropoxy)-1H-pyrazolo[3,4-c]pyridine (500 mg, 2.64 mmol, 1 eq) in DMF (30 mL) was added $I_2$ (1.34 g, 5.29 mmol, 1.06 mL, 2 eq) and KOH (444.82 mg, 7.93 mmol, 3 eq). After addition, the reaction mixture was stirred at 25° C. for 16 h. LCMS showed desired MS. TLC (petroleum ether:ethyl acetate=5:1) showed major one new spots. The reaction mixture was quenched by saturated $Na_2S_2O_3$ (30 mL) and extracted with ethyl acetate (2×30 mL). The organic layer was dried over sodium sulfate and concentrated under reduced pressure. The residue was purified by silica gel column chromatography (0 to 15% ethyl acetate in petroleum ether) to give 3-iodo-5-(1-methylcyclopropoxy)-1H-pyrazolo[3,4-c]pyridine (750 mg, 2.38 mmol, 90.07% yield) as a colorless oil

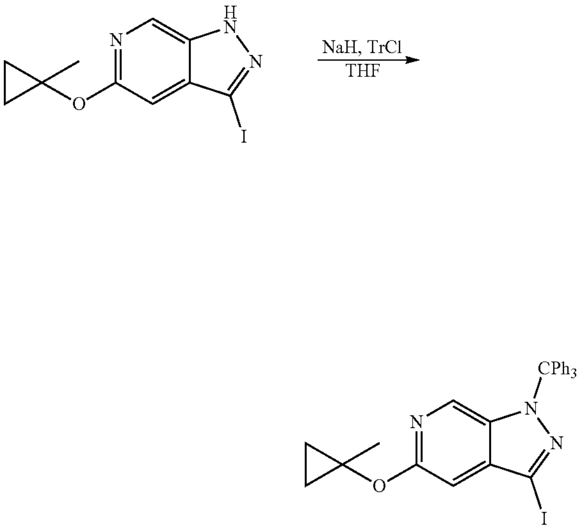

Step 7:

To a mixture of 3-iodo-5-(1-methylcyclopropoxy)-1H-pyrazolo[3,4-c]pyridine (750 mg, 2.38 mmol, 1 eq) in THF (10 mL) was added NaH (114.23 mg, 2.86 mmol, 60% purity, 1.2 eq) in one portion at 0° C. under $N_2$. The mixture was stirred at 0° C. for 30 min, then [chloro(diphenyl)methyl]benzene (796.22 mg, 2.86 mmol, 1.2 eq) was added, the solution was stirred at 20° C. for 2 h. TLC and LCMS showed the reaction was completed. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by silica gel chromatography (12 g, 0-5% (10 min) of Ethyl acetate in Petroleum ether) to give 3-iodo-5-(1-methylcyclopropoxy)-1-trityl-pyrazolo[3,4-c]pyridine (1.25 g, 2.24 mmol, 94.22% yield) as a white solid.

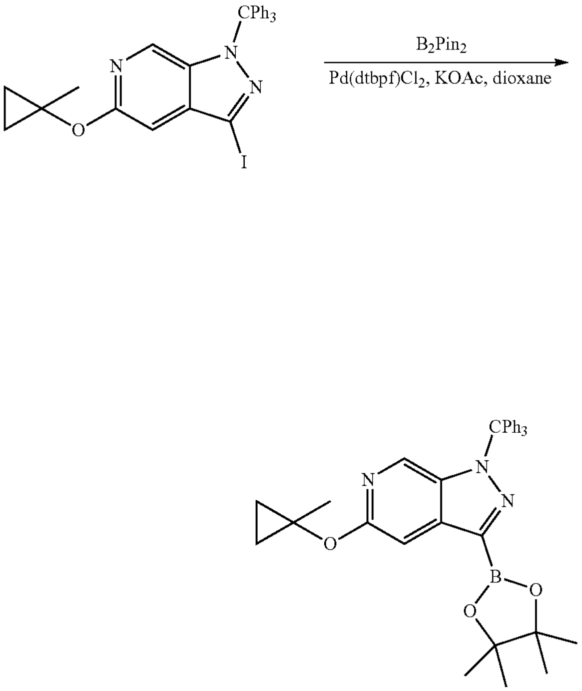

Step 8:

To a mixture of 3-iodo-5-(1-methylcyclopropoxy)-1-trityl-pyrazolo[3,4-c]pyridine (500 mg, 896.98 μmol, 1 eq), $Pin_2B_2$ (455.56 mg, 1.79 mmol, 2 eq) and KOAc (264.09 mg, 2.69 mmol, 3 eq) in dioxane (5 mL) was added ditert-butyl(cyclopentyl)phosphane; dichloropalladium; iron (29.23 mg, 44.85 μmol, 0.05 eq) in one portion at 20° C. under $N_2$. The mixture was stirred at 80° C. for 1 hour. TLC showed the reaction was completed. The mixture was cooled to 25° C., filtered and concentrated in vacuum to give 5-(1-methylcyclopropoxy)-3-(4,4,5,5-tetramethyl-1,3,2-dioxaborolan-2-yl)-1-trityl-pyrazolo[3,4-c]pyridine (800 mg, 760.55 μmol, 84.79% yield, 53% purity) as a black oil.

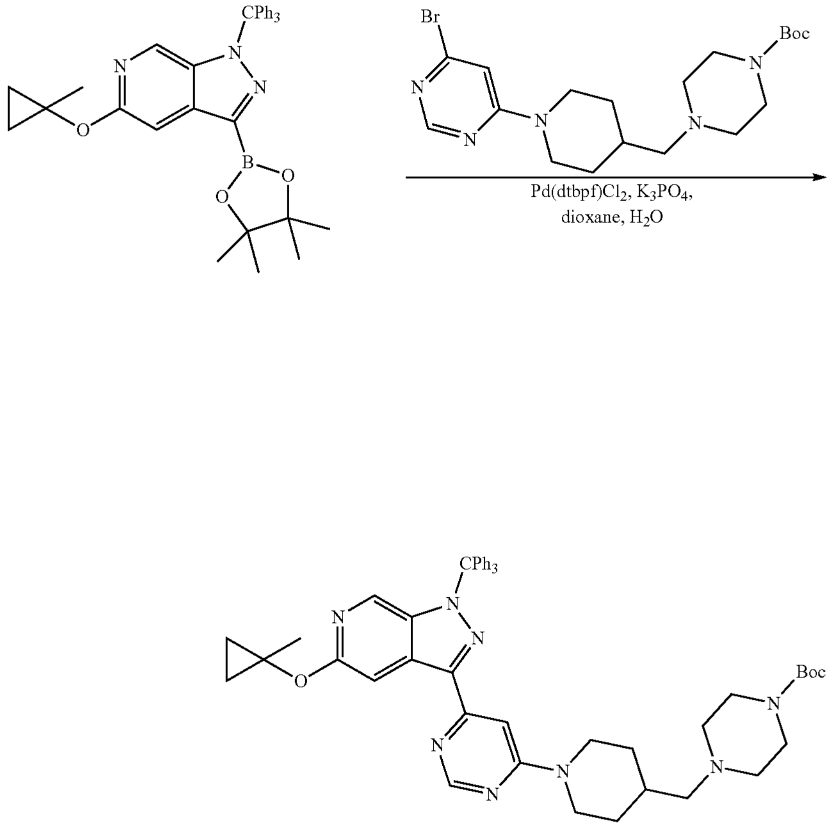

Step 9:

To a mixture of tert-butyl 4-[[1-(6-chloropyrimidin-4-yl)-4-piperidyl]methyl]piperazine-1-carboxylate (471.57 mg, 1.19 mmol, 1 eq), 5-(1-methylcyclopropoxy)-3-(4,4,5,5-tetramethyl-1,3,2-dioxaborolan-2-yl)-1-trityl-1H-pyrazolo[3,4-c]pyridine (800 mg, 1.19 mmol, 83% purity, 1 eq) and ditert-butyl(cyclopentyl)phosphane; dichloropalladium; iron (31.05 mg, 47.64 μmol, 0.04 eq) in 1,4-dioxane (10 mL) and $H_2O$ (2 mL) was added $K_3PO_4$ (581.50 mg, 2.74 mmol, 2.3 eq) in one portion at 25° C. under $N_2$. The mixture was stirred at 100° C. for 16 hours. LCMS showed there was desired MS. The mixture was cooled to 25° C., filtered and concentrated in vacuum. The residue was purified by silica gel chromatography (0-20% of Ethyl acetate in Petroleum ether) to give tert-butyl 4-((1-(6-(5-(1-methylcyclopropoxy)-1-trityl-1H-pyrazolo[3,4-c]pyridin-3-yl)pyrimidin-4-yl)piperidin-4-yl)methyl)piperazine-1-carboxylate (72.5 mg, 91.66 μmol, 7.70% yield) as a yellow gum

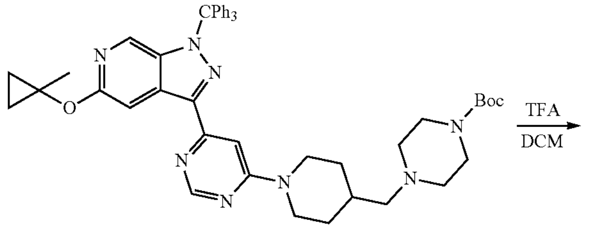

-continued

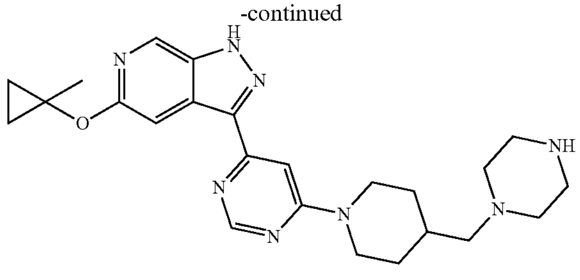

Step 10:

To a mixture of tert-butyl 4-[[1-[6-[5-(1-methylcyclopropoxy)-1-trityl-pyrazolo[3,4-c]pyridin-3-yl]pyrimidin-4-yl]-4-piperidyl]methyl]piperazine-1-carboxylate (72.5 mg, 91.66 μmol, 1 eq) in DCM (5 mL) was added TFA (209.02 mg, 1.83 mmol, 135.73 μL, 20 eq) in one portion at 20° C. The mixture was stirred at 20° C. for 1 h. TLC showed the reaction was completed. The mixture was concentrated in vacuum to give 5-(1-methylcyclopropoxy)-3-[6-[4-(piperazin-1-ylmethyl)-1-piperidyl]pyrimidin-4-yl]-1H-pyrazolo[3,4-c]pyridine (50 mg, 76.43 μmol, 83.39% yield, 86% purity, TFA) as a yellow solid.

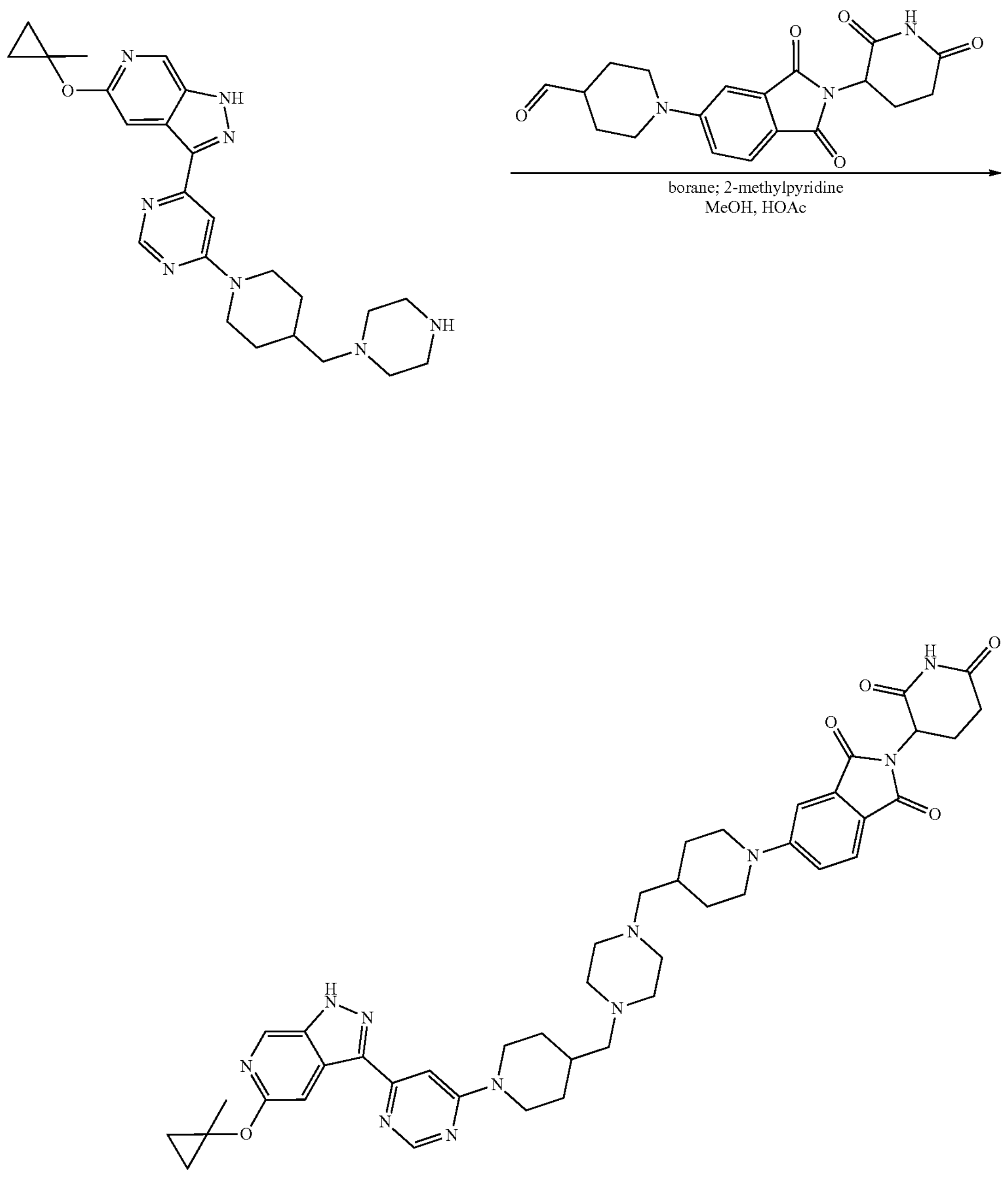

Step 11:

To a mixture of 5-(1-methylcyclopropoxy)-3-[6-[4-(piperazin-1-ylmethyl)-1-piperidyl]pyrimidin-4-yl]-1H-pyrazolo[3,4-c]pyridine (41 mg, 91.40 μmol, 1 eq) and 1-[2-(2,6-dioxo-3-piperidyl)-1,3-dioxo-isoindolin-5-yl]piperidine-4-carbaldehyde (33.76 mg, 91.40 μmol, 1 eq) in MeOH (5 mL) was added borane; 2-methylpyridine (19.55 mg, 182.81 μmol, 2 eq) and HOAc (5.49 mg, 91.40 μmol, 5.23 μL, 1 eq) in one portion at 20° C. under $N_2$. The mixture was stirred at 30° C. for 1 h to give yellow solution. LCMS showed there was ~39% of desired MS. The residue was poured into water (5 mL). The aqueous phase was extracted with ethyl acetate (5 mL*3). The combined organic phase was washed with brine (5 mL*2), dried with anhydrous $Na_2SO_4$, filtered and concentrated in vacuum. The crude product was purified by reversed-phase HPLC (column: 3_Phenomenex Luna C18 75*30 mm*3 um; mobile phase: [water (0.225% FA)-ACN]; B %: 0%-30%, 40 min). After prep. HPLC purification, the eluent was concentrated and lyophilized to give 2-(2,6-dioxo-3-piperidyl)-5-[4-[[4-[[1-[6-[5-(1-methylcyclopropoxy)-1H-pyrazolo[3,4-c]pyridin-3-yl]pyrimidin-4-yl]-4-piperidyl]methyl]piperazin-1-yl]methyl]-1-piperidyl]isoindoline-1,3-dione (30.3 mg, 35.63 μmol, 38.98% yield, 99.70% purity, FA) as a yellow solid.

Exemplary Synthesis of Compound 179

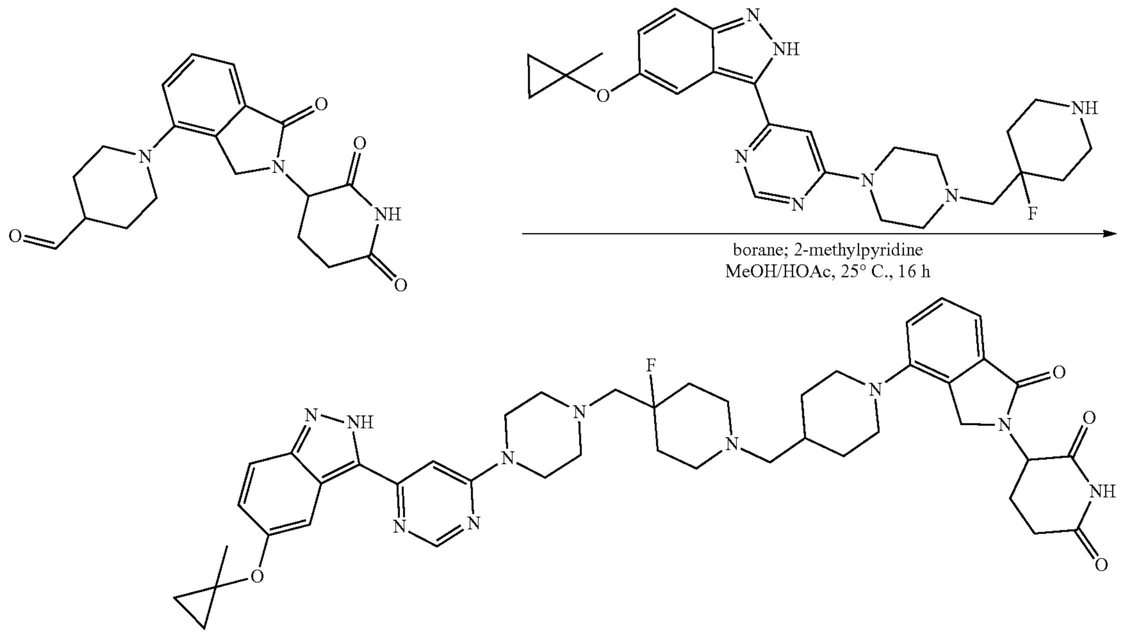

Step 1

To the mixture of 1-[2-(2,6-dioxo-3-piperidyl)-1-oxo-isoindolin-4-yl]piperidine-4-carbaldehyde (90 mg, 253.25 μmol, 1 eq) and 3-[6-[4-[(4-fluoro-4-piperidyl)methyl]piperazin-1-yl]pyrimidin-4-yl]-5-(1-methylcyclopropoxy)-2H-indazole (63.57 mg, 126.62 μmol, 0.5 eq, HCl) in HOAC (1 mL) and MeOH (10 mL) was stirred at 20° C. for 20 min, then was added borane; 2-methylpyridine (54.17 mg, 506.49 μmol, 2 eq). Then the mixture was stirred at 20° C. for 16 h under $N_2$. LCMS showed desired product. The residue was concentrated under reduced pressure to give a residue. The residue was purified by prep-HPLC (column: Xtimate C18 100*30 mm*10 um; mobile phase: [water (0.225% FA)-ACN]; B %: 0%-35%, 40 min) to give 3-[4-[4-[[4-fluoro-4-[[4-[6-[5-(1-methylcyclopropoxy)-2H-indazol-3-yl]pyrimidin-4-yl]piperazin-1-yl]methyl]-1-piperidyl]methyl]-1-piperidyl]-1-oxo-isoindolin-2-yl]piperidine-2,6-dione (32.5 mg, 38.49 μmol, 15.20% yield, 95.34% purity) as white solid.

Exemplary Synthesis of Compound 180

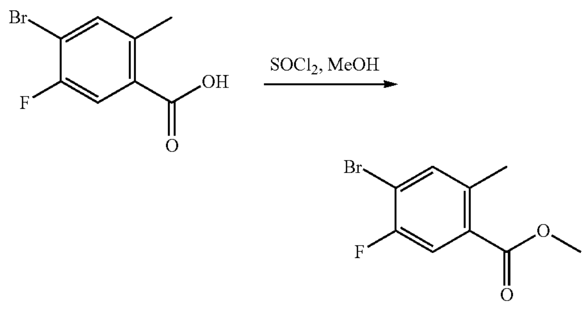

Step 1

To a solution of 4-bromo-5-fluoro-2-methyl-benzoic acid (1.5 g, 6.44 mmol, 1 eq) in MeOH (20 mL) was added $SOCl_2$ (1.91 g, 16.09 mmol, 1.17 mL, 2.5 eq). After addition, the reaction mixture was stirred at 80° C. for 1 h. LCMS (EB16-1535-P1A1) showed there was desired MS. The reaction mixture was concentrated under reduced pressure. The residue was purified by silica gel chromatography (20 g, Petroleum ether) to give methyl 4-bromo-5-fluoro-2-methyl-benzoate (1.65 g, crude) as a colorless oil.

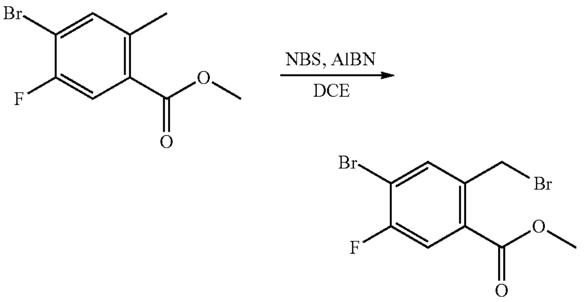

Step 2

To a stirred solution of methyl 4-bromo-5-fluoro-2-methyl-benzoate (1.54 g, 6.23 mmol, 1 eq) in DCE (10 mL) under an atmosphere of nitrogen was added NBS (1.33 g, 7.48 mmol, 1.2 eq) followed by 2-[(E)-(1-cyano-1-methyl-ethyl)azo]-2-methyl-propanenitrile (51.18 mg, 311.66 μmol, 0.05 eq) and the resulting mixture was stirred vigorously at 70° C. for 2 h. LCMS (EB16-1541-P1A1) showed there was no starting material. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by prep-HPLC (column: Xtimate C18 150*40 mm*10 um; mobile phase: [water (0.225% FA)-ACN]; B %: 60%-90%, 10 min) to give methyl 4-bromo-2-(bromomethyl)-5-fluoro-benzoate (1.3 g, 3.99 mmol, 63.98% yield) as a white solid.

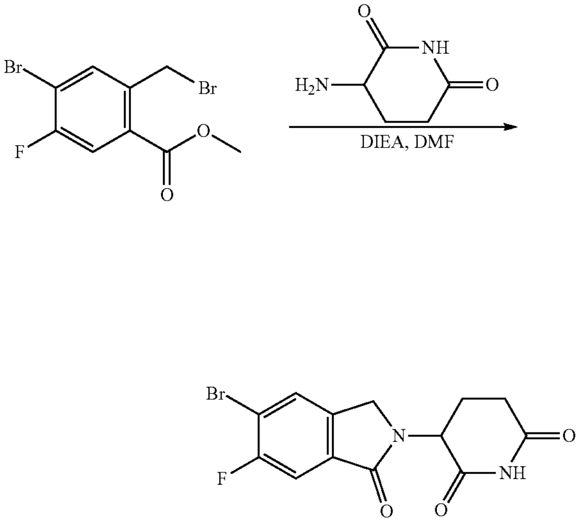

Step 3

To a mixture of methyl 4-bromo-2-(bromomethyl)-5-fluoro-benzoate (1.3 g, 3.99 mmol, 1 eq) and 3-aminopiperidine-2,6-dione (787.71 mg, 4.79 mmol, 1.2 eq, HCl) in DMF (10 mL) was added DIEA (2.58 g, 19.94 mmol, 3.47 mL, 5 eq) in one portion at 20° C. under $N_2$. The mixture was stirred at 85° C. for 48 hours. LCMS (EB16-1548-P1A2) showed there was desired MS. The crude was concentrated in vacuum. The crude product was triturated with MeCN (20 mL) and $H_2O$ (20 mL) at 20° C. The crude was filtered and solid was concentrated in vacuum to give 3-(5-bromo-6-fluoro-1-oxo-isoindolin-2-yl)piperidine-2,6-dione (830 mg, 2.43 mmol, 61.01% yield) as a dark gray solid

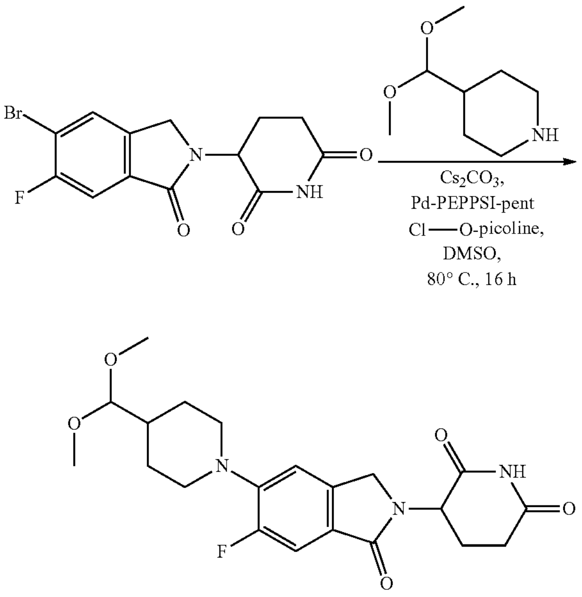

Step 4

To a solution of 3-(5-bromo-6-fluoro-1-oxo-isoindolin-2-yl)piperidine-2,6-dione (100 mg, 293.14 μmol, 1 eq) and 4-(dimethoxymethyl)piperidine (93.35 mg, 586.28 μmol, 2 eq) in DMSO (5 mL) was added $Cs_2CO3$ (191.02 mg, 586.28 μmol, 2 eq) and Pd-PEPPSI-pent Cl—O-picoline (15.92 mg, 29.31 μmol, 0.1 eq). After addition, the reaction mixture was stirred at 80° C. under $N_2$ for 12 h. LCMS (EB16-1555-P1A2) showed there was desired MS. The mixture was cooled to 20° C. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by prep-TLC (Petroleum ether/Ethyl acetate=0/1) to give 3-[5-[4-(dimethoxymethyl)-1-piperidyl]-6-fluoro-1-oxo-isoindolin-2-yl]piperidine-2,6-dione (70 mg, 91.79 μmol, 31.31% yield, 55% purity) as a yellow oil.

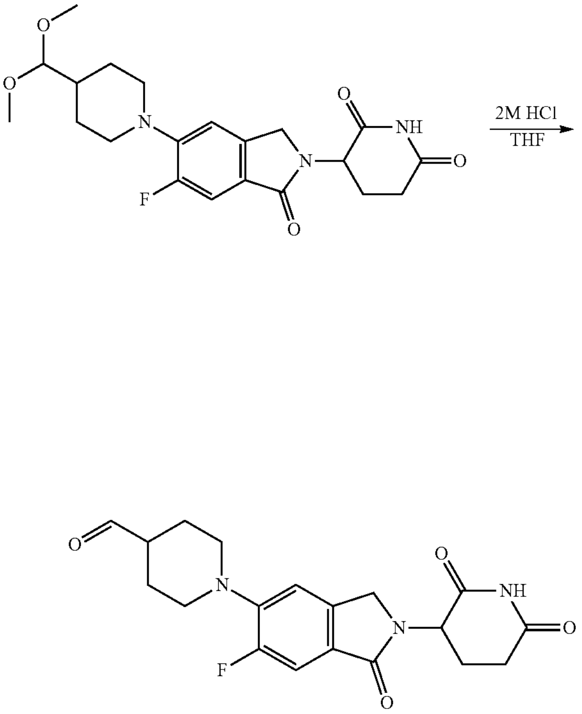

Step 5

To a mixture of 3-[5-[4-(dimethoxymethyl)-1-piperidyl]-6-fluoro-1-oxo-isoindolin-2-yl]piperidine-2,6-dione (70 mg, 166.89 μmol, 1 eq) in THF (5 mL) was added HCl (2 M, 83.44 μL, 1 eq) in one portion at 20° C. under $N_2$. The mixture was stirred at 20° C. for 2 hours to give yellow solution. TLC showed the reaction was completed. The residue was poured into saturated $NaHCO_3$ to adjust the pH=7-8. The aqueous phase was extracted with ethyl acetate (20 mL*3). The combined organic phase was washed with brine (20 mL*2), dried with anhydrous $Na_2SO_4$, filtered and concentrated in vacuum to give 1-[2-(2,6-dioxo-3-piperidyl)-6-fluoro-1-oxo-isoindolin-5-yl]piperidine-4-carbaldehyde (43 mg, 63.34 μmol, 37.95% yield, 55% purity) as a yellow solid.

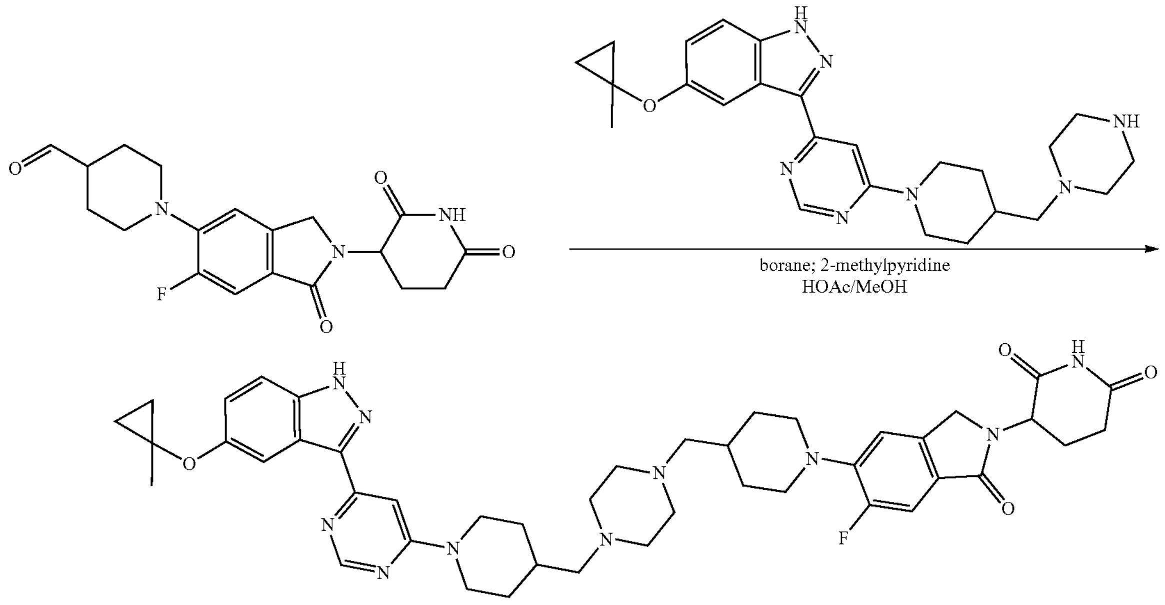

Step 6

To a mixture of 5-(1-methylcyclopropoxy)-3-[6-[4-(piperazin-1-ylmethyl)-1-piperidyl]pyrimidin-4-yl]-2H-indazole (50 mg, 111.71 μmol, 0.97 eq) and 1-[2-(2,6-dioxo-3-piperidyl)-6-fluoro-1-oxo-isoindolin-5-yl]piperidine-4-carbaldehyde (43 mg, 115.16 μmol, 1 eq) in MeOH (10 mL) was added borane; 2-methylpyridine (24.64 mg, 230.33 μmol, 2 eq) and HOAc (6.92 mg, 115.16 μmol, 6.59 μL, 1 eq) in one portion at 20° C. under $N_2$. The mixture was stirred at 20° C. for 10 h to give yellow solution. LCMS (EB16-1563-P1A1) showed there was desired MS. The resulting product was poured into $H_2O$ (20 mL). The mixture was extracted with ethyl acetate (20 mL*3). The organic phase was washed with brine (15 mL*2), dried over anhydrous $Na_2SO_4$, concentrated in vacuum to give a residue. The residue was purified by prep-HPLC (column: Phenomenex luna 30*30 mm*10 um+YMC AQ 100*30*10 um; mobile phase: [water (0.225% FA)-ACN]; B %: 2%-42%, 26 min) to give 3-[6-fluoro-5-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (12.4 mg, 15.32 μmol, 13.31% yield, 99.47% purity) as a white solid.

Exemplary Synthesis of Compound 181

-continued

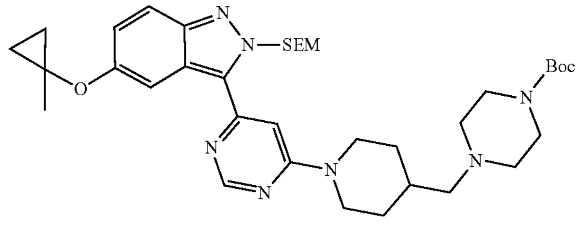

Step 1

To a solution of 2-[[3-(6-chloropyrimidin-4-yl)-5-(1-methylcyclopropoxy)indazol-2-yl]methoxy]ethyl-trimethyl-silane (1 g, 2.32 mmol, 1.32 eq) and tert-butyl 4-(4-piperidylmethyl)piperazine-1-carboxylate (500 mg, 1.76 mmol, 1 eq) in DMSO (8 mL) was added DIEA (684.05 mg, 5.29 mmol, 921.90 μL, 3 eq). After addition, the reaction solution was stirred at 90° C. for 1 h. LCMS (EB12-979-P1B) and TLC (petroleum ether:ethyl acetate=1:1) showed the reaction completed. After cooling, the reaction mixture was diluted with ethyl acetate (20 mL) and washed with brine (20 mL*3). The organic layer was dried over sodium sulfate and concentrated under reduced pressure. The residue was purified by silica gel column chromatography (0 to 68% ethyl acetate in petroleum ether) to afford tert-butyl 4-[[1-[6-[5-(1-methylcyclopropoxy)-2-(2-trimethylsilylethoxymethyl)indazol-3-yl]pyrimidin-4-yl]-4-piperidyl]methyl]piperazine-1-carboxylate (660 mg, 876.17 μmol, 49.66% yield, 90% purity) as a white solid.

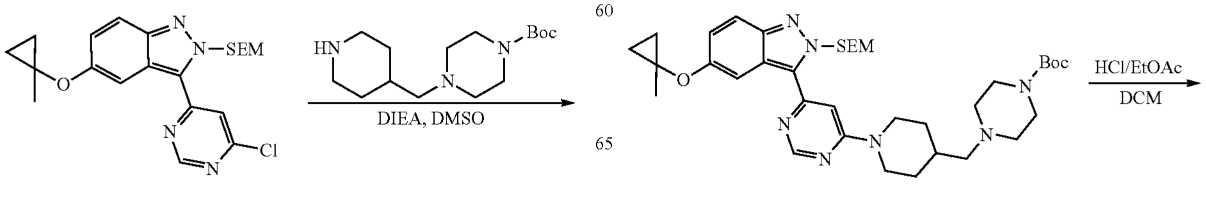

-continued

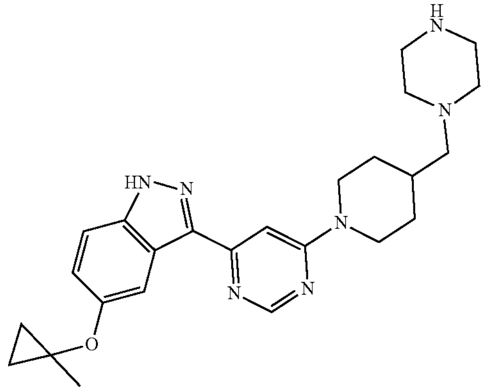

Step 2

To a solution of tert-butyl 4-[[1-[6-[5-(1-methylcyclopropoxy)-2-(2-trimethylsilylethoxymethyl)indazol-3-yl]pyrimidin-4-yl]-4-piperidyl]methyl]piperazine-1-carboxylate (658.04 mg, 970.64 μmol, 1 eq) in DCM (5 mL) was added HCl/EtOAc (4 M, 5 mL). After addition, the reaction solution was stirred at 20° C. for 12 h. LCMS (EB12-983-P1B) showed the reaction completed. The reaction mixture was concentrated under reduced pressure to afford 5-(1-methylcyclopropoxy)-3-[6-[4-(piperazin-1-ylmethyl)-1-piperidyl]pyrimidin-4-yl]-1H-indazole (450 mg, crude, HCl) as a white solid. The crude product was used for next step directly.

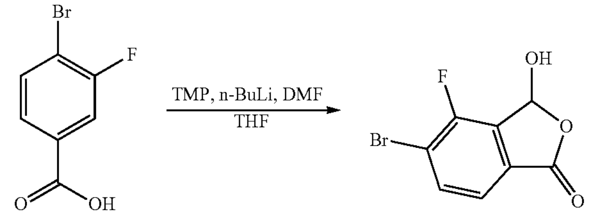 [SMILES: O=C(O)c1ccc(Br)c(F)c1 ; O=C1OC(O)c2c1ccc(Br)c2F ; "THF"]

Step 3

To a solution of TMP (4.84 g, 34.25 mmol, 5.81 mL, 2.5 eq) in THF (30 mL) was added n-BuLi (2.5 M, 13.70 mL, 2.5 eq) dropwise under $N_2$ at 0° C. and the resulting mixture was stirred at 0° C. for 30 min. The reaction mixture was then cooled to −45° C. and 4-bromo-3-fluoro-benzoic acid (3 g, 13.70 mmol, 1 eq) dissolved in THF (15 mL), was added dropwise and stirring was continued at −45° C. for 5 h. DMF (1.50 g, 20.55 mmol, 1.58 mL, 1.5 eq) was added dropwise and the reaction mixture was allowed to warm to 20° C. and stirred for 12 h. LCMS (EB12-978-P1B1) showed the starting material consumed. The reaction mixture was quenched by 3 M HCl (25 mL) at 0° C. and extracted with ethyl acetate (30 mL*3). The organic layer was dried over sodium sulfate and concentrated under reduced pressure. The residue was purified by silica gel column chromatography (0 to 58% ethyl acetate in petroleum ether) to afford 5-bromo-4-fluoro-3-hydroxy-3H-isobenzofuran-1-one (1.7 g, 6.88 mmol, 50.24% yield) as a brown solid.

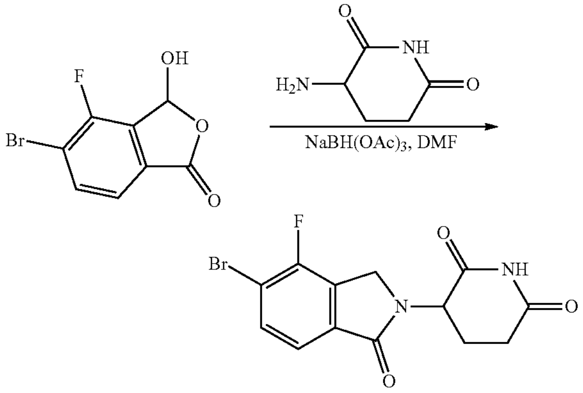

Step 4

To a solution of 5-bromo-4-fluoro-3-hydroxy-3H-isobenzofuran-1-one (500 mg, 2.02 mmol, 1 eq) in DMF (5 mL) was added 3-aminopiperidine-2,6-dione hydrochloride (499.73 mg, 3.04 mmol, 1.5 eq) and NaBH(OAc)3 (1.07 g, 5.06 mmol, 2.5 eq). After addition, the reaction mixture was stirred at 20° C. for 12 h. LCMS (EB12-984-P1B) showed the reaction completed. The reaction mixture was diluted with water (30 mL) and cooled to 0° C. with water/ice bath which resulted in the formation precipitate. The resulting mixture was filtered and the dark blue solid was washed with MTBE (30 mL*2). The obtained solid was dried under reduced pressure to afford 3-(5-bromo-4-fluoro-1-oxo-isoindolin-2-yl)piperidine-2,6-dione (340 mg, crude) as a blue solid. The crude product was used for next step directly.

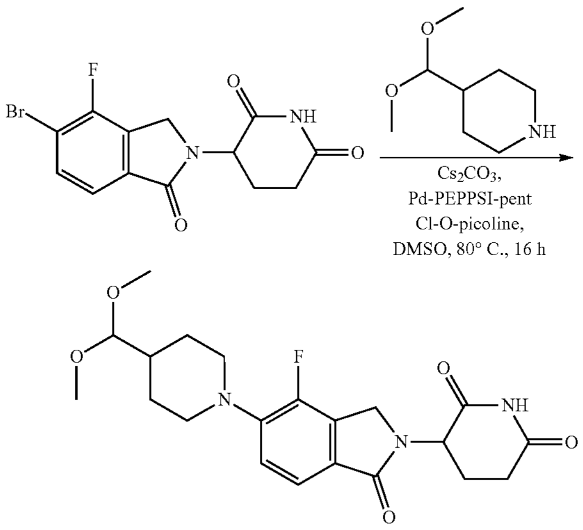

Step 5

To a solution of 3-(5-bromo-4-fluoro-1-oxo-isoindolin-2-yl)piperidine-2,6-dione (200 mg, 586.28 μmol, 1 eq) and 4-(dimethoxymethyl)piperidine (186.70 mg, 1.17 mmol, 2 eq) in DMSO (5 mL) was added Cs2CO3 (382.05 mg, 1.17 mmol, 2 eq) and Pd-PEPPSI-pent Cl—O-picoline (31.84 mg, 58.63 μmol, 0.1 eq). After addition, the reaction mixture was stirred at 80° C. under $N_2$ for 12 h. LCMS (EB12-992-P1B) and TLC (petroleum ether:ethyl acetate=0:1) showed the reaction completed. After cooling, the reaction mixture was poured into saturated $NH_4Cl$ (40 mL) and extracted with ethyl acetate (20 mL*3). The organic layer was dried over sodium sulfate and concentrated under reduced pressure. The residue was purified by prep.TLC (pure ethyl acetate) to afford 3-[5-[4-(dimethoxymethyl)-1-piperidyl]-4-fluoro-1-oxo-isoindolin-2-yl]piperidine-2,6-dione (50 mg, 119.20 μmol, 20.33% yield) as a yellow solid.

Step 6

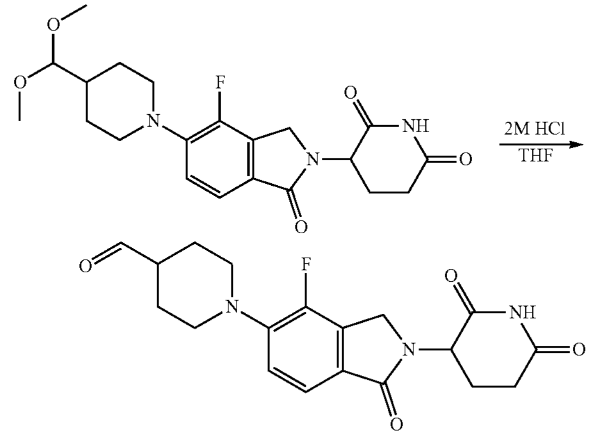

To a solution of 3-[5-[4-(dimethoxymethyl)-1-piperidyl]-4-fluoro-1-oxo-isoindolin-2-yl]piperidine-2,6-dione (50 mg, 119.20 μmol, 1 eq) in THF (2 mL) was added HCl (2 M, 2 mL, 33.56 eq). After addition, the reaction solution was stirred at 20° C. for 2 h. LCMS showed the reaction completed. The reaction mixture was quenched by saturated $NaHCO_3$ (10 mL) and extracted with ethyl acetate (10 mL*3). The organic layer was dried over sodium sulfate and concentrated under reduced pressure to afford 1-[2-(2,6-dioxo-3-piperidyl)-4-fluoro-1-oxo-isoindolin-5-yl]piperidine-4-carbaldehyde (60 mg, crude) as a yellow solid. The crude product was used for next step directly.

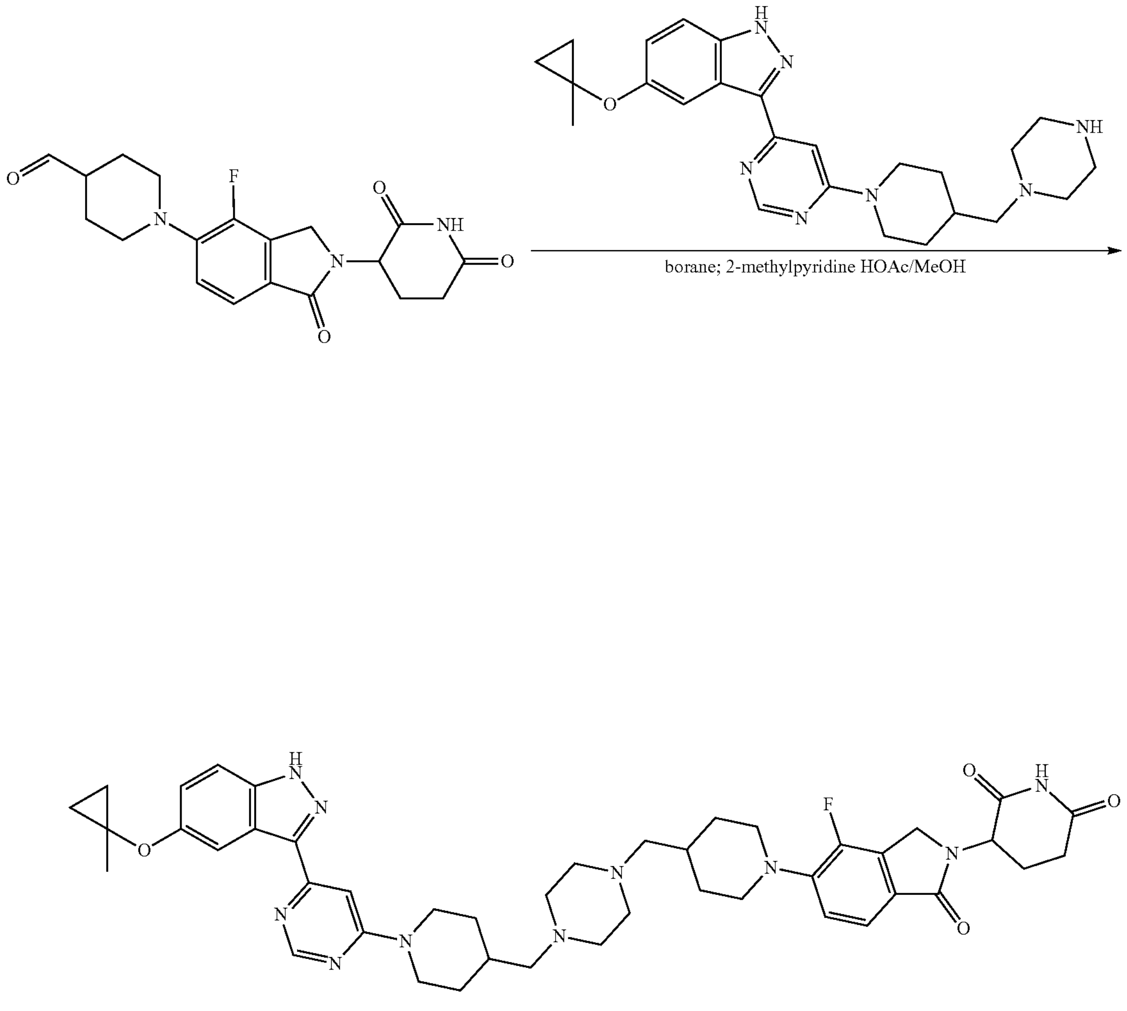

Step 7

To a mixture of 1-[2-(2,6-dioxo-3-piperidyl)-4-fluoro-1-oxo-isoindolin-5-yl]piperidine-4-carbaldehyde (15 mg, 40.17 μmol, 1.30 eq) in MeOH (5 mL) and HOAc (0.5 mL) was added a solution of 5-(1-methylcyclopropoxy)-3-[6-[4-(piperazin-1-ylmethyl)-1-piperidyl]pyrimidin-4-yl]-1H-indazole (15 mg, 30.99 μmol, 1 eq, HCl) and DIEA (4.01 mg, 30.99 μmol, 5.40 μL, 1 eq) in MeOH (1 mL). Then borane; 2-methylpyridine (6.63 mg, 61.98 μmol, 2 eq) was added to above solution. After addition, the reaction solution was stirred at 20° C. for 12 h. LCMS showed the reaction completed. The reaction solution was concentrated under reduced pressure to remove most of solvent. The residue was purified by prep.HPLC (column: Xtimate C18 100*30 mm*10 um; mobile phase: [water (0.225% FA)-ACN]; B %: 0%-35%, 40 min) to afford 3-[4-fluoro-5-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (6.9 mg, 8.51 μmol, 27.46% yield, 99.29% purity) as a white solid.

Exemplary Synthesis of Compound 182

Step 1

To a mixture of 1-[2-(2,6-dioxo-3-piperidyl)-4-fluoro-1-oxo-isoindolin-5-yl]piperidine-4-carbaldehyde (45 mg, 120.52 μmol, 1.34 eq) in MeOH (5 mL) and HOAc (0.5 mL) was added a solution of 3-[6-[4-[(4-fluoro-4-piperidyl)methyl]piperazin-1-yl]pyrimidin-4-yl]-5-(1-methylcyclopropoxy)-2H-indazole (45 mg, 89.64 μmol, 1 eq, HCl) and DIEA (11.58 mg, 89.64 μmol, 15.61 μL, 1 eq) in MeOH (1 mL). Then borane; 2-methylpyridine (19.18 mg, 179.27 μmol, 2 eq) was added to above solution. After addition, the reaction solution was stirred at 20° C. for 12 h. LCMS showed the reaction completed. The reaction solution was concentrated under reduced pressure to remove most of solvent. The residue was purified by prep.HPLC (column: Phenomenex luna 30*30 mm*10 um+YMC AQ 100*30*10 um; mobile phase: [water (0.225% FA)-ACN]; B %: 0%-40%, 26 min) to afford 3-[4-fluoro-5-[4-[[4-fluoro-4-[[4-[6-[5-(1-methylcyclopropoxy)-1H-indazol-3-yl]pyrimidin-4-yl]piperazin-1-yl]methyl]-1-piperidyl]methyl]-1-piperidyl]-1-oxo-isoindolin-2-yl]piperidine-2,6-dione (17.0 mg, 20.53 μmol, 22.90% yield, 99.38% purity) as a white solid.

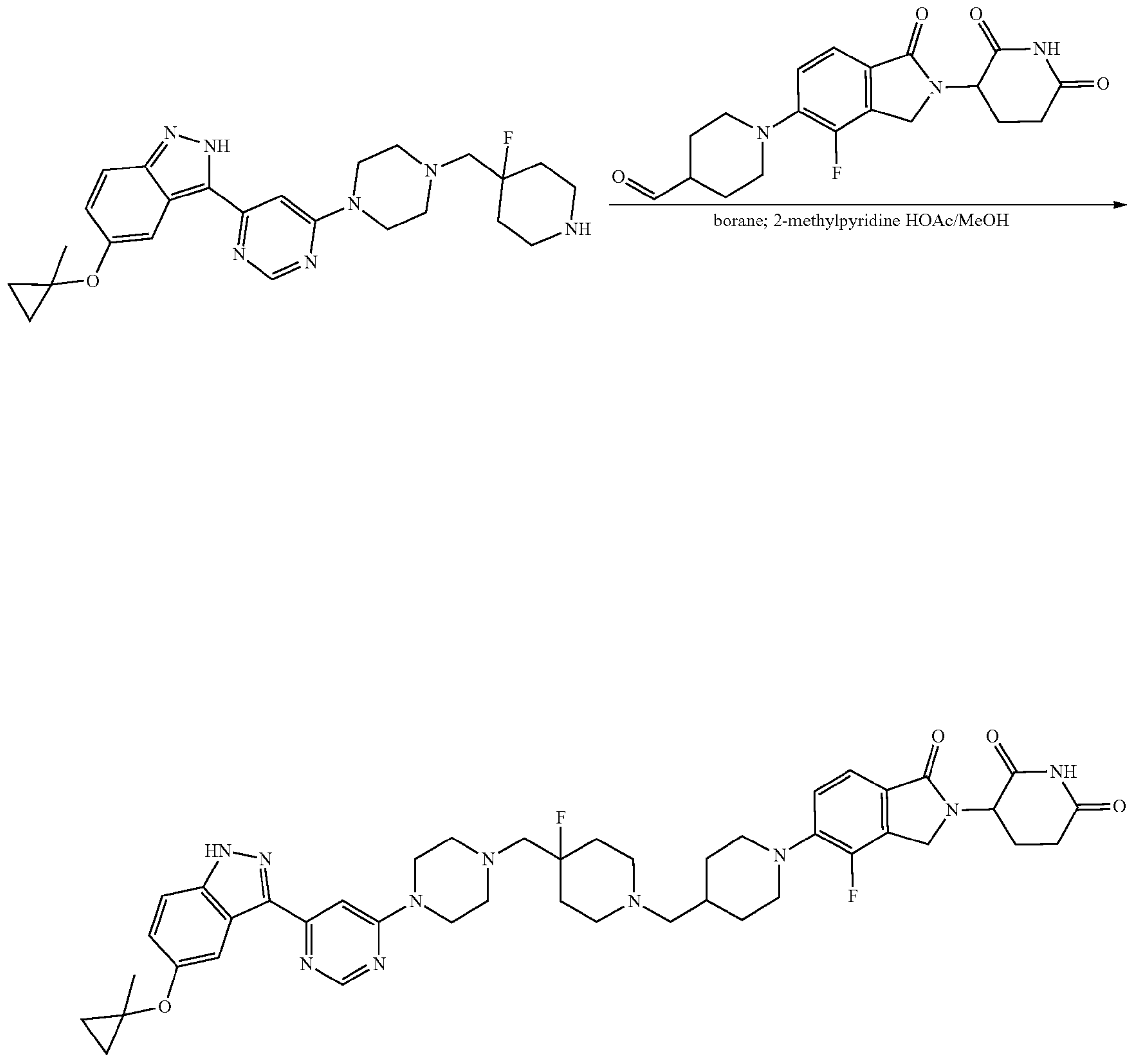

Exemplary Synthesis of Compound 183

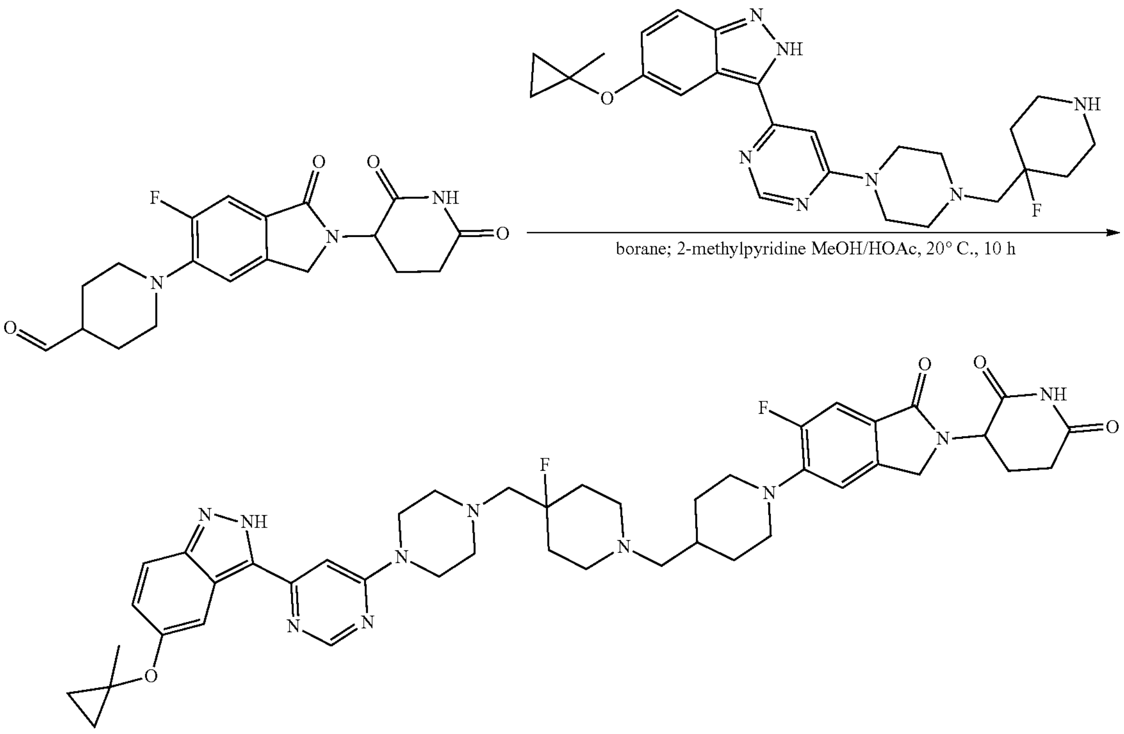

Step 1:

To a mixture of 3-[6-[4-[(4-fluoro-4-piperidyl)methyl]piperazin-1-yl]pyrimidin-4-yl]-5-(1-methylcyclopropoxy)-2H-indazole (87.28 mg, 187.48 μmol, 1 eq) and 1-[2-(2,6-dioxo-3-piperidyl)-6-fluoro-1-oxo-isoindolin-5-yl]piperidine-4-carbaldehyde (70 mg, 187.48 μmol, 1 eq) in MeOH (10 mL) was added borane; 2-methylpyridine (20.05 mg, 187.48 μmol, 1 eq) and HOAc (11.26 mg, 187.48 μmol, 10.72 μL, 1 eq) in one portion at 20° C. under $N_2$. The mixture was stirred at 20° C. for 10 hours to give yellow solution. LCMS showed the desired mass. The reaction solution was concentrated under reduced pressure to remove most of solvent. The residue was purified by prep-HPLC (column: Xtimate C18 100*30 mm*10 um; mobile phase: [water (0.225% FA)-ACN]; B %: 0%-35%, 40 min) to give 3-[6-fluoro-5-[4-[[4-fluoro-4-[[4-[6-[5-(1-methylcyclopropoxy)-2H-indazol-3-yl]pyrimidin-4-yl]piperazin-1-yl]methyl]-1-piperidyl]methyl]-1-piperidyl]-1-oxo-isoindolin-2-yl]piperidine-2,6-dione (30.7 mg, 35.72 μmol, 19.05% yield, 95.75% purity) as a white solid.

Exemplary Synthesis of Compound 184

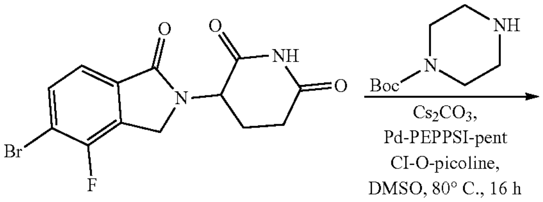

-continued

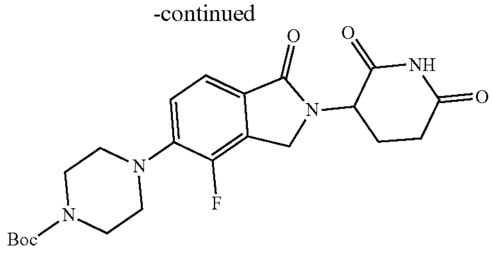

Step 1:

To a solution of 3-(5-bromo-4-fluoro-1-oxo-isoindolin-2-yl)piperidine-2,6-dione (240 mg, 703.54 μmol, 1 eq) and tert-butyl piperazine-1-carboxylate (196.55 mg, 1.06 mmol, 1.5 eq) in DMSO (10 mL) was added $Cs_2CO3$ (458.45 mg, 1.41 mmol, 2 eq) and Pd-PEPPSI-pent Cl—O-picoline (38.20 mg, 70.35 μmol, 0.1 eq), then the mixture was stirred at 80° C. for 16 hours. TLC (Petroleum ether:Ethyl acetate=1:3, $R_f$=0.2, UV=254 nm) showed new spots formed. The reaction mixture was diluted with water (50 mL) and extracted with EtOAc (50 mL*3). The combined organic layers were washed with brine (50 mL), dried over $Na_2SO_4$, filtered and concentrated under reduced pressure to give a residue. The residue was purified by flash silica gel chromatography (ISCO®; 12 g SepaFlash® Silica Flash Column, Eluent of 0-60% Ethyl acetate/Petroleum ethergradient @ 40 mL/minute). Compound tert-butyl 4-[2-(2,6-dioxo-3-piperidyl)-4-fluoro-1-oxo-isoindolin-5-yl]piperazine-1-carboxylate (90 mg, 133.04 μmol, 18.91% yield, 66% purity) was obtained as a light yellow solid.

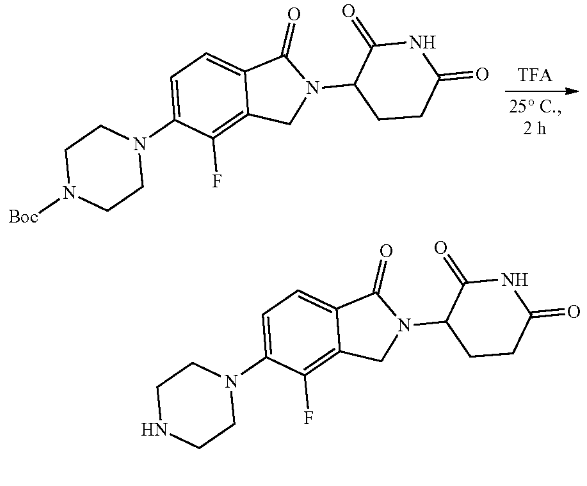

Step 2:

To a solution of tert-butyl 4-[2-(2,6-dioxo-3-piperidyl)-4-fluoro-1-oxo-isoindolin-5-yl]piperazine-1-carboxylate (260 mg, 582.34 μmol, 1 eq) in TFA (66.40 mg, 582.34 μmol, 43.12 μL, 1 eq), then the mixture was stirred at 25° C. for 2 hours. LCMS showed desire compound and the starting materials was consumed completely. The reaction mixture was concentrated under reduced pressure to give a residue. Compound 3-(4-fluoro-1-oxo-5-piperazin-1-yl-isoindolin-2-yl)piperidine-2,6-dione (300 mg, 358.40 μmol, 61.54% yield, 55% purity, TFA) was obtained as a light yellow oil.

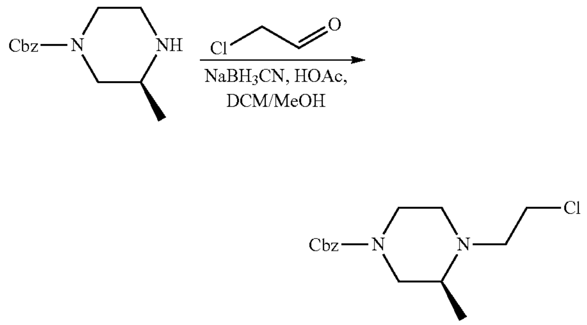

Step 3:

To a solution of benzyl (3S)-3-methylpiperazine-1-carboxylate (1.6 g, 6.83 mmol, 1 eq) and 2-chloroacetaldehyde (6.70 g, 34.15 mmol, 5.49 mL, 40% purity, 5 eq) in DCM (15 mL) and MeOH (15 mL) was added HOAc (41.01 mg, 682.90 μmol, 39.06 μL, 0.1 eq), then the mixture was stirred at 25° C. for 0.5 hour, and then $NaBH_3CN$ (858.30 mg, 13.66 mmol, 2 eq) was added the above mixture, the mixture was stirred at 25° C. for 0.5 hour. TLC (Petroleum ether: Ethyl acetate=1:1, Rf=0.52, $I_2$) showed a main spot formed. The reaction mixture was filtered and concentrated under reduced pressure to give a residue. The residue was purified by flash silica gel chromatography (ISCO®; 40 g Sepa-Flash® Silica Flash Column, Eluent of 0-44% Ethyl acetate/Petroleum ethergradient @ 50 mL/min). Compound benzyl (3S)-4-(2-chloroethyl)-3-methyl-piperazine-1-carboxylate (1.8 g, 6.06 mmol, 88.81% yield) was obtained as a colorless oil.

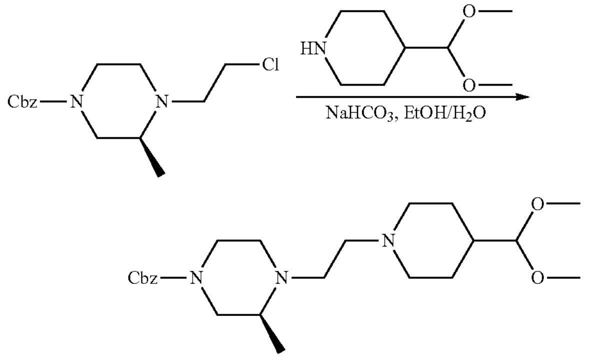

Step 4:

Benzyl (3S)-4-(2-chloroethyl)-3-methyl-piperazine-1-carboxylate (800 mg, 2.70 mmol, 1 eq) and 4-(dimethoxymethyl)piperidine (515.03 mg, 3.23 mmol, 1.2 eq) were dissolved in EtOH (10 mL) and $H_2O$ (1 mL), then $NaHCO_3$ (679.32 mg, 8.09 mmol, 314.50 μL, 3 eq) were added the reaction and stirred at 80° C. for 5 hours. TLC (Dichloromethane:Methanol=5:1, Rf=0.52, PMA) showed a main spot formed and the starting materials was consumed completely. The reaction mixture was added water (50 mL) and extracted with brine (50 mL*3). The combined organic layers were washed with brine (80 mL), dried over $Na_2SO_4$, filtered and concentrated under reduced pressure to give a residue. The residue was purified by flash silica gel chromatography (ISCO®; 12 g SepaFlash® Silica Flash Column, Eluent of 0-12% Ethyl acetate/Petroleum ethergradient @ 50 mL/min). Compound benzyl (3S)-4-[2-[4-(dimethoxymethyl)-1-piperidyl]ethyl]-3-methyl-piperazine-1-carboxylate (0.4 g, 953.39 μmol, 35.37% yield) was obtained as a colorless oil.

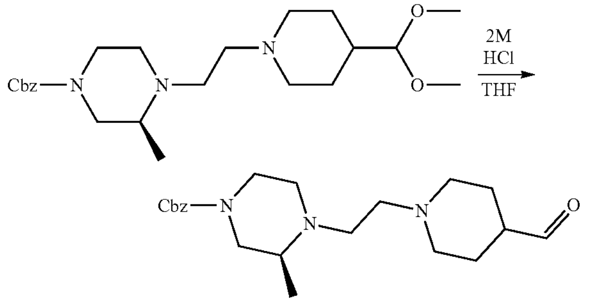

Step 5:

To a solution of benzyl (3S)-4-[2-[4-(dimethoxymethyl)-1-piperidyl]ethyl]-3-methyl-piperazine-1-carboxylate (400 mg, 953.39 μmol, 1 eq) in THF (5 mL) was added HCl (2 M, 5 mL, 10.49 eq), then the mixture was stirred at 25° C. for 2 hours. The reaction mixture was diluted with Sat. $NaHCO_3$ adjust to pH=8 and extracted with EtOAc (50 mL*3). The combined organic layers were washed with brine (50 mL), dried over $Na_2SO_4$, filtered and concentrated under reduced pressure to give a residue. Compound benzyl (3S)-4-[2-(4-formyl-1-piperidyl)ethyl]-3-methyl-piperazine-1-carboxylate (350 mg, 937.11 μmol, 98.29% yield) was obtained as a light yellow oil.

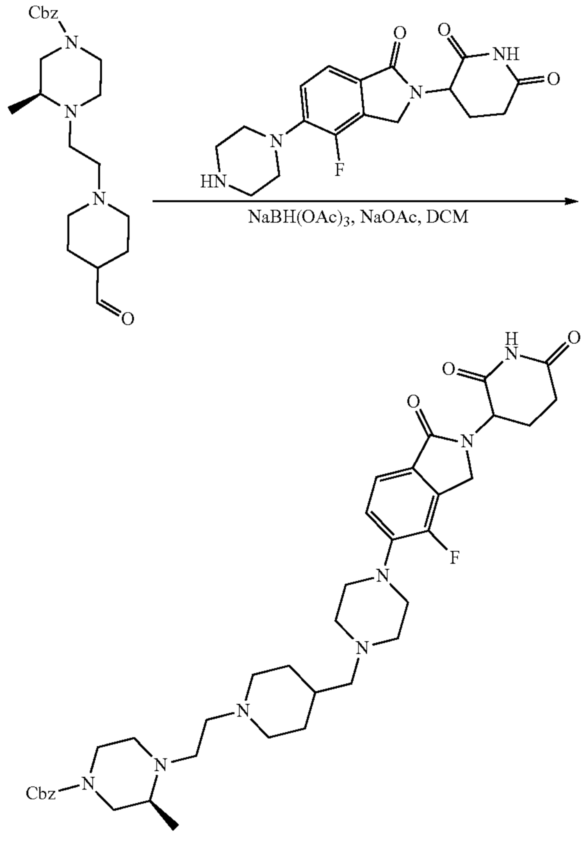

Step 6:

To a solution of 3-(4-fluoro-1-oxo-5-piperazin-1-yl-isoindolin-2-yl)piperidine-2,6-dione (300 mg, 651.64 μmol, 1 eq, TFA) and benzyl (3S)-4-[2-(4-formyl-1-piperidyl)ethyl]-3-methyl-piperazine-1-carboxylate (243.38 mg, 651.64 μmol, 1 eq) in DCM (5 mL) and MeOH (1 mL) was added NaOAc (267.28 mg, 3.26 mmol, 5 eq), then the mixture was stirred at 1 hour, and $NaBH(OAc)_3$ (276.22 mg, 1.30 mmol, 2 eq) was added the solution then the mixture was stirred at 25° C. for 2 hours. LCMS showed ~54% desire compound and TLC (Dichloromethane:Methanol=5:1, $R_f$=0.28, $I_2$) showed a main spot formed. The reaction mixture was diluted with Sat $NaHCO_3$ adjust to pH=8 and extracted with EtOAc (50 mL*3). The combined organic layers were washed with brine (50 mL), dried over $Na_2SO_4$, filtered and concentrated under reduced pressure to give a residue. The residue was purified by flash silica gel chromatography (ISCO®; 12 g SepaFlash® Silica Flash Column, Eluent of 0-14% Dichloromethane:Methanol ethergradient @ 40 mL/minute). Compound benzyl (3S)-4-[2-[4-[[4-[2-(2,6-dioxo-3-piperidyl)-4-fluoro-1-oxo-isoindolin-5-yl]piperazin-1-yl]methyl]-1-piperidyl]ethyl]-3-methyl-piperazine-1-carboxylate (150 mg, 213.12 μmol, 32.70% yield) was obtained as a white solid.

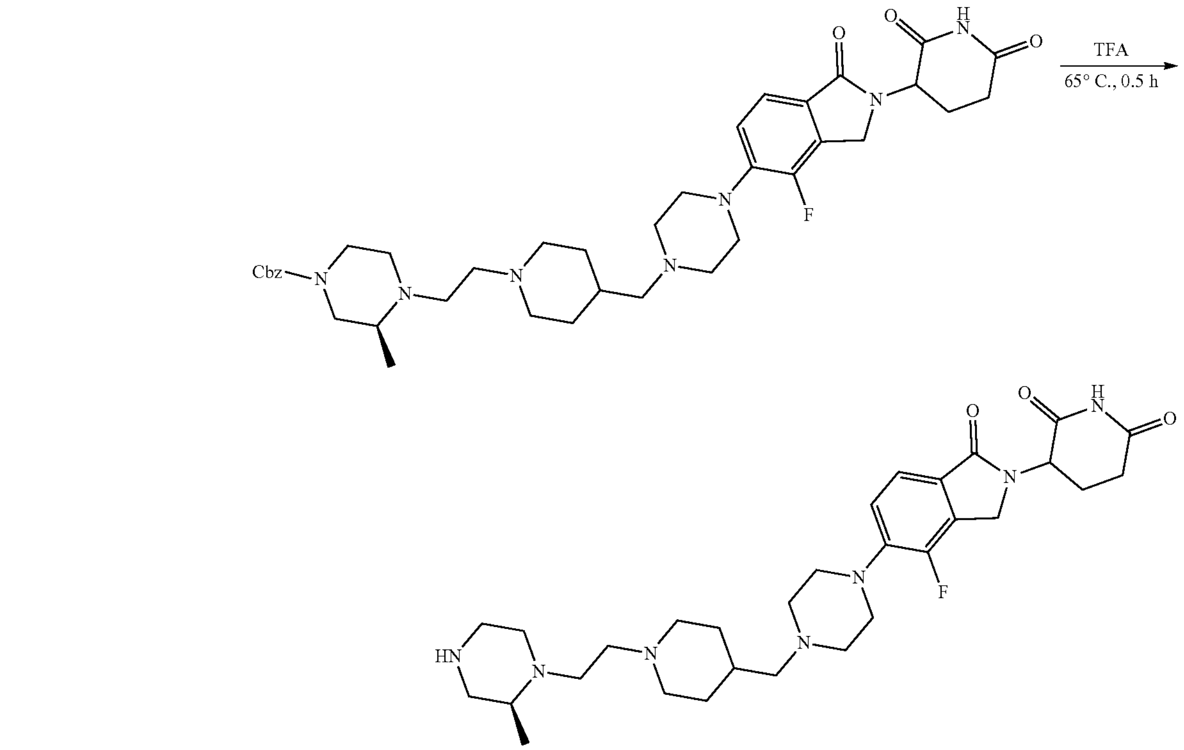

Step 7:

To a solution of benzyl (3S)-4-[2-[4-[[4-[2-(2,6-dioxo-3-piperidyl)-4-fluoro-1-oxo-isoindolin-5-yl]piperazin-1-yl]methyl]-1-piperidyl]ethyl]-3-methyl-piperazine-1-carboxylate (140 mg, 198.91 μmol, 1 eq) in TFA (4.62 g, 40.52 mmol, 3 mL, 203.70 eq), then the mixture was stirred at 65° C. for 0.5 hour. LCMS showed ~87.2% desired compound and the starting materials were consumed completely. The reaction mixture was concentrated under reduced pressure to give a residue. Compound 3-[4-fluoro-5-[4-[[1-[2-[(2S)-2-methylpiperazin-1-yl]ethyl]-4-piperidyl]methyl]piperazin-1-yl]-1-oxo-isoindolin-2-yl]piperidine-2,6-dione (140 mg, 186.94 μmol, 93.99% yield, 91.3% purity, TFA) was obtained as a light yellow oil.

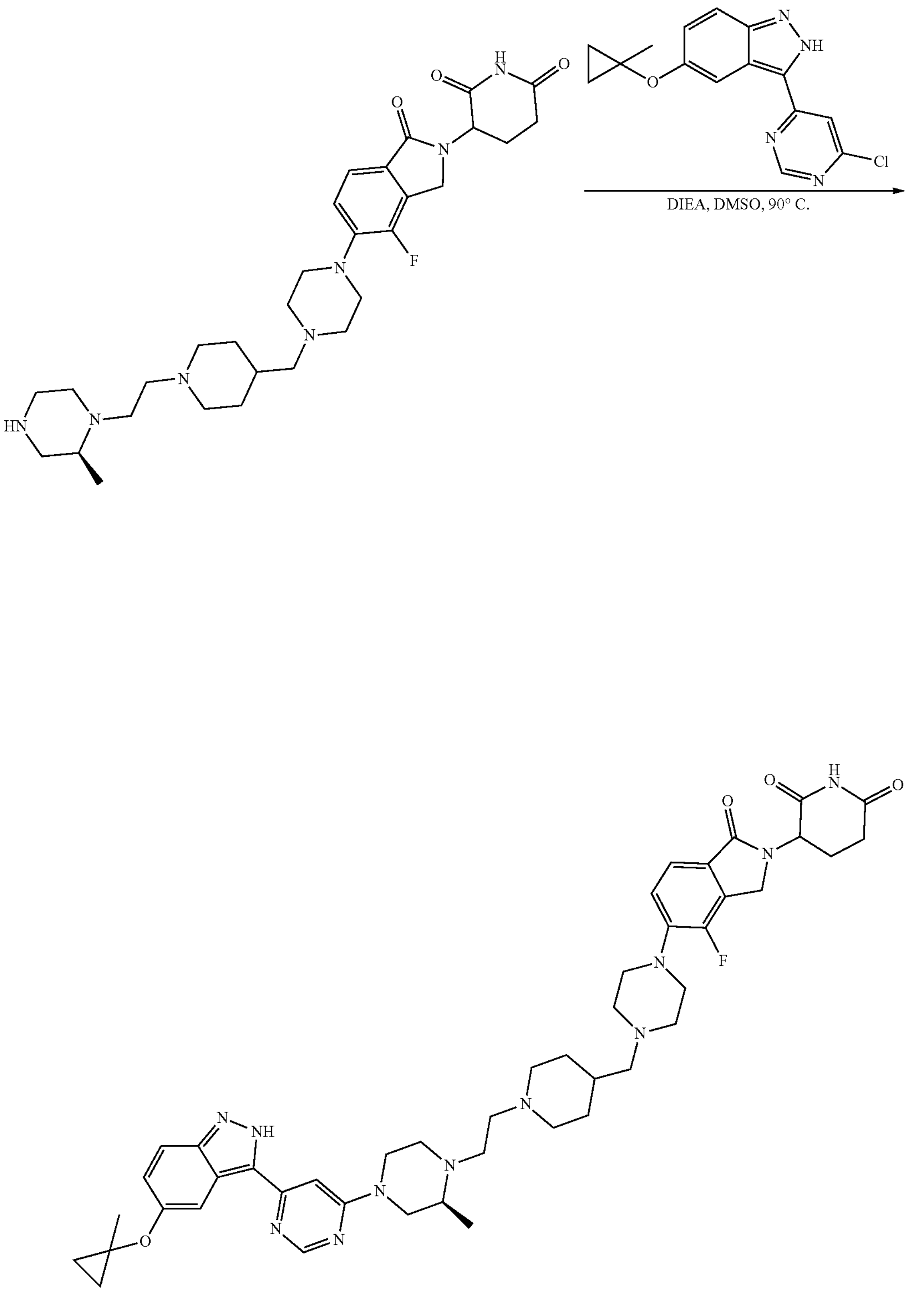

Step 8:

To a solution 3-[4-fluoro-5-[4-[[1-[2-[(2S)-2-methylpiperazin-1-yl]ethyl]-4-piperidyl]methyl]piperazin-1-yl]-1-oxo-isoindolin-2-yl]piperidine-2,6-dione (140 mg, 204.76 μmol, 1 eq, TFA) and 3-(6-chloropyrimidin-4-yl)-5-(1-methylcyclopropoxy)-2H-indazole (61.58 mg, 204.76 μmol, 1 eq) in DMSO (3 mL) was added DIEA (132.32 mg, 1.02 mmol, 178.33 μL, 5 eq), then the mixture was stirred at 90° C. for 16 hours. LCMS showed ~40.8% desired compound and the starting materials was consumed completely. The residue was purified by prep-HPLC (column: Xtimate C18 100*30 mm*10 um; mobile phase: [water (0.225% FA)-ACN]; B %: 0%-25%, 40 minutes). Compound 3-[4-fluoro-5-[4-[[1-[2-[(2S)-2-methyl-4-[6-[5-(1-methylcyclopropoxy)-2H-indazol-3-yl]pyrimidin-4-yl]piperazin-1-yl]ethyl]-4-piperidyl]methyl]piperazin-1-yl]-1-oxo-isoindolin-2-yl]piperidine-2,6-dione (31.3 mg, 37.40 μmol, 18.26% yield, 99.65% purity) was obtained as a brown solid.

Exemplary Synthesis of Compound 185

Step 1:

To a mixture of 1-[2-(2,6-dioxo-3-piperidyl)-6-fluoro-1-oxo-isoindolin-5-yl]piperidine-4-carbaldehyde (80 mg, 156.41 μmol, 73% purity, 1 eq) in MeOH (5 mL) and HOAc (0.5 mL) was added a solution of 6-fluoro-5-(1-methylcyclopropoxy)-3-[6-[4-(piperazin-1-ylmethyl)-1-piperidyl]pyrimidin-4-yl]-1H-indazole (78.52 mg, 156.41 μmol, 1 eq, HCl) and DIEA (20.21 mg, 156.41 μmol, 27.24 μL, 1 eq) in MeOH (0.5 mL). Then borane; 2-methylpyridine (33.46 mg, 312.82 μmol, 2 eq) was added to above solution. After addition, the reaction solution was stirred at 40° C. for 12 hours. LCMS showed the reaction completed. The reaction mixture was concentrated under reduced pressure to remove most of solvent. The residue was purified by prep.HPLC (column: Xtimate C18 100*30 mm*10 um; mobile phase: [water (10 mM $NH_4HCO_3$)-ACN]; B %: 20%-70%, 40 minutes) to afford 3-[6-fluoro-5-[4-[[4-[[1-[6-[6-fluoro-5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (50.4 mg, 61.24 μmol, 39.16% yield, 100% purity) as an off-white solid.

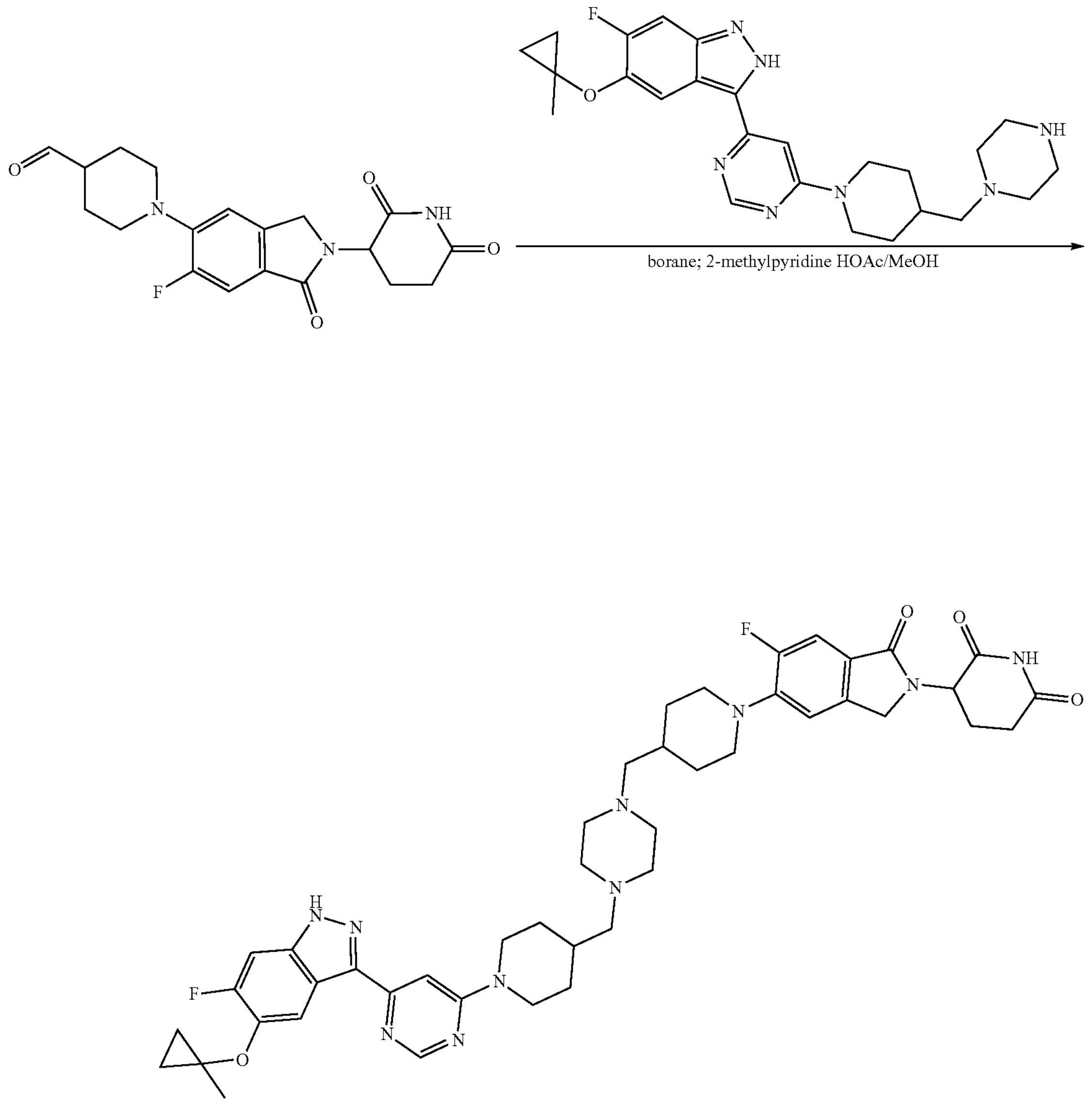

Exemplary Synthesis of Compound 186

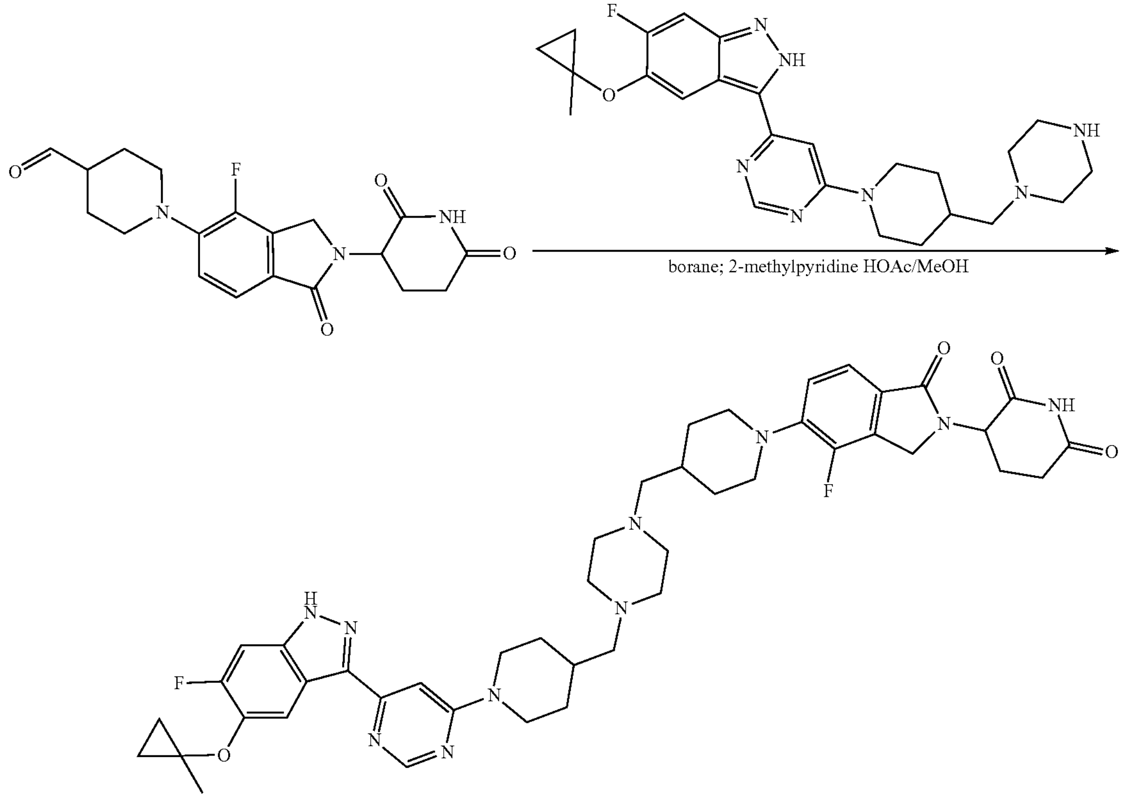

Step 1:

To a mixture of 6-fluoro-5-(1-methylcyclopropoxy)-3-[6-[4-(piperazin-1-ylmethyl)-1-piperidyl]pyrimidin-4-yl]-2H-indazole (80.67 mg, 160.70 μmol, 1 eq, HCl) in HOAC (1 mL) and MeOH (10 mL) was added a solution of 1-[2-(2,6-dioxo-3-piperidyl)-4-fluoro-1-oxo-isoindolin-5-yl]piperidine-4-carbaldehyde (60 mg, 160.70 μmol, 1 eq) and DIEA (62.31 mg, 482.09 μmol, 83.97 μL, 3 eq) in MeOH (0.5 mL). Then borane; 2-methylpyridine (34.38 mg, 321.39 μmol, 2 eq) was added to above solution. After addition, the reaction solution was stirred at 20° C. for 16 hours LCMS showed desired product. The residue was concentrated under reduced pressure to give a residue. The residue was purified by prep-HPLC (column: Xtimate C18 100*30 mm*10 um; mobile phase: [water (10 mM $NH_4HCO_3$)-ACN]; B %: 30%-80%, 40 minutes) to afford 3-[4-fluoro-5-[4-[[4-[[1-[6-[6-fluoro-5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (54.2 mg, 63.52 μmol, 39.53% yield, 96.44% purity) as white solid.

Exemplary Synthesis of Compound 187

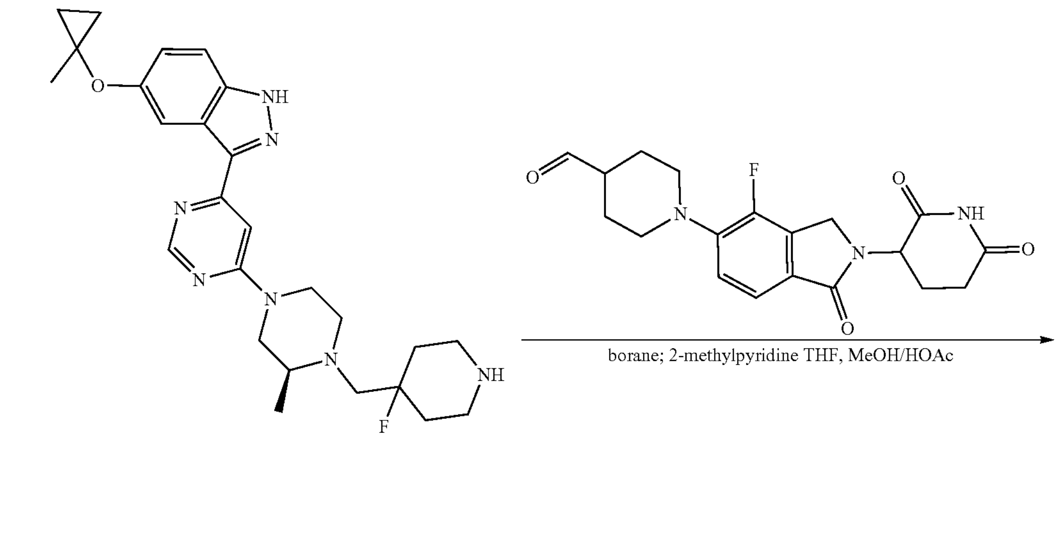

-continued

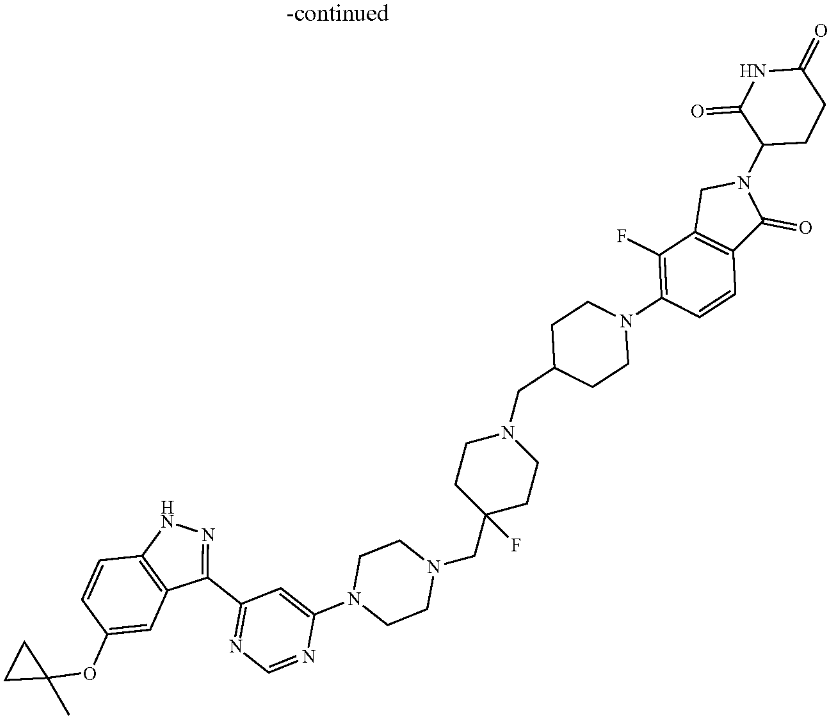

Step 1:

To a mixture of 3-[6-[(3S)-4-[(4-fluoro-4-piperidyl) methyl]-3-methyl-piperazin-1-yl]pyrimidin-4-yl]-5-(1-methylcyclopropoxy)-1H-indazole (64 mg, 133.45 μmol, 1 eq) and 1-[2-(2,6-dioxo-3-piperidyl)-4-fluoro-1-oxo-isoindolin-5-yl]piperidine-4-carbaldehyde (63.07 mg, 133.45 μmol, 79% purity, 1 eq) in MeOH (10 mL), AcOH (1 mL) and THF (10 mL) added borane; 2-methylpyridine (28.55 mg, 266.89 μmol, 2 eq). The mixture was stirred at 20° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.HPLC (column: Xtimate C18 100*30 mm*10 um; mobile phase: [water (0.225% FA)-ACN]; B %: 0%-35%, 40 minutes) to afford 3-[4-fluoro-5-[4-[[4-fluoro-4-[[(2S)-2-methyl-4-[6-[5-(1-methylcyclopropoxy)-1H-indazol-3-yl]pyrimidin-4-yl]piperazin-1-yl]methyl]-1-piperidyl]methyl]-1-piperidyl]-1-oxo-isoindolin-2-yl] piperidine-2,6-dione (16.6 mg, 19.21 μmol, 14.40% yield, 96.878% purity) as a white solid.

Exemplary Synthesis of Compound 188

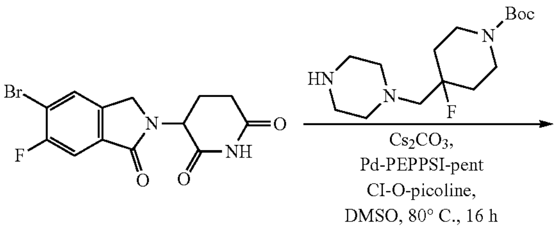

-continued

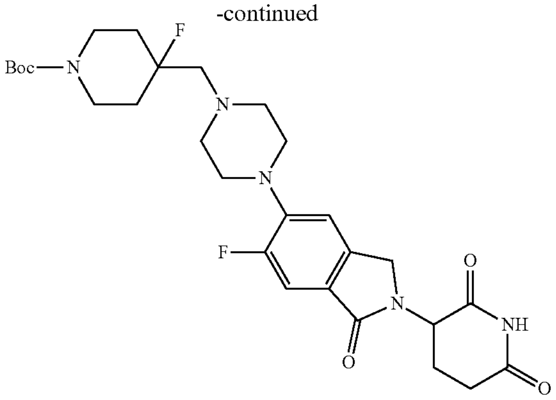

Step 1:

To a solution of 3-(5-bromo-6-fluoro-1-oxo-isoindolin-2-yl)piperidine-2,6-dione (400 mg, 1.17 mmol, 1 eq) and tert-butyl 4-fluoro-4-(piperazin-1-ylmethyl)piperidine-1-carboxylate (530.12 mg, 1.76 mmol, 1.5 eq) in DMSO (10 mL) was added $Cs_2CO_3$ (764.09 mg, 2.35 mmol, 2 eq) and Pd-PEPPSI-pent Cl—O-picoline (100.91 mg, 117.26 μmol, 0.1 eq). After addition, the reaction mixture was stirred at 80° C. under $N_2$ for 12 hours. LCMS and TLC showed the reaction was completed. After cooling, the reaction mixture was filtered and filtrate was diluted with ethyl acetate (50 mL). The organic layer was washed with brine (30 mL*2), dried over sodium sulfate and concentrated under reduced pressure. The residue was purified by silica gel column chromatography (0 to 100% ethyl acetate in petroleum ether) to afford tert-butyl 4-[[4-[2-(2,6-dioxo-3-piperidyl)-6-fluoro-1-oxo-isoindolin-5-yl]piperazin-1-yl]methyl]-4-fluoro-piperidine-1-carboxylate (240 mg, 393.15 μmol, 33.53% yield, 92% purity) as a gray solid.

-continued

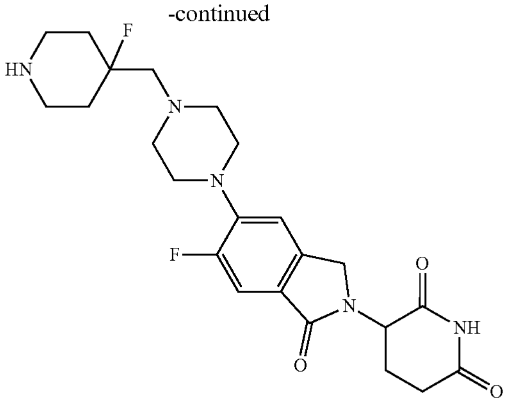

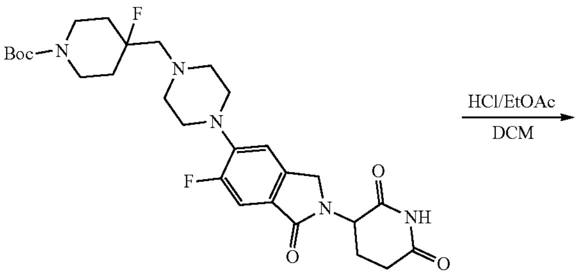

Step 2:

To a solution of tert-butyl 4-[[4-[2-(2,6-dioxo-3-piperidyl)-6-fluoro-1-oxo-isoindolin-5-yl]piperazin-1-yl]methyl]-4-fluoro-piperidine-1-carboxylate (240 mg, 427.34 μmol, 1 eq) in DCM (3 mL) was added HCl/EtOAc (4 M, 4 mL, 37.44 eq). After addition, the reaction was stirred at 20° C. for 2 hours. LCMS showed the reaction completed. The reaction mixture was concentrated under reduced pressure to remove solvent to afford 3-[6-fluoro-5-[4-[(4-fluoro-4-piperidyl)methyl]piperazin-1-yl]-1-oxo-isoindolin-2-yl]piperidine-2,6-dione (220 mg, 384.36 μmol, 89.94% yield, 87% purity, HCl) as a gray solid. The crude product was used for next step directly.

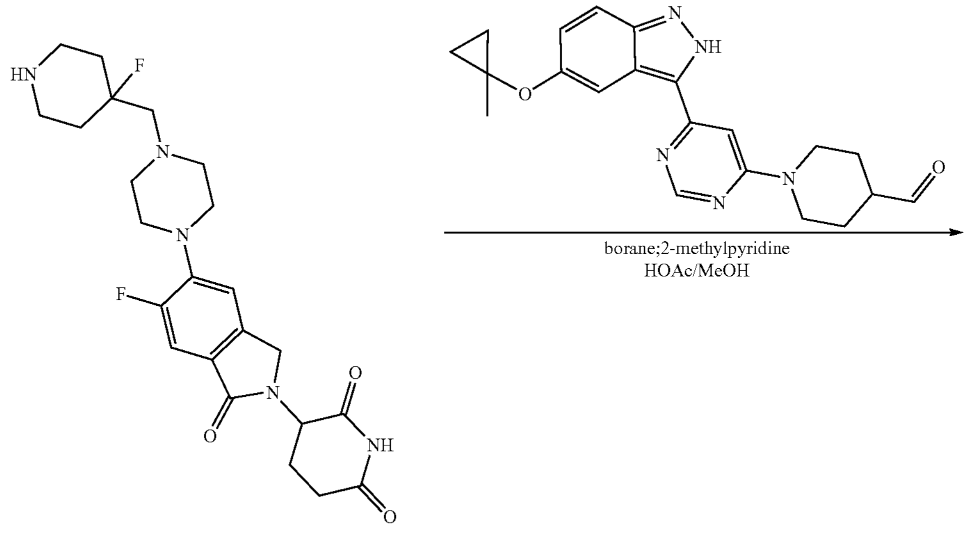

-continued

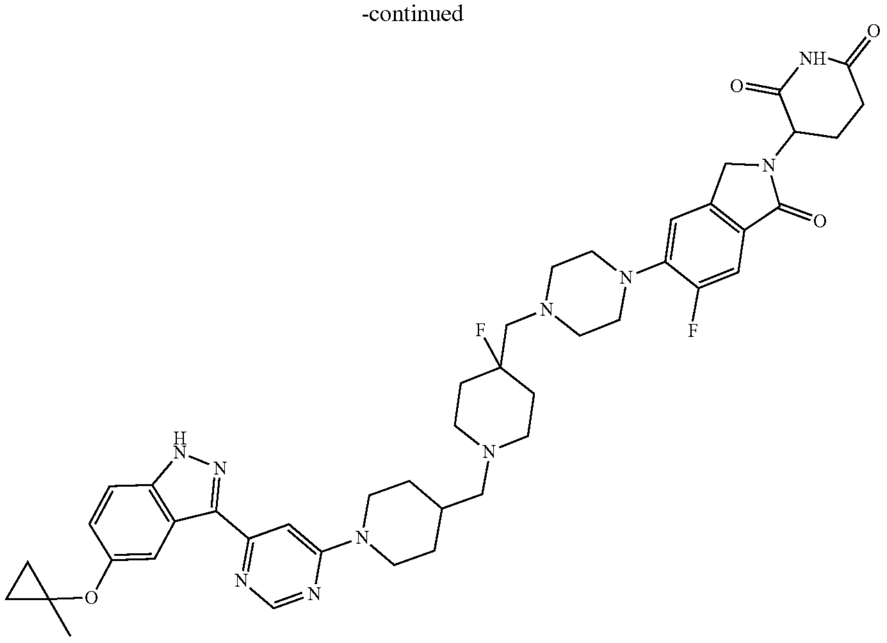

Step 3:

To a mixture of 3-[6-fluoro-5-[4-[(4-fluoro-4-piperidyl) methyl]piperazin-1-yl]-1-oxo-isoindolin-2-yl]piperidine-2,6-dione (90 mg, 157.24 μmol, 87% purity, 1 eq, HCl) in MeOH (10 mL) and HOAc (1 mL) was added a solution of 1-[6-[5-(1-methylcyclopropoxy)-2H-indazol-3-yl]pyrimidin-4-yl]piperidine-4-carbaldehyde (62 mg, 164.27 μmol, 1.04 eq) and DIEA (20.32 mg, 157.24 μmol, 27.39 μL, 1 eq) in MeOH (1 mL). Then borane; 2-methylpyridine (33.64 mg, 314.48 μmol, 2 eq) was added to above solution. After addition, the reaction solution was stirred at 25° C. for 12 hours. LCMS showed the reaction completed. The reaction mixture was concentrated under reduced pressure to remove most of solvent. The residue was purified by prep.HPLC (column: Xtimate C18 100*30 mm*10 um; mobile phase: [water (0.225% FA)-ACN]; B %: 0%-30%, 40 minutes) to afford 3-[6-fluoro-5-[4-[[4-fluoro-1-[[1-[6-[5-(1-methylcyclopropoxy)-1H-indazol-3-yl]pyrimidin-4-yl]-4-piperidyl]methyl]-4-piperidyl]methyl]piperazin-1-yl]-1-oxo-isoindolin-2-yl]piperidine-2,6-dione (37.3 mg, 45.33 μmol, 28.83% yield, 100% purity) as an off-white solid.

Exemplary Synthesis of Compound 189

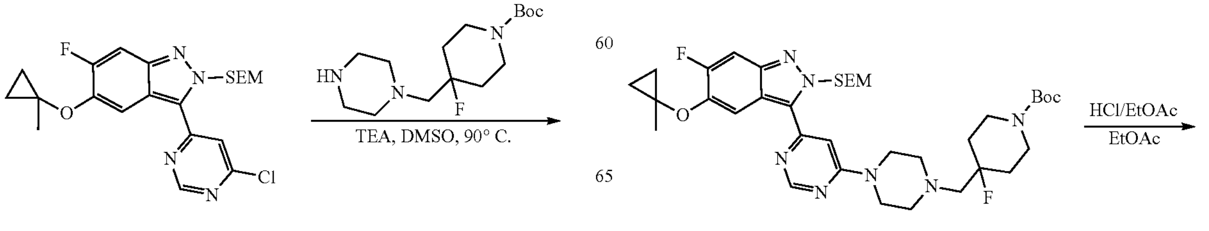

-continued

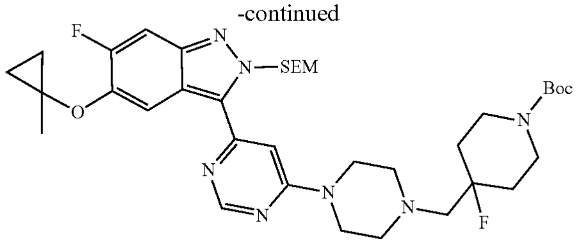

Step 1:

To a mixture of 2-[[3-(6-chloropyrimidin-4-yl)-6-fluoro-5-(1-methylcyclopropoxy)indazol-2-yl]methoxy]ethyl-trimethyl-silane (200 mg, 445.44 μmol, 1 eq) and tert-butyl 4-fluoro-4-(piperazin-1-ylmethyl)piperidine-1-carboxylate (134.26 mg, 445.44 μmol, 1 eq) in DMSO (3 mL) was added TEA (135.22 mg, 1.34 mmol, 186.00 μL, 3 eq). The mixture was stirred at 90° C. for 16 hours. LCMS showed there was desired MS. The residue was poured into water (30 mL). The aqueous phase was extracted with ethyl acetate (30 mL*3). The combined organic phase was washed with brine (30 mL*2), dried with anhydrous $Na_2SO_4$, filtered and concentrated in vacuum. The residue was purified by silica gel chromatography (12 g, 0-28% (15 minutes) of Ethyl acetate in Petroleum ether, 0-28% (10 min) of Ethyl acetate in Petroleum ether) to afford tert-butyl 4-fluoro-4-[[4-[6-[6-fluoro-5-(1-methylcyclopropoxy)-2-(2-trimethylsilylethoxymethyl)indazol-3-yl]pyrimidin-4-yl]piperazin-1-yl]methyl]piperidine-1-carboxylate (250 mg, 226.87 μmol, 50.93% yield, 64.789% purity) as a yellow gum.

-continued

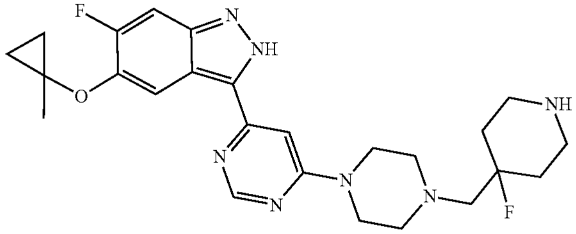

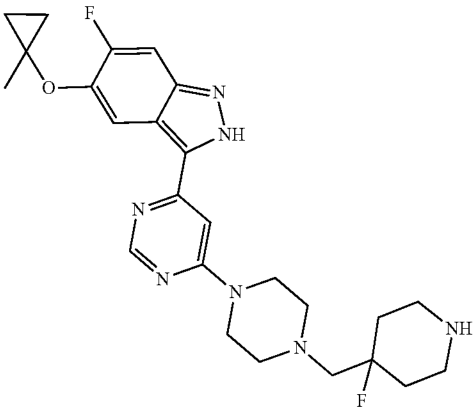

Step 2:

To a mixture of tert-butyl 4-fluoro-4-[[4-[6-[6-fluoro-5-(1-methylcyclopropoxy)-2-(2-trimethylsilylethoxymethyl) indazol-3-yl]pyrimidin-4-yl]piperazin-1-yl]methyl]piperidine-1-carboxylate (250 mg, 350.17 μmol, 1 eq) in EtOAc (2 mL) was added HCl/EtOAc (4 M, 87.54 μL, 1 eq). The mixture was stirred at 40° C. for 2 hours. TLC showed the reaction was completed. The residue was filtered and concentrated in vacuum to afford 6-fluoro-3-[6-[4-[(4-fluoro-4-piperidyl)methyl]piperazin-1-yl]pyrimidin-4-yl]-5-(1-methylcyclopropoxy)-2H-indazole (200 mg, crude, HCl) as a white solid.

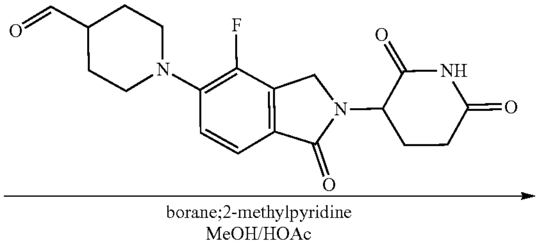

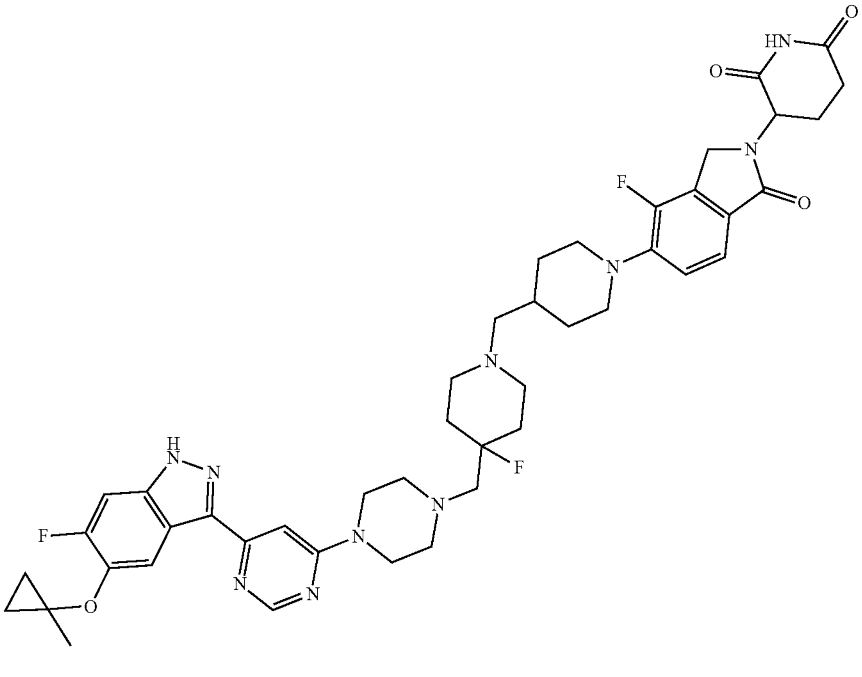

Step 3:

To a mixture of 6-fluoro-3-[6-[4-[(4-fluoro-4-piperidyl)methyl]piperazin-1-yl]pyrimidin-4-yl]-5-(1-methylcyclopropoxy)-2H-indazole (85 mg, 175.78 μmol, 1.38 eq) and 1-[2-(2,6-dioxo-3-piperidyl)-4-fluoro-1-oxo-isoindolin-5-yl]piperidine-4-carbaldehyde (60 mg, 126.95 μmol, 79% purity, 1 eq) in MeOH (10 mL), THF (10 mL) and AcOH (1 mL) added borane; 2-methylpyridine (27.16 mg, 253.90 μmol, 2 eq). The mixture was stirred at 40° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.HPLC (column: Xtimate C18 100*30 mm*10 um; mobile phase: [water (0.225% FA)-ACN]; B %: 0%-35%, 40 min) to afford 3-[4-fluoro-5-[4-[[4-fluoro-4-[[4-[6-[6-fluoro-5-(1-methylcyclopropoxy)-1H-indazol-3-yl]pyrimidin-4-yl]piperazin-1-yl]methyl]-1-piperidyl]methyl]-1-piperidyl]-1-oxo-isoindolin-2-yl]piperidine-2,6-dione (55.4 mg, 65.83 μmol, 51.86% yield, 99.927% purity) as a white solid.

Exemplary Synthesis of Compound 190

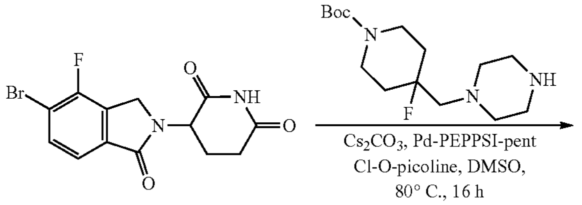

-continued

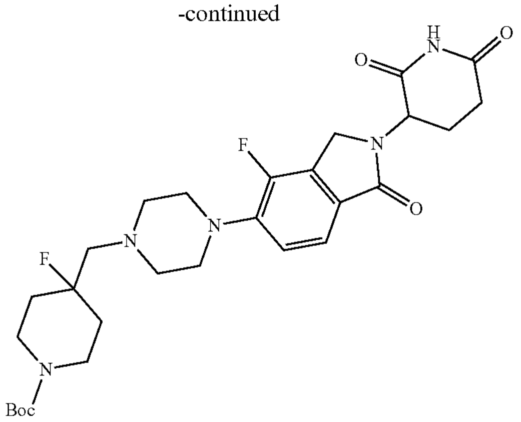

Step 1:

A mixture of 3-(5-bromo-4-fluoro-1-oxo-isoindolin-2-yl)piperidine-2,6-dione (200 mg, 586.28 μmol, 1 eq), tert-butyl 4-fluoro-4-(piperazin-1-ylmethyl)piperidine-1-carboxylate (176.71 mg, 586.28 μmol, 1 eq), $Cs_2CO_3$ (382.04 mg, 1.17 mmol, 2 eq) and Pd-PEPPSI-pent Cl—O-picoline (25.23 mg, 29.31 μmol, 0.05 eq) in DMSO (3 mL) was degassed and purged with N2 for 3 times, and then the mixture was stirred at 80° C. for 16 hours under $N_2$ atmosphere. LC-MS (EB2049-281-P1B) showed Reactant 1 was consumed completely. After cooling, the reaction mixture was filtered and filtrate was diluted with THF (5 mL) and washed with brine (5 mL*3). The organic layer was dried over sodium sulfate and concentrated under reduced pressure. The residue was purified by flash silica gel chromatography (ISCO®; 12 g SepaFlash® Silica Flash Column, Eluent of 0-35% Ethyl acetate/Petroleum ether gradient @ 75 mL/min). tert-butyl 4-[[4-[2-(2,6-dioxo-3-piperidyl)-4-fluoro-1-oxo-isoindolin-5-yl]piperazin-1-yl]methyl]-4-fluoro-piperidine-1-carboxylate (100 mg, 178.06 μmol, 30.37% yield) as a white solid

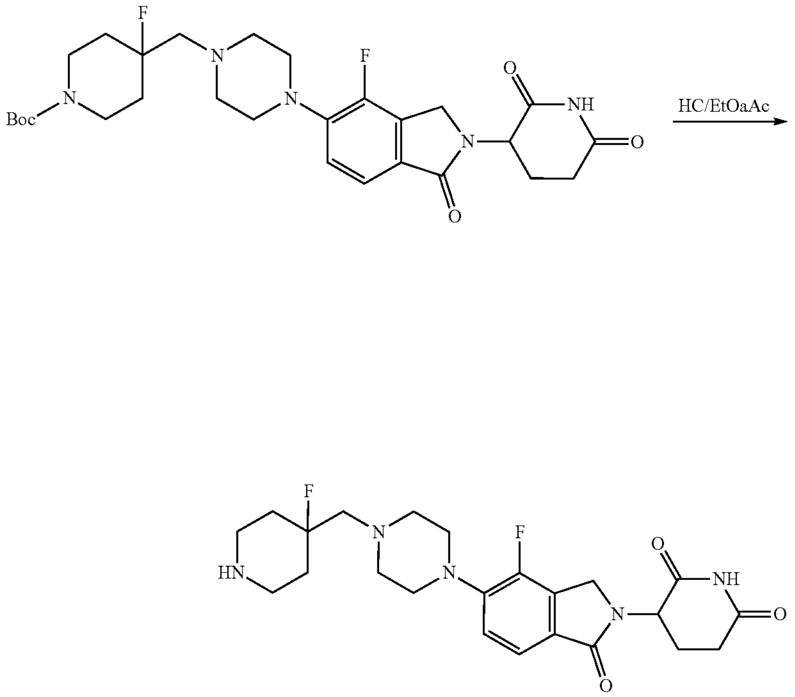

Step 2:

To a solution of tert-butyl 4-[[4-[2-(2,6-dioxo-3-piperidyl)-4-fluoro-1-oxo-isoindolin-5-yl]piperazin-1-yl]methyl]-4-fluoro-piperidine-1-carboxylate (95 mg, 169.15 μmol, 1 eq) in DCM (3 mL) was added TFA (57.86 mg, 507.46 μmol, 37.57 μL, 3 eq). The mixture was stirred at 25° C. for 1 hour. TLC indicated no Reactant 1 was remained, and one major new spot with larger polarity was detected. The reaction mixture was concentrated under reduced pressure to remove solvent. Without further purification. 3-[4-fluoro-5-[4-[(4-fluoro-4-piperidyl)methyl]piperazin-1-yl]-1-oxo-isoindolin-2-yl]piperidine-2,6-dione (83 mg, 87.97 μmol, 52.01% yield, 61% purity, TFA) as a white solid

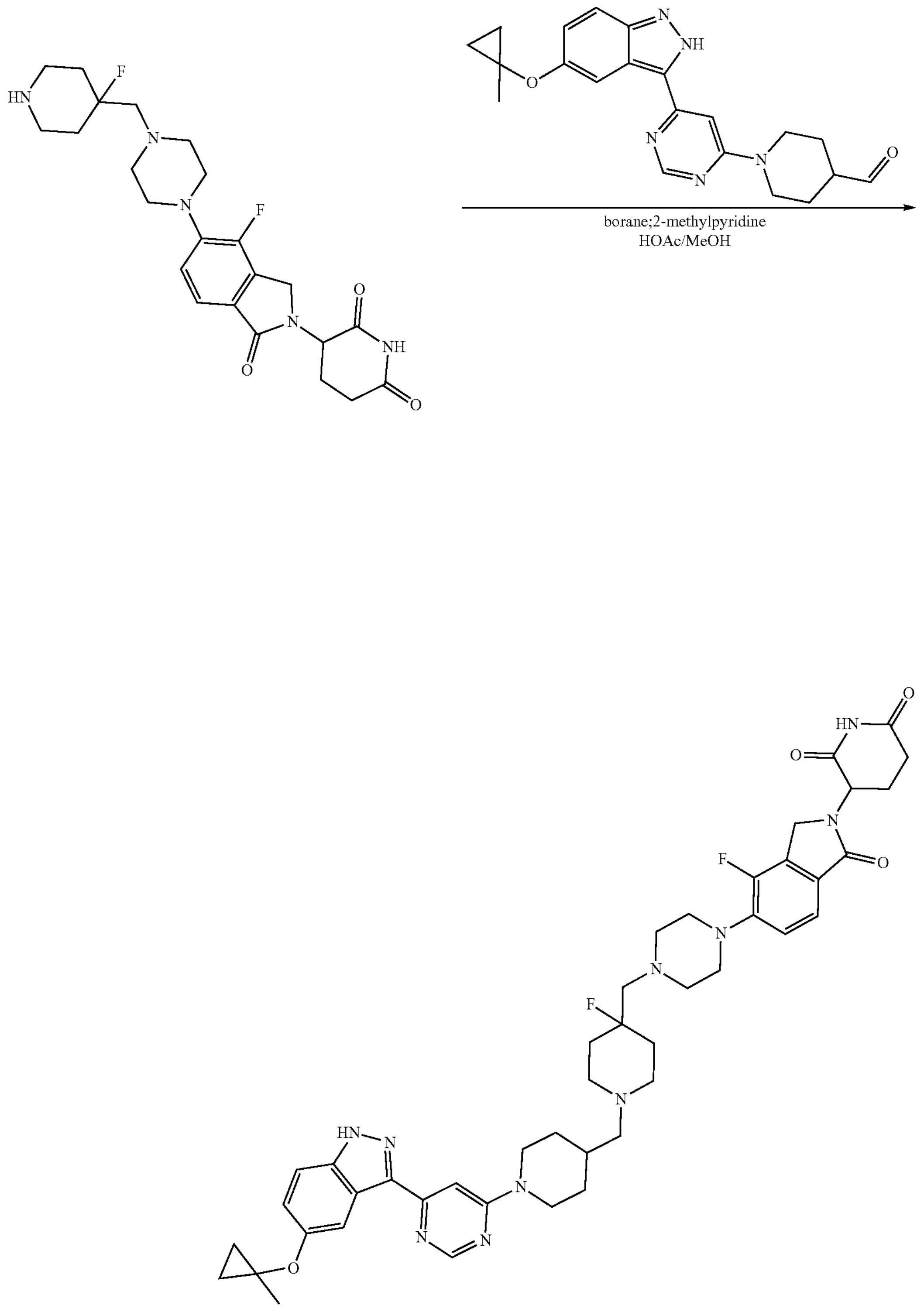

Step 3:

To a solution of 1-[6-[5-(1-methylcyclopropoxy)-2H-indazol-3-yl]pyrimidin-4-yl]piperidine-4-carbaldehyde (33 mg, 87.43 µmol, 1 eq) and 3-[4-fluoro-5-[4-[(4-fluoro-4-piperidyl)methyl]piperazin-1-yl]-1-oxo-isoindolin-2-yl]piperidine-2,6-dione (50.32 mg, 87.43 µmol, 1 eq, TFA) in AcOH (0.5 mL) and MeOH (3 mL) was added borane; 2-methylpyridine (18.70 mg, 174.86 µmol, 2 eq). The mixture was stirred at 25° C. for 16 hours. LC-MS (EB2049-284-P1A) showed Reactant 1 was consumed completely and desired mass was detected. The mixture was poured onto ice water (5 mL) and extracted with EtOAc (5 mL×2). The organic layer was washed with brine (5 mL), dried over anhydrous $Na_2SO_4$, filtered and concentrated in vacuo. The crude product was purified by reversed-phase HPLC (column: Xtimate C18 100*30 mm*10 um; mobile phase: [water (0.225% FA)-ACN]; B %: 0%-30%, 40 min) to afford 3-[4-fluoro-5-[4-[[4-fluoro-1-[[1-[6-[5-(1-methylcyclopropoxy)-1H-indazol-3-yl]pyrimidin-4-yl]-4-piperidyl]methyl]-4-piperidyl]methyl]piperazin-1-yl]-1-oxo-isoindolin-2-yl]piperidine-2,6-dione (42.4 mg, 51.33 µmol, 58.70% yield, 99.619% purity) as a white solid Exemplary Synthesis of Compound 191

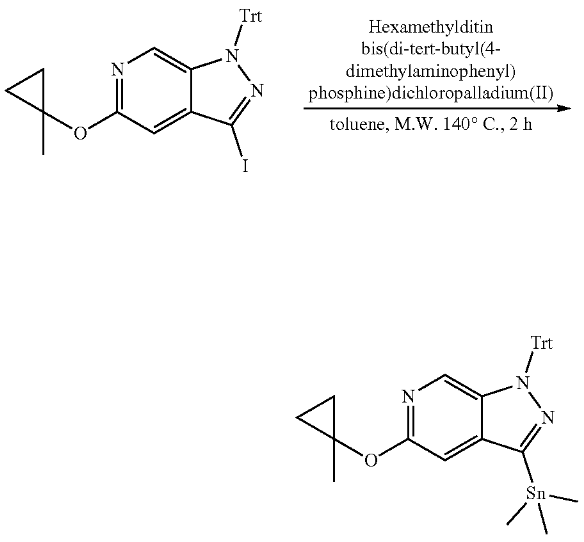

Step 1:

To a solution of 3-iodo-5-(1-methylcyclopropoxy)-1-trityl-pyrazolo[3,4-c]pyridine (2 g, 3.59 mmol, 1 eq) in toluene (20 mL) was added Hexamethylditin (2.35 g, 7.18 mmol, 1.5 mL, 2 eq) and 4-ditert-butylphosphanyl-N,N-dimethyl-aniline; dichloropalladium (254 mg, 0.36 mmol, 0.25 mL, 0.1 eq) under nitrogen. The reaction was stirred at 140° C. for 2 hours under microwave. TLC (petroleum ether:ethyl acetate=5:1) showed new spot was detected. The mixture was diluted with ethyl acetate (100 mL) and filtered through celite. The filter was concentrated in vacuum. The residue was purified by silica gel chromatography (petroleum ether: ethyl acetate=1:0 to 10:1). trimethyl-[5-(1-methylcyclopropoxy)-1-trityl-pyrazolo[3,4-c]pyridin-3-yl]stannane (1.8 g, 3.03 mmol, 84% yield) was obtained as a light yellow oil.

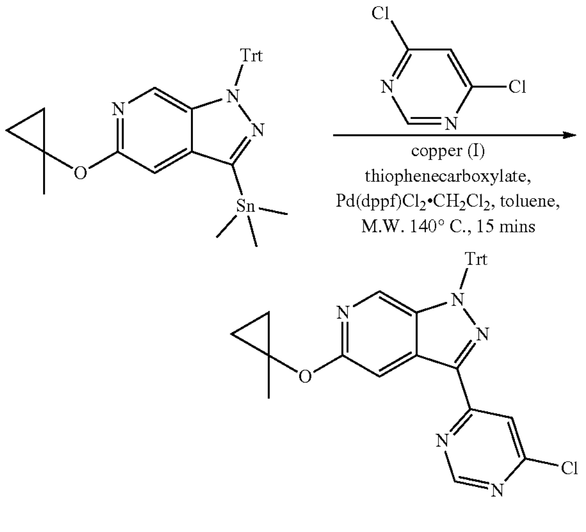

Step 2:

To a solution of trimethyl-[5-(1-methylcyclopropoxy)-1-trityl-pyrazolo[3,4-c]pyridin-3-yl] stannane (300 mg, 0.5 mmol, 1 eq), 4,6-dichloropyrimidine (113 mg, 0.76 mmol, 1.5 eq) in toluene (3 mL) was added thiophene-2-carbonyloxycopper (192 mg, 1.01 mmol, 2 eq) and 1,1-bis(diphenylphosphino)ferrocene-palladium(II) dichloridedichloromethane complex (41. mg, 0.05 mmol, 0.1 eq) under nitrogen. The reaction was stirred at 140° C. for 15 minutes under microwave. LCMS showed desired MS was detected. The mixture was filtered and the filter was concentrated in vacuum. The residue was purified by silica gel chromatography (petroleum ether:ethyl acetate=1:0 to 5:1). 3-(6-chloropyrimidin-4-yl)-5-(1-methylcyclopropoxy)-1-trityl-pyrazolo[3,4-c]pyridine (140 mg, 0.26 mmol, 51% yield) was obtained as a light yellow solid.

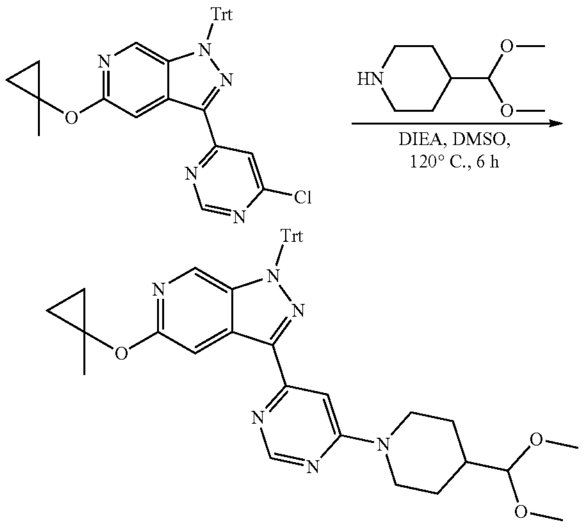

Step 3:

To a solution of 3-(6-chloropyrimidin-4-yl)-5-(1-methylcyclopropoxy)-1-trityl-pyrazolo[3,4-c] pyridine (120 mg, 0.22 mmol, 1 eq), diisopropylethylamine (85 mg, 0.66 mmol, 0.1 mL, 3 eq) in dimethyl sulfoxide (3 mL) was added 4-(dimethoxymethyl)piperidine (42 mg, 0.26 mmol, 1.2 eq).

The reaction mixture was stirred at 120° C. for 6 hours. LCMS showed desired MS was detected. The mixture was poured into water (20 mL), the aqueous phase was extracted with ethyl acetate (20 mL*3). The combined organic phase was washed with brine (20 mL*2), dried over sodium sulfate, filtered and concentrated in vacuum. The residue was purified by prep-TLC (petroleum ether:ethyl acetate=2:1). 3-[6-[4-(dimethoxymethyl)-1-piperidyl]pyrimidin-4-yl]-5-(1-methylcyclopropoxy)-1-trityl-pyrazolo[3,4-c]pyridine (95 mg, 0.14 mmol, 64% yield) was obtained as a light yellow solid.

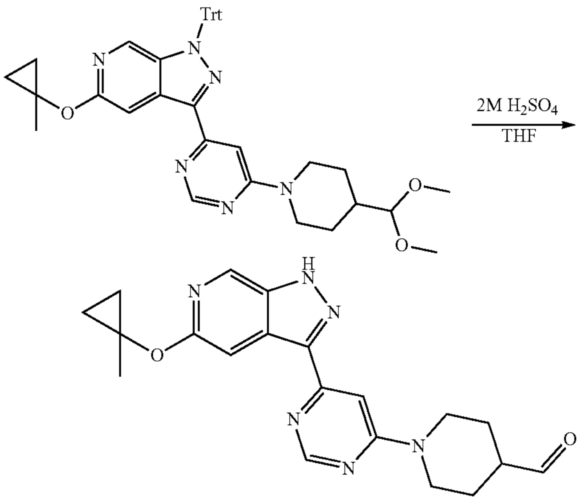

Step 4:

To a solution of 3-[6-[4-(dimethoxymethyl)-1-piperidyl]pyrimidin-4-yl]-5-(1-methylcyclopropoxy)-1-trityl-pyrazolo[3,4-c]pyridine (110 mg, 0.16 mmol, 1 eq) in tetrahydrofuran (3 mL) was added sulfuric acid solution (3 M, 1.2 mL, 22.23 eq). The reaction was stirred at 40° C. for 7 hours. LCMS showed desired MS was detected. Saturated sodium bicarbonate (50 mL) was added to the mixture, the aqueous phase was extracted with ethyl acetate (50 mL*3). The combined organic phase was washed with brine (50 mL), dried over sodium sulfate, filtered and concentrated in vacuum. The residue was used into next step directly. 1-[6-[5-(1-methylcyclopropoxy)-1H-pyrazolo[3,4-c]pyridin-3-yl]pyrimidin-4-yl]piperidine-4-carbaldehyde (60 mg, crude) was obtained as a light yellow solid.

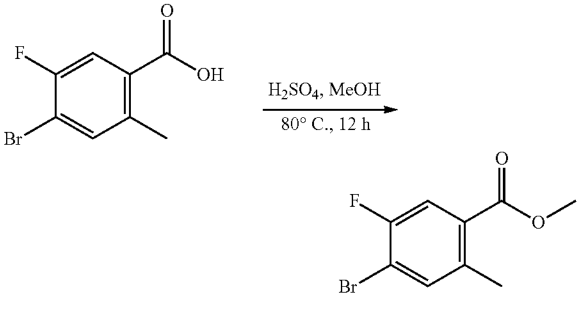

Step 5:

To a solution of 4-bromo-5-fluoro-2-methyl-benzoic acid (2 g, 8.58 mmol, 1 eq) in methanol (20 mL) was added sulfuric acid solution (421 mg, 4.29 mmol, 0.2 mL, 0.5 eq). The reaction was stirred at 80° C. for 12 hours. TLC (petroleum ether:ethyl acetate=3:1) showed new spot was detected. The mixture was poured into saturated sodium bicarbonate (50 mL), the aqueous phase was extracted with ethyl acetate (100 mL*3). The combined organic phase was washed with brine (100 mL), dried over sodium sulfate, filtered and concentrated in vacuum. The residue was purified by silica gel chromatography (petroleum ether:ethyl acetate=1:0 to 20:1). methyl 4-bromo-5-fluoro-2-methyl-benzoate (2.3 g, crude) was obtained as a colorless oil.

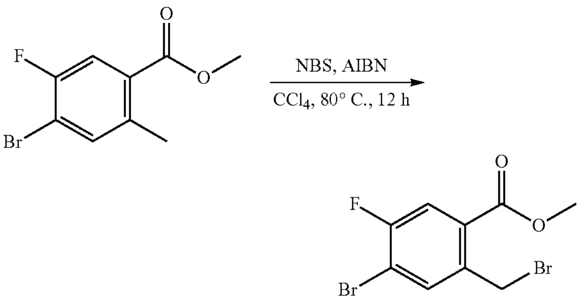

Step 6:

To a solution of methyl 4-bromo-5-fluoro-2-methyl-benzoate (2.3 g, 9.31 mmol, 1 eq) in carbon tetrachloride (25 mL) was added N-bromosuccinimide (1.66 g, 9.31 mmol, 1 eq) and 2,2-azobisisobutyronitrile (153 mg, 0.93 mmol, 0.1 eq). The reaction mixture was stirred at 80° C. for 12 hours. TLC (petroleum ether:ethyl acetate=5:1) showed new spot was detected. The mixture was filtered and the filtrate cake was washed with ethyl acetate (20 mL*2). The filtrate was concentrated in vacuum. The residue was purified by silica gel chromatography (petroleum ether:ethyl acetate=1:0 to 20:1). methyl 4-bromo-2-(bromomethyl)-5-fluoro-benzoate (1.9 g, 5.83 mmol, 62% yield) was obtained as a white solid.

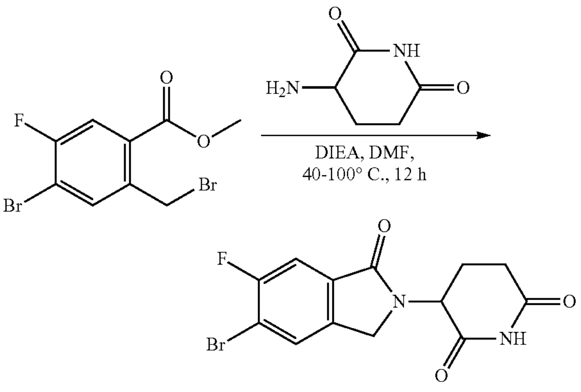

Step 7:

To a solution of methyl 4-bromo-2-(bromomethyl)-5-fluoro-benzoate (1.9 g, 5.83 mmol, 1 eq), N,N-Diisopropylethylamine (3.77 g, 29.14 mmol, 5.08 mL, 5 eq) in N,N-Dimethyl Formamide (30 mL) was added 3-aminopiperidine-2,6-dione; hydrochloride (1.01 g, 6.12 mmol, 1.05 eq). The reaction mixture was stirred at 40° C. for 1 hour and 100° C. for 11 hours. LCMS showed desired MS was detected. The mixture was poured into water (150 mL), the mixture was filtered and the filtrate cake was dried in vacuum. The mixture was triturated with petroleum ether and ethyl acetate (V/V=1:1, 20 mL). 3-(5-bromo-6-fluoro-1-oxo-isoindolin-2-yl)piperidine-2,6-dione (1.25 g, 3.45 mmol, 59% yield, 94% purity) was obtained as a gray solid.

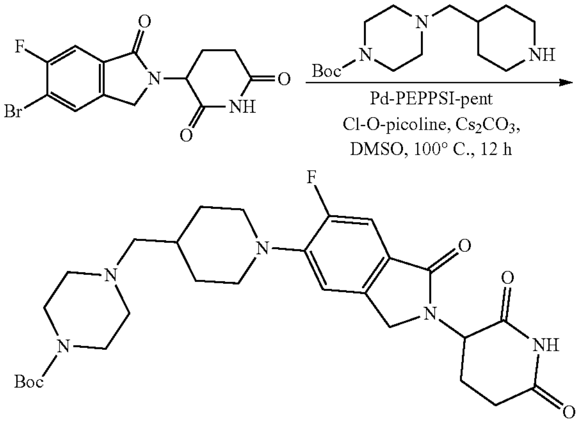

Step 8:

To a solution of 3-(5-bromo-6-fluoro-1-oxo-isoindolin-2-yl)piperidine-2,6-dione (300 mg, 0.88 mmol, 1 eq), tert-butyl 4-(4-piperidylmethyl)piperazine-1-carboxylate (299 mg, 1.06 mmol, 1.2 eq) in dimethylsulfoxide (6 mL) was added cesium carbonate (573 mg, 1.76 mmol, 2 eq) and Pd-PEPPSI-pent Cl—O-picoline, (85 mg, 0.09 mmol, 0.1 eq) under nitrogen. The reaction was stirred at 100° C. for 12 hours. LCMS showed desired MS was detected. dichloromethane (20 mL) and water (20 mL) was added to the mixture, the aqueous phase was extracted with dichloromethane (20 mL*2). The combined organic phase was washed with brine (20 mL), dried over sodium sulfate, filtered and concentrated in vacuum. The residue was purified by prep-TLC (dichloromethane:methanol=10:1). tert-butyl 4-[[1-[2-(2,6-dioxo-3-piperidyl)-6-fluoro-1-oxo-isoindolin-5-yl]-4-piperidyl]methyl]piperazine-1-carboxylate (120 mg, 0.20 mmol, 23% yield, 93% purity) was obtained as a gray solid.

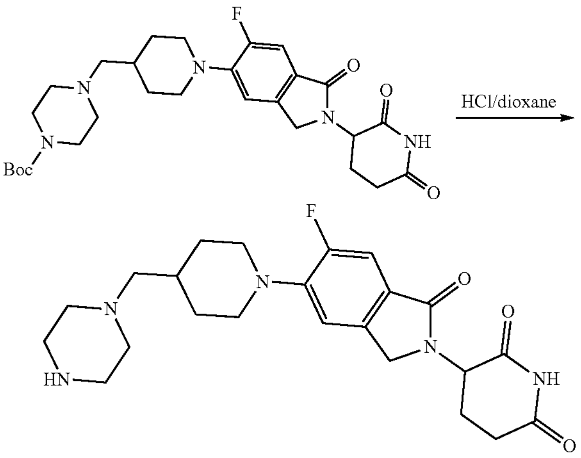

Step 9:

To a solution of tert-butyl 4-[[1-[2-(2,6-dioxo-3-piperidyl)-6-fluoro-1-oxo-isoindolin-5-yl]-4-piperidyl]methyl] piperazine-1-carboxylate (60 mg, 0.11 mmol, 1 eq) in dichloromethane (1 mL) was added hydrochloric acid solution (4 M in dioxane, 2.4 mL, 86.98 eq). The reaction was stirred at 20° C. for 1 hour. TLC (dichloromethane:methanol=10:1) showed new spot was detected. The mixture was concentrated in vacuum. The residue was used into next step directly. 3-[6-fluoro-1-oxo-5-[4-(piperazin-1-ylmethyl)-1-piperidyl]isoindolin-2-yl] piperidine-2,6-dione (52 mg, 0.11 mmol, 98% yield, hydrochloride) was obtained as a gray solid.

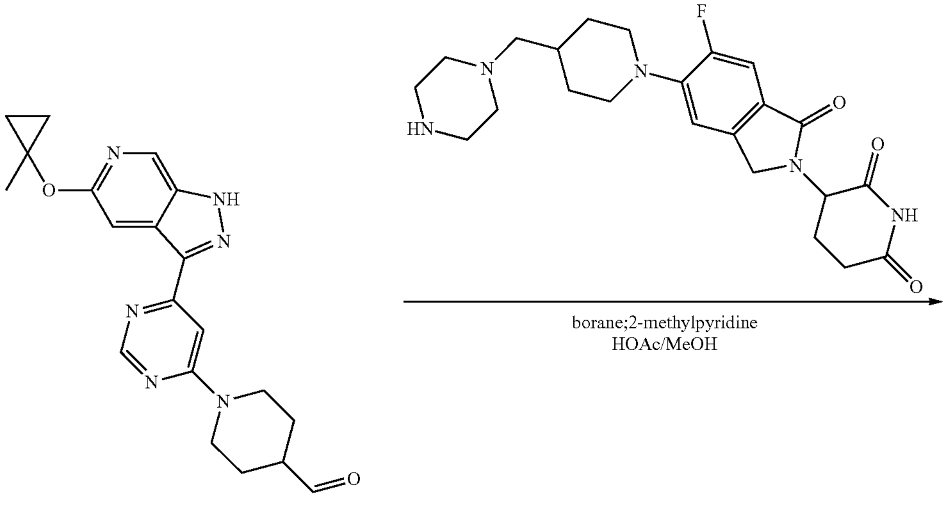

-continued

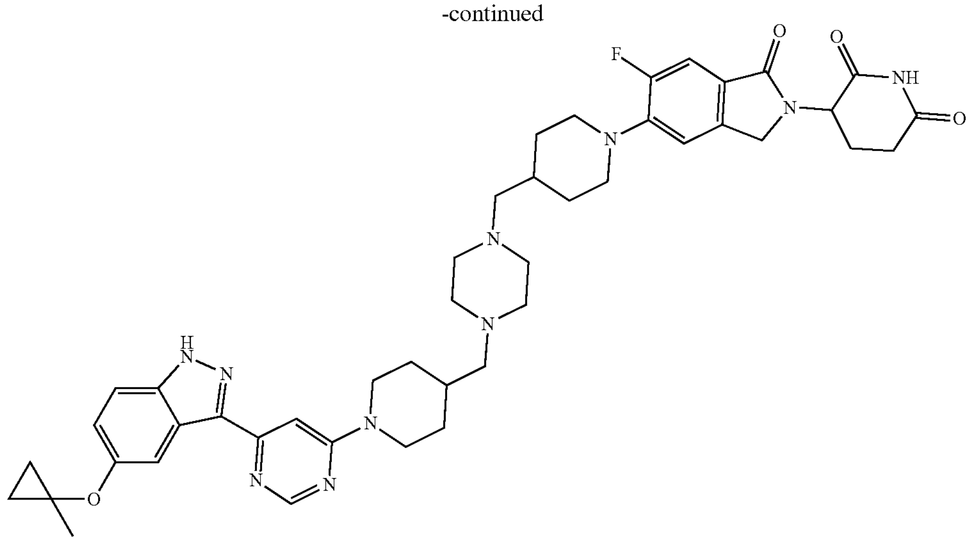

Step 10:

To a solution of 3-[6-fluoro-1-oxo-5-[4-(piperazin-1-yl-methyl)-1-piperidyl]isoindolin-2-yl] piperidine-2,6-dione (51 mg, 0.10 mmol, 1 eq, hydrochloride) in methanol (3 mL) was added sodium acetate (43 mg, 0.53 mmol, 5 eq), then 1-[6-[5-(1-methylcyclopropoxy)-1H-pyrazolo[3,4-c]pyridin-3-yl]pyrimidin-4-yl]piperidine-4-carbaldehyde (40 mg, 0.10 mmol, 1 eq) and acetic acid (0.3 mL) was added. Then the mixture was stirred at 20° C. for 0.5 hour. borane; 2-methylpyridine (22 mg, 0.21 mmol, 2 eq) was added to the mixture, the reaction mixture was stirred at 20° C. for 2 hours. LCMS showed desired MS was detected. Ethyl acetate (30 mL) was added to dilute the mixture, water (20 mL) was added to the mixture. The aqueous phase was extracted with ethyl acetate (30 mL*2). The combined organic phase was dried over sodium sulfate, filtered and concentrated in vacuum. The residue was purified by prep-HPLC (column: Unisil 3-100 C18 Ultra 150*50 mm*3 um; mobile phase: [water (0.225% FA)-ACN]; B %: 6%-36%, 10 minutes). 3-[6-fluoro-5-[4-[[4-[[1-[6-[5-(1-methylcyclopropoxy)-1H-pyrazolo[3,4-c]pyridin-3-yl]pyrimidin-4-yl]-4-piperidyl]methyl]piperazin-1-yl]methyl]-1-piperidyl]-1-oxo-isoindolin-2-yl]piperidine-2,6-dione (31.1 mg, 0.04 mmol, 34.19% yield, 99% purity, formate) was obtained as a white solid.

Exemplary Synthesis of Compound 192

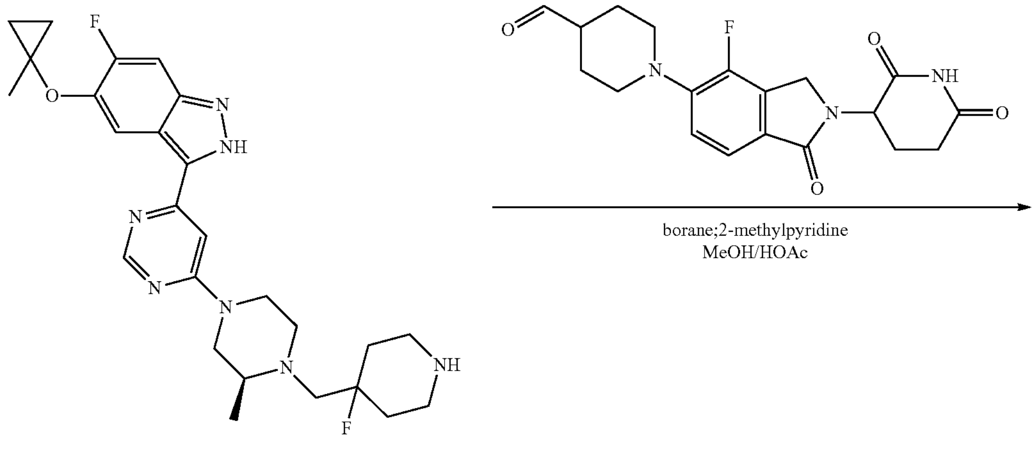

-continued

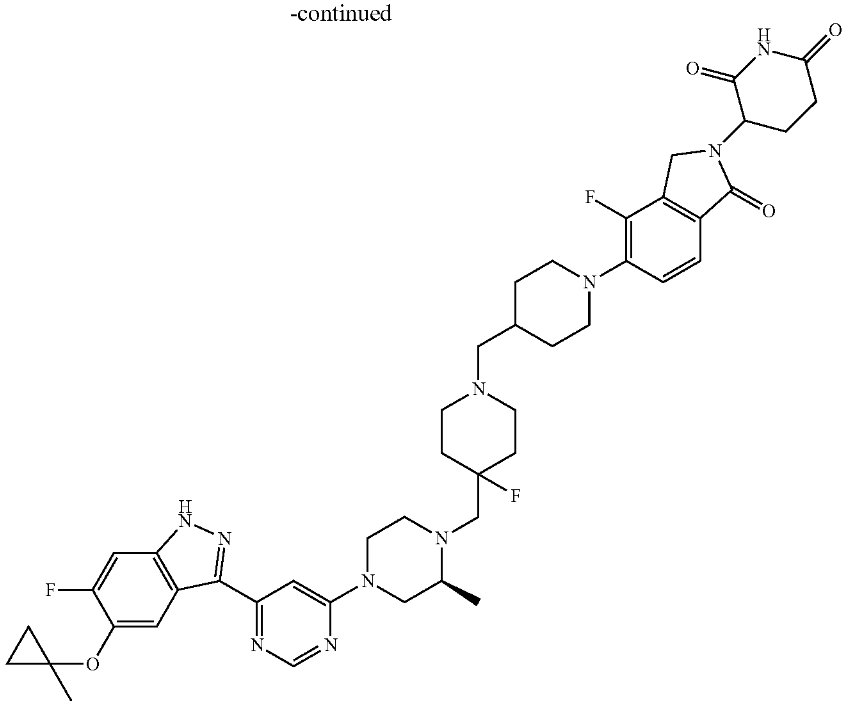

Step 1:

To the mixture of 6-fluoro-3-[6-[(3S)-4-[(4-fluoro-4-piperidyl)methyl]-3-methyl-piperazin-1-yl]pyrimidin-4-yl]-5-(1-methylcyclopropoxy)-2H-indazole (72.64 mg, 102.19 μmol, 70% purity, 1.07 eq) and 1-[2-(2,6-dioxo-3-piperidyl)-4-fluoro-1-oxo-isoindolin-5-yl]piperidine-4-carbaldehyde (45 mg, 95.21 μmol, 79% purity, 1 eq) in HOAC (1 mL) and MeOH (10 mL) was stirred at 20° C. for 20 minutes, then borane; 2-methylpyridine (20.37 mg, 190.42 μmol, 2 eq) was added. Then the mixture was stirred at 20° C. for 16 hours under $N_2$. LCMS showed desired product. The residue was concentrated under reduced pressure to give a residue. The residue was purified by prep-HPLC (column: Xtimate C18 100*30 mm*10 um; mobile phase: [water (0.225% FA)-ACN]; B %: 0%-35%, 40 min) to afford 3-[4-fluoro-5-[4-[[4-fluoro-4-[[(2S)-4-[6-[6-fluoro-5-(1-methylcyclopropoxy)-1H-indazol-3-yl]pyrimidin-4-yl]-2-methyl-piperazin-1-yl]methyl]-1-piperidyl]methyl]-1-piperidyl]-1-oxo-isoindolin-2-yl]piperidine-2,6-dione (67.6 mg, 77.60 μmol, 81.50% yield, 98.14% purity) as white solid.

Exemplary Synthesis of Compound 193

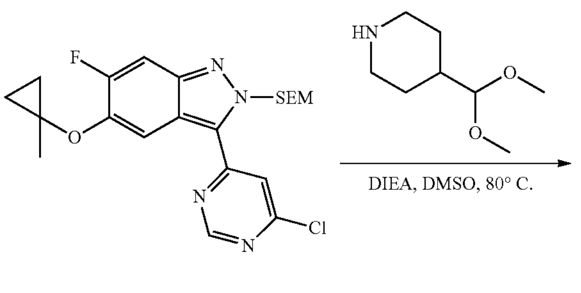

-continued

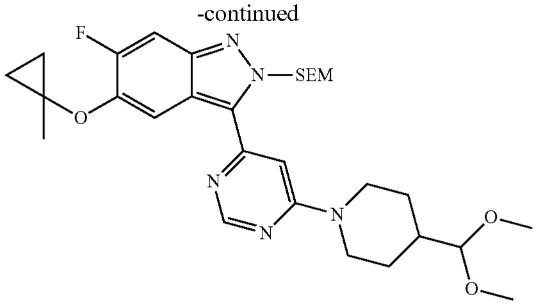

Step 1:

A mixture of 2-[[3-(6-chloropyrimidin-4-yl)-6-fluoro-5-(1-methylcyclopropoxy)indazol-2-yl]methoxy]ethyl-trimethyl-silane (200 mg, 445.44 μmol, 1 eq), 4-(dimethoxymethyl)piperidine (85.11 mg, 534.53 μmol, 1.2 eq) in DMSO (5 mL) was added DIEA (57.57 mg, 445.44 μmol, 77.59 μL, 1 eq), and then the mixture was stirred at 100° C. for 12 hours under $N_2$ atmosphere. LCMS showed desired mass. TLC (Petroleum ether:Ethyl acetate=3:1) showed one new major spot. The resulting product was poured into $H_2O$ (10 mL). The mixture was extracted with ethyl acetate (50 mL*3). The organic phase was washed with brine (50 mL), dried over anhydrous $Na_2SO_4$ concentrated in vacuum to give a residue. The residue was purified by silica gel column chromatography (0 to 27% Ethyl acetate in Petroleum ether) to give 2-[[3-[6-[4-(dimethoxymethyl)-1-piperidyl]pyrimidin-4-yl]-6-fluoro-5-(1-methylcyclopropoxy)indazol-2-yl]methoxy]ethyl-trimethyl-silane (210 mg, 367.29 μmol, 82.45% yield) as a yellow oil.

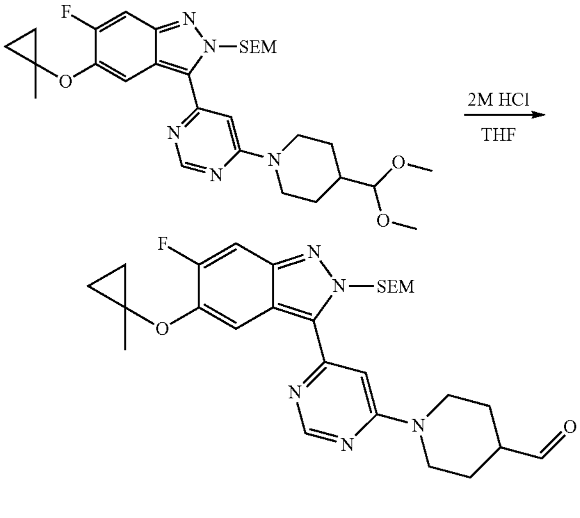

Step 2:

To a solution of 2-[[3-[6-[4-(dimethoxymethyl)-1-piperidyl]pyrimidin-4-yl]-6-fluoro-5-(1-methylcyclopropoxy) indazol-2-yl]methoxy]ethyl-trimethyl-silane (210 mg, 367.29 μmol, 1 eq) in THF (10 mL) was added HCl (2 M, 2 mL, 10.89 eq). After addition, the reaction solution was stirred at 60° C. for 2 hours. LCMS showed desired MS. After cooling, the residue was poured into $NaHCO_3$ to adjusted the pH=7-8 and washed with water (20 mL). The mixture was extracted with ethyl acetate (20 mL*3). The organic phase was washed with brine (20 mL), dried over anhydrous $Na_2SO_4$ concentrated in vacuum to give 1-[6-[6-fluoro-5-(1-methylcyclopropoxy)-2H-indazol-3-yl]pyrimidin-4-yl]piperidine-4-carbaldehyde (140 mg, 343.42 μmol, 93.50% yield, 97% purity) as a colorless oil

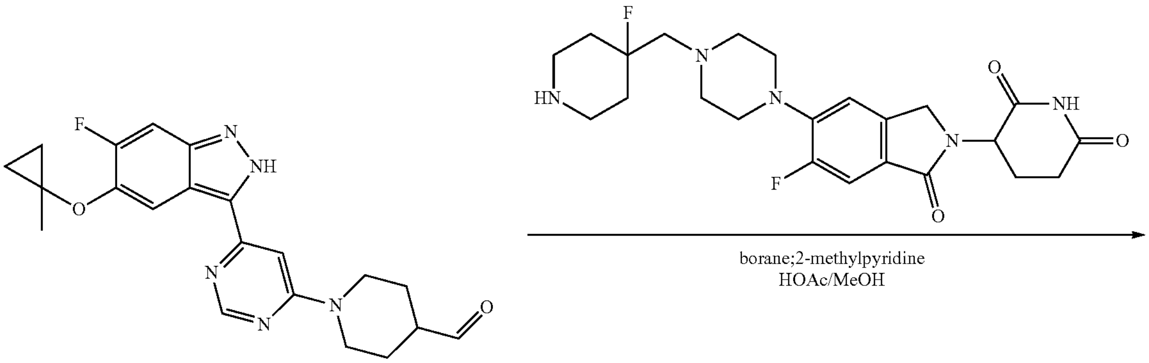

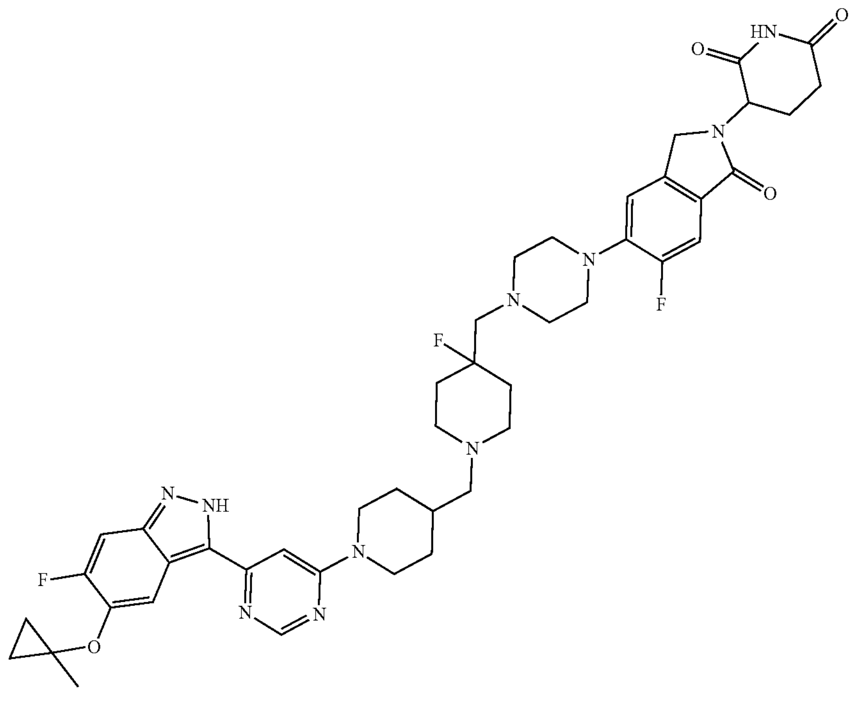

Step 3:

A mixture of 1-[6-[6-fluoro-5-(1-methylcyclopropoxy)-2H-indazol-3-yl]pyrimidin-4-yl]piperidine-4-carbaldehyde (70 mg, 177.02 μmol, 1 eq), 3-[6-fluoro-5-[4-[(4-fluoro-4-piperidyl)methyl]piperazin-1-yl]-1-oxo-isoindolin-2-yl]piperidine-2,6-dione (81.70 mg, 177.02 μmol, 1 eq) in MeOH (10 mL) and AcOH (2 mL) was added borane; 2-methylpyridine (37.87 mg, 354.05 μmol, 2 eq) and then the mixture was stirred at 25° C. for 12 hours LCMS showed desired MS. The reaction mixture was filtered and concentrated under reduced pressure to give a residue. The residue was purified by prep-HPLC (column: Xtimate C18 100*30 mm*10 um; mobile phase: [water (0.225% FA)-ACN]; B %: 0%-35%, 40 min) to give 3-[6-fluoro-5-[4-[[4-fluoro-1-[[1-[6-[6-fluoro-5-(1-methylcyclopropoxy)-2H-indazol-3-yl]pyrimidin-4-yl]-4-piperidyl]methyl]-4-piperidyl]methyl]piperazin-1-yl]-1-oxo-isoindolin-2-yl]piperidine-2,6-dione (41.4 mg, 47.75 μmol, 26.98% yield, 97% purity) as a white solid.

Exemplary Synthesis of Compound 194

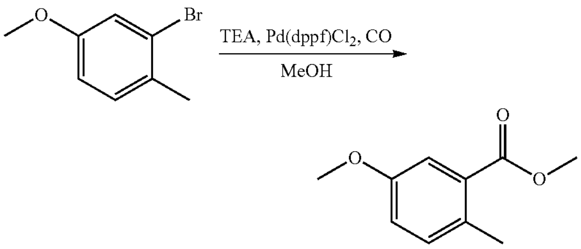

Step 1:

To a solution of 2-bromo-4-methoxy-1-methyl-benzene (19 g, 94.50 mmol, 1 eq) in MeOH (50 mL) was added Pd(dppf)Cl2 (3.46 g, 4.72 mmol, 0.05 eq) and TEA (28.69 g, 283.50 mmol, 39.46 mL, 3 eq) under $N_2$. The suspension was degassed under vacuum and purged with CO several times. The mixture was stirred under CO (3 MPa) at 100° C. for 96 hours. TLC showed the reaction was completed. The residue was filtered and concentrated in vacuum. The residue was purified by silica gel chromatography (80 g, 0-3% (15 min) of Ethyl acetate in Petroleum ether, 3% (15 min) of Ethyl acetate in Petroleum ether) to afford methyl 5-methoxy-2-methyl-benzoate (15.5 g, 86.02 mmol, 91.02% yield) as a colorless oil.

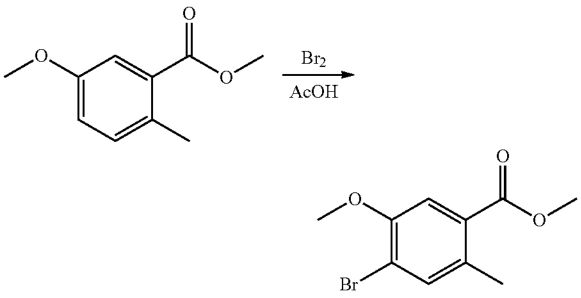

Step 2:

To a solution of methyl 5-methoxy-2-methyl-benzoate (5 g, 27.75 mmol, 1 eq) in AcOH (50 mL) was added Br2 (8.87 g, 55.49 mmol, 2.86 mL, 2 eq). After addition, the mixture was stirred at 20° C. for 2 hours. TLC showed the reaction was completed. The reaction mixture was quenched by saturated $Na_2S_2O_3$ (60 mL) and extracted with ethyl acetate (2×40 mL). The organic layer was dried over sodium sulfate and concentrated under reduced pressure. The residue was purified by silica gel chromatography (80 g, 0-3% (20 minutes) of Ethyl acetate in Petroleum ether, 3% (10 minutes) of Ethyl acetate in Petroleum ether) to afford methyl 4-bromo-5-methoxy-2-methyl-benzoate (1.1 g, 3.64 mmol, 13.13% yield, 85.784% purity) as a white solid.

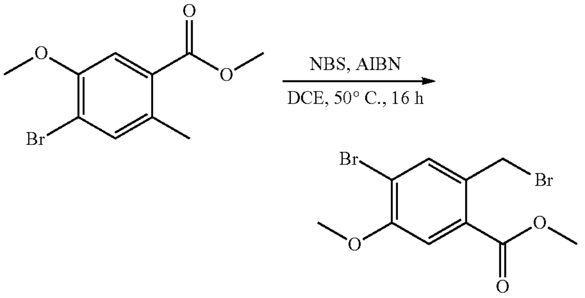

Step 3:

To a mixture of methyl 4-bromo-5-methoxy-2-methyl-benzoate (450 mg, 1.74 mmol, 1 eq) in DCE (10 mL) was added NBS (370.95 mg, 2.08 mmol, 1.2 eq) and AIBN (57.04 mg, 347.36 μmol, 0.2 eq) under $N_2$ at 20° C. Then the mixture was stirred at 50° C. for 16 hours. TLC showed one new major point. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by silica gel chromatography (20 g, 0-3% (12 minutes) of Ethyl acetate in Petroleum ether, 0-3% (12 minutes) of Ethyl acetate in Petroleum ether) to afford methyl 4-bromo-2-(bromomethyl)-5-methoxy-benzoate (200 mg, 591.73 μmol, 34.07% yield) as a white solid.

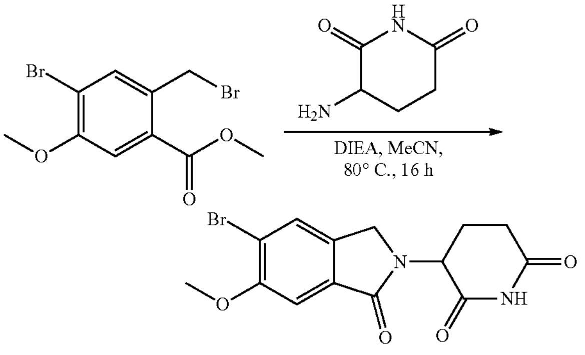

Step 4:

To a mixture of methyl 4-bromo-2-(bromomethyl)-5-methoxy-benzoate (200 mg, 591.73 μmol, 1 eq) and 3-aminopiperidine-2,6-dione (113.73 mg, 887.59 μmol, 1.5 eq) in MeCN (3 mL) was added DIEA (229.43 mg, 1.78 mmol, 309.21 uL, 3 eq). The mixture was stirred at 80° C. for 16 hours. LCMS showed there was desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.

HPLC (column: Xtimate C18 150*40 mm*10 um; mobile phase: [water (0.225% FA)-ACN]; B %: 20%-50%, 10 min) to afford 3-(5-bromo-6-methoxy-1-oxo-isoindolin-2-yl)piperidine-2,6-dione (88 mg, 249.17 μmol, 42.11% yield) as a gray solid.

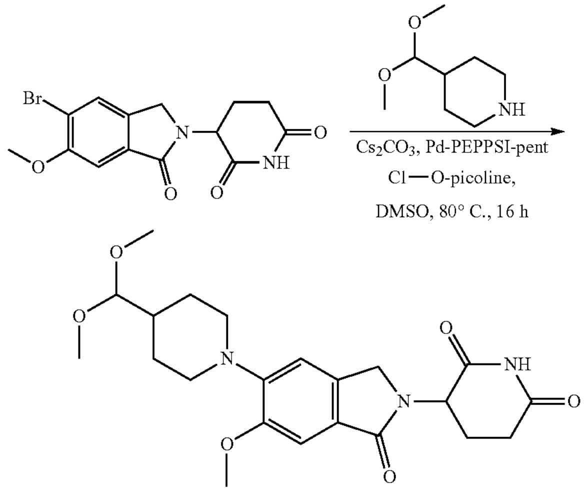

Step 5:

To a solution of 3-(5-bromo-6-methoxy-1-oxo-isoindolin-2-yl)piperidine-2,6-dione (88 mg, 249.17 μmol, 1 eq) and 4-(dimethoxymethyl)piperidine (79.35 mg, 498.35 μmol, 2 eq) in DMSO (5 mL) was added Pd-PEPPSI-pent Cl—O-picoline (21.43 mg, 24.92 μmol, 0.1 eq) and Cs2CO3 (162.37 mg, 498.35 μmol, 2 eq) under $N_2$. After addition, the mixture was stirred at 80° C. for 16 hours under $N_2$. LCMS showed there was desired MS. The residue was filtered and concentrated in vacuum. The residue was purified by silica gel chromatography (12 g, 0-100% (20 min) of Ethyl acetate in Petroleum ether, 0-15%(10 min) of Methanol in Dichloromethane, 15%(10 min) of Methanol in Dichloromethane) to afford 3-[5-[4-(dimethoxymethyl)-1-piperidyl]-6-methoxy-1-oxo-isoindolin-2-yl]piperidine-2,6-dione (50 mg, 63.73 μmol, 25.58% yield, 55% purity) as a white solid.

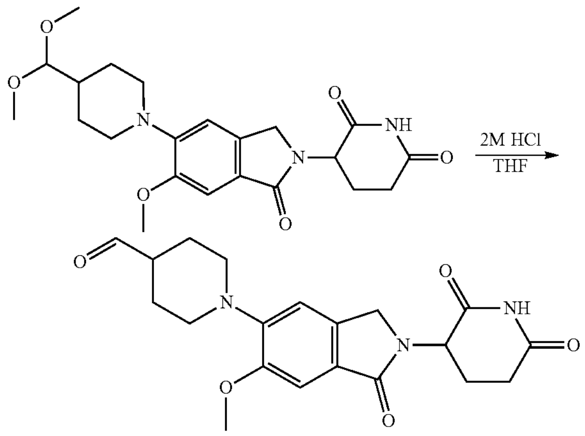

Step 6:

To a solution of 3-[5-[4-(dimethoxymethyl)-1-piperidyl]-6-methoxy-1-oxo-isoindolin-2-yl]piperidine-2,6-dione (50 mg, 115.88 μmol, 1 eq) in THF (2 mL) was added HCl (2 M, 972.11 uL, 16.78 eq). After addition, the reaction was stirred at 20° C. for 16 hours. LCMS showed there was desired MS. The residue was added $NaHCO_3$ to adjusted the pH=7-8. The aqueous phase was extracted with ethyl acetate (20 mL*3). The combined organic phase was washed with brine (20 mL*2), dried with anhydrous $Na_2SO_4$, filtered and concentrated in vacuum to afford 1-[2-(2,6-dioxo-3-piperidyl)-6-methoxy-1-oxo-isoindolin-5-yl]piperidine-4-carbaldehyde (55 mg, crude) as a white solid.

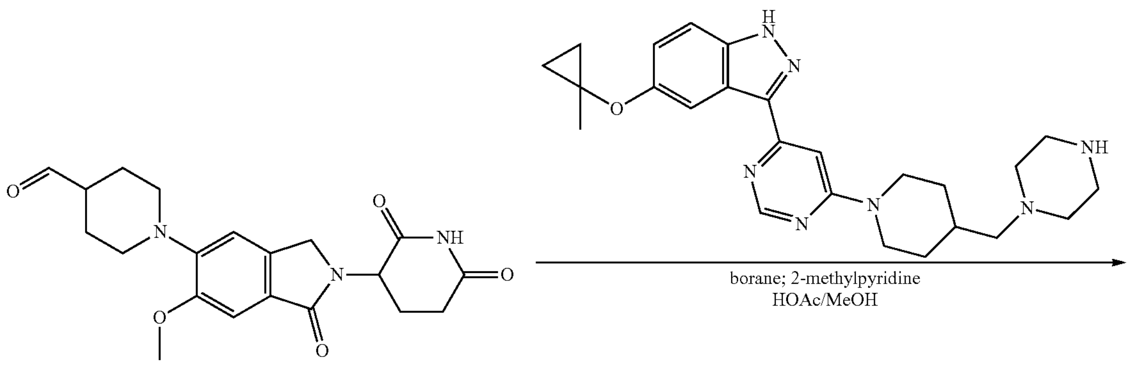

-continued

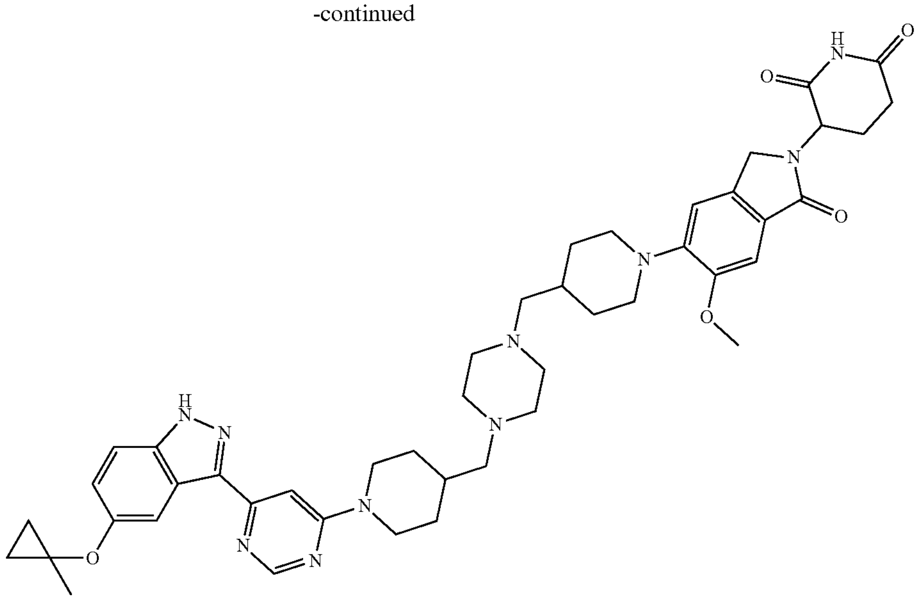

Step 7:

To a solution of 1-[2-(2,6-dioxo-3-piperidyl)-6-methoxy-1-oxo-isoindolin-5-yl]piperidine-4-carbaldehyde (55 mg, 71.35 μmol, 50% purity, 1 eq) and 5-(1-methylcyclopropoxy)-3-[6-[4-(piperazin-1-ylmethyl)-1-piperidyl]pyrimidin-4-yl]-1H-indazole (35.13 mg, 78.49 μmol, 1.1 eq) in MeOH (10 mL), THF (10 mL) and AcOH (1 mL) was added borane; 2-methylpyridine (15.26 mg, 142.70 μmol, 2 eq). After addition, the mixture was stirred at 20° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.HPLC (column: Xtimate C18 100*30 mm*10 um; mobile phase: [water (0.1% TFA)-ACN]; B %: 0%-50%, 40 min) to afford 3-[6-methoxy-5-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (22.3 mg, 26.63 μmol, 37.32% yield, 97.547% purity) as a white solid.

Exemplary Synthesis of Compound 195

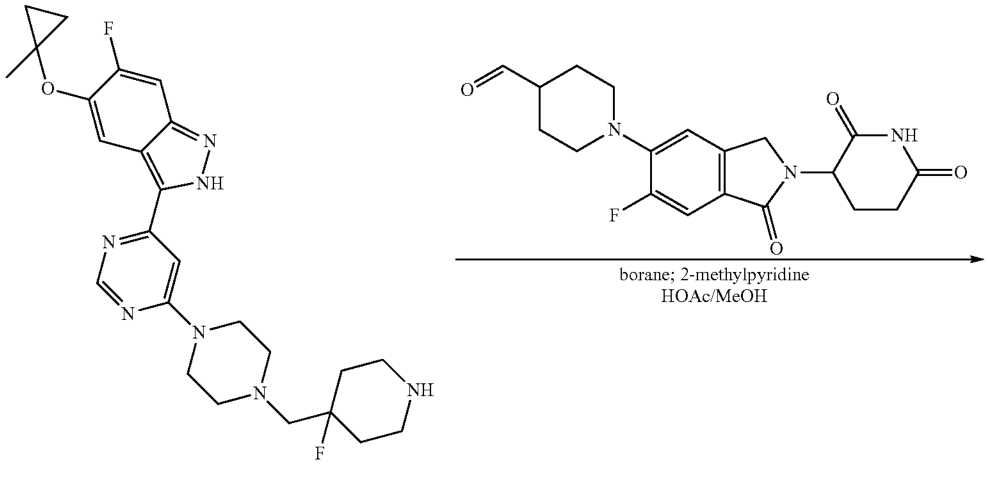

-continued

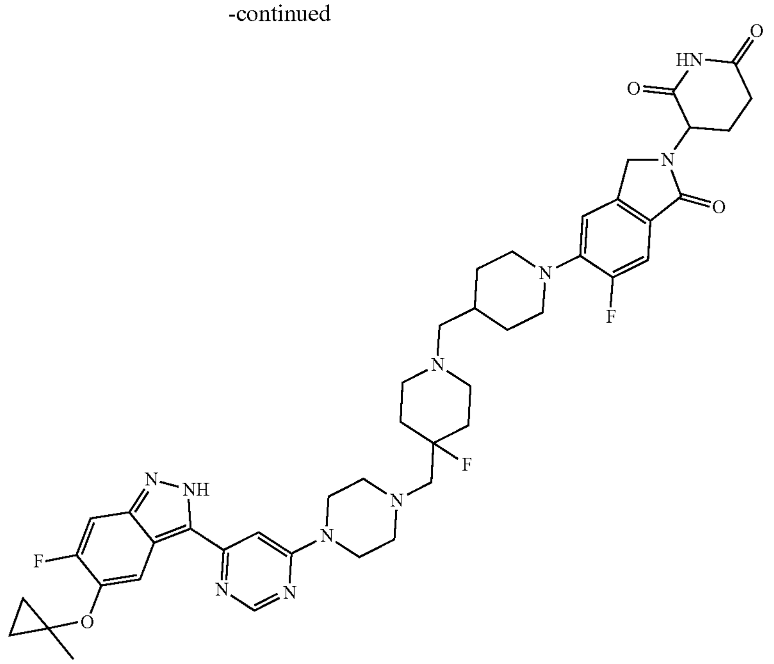

Step 1:

To a mixture of 6-fluoro-3-[6-[4-[(4-fluoro-4-piperidyl)methyl]piperazin-1-yl]pyrimidin-4-yl]-5-(1-methylcyclopropoxy)-2H-indazole (85 mg, 175.78 μmol, 1 eq) and 1-[2-(2,6-dioxo-3-piperidyl)-6-fluoro-1-oxo-isoindolin-5-yl]piperidine-4-carbaldehyde (65.63 mg, 175.78 μmol, 1 eq) in THF (10 mL), MeOH (10 mL) and AcOH (1 mL) was added borane; 2-methylpyridine (37.60 mg, 351.56 μmol, 2 eq). The mixture was stirred at 20° C. for 16 hours. LCMS showed there was desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.HPLC (column: Xtimate C18 100*30 mm*10 um; mobile phase: [water (0.225% FA)-ACN]; B %: 0%-35%, 40 min) to afford 3-[6-fluoro-5-[4-[[4-fluoro-4-[[4-[6-[6-fluoro-5-(1-methylcyclopropoxy)-2H-indazol-3-yl]pyrimidin-4-yl]piperazin-1-yl]methyl]-1-piperidyl]methyl]-1-piperidyl]-1-oxo-isoindolin-2-yl]piperidine-2,6-dione (38.3 mg, 45.47 μmol, 25.87% yield, 99.834% purity) as a white solid.

Exemplary Synthesis of Compound 196

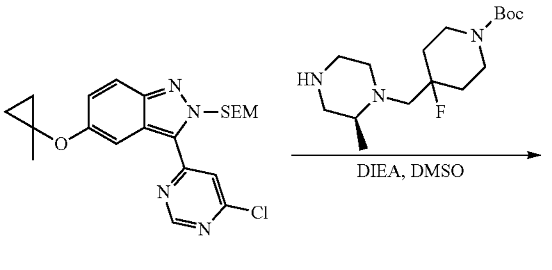

-continued

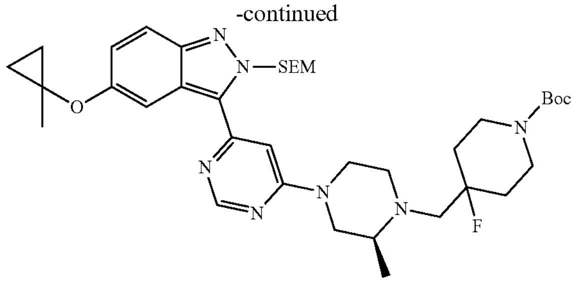

Step 1:

To a solution tert-butyl 4-fluoro-4-[[(2S)-2-methylpiperazin-1-yl]methyl]piperidine-1-carboxylate (109.78 mg, 348.03 μmol, 1.2 eq) and 2-[[3-(6-chloropyrimidin-4-yl)-5-(1-methylcyclopropoxy)indazol-2-yl]methoxy]ethyl-trimethyl-silane (150 mg, 348.03 μmol, 1 eq) in DMSO (2 mL) was added TEA (105.65 mg, 1.04 mmol, 145.32 uL, 3 eq). Then the reaction was stirred at 90° C. for 1 hour. LCMS showed one peak with desired mass was detected. The reaction mixture was diluted with water (15 mL) and extracted with dichloromethane (15 mL*3). The organic layer was dried over sodium sulfate and concentrated under reduced pressure. The residue was purified by silica gel column chromatography (0 to 30% Ethyl acetate in Petroleum ether) to give tert-butyl 4-fluoro-4-[[(2S)-2-methyl-4-[6-[5-(1-methylcyclopropoxy)-2-(2-trimethylsilylethoxymethyl)indazol-3-yl]pyrimidin-4-yl]piperazin-1-yl]methyl]piperidine-1-carboxylate (200 mg, 262.83 μmol, 75.52% yield, 93.3% purity) as a light yellow oil

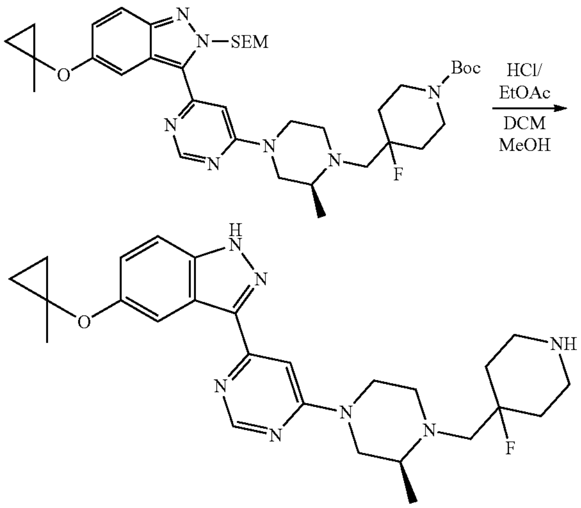

Step 2:

To a mixture of tert-butyl 4-fluoro-4-[[(2S)-2-methyl-4-[6-[5-(1-methylcyclopropoxy)-2-(2-trimethylsilylethoxymethyl)indazol-3-yl]pyrimidin-4-yl]piperazin-1-yl]methyl]piperidine-1-carboxylate (200 mg, 281.70 μmol, 1 eq) in DCM (1 mL) and MeOH (1 mL) was added HCl/EtOAc (4 M, 2 mL, 28.40 eq). The mixture was stirred at 25° C. for 1 hour. LCMS showed one peak with desired mass was detected. The mixture was concentrated in reduce pressure at 45° C. to give tert-butyl 4-fluoro-4-[[(2S)-2-methyl-4-[6-[5-(1-methylcyclopropoxy)-2-(2-trimethylsilylethoxymethyl)indazol-3-yl]pyrimidin-4-yl]piperazin-1-yl]methyl]piperidine-1-carboxylate (200 mg, 262.83 μmol, 75.52% yield, 93.3% purity) as a light yellow oil.

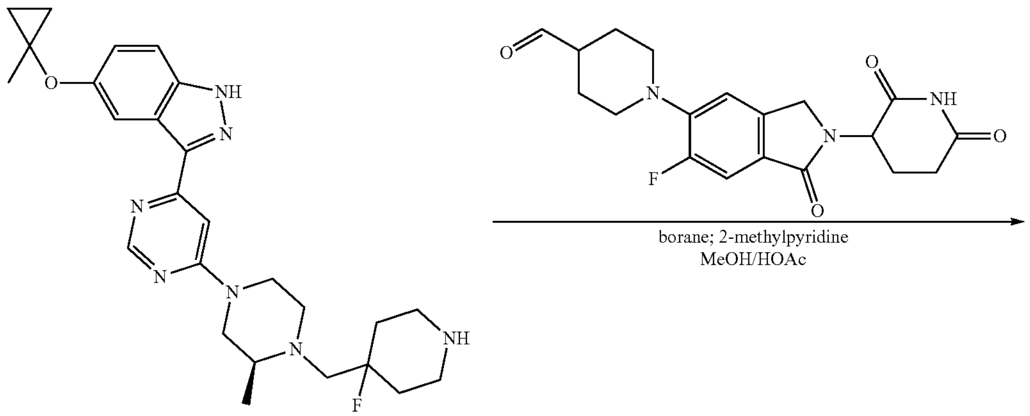

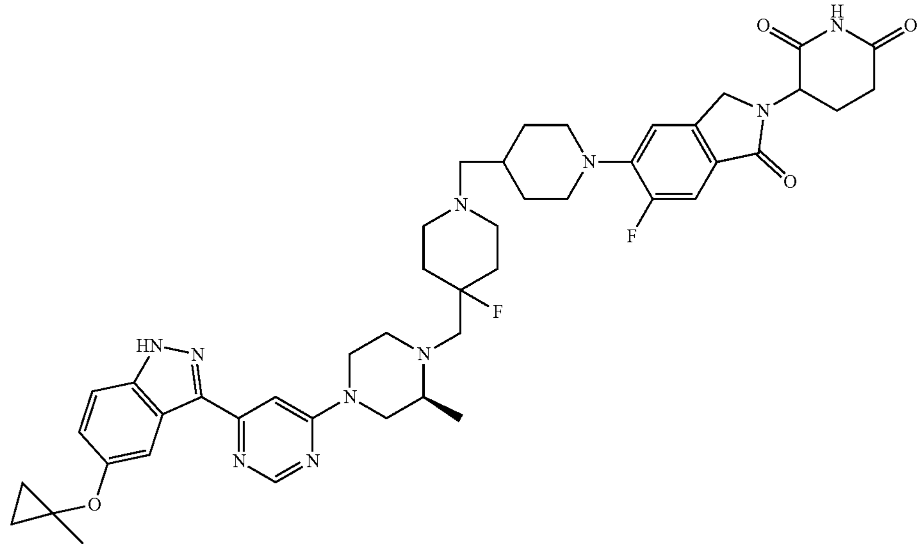

Step 3:

To the mixture of 3-[6-[(3S)-4-[(4-fluoro-4-piperidyl)methyl]-3-methyl-piperazin-1-yl]pyrimidin-4-yl]-5-(1-methylcyclopropoxy)-2H-indazole (38.90 mg, 56.78 μmol, 70% purity, 1.07 eq) and 1-[2-(2,6-dioxo-3-piperidyl)-4-fluoro-1-oxo-isoindolin-5-yl]piperidine-4-carbaldehyde (25 mg, 52.90 μmol, 79% purity, 1 eq) in HOAC (1 mL) and MeOH (10 mL) was stirred at 20° C. for 20 minutes, then was added borane; 2-methylpyridine (11.32 mg, 105.80 μmol, 2 eq). Then the mixture was stirred at 20° C. for 16 hours under $N_2$. LCMS showed desired product. The residue was concentrated under reduced pressure to give a residue. The residue was purified by prep-HPLC (column: Xtimate C18 100*30 mm*10 um; mobile phase: [water (10 mM $NH_4HCO_3$)-ACN]; B %: 10%-80%, 40 min) to afford 3-[4-fluoro-5-[4-[[4-fluoro-4-[[(2S)-2-methyl-4-[6-[5-(1-methylcyclopropoxy)-1H-indazol-3-yl]pyrimidin-4-yl]piperazin-1-yl]methyl]-1-piperidyl]methyl]-1-piperidyl]-1-oxo-isoindolin-2-yl]piperidine-2,6-dione (18.4 mg, 21.61 μmol, 40.85% yield, 98.3% purity) as white solid.

Exemplary Synthesis of Compound 197

Compound 197 was prepared in a manner analogous to compound 196 starting with 2-[[13-(6-chloropyrimidin-4-yl)-6-fluoro-5-(1-methylcyclopropoxy)indazol-2-yl]methoxy]ethyl-trimethyl-silane as the starting material.

Exemplary Synthesis of Compound 198

Step 1:

To a solution of 1-[2-(2,6-dioxo-3-piperidyl)-6-methoxy-1-oxo-isoindolin-5-yl]piperidine-4-carbaldehyde (90 mg, 168.13 μmol, 72% purity, 1 eq) and 3-[6-[4-[(4-fluoro-4-piperidyl)methyl]piperazin-1-yl]pyrimidin-4-yl]-5-(1-methylcyclopropoxy)-2H-indazole (78.28 mg, 168.13 μmol, 1 eq) in MeOH (10 mL), THF (10 mL) and AcOH (1 mL) was added borane; 2-methylpyridine (35.97 mg, 336.26 μmol, 2 eq). After addition, the mixture was stirred at 20° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous Na2SO4, filtered and concentrated in vacuum. The residue was purified by prep. HPLC (The residue was purified by prep.HPLC (column: Xtimate C18 100*30 mm*10 um; mobile phase: [water (0.1% TFA)-ACN]; B %: 0%-50%, 40 minutes) to afford 3-[5-[4-[[4-fluoro-4-[[4-[6-[5-(1-methylcyclopropoxy)-2H-indazol-3-yl]pyrimidin-4-yl]piperazin-1-yl]methyl]-1-piperidyl]methyl]-1-piperidyl]-6-methoxy-1-oxo-isoindolin-2-yl]piperidine-2,6-dione (31 mg, 36.05 μmol, 21.44% yield, 97.108% purity) as a white solid.

Exemplary Synthesis of Compound 199

Compound 199 was prepared in a manner analogous to compound 190 using 1-[6-[6-fluoro-5-(1-methylcyclopropoxy)-2H-indazol-3-yl]pyrimidin-4-yl]piperidine-4-carbaldehyde in the final step.

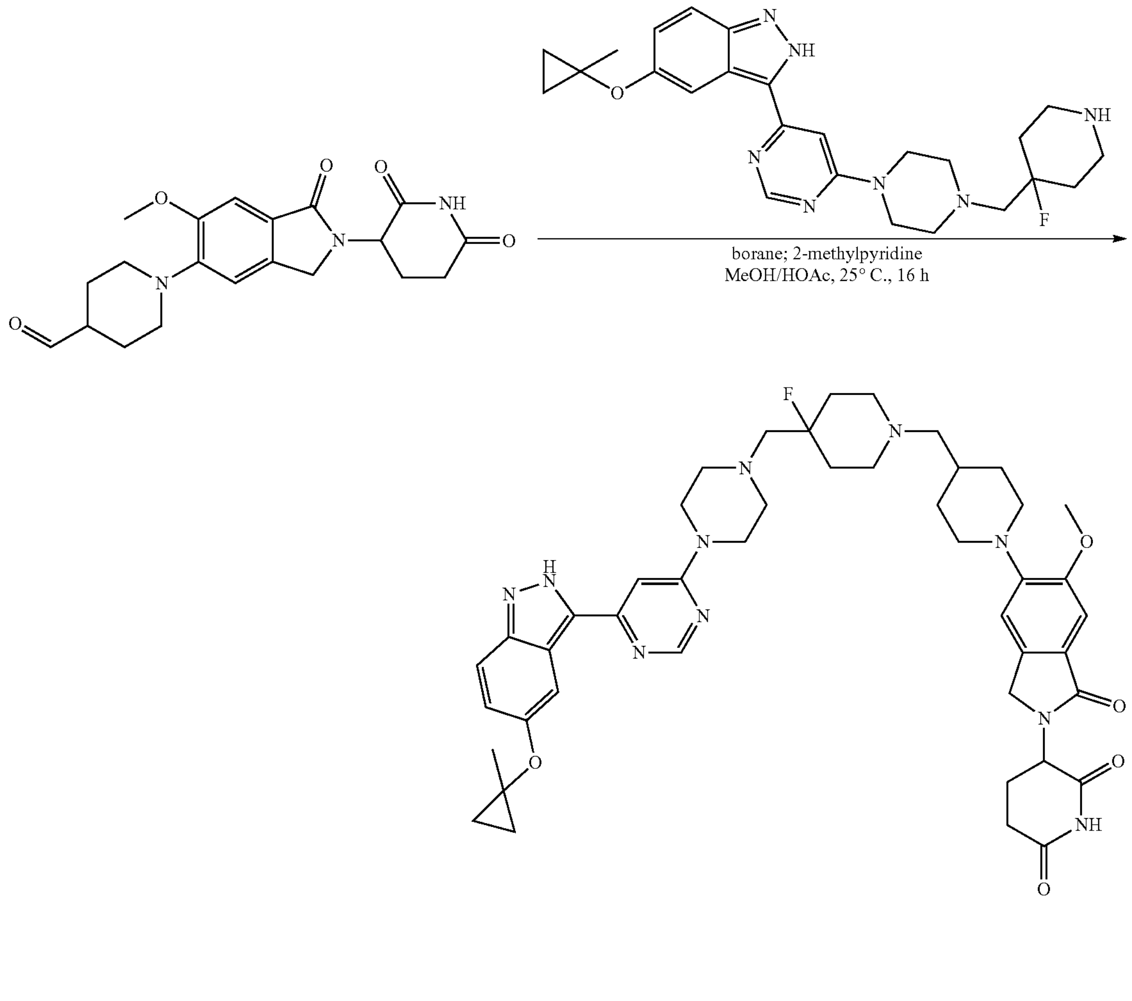

Exemplary Synthesis of Compound 200

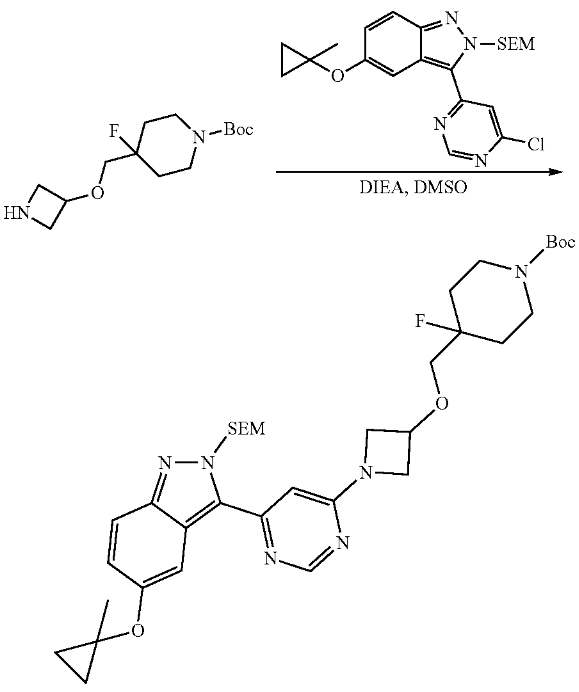

Step 1:

To a mixture of tert-butyl 4-(azetidin-3-yloxymethyl)-4-fluoro-piperidine-1-carboxylate (150 mg, 520.19 μmol, 1 eq) and 2-[[3-(6-chloropyrimidin-4-yl)-5-(1-methylcyclopropoxy)indazol-2-yl]methoxy]ethyl-trimethyl-silane (200 mg, 464.03 μmol, 8.92 e-1 eq) in DMSO (5 mL) was added TEA (52.64 mg, 520.19 μmol, 72.40 uL, 1 eq). The mixture was stirred at 90° C. for 16 hours. LCMS showed there was desired MS. The residue was poured into water (30 mL). The aqueous phase was extracted with ethyl acetate (30 mL*3). The combined organic phase was washed with brine (30 mL*2), dried with anhydrous $Na_2SO_4$, filtered and concentrated in vacuum. The residue was purified by silica gel chromatography (12 g, 0-40% (15 min) of Ethyl acetate in Petroleum ether, 40% (10 minutes) of Ethyl acetate in Petroleum ether) to afford tert-butyl 4-fluoro-4-[[1-[6-[5-(1-methylcyclopropoxy)-2-(2-trimethylsilylethoxymethyl)indazol-3-yl]pyrimidin-4-yl]azetidin-3-yl]oxymethyl]piperidine-1-carboxylate (250 mg, 343.05 μmol, 65.95% yield, 93.707% purity) as a brown solid.

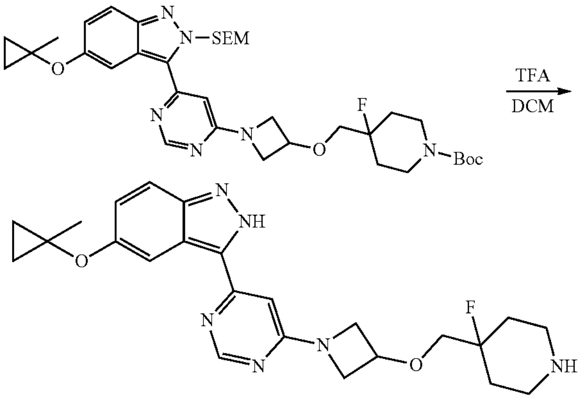

Step 2:

To a mixture of tert-butyl 4-fluoro-4-[[1-[6-[5-(1-methylcyclopropoxy)-2-(2-trimethylsilylethoxymethyl)indazol-3-yl]pyrimidin-4-yl]azetidin-3-yl]oxymethyl]piperidine-1-carboxylate (150 mg, 219.65 μmol, 1 eq) in EtOAc (4 mL) was added HCl/EtOAc (4 M, 4 mL, 72.84 eq). The mixture was stirred at 20° C. for 2 hours. TLC showed the reaction was completed. The residue was concentrated in vacuum to afford 3-[6-[3-[(4-fluoro-4-piperidyl)methoxy]azetidin-1-yl]pyrimidin-4-yl]-5-(1-methylcyclopropoxy)-2H-indazole (112 mg, crude, HCl) as a yellow solid.

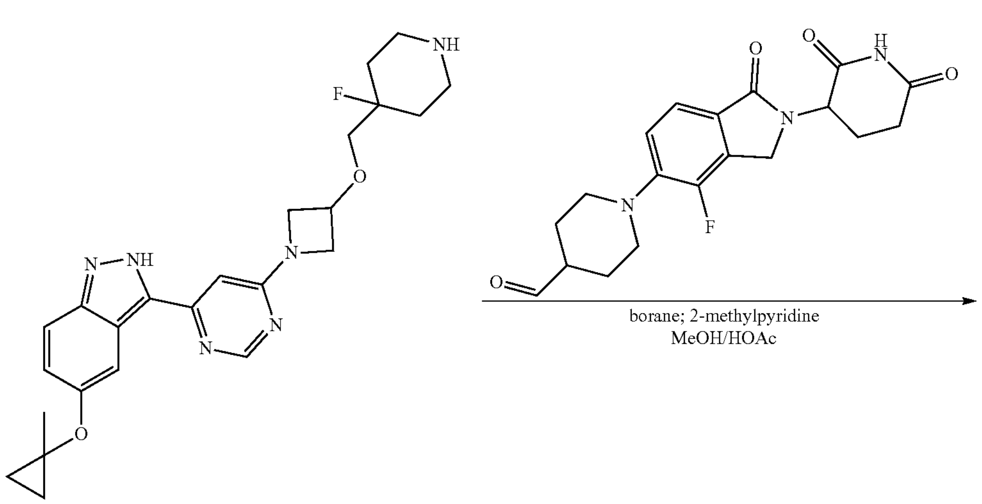

-continued

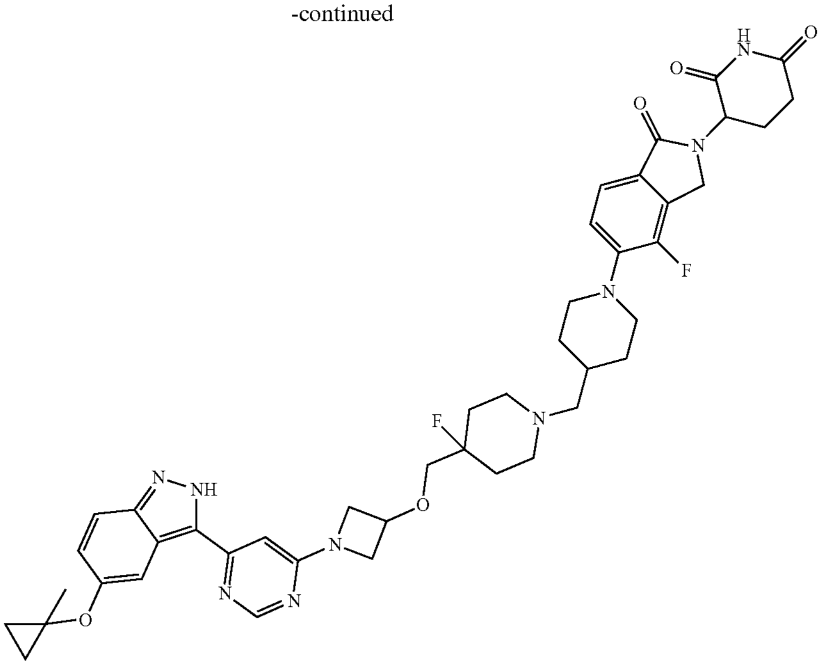

Step 3:

To a mixture of 3-[6-[3-[(4-fluoro-4-piperidyl)methoxy]azetidin-1-yl]pyrimidin-4-yl]-5-(1-methylcyclopropoxy)-2H-indazole (99 mg, 218.77 μmol, 1.36 eq) and 1-[2-(2,6-dioxo-3-piperidyl)-4-fluoro-1-oxo-isoindolin-5-yl]piperidine-4-carbaldehyde (60 mg, 160.70 μmol, 1 eq) in MeOH (10 mL), THF (10 mL) and AcOH (1 mL) was added borane; 2-methylpyridine (34.38 mg, 321.39 μmol, 2 eq). The mixture was stirred at 40° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.HPLC (column: 3_Phenomenex Luna C18 75*30 mm*3 um; mobile phase: [water (0.225% FA)-ACN]; B %: 0%-35%, 40 min) to afford 3-[4-fluoro-5-[4-[[4-fluoro-4-[[1-[6-[5-(1-methylcyclopropoxy)-2H-indazol-3-yl]pyrimidin-4-yl]azetidin-3-yl]oxymethyl]-1-piperidyl]methyl]-1-piperidyl]-1-oxo-isoindolin-2-yl]piperidine-2,6-dione (58 mg, 70.71 μmol, 44.00% yield, 98.738% purity) as a white solid.

Exemplary Synthesis of Compound 201

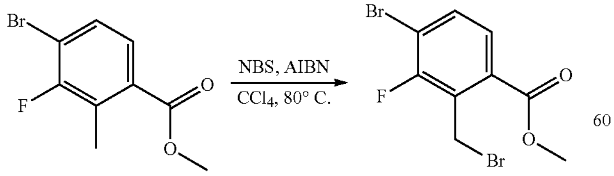

Step 1:

To a solution of methyl 4-bromo-3-fluoro-2-methyl-benzoate (2 g, 8.10 mmol, 1 eq) in $CCl_4$ (20 mL) was added AIBN (133 mg, 0.81 mmol, 0.1 eq) and NBS (1.44 g, 8.10 mmol, 1 eq). The mixture was stirred at 80° C. for 16 hours. LC-MS showed small amount of starting material remained, desired compound was detected as the major product. The reaction mixture was partitioned between water 30 mL and DCM 60 mL (20 mL*3). The organic phase was separated, dried over $Na_2SO_4$, filtered and concentrated under reduced pressure to give a residue. The residue was purified by column chromatography (SiO2, Petroleum ether/Ethyl acetate=10/1 to 6/1). Compound methyl 4-bromo-2-(bromomethyl)-3-fluoro-benzoate (2.3 g, 7.06 mmol, 87% yield) was obtained as a yellow solid.

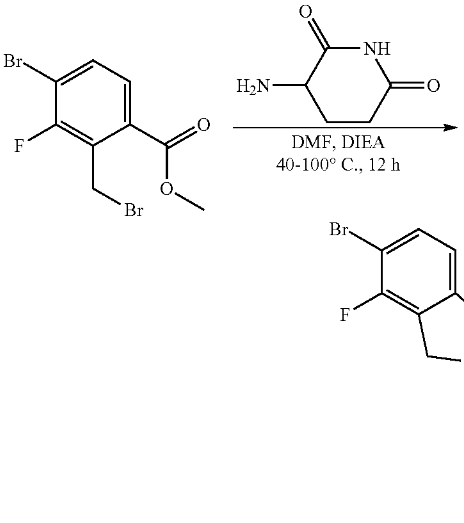

Step 2:

To a solution of 3-aminopiperidine-2,6-dione (904 mg, 5.49 mmol, 7.78 e-1 eq, HCl) in DMF (25 mL) was added DIEA (4.56 g, 35.28 mmol, 6.15 mL, 5 eq) and stirred for 30 minutes, then methyl 4-bromo-2-(bromomethyl)-3-fluorobenzoate (2.3 g, 7.06 mmol, 1 eq) was added. The mixture was stirred at 100° C. for 11.5 hours. LC-MS showed no starting material remained, desired compound was detected as the major product. The reaction mixture was poured into cold water (60 mL), the precipitate formed. The mixture was filtered and the filtrate cake was dried in vacuum. The mixture was triturated with PE and methyl-tertbutyl ether (V/V=1:1, 20 mL). Compound 3-(5-bromo-4-fluoro-1-oxo-isoindolin-2-yl)piperidine-2,6-dione (1.4 g, 4.10 mmol, 58% yield) was obtained as a gray solid.

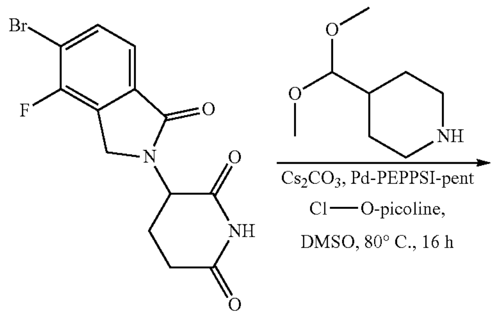

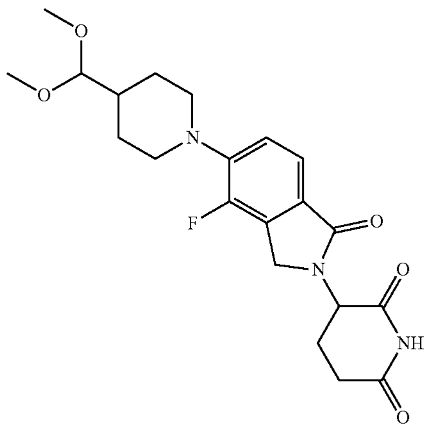

Step 3:

To a solution of 3-(5-bromo-4-fluoro-1-oxo-isoindolin-2-yl)piperidine-2,6-dione (300 mg, 0.88 mmol, 1 eq), 4-(dimethoxymethyl)piperidine (168 mg, 1.06 mmol, 1.2 eq) in DMSO (6 mL) was added $Cs_2CO_3$ (573 mg, 1.76 mmol, 2 eq) and PD-PEPPSI (86 mg, 0.088 mmol, 0.1 eq). The mixture was stirred at 100° C. for 12 h. LC-MS showed desired compound was detected. The reaction mixture was partitioned between water 6 mL and EtOAc 36 mL (12 mL*3). The organic phase was separated, dried over $Na_2SO_4$, filtered and concentrated under reduced pressure to give a residue. The residue was purified by column chromatography by prep-TLC (SiO2, DCM:MeOH=10:1). Compound 3-[5-[4-(dimethoxymethyl)-1-piperidyl]-4-fluoro-1-oxo-isoindolin-2-yl]piperidine-2,6-dione (130 mg, 0.31 mmol, 35% yield) was obtained as a yellow solid.

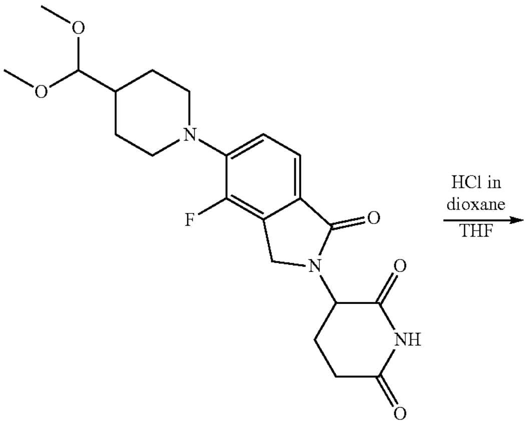

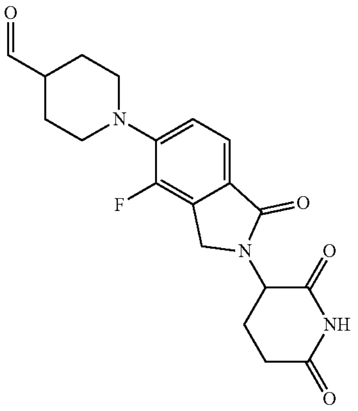

Step 4:

To a solution of 3-[5-[4-(dimethoxymethyl)-1-piperidyl]-4-fluoro-1-oxo-isoindolin-2-yl]piperidine-2,6-dione (80 mg, 0.19 mmol, 1 eq) in THF (0.5 mL) was added HCl/dioxane (4 M, 2 mL, 41.94 eq). The mixture was stirred at 25° C. for 1 hour. TLC plate showed starting material was consumed. The reaction mixture was concentrated under vacuum to give a residue. Compound 1-[2-(2,6-dioxo-3-piperidyl)-4-fluoro-1-oxo-isoindolin-5-yl]piperidine-4-carbaldehyde (70 mg, 0.19 mmol, 98% yield) was obtained as a yellow solid.

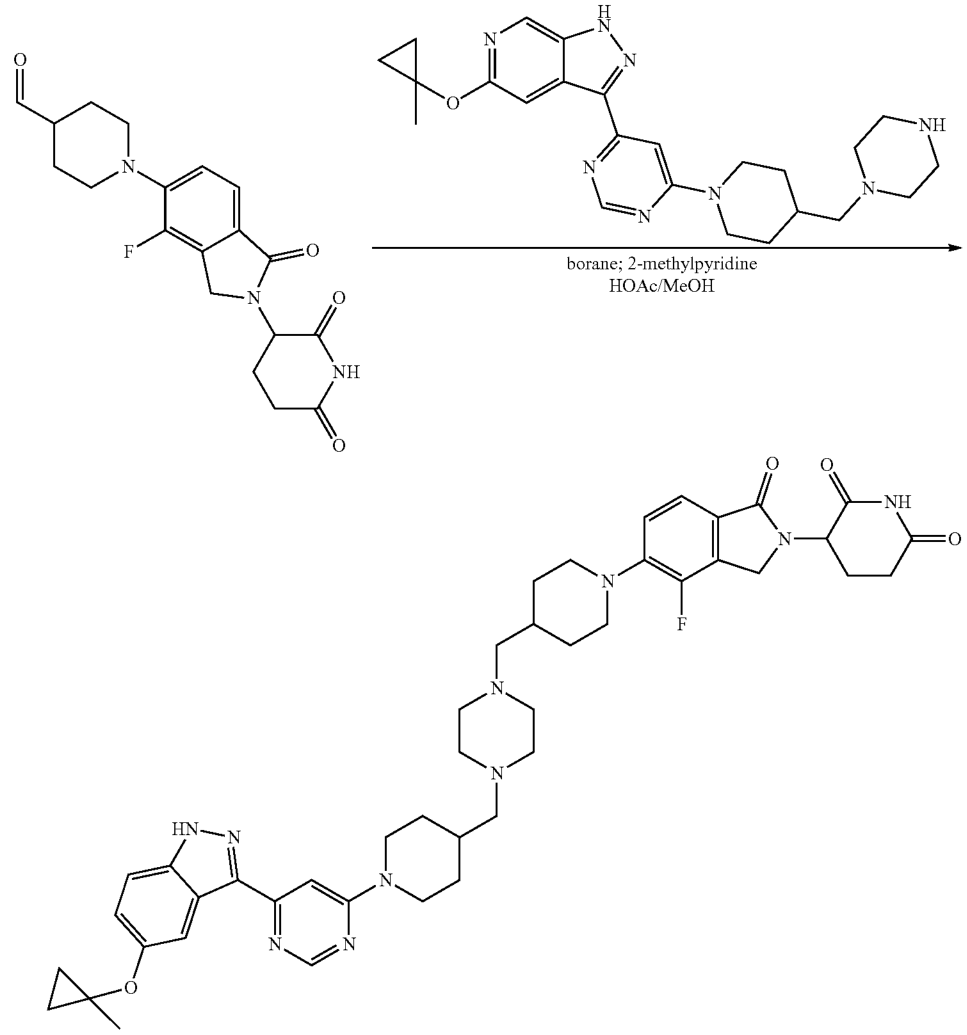

Step 5:

To a solution of 5-(1-methylcyclopropoxy)-3-[6-[4-(piperazin-1-ylmethyl)-1-piperidyl]pyrimidin-4-yl]-1H-pyrazolo[3,4-c]pyridine (43 mg, 0.089 mmol, 1 eq, HCl) in MeOH (2 mL) was added NaOAc (36 mg, 0.44 mmol, 5 eq), the mixture was stirred at 25° C. for 10 minutes, followed by addition of 1-[2-(2,6-dioxo-3-piperidyl)-4-fluoro-1-oxo-isoindolin-5-yl]piperidine-4-carbaldehyde (33 mg, 0.089 mmol, 1 eq), AcOH (0.05 mL), and keep stirring for 20 min. 2-METHYL-PYRIDINE BORANE (28 mg, 0.27 mmol, 3 eq) was then added. The mixture was stirred at 25° C. for 15.5 hours. LC-MS showed no starting material remained. Desired compound was detected as the major product. The reaction mixture was concentrated under reduced pressure to give a residue. The residue was purified by prep-HPLC (column: Phenomenex Synergi C18 150*25 mm*10 um; mobile phase: [water (0.225% FA)-ACN]; B %: 3%-33%, 10 min). Compound 3-(4-fluoro-5-(4-((4-((1-(6-(5-(1-methylcyclopropoxy)-1H-pyrazolo[3,4-c]pyridin-3-yl)pyrimidin-4-yl)piperidin-4-yl)methyl)piperazin-1-yl)methyl)piperidin-1-yl)-1-oxoisoindolin-2-yl)piperidine-2,6-dione (35.1 mg, 0.044 mmol, 49% yield) was obtained as a white solid.

Exemplary Synthesis of Compound 202

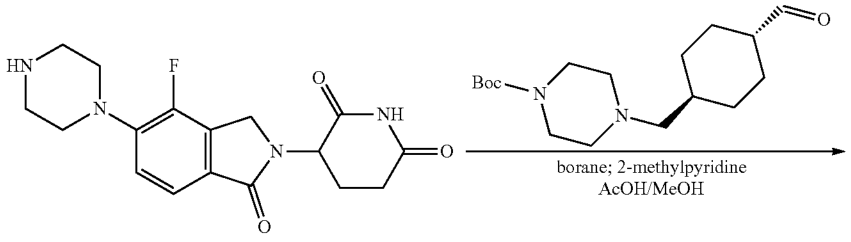

-continued

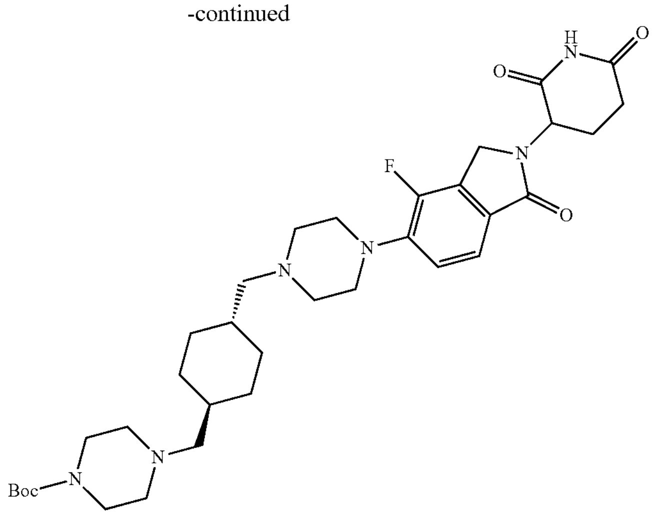

Step 1:

To a mixture of tert-butyl 4-[(4-formylcyclohexyl) methyl]piperazine-1-carboxylate (170 mg, 547.63 μmol, 1 eq) in MeOH (3 mL) and HOAc (0.5 mL) was added a solution of 3-(4-fluoro-1-oxo-5-piperazin-1-yl-isoindolin-2-yl)piperidine-2,6-dione (370 mg, 803.69 μmol, 1.47 eq, TFA) and DIEA (70.78 mg, 547.63 μmol, 95.38 uL, 1 eq) in MeOH (1 mL). Then borane; 2-methylpyridine (117.15 mg, 1.10 mmol, 2 eq) was added to above solution. After addition, the reaction solution was stirred at 20° C. for 12 h. LCMS showed the reaction completed. The reaction mixture was concentrated under reduced pressure to remove most of solvent. The residue was purified by prep.HPLC (column: Xtimate C18 150*40 mm*10 um; mobile phase: [water (0.05% $NH_3H_2O$)-ACN]; B %: 45%-75%, 10 min) to afford tert-butyl 4-[[4-[[4-[2-(2,6-dioxo-3-piperidyl)-4-fluoro-1-oxo-isoindolin-5-yl]piperazin-1-yl]methyl]cyclohexyl] methyl]piperazine-1-carboxylate (137 mg, 183.87 μmol, 33.58% yield, 86% purity) as a white solid.

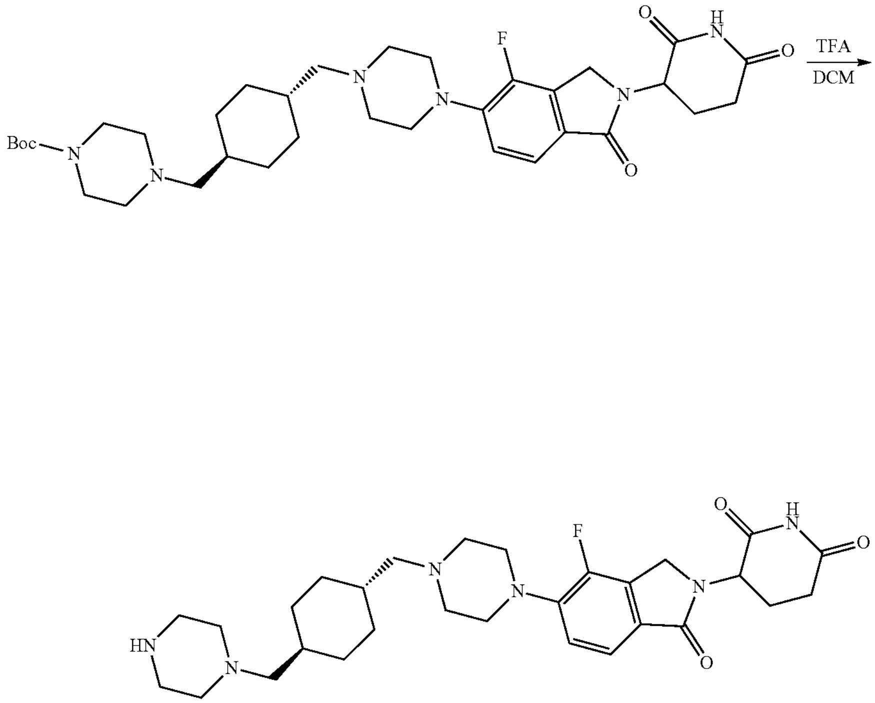

Step 2:

To a solution of tert-butyl 4-[[4-[[4-[2-(2,6-dioxo-3-piperidyl)-4-fluoro-1-oxo-isoindolin-5-yl]piperazin-1-yl]methyl]cyclohexyl]methyl]piperazine-1-carboxylate (157 mg, 245.01 μmol, 1 eq) in DCM (3 mL) was added TFA (27.94 mg, 245.01 μmol, 18.14 uL, 1 eq). After addition, the reaction solution was stirred at 20° C. for 1 hour. LCMS showed the reaction completed. The reaction mixture was concentrated under reduced pressure to remove solvent to afford 3-[4-fluoro-1-oxo-5-[4-[[4-(piperazin-1-ylmethyl)cyclohexyl]methyl]piperazin-1-yl]isoindolin-2-yl]piperidine-2,6-dione (180 mg, crude, TFA) as a brown solid. The crude product was used for next step directly.

4 hours. LCMS showed the reaction completed. The reaction mixture was diluted with water (10 mL) and extracted with dichloromethane (10 mL*3). The organic layer was dried over sodium sulfate and concentrated under reduced pressure. The residue was purified by prep.HPLC (column: Xtimate C18 100*30 mm*10 um; mobile phase: [water (0.225% FA)-ACN]; B %: 0%-30%, 40 min) to afford 3-[4-fluoro-5-[[4-[[4-[4-[6-[5-(1-methylcyclopropoxy)-1H-indazol-3-yl]pyrimidin-4-yl]piperazin-1-yl]methyl]cyclohexyl]methyl]piperazin-1-yl]-1-oxo-isoindolin-2-yl]piperidine-2,6-dione (29.9 mg, 36.71 μmol, 30.67% yield, 98.83% purity) as a light yellow solid.

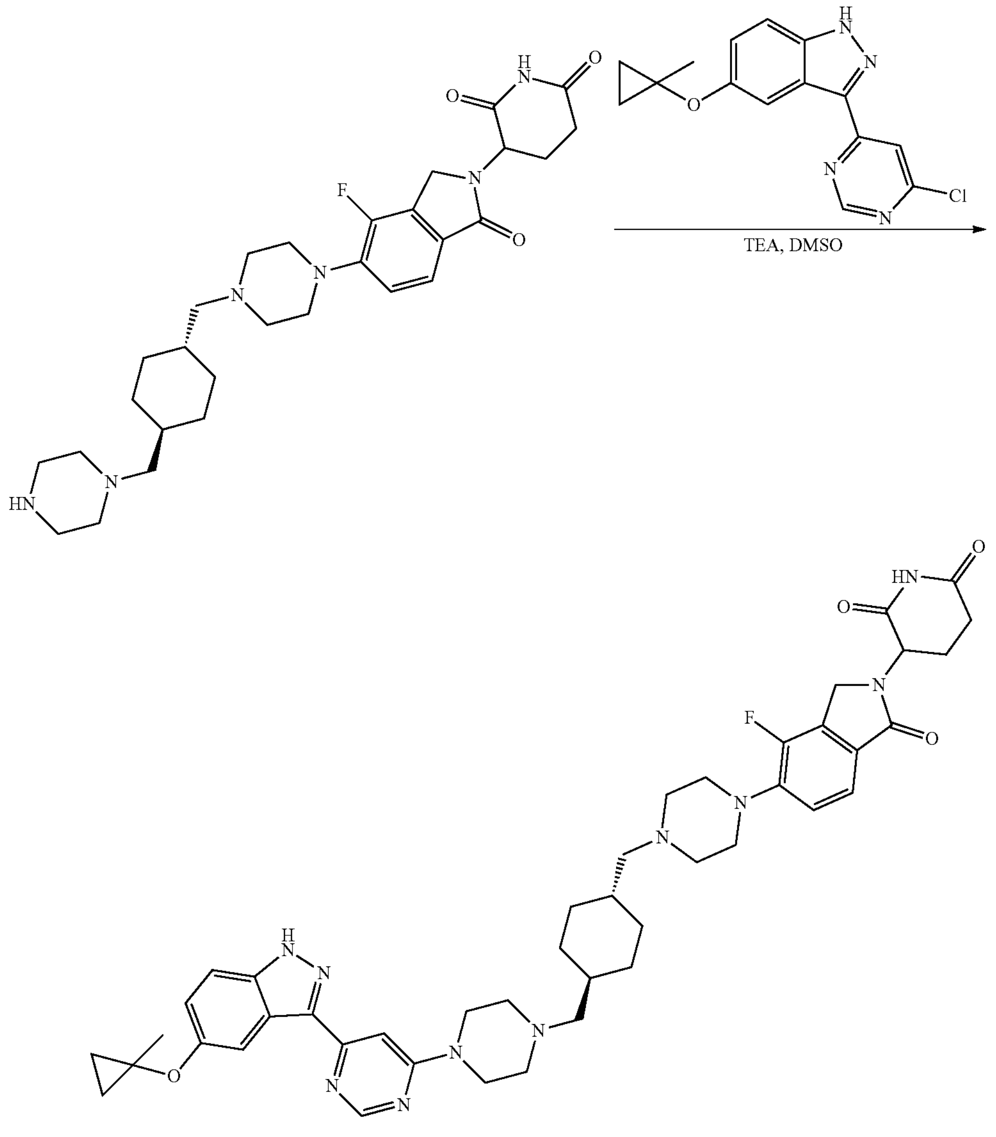

Step 3:

To a solution of 3-[4-fluoro-1-oxo-5-[4-[[4-(piperazin-1-ylmethyl)cyclohexyl]methyl]piperazin-1-yl]isoindolin-2-yl]piperidine-2,6-dione (90 mg, 137.47 μmol, 1.15 eq, TFA) and 3-(6-chloropyrimidin-4-yl)-5-(1-methylcyclopropoxy)-1H-indazole (36 mg, 119.70 μmol, 1 eq) in DMSO (2 mL) was added TEA (121.13 mg, 1.20 mmol, 166.61 uL, 10 eq). After addition, the reaction solution was stirred at 90° C. for Exemplary Synthesis of Compound 203

Compound 203 was prepared in a manner analogous to compound 202 using 3-(6-chloropyrimidin-4-yl)-6-fluoro-5-(1-methylcyclopropoxy)-1H-indazole in the final step.

Exemplary Synthesis of Compound 204

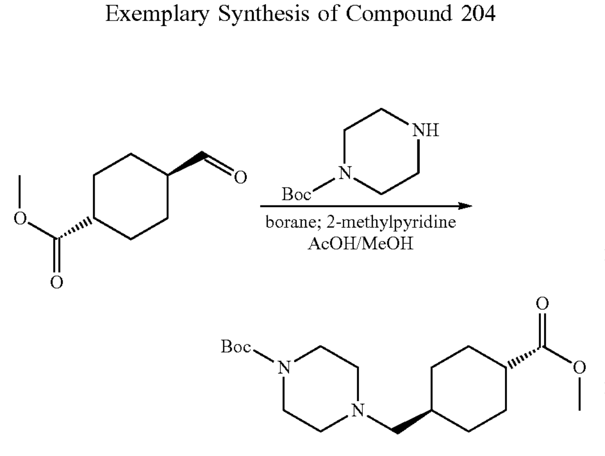

Step 1:

To a solution of methyl 4-formylcyclohexanecarboxylate (3 g, 17.63 mmol, 1 eq) and tert-butyl piperazine-1-carboxylate (3.28 g, 17.63 mmol, 1 eq) in MeOH (30 mL) and HOAc (3 mL) was added borane; 2-methylpyridine (3.77 g, 35.25 mmol, 2 eq). After addition, the reaction solution was stirred at 20° C. for 12 hours. TLC (petroleum ether:ethyl acetate=1:1) showed the reaction completed. The reaction mixture was concentrated under reduced pressure to remove most of solvent. The residue was purified by silica gel column chromatography (0 to 60% ethyl acetate in petroleum ether) to afford tert-butyl 4-[(4-methoxycarbonylcyclohexyl)methyl]piperazine-1-carboxylate (4 g, 11.75 mmol, 66.66% yield) as a colorless oil.

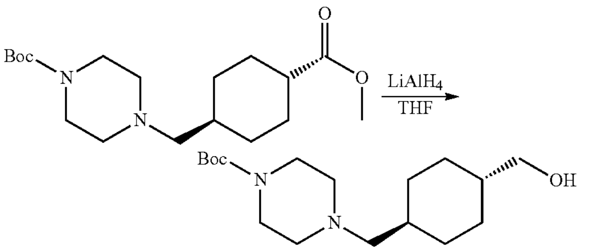

Step 2:

To a solution of tert-butyl 4-[(4-methoxycarbonylcyclohexyl)methyl]piperazine-1-carboxylate (4 g, 11.75 mmol, 1 eq) in THF (50 mL) was added $LiAlH_4$ (535.05 mg, 14.10 mmol, 1.2 eq) in portions under $N_2$ at 0° C. After addition, the reaction mixture was stirred at 0° C. for 1 hours. TLC (petroleum ether:ethyl acetate=0:1) showed the reaction completed. The reaction mixture was quenched by $H_2O$ (1 mL), followed by 15% aqueous NaOH (1 mL) and $H_2O$ (3 mL). After being stirred at room temperature for 0.5 hour, the solid was removed by filtration. The filtrate was concentrated to dryness to give crude product. The residue was purified by silica gel column chromatography (0 to 100% ethyl acetate in petroleum ether) to afford tert-butyl 4-[[4-(hydroxymethyl)cyclohexyl]methyl]piperazine-1-carboxylate (2.3 g, 7.36 mmol, 62.65% yield, 100% purity) as a colorless oil.

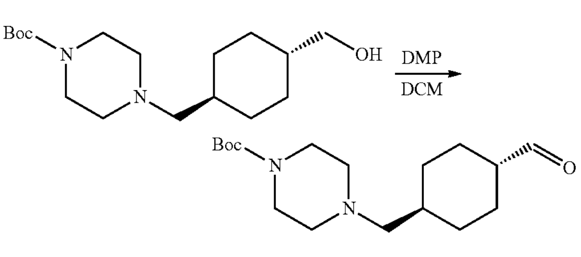

Step 3:

To a solution of tert-butyl 4-[[4-(hydroxymethyl)cyclohexyl]methyl]piperazine-1-carboxylate (220 mg, 704.12 μmol, 1 eq) in DCM (5 mL) was added DMP (597.29 mg, 1.41 mmol, 435.98 uL, 2 eq) under $N_2$ atmosphere. The mixture was stirred at 30° C. for 2 hours. TLC showed the starting material was consumed completely. The residue was poured into $NaHCO_3$ to adjusted the pH=7-8, and $Na_2SO_3$ (20 mL). The aqueous phase was extracted with DCM (30 mL*3). The combined organic phase was washed with brine (30 mL*2), dried with anhydrous $Na_2SO_4$, filtered and concentrated in vacuum to afford tert-butyl 4-[(4-formylcyclohexyl)methyl]piperazine-1-carboxylate (202 mg, 649.71 μmol, 92.27% yield, 99.846% purity) as a colorless oil.

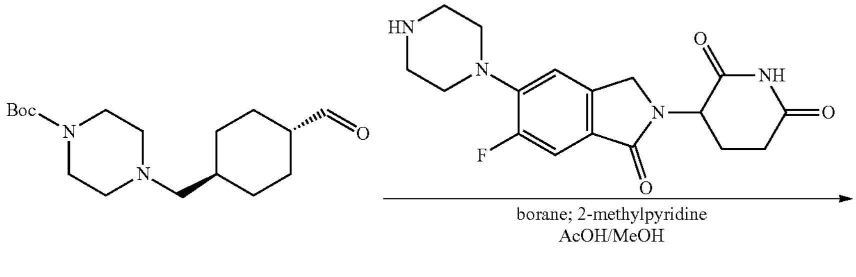

-continued

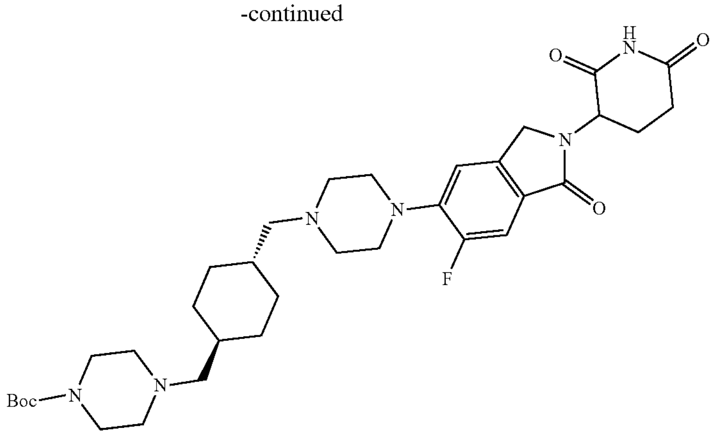

Step 4:

To a mixture of tert-butyl 4-[(4-formylcyclohexyl)methyl]piperazine-1-carboxylate (200 mg, 644.27 μmol, 1 eq) and 3-(6-fluoro-1-oxo-5-piperazin-1-yl-isoindolin-2-yl)piperidine-2,6-dione (223.15 mg, 644.27 μmol, 1 eq) in MeOH (10 mL) and AcOH (1 mL) added borane; 2-methylpyridine (137.82 mg, 1.29 mmol, 2 eq). The mixture was stirred at 40° C. for 16 hours. LCMS showed desired MS. The residue was poured into water (30 mL). The aqueous phase was extracted with ethyl acetate (30 mL*3). The combined organic phase was washed with brine (30 mL*2), dried with anhydrous $Na_2SO_4$, filtered and concentrated in vacuum. The residue was purified by prep.HPLC (column: Xtimate C18 100*30 mm*10 um; mobile phase: [water (0.225% FA)-ACN]; B %: 0%-20%, 40 min) to afford tert-butyl 4-[[4-[[4-[2-(2,6-dioxo-3-piperidyl)-6-fluoro-1-oxo-isoindolin-5-yl]piperazin-1-yl]methyl]cyclohexyl]methyl]piperazine-1-carboxylate (190 mg, 291.96 μmol, 45.32% yield, 98.465% purity) as a white solid.

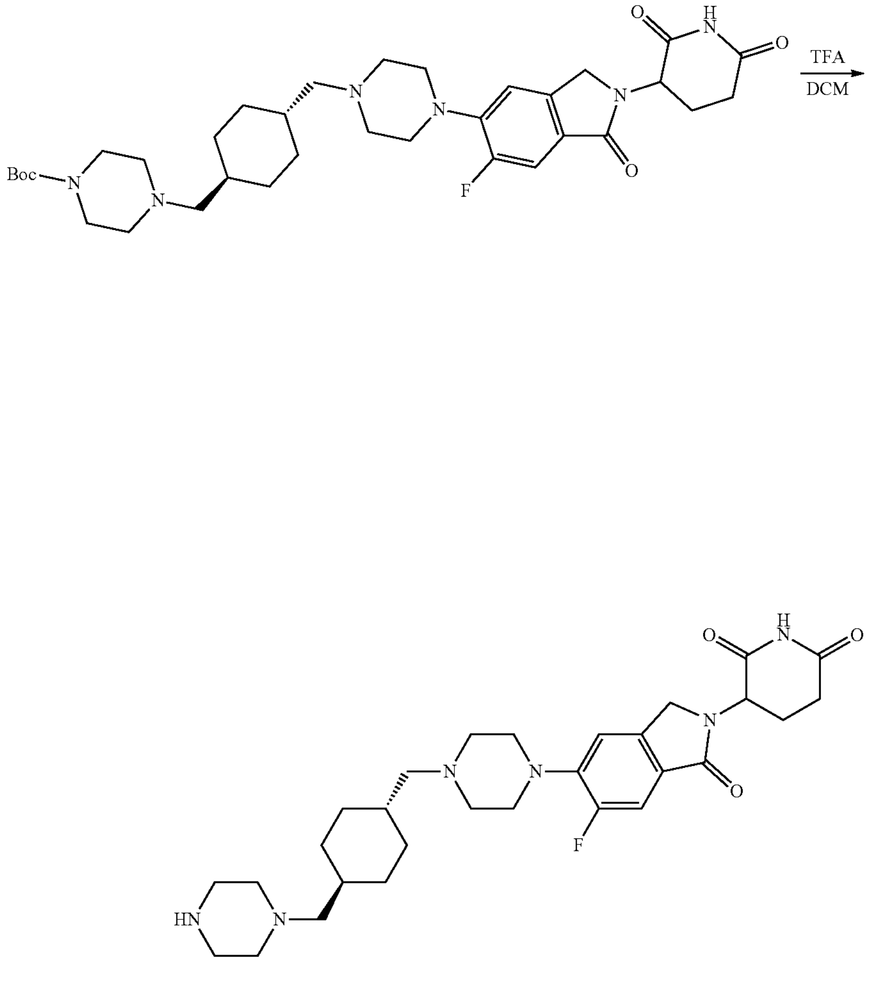

Step 5:

To a mixture of tert-butyl 4-[[4-[[4-[2-(2,6-dioxo-3-piperidyl)-6-fluoro-1-oxo-isoindolin-5-yl]piperazin-1-yl]methyl]cyclohexyl]methyl]piperazine-1-carboxylate (180 mg, 280.90 μmol, 1 eq) in DCM (2 mL) was added TFA (32.03 mg, 280.90 μmol, 20.80 uL, 1 eq). The mixture was stirred at 35° C. for 1 hour. LCMS showed there was desired MS. The residue was concentrated in vacuum to afford 3-[6-fluoro-1-oxo-5-[4-[[4-(piperazin-1-ylmethyl)cyclohexyl]methyl]piperazin-1-yl]isoindolin-2-yl]piperidine-2,6-dione (190 mg, crude, TFA) as a brown gum.

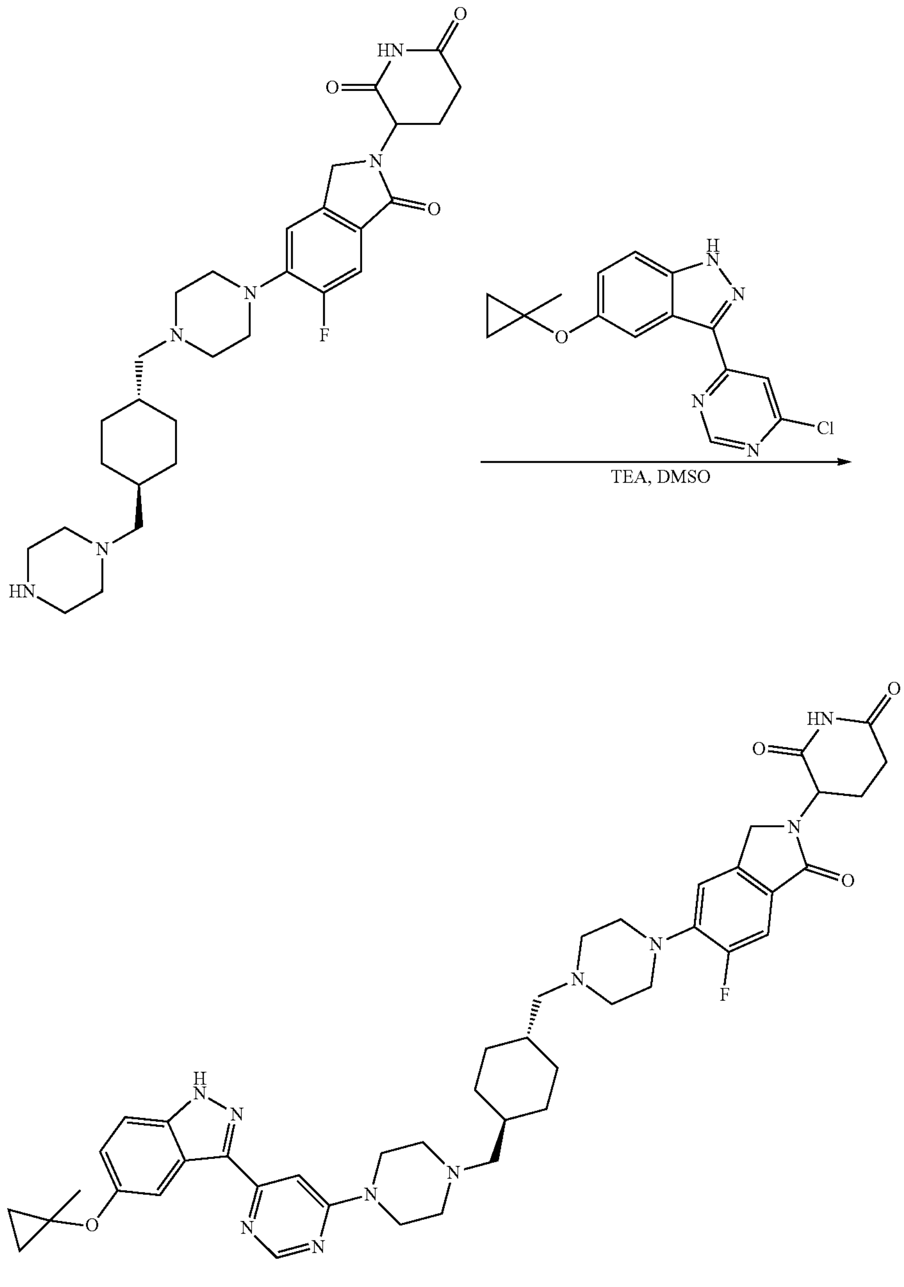 [SMILES: O=C1CCC(N2Cc3cc(N4CCN(C[C@H]5CC[C@H](CN6CCNCC6)CC5)CC4)c(F)cc3C2=O)C(=O)N1 ; CC1(Oc2ccc3[nH]nc(-c4cc(Cl)ncn4)c3c2)CC1 ; CC1(Oc2ccc3[nH]nc(-c4cc(N5CCN(C[C@H]6CC[C@H](CN7CCN(c8cc9c(cc8F)C(=O)N(C8CCC(=O)NC8=O)C9)CC7)CC6)CC5)ncn4)c3c2)CC1]

Step 6:

To a solution of 3-[6-fluoro-1-oxo-5-[4-[[4-(piperazin-1-ylmethyl)cyclohexyl]methyl]piperazin-1-yl]isoindolin-2-yl]piperidine-2,6-dione (75 mg, 138.72 μmol, 1 eq) and 3-(6-chloropyrimidin-4-yl)-5-(1-methylcyclopropoxy)-1H-indazole (41.72 mg, 138.72 μmol, 1 eq) in DMSO (2 mL) was added TEA (14.04 mg, 138.72 μmol, 19.31 uL, 1 eq). After addition, the mixture was stirred at 90° C. for 16 hours. LCMS showed there was desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.HPLC (column: Xtimate C18 100*30 mm*10 um; mobile phase: [water (0.225% FA)-ACN]; B %: 0%-35%, 40 min) to afford 3-[6-fluoro-5-[4-[[4-[[4-[6-[5-(1-methylcyclopropoxy)-1H-indazol-3-yl]pyrimidin-4-yl]piperazin-1-yl]methyl]cyclohexyl]methyl]piperazin-1-yl]-1-oxo-isoindolin-2-yl]piperidine-2,6-dione (31.8 mg, 39.40 μmol, 28.40% yield, 99.734% purity) as a white solid.

Exemplary Synthesis of Compound 205

Compound 205 was prepared in a manner analogous to compound 204 using 3-(6-chloropyrimidin-4-yl)-6-fluoro-5-(1-methylcyclopropoxy)-1H-indazole in the final step.

Exemplary Synthesis of Compound 206

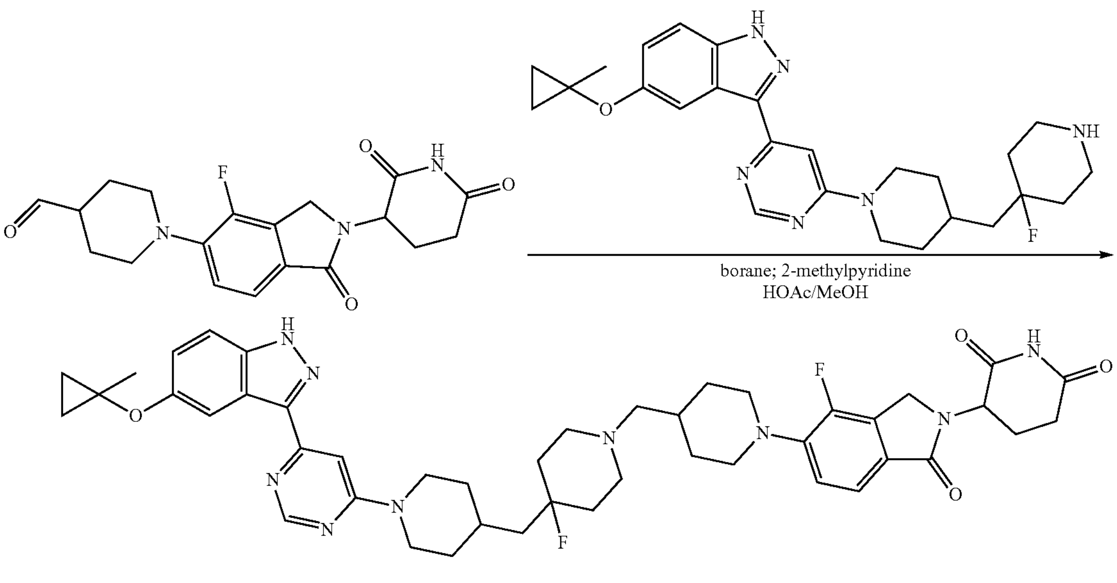

Step 1:

A mixture of 3-[6-[4-[(4-fluoro-4-piperidyl)methyl]-1-piperidyl]pyrimidin-4-yl]-5-(1-methylcyclopropoxy)-2H-indazole (70 mg, 150.67 μmol, 1 eq), 1-[2-(2,6-dioxo-3-piperidyl)-4-fluoro-1-oxo-isoindolin-5-yl]piperidine-4-carbaldehyde (56.26 mg, 150.67 μmol, 1 eq) in MeOH (10 mL) and AcOH (2 mL) was added borane; 2-methylpyridine (48.35 mg, 452.01 μmol, 3 eq) and then the mixture was stirred at 25° C. for 12 hours. LCMS showed desired MS. The reaction mixture was concentrated under reduced pressure to give a residue. The residue was purified by prep-HPLC (column: Xtimate C18 100*30 mm*10 um; mobile phase: [water (10 mM NH4HCO3)-ACN]; B %: 10%-80%, 40 min) to give 3-[4-fluoro-5-[4-[[4-fluoro-4-[[1-[6-[5-(1-methylcyclopropoxy)-1H-indazol-3-yl]pyrimidin-4-yl]-4-piperidyl]methyl]-1-piperidyl]methyl]-1-piperidyl]-1-oxo-isoindolin-2-yl]piperidine-2,6-dione (43.4 mg, 52.27 μmol, 34.69% yield, 99% purity) as a white solid.

Exemplary Synthesis of Compound 207

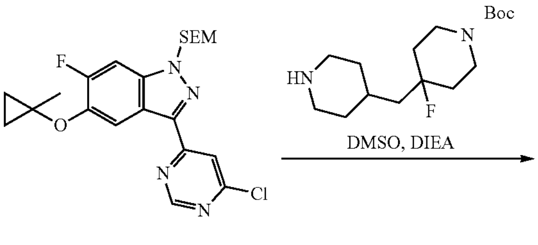

-continued

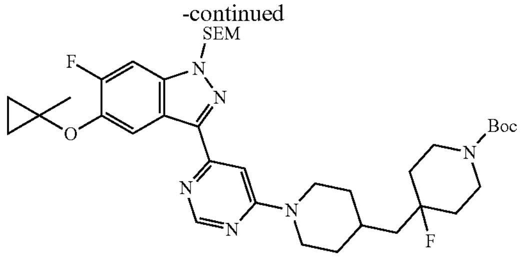

Step 1:

A mixture of tert-butyl 4-fluoro-4-(4-piperidylmethyl) piperidine-1-carboxylate (66.91 mg, 222.72 μmol, 1 eq), 2-[[3-(6-chloropyrimidin-4-yl)-6-fluoro-5-(1-methylcyclopropoxy)indazol-2-yl]methoxy]ethyl-trimethyl-silane (100 mg, 222.72 μmol, 1 eq) in DMSO (5 mL) was added DIEA (287.85 mg, 2.23 mmol, 387.94 uL, 10 eq), and then the mixture was stirred at 100° C. for 12 hours under $N_2$ atmosphere. LCMS showed desired MS. TLC (Petroleum ether:Ethyl acetate=3:1) showed one new major spot. The resulting product was poured into $H_2O$ (10 mL). The mixture was extracted with ethyl acetate (50 mL*3). The organic phase was washed with brine (50 mL), dried over anhydrous $Na_2SO_4$ concentrated in vacuum to give a residue. The residue was purified by silica gel column chromatography (0 to 27% Ethyl acetate in Petroleum ether) to give tert-butyl 4-fluoro-4-[[1-[6-[6-fluoro-5-(1-methylcyclopropoxy)-2-(2-trimethylsilylethoxymethyl)indazol-3-yl]pyrimidin-4-yl]-4-piperidyl]methyl]piperidine-1-carboxylate (100 mg, 129.04 μmol, 57.94% yield, 92% purity) as a yellow oil Step 2:

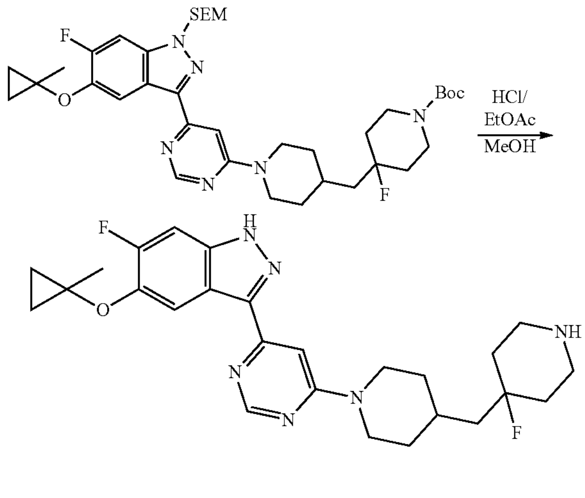

A mixture of tert-butyl 4-fluoro-4-[[1-[6-[6-fluoro-5-(1-methylcyclopropoxy)-2-(2-trimethylsilylethoxymethyl)indazol-3-yl]pyrimidin-4-yl]-4-piperidyl]methyl]piperidine-1-carboxylate (100 mg, 140.26 μmol, 1 eq), in MeOH (10 mL) was added HCl/EtOAc (4 M, 4 mL, 114.07 eq), and then the mixture was stirred at 25° C. for 2 hours under $N_2$ atmosphere. TLC (Petroleum ether:Ethyl acetate=3:1) showed one new major spot. The resulting product was concentrated in vacuum to give 6-fluoro-3-[6-[4-[(4-fluoro-4-piperidyl)methyl]-1-piperidyl]pyrimidin-4-yl]-5-(1-methylcyclopropoxy)-2H-indazole (70 mg, crude, HCl) as a yellow oil.

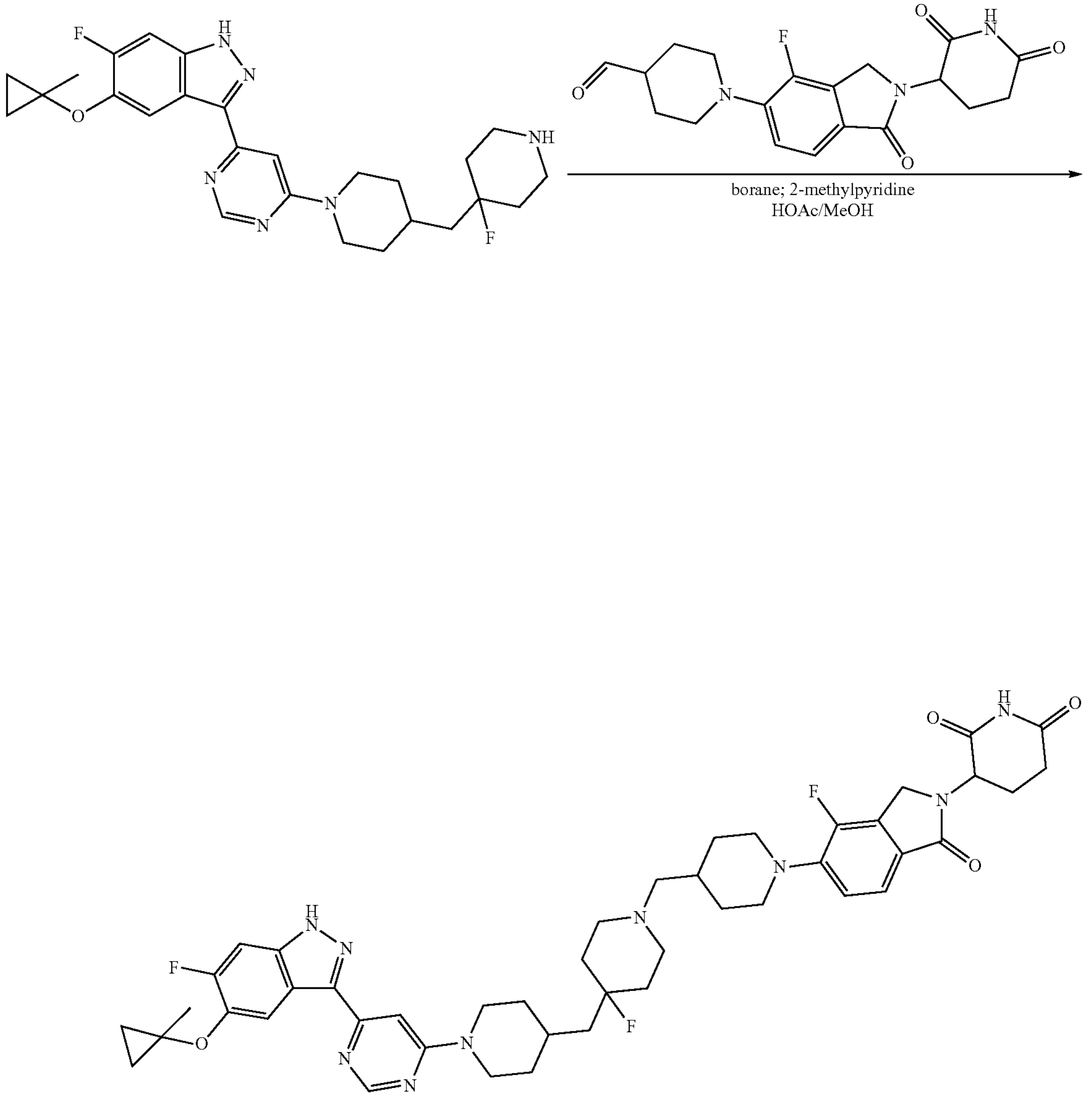

Step 3:

A mixture of 6-fluoro-3-[6-[4-[(4-fluoro-4-piperidyl) methyl]-1-piperidyl]pyrimidin-4-yl]-5-(1-methylcyclo-propoxy)-2H-indazole (40 mg, 82.89 μmol, 1 eq), 1-[2-(2,6-dioxo-3-piperidyl)-4-fluoro-1-oxo-isoindolin-5-yl] piperidine-4-carbaldehyde (30.95 mg, 82.89 μmol, 1 eq) in MeOH (10 mL) and AcOH (2 mL) was added borane; 2-methylpyridine (26.60 mg, 248.67 μmol, 3 eq) and then the mixture was stirred at 25° C. for 12 hours. LCMS showed desired MS. The reaction mixture was filtered and concentrated under reduced pressure to give a residue. The residue was purified by prep-HPLC (column: Xtimate C18 100*30 mm*10 um; mobile phase: [water (0.225% FA)-ACN]; B %: 0%-35%, 40 minutes) to give 3-[4-fluoro-5-[4-[[4-fluoro-4-[[1-[6-[6-fluoro-5-(1-methylcyclopropoxy)-1H-indazol-3-yl]pyrimidin-4-yl]-4-piperidyl]methyl]-1-piperidyl]methyl]-1-piperidyl]-1-oxo-isoindolin-2-yl] piperidine-2,6-dione (31.5 mg, 36.75 μmol, 44.34% yield, 98% purity) as a white solid.

Exemplary Synthesis of Compound 208

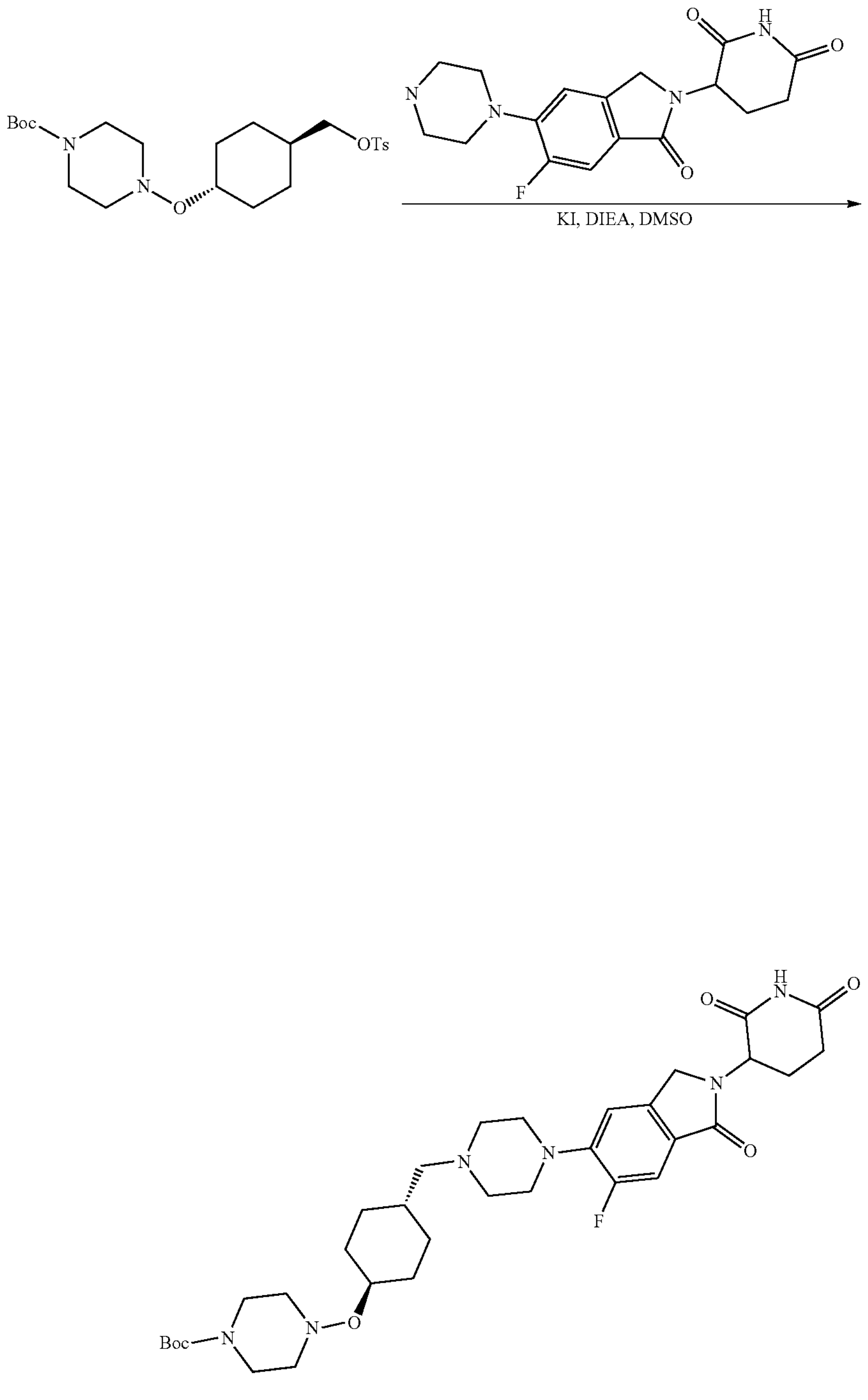

Step 1:

To a solution of 3-(6-fluoro-1-oxo-5-piperazin-1-yl-isoindolin-2-yl)piperidine-2,6-dione (300 mg, 866.16 μmol, 1 eq) and tert-butyl 4-[4-(p-tolylsulfonyloxymethyl)cyclohexoxy] piperidine-1-carboxylate (486.04 mg, 1.04 mmol, 1.2 eq) in $CH_3CN$ (5 mL) was added KI (1.44 g, 8.66 mmol, 10 eq) and DIEA (1.12 g, 8.66 mmol, 1.51 mL, 10 eq), then the mixture was stirred at 90° C. for 16 hours. LCMS showed 77.4% desire compound and TLC (Petroleum ether:Ethyl acetate=0:1, UV=254 nm) showed a new spot formed. The reaction mixture was concentrated under reduced pressure to give a residue. The residue was purified by flash silica gel chromatography (ISCO®; 20 g SepaFlash® Silica Flash Column, Eluent of 0-95% Ethyl acetate/Petroleum ethergradient @ 50 mL/minute). Compound tert-butyl 4-[4-[[4-[2-(2,6-dioxo-3-piperidyl)-6-fluoro-1-oxo-isoindolin-5-yl]piperazin-1-yl]methyl]cyclohexoxy]piperidine-1-carboxylate (0.7 g, crude) was obtained as a light yellow solid.

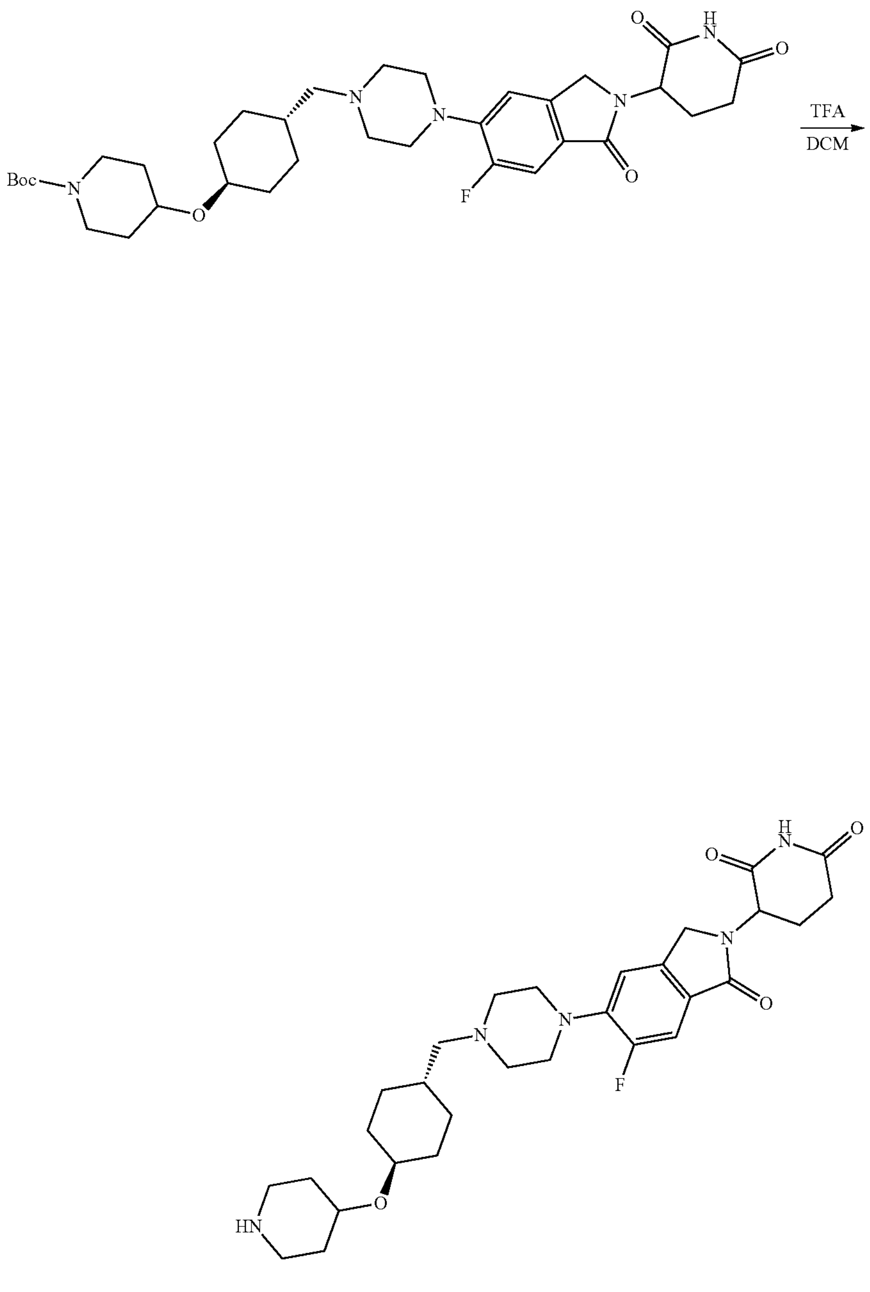

Step 2:

To a solution of tert-butyl 4-[4-[[4-[2-(2,6-dioxo-3-piperidyl)-6-fluoro-1-oxo-isoindolin-5-yl]piperazin-1-yl]methyl]cyclohexoxy]piperidine-1-carboxylate (350 mg, 545.37 μmol, 1 eq) in DCM (3 mL) was added TFA (1.54 g, 13.51 mmol, 1 mL, 24.77 eq), then the mixture was stirred at 25° C. for 2 hour. TLC (Dichloromethane:Methanol=10:1, UV=254 nm) showed a new spot formed. The reaction mixture was concentrated under reduced pressure to give a residue. Compound 3-[6-fluoro-1-oxo-5-[4-[[4-(4-piperidyloxy)cyclohexyl]methyl]piperazin-1-yl]isoindolin-2-yl]piperidine-2,6-dione (357 mg, 376.23 μmol, 68.99% yield, 69.1% purity, TFA) was obtained as a light yellow oil.

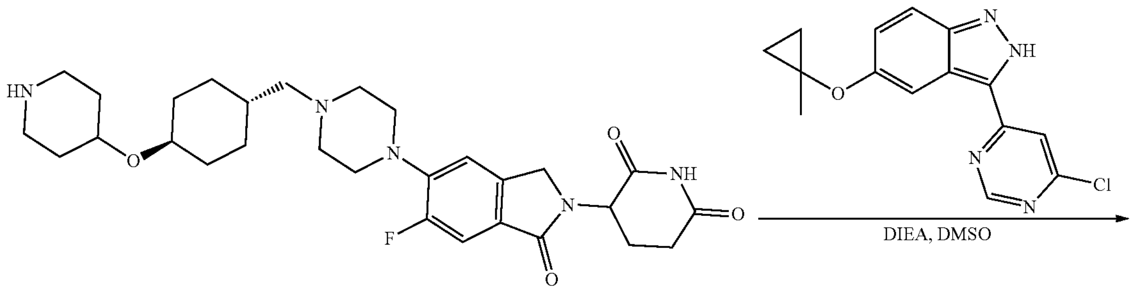

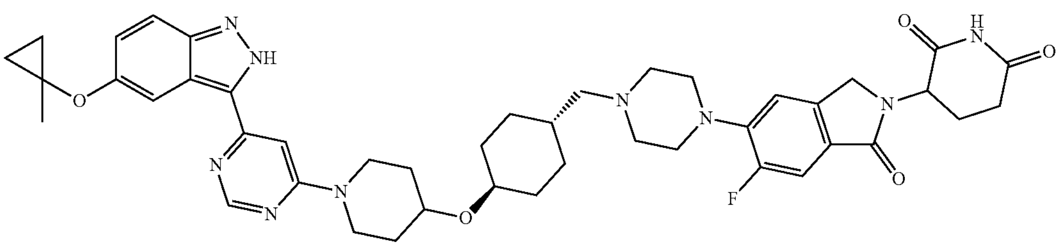

Step 3:

To a solution of 3-(6-chloropyrimidin-4-yl)-5-(1-methylcyclopropoxy)-2H-indazole (60 mg, 199.51 μmol, 1 eq) and 3-[6-fluoro-1-oxo-5-[4-[[4-(4-piperidyloxy)cyclohexyl]methyl]piperazin-1-yl]isoindolin-2-yl]piperidine-2,6-dione (170.06 mg, 259.36 μmol, 1.3 eq, TFA) in DMSO (5 mL) was added DIEA (128.92 mg, 997.53 μmol, 173.75 uL, 5 eq), then the solution was stirred at 90° C. for 16 hours. LCMS showed ~30% desire compound and the starting materials was consumed completely. The residue was purified by prep-HPLC (column: Xtimate C18 100*30 mm*10 um; mobile phase: [water (0.225% FA)-ACN]; B %: 0%-40%, 40 min). Compound 3-[6-fluoro-5-[4-[[4-[[1-[6-[5-(1-methylcyclopropoxy)-2H-indazol-3-yl]pyrimidin-4-yl]-4-piperidyl]oxy]cyclohexyl]methyl]piperazin-1-yl]-1-oxo-isoindolin-2-yl]piperidine-2,6-dione (17.6 mg, 20.80 μmol, 10.43% yield, 95.262% purity) was obtained as a white solid.

Exemplary Synthesis of Compound 209

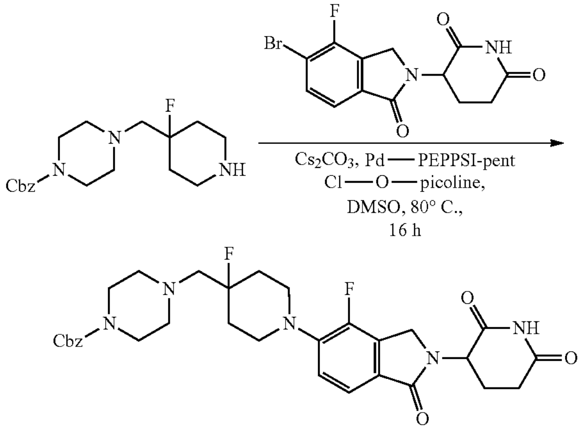

Step 1:

To a solution of benzyl 4-[(4-fluoro-4-piperidyl)methyl]piperazine-1-carboxylate (350 mg, 941.17 μmol, 1.28 eq, HCl) and 3-(5-bromo-4-fluoro-1-oxo-isoindolin-2-yl)piperidine-2,6-dione (250 mg, 732.85 μmol, 1 eq) in DMSO (5 mL) was added Pd-PEPPSI-pent Cl—O-picoline (39.79 mg, 73.29 μmol, 0.1 eq) and Cs2CO3 (477.56 mg, 1.47 mmol, 2 eq) under $N_2$. After addition, the mixture was stirred at 80° C. for 16 hours under N2. LCMS showed there was desired MS. The residue was filtered and concentrated in vacuum. The residue was purified by silica gel chromatography (12 g, 0-100% (20 minutes) of Ethyl acetate in Petroleum ether, 100% (10 minutes) of Ethyl acetate in Petroleum ether) to afford benzyl 4-[[1-[2-(2,6-dioxo-3-piperidyl)-4-fluoro-1-oxo-isoindolin-5-yl]-4-fluoro-4-piperidyl]methyl]piperazine-1-carboxylate (130 mg, 96.56 μmol, 13.18% yield, 44.242% purity) as a white solid.

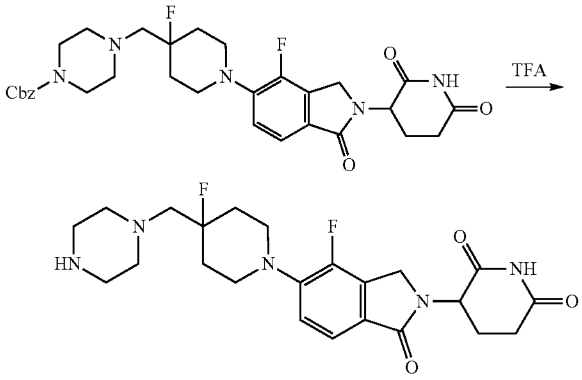

Step 2:

To a mixture of benzyl 4-[[1-[2-(2,6-dioxo-3-piperidyl)-4-fluoro-1-oxo-isoindolin-5-yl]-4-fluoro-4-piperidyl]methyl]piperazine-1-carboxylate (130 mg, 218.25 μmol, 1 eq) was added TFA (3.08 g, 27.01 mmol, 2 mL, 123.76 eq). The mixture was stirred at 70° C. for 1 hour. TLC showed the reaction was completed. The residue was concentrated in vacuum to afford 3-[4-fluoro-5-[4-fluoro-4-(piperazin-1-ylmethyl)-1-piperidyl]-1-oxo-isoindolin-2-yl]piperidine-2,6-dione (130 mg, crude, TFA) as a brown gum.

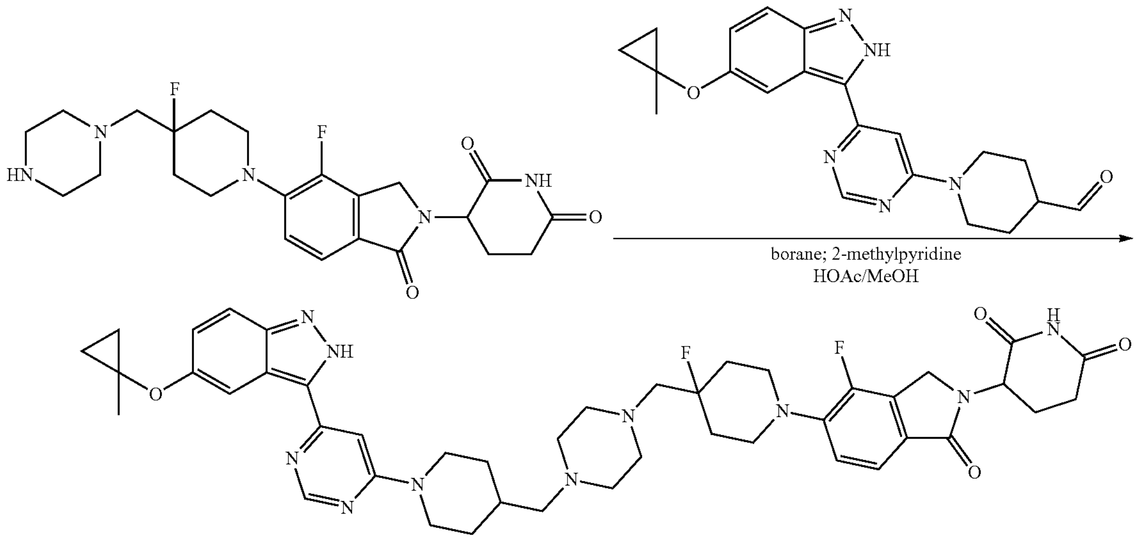

Step 3:

To a solution of 3-[4-fluoro-5-[4-fluoro-4-(piperazin-1-ylmethyl)-1-piperidyl]-1-oxo-isoindolin-2-yl]piperidine-2,6-dione (100 mg, 216.68 μmol, 1 eq) and 1-[6-[5-(1-methylcyclopropoxy)-2H-indazol-3-yl]pyrimidin-4-yl] piperidine-4-carbaldehyde (81.78 mg, 216.68 μmol, 1 eq) in MeOH (10 mL) and AcOH (1 mL) was added borane; 2-methylpyridine (46.35 mg, 433.37 μmol, 2 eq). After addition, the mixture was stirred at 20° C. for 16 hours. LCMS showed desired MS. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by prep.HPLC (column: 3_Phenomenex Luna C18 75*30 mm*3 um; mobile phase: [water (0.225% FA)-ACN]; B %: 0%-35%, 40 min) to afford 3-[4-fluoro-5-[4-fluoro-4-[[4-[[1-[6-[5-(1-methylcyclopropoxy)-2H-indazol-3-yl]pyrimidin-4-yl]-4-piperidyl]methyl]piperazin-1-yl]methyl]-1-piperidyl]-1-oxo-isoindolin-2-yl]piperidine-2,6-dione (40 mg, 47.65 μmol, 21.99% yield, 98.028% purity) as a white solid.

Exemplary Synthesis of Compound 210

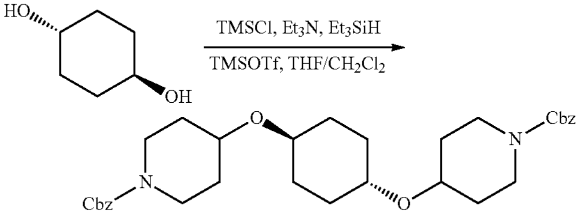

Step 1:

To a solution of cyclohexane-1,4-diol (4.2 g, 36.16 mmol, 1.00 eq) in tetrahydrofuran (80 mL) was added Triethylamine (8.42 g, 83.16 mmol, 2.30 eq) and chloro(trimethyl) silane (8.64 g, 79.55 mmol, 2.20 eq) at 0° C., and the reaction mixture was stirred at 25° C. for 0.5 hour. The reaction mixture was filtered and the filtrate was concentrated under reduced pressure to give a residue. Then to a stirred solution of above residue and benzyl 4-oxopiperidine-1-carboxylate (25.30 g, 108.47 mmol, 3.00 eq) in dichloromethane (80 mL) was added triethylsilane (14.72 g, 126.55 mmol, 3.50 eq) and trimethylsilyl trifluoromethanesulfonate (12.05 g, 54.24 mmol, 1.50 eq) dropwise at −60° C., and the reaction mixture was stirred at 25° C. under nitrogen for 12 hours. The reaction mixture was diluted with water 100 mL and extracted with dichloromethane (100 mL×2). The combined organic layers were dried over anhydrous sodium sulfate, filtered and concentrated under reduced pressure to give a residue. The residue was purified by semi-preparative reverse phase HPLC (70-90% acetonitrile+0.225% formic acid in water, 20 minutes). Compound benzyl 4-[4-[(1-benzyloxycarbonyl-4-piperidyl)oxy]cyclohexoxy]piperidine-1-carboxylate (5.3 g, 9.62 mmol, 26% yield) was obtained as a white solid.

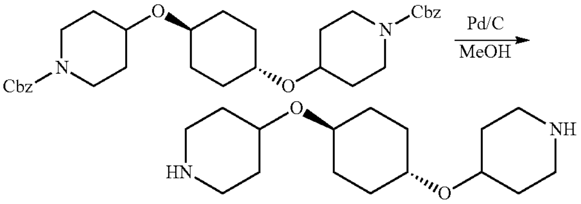

Step 2:

To a solution of benzyl 4-[4-[(1-benzyloxycarbonyl-4-piperidyl)oxy]cyclohexoxy]piperidine-1-carboxylate (5.3 g, 9.62 mmol, 1.00 eq) in methanol (100 mL) was added palladium on activated carbon catalyst (1.0 g, 9.62 mmol, 10% purity, 1.00 eq) and ammonium hydroxide (0.1 mL, 25% purity) under nitrogen atmosphere. The suspension was degassed and purged with hydrogen for 3 times. The mixture was stirred under hydrogen (15 Psi) at 25° C. for 2 hours. The reaction mixture was filtered and concentrated under reduced pressure to give 4-[4-(4-piperidyloxy)cyclohexoxy] piperidine (2.6 g, 9.21 mmol, 95% yield) as a white solid

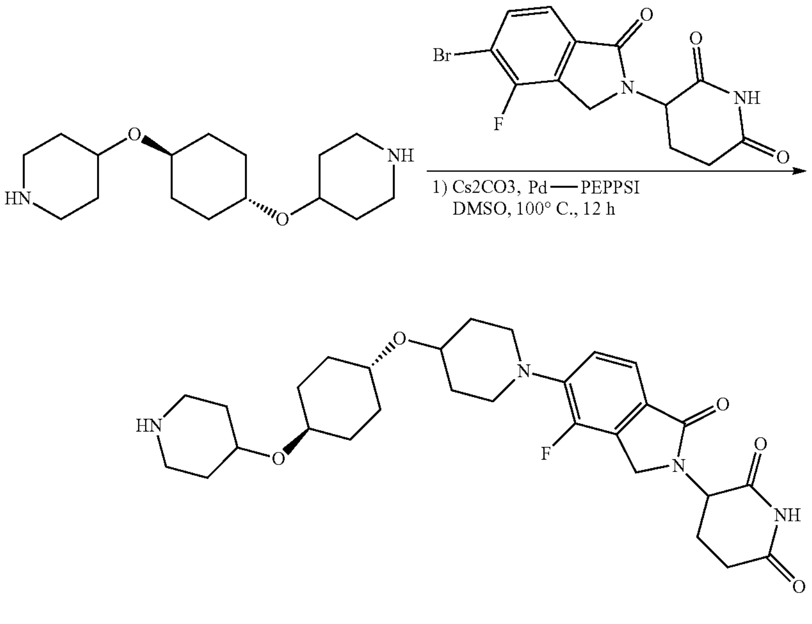

Step 3:

To a solution of 4-[4-(4-piperidyloxy)cyclohexoxy]piperidine (700 mg, 2.48 mmol, 1.97 eq) and 3-(5-bromo-4-fluoro-1-oxo-isoindolin-2-yl)piperidine-2,6-dione (430 mg, 1.26 mmol, 1.00 eq) in dimethylsulfoxide (7 mL) was added cesium carbonate (821 mg, 2.52 mmol, 2.00 eq) and 1,3-bis[2,6-bis(1-ethylpropyl)phenyl]-2H-imidazole; 3-chloropyridine;dichloropalladium (100 mg, 0.12 mmol, 0.10 eq) under nitrogen. The mixture was stirred at 100° C. for 12 hours under nitrogen. The reaction mixture was filtered to give a black liquid. Then the liquid was purified by semi-preparative reverse phase HPLC (9-39% acetonitrile+0.1% trifluoroacetic acid in water, 11 minutes). Compound 3-[4-fluoro-1-oxo-5-[4-[4-(4-piperidyloxy)cyclohexoxy]-1-piperidyl]isoindolin-2-yl]piperidine-2,6-dione (80 mg, 0.12 mmol, 9% yield, trifluoroacetic acid salt) was obtained as a white solid.

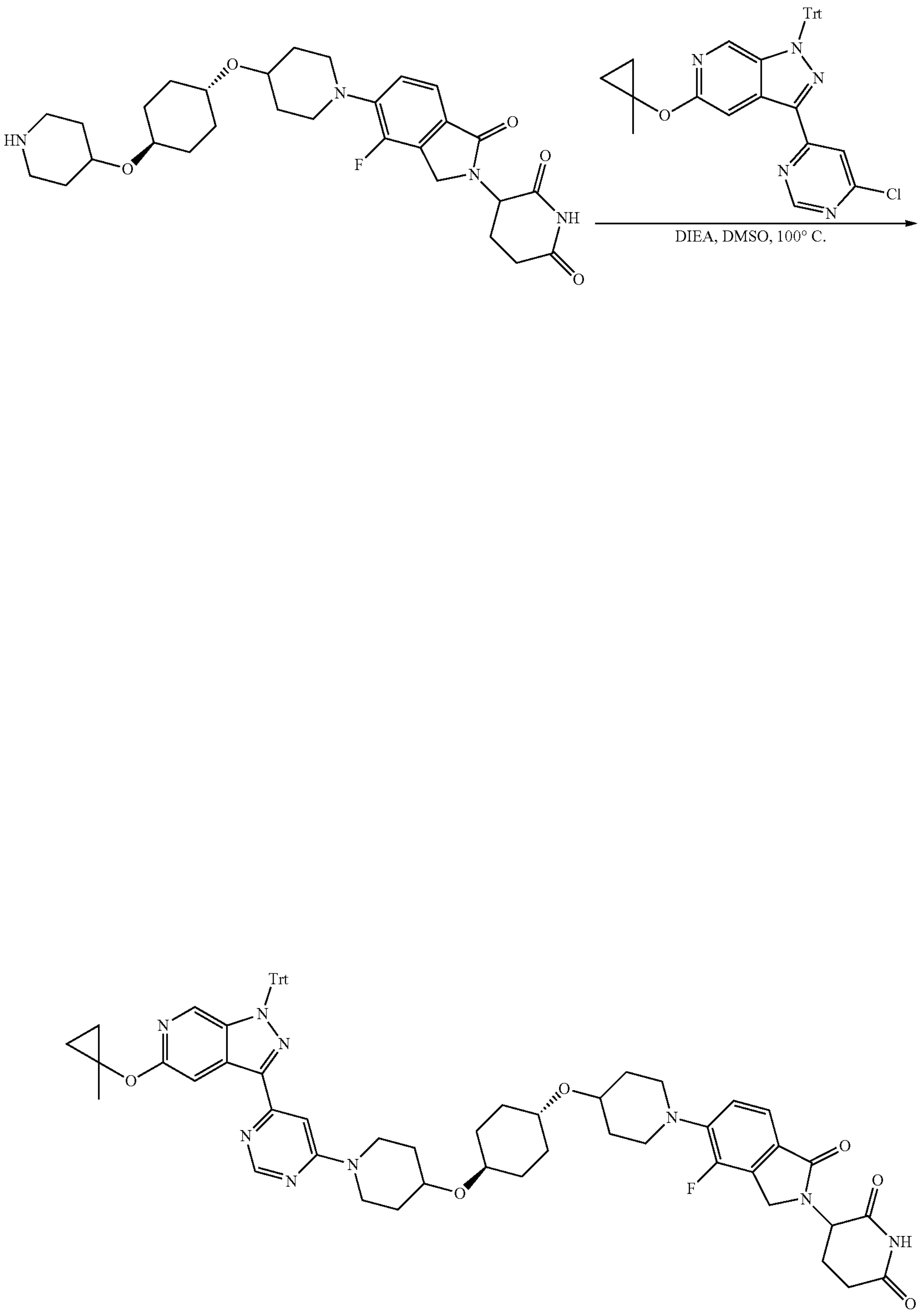

Step 4:

To a solution of 3-[4-fluoro-1-oxo-5-[4-[4-(4-piperidyloxy)cyclohexoxy]-1-piperidyl]isoindolin-2-yl]piperidine-2,6-dione (40 mg, 0.06 mmol, 1.00 eq, trifluoroacetic acid salt) and 3-(6-chloropyrimidin-4-yl)-5-(1-methylcyclopropoxy)-1-trityl-pyrazolo[3,4-c]pyridine (33 mg, 0.06 mmol, 1.00 eq) in dimethylsulfoxide (1 mL) was added N,N-diisopropylethylamine (23 mg, 0.18 mmol, 3.00 eq). The mixture was stirred at 100° C. for 0.5 hour. The reaction mixture was diluted with dichloromethane 20 mL, and washed with saturated ammonium chloride solution, dried over anhydrous sodium sulfate, filtered and concentrated under reduced pressure to give 3-[4-fluoro-5-[4-[4-[[1-[6-[5-(1-methylcyclopropoxy)-1-trityl-pyrazolo[3,4-c]pyridin-3-yl]pyrimidin-4-yl]-4-piperidyl]oxy]cyclohexoxy]-1-piperidyl]-1-oxo-isoindolin-2-yl]piperidine-2,6-dione (63 mg, 0.06 mmol, 98% yield) as a white solid.

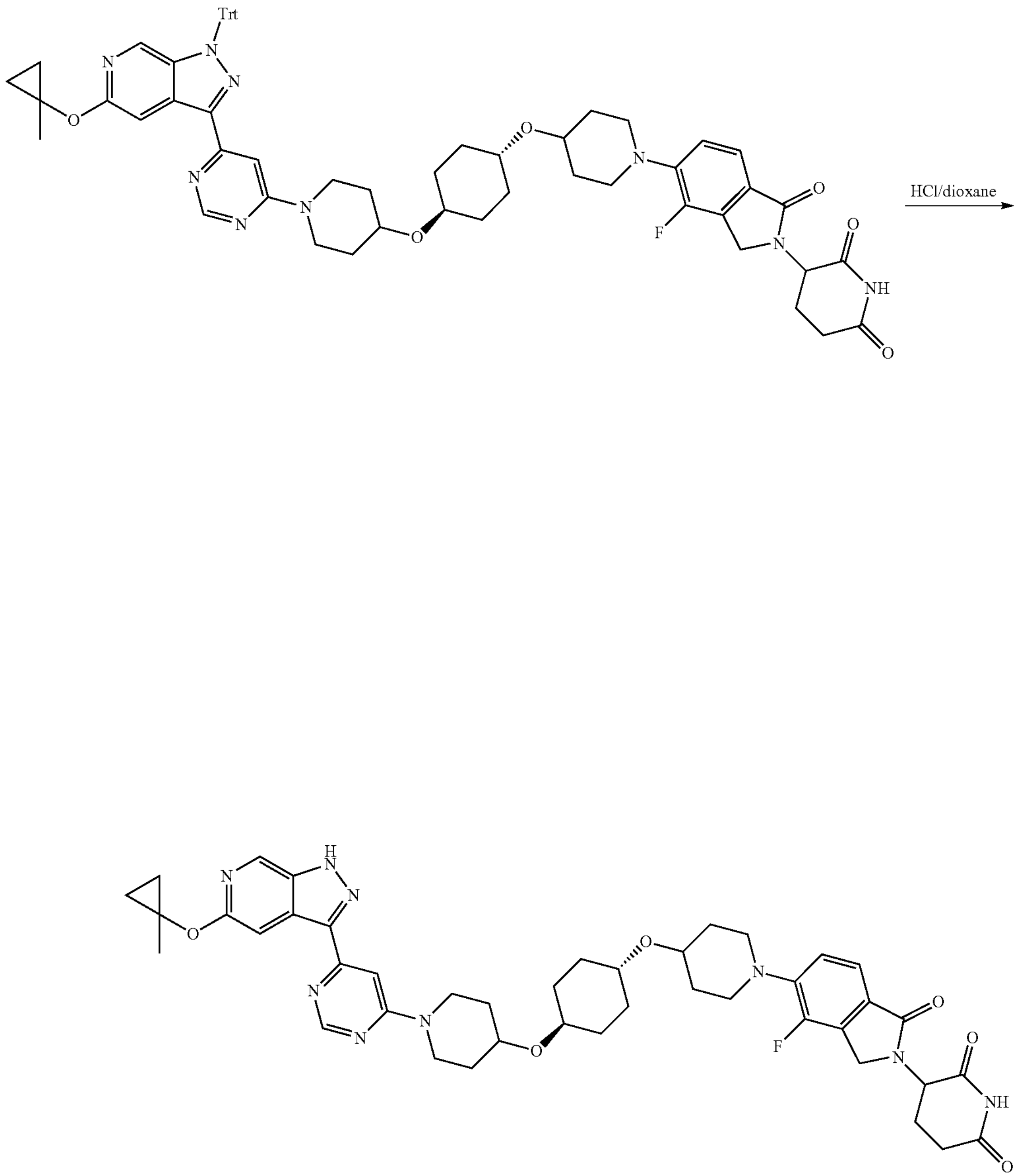

Step 5:

To a solution of 3-[4-fluoro-5-[4-[4-[[1-[6-[5-(1-methylcyclopropoxy)-1-trityl-pyrazolo[3,4-c]pyridin-3-yl]pyrimidin-4-yl]-4-piperidyl]oxy]cyclohexoxy]-1-piperidyl]-1-oxo-isoindolin-2-yl]piperidine-2,6-dione (63 mg, 0.06 mmol, 1.00 eq) in hydrogen chloride/dioxane (4 M, 1.5 mL, 100 eq) was added water (0.3 mL). The mixture was stirred at 25° C. for 1 hour. The reaction mixture was concentrated under reduced pressure to give a residue. The residue was purified by semi-preparative reverse phase HPLC (28-58% acetonitrile+0.225% formic acid in water, 7 min). Compound 3-[4-fluoro-5-[4-[4-[[1-[6-[5-(1-methylcyclopropoxy)-1H-pyrazolo[3,4-c]pyridin-3-yl]pyrimidin-4-yl]-4-piperidyl]oxy]cyclohexoxy]-1-piperidyl]-1-oxo-isoindolin-2-yl]piperidine-2,6-dione (18.0 mg, 0.02 mmol, 34% yield, 97% purity, formic acid salt) was obtained as an off-white solid.

Exemplary Synthesis of Compound 211

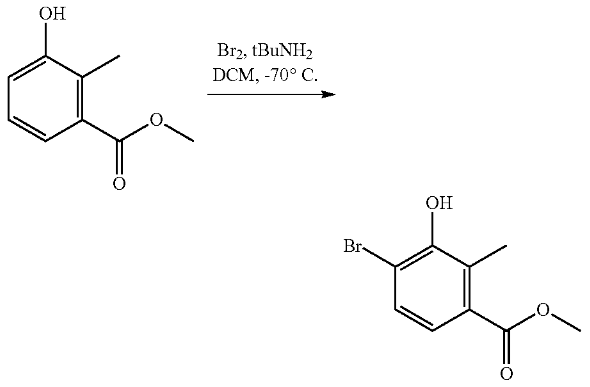

Step 1:

To a solution of 2-methylpropan-2-amine (8.80 g, 120.36 mmol, 12.65 mL, 1 eq) in DCM (50 mL) at −70° C. was added a solution of $Br_2$ (19.23 g, 120.36 mmol, 6.20 mL, 1 eq) in DCM (50 mL) dropwise and the mixture was stirred at −70° C. for 1 hour. A solution of methyl 3-hydroxy-2-methyl-benzoate (20 g, 120.36 mmol, 1 eq) in DCM (200 mL) was then added dropwise and the resulting mixture allowed to warm to 20° C. and stirred for 8 hours. TLC (petroleum ether:ethyl acetate=5:1) indicated the reaction was consumed completely. The mixture was quenched with water (100 mL), extracted with DCM (500 mL), washed with brine (500 mL), dried over $Na_2SO_4$, and concentrated under reduced pressure. It was purified by silica gel chromatography (0-3% EtOAc in Petroleum ether) to afford methyl 4-bromo-3-hydroxy-2-methyl-benzoate (7.77 g, 31.71 mmol, 26.34% yield) as a yellow solid.

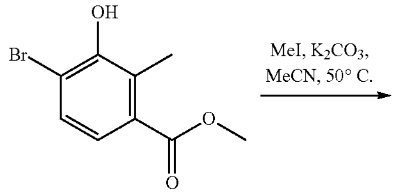

-continued

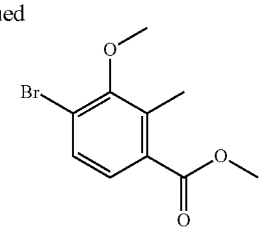

Step 2:

To a solution of methyl 4-bromo-3-hydroxy-2-methyl-benzoate (7.77 g, 31.71 mmol, 1 eq) in MeCN (70 mL) was added MeI (13.50 g, 95.12 mmol, 5.92 mL, 3 eq) and $K_2CO_3$ (5.26 g, 38.05 mmol, 1.2 eq). The mixture was stirred at 50° C. for 5 hours. TLC (Petroleum ether:Ethyl acetate=20:1) indicated the reaction was consumed completely. The mixture was quenched with water (10 mL), extracted with EtOAc (50 mL), washed with brine (50 mL), dried over $Na_2SO_4$, and concentrated under reduced pressure. It was purified by silica gel chromatography (0-3% EtOAc in Petroleum ether) to afford methyl 4-bromo-3-methoxy-2-methyl-benzoate (7.44 g, 28.72 mmol, 90.57% yield) as yellow oil.

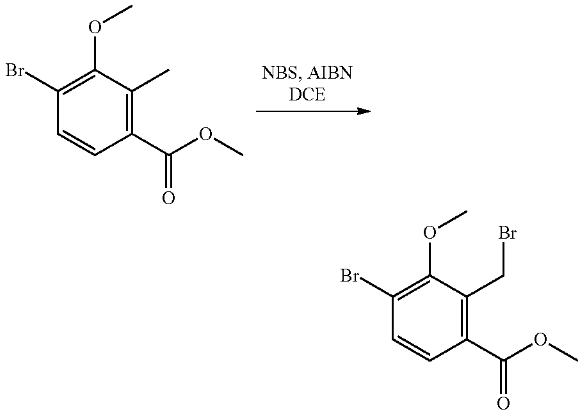

Step 3:

To a stirred solution of methyl 4-bromo-3-methoxy-2-methyl-benzoate (2 g, 7.72 mmol, 1 eq) in DCE (10 mL) under an atmosphere of nitrogen was added NBS (1.65 g, 9.26 mmol, 1.2 eq) followed by 2-[(E)-(1-cyano-1-methyl-ethyl)azo]-2-methyl-propanenitrile (63.38 mg, 385.96 μmol, 0.05 eq) and the resulting mixture was stirred vigorously at 80° C. for 1 hour to give yellow solution. The reaction mixture was concentrated under reduced pressure. The residue was purified by silica gel chromatography (10% of Ethyl acetate in Petroleum ether) to give methyl 4-bromo-2-(bromomethyl)-3-methoxy-benzoate (2.3 g, 6.80 mmol, 88.16% yield) as a yellow oil.

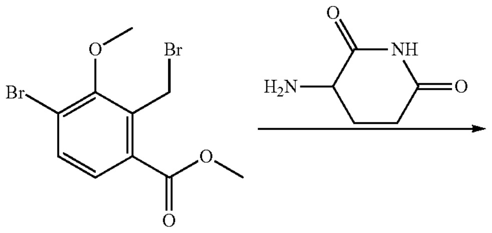

-continued

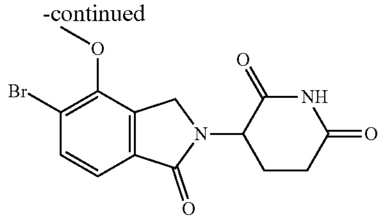

Step 4:

To a mixture of methyl 4-bromo-2-(bromomethyl)-3-methoxy-benzoate (2.3 g, 6.80 mmol, 1 eq) and 3-aminopiperidine-2,6-dione (1.34 g, 8.17 mmol, 1.2 eq, HCl) in DMF (10 mL) was added DIEA (4.40 g, 34.02 mmol, 5.93 mL, 5 eq) in one portion at 20° C. under $N_2$. The mixture was stirred at 85° C. for 48 hours. LCMS showed there was desired MS. The crude was concentrated in vacuum. The crude product was triturated with MeCN (20 mL) and $H_2O$ (20 mL) at 20° C. The crude was filtered and solid was concentrated in vacuum to give 3-(5-bromo-4-methoxy-1-oxo-isoindolin-2-yl)piperidine-2,6-dione (2 g, 5.66 mmol, 83.22% yield) as a dark gray solid

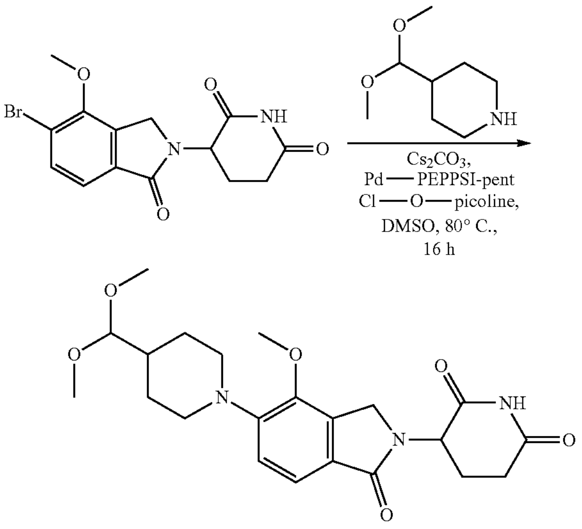

Step 5:

To a solution of 3-(5-bromo-4-methoxy-1-oxo-isoindolin-2-yl)piperidine-2,6-dione (500 mg, 1.42 mmol, 1 eq) and 4-(dimethoxymethyl)piperidine (450.85 mg, 2.83 mmol, 2 eq) in DMF (5 mL) was added $Cs_2CO_3$ (922.57 mg, 2.83 mmol, 2 eq) and Pd-PEPPSI-pent Cl—O-picoline (121.76 mg, 141.58 μmol, 0.1 eq). After addition, the reaction mixture was stirred at 80° C. under $N_2$ for 12 hours. LCMS (EB16-1785-P1A1) showed the desired MS. The mixture was cooled to 20° C. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by silica gel chromatography (0-100% (10 min) of Ethyl acetate in Petroleum ether, 100% (10 min) of Ethyl acetate in Petroleum ether) to give 3-[5-[4-(dimethoxymethyl)-1-piperidyl]-4-methoxy-1-oxo-isoindolin-2-yl]piperidine-2,6-dione (120 mg, 183.55 μmol, 12.97% yield, 66% purity) as yellow solid.

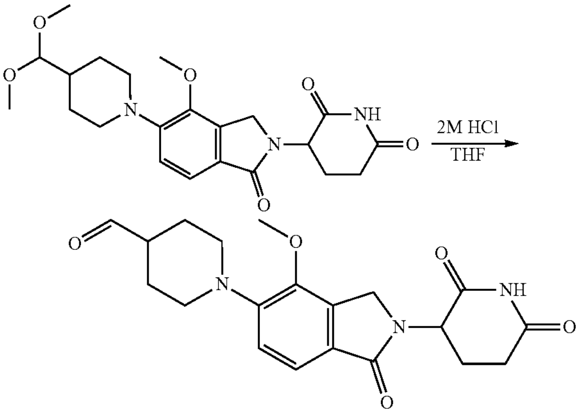

Step 6:

To a mixture of 3-[5-[4-(dimethoxymethyl)-1-piperidyl]-4-methoxy-1-oxo-isoindolin-2-yl]piperidine-2,6-dione (170.00 mg, 393.99 μmol, 1 eq) in THF (5 mL) was added HCl (2 M, 3.17 mL, 16.10 eq) in one portion at 20° C. under $N_2$. The mixture was stirred at 20° C. for 1 hour to give yellow solution. LCMS showed there was desired MS. The residue was poured into saturated $NaHCO_3$ to adjusted the pH=7-8. The aqueous phase was extracted with ethyl acetate (20 mL*3). The combined organic phase was washed with brine (20 mL*2), dried with anhydrous $Na_2SO_4$, filtered and concentrated in vacuum to give 1-[2-(2,6-dioxo-3-piperidyl)-4-methoxy-1-oxo-isoindolin-5-yl]piperidine-4-carbaldehyde (140 mg, 247.01 μmol, 62.69% yield, 68% purity) as a yellow solid.

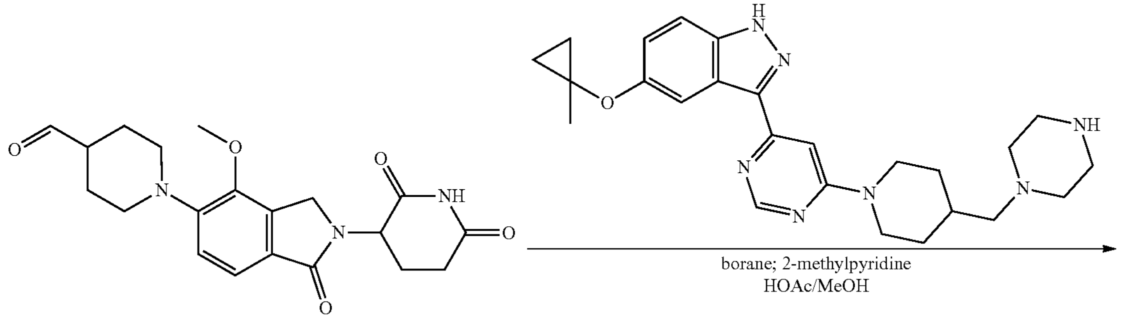

-continued

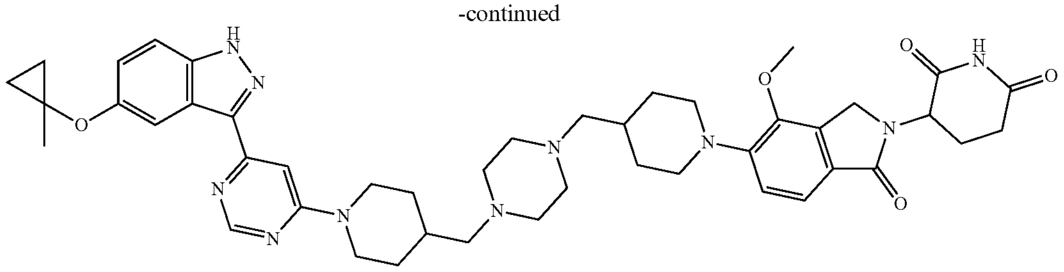

Step 7:

To a mixture of 5-(1-methylcyclopropoxy)-3-[6-[4-(piperazin-1-ylmethyl)-1-piperidyl]pyrimidin-4-yl]-2H-indazole (55.28 mg, 123.50 μmol, 1 eq) and 1-[2-(2,6-dioxo-3-piperidyl)-4-methoxy-1-oxo-isoindolin-5-yl]piperidine-4-carbaldehyde (70.00 mg, 123.50 μmol, 68% purity, 1 eq) in MeOH (10 mL) was added borane; 2-methylpyridine (26.42 mg, 247.01 μmol, 2 eq) and HOAc (7.42 mg, 123.50 μmol, 7.06 uL, 1 eq) in one portion at 20° C. under $N_2$. The mixture was stirred at 20° C. for 2 hours to give yellow solution. LCMS showed there was desired MS. The resulting product was poured into $H_2O$ (20 mL). The mixture was extracted with ethyl acetate (20 mL*3). The organic phase was washed with brine (15 mL*2), dried over anhydrous $Na_2SO_4$, concentrated in vacuum to give a residue. The residue was purified by prep-HPLC (column: Xtimate C18 100*30 mm*10 um; mobile phase: [water (0.225% FA)-ACN]; B %: 0%-40%, 40 min) to give 3-[4-methoxy-5-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (58.8 mg, 71.69 μmol, 58.05% yield, 99.61% purity, FA) as a white solid.

Exemplary Synthesis of Compound 212

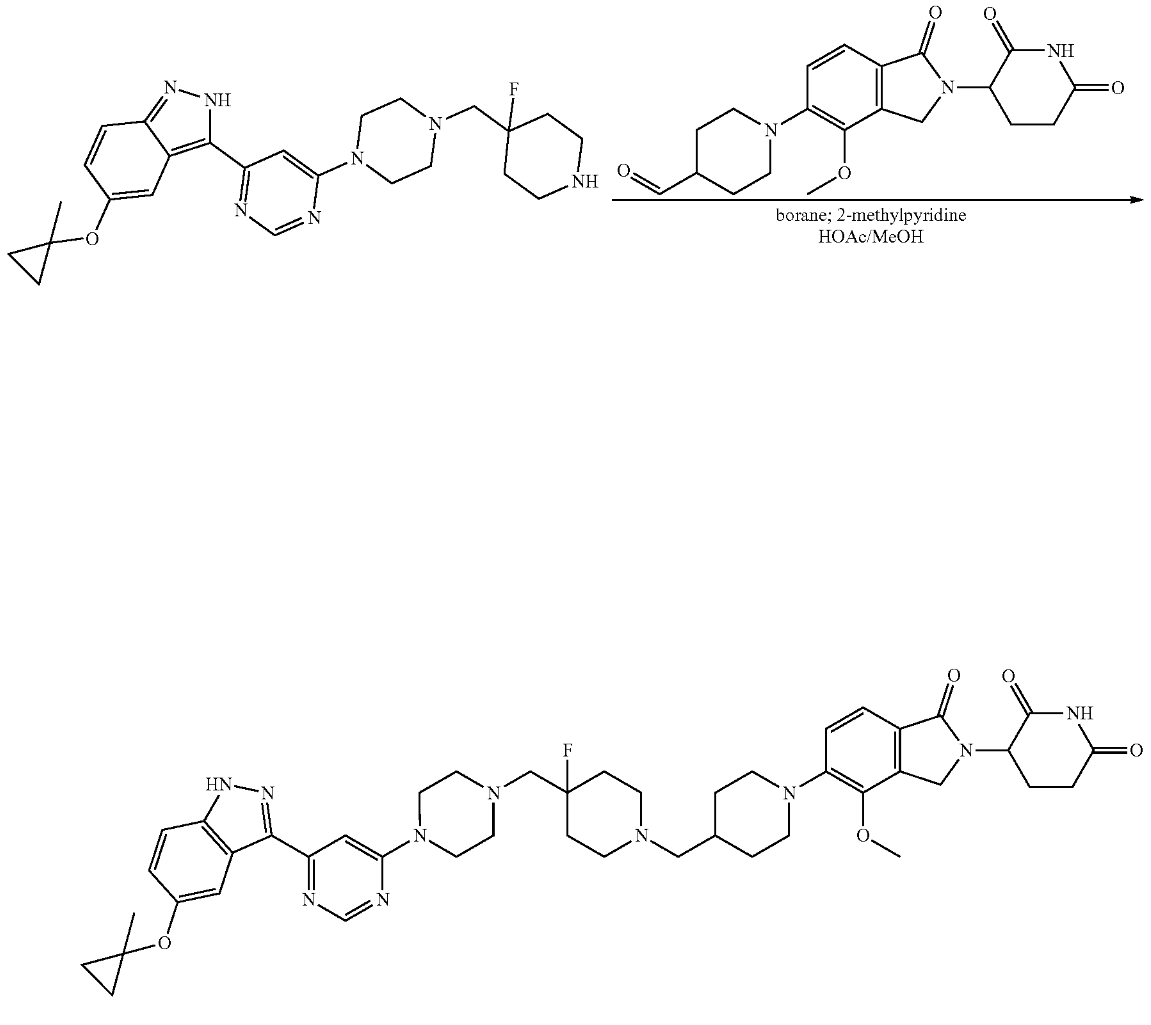

Step 1:

To a mixture of 3-[6-[4-[(4-fluoro-4-piperidyl)methyl]piperazin-1-yl]pyrimidin-4-yl]-5-(1-methylcyclopropoxy)-2H-indazole (57.50 mg, 123.50 μmol, 1 eq) and 1-[2-(2,6-dioxo-3-piperidyl)-4-methoxy-1-oxo-isoindolin-5-yl]piperidine-4-carbaldehyde (70.00 mg, 123.50 μmol, 68% purity, 1 eq) in MeOH (10 mL) was added borane; 2-methylpyridine (26.42 mg, 247.01 μmol, 2 eq) and HOAc (7.42 mg, 123.50 μmol, 7.06 uL, 1 eq) in one portion at 20° C. under $N_2$. The mixture was stirred at 20° C. for 10 hours to give yellow solution. LCMS showed there was desired MS. The resulting product was poured into $H_2O$ (20 mL). The mixture was extracted with ethyl acetate (20 mL*3). The organic phase was washed with brine (15 mL*2), dried over anhydrous $Na_2SO_4$, concentrated in vacuum to give a residue. The residue was purified by prep-HPLC (column: Xtimate C18 100*30 mm*10 um; mobile phase: [water (0.225% FA)-ACN]; B %: 0%-35%, 40 minutes) to give 3-[5-[4-[[4-fluoro-4-[[4-[6-[5-(1-methylcyclopropoxy)-1H-indazol-3-yl]pyrimidin-4-yl]piperazin-1-yl]methyl]-1-piperidyl]methyl]-1-piperidyl]-4-methoxy-1-oxo-isoindolin-2-yl]piperidine-2,6-dione (46.7 mg, 53.25 μmol, 43.12% yield, 95.21% purity, FA) as a white solid.

Exemplary Synthesis of Compound 213

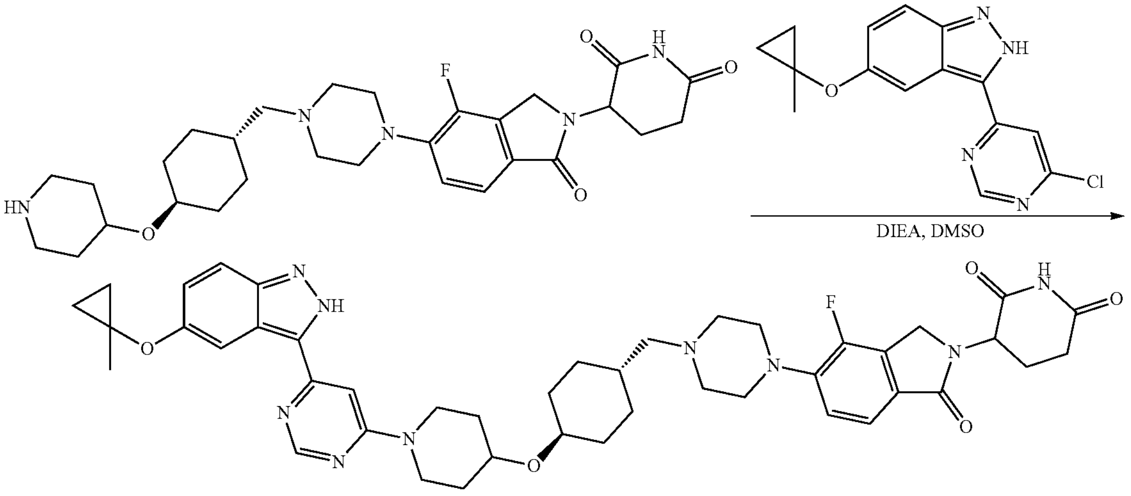

Step 1:

A mixture of 3-[4-fluoro-1-oxo-5-[4-[[4-(4-piperidyloxy)cyclohexyl]methyl]piperazin-1-yl]isoindolin-2-yl]piperidine-2,6-dione (252.15 mg, 465.51 μmol, 1 eq), 3-(6-chloropyrimidin-4-yl)-5-(1-methylcyclopropoxy)-2H-indazole (140 mg, 465.51 μmol, 1 eq) in DMSO (5 mL) was added DIEA (300.82 mg, 2.33 mmol, 405.42 uL, 5 eq), and then the mixture was stirred at 80° C. for 12 hours under $N_2$ atmosphere. LCMS showed desired MS. The resulting product was poured into $H_2O$ (10 mL). The mixture was extracted with ethyl acetate (50 mL*3). The organic phase was washed with brine (50 mL), dried over anhydrous $Na_2SO_4$ concentrated in vacuum to give a residue. The residue was purified by prep-HPLC (column: Xtimate C18 150*40 mm*10 um; mobile phase: [water (FA)-ACN]; B %: 10%-40%, 10 min) to give 3-[4-fluoro-5-[4-[[4-[[1-[6-[5-(1-methylcyclopropoxy)-2H-indazol-3-yl]pyrimidin-4-yl]-4-piperidyl]oxy]cyclohexyl]methyl]piperazin-1-yl]-1-oxo-isoindolin-2-yl]piperidine-2,6-dione (88.6 mg, 107.74 μmol, 23.14% yield, 98% purity) as a white solid.

Exemplary Synthesis of Compound 214

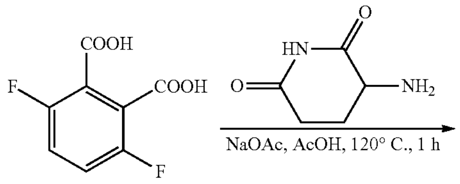

-continued

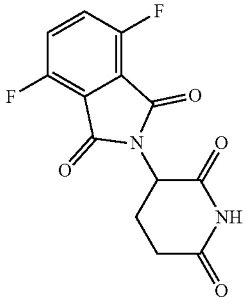

Step 1:

To a solution of 3,6-difluorophthalic acid (1.5 g, 7.42 mmol, 1 eq) and 3-aminopiperidine-2,6-dione (1.83 g, 11.13 mmol, 1.5 eq, HCl) in HOAc (20 mL) was added NaOAc (1.83 g, 22.26 mmol, 3 eq), then stirred at 120° C. for 1 h.

LCMS showed the reaction was complete. The reaction mixture was poured into water (50 mL), then filtered and the filtered cake was washed with water (20 mL×3), then concentrated to give crude product, then the crude product was triturated by methyl tert-butyl ether (26 mL), then concentrated to give a residue. The residue was used into next step directly without further purification. The product 2-(2,6-dioxo-3-piperidyl)-4,7-difluoro-isoindoline-1,3-dione (1.88 g, crude) as brown solid.

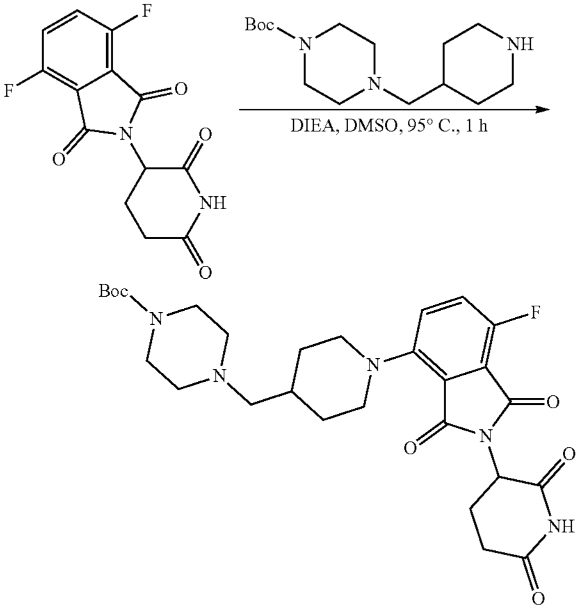

Step 2:

To a solution of 2-(2,6-dioxo-3-piperidyl)-4,7-difluoro-isoindoline-1,3-dione (2.18 g, 7.41 mmol, 1 eq) and tert-butyl 4-(4-piperidylmethyl)piperazine-1-carboxylate (2.10 g, 7.41 mmol, 1 eq) in DMSO (10 mL) was added DIEA (2.87 g, 22.23 mmol, 3.87 mL, 3 eq), then stirred at 95° C. for 1 h. LCMS showed the reaction was completed. The reaction mixture was acidified by formic acid until pH 5~6, then poured into water (10 mL). The aqueous phase was extracted with ethyl acetate (20 mL*2). The combined organic phase was washed with brine (5 mL*2), dried with anhydrous $Na_2SO_4$, filtered and concentrated in vacuum. The residue was purified by silica gel chromatography (Petroleum ether/Ethyl acetate=0/1) to afford tert-butyl 4-[[1-[2-(2,6-dioxo-3-piperidyl)-7-fluoro-1,3-dioxo-isoindolin-4-yl]-4-piperidyl]methyl]piperazine-1-carboxylate (2.6 g, 4.57 mmol, 61.67% yield, 98% purity) as yellow solid.

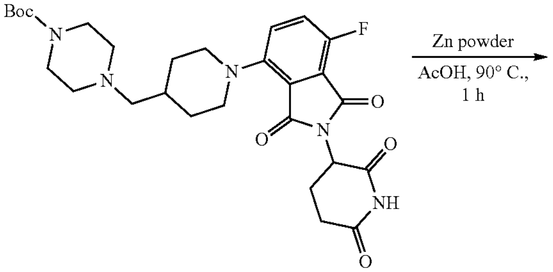

-continued

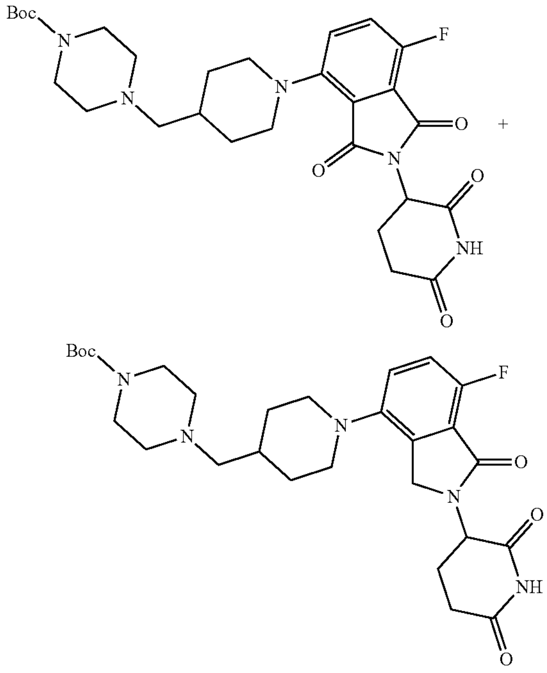

Step 3:

To a solution of tert-butyl 4-[[1-[2-(2,6-dioxo-3-piperidyl)-7-fluoro-1,3-dioxo-isoindolin-4-yl]-4-piperidyl]methyl]piperazine-1-carboxylate (2.5 g, 4.48 mmol, 1 eq) in HOAc (36 mL) was added Zn (11.5 g, 175.87 mmol, 39.23 eq). The mixture was stirred at 90° C. for 3 h. LCMS showed the reaction was completed. The reaction mixture was filtered and the filtrate was concentrated to give a residue, then water (60 mL) was added followed by saturated sodium bicarbonate aqueous solution (100 mL), the mixture was then extracted with ethyl acetate (80 mL×3). The combined organic layers were washed with brine (40 mL), dried over anhydrous sodium sulfate, filtered and concentrated in vacuum to give a residue. The residue was purified by prep-HPLC (YMC Triart C18 250*50 mm*7 um; mobile phase: [water (0.225% FA)-ACN]; B %: 5%-35%, 20 min) to afford tert-butyl 4-[[1-[2-(2,6-dioxo-3-piperidyl)-7-fluoro-1-oxo-isoindolin-4-yl]-4-piperidyl]methyl]piperazine-1-carboxylate (440 mg, 809.38 μmol, 18.05% yield) as gray solid.

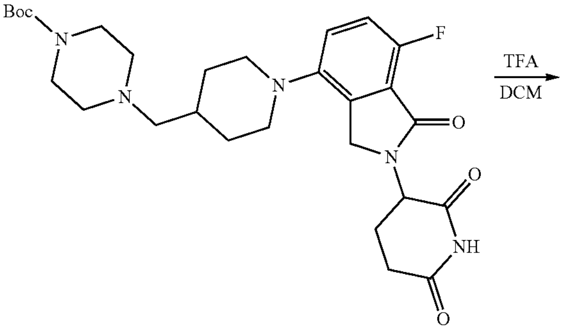

-continued

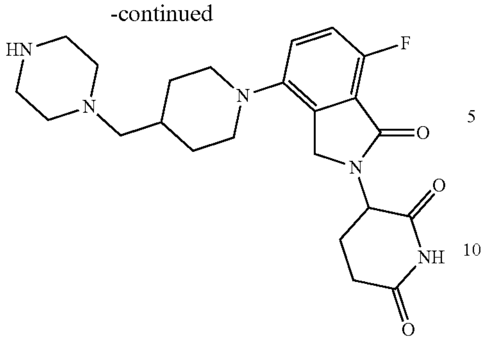

Step 4:

To a mixture of tert-butyl 4-[[1-[2-(2,6-dioxo-3-piperidyl)-7-fluoro-1-oxo-isoindolin-4-yl]-4-piperidyl]methyl] piperazine-1-carboxylate (80 mg, 147.16 μmol, 1 eq) in DCM (2 mL) was added TFA (1.23 g, 10.80 mmol, 800.00 uL, 73.42 eq) in one portion at 25° C. under $N_2$. The mixture was stirred at 25° C. for 1 hours. LCMS showed the reaction was completed. The mixture was concentrated in reduce pressure at 40° C. The residue was used into next step directly without further purification. The product 3-[7-fluoro-1-oxo-4-[4-(piperazin-1-ylmethyl)-1-piperidyl]isoindolin-2-yl]piperidine-2,6-dione (60 mg, 129.87 μmol, 88.25% yield, 96% purity) as gray solid.

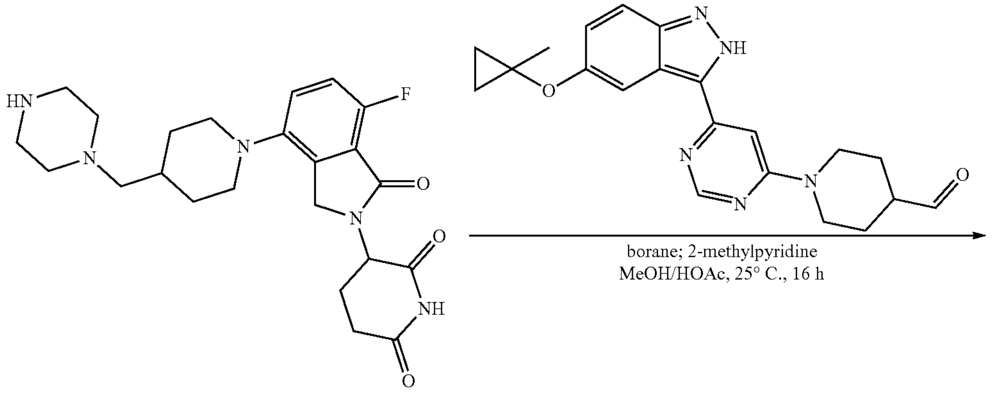

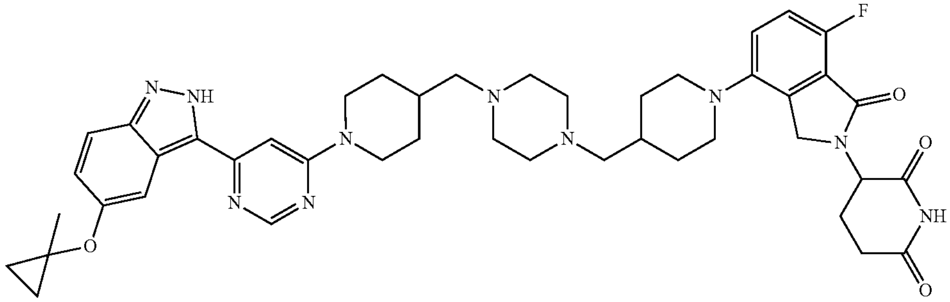

Step 5:

To a mixture of 3-[7-fluoro-1-oxo-4-[4-(piperazin-1-ylmethyl)-1-piperidyl]isoindolin-2-yl]piperidine-2,6-dione (60 mg, 135.28 μmol, 1 eq) and 1-[6-[5-(1-methylcyclopropoxy)-2H-indazol-3-yl]pyrimidin-4-yl]piperidine-4-carbaldehyde (51.06 mg, 135.28 μmol, 1 eq) in MeOH (4 mL) and HOAc (0.4 mL) was added borane; 2-methylpyridine (28.94 mg, 270.57 μmol, 2 eq) in one portion at 25° C. under $N_2$. The mixture was stirred at 25° C. for 16 hours. LCMS showed the reaction was completed. The mixture was concentrated in reduce pressure at 40° C. The residue was purified by prep-HPLC (Xtimate C18 100*30 mm*10 um; mobile phase: [water (0.225% FA)-ACN]; B %: 0%-30%, 40 min) to afford 3-[7-fluoro-4-[4-[[4-[[1-[6-[5-(1-methylcyclopropoxy)-2H-indazol-3-yl]pyrimidin-4-yl]-4-piperidyl]methyl]piperazin-1-yl]methyl]-1-piperidyl]-1-oxo-isoindolin-2-yl]piperidine-2,6-dione (24.3 mg, 28.47 μmol, 21.04% yield, 99.7% purity, FA) as gray solid.

Exemplary Synthesis of Compound 215

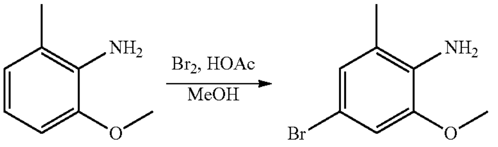

Step 1:

A solution of 2-methoxy-6-methyl-aniline (25 g, 182.24 mmol, 1 eq) in MeOH (100 mL) and AcOH (30 mL). The flask was cooled to 0° C., $Br_2$ (29.12 g, 182.24 mmol, 9.39 mL, 1 eq) in AcOH (30 mL) add was added to the reaction dropwise. The reaction mixture was stirred at 0° C. for 2 hours, then was warmed up to 20° C. for 1 hour. TLC (Petroleum ether:Ethyl acetate=10:1) showed one new spot The reaction mixture was concentrated down. 15% NaOH was added to neutralize the reaction at 0° C. Ethyl acetate (100 mL) was added to extract the reaction mixture. The organic layer was concentrated after drying over anhydrous sodium sulfate to give 4-bromo-2-methoxy-6-methyl-aniline (35 g, 161.98 mmol, 88.88% yield) as a brown oil

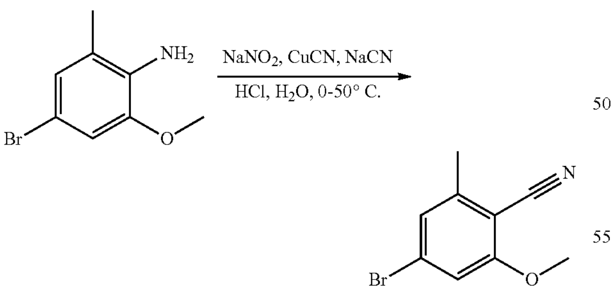

Step 2:

Synthesis of 4-bromo-2-methoxy-6-methyl-aniline (30 g, 138.84 mmol, 1 eq) was suspended in concentrated aqueous HCl (12 M, 85.71 mL, 7.41 eq) and ice-water (32.52 g, 1.81 mol, 13 eq) cooled to 0° C. A solution of $NaNO_2$ (10.06 g, 145.79 mmol, 1.05 eq) in $H_2O$ (200 mL) was added drop wise. The resulting mixture was stirred at 0° C. for 30 min and neutralized with aqueous $Na_2CO_3$ (14.72 g, 138.84 mmol, 1 eq). The initial diazonium salt mixture was then added to a suspension of CuCN (14.92 g, 166.62 mmol, 36.40 mL, 1.20 eq) in $H_2O$ (100 mL) and NaCN (20.40 g, 416.27 mmol, 3.00 eq) in $H_2O$ (100 mL), then toluene (200 mL) was added and the mixture was stirring at 0° C. for 1 h, at 25° C. for 2 h, and at 50° C. for another 1 h. TLC (Petroleum ether:Ethyl acetate=10:1, Rf=0.63) showed the reaction was completed. The mixture was cooled to 20° C. The aqueous layer was extracted with toluene, the aqueous phase was extracted with ethyl acetate (200 mL*3). The combined organic phase was washed with brine (100 mL*2), dried with anhydrous $Na_2SO_4$, filtered and concentrated in vacuum. The residue was purified by silica gel chromatography (3% of Ethyl acetate in Petroleum ether) to give 4-bromo-2-methoxy-6-methyl-benzonitrile (12.1 g, 53.52 mmol, 38.55% yield) as a yellow solid.

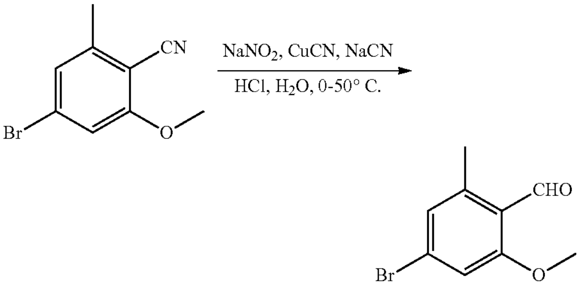

Step 3:

To a mixture of 4-bromo-2-methoxy-6-methyl-benzonitrile (4.5 g, 19.91 mmol, 1 eq) in THF (50 mL) was added DIBAL-H (1 M, 115 mL, 5.78 eq) drop-wise at −70° C. under $N_2$. The mixture was stirred at 20° C. for 10 hours. TLC showed there was a new spot. The residue was poured into HCl (2 M) to adjusted the pH=5-6. The aqueous phase was extracted with ethyl acetate (100 mL*3). The combined organic phase was washed with brine (100 mL*2), dried with anhydrous $Na_2SO_4$, filtered and concentrated in vacuum. The residue was purified by silica gel chromatography (Petroleum ether) to give 4-bromo-2-methoxy-6-methyl-benzaldehyde (2.3 g, 10.04 mmol, 50.44% yield) as a yellow solid.

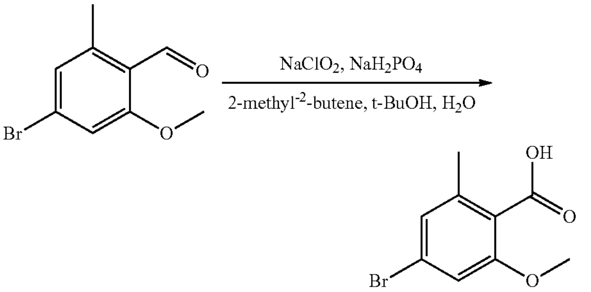

Step 4:

To a suspension of 4-bromo-2-methoxy-6-methyl-benzaldehyde (2.3 g, 10.04 mmol, 1 eq) in t-BuOH (20 mL) is added a solution of sodium chlorite (1.82 g, 20.08 mmol, 2 eq) and $NaH_2PO_4$ (4.82 g, 40.16 mmol, 4 eq) in $H_2O$ (20 mL). To the solution is added 2-methyl-2-butene (5.63 g, 80.32 mmol, 8.51 mL, 8 eq). The resulting homogeneous solution is stirred at 20° C. for 1.5 hr. TLC (Petroleum ether:Ethyl acetate=10:1, Rf=0.63) showed the reaction was completed. LCMS showed there was desired MS. The residue was poured into HCl (2 M) to adjusted the pH=5-6. The aqueous phase was extracted with ethyl acetate (20 mL*3). Then the organic phase adjusted to pH=9 with $NaHCO_3$, the combined organic phase was washed with brine (20 mL*3), the residue was poured into HCl (2 M) to adjusted the pH=5-6. The aqueous phase was extracted with ethyl acetate (20 mL*3), the combined organic phase was washed with brine (20 mL*3), dried with anhydrous $Na_2SO_4$, filtered and concentrated in vacuum to give 4-bromo-2-methoxy-6-methyl-benzoic acid (1.73 g, 7.06 mmol, 70.31% yield) as a yellow solid

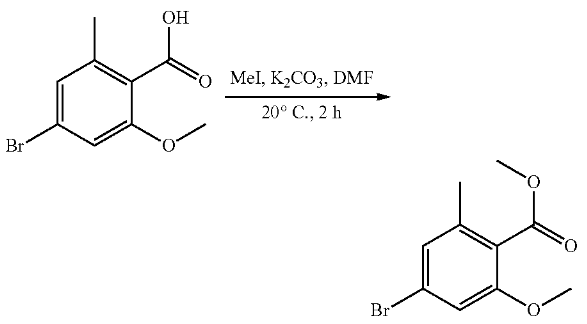

Step 5:

To a solution of 4-bromo-2-methoxy-6-methyl-benzoic acid (1.73 g, 7.06 mmol, 1 eq) in DMF (20 mL) was added MeI (2.00 g, 14.12 mmol, 878.92 uL, 2 eq) and $K_2CO_3$ (2.93 g, 21.18 mmol, 3 eq). The mixture was stirred at 20° C. for 1 hr. TLC showed the reaction was completed. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum to give methyl 4-bromo-2-methoxy-6-methyl-benzoate (1.17 g, 4.52 mmol, 63.97% yield) as a white solid.

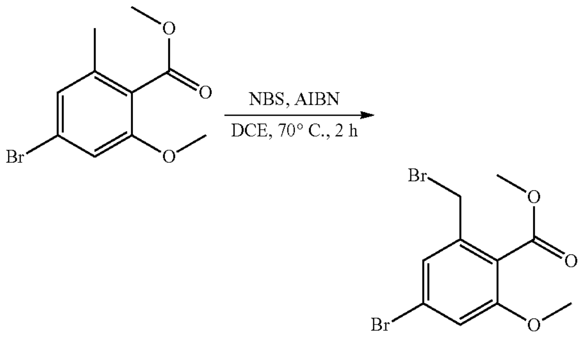

Step 6:

To a stirred solution of methyl 4-bromo-2-methoxy-6-methyl-benzoate (1.17 g, 4.52 mmol, 1 eq) in DCE (10 mL) under an atmosphere of nitrogen was added NBS (964.47 mg, 5.42 mmol, 1.2 eq) followed by 2-[(E)-(1-cyano-1-methyl-ethyl)azo]-2-methyl-propanenitrile (37.08 mg, 225.78 µmol, 0.05 eq) and the resulting mixture was stirred vigorously at 70° C. for 2 h. LCMS showed there was desired MS. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by prep-HPLC (column: Xtimate C18 150*40 mm*10 um; mobile phase: [water (0.225% FA)-ACN]; B %: 55%-85%, 10 min) to give methyl 4-bromo-2-(bromomethyl)-6-methoxy-benzoate (550 mg, 1.63 mmol, 36.04% yield) as a white solid.

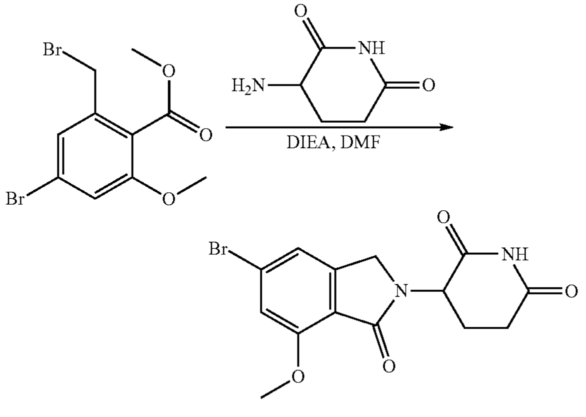

Step 7:

To a mixture of methyl 4-bromo-2-(bromomethyl)-6-methoxy-benzoate (550 mg, 1.63 mmol, 1 eq) and 3-aminopiperidine-2,6-dione (321.40 mg, 1.95 mmol, 1.2 eq, HCl) in DMF (10 mL) was added DIEA (1.05 g, 8.14 mmol, 1.42 mL, 5 eq) in one portion at 20° C. under $N_2$. The mixture was stirred at 85° C. for 48 hours. LCMS showed there was desired MS. The crude was concentrated in vacuum. The crude product was triturated with MeCN (20 mL) and $H_2O$ (20 mL) at 20° C. The crude was filtered and solid was concentrated in vacuum to give 3-(5-bromo-7-methoxy-1-oxo-isoindolin-2-yl)piperidine-2,6-dione (420 mg, 1.19 mmol, 73.08% yield) as a dark gray solid

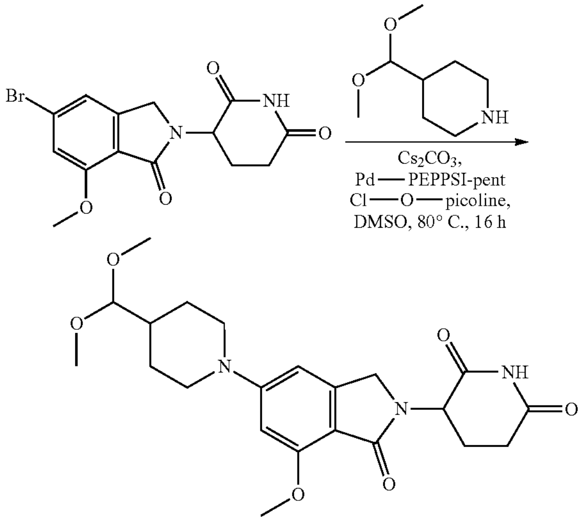

Step 8:

To a solution of 3-(5-bromo-7-methoxy-1-oxo-isoindolin-2-yl)piperidine-2,6-dione (200 mg, 566.30 µmol, 1 eq) and 4-(dimethoxymethyl)piperidine (180.34 mg, 1.13 mmol, 2 eq) in DMSO (5 mL) was added $Cs_2CO_3$ (369.03 mg, 1.13 mmol, 2 eq) and Pd-PEPPSI-pent Cl—O-picoline (30.75 mg, 56.63 μmol, 0.1 eq). After addition, the reaction mixture was stirred at 80° C. under $N_2$ for 12 h. LCMS showed there was desired MS. The mixture was cooled to 20° C. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by prep-TLC (Petroleum ether/Ethyl acetate=0/1) to give 3-[5-[4-(dimethoxymethyl)-1-piperidyl]-7-methoxy-1-oxo-isoindolin-2-yl]piperidine-2,6-dione (268 mg, 291.92 μmol, 51.55% yield, 47% purity) as yellow oil.

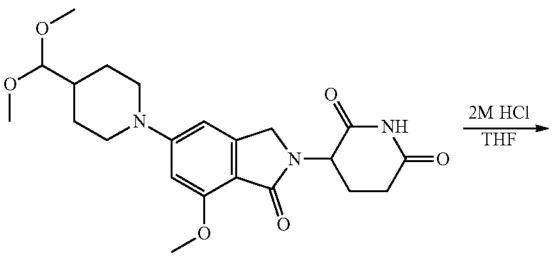

-continued

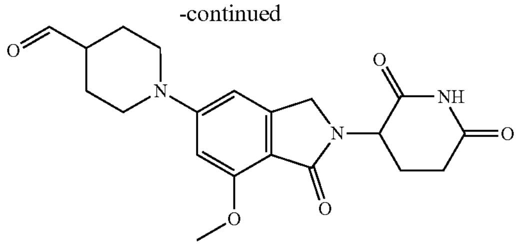

Step 9:

To a mixture of 3-[5-[4-(dimethoxymethyl)-1-piperidyl]-7-methoxy-1-oxo-isoindolin-2-yl]piperidine-2,6-dione (268 mg, 621.12 μmol, 1 eq) in THF (5 mL) was added HCl (2 M, 5 mL, 16.10 eq) in one portion at 20° C. under $N_2$. The mixture was stirred at 20° C. for 1 hour to give yellow solution. LCMS showed there was desired MS. The residue was poured into saturated $NaHCO_3$ to adjusted the pH=7-8. The aqueous phase was extracted with ethyl acetate (20 mL*3). The combined organic phase was washed with brine (20 mL*2), dried with anhydrous $Na_2SO_4$, filtered and concentrated in vacuum to give 1-[2-(2,6-dioxo-3-piperidyl)-7-methoxy-1-oxo-isoindolin-5-yl]piperidine-4-carbaldehyde (131 mg, 237.93 μmol, 38.31% yield, 70% purity) as a yellow solid.

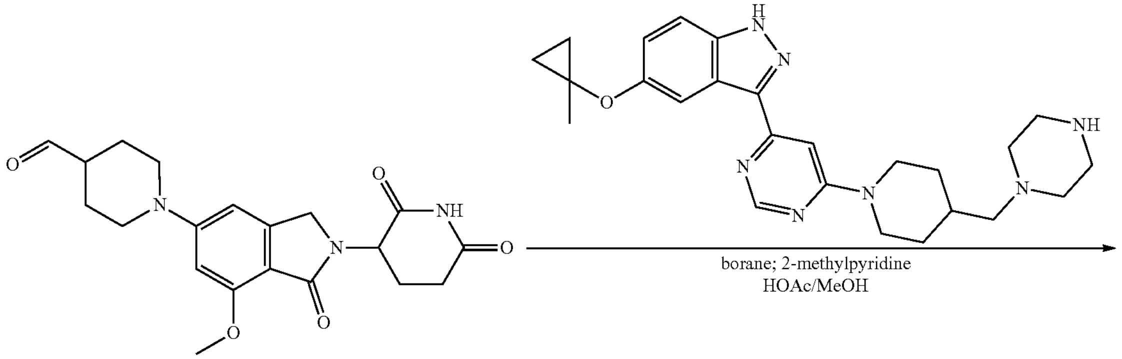

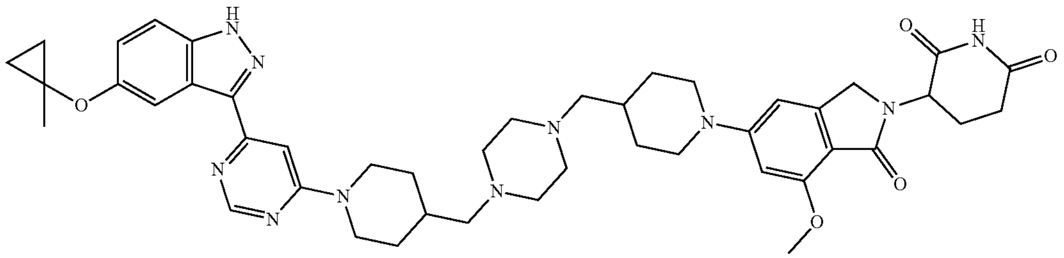

Step 10:

To a mixture of 5-(1-methylcyclopropoxy)-3-[6-[4-(piperazin-1-ylmethyl)-1-piperidyl]pyrimidin-4-yl]-2H-indazole (56.90 mg, 127.14 μmol, 1 eq) and 1-[2-(2,6-dioxo-3-piperidyl)-7-methoxy-1-oxo-isoindolin-5-yl]piperidine-4-carbaldehyde (70 mg, 127.14 μmol, 70% purity, 1 eq) in MeOH (10 mL) was added borane; 2-methylpyridine (27.20 mg, 254.27 μmol, 2 eq) and HOAc (7.63 mg, 127.14 μmol, 7.27 uL, 1 eq) in one portion at 20° C. under $N_2$. The mixture was stirred at 20° C. for 10 h to give yellow solution. LCMS showed there was desired MS. The resulting product was poured into $H_2O$ (20 mL). The mixture was extracted with ethyl acetate (20 mL*3). The organic phase was washed with brine (15 mL*2), dried over anhydrous $Na_2SO_4$, concentrated in vacuum to give a residue. The residue was purified by prep-HPLC (column: Xtimate C18 100*30 mm*10 um; mobile phase: [water (0.225% FA)-ACN]; B %: 0%-30%, 40 min) to give 3-[7-methoxy-5-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (61 mg, 73.70 μmol, 57.97% yield, 98.71% purity, FA) as a white solid.

Exemplary Synthesis of Compound 216

Compound 216 was prepared in a manner analogous to compound 215.

Exemplary Synthesis of Compound 217

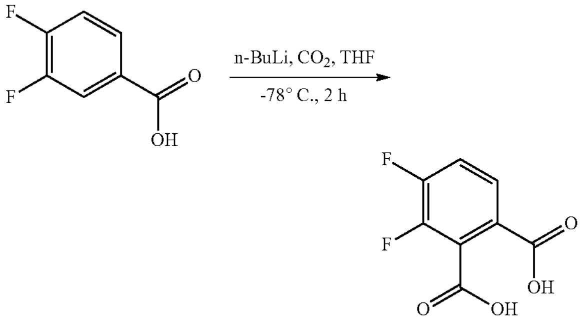

Step 1:

To a dry 3-necked round-bottomed-flask was added a solution of diisopropylamine (4.61 g, 45.54 mmol, 6.44 mL, 2.4 eq) in THF (45 mL). The flask was cooled to −78° C. and a solution of n-BuLi (2.5 M, 17.46 mL, 2.3 eq) was added dropwise. Then the reaction mixture was stirred at 0° C. to 20° C. for 30 min. A solution of 3,4-difluorobenzoic acid (3 g, 18.98 mmol, 1 eq) in THF (30 mL) was added dropwise at −78° C. and the mixture was stirred for 1.5 h then excess carbon dioxide pellets were added and the mixture was further stirred at −78° C. for 15 min then was allowed to warm to 20° C. Then the reaction mixture was stirred at 20° C. for 2 h. Sodium hydroxide solution 1 N in water (50 mL) was added. The resulting mixture was extracted with t-butyl methyl ether (20 mL×2). The aqueous layer was acidified with hydrogen chloride (6 N) to pH 1 and extracted with ethyl acetate (40 mL×3). The combined ethyl acetate extracts were dried over anhydrous sodium sulfate and concentrated to give 3,4-difluorophthalic acid (4 g, crude) as a white solid. The crude product was used for next step directly.

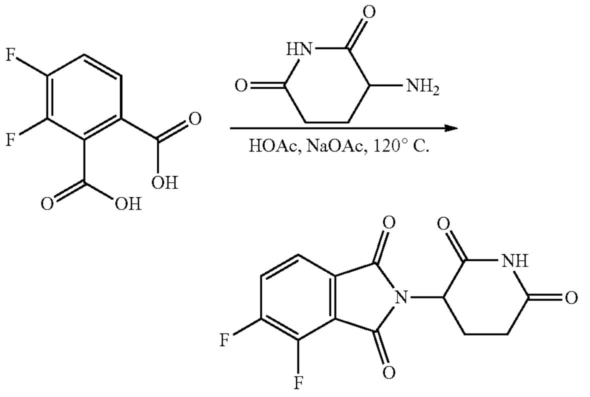

Step 2:

To a solution of 3,4-difluorophthalic acid (4 g, 19.79 mmol, 1 eq) and 3-aminopiperidine-2,6-dione (4.89 g, 29.69 mmol, 1.5 eq, HCl) in HOAc (6 mL) was added NaOAc (4.87 g, 59.37 mmol, 3 eq). The mixture was stirred at 120° C. for 12 h. LCMS showed the reaction completed. The reaction mixture was quenched by addition water (200 mL) at 0° C., and the solid was collected by filtration. 2-(2,6-dioxo-3-piperidyl)-4,5-difluoro-isoindoline-1,3-dione (3.3 g, 11.22 mmol, 56.67% yield) as a black solid. The residue was used into the next step without further purification.

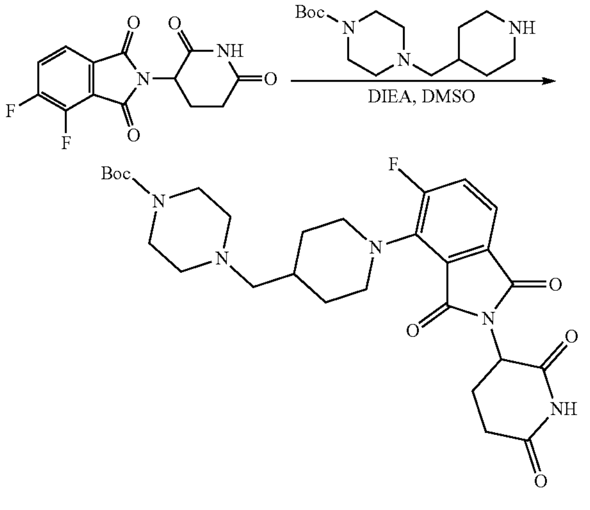

Step 3:

To a solution of 2-(2,6-dioxo-3-piperidyl)-4,5-difluoro-isoindoline-1,3-dione (1 g, 3.40 mmol, 1 eq) and tert-butyl 4-(4-piperidylmethyl)piperazine-1-carboxylate (1.00 g, 3.53 mmol, 1.04 eq) in DMSO (20 mL) was added DIEA (1.32 g, 10.20 mmol, 1.78 mL, 3 eq). After addition, the reaction mixture was stirred at 60° C. for 1 h. LCMS showed the reaction completed. After cooling, the reaction mixture was diluted with ethyl acetate (40 mL) and washed with brine (30 mL*3). The organic layer was dried over sodium sulfate and concentrated under reduced pressure. The residue was purified by silica gel column chromatography (0 to 100% ethyl acetate in petroleum ether) to afford tert-butyl 4-[[1-[2-(2,6-dioxo-3-piperidyl)-5-fluoro-1,3-dioxo-isoindolin-4-yl]-4-piperidyl]methyl]piperazine-1-carboxylate (780 mg, 1.40 mmol, 41.15% yield) as a yellow solid.

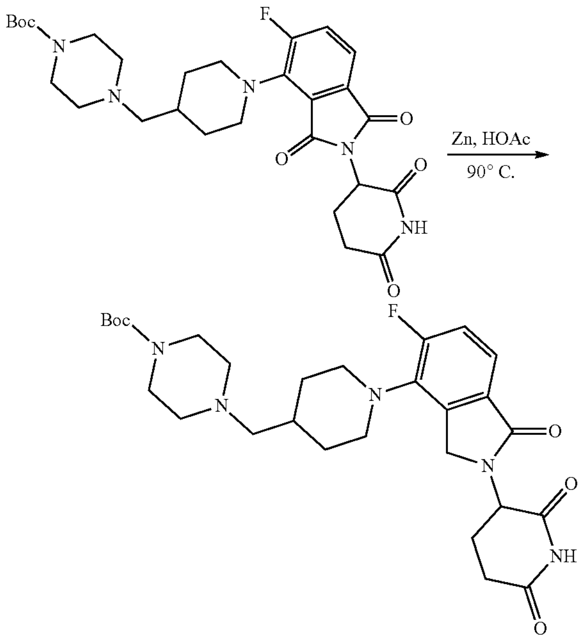

Step 4:

To a solution of tert-butyl 4-[[1-[2-(2,6-dioxo-3-piperidyl)-5-fluoro-1,3-dioxo-isoindolin-4-yl]-4-piperidyl] methyl]piperazine-1-carboxylate (780 mg, 1.40 mmol, 1 eq) in HOAc (10 mL) was added Zn (3.27 g, 50.01 mmol, 35.75 eq). After addition, the reaction mixture was stirred at 90° C. for 1 h. LCMS showed the reaction completed. The reaction mixture was filtered and the filtration was concentrated. The residue was dissolved into water (30 mL) and adjusted to pH 7~8 with saturated sodium bicarbonate solution. The mixture was extracted with ethyl acetate (20 mL×3). The combined organic phase was washed with saturated brine (30 mL×2), dried with anhydrous sodium sulfate, filtered and concentrated in vacuum. The residue was purified by prep.HPLC (column: Xtimate C18 150*40 mm*10 um; mobile phase: [water (0.225% FA)-ACN]; B %: 0%-30%, 10 min) to afford tert-butyl 4-[[1-[2-(2,6-dioxo-3-piperidyl)-5-fluoro-1-oxo-isoindolin-4-yl]-4-piperidyl]methyl]piperazine-1-carboxylate (280 mg, 504.76 μmol, 36.08% yield, 98% purity) as a white solid.

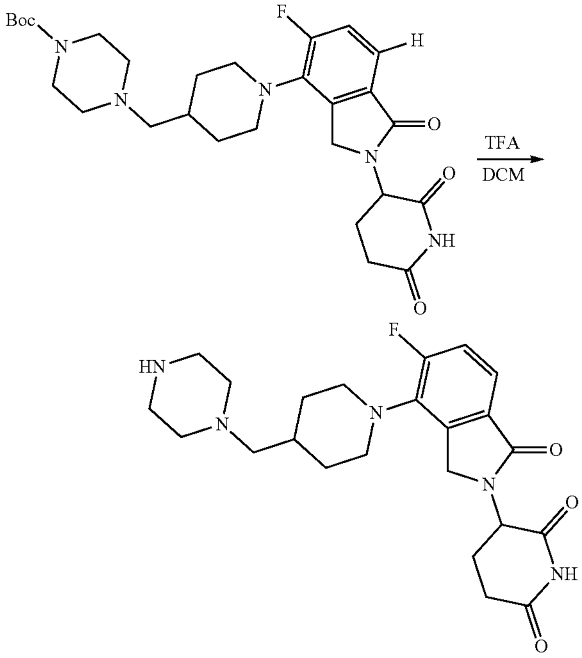

Step 5:

To a solution of tert-butyl 4-[[1-[2-(2,6-dioxo-3-piperidyl)-5-fluoro-1-oxo-isoindolin-4-yl]-4-piperidyl]methyl] piperazine-1-carboxylate (100 mg, 183.95 μmol, 1 eq) in DCM (3 mL) was added TFA (770.00 mg, 6.75 mmol, 0.5 mL, 36.71 eq). After addition, the reaction mixture was stirred at 20° C. for 1 h. LCMS showed the reaction completed. The reaction mixture was concentrated under reduced pressure to afford 3-[5-fluoro-1-oxo-4-[4-(piperazin-1-ylmethyl)-1-piperidyl]isoindolin-2-yl]piperidine-2,6-dione (100 mg, crude, TFA) as a light yellow gum.

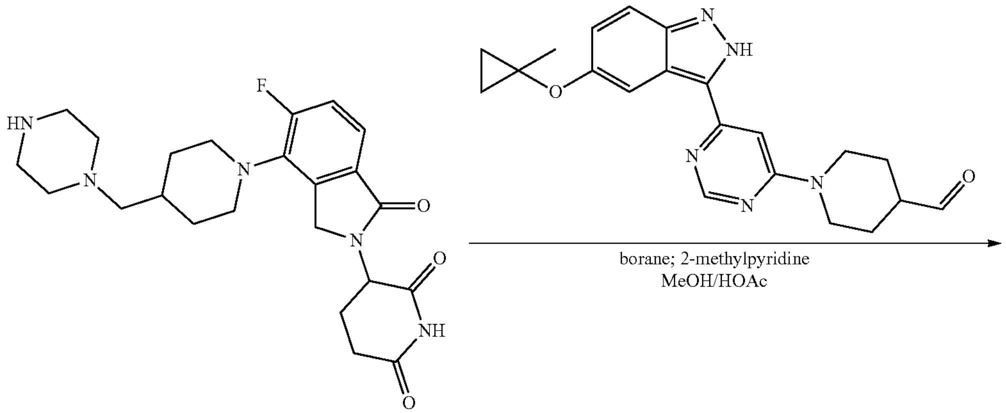

-continued

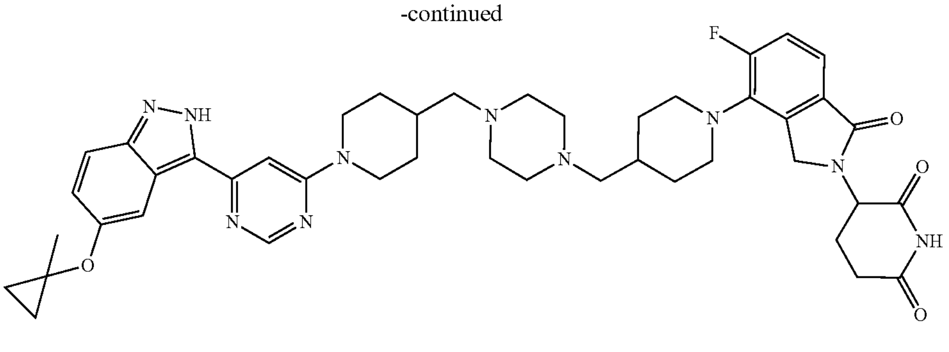

Step 6:

To a mixture of 3-[5-fluoro-1-oxo-4-[4-(piperazin-1-ylmethyl)-1-piperidyl]isoindolin-2-yl]piperidine-2,6-dione (100 mg, 179.36 μmol, 1 eq, TFA) in MeOH (5 mL) was added DIEA (23.18 mg, 179.36 μmol, 31.24 uL, 1 eq). Then 1-[6-[5-(1-methylcyclopropoxy)-2H-indazol-3-yl]pyrimidin-4-yl]piperidine-4-carbaldehyde (70 mg, 185.46 μmol, 1.03 eq) and HOAc (0.5 mL) was added. Then borane; 2-methylpyridine (38.37 mg, 358.72 μmol, 2 eq) was added to above solution. After addition, the reaction solution was stirred at 20° C. for 12 h. LCMS showed the reaction completed. The reaction mixture was concentrated under reduced pressure to remove most of solvent. The residue was purified by prep.HPLC (column: Xtimate C18 150*40 mm*10 um; mobile phase: [water (FA)-ACN]; B %: 0%-40%, 40 min) to afford 3-[5-fluoro-4-[4-[[4-[[1-[6-[5-(1-methylcyclopropoxy)-2H-indazol-3-yl]pyrimidin-4-yl]-4-piperidyl]methyl]piperazin-1-yl]methyl]-1-piperidyl]-1-oxo-isoindolin-2-yl]piperidine-2,6-dione (75.1 mg, 90.75 μmol, 50.60% yield, 97.27% purity) as a white solid.

Exemplary Synthesis of Compound 218

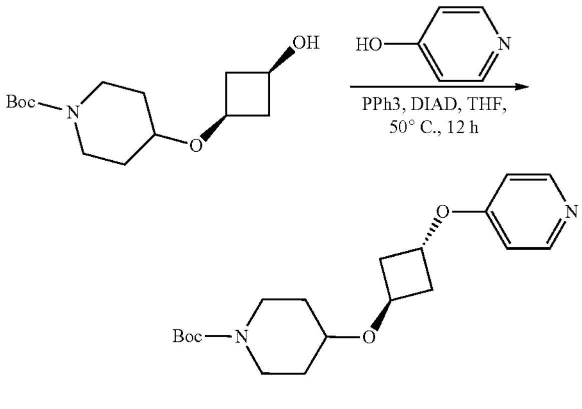

Step 1:

To a solution of tert-butyl 4-(3-hydroxycyclobutoxy)piperidine-1-carboxylate (2.8 g, 10.32 mmol, 1 eq), pyridin-4-ol (1.18 g, 12.38 mmol, 1.2 eq) in tetrahydrofuran (25 mL) was added triphenyl phosphine (3.25 g, 12.38 mmol, 1.2 eq) and Diisopropyl azodicarboxylate (2.50 g, 12.38 mmol, 2.4 mL, 1.2 eq) under nitrogen at 0° C. The reaction mixture was stirred at 50° C. for 12 h. LCMS showed desired MS was detected. The mixture was concentrated in vacuum. The residue was purified by silica gel chromatography (petroleum ether:ethyl acetate=10:1 to 0:1). tert-butyl 4-[3-(4-pyridyloxy)cyclobutoxy]piperidine-1-carboxylate (3 g, 8.61 mmol, 83% yield) was obtained as a light yellow solid.

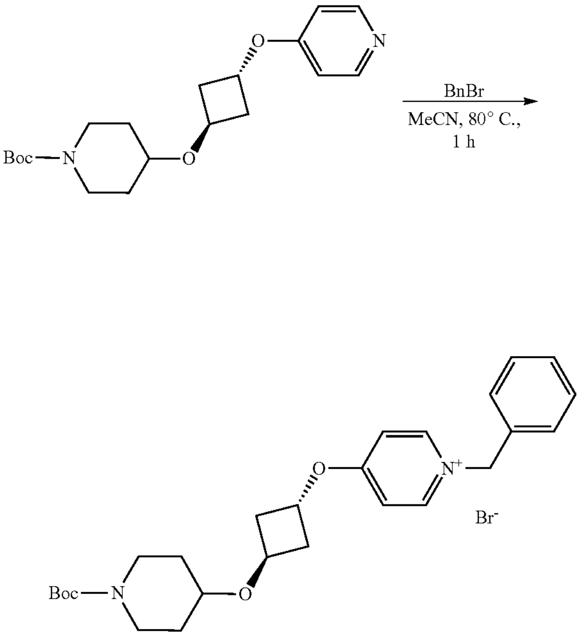

Step 2:

To a solution of tert-butyl 4-[3-(4-pyridyloxy)cyclobutoxy]piperidine-1-carboxylate (3 g, 8.61 mmol, 1 eq) in acetonitrile (30 mL) was added benzylbromide (1.77 g, 10.33 mmol, 1.2 mL, 1.2 eq). The reaction mixture was stirred at 80° C. for 1 h. LCMS showed desired MS was detected. The mixture was concentrated in vacuum. tert-butyl 4-[3-[(1-BLAH-1-benzyl-4-pyridyl)oxy]cyclobutoxy]piperidine-1-carboxylate (4.5 g, crude) was obtained as a yellow oil.

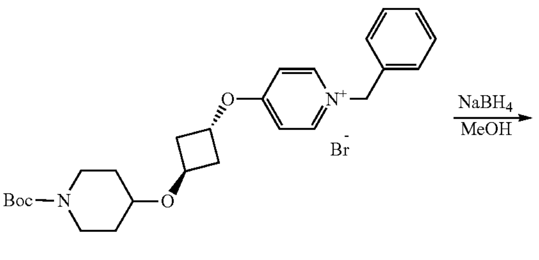

-continued

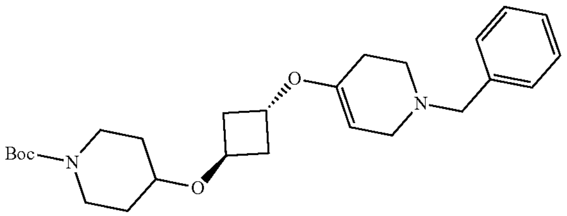

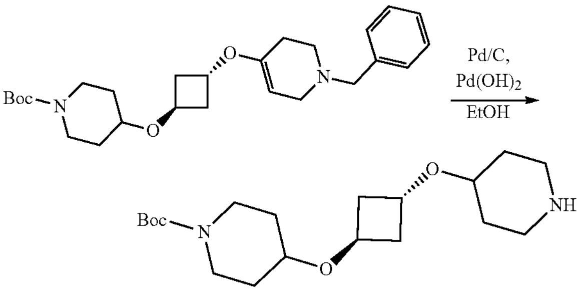

Step 3:

To a solution of tert-butyl 4-[3-[(1-BLAH-1-benzyl-4-pyridyl)oxy]cyclobutoxy]piperidine-1-carboxylate (4.5 g, 8.66 mmol, 1 eq) in methanol (40 mL) was added sodium borohydride (819 mg, 21.66 mmol, 2.5 eq) in three portions at 0° C. The reaction mixture was stirred at 20° C. for 1 h. LCMS showed desired MS was detected. Hydrochloric acid solution (1 M) was added to quench the reaction and water (100 mL) was added to quench the reaction, the aqueous phase was extracted with ethyl acetate (100 mL*3). The combined organic phase was washed with brine (100 mL), dried over sodium sulfate, filtered and concentrated in vacuum. The residue was purified by silica gel chromatography (petroleum ether:ethyl acetate=10:1 to 0:1). tert-butyl 4-[3-[(1-benzyl-3,6-dihydro-2H-pyridin-4-yl)oxy]cyclobutoxy]piperidine-1-carboxylate (900 mg, 1.89 mmol, 22% yield, 93% purity) was obtained as a light yellow solid.

Step 4:

To a solution of tert-butyl 4-[3-[(1-benzyl-3,6-dihydro-2H-pyridin-4-yl)oxy]cyclobutoxy] piperidine-1-carboxylate (900 mg, 2.03 mmol, 1 eq) in ethanol (50 mL) was added palladium on activated carbon (100 mg, 10% purity) and Palladium hydroxide on carbon (100 mg, 0.14 mmol, 20% purity, 0.07 eq) under nitrogen. The reaction mixture was stirred at 50° C. under hydrogen (50 Psi) for 16 h. TLC (petroleum ether:ethyl acetate=1:1) showed new spot was detected. LCMS showed desired MS was detected. The mixture was filtered and the filtrate was concentrated in vacuum. The residue was used into next step. tert-butyl 4-[3-(4-piperidyloxy)cyclobutoxy]piperidine-1-carboxylate (750 mg, crude) was obtained as a light yellow oil.

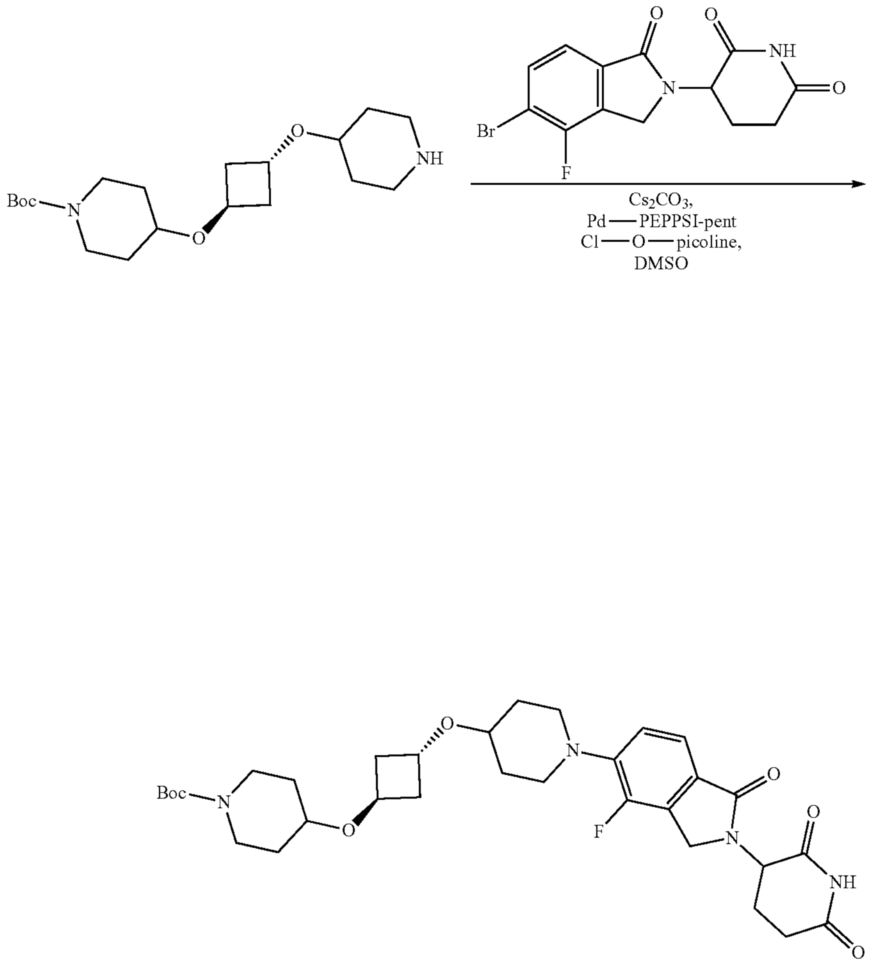

Step 5:

To a solution of 3-(5-bromo-6-fluoro-1-oxo-isoindolin-2-yl)piperidine-2,6-dione (500 mg, 1.47 mmol, 1 eq), tert-butyl 4-[3-(4-piperidyloxy)cyclobutoxy]piperidine-1-carboxylate (623 mg, 1.76 mmol, 1.2 eq) in dimethyl sulfoxide (5 mL) was added cesium carbonate (955 mg, 2.93 mmol, 2 eq) and Pd-PEPPSI-pent Cl—O-picoline, (142 mg, 0.15 mmol, 0.1 eq) under nitrogen. The reaction was stirred at 80° C. for 12 h. LCMS showed desired MS was detected. Dichloromethane (20 mL) and water (20 mL) was added to the mixture, the aqueous phase was extracted with dichloromethane (20 mL*2). The combined organic phase was washed with brine (20 mL), dried over sodium sulfate, filtered and concentrated in vacuum. The residue was purified by prep-TLC (dichloromethane:methanol=10:1). tert-butyl 4-[3-[[1-[2-(2,6-dioxo-3-piperidyl)-4-fluoro-1-oxo-isoindolin-5-yl]-4-piperidyl]oxy] cyclobutoxy]piperidine-1-carboxylate (120 mg, 0.19 mmol, 13% yield) was obtained as a light yellow solid.

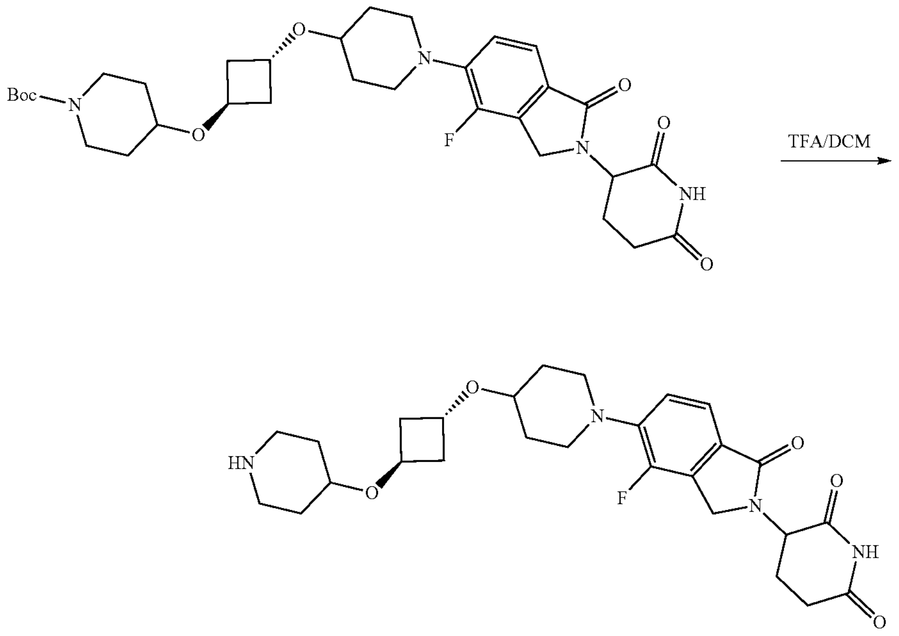

Step 6:

To a solution of tert-butyl 4-[3-[[1-[2-(2,6-dioxo-3-piperidyl)-4-fluoro-1-oxo-isoindolin-5-yl]-4-piperidyl]oxy]cyclobutoxy]piperidine-1-carboxylate (120 mg, 0.19 mmol, 1 eq) in dichloromethane (5 mL) was added trifluoroacetic acid (1.54 g, 13.51 mmol, 1 mL, 69.19 eq). The reaction mixture was stirred at 20° C. for 0.5 h. LCMS showed desired MS was detected. The mixture was concentrated in vacuum. The residue was used into next step directly. 3-[4-fluoro-1-oxo-5-[4-[3-(4-piperidyloxy)cyclobutoxy]-1-piperidyl]isoindolin-2-yl]piperidine-2,6-dione (120 mg, 0.19 mmol, 97% yield, trifluoroacetate) was obtained as a yellow oil.

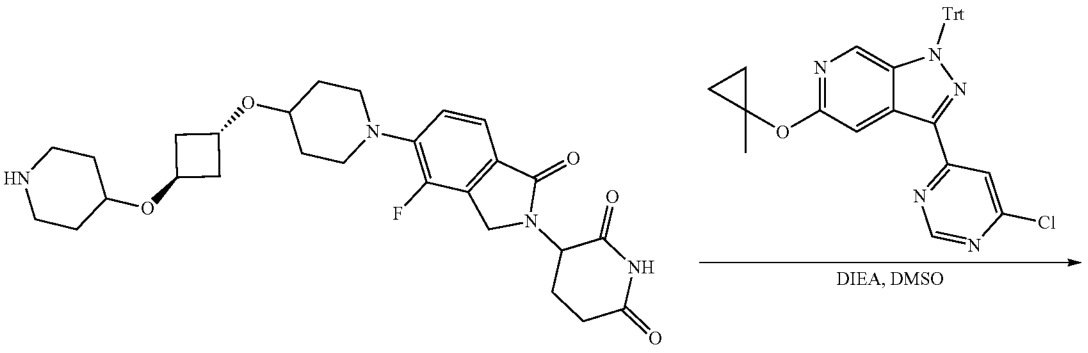

-continued

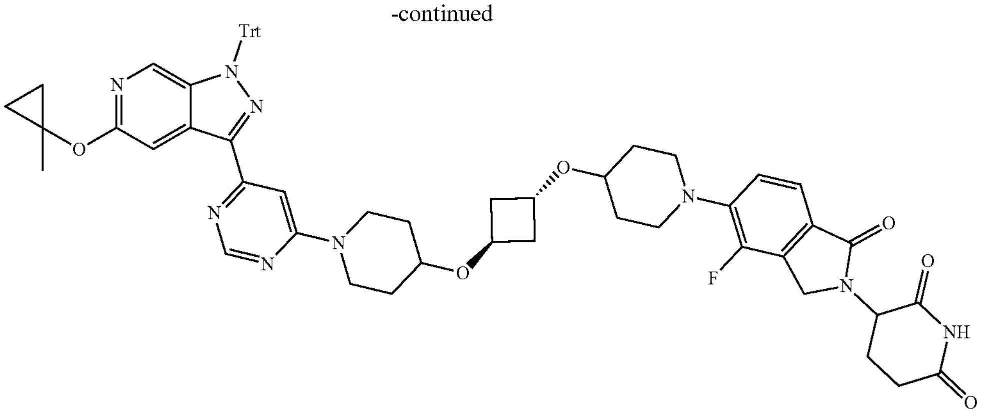

Step 7:

To a solution of 3-[4-fluoro-1-oxo-5-[4-[3-(4-piperidyloxy)cyclobutoxy]-1-piperidyl] isoindolin-2-yl]piperidine-2,6-dione (120 mg, 0.19 mmol, 1 eq, trifluoroacetate) in dimethyl sulfoxide (5 mL) was added N,N-diisopropylethylamine (123 mg, 0.95 mmol, 0.2 mL, 5 eq) and 3-(6-chloropyrimidin-4-yl)-5-(1-methylcyclopropoxy)-1-trityl-pyrazolo[3,4-c]pyridine (104 mg, 0.19 mmol, 1 eq). The reaction mixture was stirred at 90° C. for 2 h. LCMS showed desired MS was detected. Water (50 mL) was added to the mixture, the aqueous phase was extracted with ethyl acetate (50 mL*3). The combined organic phase was washed with brine (50 mL*2), dried over sodium sulfate, filtered and concentrated in vacuum. The residue was purified by prep-TLC (petroleum ether:ethyl acetate=1:2). 3-[4-fluoro-5-[4-[3-[[1-[6-[5-(1-methylcyclopropoxy)-1-trityl-pyrazolo[3,4-c]pyridin-3-yl]pyrimidin-4-yl]-4-piperidyl]oxy] cyclobutoxy]-1-piperidyl]-1-oxo-isoindolin-2-yl] piperidine-2,6-dione (120 mg, 0.11 mmol, 57% yield, 93% purity) was obtained as a light yellow solid.

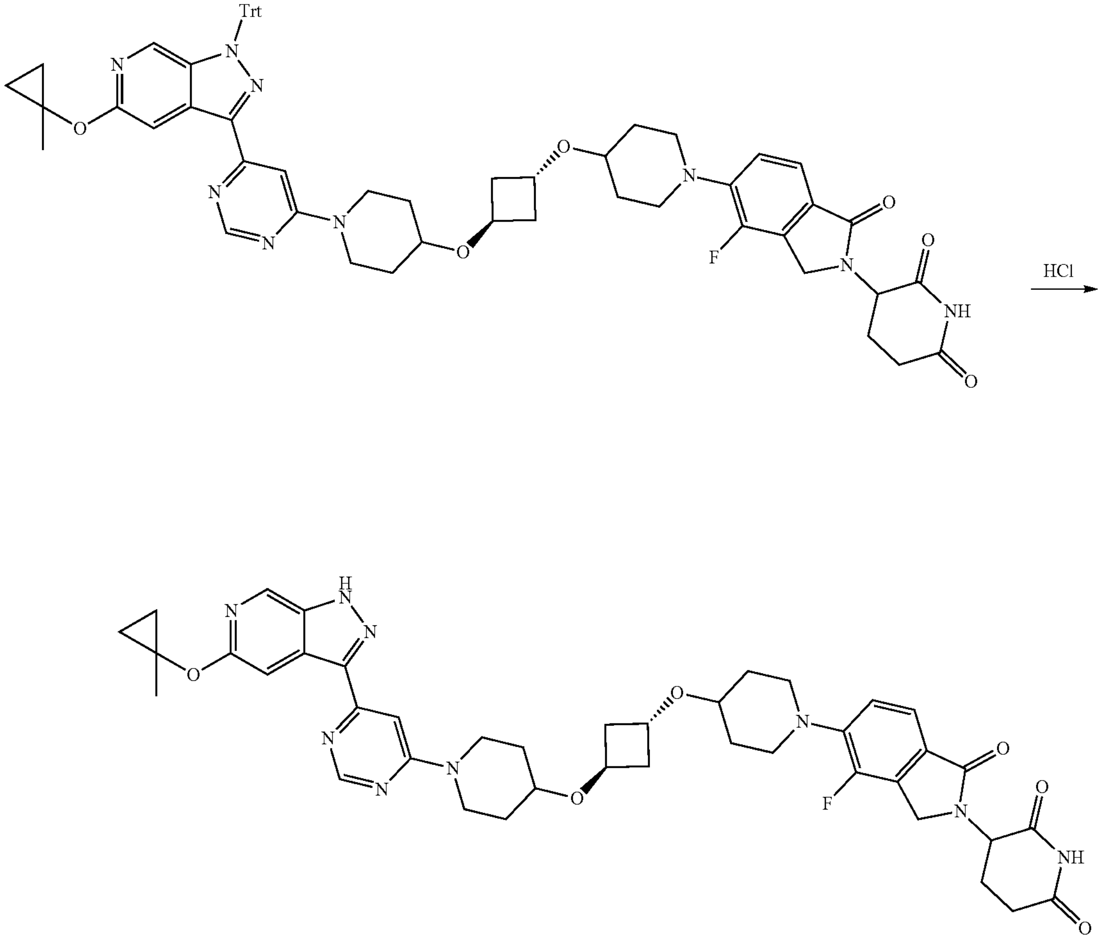

Step 8:

To a solution of 3-[4-fluoro-5-[4-[3-[[1-[6-[5-(1-methylcyclopropoxy)-1-trityl-pyrazolo[3,4-c] pyridin-3-yl]pyrimidin-4-yl]-4-piperidyl]oxy]cyclobutoxy]-1-piperidyl]-1-oxo-isoindolin-2-yl]piperidine-2,6-dione (120 mg, 0.12 mmol, 1 eq) in tetrahydrofuran (2 mL) was added hydrochloric acid (2 M, 2 mL, 34.07 eq). The reaction mixture was stirred at 40° C. for 12 h. LCMS showed desired MS was detected. The mixture was concentrated in vacuum. The residue was purified by prep-HPLC (column: Unisil 3-100 C18 Ultra 150*50 mm*3 um; mobile phase: [water (FA)-ACN]; B %: 25%-55%, 10 min). 3-[4-fluoro-5-[4-[3-[[1-[6-[5-(1-methylcyclopropoxy)-1H-pyrazolo[3,4-c]pyridin-3-yl]pyrimidin-4-yl]-4-piperidyl]oxy]cyclobutoxy]-1-piperidyl]-1-oxo-isoindolin-2-yl]piperidine-2,6-dione (35.4 mg, 0.04 mmol, 38% yield, 98% purity) was obtained as a white solid.

Exemplary Synthesis of Compound 219

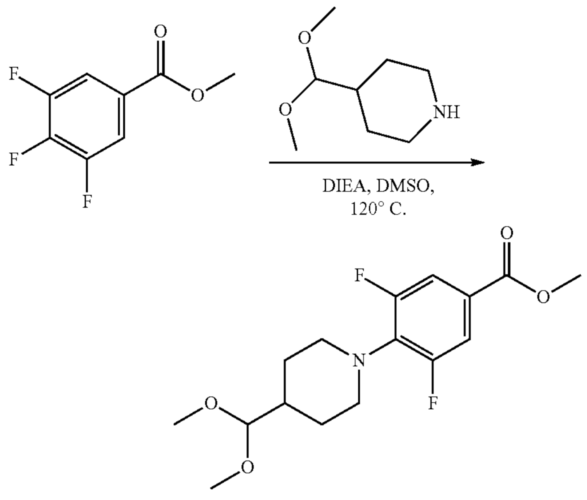

Step 1:

To a solution of methyl 3,4,5-trifluorobenzoate (2.5 g, 13.15 mmol, 1 eq) and 4-(dimethoxymethyl)piperidine (2.09 g, 13.15 mmol, 1 eq) in MeCN (15 mL) was added TEA (3.99 g, 39.45 mmol, 5.49 mL, 3 eq) stirred at 70° C. for 16 h under $N_2$. TLC (Petroleum ether:Ethyl acetate=3:1, Rf=0.3) showed the reaction a new spot. The reaction was quenched by $NH_4Cl$ (20 mL) solution and extracted with ethyl acetate (3*20 mL). The combined organic phases were washed with water, dried with $Na_2SO_4$, concentrated in vacuum to give a residue. The residue was purified by silica gel chromatography (Petroleum ether/Ethyl acetate=50/1, 1/1) to give methyl 4-[4-(dimethoxymethyl)-1-piperidyl]-3,5-difluoro-benzoate (3.4 g, 7.17 mmol, 54.56% yield, 69.5% purity) as a white solid.

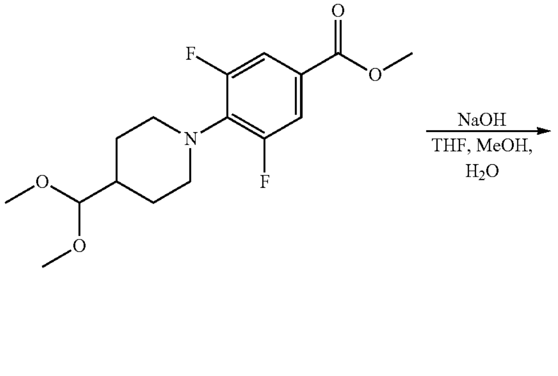

-continued

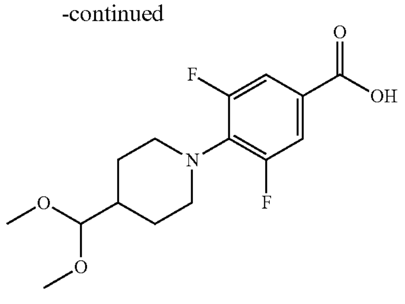

Step 2:

To a solution of methyl 4-[4-(dimethoxymethyl)-1-piperidyl]-3,5-difluoro-benzoate (3.4 g, 10.32 mmol, 1 eq) in a mixture of THF (7 mL) MeOH (7 mL) and $H_2O$ (7 mL) as added NaOH (2.06 g, 51.62 mmol, 5 eq). The mixture was stirred at 50° C. for 2 hours. The mixture was concentrated to remove most of organic solvent. The residue was extracted with ethyl acetate (30 mL). The aqueous was adjusted to pH around 4 with 0.5 N hydrochloric acid and then extracted with ethyl acetate (30 mL×3). The combined organic layers were washed with brine, dried (sodium sulfate) and concentrated. The crude was used for next step directly. 4-[4-(dimethoxymethyl)-1-piperidyl]-3,5-difluoro-benzoic acid (3.2 g, crude) was obtained as a white solid.

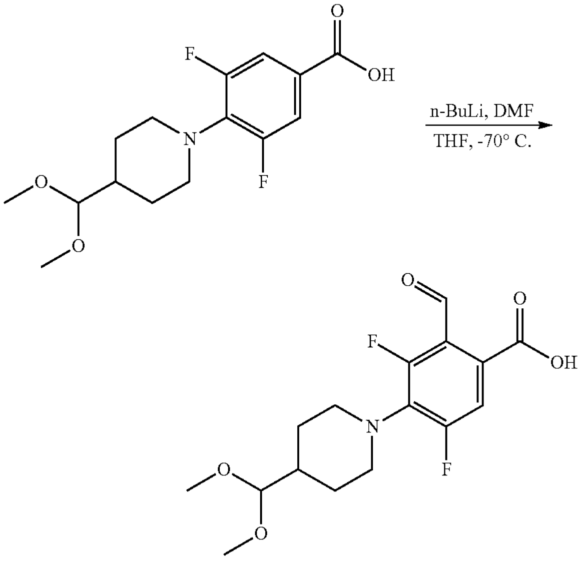

Step 3:

To a solution of 4-[4-(dimethoxymethyl)-1-piperidyl]-3,5-difluoro-benzoic acid (2.5 g, 7.93 mmol, 1 eq) in THF (20 mL) was added dropwise n-BuLi (2.5 M, 9.51 mL, 3 eq) at −78° C. After addition, the mixture was stirred at this temperature for 0.5 hour, and then DMF (5.80 g, 79.29 mmol, 6.10 mL, 10 eq) was added dropwise at −78° C. The resulting mixture was stirred at −78° C. for 0.5 hour. TLC (Petroleum ether:Ethyl acetate=3:1) one major new spot was detected. The mixture was quenched with saturated ammonium chloride solution and then adjusted pH around 4 with 0.5 N hydrogen chloride. The mixture was partitioned between ethyl acetate (30 mL) and water (20 mL). The aqueous was extracted with ethyl acetate (30 mL×2). The combined organic layers were washed with brine, dried (Sodium sulfate) and concentrated. The crude was triturated with petroleum ether/ethyl acetate (40 mL) to give 4-[4-(dimethoxymethyl)-1-piperidyl]-3,5-difluoro-2-formyl-benzoic acid (2.4 g, crude) as yellow solid.

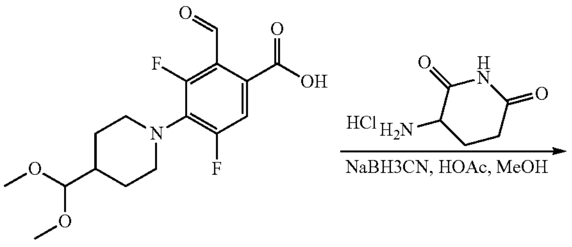

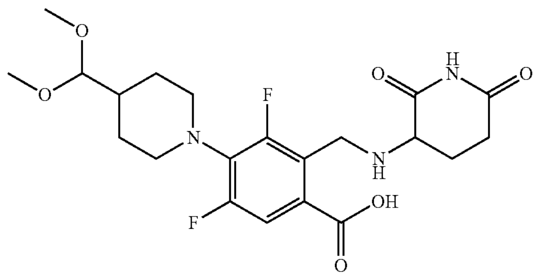

Step 4:

To a solution of 3-aminopiperidine-2,6-dione (1.73 g, 10.49 mmol, 1.5 eq, HCl) in MEOH (30 mL) was added NaOAc (2.29 g, 27.96 mmol, 4 eq). The mixture was stirred at 25° C. for 0.5 hr. 4-[4-(dimethoxymethyl)-1-piperidyl]-3,5-difluoro-2-formyl-benzoic acid (2.4 g, 6.99 mmol, 1 eq) and HOAc (1.68 g, 27.96 mmol, 1.60 mL, 4 eq) was added and the mixture was stirred at 25° C. for 0.5 hour. $NaBH_3CN$ (1.32 g, 20.97 mmol, 3 eq) was added and the mixture was stirred at 25° C. for 2 hr. The mixture was concentrated under reduce pressure to remove most of solvent. The mixture was partitioned between ethyl acetate (20 mL) and water (20 mL). The mixture was adjusted to pH around 4 with 0.5 N hydrochloric acid. The mixture was filtered and the cake was collected and dried to give a white solid. The crude was used in next step directly. 4-[4-(dimethoxymethyl)-1-piperidyl]-2-[[(2,6-dioxo-3-piperidyl)amino]methyl]-3,5-difluoro-benzoic acid (1.94 g, 3.54 mmol, 50.57% yield, 83% purity) was obtained as a white solid.

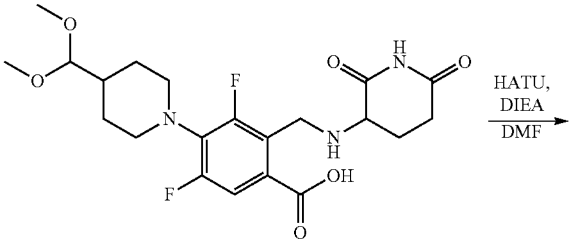

-continued

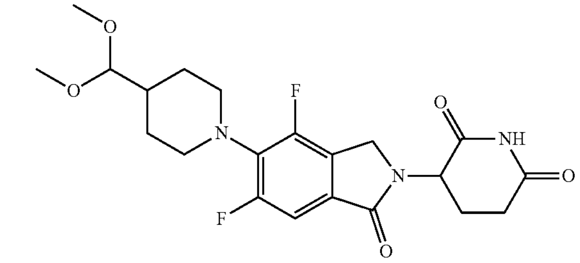

Step 5:

To a solution of 4-[4-(dimethoxymethyl)-1-piperidyl]-2-[[(2,6-dioxo-3-piperidyl)amino]methyl]-3,5-difluoro-benzoic acid (1.94 g, 4.26 mmol, 1 eq) in DMF (15 mL) was added HATU (1.94 g, 5.11 mmol, 1.2 eq) then DIEA (1.65 g, 12.78 mmol, 2.23 mL, 3 eq) was added to the mixture, the reaction mixture was stirred at 25° C. for 2 h. The mixture was poured into water (50 mL), the mixture was filtered and the filtered cake was dried under vacuum. The residue was triturated by petroleum ether and ethyl acetate (20 mL, V/V=1/1).

The filtered cake was dried under vacuum to give 3-[5-[4-(dimethoxymethyl)-1-piperidyl]-4,6-difluoro-1-oxo-isoindolin-2-yl]piperidine-2,6-dione (1.5 g, 3.36 mmol, 78.89% yield, 98% purity) as a white solid.

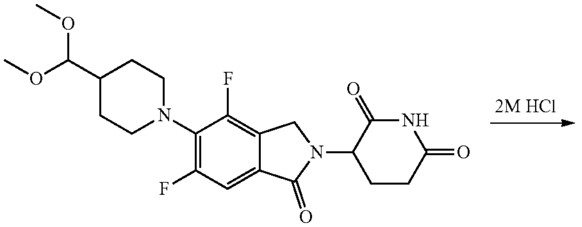

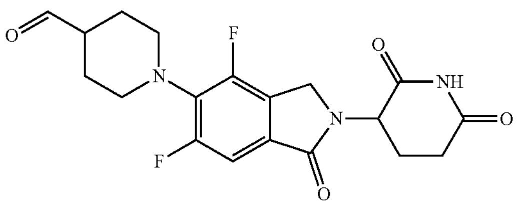

Step 6:

To a solution of 3-[5-[4-(dimethoxymethyl)-1-piperidyl]-4,6-difluoro-1-oxo-isoindolin-2-yl]piperidine-2,6-dione (1 g, 2.29 mmol, 1 eq) and in THF (5 mL) was added HCl (2 M, 5 mL, 4.37 eq) and stirred at 40° C. for 2 h under $N_2$. LCMS showed desired product. The reaction mixture was poured into $H_2O$ (20 mL) and basified with aqueous $NaHCO_3$ till PH=8. The mixture was extracted with ethyl acetate (20 mL*5). Dried over anhydrous $Na_2SO_4$, concentrated in vacuum to give a residue. The residue was without any purification, which used directly in the next step. Compound 1-[2-(2,6-dioxo-3-piperidyl)-4,6-difluoro-1-oxo-isoindolin-5-yl]piperidine-4-carbaldehyde (500 mg, 1.20 mmol, 52.53% yield, 94% purity) as a white solid.

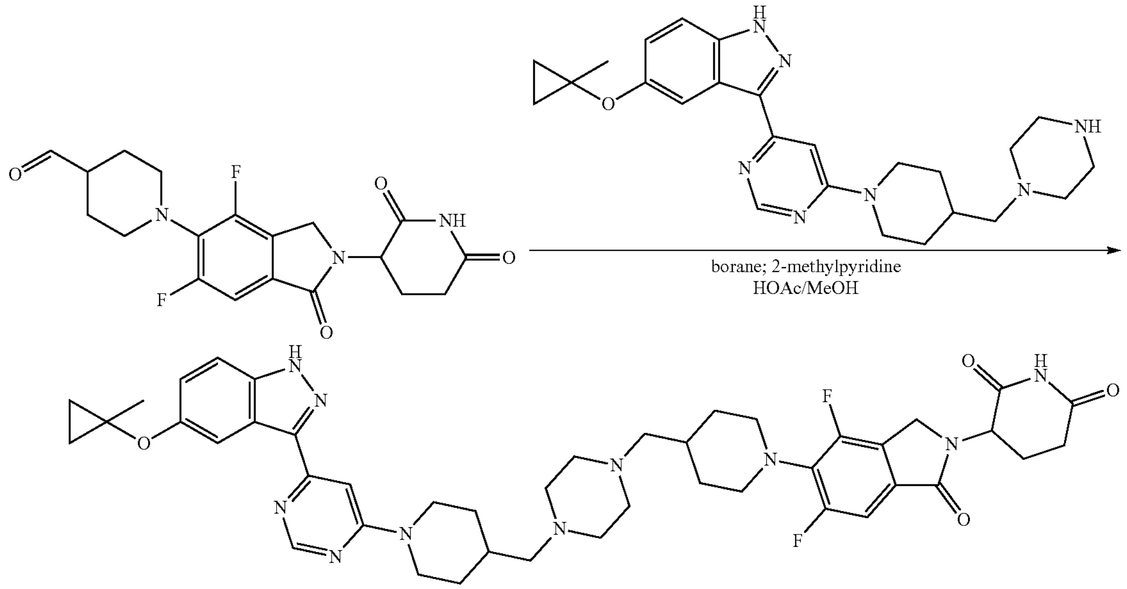

Step 7:

To a mixture of 1-[2-(2,6-dioxo-3-piperidyl)-4,6-difluoro-1-oxo-isoindolin-5-yl]piperidine-4-carbaldehyde (50 mg, 127.76 μmol, 1 eq) in HOAC (1 mL) and MeOH (10 mL) was added a solution of 5-(1-methylcyclopropoxy)-3-[6-[4-(piperazin-1-ylmethyl)-1-piperidyl]pyrimidin-4-yl]-1H-indazole (92.76 mg, 191.64 μmol, 1.5 eq, HCl) and DIEA (49.53 mg, 383.27 μmol, 66.76 uL, 3 eq) in MeOH (0.5 mL). Then borane; 2-methylpyridine (27.33 mg, 255.51 μmol, 2 eq) was added to above solution. After addition, the reaction solution was stirred at 20° C. for 16 h. LCMS showed desired product. The residue was concentrated under reduced pressure to give a residue. The residue was purified by prep-HPLC (column: Xtimate C18 100*30 mm*10 um; mobile phase: [water (FA)-ACN]; B %: 0%-35%, 35 min) to give 3-[4,6-difluoro-5-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (42.3 mg, 50.89 μmol, 39.83% yield, 99% purity) as white solid.

Exemplary Synthesis of Compound 220

Compound 220 was prepared in a manner analogous to compound 219.

Exemplary Synthesis of Compound 221

Compound 221 was prepared in a manner analogous to compound 181 using tert-butyl (3S)-3-methylpiperazine-1-carboxylate.

Exemplary Synthesis of Compound 222

Compound 221 was prepared in a manner analogous to compound 181 using tert-butyl (2S)-2-methylpiperazine-1-carboxylate.

Exemplary Synthesis of Compound 223

Compound 223 was prepared in a manner analogous to compound 219 using tert-butyl 4-fluoro-4-[[1-[6-[5-(1-methylcyclopropoxy)-2-(2-trimethylsilylethoxymethyl)indazol-3-yl]pyrimidin-4-yl]-4-piperidyl]methyl]piperidine-1-carboxylate.

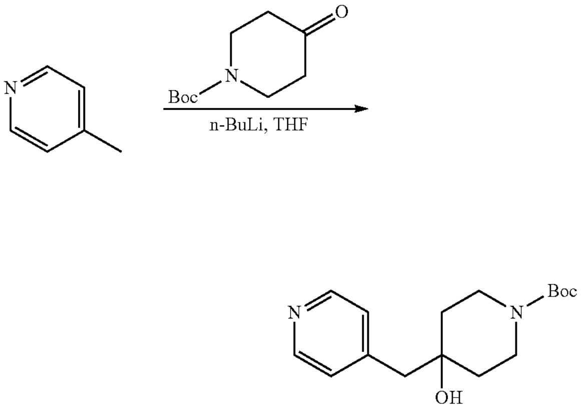

Step 1:

To a mixture of 4-methylpyridine (5 g, 53.69 mmol, 5.26 mL, 1 eq) in THF (100 mL) was dropwise added n-BuLi (2.5 M, 25.77 mL, 1.2 eq) at −70° C. under $N_2$. The mixture was stirred at −70° C. for 3 h to give orange solution, then tert-butyl 4-oxopiperidine-1-carboxylate (10.70 g, 53.69 mmol, 1 eq) in THF (10 mL) was dropwise added, and the solution was stirred at 20° C. for 2 hours to give light yellow solution. LCMS showed the desired compound was formed. The mixture was poured into water (50 mL). The aqueous phase was extracted with ethyl acetate (40 mL*3). The combined organic phase was washed with brine (30 mL*2), dried with anhydrous $Na_2SO_4$, filtered and concentrated in vacuum. The residue was purified by silica gel chromatography (Petroleum ether/Ethyl acetate=0/1) to afford tert-butyl 4-hydroxy-4-(4-pyridylmethyl)piperidine-1-carboxylate (10.33 g, 35.33 mmol, 65.81% yield) as light yellow liquid.

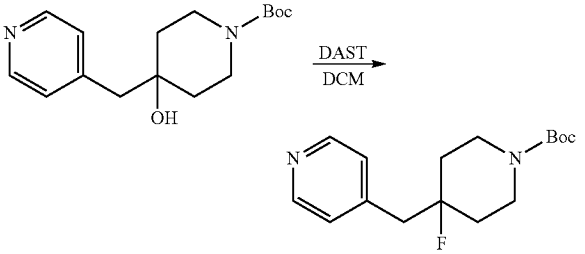

Step 2:

To a mixture of tert-butyl 4-hydroxy-4-(4-pyridylmethyl)piperidine-1-carboxylate (10 g, 34.20 mmol, 1 eq) in DCM (100 mL) was added N-ethyl-N-(trifluoro-λ4-sulfanyl)ethanamine (6.62 g, 41.04 mmol, 5.42 mL, 1.2 eq) drop-wise at −60° C. under $N_2$. The mixture was stirred at −60° C. for 10 hours. TLC (Petroleum ether:Ethyl acetate=0/1) showed the reaction was completed. The reaction was cooled to 0° C. and quenched with aqueous $NaHCO_3$ to adjusted the pH=7-8. The aqueous phase was extracted with DCM (60 mL*2). The combined organic layers were washed with brine (20 mL*2), dried over anhydrous sodium sulfate, filtered and concentrated under reduced pressure to give a residue. The residue was purified by silica gel chromatography (Petroleum ether/Ethyl acetate=1/1) to afford tert-butyl 4-fluoro-4-(4-pyridylmethyl)piperidine-1-carboxylate (7.45 g, crude) as colourless oil.

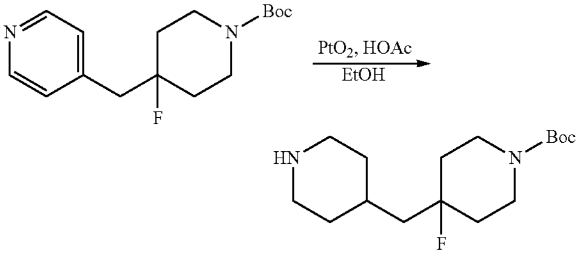

Step 3:

To a solution of tert-butyl 4-fluoro-4-(4-pyridylmethyl)piperidine-1-carboxylate (2 g, 6.79 mmol, 1 eq) in EtOH (20 mL) and HOAc (408.01 mg, 6.79 mmol, 388.58 uL, 1 eq) was added PtO2 (231.43 mg, 1.02 mmol, 0.15 eq) at 25° C. Then the mixture was stirred at 70° C. for 24 h under $H_2$ (50 psi). TLC (Petroleum ether:Ethyl acetate=3/1) showed the reaction was completed. The suspension was filtered through a pad of Celite and the pad or filter cake was washed with EtOH (100 mL×3). The combined filtrates were concentrated to dryness to give product. The residue was used into next step directly without further purification. The product tert-butyl 4-fluoro-4-(4-piperidylmethyl)piperidine-1-carboxylate (2.7 g, crude, HOAC) as brown solid.

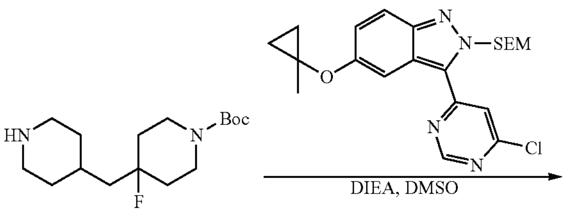

-continued

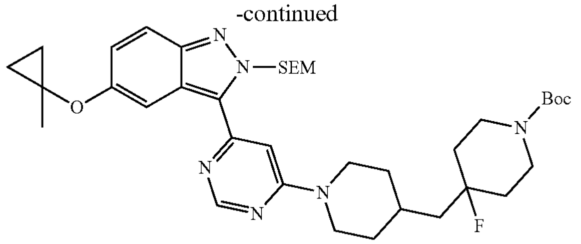

Step 4:

To a mixture of tert-butyl 4-fluoro-4-(4-piperidylmethyl)piperidine-1-carboxylate (200 mg, 554.84 μmol, 1 eq, HOAC) and 2-[[3-(6-chloropyrimidin-4-yl)-5-(1-methylcyclopropoxy)indazol-2-yl]methoxy]ethyl-trimethyl-silane (239.14 mg, 554.84 μmol, 1 eq) in DMSO (4 mL) was added DIEA (358.55 mg, 2.77 mmol, 483.22 uL, 5 eq) in one portion at 90° C. under $N_2$. The mixture was stirred at 90° C. for 2 hours. LCMS showed the reaction was completed. The mixture was cooled to 25° C. and poured into water (10 mL). The aqueous phase was extracted with ethyl acetate (10 mL*2). The combined organic phase was washed with brine (5 mL*2), dried with anhydrous $Na_2SO_4$, filtered and concentrated in vacuum. The residue was used into next step directly without further purification. The product tert-butyl 4-fluoro-4-[[1-[6-[5-(1-methylcyclopropoxy)-2-(2-trimethylsilylethoxymethyl)indazol-3-yl]pyrimidin-4-yl]-4-piperidyl]methyl]piperidine-1-carboxylate (45 mg, 60.87 μmol, 16.27% yield, 94% purity) as light yellow oil.

Exemplary Synthesis of Compound 224

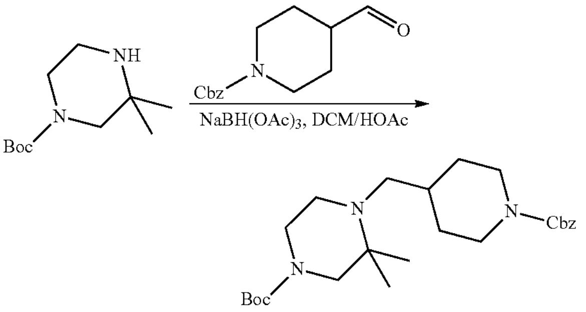

Step 1:

To a solution of benzyl 4-formylpiperidine-1-carboxylate (1.78 g, 7.21 mmol, 1 eq) and HOAC (25.98 mg, 432.69 μmol, 24.75 uL, 0.06 eq) in DCM (10 mL) was added tert-butyl 3,3-dimethylpiperazine-1-carboxylate (1.70 g, 7.93 mmol, 1.1 eq), then the mixture was stirred at 25° C. under $N_2$ for 20 hours, then $NaBH(OAc)_3$ (2.29 g, 10.80 mmol, 1.50 eq) was added the above mixture, and the mixture was stirred at 25° C. for 2 hours. The reaction mixture was quenched by addition sat. $NaHCO_3$ to pH=8-9 and extracted with DCM (20 mL*3). The combined organic layers were washed with brine (50 mL*2), dried over $Na_2SO_4$, filtered and concentrated under reduced pressure to give a residue. The residue was purified by flash silica gel chromatograph (0~25% ethyl acetate in petroleum) to give tert-butyl 4-((1-((benzyloxy)carbonyl)piperidin-4-yl)methyl)-3,3-dimethylpiperazine-1-carboxylate (2.11 g, 4.73 mmol, 65.57% yield) as colourless oil.

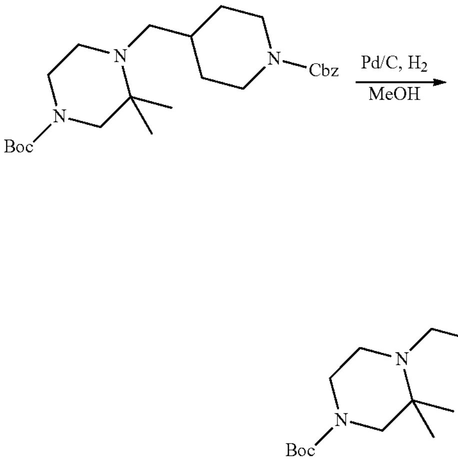

Step 2:

To a solution of tert-butyl 4-[(1-benzyloxycarbonyl-4-piperidyl)methyl]-3,3-dimethyl-piperazine-1-carboxylate (2.1 g, 4.71 mmol, 1 eq) in MeOH (20 mL) was added Pd/C (500 mg, 10% purity) under $N_2$. The suspension was degassed under vacuum and purged with $H_2$ several times. The mixture was stirred under $H_2$ (15 psi) at 25° C. for 1 hour. TLC (petroleum ether:ethyl acetate=1:1) showed the reaction completed. After cooling, the reaction mixture was filtered and filtrate was concentrated under reduced pressure to give tert-butyl 3,3-dimethyl-4-(4-piperidylmethyl)piperazine-1-carboxylate (1.39 g, 4.46 mmol, 94.70% yield) as a white gum.

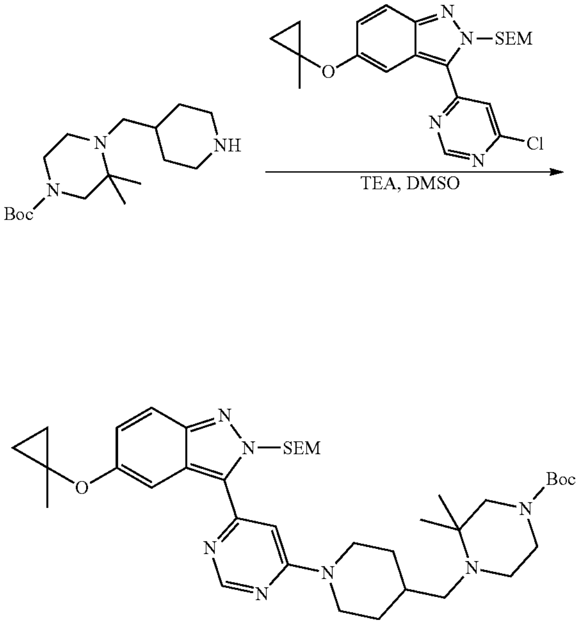

Step 3:

To a solution of 2-[[3-(6-chloropyrimidin-4-yl)-5-(1-methylcyclopropoxy)indazol-2-yl]methoxy]ethyl-trimethyl-silane (0.15 g, 348.03 μmol, 1 eq) in DMSO (3 mL) was added TEA (176.08 mg, 1.74 mmol, 242.20 uL, 5 eq) and tert-butyl 3,3-dimethyl-4-(4-piperidylmethyl)piperazine-1-carboxylate (216.79 mg, 696.05 μmol, 2 eq). The mixture was stirred at 100° C. for 1 hr. TLC indicated 2-[[3-(6-chloropyrimidin-4-yl)-5-(1-methylcyclopropoxy)indazol-2-yl]methoxy]ethyl-trimethyl-silane was consumed completely and one new spot formed. The reaction mixture was quenched by addition EtOAc (50 mL) water 50 ml at 25° C. The organic layers were washed with water (30 mL*3), dried over $Na_2SO_4$, filtered and concentrated under reduced pressure to give a residue. The residue was purified by flash silica gel chromatography (ISCO®; 4 g SepaFlash® Silica Flash Column, Eluent of 0~20% Ethylacetate/Petroleum ethergradient @ 50 mL/min) to give tert-butyl 3,3-dimethyl-4-[[1-[6-[5-(1-methylcyclopropoxy)-2-(2-trimethylsilylethoxymethyl)indazol-3-yl]pyrimidin-4-yl]-4-piperidyl]methyl]piperazine-1-carboxylate (0.19 g, 266.99 μmol, 76.72% yield, 99.210% purity) as a light yellow solid.

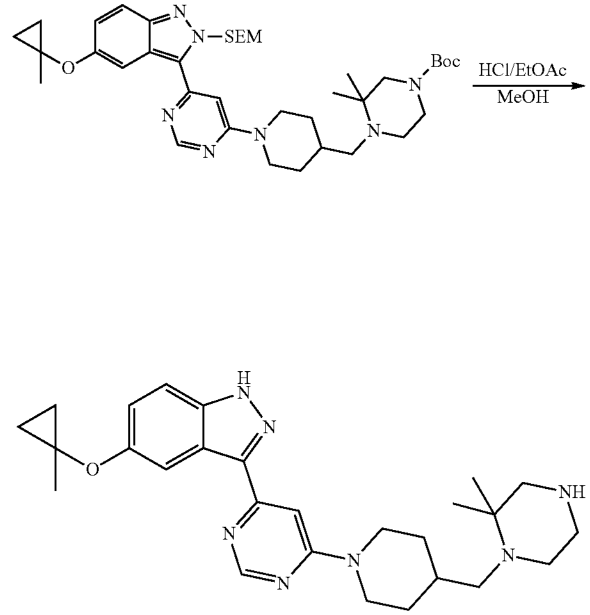

Step 4:

To a solution of tert-butyl 3,3-dimethyl-4-[[1-[6-[5-(1-methylcyclopropoxy)-2-(2-trimethylsilylethoxymethyl)indazol-3-yl]pyrimidin-4-yl]-4-piperidyl]methyl]piperazine-1-carboxylate (0.18 g, 254.96 μmol, 1 eq) in MeOH (3 mL) was added HCl/EtOAc (4 M, 127.48 uL, 2 eq). The mixture was stirred at 25° C. for 4 hr. LC-MS (EB4455-23-P1B) showed tert-butyl 3,3-dimethyl-4-[[1-[6-[5-(1-methylcyclopropoxy)-2-(2-trimethylsilylethoxymethyl)indazol-3-yl]pyrimidin-4-yl]-4-piperidyl]methyl]piperazine-1-carboxylate was consumed completely and one main peak with desired mass was detected. The mixture was concentrated in reduced pressure. The reaction mixture was concentrated under reduced pressure to remove solvent to give 3-[6-[4-[(2,2-dimethylpiperazin-1-yl)methyl]-1-piperidyl]pyrimidin-4-yl]-5-(1-methylcyclopropoxy)-1H-indazole (0.13 g, crude, HCl) as a white solid.

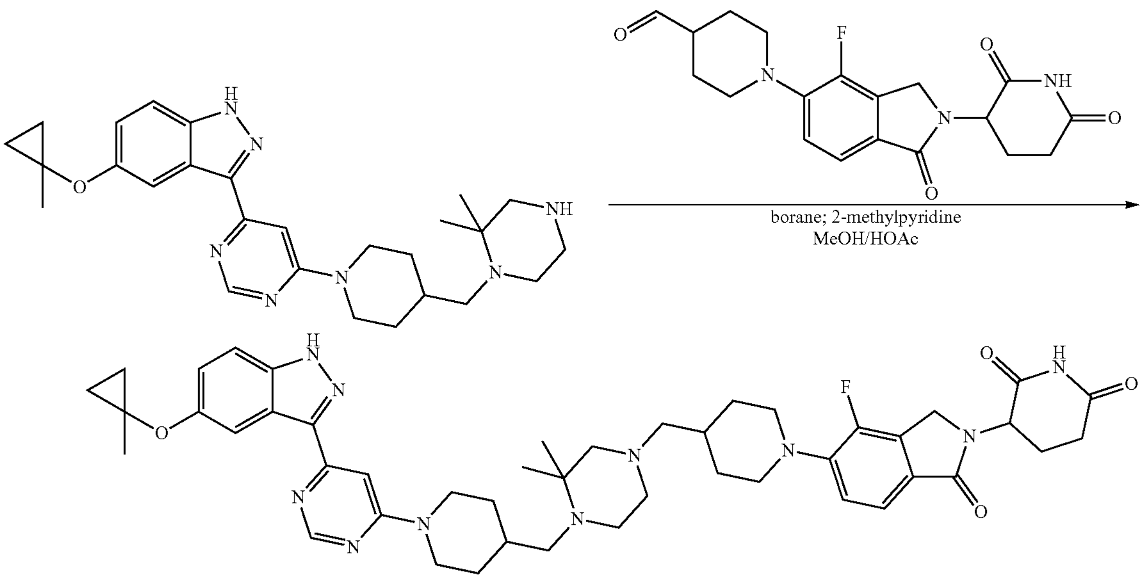

Step 5:

To a solution 1 of 3-[6-[4-[(2,2-dimethylpiperazin-1-yl)methyl]-1-piperidyl]pyrimidin-4-yl]-5-(1-methylcyclopropoxy)-1H-indazole (0.13 g, 253.86 μmol, 1.58 eq, HCl) in MeOH (5 mL) was added DIEA (60 mg, 464.24 μmol, 80.86 uL, 2.89 eq). The mixture was stirred at 25° C. for 60 min. Then to a solution 2 of 1-[2-(2,6-dioxo-3-piperidyl)-4-fluoro-1-oxo-isoindolin-5-yl]piperidine-4-carbaldehyde (60 mg, 160.70 μmol, 1 eq) in MeOH (2 mL) was added AcOH (9.65 mg, 160.70 μmol, 9.19 uL, 1 eq). The solution 2 was stirred at 25° C. for 60 min. Then solution 2 was added solution 1 and borane; 2-methylpyridine (34.38 mg, 321.40 μmol, 2 eq), then the mixture was stirred at for 16 hr. LCMS showed 1-[2-(2,6-dioxo-3-piperidyl)-4-fluoro-1-oxo-isoindolin-5-yl]piperidine-4-carbaldehyde was consumed completely and the desired mass was detected. The residue was purified by prep-HPLC (column: Gemini NX C18 5 um*10*150 mm; mobile phase: [water (FA)-ACN]; B %: 10%-40%, 20 min) to afford 3-[5-[4-[[3,3-dimethyl-4-[[1-[6-[5-(1-methylcyclopropoxy)-1H-indazol-3-yl]pyrimidin-4-yl]-4-piperidyl]methyl]piperazin-1-yl]methyl]-1-piperidyl]-4-fluoro-1-oxo-isoindolin-2-yl]piperidine-2,6-dione (57.4 mg, 65.84 μmol, 40.97% yield, 99.737% purity) as a white solid.

Exemplary Synthesis of Compound 225

Compound 225 was prepared in a manner analogous to compound 224 starting from tert-butyl 3,6-diazabicyclo[3.1.1]heptane-6-carboxylate.

Exemplary Synthesis of Compound 226

Compound 226 was prepared in a manner analogous to compound 224 starting from tert-butyl (1S,4S)-2,5-diazabicyclo[2.2.1]heptane-2-carboxylate.

Exemplary Synthesis of Compound 227

Compound 227 was prepared in a manner analogous to compound 210.

Exemplary Synthesis of Compound 228

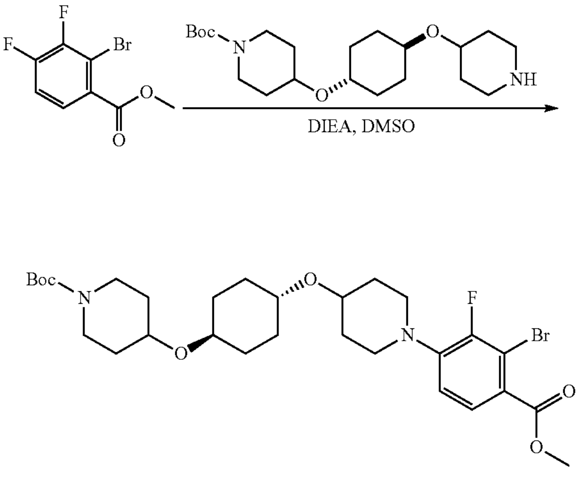

Step 1:

To a solution of methyl 2-bromo-3,4-difluoro-benzoate (1.2 g, 4.78 mmol, 1.52 eq) in MeCN (10 mL) and DMSO (3 mL) was added TEA (1.22 g, 12.02 mmol, 1.67 mL, 3.83 eq) and tert-butyl 4-[4-(4-piperidyloxy)cyclohexoxy]piperidine-1-carboxylate (1.2 g, 3.14 mmol, 1 eq) at 20° C., and the reaction mixture was stirred at 70° C. for 10 hour. TLC showed there was a new spot. The residue was poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by silica gel chromatography (0-15% of Ethyl acetate in Petroleum ether, 15% of Ethyl acetate in Petroleum ether) to give tert-butyl 4-[4-[[1-(3-bromo-2-fluoro-4-methoxycarbonyl-phenyl)-4-piperidyl]oxy]cyclohexoxy]piperidine-1-carboxylate (700 mg, 1.09 mmol, 34.86% yield, 95.84% purity) as a white solid.

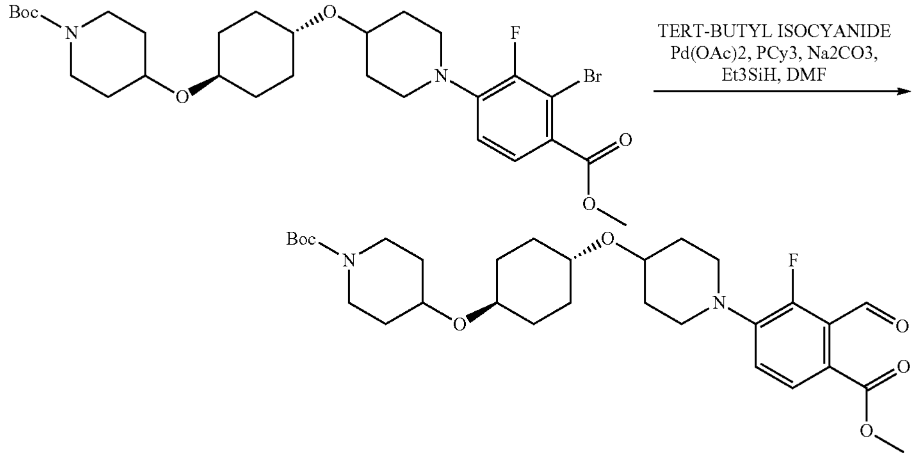

Step 2:

To a solution of tert-butyl 4-[4-[[1-(3-bromo-2-fluoro-4-methoxycarbonyl-phenyl)-4-piperidyl]oxy]cyclohexoxy]piperidine-1-carboxylate (500 mg, 814.92 μmol, 1 eq) in DMF (2 mL) was added tere-butyl idocyanide (135.49 mg, 1.63 mmol, 184.09 uL, 2 eq), $Pd(OAc)_2$ (7.32 mg, 32.60 μmol, 0.04 eq), $PCy_3$ (9.14 mg, 32.60 μmol, 10.57 uL, 0.04 eq), $Na_2CO_3$ (86.37 mg, 814.92 μmol, 1 eq) and $Et_3SiH$ (284.28 mg, 2.44 mmol, 390.49 uL, 3 eq). The mixture was stirred at 100° C. for 24 hr at teflon tank. LCMS showed there was desired MS. The mixture was cooled to 20° C. The residue was poured into water (20 mL). The aqueous phase was extracted with ethyl acetate (20 mL*3). The combined organic phase was washed with brine (20 mL*2), dried with anhydrous $Na_2SO_4$, filtered and concentrated in vacuum. The residue was purified by silica gel chromatography (0-18% of Ethyl acetate in Petroleum ether, 18% of Ethyl acetate in Petroleum ether) to give tert-butyl 4-[4-[[1-(2-fluoro-3-formyl-4-methoxycarbonyl-phenyl)-4-piperidyl]oxy]cyclohexoxy]piperidine-1-carboxylate (400 mg, 603.55 μmol, 18.52% yield, 84.9% purity) as a yellow solid.

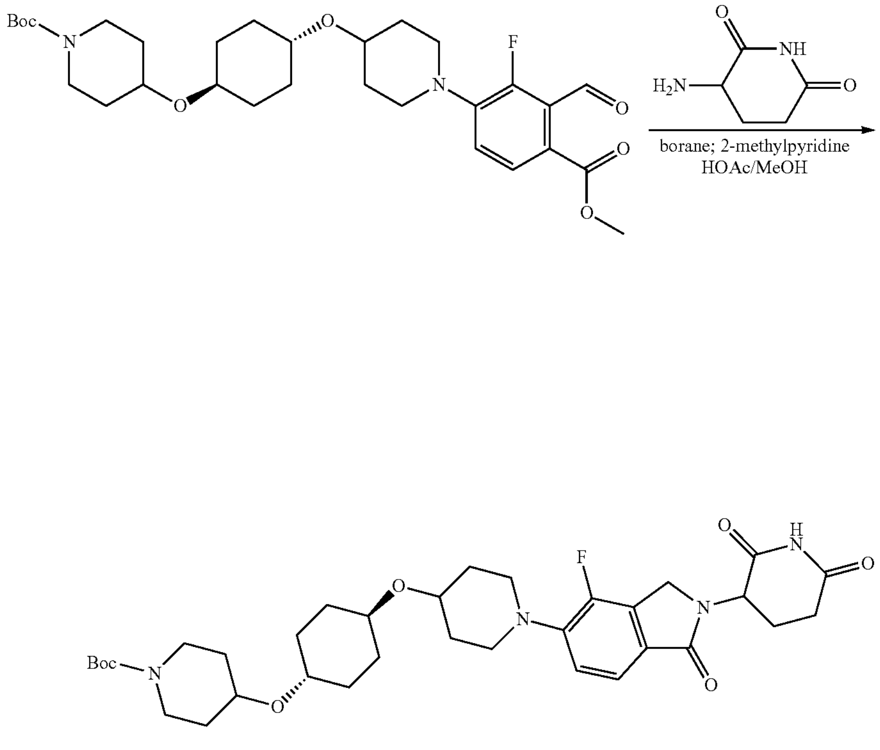

Step 3:

To a mixture of tert-butyl 4-[4-[[1-(2-fluoro-3-formyl-4-methoxycarbonyl-phenyl)-4-piperidyl]oxy]cyclohexoxy]piperidine-1-carboxylate (300 mg, 533.17 μmol, 1 eq) and 3-aminopiperidine-2,6-dione (131.63 mg, 799.76 μmol, 1.5 eq, HCl) in MeOH (10 mL) was added HOAc (0.5 mL) and borane; 2-methylpyridine (114.06 mg, 1.07 mmol, 2 eq) in one portion at 25° C. under $N_2$. The mixture was stirred at 25° C. for 16 hours to give red suspension. LCMS showed there was desired MS. The reaction mixture was filtered and the filter cake was washed with 20 mL of TBME, dried in vacuum to give tert-butyl 4-[4-[[1-[2-(2,6-dioxo-3-piperidyl)-4-fluoro-1-oxo-isoindolin-5-yl]-4-piperidyl]oxy]cyclohexoxy]piperidine-1-carboxylate (170 mg, 227.46 μmol, 42.66% yield, 86% purity) as a red solid.

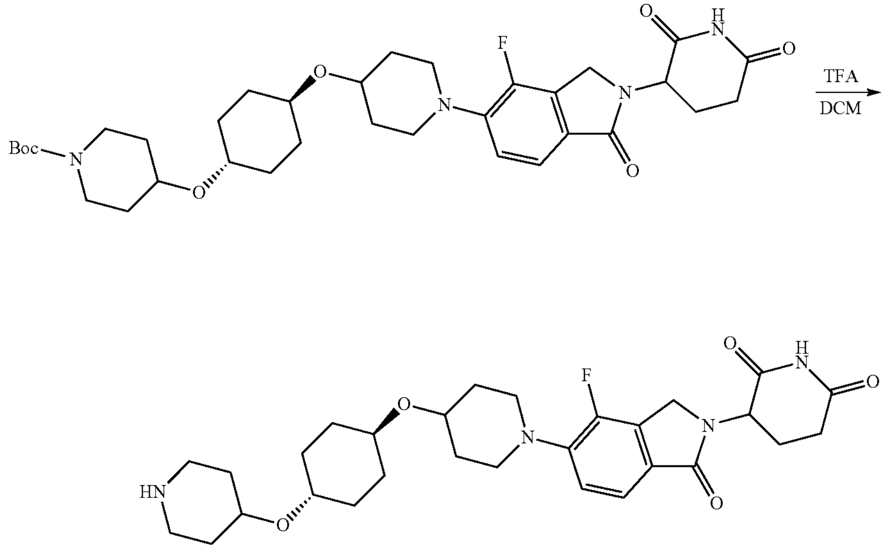

Step 4:

To a mixture of tert-butyl 4-[4-[[1-[2-(2,6-dioxo-3-piperidyl)-4-fluoro-1-oxo-isoindolin-5-yl]-4-piperidyl]oxy]cyclohexoxy]piperidine-1-carboxylate (170 mg, 264.49 μmol, 1 eq) in DCM (5 mL) was added TFA (3.08 g, 27.01 mmol, 2 mL, 102.13 eq) in one portion at 25° C. under $N_2$. The mixture was stirred at 25° C. for 30 min. TLC showed the reaction was completed. The mixture was concentrated in vacuum to give 3-[4-fluoro-1-oxo-5-[4-[4-(4-piperidyloxy)cyclohexoxy]-1-piperidyl]isoindolin-2-yl]piperidine-2,6-dione (170 mg, 199.34 μmol, 75.37% yield, 77% purity, TFA) as a red oil.

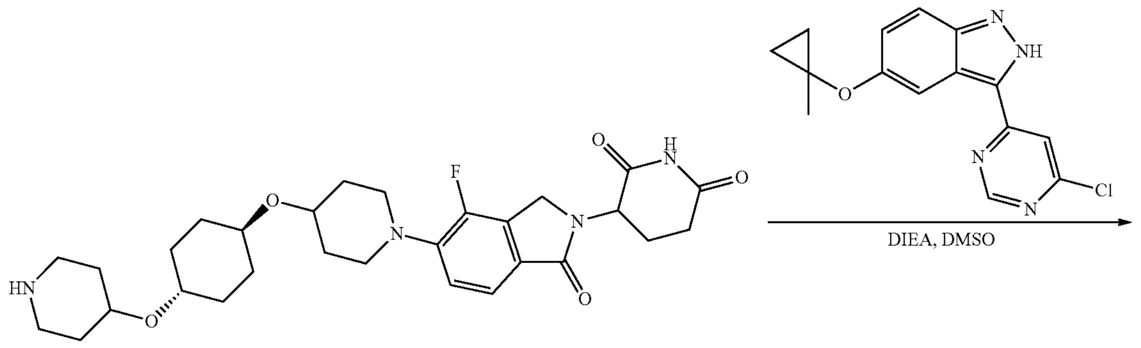

-continued

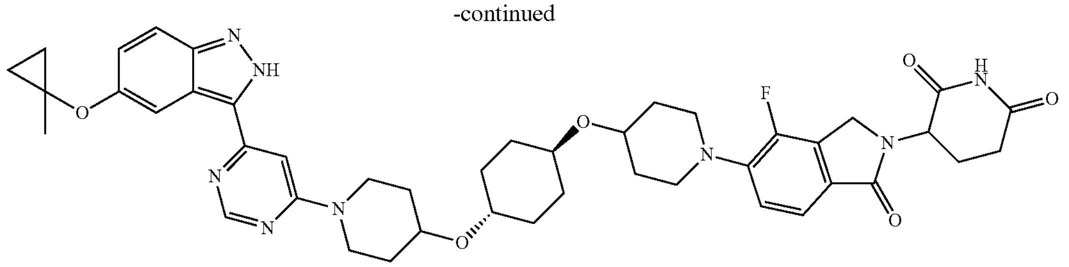

Step 5:

To a solution of 3-(6-chloropyrimidin-4-yl)-5-(1-methylcyclopropoxy)-2H-indazole (70 mg, 232.76 µmol, 8.99 e-1 eq) and 3-[4-fluoro-1-oxo-5-[4-[4-(4-piperidyloxy)cyclohexoxy]-1-piperidyl]isoindolin-2-yl]piperidine-2,6-dione (170 mg, 258.88 µmol, 1 eq, TFA) in DMSO (10 mL) and DIEA (334.58 mg, 2.59 mmol, 450.92 uL, 10 eq). The mixture was stirred at 80° C. for 10 h. LCMS showed desired product MS. The resulting product was poured into $H_2O$ (20 mL). The mixture was extracted with ethyl acetate (20 mL*3). The organic phase was washed with brine (15 mL*2), dried over anhydrous $Na_2SO_4$, concentrated in vacuum to give a residue. The residue was purified by prep-HPLC (column: Xtimate C18 100*30 mm*10 um; mobile phase: [water (FA)-ACN]; B %: 10%-50%, 35 min) to give 3-[4-fluoro-5-[4-[4-[[1-[6-[5-(1-methylcyclopropoxy)-2H-indazol-3-yl]pyrimidin-4-yl]-4-piperidyl]oxy]cyclohexoxy]-1-piperidyl]-1-oxo-isoindolin-2-yl]piperidine-2,6-dione (62.6 mg, 72.92 µmol, 28.17% yield, 94% purity) as a red solid.

Exemplary Synthesis of Compound 229

Compound 229 was prepared in a manner analogous to compound 181.

Exemplary Synthesis of Compound 230

Compound 230 was prepared in a manner analogous to compound 224 starting with tert-butyl (1R,4R)-5-(4-piperidylmethyl)-2,5-diazabicyclo[2.2.1]heptane-2-carboxylate.

Exemplary Synthesis of Compound 231

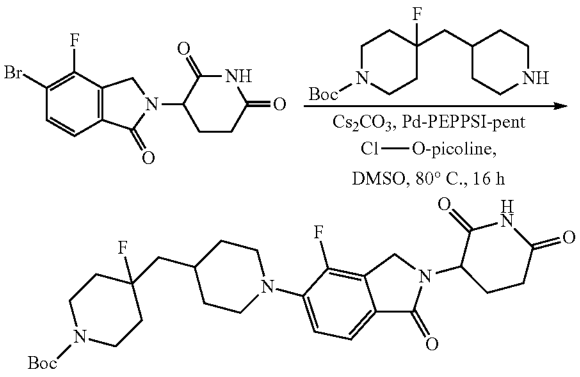

Step 1:

A mixture of 3-(5-bromo-4-fluoro-1-oxo-isoindolin-2-yl)piperidine-2,6-dione (600 mg, 1.76 mmol, 1 eq), tert-butyl 4-fluoro-4-(4-piperidylmethyl)piperidine-1-carboxylate (792.57 mg, 2.64 mmol, 1.5 eq) in DMSO (10 mL) was added $Cs_2CO_3$ (1.72 g, 5.28 mmol, 3 eq), Pd-PEPPSI-pent Cl—O-picoline (95.51 mg, 175.88 µmol, 0.1 eq), and then the mixture was stirred at 90° C. for 12 hr under $N_2$ atmosphere. TLC (Petroleum ether:Ethyl acetate=0:1) showed one new major spot. LCMS showed desired MS. The resulting product was poured into FA aqueous solution adjust pH=5-6. The mixture was extracted with ethyl acetate (20 mL*3). The organic phase was washed with brine (20 mL), dried over anhydrous $Na_2SO_4$, concentrated in vacuum to give a residue. The residue was purified by silica gel column chromatography (0 to 100% Ethyl acetate in Petroleum ether) to give tert-butyl 4-[[1-[2-(2,6-dioxo-3-piperidyl)-4-fluoro-1-oxo-isoindolin-5-yl]-4-piperidyl]methyl]-4-fluoro-piperidine-1-carboxylate (700 mg, 898.99 µmol, 51.11% yield, 72% purity) as a yellow solid.

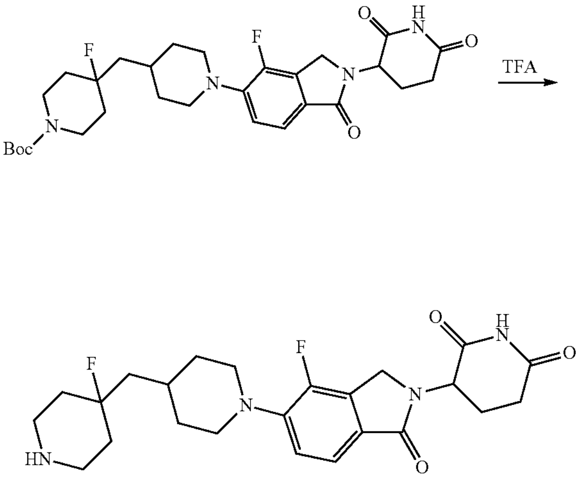

Step 2:

A mixture of tert-butyl 4-[[1-[2-(2,6-dioxo-3-piperidyl)-4-fluoro-1-oxo-isoindolin-5-yl]-4-piperidyl]methyl]-4-fluoro-piperidine-1-carboxylate (700 mg, 1.25 mmol, 1 eq) in DCM (5 mL) was added TFA (3.08 g, 27.01 mmol, 2 mL, 21.63 eq), and then the mixture was stirred at 25° C. for 1 hr under $N_2$ atmosphere. TLC (Petroleum ether:Ethyl acetate=0:1) showed one new major spot. The resulting product was concentrated in vacuum to give 3-[4-fluoro-5-[4-[(4-fluoro-4-piperidyl)methyl]-1-piperidyl]-1-oxo-isoindolin-2-yl]piperidine-2,6-dione (600 mg, 1.09 mmol, 87.65% yield, 84% purity) as a yellow solid.

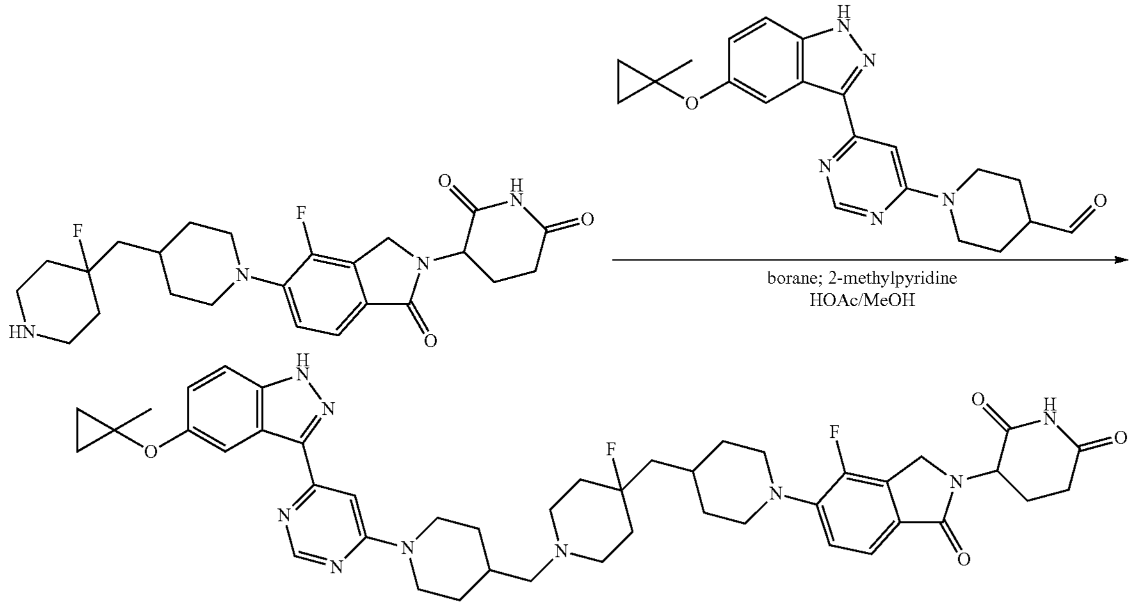

Step 3:

A mixture of 1-[6-[5-(1-methylcyclopropoxy)-1H-indazol-3-yl]pyrimidin-4-yl]piperidine-4-carbaldehyde (70 mg, 185.46 μmol, 1 eq), 3-[4-fluoro-5-[4-[(4-fluoro-4-piperidyl)methyl]-1-piperidyl]-1-oxo-isoindolin-2-yl]piperidine-2,6-dione (85.41 mg, 185.46 μmol, 1 eq) in MeOH (10 mL) and AcOH (2 mL) was added borane; 2-methylpyridine (39.67 mg, 370.92 μmol, 2 eq) and then the mixture was stirred at 25° C. for 12 hr. LCMS showed desired MS. The resulting product was poured into $H_2O$ (10 mL). The mixture was extracted with ethyl acetate (50 mL*3). The organic phase was washed with brine (50 mL), dried over anhydrous $Na_2SO_4$ concentrated in vacuum to give a residue The residue was purified by prep-HPLC (column: Xtimate C18 100*30 mm*10 um; mobile phase: [water (0.225% FA)-ACN]; B %: 0%-35%, 40 min) to give 3-[4-fluoro-5-[4-[[4-fluoro-1-[[1-[6-[5-(1-methylcyclopropoxy)-1H-indazol-3-yl]pyrimidin-4-yl]-4-piperidyl]methyl]-4-piperidyl]methyl]-1-piperidyl]-1-oxo-isoindolin-2-yl]piperidine-2,6-dione (81 mg, 97.56 μmol, 52.60% yield, 99% purity) as a white solid.

Exemplary Synthesis of Compound 232

Compound 232 was prepared in a manner analogous to compound 231.

Exemplary Synthesis of Compound 233

Compound 233 was prepared in a manner analogous to compound 126 using intermediate tert-butyl 4-[3-(4-pyridyloxy)cyclobutoxy]piperidine-1-carboxylate.

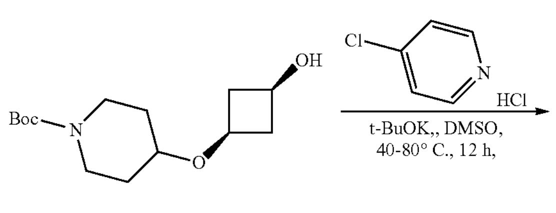

-continued

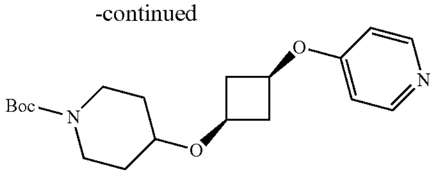

Step 1:

To a mixture of sodium tert-butoxide (3.00 g, 31.22 mmol, 2.82 eq) and tert-butyl 4-(3-hydroxycyclobutoxy)piperidine-1-carboxylate (3.00 g, 11.06 mmol, 1 eq) in dimethylsulfoxide (30 mL) was added 4-chloropyridine (2.16 g, 14.37 mmol, 1.3 eq, hydrochloride) at 40° C., then the mixture was stirred at 80° C. for 12 h. LCMS showed the desired product's mass. The reaction mixture was added water (50 mL) and extracted with ethyl acetate (30 mL*3). The combined organic layers were washed with brine (50 mL), dried over anhydrous sodium sulfate, filtered and concentrated under reduced pressure to give a residue. The residue was purified by flash silica gel chromatography (ISCO®; 12 g SepaFlash® Silica Flash Column, Eluent of 0~80% Ethylacetate/Petroleum ethergradient @ 40 mL/min). Compound tert-butyl 4-[3-(4-pyridyloxy)cyclobutoxy]piperidine-1-carboxylate (2.60 g, 7.46 mmol, 67% yield) was obtained as a yellow solid.

Exemplary Synthesis of Compound 234

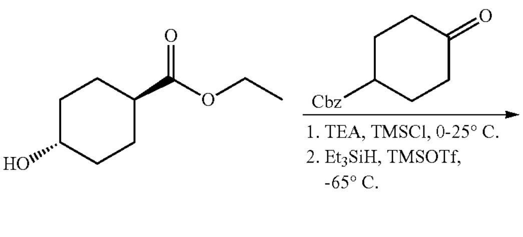

-continued

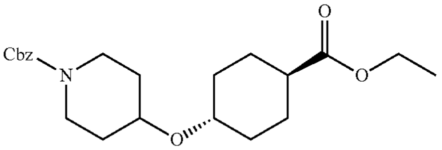

Step 1:

To a solution of ethyl 4-hydroxycyclohexanecarboxylate (20 g, 116.13 mmol, 1 eq) in THF (200 mL) was added TMSCl (13.88 g, 127.74 mmol, 16.21 mL, 1.1 eq) and TEA (14.10 g, 139.36 mmol, 19.40 mL, 1.2 eq) at 0° C., and the reaction mixture was stirred at 25° C. for 1 hour. The reaction mixture was filtered, and the filtrate was concentrated under reduced pressure to give a residue. Then to a stirred solution of above residue and benzyl 4-oxopiperidine-1-carboxylate (31.15 g, 133.55 mmol, 26.63 mL, 1.15 eq) in DCM (300 mL) was added $Et_3SiH$ (20.25 g, 174.19 mmol, 27.82 mL, 1.5 eq) and TMSOTf (14.20 g, 63.87 mmol, 11.54 mL, 0.55 eq) dropwise at −65° C. under $N_2$, and the reaction mixture was stirred at 0° C. under $N_2$ for 3 hours. TLC (Petroleum ether:Ethyl acetate=3:1, PMA, $R_f$=0.43) showed new spots formed. The reaction mixture was quenched by addition water (300 mL) and extracted with DCM (200 mL×3). The combined organic layers were washed with brine (300 mL), dried over $Na_2SO_4$, filtered and concentrated under reduced pressure to give a residue. The residue was purified by flash silica gel chromatography (ISCO®; 120 g SepaFlash® Silica Flash Column, Eluent of 0~20% Ethyl acetate/Petroleum ethergradient @ 100 mL/min). Compound benzyl 4-(4-ethoxycarbonylcyclohexoxy)piperidine-1-carboxylate (40.8 g, 104.75 mmol, 90.20% yield) was obtained as a colorless oil.

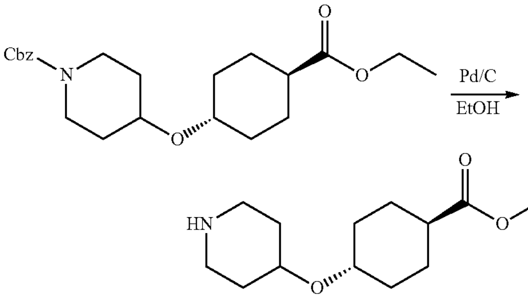

Step 2:

To a solution of benzyl 4-(4-ethoxycarbonylcyclohexoxy) piperidine-1-carboxylate (40.8 g, 104.75 mmol, 1 eq) in EtOH (40 mL) was added Pd/C (8 g, 104.75 mmol, 10% purity, 1 eq), then the solution was stirred at 25° C. under $H_2$ (15 psi) for 4 hours. TLC (Petroleum ether:Ethyl acetate=3:1, $I_2$) showed a new spot formed. The reaction mixture was filtered and concentrated under reduced pressure to give a residue. Compound ethyl 4-(4-piperidyloxy)cyclohexanecarboxylate (26.7 g, 104.56 mmol, 99.82% yield) was obtained as a colorless solid.

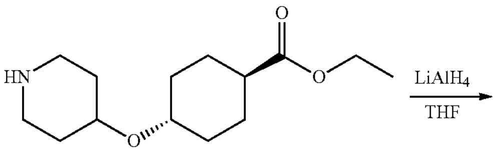

-continued

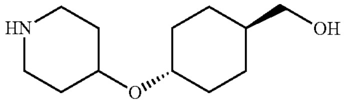

Step 3:

To a solution of ethyl 4-(4-piperidyloxy)cyclohexanecarboxylate (10 g, 39.16 mmol, 1 eq) in THF (70 mL) was added $LiAlH_4$ (2.23 g, 58.74 mmol, 1.5 eq) at 0° C., then the solution was stirred at 0° C. under $N_2$ for 2 hours. TLC (Dichloromethane:Methanol=5:1) showed starting materials was consumed completely. The reaction mixture was quenched by addition water (2 mL) and 15% NaOH (4 mL) at 0° C., and then dried over $Na_2SO_4$, filtered and concentrated under reduced pressure to give a residue. Compound [4-(4-piperidyloxy)cyclohexyl]methanol (7.9 g, 37.03 mmol, 94.57% yield) was obtained as a light yellow solid.

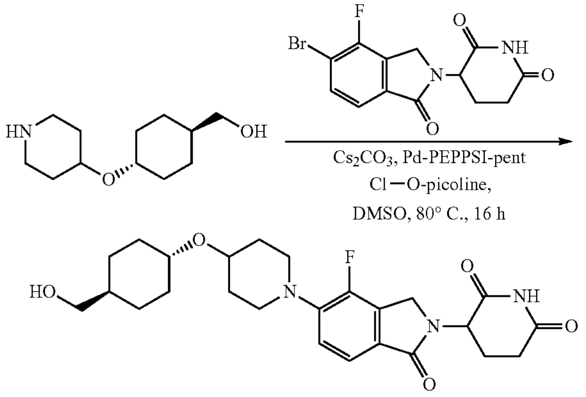

Step 4:

To a solution of 3-(5-bromo-4-fluoro-1-oxo-isoindolin-2-yl)piperidine-2,6-dione (300 mg, 879.42 μmol, 1 eq) and [4-(4-piperidyloxy)cyclohexyl]methanol (225.11 mg, 1.06 mmol, 1.2 eq) in DMSO (10 mL) was added $Cs_2CO_3$ (859.60 mg, 2.64 mmol, 3 eq) and Pd-PEPPSI-pent Cl—O-picoline (47.75 mg, 87.94 μmol, 0.1 eq) stirred at 90° C. under $N_2$ for 16 h. LCMS showed ~43% desire compound and the TLC (Petroleum ether:Ethyl acetate=0:1, $I_2$) showed a main spot formed. The reaction mixture was quenched by addition formic acid (3 mL) at 0° C., and extracted with EtOAc (50 mL×3). The combined organic layers were washed with brine (30 mL×5), dried over $Na_2SO_4$, filtered and concentrated under reduced pressure to give a residue. The residue was purified by flash silica gel chromatography (ISCO®; 12 g SepaFlash® Silica Flash Column, Eluent of 0~100% Ethyl acetate/Petroleum ethergradient @ 60 mL/min). Compound 3-[4-fluoro-5-[4-[4-(hydroxymethyl) cyclohexoxy]-1-piperidyl]-1-oxo-isoindolin-2-yl]piperidine-2,6-dione (95 mg, 193.60 μmol, 22.01% yield, 96.5% purity) was obtained as a light yellow solid.

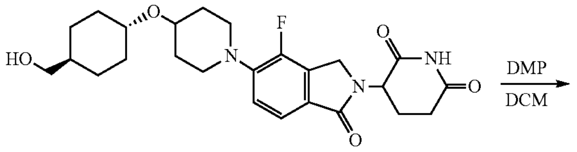

-continued

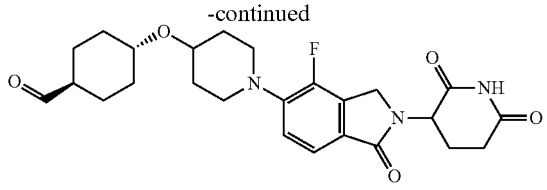

Step 5:

To a solution of 3-[4-fluoro-5-[4-[4-(hydroxymethyl)cyclohexoxy]-1-piperidyl]-1-oxo-isoindolin-2-yl]piperidine-2,6-dione (95 mg, 200.62 μmol, 1 eq) in DCM (10 mL) was added DMP (255.27 mg, 601.86 μmol, 186.33 uL, 3 eq), then the mixture was stirred at 25° C. for 2 hours. TLC (Petroleum ether:Ethyl acetate=0:1, $I_2$) showed a new spot formed. The reaction mixture was quenched by addition Sat.$NaHCO_3$ adjust pH~8 at 0° C., and extracted with DCM (30 mL*3). The combined organic layers were washed with saturated $Na_2SO_3$ (30 mL*3) and brine (30 mL*3), dried over $Na_2SO_4$, filtered and concentrated under reduced pressure to give a residue. Compound 4-[[1-[2-(2,6-dioxo-3-piperidyl)-4-fluoro-1-oxo-isoindolin-5-yl]-4-piperidyl]oxy]cyclohexanecarbaldehyde (90 mg, 164.15 μmol, 81.82% yield, 86% purity) was obtained as a light yellow solid.

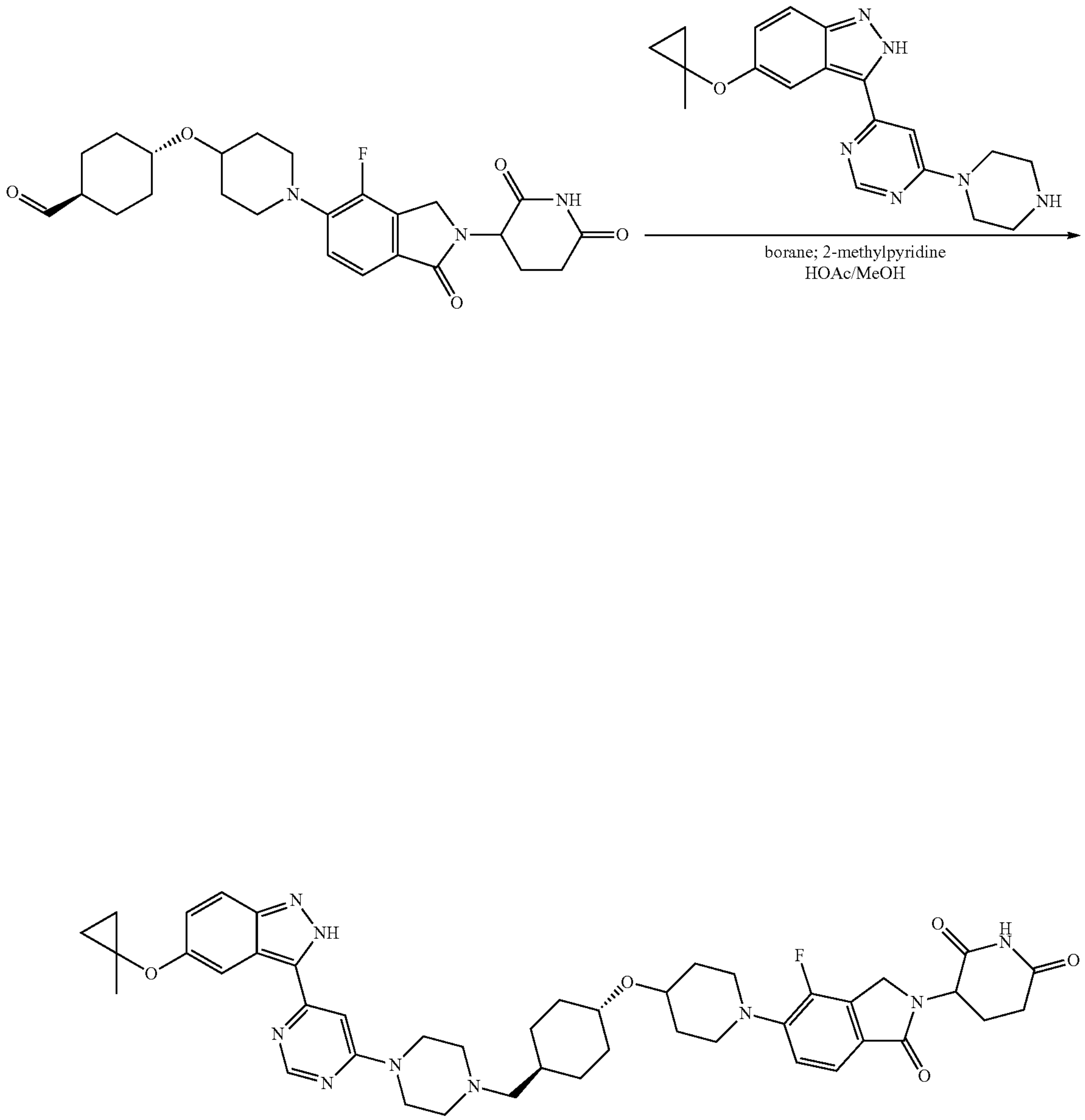

Step 6:

To a solution of 4-[[1-[2-(2,6-dioxo-3-piperidyl)-4-fluoro-1-oxo-isoindolin-5-yl]-4-piperidyl]oxy]cyclohexanecarbaldehyde (90 mg, 190.87 μmol, 1 eq) and 5-(1-methylcyclopropoxy)-3-(6-piperazin-1-ylpyrimidin-4-yl)-2H-indazole (97.51 mg, 209.96 μmol, 1.1 eq, TFA) in MeOH (20 mL) was added AcOH (2.29 mg, 38.17 μmol, 2.18 uL, 0.2 eq) and borane; 2-methylpyridine (40.83 mg, 381.74 μmol, 2 eq), then the solution was stirred at 25° C. for 16 hours. LCMS showed ~78% desire compound and the starting materials was consumed completely. The reaction mixture was concentrated under reduced pressure to give a residue. The residue was purified by prep-HPLC (column: Xtimate C18 100*30 mm*10 um; mobile phase: [water (FA)-ACN]; B %: 10%-40%, 35 min). Compound 3-[4-fluoro-5-[4-[4-[[4-[6-[5-(1-methylcyclopropoxy)-2H-indazol-3-yl]pyrimidin-4-yl]piperazin-1-yl]methyl]cyclohexoxy]-1-piperidyl]-1-oxo-isoindolin-2-yl]piperidine-2,6-dione (40.6 mg, 50.04 μmol, 26.22% yield, 99.329% purity) was obtained as a white solid.

Exemplary Synthesis of Compound 235

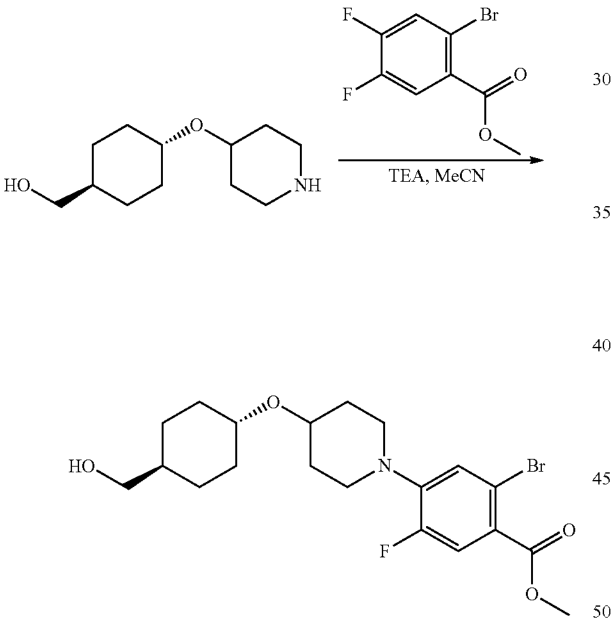

Step 1:

To a solution of [4-(4-piperidyloxy)cyclohexyl]methanol (3.9 g, 15.61 mmol, 1 eq, HCl) and methyl 2-bromo-4,5-difluoro-benzoate (3.92 g, 15.61 mmol, 1 eq) in MeCN (10 mL) was added TEA (4.74 g, 46.84 mmol, 6.52 mL, 3 eq), then the mixture was stirred at 70° C. for 16 hours. TLC (Petroleum ether:Ethyl acetate=2:1, UV=254 nm) showed a new spot formed. The reaction mixture was concentrated under reduced pressure to give a residue. The residue was purified by flash silica gel chromatography (ISCO®; 20 g SepaFlash® Silica Flash Column, Eluent of 0-34% Ethyl acetate/Petroleum ethergradient @ 60 mL/min). Compound methyl 2-bromo-5-fluoro-4-[4-[4-(hydroxymethyl)cyclohexoxy]-1-piperidyl]benzoate (2.5 g, 5.63 mmol, 36.03% yield) was obtained as a white solid.

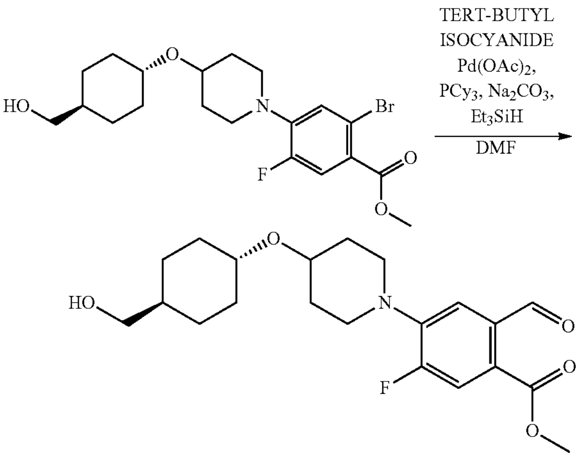

Step 2:

To a solution of methyl 2-bromo-5-fluoro-4-[4-[4-(hydroxymethyl)cyclohexoxy]-1-piperidyl]benzoate (2.5 g, 5.63 mmol, 1 eq) in DMF (20 mL) was added tert-butyl isocyanide (935.46 mg, 11.25 mmol, 1.27 mL, 2 eq), $Pd(OAc)_2$ (50.53 mg, 225.06 μmol, 0.04 eq), PCy3 (78.89 mg, 281.32 μmol, 91.20 uL, 0.05 eq), $Na_2CO_3$ (596.34 mg, 5.63 mmol, 1 eq) and $Et_3SiH$ (1.96 g, 16.88 mmol, 2.70 mL, 3 eq). The mixture was stirred at 65° C. for 16 hours under $N_2$. LCMS showed ~37% desired compound and TLC (Petroleum ether:Ethyl acetate=3:1, UV=254 nm) showed a main spot formed. The reaction mixture was added water (50 mL) and extracted with EtOAc (50 mL*3). The combined organic layers were washed with brine (50 mL*5), dried over $Na_2SO_4$, filtered and concentrated under reduced pressure to give a residue. The residue was purified by flash silica gel chromatography (ISCO®; 12 g SepaFlash® Silica Flash Column, Eluent of 0~8% Ethyl acetate/Petroleum ethergradient @ 60 mL/min). Compound methyl 5-fluoro-2-formyl-4-[4-[4-(hydroxymethyl)cyclohexoxy]-1-piperidyl]benzoate (1.5 g, 3.32 mmol, 58.95% yield, 87% purity) was obtained as a light yellow oil.

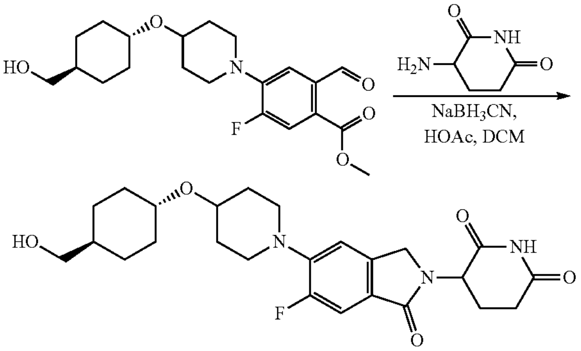

Step 3:

To a solution of 3-aminopiperidine-2,6-dione (585.66 mg, 3.56 mmol, 2 eq, HCl) in DCM (15 mL) was added NaOAc (583.80 mg, 7.12 mmol, 4 eq), then the solution was stirred at 25° C. for 1 hour, then methyl 5-fluoro-2-formyl-4-(4-(((1r,4r)-4-(hydroxymethyl)cyclohexyl)oxy)piperidin-1-yl) benzoate (0.7 g, 1.78 mmol, 1 eq) and HOAc (21.37 mg, 355.83 μmol, 20.35 uL, 0.2 eq) was added the solution, then the solution was stirred at 25° C. for 0.5 hour, then $NaBH_3CN$ (223.61 mg, 3.56 mmol, 2 eq) was added the solution, then the mixture was stirred at 25° C. for 16 hours. LCMS showed ~33% compound and the TLC (Petroleum ether:Ethyl acetate=0:1, $I_2$) starting materials was consumed completely. The reaction mixture was filtered and concentrated under reduced pressure to give a residue. Compound 3-(6-fluoro-5-(4-(((1r,4r)-4-(hydroxymethyl)cyclohexyl)oxy)piperidin-1-yl)-1-oxoisoindolin-2-yl)piperidine-2,6-dione (250 mg, 475.15 μmol, 26.71% yield, 90% purity) was obtained as a white solid.

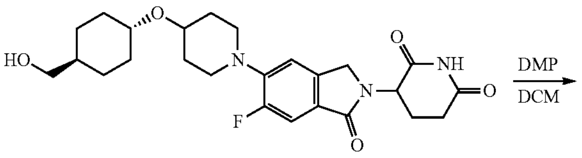

-continued

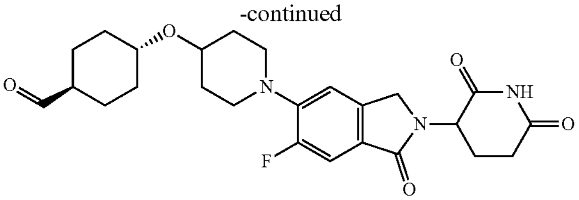

Step 4:

To a solution of 3-[6-fluoro-5-[4-[4-(hydroxymethyl)cyclohexoxy]-1-piperidyl]-1-oxo-isoindolin-2-yl]piperidine-2,6-dione (400 mg, 844.71 μmol, 1 eq) in DCM (10 mL) was added DMP (1.07 g, 2.53 mmol, 784.55 uL, 3 eq), then the solution was stirred at 0° C. for 2 hours. TLC (Petroleum ether:Ethyl acetate=0:1, PMA) showed a new spot formed. The reaction mixture was filtered and concentrated under reduced pressure to give a residue. Compound 4-[[1-[2-(2,6-dioxo-3-piperidyl)-6-fluoro-1-oxo-isoindolin-5-yl]-4-piperidyl]oxy]cyclohexanecarbaldehyde (300 mg, crude) was obtained as a white solid.

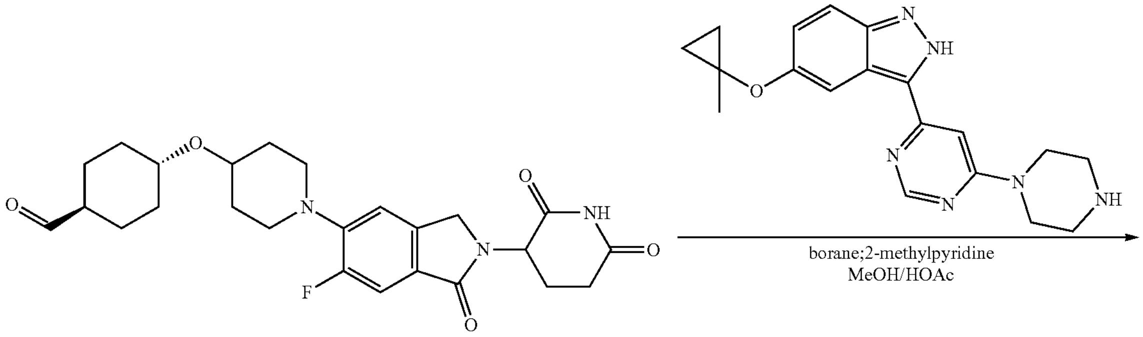

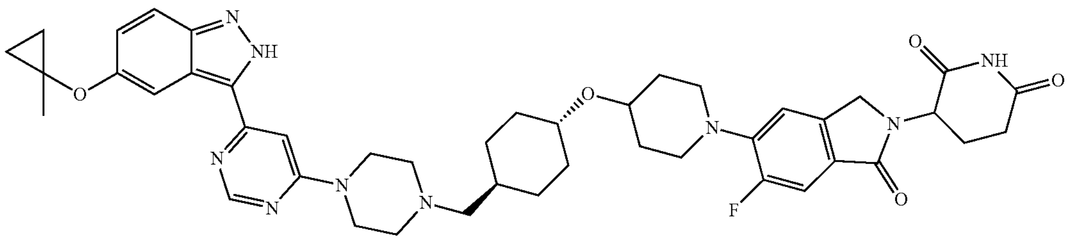

Step 5:

To a solution of 4-[[1-[2-(2,6-dioxo-3-piperidyl)-6-fluoro-1-oxo-isoindolin-5-yl]-4-piperidyl]oxy]cyclohexanecarbaldehyde (100 mg, 212.08 μmol, 1 eq) and 5-(1-methylcyclopropoxy)-3-(6-piperazin-1-ylpyrimidin-4-yl)-2H-indazole (98.50 mg, 254.50 μmol, 1.2 eq, HCl) in MeOH (5 mL) was added borane; 2-methylpyridine (45.37 mg, 424.16 μmol, 2 eq), then the solution was stirred at 25° C. for 16 hours. LCMS showed ~45.9% desire compound and the starting materials was consumed completely. The residue was purified by prep-HPLC (column: Xtimate C18 100*30 mm*10 um; mobile phase: [water (FA)-ACN]; B %: 10%-40%, 35 min). Compound 3-[6-fluoro-5-[4-[4-[[4-[6-[5-(1-methylcyclopropoxy)-2H-indazol-3-yl]pyrimidin-4-yl]piperazin-1-yl]methyl]cyclohexoxy]-1-piperidyl]-1-oxo-isoindolin-2-yl]piperidine-2,6-dione (99.2 mg, 115.93 μmol, 54.66% yield, 99.566% purity, FA) was obtained as a white solid.

Exemplary Synthesis of Compound 236

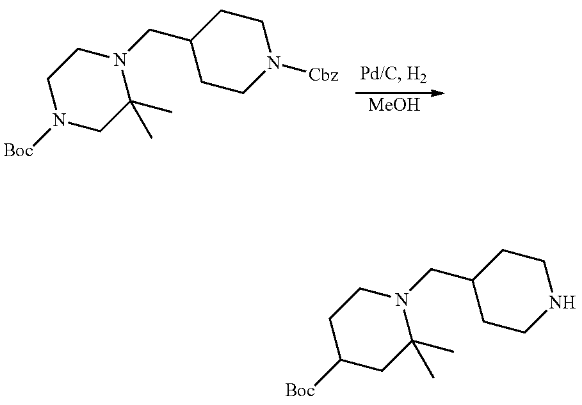 [SMILES: "MeOH" ; CC(C)(C)OC(=O)N1CCN(CC2CCN(C(=O)OCc3ccccc3)CC2)C(C)(C)C1 ; CC(C)(C)OC(=O)C1CCN(CC2CCNCC2)C(C)(C)C1]

Step 1:

To a solution of tert-butyl 4-[(1-benzyloxycarbonyl-4-piperidyl)methyl]-3,3-dimethyl-piperazine-1-carboxylate (2.1 g, 4.71 mmol, 1 eq) in MeOH (20 mL) was added Pd/C (500 mg, 10% purity) under $N_2$. The suspension was degassed under vacuum and purged with $H_2$ several times. The mixture was stirred under $H_2$ (15 psi) at 25° C. for 1 hour. TLC (petroleum ether:ethyl acetate=1:1) showed the reaction completed. After cooling, the reaction mixture was filtered and filtrate was concentrated under reduced pressure to give tert-butyl 3,3-dimethyl-4-(4-piperidylmethyl)piperazine-1-carboxylate (1.39 g, 4.46 mmol, 94.70% yield) as a white gum.

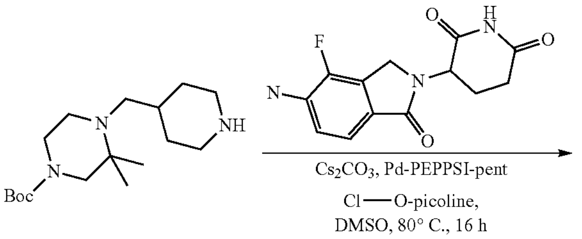

-continued

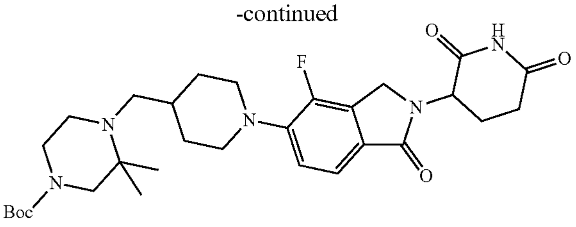

Step 2:

A mixture of tert-butyl 3,3-dimethyl-4-(4-piperidylmethyl)piperazine-1-carboxylate (547.81 mg, 1.76 mmol, 1.5 eq), 3-(5-bromo-4-fluoro-1-oxo-isoindolin-2-yl)piperidine-2,6-dione (400 mg, 1.17 mmol, 1 eq), Pd-PEPPSI-pent Cl—O-picoline (31.84 mg, 58.63 μmol, 0.05 eq), $Cs_2CO_3$ (1.15 g, 3.52 mmol, 3 eq) in DMSO (5 mL) was degassed and purged with $N_2$ for 3 times, and then the mixture was stirred at 90° C. for 20 hr. LC-MS (EB4455-29-P1D) showed 3-(5-bromo-4-fluoro-1-oxo-isoindolin-2-yl)piperidine-2,6-dione was consumed completely and the desired mass was detected. The reaction mixture was quenched by addition HCOOH to pH=2-3 and added EtOAc (50 mL*2). The combined organic layer were washed with brine (50 mL*2), dried over $Na_2SO_4$, filtered and concentrated under reduced. And the water layer was extracted with DCM (30 mL*6). The organic layer was dried over $Na_2SO_4$, filtered and concentrated under reduced. The residue was purified by silica gel chromatography (column height: 4 g, 100-200 mesh silica gel, 60% of Ethyl acetate in Petroleum ether) to give tert-butyl 4-[[1-[2-(2,6-dioxo-3-piperidyl)-4-fluoro-1-oxo-isoindolin-5-yl]-4-piperidyl]methyl]-3,3-dimethyl-piperazine-1-carboxylate (0.18 g, 275.04 μmol, 23.46% yield) as a white solid.

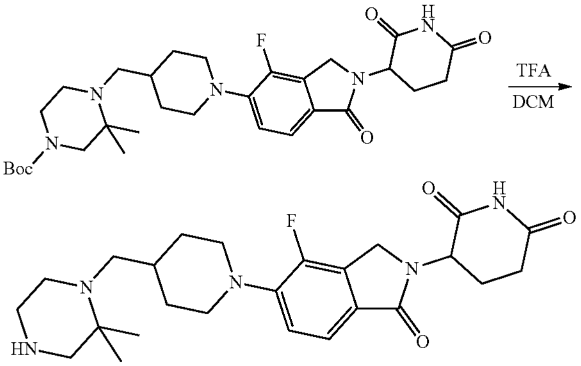

Step 3:

To a solution of tert-butyl 4-[[1-[2-(2,6-dioxo-3-piperidyl)-4-fluoro-1-oxo-isoindolin-5-yl]-4-piperidyl]methyl]-3,3-dimethyl-piperazine-1-carboxylate (170 mg, 297.37 μmol, 1 eq) in DCM (5 mL) was added TFA (1.54 g, 13.51 mmol, 1 mL, 45.42 eq). The mixture was stirred at 25° C. for 4 hr. TLC showed tert-butyl 4-[[1-[2-(2,6-dioxo-3-piperidyl)-4-fluoro-1-oxo-isoindolin-5-yl]-4-piperidyl]methyl]-3,3-dimethyl-piperazine-1-carboxylate was consumed completely and the desired spot was detected. The reaction mixture was concentrated under reduced pressure to remove solvent to give 3-(5-(4-((2,2-dimethylpiperazin-1-yl)methyl)piperidin-1-yl)-4-fluoro-1-oxoisoindolin-2-yl)piperidine-2,6-dione (0.14 g, 296.88 μmol, 99.84% yield) as a white solid.

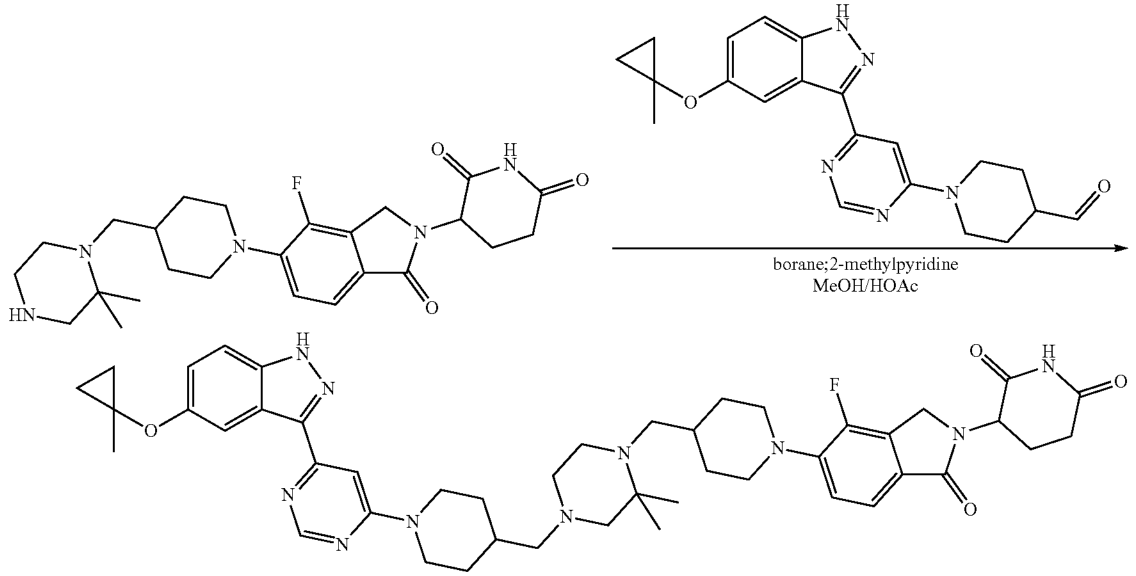

Step 4:

To a solution 1 of 3-[5-[4-[(2,2-dimethylpiperazin-1-yl) methyl]-1-piperidyl]-4-fluoro-1-oxo-isoindolin-2-yl]piperidine-2,6-dione (140 mg, 296.88 μmol, 1.60 eq) in MeOH (5 mL) was added DIEA (70.00 mg, 541.62 μmol, 94.34 uL, 2.92 eq). The mixture was stirred at 25° C. for 20 min. Then to a solution 2 of 1-[6-[5-(1-methylcyclopropoxy)-1H-indazol-3-yl]pyrimidin-4-yl]piperidine-4-carbaldehyde (70 mg, 185.46 μmol, 1 eq) in MeOH (5 mL) was added AcOH (525.00 mg, 8.74 mmol, 0.5 mL, 47.14 eq). The solution 2 was stirred at 25° C. for 10 min. Then solution 2 was added solution 1 and borane; 2-methylpyridine (39.67 mg, 370.92 μmol, 2 eq), then the mixture was stirred at for 16 hr. LC-MS showed 1-[6-[5-(1-methylcyclopropoxy)-1H-indazol-3-yl] pyrimidin-4-yl]piperidine-4-carbaldehyde was consumed completely and the desired mass was detected. The reaction mixture was concentrated under reduced pressure to remove solvent. The residue was purified by prep-HPLC (column: WHELK-01 (250 mm*30 mm, 5 um); mobile phase: [water (FA)-ACN]; B %: 10%-50%, 35 min) to afford 3-[5-[4-[[2,2-dimethyl-4-[[1-[6-[5-(1-methylcyclopropoxy)-1H-indazol-3-yl]pyrimidin-4-yl]-4-piperidyl]methyl]piperazin-1-yl] methyl]-1-piperidyl]-4-fluoro-1-oxo-isoindolin-2-yl] piperidine-2,6-dione (88 mg, 104.97 μmol, 56.60% yield, 99.360% purity) as a white solid.

Exemplary Synthesis of Compound 237

Compound 237 was prepared in a manner analogous to compound 224 starting from tert-butyl 3,6-diazabicyclo [3.1.1]heptane-6-carboxylate.

Exemplary Synthesis of Compound 238

Compound 238 was prepared in a manner analogous to compound 234.

Exemplary Synthesis of Compound 239

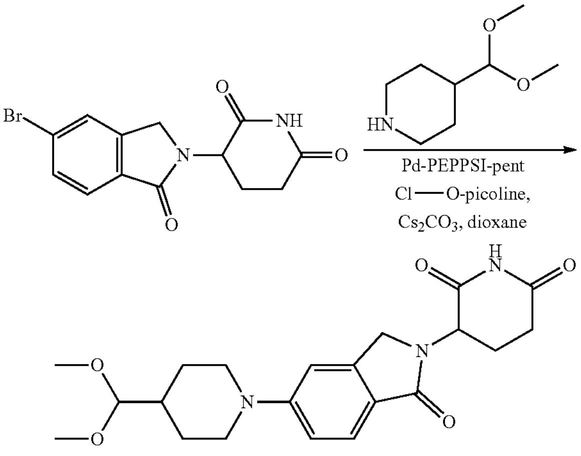

Step 1:

To a solution of 3-(5-bromo-1-oxo-isoindolin-2-yl)piperidine-2,6-dione (500 mg, 1.55 mmol, 1 eq) and 4-(dimethoxymethyl)piperidine (369.56 mg, 2.32 mmol, 1.5 eq) in DMSO (5 mL) was added $Cs_2CO_3$ (1.01 g, 3.09 mmol, 2 eq) and Pd-PEPPSI-pent Cl—O-picoline (84.02 mg, 154.73 μmol, 0.1 eq). The mixture was stirred at 80° C. for 12 hours. LC-MS (EB648-394-P1A) showed Reactant 1 was consumed completely and one main peak with desired mass was detected. After cooling, the solution was poured into HCOOH (2 mL) to adjust pH<7, the reaction solution was diluted with ethyl acetate (30 mL) and washed with water (20 mL×3). The combined organic layers were washed with brine (30 mL×2), dried over $Na_2SO_4$, filtered and concentrated under reduced pressure to give a residue. The residue was purified by flash silica gel chromatography (ISCO®; 20 g SepaFlash® Silica Flash Column, Eluent of 0~97% Ethyl acetate/Petroleum ether gradient @ 45 m/min) to afford 3-[5-[4-(dimethoxymethyl)-1-piperidyl]-1-oxo-isoindolin- 2-yl]piperidine-2,6-dione (315 mg, 784.65 μmol, 50.71% yield) was obtained as a white solid.

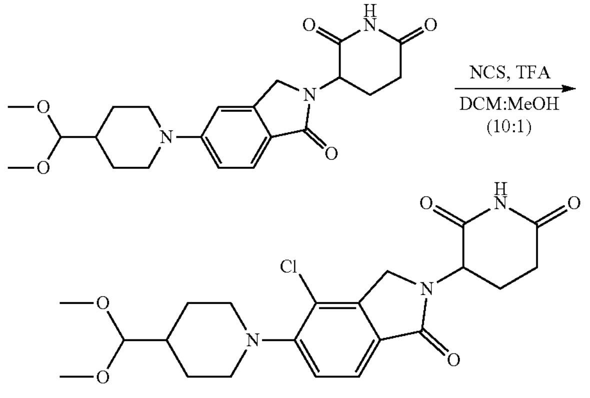

Step 2:

A mixture of 3-[5-[4-(dimethoxymethyl)-1-piperidyl]-1-oxo-isoindolin-2-yl]piperidine-2,6-dione (310 mg, 772.19 μmol, 1 eq), NCS (123.74 mg, 926.63 μmol, 1.2 eq), TFA (150.56 mg, 1.32 mmol, 97.77 uL, 1.71 eq) in DCM (20 mL) and MeOH (2 mL) was degassed and purged with $N_2$ for 3 times, and then the mixture was stirred at 25° C. for 12 hours under $N_2$ atmosphere. LC-MS (EB648-396-P1A) showed Reactant 1 was consumed completely and one main peak with desired m/z or desired mass was detected. The solution was added aq.$NaHCO_3$ to adjust pH >7, the reaction mixture was concentrated under reduced pressure to remove DCM and MeOH, filtered and the filtrate cake was concentrated under reduced pressure to give 3-[4-chloro-5-[4-(dimethoxymethyl)-1-piperidyl]-1-oxo-isoindolin-2-yl]piperidine-2,6-dione (232 mg, 532.23 μmol, 68.92% yield) as a white solid.

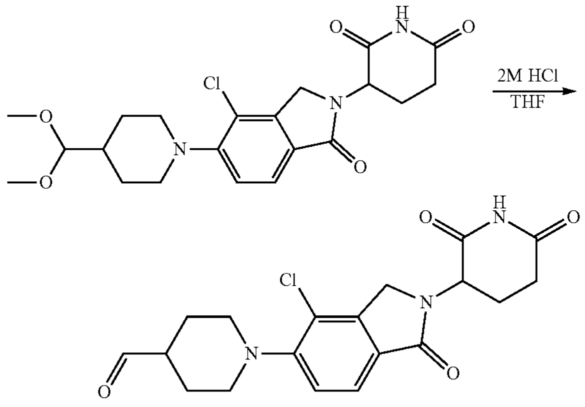

Step 3:

To a solution of 3-[4-chloro-5-[4-(dimethoxymethyl)-1-piperidyl]-1-oxo-isoindolin-2-yl]piperidine-2,6-dione (232 mg, 532.23 μmol, 1 eq) in THF (6 mL) was added HCl (2 M, 3 mL). The mixture was stirred at 40° C. for 0.5 hours. LC-MS (EB648-397-P1A) showed Reactant 1 was consumed completely and one main peak with desired mass was detected. The solution was added aq.$NaHCO_3$ to adjust pH >7, then filtered and the filtrate cake was concentrated under reduced pressure to give 1-[4-chloro-2-(2,6-dioxo-3-piperidyl)-1-oxo-isoindolin-5-yl]piperidine-4-carbaldehyde (118 mg, 302.69 μmol, 56.87% yield) as a yellow solid.

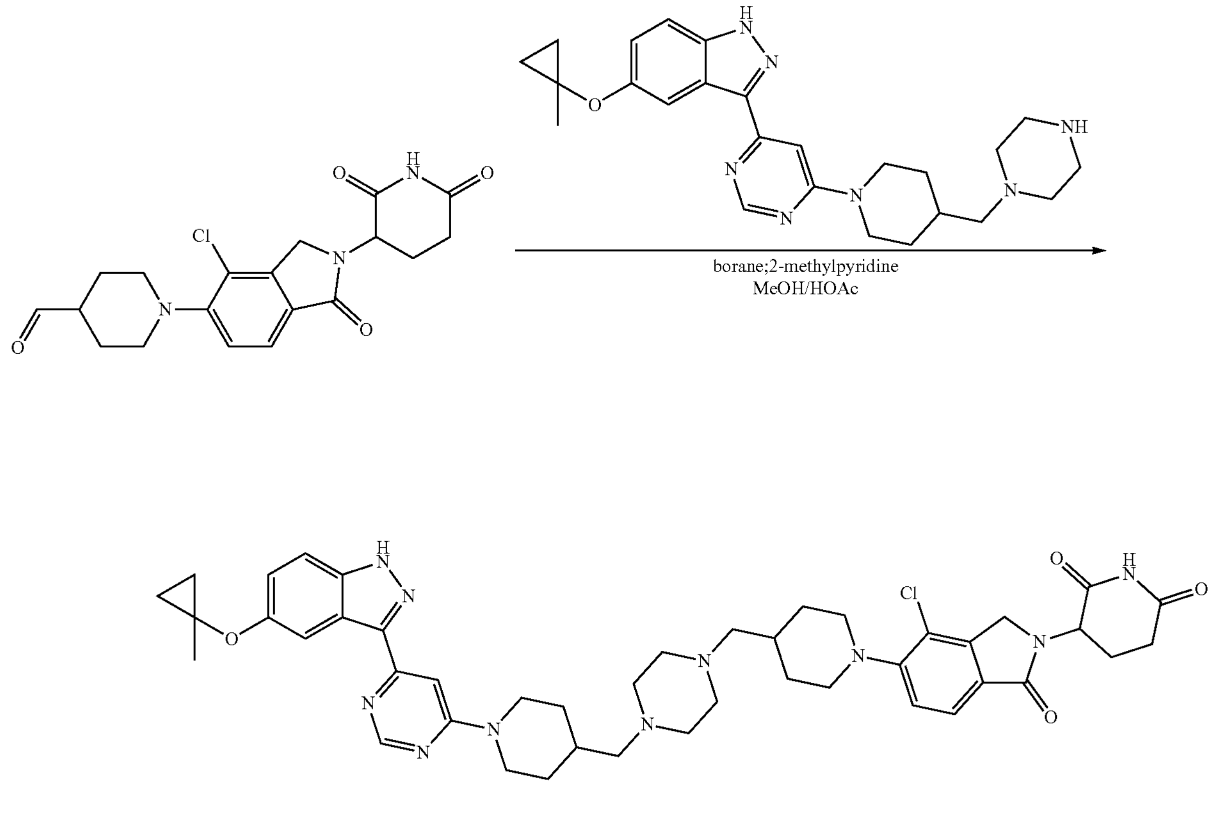

Step 4:

To a solution of 1-[4-chloro-2-(2,6-dioxo-3-piperidyl)-1-oxo-isoindolin-5-yl]piperidine-4-carbaldehyde (50 mg, 128.26 μmol, 1 eq) and 5-(1-methylcyclopropoxy)-3-[6-[4-(piperazin-1-ylmethyl)-1-piperidyl]pyrimidin-4-yl]-1H-indazole (57.41 mg, 128.26 μmol, 1 eq) in AcOH (1 mL) and MeOH (10 mL) was stirred at 20° C. for 20 min, then was added borane; 2-methylpyridine (27.44 mg, 256.52 μmol, 2 eq). The mixture was stirred at 25° C. for 12 hours under $N_2$ atmosphere. LC-MS (EB648-398-P1A) showed reactant 1 was consumed completely and one main peak with desired mass was detected. The solution was purified by prep-HPLC (Xtimate C18 100×30 mm×10 um; water (FA)-CAN, B %: 0-35%, 35 min) to afford 3-[4-chloro-5-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (59 mg, 68.02 μmol, 53.03% yield, 100% purity, FA) as a white solid.

Exemplary Synthesis of Compound 240

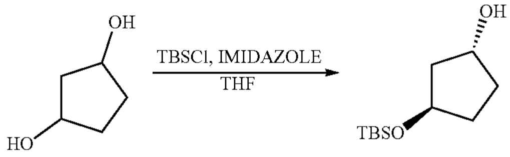 [SMILES: OC1CCC(O)C1 ; CC(C)(C)[Si](C)(C)O[C@@H]1CC[C@@H](O)C1 ; "THF"]

Step 1:

To a mixture of cyclopentane-1,3-diol (2 g, 19.58 mmol, 1 eq) and TBSCl (2.95 g, 19.58 mmol, 2.40 mL, 1 eq) in DCM (10 mL) was added IMIDAZOLE (1.33 g, 19.58 mmol, 1 eq) in one portion at 0° C. under N2. The mixture was stirred at 0° C. for 1 hours. TLC (Petroleum ether:Ethyl acetate=5/1, Rf=0.35) showed the reaction was completed. The reaction was quenched with saturated aqueous solution of ammonium chloride (20 mL), and then extracted with DCM (20 mL×3). The combined organic layers were dried over Na2SO4, and then filtered off, and then concentrated in vacuo. The residue was purified by silica gel chromatography (Petroleum ether/Ethyl acetate=10/1) to afford a mixture of 1,3-trans-3-[tert-butyl(dimethyl)silyl]oxycyclopentanol (1.14 g, 5.27 mmol, 26.90% yield) as colourless liquid.

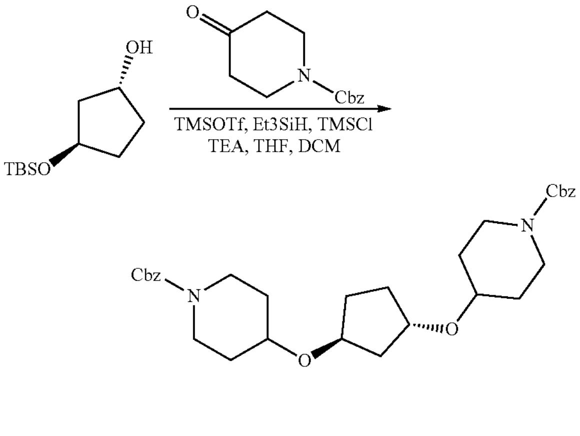

Step 2:

To a solution of 1,3-trans-3-[tert-butyl(dimethyl)silyl]oxycyclopentanol (1.5 g, 6.93 mmol, 1 eq) in THF (10 mL) was added TEA (1.05 g, 10.40 mmol, 1.45 mL, 1.5 eq) and TMSCl (828.39 mg, 7.63 mmol, 967.74 uL, 1.1 eq) at 0° C., and the reaction mixture was stirred at 25° C. for 1 hour. The reaction mixture was filtered and the filtrate was concentrated under reduced pressure to give a residue. Then to a stirred solution of above residue and benzyl 4-oxopiperidine-1-carboxylate (1.94 g, 8.32 mmol, 1.66 mL, 1.2 eq) in DCM (10 mL) was added $Et_3SiH$ (967.25 mg, 8.32 mmol, 1.33 mL, 1.2 eq) and TMSOTf (847.37 mg, 3.81 mmol, 688.92 uL, 0.55 eq) dropwise at −60° C., and the reaction mixture was stirred at 0° C. under $N_2$ for 2 hours. LCMS showed the reaction was completed. The reaction mixture was quenched by addition water 30 mL and extracted with DCM (20 mL*3). The combined organic layers were washed with brine (30 mL), dried over $Na_2SO_4$, filtered and concentrated under reduced pressure to give a residue. The residue was purified by silica gel chromatography (Petroleum ether/Ethyl acetate=5/1) to afford benzyl 4-[(1S,3S)-3-[(1-benzyloxycarbonyl-4-piperidyl)oxy]cyclopentoxy]piperidine-1-carboxylate and benzyl 4-[(1R,3R)-3-[(1-benzyloxycarbonyl-4-piperidyl)oxy]cyclopentoxy]piperidine-1-carboxylate (1.37 g, 2.55 mmol, 36.83% yield) as light yellow liquid.

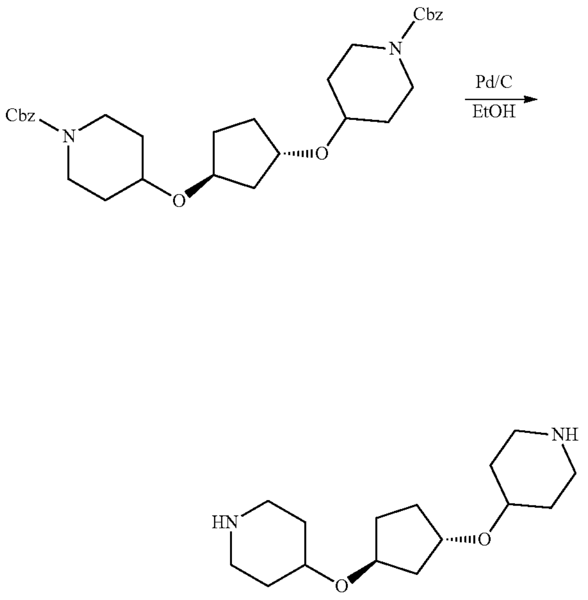

Step 3:

To a mixture of benzyl 4-[(1S,3S)-3-[(1-benzyloxycarbonyl-4-piperidyl)oxy]cyclopentoxy]piperidine-1-carboxylate and benzyl 4-[(1R,3R)-3-[(1-benzyloxycarbonyl-4-piperidyl)oxy]cyclopentoxy]piperidine-1-carboxylate (1.37 g, 2.55 mmol, 1 eq) in EtOH (10 mL) and EA (10 mL) was added Pd/C (500 mg, 10% purity, 1.00 eq) in one portion at 25° C. under N2. The mixture was stirred at 25° C. for 12 hours under H2 (15 psi). TLC (Petroleum ether:Ethyl acetate=3/1) showed the reaction was completed. The mixture was filtered and concentrated in reduce pressure at 45° C. The residue was used into next step directly without further purification. The product mixture of 4-[(1S,3S)-3-(4-piperidyloxy)cyclopentoxy]piperidine and 4-[(1R,3R)-3-(4-piperidyloxy)cyclopentoxy]piperidine (880 mg, crude) was obtained as a light yellow liquid.

Step 4:

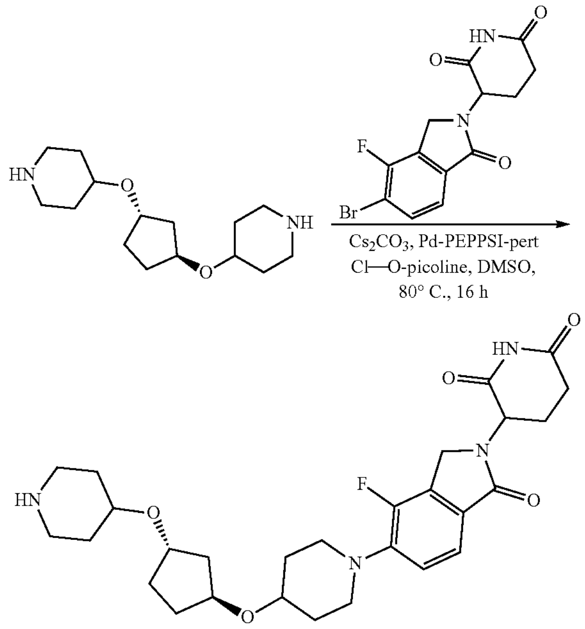

To a solution of 4-[(1S,3S)-3-(4-piperidyloxy)cyclopentoxy]piperidine and 4-[(1R,3R)-3-(4-piperidyloxy)cyclopentoxy]piperidine (500 mg, 1.86 mmol, 2 eq) and 3-(5-bromo-4-fluoro-1-oxo-isoindolin-2-yl)piperidine-2,6-dione (317.75 mg, 931.47 μmol, 1 eq) in DMSO (4 mL) was added $Cs_2CO_3$ (606.98 mg, 1.86 mmol, 2 eq) and PD-PEPPSI™-IPENT CATALYST (73.93 mg, 93.15 μmol, 0.1 eq) under $N_2$. After addition, the mixture was stirred at 90° C. for 10 hours under $N_2$. LCMS showed the reaction was completed. The mixture was filtered and concentrated in reduce pressure. The residue was purified by prep-HPLC(Xtimate C18 100*30 mm*10 um; mobile phase: [water (FA)-ACN]; B %: 0%-35%, 35 min) to afford 3-[4-fluoro-1-oxo-5-[4-[(1S,3S)-3-(4-piperidyloxy)cyclopentoxy]-1-piperidyl]isoindolin-2-yl]piperidine-2,6-dione and 3-[4-fluoro-1-oxo-5-[4-[(1R,3R)-3-(4-piperidyloxy)cyclopentoxy]-1-piperidyl]isoindolin-2-yl]piperidine-2,6-dione (130 mg, 226.23 μmol, 24.29% yield, FA) as a gray solid.

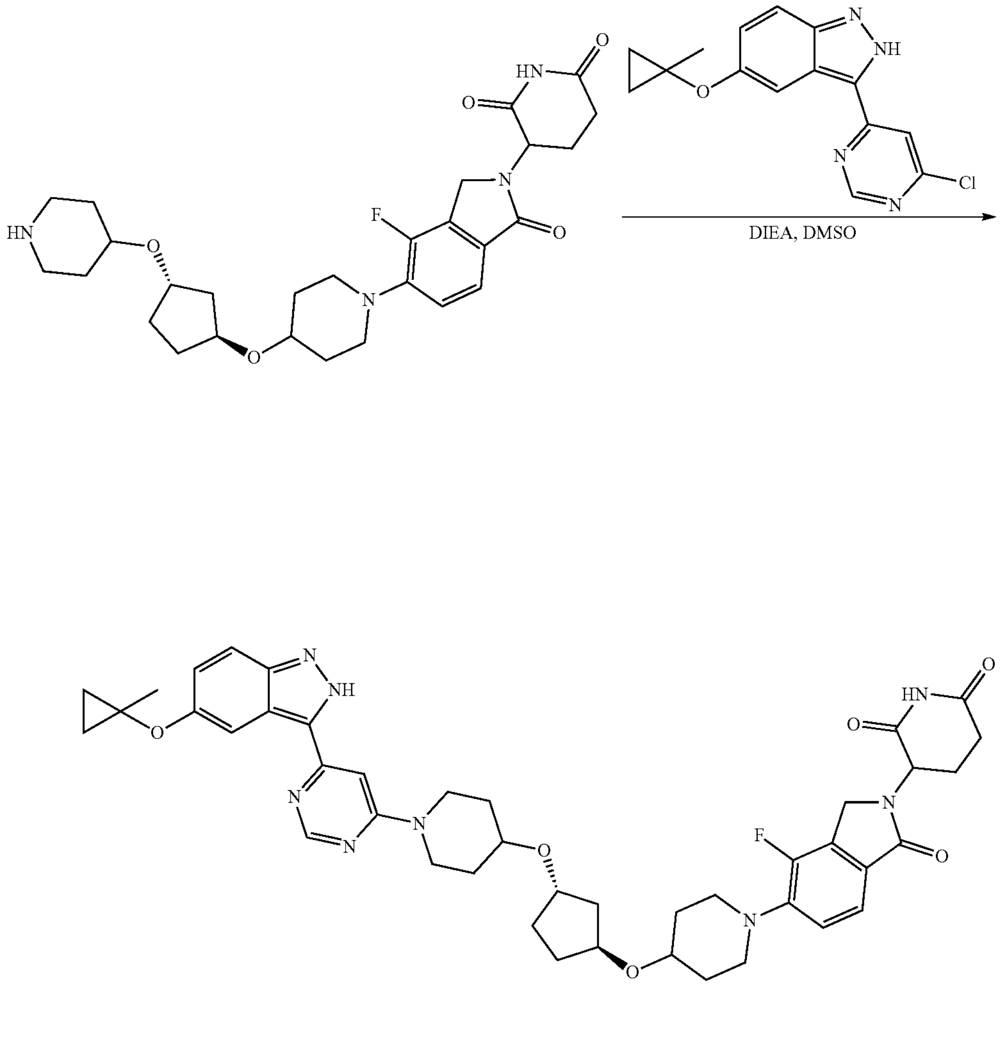

Step 5:

To a mixture of 3-[4-fluoro-1-oxo-5-[4-[(1S,3S)-3-(4-piperidyloxy)cyclopentoxy]-1-piperidyl]isoindolin-2-yl]piperidine-2,6-dione and 3-[4-fluoro-1-oxo-5-[4-[(1R,3R)-3-(4-piperidyloxy)cyclopentoxy]-1-piperidyl]isoindolin-2-yl]piperidine-2,6-dione (130 mg, 226.23 μmol, 1 eq, FA) and 3-(6-chloropyrimidin-4-yl)-5-(1-methylcyclopropoxy)-2H-indazole (68.04 mg, 226.23 μmol, 1 eq) in DMSO (2 mL) was added DIEA (146.19 mg, 1.13 mmol, 197.02 uL, 5 eq) in one portion at 25° C. under $N_2$. The mixture was stirred at 80° C. for 12 hours. LCMS showed the reaction was completed. The mixture was cooled to 25° C. and poured into water (10 mL). The aqueous phase was extracted with ethyl acetate (10 mL*3). The combined organic phase was washed with brine (10 mL*2), dried with anhydrous $Na_2SO_4$, filtered and concentrated in vacuum. The residue was purified by prep-HPLC (Xtimate C18 100*30 mm*10 um; mobile phase: [water (FA)-ACN]; B %: 15%-55%, 35 min) to afford 3-[4-fluoro-5-[4-[(1S,3S)-3-[[1-[6-[5-(1-methylcyclopropoxy)-2H-indazol-3-yl]pyrimidin-4-yl]-4-piperidyl]oxy]cyclopentoxy]-1-piperidyl]-1-oxo-isoindolin-2-yl]piperidine-2,6-dione and 3-[4-fluoro-5-[4-[(1R,3R)-3-[[1-[6-[5-(1-methylcyclopropoxy)-2H-indazol-3-yl]pyrimidin-4-yl]-4-piperidyl]oxy]cyclopentoxy]-1-piperidyl]-1-oxo-isoindolin-2-yl]piperidine-2,6-dione (102.6 mg, 128.11 μmol, 56.63% yield, 99% purity) as a gray solid.

Exemplary Synthesis of Compound 241

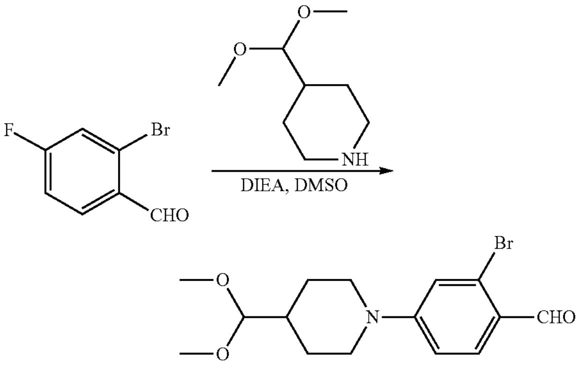

Step 1:

To a solution of 2-bromo-4-fluoro-benzaldehyde (1.00 g, 4.93 mmol, 1.0 eq) and 4-(dimethoxymethyl)piperidine (0.78 g, 4.93 mmol, 1.0 eq) in dimethyl sulfoxide (20.0 mL) was added diisopropylethylamine (1.91 g, 14.78 mmol, 2.6 mL, 3.0 eq) and the mixture was stirred for 1 hour at 90° C. LCMS showed the starting material was consumed and desired mass was detected. The mixture was partitioned between ethyl acetate (100 mL) and water (100 mL). The separated organic layer was washed with water, dried over anhydrous sodium sulfate and evaporated to dryness. The crude product was purified by silica gel chromatography (10%-30% ethyl acetate in petroleum ether). 2-bromo-4-[4-(dimethoxymethyl)-1-piperidyl]benzaldehyde (1.50 g, 4.38 mmol, 88% yield, 100% purity) was obtained as a yellow solid, which was detected by HNMR (EW29242-68-P1C1).

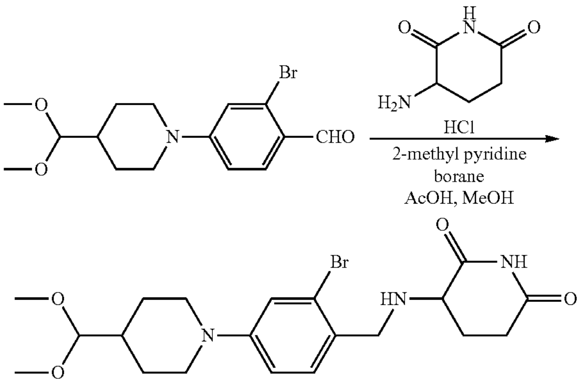

Step 2:

To a solution of 3-aminopiperidine-2,6-dione (0.81 g, 4.91 mmol, 1.2 eq) in methanol (20.0 mL) was added triethylamine (0.41 g, 4.09 mmol, 0.6 mL, 1.0 eq), the mixture was stirred for 0.5 hour. Then 2-bromo-4-[4-(dimethoxymethyl)-1-piperidyl]benzaldehyde (1.40 g, 4.09 mmol, 1.0 eq) and acetic acid (0.24 g, 4.09 mmol, 0.23 mL, 1.0 eq) was added. After stirring for 2 hour at 25° C., 2-methyl pyridine borane (0.87 g, 8.18 mmol, 2.00 eq) was added and the mixture was stirred for 1 hour at 25° C. LCMS showed the starting material was consumed and desired mass was detected. The mixture was purified by silica gel chromatography (1%-10% methanol in dichloromethane). The compound 3-[[2-bromo-4-[4-(dimethoxymethyl)-1-piperidyl]phenyl]methylamino]piperidine-2,6-dione (0.9 g, 1.98 mmol, 48% yield, 100% purity) was obtained as a off-white solid, which was detected by HNMR (EW29242-71-P1C1).

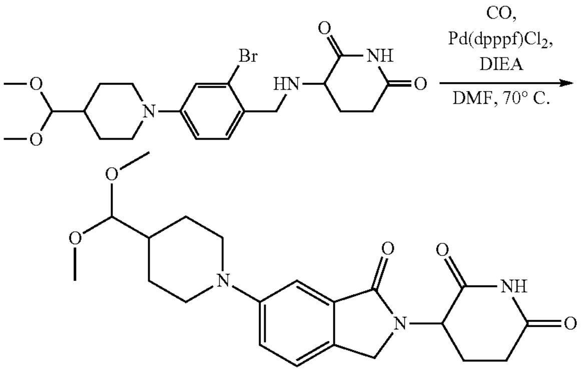

Step 3:

To a solution of 3-[[2-bromo-4-[4-(dimethoxymethyl)-1-piperidyl]phenyl]methylamino]piperidine-2,6-dione (0.70 g, 1.54 mmol, 1.0 eq) in dimethylformamide (10.0 mL) was added [1,1-Bis(diphenylphosphino)ferrocene]dichloropalladium(II) (0.34 g, 0.46 mmol, 0.3 eq), and diisopropylethylamine (0.59 g, 4.62 mmol, 0.81 mL, 3.0 eq) under nitrogen atmosphere. The suspension was degassed and purged with carbonic oxide for 3 times. LCMS showed part of the starting material was consumed and desired mass was detected. The mixture was stirred under carbonic oxide (50 Psi) at 80° C. for 12 hour. The mixture was purified by prep-HPLC (2%-35% acetonitrile+0.225% formic acid in water, 11 min). The compound 3-[6-[4-(dimethoxymethyl)-1-piperidyl]-1-oxo-isoindolin-2-yl]piperidine-2,6-dione (0.31 g, 0.77 mmol, 50% yield, 100% purity) was obtained as a white solid, which was detected by HNMR (EW29242-75-P1C1).

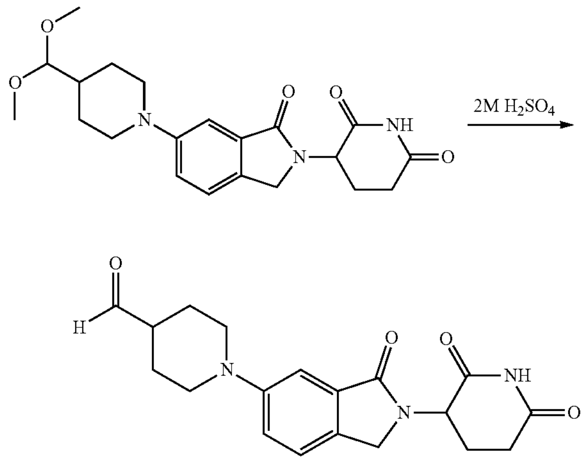 [SMILES: COC(OC)C1CCN(c2ccc3c(c2)C(=O)N(C2CCC(=O)NC2=O)C3)CC1 ; O=CC1CCN(c2ccc3c(c2)C(=O)N(C2CCC(=O)NC2=O)C3)CC1]

Step 4:

To a solution of 3-[6-[4-(dimethoxymethyl)-1-piperidyl]-1-oxo-isoindolin-2-yl]piperidine-2,6-dione (0.25 g, 0.62 mmol, 1.00 eq) in tetrahydrofuran (2.5 mL) was added 2 M sulfuric acid (0.06 g, 0.62 mmol, 2.5 mL, 1.00 eq) at 0° C. The mixture was stirred for 1.5 hour at 40° C. LCMS showed the starting material was consumed and desired mass was detected. The mixture was diluted with water (2 mL), neutralized with solid sodium bicarbonate until no sodium bicarbonate was evolved. The mixture was extracted with ethyl acetate (4 mL) twice. The organic layers were washed with water and dried over anhydrous sodium sulfate and evaporated to dryness. The product 1-[2-(2,6-dioxo-3-piperidyl)-3-oxo-isoindolin-5-yl]piperidine-4-carbaldehyde (0.22 g, 0.62 mmol, 99% yield, 100% purity) was obtained as a white solid, which was detected by HNMR (EW29242-90-P1C1).

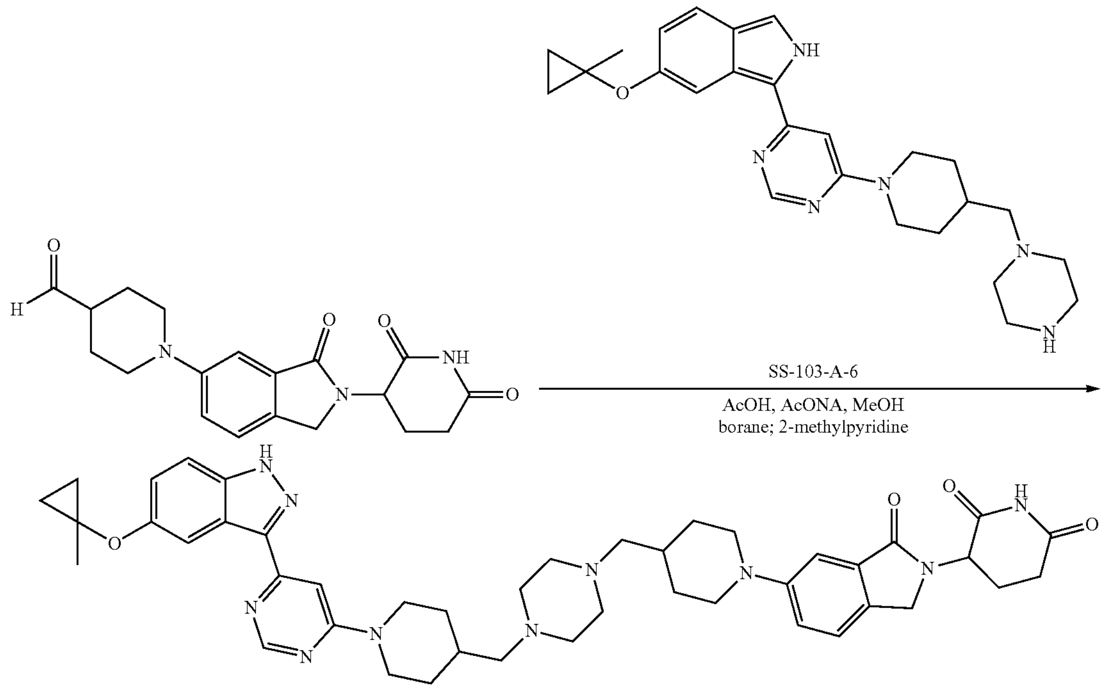

Step 5:

To a solution of 5-(1-methylcyclopropoxy)-3-[6-[4-(piperazin-1-ylmethyl)-1-piperidyl]pyrimidin-4-yl]-2H-indazole (0.07 g, 0.16 mmol, 1.0 eq) in methanol (2.0 mL) was added sodium acetate (0.06 g, 0.78 mmol, 5.0 eq) and stirred for 0.5 hour, 1-[2-(2,6-dioxo-3-piperidyl)-3-oxo-isoindolin-5-yl]piperidine-4-carbaldehyde (0.06 g, 0.17 mmol, 1.1 eq) and acetic acid (0.02 g, 0.31 mmol, 0.1 mL, 2.0 eq) was added to the above mixture, the mixture was stirred for 0.5 hour, borane; 2-methylpyridine (0.03 g, 0.31 mmol, 2.00 eq) was added and the mixture was stirred for 1 hour at 25° C. The mixture was purified by prep-HPLC (5%-29% acetonitrile+0.225% formic acid in water, 12 min). The product 3-[6-[4-[[4-[[1-[6-[5-(1-methylcyclopropoxy)-1H-indazol-3-yl]pyrimidin-4-yl]-4-piperidyl]methyl]piperazin-1-yl]methyl]-1-piperidyl]-1-oxo-isoindolin-2-yl]piperidine-2,6-dione (27 mg, 0.03 mmol, 22% yield, 98% purity) was obtained as a pink solid.

Exemplary Synthesis of Compound 242

Compound 242 was prepared in a manner analogous to compounds 219 and 223.

Exemplary Synthesis of Compound 243

Compound 243 was prepared in a manner analogous to compounds 234 and 239.

Exemplary Synthesis of Compound 244

Compound 244 was prepared in a manner analogous to compounds 210 and 235.

Exemplary Synthesis of Compound 245

Compound 245 was prepared in a manner analogous to compounds 210 and 219.

Exemplary Synthesis of Compounds 246, 255, 256, 257, 262, 264, 265, 271, 278, 285, 287, and 288

Compounds 246, 255, 256, 257, 262, 264, 265, 271, 278, 285, 287, and 288 were prepared in a manner analogous to compound 211.

Exemplary Synthesis of Compound 247 and 274

Compounds 247 and 274 were prepared in a manner analogous to compound 224.

Exemplary Synthesis of Compound 248

Compound 248 was prepared in a manner analogous to compounds 210 and 211.

Exemplary Synthesis of Compound 249

Compound 249 was prepared in a manner analogous to compounds 213 and 239.

Exemplary Synthesis of Compounds 250 and 251

Compounds 250 and 251 were prepared in a manner analogous to compounds 211 and 224.

Exemplary Synthesis of Compounds 252, 268, and 281

Compounds 252, 268, and 281 were prepared in a manner analogous to compounds 211 and 213.

Exemplary Synthesis of Compounds 253, 261, 282, and 283

Compounds 253, 261, 282, and 283 were prepared in a manner analogous to compounds 201 and 211.

Exemplary Synthesis of Compounds 254 and 259

Compounds 254 and 259 were prepared in a manner analogous to compound 213.

Exemplary Synthesis of Compounds 258 and 260

Compounds 258 and 260 were prepared in a manner analogous to compound 234.

Exemplary Synthesis of Compounds 263, 266, 267, 272, 276, and 284

Compounds 263, 266, 267, 272, 276, and 284 were prepared in a manner analogous to compound 181.

Exemplary Synthesis of Compound 269

Compound 269 was prepared in a manner analogous to compounds 213 and 219.

Exemplary Synthesis of Compound 270 and 275

Compounds 270 and 275 were prepared in a manner analogous to compound 236.

Exemplary Synthesis of Compounds 273 and 280

Compounds 273 and 280 were prepared in a manner analogous to compounds 211 and 234.

Exemplary Synthesis of Compounds 277 and 279

Compounds 277 and 279 were prepared in a manner analogous to compounds 211 and 236.

Exemplary Synthesis of Compound 286

Compound 286 was prepared in a manner analogous to compounds 219 and 234.

Exemplary Synthesis of Compound 289

Compound 289 was prepared in a manner analogous to compound 181.

Exemplary Synthesis of Compound 290

Compound 290 was prepared in a manner analogous to compound 181 using intermediate tert-butyl 4-[2-(2,6-dioxo-3-piperidyl)-4-fluoro-1-oxo-isoindolin-5-yl]piperidine-1-carboxylate.

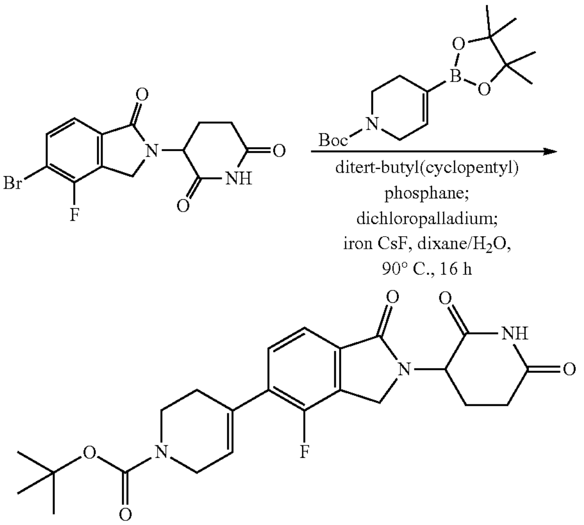

Step 1:

To a solution of tert-butyl 4-(4,4,5,5-tetramethyl-1,3,2-dioxaborolan-2-yl)-3,6-dihydro-2H-pyridine-1-carboxylate (2.72 g, 8.79 mmol, 1 eq) and 3-(5-bromo-4-fluoro-1-oxo-isoindolin-2-yl)piperidine-2,6-dione (3 g, 8.79 mmol, 1 eq) in dioxane (30 mL) and $H_2O$ (3 mL) was added CsF (4.01 g, 26.38 mmol, 972.72 uL, 3 eq) and ditert-butyl(cyclopentyl)phosphane;dichloropalladium;iron (573.16 mg, 879.42 µmol, 0.1 eq). The mixture was stirred at 90° C. for 16 hours under nitrogen atmosphere. LCMS showed the desired MS. The reaction mixture was filtered and concentrated under reduced pressure to give a residue. The residue was purified by flash silica gel chromatography (ISCO®; 40 g Sepa- Flash® Silica Flash Column, Eluent of 0~100% Ethyl acetate/Petroleum ethergradient @ 60 m/min). Compound tert-butyl 4-[2-(2,6-dioxo-3-piperidyl)-4-fluoro-1-oxo-isoindolin-5-yl]-3,6-dihydro-2H-pyridine-1-carboxylate (3.7 g, 8.34 mmol, 94.87% yield) was obtained as a white solid.

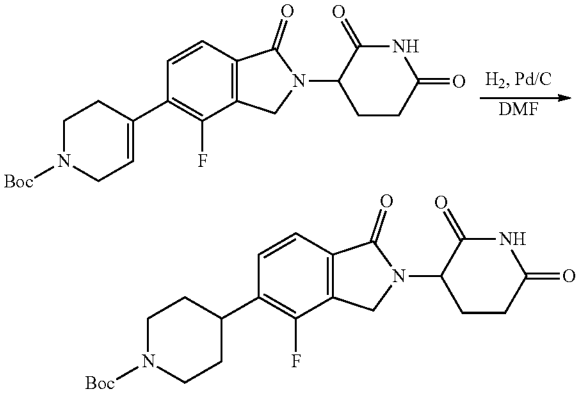

Step 2:

To a solution of tert-butyl 4-[2-(2,6-dioxo-3-piperidyl)-4-fluoro-1-oxo-isoindolin-5-yl]-3,6-dihydro-2H-pyridine-1-carboxylate (1.7 g, 3.83 mmol, 1 eq) in DMF (20 mL) was added Pd/C (2 g, 3.83 mmol, 225.50 uL, 10% purity, 1.00 eq) under $N_2$ atmosphere. The suspension was degassed and purged with $H_2$ three times. The mixture was stirred under $H_2$ (50 Psi) at 40° C. for 16 hours. LCMS showed the desired MS. The reaction mixture was filtered and concentrated under reduced pressure to give a residue and without purification. Compound tert-butyl 4-[2-(2,6-dioxo-3-piperidyl)-4-fluoro-1-oxo-isoindolin-5-yl]piperidine-1-carboxylate (1.23 g, 2.76 mmol, 72.03% yield) was obtained as an off-white solid.

Exemplary Synthesis of Compound 291

Compound 291 was prepared in a manner analogous to compound 209 using intermediate tert-butyl 4-[[(2s,5r)-5-[[4-[2-(2,6-dioxo-3-piperidyl)-4-fluoro-1-oxo-isoindolin-5-yl]piperazin-1-yl]methyl]-1,4-dioxan-2-yl]methyl]piperazine-1-carboxylate.

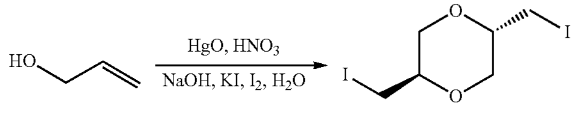

Step 1:

HgO (50.04 g, 231.04 mmol, 1 eq) were dissolved in $HNO_3$ (45.85 g, 728.21 mmol, 32.75 mL, 3.15 eq) and $H_2O$ (20 mL). Additional $H_2O$ (80 mL) was added and the solution was cooled to 0° C. Then with stirring and cooling prop-2-en-1-ol (28.03 g, 482.62 mmol, 32.82 mL, 2.09 eq) was added. Gradually a copious white precipitate formed. The mixture was left standing 6 hours. (Prolonged standing of the reaction mixture at this point may result in decomposition of the product.) The precipitate was filtered off and dissolved in 10% aqueous sodium hydroxide. Concentrated aqueous potassium iodide was then added until precipitation of trans-2,5-bis-(iodomercurimethyl)-p-dioxane was complete. It was filtered off and washed with water. The wet solid was refluxed with a solution of $I_2$ (117.28 g, 462.07 mmol, 93.08 mL, 2 eq), and KI (106.53 g, 642.28 mmol, 2.78 eq) in $H_2O$ (500 mL) of water. (A flask large enough so that only about one-third of its volume is occupied by the reactants is recommended. Toluene (20 mL) was added to wash back iodine that sublimes out on the condenser.) Refluxing (110° C.) was continued until the organic mercury compound had all reacted (about 48 hours). TLC (petroleum ether:ethyl acetate=10:1) showed a new spot. After cooling, the reaction mixture was extracted with ethyl acetate (400 mL*3). The organic layer was washed sodium bisulfite solution (300 mL*3), dried over sodium sulfate and concentrated under reduced pressure. The residue was purified by silica gel column chromatography (0 to 20% ethyl acetate in petroleum ether) to afford trans-2,5-bis(iodomethyl)-1,4-dioxane (24 g, 65.23 mmol, 28.23% yield) as a white solid.

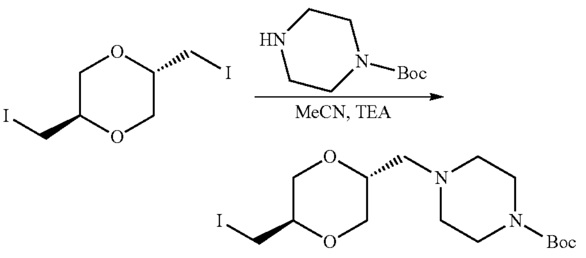

Step 2:

To a solution of trans-2,5-bis(iodomethyl)-1,4-dioxane (1.7 g, 4.62 mmol, 1 eq) and tert-butyl piperazine-1-carboxylate (774.46 mg, 4.16 mmol, 0.9 eq) in MeCN (6 mL) was added TEA (1.87 g, 18.48 mmol, 2.57 mL, 4 eq) and the reaction stirred at 80° C. for 16 hours under $N_2$. TLC (Petroleum ether:Ethyl acetate=0:1, PMA) of the reaction showed a new spot and the desired MS was detected by LCMS. The reaction was quenched by $H_2O$ (40 mL) solution and extracted with ethyl acetate (3*40 mL). The combined organic phases were washed with water, dried with $Na_2SO_4$, concentrated in vacuum to give a residue. The residue was purified by silica gel chromatography (Petroleum ether/Ethyl acetate=1:1) to afford tert-butyl 4-[[(2r,5s)-5-(iodomethyl)-1,4-dioxan-2-yl]methyl]piperazine-1-carboxylate (210 mg, 492.62 μmol, 10.66% yield) as brown solid.

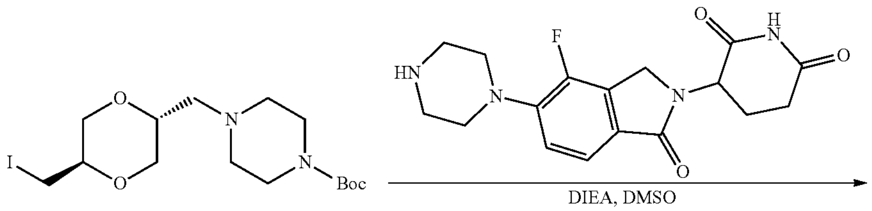

-continued

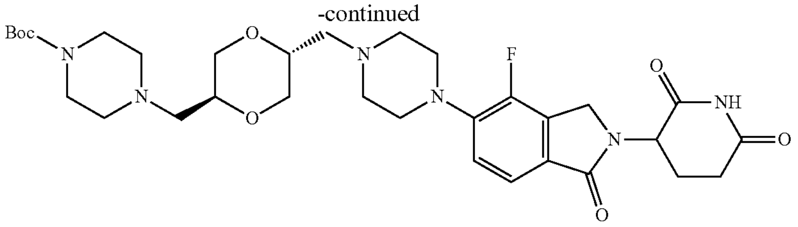

Step 3:

To a mixture of tert-butyl 4-[[(2r,5s)-5-(iodomethyl)-1,4-dioxan-2-yl]methyl]piperazine-1-carboxylate (340 mg, 797.58 μmol, 1 eq) and 3-(4-fluoro-1-oxo-5-piperazin-1-yl-isoindolin-2-yl)piperidine-2,6-dione (276.25 mg, 797.58 μmol, 1 eq) in DMSO (2 mL) was added DIEA (206.16 mg, 1.60 mmol, 277.85 uL, 2 eq) in one portion at 25° C. under $N_2$. The mixture was heated to 100° C. and stirred for 12 hours. TLC (Petroleum ether:Ethyl acetate=0:1) and LCMS showed the reaction was completed. The reaction was quenched by $H_2O$ (40 mL) solution and extracted with ethyl acetate (3*40 mL). The combined organic phases were washed with water, dried with $Na_2SO_4$, and concentrated in vacuum to give a residue. The residue was purified by silica gel chromatography (Petroleum ether/Ethyl acetate=0/1) to afford tert-butyl 4-[[(2s,5r)-5-[[4-[2-(2,6-dioxo-3-piperidyl)-4-fluoro-1-oxo-isoindolin-5-yl]piperazin-1-yl]methyl]-1,4-dioxan-2-yl]methyl]piperazine-1-carboxylate (180 mg, 279.19 μmol, 35.00% yield) as black brown solid. This compound was made as a mixture of trans-dioxane diastereomers.

Exemplary Synthesis of Compound 292

Compound 292 was prepared in a manner analogous to compounds 181 and 290 using intermediate tert-butyl 4-[2-(2,6-dioxo-3-piperidyl)-4-fluoro-1-oxo-isoindolin-5-yl]-3,6-dihydro-2H-pyridine-1-carboxylate.

Exemplary Synthesis of Compound 293

Compound 293 was prepared in a manner analogous to compound 211 using intermediate trans-[3-(4-piperidyloxy)cyclobutyl]methanol.

Exemplary Synthesis of Intermediate trans-[3-(4-piperidyloxy)cyclobutyl]methanol

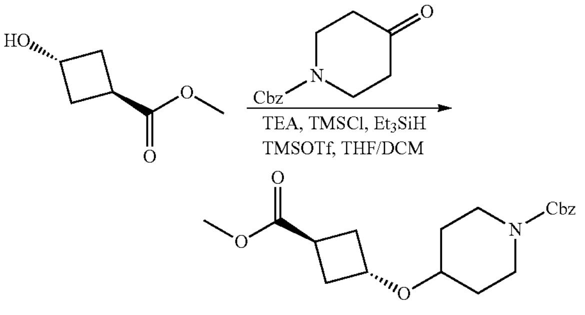

Step 1:

To a solution of methyl 3-hydroxycyclobutanecarboxylate (3.7 g, 28.43 mmol, 1 eq) in THF (10 mL) was added TEA (3.31 g, 32.70 mmol, 4.55 mL, 1.15 eq) and TMSCl (3.40 g, 31.27 mmol, 3.97 mL, 1.1 eq) at 0° C., and the reaction mixture was stirred at 20° C. for 30 minutes. The reaction mixture was filtered, and the filtrate was concentrated under reduced pressure to give a residue. Then to a stirred solution of above residue and benzyl 4-oxopiperidine-1-carboxylate (7.29 g, 31.27 mmol, 6.24 mL, 1.1 eq) in DCM (10 mL) was added Et3SiH (3.80 g, 32.70 mmol, 5.22 mL, 1.15 eq) and TMSOTf (3.16 g, 14.22 mmol, 2.57 mL, 0.5 eq) dropwise at −60° C., and the reaction mixture was stirred at 0° C. under $N_2$ for 1.5 hours LCMS showed desired MS. TLC (Petroleum ether:Ethyl acetate=3:1) showed several new spots The reaction mixture was quenched by addition sat. $NaHCO_3$ (adjust pH=8) at 0° C., and then diluted with extracted with DCM (20 mL*3). The combined organic layers were washed with brine (15 mL), dried over $Na_2SO_4$, filtered and concentrated under reduced pressure to give a residue The residue was purified by flash silica gel chromatography (0~16% Ethyl acetate in Petroleum ether) to give benzyl 4-(3-methoxycarbonylcyclobutoxy)piperidine-1-carboxylate (5 g, 11.08 mmol, 38.98% yield, 77% purity) as a colorless oil

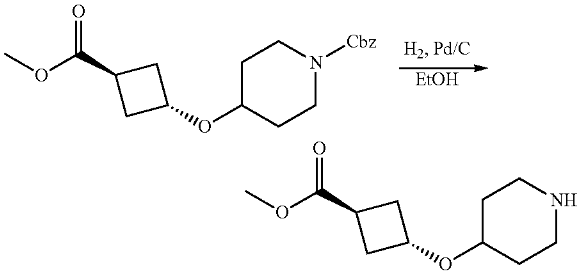

Step 2:

To a mixture of benzyl 4-(3-methoxycarbonylcyclobutoxy)piperidine-1-carboxylate (5 g, 14.39 mmol, 1 eq) in EtOH (10 mL) was added Pd/C (3 g, 14.39 mmol, 10% purity, 1 eq) at 25° C. under $H_2$ (15 PSI) for 2 hours. TLC (Petroleum ether:Ethyl acetate=3:1) showed one new major spot. The resulting product was concentrated in vacuum to give methyl 3-(4-piperidyloxy)cyclobutanecarboxylate (3.1 g, crude) as a colorless oil.

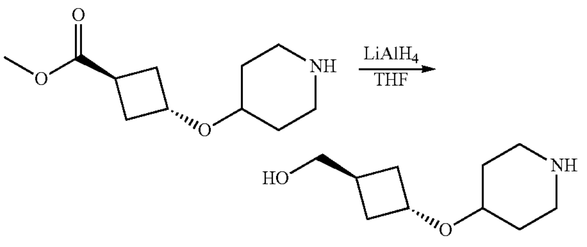

Step 3:

To a solution of methyl 3-(4-piperidyloxy)cyclobutanecarboxylate (3 g, 14.07 mmol, 1 eq) in THF (10 mL) was added $LiAlH_4$ (1.07 g, 28.13 mmol, 2 eq) at 0° C. under $N_2$ in portions. After addition, the reaction mixture was stirred at 0° C. for 1 hour. TLC (Dichloromethane:Methanol=5:1, Rf=0.07) showed no starting material and a new spot. The reaction mixture was quenched by addition of $H_2O$ (1 mL), followed by 15% aqueous NaOH (1 mL) and water (3 mL). After being stirred at room temperature for 30 min, the mixture was filtered through Celite pad to remove the solid. The filtrate was concentrated to dryness to give ((1r,3r)-3-(piperidin-4-yloxy)cyclobutyl)methanol (2 g, 10.80 mmol, 76.75% yield) as a white solid.

Exemplary Synthesis of Compound 294

Compound 294 was prepared in a manner analogous to compound 181 using intermediate benzyl (3s,4r)-3-fluoro-4-formyl-piperidine-1-carboxylate.

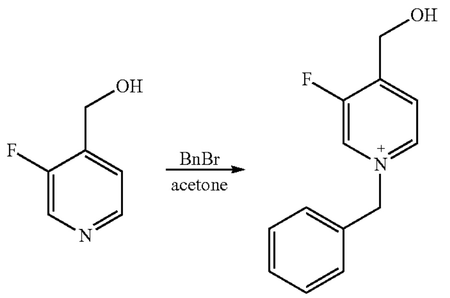

Step 1:

To a solution of (3-fluoro-4-pyridyl)methanol (14.8 g, 116.43 mmol, 1 eq) in Acetone (130 mL) was added BnBr (21.90 g, 128.07 mmol, 15.21 mL, 1.1 eq). The mixture was stirred at 65° C. for 16 hours. TLC (Petroleum ether:Ethyl acetate=0:1, Rf=0.1) showed a new spot. The reaction mixture was cooled to room temperature and diluted with MTBE (100 ml). The suspension was filtered, and the wet cake was then stirred with 25% acetone/MTBE v/v (200 ml) and filtered. The filter mass was then dried in vacuo to afford (1-benzyl-3-fluoro-pyridin-1-ium-4-yl)methanol (25 g, 114.55 mmol, 98.39% yield) as a yellow solid.

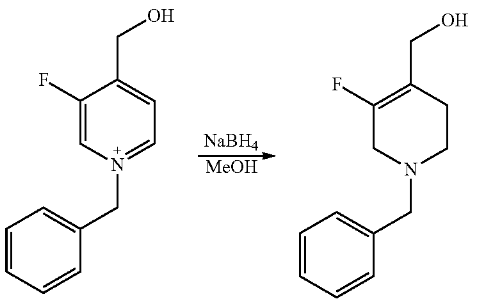

Step 2:

To a solution of (1-benzyl-3-fluoro-pyridin-1-ium-4-yl) methanol (25 g, 114.55 mmol, 1 eq) in MeOH (300 mL) at 0° C. and then was added $NaBH_4$ (6.50 g, 171.82 mmol, 1.5 eq) at 0° C. The mixture was stirred at 0° C. for 2 hours. TLC (Petroleum ether:Ethyl acetate=0:1, Rf=0.6) showed a new spot. LCMS showed the desired MS. The reaction mixture was quenched with 100 mL of $NH_4Cl$ (sat). The aqueous phase was extracted with ethyl acetate (3×100 mL). The combined organic layers were washed with brine (3×80 mL), dried over anhydrous sodium sulfate and concentrated under reduced pressure. The residue was purified by flash silica gel chromatography (ISCO®; 330 g SepaFlash® Silica Flash Column, Eluent of 0~100% Ethylacetate/Petroleum ethergradient @ 80 mL/min) to afford (1-benzyl-5-fluoro-3,6-dihydro-2H-pyridin-4-yl)methanol (13 g, 58.75 mmol, 51.29% yield) as a yellow gum.

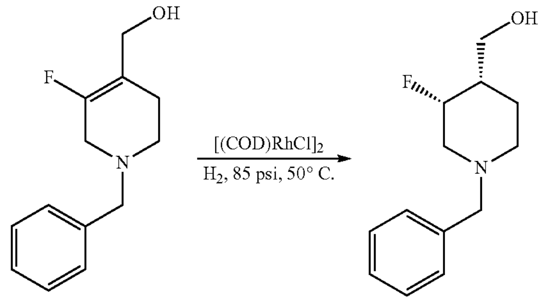

Step 3:

Under $N_2$ atmosphere, a three-necked round-bottom flask was charged with cyclopentane;dicyclohexyl-[(1R)-1-[2-(2-diphenylphosphanylphenyl)cyclopentyl]ethyl]phosphane; iron (22.5 mg, 33.55 μmol, 1.48 e-3 eq) chlororhodium; (1Z,5Z)-cycloocta-1,5-diene (7.5 mg, 15.21 μmol, 6.73 e-4 eq) and dry nitrogen degassed DCM (10 mL). The solution was stirred at ambient temperature for 45 minutes. A solution of (1-benzyl-5-fluoro-3,6-dihydro-2H-pyridin-4-yl) methanol (5 g, 22.60 mmol, 1 eq) in dry MeOH (50 mL) was added to a nitrogen purged 250 mL stainless steel pressure vessel. Subsequently, the aged catalyst solution from above was added into the vessel under nitrogen flow. The resulting mixture was degassed three times with $H_2$ and then (2.0 MPa, ca. 300 psi) heated at 50° C. under 2.0 MPa of $H_2$ for 36 hours with stirring. LCMS showed all desired product. TLC (Petroleum ether:Ethyl acetate=0:1, Rf=0.3) showed a new spot. The reaction vessel allowed to cool to room temperature and was purged with nitrogen. The reaction mixture was concentrated in vacuo to yield a dark brown oil. This concentrate was taken up in EtOAc (50 mL) and saturated aqueous $NaHCO_3$ (50 mL) was added. The mixture was stirred at room temperature for half hour and the organic phase was separated. The aqueous phase was extracted with three times with EtOAc (60 ml). The combined organic phases were washed with brine, dried over $Na_2SO_4$, and concentrated under vacuum. The residue was purified by flash silica gel chromatography (ISCO®; 330 g SepaFlash® Silica Flash Column, Eluent of 0~100% Ethylacetate/Petroleum ethergradient @ 60 mL/min) to afford (((3r,4s)-(1-benzyl-3-fluoro-4-piperidyl)methanol (2.95 g, 13.21 mmol, 58.47% yield) as yellow gum.

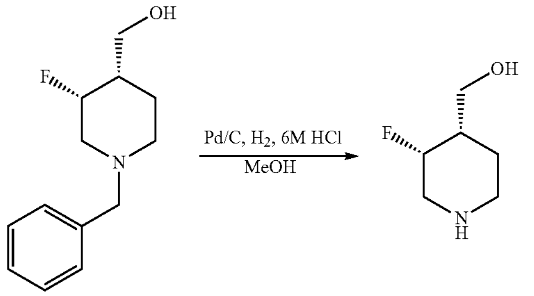 [SMILES: "MeOH" ; OC[C@@H]1CCN(Cc2ccccc2)C[C@@H]1F ; OC[C@@H]1CCNC[C@@H]1F]

Step 4:

To a stirred solution of ((3r,4s)-1-benzyl-3-fluoropiperidin-4-yl)methanol (2.95 g, 13.21 mmol, 1 eq) in MeOH (10 mL) was added Pd/C (300 mg, 13.21 mmol, 10% purity, 1 eq) and HCl (6 M, 3 mL, 1.36 eq). The mixture was purged with hydrogen three times at 15 psi. After stirring at 50° C. for 6 hours, the starting material was consumed. LCMS showed no starting material. TLC (Petroleum ether:Ethyl acetate=0:1, Rf=0.01) showed a new spot. The reaction mixture then was filtered through celite, the filter pad rinsed with MeOH, and the filtrate concentrated in vacuo to afford [(3s,4r)-3-fluoro-4-piperidyl]methanol (2.2 g, crude, HCl) as a white solid.

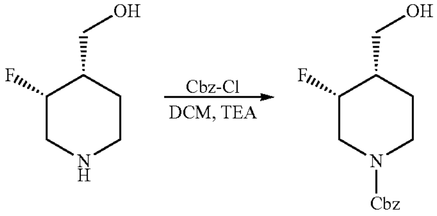 [SMILES: "Cbz-Cl" ; OC[C@@H]1CCNC[C@@H]1F ; O=C(OCc1ccccc1)N1CC[C@@H](CO)[C@@H](F)C1]

Step 5:

To a solution of [(3s,4r)-3-fluoro-4-piperidyl]methanol (2.2 g, 12.97 mmol, 1.18 eq, HCl) in DCM (50 mL) was added TEA (5.56 g, 54.96 mmol, 7.65 mL, 5 eq) at 0° C. and stirred at 0° C. for 30 minutes. Then CbzCl (3.60 g, 21.10 mmol, 3 mL, 1.92 eq) was added and stirred at 0° C. for 2 h under $N_2$. LCMS showed desired product. TLC (Petroleum ether:Ethyl acetate=0:1, Rf=0.5) of the reaction showed a new spot. The reaction diluted with water (40 mL). The mixture was extracted with ethyl acetate (50 mL*3), dried over anhydrous $Na_2SO_4$, and concentrated in vacuum to give a residue. The residue was purified by silica gel column chromatography (0-100% Ethyl acetate in Petroleum ether) to give benzyl (3s,4r)-3-fluoro-4-(hydroxymethyl)piperidine-1-carboxylate (2.8 g, 10.48 mmol, 95.30% yield) as a colorless gum.

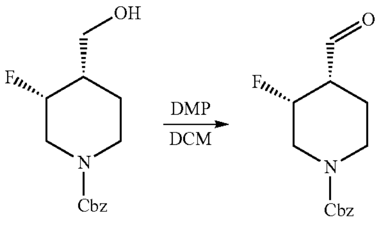 [SMILES: O=C(OCc1ccccc1)N1CC[C@@H](CO)[C@@H](F)C1 ; O=C[C@@H]1CCN(C(=O)OCc2ccccc2)C[C@@H]1F]

Step 6:

To a solution of benzyl (3s,4r)-3-fluoro-4-(hydroxymethyl)piperidine-1-carboxylate (500 mg, 1.87 mmol, 1 eq) in DCM (10 mL) at 20° C. was added DMP (1000.00 mg, 2.36 mmol, 729.93 uL, 1.26 eq) and stirred at 20° C. for 1 hour. LCMS showed desired product. TLC (Petroleum ether:Ethyl acetate=0:1, Rf=0.6) of the reaction showed a new spot. The reaction mixture was quenched by addition Sat.$NaHCO_3$ (adjust pH-8) at 0° C., and extracted with DCM (20 mL*3). The combined organic layers were washed with Sat.$NaSO_3$ (20 mL*2) and brine (10 mL*2), dried over $Na_2SO_4$, filtered, and concentrated under reduced pressure to give benzyl (3s,4r)-3-fluoro-4-formyl-piperidine-1-carboxylate (450 mg, crude) as a colorless gum.

Exemplary Synthesis of Compound 295

Compound 295 was prepared in a manner analogous to compound 181 starting from tert-butyl (3S)-3-(hydroxymethyl)pyrrolidine-1-carboxylate.

Exemplary Synthesis of Compound 296

Compound 296 was prepared in a manner analogous to compound 181 utilizing intermediate tert-butyl 4-[[(2r,5s)-5-(iodomethyl)-1,4-dioxan-2-yl]methyl]piperazine-1-carboxylate.

Exemplary Synthesis of Compound 297

Compound 297 was prepared in a manner analogous to compound 181 using intermediate (3r,4s)-tert-butyl 4-(2-(2,6-dioxopiperidin-3-yl)-4-fluoro-1-oxoisoindolin-5-yl)-3-fluoropiperidine-1-carboxylate.

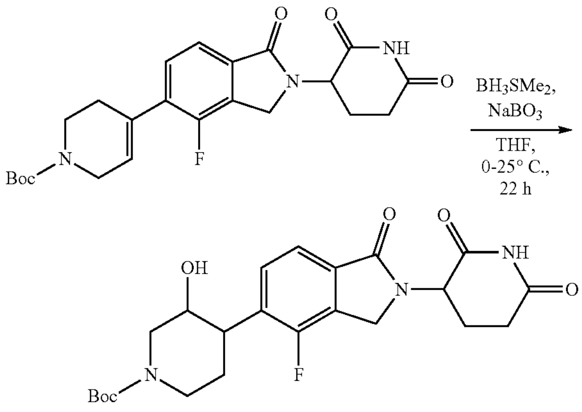

Step 1:

To a solution of tert-butyl 4-[2-(2,6-dioxo-3-piperidyl)-4-fluoro-1-oxo-isoindolin-5-yl]-3,6-dihydro-2H-pyridine-1-carboxylate (4 g, 9.02 mmol, 1 eq) in THF (400 mL) was added dropwise $BH_3$-$Me_2S$ (10 M, 9.02 mL, 10 eq) at 0° C. After addition, the mixture was stirred at 25° C. for 12 hours, and then sodium; 3-oxidodioxaborirane;tetrahydrate (4.16 g, 27.06 mmol, 5.20 mL, 3 eq) in $H_2O$ (20 mL) was added dropwise at 0° C. The resulting mixture was stirred at 25° C. for 10 hours. LCMS showed the desired mass was detected. The reaction mixture was quenched with saturated sodium sulfite solution (80 mL) and the mixture was extracted with ethyl acetate (70 mLx3). The combined organic phase was washed with brine (50 mL), dried with anhydrous sodium sulfate, filtered, and concentrated in vacuo. The residue was purified by flash silica gel chromatography (ISCO®; 40 g SepaFlash® Silica Flash Column, Eluent of 0~15% Methanol/Dichloromethane gradient @ 80 mL/min) to give tert-butyl 4-[2-(2,6-dioxo-3-piperidyl)-4-fluoro-1-oxo-isoindolin-5-yl]-3-hydroxy-piperidine-1-carboxylate (1.5 g, 2.67 mmol, 29.55% yield, 82% purity) as a white solid.

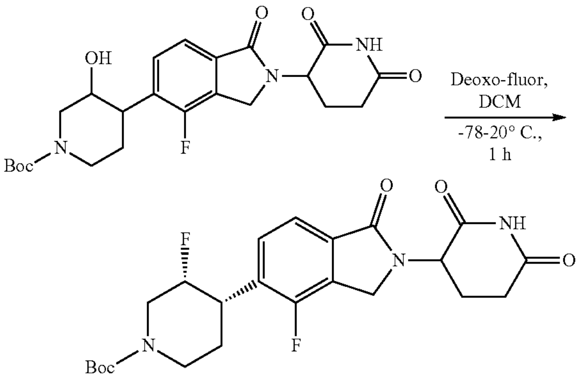

Step 2:

To a solution of tert-butyl 4-(2-(2,6-dioxopiperidin-3-yl)-4-fluoro-1-oxoisoindolin-5-yl)-3-hydroxypiperidine-1-carboxylate (1.5 g, 3.25 mmol, 1 eq) in DCM (100 mL) was N-ethyl-N-(trifluoro-X4-sulfanyl)ethanamine (2.10 g, 13.00 mmol, 1.72 mL, 4 eq) at −78° C. The mixture was stirred at 20° C. for 1 hour. TLC (Dichloromethane:Methanol=10:1) indicated reactant 1 was consumed completely and new spots formed. The reaction mixture was with $H_2O$ (20 mL) and extracted with DCM (20 mL×3). The combined organic layers were washed with brine, dried over $Na_2SO_4$, filtered, and concentrated under reduced pressure to give a residue. The residue was purified by flash silica gel chromatography (ISCO®; 40 g SepaFlash® Silica Flash Column, Eluent of 0~79% Ethyl acetate/Petroleum ether gradient @ 100 m/min) to give (3r,4s)-tert-butyl 4-(2-(2,6-dioxopiperidin-3-yl)-4-fluoro-1-oxoisoindolin-5-yl)-3-fluoropiperidine-1-carboxylate (627 mg, 1.35 mmol, 41.62% yield) as a white solid.

Exemplary Synthesis of Compound 298

Compound 298 was prepared in a manner analogous to compound 211 using intermediate tert-butyl 3-(4-piperidyloxy)azetidine-1-carboxylate.

Exemplary Synthesis of Compound 299

Compound 299 was prepared in a manner analogous to compound 181 using intermediate benzyl (3s,4r)-3-fluoro-4-(hydroxymethyl)piperidine-1-carboxylate.

Exemplary Synthesis of Compound 300

Compound 300 was prepared in a manner analogous to compound 209 using intermediate trans-[3-(4-piperidyloxy) cyclobutyl]methanol.

Exemplary Synthesis of Compound 301

Compound 301 was prepared in a manner analogous to compound 209 using intermediate tert-butyl 3-fluoro-3-(hydroxymethyl)azetidine-1-carboxylate.

Exemplary Synthesis of Compound 302

Compound 302 was prepared in a manner analogous to compound 211 using intermediates tert-butyl 4-[[(2r,5s)-5-(iodomethyl)-1,4-dioxan-2-yl]methyl]piperazine-1-carboxylate and 3-(6-chloropyrimidin-4-yl)-5-(1-methylcyclopropoxy)-1-trityl-pyrazolo[3,4-c]pyridine.

Exemplary Synthesis of Compound 303

Compound 303 was prepared in a manner analogous to compound 181 starting from tert-butyl (3S)-3-(hydroxymethyl)pyrrolidine-1-carboxylate.

Exemplary Synthesis of Compound 304

Compound 304 was prepared in a manner analogous to compound 181 using intermediate tert-butyl 4-((1r,3r)-3-(2,7-diazaspiro[3.5]nonan-7-yl)cyclobutoxy)piperidine-1-carboxylate.

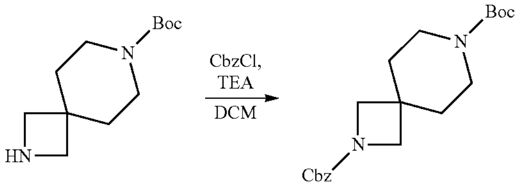 [SMILES: CC(C)(C)OC(=O)N1CCC2(CC1)CNC2 ; CC(C)(C)OC(=O)N1CCC2(CC1)CN(C(=O)OCc1ccccc1)C2]

Step 1:

To a solution of tert-butyl 2,7-diazaspiro[3.5]nonane-7-carboxylate (3 g, 13.26 mmol, 1 eq) in DCM (30 mL) was added CbzCl (2.88 g, 16.88 mmol, 2.4 mL, 1.27 eq) and TEA (4.02 g, 39.77 mmol, 5.54 mL, 3 eq) at 0° C. The mixture was stirred at 20° C. for 2 hours. LC-MS showed the reactant was consumed with one new main peak with desired m/z. The reaction mixture was diluted with $H_2O$ (50 mL) and extracted with DCM (20 mL×3). The combined organic layers were washed with brine, dried over $Na_2SO_4$, filtered, and concentrated under reduced pressure to give a residue. The residue was purified by flash silica gel chromatography (ISCO®; 40 g SepaFlash® Silica Flash Column, Eluent of 0-32% Ethyl acetate/Petroleum ethergradient @ 100 m/min) to give 02-benzyl 07-tert-butyl 2,7-diazaspiro[3.5]nonane-2,7-dicarboxylate (2.77 g, 7.68 mmol, 57.97% yield) as a colorless oil.

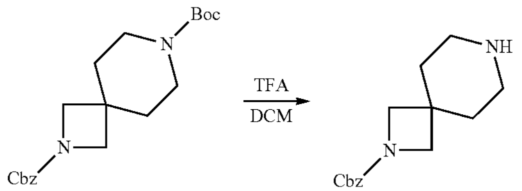 [SMILES: CC(C)(C)OC(=O)N1CCC2(CC1)CN(C(=O)OCc1ccccc1)C2 ; O=C(OCc1ccccc1)N1CC2(CCNCC2)C1]

Step 2:

To a solution of 02-benzyl 07-tert-butyl 2,7-diazaspiro [3.5]nonane-2,7-dicarboxylate (2.77 g, 7.68 mmol, 1 eq) in DCM (10 mL) was added TFA (7.70 g, 67.53 mmol, 5.00 mL, 8.79 eq). The mixture was stirred at 20° C. for 30 minutes. LC-MS showed reactant was consumed and a new main peak with desired m/z was present. The reaction mixture was concentrated under reduced pressure to remove DCM to give benzyl 2,7-diazaspiro[3.5]nonane-2-carboxylate (3.2 g, crude, TFA) as a yellow oil.

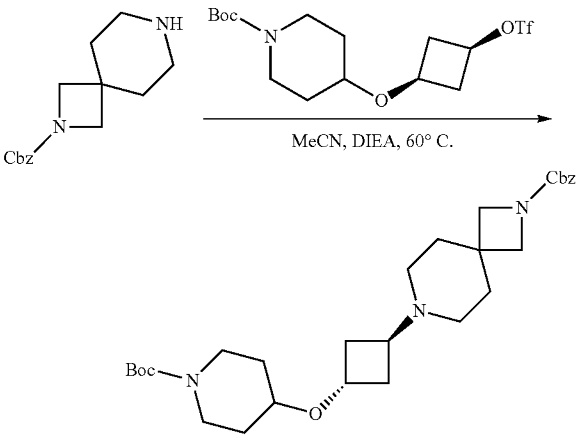

Step 3:

To a solution of benzyl 2,7-diazaspiro[3.5]nonane-2-carboxylate (1.25 g, 4.80 mmol, 1 eq) and tert-butyl 4-[3-(trifluoromethylsulfonyloxy)cyclobutoxy]piperidine-1-carboxylate (2.52 g, 6.24 mmol, 1.3 eq) in MeCN (10 mL) was added DIEA (3.10 g, 24.01 mmol, 4.18 mL, 5 eq). The mixture was stirred at 60° C. for 12 hours. LCMS showed reactant was consumed and one new main peak with desired m/z was detected. The reaction mixture was added silica powder and concentrated under reduced pressure to remove MeCN. The residue was purified by flash silica gel chromatography (ISCO®; 40 g SepaFlash® Silica Flash Column, Eluent of 0~8% Methanol/Dichloromethane gradient @ 100 m/min) to give a benzyl 7-[3-[(1-tert-butoxycarbonyl-4-piperidyl)oxy]cyclobutyl]-2,7-diazaspiro[3.5]nonane-2-carboxylate (2 g, 3.89 mmol, 81.09% yield) as a yellow solid.

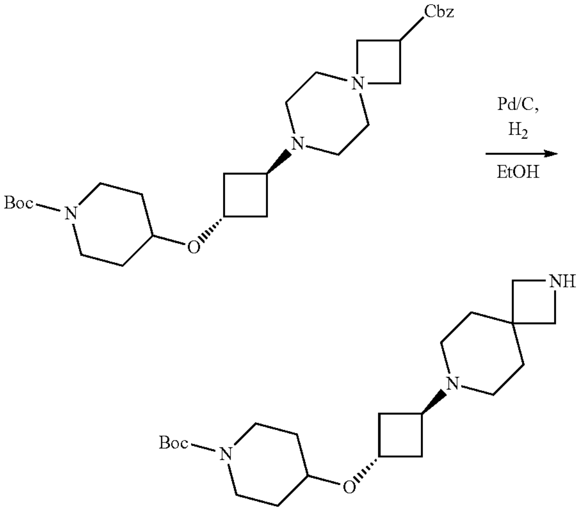

Step 4:

A mixture of benzyl 7-[3-[(1-tert-butoxycarbonyl-4-piperidyl)oxy]cyclobutyl]-2,7-diazaspiro[3.5]nonane-2-carboxylate (1 g, 1.95 mmol, 1 eq) and Pd/C (200 mg, 1.95 mmol, 10% purity, 1 eq) in EtOH (10 mL) was degassed and purged with $H_2$ for 3 times, and then the mixture was stirred at 20° C. for 2 hours under $H_2$ atmosphere. TLC (Dichloromethane:Methanol=10:1) indicated reactant was consumed and one new spot formed. The reaction was clean according to TLC. The reaction mixture was added diatomite, filtered and concentrated under reduced pressure to give a tert-butyl 4-((1r,3r)-3-(2,7-diazaspiro[3.5]nonan-7-yl)cyclobutoxy)piperidine-1-carboxylate (526 mg, crude) was obtained as a colorless oil.

Exemplary Synthesis of Compound 305

Compound 305 was prepared in a manner analogous to compound 181 using intermediate tert-butyl 4-[[(3r,6r)-6-(piperazin-1-ylmethyl)tetrahydropyran-3-yl]methyl]piperazine-1-carboxylate.

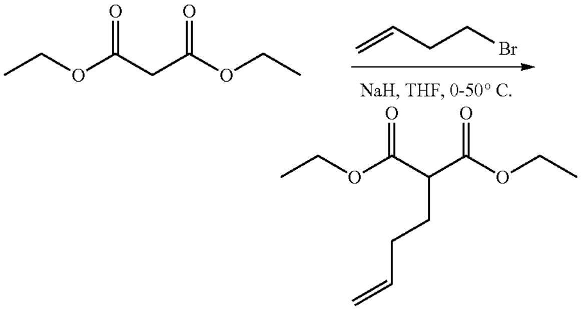

Step 1:

To a stirred solution of diethyl propanedioate (100 g, 624.35 mmol, 94.34 mL, 1 eq) in THF (800 mL) was added NaH (27.47 g, 686.78 mmol, 60% purity, 1.1 eq) at 0° C. in portions. The mixture was stirred at 0° C. for 30 minutes. 4-Bromobut-1-ene (92.72 g, 686.78 mmol, 69.71 mL, 1.1 eq) was added to the mixture. The resulting mixture was stirred at 50° C. for 12 hours. TLC (Petroleum ether:Ethyl acetate=4:1) showed a new spot was formed as the major product. The mixture was poured into cold saturated $NH_4Cl$ aqueous (1 L) and the aqueous was extracted with ethyl acetate (600 mL*3). The combined organic layer was dried over anhydrous $Na_2SO_4$, filtered, and the filtrate was concentrated under vacuum. The residue was purified by MPLC (ISCO®; X g SepaFlash® Silica Flash Column, Eluent of 0~10% Ethyl acetate/Petroleum ether gradient @ 90 m/min). diethyl 2-but-3-enylpropanedioate (72 g, 336.04 mmol, 53.82% yield) was obtained as a colorless oil.

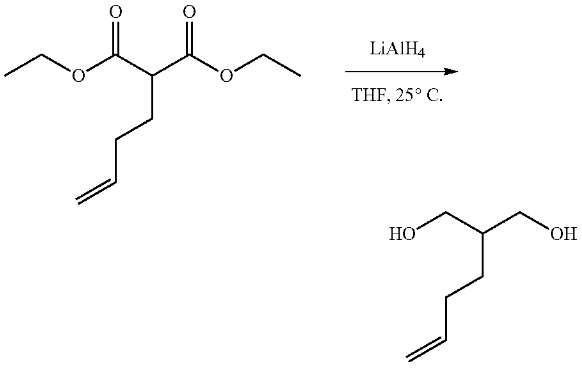

Step 2:

To a stirred solution of diethyl 2-but-3-enylpropanedioate (72 g, 336.04 mmol, 1 eq) in t-BuOH (400 mL) and MeOH (80 mL) was added $NaBH_4$ (38.71 g, 1.02 mol, 3.05 eq) in portions at 25° C. The resulting mixture was stirred at 25° C. for 12 hours. TLC (PE:EA=2:1) showed reactant was consumed and a new spot was formed. Hydrochloric acid (1 N) was added until the solution was neutral at 0° C. The aqueous was extracted with ethyl acetate (300 mL*3). The combined organic layer was dried over anhydrous $Na_2SO_4$, filtered and the filtrate was concentrated under vacuum. The residue was used directly for next step without further purification. 2-But-3-enylpropane-1,3-diol (42 g, 322.62 mmol, 96.01% yield) was obtained as a light yellow oil.

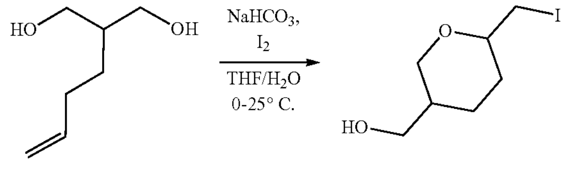

Step 3:

To a stirred suspension of iodine (122.83 g, 483.93 mmol, 97.48 mL, 1.5 eq) and $NaHCO_3$ (40.65 g, 483.93 mmol, 18.82 mL, 1.5 eq) in tetrahedronfuran (200 mL) and water (80 mL) was added the solution of 2-but-3-enylpropane-1, 3-diol (42 g, 322.62 mmol, 1 eq) in THF (200 mL) at 0° C. The mixture was stirred at 25° C. for 12 hours. LCMS showed the desired mass was detected. Saturated $Na_2S_2O_3$ aqueous (500 mL) was added to the mixture slowly at 0° C. and the mixture was stirred at 25° C. for 10 minutes. The solution was extracted with EtOAc (300 ml*3). The combined organic layer was dried over anhydrous sodium sulfate, filtered, and the filtrate was concentrated under vacuum. The residue was purified by silica gel chromatography (PE:EtOAc=100:1-1:1). [6-(iodomethyl)tetrahydropyran-3-yl]methanol (34 g, 132.77 mmol, 41.15% yield) was obtained as a light yellow oil.

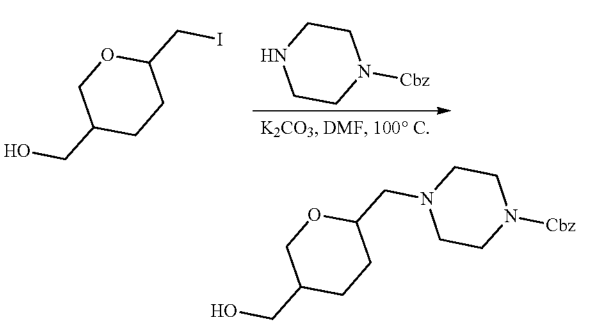

Step 4:

To a stirred solution of [6-(iodomethyl)tetrahydropyran-3-yl]methanol (12.4 g, 48.42 mmol, 1 eq) in DMF (100 mL) was added $K_2CO_3$ (16.73 g, 121.06 mmol, 2.5 eq) and benzyl piperazine-1-carboxylate (12.80 g, 58.11 mmol, 11.23 mL, 1.2 eq). The reaction mixture was stirred at 100° C. for 12 hours. LCMS showed desired mass was detected. Water (300 mL) was added to the mixture and the aqueous was extracted with ethyl acetate (200 mL*3). The combined organic layer was washed with brine (200 mL*2), dried over anhydrous $Na_2SO_4$, filtered and the filtrate was concentrated under vacuum. The residue was purified by silica gel chromatography (DCM:MeOH=100:1-10:1). Benzyl 4-[[5-(hydroxymethyl)tetrahydropyran-2-yl]methyl]piperazine-1-carboxylate (13 g, 37.31 mmol, 77.05% yield) was obtained as a mixture of diasteromers as a colorless oil.

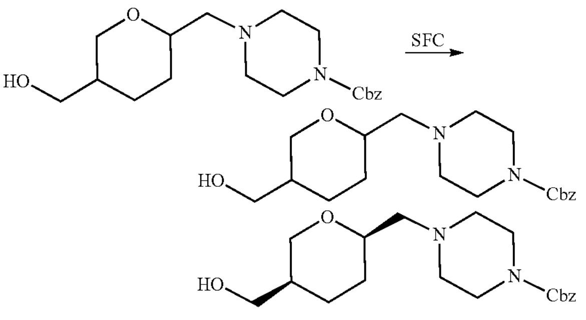

(a mixture of 1 cis isomer 2 and trans isomers)

Step 5:

The cis isomer benzyl 4-(((2R,5S)-5-(hydroxymethyl) tetrahydro-2H-pyran-2-yl)methyl)piperazine-1-carboxylate or the enantiomer thereof (1.53 g, 3.92 mmol, 11.01% yield, 89.24% purity, peak 4: de=100%, Rt=1.416 min) was obtained by SCF purification of the diastereomeric mixture of benzyl 4-[[5-(hydroxymethyl)tetrahydropyran-2-yl] methyl]piperazine-1-carboxylate (12.40 g, 35.59 mmol, 1 eq) by SFC. The first fraction obtained (10.19 g, 29.25 mmol, 82.19% yield) was a mixture of a single cis isomer (peak 2: Rt=1.161 min) and trans isomers (peak 1: Rt=1.125 min, peak 3: Rt=1.195 min)

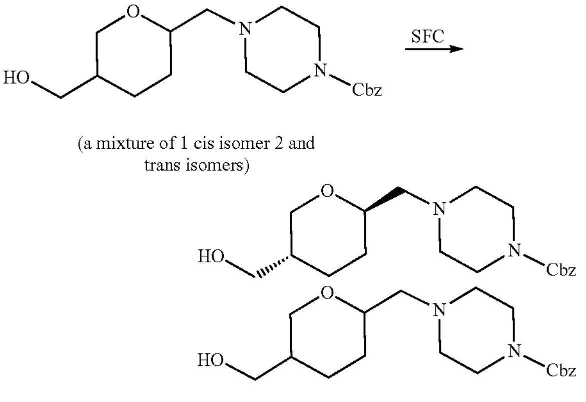

(a mixture of 1 cis isomer 2 and trans isomers)

(a mixture of 1 cis isomer 2 and the trans isomer 2)

Step 6:

Benzyl 4-[[(2R,5R)-5-(hydroxymethyl)tetrahydropyran-2-yl]methyl]piperazine-1-carboxylate or the enantiomer thereof (trans isomer confirmed by HSQC, peak 3: de %=100, Rt=2.614 min, 3.24 g, 8.86 mmol, 30.31% yield, 95.32% purity) was obtained as a light yellow oil by SFC resolution of the diastereomeric mixture of 1 cis isomer and 2 trans isomers (10.19 g, 29.25 mmol). The remaining diasteromers were obtained as a mixture (mixture of cis isomer 2 and trans isomer 2, 4.19 g, 12.03 mmol, 41.14% yield, peak 1: Rt=1.156 min, peak2: Rt=1.244 min) as a light yellow oil.

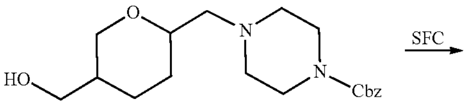

(a mixture of cis isomer 2 and the trans isomer 2)

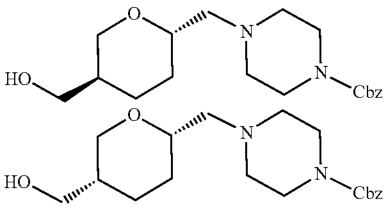

Step 7:

The trans product 4-[[(2S,5S)-5-(hydroxymethyl)tetrahydropyran-2-yl]methyl]piperazine-1-carboxylate or the enantiomer thereof (2.41 g, 6.58 mmol, 54.71% yield, 95.11% purity, yellow oil, trans isomer 2, peak 1: de=100%, Rt=1.977 min) and cis product benzyl 4-[[(2S,5R)-5-(hydroxymethyl)tetrahydropyran-2-yl]methyl]piperazine-1-carboxylate or the enantiomer thereof (3.10 g, 8.45 mmol, 70.27% yield, 94.98% purity, yellow oil, cis isomer 2, peak2: de=100%, Rt=2.088 min) were obtained by SFC separation of the cis and trans diasteromers.

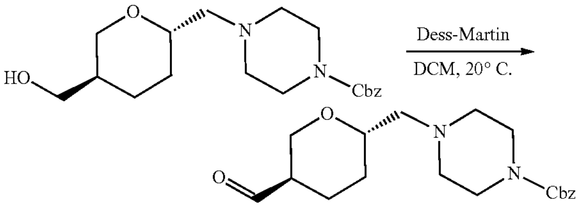

Step 8:

To a solution of benzyl 4-[[(2S,5S)-5-(hydroxymethyl)tetrahydropyran-2-yl]methyl]piperazine-1-carboxylate or the enantiomer thereof (890 mg, 2.55 mmol, 1 eq) in DCM (2 mL) was added Dess-Martin periodate (1.08 g, 2.55 mmol, 790.78 uL, 1 eq). The mixture was stirred at 20° C. for 12 hours. TLC plate showed no starting material remained and one new spot with less polarity was formed. The reaction mixture was diluted with water (10 mL), neutralized with sodium bicarbonate to pH=7, then extracted with DCM 15 mL (5 mL*3). The combined organic phase was dried over anhydrous sodium sulfate, and concentrated under vacuum to give a residue without further purification. Compound benzyl 4-[[(2S,5R)-5-formyltetrahydropyran-2-yl]methyl]piperazine-1-carboxylate or the enantiomer thereof (750 mg, 2.17 mmol, 84.76% yield) was obtained as a yellow solid.

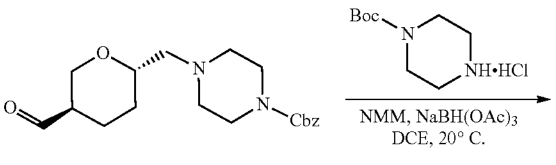

-continued

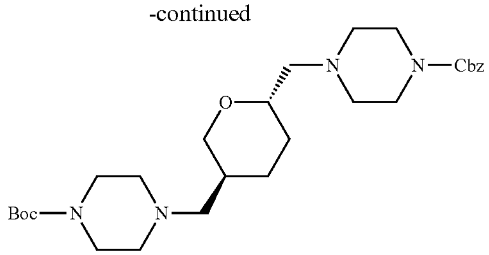

Step 9:

To a solution of tert-butyl piperazine-1-carboxylate (578.61 mg, 2.60 mmol, 1.2 eq, HCl) in DMF (5 mL) was added NMM (437.97 mg, 4.33 mmol, 476.05 uL, 2 eq), then benzyl 4-[[(2S,5R)-5-formyltetrahydropyran-2-yl]methyl]piperazine-1-carboxylate or the enantiomer thereof (750 mg, 2.17 mmol, 1 eq) and sodium borohydride acetate (917.71 mg, 4.33 mmol, 2 eq) were added. The mixture was stirred at 20° C. for 3 hours. TLC indicated one major new spot with larger polarity was detected. The reaction mixture was partitioned between water 10 mL and DCM (10 mL*3) 30 mL. The organic phase was separated, dried over anhydrous sodium sulfate, filtered, and concentrated under reduced pressure to give a residue. The residue was purified by prep-TLC (SiO2, EtOAc:PE=1:2) to afford tert-butyl 4-[[(3S,6S)-6-[(4-benzyloxycarbonylpiperazin-1-yl)methyl]tetrahydropyran-3-yl]methyl]piperazine-1-carboxylate or the enantiomer thereof (900 mg, 1.74 mmol, 80.46% yield) was obtained as a yellow solid.

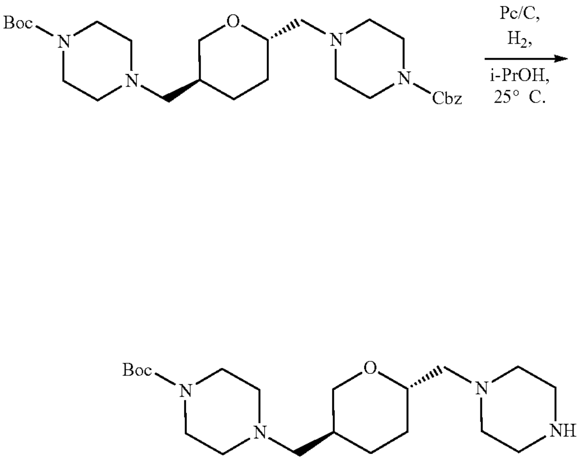

Step 10:

A mixture of tert-butyl 4-[[(3S,6S)-6-[(4-benzyloxycarbonylpiperazin-1-yl)methyl]tetrahydropyran-3-yl]methyl]piperazine-1-carboxylate or the enantiomer thereof (900 mg, 1.74 mmol, 1 eq) and Pd/C (90 mg, 10% purity) in i-PrOH (10 mL) was degassed and purged with $H_2$ for three times, and then the mixture was stirred at 25° C. for 2 hours under $H_2$ atmosphere. LC-MS showed no reactant remained. The reaction mixture was filtered and concentrated under reduced pressure to give a residue. Compound tert-butyl 4-[[(3S,6S)-6-(piperazin-1-ylmethyl)tetrahydropyran-3-yl]methyl]piperazine-1-carboxylate or the enantiomer thereof (560 mg, 1.46 mmol, 84.04% yield) was obtained as a white solid without further purification.

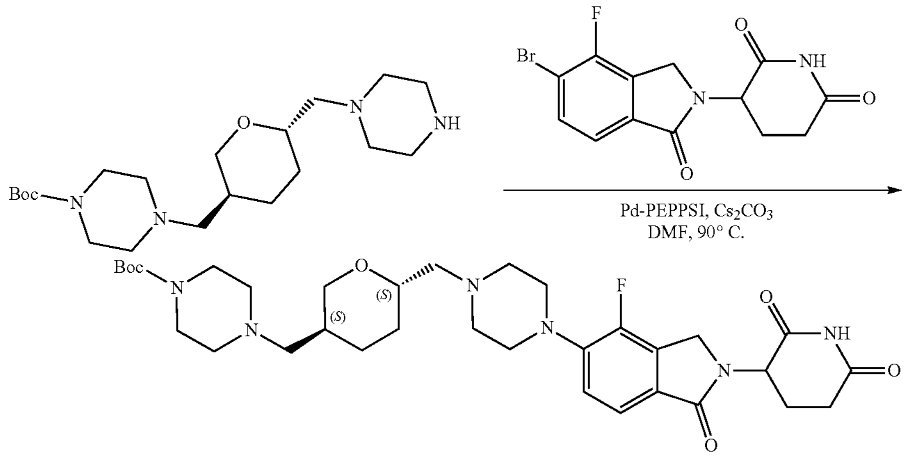

Step 11:

To a solution of tert-butyl 4-[[(3S,6S)-6-(piperazin-1-ylmethyl)tetrahydropyran-3-yl]methyl]piperazine-1-carboxylate or the enantiomer thereof (500 mg, 1.31 mmol, 1.1 eq) and 3-(5-bromo-4-fluoro-1-oxo-isoindolin-2-yl)piperidine-2,6-dione (405.34 mg, 1.19 mmol, 1 eq) in DMF (2 mL) was added cesium carbonate (619.44 mg, 1.90 mmol, 1.6 eq). After addition, the reaction was flushed with $N_2$ for 3 times, then (SP-4-1)-[1,3-Bis[2,6-bis(1-ethylpropyl)phenyl]-4,5-dichloro-1,3-dihydro-2H-imidazol-2-ylidene]dichloro(3-chloropyridine-cN)palladium (102.25 mg, 0.12 mmol, 0.1 eq) was added, the mixture was stirred at 90° C. for 16 hours under $N_2$ atmosphere. LC-MS showed desired compound was detected. The reaction mixture was filtered, then the filtrate was adjusted to pH=7 with formic acid, and concentrated under vacuum to give a residue. The residue was purified by prep-HPLC (column: Phenomenex Synergi Polar-RP 100*25 mm*4 um; mobile phase: [water (TFA)-ACN]; B %: 17%-37%, 7 min) to afford tert-butyl 4-[[(3S,6S)-6-[[4-[2-(2,6-dioxo-3-piperidyl)-4-fluoro-1-oxo-isoindolin-5-yl]piperazin-1yl]methyl]tetrahydropyran-3-yl]methyl]piperazine-1-carboxylate or the enantiomer thereof (150 mg, 233.37 μmol, 19.64% yield) as a yellow solid.

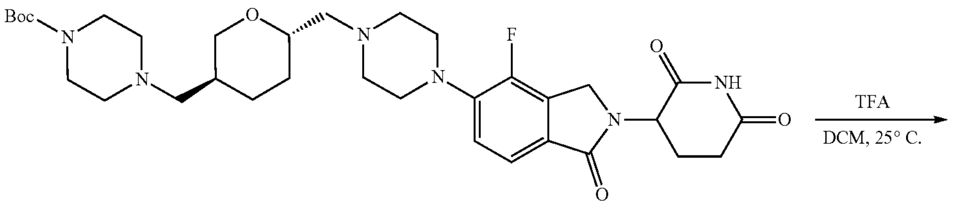

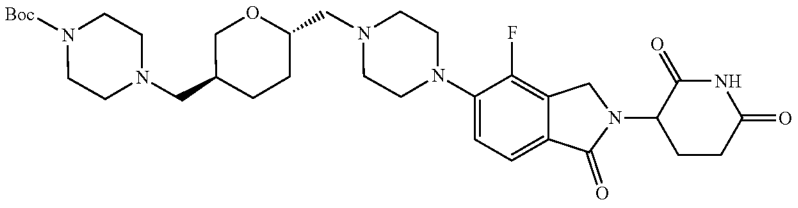

Step 12:

To a solution of tert-butyl 4-[[(3S,6S)-6-[[4-[2-(2,6-dioxo-3-piperidyl)-4-fluoro-1-oxo-isoindolin-5-yl]piperazin-1-yl]methyl]tetrahydropyran-3-yl]methyl]piperazine-1-carboxylate or the enantiomer thereof (60 mg, 0.093 mmol, 1 eq) in DCM (2 mL) was added TFA (770.00 mg, 6.75 mmol, 0.5 mL, 72.34 eq). The mixture was stirred at 25° C. for 15 minutes. TLC showed a new spot was formed. The reaction mixture was concentrated under reduced pressure to give a residue affording 3-[4-fluoro-1-oxo-5-[4-[[(2S,5S)-5-(piperazin-1-ylmethyl)tetrahydropyran-2-yl]methyl]piperazin-1-yl]isoindolin-2-yl]piperidine-2,6-dione or the enantiomer thereof (61 mg, 0.093 mmol, 99.51% yield, TFA) as a yellow oil which was used without further purification.

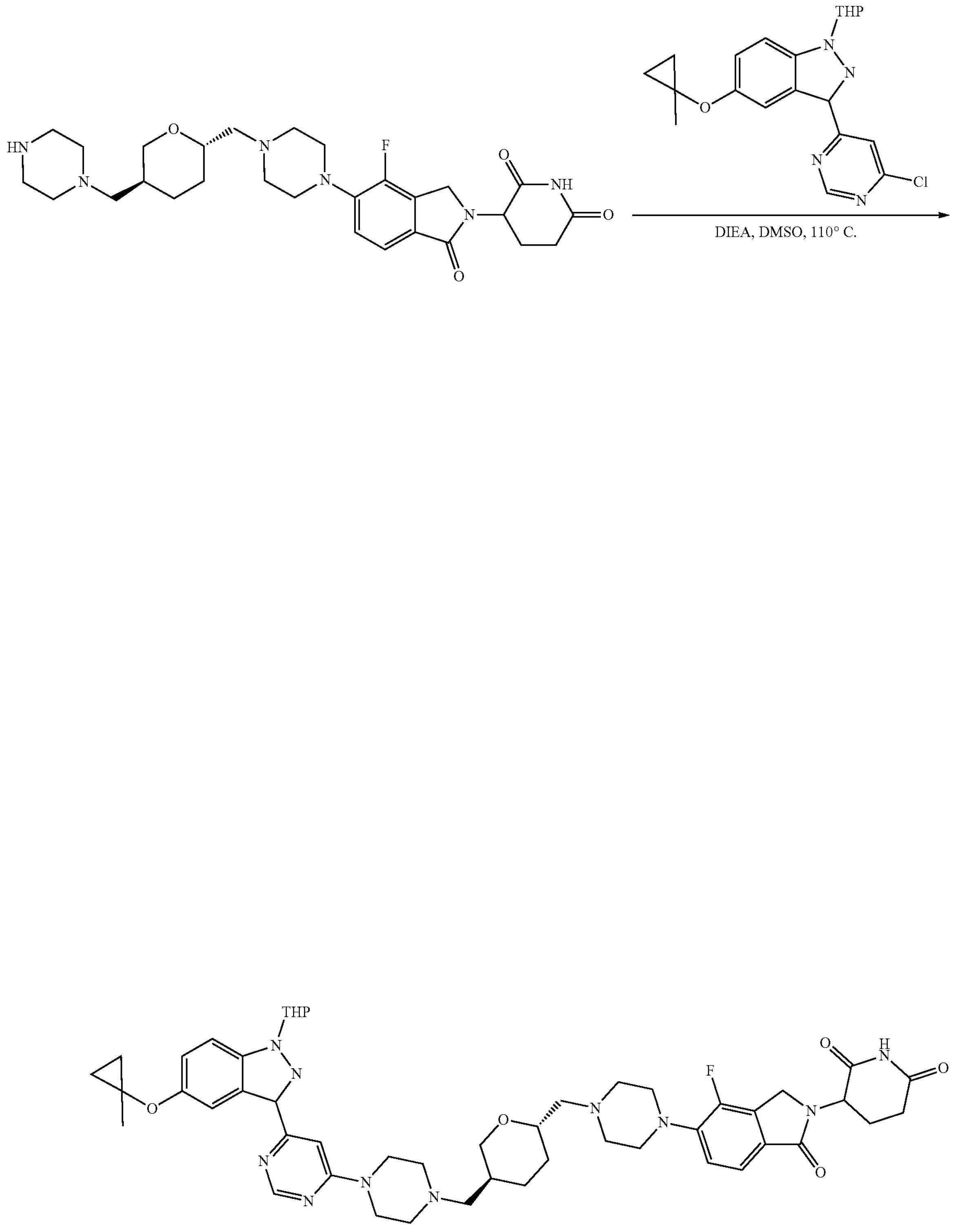

Step 13:

To a solution of 3-[4-fluoro-1-oxo-5-[4-[[(2S,5S)-5-(piperazin-1-ylmethyl)tetrahydropyran-2-yl]methyl]piperazin-1-yl]isoindolin-2-yl]piperidine-2,6-dione or the enantiomer thereof (61 mg, 0.093 mmol, 1 eq, TFA salt) and 3-(6-chloropyrimidin-4-yl)-5-(1-methylcyclopropoxy)-1-tetrahydropyran-2-yl-indazole (35.75 mg, 0.093 mmol, 1 eq) in DMSO (1 mL) was added DIEA (60.03 mg, 0.46 mmol, 0.081 mL, 5 eq). The mixture was stirred at 100° C. for 16 hours. LC-MS showed desired compound was detected. The reaction mixture was partitioned between water 2 mL and DCM 15 mL (5 mL*3). The organic phase was separated, dried over sodium sulfate, filtered, and concentrated under reduced pressure to give a residue. The residue was purified by prep-TLC (SiO2, DCM:MeOH=10:1). Then further purified by prep-HPLC (column: Unisil 3-100 C18 Ultra 150*50 mm*3 um; mobile phase: [water (FA)-ACN]; B %: 6%-36%, 7 min). Compound 3-[4-fluoro-5-[4-[[(2S,5S)-5-[[4-[6-[5-(1-methylcyclopropoxy)-1-tetrahydropyran-2-yl-indazol-3-yl]pyrimidin-4-yl]piperazin-1-yl]methyl]tetrahydropyran-2-yl]methyl]piperazin-1-yl]-1-oxo-isoindolin-2-yl]piperidine-2,6-dione or the enantiomer thereof (30 mg, 0.033 mmol, 36.25% yield) was obtained as a yellow solid.

Exemplary Synthesis of Compound 306

Compound 306 was prepared in a manner analogous to compound 181 using intermediate tert-butyl 3-fluoro-3-(hydroxymethyl)azetidine-1-carboxylate.

Exemplary Synthesis of Compound 307

Compound 307 was prepared in a manner analogous to compound 209.

Exemplary Synthesis of Compound 308

Compound 308 was prepared in a manner analogous to compound 181 using intermediate tert-butyl (4S)-4-[(1-benzyloxycarbonyl-4-piperidyl)oxy]-2,2-dimethyl-piperidine-1-carboxylate or the enantiomer thereof.

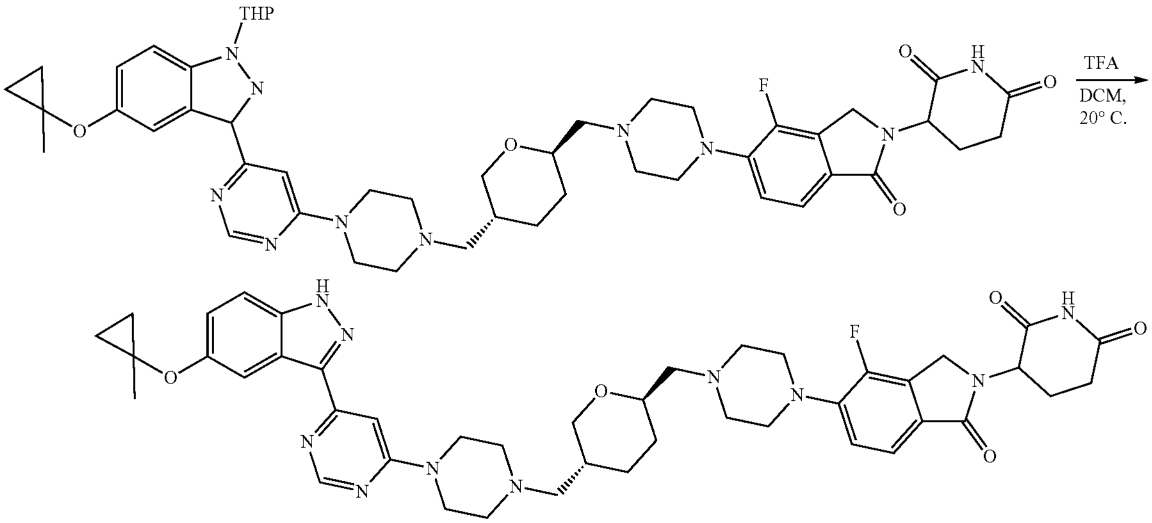

Step 14:

To a solution of 3-[4-fluoro-5-[4-[[(2S,5S)-5-[[4-[6-[5-(1-methylcyclopropoxy)-1-tetrahydropyran-2-yl-indazol-3-yl]pyrimidin-4-yl]piperazin-1-yl]methyl]tetrahydropyran-2-yl]methyl]piperazin-1-yl]-1-oxo-isoindolin-2-yl]piperidine-2,6-dione or the enantiomer thereof (25 mg, 0.028 mmol, 1 eq) in DCM (1 mL) was added TFA (1.54 g, 13.51 mmol, 1 mL, 481.38 eq). The mixture was stirred at 20° C. for 40 hours. LC-MS showed desired compound was detected. The reaction mixture was concentrated under vacuum to give a residue. The residue was purified by prep-HPLC (column: Unisil 3-100 C18 Ultra 150*50 mm*3 um; mobile phase: [water (FA)-ACN]; B %: 1%-29%, 7 min). Compound 3-[4-fluoro-5-[4-[[(2S,5S)-5-[[4-[6-[5-(1-methylcyclopropoxy)-1H-indazol-3-yl]pyrimidin-4-yl]piperazin-1-yl]methyl]tetrahydropyran-2yl]methyl]piperazin-1-yl]-1-oxo-isoindolin-2-yl]piperidine-2,6-dione or the enantiomer thereof (5.9 mg, 6.06 μmol, 21.59% yield, 82.86% purity) was obtained as a yellow solid.

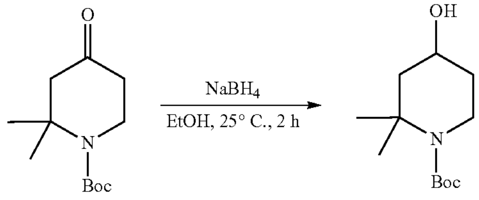 [SMILES: CC(C)(C)OC(=O)N1CCC(=O)CC1(C)C ; "NaBH4" ; CC(C)(C)OC(=O)N1CCC(O)CC1(C)C]

Step 1:

To a mixture of tert-butyl 2,2-dimethyl-4-oxo-piperidine-1-carboxylate (10 g, 43.99 mmol, 1 eq) in ethanol (100 mL) was added sodium borohydride (9.18 g, 242.62 mmol, 5.51 eq) in small portions at 0° C. The mixture was stirred at 25° C. for 2 hours. TLC showed the reaction was completed. A saturated aqueous solution of ammonium chloride was added, the ethanol was removed under reduced pressure, and then extracted with ethyl acetate (20 mL×3). The combined organic phase was washed with brine (30 mL), dried with anhydrous sodium sulfate, filtered, and concentrated in vacuum. The crude product tert-butyl 4-hydroxy-2,2-dimethyl-piperidine-1-carboxylate (10 g, crude) was obtained as a colorless oil.

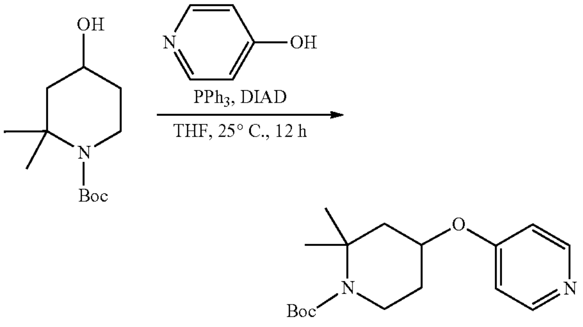

Step 2:

To a mixture of pyridin-4-ol (4.98 g, 52.33 mmol, 1.2 eq) and tert-butyl 4-hydroxy-2,2-dimethyl-piperidine-1-carboxylate (10 g, 43.61 mmol, 1 eq) in tetrahydrofuran (100 mL) was added triphenylphosphane (17.16 g, 65.41 mmol, 1.5 eq) and diisopropylazodicarboxylate (13.23 g, 65.41 mmol, 12.7 mL, 1.5 eq) at 0° C. The mixture was stirred at 25° C. for 12 hours. LCMS showed the desired m/z was detected. The mixture was concentrated in reduced pressure at 40° C. The residue was diluted with Petroleum ether/Ethyl acetate (v/v=3/1) (60 mL) and filtered. The filtrate was concentrated in vacuum. The residue was purified by column chromatography (Petroleum ether/Ethyl acetate=10/1 to 3/1 to 1/1). The crude product tert-butyl 2,2-dimethyl-4-(4-pyridyloxy)piperidine-1-carboxylate (6.6 g, crude) was obtained as a colorless oil

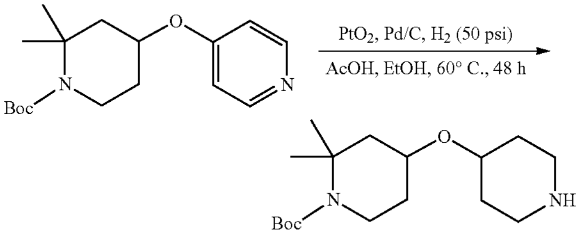

Step 3:

To a solution of tert-butyl 2,2-dimethyl-4-(4-pyridyloxy) piperidine-1-carboxylate (6.00 g, 19.6 mmol, 1 eq) in acetic acid (20 mL) was added platinum oxide (1 g, 4.40 mmol) and Pd/C (1 g, 10% purity) under nitrogen atmosphere. The suspension was degassed under vacuum and purged with $H_2$ several times. The mixture was stirred under $H_2$ (50 psi) at 60° C. for 48 hours. LCMS showed the starting material was consumed completely. The reaction mixture was filtered, and the filter was concentrated. The residue was dissolved into water (50 mL) and neutralized by 1 N sodium hydroxide solution until pH~9. The aqueous phase was extracted with ethyl acetate (30 mL×3), the combined organic phase was washed with brine (20 mL), dried with anhydrous sodium sulfate, filtered, and concentrated in vacuum. The crude product tert-butyl 2,2-dimethyl-4-(4-piperidyloxy)piperidine-1-carboxylate (5.9 g, crude) was obtained as a colorless oil.

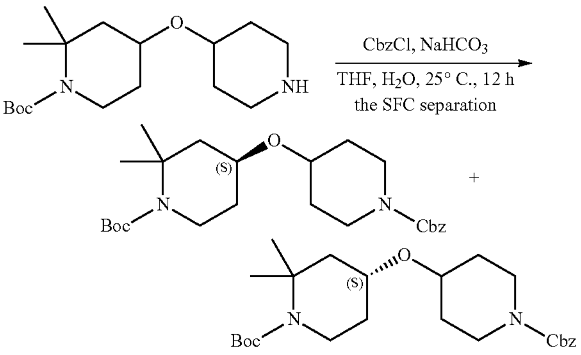

Step 4:

To a mixture of tert-butyl 2,2-dimethyl-4-(4-piperidyloxy)piperidine-1-carboxylate (5.2 g, 16.64 mmol, 1 eq) in tetrahydrofuran (100 mL) and water (50 mL) was added benzyl chloroformate (4.26 g, 24.9 mmol, 3.6 mL, 1.5 eq) and sodium hydrogen carbonate (2.80 g, 33.3 mmol, 2 eq) at 0° C. The mixture was stirred at 25° C. for 12 hours. LCMS showed the reaction was completed. The mixture was diluted with water (50 mL) and extracted with ethyl acetate (50 mL×3). The combined organic phase was washed with brine (50 mL), dried with anhydrous sodium sulfate, filtered, and concentrated in vacuum. The residue was purified by column chromatography (Petroleum ether/Ethyl acetate=20/1 to 10/1). The resulting residue was purified by prep-HPLC (column: Phenomenex luna C18 (250*70 mm, 10 um); mobile phase: [water (FA)-ACN]; B %: 70%-100%, 21 min). The residue was further separated by SFC (column: DAICEL CHIRALPAK AD (250 mm*30 mm, 10 um); mobile phase: [0.1% NH3H2O MEOH]; B %: 45%-45%, 5.2 min). Compound tert-butyl (4S)-4-[(1-benzyloxycarbonyl-4-piperidyl)oxy]-2,2-dimethyl-piperidine-1-carboxylate or the enantiomer thereof (1.25 g, 2.80 mmol, 22.32% yield) was obtained as a colorless oil (Rt=1.3 min). Compound tert-butyl (4R)-4-[(1-benzyloxycarbonyl-4-piperidyl)oxy]-2,2-dimethyl-piperidine-1-carboxylate or the enantiomer thereof (1.25 g, 2.80 mmol, 22.32% yield) was obtained as a colorless oil (Rt=2.2 min).

Exemplary Synthesis of Compound 309

Compound 309 was prepared in a manner analogous to compound 209 using intermediate tert-butyl 4-[1-[1-[2-(2,6-dioxo-3-piperidyl)-4-fluoro-1-oxo-isoindolin-5-yl]-4-piperidyl]-1-methyl-ethyl]piperazine-1-carboxylate.

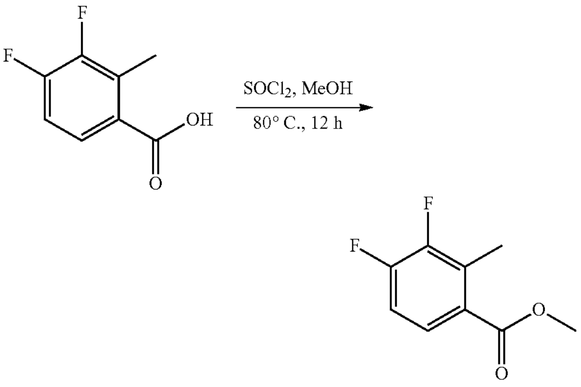

Step 1:

To a solution of 3,4-difluoro-2-methyl-benzoic acid (50.00 g, 290.48 mmol, 1 eq) in methanol (500 mL) was added thionyl chloride (103.68 g, 871.44 mmol, 63.2 mL, 3 eq) drop-wise. The mixture was stirred at 80° C. for 12 hours. Thin layer chromatography showed the reaction was completed. The mixture was poured into ice water (1 L) drop-wise at 0° C., and solid was filtered. The solid was dissolved in ethyl acetate (10 mL), filtered, and concentrated to give methyl 3,4-difluoro-2-methyl-benzoate (51.00 g, 273.97 mmol, 94% yield) as a white solid.

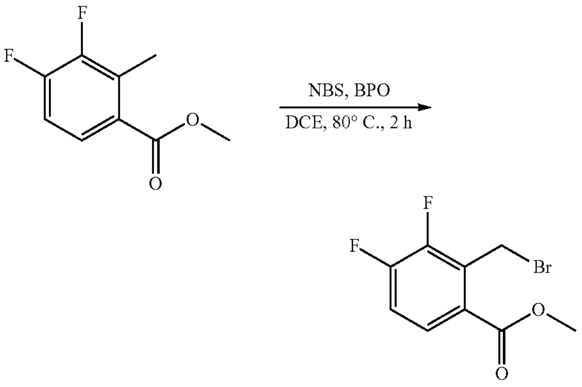

Step 2:

To a mixture of methyl 3,4-difluoro-2-methyl-benzoate (40.00 g, 214.87 mmol, 1 eq) in 1,2-dichloroethane (400 mL) was added n-bromosuccinimide (57.37 g, 322.31 mmol, 1.5 eq) and benzoyl peroxide (520 mg, 2.15 mmol, 0.01 eq). The mixture was degassed and purged with nitrogen for 3 times, and then the mixture was stirred at 80° C. for 2 hours. Thin layer chromatography indicated the reaction was completed. The mixture was cooled to 20° C., then it was filtered and concentrated under reduce pressure to give a residue. The residue was purified by silica gel column chromatography (petroleum ether:ethyl acetate=1:0 to 20:1) to give methyl 2-(bromomethyl)-3,4-difluoro-benzoate (51.00 g, 192.42 mmol, 89% yield) as a colorless oil.

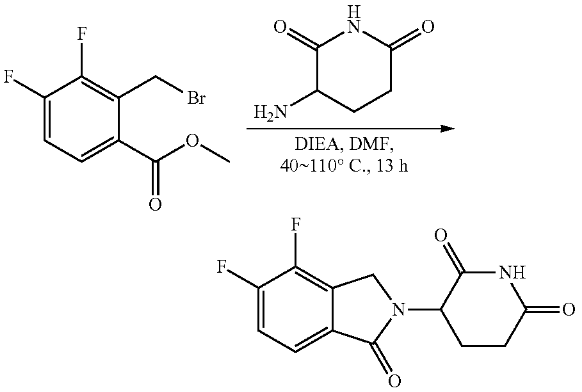

Step 3:

To a mixture of methyl 2-(bromomethyl)-3,4-difluoro-benzoate (51.00 g, 192.42 mmol, 1 eq) and 3-aminopiperidine-2,6-dione (33.25 g, 202.04 mmol, 1.05 eq, hydrochloride) in N,N-dimethylformamide (600 mL) was added diisopropylethylamine (74.61 g, 577.25 mmol, 100.5 mL, 3 eq). The mixture was stirred at 40° C. for 1 hour, and then heated to 110° C. for 12 hours. Thin layer chromatography indicated the reaction was completed. The mixture was poured into water (800 mL) and filtered to obtain a solid. The solid was dissolved in ethyl acetate (500 mL), filtered and the solid was obtained. Compound 3-(4,5-difluoro-1-oxo-isoindolin-2-yl)piperidine-2,6-dione (29.70 g, 105.99 mmol, 55% yield) was obtained as a gray solid.

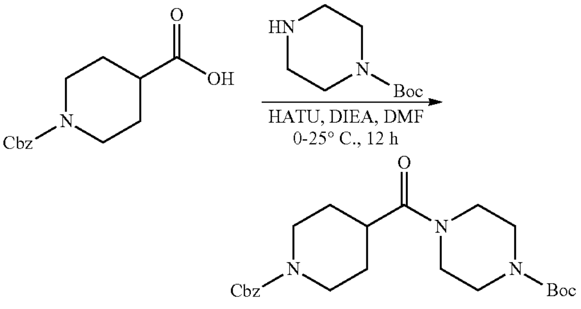

Step 4:

To a solution of 1-benzyloxycarbonylpiperidine-4-carboxylic acid (25 g, 94.95 mmol, 1 eq) and tert-butyl piperazine-1-carboxylate (17.69 g, 94.95 mmol, 1 eq) in N,N-dimethylformamide (500 mL) was added diisopropylethylamine (36.82 g, 284.86 mmol, 49.62 mL, 3 eq) and O-(7-azabenzotriazol-1-yl)-n,n,n',n'-tetramethyluronium hexafluorophosphate (43.32 g, 113.94 mmol, 1.2 eq) at 0° C. The mixture was stirred at 25° C. for 12 hours. LCMS showed the reaction was complete. The reaction mixture was quenched by water (1000 mL) at 20° C. and extracted with ethyl acetate (2000 mL×3), the combined organic layers were washed with brine (1500 mL×3), dried over anhydrous sodium sulfate, filtered, and concentrated under reduced pressure to give a residue. The residue was purified by flash silica gel chromatography (ISCO®; 80 g SepaFlash® Silica Flash Column, Eluent of 0~100% Ethylacetate/Petroleum ethergradient @ 60 m/min), and the crude product was triturated with ethyl acetate (500 mL) at 20° C. for 5 minutes. Compound tert-butyl 4-(1-benzyloxycarbonylpiperidine-4-carbonyl)piperazine-1-carboxylate (52 g, 120.50 mmol, 63% yield, 100% purity) was obtained as a yellow oil.

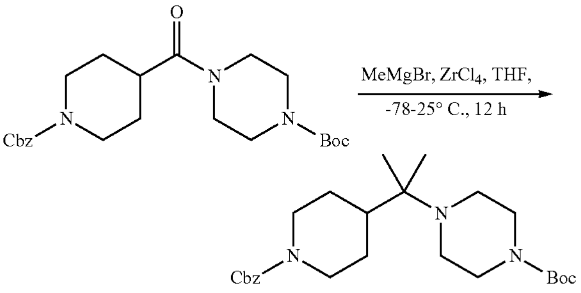

Step 5:

To a mixture of zirconium chloride (17.28 g, 74.16 mmol, 6.17 mL, 1.6 eq) in tetrahydrofuran (500 mL) was added a solution of tert-butyl 4-(1-benzyloxycarbonylpiperidine-4-carbonyl)piperazine-1-carboxylate (20 g, 46.35 mmol, 1 eq) in tetrahydrofuran (1 L) drop-wise at −78° C. over a period of 30 minutes under nitrogen. Methyl magnesium bromide (3 M, 77.25 mL, 5 eq) was then added at −78° C. and stirred for 30 minutes. The resulting mixture was warmed to 25° C. and stirred for 11 hours. LCMS showed the reaction was complete. The reaction was quenched by saturated ammonium chloride aqueous solution (1 L) and stirred for 15 minutes. The aqueous phase was extracted with ethyl acetate (1 L×3). The combined organic phase was washed with brine (1 L×2), dried with anhydrous sodium sulfate, filtered and concentrated in vacuum. The residue was purified by semi-preparative reverse phase HPLC (column: Phenomenex luna c18 250 mm*100 mm*10 um; mobile phase: [water (TFA)-ACN]; B %: 25%-50%, 18 min). Compound tert-butyl 4-[1-(1-benzyloxycarbonyl-4-piperidyl)-1-methyl-ethyl]piperazine-1-carboxylate (23 g, 51.62 mmol, 56% yield) was obtained as a colorless oil.

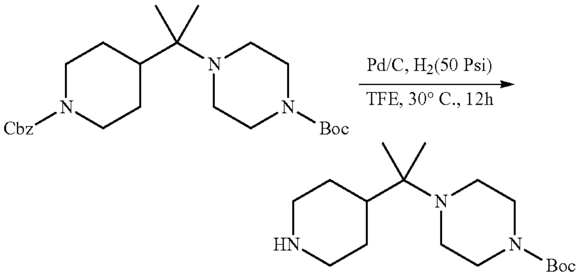

Step 6:

To a solution of tert-butyl 4-[1-(1-benzyloxycarbonyl-4-piperidyl)-1-methyl-ethyl]piperazine-1-carboxylate (5 g, 11.22 mmol, 1 eq) in trifluoroethanol (50 mL) was added palladium on carbon (2 g, 10% purity) under nitrogen. The suspension was degassed under vacuum and purged with hydrogen several times. The mixture was stirred under hydrogen (50 psi) at 30° C. for 12 hours. LCMS showed the reaction was completed. The reaction mixture was filtered, and the filtrate was concentrated. Water was added (100 mL) and the mixture was extracted with ethyl acetate (200 mL×3), the aqueous phase were poured into aqueous sodium bicarbonate (100 mL) to adjust PH about 6~7, then extracted with ethyl acetate (200 mL×3). The combined organic layers were washed with brine (150 mL×3), dried over sodium sulfate, filtered, and concentrated under reduced pressure to give a residue. Compound tert-butyl 4-[1-methyl-1-(4-piperidyl)ethyl]piperazine-1-carboxylate (3.9 g, 9.17 mmol, 81.69% yield, trifluoroacetate) was obtained as a colorless oil.

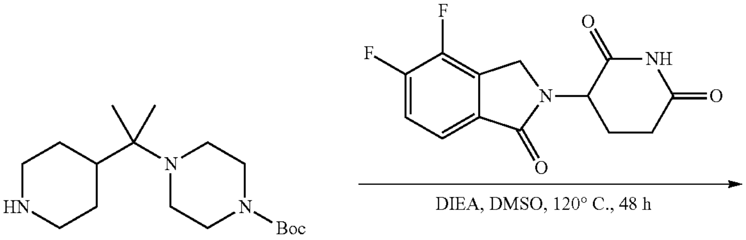

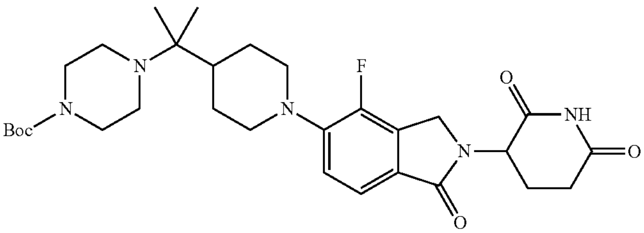

Step 7:

To a solution of tert-butyl 4-[1-methyl-1-(4-piperidyl) ethyl]piperazine-1-carboxylate (1.14 g, 2.68 mmol, 1.5 eq, trifluoroacetate) in dimethylsulfoxide (5 mL) was added diisopropylethylamine (1.15 g, 8.92 mmol, 1.55 mL, 5 eq) and 3-(4,5-difluoro-1-oxo-isoindolin-2-yl)piperidine-2,6-dione (500 mg, 1.78 mmol, 1 eq). The mixture was stirred at 120° C. for 48 hours. LCMS showed the reaction was complete. Water (10 mL) was added and the mixture was extracted with ethyl acetate (20 mL×3). The combined organic layers were washed with brine (15 mL×3), dried over sodium sulfate, filtered, and concentrated under reduced pressure to give a residue. The crude product was purified by re-crystallization from methanol (15 mL). Compound tert-butyl 4-[1-[1-[2-(2,6-dioxo-3-piperidyl)-4-fluoro-1-oxo-isoindolin-5-yl]-4-piperidyl]-1-methyl-ethyl] piperazine-1-carboxylate (280 mg, 0.49 mmol, 27% yield) was obtained as a white solid.

Exemplary Synthesis of Compound 310

Compound 310 was prepared in a manner analogous to compound 309 using intermediates 3-(4,5-difluoro-1-oxo-isoindolin-2-yl)piperidine-2,6-dione and tert-butyl (4R)-4-[(1-benzyloxycarbonyl-4-piperidyl)oxy]-2,2-dimethyl-piperidine-1-carboxylate or the enantiomer thereof.

Exemplary Synthesis of Compound 311

Compound 311 was prepared in a manner analogous to compound 181 starting from tert-butyl (3R)-3-(hydroxymethyl)pyrrolidine-1-carboxylate.

Exemplary Synthesis of Compound 312

Compound 312 was prepared in a manner analogous to compound 211.

Exemplary Synthesis of Compound 313

Compound 313 was prepared in a manner analogous to compound 310 using intermediate tert-butyl (4S)-4-[(1-benzyloxycarbonyl-4-piperidyl)oxy]-2,2-dimethyl-piperidine-1-carboxylate or the enantiomer thereof.

Exemplary Synthesis of Compound 314

Compound 314 was prepared in a manner analogous to compound 211 using intermediate trans-[3-(4-piperidyloxy) cyclobutyl]methanol.

Exemplary Synthesis of Compound 315

Compound 315 was prepared in a manner analogous to compound 211 using intermediate give tert-butyl 4-[3-[7-[2-(2,6-dioxo-3-piperidyl)-4-methoxy-1-oxo-isoindolin-5-yl]-2,7-diazaspiro[3.5]nonan-2-yl]cyclobutoxy]piperidine-1-carboxylate.

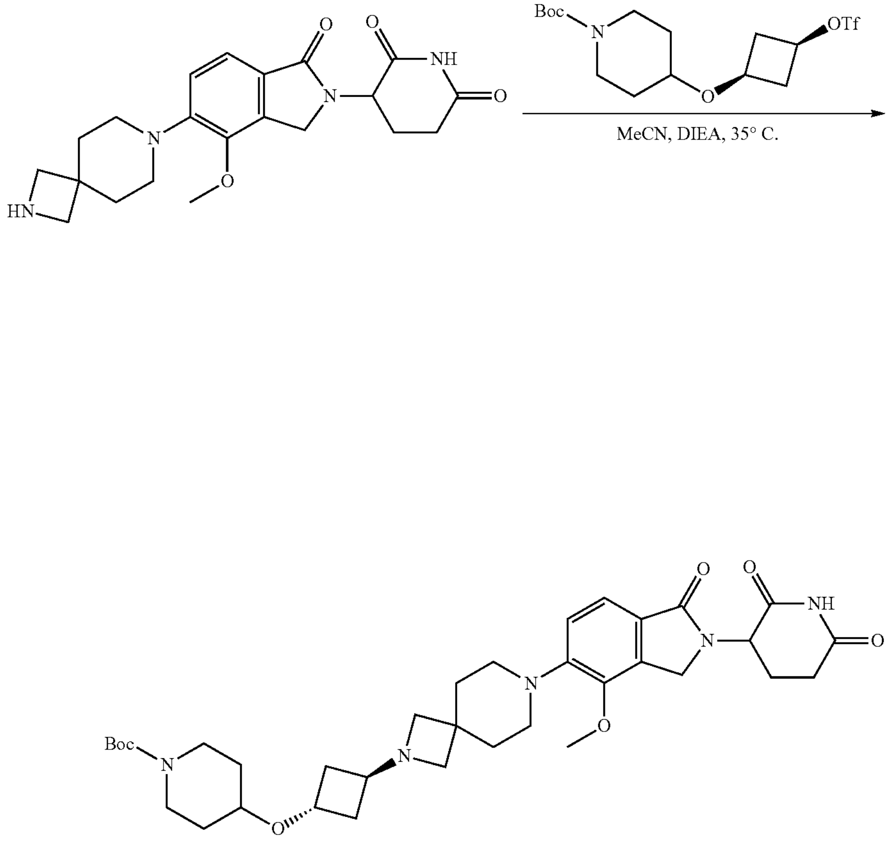

Step 1:

A solution of tert-butyl 4-((1s,3s)-3-(((trifluoromethyl)sulfonyl)oxy)cyclobutoxy)piperidine-1-carboxylate (404.98 mg, 1.00 mmol, 1 eq) and 3-[5-(2,7-diazaspiro[3.5]nonan-7-yl)-4-methoxy-1-oxo-isoindolin-2-yl]piperidine-2,6-dione (400 mg, 1.00 mmol, 1 eq) in MeCN (10 mL) was added DIEA (1.30 g, 10.04 mmol, 1.75 mL, 10 eq) and the mixture stirred at 35° C. for 48 hours to give yellow solution. LCMS showed desired MS. TLC (Dichloromethane:Methanol=10:1) showed several new spots. The reaction mixture was poured $H_2O$ (20 mL). The mixture was extracted with DCM (20 mL*3) and the organic phase was washed with brine (20 mL), dried over anhydrous $Na_2SO_4$, and concentrated under vacuum to give a residue. The residue was purified by silica gel column chromatography (0 to 10% Methanol in Dichloromethane) to give tert-butyl 4-[3-[7-[2-(2,6-dioxo-3-piperidyl)-4-methoxy-1-oxo-isoindolin-5-yl]-2,7-diazaspiro[3.5]nonan-2-yl]cyclobutoxy]piperidine-1-carboxylate (200 mg, 187.18 μmol, 18.65% yield, 61% purity) as a white solid.

Exemplary Synthesis of Compound 316

Compound 316 was prepared in a manner analogous to compound 211 using intermediate tert-butyl (4S)-4-[(1-benzyloxycarbonyl-4-piperidyl)oxy]-2,2-dimethyl-piperidine-1-carboxylate or the enantiomer thereof.

Exemplary Synthesis of Compound 317

Compound 317 was prepared in a manner analogous to compound 209 starting from tert-butyl 5,5-difluoro-2,7-diazaspiro[3.5]nonane-2-carboxylate and using intermediate tert-butyl (3S)-4-(2-chloroethyl)-3-methyl-piperazine-1-carboxylate.

Exemplary Synthesis of Compound 318

Compound 318 was prepared in a manner analogous to compound 211 using intermediate tert-butyl 4-[1-methyl-1-(4-piperidyl)ethyl]piperazine-1-carboxylate.

Exemplary Synthesis of Compound 319

Compound 319 was prepared in a manner analogous to compound 211 using intermediate tert-butyl (4R)-4-[(1-benzyloxycarbonyl-4-piperidyl)oxy]-2,2-dimethyl-piperidine-1-carboxylate or the enantiomer thereof.

Exemplary Synthesis of Compound 320

Compound 320 was prepared in a manner analogous to compound 181 using intermediate tert-butyl 4-[1-methyl-1-(4-piperidyl)ethyl]piperazine-1-carboxylate.

Exemplary Synthesis of Compound 321

Compound 321 was prepared in a manner analogous to compound 309 starting from (R)-tert-butyl 3-(hydroxymethyl)pyrrolidine-1-carboxylate or the enantiomer thereof or the enantiomer thereof.

Exemplary Synthesis of Compound 322

Compound 322 was prepared in a manner analogous to compound 211 using intermediate tert-butyl 4-[1-methyl-1-(4-piperidyl)ethyl]piperazine-1-carboxylate or the enantiomer thereof.

Exemplary Synthesis of Compound 323

Compound 323 was prepared in a manner analogous to compound 309 using intermediate cis-tert-butyl 4-[3-(trifluoromethylsulfonyloxy)cyclobutoxy]piperidine-1-carboxylate.

Exemplary Synthesis of Compound 324

Compound 324 was prepared in a manner analogous to compound 211.

Exemplary Synthesis of Compound 325

Compound 325 was prepared in a manner analogous to compound 211 using intermediate tert-butyl (4S)-4-[(1-benzyloxycarbonyl-4-piperidyl)oxy]-2,2-dimethyl-piperidine-1-carboxylate or the enantiomer thereof.

Exemplary Synthesis of Compound 326

Compound 326 was prepared in a manner analogous to compound 209 using intermediate tert-butyl 4-[cis-3-(trifluoromethylsulfonyloxy)cyclobutoxy]piperidine-1-carboxylate.

Exemplary Synthesis of Compound 327

Compound 327 was prepared in a manner analogous to compound 181 using starting from (R)-tert-butyl 3-(hydroxymethyl)pyrrolidine-1-carboxylate.

Exemplary Synthesis of Compound 328

Compound 328 was prepared in a manner analogous to compound 211 using starting from (R)-tert-butyl 3-(hydroxymethyl)pyrrolidine-1-carboxylate.

Exemplary Synthesis of Compound 329

Compound 329 was prepared in a manner analogous to compound 290 using intermediate 3-(5-bromo-4-methoxy-1-oxo-isoindolin-2-yl)piperidine-2,6-dione.

Exemplary Synthesis of Compound 330

Compound 330 was prepared in a manner analogous to compound 309 starting with (S)-tert-butyl 3-(hydroxymethyl)pyrrolidine-1-carboxylate.

Exemplary Synthesis of Compound 331

Compound 331 was prepared in a manner analogous to compound 211 using intermediate tert-butyl 4-[1-methyl-1-(4-piperidyl)ethyl]piperazine-1-carboxylate.

Exemplary Synthesis of Compound 332

Compound 332 was prepared in a manner analogous to compound 211 starting with benzyl 5,5-difluoro-2,7-diazaspiro[3.5]nonane-7-carboxylate.

Exemplary Synthesis of Compound 333

Compound 333 was prepared in a manner analogous to compound 209 using intermediate 3-(5-bromo-4-methyl-1-oxo-isoindolin-2-yl)piperidine-2,6-dione.

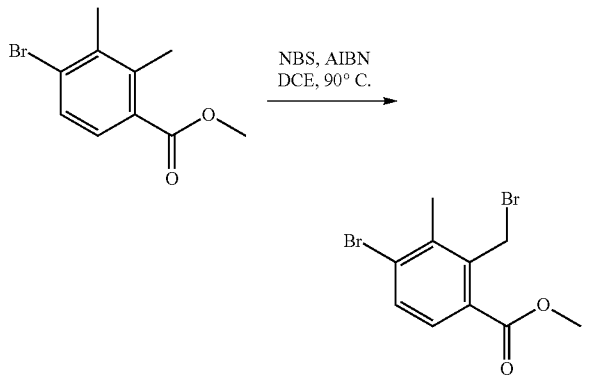

Step 1:

To a stirred solution of methyl 4-bromo-2,3-dimethyl-benzoate (1 g, 4.11 mmol, 1 eq) in DCE (10 mL) under an atmosphere of nitrogen was added NBS (878.58 mg, 4.94 mmol, 1.2 eq) followed by 2-[(E)-(1-cyano-1-methyl-ethyl)azo]-2-methyl-propanenitrile (33.77 mg, 205.68 μmol, 0.05 eq) and the resulting mixture was stirred vigorously at 90° C. for 2 hours. TLC showed the completed was completed. The residue was poured into water (10 mL). The aqueous phase was extracted with ethyl acetate (10 mL*3). The combined organic phase was washed with brine (10 mL*2), dried with anhydrous $Na_2SO_4$, filtered, and concentrated in vacuum. The residue was purified by silica gel chromatography (Petroleum ether) to give methyl 4-bromo-2-(bromomethyl)-3-methyl-benzoate (1.4 g, crude) as a yellow oil.

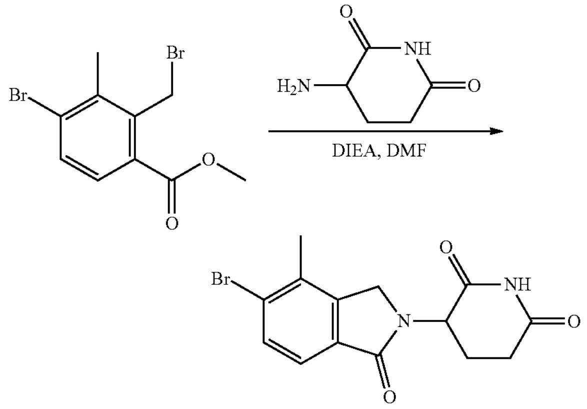

Step 2:

To a mixture of methyl 4-bromo-2-(bromomethyl)-3-methyl-benzoate (1.4 g, 4.35 mmol, 1 eq) and 3-aminopiperidine-2,6-dione (858.75 mg, 5.22 mmol, 1.2 eq, HCl) in DMF (10 mL) was added DIEA (2.81 g, 21.74 mmol, 3.79 mL, 5 eq) in one portion at 20° C. under $N_2$. The mixture was stirred at 85° C. for 10 hours. LCMS showed a new peak with the desired MS. The reaction mixture was concentrated under vacuum and the resulting mixture was triturated with MeCN (20 mL) and $H_2O$ (20 mL) at 20° C. The crude was filtered and solid was concentrated in vacuum to give 3-(5-bromo-4-methyl-1-oxo-isoindolin-2-yl)piperidine-2,6-dione (800 mg, 2.37 mmol, 54.57% yield) as a dark gray solid Exemplary Synthesis of Compound 334

Compound 334 was prepared in a manner analogous to compound 209 using intermediate tert-butyl 4-(((1r,3r)-3-formylcyclobutyl)methyl)piperazine-1-carboxylate.

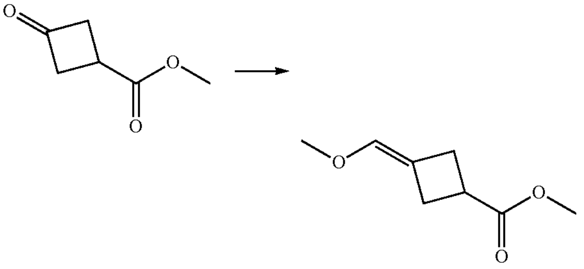

Step 1:

To a mixture of methoxymethyl(triphenyl)phosphonium; chloride (80.26 g, 234.15 mmol, 1.5 eq) in THF (50 mL) was added NaHMDS (1 M, 234.15 mL, 1.5 eq) at −40° C. under $N_2$. The mixture was stirred at 0° C. for 30 minutes, then cooled to −40° C. and a solution of methyl 3-oxocyclobutanecarboxylate (20 g, 156.10 mmol, 1 eq) in THF (20 mL) was added. The reaction mixture was stirred at 25° C. for 16 hours. TLC showed the reaction was completed. The residue was poured into sat. $NH_4Cl$ (100 mL). The aqueous phase was extracted with MTBE (3×100 mL). The combined organics were washed with brine (50 mL), dried over anhydrous $Na_2SO_4$, filtered, and concentrated under reduced pressure. The residue was purified by silica gel chromatography (220 nm, 0-2% (2 min) of MTBE in Petroleum ether, 2% (10 min) of MTBE in Petroleum ether) to give methyl 3-(methoxymethylene)cyclobutanecarboxylate (9.4 g, 60.19 mmol, 38.56% yield) as a colorless oil.

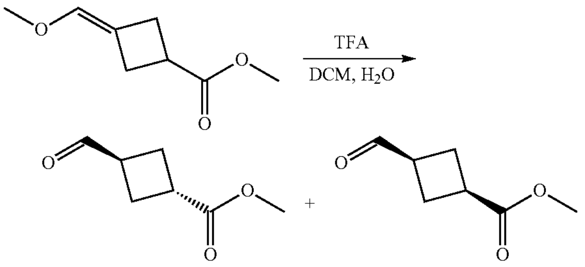

Step 2:

To a solution of the methyl 3-(methoxymethylene)cyclobutanecarboxylate (9.3 g, 59.55 mmol, 1 eq) in DCM (50 mL) was added TFA (13.58 g, 119.09 mmol, 8.82 mL, 2 eq) and $H_2O$ (5 mL). The resulting mixture was stirred at 25° C. for 2 hours. TLC showed the reaction was completed. The residue was poured into water (10 mL). The aqueous phase was extracted with ethyl acetate (10 mL*3). The combined organic phase was washed with brine (10 mL*2), dried with anhydrous $Na_2SO_4$, filtered, and concentrated under vacuum. The residue was purified by silica gel chromatography (220 nm, 80 g, 0-10% (10 min) of MTBE in Petroleum ether, 10% (30 min) of MTBE in Petroleum ether) to give trans-methyl 3-formylcyclobutanecarboxylate (1.7 g, 11.96 mmol, 20.08% yield) and cis-methyl 3-formylcyclobutanecarboxylate (3.4 g, 23.92 mmol, 40.17% yield) as a colorless oil.

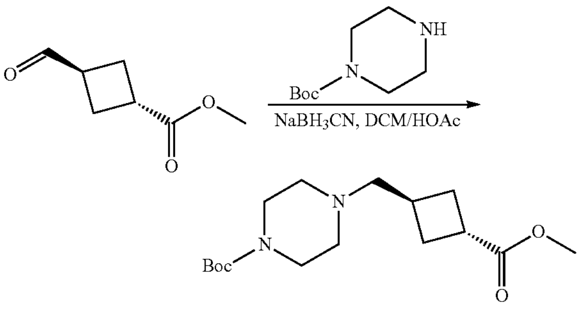

Step 3:

To a mixture of trans-methyl 3-formylcyclobutanecarboxylate (1.5 g, 10.55 mmol, 1 eq) and tert-butyl piperazine-1-carboxylate (3.93 g, 21.10 mmol, 4.08 mL, 2 eq) in DCM (30 mL) and HOAc (1 mL) was added $NaBH_3CN$ (1.33 g, 21.10 mmol, 2 eq) in one portion at 25° C. under $N_2$. The mixture was stirred at 25° C. for 1 hour. TLC and LCMS indicated the reaction was complete. The residue was poured into water (30 mL). The aqueous phase was extracted with ethyl acetate (30 mL*3). The combined organic phase was washed with brine (30 mL*2), dried with anhydrous $Na_2SO_4$, filtered, and concentrated under vacuum. The residue was purified by silica gel chromatography (0-38% (25 min) of Ethyl acetate in Petroleum ether, 38% (25 min) of Ethyl acetate in Petroleum ether) to give tert-butyl 4-[(3-methoxycarbonylcyclobutyl)methyl]piperazine-1-carboxylate (1.5 g, 4.80 mmol, 45.49% yield) as a colorless oil.

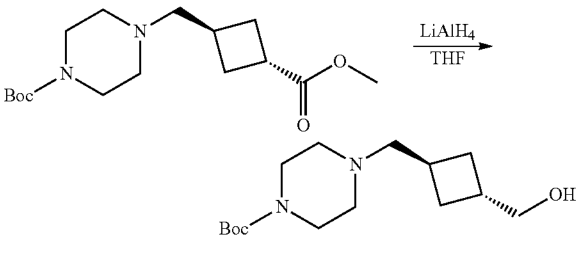

Step 4:

To a mixture of tert-butyl 4-[(3-methoxycarbonylcyclobutyl)methyl]piperazine-1-carboxylate (1.5 g, 4.80 mmol, 1 eq) in THF (30 mL) was added $LiAlH_4$ (364.43 mg, 9.60 mmol, 27.09 mL, 2 eq) at 0° C. under $N_2$. The mixture was stirred at 0° C. for 1 hour. TLC showed the reaction was completed. The residue was poured into $H_2O$ (1 mL), NaOH (1 mL, 15%), $H_2O$ (3 mL). The aqueous phase was extracted with ethyl acetate (40 mL*3). The combined organic phase was washed with brine (40 mL*2), dried with anhydrous $Na_2SO_4$, filtered, and concentrated in vacuum. The residue was purified by silica gel chromatography (0-100% of Petroleum ether in Petroleum ether) to give tert-butyl 4-[[3-(hydroxymethyl)cyclobutyl]methyl]piperazine-1-carboxylate (1.2 g, 4.01 mmol, 83.51% yield, 95% purity) as a yellow oil.

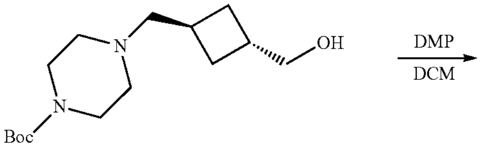

-continued

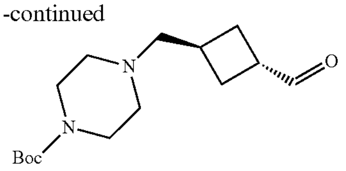

Step 5:

To a mixture of tert-butyl 4-[[3-(hydroxymethyl)cyclobutyl]methyl]piperazine-1-carboxylate (400 mg, 1.41 mmol, 1 eq) in DCM (10 mL) was added DMP (1.19 g, 2.81 mmol, 870.89 uL, 2 eq) in one portion at 25° C. under $N_2$. The mixture was stirred at 25° C. for 1 hour to give yellow solution. TLC (petroleum ether: ethyl acetate=0:1) showed the starting material was consumed completely. The residue was poured into $NaHCO_3$ to adjust the pH=7-8, and $Na_2SO_3$ (20 mL). The aqueous phase was extracted with DCM (30 mL*3). The combined organic phase was washed with brine (30 mL*2), dried with anhydrous $Na_2SO_4$, filtered, and concentrated under vacuum to give tert-butyl 4-(((1r,3r)-3-formylcyclobutyl)methyl)piperazine-1-carboxylate (400 mg, crude) as a yellow oil.

Exemplary Synthesis of Compound 335

Compound 335 was prepared in a manner analogous to compound 309 using intermediate tert-butyl 4-[cis-3-(trifluoromethylsulfonyloxy)cyclobutoxy]piperidine-1-carboxylate.

Exemplary Synthesis of Compound 336

Compound 336 was prepared in a manner analogous to compound 317.

Exemplary Synthesis of Compound 337

Compound 337 was prepared in a manner analogous to compounds 209 and 309 using intermediate tert-butyl 3-fluoro-3-(4-piperidylmethyl)azetidine-1-carboxylate.

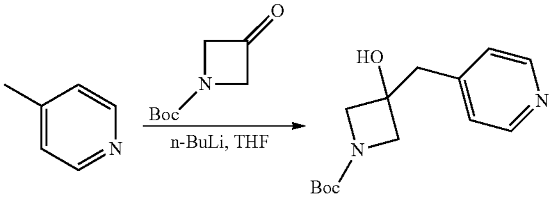

Step 1:

n-BuLi (2.5 M, 10.31 mL, 1.2 eq) was added dropwise to 4-methylpyridine (2 g, 21.48 mmol, 2.11 mL, 1 eq) in THF (20 mL at −70° C. under $N_2$. The mixture was stirred at −70° C. for 3 hours to afford an orange solution, then tert-butyl 3-oxoazetidine-1-carboxylate (3.68 g, 21.48 mmol, 1 eq) in THF (10 mL) was dropwise added, and the solution was stirred at 20° C. for 2 hours to give light yellow solution. TLC and LCMS showed the reaction was completed. The residue was poured into water (20 mL). The aqueous phase was extracted with ethyl acetate (20 mL*3). The combined organic phase was washed with brine (20 mL*2), dried with anhydrous $Na_2SO_4$, filtered, and concentrated in vacuum. The residue was purified by silica gel chromatography (40 g, 0-60% (30 minutes) of Ethyl acetate in Petroleum ether, 60%

(15 min) of Ethyl acetate in Petroleum ether) to give tert-butyl 3-hydroxy-3-(4-pyridylmethyl)azetidine-1-carboxylate (3.31 g, 12.52 mmol, 58.31% yield) as a yellow gum.

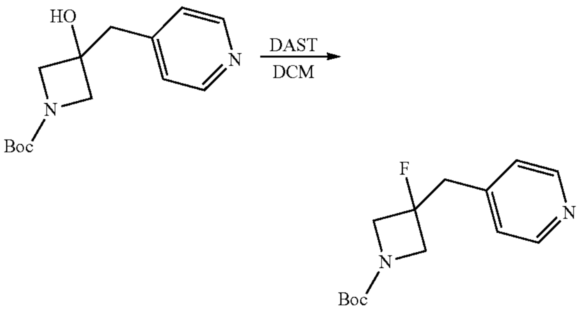

Step 2:

To a mixture of tert-butyl 3-hydroxy-3-(4-pyridylmethyl) azetidine-1-carboxylate (3.31 g, 12.52 mmol, 1 eq) in DCM (100 mL) was added DAST (2.42 g, 15.03 mmol, 1.99 mL, 1.2 eq) dropwise at −40° C. under $N_2$. The reaction was then heated to 20° C. and stirred for 30 minutes to give an orange solution. TLC (Petroleum ether:Ethyl acetate=1:1, Rf=0.74) showed no starting material and a new spot. The reaction was cooled to 0° C. and quenched with aqueous $NaHCO_3$ to pH=7-8. The aqueous phase was extracted with DCM (10 mL*3). The combined organic layers were washed with brine (10 mL*2), dried over anhydrous sodium sulfate, filtered, and concentrated under reduced pressure to give a residue. The residue was purified by silica gel chromatography (40 g, 0-18% (15 minutes) of Ethyl acetate in Petroleum ether, 18% (15 minutes) of Ethyl acetate in Petroleum ether) to give tert-butyl 3-fluoro-3-(4-pyridylmethyl)azetidine-1-carboxylate (2.33 g, 8.75 mmol, 69.87% yield) as a light-yellow solid.

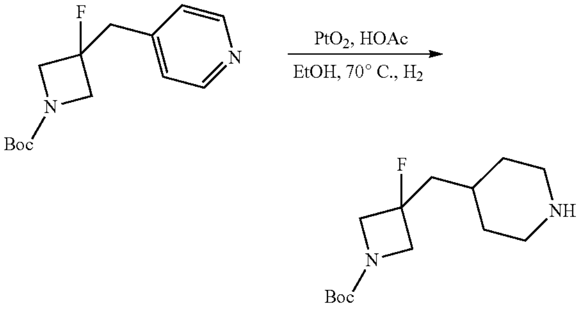

Step 3:

To a solution of tert-butyl 3-fluoro-3-(4-pyridylmethyl) azetidine-1-carboxylate (2.33 g, 8.75 mmol, 1 eq) in EtOH (20 mL) and HOAc (525.39 mg, 8.75 mmol, 500.37 uL, 1 eq) was added $PtO_2$ (298.01 mg, 1.31 mmol, 0.15 eq) at 25° C. The mixture was stirred at 70° C. for 24 hours under $H_2$ (50 psi). TLC showed the reaction was completed. The suspension was filtered through a pad of Celite and the pad was washed with EtOH (100 mL×3). The combined filtrates were concentrated to dryness to provide tert-butyl 3-fluoro-3-(4-piperidylmethyl)azetidine-1-carboxylate (2.8 g, crude) as a colorless oil.

Exemplary Synthesis of Compound 338

Compound 338 was prepared in a manner analogous to compound 211 using intermediate 3-(6-chloropyrimidin-4-yl)-5-(1-methylcyclopropoxy)-1-trityl-pyrazolo[3,4-c]pyridine.

Exemplary Synthesis of Compound 339

Compound 339 was prepared in a manner analogous to compound 209.

Exemplary Synthesis of Compound 340

Compound 340 was prepared in a manner analogous to compound 211.

Exemplary Synthesis of Compound 341

Compound 341 was prepared in a manner analogous to compound 211.

Exemplary Synthesis of Compound 342

Compound 342 was prepared in a manner analogous to compound 297 using intermediate 3-(5-bromo-1-oxo-isoindolin-2-yl)piperidine-2,6-dione and (3r,4s)-tert-butyl 4-(2-(2,6-dioxopiperidin-3-yl)-4-fluoro-1-oxoisoindolin-5-yl)-3-fluoropiperidine-1-carboxylate.

Exemplary Synthesis of Compound 343

Compound 343 was prepared in a manner analogous to compound 209.

Exemplary Synthesis of Compound 344

Compound 344 was prepared in a manner analogous to compound 211 using intermediate tert-butyl 4-((1s,3s)-3-(((trifluoromethyl)sulfonyl)oxy)cyclobutoxy)piperidine-1-carboxylate.

Exemplary Synthesis of Compound 345

Compound 345 was prepared in a manner analogous to compound 211 using intermediate tert-butyl 3-fluoro-3-(4-piperidylmethyl)azetidine-1-carboxylate.

Exemplary Synthesis of Compound 346

Compound 346 was prepared in a manner analogous to compound 209.

Exemplary Synthesis of Compound 347

Compound 347 was prepared in a manner analogous to compound 211 using intermediate benzyl 2-((1r,3r)-3-(piperidin-4-yloxy)cyclobutyl)-2,7-diazaspiro[3.5]nonane-7-carboxylate.

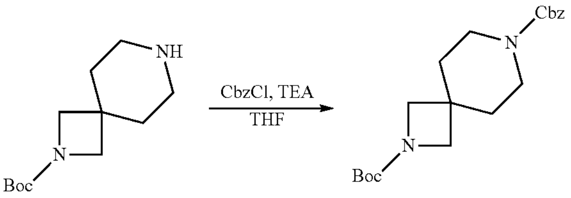 [SMILES: CC(C)(C)OC(=O)N1CC2(CCNCC2)C1 ; CC(C)(C)OC(=O)N1CC2(CCN(C(=O)OCc3ccccc3)CC2)C1 ; "THF"]

Step 1:

To a solution of tert-butyl 2,7-diazaspiro[3.5]nonane-2-carboxylate (3 g, 13.26 mmol, 1 eq) and TEA (1.61 g, 15.91 mmol, 2.21 mL, 1.2 eq) in THF (20 mL) was added CbzCl (2.71 g, 15.91 mmol, 2.26 mL, 1.2 eq) and the mixture stirred at 0° C. for 2 hours to give yellow solution. TLC (Petroleum ether:Ethyl acetate=3:1, Rf=0.17) showed no starting material and one new spot. The resulting product was poured into $H_2O$ (20 mL). The mixture was extracted with ethyl acetate (20 mL*3). The organic phase was washed with brine (20 mL), dried over anhydrous $Na_2SO_4$ concentrated in vacuum to give a residue. The residue was purified by silica gel column chromatography (0 to 20% Ethyl acetate in Petroleum ether) to give 07-benzyl 02-tert-butyl 2,7-diazaspiro[3.5]nonane-2,7-dicarboxylate (3.5 g, 9.71 mmol, 73.25% yield) as a colorless oil.

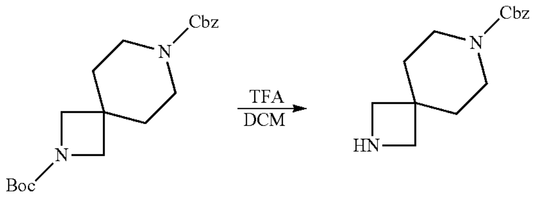

Step 2:

To a solution of 07-benzyl 02-tert-butyl 2,7-diazaspiro[3.5]nonane-2,7-dicarboxylate (3.5 g, 9.71 mmol, 1 eq) in DCM (5 mL) was added TFA (6.16 g, 54.03 mmol, 4 mL, 5.56 eq). After addition, the reaction mixture was stirred at 25° C. for 1 hour. TLC (Petroleum ether:Ethyl acetate=3:1) showed one new spot and LCMS showed desired MS. Aqueous $NaHCO_3$ was added to adjust the pH=7-8. The aqueous phase was extracted with DCM (15 mL*3). The organic layer was concentrated under reduced pressure to give benzyl 2,7-diazaspiro[3.5]nonane-7-carboxylate (2 g, 7.68 mmol, 79.12% yield) as a colorless oil.

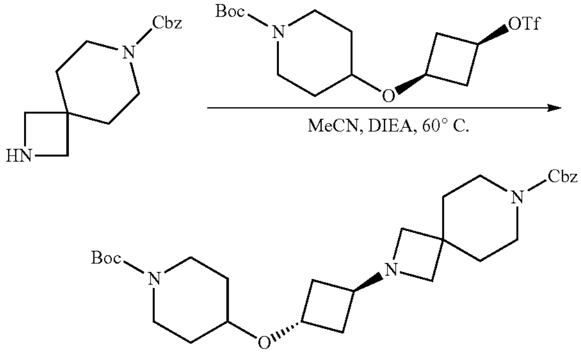

Step 3:

A solution of benzyl 2,7-diazaspiro[3.5]nonane-7-carboxylate (1.4 g, 5.38 mmol, 1 eq) and tert-butyl 4-[3-(trifluoromethylsulfonyloxy)cyclobutoxy]piperidine-1-carboxylate (2.82 g, 6.99 mmol, 1.3 eq) in MeCN (15 mL) was added DIEA (2.09 g, 16.13 mmol, 2.81 mL, 3 eq) and the mixture stirred at 60° C. for 12 hours to give yellow solution. TLC (Petroleum ether:Ethyl acetate=0:1, Rf=0.01) showed several new spots. TLC (Dichloromethane:Methanol=10:1, Rf=0.6) showed several new spots. The resulting product was poured into $H_2O$ (10 mL). The mixture was extracted with DCM (20 mL*3). The organic phase was washed with brine (20 mL), dried over anhydrous $Na_2SO_4$, concentrated in vacuum to give a residue. The residue was purified by silica gel column chromatography (0 to 100% Ethyl acetate in Petroleum ether), The residue was purified by silica gel column chromatography (0 to 10% Methanol in Dichloromethane) benzyl 2-[3-[(1-tert-butoxycarbonyl-4-piperidyl)oxy]cyclobutyl]-2,7-diazaspiro[3.5]nonane-7-carboxylate (1.67 g, 2.41 mmol, 44.74% yield, 74% purity) as a light yellow gum.

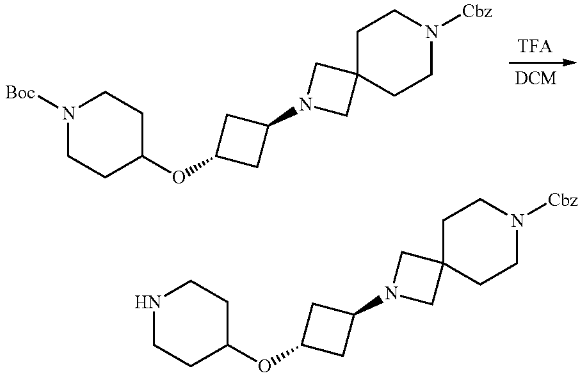

Step 4:

To a solution of benzyl 2-[3-[(1-tert-butoxycarbonyl-4-piperidyl)oxy]cyclobutyl]-2,7-diazaspiro[3.5]nonane-7-carboxylate (1.3 g, 2.53 mmol, 1 eq) in DCM (5 mL) was added TFA (3.08 g, 27.01 mmol, 2 mL, 10.67 eq). After addition, the reaction mixture was stirred at 25° C. for 1 hour. TLC (Dichloromethane:Methanol=10:1) showed one new spot and LCMS showed desired MS. Aqueous $NaHCO_3$ was added to adjust the pH=7-8. The aqueous phase was extracted with DCM (15 mL*3). The organic layer was concentrated under reduced pressure to give benzyl 2-((1r, 3r)-3-(piperidin-4-yloxy)cyclobutyl)-2,7-diazaspiro[3.5]nonane-7-carboxylate (930 mg, 2.25 mmol, 88.86% yield) as a white solid.

Exemplary Synthesis of Compound 348

Compound 348 was prepared in a manner analogous to compound 234.

Exemplary Synthesis of Compound 349

Compound 349 was prepared in a manner analogous to compounds 181 and 211.

Exemplary Synthesis of Compound 350

Compound 350 was prepared in a manner analogous to compound 309.

Exemplary Synthesis of Compound 351

Compound 351 was prepared in a manner analogous to compound 209 using intermediate ((1r,3r)-3-(piperidin-4-yloxy)cyclobutyl)methanol.

Exemplary Synthesis of Compound 352

Compound 352 was prepared in a manner analogous to compound 234.

Exemplary Synthesis of Compound 353

Compound 353 was prepared in a manner analogous to compound 309.

Exemplary Synthesis of Compound 354

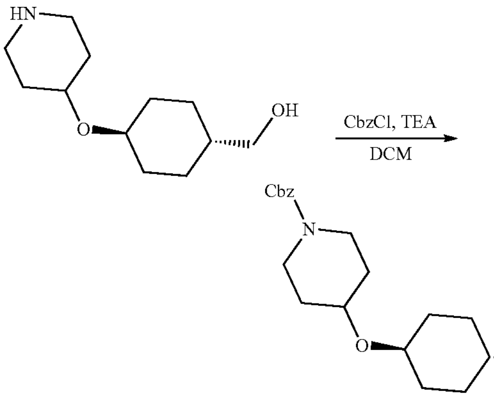

Step 1:

To a mixture of [4-(4-piperidyloxy)cyclohexyl]methanol (30 g, 140.64 mmol, 1 eq) in DCM (300 mL) was added CbzCl (31.19 g, 182.83 mmol, 25.99 mL, 1.3 eq) and TEA (42.69 g, 421.91 mmol, 58.72 mL, 3 eq) at 0° C. under $N_2$. After addition, the reaction mixture was stirred at 25° C. for 1 hour to give light yellow suspension. TLC (Petroleum ether:Ethyl acetate=1:1, Rf=0.3) showed a reaction new spot. The reaction was quenched by addition of $H_2O$ (200 mL) and extracted with ethyl acetate (3×100 mL). The combined organic phases were washed with water, dried with $Na_2SO_4$, and concentrated under vacuum to give a residue. The residue was purified by silica gel column chromatography (0-100% Ethyl acetate in Petroleum ether) to give benzyl 4-[4-(hydroxymethyl)cyclohexoxy]piperidine-1-carboxylate (37 g, 106.49 mmol, 75.72% yield) as colorless oil.

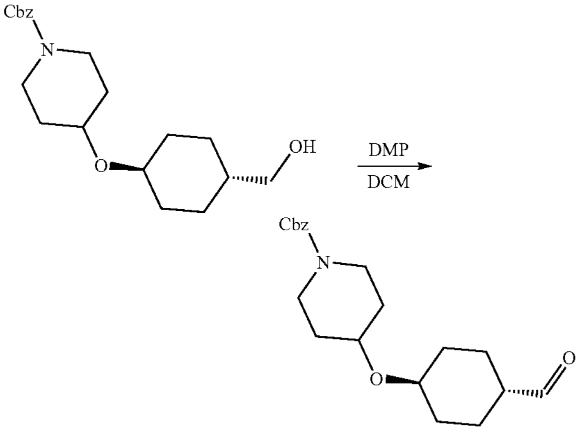

Step 2:

A solution of benzyl 4-[4-(hydroxymethyl)cyclohexoxy] piperidine-1-carboxylate (37 g, 106.49 mmol, 1 eq) in DCM (200. mL), DMP (55.50 g, 130.85 mmol, 40.51 mL, 1.23 eq) was added and the mixture stirred at 25° C. for 2 hours to give yellow solution. TLC (Petroleum ether:Ethyl acetate=1:1, Rf=0.6) showed the reaction new spot. The reaction mixture was cooled to 0° C. and quenched by addition of sat. $NaHCO_3$ to pH~8, and extracted with DCM (100 mL*3). The combined organic layers were washed with sat. $Na_2SO_3$ (100 mL*2) and brine (60 mL*2), dried over $Na_2SO_4$, filtered, and concentrated under reduced pressure to give a residue. The residue was purified by silica gel chromatography (Petroleum ether/Ethyl acetate=100/1, 1/1) to afford benzyl 4-(4-formylcyclohexoxy)piperidine-1-carboxylate (30 g, 85.98 mmol, 80.74% yield, 99% purity) as colorless oil.

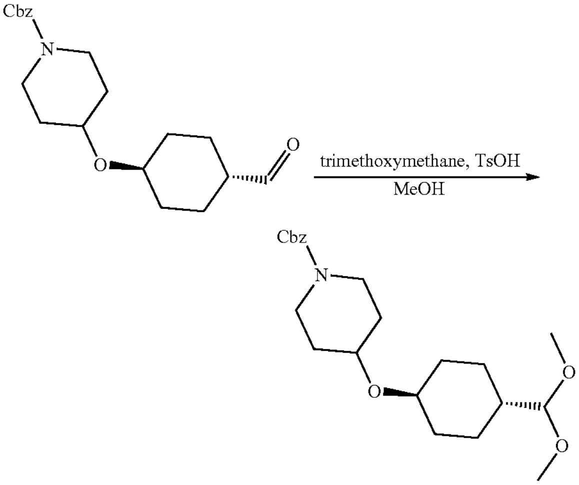 [SMILES: "MeOH" ; O=C[C@H]1CC[C@H](OC2CCN(C(=O)OCc3ccccc3)CC2)CC1 ; COC(OC)[C@H]1CC[C@H](OC2CCN(C(=O)OCc3ccccc3)CC2)CC1]

Step 3:

To a mixture of benzyl 4-(4-formylcyclohexoxy)piperidine-1-carboxylate (30 g, 86.85 mmol, 1 eq) in MeOH (200 mL) was added TosOH (747.77 mg, 4.34 mmol, 0.05 eq) and trimethoxymethane (46.08 g, 434.24 mmol, 47.60 mL, 5 eq) in one portion at 25° C. under $N_2$. The mixture was stirred at 25° C. for 2 hours. TLC (Petroleum ether:Ethyl acetate=3:1, Rf=0.5) showed the reaction new spot. The reaction was quenched by $H_2O$ (100 mL) and extracted with ethyl acetate (3*200 mL). The combined organic phases were washed with water, dried with $Na_2SO_4$, and concentrated under vacuum to give a residue. The residue was purified by silica gel column chromatography (0-30% Ethyl acetate in Petroleum ether) to give benzyl 4-[4-(dimethoxymethyl)cyclohexoxy]piperidine-1-carboxylate (31 g, 75.22 mmol, 86.62% yield, 95% purity) as colorless oil.

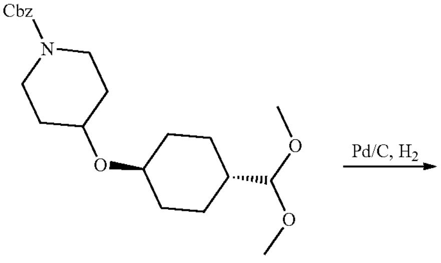

-continued

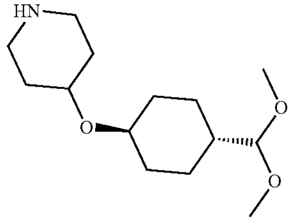

Step 4:

To a mixture of benzyl 4-[4-(dimethoxymethyl)cyclohexoxy]piperidine-1-carboxylate (31 g, 79.18 mmol, 1 eq) in EtOH (200 mL) was added Pd/C (8 g, 79.18 mmol, 10% purity, 1 eq) at 25° C. under $H_2$ (15 PSI) for 16 hours. TLC (Petroleum ether:Ethyl acetate=3:1) showed one new spot. The residue was filtered and concentrated under vacuum to give 4-[4-(dimethoxymethyl)cyclohexoxy]piperidine (18.6 g, 72.27 mmol, 91.27% yield) as a white solid.

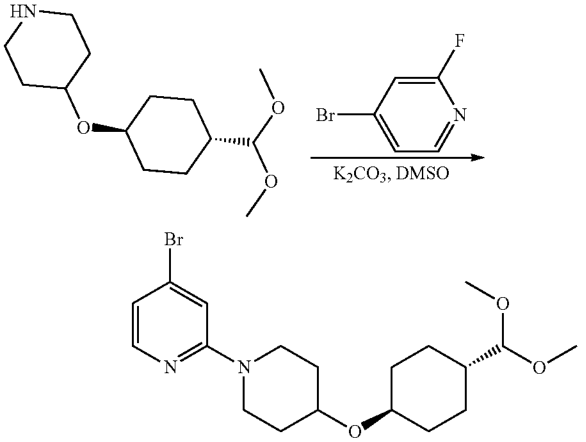

Step 5:

To a solution of 4-[4-(dimethoxymethyl)cyclohexoxy]piperidine (500 mg, 1.94 mmol, 1 eq) in DMSO (5 mL) was added 4-bromo-2-fluoro-pyridine (341.90 mg, 1.94 mmol, 1 eq) and DIEA (502.16 mg, 3.89 mmol, 676.77 uL, 2 eq). After addition, the reaction solution was stirred at 90° C. for 1 hour. LCMS showed desired MS and TLC (Petroleum ether:Ethyl acetate=5:1) showed one new spot. After cooling, the reaction solution was diluted with ethyl acetate (10 mL) and washed with water (3×10 mL). The organic layer was concentrated under reduced pressure. The residue was purified by silica gel column chromatography (0 to 20% Ethyl acetate in Petroleum ether) to give 4-bromo-2-[4-[4-(dimethoxymethyl)cyclohexoxy]-1-piperidyl]pyridine (680 mg, 1.60 mmol, 82.14% yield, 97% purity) as a yellow solid.

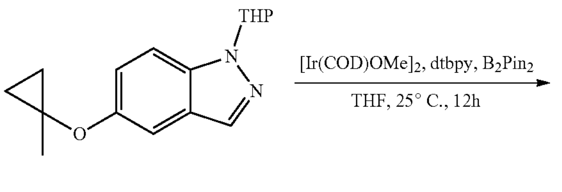

-continued

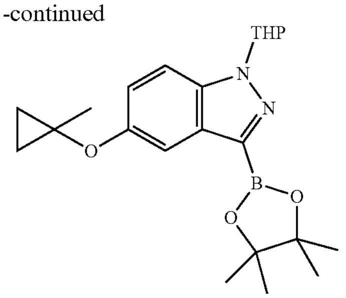

Step 6:

To a solution of 5-(1-methylcyclopropoxy)-1-tetrahydropyran-2-yl-indazole (5 g, 18.36 mmol, 1 eq) in THF (80 mL) was added $Pin_2B_2$ (11.66 g, 45.90 mmol, 2.5 eq) and (1Z,5Z)-cycloocta-1,5-diene; 2,4-dimethyl-BLAHbicyclo [1.1.0]butane (1.22 g, 1.84 mmol, 0.1 eq). After addition, the reaction mixture was stirred at 25° C. for 12 hours under $N_2$. LCMS showed a peak with the desired MS and TLC (petroleum ether:ethyl acetate=3:1) showed the reaction completed. The reaction mixture was combined with a separate reaction for work-up. The combined reaction mixtures were filtered and filtrate was concentrated under reduced pressure. The residue was purified by silica gel column chromatography (0 to 23% ethyl acetate in petroleum ether) to afford 5-(1-methylcyclopropoxy)-1-tetrahydropyran-2-yl-3-(4,4,5,5-tetramethyl-1,3,2-dioxaborolan-2-yl)indazole (9.5 g, 17.17 mmol, 93.54% yield, 72% purity) as a light yellow solid. Based on the combined reactions, the average yield was 77.9%.

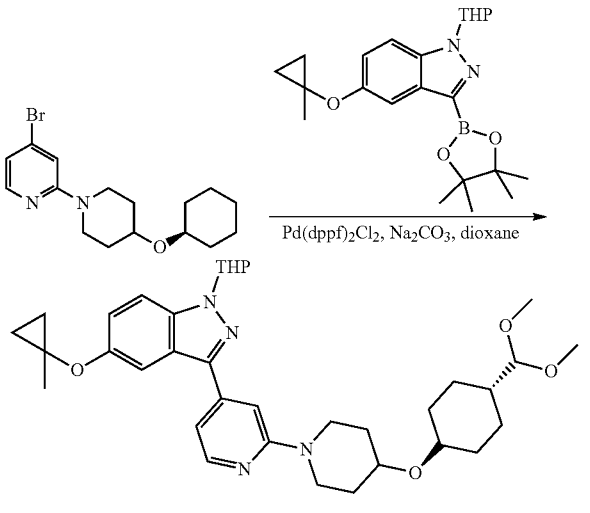

Step 7:

To a solution of 4-bromo-2-[4-[4-(dimethoxymethyl)cyclohexoxy]-1-piperidyl]pyridine (415.11 mg, 1.00 mmol, 1 eq) and 5-(1-methylcyclopropoxy)-1-tetrahydropyran-2-yl-3-(4,4,5,5-tetramethyl-1,3,2-dioxaborolan-2-yl)indazole (400 mg, 1.00 mmol, 1 eq) in dioxane (5 mL) and $H_2O$ (1 mL) was added Pd(dppf)$Cl_2$ (73.48 mg, 100.43 μmol, 0.1 eq) and $Na_2CO_3$ (319.33 mg, 3.01 mmol, 3 eq). After addition, the reaction mixture was stirred at 80° C. under $N_2$ for 16 hours. LCMS showed a new peak with the desired MS and TLC (Petroleum ether:Ethyl acetate=3:1) showed one new spot. After cooling, the reaction mixture was filtered, and filtrate was concentrated under reduced pressure. The residue was purified by silica gel column chromatography (0 to 20% Ethyl acetate in Petroleum ether) to give 3-[2-[4-[4-(dimethoxymethyl)cyclohexoxy]-1-piperidyl]-4-pyridyl]-5-(1-methylcyclopropoxy)-1-tetrahydropyran-2-yl-indazole (560 mg, 787.07 μmol, 78.37% yield, 85% purity) as a brown oil.

Step 8:

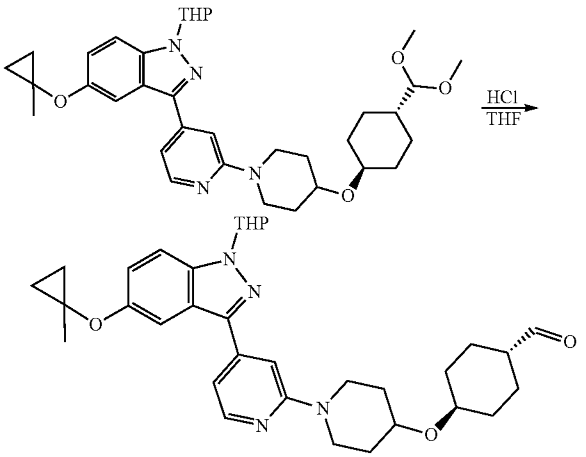

To a solution of 3-[2-[4-[4-(dimethoxymethyl)cyclohexoxy]-1-piperidyl]-4-pyridyl]-5-(1-methylcyclopropoxy)-1-tetrahydropyran-2-yl-indazole (400 mg, 661.40 μmol, 1 eq) in THF (4 mL) was added HCl (2 M, 4 mL, 12.10 eq). After addition, the reaction solution was stirred at 25° C. for 10 minutes. TLC (Petroleum ether:Ethyl acetate=3:1) showed one new spot. $NaHCO_3$ was added to the reaction mixture to adjust the pH=8-9. The mixture was extracted with ethyl acetate (10 mL) and the organic layer was washed with water (3×15 mL). The mixture was concentrated under reduced pressure to give 4-[[1-[4-[5-(1-methylcyclopropoxy)-1-tetrahydropyran-2-yl-indazol-3-yl]-2-pyridyl]-4-piperidyl]oxy]cyclohexanecarbaldehyde (300 mg, crude) as a yellow solid.

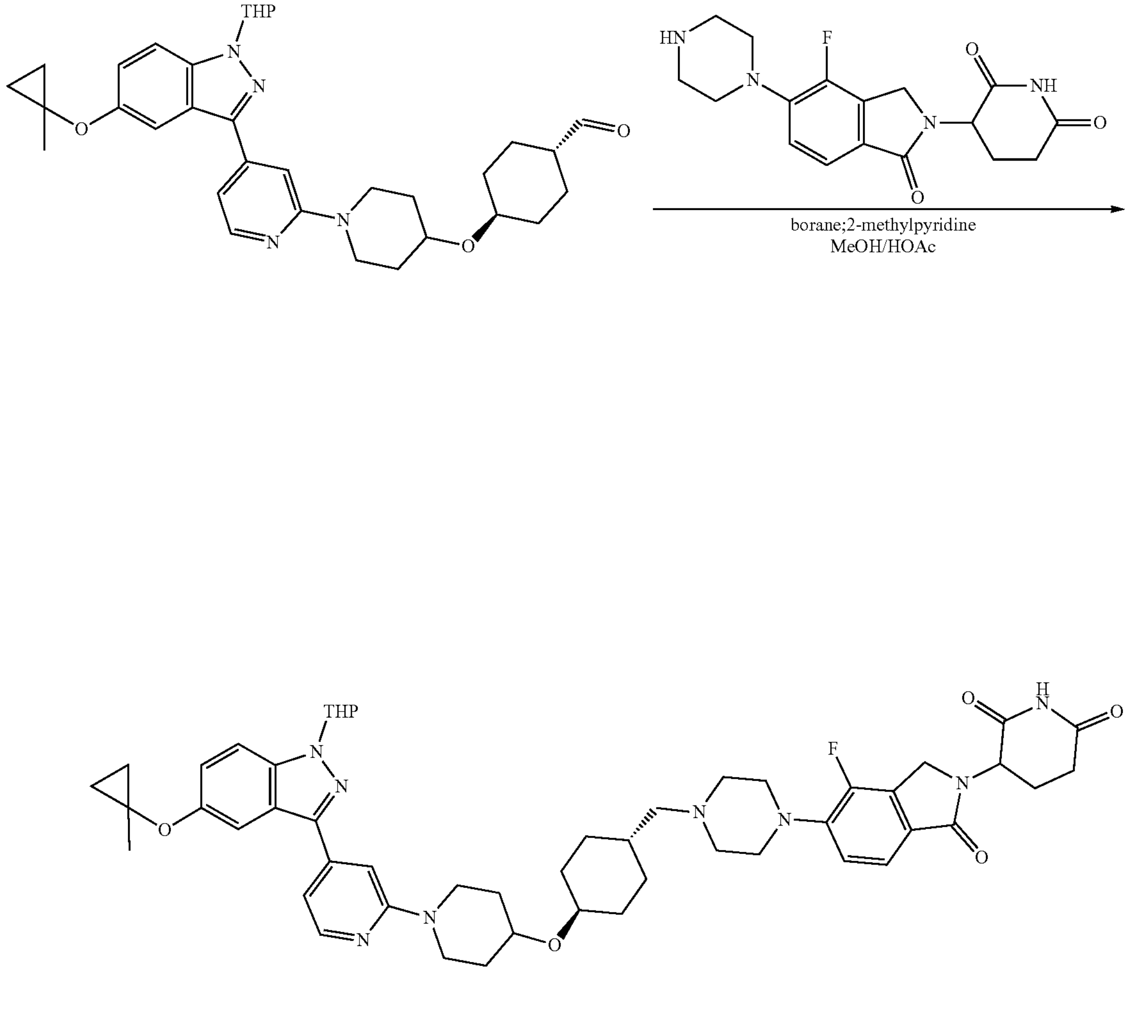

Step 9:

A mixture of 4-[[1-[4-[5-(1-methylcyclopropoxy)-1-tetrahydropyran-2-yl-indazol-3-yl]-2-pyridyl]-4-piperidyl]oxy]cyclohexanecarbaldehyde (160 mg, 286.37 μmol, 1 eq) and 3-(4-fluoro-1-oxo-5-piperazin-1-yl-isoindolin-2-yl)piperidine-2,6-dione (99.19 mg, 286.37 μmol, 1 eq) in MeOH (10 mL) and AcOH (2 mL) was added borane: 2-methylpyridine (91.89 mg, 859.12 μmol, 3 eq) and the mixture was stirred a 25° C. for 12 hours. LCMS showed desired MS and TLC (Dichloromethane:Methanol=10:1) showed one new spot. $NaHCO_3$ was added to the reaction mixture to adjust the pH=8-9 and the mixture was extracted with ethyl acetate (10 mL) and the extracts were washed with water (3×15 mL). The mixture was concentrated under reduced pressure. The residue was purified by silica gel column chromatography (0 to 10% Methanol in Dichloromethane) to give 3-[4-fluoro-5-[4-[[4-[[1-[4-[5-(1-methylcyclopropoxy)-1-tetrahydropyran-2-yl-indazol-3-yl]-2-pyridyl]-4-piperidyl]oxy]cyclohexyl]methyl]piperazin-1-yl]-1-oxo-isoindolin-2-yl]piperidine-2,6-dione (200 mg, 195.71 μmol, 68.34% yield, 87% purity) as a white solid.

Exemplary Synthesis of Compound 355

Compound 355 was prepared in a manner analogous to compound 209.

Exemplary Synthesis of Compound 356

Compound 356 was prepared in a manner analogous to compound 211 using intermediate tert-butyl 3-(4-piperidyloxy)azetidine-1-carboxylate.

Exemplary Synthesis of Compound 357

Compound 357 was prepared in a manner analogous to compound 211.

Exemplary Synthesis of Compound 358

Compound 358 was prepared in a manner analogous to compound 78.

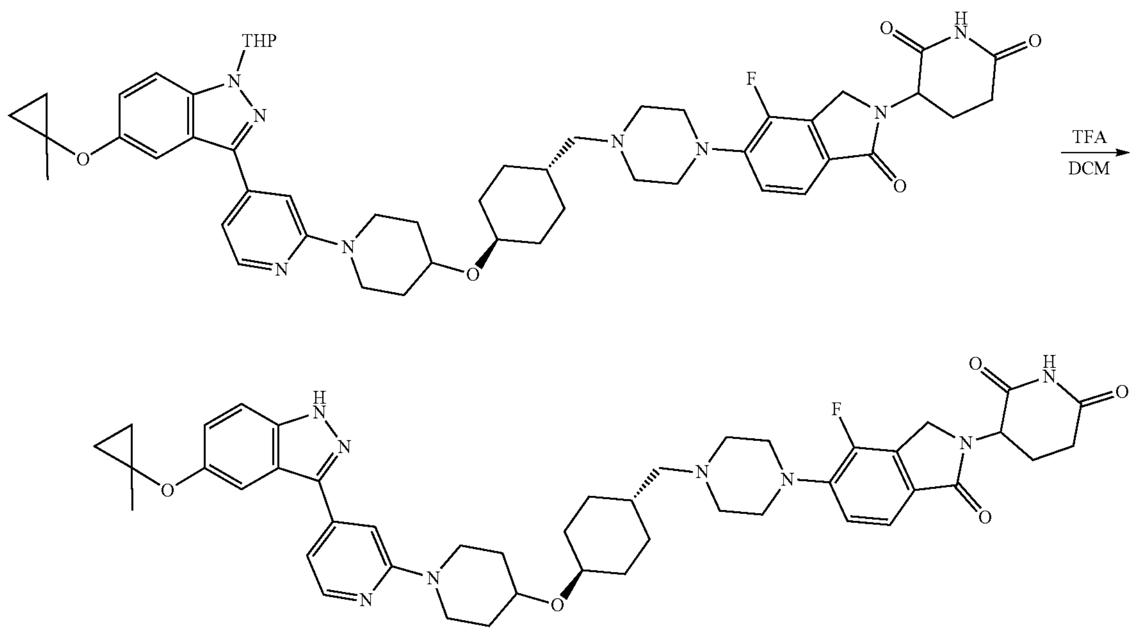

Step 10:

A mixture of 3-[4-fluoro-5-[4-[[4-[[1-[4-[5-(1-methylcyclopropoxy)-1-tetrahydropyran-2-yl-indazol-3-yl]-2-pyridyl]-4-piperidyl]oxy]cyclohexyl]methyl]piperazin-1-yl]-1-oxo-isoindolin-2-yl]piperidine-2,6-dione (150 mg, 168.72 μmol, 1 eq) in DCM (5 mL) was added TFA (3.08 g, 27.01 mmol, 2 mL, 160.11 eq) and the mixture was stirred at 25° C. for 12 hours. LCMS showed a new peak with desired MS. The mixture was concentrated and purified by prep-HPLC (column: Phenomenex C18 75*30 mm*3 um; mobile phase: [water (FA)-ACN]; B %: 6%-36%, 25 min) to give 3-[4-fluoro-5-[4-[[4-[[1-[4-[5-(1-methylcyclopropoxy)-1H-indazol-3-yl]-2-pyridyl]-4-piperidyl]oxy]cyclohexyl]methyl]piperazin-1-yl]-1-oxo-isoindolin-2-yl]piperidine-2,6-dione (36.1 mg, 44.69 μmol, 26.49% yield, 99.65% purity) as a white solid.

Exemplary Synthesis of Compound 359

Compound 359 was prepared in a manner analogous to compounds 181 and 211.

Exemplary Synthesis of Compound 360

Compound 360 was prepared in a manner analogous to compounds 211 and 234.

Exemplary Synthesis of Compound 361

Compound 361 was prepared in a manner analogous to compound 309 using intermediate tert-butyl 4-(((1r,4r)-4-((2,2-dimethylpiperazin-1-yl)methyl)cyclohexyl)oxy)piperidine-1-carboxylate.

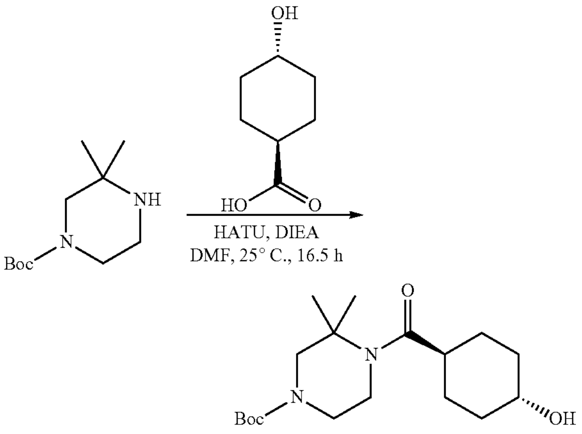

Step 1:

To a mixture of 4-hydroxycyclohexanecarboxylic acid (3.1 g, 21.50 mmol, 1 eq) in dimethylformamide (50 mL) was added O-(7-azabenzotriazole-1-yl)-N,N,N',N'-tetramethyluronium (12.26 g, 32.25 mmol, 1.5 eq) in one portion at 0° C. and the mixture was stirred for 30 minutes. Tert-butyl 3,3-dimethylpiperazine-1-carboxylate (5.07 g, 23.65 mmol, 1.1 eq) and diisopropylethylamine (5.56 g, 43.01 mmol, 7.49 mL, 2 eq) were then added at 0° C. The mixture was allowed to warm to 25° C. and stirred for 16 hours. LCMS showed the reaction was complete. Water (100 mL) was added and the mixture was extracted with ethyl acetate (50 mL×3). The combined organic phase was first washed with 0.5 mol hydrochloric acid (70 ml×1), then with saturated sodium bicarbonate solution (50 ml×1), then with water (50 mL), and finally with brine (50 mL×2). The resulting organic layer was dried with anhydrous sodium sulfate, filtered, and concentrated under vacuum. Compound tert-butyl 4-(4-hydroxycyclohexanecarbonyl)-3,3-dimethylpiperazine-1-carboxylate (11.3 g, crude) was obtained as a black oil.

Step 2:

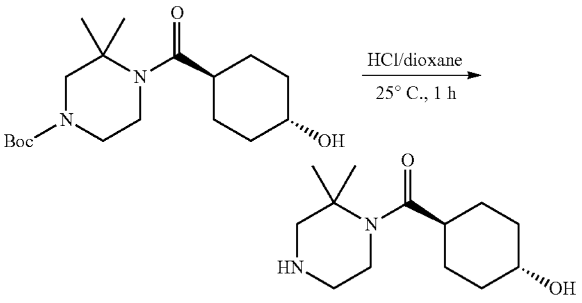

To a mixture of tert-butyl 4-(4-hydroxycyclohexanecarbonyl)-3,3-dimethyl-piperazine-1-carboxylate (7.32 g, 21.50 mmol, 1 eq) was added hydrochloride acid/dioxane (4 M, 70 mL, 13.02 eq) in one portion at 25° C. The mixture was stirred at 25° C. for 1 hour. LCMS showed the reaction was complete. The reaction mixture was concentrated under reduced pressure to remove solvent. Compound (2,2-dimethylpiperazin-1-yl)-(4-hydroxycyclohexyl)methanone (11.2 g, crude) was obtained as a black oil.

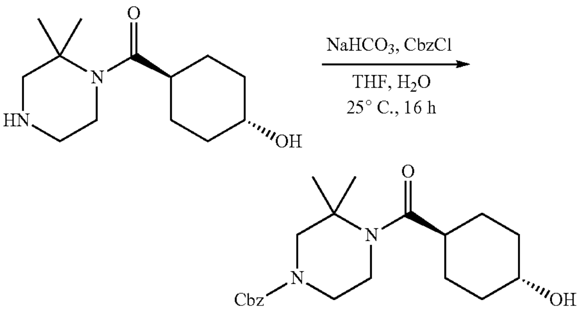

Step 3:

To a mixture of (2,2-dimethylpiperazin-1-yl)-(4-hydroxycyclohexyl)methanone (5.17 g, 21.51 mmol, 1 eq) and sodium bicarbonate (9.04 g, 107.56 mmol, 4.18 mL, 5 eq) in tetrahydrofuran (10 mL) and water (5 mL) was added benzyl chlorofoemate (4.04 g, 23.66 mmol, 3.36 mL, 1.1 eq) in one portion at 0° C. The mixture was stirred at 25° C. for 16 hours. LCMS showed the reaction was complete. The mixture was diluted with water (100 mL) and then extracted with ethyl acetate (50 mL×3). The combined organic phase was washed with brine (50 mL), dried with anhydrous sodium sulfate, filtered, and concentrated in vacuum. The residue was purified by column chromatography (Petroleum ether/Ethyl acetate=5/1 to 1/2). Benzyl 4-(4-hydroxycyclohexanecarbonyl)-3,3-dimethyl-piperazine-1-carboxylate (4.21 g, 11.24 mmol, 52% yield) was obtained as a yellow oil.

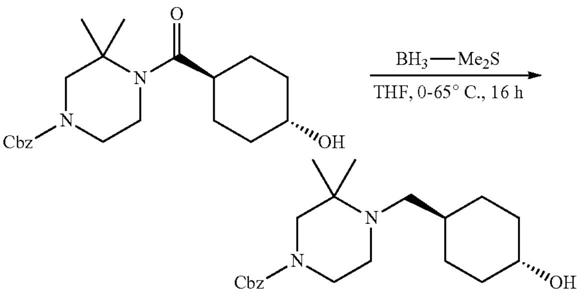

Step 4:

To a mixture of benzyl 4-(4-hydroxycyclohexanecarbonyl)-3,3-dimethyl-piperazine-1-carboxylate (4.21 g, 11.24 mmol, 1 eq) in tetrahydrofuran (40 mL) was added borane dimethyl sulfide complex (10 M, 6.75 mL, 6 eq) in one portion at 0° C. The mixture was stirred at 65° C. for 16 hours. LCMS showed the reaction was complete. The solution was quenched with 1.0 N hydrochloric acid solution (~100 mL). The impurities were extracted with ethyl acetate (40 mL×3). The aqueous phase was adjusted to pH=7-8 with a saturated sodium bicarbonate solution (~100 mL). The mixture was extracted with ethyl acetate (80 mL×3), dried with anhydrous sodium sulfate, filtered, and concentrated in vacuum to afford benzyl 4-[(4-hydroxycyclohexyl)methyl]-3,3-dimethyl-piperazine-1-carboxylate (2.95 g, 8.18 mmol, 72% yield) as a yellow oil.

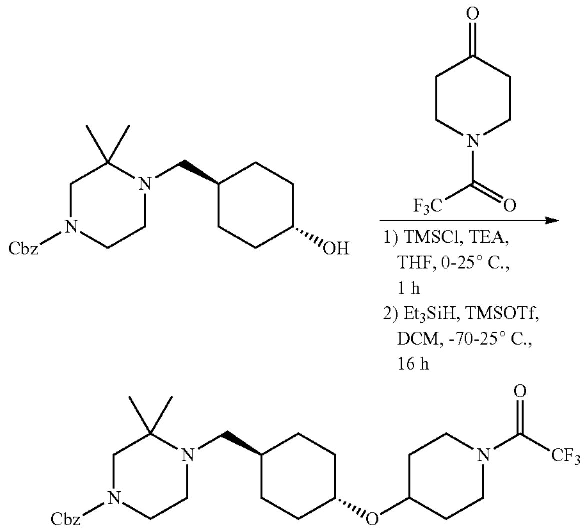

Step 5:

To a mixture of benzyl 4-[(4-hydroxycyclohexyl)methyl]-3,3-dimethyl-piperazine-1-carboxylate (2.9 g, 8.04 mmol, 1 eq) in tetrahydrofuran (30 mL) was added chlorotrimethylsilane (961.38 mg, 8.85 mmol, 1.12 mL, 1.1 eq) and trimethylamine (1.22 g, 12.07 mmol, 1.68 mL, 1.5 eq) in one portion at 0° C. The mixture was stirred at 25° C. for 1 hour. Thin layer chromatography showed the reaction was complete. The mixture was concentrated in reduced pressure at 40° C. The residue was dissolved into dichloromethane (30 mL) and 1-(2,2,2-trifluoroacetyl)piperidin-4-one (1.57 g, 8.04 mmol, 1 eq) was added and the mixture was cooled to −70° C. Triethylsilane (1.87 g, 16.09 mmol, 2.57 mL, 2 eq) was added followed by slow addition of trimethylsilyl trifluoromethanesulfonate (1.79 g, 8.04 mmol, 1.45 mL, 1 eq). The mixture was stirred at 25° C. for 16 hours. LCMS showed the reaction was complete. Saturated sodium bicarbonate aqueous (100 mL) was added to the mixture. The aqueous was extracted with ethyl acetate (100 mL×3). The combined organic layer was dried over anhydrous sodium sulfate, filtered, and the filtrate was concentrated under vacuum. Benzyl 3,3-dimethyl-4-[[4-[[1-(2,2,2-trifluoroacetyl)-4-piperidyl]oxy]cyclohexyl]methyl]piperazine-1-carboxylate (4.6 g, crude) was obtained as a yellow oil.

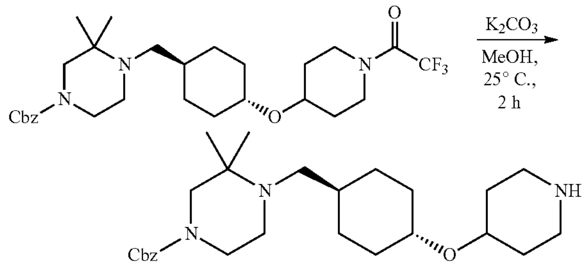

Step 6:

To a solution of benzyl 3,3-dimethyl-4-[[4-[[1-(2,2,2-trifluoroacetyl)-4-piperidyl]oxy]cyclohexyl]methyl]piperazine-1-carboxylate (2.98 g, 5.52 mmol, 1 eq) in methanol (30 mL) was added potassium carbonate (2.29 g, 16.57 mmol, 3 eq) in one portion at 25° C. The mixture was stirred at 25° C. for 2 hours. Thin layer chromatography showed the reaction was complete. The reaction mixture was filtered and the filtrate was diluted with water (100 mL) and extracted with dichloromethane with (30 mL×3). The combined organic phase was washed with brine (50 mL), dried with anhydrous sodium sulfate, filtered, and concentrated under vacuum. Benzyl 3,3-dimethyl-4-[[4-(4-piperidyloxy)cyclohexyl]methyl]piperazine-1-carboxylate (2 g, 4.51 mmol, 81% yield) was obtained as a yellow oil as used in the next step without further purification.

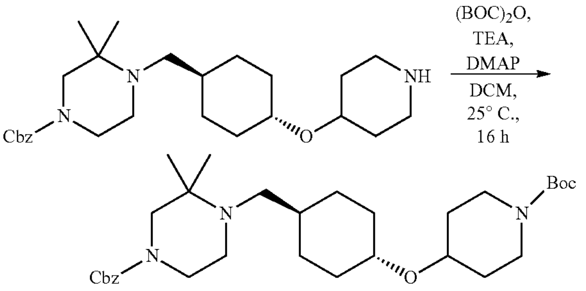

Step 7:

To a mixture of benzyl 3,3-dimethyl-4-[[4-(4-piperidyloxy)cyclohexyl]methyl]piperazine-1-carboxylate (2 g, 4.51 mmol, 1 eq) and 4-dimethylaminopyridine (55 mg, 0.45 mmol, 0.1 eq) in dichloromethane (20 mL) was added triethylamine (912 mg, 9.02 mmol, 1.3 mL, 2 eq) and di-tert-butyl dicarbonate (1.48 g, 6.76 mmol, 1.5 mL, 1.5 eq) in one portion at 0° C. The mixture was stirred at 25° C. for 16 hours. LCMS showed the reaction was complete. A saturated aqueous solution of ammonium chloride 30 mL was added. The mixture was then extracted with ethyl acetate (50 mL×3). The combined organic phase was washed with saturated sodium bicarbonate solution 30 mL, water 30 mL and brine 50 mL, dried over anhydrous sodium sulfate, filtered, and concentrated under vacuum. The residue was purified by column chromatography (Petroleum ether/Ethyl acetate=10/1 to 3/1). Benzyl 4-[[4-[(1-tert-butoxycarbonyl-4-piperidyl)oxy]cyclohexyl]methyl]-3,3-dimethyl-piperazine-1-carboxylate (1.7 g, 3.13 mmol, 69% yield) was obtained as a yellow oil.

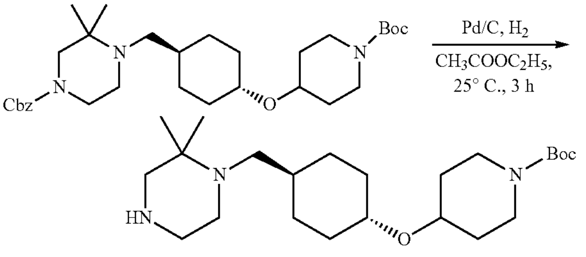

Step 8:

To a solution of benzyl 4-[[4-[(1-tert-butoxycarbonyl-4-piperidyl)oxy]cyclohexyl]methyl]-3,3-dimethyl-piperazine-1-carboxylate (1.7 g, 3.13 mmol, 1 eq) in ethyl acetate (20 mL) was added palladium on carbon (170 mg, 3.13 mmol, 10% purity, 1 eq) in one portion at 25° C. under nitrogen. The mixture was stirred at 25° C. for 3 hours under an atmosphere of hydrogen. LCMS showed the reaction was complete. The reaction mixture was filtered. Tert-butyl 4-(((1r,4r)-4-((2,2-dimethylpiperazin-1-yl)methyl)cyclohexyl)oxy)piperidine-1-carboxylate (1.28 g, crude) was obtained as an oil and used in the next step without further purification.

Exemplary Synthesis of Compound 362

Compound 362 was prepared in a manner analogous to compound 309.

Exemplary Synthesis of Compound 363

Compound 363 was prepared in a manner analogous to compound 211.

Exemplary Synthesis of Compound 364

Compound 364 was prepared in a manner analogous to compound 211.

Exemplary Synthesis of Compound 365

Compound 365 was prepared in a manner analogous to compound 354.

Exemplary Synthesis of Compound 366

Compound 366 was prepared in a manner analogous to compound 211.

Exemplary Synthesis of Compound 367

Compound 367 was prepared in a manner analogous to compounds 354 and 211.

Exemplary Synthesis of Compound 368

Compound 368 was prepared in a manner analogous to compound 235.

Exemplary Synthesis of Compound 369

Compound 369 was prepared in a manner analogous to compound 211.

Exemplary Synthesis of Compound 370

Compound 370 was prepared in a manner analogous to compound 239.

Exemplary Synthesis of Compound 371

Compound 371 was prepared in a manner analogous to compound 78 using intermediate 3-iodo-5-(1-methylcyclopropoxy)-1-trityl-pyrazolo[4,3-b]pyridine.

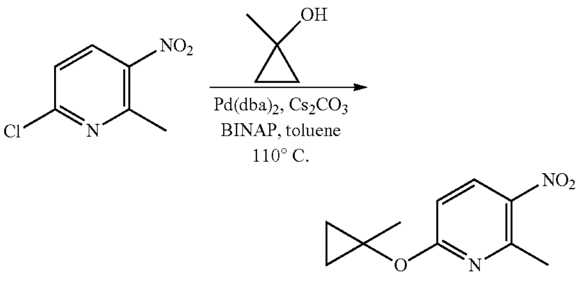

Step 1:

To a mixture of 6-bromo-2-methyl-3-nitro-pyridine (6 g, 27.65 mmol, 1 eq) and 1-methylcyclopropanol (1.99 g, 27.65 mmol, 1 eq) in toluene (10 mL) was added $Pd(dba)_2$ (317.95 mg, 552.94 μmol, 0.02 eq), $Cs_2CO_3$ (10.81 g, 33.18 mmol, 1.2 eq) and BINAP (1.03 g, 1.66 mmol, 0.06 eq) in one portion at 20° C. under $N_2$. The mixture was heated to 110° C. and stirred for 3 hours. LCMS showed desired MS. The mixture was cooled to 20° C. The residue was poured into water (10 mL). The mixture was extracted with ethyl acetate (10 mL*3). The combined organic phase was washed with brine (10 mL*2), dried with anhydrous $Na_2SO_4$, filtered, and concentrated under vacuum. The residue was purified by silica gel chromatography (Petroleum ether) to give 2-methyl-6-(1-methylcyclopropoxy)-3-nitro-pyridine (3.41 g, 16.38 mmol, 59.24% yield) as a yellow oil.

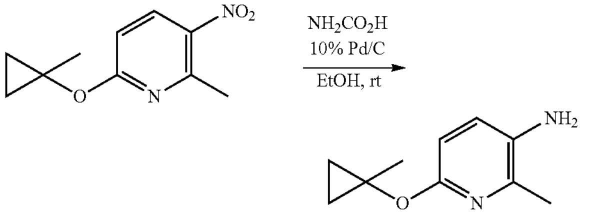

Step 2:

To a mixture of 2-methyl-6-(1-methylcyclopropoxy)-3-nitro-pyridine (3.90 g, 18.73 mmol, 1 eq) in EtOH (10 mL) was added Pd/C (500 mg, 18.73 mmol, 10% purity, 1 eq) and ammonium formate (14.17 g, 224.77 mmol, 12 eq) in one portion at 20° C. under $N_2$. The mixture was stirred at 20° C. for 1 hour to give black solution. TLC showed the reaction was complete. The mixture was filtered through a pad of silica gel with the pad was washed with EtOAc (3×200 mL) and the organics were concentrated under vacuum. The residue was purified by silica gel chromatography (100-200 mesh silica gel, 0-10% of Ethyl acetate in Petroleum ether) to give 2-methyl-6-(1-methylcyclopropoxy)pyridin-3-amine (3.5 g, crude) as a red oil.

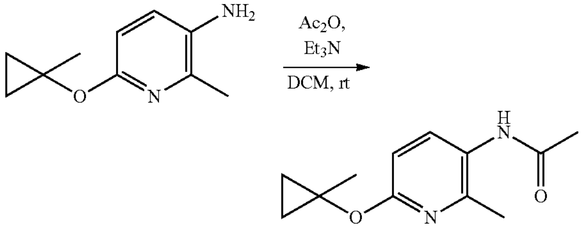

Step 3:

To a mixture of 2-methyl-6-(1-methylcyclopropoxy)pyridin-3-amine (3.54 g, 19.86 mmol, 1 eq) and $Et_3N$ (5.02 g, 49.65 mmol, 6.91 mL, 2.5 eq) in DCM (10 mL) was added $Ac_2O$ (4.06 g, 39.72 mmol, 3.72 mL, 2 eq) in one portion at 0° C. under $N_2$. The mixture was stirred at 0° C. for 30 minutes, then heated to 20° C. and stirred for 1 hour. TLC showed the reaction was complete and LCMS showed a peak with the desired MS. The reaction was quenched with saturated $NaHCO_3$ (30 mL) to adjust the pH=7-8 and the mixture was extracted with $CH_2Cl_2$ (3×50 mL). The combined organic phase was washed with brine (3×50 mL), dried with anhydrous $Na_2SO_4$, filtered, and concentrated under vacuum. The residue was purified by silica gel chromatography (100-200 mesh silica gel, 20-40% Ethyl acetate in Petroleum ether) to give N-[2-methyl-6-(1-methylcyclopropoxy)-3-pyridyl]acetamide (4.2 g, 19.07 mmol, 96.00% yield) as a red oil.

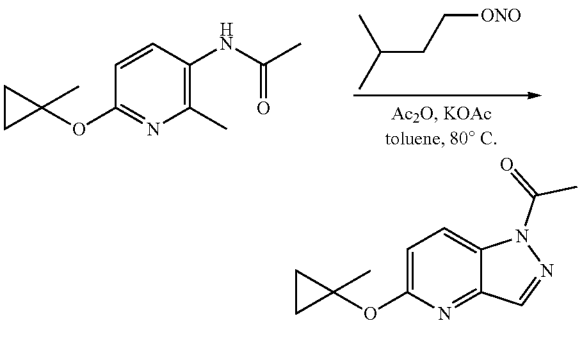

Step 4:

To a solution of N-[2-methyl-6-(1-methylcyclopropoxy)-3-pyridyl]acetamide (4.20 g, 19.07 mmol, 1 eq) in toluene (10 mL) was added KOAc (2.81 g, 28.60 mmol, 1.5 eq) and $Ac_2O$ (8.95 g, 87.71 mmol, 8.22 mL, 4.6 eq) at 20° C., the solution was heated to 80° C., then isopentyl nitrite (8.93 g, 76.27 mmol, 10.26 mL, 4 eq) was added dropwise. The mixture was stirred at 80° C. for 16 hours. TLC and LCMS showed the reaction was complete. The reaction was filtered, the resulting solid was washed with EtOAc (70 mL), and the filtrate was concentrated under vacuum. The residue was purified by silica gel chromatography (100-200 mesh silica gel, 0-10% Ethyl acetate in Petroleum ether) to give 1-[5-(1-methylcyclopropoxy)pyrazolo[4,3-b]pyridin-1-yl]ethanone (2.9 g, 12.54 mmol, 65.77% yield) as a yellow oil.

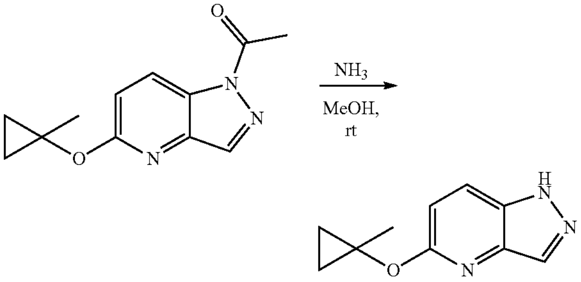

Step 5:

To a solution of 1-[5-(1-methylcyclopropoxy)pyrazolo[4,3-b]pyridin-1-yl]ethanone (2.90 g, 12.54 mmol, 1 eq) in MeOH (50 mL) was added ammonia (7 M, 1.79 mL, 1 eq) ($NH_3$ (g)/MeOH) in one portion at 20° C. The mixture was stirred at 20° C. for 30 minutes to give red solution. LCMS showed the reaction was complete. The solution was concentrated in vacuum to give 5-(1-methylcyclopropoxy)-1H-pyrazolo[4,3-b]pyridine (2.7 g, crude) as a yellow solid.

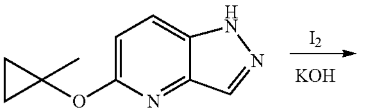

-continued

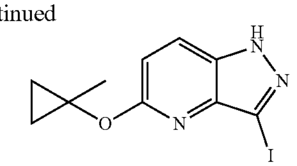

Step 6:

To a solution of 5-(1-methylcyclopropoxy)-1H-pyrazolo[4,3-b]pyridine (1.3 g, 6.87 mmol, 1 eq) in DMF (15 mL) was added $I_2$ (3.49 g, 13.74 mmol, 2.77 mL, 2 eq) and KOH (1.16 g, 20.61 mmol, 3 eq). After addition, the reaction mixture was stirred at 25° C. for 1 hour. TLC (petroleum ether:ethyl acetate=5:1) showed a major new spot and LCMS showed a peak with desired MS. The reaction mixture was quenched by addition of saturated $Na_2S_2O_3$ (30 mL) and extracted with ethyl acetate (2×30 mL). The organic layer was dried over sodium sulfate and concentrated under reduced pressure. The residue was purified by silica gel column chromatography (0 to 15% ethyl acetate in petroleum ether) to give 3-iodo-5-(1-methylcyclopropoxy)-1H-pyrazolo[4,3-b]pyridine (1.8 g, 5.71 mmol, 83.14% yield) as a colorless oil

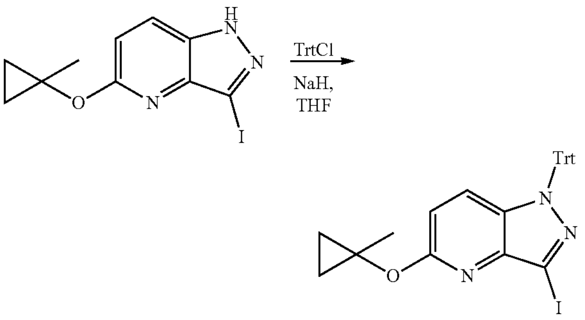

Step 7:

To a mixture of 3-iodo-5-(1-methylcyclopropoxy)-1H-pyrazolo[4,3-b]pyridine (1.8 g, 5.71 mmol, 1 eq) in THF (20 mL) was added NaH (274.19 mg, 6.85 mmol, 60% purity, 1.2 eq) in one portion at 0° C. under $N_2$. The mixture was stirred at 0° C. for 30 minutes, then [chloro(diphenyl)methyl]benzene (1.91 g, 6.85 mmol, 1.2 eq) was added and the solution was stirred at 25° C. for 2 hours. TLC and LCMS showed the reaction was complete. The residue was poured into water (20 mL). The mixture was extracted with ethyl acetate (20 mL*3). The combined organic phase was washed with brine (20 mL*2), dried with anhydrous $Na_2SO_4$, filtered, and concentrated under vacuum. The residue was purified by silica gel chromatography (40 g, 0-5% (10 minutes) of Ethyl acetate in Petroleum ether) to give 3-iodo-5-(1-methylcyclopropoxy)-1-trityl-pyrazolo[4,3-b]pyridine (2.7 g, 4.84 mmol, 84.79% yield) as a white solid.

Exemplary Synthesis of Compound 372

Compound 372 was prepared in a manner analogous to compound 209 using intermediate benzyl 4-(2-azaspiro[3.5]nonan-7-yloxymethyl)piperidine-1-carboxylate.

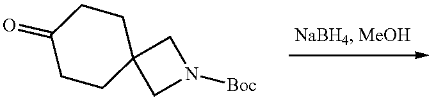

-continued

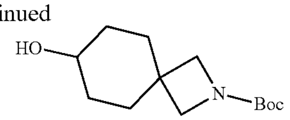

Step 1:

To a solution of tert-butyl 7-oxo-2-azaspiro[3.5]nonane-2-carboxylate (1.9 g, 7.94 mmol, 1 eq) in MeOH (20 mL) was added $NaBH_4$ (0.62 g, 16.39 mmol, 2.06 eq) at 0° C. under $N_2$. The mixture was stirred at 0° C. for 1 hour to give colorless solution. TLC (Petroleum ether:Ethyl acetate=3:1, Rf=0.22) showed the reaction was complete. The mixture was poured into HCl (10 mL, 2 M) and extracted with DCM (20 mL*3). The organic layer was washed with brine (20 mL*2), dried over anhydrous $Na_2SO_4$, filtered, and concentrated under vacuum to give tert-butyl 7-hydroxy-2-azaspiro[3.5]nonane-2-carboxylate (1.8 g, 7.46 mmol, 93.95% yield) as a white solid.

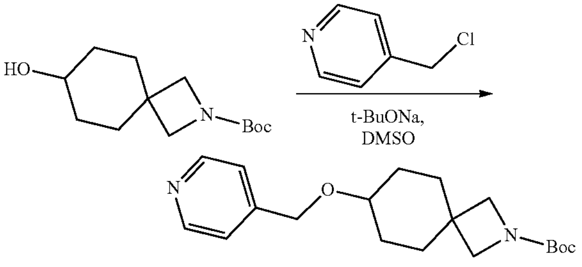

Step 2:

To a mixture of t-BuONa (1.19 g, 12.43 mmol, 2 eq) and tert-butyl 7-hydroxy-2-azaspiro[3.5]nonane-2-carboxylate (1.5 g, 6.22 mmol, 1 eq) in DMSO (10 mL) was added 4-(chloromethyl)pyridine (872.23 mg, 6.84 mmol, 1.1 eq) in one portion at 40° C. under $N_2$. The mixture was stirred at 80° C. for 10 hours. LCMS showed a peak with desired MS. The mixture was cooled to 20° C. The residue was poured into water (10 mL) and stirred for 10 minutes. The aqueous phase was extracted with ethyl acetate (10 mL*3). The combined organic phase was washed with brine (10 mL*2), dried with anhydrous $Na_2SO_4$, filtered, and concentrated under vacuum. The crude product was purified by reversed-phase HPLC (column: Welch Xtimate C18 250*50 mm*10 um; mobile phase: [water (FA)-ACN]; B %: 0%-38%, 27 min) to give tert-butyl 7-(4-pyridylmethoxy)-2-azaspiro[3.5]nonane-2-carboxylate (520 mg, 1.56 mmol, 25.17% yield) as a yellow oil.

Step 3:

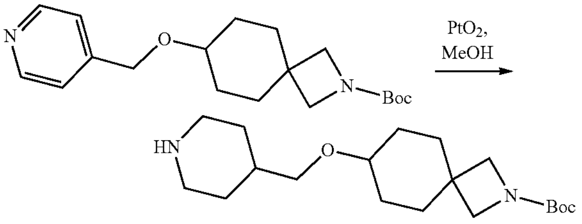

To a solution of tert-butyl 7-(4-pyridylmethoxy)-2-azaspiro[3.5]nonane-2-carboxylate (520 mg, 1.56 mmol, 1 eq) in MeOH (10 mL) was added $PtO_2$ (100 mg, 440.37 μmol, 2.82 e-1 eq) and HOAc (93.93 mg, 1.56 mmol, 89.46 uL, 1 eq) under $N_2$. The suspension was degassed under vacuum and purged with $H_2$ several times. The mixture was stirred under $H_2$ (50 psi) at 70° C. for 10 hours. LCMS showed a peak with the desired MS. The suspension was filtered through a pad of Celite and the filter cake was washed with EtOAc (20 mL×3), the filtrate was concentrated to give tert-butyl 7-(4-piperidylmethoxy)-2-azaspiro[3.5]nonane-2-carboxylate (1.13 g, crude, HOAc) as a yellow oil.

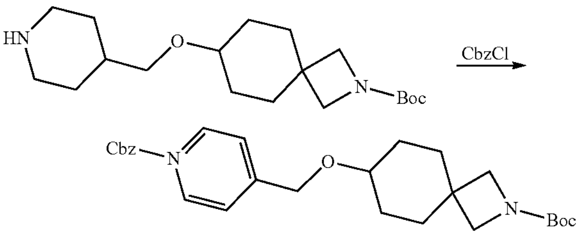

Step 4:

To a solution of tert-butyl 7-(4-piperidylmethoxy)-2-azaspiro[3.5]nonane-2-carboxylate (600 mg, 1.77 mmol, 1 eq) and $NaHCO_3$ (1.49 g, 17.73 mmol, 689.40 uL, 10 eq) in a mixed solvent of $H_2O$ (10 mL) and MeCN (10 mL) was added CbzCl (453.59 mg, 2.66 mmol, 377.99 uL, 1.5 eq) at 0° C. The reaction mixture was stirred at 0° C. for 1 hour. TLC showed the reaction was complete. The residue was poured into water (10 mL). The aqueous phase was extracted with ethyl acetate (10 mL*3). The combined organic phase was washed with brine (10 mL*2), dried with anhydrous $Na_2SO_4$, filtered, and concentrated under vacuum. The residue was purified by silica gel chromatography (0-15% of Ethyl acetate in Petroleum ether) to give tert-butyl 7-[(1-benzyloxycarbonyl-4-piperidyl)methoxy]-2-azaspiro[3.5]nonane-2-carboxylate (790 mg, 1.67 mmol, 94.30% yield) as a colorless oil.

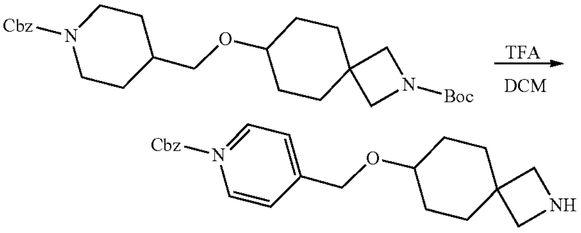

Step 5:

To a mixture of tert-butyl 7-[(1-benzyloxycarbonyl-4-piperidyl)methoxy]-2-azaspiro[3.5]nonane-2-carboxylate (860 mg, 1.82 mmol, 1 eq) in DCM (10 mL) was added TFA (2.40 g, 21.08 mmol, 1.56 mL, 11.59 eq) in one portion at 25° C. under $N_2$. The mixture was stirred at 25° C. for 30 minutes. LCMS showed the reaction was complete. The residue was poured into $NaHCO_3$ (10 mL) to adjust the pH=7-8. The aqueous phase was extracted with ethyl acetate (10 mL*3). The combined organic phase was washed with brine (10 mL*2), dried with anhydrous $Na_2SO_4$, filtered, and concentrated under vacuum to give benzyl 4-(2-azaspiro[3.5]nonan-7-yloxymethyl)piperidine-1-carboxylate (694 mg, crude) as a white solid.

Exemplary Synthesis of Compound 373

Compound 373 was prepared in a manner analogous to compound 219.

Exemplary Synthesis of Compound 374

Compound 374 was prepared in a manner analogous to compound 209.

Exemplary Synthesis of Compound 375

Compound 375 was prepared in a manner analogous to compound 78.

Exemplary Synthesis of Compound 376

Compound 376 was prepared in a manner analogous to compound 181.

Exemplary Synthesis of Compound 377

Compound 377 was prepared in a manner analogous to compound 181 using intermediate 3-(6-chloropyridazin-4-yl)-5-(1-methylcyclopropoxy)-1-tetrahydropyran-2-yl-indazole.

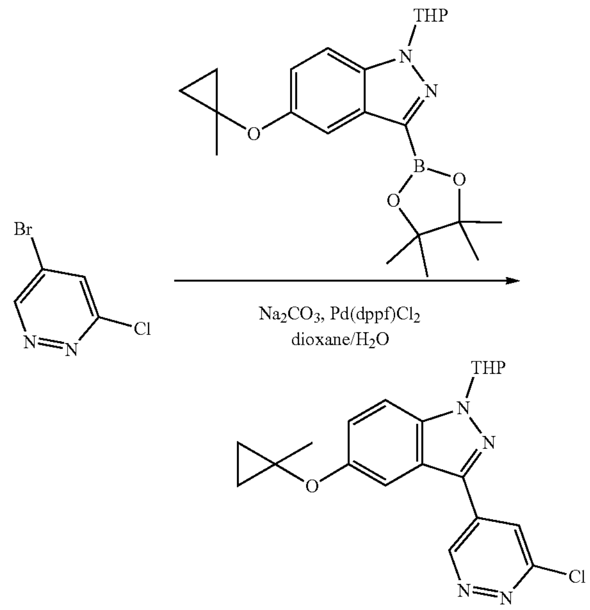

Step 1:

To a solution of 5-(1-methylcyclopropoxy)-1-tetrahydropyran-2-yl-3-(4,4,5,5-tetramethyl-1,3,2-dioxaborolan-2-yl) indazole (180 mg, 451.92 μmol, 1 eq) and 5-bromo-3-chloro-pyridazine (87.41 mg, 451.92 μmol, 1 eq) in dioxane (10 mL) and $H_2O$ (2 mL) was added $Pd(dppf)Cl_2$ (33.07 mg, 45.19 μmol, 0.1 eq) and $Na_2CO_3$ (143.70 mg, 1.36 mmol, 3 eq). After addition, the reaction mixture was stirred at 100° C. under $N_2$ for 16 hours. LCMS showed a peak with the desired MS and TLC (Petroleum ether:Ethyl acetate=3:1) showed one new spot. After cooling, the reaction mixture was filtered and filtrate was concentrated under reduced pressure. The residue was purified by silica gel column chromatography (0 to 20% Ethyl acetate in Petroleum ether) to give 3-(6-chloropyridazin-4-yl)-5-(1-methylcyclopropoxy)-1-tetrahydropyran-2-yl-indazole (150 mg, 323.50 μmol, 71.58% yield, 83% purity) as a white solid.

Exemplary Synthesis of Compound 378

Compound 378 was prepared in a manner analogous to compound 309.

Exemplary Synthesis of Compound 379

Compound 379 was prepared in a manner analogous to compound 354.

Exemplary Synthesis of Compound 380

Compound 380 was prepared in a manner analogous to compounds 210 and 211.

Exemplary Synthesis of Compound 381

Compound 381 was prepared in a manner analogous to compound 234.

Exemplary Synthesis of Compound 382

Compound 382 was prepared in a manner analogous to compound 211.

Exemplary Synthesis of Compound 383

Compound 383 was prepared in a manner analogous to compound 354 using intermediate 4-[[1-[2-(2,6-dioxo-3-piperidyl)-4-fluoro-1-oxo-isoindolin-5-yl]-4-piperidyl]oxy] cyclohexanecarbaldehyde.

Exemplary Synthesis of Compound 384

Compound 384 was prepared in a manner analogous to compounds 354 and 211.

Specific Embodiments

An aspect of the present disclosure relates to a hetero-bifunctional compound having the chemical structure:

PTM-L-CLM, or a pharmaceutically acceptable salt or solvate thereof, wherein:

(a) the CLM is a small molecule E3 ubiquitin ligase binding moiety that binds a cereblon E3 ubiquitin ligase and represented by the chemical structure:

(a1)

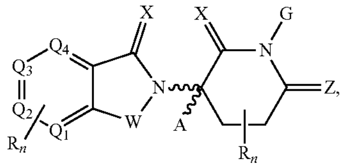

(a2)

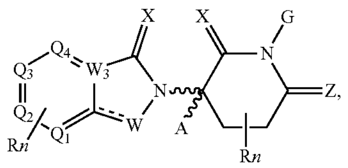

-continued (a3)

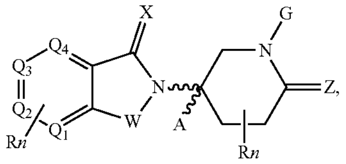

or (a4)

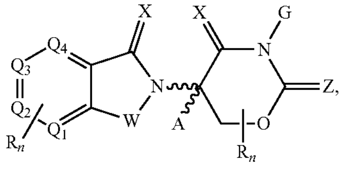

wherein:
W is $CH_2$, C═O, $SO_2$, or NH;
each X is independently selected from absent, O, and S;
Z is absent, O, or S;
G is H or unsubstituted or substituted linear or branched alkyl;
each $Q_1$, $Q_2$, $Q_3$, and $Q_4$ is independently N, CH, or CR;
A is H or unsubstituted or substituted linear or branched alkyl;
n is an integer from 1 to 10 (e.g., 1-4, 1, 2, 3, 4, 5, 6, 7, 8, 9, or 10);
R is a bond, H, O, —CONR'R", —C(═O)R', —OR', —NR'R", unsubstituted or substituted linear or branched alkyl optionally substituted alkoxyl group, —Cl, —F, —Br, —$CF_3$, or —CN, wherein one R is covalently joined to the L; and
R' and R" are independently selected from a bond, H, and optionally substituted alkyl;
 represents a single bond or a double bond; and
 represents a bond that may be stereospecific ((R) or (S)) or non-stereospecific;
(b) the PTM is a small molecule leucine-rich repeat kinase 2 (LRRK2) targeting moiety that binds to LRRK2 or a mutant form thereof represented by the chemical structure:

(PTM-IA)

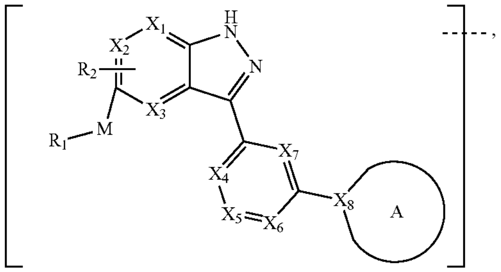

(PTM-IIIA1)

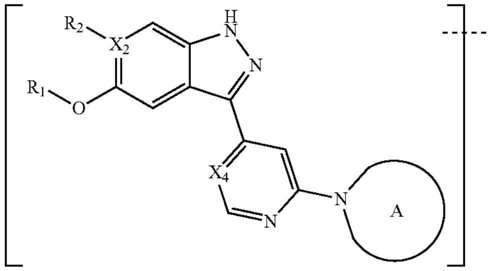

or

-continued (PTM-IIIA2)

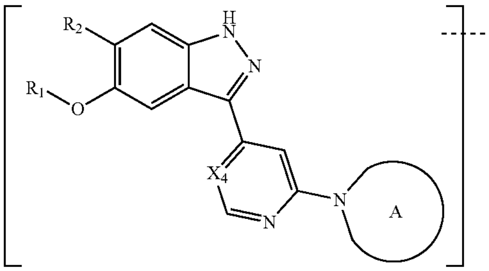

or (PTM-IIIA3)

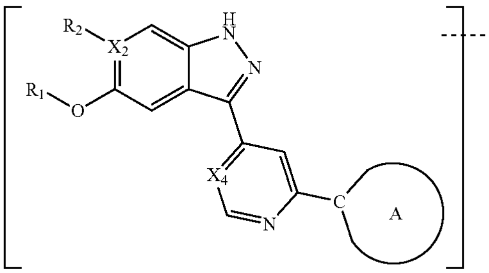

or (PTM-IIIA4)

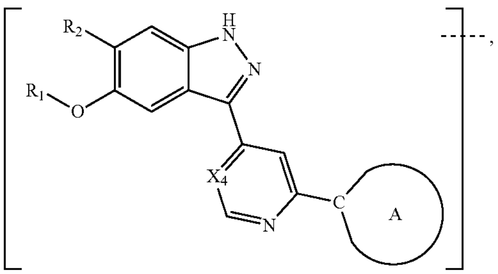

wherein:
$R_1$ is a isopropyl, tert-butyl,

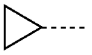

, or

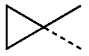

, wherein  is the point of attachment to the oxygen atom of the PTM;
$R_2$ is hydrogen, F, Cl, OH, C1-C3 alkyl, or C1-C3 fluoroalkyl;
$X_6$ and $X_7$ are each independently CH or N;
$X_1$, $X_2$, $X_3$, $X_4$, and $X_5$ are each independently a N or CH that is optionally substituted with $R_2$ when CH;
$X_8$ is CH or N;

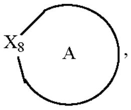

,

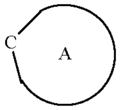

, or

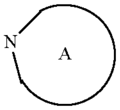

is an optionally substituted 3-10 membered cycloalkyl, heterocyloalkyl, bicycloalkyl, biheterocycloalkyl, spirocycloalkyl, or spiroheterocycloalkyl containing 1-4 (e.g., 1, 2, 3, or 4) heteroatoms selected from N, O, and S (e.g., optionally substituted with one or more (e.g., 1, 2, 3, or 4) substitutions; and of the PTM indicates the point of attachment with the L; and (c) the L is a chemical linker group that covalently couples the CLM to the PTM.

In any aspect or embodiment described herein, the PTM is represented by:

(PTM-IIIB1)

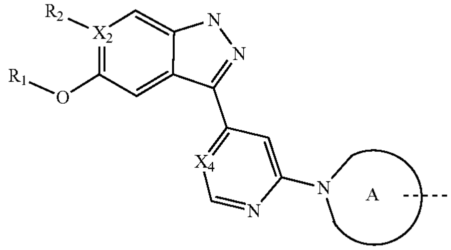

or (PTM-IIIB2)

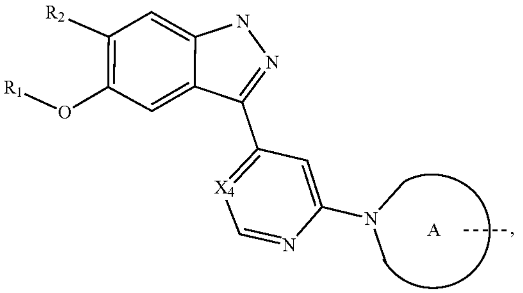

wherein of the PTM indicates the point of attachment with the L.

In any aspect or embodiment described herein, the PTM is represented by:

(PTM-IIIB3)

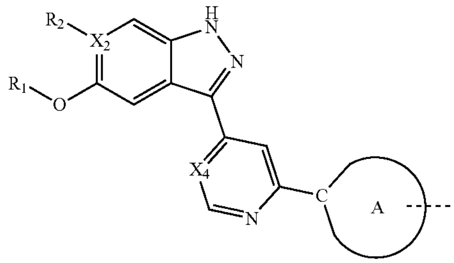

or

-continued (PTM-IIIB4)

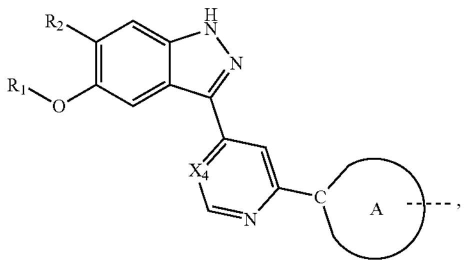

wherein of the PTM indicates the point of attachment with the L.

An aspect of the present disclosure relates to a hetero-bifunctional compound having the chemical structure:

PTM-L-CLM, or a pharmaceutically acceptable salt or solvate thereof, wherein:

(a) the CLM is a small molecule E3 ubiquitin ligase binding moiety that binds a cereblon E3 ubiquitin ligase and represented by the chemical structure:

(a1)

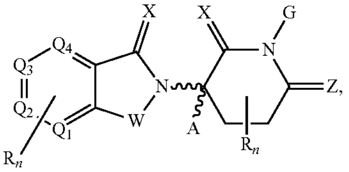

(a2)

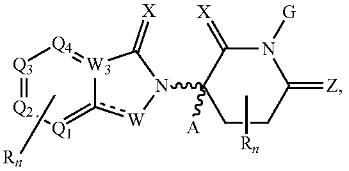

(a3)

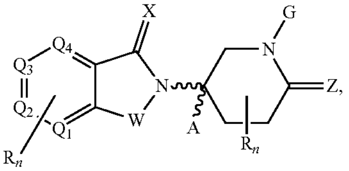

or (a4)

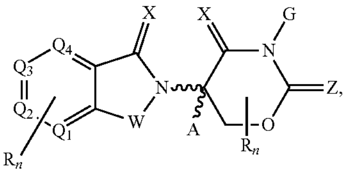

wherein:

W is $CH_2$, C═O, $SO_2$, or NH;

each X is independently selected from absent, O, and S;

Z is absent, O, or S;

G is H or unsubstituted or substituted linear or branched alkyl;

each $Q_1$, $Q_2$, $Q_3$, and $Q_4$ is independently N, CH, or CR;

A is H or unsubstituted or substituted linear or branched alkyl;

n is an integer from 1 to 10 (e.g., 1-4, 1, 2, 3, 4, 5, 6, 7, 8, 9, or 10);

R is a bond, H, O, —CONR'R", —C(═O)R', —OR', —NR'R", unsubstituted or substituted linear or branched alkyl optionally substituted alkoxyl group, —Cl, —F, —Br, —$CF_3$, or —CN, wherein one R is covalently joined to the L; and R' and R" are independently selected from a bond, H, and optionally substituted alkyl;

represents a single bond or a double bond; and represents a bond that may be stereospecific ((R) or (S)) or non-stereospecific;

(b) the PTM is a small molecule leucine-rich repeat kinase 2 (LRRK2) targeting moiety that binds to LRRK2 or a mutant form thereof represented by the chemical structure:

(PTM-IA)

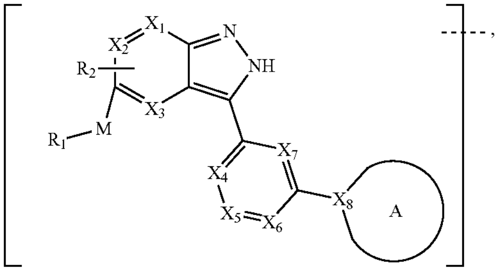

(PTM-IIIA1)

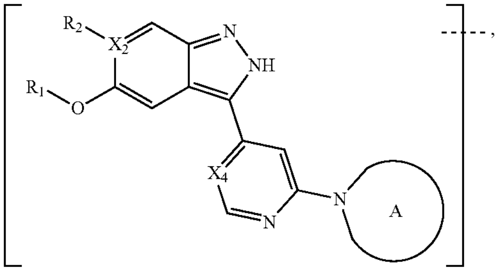

(PTM-IIIA2)

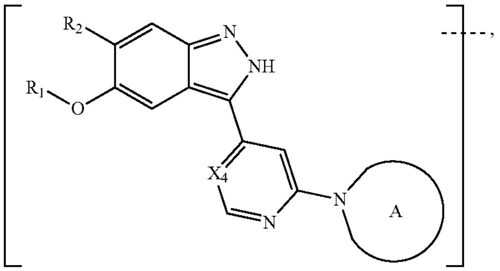

(PTM-IIIA3)

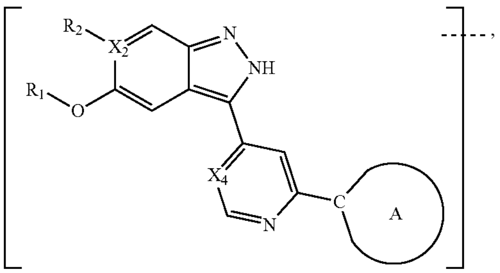

or

-continued (PTM-IIIA4)

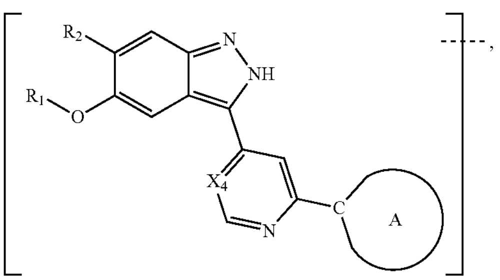

wherein:

$R_1$ is a isopropyl, tert-butyl,

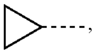

or

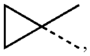

wherein is the point of attachment to the oxygen atom of the PTM;

$R_2$ is hydrogen, F, Cl, OH, C1-C3 alkyl, or C1-C3 fluoroalkyl, $X_6$ and $X_7$ are each independently CH or N;

$X_1$, $X_2$, $X_3$, $X_4$, and $X_5$ are each independently a N or CH that is optionally substituted with $R_2$ when CH;

$X_8$ is CH or N;

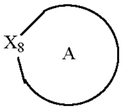

,

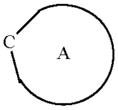

, or

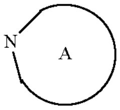

is an optionally substituted 3-10 membered cycloalkyl, heterocyloalkyl, bicycloalkyl, biheterocycloalkyl, spirocycloalkyl, or spiroheterocycloalkyl containing 1-4 (e.g., 1, 2, 3, or 4) heteroatoms selected from N, O, and S (e.g., optionally substituted with one or more (e.g., 1, 2, 3, or 4) substitutions; and of the PTM indicates the point of attachment with the L; and (c) the L is a bond or a chemical linker group that covalently couples the CLM to the PTM.

In any aspect or embodiment described herein, the PTM is represented by:

(PTM-IIIB1)

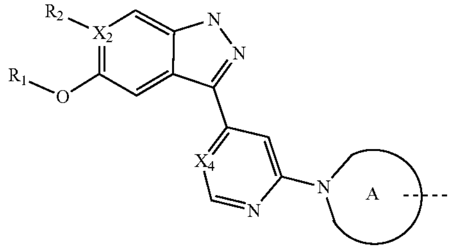

or (PTM-IIIB2)

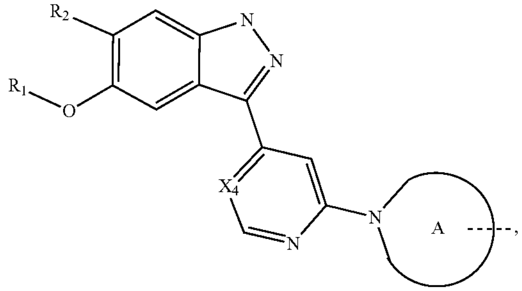

wherein ⸝⸝ of the PTM indicates the point of attachment with the L.

In any aspect or embodiment described herein, the PTM is represented by:

(PTM-IIIB3)

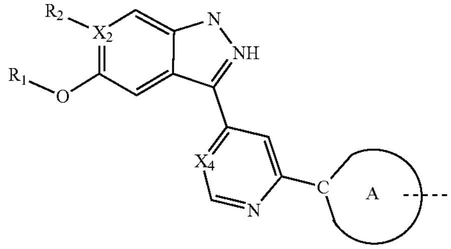

or

-continued (PTM-IIIB4)

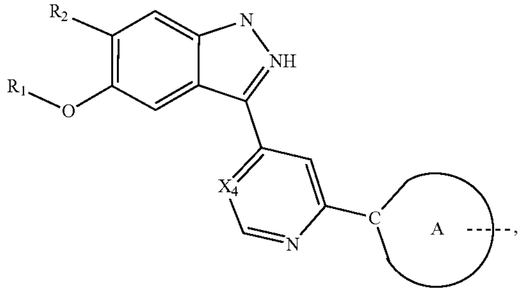

wherein ⸝⸝ of the PTM indicates the point of attachment with the L.

In any aspect or embodiment described herein, the CLM is represented by the chemical structure:

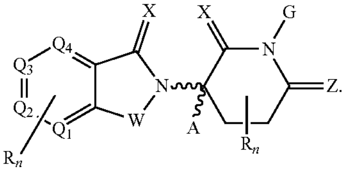

In any aspect or embodiment described herein, the compound is represented by a chemical structure selected from:

(Formula Ia)

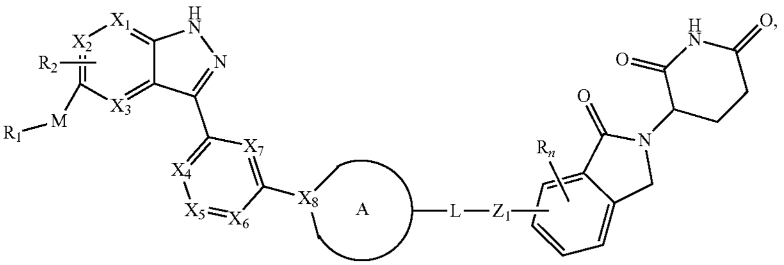

-continued (Formula IIIa)

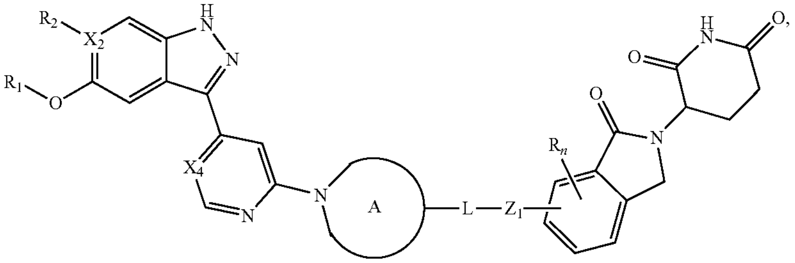

and (Formula IIIb)

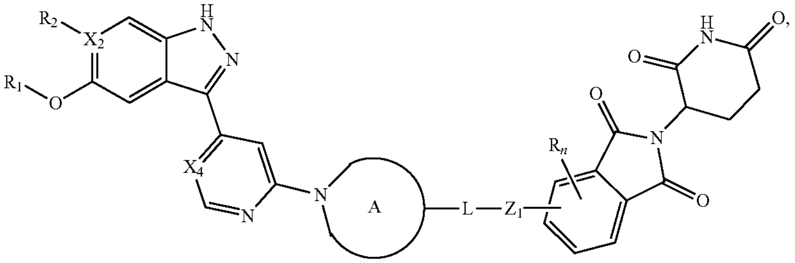

wherein:

$X_2$ is C, CH or N;

$Z_1$ is a bond a carbon shared with a cyclic group of L, or a nitrogen shared with a cyclic group of L;

n is an integer from 0 to 3 (e.g., 0, 1, 2, or 3);

R is a bond, H, O, OH, N, NH, $NH_2$, C1, —F, methyl, methoxy, or ethoxy; and $R^2$ is H, Cl, F, OH, C1-C3 alkyl, or C1-3 fluoralkyl.

In any aspect or embodiment described herein, the compound is represented by a chemical structure selected from:

(Formula IIId)

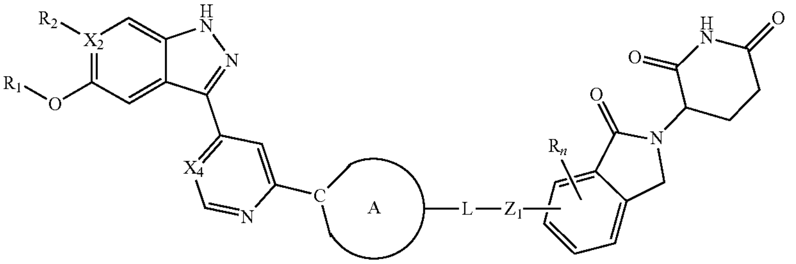

and (Formula IIIe)

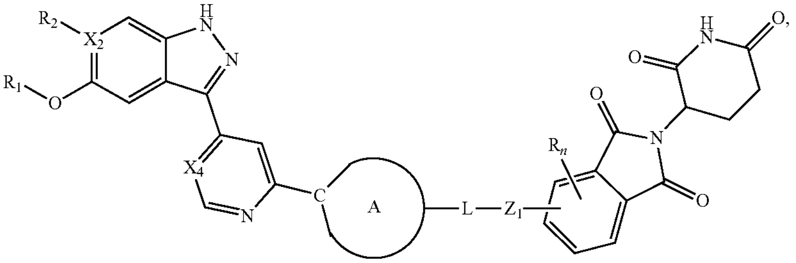

wherein:

$X_2$ is C, CH or N;

$Z_1$ is a bond a carbon shared with a cyclic group of L, or a nitrogen shared with a cyclic group of L;

n is an integer from 0 to 3 (e.g., 0, 1, 2, or 3);

R is a bond, H, O, OH, N, NH, $NH_2$, C1, —F, methyl, methoxy, or ethoxy; and $R^2$ is H, Cl, F, OH, C1-C3 alkyl, or C1-3 fluoralkyl.

In any aspect or embodiment described herein, the compound is represented by the chemical structure:

(Formula VIa)

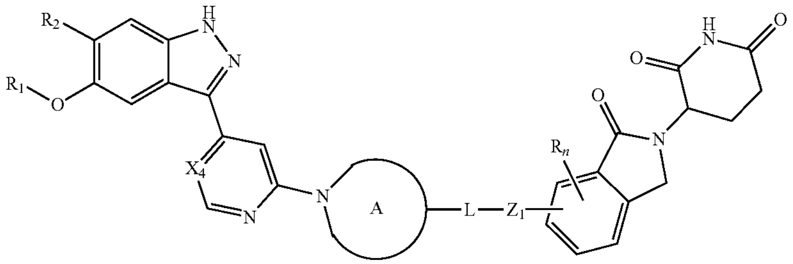

or (Formula VIb)

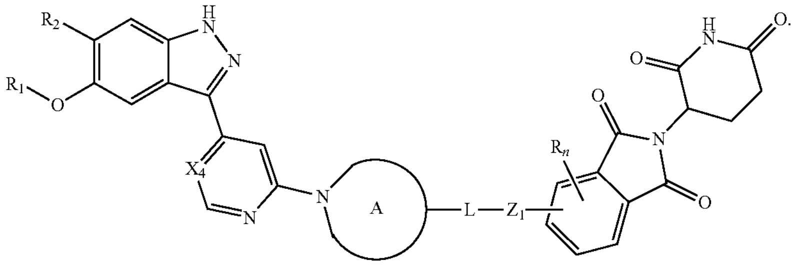

.

In any aspect or embodiment described herein, the compound is represented by the chemical structure:

(Formula VId)

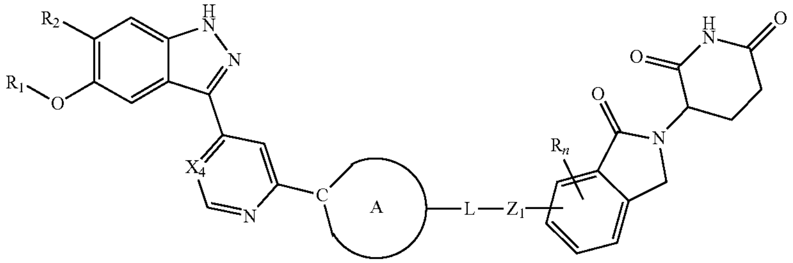

or (Formula VIe)

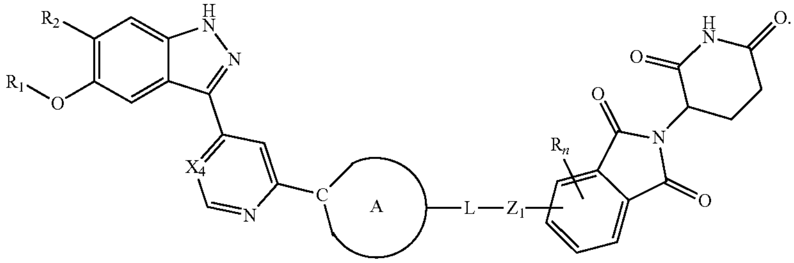

.

In any aspect or embodiment described herein,

In any aspect or embodiment described herein, each R is selected from a H, O, OH, NH, $NH_2$, —Cl, —F, CN, $CF_3$, optionally substituted linear or branched $C_{1-3}$ alkyl, optionally substituted linear or branched $C_{1-3}$ alkoxy In any aspect or embodiment described herein, each R is selected from a H, O, OH, NH, $NH_2$, —Cl, —F, —CN, $CF_3$, methyl, methoxy, and ethoxy.

In any aspect or embodiment described herein, one or more of:

(a)

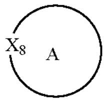 or 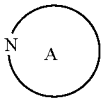

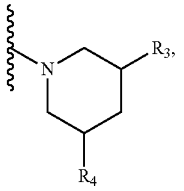 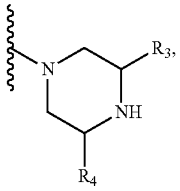

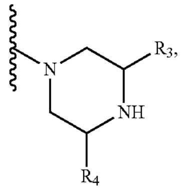 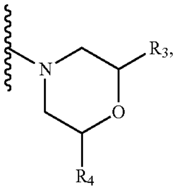

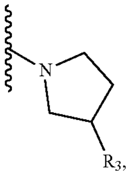

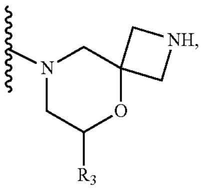

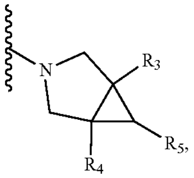 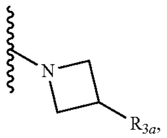

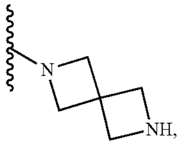 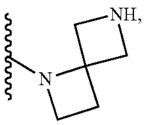

-continued

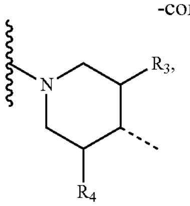 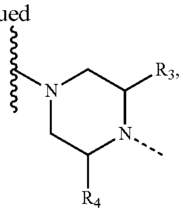

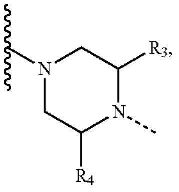 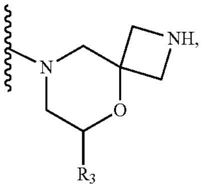

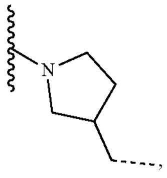 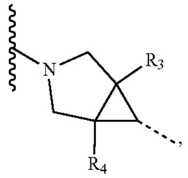

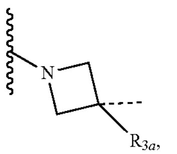 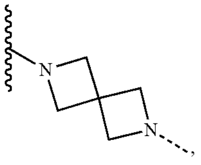

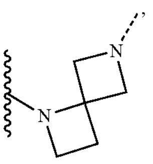 or 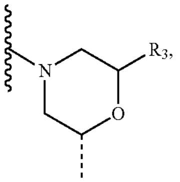

wherein: $R_3$ is H or methyl; $R_{3a}$ is H, halogen (e.g., Cl or F), or methyl; $R_4$ is H or methyl; $R_5$ is H or methyl; ⌇— indicates the point of attachment to the PTM; and ⋰ indicates the point of attachment with the L, and where ⋰ is not present, the

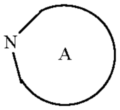 or 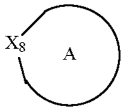

is attached to the L via an atom of a N or CH of the cyclic group, $R_3$, $R_4$, or $R_5$;

(b) $R_2$ is H or F; or (c) combinations thereof.

In any aspect or embodiment described herein,

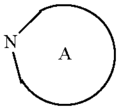

is selected from the group consisting of:
In any aspect or embodiment described herein,
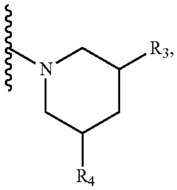
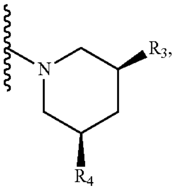
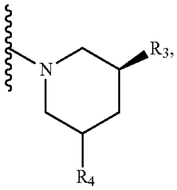
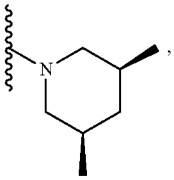
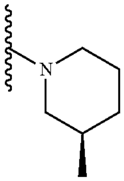
,
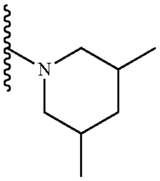
,
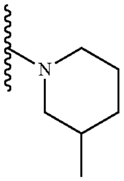
,
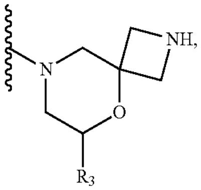
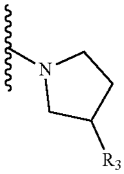
,
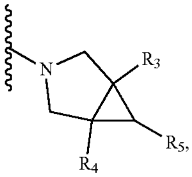
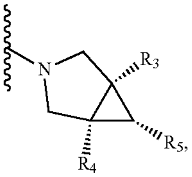
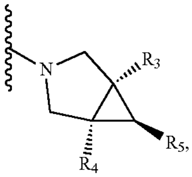
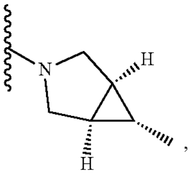
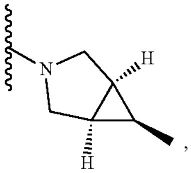
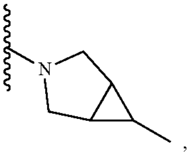
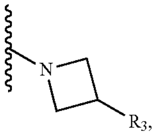
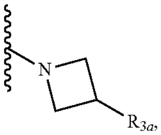
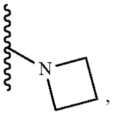
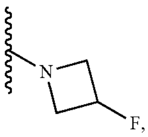
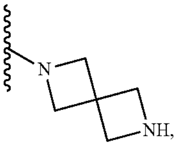
-continued
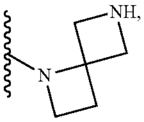
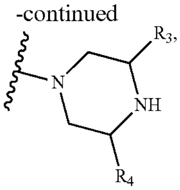
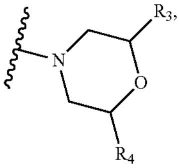
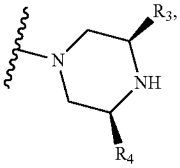
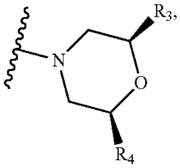
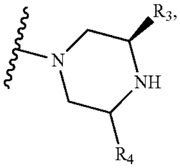
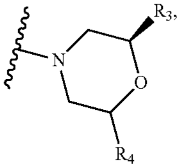
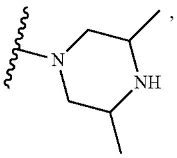
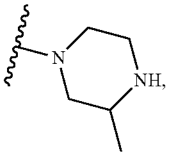
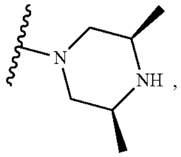
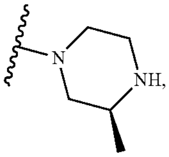
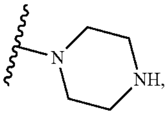
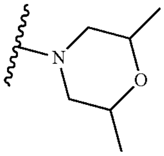
,
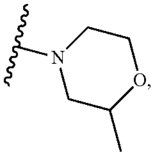
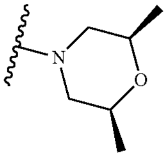
,
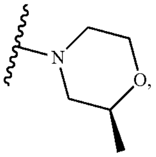
and
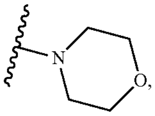
wherein the heterocycloalkyl is attached to the L or the PTM via an atom of the cyclic group or a substituent thereof.

In any aspect or embodiment described herein, the PTM is represented by chemical structure:
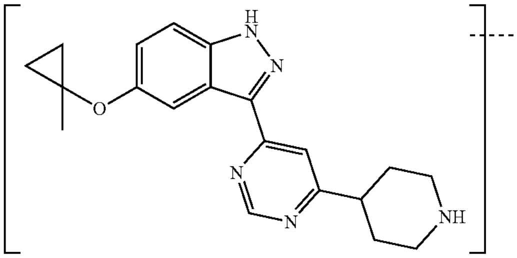
,
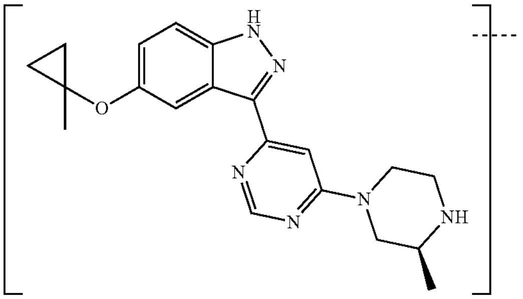
,
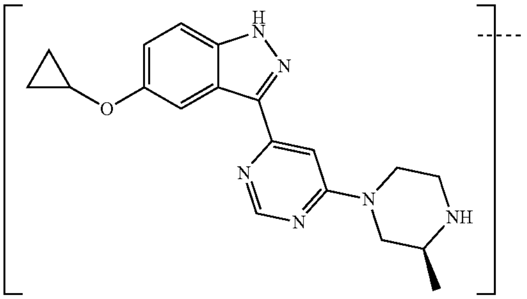
,
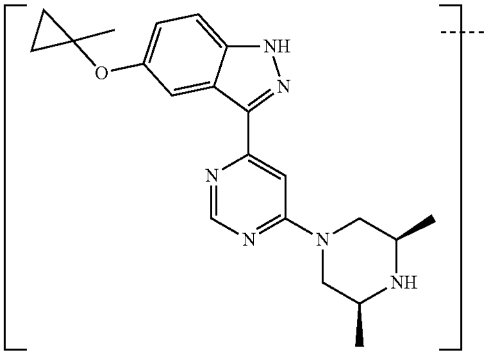
,
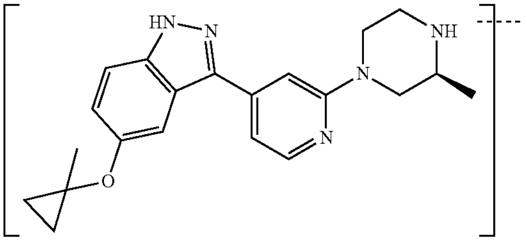
,
-continued
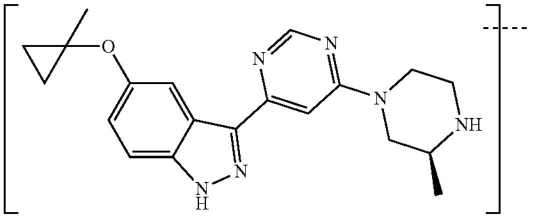
,
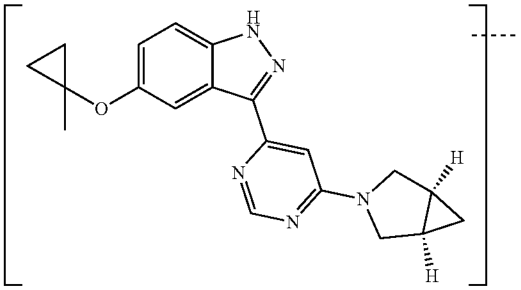
,
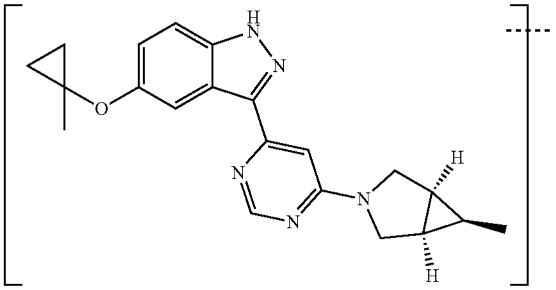
,
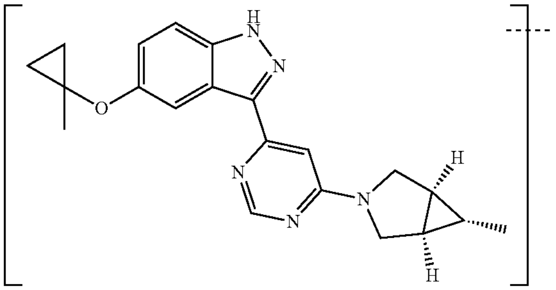
,
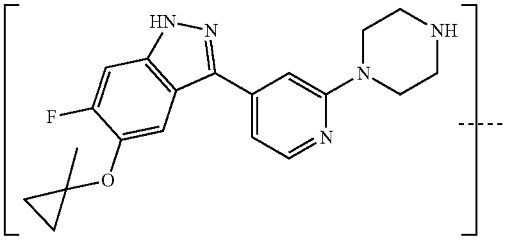
,
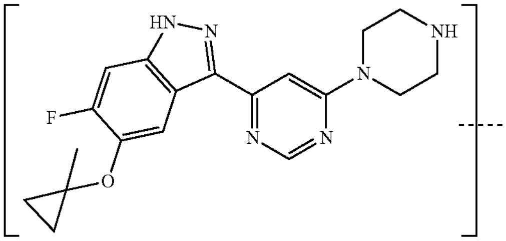
, -continued
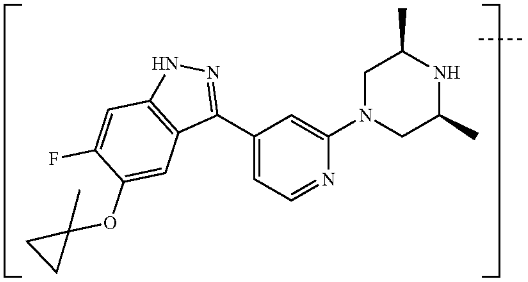
,
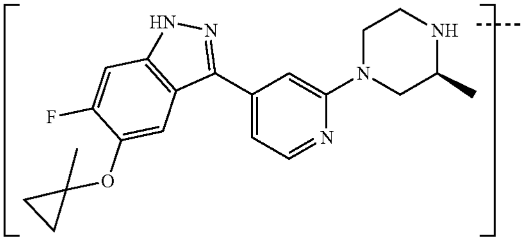
,
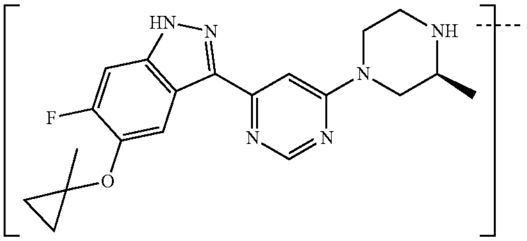
,
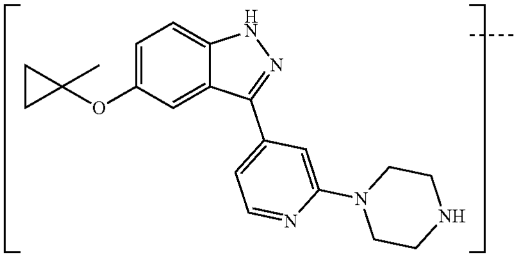
,
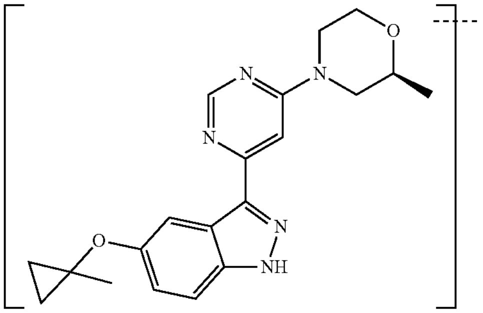
,
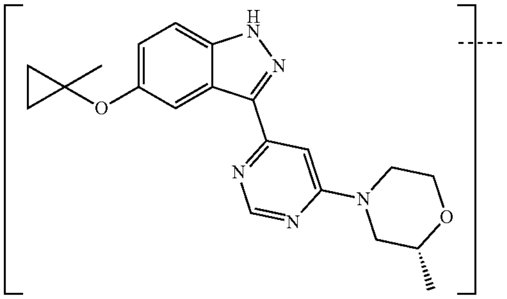
,
-continued
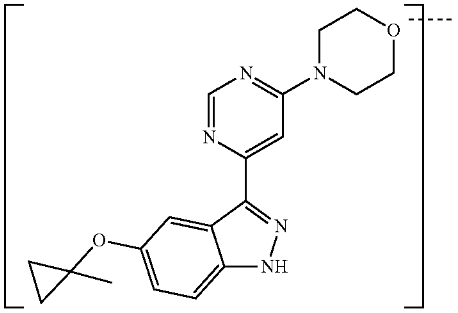
,
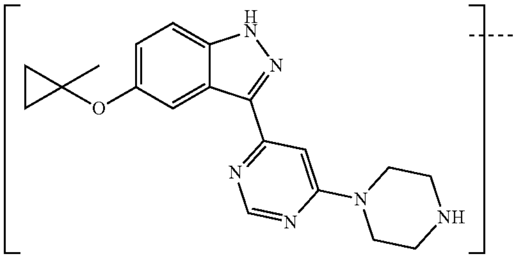
,
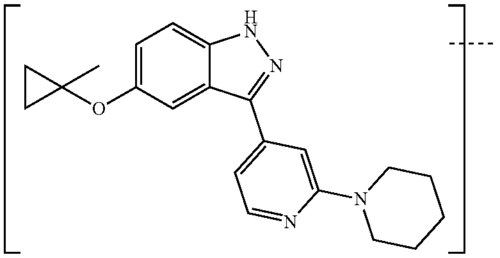
,
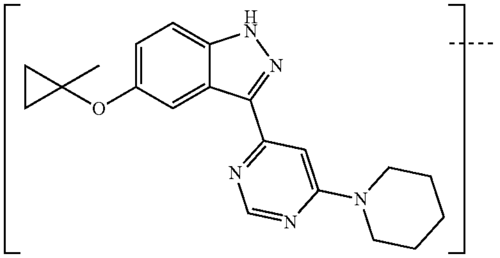
,
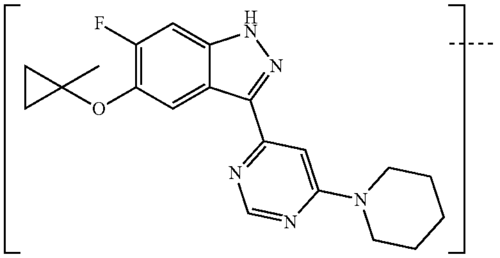
,
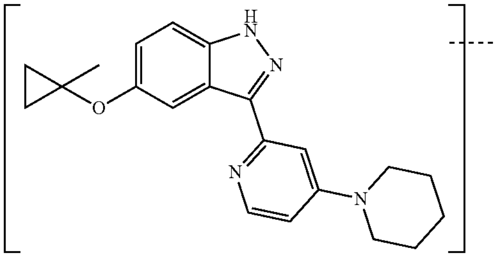
, -continued
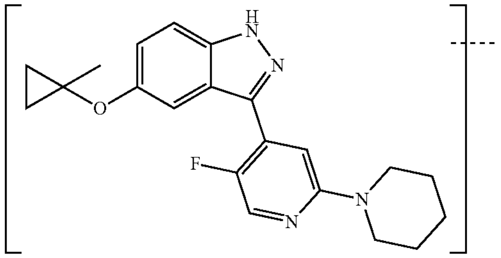,
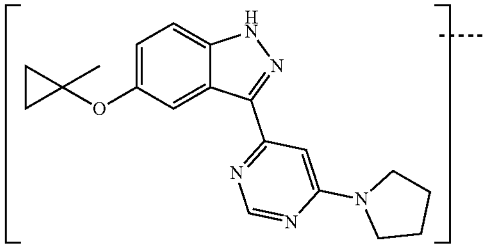,
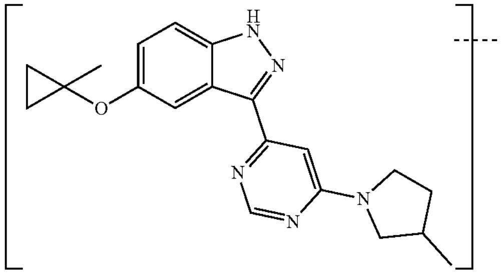,
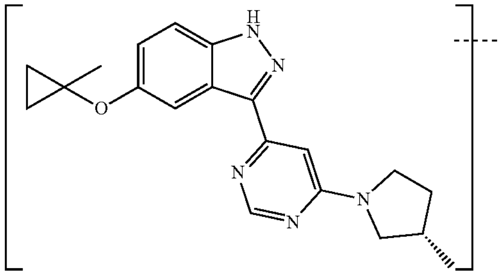,
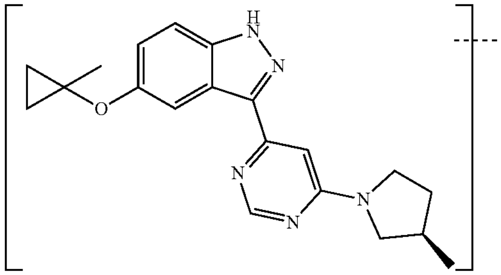,
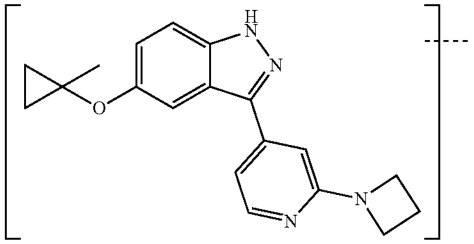,
-continued
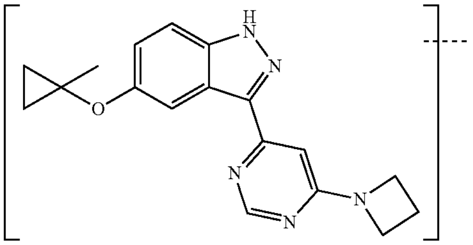,
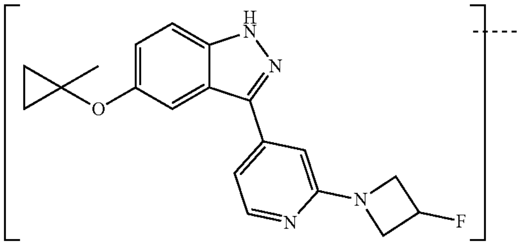,
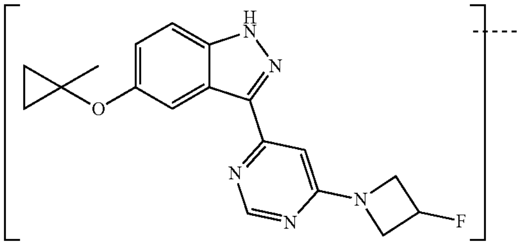,
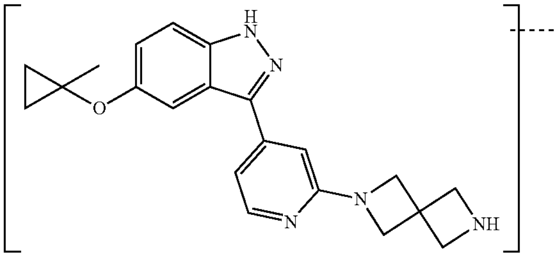,
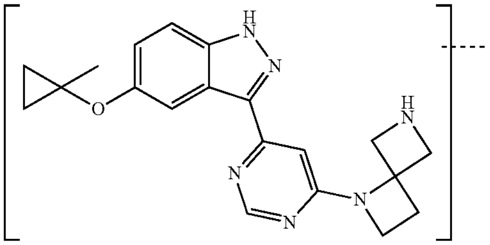,
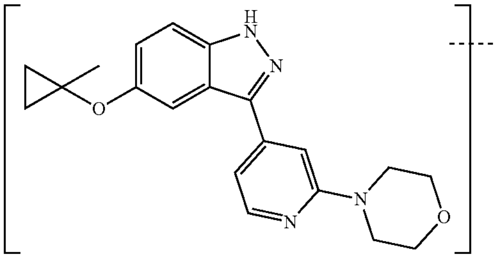, -continued

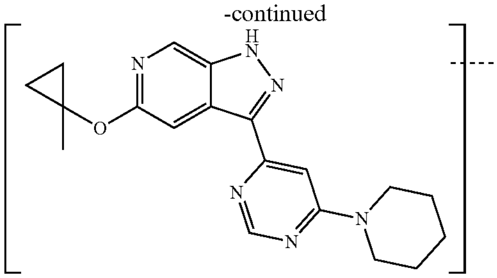

, or

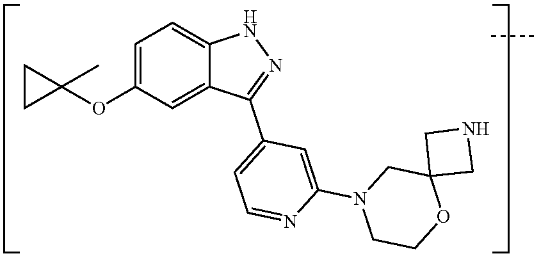

, wherein  indicates a site of attachment of the L.

In any aspect or embodiment described herein, the L comprises a chemical structural unit represented by the formula: $-(A^L)_q-$, wherein:

$-(A^L)_q-$ is a group which is connected to the CLM and the PTM;

q is an integer greater than or equal to 1;

each $A^L$ is independently selected from $CR^{L1}R^{L2}$, O, S, SO, $SO_2$, $NR^{L3}$, $SO_2NR^{L3}$, $SONR^{L3}$, $CONR^{L3}NR^{L3}CONR^{L4}$, $NR^{L3}SO_2NR^{L4}$, CO, $CR^{L1}{=}CR^{L2}$, C≡C, $C_{3-11}$ cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heteocyclyl optionally substituted with 1-6 $R^{L1}$ and/or $R^{L2}$ groups, $C_5$13 spiroheterocyclyl optionally substituted with 1-8 $R^{L1}$ and/or $R^{L2}$ groups, aryl optionally substituted with 0-6 $R^{L1}$ and/or $R^{L2}$ groups, and heteroaryl optionally substituted with 1-6 $R^{L1}$ and/or $R^{L2}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$ heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH═CH($C_{1-8}$alkyl), C($C_{1-8}$alkyl)═CH($C_{1-8}$alkyl), C($C_{1-8}$alkyl)═C($C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2$ $NH(C_{1-8}alkyl)$, NH $SO_2N(C_{1-8}alkyl)_2$, or NH $SO_2NH_2$.

In any aspect or embodiment described herein, the L includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally replaced with $CR^{L1}R^{L2}$, O, S, SO, $SO_2$, $NR^{L3}$, $SO_2NR^{L3}$, $SONR^{L3}$, $CONR^{L3}NR^{L3}CONR^{L4}$, $NR^{L3}SO_2NR^{L4}$, CO, $CR^{L1}{=}CR^{L2}$, C≡C, $C_{3-11}$ cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heteocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, or heteroaryl optionally substituted with 1-6 $R^{L1}$ and/or $R^{L2}$ groups; and $R^{L1}$, $R^{L2}$, $R^{L3}$, $R^{L4}$ and $R^{L5}$ are, each independently, H, halogen, $C_{1-8}$alkyl, $OC_{1-8}$alkyl, $SC_{1-8}$alkyl, $NHC_{1-8}$alkyl, $N(C_{1-8}\ alkyl)_2$, $C_{3-11}$ cycloalkyl, aryl, heteroaryl, $C_{3-11}$ heterocyclyl, $OC_{3-8}$cycloalkyl, $SC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH═CH($C_{1-8}$alkyl), C($C_{1-8}$alkyl)═CH($C_{1-8}$alkyl), C($C_{1-8}$alkyl)═C($C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2$ $NH(C_{1-8}alkyl)$, NH $SO_2N(C_{1-8}alkyl)_2$, or NH $SO_2NH_2$.

In any aspect or embodiment described herein, the L is selected from the group consisting of:

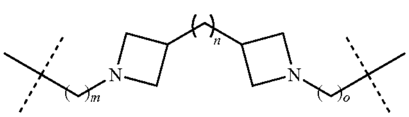

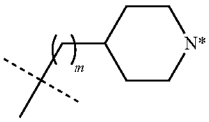

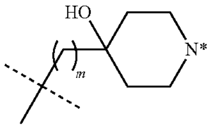

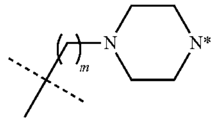

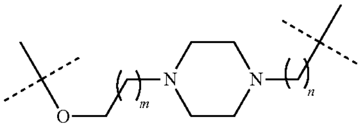

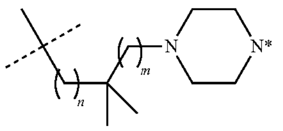

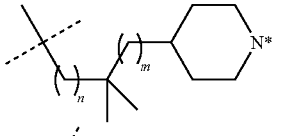

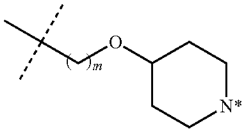

-continued
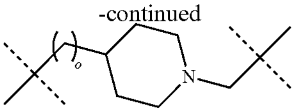
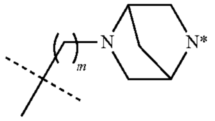
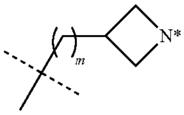
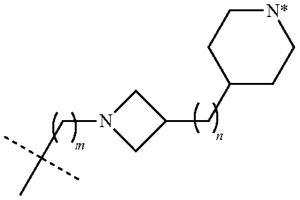
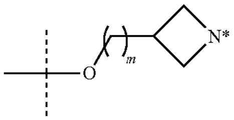
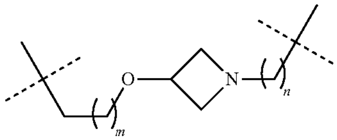
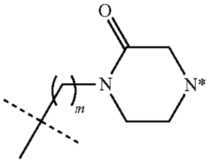
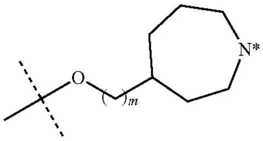
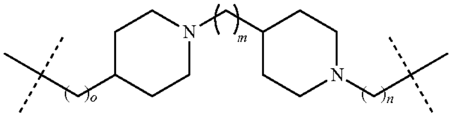
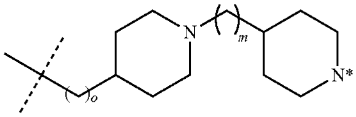
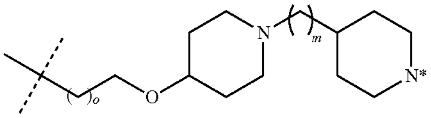
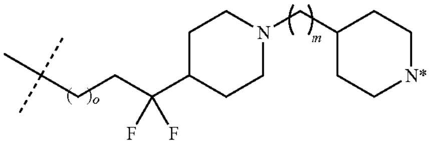
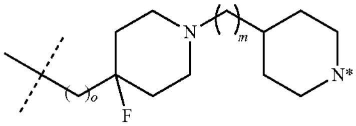
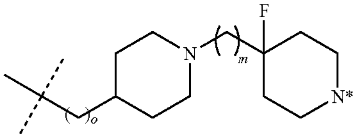
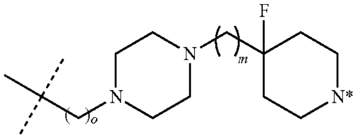
-continued
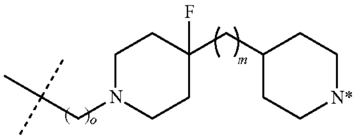
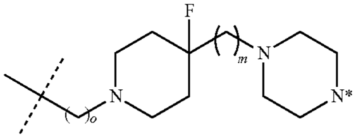
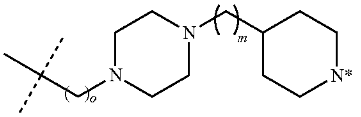
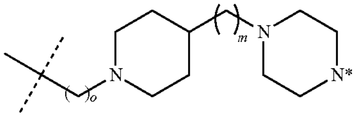
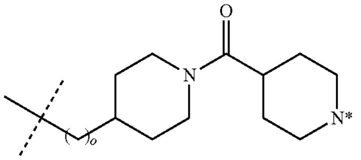
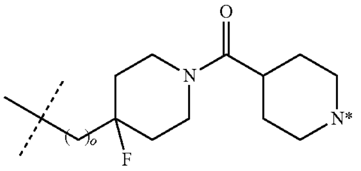
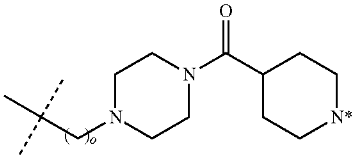
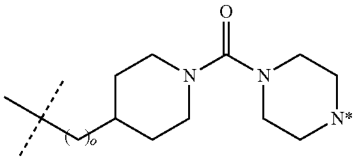
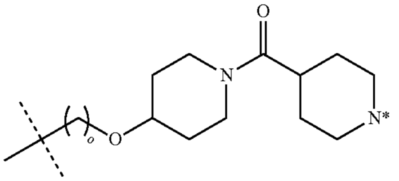
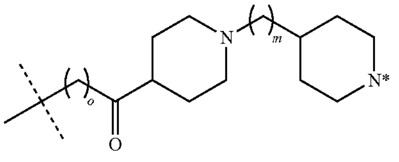
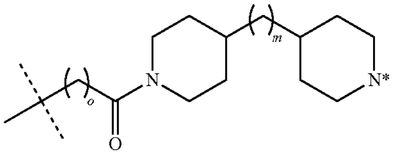

-continued
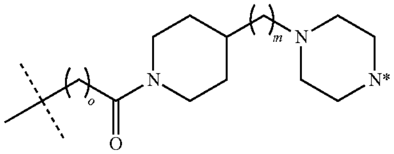
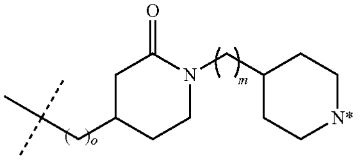
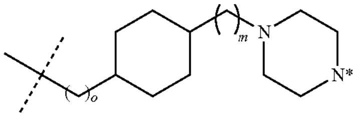
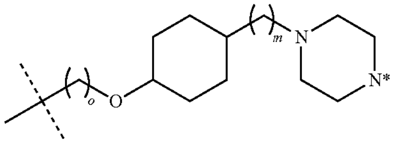
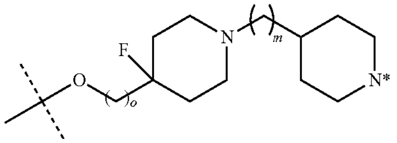
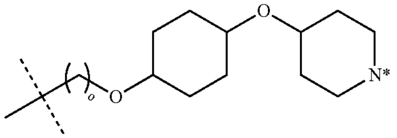
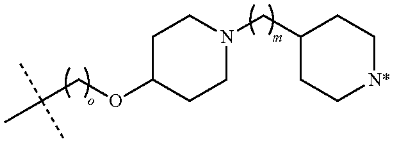
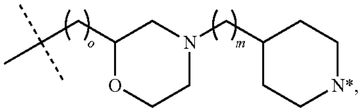
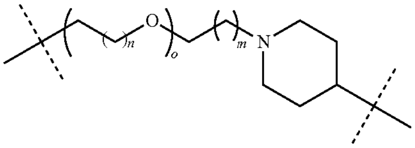
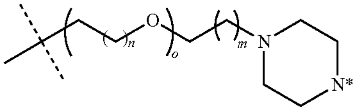
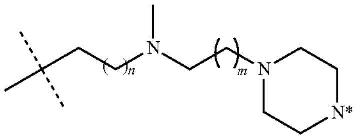
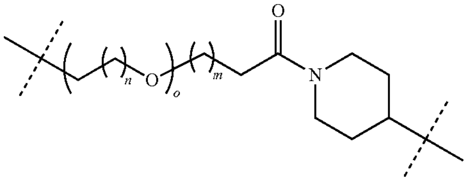
-continued
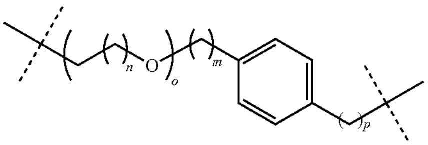
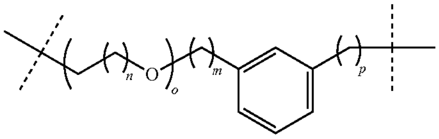
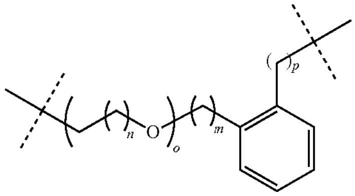
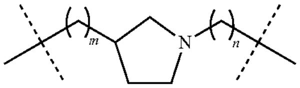
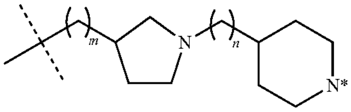
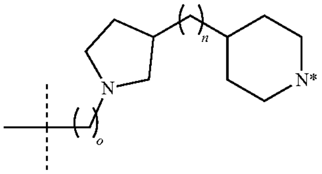
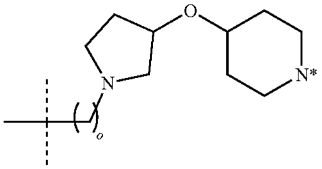
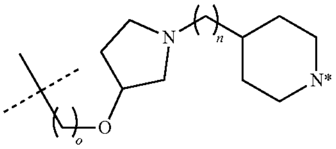
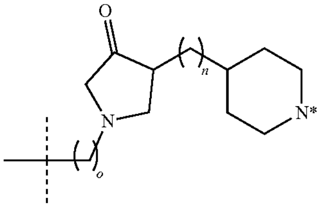
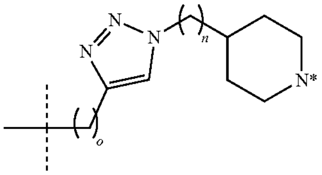
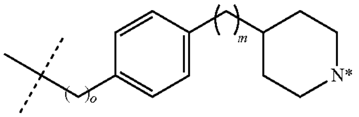

-continued
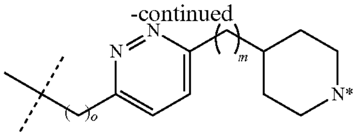
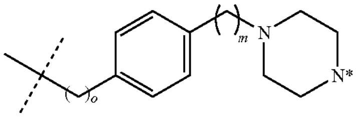
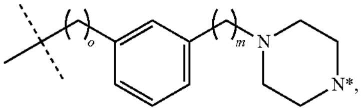
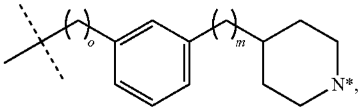
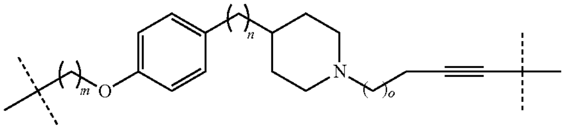
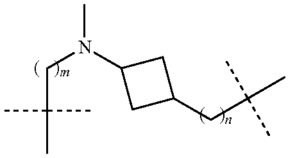
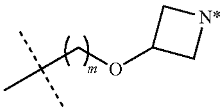
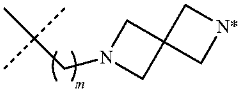
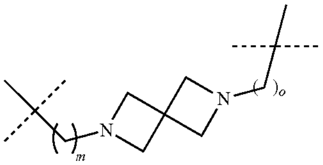
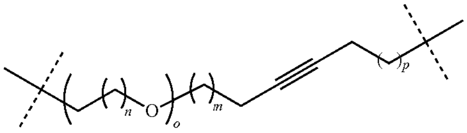
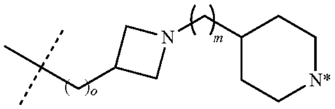
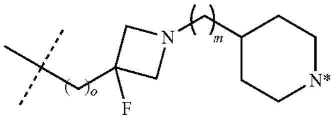
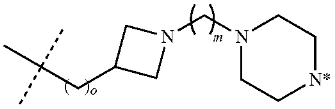
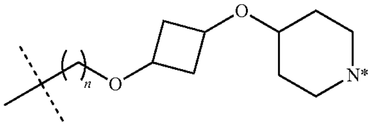
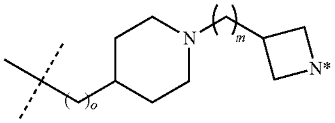
-continued
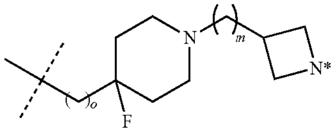
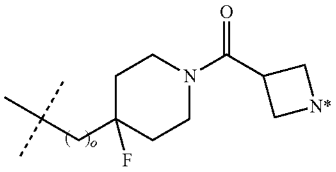
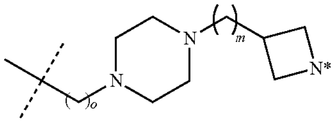
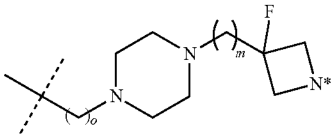
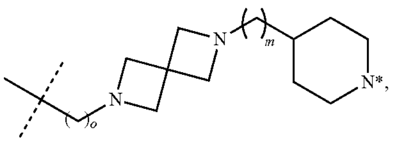
wherein:
the chemical linker group is optionally substituted with a halogen;
N* is a nitrogen atom that is covalently linked to or shared with the CLM or the PTM; and
each m, n, o, p, q, and r of the L is independently 0, 1, 2, 3, 4, 5, 6, 7, 8, 9, 10, 11, 12, 13, 14, 15, 16, 17, 18, 19, or 20.
In any aspect or embodiment described herein, one or more of:
(a) the CLM is represented by:
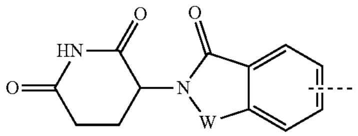
,
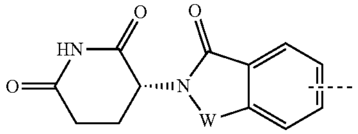
,
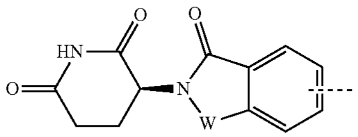
,
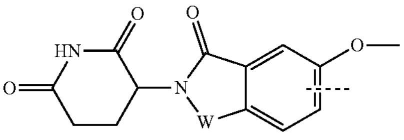
, -continued
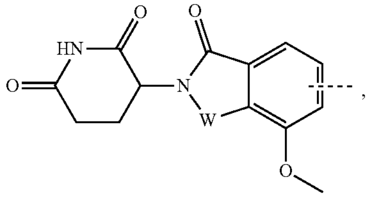
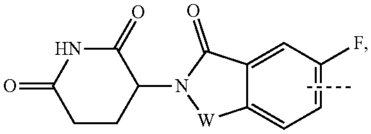
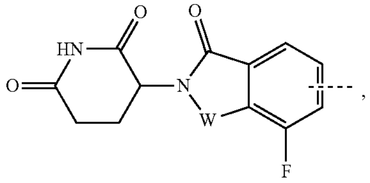
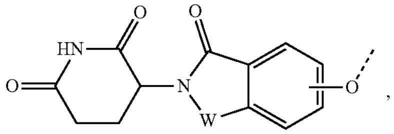
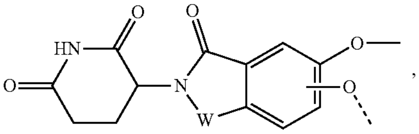
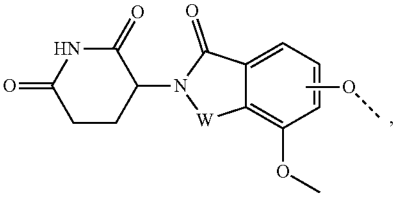
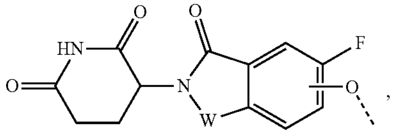
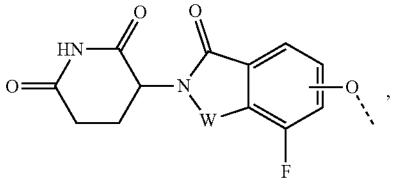
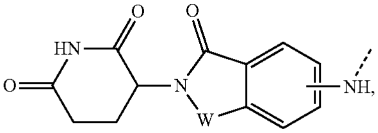
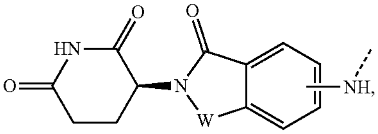
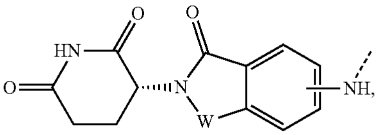
-continued
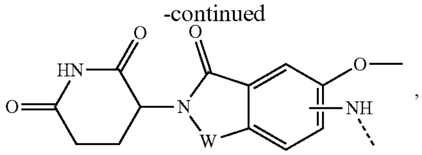
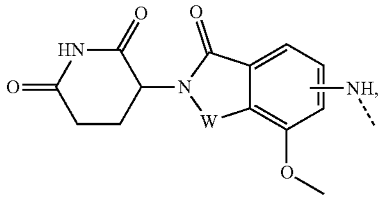
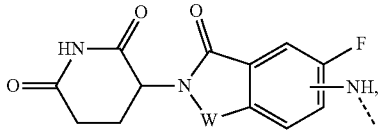
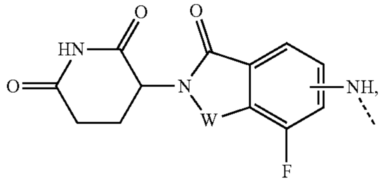
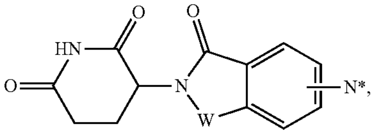
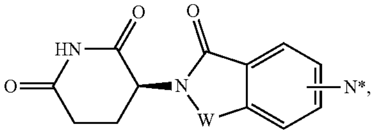
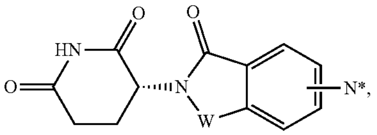
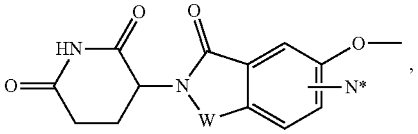
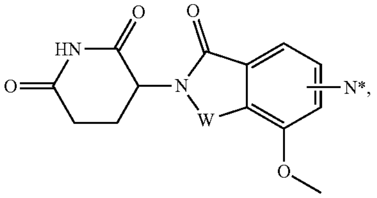
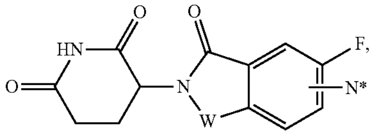
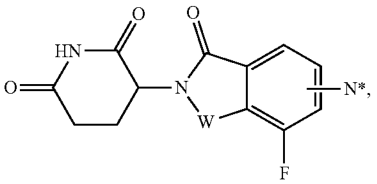

-continued
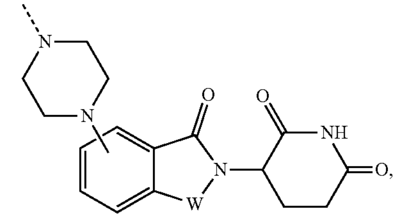
or
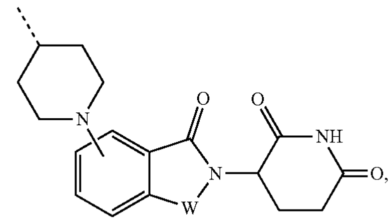
of the ULM indicates the point of attachment with the L; and
N* is a nitrogen atom that is shared with the L;
(b) the PTM is represented by:
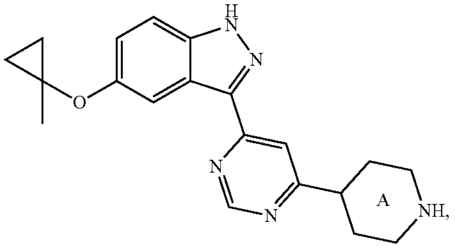
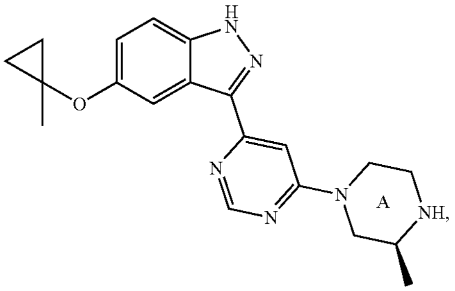
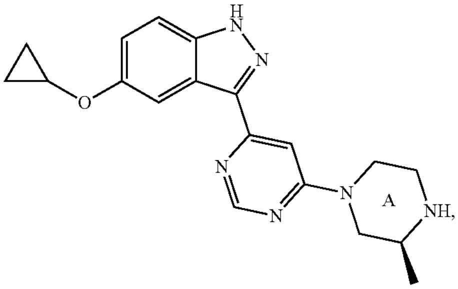
-continued
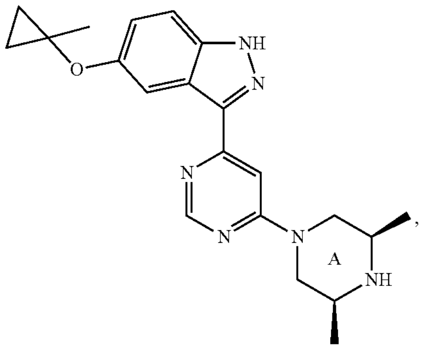
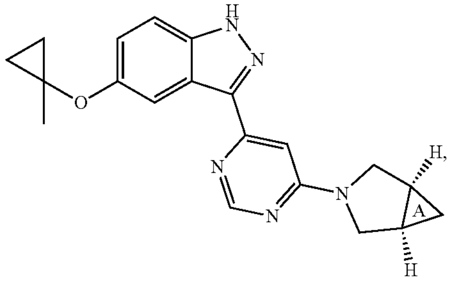
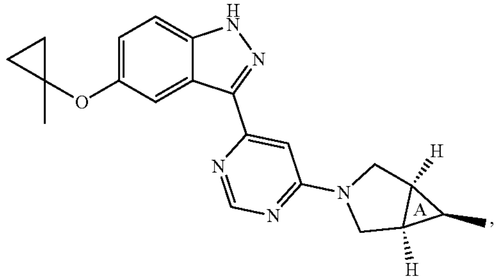
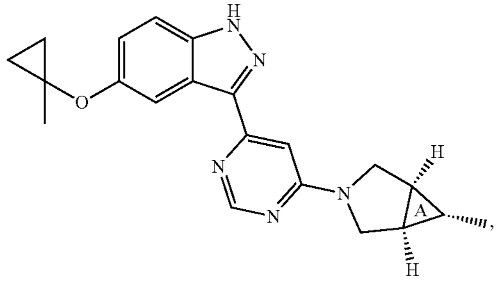
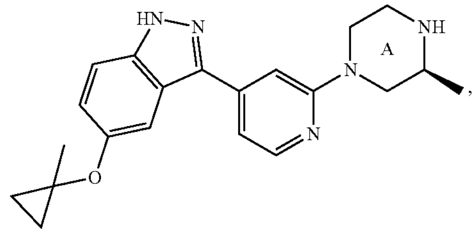
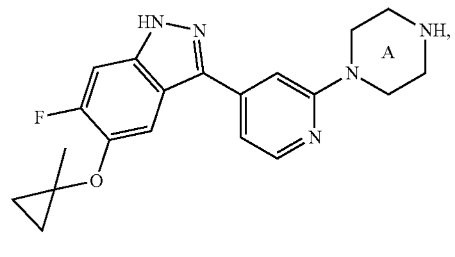

-continued
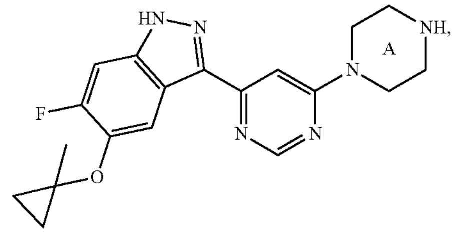
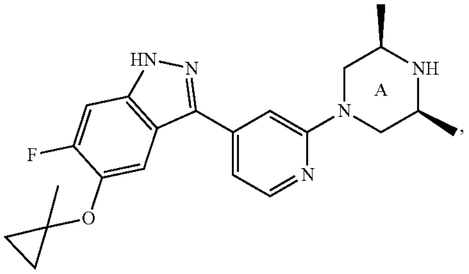
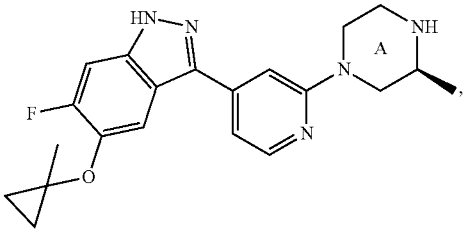
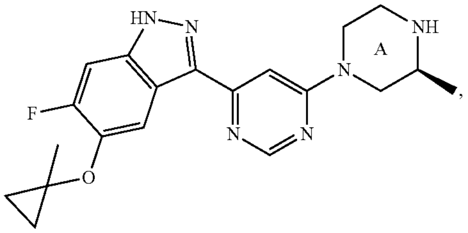
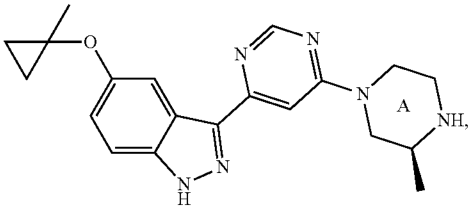
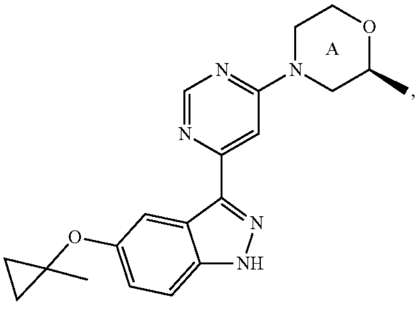
-continued
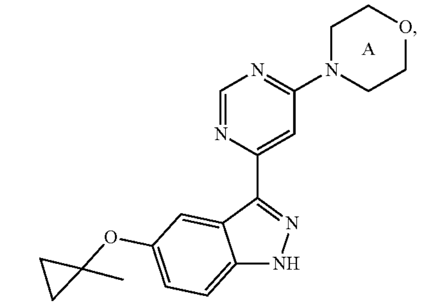
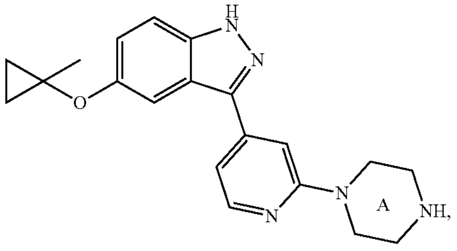
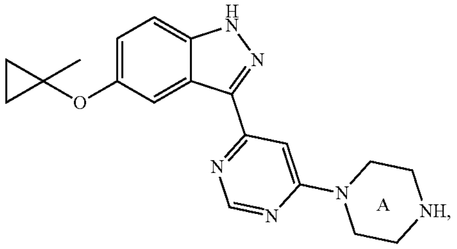
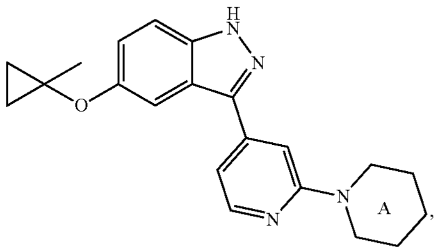
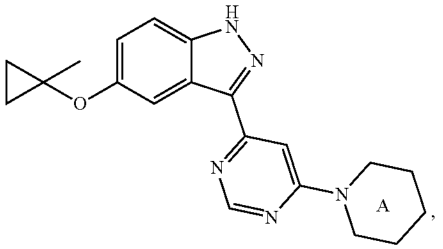
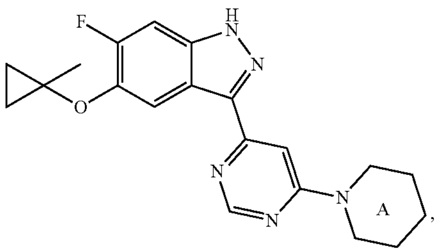

-continued
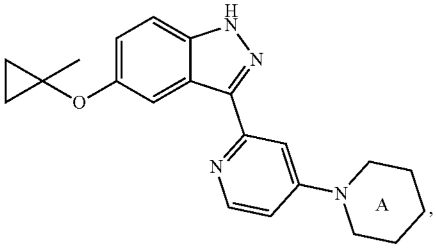
,
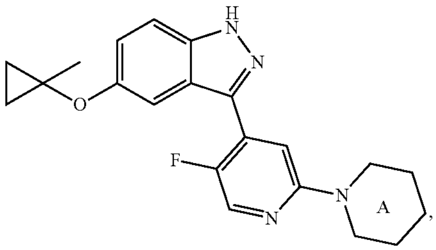
,
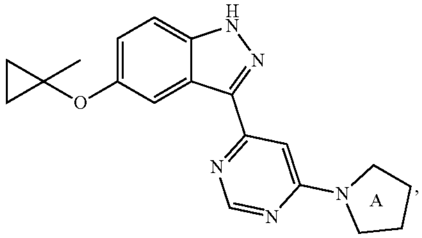
,
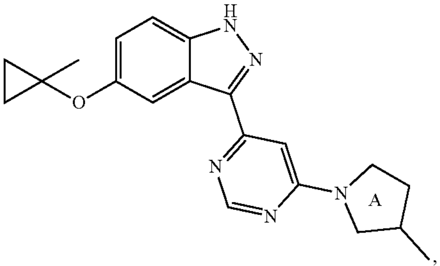
,
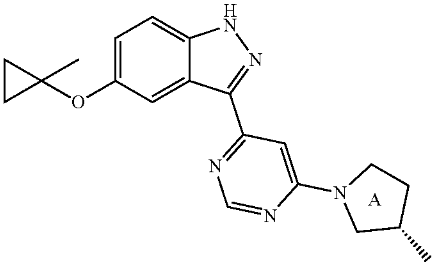
,
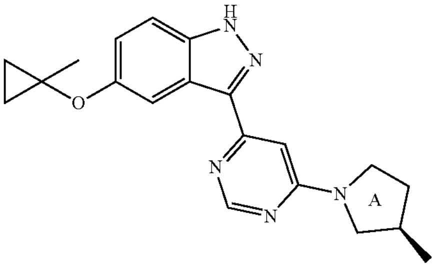
,
-continued
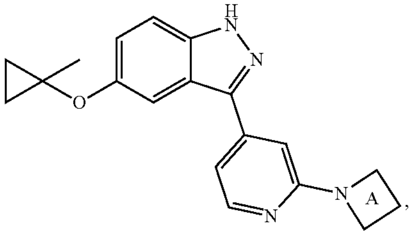
,
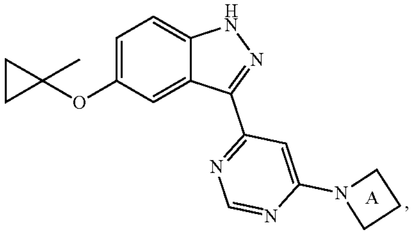
,
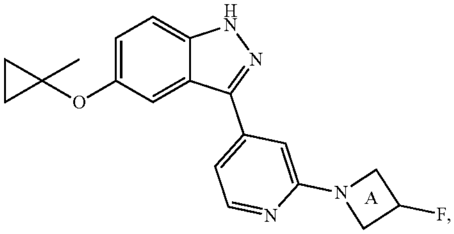
,
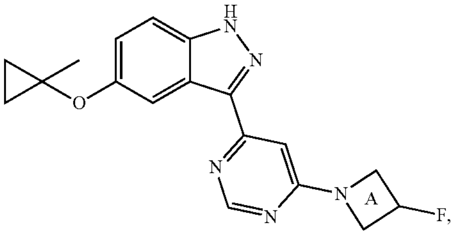
,
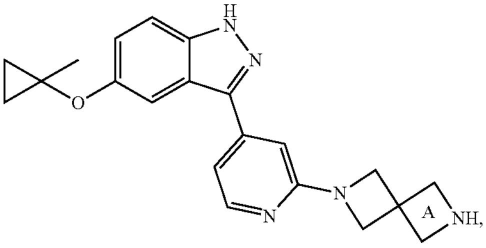
,
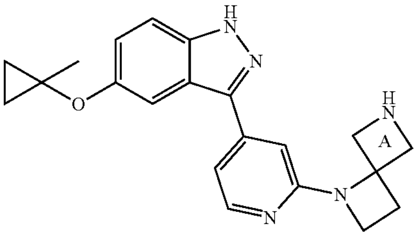
,
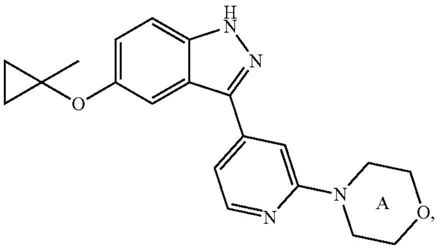
, -continued
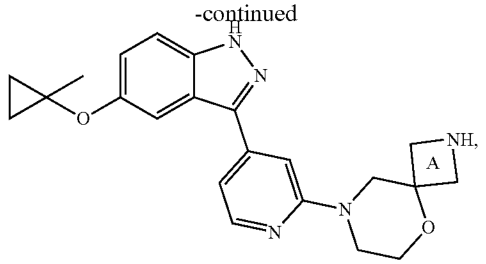
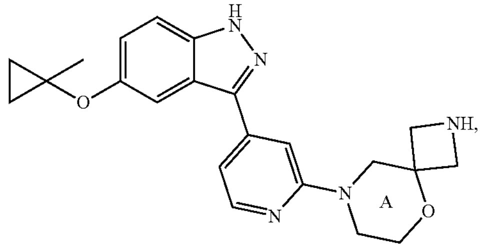
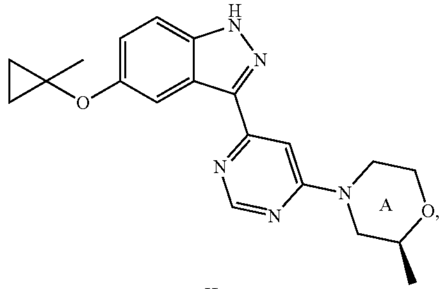
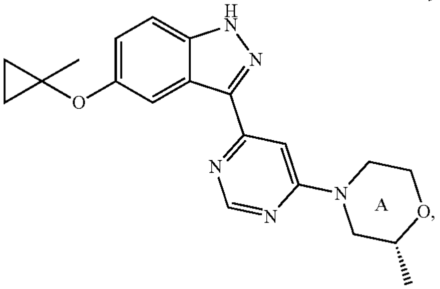
and
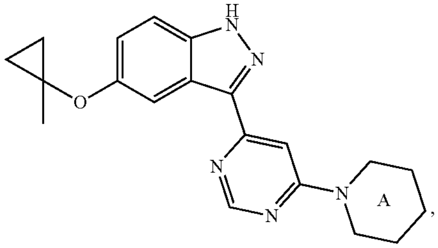
wherein the PTM is covalently linked to the L via an atom of heterocyloalkyl A or a substituent thereof;
(c) the L is a linker group (L) selected from:
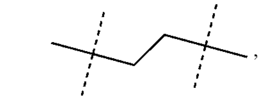
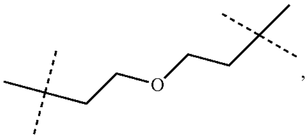
-continued
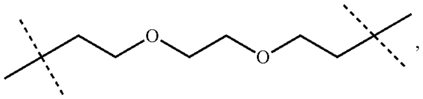
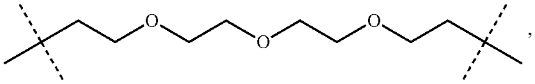
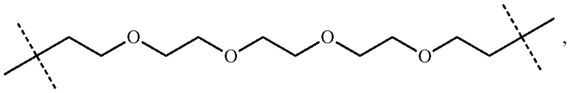
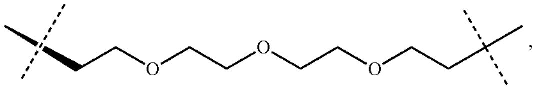
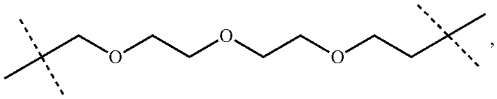
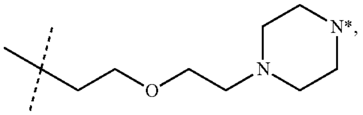
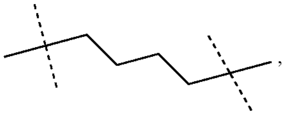
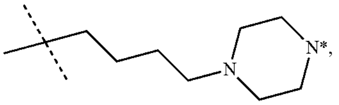
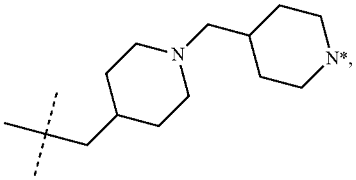
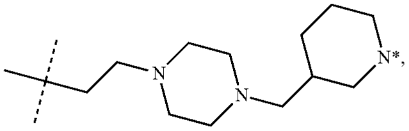
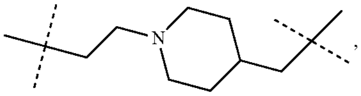
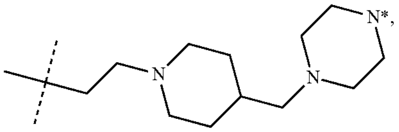
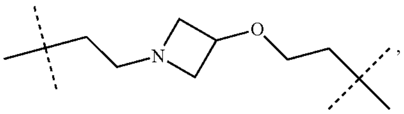
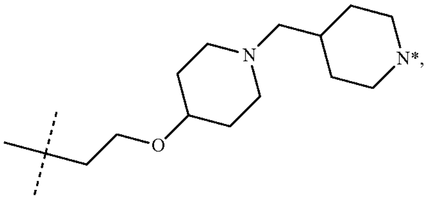

-continued
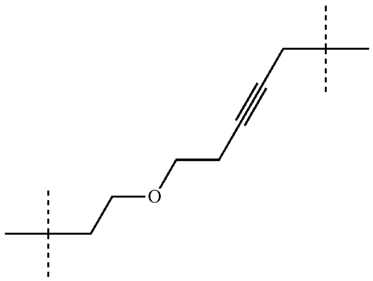
,
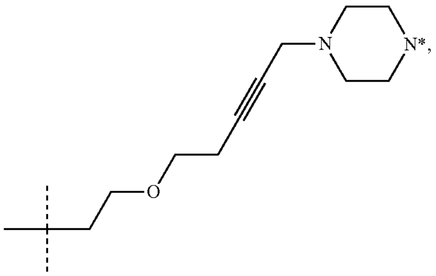
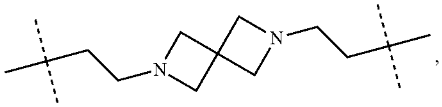
,
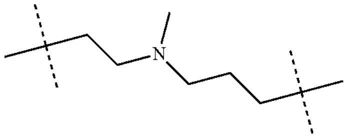
,
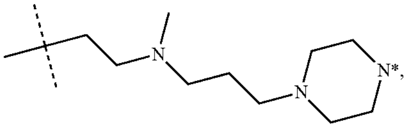
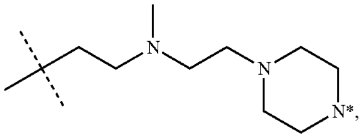
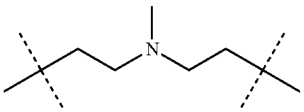
,
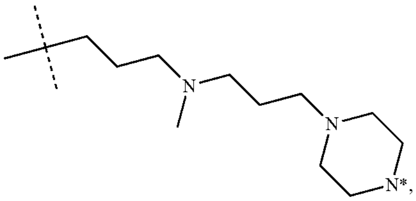
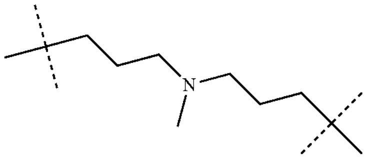
,
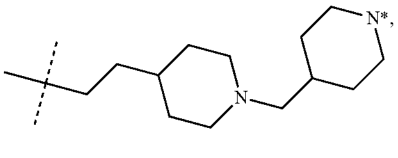
-continued
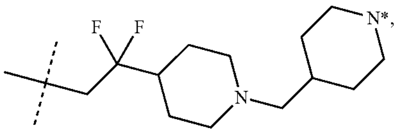
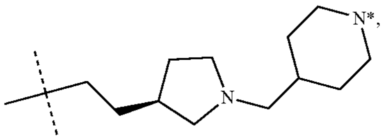
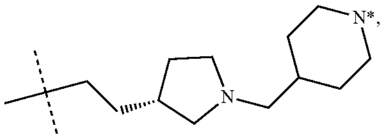
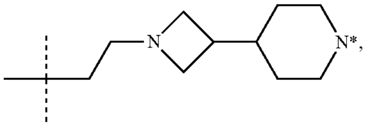
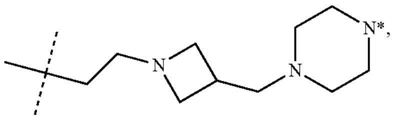
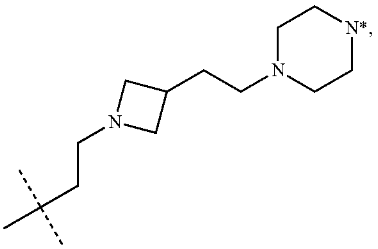
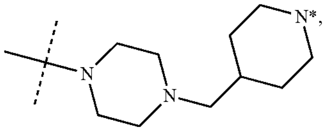
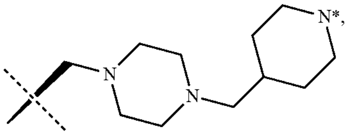
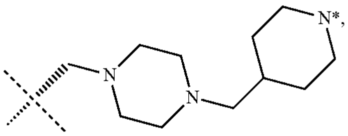
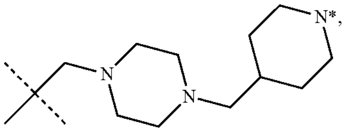
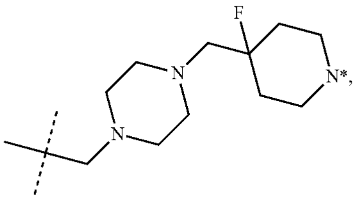

-continued
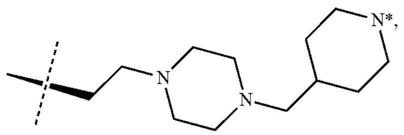
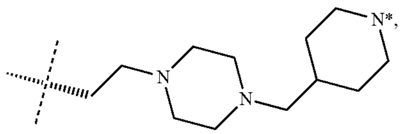
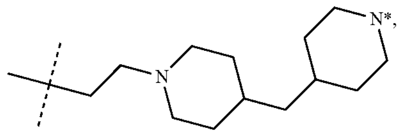
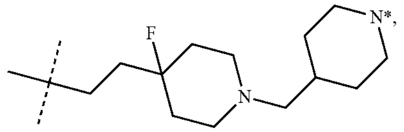
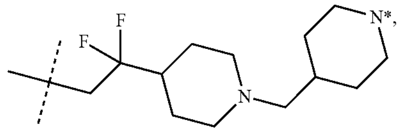
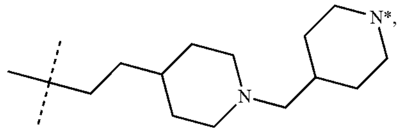
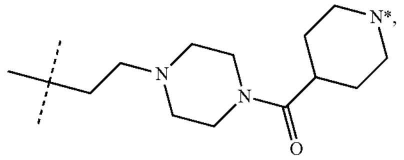
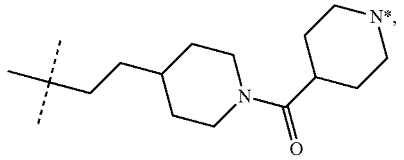
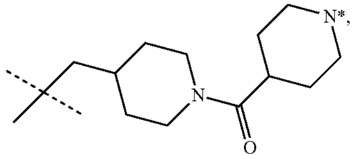
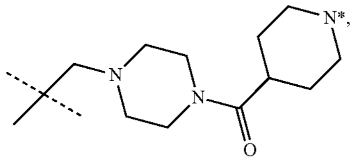
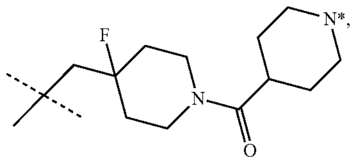
-continued
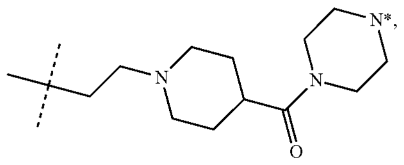
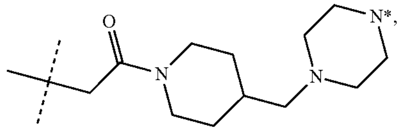
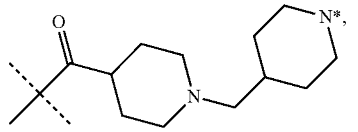
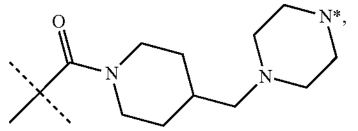
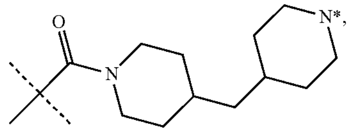
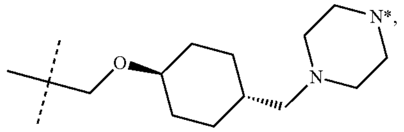
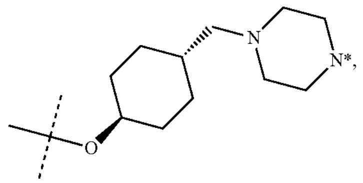
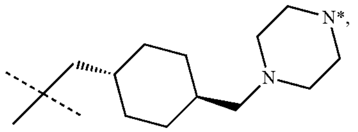
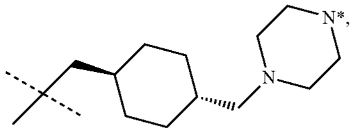
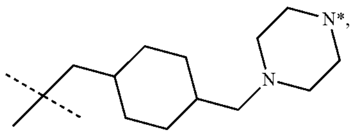
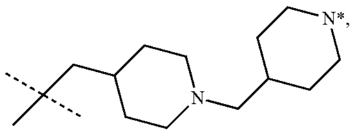
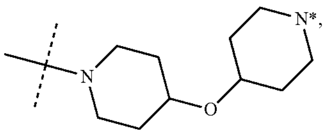

-continued
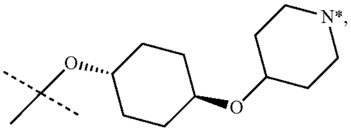
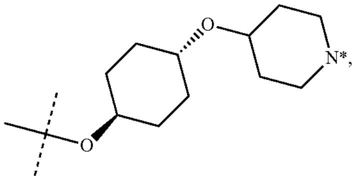
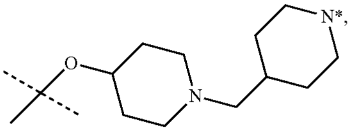
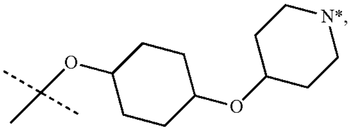
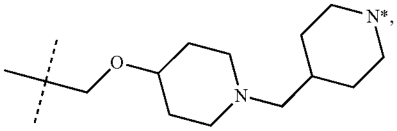
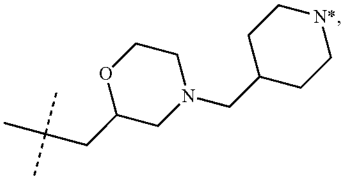
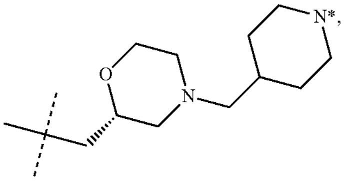
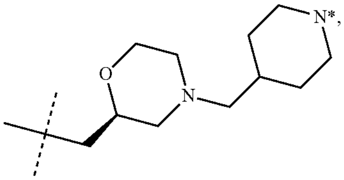
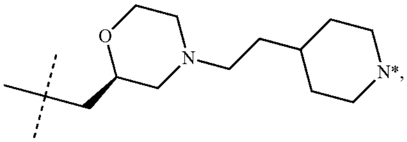
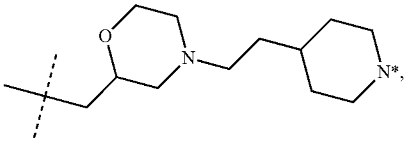
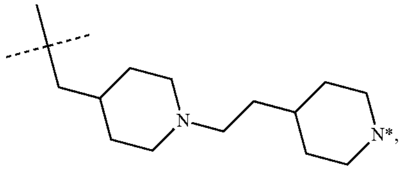
-continued
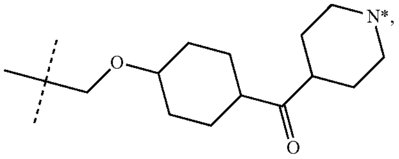
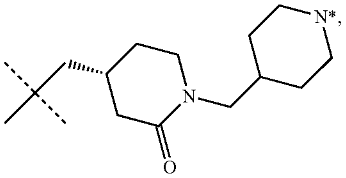
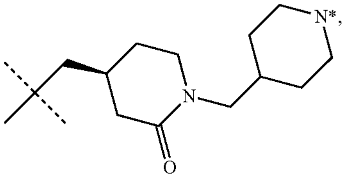
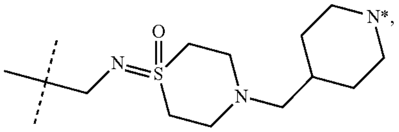
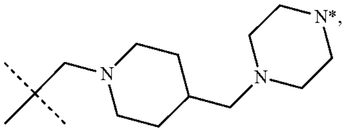
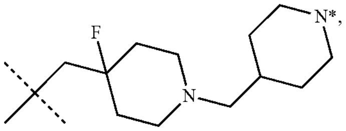
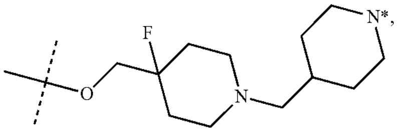
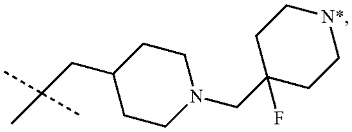
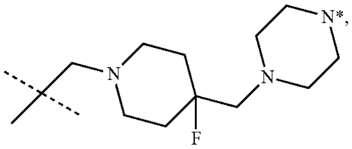
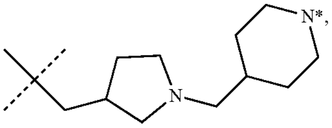
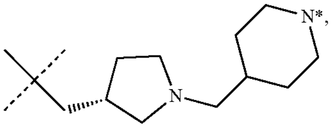
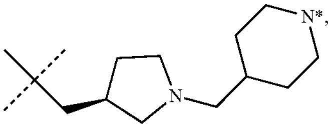

-continued
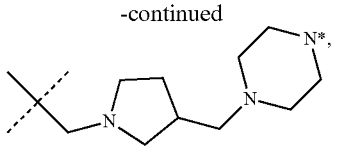
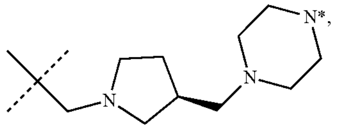
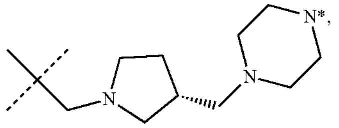
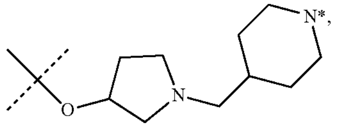
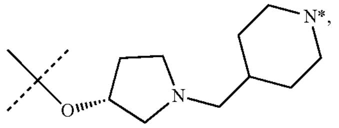
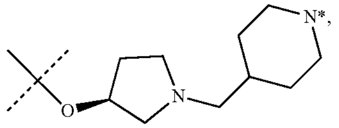
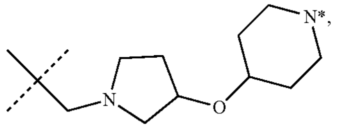
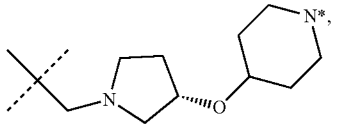
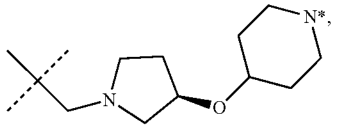
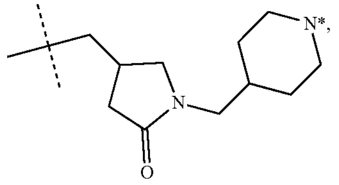
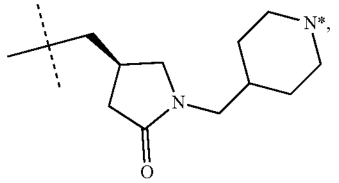
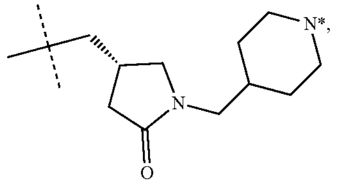
-continued
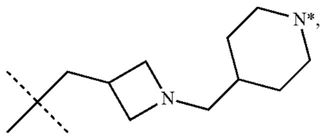
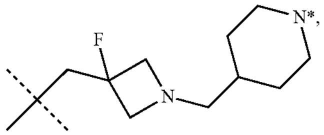
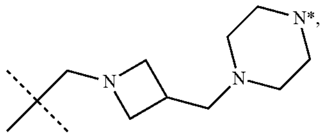
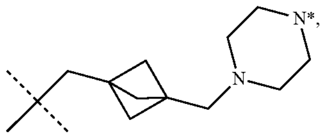
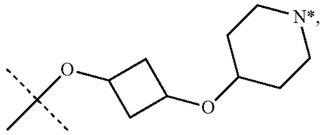
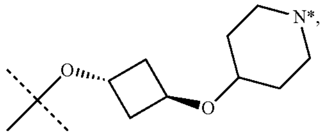
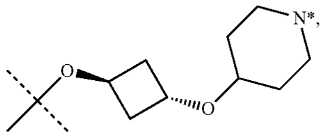
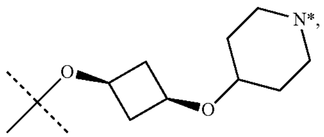
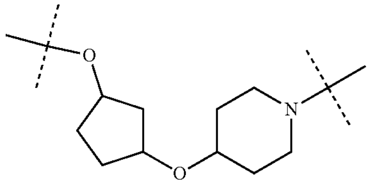
,
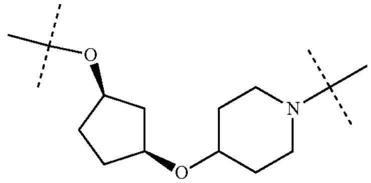
,
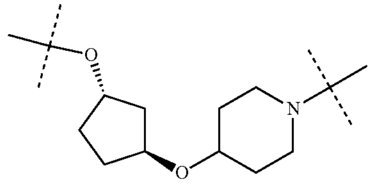
, -continued
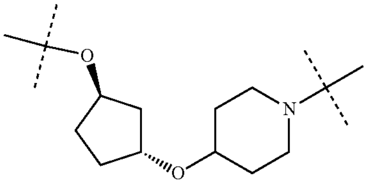,
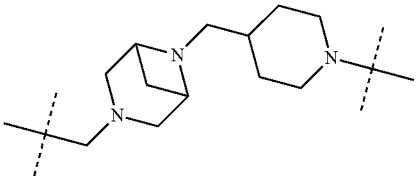,
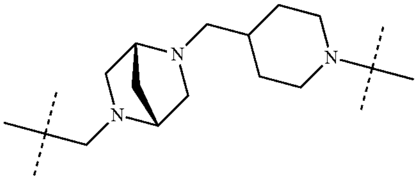,
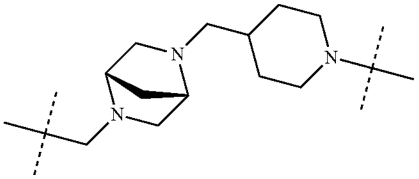,
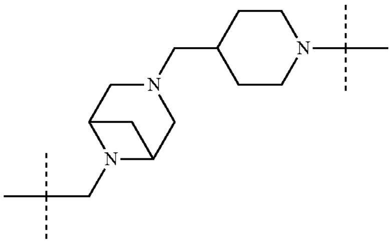,
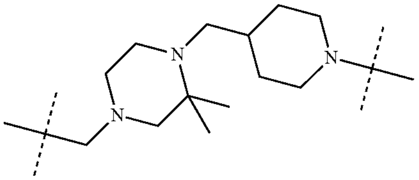,
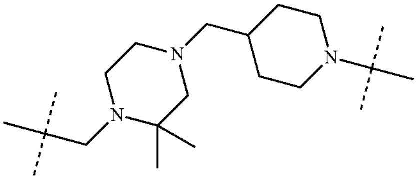,
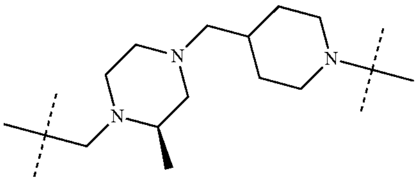,
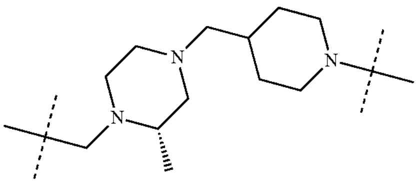,
-continued
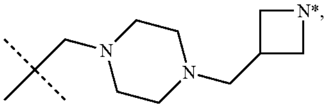,
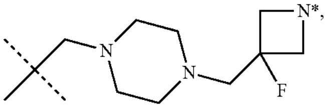,
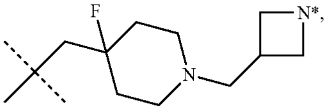,
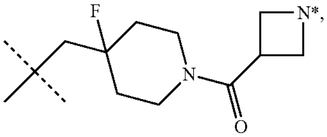,
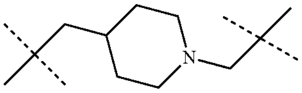,
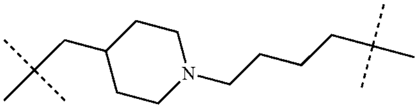,
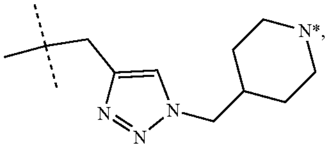,
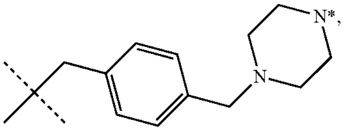,
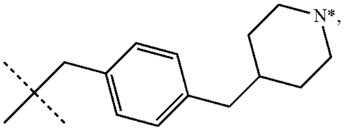,
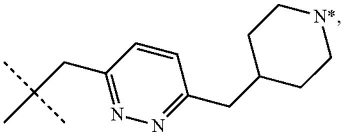,
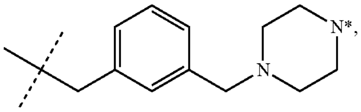,
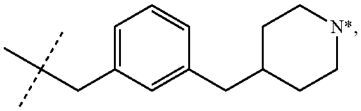,
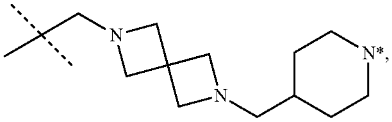, and
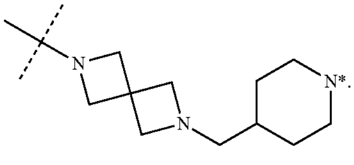.

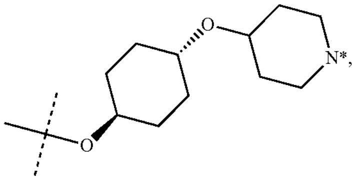
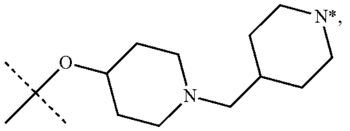
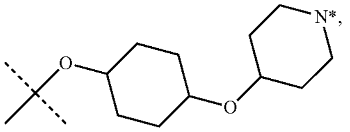
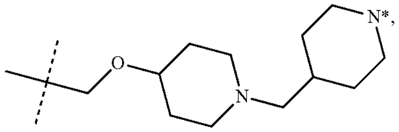
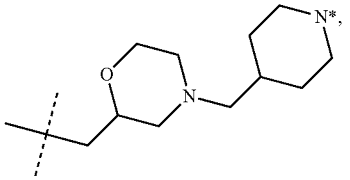
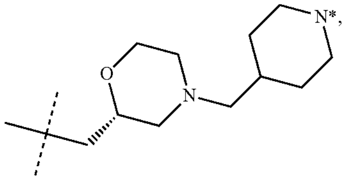
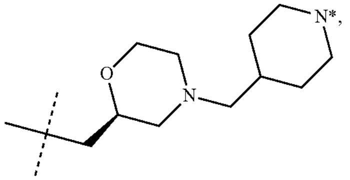
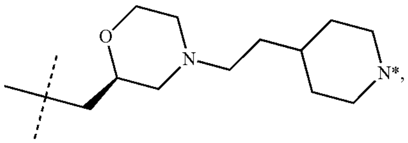
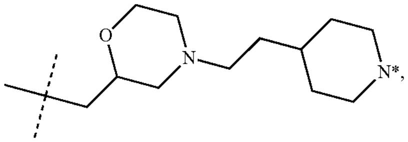
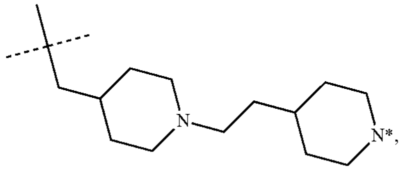
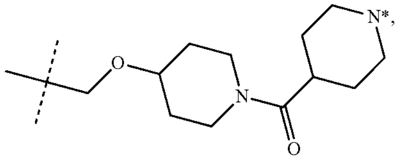
-continued
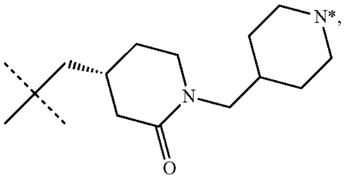
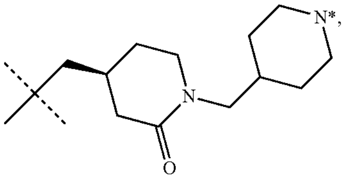
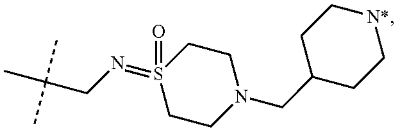
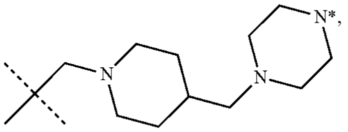
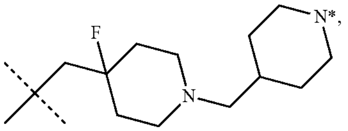
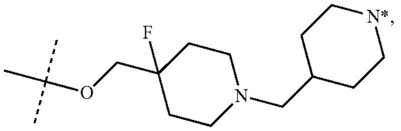
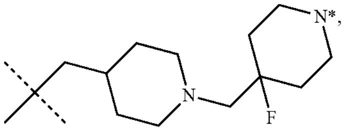
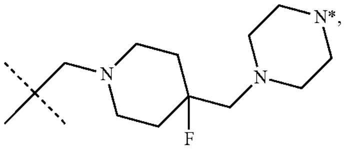
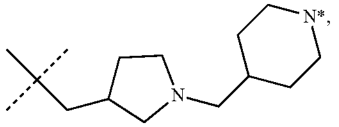
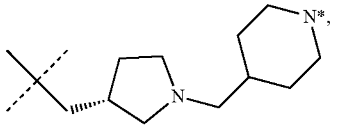
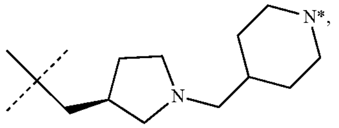
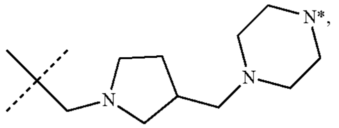

-continued
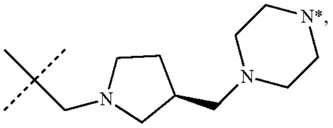
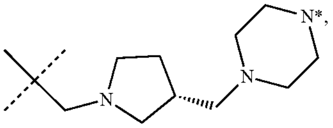
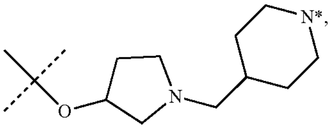
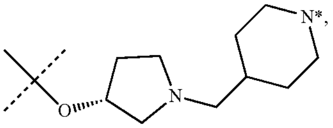
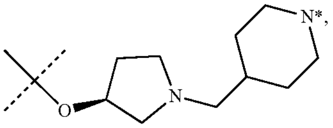
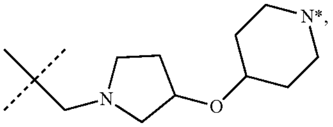
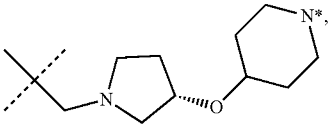
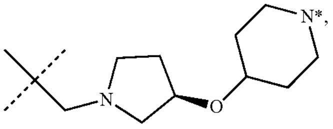
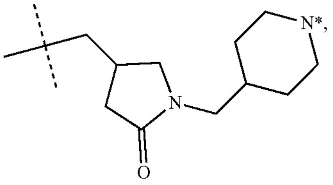
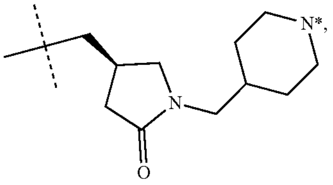
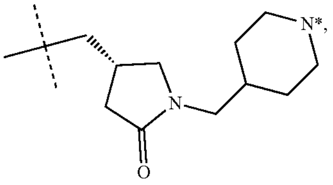
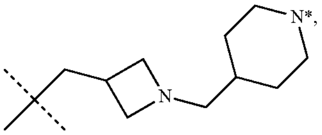
-continued
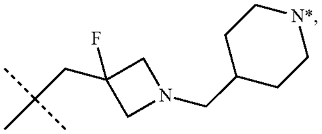
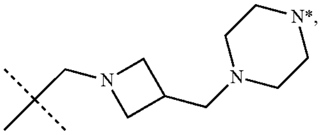
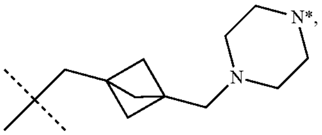
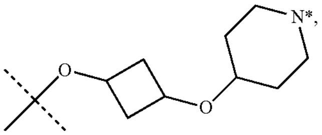
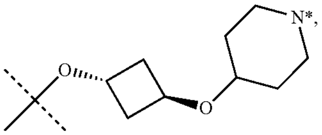
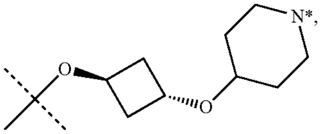
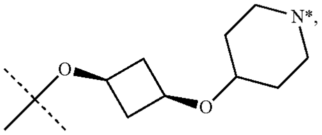
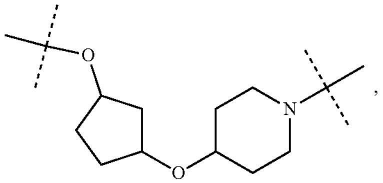
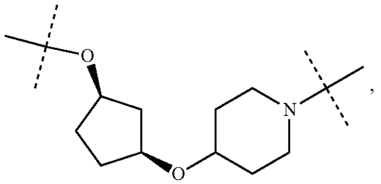
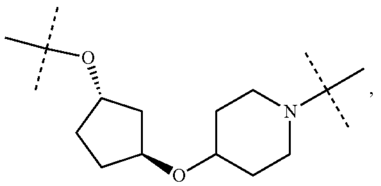
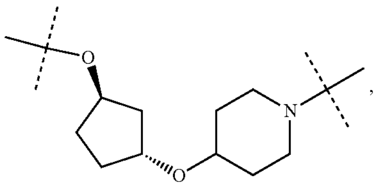

-continued
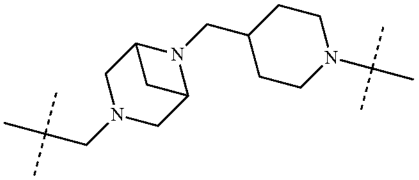,
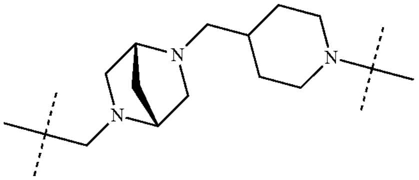,
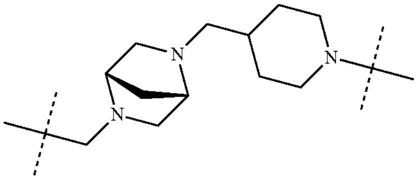,
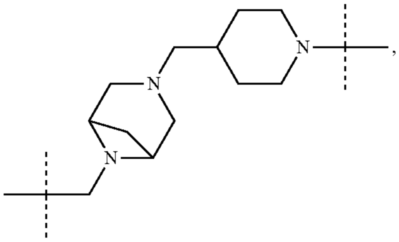,
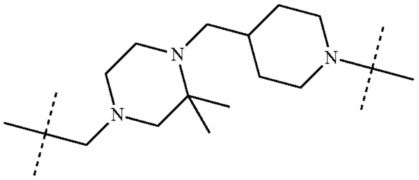,
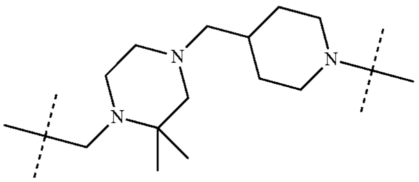,
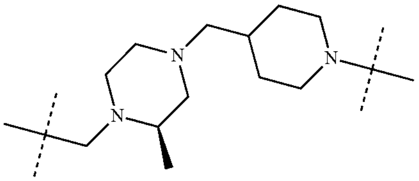,
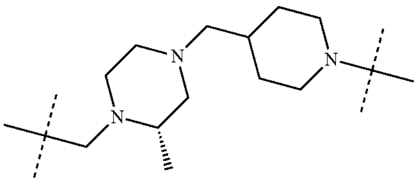,
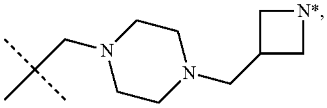,
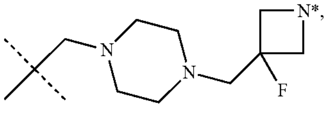
-continued
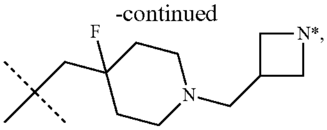,
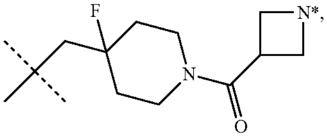,
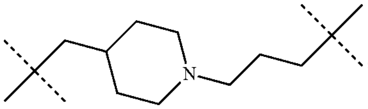,
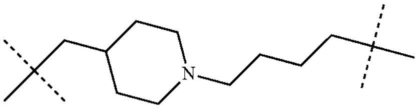,
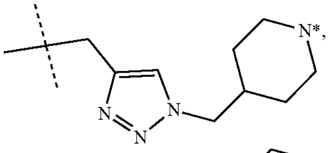,
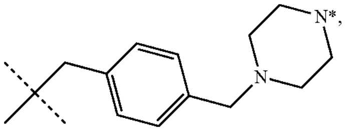,
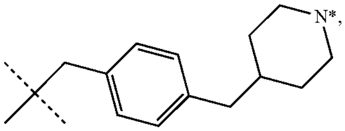,
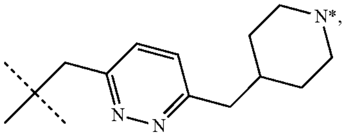,
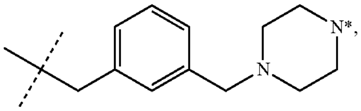,
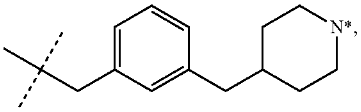,
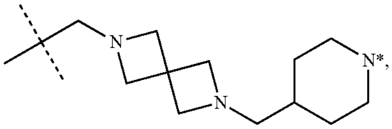, and
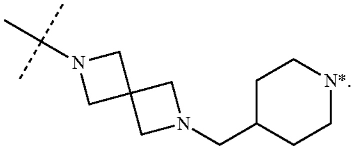.
wherein:
N* is a nitrogen atom that is covalently linked to or shared with the CLM or the PTM; and
 and  represented the point of attachment to the CLM or the PTM; or
(d) a combination thereof.

In any aspect or embodiment described herein, one or more of the PTM is a PTM selected from compounds 52-288, the CLM is a CLM selected from compounds 52-288, and the L is an L selected from compounds 52-288.

In any aspect or embodiment described herein, one or more of:

G is H or unsubstituted or substituted linear or branched $C_{1-6}$ alkyl;

A is H or unsubstituted or substituted linear or branched $C_{1-6}$ alkyl;

R is a bond, H, O, —CONR'R", —C(=O)R', —OR', —NR'R", unsubstituted or substituted linear or branched $C_{1-6}$ alkyl optionally substituted $C_{1-6}$ alkoxyl group, —Cl, —F, —Br, —$CF_3$, or —CN, wherein one R is covalently joined to the L;

R' and R" are independently selected from a bond, H, and optionally $C_{1-6}$ substituted alkyl; and

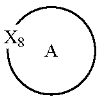, 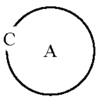, or 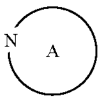

is an optionally substituted 3-10 membered cycloalkyl, optionally substituted 3-10 membered heterocyloalkyl containing 1 to 4 (e.g., 1, 2, 3, or 4) heteroatoms, optionally substituted 3-10 membered bicycloalkyl, optionally substituted 3-10 membered biheterocycloalkyl containing 1 to 4 (e.g., 1, 2, 3, or 4) heteroatoms, optionally substituted 3-10 membered spirocycloalkyl, or optionally substituted 3-10 membered spiroheterocycloalkyl containing 1 to 4 (e.g., 1, 2, 3, or 4) heteroatoms, wherein the heteroatoms are independently selected from N, O, and S.

In any aspect or embodiment described herein, the PTM has the chemical structure:

(PTM-IA1)

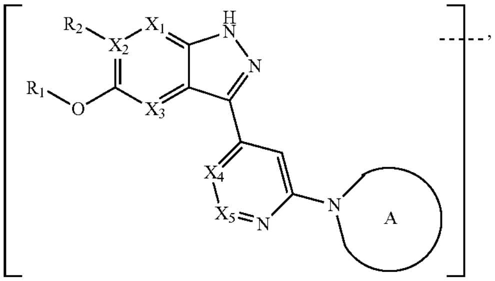

-continued (PTM-IA2)

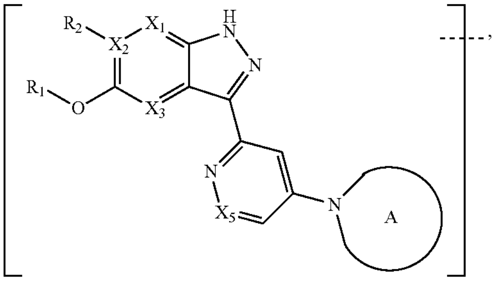

(PTM-IA1)

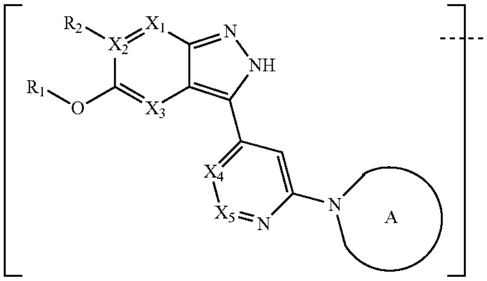

or (PTM-IA2)

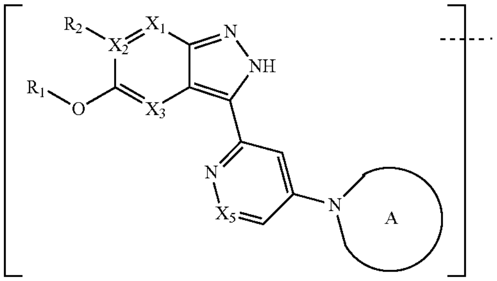

In any aspect or embodiment described herein, the compound has the chemical structure:

(Formula Ia)

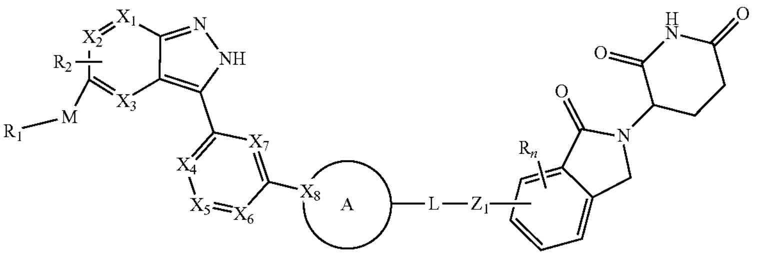
,

-continued (Formula IIIa)

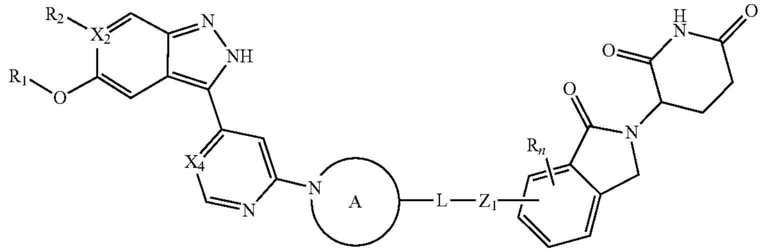

, and (Formula IIIb)

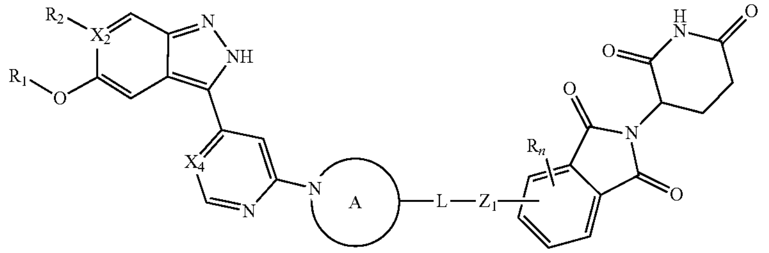

, wherein:

$X_2$ is C, CH or N;

$Z_1$ is a bond a carbon shared with a cyclic group of L, or a nitrogen shared with a cyclic group of L;

n is an integer from 0 to 3 (e.g., 0, 1, 2, or 3);

R is a bond, H, O, OH, N, NH, $NH_2$, Cl, —F, methyl, methoxy, or ethoxy; and $R^2$ is H, $C_1$, F, OH, C1-C3 alkyl, or C1-3 fluoralkyl.

In any aspect or embodiment described herein, the compound is represented by the chemical structure:

(Formula VIa)

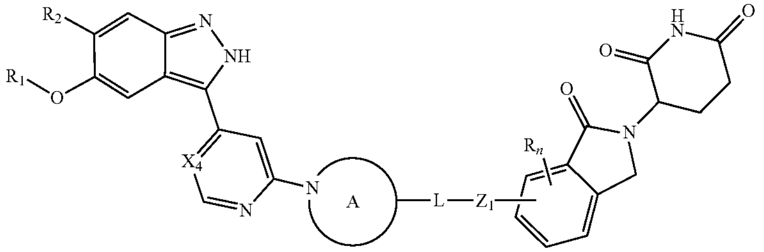

, or (Formula VIb)

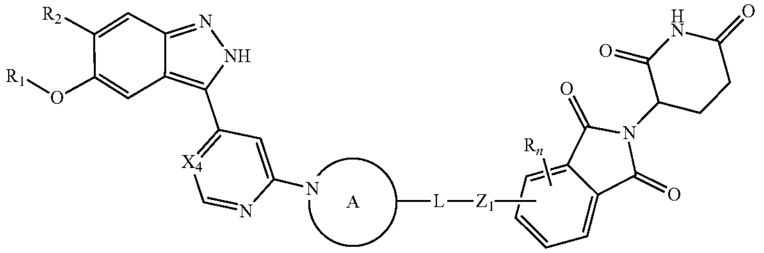

.

In any aspect or embodiment described herein, the compound is represented by the chemical structure:

(Formula VId)

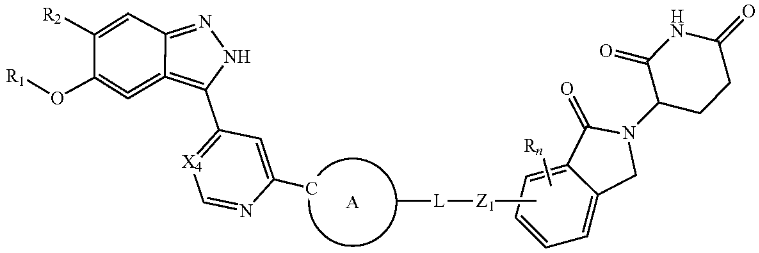

, or (Formula VIe)

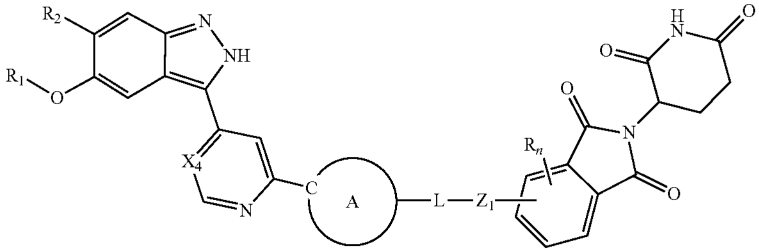

.

In any aspect or embodiment described herein, one or more of:

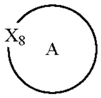

or

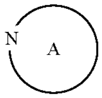

is

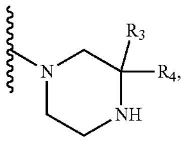

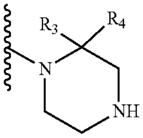

,

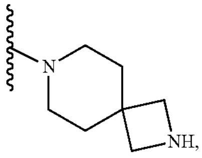

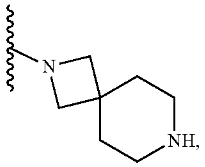

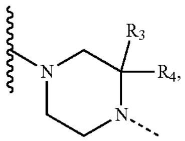

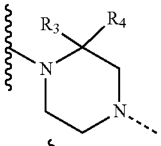

,

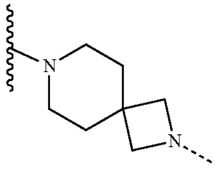

, or

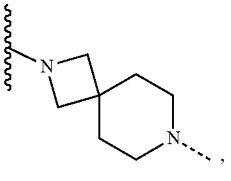

, wherein:

$R_3$ is H or methyl;

$R_{3a}$ is H, halogen, or methyl;

$R_4$ is H or methyl;

$R_5$ is H or methyl;

— indicates the point of attachment to the PTM; and indicates the point of attachment with the L, and where is not present, the

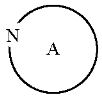

or

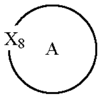

is attached to the L via an atom of a N or CH of the cyclic group, $R_3$, or $R_4$;

(b) $R_2$ is H or F; or (c) a combination thereof.

In any aspect or embodiment described herein,

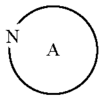

is selected from the group consisting of

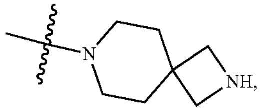

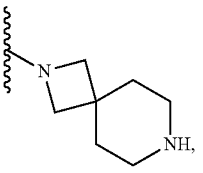

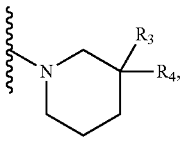

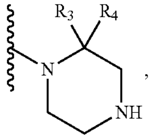

,

-continued

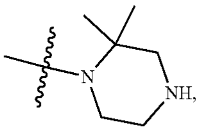

and

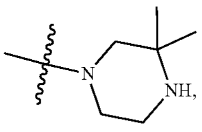

wherein the heterocycloalkyl is attached to the L or the PTM via an atom of the cyclic group or a substituent thereof.

In any aspect or embodiment described herein, the PTM is represented by chemical structure:

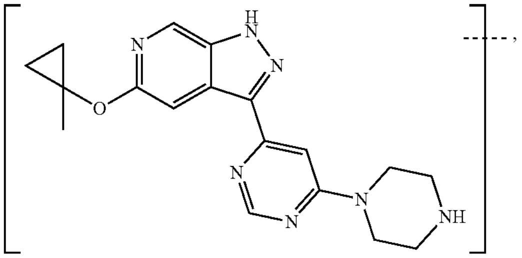

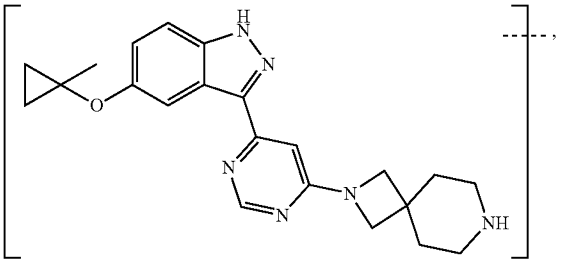

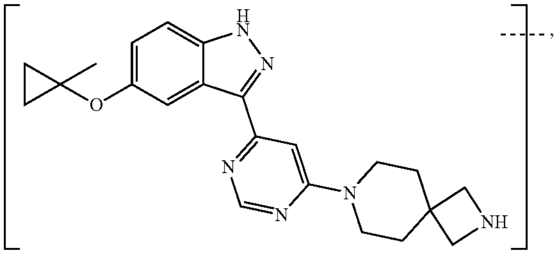

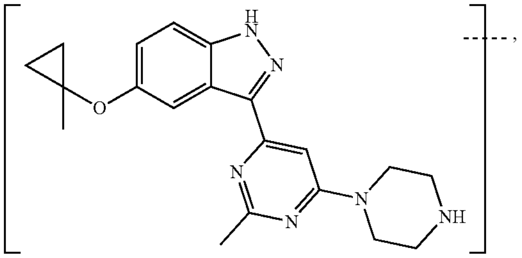

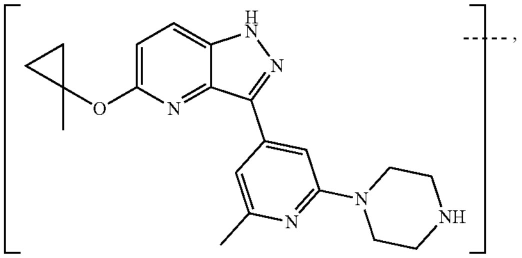

-continued

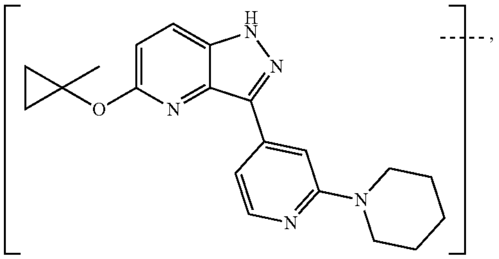

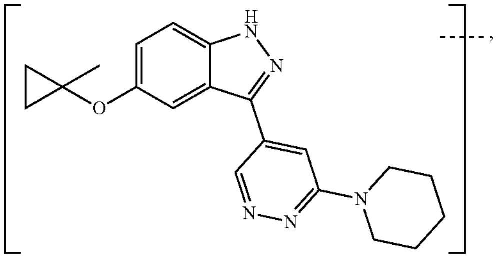

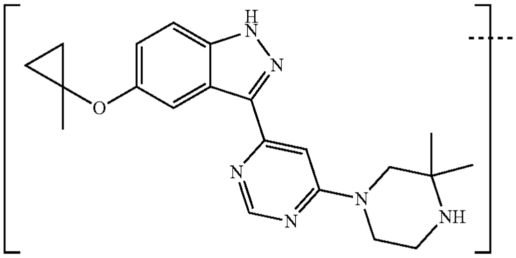

or

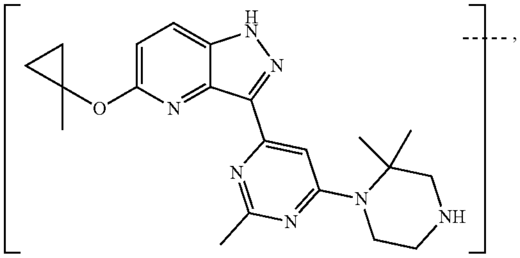

wherein  indicates a site of attachment of the L.

In any aspect or embodiment described herein, the L is selected from the group consisting of:

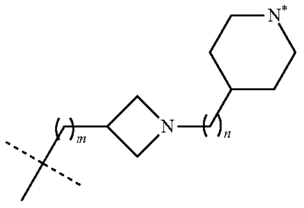

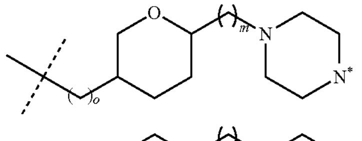

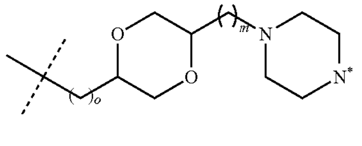

-continued

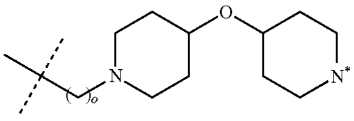

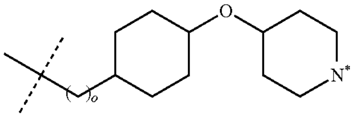

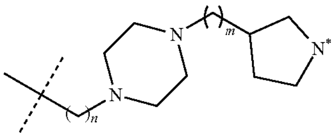

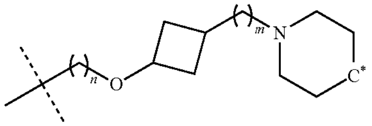

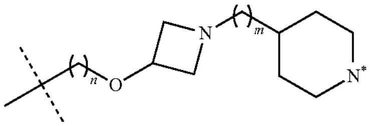

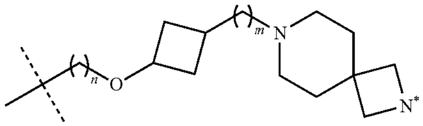

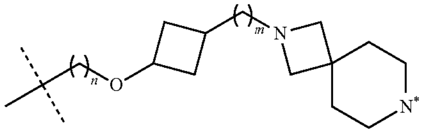

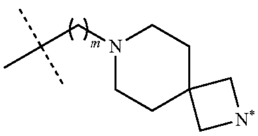

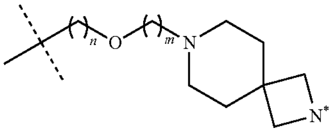

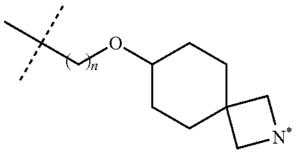

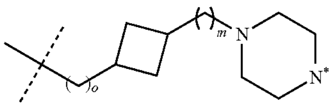

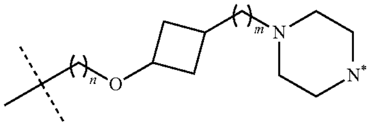

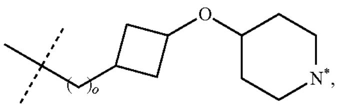

wherein:

the chemical linker group is optionally substituted with 0, 1, 2, or 3 substituents independently selected from halogen and methyl (preferably independently selected halogens);

C* is a carbon atom that is covalently linked to or shared with the CLM or the PTM;

N* is a nitrogen atom that is covalently linked to or shared with the CLM or the PTM; and each m, n, and o of the L is independently 0, 1, 2, 3, 4, 5, 6, 7, 8, 9, 10, 11, 12, 13, 14, 15, 16, 17, 18, 19, or 20.

In any aspect or embodiment described herein, one or more of:

(a) the CLM is represented by:

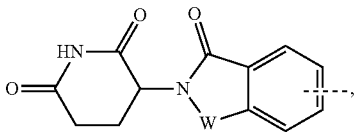

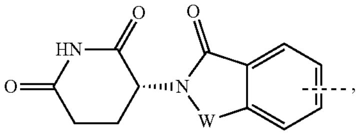

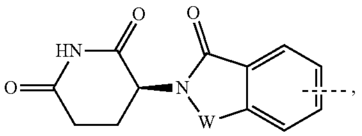

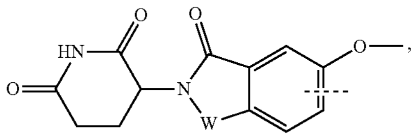

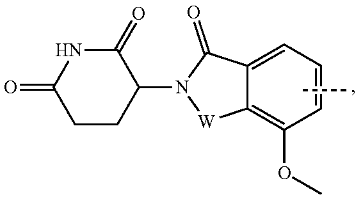

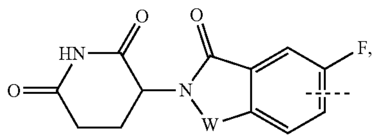

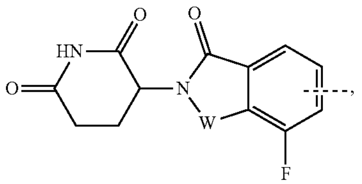

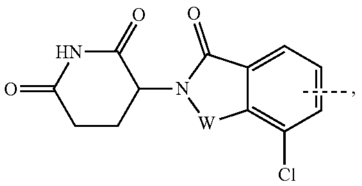

-continued
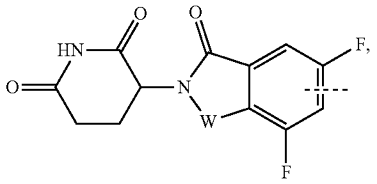
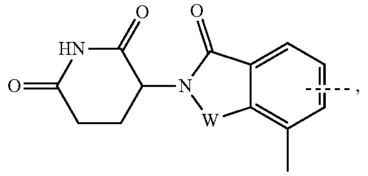
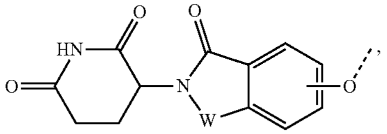
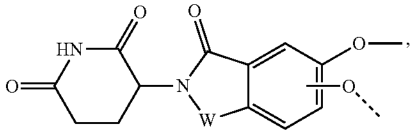
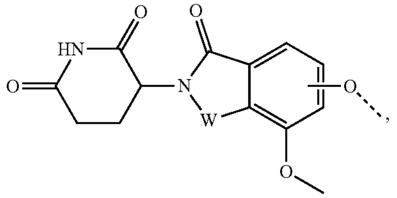
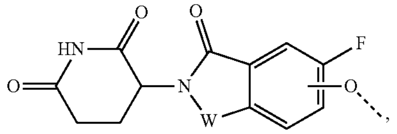
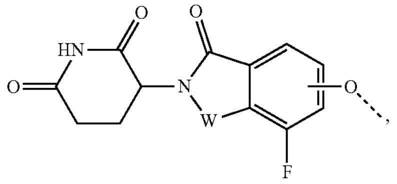
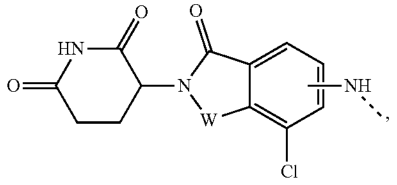
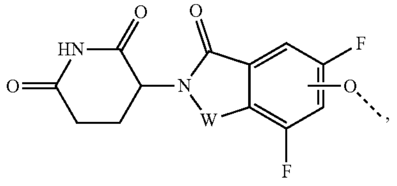
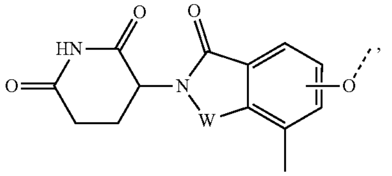
-continued
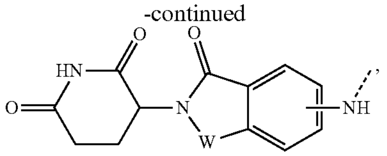
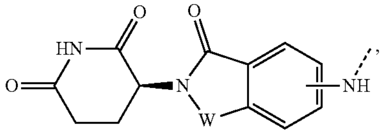
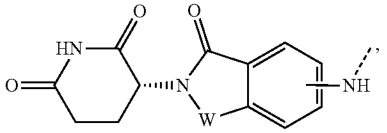
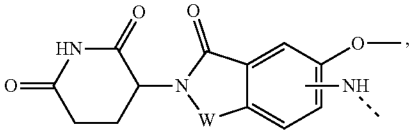
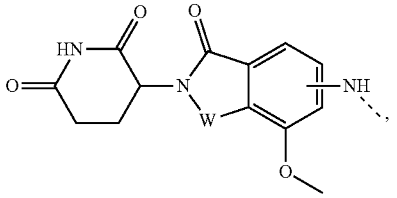
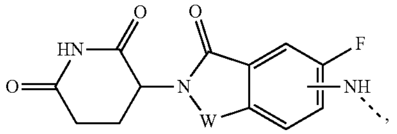
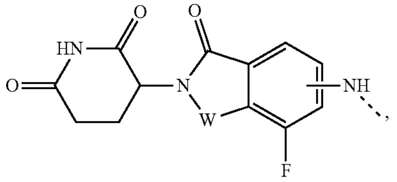
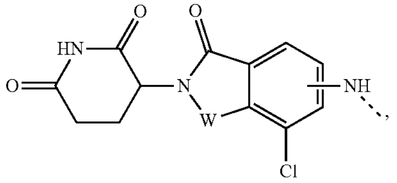
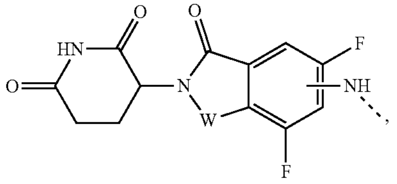
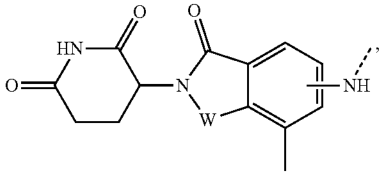
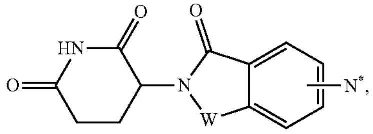

-continued
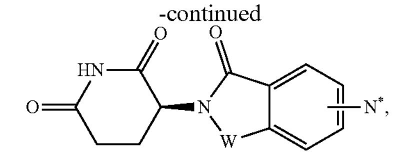
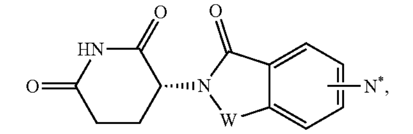
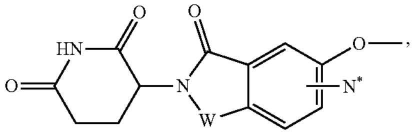
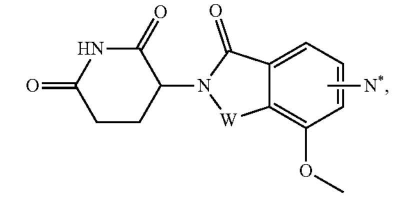
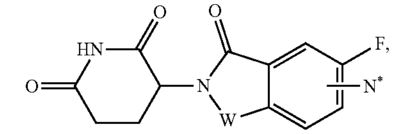
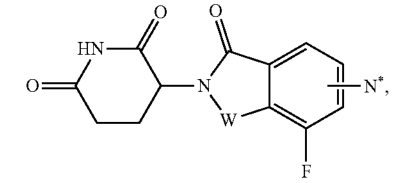
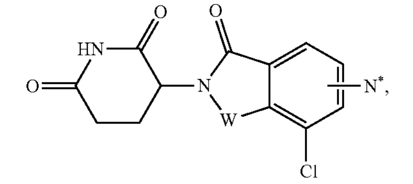
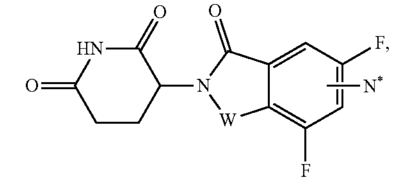
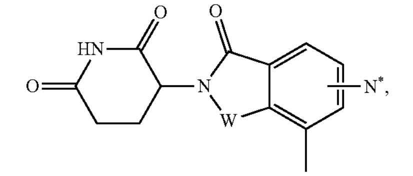
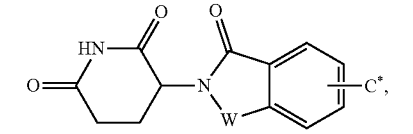
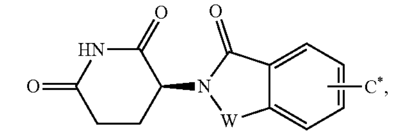
-continued
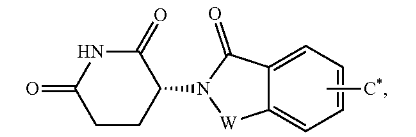
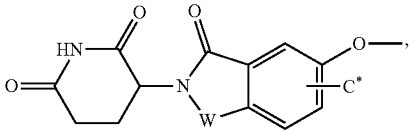
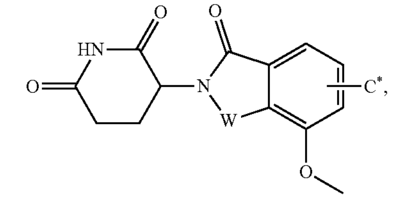
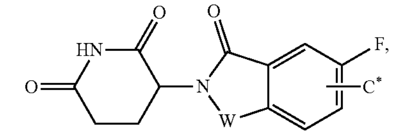
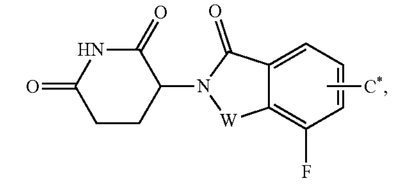
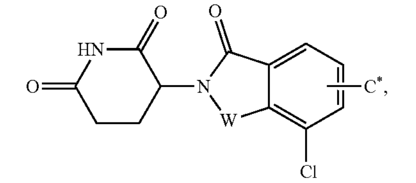
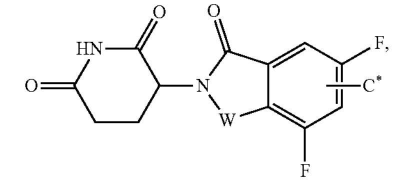
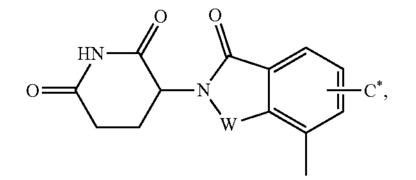
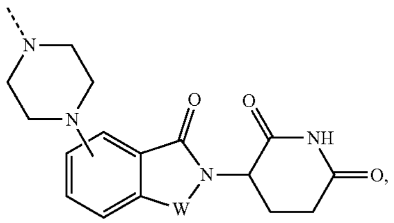 or -continued
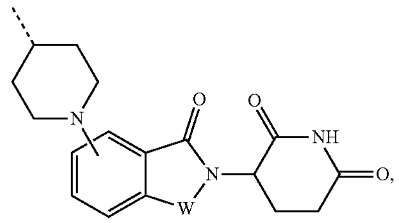
wherein
⸝⸍ of the ULM indicates the point of attachment with the L;
C* is a carbon atom that is shared with the L; and
N* is a nitrogen atom that is shared with the L;
(b) the PTM is represented by:
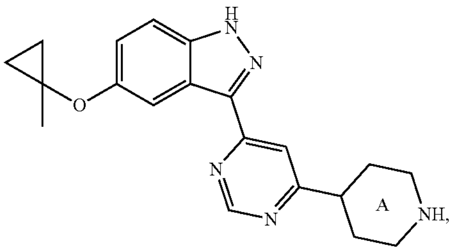
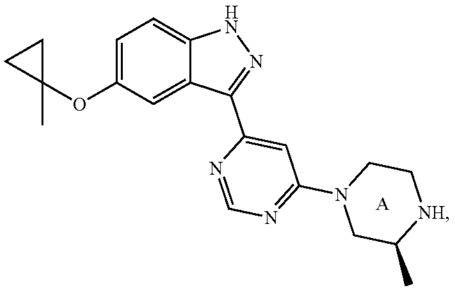
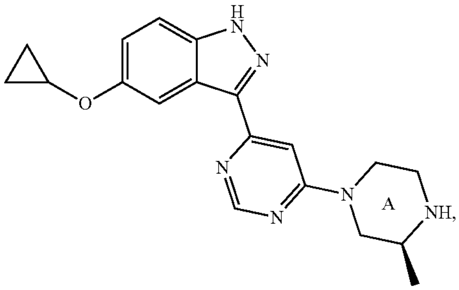
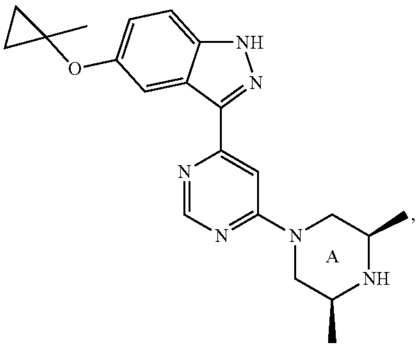
-continued
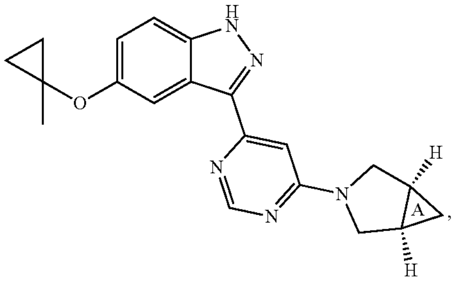
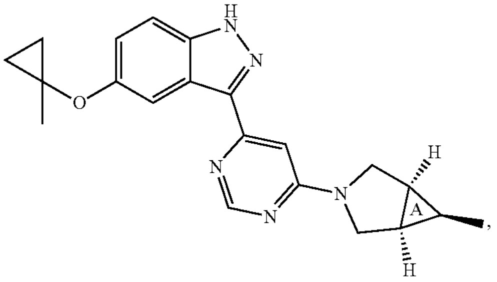
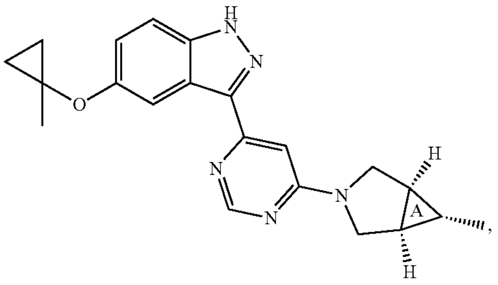
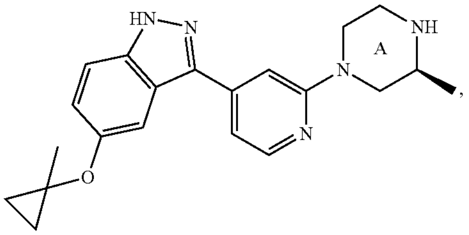
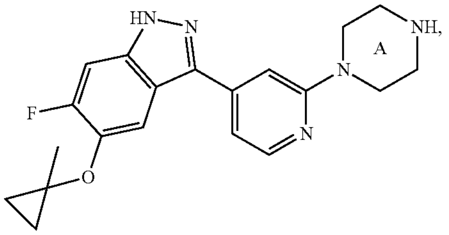
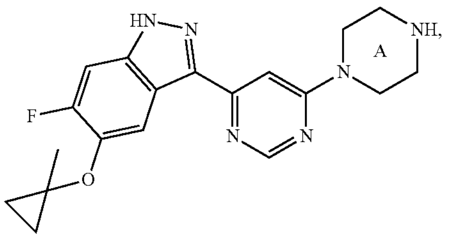

-continued
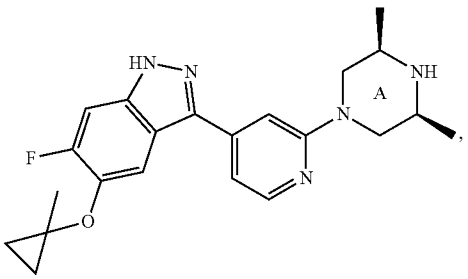
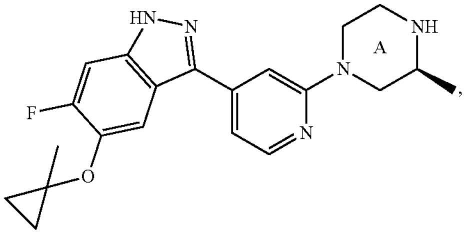
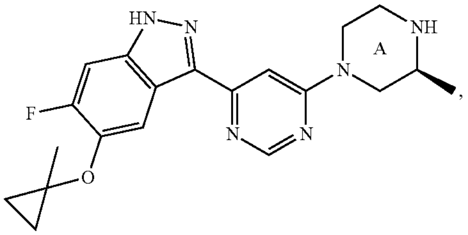
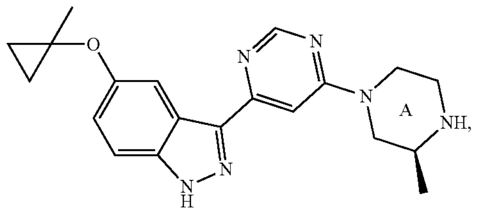
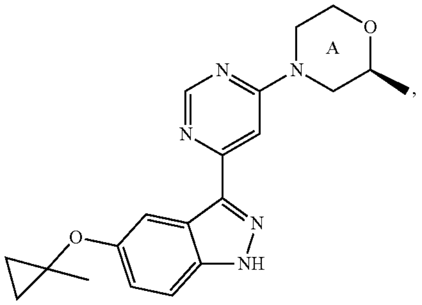
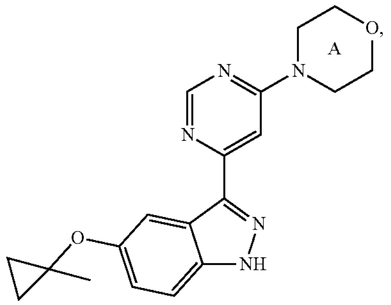
-continued
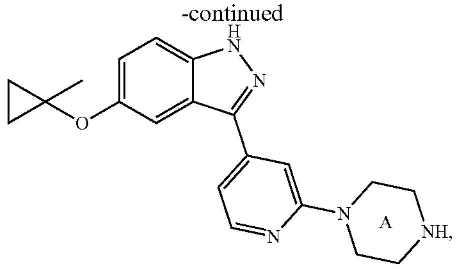
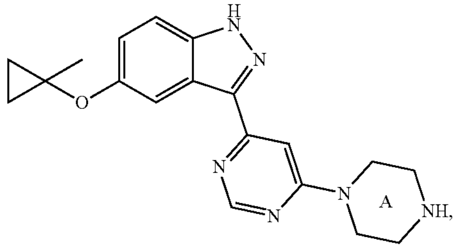
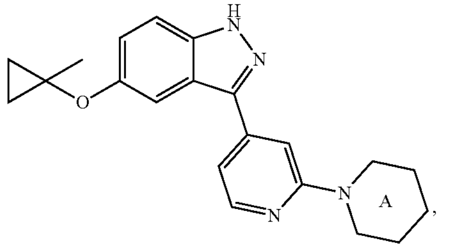
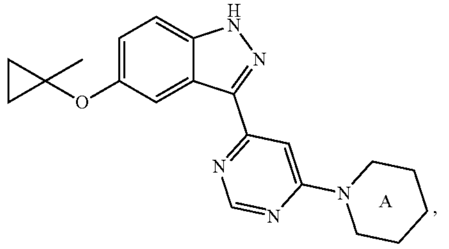
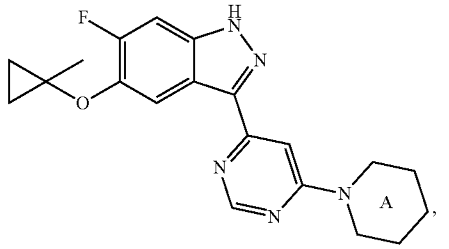
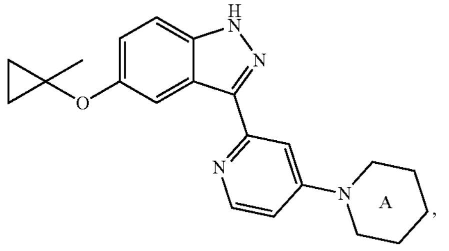
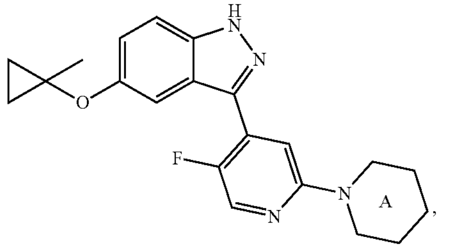

-continued
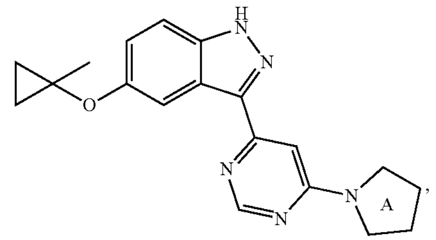
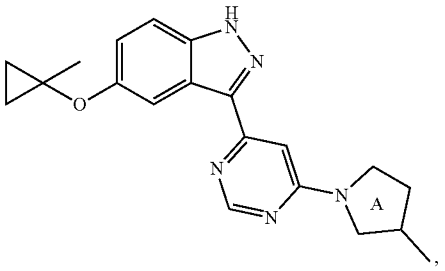
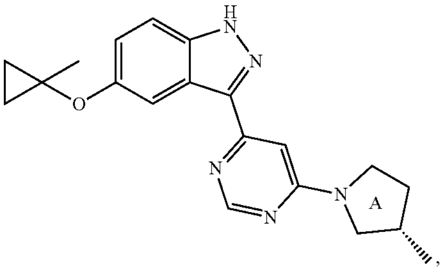
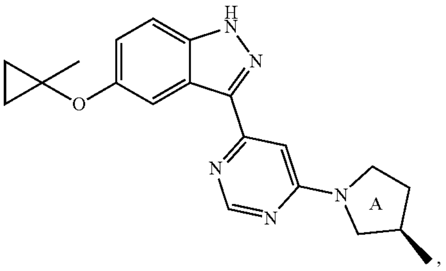
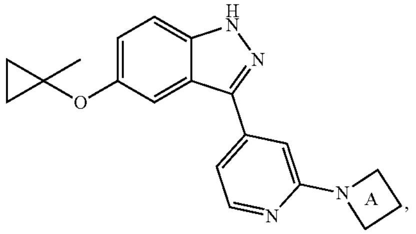
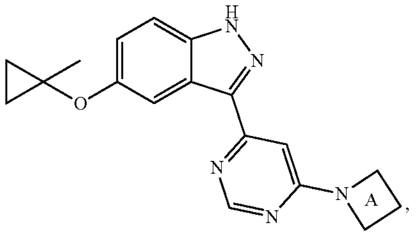
-continued
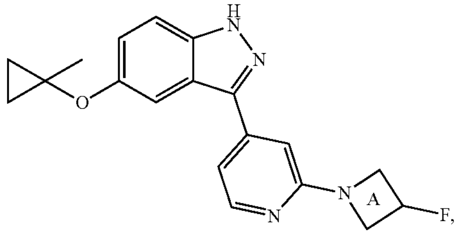
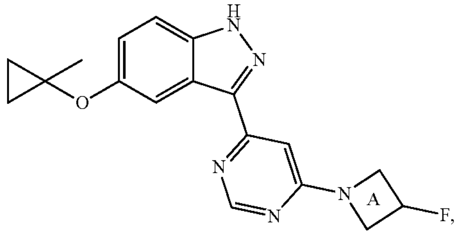
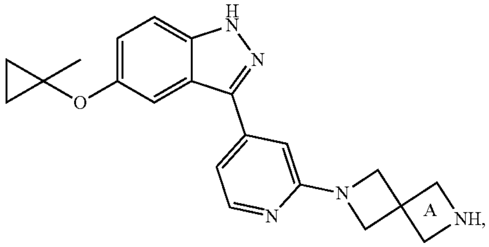
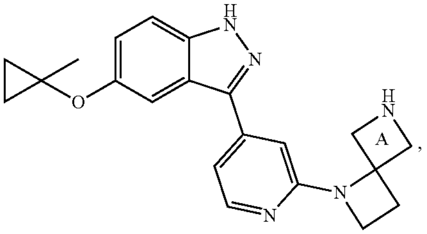
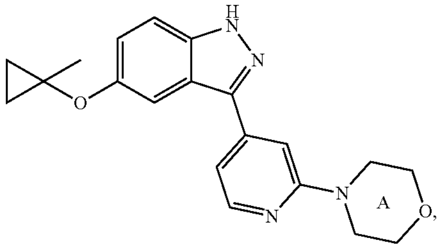
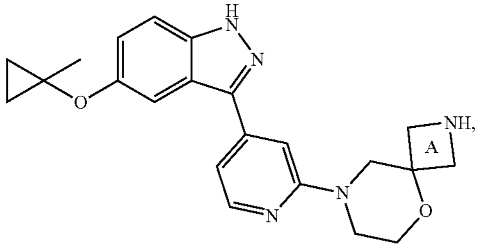
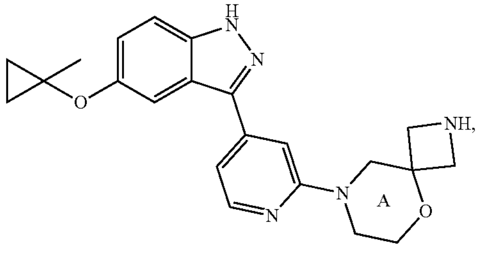

-continued
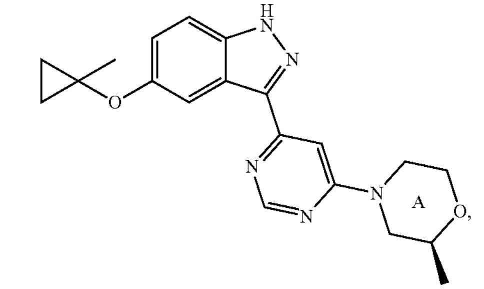
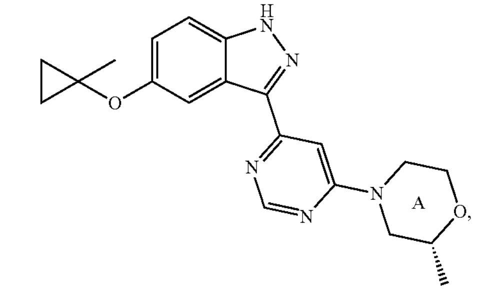
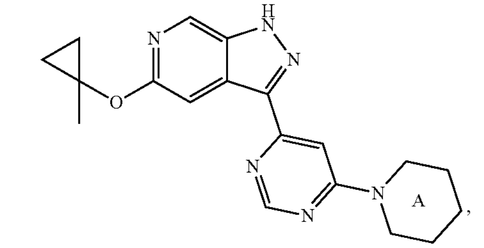
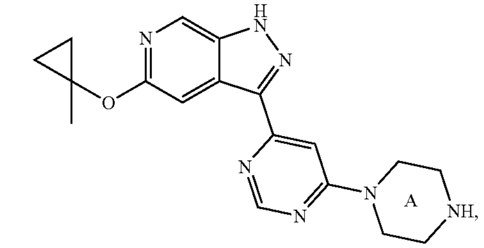
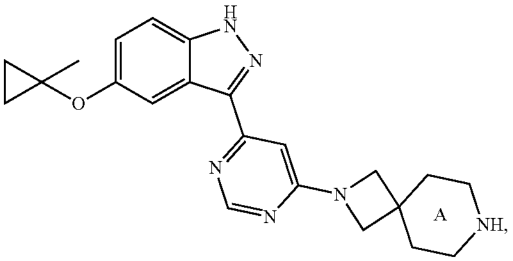
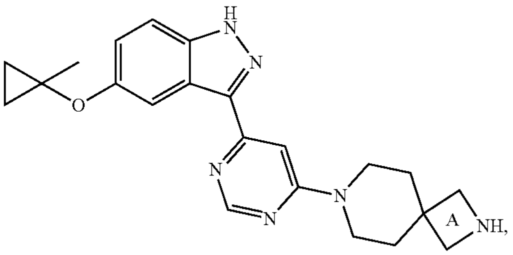
-continued
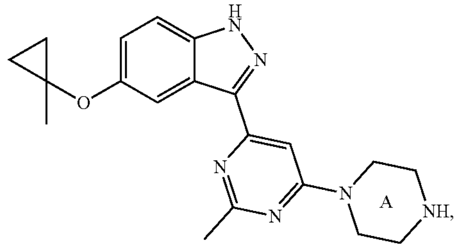
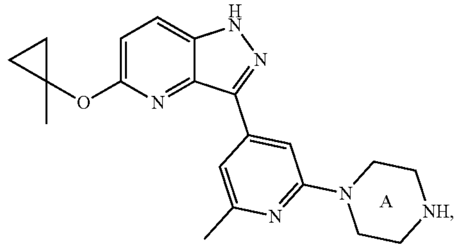
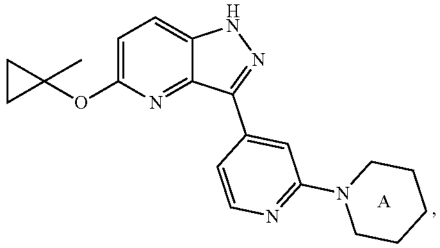
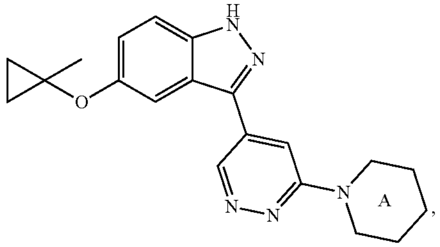
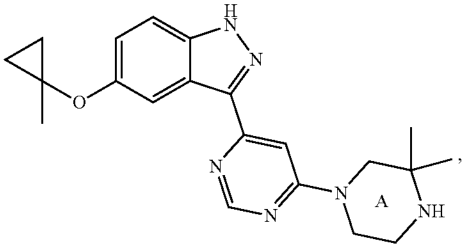
or
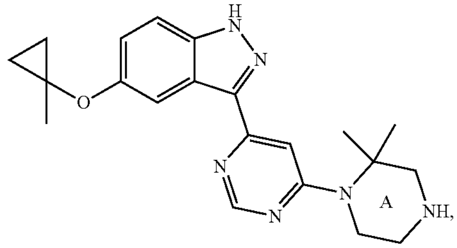
wherein the PTM is covalently linked to the L via an atom of heterocyloalkyl A or a substituent thereof;

(c) the L is a linker group (L) selected from:
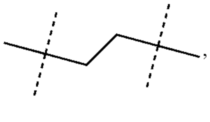
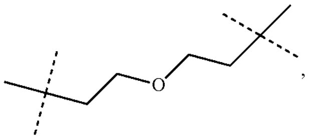
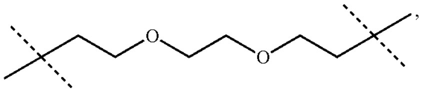
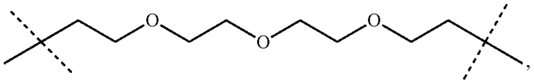
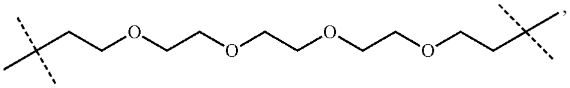
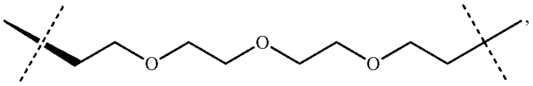
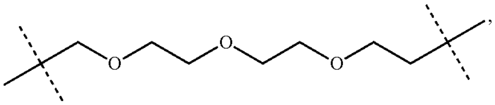
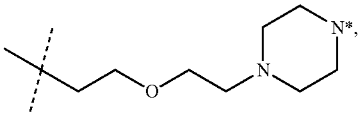
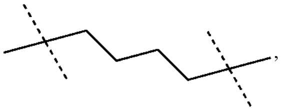
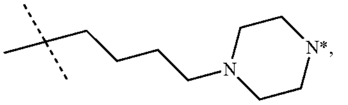
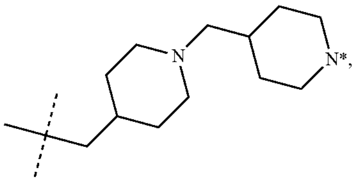
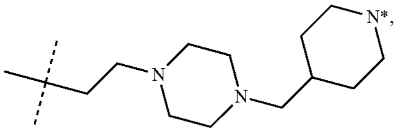
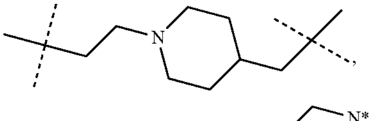
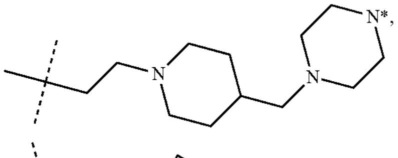
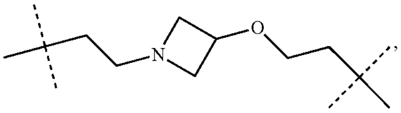
-continued
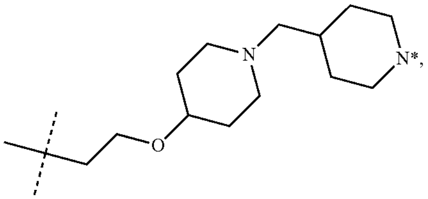
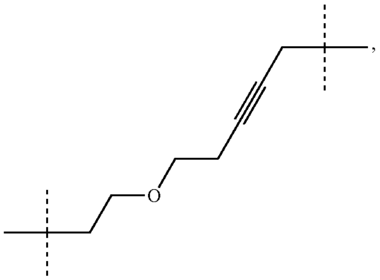
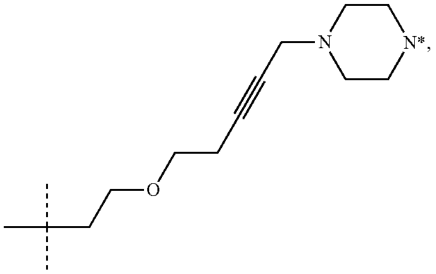
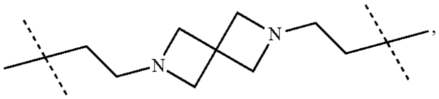
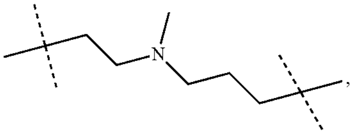
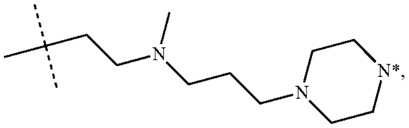
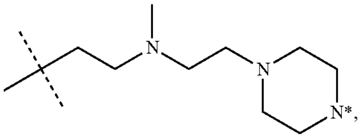
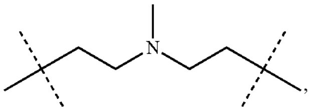
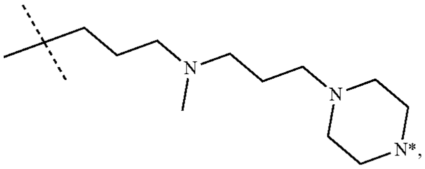
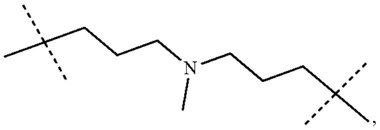

-continued
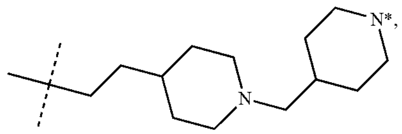
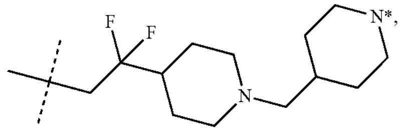
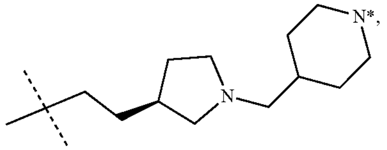
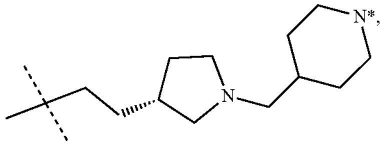
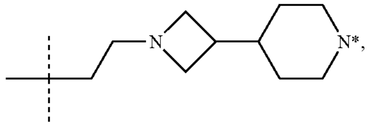
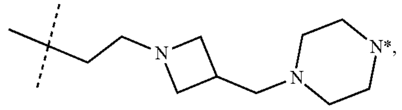
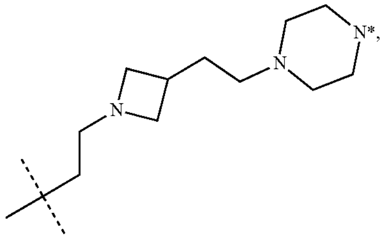
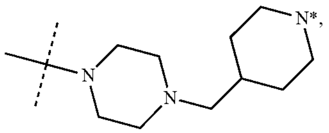
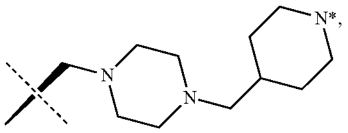
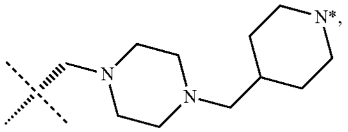
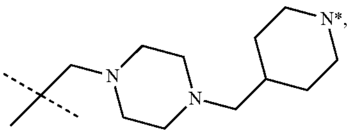
-continued
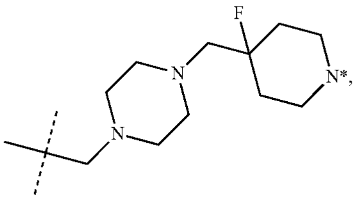
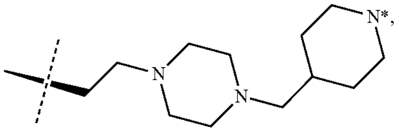
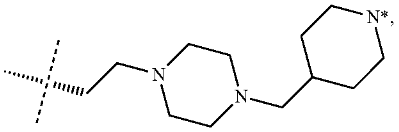
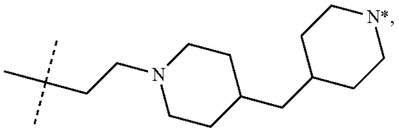
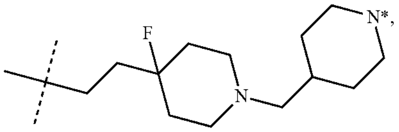
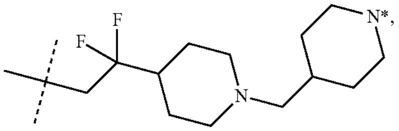
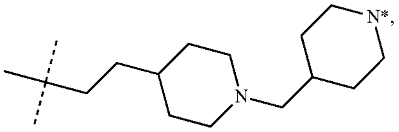
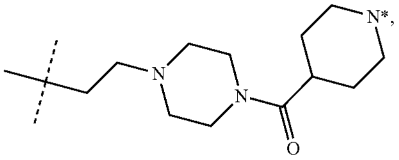
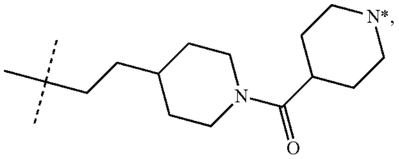
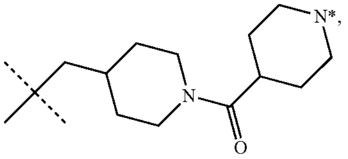
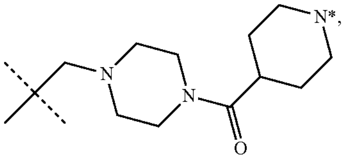

-continued
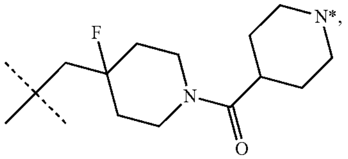
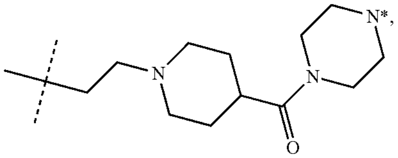
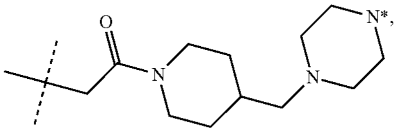
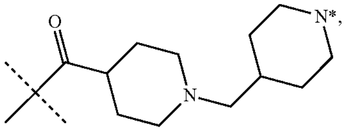
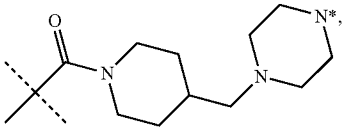
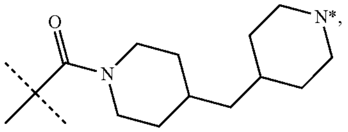
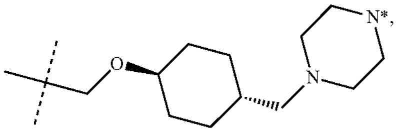
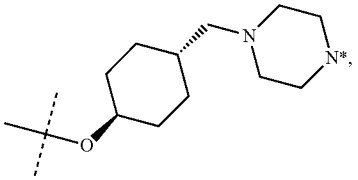
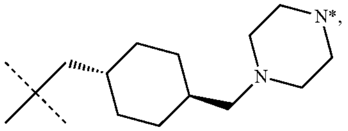
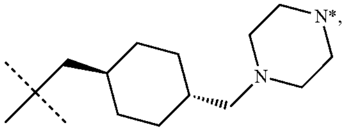
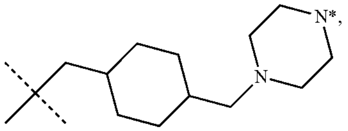
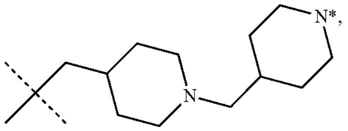
-continued
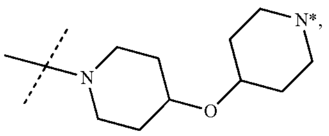
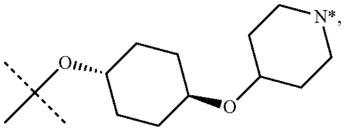
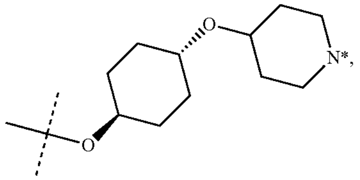
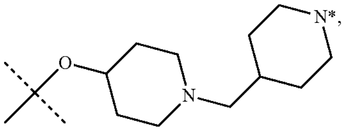
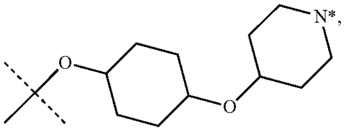
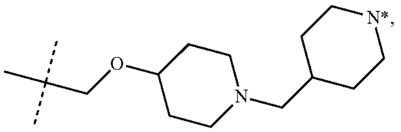
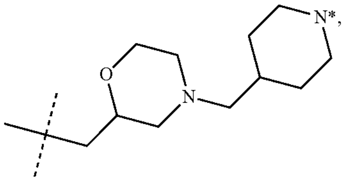
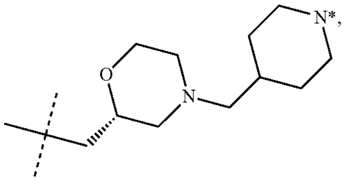
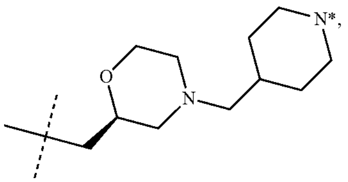
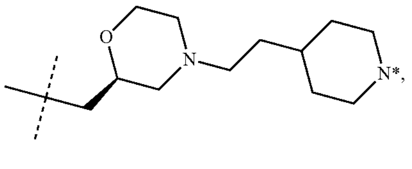

-continued
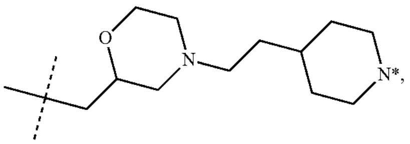
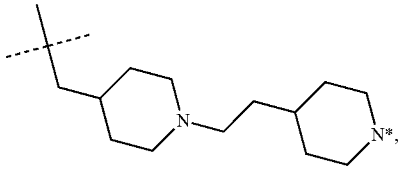
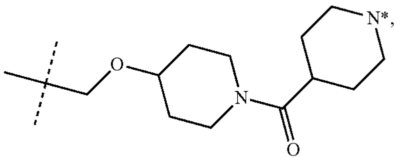
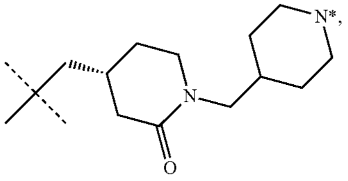
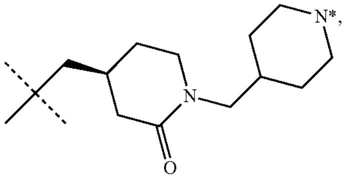
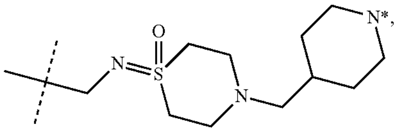
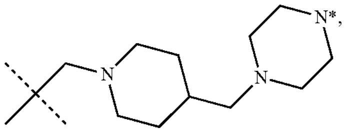
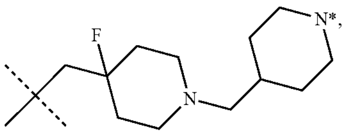
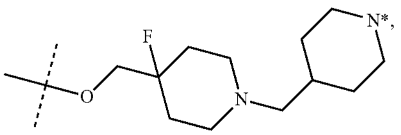
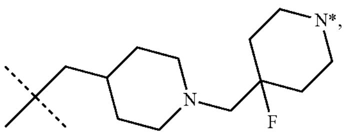
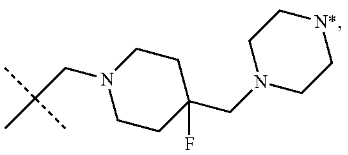
-continued
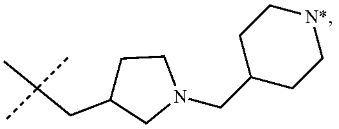
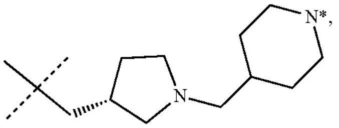
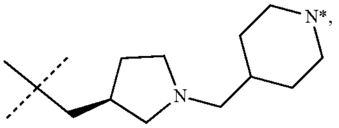
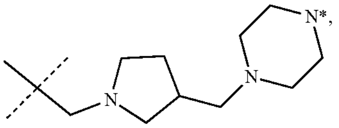
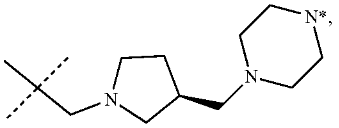
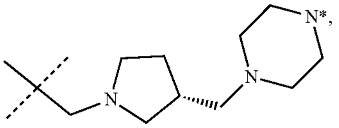
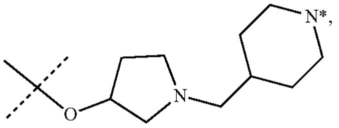
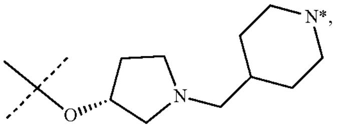
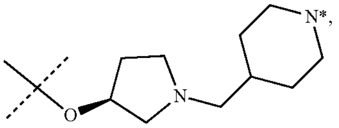
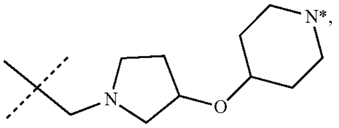
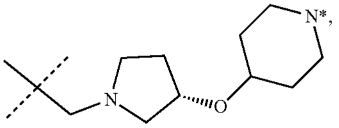
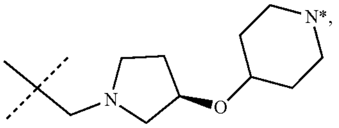
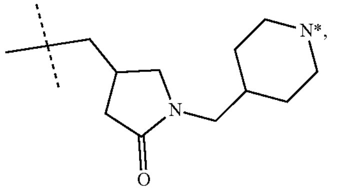

-continued
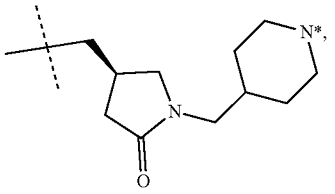
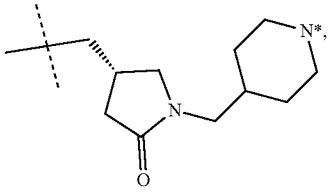
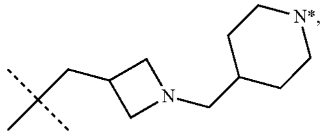
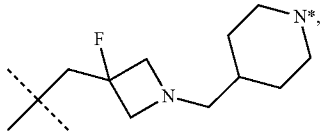
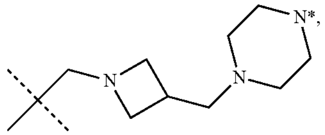
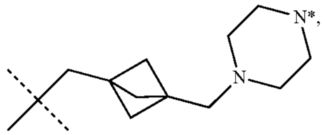
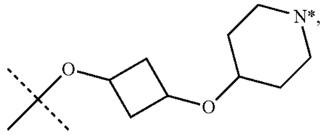
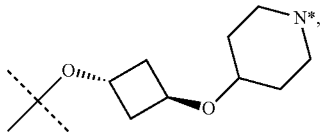
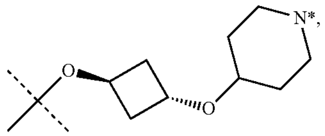
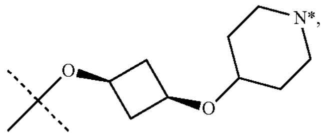
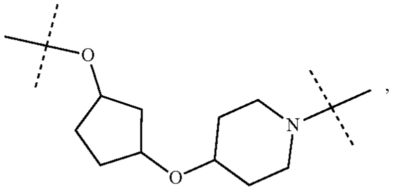
-continued
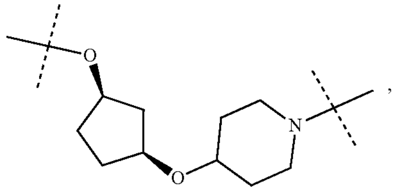
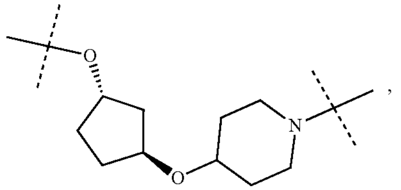
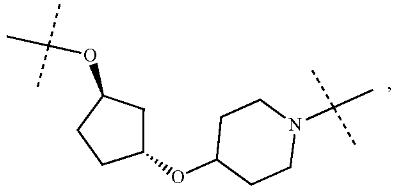
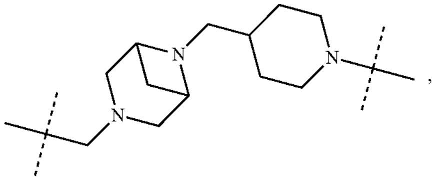
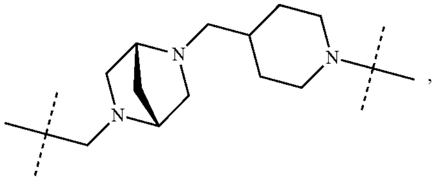
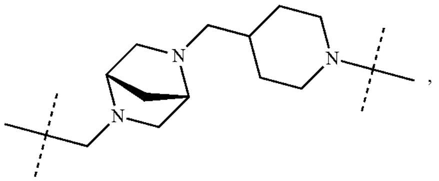
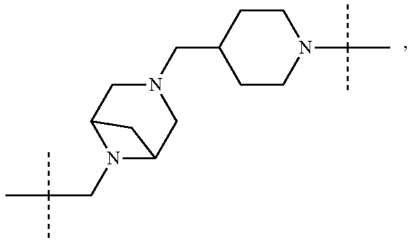
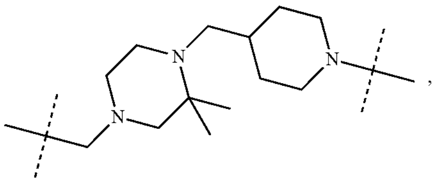
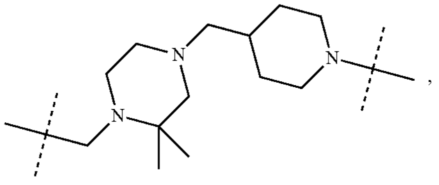

-continued
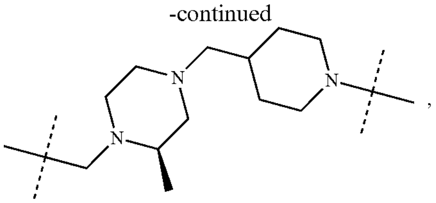
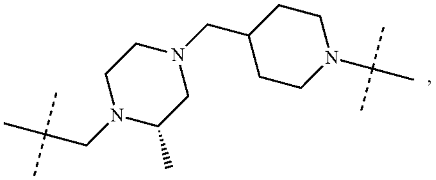
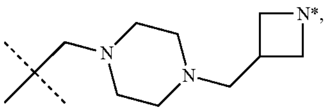
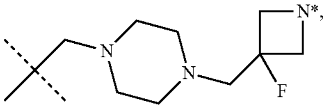
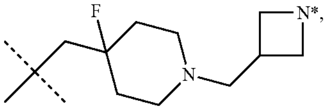
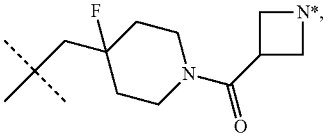
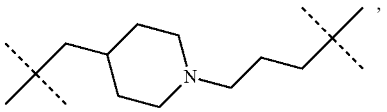
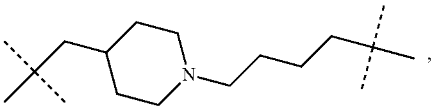
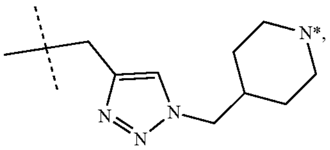
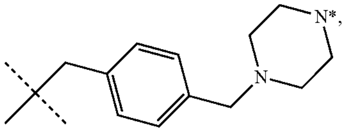
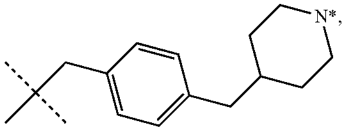
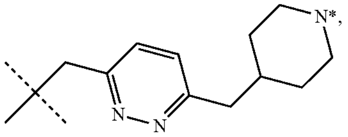
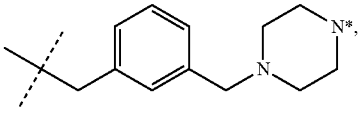
-continued
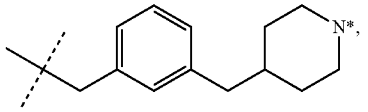
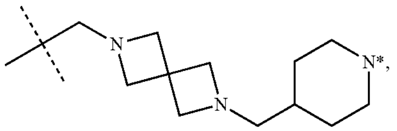
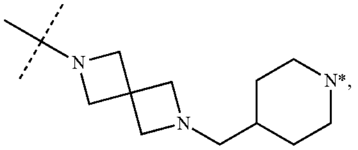
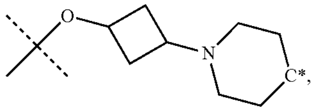
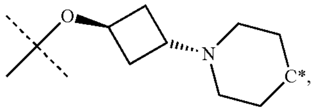
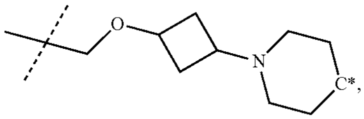
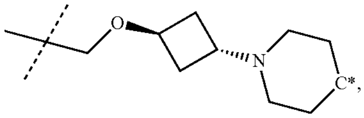
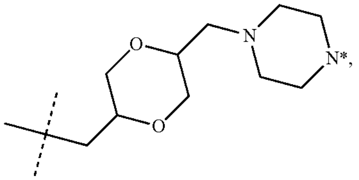
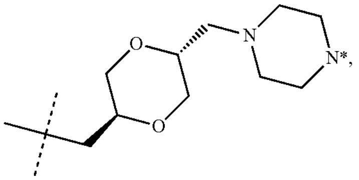
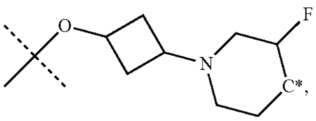
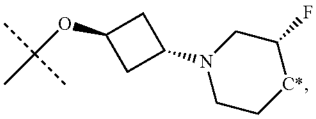
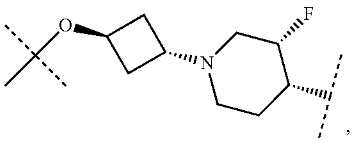

-continued
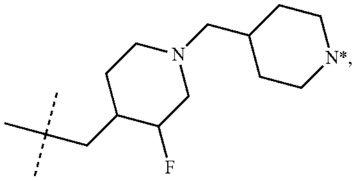
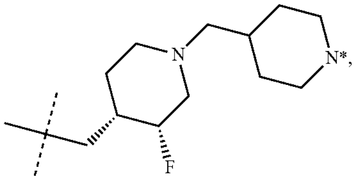
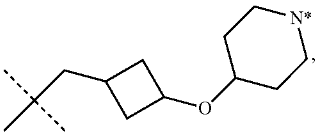
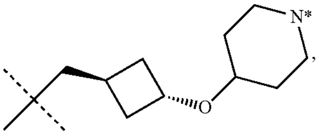
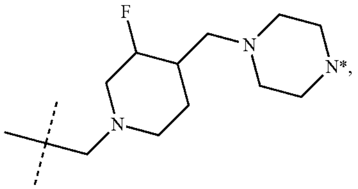
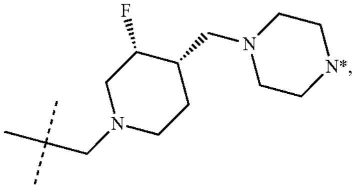
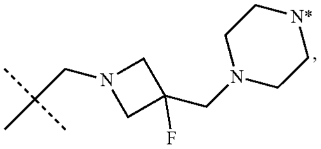
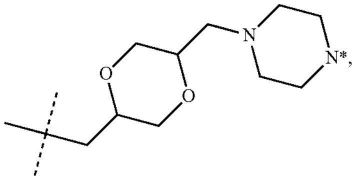
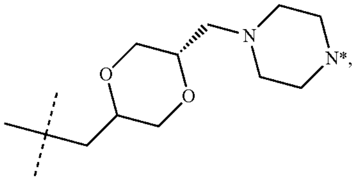
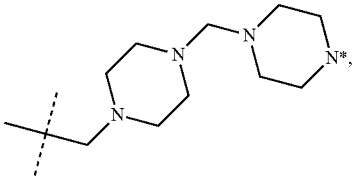
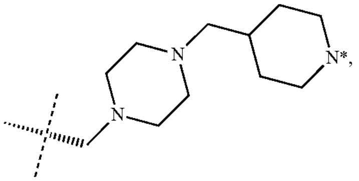
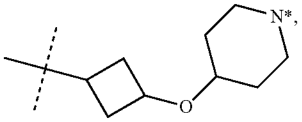
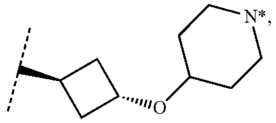
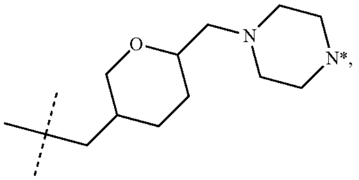
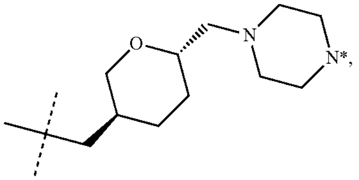
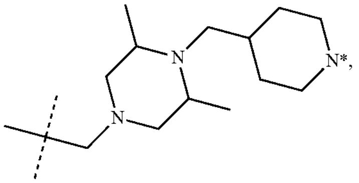
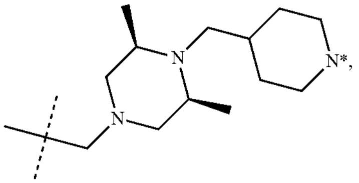
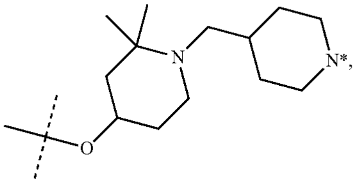
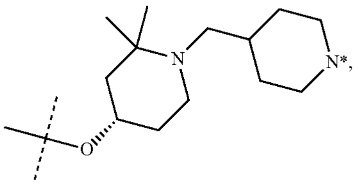
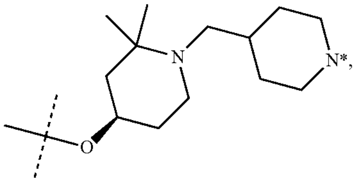

-continued
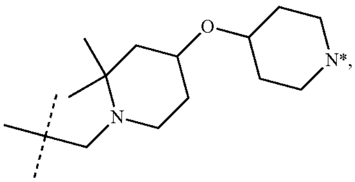
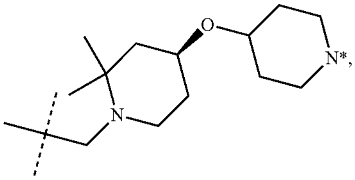
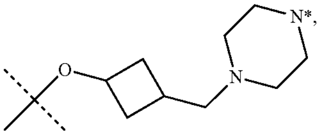
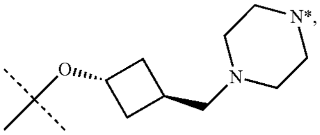
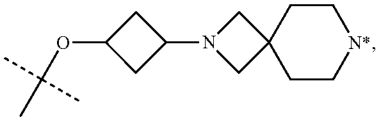
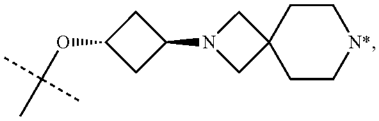
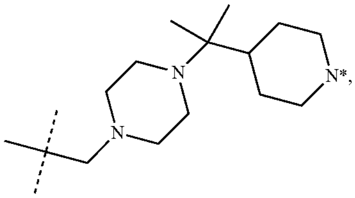
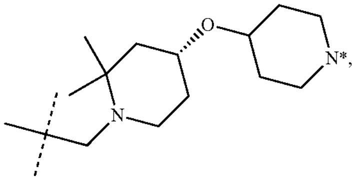
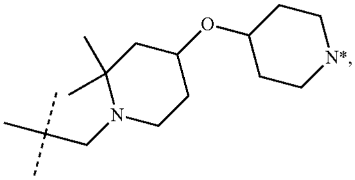
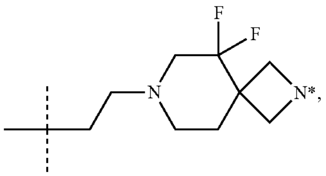
-continued
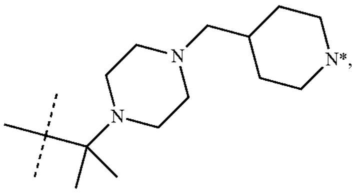
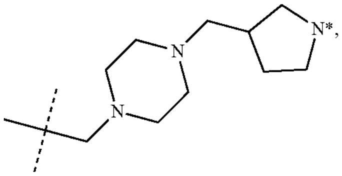
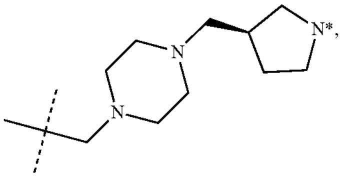
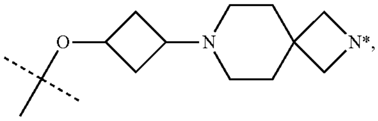
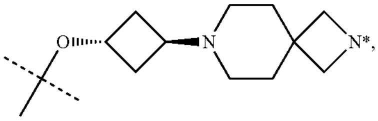
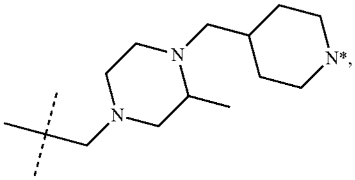
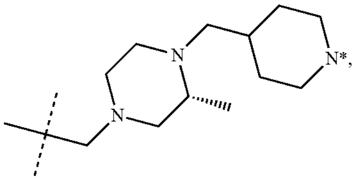
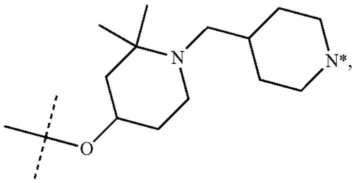
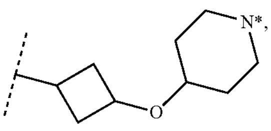
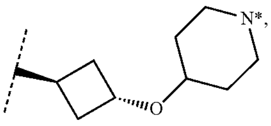

-continued
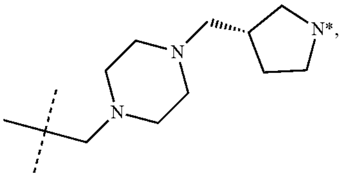
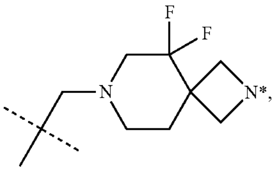
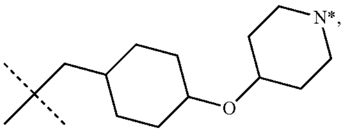
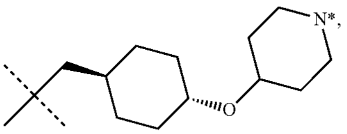
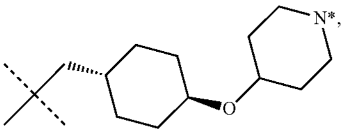
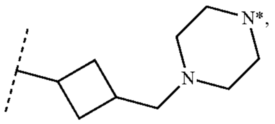
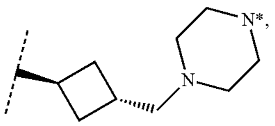
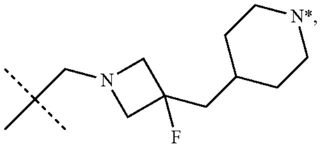
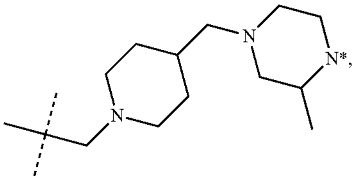
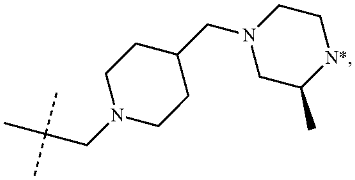
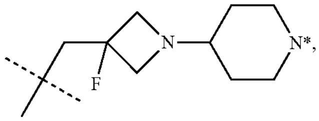
-continued
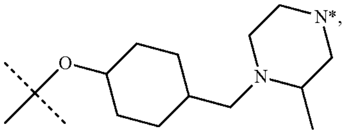
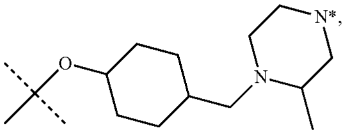
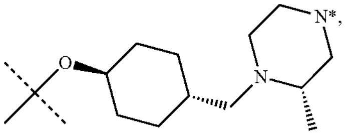
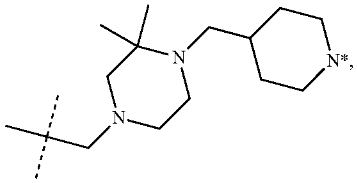
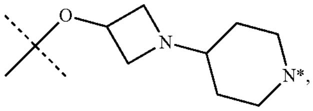
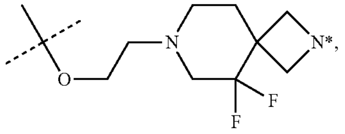
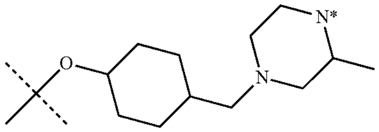
,
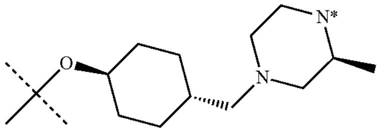
,
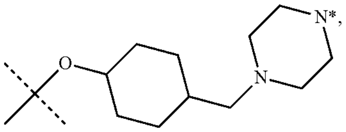
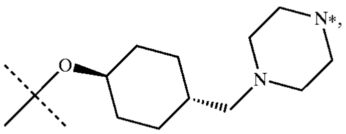
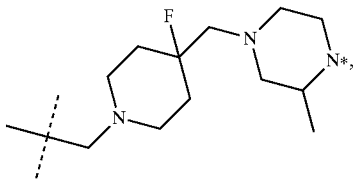
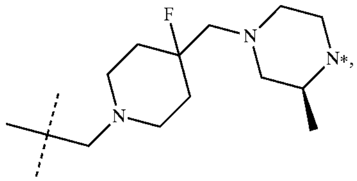

-continued

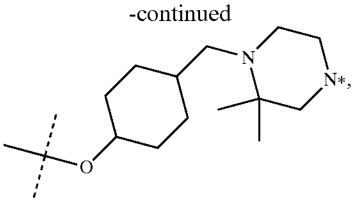

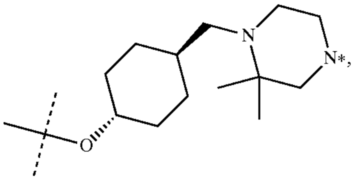

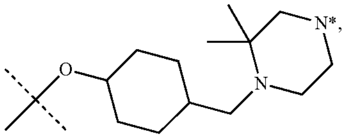

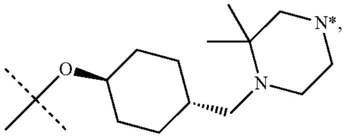

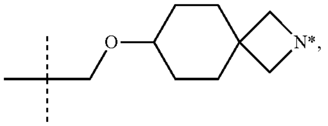

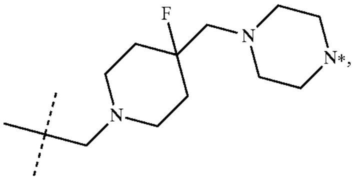

-continued

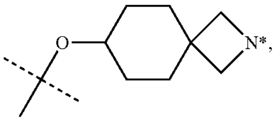

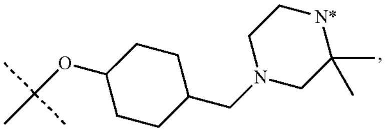

, and

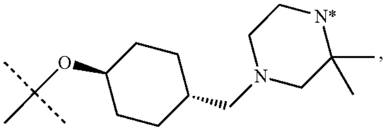

, wherein:

N* is a nitrogen atom that is covalently linked to or shared with the CLM or the PTM;

C* is a carbon atom that is covalently linked to or shared with the CLM or the PTM; and

 ,  , 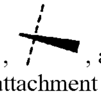 , and  and represented the point of attachment to the CLM or the PTM; or (d) a combination thereof.

In any aspect or embodiment described herein, one or more of: the PTM is a PTM selected from a compound of Table 1, the CLM is a CLM selected from a compound of Table 1, and the L is an L selected from a compound of Table 1.

In any aspect or embodiment described herein, the compound is represented by the chemical structure:

(Formula IIIa)

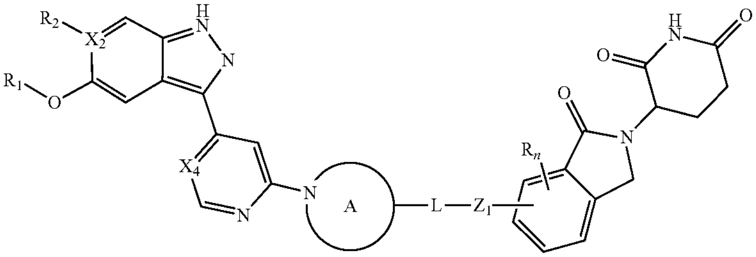

, or (Formula IIIb)

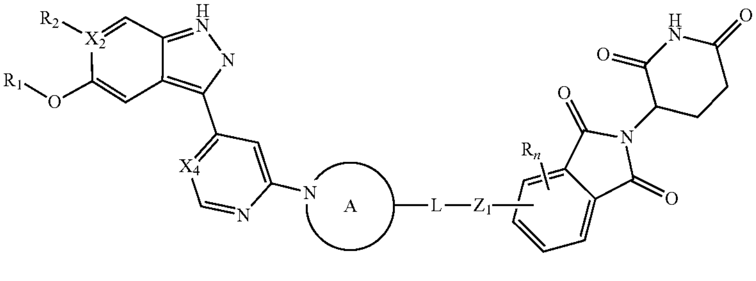

, wherein:

n is 0 or 1;

R is H, OH, —Cl, —F, or Br;

$Z_1$ is a nitrogen or carbon shared with a cyclic group of L;

$X_2$ is C or N;

$X_4$ is CH or N (preferably N);

$R_1$ is

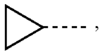 or 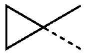 (preferably 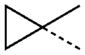), wherein  is the point of attachment to the oxygen of the PTM;

$R_2$ is a H, —Cl, or —F;

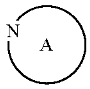

is:

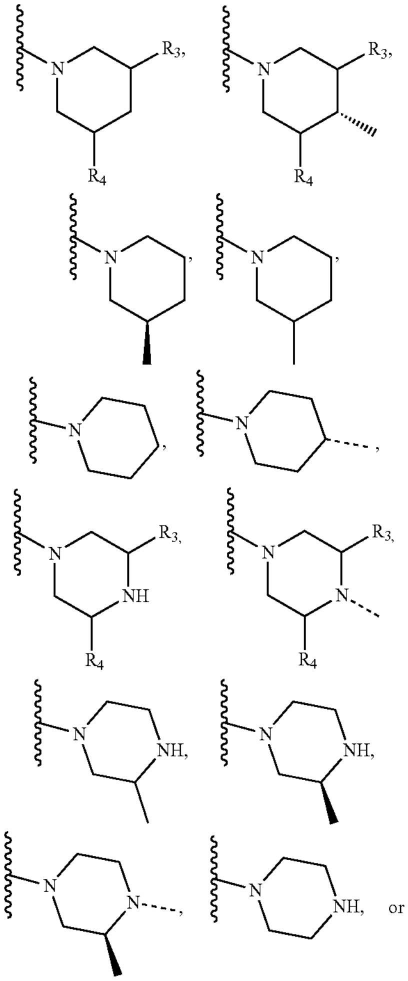

or

-continued

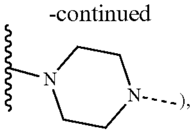

wherein:

$R_3$ is H, methyl, or ethyl;

$R_4$ is H, methyl, or ethyl;

 indicates the point of attachment of the

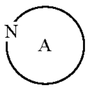

to the PTM; and

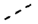 indicates the point of attachment of the PTM with the L, and when  is not present, the

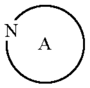

may be attached to the L via an atom of the cyclic group (e.g., a carbon or nitrogen);

L is represented by the chemical structure:

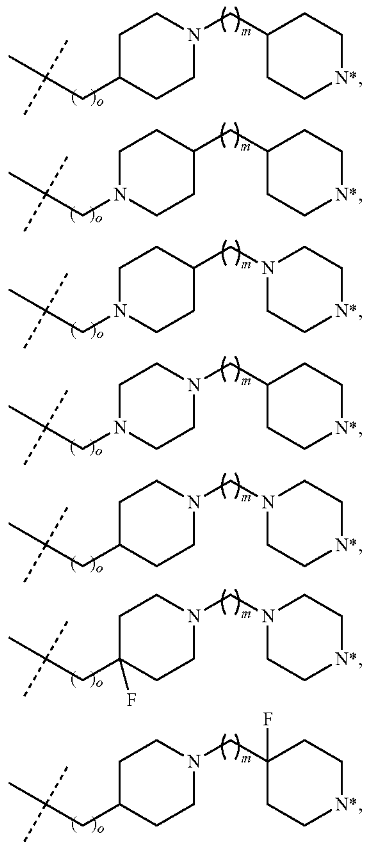

-continued

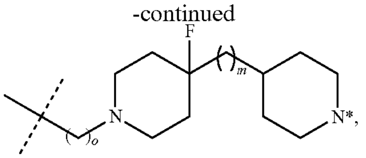,

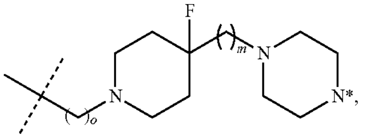,

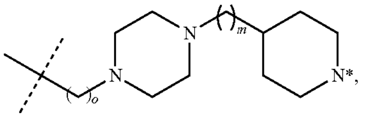,

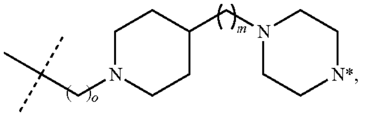,

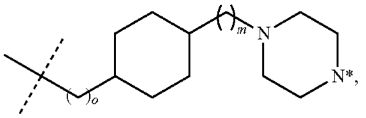, wherein:

m and n are integers independently selected from 0, 1, 2, or 3 (preferably 1); and the L is optionally substituted with 0, 1, 2, or 3 (preferably 0 or 1) groups selected from: —Cl, —F, and $C_{1-3}$ alkyl (e.g., methyl or ethyl).

In any aspect or embodiment described herein, $X_2$ is C and $X_4$ is N.

A further aspect of the present disclosure relates to a composition comprising an effective amount of a bifunctional compound of the present disclosure and a pharmaceutically acceptable carrier.

In any aspect or embodiment described herein, the composition further comprises additional bioactive agent.

In any aspect or embodiment described herein, the additional bioactive agent is an anti-inflammatory, a chemotherapy agent, or an immunomodulatory agent.

Another aspect of the present disclosure relates to a composition comprising a pharmaceutically acceptable carrier and an effective amount of at least one compound of the present disclosure for treating a disease, a disorder or a symptom causally related to LRRK2 in a subject, wherein the composition is effective in treating or ameliorating the disease, disorder, or at least one symptom of the disease or disorder.

An aspect of the present disclosure relates to a method for treating a disease, disorder, or a symptom causally related to LRRK2, wherein the method comprising administering a composition comprising a pharmaceutically acceptable carrier and an effective amount of at least one compound of the present disclosure to a subject in need thereof, wherein the composition is effective in treating or ameliorating the disease, disorder, or at least one symptom of the disease or disorder.

An additional aspect of the present disclosure relates to a method of treating or preventing a disease, a disorder, or symptom associated with LRRK2 comprising, providing a patient in need thereof, and administering an effective amount of a compound as described herein or composition comprising the same to the patient, wherein the compound or composition is effective in treating or ameliorating the disease, disorder, or at least one symptom of the disease or disorder.

In any aspect or embodiment described herein, the disease or disorder is idiopathic Parkinson's disease (PD), LRRK2 mutation associated PD, primary tauopathies, lewy body dementia, Crohn's Disease, Leprosy, neuroinflammation, Progressive Supranuclear Palsy, Picks disease, FTDtau, TDP-43 Frontal Temporal Dementia, TDP-43 ALS, c9orf ALS, Huntington's disease, spinocerebellar ataxias (SCAs) 1, 2, 3, 6, 7 and 17, dentatorubral pallidoluysian atrophy (DRPLA) or Kennedy's disease.

Protein Level Control

This description also provides methods for the control of protein levels within a cell. The method is based on the use of compounds as described herein such that degradation of the target protein LRRK2 in vivo will result in the reducing the amount of the target protein in a biological system, preferably to provide a particular therapeutic benefit.

The following examples are used to assist in describing the present disclosure, but should not be seen as limiting the present disclosure in any way.

In certain embodiments, the description provides the following exemplary LRRK2-degrading bifunctional molecules (compounds of Table 1 or compounds 52-384), including salts, polymorphs, analogs, derivatives, and deuterated forms thereof.

Exemplary Assay for Testing LRRK2 Degradation Driven by Exemplary Hetero-Bifunctional Compounds Designed to Target LRRK2

The assay measures the degradation of wildtype and G2019S LRRK2 tagged with a HiBit tag on the C-terminus of the protein that was expressed from a mammalian expression vector, driven by the ubiquitin promoter in HEK293 cells. Each compound dose-response was repeated on two separate days, on three separate plates each day.

Plasmid Preparation. Transfection mixes were assembled as follows and incubated for 30 minutes at room temperature. In a 15 mL tube, 5.25 mL Opti-MEM (no additions) was mixed with 17 μL Firefly Luciferase plasmid at 1 μg/μL and 158 μL WT plasmid DNA at 1 μg/μL (175 μg total DNA) were mixed by flicking. In a new 15 mL tube, 5.25 mL OptiMEM was mixed with 17 μL Firefly Luciferase plasmid at 1 μg/μL and 158 μL G2019S plasmid DNA at 1 μg/μL (175 μg total DNA) were mixed by flicking. X-tremeGene HP was mixed thoroughly using a vortex. Next, 175 μL was added to each tube and flicked to mix. Both tubes were left to incubate for 30 minutes at room temperature.

While the transfection mixes were incubating, HEK293 cells (acquired from ATCC; ATCC CRL-1573) were harvested with trypsin. Once cells are detached, the cells were resuspended in 12 mL OptiMEM+5% FBS and transferred to a 50 mL tube. The cells were mixed well and counted. Using OptiMEM+5% FBS, the cells were diluted in two 250 mL conical tubes at $0.71\times10^6$ cells/mL in 70 mL. One tube was labeled "WT" and the other "G2019S". The WT and G2019S transfection mixes were added dropwise to the corresponding 250 mL tubes. The tubes were mixed first by pipetting then by swirling. The tubes were incubated at room temperature for at least 5 minutes.

Each tube was swirled before dispensing and after every three plates. Seventy microliters of cells were dispensed with WT or G2019S DNA to seven plates each. Three plates of each were tested with compound plate one (preparation described below) and three plates of each were tested with compound plate two (preparation described below). The first plate from each set served as a "prime" plate and was not used to test compounds. Each plate was incubated in the hood for 10 minutes before placing in the 37° C. incubator for 24 hours.

Preparation of Compound and Assay Plates. Two compound plates were made using 96 well polypropylene plates. Compounds were made up at 10 mM and were diluted to 1 mM in 30 μL. Each dose response curve included a well of DMSO, as a negative control and for normalization, and a well of 0.5 μM of Compound 4 as a positive control. In addition to seven test compounds, each plate also included a dose response of Compound 4. The compound plates were spun down along at 1200 rpm for 2 minutes.

The two compound plates were then mixed and 2 μL was diluted in intermediate plates having 248 μL of Opti-Mem in each well. Next, 10 μL diluted compounds from the intermediate plates were added to each test plate (three WT and three G2019S plates per compound plate for a total of 12 assay plates). The plates were incubated for 24 hours at 37° C.

All assay plates and all Nano-Glo Dual-Luciferase Reporter Assay System components (except for the DLR substrate) were equilibrated to room temperature. Next, the luciferase buffer was mixed with the lyophilized amber bottle until fully dissolved, and 75 μL of the luciferase mixture was added to each well of each assay plate. The assay plates were incubated for 10 minutes at room temperature with shaking for at least 5 minutes, and then read on a plate reader.

Developing Plates and Analyzing Data. One milliliter of DLR substrate and 1 mL LgBiT Protein were added to the Stop and Glo buffer, and 75 μL of the mixture was added to each well of each plate. Optically clear seals were added to each plate and each plate was incubated for 20 minutes with shaking for at least 10 minutes, and then read on a plate reader.

As mentioned above, plates were run in triplicate and assay repeated twice (total of 6 replicates per exemplary compound). Each cell was examined for firefly luciferase for cell number and viability and Nanoluc for the LRRK2-HiBit quantification.

Ratio of (HiBit/luciferase)*1000 was determined and the data was normalized to % of DMSO median value. Curve fitting was performed on each individual plate. The data for exemplary compounds of Table 1 below is shown below in Table 2 in the *G2019S DC50 (nM), **G2019S Dmax (%), *WT DC50 (nM), and **WT Dmax (%) columns.

Exemplary Assay for Testing LRRK2 Degradation Driven by Exemplary Hetero-Bifunctional Compounds Designed to Target LRRK2

The assay measures the degradation of LRRK2 in cells where the C-terminus (3') of the endogenous gene has been tagged with a HiBit sequence in HEK293 cells. The cells also express firefly luciferase, expressed from a Cytomegalovirus promoter and introduced into the HiBit tagged cells and stably expressed. The Nano-Glo® Dual Luciferase Reporter Assay System (Promega™, Madison, WI) was utilized.

Day 1—Preparation of Compound and Assay Plates. Two sets of plates were prepared: a triplicate set for the HiBit assay in white 384-well plates and a triplicate set of plate in black 384-well plates for the Alamar Blue cell viability assay. Briefly, the growth media (DMEM+Glutamax-10% fetal bovine serum-1% Penicillin-Streptomicin) from two T128 flasks was aspirated from the flasks. Cells were washed with Dulbecco's Phosphate Buffered Saline (dPBS) and aspirated. Trypsin (3 mL per flask) was added and the flasks were incubated for 2-3 minutes.

Ten mL of OptiMEM-10% fetal bovine-1% penicillin-streptomycin (hereinafter, "OptiMEM media") was added to the flask and the cells and transferred to a 50 mL conical tube. A cell count (25 ul of cell into Effendorf vial+25 ul of Trypan Blue Stain) was performed and the cell density adjusted to 15,000 cell/45 μl/well (3.33×10^5/mL) in OptiMEM media.

Fourty-five microliters of the cell suspension (15,000 cells) was aliquoted to each well of the white 384-well plate. The plates incubated at room temperature for 10 minutes before being placed in the 37° C.+5% $CO_2$ incubator overnight Day 2—Compound Treatment. Exemplary compounds were prepared at a 1 mM starting concentration and 1:3 serial dilution for 11 points CRC prepared and stored in the freezer. The Master Compound Plate was thawed overnight at room temperature. DMSO (20 μL) was added into column 24 of the Master Compound Plate for negative control and 20 μL of 300 μM of Compound 4 in column 23 as positive control.

Intermediate Compound Plate with 4% DMSO in OptiMEM Media. DMSO was added to warm OptiMEM media to achieve a 4% DMSO solution (approximately 50 mL/plate). One-hundred microliters of the OptiMEM-4% DMSO was aliquoted to each well of 384-Well Deep Well Microplates.

The Master Compound Plate and the Intermediate Compound Plate were spun down.

One microliter of compound from the Master Compound Plate was transferred into the Intermediate plate (a 1:100 dilution). The diluted mixture was mixed and 5 μL transferred into the assay plate (a 1:10 dilution) for the final starting concentration of 1 μM. The Treated Assay plates were incubated for 24 hours at 37° C.+5% $CO_2$. The Master Compound Plate was sealed and store at room temperature for a second run that was performed within a week.

Day 3—HiBit Assay. Five microliters of Alamar Blue was added to each well of the black 384-well plates. The plates were incubated for 2 hours in the incubator (37° C.+5% $CO_2$) and at room temperature for one hour. Fluorescence of each plate was read on a plated reader for the Alamar Blue viability assay.

One set of white assay plates was warmed to room temperature (45 minute).

The One Glo luciferase mixture was prepared. The media from white 384-well assay plates was aspirated. Twenty-five μL of the One Glo luciferase mixture was added to each well of the assay plates. The plates were incubated on the bench (room temperature) for 45 minutes, including 10 minutes of shaking at 700 rpm. The luminescence of each plate was read on a plate reader.

1:100 DLR substrate and 1:100 LgBiT Protein dilution were added to the Promega Stop and Glo buffer and mixed just before addition to assay plates. Twenty-five microliters of Stop and Glo mixture was added to each well. Assay plates incubated for at least 45 minutes, including 10 minutes of shaking at 700 rpm. The luminescence of each plate was read on a plate reader.

Analysis of LRRK2 HiBit Screening assays. As mentioned above, plates were run in triplicate and the assay repeated twice (total of 6 replicate for exemplary compounds). For each treatment, measurements were taken for firefly luciferase for cell number, cell viability (Alamar Blue), and Nanoluc for the LRRK2-HiBit quantification.

The LRRK2 HiBit and alamar blue signal was normalized to % DMSO median value for each plate. Curve fitting was performed on each compound for replicates across three plates. The date for exemplary compounds of Table 1 below is shown below in Table 2 in the Endogenous *WT DC50 (nM) and **Endogenous WT Dmax columns (%).

TABLE 1

Exemplary bifunctional compounds of the present disclosure**

| Ex. No. | Chemical Structure | IUPAC Name |
|---|---|---|
| 52 | 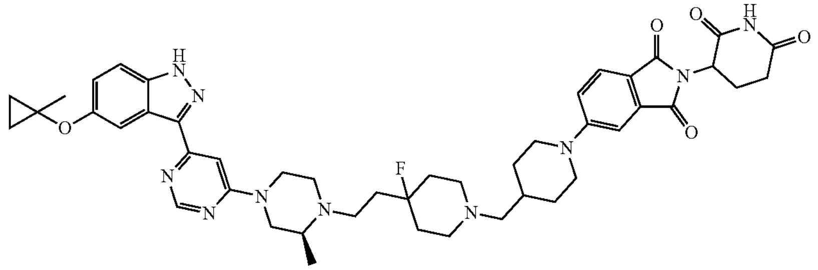 [SMILES: C[C@H]1CN(c2cc(-c3n[nH]c4ccc(OC5(C)CC5)cc34)ncn2)CCN1CCC1(F)CCN(CC2CCN(c3ccc4c(c3)C(=O)N(C3CCC(=O)NC3=O)C4=O)CC2)CC1] | 2-(2,6-dioxopiperidin-3-yl)-5-{4-[(4-fluoro-4-{2-[(2S)-2-methyl-4-{6-[5-(1-methylcyclopropoxy)-1H-indazol-3-yl]pyrimidin-4-yl}piperazin-1-yl]ethyl}piperidin-1-yl)methyl]piperidin-1-yl}-2,3-dihydro-1H-isoindole-1,3-dione |
| 53 | 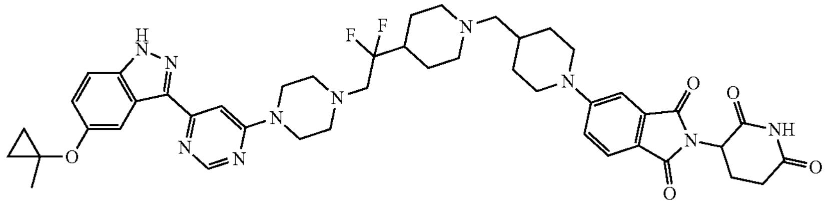 [SMILES: CC1(Oc2ccc3[nH]nc(-c4cc(N5CCN(CC(F)(F)C6CCN(CC7CCN(c8ccc9c(c8)C(=O)N(C8CCC(=O)NC8=O)C9=O)CC7)CC6)CC5)ncn4)c3c2)CC1] | 5-[4-({4-[1,1-difluoro-2-(4-{6-[5-(1-methylcyclopropoxy)-1H-indazol-3-yl]pyrimidin-4-yl}piperazin-1-yl)ethyl]piperidin-1-yl}methyl)piperidin-1-yl]-2-(2,6-dioxopiperidin-3-yl)-2,3-dihydro-1H-isoindole-1,3-dione |
| 54 | 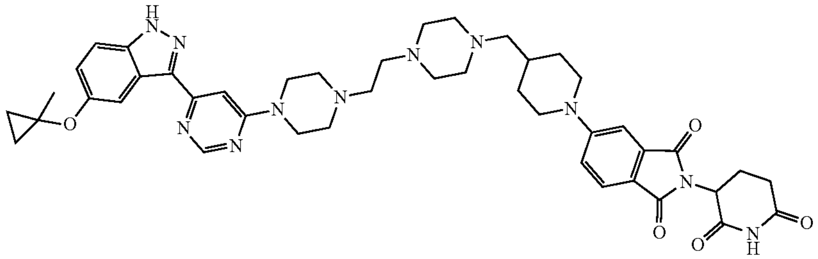 [SMILES: CC1(Oc2ccc3[nH]nc(-c4cc(N5CCN(CCN6CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({4-[2-(4-{6-[5-(1-methylcyclopropoxy)-1H-indazol-3-yl]pyrimidin-4-yl}piperazin-1-yl)ethyl]piperazin-1-yl}methyl)piperidin-1-yl]-2,3-dihydro-1H-isoindole-1,3-dione |
| 55 | 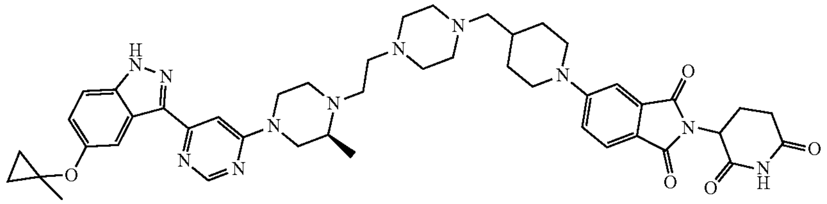 [SMILES: C[C@H]1CN(c2cc(-c3n[nH]c4ccc(OC5(C)CC5)cc34)ncn2)CCN1CCN1CCN(CC2CCN(c3ccc4c(c3)C(=O)N(C3CCC(=O)NC3=O)C4=O)CC2)CC1] | 2-(2,6-dioxopiperidin-3-yl)-5-{4-[(4-{2-[(2S)-2-methyl-4-{6-[5-(1-methylcyclopropoxy)-1H-indazol-3-yl]pyrimidin-4-yl}piperazin-1-yl]ethyl}piperazin-1-yl)methyl]piperidin-1-yl}-2,3-dihydro-1H-isoindole-1,3-dione |
| 56 | 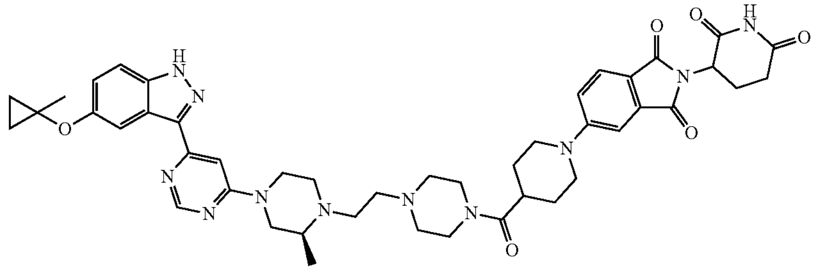 [SMILES: C[C@H]1CN(c2cc(-c3n[nH]c4ccc(OC5(C)CC5)cc34)ncn2)CCN1CCN1CCN(C(=O)C2CCN(c3ccc4c(c3)C(=O)N(C3CCC(=O)NC3=O)C4=O)CC2)CC1] | 2-(2,6-dioxopiperidin-3-yl)-5-[4-(4-{2-[(2S)-2-methyl-4-{6-[5-(1-methylcyclopropoxy)-1H-indazol-3-yl]pyrimidin-4-yl}piperazin-1-yl]ethyl}piperazine-1-carbonyl)piperidin-1-yl]-2,3-dihydro-1H-isoindole-1,3-dione |

TABLE 1-continued

| Ex. No. | Chemical Structure | IUPAC Name |
|---|---|---|
| | Exemplary bifunctional compounds of the present disclosure** | |
| 57 | 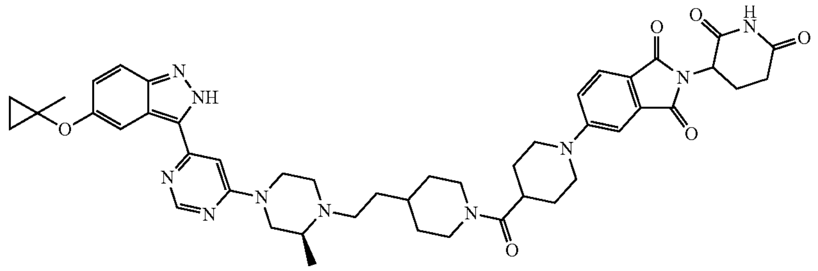 [SMILES: C[C@H]1CN(c2cc(-c3[nH]nc4ccc(OC5(C)CC5)cc34)ncn2)CCN1CCC1CCN(C(=O)C2CCN(c3ccc4c(c3)C(=O)N(C3CCC(=O)NC3=O)C4=O)CC2)CC1] | 2-(2,6-dioxopiperidin-3-yl)-5-[4-(4-{2-[(2S)-2-methyl-4-{6-[5-(1-methylcyclopropoxy)-2H-indazol-3-yl]pyrimidin-4-yl}piperazin-1-yl]ethyl}piperidine-1-carbonyl)piperidin-1-yl]-2,3-dihydro-1H-isoindole-1,3-dione |
| 58 | 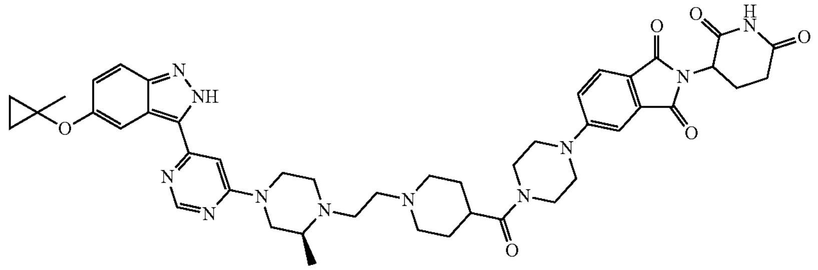 [SMILES: C[C@H]1CN(c2cc(-c3[nH]nc4ccc(OC5(C)CC5)cc34)ncn2)CCN1CCN1CCC(C(=O)N2CCN(c3ccc4c(c3)C(=O)N(C3CCC(=O)NC3=O)C4=O)CC2)CC1] | 2-(2,6-dioxopiperidin-3-yl)-5-[4-(1-{2-[(2S)-2-methyl-4-{6-[5-(1-methylcyclopropoxy)-2H-indazol-3-yl]pyrimidin-4-yl}piperazin-1-yl]ethyl}piperidine-4-carbonyl)piperazin-1-yl]-2,3-dihydro-1H-isoindole-1,3-dione |
| 59 | 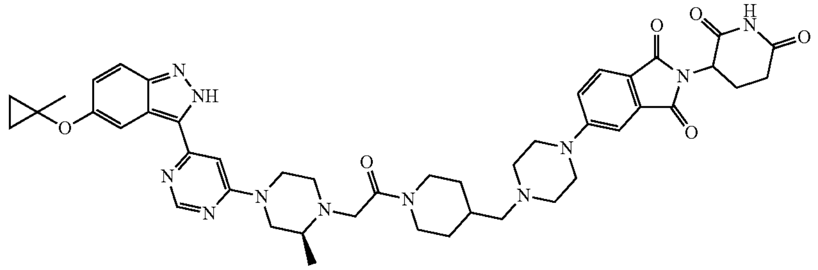 [SMILES: C[C@H]1CN(c2cc(-c3[nH]nc4ccc(OC5(C)CC5)cc34)ncn2)CCN1CC(=O)N1CCC(CN2CCN(c3ccc4c(c3)C(=O)N(C3CCC(=O)NC3=O)C4=O)CC2)CC1] | 2-(2,6-dioxopiperidin-3-yl)-5-{4-[(1-{2-[(2S)-2-methyl-4-{6-[5-(1-methylcyclopropoxy)-2H-indazol-3-yl]pyrimidin-4-yl}piperazin-1-yl]acetyl}piperidin-4-yl)methyl]piperazin-1-yl}-2,3-dihydro-1H-isoindole-1,3-dione |
| 60 | 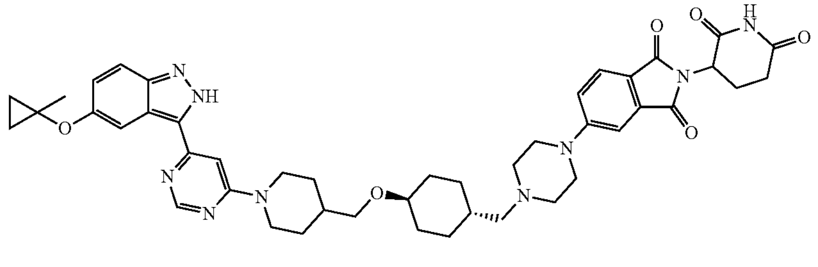 [SMILES: CC1(Oc2ccc3n[nH]c(-c4cc(N5CCC(CO[C@H]6CC[C@H](CN7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{[(1r,4r)-4-[(1-{6-[5-(1-methylcyclopropoxy)-2H-indazol-3-yl]pyrimidin-4-yl}piperidin-4-yl)methoxy]cyclohexyl]methyl}piperazin-1-yl)-2,3-dihydro-1H-isoindole-1,3-dione |
| 61 | 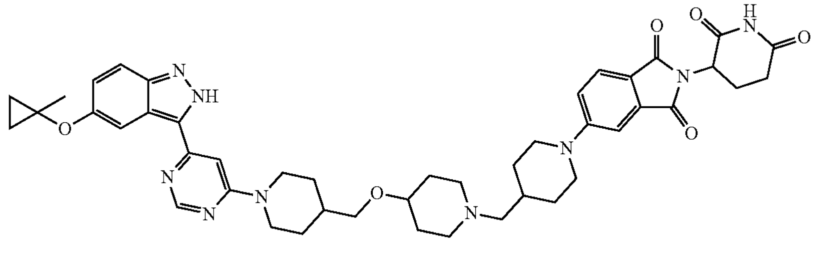 [SMILES: CC1(Oc2ccc3n[nH]c(-c4cc(N5CCC(COC6CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({4-[(1-{6-[5-(1-methylcyclopropoxy)-2H-indazol-3-yl]pyrimidin-4-yl}piperidin-4-yl)methoxy]piperidin-1-yl}methyl)piperidin-1-yl]-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 62 | 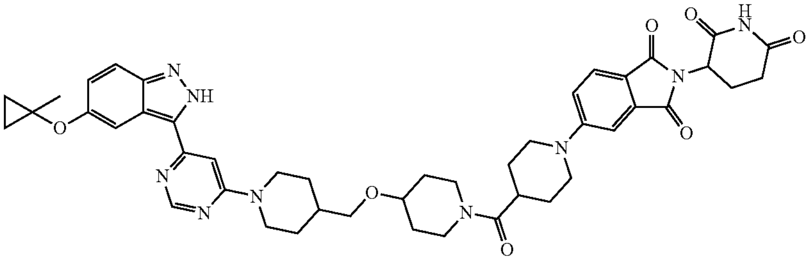 [SMILES: CC1(Oc2ccc3n[nH]c(-c4cc(N5CCC(COC6CCN(C(=O)C7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{4-[(1-{6-[5-(1-methylcyclopropoxy)-2H-indazol-3-yl]pyrimidin-4-yl}piperidin-4-yl) methoxy]piperidine-1-carbonyl}piperidin-1-yl)-2,3-dihydro-1H-isoindole-1,3-dione |
| 63 | 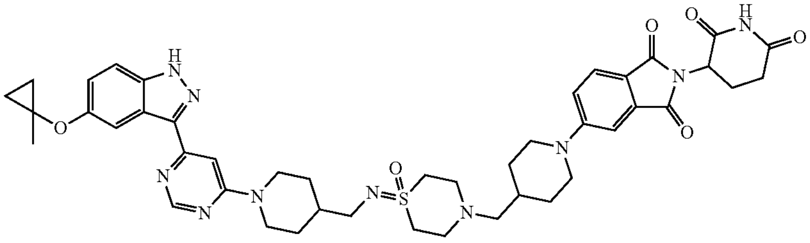 [SMILES: CC1(Oc2ccc3[nH]nc(-c4cc(N5CCC(CN=S6(=O)CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-{4-[(1-{[(1-{6-[5-(1-methylcyclopropoxy)-1H-indazol-3-yl]pyrimidin-4-yl}piperidin-4-yl)methyl]imino}-1-oxo-1λ$^6$-thiomorpholin-4-yl)methyl]piperidin-1-yl}-2,3-dihydro-1H-isoindole-1,3-dione |
| 64 | 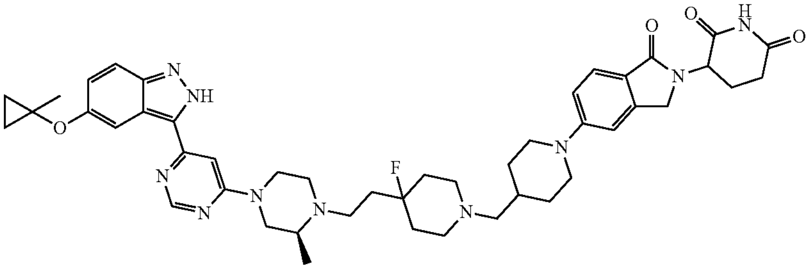 [SMILES: C[C@H]1CN(c2cc(-c3[nH]nc4ccc(OC5(C)CC5)cc34)ncn2)CCN1CCC1(F)CCN(CC2CCN(c3ccc4c(c3)CN(C3CCC(=O)NC3=O)C4=O)CC2)CC1] | 3-(5-{4-[(4-fluoro-4-{2-[(2S)-2-methyl-4-{6-[5-(1-methylcyclopropoxy)-2H-indazol-3-yl]pyrimidin-4-yl}piperazin-1-yl]ethyl}piperidin-1-yl)methyl]piperidin-1-yl}-1-oxo-2,3-dihydro-1H-isoindol-2-yl)piperidine-2,6-dione |
| 65 | 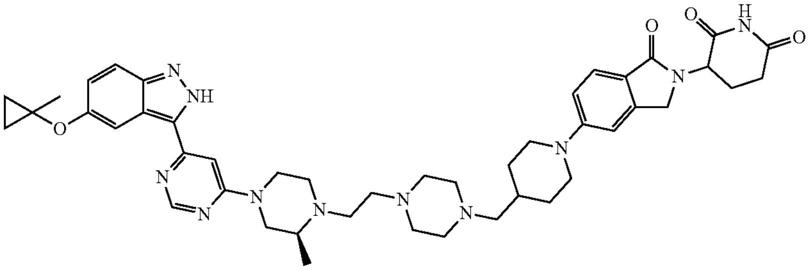 [SMILES: C[C@H]1CN(c2cc(-c3[nH]nc4ccc(OC5(C)CC5)cc34)ncn2)CCN1CCN1CCN(CC2CCN(c3ccc4c(c3)CN(C3CCC(=O)NC3=O)C4=O)CC2)CC1] | 3-(5-{4-[(4-{2-[(2S)-2-methyl-4-{6-[5-(1-methylcyclopropoxy)-2H-indazol-3-yl]pyrimidin-4-yl}piperazin-1-yl]ethyl}piperazin-1-yl)methyl]piperidin-1-yl}-1-oxo-2,3-dihydro-1H-isoindol-2-yl)piperidine-2,6-dione |
| 66 | 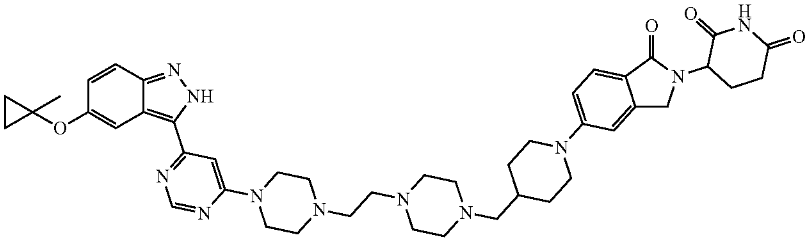 [SMILES: CC1(Oc2ccc3n[nH]c(-c4cc(N5CCN(CCN6CCN(CC7CCN(c8ccc9c(c8)CN(C8CCC(=O)NC8=O)C9=O)CC7)CC6)CC5)ncn4)c3c2)CC1] | 3-{5-[4-({4-[2-(4-{6-[5-(1-methylcyclopropoxy)-2H-indazol-3-yl]pyrimidin-4-yl}piperazin-1-yl)ethyl]piperazin-1-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 67 | 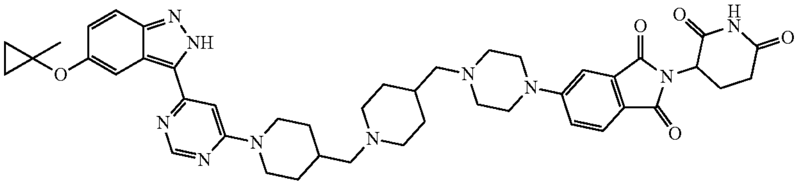 [SMILES: CC1(Oc2ccc3n[nH]c(-c4cc(N5CCC(CN6CCC(CN7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({1-[(1-{6-[5-(1-methylcyclopropoxy)-2H-indazol-3-yl]pyrimidin-4-yl}piperidin-4-yl)methyl]piperidin-4-yl}methyl)piperazin-1-yl]-2,3-dihydro-1H-isoindole-1,3-dione |
| 68 | 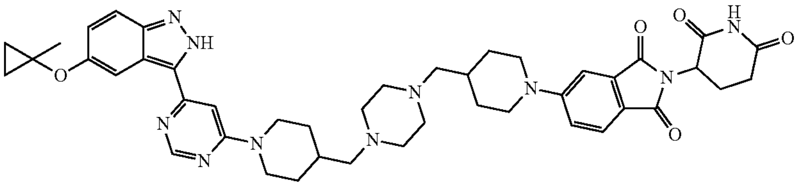 [SMILES: CC1(Oc2ccc3n[nH]c(-c4cc(N5CCC(CN6CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({4-[(1-{6-[5-(1-methylcyclopropoxy)-2H-indazol-3-yl]pyrimidin-4-yl}piperidin-4-yl)methyl]piperazin-1-yl}methyl)piperidin-1-yl]-2,3-dihydro-1H-isoindole-1,3-dione |
| 69 | 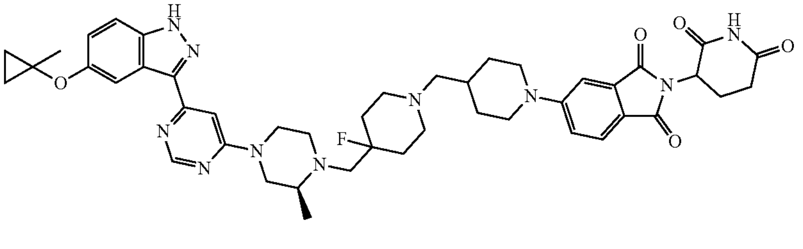 [SMILES: C[C@H]1CN(c2cc(-c3n[nH]c4ccc(OC5(C)CC5)cc34)ncn2)CCN1CC1(F)CCN(CC2CCN(c3ccc4c(c3)C(=O)N(C3CCC(=O)NC3=O)C4=O)CC2)CC1] | 2-(2,6-dioxopiperidin-3-yl)-5-{4-[(4-fluoro-4-{[(2S)-2-methyl-4-{6-[5-(1-methylcyclopropoxy)-1H-indazol-3-yl]pyrimidin-4-yl}piperazin-1-yl]methyl}piperidin-1-yl)methyl]piperidin-1-yl}-2,3-dihydro-1H-isoindole-1,3-dione |
| 70 | 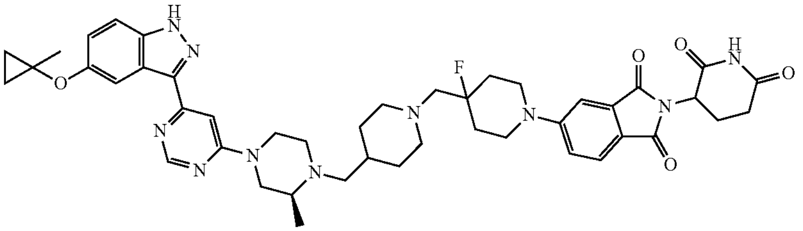 [SMILES: C[C@H]1CN(c2cc(-c3n[nH]c4ccc(OC5(C)CC5)cc34)ncn2)CCN1CC1CCN(CC2(F)CCN(c3ccc4c(c3)C(=O)N(C3CCC(=O)NC3=O)C4=O)CC2)CC1] | 2-(2,6-dioxopiperidin-3-yl)-5-{4-fluoro-4-[(4-{[(2S)-2-methyl-4-{6-[5-(1-methylcyclopropoxy)-1H-indazol-3-yl]pyrimidin-4-yl}piperazin-1-yl]methyl}piperidin-1-yl)methyl]piperidin-1-yl}-2,3-dihydro-1H-isoindole-1,3-dione |
| 71 | 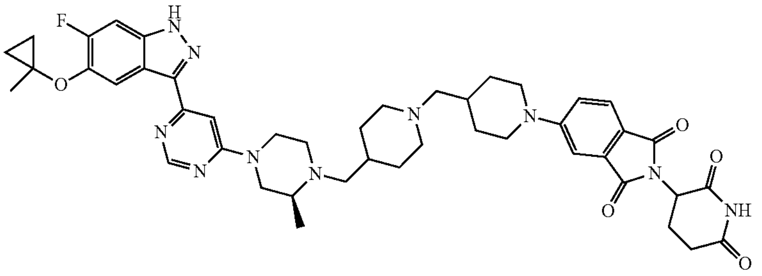 [SMILES: C[C@H]1CN(c2cc(-c3n[nH]c4cc(F)c(OC5(C)CC5)cc34)ncn2)CCN1CC1CCN(CC2CCN(c3ccc4c(c3)C(=O)N(C3CCC(=O)NC3=O)C4=O)CC2)CC1] | 2-(2,6-dioxopiperidin-3-yl)-5-{4-[(4-{[(2S)-4-{6-[6-fluoro-5-(1-methylcyclopropoxy)-1H-indazol-3-yl]pyrimidin-4-yl}-2-methylpiperazin-1-yl]methyl}piperidin-1-yl)methyl]piperidin-1-yl}-2,3-dihydro-1H-isoindole-1,3-dione |
| 72 | 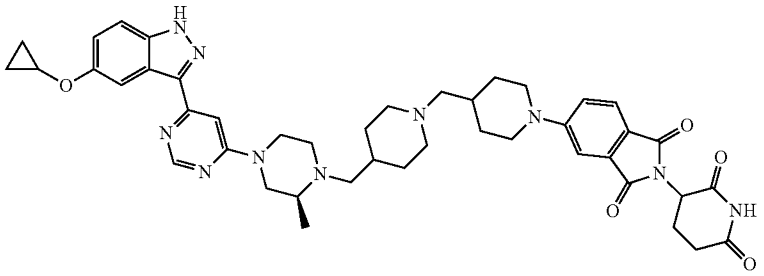 [SMILES: C[C@H]1CN(c2cc(-c3n[nH]c4ccc(OC5CC5)cc34)ncn2)CCN1CC1CCN(CC2CCN(c3ccc4c(c3)C(=O)N(C3CCC(=O)NC3=O)C4=O)CC2)CC1] | 5-{4-[(4-{[(2S)-4-[6-(5-cyclopropoxy-1H-indazol-3-yl)pyrimidin-4-yl]-2-methylpiperazin-1-yl]methyl}piperidin-1-yl)methyl]piperidin-1-yl}-2-(2,6-dioxopiperidin-3-yl)-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 73 | 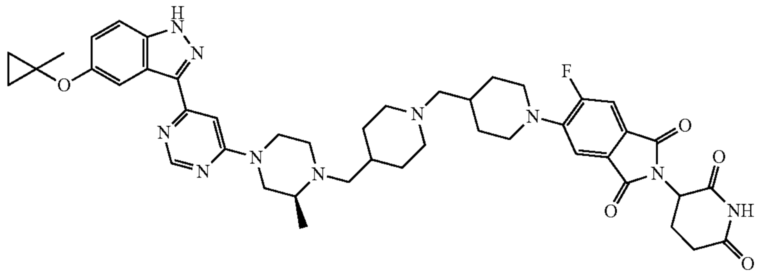 [SMILES: C[C@H]1CN(c2cc(-c3n[nH]c4ccc(OC5(C)CC5)cc34)ncn2)CCN1CC1CCN(CC2CCN(c3cc4c(cc3F)C(=O)N(C3CCC(=O)NC3=O)C4=O)CC2)CC1] | 2-(2,6-dioxopiperidin-3-yl)-5-fluoro-6-{4-[(4-{[(2S)-2-methyl-4-{6-[5-(1-methylcyclopropoxy)-1H-indazol-3-yl]pyrimidin-4-yl}piperazin-1-yl]methyl}piperidin-1-yl)methyl]piperidin-1-yl}-2,3-dihydro-1H-isoindole-1,3-dione |
| 74 | 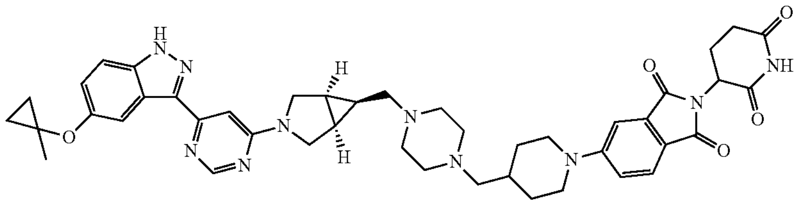 [SMILES: CC1(Oc2ccc3[nH]nc(-c4cc(N5C[C@@H]6[C@H](CN7CCN(CC8CCN(c9ccc%10c(c9)C(=O)N(C9CCC(=O)NC9=O)C%10=O)CC8)CC7)[C@@H]6C5)ncn4)c3c2)CC1] | 2-(2,6-dioxopiperidin-3-yl)-5-{4-[(4-{[(1r,5s,6r)-3-{6-[5-(1-methylcyclopropoxy)-1H-indazol-3-yl]pyrimidin-4-yl}-3-azabicyclo[3.1.0]hexan-6-yl]methyl}piperazin-1-yl)methyl]piperidin-1-yl}-2,3-dihydro-1H-isoindole-1,3-dione |
| 75 | 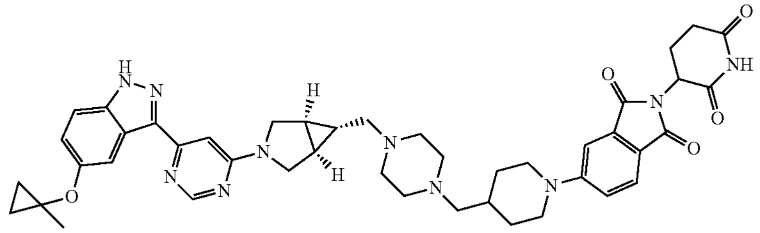 [SMILES: CC1(Oc2ccc3[nH]nc(-c4cc(N5C[C@@H]6[C@@H](CN7CCN(CC8CCN(c9ccc%10c(c9)C(=O)N(C9CCC(=O)NC9=O)C%10=O)CC8)CC7)[C@@H]6C5)ncn4)c3c2)CC1] | 2-(2,6-dioxopiperidin-3-yl)-5-{4-[(4-{[(1r,5s,6s)-3-{6-[5-(1-methylcyclopropoxy)-1H-indazol-3-yl]pyrimidin-4-yl}-3-azabicyclo[3.1.0]hexan-6-yl]methyl}piperazin-1-yl)methyl]piperidin-1-yl}-2,3-dihydro-1H-isoindole-1,3-dione |
| 76 | 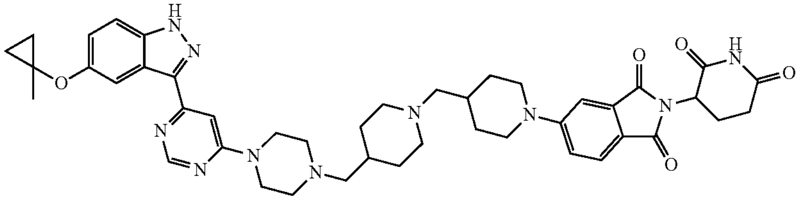 [SMILES: CC1(Oc2ccc3[nH]nc(-c4cc(N5CCN(CC6CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({4-[(4-{6-[5-(1-methylcyclopropoxy)-1H-indazol-3-yl]pyrimidin-4-yl}piperazin-1-yl)methyl]piperidin-1-yl}methyl)piperidin-1-yl]-2,3-dihydro-1H-isoindole-1,3-dione |
| 77 | 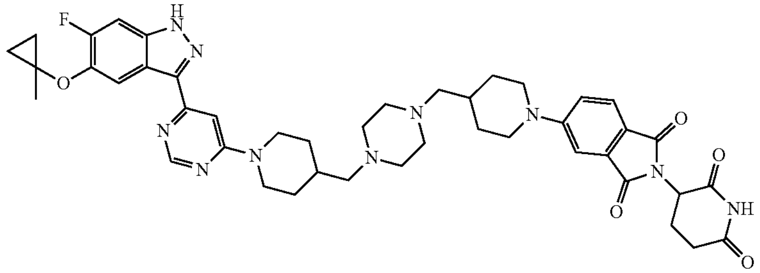 [SMILES: CC1(Oc2cc3c(-c4cc(N5CCC(CN6CCN(CC7CCN(c8ccc9c(c8)C(=O)N(C8CCC(=O)NC8=O)C9=O)CC7)CC6)CC5)ncn4)n[nH]c3cc2F)CC1] | 2-(2,6-dioxopiperidin-3-yl)-5-[4-({4-[(1-{6-[6-fluoro-5-(1-methylcyclopropoxy)-1H-indazol-3-yl]pyrimidin-4-yl}piperidin-4-yl)methyl]piperazin-1-yl}methyl)piperidin-1-yl]-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 78 | 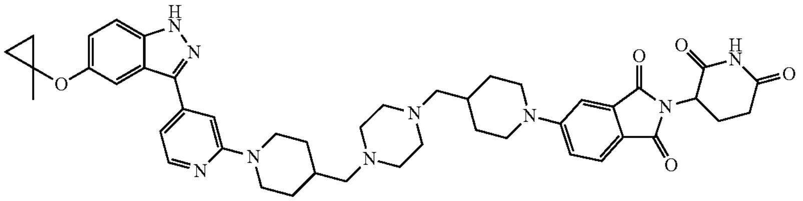 [SMILES: CC1(Oc2ccc3[nH]nc(-c4ccnc(N5CCC(CN6CCN(CC7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-[4-({4-[(1-{4-[5-(1-methylcyclopropoxy)-1H-indazol-3-yl]pyridin-2-yl}piperidin-4-yl)methyl]piperazin-1-yl}methyl)piperidin-1-yl]-2,3-dihydro-1H-isoindole-1,3-dione |
| 79 | 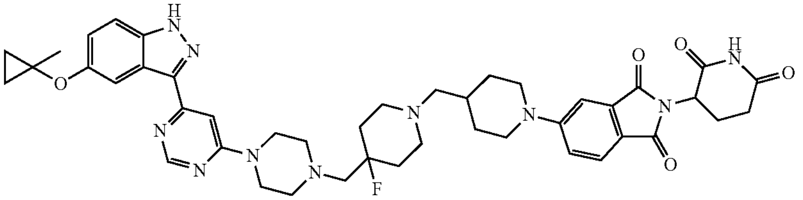 [SMILES: CC1(Oc2ccc3[nH]nc(-c4cc(N5CCN(CC6(F)CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({4-fluoro-4-[(4-{6-[5-(1-methylcyclopropoxy)-1H-indazol-3-yl]pyrimidin-4-yl}piperazin-1-yl)methyl]piperidin-1-yl}methyl)piperidin-1-yl]-2,3-dihydro-1H-isoindole-1,3-dione |
| 80 | 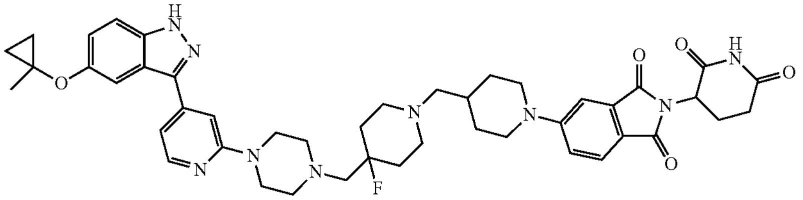 [SMILES: CC1(Oc2ccc3[nH]nc(-c4ccnc(N5CCN(CC6(F)CCN(CC7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-[4-({4-fluoro-4-[(4-{4-[5-(1-methylcyclopropoxy)-1H-indazol-3-yl]pyridin-2-yl}piperazin-1-yl)methyl]piperidin-1-yl}methyl)piperidin-1-yl]-2,3-dihydro-1H-isoindole-1,3-dione |
| 81 | 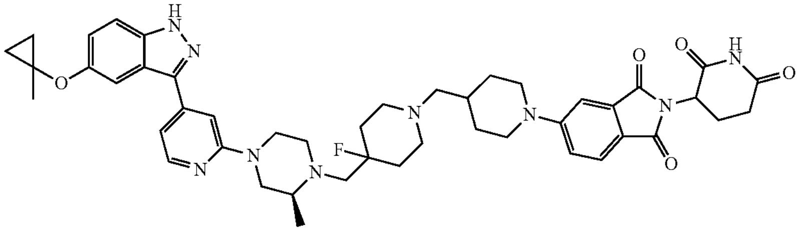 [SMILES: C[C@H]1CN(c2cc(-c3n[nH]c4ccc(OC5(C)CC5)cc34)ccn2)CCN1CC1(F)CCN(CC2CCN(c3ccc4c(c3)C(=O)N(C3CCC(=O)NC3=O)C4=O)CC2)CC1] | 2-(2,6-dioxopiperidin-3-yl)-5-{4-[(4-fluoro-4-{[(2S)-2-methyl-4-{4-[5-(1-methylcyclopropoxy)-1H-indazol-3-yl]pyridin-2-yl}piperazin-1-yl]methyl}piperidin-1-yl)methyl]piperidin-1-yl}-2,3-dihydro-1H-isoindole-1,3-dione |
| 82 | 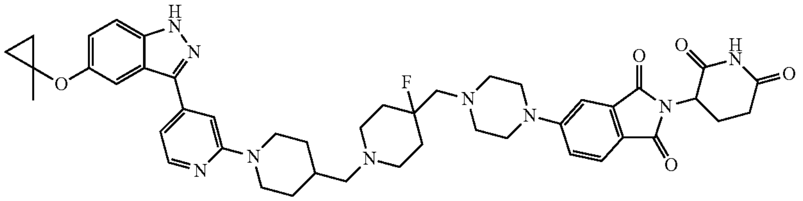 [SMILES: CC1(Oc2ccc3[nH]nc(-c4ccnc(N5CCC(CN6CCC(F)(CN7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-[4-({4-fluoro-1-[(1-{4-[5-(1-methylcyclopropoxy)-1H-indazol-3-yl]pyridin-2-yl}piperidin-4-yl)methyl]piperidin-4-yl}methyl)piperazin-1-yl]-2,3-dihydro-1H-isoindole-1,3-dione |
| 83 | 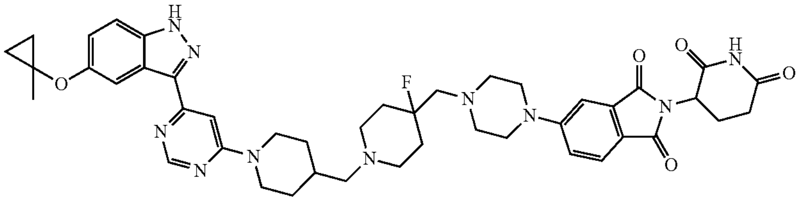 [SMILES: CC1(Oc2ccc3[nH]nc(-c4cc(N5CCC(CN6CCC(F)(CN7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({4-fluoro-1-[(1-{6-[5-(1-methylcyclopropoxy)-1H-indazol-3-yl]pyrimidin-4-yl}piperidin-4-yl)methyl]piperidin-4-yl}methyl)piperazin-1-yl]-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 84 | 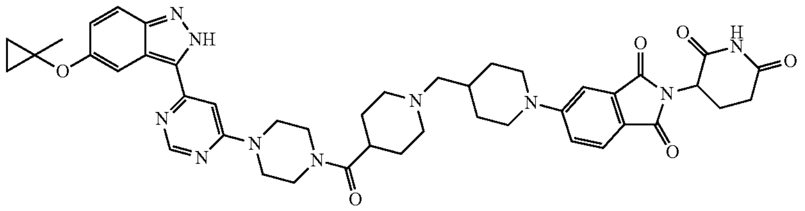 [SMILES: CC1(Oc2ccc3n[nH]c(-c4cc(N5CCN(C(=O)C6CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{[4-(4-{6-[5-(1-methylcyclopropoxy)-2H-indazol-3-yl]pyrimidin-4-yl}piperazine-1-carbonyl)piperidin-1-yl]methyl}piperidin-1-yl)-2,3-dihydro-1H-isoindole-1,3-dione |
| 85 | 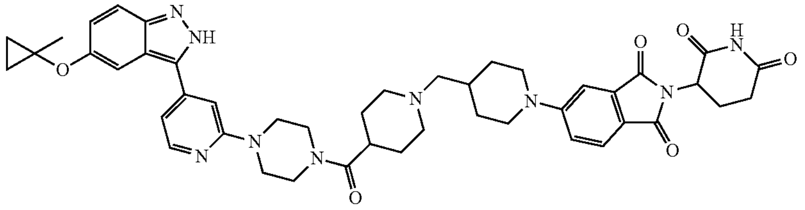 [SMILES: CC1(Oc2ccc3n[nH]c(-c4ccnc(N5CCN(C(=O)C6CCN(CC7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{[4-(4-{4-[5-(1-methylcyclopropoxy)-2H-indazol-3-yl]pyridin-2-yl}piperazine-1-carbonyl)piperidin-1-yl]methyl}piperidin-1-yl)-2,3-dihydro-1H-isoindole-1,3-dione |
| 86 | 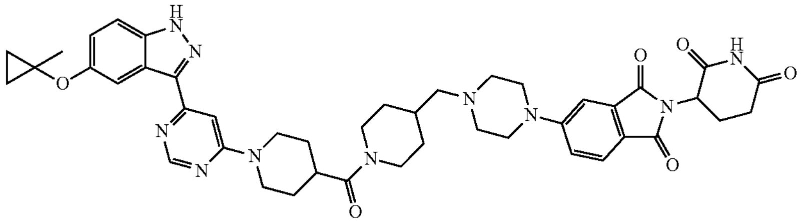 [SMILES: CC1(Oc2ccc3[nH]nc(-c4cc(N5CCC(C(=O)N6CCC(CN7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{[1-(1-{6-[5-(1-methylcyclopropoxy)-1H-indazol-3-yl]pyrimidin-4-yl}piperidine-4-carbonyl)piperidin-4-yl]methyl}piperazin-1-yl)-2,3-dihydro-1H-isoindole-1,3-dione |
| 87 | 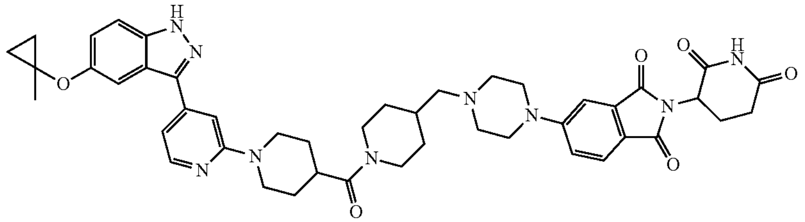 [SMILES: CC1(Oc2ccc3[nH]nc(-c4ccnc(N5CCC(C(=O)N6CCC(CN7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{[1-(1-{4-[5-(1-methylcyclopropoxy)-1H-indazol-3-yl]pyridin-2-yl}piperidine-4-carbonyl)piperidin-4-yl]methyl}piperazin-1-yl)-2,3-dihydro-1H-isoindole-1,3-dione |
| 88 | 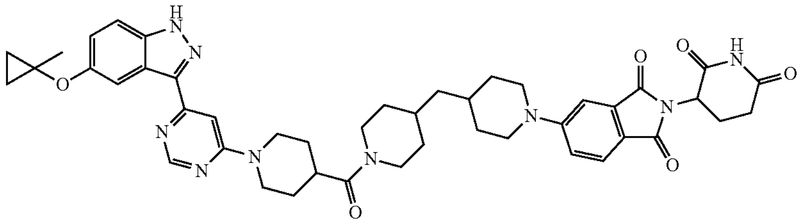 [SMILES: CC1(Oc2ccc3[nH]nc(-c4cc(N5CCC(C(=O)N6CCC(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{[1-(1-{6-[5-(1-methylcyclopropoxy)-1H-indazol-3-yl]pyrimidin-4-yl}piperidine-4-carbonyl)piperidin-4-yl]methyl}piperidin-1-yl)-2,3-dihydro-1H-isoindole-1,3-dione |
| 89 | 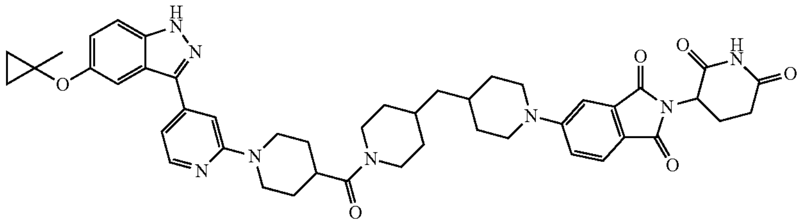 [SMILES: CC1(Oc2ccc3[nH]nc(-c4ccnc(N5CCC(C(=O)N6CCC(CC7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{[1-(1-{4-[5-(1-methylcyclopropoxy)-1H-indazol-3-yl]pyridin-2-yl}piperidine-4-carbonyl)piperidin-4-yl]methyl}piperidin-1-yl)-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 90 | 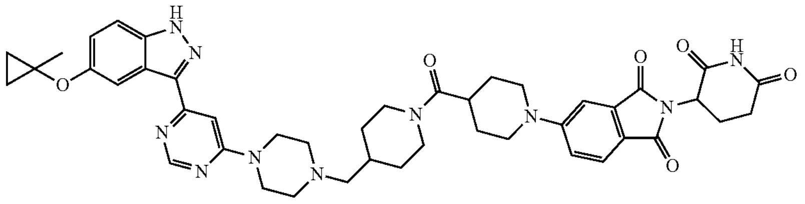 [SMILES: CC1(Oc2ccc3[nH]nc(-c4cc(N5CCN(CC6CCN(C(=O)C7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{4-[(4-{6-[5-(1-methylcyclopropoxy)-1H-indazol-3-yl]pyrimidin-4-yl}piperazin-1-yl)methyl]piperidine-1-carbonyl}piperidin-1-yl)-2,3-dihydro-1H-isoindole-1,3-dione |
| 91 | 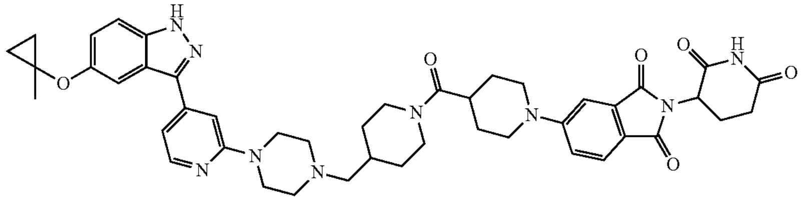 [SMILES: CC1(Oc2ccc3[nH]nc(-c4ccnc(N5CCN(CC6CCN(C(=O)C7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{4-[(4-{4-[5-(1-methylcyclopropoxy)-1H-indazol-3-yl]pyridin-2-yl}piperazin-1-yl)methyl]piperidine-1-carbonyl}piperidin-1-yl)-2,3-dihydro-1H-isoindole-1,3-dione |
| 92 | 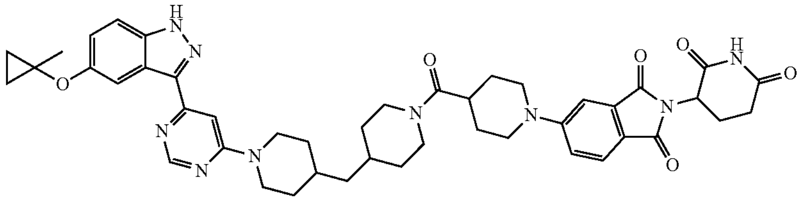 [SMILES: CC1(Oc2ccc3[nH]nc(-c4cc(N5CCC(CC6CCN(C(=O)C7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{4-[(1-{6-[5-(1-methylcyclopropoxy)-1H-indazol-3-yl]pyrimidin-4-yl}piperidin-4-yl)methyl]piperidine-1-carbonyl}piperidin-1-yl)-2,3-dihydro-1H-isoindole-1,3-dione |
| 93 | 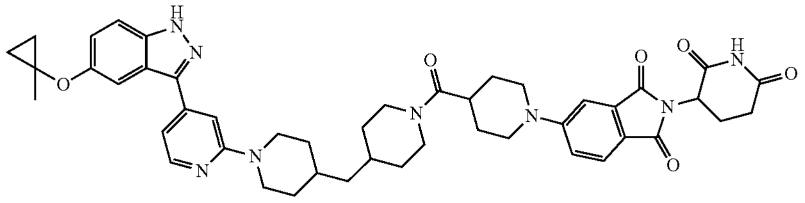 | 2-(2,6-dioxopiperidin-3-yl)-5-(4-{4-[(1-{4-[5-(1-methylcyclopropoxy)-1H-indazol-3-yl]pyridin-2-yl}piperidin-4-yl)methyl]piperidine-1-carbonyl}piperidin-1-yl)-2,3-dihydro-1H-isoindole-1,3-dione |
| 94 | 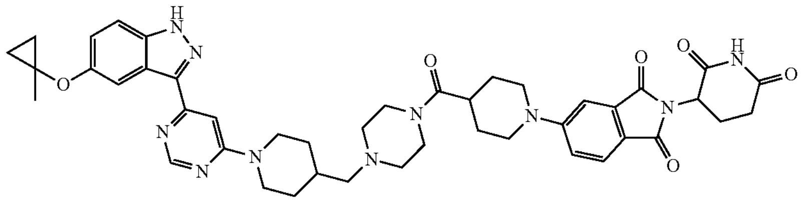 [SMILES: CC1(Oc2ccc3[nH]nc(-c4cc(N5CCC(CN6CCN(C(=O)C7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{4-[(1-{6-[5-(1-methylcyclopropoxy)-1H-indazol-3-yl]pyrimidin-4-yl}piperidin-4-yl)methyl]piperazine-1-carbonyl}piperidin-1-yl)-2,3-dihydro-1H-isoindole-1,3-dione |
| 95 | 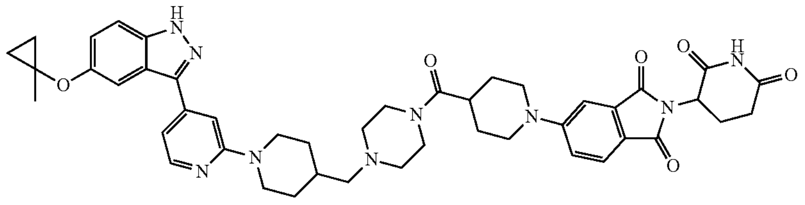 [SMILES: CC1(Oc2ccc3[nH]nc(-c4ccnc(N5CCC(CN6CCN(C(=O)C7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{4-[(1-{4-[5-(1-methylcyclopropoxy)-1H-indazol-3-yl]pyridin-2-yl}piperidin-4-yl)methyl]piperazine-1-carbonyl}piperidin-1-yl)-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 96 | 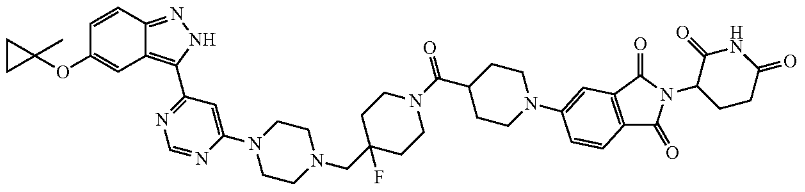 [SMILES: CC1(Oc2ccc3n[nH]c(-c4cc(N5CCN(CC6(F)CCN(C(=O)C7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{4-fluoro-4-[(4-{6-[5-(1-methylcyclopropoxy)-2H-indazol-3-yl]pyrimidin-4-yl}piperazin-1-yl)methyl]piperidine-1-carbonyl}piperidin-1-yl)-2,3-dihydro-1H-isoindole-1,3-dione |
| 97 | 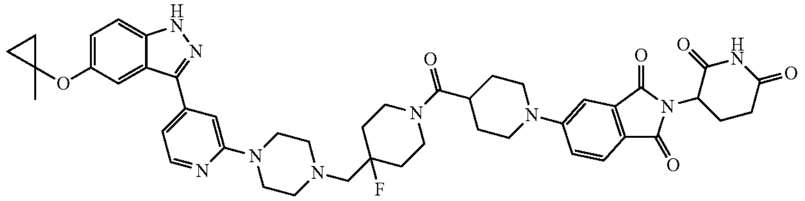 [SMILES: CC1(Oc2ccc3[nH]nc(-c4ccnc(N5CCN(CC6(F)CCN(C(=O)C7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{4-fluoro-4-[(4-{4-[5-(1-methylcyclopropoxy)-1H-indazol-3-yl]pyridin-2-yl}piperazin-1-yl)methyl]piperidine-1-carbonyl}piperidin-1-yl)-2,3-dihydro-1H-isoindole-1,3-dione |
| 98 | 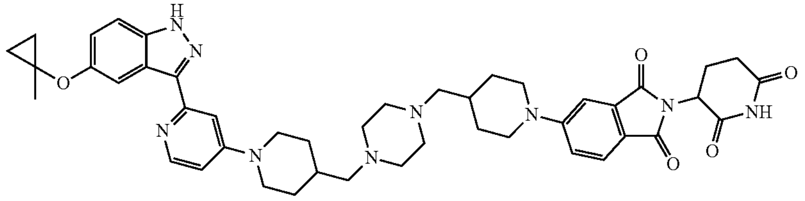 [SMILES: CC1(Oc2ccc3[nH]nc(-c4cc(N5CCC(CN6CCN(CC7CCN(c8ccc9c(c8)C(=O)N(C8CCC(=O)NC8=O)C9=O)CC7)CC6)CC5)ccn4)c3c2)CC1] | 2-(2,6-dioxopiperidin-3-yl)-5-[4-({4-[(1-{2-[5-(1-methylcyclopropoxy)-1H-indazol-3-yl]pyridin-4-yl}piperidin-4-yl)methyl]piperazin-1-yl}methyl)piperidin-1-yl]-2,3-dihydro-1H-isoindole-1,3-dione |
| 99 | 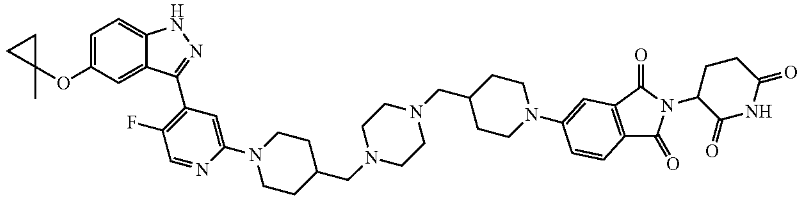 [SMILES: CC1(Oc2ccc3[nH]nc(-c4cc(N5CCC(CN6CCN(CC7CCN(c8ccc9c(c8)C(=O)N(C8CCC(=O)NC8=O)C9=O)CC7)CC6)CC5)ncc4F)c3c2)CC1] | 2-(2,6-dioxopiperidin-3-yl)-5-[4-({4-[(1-{5-fluoro-4-[5-(1-methylcyclopropoxy)-1H-indazol-3-yl]pyridin-2-yl}piperidin-4-yl)methyl]piperazin-1-yl}methyl)piperidin-1-yl]-2,3-dihydro-1H-isoindole-1,3-dione |
| 100 | 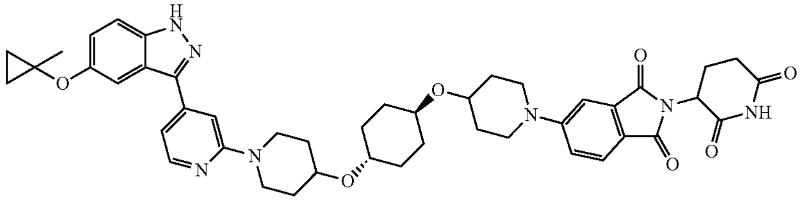 [SMILES: CC1(Oc2ccc3[nH]nc(-c4ccnc(N5CCC(O[C@H]6CC[C@H](OC7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{[(1r,4r)-4-[(1-{4-[5-(1-methylcyclopropoxy)-1H-indazol-3-yl]pyridin-2-yl}piperidin-4-yl)oxy]cyclohexyl]oxy}piperidin-1-yl)-2,3-dihydro-1H-isoindole-1,3-dione |
| 101 | 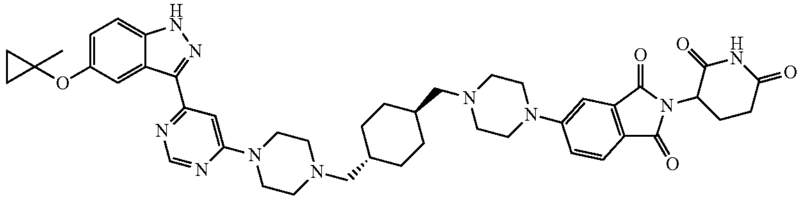 [SMILES: CC1(Oc2ccc3[nH]nc(-c4cc(N5CCN(C[C@H]6CC[C@H](CN7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{[(1r,4r)-4-[(4-{6-[5-(1-methylcyclopropoxy)-1H-indazol-3-yl]pyrimidin-4-yl}piperazin-1-yl)methyl]cyclohexyl]methyl}piperazin-1-yl)-2,3-dihydro-1H-isoindole-1,3-dione |

TABLE 1-continued

Exemplary bifunctional compounds of the present disclosure**

| Ex. No. | Chemical Structure | IUPAC Name |
|---|---|---|
| 102 | 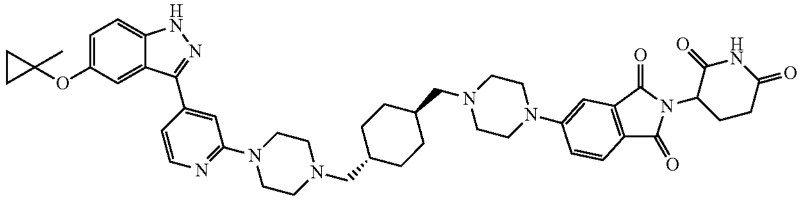 [SMILES: CC1(Oc2ccc3[nH]nc(-c4ccnc(N5CCN(C[C@H]6CC[C@H](CN7CCN(c8ccc9c(c8)C(=O)N(C8CCC(=O)NC8=O)C9=O)CC7)CC6)CC5)c4)c3c2)CC1] | 2-(2,6-dioxopiperidin-3-yl)-5-(4-{[(1r,4r)-4-[(4-{4-[5-(1-methylcyclopropoxy)-1H-indazol-3-yl]pyridin-2-yl}piperazin-1-yl)methyl]cyclohexyl]methyl}piperazin-1-yl)-2,3-dihydro-1H-isoindole-1,3-dione |
| 103 | 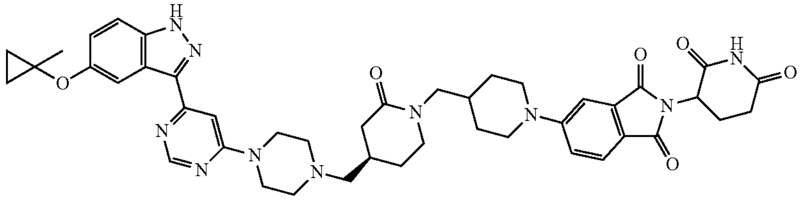 [SMILES: CC1(Oc2ccc3[nH]nc(-c4cc(N5CCN(C[C@@H]6CCN(CC7CCN(c8ccc9c(c8)C(=O)N(C8CCC(=O)NC8=O)C9=O)CC7)C(=O)C6)CC5)ncn4)c3c2)CC1] | 2-(2,6-dioxopiperidin-3-yl)-5-(4-{[(4R)-4-[(4-{6-[5-(1-methylcyclopropoxy)-1H-indazol-3-yl]pyrimidin-4-yl}piperazin-1-yl)methyl]-2-oxopiperidin-1-yl]methyl}piperidin-1-yl)-2,3-dihydro-1H-isoindole-1,3-dione |
| 104 | 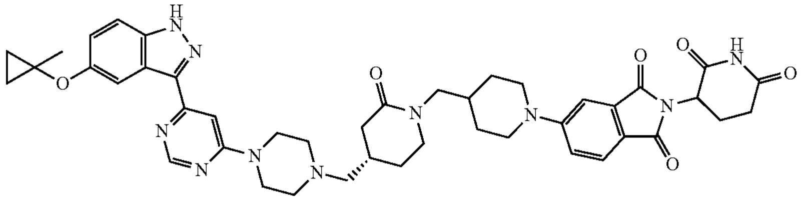 [SMILES: CC1(Oc2ccc3[nH]nc(-c4cc(N5CCN(C[C@H]6CCN(CC7CCN(c8ccc9c(c8)C(=O)N(C8CCC(=O)NC8=O)C9=O)CC7)C(=O)C6)CC5)ncn4)c3c2)CC1] | 2-(2,6-dioxopiperidin-3-yl)-5-(4-{[(4S)-4-[(4-{6-[5-(1-methylcyclopropoxy)-1H-indazol-3-yl]pyrimidin-4-yl}piperazin-1-yl)methyl]-2-oxopiperidin-1-yl]methyl}piperidin-1-yl)-2,3-dihydro-1H-isoindole-1,3-dione |
| 105 | 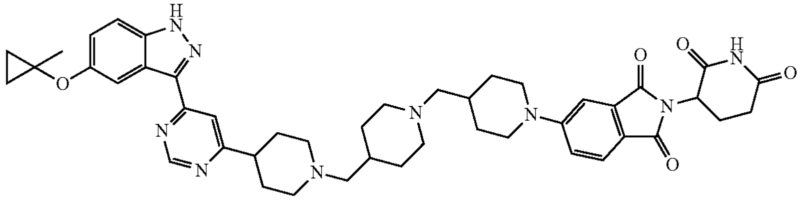 [SMILES: CC1(Oc2ccc3[nH]nc(-c4cc(C5CCN(CC6CCN(CC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-[4-({4-[(4-{6-[5-(1-methylcyclopropoxy)-1H-indazol-3-yl]pyrimidin-4-yl}piperidin-1-yl)methyl]piperidin-1-yl}methyl)piperidin-1-yl]-2,3-dihydro-1H-isoindole-1,3-dione |
| 106 | 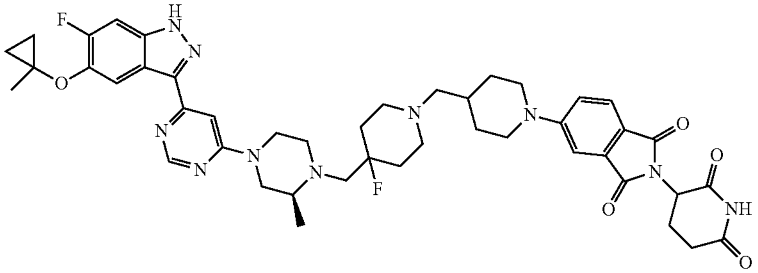 [SMILES: C[C@H]1CN(c2cc(-c3n[nH]c4cc(F)c(OC5(C)CC5)cc34)ncn2)CCN1CC1(F)CCN(CC2CCN(c3ccc4c(c3)C(=O)N(C3CCC(=O)NC3=O)C4=O)CC2)CC1] | 2-(2,6-dioxopiperidin-3-yl)-5-{4-[(4-fluoro-4-{[(2S)-4-{6-[6-fluoro-5-(1-methylcyclopropoxy)-1H-indazol-3-yl]pyrimidin-4-yl}-2-methylpiperazin-1-yl]methyl}piperidin-1-yl)methyl]piperidin-1-yl}-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 107 | 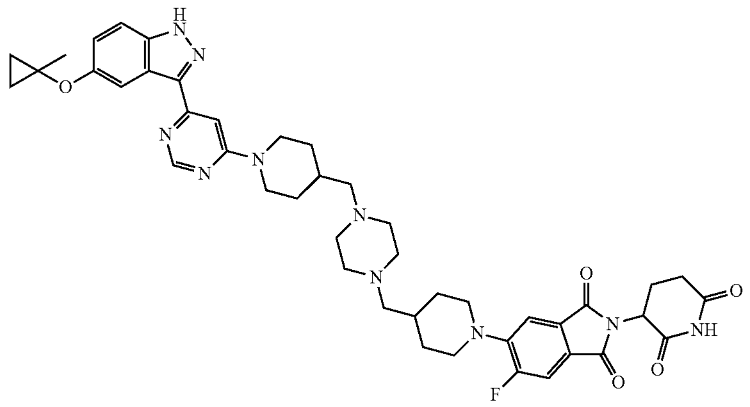 [SMILES: CC1(Oc2ccc3[nH]nc(-c4cc(N5CCC(CN6CCN(CC7CCN(c8cc9c(cc8F)C(=O)N(C8CCC(=O)NC8=O)C9=O)CC7)CC6)CC5)ncn4)c3c2)CC1] | 2-(2,6-dioxopiperidin-3-yl)-5-fluoro-6-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-2,3-dihydro-1H-isoindole-1,3-dione |
| 108 | 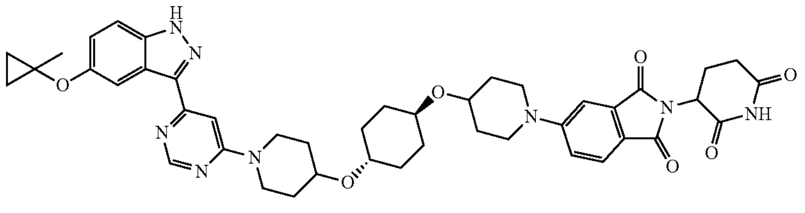 [SMILES: CC1(Oc2ccc3[nH]nc(-c4cc(N5CCC(O[C@H]6CC[C@H](OC7CCN(c8ccc9c(c8)C(=O)N(C8CCC(=O)NC8=O)C9=O)CC7)CC6)CC5)ncn4)c3c2)CC1] | 2-(2,6-dioxopiperidin-3-yl)-5-(4-{[(1r,4r)-4-[(1-{6-[5-(1-methylcyclopropoxy)-1H-indazol-3-yl]pyrimidin-4-yl}piperidin-4-yl)oxy]cyclohexyl]oxy}piperidin-1-yl)-2,3-dihydro-1H-isoindole-1,3-dione |
| 109 | 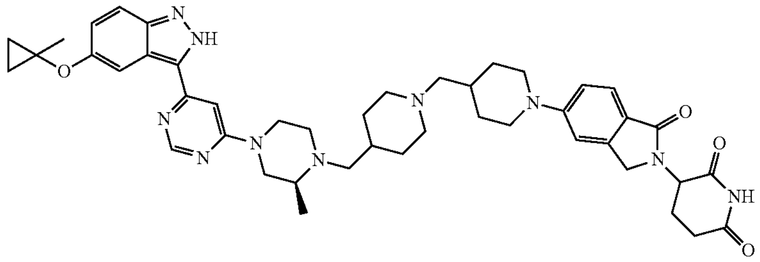 [SMILES: C[C@H]1CN(c2cc(-c3[nH]nc4ccc(OC5(C)CC5)cc34)ncn2)CCN1CC1CCN(CC2CCN(c3ccc4c(c3)CN(C3CCC(=O)NC3=O)C4=O)CC2)CC1] | 3-(5-{4-[(4-{[(2S)-2-methyl-4-{6-[5-(1-methylcyclopropoxy)-2H-indazol-3-yl]pyrimidin-4-yl}piperazin-1-yl]methyl}piperidin-1-yl)methyl]piperidin-1-yl}-1-oxo-2,3-dihydro-1H-isoindol-2-yl)piperidine-2,6-dione |
| 110 | 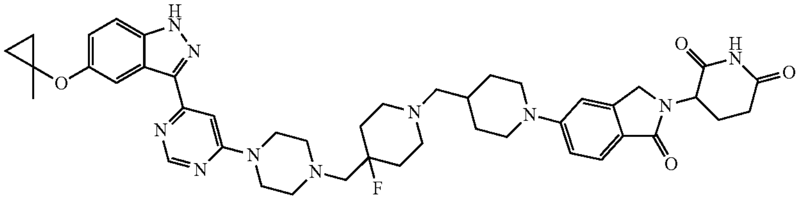 [SMILES: CC1(Oc2ccc3[nH]nc(-c4cc(N5CCN(CC6(F)CCN(CC7CCN(c8ccc9c(c8)CN(C8CCC(=O)NC8=O)C9=O)CC7)CC6)CC5)ncn4)c3c2)CC1] | 3-{5-[4-({4-fluoro-4-[(4-{6-[5-(1-methylcyclopropoxy)-1H-indazol-3-yl]pyrimidin-4-yl}piperazin-1-yl)methyl]piperidin-1-yl}methyl)piperidin-1-yl]-1-oxo-2,3-dihydro-1H-isoindol-2-yl}piperidine-2,6-dione |
| 111 | 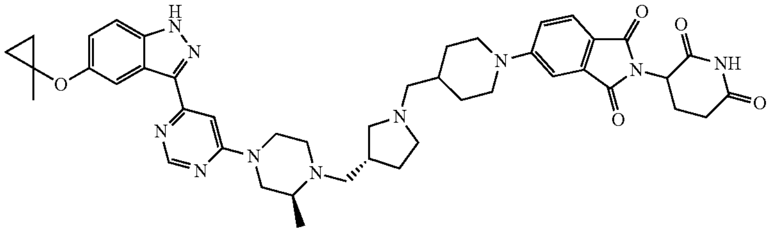 [SMILES: C[C@H]1CN(c2cc(-c3n[nH]c4ccc(OC5(C)CC5)cc34)ncn2)CCN1C[C@H]1CCN(CC2CCN(c3ccc4c(c3)C(=O)N(C3CCC(=O)NC3=O)C4=O)CC2)C1] | 2-(2,6-dioxopiperidin-3-yl)-5-(4-{[(3S)-3-{[(2S)-2-methyl-4-{6-[5-(1-methylcyclopropoxy)-1H-indazol-3-yl]pyrimidin-4-yl}piperazin-1-yl]methyl}pyrrolidin-1-yl]methyl}piperidin-1-yl)-2,3-dihydro-1H-isoindole-1,3-dione |

TABLE 1-continued

Exemplary bifunctional compounds of the present disclosure**

| Ex. No. | Chemical Structure | IUPAC Name |
|---|---|---|
| 112 | 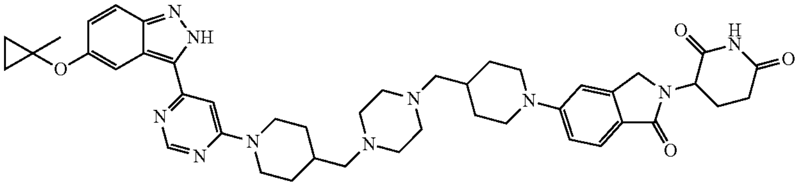 [SMILES: CC1(Oc2ccc3n[nH]c(-c4cc(N5CCC(CN6CCN(CC7CCN(c8ccc9c(c8)CN(C8CCC(=O)NC8=O)C9=O)CC7)CC6)CC5)ncn4)c3c2)CC1] | 3-{5-[4-({4-[(1-{6-[5-(1-methylcyclopropoxy)-2H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 113 | 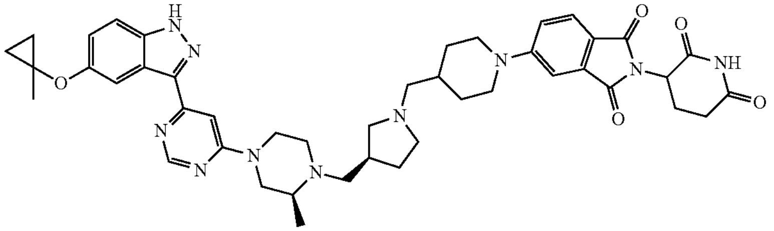 [SMILES: C[C@H]1CN(c2cc(-c3n[nH]c4ccc(OC5(C)CC5)cc34)ncn2)CCN1C[C@@H]1CCN(CC2CCN(c3ccc4c(c3)C(=O)N(C3CCC(=O)NC3=O)C4=O)CC2)C1] | 2-(2,6-dioxopiperidin-3-yl)-5-(4-{[(3R)-3-{[(2S)-2-methyl-4-{6-[5-(1-methylcyclopropoxy)-1H-indazol-3-yl]pyrimidin-4-yl}piperazin-1-yl]methyl}pyrrolidin-1-yl]methyl}piperidin-1-yl)-2,3-dihydro-1H-isoindole-1,3-dione |
| 114 | 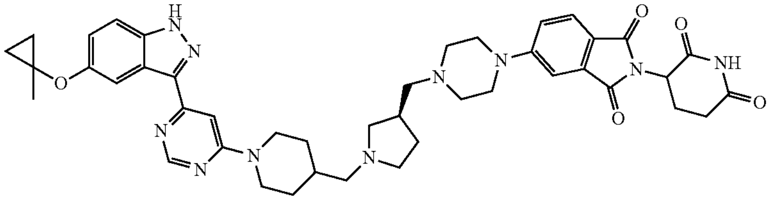 [SMILES: CC1(Oc2ccc3[nH]nc(-c4cc(N5CCC(CN6CC[C@H](CN7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(3S)-1-[(1-{6-[5-(1-methylcyclopropoxy)-1H-indazol-3-yl]pyrimidin-4-yl}piperidin-4-yl)methyl]pyrrolidin-3-yl]methyl}piperazin-1-yl)-2,3-dihydro-1H-isoindole-1,3-dione |
| 115 | 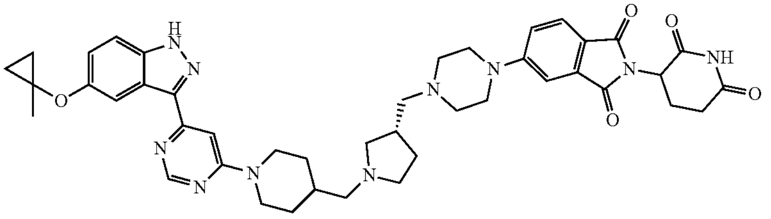 [SMILES: CC1(Oc2ccc3[nH]nc(-c4cc(N5CCC(CN6CC[C@@H](CN7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(3R)-1-[(1-{6-[5-(1-methylcyclopropoxy)-1H-indazol-3-yl]pyrimidin-4-yl}piperidin-4-yl)methyl]pyrrolidin-3-yl]methyl}piperazin-1-yl)-2,3-dihydro-1H-isoindole-1,3-dione |
| 116 | 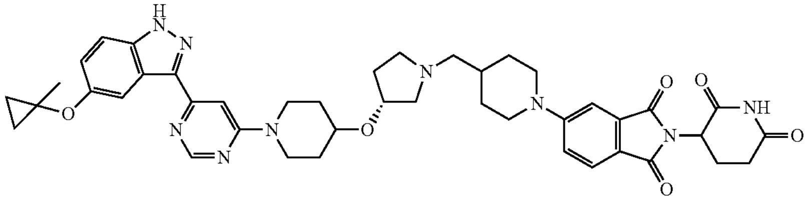 [SMILES: CC1(Oc2ccc3[nH]nc(-c4cc(N5CCC(O[C@@H]6CCN(CC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(3R)-3-[(1-{6-[5-(1-methylcyclopropoxy)-1H-indazol-3-yl]pyrimidin-4-yl}piperidin-4-yl)oxy]pyrrolidin-1-yl]methyl}piperidin-1-yl)-2,3-dihydro-1H-isoindole-1,3-dione |
| 117 | 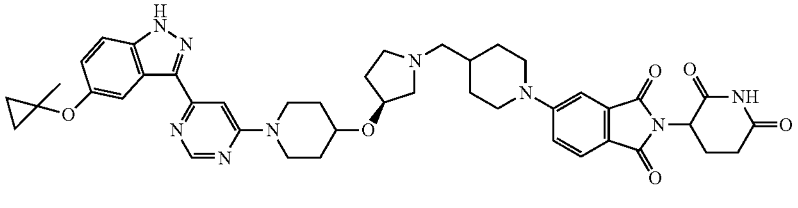 [SMILES: CC1(Oc2ccc3[nH]nc(-c4cc(N5CCC(O[C@H]6CCN(CC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(3S)-3-[(1-{6-[5-(1-methylcyclopropoxy)-1H-indazol-3-yl]pyrimidin-4-yl}piperidin-4-yl)oxy]pyrrolidin-1-yl]methyl}piperidin-1-yl)-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 118 | 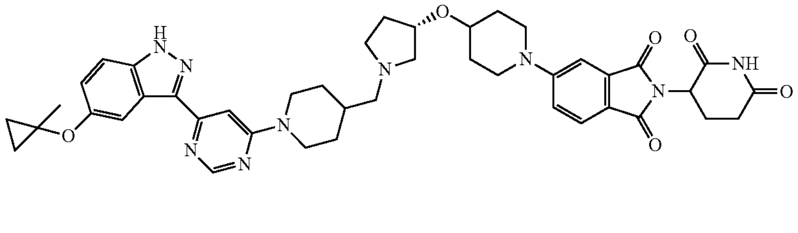 [SMILES: CC1(Oc2ccc3[nH]nc(-c4cc(N5CCC(CN6CC[C@H](OC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(3S)-1-[(1-{6-[5-(1-methylcyclopropoxy)-1H-indazol-3-yl]pyrimidin-4-yl}piperidin-4-yl)methyl]pyrrolidin-3-yl]oxy}piperidin-1-yl)-2,3-dihydro-1H-isoindole-1,3-dione |
| 119 | 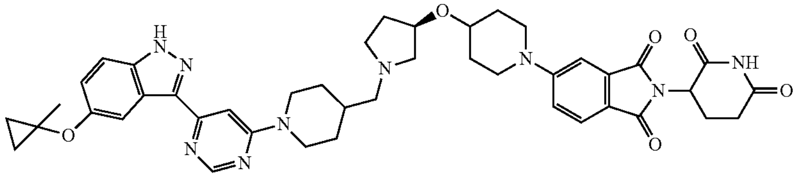 [SMILES: CC1(Oc2ccc3[nH]nc(-c4cc(N5CCC(CN6CC[C@@H](OC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(3R)-1-[(1-{6-[5-(1-methylcyclopropoxy)-1H-indazol-3-yl]pyrimidin-4-yl}piperidin-4-yl)methyl]pyrrolidin-3-yl]oxy}piperidin-1-yl)-2,3-dihydro-1H-isoindole-1,3-dione |
| 120 | 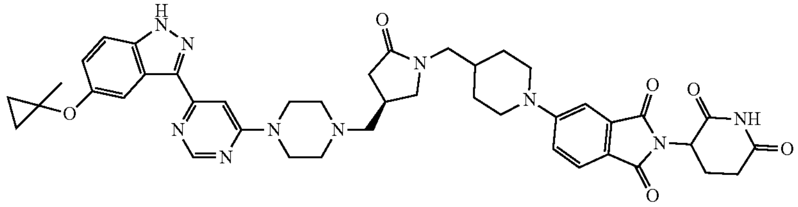 [SMILES: CC1(Oc2ccc3[nH]nc(-c4cc(N5CCN(C[C@H]6CC(=O)N(CC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(4R)-4-[(4-{6-[5-(1-methylcyclopropoxy)-1H-indazol-3-yl]pyrimidin-4-yl}piperazin-1-yl)methyl]-2-oxopyrrolidin-1-yl]methyl}piperidin-1-yl)-2,3-dihydro-1H-isoindole-1,3-dione |
| 121 | 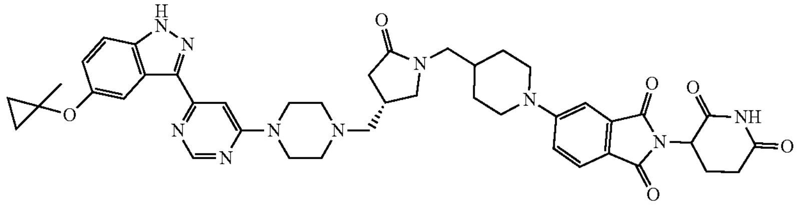 [SMILES: CC1(Oc2ccc3[nH]nc(-c4cc(N5CCN(C[C@@H]6CC(=O)N(CC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-(4-{[(4S)-4-[(4-{6-[5-(1-methylcyclopropoxy)-1H-indazol-3-yl]pyrimidin-4-yl}piperazin-1-yl)methyl]-2-oxopyrrolidin-1-yl]methyl}piperidin-1-yl)-2,3-dihydro-1H-isoindole-1,3-dione |
| 122 | 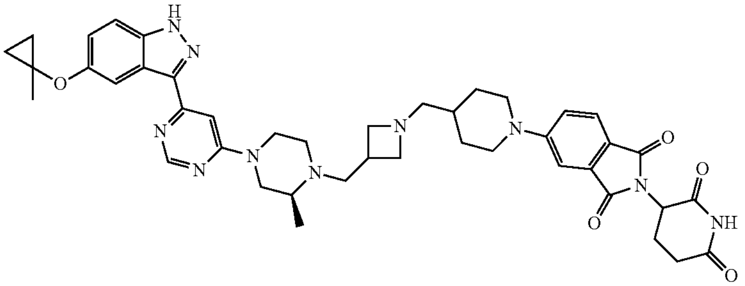 [SMILES: C[C@H]1CN(c2cc(-c3n[nH]c4ccc(OC5(C)CC5)cc34)ncn2)CCN1CC1CN(CC2CCN(c3ccc4c(c3)C(=O)N(C3CCC(=O)NC3=O)C4=O)CC2)C1] | 2-(2,6-dioxopiperidin-3-yl)-5-{4-[(3-{[(2S)-2-methyl-4-{6-[5-(1-methylcyclopropoxy)-1H-indazol-3-yl]pyrimidin-4-yl}piperazin-1-yl]methyl}azetidin-1-yl)methyl]piperidin-1-yl}-2,3-dihydro-1H-isoindole-1,3-dione |

TABLE 1-continued

Exemplary bifunctional compounds of the present disclosure**

| Ex. No. | Chemical Structure | IUPAC Name |
| --- | --- | --- |
| 123 | 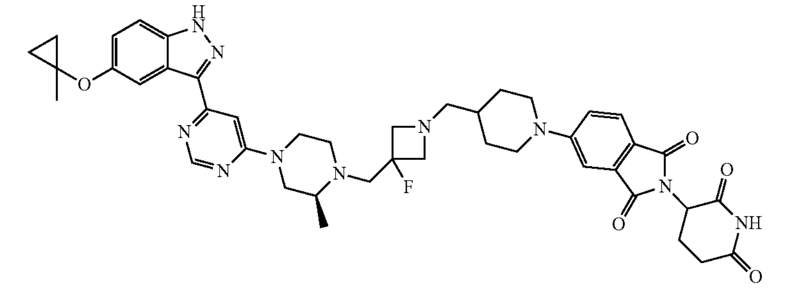 [SMILES: C[C@H]1CN(c2cc(-c3n[nH]c4ccc(OC5(C)CC5)cc34)ncn2)CCN1CC1(F)CN(CC2CCN(c3ccc4c(c3)C(=O)N(C3CCC(=O)NC3=O)C4=O)CC2)C1] | 2-(2,6-dioxopiperidin-3-yl)-5-{4-[(3-fluoro-3-{[(2S)-2-methyl-4-{6-[5-(1-methylcyclopropoxy)-1H-indazol-3-yl]pyrimidin-4-yl}piperazin-1-yl]methyl}azetidin-1-yl)methyl]piperidin-1-yl}-2,3-dihydro-1H-isoindole-1,3-dione |
| 124 | 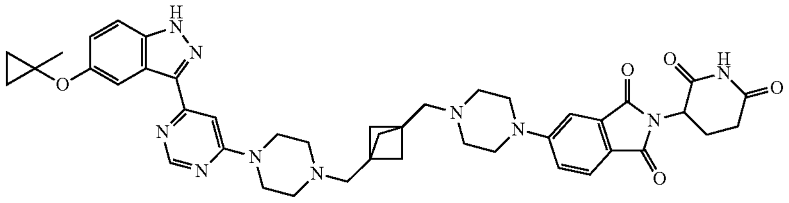 [SMILES: CC1(Oc2ccc3[nH]nc(-c4cc(N5CCN(CC67CC(CN8CCN(c9ccc%10c(c9)C(=O)N(C9CCC(=O)NC9=O)C%10=O)CC8)(C6)C7)CC5)ncn4)c3c2)CC1] | 2-(2,6-dioxopiperidin-3-yl)-5-[4-({3-[(4-{6-[5-(1-methylcyclopropoxy)-1H-indazol-3-yl]pyrimidin-4-yl}piperazin-1-yl)methyl]bicyclo[1.1.1]pentan-1-yl}methyl)piperazin-1-yl]-2,3-dihydro-1H-isoindole-1,3-dione |
| 125 | 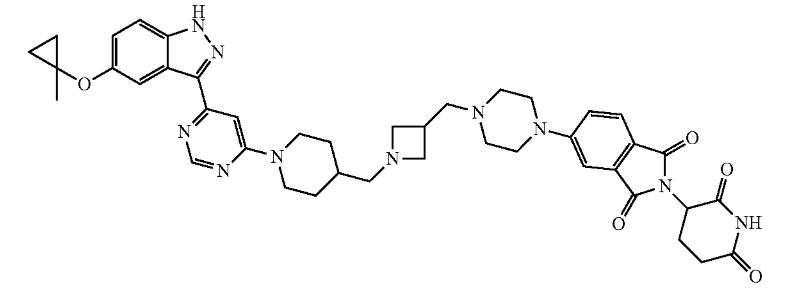 [SMILES: CC1(Oc2ccc3[nH]nc(-c4cc(N5CCC(CN6CC(CN7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-[4-({1-[(1-{6-[5-(1-methylcyclopropoxy)-1H-indazol-3-yl]pyrimidin-4-yl}piperidin-4-yl)methyl]azetidin-3-yl}methyl)piperazin-1-yl]-2,3-dihydro-1H-isoindole-1,3-dione |
| 126 | 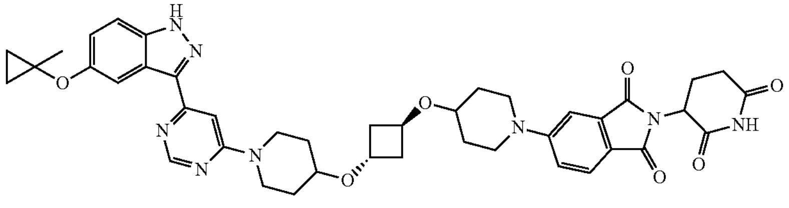 [SMILES: CC1(Oc2ccc3[nH]nc(-c4cc(N5CCC(O[C@H]6C[C@H](OC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-{4-[(1r,3r)-3-[(1-{6-[5-(1-methylcyclopropoxy)-1H-indazol-3-yl]pyrimidin-4-yl}piperidin-4-yl)oxy]cyclobutoxy]piperidin-1-yl}-2,3-dihydro-1H-isoindole-1,3-dione |
| 127 | 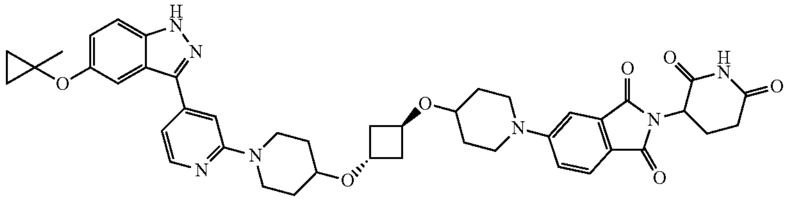 [SMILES: CC1(Oc2ccc3[nH]nc(-c4ccnc(N5CCC(O[C@H]6C[C@H](OC7CCN(c8ccc9c(c8)C(=O)N(C8CCC(=O)NC8=O)C9=O)CC7)C6)CC5)c4)c3c2)CC1] | 2-(2,6-dioxopiperidin-3-yl)-5-{4-[(1r,3r)-3-[(1-{4-[5-(1-methylcyclopropoxy)-1H-indazol-3-yl]pyridin-2-yl}piperidin-4-yl)oxy]cyclobutoxy]piperidin-1-yl}-2,3-dihydro-1H-isoindole-1,3-dione |
| 128 | 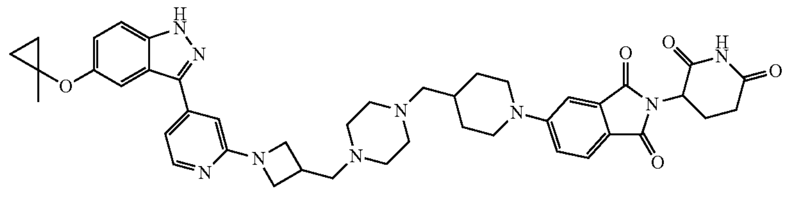 [SMILES: CC1(Oc2ccc3[nH]nc(-c4ccnc(N5CC(CN6CCN(CC7CCN(c8ccc9c(c8)C(=O)N(C8CCC(=O)NC8=O)C9=O)CC7)CC6)C5)c4)c3c2)CC1] | 2-(2,6-dioxopiperidin-3-yl)-5-[4-({4-[(1-{4-[5-(1-methylcyclopropoxy)-1H-indazol-3-yl]pyridin-2-yl}azetidin-3-yl)methyl]piperazin-1-yl}methyl)piperidin-1-yl]-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 129 | 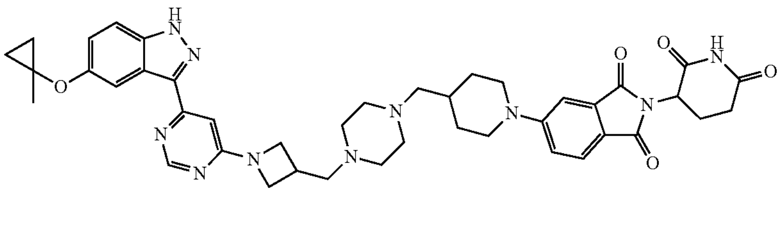 [SMILES: CC1(Oc2ccc3[nH]nc(-c4cc(N5CC(CN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-[4-({4-[(1-{6-[5-(1-methylcyclopropoxy)-1H-indazol-3-yl]pyrimidin-4-yl}azetidin-3-yl)methyl]piperazin-1-yl}methyl)piperidin-1-yl]-2,3-dihydro-1H-isoindole-1,3-dione |
| 130 | 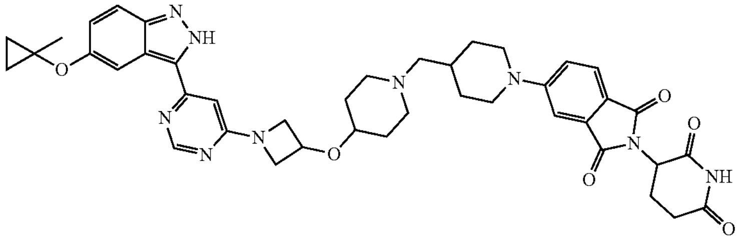 [SMILES: CC1(Oc2ccc3n[nH]c(-c4cc(N5CC(OC6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-[4-({4-[(1-{6-[5-(1-methylcyclopropoxy)-2H-indazol-3-yl]pyrimidin-4-yl}azetidin-3-yl)oxy]piperidin-1-yl}methyl)piperidin-1-yl]-2,3-dihydro-1H-isoindole-1,3-dione |
| 131 | 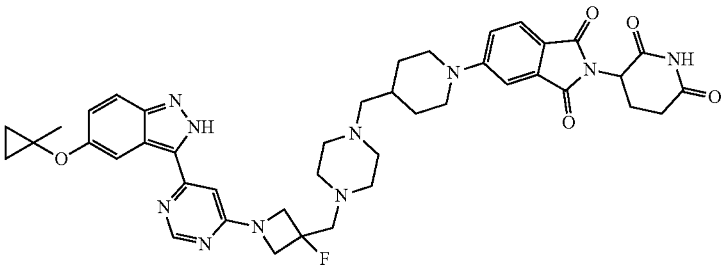 [SMILES: CC1(Oc2ccc3n[nH]c(-c4cc(N5CC(F)(CN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-[4-({4-[(3-fluoro-1-{6-[5-(1-methylcyclopropoxy)-2H-indazol-3-yl]pyrimidin-4-yl}azetidin-3-yl)methyl]piperazin-1-yl}methyl)piperidin-1-yl]-2,3-dihydro-1H-isoindole-1,3-dione |
| 132 | 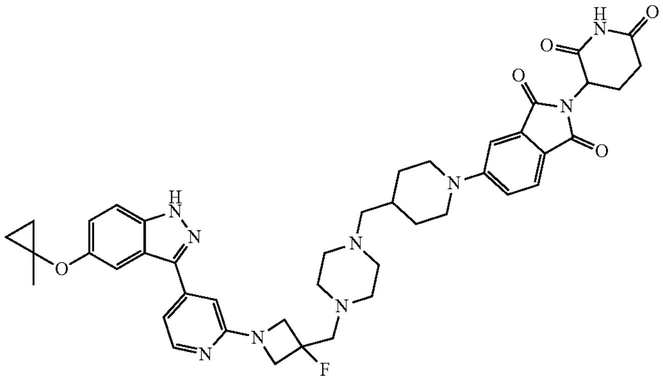 [SMILES: CC1(Oc2ccc3[nH]nc(-c4ccnc(N5CC(F)(CN6CCN(CC7CCN(c8ccc9c(c8)C(=O)N(C8CCC(=O)NC8=O)C9=O)CC7)CC6)C5)c4)c3c2)CC1] | 2-(2,6-dioxopiperidin-3-yl)-5-[4-({4-[(3-fluoro-1-{4-[5-(1-methylcyclopropoxy)-1H-indazol-3-yl]pyridin-2-yl}azetidin-3-yl)methyl]piperazin-1-yl}methyl)piperidin-1-yl]-2,3-dihydro-1H-isoindole-1,3-dione |
| 133 | 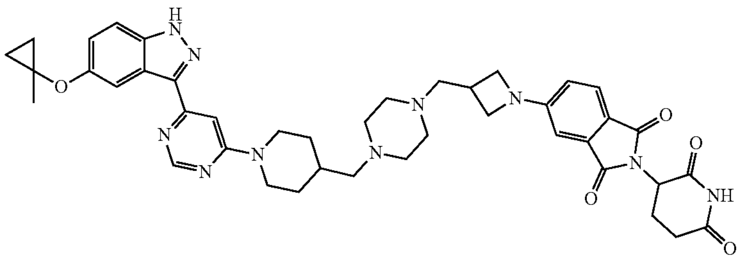 [SMILES: CC1(Oc2ccc3[nH]nc(-c4cc(N5CCC(CN6CCN(CC7CN(c8ccc9c(c8)C(=O)N(C8CCC(=O)NC8=O)C9=O)C7)CC6)CC5)ncn4)c3c2)CC1] | 2-(2,6-dioxopiperidin-3-yl)-5-[3-({4-[(1-{6-[5-(1-methylcyclopropoxy)-1H-indazol-3-yl]pyrimidin-4-yl}piperidin-4-yl)methyl]piperazin-1-yl}methyl)azetidin-1-yl]-2,3-dihydro-1H-isoindole-1,3-dione |

TABLE 1-continued

| Ex. No. | Chemical Structure | IUPAC Name |
| --- | --- | --- |
| | Exemplary bifunctional compounds of the present disclosure** | |
| 134 | 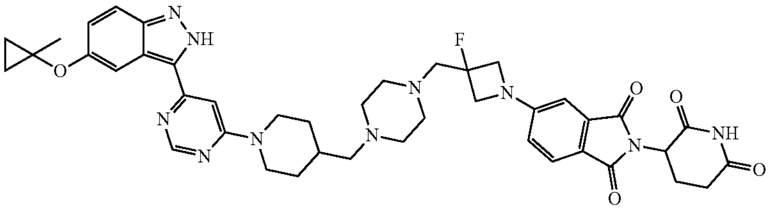 [SMILES: CC1(Oc2ccc3n[nH]c(-c4cc(N5CCC(CN6CCN(CC7(F)CN(c8ccc9c(c8)C(=O)N(C8CCC(=O)NC8=O)C9=O)C7)CC6)CC5)ncn4)c3c2)CC1] | 2-(2,6-dioxopiperidin-3-yl)-5-[3-fluoro-3-({4-[(1-{6-[5-(1-methylcyclopropoxy)-2H-indazol-3-yl]pyrimidin-4-yl}piperidin-4-yl)methyl]piperazin-1-yl}methyl)azetidin-1-yl]-2,3-dihydro-1H-isoindole-1,3-dione |
| 135 | 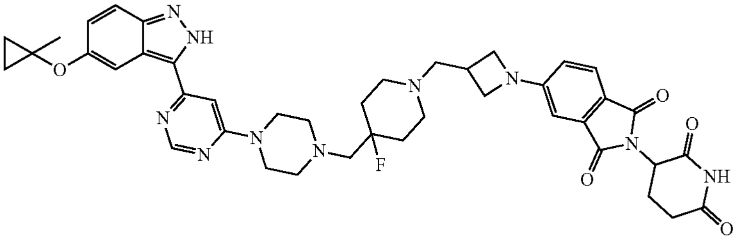 [SMILES: CC1(Oc2ccc3n[nH]c(-c4cc(N5CCN(CC6(F)CCN(CC7CN(c8ccc9c(c8)C(=O)N(C8CCC(=O)NC8=O)C9=O)C7)CC6)CC5)ncn4)c3c2)CC1] | 2-(2,6-dioxopiperidin-3-yl)-5-[3-({4-fluoro-4-[(4-{6-[5-(1-methylcyclopropoxy)-2H-indazol-3-yl]pyrimidin-4-yl}piperazin-1-yl)methyl]piperidin-1-yl}methyl)azetidin-1-yl]-2,3-dihydro-1H-isoindole-1,3-dione |
| 136 | 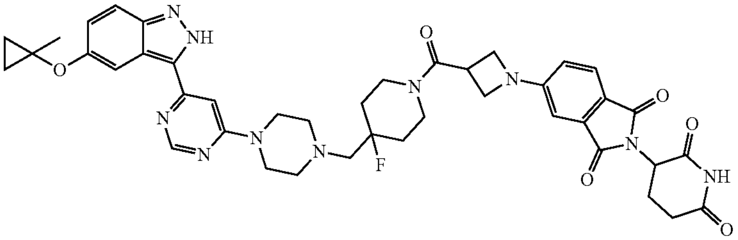 [SMILES: CC1(Oc2ccc3n[nH]c(-c4cc(N5CCN(CC6(F)CCN(C(=O)C7CN(c8ccc9c(c8)C(=O)N(C8CCC(=O)NC8=O)C9=O)C7)CC6)CC5)ncn4)c3c2)CC1] | 2-(2,6-dioxopiperidin-3-yl)-5-(3-{4-fluoro-4-[(4-{6-[5-(1-methylcyclopropoxy)-2H-indazol-3-yl]pyrimidin-4-yl}piperazin-1-yl)methyl]piperidine-1-carbonyl}azetidin-1-yl)-2,3-dihydro-1H-isoindole-1,3-dione |
| 137 | 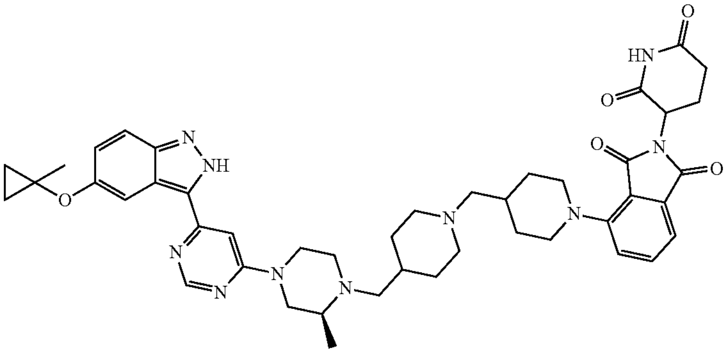 [SMILES: C[C@H]1CN(c2cc(-c3[nH]nc4ccc(OC5(C)CC5)cc34)ncn2)CCN1CC1CCN(CC2CCN(c3cccc4c3C(=O)N(C3CCC(=O)NC3=O)C4=O)CC2)CC1] | 2-(2,6-dioxopiperidin-3-yl)-4-{4-[(4-{[(2S)-2-methyl-4-{6-[5-(1-methylcyclopropoxy)-2H-indazol-3-yl]pyrimidin-4-yl}piperazin-1-yl]methyl}piperidin-1-yl)methyl]piperidin-1-yl}-2,3-dihydro-1H-isoindole-1,3-dione |
| 138 | 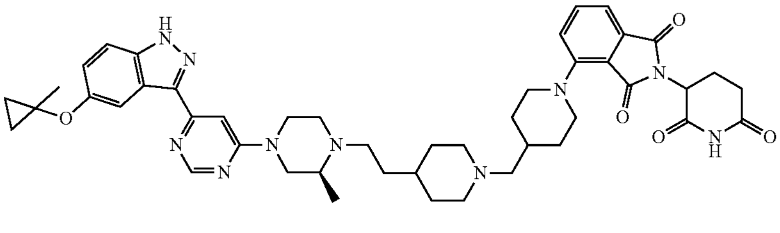 [SMILES: C[C@H]1CN(c2cc(-c3n[nH]c4ccc(OC5(C)CC5)cc34)ncn2)CCN1CCC1CCN(CC2CCN(c3cccc4c3C(=O)N(C3CCC(=O)NC3=O)C4=O)CC2)CC1] | 2-(2,6-dioxopiperidin-3-yl)-4-{4-[(4-{2-[(2S)-2-methyl-4-{6-[5-(1-methylcyclopropoxy)-1H-indazol-3-yl]pyrimidin-4-yl}piperazin-1-yl]ethyl}piperidin-1-yl)methyl]piperidin-1-yl}-2,3-dihydro-1H-isoindole-1,3-dione |

TABLE 1-continued

| Ex. No. | Chemical Structure | IUPAC Name |
|---|---|---|
| | Exemplary bifunctional compounds of the present disclosure** | |
| 139 | 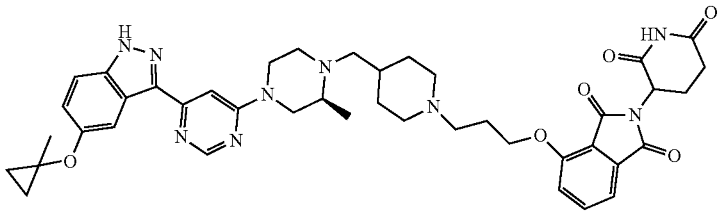 [SMILES: C[C@H]1CN(c2cc(-c3n[nH]c4ccc(OC5(C)CC5)cc34)ncn2)CCN1CC1CCN(CCCOc2cccc3c2C(=O)N(C2CCC(=O)NC2=O)C3=O)CC1] | 2-(2,6-dioxopiperidin-3-yl)-4-[3-(4-{[(2S)-2-methyl-4-{6-[5-(1-methylcyclopropoxy)-1H-indazol-3-yl]pyrimidin-4-yl}piperazin-1-yl]methyl}piperidin-1-yl)propoxy]-2,3-dihydro-1H-isoindole-1,3-dione |
| 140 | 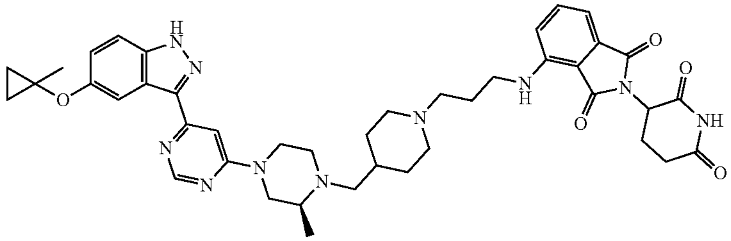 [SMILES: C[C@H]1CN(c2cc(-c3n[nH]c4ccc(OC5(C)CC5)cc34)ncn2)CCN1CC1CCN(CCCNc2cccc3c2C(=O)N(C2CCC(=O)NC2=O)C3=O)CC1] | 2-(2,6-dioxopiperidin-3-yl)-4-{[3-(4-{[(2S)-2-methyl-4-{6-[5-(1-methylcyclopropoxy)-1H-indazol-3-yl]pyrimidin-4-yl}piperazin-1-yl]methyl}piperidin-1-yl)propyl]amino}-2,3-dihydro-1H-isoindole-1,3-dione |
| 141 | 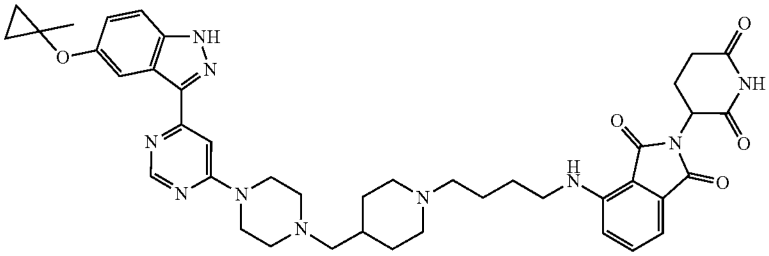 [SMILES: CC1(Oc2ccc3[nH]nc(-c4cc(N5CCN(CC6CCN(CCCCNc7cccc8c7C(=O)N(C7CCC(=O)NC7=O)C8=O)CC6)CC5)ncn4)c3c2)CC1] | 2-(2,6-dioxopiperidin-3-yl)-4-[(4-{4-[(4-{6-[5-(1-methylcyclopropoxy)-1H-indazol-3-yl]pyrimidin-4-yl}piperazin-1-yl)methyl]piperidin-1-yl}butyl)amino]-2,3-dihydro-1H-isoindole-1,3-dione |
| 142 | 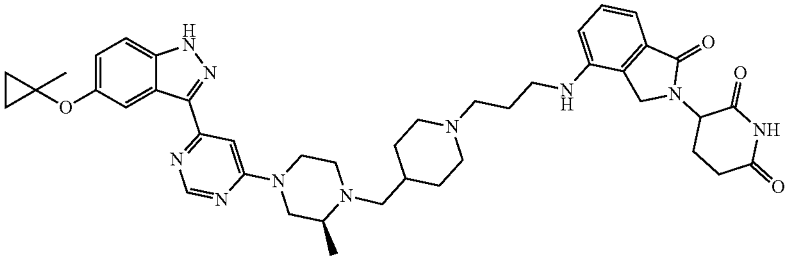 [SMILES: C[C@H]1CN(c2cc(-c3n[nH]c4ccc(OC5(C)CC5)cc34)ncn2)CCN1CC1CCN(CCCNc2cccc3c2CN(C2CCC(=O)NC2=O)C3=O)CC1] | 3-(4-{[3-(4-{[(2S)-2-methyl-4-{6-[5-(1-methylcyclopropoxy)-1H-indazol-3-yl]pyrimidin-4-yl}piperazin-1-yl]methyl}piperidin-1-yl)propyl]amino}-1-oxo-2,3-dihydro-1H-isoindol-2-yl)piperidine-2,6-dione |
| 143 | 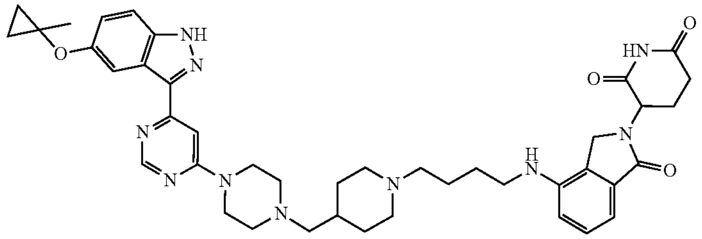 [SMILES: CC1(Oc2ccc3[nH]nc(-c4cc(N5CCN(CC6CCN(CCCCNc7cccc8c7CN(C7CCC(=O)NC7=O)C8=O)CC6)CC5)ncn4)c3c2)CC1] | 3-{4-[(4-{4-[(4-{6-[5-(1-methylcyclopropoxy)-1H-indazol-3-yl]pyrimidin-4-yl}piperazin-1-yl)methyl]piperidin-1-yl}butyl)amino]-1-oxo-2,3-dihydro-1H-isoindol-2-yl}piperidine-2,6-dione |
| 144 | 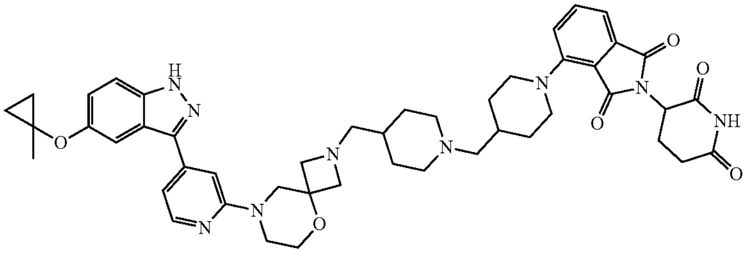 [SMILES: CC1(Oc2ccc3[nH]nc(-c4ccnc(N5CCOC6(CN(CC7CCN(CC8CCN(c9cccc%10c9C(=O)N(C9CCC(=O)NC9=O)C%10=O)CC8)CC7)C6)C5)c4)c3c2)CC1] | 2-(2,6-dioxopiperidin-3-yl)-4-[4-({4-[(8-{4-[5-(1-methylcyclopropoxy)-1H-indazol-3-yl]pyridin-2-yl}-5-oxa-2,8-diazaspiro[3.5]nonan-2-yl)methyl]piperidin-1-yl}methyl)piperidin-1-yl]-2,3-dihydro-1H-isoindole-1,3-dione |

TABLE 1-continued

Exemplary bifunctional compounds of the present disclosure**

| Ex. No. | Chemical Structure | IUPAC Name |
|---|---|---|
| 145 | 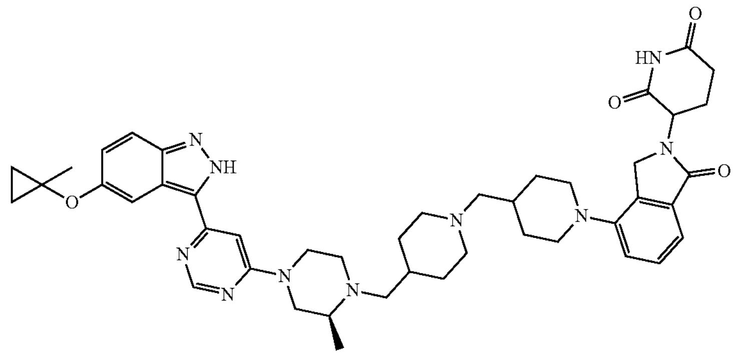 [SMILES: C[C@H]1CN(c2cc(-c3[nH]nc4ccc(OC5(C)CC5)cc34)ncn2)CCN1CC1CCN(CC2CCN(c3cccc4c3CN(C3CCC(=O)NC3=O)C4=O)CC2)CC1] | 3-(4-{4-[(4-{[(2S)-2-methyl-4-{6-[5-(1-methylcyclopropoxy)-2H-indazol-3-yl]pyrimidin-4-yl}piperazin-1-yl]methyl}piperidin-1-yl)methyl]piperidin-1-yl}-1-oxo-2,3-dihydro-1H-isoindol-2-yl)piperidine-2,6-dione |
| 146 | 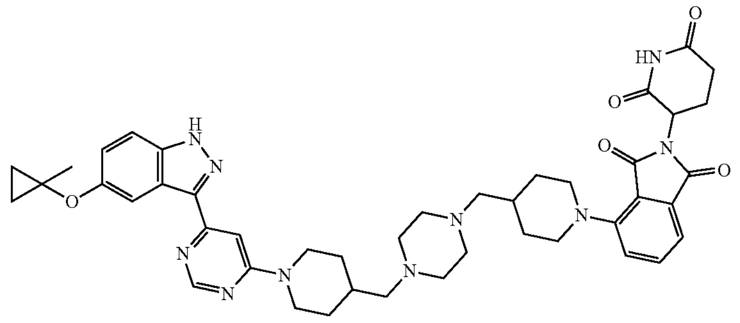 [SMILES: CC1(Oc2ccc3[nH]nc(-c4cc(N5CCC(CN6CCN(CC7CCN(c8cccc9c8C(=O)N(C8CCC(=O)NC8=O)C9=O)CC7)CC6)CC5)ncn4)c3c2)CC1] | 2-(2,6-dioxopiperidin-3-yl)-4-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-2,3-dihydro-1H-isoindole-1,3-dione |
| 147 | 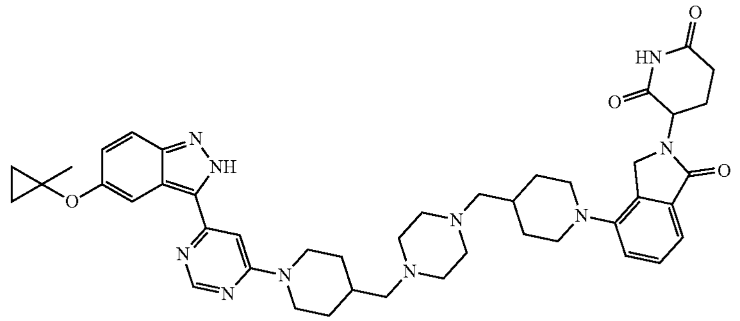 [SMILES: CC1(Oc2ccc3n[nH]c(-c4cc(N5CCC(CN6CCN(CC7CCN(c8cccc9c8CN(C8CCC(=O)NC8=O)C9=O)CC7)CC6)CC5)ncn4)c3c2)CC1] | 3-{4-[4-({4-[(1-{6-[5-(1-methylcyclopropoxy)-2H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 148 | 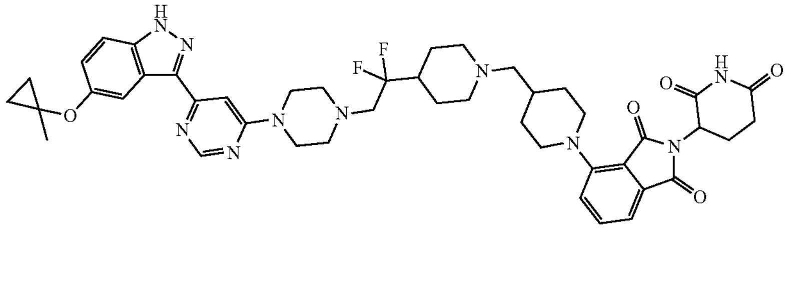 [SMILES: CC1(Oc2ccc3[nH]nc(-c4cc(N5CCN(CC(F)(F)C6CCN(CC7CCN(c8cccc9c8C(=O)N(C8CCC(=O)NC8=O)C9=O)CC7)CC6)CC5)ncn4)c3c2)CC1] | 4-[4-({4-[1,1-difluoro-2-(4-{6-[5-(1-methylcyclopropoxy)-1H-indazol-3-yl]pyrimidin-4-yl}piperazin-1-yl)ethyl]piperidin-1-yl}methyl)piperidin-1-yl]-2-(2,6-dioxopiperidin-3-yl)-2,3-dihydro-1H-isoindole-1,3-dione |
| 149 | 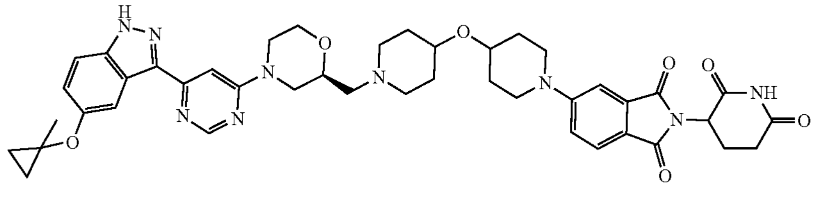 [SMILES: CC1(Oc2ccc3[nH]nc(-c4cc(N5CCO[C@@H](CN6CCC(OC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(1-{[(2S)-4-{6-[5-(1-methylcyclopropoxy)-1H-indazol-3-yl]pyrimidin-4-yl}morpholin-2-yl]methyl}piperidin-4-yl)oxy]piperidin-1-yl}-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 150 | 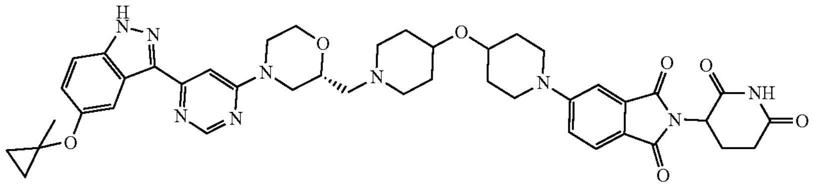 [SMILES: CC1(Oc2ccc3[nH]nc(-c4cc(N5CCO[C@H](CN6CCC(OC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(1-{[(2R)-4-{6-[5-(1-methylcyclopropoxy)-1H-indazol-3-yl]pyrimidin-4-yl}morpholin-2-yl]methyl}piperidin-4-yl)oxy]piperidin-1-yl}-2,3-dihydro-1H-isoindole-1,3-dione |
| 151 | 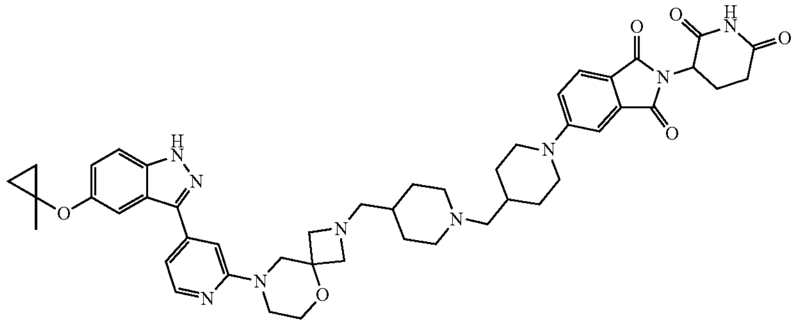 [SMILES: CC1(Oc2ccc3[nH]nc(-c4ccnc(N5CCOC6(CN(CC7CCN(CC8CCN(c9ccc%10c(c9)C(=O)N(C9CCC(=O)NC9=O)C%10=O)CC8)CC7)C6)C5)c4)c3c2)CC1] | 2-(2,6-dioxopiperidin-3-yl)-5-[4-({4-[(8-{4-[5-(1-methylcyclopropoxy)-1H-indazol-3-yl]pyridin-2-yl}-5-oxa-2,8-diazaspiro[3.5]nonan-2-yl)methyl]piperidin-1-yl}methyl)piperidin-1-yl]-2,3-dihydro-1H-isoindole-1,3-dione |
| 152 | 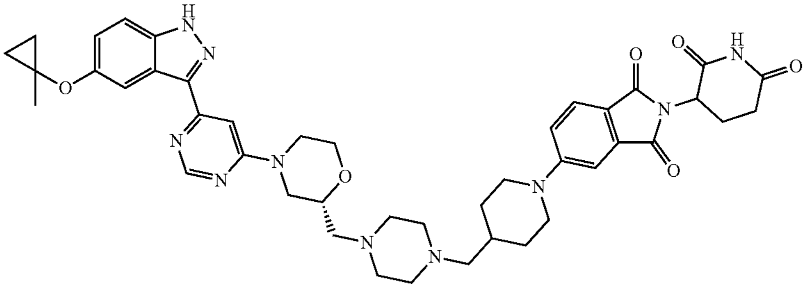 [SMILES: CC1(Oc2ccc3[nH]nc(-c4cc(N5CCO[C@H](CN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(4-{[(2R)-4-{6-[5-(1-methylcyclopropoxy)-1H-indazol-3-yl]pyrimidin-4-yl}morpholin-2-yl]methyl}piperazin-1-yl)methyl]piperidin-1-yl}-2,3-dihydro-1H-isoindole-1,3-dione |
| 153 | 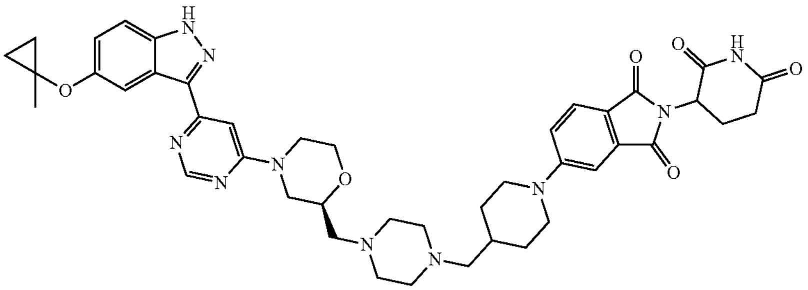 [SMILES: CC1(Oc2ccc3[nH]nc(-c4cc(N5CCO[C@@H](CN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(4-{[(2S)-4-{6-[5-(1-methylcyclopropoxy)-1H-indazol-3-yl]pyrimidin-4-yl}morpholin-2-yl]methyl}piperazin-1-yl)methyl]piperidin-1-yl}-2,3-dihydro-1H-isoindole-1,3-dione |
| 154 | 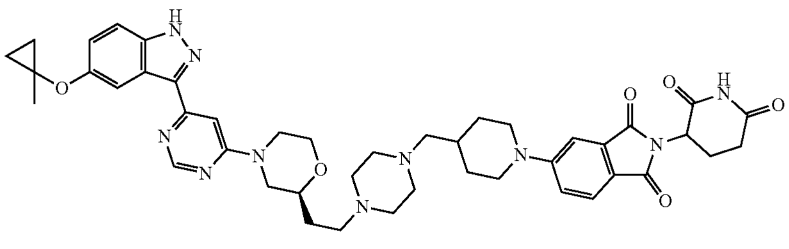 [SMILES: CC1(Oc2ccc3[nH]nc(-c4cc(N5CCO[C@@H](CCN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(4-{2-[(2S)-4-{6-[5-(1-methylcyclopropoxy)-1H-indazol-3-yl]pyrimidin-4-yl}morpholin-2-yl]ethyl}piperazin-1-yl)methyl]piperidin-1-yl}-2,3-dihydro-1H-isoindole-1,3-dione |

TABLE 1-continued

| Ex. No. | Chemical Structure | IUPAC Name |
|---|---|---|
| Exemplary bifunctional compounds of the present disclosure** | | |
| 155 | 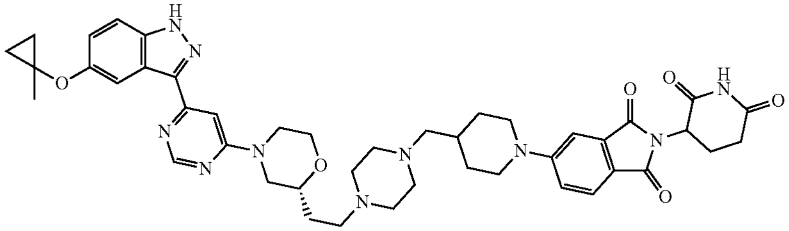 [SMILES: CC1(Oc2ccc3[nH]nc(-c4cc(N5CCO[C@H](CCN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(4-{2-[(2R)-4-{6-[5-(1-methylcyclopropoxy)-1H-indazol-3-yl]pyrimidin-4-yl}morpholin-2-yl]ethyl}piperazin-1-yl)methyl]piperidin-1-yl}-2,3-dihydro-1H-isoindole-1,3-dione |
| 156 | 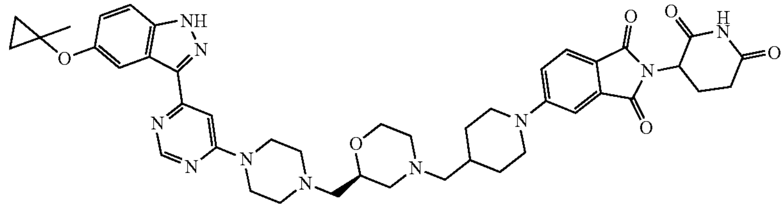 [SMILES: CC1(Oc2ccc3[nH]nc(-c4cc(N5CCN(C[C@@H]6CN(CC7CCN(c8ccc9c(c8)C(=O)N(C8CCC(=O)NC8=O)C9=O)CC7)CCO6)CC5)ncn4)c3c2)CC1] | 2-(2,6-dioxopiperidin-3-yl)-5-(4-{[(2R)-2-[(4-{6-[5-(1-methylcyclopropoxy)-1H-indazol-3-yl]pyrimidin-4-yl}piperazin-1-yl)methyl]morpholin-4-yl]methyl}piperidin-1-yl)-2,3-dihydro-1H-isoindole-1,3-dione |
| 157 | 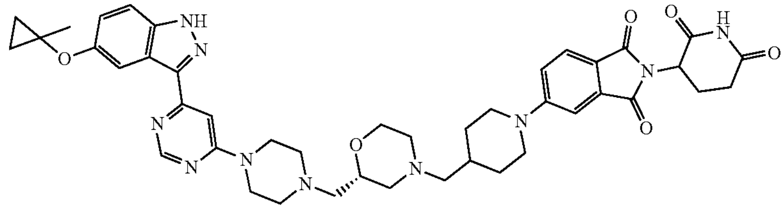 [SMILES: CC1(Oc2ccc3[nH]nc(-c4cc(N5CCN(C[C@H]6CN(CC7CCN(c8ccc9c(c8)C(=O)N(C8CCC(=O)NC8=O)C9=O)CC7)CCO6)CC5)ncn4)c3c2)CC1] | 2-(2,6-dioxopiperidin-3-yl)-5-(4-{[(2S)-2-[(4-{6-[5-(1-methylcyclopropoxy)-1H-indazol-3-yl]pyrimidin-4-yl}piperazin-1-yl)methyl]morpholin-4-yl]methyl}piperidin-1-yl)-2,3-dihydro-1H-isoindole-1,3-dione |
| 158 | 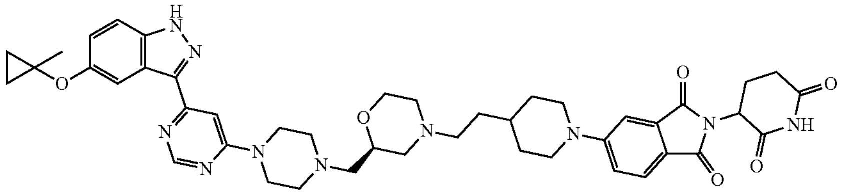 [SMILES: CC1(Oc2ccc3[nH]nc(-c4cc(N5CCN(C[C@@H]6CN(CCC7CCN(c8ccc9c(c8)C(=O)N(C8CCC(=O)NC8=O)C9=O)CC7)CCO6)CC5)ncn4)c3c2)CC1] | 2-(2,6-dioxopiperidin-3-yl)-5-(4-{2-[(2R)-2-[(4-{6-[5-(1-methylcyclopropoxy)-1H-indazol-3-yl]pyrimidin-4-yl}piperazin-1-yl)methyl]morpholin-4-yl]ethyl}piperidin-1-yl)-2,3-dihydro-1H-isoindole-1,3-dione |
| 159 | 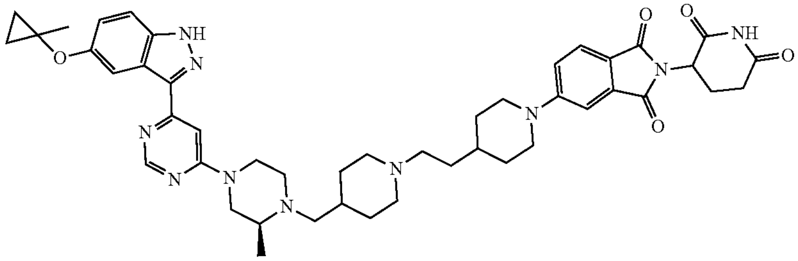 [SMILES: C[C@H]1CN(c2cc(-c3n[nH]c4ccc(OC5(C)CC5)cc34)ncn2)CCN1CC1CCN(CCC2CCN(c3ccc4c(c3)C(=O)N(C3CCC(=O)NC3=O)C4=O)CC2)CC1] | 2-(2,6-dioxopiperidin-3-yl)-5-{4-[2-(4-{[(2S)-2-methyl-4-{6-[5-(1-methylcyclopropoxy)-1H-indazol-3-yl]pyrimidin-4-yl}piperazin-1-yl]methyl}piperidin-1-yl)ethyl]piperidin-1-yl}-2,3-dihydro-1H-isoindole-1,3-dione |
| 160 | 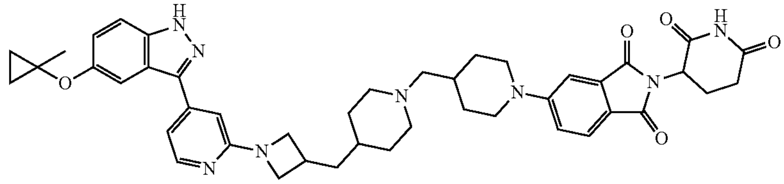 [SMILES: CC1(Oc2ccc3[nH]nc(-c4ccnc(N5CC(CC6CCN(CC7CCN(c8ccc9c(c8)C(=O)N(C8CCC(=O)NC8=O)C9=O)CC7)CC6)C5)c4)c3c2)CC1] | 2-(2,6-dioxopiperidin-3-yl)-5-[4-({4-[(1-{4-[5-(1-methylcyclopropoxy)-1H-indazol-3-yl]pyridin-2-yl}azetidin-3-yl)methyl]piperidin-1-yl}methyl)piperidin-1-yl]-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 161 | 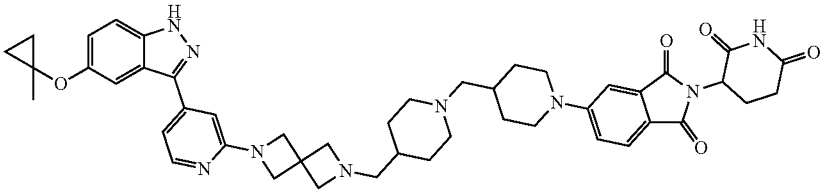 [SMILES: CC1(Oc2ccc3[nH]nc(-c4ccnc(N5CC6(CN(CC7CCN(CC8CCN(c9ccc%10c(c9)C(=O)N(C9CCC(=O)NC9=O)C%10=O)CC8)CC7)C6)C5)c4)c3c2)CC1] | 2-(2,6-dioxopiperidin-3-yl)-5-[4-({4-[(6-{4-[5-(1-methylcyclopropoxy)-1H-indazol-3-yl]pyridin-2-yl}-2,6-diazaspiro[3.3]heptan-2-yl)methyl]piperidin-1-yl}methyl)piperidin-1-yl]-2,3-dihydro-1H-isoindole-1,3-dione |
| 162 | 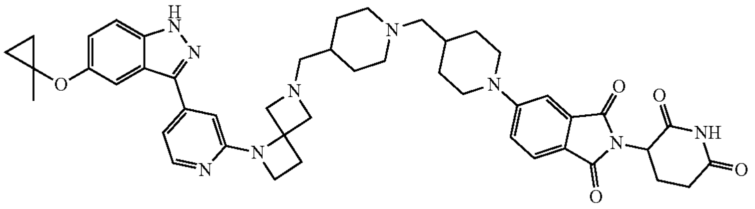 [SMILES: CC1(Oc2ccc3[nH]nc(-c4ccnc(N5CCC56CN(CC5CCN(CC7CCN(c8ccc9c(c8)C(=O)N(C8CCC(=O)NC8=O)C9=O)CC7)CC5)C6)c4)c3c2)CC1] | 2-(2,6-dioxopiperidin-3-yl)-5-[4-({4-[(1-{4-[5-(1-methylcyclopropoxy)-1H-indazol-3-yl]pyridin-2-yl}-1,6-diazaspiro[3.3]heptan-6-yl)methyl]piperidin-1-yl}methyl)piperidin-1-yl]-2,3-dihydro-1H-isoindole-1,3-dione |
| 163 | 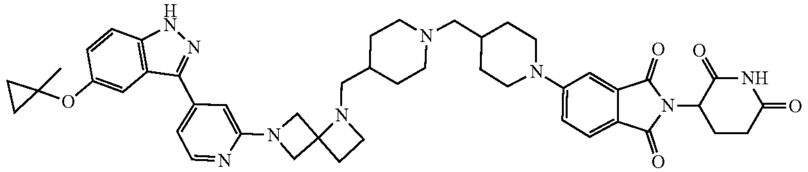 [SMILES: CC1(Oc2ccc3[nH]nc(-c4ccnc(N5CC6(CCN6CC6CCN(CC7CCN(c8ccc9c(c8)C(=O)N(C8CCC(=O)NC8=O)C9=O)CC7)CC6)C5)c4)c3c2)CC1] | 2-(2,6-dioxopiperidin-3-yl)-5-[4-({4-[(6-{4-[5-(1-methylcyclopropoxy)-1H-indazol-3-yl]pyridin-2-yl}-1,6-diazaspiro[3.3]heptan-1-yl)methyl]piperidin-1-yl}methyl)piperidin-1-yl]-2,3-dihydro-1H-isoindole-1,3-dione |
| 164 | 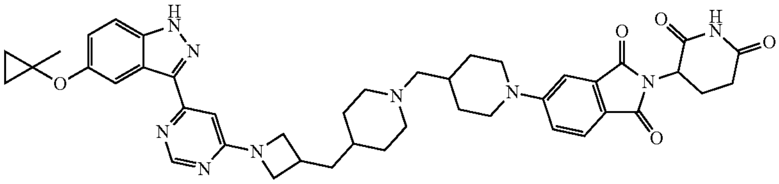 [SMILES: CC1(Oc2ccc3[nH]nc(-c4cc(N5CC(CC6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-[4-({4-[(1-{6-[5-(1-methylcyclopropoxy)-1H-indazol-3-yl]pyrimidin-4-yl}azetidin-3-yl)methyl]piperidin-1-yl}methyl)piperidin-1-yl]-2,3-dihydro-1H-isoindole-1,3-dione |
| 165 | 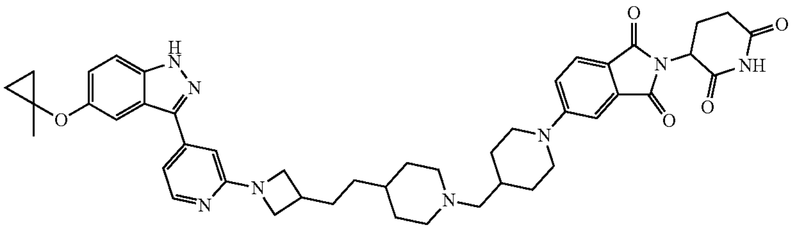 [SMILES: CC1(Oc2ccc3[nH]nc(-c4ccnc(N5CC(CCC6CCN(CC7CCN(c8ccc9c(c8)C(=O)N(C8CCC(=O)NC8=O)C9=O)CC7)CC6)C5)c4)c3c2)CC1] | 2-(2,6-dioxopiperidin-3-yl)-5-[4-({4-[2-(1-{4-[5-(1-methylcyclopropoxy)-1H-indazol-3-yl]pyridin-2-yl}azetidin-3-yl)ethyl]piperidin-1-yl}methyl)piperidin-1-yl]-2,3-dihydro-1H-isoindole-1,3-dione |
| 166 | 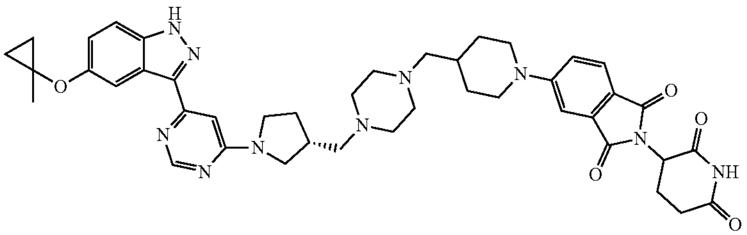 [SMILES: CC1(Oc2ccc3[nH]nc(-c4cc(N5CC[C@H](CN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(4-{[(3R)-1-{6-[5-(1-methylcyclopropoxy)-1H-indazol-3-yl]pyrimidin-4-yl}pyrrolidin-3-yl]methyl}piperazin-1-yl)methyl]piperidin-1-yl}-2,3-dihydro-1H-isoindole-1,3-dione |

TABLE 1-continued

| Ex. No. | Chemical Structure | IUPAC Name |
|---|---|---|
| | Exemplary bifunctional compounds of the present disclosure** | |
| 167 | 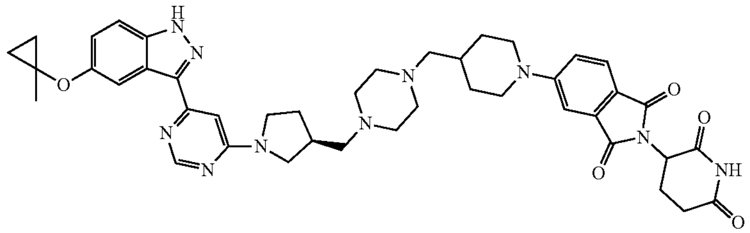 [SMILES: CC1(Oc2ccc3[nH]nc(-c4cc(N5CC[C@@H](CN6CCN(CC7CCN(c8ccc9c(c8)C(=O)N(C8CCC(=O)NC8=O)C9=O)CC7)CC6)C5)ncn4)c3c2)CC1] | 2-(2,6-dioxopiperidin-3-yl)-5-{4-[(4-{[(3S)-1-{6-[5-(1-methylcyclopropoxy)-1H-indazol-3-yl]pyrimidin-4-yl}pyrrolidin-3-yl]methyl}piperazin-1-yl)methyl]piperidin-1-yl}-2,3-dihydro-1H-isoindole-1,3-dione |
| 168 | 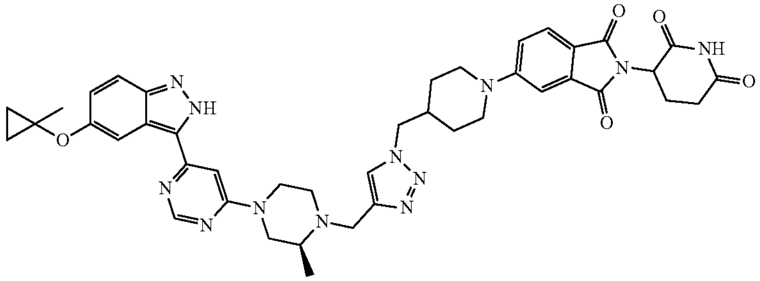 [SMILES: C[C@H]1CN(c2cc(-c3[nH]nc4ccc(OC5(C)CC5)cc34)ncn2)CCN1Cc1cn(CC2CCN(c3ccc4c(c3)C(=O)N(C3CCC(=O)NC3=O)C4=O)CC2)nn1] | 2-(2,6-dioxopiperidin-3-yl)-5-{4-[(4-{[(2S)-2-methyl-4-{6-[5-(1-methylcyclopropoxy)-2H-indazol-3-yl]pyrimidin-4-yl}piperazin-1-yl]methyl}-1H-1,2,3-triazol-1-yl)methyl]piperidin-1-yl}-2,3-dihydro-1H-isoindole-1,3-dione |
| 169 | 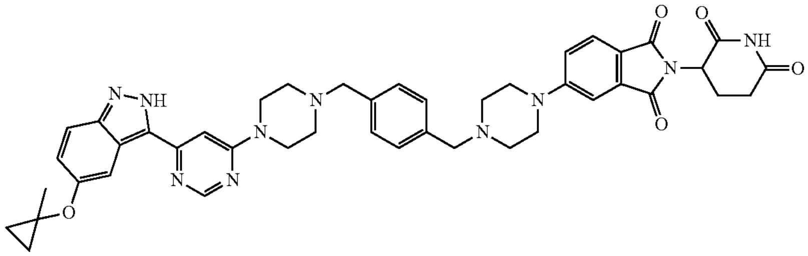 [SMILES: CC1(Oc2ccc3n[nH]c(-c4cc(N5CCN(Cc6ccc(CN7CCN(c8ccc9c(c8)C(=O)N(C8CCC(=O)NC8=O)C9=O)CC7)cc6)CC5)ncn4)c3c2)CC1] | 2-(2,6-dioxopiperidin-3-yl)-5-[4-({4-[(4-{6-[5-(1-methylcyclopropoxy)-2H-indazol-3-yl]pyrimidin-4-yl}piperazin-1-yl)methyl]phenyl}methyl)piperazin-1-yl]-2,3-dihydro-1H-isoindole-1,3-dione |
| 170 | 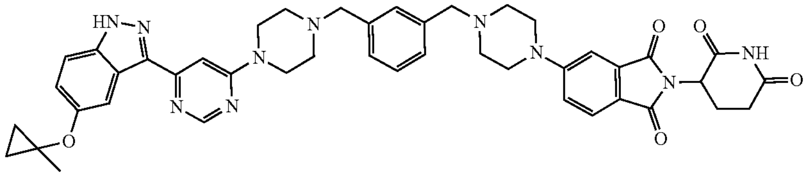 [SMILES: CC1(Oc2ccc3[nH]nc(-c4cc(N5CCN(Cc6cccc(CN7CCN(c8ccc9c(c8)C(=O)N(C8CCC(=O)NC8=O)C9=O)CC7)c6)CC5)ncn4)c3c2)CC1] | 2-(2,6-dioxopiperidin-3-yl)-5-[4-({3-[(4-{6-[5-(1-methylcyclopropoxy)-1H-indazol-3-yl]pyrimidin-4-yl}piperazin-1-yl)methyl]phenyl}methyl)piperazin-1-yl]-2,3-dihydro-1H-isoindole-1,3-dione |
| 171 | 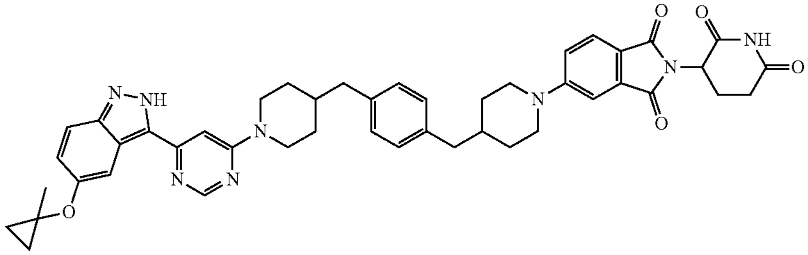 [SMILES: CC1(Oc2ccc3n[nH]c(-c4cc(N5CCC(Cc6ccc(CC7CCN(c8ccc9c(c8)C(=O)N(C8CCC(=O)NC8=O)C9=O)CC7)cc6)CC5)ncn4)c3c2)CC1] | 2-(2,6-dioxopiperidin-3-yl)-5-[4-({4-[(1-{6-[5-(1-methylcyclopropoxy)-2H-indazol-3-yl]pyrimidin-4-yl}piperidin-4-yl)methyl]phenyl}methyl)piperidin-1-yl]-2,3-dihydro-1H-isoindole-1,3-dione |
| 172 | 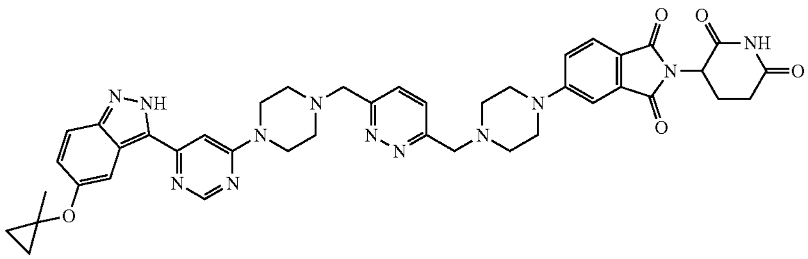 | 2-(2,6-dioxopiperidin-3-yl)-5-[4-({6-[(4-{6-[5-(1-methylcyclopropoxy)-2H-indazol-3-yl]pyrimidin-4-yl}piperazin-1-yl)methyl]pyridazin-3-yl}methyl)piperazin-1-yl]-2,3-dihydro-1H-isoindole-1,3-dione |

TABLE 1-continued

| Exemplary bifunctional compounds of the present disclosure** | | |
|---|---|---|
| Ex. No. | Chemical Structure | IUPAC Name |
| 173 | 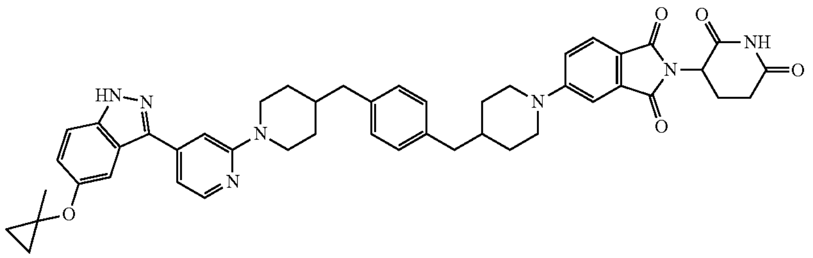 [SMILES: CC1(Oc2ccc3[nH]nc(-c4ccnc(N5CCC(Cc6ccc(CC7CCN(c8ccc9c(c8)C(=O)N(C8CCC(=O)NC8=O)C9=O)CC7)cc6)CC5)c4)c3c2)CC1] | 2-(2,6-dioxopiperidin-3-yl)-5-[4-({4-[(1-{4-[5-(1-methylcyclopropoxy)-1H-indazol-3-yl]pyridin-2-yl}piperidin-4-yl)methyl]phenyl}methyl)piperidin-1-yl]-2,3-dihydro-1H-isoindole-1,3-dione |
| 174 | 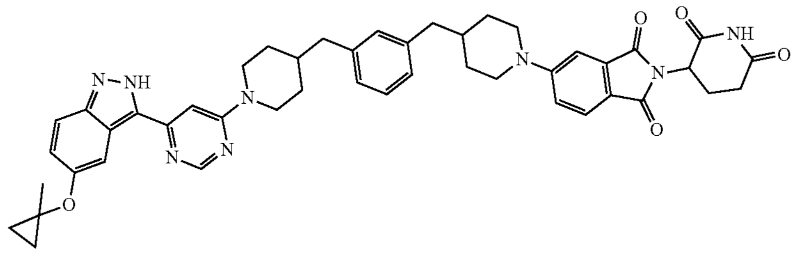 [SMILES: CC1(Oc2ccc3n[nH]c(-c4cc(N5CCC(Cc6cccc(CC7CCN(c8ccc9c(c8)C(=O)N(C8CCC(=O)NC8=O)C9=O)CC7)c6)CC5)ncn4)c3c2)CC1] | 2-(2,6-dioxopiperidin-3-yl)-5-[4-({3-[(1-{6-[5-(1-methylcyclopropoxy)-2H-indazol-3-yl]pyrimidin-4-yl}piperidin-4-yl)methyl]phenyl}methyl)piperidin-1-yl]-2,3-dihydro-1H-isoindole-1,3-dione |
| 175 | 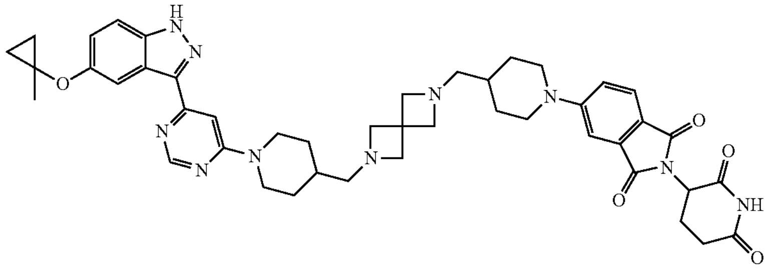 [SMILES: CC1(Oc2ccc3[nH]nc(-c4cc(N5CCC(CN6CC7(CN(CC8CCN(c9ccc%10c(c9)C(=O)N(C9CCC(=O)NC9=O)C%10=O)CC8)C7)C6)CC5)ncn4)c3c2)CC1] | 2-(2,6-dioxopiperidin-3-yl)-5-[4-({6-[(1-{6-[5-(1-methylcyclopropoxy)-1H-indazol-3-yl]pyrimidin-4-yl}piperidin-4-yl)methyl]-2,6-diazaspiro[3.3]heptan-2-yl}methyl)piperidin-1-yl]-2,3-dihydro-1H-isoindole-1,3-dione |
| 176 | 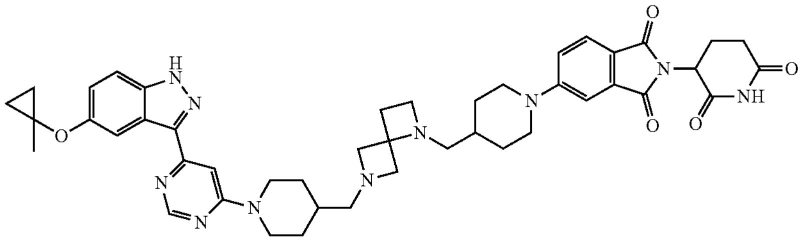 [SMILES: CC1(Oc2ccc3[nH]nc(-c4cc(N5CCC(CN6CC7(CCN7CC7CCN(c8ccc9c(c8)C(=O)N(C8CCC(=O)NC8=O)C9=O)CC7)C6)CC5)ncn4)c3c2)CC1] | 2-(2,6-dioxopiperidin-3-yl)-5-[4-({6-[(1-{6-[5-(1-methylcyclopropoxy)-1H-indazol-3-yl]pyrimidin-4-yl}piperidin-4-yl)methyl]-1,6-diazaspiro[3.3]heptan-1-yl}methyl)piperidin-1-yl]-2,3-dihydro-1H-isoindole-1,3-dione |
| 177 | 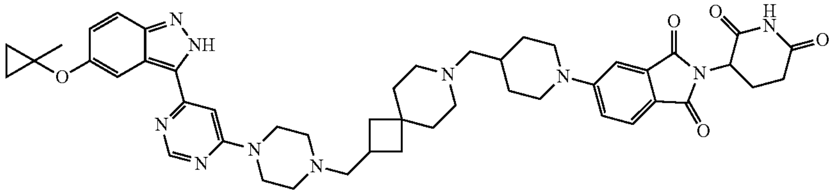 [SMILES: CC1(Oc2ccc3n[nH]c(-c4cc(N5CCN(CC6CC7(CCN(CC8CCN(c9ccc%10c(c9)C(=O)N(C9CCC(=O)NC9=O)C%10=O)CC8)CC7)C6)CC5)ncn4)c3c2)CC1] | 2-(2,6-dioxopiperidin-3-yl)-5-[4-({2-[(4-{6-[5-(1-methylcyclopropoxy)-2H-indazol-3-yl]pyrimidin-4-yl}piperazin-1-yl)methyl]-7-azaspiro[3.5]nonan-7-yl}methyl)piperidin-1-yl]-2,3-dihydro-1H-isoindole-1,3-dione |

TABLE 1-continued

Exemplary bifunctional compounds of the present disclosure**

| Ex. No. | Chemical Structure | IUPAC Name |
| --- | --- | --- |
| 178 | 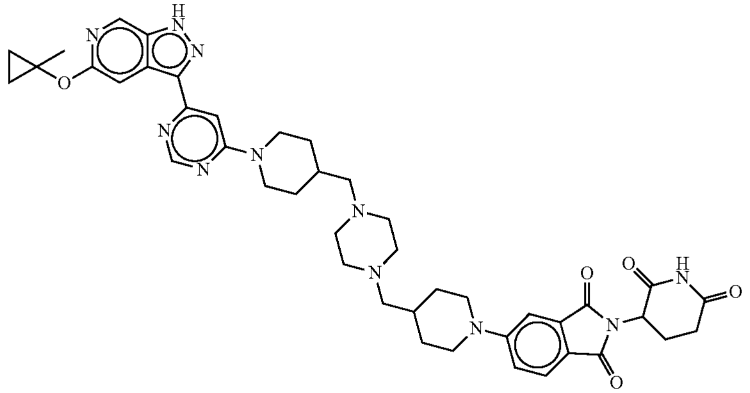 | 2-(2,6-dioxopiperidin-3-yl)-5-[4-({4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-2,3-dihydro-1H-isoindole-1,3-dione |
| 179 | 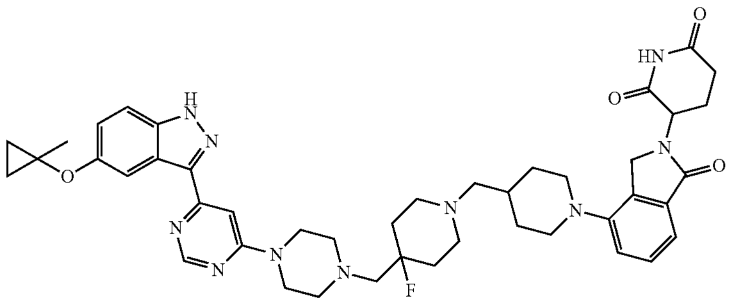 [SMILES: CC1(Oc2ccc3[nH]nc(-c4cc(N5CCN(CC6(F)CCN(CC7CCN(c8cccc9c8CN(C8CCC(=O)NC8=O)C9=O)CC7)CC6)CC5)ncn4)c3c2)CC1] | 3-{4-[4-({4-fluoro-4-[(4-{6-[5-(1-methylcyclopropoxy)-2H-indazol-3-yl]pyrimidin-4-yl}piperazin-1-yl)methyl]piperidin-1-yl}methyl)piperidin-1-yl]-1-oxo-2,3-dihydro-1H-isoindol-2-yl}piperidine-2,6-dione |
| 180 | 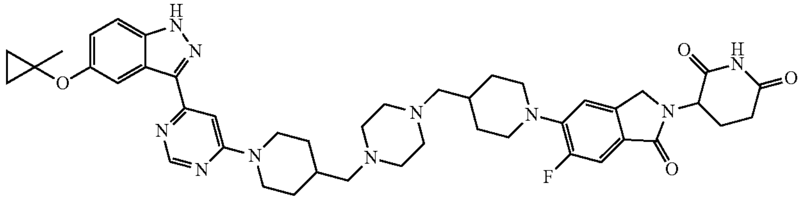 [SMILES: CC1(Oc2ccc3[nH]nc(-c4cc(N5CCC(CN6CCN(CC7CCN(c8cc9c(cc8F)C(=O)N(C8CCC(=O)NC8=O)C9)CC7)CC6)CC5)ncn4)c3c2)CC1] | 3-{6-fluoro-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 181 | 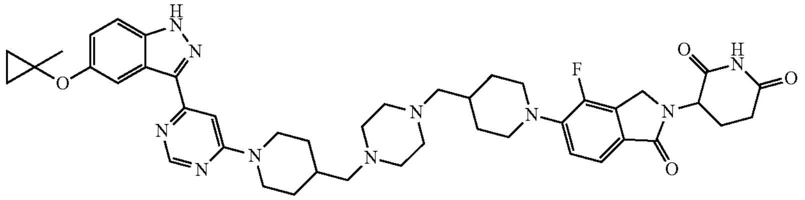 [SMILES: CC1(Oc2ccc3[nH]nc(-c4cc(N5CCC(CN6CCN(CC7CCN(c8ccc9c(c8F)CN(C8CCC(=O)NC8=O)C9=O)CC7)CC6)CC5)ncn4)c3c2)CC1] | 3-{4-fluoro-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 182 | 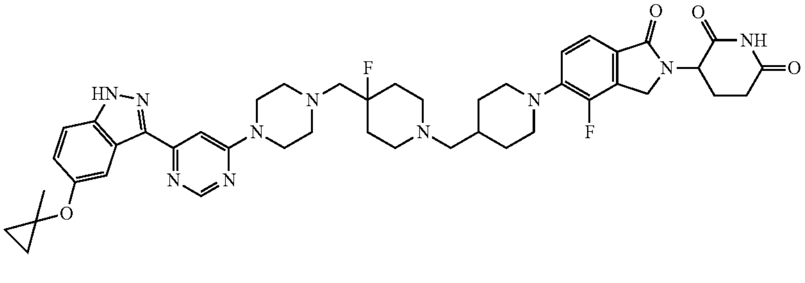 [SMILES: CC1(Oc2ccc3[nH]nc(-c4cc(N5CCN(CC6(F)CCN(CC7CCN(c8ccc9c(c8F)CN(C8CCC(=O)NC8=O)C9=O)CC7)CC6)CC5)ncn4)c3c2)CC1] | 3-{4-fluoro-5-[4-({4-fluoro-4-[(4-{6-[5-(1-methylcyclopropoxy)-1H-indazol-3-yl]pyrimidin-4-yl}piperazin-1-yl)methyl]piperidin-1-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 183 | 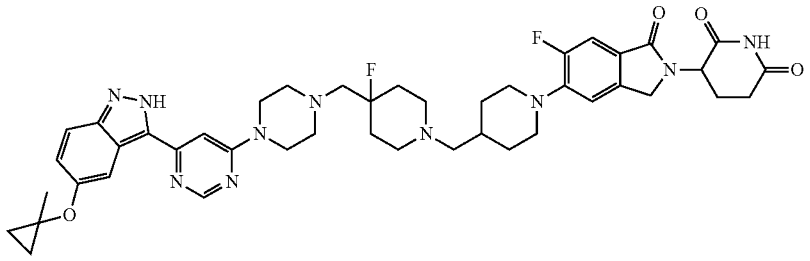 [SMILES: CC1(Oc2ccc3n[nH]c(-c4cc(N5CCN(CC6(F)CCN(CC7CCN(c8cc9c(cc8F)C(=O)N(C8CCC(=O)NC8=O)C9)CC7)CC6)CC5)ncn4)c3c2)CC1] | 3-{6-fluoro-5-[4-({4-fluoro-4-[(4-{6-[5-(1-methylcyclopropoxy)-2H-indazol-3-yl]pyrimidin-4-yl}piperazin-1-yl)methyl]piperidin-1-yl}methyl)piperidin-1-yl]-1-oxo-2,3-dihydro-1H-isoindol-2-yl}piperidine-2,6-dione |
| 184 | 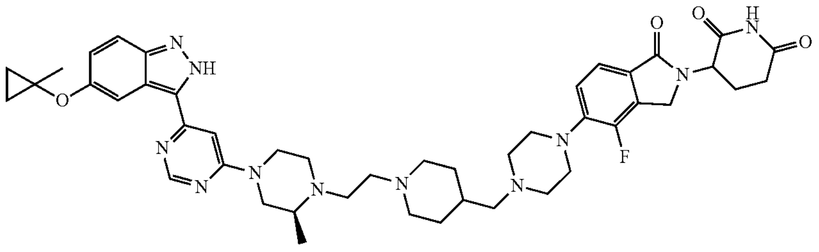 [SMILES: C[C@H]1CN(c2cc(-c3[nH]nc4ccc(OC5(C)CC5)cc34)ncn2)CCN1CCN1CCC(CN2CCN(c3ccc4c(c3F)CN(C3CCC(=O)NC3=O)C4=O)CC2)CC1] | 3-(4-fluoro-5-{4-[(1-{2-[(2S)-2-methyl-4-{6-[5-(1-methylcyclopropoxy)-2H-indazol-3-yl]pyrimidin-4-yl}piperazin-1-yl]ethyl}piperidin-4-yl)methyl]piperazin-1-yl}-1-oxo-2,3-dihydro-1H-isoindol-2-yl)piperidine-2,6-dione |
| 185 | 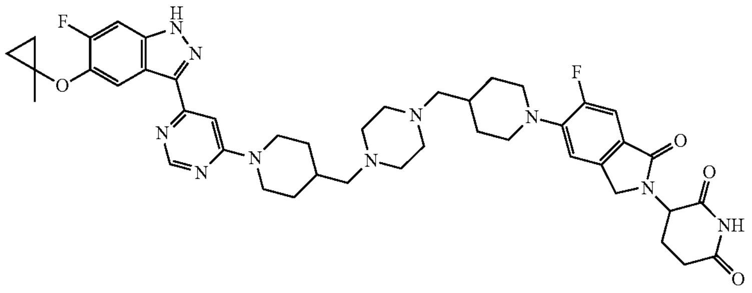 [SMILES: CC1(Oc2cc3c(-c4cc(N5CCC(CN6CCN(CC7CCN(c8cc9c(cc8F)C(=O)N(C8CCC(=O)NC8=O)C9)CC7)CC6)CC5)ncn4)n[nH]c3cc2F)CC1] | 3-{6-fluoro-5-[4-({4-[(1-{6-[6-fluoro-5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 186 | 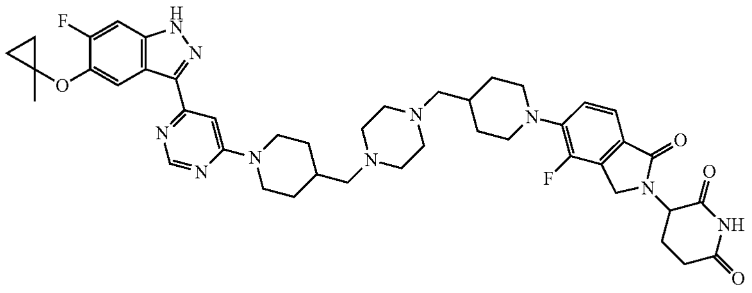 [SMILES: CC1(Oc2cc3c(-c4cc(N5CCC(CN6CCN(CC7CCN(c8ccc9c(c8F)CN(C8CCC(=O)NC8=O)C9=O)CC7)CC6)CC5)ncn4)n[nH]c3cc2F)CC1] | 3-{4-fluoro-5-[4-({4-[(1-{6-[6-fluoro-5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 187 | 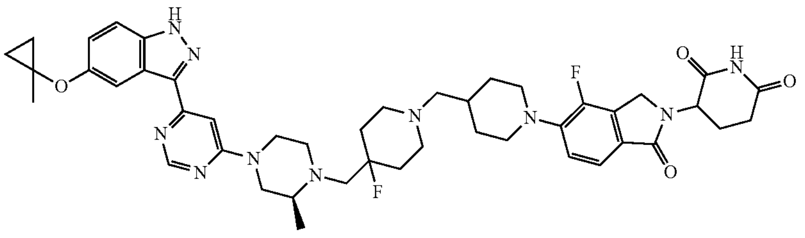 [SMILES: C[C@H]1CN(c2cc(-c3n[nH]c4ccc(OC5(C)CC5)cc34)ncn2)CCN1CC1(F)CCN(CC2CCN(c3ccc4c(c3F)CN(C3CCC(=O)NC3=O)C4=O)CC2)CC1] | 3-(4-fluoro-5-{4-[(4-fluoro-4-{[(2S)-2-methyl-4-{6-[5-(1-methylcyclopropoxy)-1H-indazol-3-yl]pyrimidin-4-yl}piperazin-1-yl]methyl}piperidin-1-yl)methyl]piperidin-1-yl}-1-oxo-2,3-dihydro-1H-isoindol-2-yl)piperidine-2,6-dione |

TABLE 1-continued

| Ex. No. | Chemical Structure | IUPAC Name |
|---|---|---|
| | Exemplary bifunctional compounds of the present disclosure** | |
| 188 | 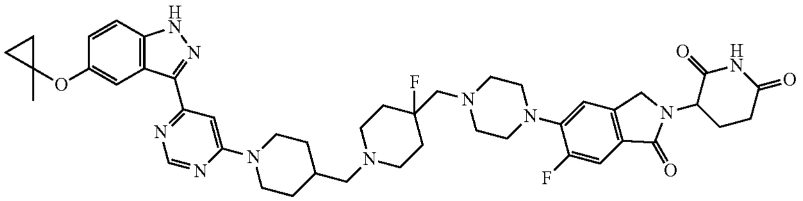 [SMILES: CC1(Oc2ccc3[nH]nc(-c4cc(N5CCC(CN6CCC(F)(CN7CCN(c8cc9c(cc8F)C(=O)N(C8CCC(=O)NC8=O)C9)CC7)CC6)CC5)ncn4)c3c2)CC1] | 3-{6-fluoro-5-[4-({4-fluoro-1-[(1-{6-[5-(1-methylcyclopropoxy)-1H-indazol-3-yl]pyrimidin-4-yl}piperidin-4-yl)methyl]piperidin-4-yl}methyl)piperazin-1-yl]-1-oxo-2,3-dihydro-1H-isoindol-2-yl}piperidine-2,6-dione |
| 189 | 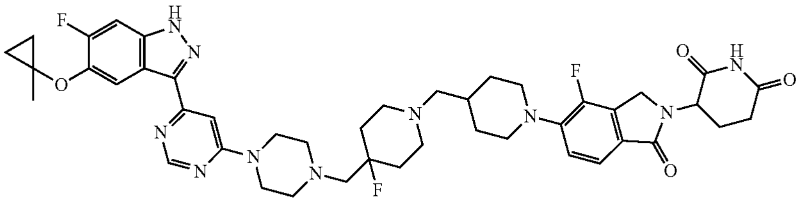 [SMILES: CC1(Oc2cc3c(-c4cc(N5CCN(CC6(F)CCN(CC7CCN(c8ccc9c(c8F)CN(C8CCC(=O)NC8=O)C9=O)CC7)CC6)CC5)ncn4)n[nH]c3cc2F)CC1] | 3-{4-fluoro-5-[4-({4-fluoro-4-[(4-{6-[6-fluoro-5-(1-methylcyclopropoxy)-1H-indazol-3-yl]pyrimidin-4-yl}piperazin-1-yl)methyl]piperidin-1-yl}methyl)piperidin-1-yl]-1-oxo-2,3-dihydro-1H-isoindol-2-yl}piperidine-2,6-dione |
| 190 | 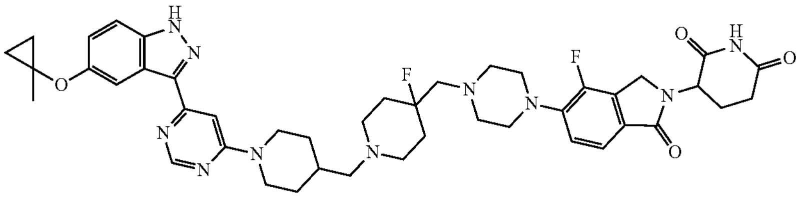 [SMILES: CC1(Oc2ccc3[nH]nc(-c4cc(N5CCC(CN6CCC(F)(CN7CCN(c8ccc9c(c8F)CN(C8CCC(=O)NC8=O)C9=O)CC7)CC6)CC5)ncn4)c3c2)CC1] | 3-{4-fluoro-5-[4-({4-fluoro-1-[(1-{6-[5-(1-methylcyclopropoxy)-1H-indazol-3-yl]pyrimidin-4-yl}piperidin-4-yl)methyl]piperidin-4-yl}methyl)piperazin-1-yl]-1-oxo-2,3-dihydro-1H-isoindol-2-yl}piperidine-2,6-dione |
| 191 | 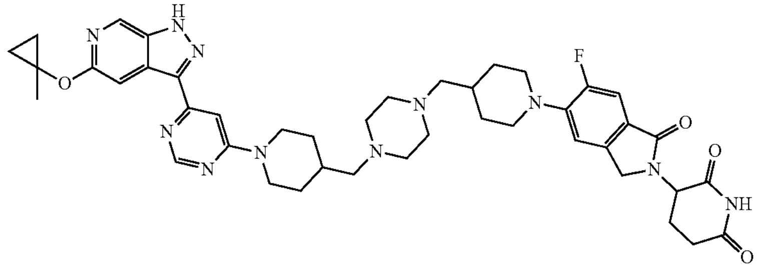 [SMILES: CC1(Oc2cc3c(-c4cc(N5CCC(CN6CCN(CC7CCN(c8cc9c(cc8F)C(=O)N(C8CCC(=O)NC8=O)C9)CC7)CC6)CC5)ncn4)n[nH]c3cn2)CC1] | 3-{6-fluoro-5-[4-({4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 192 | 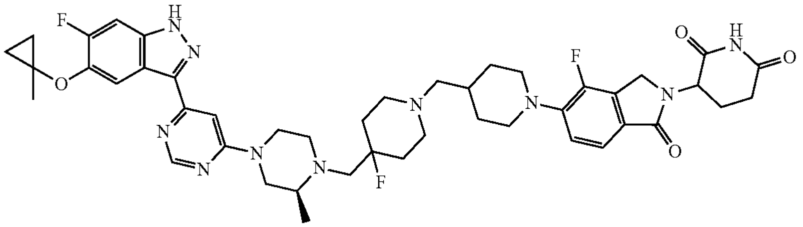 [SMILES: C[C@H]1CN(c2cc(-c3n[nH]c4cc(F)c(OC5(C)CC5)cc34)ncn2)CCN1CC1(F)CCN(CC2CCN(c3ccc4c(c3F)CN(C3CCC(=O)NC3=O)C4=O)CC2)CC1] | 3-(4-fluoro-5-{4-[(4-fluoro-4-{[(2S)-4-{6-[6-fluoro-5-(1-methylcyclopropoxy)-1H-indazol-3-yl]pyrimidin-4-yl}-2-methylpiperazin-1-yl]methyl}piperidin-1-yl)methyl]piperidin-1-yl}-1-oxo-2,3-dihydro-1H-isoindol-2-yl)piperidine-2,6-dione |

TABLE 1-continued

| Exemplary bifunctional compounds of the present disclosure** | | |
|---|---|---|
| Ex. No. | Chemical Structure | IUPAC Name |
| 193 | 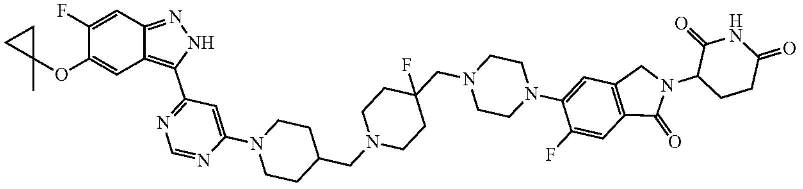 [SMILES: CC1(Oc2cc3c(-c4cc(N5CCC(CN6CCC(F)(CN7CCN(c8cc9c(cc8F)C(=O)N(C8CCC(=O)NC8=O)C9)CC7)CC6)CC5)ncn4)[nH]nc3cc2F)CC1] | 3-{6-fluoro-5-[4-({4-fluoro-1-[(1-{6-[6-fluoro-5-(1-methylcyclopropoxy)-2H-indazol-3-yl]pyrimidin-4-yl}piperidin-4-yl)methyl]piperidin-4-yl}methyl)piperazin-1-yl]-1-oxo-2,3-dihydro-1H-isoindol-2-yl}piperidine-2,6-dione |
| 194 | 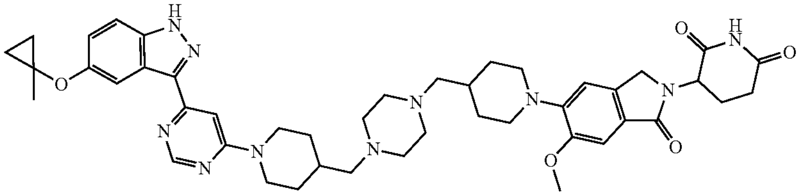 [SMILES: COc1cc2c(cc1N1CCC(CN3CCN(CC4CCN(c5cc(-c6n[nH]c7ccc(OC8(C)CC8)cc67)ncn5)CC4)CC3)CC1)CN(C1CCC(=O)NC1=O)C2=O] | 3-{6-methoxy-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 195 | 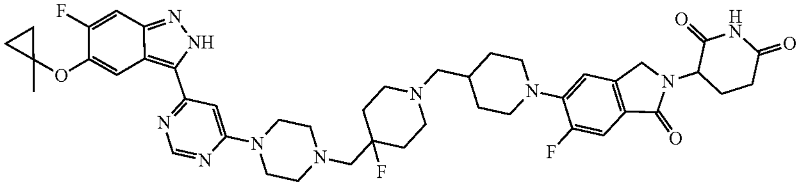 [SMILES: CC1(Oc2cc3c(-c4cc(N5CCN(CC6(F)CCN(CC7CCN(c8cc9c(cc8F)C(=O)N(C8CCC(=O)NC8=O)C9)CC7)CC6)CC5)ncn4)[nH]nc3cc2F)CC1] | 3-{6-fluoro-5-[4-({4-fluoro-4-[(4-{6-[6-fluoro-5-(1-methylcyclopropoxy)-2H-indazol-3-yl]pyrimidin-4-yl}piperazin-1-yl)methyl]piperidin-1-yl}methyl)piperidin-1-yl]-1-oxo-2,3-dihydro-1H-isoindol-2-yl}piperidine-2,6-dione |
| 196 | 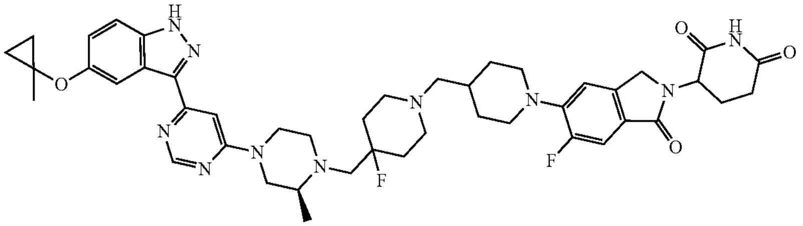 [SMILES: C[C@H]1CN(c2cc(-c3n[nH]c4ccc(OC5(C)CC5)cc34)ncn2)CCN1CC1(F)CCN(CC2CCN(c3cc4c(cc3F)C(=O)N(C3CCC(=O)NC3=O)C4)CC2)CC1] | 3-(6-fluoro-5-{4-[(4-fluoro-4-{[(2S)-2-methyl-4-{6-[5-(1-methylcyclopropoxy)-1H-indazol-3-yl]pyrimidin-4-yl}piperazin-1-yl]methyl}piperidin-1-yl)methyl]piperidin-1-yl}-1-oxo-2,3-dihydro-1H-isoindol-2-yl)piperidine-2,6-dione |
| 197 | 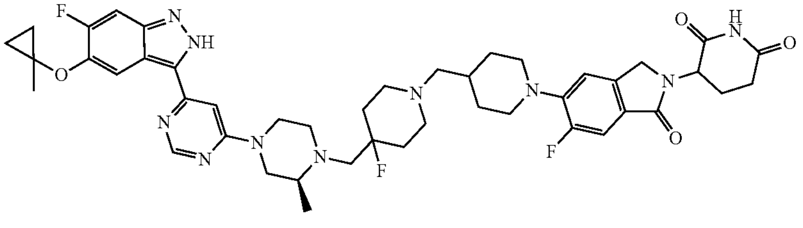 [SMILES: C[C@H]1CN(c2cc(-c3[nH]nc4cc(F)c(OC5(C)CC5)cc34)ncn2)CCN1CC1(F)CCN(CC2CCN(c3cc4c(cc3F)C(=O)N(C3CCC(=O)NC3=O)C4)CC2)CC1] | 3-(6-fluoro-5-{4-[(4-fluoro-4-{[(2S)-4-{6-[6-fluoro-5-(1-methylcyclopropoxy)-2H-indazol-3-yl]pyrimidin-4-yl}-2-methylpiperazin-1-yl]methyl}piperidin-1-yl)methyl]piperidin-1-yl}-1-oxo-2,3-dihydro-1H-isoindol-2-yl)piperidine-2,6-dione |

TABLE 1-continued

| Exemplary bifunctional compounds of the present disclosure** | | |
|---|---|---|
| Ex. No. | Chemical Structure | IUPAC Name |
| 198 | 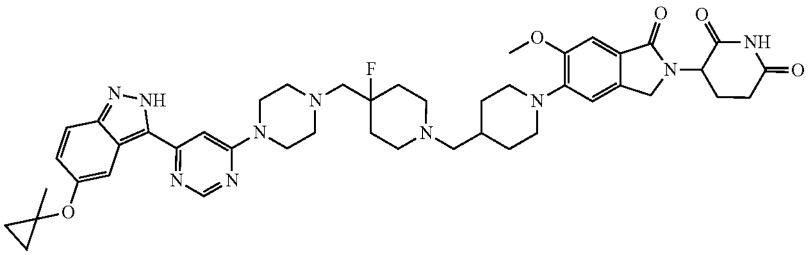 [SMILES: COc1cc2c(cc1N1CCC(CN3CCC(F)(CN4CCN(c5cc(-c6[nH]nc7ccc(OC8(C)CC8)cc67)ncn5)CC4)CC3)CC1)CN(C1CCC(=O)NC1=O)C2=O] | 3-{5-[4-({4-fluoro-4-[(4-{6-[5-(1-methylcyclopropoxy)-2H-indazol-3-yl]pyrimidin-4-yl}piperazin-1-yl)methyl]piperidin-1-yl}methyl)piperidin-1-yl]-6-methoxy-1-oxo-2,3-dihydro-1H-isoindol-2-yl}piperidine-2,6-dione |
| 199 | 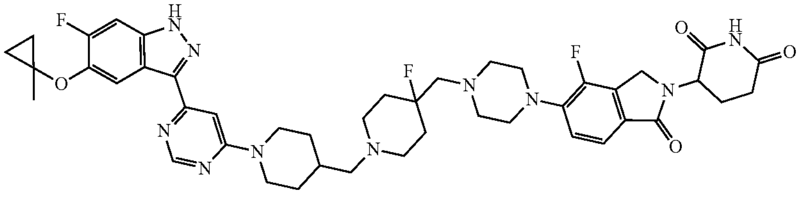 [SMILES: CC1(Oc2cc3c(-c4cc(N5CCC(CN6CCC(F)(CN7CCN(c8ccc9c(c8F)CN(C8CCC(=O)NC8=O)C9=O)CC7)CC6)CC5)ncn4)n[nH]c3cc2F)CC1] | 3-{4-fluoro-5-[4-({4-fluoro-1-[(1-{6-[6-fluoro-5-(1-methylcyclopropoxy)-1H-indazol-3-yl]pyrimidin-4-yl}piperidin-4-yl)methyl]piperidin-4-yl}methyl)piperazin-1-yl]-1-oxo-2,3-dihydro-1H-isoindol-2-yl}piperidine-2,6-dione |
| 200 | 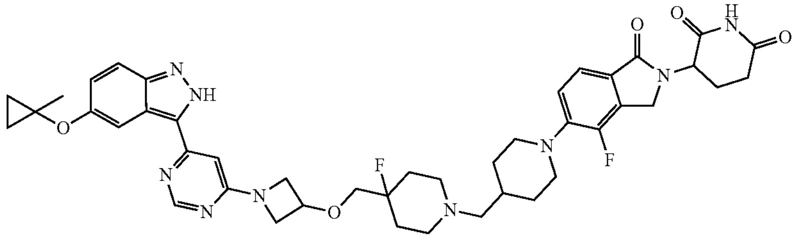 [SMILES: CC1(Oc2ccc3n[nH]c(-c4cc(N5CC(OCC6(F)CCN(CC7CCN(c8ccc9c(c8F)CN(C8CCC(=O)NC8=O)C9=O)CC7)CC6)C5)ncn4)c3c2)CC1] | 3-(4-fluoro-5-{4-[(4-fluoro-4-{[(1-{6-[5-(1-methylcyclopropoxy)-2H-indazol-3-yl]pyrimidin-4-yl}azetidin-3-yl)oxy]methyl}piperidin-1-yl)methyl]piperidin-1-yl}-1-oxo-2,3-dihydro-1H-isoindol-2-yl)piperidine-2,6-dione |
| 201 | 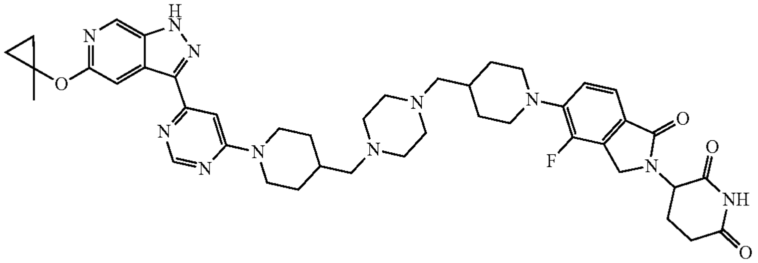 [SMILES: CC1(Oc2cc3c(-c4cc(N5CCC(CN6CCN(CC7CCN(c8ccc9c(c8F)CN(C8CCC(=O)NC8=O)C9=O)CC7)CC6)CC5)ncn4)n[nH]c3cn2)CC1] | 3-{4-fluoro-5-[4-({4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 202 | 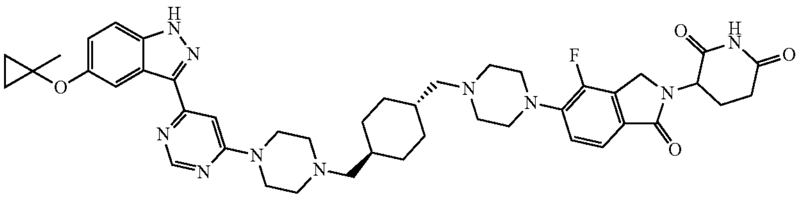 [SMILES: CC1(Oc2ccc3[nH]nc(-c4cc(N5CCN(C[C@H]6CC[C@H](CN7CCN(c8ccc9c(c8F)CN(C8CCC(=O)NC8=O)C9=O)CC7)CC6)CC5)ncn4)c3c2)CC1] | 3-[4-fluoro-1-oxo-5-(4-{[(1r,4r)-4-[(4-{6-[5-(1-methylcyclopropoxy)-1H-indazol-3-yl]pyrimidin-4-yl}piperazin-1-yl)methyl]cyclohexyl]methyl}piperazin-1-yl)-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 203 | 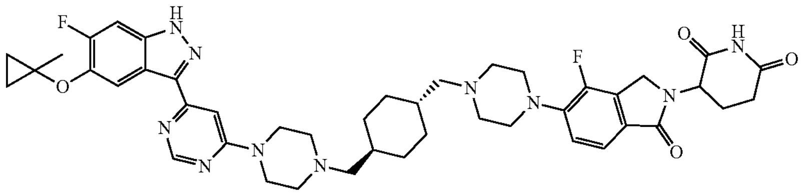 [SMILES: CC1(Oc2cc3c(-c4cc(N5CCN(C[C@H]6CC[C@H](CN7CCN(c8ccc9c(c8F)CN(C8CCC(=O)NC8=O)C9=O)CC7)CC6)CC5)ncn4)n[nH]c3cc2F)CC1] | 3-[4-fluoro-1-oxo-5-(4-{[(1r,4r)-4-[(4-{6-[6-fluoro-5-(1-methylcyclopropoxy)-1H-indazol-3-yl]pyrimidin-4-yl}piperazin-1-yl)methyl]cyclohexyl]methyl}piperazin-1-yl)-2,3-dihydro-1H-isoindol-2-yl]piperidine-2,6-dione |
| 204 | 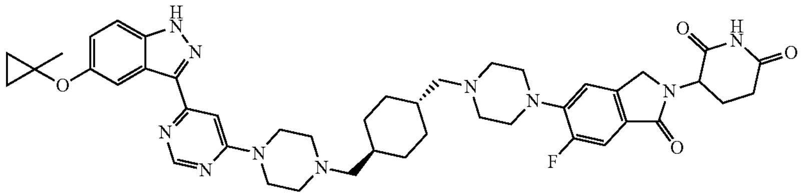 [SMILES: CC1(Oc2ccc3[nH]nc(-c4cc(N5CCN(C[C@H]6CC[C@H](CN7CCN(c8cc9c(cc8F)C(=O)N(C8CCC(=O)NC8=O)C9)CC7)CC6)CC5)ncn4)c3c2)CC1] | 3-[6-fluoro-1-oxo-5-(4-{[(1r,4r)-4-[(4-{6-[5-(1-methylcyclopropoxy)-1H-indazol-3-yl]pyrimidin-4-yl}piperazin-1-yl)methyl]cyclohexyl]methyl}piperazin-1-yl)-2,3-dihydro-1H-isoindol-2-yl]piperidine-2,6-dione |
| 205 | 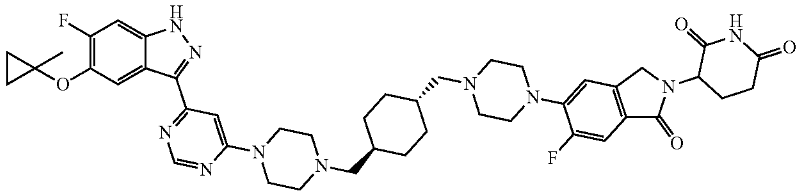 [SMILES: CC1(Oc2cc3c(-c4cc(N5CCN(C[C@H]6CC[C@H](CN7CCN(c8cc9c(cc8F)C(=O)N(C8CCC(=O)NC8=O)C9)CC7)CC6)CC5)ncn4)n[nH]c3cc2F)CC1] | 3-[6-fluoro-1-oxo-5-(4-{[(1r,4r)-4-[(4-{6-[6-fluoro-5-(1-methylcyclopropoxy)-1H-indazol-3-yl]pyrimidin-4-yl}piperazin-1-yl)methyl]cyclohexyl]methyl}piperazin-1-yl)-2,3-dihydro-1H-isoindol-2-yl]piperidine-2,6-dione |
| 206 | 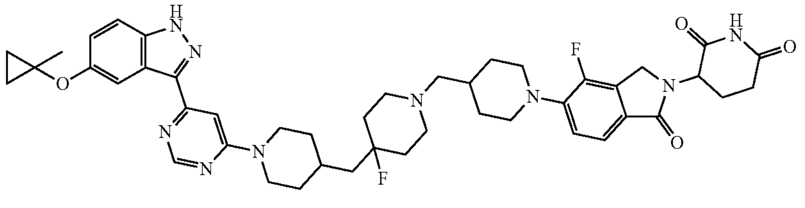 [SMILES: CC1(Oc2ccc3[nH]nc(-c4cc(N5CCC(CC6(F)CCN(CC7CCN(c8ccc9c(c8F)CN(C8CCC(=O)NC8=O)C9=O)CC7)CC6)CC5)ncn4)c3c2)CC1] | 3-{4-fluoro-5-[4-({4-fluoro-4-[(1-{6-[5-(1-methylcyclopropoxy)-1H-indazol-3-yl]pyrimidin-4-yl}piperidin-4-yl)methyl]piperidin-1-yl}methyl)piperidin-1-yl]-1-oxo-2,3-dihydro-1H-isoindol-2-yl}piperidine-2,6-dione |
| 207 | 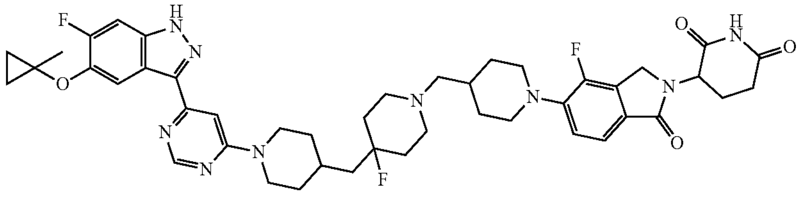 [SMILES: CC1(Oc2cc3c(-c4cc(N5CCC(CC6(F)CCN(CC7CCN(c8ccc9c(c8F)CN(C8CCC(=O)NC8=O)C9=O)CC7)CC6)CC5)ncn4)n[nH]c3cc2F)CC1] | 3-{4-fluoro-5-[4-({4-fluoro-4-[(1-{6-[6-fluoro-5-(1-methylcyclopropoxy)-1H-indazol-3-yl]pyrimidin-4-yl}piperidin-4-yl)methyl]piperidin-1-yl}methyl)piperidin-1-yl]-1-oxo-2,3-dihydro-1H-isoindol-2-yl}piperidine-2,6-dione |

TABLE 1-continued

Exemplary bifunctional compounds of the present disclosure**

| Ex. No. | Chemical Structure | IUPAC Name |
| --- | --- | --- |
| 208 | 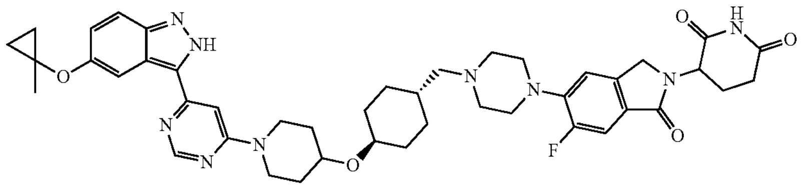 | 3-[6-fluoro-1-oxo-5-(4-{[(1r,4r)-4-[(1-{6-[5-(1-methylcyclopropoxy)-2H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 209 | 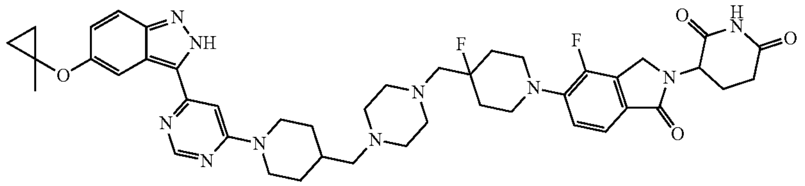 [SMILES: CC1(Oc2ccc3n[nH]c(-c4cc(N5CCC(CN6CCN(CC7(F)CCN(c8ccc9c(c8F)CN(C8CCC(=O)NC8=O)C9=O)CC7)CC6)CC5)ncn4)c3c2)CC1] | 3-{4-fluoro-5-[4-fluoro-4-({4-[(1-{6-[5-(1-methylcyclopropoxy)-2H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 210 | 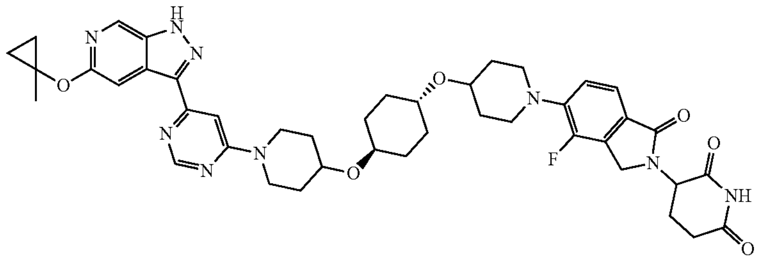 [SMILES: CC1(Oc2cc3c(-c4cc(N5CCC(O[C@H]6CC[C@H](OC7CCN(c8ccc9c(c8F)CN(C8CCC(=O)NC8=O)C9=O)CC7)CC6)CC5)ncn4)n[nH]c3cn2)CC1] | 3-[4-fluoro-1-oxo-5-(4-{[(1r,4r)-4-[(1-{6-[5-(1-methylcyclopropoxy)-1H-pyrazolo[3,4-c]pyridin-3-yl]pyrimidin-4-yl}piperidin-4-yl)oxy]cyclohexyl]oxy}piperidin-1-yl)-2,3-dihydro-1H-isoindol-2-yl]piperidine-2,6-dione |
| 211 | 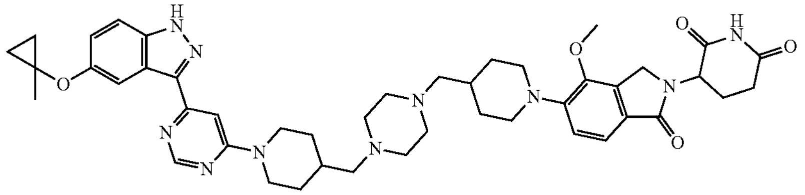 [SMILES: COc1c(N2CCC(CN3CCN(CC4CCN(c5cc(-c6n[nH]c7ccc(OC8(C)CC8)cc67)ncn5)CC4)CC3)CC2)ccc2c1CN(C1CCC(=O)NC1=O)C2=O] | 3-{4-methoxy-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 212 | 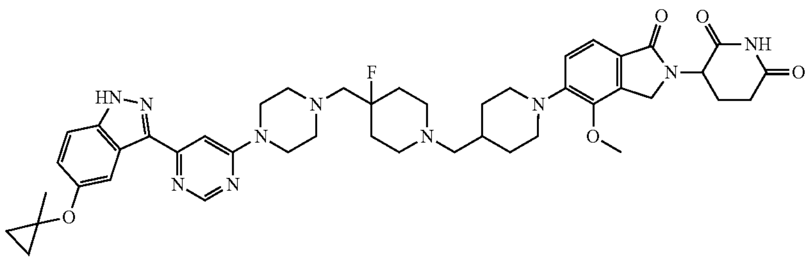 [SMILES: COc1c(N2CCC(CN3CCC(F)(CN4CCN(c5cc(-c6n[nH]c7ccc(OC8(C)CC8)cc67)ncn5)CC4)CC3)CC2)ccc2c1CN(C1CCC(=O)NC1=O)C2=O] | 3-{5-[4-({4-fluoro-4-[(4-{6-[5-(1-methylcyclopropoxy)-1H-indazol-3-yl]pyrimidin-4-yl}piperazin-1-yl)methyl]piperidin-1-yl}methyl)piperidin-1-yl]-4-methoxy-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 213 | 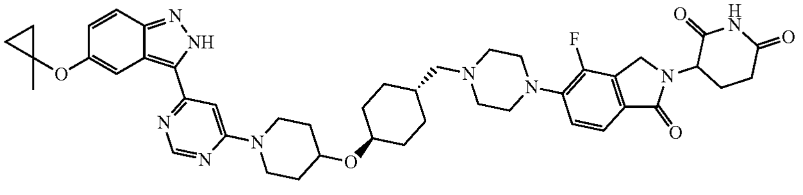 [SMILES: CC1(Oc2ccc3n[nH]c(-c4cc(N5CCC(O[C@H]6CC[C@H](CN7CCN(c8ccc9c(c8F)CN(C8CCC(=O)NC8=O)C9=O)CC7)CC6)CC5)ncn4)c3c2)CC1] | 3-[4-fluoro-1-oxo-5-(4-{[(1r,4r)-4-[(1-{6-[5-(1-methylcyclopropoxy)-2H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 214 | 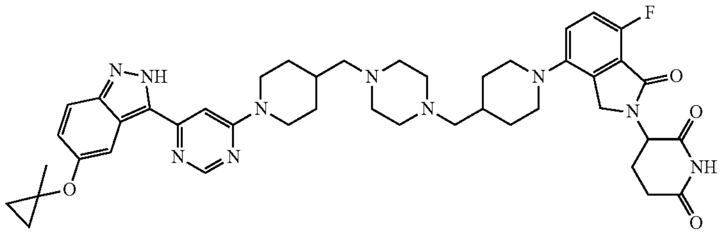 [SMILES: CC1(Oc2ccc3n[nH]c(-c4cc(N5CCC(CN6CCN(CC7CCN(c8ccc(F)c9c8CN(C8CCC(=O)NC8=O)C9=O)CC7)CC6)CC5)ncn4)c3c2)CC1] | 3-{7-fluoro-4-[4-({4-[(1-{6-[5-(1-methylcyclopropoxy)-2H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 215 | 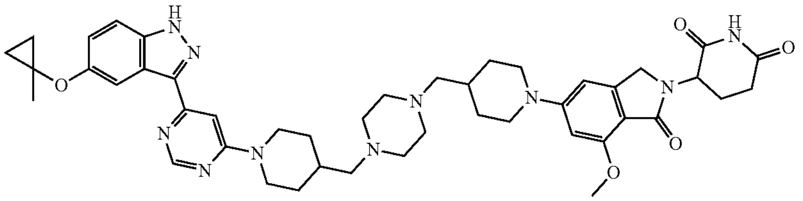 [SMILES: COc1cc(N2CCC(CN3CCN(CC4CCN(c5cc(-c6n[nH]c7ccc(OC8(C)CC8)cc67)ncn5)CC4)CC3)CC2)cc2c1C(=O)N(C1CCC(=O)NC1=O)C2] | 3-{7-methoxy-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 216 | 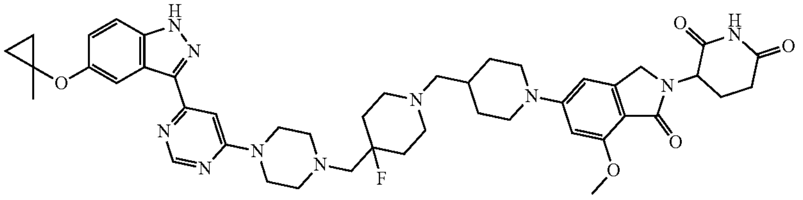 [SMILES: COc1cc(N2CCC(CN3CCC(F)(CN4CCN(c5cc(-c6n[nH]c7ccc(OC8(C)CC8)cc67)ncn5)CC4)CC3)CC2)cc2c1C(=O)N(C1CCC(=O)NC1=O)C2] | 3-{5-[4-({4-fluoro-4-[(4-{6-[5-(1-methylcyclopropoxy)-1H-indazol-3-yl]pyrimidin-4-yl}piperazin-1-yl)methyl]piperidin-1-yl}methyl)piperidin-1-yl]-7-methoxy-1-oxo-2,3-dihydro-1H-isoindol-2-yl}piperidine-2,6-dione |
| 217 | 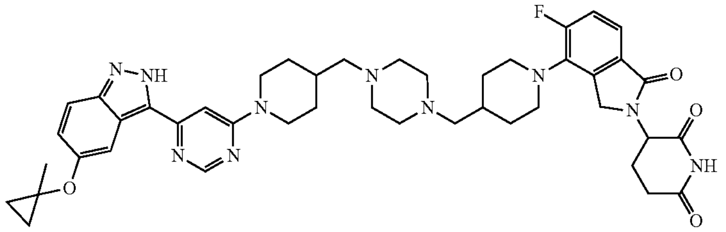 [SMILES: CC1(Oc2ccc3n[nH]c(-c4cc(N5CCC(CN6CCN(CC7CCN(c8c(F)ccc9c8CN(C8CCC(=O)NC8=O)C9=O)CC7)CC6)CC5)ncn4)c3c2)CC1] | 3-{5-fluoro-4-[4-({4-[(1-{6-[5-(1-methylcyclopropoxy)-2H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 218 | 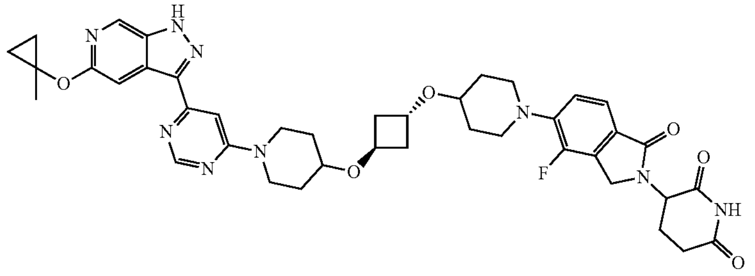 [SMILES: CC1(Oc2cc3c(-c4cc(N5CCC(O[C@H]6C[C@H](OC7CCN(c8ccc9c(c8F)CN(C8CCC(=O)NC8=O)C9=O)CC7)C6)CC5)ncn4)n[nH]c3cn2)CC1] | 3-(4-fluoro-1-oxo-5-{4-[(1r,3r)-3-[(1-{6-[5-(1-methylcyclopropoxy)-1H-pyrazolo[3,4-c]pyridin-3-yl]pyrimidin-4-yl}piperidin-4-yl)oxy]cyclobutoxy] piperidin-1-yl}-2,3-dihydro-1H-isoindol-2-yl)piperidine-2,6-dione |
| 219 | 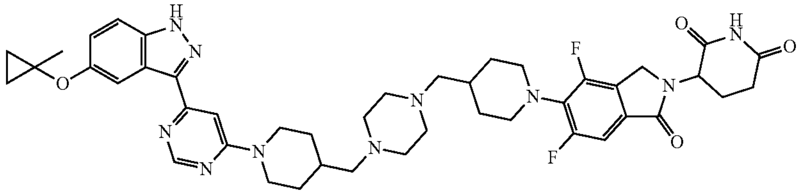 [SMILES: CC1(Oc2ccc3[nH]nc(-c4cc(N5CCC(CN6CCN(CC7CCN(c8c(F)cc9c(c8F)CN(C8CCC(=O)NC8=O)C9=O)CC7)CC6)CC5)ncn4)c3c2)CC1] | 3-{4,6-difluoro-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 220 | 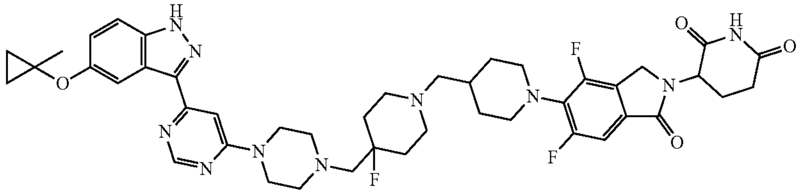 [SMILES: CC1(Oc2ccc3[nH]nc(-c4cc(N5CCN(CC6(F)CCN(CC7CCN(c8c(F)cc9c(c8F)CN(C8CCC(=O)NC8=O)C9=O)CC7)CC6)CC5)ncn4)c3c2)CC1] | 3-{4,6-difluoro-5-[4-({4-fluoro-4-[(4-{6-[5-(1-methylcyclopropoxy)-1H-indazol-3-yl]pyrimidin-4-yl}piperazin-1-yl)methyl]piperidin-1-yl}methyl)piperidin-1-yl]-1-oxo-2,3-dihydro-1H-isoindol-2-yl}piperidine-2,6-dione |
| 221 | 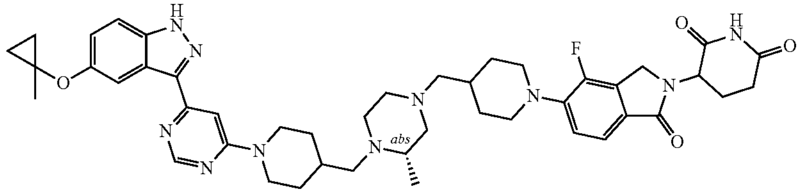 [SMILES: C[C@H]1CN(CC2CCN(c3ccc4c(c3F)CN(C3CCC(=O)NC3=O)C4=O)CC2)CCN1CC1CCN(c2cc(-c3n[nH]c4ccc(OC5(C)CC5)cc34)ncn2)CC1] | 3-[4-fluoro-5-(4-{[(3S)-3-methyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 222 | 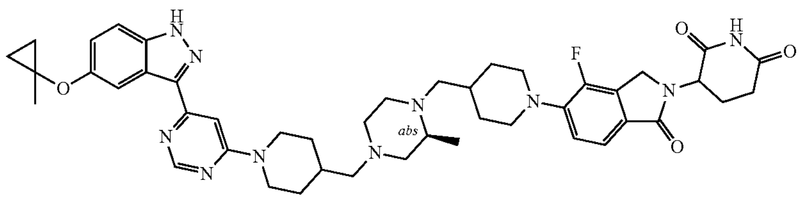 [SMILES: C[C@H]1CN(CC2CCN(c3cc(-c4n[nH]c5ccc(OC6(C)CC6)cc45)ncn3)CC2)CCN1CC1CCN(c2ccc3c(c2F)CN(C2CCC(=O)NC2=O)C3=O)CC1] | 3-[4-fluoro-5-(4-{[(2S)-2-methyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 223 | 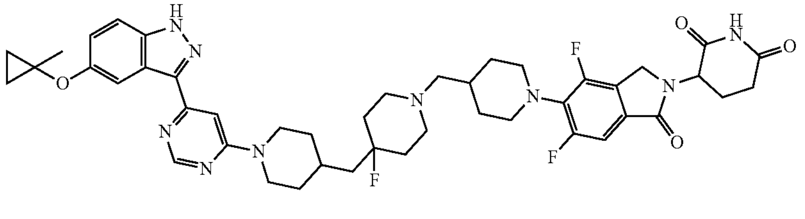 [SMILES: CC1(Oc2ccc3[nH]nc(-c4cc(N5CCC(CC6(F)CCN(CC7CCN(c8c(F)cc9c(c8F)CN(C8CCC(=O)NC8=O)C9=O)CC7)CC6)CC5)ncn4)c3c2)CC1] | 3-{4,6-difluoro-5-[4-({4-fluoro-4-[(1-{6-[5-(1-methylcyclopropoxy)-1H-indazol-3-yl]pyrimidin-4-yl}piperidin-4-yl)methyl]piperidin-1-yl}methyl)piperidin-1-yl]-1-oxo-2,3-dihydro-1H-isoindol-2-yl}piperidine-2,6-dione |
| 224 | 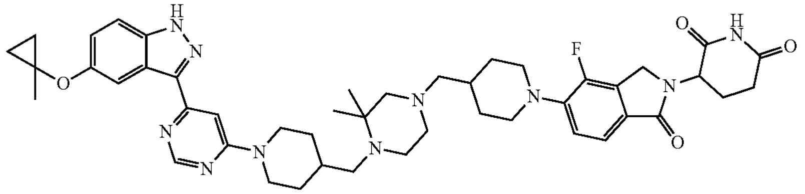 [SMILES: CC1(Oc2ccc3[nH]nc(-c4cc(N5CCC(CN6CCN(CC7CCN(c8ccc9c(c8F)CN(C8CCC(=O)NC8=O)C9=O)CC7)CC6(C)C)CC5)ncn4)c3c2)CC1] | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-4-fluoro-1-oxo-2,3-dihydro-1H-isoindol-2-yl}piperidine-2,6-dione |
| 225 | 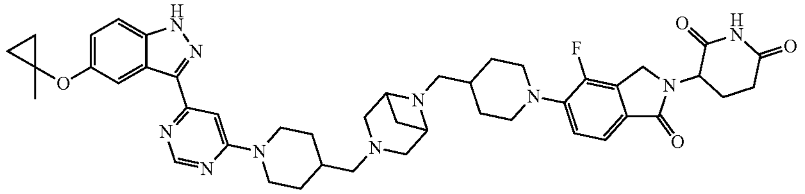 [SMILES: CC1(Oc2ccc3[nH]nc(-c4cc(N5CCC(CN6CC7CC(C6)N7CC6CCN(c7ccc8c(c7F)CN(C7CCC(=O)NC7=O)C8=O)CC6)CC5)ncn4)c3c2)CC1] | 3-{4-fluoro-5-[4-({3-[(1-{6-[5-(1-methylcyclopropoxy)-1H-indazol-3-yl]pyrimidin-4-yl}piperidin-4-yl)methyl]-3,6-diazabicyclo[3.1.1]heptan-6-yl}methyl)piperidin-1-yl]-1-oxo-2,3-dihydro-1H-isoindol-2-yl}piperidine-2,6-dione |
| 226 | 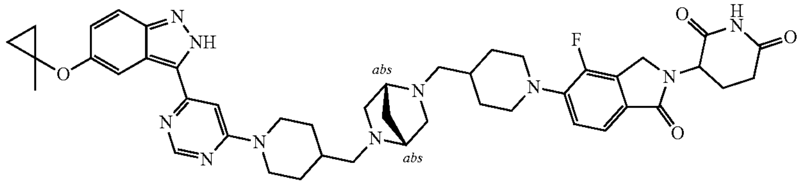 [SMILES: CC1(Oc2ccc3n[nH]c(-c4cc(N5CCC(CN6C[C@H]7C[C@@H]6CN7CC6CCN(c7ccc8c(c7F)CN(C7CCC(=O)NC7=O)C8=O)CC6)CC5)ncn4)c3c2)CC1] | 3-[4-fluoro-5-(4-{[(1R,4R)-5-[(1-{6-[5-(1-methylcyclopropoxy)-2H-indazol-3-yl]pyrimidin-4-yl}piperidin-4-yl)methyl]-2,5-diazabicyclo[2.2.1]heptan-2-yl]methyl}piperidin-1-yl)-1-oxo-2,3-dihydro-1H-isoindol-2-yl]piperidine-2,6-dione |
| 227 | 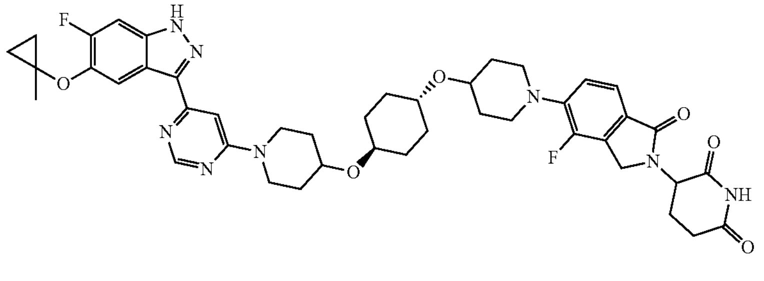 [SMILES: CC1(Oc2cc3c(-c4cc(N5CCC(O[C@H]6CC[C@H](OC7CCN(c8ccc9c(c8F)CN(C8CCC(=O)NC8=O)C9=O)CC7)CC6)CC5)ncn4)n[nH]c3cc2F)CC1] | 3-[4-fluoro-1-oxo-5-(4-{[(1r,4r)-4-[(1-{6-[6-fluoro-5-(1-methylcyclopropoxy)-1H-indazol-3-yl]pyrimidin-4-yl}piperidin-4-yl)oxy]cyclohexyl]oxy}piperidin-1-yl)-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 228 | 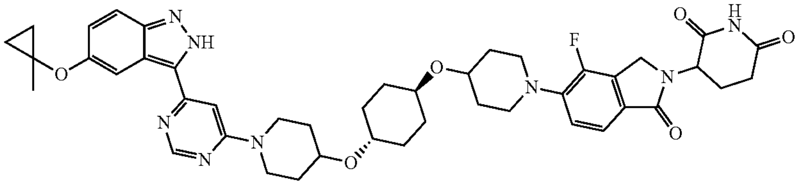 [SMILES: CC1(Oc2ccc3n[nH]c(-c4cc(N5CCC(O[C@H]6CC[C@H](OC7CCN(c8ccc9c(c8F)CN(C8CCC(=O)NC8=O)C9=O)CC7)CC6)CC5)ncn4)c3c2)CC1] | 3-[4-fluoro-1-oxo-5-(4-{[(1r,4r)-4-[(1-{6-[5-(1-methylcyclopropoxy)-2H-indazol-3-yl]pyrimidin-4-yl}piperidin-4-yl)oxy]cyclohexyl]oxy}piperidin-1-yl)-2,3-dihydro-1H-isoindol-2-yl]piperidine-2,6-dione |
| 229 | 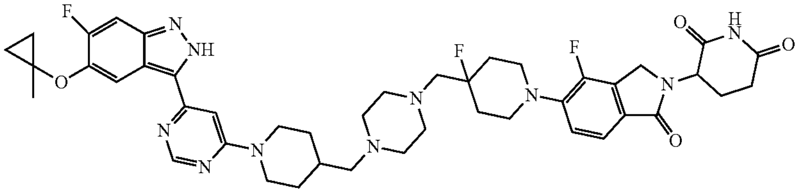 [SMILES: CC1(Oc2cc3c(-c4cc(N5CCC(CN6CCN(CC7(F)CCN(c8ccc9c(c8F)CN(C8CCC(=O)NC8=O)C9=O)CC7)CC6)CC5)ncn4)[nH]nc3cc2F)CC1] | 3-{4-fluoro-5-[4-fluoro-4-({4-[(1-{6-[6-fluoro-5-(1-methylcyclopropoxy)-2H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 230 | 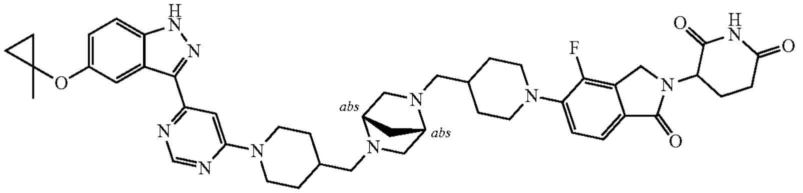 [SMILES: CC1(Oc2ccc3[nH]nc(-c4cc(N5CCC(CN6C[C@@H]7C[C@H]6CN7CC6CCN(c7ccc8c(c7F)CN(C7CCC(=O)NC7=O)C8=O)CC6)CC5)ncn4)c3c2)CC1] | 3-[4-fluoro-5-(4-{[(1S,4S)-5-[(1-{6-[5-(1-methylcyclopropoxy)-1H-indazol-3-yl]pyrimidin-4-yl}piperidin-4-yl)methyl]-2,5-diazabicyclo[2.2.1]heptan-2-yl]methyl}piperidin-1-yl)-1-oxo-2,3-dihydro-1H-isoindol-2-yl]piperidine-2,6-dione |
| 231 | 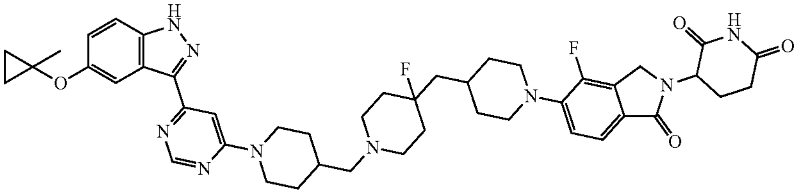 [SMILES: CC1(Oc2ccc3[nH]nc(-c4cc(N5CCC(CN6CCC(F)(CC7CCN(c8ccc9c(c8F)CN(C8CCC(=O)NC8=O)C9=O)CC7)CC6)CC5)ncn4)c3c2)CC1] | 3-{4-fluoro-5-[4-({4-fluoro-1-[(1-{6-[5-(1-methylcyclopropoxy)-1H-indazol-3-yl]pyrimidin-4-yl}piperidin-4-yl)methyl]piperidin-4-yl}methyl)piperidin-1-yl]-1-oxo-2,3-dihydro-1H-isoindol-2-yl}piperidine-2,6-dione |
| 232 | 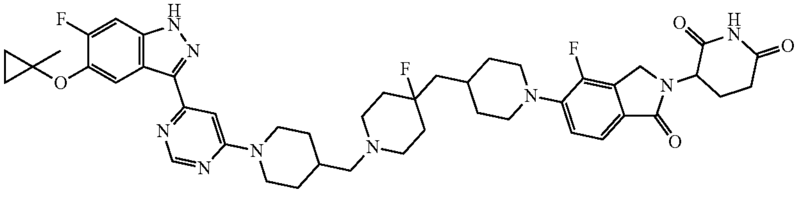 [SMILES: CC1(Oc2cc3c(-c4cc(N5CCC(CN6CCC(F)(CC7CCN(c8ccc9c(c8F)CN(C8CCC(=O)NC8=O)C9=O)CC7)CC6)CC5)ncn4)n[nH]c3cc2F)CC1] | 3-{4-fluoro-5-[4-({4-fluoro-1-[(1-{6-[6-fluoro-5-(1-methylcyclopropoxy)-1H-indazol-3-yl]pyrimidin-4-yl}piperidin-4-yl)methyl]piperidin-4-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 233 | 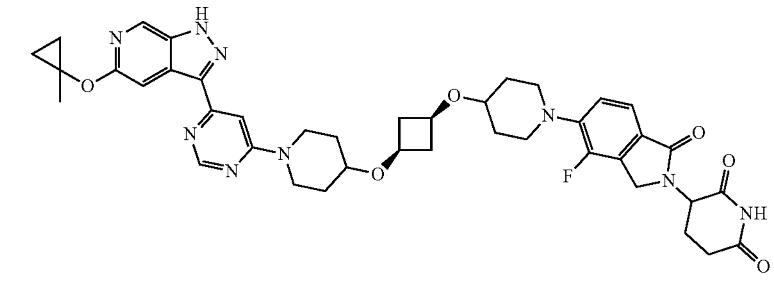 [SMILES: CC1(Oc2cc3c(-c4cc(N5CCC(O[C@H]6C[C@@H](OC7CCN(c8ccc9c(c8F)CN(C8CCC(=O)NC8=O)C9=O)CC7)C6)CC5)ncn4)n[nH]c3cn2)CC1] | 3-(4-fluoro-1-oxo-5-{4-[(1s,3s)-3-[(1-{6-[5-(1-methylcyclopropoxy)-1H-pyrazolo[3,4-c]pyridin-3-yl]pyrimidin-4-yl}piperidin-4-yl)oxy]cyclobutoxy]piperidin-1-yl}-2,3-dihydro-1H-isoindol-2-yl)piperidine-2,6-dione |
| 234 | 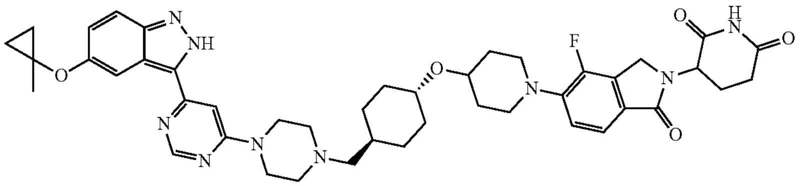 [SMILES: CC1(Oc2ccc3n[nH]c(-c4cc(N5CCN(C[C@H]6CC[C@H](OC7CCN(c8ccc9c(c8F)CN(C8CCC(=O)NC8=O)C9=O)CC7)CC6)CC5)ncn4)c3c2)CC1] | 3-[4-fluoro-1-oxo-5-(4-{[(1r,4r)-4-[(4-{6-[5-(1-methylcyclopropoxy)-2H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 235 | 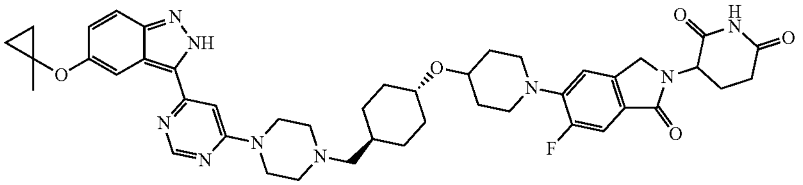 [SMILES: CC1(Oc2ccc3n[nH]c(-c4cc(N5CCN(C[C@H]6CC[C@H](OC7CCN(c8cc9c(cc8F)C(=O)N(C8CCC(=O)NC8=O)C9)CC7)CC6)CC5)ncn4)c3c2)CC1] | 3-[6-fluoro-1-oxo-5-(4-{[(1r,4r)-4-[(4-{6-[5-(1-methylcyclopropoxy)-2H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 236 | 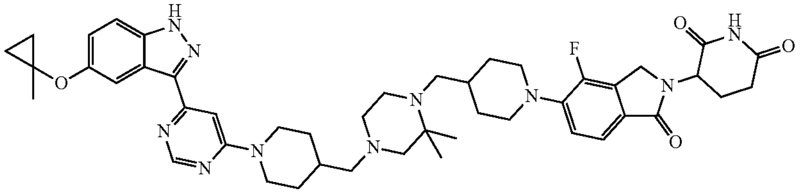 [SMILES: CC1(Oc2ccc3[nH]nc(-c4cc(N5CCC(CN6CCN(CC7CCN(c8ccc9c(c8F)CN(C8CCC(=O)NC8=O)C9=O)CC7)C(C)(C)C6)CC5)ncn4)c3c2)CC1] | 3-{5-[4-({2,2-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-4-fluoro-1-oxo-2,3-dihydro-1H-isoindol-2-yl}piperidine-2,6-dione |
| 237 | 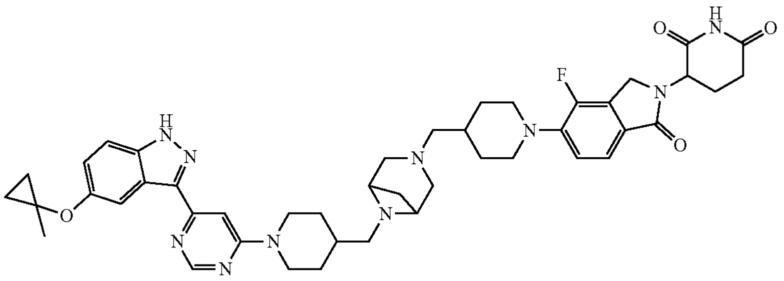 [SMILES: CC1(Oc2ccc3[nH]nc(-c4cc(N5CCC(CN6C7CC6CN(CC6CCN(c8ccc9c(c8F)CN(C8CCC(=O)NC8=O)C9=O)CC6)C7)CC5)ncn4)c3c2)CC1] | 3-{4-fluoro-5-[4-({6-[(1-{6-[5-(1-methylcyclopropoxy)-1H-indazol-3-yl]pyrimidin-4-yl}piperidin-4-yl)methyl]-3,6-diazabicyclo[3.1.1]heptan-3-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 238 | 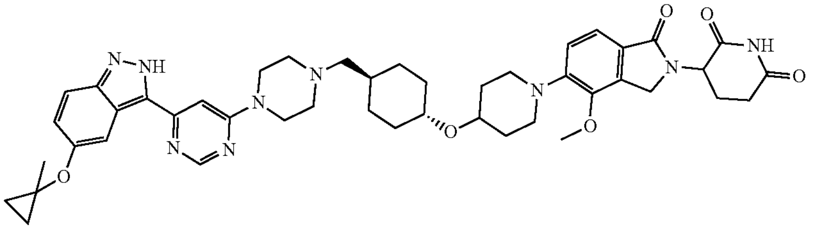 [SMILES: COc1c(N2CCC(O[C@H]3CC[C@H](CN4CCN(c5cc(-c6[nH]nc7ccc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(4-{6-[5-(1-methylcyclopropoxy)-2H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 239 | 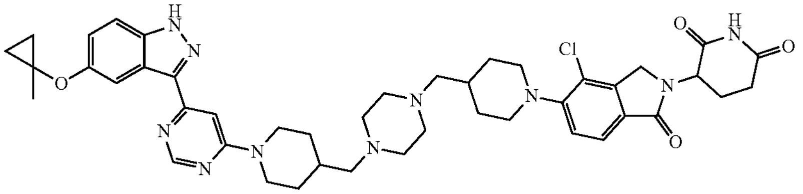 [SMILES: CC1(Oc2ccc3[nH]nc(-c4cc(N5CCC(CN6CCN(CC7CCN(c8ccc9c(c8Cl)CN(C8CCC(=O)NC8=O)C9=O)CC7)CC6)CC5)ncn4)c3c2)CC1] | 3-{4-chloro-5-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 240 | 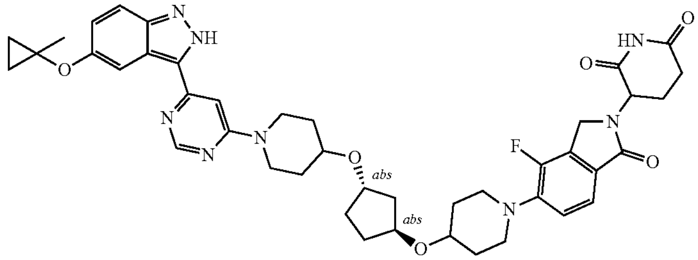 [SMILES: CC1(Oc2ccc3n[nH]c(-c4cc(N5CCC(O[C@H]6CC[C@H](OC7CCN(c8ccc9c(c8F)CN(C8CCC(=O)NC8=O)C9=O)CC7)C6)CC5)ncn4)c3c2)CC1] | 3-[4-fluoro-5-(4-{[(1S,3S)-3-[(1-{6-[5-(1-methylcyclopropoxy)-2H-indazol-3-yl]pyrimidin-4-yl}piperidin-4-yl)oxy]cyclopentyl]oxy}piperidin-1-yl)-1-oxo-2,3-dihydro-1H-isoindol-2-yl]piperidine-2,6-dione |
| 241 | 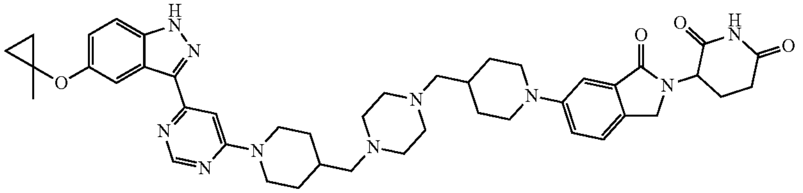 [SMILES: CC1(Oc2ccc3[nH]nc(-c4cc(N5CCC(CN6CCN(CC7CCN(c8ccc9c(c8)C(=O)N(C8CCC(=O)NC8=O)C9)CC7)CC6)CC5)ncn4)c3c2)CC1] | 3-{6-[4-({4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 242 | 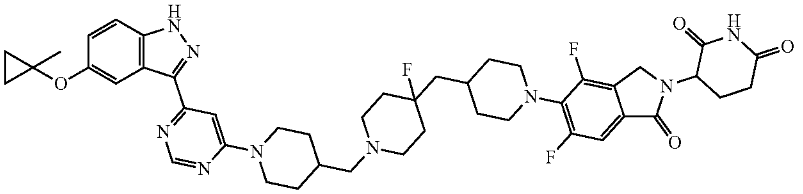 [SMILES: CC1(Oc2ccc3[nH]nc(-c4cc(N5CCC(CN6CCC(F)(CC7CCN(c8c(F)cc9c(c8F)CN(C8CCC(=O)NC8=O)C9=O)CC7)CC6)CC5)ncn4)c3c2)CC1] | 3-{4,6-difluoro-5-[4-({4-fluoro-1-[(1-{6-[5-(1-methylcyclopropoxy)-1H-indazol-3-yl]pyrimidin-4-yl}piperidin-4-yl)methyl]piperidin-4-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 243 | 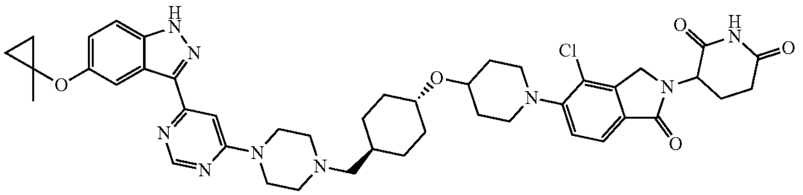 [SMILES: CC1(Oc2ccc3[nH]nc(-c4cc(N5CCN(C[C@H]6CC[C@H](OC7CCN(c8ccc9c(c8Cl)CN(C8CCC(=O)NC8=O)C9=O)CC7)CC6)CC5)ncn4)c3c2)CC1] | 3-[4-chloro-1-oxo-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 244 | 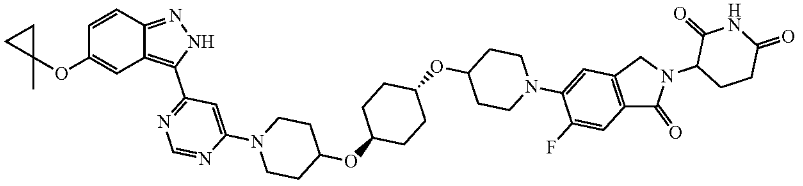 [SMILES: CC1(Oc2ccc3n[nH]c(-c4cc(N5CCC(O[C@H]6CC[C@H](OC7CCN(c8cc9c(cc8F)C(=O)N(C8CCC(=O)NC8=O)C9)CC7)CC6)CC5)ncn4)c3c2)CC1] | 3-[6-fluoro-1-oxo-5-(4-{[(1r,4r)-4-[(1-{6-[5-(1-methylcyclopropoxy)-2H-indazol-3-yl]pyrimidin-4-yl}piperidin-4-yl)oxy]cyclohexyl]oxy}piperidin-1-yl)-2,3-dihydro-1H-isoindol-2-yl]piperidine-2,6-dione |
| 245 | 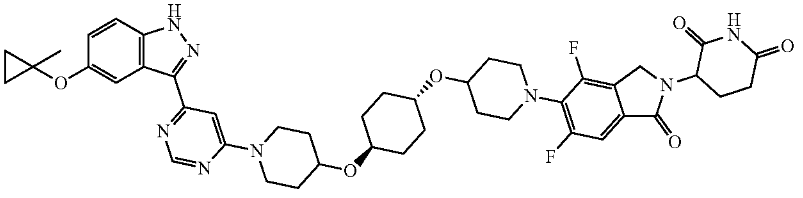 [SMILES: CC1(Oc2ccc3[nH]nc(-c4cc(N5CCC(O[C@H]6CC[C@H](OC7CCN(c8c(F)cc9c(c8F)CN(C8CCC(=O)NC8=O)C9=O)CC7)CC6)CC5)ncn4)c3c2)CC1] | 3-[4,6-difluoro-1-oxo-5-(4-{[(1r,4r)-4-[(1-{6-[5-(1-methylcyclopropoxy)-1H-indazol-3-yl]pyrimidin-4-yl}piperidin-4-yl)oxy]cyclohexyl]oxy}piperidin-1-yl)-2,3-dihydro-1H-isoindol-2-yl]piperidine-2,6-dione |
| 246 | 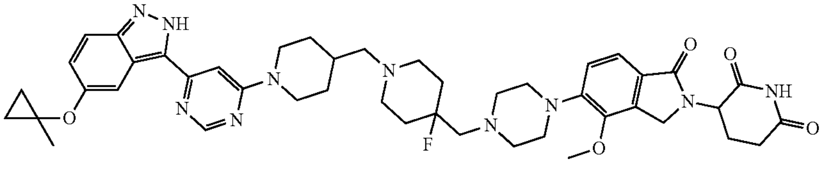 [SMILES: COc1c(N2CCN(CC3(F)CCN(CC4CCN(c5cc(-c6[nH]nc7ccc(OC8(C)CC8)cc67)ncn5)CC4)CC3)CC2)ccc2c1CN(C1CCC(=O)NC1=O)C2=O] | 3-{5-[4-({4-fluoro-1-[(1-{6-[5-(1-methylcyclopropoxy)-2H-indazol-3-yl]pyrimidin-4-yl}piperidin-4-yl)methyl]piperidin-4-yl}methyl)piperazin-1-yl]-4-methoxy-1-oxo-2,3-dihydro-1H-isoindol-2-yl}piperidine-2,6-dione |
| 247 | 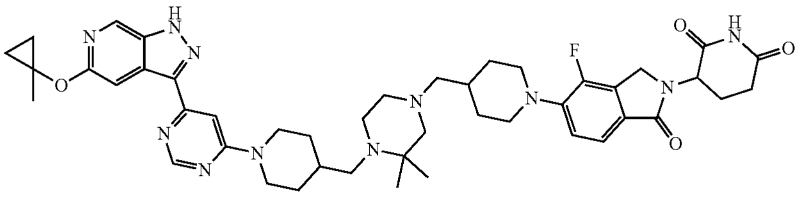 [SMILES: CC1(Oc2cc3c(-c4cc(N5CCC(CN6CCN(CC7CCN(c8ccc9c(c8F)CN(C8CCC(=O)NC8=O)C9=O)CC7)CC6(C)C)CC5)ncn4)n[nH]c3cn2)CC1] | 3-{5-[4-({3,3-dimethyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-4-fluoro-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 248 | 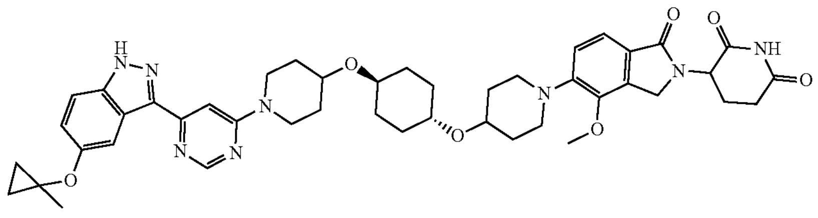 [SMILES: COc1c(N2CCC(O[C@H]3CC[C@H](OC4CCN(c5cc(-c6n[nH]c7ccc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(1-{6-[5-(1-methylcyclopropoxy)-1H-indazol-3-yl]pyrimidin-4-yl}piperidin-4-yl)oxy]cyclohexyl]oxy}piperidin-1-yl)-2,3-dihydro-1H-isoindol-2-yl]piperidine-2,6-dione |
| 249 | 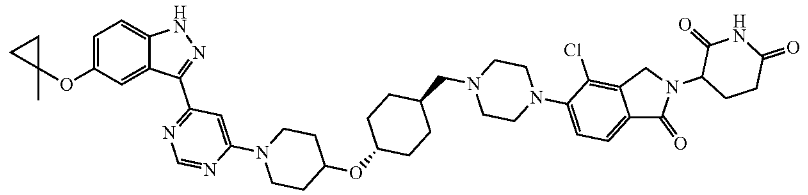 [SMILES: CC1(Oc2ccc3[nH]nc(-c4cc(N5CCC(O[C@H]6CC[C@H](CN7CCN(c8ccc9c(c8Cl)CN(C8CCC(=O)NC8=O)C9=O)CC7)CC6)CC5)ncn4)c3c2)CC1] | 3-[4-chloro-1-oxo-5-(4-{[(1r,4r)-4-[(1-{6-[5-(1-methylcyclopropoxy)-1H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 250 | 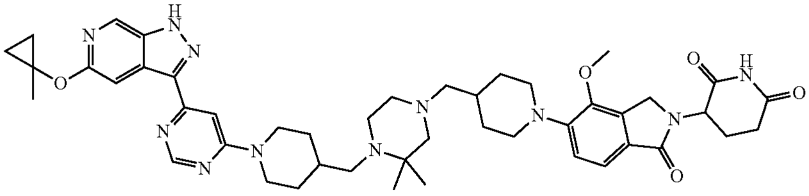 [SMILES: COc1c(N2CCC(CN3CCN(CC4CCN(c5cc(-c6n[nH]c7cnc(OC8(C)CC8)cc67)ncn5)CC4)C(C)(C)C3)CC2)ccc2c1CN(C1CCC(=O)NC1=O)C2=O] | 3-{5-[4-({3,3-dimethyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-4-methoxy-1-oxo-2,3-dihydro-1H-isoindol-2-yl}piperidine-2,6-dione |
| 251 | 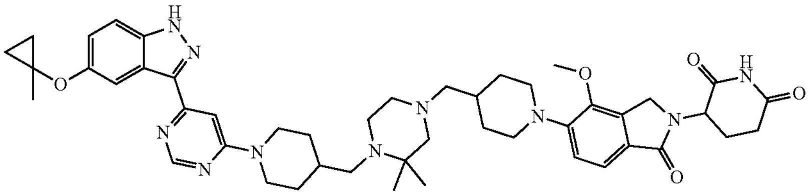 [SMILES: COc1c(N2CCC(CN3CCN(CC4CCN(c5cc(-c6n[nH]c7ccc(OC8(C)CC8)cc67)ncn5)CC4)C(C)(C)C3)CC2)ccc2c1CN(C1CCC(=O)NC1=O)C2=O] | 3-{5-[4-({3,3-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-4-methoxy-1-oxo-2,3-dihydro-1H-isoindol-2-yl}piperidine-2,6-dione |
| 252 | 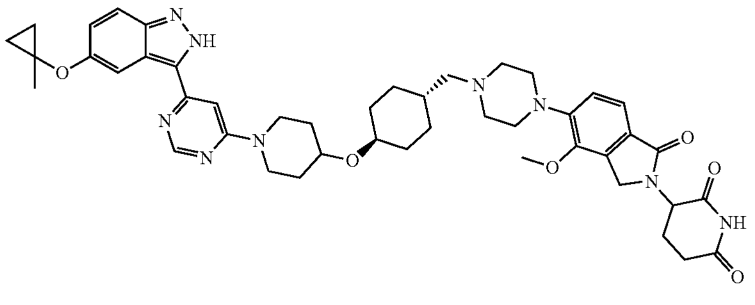 [SMILES: COc1c(N2CCN(C[C@H]3CC[C@H](OC4CCN(c5cc(-c6[nH]nc7ccc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(1-{6-[5-(1-methylcyclopropoxy)-2H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 253 | 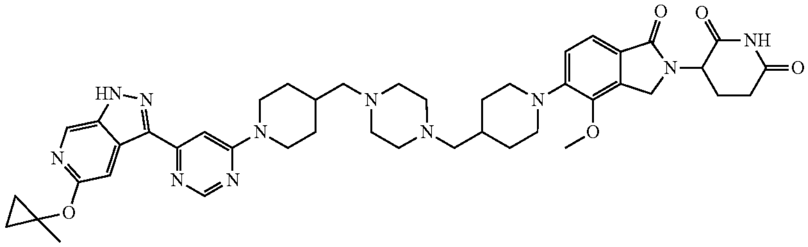 [SMILES: COc1c(N2CCC(CN3CCN(CC4CCN(c5cc(-c6n[nH]c7cnc(OC8(C)CC8)cc67)ncn5)CC4)CC3)CC2)ccc2c1CN(C1CCC(=O)NC1=O)C2=O] | 3-{4-methoxy-5-[4-({4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-1-oxo-2,3-dihydro-1H-isoindol-2-yl}piperidine-2,6-dione |
| 254 | 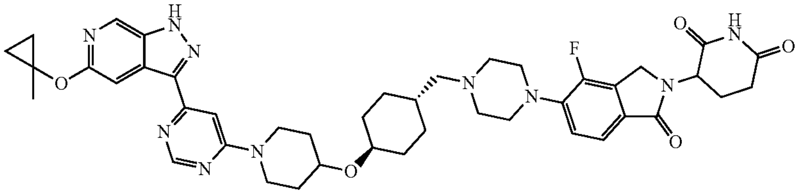 | 3-[4-fluoro-1-oxo-5-(4-{[(1r,4r)-4-[(1-{6-[5-(1-methylcyclopropoxy)-1H-pyrazolo[3,4-c]pyridin-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 255 | 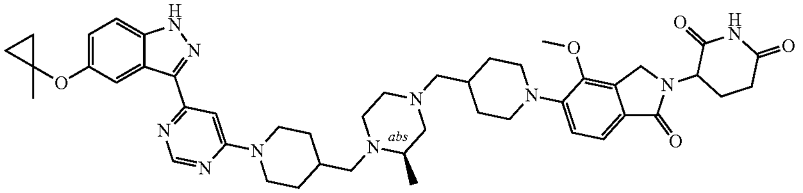 [SMILES: COc1c(N2CCC(CN3CCN(CC4CCN(c5cc(-c6n[nH]c7ccc(OC8(C)CC8)cc67)ncn5)CC4)[C@H](C)C3)CC2)ccc2c1CN(C1CCC(=O)NC1=O)C2=O] | 3-[4-methoxy-5-(4-{[(3R)-3-methyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 256 | 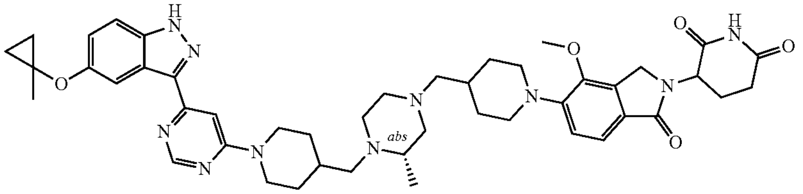 [SMILES: COc1c(N2CCC(CN3CCN(CC4CCN(c5cc(-c6n[nH]c7ccc(OC8(C)CC8)cc67)ncn5)CC4)[C@@H](C)C3)CC2)ccc2c1CN(C1CCC(=O)NC1=O)C2=O] | 3-[4-methoxy-5-(4-{[(3S)-3-methyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 257 | 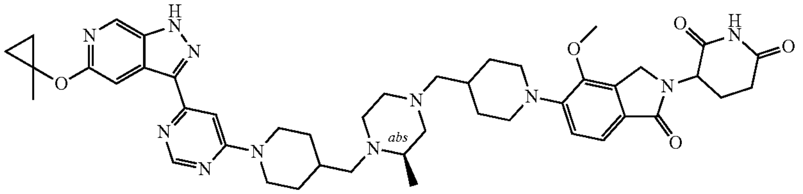 [SMILES: COc1c(N2CCC(CN3CCN(CC4CCN(c5cc(-c6n[nH]c7cnc(OC8(C)CC8)cc67)ncn5)CC4)[C@H](C)C3)CC2)ccc2c1CN(C1CCC(=O)NC1=O)C2=O] | 3-[4-methoxy-5-(4-{[(3R)-3-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 258 | 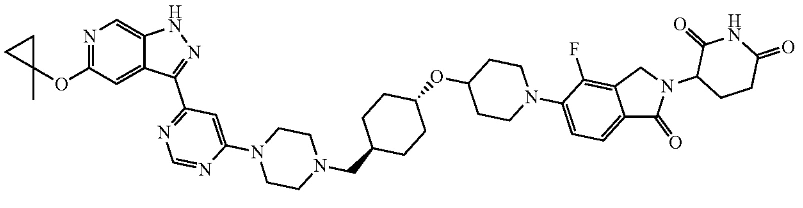 | 3-[4-fluoro-1-oxo-5-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 259 | 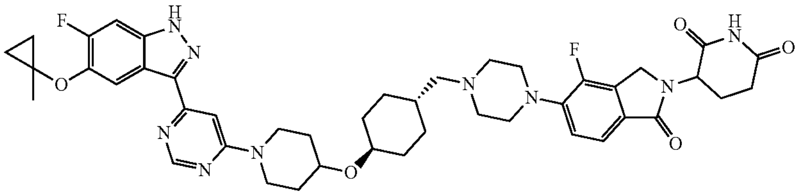 [SMILES: CC1(Oc2cc3c(-c4cc(N5CCC(O[C@H]6CC[C@H](CN7CCN(c8ccc9c(c8F)CN(C8CCC(=O)NC8=O)C9=O)CC7)CC6)CC5)ncn4)n[nH]c3cc2F)CC1] | 3-[4-fluoro-1-oxo-5-(4-{[(1r,4r)-4-[(1-{6-[6-fluoro-5-(1-methylcyclopropoxy)-1H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 260 | 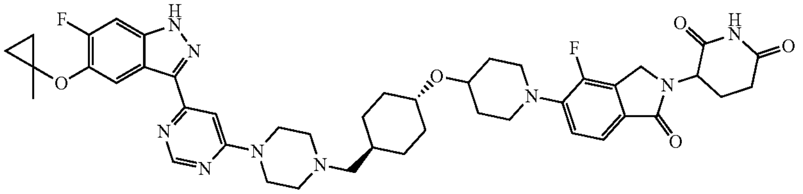 | 3-[4-fluoro-1-oxo-5-(4-{[(1r,4r)-4-[(4-{6-[6-fluoro-5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 261 | 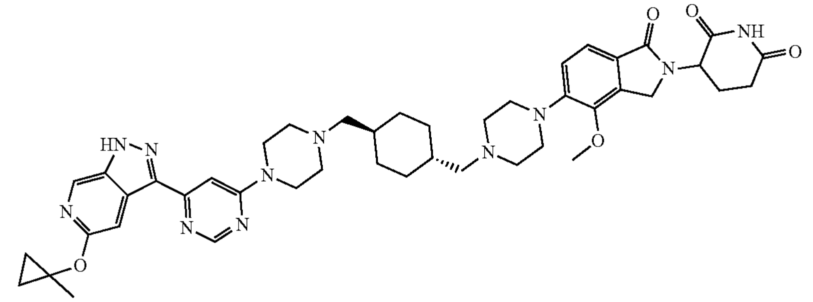 [SMILES: COc1c(N2CCN(C[C@H]3CC[C@H](CN4CCN(c5cc(-c6n[nH]c7cnc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]methyl}piperazin-1-yl)-2,3-dihydro-1H-isoindol-2-yl]piperidine-2,6-dione |
| 262 | 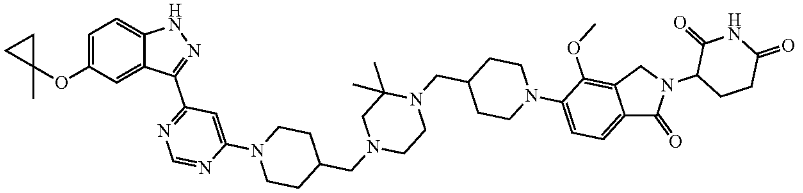 [SMILES: COc1c(N2CCC(CN3CCN(CC4CCN(c5cc(-c6n[nH]c7ccc(OC8(C)CC8)cc67)ncn5)CC4)CC3(C)C)CC2)ccc2c1CN(C1CCC(=O)NC1=O)C2=O] | 3-{5-[4-({2,2-dimethyl-4-[(1-{6-[5-(1-methylcyclopropoxy)-1H-indazol-3-yl]pyrimidin-4-yl}piperidin-4-yl)methyl]piperazin-1-yl}methyl)piperidin-1-yl]-4-methoxy-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 263 | 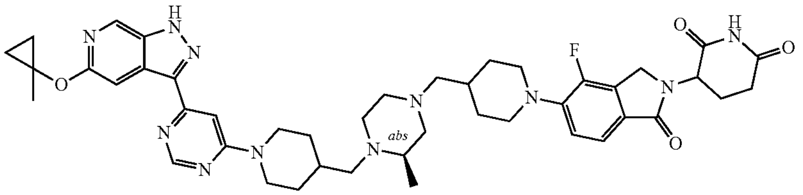 [SMILES: C[C@@H]1CN(CC2CCN(c3ccc4c(c3F)CN(C3CCC(=O)NC3=O)C4=O)CC2)CCN1CC1CCN(c2cc(-c3n[nH]c4cnc(OC5(C)CC5)cc34)ncn2)CC1] | 3-[4-fluoro-5-(4-{[(3R)-3-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 264 | 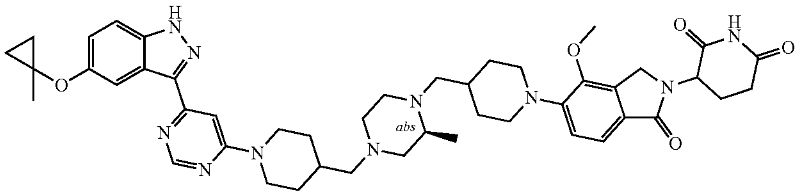 [SMILES: COc1c(N2CCC(CN3CCN(CC4CCN(c5cc(-c6n[nH]c7ccc(OC8(C)CC8)cc67)ncn5)CC4)C[C@@H]3C)CC2)ccc2c1CN(C1CCC(=O)NC1=O)C2=O] | 3-[4-methoxy-5-(4-{[(2S)-2-methyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 265 | 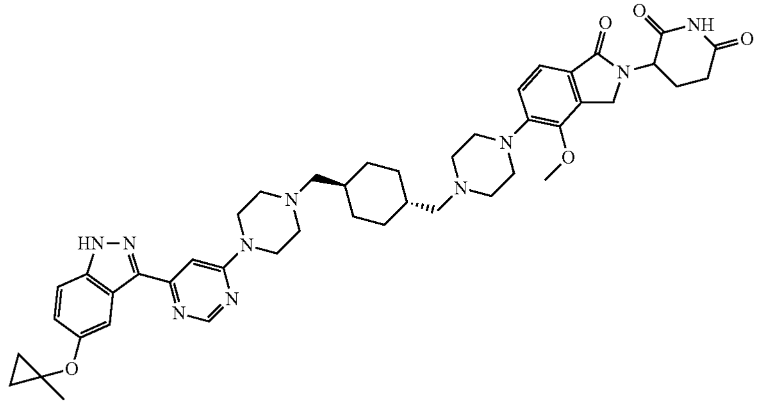 [SMILES: COc1c(N2CCN(C[C@H]3CC[C@H](CN4CCN(c5cc(-c6n[nH]c7ccc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(4-{6-[5-(1-methylcyclopropoxy)-1H-indazol-3-yl]pyrimidin-4-yl}piperazin-1-yl)methyl]cyclohexyl]methyl}piperazin-1-yl)-2,3-dihydro-1H-isoindol-2-yl]piperidine-2,6-dione |
| 266 | 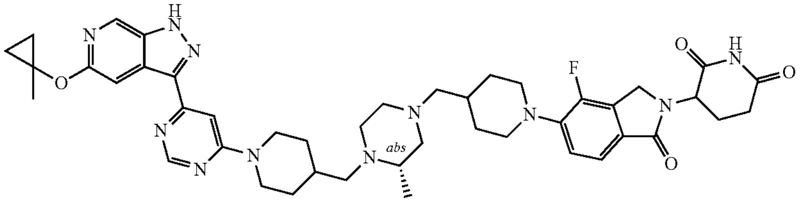 [SMILES: C[C@H]1CN(CC2CCN(c3ccc4c(c3F)CN(C3CCC(=O)NC3=O)C4=O)CC2)CCN1CC1CCN(c2cc(-c3n[nH]c4cnc(OC5(C)CC5)cc34)ncn2)CC1] | 3-[4-fluoro-5-(4-{[(3S)-3-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |

TABLE 1-continued

| Ex. No. | Chemical Structure | IUPAC Name |
|---|---|---|
| Exemplary bifunctional compounds of the present disclosure** | | |
| 267 | 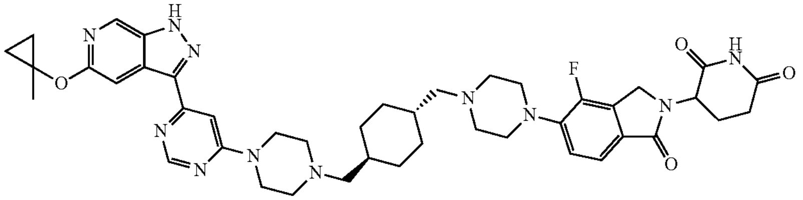 [SMILES: CC1(Oc2cc3c(-c4cc(N5CCN(C[C@H]6CC[C@H](CN7CCN(c8ccc9c(c8F)CN(C8CCC(=O)NC8=O)C9=O)CC7)CC6)CC5)ncn4)n[nH]c3cn2)CC1] | 3-[4-fluoro-1-oxo-5-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]methyl}piperazin-1-yl)-2,3-dihydro-1H-isoindol-2-yl]piperidine-2,6-dione |
| 268 | 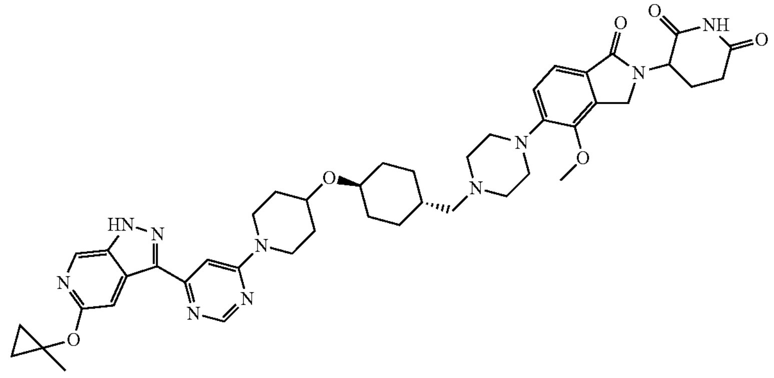 [SMILES: COc1c(N2CCN(C[C@H]3CC[C@H](OC4CCN(c5cc(-c6n[nH]c7cnc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(1-{6-[5-(1-methylcyclopropoxy)-1H-pyrazolo[3,4-c]pyridin-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 269 | 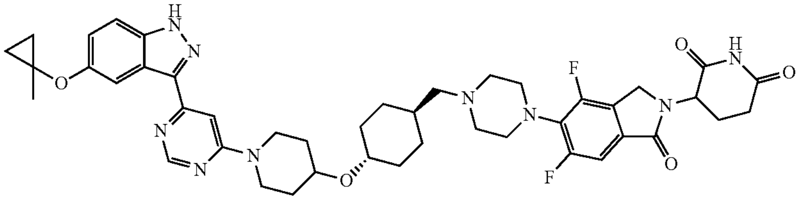 [SMILES: CC1(Oc2ccc3[nH]nc(-c4cc(N5CCC(O[C@H]6CC[C@H](CN7CCN(c8c(F)cc9c(c8F)CN(C8CCC(=O)NC8=O)C9=O)CC7)CC6)CC5)ncn4)c3c2)CC1] | 3-[4,6-difluoro-1-oxo-5-(4-{[(1r,4r)-4-[(1-{6-[5-(1-methylcyclopropoxy)-1H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 270 | 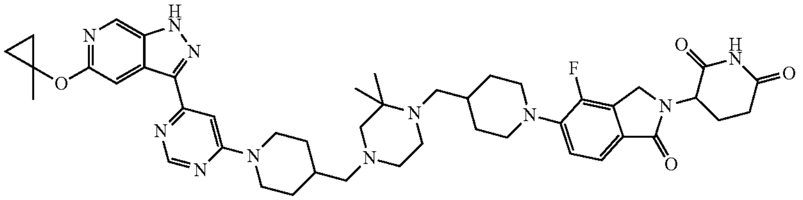 [SMILES: CC1(Oc2cc3c(-c4cc(N5CCC(CN6CCN(CC7CCN(c8ccc9c(c8F)CN(C8CCC(=O)NC8=O)C9=O)CC7)C(C)(C)C6)CC5)ncn4)n[nH]c3cn2)CC1] | 3-{5-[4-({2,2-dimethyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-4-fluoro-1-oxo-2,3-dihydro-1H-isoindol-2-yl}piperidine-2,6-dione |

TABLE 1-continued

| Ex. No. | Chemical Structure | IUPAC Name |
|---|---|---|
| | Exemplary bifunctional compounds of the present disclosure** | |
| 271 | 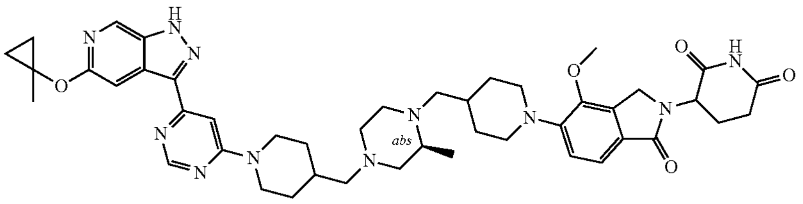 [SMILES: COc1c(N2CCC(CN3CCN(CC4CCN(c5cc(-c6n[nH]c7cnc(OC8(C)CC8)cc67)ncn5)CC4)C[C@@H]3C)CC2)ccc2c1CN(C1CCC(=O)NC1=O)C2=O] | 3-[4-methoxy-5-(4-{[(2S)-2-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 272 | 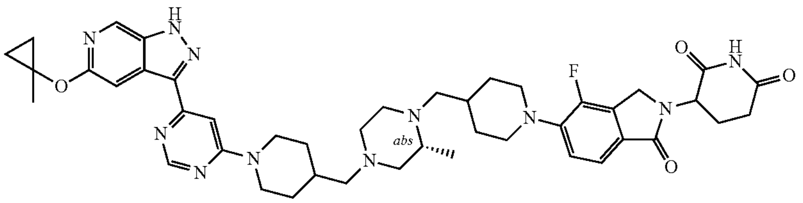 [SMILES: C[C@@H]1CN(CC2CCN(c3cc(-c4n[nH]c5cnc(OC6(C)CC6)cc45)ncn3)CC2)CCN1CC1CCN(c2ccc3c(c2F)CN(C2CCC(=O)NC2=O)C3=O)CC1] | 3-[4-fluoro-5-(4-{[(2R)-2-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 273 | 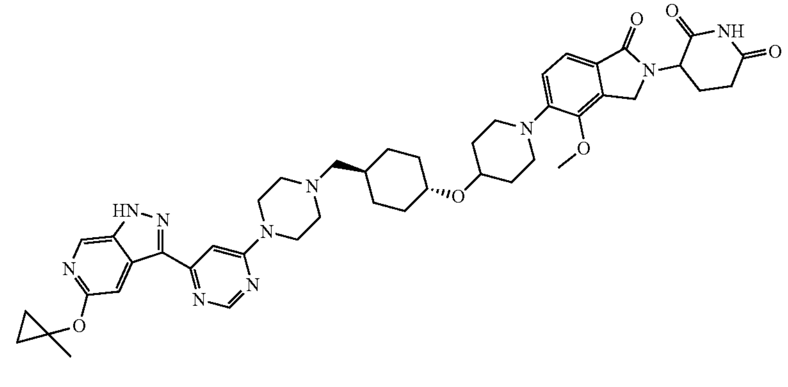 [SMILES: COc1c(N2CCC(O[C@H]3CC[C@H](CN4CCN(c5cc(-c6n[nH]c7cnc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(4-{6-[5-(1-methylcyclopropoxy)-1H-pyrazolo[3,4-c]pyridin-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 274 | 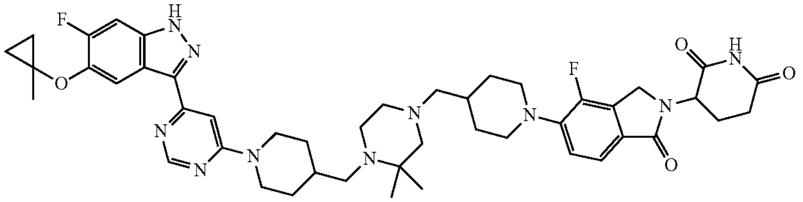 [SMILES: CC1(Oc2cc3c(-c4cc(N5CCC(CN6CCN(CC7CCN(c8ccc9c(c8F)CN(C8CCC(=O)NC8=O)C9=O)CC7)CC6(C)C)CC5)ncn4)n[nH]c3cc2F)CC1] | 3-{4-fluoro-5-[4-({4-[(1-{6-[6-fluoro-5-(1-methylcyclopropoxy)-1H-indazol-3-yl]pyrimidin-4-yl}piperidin-4-yl)methyl]-3,3-dimethylpiperazin-1-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 275 | 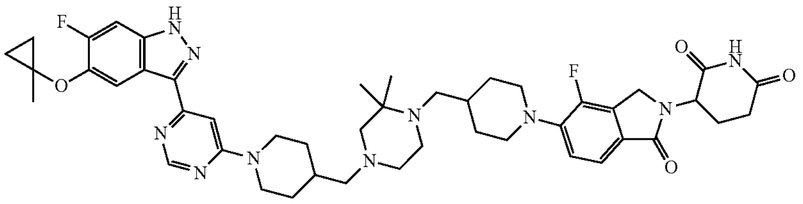 [SMILES: CC1(Oc2cc3c(-c4cc(N5CCC(CN6CCN(CC7CCN(c8ccc9c(c8F)CN(C8CCC(=O)NC8=O)C9=O)CC7)C(C)(C)C6)CC5)ncn4)n[nH]c3cc2F)CC1] | 3-{4-fluoro-5-[4-({4-[(1-{6-[6-fluoro-5-(1-methylcyclopropoxy)-1H-indazol-3-yl]pyrimidin-4-yl}piperidin-4-yl)methyl]-2,2-dimethylpiperazin-1-yl}methyl)piperidin-1-yl]-1-oxo-2,3-dihydro-1H-isoindol-2-yl}piperidine-2,6-dione |
| 276 | 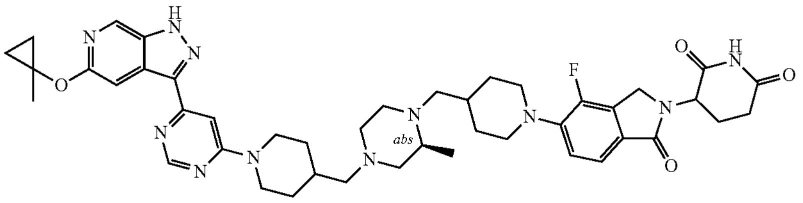 [SMILES: C[C@H]1CN(CC2CCN(c3cc(-c4n[nH]c5cnc(OC6(C)CC6)cc45)ncn3)CC2)CCN1CC1CCN(c2ccc3c(c2F)CN(C2CCC(=O)NC2=O)C3=O)CC1] | 3-[4-fluoro-5-(4-{[(2S)-2-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 277 | 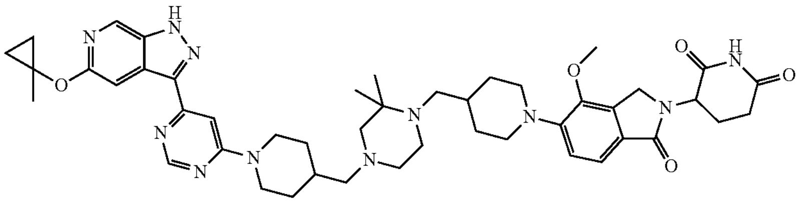 [SMILES: COc1c(N2CCC(CN3CCN(CC4CCN(c5cc(-c6n[nH]c7cnc(OC8(C)CC8)cc67)ncn5)CC4)CC3(C)C)CC2)ccc2c1CN(C1CCC(=O)NC1=O)C2=O] | 3-{5-[4-({2,2-dimethyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-4-methoxy-1-oxo-2,3-dihydro-1H-isoindol-2-yl}piperidine-2,6-dione |
| 278 | 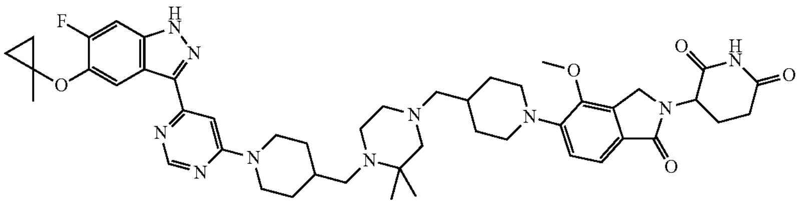 [SMILES: COc1c(N2CCC(CN3CCN(CC4CCN(c5cc(-c6n[nH]c7cc(F)c(OC8(C)CC8)cc67)ncn5)CC4)C(C)(C)C3)CC2)ccc2c1CN(C1CCC(=O)NC1=O)C2=O] | 3-{5-[4-({4-[(1-{6-[6-fluoro-5-(1-methylcyclopropoxy)-1H-indazol-3-yl]pyrimidin-4-yl}piperidin-4-yl)methyl]-3,3-dimethylpiperazin-1-yl}methyl)piperidin-1-yl]-4-methoxy-1-oxo-2,3-dihydro-1H-isoindol-2-yl}piperidine-2,6-dione |
| 279 | 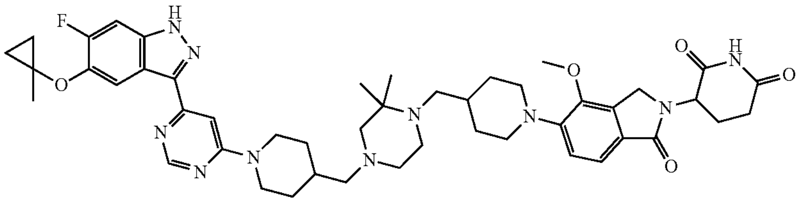 [SMILES: COc1c(N2CCC(CN3CCN(CC4CCN(c5cc(-c6n[nH]c7cc(F)c(OC8(C)CC8)cc67)ncn5)CC4)CC3(C)C)CC2)ccc2c1CN(C1CCC(=O)NC1=O)C2=O] | 3-{5-[4-({4-[(1-{6-[6-fluoro-5-(1-methylcyclopropoxy)-1H-indazol-3-yl]pyrimidin-4-yl}piperidin-4-yl)methyl]-2,2-dimethylpiperazin-1-yl}methyl)piperidin-1-yl]-4-methoxy-1-oxo-2,3-dihydro-1H-isoindol-2-yl}piperidine-2,6-dione |

TABLE 1-continued

| Ex. No. | Chemical Structure | IUPAC Name |
|---|---|---|
| 280 | 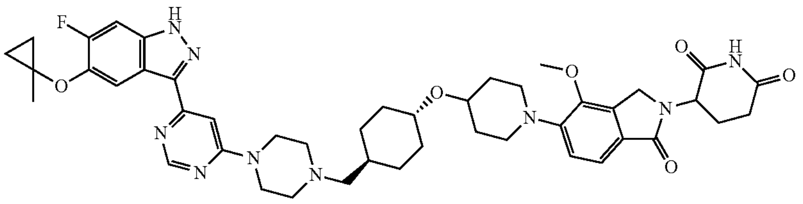 [SMILES: COc1c(N2CCC(O[C@H]3CC[C@H](CN4CCN(c5cc(-c6n[nH]c7cc(F)c(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(4-{6-[6-fluoro-5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 281 | 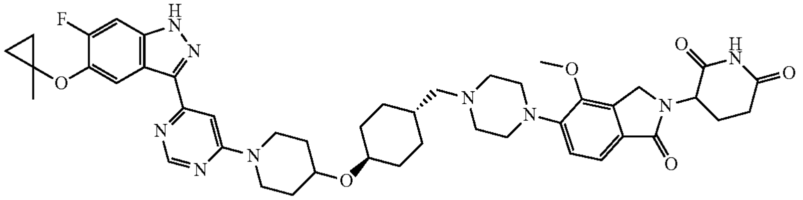 [SMILES: COc1c(N2CCN(C[C@H]3CC[C@H](OC4CCN(c5cc(-c6n[nH]c7cc(F)c(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(1-{6-[6-fluoro-5-(1-methylcyclopropoxy)-1H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 282 | 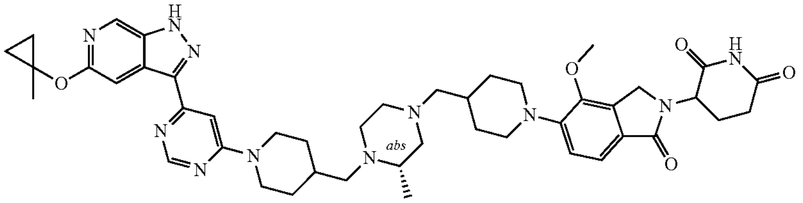 [SMILES: COc1c(N2CCC(CN3CCN(CC4CCN(c5cc(-c6n[nH]c7cnc(OC8(C)CC8)cc67)ncn5)CC4)[C@@H](C)C3)CC2)ccc2c1CN(C1CCC(=O)NC1=O)C2=O] | 3-[4-methoxy-5-(4-{[(3S)-3-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 283 | 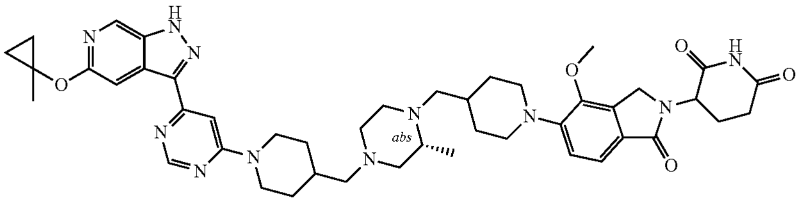 [SMILES: COc1c(N2CCC(CN3CCN(CC4CCN(c5cc(-c6n[nH]c7cnc(OC8(C)CC8)cc67)ncn5)CC4)C[C@H]3C)CC2)ccc2c1CN(C1CCC(=O)NC1=O)C2=O] | 3-[4-methoxy-5-(4-{[(2R)-2-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 284 | 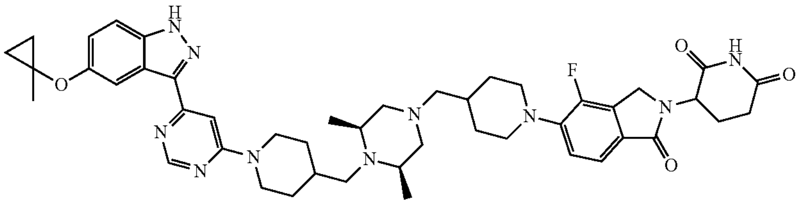 [SMILES: C[C@@H]1CN(CC2CCN(c3ccc4c(c3F)CN(C3CCC(=O)NC3=O)C4=O)CC2)C[C@H](C)N1CC1CCN(c2cc(-c3n[nH]c4ccc(OC5(C)CC5)cc34)ncn2)CC1] | 3-[5-(4-{[(3R,5S)-3,5-dimethyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-4-fluoro-1-oxo-2,3-dihydro-1H-isoindol-2-yl]piperidine-2,6-dione |

TABLE 1-continued

| Ex. No. | Chemical Structure | IUPAC Name |
|---|---|---|
| Exemplary bifunctional compounds of the present disclosure** | | |
| 285 | 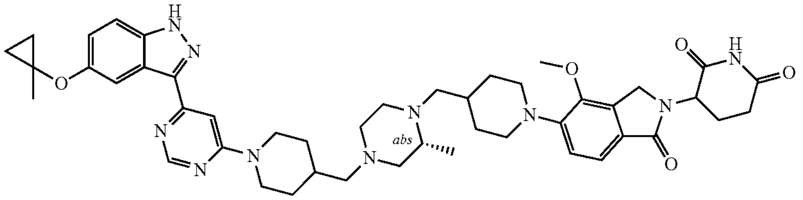 [SMILES: COc1c(N2CCC(CN3CCN(CC4CCN(c5cc(-c6n[nH]c7ccc(OC8(C)CC8)cc67)ncn5)CC4)C[C@H]3C)CC2)ccc2c1CN(C1CCC(=O)NC1=O)C2=O] | 3-[4-methoxy-5-(4-{[(2R)-2-methyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 286 | 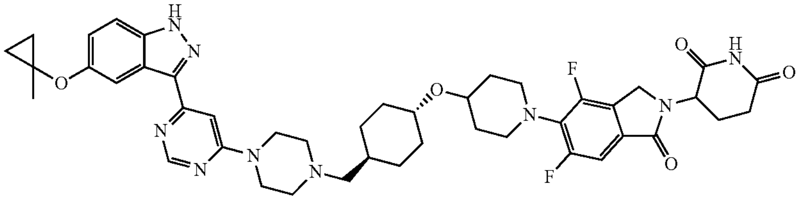 [SMILES: CC1(Oc2ccc3[nH]nc(-c4cc(N5CCN(C[C@H]6CC[C@H](OC7CCN(c8c(F)cc9c(c8F)CN(C8CCC(=O)NC8=O)C9=O)CC7)CC6)CC5)ncn4)c3c2)CC1] | 3-[4,6-difluoro-1-oxo-5-(4-{[(1r,4r)-4-[(4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 287 | 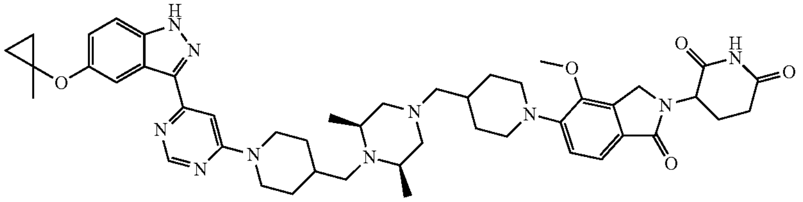 [SMILES: COc1c(N2CCC(CN3C[C@@H](C)N(CC4CCN(c5cc(-c6n[nH]c7ccc(OC8(C)CC8)cc67)ncn5)CC4)[C@@H](C)C3)CC2)ccc2c1CN(C1CCC(=O)NC1=O)C2=O] | 3-[5-(4-{[(3R,5S)-3,5-dimethyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-4-methoxy-1-oxo-2,3-dihydro-1H-isoindol-2-yl]piperidine-2,6-dione |
| 288 | 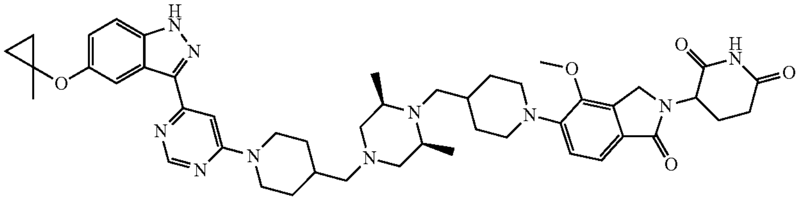 [SMILES: COc1c(N2CCC(CN3[C@H](C)CN(CC4CCN(c5cc(-c6n[nH]c7ccc(OC8(C)CC8)cc67)ncn5)CC4)C[C@@H]3C)CC2)ccc2c1CN(C1CCC(=O)NC1=O)C2=O] | 3-[5-(4-{[(2R,6S)-2,6-dimethyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-4-methoxy-1-oxo-2,3-dihydro-1H-isoindol-2-yl]piperidine-2,6-dione |
| 289 | 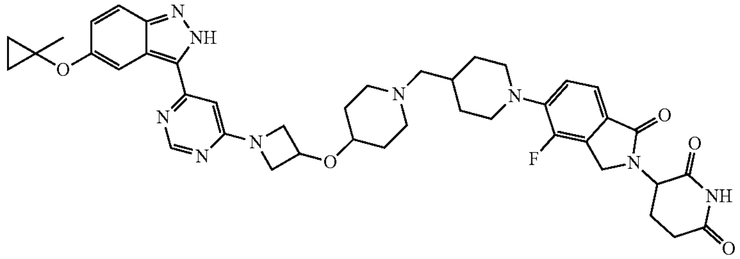 [SMILES: CC1(Oc2ccc3n[nH]c(-c4cc(N5CC(OC6CCN(CC7CCN(c8ccc9c(c8F)CN(C8CCC(=O)NC8=O)C9=O)CC7)CC6)C5)ncn4)c3c2)CC1] | 3-{4-fluoro-5-[4-({4-[(1-{6-[5-(1-methylcyclopropoxy)-2H-indazol-3-yl]pyrimidin-4-yl}azetidin-3-yl)oxy]piperidin-1-yl}methyl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 290 | 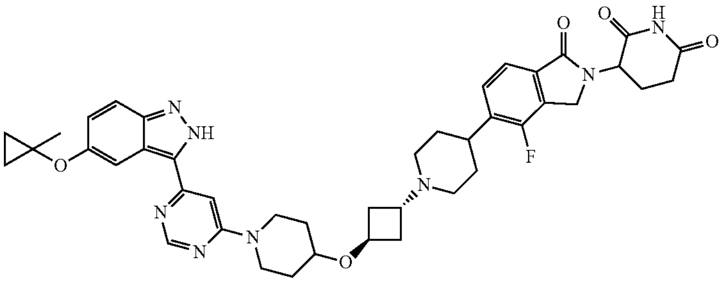 [SMILES: CC1(Oc2ccc3n[nH]c(-c4cc(N5CCC(O[C@H]6C[C@H](N7CCC(c8ccc9c(c8F)CN(C8CCC(=O)NC8=O)C9=O)CC7)C6)CC5)ncn4)c3c2)CC1] | 3-(4-fluoro-1-oxo-5-{1-[(1r,3r)-3-[(1-{6-[5-(1-methylcyclopropoxy)-2H-indazol-3-yl]pyrimidin-4-yl}piperidin-4-yl)oxy]cyclobutyl] piperidin-4-yl}-2,3-dihydro-1H-isoindol-2-yl)piperidine-2,6-dione |
| 291 | 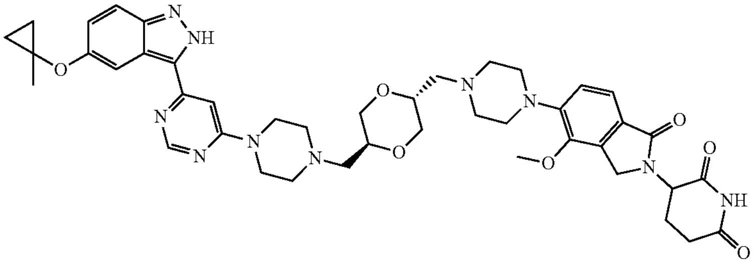 [SMILES: COc1c(N2CCN(C[C@@H]3CO[C@@H](CN4CCN(c5cc(-c6[nH]nc7ccc(OC8(C)CC8)cc67)ncn5)CC4)CO3)CC2)ccc2c1CN(C1CCC(=O)NC1=O)C2=O] | 3-[4-methoxy-5-(4-{[(2r,5s)-5-[(4-{6-[5-(1-methylcyclopropoxy)-2H-indazol-3-yl]pyrimidin-4-yl}piperazin-1-yl)methyl]-1,4-dioxan-2-yl]methyl}piperazin-1-yl)-1-oxo-2,3-dihydro-1H-isoindol-2-yl]piperidine-2,6-dione |
| 292 | 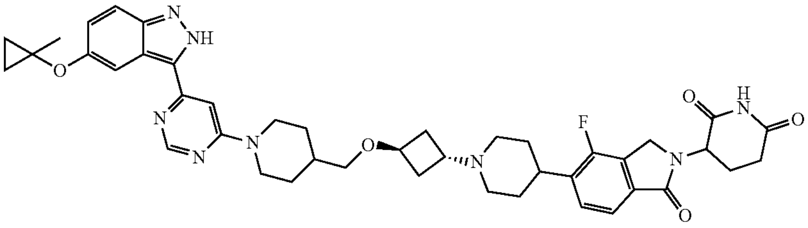 [SMILES: CC1(Oc2ccc3n[nH]c(-c4cc(N5CCC(CO[C@H]6C[C@H](N7CCC(c8ccc9c(c8F)CN(C8CCC(=O)NC8=O)C9=O)CC7)C6)CC5)ncn4)c3c2)CC1] | 3-(4-fluoro-1-oxo-5-{1-[(1r,3r)-3-[(1-{6-[5-(1-methylcyclopropoxy)-2H-indazol-3-yl]pyrimidin-4-yl}piperidin-4-yl)methoxy]cyclobutyl] piperidin-4-yl}-2,3-dihydro-1H-isoindol-2-yl)piperidine-2,6-dione |
| 293 | 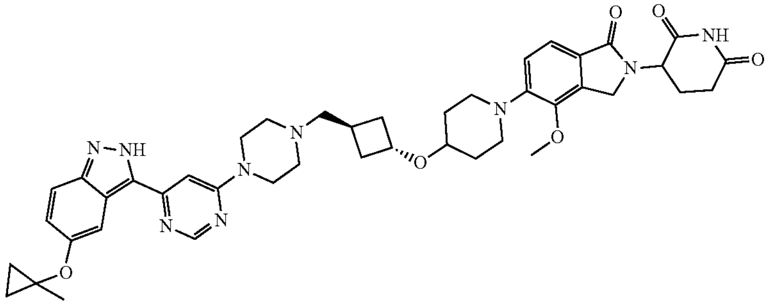 [SMILES: COc1c(N2CCC(O[C@H]3C[C@H](CN4CCN(c5cc(-c6[nH]nc7ccc(OC8(C)CC8)cc67)ncn5)CC4)C3)CC2)ccc2c1CN(C1CCC(=O)NC1=O)C2=O] | 3-(4-methoxy-1-oxo-5-{4-[(1r,3r)-3-[(4-{6-[5-(1-methylcyclopropoxy)-2H-indazol-3-yl]pyrimidin-4-yl}piperazin-1-yl)methyl]cyclobutoxy] piperidin-1-yl}-2,3-dihydro-1H-isoindol-2-yl)piperidine-2,6-dione |
| 294 | 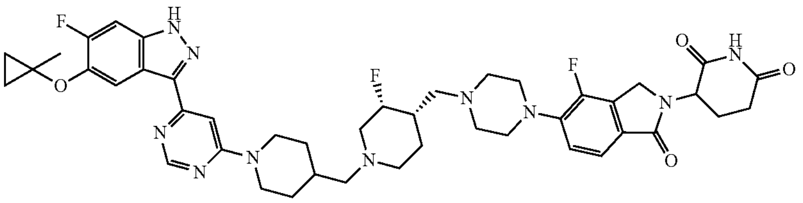 [SMILES: CC1(Oc2cc3c(-c4cc(N5CCC(CN6CC[C@@H](CN7CCN(c8ccc9c(c8F)CN(C8CCC(=O)NC8=O)C9=O)CC7)[C@@H](F)C6)CC5)ncn4)n[nH]c3cc2F)CC1] | 3-[4-fluoro-5-(4-{[(3r,4s)-3-fluoro-1-[(1-{6-[6-fluoro-5-(1-methylcyclopropoxy)-1H-indazol-3-yl]pyrimidin-4-yl}piperidin-4-yl)methyl]piperidin-4-yl]methyl}piperazin-1-yl)-1-oxo-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 295 | 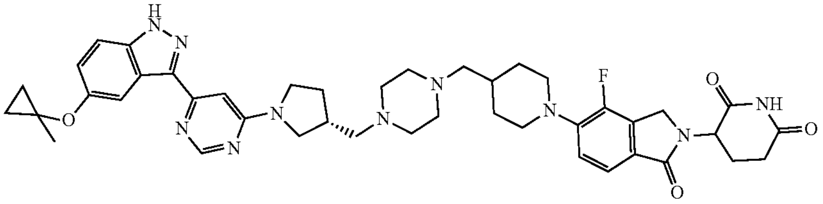 [SMILES: CC1(Oc2ccc3[nH]nc(-c4cc(N5CC[C@H](CN6CCN(CC7CCN(c8ccc9c(c8F)CN(C8CCC(=O)NC8=O)C9=O)CC7)CC6)C5)ncn4)c3c2)CC1] | 3-(4-fluoro-5-{4-[(4-{[(3R)-1-{6-[5-(1-methylcyclopropoxy)-1H-indazol-3-yl]pyrimidin-4-yl}pyrrolidin-3-yl]methyl}piperazin-1-yl)methyl]piperidin-1-yl}-1-oxo-2,3-dihydro-1H-isoindol-2-yl)piperidine-2,6-dione |
| 296 | 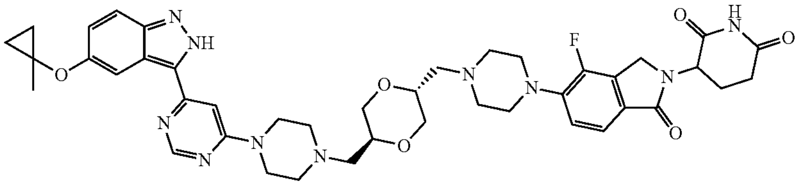 [SMILES: CC1(Oc2ccc3n[nH]c(-c4cc(N5CCN(C[C@H]6CO[C@H](CN7CCN(c8ccc9c(c8F)CN(C8CCC(=O)NC8=O)C9=O)CC7)CO6)CC5)ncn4)c3c2)CC1] | 3-[4-fluoro-5-(4-{[(2r,5s)-5-[(4-{6-[5-(1-methylcyclopropoxy)-2H-indazol-3-yl]pyrimidin-4-yl}piperazin-1-yl)methyl]-1,4-dioxan-2-yl]methyl}piperazin-1-yl)-1-oxo-2,3-dihydro-1H-isoindol-2-yl]piperidine-2,6-dione |
| 297 | 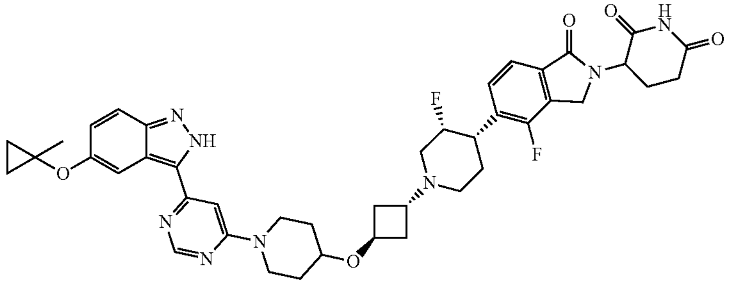 | 3-{4-fluoro-5-[(3r,4s)-3-fluoro-1-[(1r,3r)-3-[(1-{6-[5-(1-methylcyclopropoxy)-2H-indazol-3-yl]pyrimidin-4-yl}piperidin-4-yl)oxy]cyclobutyl]piperidin-4-yl]-1-oxo-2,3-dihydro-1H-isoindol-2-yl}piperidine-2,6-dione |
| 298 | 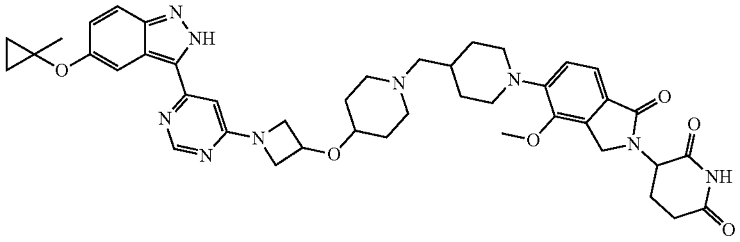 [SMILES: COc1c(N2CCC(CN3CCC(OC4CN(c5cc(-c6[nH]nc7ccc(OC8(C)CC8)cc67)ncn5)C4)CC3)CC2)ccc2c1CN(C1CCC(=O)NC1=O)C2=O] | 3-{4-methoxy-5-[4-({4-[(1-{6-[5-(1-methylcyclopropoxy)-2H-indazol-3-yl]pyrimidin-4-yl}azetidin-3-yl)oxy]piperidin-1-yl}methyl)piperidin-1-yl]-1-oxo-2,3-dihydro-1H-isoindol-2-yl}piperidine-2,6-dione |
| 299 | 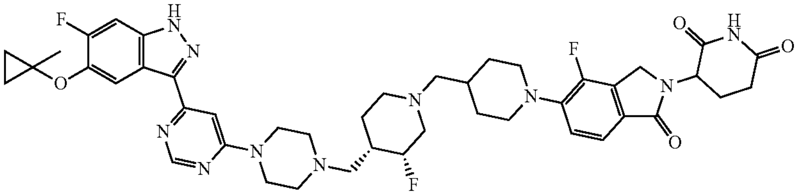 [SMILES: CC1(Oc2cc3c(-c4cc(N5CCN(C[C@@H]6CCN(CC7CCN(c8ccc9c(c8F)CN(C8CCC(=O)NC8=O)C9=O)CC7)C[C@@H]6F)CC5)ncn4)n[nH]c3cc2F)CC1] | 3-[4-fluoro-5-(4-{[(3r,4s)-3-fluoro-4-[(4-{6-[6-fluoro-5-(1-methylcyclopropoxy)-1H-indazol-3-yl]pyrimidin-4-yl}piperazin-1-yl)methyl]piperidin-1-yl]methyl}piperidin-1-yl)-1-oxo-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 300 | 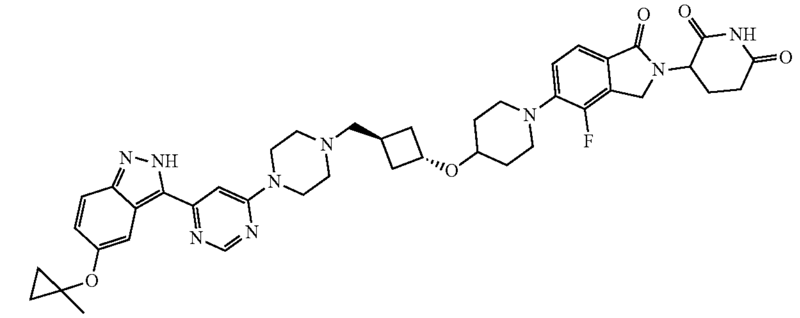 [SMILES: CC1(Oc2ccc3n[nH]c(-c4cc(N5CCN(C[C@H]6C[C@H](OC7CCN(c8ccc9c(c8F)CN(C8CCC(=O)NC8=O)C9=O)CC7)C6)CC5)ncn4)c3c2)CC1] | 3-(4-fluoro-1-oxo-5-{4-[(1r,3r)-3-[(4-{6-[5-(1-methylcyclopropoxy)-2H-indazol-3-yl]pyrimidin-4-yl}piperazin-1-yl)methyl]cyclobutoxy]piperidin-1-yl}-2,3-dihydro-1H-isoindol-2-yl)piperidine-2,6-dione |
| 301 | 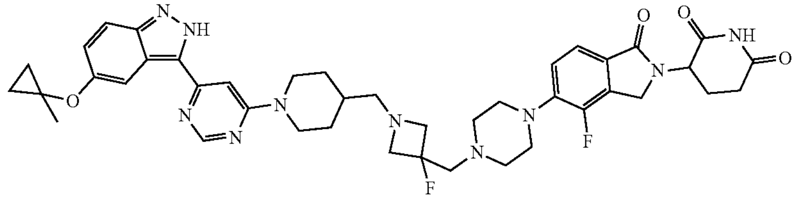 [SMILES: CC1(Oc2ccc3n[nH]c(-c4cc(N5CCC(CN6CC(F)(CN7CCN(c8ccc9c(c8F)CN(C8CCC(=O)NC8=O)C9=O)CC7)C6)CC5)ncn4)c3c2)CC1] | 3-{4-fluoro-5-[4-({3-fluoro-1-[(1-{6-[5-(1-methylcyclopropoxy)-2H-indazol-3-yl]pyrimidin-4-yl}piperidin-4-yl)methyl]azetidin-3-yl}methyl)piperazin-1-yl]-1-oxo-2,3-dihydro-1H-isoindol-2-yl}piperidine-2,6-dione |
| 302 | 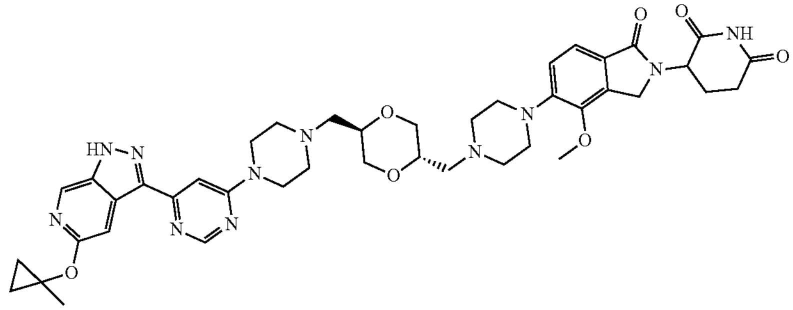 [SMILES: COc1c(N2CCN(C[C@H]3CO[C@H](CN4CCN(c5cc(-c6n[nH]c7cnc(OC8(C)CC8)cc67)ncn5)CC4)CO3)CC2)ccc2c1CN(C1CCC(=O)NC1=O)C2=O] | 3-[4-methoxy-5-(4-{[(2s,5r)-5-[(4-{6-[5-(1-methylcyclopropoxy)-1H-pyrazolo[3,4-c]pyridin-3-yl]pyrimidin-4-yl}piperazin-1-yl)methyl]-1,4-dioxan-2-yl]methyl}piperazin-1-yl)-1-oxo-2,3-dihydro-1H-isoindol-2-yl]piperidine-2,6-dione |
| 303 | 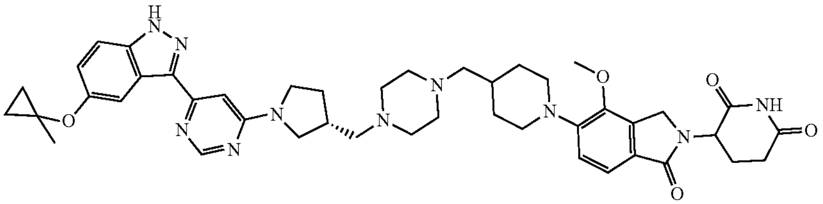 [SMILES: COc1c(N2CCC(CN3CCN(C[C@H]4CCN(c5cc(-c6n[nH]c7ccc(OC8(C)CC8)cc67)ncn5)C4)CC3)CC2)ccc2c1CN(C1CCC(=O)NC1=O)C2=O] | 3-(4-methoxy-5-{4-[(4-{[(3R)-1-{6-[5-(1-methylcyclopropoxy)-1H-indazol-3-yl]pyrimidin-4-yl}pyrrolidin-3-yl]methyl}piperazin-1-yl)methyl]piperidin-1-yl}-1-oxo-2,3-dihydro-1H-isoindol-2-yl)piperidine-2,6-dione |
| 304 | 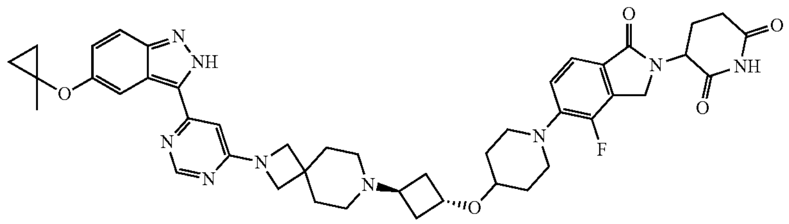 [SMILES: CC1(Oc2ccc3n[nH]c(-c4cc(N5CC6(CCN([C@H]7C[C@H](OC8CCN(c9ccc%10c(c9F)CN(C9CCC(=O)NC9=O)C%10=O)CC8)C7)CC6)C5)ncn4)c3c2)CC1] | 3-(4-fluoro-1-oxo-5-{4-[(1r,3r)-3-(2-{6-[5-(1-methylcyclopropoxy)-2H-indazol-3-yl]pyrimidin-4-yl}-2,7-diazaspiro[3.5]nonan-7-yl)cyclobutoxy]piperidin-1-yl}-2,3-dihydro-1H-isoindol-2-yl)piperidine-2,6-dione |

TABLE 1-continued

| Exemplary bifunctional compounds of the present disclosure** | | |
|---|---|---|
| Ex. No. | Chemical Structure | IUPAC Name |
| 305 | 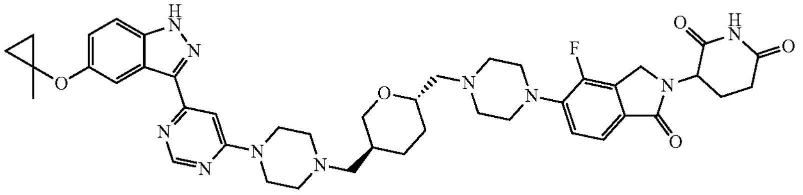 [SMILES: CC1(Oc2ccc3[nH]nc(-c4cc(N5CCN(C[C@@H]6CC[C@@H](CN7CCN(c8ccc9c(c8F)CN(C8CCC(=O)NC8=O)C9=O)CC7)OC6)CC5)ncn4)c3c2)CC1] | 3-[4-fluoro-5-(4-{[(2S,5S)-5-[(4-{6-[5-(1-methylcyclopropoxy)-1H-indazol-3-yl]pyrimidin-4-yl}piperazin-1-yl)methyl]oxan-2-yl]methyl}piperazin-1-yl)-1-oxo-2,3-dihydro-1H-isoindol-2-yl]piperidine-2,6-dione |
| 306 | 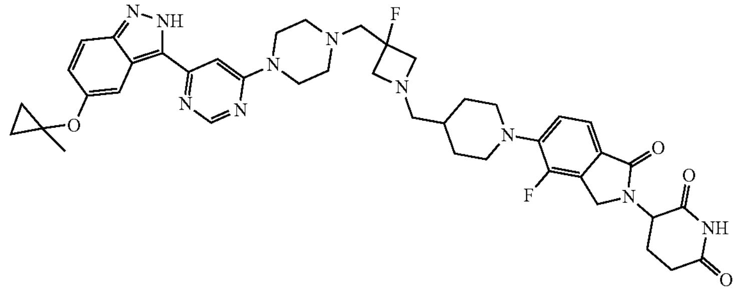 [SMILES: CC1(Oc2ccc3n[nH]c(-c4cc(N5CCN(CC6(F)CN(CC7CCN(c8ccc9c(c8F)CN(C8CCC(=O)NC8=O)C9=O)CC7)C6)CC5)ncn4)c3c2)CC1] | 3-{4-fluoro-5-[4-({3-fluoro-3-[(4-{6-[5-(1-methylcyclopropoxy)-2H-indazol-3-yl]pyrimidin-4-yl}piperazin-1-yl)methyl]azetidin-1-yl}methyl)piperidin-1-yl]-1-oxo-2,3-dihydro-1H-isoindol-2-yl}piperidine-2,6-dione |
| 307 | 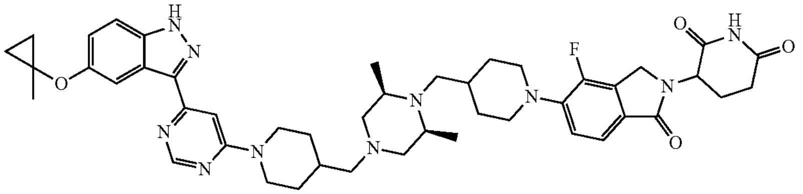 [SMILES: C[C@@H]1CN(CC2CCN(c3cc(-c4n[nH]c5ccc(OC6(C)CC6)cc45)ncn3)CC2)C[C@H](C)N1CC1CCN(c2ccc3c(c2F)CN(C2CCC(=O)NC2=O)C3=O)CC1] | 3-[5-(4-{[(2R,6S)-2,6-dimethyl-4-[(1-{6-[5-(1-methylcyclopropoxy)-1H-indazol-3-yl]pyrimidin-4-yl}piperidin-4-yl)methyl]piperazin-1-yl]methyl}piperidin-1-yl)-4-fluoro-1-oxo-2,3-dihydro-1H-isoindol-2-yl]piperidine-2,6-dione |
| 308 | 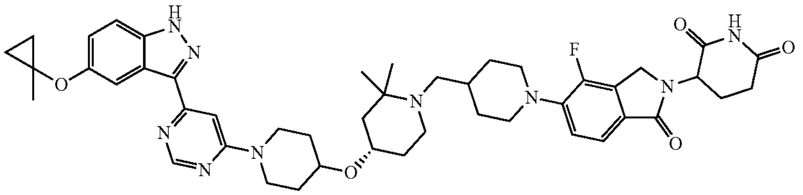 [SMILES: CC1(Oc2ccc3[nH]nc(-c4cc(N5CCC(O[C@H]6CCN(CC7CCN(c8ccc9c(c8F)CN(C8CCC(=O)NC8=O)C9=O)CC7)C(C)(C)C6)CC5)ncn4)c3c2)CC1] | 3-(5-(4-(((S)-2,2-dimethyl-4-((1-(6-(5-(1-methylcyclopropoxy)-1H-indazol-3-yl)pyrimidin-4-yl)piperidin-4-yl)oxy)piperidin-1-yl)methyl)piperidin-1-yl)-4-fluoro-1-oxoisoindolin-2-yl)piperidine-2,6-dione |
| 309 | 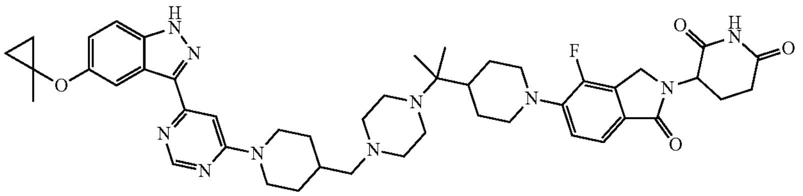 [SMILES: CC1(Oc2ccc3[nH]nc(-c4cc(N5CCC(CN6CCN(C(C)(C)C7CCN(c8ccc9c(c8F)CN(C8CCC(=O)NC8=O)C9=O)CC7)CC6)CC5)ncn4)c3c2)CC1] | 3-{4-fluoro-5-[4-(2-{4-[(1-{6-[5-(1-methylcyclopropoxy)-1H-indazol-3-yl]pyrimidin-4-yl}piperidin-4-yl)methyl]piperazin-1-yl}propan-2-yl)piperidin-1-yl]-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 310 | 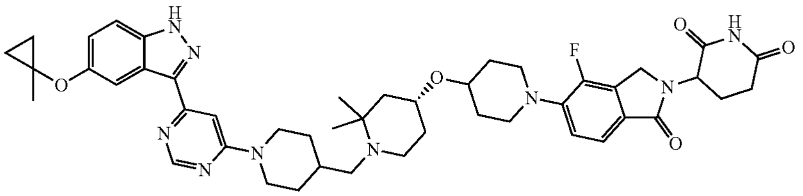 [SMILES: CC1(Oc2ccc3[nH]nc(-c4cc(N5CCC(CN6CC[C@@H](OC7CCN(c8ccc9c(c8F)CN(C8CCC(=O)NC8=O)C9=O)CC7)CC6(C)C)CC5)ncn4)c3c2)CC1] | 3-[5-(4-{[(4R)-2,2-dimethyl-1-[(1-{6-[5-(1-methylcyclopropoxy)-1H-indazol-3-yl]pyrimidin-4-yl}piperidin-4-yl)methyl]piperidin-4-yl]oxy}piperidin-1-yl)-4-fluoro-1-oxo-2,3-dihydro-1H-isoindol-2-yl]piperidine-2,6-dione |
| 311 | 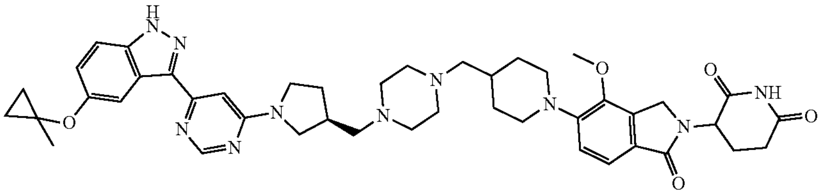 [SMILES: COc1c(N2CCC(CN3CCN(C[C@@H]4CCN(c5cc(-c6n[nH]c7ccc(OC8(C)CC8)cc67)ncn5)C4)CC3)CC2)ccc2c1CN(C1CCC(=O)NC1=O)C2=O] | 3-(4-methoxy-5-{4-[(4-{[(3S)-1-{6-[5-(1-methylcyclopropoxy)-1H-indazol-3-yl]pyrimidin-4-yl}pyrrolidin-3-yl]methyl}piperazin-1-yl)methyl]piperidin-1-yl}-1-oxo-2,3-dihydro-1H-isoindol-2-yl)piperidine-2,6-dione |
| 312 | 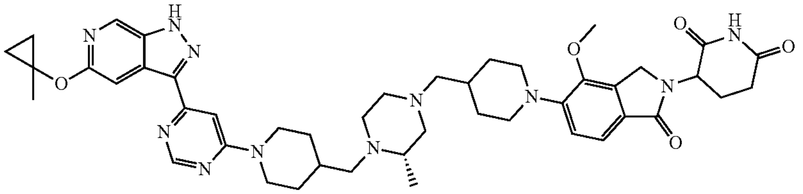 [SMILES: COc1c(N2CCC(CN3CCN(CC4CCN(c5cc(-c6n[nH]c7cnc(OC8(C)CC8)cc67)ncn5)CC4)[C@@H](C)C3)CC2)ccc2c1CN(C1CCC(=O)NC1=O)C2=O] | 3-[4-methoxy-5-(4-{[(3S)-3-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |
| 313 | 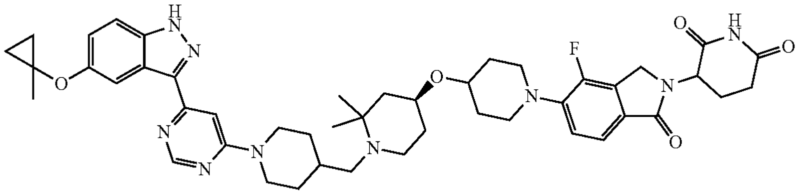 | 3-[5-(4-{[(4S)-2,2-dimethyl-1-[(1-{6-[5-(1-methylcyclopropoxy)-1H-indazol-3-yl]pyrimidin-4-yl}piperidin-4-yl)methyl]piperidin-4-yl]oxy}piperidin-1-yl)-4-fluoro-1-oxo-2,3-dihydro-1H-isoindol-2-yl]piperidine-2,6-dione |
| 314 | 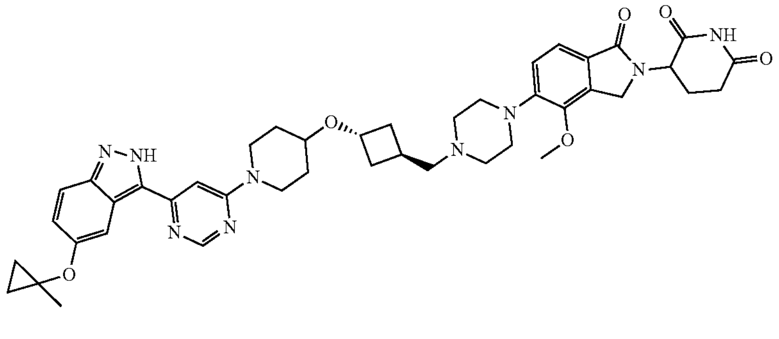 [SMILES: COc1c(N2CCN(C[C@H]3C[C@H](OC4CCN(c5cc(-c6[nH]nc7ccc(OC8(C)CC8)cc67)ncn5)CC4)C3)CC2)ccc2c1CN(C1CCC(=O)NC1=O)C2=O] | 3-[4-methoxy-1-oxo-5-(4-{[(1r,3r)-3-[(1-{6-[5-(1-methylcyclopropoxy)-2H-indazol-3-yl]pyrimidin-4-yl}piperidin-4-yl)oxy]cyclobutyl]methyl}piperazin-1-yl)-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 315 | 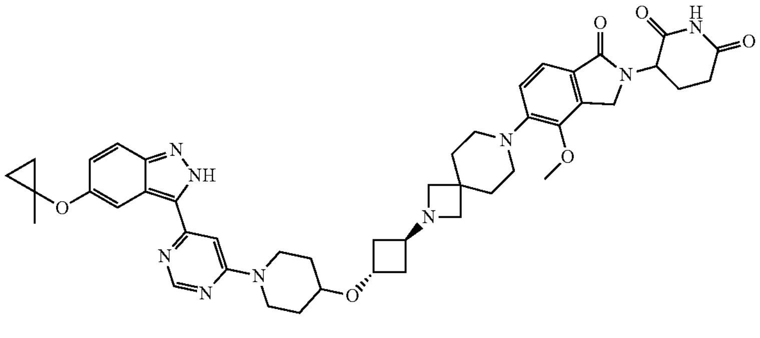 [SMILES: COc1c(N2CCC3(CC2)CN([C@H]2C[C@H](OC4CCN(c5cc(-c6[nH]nc7ccc(OC8(C)CC8)cc67)ncn5)CC4)C2)C3)ccc2c1CN(C1CCC(=O)NC1=O)C2=O] | 3-(4-methoxy-1-oxo-5-{2-[(1r,3r)-3-[(1-{6-[5-(1-methylcyclopropoxy)-2H-indazol-3-yl]pyrimidin-4-yl}piperidin-4-yl)oxy]cyclobutyl]-2,7-diazaspiro[3.5]nonan-7-yl}-2,3-dihydro-1H-isoindol-2-yl)piperidine-2,6-dione |
| 316 | 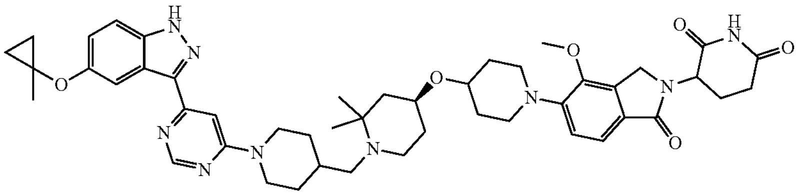 [SMILES: COc1c(N2CCC(O[C@H]3CCN(CC4CCN(c5cc(-c6n[nH]c7ccc(OC8(C)CC8)cc67)ncn5)CC4)C(C)(C)C3)CC2)ccc2c1CN(C1CCC(=O)NC1=O)C2=O] | 3-[5-(4-{[(4S)-2,2-dimethyl-1-[(1-{6-[5-(1-methylcyclopropoxy)-1H-indazol-3-yl]pyrimidin-4-yl}piperidin-4-yl)methyl]piperidin-4-yl]oxy}piperidin-1-yl)-4-methoxy-1-oxo-2,3-dihydro-1H-isoindol-2-yl]piperidine-2,6-dione |
| 317 | 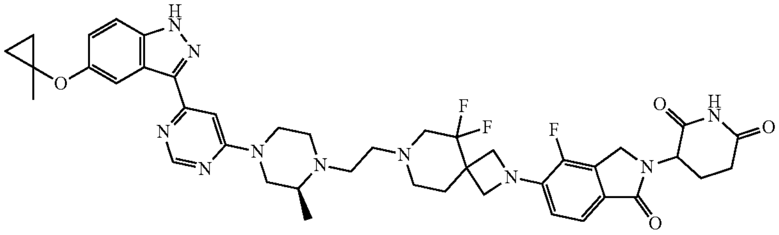 [SMILES: C[C@H]1CN(c2cc(-c3n[nH]c4ccc(OC5(C)CC5)cc34)ncn2)CCN1CCN1CCC2(CN(c3ccc4c(c3F)CN(C3CCC(=O)NC3=O)C4=O)C2)C(F)(F)C1] | 3-[5-(5,5-difluoro-7-{2-[(2S)-2-methyl-4-{6-[5-(1-methylcyclopropoxy)-1H-indazol-3-yl]pyrimidin-4-yl}piperazin-1-yl]ethyl}-2,7-diazaspiro[3.5]nonan-2-yl)-4-fluoro-1-oxo-2,3-dihydro-1H-isoindol-2-yl]piperidine-2,6-dione |
| 318 | 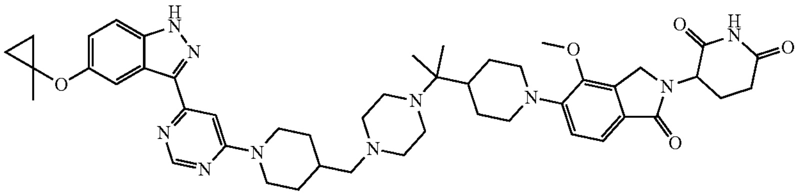 [SMILES: COc1c(N2CCC(C(C)(C)N3CCN(CC4CCN(c5cc(-c6n[nH]c7ccc(OC8(C)CC8)cc67)ncn5)CC4)CC3)CC2)ccc2c1CN(C1CCC(=O)NC1=O)C2=O] | 3-{4-methoxy-5-[4-(2-{4-[(1-{6-[5-(1-methylcyclopropoxy)-1H-indazol-3-yl]pyrimidin-4-yl}piperidin-4-yl)methyl]piperazin-1-yl}propan-2-yl)piperidin-1-yl]-1-oxo-2,3-dihydro-1H-isoindol-2-yl}piperidine-2,6-dione |
| 319 | 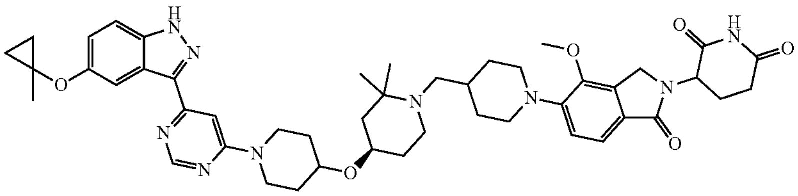 [SMILES: COc1c(N2CCC(CN3CC[C@@H](OC4CCN(c5cc(-c6n[nH]c7ccc(OC8(C)CC8)cc67)ncn5)CC4)CC3(C)C)CC2)ccc2c1CN(C1CCC(=O)NC1=O)C2=O] | 3-(5-(4-(((R)-2,2-dimethyl-4-((1-(6-(5-(1-methylcyclopropoxy)-1H-indazol-3-yl)pyrimidin-4-yl)piperidin-4-yl)oxy)piperidin-1-yl)methyl)piperidin-1-yl)-4-methoxy-1-oxoisoindolin-2-yl)piperidine-2,6-dione |

TABLE 1-continued

Exemplary bifunctional compounds of the present disclosure**

| Ex. No. | Chemical Structure | IUPAC Name |
|---|---|---|
| 320 | 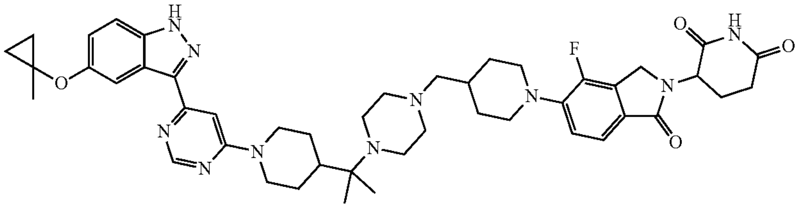 [SMILES: CC1(Oc2ccc3[nH]nc(-c4cc(N5CCC(C(C)(C)N6CCN(CC7CCN(c8ccc9c(c8F)CN(C8CCC(=O)NC8=O)C9=O)CC7)CC6)CC5)ncn4)c3c2)CC1] | 3-{4-fluoro-5-[4-({4-[2-(1-{6-[5-(1-methylcyclopropoxy)-1H-indazol-3-yl]pyrimidin-4-yl}piperidin-4-yl)propan-2-yl]piperazin-1-yl}methyl)piperidin-1-yl]-1-oxo-2,3-dihydro-1H-isoindol-2-yl}piperidine-2,6-dione |
| 321 | 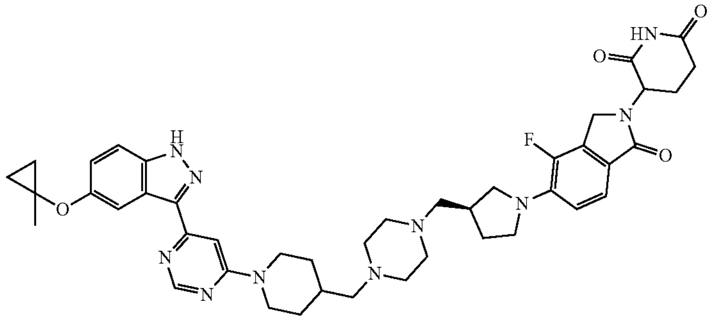 [SMILES: CC1(Oc2ccc3[nH]nc(-c4cc(N5CCC(CN6CCN(C[C@@H]7CCN(c8ccc9c(c8F)CN(C8CCC(=O)NC8=O)C9=O)C7)CC6)CC5)ncn4)c3c2)CC1] | 3-{4-fluoro-5-[(3S)-3-({4-[(1-{6-[5-(1-methylcyclopropoxy)-1H-indazol-3-yl]pyrimidin-4-yl}piperidin-4-yl)methyl]piperazin-1-yl}methyl)pyrrolidin-1-yl]-1-oxo-2,3-dihydro-1H-isoindol-2-yl}piperidine-2,6-dione |
| 322 | 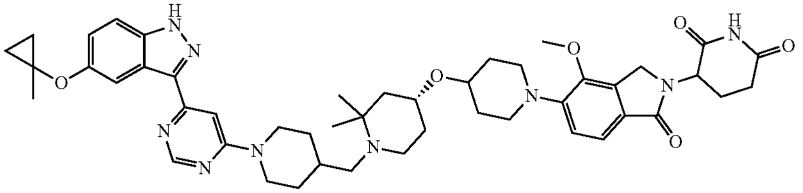 [SMILES: COc1c(N2CCC(O[C@@H]3CCN(CC4CCN(c5cc(-c6n[nH]c7ccc(OC8(C)CC8)cc67)ncn5)CC4)C(C)(C)C3)CC2)ccc2c1CN(C1CCC(=O)NC1=O)C2=O] | 3-[5-(4-{[(4R)-2,2-dimethyl-1-[(1-{6-[5-(1-methylcyclopropoxy)-1H-indazol-3-yl]pyrimidin-4-yl}piperidin-4-yl)methyl]piperidin-4-yl]oxy}piperidin-1-yl)-4-methoxy-1-oxo-2,3-dihydro-1H-isoindol-2-yl]piperidine-2,6-dione |
| 323 | 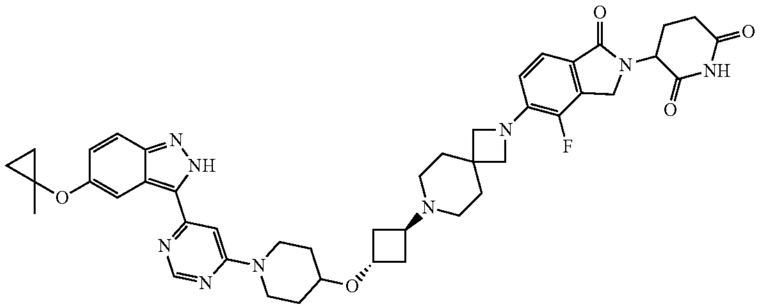 [SMILES: CC1(Oc2ccc3n[nH]c(-c4cc(N5CCC(O[C@H]6C[C@H](N7CCC8(CC7)CN(c7ccc9c(c7F)CN(C7CCC(=O)NC7=O)C9=O)C8)C6)CC5)ncn4)c3c2)CC1] | 3-(4-fluoro-1-oxo-5-{7-[(1r,3r)-3-[(1-{6-[5-(1-methylcyclopropoxy)-2H-indazol-3-yl]pyrimidin-4-yl}piperidin-4-yl)oxy]cyclobutyl]-2,7-diazaspiro[3.5]nonan-2-yl}-2,3-dihydro-1H-isoindol-2-yl)piperidine-2,6-dione |
| 324 | 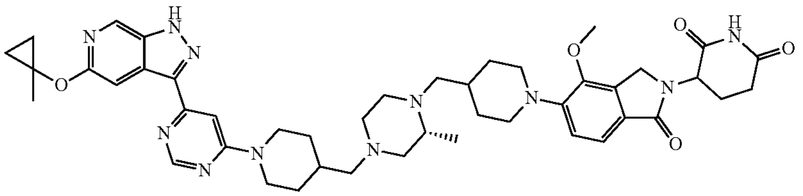 [SMILES: COc1c(N2CCC(CN3CCN(CC4CCN(c5cc(-c6n[nH]c7cnc(OC8(C)CC8)cc67)ncn5)CC4)C[C@H]3C)CC2)ccc2c1CN(C1CCC(=O)NC1=O)C2=O] | 3-[4-methoxy-5-(4-{[(2R)-2-methyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl]methyl}piperidin-1-yl)-1-oxo-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 325 | 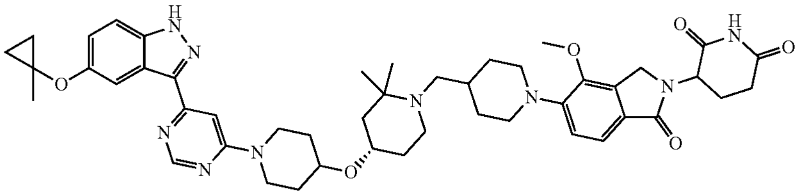 [SMILES: COc1c(N2CCC(CN3CC[C@H](OC4CCN(c5cc(-c6n[nH]c7ccc(OC8(C)CC8)cc67)ncn5)CC4)CC3(C)C)CC2)ccc2c1CN(C1CCC(=O)NC1=O)C2=O] | 3-(5-(4-(((S)-2,2-dimethyl-4-((1-(6-(5-(1-methylcyclopropoxy)-1H-indazol-3-yl)pyrimidin-4-yl)piperidin-4-yl)oxy)piperidin-1-yl)methyl)piperidin-1-yl)-4-methoxy-1-oxoisoindolin-2-yl)piperidine-2,6-dione |
| 326 | 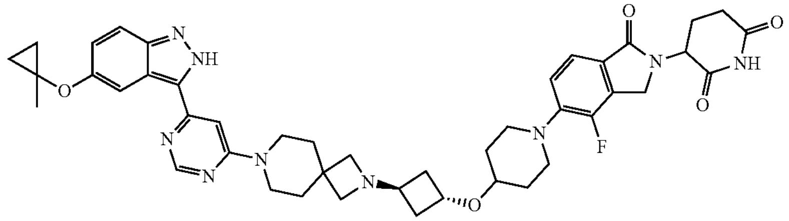 [SMILES: CC1(Oc2ccc3n[nH]c(-c4cc(N5CCC6(CC5)CN([C@H]5C[C@H](OC7CCN(c8ccc9c(c8F)CN(C8CCC(=O)NC8=O)C9=O)CC7)C5)C6)ncn4)c3c2)CC1] | 3-(4-fluoro-1-oxo-5-{4-[(1r,3r)-3-(7-{6-[5-(1-methylcyclopropoxy)-2H-indazol-3-yl]pyrimidin-4-yl}-2,7-diazaspiro[3.5]nonan-2-yl)cyclobutoxy]piperidin-1-yl}-2,3-dihydro-1H-isoindol-2-yl)piperidine-2,6-dione |
| 327 | 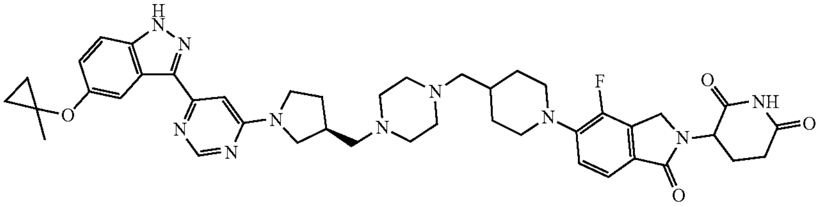 [SMILES: CC1(Oc2ccc3[nH]nc(-c4cc(N5CC[C@@H](CN6CCN(CC7CCN(c8ccc9c(c8F)CN(C8CCC(=O)NC8=O)C9=O)CC7)CC6)C5)ncn4)c3c2)CC1] | 3-(4-fluoro-5-{4-[(4-{[(3S)-1-{6-[5-(1-methylcyclopropoxy)-1H-indazol-3-yl]pyrimidin-4-yl}pyrrolidin-3-yl]methyl}piperazin-1-yl)methyl]piperidin-1-yl}-1-oxo-2,3-dihydro-1H-isoindol-2-yl)piperidine-2,6-dione |
| 328 | 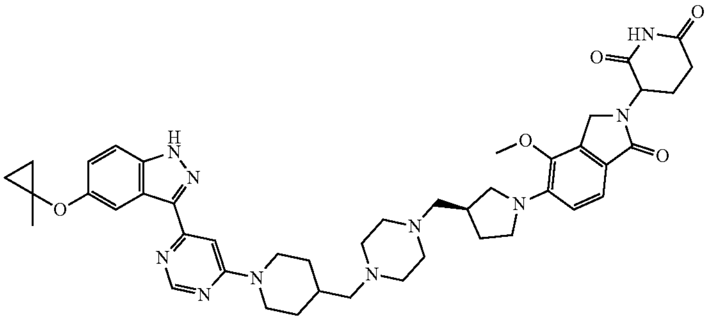 [SMILES: COc1c(N2CC[C@@H](CN3CCN(CC4CCN(c5cc(-c6n[nH]c7ccc(OC8(C)CC8)cc67)ncn5)CC4)CC3)C2)ccc2c1CN(C1CCC(=O)NC1=O)C2=O] | 3-{4-methoxy-5-[(3S)-3-({4-[(1-{6-[5-(1-methylcyclopropoxy)-1H-indazol-3-yl]pyrimidin-4-yl}piperidin-4-yl)methyl]piperazin-1-yl}methyl)pyrrolidin-1-yl]-1-oxo-2,3-dihydro-1H-isoindol-2-yl}piperidine-2,6-dione |
| 329 | 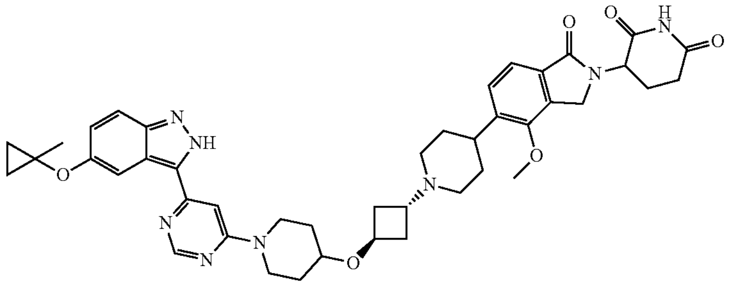 [SMILES: COc1c(C2CCN([C@H]3C[C@H](OC4CCN(c5cc(-c6[nH]nc7ccc(OC8(C)CC8)cc67)ncn5)CC4)C3)CC2)ccc2c1CN(C1CCC(=O)NC1=O)C2=O] | 3-(4-methoxy-1-oxo-5-{1-[(1r,3r)-3-[(1-{6-[5-(1-methylcyclopropoxy)-2H-indazol-3-yl]pyrimidin-4-yl}piperidin-4-yl)oxy]cyclobutyl]piperidin-4-yl}-2,3-dihydro-1H-isoindol-2-yl)piperidine-2,6-dione |

TABLE 1-continued

| Exemplary bifunctional compounds of the present disclosure** | | |
|---|---|---|
| Ex. No. | Chemical Structure | IUPAC Name |
| 330 | 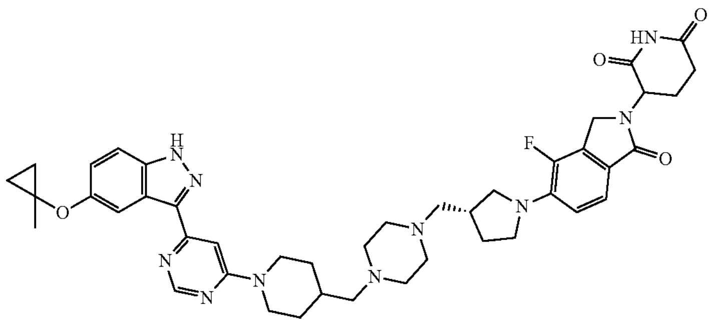 [SMILES: CC1(Oc2ccc3[nH]nc(-c4cc(N5CCC(CN6CCN(C[C@H]7CCN(c8ccc9c(c8F)CN(C8CCC(=O)NC8=O)C9=O)C7)CC6)CC5)ncn4)c3c2)CC1] | 3-{4-fluoro-5-[(3R)-3-({4-[(1-{6-[5-(1-methylcyclopropoxy)-1H-indazol-3-yl]pyrimidin-4-yl}piperidin-4-yl)methyl]piperazin-1-yl}methyl)pyrrolidin-1-yl]-1-oxo-2,3-dihydro-1H-isoindol-2-yl}piperidine-2,6-dione |
| 331 | 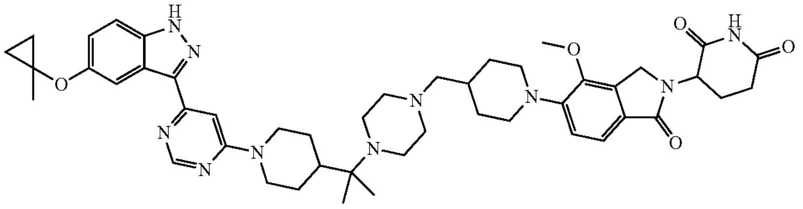 [SMILES: COc1c(N2CCC(CN3CCN(C(C)(C)C4CCN(c5cc(-c6n[nH]c7ccc(OC8(C)CC8)cc67)ncn5)CC4)CC3)CC2)ccc2c1CN(C1CCC(=O)NC1=O)C2=O] | 3-{4-methoxy-5-[4-({4-[2-(1-{6-[5-(1-methylcyclopropoxy)-1H-indazol-3-yl]pyrimidin-4-yl}piperidin-4-yl)propan-2-yl]piperazin-1-yl}methyl)piperidin-1-yl]-1-oxo-2,3-dihydro-1H-isoindol-2-yl}piperidine-2,6-dione |
| 332 | 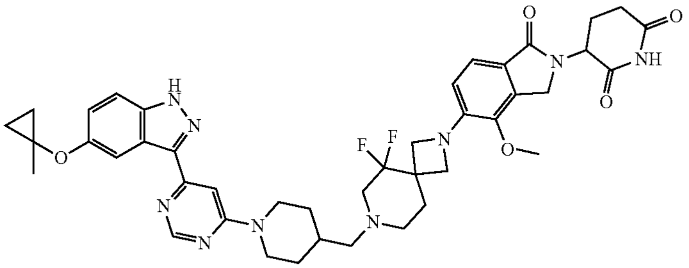 [SMILES: COc1c(N2CC3(CCN(CC4CCN(c5cc(-c6n[nH]c7ccc(OC8(C)CC8)cc67)ncn5)CC4)CC3(F)F)C2)ccc2c1CN(C1CCC(=O)NC1=O)C2=O] | 3-(5-{5,5-difluoro-7-[(1-{6-[5-(1-methylcyclopropoxy)-1H-indazol-3-yl]pyrimidin-4-yl}piperidin-4-yl)methyl]-2,7-diazaspiro[3.5]nonan-2-yl}-4-methoxy-1-oxo-2,3-dihydro-1H-isoindol-2-yl)piperidine-2,6-dione |
| 333 | 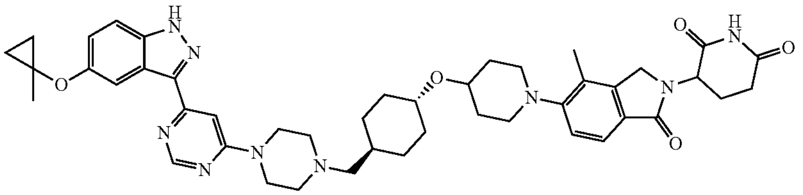 [SMILES: Cc1c(N2CCC(O[C@H]3CC[C@H](CN4CCN(c5cc(-c6n[nH]c7ccc(OC8(C)CC8)cc67)ncn5)CC4)CC3)CC2)ccc2c1CN(C1CCC(=O)NC1=O)C2=O] | 3-(4-methyl-5-(4-(((1r,4r)-4-((4-(6-(5-(1-methylcyclopropoxy)-1H-indazol-3-yl)pyrimidin-4-yl)piperazin-1-yl)methyl)cyclohexyl)oxy)piperidin-1-yl)-1-oxoisoindolin-2-yl)piperidine-2,6-dione |
| 334 | 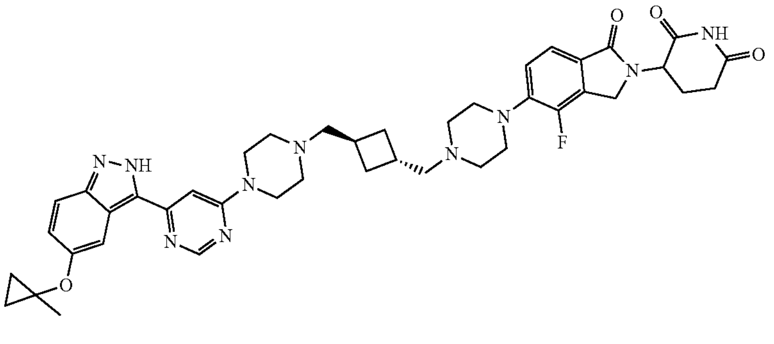 [SMILES: CC1(Oc2ccc3n[nH]c(-c4cc(N5CCN(C[C@H]6C[C@H](CN7CCN(c8ccc9c(c8F)CN(C8CCC(=O)NC8=O)C9=O)CC7)C6)CC5)ncn4)c3c2)CC1] | 3-[4-fluoro-1-oxo-5-(4-{[(1r,3r)-3-[(4-{6-[5-(1-methylcyclopropoxy)-2H-indazol-3-yl]pyrimidin-4-yl}piperazin-1-yl)methyl]cyclobutyl]methyl}piperazin-1-yl)-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 335 | 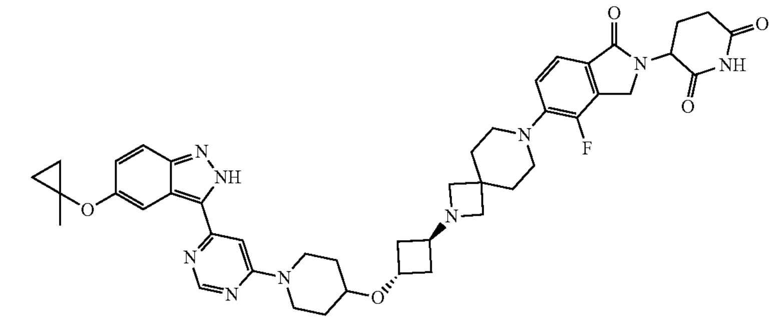 [SMILES: CC1(Oc2ccc3n[nH]c(-c4cc(N5CCC(O[C@H]6C[C@H](N7CC8(CCN(c9ccc%10c(c9F)CN(C9CCC(=O)NC9=O)C%10=O)CC8)C7)C6)CC5)ncn4)c3c2)CC1] | 3-(4-fluoro-1-oxo-5-{2-[(1r,3r)-3-[(1-{6-[5-(1-methylcyclopropoxy)-2H-indazol-3-yl]pyrimidin-4-yl}piperidin-4-yl)oxy]cyclobutyl]-2,7-diazaspiro[3.5]nonan-7-yl}-2,3-dihydro-1H-isoindol-2-yl)piperidine-2,6-dione |
| 336 | 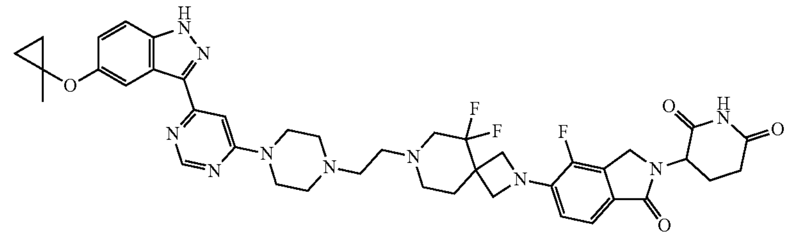 [SMILES: CC1(Oc2ccc3[nH]nc(-c4cc(N5CCN(CCN6CCC7(CN(c8ccc9c(c8F)CN(C8CCC(=O)NC8=O)C9=O)C7)C(F)(F)C6)CC5)ncn4)c3c2)CC1] | 3-(5-{5,5-difluoro-7-[2-(4-{6-[5-(1-methylcyclopropoxy)-1H-indazol-3-yl]pyrimidin-4-yl}piperazin-1-yl)ethyl]-2,7-diazaspiro[3.5]nonan-2-yl}-4-fluoro-1-oxo-2,3-dihydro-1H-isoindol-2-yl)piperidine-2,6-dione |
| 337 | 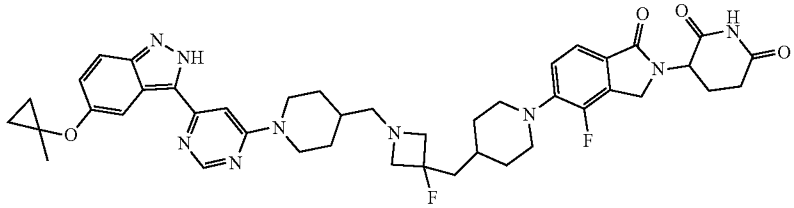 [SMILES: CC1(Oc2ccc3n[nH]c(-c4cc(N5CCC(CN6CC(F)(CC7CCN(c8ccc9c(c8F)CN(C8CCC(=O)NC8=O)C9=O)CC7)C6)CC5)ncn4)c3c2)CC1] | 3-{4-fluoro-5-[4-({3-fluoro-1-[(1-{6-[5-(1-methylcyclopropoxy)-2H-indazol-3-yl]pyrimidin-4-yl}piperidin-4-yl)methyl]azetidin-3-yl}methyl)piperidin-1-yl]-1-oxo-2,3-dihydro-1H-isoindol-2-yl}piperidine-2,6-dione |
| 338 | 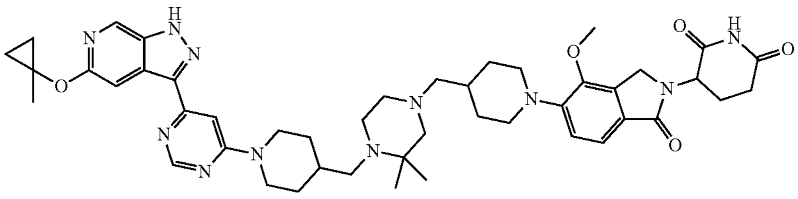 | 3-{5-[4-({3,3-dimethyl-4-[(1-{6-[5-(1-methylcyclopropoxy)-1H-pyrazolo[3,4-c]pyridin-3-yl]pyrimidin-4-yl}piperidin-4-yl)methyl]piperazin-1-yl}methyl)piperidin-1-yl]-4-methoxy-1-oxo-2,3-dihydro-1H-isoindol-2-yl}piperidine-2,6-dione |
| 339 | 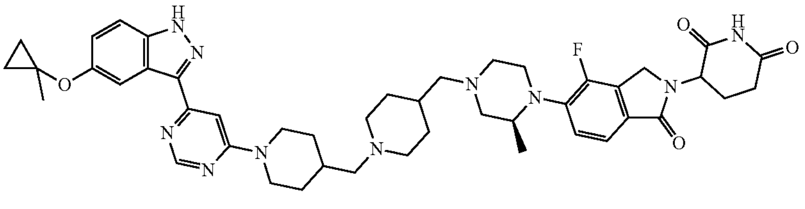 [SMILES: C[C@H]1CN(CC2CCN(CC3CCN(c4cc(-c5n[nH]c6ccc(OC7(C)CC7)cc56)ncn4)CC3)CC2)CCN1c1ccc2c(c1F)CN(C1CCC(=O)NC1=O)C2=O] | 3-{4-fluoro-5-[(2S)-2-methyl-4-({1-[(1-{6-[5-(1-methylcyclopropoxy)-1H-indazol-3-yl]pyrimidin-4-yl}piperidin-4-yl)methyl]piperidin-4-yl}methyl)piperazin-1-yl]-1-oxo-2,3-dihydro-1H-isoindol-2-yl}piperidine-2,6-dione |

TABLE 1-continued

Exemplary bifunctional compounds of the present disclosure**

| Ex. No. | Chemical Structure | IUPAC Name |
|---|---|---|
| 340 | 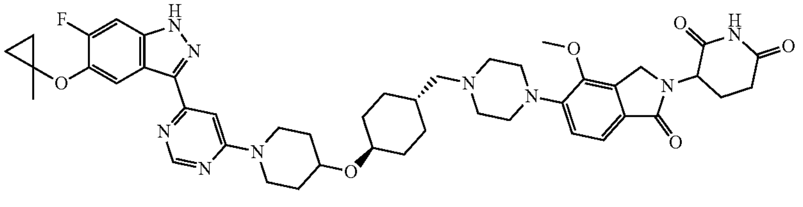 [SMILES: COc1c(N2CCN(C[C@H]3CC[C@H](OC4CCN(c5cc(-c6n[nH]c7cc(F)c(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(1-{6-[6-fluoro-5-(1-methylcyclopropoxy)-1H-indazol-3-yl]pyrimidin-4-yl}piperidin-4-yl)oxy]cyclohexyl]methyl}piperazin-1-yl)-2,3-dihydro-1H-isoindol-2-yl]piperidine-2,6-dione |
| 341 | 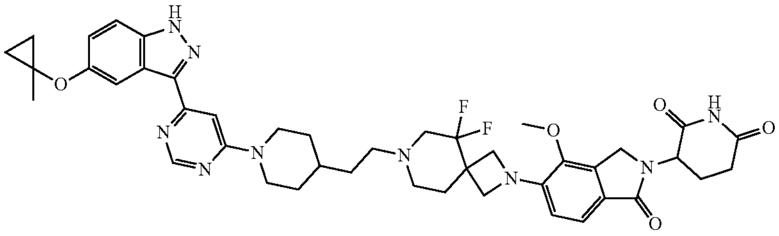 [SMILES: COc1c(N2CC3(CCN(CCC4CCN(c5cc(-c6n[nH]c7ccc(OC8(C)CC8)cc67)ncn5)CC4)CC3(F)F)C2)ccc2c1CN(C1CCC(=O)NC1=O)C2=O] | 3-(5-{5,5-difluoro-7-[2-(1-{6-[5-(1-methylcyclopropoxy)-1H-indazol-3-yl]pyrimidin-4-yl}piperidin-4-yl)ethyl]-2,7-diazaspiro[3.5]nonan-2-yl}-4-methoxy-1-oxo-2,3-dihydro-1H-isoindol-2-yl)piperidine-2,6-dione |
| 342 | 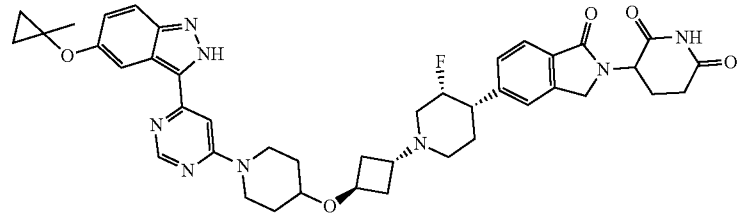 [SMILES: CC1(Oc2ccc3n[nH]c(-c4cc(N5CCC(O[C@H]6C[C@H](N7CC[C@@H](c8ccc9c(c8)CN(C8CCC(=O)NC8=O)C9=O)[C@@H](F)C7)C6)CC5)ncn4)c3c2)CC1] | 3-{5-[(3r,4s)-3-fluoro-1-[(1r,3r)-3-[(1-{6-[5-(1-methylcyclopropoxy)-2H-indazol-3-yl]pyrimidin-4-yl}piperidin-4-yl)oxy]cyclobutyl]piperidin-4-yl]-1-oxo-2,3-dihydro-1H-isoindol-2-yl}piperidine-2,6-dione |
| 343 | 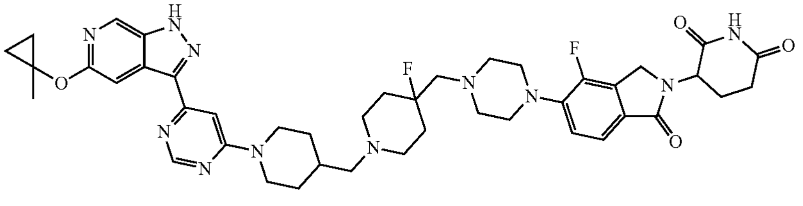 [SMILES: CC1(Oc2cc3c(-c4cc(N5CCC(CN6CCC(F)(CN7CCN(c8ccc9c(c8F)CN(C8CCC(=O)NC8=O)C9=O)CC7)CC6)CC5)ncn4)n[nH]c3cn2)CC1] | 3-{4-fluoro-5-[4-({4-fluoro-1-[(1-{6-[5-(1-methylcyclopropoxy)-1H-pyrazolo[3,4-c]pyridin-3-yl]pyrimidin-4-yl}piperidin-4-yl)methyl]piperidin-4-yl}methyl)piperazin-1-yl]-1-oxo-2,3-dihydro-1H-isoindol-2-yl}piperidine-2,6-dione |
| 344 | 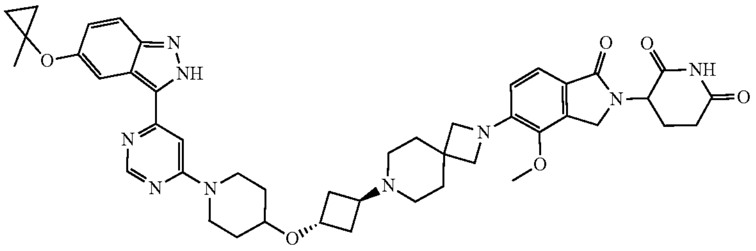 [SMILES: COc1c(N2CC3(CCN([C@H]4C[C@H](OC5CCN(c6cc(-c7[nH]nc8ccc(OC9(C)CC9)cc78)ncn6)CC5)C4)CC3)C2)ccc2c1CN(C1CCC(=O)NC1=O)C2=O] | 3-(4-methoxy-1-oxo-5-{7-[(1r,3r)-3-[(1-{6-[5-(1-methylcyclopropoxy)-2H-indazol-3-yl]pyrimidin-4-yl}piperidin-4-yl)oxy]cyclobutyl]-2,7-diazaspiro[3.5]nonan-2-yl}-2,3-dihydro-1H-isoindol-2-yl)piperidine-2,6-dione |

TABLE 1-continued

| Exemplary bifunctional compounds of the present disclosure** | | |
|---|---|---|
| Ex. No. | Chemical Structure | IUPAC Name |
| 345 | 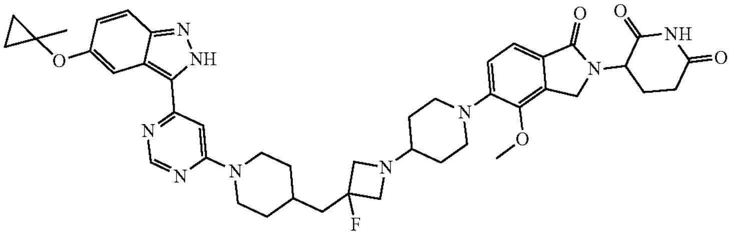 [SMILES: COc1c(N2CCC(N3CC(F)(CC4CCN(c5cc(-c6[nH]nc7ccc(OC8(C)CC8)cc67)ncn5)CC4)C3)CC2)ccc2c1CN(C1CCC(=O)NC1=O)C2=O] | 3-(5-(4-(3-fluoro-3-((1-(6-(5-(1-methylcyclopropoxy)-2H-indazol-3-yl)pyrimidin-4-yl)piperidin-4-yl)methyl)azetidin-1-yl)piperidin-1-yl)-4-methoxy-1-oxoisoindolin-2-yl)piperidine-2,6-dione |
| 346 | 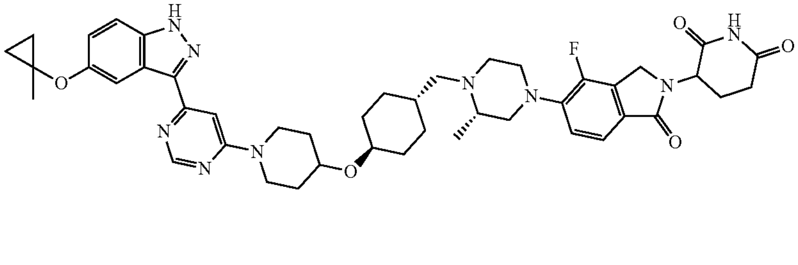 [SMILES: C[C@H]1CN(c2ccc3c(c2F)CN(C2CCC(=O)NC2=O)C3=O)CCN1C[C@H]1CC[C@H](OC2CCN(c3cc(-c4n[nH]c5ccc(OC6(C)CC6)cc45)ncn3)CC2)CC1] | 3-{4-fluoro-5-[(3S)-3-methyl-4-{[(1r,4r)-4-[(1-{6-[5-(1-methylcyclopropoxy)-1H-indazol-3-yl]pyrimidin-4-yl}piperidin-4-yl)oxy]cyclohexyl]methyl}piperazin-1-yl]-1-oxo-2,3-dihydro-1H-isoindol-2-yl}piperidine-2,6-dione |
| 347 | 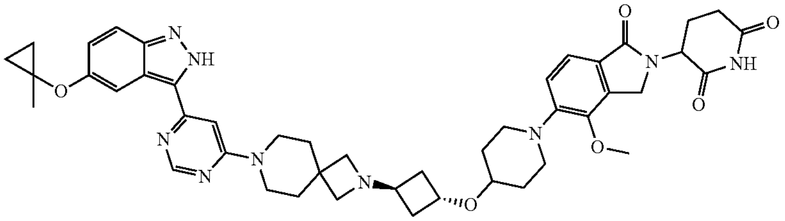 [SMILES: COc1c(N2CCC(O[C@H]3C[C@H](N4CC5(CCN(c6cc(-c7[nH]nc8ccc(OC9(C)CC9)cc78)ncn6)CC5)C4)C3)CC2)ccc2c1CN(C1CCC(=O)NC1=O)C2=O] | 3-(4-methoxy-1-oxo-5-{4-[(1r,3r)-3-(7-{6-[5-(1-methylcyclopropoxy)-2H-indazol-3-yl]pyrimidin-4-yl}-2,7-diazaspiro[3.5]nonan-2-yl)cyclobutoxy]piperidin-1-yl}-2,3-dihydro-1H-isoindol-2-yl)piperidine-2,6-dione |
| 348 | 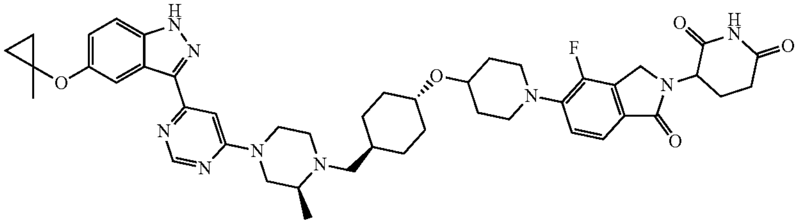 [SMILES: C[C@H]1CN(c2cc(-c3n[nH]c4ccc(OC5(C)CC5)cc34)ncn2)CCN1C[C@H]1CC[C@H](OC2CCN(c3ccc4c(c3F)CN(C3CCC(=O)NC3=O)C4=O)CC2)CC1] | 3-(4-fluoro-5-(4-(((1s,4r)-4-(((S)-2-methyl-4-(6-(5-(1-methylcyclopropoxy)-1H-indazol-3-yl)pyrimidin-4-yl)piperazin-1-yl)methyl)cyclohexyl)oxy)piperidin-1-yl)-1-oxoisoindolin-2-yl)piperidine-2,6-dione |
| 349 | 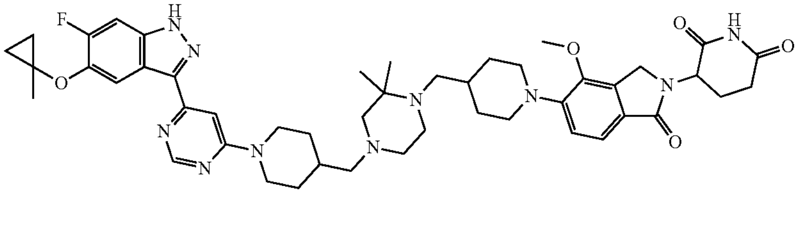 [SMILES: COc1c(N2CCC(CN3CCN(CC4CCN(c5cc(-c6n[nH]c7cc(F)c(OC8(C)CC8)cc67)ncn5)CC4)CC3(C)C)CC2)ccc2c1CN(C1CCC(=O)NC1=O)C2=O] | 3-{5-[4-({4-[(1-{6-[6-fluoro-5-(1-methylcyclopropoxy)-1H-indazol-3-yl]pyrimidin-4-yl}piperidin-4-yl)methyl]-2,2-dimethylpiperazin-1-yl}methyl)piperidin-1-yl]-4-methoxy-1-oxo-2,3-dihydro-1H-isoindol-2-yl}piperidine-2,6-dione |

TABLE 1-continued

| Ex. No. | Chemical Structure | IUPAC Name |
|---|---|---|
| | Exemplary bifunctional compounds of the present disclosure** | |
| 350 | 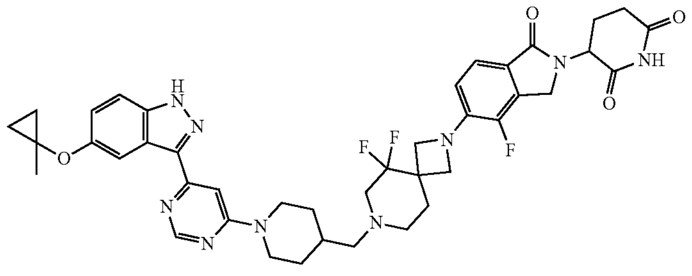 [SMILES: CC1(Oc2ccc3[nH]nc(-c4cc(N5CCC(CN6CCC7(CN(c8ccc9c(c8F)CN(C8CCC(=O)NC8=O)C9=O)C7)C(F)(F)C6)CC5)ncn4)c3c2)CC1] | 3-(5-{5,5-difluoro-7-[(1-{6-[5-(1-methylcyclopropoxy)-1H-indazol-3-yl]pyrimidin-4-yl}piperidin-4-yl)methyl]-2,7-diazaspiro[3.5]nonan-2-yl}-4-fluoro-1-oxo-2,3-dihydro-1H-isoindol-2-yl)piperidine-2,6-dione |
| 351 | 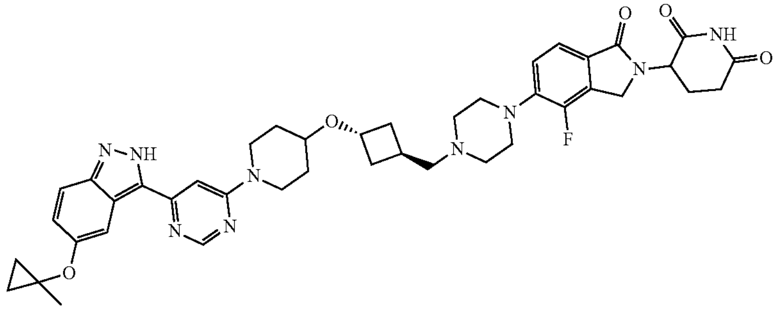 [SMILES: CC1(Oc2ccc3n[nH]c(-c4cc(N5CCC(O[C@H]6C[C@H](CN7CCN(c8ccc9c(c8F)CN(C8CCC(=O)NC8=O)C9=O)CC7)C6)CC5)ncn4)c3c2)CC1] | 3-[4-fluoro-1-oxo-5-(4-{[(1r,3r)-3-[(1-{6-[5-(1-methylcyclopropoxy)-2H-indazol-3-yl]pyrimidin-4-yl}piperidin-4-yl)oxy]cyclobutyl]methyl}piperazin-1-yl)-2,3-dihydro-1H-isoindol-2-yl]piperidine-2,6-dione |
| 352 | 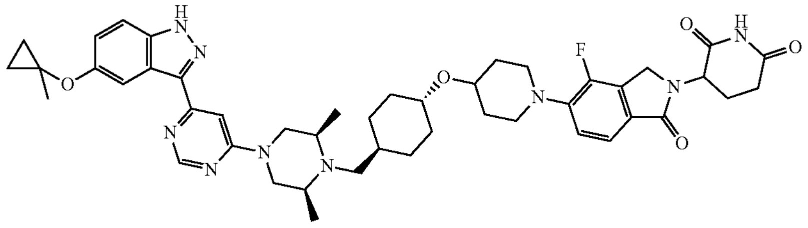 [SMILES: C[C@@H]1CN(c2cc(-c3n[nH]c4ccc(OC5(C)CC5)cc34)ncn2)C[C@H](C)N1C[C@H]1CC[C@H](OC2CCN(c3ccc4c(c3F)CN(C3CCC(=O)NC3=O)C4=O)CC2)CC1] | 3-[4-fluoro-1-oxo-5-(4-{[(1r,4r)-4-{[(2R,6S)-2,6-dimethyl-4-{6-[5-(1-methylcyclopropoxy)-1H-indazol-3-yl]pyrimidin-4-yl}piperazin-1-yl]methyl}cyclohexyl]oxy}piperidin-1-yl)-2,3-dihydro-1H-isoindol-2-yl]piperidine-2,6-dione |
| 353 | 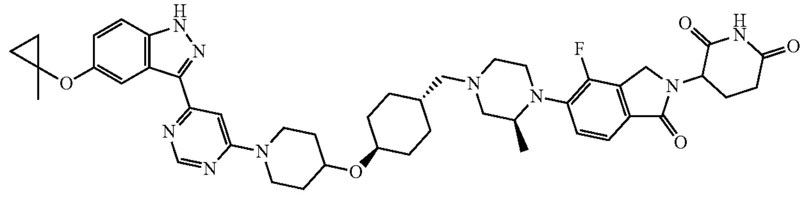 [SMILES: C[C@H]1CN(C[C@H]2CC[C@H](OC3CCN(c4cc(-c5n[nH]c6ccc(OC7(C)CC7)cc56)ncn4)CC3)CC2)CCN1c1ccc2c(c1F)CN(C1CCC(=O)NC1=O)C2=O] | 3-{4-fluoro-5-[(2S)-2-methyl-4-{[(1r,4r)-4-[(1-{6-[5-(1-methylcyclopropoxy)-1H-indazol-3-yl]pyrimidin-4-yl}piperidin-4-yl)oxy]cyclohexyl]methyl}piperazin-1-yl]-1-oxo-2,3-dihydro-1H-isoindol-2-yl}piperidine-2,6-dione |
| 354 | 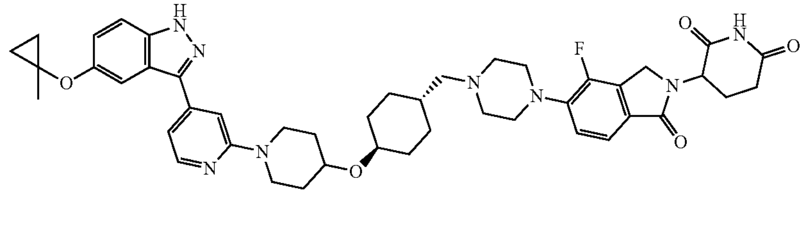 [SMILES: CC1(Oc2ccc3[nH]nc(-c4ccnc(N5CCC(O[C@H]6CC[C@H](CN7CCN(c8ccc9c(c8F)CN(C8CCC(=O)NC8=O)C9=O)CC7)CC6)CC5)c4)c3c2)CC1] | 3-(4-fluoro-5-(4-(((1r,4r)-4-((1-(4-(5-(1-methylcyclopropoxy)-1H-indazol-3-yl)pyridin-2-yl)piperidin-4-yl)oxy)cyclohexyl)methyl)piperazin-1-yl)-1-oxoisoindolin-2-yl)piperidine-2,6-dione |

TABLE 1-continued

| Exemplary bifunctional compounds of the present disclosure** | | |
|---|---|---|
| Ex. No. | Chemical Structure | IUPAC Name |
| 355 | 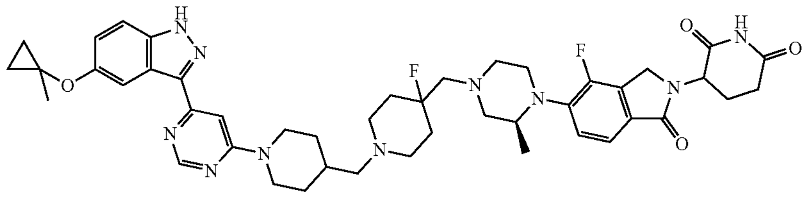 [SMILES: C[C@H]1CN(CC2(F)CCN(CC3CCN(c4cc(-c5n[nH]c6ccc(OC7(C)CC7)cc56)ncn4)CC3)CC2)CCN1c1ccc2c(c1F)CN(C1CCC(=O)NC1=O)C2=O] | 3-{4-fluoro-5-[(2S)-4-({4-fluoro-1-[(1-{6-[5-(1-methylcyclopropoxy)-1H-indazol-3-yl]pyrimidin-4-yl}piperidin-4-yl)methyl]piperidin-4-yl}methyl)-2-methylpiperazin-1-yl]-1-oxo-2,3-dihydro-1H-isoindol-2-yl}piperidine-2,6-dione |
| 356 | 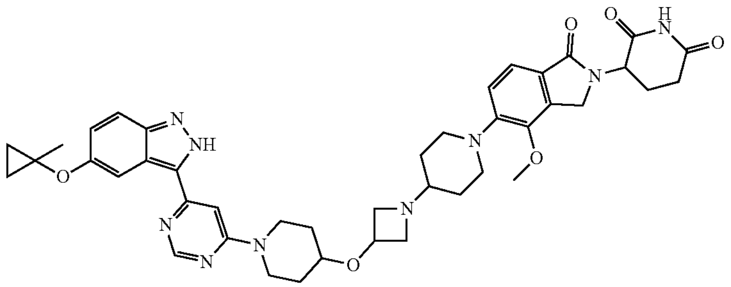 [SMILES: COc1c(N2CCC(N3CC(OC4CCN(c5cc(-c6[nH]nc7ccc(OC8(C)CC8)cc67)ncn5)CC4)C3)CC2)ccc2c1CN(C1CCC(=O)NC1=O)C2=O] | 3-[4-methoxy-5-(4-{3-[(1-{6-[5-(1-methylcyclopropoxy)-2H-indazol-3-yl]pyrimidin-4-yl}piperidin-4-yl)oxy]azetidin-1-yl}piperidin-1-yl)-1-oxo-2,3-dihydro-1H-isoindol-2-yl]piperidine-2,6-dione |
| 357 | 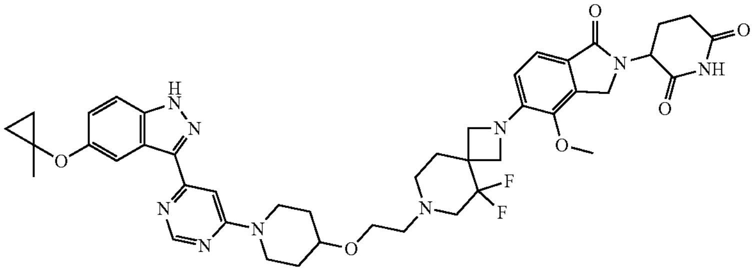 [SMILES: COc1c(N2CC3(CCN(CCOC4CCN(c5cc(-c6n[nH]c7ccc(OC8(C)CC8)cc67)ncn5)CC4)CC3(F)F)C2)ccc2c1CN(C1CCC(=O)NC1=O)C2=O] | 3-[5-(5,5-difluoro-7-{2-[(1-{6-[5-(1-methylcyclopropoxy)-1H-indazol-3-yl]pyrimidin-4-yl}piperidin-4-yl)oxy]ethyl}-2,7-diazaspiro[3.5]nonan-2-yl)-4-methoxy-1-oxo-2,3-dihydro-1H-isoindol-2-yl]piperidine-2,6-dione |
| 358 | 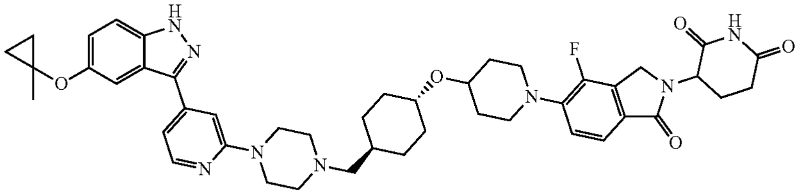 | 3-[4-fluoro-1-oxo-5-(4-{[(1r,4r)-4-[(4-{4-[5-(1-methylcyclopropoxy)-1H-indazol-3-yl]pyridin-2-yl}piperazin-1-yl)methyl]cyclohexyl]oxy}piperidin-1-yl)-2,3-dihydro-1H-isoindol-2-yl]piperidine-2,6-dione |
| 359 | 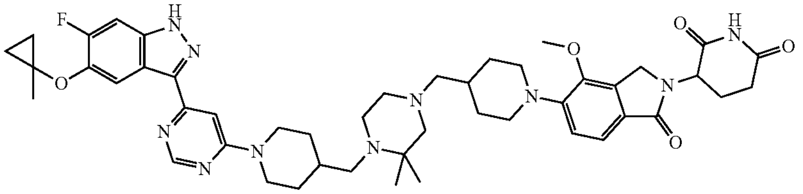 [SMILES: COc1c(N2CCC(CN3CCN(CC4CCN(c5cc(-c6n[nH]c7cc(F)c(OC8(C)CC8)cc67)ncn5)CC4)C(C)(C)C3)CC2)ccc2c1CN(C1CCC(=O)NC1=O)C2=O] | 3-{5-[4-({4-[(1-{6-[6-fluoro-5-(1-methylcyclopropoxy)-1H-indazol-3-yl]pyrimidin-4-yl}piperidin-4-yl)methyl]-3,3-dimethylpiperazin-1-yl}methyl)piperidin-1-yl]-4-methoxy-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 360 | 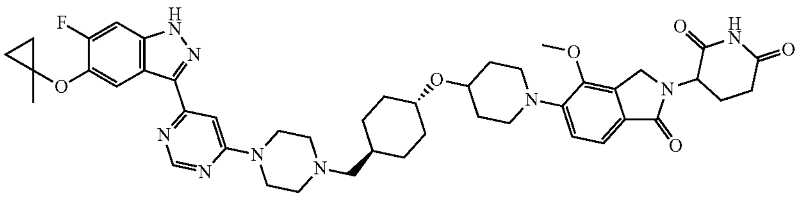 [SMILES: COc1c(N2CCC(O[C@H]3CC[C@H](CN4CCN(c5cc(-c6n[nH]c7cc(F)c(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(4-{6-[6-fluoro-5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 361 | 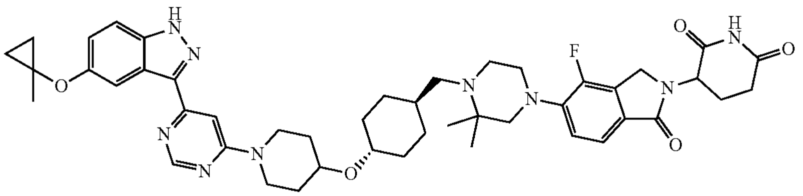 [SMILES: CC1(Oc2ccc3[nH]nc(-c4cc(N5CCC(O[C@H]6CC[C@H](CN7CCN(c8ccc9c(c8F)CN(C8CCC(=O)NC8=O)C9=O)CC7(C)C)CC6)CC5)ncn4)c3c2)CC1] | 3-[5-(3,3-dimethyl-4-{[(1r,4r)-4-[(1-{6-[5-(1-methylcyclopropoxy)-1H-indazol-3-yl]pyrimidin-4-yl}piperidin-4-yl)oxy]cyclohexyl]methyl}piperazin-1-yl)-4-fluoro-1-oxo-2,3-dihydro-1H-isoindol-2-yl]piperidine-2,6-dione |
| 362 | 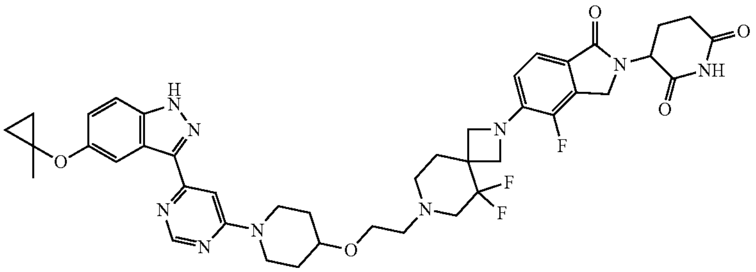 [SMILES: CC1(Oc2ccc3[nH]nc(-c4cc(N5CCC(OCCN6CCC7(CN(c8ccc9c(c8F)CN(C8CCC(=O)NC8=O)C9=O)C7)C(F)(F)C6)CC5)ncn4)c3c2)CC1] | 3-[5-(5,5-difluoro-7-{2-[(1-{6-[5-(1-methylcyclopropoxy)-1H-indazol-3-yl]pyrimidin-4-yl}piperidin-4-yl)oxy]ethyl}-2,7-diazaspiro[3.5]nonan-2-yl)-4-fluoro-1-oxo-2,3-dihydro-1H-isoindol-2-yl]piperidine-2,6-dione |
| 363 | 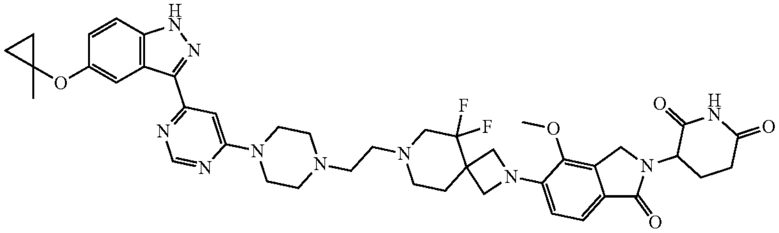 | 3-(5-{5,5-difluoro-7-[2-(4-{6-[5-(1-methylcyclopropoxy)-1H-indazol-3-yl]pyrimidin-4-yl}piperazin-1-yl)ethyl]-2,7-diazaspiro[3.5]nonan-2-yl}-4-methoxy-1-oxo-2,3-dihydro-1H-isoindol-2-yl)piperidine-2,6-dione |
| 364 | 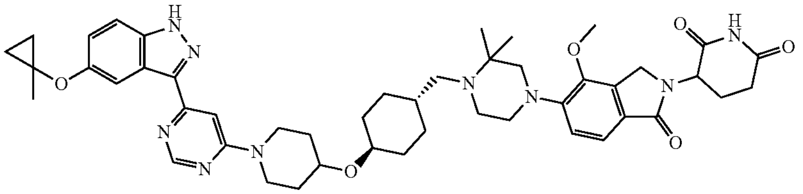 [SMILES: COc1c(N2CCN(C[C@H]3CC[C@H](OC4CCN(c5cc(-c6n[nH]c7ccc(OC8(C)CC8)cc67)ncn5)CC4)CC3)C(C)(C)C2)ccc2c1CN(C1CCC(=O)NC1=O)C2=O] | 3-[5-(3,3-dimethyl-4-{[(1r,4r)-4-[(1-{6-[5-(1-methylcyclopropoxy)-1H-indazol-3-yl]pyrimidin-4-yl}piperidin-4-yl)oxy]cyclohexyl]methyl}piperazin-1-yl)-4-methoxy-1-oxo-2,3-dihydro-1H-isoindol-2-yl]piperidine-2,6-dione |

TABLE 1-continued

| Exemplary bifunctional compounds of the present disclosure** | | |
|---|---|---|
| Ex. No. | Chemical Structure | IUPAC Name |
| 365 | 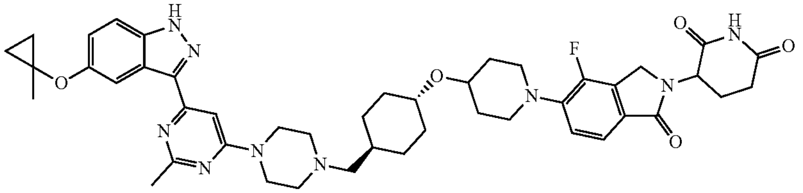 | 3-[4-fluoro-1-oxo-5-(4-{[(1r,4r)-4-[(4-{2-methyl-6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 366 | 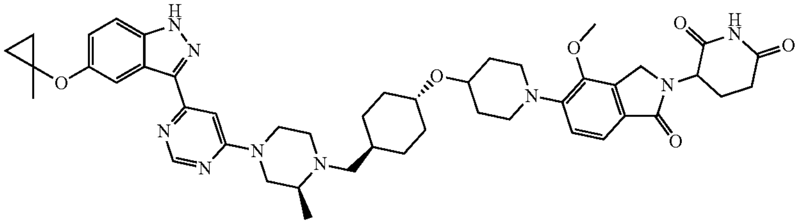 [SMILES: COc1c(N2CCC(O[C@H]3CC[C@H](CN4CCN(c5cc(-c6n[nH]c7ccc(OC8(C)CC8)cc67)ncn5)C[C@@H]4C)CC3)CC2)ccc2c1CN(C1CCC(=O)NC1=O)C2=O] | 3-[4-methoxy-1-oxo-5-(4-{[(1r,4r)-4-{[(2S)-2-methyl-4-{6-[5-(1-methylcyclopropoxy)-1H-indazol-3-yl]pyrimidin-4-yl}piperazin-1-yl]methyl}cyclohexyl]oxy}piperidin-1-yl)-2,3-dihydro-1H-isoindol-2-yl]piperidine-2,6-dione |
| 367 | 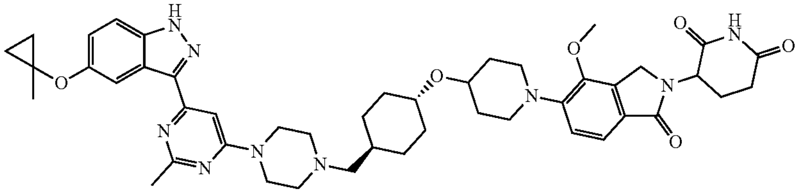 [SMILES: COc1c(N2CCC(O[C@H]3CC[C@H](CN4CCN(c5cc(-c6n[nH]c7ccc(OC8(C)CC8)cc67)nc(C)n5)CC4)CC3)CC2)ccc2c1CN(C1CCC(=O)NC1=O)C2=O] | 3-[4-methoxy-1-oxo-5-(4-{[(1r,4r)-4-[(4-{2-methyl-6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 368 | 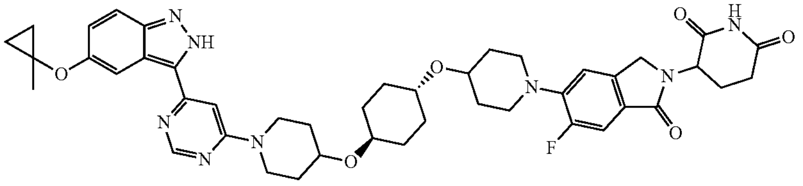 [SMILES: CC1(Oc2ccc3n[nH]c(-c4cc(N5CCC(O[C@H]6CC[C@H](OC7CCN(c8cc9c(cc8F)C(=O)N(C8CCC(=O)NC8=O)C9)CC7)CC6)CC5)ncn4)c3c2)CC1] | 3-[6-fluoro-1-oxo-5-(4-{[(1r,4r)-4-[(1-{6-[5-(1-methylcyclopropoxy)-2H-indazol-3-yl]pyrimidin-4-yl}piperidin-4-yl)oxy]cyclohexyl]oxy}piperidin-1-yl)-2,3-dihydro-1H-isoindol-2-yl]piperidine-2,6-dione |
| 369 | 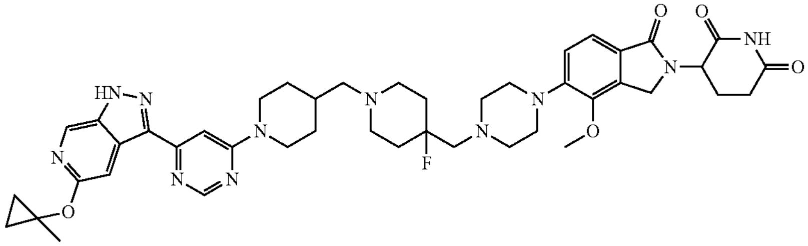 [SMILES: COc1c(N2CCN(CC3(F)CCN(CC4CCN(c5cc(-c6n[nH]c7cnc(OC8(C)CC8)cc67)ncn5)CC4)CC3)CC2)ccc2c1CN(C1CCC(=O)NC1=O)C2=O] | 3-{5-[4-({4-fluoro-1-[(1-{6-[5-(1-methylcyclopropoxy)-1H-pyrazolo[3,4-c]pyridin-3-yl]pyrimidin-4-yl}piperidin-4-yl)methyl]piperidin-4-yl}methyl)piperazin-1-yl]-4-methoxy-1-oxo-2,3-dihydro-1H-isoindol-2-yl}piperidine-2,6-dione |

TABLE 1-continued

| Exemplary bifunctional compounds of the present disclosure** | | |
|---|---|---|
| Ex. No. | Chemical Structure | IUPAC Name |
| 370 | 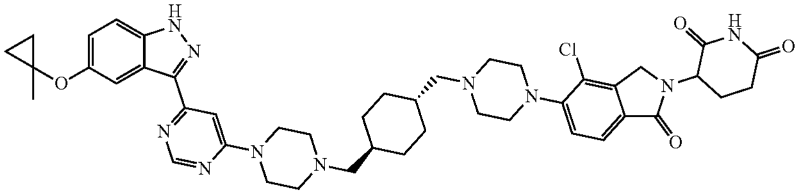 | 3-[4-chloro-1-oxo-5-(4-{[(1r,4r)-4-[(4-{6-[5-(1-methylcyclopropoxy)-1H-indazol-3-yl]pyrimidin-4-yl}piperazin-1-yl)methyl]cyclohexyl]methyl}piperazin-1-yl)-2,3-dihydro-1H-isoindol-2-yl]piperidine-2,6-dione |
| 371 | 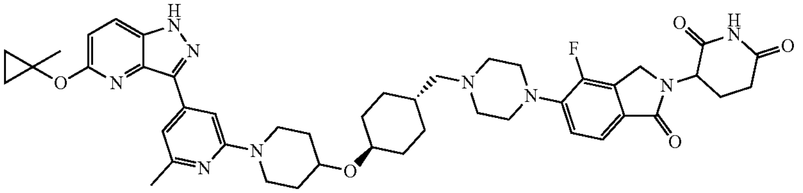 [SMILES: Cc1cc(-c2n[nH]c3ccc(OC4(C)CC4)nc23)cc(N2CCC(O[C@H]3CC[C@H](CN4CCN(c5ccc6c(c5F)CN(C5CCC(=O)NC5=O)C6=O)CC4)CC3)CC2)n1] | 3-[4-fluoro-1-oxo-5-(4-{[(1r,4r)-4-[(1-{6-methyl-4-[5-(1-methylcyclopropoxy)-1H-pyrazolo[4,3-b]pyridin-3-yl]pyridin-2-yl}piperidin-4-yl)oxy]cyclohexyl]methyl}piperazin-1-yl)-2,3-dihydro-1H-isoindol-2-yl]piperidine-2,6-dione |
| 372 | 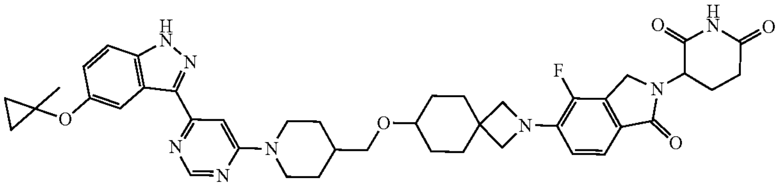 [SMILES: CC1(Oc2ccc3[nH]nc(-c4cc(N5CCC(COC6CCC7(CC6)CN(c6ccc8c(c6F)CN(C6CCC(=O)NC6=O)C8=O)C7)CC5)ncn4)c3c2)CC1] | 3-(4-fluoro-5-{7-[(1-{6-[5-(1-methylcyclopropoxy)-1H-indazol-3-yl]pyrimidin-4-yl}piperidin-4-yl)methoxy]-2-azaspiro[3.5]nonan-2-yl}-1-oxo-2,3-dihydro-1H-isoindol-2-yl)piperidine-2,6-dione |
| 373 | 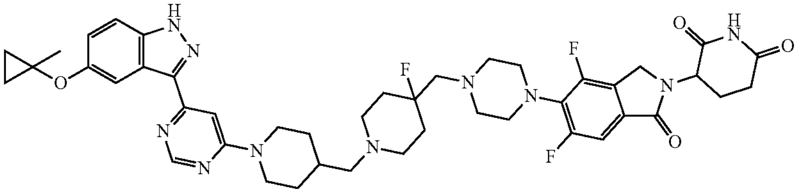 | 3-{4,6-difluoro-5-[4-({4-fluoro-1-[(1-{6-[5-(1-methylcyclopropoxy)-1H-indazol-3-yl]pyrimidin-4-yl}piperidin-4-yl)methyl]piperidin-4-yl}methyl)piperazin-1-yl]-1-oxo-2,3-dihydro-1H-isoindol-2-yl}piperidine-2,6-dione |
| 374 | 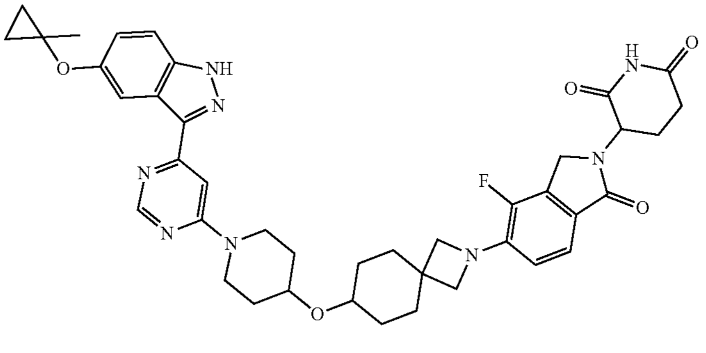 [SMILES: CC1(Oc2ccc3[nH]nc(-c4cc(N5CCC(OC6CCC7(CC6)CN(c6ccc8c(c6F)CN(C6CCC(=O)NC6=O)C8=O)C7)CC5)ncn4)c3c2)CC1] | 3-(4-fluoro-5-{7-[(1-{6-[5-(1-methylcyclopropoxy)-1H-indazol-3-yl]pyrimidin-4-yl}piperidin-4-yl)oxy]-2-azaspiro[3.5]nonan-2-yl}-1-oxo-2,3-dihydro-1H-isoindol-2-yl)piperidine-2,6-dione |

TABLE 1-continued

| Exemplary bifunctional compounds of the present disclosure** | | |
|---|---|---|
| Ex. No. | Chemical Structure | IUPAC Name |
| 375 | 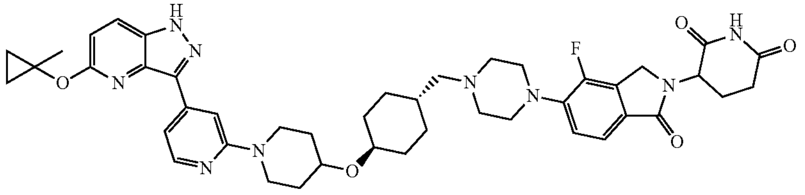 [SMILES: CC1(Oc2ccc3[nH]nc(-c4ccnc(N5CCC(O[C@H]6CC[C@H](CN7CCN(c8ccc9c(c8F)CN(C8CCC(=O)NC8=O)C9=O)CC7)CC6)CC5)c4)c3n2)CC1] | 3-(4-fluoro-5-(4-(((1r,4r)-4-((1-(4-(5-(1-methylcyclopropoxy)-1H-pyrazolo[4,3-b]pyridin-3-yl)pyridin-2-yl)piperidin-4-yl)oxy)cyclohexyl)methyl)piperazin-1-yl)-1-oxoisoindolin-2-yl)piperidine-2,6-dione |
| 376 | 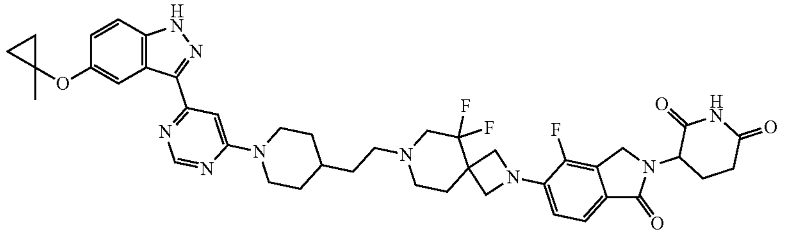 [SMILES: CC1(Oc2ccc3[nH]nc(-c4cc(N5CCC(CCN6CCC7(CN(c8ccc9c(c8F)CN(C8CCC(=O)NC8=O)C9=O)C7)C(F)(F)C6)CC5)ncn4)c3c2)CC1] | 3-(5-{5,5-difluoro-7-[2-(1-{6-[5-(1-methylcyclopropoxy)-1H-indazol-3-yl]pyrimidin-4-yl}piperidin-4-yl)ethyl]-2,7-diazaspiro[3.5]nonan-2-yl}-4-fluoro-1-oxo-2,3-dihydro-1H-isoindol-2-yl)piperidine-2,6-dione |
| 377 | 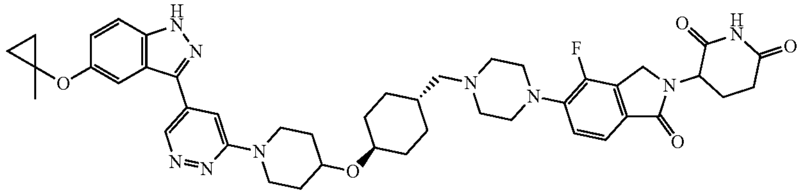 [SMILES: CC1(Oc2ccc3[nH]nc(-c4cnnc(N5CCC(O[C@H]6CC[C@H](CN7CCN(c8ccc9c(c8F)CN(C8CCC(=O)NC8=O)C9=O)CC7)CC6)CC5)c4)c3c2)CC1] | 3-[4-fluoro-1-oxo-5-(4-{[(1r,4r)-4-[(1-{5-[5-(1-methylcyclopropoxy)-1H-indazol-3-yl]pyridazin-3-yl}piperidin-4-yl)oxy]cyclohexyl]methyl}piperazin-1-yl)-2,3-dihydro-1H-isoindol-2-yl]piperidine-2,6-dione |
| 378 | 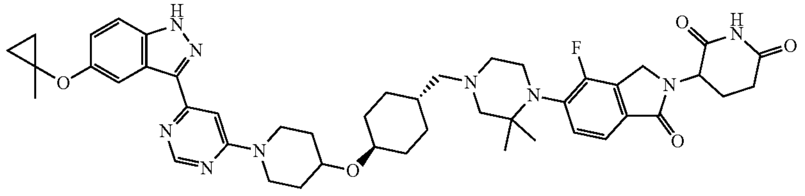 [SMILES: CC1(Oc2ccc3[nH]nc(-c4cc(N5CCC(O[C@H]6CC[C@H](CN7CCN(c8ccc9c(c8F)CN(C8CCC(=O)NC8=O)C9=O)C(C)(C)C7)CC6)CC5)ncn4)c3c2)CC1] | 3-[5-(2,2-dimethyl-4-{[(1r,4r)-4-[(1-{6-[5-(1-methylcyclopropoxy)-1H-indazol-3-yl]pyrimidin-4-yl}piperidin-4-yl)oxy]cyclohexyl]methyl}piperazin-1-yl)-4-fluoro-1-oxo-2,3-dihydro-1H-isoindol-2-yl]piperidine-2,6-dione |
| 379 | 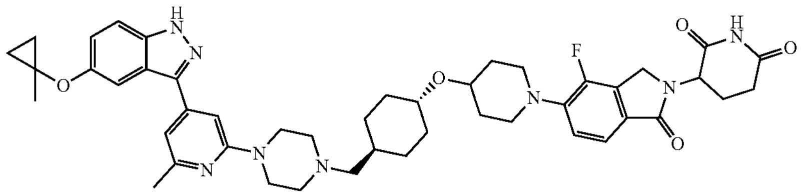 [SMILES: Cc1cc(-c2n[nH]c3ccc(OC4(C)CC4)cc23)cc(N2CCN(C[C@H]3CC[C@H](OC4CCN(c5ccc6c(c5F)CN(C5CCC(=O)NC5=O)C6=O)CC4)CC3)CC2)n1] | 3-[4-fluoro-1-oxo-5-(4-{[(1r,4r)-4-[(4-{6-methyl-4-[5-(1-methylcyclopropoxy)-1H-indazol-3-yl]pyridin-2-yl}piperazin-1-yl)methyl]cyclohexyl]oxy}piperidin-1-yl)-2,3-dihydro-1H-isoindol-2-yl]piperidine-2,6-dione |

TABLE 1-continued

| Ex. No. | Chemical Structure | IUPAC Name |
|---|---|---|
| | Exemplary bifunctional compounds of the present disclosure** | |
| 380 | 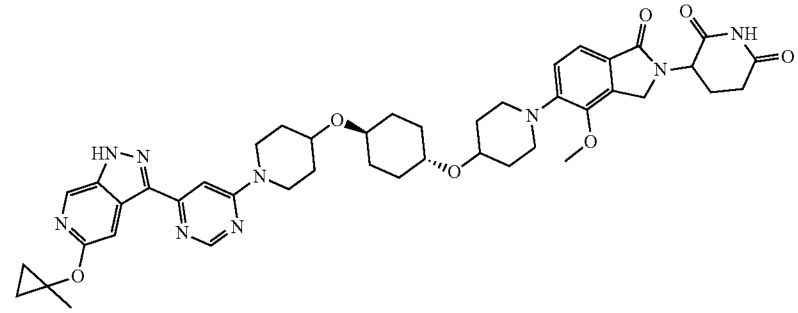 [SMILES: COc1c(N2CCC(O[C@H]3CC[C@H](OC4CCN(c5cc(-c6n[nH]c7cnc(OC8(C)CC8)cc67)ncn5)CC4)CC3)CC2)ccc2c1CN(C1CCC(=O)NC1=O)C2=O] | 3-[4-methoxy-1-oxo-5-(4-{[(1r,4r)-4-[(1-{6-[5-(1-methylcyclopropoxy)-1H-pyrazolo[3,4-c]pyridin-3-yl]pyrimidin-4-yl}piperidin-4-yl)oxy]cyclohexyl]oxy}piperidin-1-yl)-2,3-dihydro-1H-isoindol-2-yl]piperidine-2,6-dione |
| 381 | 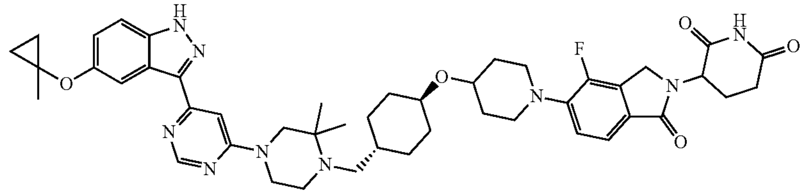 [SMILES: CC1(Oc2ccc3[nH]nc(-c4cc(N5CCN(C[C@H]6CC[C@H](OC7CCN(c8ccc9c(c8F)CN(C8CCC(=O)NC8=O)C9=O)CC7)CC6)C(C)(C)C5)ncn4)c3c2)CC1] | 3-[4-fluoro-1-oxo-5-(4-{[(1r,4r)-4-[(2,2-dimethyl-4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 382 | 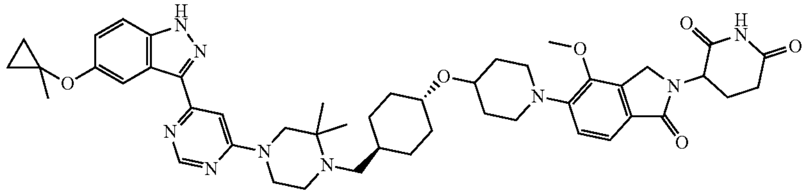 [SMILES: COc1c(N2CCC(O[C@H]3CC[C@H](CN4CCN(c5cc(-c6n[nH]c7ccc(OC8(C)CC8)cc67)ncn5)CC4(C)C)CC3)CC2)ccc2c1CN(C1CCC(=O)NC1=O)C2=O] | 3-[4-methoxy-1-oxo-5-(4-{[(1r,4r)-4-[(2,2-dimethyl-4-{6-[5-(1-methylcyclopropoxy)-1H-indazol-3-yl]pyrimidin-4-yl}piperazin-1-yl)methyl]cyclohexyl]oxy}piperidin-1-yl)-2,3-dihydro-1H-isoindol-2-yl]piperidine-2,6-dione |
| 383 | 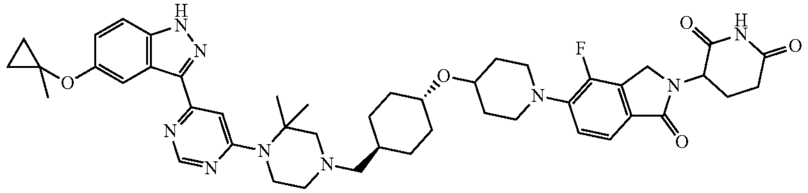 [SMILES: CC1(Oc2ccc3[nH]nc(-c4cc(N5CCN(C[C@H]6CC[C@H](OC7CCN(c8ccc9c(c8F)CN(C8CCC(=O)NC8=O)C9=O)CC7)CC6)CC5(C)C)ncn4)c3c2)CC1] | 3-(5-(4-(((1r,4r)-4-((3,3-dimethyl-4-(6-(5-(1-methylcyclopropoxy)-1H-indazol-3-yl)pyrimidin-4-yl)piperazin-1-yl)methyl)cyclohexyl)oxy)piperidin-1-yl)-4-fluoro-1-oxoisoindolin-2-yl)piperidine-2,6-dione |
| 384 | 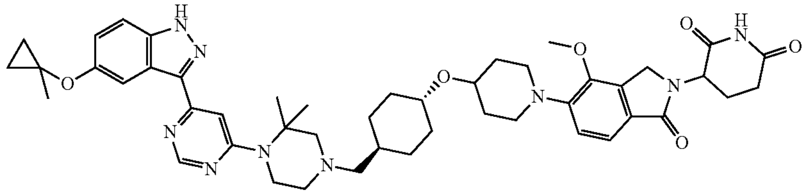 [SMILES: COc1c(N2CCC(O[C@H]3CC[C@H](CN4CCN(c5cc(-c6n[nH]c7ccc(OC8(C)CC8)cc67)ncn5)C(C)(C)C4)CC3)CC2)ccc2c1CN(C1CCC(=O)NC1=O)C2=O] | 3-(5-(4-(((1r,4r)-4-((3,3-dimethyl-4-(6-(5-(1-methylcyclopropoxy)-1H-indazol-3-yl)pyrimidin-4-yl)piperazin-1-yl)methyl)cyclohexyl)oxy)piperidin-1-yl)-4-methoxy-1-oxoisoindolin-2-yl)piperidine-2,6-dione |

**or enantiomers thereof.

TABLE 2

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 52 | $^1$H NMR: 400 MHz, MeOD) δ: 8.67-8.59 (m, 1H), 8.16-8.06 (m, 1H), 7.67 (d, J = 8.6 Hz, 1H), 7.51-7.38 (m, 2H), 7.35 (d, J = 2.0 Hz, 1H), 7.26-7.18 (m, 1H), 7.13-7.05 (m, 1H), 5.08 (d, J = 5.6 Hz, 1H), 4.25-4.17 (m, 2H), 4.11-4.01 (m, 2H), 3.52-3.39 (m, 1H), 3.09-2.89 (m, 9H), 2.89-2.79 (m, 3H), 2.78-2.60 (m, 5H), 2.57-2.48 (m, 1H), 2.15-1.86 (m, 9H), 1.62-1.58 (m, 3H), 1.41-1.35 (m, 2H), 1.24-1.15 (m, 3H), 1.06-0.96 (m, 2H), 0.82-0.72 (m, 2H). | 847.01 (846.43) | 847.6 | A | B | A | B | B | A |
| 53 | $^1$H NMR: E (400 MHz, MeOD) δ: 8.64 (s, 1H), 8.53-8.48 (m, 1H), 8.51 (br s, 1H), 8.11 (s, 1H), 7.46 (d, J = 9.1 Hz, 1H), 7.40 (s, 1H), 7.35 (d, J = 2.1 Hz, 1H), 7.22 (dd, J = 2.3, 8.6 Hz, 1H), 7.09 (dd, J = 2.3, 9.1 Hz, 1H), 5.06 (br dd, J = 5.4, 12.4 Hz, 1H), 4.07 (br d, J = 13.3 Hz, 2H), 3.78 (br s, 4H), 3.02 (br t, J = 11.7 Hz, 3H), 2.92-2.80 (m, 5H), 2.79-2.69 (m, 8H), 2.52 (br s, 1H), 2.61-2.44 (m, 2H), 2.61-2.44 (m, 1H), 2.29 (br s, 4H), 2.14-2.09 (m, 2H), 1.92 (br d, J = 13.1 Hz, 3H), 1.73 (br d, J = 10.6 Hz, 2H), 1.61 (s, 2H), 1.05-0.96 (m, 2H) | 850.9 (850.41)7 | 851.6 | A | B | A | B | N.D. | N.D. |
| 54 | $^1$H NMR: (400 MHz, MeOD) δ: 8.66 (d, J = 0.9 Hz, 1H), 8.11 (d, J = 2.0 Hz, 1H), 7.67 (d, J = 8.6 Hz, 1H), 7.51-7.42 (m, 2H), 7.35 (d, J = 1.5 Hz, 1H), 7.27-7.17 (m, 1H), 7.13 (s, 1H), 5.06 (d, J = 5.3 Hz, 1H), 4.10-4.02 (m, 2H), 3.89-3.81 (m, 4H), 3.25-3.11 (m, 6H), 3.01 (s, 2H), 2.94-2.82 (m, 6H), 2.80-2.69 (m, 6H), 2.54 (d, J = 6.6 Hz, 2H), 2.16-2.07 (m, 1H), 2.02-1.87 (m, 3H), 1.61 (s, 3H), 1.37 (s, 3H), 1.02 (s, 2H), 0.79 (d, J = 1.8 Hz, 2H) | 815.98 (815.42) | 816.6 | A | A | A | A | N.D. | N.D. |
| 55 | $^1$H NMR: (400 MHz, METHANOL-d4) δ: 8.64 (s, 1H), 8.41 (t, J = 0.9 Hz, 1H), 8.12-8.10 (m, 1H), 7.68-7.65 (m, 1H), 7.49-7.45 (m, 1H), 7.44-7.42 (m, 1H), 7.34 (s, 1H), 7.23-7.20 (m, 1H), 7.10 (d, J = 9.1 Hz, 1H), 5.09-5.04 (m, 1H), 4.12-4.01 (m, 4H), 3.54 (br d, J = 10.0 Hz, 1H), 3.14-2.97 (m, 10H), 2.82-2.58 (m, 11H), 2.46-2.39 (m, 2H), 2.14-2.07 (m, 1H), 1.91 (td, J = 1.6, 11.5 Hz, 3H), 1.61 (t, J = 0.9 Hz, 3H), 1.31 (td, J = 1.7, 11.1 Hz, 2H), 1.21 (td, J = 1.0, 6.3 Hz, 3H), 1.05-0.99 (m, 2H), 0.81-0.76 (m, 2H) | 830.01 (829.44) | 830.6 | A | A | A | A | N.D. | N.D. |
| 56 | $^1$H NMR: (400 MHz, METHANOL-$d_4$) δ: 8.65 (d, J = 1.0 Hz, 1H), 8.35 (s, 0.38H), 8.11 (d, J = 2.4 Hz, 1H), 7.68 (d, J = 8.5 Hz, 1H), 7.50-7.42 (m, 2H), 7.36 (d, J = 2.3 Hz, 1H), 7.23 (dd, J = 2.3, 8.6 Hz, 1H), 7.10 (dd, J = 2.3, 9.0 Hz, 1H), 5.10-5.04 (m, 1H), 4.28-4.14 (m, 2H), 4.13-4.03 (m, 2H), 3.75-3.58 (m, 4H), 3.54-3.43 (m, 1H), 3.25-2.94 (m, | 843.99 (843.42) | 844.7 | A | A | A | A | N.D. | N.D. |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | Degradation and characterization of exemplary bifunctional compounds of the present disclosure | | | | | | | | |
| | 6H), 2.92-2.50 (m, 12H), 2.10 (ddt, J = 2.7, 4.9, 7.8 Hz, 1H), 1.88-1.75 (m, 4H), 1.61 (s, 3H), 1.26 (d, J = 6.3 Hz, 3H), 1.06-0.98 (m, 2H), 0.82-0.75 (m, 2H) | | | | | | | | |
| 57 | 1H NMR: (400 MHz, METHANOL-d4) δ: 8.70-8.63 (m, 1H), 8.14-8.09 (m, 1H), 7.71-7.64 (m, 1H), 7.50-7.44 (m, 2H), 7.40-7.34 (m, 1H), 7.27-7.20 (m, 1H), 7.13-7.07 (m, 1H), 5.11-5.03 (m, 1H), 4.58-4.50 (m, 1H), 4.33-4.18 (m, 2H), 4.17-4.03 (m, 3H), 3.49 (br s, 1H), 3.27-3.18 (m, 2H), 3.15-2.98 (m, 5H), 2.96-2.81 (m, 2H), 2.79-2.59 (m, 5H), 2.16-2.06 (m, 1H), 1.94-1.75 (m, 6H), 1.72-1.54 (m, 6H), 1.31-1.15 (m, 5H), 1.07-0.97 (m, 2H), 0.86-0.72 (m, 2H) | 843.00 (842.42) | 843.7 | N.D. | N.D. | N.D. | N.D. | A | A |
| 58 | $^1$H NMR: (400 MHz, $CD_3OD$) δ: 8.68-8.60 (m, 1H), 8.51-8.42 (m, 1H), 8.13-8.07 (m, 1H), 7.75-7.68 (m, 1H), 7.52-7.34 (m, 3H), 7.30-7.22 (m, 1H), 7.13-7.06 (m, 1H), 5.12-5.03 (m, 1H), 4.14-4.01 (m, 2H), 3.87-3.72 (m, 4H), 3.61-3.43 (m, 7H), 3.29-3.22 (m, 1H), 3.18-2.96 (m, 5H), 2.93-2.65 (m, 7H), 2.58-2.49 (m, 1H), 2.17-2.07 (m, 1H), 2.03 (s, 4H), 1.65-1.54 (m, 3H), 1.27-1.16 (m, 3H), 1.06-0.97 (m, 2H), 0.83-0.73 (m, 2H). | 843.99 (843.42) | 844.7 | N.D. | N.D. | N.D. | N.D. | A | B |
| 59 | $^1$H NMR: (400 MHz, METHANOL-$d_4$) δ 8.66-8.64 (m, 1H), 8.20 (s, 2H), 8.11-8.06 (m, 1H), 7.72-7.66 (m, 1H), 7.49-7.42 (m, 2H), 7.40-7.36 (m, 1H), 7.28-7.21 (m, 1H), 7.13-7.07 (m, 1H), 5.08 (dd, J = 5.4, 12.4 Hz, 1H), 4.58-4.49 (m, 1H), 4.28-4.06 (m, 3H), 3.96 (br d, J = 14.5 Hz, 1H), 3.65-3.44 (m, 6H), 3.16-3.07 (m, 2H), 2.96-2.80 (m, 6H), 2.78-2.62 (m, 5H), 2.56-2.49 (m, 2H), 2.16-2.06 (m, 1H), 2.04-1.84 (m, 3H), 1.61 (s, 3H), 1.33-1.23 (m, 4H), 1.19-1.11 (m, 1H), 1.05-0.99 (m, 2H), 0.81-0.76 (m, 2H) | 843.99 (843.42) | 844.7 | N.D. | N.D. | N.D. | N.D. | A | A |
| 60 | $^1$H NMR: (400 MHz, MeOD) δ: 8.64-8.55 (m, 1H), 8.12-8.02 (m, 1H), 7.74-7.64 (m, 1H), 7.52-7.44 (m, 1H), 7.42-7.34 (m, 2H), 7.29-7.20 (m, 1H), 7.13-7.06 (m, 1H), 5.12-5.03 (m, 1H), 4.58 (br s, 2H), 3.54-3.45 (m, 4H), 3.44-3.38 (m, 2H), 3.27-3.20 (m, 1H), 3.10-2.98 (m, 2H), 2.92-2.81 (m, 1H), 2.79-2.63 (m, 6H), 2.37-2.26 (m, 2H), 2.16-2.04 (m, 3H), 1.99-1.83 (m, 5H), 1.67-1.61 (m, 3H), 1.61-1.54 (m, 1H), 1.33-1.19 (m, 4H), 1.09-0.98 (m, 4H), 0.82-0.75 (m, 2H). | 815.98 (815.41) | 816.7 | N.D. | N.D. | N.D. | N.D. | A | A |
| 61 | $^1$H NMR: (400 MHz, METHANOL-$d_4$) δ: 8.61 (s, 1H), 8.46 (s, 1H), 8.08 (d, J = 2.0 Hz, 1H), 7.67 (d, J = 8.6 Hz, 1H), 7.47 (d, J = 9.0 Hz, 1H), 7.41-7.33 (m, 2H), 7.23 (dd, J = 2.3, 8.7 Hz, 1H), | 815.98 (815.41) | 816.7 | A | A | A | A | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 7.10 (dd, J = 2.3, 9.0 Hz, 1H), 5.07 (dd, J = 5.4, 12.4 Hz, 1H), 4.63-4.54 (m, 4H), 4.07 (br d, J = 13.4 Hz, 2H), 3.68-3.53 (m, 1H), 3.41 (d, J = 6.0 Hz, 2H), 3.20 (br d, J = 8.1 Hz, 2H), 3.10-2.98 (m, 5H), 2.93-2.80 (m, 3H), 2.79-2.65 (m, 2H), 2.07-1.85 (m, 9H), 1.61 (s, 3H), 1.47-1.26 (m, 5H), 1.11-0.95 (m, 2H), 0.86-0.71 (m, 2H) | | | | | | | | |
| 62 | $^1H$ NMR: (400 MHz, METHANOL-$d_4$) δ: 8.62 (d, J = 0.8 Hz, 1H), 8.42 (s, 1H), 8.09 (d, J = 1.9 Hz, 1H), 7.69 (d, J = 8.5 Hz, 1H), 7.48 (d, J = 9.1 Hz, 1H), 7.41 (s, 1H), 7.37 (d, J = 2.1 Hz, 1H), 7.23 (br d, J = 2.4 Hz, 1H), 7.11 (dd, J = 2.3, 9.1 Hz, 1H), 5.08 (dd, J = 5.4, 12.6 Hz, 1H), 4.59 (br s, 2H), 4.08 (br d, J = 13.1 Hz, 2H), 3.93-3.81 (m, 2H), 3.62 (tt, J = 3.5, 7.2 Hz, 1H), 3.52-3.39 (m, 4H), 3.13-3.00 (m, 5H), 2.94-2.83 (m, 1H), 2.80-2.67 (m, 2H), 2.12 (tdd, J = 2.6, 5.3, 12.6 Hz, 1H), 1.96-1.80 (m, 8H), 1.69-1.55 (m, 5H), 1.38-1.30 (m, 3H), 1.06-1.02 (m, 2H), 0.82-0.78 (m, 2H) | 829.96 (829.39) | 830.6 | N.D. | N.D. | N.D. | N.D. | A | A |
| 63 | $^1H$ NMR: (400 MHz, $CD_3OD$) δ: 8.60 (s, 1H), 8.26 (s, 1H), 8.04 (s, 1H), 7.66 (d, J = 8.5 Hz, 1H), 7.47 (d, J = 9.1 Hz, 1H), 7.39 (s, 1H), 7.34 (d, J = 2.3 Hz, 1H), 7.21 (dd, J = 2.4, 8.6 Hz, 1H), 7.10 (dd, J = 2.3, 9.1 Hz, 1H), 5.06 (dd, J = 5.4, 12.6 Hz, 1H), 4.04 (br d, J = 12.9 Hz, 2H), 3.26-3.13 (m, 5H), 3.11-2.81 (m, 11H), 2.79-2.66 (m, 2H), 2.39 (d, J = 7.0 Hz, 1H), 2.42-2.35 (m, 1H), 2.15-2.06 (m, 1H), 2.02-1.78 (m, 1H), 2.02-1.78 (m, 5H), 1.61 (s, 3H), 1.36-1.20 (m, 5H), 1.04-0.99 (m, 2H), 0.81-0.76 (m, 2H) | 849.02 (848.38) | 849.6 | A | A | A | A | N.D. | N.D. |
| 64 | 1H NMR: (400 MHz, MeOD) δ: 8.64 (s, 1H), 8.11 (d, J = 2.1 Hz, 1H), 7.62 (d, J = 8.5 Hz, 1H), 7.47 (d, J = 9.1 Hz, 1H), 7.43 (s, 1H), 7.13-7.05 (m, 3H), 5.09 (dd, J = 5.1, 13.3 Hz, 1H), 4.48-4.31 (m, 2H), 4.29-4.14 (m, 2H), 3.95 (d, J = 12.9 Hz, 2H), 3.44 (s, 1H), 3.35 (d, J = 11.9 Hz, 2H), 3.21-3.11 (m, 1H), 3.11-2.97 (m, 4H), 2.95-2.83 (m, 5H), 2.77 (td, J = 2.3, 15.5 Hz, 3H), 2.59-2.38 (m, 2H), 2.21-1.85 (m, 10H), 1.61 (s, 3H), 1.49-1.33 (m, 2H), 1.22 (d, J = 6.4 Hz, 3H), 1.08-0.96 (m, 2H), 0.85-0.72 (m, 2H). | 833.03 (832.45) | 833.7 | A | A | A | A | A | A |
| 65 | 1H NMR: (400 MHz, MeOD) δ: 8.66 (s, 1H), 8.40 (s, 1H), 8.13 (d, J = 2.1 Hz, 1H), 7.64 (br d, J = 8.6 Hz, 1H), 7.50-7.42 (m, 2H), 7.14-7.05 (m, 3H), 5.12 (br dd, J = 5.1, 13.3 Hz, 1H), 4.42-4.35 (m, 2H), 4.17-4.09 (m, 2H), 3.99-3.92 (m, 2H), 3.59-3.47 (m, 1H), 3.09 (br s, 8H), 2.94-2.77 (m, 9H), 2.72-2.67 (m, 1H), 2.62-2.57 (m, 1H), 2.49 (br s, 3H), 2.21-2.13 (m, 1H), 1.91 (br d, J = 11.9 Hz, 3H), 1.63 (s, 3H), 1.42-1.28 | 816.02 (815.46) | 816.7 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 3H), 1.23 (br d, J = 6.3 Hz, 3H), 1.06-1.01 (m, 2H), 0.83-0.77 (m, 2H) | | | | | | | | |
| 66 | 1H NMR: (400 MHz, CD3OD) δ: 8.64 (s, 1H), 8.38 (s, 1H), 8.11 (d, J = 2.0 Hz, 1H), 7.61 (d, J = 8.8 Hz, 1H), 7.48-7.37 (m, 2H), 7.15-7.01 (m, 3H), 5.09 (dd, J = 5.1, 13.3 Hz, 1H), 4.44-4.32 (m, 2H), 3.98-3.88 (m, 2H), 3.80 (br d, J = 4.5 Hz, 4H), 3.17-2.99 (m, 6H), 2.91-2.66 (m, 14H), 2.52-2.36 (m, 3H), 2.20-2.09 (m, 1H), 1.96-1.81 (m, 3H), 1.60 (s, 3H), 1.38-1.29 (m, 2H), 1.05-0.95 (m, 2H), 0.81-0.73 (m, 2H) | 802.00 (801.44) | 802.7 | N.D. | N.D. | N.D. | N.D. | A | A |
| 67 | 1H NMR:(400 MHz, DMSO) δ: 13.37 (s, 1H), 11.08 (s, 1H), 8.62 (s, 1H), 8.15 (d, J = 2.1 Hz, 1H), 7.67 (d, J = 8.5 Hz, 1H), 7.50 (d, J = 9.0 Hz, 1H), 7.35 (d, J = 15.4 Hz, 2H), 7.28-7.21 (m, 1H), 7.06 (dd, J = 2.4, 9.0 Hz, 1H), 5.07 (dd, J = 5.4, 12.9 Hz, 1H), 4.44 (d, J = 9.6 Hz, 2H), 3.46-3.40 (m, 4H), 3.02-2.81 (m, 5H), 2.64-2.55 (m, 2H), 2.46 (s, 4H), 2.17 (d, J = 6.1 Hz, 4H), 2.06-1.64 (m, 9H), 1.54 (s, 3H), 1.22-1.02 (m, 4H), 0.98-0.91 (m, 2H), 0.80-0.74 (m, 2H). | 800.97 (800.41) | 801.3 | A | A | A | A | N.D. | N.D. |
| 68 | 1H NMR: (400 MHz, MeOD-d4) δ: 8.61 (s, 1H), 8.42 (s, 1H), 8.07 (s, 1H), 7.66 (d, J = 8.6 Hz, 1H), 7.46 (d, J = 8.9 Hz, 1H), 7.39 (s, 1H), 7.34 (d, J = 2.1 Hz, 1H), 7.22 (dd, J = 2.3, 8.3 Hz, 1H), 7.09 (dd, J = 2.3, 9.0 Hz, 1H), 5.06 (dd, J = 5.4, 12.5 Hz, 1H), 4.56 (br s, 5H), 4.06 (br d, J = 12.6 Hz, 2H), 3.09-2.94 (m, 5H), 2.89-2.81 (m, 5H), 2.78-2.68 (m, 3H), 2.54 (br s, 4H), 2.15-2.05 (m, 1H), 1.92 (br d, J = 13.9 Hz, 5H), 1.60 (s, 3H), 1.40-1.25 (m, 4H), 1.04-0.99 (m, 2H), 0.81-0.75 (m, 2H) | 800.97 (800.41) | 801.5 | A | A | A | A | A | A |
| 69 | 1H NMR: (400 MHz, MeOD) δ: 8.62 (s, 1H), 8.10 (s, 1H), 7.67 (d, J = 8.4 Hz, 1H), 7.47 (d, J = 9.0 Hz, 1H), 7.37 (d, J = 11.4 Hz, 2H), 7.23 (d, J = 8.3 Hz, 1H), 7.14-7.04 (m, 1H), 5.13-5.02 (m, 1H), 4.08 (d, J = 12.5 Hz, 2H), 4.04-3.91 (m, 2H), 3.63-3.52 (m, 1H), 3.12 (d, J = 11.0 Hz, 2H), 3.02 (q, J = 13.5 Hz, 4H), 2.93-2.82 (m, 5H), 2.80-2.65 (m, 4H), 2.61-2.52 (m, 2H), 2.28 (s, 1H), 2.12 (s, 3H), 2.05-1.87 (m, 4H), 1.61 (s, 3H), 1.48-1.34 (m, 2H), 1.13 (d, J = 6.1 Hz, 3H), 1.02 (s, 2H), 0.82-0.74 (m, 2H). | 832.98 (832.42) | 833.6 | A | C | A | C | A | B |
| 70 | δ: 8.64 (s, 1H), 8.10 (d, J = 2.1 Hz, 1H), 7.70 (d, J = 8.5 Hz, 1H), 7.44-7.38 (m, 3H), 7.28 (dd, J = 2.1, 8.6 Hz, 1H), 7.10 (dd, J = 2.3, 9.1 Hz, 1H), 5.09-4.99 (m, 1H), 4.14 (d, J = 11.5 Hz, 2H), 3.92 (d, J = 13.3 Hz, 2H), 3.56-3.46 (m, 1H), 3.39-3.33 (m, 4H), 3.27-3.19 (m, 2H), 3.15 (d, J = 12.8 Hz, 1H), 3.05-2.93 (m, 2H), 2.90-2.66 (m, 6H), 2.53 (s, 2H), 2.33 (d, J = 13.1 Hz, 1H), 2.16-2.01 (m, 3H), 1.97-1.71 (m, 4H), 1.61 (s, 3H), 1.48- | 832.98 (832.42) | 833.6 | A | C | A | C | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1.35 (m, 2H), 1.21 (d, J = 6.3 Hz, 3H), 1.05-0.96 (m, 2H), 0.82-0.75 (m, 2H). | | | | | | | | |
| 71 | 1H NMR: (400 MHz, MeOD-d4) δ: 8.65-8.61 (m, 1H), 8.36-8.31 (m, 1H), 7.71-7.66 (m, 1H), 7.43-7.39 (m, 1H), 7.38-7.35 (m, 1H), 7.32-7.27 (m, 1H), 7.27-7.21 (m, 1H), 5.11-5.04 (m, 1H), 4.13-4.06 (m, 4H), 3.52-3.42 (m, 3H), 3.20-3.14 (m, 1H), 3.08-2.96 (m, 4H), 2.94-2.77 (m, 8H), 2.40-2.31 (m, 1H), 2.20-2.10 (m, 4H), 2.02-1.86 (m, 4H), 1.67-1.61 (m, 3H), 1.52-1.43 (m, 4H), 1.17-1.12 (m, 3H), 1.10-1.05 (m, 2H), 0.84-0.79 (m, 2H). | 832.98 (832.42) | 833.6 | A | C | A | B | N.D. | N.D. |
| 72 | 1H NMR: (400 MHz, MeOD-d4) δ: 8.63-8.59 (m, 1H), 8.17-8.12 (m, 1H), 7.71-7.66 (m, 1H), 7.49-7.45 (m, 1H), 7.41 (s, 1H), 7.38-7.35 (m, 1H), 7.26-7.21 (m, 1H), 7.14-7.07 (m, 1H), 5.11-5.03 (m, 1H), 4.14-4.06 (m, 4H), 3.92-3.86 (m, 1H), 3.51-3.43 (m, 3H), 3.20-3.12 (m, 1H), 3.09-2.97 (m, 3H), 2.92-2.62 (m, 8H), 2.60-2.54 (m, 1H), 2.39-2.31 (m, 1H), 2.21-2.09 (m, 4H), 1.99-1.86 (m, 4H), 1.54-1.38 (m, 4H), 1.17-1.12 (m, 2H), 0.86-0.81 (m, 2H), 0.77-0.72 (m, 2H). | 800.97 (800.41) | 801.6 | B | B | B | B | N.D. | N.D. |
| 73 | 1H NMR: (400 MHz, MeOD-d4) δ: 8.71 (s, 1H), 8.46 (s, 1H), 8.19 (d, J = 2.0 Hz, 1H), 7.68-7.53 (m, 3H), 7.49 (s, 1H), 7.19 (dd, J = 2.1, 9.0 Hz, 1H), 5.19 (dd, J = 5.4, 12.4 Hz, 1H), 4.28-4.11 (m, 2H), 3.80 (br d, J = 12.5 Hz, 2H), 3.70 (br d, J = 8.4 Hz, 2H), 3.61-3.50 (m, 1H), 3.33-2.71 (m, 12H), 2.72-2.62 (m, 1H), 2.45 (br t, J = 9.1 Hz, 1H), 2.29 (br dd, J = 5.0, 12.8 Hz, 2H), 2.35-2.25 (m, 2H), 2.25-2.17 (m, 1H), 2.03 (br d, J = 11.5 Hz, 3H), 1.70 (s, 3H), 1.67-1.50 (m, 4H), 1.41-1.35 (m, 1H), 1.24 (d, J = 6.1 Hz, 3H), 1.14-1.08 (m, 2H), 0.90-0.84 (m, 1H) | 832.98 (832.42) | 833.7 | A | C | A | C | N.D. | N.D. |
| 74 | 1H NMR: (400 MHz, MeOD-d4) δ: 8.62 (s, 1H), 8.40 (s, 1H), 8.11 (d, J = 1.9 Hz, 1H), 7.65 (d, J = 8.5 Hz, 1H), 7.47 (d, J = 9.0 Hz, 1H), 7.32 (d, J = 2.4 Hz, 1H), 7.22-7.17 (m, 1H), 7.15 (s, 1H), 7.10 (dd, J = 2.4, 9.0 Hz, 1H), 5.10-5.02 (m, 1H), 4.03 (br d, J = 13.0 Hz, 2H), 3.76 (br d, J = 7.9 Hz, 4H), 2.98 (br t, J = 11.9 Hz, 5H), 2.90-2.64 (m, 10H), 2.43 (br s, 2H), 2.13-2.04 (m, 3H), 1.88 (br d, J = 10.6 Hz, 3H), 1.61 (s, 3H), 1.34-1.27 (m, 3H), 1.04-1.00 (m, 2H), 0.81-0.77 (m, 2H) | 798.95 (798.40) | 799.6 | C | C | C | B | N.D. | N.D. |
| 75 | 1H NMR: (400 MHz, MeOD-d4) δ: 8.60 (d, J = 1.1 Hz, 1H), 8.52 (br s, 0.45H), 8.14-8.10 (m, 1H), 7.68 (d, J = 8.5 Hz, 1H), 7.48 (d, J = 9.3 Hz, 1H), 7.37-7.34 (m, 1H), 7.23 (d, J = 8.2 Hz, 1H), 7.17-7.09 (m, 2H), 5.11-5.05 (m, 1H), 4.07 (td, J = 1.6, 12.9 Hz, 2H), 4.01-3.78 (m, 2H), 3.68-3.61 | 798.95 (798.40) | 799.6 | A | A | A | A | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 2H), 3.07-2.82 (m, 7H), 2.80-2.62 (m, 7H), 2.40-2.33 (m, 2H), 2.16-2.08 (m, 1H), 1.93 (td, J = 1.8, 11.7 Hz, 3H), 1.85-1.78 (m, 2H), 1.62 (t, J = 0.9 Hz, 3H), 1.32 (td, J = 1.5, 11.7 Hz, 3H), 1.06-1.00 (m, 2H), 0.96-0.86 (m, 1H), 0.84-0.77 (m, 2H) | | | | | | | | |
| 76 | 1H NMR: (400 MHz, MeOD-d4) δ: 8.64 (d, J = 1.0 Hz, 1H), 8.43 (s, 1H), 8.11 (d, J = 2.0 Hz, 1H), 7.69 (d, J = 8.5 Hz, 1H), 7.47 (d, J = 9.0 Hz, 1H), 7.41 (s, 1H), 7.38 (d, J = 2.3 Hz, 1H), 7.25 (dd, J = 2.3, 8.6 Hz, 1H), 7.10 (dd, J = 2.3, 9.1 Hz, 1H), 5.08 (dd, J = 5.4, 12.4 Hz, 1H), 4.11 (br d, J = 13.3 Hz, 2H), 3.78 (br s, 4H), 3.57 (br s, 2H), 3.11-2.96 (m, 5H), 2.95-2.81 (m, 2H), 2.79-2.69 (m, 2H), 2.59 (br t, J = 4.9 Hz, 4H), 2.35 (br d, J = 7.0 Hz, 2H), 2.18 (br s, 1H), 2.14-2.04 (m, 3H), 1.92 (br d, J = 12.1 Hz, 3H), 1.61 (s, 3H), 1.56-1.36 (m, 4H), 1.04-0.99 (m, 2H), 0.81-0.75 (m, 2H) | 800.97 (800.41) | 801.7 | A | B | A | C | N.D. | N.D. |
| 77 | 1H NMR: (400 MHz, MeOD-d4) δ: 8.62 (d, J = 0.8 Hz, 1H), 8.32 (d, J = 8.1 Hz, 1H), 7.67 (d, J = 8.5 Hz, 1H), 7.43-7.33 (m, 2H), 7.29 (d, J = 10.5 Hz, 1H), 7.25-7.19 (m, 1H), 5.11-5.04 (m, 1H), 4.62 -4.52 (m, 2H), 4.11-4.02 (m, 2H), 3.14-2.82 (m, 13H), 2.63 (d, J = 6.1 Hz, 6H), 2.15-1.98 (m, 3H), 1.92 (d, J = 13.1 Hz, 4H), 1.64 (s, 3H), 1.42-1.22 (m, 4H), 1.07 (s, 2H), 0.81 (d, J = 1.6 Hz, 2H). | 818.96 (818.40) | 819.7 | A | C | A | B | A | B |
| 78 | 1H NMR: (400 MHz, MeOD-d4) δ: 8.38 (s, 1H), 8.23 (d, J = 5.5 Hz, 1H), 7.69 (d, J = 8.5 Hz, 1H), 7.61 (d, J = 1.8 Hz, 1H), 7.53 (d, J = 9.0 Hz, 1H), 7.39-7.33 (m, 2H), 7.27-7.20 (m, 2H), 7.15 (dd, J = 2.2, 9.1 Hz, 1H), 5.09 (br dd, J = 5.5, 12.5 Hz, 1H), 4.45-4.37 (m, 2H), 4.13-4.05 (m, 2H), 3.10-2.96 (m, 8H), 2.89 (ddd, J = 5.2, 14.1, 17.6 Hz, 4H), 2.80-2.70 (m, 5H), 2.62 (br s, 2H), 2.17-2.01 (m, 2H), 1.94 (br d, J = 14.0 Hz, 4H), 1.62 (s, 3H), 1.47-1.22 (m, 5H), 1.09-1.01 (m, 2H), 0.85-0.77 (m, 2H) | 799.98 (799.42) | 800.6 | A | B | A | B | N.D. | N.D. |
| 79 | 1H NMR: (400 MHz, MeOD-d4) δ: 8.65 (d, J = 1.0 Hz, 1H), 8.41 (s, 1H), 8.12 (d, J = 2.0 Hz, 1H), 7.70 (d, J = 8.6 Hz, 1H), 7.48 (d, J = 9.0 Hz, 1H), 7.42 (s, 1H), 7.38 (d, J = 2.3 Hz, 1H), 7.26 (dd, J = 2.4, 8.6 Hz, 1H), 7.11 (dd, J = 2.3, 9.0 Hz, 1H), 5.09 (dd, J = 5.4, 12.6 Hz, 1H), 4.11 (br d, J = 13.3 Hz, 2H), 3.79 (br s, 4H), 3.28 (br d, J = 9.8 Hz, 2H), 3.06 (br t, J = 11.7 Hz, 2H), 3.01-2.91 (m, 2H), 2.90-2.81 (m, 3H), 2.81-2.62 (m, 9H), 2.27-2.09 (m, 4H), 1.95 (br d, J = 13.6 Hz, 3H), 1.63 (s, 3H), 1.49-1.36 (m, 2H), 1.06-0.99 (m, 2H), 0.83-0.76 (m, 2H) | 818.96 (818.40) | 819.7 | A | B | A | C | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 80 | 1H NMR: (400 MHz, MeOD-d4) δ: 8.23 (d, J = 5.5 Hz, 1H), 7.67 (d, J = 8.6 Hz, 1H), 7.59 (d, J = 1.8 Hz, 1H), 7.51 (d, J = 9.0 Hz, 1H), 7.38-7.29 (m, 2H), 7.26-7.20 (m, 2H), 7.15-7.11 (m, 1H), 5.11-5.04 (m, 1H), 4.08 (d, J = 13.3 Hz, 2H), 3.68-3.57 (m, 4H), 3.39 -3.33 (m, 2H), 3.03 (t, J = 12.4 Hz, 4H), 2.91 (d, J = 7.0 Hz, 2H), 2.88-2.82 (m, 1H), 2.79-2.64 (m, 8H), 2.27-2.19 (m, 2H), 2.16-2.03 (m, 3H), 1.94 (d, J = 13.5 Hz, 3H), 1.60 (s, 3H), 1.46-1.34 (m, 2H), 1.07-1.00 (m, 2H), 0.82-0.76 (m, 2H). | 817.97 (817.41) | 818.6 | A | B | A | C | N.D. | N.D. |
| 81 | 1H NMR: (400 MHz, MeOD-d4) δ 8.47-8.46 (m, 1H), 8.21 (d, J = 5.3 Hz, 1H), 7.67 (d, J = 8.5 Hz, 1H), 7.58 (d, J = 2.0 Hz, 1H), 7.50 (d, J = 9.0 Hz, 1H), 7.35 (d, J = 2.1 Hz, 1H), 7.30 (s, 1H), 7.24-7.20 (m, 2H), 7.12 (dd, J = 2.2, 9.1 Hz, 1H), 5.11-5.03 (m, 1H), 4.11 -4.03 (m, 2H), 3.94-3.81 (m, 2H), 3.40-3.33 (m, 1H), 3.29-3.20 (m, 2H), 3.19-3.13 (m, 1H), 3.09-2.98 (m, 3H), 2.97-2.84 (m, 4H), 2.83-2.75 (m, 3H), 2.74-2.66 (m, 2H), 2.49 (s, 2H), 2.31-2.22 (m, 1H), 2.15-2.05 (m, 3H), 1.84 (br s, 4H), 1.60 (s, 3H), 1.44-1.34 (m, 2H), 1.16 (d, J = 6.1 Hz, 3H), 1.06-1.01 (m, 2H), 0.81-0.76 (m, 2H) | 831.99 (831.42) | 832.4 | A | C | A | C | N.D. | N.D. |
| 82 | 1H NMR: (400 MHz, MeOD-d4) δ: 8.49 (s, 1H), 8.23 (d, J = 5.3 Hz, 1H), 7.70 (d, J = 8.6 Hz, 1H), 7.61 (d, J = 2.0 Hz, 1H), 7.52 (d, J = 9.1 Hz, 1H), 7.39-7.34 (m, 2H), 7.28-7.20 (m, 2H), 7.15 (dd, J = 2.2, 9.1 Hz, 1H), 5.09 (dd, J = 5.4, 12.6 Hz, 1H), 4.42 (br d, J = 13.0 Hz, 2H), 3.52-3.44 (m, 4H), 3.20 (br s, 2H), 3.08-2.99 (m, 2H), 2.94-2.83 (m, 3H), 2.81-2.68 (m, 9H), 2.64 (s, 1H), 2.23-2.07 (m, 4H), 2.02-1.85 (m, 4H), 1.62 (s, 3H), 1.47-1.34 (m, 2H), 1.08-1.02 (m, 2H), 0.84-0.78 (m, 2H) | 817.97 (817.41) | 818.6 | B | B | B | B | N.D. | N.D. |
| 83 | 1H NMR: (400 MHz, MeOD-d4) δ: 8.62 (s, 1H), 8.44 (s, 1H), 8.08 (d, J = 2.0 Hz, 1H), 7.68 (d, J = 8.5 Hz, 1H), 7.47 (d, J = 9.0 Hz, 1H), 7.41 (s, 1H), 7.35 (d, J = 2.0 Hz, 1H), 7.22 (dd, J = 2.1, 8.6 Hz, 1H), 7.09 (dd, J = 2.3, 9.1 Hz, 1H), 5.07 (dd, J = 5.4, 12.6 Hz, 1H), 4.60 (br d, J = 12.6 Hz, 2H), 3.50-3.43 (m, 4H), 3.30-3.24 (m, 2H), 3.06 (br t, J = 12.1 Hz, 2H), 3.00-2.89 (m, 2H), 2.89-2.80 (m, 3H), 2.79-2.70 (m, 6H), 2.69-2.62 (m, 2H), 2.25-2.13 (m, 3H), 2.12-1.97 (m, 2H), 1.93 (br d, J = 13.4 Hz, 3H), 1.61 (s, 3H), 1.36-1.26 (m, 2H), 1.05-0.98 (m, 2H), 0.82 -0.74 (m, 2H) | 818.96 (818.40) | 819.7 | A | A | A | B | N.D. | N.D. |
| 84 | 1H NMR: (400 MHz, MeOD-d4) δ 8.73-8.63 (m, 1H), 8.52-8.45 (m, 1H), 8.18-8.09 (m, 1H), 7.73-7.63 (m, 1H), 7.51-7.43 (m, 2H), 7.39-7.33 (m, 1H), 7.28-7.19 (m, 1H), 7.13-7.03 (m, 1H), | 814.95 (814.39) | 815.3 | A | C | A | B | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 5.09 (br d, J = 5.1 Hz, 1H), 4.13-4.05 (m, 2H), 3.88 (br d, J = 1.5 Hz, 2H), 3.79 (br s, 4H), 3.47-3.38 (m, 2H), 3.04 (br t, J = 12.2-Hz, 4H), 2.84-2.68 (m, 6H), 2.10 1.91 (m, 7H), 1.61 (s, 3H), 1.46-1.23 (m, 5H), 1.02 (br s, 2H), 0.82-0.76 (m, 2H) | | | | | | | | |
| 85 | 1H NMR: (400 MHz, DMSO-d6) δ: 13.35 (br s, 1 H), 11.08 (s, 1 H), 8.25 (d, J = 5.25 Hz, 1 H), 8.14-8.19 (m, 1 H), 7.64 (d, J = 8.50 Hz, 1 H), 7.51-7.56 (m, 2 H), 7.30 (s, 1 H), 7.27 (s, 1 H), 7.18-7.24 (m, 2 H), 7.07-7.12 (m, 1 H), 5.06 (dd, J = 12.88, 5.38 Hz, 1 H), 4.03 (br d, J = 12.38 Hz, 2 H), 3.64 (br s, 8 H), 2.80-3.01 (m, 5 H), 2.54-2.68 (m, 3 H), 2.15 (br d, J = 6.38 Hz, 2 H), 1.93-2.03 (m, 3 H), 1.78 (br d, J = 12.13 Hz, 3 H), 1.62 (br d, J = 1.75 Hz, 4 H), 1.54 (s, 3 H), 1.13 (q, J = 10.38 Hz, 2 H), 0.96-1.03 (m, 2 H), 0.75-0.81 (m, 2 H). | 813.96 (813.40) | 814.6 | A | C | A | C | N.D. | N.D. |
| 86 | 1H NMR: (400 MHz, DMSO-d6) δ: 13.40 (br s, 1 H), 11.10 (s, 1 H), 8.65 (d, J = 0.63 Hz, 1 H), 8.16 (d, J = 1.88 Hz, 1 H), 8.14 (s, 1 H), 7.69 (d, J = 8.50 Hz, 1 H), 7.51 (d, J = 9.01 Hz, 1 H), 7.40 (s, 1 H), 7.35 (s, 1 H), 7.26 (br d, J = 8.50 Hz, 1 H), 7.07 (dd, J = 8.94, 2.31 Hz, 1 H), 5.08 (dd, J = 12.88, 5.38 Hz, 1 H), 4.35-4.50 (m, 3 H), 4.04 (br d, J = 12.26 Hz, 1 H), 3.43-3.46 (m, 7 H), 2.98-3.12 (m, 5 H), 2.86-2.93 (m, 1 H), 2.54-2.64 (m, 3 H), 2.21 (br d, J = 6.25 Hz, 2 H), 1.99-2.07 (m, 1 H), 1.82 (br d, J = 9.76 Hz, 2 H), 1.73 (br d, J = 10.76 Hz, 3 H), 1.55 (s, 5 H), 1.06 (br d, J = 10.88 Hz, 1 H), 0.88-0.97 (m, 3 H), 0.73-0.80 (m, 2 H). | 814.95 (814.39) | 815.6 | A | B | A | B | N.D. | N.D. |
| 87 | δ: 8.23 (d, J = 5.4 Hz, 1H), 7.71 (d, J = 8.5 Hz, 1H), 7.62 (d, J = 1.9 Hz, 1H), 7.52 (d, J = 9.0 Hz, 1H), 7.39 (d, J = 2.1 Hz, 1H), 7.36 (s, 1H), 7.26 (dd, J = 2.4, 8.6 Hz, 1H), 7.23-7.20 (m, 1H), 7.13 (dd, J = 2.2, 9.1 Hz, 1H), 5.09 (br dd, J = 5.5, 12.5 Hz, 1H), 4.57 (br d, J = 13.3 Hz, 1H), 4.43 (br d, J = 13.4 Hz, 2H), 4.23-4.15 (m, 1H), 3.53-3.48 (m, 4H), 3.23-3.06 (m, 4H), 2.90-2.83 (m, 1H), 2.80-2.69 (m, 3H), 2.67-2.62 (m, 4H), 2.33 (br d, J = 6.9 Hz, 2H), 2.17-2.09 (m, 1H), 2.02-1.90 (m, 3H), 1.88-1.82 (m, 4H), 1.62 (s, 3H), 1.26-1.10 (m, 2H), 1.08-1.04 (m, 2H), 0.83-0.79 (m, 2H) | 813.96 (813.40) | 814.6 | A | C | A | C | N.D. | N.D. |
| 88 | 1H NMR: (400 MHz, DMSO-d6) δ: 13.25-13.48 (m, 1 H), 10.97-11.15 (m, 1 H), 8.55-8.68 (m, 1 H), 8.10-8.22 (m, 1 H), 7.60-7.68 (m, 1 H), 7.46-7.54 (m, 1 H), 7.34-7.41 (m, 1 H), 7.27-7.32 (m, 1 H), 7.17-7.26 (m, 1 H), 7.02-7.10 (m, 1 H), 5.00-5.11 (m, 1 H), 4.28-4.55 (m, 3 H), 3.90-4.14 (m, 3 H), 2.79-3.20 (m, 8 H), 2.53-2.63 (m, 2 | 813.96 (813.40) | 814.6 | B | B | B | C | N.D. | N.D. |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | Degradation and characterization of exemplary bifunctional compounds of the present disclosure | | | | | | | | |
| | H), 1.95-2.05 (m, 1 H), 1.57-1.84 (m, 9 H), 1.53-1.56 (m, 3 H), 1.44-1.53 (m, 1 H), 1.10-1.21 (m, 4 H), 0.99-1.07 (m, 1 H), 0.92-0.98 (m, 2 H), 0.83-0.92 (m, 1 H), 0.72-0.81 (m, 2 H). | | | | | | | | |
| 89 | 1H NMR: (400 MHz, MeOD-d4) δ: 8.23-8.16 (m, 1H), 7.68-7.62 (m, 1H), 7.61-7.58 (m, 1H), 7.53-7.47 (m, 1H), 7.39-7.29 (m, 2H), 7.25-7.16 (m, 2H), 7.14-7.08 (m, 1H), 5.11-5.02 (m, 1H), 4.61-4.49 (m, 1H), 4.45-4.36 (m, 2H), 4.19-4.10 (m, 1H), 4.08-3.98 (m, 2H), 3.18-2.94 (m, 6H), 2.92-2.80 (m, 1H), 2.78-2.59 (m, 3H), 2.15-2.06 (m, 1H), 1.90-1.69 (m, 10H), 1.63-1.58 (m, 3H), 1.34-1.06 (m, 6H), 1.05-1.01 (m, 2H), 0.81-0.76 (m, 2H) | 812.97 (812.40) | 813.6 | B | C | B | C | N.D. | N.D. |
| 90 | 1H NMR: (400 MHz, MeOD-d4) δ: 8.63 (s, 1H), 8.10 (d, J = 1.6 Hz, 1H), 7.68 (d, J = 8.4 Hz, 1H), 7.47 (d, J = 8.8 Hz, 1H), 7.41 (s, 1H), 7.37 (d, J = 2.0 Hz, 1H), 7.24 (dd, J = 2.0, 8.0 Hz, 1H), 7.09 (dd, J = 2.0, 8.0 Hz, 1H), 5.10-5.04 (m, 1H), 4.65-4.50 (m, 4H), 4.20-4.05 (m, 3H), 3.85-3.70 (m, 4H), 3.20-3.00 (m, 4H), 2.90-2.80 (m, 1H), 2.79-2.75 (m, 1H), 2.74-2.65 (m, 2H), 2.64-2.55 (m, 4H), 2.40-2.30 (m, 2H), 2.15-2.05 (m, 1H), 2.04-1.95 (m, 2H), 1.90-1.75 (m, 5H), 1.60 (s, 3H), 1.15-1.05 (m, 1H), 1.05-0.95 (m, 2H), 0.80-0.70 (m, 2H). | 814.95 (814.39) | 815.3 | A | B | A | C | N.D. | N.D. |
| 91 | 1H NMR: (400 MHz, MeOD-d4) δ: 8.25 (d, J = 5.3 Hz, 1H), 7.69 (d, J = 8.5 Hz, 1H), 7.61 (d, J = 2.0 Hz, 1H), 7.52 (d, J = 9.0 Hz, 1H), 7.38 (d, J = 2.3 Hz, 1H), 7.34 (s, 1H), 7.28-7.23 (m, 2H), 7.15 (dd, J = 2.1, 9.0 Hz, 1H), 5.09 (dd, J = 5.5, 12.5 Hz, 1H), 4.56 (br d, J = 13.0 Hz, 1H), 4.17 (br d, J = 13.3 Hz, 1H), 4.10 (br d, J = 10.5 Hz, 2H), 3.70-3.61 (m, 4H), 3.25-2.99 (m, 4H), 2.94-2.69 (m, 4H), 2.65 (br d, J = 4.6 Hz, 4H), 2.34 (br d, J = 6.8 Hz, 2H), 2.17-2.09 (m, 1H), 2.04-1.95 (m, 2H), 1.92-1.80 (m, 5H), 1.62 (s, 3H), 1.38-1.09 (m, 2H), 1.08-1.03 (m, 2H), 0.84-0.78 (m, 2H) | 813.96 (813.40) | 814.6 | A | B | A | B | N.D. | N.D. |
| 92 | 1H NMR: (400 MHz, MeOD-d4) δ: 8.65-8.59 (m, 1H), 8.11-8.03 (m, 1H), 7.69 (d, J = 8.6 Hz, 1H), 7.49 (d, J = 9.1 Hz, 1H), 7.43-7.36 (m, 2H), 7.30-7.21 (m, 1H), 7.15-7.07 (m, 1H), 5.14-5.04 (m, 1H), 4.59-4.49 (m, 3H), 4.19-4.02 (m, 3H), 3.21-2.97 (m, 6H), 2.94-2.58 (m, 4H), 2.20-2.07 (m, 1H), 1.96-1.74 (m, 10H), 1.66-1.57 (m, 3H), 1.35-1.07 (m, 6H), 1.06-1.02 (m, 2H), 0.84-0.71 (m, 2H) | 813.96 (813.40) | 814.7 | B | B | A | B | N.D. | N.D. |
| 93 | 1H NMR: (400 MHz, MeOD-d4) δ: 8.27-8.24 (m, 0.13H), 8.22-8.15 (m, 1H), 7.72-7.65 (m, 1H), 7.64-7.58 (m, 1H), 7.56-7.46 (m, 1H), 7.42-7.33 (m, 2H), 7.30- | 812.97 (812.40) | 813.6 | B | C | B | B | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 7.19 (m, 2H), 7.17-7.10 (m, 1H), 5.18-4.99 (m, 1H), 4.58-4.49 (m, 1H), 4.40-4.26 (m, 2H), 4.20-4.04 (m, 3H), 3.25-2.97 (m, 6H), 2.90-2.63 (m, 4H), 2.17-2.08 (m, 1H), 1.97-1.69 (m, 10H), 1.66-1.57 (m, 3H), 1.37-1.24 (m, 4H), 1.08-1.08 (m, 1H), 1.24-1.08 (m, 1H), 1.07-1.03 (m, 2H), 0.85-0.73 (m, 2H). | | | | | | | | |
| 94 | 1H NMR: (400 MHz, MeOD-d4) 0: 8.62 (s, 1H), 8.24 (s, 1H), 8.07 (d, J = 2.0 Hz, 1H), 7.69 (d, J = 8.5 Hz, 1H), 7.49 (d, J = 9.1 Hz, 1H), 7.42-7.36 (m, 2H), 7.26 (dd, J = 2.2, 8.7 Hz, 1H), 7.12 (dd, J = 2.3, 9.0 Hz, 1H), 5.09 (dd, J = 5.5, 12.5 Hz, 1H), 4.59 (br d, J = 12.5 Hz, 2H), 4.10 (br d, J = 13.0 Hz, 2H), 3.75-3.63 (m, 4H), 3.17-2.98 (m, 5H), 2.94-2.67 (m, 4H), 2.62-2.50 (m, 4H), 2.37 (br d, J = 6.8 Hz, 2H), 2.16-2.10 (m, 1H), 1.97 (br d, J = 13.1 Hz, 2H), 1.90-1.81 (m, 4H), 1.63 (s, 3H), 1.33-1.22 (m, 2H), 1.07-1.02 (m, 2H), 0.82-0.78 (m, 2H) | 814.95 (814.39) | 815.6 | A | B | A | B | N.D. | N.D. |
| 95 | 1H NMR: (400 MHz, MeOD-d4) δ: 8.22 (s, 1H), 8.18 (d, J = 5.5 Hz, 1H), 7.67 (d, J = 8.5 Hz, 1H), 7.60 (d, J = 2.0 Hz, 1H), 7.51 (d, J = 9.0 Hz, 1H), 7.36 (s, 2H), 7.25-7.19 (m, 2H), 7.12 (dd, J = 2.2, 9.1 Hz, 1H), 5.07 (dd, J = 5.4, 12.6 Hz, 1H), 4.41-4.32 (m, 2H), 4.08 (br d, J = 13.1 Hz, 2H), 3.74-3.62 (m, 4H), 3.12-2.97 (m, 5H), 2.90-2.81 (m, 1H), 2.78-2.68 (m, 2H), 2.65-2.51 (m, 4H), 2.39 (br d, J = 6.6 Hz, 2H), 2.15-2.07 (m, 1H), 2.00-1.89 (m, 3H), 1.87-1.75 (m, 4H), 1.61 (s, 3H), 1.40-1.27 (m, 2H), 1.07-1.01 (m, 2H), 0.82-0.77 (m, 2H) | 813.96 (813.40) | 814.6 | A | B | A | B | N.D. | N.D. |
| 96 | 1H NMR: (400 MHz, DMSO-d6) δ: 13.55-13.38 (m, 1H), 11.08 (s, 1H), 8.65 (s, 1H), 8.20-8.08 (m, 1H), 7.66 (d, J = 8.5 Hz, 1H), 7.51 (d, J = 9.0 Hz, 1H), 7.43-7.37 (m, 1H), 7.32 (d, J = 1.8 Hz, 1H), 7.27-7.20 (m, 1H), 7.12-7.04 (m, 1H), 5.11-4.98 (m, 1H), 4.19-4.10 (m, 1H), 4.10-4.01 (m, 2H), 3.95-3.80 (m, 1H), 3.76-3.59 (m, 4H), 3.15-2.86 (m, 5H), 2.84-2.50 (m, 9H), 2.06-1.83 (m, 3H), 1.76-1.57 (m, 6H), 1.54 (s, 3H), 0.94 (s, 2H), 0.77 (d, J = 1.8 Hz, 2H). | 832.94 (832.38) | 833.6 | A | B | A | B | N.D. | N.D. |
| 97 | 1H NMR: (400 MHz, MeOD-d4) δ: 8.22-8.15 (m, 1H), 7.70-7.65 (m, 1H), 7.62-7.57 (m, 1H), 7.55-7.50 (m, 1H), 7.47-7.41 (m, 1H), 7.38-7.32 (m, 2H), 7.27-7.20 (m, 1H), 7.18-7.13 (m, 1H), 5.10-5.04 (m, 1H), 4.40-4.32 (m, 1H), 4.13-4.04 (m, 2H), 4.04-3.96 (m, 1H), 3.79-3.61 (m, 4H), 3.53-3.42 (m, 1H), 3.14-3.00 (m, 4H), 2.92-2.65 (m, 9H), 2.17-1.99 (m, 3H), 1.91-1.68 (m, 6H), 1.60 (s, 3H), 1.07-1.00 (m, 2H), 0.83-0.77 (m, 2H). | 831.95 (831.39) | 832.6 | A | C | A | B | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 98 | 1H NMR: (400 MHz, MeOD-d4) δ: 8.43 (s, 1H), 8.13 (d, J = 7.6 Hz, 1H), 7.70-7.65 (m, 2H), 7.57 (d, J = 8.0 Hz, 1H), 7.50-7.45 (m, 1H), 7.35-7.30 (m, 1H), 7.25-7.15 (m, 2H), 7.10-7.00 (m, 1H), 5.15-5.00 (m, 1H), 4.90-4.85 (m, 1H), 4.35-4.20 (m, 2H), 4.15-4.00 (m, 2H), 3.30-3.20 (m, 2H), 3.05-2.95 (m, 2H), 2.90-2.60 (m, 10H), 2.55-2.40 (m, 4H), 2.20-1.80 (m, 7H), 1.62 (s, 3H), 1.45-1.25 (m, 4H), 1.10-1.00 (m, 2H), 0.85-0.75 (m, 2H). | 799.98 (799.42) | 800.7 | D | N.D. | D | N.D. | N.D. | N.D. |
| 99 | 1H NMR: (400 MHz, MeOD-d4) δ: 8.18-8.14 (m, 1H), 7.70-7.63 (m, 1H), 7.52-7.46 (m, 1H), 7.43-7.40 (m, 1H), 7.35-7.32 (m, 1H), 7.23-7.19 (m, 1H), 7.17 (d, J = 4.9 Hz, 1H), 7.11-7.06 (m, 1H), 5.10-5.02 (m, 1H), 4.36-4.25 (m, 2H), 4.10-4.00 (m, 2H), 3.06-2.66 (m, 15H), 2.58-2.43 (m, 4H), 2.14-2.05 (m, 1H), 1.99-1.82 (m, 6H), 1.57 (s, 3H), 1.40-1.25 (m, 4H), 1.07-0.94 (m, 2H), 0.81-0.69 (m, 2H). | 817.97 (817.41) | 819.4 | C | C | C | C | N.D. | N.D. |
| 100 | 1H NMR: (400 MHz, MeOD-d4) δ: 8.20-8.17 (m, 1H), 7.69-7.63 (m, 1H), 7.61-7.57 (m, 1H), 7.53-7.47 (m, 1H), 7.35 (s, 2H), 7.25-7.19 (m, 2H), 7.14-7.08 (m, 1H), 5.10-5.03 (m, 1H), 4.12-4.03 (m, 2H), 3.86-3.71 (m, 4H), 3.59-3.49 (m, 2H), 3.34 (d, J = 3.1 Hz, 1H), 3.30 (s, 3H), 2.91-2.64 (m, 3H), 2.14-2.06 (m, 1H), 2.00 (s, 8H), 1.60 (s, 7H), 1.37 (s, 4H), 1.03 (s, 2H), 0.79 (d, J = 1.8 Hz, 2H). | 801.95 (801.38) | 802.6 | B | B | B | C | N.D. | N.D. |
| 101 | 1H NMR: (400 MHz, DMSO-d6) δ: 13.26-13.44 (m, 1 H), 11.02-11.15 (m, 1 H), 8.61-8.67 (m, 1 H), 8.13-8.18 (m, 2 H), 7.63-7.72 (m, 1 H), 7.46-7.54 (m, 1 H), 7.32-7.42 (m, 2 H), 7.22-7.29 (m, 1 H), 7.04-7.14 (m, 1 H), 4.94-5.12 (m, 1 H), 3.62-3.72 (m, 4 H), 3.44 (br s, 4 H), 2.78-2.96 (m, 1 H), 2.55 (br d, J = 1.63 Hz, 2 H), 2.41-2.49 (m, 8 H), 2.12-2.19 (m, 4 H), 1.98-2.06 (m, 1 H), 1.78-1.87 (m, 4 H), 1.54-1.59 (m, 3 H), 1.45-1.53 (m, 2 H), 0.93-0.99 (m, 2 H), 0.86-0.92 (m, 3 H), 0.75-0.82 (m, 2 H) | 800.97 (800.41) | 801.5 | A | C | B | B | N.D. | N.D. |
| 102 | 1H NMR: (400 MHz, MeOD-d4) δ: 8.08-8.20 (m, 1 H), 7.57-7.65 (m, 1 H), 7.48-7.55 (m, 1 H), 7.43 (d, J = 9.01 Hz, 1 H), 7.21-7.32 (m, 2 H), 7.13-7.20 (m, 2 H), 6.99-7.10 (m, 1 H), 4.91-5.06 (m, 1 H), 4.53 (s, 6 H), 3.48-3.63 (m, 4 H), 3.35-3.44 (m, 4 H), 2.74-2.85 (m, 1 H), 2.62 (br d, J = 3.88 Hz, 2 H), 2.51-2.55 (m, 5 H), 2.16-2.28 (m, 4 H), 1.96-2.08 (m, 1 H), 1.75-1.89 (m, 4 H), 1.52-1.54 (m, 3 H), 1.18-1.24 (m, 2 H), 0.93-0.97 (m, 3 H), 0.65-0.77 (m, 2 H). | 799.98 (799.42) | 800.4 | B | C | B | C | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 103 | 1H NMR: (400 MHz, MeOD-d4) δ: 8.68-8.62 (m, 1H), 8.12-8.08 (m, 1H), 7.73-7.65 (m, 1H), 7.52-7.47 (m, 1H), 7.46-7.40 (m, 1H), 7.39-7.34 (m, 1H), 7.27-7.20 (m, 1H), 7.15-7.09 (m, 1H), 5.08 (dd, J = 5.4, 12.4 Hz, 1H), 4.12-4.04 (m, 2H), 3.83 (br s, 4H), 3.50-3.43 (m, 2H), 3.38-3.35 (m, 1H), 3.07-2.96 (m, 2H), 2.94-2.83 (m, 1H), 2.80-2.77 (m, 1H), 2.80-2.70 (m, 1H), 2.66 (br t, J = 4.8 Hz, 4H), 2.61 (br d, J = 3.9 Hz, 1H), 2.47-2.37 (m, 2H), 2.30-2.20 (m, 1H), 2.16-2.05 (m, 4H), 1.85-1.76 (m, 2H), 1.65-1.61 (m, 3H), 1.61-1.50 (m, 1H), 1.46-1.26 (m, 3H), 1.07-1.00 (m, 2H), 0.85-0.78 (m, 2H) | 814.95 (814.39) | 815.7 | A | B | A | B | N.D. | N.D. |
| 104 | 1H NMR: (400 MHz, MeOD-d4) δ: 8.66 (s, 1H), 8.22 (s, 1H), 8.10 (d, J = 2.1 Hz, 1H), 7.68 (d, J = 8.6 Hz, 1H), 7.49 (d, J = 9.0 Hz, 1H), 7.43 (s, 1H), 7.36 (d, J = 2.3 Hz, 1H), 7.23 (dd, J = 2.3, 8.6 Hz, 1H), 7.12 (dd, J = 2.3, 9.1 Hz, 1H), 5.08 (dd, J = 5.4, 12.6 Hz, 1H), 4.08 (br d, J = 13.0 Hz, 2H), 3.83 (br s, 4H), 3.46 (br dd, J = 3.9, 7.9 Hz, 2H), 3.40-3.35 (m, 1H), 3.01 (br t, J = 11.5 Hz, 2H), 2.94-2.85 (m, 1H), 2.80-2.71 (m, 2H), 2.70-2.63 (m, 4H), 2.59 (br dd, J = 3.7, 17.4 Hz, 1H), 2.46-2.39 (m, 2H), 2.25 (br s, 1H), 2.16-2.06 (m, 4H), 1.80 (br d, J = 11.5 Hz, 2H), 1.63 (s, 3H), 1.60-1.53 (m, 1H), 1.46-1.30 (m, 3H), 1.08-1.01 (m, 2H), 0.83-0.77 (m, 2H) | 814.95 (814.39) | 815.6 | A | C | A | B | N.D. | N.D. |
| 105 | 1H NMR: (400 MHz, MeOD-d4) δ: 9.16 (d, J = 1.4 Hz, 1H), 8.49 (br d, J = 6.4 Hz, 1H), 8.27 (d, J = 2.1 Hz, 1H), 8.10 (d, J = 1.3 Hz, 1H), 7.68 (d, J = 8.5 Hz, 1H), 7.50 (d, J = 9.0 Hz, 1H), 7.36 (d, J = 2.4 Hz, 1H), 7.24 (dd, J = 2.4, 8.6 Hz, 1H), 7.11 (dd, J = 2.3, 9.1 Hz, 1H), 5.07 (dd, J = 5.4, 12.4 Hz, 1H), 4.13-4.02 (m, 2H), 3.44-3.34 (m, 3H), 3.09-2.97 (m, 2H), 2.95-2.63 (m, 8H), 2.63-2.44 (m, 4H), 2.19-1.81 (m, 12H), 1.62 (s, 3H), 1.56-1.33 (m, 4H), 1.06-0.98 (m, 2H), 0.84-0.77 (m, 2H) | 799.98 (799.42) | 800.7 | N.D. | N.D. | N.D. | N.D. | D | B |
| 106 | 1H NMR: (400 MHz, MeOD-d4) δ: 8.66-8.59 (m, 1H), 8.39-8.31 (m, 1H), 7.67 (d, J = 8.5 Hz, 1H), 7.43-7.39 (m, 1H), 7.38-7.35 (m, 1H), 7.31-7.26 (m, 1H), 7.26-7.20 (m, 1H), 5.10-5.04 (m, 1H), 4.11-4.04 (m, 2H), 4.04-3.92 (m, 2H), 3.60-3.52 (m, 1H), 3.19-3.10 (m, 3H), 3.03 (t, J = 11.9 Hz, 2H), 2.94-2.66 (m, 11H), 2.59-2.50 (m, 2H), 2.26-2.18 (m, 1H), 2.14-2.01 (m, 3H), 1.99-1.88 (m, 3H), 1.67-1.60 (m, 3H), 1.43-1.28 (m, 2H), 1.18-1.11 (m, 3H), 1.10-1.04 (m, 2H), 0.85-0.77 (m, 2H). | 850.97 (850.41) | 851.6 | A | C | A | C | N.D. | N.D. |
| 107 | 1H NMR: (400 MHz, MeOD-d4) δ: 8.63 (s, 1H), 8.51 (s, 1H), 8.09 (d, J = 1.5 Hz, 1H), 7.55 (d, J = 11.1 Hz, 1H), 7.52-7.46 (m, 2H), 7.41 | 818.96 (818.40) | 819.6 | B | B | A | C | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (s, 1H), 7.11 (dd, J = 2.2, 9.1 Hz, 1H), 5.11 (dd, J = 5.4, 12.5 Hz, 1H), 3.76-3.64 (m, 2H), 3.06 (br t, J = 12.2 Hz, 2H), 2.99-2.65 (m, 14H), 2.60-2.45 (m, 4H), 2.20-2.09 (m, 1H), 2.05 (br s, 1H), 1.94 (br d, J = 12.1 Hz, 5H), 1.63 (s, 3H), 1.52-1.39 (m, 2H), 1.36-1.23 (m, 3H), 1.07-1.00 (m, 2H), 0.84-0.76 (m, 2H) | | | | | | | | |
| 108 | 1H NMR: (400 MHz, MeOD-d4) δ: 8.64-8.58 (m, 1H), 8.10-8.03 (m, 1H), 7.69-7.62 (m, 1H), 7.51-7.44 (m, 1H), 7.42-7.33 (m, 2H), 7.27-7.17 (m, 1H), 7.14-7.03 (m, 1H), 5.10-5.02 (m, 1H), 4.19-4.10 (m, 2H), 3.86-3.71 (m, 4H), 3.58-3.42 (m, 4H), 3.30-3.21 (m, 2H), 2.92-2.65 (m, 3H), 2.15-2.07 (m, 1H), 2.05-1.91 (m, 8H), 1.61 (s, 7H), 1.43-1.32 (m, 4H), 1.06-0.98 (m, 2H), 0.82-0.74 (m, 2H). | 802.93 (802.38) | 803.6 | B | C | B | B | N.D. | N.D. |
| 109 | 1H NMR: (400 MHz, MeOD-d4) δ: 8.62 (s, 1H), 8.49 (s, 1H), 8.10 (d, J = 2.4 Hz, 1H), 7.63 (d, J = 8.0 Hz, 1H), 7.46 (d, J = 8.0 Hz, 1H), 7.39 (s, 1H), 7.11-7.08 (m, 3H), 5.10-5.07 (m, 1H), 4.44-4.34 (m, 2H), 4.11-4.05 (m, 2H), 3.98-3.95 (m, 2H), 3.57-3.42 (m, 3H), 3.20-3.14 (m, 1H), 3.01-2.87 (m, 8H), 2.85-2.80 (m, 1H), 2.75-2.34 (m, 4H), 2.17-2.12 (m, 4H), 2.00-1.90 (m, 4H), 1.60 (s, 3H), 1.53-1.42 (m, 4H), 1.15-1.13 (m, 3H), 1.03-1.00 (m, 2H), 0.79-0.76 (m, 2H). | 801.01 (800.45) | 801.7 | A | B | A | B | N.D. | N.D. |
| 110 | 1H NMR: (400 MHz, MeOD-d4) δ: 8.62 (s, 1H), 8.49 (s, 1H), 8.10 (d, J = 2.4 Hz, 1H), 7.63 (d, J = 8.0 Hz, 1H), 7.46 (d, J = 8.0 Hz, 1H), 7.39 (s, 1H), 7.11-7.08 (m, 3H), 5.10-5.07 (m, 1H), 4.44-4.34 (m, 2H), 3.98-3.95 (m, 2H), 3.80-3.70 (m, 4H), 3.36-3.35 (m, 2H), 3.07-2.87 (m, 7H), 2.80-2.64 (m, 7H), 2.48-2.43 (m, 1H), 2.26-1.93 (m, 8H), 1.60 (s, 3H), 1.43-1.40 (m, 2H), 1.03-1.00 (m, 2H), 0.79-0.76 (m, 2H). | 804.97 (804.42) | 805.6 | A | B | A | B | N.D. | N.D. |
| 111 | 1H NMR: (400 MHz, MeOD-d4) δ: 8.63 (s, 1H), 8.45 (s, 1H), 8.13-8.08 (m, 1H), 7.69 (d, J = 8.5 Hz, 1H), 7.47 (d, J = 9.0 Hz, 1H), 7.40 (s, 1H), 7.37 (d, J = 2.1 Hz, 1H), 7.25 (dd, J = 2.4, 8.6 Hz, 1H), 7.10 (dd, J = 2.3, 9.0 Hz, 1H), 5.07 (dd, J = 5.4, 12.4 Hz, 1H), 4.11 (br d, J = 12.8 Hz, 2H), 4.01 (br d, J = 12.4 Hz, 2H), 3.79-3.65 (m, 1H), 3.59 (br s, 1H), 3.12 (br d, J = 6.8 Hz, 2H), 3.10-3.01 (m, 3H), 2.98 (br s, 1H), 2.86 (td, J = 4.3, 8.8 Hz, 2H), 2.80-2.72 (m, 3H), 2.71-2.65 (m, 2H), 2.46 (br s, 1H), 2.39 (dd, J = 6.6, 12.4 Hz, 1H), 2.28 (br d, J = 6.9 Hz, 1H), 2.15-2.08 (m, 2H), 1.93 (br d, J = 11.9 Hz, 1H), 2.02-1.87 (m, 1H), 1.61 (s, 3H), 1.48-1.40 (m, 2H), 1.37 (d, J = 6.5 Hz, 2H), 1.16 (d, J = 6.3 Hz, 3H), 1.06-0.97 (m, 2H), 0.83-0.82 (m, 1H), 0.83-0.76 (m, 1H) | 800.97 (800.41) | 801.6 | N.D. | N.D. | A | A | N.D. | N.D. |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| Degradation and characterization of exemplary bifunctional compounds of the present disclosure | | | | | | | | | |
| 112 | 1H NMR: (400 MHz, MeOD-d4) δ: 8.61 (s, 1H), 8.48 (s, 1H), 8.08 (d, J = 2.1 Hz, 1H), 7.62 (d, J = 8.5 Hz, 1H), 7.47 (d, J = 9.0 Hz, 1H), 7.39 (s, 1H), 7.14-7.03 (m, 3H), 5.09 (dd, J = 5.1, 13.3 Hz, 1H), 4.56 (br d, J = 12.8 Hz, 2H), 4.46-4.28 (m, 2H), 3.93 (br d, J = 12.8 Hz, 2H), 3.06-2.97 (m, 2H), 2.97-2.65 (m, 12H), 2.58-2.42 (m, 5H), 2.14 (dtd, J = 2.4, 5.2, 12.7 Hz, 1H), 2.07-1.96 (m, 1H), 1.95-1.80 (m, 5H), 1.61 (s, 3H), 1.39-1.17 (m, 4H), 1.04-0.98 (m, 2H), 0.80-0.74 (m, 2H) | 786.98 (786.43) | 787.7 | A | A | A | A | A | A |
| 113 | 1H NMR: (400 MHz, MeOD-d4) δ: 8.67 (s, 1H), 8.10 (d, J = 1.9 Hz, 1H), 7.68 (d, J = 8.5 Hz, 1H), 7.47 (d, J = 9.0 Hz, 1H), 7.42-7.32 (m, 2H), 7.28-7.19 (m, 1H), 7.14-7.05 (m, 1H), 5.12-4.90 (m, 1H), 4.19-4.09 (m, 3H), 3.57-3.48 (m, 1H), 3.45-3.34 (m, 1H), 3.17-3.00 (m, 7H), 2.89-2.70 (m, 7H), 2.61-2.53 (m, 1H), 2.44-2.32 (m, 2H), 2.28-2.21 (m, 1H), 2.16-2.05 (m, 2H), 1.98-1.90 (m, 2H), 1.80-1.69 (m, 1H), 1.64-1.56 (m, 3H), 1.47-1.30 (m, 3H), 1.22-1.12 (m, 3H), 1.06-0.97 (m, 2H), 0.83-0.74 (m, 2H). | 800.97 (800.41) | 801.6 | A | C | A | B | N.D. | N.D. |
| 114 | 1H NMR: (400 MHz, MeOD-d4) δ: 8.63 (s, 1H), 8.34 (s, 1H), 8.09 (d, J = 1.9 Hz, 1H), 7.70 (d, J = 8.5 Hz, 1H), 7.47 (d, J = 9.1 Hz, 1H), 7.43 (s, 1H), 7.37 (d, J = 2.1 Hz, 1H), 7.28-7.22 (m, 1H), 7.10 (dd, J = 2.4, 9.0 Hz, 1H), 5.10-5.05 (m, 1H), 3.48 (br t, J = 4.9 Hz, 4H), 3.30-3.25 (m, 2H), 3.19-3.04 (m, 5H), 2.89-2.80 (m, 2H), 2.77 (br s, 1H), 2.71 (br d, J = 11.1 Hz, 3H), 2.75-2.59 (m, 4H), 2.54 (br d, J = 7.4 Hz, 2H), 2.29 (br d, J = 7.6 Hz, 1H), 2.20 (br s, 1H), 2.13-2.06 (m, 1H), 1.94 (br d, J = 12.0 Hz, 2H), 1.85 (br s, 1H), 1.61 (s, 3H), 1.43-1.25 (m, 3H), 1.05-0.98 (m, 2H), 0.82-0.74 (m, 2H) | 786.94 (786.40) | 787.6 | N.D. | N.D. | A | B | N.D. | N.D. |
| 115 | 1H NMR: (400 MHz, MeOD-d4) δ: 8.66-8.59 (m, 1H), 8.13-8.05 (m, 1H), 7.74-7.66 (m, 1H), 7.47 (d, J = 9.1 Hz, 1H), 7.44-7.33 (m, 2H), 7.27-7.20 (m, 1H), 7.14-7.04 (m, 1H), 5.13-5.02 (m, 1H), 4.63 (s, 2H), 3.69-3.58 (m, 1H), 3.54-3.37 (m, 6H), 3.18-3.05 (m, 5H), 2.88-2.61 (m, 8H), 2.56-2.49 (m, 2H), 2.36-2.07 (m, 3H), 1.99-1.90 (m, 2H), 1.89-1.77 (m, 1H), 1.66-1.57 (m, 3H), 1.43-1.27 (m, 2H), 1.06-0.97 (m, 2H), 0.85-0.73 (m, 2H). | 786.94 (786.40) | 787.5 | A | B | A | B | N.D. | N.D. |
| 116 | 1H NMR: (400 MHz, MeOD-d4) δ: 8.63 (d, J = 0.9 Hz, 1H), 8.48 (s, 1H), 8.14-8.08 (m, 1H), 7.72-7.64 (m, 1H), 7.43 (d, J = 0.9 Hz, 2H), 7.39-7.34 (m, 1H), 7.27-7.21 (m, 1H), 7.13-7.07 (m, 1H), 5.11-5.04 (m, 1H), 4.54-4.48 (m, 1H), 4.23-4.14 (m, 2H), 4.13-4.06 (m, 2H), 3.86-3.77 (m, 1H), 3.53-3.45 (m, 2H), 3.44- | 787.92 (787.38) | 788.6 | A | C | A | B | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 3.34 (m, 3H), 3.29-3.22 (m, 1H), 3.09-2.98 (m, 4H), 2.89-2.68 (m, 3H), 2.35-2.24 (m, 1H), 2.20-1.99 (m, 5H), 1.98-1.88 (m, 2H), 1.62 (s, 5H), 1.47-1.32 (m, 2H), 1.03 (s, 2H), 0.79 (d, J = 1.8 Hz, 2H). | | | | | | | | |
| 117 | 1H NMR: (400 MHz, MeOD-d4) δ: 8.62 (d, J = 0.8 Hz, 1H), 8.09 (s, 1H), 7.66 (s, 1H), 7.54-7.31 (m, 3H), 7.28-7.16 (m, 1H), 7.15-7.01 (m, 1H), 5.12-5.03 (m, 1H), 4.22-4.04 (m, 4H), 3.92-3.76 (m, 1H), 3.46 (s, 6H), 3.17-2.97 (m, 4H), 2.91-2.63 (m, 3H), 2.40-1.86 (m, 9H), 1.71-1.63 (m, 2H), 1.61 (s, 3H), 1.47-1.35 (m, 2H), 1.02 (s, 2H), 0.78 (d, J = 1.6 Hz, 2H). | 787.92 (787.38) | 788.6 | A | C | A | C | N.D. | N.D. |
| 118 | 1H NMR: (400 MHz, MeOD-d4) δ: 8.66-8.56 (m, 1H), 8.17-8.01 (m, 1H), 7.66 (d, J = 8.6 Hz, 1H), 7.51-7.43 (m, 1H), 7.40-7.31 (m, 2H), 7.25-7.19 (m, 1H), 7.13-7.05 (m, 1H), 5.10-5.03 (m, 1H), 4.59-4.50 (m, 2H), 4.37-4.25 (m, 1H), 3.84-3.74 (m, 2H), 3.72-3.61 (m, 1H), 3.29-3.20 (m, 2H), 3.10-2.97 (m, 2H), 2.94-2.56 (m, 7H), 2.52-2.37 (m, 2H), 2.22-2.07 (m, 2H), 2.06-1.78 (m, 6H), 1.61 (s, 5H), 1.26 (dt, J = 2.9, 12.5 Hz, 2H), 1.06-0.98 (m, 2H), 0.83-0.73 (m, 2H). | 787.92 (787.38) | 788.6 | B | C | B | B | N.D. | N.D. |
| 119 | 1H NMR: (400 MHz, MeOD-d4) δ: 8.62 (d, J = 1.0 Hz, 1H), 8.12-8.05 (m, 1H), 7.67-7.66 (m, 1H), 7.69-7.65 (m, 1H), 7.50-7.39 (m, 2H), 7.39-7.32 (m, 1H), 7.27-7.16 (m, 1H), 7.12-7.06 (m, 1H), 5.12-5.02 (m, 1H), 4.68-4.54 (m, 3H), 4.53-4.46 (m, 1H), 3.88-3.71 (m, 3H), 3.49-3.35 (m, 3H), 3.30-3.23 (m, 2H), 3.12-3.00 (m, 4H), 2.89-2.68 (m, 3H), 2.34-2.23 (m, 1H), 2.20-2.07 (m, 3H), 2.02 (ddd, J = 3.5, 6.1, 9.3 Hz, 2H), 1.97-1.88 (m, 2H), 1.74-1.65 (m, 2H), 1.60 (s, 3H), 1.39-1.28 (m, 2H), 1.07-0.97 (m, 2H), 0.78 (d, J = 1.8 Hz, 2H) | 787.92 (787.38) | 788 | A | C | A | C | N.D. | N.D. |
| 120 | 1H NMR: (400 MHz, MeOD-d4) δ: 8.65 (s, 1H), 8.37 (s, 1H), 8.12 (s, 1H), 7.69 (d, J = 8.6 Hz, 1H), 7.48 (d, J = 9.3 Hz, 1H), 7.42 (s, 1H), 7.37 (d, J = 2.1 Hz, 1H), 7.24 (dd, J = 2.4, 8.6 Hz, 1H), 7.11 (dd, J = 2.3, 9.1 Hz, 1H), 5.08 (br dd, J = 5.6, 12.3 Hz, 1H), 4.09 (br d, J = 11.4 Hz, 2H), 3.80 (br s, 4H), 3.69-3.63 (m, 1H), 3.25-3.19 (m, 2H), 3.03 (br t, J = 11.6 Hz, 2H), 2.92-2.72 (m, 4H), 2.69-2.58 (m, 5H), 2.49 (br d, J = 8.0 Hz, 2H), 2.28 (dd, J = 6.3, 17.3 Hz, 1H), 2.17-2.09 (m, 1H), 2.02 (br s, 1H), 1.81 (br d, J = 13.5 Hz, 2H), 1.63 (s, 3H), 1.44-1.31 (m, 3H), 1.07-1.01 (m, 2H), 0.83-0.76 (m, 2H) | 800.92 (800.38) | 801.7 | A | B | A | B | A | B |
| 121 | 1H NMR: (400 MHz, MeOD-d4) δ = 8.71-8.56 (m, 1H), 8.15-8.04 (m, 1H), 7.67 (d, J = 8.6 Hz, 1H), | 800.92 (800.38) | 801.7 | A | B | A | B | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 7.52-7.43 (m, 1H), 7.43-7.39 (m, 1H), 7.37-7.32 (m, 1H), 7.25-7.19 (m, 1H), 7.13-7.05 (m, 1H), 5.09-5.03 (m, 1H), 4.14-3.96 (m, 2H), 3.78 (br t, J = 5.0 Hz, 4H), 3.67-3.60 (m, 1H), 3.25-3.16 (m, 2H), 3.07-2.96 (m, 2H), 2.90-2.80 (m, 1H), 2.79-2.68 (m, 3H), 2.67-2.54 (m, 5H), 2.53-2.42 (m, 2H), 2.31-2.20 (m, 1H), 2.16-1.94 (m, 2H), 1.84-1.72 (m, 2H), 1.66-1.55 (m, 3H), 1.42-1.26 (m, 3H), 1.06-0.96 (m, 2H), 0.84-0.72 (m, 2H) | | | | | | | | |
| 122 | 1H NMR: (400 MHz, MeOD-d4) δ: 8.64 (d, J = 0.9 Hz, 1H), 8.11 (d, J = 2.0 Hz, 1H), 7.68 (d, J = 8.5 Hz, 1H), 7.51-7.44 (m, 1H), 7.43-7.40 (m, 1H), 7.39-7.32 (m, 1H), 7.29-7.20 (m, 1H), 7.15-7.06 (m, 1H), 5.12-5.05 (m, 1H), 4.19-4.07 (m, 5H), 3.81-3.71 (m, 2H), 3.45-3.37 (m, 1H), 3.18-2.98 (m, 6H), 2.96-2.82 (m, 3H), 2.79-2.68 (m, 3H), 2.63-2.54 (m, 2H), 2.41-2.33 (m, 1H), 2.16-2.07 (m, 1H), 1.97-1.88 (m, 1H), 1.88-1.80 (m, 2H), 1.64-1.59 (m, 3H), 1.46-1.35 (m, 2H), 1.23-1.16 (m, 3H), 1.06-0.99 (m, 2H), 0.82-0.76 (m, 2H). | 786.94 (786.40) | 787.6 | A | B | A | B | N.D. | N.D. |
| 123 | 1H NMR: (400 MHz, DMSO-d6) 8 13.40 (1H, s), 11.08 (1H, br s), 8.63 (1H, d, J = 0.8 Hz), 8.15 (1H, d, J = 2.0 Hz), 7.64 (1H, d, J = 8.4 Hz), 7.50 (1H, d, J = 9.0 Hz), 7.38 (1H, s), 7.30 (1H, d, J = 1.6Hz), 7.22 (1H, dd, J = 8.6, 2.0 Hz), 7.06 (1 H, dd, J = 9.01, 2.25 Hz), 5.06 (1 H, dd, J = 12.8, 5.4Hz), 4.93 (1H, s), 4.81 (1 H, s), 4.24 (2H, br s), 4.03 (2 H, br d, J = 12.8 Hz), 2.54-2.97 (13 H, m), 2.38-2.44 (1H, m), 2.29-2.35 (2H, m), 1.96-2.04 (1H, m), 1.76 (2H, br d, J = 12.8 Hz), 1.60 (1H, br s), 1.54 (3H, s) 1.11-1.20 (2H, m), 1.00 (3H, br d, J = 5.8 Hz), 0.91-0.96 (2H, m), 0.74-0.80 (2H, m). | 804.93 (804.39) | 805.6 | N.D. | N.D. | N.D. | N.D. | A | C |
| 124 | 1H NMR: (400 MHz, MeOD-d4) δ: 8.65 (d, J = 1.0 Hz, 1H), 8.34 (s, 1H), 8.11 (d, J = 2.1 Hz, 1H), 7.70 (d, J = 8.6 Hz, 1H), 7.46 (d, J = 9.0 Hz, 1H), 7.43 (d, J = 1.0 Hz, 1H), 7.38 (d, J = 2.3 Hz, 1H), 7.25 (dd, J = 2.4, 8.6 Hz, 1H), 7.09 (dd, J = 2.3, 9.1 Hz, 1H), 5.11-5.04 (m, 1H), 3.84 (td, J = 2.4, 4.9 Hz, 4H), 3.56-3.48 (m, 4H), 2.91-2.75 (m, 10H), 2.74-2.67 (m, 5H), 2.18-2.06 (m, 1H), 1.95-1.86 (m, 6H), 1.61 (s, 3H), 1.06-0.97 (m, 2H), 0.81-0.76 (m, 2H) | 784.92 (784.38) | 785.6 | B | C | A | C | N.D. | N.D. |
| 125 | 1H NMR: (400 MHz, MeOD-d4) δ: 8.67-8.63 (m, 1H), 8.29 (t, J = 1.1 Hz, 1H), 8.13-8.09 (m, 1H), 7.72 (td, J = 1.1, 8.5 Hz, 1H), 7.51-7.46 (m, 1H), 7.46-7.42 (m, 1H), 7.41-7.37 (m, 1H), 7.29-7.24 (m, 1H), 7.14-7.10 (m, 1H), 5.09 (dd, J = 5.6, 12.6 Hz, 1H), 4.36-4.27 (m, 2H), 3.99 (ddd, J = 1.5, 9.0, 10.5 Hz, 2H), 3.55-3.45 | 772.91 (772.38) | 773.6 | A | B | A | B | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 4H), 3.25-3.01 (m, 6H), 2.95-2.82 (m, 2H), 2.81-2.71 (m, 4H), 2.70-2.62 (m, 4H), 2.16-2.02 (m, 2H), 1.91-1.82 (m, 2H), 1.62 (t, J = 0.9 Hz, 3H), 1.41-1.30 (m, 2H), 1.07-0.98 (m, 2H), 0.85-0.74 (m, 2H) | | | | | | | | |
| 126 | 1H NMR: (400 MHz, MeOD-d4) δ: 8.63-8.59 (m, 1H), 8.24 (s, 0.2H), 8.08-8.04 (m, 1H), 7.66 (d, J = 8.5 Hz, 1H), 7.47 (d, J = 9.0 Hz, 1H), 7.43-7.38 (m, 1H), 7.37-7.33 (m, 1H), 7.22 (d, J = 8.7 Hz, 1H), 7.10 (dd, J = 2.3, 9.1 Hz, 1H), 5.09-5.04 (m, 1H), 4.40-4.33 (m, 2H), 4.17 (td, J = 1.5, 15.1 Hz, 2H), 3.87-3.78 (m, 2H), 3.72-3.59 (m, 2H), 3.52-3.41 (m, 2H), 3.29-3.22 (m, 2H), 2.91-2.66 (m, 3H), 2.28 (tt, J = 1.0, 5.7 Hz, 4H), 2.15-2.07 (m, 1H), 2.02-1.93 (m, 4H), 1.67-1.57 (m, 7H), 1.06-0.98 (m, 2H), 0.82-0.74 (m, 2H) | 774.88 (774.35) | 775.6 | B | C | B | C | N.D. | N.D. |
| 127 | 1H NMR: (400 MHz, MeOD-d4) δ: 8.22-8.16 (m, 1H), 7.69-7.64 (m, 1H), 7.62-7.57 (m, 1H), 7.50 (d, J = 9.1 Hz, 1H), 7.37-7.33 (m, 2H), 7.25-7.18 (m, 2H), 7.14-7.08 (m, 1H), 5.09 (s, 1H), 4.40-4.33 (m, 2H), 4.13-4.04 (m, 2H), 3.87-3.78 (m, 2H), 3.68-3.59 (m, 2H), 3.29 (br s, 4H), 2.92-2.81 (m, 1H), 2.78-2.66 (m, 2H), 2.31-2.25 (m, 4H), 2.15-2.06 (m, 1H), 2.02-1.94 (m, 4H), 1.69-1.61 (m, 4H), 1.61-1.57 (m, 3H), 1.06-1.01 (m, 2H), 0.82-0.76 (m, 2H) | 773.89 (773.35) | 774.6 | B | C | B | C | N.D. | N.D. |
| 128 | 1H NMR: (400 MHz, DMSO-d6) δ: 13.83-12.91 (m, 1H), 11.23-10.87 (m, 1H), 8.17-8.15 (m, 1H), 8.15-8.14 (m, 1H), 7.68-7.61 (m, 1H), 7.58-7.55 (m, 1H), 7.55-7.51 (m, 1H), 7.31-7.28 (m, 1H), 7.24-7.18 (m, 1H), 7.17-7.13 (m, 1H), 7.10-7.05 (m, 1H), 6.81-6.78 (m, 1H), 5.12-4.99 (m, 1H), 4.16-4.07 (m, 2H), 4.06-3.95 (m, 2H), 3.68 (s, 4H), 3.03-2.81 (m, 4H), 2.68-2.58 (m, 3H), 2.58-2.52 (m, 1H), 2.48-2.27 (m, 6H), 2.19-2.09 (m, 2H), 2.05-1.93 (m, 1H), 1.88-1.69 (m, 3H), 1.60-1.49 (m, 3H), 1.21-1.04 (m, 2H), 1.03-0.94 (m, 2H), 0.82-0.73 (m, 2H) | 771.92 (771.39) | 772.7 | A | B | A | B | N.D. | N.D. |
| 129 | 1H NMR: (400 MHz, DMSO-d6) δ: 13.49-13.30 (m, 1H), 11.17-10.94 (m, 1H), 8.68-8.51 (m, 1H), 8.25-8.07 (m, 2H), 7.67-7.62 (m, 1H), 7.52-7.47 (m, 1H), 7.32-7.28 (m, 1H), 7.25-7.19 (m, 1H), 7.09-7.04 (m, 1H), 6.96-6.92 (m, 1H), 5.17-4.96 (m, 1H), 4.27-4.10 (m, 2H), 4.09-3.97 (m, 2H), 3.80-3.65 (m, 2H), 3.05-2.80 (m, 5H), 2.6-2.58 (m, 3H), 2.58-2.52 (m, 3H), 2.46-2.34 (m, 5H), 2.17-2.10 (m, 2H), 2.05-1.96 (m, 1H), 1.87-1.71 (m, 3H), 1.58-1.47 (m, 3H), 1.21-1.04 (m, 2H), 1.00-0.87 (m, 2H), 0.8-0.70 (m, 2H) | 772.91 (772.38) | 773.3 | A | A | A | A | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 130 | 1H NMR: (400 MHz, MeOD-d4) δ: 8.59 (d, J = 1.0 Hz, 1H), 8.42 (s, 1H), 8.15-8.09 (m, 1H), 7.66 (s, 1H), 7.49-7.44 (m, 1H), 7.38-7.33 (m, 1H), 7.26-7.20 (m, 1H), 7.12-7.06 (m, 1H), 7.03 (d, J = 1.1 Hz, 1H), 5.14-5.02 (m, 1H), 4.73-4.63 (m, 2H), 4.48-4.35 (m, 2H), 4.06 (s, 4H), 3.84-3.69 (m, 1H), 3.37-3.32 (m, 1H), 3.15-2.63 (m, 9H), 2.19-2.03 (m, 4H), 2.00-1.86 (m, 4H), 1.60 (s, 3H), 1.46-1.32 (m, 2H), 1.01 (s, 2H), 0.78 (d, J = 1.9 Hz, 2H). | 773.90 (773.36) | 774.6 | A | B | A | B | A | A |
| 131 | 1H NMR: (400 MHz, MeOD-d4) δ = 8.63 (d, J = 1.2 Hz, 1H), 8.14 (d, J = 2.0 Hz, 1H), 7.65 (d, J = 8.4 Hz, 1H), 7.46 (d, J = 9.2 Hz, 1H), 7.33 (d, J = 2.4 Hz, 1H), 7.20 (dd, J = 2.4, 8.8 Hz, 1H), 7.13-7.03 (m, 2H), 5.06 (dd, J = 5.2, 12.4 Hz, 1H), 4.37-4.18 (m, 4H), 4.03 (d, J = 12.8 Hz, 2H), 3.05-2.85 (m, 5H), 2.76-2.66 (m, 5H), 2.63-2.42 (m, 4H), 2.26 (d, J = 6.3 Hz, 2H), 2.14-2.05 (m, 1H), 1.95-1.83 (m, 3H), 1.61 (s, 3H), 1.37-1.24 (m, 3H), 1.07-0.99 (m, 2H), 0.84-0.76 (m, 2H) | 790.90 (790.37) | 791.3 | A | A | A | A | A | A |
| 132 | 1H NMR: (400 MHz, DMSO-d6) 8 = 13.35 (s, 1H), 11.07 (s, 1H), 8.20 (d, J = 5.3 Hz, 1H), 8.15 (s, 1H), 7.64 (d, J = 8.5 Hz, 1H), 7.59-7.48 (m, 2H), 7.29 (s, 1H), 7.22 (d, J = 6.4 Hz, 2H), 7.08 (dd, J = 2.0, 9.2 Hz, 1H), 6.91 (s, 1H), 5.05 (dd, J = 5.2, 13.2 Hz, 1H), 4.25-3.96 (m, 7H), 3.01-2.83 (m, 7H), 2.70-2.66 (m, 1H), 2.60 (s, 1H), 2.42-2.28 (m, 5H), 2.12 (d, J = 6.4 Hz, 2H), 2.05-1.98 (m, 1H), 1.87-1.75 (m, 3H), 1.55 (s, 3H), 1.13 (br d, J = 12.4 Hz, 2H), 1.03-0.96 (m, 2H), 0.83-0.77 (m, 2H) | 789.91 (789.38) | 790.7 | A | B | A | B | A | A |
| 133 | 1H NMR: (400 MHz, CDCl3) δ 8.60-8.56 (m, 1H), 8.39-8.36 (m, 1H), 8.08-8.04 (m, 1H), 7.64-7.59 (m, 1H), 7.47-7.42 (m, 1H), 7.40-7.35 (m, 1H), 7.10-7.04 (m, 1H), 6.80-6.77 (m, 1H), 6.65-6.60 (m, 1H), 5.07-5.00 (m, 1H), 4.58-4.51 (m, 2H), 4.23-4.15 (m, 2H), 3.78-3.71 (m, 2H), 3.15-2.59 (m, 16H), 2.55-2.46 (m, 2H), 2.10-1.99 (m, 2H), 1.95-1.86 (m, 2H), 1.61-1.56 (m, 3H), 1.30-1.19 (m, 2H), 1.02-0.97 (m, 2H), 0.81-0.71 (m, 2H) | 772.91 (772.38) | 773.6 | A | B | A | B | N.D. | N.D. |
| 134 | 1H NMR: (400 MHz, MeOD-d4) δ = 8.63 (s, 1H), 8.12 (s, 1H), 8.07 (d, J = 2.0 Hz, 1H), 7.68 (d, J = 8.4 Hz, 1H), 7.48 (d, J = 9.2 Hz, 1H), 7.44-7.40 (m, 1H), 7.11 (dd, J = 2.4, 9.2 Hz, 1H), 6.91 (d, J = 2.0 Hz, 1H), 6.75 (dd, J = 2.0, 8.4 Hz, 1H), 5.07 (dd, J = 5.2, 12.4 Hz, 1H), 4.63 (br d, J = 13.2 Hz, 2H), 4.32-4.21 (m, 2H), 4.19-4.08 (m, 2H), 3.50-3.38 (m, 1H), | 790.90 (790.37) | 791.6 | A | B | A | B | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 3.25-2.60 (m, 16H), 2.25 (td, J = 3.6, 7.6 Hz, 1H), 2.14-2.04 (m, 1H), 1.93 (br d, J = 11.6 Hz, 2H), 1.61 (s, 3H), 1.36 (dq, J = 3.6, 12.4 Hz, 2H), 1.05-1.00 (m, 2H), 0.82-0.75 (m, 2H) | | | | | | | | |
| 135 | 1H NMR: (400 MHz, MeOD-d4) δ: 8.69-8.60 (m, 1H), 8.16-8.07 (m, 1H), 7.70-7.61 (m, 1H), 7.51-7.45 (m, 1H), 7.43-7.38 (m, 1H), 7.16-7.06 (m, 1H), 6.87-6.81 (m, 1H), 6.72-6.63 (m, 1H), 5.11-5.04 (m, 1H), 4.31-4.21 (m, 2H), 3.84-3.73 (m, 6H), 3.23-3.12 (m, 1H), 3.04-2.88 (m, 4H), 2.88-2.75 (m, 2H), 2.75-2.57 (m, 9H), 2.15-2.04 (m, 3H), 1.95-1.76 (m, 2H), 1.65-1.59 (m, 3H), 1.08-0.99 (m, 2H), 0.84-0.75 (m, 2H) | 790.90 (790.37) | 791.6 | A | B | A | C | N.D. | N.D. |
| 136 | 1H NMR: (400 MHz, DMSO-d6) δ: 13.44-13.38 (m, 1H), 11.14-11.02 (m, 1H), 8.67-8.60 (m, 1H), 8.19-8.11 (m, 1H), 7.69-7.62 (m, 1H), 7.54-7.48 (m, 1H), 7.40-7.36 (m, 1H), 7.11-7.04 (m, 1H), 6.87-6.82 (m, 1H), 6.73-6.67 (m, 1H), 5.12-4.98 (m, 1H), 4.31-4.20 (m, 2H), 4.19-4.10 (m, 2H), 3.98-3.87 (m, 1H), 3.73-3.63 (m, 4H), 3.56-3.47 (m, 2H), 3.04-2.81 (m, 3H), 2.65-2.57 (m, 6H), 2.56-2.51 (m, 2H), 2.05-1.98 (m, 1H), 1.97-1.83 (m, 2H), 1.82-1.60 (m, 2H), 1.58-1.48 (m, 3H), 0.99-0.90 (m, 2H), 0.81-0.73 (m, 2H) | 804.88 (804.35) | 805.6 | A | B | A | B | N.D. | N.D. |
| 137 | 1H NMR: (400 MHz, MeOD-d4) δ: 8.61 (d, J = 1.0 Hz, 1H), 8.10 (d, J = 2.0 Hz, 1H), 7.66 (dd, J = 7.2, 8.3 Hz, 1H), 7.46 (d, J = 9.0 Hz, 1H), 7.40-7.35 (m, 2H), 7.33 (d, J = 8.4 Hz, 1H), 7.09 (dd, J = 2.3, 9.1 Hz, 1H), 5.10 (dd, J = 5.5, 12.4 Hz, 1H), 4.15-4.02 (m, 2H), 3.80 (br d, J = 12.3 Hz, 2H), 3.50-3.40 (m, 2H), 3.16 (br dd, J = 8.6, 13.0 Hz, 1H), 3.04-2.88 (m, 6H), 2.88-2.81 (m, 2H), 2.79-2.70 (m, 3H), 2.67 (br dd, J = 4.0, 13.5 Hz, 2H), 2.58-2.50 (m, 1H), 2.34 (br s, 1H), 2.21-2.08 (m, 3H), 2.01 (br d, J = 15.9 Hz, 1H), 1.91 (br d, J = 12.9 Hz, 3H), 1.66-1.55 (m, 5H), 1.45 (br d, J = 8.9 Hz, 2H), 1.14 (d, J = 6.1 Hz, 3H), 1.05-0.98 (m, 2H), 0.82-0.75 (m, 2H) | 814.99 (814.43) | 815.6 | A | A | A | A | B | A |
| 138 | 1H NMR: (400 MHz, MeOD-d4) δ: 8.63 (d, J = 0.9 Hz, 1H), 8.54 (s, 1H), 8.11 (d, J = 2.0 Hz, 1H), 7.68-7.62 (m, 1H), 7.46 (d, J = 9.0 Hz, 1H), 7.41 (s, 1H), 7.34 (dd, J = 7.8, 14.9 Hz, 2H), 7.09 (dd, J = 2.3, 9.1 Hz, 1H), 5.10 (dd, J = 5.5, 12.5 Hz, 1H), 4.25-4.12 (m, 2H), 3.78 (br d, J = 12.4 Hz, 2H), 3.38 (br t, J = 10.4 Hz, 1H), 3.27-3.23 (m, 1H), 3.09 (br dd, J = 9.3, 13.1 Hz, 1H), 3.02 (br d, J = 11.5 Hz, 1H), 2.97-2.79 (m, 5H), 2.77 (br d, J = 2.4 Hz, 1H), 2.73 (s, 1H), 2.70 (br d, J = 3.9 Hz, 2H), 2.59 (br s, 1H), 2.54-2.36 (m, 4H), 2.15-2.06 (m, 1H), 1.89 (br d, J = 12.6 Hz, 5H), 1.61 (s, 3H), 1.58-1.40 | 829.02 (828.44) | 829.3 | A | A | B | A | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 7H), 1.18 (d, J = 6.3 Hz, 3H), 1.05-0.99 (m, 2H), 0.81-0.76 (m, 2H) | | | | | | | | |
| 139 | 1H NMR: (400 MHz, DMSO-d6) δ: 13.41 (s, 1H), 11.11 (s, 1H), 8.62 (d, J = 0.9 Hz, 1H), 8.19 (s, 1H), 8.14 (d, J = 2.4Hz, 1H), 7.85-7.78 (m, 1H), 7.55-7.48 (m, 2H), 7.45 (d, J = 7.2 Hz, 1H), 7.37 (s, 1H), 7.07 (dd, J = 2.4, 9.0 Hz, 1H), 5.08 (dd, J = 5.4, 12.8 Hz, 1H), 4.25 (t, J = 5.6 Hz, 2H), 4.00 (d, J = 10.1 Hz, 2H), 3.36-3.25 (m, 1H), 3.08-2.96 (m, 3H), 2.94-2.81 (m, 2H), 2.69-2.59 (m, 4H), 2.44-2.35 (m, 2H), 2.16 (q, J = 10.4 Hz, 3H), 2.07-1.92 (m, 4H), 1.83 (d, J = 12.4 Hz, 1H), 1.67 (d, J = 12.0 Hz, 1H), 1.54 (s, 4H), 1.27-1.08 (m, 2H), 1.02 (d, J = 6.0 Hz, 3H), 0.97-0.91 (m, 2H), 0.79-0.74 (m, 2H) | 775.91 (775.38) | 776.4 | B | C | B | C | N.D. | N.D. |
| 140 | 1H NMR: (400 MHz, MeOD-d4) δ:8.62 (s, 1H), 8.10 (d, J = 1.9 Hz, 1H), 7.64-7.55 (m, 1H), 7.47 (d, J = 9.0 Hz, 1H), 7.39 (s, 1H), 7.14-7.05 (m, 3H), 5.07 (dd, J = 5.4, 12.4 Hz, 1H), 4.06 (d, J = 10.8 Hz, 2H), 3.75-3.58 (m, 1H), 3.58-3.39 (m, 5H), 3.21-3.10 (m, 3H), 3.01-2.81 (m, 4H), 2.81-2.68 (m, 2H), 2.63 (dd, J = 9.5, 13.1 Hz, 1H), 2.56 (d, J = 5.5 Hz, 1H), 2.33 (t, J = 9.1 Hz, 1H), 2.21-2.03 (m, 5H), 1.98 (d, J = 13.8 Hz, 1H), 1.90-1.79 (m, 1H), 1.61 (s, 3H), 1.54-1.34 (m, 2H), 1.12 (d, J = 6.1 Hz, 3H), 1.06-0.99 (m, 2H), 0.82-0.75 (m, 2H). | 774.93 (774.40) | 775.5 | A | C | A | C | N.D. | N.D. |
| 141 | 1H NMR: (400 MHz, MeOD-d4) δ: 8.63 (s, 1H), 8.49 (s, 1H), 8.10 (d, J = 2.1 Hz, 1H), 7.58 (dd, J = 7.1, 8.5 Hz, 1H), 7.47 (d, J = 9.0 Hz, 1H), 7.40 (s, 1H), 7.12-7.06 (m, 3H), 5.07 (dd, J = 5.5, 12.5 Hz, 1H), 3.77 (br s, 4H), 3.53 (br d, J = 11.4 Hz, 2H), 3.44 (br t, J = 6.6 Hz, 2H), 3.14-3.07 (m, 2H), 2.97-2.66 (m, 5H), 2.57 (br t, J = 4.8 Hz, 4H), 2.32 (br d, J = 7.1 Hz, 2H), 2.15-2.04 (m, 3H), 1.93 (br s, 1H), 1.89-1.80 (m, 2H), 1.78-1.71 (m, 2H), 1.60 (s, 3H), 1.45 (br d, J = 11.3 Hz, 2H), 1.05-0.97 (m, 2H), 0.82-0.73 (m, 2H) | 774.93 (774.40) | 775.3 | A | C | A | C | N.D. | N.D. |
| 142 | 1H NMR: (400 MHz, DMSO-d6) δ: 13.69-13.06 (m, 1H), 11.03(s, 1H), 8.62 (d, J = 0.8 Hz, 1H), 8.23 (s, 1H), 8.14 (d, J = 2.0 Hz, 1H), 7.51 (d, J = 9.0 Hz, 1H), 7.37 (s, 1H), 7.29 (t, J = 7.6 Hz, 1H), 7.06 (dd, J = 2.4, 9.0 Hz, 1H), 6.94 (d, J = 7.4 Hz, 1H), 6.76 (d, J = 8.0 Hz, 1H), 5.87-5.53 (m, 1H), 5.12 (dd, J = 4.2, 13.2 Hz, 1H), 4.28-4.07 (m, 2H), 4.05-3.92 (m, 2H), 3.29 (s, 3H), 3.17 (t, J = 6.4 Hz, 2H), 3.08-2.81 (m, 5H), 2.69-2.57 (m, 2H), 2.47-2.36 (m, 1H), 2.36-2.12 (m, 2H), 2.10-1.93 (m, 4H), 1.88-1.73 (m, 3H), 1.67 (d, J = 12.4 Hz, 1H), 1.54 (s, 4H), 1.24-1.06 (m, 2H), 1.02 (d, J = 6.0 Hz, 3H), 0.98-0.90 (m, 2H), 0.80-0.74 (m, 2H) | 760.94 (760.42) | 761.5 | B | C | C | C | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 143 | 1H NMR: (400 MHz, MeOD-d4) δ: 8.63 (s, 1H), 8.56-8.54 (m, 1H), 8.10 (d, J = 2.0 Hz, 1H), 7.47 (d, J = 9.0 Hz, 1H), 7.40 (s, 1H), 7.34 (t, J = 7.8 Hz, 1H), 7.13-7.06 (m, 2H), 6.86 (d, J = 8.1 Hz, 1H), 5.16 (dd, J = 5.1, 13.3 Hz, 1H), 4.29 (d, J = 5.3 Hz, 2H), 3.77 (br s, 4H), 3.29 (br d, J = 6.3 Hz, 2H), 3.08-3.01 (m, 2H), 2.91 (dd, J = 5.2, 13.4 Hz, 1H), 2.85-2.75 (m, 2H), 2.59-2.53 (m, 4H), 2.50-2.45 (m, 2H), 2.28 (br d, J = 7.0 Hz, 2H), 2.23-2.12 (m, 3H), 1.90-1.82 (m, 2H), 1.69 (br s, 5H), 1.61 (s, 3H), 1.32-1.29 (m, 2H), 1.04-1.00 (m, 2H), 0.81-0.75 (m, 2H) | 760.94 (760.42) | 761.7 | B | B | B | C | N.D. | N.D. |
| 144 | 1H NMR: (400 MHz, MeOD-d4) δ = 8.49 (s, 1H), 8.26 (d, J = 5.3 Hz, 1H), 7.69-7.63 (m, 1H), 7.59 (d, J = 1.9 Hz, 1H), 7.51 (d, J = 9.1 Hz, 1H), 7.39-7.35 (m, 2H), 7.34-7.27 (m, 2H), 7.14 (dd, J = 2.0, 9.0 Hz, 1H), 5.09 (dd, J = 5.5, 12.4 Hz, 1H), 3.86-3.73 (m, 6H), 3.63-3.50 (m, 4H), 3.43 (br d, J = 11.1 Hz, 2H), 3.20 (br d, J = 7.9 Hz, 2H), 2.99-2.58 (m, 11H), 2.16-2.07 (m, 1H), 2.05-1.84 (m, 5H), 1.70 (br s, 1H), 1.64-1.39 (m, 7H), 1.07-0.99 (m, 2H), 0.84-0.75 (m, 2H) | 842.01 (841.43) | 842.6 | B | B | B | B | N.D. | N.D. |
| 145 | 1H NMR: (400 MHz, MeOD-d4) δ: 8.62 (s, 1H), 8.56 (s, 1H), 8.10 (d, J = 1.8 Hz, 1H), 7.51-7.42 (m, 3H), 7.40 (s, 1H), 7.26 (dd, J = 1.1, 7.4 Hz, 1H), 7.12-7.07 (m, 1H), 5.16 (dd, J = 5.3, 13.4 Hz, 1H), 4.60 (br s, 2H), 4.56-4.41 (m, 2H), 4.19-4.06 (m, 2H), 3.42 (br d, J = 4.5 Hz, 2H), 3.19-3.12 (m, 1H), 3.09-2.87 (m, 4H), 2.86-2.74 (m, 3H), 2.68-2.60 (m, 1H), 2.59-2.48 (m, 2H), 2.46-2.26 (m, 3H), 2.24-2.09 (m, 3H), 1.98-1.88 (m, 3H), 1.85-1.73 (m, 2H), 1.62 (s, 4H), 1.50-1.30 (m, 4H), 1.15 (d, J = 6.3 Hz, 3H), 1.05-0.99 (m, 2H), 0.82-0.75 (m, 2H) | 801.01 (800.45) | 801.7 | A | B | A | C | N.D. | N.D. |
| 146 | 1H NMR: (400 MHz, MeOD-d4) δ: 8.63 (s, 1H), 8.45 (s, 1H), 8.10 (d, J = 2.0 Hz, 1H), 7.73-7.64 (m, 1H), 7.49 (d, J = 9.0 Hz, 1H), 7.42 (s, 1H), 7.36 (dd, J = 7.9, 13.8 Hz, 2H), 7.12 (dd, J = 2.3, 9.1 Hz, 1H), 5.12 (dd, J = 5.5, 12.3 Hz, 1H), 3.81 (br d, J = 10.5 Hz, 2H), 3.07 (br t, J = 11.7 Hz, 4H), 3.00-2.79 (m, 10H), 2.75 (br s, 2H), 2.72-2.65 (m, 1H), 2.71 (br s, 1H), 2.57 (br s, 2H), 2.18-2.11 (m, 1H), 1.94 (br s, 5H), 1.63 (s, 3H), 1.56 (br d, J = 10.9 Hz, 2H), 1.36-1.23 (m, 1H), 1.36-1.23 (m, 1H), 1.36-1.23 (m, 1H), 1.06-1.01 (m, 2H), 0.84-0.76 (m, 2H) | 800.97 (800.41) | 801.6 | N.D. | N.D. | B | B | N.D. | N.D. |
| 147 | 1H NMR: (400 MHz, MeOD-d4) δ: 8.61 (s, 1H), 8.44 (s, 1H), 8.08 (d, J = 2.0 Hz, 1H), 7.49-7.42 (m, 3H), 7.40 (s, 1H), 7.27-7.23 (m, 1H), 7.10 (dd, J = 2.3, 9.1 Hz, 1H), 5.16 (dd, J = 5.2, 13.3 Hz, 1H), | 786.98 (786.43) | 787.7 | A | A | A | A | N.D. | N.D. |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | Degradation and characterization of exemplary bifunctional compounds of the present disclosure | | | | | | | | |
| | 4.62-4.52 (m, 2H), 4.51-4.42 (m, 2H), 3.42 (br d, J = 11.9 Hz, 2H), 3.10-2.77 (m, 14H), 2.70-2.61 (m, 2H), 2.59-2.45 (m, 3H), 2.18 (dtd, J = 2.4, 5.2, 12.7 Hz, 1H), 2.10-2.00 (m, 1H), 1.97-1.84 (m, 5H), 1.61 (s, 3H), 1.49-1.37 (m, 2H), 1.34-1.19 (m, 2H), 1.04-0.99 (m, 2H), 0.82-0.76 (m, 2H) | | | | | | | | |
| 148 | 1H NMR: (400 MHz, MeOD-d4) δ: 8.73 (s, 1H), 7.73-7.65 (m, 3H), 7.47 (s, 1H), 7.43-7.35 (m, 3H), 5.12 (dd, J = 5.6, 12.4 Hz, 1H), 4.30 (br s, 4H), 3.91-3.75 (m, 4H), 3.64-3.45 (m, 2H), 3.32-3.26 (m, 2H), 3.20-3.09 (m, 4H), 3.00 (br t, J = 11.7 Hz, 2H), 2.95-2.50 (m, 5H), 2.33-2.08 (m, 5H), 2.07-1.93 (m, 4H), 1.72-1.64 (m, 2H), 1.63 (s, 3H), 1.11-1.05 (m, 2H), 0.87-0.82 (m, 2H) | 850.97 (850.41) | 851.6 | B | B | B | C | N.D. | N.D. |
| 149 | 1H NMR: (400 MHz, MeOD-d4) δ: 8.68 (s, 1H), 8.13 (d, J = 1.8 Hz, 1H), 7.67 (d, J = 8.5 Hz, 1H), 7.51-7.40 (m, 2H), 7.36 (d, J = 2.0 Hz, 1H), 7.23 (dd, J = 2.3, 8.6 Hz, 1H), 7.10 (dd, J = 2.2, 9.1 Hz, 1H), 5.07 (dd, J = 5.5, 12.5 Hz, 1H), 4.48 (d, J = 11.9 Hz, 1H), 4.33 (d, J = 13.6 Hz, 1H), 4.10 (d, J = 9.4 Hz, 1H), 3.94 (s, 1H), 3.86-3.66 (m, 5H), 3.21-2.63 (m, 13H), 2.14-1.64(m, 7H), 1.73-1.64 (m, 2H), 1.61 (s, 3H), 1.07-0.99 (m, 2H), 0.82-0.74 (m, 2H). | 803.92 (803.38) | 804.6 | B | B | B | B | N.D. | N.D. |
| 150 | 1H NMR: (400 MHz, MeOD-d4) δ: 8.68 (s, 1H), 8.13 (d, J = 1.8 Hz, 1H), 7.67 (d, J = 8.5 Hz, 1H), 7.51-7.40 (m, 2H), 7.36 (d, J = 2.0 Hz, 1H), 7.23 (dd, J = 2.3, 8.6 Hz, 1H), 7.10 (dd, J = 2.2, 9.1 Hz, 1H), 5.07 (dd, J = 5.5, 12.5 Hz, 1H), 4.48 (d, J = 11.9 Hz, 1H), 4.33 (d, J = 13.6 Hz, 1H), 4.10 (d, J = 9.4 Hz, 1H), 3.94 (s, 1H), 3.86-3.66 (m, 5H), 3.21-2.63 (m, 13H), 2.14-1.64(m, 7H), 1.73-1.64 (m, 2H), 1.61 (s, 3H), 1.07-0.99 (m, 2H), 0.82-0.74 (m, 2H). | 803.92 (803.38) | 804.3 | A | B | A | B | N.D. | N.D. |
| 151 | 1H NMR: (400 MHz, MeOD-d4) δ: 8.43 (s, 1H), 8.27 (d, J = 5.3 Hz, 1H), 7.68 (d, J = 8.5 Hz, 1H), 7.59 (d, J = 1.9 Hz, 1H), 7.51 (d, J = 9.0 Hz, 1H), 7.39-7.33 (m, 2H), 7.29 (d, J = 5.3 Hz, 1H), 7.23 (dd, J = 2.3, 8.6 Hz, 1H), 7.15 (dd, J = 2.1, 9.1 Hz, 1H), 5.07 (dd, J = 5.4, 12.4 Hz, 1H), 4.08 (br d, J = 13.0 Hz, 2H), 3.86-3.80 (m, 2H), 3.77 (s, 2H), 3.64 (br d, J = 8.3 Hz, 2H), 3.58-3.52 (m, 2H), 3.44 (br d, J = 11.8 Hz, 2H), 3.29-3.23 (m, 2H), 3.03 (br t, J = 11.9 Hz, 2H), 2.91-2.63 (m, 9H), 2.17-2.04 (m, 2H), 2.02-1.86 (m, 4H), 1.72 (br s, 1H), 1.60 (s, 3H), 1.54-1.33 (m, 4H), 1.07-1.00 (m, 2H), 0.83-0.77 (m, 2H) | 842.01 (841.43) | 842.6 | A | B | A | B | N.D. | N.D. |
| 152 | 1H NMR: (400 MHz, MeOD-d4) δ: 8.66 (s, 1H), 8.44 (s, 1H), 8.12 (d, J = 2.1 Hz, 1H), 7.65 (d, J = 8.4 Hz, 1H), 7.50-7.40 (m, 2H), 7.10 (dd, J = 2.2, 9.1 Hz, 1H), 6.98 (d, | 802.94 (802.39) | 803.6 | A | C | A | C | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | J = 2.0 Hz, 1H), 6.82 (dd, J = 2.1, 8.6 Hz, 1H), 5.06 (dd, J = 5.3, 12.4 Hz, 1H), 4.43 (br d, J = 12.8 Hz, 1H), 4.30 (br d, J = 12.6 Hz, 1H), 4.10-4.02 (m, 1H), 3.82 (br d, J = 6.8 Hz, 1H), 3.74-3.63 (m, 2H), 3.61-3.53 (m, 1H), 3.48-3.42 (m, 1H), 3.20-3.07 (m, 3H), 3.04-2.79 (m, 10H), 2.78-2.64 (m, 5H), 2.45-2.34 (m, 1H), 2.34-2.24 (m, 1H), 2.14-2.04 (m, 1H), 1.87-1.73 (m, 3H), 1.61 (s, 3H), 1.05-0.97 (m, 2H), 0.82-0.74 (m, 2H) | | | | | | | | |
| 153 | 1H NMR: (400 MHz, MeOD-d4) δ: 8.66 (s, 1H), 8.11 (s, 1H), 7.66 (d, J = 8.6 Hz, 1H), 7.50-7.41 (m, 2H), 7.34 (d, J = 2.0 Hz, 1H), 7.22 (dd, J = 2.2, 8.7 Hz, 1H), 7.10 (dd, J = 2.3, 9.0 Hz, 1H), 5.06 (dd, J = 5.4, 12.6 Hz, 1H), 4.43 (br d, J = 11.9 Hz, 1H), 4.31 (br d, J = 13.9 Hz, 1H), 4.05 (br d, J = 11.6 Hz, 3H), 3.81 (br s, 1H), 3.74-3.64 (m, 1H), 3.19-3.12 (m, 1H), 3.00 (br t, J = 11.9 Hz, 2H), 2.91-2.58 (m, 14H), 2.40 (br s, 2H), 2.15-2.05 (m, 1H), 1.91 (br d, J = 12.0 Hz, 3H), 1.61 (s, 3H), 1.32 (br d, J = 11.1 Hz, 2H), 1.06-0.99 (m, 2H), 0.82-0.75 (m, 2H) | 802.94 (802.39) | 803.6 | A | C | A | C | N.D. | N.D. |
| 154 | 1H NMR: (400 MHz, CDCl3) δ: 8.72-8.64 (m, 1H), 8.17-8.09 (m, 1H), 7.70-7.64 (m, 1H), 7.52-7.43 (m, 2H), 7.37-7.29 (m, 1H), 7.27-7.17 (m, 1H), 7.14-7.06 (m, 1H), 5.12-5.06 (m, 1H), 4.46-4.38 (m, 1H), 4.37-4.26 (m, 1H), 4.07-4.06 (m, 1H), 4.12-4.00 (m, 3H), 3.74-3.60 (m, 2H), 3.19-2.97 (m, 8H), 2.94-2.63 (m, 8H), 2.49-2.40 (m, 2H), 2.18-2.07 (m, 1H), 2.00-1.85 (m, 5H), 1.61 (s, 3H), 1.38-1.26 (m, 2H), 1.06-1.00 (m, 2H), 0.83-0.75 (m, 2H). | 816.96 (816.41) | 817.6 | A | B | A | B | N.D. | N.D. |
| 155 | 1H NMR: (400 MHz, CDCl3) δ: 8.72-8.64 (m, 1H), 8.17-8.09 (m, 1H), 7.70-7.64 (m, 1H), 7.52-7.43 (m, 2H), 7.37-7.29 (m, 1H), 7.27-7.17 (m, 1H), 7.14-7.06 (m, 1H), 5.12-5.06 (m, 1H), 4.46-4.38 (m, 1H), 4.37-4.26 (m, 1H), 4.07-4.06 (m, 1H), 4.12-4.00 (m, 3H), 3.74-3.60 (m, 2H), 3.19-2.97 (m, 8H), 2.94-2.63 (m, 8H), 2.49-2.40 (m, 2H), 2.18-2.07 (m, 1H), 2.00-1.85 (m, 5H), 1.61 (s, 3H), 1.38-1.26 (m, 2H), 1.06-1.00 (m, 2H), 0.83-0.75 (m, 2H). | 816.96 (816.41) | 817.6 | A | B | A | B | N.D. | N.D. |
| 156 | 1H NMR: (400 MHz, MeOD-d4) δ: 8.67 (s, 1H), 8.19 (s, 0.3H), 8.11 (d, J = 2.0 Hz, 1H), 7.66 (d, J = 8.6 Hz, 1H), 7.53-7.41 (m, 2H), 7.35 (d, J = 2.3 Hz, 1H), 7.22 (dd, J = 2.3, 8.6 Hz, 1H), 7.10 (dd, J = 2.3, 9.1 Hz, 1H), 5.06 (dd, J = 5.4, 12.6 Hz, 1H), 4.06 (br d, J = 13.1 Hz, 2H), 4.01-3.81 (m, 6H), 3.80-3.70 (m, 1H), 3.08-2.91 (m, 8H), 2.85-2.71 (m, 5H), 2.52-2.32 (m, 3H), 2.19-1.86 (m, 5H), 1.61 (s, 3H), 1.33 (q, J = 11.3 Hz, 2H), 1.06-0.97 (m, 2H), 0.83-0.72 (m, 2H) | 802.94 (802.39) | 803.5 | A | C | A | B | N.D. | N.D. |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| Degradation and characterization of exemplary bifunctional compounds of the present disclosure | | | | | | | | | |
| 157 | 1H NMR: (400 MHz, MeOD-d4) δ: 8.65 (s, 1H), 8.28 (s, 1H), 8.11 (d, J = 2.1 Hz, 1H), 7.66 (d, J = 8.6 Hz, 1H), 7.47 (d, J = 9.0 Hz, 1H), 7.43 (s, 1H), 7.34 (d, J = 2.3 Hz, 1H), 7.22 (dd, J = 2.3, 8.7 Hz, 1H), 7.09 (dd, J = 2.3, 9.0 Hz, 1H), 5.06 (dd, J = 5.4, 12.6 Hz, 1H), 4.06 (br d, J = 12.6 Hz, 2H), 3.96-3.78 (m, 6H), 3.77-3.68 (m, 1H), 3.01 (br t, J = 12.1 Hz, 2H), 2.94 (br d, J = 11.8 Hz, 1H), 2.90-2.86 (m, 1H), 2.82 (br d, J = 3.0 Hz, 4H), 2.78-2.69 (m, 4H), 2.65-2.58 (m, 1H), 2.37 (br d, J = 6.5 Hz, 2H), 2.31-2.21 (m, 1H), 2.14-2.06 (m, 1H), 2.05-1.88 (m, 4H), 1.61 (s, 3H), 1.39-1.24 (m, 2H), 1.05-0.98 (m, 2H), 0.82-0.75 (m, 2H) | 802.94 (802.39) | 803.6 | A | A | A | B | N.D. | N.D. |
| 158 | 1H NMR: (400 MHz, MeOD-d4) δ: 8.65 (s, 1H), 8.20 (s, 1H), 8.11 (d, J = 2.0 Hz, 1H), 7.66 (d, J = 8.5 Hz, 1H), 7.47 (d, J = 9.1 Hz, 1H), 7.43 (s, 1H), 7.34 (d, J = 2.3 Hz, 1H), 7.21 (dd, J = 2.4, 8.6 Hz, 1H), 7.10 (dd, J = 2.3, 9.0 Hz, 1H), 5.06 (dd, J = 5.4, 12.6 Hz, 1H), 4.05 (br d, J = 11.4 Hz, 3H), 3.90 (br d, J = 6.8 Hz, 1H), 3.83 (br s, 3H), 3.80-3.71 (m, 1H), 3.27-3.15 (m, 2H), 3.05-2.96 (m, 2H), 2.90 (br d, J = 4.4 Hz, 2H), 2.83-2.62 (m, 12H), 2.47 (br t, J = 10.6 Hz, 1H), 2.15-2.05 (m, 1H), 1.87 (br d, J = 12.8 Hz, 2H), 1.69-1.63 (m, 2H), 1.61 (s, 3H), 1.43-1.30 (m, 2H), 1.06-0.97 (m, 2H), 0.82-0.74 (m, 2H) | 816.96 (816.41) | 817.5 | A | A | A | A | N.D. | N.D. |
| 159 | 1H NMR: (400 MHz, MeOD-d4) δ: 8.62 (d, J = 0.9 Hz, 1H), 8.10 (d, J = 2.0 Hz, 1H), 7.67 (d, J = 8.6 Hz, 1H), 7.46 (d, J = 9.1 Hz, 1H), 7.40 (s, 1H), 7.35 (d, J = 2.1 Hz, 1H), 7.22 (dd, J = 2.3, 8.7 Hz, 1H), 7.09 (dd, J = 2.3, 9.1 Hz, 1H), 5.07 (dd, J = 5.4, 12.6 Hz, 1H), 4.07 (d, J = 13.1 Hz, 4H), 3.65-3.51 (m, 2H), 3.46 (d, J = 12.6 Hz, 1H), 3.22-3.12 (m, 3H), 3.06-2.56 (m, 10H), 2.35 (t, J = 9.1 Hz, 1H), 2.26-2.01 (m, 4H), 1.87 (d, J = 12.0 Hz, 3H), 1.80-1.67 (m, 3H), 1.61 (s, 3H), 1.51-1.32 (m, 4H), 1.14 (d, J = 6.3 Hz, 3H), 1.07-0.97 (m, 2H), 0.83-0.75 (m, 2H). | 829.02 (828.44) | 829.4 | A | B | A | C | N.D. | N.D. |
| 160 | 1H NMR: (400 MHz, MeOD-d4) δ: 8.12 (d, J = 5.5 Hz, 1H), 7.66 (d, J = 8.5 Hz, 1H), 7.59 (d, J = 1.8 Hz, 1H), 7.50 (d, J = 9.1 Hz, 1H), 7.34 (d, J = 2.3 Hz, 1H), 7.24-7.17 (m, 2H), 7.12 (dd, J = 2.2, 9.1 Hz, 1H), 6.88 (s, 1H), 5.07 (dd, J = 5.4, 12.4 Hz, 1H), 4.24 (t, J = 7.8 Hz, 2H), 4.05 (br d, J = 13.3 Hz, 2H), 3.75-3.68 (m, 2H), 3.05-2.99 (m, 3H), 2.97 (br s, 1H), 2.91 (br d, J = 6.0 Hz, 1H), 2.88-2.85 (m, 1H), 2.83 (br d, J = 5.3 Hz, 1H), 2.77 (br d, J = 2.5 Hz, 1H), 2.73 (br s, 1H), 2.71-2.65 (m, 1H), 2.31 (br s, | 770.94 (770.39) | 771.5 | A | B | A | B | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1H), 2.14-2.06 (m, 2H), 1.91 (br d, J = 10.6 Hz, 2H), 1.78-1.66 (m, 4H), 1.61 (s, 3H), 1.42-1.28 (m, 6H), 1.07-1.02 (m, 2H), 0.83-0.78 (m, 2H) | | | | | | | | |
| 161 | δ: 8.32 (s, 1H), 8.15 (d, J = 5.5 Hz, 1H), 7.68 (d, J = 8.5 Hz, 1H), 7.58 (d, J = 2.0 Hz, 1H), 7.51 (d, J = 9.0 Hz, 1H), 7.36 (d, J = 2.1 Hz, 1H), 7.30-7.19 (m, 2H), 7.14 (dd, J = 2.1, 9.1 Hz, 1H), 6.93 (s, 1H), 5.07 (dd, J = 5.4, 12.4 Hz, 1H), 4.25 (s, 4H), 4.08 (br d, J = 13.1 Hz, 2H), 3.93 (br s, 4H), 3.51-3.40 (m, 2H), 3.03 (br t, J = 11.7 Hz, 2H), 2.88-2.68 (m, 9H), 2.17-2.03 (m, 2H), 1.93 (br t, J = 13.8 Hz, 4H), 1.76 (br s, 1H), 1.61 (s, 3H), 1.57-1.32 (m, 4H), 1.06-1.01 (m, 2H), 0.84-0.78 (m, 2H) | 811.99 (811.42) | 812.6 | B | B | B | B | N.D. | N.D. |
| 162 | 1H NMR: (400 MHz, DMSO-d6) δ: 13.33 (s, 1H), 11.10 (s, 1H), 8.23-8.15 (m, 2H), 7.65 (d, J = 8.4 Hz, 1H), 7.57-7.48 (m, 2H), 7.30 (s, 1H), 7.22 (d, J = 8.8 Hz, 1H), 7.18-7.08 (m, 2H), 5.06 (dd, J = 5.2, 12.8 Hz, 1H), 4.15-3.97 (m, 4H), 3.84 (t, J = 6.8 Hz, 2H), 3.47 (s, 4H), 3.03-2.80 (m, 4H), 2.77-2.65 (m, 2H), 2.63-2.52 (m, 4H), 2.11 (d, J = 6.2 Hz, 2H), 2.06-1.95 (m, 1H), 1.86-1.67 (m, 5H), 1.62-1.48 (m, 4H), 1.27 (s, 1H), 1.17-0.99 (m, 4H), 0.99-0.89 (m, 2H), 0.82-0.69 (m, 2H) | 811.99 (811.42) | 812.5 | D | C | C | C | N.D. | N.D. |
| 163 | 1H NMR: (400 MHz, MeOD-d4) δ: 8.42 (br s, 1H), 8.15 (d, J = 5.5 Hz, 1H), 7.66 (d, J = 8.6 Hz, 1H), 7.58 (d, J = 2.0 Hz, 1H), 7.51 (d, J = 9.1 Hz, 1H), 7.34 (d, J = 1.9 Hz, 1H), 7.25 (dd, J = 0.9, 5.5 Hz, 1H), 7.21 (dd, J = 2.0, 8.5 Hz, 1H), 7.14 (dd, J = 2.1, 9.1 Hz, 1H), 6.95 (s, 1H), 5.06 (dd, J = 5.4, 12.3 Hz, 1H), 4.32 (d, J = 9.3 Hz, 2H), 4.11 (d, J = 9.1 Hz, 2H), 4.05 (br d, J = 13.1 Hz, 2H), 3.52 (br d, J = 11.6 Hz, 2H), 3.26 (br t, J = 6.8 Hz, 2H), 3.05-2.94 (m, 4H), 2.91-2.84 (m, 2H), 2.82 (br d, J = 5.9 Hz, 1H), 2.80-2.74 (m, 1H), 2.73-2.67 (m, 1H), 2.62 (br d, J = 6.6 Hz, 2H), 2.44 (br t, J = 6.8 Hz, 2H), 2.15-2.02 (m, 4H), 1.87 (br d, J = 12.0 Hz, 2H), 1.72 (br s, 1H), 1.60 (s, 3H), 1.58-1.47 (m, 2H), 1.38 (br d, J = 10.1 Hz, 1H), 1.43-1.32 (m, 1H), 1.06-1.00 (m, 2H), 0.83-0.78 (m, 2H) | 811.99 (811.42) | 812.6 | B | C | B | C | N.D. | N.D. |
| 164 | 1H NMR: (400 MHz, MeOD-d4) δ: 8.57 (s, 1H), 8.51 (br s, 1H), 8.11 (s, 1H), 7.68 (d, J = 8.5 Hz, 1H), 7.47 (d, J = 8.9 Hz, 1H), 7.37 (d, J = 2.0 Hz, 1H), 7.24 (dd, J = 2.0, 8.6 Hz, 1H), 7.10 (dd, J = 2.3, 9.0 Hz, 1H), 6.99 (s, 1H), 5.07 (dd, J = 5.5, 12.4 Hz, 1H), 4.32 (br t, J = 8.4 Hz, 2H), 4.09 (br d, J = 13.6-Hz, 2H), 3.84-3.78 (m, 2H), 3.56 3.39 (m, 2H), 3.10-2.95 (m, 4H), 2.90 (br s, 2H), 2.86-2.81 (m, 2H), 2.80-2.69 (m, 4H), 2.16-2.06 (m, 2H), 1.99-1.89 (m, 4H), 1.76 (br t, J = 6.9 Hz, 1H), | 771.92 (771.39) | 772.6 | A | A | A | B | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1.60 (s, 3H), 1.53 (br d, J = 11.4 Hz, 2H), 1.44-1.35 (m, 2H), 1.04-0.96 (m, 2H), 0.78 (d, J = 1.6 Hz, 2H) | | | | | | | | |
| 165 | 1H NMR: (400 MHz, MeOD-d4) δ: 8.49 (s, 1H), 8.13 (d, J = 6.4 Hz, 1H), 7.69 (d, J = 8.0 Hz, 1H), 7.58 (d, J = 1.6 Hz, 1H), 7.51 (d, J = 8.0 Hz, 1H), 7.36 (d, J = 2.4 Hz, 1H), 7.25-7.20 (m, 2H), 7.14-7.12 (m, 1H), 6.88 (s, 1H), 5.15-5.00 (m, 1H), 4.22 (t, J = 8.0 Hz, 2H), 4.15-4.00 (m, 2H), 3.80-3.70 (m, 2H), 3.55-3.45 (m, 2H), 3.15-3.00 (m, 2H), 2.95-2.65 (m, 8H), 2.20-2.10 (m, 2H), 2.01-1.97 (m, 2H), 1.92-1.89 (m, 2H), 1.77-1.75 (m, 2H), 1.60 (s, 4H), 1.55-1.35 (m, 6H), 1.05-1.02 (m, 2H), 0.81-0.78 (m, 2H). | 784.96 (784.41) | 785.6 | A | B | A | C | N.D. | N.D. |
| 166 | 1H NMR: (400 MHz, MeOD-d4) δ: 8.58 (s, 1H), 8.41 (s, 1H), 8.08 (s, 1H), 7.65 (d, J = 8.5 Hz, 1H), 7.47 (d, J = 9.0 Hz, 1H), 7.16-7.06 (m, 2H), 6.99 (d, J = 2.0 Hz, 1H), 6.83 (dd, J = 2.1, 8.6 Hz, 1H), 5.06 (br dd, J = 5.4, 12.4 Hz, 1H), 3.98-3.64 (m, 4H), 3.62-3.51 (m, 3H), 3.50-3.43 (m, 2H), 3.18-2.57 (m, 15H), 2.47-2.35 (m, 1H), 2.29 (br s, 2H), 2.14-2.05 (m, 1H), 1.98-1.70 (m, 4H), 1.61 (s, 3H), 1.05-0.99 (m, 2H), 0.84-0.75 (m, 2H) | 786.94 (786.40) | 787.6 | A | C | A | C | N.D. | N.D. |
| 167 | 1H NMR: (400 MHz, MeOD-d4) δ: 8.62-8.55 (m, 1H), 8.15-8.06 (m, 1H), 7.69-7.60 (m, 1H), 7.52-7.42 (m, 1H), 7.15-7.06 (m, 2H), 7.03-6.96 (m, 1H), 6.88-6.79 (m, 1H), 5.09-4.93 (m, 1H), 3.70-3.61 (m, 2H), 3.61-3.53 (m, 2H), 3.50-3.40 (m, 2H), 3.15-3.08 (m, 2H), 3.06-2.99 (m, 2H), 2.96-2.89 (m, 2H), 2.87 (d, J = 3.5 Hz, 1H), 2.82 (d, J = 5.4 Hz, 1H), 2.76 (d, J = 2.4 Hz, 2H), 2.72 (s, 1H), 2.69 (d, J = 3.6 Hz, 1H), 2.67-2.64 (m, 1H), 2.63-2.54 (m, 3H), 2.47-2.39 (m, 1H), 2.34-2.24 (m, 2H), 2.16-2.06 (m, 1H), 1.91-1.71 (m, 4H), 1.65-1.57 (m, 3H), 1.33-1.25 (m, 2H), 1.07-0.97 (m, 2H), 0.83-0.76 (m, 2H). | 786.94 (786.40) | 787.6 | A | B | A | B | N.D. | N.D. |
| 168 | 1H NMR: (400 MHz, DMSO-d6) δ: 13.46-13.31 (m, 1H), 11.20-10.95 (m, 1H), 8.73-8.54 (m, 1H), 8.16-8.11 (m, 1H), 8.03-7.98 (m, 1H), 7.64-7.57 (m, 1H), 7.52-7.45 (m, 1H), 7.39-7.34 (m, 1H), 7.32-7.27 (m, 1H), 7.20-7.14 (m, 1H), 7.08-7.02 (m, 1H), 5.13-4.98 (m, 1H), 4.29-4.22 (m, 2H), 4.21-4.11 (m, 2H), 4.07-3.97 (m, 2H), 3.92-3.71 (m, 2H), 3.20-3.09 (m, 1H), 2.96-2.77 (m, 5H), 2.62-2.52 (m, 2H), 2.35-2.20 (m, 2H), 2.19-2.09 (m, 1H), 2.04-1.94 (m, 1H), 1.56-1.46 (m, 5H), 1.30-1.13 (m, 5H), 0.97-0.88 (m, 2H), 0.76-0.71 (m, 2H) | 798.91 (798.37) | 799.5 | B | C | A | C | N.D. | N.D. |
| 169 | 1H NMR: (400 MHz, DMSO-d6) δ: 13.52-13.27 (m, 1H), 11.16-10.98 (m, 1H), 8.64-8.61 (m, 1H), | 794.92 (794.37) | 795.3 | B | B | A | C | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 8.17-8.15 (m, 1H), 8.14-8.12 (m, 1H), 7.68-7.64 (m, 1H), 7.52-7.48 (m, 1H), 7.38-7.35 (m, 1H), 7.33-7.27 (m, 5H), 7.25-7.20 (m, 1H), 7.09-7.03 (m, 1H), 5.09-5.01 (m, 1H), 3.72-3.62 (m, 4H), 3.45-3.38 (m, 8H), 2.93-2.78 (m, 1H), 2.62-2.52 (m, 2H), 2.48-2.42 (m, 8H), 2.05-1.95 (m, 1H), 1.56-1.48 (m, 3H), 0.96-0.89 (m, 2H), 0.79-0.73 (m, 2H) | | | | | | | | |
| 170 | δ: 8.67-8.63 (m, 1H), 8.13-8.08 (m, 1H), 7.72-7.66 (m, 1H), 7.45 (br dd, J = 9.5, 13.9 Hz, 4H), 7.38 (s, 3H), 7.27-7.22 (m, 1H), 7.13-7.08 (m, 1H), 5.11-5.07 (m, 1H), 3.87-3.78 (m, 4H), 3.73-3.65 (m, 4H), 3.54-3.48 (m, 4H), 2.82-2.73 (m, 4H), 2.72-2.65 (m, 7H), 2.15-2.09 (m, 1H), 1.66-1.57 (m, 3H), 1.08-0.97 (m, 2H), 0.84-0.75 (m, 2H) | 794.92 (794.37) | 795.6 | D | N.D. | D | N.D. | N.D. | N.D. |
| 171 | 1H NMR: (400 MHz, DMSO-d6) δ: 13.26-13.43 (m, 1 H), 11.02-11.12 (m, 1 H), 8.56-8.67 (m, 1 H), 8.25-8.29 (m, 0.2 H), 8.06-8.17 (m, 1 H), 7.59-7.66 (m, 1 H), 7.45-7.53 (m, 1 H), 7.33-7.39 (m, 1 H), 7.26-7.30 (m, 1 H), 7.19-7.25 (m, 1 H), 7.00-7.14 (m, 5 H), 5.05 (dd, J = 12.88, 5.38 Hz, 1 H), 4.36-4.52 (m, 2 H), 3.99-4.08 (m, 2 H), 2.83 (br d, J = 5.75 Hz, 6 H), 2.54-2.63 (m, 2 H), 1.81 (br d, J = 7.50 Hz, 4 H), 1.59-1.71 (m, 4 H), 1.47-1.55 (m, 3 H), 1.04-1.40 (m, 6 H), 0.90-0.97 (m, 2 H), 0.70-0.80 (m, 2 H). | 792.94 (792.37) | 793.6 | D | C | D | N.D. | N.D. | N.D. |
| 172 | 1H NMR: (400 MHz, DMSO-d6) δ: 13.42 (br s, 1 H), 11.10 (s, 1 H), 10.99-11.18 (m, 1 H), 8.66 (d, J = 0.88 Hz, 1 H), 8.14-8.17 (m, 1 H), 7.78 (s, 2 H), 7.69 (d, J = 8.50 Hz, 1 H), 7.51 (d, J = 9.01 Hz, 1 H), 7.40 (s, 1 H), 7.36 (d, J = 1.88 Hz, 1 H), 7.26 (dd, J = 8.69, 2.06 Hz, 1 H), 7.07 (dd, J = 9.01, 2.38 H), 5.08 (dd, J = 12.82, 5.44 Hz, 1 H), 3.87 (s, 4 H), 3.71 (br s, 4 H), 3.46 (br d, J = 4.50 Hz, 3 H), 2.89 (ddd, J = 17.29, 14.04, 5.44 Hz, 1 H), 2.53-2.62 (m, 10 H), 2.00-2.07 (m, 1 H), 1.55 (s, 3 H), 0.92-0.98 (m, 2 H), 0.75-0.81 (m, 2 H). | 796.89 (796.36) | 797.6 | A | B | A | B | N.D. | N.D. |
| 173 | 1H NMR: (400 MHz, MeOD-d4) δ: 8.24-8.21 (m, 0.2H), 8.16 (d, J = 5.4 Hz, 1H), 7.64 (d, J = 8.6 Hz, 1H), 7.58 (d, J = 2.0 Hz, 1H), 7.50 (d, J = 9.0 Hz, 1H), 7.34 (d, J = 1.5 Hz, 1H), 7.31 (d, J = 2.3 Hz, 1H), 7.23-7.14 (m, 2H), 7.14-7.08 (m, 5H), 5.06 (dd, J = 5.5, 12.5 Hz, 1H), 4.33 (br d, J = 13.3 Hz, 2H), 4.05-3.97 (m, 2H), 3.00-2.80 (m, 5H), 2.78-2.65 (m, 2H), 2.57 (tt, J = 1.5, 6.7 Hz, 4H), 2.17-2.02 (m, 1H), 1.94-1.71 (m, 6H), 1.59 (t, J = 0.8 Hz, 3H), 1.39-1.28 (m, 4H), 1.08-0.97 (m, 2H), 0.80-0.75 (m, 2H) | 791.95 (791.38) | 792.6 | D | N.D. | D | N.D. | N.D. | N.D. |
| 174 | 1H NMR: (400 MHz, MeOD-d4) δ: 8.59 (s, 1H), 8.10-7.98 (m, 1H), 7.66-7.57 (m, 1H), 7.49- | 792.94 (792.37) | 793.6 | D | N.D. | D | N.D. | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 7.42 (m, 1H), 7.39-7.35 (m, 1H), 7.32-7.27 (m, 1H), 7.24-7.13 (m, 2H), 7.11-7.05 (m, 1H), 7.05-6.95 (m, 3H), 5.08-5.03 (m, 1H), 4.58-4.49 (m, 2H), 4.06-3.94 (m, 2H), 2.89 (s, 4H), 2.87-2.79 (m, 1H), 2.76-2.66 (m, 2H), 2.62-2.50 (m, 4H), 2.13-2.05 (m, 1H), 1.98-1.90 (m, 1H), 1.88-1.70 (m, 5H), 1.62-1.58 (m, 3H), 1.37-1.26 (m, 4H), 1.06-0.96 (m, 2H), 0.83-0.71 (m, 2H) | | | | | | | | |
| 175 | 1H NMR: (400 MHz, MeOD-d4) δ: 8.63 (d, J = 1.0 Hz, 1H), 8.49 (s, 1H), 8.10 (d, J = 2.0 Hz, 1H), 7.69 (d, J = 8.5 Hz, 1H), 7.49 (d, J = 9.0 Hz, 1H), 7.41 (s, 1H), 7.36 (d, J = 2.3 Hz, 1H), 7.24 (dd, J = 2.3, 8.7 Hz, 1H), 7.11 (dd, J = 2.3, 9.1 Hz, 1H), 5.09 (dd, J = 5.5, 12.4 Hz, 1H), 4.08 (br d, J = 13.1 Hz, 2H), 3.84 (br d, J = 7.6 Hz, 8H), 3.08-2.96 (m, 4H), 2.90-2.83 (m, 1H), 2.81-2.66 (m, 6H), 2.17-2.07 (m, 1H), 1.84 (br d, J = 14.8 Hz, 7H), 1.62 (s, 3H), 1.43-1.19 (m, 5H), 1.06-1.00 (m, 2H), 0.83-0.77 (m, 2H) | 812.98 (812.41) | 813.7 | A | B | A | B | N.D. | N.D. |
| 176 | 1H NMR: (400 MHz, MeOD-d4) δ: 8.63 (s, 1H), 8.48 (s, 1H), 8.10 (s, 1H), 7.67 (d, J = 8.6 Hz, 1H), 7.48 (d, J = 9.1 Hz, 1H), 7.42 (s, 1H), 7.35 (s, 1H), 7.22 (br d, J = 8.5 Hz, 1H), 7.11 (br d, J = 9.1 Hz, 1H), 5.11-5.08 (m, 1H), 4.09 (br s, 2H), 3.96-3.91 (m, 2H), 3.15 (br s, 2H), 3.08-3.00 (m, 6H), 2.88 (br s, 4H), 2.84 (br d, J = 6.4 Hz, 4H), 2.78 (br s, 2H), 2.48 (br d, J = 7.0 Hz, 2H), 2.11 (br s, 2H), 1.85 (br d, J = 12.5 Hz, 4H), 1.62 (s, 3H), 1.34 (br d, J = 11.9 Hz, 4H), 1.03 (s, 2H), 0.80 (s, 2H) | 812.98 (812.41) | 813.6 | A | C | A | B | N.D. | N.D. |
| 177 | 1H NMR: (400 MHz, MeOD-d4) δ: 8.66 (s, 1H), 8.41 (s, 1H), 8.13 (d, J = 2.0 Hz, 1H), 7.70 (d, J = 8.5 Hz, 1H), 7.48 (d, J = 9.0 Hz, 1H), 7.43 (s, 1H), 7.39 (d, J = 2.3 Hz, 1H), 7.26 (dd, J = 2.3, 8.6 Hz, 1H), 7.12 (dd, J = 2.4, 9.0 Hz, 1H), 5.09 (dd, J = 5.4, 12.4 Hz, 1H), 4.11 (br d, J = 13.0 Hz, 2H), 3.81 (br s, 4H), 3.11-2.99 (m, 5H), 2.94-2.83 (m, 2H), 2.80-2.71 (m, 3H), 2.69-2.59 (m, 8H), 2.22-2.08 (m, 4H), 2.04-1.89 (m, 4H), 1.84 (br t, J = 5.5 Hz, 2H), 1.68 (br d, J = 10.5 Hz, 2H), 1.63 (s, 3H), 1.50-1.37 (m, 2H), 1.06-1.01 (m, 2H), 0.83-0.77 (m, 2H) | 841.03 (840.44) | 841.7 | B | B | B | B | N.D. | N.D. |
| 178 | 1H NMR: (400 MHz, MeOD-d4) δ: 8.68 (d, J = 1.1 Hz, 1H), 8.64 (d, J = 0.9 Hz, 1H), 8.50-8.36 (m, 1H), 7.98 (d, J = 1.1 Hz, 1H), 7.67 (s, 1H), 7.47 (d, J = 0.8 Hz, 1H), 7.38-7.33 (m, 1H), 7.26-7.20 (m, 1H), 5.12-5.02 (m, 1H), 4.65-4.53 (m, 2H), 4.14-4.03 (m, 2H), 3.11-2.97 (m, 5H), 2.94-2.81 (m, 6H), 2.79-2.65 (m, 3H), 2.62-2.53 (m, 4H), 2.18-1.97 (m, 3H), 1.97-1.88 (m, 4H), 1.68 (s, 3H), 1.40-1.24 (m, 4H), 1.06 (s, 2H), 0.85 (d, J = 1.6 Hz, 2H). | 801.95 (801.41) | 802.7 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 179 | 1H NMR: (400 MHz, METHANOL-d4) ?: 8.64 (s, 1H), 8.34 (s, 1H), 8.11 (d, J = 2.0 Hz, 1H), 7.52-7.43 (m, 3H), 7.41 (s, 1H), 7.30-7.25 (m, 1H), 7.10 (dd, J = 2.3, 9.0 Hz, 1H), 5.21-5.13 (m, 1H), 4.50 (d, J = 5.4 Hz, 2H), 3.78 (br s, 4H), 3.51-3.39 (m, 4H), 3.18-3.08 (m, 2H), 3.01 (br d, J = 5.5 Hz, 2H), 2.96-2.81 (m, 4H), 2.75-2.69 (m, 5H), 2.66 (d, J = 1.4 Hz, 1H), 2.58-2.49 (m, 1H), 2.30-2.15 (m, 3H), 2.08-1.90 (m, 5H), 1.61 (s, 3H), 1.57-1.45 (m, 2H), 1.06-1.00 (m, 2H), 0.81-0.76 (m, 2H) | 804.97 (804.42) | 805.6 | N.D. | N.D. | N.D. | N.D. | A | B |
| 180 | 1H NMR: (400 MHz, METHANOL-d4) ?: 8.62 (s, 1H), 8.13-8.03 (m, 1H), 7.41 (s, 3H), 7.27-7.19 (m, 1H), 7.14-7.07 (m, 1H), 5.16-5.05 (m, 1H), 4.64-4.52 (m, 2H), 4.47-4.33 (m, 2H), 3.68-3.54 (m, 2H), 3.14-2.73 (m, 14H), 2.70-2.43 (m, 5H), 2.21-2.01 (m, 2H), 1.91 (s, 5H), 1.62 (s, 3H), 1.55-1.41 (m, 2H), 1.34-1.21 (m, 2H), 1.03 (s, 2H), 0.82-0.74 (m, 2H) | 804.97 (804.42) | 805.6 | N.D. | N.D. | N.D. | N.D. | A | A |
| 181 | 1H NMR: (400 MHz, METHANOL-d4) ?: 8.61 (s, 1H), 8.45 (s, 1H), 8.11-8.05 (m, 1H), 7.54 (d, J = 8.3 Hz, 1H), 7.46 (d, J = 8.9 Hz, 1H), 7.40 (s, 1H), 7.19 (t, J = 7.9 Hz, 1H), 7.12-7.06 (m, 1H), 5.15-5.08 (m, 1H), 4.59-4.43 (m, 4H), 3.65-3.57 (m, 2H), 3.09-2.99 (m, 2H), 2.96-2.64 (m, 11H), 2.62-2.43 (m, 5H), 2.21-2.11 (m, 1H), 2.10-1.77 (m, 7H), 1.63-1.59 (m, 3H), 1.51-1.39 (m, 2H), 1.32-1.25 (m, 2H), 1.05-0.99 (m, 2H), 0.81-0.75 (m, 2H) | 804.97 (804.42) | 805.7 | N.D. | N.D. | N.D. | N.D. | A | A |
| 182 | 1H NMR: (400 MHz, METHANOL-d4) ?: 8.63 (s, 1H), 8.48 (br s, 1H), 8.10 (d, J = 2.4 Hz, 1H), 7.54 (d, J = 8.3 Hz, 1H), 7.46 (d, J = 9.0 Hz, 1H), 7.39 (s, 1H), 7.19 (t, J = 7.9 Hz, 1H), 7.09 (dd, J = 2.3, 9.1 Hz, 1H), 5.12 (dd, J = 5.1, 13.4 Hz, 1H), 4.57-4.43 (m, 2H), 3.82-3.72 (m, 4H), 3.67-3.58 (m, 2H), 3.15-3.02 (m, 2H), 2.92-2.83 (m, 3H), 2.81-2.58 (m, 11H), 2.56-2.45 (m, 1H), 2.21-2.08 (m, 3H), 2.01-1.83 (m, 5H), 1.61 (s, 3H), 1.55-1.41 (m, 2H), 1.05-0.97 (m, 2H), 0.82-0.73 (m, 2H) | 822.96 (822.41) | 823.6 | N.D. | N.D. | N.D. | N.D. | A | A |
| 183 | 1H NMR: (400 MHz, DMSO-d6) δ: 13.52-13.28 (m, 1H), 10.97 (s, 1H), 8.64 (s, 1H), 8.16 (s, 1H), 8.15 (d, J = 1.8 Hz, 1H), 7.49 (s, 1H), 7.44-7.34 (m, 2H), 7.26-7.19 (m, 1H), 7.12-7.02 (m, 1H), 5.14-5.02 (m, 1H), 4.41-4.15 (m, 2H), 3.67 (s, 4H), 3.52-3.44 (m, 3H), 2.96-2.84 (m, 1H), 2.81-2.70 (m, 2H), 2.58 (d, J = 4.5 Hz, 8H), 2.39-2.34 (m, 1H), 2.21 (d, J = 5.9 Hz, 4H), 2.03-1.92 (m, 1H), 1.83 (s, 7H), 1.54 (s, 3H), 1.36-1.20 (m, 2H), 0.95 (s, 2H), 0.77 (d, J = 1.6 Hz, 2H). | 822.96 (822.41) | 823.33 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 184 | 1H NMR: (400 MHz, $CD_3OD$) δ: 8.71-8.58 (m, 1H), 8.46-8.36 (m, 1H), 8.17-8.06 (m, 1H), 7.60-7.52 (m, 1H), 7.51-7.45 (m, 1H), 7.44-7.36 (m, 1H), 7.23-7.14 (m, 1H), 7.14-7.06 (m, 1H), 5.18-5.07 (m, 1H), 4.60-4.42 (m, 2H), 4.11-3.95 (m, 2H), 3.71-3.55 (m, 3H), 3.40-3.33 (m, 2H), 3.29-3.21 (m, 5H), 3.21-3.13 (m, 1H), 3.10-2.98 (m, 3H), 2.97-2.86 (m, 1H), 2.84-2.70 (m, 3H), 2.69-2.62 (m, 4H), 2.57-2.47 (m, 2H), 2.42-2.31 (m, 2H), 2.21-2.13 (m, 1H), 2.13-2.04 (m, 2H), 2.02-1.88 (m, 1H), 1.66-1.59 (m, 3H), 1.59-1.45 (m, 2H), 1.25-1.16 (m, 3H), 1.08-0.96 (m, 2H), 0.85-0.72 (m, 2H). | 834.01 (833.45) | 834.27 | N.D. | N.D. | N.D. | N.D. | A | A |
| 185 | 1H NMR: (400 MHz, DMSO-d6) δ: 13.78-12.95 (m, 1H), 11.26-10.64 (m, 1H), 8.63 (d, J = 0.9 Hz, 1H), 8.37 (d, J = 8.5 Hz, 1H), 7.48-7.35 (m, 3H), 7.22 (d, J = 7.8 Hz, 1H), 5.12-4.98 (m, 1H), 4.54-4.18 (m, 4H), 3.50-3.44 (m, 2H), 3.00-2.87 (m, 3H), 2.78-2.69 (m, 2H), 2.63-2.55 (m, 2H), 2.44-2.33 (m, 8H), 2.15 (br dd, J = 6.7, 13.3 Hz, 4H), 2.01-1.93 (m, 1H), 1.89-1.75 (m, 5H), 1.72-1.63 (m, 1H), 1.57 (s, 3H), 1.33-1.22 (m, 2H), 1.07 (br d, J = 11.1 Hz, 2H), 1.02-0.96 (m, 2H), 0.85-0.76 (m, 2H) | 822.96 (822.41) | 823.23 | N.D. | N.D. | N.D. | N.D. | | |
| 186 | 1H NMR: (400 MHz, DMSO-d6) δ: 13.43 (s, 1H), 10.96 (s, 1H), 8.62 (s, 1H), 8.38 (br d, J = 8.3 Hz, 1H), 7.40-7.48 (m, 2H), 7.36 (s, 1H), 7.15 (t, J = 7.9 Hz, 1H), 5.02-5.10 (m, 1H), 4.20-4.54 (m, 4H), 3.45-3.52 (m, 2H), 2.84-3.00 (m, 3H), 2.76 (br t, J = 11.7 Hz, 2H), 2.52-2.69 (m, 4H), 2.34-2.41 (m, 6H), 2.15 (br dd, J = 12.3, 6.9 Hz, 4H), 1.85-2.03 (m, 2H), 1.80 (br d, J = 12.9 Hz, 4H), 1.62-1.73 (m, 1H), 1.57 (s, 3H), 1.19-1.32 (m, 2H), 1.04-1.16 (m, 2H), 0.96-1.02 (m, 2H), 0.77-0.83 (m, 2H) | 822.96 (822.41) | 823.40 | N.D. | N.D. | N.D. | N.D. | A | A |
| 187 | 1H NMR: (400 MHz, $CD_3OD$) δ: 8.75-8.60 (m, 1H), 8.18-8.02 (m, 1H), 7.59-7.53 (m, 1H), 7.51-7.46 (m, 1H), 7.43-7.38 (m, 1H), 7.25-7.18 (m, 1H), 7.15-7.02 (m, 1H), 5.29-5.05 (m, 1H), 4.56-4.42 (m, 2H), 4.09-3.84 (m, 2H), 3.72-3.53 (m, 3H), 3.31-3.09 (m, 4H), 3.02-2.66 (m, 10H), 2.64-2.46 (m, 3H), 2.31-2.05 (m, 3H), 2.02-1.78 (m, 5H), 1.67-1.59 (m, 3H), 1.58-1.44 (m, 2H), 1.20-1.11 (m, 3H), 1.07-0.97 (m, 2H), 0.86-0.74 (m, 2H) | 836.99 (836.43) | 837.59 | N.D. | N.D. | N.D. | N.D. | A | A |
| 188 | 1H NMR: (400 MHz, DMSO-d6) δ: 13.36 (s, 1H), 10.97 (s, 1H), 8.62 (d, J = 1.0 Hz, 1H), 8.14 (s, 1H), 7.50 (d, J = 9.0 Hz, 1H), 7.42 (d, J = 11.6 Hz, 1H), 7.37 (s, 1H), 7.23 (d, J = 7.6 Hz, 1H), 7.06 (dd, J = 2.4, 9.0 Hz, 1H), 5.07 (dd, J = 5.1, 13.4 Hz, 1H), 4.52-4.18 (m, 4H), 3.11 (br s, 4H), 2.99-2.85 (m, 3H), 2.63-2.56 (m, 4H), 2.44-2.34 (m, 4H), 2.28-2.13 (m, 5H), 2.02-1.94 (m, 1H), 1.92-1.59 (m, 8H), 1.54 (s, 3H), 1.13-1.02 (m, 2H), 0.99-0.91 (m, 2H), 0.82-0.72 (m, 2H) | 822.96 (822.41) | 823.50 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 189 | 1H NMR: (400 MHz, $CD_3OD$) δ: 8.67-8.59 (m, 1H), 8.37-8.28 (m, 1H), 7.58-7.51 (m, 1H), 7.45-7.38 (m, 1H), 7.33-7.24 (m, 1H), 7.23-7.14 (m, 1H), 5.18-5.06 (m, 1H), 4.57-4.44 (m, 2H), 3.83-3.70 (m, 4H), 3.68-3.56 (m, 2H), 3.18-3.05 (m, 2H), 2.96-2.59 (m, 14H), 2.56-2.45 (m, 1H), 2.21-2.08 (m, 3H), 2.01-1.80 (m, 5H), 1.69-1.60 (m, 3H), 1.55-1.41 (m, 2H), 1.11-1.02 (m, 2H), 0.86-0.77 (m, 2H) | 840.95 (840.40) | 841.49 | N.D. | N.D. | N.D. | N.D. | A | A |
| 190 | 1H NMR: (400 MHz, $CD_3OD$) δ: 8.64-8.61 (m, 1H), 8.36-8.29 (m, 1H), 8.11-8.07 (m, 1H), 7.57-7.52 (m, 1H), 7.50-7.40 (m, 2H), 7.21-7.13 (m, 1H), 7.13-7.07 (m, 1H), 5.14-5.08 (m, 1H), 4.61 (br d, J = 13.1 Hz, 2H), 4.53-4.44 (m, 2H), 3.39 (br d, J = 10.4 Hz, 2H), 3.27-3.21 (m, 4H), 3.13-3.04 (m, 4H), 2.98-2.93 (m, 2H), 2.91 (br s, 1H), 2.82-2.74 (m, 5H), 2.71 (s, 1H), 2.67-2.64 (m, 1H), 2.55-2.43 (m, 1H), 2.28-2.13 (m, 4H), 2.09-2.00 (m, 1H), 1.99-1.90 (m, 3H), 1.63-1.59 (m, 3H), 1.35 (dq, J = 3.8, 12.1 Hz, 2H), 1.05-0.99 (m, 2H), 0.81-0.75 (m, 2H) | 822.96 (822.41) | 823.50 | N.D. | N.D. | N.D. | N.D. | A | A |
| 191 | 1H NMR: (400 MHz, DMSO-d6) δ: 10.97 (s, 1H), 8.78 (d, J = 0.8 Hz, 1H), 8.62 (s, 1H), 8.18 (s, 1H), 7.79 (d, J = 1.2 Hz, 1H), 7.42-7.35 (m, 2H), 7.22 (d, J = 7.8 Hz, 1H), 5.06 (dd, J = 5.2, 13.2 Hz, 1H), 4.53-4.39 (m, 2H), 4.38-4.30 (m, 1H), 4.27-4.19 (m, 1H), 3.45 (br d, J = 5.2 Hz, 4H), 3.03-2.81 (m, 4H), 2.77-2.67 (m, 2H), 2.63-2.55 (m, 1H), 2.41-2.32 (m, 6H), 2.16 (br dd, J = 6.8, 13.2 Hz, 4H), 2.03-1.93 (m, 1H), 1.88-1.75 (m, 5H), 1.74-1.64 (m, 1H), 1.61 (s, 3H), 1.34-1.19 (m, 2H), 1.15-1.01 (m, 2H), 0.96-0.89 (m, 2H), 0.79-0.73 (m, 2H). | 805.96 (805.42) | | N.D. | N.D. | N.D. | N.D. | A | A |
| 192 | 1H NMR: (400 MHz, $CD_3OD$) δ: 8.64 (d, J = 0.9 Hz, 1H), 8.45 (s, 1H), 8.35 (d, J = 8.1 Hz, 1H), 7.56 (d, J = 8.3 Hz, 1H), 7.43 (s, 1H), 7.31 (d, J = 10.5 Hz, 1H), 7.22 (t, J = 7.9 Hz, 1H), 5.14 (dd, J = 13.3, 5.1 Hz, 1H), 4.44-4.57 (m, 2H), 3.93-4.06 (m, 2H), 3.51-3.71 (m, 4H), 3.11-3.17 (m, 1H), 2.86-3.07 (m, 9H), 2.73-2.84 (m, 2H), 2.43-2.70 (m, 4H), 2.24-2.34 (m, 1H), 2.11-2.23 (m, 2H), 1.88-2.05 (m, 5H), 1.66 (s, 3H), 1.48-1.58 (m, 2H), 1.16 (d, J = 6.3 Hz, 3H), 1.06-1.11 (m, 2H), 0.80-0.86 (m, 2H) | 854.98 (854.42) | 855.43 | N.D. | N.D. | N.D. | N.D. | A | A |
| 193 | 1H NMR: (400 MHz, $CD_3OD$) δ: 8.65 (s, 1H), 8.39 (br s, 1H), 8.35 (br d, J = 8.1 Hz, 1H), 7.49-7.40 (m, 2H), 7.31 (d, J = 10.6 Hz, 1H), 7.22 (br d, J = 7.3 Hz, 1H), 5.13 (br dd, J = 5.2, 13.1 Hz, 1H), 4.43 (br d, J = 6.4 Hz, 2H), 3.43-3.37 (m, 2H), 3.26-3.05 (m, 10H), 2.94 (br d, J = 12.5 Hz, 5H), 2.81 (br s, 3H), 2.74-2.65 (m, 1H), 2.22 (br d, J = 7.8 Hz, 4H), 2.15-2.04 (m, 1H), 1.96 (br d, J = 13.0 Hz, 4H), 1.66 (s, 3H), 1.42-1.27 (m, 3H), 1.12-1.04 (m, 2H), 0.85-0.79 (m, 2H) | 840.95 (840.40) | 841.43 | N.D. | N.D. | N.D. | N.D. | A | A |
| 194 | 1H NMR: (400 MHz, DMSO-d6) δ: 13.53-13.13 (m, 1H), 11.18-10.83 (m, 1H), 8.20-8.17 (m, 1H), 8.16- | 817.01 (816.44) | 817.47 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 8.13 (m, 1H), 7.62-7.48 (m, 1H), 7.41-7.33 (m, 1H), 7.22-7.11 (m, 1H), 7.10-7.02 (m, 2H), 5.11-5.03 (m, 1H), 4.50-4.39 (m, 2H), 4.31-4.18 (m, 2H), 3.87-3.84 (m, 3H), 2.99-2.85 (m, 4H), 2.63-2.54 (m, 6H), 2.46-2.34 (m, 7H), 2.23-2.10 (m, 4H), 2.03-1.93 (m, 1H), 1.92-1.73 (m, 5H), 1.72-1.60 (m, 1H), 1.59-1.50 (m, 3H), 1.32-1.20 (m, 2H), 1.15-1.00 (m, 2H), 0.99-0.88 (m, 2H), 0.83-0.70 (m, 2H) | | | | | | | | |
| 195 | 1H NMR: (400 MHz, DMSO-d6) δ: 13.60-13.40 (m, 1H), 11.07-10.88 (m, 1H), 8.70-8.60 (m, 1H), 8.45-8.34 (m, 1H), 7.51-7.36 (m, 3H), 7.26-7.19 (m, 1H), 5.12-5.02 (m, 1H), 4.38 (s, 2H), 3.74-3.60 (m, 4H), 3.52-3.47 (m, 2H), 2.96-2.85 (m, 1H), 2.81-2.70 (m, 2H), 2.55 (br s, 8H), 2.39-2.30 (m, 2H), 2.28-2.15 (m, 4H), 2.03-1.62 (m, 8H), 1.60-1.54 (m, 3H), 1.34-1.19 (m, 2H), 1.06-0.94 (m, 2H), 0.85-0.70 (m, 2H) | 840.95 (840.40) | 841.42 | N.D. | N.D. | N.D. | N.D. | A | A |
| 196 | 1H NMR: (400 MHz, $CD_3OD$) δ: 8.62 (s, 1H), 8.43 (br s, 1H), 8.10 (d, J = 2.0 Hz, 1H), 7.36-7.49 (m, 3H), 7.22 (d, J = 7.3 Hz, 1H), 7.09 (dd, J = 9.0, 2.3 Hz, 1H), 5.11 (dd, J = 13.3, 5.1 Hz, 1H), 4.33-4.47 (m, 2H), 3.90-4.06 (m, 2H), 3.54-3.67 (m, 3H), 3.37 (br s, 2H), 2.67-3.19 (m, 12H), 2.51-2.63 (m, 2H), 2.39-2.49 (m, 1H), 2.24-2.36 (m, 1H), 2.12-2.22 (m, 2H), 1.89-2.09 (m, 5H), 1.61 (s, 3H), 1.45-1.58 (m, 2H), 1.14 (d, J = 6.3 Hz, 3H), 0.98-1.05 (m, 2H), 0.74-0.82 (m, 2H) | 836.99 (836.43) | 837.25 | N.D. | N.D. | N.D. | N.D. | A | A |
| 197 | 1H NMR: (400 MHz, $CD_3OD$) δ: 8.63 (s, 1H), 8.41 (s, 1H), 8.33 (d, J = 8.1 Hz, 1H), 7.35-7.45 (m, 2H), 7.29 (d, J = 10.5 Hz, 1H), 7.22 (br d, J = 7.3 Hz, 1H), 5.12 (br d, J = 8.3 Hz, 1H), 4.36-4.44 (m, 2H), 3.91-4.03 (m, 2H), 3.50-3.67 (m, 4H), 3.14 (br d, J = 8.3 Hz, 2H), 2.89-3.07 (m, 6H), 2.78-2.89 (m, 4H), 2.37-2.78 (m, 6H), 2.26-2.35 (m, 1H), 2.11-2.21 (m, 2H), 1.88-2.06 (m, 5H), 1.64 (s, 3H), 1.48-1.58 (m, 2H), 1.14 (br d, J = 6.1 Hz, 3H), 1.04-1.09 (m, 2H), 0.78-0.84 (m, 2H) | 854.98 (854.42) | 855.24 | N.D. | N.D. | N.D. | N.D. | A | A |
| 198 | 1H NMR: (400 MHz, $CD_3OD$) δ: 8.66-8.59 (m, 1H), 8.15-8.06 (m, 1H), 7.52-7.43 (m, 1H), 7.43-7.36 (m, 1H), 7.34-7.28 (m, 1H), 7.19-7.13 (m, 1H), 7.12-7.05 (m, 1H), 5.18-5.07 (m, 1H), 4.44-4.31 (m, 2H), 3.96-3.90 (m, 3H), 3.82-3.70 (m, 4H), 3.64-3.55 (m, 2H), 3.28-3.21 (m, 2H), 2.75 (br s, 6H), 2.75-2.65 (m, 7H), 2.65-2.60 (m, 1H), 2.53-2.43 (m, 1H), 2.28-2.10 (m, 3H), 2.05-1.84 (m, 5H), 1.65-1.58 (m, 3H), 1.58-1.45 (m, 2H), 1.06-0.96 (m, 2H), 0.84-0.70 (m, 2H) | 835.00 (834.43) | 835.25 | N.D. | N.D. | N.D. | N.D. | A | A |
| 199 | 1H NMR: (400 MHz, $CD_3OD$) δ: 8.65 (d, J = 0.9 Hz, 1H), 8.42 (s, 1H), 8.34 (d, J = 8.3 Hz, 1H), 7.57 (d, J = 8.3 Hz, 1H), 7.46 (s, 1H), 7.31 (d, J = 10.6 Hz, 1H), 7.19 (t, J = 7.9 Hz, 1H), 5.14 (dd, J = 5.1, 13.4 Hz, 1H), 4.66-4.58 (m, 3H), 4.56-4.46 (m, 2H), 3.26 (br s, 4H), 3.13-2.85 (m, 8H), 2.83-2.77 (m, 5H), 2.73-2.65 (m, 2H), 2.58- | 840.95 (840.40) | 841.23 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 2.46 (m, 1H), 2.25-2.15 (m, 4H), 2.03-1.90 (m, 4H), 1.66 (s, 3H), 1.42-1.31 (m, 2H), 1.12-1.06 (m, 2H), 0.86-0.81 (m, 2H) | | | | | | | | |
| 200 | 1H NMR: (400 MHz, $CD_3OD$) δ: 8.73-8.54 (m, 1H), 8.39 (br s, 1H), 7.58-7.52 (m, 1H), 7.51-7.46 (m, 1H), 7.24-7.15 (m, 1H), 7.14-7.09 (m, 1H), 7.08-7.02 (m, 1H), 5.18-5.08 (m, 1H), 4.57-4.47 (m, 2H), 4.46-4.37 (m, 2H), 4.13-3.99 (m, 2H), 3.75-3.58 (m, 4H), 3.56-3.43 (m, 1H), 3.28-3.17 (m, 2H), 3.07-2.75 (m, 8H), 2.58-2.43 (m, 1H), 2.25-1.88 (m, 8H), 1.68-1.59 (m, 3H), 1.58-1.44 (m, 2H), 1.09-0.96 (m, 2H), 0.86-0.73 (m, 2H) | 809.92 (809.38) | 810.20 | N.D. | N.D. | N.D. | N.D. | A | A |
| 201 | 1H NMR: (400 MHz, DMSO-d6) δ: 10.98 (s, 1H), 8.78 (s, 1H), 8.62 (s, 1H), 8.24 (s, 1H), 7.79 (s, 1H), 7.46 (d, J = 8.0 Hz, 1H), 7.37 (s, 1H), 7.15 (t, J = 7.6 Hz, 1H), 5.07 (dd, J = 5.2, 13.2 Hz, 1H), 4.58-4.17 (m, 4H), 3.03-2.56 (m, 10H), 2.42-2.26 (m, 5H), 2.20-2.11 (m, 5H), 2.01-1.92 (m, 2H), 1.88-1.74 (m, 5H), 1.89-1.73 (m, 1H), 1.60 (m, 3H), 1.33-1.17 (m, 2H), 1.14-0.98 (m, 2H), 0.97-0.85 (m, 2H), 0.81-0.66 (m, 2H). | 805.96 (805.42) | 806.24 | N.D. | N.D. | N.D. | N.D. | A | A |
| 202 | 1H NMR: (400 MHz, DMSO-d6) δ: 13.47 (br s, 1H), 11.06 (s, 1H), 8.71 (d, J = 0.9 Hz, 1H), 8.22 (s, 2H), 7.60-7.49 (m, 2H), 7.44 (s, 1H), 7.22 (t, J = 8.0 Hz, 1H), 7.13 (dd, J = 2.4, 9.0 Hz, 1H), 5.14 (dd, J = 5.1, 13.3 Hz, 1H), 4.59-4.33 (m, 2H), 3.73 (br s, 4H), 3.20 (br s, 4H), 3.03-2.93 (m, 1H), 2.69-2.59 (m, 4H), 2.51-2.43 (m, 6H), 2.34-2.27 (m, 1H), 2.21 (br t, J = 6.8 Hz, 3H), 2.08-1.99 (m, 1H), 1.88 (br d, J = 8.0 Hz, 4H), 1.63-1.53 (m, 5H), 1.04-0.87 (m, 6H), 0.87-0.81 (m, 2H) | 804.97 (804.42) | 805.44 | N.D. | N.D. | N.D. | N.D. | A | A |
| 203 | 1H NMR: (400 MHz, DMSO-d6): 13.55 (br s, 1H), 11.06 (s, 1H), 8.72 (d, J = 0.8 Hz, 1H), 8.45 (d, J = 8.3 Hz, 1H), 8.22 (s, 1H), 7.58-7.48 (m, 2H), 7.45 (s, 1H), 7.22 (t, J = 7.9 Hz, 1H), 5.14 (dd, J = 5.0, 13.3 Hz, 1H), 4.60-4.31 (m, 2H), 3.74 (br s, 4H), 3.20 (br dd, J = 1.5, 2.3 Hz, 4H), 3.02-2.92 (m, 1H), 2.70-2.59 (m, 4H), 2.48 (br d, J = 5.3 Hz, 6H), 2.31 (br t, J = 6.4 Hz, 1H), 2.21 (br t, J = 7.0 Hz, 3H), 2.09-1.99 (m, 1H), 1.96-1.77 (m, 4H), 1.64 (s, 3H), 1.60-1.52 (m, 2H), 1.09-1.04 (m, 2H), 1.02-0.89 (m, 4H), 0.89-0.85 (m, 2H) | 822.96 (822.41) | 823.43 | N.D. | N.D. | N.D. | N.D. | A | A |
| 204 | 1H NMR: (400 MHz, DMSO-d6) δ: 13.55-13.27 (m, 1H), 10.99-10.94 (m, 1H), 8.69-8.60 (m, 1H), 8.16-8.14 (m, 1H), 7.56-7.47 (m, 1H), 7.47-7.40 (m, 1H), 7.39-7.36 (m, 1H), 7.26-7.20 (m, 1H), 7.11-7.05 (m, 1H), 5.15-4.98 (m, 1H), 4.43-4.20 (m, 2H), 3.70-3.65 (m, 4H), 3.14-3.10 (m, 4H), 2.99-2.85 (m, 2H), 2.65-2.56 (m, 2H), 2.46-2.36 (m, 6H), 2.29-2.20 (m, 1H), 2.20-2.10 (m, 4H), 2.03-1.94 (m, 1H), | 804.97 (804.42) | 805.29 | N.D. | N.D. | N.D. | N.D. | N.D. | N.D. |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1.89-1.75 (m, 4H), 1.58-1.54 (m, 3H), 1.53-1.44 (m, 2H), 0.98-0.93 (m, 2H), 0.93-0.81 (m, 4H), 0.80-0.75 (m, 2H) | | | | | | | | |
| 205 | 1H NMR: (400 MHz, DMSO-d6) δ: 13.67-13.31 (m, 1H), 11.14-10.84 (m, 1H), 8.71-8.62 (m, 1H), 8.45-8.33 (m, 1H), 7.54-7.34 (m, 3H), 7.28-7.18 (m, 1H), 5.14-5.00 (m, 1H), 4.40-4.22 (m, 2H), 3.70-3.65 (m, 4H), 3.14-3.11 (m, 4H), 2.95-2.86 (m, 2H), 2.63-2.57 (m, 2H), 2.45-2.38 (m, 6H), 2.29-2.23 (m, 1H), 2.22-2.11 (m, 4H), 2.03-1.96 (m, 1H), 1.89-1.74 (m, 4H), 1.61-1.56 (m, 3H), 1.54-1.46 (m, 2H), 1.03-0.98 (m, 2H), 0.98-0.83 (m, 4H), 0.83-0.79 (m, 2H) | 822.96 (822.41) | 823.28 | N.D. | N.D. | N.D. | N.D. | N.D. | N.D. |
| 206 | 1H NMR: (400 MHz, DMSO-d6) δ: 13.38 (s, 1H), 10.99 (s, 1H), 8.62 (s, 1H), 8.16 (d, J = 2.1 Hz, 1H), 7.49 (dd, J = 8.6, 13.6 Hz, 2H), 7.37 (s, 1H), 7.17 (t, J = 7.9 Hz, 1H), 7.07 (dd, J = 2.3, 8.9 Hz, 1H), 5.08 (dd, J = 5.1, 13.2 Hz, 1H), 4.54-4.27 (m, 4H), 3.55-3.46 (m, 3H), 3.03-2.87 (m, 3H), 2.78 (br t, J = 11.9 Hz, 2H), 2.61 (br s, 3H), 2.24-2.13 (m, 4H), 2.02-1.88 (m, 2H), 1.82 (br s, 6H), 1.70 (br t, J = 10.1 Hz, 2H), 1.61-1.51 (m, 5H), 1.35-1.13 (m, 5H), 0.99-0.92 (m, 2H), 0.81-0.75 (m, 2H) | 821.98 (821.42) | 822.36 | N.D. | N.D. | N.D. | N.D. | A | A |
| 207 | 1H NMR: (400 MHz, DMSO-d6) δ: 13.46 (s, 1H), 10.99 (s, 1H), 8.63 (s, 1H), 8.39 (br d, J = 8.3 Hz, 1H), 8.16 (s, 1H), 7.50-7.43 (m, 2H), 7.37 (s, 1H), 7.17 (t, J = 7.9 Hz, 1H), 5.08 (dd, J = 4.9, 13.2 Hz, 1H), 4.53-4.30 (m, 4H), 3.03-2.89 (m, 4H), 2.78 (br t, J = 11.6 Hz, 3H), 2.62 (br s, 3H), 2.25-2.14 (m, 4H), 2.03-1.89 (m, 2H), 1.82 (br s, 6H), 1.72 (br d, J = 10.6 Hz, 2H), 1.64 (br s, 2H), 1.58 (s, 3H), 1.52 (br d, J = 5.5 Hz, 1H), 1.34-1.21 (m, 3H), 1.19-1.11 (m, 2H), 1.04-0.97 (m, 2H), 0.86-0.77 (m, 2H) | 839.97 (839.41) | 840.35 | N.D. | N.D. | N.D. | N.D. | B | B |
| 208 | 1H NMR: (400 MHz, DMSO-d6) δ: 13.39 (s, 1H), 11.04-10.88 (m, 1H), 8.68-8.57 (m, 1H), 8.26-8.02 (m, 1H), 7.56-7.46 (m, 1H), 7.45-7.31 (m, 2H), 7.31-7.14 (m, 1H), 7.12-6.94 (m, 1H), 5.14-5.00 (m, 1H), 4.42-4.20 (m, 2H), 4.13-3.99 (m, 2H), 3.79-3.69 (m, 1H), 3.18-3.04 (m, 5H), 2.93-2.82 (m, 1H), 2.70-2.54 (m, 2H), 2.49-2.45 (m, 3H), 2.43-2.27 (m, 2H), 2.17-2.09 (m, 2H), 2.04-1.91 (m, 3H), 1.89-1.73 (m, 4H), 1.54 (s, 3H), 1.52-1.35 (m, 3H), 1.26 (br s, 1H), 1.24-1.09 (m, 2H), 1.00-0.94 (m, 2H), 0.93-0.82 (m, 2H), 0.80-0.72 (m, 2H) | 805.96 (805.41) | 806.40 | N.D. | N.D. | N.D. | N.D. | A | B |
| 209 | 1H NMR: (400 MHz, DMSO-d6): 13.50-13.34 (m, 1H), 11.06-10.91 (m, 1H), 8.69-8.58 (m, 1H), 8.24-8.15 (m, 1H), 7.57-7.46 (m, 2H), 7.41-7.34 (m, 1H), 7.29-7.18 (m, 1H), 7.16-7.02 (m, 1H), 5.14-5.06 (m, 1H), 4.64-4.26 (m, 4H), 3.35 (br s, 6H), 3.08-2.92 (m, 4H), 2.67-2.57 (m, 4H), 2.49-2.38 (m, 4H), | 822.96 (822.41) | 823.35 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 2.23-2.10 (m, 2H), 2.06-1.72 (m, 8H), 1.61-1.52 (m, 3H), 1.17-1.04 (m, 2H), 1.02-0.92 (m, 2H), 0.80-0.79 (m, 1H), 0.87-0.69 (m, 2H) | | | | | | | | |
| 210 | 1H NMR: (400 MHz, DMSO-d6) δ: 11.13-10.91 (m, 1H), 8.78 (s, 1H), 8.63 (s, 1H), 8.41 (s, 1H), 7.84-7.76 (m, 1H), 7.51-7.36 (m, 2H), 7.16 (t, J = 8.0 Hz, 1H), 5.07 (dd, J = 5.2, 13.2 Hz, 1H), 4.47 (d, J = 17.2 Hz, 1H), 4.30 (d, J = 17.2 Hz, 1H), 4.11-4.02 (m, 2H), 3.74-3.67 (m, 2H), 3.60-3.56 (m, 2H), 2.99-2.84 (m, 4H), 2.61 (s, 1H), 2.56 (s, 1H), 2.41 (dd, J = 4.8, 13.2 Hz, 1H), 1.99-1.83 (m, 10H), 1.61 (s, 3H), 1.56 (d, J = 9.6 Hz, 2H), 1.48-1.37 (m, 2H), 1.25 (d, J = 8.4 Hz, 5H), 0.96-0.89 (m, 2H), 0.79-0.72 (m, 2H) | 807.93 (807.39) | 808.39 | N.D. | N.D. | N.D. | N.D. | A | A |
| 211 | 1H NMR: (400 MHz, $CD_3OD$) δ: 8.61 (d, J = 0.6 Hz, 1H), 8.44 (s, 1H), 8.08 (d, J = 2.1 Hz, 1H), 7.47 (dd, J = 4.3, 8.6 Hz, 2H), 7.40 (d, J = 0.9 Hz, 1H), 7.18-7.05 (m, 2H), 5.15-5.07 (m, 1H), 4.64-4.54 (m, 2H), 4.46 (d, J = 12.0 Hz, 2H), 3.94 (d, J = 9.9 Hz, 3H), 3.72-3.62 (m, 2H), 3.09-2.83 (m, 10H), 2.81-2.63 (m, 6H), 2.55 (d, J = 6.9 Hz, 3H), 2.21-2.12 (m, 1H), 2.08-1.99 (m, 1H), 1.93 (d, J = 13.0 Hz, 5H), 1.61 (s, 3H), 1.55-1.41 (m, 2H), 1.35-1.19 (m, 2H), 1.02 (s, 2H), 0.78 (d, J = 1.8 Hz, 2H). | 817.01 (816.44) | 817.7 | N.D. | N.D. | N.D. | N.D. | A | A |
| 212 | 1H NMR: (400 MHz, $CD_3OD$) δ: 8.62 (d, J = 1.0 Hz, 1H), 8.45 (s, 1H), 8.10 (s, 1H), 7.47 (t, J = 8.3 Hz, 2H), 7.39 (s, 1H), 7.19-7.05 (m, 2H), 5.13-5.08 (m, 1H), 4.46 (d, J = 12.1 Hz, 2H), 3.92 (s, 3H), 3.76 (s, 4H), 3.72-3.65 (m, 2H), 3.27-3.23 (m, 2H), 3.00-2.84 (m, 5H), 2.81-2.68 (m, 8H), 2.65-2.60 (m, 1H), 2.56-2.43 (m, 1H), 2.25-2.12 (m, 3H), 2.05-1.89 (m, 5H), 1.60 (s, 3H), 1.57-1.46 (m, 2H), 1.01 (s, 2H), 0.77 (d, J = 1.8 Hz, 2H). | 835.00 (834.43) | 835.7 | N.D. | N.D. | N.D. | N.D. | A | B |
| 213 | 1H NMR: (400 MHz, DMSO-d6) δ: 13.38 (s, 1H), 10.98 (s, 1H), 8.63 (s, 1H), 8.15 (s, 2H), 7.53-7.45 (m, 2H), 7.39 (s, 1H), 7.15 (br t, J = 7.9 Hz, 1H), 7.06 (dd, J = 2.3, 9.0 Hz, 1H), 5.07 (dd, J = 5.1, 13.2 Hz, 1H), 4.51-4.28 (m, 2H), 4.06 (br s, 2H), 3.74 (br s, 1H), 3.13 (br s, 3H), 2.97-2.85 (m, 1H), 2.63-2.52 (m, 4H), 2.47-2.35 (m, 4H), 2.14 (br d, J = 6.9 Hz, 2H), 1.96 (br d, J = 10.9 Hz, 4H), 1.88-1.77 (m, 4H), 1.54 (s, 3H), 1.51-1.32 (m, 4H), 1.22-1.12 (m, 2H), 0.97-0.85 (m, 4H), 0.80-0.73 (m, 2H) | 805.96 (805.41) | 806.6 | N.D. | N.D. | N.D. | N.D. | A | A |
| 214 | 1H NMR: (400 MHz, DMSO-d6) δ: 13.63-13.12 (m, 1H), 11.15-10.75 (m, 1H), 8.83-8.55 (m, 1H), 8.24-8.02 (m, 2H), 7.57-7.46 (m, 1H), 7.39-7.33 (m, 1H), 7.23-7.16 (m, 2H), 7.10-6.99 (m, 1H), 5.23-4.95 (m, 1H), 4.57-4.13 (m, 4H), 3.29-3.13 (m, 3H), 3.04-2.82 (m, 4H), 2.77-2.56 (m, 4H), 2.44-2.27 (m, 6H), 2.24-2.09 (m, 4H), 2.05-1.92 (m, 1H), 1.90-1.70 (m, 5H), 1.68-1.58 (m, 1H), 1.57-1.50 (m, 3H), 1.32-1.18 (m, 2H), 1.16-1.00 (m, 2H), 0.98-0.90 (m, 2H), 0.80-0.70 (m, 2H) | 804.97 (804.42) | 805.58 | N.D. | N.D. | N.D. | N.D. | A | A |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| Degradation and characterization of exemplary bifunctional compounds of the present disclosure | | | | | | | | | |
| 215 | 1H NMR: (400 MHz, $CD_3OD$) δ: 8.68-8.55 (m, 1H), 8.44-8.33 (m, 1H), 8.13-8.04 (m, 1H), 7.52-7.44 (m, 1H), 7.43-7.33 (m, 1H), 7.17-7.06 (m, 1H), 6.71-6.59 (m, 1H), 6.53-6.40 (m, 1H), 5.11-4.99 (m, 1H), 4.62-4.53 (m, 2H), 4.37-4.23 (m, 2H), 4.00-3.92 (m, 2H), 3.90 (s, 3H), 3.10-3.00 (m, 3H), 2.98-2.84 (m, 9H), 2.80-2.72 (m, 2H), 2.68-2.54 (m, 4H), 2.46-2.38 (m, 1H), 2.18-2.02 (m, 2H), 1.98-1.85 (m, 5H), 1.61 (s, 3H), 1.43-1.26 (m, 4H), 1.06-0.98 (m, 2H), 0.78 (d, J = 1.5 Hz, 2H). | 817.01 (816.44) | 817.46 | N.D. | N.D. | N.D. | N.D. | A | A |
| 216 | 1H NMR: (400 MHz, $CD_3OD$) δ: 8.66-8.59 (m, 1H), 8.41 (d, J = 4.6 Hz, 1H), 8.15-8.06 (m, 1H), 7.53-7.43 (m, 1H), 7.41-7.36 (m, 1H), 7.15-7.05 (m, 1H), 6.67-6.59 (m, 1H), 6.55-6.42 (m, 1H), 5.09-5.00 (m, 1H), 4.41-4.24 (m, 2H), 4.02-3.93 (m, 2H), 3.90 (s, 3H), 3.82-3.71 (m, 4H), 3.26-3.16 (m, 2H), 3.01-2.77 (m, 8H), 2.74-2.61 (m, 6H), 2.49-2.36 (m, 1H), 2.23-2.07 (m, 3H), 2.07-1.97 (m, 2H), 1.95-1.85 (m, 3H), 1.61 (s, 3H), 1.46-1.35 (m, 2H), 1.05-0.98 (m, 2H), 0.81-0.74 (m, 2H). | 835.00 (834.43) | 835.45 | N.D. | N.D. | N.D. | N.D. | A | A |
| 217 | 1H NMR: (400 MHz, DMSO-d6) δ: 13.37 (br s, 1H), 10.98 (s, 1H), 8.62 (d, J = 0.9 Hz, 1H), 8.17-8.12 (m, 2H), 7.50 (d, J = 9.0 Hz, 1H), 7.42-7.34 (m, 2H), 7.29 (dd, J = 8.3, 12.3 Hz, 1H), 7.06 (dd, J = 2.4, 9.0 Hz, 1H), 5.09 (dd, J = 5.1, 13.3 Hz, 1H), 4.56-4.33 (m, 4H), 3.25-3.20 (m, 4H), 3.07-2.87 (m, 7H), 2.62-2.55 (m, 1H), 2.38 (br d, J = 0.9 Hz, 5H), 2.16 (br dd, J = 6.9, 12.7 Hz, 4H), 2.02-1.94 (m, 1H), 1.86-1.73 (m, 5H), 1.69-1.58 (m, 1H), 1.54 (s, 3H), 1.30-1.17 (m, 2H), 1.13-1.01 (m, 2H), 0.97-0.90 (m, 2H), 0.80-0.69 (m, 2H) | 804.97 (804.42) | 805.43 | N.D. | N.D. | N.D. | N.D. | B | B |
| 218 | 1H NMR: (400 MHz, $CD_3OD$) δ: 8.78 (d, J = 1.2 Hz, 1H), 8.63 (s, 1H), 8.43 (s, 1H), 7.79 (d, J = 1.2 Hz, 1H), 7.46 (d, J = 8.0 Hz, 1H), 7.40 (s, 1H), 7.17 (t, J = 8.0 Hz, 1H), 5.07 (dd, J = 4.8, 13.2 Hz, 1H), 4.48 (d, J = 17.2 Hz, 1H), 4.34-4.23 (m, 3H), 4.17-4.06 (m, 2H), 3.64-3.53 (m, 2H), 3.52-3.41 (m, 4H), 2.98-2.85 (m, 3H), 2.63-2.55 (m, 1H), 2.45-2.31 (m, 1H), 2.18 (t, J = 5.6 Hz, 4H), 2.02-1.84 (m, 5H), 1.65-1.53 (m, 5H), 1.49-1.37 (m, 2H), 0.96-0.88 (m, 2H), 0.79-0.72 (m, 2H). | 779.87 (779.36) | 780.4 | N.D. | N.D. | N.D. | N.D. | A | B |
| 219 | 1H NMR: (400 MHz, DMSO-d6) δ: 13.37 (s, 1H), 10.99 (s, 1H), 8.62 (s, 1H), 8.15 (s, 1H), 7.50 (d, J = 9.0 Hz, 1H), 7.31-7.42 (m, 2H), 7.06 (dd, J = 9.0, 2.4 Hz, 1H), 5.07 (dd, J = 13.1, 5.0 Hz, 1H), 4.26-4.49 (m, 4H), 3.09 (br t, J = 11.4 Hz, 4H), 2.86-2.99 (m, 4H), 2.61 (br d, J = 2.3 Hz, 4H), 2.37-2.43 (m, 4H), 2.16 (br dd, J = 11.9, 6.9 Hz, 4H), 1.96-2.02 (m, 1H), 1.73-1.93 (m, 6H), 1.64-1.73 (m, 1H), 1.54 (s, 3H), 1.15-1.27 (m, 2H), 1.01-1.13 (m, 2H), 0.91-0.98 (m, 2H), 0.73-0.82 (m, 2H) | 822.96 (822.41) | 823.7 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 220 | 1H NMR: (400 MHz, DMSO-d6) δ: 13.39 (br s, 1H), 10.99 (s, 1H), 8.64 (d, J = 0.9 Hz, 1H), 8.15 (s, 1H), 7.50 (d, J = 9.0 Hz, 1H), 7.31-7.42 (m, 2H), 7.07 (dd, J = 9.0, 2.4 Hz, 1H), 5.07 (dd, J = 13.3, 5.0 Hz, 1H), 4.25-4.53 (m, 2H), 3.67 (br s, 4H), 3.26-3.29 (m, 2H), 3.09 (br t, J = 11.5 Hz, 4H), 2.86-2.96 (m, 1H), 2.55-2.68 (m, 8H), 2.35-2.47 (m, 2H), 2.14-2.27 (m, 4H), 1.93-2.02 (m, 1H), 1.81-1.92 (m, 2H), 1.68-1.80 (m, 4H), 1.54 (s, 3H), 1.16-1.30 (m, 2H), 0.91-0.98 (m, 2H), 0.74-0.80 (m, 2H) | 840.95 (840.40) | 841.7 | N.D. | N.D. | N.D. | N.D. | A | B |
| 221 | 1H NMR: (400 MHz, CDCl3) δ: 8.60 (s, 1H), 8.39 (s, 1H), 8.07 (d, J = 2.0 Hz, 1H), 7.54-7.50 (m, 1H), 7.45 (d, J = 9.0 Hz, 1H), 7.39 (s, 1H), 7.17 (t, J = 7.9 Hz, 1H), 7.08 (dd, J = 2.3, 9.0 Hz, 1H), 5.10 (dd, J = 5.2, 13.3 Hz, 1H), 4.60-4.54 (m, 2H), 4.52-4.42 (m, 2H), 3.60 (br d, J = 10.0 Hz, 2H), 3.35 (br s, 1H), 3.13-2.98 (m, 5H), 2.95-2.83 (m, 4H), 2.82-2.77 (m, 2H), 2.76-2.61 (m, 2H), 2.57 (br d, J = 4.9 Hz, 2H), 2.48 (dq, J = 4.6, 13.2 Hz, 3H), 2.15 (dtd, J = 2.3, 5.2, 12.7 Hz, 1H), 2.08-1.97 (m, 2H), 1.92-1.82 (m, 4H), 1.59 (s, 3H), 1.49-1.39 (m, 2H), 1.30-1.22 (m, 4H), 1.03-0.98 (m, 2H), 0.81-0.72 (m, 2H) | 819.00 (818.44) | 819.7 | N.D. | N.D. | N.D. | N.D. | A | B |
| 222 | 1H NMR: (400 MHz, CD3OD) δ: 8.67-8.57 (m, 1H), 8.53-8.44 (m, 1H), 8.14-8.04 (m, 1H), 7.59-7.50 (m, 1H), 7.49-7.42 (m, 1H), 7.41-7.37 (m, 1H), 7.22-7.15 (m, 1H), 7.12-7.06 (m, 1H), 5.19-5.06 (m, 1H), 4.56 (br s, 4H), 3.67-3.57 (m, 2H), 3.11-2.64 (m, 12H), 2.59-2.27 (m, 6H), 2.20-2.12 (m, 1H), 2.03-1.81 (m, 6H), 1.63-1.58 (m, 3H), 1.52-1.39 (m, 2H), 1.33-1.18 (m, 5H), 1.08-0.98 (m, 2H), 0.82-0.72 (m, 2H) | 819.00 (818.44) | 819.7 | N.D. | N.D. | N.D. | N.D. | A | A |
| 223 | 1H NMR: (400 MHz, CD3OD) δ: 8.62 (s, 1H), 8.48-8.23 (m, 1H), 8.09 (d, J = 2.1 Hz, 1H), 7.49 (d, J = 9.0 Hz, 1H), 7.40 (s, 1H), 7.36 (d, J = 9.8 Hz, 1H), 7.11 (dd, J = 2.3, 9.0 Hz, 1H), 5.14 (dd, J = 5.1, 13.3 Hz, 1H), 4.57-4.48 (m, 4H), 3.53-3.42 (m, 2H), 3.27 (br d, J = 10.4 Hz, 4H), 3.12-2.79 (m, 8H), 2.58-2.47 (m, 1H), 2.24-2.12 (m, 2H), 2.10-1.78 (m, 9H), 1.77-1.65 (m, 2H), 1.63 (s, 3H), 1.50 (br d, J = 11.4 Hz, 2H), 1.38-1.30 (m, 2H), 1.06-1.02 (m, 2H), 0.84-0.77 (m, 2H) | 839.97 (839.41) | 840.7 | N.D. | N.D. | N.D. | N.D. | B | B |
| 224 | 1H NMR: (400 MHz, CD3OD) δ: 8.62 (s, 1H), 8.43 (s, 1H), 8.08 (d, J = 2.0 Hz, 1H), 7.53 (d, J = 8.3 Hz, 1H), 7.46 (d, J = 9.1 Hz, 1H), 7.41 (s, 1H), 7.18 (t, J = 7.8 Hz, 1H), 7.09 (dd, J = 2.3, 9.1 Hz, 1H), 5.15-5.05 (m, 1H), 4.57-4.41 (m, 4H), 3.66-3.56 (m, 2H), 3.29-3.21 (m, 2H), 3.17-2.98 (m, 4H), 2.92-2.73 (m, 6H), 2.55-2.43 (m, 3H), 2.41-2.32 (m, 2H), 2.18-2.12 (m, 1H), 2.08-1.86 (m, 5H), 1.82-1.72 (m, 1H), 1.63-1.59 (m, 3H), 1.49-1.27 (m, 10H), 1.07-0.98 (m, 2H), 0.81-0.75 (m, 2H) | 833.03 (832.45) | 833.7 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 225 | 1H NMR: (400 MHz, CD3OD) δ: 8.63 (d, J = 0.9 Hz, 1H), 8.44 (br s, 1H), 8.10 (d, J = 2.1 Hz, 1H), 7.59-7.54 (m, 1H), 7.49 (d, J = 9.0 Hz, 1H), 7.42 (s, 1H), 7.20 (br t, J = 7.6 Hz, 1H), 7.12 (dd, J = 2.4, 9.0 Hz, 1H), 5.14 (dd, J = 5.1, 13.3 Hz, 1H), 4.59-4.45 (m, 4H), 4.44-4.33 (m, 2H), 3.65 (br d, J = 9.6 Hz, 2H), 3.52-3.41 (m, 2H), 3.25-3.16 (m, 2H), 3.11-2.81 (m, 8H), 2.78-2.60 (m, 3H), 2.58-2.41 (m, 2H), 2.19 (tdd, J = 2.5, 5.1, 12.6 Hz, 1H), 2.05-1.87 (m, 6H), 1.63 (d, J = 0.8 Hz, 3H), 1.59 (br d, J = 8.3 Hz, 2H), 1.33-1.21 (m, 2H), 1.06-1.01 (m, 2H), 0.82-0.77 (m, 2H) | 816.98 (816.42) | 817.7 | N.D. | N.D. | N.D. | N.D. | A | B |
| 226 | 1H NMR: (400 MHz, DMSO-d6) δ: 13.49-13.22 (m, 1H), 11.08-10.83 (m, 1H), 8.67-8.54 (m, 1H), 8.25-8.00 (m, 2H), 7.54-7.43 (m, 2H), 7.40-7.34 (m, 1H), 7.21-7.12 (m, 1H), 7.09-7.02 (m, 1H), 5.17-4.99 (m, 1H), 4.54-4.22 (m, 4H), 3.02-2.84 (m, 4H), 2.81-2.64 (m, 8H), 2.58-2.55 (m, 2H), 2.44-2.37 (m, 5H), 2.04-1.93 (m, 1H), 1.89-1.79 (m, 4H), 1.73-1.61 (m, 4H), 1.58-1.48 (m, 3H), 1.37-1.22 (m, 2H), 1.18-1.04 (m, 2H), 0.99-0.92 (m, 2H), 0.80-0.73 (m, 2H). | 816.98 (816.42) | 817.7 | N.D. | N.D. | N.D. | N.D. | A | B |
| 227 | 1H NMR: (400 MHz, DMSO-d6) δ: 10.97 (s, 1H), 8.66 (s, 1H), 8.37-8.21 (m, 1H), 7.54-7.34 (m, 3H), 7.16 (t, J = 8.0 Hz, 1H), 5.06 (dd, J = 5.2, 13.2 Hz, 1H), 4.47 (d, J = 17.2 Hz, 1H), 4.31 (d, J = 16.8 Hz, 1H), 4.12-4.02 (m, 2H), 3.72 (d, J = 7.2 Hz, 2H), 3.61-3.57 (m, 2H), 3.00-2.83 (m, 4H), 2.63-2.53 (m, 3H), 2.41 (dd, J = 4.8, 13.2 Hz, 1H), 2.03-1.79 (m, 10H), 1.62-1.51 (m, 5H), 1.50-1.39 (m, 2H), 1.31-1.22 (m, 4H), 1.05-0.97 (m, 2H), 0.84-0.76 (m, 2H) | 824.93 (824.38) | 825.4 | N.D. | N.D. | N.D. | N.D. | A | B |
| 228 | 1H NMR: (400 MHz, DMSO-d6) δ: 13.49-13.27 (m, 1H), 11.09-10.95 (m, 1H), 8.70-8.57 (m, 1H), 8.20-8.10 (m, 1H), 7.56-7.44 (m, 2H), 7.42-7.35 (m, 1H), 7.22-7.12 (m, 1H), 7.10-7.03 (m, 1H), 5.14-5.00 (m, 1H), 4.55-4.26 (m, 2H), 4.14-4.00 (m, 2H), 3.77-3.67 (m, 1H), 3.64-3.54 (m, 1H), 3.51-3.40 (m, 4H), 2.99-2.88 (m, 3H), 2.70-2.55 (m, 2H), 2.45-2.36 (m, 1H), 2.01-1.81 (m, 10H), 1.54 (s, 5H), 1.46-1.37 (m, 2H), 1.31-1.21 (m, 4H), 1.01-0.89 (m, 2H), 0.82-0.73 (m, 2H). | 806.94 (806.39) | 807.6 | N.D. | N.D. | N.D. | N.D. | B | B |
| 229 | 1H NMR: (400 MHz, DMSO-d6) δ: 13.60-13.38 (m, 1H), 11.09-10.88 (m, 1H), 8.71-8.62 (m, 1H), 8.46-8.34 (m, 1H), 7.56-7.42 (m, 2H), 7.41-7.34 (m, 1H), 7.29-7.15 (m, 1H), 5.19-5.04 (m, 1H), 4.65-4.23 (m, 4H), 3.31-3.24 (m, 2H), 3.20-2.86 (m, 6H), 2.67-2.56 (m, 5H), 2.50-2.37 (m, 6H), 2.22-2.12 (m, 2H), 2.05-1.78 (m, 8H), 1.65-1.52 (m, 3H), 1.18-1.05 (m, 2H), 1.05-0.98 (m, 2H), 0.86-0.78 (m, 2H) | 840.95 (840.40) | 841.7 | N.D. | N.D. | N.D. | N.D. | A | B |
| 230 | 1H NMR: (400 MHz, DMSO-d6) δ: 13.54-13.03 (m, 1H), 11.18-10.77 (m, 1H), 8.64-8.58 (m, 1H), 8.17- | 816.98 (816.42) | 817.7 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 8.11 (m, 1H), 7.54-7.43 (m, 2H), 7.39-7.32 (m, 1H), 7.20-7.12 (m, 1H), 7.09-7.01 (m, 1H), 5.23-4.82 (m, 1H), 4.55-4.21 (m, 4H), 3.27-3.20 (m, 4H), 3.01-2.83 (m, 4H), 2.81-2.69 (m, 2H), 2.64-2.58 (m, 4H), 2.58-2.52 (m, 2H), 2.44-2.37(m, 3H), 2.04-1.93 (m, 1H), 1.89-1.78 (m, 4H), 1.73-1.42 (m, 7H), 1.37-1.19 (m, 2H), 1.17-1.00 (m, 2H), 0.96-0.90 (m, 2H), 0.81-0.69 (m, 2H) | | | | | | | | |
| 231 | 1H NMR: (400 MHz, DMSO-d6) δ: 13.37 (s, 1H), 10.98 (s, 1H), 8.62 (d, J = 0.8 Hz, 1H), 8.15 (d, J = 2.0 Hz, 1H), 8.14 (s, 1H), 7.48 (dd, J = 8.6, 14.4 Hz, 2H), 7.37 (s, 1H), 7.15 (s, 1H), 7.06 (dd, J = 2.3, 9.0 Hz, 1H), 5.07 (dd, J = 5.0, 13.3 Hz, 1H), 4.50-4.28 (m, 4H), 3.00-2.86 (m, 4H), 2.78 (br t, J = 11.9 Hz, 2H), 2.69-2.58 (m, 4H), 2.41 (br dd, J = 4.4, 13.1 Hz, 2H), 2.19 (br s, 4H), 2.03-1.94 (m, 1H), 1.82 (br d, J = 9.1 Hz, 6H), 1.72 (br d, J = 10.1 Hz, 2H), 1.65-1.58 (m, 2H), 1.57-1.52 (m, 4H), 1.42-1.30 (m, 2H), 1.15-1.02 (m, 2H), 0.97-0.91 (m, 2H), 0.80-0.74 (m, 2H) | 821.98 (821.42) | 822.7 | N.D. | N.D. | N.D. | N.D. | A | B |
| 232 | 1H NMR: (400 MHz, DMSO-d6) δ: 13.46 (s, 1H), 10.99 (s, 1H), 8.64 (s, 1H), 8.39 (d, J = 8.4 Hz, 1H), 8.14 (s, 1H), 7.50-7.43 (m, 2H), 7.38 (s, 1H), 7.16 (t, J = 7.9 Hz, 1H), 5.08 (dd, J = 5.1, 13.3 Hz, 1H), 4.52-4.26 (m, 4H), 3.02-2.88 (m, 4H), 2.82-2.75 (m, 2H), 2.63 (br d, J = 10.8 Hz, 2H), 2.59-2.55 (m, 2H), 2.41 (br s, 3H), 2.20 (br s, 3H), 2.04-1.92 (m, 1H), 1.82 (br s, 7H), 1.73 (br d, J = 10.9 Hz, 2H), 1.64-1.53 (m, 5H), 1.42-1.33 (m, 2H), 1.09 (br d, J = 12.8 Hz, 2H), 1.03-0.98 (m, 2H), 0.84-0.78 (m, 2H) | 839.97 (839.41) | 840.7 | N.D. | N.D. | N.D. | N.D. | A | B |
| 233 | 1H NMR: (400 MHz, CD3OD) δ = 8.67 (d, J = 17.6 Hz, 2H), 7.98 (s, 1H), 7.55 (d, J = 8.0 Hz, 1H), 7.49 (s, 1H), 7.24-7.16 (m, 1H), 5.13 (br d, J = 8.4 Hz, 1H), 4.52 (br d, J = 14.4 Hz, 2H), 4.23-4.15 (m, 2H), 3.90-3.81 (m, 2H), 3.75-3.70 (m, 1H), 3.58 (br dd, J = 4.4, 8.4 Hz, 1H), 3.52-3.47 (m, 4H), 3.05-2.98 (m, 2H), 2.94-2.87 (m, 1H), 2.86-2.79 (m, 1H), 2.78-2.71 (m, 2H), 2.51 (dt, J = 8.4, 13.2 Hz, 1H), 2.22-2.15 (m, 1H), 2.05-1.95 (m, 6H), 1.78-1.71 (m, 2H), 1.69 (s, 3H), 1.67-1.60 (m, 2H), 1.11-1.05 (m, 2H), 0.88-0.83 (m, 2H) | 779.87 (779.36) | 780.4 | N.D. | N.D. | N.D. | N.D. | A | B |
| 234 | 1H NMR: (400 MHz, DMSO-d6) δ: 13.48-13.27 (m, 1H), 11.02-10.85 (m, 1H), 8.70-8.55 (m, 1H), 8.18-8.17 (m, 1H), 8.17-8.11 (m, 1H), 7.53-7.42 (m, 2H), 7.40-7.33 (m, 1H), 7.21-7.11 (m, 1H), 7.10-7.01 (m, 1H), 5.13-5.01 (m, 1H), 4.55-4.21 (m, 2H), 3.74-3.56 (m, 5H), 3.01-2.84 (m, 3H), 2.69-2.53 (m, 2H), 2.46-2.29 (m, 6H), 2.19-2.06 (m, 2H), 2.02-1.87 (m, 5H), 1.86-1.74 (m, 2H), 1.63-1.55 (m, 2H), 1.55-1.51 (m, 3H), 1.51-1.42 (m, 1H), 1.25-1.11 (m, 2H), 1.00-0.84 (m, 4H), 0.81-0.71 (m, 2H). | 805.94 (805.41) | 806.6 | N.D. | N.D. | N.D. | N.D. | A | B |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | Degradation and characterization of exemplary bifunctional compounds of the present disclosure | | | | | | | | |
| 235 | 1H NMR: (400 MHz, DMSO-d6) δ: 13.48-13.33 (m, 1H), 11.03-10.90 (m, 1H), 8.69-8.58 (m, 1H), 8.18-8.14 (m, 1H), 8.14-8.13 (m, 1H), 7.54-7.46 (m, 1H), 7.44-7.38 (m, 1H), 7.38-7.34 (m, 1H), 7.29-7.20 (m, 1H), 7.11-7.02 (m, 1H), 5.13-4.99 (m, 1H), 4.44-4.13 (m, 2H), 3.77-3.55 (m, 5H), 2.98-2.82 (m, 3H), 2.69-2.54 (m, 2H), 2.46-2.28 (m, 6H), 2.19-2.07 (m, 2H), 2.03-1.87 (m, 5H), 1.86-1.74 (m, 2H), 1.64-1.55 (m, 2H), 1.55-1.53 (m, 3H), 1.52-1.43 (m, 1H), 1.26-1.10 (m, 2H), 0.98-0.94 (m, 2H), 0.94-0.84 (m, 2H), 0.81-0.73 (m, 2H). | 805.94 (805.41) | 806.7 | N.D. | N.D. | N.D. | N.D. | A | B |
| 236 | 1H NMR: (400 MHz, DMSO-d6) δ: 13.42-13.36 (m, 1H), 11.02-10.97 (m, 1H), 8.65-8.62 (m, 1H), 8.18-8.16 (m, 1H), 8.16-8.15 (m, 1H), 7.55-7.44 (m, 2H), 7.40-7.36 (m, 1H), 7.21-7.13 (m, 1H), 7.11-7.05 (m, 1H), 5.12-5.05 (m, 1H), 4.34 (s, 4H), 3.54-3.46 (m, 2H), 2.88 (br d, J = 5.1 Hz, 3H), 2.81-2.71 (m, 2H), 2.64-2.54 (m, 2H), 2.38 (br s, 4H), 2.30-2.04 (m, 6H), 2.02-1.96 (m, 1H), 1.92-1.78 (m, 5H), 1.61-1.50 (m, 4H), 1.30-1.20 (m, 2H), 1.14-1.04 (m, 2H), 1.02-0.98 (m, 6H), 0.97-0.93 (m, 2H), 0.81-0.76 (m, 2H) | 833.01 (832.45) | 833.7 | N.D. | N.D. | N.D. | N.D. | A | B |
| 237 | 1H NMR: (400 MHz, CDCl3) δ 13.40 (br s, 1H), 11.00 (s, 1H), 8.63 (s, 1H), 8.25-8.19 (m, 1H), 8.16 (d, J = 2.0 Hz, 1H), 7.50 (dd, J = 8.6, 16.7 Hz, 2H), 7.38 (s, 1H), 7.17 (t, J = 8.0 Hz, 1H), 7.08 (dd, J = 2.3, 9.0 Hz, 1H), 5.08 (dd, J = 5.0, 13.3 Hz, 1H), 4.54-4.40 (m, 3H), 4.36-4.26 (m, 1H), 3.75-3.65 (m, 2H), 3.00-2.72 (m, 10H), 2.70-2.58 (m, 2H), 2.50-2.40 (m, 2H), 2.40-2.21 (m, 3H), 2.03-1.94 (m, 1H), 1.83 (br d, J = 11.8 Hz, 5H), 1.77-1.62 (m, 2H), 1.56 (s, 3H), 1.36-1.23 (m, 2H), 1.21-1.07 (m, 2H), 1.00-0.92 (m, 2H), 0.85-0.73 (m, 2H) | 816.96 (816.42) | 817.7 | N.D. | N.D. | N.D. | N.D. | A | A |
| 238 | 1H NMR: (400 MHz, DMSO-d6) δ: 13.53-13.31 (m, 1H), 11.12-10.84 (m, 1H), 8.67-8.59 (m, 1H), 8.22-8.17 (m, 1H), 8.17-8.11 (m, 1H), 7.53-7.47 (m, 1H), 7.40-7.32 (m, 2H), 7.11-7.01 (m, 2H), 5.13-4.97 (m, 1H), 4.48-4.38 (m, 1H), 4.32-4.19 (m, 1H), 3.87-3.82 (m, 3H), 3.70-3.64 (m, 4H), 3.59 (br d, J = 3.6 Hz, 1H), 3.15 (br d, J = 9.5 Hz, 1H), 2.91-2.78 (m, 3H), 2.62-2.55 (m, 1H), 2.45-2.40 (m, 4H), 2.16-2.08 (m, 2H), 2.01-1.89 (m, 5H), 1.86-1.76 (m, 2H), 1.65-1.54 (m, 3H), 1.54-1.51 (m, 3H), 1.51-1.41 (m, 1H), 1.36-1.25 (m, 1H), 1.22-1.11 (m, 1H), 1.22-1.09 (m, 1H), 0.98-0.94 (m, 1H), 0.99-0.85 (m, 4H), 0.81-0.71 (m, 2H). | 817.97 (817.43) | 818.7 | N.D. | N.D. | N.D. | N.D. | A | B |
| 239 | 1H NMR: (400 MHz, DMSO-d6) δ: 13.45-13.29 (m, 1H), 11.09-10.83 (m, 1H), 8.68-8.55 (m, 1H), 8.21-8.07 (m, 2H), 7.64 (d, J = 8.1 Hz, 1H), 7.54-7.47 (m, 1H), 7.37 (s, 1H), 7.29-7.21 (m, 1H), 7.11-7.03 (m, 1H), 5.14-5.05 (m, 1H), 4.54-4.42 (m, | 821.41 (820.39) | 821.6 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 2H), 4.40-4.22 (m, 2H), 3.06-2.88 (m, 4H), 2.76-2.69 (m, 2H), 2.63-2.55 (m, 2H), 2.47-2.35 (m, 9H), 2.25-2.16 (m, 4H), 2.03-1.97 (m, 1H), 1.81 (br d, J = 10.4 Hz, 5H), 1.74-1.66 (m, 1H), 1.58-1.52 (m, 3H), 1.37-1.24 (m, 2H), 1.14-1.02 (m, 2H), 0.98-0.91 (m, 2H), 0.81-0.73 (m, 2H) | | | | | | | | |
| 240 | 1H NMR: (400 MHz, DMSO-d6) δ: 13.47-13.26 (m, 1H), 11.05-10.90 (m, 1H), 8.67-8.59 (m, 1H), 8.21-8.11 (m, 1H), 7.54-7.42 (m, 2H), 7.41-7.36 (m, 1H), 7.20-7.13 (m, 1H), 7.10-7.01 (m, 1H), 5.12-4.99 (m, 1H), 4.58-4.27 (m, 2H), 4.23-4.00 (m, 4H), 3.68-3.57 (m, 1H), 3.55-3.45 (m, 1H), 3.30 (br s, 2H), 3.00-2.82 (m, 3H), 2.64-2.53 (m, 2H), 2.47-2.34 (m, 2H), 2.02-1.84 (m, 7H), 1.84-1.78 (m, 2H), 1.62-1.47 (m, 7H), 1.47-1.34 (m, 2H), 0.98-0.88 (m, 2H), 0.83-0.70 (m, 2H) | 792.90 (792.38) | 793.6 | N.D. | N.D. | N.D. | N.D. | A | B |
| 241 | 1H NMR: (400 MHz, DMSO-d6) δ: 13.37 (s, 1H), 10.96 (s, 1H), 8.61 (s, 1H), 8.24 (s, 1H), 8.14 (s, 1H), 7.50 (d, J = 9.2 Hz, 1H), 7.40 (d, J = 8.4 Hz, 1H), 7.36 (s, 1H), 7.26-7.22 (m, 1H), 7.14 (d, J = 1.6 Hz, 1H), 7.06 (dd, J = 2.4, 9.2 Hz, 1H), 5.10-5.06 (m, 1H), 4.50-4.39 (m, 4H), 4.30 (s, 1H), 4.21 (s, 1H), 3.74 (d, J = 11.2 Hz, 4H), 2.98 (d, J = 2.0 Hz, 4H), 2.87 (s, 1H), 2.70 (s, 4H), 2.61 (s, 1H), 2.38 (s, 1H), 2.14 (d, J = 4.4 Hz, 4H), 2.01-1.98 (m, 1H), 1.82-1.77 (m, 4H), 1.70-1.65 (m, 1H), 1.54 (s, 3H), 1.24-1.18 (m, 2H), 1.10-1.04 (m, 2H), 0.96-0.93 (m, 2H), 0.79-0.75 (m, 2H) | 786.96 (786.43) | 787.4 | N.D. | N.D. | N.D. | N.D. | A | B |
| 242 | 1H NMR: (400 MHz, DMSO-d6) δ: 13.37 (s, 1H), 10.99 (s, 1H), 8.62 (d, J = 0.9 Hz, 1H), 8.16 (s, 0.3H), 8.15 (br d, J = 2.1 Hz, 1H), 7.50 (d, J = 9.0 Hz, 1H), 7.41-7.32 (m, 2H), 7.06 (dd, J = 2.4, 9.0 Hz, 1H), 5.07 (dd, J = 5.1, 13.3 Hz, 1H), 4.54-4.23 (m, 4H), 3.12 (br d, J = 12.0 Hz, 2H), 2.98-2.86 (m, 3H), 2.65-2.52 (m, 4H), 2.42-2.35 (m, 2H), 2.22-2.10 (m, 4H), 2.02-1.94 (m, 1H), 1.90-1.67 (m, 9H), 1.66-1.51 (m, 6H), 1.39-1.26 (m, 2H), 1.15-1.00 (m, 2H), 0.98-0.90 (m, 2H), 0.80-0.73 (m, 2H) | 839.95 (839.41) | 840.6 | N.D. | N.D. | N.D. | N.D. | A | B |
| 243 | 1H NMR: (400 MHz, DMSO-d6) δ: 13.54-13.28 (m, 1H), 11.12-10.82 (m, 1H), 8.74-8.56 (m, 1H), 8.15 (br s, 1H), 7.66-7.58 (m, 1H), 7.50 (br d, J = 8.9 Hz, 1H), 7.41-7.34 (m, 1H), 7.33-7.22 (m, 1H), 7.14-7.02 (m, 1H), 5.18-5.01 (m, 1H), 4.42-4.22 (m, 2H), 3.66 (br s, 6H), 2.89 (br d, J = 6.3 Hz, 2H), 2.67-2.59 (m, 5H), 2.44-2.30 (m, 6H), 2.29-2.18 (m, 1H), 2.13 (br s, 2H), 1.95 (br s, 4H), 1.81 (br d, J = 9.1 Hz, 2H), 1.57-1.51 (m, 2H), 1.64-1.46 (m, 1H), 1.32-1.05 (m, 3H), 1.01-0.88 (m, 4H), 0.84-0.74 (m, 2H) | 822.39 (821.38) | | N.D. | N.D. | N.D. | N.D. | A | B |
| 244 | 1H NMR: (400 MHz, DMSO-d6) δ: 13.52-13.30 (m, 1H), 11.25-10.80 (m, 1H), 8.72-8.49 (m, 1H), 8.17- | 806.92 (806.39) | 807.6 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 8.07 (m, 1H), 7.56-7.46 (m, 1H), 7.44-7.33 (m, 2H), 7.27-7.18 (m, 1H), 7.10-6.98 (m, 1H), 5.15-4.99 (m, 1H), 4.41-4.17 (m, 2H), 4.13-3.96 (m, 2H), 3.77-3.53 (m, 2H), 3.50-3.40 (m, 2H), 2.98-2.82 (m, 3H), 2.52 (br s, 4H), 2.39 (br s, 2H), 2.01-1.78 (m, 9H), 1.65-1.49 (m, 5H), 1.47-1.37 (m, 2H), 1.33-1.19 (m, 4H), 1.00-0.89 (m, 2H), 0.81-0.72 (m, 2H) | | | | | | | | |
| 245 | 1H NMR: (400 MHz, DMSO-d6) δ: 13.39 (s, 1H), 11.00 (br d, J = 1.0 Hz, 1H), 8.63 (d, J = 0.9 Hz, 1H), 8.47 (s, 0.1H), 8.16 (d, J = 2.4 Hz, 1H), 7.51 (d, J = 9.0 Hz, 1H), 7.44-7.33 (m, 2H), 7.07 (dd, J = 2.4, 9.0 Hz, 1H), 5.13-5.01 (m, 1H), 4.55-4.41 (m, 1H), 4.31 (d, J = 16.9 Hz, 1H), 4.15-3.99 (m, 2H), 3.79-3.68 (m, 1H), 3.66-3.53 (m, 1H), 3.50-3.38 (m, 4H), 3.15-3.04 (m, 3H), 2.96-2.86 (m, 1H), 2.64-2.55 (m, 2H), 2.41 (br s, 1H), 2.03-1.84 (m, 9H), 1.61-1.50 (m, 5H), 1.48-1.38 (m, 2H), 1.32-1.22 (m, 4H), 0.99-0.92 (m, 2H), 0.81-0.74 (m, 2H) | 824.91 (824.38) | 825.7 | N.D. | N.D. | N.D. | N.D. | N.D. | N.D. |
| 246 | 1H NMR: (400 MHz, DMSO-d6) δ: 13.41-13.35 (m, 1H), 10.98-10.95 (m, 1H), 8.63 (s, 1H), 8.16 (s, 2H), 7.51 (d, J = 9.0 Hz, 1H), 7.40-7.37 (m, 2H), 7.09-7.06 (m, 2H), 5.07 (br d, J = 8.3 Hz, 1H), 4.45 (br d, J = 16.9 Hz, 3H), 4.28 (br d, J = 16.9 Hz, 1H), 3.86 (s, 2H), 3.87-3.86 (m, 1H), 3.12 (br s, 2H), 2.94 (br d, J = 13.1 Hz, 4H), 2.60 (br d, J = 5.8 Hz, 8H), 2.36-2.31 (m, 1H), 2.43-2.31 (m, 1H), 2.23-2.18 (m, 4H), 2.00-1.95 (m, 1H), 1.90-1.78 (m, 7H),, 1.56-1.54 (m, 3H), 1.09 (br d, J = 11.3 Hz, 2H), 0.95 (s, 2H), 0.85-0.71 (m, 3H) | 834.98 (834.43) | 835.7 | N.D. | N.D. | N.D. | N.D. | A | B |
| 247 | 1H NMR: (400 MHz, DMSO-d6) δ: 14.04-13.77 (m, 1H), 10.99-10.95 (m, 1H), 8.80-8.77 (m, 1H), 8.63-8.60 (m, 1H), 8.20-8.15 (m, 1H), 7.81-7.77 (m, 1H), 7.48-7.43 (m, 1H), 7.37 (s, 1H), 7.18-7.12 (m, 1H), 5.10-5.03 (m, 1H), 4.51-4.30 (m, 4H), 3.00-2.86 (m, 4H), 2.84-2.70 (m, 3H), 2.69-2.62 (m, 1H), 2.37 (br s, 1H), 2.17-2.06 (m, 5H), 2.02-1.93 (m, 2H), 1.88-1.75 (m, 5H), 1.73-1.66 (m, 2H), 1.64 (br s, 4H), 1.30-1.22 (m, 2H), 1.09-0.88 (m, 11H), 0.78-0.74 (m, 2H) | 833.99 (833.45) | 834.7 | N.D. | N.D. | N.D. | N.D. | A | B |
| 248 | 1H NMR: (400 MHz, DMSO-d6) δ: 13.39 (s, 1H), 10.96 (s, 1H), 8.63 (s, 1H), 8.15 (s, 1H), 7.51 (d, J = 9.0 Hz, 1H), 7.43-7.27 (m, 2H), 7.13-6.96 (m, 2H), 5.13-5.00 (m, 1H), 4.47-4.23 (m, 2H), 4.16-4.00 (m, 2H), 3.86 (s, 3H), 3.75-3.68 (m, 1H), 3.60-3.54 (m, 1H), 2.91-2.80 (m, 3H), 2.61-2.53 (m, 4H), 2.45-2.36 (m, 3H), 1.99-1.84 (m, 10H), 1.59 (d, J = 9.3 Hz, 2H), 1.54 (s, 3H), 1.42 (d, J = 8.9 Hz, 2H), 1.35-1.20 (m, 4H), 0.98-0.91 (m, 2H), 0.80-0.74 (m, 2H) | 818.96 (818.41) | 819.7 | N.D. | N.D. | N.D. | N.D. | A | B |
| 249 | 1H NMR: (400 MHz, DMSO-d6) δ: 13.43-13.33 (m, 1H), 11.01-10.96 (m, 1H), 8.66-8.58 (m, 1H), 8.18-8.14 (m, 1H), 7.71-7.63 (m, 1H), 7.50 (d, J = 9.0 Hz, 1H), 7.40-7.37 | 822.39 (821.38) | 822.4 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 1H), 7.31-7.21 (m, 1H), 7.12-7.04 (m, 1H), 5.13-5.06 (m, 1H), 4.44-4.23 (m, 2H), 4.07 (br d, J = 12.6 Hz, 2H), 3.77-3.71 (m, 1H), 3.14-3.03 (m, 5H), 2.95-2.88 (m, 1H), 2.61-2.52 (m, 4H), 2.45-2.38 (m, 4H), 2.15 (br d, J = 7.0 Hz, 2H), 2.01-1.93 (m, 3H), 1.89-1.78 (m, 4H), 1.56-1.53 (m, 3H), 1.49-1.38 (m, 3H), 1.22-1.12 (m, 2H), 0.98-0.89 (m, 4H), 0.79-0.75 (m, 2H) | | | | | | | | |
| 250 | 1H NMR: (400 MHz, DMSO-d6) δ: 13.88 (s, 1H), 10.96 (s, 1H), 8.79 (s, 1H), 8.63 (s, 1H), 8.13 (s, 1H), 7.79 (s, 1H), 7.37 (d, J = 8.0 Hz, 2H), 7.08 (d, J = 8.3 Hz, 1H), 5.06 (dd, J = 4.9, 13.4 Hz, 1H), 4.54-4.36 (m, 3H), 4.26 (d, J = 17.0 Hz, 1H), 3.85 (s, 3H), 3.60-3.49 (m, 2H), 3.08-2.83 (m, 4H), 2.72-2.57 (m, 6H), 2.36-2.29 (m, 3H), 2.21-2.07 (m, 4H), 2.02-1.91 (m, 2H), 1.83 (br d, J = 11.8 Hz, 3H), 1.76-1.64 (m, 2H), 1.61 (s, 3H), 1.38-1.21 (m, 3H), 1.20-1.11 (m, 1H), 1.11-1.02 (m, 2H), 0.99-0.89 (m, 6H), 0.79-0.73 (m, 2H) | 846.03 (845.47) | 846.8 | N.D. | N.D. | N.D. | N.D. | A | B |
| 251 | 1H NMR: (400 MHz, DMSO-d6) δ: 13.37 (s, 1H), 10.96 (s, 1H), 8.61 (d, J = 0.8 Hz, 1H), 8.15 (s, 1H), 8.15-8.12 (m, 1H), 7.50 (d, J = 9.0 Hz, 1H), 7.41-7.33 (m, 2H), 7.07 (dt, J = 2.8, 5.8 Hz, 2H), 5.06 (dd, J = 5.0, 13.3 Hz, 1H), 4.43 (br d, J = 16.9 Hz, 3H), 4.26 (d, J = 16.9 Hz, 1H), 3.85 (s, 3H), 3.60-3.49 (m, 2H), 3.00-2.87 (m, 3H), 2.76-2.54 (m, 6H), 2.45-2.39 (m, 2H), 2.35-2.28 (m, 2H), 2.18-2.08 (m, 4H), 2.00-1.94 (m, 1H), 1.83 (br d, J = 10.5 Hz, 4H), 1.72-1.61 (m, 2H), 1.54 (s, 3H), 1.38-1.23 (m, 2H), 1.11-1.00 (m, 2H), 0.98-0.92 (m, 8H), 0.81-0.74 (m, 2H) | 845.04 (844.47) | 845.7 | N.D. | N.D. | N.D. | N.D. | A | B |
| 252 | 1H NMR: (400 MHz, DMSO-d6) δ: 13.48-13.24 (m, 1H), 11.00-10.79 (m, 1H), 8.70-8.50 (m, 1H), 8.23-7.98 (m, 1H), 7.54-7.48 (m, 1H), 7.42-7.34 (m, 2H), 7.09-7.03 (m, 2H), 5.17-4.94 (m, 1H), 4.49-4.22 (m, 2H), 4.15-4.01 (m, 2H), 3.89-3.82 (m, 3H), 3.78-3.67 (m, 1H), 3.16-3.04 (m, 4H), 2.97-2.84 (m, 1H), 2.64-2.54 (m, 6H), 2.46-2.34 (m, 3H), 2.18-2.10 (m, 2H), 2.03-1.91 (m, 3H), 1.90-1.74 (m, 4H), 1.58-1.34 (m, 6H), 1.25-1.08 (m, 2H), 1.01-0.83 (m, 4H), 0.82-0.71 (m, 2H) | 817.97 (817.43) | 818.7 | N.D. | N.D. | N.D. | N.D. | A | B |
| 253 | 1H NMR: (400 MHz, DMSO-d6) δ: 14.24-13.58 (m, 1H), 10.96 (s, 1H), 8.78 (s, 1H), 8.62 (s, 1H), 8.18 (s, 1H), 7.79 (s, 1H), 7.45-7.28 (m, 2H), 7.06 (d, J = 8.0 Hz, 1H), 5.06 (dd, J = 4.8, 13.2 Hz, 1H), 4.57-4.35 (m, 3H), 4.29-4.22 (m, 1H), 3.85 (s, 3H), 3.56-3.54 (m, 2H), 3.00-2.85 (m, 3H), 2.69-2.56 (m, 4H), 2.46-2.29 (m, 8H), 2.21-2.11 (m, 4H), 2.01-1.91 (m, 1H), 1.89-1.75 (m, 5H), 1.71-1.56 (m, 4H), 1.36-1.18 (m, 2H), 1.14-1.00 (m, 2H), 0.99-0.87 (m, 2H), 0.83-0.67 (m, 2H). | 817.98 (817.44) | 818.3 | N.D. | N.D. | N.D. | N.D. | A | B |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | Degradation and characterization of exemplary bifunctional compounds of the present disclosure | | | | | | | | |
| 254 | 1H NMR: (400 MHz, CDCl3) δ: 8.66 (s, 2H), 8.01 (br s, 1H), 7.91 (s, 1H), 7.52 (d, J = 8.4 Hz, 1H), 7.27 (s, 1H), 6.97 (t, J = 8.0 Hz, 1H), 5.12 (dd, J = 5.2, 13.2 Hz, 1H), 4.46-4.38 (m, 1H), 4.31-4.24 (m, 1H), 4.11-4.01 (m, 2H), 3.72-3.63 (m, 1H), 3.41-3.25 (m, 3H), 3.20-3.12 (m, 4H), 2.91-2.82 (m, 1H), 2.82-2.71 (m, 1H), 2.59-2.50 (m, 4H), 2.32-2.26 (m, 1H), 2.18-2.14 (m, 3H), 2.00-1.95 (m, 2H), 1.89-1.83 (m, 4H), 1.63 (s, 3H), 1.60-1.56 (m, 2H), 1.48-1.44 (m, 1H), 1.27-1.23 (m, 1H), 1.21-1.18 (s, 2H), 1.04-1.00 (m, 2H), 0.94-0.86 (m, 2H), 0.74-0.70 (m, 2H). | 806.93 (806.40) | 807.3 | N.D. | N.D. | N.D. | N.D. | A | B |
| 255 | 1H NMR: (400 MHz, DMSO-d6) δ: 13.49-13.27 (m, 1H), 11.05-10.85 (m, 1H), 8.66-8.51 (m, 1H), 8.23-8.17 (m, 1H), 8.17-8.11 (m, 1H), 7.55-7.45 (m, 1H), 7.41-7.30 (m, 2H), 7.11-7.00 (m, 2H), 5.12-4.99 (m, 1H), 4.23 (s, 4H), 3.87-3.79 (m, 3H), 3.56-3.51 (m, 2H), 3.01-2.88 (m, 3H), 2.87 (br s, 2H), 2.71-2.59 (m, 4H), 2.41-2.25 (m, 2H), 2.21-2.04 (m, 4H), 2.02-1.88 (m, 3H), 1.87-1.59 (m, 6H), 1.58-1.48 (m, 3H), 1.37-1.20 (m, 2H), 1.18-0.98 (m, 3H), 0.98-0.87 (m, 5H), 0.82-0.71 (m, 2H). | 831.01 (830.46) | 831.7 | N.D. | N.D. | N.D. | N.D. | A | B |
| 256 | 1H NMR: (400 MHz, DMSO-d6) δ: 13.37 (br s, 1H), 10.96 (s, 1H), 8.62 (s, 1H), 8.16-8.14 (m, 1H), 7.50 (d, J = 9.0 Hz, 1H), 7.39-7.35 (m, 2H), 7.07 (td, J = 2.3, 8.8 Hz, 2H), 5.06 (dd, J = 5.1, 13.2 Hz, 1H), 4.53-4.37 (m, 3H), 4.26 (d, J = 16.9 Hz, 1H), 3.85 (s, 3H), 3.56-3.51 (m, 2H), 3.02-2.79 (m, 5H), 2.70-2.58 (m, 6H), 2.34-2.31 (m, 1H), 2.14 (br d, J = 7.3 Hz, 4H), 2.00-1.89 (m, 3H), 1.82 (br d, J = 11.0 Hz, 4H), 1.75-1.64 (m, 2H), 1.54 (s, 3H), 1.33-1.23 (m, 2H), 1.15-1.01 (m, 2H), 0.95 (br d, J = 6.0 Hz, 5H), 0.81-0.73 (m, 2H) | 831.01 (830.46) | 831.7 | N.D. | N.D. | N.D. | N.D. | A | B |
| 257 | 1H NMR: (400 MHz, CD3OD) δ: 8.70-8.65 (m, 1H), 8.65-8.58 (m, 1H), 8.48-8.35 (m, 1H), 8.00-7.88 (m, 1H), 7.54-7.40 (m, 2H), 7.17-7.08 (m, 1H), 5.16-5.08 (m, 1H), 4.65-4.55 (m, 2H), 4.54-4.40 (m, 2H), 4.00-3.85 (m, 3H), 3.73-3.60 (m, 2H), 3.41-3.33 (m, 1H), 3.24-2.83 (m, 8H), 2.82-2.72 (m, 4H), 2.66 (br s, 2H), 2.59-2.43 (m, 3H), 2.20-2.12 (m, 1H), 2.10-1.98 (m, 2H), 1.97-1.83 (m, 4H), 1.69-1.63 (m, 3H), 1.55-1.39 (m, 2H), 1.38-1.28 (m, 2H), 1.28-1.21 (m, 3H), 1.09-1.00 (m, 2H), 0.89-0.79 (m, 2H). | 832.00 (831.45) | 832.7 | N.D. | N.D. | N.D. | N.D. | A | B |
| 258 | 1H NMR: (400 MHz, DMSO-d6) δ: 10.97 (s, 1H), 8.78 (d, J = 1.2 Hz, 1H), 8.64 (d, J = 0.8 Hz, 1H), 7.79 (d, J = 1.2 Hz, 1H), 7.49-7.41 (m, 1H), 7.38 (s, 1H), 7.20-7.14 (m, 1H), 5.06 (dd, J = 4.8, 13.2 Hz, 1H), 4.48 (d, J = 16.8 Hz, 1H), 4.35-4.27 (m, 1H), 3.67 (s, 4H), 2.98-2.85 (m, 4H), 2.60 (d, J = 3.2 Hz, 2H), 2.42 (s, 5H), 2.12 (d, J = 7.2 Hz, 2H), 1.98-1.88 (m, | 806.93 (806.40) | 807.3 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 5H), 1.85-1.77 (m, 2H), 1.61 (s, 3H), 1.59-1.47 (m, 3H), 1.26-1.10 (m, 3H), 0.98-0.84 (m, 5H), 0.78-0.74 (m, 2H) | | | | | | | | |
| 259 | 1H NMR: (400 MHz, DMSO-d6) δ: 13.47 (br s, 1H), 10.99 (s, 1H), 8.65 (s, 1H), 8.39 (d, J = 8.8 Hz, 1H), 7.51-7.44 (m, 2H), 7.40 (s, 1H), 7.16 (t, J = 8.0 Hz, 1H), 5.08 (dd, J = 5.2, 13.2 Hz, 1H), 4.53-4.46 (m, 1H), 4.37-4.28 (m, 1H), 4.13-4.04 (m, 2H), 3.80-3.71 (m, 1H), 3.16-3.12 (m, 4H), 2.97-2.87 (m, 1H), 2.64-2.61 (m, 1H), 2.56-2.54 (m, 4H), 2.45-2.39 (m, 2H), 2.17-2.12 (m, 2H), 2.03-1.93 (m, 4H), 1.91-1.77 (m, 5H), 1.59 (s, 3H), 1.51-1.40 (m, 3H), 1.23-1.14 (m, 2H), 1.03-0.99 (m, 2H), 0.97-0.87 (m, 2H), 0.84-0.79 (m, 2H) | 823.93 (823.40) | 824.3 | N.D. | N.D. | N.D. | N.D. | A | B |
| 260 | 1H NMR: (400 MHz, DMSO-d6) δ: 10.97 (s, 1H), 8.65 (s, 1H), 8.38 (d, J = 8.4 Hz, 1H), 7.48-7.42 (m, 2H), 7.38 (s, 1H), 7.17 (t, J = 8.0 Hz, 1H), 5.10-5.03 (m, 1H), 4.48 (d, J = 16.8 Hz, 1H), 4.31 (d, J = 16.8 Hz, 1H), 3.67 (s, 4H), 3.32 (d, J = 1.2 Hz, 2H), 2.98-2.89 (m, 3H), 2.63-2.53 (m, 2H), 2.41 (d, J = 5.2 Hz, 6H), 2.12 (d, J = 6.8 Hz, 2H), 2.01-1.87 (m, 6H), 1.85-1.77 (m, 2H), 1.57 (s, 3H), 1.50-1.44 (m, 1H), 1.25-1.11 (m, 3H), 1.03-0.97 (m, 2H), 0.97-0.91 (m, 1H), 0.91-0.85 (m, 1H), 0.83-0.78 (m, 2H) | 823.93 (823.40) | 824.3 | N.D. | N.D. | N.D. | N.D. | A | B |
| 261 | 1H NMR: (400 MHz, DMSO-d6) δ = 13.92 (br s, 1H), 10.96 (s, 1H), 8.79 (d, J = 1.2 Hz, 1H), 8.65 (d, J = 0.8 Hz, 1H), 8.15 (s, 1H), 7.80 (d, J = 1.2 Hz, 1H), 7.42-7.33 (m, 2H), 7.08 (d, J = 8.4 Hz, 1H), 5.06 (dd, J = 5.2, 13.6 Hz, 1H), 4.44 (br d, J = 16.8 Hz, 1H), 4.27 (br d, J = 17.2 Hz, 1H), 3.85 (s, 3H), 3.68 (br s, 6H), 3.12 (br s, 4H), 2.93-2.88 (m, 2H), 2.60 (br s, 3H), 2.43 (br d, J = 3.2 Hz, 4H), 2.19-2.11 (m, 4H), 2.00-1.94 (m, 1H), 1.86-1.78 (m, 4H), 1.61 (s, 3H), 1.53-1.45 (m, 2H), 0.96-0.85 (m, 6H), 0.79-0.73 (m, 2H) | 817.98 (817.44) | 818.4 | N.D. | N.D. | N.D. | N.D. | A | B |
| 262 | 1H NMR: (400 MHz, DMSO-d6) δ: 13.45-13.24 (m, 1H), 11.01-10.88 (m, 1H), 8.69-8.55 (m, 1H), 8.21-8.07 (m, 1H), 7.53-7.47 (m, 1H), 7.40-7.35 (m, 2H), 7.11-7.02 (m, 2H), 5.09-5.01 (m, 1H), 4.52-4.19 (m, 4H), 3.88-3.83 (m, 3H), 3.61-3.47 (m, 2H), 3.03-2.83 (m, 3H), 2.64-2.58 (m, 2H), 2.45-2.34 (m, 3H), 2.25-2.10 (m, 5H), 2.03-1.92 (m, 1H), 1.91-1.73 (m, 5H), 1.57-1.52 (m, 3H), 1.51-1.44 (m, 1H), 1.32-1.18 (m, 2H), 1.16-1.02 (m, 2H), 1.02-0.91 (m, 8H), 0.80-0.71 (m, 2H) | 845.04 (844.47) | 845.8 | N.D. | N.D. | N.D. | N.D. | A | B |
| 263 | 1H NMR: (400 MHz, DMSO-d6) δ: 14.22-13.44 (m, 1H), 11.04-10.91 (m, 1H), 8.82-8.73 (m, 1H), 8.67-8.57 (m, 1H), 8.19-8.12 (m, 1H), 7.81-7.72 (m, 1H), 7.49-7.42 (m, 1H), 7.41-7.31 (m, 1H), 7.21-7.10 (m, 1H), 5.13-4.97 (m, 1H), 4.30 (d, J = 16.9 Hz, 3H), 4.35-4.23 (m, 1H), 3.02-2.83 (m, 4H), 2.83-2.71 (m, | 819.97 (819.43) | 820.7 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 3H), 2.68-2.52 (m, 4H), 2.45-2.27 (m, 3H), 2.21-2.04 (m, 4H), 2.02-1.65 (m, 9H), 1.63-1.52 (m, 3H), 1.32-1.19 (m, 2H), 1.16-0.98 (m, 2H), 0.97-0.81 (m, 5H), 0.80-0.67 (m, 2H) | | | | | | | | |
| 264 | 1H NMR: (400 MHz, CD3OD) δ: 8.63 (d, J = 0.8 Hz, 1H), 8.44 (s, 1H), 8.10 (d, J = 2.0 Hz, 1H), 7.55-7.39 (m, 3H), 7.19-7.09 (m, 2H), 5.13 (dd, J = 5.1, 13.4 Hz, 1H), 4.60-4.41 (m, 4H), 3.95 (s, 3H), 3.72 (br d, J = 11.5 Hz, 2H), 3.40 (br s, 1H), 3.07 (br t, J = 12.4 Hz, 5H), 2.98-2.87 (m, 2H), 2.85-2.73 (m, 3H), 2.69-2.35 (m, 6H), 2.25-2.13 (m, 1H), 2.09-1.84 (m, 6H), 1.67-1.61 (m, 3H), 1.59-1.45 (m, 2H), 1.39-1.17 (m, 6H), 1.10-1.00 (m, 2H), 0.84-0.76 (m, 2H) | 831.01 (830.46) | 831.7 | N.D. | N.D. | N.D. | N.D. | A | A |
| 265 | 1H NMR: (400 MHz, CD3OD) δ: 8.67 (s, 1H), 8.38 (s, 1H), 8.13 (d, J = 2.1 Hz, 1H), 7.56-7.47 (m, 2H), 7.45 (s, 1H), 7.19 (d, J = 8.3 Hz, 1H), 7.12 (dd, J = 2.4, 9.0 Hz, 1H), 5.14 (dd, J = 5.2, 13.3 Hz, 1H), 4.64 (br s, 2H), 4.59-4.47 (m, 2H), 3.97 (s, 3H), 3.86 (br s, 4H), 3.46-3.35 (m, 4H), 3.16 (br s, 4H), 2.99-2.69 (m, 7H), 2.57-2.48 (m, 1H), 2.43 (br d, J = 7.0 Hz, 2H), 2.19 (tdd, J = 2.7, 5.2, 10.1 Hz, 1H), 2.07-1.88 (m, 4H), 1.82-1.68 (m, 2H), 1.65-1.61 (m, 1H), 1.63 (s, 2H), 1.16-1.07 (m, 3H), 1.05-1.01 (m, 2H), 0.83-0.78 (m, 2H) | 816.99 (816.44) | 817.7 | N.D. | N.D. | N.D. | N.D. | A | A |
| 266 | 1H NMR: (400 MHz, DMSO-d6) δ: 14.17-13.99 (m, 1H), 10.98 (s, 1H), 8.84 (s, 1H), 8.67 (s, 1H), 7.74 (s, 1H), 7.53-7.40 (m, 2H), 7.25-6.93 (m, 2H), 5.07 (dd, J = 5.1, 13.3 Hz, 1H), 4.64-4.51 (m, 2H), 4.48 (br d, J = 16.9 Hz, 1H), 4.31 (br d, J = 16.9 Hz, 1H), 3.52 (br s, 3H), 3.05 (br d, J = 10.9 Hz, 4H), 2.98-2.86 (m, 3H), 2.84-2.75 (m, 3H), 2.63-2.54 (m, 3H), 2.46-2.35 (m, 4H), 1.97 (br dd, J = 4.9, 9.9 Hz, 3H), 1.89-1.75 (m, 4H), 1.62 (s, 3H), 1.41-1.28 (m, 3H), 1.27-1.13 (m, 4H), 0.95-0.91 (m, 2H), 0.79-0.74 (m, 2H) | 819.97 (819.43) | 820.7 | N.D. | N.D. | N.D. | N.D. | A | A |
| 267 | 1H NMR: (400 MHz, DMSO-d6) δ: 10.98 (s, 1H), 8.79-8.77 (m, 1H), 8.65-8.63 (m, 1H), 8.17 (s, 2H), 7.79 (d, J = 0.8 Hz, 1H), 7.48 (d, J = 8.4 Hz, 1H), 7.38 (s, 1H), 7.16 (t, J = 7.9 Hz, 1H), 5.07 (dd, J = 5.2, 13.3 Hz, 1H), 4.48 (d, J = 17.2 Hz, 1H), 4.31 (d, J = 17.2 Hz, 1H), 3.69-3.66 (m, 4H), 3.14 (br s, 4H), 2.94-2.87 (m, 2H), 2.61 (br d, J = 1.6 Hz, 1H), 2.44-2.39 (m, 6H), 2.14 (br t, J = 7.2 Hz, 4H), 2.02-1.92 (m, 2H), 1.81 (br d, J = 7.4 Hz, 4H), 1.61 (s, 3H), 1.56-1.43 (m, 3H), 0.94-0.85 (m, 6H), 0.78-0.74 (m, 2H) | 805.94 (805.42) | 806.4 | N.D. | N.D. | N.D. | N.D. | A | A |
| 268 | 1H NMR: (400 MHz, DMSO-d6) δ: 10.96 (s, 1H), 8.78 (s, 1H), 8.63 (s, 1H), 8.15 (s, 1H), 7.79 (s, 1H), 7.40-7.37 (m, 2H), 7.07 (d, J = 8.4 Hz, 1H), 5.05 (dd, J = 5.2, 13.2 Hz, 1H), 4.44 (d, J = 17.2 Hz, 1H), 4.26 (d, J = 16.8 Hz, 1H), 4.13-4.03 (m, 2H), 3.85 (s, 3H), 3.11 (br s, 7H), 2.97-2.83 (m, 3H), 2.62-2.59 (m, 2H), 2.14 (br d, J = | 818.96 (818.42) | 819.4 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 6.8 Hz, 2H), 2.00-1.92 (m, 4H), 1.89-1.77 (m, 5H), 1.61 (s, 3H), 1.48-1.38 (m, 3H), 1.20-1.14 (m, 2H), 0.98-0.86 (m, 5H), 0.78-0.73 (m, 2H) | | | | | | | | |
| 269 | 1H NMR (400 MHz, CDCl3) δ: 13.47-13.25 (m, 1H), 11.09-10.87 (m, 1H), 8.69-8.56 (m, 1H), 8.17-8.13 (m, 1H), 7.54-7.47 (m, 1H), 7.43-7.35 (m, 2H), 7.11-7.02 (m, 1H), 5.12-5.03 (m, 1H), 4.55-4.27 (m, 2H), 4.16-4.00 (m, 2H), 3.81-3.67 (m, 1H), 3.26-3.14 (m, 6H), 2.98-2.83 (m, 1H), 2.65-2.54 (m, 2H), 2.47-2.34 (m, 4H), 2.17-2.08 (m, 2H), 2.03-1.91 (m, 3H), 1.91-1.74 (m, 4H), 1.57-1.52 (m, 3H), 1.51-1.35 (m, 3H), 1.26-1.07 (m, 3H), 0.98-0.82 (m, 4H), 0.81-0.70 (m, 2H) | 823.93 (823.40) | 824.7 | N.D. | N.D. | N.D. | N.D. | A | B |
| 270 | 1H NMR: (400 MHz, DMSO-d6) δ: 14.01-13.65 (m, 1H), 11.12-10.83 (m, 1H), 8.82-8.75 (m, 1H), 8.66-8.59 (m, 1H), 8.19-8.09 (m, 1H), 7.82-7.75 (m, 1H), 7.50-7.44 (m, 1H), 7.40-7.36 (m, 1H), 7.20-7.10 (m, 1H), 5.11-4.94 (m, 1H), 4.57-4.14 (m, 4H), 3.53-3.43 (m, 2H), 3.01-2.84 (m, 4H), 2.80-2.69 (m, 2H), 2.65-2.55 (m, 2H), 2.44-2.34 (m, 2H), 2.21-2.13 (m, 2H), 2.12-2.02 (m, 3H), 2.02-1.92 (m, 2H), 1.91-1.72 (m, 5H), 1.65-1.58 (m, 3H), 1.58-1.45 (m, 1H), 1.30-1.15 (m, 2H), 1.14-1.01 (m, 3H), 1.00-0.95 (m, 6H), 0.95-0.90 (m, 2H), 0.78-0.73 (m, 2H) | 833.99 (833.45) | 834.7 | N.D. | N.D. | N.D. | N.D. | A | A |
| 271 | 1H NMR: (400 MHz, CD3OD) δ: 8.68 (d, J = 1.1 Hz, 1H), 8.63 (d, J = 1.0 Hz, 1H), 8.46 (s, 1H), 7.98 (d, J = 1.1 Hz, 1H), 7.53-7.44 (m, 2H), 7.15 (d, J = 8.3 Hz, 1H), 5.12 (dd, J = 5.1, 13.3 Hz, 1H), 4.90 (br s, 1H), 4.59-4.54 (m, 2H), 4.54-4.41 (m, 2H), 3.94 (s, 3H), 3.70 (br d, J = 11.1 Hz, 2H), 3.12-2.84 (m, 7H), 2.83-2.70 (m, 4H), 2.65-2.28 (m, 6H), 2.23-2.14 (m, 1H), 2.08-1.81 (m, 6H), 1.68 (s, 3H), 1.60-1.40 (m, 2H), 1.34-1.21 (m, 5H), 1.11-1.02 (m, 2H), 0.90-0.80 (m, 2H) | 832.00 (831.45) | 832.7 | N.D. | N.D. | N.D. | N.D. | A | B |
| 272 | 1H NMR: (400 MHz, DMSO-d6) δ: 14.46-13.23 (m, 1H), 11.00 (s, 1H), 8.79 (s, 1H), 8.63 (s, 1H), 8.17 (s, 1H), 7.80 (s, 1H), 7.47 (d, J = 8.1 Hz, 1H), 7.38 (s, 1H), 7.15 (br t, J = 7.9 Hz, 1H), 5.07 (dd, J = 5.0, 13.3 Hz, 1H), 4.57-4.39 (m, 3H), 4.31 (br d, J = 16.9 Hz, 1H), 3.04-2.85 (m, 4H), 2.83-2.64 (m, 4H), 2.64-2.54 (m, 4H), 2.44-2.34 (m, 2H), 2.19-2.06 (m, 4H), 2.02-1.93 (m, 2H), 1.90-1.69 (m, 6H), 1.61 (s, 4H), 1.36-1.17 (m, 2H), 1.14-1.03 (m, 2H), 0.98 (br d, J = 5.9 Hz, 3H), 0.95-0.91 (m, 2H), 0.80-0.73 (m, 2H) | 819.97 (819.43) | 820.6 | N.D. | N.D. | N.D. | N.D. | A | B |
| 273 | 1H NMR: (400 MHz, DMSO-d6) δ = 10.96 (s, 1H), 8.79 (d, J = 1.2 Hz, 1H), 8.65 (s, 1H), 8.32 (s, 1H), 7.80 (d, J = 1.2 Hz, 1H), 7.45-7.35 (m, 2H), 7.09 (d, J = 8.0 Hz, 1H), 5.13-5.00 (m, 1H), 4.44 (d, J = 17.2 Hz, 1H), 4.26 (d, J = 16.8 Hz, 1H), 3.86 (s, 3H), 3.68 (br s, 4H), 3.65-3.60 | 818.96 (818.42) | 819.4 | N.D. | N.D. | N.D. | N.D. | A | C |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 1H), 2.96-2.76 (m, 4H), 2.63-2.55 (m, 2H), 2.45-2.39 (m, 6H), 2.13 (br d, J = 6.8 Hz, 2H), 1.95 (br dd, J = 4.2, 8.0 Hz, 5H), 1.86-1.78 (m, 2H), 1.65-1.57 (m, 5H), 1.54-1.46 (m, 1H), 1.24-1.15 (m, 2H), 0.97-0.88 (m, 4H), 0.79-0.74 (m, 2H) | | | | | | | | |
| 274 | 1H NMR: (400 MHz, CD3OD) δ: 8.63 (s, 1H), 8.44 (s, 1H), 8.32 (d, J = 8.3 Hz, 1H), 7.53 (d, J = 8.3 Hz, 1H), 7.43 (s, 1H), 7.29 (d, J = 10.5 Hz, 1H), 7.17 (t, J = 7.8 Hz, 1H), 5.11 (dd, J = 5.1, 13.3 Hz, 1H), 4.60 (d, J = 12.8 Hz, 2H), 4.56-4.41 (m, 2H), 3.59 (d, J = 9.9 Hz, 2H), 3.28 (d, J = 1.5 Hz, 3H), 3.10-2.99 (m, 2H), 2.96-2.59 (m, 8H), 2.56-2.33 (m, 4H), 2.22-2.11 (m, 1H), 2.10-1.86 (m, 5H), 1.78 (s, 1H), 1.64 (s, 3H), 1.47-1.25 (m, 10H), 1.13-1.02 (m, 2H), 0.88-0.73 (m, 2H). | 851.00 (850.45) | 426.3 $[M/2+1]^+$ | N.D. | N.D. | N.D. | N.D. | A | B |
| 275 | 1H NMR: (400 MHz, CD3OD) δ: 8.67-8.57 (m, 1H), 8.53-8.44 (m, 1H), 8.35-8.27 (m, 1H), 7.58-7.50 (m, 1H), 7.41 (s, 1H), 7.32-7.25 (m, 1H), 7.23-7.15 (m, 1H), 5.16-5.08 (m, 1H), 4.56-4.42 (m, 4H), 3.68-3.57 (m, 2H), 3.19-2.99 (m, 4H), 2.92-2.74 (m, 6H), 2.72-2.59 (m, 2H), 2.56-2.43 (m, 2H), 2.35-2.25 (m, 2H), 2.20-2.12 (m, 1H), 2.03-1.89 (m, 5H), 1.86-1.75 (m, 1H), 1.64 (s, 3H), 1.55-1.42 (m, 2H), 1.40-1.26 (m, 6H), 1.26-1.16 (m, 2H), 1.12-0.97 (m, 2H), 0.84-0.74 (m, 2H). | 851.00 (850.45) | 426.3 $[M/2+1]^+$ | N.D. | N.D. | N.D. | N.D. | A | B |
| 276 | 1H NMR: (400 MHz, CD3OD) δ: 8.74 (d, J = 0.8 Hz, 1H), 8.63 (s, 1H), 7.78 (br s, 1H), 7.54 (d, J = 8.3 Hz, 1H), 7.44 (s, 1H), 7.19 (t, J = 7.9 Hz, 1H), 5.12 (dd, J = 5.1, 13.4 Hz, 1H), 4.75-4.61 (m, 2H), 4.50 (d, J = 15.5 Hz, 2H), 3.64 (br d, J = 11.3 Hz, 2H), 3.24-3.10 (m, 6H), 2.88-2.52 (br dd, J = 4.5, 12.8 Hz, 6H), 2.50-2.47 (br dd, J = 4.7, 13.2 Hz, 6H), 2.25-2.04 (m, 2H), 1.99 (br d, J = 12.3 Hz, 4H), 1.85 (br s, 1H), 1.68 (s, 3H), 1.60-1.46 (m, 2H), 1.44-1.20 (m, 5H), 1.05 (s, 2H), 0.85-0.80 (m, 2H) | 819.97 (819.43) | 820.4 | N.D. | N.D. | N.D. | N.D. | A | B |
| 277 | 1H NMR: (400 MHz, DMSO-d6) δ: 14.20-13.65 (m, 1H), 11.03-10.79 (m, 1H), 8.83-8.70 (m, 1H), 8.65-8.55 (m, 1H), 8.21-8.11 (m, 1H), 7.83-7.71 (m, 1H), 7.44-7.25 (m, 2H), 7.12-7.00 (m, 1H), 5.05-5.0(m, 1H), 4.54-4.37 (m, 4H), 3.93-3.79 (m, 3H), 3.63-3.49 (m, 4H), 3.06-2.82 (m, 4H), 2.66-2.55 (m, 4H), 2.45-2.35 (m, 2H), 2.25-2.12 (m, 2H), 2.10-2.04 (m, 2H), 2.01-1.93 (m, 2H), 1.89-1.76 (m, 5H), 1.65-1.58 (m, 3H), 1.55-1.43 (m, 1H), 1.32-1.15 (m, 2H), 1.15-1.04 (m, 2H), 1.01-0.96 (m, 6H), 0.95-0.89 (m, 2H), 0.79-0.72 (m, 2H) | 846.03 (845.47) | 846.8 | N.D. | N.D. | N.D. | N.D. | A | B |
| 278 | 1H NMR: (400 MHz, DMSO-d6) δ: 13.53-13.37 (m, 1H), 10.96 (s, 1H), 8.62 (s, 1H), 8.37 (s, 1H), 7.51-7.42 (m, 1H), 7.45 (d, J = 10.8 Hz, 1H), 7.41-7.33 (m, 2H), 7.07 (d, J = 8.3 Hz, 1H), 5.11-5.00 (m, 1H), 4.53-4.22 (m, 4H), 3.85 (s, 3H), 3.59-3.49 | 863.03 (862.47) | 864.5 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 3H), 2.92 (d, J = 12.4 Hz, 3H), 2.71-2.58 (m, 3H), 2.58-2.54 (m, 1H), 2.45-2.35 (m, 2H), 2.11 (d, J = 6.8 Hz, 7H), 1.88-1.75 (m, 4H), 1.74-1.61 (m, 2H), 1.57 (s, 3H), 1.36-1.22 (m, 2H), 1.09-0.97 (m, 4H), 0.95 (s, 6H), 0.83-0.77 (m, 2H) | | | | | | | | |
| 279 | 1H NMR: (400 MHz, DMSO-d6) δ: 13.46 (s, 1H), 10.97 (s, 1H), 8.63 (s, 1H), 8.38 (d, J = 8.4 Hz, 1H), 8.14 (s, 1H), 7.46 (d, J = 10.9 Hz, 1H), 7.41-7.33 (m, 2H), 7.08 (d, J = 8.3 Hz, 1H), 5.11-5.03 (m, 1H), 4.54-4.21 (m, 4H), 3.86 (s, 3H), 3.60-3.50 (m, 3H), 2.96 (t, J = 11.7 Hz, 3H), 2.71-2.53 (m, 6H), 2.42 (dd, J = 4.4, 13.2 Hz, 2H), 2.09 (d, J = 5.9 Hz, 5H), 2.01-1.93 (m, 1H), 1.81 (d, J = 11.8 Hz, 5H), 1.58 (s, 3H), 1.54-1.45 (m, 1H), 1.26 (d, J = 10.4 Hz, 2H), 1.16-1.05 (m, 2H), 1.01 (s, 8H), 0.84-0.75 (m, 2H) | 863.03 (862.47) | 863.8 | N.D. | N.D. | N.D. | N.D. | A | A |
| 280 | 1H NMR: (400 MHz, DMSO-d6) δ: 13.51-13.38 (m, 1H), 10.96 (s, 1H), 8.65 (s, 1H), 8.41-8.33 (m, 1H), 7.50-7.43 (m, 1H), 7.40-7.33 (m, 2H), 7.12-7.04 (m, 1H), 5.10-5.01 (m, 1H), 4.49-4.22 (m, 2H), 3.86 (s, 3H), 3.73-3.55 (m, 5H), 3.44-3.38 (m, 3H), 2.95-2.79 (m, 3H), 2.62-2.55 (m, 1H), 2.44 (br d, J = 3.9 Hz, 5H), 2.21-2.09 (m, 2H), 2.02-1.88 (m, 5H), 1.84-1.74 (m, 2H), 1.57 (s, 5H), 1.53-1.42 (m, 1H), 1.25-1.08 (m, 2H), 1.00 (s, 2H), 0.97-0.85 (m, 2H), 0.80 (s, 2H) | 835.96 (835.42) | 836.7 | N.D. | N.D. | N.D. | N.D. | A | B |
| 281 | 1H NMR: (400 MHz, DMSO-d6) δ: 13.49 (s, 1H), 10.99 (s, 1H), 8.64 (s, 1H), 8.38 (d, J = 8.4 Hz, 1H), 7.51-7.34 (m, 3H), 7.10 (d, J = 8.0 Hz, 1H), 5.07 (dd, J = 5.0, 13.3 Hz, 1H), 4.55-4.25 (m, 2H), 4.08 (d, J = 11.4 Hz, 2H), 3.87 (s, 3H), 3.75 (s, 1H), 3.21 (s, 11H), 2.98-2.84 (m, 2H), 2.68-2.54 (m, 2H), 2.43 (dd, J = 4.4, 13.1 Hz, 1H), 2.03-1.92 (m, 3H), 1.84 (dd, J = 14.0, 18.5 Hz, 4H), 1.71-1.61 (m, 1H), 1.57 (s, 3H), 1.42 (d, J = 8.8 Hz, 2H), 1.29-1.13 (m, 2H), 1.08-0.91 (m, 4H), 0.84-0.74 (m, 2H) | 835.96 (835.42) | 836.7 | N.D. | N.D. | N.D. | N.D. | A | B |
| 282 | 1H NMR: (400 MHz, CD3OD) δ: 8.64 (dd, J = 1.1, 17.3 Hz, 2H), 8.39 (s, 1H), 7.96 (d, J = 1.1 Hz, 1H), 7.49-7.43 (m, 2H), 7.12 (d, J = 8.3 Hz, 1H), 5.10 (dd, J = 5.1, 13.3 Hz, 2H), 4.59 (br d, J = 12.8 Hz, 2H), 4.51-4.39 (m, 2H), 3.92 (s, 3H), 3.67 (br d, J = 11.8 Hz, 2H), 3.37 (br d, J = 12.5 Hz, 1H), 3.16-2.98 (m, 5H), 2.95-2.84 (m, 2H), 2.82-2.68 (m, 5H), 2.67-2.61 (m, 2H), 2.57-2.43 (m, 3H), 2.15 (dtd, J = 2.3, 5.2, 12.7 Hz, 1H), 2.07-1.97 (m, 2H), 1.95-1.82 (m, 4H), 1.66 (s, 3H), 1.53-1.42 (m, 2H), 1.33-1.20 (m, 5H), 1.09-1.01 (m, 2H), 0.86-0.79 (m, 2H) | 832.00 (831.45) | 832.7 | N.D. | N.D. | N.D. | N.D. | A | A |
| 283 | 1H NMR: (400 MHz, DMSO-d6) δ: 14.03-13.79 (m, 1H), 11.01-10.88 (m, 1H), 8.88-8.69 (m, 1H), 8.67-8.60 (m, 1H), 8.15-8.11 (m, 1H), 7.83-7.76 (m, 1H), 7.42-7.35 (m, 2H), 7.30-7.11 (m, 1H), 5.12-4.98 (m, 1H), 4.58-4.37 (m, 4H), 3.92-3.80 (m, 3H), 3.60-3.49 (m, 4H), | 832.00 (831.45) | 832.8 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 3.04-2.83 (m, 5H), 2.77-2.58 (m, 5H), 2.58-2.52 (m, 1H), 2.45-2.35 (m, 1H), 2.31-2.09 (m, 4H), 2.03-1.72 (m, 7H), 1.70-1.56 (m, 3H), 1.42-1.18 (m, 2H), 1.16-0.99 (m, 5H), 0.97-0.89 (m, 2H), 0.79-0.70 (m, 2H) | | | | | | | | |
| 284 | 1H NMR: (400 MHz, DMSO-d6) δ = 13.43-13.33 (m, 1H), 10.98 (s, 1H), 8.61 (s, 1H), 8.19 (s, 1H), 8.16-8.11 (m, 1H), 7.48 (dd, J = 8.8, 15.6 Hz, 2H), 7.36 (s, 1H), 7.15 (t, J = 8.0 Hz, 1H), 7.09-7.03 (m, 1H), 5.06 (dd, J = 5.2, 13.2 Hz, 1H), 4.58-4.40 (m, 3H), 4.30 (d, J = 16.8 Hz, 1H), 2.94-2.85 (m, 4H), 2.80-2.72 (m, 3H), 2.64 (br s, 1H), 2.61 (br s, 1H), 2.55 (br s, 2H), 2.52 (br s, 1H), 2.47-2.40 (m, 2H), 2.30 (br s, 1H), 2.12-2.06 (m, 2H), 2.00-1.94 (m, 1H), 1.87-1.77 (m, 4H), 1.69 (br t, J = 10.4 Hz, 4H), 1.54 (s, 3H), 1.30-1.20 (m, 2H), 1.10-1.02 (m, 2H), 0.99 (br d, J = 6.0 Hz, 6H), 0.96-0.92 (m, 2H), 0.80-0.74 (m, 2H) | 833.01 (832.45) | 833.4 | N.D. | N.D. | N.D. | N.D. | A | B |
| 285 | 1H NMR: (400 MHz, DMSO-d6) δ: 13.67-13.41 (m, 1H), 11.15 (s, 1H), 8.80 (s, 1H), 8.32 (d, J = 2.0 Hz, 1H), 8.32 (s, 1H), 7.68 (d, J = 9.0 Hz, 1H), 7.60-7.48 (m, 2H), 7.29-7.16 (m, 2H), 5.31-5.18 (m, 1H), 4.61 (br d, J = 16.9 Hz, 3H), 4.46 (s, 1H), 4.04 (s, 3H), 3.13 (br s, 5H), 2.90-2.73 (m, 7H), 2.60 (br dd, J = 4.6, 13.1 Hz, 2H), 2.34 (br d, J = 5.4 Hz, 12H), 1.87 -1.75 (m, 1H), 1.72 (s, 3H), 1.58-1.37 (m, 2H), 1.33-1.23 (m, 2H), 1.19 (br d, J = 6.0 Hz, 3H), 1.12 (s, 2H), 0.95 (d, J = 1.6 Hz, 2H) | 831.01 (830.46) | 831.7 | N.D. | N.D. | N.D. | N.D. | A | A |
| 286 | 1H NMR: (400 MHz, DMSO-d6) δ: 13.49-13.26 (m, 1H), 11.11-10.95 (m, 1H), 8.72-8.59 (m, 1H), 8.20-8.13 (m, 1H), 7.55-7.47 (m, 1H), 7.43-7.36 (m, 2H), 7.11-7.02 (m, 1H), 5.15-5.01 (m, 1H), 4.54-4.20 (m, 2H), 3.78-3.52 (m, 5H), 3.19-3.05 (m, 2H), 2.98-2.84 (m, 1H), 2.64-2.53 (m, 2H), 2.48-2.36 (m, 7H), 2.17-2.09 (m, 2H), 2.03-1.76 (m, 7H), 1.62-1.39 (m, 6H), 1.26-1.10 (m, 2H), 1.01-0.84 (m, 4H), 0.82-0.73 (m, 2H) | 823.93 (823.40) | 824.7 | N.D. | N.D. | N.D. | N.D. | B | A |
| 287 | 1H NMR: (400 MHz, DMSO-d6) δ = 13.38 (br s, 1H), 10.96 (s, 1H), 8.61 (s, 1H), 8.24 (s, 1H), 8.15 (d, J = 2.0 Hz, 1H), 7.50 (d, J = 9.2 Hz, 1H), 7.42-7.33 (m, 2H), 7.06 (td, J = 2.4, 8.8 Hz, 2H), 5.06 (dd, J = 5.2, 13.2 Hz, 1H), 4.58-4.40 (m, 3H), 4.26 (d, J = 17.2 Hz, 1H), 3.85 (s, 3H), 3.52 (br d, J = 11.2 Hz, 2H), 2.95-2.85 (m, 3H), 2.66 (br d, J = 10.4 Hz, 4H), 2.61 (br s, 1H), 2.52 (br s, 1H), 2.45 (br d, J = 8.4 Hz, 1H), 2.40 (br d, J = 4.0 Hz, 1H), 2.34-2.29 (m, 2H), 2.12-2.06 (m, 2H), 2.00-1.93 (m, 1H), 1.83 (br t, J = 12.4 Hz, 4H), 1.73-1.62 (m, 4H), 1.54 (s, 3H), 1.33-1.22 (m, 2H), 1.11-1.02 (m, 2H), 0.99 (d, J = 6.0 Hz, 6H), 0.96-0.92 (m, 2H), 0.80-0.74 (m, 2H) | 845.04 (844.47) | 845.4 | N.D. | N.D. | N.D. | N.D. | A | B |
| 288 | 1H NMR: (400 MHz, DMSO-d6) δ = 13.39 (br s, 1H), 10.97 (s, 1H), 8.63 (s, 1H), 8.25 (s, 1H), 8.16 (d, J = 2.0 | 845.04 (844.47) | 845.4 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | Hz, 1H), 7.51 (d, J = 9.0 Hz, 1H), 7.44-7.35 (m, 2H), 7.08 (td, J = 2.2, 8.8 Hz, 2H), 5.07 (dd, J = 5.0, 13.3 Hz, 1H), 4.56-4.38 (m, 3H), 4.27 (d, J = 16.9 Hz, 1H), 3.95-3.75 (m, 3H), 3.55 (br d, J = 9.8 Hz, 3H), 3.05-2.84 (m, 3H), 2.72-2.56 (m, 5H), 2.42-2.31 (m, 3H), 2.13-2.06 (m, 2H), 2.01-1.92 (m, 1H), 1.92-1.76 (m, 5H), 1.70 (br t, J = 10.2 Hz, 2H), 1.57-1.44 (m, 4H), 1.36-1.21 (m, 2H), 1.11-0.98 (m, 9H), 0.97-0.87 (m, 2H), 0.81-0.72 (m, 2H) | | | | | | | | |
| 289 | 1H NMR (400 MHz, $CDCl_3$) δ 13.41 (s, 1H), 10.98 (s, 1H), 8.61 (d, J = 1.1 Hz, 1H), 8.16 (br s, 1H), 8.16-8.13 (m, 1H), 7.48 (dd, J = 8.6, 16.1 Hz, 2H), 7.16 (t, J = 7.9 Hz, 1H), 7.06 (dd, J = 2.4, 9.0 Hz, 1H), 6.98 (d, J = 0.9 Hz, 1H), 5.06 (dd, J = 5.1, 13.3 Hz, 1H), 4.61 (br t, J = 4.4 Hz, 1H), 4.48 (d, J = 17.0 Hz, 1H), 4.38-4.28 (m, 3H), 3.89 (br dd, J = 4.1, 9.3 Hz, 2H), 2.95 (br s, 2H), 2.83-2.63 (m, 6H), 2.35-2.31 (m, 1H), 2.18 (br d, J = 6.9 Hz, 2H), 2.11-2.02 (m, 2H), 1.99-1.92 (m, 1H), 1.82 (br t, J = 13.3 Hz, 4H), 1.72-1.62 (m, 1H), 1.54 (s, 3H), 1.51-1.42 (m, 2H), 1.34-1.01 (m, 3H), 0.97-0.91 (m, 2H), 0.80-0.75 (m, 2H) | 777.88 (777.38) | 778.6 | N.D. | N.D. | N.D. | N.D. | A | A |
| 290 | 1H NMR (400 MHz, METHANOL-d4): δ 8.62 (s, 1H), 8.31-8.21 (m, 2H), 8.08 (d, J = 1.9 Hz, 1H), 7.65 (d, J = 7.9 Hz, 1H), 7.57-7.49 (m, 1H), 7.49-7.45 (m, 1H), 7.43-7.40 (m, 1H), 7.14-7.07 (m, 1H), 5.20-5.12 (m, 1H), 4.64-4.49 (m, 2H), 4.45-4.35 (m, 1H), 4.25-4.10 (m, 2H), 3.97-3.83 (m, 1H), 3.79-3.69 (m, 1H), 3.66-3.56 (m, 2H), 3.55-3.44 (m, 2H), 3.37-3.32 (m, 1H), 3.02-2.74 (m, 4H), 2.63-2.41 (m, 5H), 2.23-2.06 (m, 5H), 2.04-1.92 (m, 2H), 1.70-1.58 (m, 5H), 1.05-0.98 (m, 2H), 0.82-0.73 (m, 2H) | 762.87 (762.37) | 763.6 | N.D. | N.D. | N.D. | N.D. | A | A |
| 291 | 1H NMR (400 MHz, MeOD): δ 8.70-8.60 (m, 1H), 8.17-8.14 (m, 1H), 7.58-7.37 (m, 3H), 7.21-7.07 (m, 2H), 5.17-5.08 (m, 1H), 4.66-4.41 (m, 2H), 4.12-4.07 (m, 3H), 4.00-3.94 (m, 6H), 3.51-3.39 (m, 6H), 3.24-3.11 (m, 8H), 2.97-2.86 (m, 2H), 2.82-2.74 (m, 4H), 2.68-2.60 (m, 2H), 2.56-2.46 (m, 1H), 2.20-2.12 (m, 1H), 1.67-1.55 (m, 3H), 1.06-0.98 (m, 2H), 0.82-0.73 (m, 2H) | 820.93 (820.40) | 821.6 | N.D. | N.D. | N.D. | N.D. | A | A |
| 292 | 1H NMR (400 MHz, METHANOL-d4): δ 8.63-8.57 (m, 1H), 8.27 (br s, 1H), 8.06 (d, J = 1.9 Hz, 1H), 7.64 (d, J = 7.9 Hz, 1H), 7.55-7.44 (m, 2H), 7.39 (s, 1H), 7.13-7.07 (m, 1H), 5.18-5.12 (m, 1H), 4.63-4.53 (m, 4H), 4.16-4.08 (m, 1H), 3.92-3.80 (m, 1H), 3.59 (br d, J = 11.8 Hz, 2H), 3.11-2.84 (m, 6H), 2.83-2.74 (m, 1H), 2.58-2.50 (m, 2H), 2.49-2.37 (m, 4H), 2.23-1.93 | 776.90 (776.38) | 777.7 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 7H), 1.89 (br d, J = 13.3 Hz, 2H), 1.64-1.57 (m, 3H), 1.41-1.30 (m, 2H), 1.05-0.99 (m, 2H), 0.81-0.76 (m, 2H) | | | | | | | | |
| 293 | 1H NMR (400 MHz, DMSO-d6): δ 13.41 (s, 1H), 10.97 (s, 1H), 8.64 (s, 1H), 8.28-8.12 (m, 1H), 7.51 (d, J = 8.9 Hz, 1H), 7.41-7.36 (m, 2H), 7.13-7.05 (m, 2H), 5.06 (dd, J = 4.9, 12.9 Hz, 1H), 4.48-4.41 (m, 1H), 4.29-4.24 (m, 1H), 3.86 (s, 3H), 3.67 (br s, 4H), 2.69-2.67 (m, 4H), 2.43 (br d, J = 14.0 Hz, 9H), 2.35-2.32 (m, 4H), 2.04 (br s, 3H), 1.96 (br s, 3H), 1.66-1.51 (m, 6H), 0.95 (s, 2H), 0.81-0.75 (m, 2H) | 789.92 (789.40) | 790.6 | N.D. | N.D. | N.D. | N.D. | A | B |
| 294 | 1H NMR (400 MHz, DMSO-d6): δ 13.46 (br s, 1H), 10.99 (s, 1H), 8.64 (d, J = 0.8 Hz, 1H), 8.38 (d, J = 8.4 Hz, 1H), 8.17 (s, 1H), 7.52-7.43 (m, 2H), 7.38 (s, 1H), 7.16 (t, J = 7.9 Hz, 1H), 5.13-5.03 (m, 1H), 4.84-4.64 (m, 1H), 4.55-4.24 (m, 4H), 3.19-3.06 (m, 5H), 3.00-2.83 (m, 4H), 2.61-2.51 (m, 6H), 2.47-2.36 (m, 2H), 2.25-2.13 (m, 3H), 2.01-1.93 (m, 2H), 1.91-1.66 (m, 4H), 1.58 (s, 3H), 1.54-1.40 (m, 2H), 1.17-1.05 (m, 2H), 1.02-0.96 (m, 2H), 0.85-0.74 (m, 2H) | 840.93 (840.40) | 421.4 [M/2 + 1]+ | N.D. | N.D. | N.D. | N.D. | A | B |
| 295 | 1H NMR (400 MHz, DMSO-d6): δ 13.61-13.16 (m, 1H), 11.53-10.78 (m, 1H), 8.68-8.50 (m, 1H), 8.21-8.16 (m, 1H), 7.56-7.42 (m, 2H), 7.20-7.12 (m, 1H), 7.10-7.01 (m, 2H), 5.15-4.98 (m, 1H), 4.53-4.27 (m, 2H), 3.78-3.47 (m, 6H), 2.96-2.86 (m, 1H), 2.77 (br t, J = 11.6 Hz, 2H), 2.62-2.52 (m, 4H), 2.47-2.32 (m, 9H), 2.24-2.16 (m, 2H), 2.13-2.02 (m, 1H), 2.02-1.91 (m, 1H), 1.87-1.77 (m, 2H), 1.76-1.61 (m, 2H), 1.59-1.50 (m, 3H), 1.34-1.15 (m, 2H), 1.01-0.90 (m, 2H), 0.82-0.73 (m, 2H) | 790.93 (790.41) | 791.5 | N.D. | N.D. | N.D. | N.D. | A | B |
| 296 | 1H NMR (400 MHz, DMSO-d6): δ 13.49-13.34 (m, 1H), 11.04-10.89 (m, 1H), 8.72-8.56 (m, 1H), 8.20-8.17 (m, 1H), 8.17-8.14 (m, 1H), 7.54-7.47 (m, 2H), 7.41-7.37 (m, 1H), 7.20-7.13 (m, 1H), 7.10-7.05 (m, 1H), 5.13-5.00 (m, 1H), 4.54-4.26 (m, 2H), 3.87-3.77 (m, 2H), 3.75-3.55 (m, 6H), 3.22-3.05 (m, 6H), 2.97-2.83 (m, 1H), 2.65-2.52 (m, 8H), 2.47-2.34 (m, 6H), 2.03-1.89 (m, 1H), 1.56-1.50 (m, 3H), 0.98-0.91 (m, 2H), 0.80-0.74 (m, 2H) | 808.90 (808.38) | 808.9 | N.D. | N.D. | N.D. | N.D. | A | B |
| 297 | 1H NMR (400 MHz, DMSO-d6) δ: $^{1}$H NMR (400 MHz, DMSO-d6) 8 = 13.43-13.29 (m, 1H), 11.02-10.97 (m, 1H), 8.72-8.58 (m, 1H), 8.18-8.11 (m, 1H), 7.67 (br t, J = 5.6 Hz, 1H), 7.58 (br d, J = 7.5 Hz, 1H), 7.53-7.48 (m, 1H), 7.42-7.36 (m, 1H), 7.10-7.04 (m, 1H), 5.18-5.06 (m, 1H), 5.00-4.72 (m, 1H), 4.62-4.52 (m, 1H), 4.47-4.34 (m, 1H), 4.27- | 780.86 (780.36) | 781.6 | N.D. | N.D. | N.D. | N.D. | A | B |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 4.17 (m, 1H), 4.15-4.06 (m, 2H), 3.61 (br s, 1H), 3.47-3.41 (m, 1H), 3.22-3.08 (m, 2H), 3.01-2.86 (m, 3H), 2.60 (br d, J = 17.0 Hz, 1H), 2.48-2.35 (m, 2H), 2.27-2.14 (m, 2H), 2.08-1.97 (m, 3H), 1.95-1.73 (m, 6H), 1.54 (s, 3H), 1.50-1.41 (m, 2H), 0.98-0.92 (m, 2H), 0.80-0.73 (m, 2H) | | | | | | | | |
| 298 | 1H NMR (400 MHz, DMSO-d6) δ: 13.41 (s, 1H), 10.96 (s, 1H), 8.66-8.53 (m, 1H), 8.16 (d, J = 9.0 Hz, 1H), 7.51 (d, J = 9.0 Hz, 1H), 7.38 (d, J = 8.1 Hz, 1H), 7.07 (dt, J = 2.6, 5.8 Hz, 2H), 7.01-6.96 (m, 1H), 5.06 (dd, J = 5.1, 13.2 Hz, 1H), 4.67-4.58 (m, 1H), 4.44 (d, J = 16.9 Hz, 1H), 4.38-4.32 (m, 2H), 4.26 (br d, J = 16.9 Hz, 1H), 3.90 (br dd, J = 4.0, 9.3 Hz, 2H), 3.86 (s, 3H), 3.54 (br d, J = 9.5 Hz, 2H), 2.89 (br dd, J = 4.6, 13.0 Hz, 1H), 2.76 (br s, 2H), 2.70-2.61 (m, 3H), 2.42 (br s, 2H), 2.24 (br s, 2H), 2.12 (br s, 2H), 2.01-1.94 (m, 1H), 1.83 (br d, J = 12.0 Hz, 4H), 1.67 (br s, 1H), 1.57-1.49 (m, 5H), 1.30 (q, J = 11.1 Hz, 2H), 0.98-0.91 (m, 2H), 0.81-0.73 (m, 2H) | 789.92 (789.40) | 790.6 | N.D. | N.D. | N.D. | N.D. | A | B |
| 299 | 1H NMR (400 MHz, DMSO-d6) δ: 13.49 (br s, 1H), 10.99 (s, 1H), 8.66 (s, 1H), 8.39 (d, J = 8.4 Hz, 1H), 8.17 (s, 1H), 7.51-7.44 (m, 2H), 7.39 (s, 1H), 7.17 (t, J = 7.9 Hz, 1H), 5.12-5.03 (m, 1H), 4.85-4.66 (m, 1H), 4.48 (d, J = 17.0 Hz, 1H), 4.31 (d, J = 16.8 Hz, 1H), 3.48 (br d, J = 6.9 Hz, 4H), 3.16-3.05 (m, 2H), 2.96-2.72 (m, 5H), 2.63-2.52 (m, 2H), 2.49-2.40 (m, 4H), 2.26-2.05 (m, 4H), 2.03-1.91 (m, 2H), 1.86-1.64 (m, 4H), 1.58 (s, 3H), 1.55-1.40 (m, 2H), 1.34-1.20 (m, 2H), 1.06 (t, J = 7.3 Hz, 1H), 1.01 (s, 2H), 0.85-0.77 (m, 2H) | 840.93 (840.40) | 421.4 $[M/2 + 1]^+$ | N.D. | N.D. | N.D. | N.D. | A | B |
| 300 | 1H NMR (400 MHz, DMSO-d6) δ: 13.42 (s, 1H), 11.01 (s, 1H), 8.66 (s, 1H), 8.20-8.12 (m, 1H), 7.50 (dd, J = 8.6, 16.6 Hz, 2H), 7.39 (s, 1H), 7.19 (t, J = 7.9 Hz, 1H), 7.08 (dd, J = 2.3, 9.1 Hz, 1H), 5.09 (dd, J = 4.9, 13.3 Hz, 1H), 4.53-4.28 (m, 2H), 4.27-3.91 (m, 1H), 3.67 (br s, 4H), 3.54-3.46 (m, 1H), 3.33 (s, 6H), 2.99-2.85 (m, 3H), 2.60 (br d, J = 17.9 Hz, 1H), 2.42 (br d, J = 5.8 Hz, 6H), 2.05-1.92 (m, 4H), 1.61-1.53 (m, 6H), 0.99-0.94 (m, 2H), 0.82-0.76 (m, 2H) | 777.88 (777.38) | 778.7 | N.D. | N.D. | N.D. | N.D. | A | B |
| 301 | 1H NMR (400 MHz, DMSO-d6) δ: 13.74-13.15 (m, 1H), 11.39-10.89 (m, 1H), 8.70-8.60 (m, 1H), 8.18-8.12 (m, 1H), 7.54-7.44 (m, 2H), 7.39-7.33 (m, 1H), 7.20-7.13 (m, 1H), 7.09-7.02 (m, 1H), 5.15-4.93 (m, 1H), 4.61-4.25 (m, 4H), 3.49-3.42 (m, 2H), 3.13-3.04 (m, 2H), 2.99-2.86 (m, 3H), 2.86-2.75 (m, 2H), 2.70-2.65 (m, 4H), 2.64-2.53 (m, 4H), 2.47-2.36 (m, 4H), 2.06-1.93 (m, 1H), 1.83-1.74 (m, 2H), 1.71-1.59 (m, 1H), 1.59- | 794.89 (794.38) | 795.6 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1.49 (m, 3H), 1.19-1.04 (m, 2H), 1.00-0.89 (m, 2H), 0.84-0.72 (m, 2H) | | | | | | | | |
| 302 | 1H NMR (400 MHz, DMSO-d6) δ = 10.97 (s, 1H), 8.79 (s, 1H), 8.64 (s, 1H), 8.24 (s, 2H), 7.79 (s, 1H), 7.40-7.32 (m, 2H), 7.06 (d, J = 8.2 Hz, 1H), 5.06 (dd, J = 5.2, 13.2 Hz, 2H), 4.52-4.15 (m, 2H), 3.94-3.73 (m, 7H), 3.72-3.61 (m, 5H), 3.28 (br t, J = 10.8 Hz, 3H), 3.10 (br s, 4H), 2.99-2.77 (m, 1H), 2.71-2.52 (m, 6H), 2.46-2.36 (m, 4H), 2.06-1.83 (m, 1H), 1.61 (s, 3H), 1.00-0.85 (m, 2H), 0.82-0.61 (m, 2H) | 821.92 (821.40) | 822.3 | N.D. | N.D. | N.D. | N.D. | A | B |
| 303 | 1H NMR (400 MHz, DMSO-d6) δ: 13.49-13.13 (m, 1H), 11.02-10.77 (m, 1H), 8.71-8.46 (m, 1H), 8.19-8.16 (m, 1H), 7.57-7.47 (m, 1H), 7.42-7.33 (m, 1H), 7.17-6.98 (m, 3H), 5.26-4.98 (m, 1H), 4.59-4.19 (m, 2H), 3.94-3.79 (m, 3H), 3.69-3.43 (m, 6H), 2.98-2.85 (m, 1H), 2.53 (br s, 6H), 2.49-2.35 (m, 9H), 2.25-2.16 (m, 2H), 2.16-2.05 (m, 1H), 2.02-1.92 (m, 1H), 1.88-1.78 (m, 2H), 1.75-1.61 (m, 2H), 1.59-1.48 (m, 3H), 1.36-1.24 (m, 2H), 1.01-0.91 (m, 2H), 0.86-0.69 (m, 2H) | 802.96 (802.43) | 803.6 | N.D. | N.D. | N.D. | N.D. | A | B |
| 304 | 1H NMR (400 MHz, DMSO-d6) δ: 13.43-13.32 (m, 1H), 10.99-10.93 (m, 1H), 8.64-8.54 (m, 1H), 8.17-8.11 (m, 1H), 7.58-7.41 (m, 2H), 7.23-7.13 (m, 1H), 7.10-7.04 (m, 1H), 6.97 (s, 1H), 5.15-4.99 (m, 1H), 4.51-4.29 (m, 2H), 4.20 (br s, 1H), 3.82 (s, 4H), 3.54-3.44 (m, 3H), 2.98-2.83 (m, 4H), 2.63-2.53 (m, 2H), 2.47-2.35 (m, 3H), 2.29-2.20 (m, 2H), 2.07 (br s, 2H), 2.03-1.89 (m, 4H), 1.84 (br s, 4H), 1.65-1.56 (m, 2H), 1.54 (s, 3H), 1.01-0.91 (m, 2H), 0.81-0.72 (m, 2H) | 803.92 (803.39) | 804.7 | N.D. | N.D. | N.D. | N.D. | A | B |
| 305 | 1H NMR (400 MHz, CDCl3) δ: 8.76 (s, 1H), 8.28 (s, 1H), 8.18-8.01 (m, 1H), 7.73-7.56 (m, 1H), 7.49-7.37 (m, 1H), 7.36-7.31 (m, 1H), 7.15 (dd, J = 2.3, 9.0 Hz, 1H), 7.11-7.04 (m, 1H), 5.29-5.12 (m, 1H), 4.58-4.31 (m, 2H), 4.26-4.08 (m, 1H), 3.82-3.69 (m, 4H), 3.63 (td, J = 6.8, 8.0 Hz, 1H), 3.35-3.32 (m, 4H), 3.17-3.07 (m, 1H), 2.98-2.78 (m, 4H), 2.59-2.45 (m, 6H), 2.27-2.14 (m, 4H), 1.86-1.70 (m, 3H), 1.65 (s, 3H), 1.51-1.17 (m, 5H), 1.12-1.05 (m, 2H), 0.89-0.65 (m, 2H) | 806.93 (806.40) | 807.4 | N.D. | N.D. | N.D. | N.D. | A | B |
| 306 | 1H NMR (400 MHz, DMSO-d6) δ: 13.73-13.15 (m, 1H), 11.32-10.71 (m, 1H), 8.69-8.60 (m, 1H), 8.17-8.12 (m, 1H), 7.57-7.42 (m, 2H), 7.41-7.35 (m, 1H), 7.22-7.12 (m, 1H), 7.10-7.03 (m, 1H), 5.13-5.03 (m, 1H), 4.55-4.27 (m, 2H), 3.73-3.64 (m, 4H), 3.47 (br d, J = 5.6 Hz, 4H), 3.10 (br d, J = 13.5 Hz, 2H), 2.95-2.88 (m, 1H), 2.84-2.71 (m, 4H), 2.62-2.57 (m, 4H), 2.42 (br d, J = | 794.89 (794.38) | 795.6 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 6.8 Hz, 4H), 2.03-1.93 (m, 1H), 1.84-1.73 (m, 2H), 1.59-1.52 (m, 3H), 1.51-1.41 (m, 1H), 1.37-1.24 (m, 2H), 1.00-0.91 (m, 2H), 0.84-0.72 (m, 2H) | | | | | | | | |
| 307 | 1H NMR (400 MHz, DMSO-d6) δ: 13.38 (br s, 1 H), 10.98 (s, 1 H), 8.62 (s, 1 H), 8.20 (s, 1 H), 8.14 (d, J = 0.88 Hz, 1 H), 7.48 (dd, J = 14.8, 8.4 Hz, 2 H), 7.36 (s, 1 H), 7.12 (t, J = 8.0 Hz, 1 H), 7.06 (dd, J = 8.8, 2.0 Hz, 1 H), 5.06 (dd, J = 13.2, 5.2 Hz, 1 H), 4.39-4.53 (m, 3 H), 4.30 (d, J = 16.8 Hz, 1 H), 2.84-3.00 (m, 4 H), 2.59-2.77 (m, 6 H), 2.29-2.40 (m, 3 H), 2.06 (br d, J = 6.4 Hz, 2 H), 1.94-2.00 (m, 1 H), 1.82 (br t, J = 14.4 Hz, 5 H), 1.68 (br t, J = 10.4 Hz, 2 H), 1.54 (s, 4 H), 1.24 (br d, J = 11.2 Hz, 3 H), 0.90-1.10 (m, 11 H), 0.74-0.80 (m, 2 H). | 833.01 (832.45) | 833.3 | N.D. | N.D. | N.D. | N.D. | A | B |
| 308 | 1H NMR (400 MHz, DMSO-d6)δ: 13.38 (s, 1H), 10.98 (s, 1H), 8.63 (s, 1H), 8.19 (s, 1H), 8.18-8.13 (m, 1H), 7.51-7.45 (m, 2H), 7.39 (s, 1H), 7.15 (t, J = 8.0 Hz, 1H), 7.06 (dd, J = 2.4, 8.8 Hz, 1H), 5.07 (dd, J = 4.8, 13.2 Hz, 1H), 4.48 (d, J = 16.8 Hz, 1H), 4.30 (d, J = 16.8 Hz, 1H), 4.12-4.03 (m, 2H), 3.77-3.67 (m, 1H), 3.66-3.55 (m, 1H), 3.52-3.44 (m, 2H), 3.38-3.36 (m, 2H), 2.95-2.83 (m, 1H), 2.77-2.70 (m, 2H), 2.60-2.56 (m, 1H), 2.45-2.38 (m, 3H), 2.32-2.27 (m, 1H), 2.00-1.83 (m, 6H), 1.72-1.67 (m, 2H), 1.56-1.48 (m, 4H), 1.46-1.37 (m, 2H), 1.33-1.12 (m, 4H), 1.06 (s, 3H), 0.97-0.89 (m, 5H), 0.81-0.73 (m, 2H) | 833.99 (833.44) | 834.3 | N.D. | N.D. | N.D. | N.D. | A | B |
| 309 | 1H NMR (400 MHz, DMSO-d6) δ: 13.36 (s, 1 H), 10.97 (s, 1 H), 8.62 (s, 1 H), 8.15 (s, 1 H), 7.48 (dd, J = 17.06, 8.50 Hz, 2 H), 7.36 (s, 1 H), 7.15 (s, 1 H), 7.06 (d, J = 9.17 Hz, 1 H), 5.07 (d, J = 11.13 Hz, 1 H), 4.38-4.52 (m, 3 H), 4.30 (d, J = 16.63 Hz, 1 H), 3.56 (s, 2 H), 2.93 (d, J = 13.33 Hz, 4 H), 2.58-2.78 (m, 2 H), 2.53-2.56 (m, 3 H), 2.33-2.44 (m, 6 H), 2.11 (s, 2 H), 1.98 (s, 1 H), 1.79 (s, 5 H), 1.68 (s, 1 H), 1.54 (s, 3 H), 1.35 (s, 2 H), 1.06 (s, 2 H), 0.94 (s, 2 H), 0.89 (s, 6 H), 0.77 (s, 2 H). | 833.01 (832.45) | 834.3 | N.D. | N.D. | N.D. | N.D. | A | A |
| 310 | 1H NMR (400 MHz, DMSO-d6) δ: 13.36 (s, 1H), 10.97 (s, 1H), 8.61 (d, J = 0.8 Hz, 1H), 8.15 (d, J = 2.0 Hz, 1H), 7.51-7.46 (m, 2H), 7.37 (s, 1H), 7.20-7.14 (m, 1H), 7.09-7.04 (m, 1H), 5.10-5.04 (m, 1H), 4.52-4.41 (m, 3H), 4.34-4.28 (m, 1H), 3.66-3.55 (m, 2H), 3.30-3.29 (m, 3H), 2.96-2.90 (m, 4H), 2.74-2.71 (m, 1H), 2.44-2.38 (m, 3H), 2.00-1.87 (m, 6H), 1.74-1.65 (m, 3H), 1.60-1.52 (m, 6H), 1.33-1.22 (m, 2H), 1.17-1.11 (m, 2H), 1.05-1.00 (m, 3H), 0.97-0.92 (m, 3H), 0.91-0.87 (m, 2H), 0.79-0.75 (m, 2H) | 833.99 (833.44) | 834.4 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| 311 | 1H NMR (400 MHz, DMSO-d6) δ: 13.44-13.31 (m, 1H), 10.96 (s, 1H), 8.59 (s, 1H), 8.15 (s, 1H), 7.56-7.46 (m, 1H), 7.36 (s, 1H), 7.12-6.98 (m, 3H), 5.17-4.94 (m, 1H), 4.57-4.17 (m, 2H), 3.85 (s, 3H), 3.53 (d, J = 9.9 Hz, 7H), 2.97-2.85 (m, 2H), 2.69-2.58 (m, 4H), 2.45-2.30 (m, 9H), 2.24-2.18 (m, 2H), 2.15-2.04 (m, 1H), 2.00-1.92 (m, 1H), 1.86-1.79 (m, 2H), 1.75-1.61 (m, 2H), 1.54 (s, 3H), 1.39-1.22 (m, 2H), 0.95 (s, 2H), 0.78 (d, J = 1.3 Hz, 2H) | 802.96 (802.43) | 803.7 | N.D. | N.D. | N.D. | N.D. | A | B |
| 312 | 1H NMR (400 MHz, METHANOL-d4) δ: 8.64 (dd, J = 1.1, 17.3 Hz, 2H), 8.39 (s, 1H), 7.96 (d, J = 1.1 Hz, 1H), 7.49-7.43 (m, 2H), 7.12 (d, J = 8.3 Hz, 1H), 5.10 (dd, J = 5.1, 13.3 Hz, 2H), 4.59 (br d, J = 12.8 Hz, 2H), 4.51-4.39 (m, 2H), 3.92 (s, 3H), 3.67 (br d, J = 11.8 Hz, 2H), 3.37 (br d, J = 12.5 Hz, 1H), 3.16-2.98 (m, 5H), 2.95-2.84 (m, 2H), 2.82-2.68 (m, 5H), 2.67-2.61 (m, 2H), 2.57-2.43 (m, 3H), 2.15 (dtd, J = 2.3, 5.2, 12.7 Hz, 1H), 2.07-1.97 (m, 2H), 1.95-1.82 (m, 4H), 1.66 (s, 3H), 1.53-1.42 (m, 2H), 1.33-1.20 (m, 5H), 1.09-1.01 (m, 2H), 0.86-0.79 (m, 2H) | 832.00 (831.45) | 832.7 | N.D. | N.D. | N.D. | N.D. | A | A |
| 313 | 1H NMR (400 MHz, CD3OD) δ: 8.63 (s, 1H), 8.11-8.08 (m, 1H), 7.54-7.43 (m, 3H), 7.21-7.16 (m, 1H), 7.12-7.08 (m, 1H), 5.14-5.09 (m, 2H), 4.69-4.44 (m, 4H), 3.99-3.70 (m, 1H), 3.56-3.44 (m, 3H), 3.15-2.99 (m, 5H), 2.96-2.85 (m, 2H), 2.81-2.69 (m, 2H), 2.57-2.44 (m, 1H), 2.19-2.10 (m, 3H), 2.07-2.01 (m, 3H), 1.80-1.71 (m, 2H), 1.61 (s, 3H), 1.54-1.48 (m, 2H), 1.45-1.38 (m, 4H), 1.34-1.27 (m, 5H), 1.04-0.93 (m, 3H), 0.80-0.75 (m, 2H) | 833.99 (833.44) | 834.3 | N.D. | N.D. | N.D. | N.D. | A | B |
| 314 | 1H NMR (400 MHz, DMSO-d6) δ: 13.41 (s, 1H), 10.99 (s, 1H), 8.65 (s, 1H), 8.16 (d, J = 6.5 Hz, 2H), 7.52 (d, J = 9.0 Hz, 1H), 7.41 (t, J = 3.8 Hz, 2H), 7.14-7.04 (m, 2H), 5.08 (br dd, J = 5.1, 13.3 Hz, 1H), 4.47 (br d, J = 16.9 Hz, 1H), 4.29 (br d, J = 16.9 Hz, 1H), 4.11 (br s, 2H), 4.06-3.94 (m, 1H), 3.87 (s, 3H), 3.65-3.57 (m, 1H), 3.14 (br s, 4H), 2.99-2.87 (m, 1H), 2.62 (br s, 4H), 2.43 (br s, 7H), 2.10-2.03 (m, 2H), 2.01-1.95 (m, 1H), 1.87 (br s, 2H), 1.56 (s, 4H), 1.44 (s, 3H), 0.96 (s, 2H), 0.83-0.75 (m, 2H) | 789.92 (789.40) | 790.6 | N.D. | N.D. | N.D. | N.D. | A | B |
| 315 | 1H NMR (400 MHz, DMSO-d6) δ: 13.40 (s, 1H), 10.97 (s, 1H), 8.64 (s, 1H), 8.22-8.10 (m, 1H), 7.51 (d, J = 8.9 Hz, 1H), 7.43-7.37 (m, 2H), 7.11-7.03 (m, 2H), 5.06 (dd, J = 5.3, 13.1 Hz, 1H), 4.45 (d, J = 16.8 Hz, 1H), 4.34-4.24 (m, 2H), 4.10 (br s, 2H), 3.86 (s, 3H), 3.62 (br s, 1H), 3.51 (br d, J = 7.4 Hz, 4H), 3.04 (br s, 6H), 2.61 (br | 815.96 (815.41) | 816.7 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | s, 1H), 2.46-2.39 (m, 2H), 2.37-2.28 (m, 2H), 2.23-2.10 (m, 2H), 1.92 (br s, 8H), 1.55 (s, 3H), 1.44 (br d, J = 9.1 Hz, 2H), 0.97-0.93 (m, 2H), 0.80-0.76 (m, 2H) | | | | | | | | |
| 316 | 1H NMR (400 MHz, DMSO-d6) δ: 13.38 (s, 1H), 10.96 (s, 1H), 8.68-8.55 (m, 1H), 8.18 (s, 1H), 8.15 (d, J = 1.6 Hz, 1H), 7.50 (d, J = 8.8 Hz, 1H), 7.38-7.36 (m, 2H), 7.09-7.04 (m, 2H), 5.06 (dd, J = 5.2, 13.6 Hz, 1H), 4.54-4.35 (m, 3H), 4.26 (d, J = 16.8 Hz, 1H), 3.95-3.77 (m, 3H), 3.64-3.53 (m, 2H), 3.48-3.38 (m, 2H), 2.96-2.82 (m, 4H), 2.76-2.69 (m, 1H), 2.61-2.59 (m, 1H), 2.42-2.38 (m, 2H), 2.01-1.88 (m, 6H), 1.72-1.67 (m, 3H), 1.64-1.56 (m, 2H), 1.54 (s, 3H), 1.33-1.20 (m, 4H), 1.10-0.99 (m, 5H), 0.98-0.94 (m, 2H), 0.90 (s, 3H), 0.79-0.75 (m, 2H) | 846.03 (845.46) | 846.3 | N.D. | N.D. | N.D. | N.D. | A | B |
| 317 | 1H NMR (400 MHz, DMSO) δ: 13.51-13.31 (m, 1H), 10.97 (s, 1H), 8.67 (br s, 1H), 8.21-8.09 (m, 1H), 7.56-7.32 (m, 3H), 7.08 (dd, J = 2.4, 9.0 Hz, 1H), 6.67 (t, J = 8.1 Hz, 1H), 5.05 (dd, J = 5.1, 13.3 Hz, 1H), 4.45 (d, J = 16.9 Hz, 1H), 4.28 (d, J = 16.9 Hz, 1H), 4.11 (br d, J = 7.4 Hz, 4H), 3.88 (br s, 2H), 3.17-3.06 (m, 2H), 2.97-2.73 (m, 5H), 2.66-2.53 (m, 4H), 2.49-2.29 (m, 4H), 2.08-1.92 (m, 3H), 1.55 (s, 3H), 1.28-1.07 (m, 4H), 0.98-0.91 (m, 2H), 0.82-0.74 (m, 2H) | 812.88 (812.37) | 813.7 | N.D. | N.D. | N.D. | N.D. | A | B |
| 318 | 1H NMR (400 MHz, DMSO-d6) δ = 13.37 (s, 1H), 10.96 (s, 1H), 8.62 (s, 1H), 8.16-8.13 (m, 1H), 7.50 (d, J = 8.8 Hz, 1H), 7.40-7.33 (m, 2H), 7.11-7.03 (m, 2H), 5.06 (dd, J = 5.2, 13.2 Hz, 1H), 4.54-4.37 (m, 3H), 4.26 (d, J = 17.2 Hz, 1H), 3.86 (s, 3H), 3.68-3.59 (m, 2H), 2.99-2.86 (m, 3H), 2.63-2.55 (m, 4H), 2.52 (br s, 3H), 2.47-2.34 (m, 5H), 2.21-2.11 (m, 2H), 2.01-1.93 (m, 1H), 1.91-1.75 (m, 5H), 1.71-1.62 (m, 1H), 1.54 (s, 3H), 1.46-1.31 (m, 2H), 1.14-1.04 (m, 2H), 0.97-0.86 (m, 8H), 0.80-0.74 (m, 2H) | 845.04 (844.47) | 845.4 | N.D. | N.D. | N.D. | N.D. | A | A |
| 319 | 1H NMR (400 MHz, DMSO-d6) δ: 13.38 (s, 1H), 10.95 (s, 1H), 8.63 (s, 1H), 8.16 (s, 1H), 8.15 (d, J = 2.0 Hz, 1H), 7.50 (d, J = 8.8 Hz, 1H), 7.39-7.36 (m, 2H), 7.16-6.98 (m, 2H), 5.06 (dd, J = 4.8, 13.2 Hz, 1H), 4.43 (d, J = 16.8 Hz, 1H), 4.26 (d, J = 16.8 Hz, 1H), 4.12-4.01 (m, 2H), 3.86 (s, 3H), 3.77-3.68 (m, 1H), 3.65-3.49 (m, 3H), 3.40-3.36 m, 2H), 2.95-2.84 (m, 1H), 2.73-2.69 (m, 1H), 2.65-2.59 (m, 2H), 2.57-2.54 (m, 1H), 2.45-2.39 (m, 2H), 2.37-2.34 (m, 1H), 2.00-1.91 (m, 3H), 1.90-1.83 (m, 3H), 1.75-1.66 (m, 2H), 1.54 (s, 3H), 1.53-1.47 (m, 1H), 1.47-1.38 (m, 2H), | 846.03 (845.46) | 846.3 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1.34-1.13 (m, 4H), 1.07 (s, 3H), 0.97-0.90 (m, 5H), 0.80-0.74 (m, 2H) | | | | | | | | |
| 320 | 1H NMR (400 MHz, DMSO-d6) δ: 13.39 (s, 1 H), 10.99 (s, 1 H), 8.62 (s, 1 H), 8.23 (s, 1 H), 8.15 (s, 1 H), 7.48 (dd, J = 15.16, 8.56 Hz, 2 H), 7.37 (s, 1 H), 7.15 (s, 1 H), 7.06 (dd, J = 9.05, 2.32 Hz, 1 H), 5.07 (dd, J = 13.20, 5.01 Hz, 1 H), 4.43-4.61 (m, 3 H), 4.30 (d, J = 16.87 Hz, 1 H), 3.42-3.54 (m, 2 H), 2.71-2.98 (m, 6 H), 2.58 (d, J = 17.97 Hz, 2 H), 2.52 (d, J = 1.83 Hz, 3 H), 2.34-2.45 (m, 4 H), 2.15 (d, J = 5.99 Hz, 2 H), 1.93-2.01 (m, 1 H), 1.80 (d, J = 12.23 Hz, 5 H), 1.67 (s, 1 H), 1.54 (s, 3 H), 1.12-1.30 (m, 4 H), 0.91-0.98 (m, 2 H), 0.85 (s, 6 H), 0.74-0.79 (m, 2 H). | 833.01 (832.45) | 834.4 | N.D. | N.D. | N.D. | N.D. | A | B |
| 321 | 1H NMR (400 MHz, MeOH-d4) δ: 8.59 (d, J = 0.9 Hz, 1H), 8.06 (d, J = 1.8 Hz, 1H), 7.48-7.32 (m, 3H), 7.08 (dd, J = 2.3, 9.0 Hz, 1H), 6.81 (t, J = 8.1 Hz, 1H), 5.08 (dd, J = 5.1, 13.4 Hz, 1H), 4.55-4.37 (m, 4H), 3.75-3.42 (m, 4H), 3.02 (t, J = 12.0 Hz, 2H), 2.87 (dd, J = 5.3, 13.4 Hz, 1H), 2.82-2.73 (m, 1H), 2.70-2.37 (m, 12H), 2.27 (d, J = 6.5 Hz, 2H), 2.20-2.11 (m, 2H), 2.03-1.86 (m, 3H), 1.74 (dd, J = 8.4, 12.1 Hz, 1H), 1.60 (s, 3H), 1.23 (d, J = 10.1 Hz, 2H), 1.01 (s, 2H), 0.81-0.74 (m, 2H) | 790.93 (790.41) | 791.4 | N.D. | N.D. | N.D. | N.D. | A | B |
| 322 | 1H NMR(400 MHz, DMSO-d6) δ: 13.38 (s, 1H), 10.96 (s, 1H), 8.65 (s, 1H), 8.16 (d, J = 2.0 Hz, 1H), 8.15-8.13 (m, 1H), 7.52 (d, J = 8.8 Hz, 1H), 7.43-7.39 (m, 2H), 7.18-7.01 (m, 2H), 5.07 (dd, J = 5.2, 13.6 Hz, 1H), 4.61-4.38 (m, 3H), 4.27 (d, J = 16.8 Hz, 1H), 3.87 (s, 3H), 3.73-3.51 (m, 2H), 3.45-3.39 (m, 2H), 3.05-2.81 (m, 5H), 2.64-2.61 (m, 3H), 2.45-2.42 (m, 2H), 2.10-2.02 (m, 3H), 2.02-1.91 (m, 4H), 1.89-1.81 (m, 1H), 1.75-1.58 (m, 4H), 1.55 (s, 3H), 1.43-1.34 (m, 3H), 1.32-1.23 (m, 3H), 1.16-1.00 (m, 2H), 1.00-0.89 (m, 3H), 0.83-0.74 (m, 2H) | 846.03 (845.46) | 846.3 | N.D. | N.D. | N.D. | N.D. | A | B |
| 323 | 1H NMR (400 MHz, DMSO-d6) δ: 13.42-13.33 (m, 1H), 10.99-10.90 (m, 1H), 8.65-8.61 (m, 1H), 8.17-8.12 (m, 1H), 7.54-7.46 (m, 1H), 7.41-7.34 (m, 2H), 7.10-7.02 (m, 1H), 6.64-6.55 (m, 1H), 5.08-4.98 (m, 1H), 4.34 (s, 2H), 4.17 (br d, J = 4.8 Hz, 1H), 4.14-4.04 (m, 2H), 3.83-3.72 (m, 4H), 3.61-3.55 (m, 1H), 2.97-2.78 (m, 3H), 2.60-2.55 (m, 1H), 2.44-2.35 (m, 2H), 2.31-2.11 (m, 5H), 2.05-1.95 (m, 3H), 1.90-1.84 (m, 2H), 1.77 (br s, 4H), 1.58-1.53 (m, 3H), 1.51-1.33 (m, 3H), 0.97-0.93 (m, 2H), 0.80-0.75 (m, 2H) | 803.92 (803.39) | 804.6 | N.D. | N.D. | N.D. | N.D. | A | B |
| 324 | 1HNMR (400 MHz, DMSO-d6) δ: 14.03-13.79 (m, 1H), 11.01-10.88 (m, 1H), 8.88-8.69 (m, | 832.00 (831.45) | 832.8 | N.D. | N.D. | N.D. | N.D. | A | A |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| Degradation and characterization of exemplary bifunctional compounds of the present disclosure | | | | | | | | | |
| | 1H), 8.67-8.60 (m, 1H), 8.15-8.11 (m, 1H), 7.83-7.76 (m, 1H), 7.42-7.35 (m, 2H), 7.30-7.11 (m, 1H), 5.12-4.98 (m, 1H), 4.58-4.37 (m, 4H), 3.92-3.80 (m, 3H), 3.60-3.49 (m, 4H), 3.04-2.83 (m, 5H), 2.77-2.58 (m, 5H), 2.58-2.52 (m, 1H), 2.45-2.35 (m, 1H), 2.31-2.09 (m, 4H), 2.03-1.72 (m, 7H), 1.70-1.56 (m, 3H), 1.42-1.18 (m, 2H), 1.16-0.99 (m, 5H), 0.97-0.89 (m, 2H), 0.79-0.70 (m, 2H) | | | | | | | | |
| 325 | 1H NMR (400 MHz, DMSO-d6) δ: 13.38 (s, 1H), 10.96 (s, 1H), 8.63 (s, 1H), 8.17 (s, 1H), 8.16-8.14 (m, 1H), 7.50 (d, J = 8.8 Hz, 1H), 7.39-7.36 (m, 2H), 7.09-7.05 (m, 2H), 5.06 (dd, J = 4.8, 13.2 Hz, 1H), 4.43 (d, J = 16.8 Hz, 1H), 4.26 (d, J = 16.8 Hz, 1H), 4.15-4.00 (m, 2H), 3.86 (s, 3H), 3.77-3.69 (m, 1H), 3.64-3.51 (m, 3H), 3.44-3.35 (m, 2H), 2.98-2.83 (m, 1H), 2.75-2.68 (m, 1H), 2.66-2.56 (m, 3H), 2.47-2.40 (m, 2H), 2.39-2.32 (m, 1H), 1.97-1.93 (m, 3H), 1.91-1.83 (m, 3H), 1.76-1.65 (m, 2H), 1.54 (s, 3H), 1.52-1.37 (m, 3H), 1.36-1.18 (m, 4H), 1.07 (s, 3H), 0.98-0.89 (m, 5H), 0.82-0.73 (m, 2H) | 846.03 (845.46) | 846.4 | N.D. | N.D. | N.D. | N.D. | A | B |
| 326 | 1H NMR (400 MHz, DMSO-d6) δ: 13.39 (br s, 1H), 10.98 (s, 1H), 8.67-8.56 (m, 1H), 8.20 (s, 1H), 8.19-8.13 (m, 1H), 7.59-7.26 (m, 3H), 7.17 (br t, J = 7.9 Hz, 1H), 7.08-7.05 (m, 1H), 5.07 (dd, J = 4.9, 13.3 Hz, 1H), 4.52-4.44 (m, 1H), 4.34-4.20 (m, 2H), 3.64 (br s, 2H), 3.02 (br d, J = 6.9 Hz, 1H), 2.94 (s, 3H), 2.93-2.85 (m, 4H), 2.59 (br d, J = 16.4 Hz, 2H), 2.54-2.52 (m, 1H), 2.42 (td, J = 4.3, 8.6 Hz, 2H), 2.20 (br s, 1H), 2.05-1.85 (m, 8H), 1.84-1.65 (m, 4H), 1.62-1.52 (m, 5H), 0.95 (s, 2H), 0.81-0.75 (m, 2H) | 803.92 (803.39) | 804.7 | N.D. | N.D. | N.D. | N.D. | A | B |
| 327 | 1H NMR (400 MHz, DMSO-d6) δ: 13.52-13.20 (m, 1H), 10.98 (s, 1H), 8.59 (s, 1H), 8.21-8.09 (m, 1H), 7.46 (d, J = 8.1 Hz, 2H), 7.20-7.13 (m, 1H), 7.05 (s, 2H), 5.19-5.00 (m, 1H), 4.32 (s, 2H), 3.57 (s, 7H), 3.00-2.86 (m, 2H), 2.83-2.71 (m, 2H), 2.65-2.54 (m, 3H), 2.44-2.30 (m, 8H), 2.19 (d, J = 6.9 Hz, 2H), 2.14-2.03 (m, 1H), 2.02-1.93 (m, 1H), 1.87-1.76 (m, 2H), 1.76-1.62 (m, 2H), 1.54 (s, 3H), 1.33-1.18 (m, 2H), 0.95 (s, 2H), 0.77 (d, J = 1.5 Hz, 2H). | 790.93 (790.41) | 791.7 | N.D. | N.D. | N.D. | N.D. | A | B |
| 328 | 1H NMR (400 MHz, MeOD) δ: 8.59 (d, J = 0.8 Hz, 1H), 8.06 (d, J = 1.8 Hz, 1H), 7.49-7.31 (m, 3H), 7.08 (dd, J = 2.3, 9.1 Hz, 1H), 6.84 (d, J = 8.5 Hz, 1H), 5.11-5.05 (m, 1H), 4.56-4.38 (m, 4H), 3.73 (d, J = 0.8 Hz, 3H), 3.64-3.55 (m, 2H), 3.51 (dd, J = 5.6, 7.9 Hz, 2H), 3.02 (t, J = 11.9 Hz, 2H), 2.87 (dd, J = 5.3, 13.4 Hz, 1H), 2.81-2.73 (m, 1H), 2.68-2.42 (m, 12H), 2.27 (d, J = 6.5 Hz, 2H), 2.15 (dd, J = 6.1, | 802.96 (802.43) | 803.4 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 11.8 Hz, 2H), 1.91 (d, J = 12.6 Hz, 3H), 1.71 (dd, J = 8.3, 11.9 Hz, 1H), 1.60 (s, 3H), 1.22 (d, J = 10.3 Hz, 2H), 1.01 (s, 2H), 0.77 (d, J = 1.6 Hz, 2H) | | | | | | | | |
| 329 | 1H NMR (400 MHz, DMSO-d6) δ: 13.39 (s, 1H), 10.99 (s, 1H), 8.63 (d, J = 1.0 Hz, 1H), 8.15 (d, J = 2.3 Hz, 1H), 7.50 (d, J = 9.1 Hz, 1H), 7.45-7.33 (m, 3H), 7.07 (dd, J = 2.4, 9.0 Hz, 1H), 5.10 (dd, J = 5.1, 13.4 Hz, 1H), 4.64 (d, J = 17.1 Hz, 1H), 4.46 (d, J = 17.0 Hz, 1H), 4.25-4.04 (m, 3H), 3.96-3.82 (m, 3H), 3.65-3.54 (m, 1H), 3.05-2.91 (m, 4H), 2.88-2.80 (m, 1H), 2.62 (br s, 1H), 2.52 (br s, 2H), 2.43 (br s, 1H), 2.23-2.11 (m, 2H), 2.06-1.95 (m, 3H), 1.93-1.84 (m, 2H), 1.84-1.75 (m, 2H), 1.73-1.60 (m, 4H), 1.54 (s, 3H), 1.44 (dt, J = 4.4, 8.6 Hz, 2H), 0.99-0.91 (m, 2H), 0.80-0.73 (m, 2H) | 774.91 (774.39) | 775.4 | N.D. | N.D. | N.D. | N.D. | A | B |
| 330 | 1H NMR (400 MHz, METHANOL-d4) δ: 8.61 (s, 1H), 8.45 (s, 1H), 8.08 (d, J = 2.0 Hz, 1H), 7.45 (t, J = 9.2 Hz, 2H), 7.40 (s, 1H), 7.09 (dd, J = 2.4, 9.2 Hz, 1H), 6.82 (t, J = 8.4 Hz, 1H), 5.11 (d, J = 5.2 Hz, 1H), 4.57 (d, J = 16.0 Hz, 2H), 4.52-4.38 (m, 2H), 3.69 (d, J = 6.8 Hz, 1H), 3.64-3.54 (m, 2H), 3.04 (t, J = 11.6 Hz, 3H), 2.96-2.73 (m, 9H), 2.72-2.55 (m, 6H), 2.48 (dt, J = 8.4, 13.2 Hz, 1H), 2.22-2.11 (m, 2H), 2.10-2.02 (m, 1H), 1.92 (d, J = 11.6 Hz, 2H), 1.77 (dd, J = 8.4, 12.4 Hz, 1H), 1.61 (s, 3H), 1.33-1.21 (m, 2H), 1.05-0.98 (m, 2H), 0.80-0.75 (m, 2H) | 790.93 (790.41) | 791.7 | N.D. | N.D. | N.D. | N.D. | A | B |
| 331 | 1H NMR (400 MHz, DMSO-d6) δ: 13.37 (s, 1 H), 10.95 (s, 1 H), 8.61 (s, 1 H), 8.32 (s, 1 H), 8.15 (s, 1 H), 7.50 (d, J = 9.01 Hz, 1 H), 7.34-7.40 (m, 2 H), 7.03-7.11 (m, 2 H), 5.06 (dd, J = 13.32, 4.82 Hz, 1 H), 4.54 (s, 2 H), 4.43 (d, J = 16.88 Hz, 1 H), 4.26 (d, J = 17.01 Hz, 1 H), 3.86 (s, 3 H), 3.53 (d, J = 8.51 Hz, 2 H), 2.82-2.93 (m, 3 H), 2.63 (d, J = 14.51 Hz, 2 H), 2.54-2.57 (m, 1 H), 2.34-2.47 (m, 7 H), 2.17 (d, J = 6.25 Hz, 2 H), 1.77-2.01 (m, 7 H), 1.66 (s, 1 H), 1.54 (s, 3 H), 1.07-1.36 (m, 5 H), 0.92-0.97 (m, 2 H), 0.86 (s, 6 H), 0.83-0.89 (m, 1 H), 0.74-0.79 (m, 2 H). | 845.04 (844.47) | 846.4 | N.D. | N.D. | N.D. | N.D. | A | B |
| 332 | 1H NMR (400 MHz, DMSO-d6) δ: 13.48-13.32 (m, 1H), 11.12-10.77 (m, 1H), 8.62 (s, 1H), 8.28-8.09 (m, 1H), 7.50 (d, J = 9.0 Hz, 1H), 7.37 (s, 1H), 7.31 (d, J = 8.1 Hz, 1H), 7.08 (d, J = 2.3 Hz, 1H), 6.57 (d, J = 8.3 Hz, 1H), 5.13-5.00 (m, 1H), 4.54-4.25 (m, 4H), 4.04 (d, J = 8.1 Hz, 2H), 3.80 (d, J = 8.0 Hz, 2H), 3.75 (s, 3H), 2.96 (s, 4H), 2.67 (d, J = 1.6 Hz, 3H), | 795.87 (795.37) | 796.4 | N.D. | N.D. | N.D. | N.D. | A | B |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| Degradation and characterization of exemplary bifunctional compounds of the present disclosure | | | | | | | | | |
| | 2.43 (d, J = 4.0 Hz, 2H), 2.24 (d, J = 6.9 Hz, 2H), 2.02 (s, 4H), 1.78 (s, 2H), 1.54 (s, 3H), 1.16-1.03 (m, 2H), 0.94 (s, 2H), 0.77 (d, J = 1.1 Hz, 2H). | | | | | | | | |
| 333 | 1H NMR (400 MHz, DMSO-d6) δ: 13.40 (s, 1H), 10.98 (s, 1H), 8.64 (s, 1H), 8.15 (d, J = 1.5 Hz, 1H), 7.57-7.44 (m, 2H), 7.38 (s, 1H), 7.14 (d, J = 8.1 Hz, 1H), 7.10-7.02 (m, 1H), 5.20-5.02 (m, 1H), 4.44-4.12 (m, 2H), 3.67 (s, 5H), 3.12-3.01 (m, 2H), 2.97-2.85 (m, 1H), 2.81-2.69 (m, 2H), 2.65-2.56 (m, 1H), 2.47-2.34 (m, 6H), 2.20 (s, 3H), 2.17-2.10 (m, 2H), 1.96 (d, J = 10.5 Hz, 5H), 1.87-1.76 (m, 2H), 1.67-1.57 (m, 2H), 1.54 (s, 3H), 1.52-1.43 (m, 1H), 1.27-1.08 (m, 2H), 0.99-0.84 (m, 4H), 0.77 (d, J = 1.5 Hz, 2H). | 801.97 (801.43) | 401.8 $[M/2 + 1]^+$ | N.D. | N.D. | N.D. | N.D. | A | B |
| 334 | 1H NMR (400 MHz, DMSO-d6) δ: 13.44 (s, 1H), 10.98 (s, 1H), 8.68 (s, 1H), 8.19-8.12 (m, 1H), 7.51 (d, J = 9.3 Hz, 2H), 7.43 (s, 1H), 7.27-7.14 (m, 1H), 7.13-7.01 (m, 1H), 5.15-5.01 (m, 1H), 4.57-4.28 (m, 2H), 3.93-3.56 (m, 4H), 3.25-3.13 (m, 5H), 3.00-2.54 (m, 14H), 2.45-2.36 (m, 2H), 2.34-2.22 (m, 2H), 2.04-1.85 (m, 2H), 1.54 (s, 3H), 1.50-1.43 (m, 1H), 0.94 (s, 2H), 0.77 (d, J = 1.4 Hz, 2H) | 776.90 (776.39) | 777.4 | N.D. | N.D. | N.D. | N.D. | A | B |
| 335 | 1H NMR (400 MHz, DMSO-d6) δ: 13.40 (br s, 1H), 10.99 (s, 1H), 8.63 (s, 1H), 8.15 (s, 2H), 7.49 (dd, J = 8.6, 15.2 Hz, 2H), 7.39 (s, 1H), 7.16 (t, J = 7.9 Hz, 1H), 7.07 (dd, J = 2.4, 9.0 Hz, 1H), 5.08 (dd, J = 5.1, 13.3 Hz, 1H), 4.48 (d, J = 17.0 Hz, 1H), 4.31 (d, J = 16.9 Hz, 1H), 4.27-4.20 (m, 1H), 4.09 (br d, J = 13.0 Hz, 2H), 3.62-3.53 (m, 1H), 3.06 (br s, 5H), 3.00 (br s, 4H), 2.95-2.88 (m, 1H), 2.59 (br d, J = 16.3 Hz, 1H), 2.54-2.52 (m, 2H), 2.45-2.37 (m, 1H), 2.09-2.00 (m, 2H), 1.99-1.86 (m, 4H), 1.83 (br d, J = 4.4 Hz, 5H), 1.55 (s, 3H), 1.42 (br d, J = 8.8 Hz, 2H), 0.98-0.92 (m, 2H), 0.81-0.75 (m, 2H) | 803.92 (803.39) | 402.9 $[M/2 + 1]^+$ | N.D. | N.D. | N.D. | N.D. | A | B |
| 336 | 1H NMR (400 MHz, DMSO-d6) δ: 13.42 (s, 1H), 10.98 (s, 1H), 8.65 (s, 1H), 8.19-8.13 (m, 1H), 7.51 (d, J = 9.0 Hz, 1H), 7.43-7.37 (m, 2H), 7.07 (dd, J = 2.3, 9.1 Hz, 1H), 6.68 (t, J = 8.1 Hz, 1H), 5.05 (dd, J = 5.0, 13.4 Hz, 1H), 4.50-4.27 (m, 2H), 4.11 (br d, J = 7.8 Hz, 2H), 3.88 (br s, 2H), 3.67 (br s, 4H), 2.97-2.86 (m, 1H), 2.77 (br s, 2H), 2.63-2.55 (m, 5H), 2.40 (br dd, J = 4.6, 12.9 Hz, 4H), 2.09-1.88 (m, 4H), 1.55 (s, 3H), 1.26-1.14 (m, 2H), 0.97-0.93 (m, 2H), 0.80-0.76 (m, 2H) | 798.85 (798.36) | 799.6 | N.D. | N.D. | N.D. | N.D. | A | B |
| 337 | 1H NMR (400 MHz, METHANOL-d4)δ 8.63 (br d, J = 3.0 Hz, 1H), 8.38-8.35 (m, 1H), 8.10 (s, 1H), 7.55-7.50 (m, 1H), 7.48-7.44 (m, 1H), 7.41-7.37 | 793.90 (793.39) | 794.7 | N.D. | N.D. | N.D. | N.D. | A | A |

TABLE 2-continued

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | Degradation and characterization of exemplary bifunctional compounds of the present disclosure | | | | | | | | |
| | (m, 1H), 7.20-7.14 (m, 1H), 7.11-7.07 (m, 1H), 5.15-5.07 (m, 1H 0-4.41 (m, 4H), 3.87-3.69 (m, 4H), 3.62-3.53 (m, 2H), 3.08-2.97 (m, 2H), 2.95 (s, 6H), 2.55 (s, 1H), 2.20-2.12 (m, 1H), 1.99-1.95 (m, 1H), 1.94-1.71 (m, 7H), 1.61 (s, 3H), 1.57-1.46 (m, 2H), 1.36-1.21 (m, 2H), 1.05-0.99 (m, 2H), 0.81-0.75 (m, 2H) | | | | | | | | |
| 338 | 1H NMR (400 MHz, DMSO-d6) δ: 13.88 (s, 1H), 10.96 (s, 1H), 8.79 (s, 1H), 8.63 (s, 1H), 8.13 (s, 1H), 7.79 (s, 1H), 7.37 (d, J = 8.0 Hz, 2H), 7.08 (d, J = 8.3 Hz, 1H), 5.06 (dd, J = 4.9, 13.4 Hz, 1H), 4.54-4.36 (m, 3H), 4.26 (d, J = 17.0 Hz, 1H), 3.85 (s, 3H), 3.60-3.49 (m, 2H), 3.08-2.83 (m, 4H), 2.72-2.57 (m, 6H), 2.36-2.29 (m, 3H), 2.21-2.07 (m, 4H), 2.02-1.91 (m, 2H), 1.83 (br d, J = 11.8 Hz, 3H), 1.76-1.64 (m, 2H), 1.61 (s, 3H), 1.38-1.21 (m, 3H), 1.20-1.11 (m, 1H), 1.11-1.02 (m, 2H), 0.99-0.89 (m, 6H), 0.79-0.73 (m, 2H) | 846.03 (845.47) | 846.8 | N.D. | N.D. | N.D. | N.D. | A | B |
| 339 | 1H NMR (400 MHz, DMSO-d6 δ: 10.76-10.63 (m, 1H), 8.68-8.64 (m, 1H), 8.14-8.10 (m, 1H), 7.54-7.47 (m, 2H), 7.42-7.38 (m, 1H), 7.23-7.17 (m, 1H), 7.14-7.08 (m, 1H), 5.10-4.93 (m, 1H), 4.53-4.44 (m, 3H), 4.41-4.33 (m, 1H), 3.65-3.34 (m, 6H), 3.09-2.97 (m, 6H), 2.95-2.83 (m, 4H), 2.64-2.58 (m, 2H), 2.46-2.39 (m, 2H), 2.28-2.00 (m, 5H), 1.96-1.85 (m, 3H), 1.59-1.54 (m, 3H), 1.38-1.18 (m, 6H), 1.01-0.95 (m, 2H), 0.80-0.74 (m, 2H) | 818.98 (818.44) | 819.8 | N.D. | N.D. | N.D. | N.D. | A | B |
| 340 | 1H NMR (400 MHz, DMSO-d6) δ: 13.49 (s, 1H), 10.99 (s, 1H), 8.64 (s, 1H), 8.38 (d, J = 8.4 Hz, 1H), 7.51-7.34 (m, 3H), 7.10 (d, J = 8.0 Hz, 1H), 5.07 (dd, J = 5.0, 13.3 Hz, 1H), 4.55-4.25 (m, 2H), 4.08 (d, J = 11.4 Hz, 2H), 3.87 (s, 3H), 3.75 (s, 1H), 3.21 (s, 11H), 2.98-2.84 (m, 2H), 2.68-2.54 (m, 2H), 2.43 (dd, J = 4.4, 13.1 Hz, 1H), 2.03-1.92 (m, 3H), 1.84 (dd, J = 14.0, 18.5 Hz, 4H), 1.71-1.61 (m, 1H), 1.57 (s, 3H), 1.42 (d, J = 8.8 Hz, 2H), 1.29-1.13 (m, 2H), 1.08-0.91 (m, 4H), 0.84-0.74 (m, 2H). | 835.96 (835.42) | 418.8 $[M/2 + 1]^+$ | N.D. | N.D. | N.D. | N.D. | A | B |
| 341 | 1H NMR (400 MHz, MeOD) δ: 8.67-8.54 (m, 1H), 8.20 (s, 2H), 8.09-7.97 (m, 1H), 7.54-7.34 (m, 3H), 7.17-7.06 (m, 1H), 6.67-6.55 (m, 1H), 5.13-5.05 (m, 1H), 4.58-4.48 (m, 4H), 4.20-4.12 (m, 2H), 3.88-3.81 (m, 2H), 3.79 (s, 3H), 3.09-3.01 (m, 2H), 2.94-2.85 (m, 1H), 2.82-2.71 (m, 2H), 2.62-2.46 (m, 4H), 2.21-2.10 (m, 3H), 1.93-1.85 (m, 2H), 1.79-1.71 (m, 1H), 1.61 (s, 3H), 1.57-1.51 (m, 2H), 1.34-1.26 (m, 2H), 1.06-0.99 (m, 2H), 0.84-0.75 (m, 2H), 0.82-0.75 (m, 2H). | 809.90 (809.38) | 810.5 | N.D. | N.D. | N.D. | N.D. | A | B |

TABLE 2-continued

| Degradation and characterization of exemplary bifunctional compounds of the present disclosure | | | | | | | | | |
|---|---|---|---|---|---|---|---|---|---|
| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
| 342 | 1H NMR (400 MHz, DMSO-d6) δ: 13.39 (s, 1H), 11.00 (s, 1H), 8.63 (s, 1H), 8.15 (d, J = 1.5 Hz, 1H), 7.74 (d, J = 8.0 Hz, 1H), 7.69 (s, 1H), 7.59 (s, 1H), 7.50 (d, J = 9.0 Hz, 1H), 7.40 (s, 1H), 7.07 (s, 1H), 5.18-5.03 (m, 1H), 4.52-4.31 (m, 2H), 4.26-4.18 (m, 1H), 4.16-4.03 (m, 2H), 3.65-3.57 (m, 2H), 3.05-2.93 (m, 2H), 2.88 (s, 2H), 2.60 (d, J = 16.6 Hz, 1H), 2.40 (dd, J = 4.3, 12.9 Hz, 1H), 2.27-1.84 (m, 14H), 1.54 (s, 3H), 1.50-1.37 (m, 2H), 0.99-0.91 (m, 2H), 0.77 (s, 2H). | 762.87 (762.37) | 763.4 | N.D. | N.D. | N.D. | N.D. | A | B |
| 343 | 1H NMR (400 MHz, DMSO-d6) δ = 14.14-13.64 (m, 1H), 10.98 (s, 1H), 8.78 (d, J = 0.8 Hz, 1H), 8.62 (s, 1H), 8.16 (s, 1H), 7.79 (d, J = 1.2 Hz, 1H), 7.48 (d, J = 8.4 Hz, 1H), 7.37 (s, 1H), 7.15 (t, J = 8.0 Hz, 1H), 5.07 (dd, J = 5.2, 13.6 Hz, 1H), 4.54-4.38 (m, 3H), 4.31 (d, J = 12.8 Hz, 1H), 3.13 (br s, 4H), 3.02-2.82 (m, 4H), 2.71-2.55 (m, 8H), 2.45-2.34 (m, 1H), 2.28-2.12 (m, 4H), 2.03-1.93 (m, 1H), 1.90-1.68 (m, 6H), 1.61 (s, 4H), 1.17-1.00 (m, 2H), 0.96-0.88 (m, 2H), 0.79-0.71 (m, 2H). | 823.93 (823.41) | 824.3 | N.D. | N.D. | N.D. | N.D. | A | B |
| 344 | 1H NMR (400 MHz, DMSO-d6) δ: 13.43-13.32 (m, 1H), 11.04-10.88 (m, 1H), 8.66-8.60 (m, 1H), 8.15 (s, 1H), 7.50 (d, J = 9.1 Hz, 1H), 7.41-7.38 (m, 1H), 7.30-7.26 (m, 1H), 7.09-7.04 (m, 1H), 6.55-6.48 (m, 1H), 5.09-4.97 (m, 1H), 4.49-4.24 (m, 2H), 4.21-4.15 (m, 1H), 4.15-4.03 (m, 2H), 3.72 (s, 3H), 3.71-3.68 (m, 3H), 3.61-3.55 (m, 1H), 2.95-2.86 (m, 2H), 2.78 (br s, 2H), 2.58 (br d, J = 17.5 Hz, 1H), 2.43-2.37 (m, 2H), 2.22 (br s, 1H), 2.20-2.12 (m, 3H), 2.05-1.92 (m, 4H), 1.92-1.85 (m, 2H), 1.75 (br s, 5H), 1.54 (s, 3H), 1.43 (br d, J = 8.8 Hz, 2H), 0.97-0.92 (m, 2H), 0.80-0.75 (m, 2H) | 815.96 (815.41) | 816.7 | N.D. | N.D. | N.D. | N.D. | A | B |
| 345 | 1H NMR (400 MHz, DMSO-d6) δ: 13.39 (s, 1H), 10.97 (s, 1H), 8.63 (s, 1H), 8.29 (s, 0.1H), 8.16 (s, 1H), 7.51 (d, J = 9.0 Hz, 1H), 7.41-7.35 (m, 2H), 7.11-7.04 (m, 2H), 5.06 (dd, J = 5.0, 13.3 Hz, 1H), 4.48-4.22 (m, 4H), 3.85 (s, 3H), 3.46 (br s, 2H), 3.27-3.19 (m, 2H), 2.99-2.86 (m, 3H), 2.74 (br s, 2H), 2.25 (br s, 2H), 2.01-1.84 (m, 4H), 1.79 (br d, J = 6.3 Hz, 6H), 1.55 (s, 3H), 1.37 (br d, J = 10.0 Hz, 2H), 1.29-1.13 (m, 3H), 0.97-0.93 (m, 2H), 0.80-0.75 (m, 2H) | 791.91 (791.39) | 792.7 | N.D. | N.D. | N.D. | N.D. | A | B |
| 346 | 1H NMR (400 MHz, DMSO-d6) δ:13.39 (s, 1H), 10.99 (s, 1H), 8.63 (s, 1H), 8.15 (s, 2H), 7.49 (dd, J = 8.6, 11.5 Hz, 2H), 7.39 (s, 1H), 7.14 (br t, J = 7.9 Hz, 1H), 7.06 (dd, J = 2.3, 9.0 Hz, 1H), 5.07 (dd, J = 5.0, 13.3 Hz, 1H), 4.48 (br d, J = 17.0 Hz, 1H), 4.31 (d, J = 16.9 Hz, 1H), 4.12-4.03 (m, 2H), 3.78-3.71 (m, 1H), 3.01-2.84 (m, | 819.96 (819.42) | 820.8 | N.D. | N.D. | N.D. | N.D. | A | B |

TABLE 2-continued

| Degradation and characterization of exemplary bifunctional compounds of the present disclosure | | | | | | | | |
|---|---|---|---|---|---|---|---|---|
| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
| | 4H), 2.74-2.67 (m, 1H), 2.62-2.53 (m, 2H), 2.46-2.39 (m, 2H), 2.37-2.17 (m, 2H), 1.99-1.82 (m, 8H), 1.71 (br d, J = 11.0 Hz, 1H), 1.54 (s, 3H), 1.42 (br d, J = 8.8 Hz, 4H), 1.27-1.08 (m, 3H), 1.03 (br d, J = 6.1 Hz, 3H), 0.94 (br t, J = 5.6 Hz, 3H), 0.89-0.83 (m, 1H), 0.79-0.75 (m, 2H) | | | | | | | | |
| 347 | 1H NMR (400 MHz, DMSO-d6) δ: 13.38 (br s, 1H), 11.32-10.40 (m, 1H), 8.63 (d, J = 0.8 Hz, 1H), 8.24 (s, 2H), 8.15 (d, J = 2.1 Hz, 1H), 7.51 (d, J = 9.0 Hz, 1H), 7.41-7.34 (m, 2H), 7.12-7.04 (m, 2H), 5.06 (dd, J = 5.1, 13.2 Hz, 1H), 4.44 (d, J = 16.9 Hz, 1H), 4.31-4.23 (m, 2H), 3.86 (s, 3H), 3.65 (br s, 2H), 3.02 (br s, 2H), 2.97-2.90 (m, 6H), 2.84 (br d, J = 12.1 Hz, 2H), 2.61 (br d, J = 2.5 Hz, 1H), 2.56 (br d, J = 8.3 Hz, 1H), 2.43 (br dd, J = 4.5, 13.1 Hz, 2H), 2.04-1.84 (m, 8H), 1.72 (br s, 4H), 1.65-1.57 (m, 2H), 1.55 (s, 3H), 0.98-0.93 (m, 2H), 0.81-0.75 (m, 2H) | 815.96 (815.41) | 816.8 | N.D. | N.D. | N.D. | N.D. | A | B |
| 348 | 1H NMR (400 MHz, METHANOL-d4) δ: 8.68-8.59 (m, 1H), 8.45-8.34 (m, 1H), 8.19 (s, 1H), 7.50 (br s, 1H), 7.49-7.44 (m, 1H), 7.42 (s, 1H), 7.22-7.14 (m, 1H), 7.12-7.06 (m, 1H), 5.15-5.07 (m, 1H), 4.57-4.39 (m, 2H), 4.25-4.07 (m, 2H), 3.72-3.67 (m, 1H), 3.55-3.41 (m, 4H), 3.18-3.12 (m, 1H), 3.07-2.96 (m, 2H), 2.93-2.64 (m, 4H), 2.57-2.41 (m, 2H), 2.29-2.15 (m, 2H), 2.14-1.95 (m, 5H), 1.87-1.81 (m, 1H), 1.77-1.68 (m, 2H), 1.61 (s, 3H), 1.37 (d, J = 6.5 Hz, 2H), 1.34-1.26 (m, 2H), 1.26-1.18 (m, 3H), 1.11-0.93 (m, 4H), 0.82-0.75 (m, 2H) | 819.96 (819.42) | 820.7 | N.D. | N.D. | N.D. | N.D. | A | B |
| 349 | 1H NMR (400 MHz, DMSO-d6) δ: 13.46 (s, 1H), 10.97 (s, 1H), 8.63 (s, 1H), 8.38 (d, J = 8.4 Hz, 1H), 8.14 (s, 1H), 7.46 (d, J = 10.9 Hz, 1H), 7.41-7.33 (m, 2H), 7.08 (d, J = 8.3 Hz, 1H), 5.11-5.03 (m, 1H), 4.54-4.21 (m, 4H), 3.86 (s, 3H), 3.60-3.50 (m, 3H), 2.96 (t, J = 11.7 Hz, 3H), 2.71-2.53 (m, 6H), 2.42 (dd, J = 4.4, 13.2 Hz, 2H), 2.09 (d, J = 5.9 Hz, 5H), 2.01-1.93 (m, 1H), 1.81 (d, J = 11.8 Hz, 5H), 1.58 (s, 3H), 1.54-1.45 (m, 1H), 1.26 (d, J = 10.4 Hz, 2H), 1.16-1.05 (m, 2H), 1.01 (s, 8H), 0.84-0.75 (m, 2H). | 863.03 (862.47) | 432.4 $[M/2 + 1]^+$ | N.D. | N.D. | N.D. | N.D. | A | A |
| 350 | 1H NMR (400 MHz, DMSO-d6) δ: 13.48-13.30 (m, 1H), 10.96 (s, 1H), 8.62 (s, 1H), 8.21-8.10 (m, 1H), 7.50 (d, J = 9.0 Hz, 1H), 7.43-7.35 (m, 2H), 7.06 (dd, J = 2.3, 9.0 Hz, 1H), 6.67 (t, J = 8.1 Hz, 1H), 5.04 (dd, J = 5.0, 13.3 Hz, 1H), 4.51-4.23 (m, 4H), 4.11 (d, J = 7.5 Hz, 2H), 3.87 (s, 2H), 3.02-2.85 (m, 4H), 2.76-2.58 (m, 3H), 2.41 (dt, J = 4.4, 12.9 Hz, 2H), 2.24 (d, J = 6.9 Hz, 2H), 2.09- | 783.84 (783.35) | 784.4 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1.85 (m, 4H), 1.79 (d, J = 12.0 Hz, 2H), 1.54 (s, 3H), 1.08 (d, J = 10.0 Hz, 2H), 1.00-0.91 (m, 2H), 0.81-0.74 (m, 2H). | | | | | | | | |
| 351 | 1H NMR (400 MHz, DMSO-d6) δ: 13.39 (s, 1H), 10.99 (s, 1H), 8.63 (s, 1H), 8.16 (s, 2H), 7.50 (t, J = 9.5 Hz, 2H), 7.39 (s, 1H), 7.15 (br t, J = 7.6 Hz, 1H), 7.07 (dd, J = 2.2, 8.9 Hz, 1H), 5.08 (dd, J = 4.8, 13.3 Hz, 1H), 4.54-4.45 (m, 1H), 4.31 (br d, J = 17.1 Hz, 1H), 4.10 (br s, 2H), 4.01-3.89 (m, 1H), 2.98-2.81 (m, 3H), 2.61 (br s, 7H), 2.42 (br d, J = 7.0 Hz, 7H), 2.02 (br d, J = 6.5 Hz, 3H), 1.86 (br s, 2H), 1.55 (s, 5H), 1.43 (br d, J = 9.0 Hz, 2H), 0.95 (s, 2H), 0.80-0.75 (m, 2H) | 777.88 (777.38) | 778.6 | N.D. | N.D. | N.D. | N.D. | A | B |
| 352 | 1H NMR (400 MHz, DMSO-d6) δ: 13.40 (br s, 1H), 10.99 (s, 1H), 8.64 (br s, 1H), 8.16 (d, J = 2.3 Hz, 1H), 8.14 (s, 0.23H), 7.55-7.43 (m, 2H), 7.38 (br s, 1H), 7.17 (t, J = 8.0 Hz, 1H), 7.07 (dd, J = 2.3, 9.0 Hz, 1H), 5.08 (dd, J = 5.1, 13.4 Hz, 1H), 4.48 (d, J = 16.9 Hz, 1H), 4.31 (d, J = 16.8 Hz, 1H), 4.25-4.08 (m, 1H), 3.70-3.57 (m, 1H), 3.01-2.74 (m, 5H), 2.65-2.53 (m, 6H), 2.42 (br dd, J = 4.9, 13.2 Hz, 2H), 2.30 (br dd, J = 1.6, 3.8 Hz, 1H), 2.04-1.79 (m, 7H), 1.64-1.50 (m, 5H), 1.47-1.27 (m, 2H), 1.24-1.01 (m, 8H), 0.99-0.84 (m, 4H), 0.81-0.73 (m, 2H) | 833.99 (833.44) | 834.3 | N.D. | N.D. | N.D. | N.D. | A | B |
| 353 | 1H NMR (400 MHz, DMSO-d6) δ: 13.91-13.09 (m, 1H), 11.35-10.65 (m, 1H), 8.70-8.58 (m, 1H), 8.17-8.14 (m, 1H), 7.56-7.42 (m, 2H), 7.42-7.35 (m, 1H), 7.19-7.10 (m, 1H), 7.10-7.02 (m, 1H), 5.16-4.99 (m, 1H), 4.55-4.26 (m, 2H), 4.17-4.01 (m, 2H), 3.83-3.68 (m, 1H), 3.38 (br s, 2H), 3.29-3.20 (m, 2H), 3.04-2.83 (m, 3H), 2.76-2.68 (m, 1H), 2.64-2.53 (m, 2H), 2.49-2.37 (m, 5H), 2.32-2.22 (m, 1H), 2.04-1.81 (m, 7H), 1.77-1.67 (m, 1H), 1.59-1.51 (m, 3H), 1.49-1.36 (m, 3H), 1.23-1.11 (m, 2H), 1.06-0.99 (m, 3H), 0.95 (br t, J = 5.6 Hz, 2H), 0.81-0.73 (m, 2H) | 819.96 (819.42) | 820.8 | N.D. | N.D. | N.D. | N.D. | A | B |
| 354 | 1H NMR (400 MHz, DMSO-d6) δ: 13.32 (s, 1H), 10.99 (s, 1H), 8.22 (br d, J = 5.0 Hz, 1H), 8.14 (s, 1H), 7.60-7.46 (m, 3H), 7.26 (s, 1H), 7.20-7.03 (m, 3H), 5.08 (br dd, J = 4.8, 13.1 Hz, 1H), 4.51-4.29 (m, 2H), 4.07 (br d, J = 13.3 Hz, 2H), 3.71 (br s, 1H), 3.27-3.18 (m, 3H), 3.14 (br s, 4H), 2.99-2.86 (m, 1H), 2.65-2.59 (m, 4H), 2.43 (br d, J = 12.8 Hz, 1H), 2.16 (br s, 2H), 2.03-1.85 (m, 6H), 1.81 (br d, J = 10.9 Hz, 2H), 1.55 (s, 3H), 1.45 (br d, J = 9.1 Hz, 3H), 1.24-1.10 (m, 2H), 0.99 (br s, 2H), 0.91 (br d, J = 12.6 Hz, 2H), 0.78 (br s, 2H) | 804.95 (804.41) | 805.3 | N.D. | N.D. | N.D. | N.D. | A | B |
| 355 | 1H NMR (400 MHz, DMSO-d6) δ: 13.37 (br s, 1H), 10.98 (s, 1H), 8.62 (s, 1H), 8.14 (s, 2H), 7.49 (dd, J = 8.8, 10.5 Hz, 2H), 7.37 (s, | 836.97 (836.43) | 837.8 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1H), 7.14 (t, J = 7.9 Hz, 1H), 7.06 (dd, J = 2.4, 9.0 Hz, 1H), 5.07 (dd, J = 5.0, 13.3 Hz, 1H), 4.52-4.41 (m, 3H), 4.31 (d, J = 16.9 Hz, 1H), 3.25 (br s, 3H), 3.07-2.89 (m, 6H), 2.87 (br d, J = 5.9 Hz, 1H), 2.83-2.72 (m, 2H), 2.64 (br dd, J = 7.9, 11.0 Hz, 4H), 2.43-2.32 (m, 2H), 2.19 (br d, J = 6.3 Hz, 4H), 1.96 (br dd, J = 6.1, 11.2 Hz, 1H), 1.89 (br d, J = 11.5 Hz, 2H), 1.84-1.73 (m, 4H), 1.70-1.61 (m, 1H), 1.54 (s, 3H), 1.06 (br d, J = 6.0 Hz, 3H), 0.96-0.93 (m, 2H), 0.79-0.75 (m, 2H) | | | | | | | | |
| 356 | 1H NMR (400 MHz, DMSO-d6) δ: 13.57-13.29 (m, 1H), 10.97 (s, 1H), 8.64 (s, 1H), 8.15 (s, 1H), 7.51 (d, J = 9.0 Hz, 1H), 7.40 (s, 1H), 7.37 (d, J = 8.0 Hz, 1H), 7.07 (td, J = 2.2, 8.8 Hz, 2H), 5.13-4.95 (m, 1H), 4.53-4.20 (m, 4H), 4.18-4.05 (m, 2H), 3.84 (s, 3H), 3.73-3.64 (m, 2H), 3.37-3.32 (m, 4H), 2.99 (s, 2H), 2.92-2.86 (m, 1H), 2.72 (s, 2H), 2.62-2.54 (m, 2H), 2.44-2.34 (m, 1H), 2.01-1.77 (m, 5H), 1.54 (s, 3H), 1.50-1.33 (m, 4H), 0.99-0.90 (m, 2H), 0.83-0.74 (m, 2H). | 775.89 (775.38) | 776.4 | N.D. | N.D. | N.D. | N.D. | A | B |
| 357 | 1H NMR (400 MHz, DMSO-d6) δ: 13.39 (s, 1H), 10.96 (s, 1H), 8.64 (s, 1H), 8.16 (d, J = 1.9 Hz, 1H), 7.51 (d, J = 9.0 Hz, 1H), 7.41 (s, 1H), 7.30 (d, J = 8.0 Hz, 1H), 7.07 (dd, J = 2.3, 9.1 Hz, 1H), 6.56 (d, J = 8.1 Hz, 1H), 5.04 (dd, J = 5.2, 13.3 Hz, 1H), 4.52-4.24 (m, 2H), 4.03 (br d, J = 8.4 Hz, 4H), 3.80 (br d, J = 8.1 Hz, 2H), 3.74 (s, 3H), 3.61 (br t, J = 5.5 Hz, 3H), 3.42 (br t, J = 9.5 Hz, 2H), 2.98-2.85 (m, 1H), 2.77 (br s, 2H), 2.62 (br d, J = 5.8 Hz, 2H), 2.58-2.55 (m, 1H), 2.45-2.37 (m, 2H), 2.06-1.87 (m, 6H), 1.55 (s, 3H), 1.49 (br d, J = 9.0 Hz, 2H), 0.98-0.93 (m, 2H), 0.81-0.75 (m, 2H) | 825.90 (825.38) | 826.7 | N.D. | N.D. | N.D. | N.D. | A | B |
| 358 | 1H NMR (400 MHz, DMSO-d6) δ: 13.32 (br s, 1H), 10.97 (br s, 1H), 8.23 (br d, J = 4.3 Hz, 1H), 7.56-7.51 (m, 2H), 7.48-7.43 (m, 1H), 7.23 (br s, 1H), 7.16 (br s, 2H), 7.08 (br d, J = 9.0 Hz, 1H), 5.09-5.04 (m, 1H), 4.48 (br d, J = 17.1 Hz, 1H), 4.31 (br d, J = 16.6 Hz, 1H), 3.56 (br s, 8H), 2.99-2.83 (m, 5H), 2.46 (br s, 2H), 2.12 (br d, J = 3.4 Hz, 2H), 1.99-1.78 (m, 8H), 1.61-1.51 (m, 6H), 1.25-1.07 (m, 3H), 0.98 (br s, 2H), 0.94-0.84 (m, 2H), 0.77 (br s, 2H) | 804.95 (804.41) | 805.4 | N.D. | N.D. | N.D. | N.D. | A | B |
| 359 | 1H NMR (400 MHz, DMSO-d6) δ: 13.53-13.37 (m, 1H), 10.96 (s, 1H), 8.62 (s, 1H), 8.37 (s, 1H), 7.51-7.42 (m, 1H), 7.45 (d, J = 10.8 Hz, 1H), 7.41-7.33 (m, 2H), 7.07 (d, J = 8.3 Hz, 1H), 5.11-5.00 (m, 1H), 4.53-4.22 (m, 4H), 3.85 (s, 3H), 3.59-3.49 (m, 3H), 2.92 (d, J = 12.4 Hz, 3H), 2.71-2.58 (m, 3H), 2.58-2.54 (m, 1H), 2.45-2.35 (m, 2H), 2.11 (d, J = 6.8 Hz, 7H), 1.88-1.75 (m, 4H), | 863.03 (862.47) | 432.4 $[M/2+1]^+$ | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 1.74-1.61 (m, 2H), 1.57 (s, 3H), 1.36-1.22 (m, 2H), 1.09-0.97 (m, 4H), 0.95 (s, 6H), 0.83-0.77 (m, 2H). | | | | | | | | |
| 360 | 1H NMR (400 MHz, DMSO-d6) δ: 13.51-13.38 (m, 1H), 10.96 (s, 1H), 8.65 (s, 1H), 8.41-8.33 (m, 1H), 7.50-7.43 (m, 1H), 7.40-7.33 (m, 2H), 7.12-7.04 (m, 1H), 5.10-5.01 (m, 1H), 4.49-4.22 (m, 2H), 3.86 (s, 3H), 3.73-3.55 (m, 5H), 3.44-3.38 (m, 3H), 2.95-2.79 (m, 3H), 2.62-2.55 (m, 1H), 2.44 (br d, J = 3.9 Hz, 5H), 2.21-2.09 (m, 2H), 2.02-1.88 (m, 5H), 1.84-1.74 (m, 2H), 1.57 (s, 5H), 1.53-1.42 (m, 1H), 1.25-1.08 (m, 2H), 1.00 (s, 2H), 0.97-0.85 (m, 2H), 0.80 (s, 2H) | 835.96 (835.42) | 418.8 $[M/2 + 1]^+$ | N.D. | N.D. | N.D. | N.D. | A | B |
| 361 | 1HNMR (400 MHz, DMSO-d6) δ: 13.38 (s, 1H), 10.98 (s, 1H), 8.63 (s, 1H), 8.17-8.13 (m, 1H), 7.50 (m, 1H), 7.47 (br d, J = 8.4 Hz, 1H), 7.39 (s, 1H), 7.12 (br t, J = 7.6 Hz, 1H), 7.06 (dd, J = 2.0, 9.2 Hz, 1H), 5.07 (br dd, J = 4.8, 13.2 Hz, 1H), 4.48 (m, 1H), 4.31 (m, 1H), 4.12-4.02 (m, 2H), 3.74 (m, 1H), 3.10 (br s, 2H), 2.94-2.81 (m, 3H), 2.65-2.55 (m, 3H), 2.44-2.35 (m, 1H), 2.12 (m, 2H), 2.00-1.92 (m, 3H), 1.91-1.73 (m, 5H), 1.54 (s, 3H), 1.47-1.38 (m, 2H), 1.36-1.27 (m, 1H), 1.24-1.08 (m, 3H), 1.03 (s, 6H), 0.97-0.90 (m, 3H), 0.87 (m, 2H), 0.80-0.74 (m, 2H) | 833.99 (833.44) | 834.1 | N.D. | N.D. | N.D. | N.D. | A | B |
| 362 | 1H NMR (400 MHz, DMSO-d6) δ: 13.51-13.31 (m, 1H), 11.13-10.85 (m, 1H), 8.64 (s, 1H), 8.26-8.10 (m, 1H), 7.61-7.46 (m, 1H), 7.41 (s, 2H), 7.15-7.01 (m, 1H), 6.75-6.49 (m, 1H), 5.12-4.98 (m, 1H), 4.49-4.23 (m, 2H), 4.15-3.99 (m, 4H), 3.87 (s, 2H), 3.60 (s, 3H), 3.49 (s, 2H), 2.97-2.84 (m, 1H), 2.84-2.72 (m, 2H), 2.61 (s, 4H), 2.43-2.30 (m, 2H), 2.07-1.85 (m, 5H), 1.61-1.43 (m, 5H), 0.95 (s, 2H), 0.82-0.70 (m, 2H). | 813.87 (813.36) | 814.3 | N.D. | N.D. | N.D. | N.D. | A | B |
| 363 | 1H NMR (400 MHz, DMSO-d6) δ: 13.42 (br s, 1H), 10.97 (s, 1H), 8.64 (s, 1H), 8.16 (br d, J = 9.5 Hz, 1H), 7.51 (d, J = 9.0 Hz, 1H), 7.39 (s, 1H), 7.30 (d, J = 8.0 Hz, 1H), 7.11-6.98 (m, 1H), 6.57 (d, J = 8.1 Hz, 1H), 5.14-4.96 (m, 1H), 4.48 (br d, J = 16.9 Hz, 1H), 4.30 (br d, J = 16.8 Hz, 1H), 4.03 (br d, J = 8.3 Hz, 2H), 3.80 (br d, J = 7.6 Hz, 2H), 3.75 (s, 3H), 3.66 (br s, 4H), 2.98-2.82 (m, 2H), 2.80-2.67 (m, 2H), 2.63-2.52 (m, 6H), 2.49-2.36 (m, 4H), 2.14-1.77 (m, 4H), 1.54 (s, 3H), 1.00-0.88 (m, 2H), 0.82-0.74 (m, 2H) | 810.89 (810.38) | 811.7 | N.D. | N.D. | N.D. | N.D. | A | B |
| 364 | 1H NMR (400 MHz, DMSO) δ: 13.38 (s, 1H), 10.97 (s, 1H), 8.63 (s, 1H), 8.18-8.15 (m, 1H), 8.15-8.13 (m, 1H), 7.51 (d, J = 9.0 Hz, 1H), 7.44-7.37 (m, 2H), 7.11-7.02 (m, 2H), 5.07 (dd, J = 4.9, 13.3 Hz, 1H), 4.56-4.42 (m, 1H), 4.34-4.26 (m, 1H), 4.13-4.03 | 846.03 (845.46) | 846.7 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | (m, 2H), 3.85 (s, 3H), 3.80-3.71 (m, 1H), 3.39-3.36 (m, 2H), 3.16-3.00 (m, 2H), 2.95 (br d, J = 5.5 Hz, 1H), 2.88-2.79 (m, 2H), 2.58 (br s, 3H), 2.46-2.38 (m, 1H), 2.23-2.07 (m, 2H), 2.03-1.93 (m, 3H), 1.90-1.79 (m, 4H), 1.59-1.53 (m, 3H), 1.50-1.32 (m, 3H), 1.22-1.12 (m, 2H), 1.11-1.01 (m, 6H), 0.97-0.93 (m, 2H), 0.92-0.82 (m, 2H), 0.80-0.74 (m, 2H) | | | | | | | | |
| 365 | 1H NMR (400 MHz, DMSO-d6) δ: 13.50-13.17 (m, 1H), 11.07-10.89 (m, 1H), 8.40-8.24 (m, 1H), 7.52-7.41 (m, 2H), 7.19 (s, 2H), 7.08-6.98 (m, 1H), 5.14-5.02 (m, 1H), 4.57-4.24 (m, 2H), 3.65 (s, 5H), 3.41-3.36 (m, 2H), 3.02-2.82 (m, 3H), 2.62-2.53 (m, 1H), 2.52 (s, 3H), 2.44-2.37 (m, 5H), 2.16-2.08 (m, 2H), 2.02-1.88 (m, 6H), 1.86-1.76 (m, 2H), 1.56 (s, 6H), 1.23-1.12 (m, 2H), 0.96 (s, 2H), 0.93-0.84 (m, 2H), 0.78 (d, J = 1.4 Hz, 2H). | 819.96 (819.42) | 820.4 | N.D. | N.D. | N.D. | N.D. | A | B |
| 366 | 1H NMR (400 MHz, DMSO-d6) δ: 13.43-13.35 (m, 1H), 10.96 (s, 1H), 8.63 (s, 1H), 8.17-8.13 (m, 1H), 7.50 (d, J = 9.0 Hz, 1H), 7.41-7.33 (m, 2H), 7.12-6.98 (m, 2H), 5.11-4.97 (m, 1H), 4.47-4.22 (m, 2H), 4.11-3.93 (m, 2H), 3.86 (s, 3H), 3.64-3.56 (m, 1H), 3.45-3.36 (m, 3H), 3.28 (br s, 1H), 3.08-2.98 (m, 1H), 2.94-2.78 (m, 4H), 2.58 (br d, J = 16.8 Hz, 1H), 2.47-2.35 (m, 3H), 2.16 (br t, J = 9.2 Hz, 1H), 1.95 (br d, J = 11.4 Hz, 7H), 1.75-1.67 (m, 1H), 1.65-1.56 (m, 2H), 1.54 (s, 3H), 1.49-1.39 (m, 1H), 1.23-1.11 (m, 2H), 1.03 (d, J = 6.1 Hz, 3H), 0.97-0.82 (m, 4H), 0.79-0.74 (m, 2H) | 832.00 (831.44) | 832.7 | N.D. | N.D. | N.D. | N.D. | A | B |
| 367 | 1H NMR (400 MHz, DMSO-d6) δ: 13.36-13.28 (m, 1H), 10.96 (s, 1H), 8.36-8.26 (m, 1H), 7.52-7.45 (m, 1H), 7.41-7.32 (m, 1H), 7.19 (s, 1H), 7.11-7.06 (m, 1H), 7.05-6.98 (m, 1H), 5.14-5.00 (m, 1H), 4.48-4.19 (m, 2H), 3.86 (s, 3H), 3.65 (s, 5H), 3.48-3.36 (m, 4H), 2.95-2.79 (m, 3H), 2.63-2.52 (m, 1H), 2.41 (s, 7H), 2.16-2.06 (m, 2H), 2.01-1.89 (m, 5H), 1.86-1.74 (m, 2H), 1.56 (s, 5H), 1.53-1.41 (m, 1H), 1.24-1.15 (m, 2H), 0.96 (s, 4H), 0.78 (d, J = 1.1 Hz, 2H). | 832.00 (831.44) | 416.8 [M/2 + 1]+ | N.D. | N.D. | N.D. | N.D. | A | B |
| 368 | 1H NMR (400 MHz, DMSO-d6) δ: 13.52-13.30 (m, 1H), 11.25-10.80 (m, 1H), 8.72-8.49 (m, 1H), 8.17-8.07 (m, 1H), 7.56-7.46 (m, 1H), 7.44-7.33 (m, 2H), 7.27-7.18 (m, 1H), 7.10-6.98 (m, 1H), 5.15-4.99 (m, 1H), 4.41-4.17 (m, 2H), 4.13-3.96 (m, 2H), 3.77-3.53 (m, 2H), 3.50-3.40 (m, 2H), 2.98-2.82 (m, 3H), | 806.92 (806.39) | 807.6 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 2.52 (br s, 4H), 2.39 (br s, 2H), 2.01-1.78 (m, 9H), 1.65-1.49 (m, 5H), 1.47-1.37 (m, 2H), 1.33-1.19 (m, 4H), 1.00-0.89 (m, 2H), 0.81-0.72 (m, 2H) | | | | | | | | |
| 369 | 1H NMR (400 MHz, DMSO-d6) δ: 13.90 (s, 1H), 10.96 (s, 1H), 8.78 (s, 1H), 8.63 (s, 1H), 8.13 (s, 1H), 7.79 (s, 1H), 7.39 (d, J = 5.0 Hz, 1H), 7.07 (d, J = 8.2 Hz, 1H), 5.06 (dd, J = 4.9, 13.2 Hz, 1H), 4.46 (s, 1H), 4.27 (d, J = 17.1 Hz, 1H), 3.85 (s, 3H), 3.11 (s, 4H), 3.02-2.82 (m, 2H), 2.75-2.64 (m, 4H), 2.58-2.52 (m, 6H), 2.43 (d, J = 13.9 Hz, 4H), 2.07 (s, 1H), 2.01-1.70 (m, 8H), 1.61 (s, 3H), 1.28-1.01 (m, 4H), 0.96-0.87 (m, 2H), 0.81-0.72 (m, 2H). | 835.97 (835.43) | 836.3 | N.D. | N.D. | N.D. | N.D. | A | B |
| 370 | 1H NMR (400 MHz, DMSO-d6) δ: 13.46-13.31 (m, 1H), 11.02-10.95 (m, 1H), 8.67-8.60 (m, 1H), 8.20-8.14 (m, 1H), 7.70-7.62 (m, 1H), 7.55-7.48 (m, 1H), 7.39-7.34 (m, 1H), 7.31-7.24 (m, 1H), 7.10-7.03 (m, 1H), 5.15 (s, 1H), 4.47-4.22 (m, 2H), 3.75-3.61 (m, 4H), 3.09 (br s, 4H), 2.95-2.85 (m, 1H), 2.64-2.52 (m, 6H), 2.43 (br d, J = 4.1 Hz, 4H), 2.22-2.13 (m, 4H), 2.03-1.94 (m, 1H), 1.87-1.76 (m, 4H), 1.55-1.43 (m, 5H), 0.96-0.93 (m, 2H), 0.83 (br s, 4H), 0.80-0.74 (m, 2H) | 821.41 (820.39) | 821.4 | N.D. | N.D. | N.D. | N.D. | A | B |
| 371 | 1H NMR (400 MHz, DMSO-d6) δ: 13.45 (br s, 1H), 10.99 (s, 1H), 8.16 (s, 1H), 8.01-7.92 (m, 2H), 7.51-7.42 (m, 2H), 7.15 (t, J = 7.9 Hz, 1H), 6.82 (d, J = 9.0 Hz, 1H), 5.07 (dd, J = 5.1, 13.3 Hz, 1H), 4.48 (d, J = 17.0 Hz, 1H), 4.31 (d, J = 16.9 Hz, 1H), 4.13-4.05 (m, 2H), 3.70-3.64 (m, 1H), 3.39 (br s, 3H), 3.25-3.07 (m, 7H), 2.95-2.85 (m, 1H), 2.68-2.52 (m, 2H), 2.45-2.40 (m, 1H), 2.37 (s, 3H), 2.13 (br d, J = 7.0 Hz, 2H), 1.99-1.85 (m, 5H), 1.80 (br d, J = 11.6 Hz, 2H), 1.74 (s, 3H), 1.49-1.35 (m, 3H), 1.24-1.11 (m, 2H), 0.98-0.94 (m, 2H), 0.93-0.83 (m, 2H), 0.83-0.74 (m, 2H) | 819.96 (819.42) | 820.7 | N.D. | N.D. | N.D. | N.D. | A | B |
| 372 | 1H NMR (400 MHz, DMSO-d6) δ: 13.38 (s, 1H), 10.95 (s, 1H), 8.62 (s, 1H), 8.14 (s, 1H), 7.50 (d, J = 8.9 Hz, 1H), 7.41-7.33 (m, 2H), 7.06 (dd, J = 2.1, 9.0 Hz, 1H), 6.58 (t, J = 8.1 Hz, 1H), 5.03 (dd, J = 5.0, 13.3 Hz, 1H), 4.53-4.18 (m, 4H), 3.74 (s, 4H), 3.29 (s, 2H), 3.01-2.86 (m, 3H), 2.61-2.53 (m, 2H), 2.42-2.30 (m, 1H), 2.01-1.68 (m, 8H), 1.60-1.48 (m, 5H), 1.35 (d, J = 9.0 Hz, 2H), 1.24-1.10 (m, 2H), 0.98-0.90 (m, 2H), 0.76-0.75 (m, 1H), 0.80-0.72 (m, 1H) | 762.87 (762.37) | 763.9 | N.D. | N.D. | N.D. | N.D. | A | B |
| 373 | 1H NMR (400 MHz, DMSO-d6) δ: 13.37 (s, 1H), 11.00 (s, 1H), 8.62 (d, J = 0.8 Hz, 1H), 8.15 (d, J = 2.3 Hz, 1H), 8.13 (s, 1H), 7.50 (d, J = 9.0 Hz, 1H), 7.43-7.33 (m, 2H), 7.06 (dd, J = 2.4, 9.0 Hz, 1H), | 840.93 (840.40) | 841.7 | N.D. | N.D. | N.D. | N.D. | A | A |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 5.08 (dd, J = 5.1, 13.1 Hz, 1H), 4.55-4.23 (m, 4H), 3.22 (br s, 4H), 3.02-2.84 (m, 3H), 2.65-2.55 (m, 6H), 2.54-2.52 (m, 3H), 2.43 (br d, J = 4.8 Hz, 2H), 2.31-2.19 (m, 3H), 2.04-1.94 (m, 1H), 1.91-1.63 (m, 7H), 1.54 (s, 3H), 1.17-1.03 (m, 2H), 0.97-0.91 (m, 2H), 0.80-0.74 (m, 2H) | | | | | | | | |
| 374 | 1H NMR (400 MHz, MeOD) δ: 8.64-8.55 (m, 1H), 8.09-8.01 (m, 1H), 7.54-7.31 (m, 3H), 7.13-7.03 (m, 1H), 6.64-6.56 (m, 1H), 5.12-5.04 (m, 1H), 4.50-4.36 (m, 2H), 4.21-4.06 (m, 2H), 3.87-3.83 (m, 2H), 3.82-3.76 (m, 2H), 3.64-3.55 (m, 1H), 3.53-3.44 (m, 2H), 3.06 (br d, J = 1.9 Hz, 1H), 2.92-2.74 (m, 2H), 2.54-2.40 (m, 1H), 2.18-2.09 (m, 1H), 2.07-1.94 (m, 4H), 1.91-1.79 (m, 2H), 1.71-1.62 (m, 3H), 1.62-1.60 (m, 3H), 1.60-1.56 (m, 1H), 1.54-1.42 (m, 2H), 1.07-0.96 (m, 2H), 0.83-0.72 (m, 2H) | 748.84 (748.35) | 749.6 | N.D. | N.D. | N.D. | N.D. | A | B |
| 375 | 1H NMR (400 MHz, DMSO-d6) δ: 13.48 (s, 1H), 10.99 (s, 1H), 8.21-8.16 (m, 2H), 8.14 (s, 1H), 7.99 (d, J = 9.0 Hz, 1H), 7.51-7.45 (m, 2H), 7.16 (t, J = 7.9 Hz, 1H), 6.84 (d, J = 9.0 Hz, 1H), 5.08 (dd, J = 4.9, 13.2 Hz, 1H), 4.52-4.26 (m, 2H), 4.09 (br d, J = 13.5 Hz, 2H), 3.70 (br s, 1H), 3.22 (br d, J = 10.6 Hz, 2H), 3.14 (br s, 4H), 2.91 (br s, 1H), 2.60-2.55 (m, 2H), 2.44-2.37 (m, 2H), 2.15 (br d, J = 6.6 Hz, 2H), 1.96 (br s, 6H), 1.80 (br d, J = 11.4 Hz, 2H), 1.75 (s, 3H), 1.43 (br d, J = 9.5 Hz, 3H), 1.27-1.09 (m, 4H), 0.96 (s, 2H), 0.93-0.85 (m, 2H), 0.82-0.77 (m, 2H) | 805.94 (805.41) | 806.7 | N.D. | N.D. | N.D. | N.D. | A | B |
| 376 | 1H NMR (400 MHz, MeOD) δ: 8.71-8.53 (m, 1H), 8.26-8.15 (m, 1H), 8.06-8.00 (m, 1H), 7.54-7.44 (m, 2H), 7.42-7.30 (m, 1H), 7.14-7.03 (m, 1H), 6.74-6.55 (m, 1H), 5.15-5.06 (m, 1H), 4.56-4.39 (m, 4H), 4.27-4.17 (m, 2H), 3.96-3.79 (m, 2H), 3.11-2.97 (m, 2H), 2.96-2.65 (m, 4H), 2.60-2.39 (m, 5H), 2.23-2.08 (m, 3H), 1.94-1.83 (m, 2H), 1.80-1.67 (m, 1H), 1.61 (s, 3H), 1.56-1.47 (m, 2H), 1.36-1.22 (m, 2H), 1.09-0.99 (m, 2H), 0.85-0.75 (m, 2H) | 797.87 (797.36) | 798.5 | N.D. | N.D. | N.D. | N.D. | A | B |
| 377 | 1H NMR (400 MHz, METHANOL-d4) δ: 9.12 (s, 1H), 7.91 (s, 1H), 7.67-7.56 (m, 3H), 7.35-7.21 (m, 2H), 5.16 (dd, J = 5.1, 13.4 Hz, 1H), 4.64-4.48 (m, 2H), 4.18-4.08 (m, 2H), 3.98-3.90 (m, 1H), 3.75 (br s, 3H), 3.67-3.59 (m, 3H), 3.58-3.48 (m, 2H), 3.37 (br s, 3H), 3.18-3.12 (m, 2H), 2.98-2.87 (m, 1H), 2.84-2.76 (m, 1H), 2.52 (dq, J = 4.6, 13.2 Hz, 1H), 2.23-2.13 (m, 3H), 2.08 (br dd, J = 3.5, 12.9 Hz, 2H), 1.96 (br d, J = 12.5 Hz, 3H), 1.77 (br dd, J = 4.5, 8.5 Hz, | 805.94 (805.41) | 806.7 | N.D. | N.D. | N.D. | N.D. | A | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 2H), 1.63 (s, 3H), 1.44-1.34 (m, 2H), 1.28-1.17 (m, 2H), 1.11-1.05 (m, 2H), 0.85-0.80 (m, 2H) | | | | | | | | |
| 378 | 1H NMR (400 MHz, DMSO-d6) δ: 13.43-13.33 (m, 1H), 11.07-10.88 (m, 1H), 8.66-8.59 (m, 1H), 8.20-8.10 (m, 1H), 7.63-7.43 (m, 2H), 7.39 (s, 1H), 7.19-7.01 (m, 2H), 5.14-4.97 (m, 1H), 4.53-4.26 (m, 2H), 4.15-3.99 (m, 2H), 3.80-3.70 (m, 1H), 3.16-3.08 (m, 2H), 2.95-2.80 (m, 3H), 2.61 (br s, 2H), 2.45-2.36 (m, 3H), 2.13 (br s, 2H), 2.00-1.91 (m, 3H), 1.84 (br t, J = 13.8 Hz, 4H), 1.54 (s, 3H), 1.50-1.27 (m, 4H), 1.26-1.08 (m, 3H), 1.04-1.04 (m, 1H), 1.03 (s, 5H), 0.96-0.84 (m, 4H), 0.79-0.74 (m, 2H) | 833.99 (833.44) | 834.7 | N.D. | N.D. | N.D. | N.D. | A | B |
| 379 | 1H NMR (400 MHz, DMSO-d6) δ: 13.61-12.97 (m, 1H), 11.59-10.84 (m, 1H), 7.60-7.43 (m, 3H), 7.23-7.14 (m, 1H), 7.13-7.07 (m, 1H), 7.06-7.00 (m, 2H), 5.24-4.97 (m, 1H), 4.54-4.20 (m, 2H), 3.67-3.60 (m, 1H), 3.59-3.49 (m, 4H), 3.43-3.35 (m, 3H), 3.01-2.84 (m, 3H), 2.64-2.53 (m, 2H), 2.46 (br s, 4H), 2.42-2.39 (m, 3H), 2.18-2.09 (m, 2H), 2.03-1.87 (m, 5H), 1.86-1.76 (m, 2H), 1.65-1.43 (m, 6H), 1.24-1.11 (m, 2H), 1.04-0.97 (m, 2H), 0.96-0.83 (m, 2H), 0.82-0.70 (m, 2H) | 818.98 (818.43) | 819.7 | N.D. | N.D. | N.D. | N.D. | A | B |
| 380 | 1H NMR (400 MHz, DMSO-d6) δ: 10.76-11.09 (1 H, m), 8.78 (1 H, s), 8.63 (1 H, s), 7.79 (1 H, s), 7.35-7.41 (2 H, m), 7.05-7.11 (1 H, m), 5.03-5.08 (1 H, m), 5.05 (1 H, dd, J = 13.12, 4.95 Hz), 4.43 (1 H, d, J = 17.00 Hz), 4.23-4.30 (1 H, m), 4.00-4.13 (2 H, m), 3.85 (4 H, s), 3.67-3.74 (1 H, m), 3.52-3.60 (1 H, m), 3.43 (2 H, dd, J = 6.97, 5.14 Hz), 3.31 (5 H, s), 2.81-2.86 (2 H, m), 2.60 (2 H, d, J = 2.20 Hz), 1.84-1.92 (8 H, m), 1.61 (3 H, s), 1.22-1.30 (8 H, m), 0.91-0.94 (2 H, m), 0.74-0.77 (2 H, m). | 819.95 (819.41) | 820.3 | N.D. | N.D. | N.D. | N.D. | A | B |
| 381 | 1H NMR (400 MHz, DMSO-d6) δ: 13.37 (s, 1H), 10.99 (s, 1H), 8.61 (s, 1H), 8.15 (d, J = 2.3 Hz, 1H), 8.13 (s, 1H), 7.48 (dd, J = 8.6, 16.7 Hz, 2H), 7.37 (s, 1H), 7.17 (t, J = 7.9 Hz, 1H), 7.06 (dd, J = 2.3, 9.0 Hz, 1H), 5.07 (dd, J = 5.1, 13.3 Hz, 1H), 4.55-4.24 (m, 2H), 3.77-3.56 (m, 3H), 3.45 (s, 1H), 3.35 (s, 1H), 2.99-2.83 (m, 3H), 2.63-2.53 (m, 3H), 2.42 (dd, J = 4.6, 13.2 Hz, 3H), 2.10 (s, 2H), 2.02-1.88 (m, 5H), 1.83 (d, J = 13.0 Hz, 2H), 1.63-1.50 (m, 5H), 1.44-1.29 (m, 1H), 1.26-1.10 (m, 3H), 1.06-0.81 (m, 10H), 0.80-0.74 (m, 2H) | 833.99 (833.44) | 417.8 $[M/2 + 1]^+$ | N.D. | N.D. | N.D. | N.D. | B | C |
| 382 | 1H NMR (400 MHz, DMSO-d6) δ: 13.37 (s, 1H), 10.96 (s, 1H), 8.60 (d, J = 0.8 Hz, 1H), 8.15 (s, 0.23H), 8.14 (s, 1H), 7.50 (d, J = 9.0 Hz, 1H), 7.42-7.31 (m, 2H), 7.14-7.00 (m, 2H), 5.06 (dd, J = | 846.03 (845.46) | 846.7 | N.D. | N.D. | N.D. | N.D. | B | B |

TABLE 2-continued

Degradation and characterization of exemplary bifunctional compounds of the present disclosure

| Ex. No. | 1H NMR | Mol Weight (Exact Mass) | Mean Observed Mass | *G2019S $DC_{50}$ (nM) | G2019S $D_{max}$ (%) | *WT $DC_{50}$ (nM) | **WT $D_{max}$ (%) | *Endogenous WT $DC_{50}$ (nM) | **Endogenous WT $D_{max}$ (%) |
|---|---|---|---|---|---|---|---|---|---|
| | 5.0, 13.3 Hz, 1H), 4.43 (d, J = 17.0 Hz, 1H), 4.26 (d, J = 17.0 Hz, 1H), 3.86 (s, 3H), 3.70 (br d, J = 1.6 Hz, 2H), 3.60 (td, J = 4.2, 8.4 Hz, 1H), 3.45 (br s, 4H), 2.97-2.77 (m, 3H), 2.64-2.52 (m, 4H), 2.47-2.35 (m, 1H), 2.11 (br d, J = 6.6 Hz, 2H), 2.02-1.89 (m, 5H), 1.88-1.78 (m, 2H), 1.66-1.56 (m, 2H), 1.54 (s, 3H), 1.40-1.28 (m, 1H), 1.22-1.10 (m, 2H), 1.02-0.81 (m, 10H), 0.80-0.74 (m, 2H) | | | | | | | | |
| 383 | 1H NMR (400 MHz, DMSO-d6) δ: 13.39 (s, 1H), 10.98 (s, 1H), 8.71 (s, 1H), 8.14 (d, J = 2.6 Hz, 1H), 7.55-7.42 (m, 3H), 7.17 (t, J = 8.1 Hz, 1H), 7.07 (dd, J = 2.3, 8.9 Hz, 1H), 5.07 (dd, J = 5.1, 13.3 Hz, 1H), 4.48 (d, J = 17.1 Hz, 1H), 4.30 (d, J = 16.9 Hz, 1H), 3.69-3.53 (m, 3H), 3.42-3.37 (m, 2H), 3.32-3.29 (m, 2H), 2.98-2.84 (m, 3H), 2.62-2.53 (m, 2H), 2.47-2.35 (m, 2H), 2.26 (br s, 2H), 2.11 (br d, J = 6.8 Hz, 2H), 2.04-1.88 (m, 5H), 1.83 (br d, J = 11.5 Hz, 2H), 1.64-1.46 (m, 11H), 1.25-1.12 (m, 2H), 0.98-0.84 (m, 4H), 0.80-0.74 (m, 2H) | 833.99 (833.44) | 417.8 $[M/2 + 1]^+$ | N.D. | N.D. | N.D. | N.D. | C | C |
| 394 | 1H NMR (400 MHz, DMSO-d6) δ: 13.38 (s, 1H), 10.96 (s, 1H), 8.71 (d, J = 1.0 Hz, 1H), 8.14 (d, J = 2.3 Hz, 1H), 7.54-7.49 (m, 2H), 7.37 (d, J = 8.1 Hz, 1H), 7.11-7.05 (m, 2H), 5.06 (dd, J = 5.0, 13.3 Hz, 1H), 4.43 (d, J = 17.0 Hz, 1H), 4.26 (d, J = 16.9 Hz, 1H), 3.90-3.82 (m, 3H), 3.64-3.53 (m, 3H), 3.46-3.35 (m, 3H), 2.96-2.78 (m, 3H), 2.63-2.54 (m, 2H), 2.42 (br dd, J = 4.8, 13.6 Hz, 2H), 2.26 (s, 2H), 2.11 (br d, J = 7.3 Hz, 2H), 1.96 (dt, J = 2.7, 4.9 Hz, 5H), 1.83 (br d, J = 12.3 Hz, 2H), 1.65-1.44 (m, 12H), 1.25-1.12 (m, 2H), 1.01-0.85 (m, 4H), 0.80-0.73 (m, 2H) | 846.03 (845.46) | 846.7 | N.D. | N.D. | N.D. | N.D. | D | C |

*$DC_{50}$ Ranges: A < 10; 10 ≤ B < 50; 50 ≤ C < 100; D ≥ 100.
**$D_{Max}$ Ranges: A ≥ 70; 50 ≤ B < 70; C < 50
N.D.: Not Determined A novel bifunctional molecule, which contains a LRRK2 recruiting moiety and an E3 ubiquitin ligase recruiting moiety is described. The bifunctional molecules of the present disclosure actively degrades LRRK2, leading to robust cellular proliferation suppression and apoptosis induction. Protein degradation mediated by the bifunctional compounds of the present disclosure provides a promising strategy in targeting the “undruggable” pathological proteins by traditional approaches.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

Thus, those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A compound, wherein the compound is:

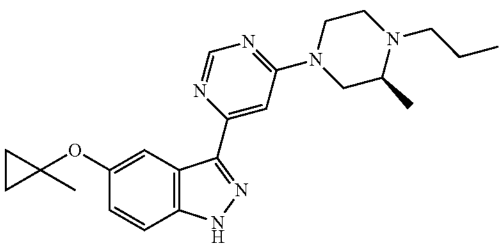

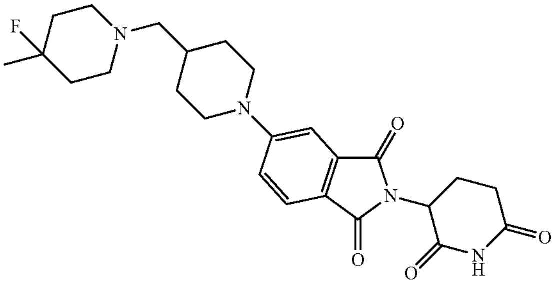

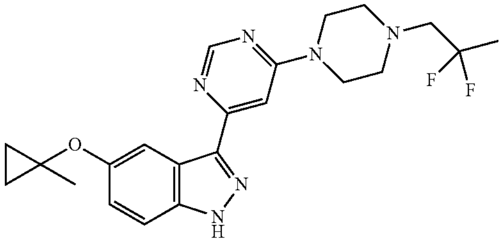

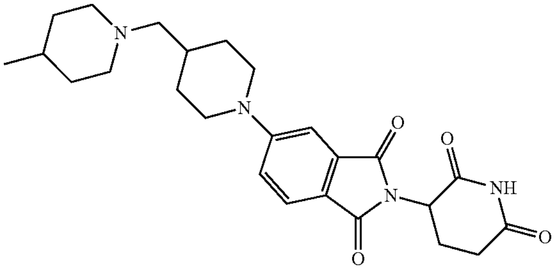

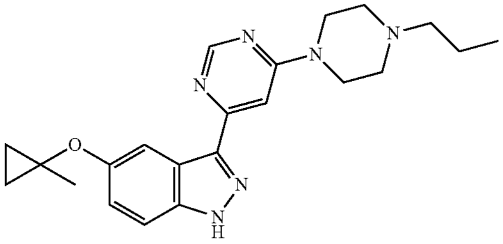

-continued

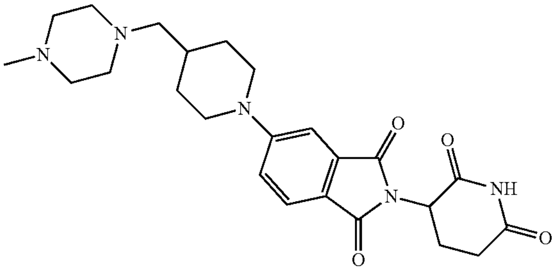

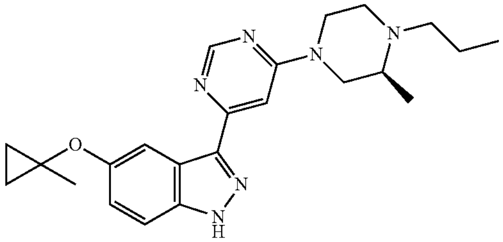

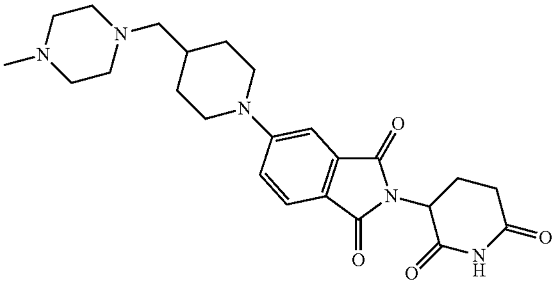

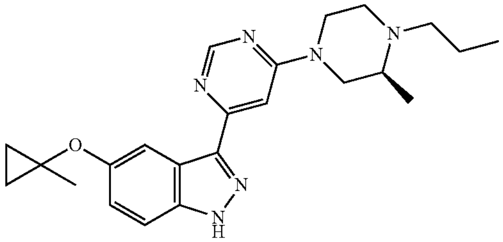

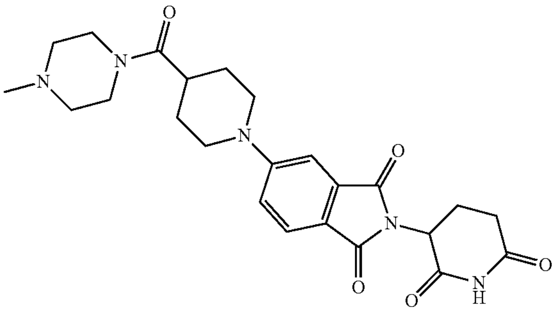

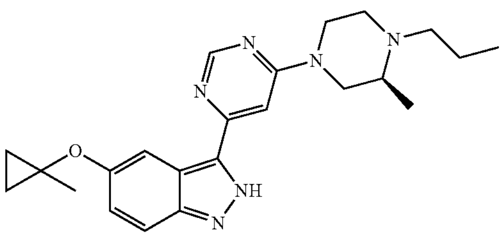

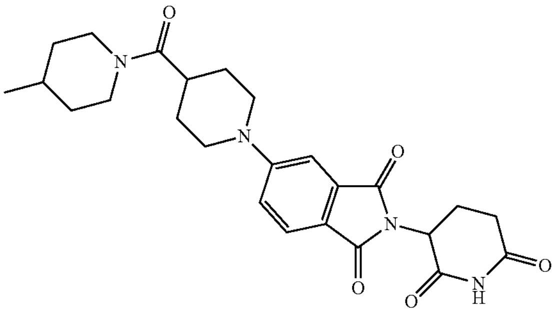
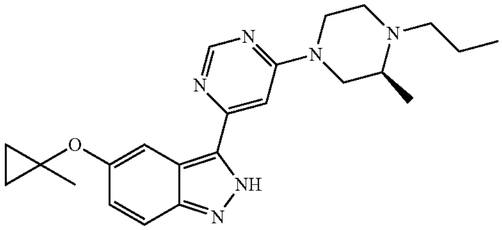
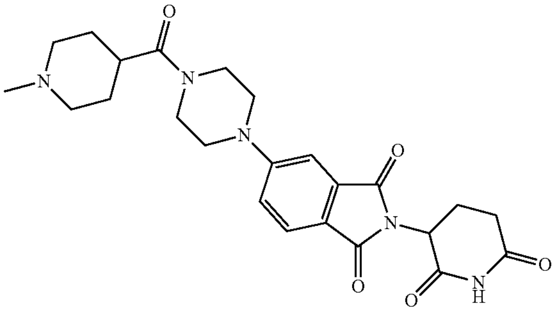
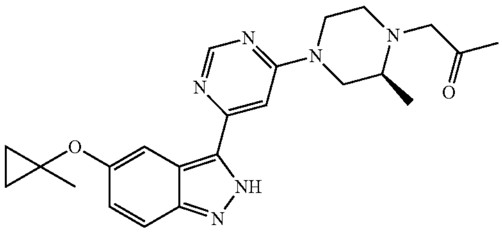
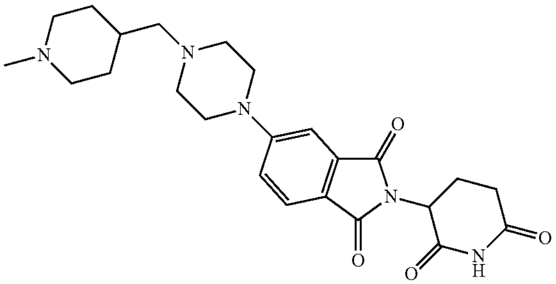
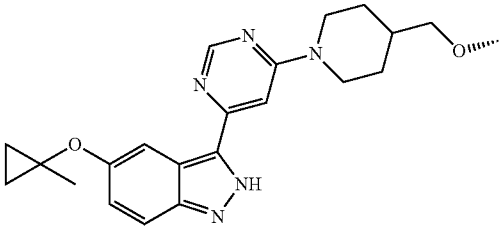
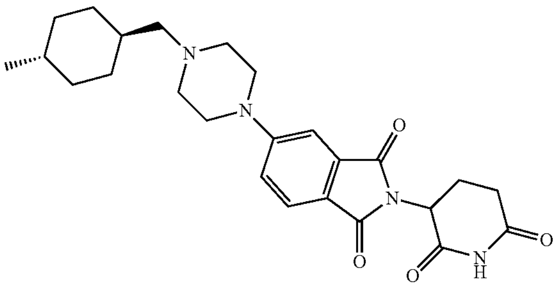
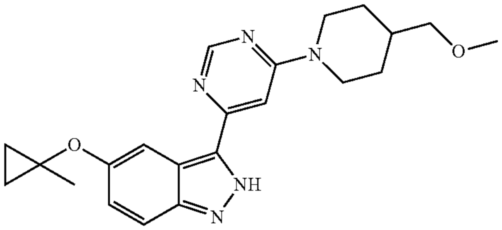
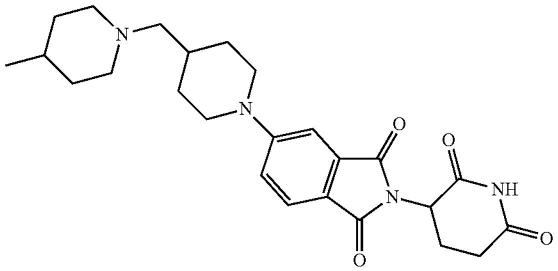
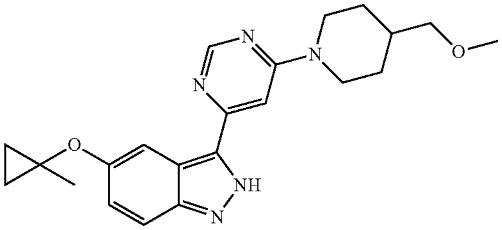
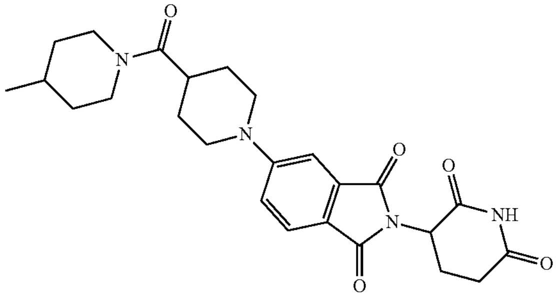
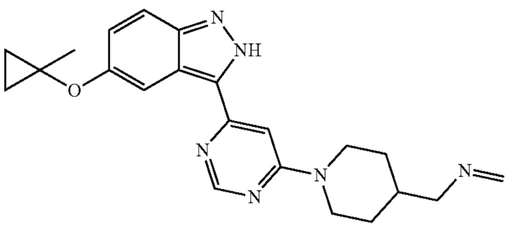

-continued
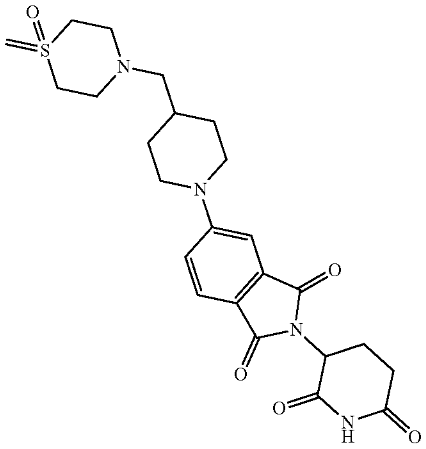
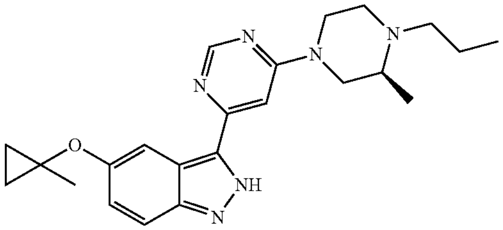
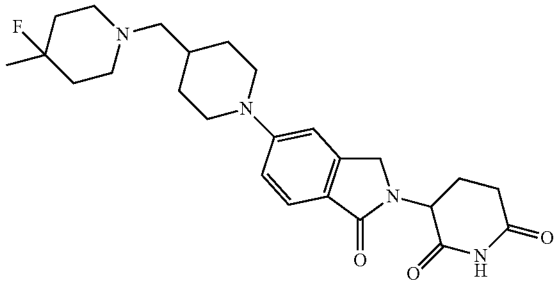
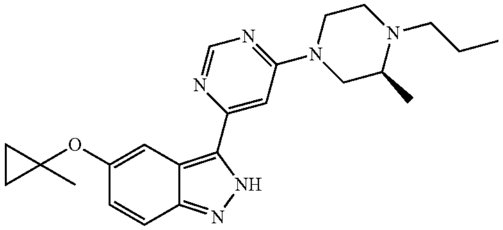
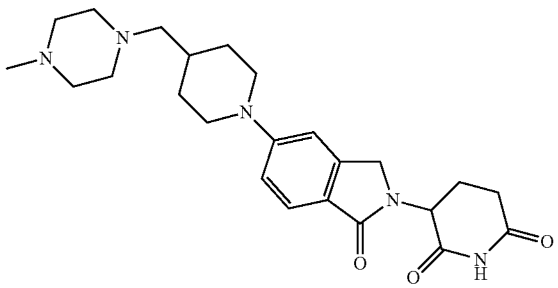
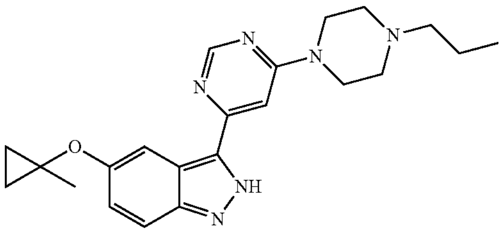
-continued
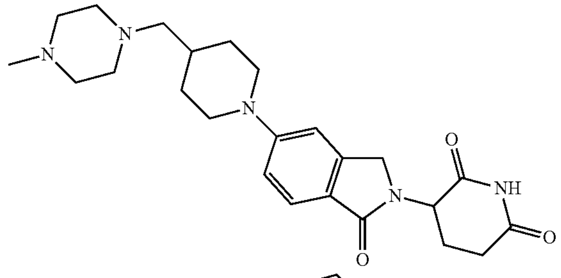
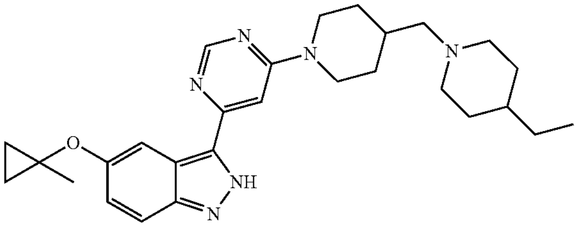
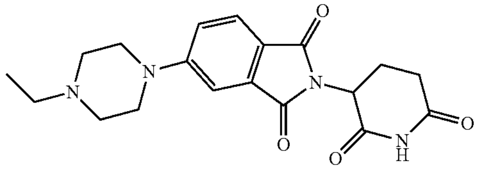
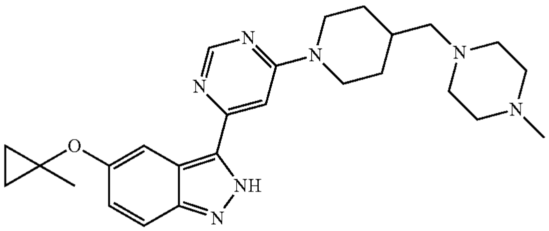
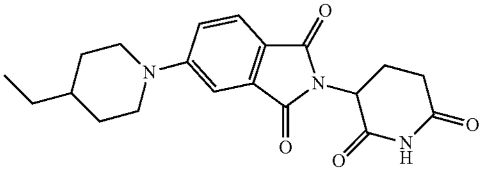
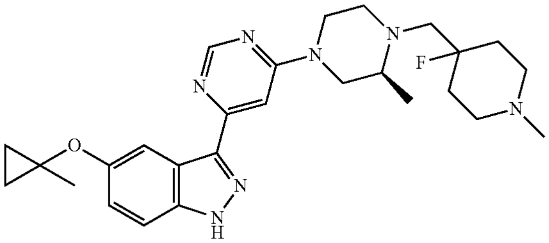
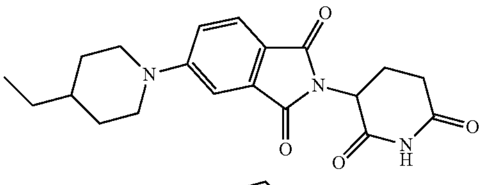
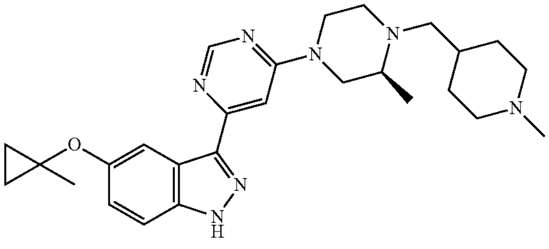

-continued
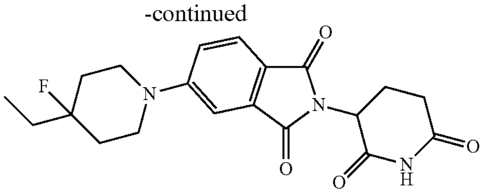
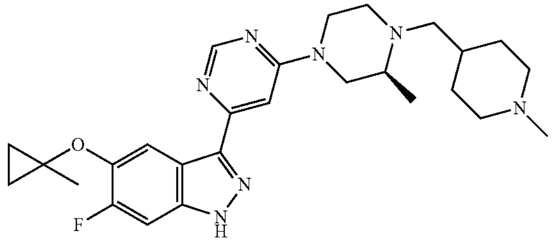
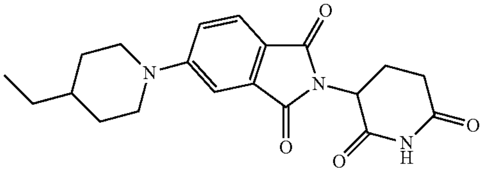
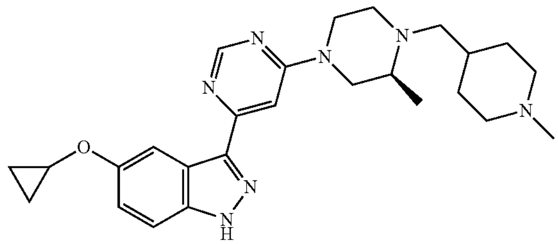
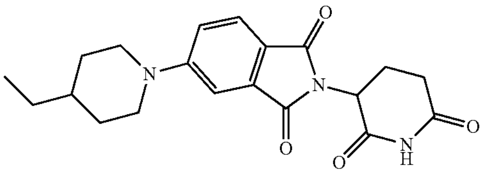
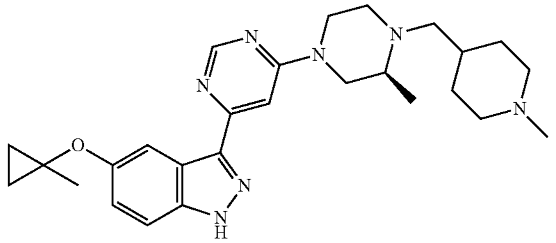
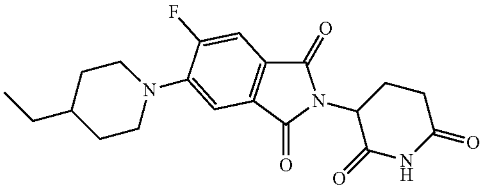
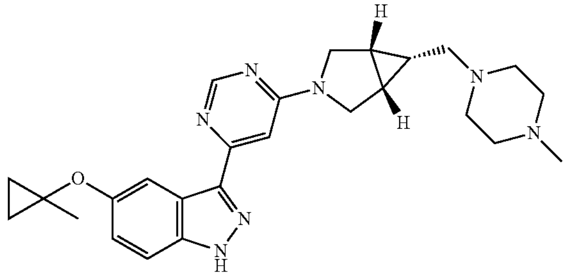
-continued
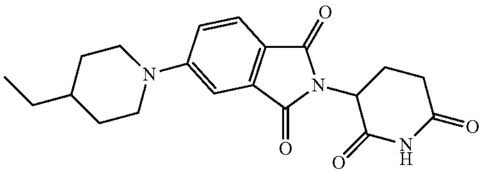
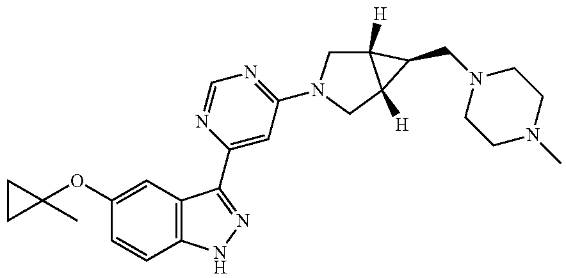
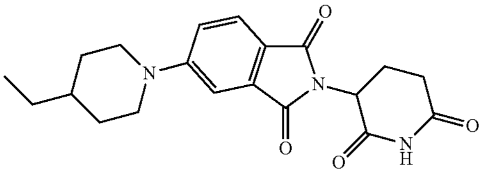
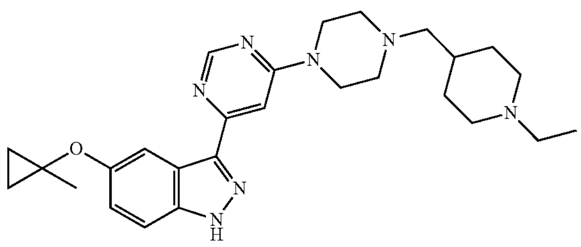
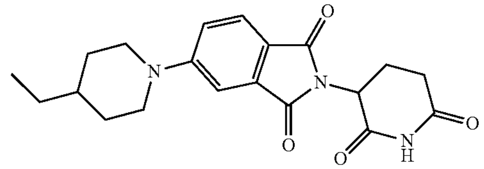
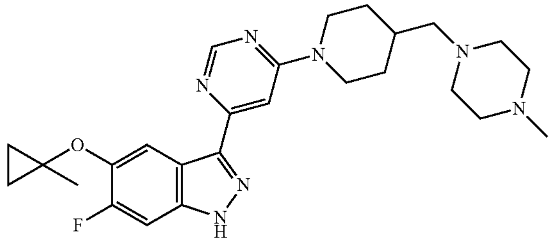
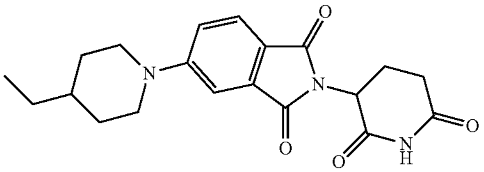
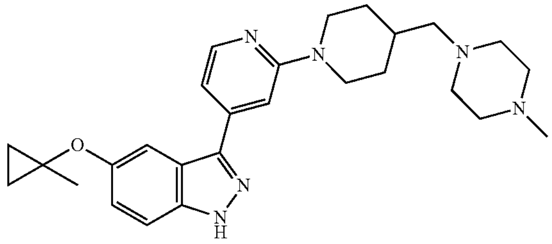

-continued
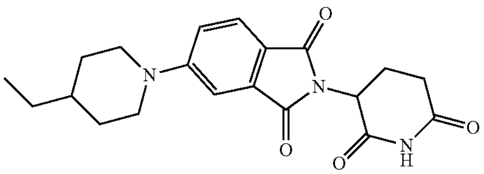
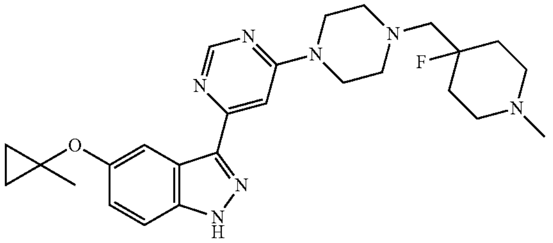
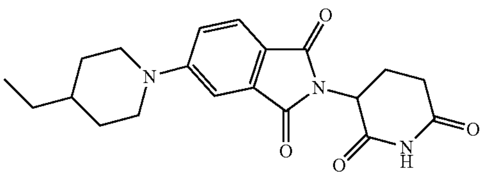
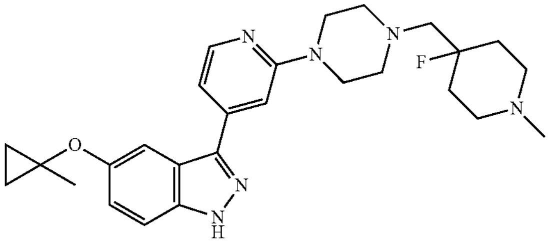
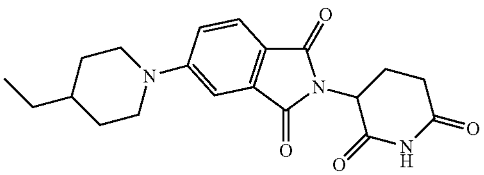
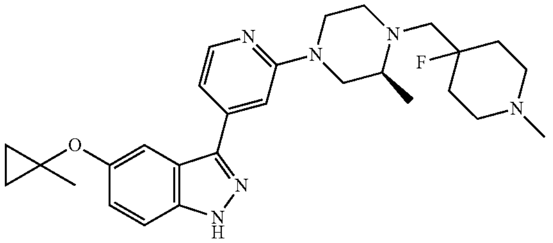
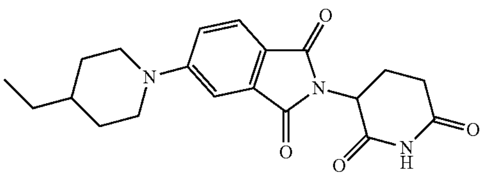
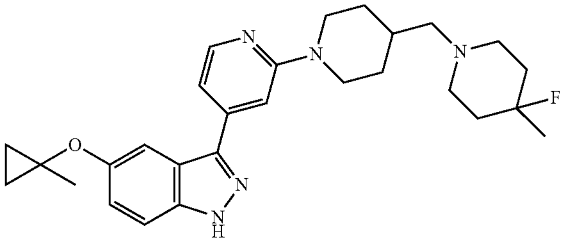
-continued
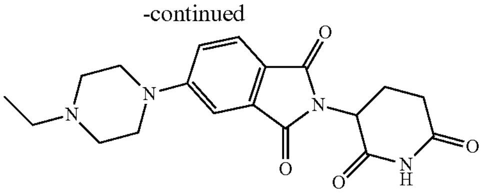
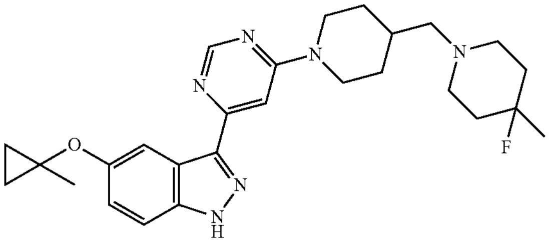
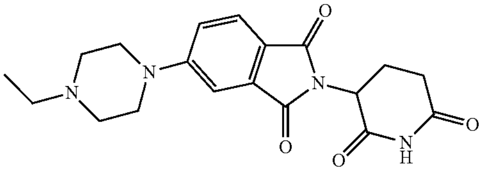
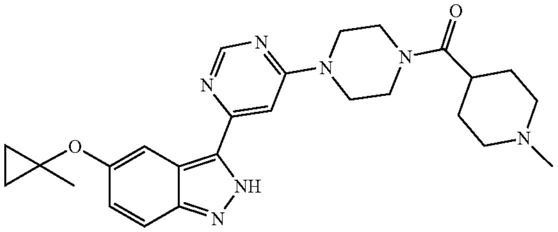
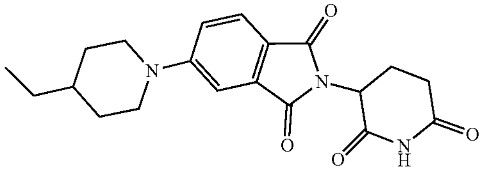
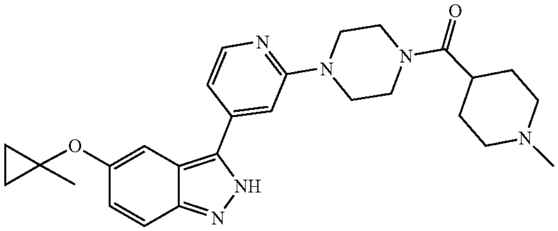
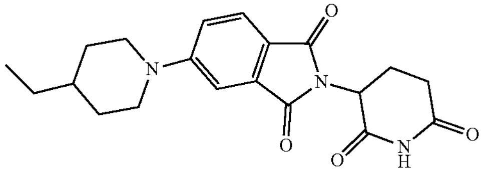
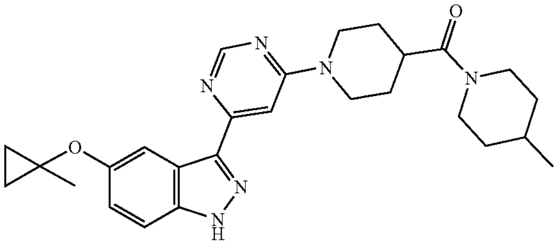

-continued
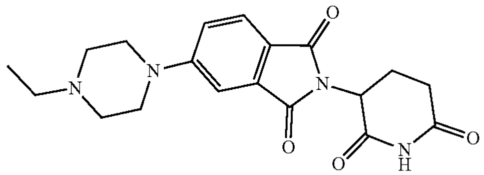
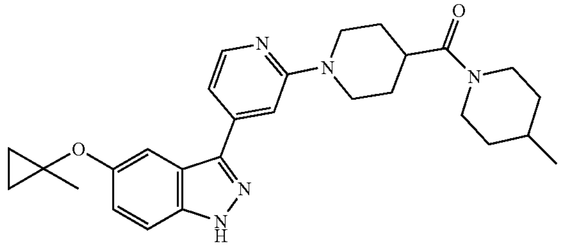
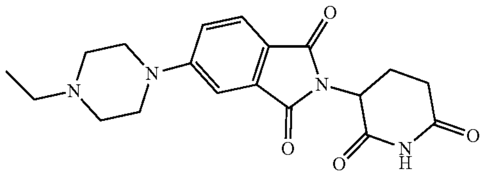
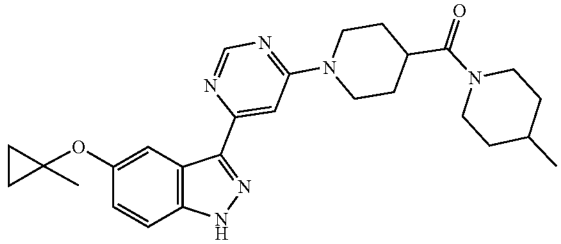
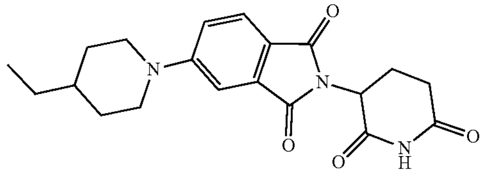
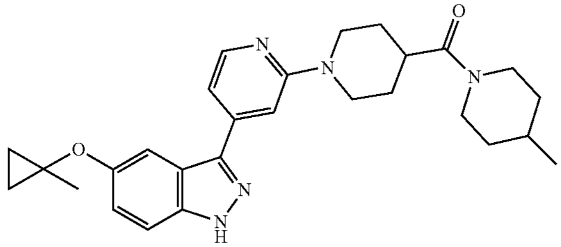
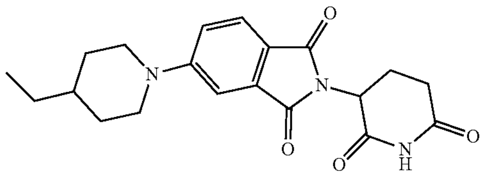
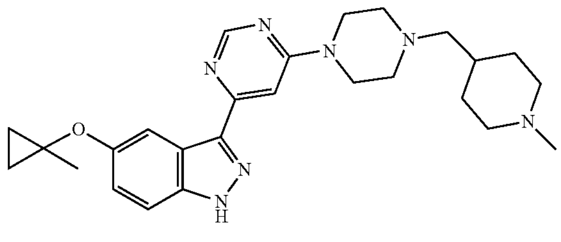
-continued
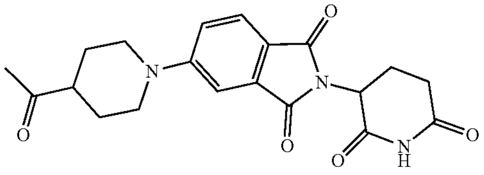
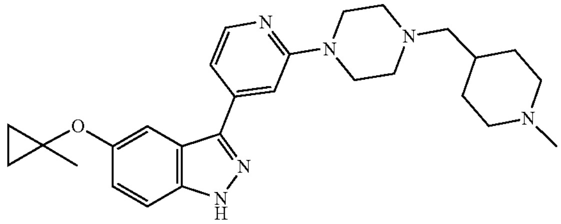
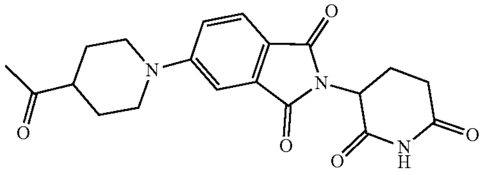
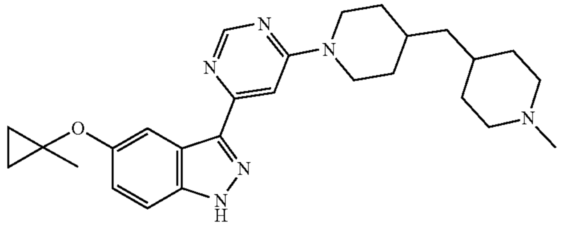
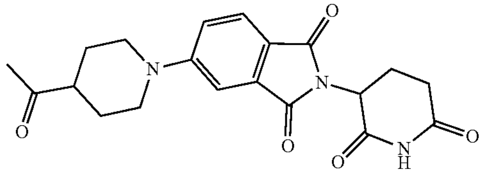
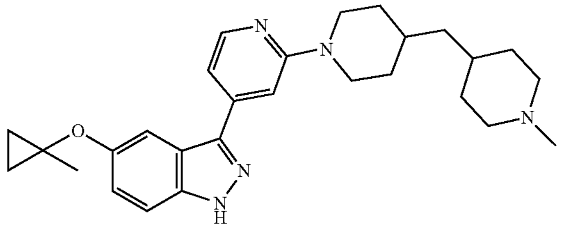
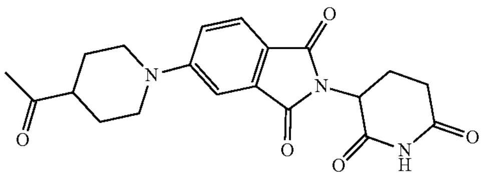
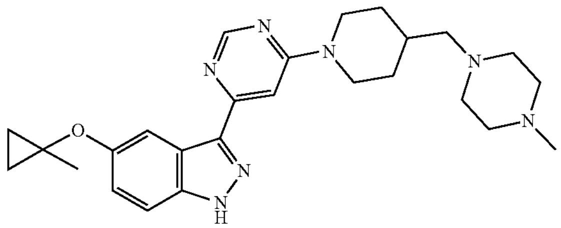

-continued
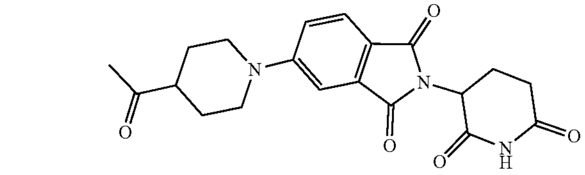
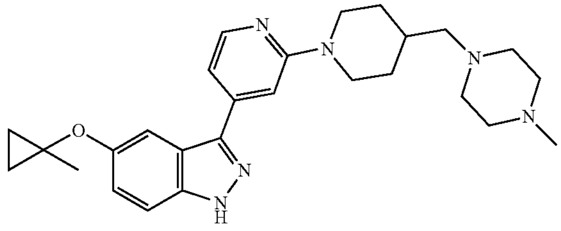
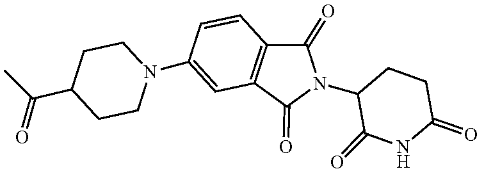
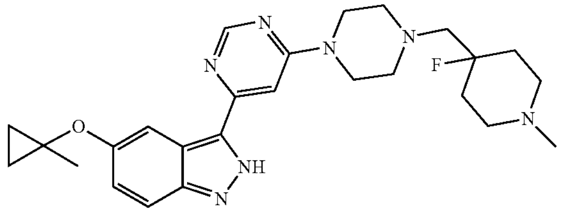
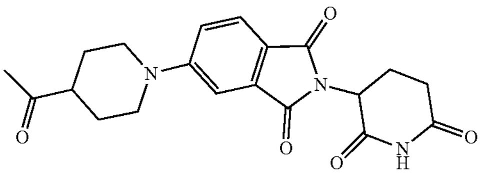
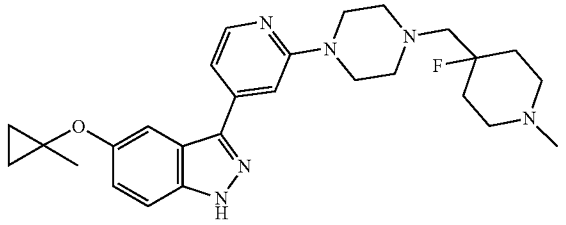
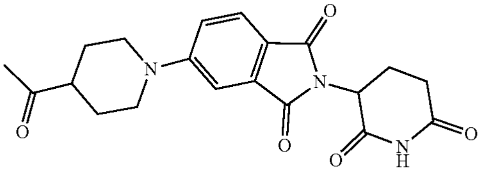
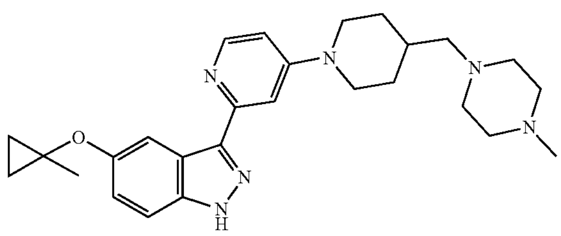
-continued
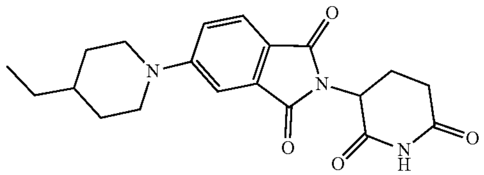
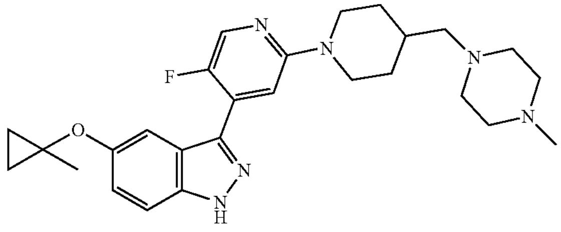
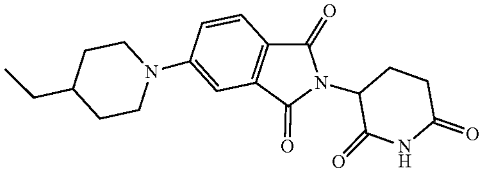
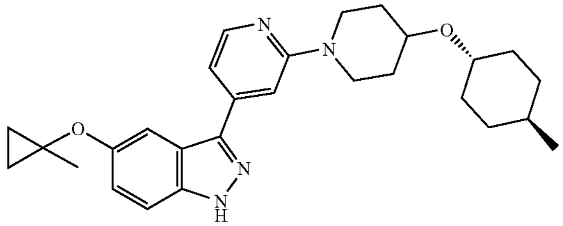
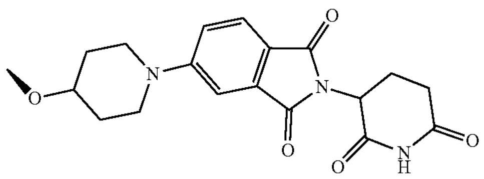
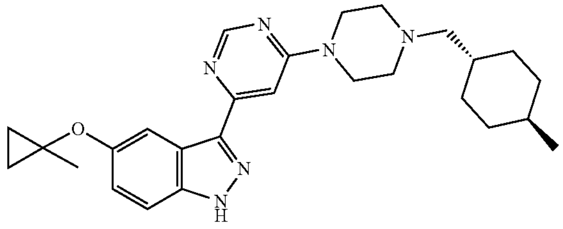
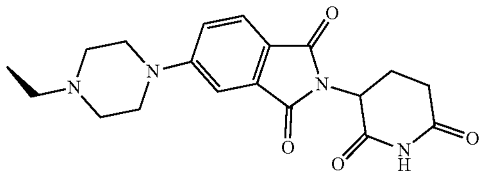
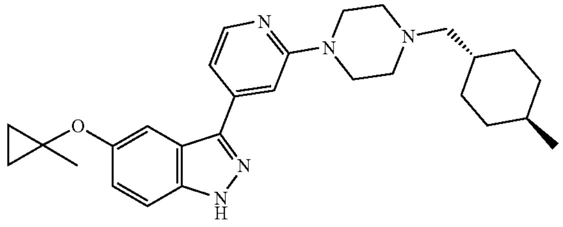

-continued
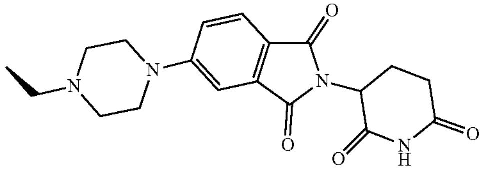
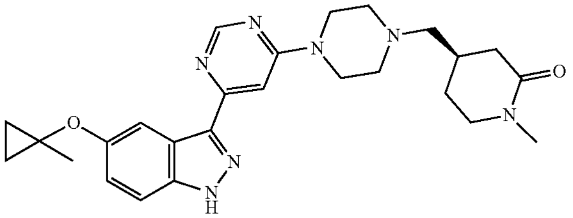
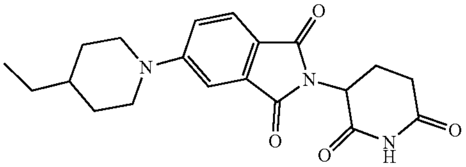
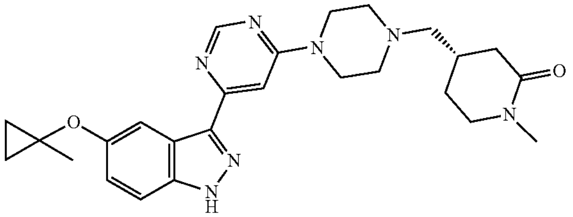
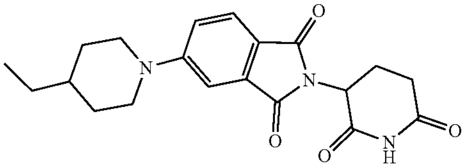
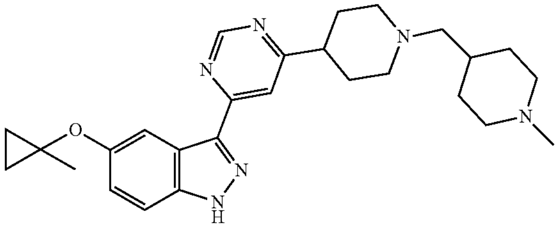
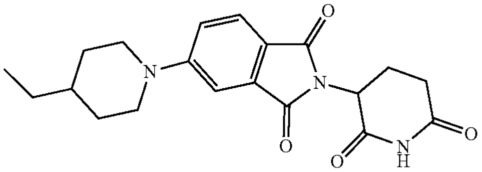
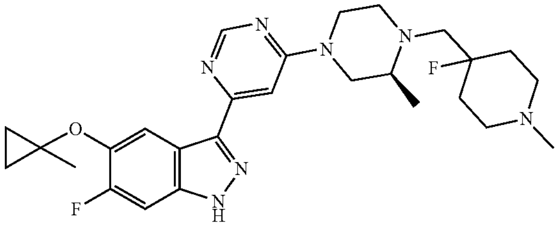
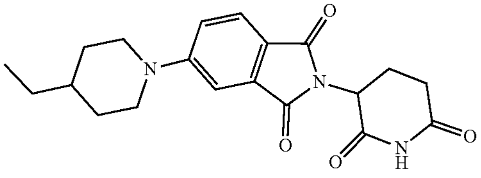
-continued
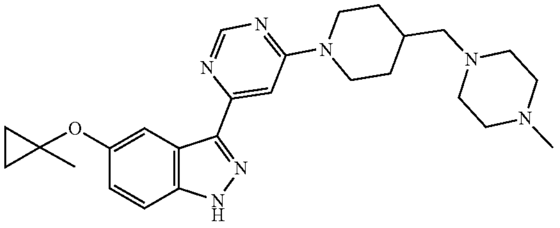
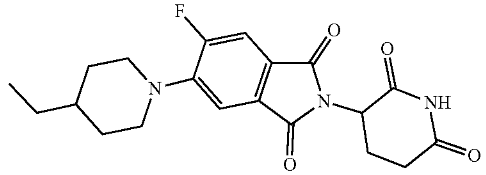
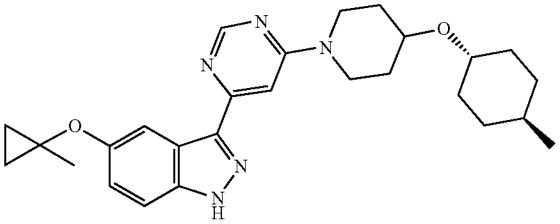
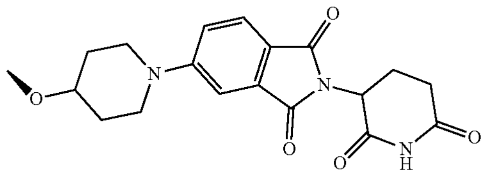
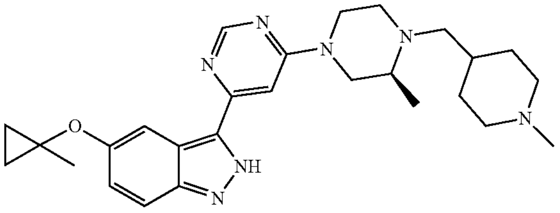
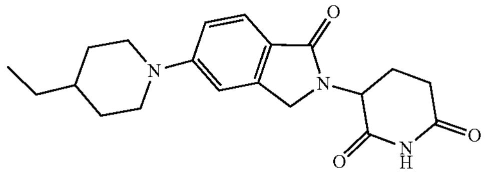
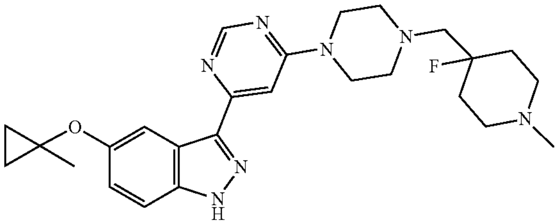
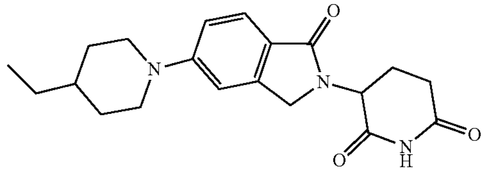

-continued
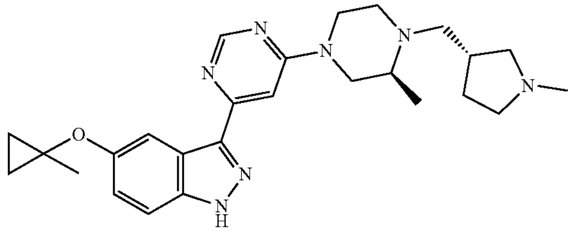
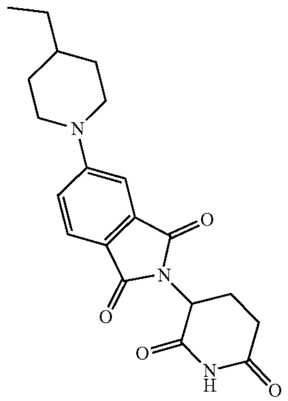
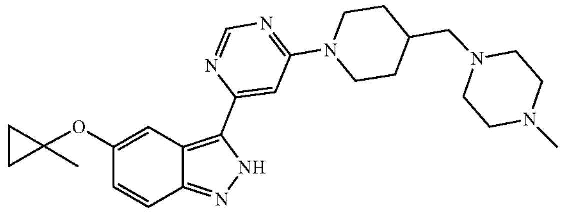
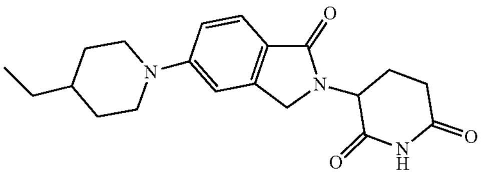
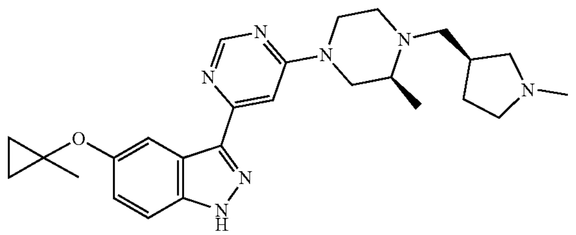
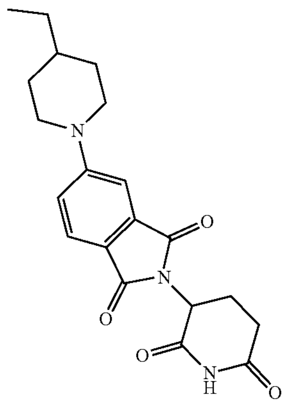
-continued
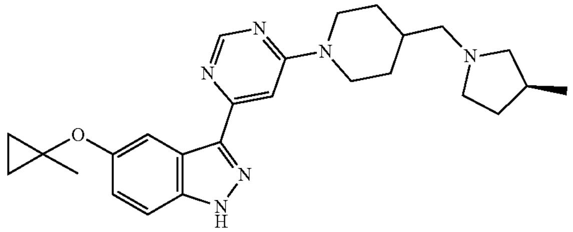
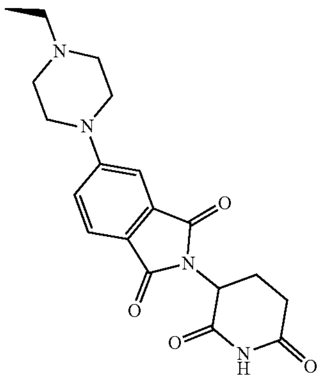
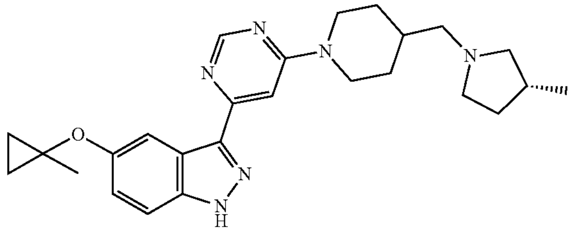
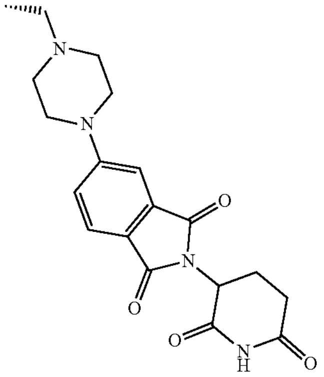
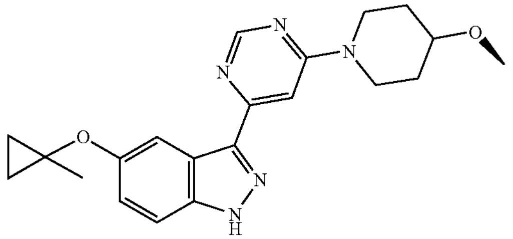

-continued
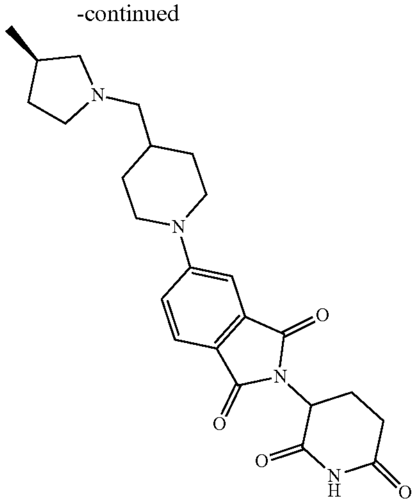
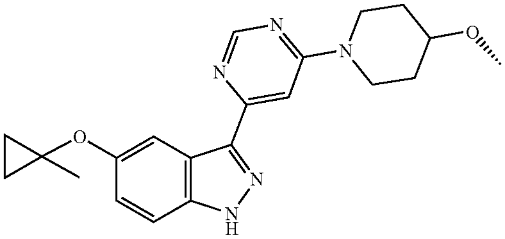
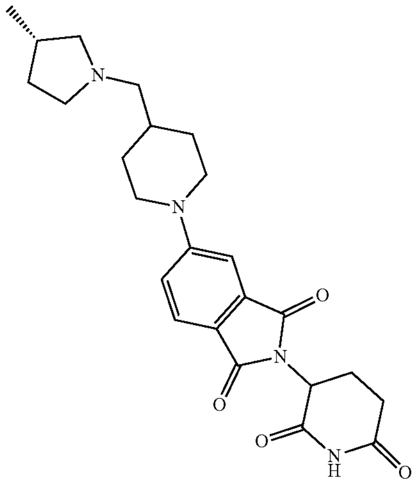
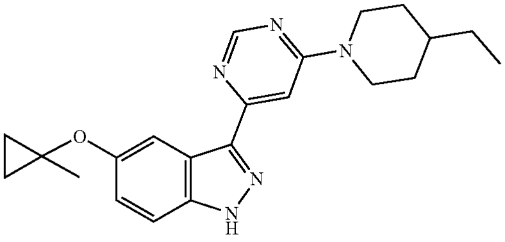
-continued
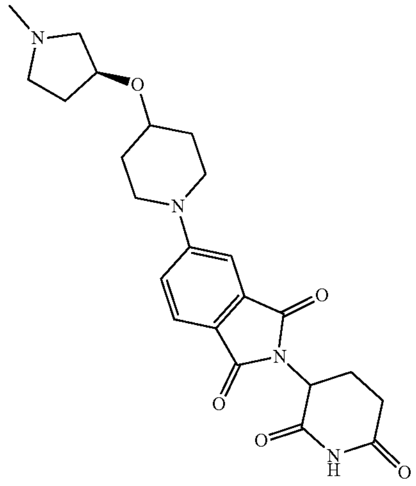
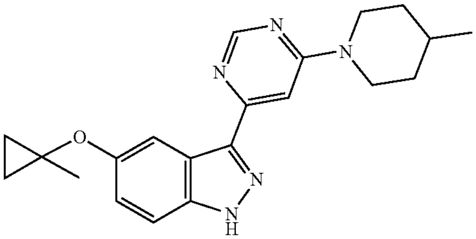
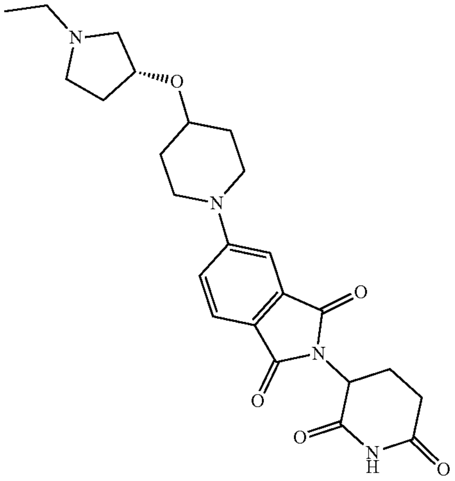
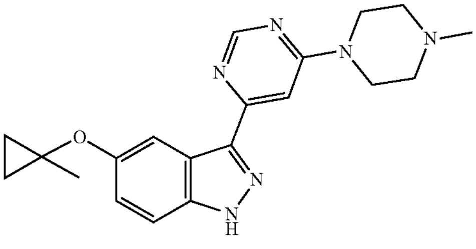

-continued
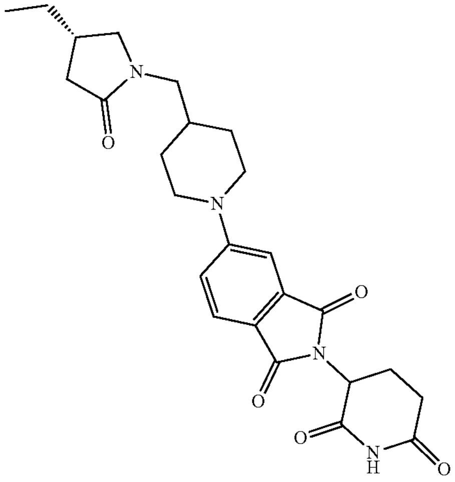
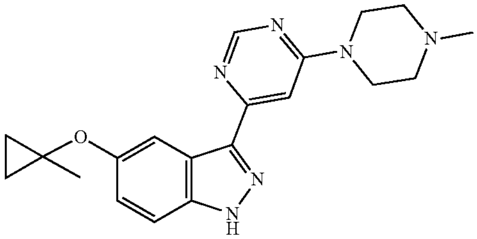
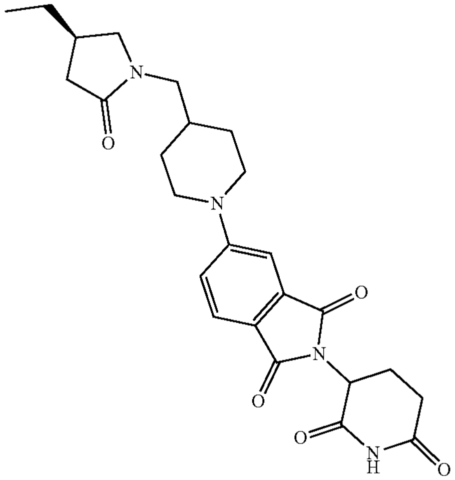
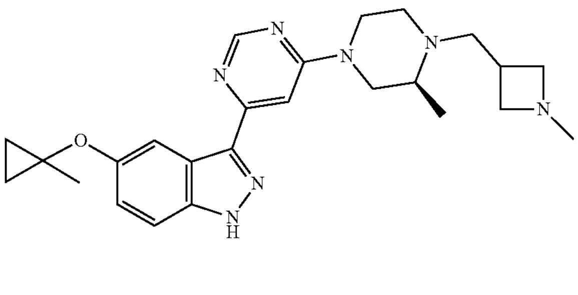
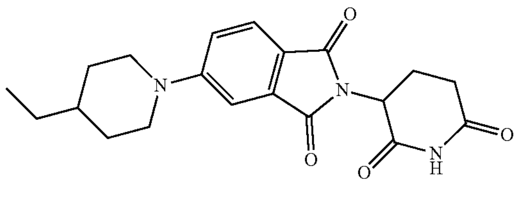
-continued
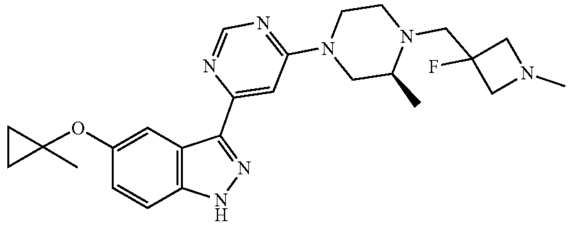
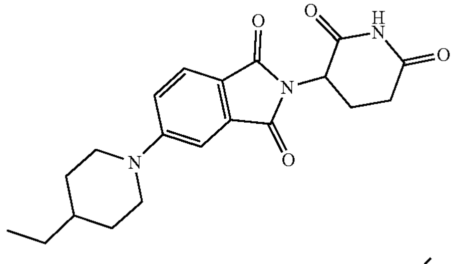
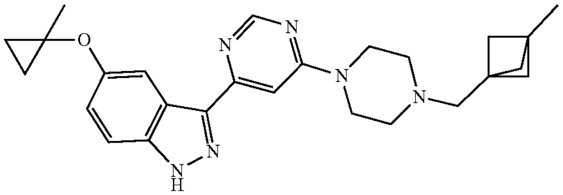
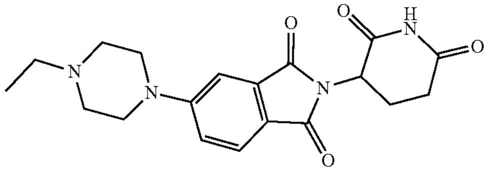
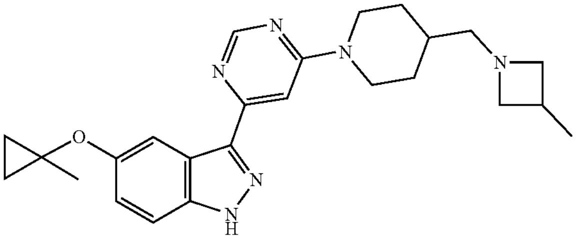
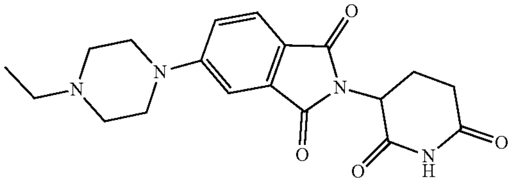
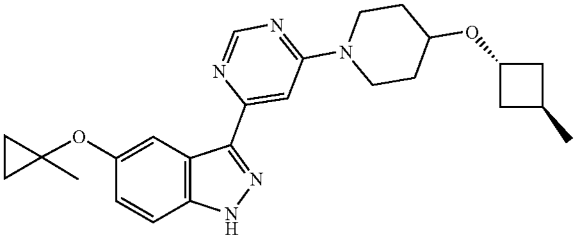
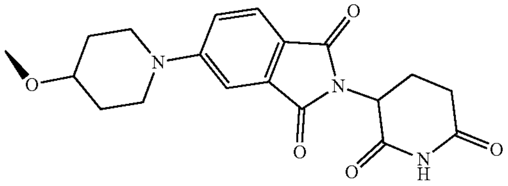

-continued
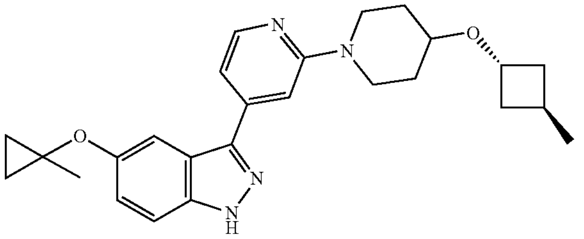
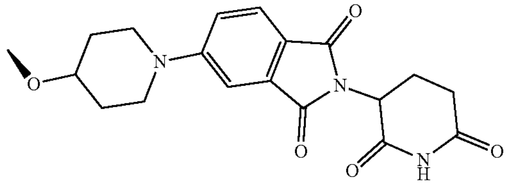
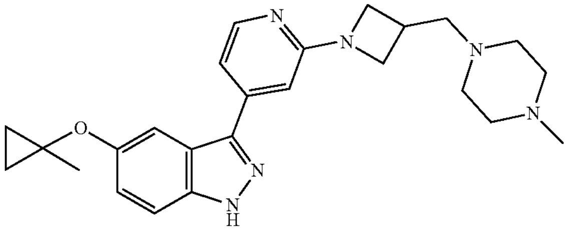
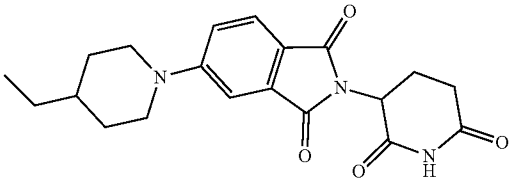
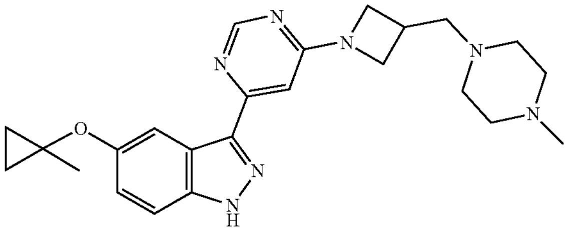
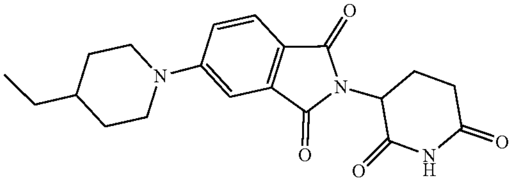
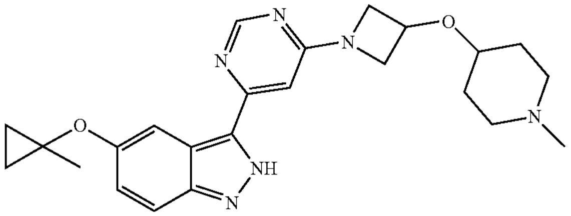
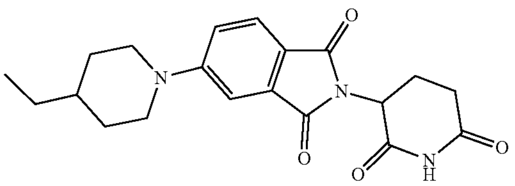
-continued
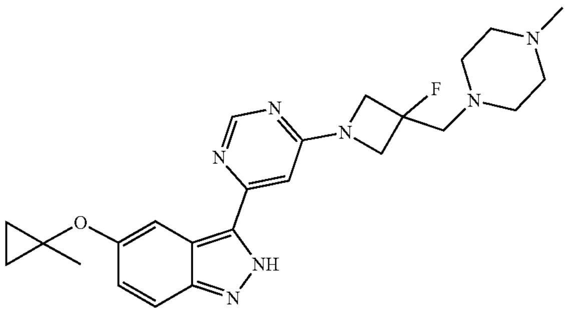
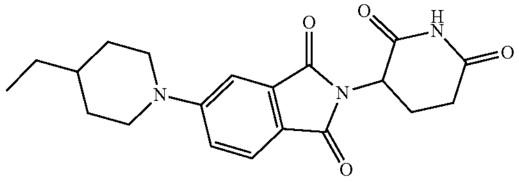
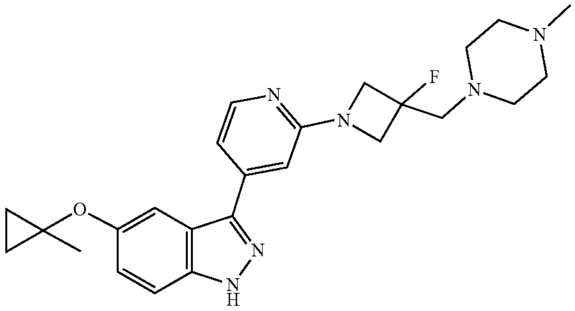
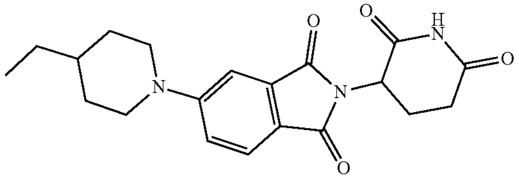
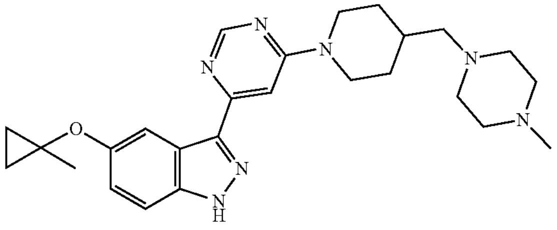
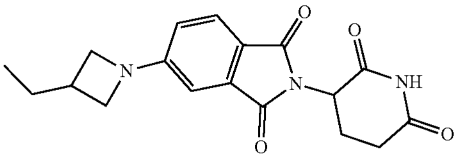
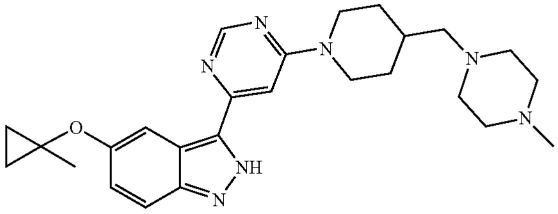

-continued
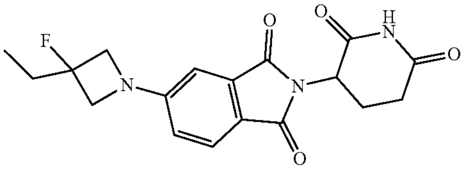
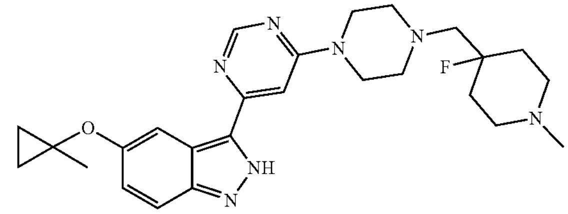
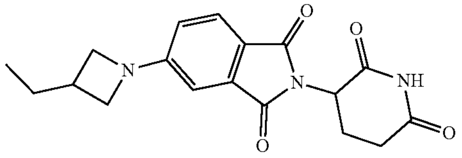
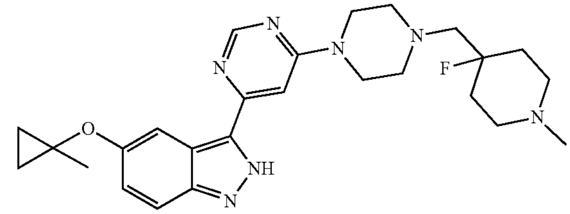
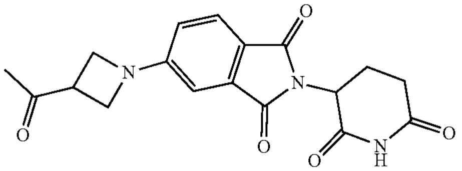
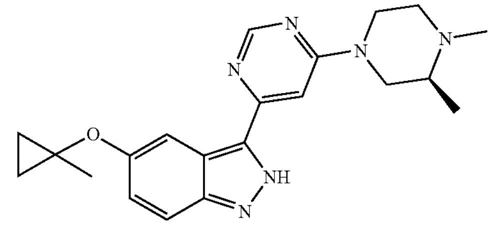
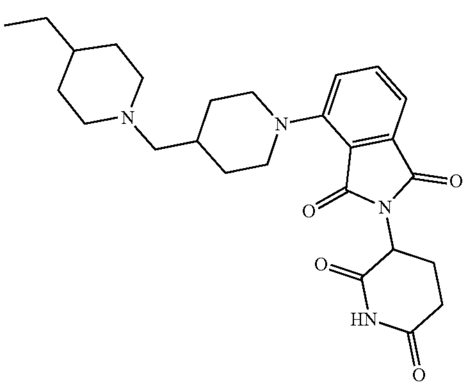
-continued
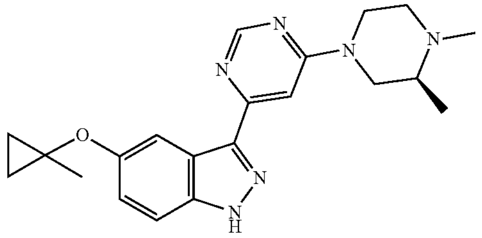
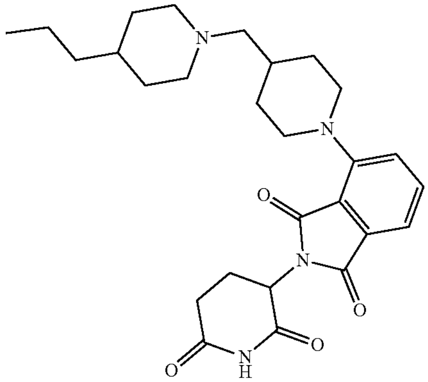
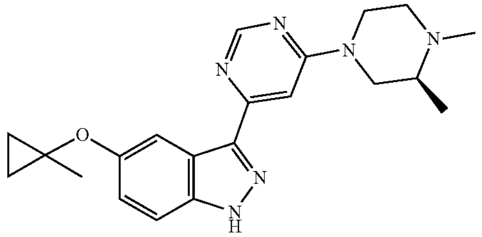
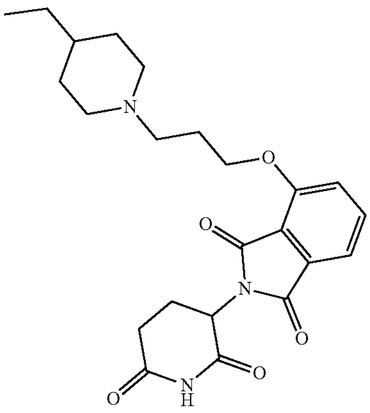
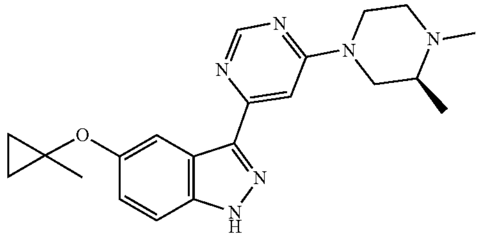

-continued
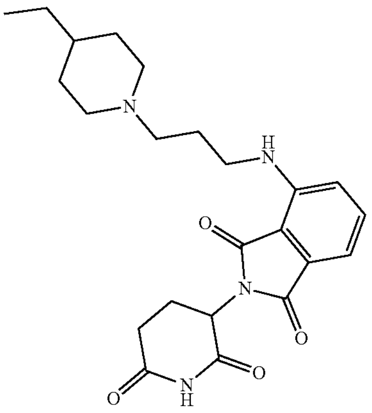
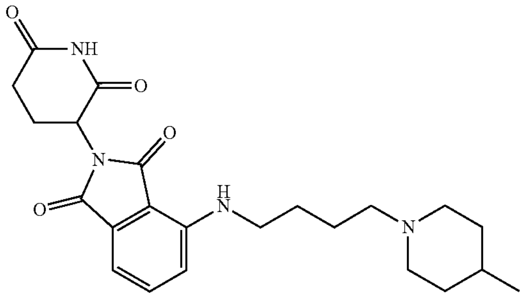
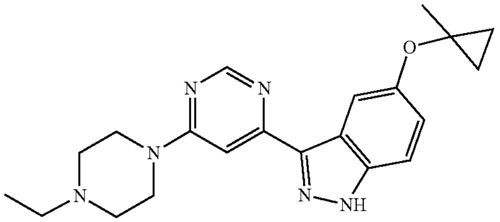
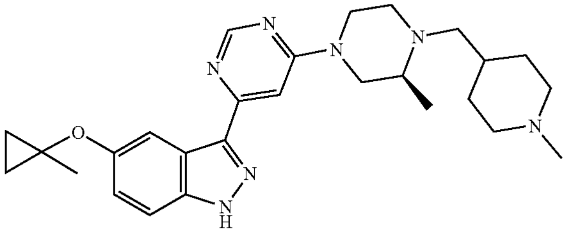
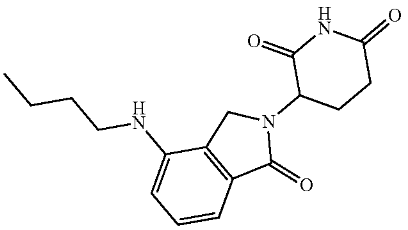
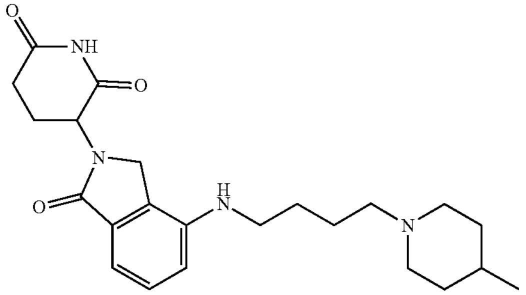
-continued
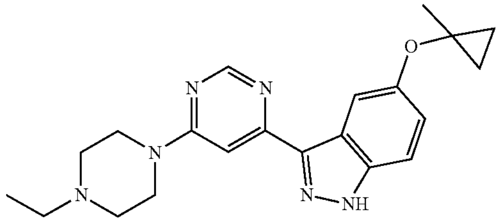
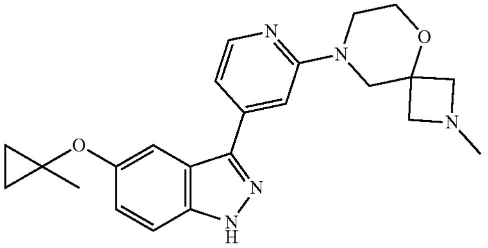
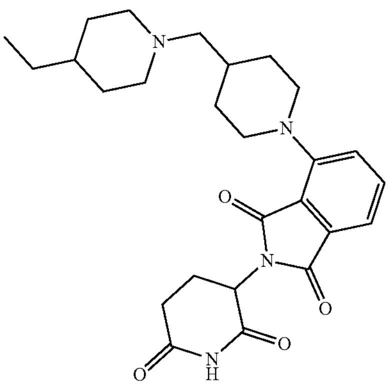
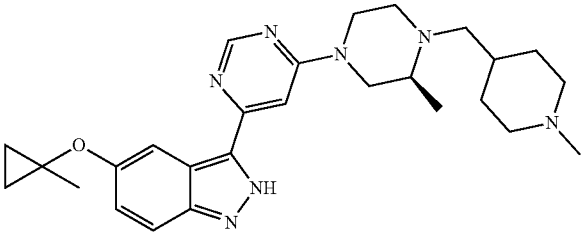
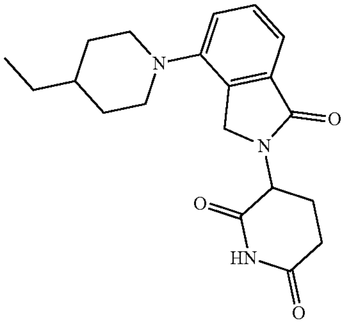

-continued
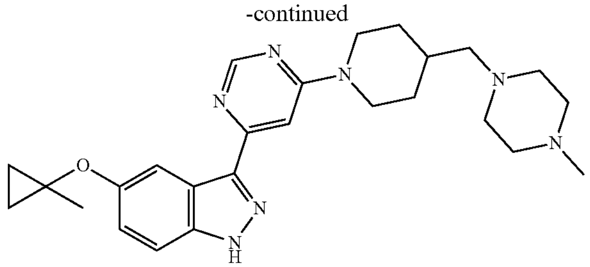
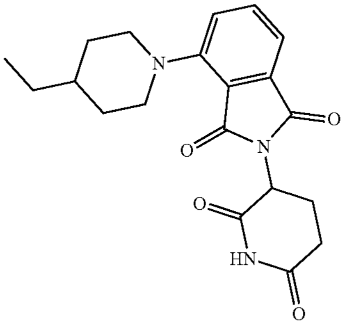
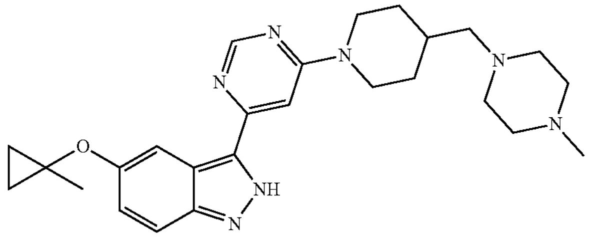
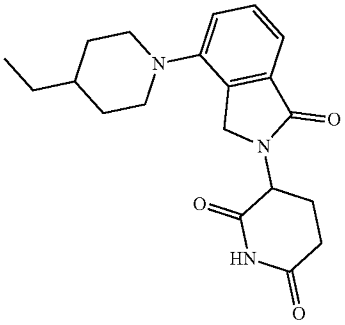
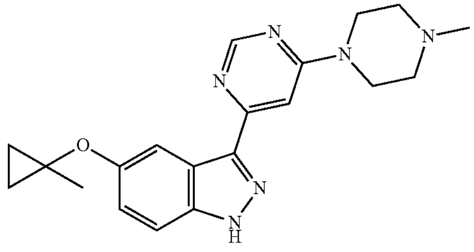
-continued
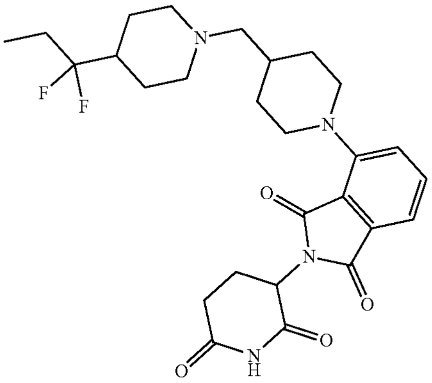
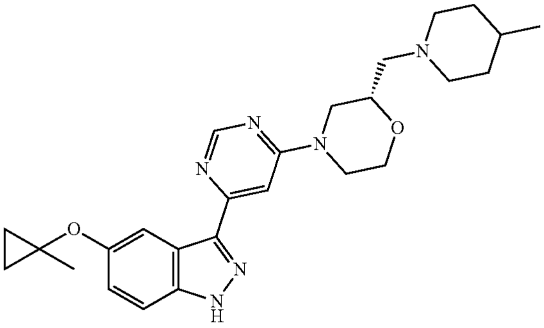
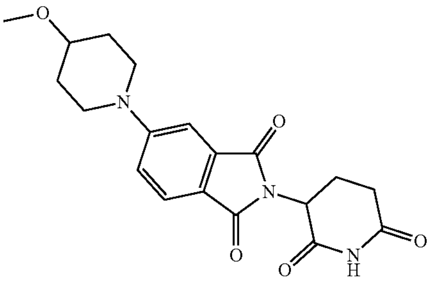
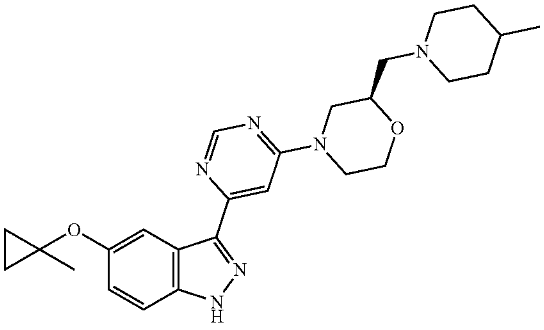
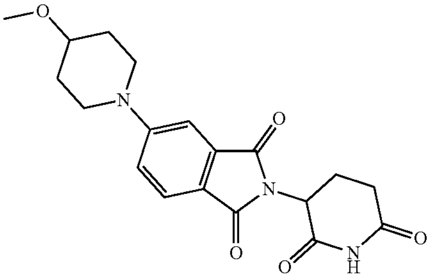

-continued
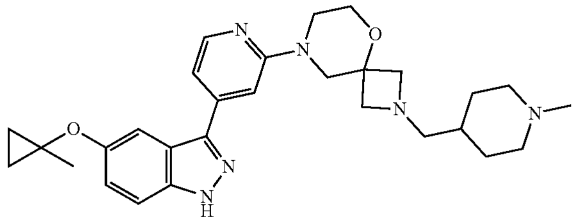
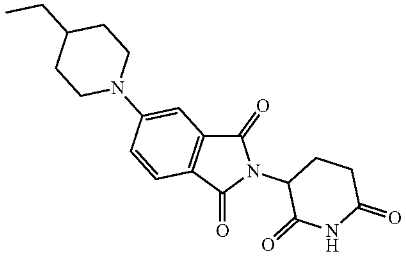
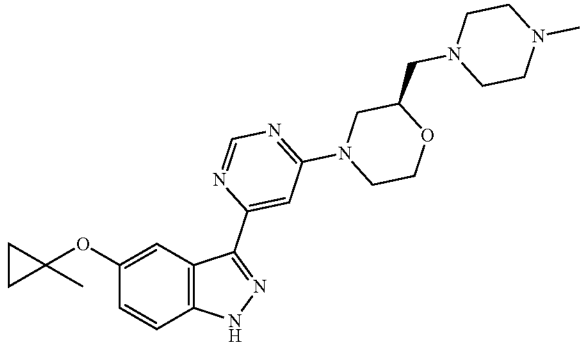
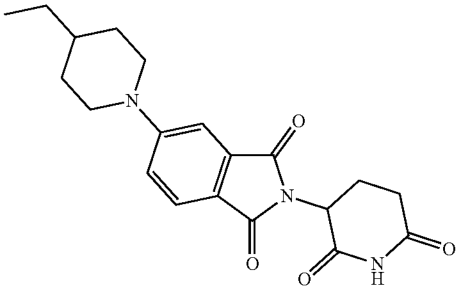
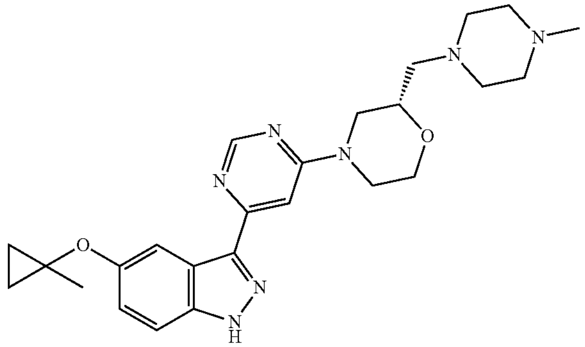
-continued
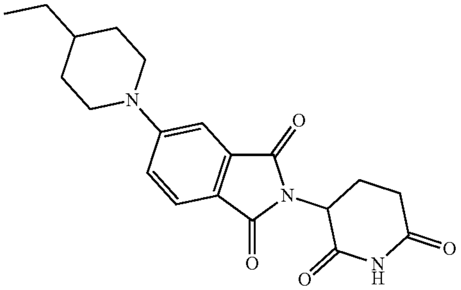
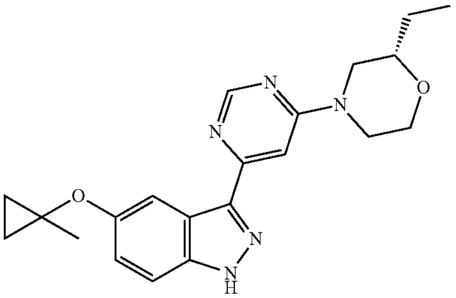
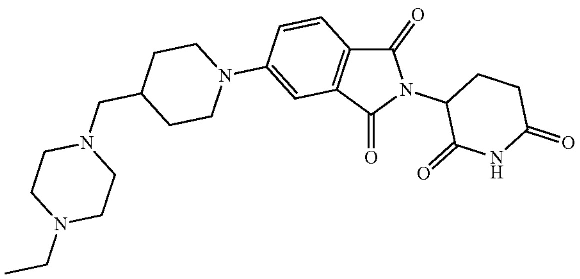
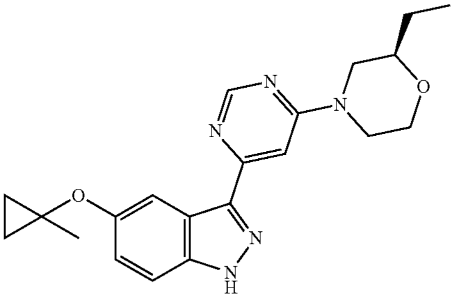
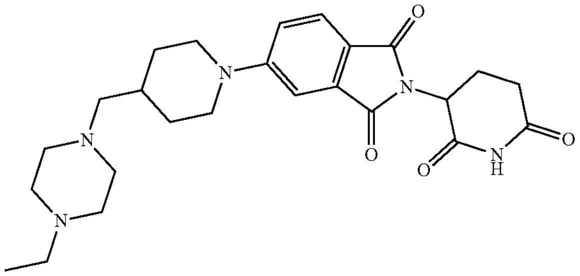
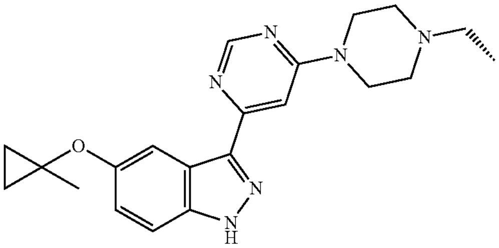

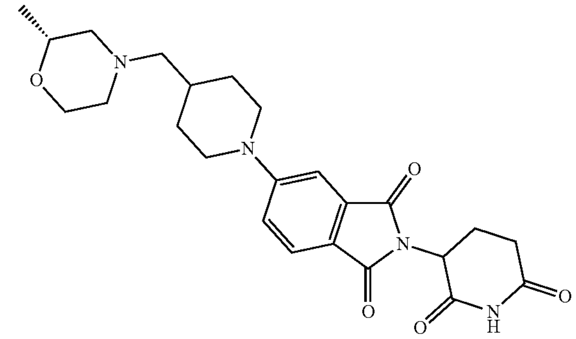
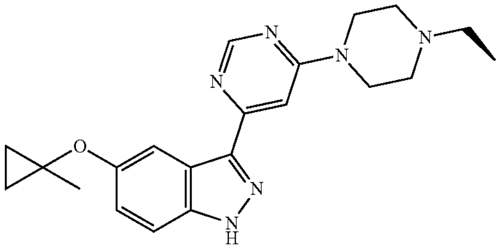
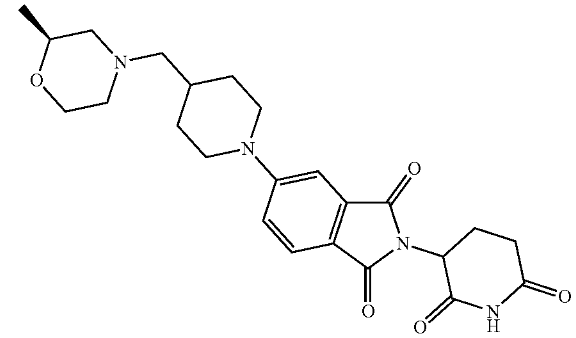
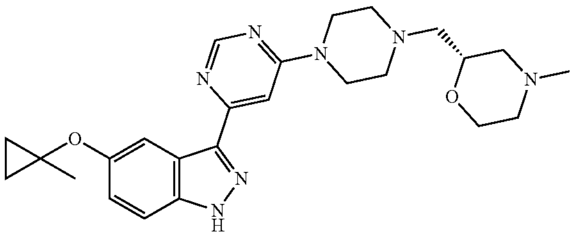
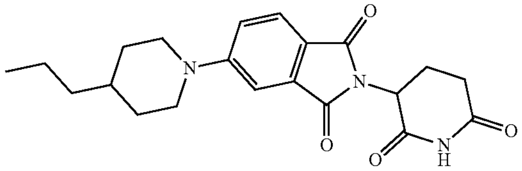
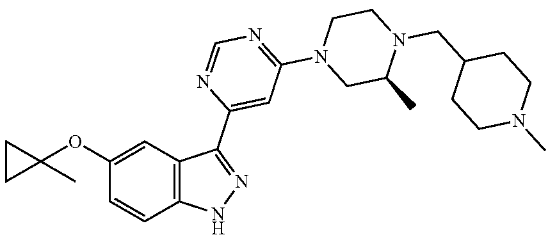
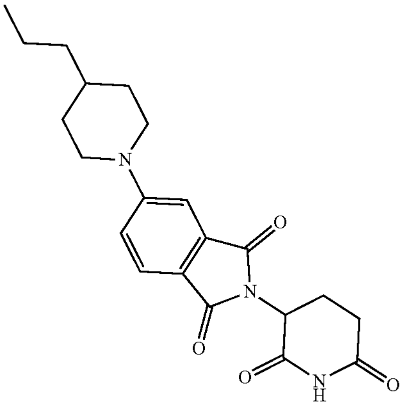
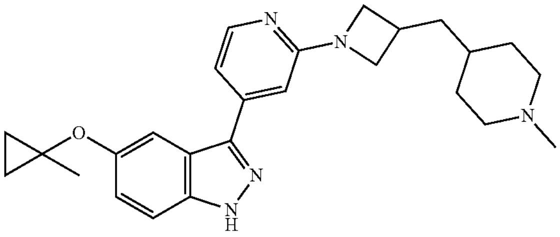
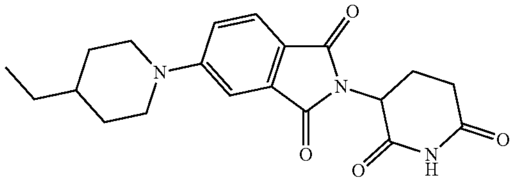
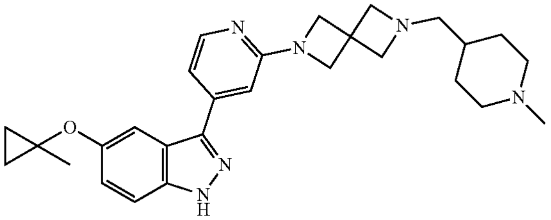
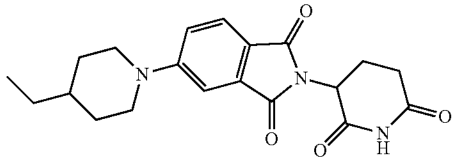

-continued
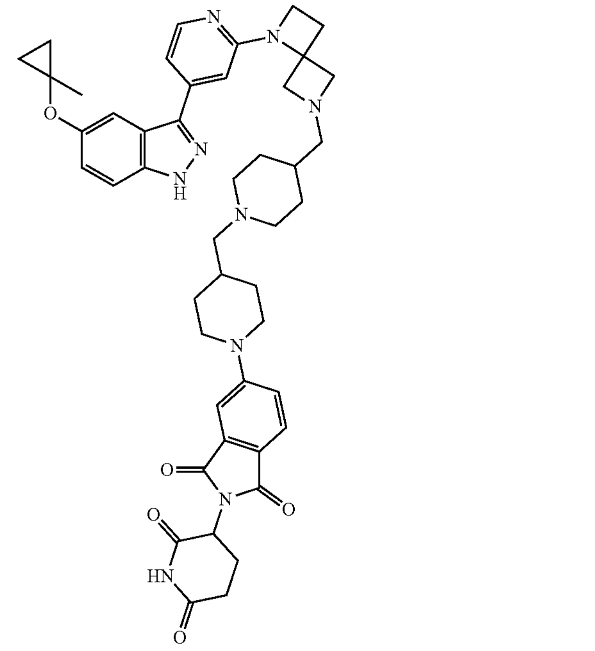
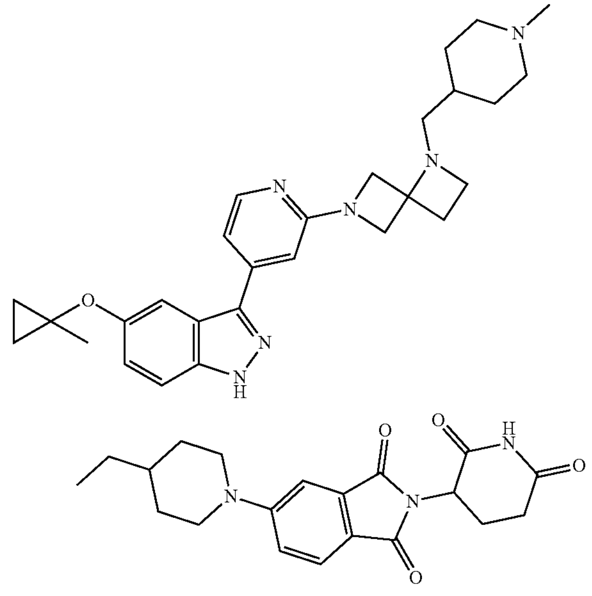
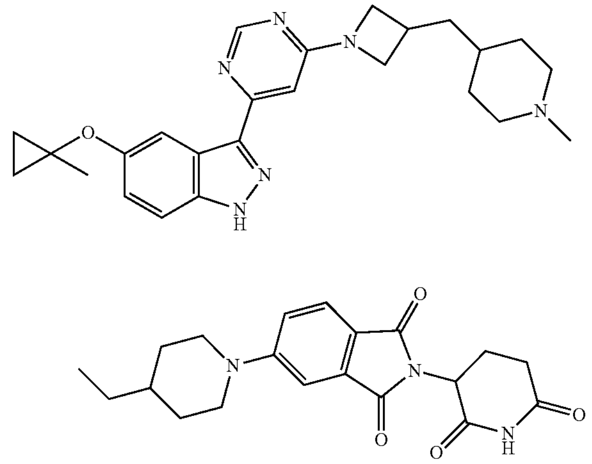
-continued
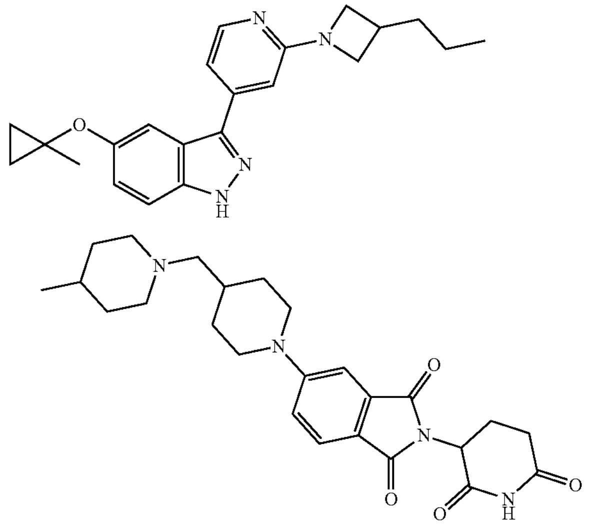
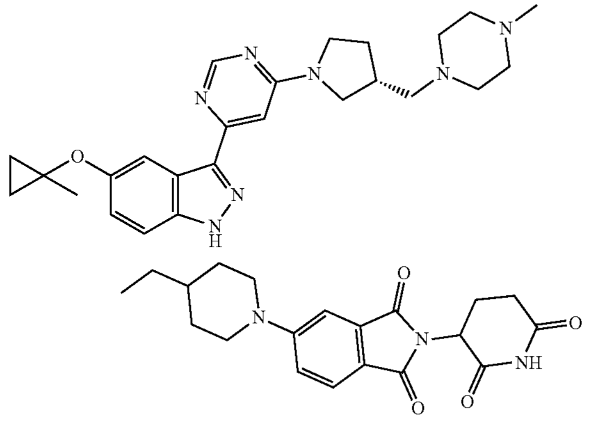
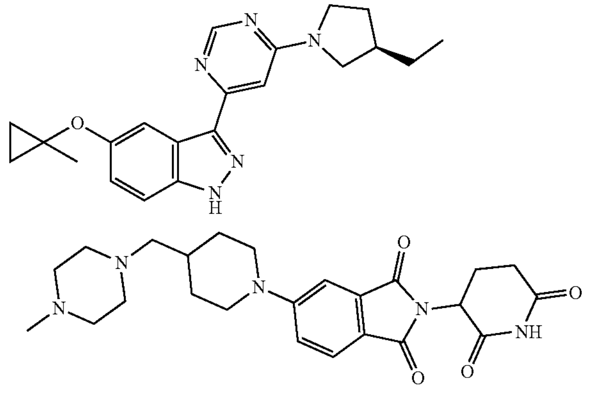
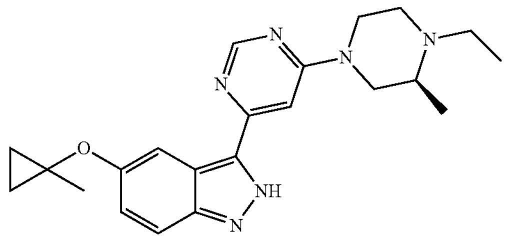

-continued
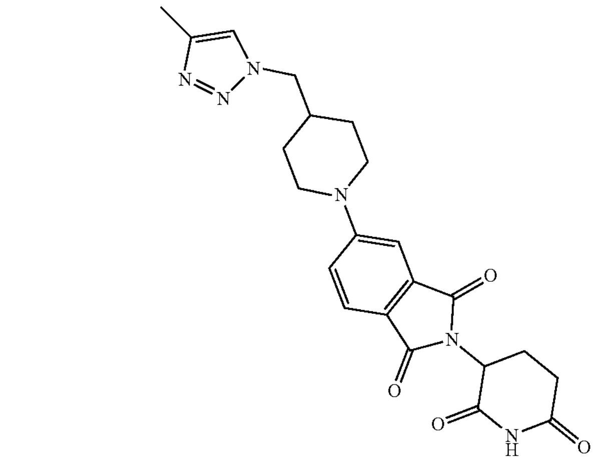
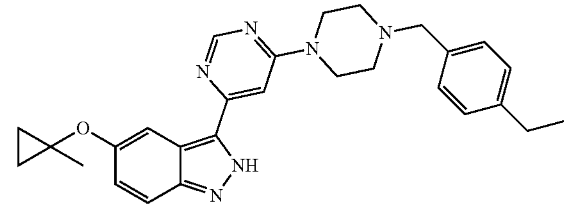
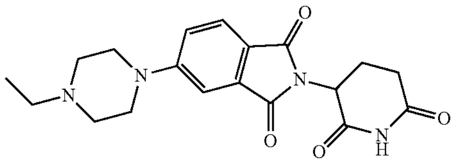
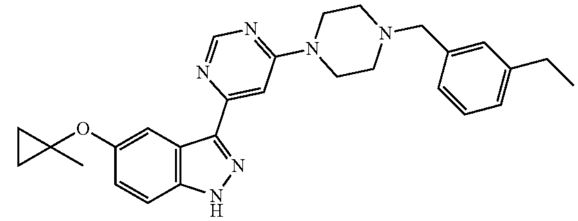
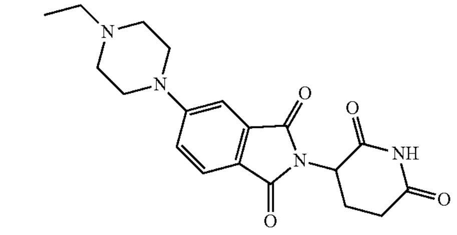
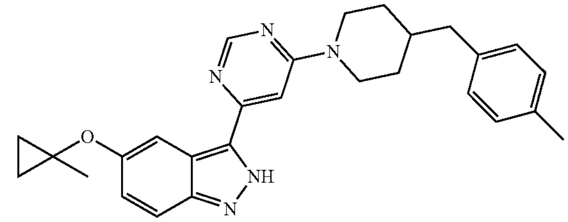
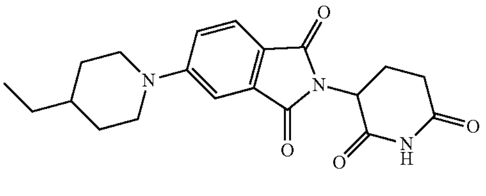
-continued
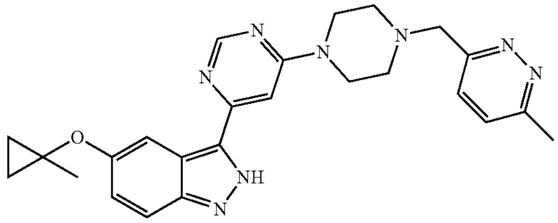
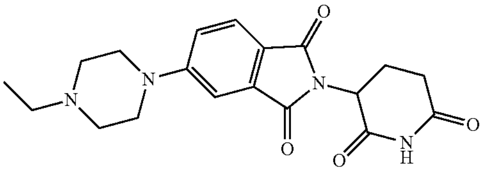
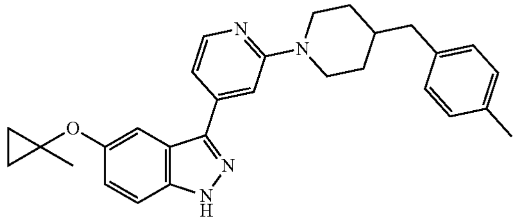
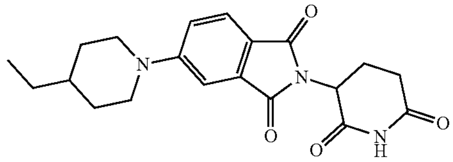
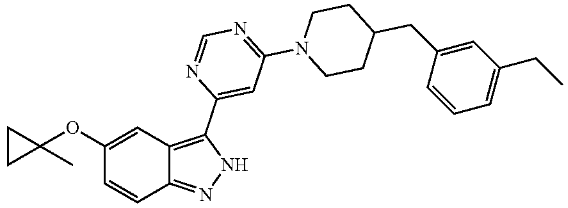
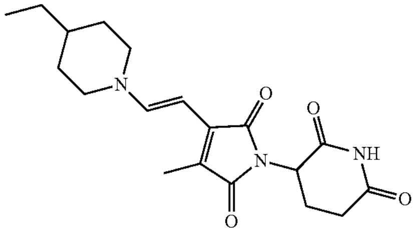
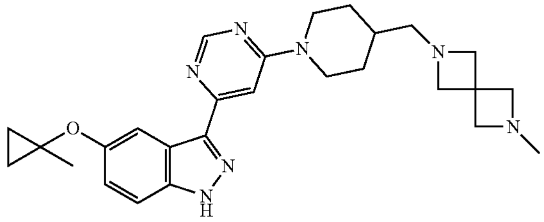
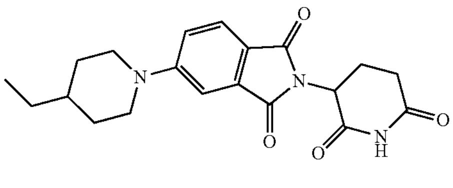

-continued
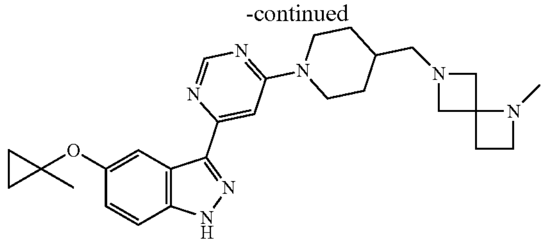
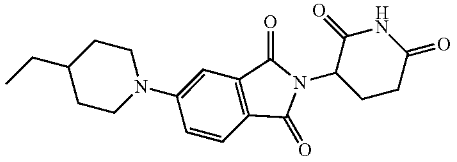
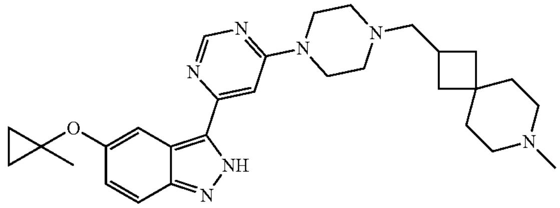
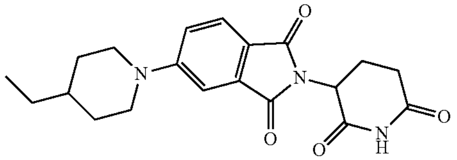
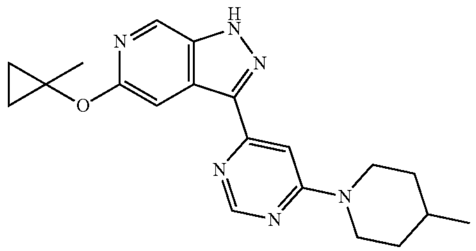
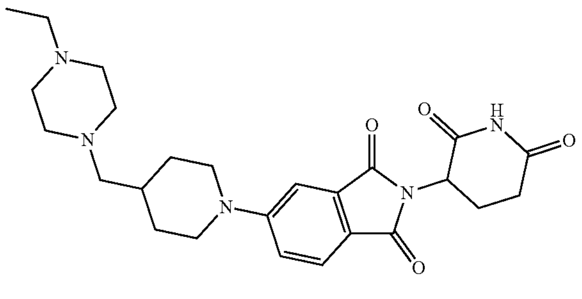
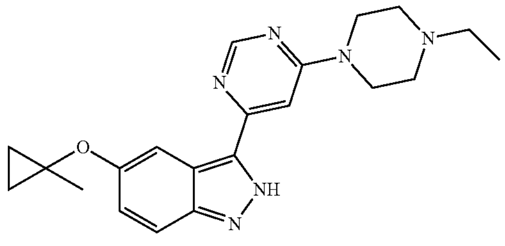
-continued
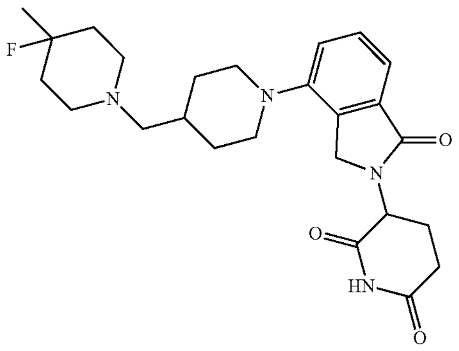
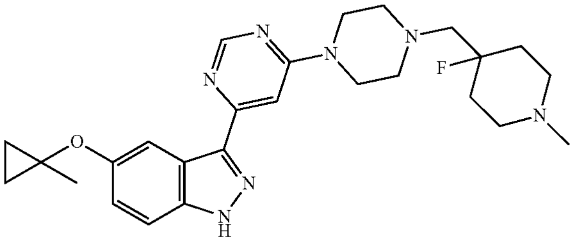
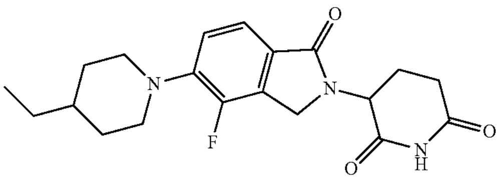
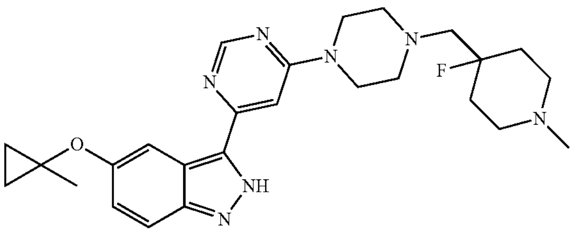
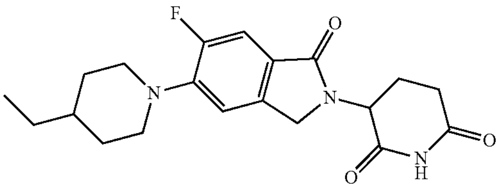
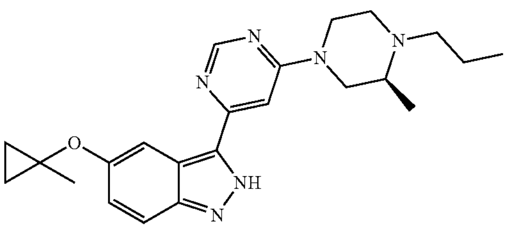
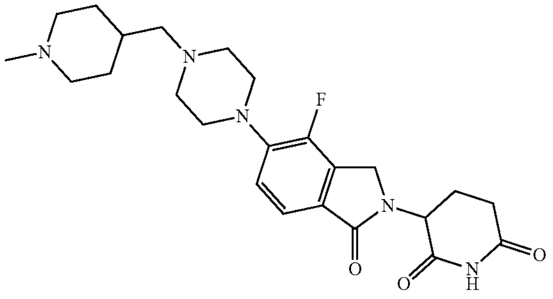

-continued
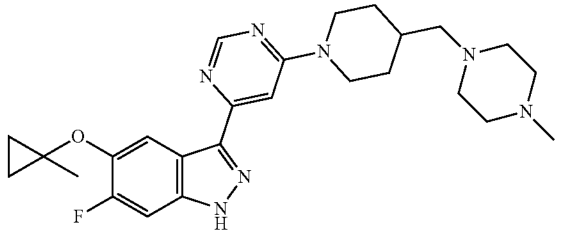
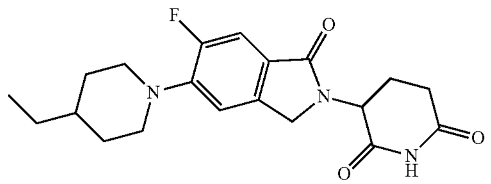
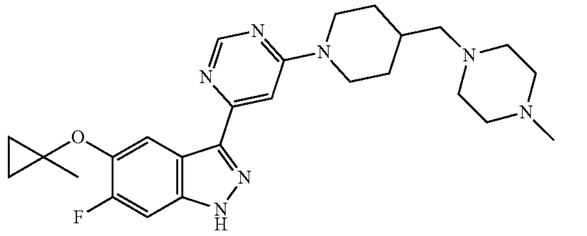
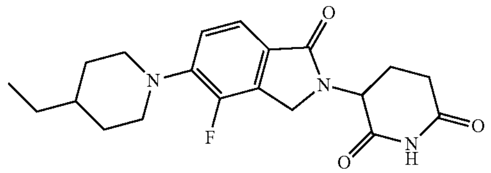
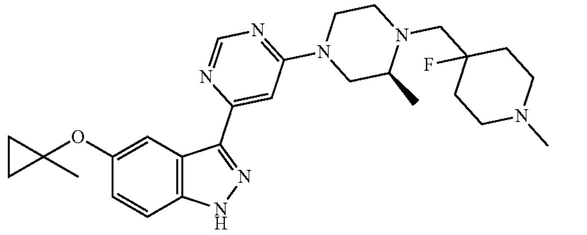
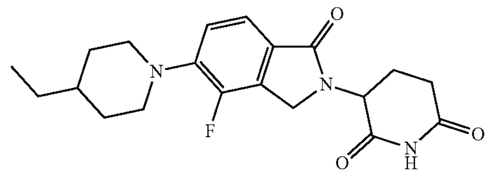
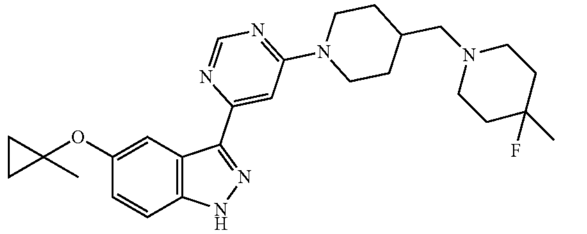
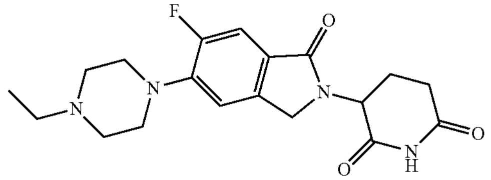
-continued
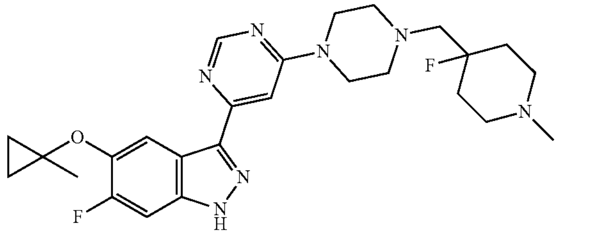
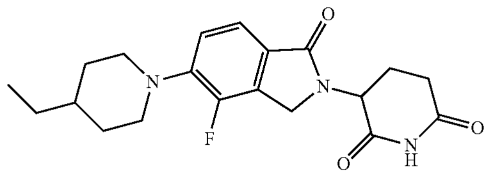
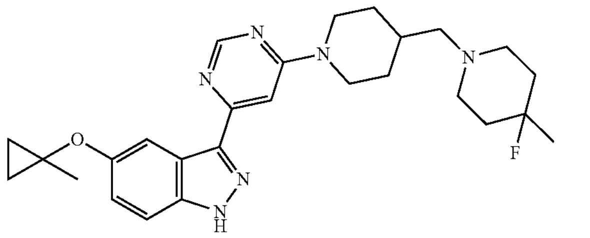
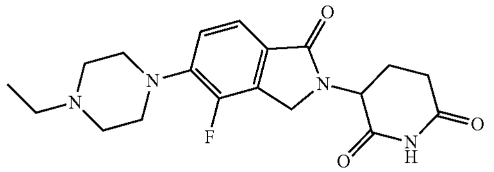
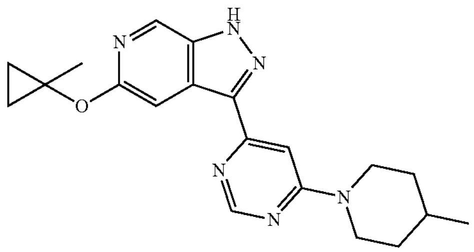
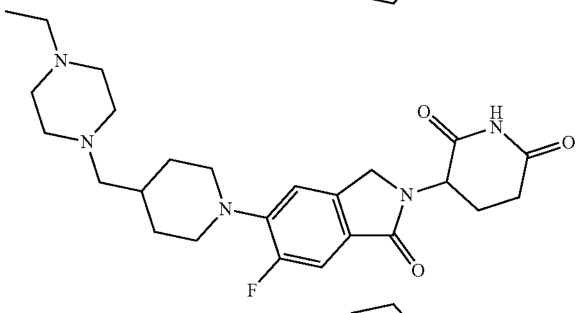
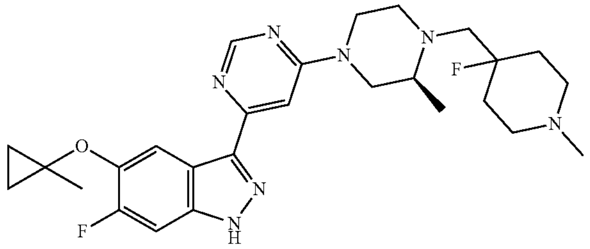

-continued
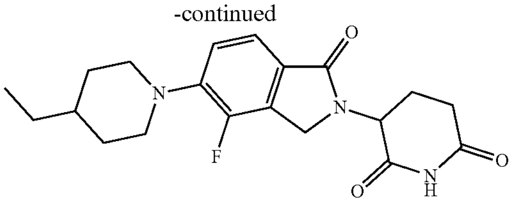
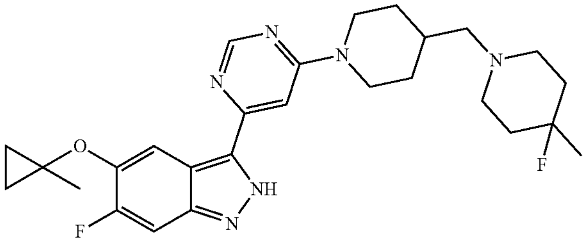
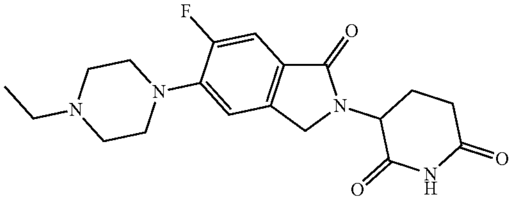
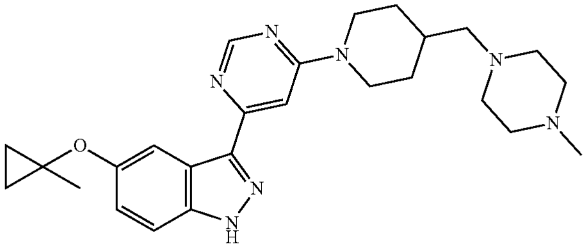
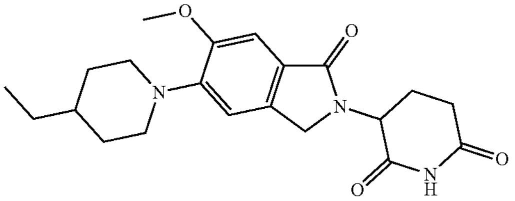
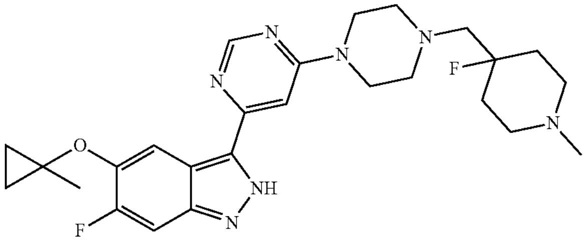
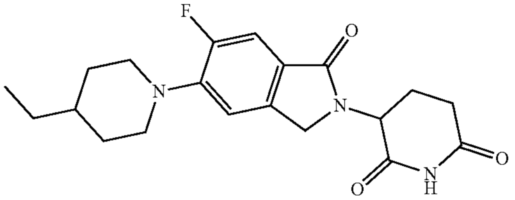
-continued
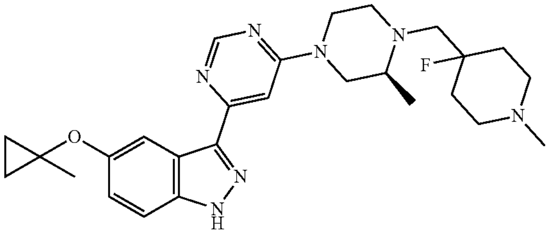
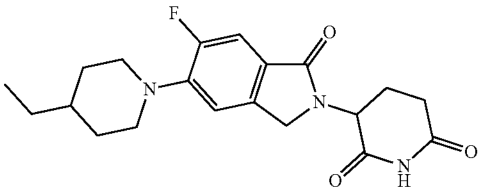
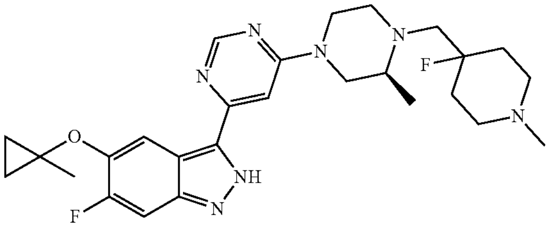
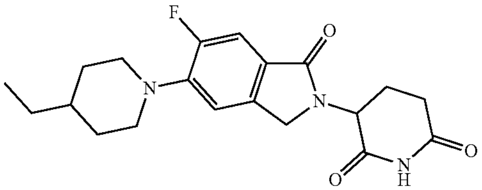
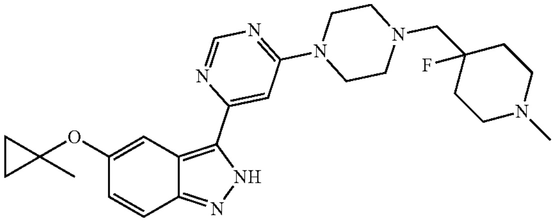
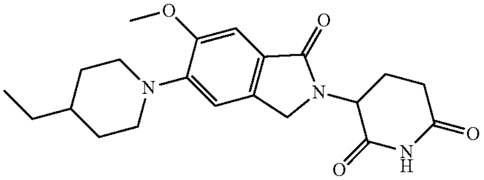
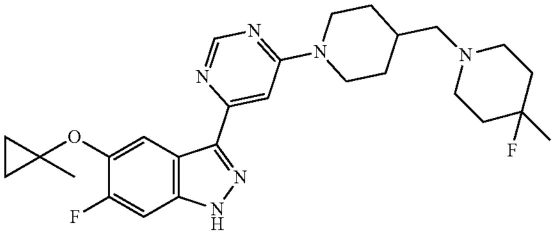
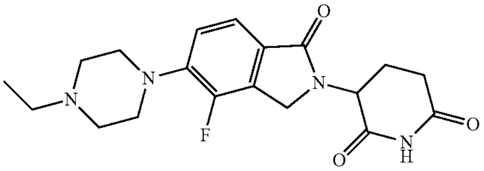

-continued
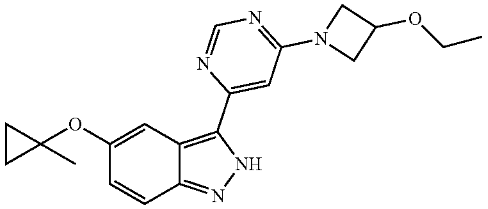
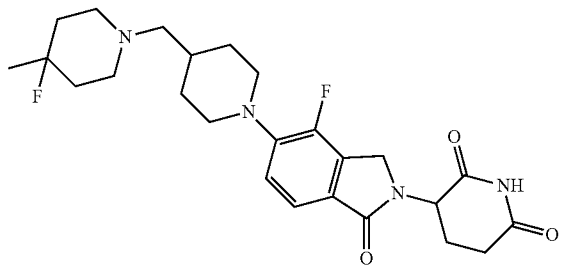
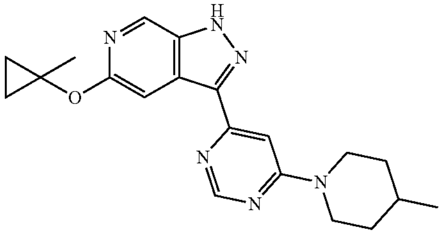
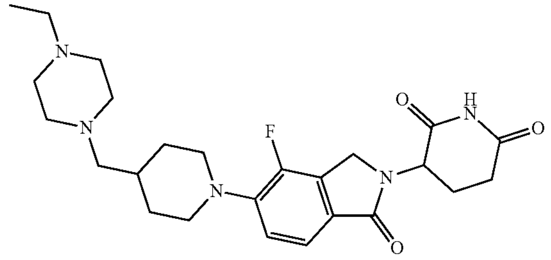
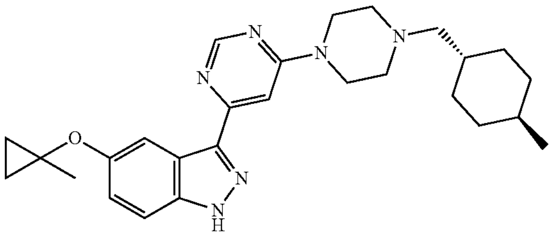
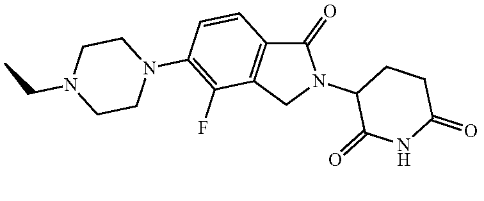
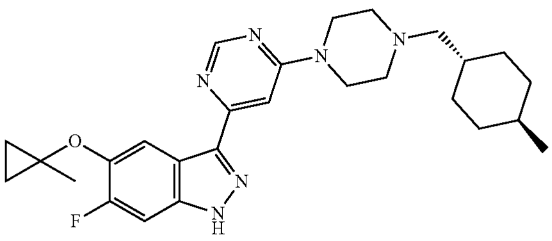
-continued
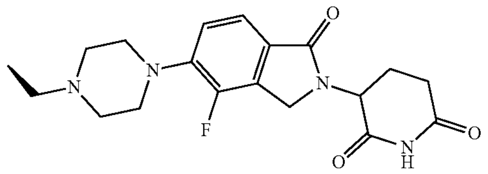
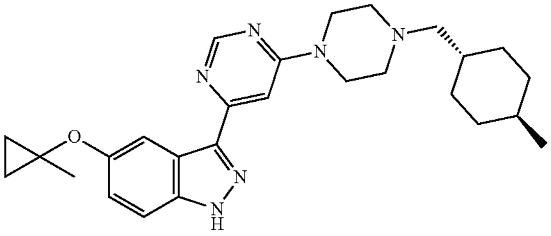
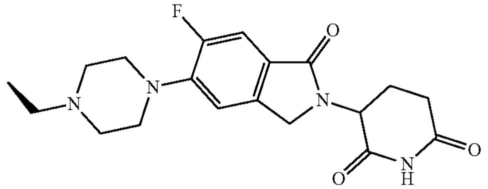
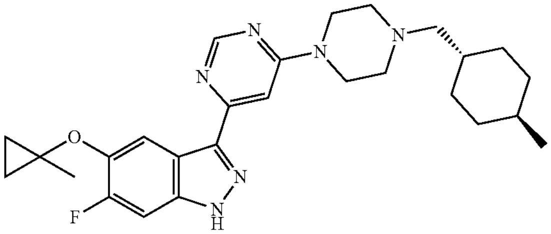
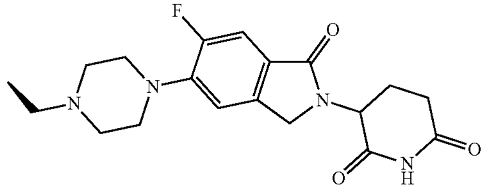
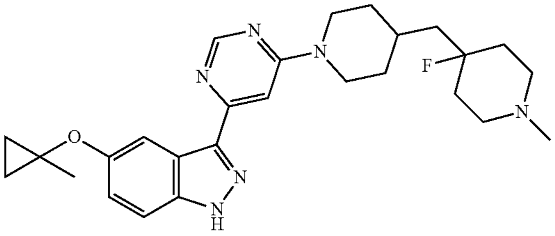
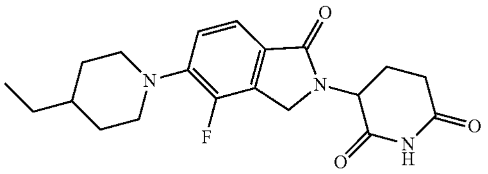
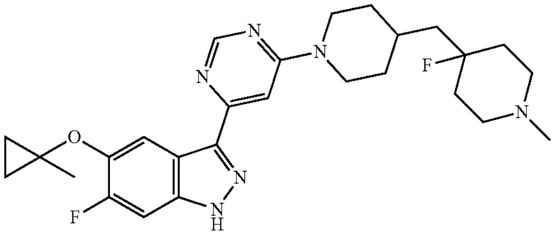

-continued
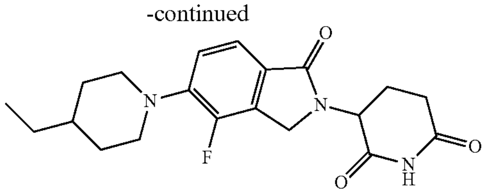
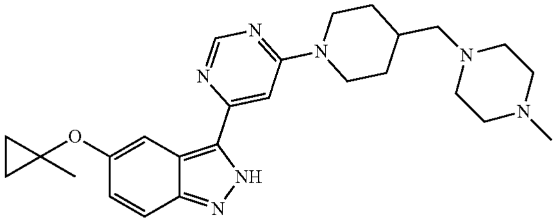
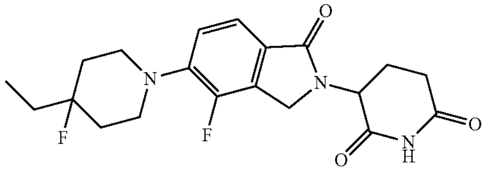
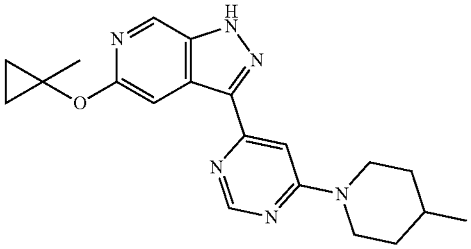
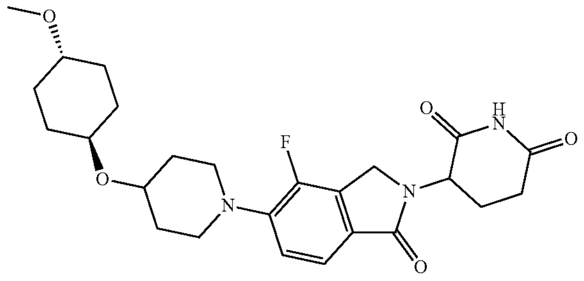
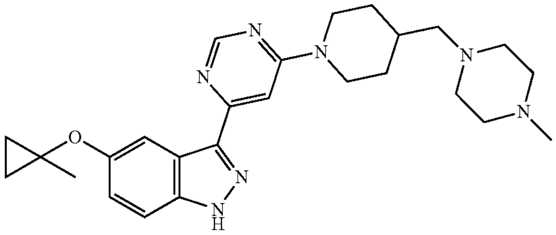
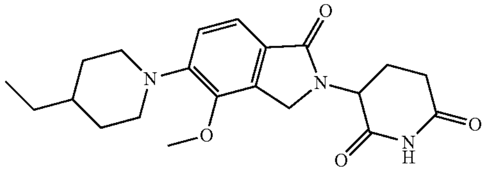
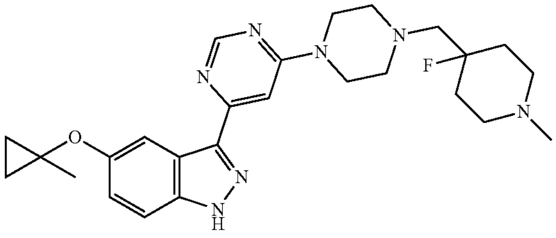
-continued
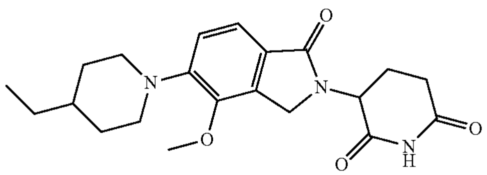
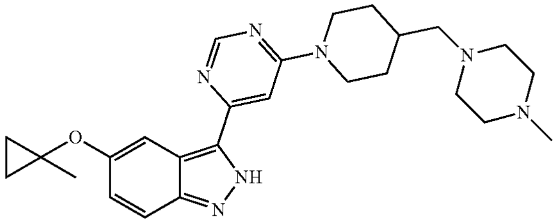
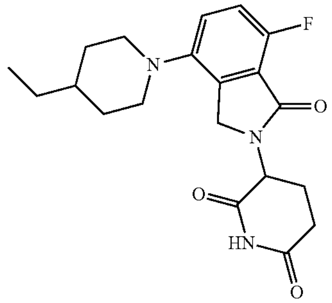
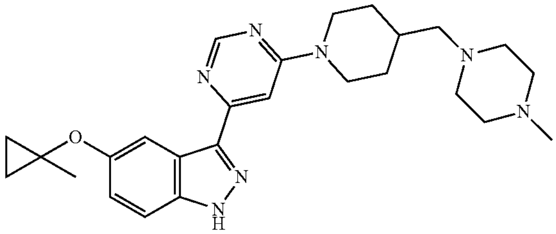
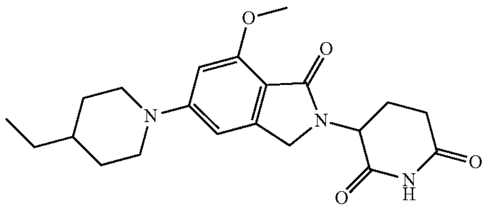
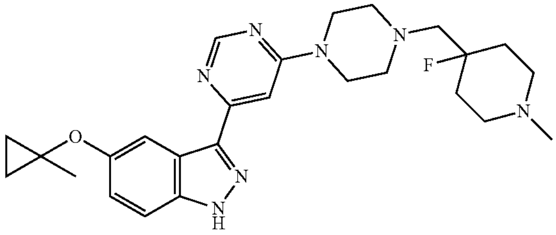
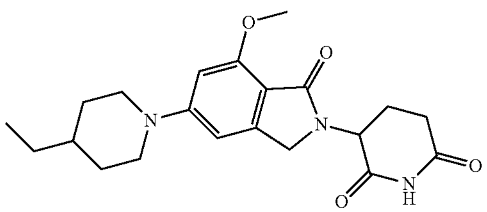

-continued
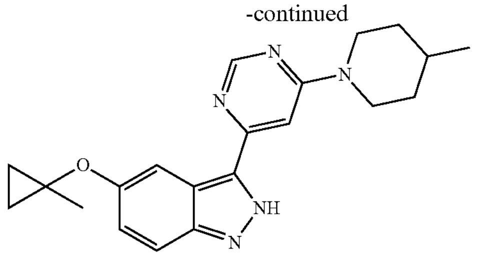
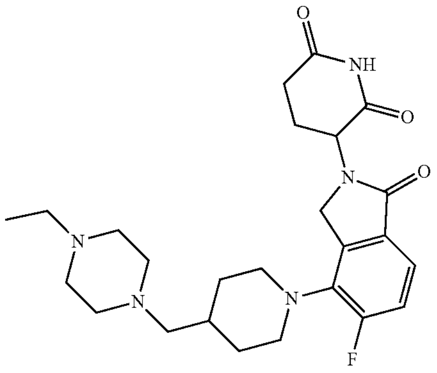
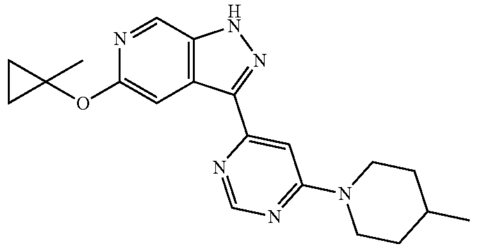
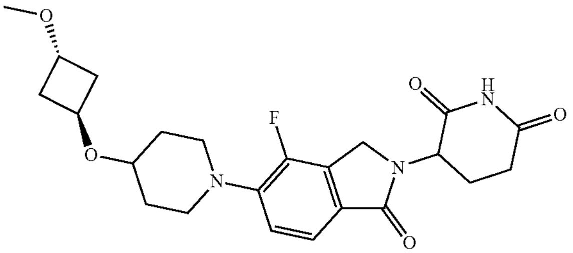
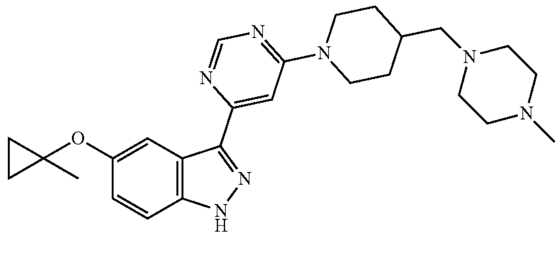
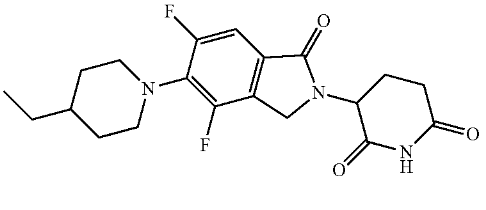
-continued
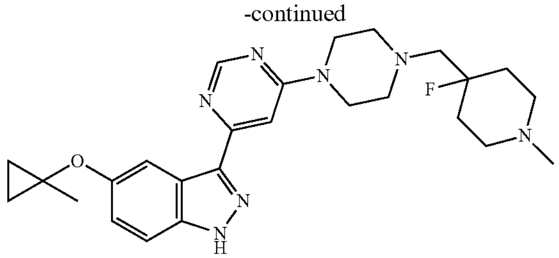
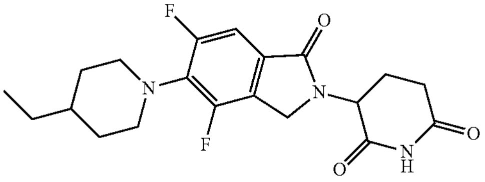
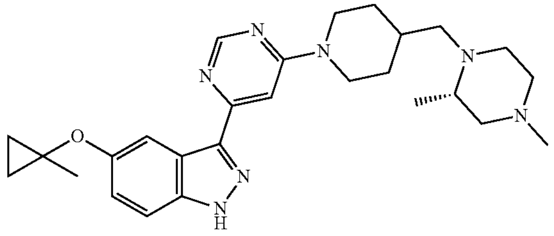
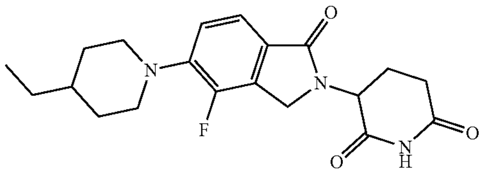
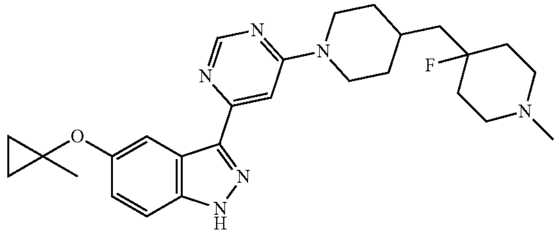
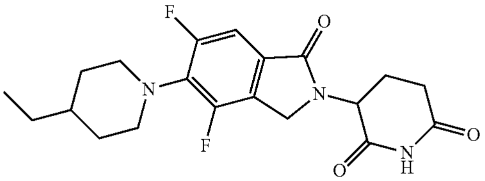
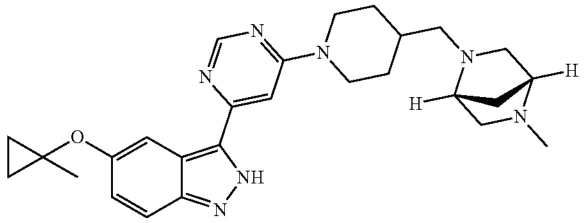
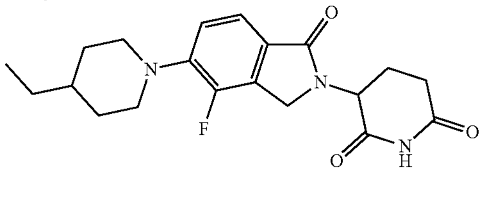

-continued
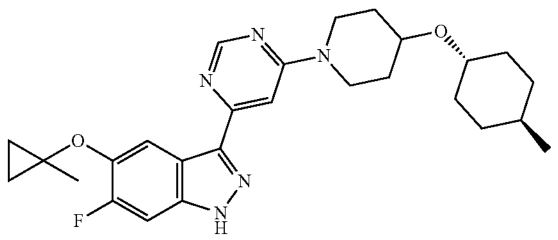
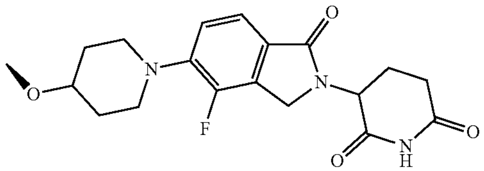
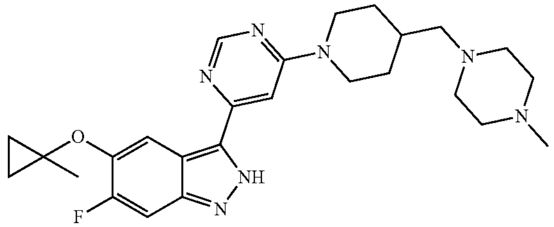
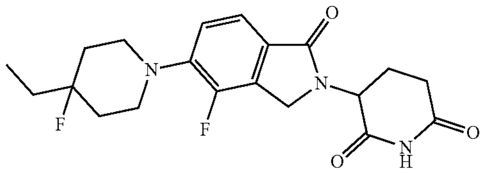
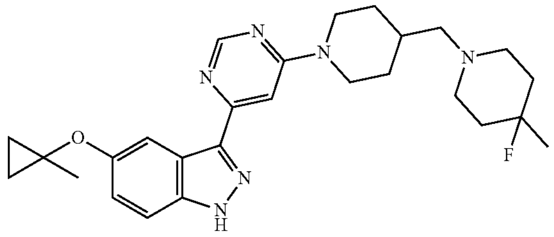
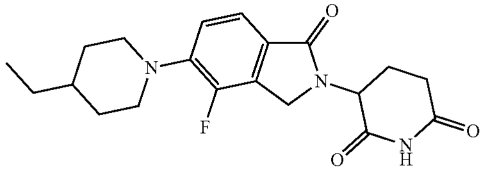
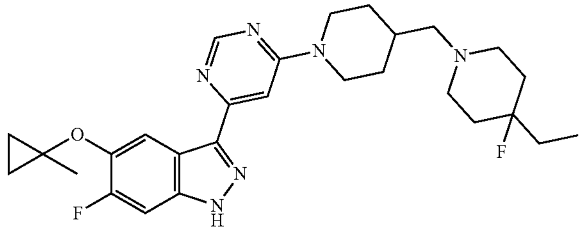
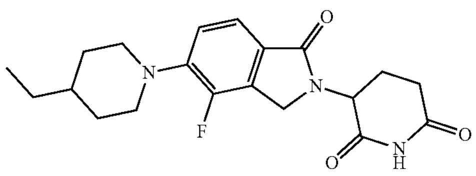
-continued
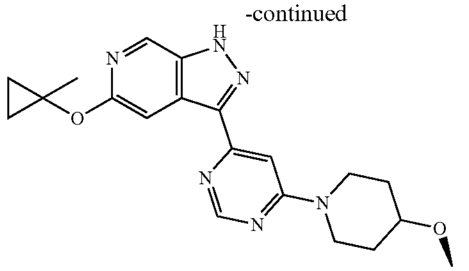
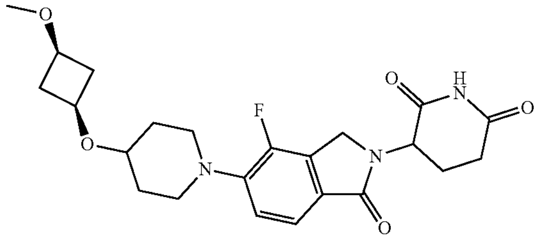
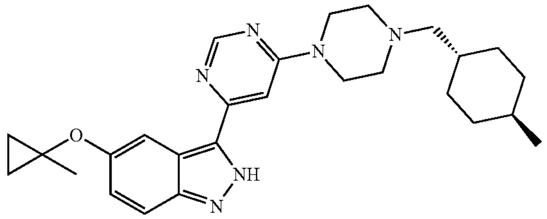
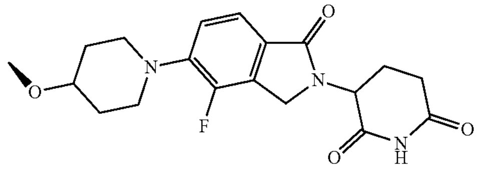
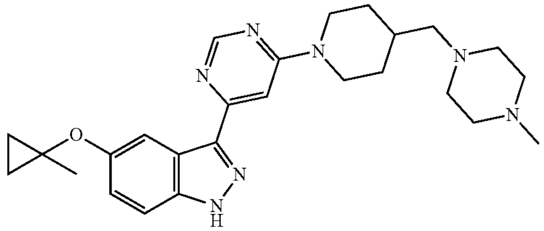
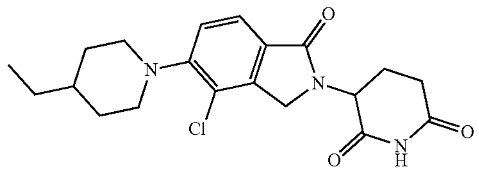
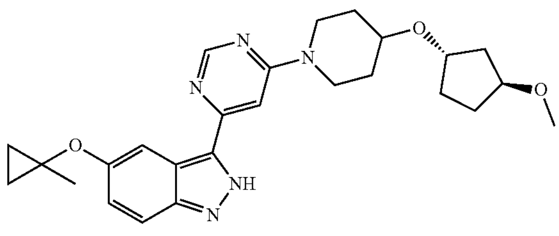

-continued
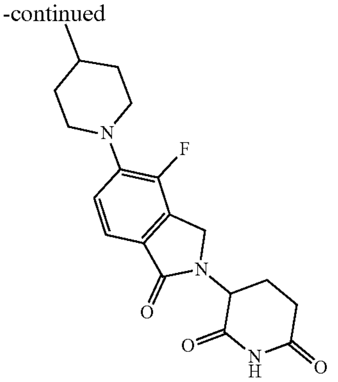
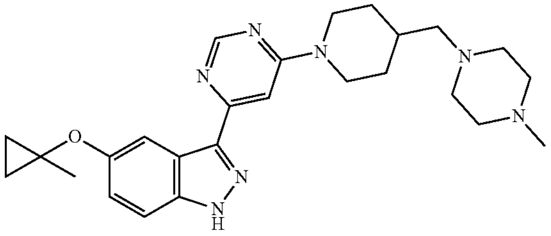
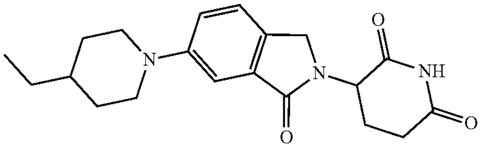
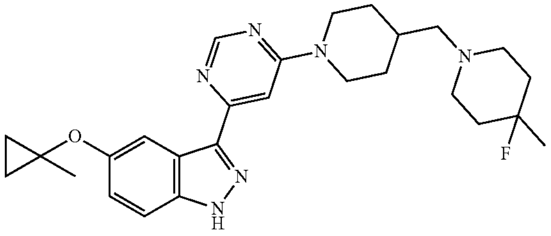
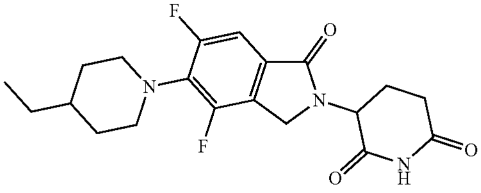
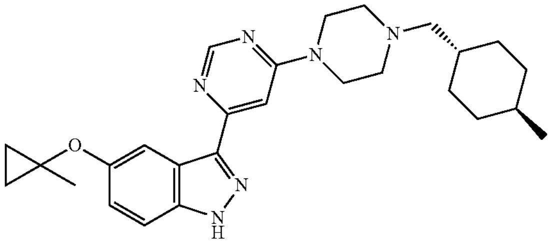
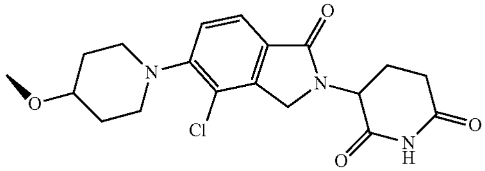
-continued
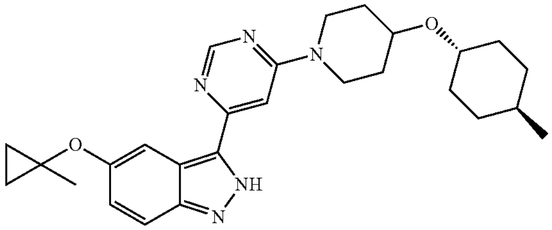
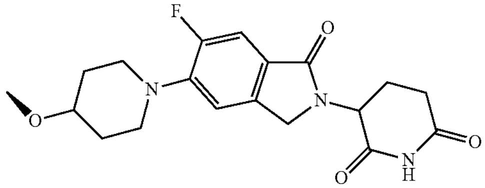
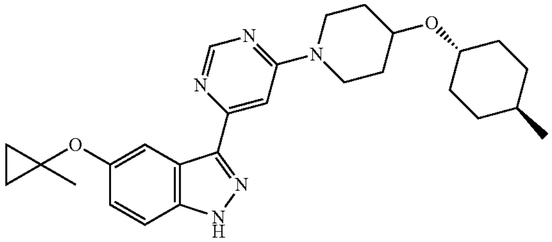
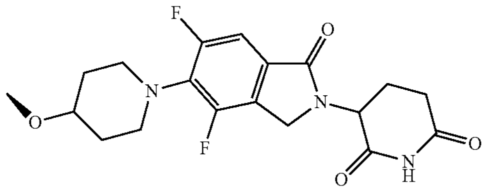
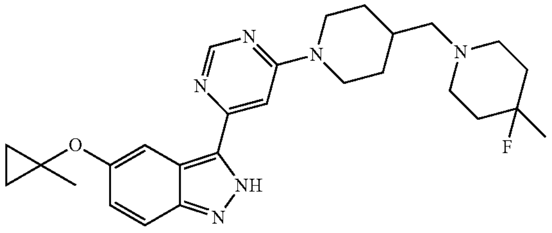
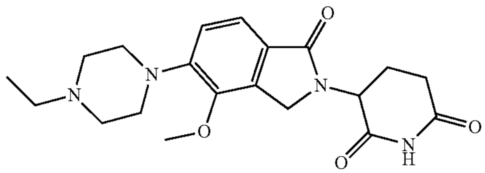
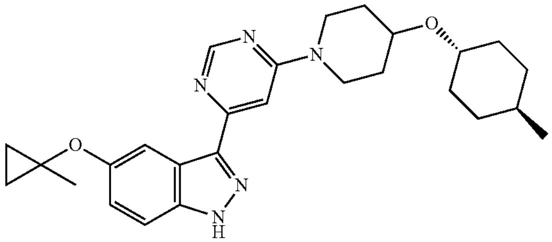
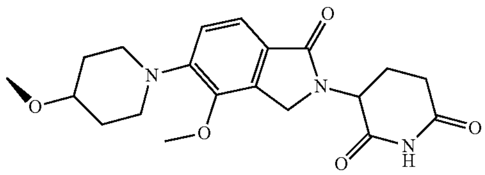

-continued
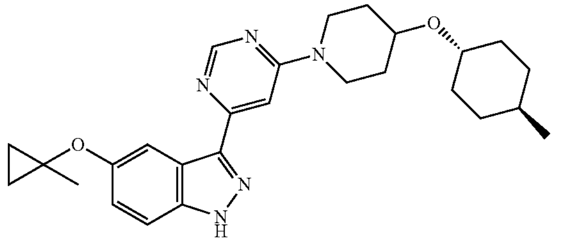
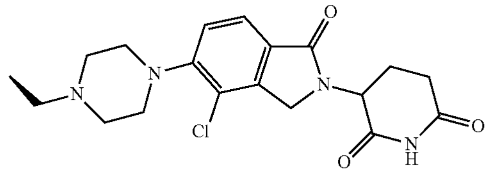
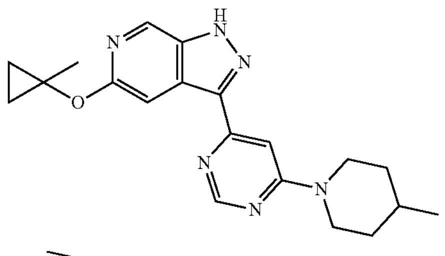
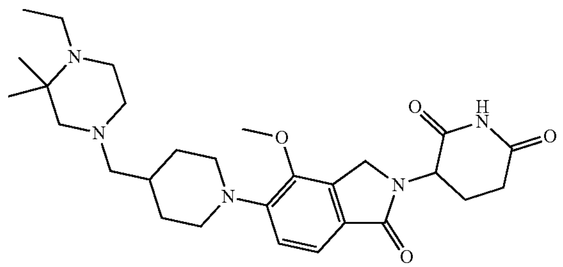
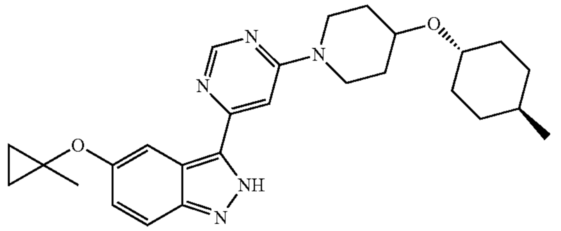
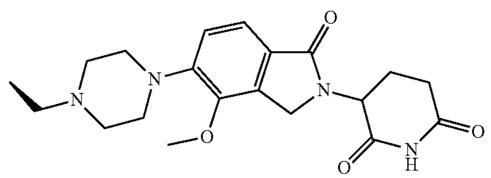
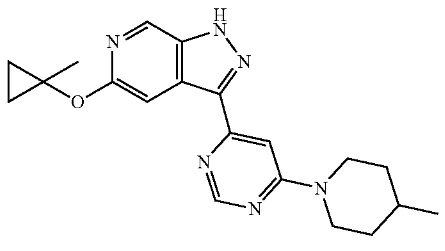
-continued
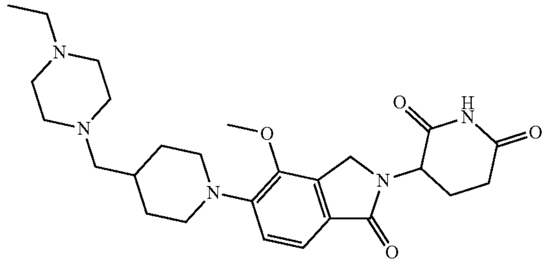
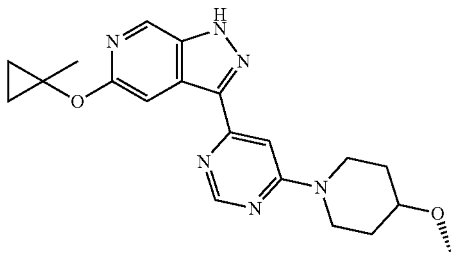
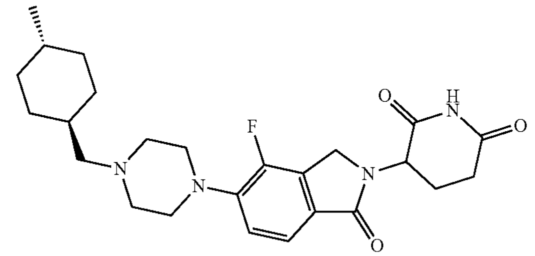
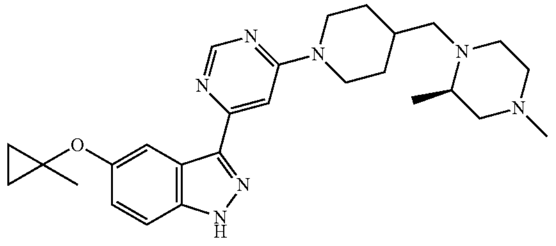
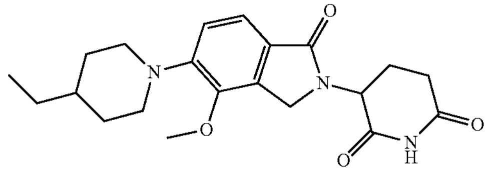
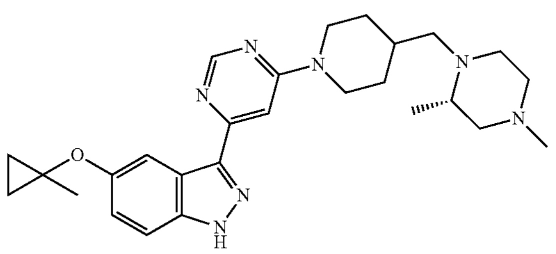
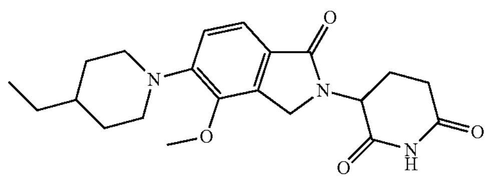

-continued
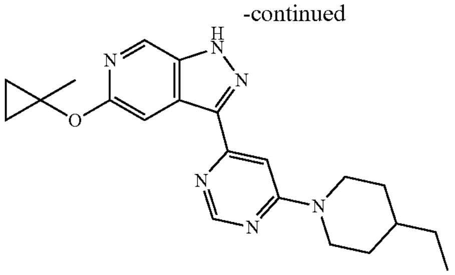
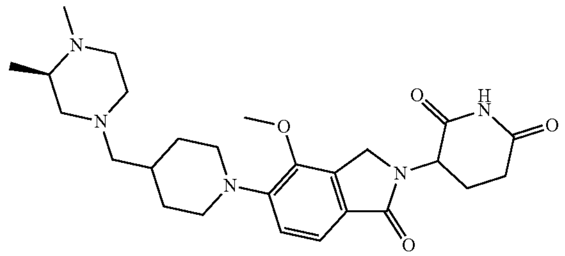
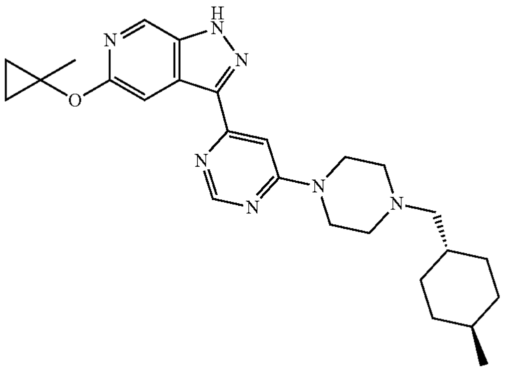
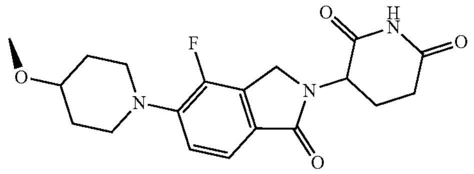
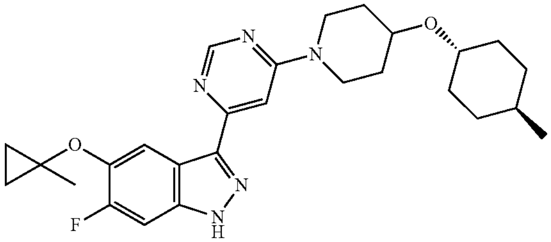
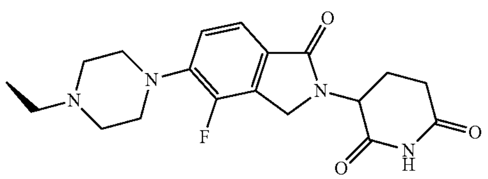
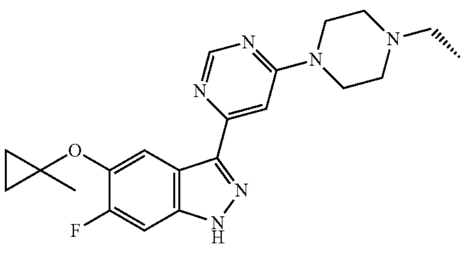
-continued
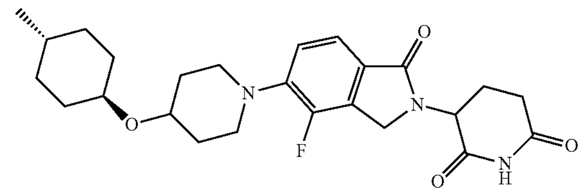
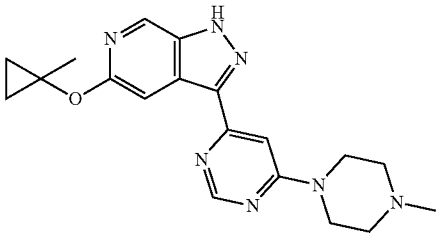
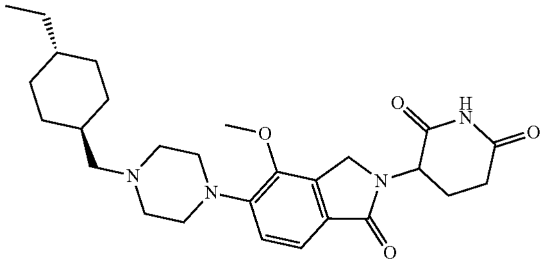
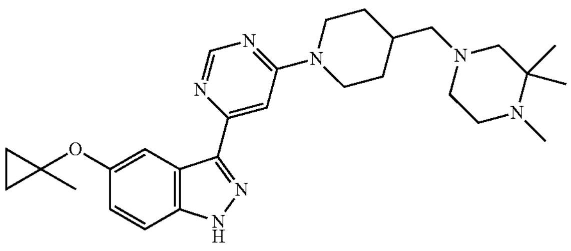
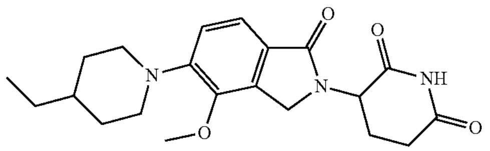
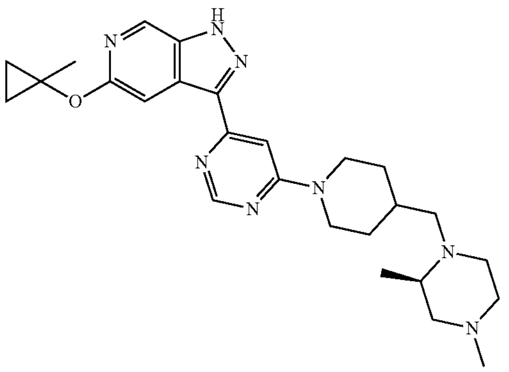
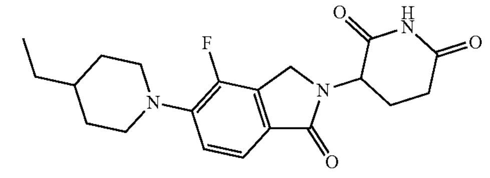

-continued
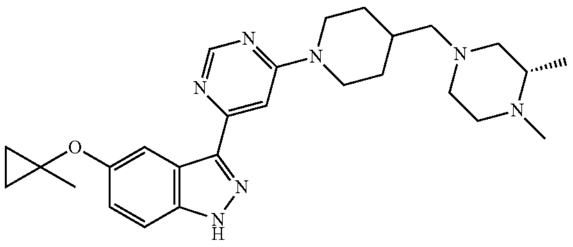
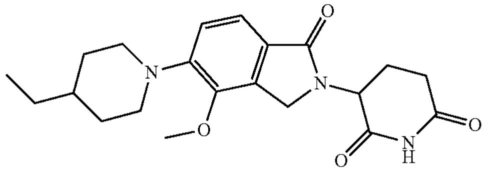
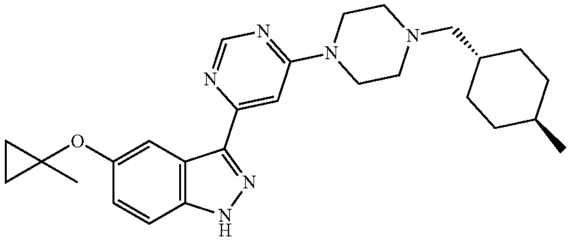
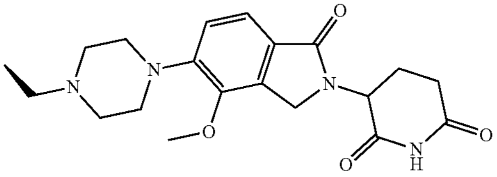
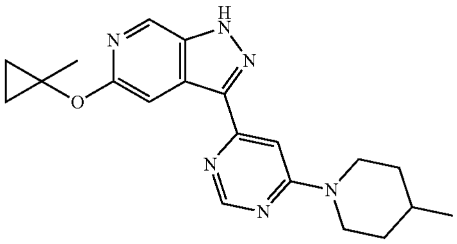
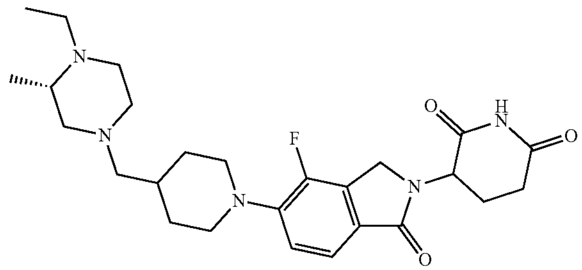
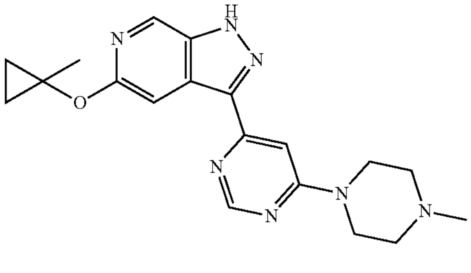
-continued
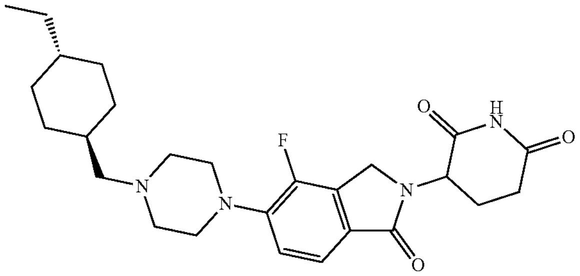
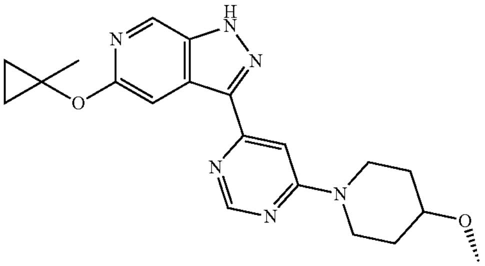
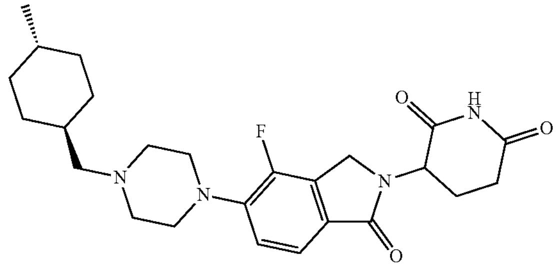
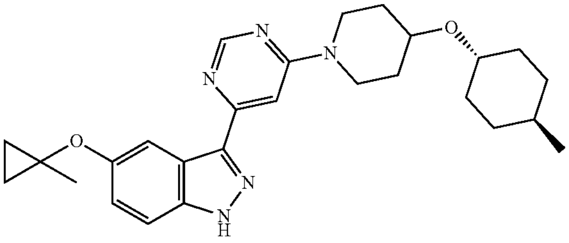
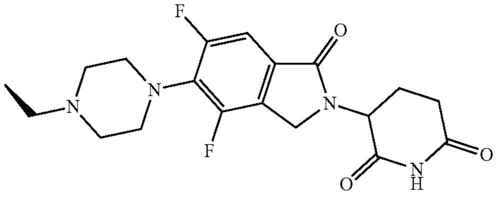
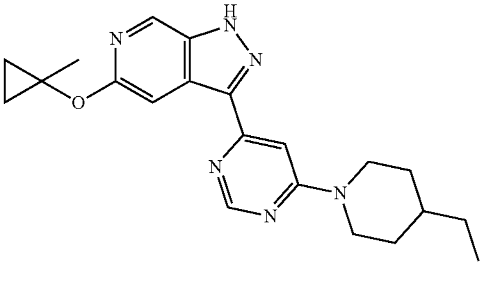

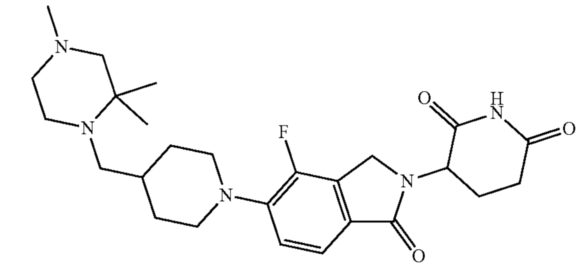
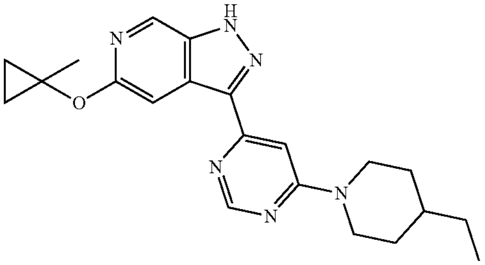
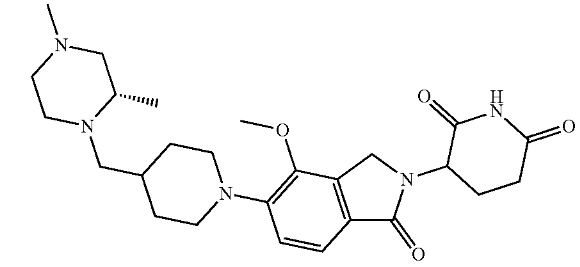
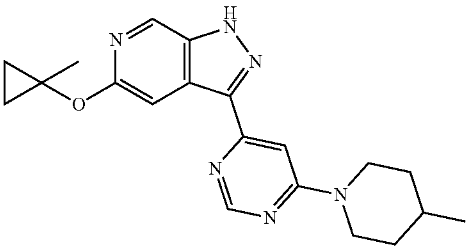
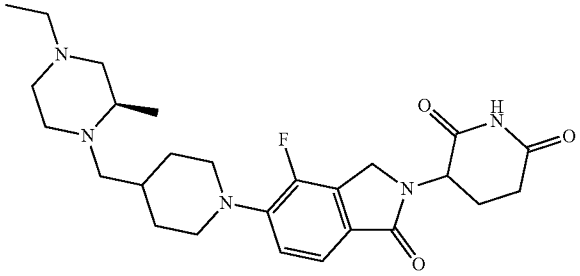
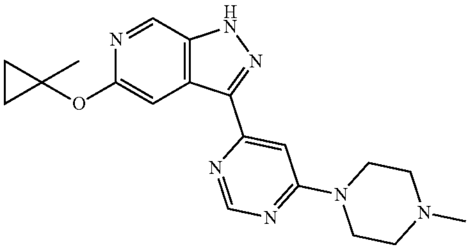
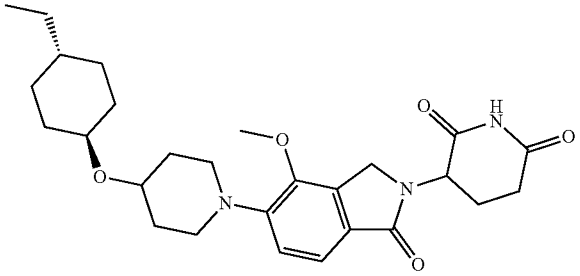
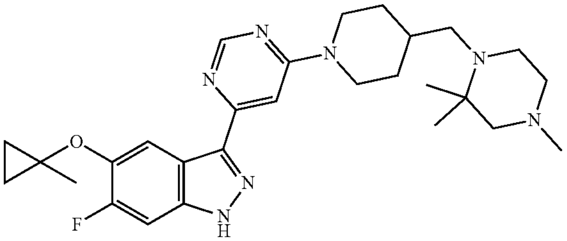
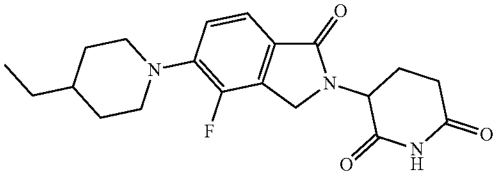
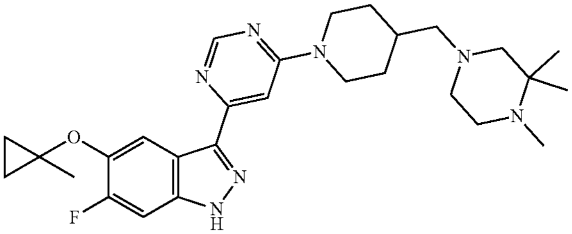
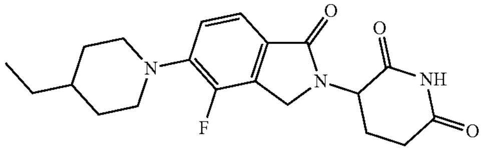
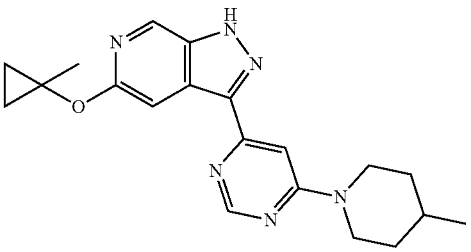
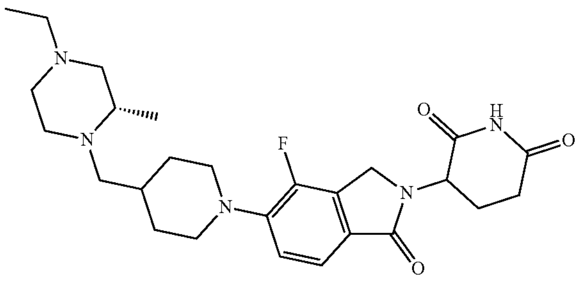

-continued
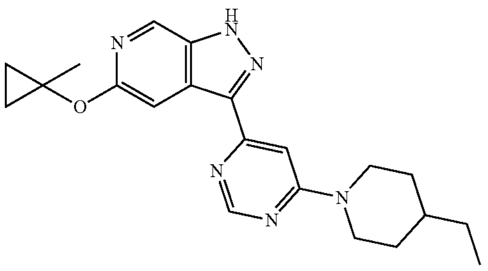
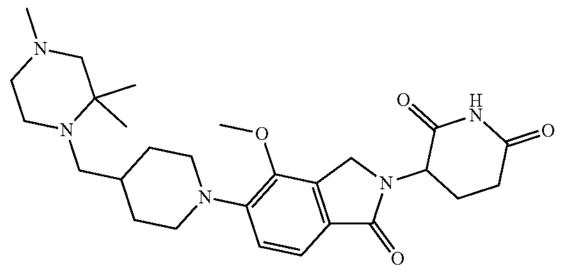
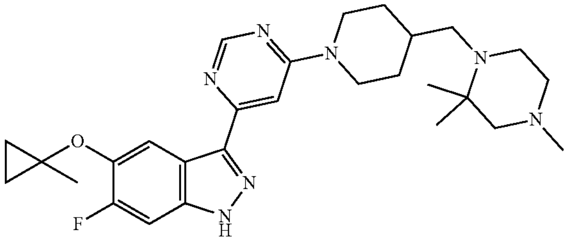
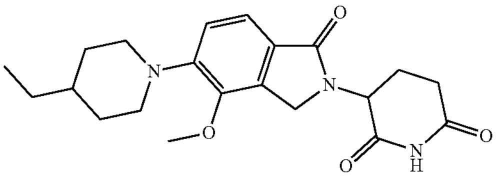
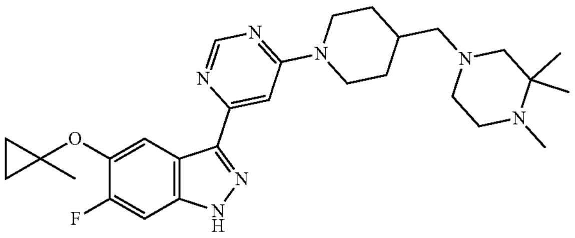
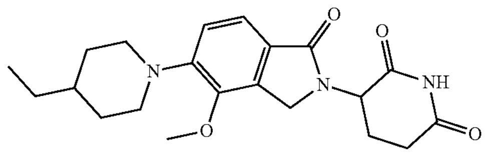
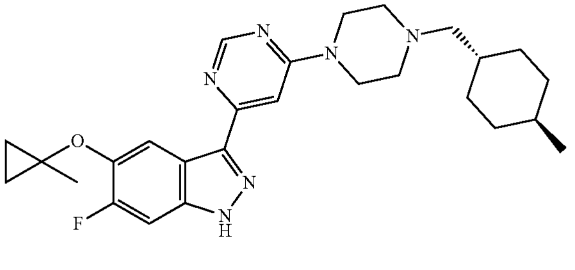
-continued
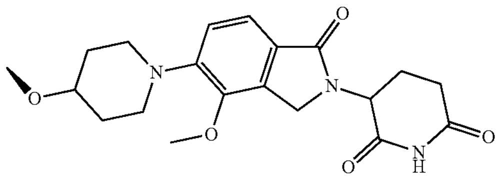
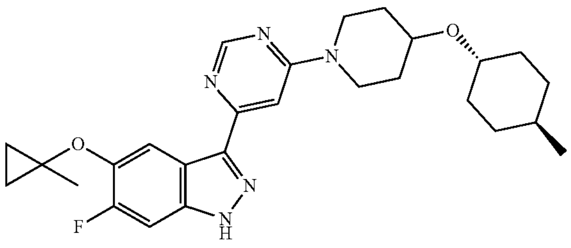
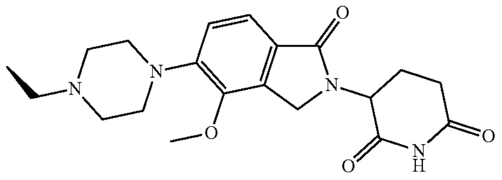
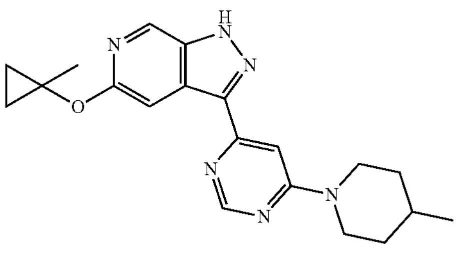
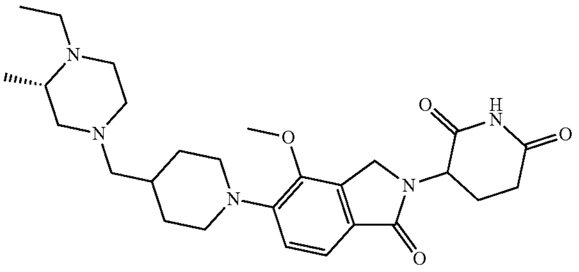
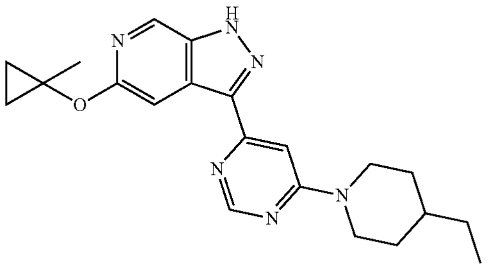
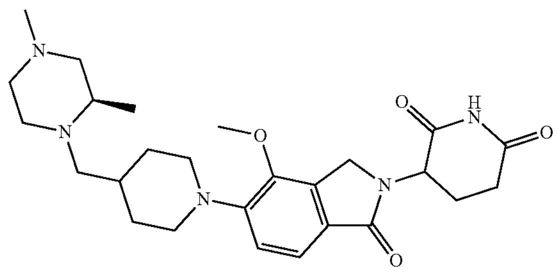

-continued
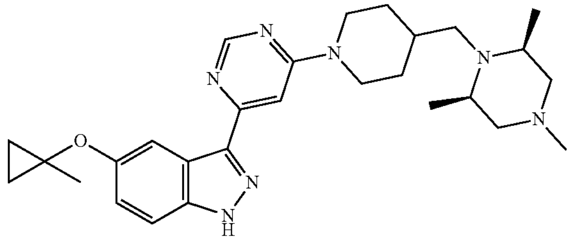
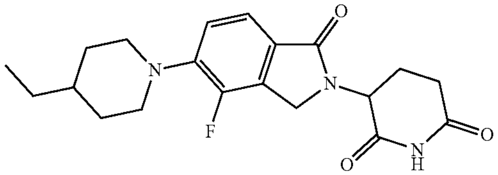
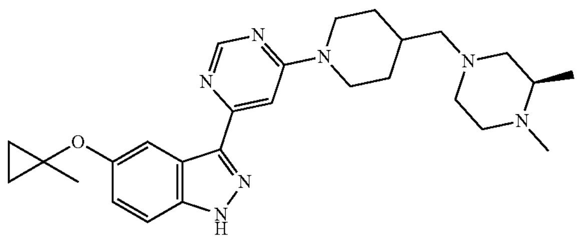
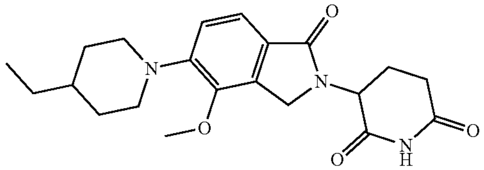
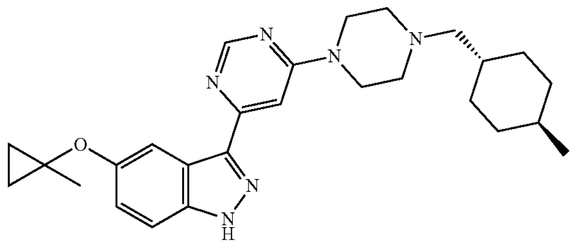
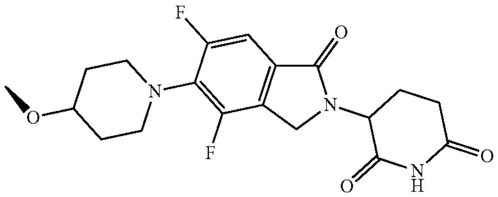
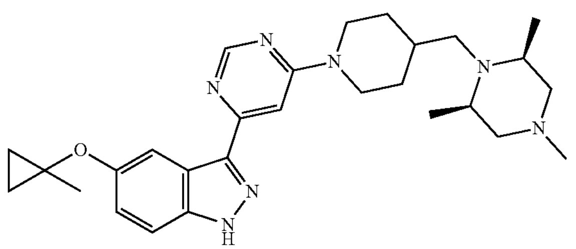
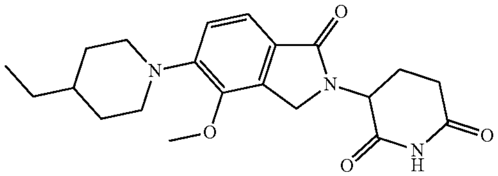
-continued
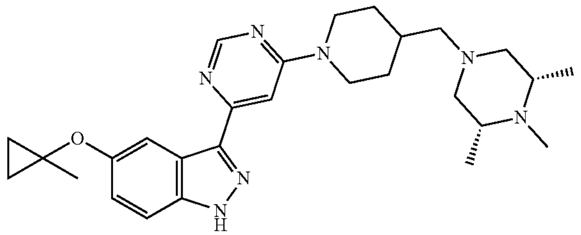
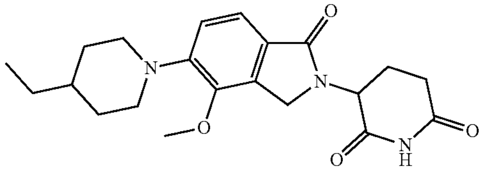
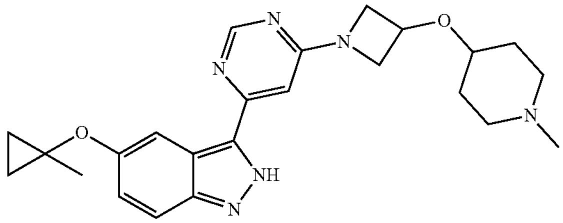
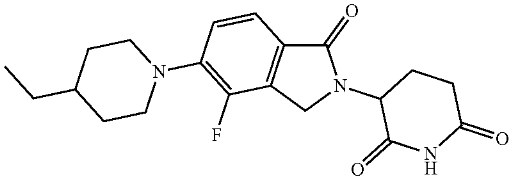
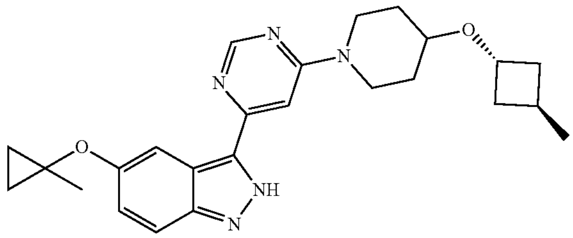
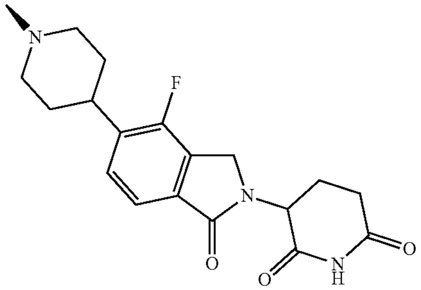
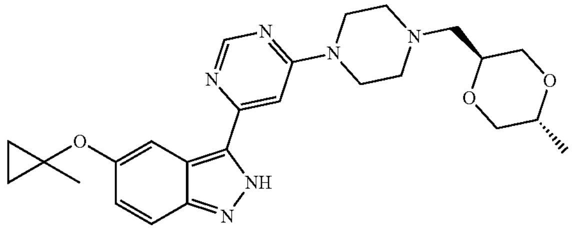

-continued
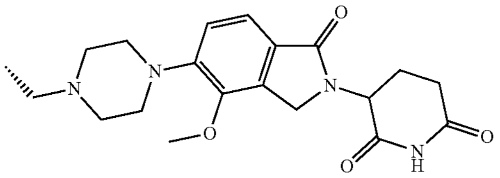
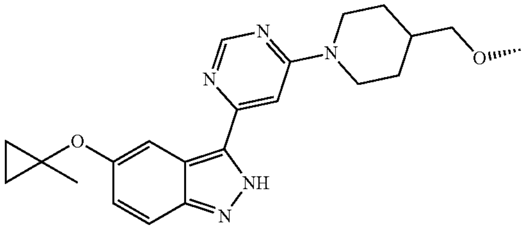
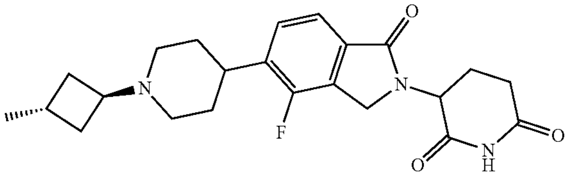
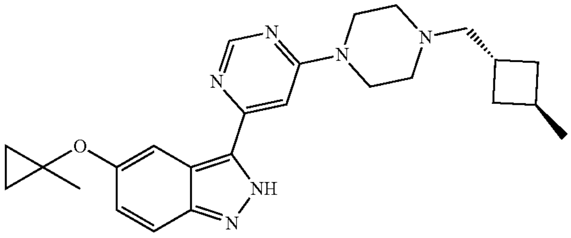
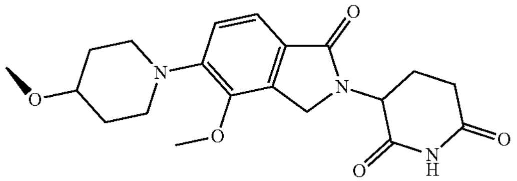
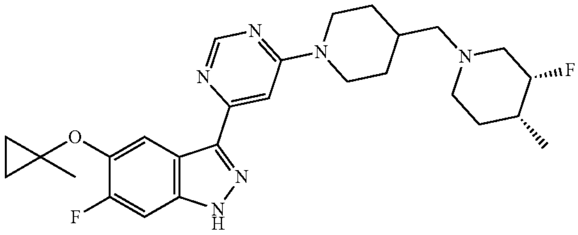
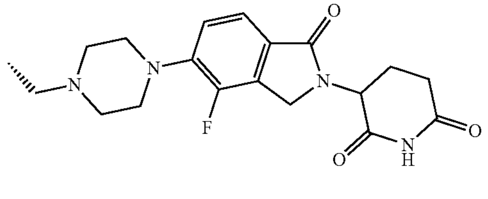
-continued
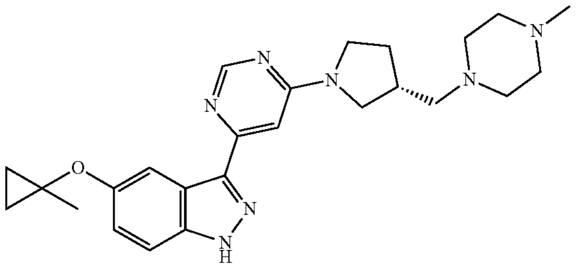
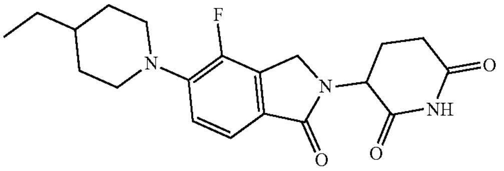
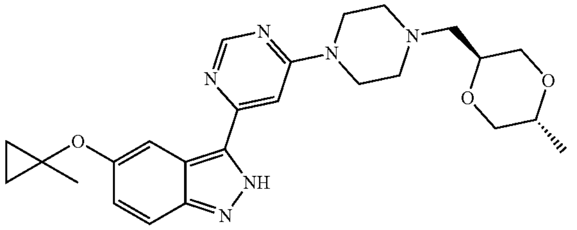
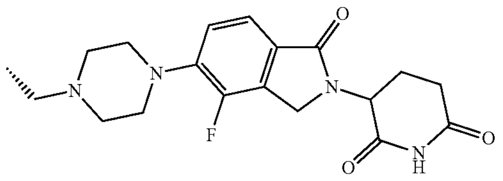
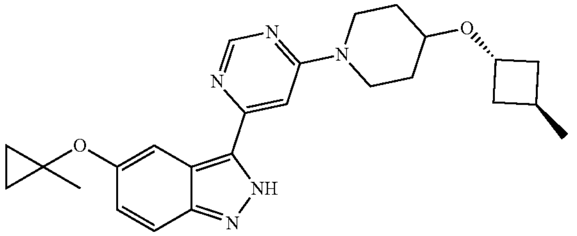
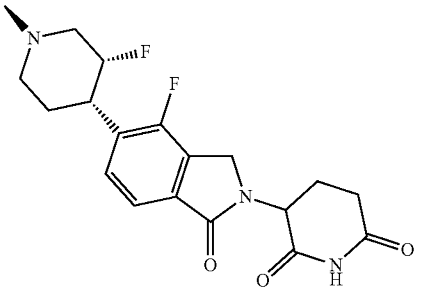
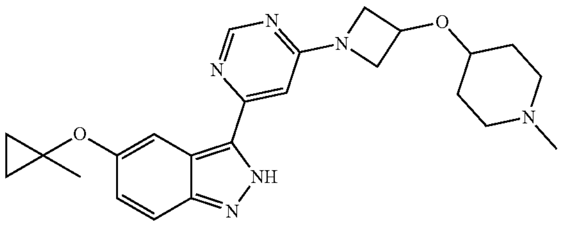

-continued
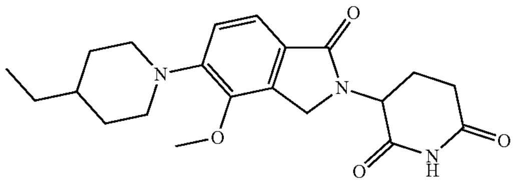
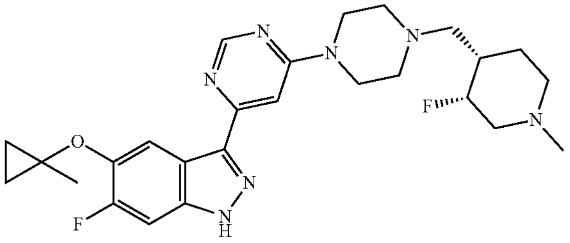
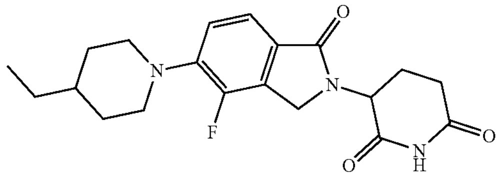
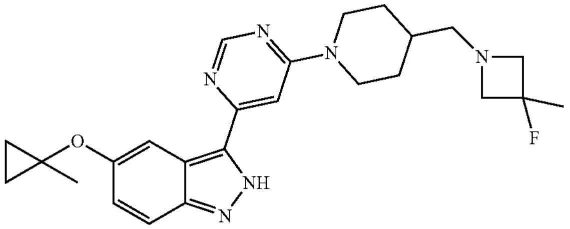
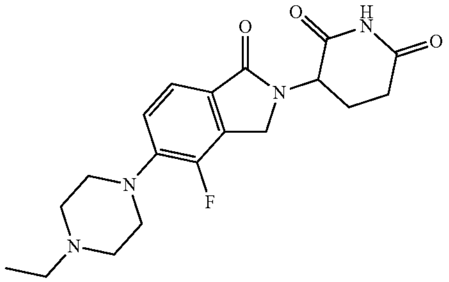
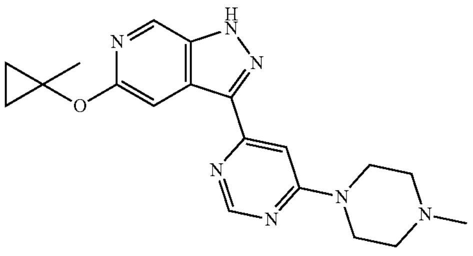
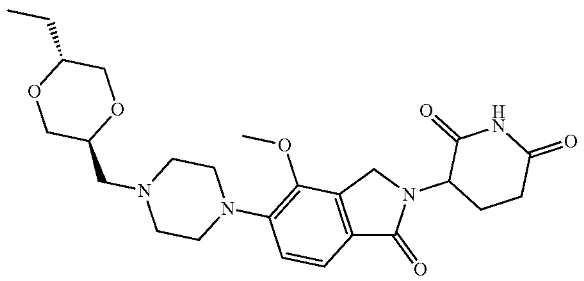
-continued
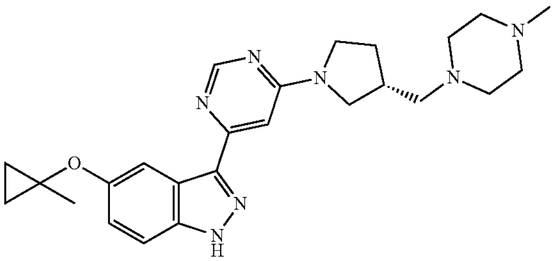
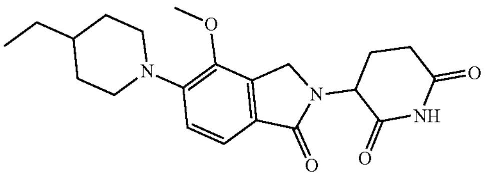
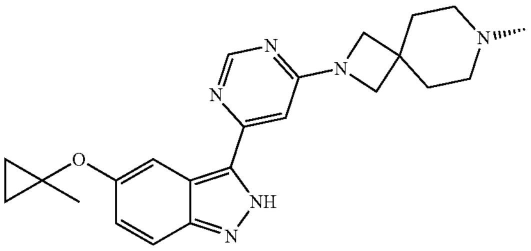
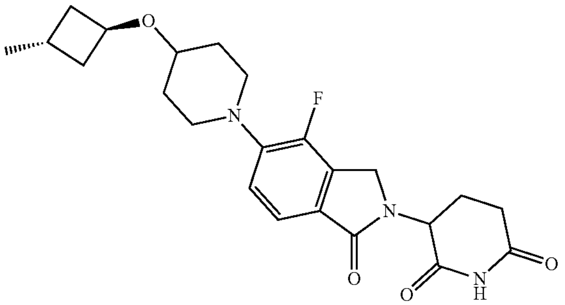
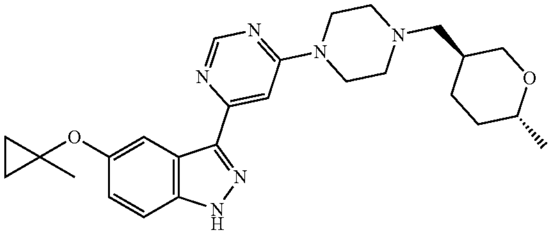
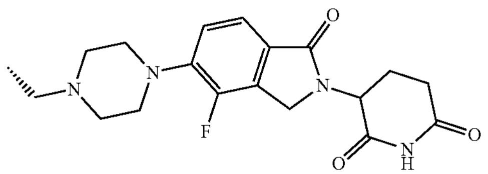
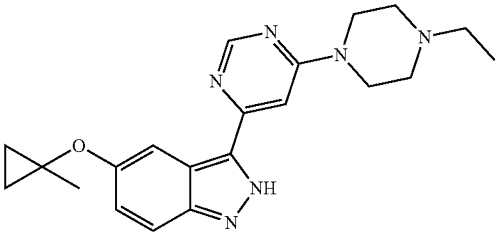

-continued
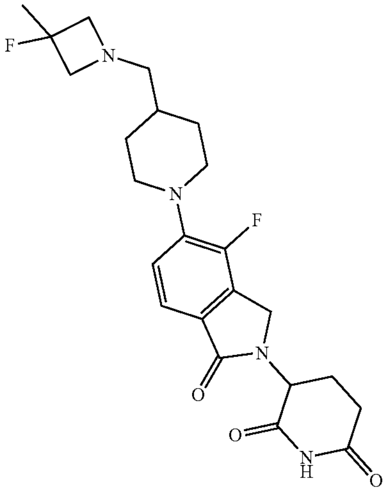
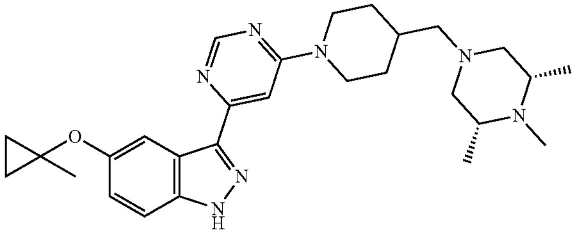
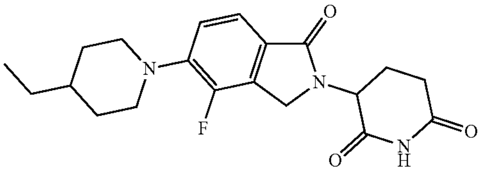
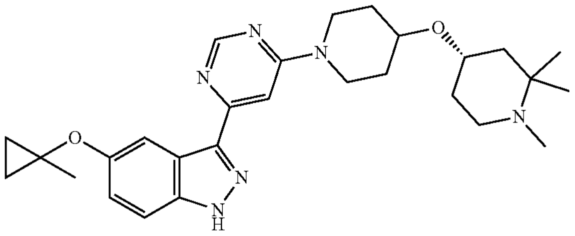
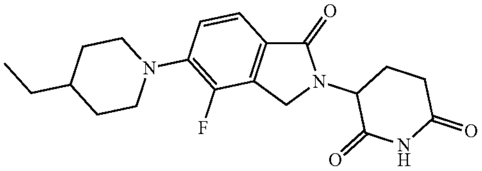
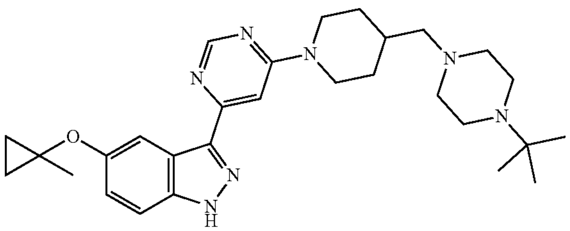
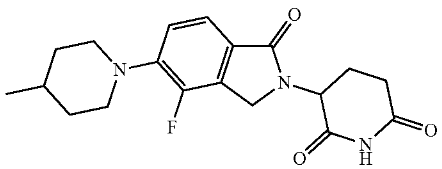
-continued
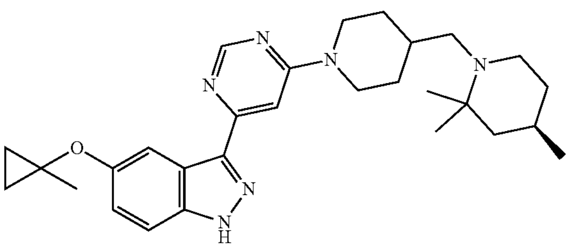
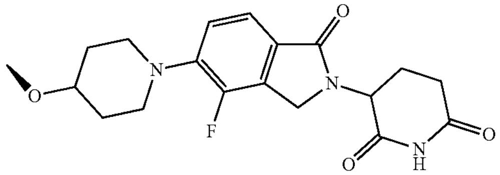
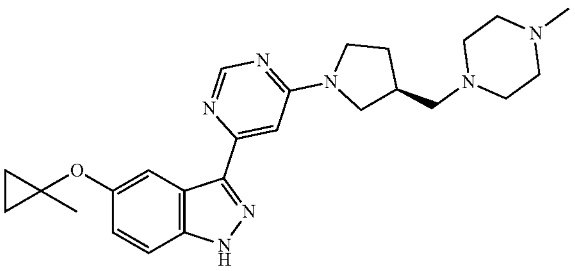
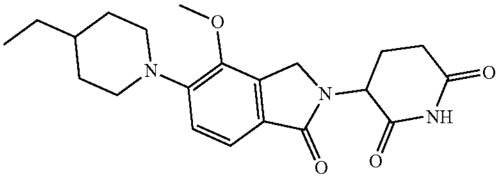
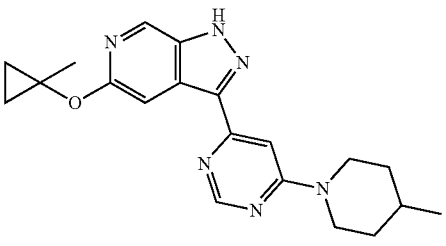
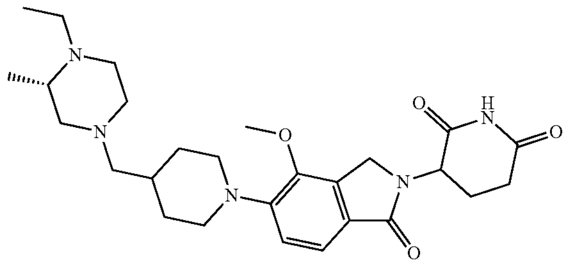
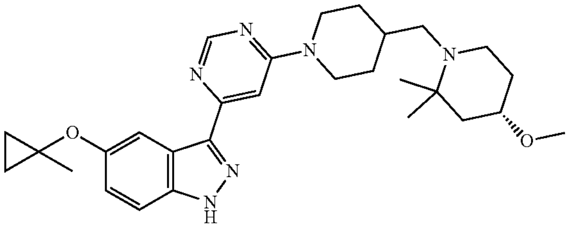

-continued
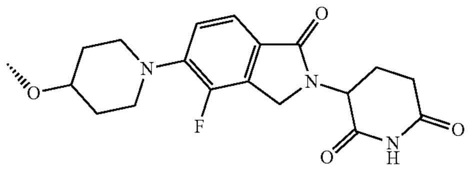
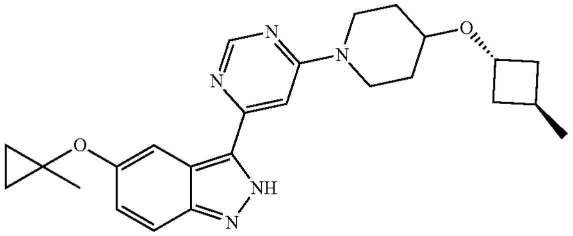
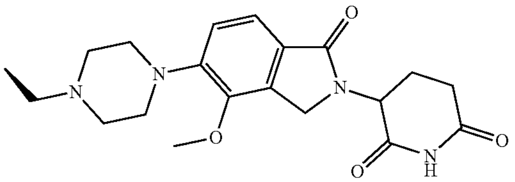
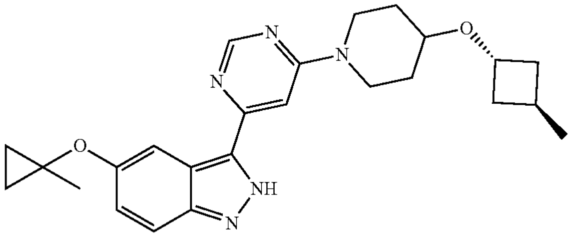
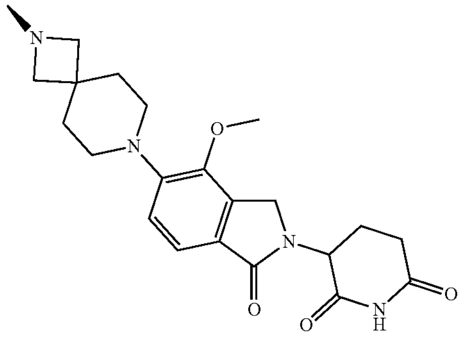
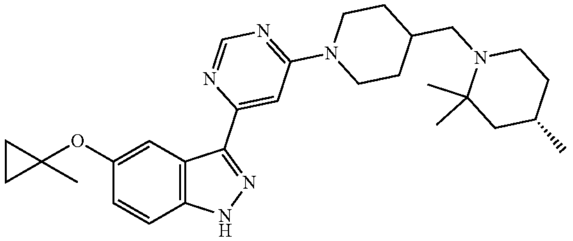
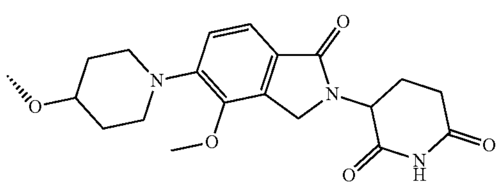
-continued
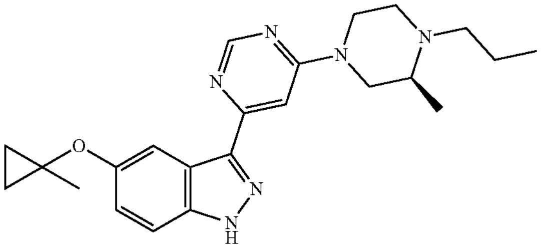
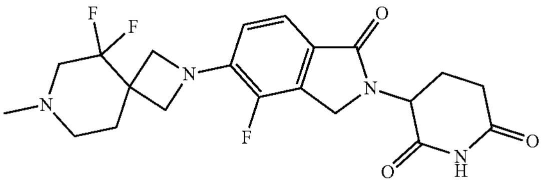
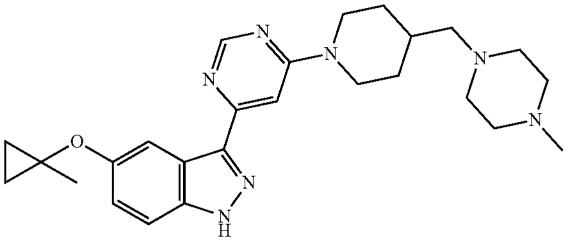
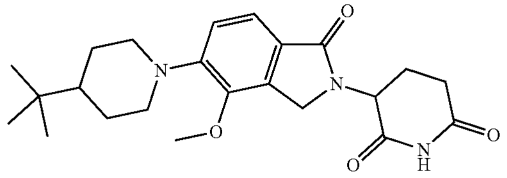
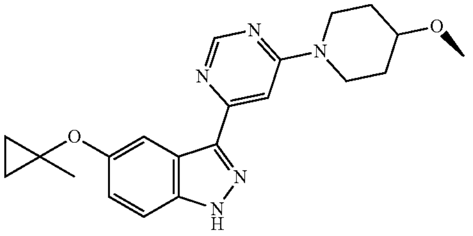
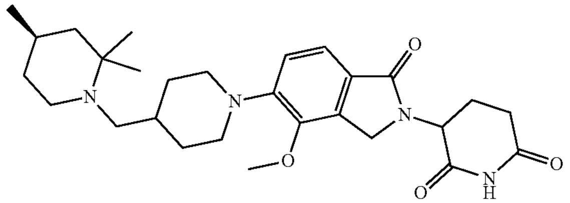
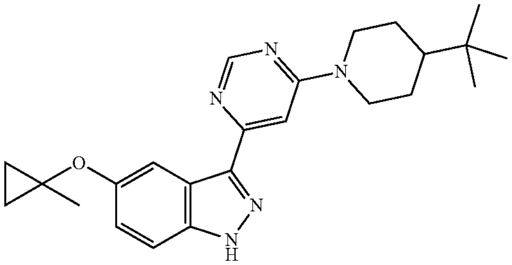

-continued
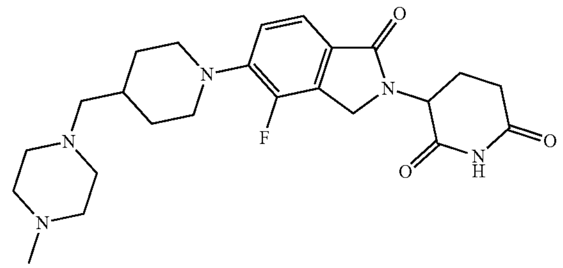
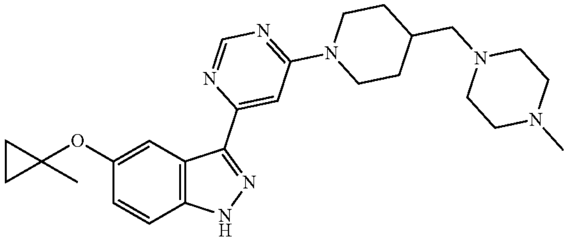
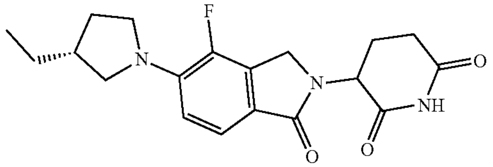
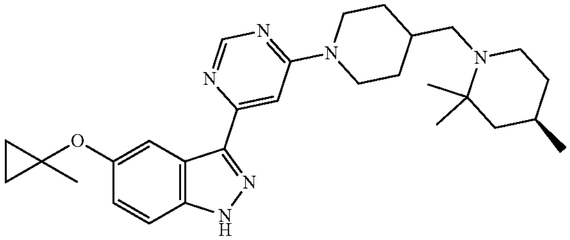
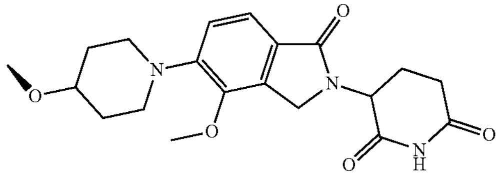
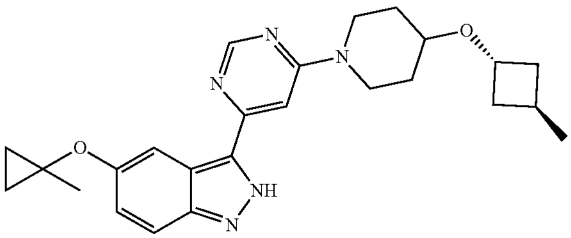
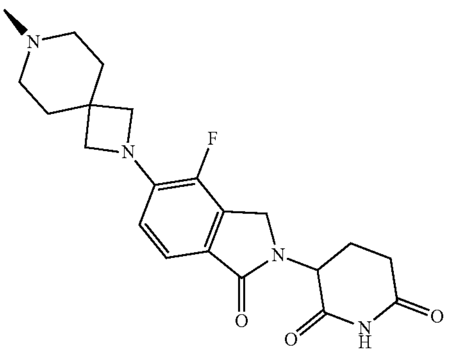
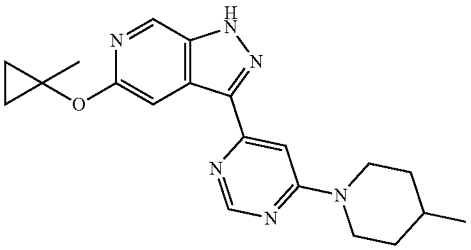
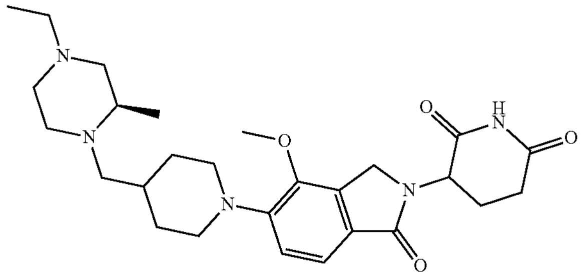
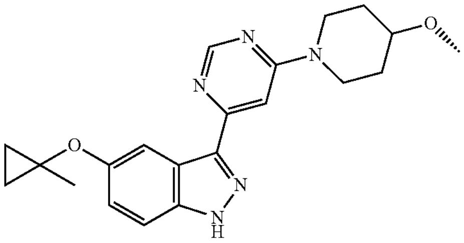
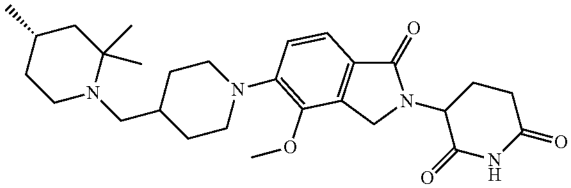
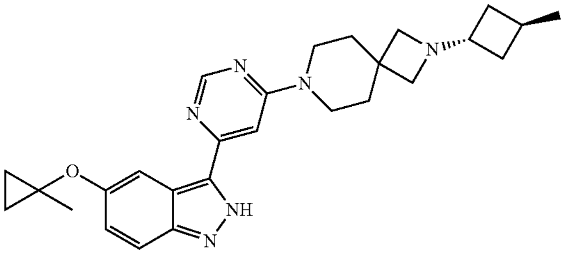
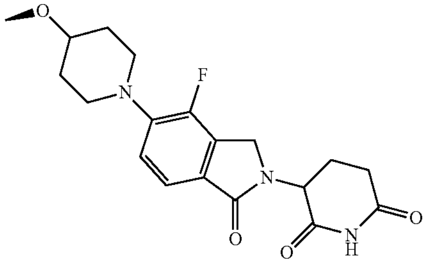
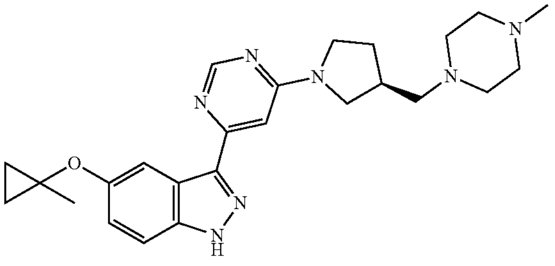

-continued
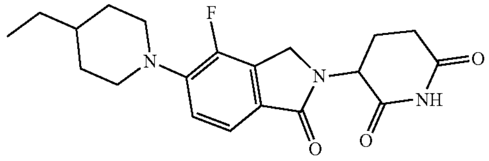
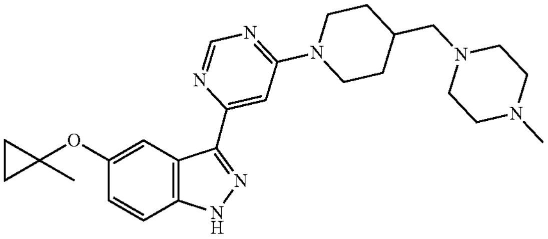
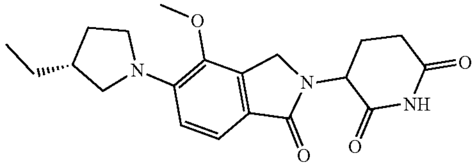
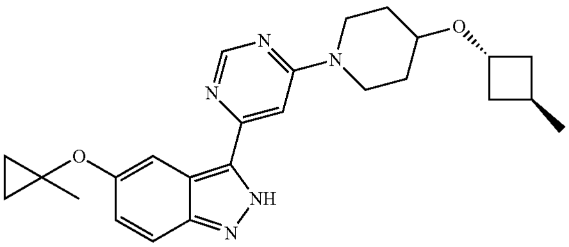
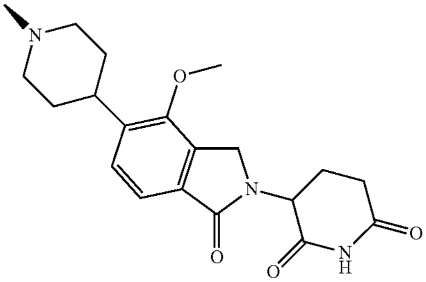
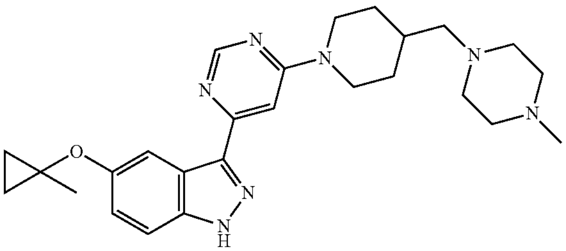
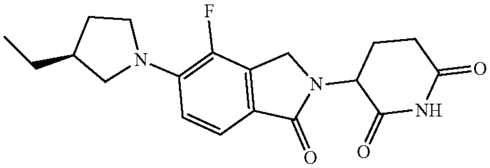
-continued
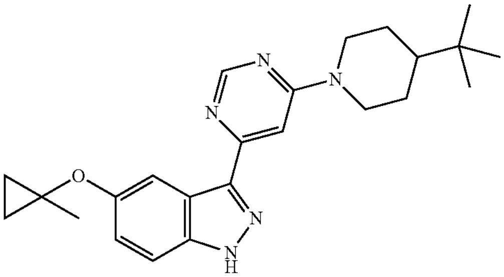
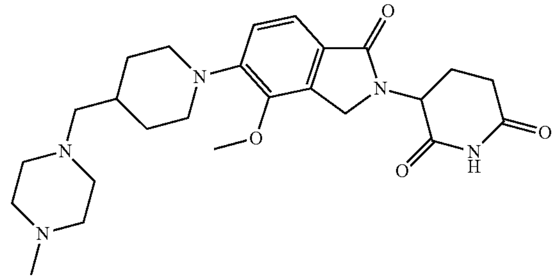
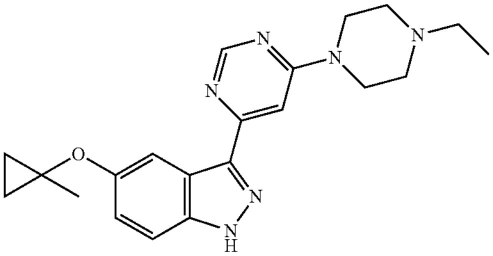
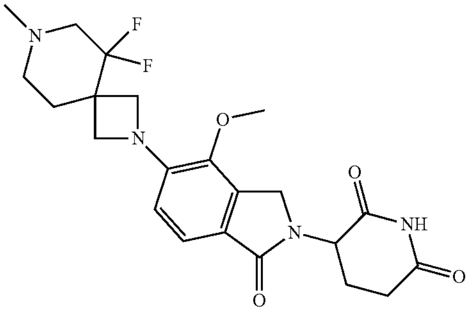
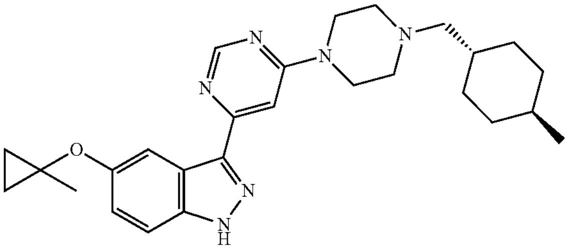
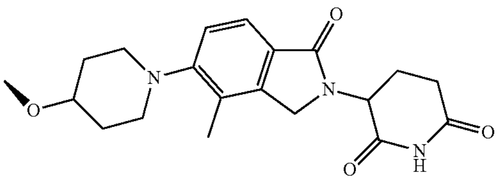

-continued
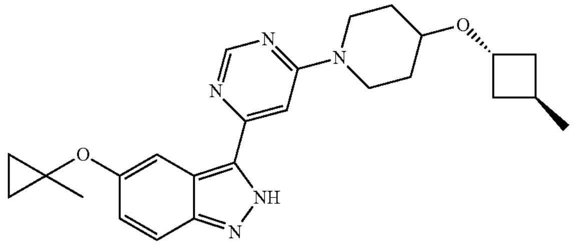
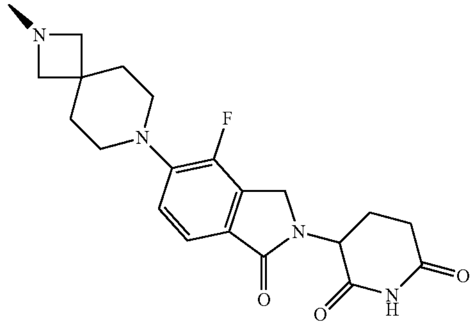
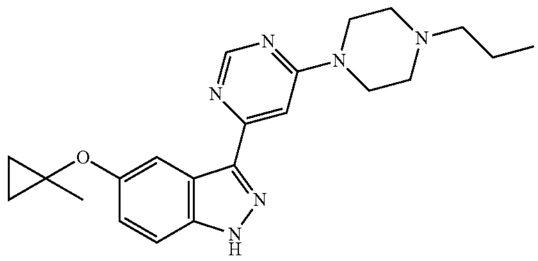
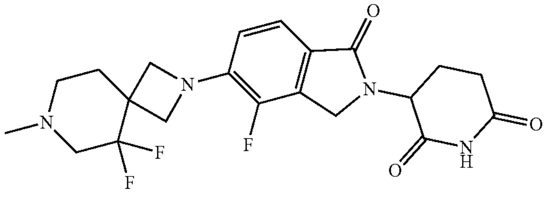
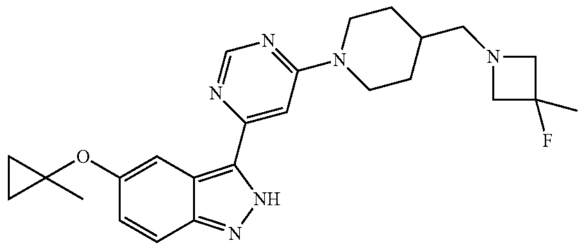
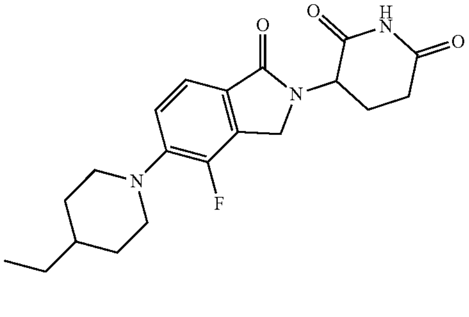
-continued
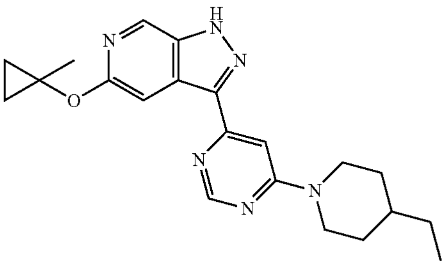
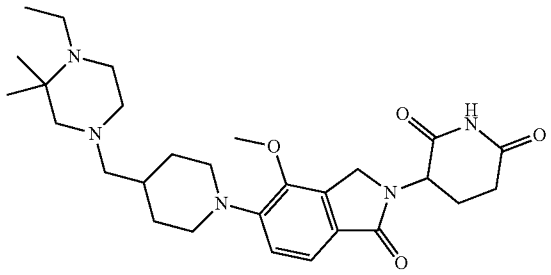
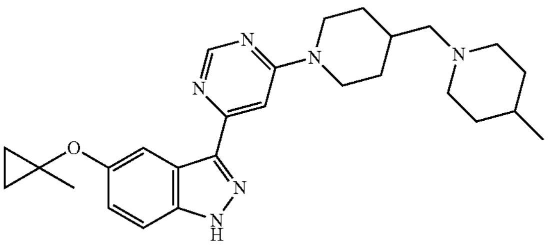
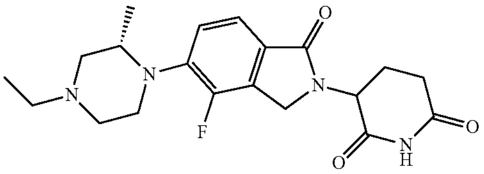
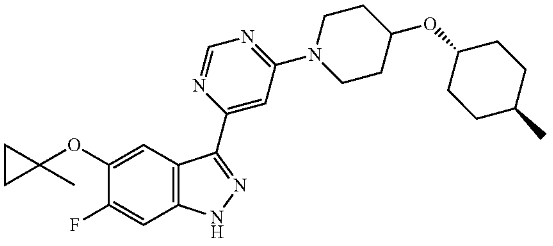
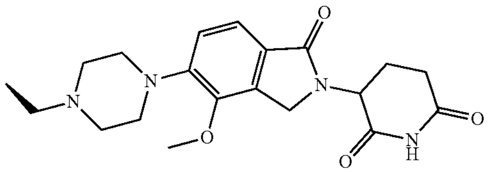
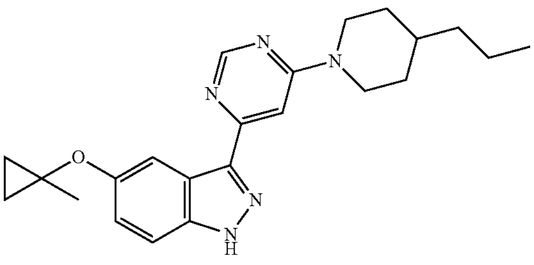

-continued
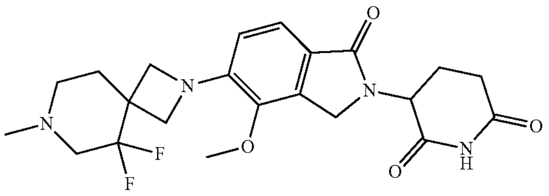
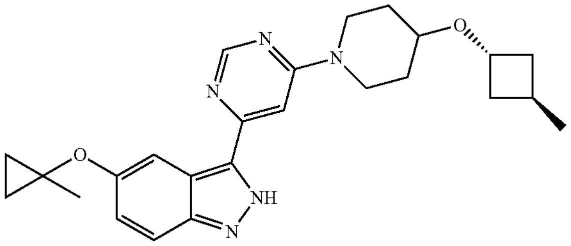
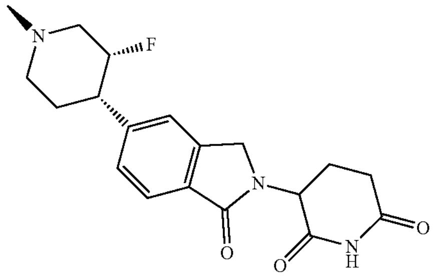
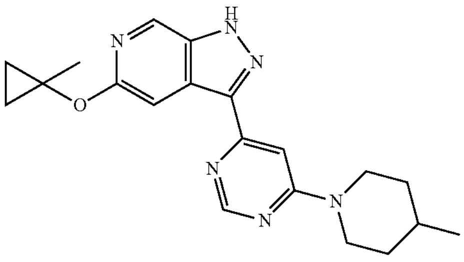
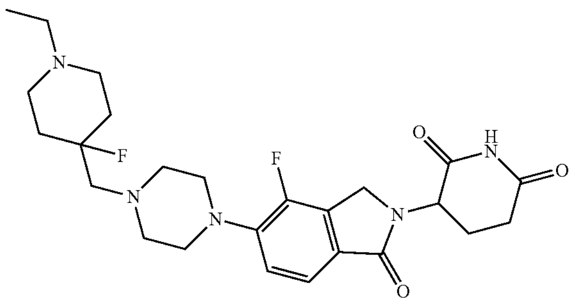
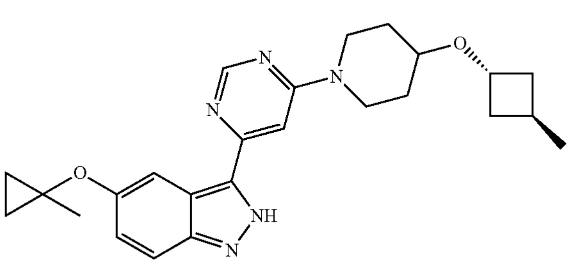
-continued
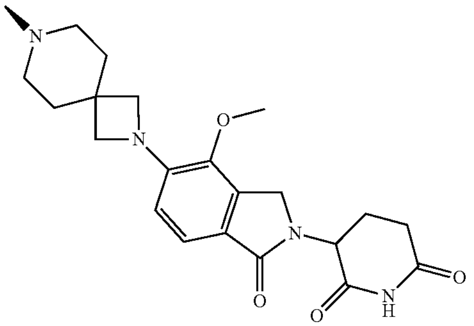
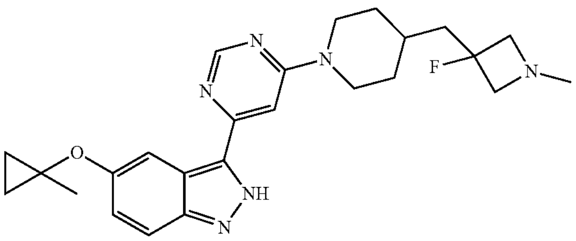
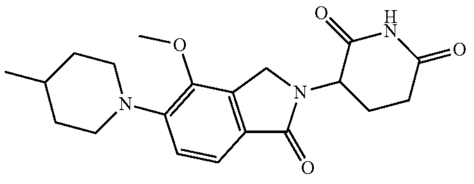
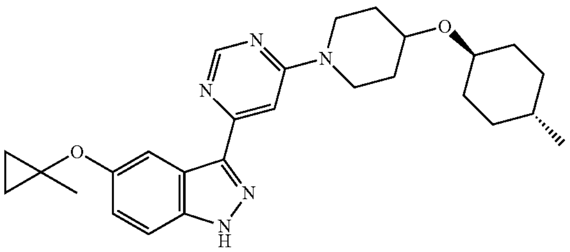
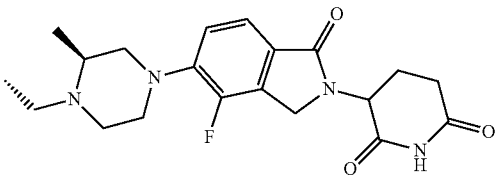
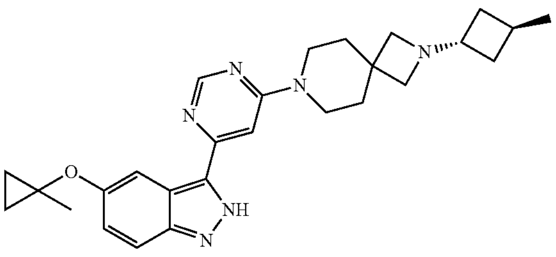
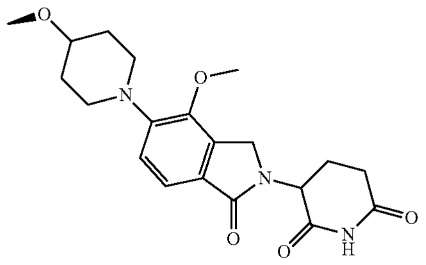

-continued
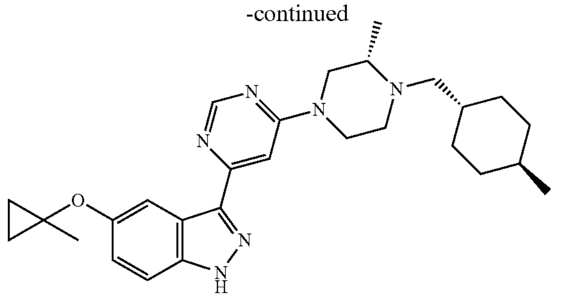
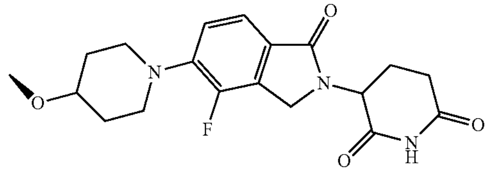
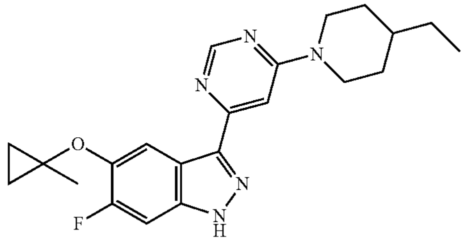
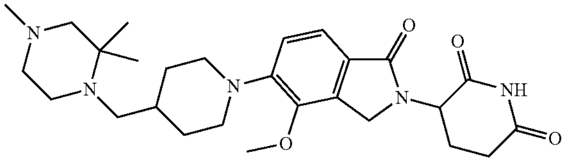
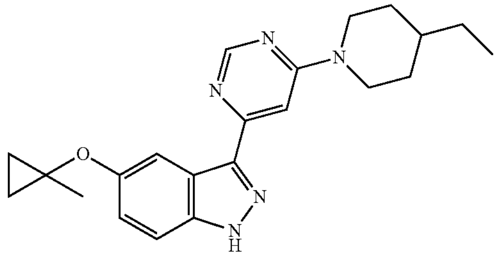
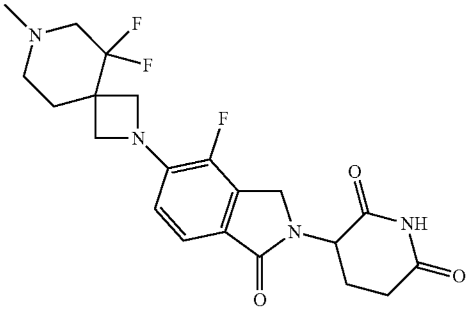
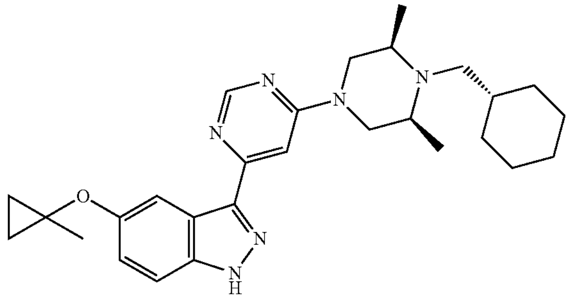
-continued
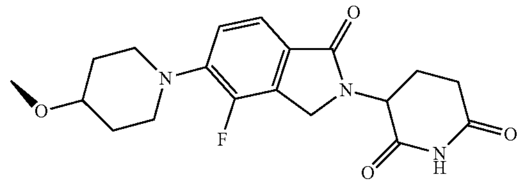
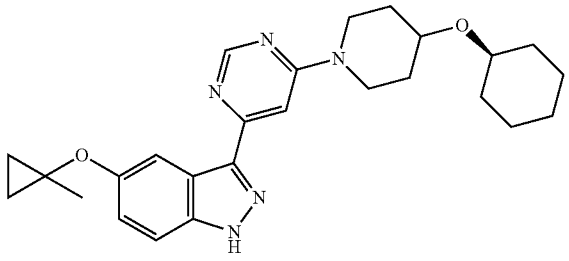
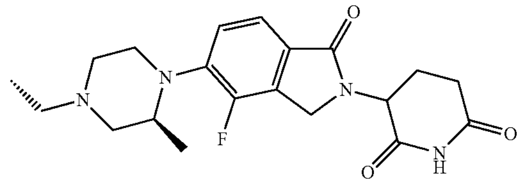
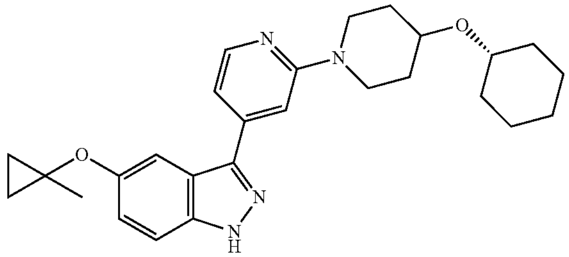
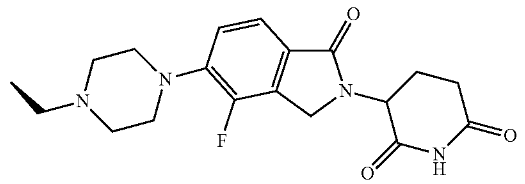
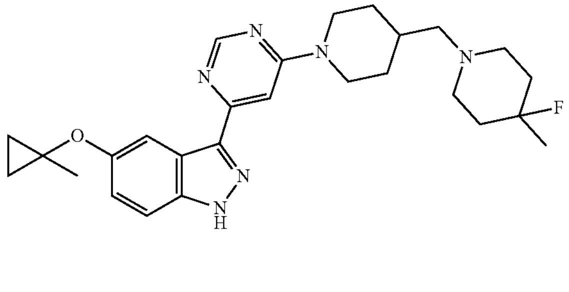
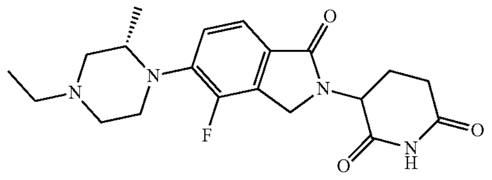

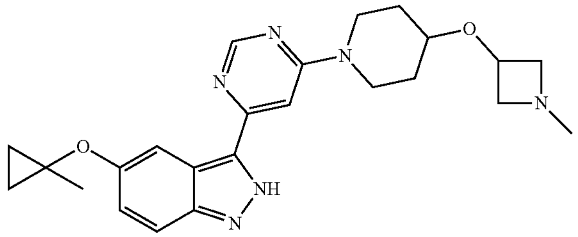
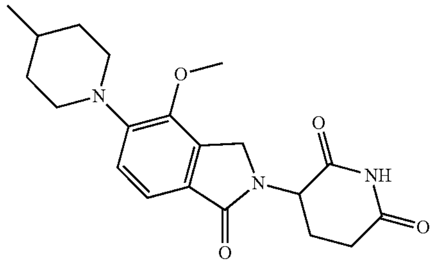
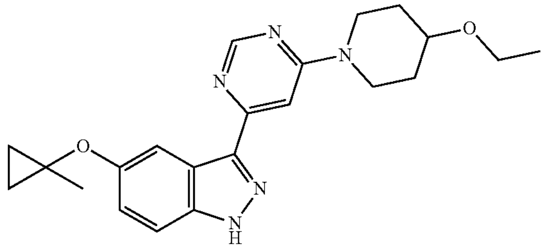
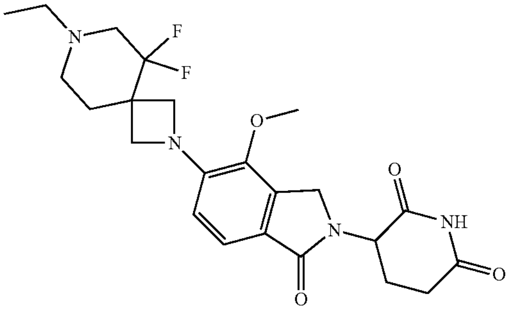
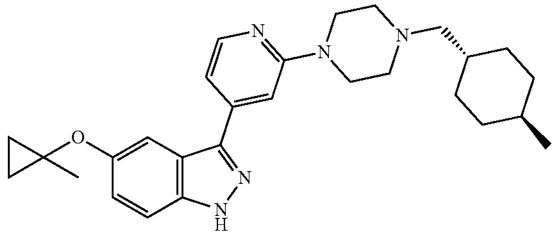
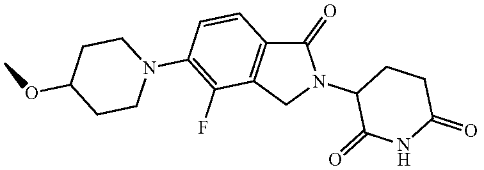
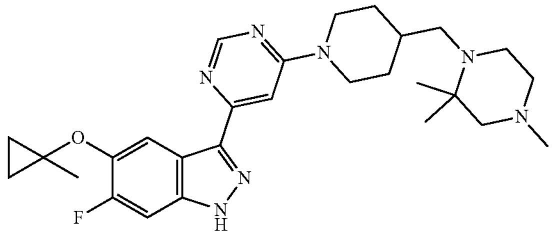
-continued
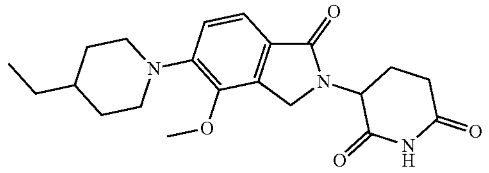
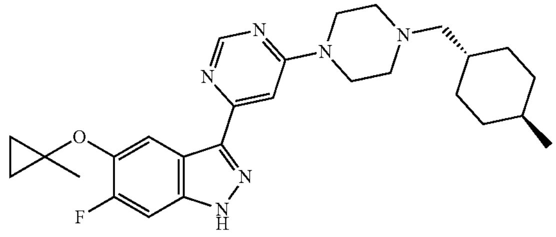
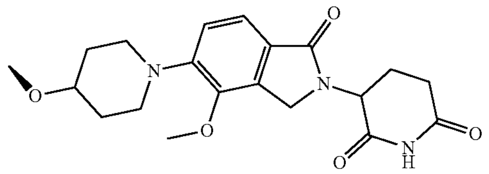
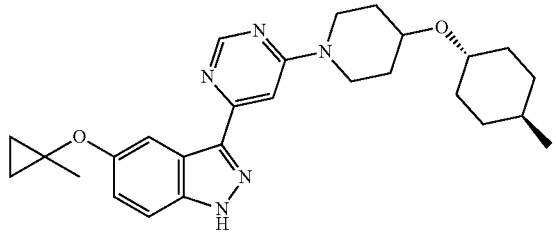
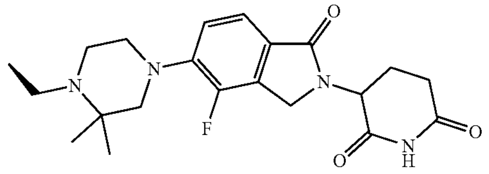
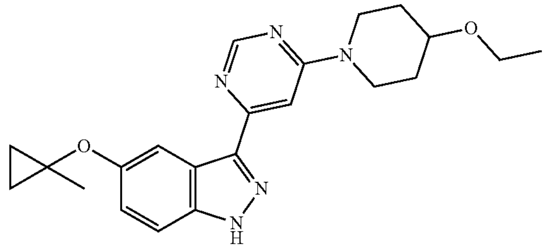
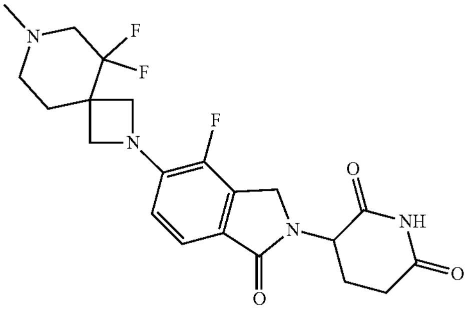

-continued
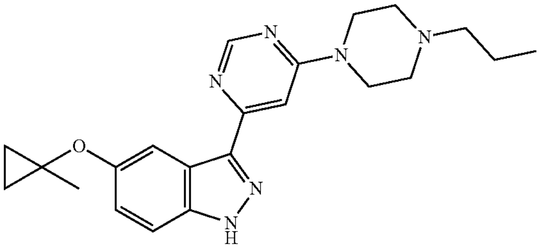
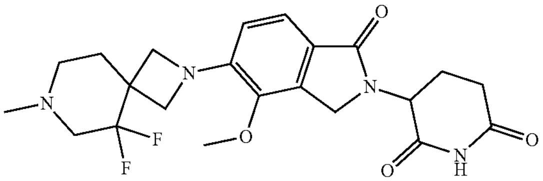
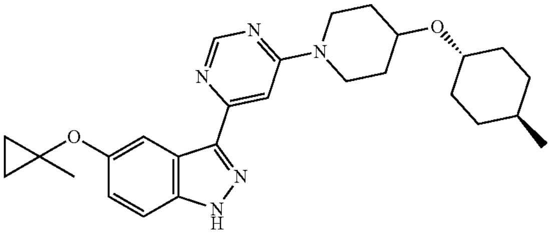
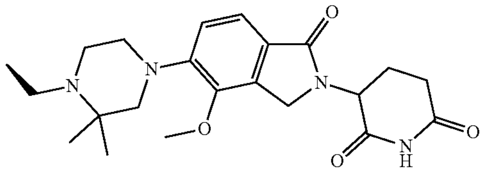
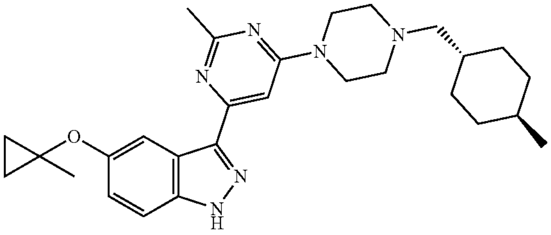
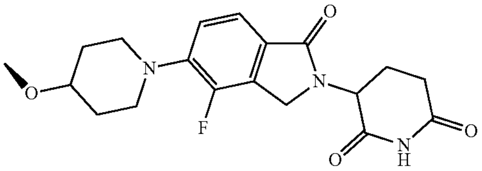
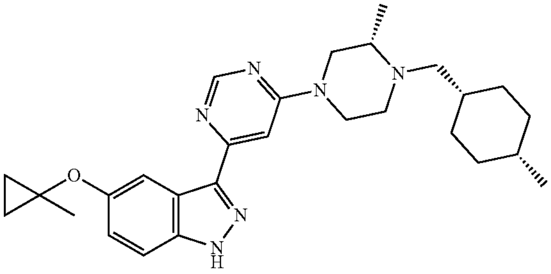
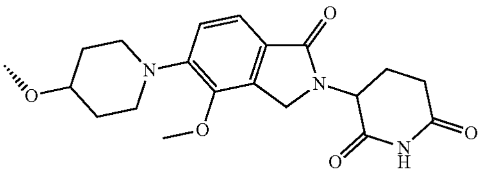
-continued
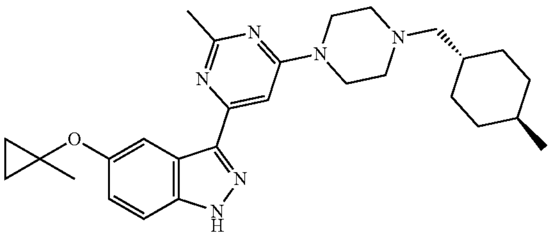
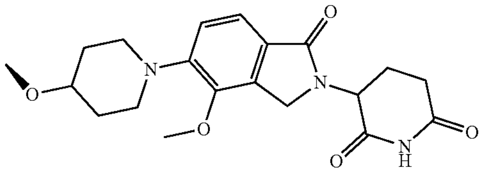
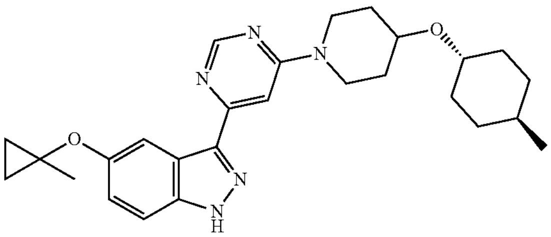
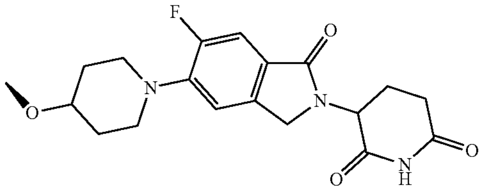
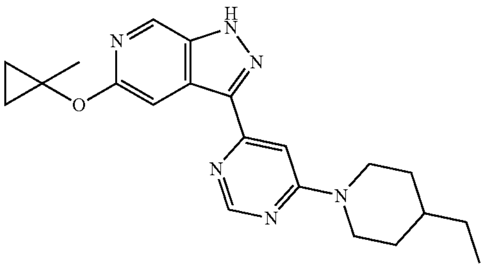
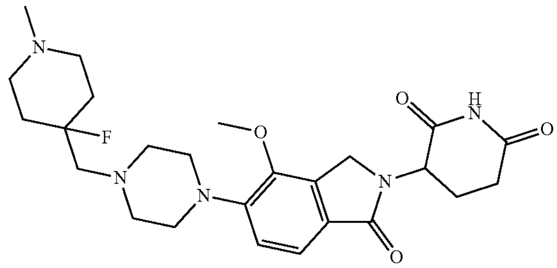
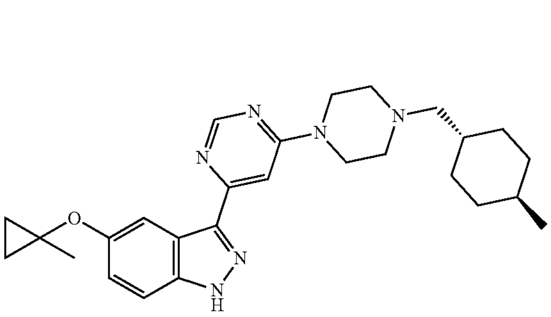

-continued
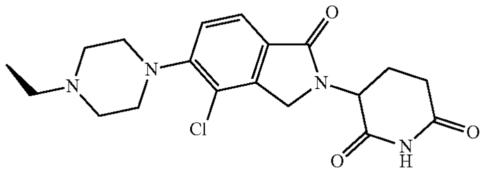
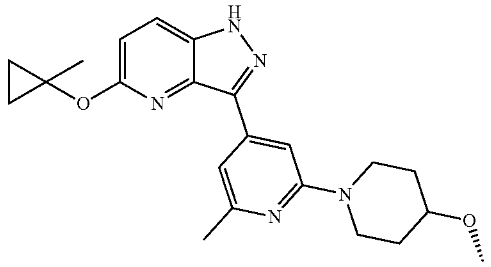
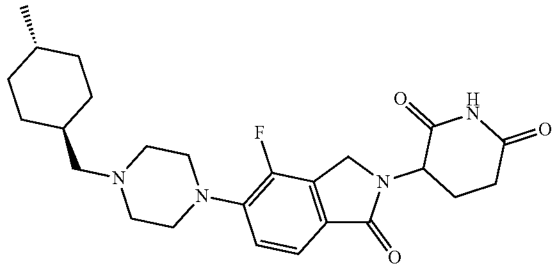
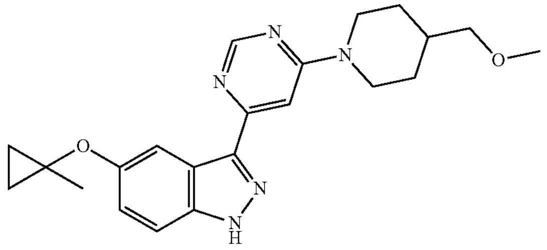
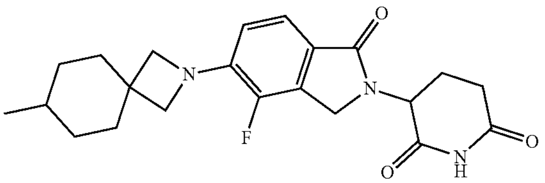
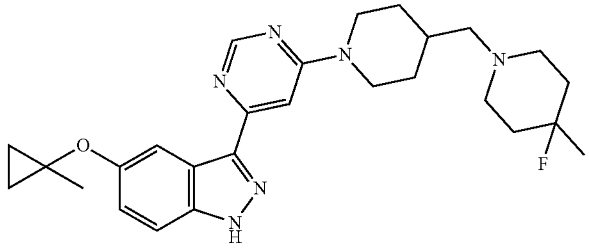
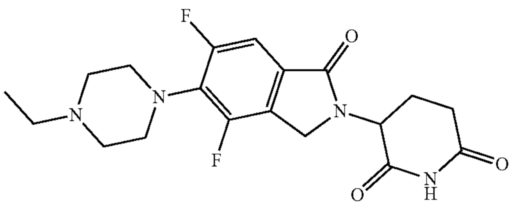
-continued
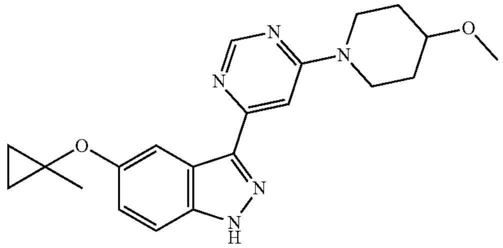
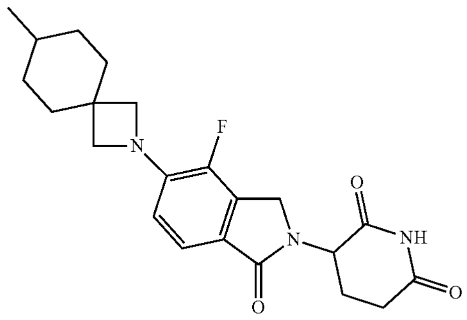
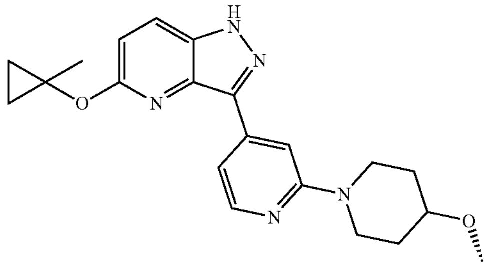
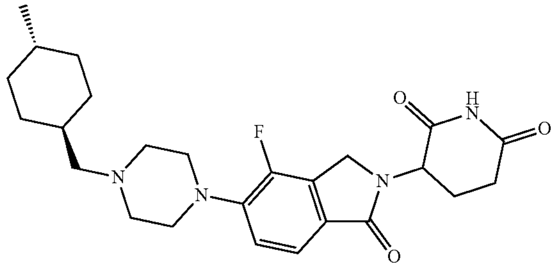
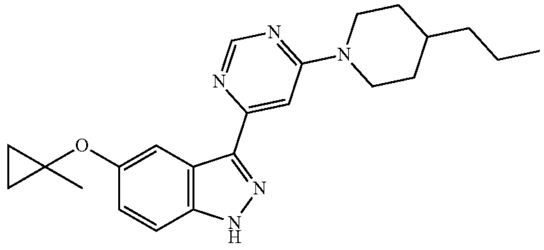
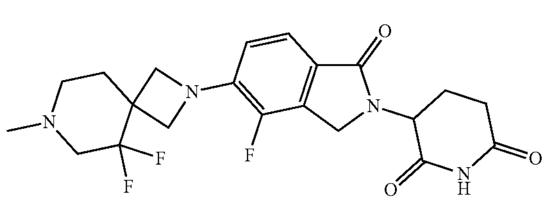

-continued
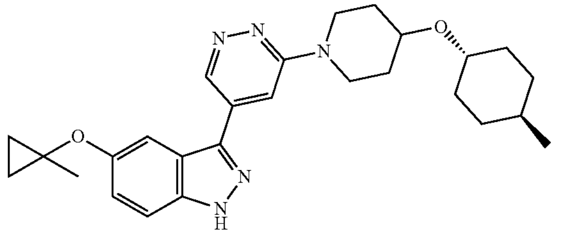
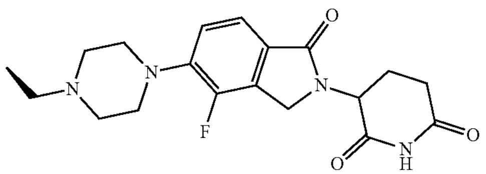
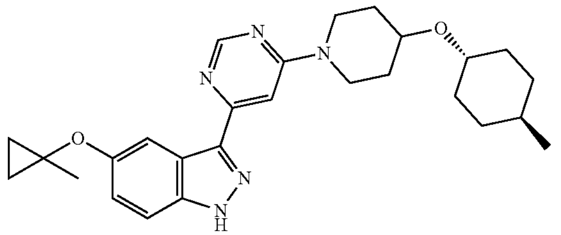
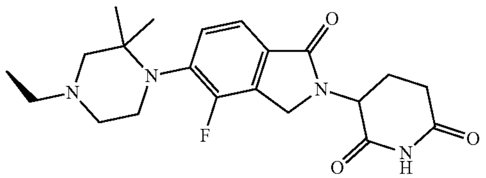
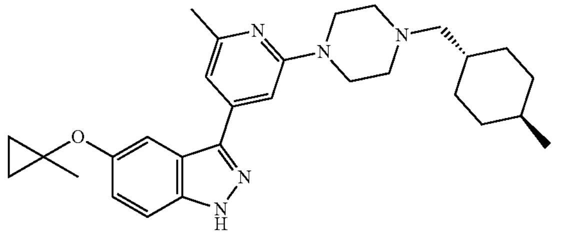
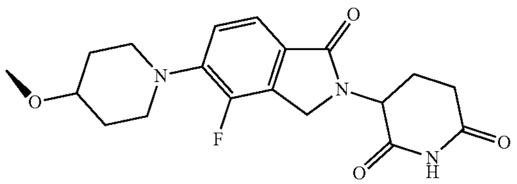
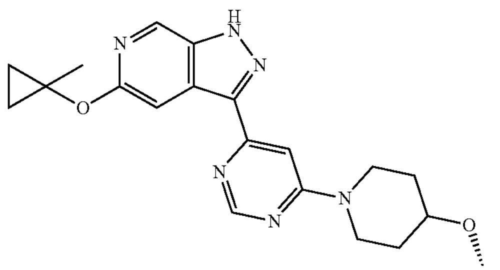
-continued
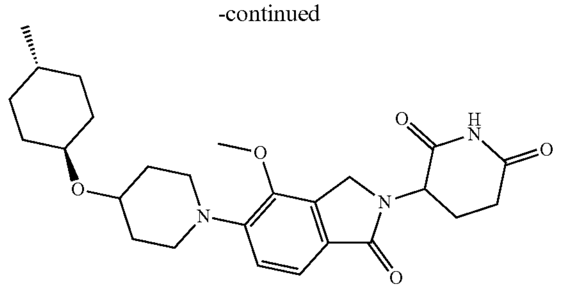
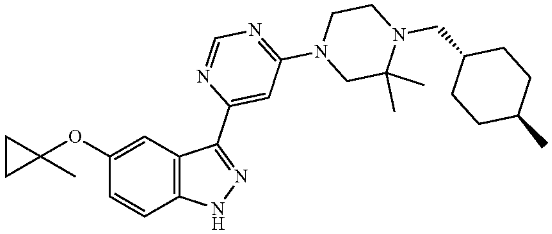
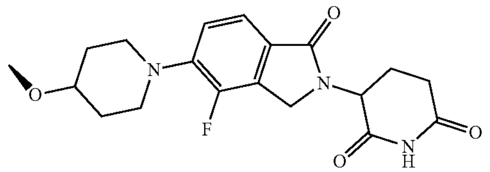
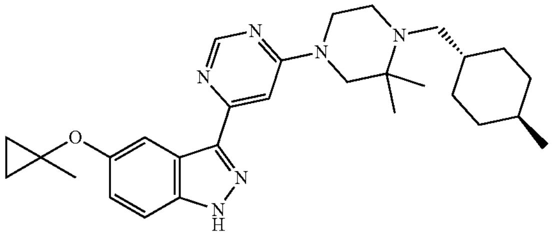
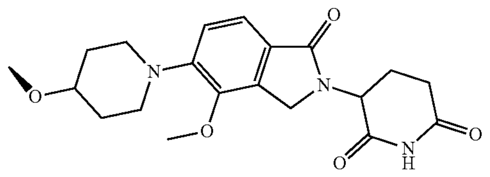
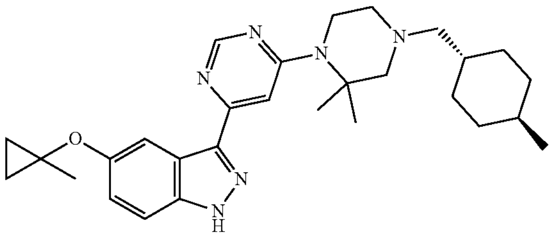
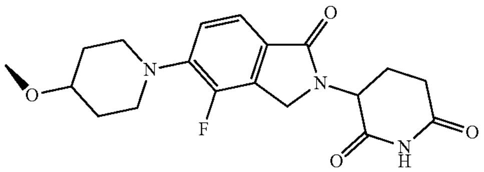
or
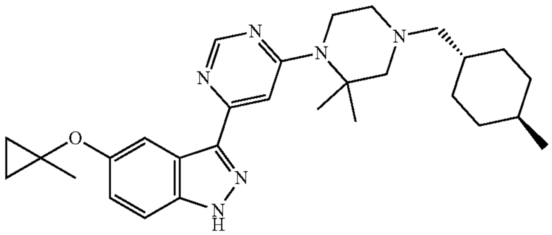

-continued

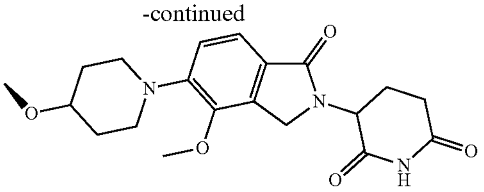

or a pharmaceutically acceptable salt thereof.

2. A compound, wherein the compound is:

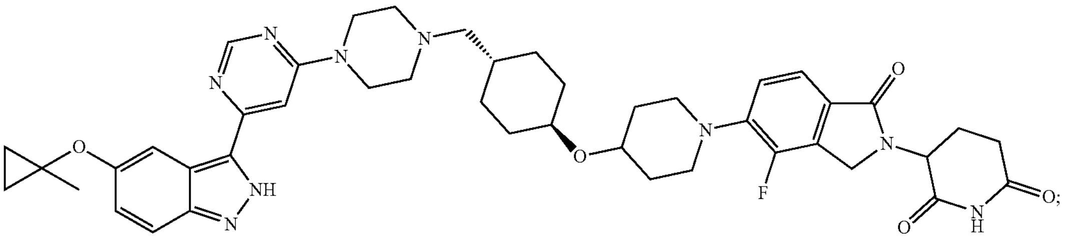 [SMILES: CC1(Oc2ccc3n[nH]c(-c4cc(N5CCN(C[C@H]6CC[C@H](OC7CCN(c8ccc9c(c8F)CN(C8CCC(=O)NC8=O)C9=O)CC7)CC6)CC5)ncn4)c3c2)CC1]

or a pharmaceutically acceptable salt thereof.

3. A pharmaceutical composition comprising a compound of claim 1, or a pharmaceutically acceptable salt thereof, and a pharmaceutically acceptable excipient.

4. A pharmaceutical composition comprising the compound of claim 2, or a pharmaceutically acceptable salt thereof, and a pharmaceutically acceptable excipient.

5. The pharmaceutical composition of claim 3, wherein the composition further comprises an additional bioactive agent.

6. The pharmaceutical composition of claim 4, wherein the composition further comprises an additional bioactive agent.

7. The pharmaceutical composition of claim 5, wherein the additional bioactive agent is an anti-inflammatory agent, a chemotherapy agent, or an immunomodulatory agent.

8. The pharmaceutical composition of claim 6, wherein the additional bioactive agent is an anti-inflammatory agent, a chemotherapy agent, or an immunomodulatory agent.

9. A method of treating a disease, a disorder, or a symptom causally related to LRRK2 in a subject, comprising administering to the subject a compound, or pharmaceutically acceptable salt thereof, of claim 1, or a pharmaceutical composition comprising a compound of claim 2, or a pharmaceutically acceptable salt thereof, and a pharmaceutically acceptable excipient.

10. A method of treating a disease, a disorder, or a symptom causally related to LRRK2 in a subject, comprising administering to the subject a compound, or pharmaceutically acceptable salt thereof, of claim 2, or a pharmaceutical composition comprising a compound of claim 2, or a pharmaceutically acceptable salt thereof, and a pharmaceutically acceptable excipient.

11. The method of claim 9, wherein the disease or disorder is Parkinson's disease (PD) primary tauopathies, Lewy body dementia, Crohn's Disease, leprosy, neuroinflammation, Progressive Supranuclear Palsy, Picks disease, FTDtau, TDP-43 Frontal Temporal Dementia, TDP-43 ALS, c9orf ALS, Huntington's disease, any of spinocerebellar ataxias (SCAs) 1, 2, 3, 6, 7, and 17, dentatorubral pallidoluysian atrophy (DRPLA), or Kennedy's disease.

12. The method of claim 11, wherein the PD is idiopathic PD or LRRK2 mutation associated PD.

13. The method of claim 10, wherein the disease or disorder is Parkinson's disease (PD) primary tauopathies, Lewy body dementia, Crohn's Disease, leprosy, neuroinflammation, Progressive Supranuclear Palsy, Picks disease, FTDtau, TDP-43 Frontal Temporal Dementia, TDP-43 ALS, c9orf ALS, Huntington's disease, any of spinocerebellar ataxias (SCAs) 1, 2, 3, 6, 7, and 17, dentatorubral pallidoluysian atrophy (DRPLA), or Kennedy's disease.

14. The method of claim 13, wherein the PD is idiopathic PD or LRRK2 mutation associated PD.

15. A method of treating a subject having PD, a primary tauopathy, Lewy body dementia, Crohn's Disease, leprosy, neuroinflammation, Progressive Supranuclear Palsy, Picks disease, FTDtau, TDP-43 Frontal Temporal Dementia, TDP-43 ALS, c9orf ALS, Huntington's disease, any of SCAs 1, 2, 3, 6, 7, and 17, DRPLA or Kennedy's disease, the method comprising administering to the subject a compound, or pharmaceutically acceptable salt thereof, of claim 1, or a pharmaceutical composition comprising a compound of claim 1, or a pharmaceutically acceptable salt thereof, and a pharmaceutically acceptable excipient.

16. The method of claim 15, wherein the subject has PD.

17. The method of claim 16, wherein the subject has Progressive Supranuclear Palsy.

18. A method of treating a subject having PD, a primary tauopathy, Lewy body dementia, Crohn's Disease, leprosy, neuroinflammation, Progressive Supranuclear Palsy, Picks disease, FTDtau, TDP-43 Frontal Temporal Dementia, TDP-43 ALS, c9orf ALS, Huntington's disease, any of SCAs 1, 2, 3, 6, 7, and 17, DRPLA or Kennedy's disease, the method comprising administering to the subject a compound, or pharmaceutically acceptable salt thereof, of claim 2, or a pharmaceutical composition comprising a compound of claim 2, or a pharmaceutically acceptable salt thereof, and a pharmaceutically acceptable excipient.

19. The method of claim 18, wherein the subject has PD.

20. The method of claim 19, wherein the subject has Progressive Supranuclear Palsy.

* * * * *